(12) United States Patent
Sette et al.

(10) Patent No.: US 7,026,443 B1
(45) Date of Patent: Apr. 11, 2006

(54) INDUCING CELLULAR IMMUNE RESPONSES TO HUMAN PAPILLOMAVIRUS USING PEPTIDE AND NUCLEIC ACID COMPOSITIONS

(75) Inventors: Alessandro Sette, La Jolla, CA (US); John Sidney, San Diego, CA (US); Scott Southwood, Santee, CA (US); Robert Chesnut, Cardiff-by-the-Sea, CA (US); Esteban Celis, Rochester, MN (US); Howard M. Grey, La Jolla, CA (US)

(73) Assignee: Epimmune Inc., San Diego, CA (US)

( * ) Notice: Subject to any disclaimer, the term of this patent is extended or adjusted under 35 U.S.C. 154(b) by 588 days.

(21) Appl. No.: 09/641,528

(22) Filed: Aug. 15, 2000

Related U.S. Application Data

(60) Provisional application No. 60/172,705, filed on Dec. 10, 1999.

(51) Int. Cl.
*C07K 7/00* (2006.01)

(52) U.S. Cl. .................. 530/300; 424/184.1; 424/192.1; 424/193.1; 424/194.1; 424/204.1

(58) Field of Classification Search .............. 424/184.1, 424/192.1, 193.1, 194.1, 204.1; 530/300
See application file for complete search history.

(56) References Cited

U.S. PATENT DOCUMENTS

| | | | |
|---|---|---|---|
| 5,180,806 A | 1/1993 | Dillner et al. | |
| 5,200,320 A | 4/1993 | Sette et al. | |
| 5,503,829 A | 4/1996 | Ladant et al. | |
| 5,618,536 A | 4/1997 | Lowy et al. | |
| 5,662,907 A | 9/1997 | Kubo et al. | |
| 5,716,620 A | 2/1998 | Lowy et al. | |
| 5,753,233 A | 5/1998 | Bleul et al. | |
| 5,853,755 A | 12/1998 | Foldvari et al. | |
| 5,855,891 A | 1/1999 | Lowy et al. | |
| 5,871,998 A | 2/1999 | Lowy et al. | |
| 5,985,610 A | 11/1999 | Lowy et al. | |
| 6,034,214 A | 3/2000 | Boon et al. | |
| 6,037,135 A * | 3/2000 | Kubo et al. ................. | 435/7.24 |
| 2002/0098197 A1 | 7/2002 | Sette et al. | |
| 2002/0168374 A1 | 11/2002 | Kubo et al. | |
| 2002/0177694 A1 | 11/2002 | Sette et al. | |

FOREIGN PATENT DOCUMENTS

| | | |
|---|---|---|
| EP | 0 044 710 A1 | 1/1982 |
| EP | 0 226 513 A1 | 6/1987 |
| WO | WO 91/18294 | 11/1991 |
| WO | WO 92/02543 A1 | 2/1992 |
| WO | WO 92/12996 A2 | 8/1992 |
| WO | WO 92/21033 A1 | 11/1992 |
| WO | WO 93/03764 A1 | 3/1993 |
| WO | WO 93/22338 A1 | 11/1993 |
| WO | WO 94/03205 A1 | 2/1994 |
| WO | WO 94/11738 A1 | 5/1994 |
| WO | WO 94/20127 A1 | 9/1994 |
| WO | WO 95/31476 A1 | 11/1995 |
| WO | WO 96/03140 A1 | 2/1996 |
| WO | WO 96/19496 A1 | 6/1996 |
| WO | WO 99/45954 | 9/1999 |

OTHER PUBLICATIONS

NCBI Accession No.–X74479.*
Azoury–Ziadeh et al., Viral Immunology 1999 vol. 12 pp. 297–312.*
Murakami et al., Cancer Research , Mar. 15, 1999 pp. 1184–1187.*
Castellanos, M.R., et al., "Synthetic Peptides Induce a Cytotoxic Response against Human Paillomavirus Type–18," *Gynecol. Oncol.* 82:77–83, Academic Press (Jul. 2001).
Castellanos, M.R., et al., A rapid method to identify cytotoxic T–lymphocyte peptide epitopes from HLA–A2 (+) donors, *Crit. Rev. Oncol. Hematol.* 39:133–138, Elsevier Science Ireland, Ltd. (Jul./Aug. 2001).
"HPV and Animal PV Nucleic Acid Sequences," *Human Papillomaviruses 1997 Compendium, Part I. HPV and Animal PV Nucleotide Sequences in GenBank style*, pp. I–1–I17, The Human Papillomavirus Database (Sep. 1997).
Kast, W.M., et al., "Role of HLA–A Motifs in Identification of Potential CTL Epitopes in Human Papillomavirus Type 16 E6 and E7 Proteins," *J. Immunol.* 152:3904–3912, The American Association of Immunologists (Apr. 1994).
Ressing, M.E., et al., "Human CTL Epitopes Encoded by Human Papillomavirus Type 15 E6 and E7 Identified Through In Vivo and In Vitro Immunogenecity Studies of HLA–A*0201–Binding Peptides," *J. Immunol.* 154:5934–5942, The American Association of Immunologists (Jun. 1995).
Rowen, D., and Lacey, C., "Toward a human papillomavirus vaccine," *Dermatologic Clinics 16*:835–838, W.B. Saunders (Oct. 1998).
Yoon, H., et al., "Synthetic peptides of human papillomavirus type 185 E6 harboring HLA–A2.1 motif can induce peptide–specific cytotoxic T–cells from peripheral blood mononuclear cells of healthy donors," *Virus Res.* 54:23–29, Elsevier Science B.V. (Mar. 1998).
Copy of co–pending U.S. Appl. No. 08/205,713, filed Mar. 4, 1974, inventor Gray (Not Published).
Copy of co–pending U.S. Appl. No. 08/344,824, filed Nov. 23, 1994, inventors Sette et al., (Not Published).

(Continued)

*Primary Examiner*—James Housel
*Assistant Examiner*—Myron G. Hill
(74) *Attorney, Agent, or Firm*—Sterne, Kessler, Goldstein & Fox P.L.L.C.

(57) ABSTRACT

This invention uses our knowledge of the mechanisms by which antigen is recognized by T cells to identify and prepare human papillomavirus (HPV) epitopes, and to develop epitope-based vaccines directed towards HPV. More specifically, this application communicates our discovery of pharmaceutical compositions and methods of use in the prevention and treatment of HPV infection.

10 Claims, No Drawings

OTHER PUBLICATIONS

Copy of co–pending U.S. Appl. No. 08/347,610, filed Dec. 1, 1994, inventors Kubo et al., (Not Published).

Copy of co–pending U.S. Appl. No. 09/017,524, filed Feb. 3, 1998, inventors Kubo et al., (Not Published).

Copy of co–pending U.S. Appl. No. 10/149,136, filed Jun. 10, 2002, inventors Sette et al., (Published).

Aichele, P., et al., "Antiviral cytotoxic T cell response induced by in vivo priming with a free synthetic peptide," *J. Exp. Med.* 171:1815–1820, Rockefeller University Press (1990).

Alexander, J., et al., "Derivation of HLA–A11/$K^b$ Transgenic Mice. Functional CTL Repertoire and Recognition of Human A11–Restricted CTL Epitopes," *J. Immunol.* 159:4753–4761, The American Association of Immunologists (Nov. 1997).

Bergmann, C.C., et al., "Differential Effects of Flanking Residues on Presentation of Epitopes from Chimeric Peptides," *J. Virol.* 68:5306–5310, American Society for Microbiology (Aug. 1994).

Bertoni, R., et al., "Human Histocompatibility Leukocyte Antigen–binding Supermotifs Predict Broadly Cross–reactive Cytotoxic T Lymphocyte Responses in Patients with Acute Hepatitis," *J. Clin. Invest.* 100:503–513, The American Society for Clinical Investigation, Inc. (Aug. 1997).

Bertoni, R., et al., "Human Class I Supertypes and CTL Repertoires Extend to Chimpanzees," *J. Immunol.* 161:4447–4455, American Association of Immunologists (Oct. 1998).

Bjorkman, P.J., et al., "Structure of the human class I histocompatibility antigen, HLA–A2," *Nature* 329:506–512, Macmillan Publishers, Ltd. (1987).

Bjorkman, P.J., et al., "The foreign antigen binding site and T cell recognition regions of class I histocompatibility antigens," *Nature* 329:512–518, Macmillan Publishers, Ltd. (1987).

Buus, S., et al., "Autologous Peptides Constitutively Occupy the Antigen Binding Site on Ia," *Science* 242:1045–1047, American Association for the Advancement of Science (1988).

Carreno, B.M., et al., "HLA–B37 and HLA–A2.1 molecules bind largely nonoverlapping sets of peptides," *Proc. Natl. Acad. Sci. USA* 87:3420–3424, National Academy Press (1990).

Corr, M., et al., "Endogenous Peptides of a Soluble Major Histocompatibility Complex Class I Molecule, H–2$L^{ds}$: Sequence Motif, Quantitative Binding, and Molecular Modeling of the Complex," *J. Exp. Med.* 176:1681–1692, Rockefeller University Press (Dec. 1992).

De Bruijn, M.L.H., et al., "Peptide loading of empty major histocompatibility complex molecules on RMA–S cells allows the induction of primary cytotoxic T lymphocyte responses," *Eur. J. Immunol.* 21:2963–2970, VCH Verlagsgesellschaft mbH (1991).

Del Val, M., et al., "Efficient Processing of an Antigenic Sequence for Presentation by MHC Class I Molecules Depends on Its Neighboring Residues in the Protein," *Cell* 66:1145–1153, Cell Press (1991).

Deres, K., et al., "In vivo priming of virus–specific cytotoxic T lymphocytes with synthetic lipopetide vaccine," *Nature* 342:561–564, Macmillan Publishers, Ltd. (1989).

Dibrino, M., et al., "HLA–A1 and HLA–A3 T Cell Epitopes Derived from Influenza Virus Proteins Predicted from Peptide Binding Motifs," *J. Immunol.* 151:5930–5935, The Association of Immunologists (Dec. 1993).

DiBrino, M., et al., "Endogenous peptides bound to HLA–A3 possess a specific combination of anchor residues that permit identification of potential antigenic peptides," *Proc. Natl. Acad. Sci. USA* 90:1508–1512, National Academy Press (Feb. 1993).

Ding, Y.–H., et al., "Two Human T Cell Receptors Bind in a Similar Diagonal Mode to the HLA–A2/Tax Peptide Complex Using Different TCR Amino Acids," *Immunity* 8:403–11, Cell Press (Apr. 1998).

Eisenlohr, L.C., et al., "Flanking Sequences Influence the Presentation of an Endogenously Synthesized Peptide to Cytotoxic T Lymphocytes," *J. Exp. Med.* 175:481–487, The Rockefeller University Press (Feb. 1992).

Engelhard, V.H., "Structure of peptides associated with MHC Class I molecules," *Curr. Opin. Immunol.* 6:13–23, Current Biology, Ltd. (Feb. 1994).

Falk, K., et al., "Allele–specific motifs revealed by sequencing of self–peptides eluted from MHC molecules," *Nature* 351:290–296, Macmillan Publishers, Ltd. (1991).

Falk, K., et al., "MHC peptide motif register. Peptide motifs of HLA–B35 and –B37 molecules," *Immunogenetics* 38:161–162, Springer–Verlag (Apr. 1993).

Falk, K., et al., "Allele–specific peptide ligand motifs of HLA–C molecules," *Proc. Natl. Acad. Sci. USA* 90:12005–12009, National Academy Press (Dec. 1993).

Falk, K., et al., "Pool sequencing of natural HLA–DR, DQ, and DP ligands reveals detailed peptide motifs, constraints of processing, and general rules," *Immunogenetics* 39:230–242, Springer–Verlag (Feb. 1994).

Falk, K., et al., "Peptide motifs of HLA–A1, –A11, –A31, and –A33 molecules," *Immunogenetics* 40:238–241, Springer–Verlag (Jul. 1994).

Foon, K.A., "Biological Response Modifiers: The New Immunotherapy," *Cancer Res.* 49:1621–1639, American Association for Cancer Research (1989).

Geysen, H.M., et al., "Cognitive Features of Continuous Antigenic Determinants," *J. Mol. Recognit.* 1:32–41, Heyden & sons, Ltd. (1988).

Guo, H.–C., et al., "Different length peptides bind to HLA–Aw68 similarly at their ends but bulge out in the middle," *Nature* 360:364–366, Macmillan Publishers, Ltd. (Nov. 1992).

Henderson, R.A., et al., "HLA–A2.1–Associated Peptides from a Mutant Cell Line: A Second Pathway of Antigen Presentation," *Science* 255:1264–1266, American Association for the Advancement of Science (Mar. 1992).

Hill, A., et al., "Characterization of two Epstein–Barr virus epitopes restricted by HLA–B7," *Eur. J. Immunol.* 25:18–24, VCH Verlagsgesellschaft mbH (Jan. 1995).

Hunt, D.F., et al., "Characterization of Peptides Bound to the Class I MHC Molecule HLA–A2.1 by Mass Spectrometry," *Science* 255:1261–1263, American Association for the Advancement of Science (Mar. 1992).

Ishioka, G.Y., et al., "Utilization of MHC Class I Transgenic Mice for Development of Minigene DNA Vaccines Encoding Multiple HLA–Restricted CTL Epitopes," *J. Immunol.* 162:3915–3925, The American Association of Immunologists (Apr. 1999).

Jameson, S.C., and Bevan, M.J., "Dissection of major histocompatibility complex (MHC) and T cell receptor contact residues in a $K^b$–restricted ovalbumin peptide and an assessment of the predictive power of MHC–binding motifs," *Eur. J. Immunol.* 22:2663–2667, VCH Verlagsgesellschaft mbH (Oct. 1992).

Jardetzky, T.S., et al., "Identification of self peptides bound to purified HLA–B27," *Nature* 353:326–329, Macmillan Publishers, Ltd. (1991).

Kannagi, M., et al., "Target Epitope in the Tax Protein of Human T–Cell Leukemia Virus Type I Recognized by Class I Major Histocompatibility Complex–Restricted Cells," *J. Virol.* 66:2928–2933, American Society for Microbiology (May 1992).

Kast, W.M., et al., "Protection against lethal Sendai virus infection by in vivo priming of virus–specific cytotoxic T lymphocytes with a free synthetic peptide," *Proc. Natl. Acad. Sci. USA* 88:2283–2287, National Academy Press (1991).

Kast, W.M., et al., "Strict peptide length is not required for the induction of cytotoxic T lymphocyte–mediated antiviral protection by peptide vaccination," *Eur. J. Immunol.* 23:1189–1192, VCH Verlagsgesellschaft mbH (May 1993).

Krieger, J.I., et al., "Single amino acid changes in DR and antigen define residues critical for peptide–MHC binding and T cell recognition," *J. Immunol.* 146:2331–2340, American Association of Immunologists (1991).

Lipford, G.B., et al., "Primary in Vivo Responses to Ovalbumin. Probind the Predictive Value of the $K^b$ Binding Motif," *J. Immunol.* 150:1212–1222, The American Association of Immunologists (Feb. 1993).

Maryanski, J.L., et al., "Synthetic peptides as antigens and competitors in recognition by H–2–restricted cytolytic T cells specific for HLA," *J. Exp. Med.* 167:1391–1405, Rockefeller University Press (1988).

Maryanski, J.L., et al., "Competitor Analogs for Defined T Cell Antigens: Peptides Incorporating a Putative Binding Motif and Polyproline or Polyglycine Spacers," *Cell* 60:63–72, Cell Press (1990).

Morrison, J., et al., "Identification of the nonamer peptide from influenza A matrix protein and the role of pockets of HLA–A2 in its recognition by cytotoxic T lymphocytes," *Eur. J. Immunol.* 22:903–907, VCH Verlagsgesellschaft mbH (Apr. 1992).

Niedermann, G., et al., "The proteolytic fragments generated by vertebrate proteosomes: Structural relationships to major histocompatibility complex class I binding peptides," *Proc. Natl. Acad. Sci. USA* 93:8572–8577, National Academy Press (Aug. 1996).

Ochoa–Garay, J., et al., "The ability of peptides to induce cytotoxic T cells in vitro does not strongly correlate with their affinity for the $H–2L^d$ molecule: implications for vaccine design and immunotherapy," *Mol. Immunol.* 34:273–281, Elsevier Science, Ltd. (Feb. 1997).

Pamer, E.G., et al., "Precise prediction of a dominant class I MHC–restricted epitome of Listeria monocytogenes," *Nature* 353:852–855, Macmillan Publishers, Ltd. (1991).

Parham, P., et al., "The Origins of HLA–A, B, C Polymorphism," *Immunol. Rev.* 143:141–180, Munksgaard (Feb. 1995).

Parker, K.C., et al., "Peptide Binding to HLA–A2 and HLA–B27 Isolated from *Escherichia coli*," *J. Biol. Chem.* 267:5451–5459, American Society for Biochemistry and Molecular Biology, Inc. (Mar. 1992).

Parker, K.C., et al., "Sequence motifs important for peptide binding to the human MHC class I molecule, HLA–A2," *J. Immunol.* 149:3580–3587, American Association of Immunologists (Dec. 1992).

Rammensee, H.–G., et al., "Peptides Naturally Presented by MHC Class I Molecules," *Annu. Rev. Immunol.* 11:213–244, Annual Reviews, Inc. (Jan. 1993).

Rammensee, H.–G., et al., "MHC ligands and peptide motifs: first listing," *Immunogenetics* 41:178–228, Springer–Verlag (Feb. 1995).

Reddehase, M.J., et al., "A pentapeptide as minimal antigenic determinant for MHC class I–restricted T lymphocytes," *Nature* 337:651–653, Macmillan Publishers, Ltd. (1989).

Romero, P., et al., "$H–2k^d$–restricted Antigenic Peptides Share a Simple Binding Motif," *J. Exp. Med.* 174:603–612, Rockefeller University Press (1991).

Rothbard, J.B., "Major histocompatibility complex–peptide interactions," *Curr. Opin. Immunol.* 2:99–105, Current Biology, Ltd. (1989).

Rötzschke, O., et al., "Isolation and analysis of naturally processed viral peptides as recognized by cytotoxic T cells," *Nature* 348:252–254, Macmillan Publishers, Ltd. (1990).

Rötzschke, O., et al., "Characterization of Naturally Occurring Minor Histocompatibility Peptides Including H–4 and H–Y," *Science* 249:283–287, American Association for the Advancement of Science (1990).

Rötzschke, O., and Falk, K., "Naturally–occurring peptide antigens derived from the MHC class–I–restricted processing pathway," *Immunol. Today* 12:447–455, Elsevier Science Publishers, Ltd. (1991).

Rotzschke, O., et al., "Peptide motifs of closely related HLA class I molecules encompass substantial differences," *Eur. J. Immunol.* 22:2453–2456, VCH Verlagsgesellschaft mbH (Sep. 1992).

Rötzschke, O., and Falk, K., "Origin, structure and motifs of naturally processed MHC class II ligands," *Curr. Opin. Immunol.* 6:45–51, Current Biology, Ltd. (Feb. 1994).

Rudinger, J., "Characteristics of the amino acids as components of a peptide hormone sequence," in *Peptide Hormones*, Parsons, J.A., ed., University Park Press, Baltimore, MD, pp. 1–7 (1976).

Ruppert, J., et al., "Prominent Role of Secondary Anchor Residues in Peptide Binding to HLA–A2.1 Molecules," *Cell* 74:929–937, Cell Press (Sep. 1993).

Schulz, M., et al., "Major histocompatibility complex binding and T cell recognition of a viral nonapeptide containing a minimal tetrapeptide," *Eur. J. Immunol.* 21:1181–1185, VCH Verlagsgesellschaft mbH (1991).

Sette, A., et al., "Prediction of major histocompatibility complex binding regions of protein antigens by sequence pattern analysis," *Proc. Natl. Acad. Sci. USA* 86:3296–3300, National Academy Press (1989).

Sette, A., et al., "Random association between the peptide repertoire of A2.1 class I and several different DR class II molecules," *J. Immunol.* 147:3893–3900, The American Association of Immunologists (1991).

Sette, A., et al., "The Relationship Between Class I Binding Affinity and Immunogenicity of Potential Cytotoxic T Cell Epitopes," *J. Immunol.* 153:5586–5592, The American Association of Immunologists (Dec. 1994).

Shastri, N., et al., "Presentation of Endogenous Peptide/MHC Class I Complexes Is Profoundly Influenced by Specific C–Terminal Flanking Residues," *J. Immunol.* 155:4339–4346, The American Association of Immunologists (Nov. 1995).

Sherman, L.A., et al., "Extracellular Processing of Peptide Antigens That Bind Class I Major Histocompatibility Molecules," *J. Exp. Med.* 175:1221–1226, The Rockefeller University Press (May 1992).

Shimojo, N., et al., "Specificity of peptide binding by the HLA–A2.1 molecule," *J. Immunol.* 143:2939–2947, The American Association of Immunologists (1989).

Sidney, J., et al., "Several HLA Alleles Share Overlapping Peptide Specificities," *J. Immunol.* 154:247–259, The American Association of Immunologists (Jan. 1995).

Threlkeld, S.C., et al., "Degenerate and Promiscuous Recognition by CTL of Peptides Presented by the MHC Class I A3–like Superfamily. Implications for Vaccine Development," *J. Immunol.* 159:1648–1657, The American Association of Immunologists (Aug. 1997).

Wentworth, P.A., et al., "Differences and similarities in the A2.1–restricted cytotoxic T cell repertoire in humans and human leukocyte antigen–transgenic mice," *Eur. J. Immunol.* 26:97–101, VCH Verlagsgesellschaft mbH (Jan. 1996).

Whitton, J.L., et al., "Molecular Analyses of a Five–Amino–Acid Cytotoxic T–Lymphocyte (CTL) Epitope: an Immunodominant Region Which Induces Nonreciprocal CTL Cross–Reactivity," *J. Virol.* 63:4303–4310, American Society for Microbiology (1989).

Yewdell, J.W., and Bennink, J.R., "Cell Biology of Antigen Processing and Presentation to Major Histocompatibility Complex Class I Molecule–Restricted T Lymphocytes," *Adv. Immunol.* 52:1–123, Academic Press (Jul. 1992).

York, I.A., and Rock, K.L., "Antigen processing and presentation by the class I major histocompatibility complex," *Annu. Rev. Immunol.* 14:369–396, Annual Reviews, Inc. (Apr. 1996).

Zhang, Q–J., et al., "An HLA–All–specific motifs in nonamer peptides derived from viral and cellular proteins," *Proc. Natl. Acad. Sci. USA* 90:2217–2221, National Academy Press (Mar. 1993).

Parker, K.C., et al., "Scheme for Ranking Potential HLA–A2 Binding Peptides Based on Independent Binding of Individual Peptide Side–Chains," *J. Immunol.* 152:163–175, The American Association of Immunologists (Jan. 1994).

Dialog File 351, Accession No. 7180926, Derwent WPI English language abstract for EP 0 226 513.

Dialog File 351, Accession No. 9263567, Derwent WPI English language abstract for WO 92/21033.

Dialog File 351, Accession No. 9888606, Derwent WPI English language abstract for WO 94/11738.

Altuvia, Y. et al., "A Structure–Based Algorithm to Predict Potential Binding Peptides to MHC Molecules with Hydrophobic Binding Pockets," *Human Immunol.* 58:1–11, Elsevier Science Inc. (1997).

* cited by examiner

INDUCING CELLULAR IMMUNE RESPONSES TO HUMAN PAPILLOMAVIRUS USING PEPTIDE AND NUCLEIC ACID COMPOSITIONS

CROSS-REFERENCES TO RELATED APPLICATIONS

The present application claims priority to U.S. Ser. No. 60/172,705 filed Dec. 10, 1999. The application is also related to U.S. Ser. No. 09/189,702, filed Nov. 10, 1998, which is a CIP of U.S. Ser. No. 08/205,713 filed Mar. 4, 1994, which is a CIP of abandoned U.S. Ser. No. 08/159,184 filed Nov. 29, 1993, which is a CIP of abandoned U.S. Ser. No. 08/073,205 filed Jun. 4, 1993 which is a CIP of abandoned U.S. Ser. No. 08/027,146 filed Mar. 5, 1993. Additionally, the present application is related to U.S. Ser. No. 09/226,775, which is a CIP of abandoned U.S. Ser. No. 08/815,396, which claims benefit of abandoned U.S. Ser. No. 60/013,113. Furthermore, the present application is related to U.S. Ser. No. 09/017,735, which is a CIP of abandoned U.S. Ser. No. 08/589,108; U.S. Ser. No. 08/454,033; and U.S. Ser. No. 08/349,177. The present application is also related to U.S. Ser. No. 09/017,524, U.S. Ser. No. 08/821,739, which claims benefit of abandoned U.S. Ser. No. 60/013,833; and U.S. Ser. No. 08/347,610, which is a CIP of U.S. Ser. No. 08/159,339, which is a CIP of abandoned U.S. Ser. No. 08/103,396, which is a CIP of abandoned U.S. Ser. No. 08/027,746, which is a CIP of abandoned U.S. Ser. No. 07/926,666. The present application is also related to U.S. Ser. No. 09/017,743, which is a CIP of abandoned U.S. Ser. No. 08/590,298; and U.S. Ser. No. 08/452,843, which is a CIP of U.S. Ser. No. 08/344,824, which is a CIP of abandoned U.S. Ser. No. 08/278,634. The present application is also related to PCT application 99/12066 filed May 28, 1999 which claims benefit of provisional U.S. Ser. No. 60/087,192; U.S. Ser. No. 09/009,953, which is a CIP of abandoned U.S. Ser. No. 60/036,713; and abandoned U.S. Ser. No. 60/037,432. In addition, the present application is related to U.S. Ser. No. 09/098,584; U.S. Ser. No. 09/239,043; U.S. Ser. No. 60/117,486; U.S. Ser. No. 09/350,401; U.S. Ser. No. 09/357,737; and U.S. Ser. No. 09/390,061. All of the above applications are incorporated herein by reference.

FEDERALLY SPONSORED RESEARCH AND DEVELOPMENT

This invention was funded, in part, by the United States government under grants with the National Institutes of Health. The U.S. government has certain rights in this invention.

REFERENCE TO MICROFICHE APPENDIX/ SEQUENCE LISTING/TABLE/COMPUTER PROGRAM LISTING APPENDIX

(SUBMITTED ON A COMPACT DISC AND AN INCORPORATION-BY-REFERENCE OF THE MATERIAL ON THE COMPACT DISC)

The Substitute Sequence Listing written in file Sequence Listing 2060_0100001, created on Oct. 17, 2003 on compact disc for application Ser. No. 09/641,528, Sette et al., Inducing Cellular Immune Responses to Human Papillomavirus Using Peptide and Nucleic Acid Compositions, is herein incorporated-by-reference.

I. Background of the Invention
II. Summary of the Invention
III. Detailed Description of the Invention
   A. Definitions
   B. Stimulation of CTL and HTL responses
   C. Binding Affinity of Peptide Epitopes for HLA Molecules
   D. Peptide Epitope Binding Motifs and Supermotifs
      1. HLA-A1 supermotif
      2. HLA-A2 supermotif
      3. HLA-A3 supermotif
      4. HLA-A24 supermotif
      5. HLA-B7 supermotif
      6. HLA-B27 supermotif
      7. HLA-B44 supermotif
      8. HLA-B58 supermotif
      9. HLA-B62 supermotif
      10. HLA-A1 motif
      11. HLA-A2.1 motif
      12. HLA-A3 motif
      13. HLA-A11 motif
      14. HLA-A24 motif
      15. HLA-DR-1-4-7 supermotif
      16. HLA-DR3 motifs
   E. Enhancing Population Coverage of the Vaccine
   F. Immune Response-Stimulating Peptide Epitope Analogs
   G. Computer Screening of Protein Sequences from Disease-Related Antigens for Supermotif- or Motif-Containing Epitopes
   H. Preparation of Peptide Epitopes
   I. Assays to Detect T-Cell Responses
   J. Use of Peptide Epitopes for Evaluating Immune Responses
   K. Vaccine Compositions
      1. Minigene Vaccines
      2. Combinations of CTL Peptides with Helper Peptides
      3. Combinations of CTL Peptides with T Cell Priming Agents
      4. Vaccine Compositions Comprising Dendritic Cells Pulsed with CTL and/or HTL Peptides
   L. Administration of Vaccines for Therapeutic or Prophylactic Purposes
   M. Kits
V. Examples
VI. Claims
VII. Abstract

I. BACKGROUND OF THE INVENTION

Human papillomavirus (HPV) is a member of the papillomaviridae, a group of small DNA viruses that infect a variety of higher vertebrates. More than 80 types of HPVs have been identified. Of these, more than 30 can infect the genital tract. Some types, generally types 6 and 11, may cause genital warts, which are typically benign and rarely develop into cancer. Other strains of HPV, "cancer-associated", or "high-risk" types, can lead to the development of cancer.

Cancer-associated HPVs have been linked with cancer in both men and women; they include, but are not limited to, HPV-16, HPV-18, HPV-31, HPV-45, HPV-33 and HPV-56. Other HPV strains, including types 6 and 11 as well as others, e.g., HPV-5 and HPV-8, are less frequently associated with cancer. The high risk types are typically associated with the development of cervical carcinoma and premalignant lesions of the cervix in women, but are also associated with similar malignant and premalignant lesions at other anatomic sites within the lower genital or anogenital tract. These lesions include neoplasia of the vagina, vulva, perineum, the penis, and the anus. HPV infection has also been associated with respiratory tract papillomas, and rarely, cancer, as well as abnormal growth or neoplasia in other epithelial tissues. See, e.g. VIROLOGY, $2^{ND}$ ED, Fields et at., Eds. Raven Press, New York, 1990, Chapters 58 and 59, for a review of HPV association with cancer.

The HPV genome consists of three functional regions, the early region, the late region, and the "long control region". The early region gene products control viral replication, transcription and cellular transformation They include the HPV E1 and E2 proteins, which play a role in HPV DNA replication, and the E6 and E7 oncoproteins, which are involved in the control of cellular proliferation. The late region include the genes that encode the structural proteins L1 and L2, which are the major and minor capsid proteins, respectively. The "long control region" contains such sequences as enhancer and promoter regulatory regions.

HPV expresses different proteins at different stages of the infection, for example early, as well as late, proteins. Even in latent infections, however, early proteins are often expressed and are therefore useful targets for vaccine-based therapies. For example, high-grade dysplasia and cervical squamous cell carcinoma continue to express E6 and E7, which therefore can be targeted to treat disease at both early and late stages of infection.

Treatment for HPV infection is often unsatisfactory because of persistence of virus after treatment and recurrence of clinically apparent disease is common. Thus, a need exists for an efficacious vaccine to both prevent and treat HPV infection and to treat cancer that is associated with HPV infection. Effective HPV vaccines would be a significant advance in the control of sexually transmissable infections and could also protect against clinical disease, particularly cancers such as cervical cancer. (see, e.g., Rowen, P. & Lacey, C., *Dermatologic Clinics* 16(4):835–838, 1998).

Virus-specific, human leukocyte antigen (HLA) class I-restricted cytotoxic T lymphocytes (CTL) are known to play a major role in the prevention and clearance of virus infections in vivo (Oldstone et al., *Nature* 321:239, 1989; Jamieson et al., *J. Virol.* 61:3930, 1987; Yap et al, *Nature* 273:238, 1978; Lukacher et al., *J. Exp. Med.* 160:814, 1994; McMichael et al., *N. Engl. J. Med.* 309:13, 1983; Sethi et al., *J. Gen. Virol.* 64:443, 1983; Watari et al. *J. Exp. Med.* 65:459, 1987; Yasukawa et al., *J. Immunol.* 143:2051, 1989; Tigges et al., *J. Virol.* 66:1622, 1993; Reddenhase et al., *J. Virol.* 55:263, 1985; Quinnan et al., *N. Engl. J. Med.* 307:6, 1982). HLA class I molecules are expressed on the surface of almost all nucleated cells. Following intracellular processing of antigens, epitopes from the antigens are presented as a complex with the HLA class I molecules on the surface of such cells. CTL recognize the peptide-HLA class I complex, which then results in the destruction of the cell bearing the HLA-peptide complex directly by the CTL and/or via the activation of non-destructive mechanisms e.g., the production of interferon, that inhibit viral replication.

Virus-specific T helper lymphocytes are also known to be critical for maintaining effective immunity in chronic viral infections. Historically, HTL responses were viewed as primarily supporting the expansion of specific CTL and B cell populations; however, more recent data indicate that HTL may directly contribute to the control of virus replication. For example, a decline in $CD4^+$T cells and a corresponding loss in HTL function characterize infection with HIV (Lane et al., *New Engl. J. Med.* 313:79, 1985). Furthermore, studies in HIV infected patients have also shown that there is an inverse relationship between virus-specific HTL responses and viral load, suggesting that HTL plays a role in viremia (see, e.g., Rosenberg et al., *Science* 278:1447, 1997).

The development of vaccines with prophylactic and therapeutic efficacy against HPV is ongoing. Early vaccine development was hampered by the inability to culture HPV. With the introduction of cloning techniques and protein expression, however, some attempts have been made to stimulate humoral and CTL response to HPV (See, e.g., Rowen, P. & Lacey, C., *Dermatologic Clinics* 16(4):835–838 (1998)). Studies to date, however, have been inconclusive.

Activation of T helper cells and cytotoxic lymphocytes (CTLs) in the development of vaccines has also been analyzed. Lehtinen, M., et al. for instance, has shown that some peptides from the E2 protein of HPV type 16 activate T helper cells and CTLs (*Biochem. Biophys. Res. Commun.* 209(2):541–6 (1995). Similarly, Tarpey et al, has shown that some peptides from HPV type 11 E7 protein can stimulate human HPV-specific CTLs in vitro (*Immunology* 81:222–227 (1994)) and Borysiewicz et al. have reported a recombinant vaccinia virus expressing HPV 16 and HPV 17 E6 and E7 that stimulated CTL responses in at least one patient (*Lancet* 347:1347–1357, 1996).

The epitope approach, as we have described, allows the incorporation of various antibody, CTL and HTL epitopes, from various proteins, in a single vaccine composition. Such a composition may simultaneously target multiple dominant and subdominant epitopes and thereby be used to achieve effective immunization in a diverse population.

The information provided in this section is intended to disclose the presently understood state of the art as of the filing date of the present application. Information is included in this section which was generated subsequent to the priority date of this application. Accordingly, information in this section is not intended, in any way, to delineate the priority date for the invention.

II. SUMMARY OF THE INVENTION

This invention applies our knowledge of the mechanisms by which antigen is recognized by T cells, for example, to develop epitope-based vaccines directed towards HPV. More specifically, this application communicates our discovery of specific epitope pharmaceutical compositions and methods of use in the prevention and treatment of HPV infection.

Upon development of appropriate technology, the use of epitope-based vaccines has several advantages over current vaccines, particularly when compared to the use of whole antigens in vaccine compositions. There is evidence that the immune response to whole antigens is directed largely toward variable regions of the antigen, allowing for immune escape due to mutations. The epitopes for inclusion in an epitope-based vaccine may be selected from conserved regions of viral or tumor-associated antigens, which thereby reduces the likelihood of escape mutants. Furthermore, immunosuppressive epitopes that may be present in whole antigens can be avoided with the use of epitope-based vaccines.

An additional advantage of an epitope-based vaccine approach is the ability to combine selected epitopes (CTL and HTL), and further, to modify the composition of the epitopes, achieving, for example, enhanced immunogenicity. Accordingly, the immune response can be modulated, as appropriate, for the target disease. Similar engineering of the response is not possible with traditional approaches.

Another major benefit of epitope-based immune-stimulating vaccines is their safety. The possible pathological side effects caused by infectious agents or whole protein antigens, which might have their own intrinsic biological activity, is eliminated.

An epitope-based vaccine also provides the ability to direct and focus an immune response to multiple selected antigens from the sane pathogen. Thus, patient-by-patient variability in the immune response to a particular pathogen may be alleviated by inclusion of epitopes from multiple antigens from the pathogen in a vaccine composition. In the case of HPV, epitopes derived from multiple strains may also be included. A "pathogen" may be an infectious agent or a tumor associated molecule.

One of the most formidable obstacles to the development of broadly efficacious epitope-based immunotherapeutics, however, has been the extreme polymorphism of HLA molecules. To date, effective non-genetically biased coverage of a population has been a task of considerable complexity; such coverage has required that epitopes be used that are specific for HLA molecules corresponding to each individual HLA allele. Impractically large numbers of epitopes would therefore have to be used in order to cover ethnically diverse populations. Thus, there has existed a need for peptide epitopes that are bound by multiple HLA antigen molecules for use in epitope-based vaccines. The greater the number of HLA antigen molecules bound, the greater the breadth of population coverage by the vaccine.

Furthermore, as described herein in greater detail, a need has existed to modulate peptide binding properties, e.g., so that peptides that are able to bind to multiple HLA antigens do so with an affinity that will stimulate an immune response. Identification of epitopes restricted by more than one HLA allele at an affinity that correlates with immunogenicity is important to provide thorough population coverage, and to allow the elicitation of responses of sufficient vigor to prevent or clear an infection in a diverse segment of the population. Such a response can also target a broad array of epitopes. The technology disclosed herein provides for such favored immune responses.

In a preferred embodiment, epitopes for inclusion in vaccine compositions of the invention are selected by a process whereby protein sequences of known antigens are evaluated for the presence of motif or supermotif-bearing epitopes. Peptides corresponding to a motif- or supermotif-bearing epitope are then synthesized and tested for the ability to bind to the HLA molecule that recognizes the selected motif. Those peptides that bind at an intermediate or high affinity i.e., an $IC_{50}$ (or a $K_D$ value) of 500 nM or less for HLA class I molecules or an $IC_{50}$ of 1000 nM or less for HLA class II molecules, are further evaluated for their ability to induce a CTL or HTL response. Immunogenic peptide epitopes are selected for inclusion in vaccine compositions.

Supermotif-bearing peptides may additionally be tested for the ability to bind to multiple alleles within the HLA supertype family. Moreover, peptide epitopes may be analogued to modify binding affinity and/or the ability to bind to multiple alleles within an HLA supertype.

The invention also includes embodiments comprising methods for monitoring or evaluating an immune response to HPV in a patient having a known HLA-type. Such methods comprise incubating a T lymphocyte sample from the patient with a peptide composition comprising an HPV epitope that has an amino acid sequence described in Tables VII to Table XX which binds the product of at least one HLA allele present in the patient, and detecting for the presence of a T lymphocyte that binds to the peptide. A CTL peptide epitope may, for example, be used as a component of a tetrameric complex for this type of analysis.

An alternative modality for defining the peptide epitopes in accordance with the invention is to recite the physical properties, such as length; primary structure; or charge, which are correlated with binding to a particular allele-specific HLA molecule or group of allele-specific HLA molecules. A further modality for defining peptide epitopes is to recite the physical properties of an HLA binding pocket, or properties shared by several allele-specific HLA binding pockets (e.g. pocket configuration and charge distribution) and reciting that the peptide epitope fits and binds to the pocket or pockets.

As will be apparent from the discussion below, other methods and embodiments are also contemplated. Further, novel synthetic peptides produced by any of the methods described herein are also part of the invention.

III. DETAILED DESCRIPTION OF THE INVENTION

The peptides and corresponding nucleic acid compositions of the present invention are useful for stimulating an immune response to HPV by stimulating the production of CTL or HTL responses. The peptide epitopes, which are derived directly or indirectly from native HPV protein amino acid sequences, are able to bind to HLA molecules and stimulate an immune response to HPV. The complete sequence of the HPV proteins to be analyzed can be obtained from Genbank. Epitopes and analogs thereof can also be readily determined from sequence information that may subsequently be discovered for heretofore unknown variants of HPV, as will be clear from the disclosure provided below.

The epitopes of the invention have been identified in a number of ways, as will be discussed below. Also discussed in greater detail is that analog peptides have been derived and the binding activity for HLA molecules modulated by modifying specific amino acid residues to create peptide analogs exhibiting altered imunogenicity. Further, the present invention provides compositions and combinations of compositions that enable epitope-based vaccines that are capable of interacting with HLA molecules encoded by various genetic alleles to provide broader population coverage than prior vaccines.

III.A. Definitions

The invention can be better understood with reference to the following definitions, which are listed alphabetically:

A "computer" or "computer system" generally includes: a processor; at least one information storage/retrieval apparatus such as, for example, a hard drive, a disk drive or a tape drive; at least one input apparatus such as, for example, a keyboard, a mouse, a touch screen, or a microphone; and display structure. Additionally, the computer may include a communication channel in communication with a network. Such a computer may include more or less than what is listed above.

A "construct" as used herein generally denotes a composition that does not occur in nature. A construct can be produced by synthetic technologies, e.g., recombinant DNA preparation and expression or chemical synthetic techniques for nucleic or amino acids. A construct can also be produced by the addition or affiliation of one material with another such that the result is not found in nature in that form.

"Cross-reactive binding" indicates that a peptide is bound by more than one HLA molecule; a synonym is degenerate binding.

A "cryptic epitope" elicits a response by immunization with an isolated peptide, but the response is not cross-reactive in vitro when intact whole protein which comprises the epitope is used as an antigen.

A "dominant epitope" is an epitope that induces an immune response upon immunization with a whole native antigen (see, e.g., Sercarz, et al., *Annu. Rev. Immunol.* 11:729–766, 1993). Such a response is cross-reactive in vitro with an isolated peptide epitope.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vivo or in vitro, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably. It is to be appreciated, however, that isolated or purified protein or peptide molecules larger than and comprising an epitope of the invention are still within the bounds of the invention.

"Human Leukocyte Antigen" or "HLA" is a human class I or class II Major Histocompatibility Complex (MHC) protein (see, e.g., Stites, et al., IMMUNOLOGY, $8^{TH}$ ED., Lange Publishing, Los Altos, Calif. (1994).

An "HLA supertype or family", as used herein, describes sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, HLA family, and HLA xx-like molecules (where xx denotes a particular HLA type), are synonyms.

Throughout this disclosure, results are expressed in terms of "$IC_{50}$'s." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. Assays for determining binding are described in detail, e.g., in PCT publications WO 94/20127 and WO 94/03205. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand.

Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide.

Binding may also be determined using other assay systems including those using: live cells (e.g., Ceppellini et al., *Nature* 339:392, 1989; Christnick et al., *Nature* 352:67, 1991; Busch et al., *Int. Immunol.* 2:443, 19990; Hill et al., *J. Immunol.* 147:189, 1991; del Guercio et al., *J. Immunol.* 154:685, 1995), cell free systems using detergent lysates (e.g., Cerundolo et a., *J. Immunol.* 21:2069, 1991), immobilized purified MHC (e.g., Hill et al., *J. Immunol.* 152, 2890, 1994; Marshall et al., *J. Immunol.* 152:4946, 1994), ELISA systems (e.g., Reay et al., *EMBO J.* 11:2829, 1992), surface plasmon resonance (e.g., Khilko et al., *J. Biol. Chem.* 268:15425, 1993); high flux soluble phase assays (Hammer et al., *J. Exp. Med.* 180:2353, 1994), and measurement of class I MHC stabilization or assembly (e.g., Ljunggren et al., *Nature* 346:476, 1990; Schumacher et al., *Cell* 62:563, 1990; Townsend et al., *Cell* 62:285, 1990; Parker et al., *J. Immunol.* 149:1896, 1992).

As used herein, "high affinity" with respect to HLA class I molecules is defined as binding with an $IC_{50}$, or $K_D$ value, of 50 nM or less; "intermediate affinity" is binding with an $IC_{50}$ or $K_D$ value of between about 50 and about 500 nM. "High affinity" with respect to binding to HLA class II molecules is defined as binding with an $IC_{50}$ or $K_D$ value of 100 nM or less; "intermediate affinity" is binding with an $IC_{50}$ or $K_D$ value of between about 100 and about 1000 nM.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

An "immunogenic peptide" or "peptide epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment.

"Link" or "join" refers to any method known in the art for functionally connecting peptides, including, without limitation, recombinant fusion, covalent bonding, disulfide bonding, ionic bonding, hydrogen bonding, and electrostatic bonding.

"Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, Paul, FUNDAMENTAL IMMUNOLOGY, $3^{RD}$ ED., Raven Press, New York, 1993.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "negative binding residue" or "deleterious residue" is an amino acid which, if present at certain positions (typically not primary anchor positions) in a peptide epitope, results in decreased binding affinity of the peptide for the peptide's corresponding HLA molecule.

A "non-native" sequence or "construct" refers to a sequence that is not found in nature, i.e., is "non-naturally occurring". Such sequences include, e.g., peptides that are lipidated or otherwise modified, and polyepitopic compositions that contain epitopes that are not contiguous in a native protein sequence.

The term "peptide" is used interchangeably with "oligopeptide" in the present specification to designate a series of residues, typically L-amino acids, connected one to the other, typically by peptide bonds between the α-amino and carboxyl groups of adjacent amino acids. The preferred CTL-inducing peptides of the invention are 13 residues or less in length and usually consist of between about 8 and about 11 residues, preferably 9 or 10 residues. The preferred HTL-inducing oligopeptides are less than about 50 residues in length and usually consist of between about 6 and about 30 residues, more usually between about 12 and 25, and often between about 15 and 20 residues.

It is to be appreciated that protein or peptide molecules that comprise an epitope of the invention as well as additional amino acid(s) are within the bounds of the invention. In certain embodiments, there is a limitation on the length of a peptide of the invention which is not otherwise a construct as defined herein. An embodiment that is length-limited occurs when the protein/peptide comprising an epitope of the invention comprises a region (i.e., a contiguous series of amino acids) having 100% identity with a native sequence. In order to avoid a recited definition of epitope from reading, e.g., on whole natural molecules, the length of any region that has 100% identity with a native peptide sequence is limited. Thus, for a peptide comprising an epitope of the invention and a region with 100% identity with a native peptide sequence (and which is not otherwise a construct), the region with 100% identity to a native sequence generally has a length of: less than or equal to 600 amino acids, often less than or equal to 500 amino acids, often less than or equal to 400 amino acids, often less than or equal to 250 amino acids, often less than or equal to 100 amino acids, often less than or equal to 85 amino acids, often less than or equal to 75 amino acids, often less than or equal to 65 amino acids, and often less than or equal to 50 amino acids. In certain embodiments, an "epitope" of the invention which is not a construct is comprised by a peptide having a region with less than 51 amino acids that has 100% identity to a native peptide sequence, in any increment of (50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5) down to 5 amino acids.

Certain peptide or protein sequences longer than 600 amino acids are within the scope of the invention. Such longer sequences are within the scope of the invention so long as they do not comprise any contiguous sequence of more than 600 amino acids that have 100% identity with a native peptide sequence, or if longer than 600 amino acids, they are a construct. For any peptide that has five contiguous residues or less that correspond to a native sequence, there is no limitation on the maximal length of that peptide in order to fall within the scope of the invention. It is presently preferred that a CTL epitope of the invention be less than 600 residues long in any increment down to eight amino acid residues.

"Pharmaceutically acceptable" refers to a non-toxic, inert, and/or physiologically compatible composition.

A "pharmaceutical excipient" comprises a material such as an adjuvant, a carrier, pH-adjusting and buffering agents, tonicity adjusting agents, wetting agents, preservative, and the like.

A "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding grooves of an HLA molecule, with their side chains buried in specific pockets of the binding grooves themselves. In one embodiment, for example, the primary anchor residues are located at position 2 (from the amino terminal position) and at the carboxyl terminal position of a 9-residue peptide epitope in accordance with the invention. The primary anchor positions for each motif and supermotif are set forth in Table 1. For example, analog peptides can be created by altering the presence or absence of particular residues in these primary anchor positions. Such analogs are used to modulate the binding affinity of a peptide comprising a particular motif or supermotif.

"Promiscuous recognition" is where a distinct peptide is recognized by the same T cell clone in the context of various HLA molecules. Promiscuous recognition or binding is synonymous with cross-reactive binding.

A "protective immune response" or "therapeutic immune response" refers to a CTL and/or an HTL response to an antigen derived from an infectious agent or a tumor antigen, which prevents or at least partially arrests disease symptoms or progression. The immune response may also include an antibody response which has been facilitated by the stimulation of helper T cells.

The term "residue" refers to an amino acid or amino acid mimetic incorporated into an oligopeptide by an amide bond or amide bond mimetic.

A "secondary anchor residue" is an amino acid at a position other than a primary anchor position in a peptide which may influence peptide binding. A secondary anchor residue occurs at a significantly higher frequency amongst bound peptides than would be expected by random distribution of amino acids at one position. The secondary anchor residues are said to occur at "secondary anchor positions." A secondary anchor residue can be identified as a residue which is present at a higher frequency among high or intermediate affinity binding peptides, or a residue otherwise associated with high or intermediate affinity binding. For example, analog peptides can be created by altering the presence or absence of particular residues in these secondary anchor positions. Such analogs are used to finely modulate the binding affinity of a peptide comprising a particular motif or supermotif.

A "subdominant epitope" is an epitope which evokes little or no response upon immunization with whole antigens which comprise the epitope, but for which a response can be obtained by immunization with an isolated peptide, and this response (unlike the case of cryptic epitopes) is detected when whole protein is used to recall the response in vitro or in vivo.

A "supermotif" is a peptide binding specificity shared by HLA molecules encoded by two or more HLA alleles. Preferably, a supermotif-bearing peptide is recognized with high or intermediate affinity (as defined herein) by two or more HLA antigens.

"Synthetic peptide" refers to a peptide that is man-made using such methods as chemical synthesis or recombinant DNA technology.

As used herein, a "vaccine" is a composition that contains one or more peptides of the invention. There are numerous embodiments of vaccines in accordance with the invention, such as by a cocktail of one or more peptides; one or more epitopes of the invention comprised by a polyepitopic peptide; or nucleic acids that encode such peptides or polypeptides, e.g., a minigene that encodes a polyepitopic peptide. The "one or more peptides" can include any whole unit integer from 1–150, e.g., at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 105, 110, 115, 120, 125, 130, 135, 140, 145, or 150 or more peptides of the invention. The peptides or polypeptides can optionally be modified, such as by lipidation, addition of targeting or other sequences. HLA class I-binding peptides of the invention can be admixed with, or linked to, HLA class II-binding peptides, to facilitate activation of both cytotoxic T lymphocytes and helper T lymphocytes. Vaccines can also comprise peptide-pulsed antigen presenting cells, e.g., dendritic cells.

The nomenclature used to describe peptide compounds follows the conventional practice wherein the amino group is presented to the left (the N-terminus) and the carboxyl group to the right (the C-terminus) of each amino acid residue. When amino acid residue positions are referred to in a peptide epitope they are numbered in an amino to carboxyl direction with position one being the position closest to the amino terminal end of the epitope, or the peptide or protein of which it may be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G. Symbols for the amino acids are shown below.

| Single Letter Symbol | Three Letter Symbol | Amino Acids |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |

-continued

| Single Letter Symbol | Three Letter Symbol | Amino Acids |
|---|---|---|
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

III.B. Stimulation of CTL and HTL Responses

The mechanism by which T cells recognize antigens has been delineated during the past ten years. Based on our understanding of the immune system we have developed efficacious peptide epitope vaccine compositions that can induce a therapeutic or prophylactic immune response to HPV in a broad population. For an understanding of the value and efficacy of the claimed compositions, a brief review of immunology-related technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317:359, 1985; Townsend, A. and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are described herein and are set forth in Tables I, II, and III (see also, e.g., Southwood, et al, *J. Immunol.* 160:3363, 1998; Rammensee, et al., *Immunogenetics* 41:178, 1995; Rammensee et al., SYFPEITHI, access via web at: http://134.2.96.221/scripts.hlaserver.dll/home.htm; Sette, A. and Sidney, *J. Curr. Opin. Immunol.* 10:478, 1998; Engelhard, V. H., *Curr. Opin. Immunol.* 6:13, 1994; Sette, A. and Grey, H. M., *Curr. Opin. Immunol.* 4:79, 1992; Sinigaglia, F. and Hammer, *J. Curr. Biol.* 6:52, 1994; Ruppert et al, *Cell* 74:929–937, 1993; Kondo et al., *J. Immunol.* 155:4307–4312, 1995; Sidney et al, *J. Immunol.* 157:3480–3490, 1996; Sidney et a., *Human Immunol.* 45:79–93, 1996; Sette, A. and Sidney, *J. Immunogenetics*, in press, 1999).

Furthermore, x-ray crystallographic analysis of HLA-peptide complexes has revealed pockets within the peptide binding cleft of HLA molecules which accommodate, in an allele-specific mode, residues borne by peptide ligands; these residues in turn determine the HLA binding capacity of the peptides in which they are present. (See, e.g., Madden, D. R. *Annu. Rev. Immunol.* 13:587, 1995; Smith, et al., *Immunity* 4:203, 1996; Fremont et al., *Immunity* 8:305, 1998; Stem et al., *Structure* 2:245, 1994; Jones, E. Y. *Curr. Opin. Immunol.* 9:75, 1997; Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991.)

Accordingly, the definition of class I and class II allele-specific HLA binding motifs, or class I or class II supermotifs allows identification of regions within a protein that have the potential of binding particular HLA antigen(s).

The present inventors have found that the correlation of binding affinity with immunogenicity, which is disclosed herein, is an important factor to be considered when evaluating candidate peptides. Thus, by a combination of motif searches and HLA-peptide binding assays, candidates for epitope-based vaccines have been identified. After determining their binding affinity, additional confirmatory work can be performed to select, amongst these vaccine candidates, epitopes with preferred characteristics in terms of population coverage, antigenicity, and immunogenicity.

Various strategies can be utilized to evaluate immunogenicity, including:

1) Evaluation of primary T cell cultures from normal individuals (see, e.g., Wentworth, P. A. et al., *Mol. Immunol.* 32:603, 1995; Celis, E. et al., *Proc. Natl. Acad. Sci. USA* 91:2105, 1994; Tsai, V. et al., *J. Immunol.* 158:1796, 1997; Kawashima, I. et al., *Human Immunol.* 59:1, 1998); This procedure involves the stimulation of peripheral blood lymphocytes (PBL) from normal subjects with a test peptide in the presence of antigen presenting cells in vitro over a period of several weeks. T cells specific for the peptide become activated during this time and are detected using, e.g., a lymphokine- or $^{51}$Cr-release assay involving peptide sensitized target cells.

2) Immunization of HLA transgenic mice (see, e.g., Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997); In this method, peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using, e.g., a $^{51}$Cr-release assay involving peptide sensitized target cells and target cells expressing endogenously generated antigen.

3) Demonstration of recall T cell responses from immune individuals who have effectively been vaccinated, recovered from infection, and/or from chronically infected patients (see, e.g., Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997); In applying this strategy, recall responses are detected by culturing PBL from subjects that have been naturally exposed to the antigen, for instance through infection, and thus have generated an immune response "naturally", or from patients who were vaccinated against the infection. PBL from subjects are cultured in vitro for 1–2 weeks in the presence of test peptide plus antigen presenting cells (APC) to allow activation of "memory" T cells, as compared to "naive" T cells. At the end of the culture period, T cell activity is detected using assays for T cell activity including $^{51}$Cr release involving peptide-sensitized targets, T cell proliferation, or lymphokine release.

The following describes the peptide epitopes and corresponding nucleic acids of the invention.

III.C. Binding Affinity of Peptide Epitopes for HLA Molecules

As indicated herein, the large degree of HLA polymorphism is an important factor to be taken into account with the epitope-based approach to vaccine development. To address this factor, epitope selection encompassing identification of peptides capable of binding at high or intermediate affinity to multiple HLA molecules is preferably utilized, most preferably these epitopes bind at high or intermediate affinity to two or more allele-specific HLA molecules.

CTL-inducing peptides of interest for vaccine compositions preferably include those that have an $IC_{50}$ or binding affinity value for class I HLA molecules of 500 nM or better (i.e., the value is $\leq 500$ nM). HTL-inducing peptides preferably include those that have an $IC_{50}$ or binding affinity value for class II HLA molecules of 1000 nM or better, (i.e., the value is $\leq 1,000$ nM). For example, peptide binding is assessed by testing the capacity of a candidate peptide to bind to a purified HLA molecule in vitro. Peptides exhibiting high or intermediate affinity are then considered for further analysis. Selected peptides are tested on other members of the supertype family. In preferred embodiments, peptides that exhibit cross-reactive binding are then used in cellular screening analyses or vaccines.

As disclosed herein, higher HLA binding affinity is correlated with greater immunogenicity. Greater immunogenicity can be manifested in several different ways. Immunogenicity corresponds to whether an immune response is elicited at all, and to the vigor of any particular response, as well as to the extent of a population in which a response is elicited. For example, a peptide might elicit an immune response in a diverse array of the population, yet in no instance produce a vigorous response. In accordance with these principles, close to 90% of high binding peptides have been found to be immunogenic, as contrasted with about 50% of the peptides which bind with intermediate affinity. Moreover, higher binding affinity peptides lead to more vigorous immunogenic responses. As a result, less peptide is required to elicit a similar biological effect if a high affinity binding peptide is used. Thus, in preferred embodiments of the invention, high affinity binding epitopes are particularly useful.

The relationship between binding affinity for HLA class I molecules and immunogenicity of discrete peptide epitopes on bound antigens has been determined for the first time in the art by the present inventors. The correlation between binding affinity and immunogenicity was analyzed in two different experimental approaches (see, e.g., Sette, et al., *J. Immunol.* 153:5586–5592, 1994). In the first approach, the immunogenicity of potential epitopes ranging in HLA binding affinity over a 10,000-fold range was analyzed in HLA-A*0201 transgenic mice. In the second approach, the antigenicity of approximately 100 different hepatitis B virus (HBV)-derived potential epitopes, all carrying A*0201 binding motifs, was assessed by using PBL from acute hepatitis patients. Pursuant to these approaches, it was determined that an affinity threshold value of approximately 500 nM (preferably 50 nM or less) determines the capacity of a peptide epitope to elicit a CTL response. These data are true for class I binding affinity measurements for naturally processed peptides and for synthesized T cell epitopes. These data also indicate the important role of determinant selection in the shaping of T cell responses (see, e.g., Schaeffer et al. *Proc. Natl. Acad. Sci. USA* 86:4649–4653, 1989).

An affinity threshold associated with immunogenicity in the context of HLA class II DR molecules has also been delineated (see, e.g., Southwood et al. *J. Immunology* 160:3363–3373,1998, and co-pending U.S. Ser. No. 09/009, 953 filed Jan. 21, 1998). In order to define a biologically significant threshold of DR binding affinity, a database of the binding affinities of 32 DR-restricted epitopes for their restricting element (i.e., the HLA molecule that binds the motif) was compiled. In approximately half of the cases (15 of 32 epitopes), DR restriction was associated with high binding affinities, i.e. binding affinity values of 100 nM or less. In the other half of the cases (16 of 32), DR restriction was associated with intermediate affinity (binding affinity values in the 100–1000 nM range). In only one of 32 cases was DR restriction associated with an $IC_{50}$ of 1000 nM or greater. Thus, 1000 nM can be defined as an affinity threshold associated with immunogenicity in the context of DR molecules.

In the case of tumor-associated antigens, many CTL peptide epitopes that have been shown to induce CTL that lyse peptide-pulsed target cells and tumor cell targets endogenously expressing the epitope exhibit binding affinity or $IC_{50}$ values of 200 nM or less. In a study that evaluated the association of binding affinity and immunogenicity of a small set of such TAA epitopes, 100% (10/10) of the high binders, i.e., peptide epitopes binding at an affinity of 50 nM or less, were immunogenic and 80% (8/10) of them elicited CTLs that specifically recognized tumor cells. In the 51 to 200 nM range, very similar figures were obtained. With respect to analog peptides, CTL inductions positive for wildtype peptide and tumor cells were noted for 86% (6/7) and 71% (5/7) of the peptides, respectively. In the 201–500 nM range, most peptides (4/5 wildtype) were positive for induction of CTL recognizing wildtype peptide, but tumor recognition was not detected.

The binding affinity of peptides for HLA molecules can be determined as described in Example 1, below.

III.D. Peptide Epitope Binding Motifs and Supermotifs

Through the study of single amino acid substituted antigen analogs and the sequencing of endogenously bound, naturally processed peptides, critical residues required for allele-specific binding to HLA molecules have been identified. The presence of these residues correlates with binding affinity for HLA molecules. The identification of motifs and/or supermotifs that correlate with high and intermediate affinity binding is an important issue with respect to the identification of immunogenic peptide epitopes for the inclusion in a vaccine. Kast et al. (*J. Immunol.* 152:3904–3912, 1994) have shown that motif-bearing peptides account for 90% of the epitopes that bind to allele-specific HLA class I molecules. In this study all possible peptides of 9 amino acids in length and overlapping by eight amino acids (240 peptides), which cover the entire sequence of the E6 and E7 proteins of human papillomavirus type 16, were evaluated for binding to five allele-specific HLA molecules that are expressed at high frequency among different ethnic groups. This unbiased set of peptides allowed an evaluation of the predictive value of HLA class I motifs. From the set of 240 peptides, 22 peptides were identified that bound to an allele-specific HLA molecule with high or intermediate affinity. Of these 22 peptides, 20 (i.e. 91%) were motif-bearing. Thus, this study demonstrates the value of motifs for the identification of peptide epitopes for inclusion in a vaccine: application of motif-based identification techniques will identify about 90% of the potential epitopes in a target antigen protein sequence.

Such peptide epitopes are identified in the Tables described below.

Peptides of the present invention may also comprise epitopes that bind to MHC class II DR molecules. A greater degree of heterogeneity in both size and binding frame position of the motif, relative to the N and C termini of the peptide, exists for class II peptide ligands. This increased heterogeneity of HLA class II peptide ligands is due to the structure of the binding groove of the HLA class II molecule which, unlike its class I counterpart, is open at both ends. Crystallographic analysis of HLA class II DRB*0101-peptide complexes showed that the major energy of binding is contributed by peptide residues complexed with complementary pockets on the DRB*0101 molecules. An important anchor residue engages the deepest hydrophobic pocket (see, e.g., Madden, D. R. *Ann. Rev. Immunol.* 13:587, 1995) and is referred to as position 1 (P1). P1 may represent the N-terminal residue of a class II binding peptide epitope, but more typically is flanked towards the N-terminus by one or more residues. Other studies have also pointed to an important role for the peptide residue in the $6^{th}$ position towards the C-terminus, relative to P1, for binding to various DR molecules.

In the past few years evidence has accumulated to demonstrate that a large fraction of HLA class I and class II molecules can be classified into a relatively few supertypes, each characterized by largely overlapping peptide binding repertoires, and consensus structures of the main peptide binding pockets. Thus, peptides of the present invention are identified by any one of several HLA-specific amino acid motifs (see, e.g., Tables I–III), or if the presence of the motif corresponds to the ability to bind several allele-specific HLA antigens, a supermotif. The HLA molecules that bind to peptides that possess a particular amino acid supermotif are collectively referred to as an HLA "supertype."

The peptide motifs and supermotifs described below, and summarized in Tables I–III, provide guidance for the identification and use of peptide epitopes in accordance with the invention.

Examples of peptide epitopes bearing a respective supermotif or motif are included in Tables as designated in the description of each motif or supermotif below. The Tables include a binding affinity ratio listing for some of the peptide epitopes. The ratio may be converted to $IC_{50}$ by using the following formula: $IC_{50}$ of the standard peptide/ratio = $IC_{50}$ of the test peptide (i.e., the peptide epitope). The $IC_{50}$ values of standard peptides used to determine binding affinities for Class I peptides are shown in Table IV. The $IC_{50}$ values of standard peptides used to determine binding affinities for Class II peptides are shown in Table V. For example, where an HLA-A2.1 motif-bearing peptide shows a relative binding ratio of 0.01 for HLA-A*0201, the $IC_{50}$ value is 500 nM, and where an HLA-A2.1 motif-bearing peptide shows a relative binding ratio of 0.1 for HLA-A 0201, the $IC_{50}$ value is 50 nM.

The peptides used as standards for the binding assays described herein are examples of standards; alternative standard peptides can also be used when performing binding studies.

To obtain the peptide epitope sequences listed in each Table, protein sequence data for HPV types 16, 18, 31, 33, 45, and 56 were evaluated for the presence of the designated supermotif or motif. Seven HPV structural and regulatory proteins, E1, E2, E5, E6, E7, L1 and L2 were included in the analysis. Peptide epitopes can additionally be evaluated on the basis of their conservancy (i.e., the amount of variance) among the available protein sequences for each HPV antigen. The "number of amino acids" in the Tables indicates the number of residues in the epitope sequence.

HLA Class I Motifs Indicative of CTL Inducing Peptide Epitopes:

The primary anchor residues of the HLA class I peptide epitope supermotifs and motifs delineated below are summarized in Table I. The HLA class I motifs set out in Table I(a) are those most particularly relevant to the invention claimed here. Primary and secondary anchor positions are summarized in Table II. Allele-specific HLA molecules that comprise HLA class I supertype families are listed in Table VI. In some cases, peptide epitopes may be listed in both a motif and a supermotif Table. The relationship of a particular motif and respective supermotif is indicated in the description of the individual motifs.

III.D.1. HLA-A1 Supermotif

The HLA-A1 supermotif is characterized by the presence in peptide ligands of a small (T or S) or hydrophobic (L, I, V, or M) primary anchor residue in position 2, and an aromatic (Y, F, or W) primary anchor residue at the C-terminal position of the epitope. The corresponding family of HLA molecules that bind to the A1 supermotif (i.e., the HLA-A1 supertype) is comprised of at least A*0101, A*2601, A*2602, A*2501, and A*3201 (see, e.g., DiBrino, M. et al., *J. Immunol.* 151:5930, 1993; DiBrino, M. et al., *J. Immunol.* 152:620, 1994; Kondo, A. et al., *Immunogenetics* 45:249, 1997). Other allele-specific HLA molecules predicted to be members of the A1 superfamily are shown in Table VI. Peptides binding to each of the individual HLA proteins can be modulated by substitutions at primary and/or secondary anchor positions, preferably choosing respective residues specified for the supermotif.

Representative peptide epitopes that comprise the A1 supermotif are set forth in Table VII.

III.D.2. HLA-A2 Supermotif

Primary anchor specificities for allele-specific HLA-A2.1 molecules (see, e.g., Falk et al., *Nature* 351:290–296, 1991; Hunt et al., *Science* 255:1261–1263, 1992; Parker et al., *J. Immunol.* 149:3580–3587, 1992; Ruppert et al., *Cell* 74:929–937, 1993) and cross-reactive binding among HLA-A2 and -A28 molecules have been described. (See, e.g., Fruci et al., *Human Immunol.* 38:187–192, 1993; Tanigaki et al., *Human Immunol.* 39:155–162, 1994; Del Guercio et al., *J. Immunol.* 154:685–693, 1995; Kast et al., *J. Immunol.* 152:3904–3912, 1994 for reviews of relevant data.) These primary anchor residues define the HLA-A2 supermotif; which presence in peptide ligands corresponds to the ability to bind several different HLA-A2 and -A28 molecules. The HLA-A2 supermotif comprises peptide ligands with L, I, V, M, A, T, or Q as a primary anchor residue at position 2 and L, I, V, M, A, or T as a primary anchor residue at the C-terminal position of the epitope.

The corresponding family of HLA molecules (i.e., the HLA-A2 supertype that binds these peptides) is comprised of at least: A*0201, A*0202, A*0203, A*0204, A*0205, A*0206, A*0207, A*0209, A*0214, A*6802, and A*6901. Other allele-specific HLA molecules predicted to be members of the A2 superfamily are shown in Table VI. As explained in detail below, binding to each of the individual allele-specific HLA molecules can be modulated by substitutions at the primary anchor and/or secondary anchor positions, preferably choosing respective residues specified for the supermotif.

Representative peptide epitopes that comprise an A2 supermotif are set forth in Table VIII. The motifs comprising the primary anchor residues V, A, T, or Q at position 2 and L, I, V, A, or T at the C-terminal position are those most particularly relevant to the invention claimed herein.

III.D.3. HLA-A3 Supermotif

The HLA-A3 supermotif is characterized by the presence in peptide ligands of A, L, I, V, M, S, or, T as a primary anchor at position 2, and a positively charged residue, R or K, at the C-terminal position of the epitope, e.g., in position 9 of 9-mers (see, e.g., Sidney et al, *Hum. Immunol.* 45:79, 1996). Exemplary members of the corresponding family of HLA molecules (the HLA-A3 supertype) that bind the A3 supermotif include at least A*0301, A*1101, A 3101, A*3301, and A*6801. Other allele-specific HLA molecules predicted to be members of the A3 supertype are shown in Table VI. As explained in detail below, peptide binding to each of the individual allele-specific HLA proteins can be modulated by substitutions of amino acids at the primary and/or secondary anchor positions of the peptide, preferably choosing respective residues specified for the supermotif.

Representative peptide epitopes that comprise the A3 supermotif are set forth in Table IX.

III.D.4. HLA-A24 Supermotif

The HLA-A24 supermotif is characterized by the presence in peptide ligands of an aromatic (F, W, or Y) or hydrophobic aliphatic (L, I, V, M, or T) residue as a primary anchor in position 2, and Y, F, W, L, I, or M as primary anchor at the C-terminal position of the epitope (see, e.g., Sette and Sidney, *Immunogenetics*, in press, 1999). The corresponding family of HLA molecules that bind to the A24 supermotif (i.e., the A24 supertype) includes at least A*2402, A*3001, and A*2301. Other allele-specific HLA molecules predicted to be members of the A24 supertype are shown in Table VI. Peptide binding to each of the allele-specific HLA molecules can be modulated by substitutions at primary and/or secondary anchor positions, preferably choosing respective residues specified for the supermotif.

Representative peptide epitopes that comprise the A24 supermotif are set forth in Table X.

III.D.5. HLA-B7 Supermotif

The HLA-B7 supermotif is characterized by peptides bearing proline in position 2 as a primary anchor, and a hydrophobic or aliphatic amino acid (L, I, V, M, A, F, W, or Y) as the primary anchor at the C-terminal position of the epitope. The corresponding family of HLA molecules that bind the B7 supermotif (i.e., the HLA-B7 supertype) is comprised of at least twenty six HLA-B proteins including: B*0702, B*0703, B*0704, B*0705, B*1508, B*3501, B*3502, B*3503, B*3504, B*3505, B 3506,B*3507, B*3508, B*5101, B*5102, B*5103, B*5104, B*5105, B*5301, B*5401, B*5501, B*5502, B*5601, B*5602, B*6701, and B*7801 (see, e.g., Sidney, et al., *J. Immunol.* 154:247, 1995; Barber, et al., *Curr. Biol.* 5:179, 1995; Hill, et al., *Nature* 360:434, 1992; Rammensee, et al., *Immunogenetics* 41:178, 1995 for reviews of relevant data). Other allele-specific HLA molecules predicted to be members of the B7 supertype are shown in Table VI. As explained in detail below, peptide binding to each of the individual allele-specific HLA proteins can be modulated by substitutions at the primary and/or secondary anchor positions of the peptide, preferably choosing respective residues specified for the supermotif.

Representative peptide epitopes that comprise the 137 supermotif are set forth in Table XI.

III.D.6. HLA-B27 Supermotif

The HLA-B27 supermotif is characterized by the presence in peptide ligands of a positively charged (R, H, or K) residue as a primary anchor at position 2, and a hydrophobic (F, Y, L, W, M, I, A, or V) residue as a primary anchor at the C-terminal position of the epitope (see, e.g., Sidney and Sette, *Immunogenetics*, in press, 1999). Exemplary members of the corresponding family of HLA molecules that bind to the B27 supermotif (i.e., the B27 supertype) include at least B*1401, B*1402, B*1509, B*2702, B*2703, B*2704, B*2705, B*2706, B*3801, B*3901, B*3902, and B*7301. Other allele-specific HLA molecules predicted to be members of the B27 supertype are shown in Table VI. Peptide binding to each of the allele-specific HLA molecules can be modulated by substitutions at primary and/or secondary anchor positions, preferably choosing respective residues specified for the supermotif.

Representative peptide epitopes that comprise the B27 supermotif are set forth in Table XII.

III.D.7. HLA-B44 Supermotif

The HLA-B44 supermotif is characterized by the presence in peptide ligands of negatively charged (D or E) residues as a primary anchor in position 2, and hydrophobic residues (F, W, Y, L, I, M, V, or A) as a primary anchor at the C-terminal position of the epitope (see, e.g., Sidney et al., *Immunol. Today* 17:261, 1996). Exemplary members of the corresponding family of HLA molecules that bind to the B44 supermotif(i.e., the B44 supertype) include at least: B*1801, B*1802, B*3701, B*4001, B*4002, B*4006, B 4402, B*4403, and B*4006. Peptide binding to each of the allele-specific HLA molecules can be modulated by substitutions at primary and/or secondary anchor positions; preferably choosing respective residues specified for the supermotif.

III.D.8. HLA-B58 Supermotif

The HLA-B58 supermotif is characterized by the presence in peptide ligands of a small aliphatic residue (A, S, or T) as a primary anchor residue at position 2, and an aromatic or hydrophobic residue (F, W, Y, L, I, V, M, or A) as a primary anchor residue at the C-terminal position of the epitope (see, e.g., Sidney and Sette, *Immunogenetics*, in press, 1999 for reviews of relevant data). Exemplary members of the corresponding family of HLA molecules that bind to the B58 supermotif (i.e., the B58 supertype) include at least: B*1516, B*1517, B*5701, B*5702, and B*5801. Other allele-specific HLA molecules predicted to be members of the B58 supertype are shown in Table VI. Peptide binding to each of the allele-specific HLA molecules can be modulated by substitutions at primary and/or secondary anchor positions, preferably choosing respective residues specified for the supermotif.

Representative peptide epitopes that comprise the B58 supermotif are set forth in Table XIII.

III.D.9. HLA-B62 Supermotif

The HLA-B62 supermotif is characterized by the presence in peptide ligands of the polar aliphatic residue Q or a hydrophobic aliphatic residue (L, V, M, I, or P) as a primary anchor in position 2, and a hydrophobic residue (F, W, Y, M, I, V, L, or A) as a primary anchor at the C-terminal position of the epitope (see, e.g., Sidney and Sette, *Immunogenetics*, in press, 1999). Exemplary members of the corresponding family of HLA molecules that bind to the B62 supermotif (i.e., the B62 supertype) include at least: B*1501, B*1502, B*1513, and B5201. Other allele-specific HLA molecules predicted to be members of the B62 supertype are shown in Table VI. Peptide binding to each of the allele-specific HLA molecules can be modulated by substitutions at primary and/or secondary anchor positions, preferably choosing respective residues specified for the supermotif.

Representative peptide epitopes that comprise the B62 supermotif are set forth in Table XIV.

III.D.10. HLA-A1 Motif

The HLA-A1 motif is characterized by the presence in peptide ligands of T, S, or M as a primary anchor residue at position 2 and the presence of Y as a primary anchor residue at the C-terminal position of the epitope. An alternative allele-specific A1 motif is characterized by a primary anchor residue at position 3 rather than position 2. This motif is characterized by the presence of D, E, A, or S as a primary anchor residue in position 3, and a Y as a primary anchor residue at the C-terminal position of the epitope (see, e.g., DiBrino et al., *J. Immunol.*, 152:620, 1994; Kondo et al., *Immunogenetics* 45:249, 1997; and Kubo et al., *J. Immunol.* 152:3913, 1994 for reviews of relevant data). Peptide binding to HLA A1 can be modulated by substitutions at primary and/or secondary anchor positions, preferably choosing respective residues specified for the motif.

Representative peptide epitopes that comprise either A1 motif are set forth in Table XV. Those epitopes comprising T, S, or M at position 2 and Y at the C-terminal position are also included in the listing of HLA-A1 supermotif-bearing peptides listed in Table VII, as these residues are a subset of the A1 supermotif primary anchors.

III.D.11. HLA-A*0201 Motif

An HLA-A2*0201 motif was determined to be characterized by the presence in peptide ligands of L or M as a primary anchor residue in position 2, and L or V as a primary anchor residue at the C-terminal position of a 9-residue peptide (see, e.g., Falk et al., *Nature* 351:290–296,1991) and was further found to comprise an I at position 2 and I or A at the C-terminal position of a nine amino acid peptide (see, e.g., Hunt et al., *Science* 255:1261–1263, Mar. 6, 1992; Parker et al., *J. Immunol.* 149:3580–3587, 1992). The A*0201 allele-specific motif has also been defined by the present inventors to additionally comprise V, A, T, or Q as a primary anchor residue at position 2, and M or T as a primary anchor residue at the C-terminal position of the epitope (see, e.g., Kast et al., *J. Immunol.* 152:3904–3912, 1994). Thus, the HLA-A*0201 motif comprises peptide ligands with L, I, V, M, A, T, or Q as primary anchor residues at position 2 and L, I, V, M, A, or T as a primary anchor residue at the C-terminal position of the epitope. The preferred and tolerated residues that characterize the primary anchor positions of the HLA-A*0201 motif are identical to the residues describing the A2 supermotif. (For reviews of relevant data, see, e.g., Del Guercio et al., *J. Immunol.* 154:685–693, 1995; Ruppert et al., *Cell* 74:929–937, 1993; Sidney et al., *Immunol. Today* 17:261–266, 1996; Sette and Sidney, *Curr. Opin. in Immunol.* 10:478–482, 1998). Secondary anchor residues that characterize the A 0201 motif have additionally been defined (see, e.g., Ruppert et al., *Cell* 74:929–937, 1993). These are shown in Table II. Peptide binding to HLA-A 0201 molecules can be modulated by substitutions at primary and/or secondary anchor positions, preferably choosing respective residues specified for the motif.

Representative peptide epitopes that comprise an A*0201 motif are set forth in Table VIII. The A*0201 motifs comprising the primary anchor residues V, A, T, or Q at position 2 and L, I, V, A, or T at the C-terminal position are those most particularly relevant to the invention claimed herein.

III.D.12. HLA-A3 Motif

The HLA-A3 motif is characterized by the presence in peptide ligands of L, M, V, I, S, A, T, F, C, G, or D as a primary anchor residue at position 2, and the presence of K, Y, R, H, F, or A as a primary anchor residue at the C-terminal position of the epitope (see, e.g., DiBrino et al., *Proc. Natl. Acad. Sci USA* 90:1508,1993; and Kubo et al., *J. Immunol.* 152:3913–3924, 1994). Peptide binding to HLA-A3 can be modulated by substitutions at primary and/or secondary anchor positions, preferably choosing respective residues specified for the motif.

Representative peptide epitopes that comprise the A3 motif are set forth in Table XVI. Those epitopes that also comprise the A3 supermotif are also listed in Table IX. The A3 supermotif primary anchor residues comprise a subset of the A3- and A11-allele specific motif primary anchor residues.

III.D.13. HLA-A11 Motif

The HLA-A11 motif is characterized by the presence in peptide ligands of V, T, M, L, I, S, A, G, N, C, D, or F as a primary anchor residue in-position 2, and K, R, Y, or H as a primary anchor residue at the C-terminal position of the epitope (see, e.g., Zhang et al., *Proc. Natl. Acad. Sci USA* 90:2217–2221, 1993; and Kubo et al., *J. Immunol.* 152:3913–3924, 1994). Peptide binding to HLA-A11 can be modulated by substitutions at primary and/or secondary anchor positions, preferably choosing respective residues specified for the motif.

Representative peptide epitopes that comprise the A11 motif are set forth in Table XVII; peptide epitopes comprising the A3 allele-specific motif are also present in this Table because of the extensive overlap between the A3 and A11 motif primary anchor specificities. Further, those peptide epitopes that comprise the A3 supermotif are also listed in Table IX.

III.D.14. HLA-A24 Motif

The HLA-A24 motif is characterized by the presence in peptide ligands of Y, F, W, or M as a primary anchor residue in position 2, and F, L, I, or W as a primary anchor residue at the C-terminal position of the epitope (see, e.g., Kondo et al., *J. Immunol.* 155:4307–4312, 1995; and Kubo et al., *J. Immunol.* 152:3913–3924, 1994). Peptide binding to HLA-A24 molecules can be modulated by substitutions at primary and/or secondary anchor positions; preferably choosing respective residues specified for the motif.

Representative peptide epitopes that comprise the A24 motif are set forth in Table XVIII. These epitopes are also listed in Table X, which sets forth HLA-A24-supermotif-bearing peptides, as the primary anchor residues characterizing the A24 allele-specific motif comprise a subset of the A24 supermotif primary anchor residues.

Motifs Indicative of Class II HTL Inducing Peptide Epitopes

The primary and secondary anchor residues of the HLA class II peptide epitope supermotifs and motifs delineated below are summarized in Table III.

III.D.15. HLA DR-1-4-7 Supermotif

Motifs have also been identified for peptides that bind to three common HLA class II allele-specific HLA molecules: HLA DRB1*0401, DRB1*0101, and DRB1*0701 (see, e.g., the review by Southwood et al. *J. Immunology* 160:3363–3373,1998). Collectively, the common residues from these motifs delineate the HLA DR-1-4-7 supermotif. Peptides that bind to these DR molecules carry a supermotif characterized by a large aromatic or hydrophobic residue (Y, F, W, L, I, V, or M) as a primary anchor residue in position 1, and a small, non-charged residue (S, T, C, A, P, V, I, L, or M) as a primary anchor residue in position 6 of a 9-mer core region. Allele-specific secondary effects and secondary anchors for each of these HLA types have also been identified (Southwood et al., supra). These are set forth in Table III. Peptide binding to HLA- DRB1*0401, DRB1*0101, and/or DRB1*0701 can be modulated by substitutions at primary and/or secondary anchor positions, preferably choosing respective residues specified for the supermotif.

Representative 9-mer epitopes comprising the DR-1-4-7 supermotif, wherein position 1 of the supermotif is at position 1 of the nine-residue core, are set forth in Table XIX. Respective exemplary peptide epitopes of 15 amino acid residues in length, each of which comprise a conserved nine residue core, are also shown in the Table.

III.D.16. HLA DR3 Motifs

Two alternative motifs (i.e., submotifs) characterize peptide epitopes that bind to HLA-DR3 molecules (see, e.g., Geluk et al., *J. Immunol.* 152:5742, 1994). In the first motif (submotif DR3A) a large, hydrophobic residue (L, I, V, M, F, or Y) is present in anchor position 1 of a 9-mer core, and D is present as an anchor at position 4, towards the carboxyl terminus of the epitope. As in other class II motifs, core position 1 may or may not occupy the peptide N-terminal position.

The alternative DR3 submotif provides for lack of the large, hydrophobic residue at anchor position 1, and/or lack of the negatively charged or amide-like anchor residue at position 4, by the presence of a positive charge at position 6 towards the carboxyl terminus of the epitope. Thus, for the alternative allele-specific DR3 motif (submotif DR3B): L, I, V, M, F, Y, A, or Y is present at anchor position 1; D, N, Q, E, S, or T is present at anchor position 4; and K, R, or H is present at anchor position 6. Peptide binding to HLA-DR3 can be modulated by substitutions at primary and/or secondary anchor positions, preferably choosing respective residues specified for the motif.

Representative 9-mer epitopes corresponding to a nine residue sequence comprising the DR3a and DR3b submotifs (wherein position 1 of the motif is at position 1 of the nine residue core) are set forth in Table XXa and b. Respective exemplary peptide epitopes of 15 amino acid residues in length, each of which comprise a conserved nine residue core, are also shown in Table XX.

Each of the HLA class I or class II epitopes set out in the Tables herein are deemed singly to be an inventive aspect of this application. Further, it is also an inventive aspect of this application that each epitope may be used in combination with any other epitope.

III.E. Enhancing Population Coverage of the Vaccine

Vaccines that have broad population coverage are preferred because they are more commercially viable and generally applicable to the most people. Broad population coverage can be obtained using the peptides of the invention (and nucleic acid compositions that encode such peptides) through selecting peptide epitopes that bind to HLA alleles which, when considered in total, are present in most of the population. Table XXI lists the overall frequencies of the HLA class I supertypes in various ethnicities (Table XXIa) and the combined population coverage achieved by the A2-, A3-, and B7-supertypes (Table XXIb). The A2-, A3-, and B7 supertypes are each present on the average of over 40% in each of these five major ethnic groups. Coverage in excess of 80% is achieved with a combination of these supermotifs. These results suggest that effective and non-ethnically biased population coverage is achieved upon use of a limited number of cross-reactive peptides. Although the population coverage reached with these three main peptide specificities is high, coverage can be expanded to reach 95% population coverage and above, and more easily achieve truly multi specific responses upon use of additional supermotif or allele-specific motif bearing peptides.

The B44-, A1-, and A24-supertypes are each present, on average, in a range from 25% to 40% in these major ethnic populations (Table XXIa). While less prevalent overall, the B27-, B58-, and B62 supertypes are each present with a frequency >25% in at least one major ethnic group (Table XXIa). Table XXIb summarizes the estimated prevalence of combinations of HLA supertypes that have been identified in five major ethnic groups. The incremental coverage obtained by the inclusion of A1,- A24-, and B44-supertypes to the A2, A3, and B7 coverage and coverage obtained with all of the supertypes described herein, is shown.

The data presented herein, together with the previous definition of the A2-, A3-, and B7-supertypes, indicates that all antigens, with the possible exception of A29, B8, and B46, can be classified into a total of nine HLA supertypes. By including epitopes from the six most frequent supertypes, an average population coverage of 99% is obtained for five major ethnic groups.

III.F. Immune Response-Stimulating Peptide Analogs

In general, CTL and HTL responses to whole antigens are not directed against all possible epitopes. Rather, they are restricted to a few "immunodominant" determinants (Zinkemagel, et al., *Adv. Immunol.* 27:5159, 1979; Bennink, et al., *J. Exp. Med.* 168:19351939, 1988; Rawle, et al., *J. Immunol.* 146:3977–3984,1991). It has been recognized that immunodominance (Benacerraf, et al., *Science* 175:273–279, 1972) could be explained by either the ability of a given epitope to selectively bind a particular HLA protein (determinant selection theory) (Vitiello, et al, *J. Immunol.* 131:1635, 1983); Rosenthal, et al., *Nature* 267:156–158, 1977), or to be selectively recognized by the existing TCR (T cell receptor) specificities (repertoire theory) (Klein, J. , IMMUNOLOGY, THE SCIENCE OF SELFNON-SELF DISCRIMINATION, John Wiley & Sons, New York, pp. 270–310, 1982). It has been demonstrated that additional factors, mostly linked to processing events, can also play a key role in dictating, beyond strict immunogenicity, which of the many potential determinants will be presented as immunodominant (Sercarz, et al., *Annu. Rev. Immunol.* 11:729–766, 1993).

The concept of dominance and subdominance is relevant to immunotherapy of both infectious diseases and cancer. For example, in the course of chronic viral disease, recruitment of subdominant epitopes can be important for successful clearance of the infection, especially if dominant CTL or HTL specificities have been inactivated by functional tolerance, suppression, mutation of viruses and other mechanisms (Franco, et al., *Curr. Opin. Immunol.* 7:524–531, 1995). In the case of cancer and tumor antigens, CTLs recognizing at least some of the highest binding affinity peptides might be functionally inactivated. Lower binding affinity peptides are preferentially recognized at these times, and may therefore be preferred in therapeutic or prophylactic anti-cancer vaccines.

In particular, it has been noted that a significant number of epitopes derived from known non-viral tumor associated antigens (TAA) bind HLA class I with intermediate affinity ($IC_{50}$ in the 50–500 nM range). For example, it has been found that 8 of 15 known TAA peptides recognized by tumor infiltrating lymphocytes (TIL) or CTL bound in the 50–500 nM range. (These data are in contrast with estimates that 90% of known viral antigens were bound by HLA class I molecules with $IC_{50}$ of 50 nM or less, while only approximately 10% bound in the 50–500 nM range (Sette, et al., *J. Immunol.*, 153:558–5592, 1994). In the cancer setting this phenomenon is probably due to elimination or functional inhibition of the CTL recognizing several of the highest binding peptides, presumably because of T cell tolerization events.

Without intending to be bound by theory, it is believed that because T cells to dominant epitopes may have been clonally deleted, selecting subdominant epitopes may allow existing T cells to be recruited, which will then lead to a therapeutic or prophylactic response. However, the binding of HLA molecules to subdominant epitopes is often less vigorous than to dominant ones. Accordingly, there is a need to be able to modulate the binding affinity of particular immunogenic epitopes for one or more HLA molecules, and thereby to modulate the immune response elicited by the peptide, for example to prepare analog peptides which elicit a more vigorous response. This ability would greatly enhance the usefulness of peptide epitope-based vaccines and therapeutic agents.

Although peptides with suitable cross-reactivity among all alleles of a superfamily are identified by the screening procedures described above, cross-reactivity is not always as complete as possible, and in certain cases procedures to increase cross-reactivity of peptides can be useful; moreover, such procedures can also be used to modify other properties of the peptides such as binding affinity or peptide stability. Having established the general rules that govern cross-reactivity of peptides for HLA alleles within a given motif or supermotif, modification (i.e., analoging) of the structure of peptides of particular interest in order to achieve broader (or otherwise modified) HLA binding capacity can be performed. More specifically, peptides which exhibit the broadest cross-reactivity patterns, can be produced in accordance with the teachings herein. The present concepts related to analog generation are set forth in greater detail in co-pending U.S. Ser. No. 09/226,775 filed Jan. 6, 1999.

In brief, the strategy employed utilizes the motifs or supermotifs which correlate with binding to certain HLA molecules. The motifs or supermotifs are defined by having primary anchors, and in many cases secondary anchors. Analog peptides can be created by substituting amino acid residues at primary anchor, secondary anchor, or at primary and secondary anchor positions. Generally, analogs are made for peptides that already bear a motif or supermotif. Preferred secondary anchor residues of supermotifs and motifs that have been defined for HLA class I and class II binding peptides are shown in Tables II and III, respectively.

For a number of the motifs or supermotifs in accordance with the invention, residues are defined which are deleterious to binding to allele-specific HLA molecules or members of HLA supertypes that bind the respective motif or supermotif (Tables II and III). Accordingly, removal of such residues that are detrimental to binding can be performed in accordance with the present invention. For example, in the case of the A3 supertype, when all peptides that have such deleterious residues are removed from the population of peptides used in the analysis, the incidence of cross-reactivity increased from 22% to 37% (see, e.g., Sidney, J. et al., *Hu. Immunol.* 45:79, 1996). Thus, one strategy to improve the cross-reactivity of peptides within a given supermotif is simply to delete one or more of the deleterious residues present within a peptide and substitute a small "neutral" residue such as Ala (that may not influence T cell recognition of the peptide). An enhanced likelihood of cross-reactivity is expected if, together with elimination of detrimental residues within a peptide, "preferred" residues associated with high affinity binding to an allele-specific HLA molecule or to multiple HLA molecules within a superfamily are inserted.

To ensure that an analog peptide, when used as a vaccine, actually elicits a CTL response to the native epitope in vivo (or, in the case of class II epitopes, elicits helper T cells that cross-react with the wild type peptides), the analog peptide may be used to immunize T cells in vitro from individuals of the appropriate HLA allele. Thereafter, the immunized cells' capacity to induce lysis of wild type peptide sensitized target cells is evaluated. It will be desirable to use as antigen presenting cells, cells that have been either infected, or transfected with the appropriate genes, or, in the case of class II epitopes only, cells that have been pulsed with whole protein antigens, to establish whether endogenously produced antigen is also recognized by the relevant T cells.

Another embodiment of the invention is to create analogs of weak binding peptides, to thereby ensure adequate numbers of cross-reactive cellular binders. Class I binding peptides exhibiting binding affinities of 500–5000 nM, and carrying an acceptable but suboptimal primary anchor residue at one or both positions can be "fixed" by substituting preferred anchor residues in accordance with the respective supertype. The analog peptides can then be tested for crossbinding activity.

Another embodiment for generating effective peptide analogs involves the substitution of residues that have an adverse impact on peptide stability or solubility in, e.g., a liquid environment. This substitution may occur at any position of the peptide epitope. For example, a cysteine (C) can be substituted out in favor of α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances (see, e.g., the review by Sette et al., In: *Persistent Viral Infections*, Eds. R. Ahmed and I. Chen, John Wiley & Sons, England, 1999). Substitution of cysteine with a-amino butyric acid may occur at any residue of a peptide epitope, i.e. at either anchor or non-anchor positions.

III.G. Computer Screening of Protein Sequences from Disease-Related Antigens for Supermotif- or Motif-Bearing Peptides In order to identify supermotif- or motif-bearing epitopes in a target antigen, a native protein sequence, e.g., a tumor-associated antigen, or sequences from an infectious organism, or a donor tissue for transplantation, is screened using a means for computing, such as an intellectual calculation or a computer, to determine the presence of a supermotif or motif within the sequence. The information obtained from the analysis of native peptide can be used directly to evaluate the status of the native peptide or may be utilized subsequently to generate the peptide epitope.

Computer programs that allow the rapid screening of protein sequences for the occurrence of the subject supermotifs or motifs are encompassed by the present invention; as are programs that permit the generation of analog peptides. These programs are implemented to analyze any identified amino acid sequence or operate on an unknown sequence and simultaneously determine the sequence and identify motif-bearing epitopes thereof; analogs can be simultaneously determined as well. Generally, the identified sequences will be from a pathogenic organism or a tumor-associated peptide. For example, the target molecules considered herein include, without limitation, the E1, E2, E4, E5a, E5b, E6, E7, L1 and L2 proteins of HPV.

In cases where the sequences of multiple variants of the same target protein are available, potential peptide epitopes can also be selected on the basis of their conservancy. For example, a criterion for conservancy may define that the entire sequence of an HLA class I binding peptide or the entire 9-mer core of a class II binding peptide, be conserved in a designated percentage, of the sequences evaluated for a specific protein antigen.

To target a broad population that may be infected with a number of different strains, it is preferable to include in vaccine compositions epitopes that are representative of HPV antigen sequences from different HPV strains. As appreciated by those in the art, regions with greater or lessor degrees of conservancy among HPV 6a, HPV 6b and/or HPV 11 can be employed as appropriate for a given antigenic target.

It is important that the selection criteria utilized for prediction of peptide binding are as accurate as possible, to correlate most efficiently with actual binding. Prediction of peptides that bind, for example, to HLA-A*0201, on the basis of the presence of the appropriate primary anchors, is positive at about a 30% rate (see, e.g., Ruppert, J. et al. *Cell* 74:929, 1993). However, by extensively analyzing peptide-HLA binding data disclosed herein, data in related patent applications, and data in the art, the present inventors have developed a number of allele-specific polynomial algorithms that dramatically increase the predictive value over identification on the basis of the presence of primary anchor residues alone. These algorithms take into account not only the presence or absence of primary anchors, but also consider the positive or deleterious presence of secondary anchor residues (to account for the impact of different amino acids at different positions). The algorithms are essentially based on the premise that the overall affinity (or ΔG) of peptide-HLA interactions can be approximated as a linear polynomial function of the type:

$$\Delta G = a_{1i} \times a_{2i} \times a_{3i} \ldots \times a_{ni}$$

where $a_{ji}$ is a coefficient that represents the effect of the presence of a given amino acid (j) at a given position (i) along the sequence of a peptide of n amino acids. An important assumption of this method is that the effects at each position are essentially independent of each other. This assumption is justified by studies that demonstrated that peptides are bound to HLA molecules and recognized by T cells in essentially an extended conformation. Derivation of specific algorithm coefficients has been described, for example, in Gulukota, K. et al., *J. Mol. Biol.* 267:1258, 1997.

Additional methods to identify preferred peptide sequences, which also make use of specific motifs, include the use of neural networks and molecular modeling programs (see, e.g., Milik et al., *Nature Biotechnology* 16:753, 1998; Altuvia et al., *Hum. Immunol.* 58:1, 1997; Altuvia et al, *J. Mol. Biol.* 249:244, 1995; Buus, S. *Curr. Opin. Immunol.* 11:209–213, 1999; Brusic, V. et al., *Bioinformatics* 14:121–130, 1998; Parker et al., *J. Immunol.* 152:163, 1993; Meister et al., *Vaccine* 13:581, 1995; Hammer et al., *J. Exp. Med.* 180:2353, 1994; Sturniolo et al., *Nature Biotechnol.* 17:555 1999).

For example, it has been shown that in sets of A*0201 motif-bearing peptides containing at least one preferred secondary anchor residue while avoiding the presence of any deleterious secondary anchor residues, 69% of the peptides will bind A*0201 with an $IC_{50}$ less than 500 nM (Ruppert, J. et al. *Cell* 74:929, 1993). These algorithms are also flexible in that cut-off scores may be adjusted to select sets of peptides with greater or lower predicted binding properties, as desired.

In utilizing computer screening to identify peptide epitopes, a protein sequence or translated sequence may be analyzed using software developed to search for motifs, for example the "FINDPATTERNS" program (Devereux, et al. *Nucl. Acids Res.* 12:387–395, 1984) or MotifSearch 1.4 software program (D. Brown, San Diego, Calif.) to identify potential peptide sequences containing appropriate HLA binding motifs. The identified peptides can be scored using customized polynomial algorithms to predict their capacity to bind specific HLA class I or class II alleles. As appreciated by one of ordinary skill in the art, a large array of computer programming software and hardware options are available in the relevant art which can be employed to implement the motifs of the invention in order to evaluate (e.g., without limitation, to identify epitopes, identify epitope concentration per peptide length, or to generate analogs) known or unknown peptide sequences.

In accordance with the procedures described above, HPV peptide epitopes and analogs thereof that are able to bind HLA supertype groups or allele-specific HLA molecules have been identified (Tables VII–XX).

III.H. Preparation of Peptide Epitopes

Peptides in accordance with the invention can be prepared synthetically, by recombinant DNA technology or chemical synthesis, or from natural sources such as native tumors or pathogenic organisms. Peptide epitopes may be synthesized individually or as polyepitopic peptides. Although the peptide will preferably be substantially free of other naturally occurring host cell proteins and fragments thereof, in some embodiments the peptides may be synthetically conjugated to native fragments or particles.

The peptides in accordance with the invention can be a variety of lengths, and either in their neutral (uncharged) forms or in forms which are salts. The peptides in accordance with the invention are either free of modifications such as glycosylation, side chain oxidation, or phosphorylation; or they contain these modifications, subject to the condition that modifications do not destroy the biological activity of the peptides as described herein.

When possible, it may be desirable to optimize HLA class I binding epitopes of the invention, such as can be used in a polyepitopic construct, to a length of about 8 to about 13 amino acid residues, often 8 to 11, preferably 9 to 10. HLA class II binding peptide epitopes of the invention may be optimized to a length of about 6 to about 30 amino acids in length, preferably to between about 13 and about 20 residues. Preferably, the peptide epitopes are commensurate in size with endogenously processed pathogen-derived peptides or tumor cell peptides that are bound to the relevant HLA molecules, however, the identification and preparation of peptides that comprise epitopes of the invention can also be carried out using the techniques described herein.

In alternative embodiments, epitopes of the invention can be linked as a polyepitopic peptide, or as a minigene that encodes a polyepitopic peptide.

In another embodiment, it is preferred to identify native peptide regions that contain a high concentration of class I and/or class II epitopes. Such a sequence is generally selected on the basis that it contains the greatest number of epitopes per amino acid length. It is to be appreciated that epitopes can be present in a nested or overlapping manner, e.g. a 10 amino acid long peptide could contain two 9 amino acid long epitopes and one 10 amino acid long epitope; upon intracellular processing, each epitope can be exposed and bound by an HLA molecule upon administration of such a peptide. This larger, preferably multi-epitopic, peptide can be generated synthetically, recombinantly, or via cleavage from the native source.

The peptides of the invention can be prepared in a wide variety of ways. For the preferred relatively short size, the peptides can be synthesized in solution or on a solid support in accordance with conventional techniques. Various automatic synthesizers are commercially available and can be used in accordance with known protocols. (See, for example, Stewart & Young, SOLID PHASE PEPTIDE SYNTHESIS, 2D. ED., Pierce Chemical Co., 1984). Further, individual peptide epitopes can be joined using chemical ligation to produce larger peptides that are still within the bounds of the invention.

Alternatively, recombinant DNA technology can be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., MOLECULAR CLONING, A LABORATORY MANUAL, Cold Spring Harbor Press, Cold Spring Harbor, N.Y. (1989). Thus, recombinant polypeptides which comprise one or more peptide sequences of the invention can be used to present the appropriate T cell epitope.

The nucleotide coding sequence for peptide epitopes of the preferred lengths contemplated herein can be synthesized by chemical techniques, for example, the phosphotriester method of Matteucci, et al., *J. Am. Chem. Soc.* 103:3185 (1981). Peptide analogs can be made simply by substituting the appropriate and desired nucleic acid base(s) for those that encode the native peptide sequence; exemplary nucleic acid substitutions are those that encode an amino acid defined by the motifs/supermotifs herein. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast, insect or mammalian cell hosts may also be used, employing suitable vectors and control sequences.

III.I. Assays to Detect T-Cell Responses

Once HLA binding peptides are identified, they can be tested for the ability to elicit a T-cell response. The preparation and evaluation of motif-bearing peptides are described in PCT publications WO 94/20127 and WO 94/03205. Briefly, peptides comprising epitopes from a particular antigen are synthesized and tested for their ability to bind to the appropriate HLA proteins. These assays may involve evaluating the binding of a peptide of the invention to purified HLA class I molecules in relation to the binding of a radioiodinated reference peptide. Alternatively, cells expressing empty class I molecules (i.e. lacking peptide therein) may be evaluated for peptide binding by immunofluorescent staining and flow microfluorimetry. Other assays that may be used to evaluate peptide binding include peptide-dependent class I assembly assays and/or the inhibition of CTL recognition by peptide competition. Those peptides that bind to the class I molecule, typically with an affinity of 500 nM or less, are further evaluated for their ability to serve as targets for CTLs derived from infected or immunized individuals, as well as for their capacity to induce primary in vitro or in vivo CTL responses that can give rise to CTL populations capable of reacting with selected target cells associated with a disease.

Analogous assays are used for evaluation of HLA class II binding peptides. HLA class II motif-bearing peptides that are shown to bind, typically at an affinity of 1000 nM or less, are further evaluated for the ability to stimulate HTL responses.

Conventional assays utilized to detect T cell responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations. Antigen-presenting cells can be normal cells such as peripheral blood mononuclear cells or dendritic cells. Alternatively, mutant non-human mammalian cell lines that are deficient in their ability to load class I molecules with internally processed peptides and that have been transfected with the appropriate human class I gene, may be used to test for the capacity of the peptide to induce in vitro primary CTL responses.

Peripheral blood mononuclear cells (PBMCs) may be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

Additionally, a method has been devised which allows direct quantification of antigen-specific T cells by staining with Fluorescein-labelled HLA tetrameric complexes (Altman, J. D. et al., *Proc. Natl. Acad. Sci. USA* 90:10330, 1993; Altman, J. D. et al., *Science* 274:94, 1996). Other relatively recent technical developments include staining for intracellular lymphokines, and interferon release assays or ELISPOT assays. Tetramer staining, intracellular lymphokine staining and ELISPOT assays all appear to be at least 10-fold more sensitive than more conventional assays (Lalvani, A. et al., *J. Exp. Med.* 186:859, 1997; Dunbar, P. R. et al., *Curr. Biol.* 8:413, 1998; Murali-Krishna, K. et al., *Immunity* 8:177, 1998).

HTL activation may also be assessed using such techniques known to those in the art such as T cell proliferation and secretion of lymphokines, e.g. IL-2 (see, e.g. Alexander et al., *Immunity* 1:751–761, 1994).

Alternatively, immunization of HLA transgenic mice can be used to determine immunogenicity of peptide epitopes. Several transgenic mouse models including mice with human A2.1, A11 (which can additionally be used to analyze HLA-A3 epitopes), and B7 alleles have been characterized and others (e.g., transgenic mice for HLA-A1 and A24) are being developed. HLA-DR1 and HLA-DR3 mouse models have also been developed. Additional transgenic mouse models with other HLA alleles may be generated as necessary. Mice may be immunized with peptides emulsified in Incomplete Freund's Adjuvant and the resulting T cells tested for their capacity to recognize peptide-pulsed target cells and target cells transfected with appropriate genes. CTL responses may be analyzed using cytotoxicity assays described above. Similarly, HTL responses may be analyzed using such assays as T cell proliferation or secretion of lymphokines.

III.J. Use of Peptide Epitopes as Diagnostic Agents and for Evaluating Immune Responses In one aspect of the invention, HLA class I and class II binding peptides as described herein can be used as reagents to evaluate an immune response. The immune response to be evaluated is induced by using as an immunogen any agent that may result in the production of antigen-specific CTLs or HTLs that recognize and bind to the peptide epitope(s) to be employed as the reagent. The peptide reagent need not be used as the immunogen. Assay systems that are used for such an analysis include relatively recent technical developments such as tetramers, staining for intracellular lymphokines and interferon release assays, or ELISPOT assays.

For example, a peptide of the invention is used in a tetramer staining assay to assess peripheral blood mononuclear cells for the presence of antigen-specific CTLs following exposure to a pathogen or immunogen. The HLA-tetrameric complex is used to directly visualize antigen-specific CTLs (see, e.g., Ogg et al., *Science* 279:2103–2106, 1998; and Altman et al., *Science* 174:94–96, 1996) and determine the frequency of the antigen-specific CTL population in a sample of peripheral blood mononuclear cells.

A tetramer reagent using a peptide of the invention is generated as follows: A peptide that binds to an HLA molecule is refolded in the presence of the corresponding HLA heavy chain and $\beta_2$-microglobulin to generate a tri-molecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells can then be readily identified, for example, by flow cytometry. Such procedures are used for diagnostic or prognostic purposes. Cells identified by the procedure can also be used for therapeutic purposes.

Peptides of the invention are also used as reagents to evaluate immune recall responses. (see, e.g., Bertoni et al., *J. Clin. Invest.* 100:503–513, 1997 and Penna et al., *J. Exp. Med.* 174:1565–1570, 1991.) For example, patient PBMC samples from individuals infected with HPV are analyzed for the presence of antigen-specific CTLs or HTLs using specific peptides. A blood sample containing mononuclear cells may be evaluated by cultivating the PBMCs and stimulating the cells with a peptide of the invention. After an appropriate cultivation period, the expanded cell population may be analyzed, for example, for CTL or for HTL activity.

The peptides are also used as reagents to evaluate the efficacy of a vaccine. PBMCs obtained from a patient vaccinated with an immunogen are analyzed using, for example, either of the methods described above. The patient is HLA typed, and peptide epitope reagents that recognize the allele-specific molecules present in that patient are selected for the analysis. The immunogenicity of the vaccine is indicated by the presence of HPV epitope-specific CTLs and/or HTLs in the PBMC sample.

The peptides of the invention are also be used to make antibodies, using techniques well known in the art (see, e.g. CURRENT PROTOCOLS IN IMMUNOLOGY, Wiley/Greene, NY; and *Antibodies A Laboratory Manual Harlow*, Harlow and Lane, Cold Spring Harbor Laboratory Press, 1989), which may be useful as reagents to diagnose HPV infection. Such antibodies include those that recognize a peptide in the context of an HLA molecule, i.e., antibodies that bind to a peptide-MHC complex.

III.K. Vaccine Compositions

Vaccines and methods of preparing vaccines that contain an immunogenically effective amount of one or more peptides as described herein are further embodiments of the invention. Once appropriately immunogenic epitopes have been defined, they can be sorted and delivered by various means, herein referred to as "vaccine" compositions. Such vaccine compositions can include, for example, lipopeptides (e.g., Vitiello, A. et al., *J. Clin. Invest*. 95:341, 1995), peptide compositions encapsulated in poly(DL-lactide-co-glycolide) ("PLG") microspheres (see, e.g., Eldridge, et al.,*Molec. Immunol*. 28:287–294, 1991: Alonso et al., *Vaccine* 12:299–306, 1994; Jones et al., *Vaccine* 13:675–681, 1995), peptide compositions contained in immune stimulating complexes (ISCOMS) (see, e.g., Takahashi et al., *Nature* 344:873–875, 1990; Hu et al.,*Clin Exp Immunol*. 113:235–243, 1998), multiple antigen peptide systems (MAPs) (see e.g., Tam, J. P., *Proc. Natl. Acad. Sci. U.S.A.* 85:5409–5413, 1988; Tam, J. P., *J. Immunol. Methods* 196:17–32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis*. 124:148, 1971; Chanda, P. K. et al., *Virology* 175:535, 1990), particles of viral or synthetic origin (e.g., Kofler, N. et al., *J. Immunol. Methods*. 192:25, 1996; Eldridge, J. H. et al., *Sem. Hematol*. 30:16, 1993; Falo, L. D., Jr. et al., *Nature Med*. 7:649, 1995), adjuvants (Warren, H. S., Vogel, F. R., and Chedid, L. A. *Annu. Rev. Immunol*. 4:369,1986; Gupta, R. K. et al., *Vaccine* 11:293, 1993), liposomes (Reddy, R. et al, *J. Immunol*. 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol*. 12:923, 1994 and Eldridge, J. H. et al., *Sem. Hematol*. 30:16, 1993). Toxin-targeted delivery technologies, also known as receptor mediated targeting, such as those of Avant Immunotherapeutics, Inc. (Needham, Mass.) may also be used.

Vaccine compositions of the invention include nucleic acid-mediated modalities. DNA or RNA encoding one or more of the peptides of the invention can also be administered to a patient. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720; and in more detail below. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Patent No. 5,922,687).

For therapeutic or prophylactic immunization purposes, the peptides of the invention can be expressed by viral or bacterial vectors. Examples of expression vectors include attenuated viral hosts, such as vaccinia or fowlpox. This approach involves the use of vaccinia virus, for example, as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456–460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$).

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later infection, or at least partially resistant to developing an ongoing chronic infection, or derives at least some therapeutic benefit when the antigen was tumor-associated.

In some embodiments, it may be desirable to combine the class I peptide components with components that induce or facilitate neutralizing antibody and or helper T cell responses to the target antigen of interest. A preferred embodiment of such a composition comprises class I and class II epitopes in accordance with the invention. An alternative embodiment of such a composition comprises a class I and/or class II epitope in accordance with the invention, along with a PADRE™ (Epimmune, San Diego, Calif.) molecule (described, for example, in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo.

Vaccine compositions, either DNA- or peptide-based, can also be administered in vivo in combination with dendritic cell mobilization whereby loading of dendritic cells occurs in vivo.

Antigenic peptides are used to elicit a CTL and/or HTL response ex vivo, as well. The resulting CTL or HTL cells, can be used to treat chronic infections, or tumors in patients that do not respond to other conventional forms of therapy, or will not respond to a therapeutic vaccine peptide or nucleic acid in accordance with the invention. Ex vivo CTL or HTL responses to a particular antigen (infectious or tumor-associated antigen) are induced by incubating in tissue culture the patient's, or genetically compatible, CTL or HTL precursor cells together with a source of antigen-presenting cells (APC), such as dendritic cells, and the appropriate immunogenic peptide. After an appropriate incubation time (typically about 7–28 days), in which the precursor cells are activated and expanded into effector cells, the cells are infused back into the patient, where they will destroy (CTL) or facilitate destruction (HTL) of their specific target cell (an infected cell or a tumor cell). Transfected dendritic cells may also be used as antigen presenting cells.

The vaccine compositions of the invention can also be used in combination with other treatments used for cancer, including use in combination with immune adjuvants such as IL-2, IL-12, GM-CSF, and the like.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles are balanced in order to make the selection. The multiple epitopes to be incorporated in a given vaccine composition may be, but need not be, contiguous in sequence in the native antigen from which the epitopes are derived.

1.) Epitopes are selected which, upon administration, mimic immune responses that have been observed to be correlated with clearance of HPV infection or tumor clearance. For HLA Class I this includes 3–4 epitopes that come from at least one TAA. For HLA Class II a similar rationale is employed; again 3–4 epitopes are selected from at least one TAA (see, e.g., Rosenberg et al., *Science* 278:1447–1450). Epitopes from one TAA may be used in combination with epitopes from one or more additional TAAs to produce a vaccine that targets tumors with varying expression patterns of frequently-expressed TAAs as described, e.g., in Example 15.

2.) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3.) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4.) When selecting epitopes from cancer-related antigens it is often useful to select analogs because the patient may have developed tolerance to the native epitope. When selecting epitopes for infectious disease-related antigens it is preferable to select either native or analoged epitopes.

5.) Of particular relevance are epitopes referred to as "nested epitopes." Nested epitopes occur where at least two epitopes overlap in a given peptide sequence. A nested peptide sequence can comprise both HLA class I and HLA class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6.) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

7.) In cases where the sequences of multiple variants of the same target protein are available, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

8.) When selecting an array of epitopes of an infectious agent, it is preferred that at least some of the epitopes are derived from early and late proteins. The early proteins of HPV are expressed when the virus is replicating, either following acute or dormant infection. Therefore, it is particularly preferred to use epitopes from early stage proteins to alleviate disease manifestations at the earliest stage possible.

III.K.1. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, e.g., co-pending application U.S. Ser. No. 09/311,784; Ishioka et al., *J. Immunol.* 162:3915–3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes derived from multiple regions of one or more HPV antigens, the PADRE™ universal helper T cell epitope (or multiple HTL epitopes from HPV antigens), and an endoplasmic reticulum-translocating signal sequence can be engineered. A vaccine may also comprise epitopes that are derived from other TAAs.

The immunogenicity of a multi-epitopic minigene can be tested in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created; To optimize expression and/or immunogenicity, additional elements can be incorporated into the minigene design. Examples of amino acid sequences that can be reverse translated and included in the minigene sequence include: HLA class I epitopes, HLA class II epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30–100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving HTL induction. In contrast to HTL or CTL induction, specifically decreasing the immune response by co-expression of immunosuppressive molecules (e.g. TGF-β, may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, BioTechniques 6(7): 682 (1988); U.S. Pat. No. 5,279,833; WO 91/06309; and Felgner, et al., Proc. Nat'l Acad. Sci. USA 84:7413 (1987). In addition, peptides and compounds referred to collectively as protective, interactive, noncondensing compounds (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, intraperitoneal (i.p.) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is evaluated in transgenic mice in an analogous manner.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

III.K2. Combinations of CTL Peptides with Helper Peptides

Vaccine compositions comprising CTL peptides of the invention can be modified to provide desired attributes, such as improved serum half life, broadened population coverage or enhanced immunogenicity.

For instance, the ability of a peptide to induce CTL activity can be enhanced by linking the peptide to a sequence which contains at least one epitope that is capable of inducing a T helper cell response. The use of T helper epitopes in conjunction with CTL epitopes to enhance immunogenicity is illustrated, for example, in the co-pending applications U.S. Ser. No. 08/820,360, U.S. Ser. No. 08/197,484, and U.S. Ser. No. 08/464,234.

Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in the majority of the population. This can be accomplished by selecting peptides that bind to many, most, or all of the HLA class II molecules. These are known as "loosely HLA-restricted" or "promiscuous" T helper sequences. Examples of amino acid sequences that are promiscuous include sequences from antigens such as tetanus toxoid at positions 830–843 (QYIKANSKFIGITE; SEQ ID NO: 51484), Plasmodium falciparum circumsporozoite (CS) protein at positions 378–398 (DIEKKIAKMEKASSVFNVVNS; SEQ ID NO: 51485), and Streptococcus 18 kD protein at positions 116 (GAVDSILGGVATYGAA; SEQ ID NO: 51486). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE®, Epimmune, Inc., San Diego, Calif.) are designed to most preferably bind most HLA-DR (human HLA class II) molecules. For instance, a pan-DR-binding epitope peptide having the formula: aKXVAAWTLKAAa (SEQ ID NO: 51505), where "X" is either cyclohexylalanine, phenylalanine, or tyrosine, and a is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

III.K3. Combinations of CTL Peptides with T Cell Priming Agents

In some embodiments it may be desirable to include in the pharmaceutical compositions of the invention at least one component which primes cytotoxic T lymphocytes. Lipids have been identified as agents capable of priming CTL in vivo against viral antigens. For example, palmitic acid residues can be attached to the ε- and α-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic composition comprises palmitic acid attached to ε- and α- amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide (see, e.g., Deres, et al., *Nature* 342:561, 1989). Peptides of the invention can be coupled to $P_3CSS$, for example, and the lipopeptide administered to an individual to specifically prime a CTL response to the target antigen. Moreover, because the induction of neutralizing antibodies can also be primed with $P_3CSS$-conjugated epitopes, two such compositions can be combined to more effectively elicit both humoral and cell-mediated responses.

CTL and/or HTL peptides can also be modified by the addition of amino acids to the termini of a peptide to provide for ease of linking peptides one to another, for coupling to a carrier support or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide; particularly class I peptides. However, it is to be noted that modification at the carboxyl terminus of a CTL epitope may, in some cases, alter binding characteristics of the peptide. In addition, the peptide or oligopeptide sequences can differ from the natural sequence by being modified by terminal-$NH_2$ acylation, e.g., by alkanoyl (C1–C20) or thioglycolyl acetylation, terminal-carboxyl amidation, e.g., ammonia, methylamine, etc. In some instances these modifications may provide sites for linking to a support or other molecule.

IV.J.4. Vaccine Compositions Comprising DC Pulsed with CTL and/or HTL Peptides An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs which present the pulsed peptide epitopes complexed with HLA molecules on their surfaces.

The DC can be pulsed ex vivo with a cocktail of peptides, some of which stimulate CTL responses to one or more HPV antigens of interest. Optionally, a helper T cell (HTL) peptide such as a PADRE family molecule, can be included to facilitate the CTL response. Thus, a vaccine in accordance with the invention, preferably comprising epitopes from multiple HPV antigens, is used to treat HPV infection or cancer resulting from HPV infection.

III.L. Administration of Vaccines for Therapeutic or Prophylactic Purposes

The peptides of the present invention and pharmaceutical and vaccine compositions of the invention are typically used to treat and/or prevent cancer associated with HPV infection. Vaccine compositions containing the peptides of the invention are administered to a patient infected with HPV or to an individual susceptible to, or otherwise at risk for, HPV infection to elicit an immune response against HPV antigens and thus enhance the patient's own immune response capabilities.

As noted above, peptides comprising CTL and/or HTL epitopes of the invention induce immune responses when presented by HLA molecules and contacted with a CTL or HTL specific for an epitope comprised by the peptide. The peptides (or DNA encoding them) can be administered individually or as fusions of one or more peptide sequences. The manner in which the peptide is contacted with the CTL or HTL is not critical to the invention. For instance, the peptide can be contacted with the CTL or HTL either in vivo or in vitro. If the contacting occurs in vivo, the peptide itself can be administered to the patient, or other vehicles, e.g., DNA vectors encoding one or more peptides, viral vectors encoding the peptide(s), liposomes and the like, can be used, as described herein.

When the peptide is contacted in vitro, the vaccinating agent can comprise a population of cells, e.g., peptide-pulsed dendritic cells, or HPV-specific CTLs, which have been induced by pulsing antigen-presenting cells in vitro with the peptide or by transfecting antigen-presenting cells with a minigene of the invention. Such a cell population is subsequently administered to a patient in a therapeutically effective dose.

In therapeutic applications, peptide and/or nucleic acid compositions are administered to a patient in an amount sufficient to elicit an effective CTL and/or HTL response to the virus antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

For pharmaceutical compositions, the immunogenic peptides of the invention, or DNA encoding them, are generally administered to an individual already infected with HPV. The peptides or DNA encoding them can be administered individually or as fusions of one or more peptide sequences. HPV-infected patients, with or without neoplasia, can be treated with the immunogenic peptides separately or in conjunction with other treatments, such as surgery, as appropriate.

For therapeutic use, administration should generally begin at the first diagnosis of HPV infection or HPV-associated cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, in a patient with a tumor that expresses HPV antigens, a vaccine comprising HPV-specific CTL may be more efficacious in killing tumor cells in patient with advanced disease than alternative embodiments.

Where susceptible individuals are identified prior to or during infection, the composition can be targeted to them, thus minimizing the need for administration to a larger population. Susceptible populations include those individuals who are sexually active.

The peptide or other compositions used for the treatment or prophylaxis of HPV infection can be used, e.g., in persons who have not manifested symptoms, e.g., neoplasia. In this context, it is generally important to provide an amount of the peptide epitope delivered by a mode of administration sufficient to effectively stimulate a cytotoxic T cell response; compositions which stimulate helper T cell responses can also be given in accordance with this embodiment of the invention.

The dosage for an initial therapeutic immunization generally occurs in a unit dosage range where the lower value is about 1, 5, 50, 500, or 1,000 μg and the higher value is about 10,000; 20,000; 30,000; or 50,000 μg. Dosage values for a human typically range from about 500 μg to about 50,000 μg per 70 kilogram patient. Boosting dosages of between about 1.0 μg to about 50,000 μg of peptide pursuant to a boosting regimen over weeks to months may be administered depending upon the patient's response and condition as determined by measuring the specific activity of CTL and HTL obtained from the patient's blood. Administration should continue until at least clinical symptoms or laboratory tests indicate that the viral infection, or neoplasia, has been eliminated or reduced and for a period thereafter. The dosages, routes of administration, and dose schedules are adjusted in accordance with methodologies known in the art.

In certain embodiments, the peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used purely as prophylactic agents. Generally the dosage for an initial prophylactic immunization generally occurs in a unit dosage range where the lower value is about 1, 5, 50, 500, or 1000 μg and the higher value is about 10,000; 20,000; 30,000; or 50,000 μg. Dosage values for a human typically range from about 500 μg to about 50,000 μg per 70 kilogram patient. This is followed by boosting dosages of between about 1.0 μg to about 50,000 μg of peptide administered at defined intervals from about four weeks to six months after the initial administration of vaccine. The immunogenicity of the vaccine can be assessed by measuring the specific activity of CTL and HTL obtained from a sample of the patient's blood.

The pharmaceutical compositions for therapeutic treatment are intended for parenteral, topical, oral, intrathecal, or local (e.g. as a cream or topical ointment) administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of the peptide composition is typically included in a pharmaceutical composition that comprises a human unit dose of an acceptable carrier, preferably an aqueous carrier, and is administered in a volume of fluid that is known by those of skill in the art to be used for administration of such compositions to humans (see, e.g., *Remington's Pharmaceutical Sciences*, $17^{th}$ Edition, A. Gennaro, Editor, Mack Publishing Co., Easton, Pa., 1985).

The peptides of the invention, and/or nucleic acids encoding the peptides, can also be administered via liposomes, which may also serve to target the peptides to a particular tissue, such as lymphoid tissue, or to target selectively to infected cells, as well as to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the immunogenic peptides are preferably supplied in finely divided form along with a surfactant and propellant. Typical percentages of peptides are 0.01%–20% by weight, preferably 11%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

III.M. Kits

The peptide and nucleic acid compositions of this invention can be provided in kit form together with instructions for vaccine administration. Typically the kit would include desired peptide compositions in a container, preferably in unit dosage form and instructions for administration. An alternative kit would include a minigene construct with desired nucleic acids of the invention in a container, preferably in unit dosage form together with instructions for administration. Lymphokines such as IL-2 or IL-12 may also be included in the kit. Other kit components that may also be desirable include, for example, a sterile syringe, booster dosages, and other desired excipients.

Epitopes in accordance with the present invention were successfully used to induce an immune response. Immune responses with these epitopes have been induced by administering the epitopes in various forms. The epitopes have been administered as peptides, as nucleic acids, and as viral vectors comprising nucleic acids that encode the epitope(s) of the invention. Upon administration of peptide-based epitope forms, immune responses have been induced by direct loading of an epitope onto an empty HLA molecule that is expressed on a cell, and via internalization of the epitope and processing via the HLA class I pathway; in either event, the HLA molecule expressing the epitope was then able to interact with and induce a CTL response. Peptides can be delivered directly or using such agents as liposomes. They can additionally be delivered using ballistic delivery, in which the peptides are typically in a crystalline form. When DNA is used to induce an immune response, it is administered either as naked DNA, generally in a dose range of approximately 1–5mg, or via the ballistic "gene gun" delivery, typically in a dose range of approximately 10–100 µg. The DNA can be delivered in a variety of conformations, e.g., linear, circular etc. Various viral vectors have also successfully been used that comprise nucleic acids which encode epitopes in accordance with the invention.

Accordingly compositions in accordance with the invention exist in several forms. Embodiments of each of these composition forms in accordance with the invention have been successfully used to induce an immune response.

One composition in accordance with the invention comprises a plurality of peptides. This plurality or cocktail of peptides is generally admixed with one or more pharmaceutically acceptable excipients. The peptide cocktail can comprise multiple copies of the same peptide or can comprise a mixture of peptides. The peptides can be analogs of naturally occurring epitopes. The peptides can comprise artificial amino acids and/or chemical modifications such as addition of a surface active molecule, e.g., lipidation; acetylation, glycosylation, biotinylation, phosphorylation etc. The peptides can be CTL or HTL epitopes. In a preferred embodiment the peptide cocktail comprises a plurality of different CTL epitopes and at least one HTL epitope. The HTL epitope can be naturally or non-naturally (e.g., PADRE®, Epimmune Inc., San Diego, Calif.). The number of distinct epitopes in an embodiment of the invention is generally a whole unit integer from one through one hundred fifty (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 150).

An additional embodiment of a composition in accordance with the invention comprises a polypeptide multi-epitope construct, i.e., a polyepitopic peptide. Polyepitopic peptides in accordance with the invention are prepared by use of. technologies well-known in the art. By use of these known technologies, epitopes in accordance with the invention are connected one to another. The polyepitopic peptides can be linear or non-linear, e.g., multivalent. These polyepitopic constructs can comprise artificial amino acids, spacing or spacer amino acids, flanking amino acids, or chemical modifications between adjacent epitope units. The polyepitopic construct can be a heteropolymer or a homopolymer. The polyepitopic constructs generally comprise epitopes in a quantity of any whole unit integer between 2–150 (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or 150). The polyepitopic construct can comprise CTL and/or HTL epitopes. One or more of the epitopes in the construct can be modified, e.g., by addition of a surface active material, e.g. a lipid, or chemically modified, e.g., acetylation, etc. Moreover, bonds in the multiepitopic construct can be other than peptide bonds, e.g., covalent bonds, ester or ether bonds, disulfide bonds, hydrogen bonds, ionic bonds etc.

Alternatively, a composition in accordance with the invention comprises construct which comprises a series, sequence, stretch, etc., of amino acids that have homology to (i.e., corresponds to or is contiguous with) to a native sequence. This stretch of amino acids comprises at least one subsequence of amino acids that, if cleaved or isolated from the longer series of amino acids, functions as an HLA class I or HLA class II epitope in accordance with the invention. In this embodiment, the peptide sequence is modified, so as to become a construct as defined herein, by use of any number of techniques known or to be provided in the art. The polyepitopic constructs can contain homology to a native sequence in any whole unit integer increment from 70–100%, e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or, 100 percent.

A further embodiment of a composition in accordance with the invention is an antigen presenting cell that comprises one or more epitopes in accordance with the invention. The antigen presenting cell can be a "professional" antigen presenting cell, such as a dendritic cell. The antigen presenting cell can comprise the epitope of the invention by any means known or to be determined in the art. Such means include pulsing of dendritic cells with one or more individual epitopes or with one or more peptides that comprise multiple epitopes, by nucleic acid administration such as ballistic nucleic acid delivery or by other techniques in the art for administration of nucleic acids, including vector-based, e.g. viral vector, delivery of nucleic acids.

Further embodiments of compositions in accordance with the invention comprise nucleic acids that encode one or more peptides of the invention, or nucleic acids which encode a polyepitopic peptide in accordance with the invention. As appreciated by one of ordinary skill in the art, various nucleic acids compositions will encode the same peptide due to the redundancy of the genetic code. Each of these nucleic acid compositions falls within the scope of the present invention. This embodiment of the invention comprises DNA or RNA, and in certain embodiments a combination of DNA and RNA. It is to be appreciated that any composition comprising nucleic acids that will encode a peptide in accordance with the invention or any other peptide based composition in accordance with the invention, falls within the scope of this invention.

It is to be appreciated that peptide-based forms of the invention (as well as the nucleic acids that encode them) can comprise analogs of epitopes of the invention generated using priniciples already known, or to be known, in the art. Principles related to analoging are now known in the art, and are disclosed herein; moreover, analoging principles (heteroclitic analoging) are disclosed in co-pending application serial number U.S. Ser. No. 09/226,775 filed 6 Jan. 1999. Generally the compositions of the invention are isolated or purified.

The invention will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments in accordance with the invention.

IV. EXAMPLES

The following example of peptide binding to HLA molecules demonstrates quantification of binding affinities of HLA class I and class II peptides. Binding assays can be performed with peptides that are either motif-bearing or not motif-bearing.

Example 1. HLA Class I and Class II Binding Assays

Cell lysates were prepared and HLA molecules purified in accordance with disclosed protocols (Sidney et al., *Current Protocols in Immunology* 18.3.1 (1998); Sidney, et al., *J. Immunol.* 154:247 (1995); Sette, et al., *Mol. Immunol.* 31:813 (1994)). The cell lines used as sources of HLA molecules and the antibodies used for the extraction of the HLA molecules from the cell lysates are also described in these publications.

Epstein-Barr virus (EBV)-transformed homozygous cell lines, fibroblasts, CIR, or 721.221-transfectants were used as sources of HLA class I molecules. These cells were maintained in vitro by culture in RPMI 1640 medium supplemented with 2 mM L-glutamine (GIBCO, Grand Island, N.Y.), 50 µM 2-ME, 100 µg/ml of streptomycin, 100 U/ml of penicillin (Irvine Scientific) and 10% heat-inactivated FCS (Irvine Scientific, Santa Ana, Calif.). Cells were grown in 225-cm$^2$ tissue culture flasks or, for large-scale cultures, in roller bottle apparatuses.

Cell lysates were prepared and HLA molecules purified in accordance with disclosed protocols (Sidney et al., *Current Protocols in Immunology* 18.3.1 (1998); Sidney, et al, *J. Immunol.* 154:247 (1995); Sette, et al., *Mol. Immunol.* 31:813 (1994)). Briefly, cells were lysed at a concentration of 10$^8$ cells/ml in 50 mM Tris-HCl, pH 8.5, containing 1% Nonidet P-40 (Fluka Biochemika, Buchs, Switzerland), 150 mM NaCl, 5 mM EDTA, and 2 mM PMSF. Lysates were cleared of debris and nuclei by centrifugation at 15,000×g for 30 min.

HLA molecules were purified from lysates by affinity chromatography. Lysates prepared as above were passed twice through two pre-columns of inactivated Sepharose CL4-B and protein A-Sepharose. Next, the lysate was passed over a column of Sepharose CL-4B beads coupled to an appropriate antibody. The anti-HLA column was then washed with 10-column volumes of 10 mM Tris-HCL, pH 8.0, in 1% NP-40, PBS, 2-column volumes of PBS, and 2-column volumes of PBS containing 0.4% n-octylglucoside. Finally, MHC molecules were eluted with 50 mM diethylamine in 0.15 mM NaCl containing 0.4% n-octylglucoside, pH 11.5. A 1/25 volume of 2.0M Tris, pH 6.8, was added to the eluate to reduce the pH to ~8.0. Eluates were then concentrated by centrifugation in Centriprep 30 concentrators at 2000 rpm (Amicon, Beverly, Mass.). Protein content was evaluated by a BCA protein assay (Pierce Chemical Co., Rockford, Ill.) and confirmed by SDS-PAGE.

A detailed description of the protocol utilized to measure the binding of peptides to Class I and Class II MHC has been published (Sette et al., *Mol. Immunol.* 31:813, 1994; Sidney et al., in *Current Protocols in Immunology*, Margulies, Ed., John Wiley & Sons, New York, Section 18.3, 1998). Briefly, purified MHC molecules (5 to 500 nM) were incubated with various unlabeled peptide inhibitors and 1–10 nM $^{125}$I-radiolabeled probe peptides for 48 h in PBS containing 0.05% Nonidet P-40 (NP40) (or 20% w/v digitonin for H-2 IA assays) in the presence of a protease inhibitor cocktail. The final concentrations of protease inhibitors (each from CalBioChem, La Jolla, Calif.) were 1 mM PMSF, 1.3 nM 1.10 phenanthroline, 73 µM pepstatin A, 8 mM EDTA, 6 mM N-ethylmaleimide (for Class II assays), and 200 µM N alpha-p-tosyl-L-lysine chloromethyl ketone (TLCK). All assays were performed at pH 7.0 with the exception of DRB1*0301, which was performed at pH 4.5, and DRB1 1601 (DR2w21β$_1$) and DRB4*0101 (DRw53), which were performed at pH 5.0. pH was adjusted as described elsewhere (see Sidney et al., in *Current Protocols in Immunology*, Margulies, Ed., John Wiley & Sons, New York, Section 18.3, 1998).

Following incubation, MHC-peptide complexes were separated from free peptide by gel filtration on 7.8 mm×15 cm TSK200 columns (TosoHaas 16215, Montgomeryville, Pa.), eluted at 1.2 mls/min with PBS pH 6.5 containing 0.5% NP40 and 0.1% NaN$_3$. Because the large size of the radiolabeled peptide used for the DRB1*1501 (DR2w2β$_1$) assay makes separation of bound from unbound peaks more difficult under these conditions, all DRB1*1501 (DR2w2β$_1$) assays were performed using a 7.8 mm×30 cm TSK2000 column eluted at 0.6 mls/min. The eluate from the TSK columns was passed through a Beckman 170 radioisotope detector, and radioactivity was plotted and integrated using a Hewlett-Packard 3396A integrator, and the fraction of peptide bound was determined.

Radiolabeled peptides were iodinated using the chloramine-T method. Representative radiolabeled probe peptides utilized in each assay, and its assay specific $IC_{50}$ nM, are summarized in Tables IV and V. Typically, in preliminary experiments, each MHC preparation was titered in the presence of fixed amounts of radiolabeled peptides to determine the concentration of HLA molecules necessary to bind 10–20% of the total radioactivity. All subsequent inhibition and direct binding assays were performed using these HLA concentrations.

Since under these conditions [label]<[HLA] and $IC_{50} \geq$ [HLA], the measured $IC_{50}$ values are reasonable approximations of the true $K_D$ values. Peptide inhibitors are typically tested at concentrations ranging from 120 µg/ml to 1.2 ng/ml, and are tested in two to four completely independent experiments. To allow comparison of the data obtained in different experiments, a relative binding figure is calculated for each peptide by dividing the $IC_{50}$ of a positive control for inhibition by the $IC_{50}$ for each tested peptide (typically unlabeled versions of the radiolabeled probe peptide). For inter-experiment comparisons, relative binding values are compiled. These values can subsequently be converted back into $IC_{50}$ nM values by dividing the $IC_{50}$ nM of the positive controls for inhibition by the relative binding of the peptide of interest. This method of data compilation has proven to be the most accurate and consistent for comparing peptides that have been tested on different days, or with different lots of purified MHC.

Because the antibody used for HLA-DR purification (LB3.1) is α-chain specific, $β_1$ molecules are not separated from $β_3$ (and/or $β_4$ and $β_5$) molecules. The $β_1$ specificity of the binding assay is obvious in the cases of DRB1*0101 (DR1), DRB1*0802 (DR8w2), and DRB1*0803 (DR8w3), where no $β_3$ is expressed. It has also been demonstrated for DRB1*0301 (DR3) and DRB3*0101 (DR52a), DRB1*0401 (DR4w4), DRB1*0404 (DR4w14), DRB1*0405 (DR4w15), DRB1*1101 (DR5), DRB1*1201 (DR5w12), DRB1*1302 (DR6w19) and DRB1*0701 (DR7). The problem of β chain specificity for DRB1*1501 (DR2w2$β_1$), DRB5*0101 (DR2w2$β_2$), DRB1*1601 (DR2w21$β_1$), DRB5*0201 (DR51Dw21), and DRB4*0101 (DRw53) assays is circumvented by the use of fibroblasts. Development and validation of assays with regard to DRβ molecule specificity have been described previously (see, e.g., Southwood et al.; *J. Immunol.* 160:3363–3373, 1998).

Binding assays as outlined above may be used to analyze supermotif and/or motif-bearing epitopes as, for example, described in Example 2.

Example 2

Identification of HLA Supermotif- and Motif-bearing CTL Candidate Epitopes

Vaccine compositions of the invention can include multiple epitopes that comprise multiple HLA supermotifs or motifs to achieve broad population coverage. This example illustrates the identification of supermotif- and motif-bearing epitopes for the inclusion in such a vaccine composition. Calculation of population coverage was performed using the strategy described below.

Computer Searches and Algorthims for Identification of Supermotif and/or Motif-bearing Epitopes The searches performed to identify the motif-bearing peptide sequences in Examples 2 and 5 employed the protein sequence data from seven proteins (E1, E2, E5, E6, E7, L1 and L2) from HPV types 16, 18, 31, 33, 45, and 56. (See, Table XXII for Accession numbers.)

Computer searches for epitopes bearing HLA Class I or Class II supermotifs or motifs were performed as follows.

All translated HPV protein sequences were analyzed using a text string search software program, e.g., MotifSearch 1.4 (D. Brown, San Diego) to identify potential peptide sequences containing appropriate HLA binding motifs; alternative programs are readily produced in accordance with information in the art in view of the motif/supermotif disclosure herein. Furthermore, such calculations can be made mentally.

Identified A2-, A3-, and DR-supermotif sequences were scored using polynomial algorithms to predict their capacity to bind to specific HLA-Class I or Class II molecules. These polynomial algorithms take into account both extended and refined motifs (that is, to account for the impact of different amino acids at different positions), and are essentially based on the premise that the overall affinity (or $\Delta G$) of peptide-HLA molecule interactions can be approximated as a linear polynomial function of the type:

$$\text{``}\Delta G\text{''} = a_{1i} \times a_{2i} \times a_{3i} \ldots \times a_{ni}$$

where $a_{ji}$ is a coefficient which represents the effect of the presence of a given amino acid (j) at a given position (i) along the sequence of a peptide of n amino acids. The crucial assumption of this method is that the effects at each position are essentially independent of each other (i.e., independent binding of individual side-chains). When residue j occurs at position i in the peptide, it is assumed to contribute a constant amount $j_i$ to the free energy of binding of the peptide irrespective of the sequence of the rest of the peptide. This assumption is justified by studies from our laboratories that demonstrated that peptides are bound to MHC and recognized by T cells in essentially an extended conformation (data omitted herein).

The method of derivation of specific algorithm coefficients has been described in Gulukota et al., *J. Mol. Biol.* 267:1258–126, 1997; (see also Sidney et al., *Human Immunol.* 45:79–93, 1996; and Southwood et al., *J. Immunol.* 160:3363–3373, 1998). Briefly, for all i positions, anchor and non-anchor alike, the geometric mean of the average relative binding (ARB) of all peptides carrying j is calculated relative to the remainder of the group, and used as the estimate of $j_i$. For Class II peptides, if multiple alignments are possible, only the highest scoring alignment is utilized, following an iterative procedure. To calculate an algorithm score of a given peptide in a test set, the ARB values corresponding to the sequence of the peptide are multiplied. If this product exceeds a chosen threshold, the peptide is predicted to bind. Appropriate thresholds are chosen as a function of the degree of stringency of prediction desired.

Selection of HLA-A2 Supertype Cross-reactive Peptides

Complete protein sequences from the seven HPV structural and regulatory proteins of the HPV strains listed above were aligned, then scanned, utilizing motif identification software, to identify 9- and 10-mer sequences containing the HLA-A2-supermotif main anchor specificity.

HLA-A2 supermotif-bearing sequences are shown in Table VIII. Typically, these sequences are then scored using the A2 algorithm and the peptides corresponding to the positive-scoring sequences are synthesized and tested for their capacity to bind purified HLA-A*0201 molecules in vitro (HLA-A*0201 is considered a prototype A2 supertype molecule).

Examples of peptides that bind to HLA-A*0201 with $IC_{50}$ values $\leq$500 nM are shown in Table VII. These peptides are then tested for the capacity to bind to additional A2-supertype molecules (A*0202, A*0203, A*0206, and A*6802). Peptides that bind to at least three of the five A2-supertype alleles tested are typically deemed A2-supertype cross-reactive binders. Preferred peptides bind at an affinity equal to or less than 500 nM to three or more HLA-A2 supertype molecules.

Selection of HLA-A3 Supermotif-bearing Epitopes

The HPV protein sequences scanned above were also examined for the presence of peptides with the HLA-A3-supermotif primary anchors (Table IX).

Peptides corresponding to the supermotif-bearing sequences are then synthesized and tested for binding to HLA-A*0301 and HLA-A*1101 molecules, the two most prevalent A3-supertype alleles. The peptides that are found to bind one of the two alleles with binding affinities of $\leq 500$ nM, often $\leq 200$ nM, are then tested for binding cross-reactivity to the other common A3-supertype alleles (A*310, A*3301, and A*6801) to identify those that can bind at least three of the five HLA-A3-supertype molecules tested.

Selection of HLA-B7 Supermotif Bearing Epitopes

The same HPV target antigen protein sequences were also analyzed for the presence of 9- or 10-mer peptides with the HLA-B7-supermotif (Table XI).

Corresponding peptides are synthesized and tested for binding to HLA-B*0702, the most common B7-supertype allele (i.e., the prototype B7 supertype allele). Peptides binding B 0702 with $IC_{50}$ of $\leq 500$ nM are identified using standard methods. These peptides are then tested for binding to other common B7-supertype molecules (B*3501, B*5101, B*5301, and B*5401). Peptides capable of binding to three or more of the five B7-supertype alleles tested are thereby identified.

Selection of A1 and A24 Motif-bearing Epitopes

To further increase population coverage, HLA-A1 and -A24 epitopes can, for example, also be incorporated into potential vaccine constructs. An analysis of the protein sequence data from the HPV target antigens utilized above can also be performed to identify HLA-A1- and A24-motif-containing sequences.

High affinity and/or cross-reactive binding epitopes that bear other motif and/or supermotifs can be identified using analogous methodology.

Example 3

Confirmation of Immunogenicity

Cross-reactive candidate CTL A2-supermotif-bearing peptides that are identified as described in Example 2 were selected for in vitro immunogenicity testing. Testing was performed using the following methodology:

Target Cell Lines for Cellular Screening:

The .221A2.1 cell line, produced by transferring the HLA-A2.1 gene into the HLA-A, -B, -C null mutant human B-lymphoblastoid cell line 721.221, is used as the peptide-loaded target to measure activity of HLA-A2.1-restricted CTL. This cell line is grown in RPMI-1640 medium supplemented with antibiotics, sodium pyruvate, nonessential amino acids and 10% (v/v) heat inactivated FCS. Cells that express an antigen of interest, or transfectants comprising the gene encoding the antigen of interest, can be used as target cells to test the ability of peptide-specific CTLs to recognize endogenous antigen.

Primary CTL Induction Cultures:

Generation of Dendritic Cells (DC): PBMCs are thawed in RPMI with 30 μg/ml DNAse, washed twice and resuspended in complete medium (RPMI-1640 plus 5% AB human serum, non-essential amino acids, sodium pyruvate, L-glutamine and penicillin/strpetomycin). The monocytes are purified by plating 10×10⁶ PBMC/well in a 6-well plate. After 2 hours at 37° C., the non-adherent cells are removed by gently shaking the plates and aspirating the supernatants. The wells are washed a total of three times with 3 ml RPMI to remove most of the non-adherent and loosely adherent cells. Three ml of complete medium containing 50 ng/ml of GM-CSF and 1,000 U/ml of IL4 are then added to each well. TNFα is added to the DCs on day 6 at 75 ng/ml and the cells are used for CTL induction cultures on day 7.

Induction of CTL with DC and Peptide: CD8+ T-cells are isolated by positive selection with Dyna1 immunomagnetic beads (Dynabeads® M-450) and the detacha-bead® reagent. Typically about 200–250×10⁶ PBMC are processed to obtain 24×10⁶ CD8+ T-cells (enough for a 48-well plate culture). Briefly, the PBMCs are thawed in RPMI with 30 μg/ml DNAse, washed once with PBS containing 1% human AB serum and resuspended in PBS/1% AB serum at a concentration of 20×10⁶ cells/ml. The magnetic beads are washed 3 times with PBS/AB serum, added to the cells (140 μl beads/20×10⁶ cells) and incubated for 1 hour at 4° C. with continuous mixing. The beads and cells are washed 4× with PBS/AB serum to remove the nonadherent cells and resuspended at 100×10⁶ cells/ml (based on the original cell number) in PBS/AB serum containing 100 μl/ml detacha-bead® reagent and 30 μg/ml DNAse. The mixture is incubated for 1 hour at room temperature with continuous mixing. The beads are washed again with PBS/AB/DNAse to collect the CD8+ T-cells. The DC are collected and centrifuged at 1300 rpm for 5–7 minutes, washed once with PBS with 1% BSA, counted and pulsed with 40 μg/ml of peptide at a cell concentration of 1–2×10⁶/ml in the presence of 3 μg/ml $β_2$-microglobulin for 4 hours at 20° C. The DC are then irradiated (4,200 rads), washed 1 time with medium and counted again.

Setting up induction cultures: 0.25 ml cytokine-generated DC (@1×10⁵ cells/ml) are co-cultured with 0.25 ml of CD8+ T-cells (@2×10⁶ cell/ml) in each well of a 48-well plate in the presence of 10 ng/ml of IL-7. Recombinant human IL10 is added the next day at a final concentration of 10 ng/ml and rhuman IL2 is added 48 hours later at 10 IU/ml.

Restimulation of the induction cultures with peptide-pulsed adherent cells: Seven and fourteen days after the primary induction the cells are restimulated with peptide-pulsed adherent cells. The PBMCS are thawed and washed twice with RPMI and DNAse. The cells are resuspended at 5×10⁶ cells/ml and irradiated at ~4200 rads. The PBMCs are plated at 2×10⁶ in 0.5 ml complete medium per well and incubated for 2 hours at 37° C. The plates are washed twice with RPMI by tapping the plate gently to remove the nonadherent cells and the adherent cells pulsed with 10 μg/ml of peptide in the presence of 3 μg/ml $β_2$ microglobulin in 0.25 ml RPMI/5% AB per well for 2 hours at 37° C. Peptide solution from each well is aspirated and the wells are washed once with RPMI. Most of the media is aspirated from the induction cultures (CD8+ cells) and brought to 0.5 ml with fresh media. The cells are then transferred to the wells containing the peptide-pulsed adherent cells. Twenty four hours later rhuman IL10 is added at a final concentration of 10 ng/ml and rhuman IL2 is added the next day and again 2–3 days later at 50 IU/ml (Tsai et al., *Critical Reviews in Immunology* 18(1–2):65–75, 1998). Seven days later the cultures are assayed for CTL activity in a $^{51}$Cr release assay. In some experiments the cultures are assayed for peptide-specific recognition in the in situ IFNγ ELISA at the time of the second restimulation followed by assay of endogenous recognition 7 days later. After expansion, activity is measured in both assays for a side by side comparison.

Measurement of CTL Lytic Activity by $^{51}$Cr Release.

Seven days after the second restimulation, cytotoxicity is determined in a standard (5 hr) $^{51}$Cr release assay by assaying individual wells at a single E:T. Peptide-pulsed targets are prepared by incubating the cells with 10 µg/ml peptide overnight at 37° C.

Adherent target cells are removed from culture flasks with trypsin-EDTA. Target cells are labelled with 200 µCi of $^{51}$Cr sodium chromate (Dupont, Wilmington, Del.) for 1 hour at 37° C. Labelled target cells are resuspended at $10^6$ per ml and diluted 1:10 with K562 cells at a concentration of $3.3 \times 10^6$/ml (an NK-sensitive erythroblastoma cell line used to reduce non-specific lysis). Target cells (100 µl) and 100 µl of effectors are plated in 96 well round-bottom plates and incubated for 5 hours at 37° C. At that time, 100 µl of supernatant are collected from each well and percent lysis is determined according to the formula: [(cpm of the test sample-cpm of the spontaneous $^{51}$Cr release sample)/(cpm of the maximal $^{51}$Cr release sample-cpm of the spontaneous $^{51}$Cr release sample)]×100. Maximum and spontaneous release are determined by incubating the labelled targets with 1% Triton X-100 and media alone, respectively. A positive culture is defined as one in which the specific lysis (sample-background) is 10% or higher in the case of individual wells and is 15% or more at the 2 highest E:T ratios when expanded cultures are assayed.

In situ Measurement of Human γIFN Production as an Indicator of Peptide-specific and Endogenous Recognition Immulon 2 plates are coated with mouse anti-human IFNγ monoclonal antibody (4 µg/ml 0.1M NaHCO$_3$, pH8.2) overnight at 4° C. The plates are washed with Ca$^{2+}$, Mg$^{2+}$-free PBS/0.05% Tween 20 and blocked with PBS/10% FCS for 2 hours, after which the CTLs (100 µ/well) and targets (100 µl/well) are added to each well, leaving empty wells for the standards and blanks (which received media only). The target cells, either peptide-pulsed or endogenous targets, are used at a concentration of $1 \times 10^6$ cells/ml. The plates are incubated for 48 hours at 37° C. with 5% CO$_2$.

Recombinant human IFNγ is added to the standard wells starting at 400 pg or 1200 pg/100 µl/well and the plate incubated for 2 hours at 37° C. The plates are washed and 100 µl of biotinylated mouse anti-human IFNγ monoclonal antibody (2 µg/ml in PBS/3% FCS/0.05% Tween 20) are added and incubated for 2 hours at room temperature. After washing again, 100 µl HRP-streptavidin (1:4000) are added and the plates incubated for 1 hour at room temperature. The plates are then washed 6× with wash buffer, 100 µl/well developing solution (TMB 1:1) are added, and the plates allowed to develop for 5–15 minutes. The reaction is stopped with 50 µl/well 1M H$_3$PO$_4$ and read at OD450. A culture is considered positive if it measured at least 50 pg of IFNγ/well above background and is twice the background level of expression.

CTL Expansion. Those cultures that demonstrate specific lytic activity against peptide-pulsed targets and/or tumor targets are expanded over a two week period with anti-CD3. Briefly, $5 \times 10^4$ CD8+ cells are added to a T25 flask containing the following: $1 \times 10^6$ irradiated (4,200 rad) PBMC (autologous or allogeneic) per ml, $2 \times 10^5$ irradiated (8,000 rad) EBV-transformed cells per ml, and OKT3 (anti-CD3) at 30 ng per ml in RPMI-1640 containing 10% (v/v) human AB serum, non-essential amino acids, sodium pyruvate, 25 µM 2-mercaptoethanol, L-glutamnine and penicillin/streptomycin. Rhuman IL2 is added 24 hours later at a final concentration of 200 IU/ml and every 3 days thereafter with fresh media at 50 IU/ml. The cells are split if the cell concentration exceeded $1 \times 10^6$/ml and the cultures are assayed between days 13 and 15 at E:T ratios of 30 30, 10, 3 and 1:1 in the $^{51}$Cr release assay or at $1 \times 10^6$/ml in the in situ IFNγ assay using the same targets as before the expansion.

Cultures are expanded in the absence of anti-CD3+ as follows. Those cultures that demonstrate specific lytic activity against peptide and endogenous targets are selected and $5 \times 10^4$ CD8+ cells are added to a T25 flask containing the following: $1 \times 10^6$ autologous PBMC per ml which have been peptide-pulsed with 10 µg/ml peptide for 2 hours at 37° C. and irradiated (4,200 rad); $2 \times 10^5$ irradiated (8,000 rad) EBV-transformed cells per ml RPMI-1640 containing 10% (v/v) human AB serum, non-essential AA, sodium pyruvate, 25 mM 2-ME, L-glutamine and gentamicin.

Immunogenicity of A2 Supermotif-bearing Peptides

A2-supermotif cross-reactive binding peptides are tested in the cellular assay for the ability to induce peptide-specific CTL in normal individuals. In this analysis, a peptide is typically considered to be an epitope if it induces peptide-specific CTLs in at least 2 donors (unless otherwise noted) and preferably, also recognizes the endogenously expressed peptide.

Immunogenicity is additionally confirmed using PBMCs isolated from HPV-infected patients. Briefly, PBMCs are isolated from patients, re-stimulated with peptide-pulsed monocytes and assayed for the ability to recognize peptide-pulsed target cells as well as transfected cells endogenously expressing the antigen.

Evaluation of A*03/A11 Immunogenicity

HLA-A3 supermotif-bearing cross-reactive binding peptides are also evaluated for immunogenicity using methodology analogous for that used to evaluate the immunogenicity of the HLA-A2 supermotif peptides.

Evaluation of B7 Immunogenicity

Immunogenicity screening of the B7-supertype cross-reactive binding peptides identified in Example 2 are evaluated in a manner analogous to the evaluation of A2- and A3-supermotif-bearing peptides.

Peptides bearing other supermotifs/motifs, e.g., HLA-A1, HLA-A24 etc. are also evaluated using similar methodology Example 4

Implementation of the Extended Supermotif to Improve the Binding Capacity of Native Epitopes by Creating Analogs HLA motifs and supermotifs (comprising primary and/or secondary residues) are useful in the identification and preparation of highly cross-reactive native peptides, as demonstrated herein. Moreover, the definition of HLA motifs and supermotifs also allows one to engineer highly cross-reactive epitopes by identifying residues within a native peptide sequence which can be analoged, or "fixed" to confer upon the peptide certain characteristics, e.g. greater cross-reactivity within the group of HLA molecules that comprise a supertype, and/or greater binding affinity for some or all of those HLA molecules. Examples of analoging peptides to exhibit modulated binding affinity are set forth in this example.

Analoging at Primary Anchor Residues

Peptide engineering strategies are implemented to further increase the cross-reactivity of the epitopes. For example, on the basis of the data disclosed, e.g., in related and co-pending U.S. Ser. No. 09/226,775, the main anchors of A2-supermotif-bearing peptides are altered, for example, to introduce a preferred L, I, V, or M at position 2, and I or V at the C-terminus.

To analyze the cross-reactivity of the analog peptides, each engineered analog is initially tested for binding to the prototype A2 supertype allele A*0201, then, if A*0201 binding capacity is maintained, for A2-supertype cross-reactivity.

Alternatively, a peptide is tested for binding to one or all supertype members and then analogued to modulate binding affinity to any one (or more) of the supertype members to add population coverage.

The selection of analogs for immunogenicity in a cellular screening analysis is typically further restricted by the capacity of the parent peptide to bind at least weakly, i.e., bind at an $IC_{50}$ of 5000 nM or less, to three of more A2 supertype alleles. The rationale for this requirement is that the WT peptides must be present endogenously in sufficient quantity to be biologically relevant. Analoged peptides have been shown to have increased immunogenicity and cross-reactivity by T cells specific for the parent epitope (see, e.g., Parkhurst et al., *J. Immunol.* 157:2539, 1996; and Pogue et al., *Proc. Natl. Acad. Sci. USA* 92:8166, 1995).

In the cellular screening of these peptide analogs, it is important to demonstrate that analog-specific CTLs are also able to recognize the wild-type peptide and, when possible, target cells that endogenously express the epitope.

Analoging of HLA-A3 and B7-supermotif-bearing Peptides

Analogs of HLA-A3 supermotif-bearing epitopes are generated using strategies similar to those employed in analoging HLA-A2 supermotif-bearing peptides. For example, peptides binding to 3/5 of the A3-supertype molecules are engineered at primary anchor residues to possess a preferred residue (V, S, M, or A) at position 2.

The analog peptides are then tested for the ability to bind A*03 and A*11 (prototype A3 supertype alleles). Those peptides that demonstrate ≦500 nM binding capacity are then tested for A3-supertype cross-reactivity.

Similarly to the A2- and A3-motif bearing peptides, peptides binding 3 or more B7-supertype alleles can be improved, where possible, to achieve increased cross-reactive binding. B7 supermotif-bearing peptides are, for example, engineered to possess a preferred residue V, I, L, or F) at the C-terminal primary anchor position, as demonstrated by Sidney et al. (*J. Immunol.* 157:3480–3490, 1996).

Analoguing at primary anchor residues of other motif and/or supermotif-bearing epitopes is performed in a like manner.

The analog peptides are then be tested for immunogenicity, typically in a cellular screening assay. Again, it is generally important to demonstrate that analog-specific CTLs are also able to recognize the wild-type peptide and, when possible, targets that endogenously express the epitope.

Analoging at Secondary Anchor Residues

Moreover, HLA supermotifs are of value in engineering highly cross-reactive peptides and/or peptides that bind HLA molecules with increased affinity by identifying particular residues at secondary anchor positions that are associated with such properties. For example, the binding capacity of a B7 supermotif-bearing peptide with an F residue at postion 1 is analyzed. The peptide is then analoged to, for example, substitute L for F at position 1. The analoged peptide is evaluated for increased binding affinity/and or increased cross-reactivity: Such a procedure identifies analoged peptides with modulated binding affinity.

Engineered analogs with sufficiently improved binding capacity or cross-reactivity can also be tested for immunogenicity in HLA-B7-transgenic mice, following for example, IFA immunization or lipopeptide immunization. Analogued peptides are additionally tested for the ability to stimulate a recall response using PBMC from HPV-infected patients.

Other Analoguing Strategies

Another form of peptide analoguing, unrelated to the anchor positions, involves the substitution of a cysteine with α-amino butyric acid. Due to its chemical nature, cysteine has the propensity to form disulfide bridges and sufficiently alter the peptide structurally so as to reduce binding capacity. Subtitution of α-amino butyric acid for cysteine not only alleviates this problem, but has been shown to improve binding and crossbinding capabilities in some instances (see, e.g., the review by Sette et al., In: Persistent Viral Infections, Eds. R. Ahmed and I. Chen, John Wiley & Sons, England, 1999).

Thus, by the use of even single amino acid substitutions, the binding affinity and/or cross-reactivity of peptide ligands for HLA supertype molecules can be modulated.

Example 5

Identification of HPV-derived Sequences with HLA-DR Binding Motifs

Peptide epitopes bearing an HLA class II supermotif or motif are identified as outlined below using methodology similar to that described in Examples 1–3.

Selection of HLA-DR-supermotif-bearing Epitopes.

To identify HPV-derived, HLA class II HTL epitopes, the protein sequences from the same HPV antigens used for the identification of HLA Class I supermotif/motif sequences were analyzed for the presence of sequences bearing an HLA-DR-motif or supermotif. Specifically, 15-mer sequences were selected comprising a DR-supermotif, further comprising a 9-mer core, and three-residue N- and C-terminal flanking regions (15 amino acids total).

Protocols for predicting peptide binding to DR molecules have been developed (Southwood et al., *J. Immunol.* 160:3363–3373, 1998). These protocols, specific for individual DR molecules, allow the scoring, and ranking, of 9-mer core regions. Each protocol not only scores peptide sequences for the presence of DR-supermotif primary anchors (i.e., at position 1 and position 6) within a 9-mer core, but additionally evaluates sequences for the presence of secondary anchors. Using allele specific selection tables (see, e.g., Southwood et al., ibid.), it has been found that these protocols efficiently select peptide sequences with a high probability of binding a particular DR molecule. Additionally, it has been found that performing these protocols in tandem, specifically those for DR1, DR4w4, and DR7, can efficiently select DR cross-reactive peptides.

The HPV-derived peptides identified above are tested for their binding capacity for various common HLA-DR molecules. All peptides are initially tested for binding to the DR molecules in the primary panel: DR1, DR4w4, and DR7. Peptides binding at least 2 of these 3 DR molecules are then tested for binding to DR2w2 β1, DR2w2 β2, DR6w19, and DR9 molecules in secondary assays. Finally, peptides binding at least 2 of the 4 secondary panel DR molecules, and thus cumulatively at least 4 of 7 different DR molecules, are screened for binding to DR4w15, DR5w11, and DR8w2 molecules in tertiary assays. Peptides binding at least 7 of the 10 DR molecules comprising the primary, secondary, and tertiary screening assays are considered cross-reactive DR binders. HPV-derived peptides found to bind common HLA-DR alleles are of particular interest.

Selection of DR3 Motif Peptides

Because HLA-DR3 is an allele that is prevalent in Caucasian, Black, and Hispanic populations, DR3 binding capacity is an important criterion in the selection of HTL epitopes. However, data generated previously indicated that DR3 only rarely cross-reacts with other DR alleles (Sidney et al., *J. Immunol.* 149:2634–2640, 1992; Geluk et al., *J. Immunol.* 152:5742–5748, 1994; Southwood et al., *J. Immu-* nol. 160:3363–3373, 1998). This is not entirely surprising in that the DR3 peptide-binding motif appears to be distinct from the specificity of most other DR alleles. For maximum efficiency in developing vaccine candidates it would be desirable for DR3 motifs to be clustered in proximity with DR supermotif regions. Thus, peptides shown to be candidates may also be assayed for their DR3 binding capacity. However, in view of the distinct binding specificity of the DR3 motif, peptides binding only to DR3 can also be considered as candidates for inclusion in a vaccine formulation.

To efficiently identify peptides that bind DR3, target HPV antigens are analyzed for sequences carrying one of the two DR3 specific binding motifs reported by Geluk et al. (*J. Immunol.* 152:5742–5748, 1994). The corresponding peptides are then synthesized and tested for the ability to bind DR3 with an affinity of 1 µM or better, i.e., less than 1 µM. Peptides are found that meet this binding criterion and qualify as HLA class II high affinity binders.

DR3 binding epitopes identified in this manner are included in vaccine compositions with DR supermotif-bearing peptide epitopes.

Similarly to the case of HLA class I motif-bearing peptides, the class II motif-bearing peptides are analoged to improve affinity or cross-reactivity. For example, aspartic acid at position 4 of the 9-mer core sequence is an optimal residue for DR3 binding, and substitution for that residue often improves DR 3 binding.

Example 6

Immunogenicity of HPV-derived HTL Epitopes

This example determines immunogenic DR supermotif- and DR3 motif-bearing epitopes among those identified using the methodology in Example 5.

Immunogenicity of HTL epitopes are evaluated in a manner analogous to the determination of immunogenicity of CTL epitopes by assessing the ability to stimulate HTL responses and/or by using appropriate transgenic mouse models. Immunogenicity is determined by screening for: 1.) in vitro primary induction using normal PBMC or 2.) recall responses from cancer patient PBMCs.

Example 7

Calculation of Phenotypic Frequencies of HLA-supertypes in Various Ethnic Backgrounds to Determine Breadth of Population Coverage This example illustrates the assessment of the breadth of population coverage of a vaccine composition comprised of multiple epitopes comprising multiple supermotifs and/or motifs.

In order to analyze population coverage, gene frequencies of HLA alleles were determined. Gene frequencies for each HLA allele were calculated from antigen or allele frequencies utilizing the binomial distribution formulae gf=1−(SQRT(1−af)) (see, e.g., Sidney et al., *Human Immunol.* 45:79–93, 1996). To obtain overall phenotypic frequencies, cumulative gene frequencies were calculated, and the cumulative antigen frequencies derived by the use of the inverse formula [af=1−(1−Cgf)²].

Where frequency data was not available at the level of DNA typing, correspondence to the serologically defined antigen frequencies was assumed. To obtain total potential supertype population coverage no linkage disequilibrium was assumed, and only alleles confirmed to belong to each of the supertypes were included (minimal estimates). Estimates of total potential coverage achieved by inter-loci combinations were made by adding to the A coverage the proportion of the non-A covered population that could be expected to be covered by the B alleles considered (e.g., total=A+B*(1−A)). Confirmed members of the A3-like supertype are A3, A11, A31, A*3301, and A*6801. Although the A3-like supertype may also include A34, A66, and A*7401, these alleles were not included in overall frequency calculations. Likewise, confirmed members of the A2-like supertype family are A*0201, A*0202, A*0203, A*0204, A*0205, A*0206, A*0207, A*6802, and A*6901. Finally, the B7-like supertype-confirmed alleles are: B7, B*3501–03, B51, B*5301, B*5401, B*5501–2, B*5601, B*6701, and B*7801 (potentially also B*1401, B*3504–06, B*4201, and B*5602).

Population coverage achieved by combining the A2-, A3- and B7-supertypes is approximately 86% in five major ethnic groups (see Table XXI). Coverage may be extended by including peptides bearing the A1 and A24 motifs. On average, A1 is present in 12% and A24 in 29% of the population across five different major ethnic groups (Caucasian, North American Black, Chinese, Japanese, and Hispanic). Together, these alleles are represented with an average frequency of 39% in these same ethnic populations. The total coverage across the major ethnicities when A1 and A24 are combined with the coverage of the A2-, A3- and B7-supertype alleles is >95%. An analagous approach can be used to estimate population coverage achieved with combinations of class II motif-bearing epitopes.

Immunogenicity studies in humans (e.g., Bertoni et al., *J. Clin. Invest.* 100:503, 1997; Doolan et al., *Immunity* 7:97, 1997; and Threlkeld et al., *J. Immunol.* 159:1648, 1997) have shown that highly cross-reactive binding peptides are almost always recognized as epitopes. The use of highly cross-reactive binding peptides is an important selection criterion in identifying candidate epitopes for inclusion in a vaccine that is immunogenic in a diverse population.

With a sufficient number of epitopes (as disclosed herein and from the art), an average population coverage is predicted to be greater than 95% in each of five major ethnic populations. The game theory Monte Carlo simulation analysis, which is known in the art (see e.g., Osborne, M. J. and Rubinstein, A. "A course in game theory" MIT Press, 1994), can be used to estimate what percentage of the individuals in a population comprised of the Caucasian, North American Black, Japanese, Chinese, and Hispanic ethnic groups would recognize the vaccine epitopes described herein. A preferred percentage is 90%. A more preferred percentage is 95%.

Example 8

CTL Recognition of Endogenous Processed Antigens After Priming

This example determines that CTL induced by native or analogued peptide epitopes identified and selected as described in Examples 1–6 recognize endogenously synthesized, i.e., native antigens.

Effector cells isolated from transgenic mice that are immunized with peptide epitopes as in Example 3, for example HLA-A2 supermotif-bearing epitopes, are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled Jurkat-A2.1/K$^b$ target cells in the absence or presence of peptide, and also tested on $^{51}$Cr labeled target cells bearing the endogenously synthesized antigen, i.e. cells that are stably transfected with HPV expression vectors.

The result will demonstrate that CTL lines obtained from animals primed with peptide epitope recognize endogenously synthesized HPV antigen. The choice of transgenic mouse model to be used for such an analysis depends upon the epitope(s) that is being evaluated. In addition to HLA-A*0201/K$^b$ transgenic mice, several other transgenic mouse models including mice with human A11, which may also be used to evaluate A3 epitopes, and B7 alleles have been characterized and others (e.g., transgenic mice for HLA-A1 and A24) are being developed. HLA-DR1 and HLA-DR3 mouse models have also been developed, which may be used to evaluate HTL epitopes.

Example 9

Activity of CTL-HTL Conjugated Epitopes in Transgenic Mice

This example illustrates the induction of CTLs and HTLs in transgenic mice by use of a tumor associated antigen CTL/HTL peptide conjugate whereby the vaccine composition comprises peptides to be administered to an HPV-infected patient. The peptide composition can comprise multiple CTL and/or HTL epitopes and further, can comprise epitopes selected from multiple HPV target antigens. The epitopes are identified using methodology as described in Examples 1–6 This analysis demonstrates the enhanced immunogenicity that can be achieved by inclusion of one or more HTL epitopes in a vaccine composition. Such a peptide composition can comprise an HTL epitope conjugated to a preferred CTL epitope containing, for example, at least one CTL epitope that binds to multiple HLA family members at an affinity of 500 nM or less, or analogs of that epitope. The peptides may be lipidated, if desired.

Immunization procedures: Immunization of transgenic mice is performed as described (Alexander et al., *J. Immunol.* 159:4753–4761, 1997). For example, A2/K$^b$ mice, which are transgenic for the human HLA A2.1 allele and are useful for the assessment of the immunogenicity of HLA-A*0201 motif- or HLA-A2 supermotif-bearing epitopes, are primed subcutaneously (base of the tail) with a 0.1 ml of peptide in Incomplete Freund's Adjuvant, or if the peptide composition is a lipidated CT/HTL conjugate, in DMSO/saline or if the peptide composition is a polypeptide, in PBS or Incomplete Freund's Adjuvant. Seven days after priming, splenocytes obtained from these animals are restimulated with syngenic irradiated LPS-activated lymphoblasts coated with peptide.

Cell lines: Target cells for peptide-specific cytotoxicity assays are Jurkat cells transfected with the HLA-A2.1/K$^b$ chimeric gene (e.g., Vitiello et al., *J. Exp. Med.* 173:1007, 1991)

In vitro CTL activation: One week after priming, spleen cells (30×10$^6$ cells/flask) are co-cultured at 37° C. with syngeneic, irradiated (3000 rads), peptide coated lymphoblasts (10×10$^6$ cells/flask) in 10 ml of culture medium/T25 flask. After six days, effector cells are harvested and assayed for cytotoxic activity.

Assay for cytotoxic activity: Target cells (1.0 to 1.5×10$^6$) are incubated at 37° C. in the presence of 200 μl of $^{51}$Cr. After 60 minutes, cells are washed three times and resuspended in R10 medium. Peptide is added where required at a concentration of 1 μg/ml. For the assay, 10$^4$ $^{51}$Cr-labeled target cells are added to different concentrations of effector cells (final volume of 200 μl) in U-bottom 96-well plates. After a 6 hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/10$^6$ cells. One lytic unit is arbitrarily defined as the number of effector cells required to achieve 30% lysis of 10,000 target cells in a 6 hour $^{51}$Cr release assay. To obtain specific lytic units/10$^6$, the lytic units/10$^6$ obtained in the absence of peptide is subtracted from the lytic units/10$^6$ obtained in the presence of peptide. For example, if 30% $^{51}$Cr release is obtained at the effector (E): target (T) ratio of 50:1 (i.e., 5×10$^5$ effector cells for 10,000 targets) in the absence of peptide and 5:1 (i.e., 5×10$^4$ effector cells for 10,000 targets) in the presence of peptide, the specific lytic units would be: [(1/50,000)−(1/500,000)]×10$^6$=18 LU.

The results are analyzed to assess the magnitude of the CTL responses of animals injected with the immunogenic CTL/HTL conjugate vaccine preparation and are compared to the magnitude of the CTL response achieved using the CTL epitope as outlined in Example 3. Analyses similar to this may be performed to evaluate the immunogenicity of peptide conjugates containing multiple CTL epitopes and/or multiple HTL epitopes. In accordance with these procedures it is found that a CTL response is induced, and concomitantly that an HTL response is induced upon administration of such compositions.

Example 10

Selection of CTL and HTL Epitopes for Inclusion in an HPV-specific Vaccine

This example illustrates the procedure for the selection of peptide epitopes for vaccine compositions of the invention. The peptides in the composition can be in the form of a nucleic acid sequence, either single or one or more sequences (i.e., minigene) that encodes peptide(s), or can be single and/or polyepitopic peptides.

The following principles are utilized when selecting an array of epitopes for inclusion in a vaccine composition. Each of the following principles is balanced in order to make the selection.

Epitopes are selected which, upon administration, mimic immune responses that have been observed to be correlated with HPV clearance. The number of epitopes used depends on observations of patients who spontaneously clear HPV. For example, if it has been observed that patients who spontaneously clear HPV generate an immune response to at least 3 epitopes on at least one HPV antigen, then 3–4 epitopes should be included for HLA class I. A similar rationale is used to determine HLA class II epitopes.

When selecting an array of HPV epitopes, it is preferred that at least some of the epitopes are derived from early and late proteins. The early proteins of HPV are expressed when the virus is replicating, either following acute or dormant infection. Therefore, it is particularly preferred to use epitopes from early stage proteins to alleviate disease manifestations at the earliest stage possible.

Epitopes are often selected that have a binding affinity of an IC$_{50}$ of 500 nM or less for an HLA class I molecule, or for class II, an IC$_{50}$ of 1000 nM or less.

Sufficient supermotif bearing peptides, or a sufficient array of allele-specific motif bearing peptides, are selected to give broad population coverage. For example, epitopes are selected to provide at least 80% population coverage. A Monte Carlo analysis, a statistical evaluation known in the art, can be employed to assess breadth, or redundancy, of population coverage.

When creating a polyepitopic compositions, e.g. a minigene, it is typically desirable to generate the smallest peptide possible that encompasses the epitopes of interest. The principles employed are similar, if not the same, as those employed when selecting a peptide comprising nested epitopes.

In cases where the sequences of multiple variants of the same target protein are available, potential peptide epitopes can also be selected on the basis of their conservancy. For example, a criterion for conservancy may define that the entire sequence of an HLA class I binding peptide or the entire 9-mer core of a class II binding peptide be conserved in a designated percentage of the sequences evaluated for a specific protein antigen.

A vaccine composition comprised of selected peptides, when administered, is safe, efficacious, and elicits an immune response similar in magnitude to an immune response that controls or clears an acute HPV infection.

Example 11

Construction of Minigene Multi-epitope DNA Plasmids

This example provides general guidance for the construction of a minigene expression plasmid. Minigene plasmids may, of course, contain various configurations of CTL and/or HTL epitopes or epitope analogs as described herein. Examples of the construction and evaluation of expression plasmids are described, for example, in co-pending U.S. Ser. No. 09/311,784 filed May 13, 1999.

A minigene expression plasmid typically includes multiple CTL and HTL peptide epitopes. In the present example, HLA-A2, -A3, -B7 supermotif-bearing peptide epitopes and HLA-A1 and -A24 motif-bearing peptide epitopes are used in conjunction with DR supermotif-bearing epitopes and/or DR3 epitopes. HLA class I supermotif or motif-bearing peptide epitopes derived from multiple HPV antigens, preferably including both early and late phase antigens, are selected such that multiple supermotifs/motifs are represented to ensure broad population coverage. Similarly, HLA class II epitopes are selected from multiple HPV antigens to provide broad population coverage, i.e. both HLA DR-1-4-7 supermotif-bearing epitopes and HLA DR-3 motif-bearing epitopes are selected for inclusion in the minigene construct. The selected CTL and HTL epitopes are then incorporated into a minigene for expression in an expression vector.

Such a construct may additionally include sequences that direct the HTL epitopes to the endoplasmic reticulum. For example, the Ii protein may be fused to one or more HTL epitopes as described in co-pending application U.S. Ser. No. 09/311,784 filed May 13, 1999, wherein the CLIP sequence of the Ii protein is removed and replaced with an HLA class II epitope sequence so that HLA class II epitope is directed to the endoplasmic reticulum, where the epitope binds to an HLA class II molecules.

This example illustrates the methods to be used for construction of a minigene-bearing expression plasmid. Other expression vectors that may be used for minigene compositions are available and known to those of skill in the art.

The minigene DNA plasmid of this example contains a consensus Kozak sequence and a consensus murine kappa Ig-light chain signal sequence followed by CTL and/or HTL epitopes selected in accordance with principles disclosed herein. The sequence encodes an open reading frame fused to the Myc and His antibody epitope tag coded for by the pcDNA 3.1 Myc-His vector.

Overlapping oligonucleotides that can, for example, average about 70 nucleotides in length with 15 nucleotide overlaps, are synthesized and HPLC-purified. The oligonucleotides encode the selected peptide epitopes as well as appropriate linker nucleotides, Kozak sequence, and signal sequence. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For example, a minigene can be prepared as follows. For a first PCR reaction, 5 µg of each of two oligonucleotides are annealed and extended: In an example using eight oligonucleotides, i.e., four pairs of primers, oligonucleotides 1+2, 3+4, 5+6, and 7+8 are combined in 100 µl reactions containing Pfu polymerase buffer (1×=10 mM KCL, 10 mM $(NH4)_2SO_4$, 20 mM Tris-chloride, pH 8.75, 2 mM $MgSO_4$, 0.1% Triton X-100, 100 µg/ml BSA), 0.25 mM each dNTP, and 2.5 U of Pfu polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product. The full-length product is gel-purified and cloned into pCR-blunt (Invitrogen) and individual clones are screened by sequencing.

Example 12

The Plasmid Construct and the Degree to which it Induces Immunogenicity

The degree to which a plasmid construct, for example a plasmid constructed in accordance with Example 11, is able to induce immunogenicity can be evaluated in vitro by testing for epitope presentation by APC following transduction or transfection of the APC with an epitope-expressing nucleic acid construct. Such a study determines "antigenicity" and allows the use of human APC. The assay determines the ability of the epitope to be presented by the APC in a context that is recognized by a T cell by quantifying the density of epitope-HLA class I complexes on the cell surface. Quantitation can be performed by directly measuring the amount of peptide eluted from the APC (see, e.g., Sijts et al., *J. Immunol.* 156:683–692, 1996; Demotz et al., *Nature* 342:682–684, 1989); or the number of peptide-HLA class I complexes can be estimated by measuring the amount of lysis or lymphokine release induced by infected or transfected target cells, and then determining the concentration of peptide necessary to obtained equivalent levels of lysis or lymphokine release (see, e.g., Kageyama et al., *J. Immunol.* 154:567–576, 1995).

Alternatively, immunogenicity can be evaluated through in vivo injections into mice and subsequent in vitro assessment of CTL and HTL activity, which are analysed using cytotoxicity and proliferation assays, respectively, as detailed e.g., in copending U.S. Ser. No. 09/311,784 filed May 13, 1999 and Alexander et al., *Immunity* 1:751–761, 1994.

For example, to assess the capacity of a DNA minigene construct (e.g., a pMin minigene construct generated as described in U.S. Ser. No. 09/311,784) containing at least one HLA-A2 supermotif peptide to induce CTLs in vivo, HLA-A2.1/K$^b$ transgenic mice, for example, are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide as they would be encoded by the minigene.

Splenocytes from immunized animals are stimulated twice with each of the respective compositions (peptide epitopes encoded in the minigene or the polyepitopic peptide), then assayed for peptide-specific cytotoxic activity in a $^{51}$Cr release assay. The results indicate the magnitude of the CTL response directed against the A2-restricted epitope, thus indicating the in vivo immunogenicity of the minigene vaccine and polyepitopic vaccine. It is, therefore, found that the minigene elicits immune responses directed toward the HLA-A2 supermotif peptide epitopes as does the poly-epitopic peptide vaccine. A similar analysis is also performed using other HLA-A3 and HLA-B7 transgenic mouse models to assess CTL induction by HLA-A3 and HLA-B7 motif or supermotif epitopes.

To assess the capacity of a class II epitope encoding minigene to induce HTLs in vivo, DR transgenic mice, or for those epitope that cross react with the appropriate mouse MHC molecule, I-A$^b$-restricted mice, for example, are immunized intramuscularly with 100 μg of plasmid DNA. As a means of comparing the level of HTLs induced by DNA immunization, a group of control animals is also immunized with an actual peptide composition emulsified in complete Freund's adjuvant. CD4+ T cells, i.e. HTLs, are purified from splenocytes of immunized animals and stimulated with each of the respective compositions (peptides encoded in the minigene). The HTL response is measured using a $^3$H-thymidine incorporation proliferation assay, (see, e.g., Alexander et al. Immunity 1:751–761, 1994). The results indicate the magnitude of the HTL response, thus demonstrating the in vivo immunogenicity of the minigene.

DNA minigenes, constructed as described in Example 11, may also be evaluated as a vaccine in combination with a boosting agent using a prime boost protocol. The boosting agent can consist of recombinant protein (e.g., Barnett et al., *Aids Res. and Human Retroviruses* 14, Supplement 3:S299–S309, 1998) or recombinant vaccinia, for example, expressing a minigene or DNA encoding the complete protein of interest (see, e.g., Hanke et al., *Vaccine* 16:439–445, 1998; Sedegah et al., *Proc. Natl. Acad. Sci USA* 95:7648–53, 1998; Hanke and McMichael, *Immunol. Letters* 66:177–181, 1999; and Robinson et al., *Nature Med.* 5:526–34, 1999).

For example, the efficacy of the DNA minigene used in a prime boost protocol is initially evaluated in transgenic mice. In this example, A2.1/K$^b$ transgenic mice are immunized IM with 100 μg of a DNA minigene encoding the immunogenic peptides including at least one HLA-A2 supermotif-bearing peptide. After an incubation period (ranging from 3–9 weeks), the mice are boosted IP with 10$^7$ pfu/mouse of a recombinant vaccinia virus expressing the same sequence encoded by the DNA minigene. Control mice are immunized with 100 μg of DNA or recombinant vaccinia without the minigene sequence, or with DNA encoding the minigene, but without the vaccinia boost. After an additional incubation period of two weeks, splenocytes from the mice are immediately assayed for peptide-specific activity in an ELISPOT assay. Additionally, splenocytes are stimulated in vitro with the A2-restricted peptide epitopes encoded in the minigene and recombinant vaccinia, then assayed for peptide-specific activity in an IFN-γ ELISA.

It is found that the minigene utilized in a prime-boost protocol elicits greater immune responses toward the HLA-A2 supermotif peptides than with DNA alone. Such an analysis can also be performed using HLA-A11 or HLA-B7 transgenic mouse models to assess CTL induction by HLA-A3 or HLA-B7 motif or supermotif epitopes.

The use of prime boost protocols in humans is described in Example 20.

Example 13

Peptide Composition for Prophylactic Uses

Vaccine compositions of the present invention can be used to prevent HPV infection in persons who are at risk for such infection. For example, a polyepitopic peptide epitope composition (or a nucleic acid comprising the same) containing multiple CTL and HTL epitopes such as those selected in Examples 9 and/or 10, which are also selected to target greater than 80% of the population, is administered to individuals at risk for HPV infection.

For example, a peptide-based composition can be provided as a single polypeptide that encompasses multiple epitopes. The vaccine is typically administered in a physiological solution that comprises an adjuvant, such as Incomplete Freunds Adjuvant. The dose of peptide for the initial immunization is from about 1 to about 50,000 μg, generally 100–5,000 μg, for a 70 kg patient. The initial administration of vaccine is followed by booster dosages at 4 weeks followed by evaluation of the magnitude of the immune response in the patient, by techniques that determine the presence of epitope-specific CTL populations in a PBMC sample. Additional booster doses are administered as required. The composition is found to be both safe and efficacious as a prophylaxis against HPV infection.

Alternatively, a composition typically comprising transfecting agents can be used for the administration of a nucleic acid-based vaccine in accordance with methodologies known in the art and disclosed herein.

Example 14

Polyepitopic Vaccine Compositions Derived from Native HPV Sequences

A native HPV polyprotein sequence is screened, preferably using computer algorithms defined for each class I and/or class II supermotif or motif, to identify "relatively short" regions of the polyprotein that comprise multiple epitopes and is preferably less in length than an entire native antigen. This relatively short sequence that contains multiple distinct,-even overlapping, epitopes is selected and used to generate a minigene construct. The construct is engineered to express the peptide, which corresponds to the native protein sequence. The "relatively short" peptide is generally less than 250 amino acids in length, often less than 100 amino acids in length, preferably less than 75 amino acids in length, and more preferably less than 50 amino acids in length. The protein sequence of the vaccine composition is selected because it has maximal number of epitopes contained within the sequence, i.e., it has a high concentration of epitopes. As noted herein, epitope motifs may be nested or overlapping (i.e., frame shifted relative to one another). For example, with f overlapping epitopes, two 9-mer epitopes and one 10-mer epitope can be present in a 10 amino acid peptide. Such a vaccine composition is administered for therapeutic or prophylactic purposes.

The vaccine composition will include, for example, three CTL epitopes from at least one HPV target antigen and at least one HTL epitope. This polyepitopic native sequence is administered either as a peptide or as a nucleic acid sequence which encodes the peptide. Alternatively, an analog can be made of this native sequence, whereby one or more of the epitopes comprise substitutions that alter the cross-reactivity and/or binding affinity properties of the polyepitopic peptide.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment (absent analogs) directs the immune response to multiple peptide sequences that are actually present in native HPV antigens thus avoiding the need to evaluate any junctional epitopes. Lastly, the embodiment provides an economy of scale when producing nucleic acid vaccine compositions.

Related to this embodiment, computer programs can be derived in accordance with principles in the art, which identify in a target sequence, the greatest number of epitopes per sequence length.

Example 15

Polyepitopic Vaccine Compositions from Multiple Antigens

The HPV peptide epitopes of the present invention are used in conjunction with peptide epitopes from other target tumor-associated antigens to create a vaccine composition that is useful for the prevention or treatment of cancer resulting from HPV infection in multiple patients.

For example, a vaccine composition can be provided as a single polypeptide that incorporates multiple epitopes from HPV antigens as well as other TAAs that are often expressed with a target cancer, e.g., cervical cancer, associated with HPV infection, or can be administered as a composition comprising one or more discrete epitopes. Alternatively, the vaccine can be administered as a minigene construct or as dendritic cells which have been loaded with the peptide epitopes in vitro.

Example 16

Use of Peptides to Evaluate an Immune Response

Peptides of the invention may be used to analyze an immune response for the presence of specific CTL or HTL populations directed to HPV. Such an analysis may be performed in a manner as that described by Ogg et al., Science 279:2103–2106, 1998. In the following example, peptides in accordance with the invention are used as a reagent for diagnostic or prognostic purposes, not as an immunogen.

In this example highly sensitive human leukocyte antigen tetrameric complexes ("tetramers") are used for a cross-sectional analysis of, for example, HPV HLA-A*0201-specific CTL frequencies from HLA A*0201-positive individuals at different stages of infection or following immunization using an HPV peptide containing an A*0201 motif. Tetrameric complexes are synthesized as described (Musey et al., N. Engl. J. Med. 337:1267, 1997). Briefly, purified HLA heavy chain (A*0201 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5'triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

For the analysis of patient blood samples, approximately one million PBMCs are centrifuged at 300 g for 5 minutes and resuspended in 50 µl of cold phosphate-buffered saline. Tri-color analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixation. Gates are applied to contain >99.98% of control samples. Controls for the tetramers include both A*0201-negative individuals and A*0201-positive uninfected donors. The percentage of cells stained with the tetramer is then determined by flow cytometry. The results indicate the number of cells in the PBMC sample that contain epitope-restricted CTLs, thereby readily indicating the extent of immune response to the HPV epitope, and thus the stage of infection with HPV, the status of exposure to HPV, or exposure to a vaccine that elicits a protective or therapeutic response.

Example 17

Use of Peptide Epitopes to Evaluate Recall Responses

The peptide epitopes of the invention are used as reagents to evaluate T cell responses, such as acute or recall responses, in patients. Such an analysis may be performed on patients who have recovered from infection, who are chronically infected with HPV, or who have been vaccinated with an HPV vaccine.

For example, the class I restricted CTL response of persons who have been vaccinated may be analyzed. The vaccine may be any HPV vaccine. PBMC are collected from vaccinated individuals and HLA typed. Appropriate peptide epitopes of the invention that, optimally, bear supermotifs to provide cross-reactivity with multiple HLA supertype family members, are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. A synthetic peptide comprising an epitope of the invention is added at 10 µg/ml to each well and HBV core 128–140 epitope is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 ml of complete RPMI and 20 U/ml final concentration of rIL-2 are added to each well. On day 7 the cultures are transferred into a 96-well flat-bottom plate and restimulated with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with uninfected control subjects as previously described (Rehermann, et al., Nature Med. 2:1104,1108, 1996; Rehermann et al., J. Clin. Invest. 97:1655–1665, 1996; and Rehermann et al. J. Clin. Invest. 98:1432–1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. J. Virol. 66:2670–2678, 1992).

Cytotoxicity assays are performed in the following manner. Target cells consist of either allogeneic HLA-matched or autologous EBV-transformed B lymphoblastoid cell line that are incubated overnight with the synthetic peptide epitope of the invention at 10 µM, and labeled with 100 µCi of $^{51}$Cr (Amershamn Corp., Arlington Heights, Ill.) for 1 hour after which they are washed four times with HBSS.

Cytolytic activity is determined in a standard 4-h, split well $^{51}$Cr release assay using U-bottomed 96 well plates containing 3,000 targets/well. Stimulated PBMC are tested at effector/target (E/T) ratios of 20–50:1 on day 14. Percent cytotoxicity is determined from the formula: 100× [(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis indicate the extent to which HLA-restricted CTL populations have been stimulated by previous exposure to HPV or an HPV vaccine.

The class II restricted HTL responses may also be analyzed. Purified PBMC are cultured in a 96-well flat bottom plate at a density of $1.5\times10^5$ cells/well and are stimulated with 10 µg/ml synthetic peptide, whole antigen, or PHA. Cells are routinely plated in replicates of 4–6 wells for each condition. After seven days of culture, the medium is removed and replaced with fresh medium containing 10 U/ml IL-2. Two days later, 1 µCi $^3$H-thymidine is added to each well and incubation is continued for an additional 18 hours. Cellular DNA is then harvested on glass fiber mats and analyzed for $^3$H-thymidine incorporation. Antigen-specific T cell proliferation is calculated as the ratio of $^3$H-thymidine incorporation in the presence of antigen divided by the $^3$H-thymidine incorporation in the absence of antigen.

Example 18

Induction of Specific CTL Response in Humans

A human clinical trial for an immunogenic composition comprising CTL and HTL epitopes of the invention is set up as an IND Phase I, dose escalation study and carried out as a randomized, double-blind, placebo-controlled trial. Such a trial is designed, for example, as follows:

A total of about 27 individuals are enrolled and divided into 3 groups:

Group I: 3 subjects are injected with placebo and 6 subjects are injected with 5 µg of peptide composition;

Group II: 3 subjects are injected with placebo and 6 subjects are injected with 50 µg peptide composition;

Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

The vaccine is found to be both safe and efficacious.

Example 19

Phase II Trials in Patients Infected with HPV

Phase II trials are performed to study the effect of administering the CTL-HTL peptide compositions to patients having cancer associated with HPV infection. The main objectives of the trials are to determine an effective dose and regimen for inducing CTLs in HPV-infected patients with cancer, to establish the safety of inducing a CTL and HTL response in these patients, and to see to what extent activation of CTLs improves the clinical picture of chronically infected HPV patients, as manifested by a reduction in viral load, e.g., the reduction and/or shrinking of lesions. Such a study is designed, for example, as follows:

The studies are performed in multiple centers. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects (severity and reversibility) are recorded.

There are three patient groupings. The first group is injected with 50 micrograms of the peptide composition and the second and third groups with 500 and 5,000 micrograms of peptide composition, respectively. The patients within each group range in age from 21–65 and represent diverse ethnic backgrounds. All of them are infected with HPV and are HIV, HCV, HBV and delta hepatitis virus (HDV) negative, but are positive for HPV DNA as monitered by PCR.

Clinical manifestations or antigen-specific T-cell responses are monitored to assess the effects of administering the peptide compositions. The vaccine composition is found to be both safe and efficacious in the treatment of HPV infection.

Example 20

Induction of CTL Responses Using a Prime Boost Protocol

A prime boost protocol similar in its underlying principle to that used to valuate the efficacy of a DNA vaccine in transgenic mice, such as described in Example 12, can also be used for the administration of the vaccine to humans. Such a vaccine regimen can include an initial administration of, for example, naked DNA followed by a boost using recombinant virus encoding the vaccine, or recombinant protein/polypeptide or a peptide mixture administered in an adjuvant.

For example, the initial immunization may be performed using an expression vector, such as that constructed in Example 11, in the form of naked nucleic acid administered IM (or SC or ID) in the amounts of 0.5–5 mg at multiple sites. The nucleic acid (0.1 to 1000 μg) can also be administered using a gene gun. Following an incubation period of 3–4 weeks, a booster dose is then administered. The booster can be recombinant fowlpox virus administered at a dose of $5$–$10^7$ to $5 \times 10^9$ pfu. An alternative recombinant virus, such as an MVA, canarypox, adenovirus, or adeno-associated virus, can also be used for the booster, or the polyepitopic protein or a mixture of the peptides can be administered. For evaluation of vaccine efficacy, patient blood samples will be obtained before immunization as well as at intervals following administration of the initial vaccine and booster doses of the vaccine. Peripheral blood mononuclear cells are isolated from fresh heparinized blood by Ficoll-Hypaque density gradient centrifugation, aliquoted in freezing media and stored frozen. Samples are assayed for CTL and HTL activity.

Analysis of the results indicates that a magnitude of response sufficient to achieve protective immunity against HPV is generated.

Example 21

Administration of Vaccine Compositions Using Dendritic Cells (DC)

Vaccines comprising peptide epitopes of the invention can be administered using APCs, or "professional" APCs such as DC. In this example, the peptide-pulsed DC are administered to a patient to stimulate a CTL response in vivo. In this method, dendritic cells are isolated, expanded, and pulsed with a vaccine comprising peptide CTL and HTL epitopes of the invention. The dendritic cells are infused back into the patient to elicit CTL and HTL responses in vivo. The induced CTL and HTL then destroy or facilitate destruction of the specific target cells that bear the proteins from which the epitopes in the vaccine are derived.

For example, a cocktail of epitope-bearing peptides is administered ex vivo to PBMC, or isolated DC therefrom. A pharmaceutical to facilitate harvesting of DC can be used, such as Progenipoietin™ (Monsanto, St. Louis, Mo.) or GM-CSF/IL-4. After pulsing the DC with peptides and prior to reinfusion into patients, the DC are washed to remove unbound peptides.

As appreciated clinically, and readily determined by one of skill based on clinical outcomes, the number of DC reinfused into the patient can vary (see, e.g., *Nature Med.* 4:328, 1998; *Nature Med.* 2:52, 1996 and *Prostate* 32:272, 1997). Although $2$–$50 \times 10^6$ DC per patient are typically administered, larger number of DC, such as $10^7$ or $10^8$ can also be provided. Such cell populations typically contain between 50–90% DC.

In some embodiments, peptide-loaded PBMC are injected into patients without purification of the DC. For example, PBMC containing DC generated after treatment with an agent such as Progenipoietin™ are injected into patients without purification of the DC. The total number of PBMC that are administered often ranges from $10^8$ to $10^{10}$. Generally, the cell doses injected into patients is based on the percentage of DC in the blood of each patient, as determined, for example, by immunofluorescence analysis with specific anti-DC antibodies. Thus, for example, if Progenipoietin™ mobilizes 2% DC in the peripheral blood of a given patient, and that patient is to receive $5 \times 10^6$ DC, then the patient will be injected with a total of $2.5 \times 10^8$ peptide-loaded PBMC. The percent DC mobilized by an agent such as Progenipoietimm is typically estimated to be between 2–10%, but can vary as appreciated by one of skill in the art.

Ex vivo Activation of CTL/HTL Responses

Alternatively, ex vivo CTL or HTL responses to HPV antigens can be induced by incubating in tissue culture the patient's, or genetically compatible, CTL or HTL precursor cells together with a source of APC, such as DC, and the appropriate immunogenic peptides. After an appropriate incubation time (typically about 7–28 days), in which the precursor cells are activated and expanded into effector cells, the cells are infused back into the patient, where they will destroy (CTL) or facilitate destruction (HTL) of their specific target cells, i.e., tumor cells.

Example 22

Alternative Method of Identifying Motif-bearing Peptides

Another method of identifying motif-bearing peptides is to elute them from cells bearing defined MHC molecules. For example, EBV transformed B cell lines used for tissue typing have been extensively characterized to determine which HLA molecules they express. In certain cases these cells express only a single type of HLA molecule. These cells can be infected with a pathogenic organism or transfected with nucleic acids that express the antigen of interest, e.g. HPV regulatory or structural proteins. Peptides produced by endogenous antigen processing of peptides produced consequent to infection (or as a result of transfection) will then bind to HLA molecules within the cell and be transported and displayed on the cell surface. Peptides are then eluted from the HLA molecules by exposure to mild acid conditions and their amino acid sequence determined, e.g., by mass spectral analysis (e.g., Kubo et at., *J. Immunol.* 152:3913, 1994). Because the majority of peptides that bind a particular HLA molecule are motif-bearing, this is an alternative modality for obtaining the motif-bearing peptides correlated with the particular HLA molecule expressed on the cell.

Alternatively, cell lines that do not express endogenous HLA molecules can be transfected with an expression construct encoding a single HLA allele. These cells can then be used as described, i.e., they can be infected with a pathogen or transfected with nucleic acid encoding an antigen of interest to isolate peptides corresponding to the pathogen or antigen of interest that have been presented on the cell surface. Peptides obtained from such an analysis will bear motif(s) that correspond to binding to the single HLA allele that is expressed in the cell.

As appreciated by one in the art, one can perform a similar analysis on a cell bearing more than one HLA allele and subsequently determine peptides specific for each HLA allele expressed. Moreover, one of skill would also recognize that means other than infection or transfection, such as loading with a protein antigen, can be used to provide a source of antigen to the cell.

The above examples are provided to illustrate the invention but not to limit its scope. For example, the human terminology for the Major Histocompatibility Complex, namely HLA, is used throughout this document. It is to be appreciated that these principles can be extended to other species as well. Thus, other variants of the invention will be readily apparent to one of ordinary skill in the art and are encompassed by the appended claims. All publications, patents, and patent application cited herein are hereby incorporated by reference for all purposes.

TABLE I

|  | POSITION 2 (Primary Anchor) | POSITION 3 (Primary Anchor) | POSITION C Terminus (Primary Anchor) |
|---|---|---|---|
| SUPERMOTIFS |  |  |  |
| A1 | T, I, L, V, M, S |  | F, W, Y |
| A2 | L, I, V, M, A, T, Q |  | I, V, M, A, T, L |
| A3 | V, S, M, A, T, L, I |  | R, K |
| A24 | Y, F, W, I, V, L, M, T |  | F, I, Y, W, L, M |
| B7 | P |  | V, I, L, F, M, W, Y, A |
| B27 | R, H, K |  | F, Y, L, W, M, I, V, A |
| B44 | E, D |  | F, W, L, I, M, V, A |
| B58 | A, T, S |  | F, W, Y, L, I, V, M, A |
| B62 | Q, L, I, V, M, P |  | F, W, Y, M, I, V, L, A |
| MOTIFS |  |  |  |
| A1 | T, S, M |  | Y |
| A1 |  | D, E, A, S | Y |
| A2.1 | L, M, V, Q, I, A, T |  | V, L, I, M, A, T |
| A3 | L, M, V, I, S, A, T, F, C, G, D |  | K, Y, R, H, F, A |
| A11 | V, T, M, L, I, S, A, G, N, C, D, F |  | K, R, Y, H |
| A24 | Y, F, W, M |  | F, L, I, W |
| A*3101 | M, V, T, A, L, I, S |  | R, K |
| A*3301 | M, V, A, L, F, I, S, T |  | R, K |
| A*6801 | A, V, T, M, S, L, I |  | R, K |
| B*0702 | P |  | L, M, F, W, Y, A, I, V |
| B*3501 | P |  | L, M, F, W, Y, I, V, A |
| B51 | P |  | L, I, V, F, W, Y, A, M |
| B*5301 | P |  | I, M, F, W, Y, A, L, V |
| B*5401 | P |  | A, T, I, V, L, M, F, W, Y |

Bolded residues are preferred, italicized residues are less preferred: A peptide is considered motif-bearing if it has primary anchors at each primary anchor position for a motif or supermotif as specified in the above table.

TABLE Ia

|  | POSITION 2 (Primary Anchor) | POSITION 3 (Primary Anchor) | POSITION C Terminus (Primary Anchor) |
|---|---|---|---|
| SUPERMOTIFS |  |  |  |
| A1 | T, I, L, V, M, S |  | F, W, Y |
| A2 | V, Q, A, T |  | I, V, L, M, A, T |
| A3 | V, S, M, A, T, L, I |  | R, K |
| A24 | Y, F, W, I, V, L, M, T |  | F, I, Y, W, L, M |
| B7 | P |  | V, I, L, F, M, W, Y, A |
| B27 | R, H, K |  | F, Y, L, W, M, I, V, A |
| B58 | A, T, S |  | F, W, Y, L, I, V, M, A |
| B62 | Q, L, I, V, M, P |  | F, W, Y, M, I, V, L, A |
| MOTIFS |  |  |  |
| A1 | T, S, M |  | Y |
| A1 |  | D, E, A, S | Y |
| A2.1 | V, Q, A, T* |  | V, L, I, M, A, T |
| A3.2 | L, M, V, I, S, A, T, F, C, G, D |  | K, Y, R, H, F, A |
| A11 | V, T, M, L, I, S, A, G, N, C, D, F |  | K, R, H, Y |
| A24 | Y, F, W |  | F, L, I, W |

*If 2 is V, or Q, the C-term is not L
Bolded residues are preferred, italicized residues are less preferred: A peptide is considered motif-bearing if it has primary anchors at each primary anchor position for a motif or supermotif as specified in the above table.

TABLE II

| | | 1 | 2 | 3 | 4 | 5 | 6 | 7 | 8 | C-terminus |
|---|---|---|---|---|---|---|---|---|---|---|
| SUPERMOTIFS | | | | | | | | | | |
| A1 | | | 1°Anchor T, I, L, *V, M, S* | | | | | | | 1°Anchor F, W, Y |
| A2 | | | 1°Anchor L, I, V, M, *A, T, Q* | | | | | | | 1°Anchor L, I, V, M, A, T |
| A3 | preferred | | 1°Anchor V, S, M, A, *T, L, I* | Y, F, W, (4/5) | | | Y, F, W, (3/5) | Y, F, W, (4/5) | P, (4/5) | 1°Anchor R, K |
| | deleterious | D, E (3/5); P, (5/5) | | D, E, (4/5) | | | | | | |
| A24 | preferred | | 1°Anchor Y, F, *W, I, V, L, M, T* | | | | | | | 1°Anchor F, I, *Y, W, L, M* |
| B7 | preferred | F, W, Y (5/5) L, I, V, M, (3/5) | 1°Anchor P | F, W, Y, (4/5) | | | | | F, W, Y, (3/5) | 1°Anchor V, I, L, F, *M, W, Y, A* |
| | deleterious | D, E (3/5); P(5/5); G(4/5); A(3/5); Q, N, (3/5) | | | | D, E, (3/5) | G, (4/5) | Q, N, (4/5) | D, E (4/5) | |
| B27 | | | 1°Anchor R, H, K | | | | | | | 1°Anchor F, Y, L, *W, M, V, A* |
| B44 | | | 1°Anchor E, *D* | | | | | | | 1°Anchor F, W, Y, L, I, M, V, A |
| B58 | | | 1°Anchor A, T, S | | | | | | | 1°Anchor F, W, Y, L, I, V, M, A |
| B62 | | | 1°Anchor Q, L, I, V, M, P | | | | | | | 1°Anchor F, W, Y, M, I, V, L, A |
| MOTIFS | | | | | | | | | | |
| A1 9-mer | preferred | G, F, Y, W, | 1°Anchor S, T, M, | D, E, A, | Y, F, W, | | P, | D, E, Q, N, | Y, F, W, | 1°Anchor Y |
| | deleterious | D, E, | | R, H, K, L, I, V M, P, | A, | G, | A, | | | |
| A1 9-mer | preferred | G, R, H, K | A, S, T, C, L, I V, M, | 1°Anchor D, E, *A, S* | G, S, T, C, | | A, S, T, C, | L, I, V, M, | D, E, | 1°Anchor Y |
| | deleterious | A | R, H, K, D, E, P, Y, F, W, | | D, E, | P, Q, N, | R, H, K, | P, G, | G, P, | |

TABLE II-continued

| | | 1 | 2 | 3 | 4 | 5 | 6 | 7 | 8 | 9 or C-terminus | C-terminus |
|---|---|---|---|---|---|---|---|---|---|---|---|
| A1 10-mer | preferred | Y, F, W, | 1°Anchor S, T, M | D, E, A, Q, N, | A, | Y, F, W, Q, N, | | P, A, S, T, C, | G, D, E, | P, | 1°Anchor Y |
| | deleterious | G, P, | | R, H, K, G, L, I | D, E | R, H, K, | Q, N, A | R, H, K, Y, F, W, | R, H, K, | A | |
| A1 10-mer | preferred | Y, F, W, | S, T, C, L, I, V, M, | 1°Anchor D, E, A, S | A, | Y, F, W, | | P, G, | G, | Y, F, W, | 1°Anchor Y |
| | deleterious | R, H, K, | R, H, K, D, E, P, Y, F, W, | | S, T, C, | P, | G, | | P, R, H, K, | Q, N, | |
| A2.1 9-mer | preferred | Y, F, W, | 1°Anchor L, M, I, V, Q, A, T | Y, F, W, | S, T, C, | Y, F, W, | | A, | P, | 1°Anchor V, L, I, M, A, T | |
| A2.1 10-mer | deleterious | D, E, R, K, H | | | | | | | | | |
| | preferred | A, Y, F, W, | 1°Anchor L, M, I, V, Q, A, T | D, E, R, K, H L, V, I, M, | G, | | R, K, H G, | D, E, R, K, H | F, Y, W, L, V, I, M, | | 1°Anchor V, L, I, M, A, T |
| | deleterious | D, E, P, | | D, E, | R, K, H, A, | P, | | R, K, H, | D, E, R, K, H | | |
| A3 | preferred | R, H, K, | 1°Anchor L, M, V, I, S, A, T, F, C, G, D | Y, F, W, | P, R, H, K, Y, F, W, | A, | Y, F, W, | | P, | 1°Anchor K, Y, R, H, F, A | |
| A11 | deleterious | D, E, P, | | D, E Y, F, W, | | | | | | | |
| | preferred | A, | 1°Anchor V, T, L, M, I, S, A, G, N, C, D, F | | Y, FW, | A, | Y, F, W, | Y, FW, | P, | 1°Anchor K,, RY, H | |
| A24 9-mer | deleterious | D, E, P, | | | | | | A Y, F, W, | G, Y, F, W, | 1°Anchor F, L, I, W | |
| | preferred | Y, F, W, R, H, K, | 1°Anchor Y, F, W, M | | S, T, C | Q, N, P, Y, F, W, P, | D, E, R, H, K, | G, P, | A, Q, N, | | |
| A24 10-mer | deleterious | D, E, G, | 1°Anchor Y, F, W, M | D, E, | G, P, | | | | | | 1°Anchor F, L, I, W |
| | preferred | R, H, K, | 1°Anchor M, V, T, A, L, I, S | G, D, E Y, F, W, | Q, N P, | R, H, K | D, E Y, F, W, | A Y, F, W, | Q, N, A, P, | D, E, A, 1°Anchor R, K | |
| A3101 | deleterious | D, E, P, | | D, E, | | A, D, E, | D, E, | D, E, | D, E, | | |

TABLE II-continued

| | | | | | | | | | |
|---|---|---|---|---|---|---|---|---|---|
| A3301 | preferred | 1°Anchor M, V, A, L, F, I, S, T | Y, F, W | | | | | | A, Y, F, W | 1°Anchor R, K |
| | deleterious | G, P | | | | | | | | |
| A6801 | preferred | Y, F, W, S, T, C | 1°Anchor A, V, T, M, S, L, I | D, E | | Y, F, W, L, I, V, M | R, H, K | | Y, F, W, | 1°Anchor R, K |
| | deleterious | G, P | | | | R, H, K | | | P, | |
| B0702 | preferred | R, H, K, F, W, Y | 1°Anchor P | D, E, G, R, H, K | | R, H, K | R, H, K | | R, H, K | 1°Anchor L, M, F, W, Y, A, I, V |
| | deleterious | | | | | | | | A, P, A, | |
| B3501 | preferred | D, E, Q, N, P, F, W, Y, L, I, V, M | 1°Anchor P | D, E, P, F, W, Y | D, E | D, E | G, D, E | | Q, N, F, W, Y | 1°Anchor L, M, F, W, Y, I, V, A |
| | deleterious | | | | | | | | D, E | |
| B51 | preferred | A, G, P, L, I, V, M, F, W, Y | 1°Anchor P | F, W, Y | S, T, C | G, F, W, Y | G, | | G, | 1°Anchor L, I, V, F, W, Y, A, M |
| | deleterious | A, G, P, D, E, R, H, K, S, T, C | | | | | | | F, W, Y, | |
| B5301 | preferred | L, I, V, M, F, W, Y | 1°Anchor P | F, W, Y | S, T, C | F, W, Y | G, | | D, E, Q, N, | 1°Anchor I, M, F, W, Y, A, L, V |
| | deleterious | | | | | | | | G, D, E, | |
| B5401 | preferred | A, G, P, Q, N, F, W, Y | 1°Anchor P | F, W, Y, L, I, V, M | | L, I, V, M | G, | | L, I, V, M, F, W, Y, | 1°Anchor A, T, I, V, L, M, F, W, Y |
| | deleterious | | | | | | | | R, H, K, Q, N, D, E, F, W, Y, A, P, | |
| | deleterious | G, P, Q, N, D, E | | G, D, E, S, T, C | | R, H, K, D, E | D, E | | Q, N, D, G, E, | D, E |

Italicized residues indicate less preferred or "tolerated" residues.
The information in Table II is specific for 9-mers unless otherwise specified.
Secondary anchor specificities are designated for each position independently.

TABLE III

| SEQ ID NO: | MOTIFS | | 1° anchor 1 | 2 | 3 | 4 | 5 | 1° anchor 6 | 7 | 8 | 9 |
|---|---|---|---|---|---|---|---|---|---|---|---|
| | DR4 | preferred | F, M, Y, *L, I, V, W,* | M, T, | | | I, | V, S, T, *C, P, A, L, I, M,* | M, H, | | M, H |
| | | deleterious | | | | W, | | | R, | | W, D, E |
| | DR1 | preferred | M, F, *L, I, V, W, Y,* | | | P, A, M, Q, | | V, M, A, T, *S, P, L, I, C,* | M, | | A, V, M |
| | | deleterious | | C | C, H | F, D | C, W, D | | G, D, E, | D | |
| 51503 | DR7 | preferred | M, F, *L, I, V, W, Y,* | M, W, | | A, | | I, V, M, S, A, *C, T, P, L,* | M, | | I,V |
| 51504 | | deleterious | | C, | | G, | | | G, R, D, | N | G |
| | DR | Supermotif | M, F, *L, I, V, W, Y,* | | | | | V, M, S, T, A, *C, P, L, I,* | | | |

| | | 1° anchor 1 | 2 | 3 | 1° anchor 4 | 5 | 1° anchor 6 |
|---|---|---|---|---|---|---|---|
| DR3 MOTIFS | | | | | | | |
| motif a | preferred | L, I, V, M, F, Y, | | | D | | |
| motif b | preferred | L, I, V, M, F, A, Y, | | | D, N, Q, E, S, T | | K, R, H |

Italicized reidues indicate less preferred or "tolerated" residues. Secondary anchor specificities are designated for each position independently.

TABLE IV

HLA Class I Standard Peptide Binding Affinity.

| ALLELE | STANDARD PEPTIDE | SEQUENCE | SEQ ID NO: | STANDARD BINDING AFFINITY (nM) |
|---|---|---|---|---|
| A*0101 | 944.02 | YLEPAIAKY | 51487 | 25 |
| A*0201 | 941.01 | FLPSDYFPSV | 51488 | 5.0 |
| A*0202 | 941.01 | FLPSDYFPSV | 51488 | 4.3 |
| A*0203 | 941.01 | FLPSDYFPSV | 51488 | 10 |
| A*0205 | 941.01 | FLPSDYFPSV | 51488 | 4.3 |
| A*0206 | 941.01 | FLPSDYFPSV | 51488 | 3.7 |
| A*0207 | 941.01 | FLPSDYFPSV | 51488 | 23 |
| A*6802 | 1072.34 | YVIKVSARV | 51489 | 8.0 |
| A*0301 | 941.12 | KVFPYALINK | 51490 | 11 |
| A*1101 | 940.06 | AVDLYHFLK | 51491 | 6.0 |
| A*3101 | 941.12 | KVFPYALINK | 51490 | 18 |
| A*3301 | 1083.02 | STLPETYVVRR | 51492 | 29 |
| A*6801 | 941.12 | KVFPYALINK | 51490 | 8.0 |
| A*2402 | 979.02 | AYIDNYNKF | 51493 | 12 |
| B*0702 | 1075.23 | APRTLVYLL | 51494 | 5.5 |
| B*3501 | 1021.05 | FPFKYAAAF | 51495 | 7.2 |
| B51 | 1021.05 | FPFKYAAAF | 51495 | 5.5 |
| B*5301 | 1021.05 | FPFKYAAAF | 51495 | 9.3 |
| B*5401 | 1021.05 | FPFKYAAAF | 51495 | 10 |

TABLE V

HLA Class II Standard Peptide Binding Affinity.

| Allele | Nomenclature | Standard Peptide | Sequence | SEQ ID NO: | Binding Affinity (nM) |
|---|---|---|---|---|---|
| DRB1*0101 | DR1 | 515.01 | PKYVKQNTLKLAT | 51496 | 5.0 |
| DRB1*0301 | DR3 | 829.02 | YKTIAFDEEARR | 51497 | 300 |
| DRB1*0401 | DR4w4 | 515.01 | PKYVKQNTLKLAT | 51496 | 45 |
| DRB1*0404 | DR4w14 | 717.01 | YARFQSQTTLKQKT | 51498 | 50 |
| DRB1*0405 | DR4w15 | 717.01 | YARFQSQTTLKQKT | 51498 | 38 |
| DRB1*0701 | DR7 | 553.01 | QYIKANSKFIGITE | 51499 | 25 |
| DRB1*0802 | DR8w2 | 553.01 | QYIKANSKFIGITE | 51499 | 49 |
| DRB1*0803 | DR8w3 | 553.01 | QYIKANSKFIGITE | 51499 | 1600 |
| DRB1*0901 | DR9 | 553.01 | QYIKANSKFIGITE | 51499 | 75 |
| DRB1*1101 | DR5w11 | 553.01 | QYIKANSKFIGITE | 51499 | 20 |
| DRB1*1201 | DR5w12 | 1200.05 | EALIHQLKINPYVLS | 51500 | 298 |
| DRB1*1302 | DR6w19 | 650.22 | QYIKANAKFIGITE | 51499 | 3.5 |
| DRB1*1501 | DR2w2β1 | 507.02 | GRTQDENPVVHFFKNIVTPRTPPP | 51501 | 9.1 |

TABLE V-continued

HLA Class II Standard Peptide Binding Affinity.

| Allele | Nomenclature | Standard Peptide | Sequence | SEQ ID NO: | Binding Affinity (nM) |
|---|---|---|---|---|---|
| DRB3*0101 | DR52a | 511 | NGQIGNDPNRDIL | 51502 | 470 |
| DRB4*0101 | DRw53 | 717.01 | YARFQSQTTLKQKT | 51498 | 58 |
| DRB5*0101 | DR2w2β2 | 553.01 | QYIKANSKFIGITE | 51499 | 20 |

TABLE VI

Allele-specific HLA-supertype members

| HLA-supertype | Verified[a] | Predicted[b] |
|---|---|---|
| A1 | A*0101, A*2501, A*2601, A*2602, A*3201 | A*0102, A*2604, A*3601, A*4301, A*8001 |
| A2 | A*0201, A*0202, A*0203, A*0204, A*0205, A*0206, A*0207, A*209, A*0214, A*6802, A*6901 | A*0208, A*0210, A*0211, A*0212, A*0213 |
| A3 | A*0301, A*1101, A*3101, A*3301, A*6801 | A*0302, A*1102, A*2603, A*3302, A*3303, A*3401, A*3402, A*6601, A*6602, A*7401 |
| A24 | A*2301, A*2402, A*3001 | A*2403, A*2404, A*3002, A*3003 |
| B7 | B*0702, B*0703, B*0704, B*0705, B*1508, B*3501, B*3502, B*3503, B*3503, B*3504, B*3505, B*3506, B*3507, B*3508, B*5101, B*5102 B*5103, B*5104, B*5105, B*5301, B*5401, B*5501, B*5502, B*5601, B*5602, B*6701, B*7801 | |
| B27 | B*1401, B*1402, B*1509, B*2702, B*2703, B*2704, B*2705, B*2706, B*3801, B*3901, B*3902, B*7301 | B*2701, B*2707, B*2708, B*3802, B*3903, B*3904, B*3905, B*4801, B*4802, B*1510, B*1518, B*1503 |
| B44 | B*1801, B*1802, B*3701, B*4402, B*4403, B*4404, B*4001, B*4002, B*4006 | B*4101, B*4501, B*4701, B*4901, B*5001 |
| B58 | B*5701, B*5702, B*5801, B*5802, B*1516, B*1517 | |
| B62 | B*1501, B*1502, B*1513, B*5201 | B*1301, B*1302, B*1504, B*1505, B*1506, B*1507, B*1515, B*1520, B*1521, B*1512, B*1514, B*1510 |

[a] Verified alleles include alleles whose specificity has been determined by pool sequencing analysis, peptide binding assays, or by analysis of the sequences of CTL epitopes.
[b] Predicted alleles are alleles whose specificity is predicted on the basis of B and F pocket structure to overlap with the supertype specificity.

TABLE VII

A01 Supermotif Peptides

| Type | Protein | Position | No. of Amino Acids | Sequence | A*0101 | Seq. Id. No. |
|---|---|---|---|---|---|---|
| HPV16 | E1 | 206 | 10 | AMLAKFKELY | | 1 |
| HPV16 | E1 | 524 | 8 | ATVPCWNY | | 2 |
| HPV16 | E1 | 82 | 9 | AVQVLKRKY | | 3 |
| HPV16 | E1 | 353 | 11 | CTFELSQMVQW | | 4 |
| HPV16 | E1 | 368 | 10 | DIVDDSEIAY | | 5 |
| HPV16 | E1 | 41 | 11 | DSDTGEDLVDF | | 6 |
| HPV16 | E1 | 372 | 8 | DSEIAYKY | | 7 |
| HPV16 | E1 | 249 | 10 | DSIKTLLQQY | | 8 |
| HPV16 | E1 | 43 | 9 | DTGEDLVDF | | 9 |
| HPV16 | E1 | 384 | 9 | DTNSNASAF | | 10 |
| HPV16 | E1 | 603 | 10 | ELNDKNWKSF | | 11- |
| HPV16 | E1 | 603 | 11 | ELNDKNWKSFF | | 12 |
| HPV16 | E1 | 356 | 8 | ELSQMVQW | | 13 |
| HPV16 | E1 | 356 | 10 | ELSQMVQWAY | | 14 |
| HPV16 | E1 | 63 | 9 | ETETAHALF | | 15 |
| HPV16 | E1 | 152 | 9 | ETETPCSQY | | 16 |
| HPV16 | E1 | 331 | 9 | EVYGDTPEW | | 17 |
| HPV16 | E1 | 51 | 8 | FIVNDNDY | | 18 |
| HPV16 | E1 | 493 | 9 | FLQGSVICF | | 19 |
| HPV16 | E1 | 445 | 9 | FLRYQGVEF | | 20 |
| HPV16 | E1 | 456 | 8 | FLTALKRF | | 21 |
| HPV16 | E1 | 453 | 11 | FMSFLTALKRF | | 22 |
| HPV16 | E1 | 219 | 8 | FSELVRPF | | 23 |
| HPV16 | E1 | 586 | 9 | FTFPNEFPF | | 24 |
| HPV16 | E1 | 501 | 8 | FVNSKSHF | | 25 |
| HPV16 | E1 | 501 | 9 | FVNSKSHFW | | 26 |
| HPV16 | E1 | 466 | 11 | GIPKKNCILLY | | 27 |
| HPV16 | E1 | 325 | 9 | GISNISEVY | | 28 |
| HPV16 | E1 | 519 | 11 | GMLDDATVPCW | | 29 |

TABLE VII-continued

A01 Supermotif Peptides

| Type | Protein | Position | No. of Amino Acids | Sequence | A*0101 | Seq. Id. No. |
|---|---|---|---|---|---|---|
| HPV16 | E1 | 272 | 10 | GMVVLLLVRY | | 30 |
| HPV16 | E1 | 163 | 9 | GSGGGCSQY | | 31 |
| HPV16 | E1 | 571 | 8 | GTDSRWPY | | 32 |
| HPV16 | E1 | 12 | 8 | GTGCNGWF | | 33 |
| HPV16 | E1 | 12 | 9 | GTGCNGWFY | 3.9000 | 34 |
| HPV16 | E1 | 216 | 11 | GVSFSELVRPF | | 35 |
| HPV16 | E1 | 263 | 9 | HIQSLACSW | | 36 |
| HPV16 | E1 | 348 | 8 | HSFNDCTF | | 37 |
| HPV16 | E1 | 329 | 11 | ISEVYGDTPEW | | 38 |
| HPV16 | E1 | 326 | 8 | ISNISEVY | | 39 |
| HPV16 | E1 | 369 | 9 | IVDDSEIAY | | 40 |
| HPV16 | E1 | 369 | 11 | IVDDSEIAYKY | | 41 |
| HPV16 | E1 | 311 | 10 | KLRSTAAALY | | 42 |
| HPV16 | E1 | 311 | 11 | KLRSTAAALYW | | 43 |
| HPV16 | E1 | 610 | 8 | KSFFSRTW | | 44 |
| HPV16 | E1 | 483 | 11 | KSLFGMSLMKF | | 45 |
| HPV16 | E1 | 227 | 10 | KSNKSTCCDW | | 46 |
| HPV16 | E1 | 323 | 11 | KTGISNISEVY | | 47 |
| HPV16 | E1 | 252 | 10 | KTLLQQYCLY | | 48 |
| HPV16 | E1 | 254 | 8 | LLQQYCLY | | 49 |
| HPV16 | E1 | 357 | 9 | LSQMVQWAY | | 50 |
| HPV16 | E1 | 48 | 11 | LVDFIVNDNDY | | 51 |
| HPV16 | E1 | 583 | 10 | LVVFTFPNEF | | 52 |
| HPV16 | E1 | 207 | 9 | MLAKFKELY | | 53 |
| HPV16 | E1 | 520 | 10 | MLDDATVPCW | | 54 |
| HPV16 | E1 | 454 | 10 | MSFLTALKRF | | 55 |
| HPV16 | E1 | 420 | 9 | MSMSQWIKY | | 56 |
| HPV16 | E1 | 273 | 9 | MVVLLLVRY | | 57 |
| HPV16 | E1 | 567 | 10 | NINAGTDSRW | | 58 |
| HPV16 | E1 | 600 | 10 | PVYELNDKNW | | 59 |
| HPV16 | E1 | 441 | 8 | QIVMFLRY | | 60 |
| HPV16 | E1 | 419 | 10 | QMSMSQWIKY | | 61 |
| HPV16 | E1 | 118 | 10 | QSRAAKRRLF | | 62 |
| HPV16 | E1 | 343 | 8 | QTVLQHSF | | 63 |
| HPV16 | E1 | 125 | 10 | RLFESEDSGY | | 64 |
| HPV16 | E1 | 582 | 11 | RLVVFTFPNEF | | 65 |
| HPV16 | E1 | 313 | 8 | RSTAAALY | | 66 |
| HPV16 | E1 | 313 | 9 | RSTAAALYW | | 67 |
| HPV16 | E1 | 313 | 10 | RSTAAALYWY | | 68 |
| HPV16 | E1 | 432 | 8 | RVDDGGDW | | 69 |
| HPV16 | E1 | 250 | 9 | SIKTLLQQY | | 70 |
| HPV16 | E1 | 484 | 10 | SLFGMSLMKF | | 71 |
| HPV16 | E1 | 421 | 8 | SMSQWIKY | | 72 |
| HPV16 | E1 | 314 | 8 | STAAALYW | | 73 |
| HPV16 | E1 | 314 | 9 | STAAALYWY | | 74 |
| HPV16 | E1 | 231 | 11 | STCCDWCIAAF | | 75 |
| HPV16 | E1 | 253 | 9 | TLLQQYCLY | | 76 |
| HPV16 | E1 | 498 | 11 | VICFVNSKSHF | | 77 |
| HPV16 | E1 | 345 | 11 | VLQHSFNDCTF | | 78 |
| HPV16 | E1 | 443 | 11 | VMFLRYQGVEF | | 79 |
| HPV16 | E1 | 217 | 10 | VSFSELVRPF | | 80 |
| HPV16 | E1 | 584 | 9 | VVFTFPNEF | | 81 |
| HPV16 | E1 | 584 | 11 | VVFTFPNEFPF | | 82 |
| HPV16 | E1 | 274 | 8 | VVLLLVRY | | 83 |
| HPV16 | E1 | 261 | 11 | YLHIQSLACSW | | 84 |
| HPV16 | E1 | 578 | 9 | YLHNRLVVF | | 85 |
| HPV16 | E1 | 578 | 11 | YLHNRLVVFTF | | 86 |
| HPV16 | E2 | 331 | 11 | AIVTLTYDSEW | | 87 |
| HPV16 | E2 | 41 | 11 | AIYYKAREMGF | | 88 |
| HPV16 | E2 | 314 | 8 | AVSSTWHW | | 89 |
| HPV16 | E2 | 309 | 11 | CTLYTAVSSTW | | 90 |
| HPV16 | E2 | 124 | 8 | DICNTMHY | | 91 |
| HPV16 | E2 | 124 | 11 | DICNTMHYTNW | | 92 |
| HPV16 | E2 | 25 | 8 | DLRDHIDY | | 93 |
| HPV16 | E2 | 25 | 9 | DLRDHIDYW | | 94 |
| HPV16 | E2 | 263 | 9 | DSAPILTAF | | 95 |
| HPV16 | E2 | 338 | 9 | DSEWQRDQF | | 96 |
| HPV16 | E2 | 22 | 11 | DSTDLRDHIDY | | 97 |
| HPV16 | E2 | 74 | 10 | ELQLTLETIY | | 98 |
| HPV16 | E2 | 80 | 8 | ETIYNSQY | | 99 |
| HPV16 | E2 | 168 | 11 | FVQFKDDAEKY | | 100 |
| HPV16 | E2 | 163 | 9 | GIRTYFVQF | | 101 |
| HPV16 | E2 | 35 | 9 | HMRLECAIY | | 102 |
| HPV16 | E2 | 35 | 10 | HMRLECAIYY | | 103 |

TABLE VII-continued

A01 Supermotif Peptides

| Type | Protein | Position | No. of Amino Acids | Sequence | A*0101 | Seq. Id. No. |
|---|---|---|---|---|---|---|
| HPV16 | E2 | 193 | 8 | ILCPTSVF | | 104 |
| HPV16 | E2 | 332 | 10 | IVTLTYDSEW | | 105 |
| HPV16 | E2 | 329 | 9 | KSAIVTLTY | | 106 |
| HPV16 | E2 | 354 | 9 | KTITVSTGF | | 107 |
| HPV16 | E2 | 77 | 11 | LTLETIYNSQY | | 108 |
| HPV16 | E2 | 84 | 9 | NSQYSNEKW | | 109 |
| HPV16 | E2 | 296 | 8 | NTLKCLRY | | 110 |
| HPV16 | E2 | 296 | 10 | NTLKCLRYRF | | 111 |
| HPV16 | E2 | 127 | 8 | NTMHYTNW | | 112 |
| HPV16 | E2 | 9 | 11 | NVCQDKILTHY | | 113 |
| HPV16 | E2 | 106 | 10 | PTGCIKKHGY | | 114 |
| HPV16 | E2 | 76 | 8 | QLTLETIY | | 115 |
| HPV16 | E2 | 151 | 8 | QVDYYGLY | | 116 |
| HPV16 | E2 | 151 | 9 | QVDYYGLYY | | 117 |
| HPV16 | E2 | 191 | 10 | QVILCPTSVF | | 118 |
| HPV16 | E2 | 37 | 8 | RLECAIYY | | 119 |
| HPV16 | E2 | 23 | 10 | STDLRDHIDY | | 120 |
| HPV16 | E2 | 23 | 11 | STDLRDHIDYW | | 121 |
| HPV16 | E2 | 261 | 11 | SVDSAPILTAF | | 122 |
| HPV16 | E2 | 144 | 11 | SVTTVEGQVDY | | 123 |
| HPV16 | E2 | 355 | 8 | TITVSTGF | | 124 |
| HPV16 | E2 | 78 | 10 | TLETIYNSQY | | 125 |
| HPV16 | E2 | 297 | 9 | TLKCLRYRF | | 126 |
| HPV16 | E2 | 93 | 10 | TLQDVSLEVY | | 127 |
| HPV16 | E2 | 334 | 8 | TLTYDSEW | | 128 |
| HPV16 | E2 | 310 | 10 | TLYTAVSSTW | | 129 |
| HPV16 | E2 | 128 | 11 | TMHYTNWTHIY | | 130 |
| HPV16 | E2 | 146 | 9 | TVVEGQVDY | | 131 |
| HPV16 | E2 | 146 | 10 | TVVEGQVDYY | | 132 |
| HPV16 | E2 | 192 | 9 | VILCPTSVF | | 133 |
| HPV16 | E2 | 333 | 9 | VTLTYDSEW | | 134 |
| HPV16 | E2 | 145 | 10 | VTVVEGQVDY | | 135 |
| HPV16 | E2 | 145 | 11 | VTVVEGQVDYY | | 136 |
| HPV16 | E2 | 147 | 8 | VVEGQVDY | | 137 |
| HPV16 | E2 | 147 | 9 | VVEGQVDYY | | 138 |
| HPV16 | E2 | 92 | 11 | WTLQDVSLEVY | | 139 |
| HPV16 | E2 | 312 | 8 | YTAVSSTW | | 140 |
| HPV16 | E2 | 312 | 10 | YTAVSSTWHW | | 141 |
| HPV16 | E2 | 131 | 8 | YTNWTHIY | | 142 |
| HPV16 | E2 | 159 | 9 | YVHEGIRTY | | 143 |
| HPV16 | E2 | 159 | 10 | YVHEGIRTYF | | 144 |
| HPV16 | E5 | 54 | 10 | ASAFRCFIVY | | 145 |
| HPV16 | E5 | 7 | 9 | ASTTLLACF | | 146 |
| HPV16 | E5 | 5 | 11 | DTASTTLLACF | | 147 |
| HPV16 | E5 | 60 | 9 | FIVYIIFVY | | 148 |
| HPV16 | E5 | 72 | 9 | FLIHTHARF | | 149 |
| HPV16 | E5 | 64 | 9 | IIFVYIPLF | | 150 |
| HPV16 | E5 | 43 | 8 | IILVLLLW | | 151 |
| HPV16 | E5 | 51 | 10 | ITAASAFRCF | | 152 |
| HPV16 | E5 | 61 | 8 | IVYIIFVY | | 153 |
| HPV16 | E5 | 73 | 8 | LIHTHARF | | 154 |
| HPV16 | E5 | 42 | 9 | LIILVLLLW | | 155 |
| HPV16 | E5 | 11 | 9 | LLACFLLCF | | 156 |
| HPV16 | E5 | 32 | 8 | LLLSVSTY | | 157 |
| HPV16 | E5 | 47 | 11 | LLLWITAASAF | | 158 |
| HPV16 | E5 | 48 | 10 | LLWITAASAF | | 159 |
| HPV16 | E5 | 70 | 11 | PLFLIHTHARF | | 160 |
| HPV16 | E5 | 31 | 9 | PLLLSVSTY | | 161 |
| HPV16 | E5 | 41 | 10 | SLIILVLLLW | | 162 |
| HPV16 | E5 | 8 | 8 | STTLLACF | | 163 |
| HPV16 | E5 | 10 | 10 | TLLACFLLCF | | 164 |
| HPV16 | E5 | 40 | 11 | TSLIILVLLLW | | 165 |
| HPV16 | E5 | 9 | 11 | TTLLACFLLCF | | 166 |
| HPV16 | E5 | 50 | 8 | WITAASAF | | 167 |
| HPV16 | E5 | 50 | 11 | WITAASAFRCF | | 168 |
| HPV16 | E5 | 63 | 10 | YIIFVYIPLF | | 169 |
| HPV16 | E6 | 68 | 9 | AVCDKCLKF | | 170 |
| HPV16 | E6 | 68 | 10 | AVCDKCLKFY | 0.0095 | 171 |
| HPV16 | E6 | 58 | 10 | CIVYRDGNPY | 0.0015 | 172 |
| HPV16 | E6 | 73 | 11 | CLKFYSKISEY | | 173 |
| HPV16 | E6 | 32 | 8 | DIILECVY | | 174-- |
| HPV16 | E6 | 92 | 8 | GTTLEQQY | 0.0006 | 175 |
| HPV16 | E6 | 125 | 8 | HLDKKQRF | | 176 |
| HPV16 | E6 | 80 | 9 | ISEYRHYCY | 0.3100 | 177 |

TABLE VII-continued

A01 Supermotif Peptides

| Type | Protein | Position | No. of Amino Acids | Sequence | A*0101 | Seq. Id. No. |
|---|---|---|---|---|---|---|
| HPV16 | E6 | 59 | 9 | IVYRDGNPY | 0.0018 | 178 |
| HPV16 | E6 | 79 | 8 | KISEYRHY | | 179 |
| HPV16 | E6 | 79 | 10 | KISEYRHYCY | 0.0090 | 180 |
| HPV16 | E6 | 44 | 9 | LLRREVYDF | | 181 |
| HPV16 | E6 | 44 | 11 | LLRREVYDFAF | | 182 |
| HPV16 | E6 | 43 | 8 | QLLRREVY | | 183 |
| HPV16 | E6 | 43 | 10 | QLLRREVYDF | | 184 |
| HPV16 | E6 | 89 | 11 | SLYGTTLEQQY | | 185 |
| HPV16 | E6 | 29 | 11 | TIHDIILECVY | | 186 |
| HPV16 | E6 | 77 | 10 | YSKISEYRHY | 0.0150 | 187 |
| HPV16 | E7 | 14 | 10 | DLQPETTDLY | 0.0020 | 188 |
| HPV16 | E7 | 4 | 8 | DTPTLHEY | 0.0002 | 189 |
| HPV16 | E7 | 18 | 8 | ETTDLYCY | 0.0780 | 190 |
| HPV16 | L1 | 373 | 9 | AISTSETYY | | 191 |
| HPV16 | L1 | 292 | 11 | AVGENVPDDLY | | 192 |
| HPV16 | L1 | 251 | 10 | CTSICKYPDY | | 193 |
| HPV16 | L1 | 249 | 9 | DICTSICKY | | 194 |
| HPV16 | L1 | 484 | 11 | DLDQFPLGRKF | | 195 |
| HPV16 | L1 | 154 | 8 | DTENASAY | | 196 |
| HPV16 | L1 | 228 | 9 | DTGFGAMDF | | 197 |
| HPV16 | L1 | 17 | 8 | DVNVYHIF | | 198 |
| HPV16 | L1 | 17 | 9 | DVNVYHIFF | | 199 |
| HPV16 | L1 | 378 | 9 | ETTYKNTNF | | 200 |
| HPV16 | L1 | 474 | 8 | EVNLKEKF | | 201 |
| HPV16 | L1 | 5 | 10 | FIYILVITCY | | 202 |
| HPV16 | L1 | 481 | 8 | FSADLDQF | | 203 |
| HPV16 | L1 | 348 | 9 | GICWGNQLF | | 204 |
| HPV16 | L1 | 499 | 8 | GLKAKPKF | | 205 |
| HPV16 | L1 | 323 | 11 | GSMVTSDAQIF | | 206 |
| HPV16 | L1 | 307 | 11 | GSTANLASSNY | | 207 |
| HPV16 | L1 | 438 | 9 | GTLEDTYRF | | 208 |
| HPV16 | L1 | 22 | 9 | HIFFQMSLW | | 209 |
| HPV16 | L1 | 102 | 8 | HLPDPNKF | | 210 |
| HPV16 | L1 | 102 | 10 | HLPDPNKFGF | | 211 |
| HPV16 | L1 | 418 | 11 | HSMNSTILEDW | | 212 |
| HPV16 | L1 | 86 | 11 | ILVPKVSGLQY | | 213 |
| HPV16 | L1 | 374 | 8 | ISTSETTY | | 214 |
| HPV16 | L1 | 11 | 11 | ITCYENDVNVY | | 215 |
| HPV16 | L1 | 407 | 10 | ITLTADVMTY | | 216 |
| HPV16 | L1 | 406 | 11 | KITLTADVMTY | | 217 |
| HPV16 | L1 | 151 | 11 | KLDDTENASAY | | 218 |
| HPV16 | L1 | 90 | 10 | KVSGLQYRVF | | 219 |
| HPV16 | L1 | 46 | 8 | KVVSTDEY | | 220 |
| HPV16 | L1 | 68 | 8 | LLAVGHPY | | 221 |
| HPV16 | L1 | 68 | 9 | LLAVGHPYF | | 222 |
| HPV16 | L1 | 409 | 8 | LTADVMTY | | 223 |
| HPV16 | L1 | 87 | 10 | LVPKVSGLQY | | 224 |
| HPV16 | L1 | 226 | 11 | MVDTGFGAMDF | | 225 |
| HPV16 | L1 | 263 | 11 | MVSEPYGDSLF | | 226 |
| HPV16 | L1 | 325 | 9 | MVTSDAQIF | | 227 |
| HPV16 | L1 | 311 | 8 | NLASSNYF | | 228 |
| HPV16 | L1 | 421 | 8 | NSTILEDW | | 229 |
| HPV16 | L1 | 421 | 10 | NSTILEDWNF | | 230 |
| HPV16 | L1 | 247 | 11 | PLDICTSICKY | | 231 |
| HPV16 | L1 | 466 | 8 | PLKKYTFW | | 232 |
| HPV16 | L1 | 43 | 11 | PVSKVVSTDEY | | 233 |
| HPV16 | L1 | 331 | 8 | QIFNKPYW | | 234 |
| HPV16 | L1 | 280 | 8 | QMFVRHLF | | 235 |
| HPV16 | L1 | 100 | 10 | RIHLPDPNKF | | 236 |
| HPV16 | L1 | 67 | 9 | RLLAVGHPY | | 237 |
| HPV16 | L1 | 67 | 10 | RLLAVGHPYF | | 238 |
| HPV16 | L1 | 253 | 8 | SICKYPDY | | 239 |
| HPV16 | L1 | 28 | 11 | SLWLPSEATVY | | 240 |
| HPV16 | L1 | 419 | 10 | SMNSTILEDW | | 241 |
| HPV16 | L1 | 324 | 10 | SMVTSDAQIF | | 242 |
| HPV16 | L1 | 308 | 10 | STANLASSNY | | 243 |
| HPV16 | L1 | 308 | 11 | STANLASSNYF | | 244 |
| HPV16 | L1 | 422 | 9 | STILEDWNF | | 245 |
| HPV16 | L1 | 423 | 8 | TILEDWNF | | 246 |
| HPV16 | L1 | 439 | 8 | TLEDTYRF | | 247 |
| HPV16 | L1 | 408 | 9 | TLTADVMTY | | 248 |
| HPV16 | L1 | 327 | 11 | TSDAQIFNKPY | | 249 |
| HPV16 | L1 | 376 | 11 | TSETTYKNTNF | | 250 |
| HPV16 | L1 | 252 | 9 | TSICKYPDY | | 251 |

TABLE VII-continued

A01 Supermotif Peptides

| Type | Protein | Position | No. of Amino Acids | Sequence | A*0101 | Seq. Id. No. |
|---|---|---|---|---|---|---|
| HPV16 | L1 | 65 | 11 | TSRLLAVGHPY | | 252 |
| HPV16 | L1 | 379 | 8 | TTYKNTNF | | 253 |
| HPV16 | L1 | 379 | 11 | TTYKNTNFKEY | | 254 |
| HPV16 | L1 | 264 | 10 | VSEPYGDSLF | | 255 |
| HPV16 | L1 | 264 | 11 | VSEPYGDSLFF | | 256 |
| HPV16 | L1 | 91 | 9 | VSGLQYRVF | | 257 |
| HPV16 | L1 | 44 | 10 | VSKVVSTDEY | | 258 |
| HPV16 | L1 | 326 | 8 | VTSDAQIF | | 259 |
| HPV16 | L1 | 30 | 9 | WLPSEATVY | | 260 |
| HPV16 | L1 | 260 | 9 | YIKMVSEPY | | 261 |
| HPV16 | L1 | 7 | 8 | YILVITCY | | 262 |
| HPV16 | L1 | 389 | 8 | YLRHGEEY | | 263 |
| HPV16 | L1 | 275 | 8 | YLRREQMF | | 264 |
| HPV16 | L1 | 53 | 8 | YVARTNIY | | 265 |
| HPV16 | L1 | 53 | 9 | YVARTNIYY | | 266 |
| HPV16 | L2 | 356 | 11 | ALPTSINNGLY | | 267 |
| HPV16 | L2 | 293 | 11 | ALTSRRTGIRY | | 268 |
| HPV16 | L2 | 261 | 8 | DVDNTLYF | | 269 |
| HPV16 | L2 | 340 | 10 | ELQTITPSTY | | 270 |
| HPV16 | L2 | 242 | 11 | FITTPTKLITY | | 271 |
| RPV16 | L2 | 259 | 9 | GIDVDNTLY | | 272 |
| HPV16 | L2 | 259 | 10 | GIDVDNTLYF | | 273 |
| HPV16 | L2 | 364 | 10 | GLYDIYADDF | | 274 |
| HPV16 | L2 | 63 | 10 | GSGTGGRTGY | | 275 |
| HPV16 | L2 | 218 | 11 | GSRPVARLGLY | | 276 |
| HPV16 | L2 | 65 | 8 | GTGGRTGY | | 277 |
| HPV16 | L2 | 439 | 8 | IIADAGDF | | 278 |
| HPV16 | L2 | 439 | 9 | IIADAGDFY | | 279 |
| HPV16 | L2 | 45 | 10 | ILQYGSMGVF | | 280 |
| HPV16 | L2 | 45 | 11 | ILQYGSMGVFF | | 281- |
| HPV16 | L2 | 243 | 10 | ITTPTKLITY | | 282 |
| HPV16 | L2 | 250 | 8 | ITYDNPAY | | 283 |
| HPV16 | L2 | 430 | 8 | IVPGSPQY | | 284 |
| HPV16 | L2 | 105 | 10 | IVSLVEFTSF | | 285 |
| HPV16 | L2 | 248 | 10 | KLITYDNPAY | | 286 |
| HPV16 | L2 | 318 | 9 | KSIGAKVHY | | 287 |
| HPV16 | L2 | 318 | 10 | KSIGAKVHYY | | 288 |
| HPV16 | L2 | 318 | 11 | KSIGAKVHYYY | | 289 |
| HPV16 | L2 | 39 | 10 | KTIADQILQY | | 290 |
| HPV16 | L2 | 323 | 8 | KVHYYYDF | | 291 |
| HPV16 | L2 | 427 | 11 | LIPIVPGSPQY | | 292 |
| HPV16 | L2 | 249 | 9 | LITYDNPAY | | 293 |
| HPV16 | L2 | 183 | 11 | LSSSTISTHNY | | 294 |
| HPV16 | L2 | 294 | 10 | LTSRRTGIRY | | 295 |
| HPV16 | L2 | 454 | 11 | MLRKRRKRLPY | | 296 |
| HPV16 | L2 | 276 | 8 | NIAPDPDF | | 297 |
| HPV16 | L2 | 273 | 11 | NSINIAPDPDF | | 298 |
| HPV16 | L2 | 397 | 10 | NTTIPFGGAY | | 299 |
| HPV16 | L2 | 429 | 9 | PIVPGSPQY | | 300 |
| HPV16 | L2 | 124 | 10 | PSIPPDVSGF | | 301 |
| HPV16 | L2 | 386 | 8 | PSTSLSGY | | 302 |
| HPV16 | L2 | 383 | 11 | PSVPSTSLSGY | | 303 |
| HPV16 | L2 | 172 | 10 | PTPAETGGHF | | 304 |
| HPV16 | L2 | 358 | 9 | PTSINNGLY | | 305 |
| HPV16 | L2 | 221 | 8 | PVARLGLY | | 306 |
| HPV16 | L2 | 44 | 11 | QILQYGSMGVF | | 307 |
| HPV16 | L2 | 342 | 8 | QTITPSTY | | 308 |
| HPV16 | L2 | 234 | 9 | QVKVVDPAF | | 309 |
| HPV16 | L2 | 9 | 11 | RTKRASATQLY | | 310 |
| HPV16 | L2 | 319 | 8 | SIGAKVHY | | 311 |
| HPV16 | L2 | 319 | 9 | SIGAKVHYY | | 312 |
| HPV16 | L2 | 319 | 10 | SIGAKVHYYY | | 313 |
| HPV16 | L2 | 274 | 10 | SINIAPDPDF | | 314 |
| HPV16 | L2 | 360 | 10 | SINNGLYDIY | | 315 |
| HPV16 | L2 | 125 | 9 | SIPPDVSGF | | 316 |
| HPV16 | L2 | 104 | 11 | SIVSLVEETSF | | 317 |
| HPV16 | L2 | 107 | 8 | SLVEETSF | | 318 |
| HPV16 | L2 | 184 | 10 | SSSTISTHNY | | 319 |
| HPV16 | L2 | 185 | 9 | SSTISTHNY | | 320 |
| HPV16 | L2 | 186 | 8 | STISTHNY | | 321 |
| HPV16 | L2 | 384 | 10 | SVPSTSLSGY | | 322 |
| HPV16 | L2 | 40 | 9 | TIADQILQY | | 323 |
| HPV16 | L2 | 438 | 9 | TIIADAGDF | | 324 |
| HPV16 | L2 | 438 | 10 | TIIADAGDFY | | 325 |

TABLE VII-continued

A01 Supermotif Peptides

| Type | Protein | Position | No. of Amino Acids | Sequence | A*0101 | Seq. Id. No. |
|---|---|---|---|---|---|---|
| MPV16 | L2 | 399 | 8 | TIPFGGAY | | 326 |
| HPV16 | L2 | 359 | 8 | TSINNGLY | | 327 |
| HPV16 | L2 | 359 | 11 | TSINNGLYDIY | | 328 |
| HPV16 | L2 | 295 | 9 | TSRRTGIRY | | 329 |
| HPV16 | L2 | 156 | 8 | TTHNNPTF | | 330 |
| HPV16 | L2 | 398 | 9 | TTIPFGGAY | | 331 |
| HPV16 | L2 | 244 | 9 | TTPTKLITY | | 332 |
| HPV16 | L2 | 153 | 11 | TTVTTHNNPTF | | 333 |
| HPV16 | L2 | 154 | 10 | TVTTHNNPTF | | 334 |
| HPV16 | L2 | 106 | 9 | VSLVEETSF | | 335- |
| HPV16 | L2 | 155 | 9 | VTTHNNPTF | | 336 |
| HPV16 | L2 | 393 | 10 | YIPANTTIPF | | 337 |
| HPV16 | L2 | 437 | 10 | YTIIADAGDF | | 338 |
| HPV16 | L2 | 437 | 11 | YTIIADAGDFY | | 339 |
| HPV18 | E1 | 213 | 10 | AMLAVFKDTY | | 340 |
| HPV18 | E1 | 526 | 11 | AMLDDATTTCW | | 341 |
| HPV18 | E1 | 40 | 11 | ATDTGSDMVDF | | 342 |
| HPV18 | E1 | 531 | 8 | ATTTCWTY | | 343 |
| HPV18 | E1 | 531 | 9 | ATTTCWTYF | | 344 |
| HPV18 | E1 | 216 | 11 | AVFKDTYGLSF | | 345 |
| HPV18 | E1 | 437 | 10 | CSKIDEGGDW | | 346 |
| HPV18 | E1 | 240 | 9 | CTDWVTAIF | | 347 |
| HPV18 | E1 | 363 | 8 | DLSEMVQW | | 348 |
| HPV18 | E1 | 363 | 10 | DLSEMVQWAF | | 349 |
| HPV18 | E1 | 391 | 9 | DSNSNAAAF | | 350 |
| HPV18 | E1 | 637 | 10 | DTEGNPFGTF | | 351 |
| HPV18 | E1 | 42 | 9 | DTGSDMVDF | | 352 |
| HPV18 | E1 | 610 | 10 | EINDKNWKCF | | 353 |
| HPV18 | E1 | 610 | 11 | EINDKNWKCFF | | 354 |
| HPV18 | E1 | 62 | 9 | ELETAQALF | | 355 |
| HPV18 | E1 | 375 | 10 | ELTDESDMAF | | 356 |
| HPV18 | E1 | 379 | 8 | ESDMAFEY | | 357 |
| HPV18 | E1 | 587 | 9 | ESRITVFEF | | 358 |
| HPV18 | E1 | 338 | 9 | EVMGDTPEW | | 359 |
| HPV18 | E1 | 50 | 8 | FIDTQGTF | | 360 |
| HPV18 | E1 | 500 | 9 | FIQGAVISF | | 361 |
| HPV18 | E1 | 460 | 11 | FITFLGALKSF | | 362 |
| HPV18 | E1 | 463 | 8 | FLGALKSF | | 363 |
| HPV18 | E1 | 399 | 10 | FLKSNCQAKY | | 364 |
| HPV18 | E1 | 452 | 9 | FLRYQQIEF | | 365 |
| HPV18 | E1 | 226 | 8 | FTDLVRNF | | 366 |
| HPV18 | E1 | 130 | 8 | FTISDSGY | | 367 |
| HPV18 | E1 | 508 | 8 | FVNSTSHF | | 368 |
| HPV18 | E1 | 508 | 9 | FVNSTSHFW | | 369 |
| HPV18 | E1 | 223 | 11 | GLSFTDLVRNF | | 370 |
| HPV18 | E1 | 11 | 8 | GTGCNGWF | | 371 |
| HPV18 | E1 | 11 | 9 | GTGCNGWFY | 3.9000 | 372 |
| HPV18 | E1 | 473 | 10 | GTPKKNCLVF | | 373 |
| HPV18 | E1 | 279 | 10 | GVLILALLRY | | 374 |
| HPV18 | E1 | 249 | 10 | GVNPTIAEGF | | 375 |
| HPV18 | E1 | 270 | 9 | HIQCLDCKW | | 376 |
| HPV18 | E1 | 352 | 11 | IIQHGIDDSNF | | 377 |
| HPV18 | E1 | 336 | 11 | ISEVMGDTPEW | | 378 |
| HPV18 | E1 | 506 | 10 | ISFVNSTSHF | | 379 |
| HPV18 | E1 | 506 | 11 | ISFVNSTSHFW | | 380 |
| HPV18 | E1 | 461 | 10 | ITFLGALKSF | | 381 |
| HPV18 | E1 | 590 | 10 | ITVFEFPNAF | | 382 |
| HPV18 | E1 | 439 | 8 | KIDEGGDW | | 383 |
| HPV18 | E1 | 318 | 10 | KLRSSVAALY | | 384 |
| HPV18 | E1 | 318 | 11 | KLRSSVAALYW | | 385 |
| HPV18 | E1 | 234 | 10 | KSDKTTCTDW | | 386 |
| HPV18 | E1 | 401 | 8 | KSNCQAKY | | 387 |
| HPV18 | E1 | 490 | 8 | KSYFGMSF | | 388 |
| HPV18 | E1 | 490 | 11 | KSYFGMSFIHF | | 389 |
| HPV18 | E1 | 259 | 10 | KTLIQPFILY | | 390 |
| HPV18 | E1 | 281 | 8 | LILALLRY | | 391 |
| HPV18 | E1 | 261 | 8 | LIQPFILY | | 392 |
| HPV18 | E1 | 364 | 9 | LSEMVQWAF | | 393 |
| HPV18 | E1 | 224 | 10 | LSFTDLVRNF | | 394 |
| HPV18 | E1 | 376 | 9 | LTDESDMAF | | 395 |
| HPV18 | E1 | 376 | 11 | LTDESDMAFEY | | 396 |
| HPV18 | E1 | 214 | 9 | MLAVFKDTY | | 397 |
| HPV18 | E1 | 527 | 10 | MLDDATTTCW | | 398 |
| HPV18 | E1 | 47 | 11 | MVDFIDTQGTF | | 399 |

TABLE VII-continued

A01 Supermotif Peptides

| Type | Protein | Position | No. of Amino Acids | Sequence | A*0101 | Seq. Id. No. |
|---|---|---|---|---|---|---|
| HPV18 | E1 | 574 | 10 | NIHPAKDNRW | | 400 |
| HPV18 | E1 | 428 | 8 | NMSQWIRF | | 401 |
| HPV18 | E1 | 487 | 11 | NTGKSYFGMSF | | 402 |
| HPV18 | E1 | 448 | 8 | PIVQFLRY | | 403 |
| HPV18 | E1 | 607 | 10 | PVYEINDKNW | | 404 |
| HPV18 | E1 | 426 | 10 | QMNMSQWIRF | | 405 |
| HPV18 | E1 | 80 | 10 | QVLHVLKRKF | | 406 |
| HPV18 | E1 | 589 | 11 | RITVFEFPNAF | | 407 |
| HPV18 | E1 | 128 | 10 | RLFTISDSGY | | 408 |
| HPV18 | E1 | 320 | 8 | RSSVAALY | | 409 |
| HPV18 | E1 | 320 | 9 | RSSVAALYW | | 410 |
| HPV18 | E1 | 320 | 10 | RSSVAALYWY | | 411 |
| HPV18 | E1 | 321 | 8 | SSVAALYW | | 412 |
| HPV18 | E1 | 321 | 9 | SSVAALYWY | | 413 |
| HPV18 | E1 | 322 | 8 | SVAALYWY | | 414 |
| HPV18 | E1 | 260 | 9 | TLIQPFILY | | 415 |
| HPV18 | E1 | 238 | 11 | TTCTDWVTAIF | | 416 |
| HPV18 | E1 | 533 | 10 | TTCWTYFDTY | | 417 |
| HPV18 | E1 | 532 | 8 | TTTCWTYF | | 418 |
| HPV18 | E1 | 532 | 11 | TTTCWTYFDTY | | 419 |
| HPV18 | E1 | 591 | 9 | TVFEFPNAF | | 420 |
| HPV18 | E1 | 591 | 11 | TVFEFPNAFPF | | 421 |
| HPV18 | E1 | 505 | 11 | VISFVNSTSHF | | 422 |
| HPV18 | E1 | 81 | 9 | VLHVLKRKF | | 423 |
| HPV18 | E1 | 280 | 9 | VLILALLRY | | 424 |
| HPV18 | E1 | 339 | 8 | VMGDTPEW | | 425 |
| HPV18 | E1 | 585 | 9 | YLESRITVF | | 426 |
| HPV18 | E1 | 585 | 11 | YLESRITVFEF | | 427 |
| HPV18 | E2 | 82 | 10 | ALQGLAQSRY | | 428 |
| HPV18 | E2 | 154 | 10 | ATCVSHRGLY | | 429 |
| HPV18 | E2 | 154 | 11 | ATCVSHRGLYY | | 430 |
| HPV18 | E2 | 132 | 11 | CMTYVAWDSVY | | 431 |
| HPV18 | E2 | 14 | 10 | CVQDKIIDHY | | 432 |
| HPV18 | E2 | 156 | 8 | CVSHRGLY | | 433 |
| HPV18 | E2 | 156 | 9 | CVSHRGLYY | | 434 |
| HPV18 | E2 | 29 | 8 | DIDSQIQY | | 435 |
| HPV18 | E2 | 29 | 9 | DIDSQIQYW | | 436 |
| HPV18 | E2 | 315 | 8 | DISSTWHW | | 437 |
| HPV18 | E2 | 26 | 11 | DSKDIDSQIQY | | 438 |
| HPV18 | E2 | 354 | 9 | DSVQILVGY | | 439 |
| HPV18 | E2 | 104 | 11 | ELWNTEPTHCF | | 440 |
| HPV18 | E2 | 161 | 9 | GLYYVKEGY | | 441 |
| HPV18 | E2 | 338 | 9 | HSETQRTKF | | 442 |
| HPV18 | E2 | 329 | 9 | KTGILTVTY | | 443 |
| HPV18 | E2 | 39 | 9 | LIRWENAIF | | 444 |
| HPV18 | E2 | 39 | 10 | LIRWENAIFF | | 445 |
| HPV18 | E2 | 133 | 10 | MTYVAWDSVY | | 446 |
| HPV18 | E2 | 133 | 11 | MTYVAWDSVYY | | 447 |
| HPV18 | E2 | 297 | 8 | NSLKCLRY | | 448 |
| HPV18 | E2 | 107 | 8 | NTEPTHCF | | 449 |
| HPV18 | E2 | 185 | 9 | NTGTWEVHF | | 450 |
| HPV18 | E2 | 33 | 10 | QIQYWQLIRW | | 451 |
| HPV18 | E2 | 38 | 10 | QLIRWENAIF | | 452 |
| HPV18 | E2 | 38 | 11 | QLIRWENAIFF | | 453 |
| HPV18 | E2 | 220 | 9 | QLQHTPSPY | | 454 |
| HPV18 | E2 | 88 | 9 | QSRYKTEDW | | 455 |
| HPV18 | E2 | 56 | 11 | QTLNHQVVPAY | | 456 |
| HPV18 | E2 | 305 | 9 | RLRKHSDHY | | 457 |
| HPV18 | E2 | 230 | 11 | STVSVGTAKTY | | 458 |
| HPV18 | E2 | 233 | 8 | SVGTAKTY | | 459 |
| HPV18 | E2 | 355 | 8 | SVQILVGY | | 460 |
| HPV18 | E2 | 140 | 11 | SVYYMTDAGTW | | 461 |
| HPV18 | E2 | 57 | 10 | TLNHQVVPAY | | 462 |
| HPV18 | E2 | 97 | 10 | TLQDTCEELW | | 463 |
| HPV18 | E2 | 231 | 10 | TVSVGTAKTY | | 464 |
| HPV18 | E2 | 157 | 8 | VSHRGLYY | | 465 |
| HPV18 | E2 | 232 | 9 | VSVGTAKTY | | 466 |
| HPV18 | E2 | 96 | 11 | WTLQDTCEELW | | 467 |
| HPV18 | E2 | 173 | 11 | YIEFKSECEKY | | 468 |
| HPV18 | E2 | 143 | 8 | YMTDAGTW | | 469 |
| HPV18 | E2 | 135 | 8 | YVAWDSVY | | 470 |
| HPV18 | E2 | 135 | 9 | YVAWDSVYY | | 471 |
| HPV18 | E2 | 164 | 9 | YVKEGYNTF | | 472 |
| HPV18 | E2 | 164 | 10 | YVKEGYNTFY | | 473 |

TABLE VII-continued

A01 Supermotif Peptides

| Type | Protein | Position | No. of Amino Acids | Sequence | A*0101 | Seq. Id. No. |
|---|---|---|---|---|---|---|
| HPV18 | E5 | 47 | 9 | ATAFTVYVF | | 474 |
| HPV18 | E5 | 47 | 11 | ATAFTVYVFCF | | 475 |
| HPV18 | E5 | 27 | 11 | CMCAYAWVLVF | | 476 |
| HPV18 | E5 | 6 | 10 | FLFCFCVCMY | | 477 |
| HPV18 | E5 | 50 | 8 | FTVYVFCF | | 478 |
| HPV18 | E5 | 43 | 8 | ITSPATAF | | 479 |
| HPV18 | E5 | 43 | 11 | ITSPATAFTVY | | 480 |
| HPV18 | E5 | 40 | 11 | IVVITSPATAF | | 481 |
| HPV18 | E5 | 22 | 10 | LLPSVCMCAY | | 482 |
| HPV18 | E5 | 2 | 9 | LSLIFLFCF | | 483 |
| HPV18 | E5 | 1 | 8 | MLSLIFLF | | 484 |
| HPV18 | E5 | 1 | 10 | MLSLIFLFCF | | 485 |
| HPV18 | E5 | 21 | 11 | PLLPSVCMCAY | | 486 |
| HPV18 | E5 | 24 | 8 | PSVCMCAY | | 487 |
| HPV18 | E5 | 24 | 10 | PSVCMCAYAW | | 488 |
| HPV18 | E5 | 3 | 8 | SLIFLFCF | | 489 |
| HPV18 | E5 | 25 | 9 | SVCMCAYAW | | 490 |
| HPV18 | E5 | 44 | 10 | TSPATAFTVY | | 491 |
| HPV18 | E5 | 42 | 9 | VITSPATAF | | 492 |
| HPV18 | E5 | 41 | 10 | VVITSPATAF | | 493 |
| HPV18 | E6 | 27 | 8 | DIEITCVY | 0.0025 | 494 |
| HPV18 | E6 | 77 | 10 | ELRHYSDSVY | 0.0037 | 495 |
| HPV18 | E6 | 40 | 8 | ELTEVFEF | | 496 |
| HPV18 | E6 | 40 | 10 | ELTEVFEFAF | | 497 |
| HPV18 | E6 | 43 | 11 | EVFEFAFKDLF | | 498 |
| HPV18 | E6 | 120 | 8 | HLNEKRRF | | 499 |
| HPV18 | E6 | 117 | 11 | KLRHLNEKRRF | | 500 |
| HPV18 | E6 | 92 | 8 | KLTNTGLY | | 501 |
| HPV18 | E6 | 36 | 10 | KTVLELTEVF | | 502 |
| HPV18 | E6 | 41 | 9 | LTEVFEFAF | | 503 |
| HPV18 | E6 | 74 | 8 | RIRELRHY | | 504 |
| HPV18 | E6 | 24 | 11 | SLQDIEITCVY | | 505 |
| HPV18 | E6 | 89 | 11 | TLEKLTNTGLY | 5.9000 | 506 |
| HPV18 | E6 | 37 | 9 | TVLELTEVF | | 507 |
| HPV18 | E6 | 37 | 11 | TVLELTEVFEF | | 508 |
| HPV18 | E6 | 38 | 8 | VLELTEVF | | 509 |
| HPV18 | E6 | 38 | 10 | VLELTEVFEF | | 510 |
| HPV18 | E6 | 72 | 10 | YSRIRELRHY | 0.0008 | 511 |
| HPV18 | E7 | 82 | 9 | DLRAFQQLF | | 512 |
| HPV18 | E7 | 77 | 10 | ESSADDLRAF | | 513 |
| HPV18 | E7 | 90 | 11 | FLNTLSFVCPW | | 514 |
| HPV18 | E7 | 92 | 9 | NTLSFVCPW | | 515 |
| HPV18 | E7 | 88 | 9 | QLFLNTLSF | | 516 |
| HPV18 | E7 | 78 | 9 | SSADDLRAF | | 517 |
| HPV18 | E7 | 93 | 8 | TLSFVCPW | | 518 |
| HPV18 | L1 | 63 | 11 | ALWRPSDNTVY | | 519 |
| HPV18 | L1 | 345 | 8 | ASPGSCVY | | 520 |
| HPV18 | L1 | 407 | 11 | ASTQSPVPGQY | | 521 |
| HPV18 | L1 | 310 | 8 | CLRREQLF | | 522 |
| HPV18 | L1 | 2 | 11 | CLYTRVLILHY | | 523 |
| HPV18 | L1 | 284 | 9 | DICQSICKY | | 524 |
| HPV18 | L1 | 122 | 8 | DIPKVSAY | | 525 |
| HPV18 | L1 | 122 | 10 | DIPKVSAYQY | | 526 |
| HPV18 | L1 | 520 | 11 | DLDQYPLGRKF | | 527 |
| HPV18 | L1 | 364 | 9 | DSQLFNKPY | | 528 |
| HPV18 | L1 | 364 | 10 | DSQLFNKPYW | | 529 |
| HPV18 | L1 | 263 | 9 | DTGYGAMDF | | 530 |
| HPV18 | L1 | 330 | 9 | DTVPQSLY | | 531 |
| HPV18 | L1 | 203 | 10 | DVRDNVSVDY | | 532 |
| HPV18 | L1 | 49 | 8 | FLRNVNVF | | 533 |
| HPV18 | L1 | 49 | 11 | FLRNVNVFPIF | | 534 |
| HPV18 | L1 | 517 | 8 | FSLDLDQY | | 535 |
| HPV18 | L1 | 145 | 8 | GLPDTSIY | | 536 |
| HPV18 | L1 | 177 | 8 | GLSGHPFY | | 537 |
| HPV18 | L1 | 342 | 11 | GMPASPGSCVY | | 538 |
| HPV18 | L1 | 358 | 11 | GSIVTSDSQLF | | 539 |
| HPV18 | L1 | 383 | 9 | GVCWHNQLF | | 540 |
| HPV18 | L1 | 175 | 9 | GVGLSGHPF | | 541 |
| HPV18 | L1 | 175 | 10 | GVGLSGHPFY | | 542 |
| HPV18 | L1 | 38 | 8 | HIIICGHY | | 543 |
| HPV18 | L1 | 13 | 10 | HLLPLYGPLY | | 544 |
| HPV18 | L1 | 454 | 11 | HSMNSSILEDW | | 545 |
| HPV18 | L1 | 428 | 9 | HVEEYDLQF | | 546 |
| HPV18 | L1 | 428 | 11 | HVEEYDLQFIF | | 547 |

TABLE VII-continued

A01 Supermotif Peptides

| Type | Protein | Position | No. of Amino Acids | Sequence | A*0101 | Seq. Id. No. |
|---|---|---|---|---|---|---|
| HPV18 | L1 | 40 | 10 | IICGHYIILF | | 548 |
| HPV18 | L1 | 39 | 11 | IIICGHYIILF | | 549 |
| HPV18 | L1 | 46 | 11 | IILFLRNVNVF | | 550 |
| HPV18 | L1 | 47 | 10 | ILFLRNVNVF | | 551 |
| HPV18 | L1 | 9 | 10 | ILHYHLLPLY | | 552 |
| HPV18 | L1 | 443 | 10 | ITLTADVMSY | | 553 |
| HPV18 | L1 | 360 | 9 | IVTSDSQLF | | 554 |
| HPV18 | L1 | 125 | 10 | KVSAYQYRVF | | 555 |
| HPV18 | L1 | 8 | 11 | LILHYHLLPLY | | 556 |
| HPV18 | L1 | 14 | 9 | LLPLYGPLY | | 557 |
| HPV18 | L1 | 103 | 8 | LLTVGNPY | | 558 |
| HPV18 | L1 | 103 | 9 | LLTVGNPYF | | 559 |
| HPV18 | L1 | 445 | 8 | LTADVMSY | | 560 |
| HPV18 | L1 | 104 | 8 | LTVGNPYF | | 561 |
| HPV18 | L1 | 298 | 11 | MSADPYGDSMF | | 562 |
| HPV18 | L1 | 261 | 11 | MVDTGYGAMDF | | 563 |
| HPV18 | L1 | 36 | 10 | MVHIIICGHY | | 564 |
| HPV18 | L1 | 457 | 8 | NSSILEDW | | 565 |
| HPV18 | L1 | 457 | 10 | NSSILEDWNF | | 566 |
| HPV18 | L1 | 510 | 8 | NVDLKEKF | | 567 |
| HPV18 | L1 | 52 | 8 | NVNVFPIF | | 568 |
| HPV18 | L1 | 57 | 9 | PIFLQMALW | | 569 |
| HPV18 | L1 | 282 | 11 | PLDICQSICKY | | 570 |
| HPV18 | L1 | 173 | 11 | PLGVGLSGHPF | | 571 |
| HPV18 | L1 | 28 | 8 | PLHSILVY | | 572 |
| HPV18 | L1 | 26 | 10 | PLPLHSILVY | | 573 |
| HPV18 | L1 | 472 | 9 | PTTSLVDTY | | 574 |
| HPV18 | L1 | 472 | 11 | PTTSLVDTYRF | | 575 |
| HPV18 | L1 | 412 | 11 | PVPGQYDATKF | | 576 |
| HPV18 | L1 | 315 | 8 | QLFARHFW | | 577 |
| HPV18 | L1 | 366 | 8 | QLFNKPYW | | 578 |
| HPV18 | L1 | 137 | 8 | QLPDPNKF | | 579 |
| HPV18 | L1 | 287 | 9 | QSICKYPDY | | 580 |
| HPV18 | L1 | 410 | 8 | QSPVPGQY | | 581 |
| HPV18 | L1 | 102 | 9 | RLLTVGNPY | | 582 |
| HPV18 | L1 | 102 | 10 | RLLTVGNPYF | | 583 |
| HPV18 | L1 | 135 | 10 | RVQLPDPNKF | | 584 |
| HPV18 | L1 | 81 | 8 | RVVNTDDY | | 585 |
| HPV18 | L1 | 288 | 8 | SICKYPDY | | 586 |
| HPV18 | L1 | 459 | 8 | SILEDWNF | | 587 |
| HPV18 | L1 | 359 | 10 | SIVTSDSQLF | | 588 |
| HPV18 | L1 | 475 | 8 | SLVDTYRF | | 589 |
| HPV18 | L1 | 455 | 10 | SMNSSILEDW | | 590 |
| HPV18 | L1 | 458 | 9 | SSILEDWNF | | 591 |
| HPV18 | L1 | 100 | 11 | SSRLLTVGNPY | | 592 |
| HPV18 | L1 | 408 | 10 | STQSPVPGQY | | 593 |
| HPV18 | L1 | 78 | 11 | SVARVVNTDDY | | 594 |
| HPV18 | L1 | 442 | 11 | TITLTADVMSY | | 595 |
| HPV18 | L1 | 444 | 9 | TLTADVMSY | | 596 |
| HPV18 | L1 | 327 | 11 | TMGDTVPQSLY | | 597 |
| HPV18 | L1 | 362 | 11 | TSDSQLFNKPY | | 598 |
| HPV18 | L1 | 474 | 9 | TSLVDTYRF | | 599 |
| HPV18 | L1 | 473 | 8 | TTSLVDTY | | 600 |
| HPV18 | L1 | 473 | 10 | TTSLVDTYRF | | 601 |
| HPV18 | L1 | 126 | 9 | VSAYQYRVF | | 602 |
| HPV18 | L1 | 89 | 8 | VTPTSIFY | | 603 |
| HPV18 | L1 | 361 | 8 | VTSDSQLF | | 604 |
| HPV18 | L1 | 295 | 9 | YLQMSADPY | | 605 |
| HPV18 | L1 | 35 | 11 | YMVHIIICGHY | | 606 |
| HPV18 | L1 | 425 | 8 | YSRHVEEY | | 607 |
| HPV18 | L1 | 4 | 9 | YTRVLILHY | | 608 |
| HPV18 | L1 | 88 | 8 | YVTPTSIF | | 609 |
| HPV18 | L1 | 88 | 9 | YVTPTSIFY | | 610 |
| HPV18 | L2 | 286 | 11 | ALTSRRGTVRF | | 611 |
| HPV18 | L2 | 341 | 8 | ATEDNDLF | | 612 |
| HPV18 | L2 | 341 | 11 | ATEDNDLFDIY | | 613 |
| HPV18 | L2 | 322 | 11 | DISPIAPSPEY | | 614 |
| HPV18 | L2 | 404 | 11 | DITLPSTTSVW | | 615 |
| HPV18 | L2 | 443 | 11 | FIPKKRKRVPY | | 616 |
| HPV18 | L2 | 241 | 11 | FLTRPSSLITY | | 617 |
| HPV18 | L2 | 296 | 11 | FSRLGQRATMF | | 618 |
| HPV18 | L2 | 429 | 8 | GIHGTHYY | | 619 |
| HPV18 | L2 | 429 | 10 | GIHGTHYYLW | | 620 |
| HPV18 | L2 | 62 | 10 | GSGTGGRTGY | | 621 |

TABLE VII-continued

A01 Supermotif Peptides

| Type | Protein | Position | No. of Amino Acids | Sequence | A*0101 | Seq. Id. No. |
|---|---|---|---|---|---|---|
| HPV18 | L2 | 64 | 8 | GTGGRTGY | | 622 |
| HPV18 | L2 | 432 | 10 | GTHYYLWPLY | | 623 |
| HPV18 | L2 | 432 | 11 | GTHYYLWPLYY | | 624 |
| HPV18 | L2 | 183 | 10 | GTPTSGTHGY | | 625 |
| HPV18 | L2 | 310 | 10 | GTQIGARVHF | | 626 |
| HPV18 | L2 | 310 | 11 | GTQIGARVHFY | | 627 |
| HPV18 | L2 | 37 | 11 | GTTLADKILQW | | 628 |
| HPV18 | L2 | 44 | 10 | ILQWSSLGIF | | 629 |
| HPV18 | L2 | 323 | 10 | ISPIAPSPEY | | 630 |
| HPV18 | L2 | 152 | 11 | ISTTNFTNPAF | | 631 |
| HPV18 | L2 | 405 | 10 | ITLPSTTSVW | | 632 |
| HPV18 | L2 | 249 | 8 | ITYDNPAF | | 633 |
| HPV18 | L2 | 43 | 11 | KILQWSSLGIF | | 634 |
| HPV18 | L2 | 248 | 9 | LITYDNPAF | | 635 |
| HPV18 | L2 | 242 | 10 | LTRPSSLITY | | 636 |
| HPV18 | L2 | 287 | 10 | LTSRRGTVRF | | 637 |
| HPV18 | L2 | 391 | 10 | LTSSWDVPVY | | 638 |
| HPV18 | L2 | 338 | 11 | LVSATEDNDLF | | 639 |
| HPV18 | L2 | 386 | 10 | NVTVPLTSSW | | 640 |
| HPV18 | L2 | 325 | 8 | PIAPSPEY | | 641 |
| HPV18 | L2 | 390 | 11 | PLTSSWDVPVY | | 642 |
| HPV18 | L2 | 362 | 8 | PSRSTTSF | | 643 |
| HPV18 | L2 | 362 | 10 | PSRSTTSFAF | | 644 |
| HPV18 | L2 | 362 | 11 | PSRSTTSFAFF | | 645 |
| HPV18 | L2 | 419 | 9 | PTAPASTQY | | 646 |
| HPV18 | L2 | 120 | 9 | PTFTGTSGF | | 647 |
| HPV18 | L2 | 376 | 9 | PTISSASSY | | 648 |
| HPV18 | L2 | 185 | 8 | PTSGTHGY | | 649 |
| HPV18 | L2 | 258 | 8 | PVDTTLTF | | 650 |
| HPV18 | L2 | 360 | 10 | PVPSRSTTSF | | 651 |
| HPV18 | L2 | 312 | 8 | QIGARVHF | | 652 |
| HPV18 | L2 | 312 | 9 | QIGARVHFY | | 653 |
| HPV18 | L2 | 172 | 10 | QTGEVAGNVF | | 654 |
| HPV18 | L2 | 233 | 9 | QVSVANPEF | | 655 |
| HPV18 | L2 | 298 | 9 | RLGQRATMF | | 656 |
| HPV18 | L2 | 268 | 9 | RSDVPDSDF | | 657 |
| HPV18 | L2 | 364 | 8 | RSTTSFAF | | 658 |
| HPV18 | L2 | 364 | 9 | RSTTSFAFF | | 659 |
| HPV18 | L2 | 364 | 11 | RSTTSFAFFKY | | 660 |
| HPV18 | L2 | 220 | 8 | RVAGPRLY | | 661 |
| HPV18 | L2 | 450 | 10 | RVPYFFADGF | | 662 |
| HPV18 | L2 | 247 | 10 | SLITYDNPAF | | 663 |
| HPV18 | L2 | 246 | 11 | SSLITYDNPAF | | 664 |
| HPV18 | L2 | 393 | 8 | SSWDVPVY | | 665 |
| HPV18 | L2 | 147 | 11 | STSVSISTTNF | | 666 |
| HPV18 | L2 | 153 | 10 | STTNFTNPAF | | 667 |
| HPV18 | L2 | 365 | 8 | STTSFAFF | | 668 |
| HPV18 | L2 | 365 | 10 | STTSFAFFKY | | 669 |
| HPV18 | L2 | 149 | 9 | SVSISTTNF | | 670 |
| HPV18 | L2 | 377 | 8 | TISSASSY | | 671 |
| HPV18 | L2 | 39 | 9 | TLADKILQW | | 672 |
| HPV18 | L2 | 406 | 9 | TLPSTTSVW | | 673 |
| HPV18 | L2 | 367 | 8 | TSFAFFKY | | 674 |
| HPV18 | L2 | 114 | 9 | TSGAPRPTF | | 675 |
| HPV18 | L2 | 288 | 9 | TSRRGTVRF | | 676 |
| HPV18 | L2 | 392 | 9 | TSSWDVPVY | | 677 |
| HPV18 | L2 | 148 | 10 | TSVSISTTNF | | 678 |
| HPV18 | L2 | 38 | 10 | TTLADKILQW | | 679 |
| HPV18 | L2 | 154 | 9 | TTNFTNPAF | | 680 |
| HPV18 | L2 | 366 | 9 | TTSFAFFKY | | 681 |
| HPV18 | L2 | 388 | 8 | TVPLTSSW | | 682 |
| HPV18 | L2 | 217 | 11 | TVRRVAGPRLY | | 683 |
| HPV18 | L2 | 339 | 10 | VSATEDNDLF | | 684 |
| HPV18 | L2 | 150 | 8 | VSISTTNF | | 685 |
| HPV18 | L2 | 417 | 11 | VSPTAPASTQY | | 686 |
| HPV18 | L2 | 234 | 8 | VSVANPEF | | 687 |
| HPV18 | L2 | 113 | 10 | VTSGAPRPTF | | 688 |
| HPV18 | L2 | 387 | 9 | VTVPLTSSW | | 689 |
| HPV18 | L2 | 112 | 11 | VVTSGAPRPTF | | 690 |
| HPV18 | L2 | 427 | 9 | TIGIHGTHY | | 691 |
| HPV18 | L2 | 427 | 10 | YIGIHGTHYY | | 692 |
| HPV18 | L2 | 436 | 8 | YLWPLYYF | | 693 |
| HPV18 | L2 | 374 | 11 | YSPTISSASSY | | 694 |
| HPV31 | E1 | 186 | 10 | AMLGKFKELY | | 695 |

TABLE VII-continued

A01 Supermotif Peptides

| Type | Protein | Position | No. of Amino Acids | Sequence | A*0101 | Seq. Id. No. |
|---|---|---|---|---|---|---|
| HPV31 | E1 | 504 | 8 | ATTPCWHY | | 696 |
| HPV31 | E1 | 81 | 9 | AVQVLKRKY | | 697 |
| HPV31 | E1 | 213 | 9 | CTDWCVAAF | | 698 |
| HPV31 | E1 | 96 | 8 | DISSCVDY | | 699 |
| HPV31 | E1 | 421 | 8 | DIVKFLRY | | 700 |
| HPV31 | E1 | 336 | 8 | DLSQMVQW | | 701 |
| HPV31 | E1 | 336 | 10 | DLSQMVQWAY | | 702 |
| HPV31 | E1 | 364 | 9 | DSDSNACAF | | 703 |
| HPV31 | E1 | 352 | 8 | DSELAYKY | | 704 |
| HPV31 | E1 | 42 | 9 | DTGEDMVDF | | 705 |
| HPV31 | E1 | 348 | 10 | DVMDDSELAY | | 706 |
| HPV31 | E1 | 311 | 9 | DVYGETPEW | | 707 |
| HPV31 | E1 | 583 | 10 | ELSDKNWKSF | | 708 |
| HPV31 | E1 | 583 | 11 | ELSDKNWKSFF | | 709 |
| HPV31 | E1 | 50 | 8 | FIDNCNVY | | 710 |
| HPV31 | E1 | 473 | 9 | FLQGCIISY | | 711 |
| HPV31 | E1 | 425 | 9 | FLRYQQIEF | | 712 |
| HPV31 | E1 | 436 | 8 | FLSALKLF | | 713 |
| HPV31 | E1 | 199 | 8 | FMELIRPF | | 714 |
| HPV31 | E1 | 566 | 9 | FTFPNPFPF | | 715 |
| HPV31 | E1 | 433 | 11 | FVSFLSALKFL | | 716 |
| HPV31 | E1 | 499 | 11 | GMLDDATTPCW | | 717 |
| HPV31 | E1 | 305 | 9 | GMSNISDVY | | 718 |
| HPV31 | E1 | 252 | 10 | GMVMLMLVRF | | 719 |
| HPV31 | E1 | 11 | 8 | GTGCNGWF | | 720 |
| HPV31 | E1 | 11 | 9 | GTGCNGWFY | 3.9000 | 721 |
| HPV31 | E1 | 196 | 11 | GVSFMELIRPF | | 722 |
| HPV31 | E1 | 222 | 10 | GVTGTVAEGF | | 723 |
| HPV31 | E1 | 243 | 9 | HLQSLACSW | | 724 |
| HPV31 | E1 | 328 | 8 | HSFNDTTF | | 725 |
| HPV31 | E1 | 560 | 9 | HSRLVVFTF | | 726 |
| HPV31 | E1 | 478 | 11 | IISYANSKSHF | | 727 |
| HPV31 | E1 | 309 | 11 | ISDVYGETPEW | | 728 |
| HPV31 | E1 | 471 | 11 | ISFLQGCIISY | | 729 |
| HPV31 | E1 | 479 | 10 | ISYANSKSHF | | 730 |
| HPV31 | E1 | 479 | 11 | ISYANSKSHFW | | 731 |
| HPV31 | E1 | 291 | 10 | KLRSTAAALY | | 732 |
| HPV31 | E1 | 291 | 11 | KLRSTAAALYW | | 733 |
| HPV31 | E1 | 590 | 8 | KSFFSRTW | | 734 |
| HPV31 | E1 | 463 | 11 | KSYFGMSLISF | | 735 |
| HPV31 | E1 | 119 | 8 | KTAKRRLF | | 736 |
| HPV31 | E1 | 232 | 10 | KTLLQPYCLY | | 737 |
| HPV31 | E1 | 412 | 8 | KVSDEGDW | | 738 |
| HPV31 | E1 | 234 | 8 | LLQPYCLY | | 739 |
| HPV31 | E1 | 94 | 10 | LSDISSCVDY | | 740 |
| HPV31 | E1 | 584 | 9 | LSDKNWKSF | | 741 |
| HPV31 | E1 | 584 | 10 | LSDKNWKSFF | | 742 |
| HPV31 | E1 | 337 | 9 | LSQMVQWAY | | 743 |
| HPV31 | E1 | 563 | 10 | LVVFTFPNPF | | 744 |
| HPV31 | E1 | 500 | 10 | MLDDATTPCW | | 745 |
| HPV31 | E1 | 187 | 9 | MLGKFKELY | | 746 |
| HPV31 | E1 | 306 | 8 | MSNISDVY | | 747 |
| HPV31 | E1 | 47 | 11 | MVDFIDNCNVY | | 748 |
| HPV31 | E1 | 253 | 9 | MVMLMLVRF | | 749 |
| HPV31 | E1 | 547 | 10 | NINAGKDDRW | | 750 |
| HPV31 | E1 | 117 | 10 | NSKTAKRRLF | | 751 |
| HPV31 | E1 | 93 | 11 | PLSDISSCVDY | | 752 |
| HPV31 | E1 | 580 | 10 | PVYELSDKNW | | 753 |
| HPV31 | E1 | 207 | 10 | QSKNSTCTDW | | 754 |
| HPV31 | E1 | 323 | 8 | QTVLQHSF | | 755 |
| HPV31 | E1 | 124 | 10 | RLFELPDSGY | | 756 |
| HPV31 | E1 | 562 | 11 | RLVVFTFPNPF | | 757 |
| HPV31 | E1 | 293 | 8 | RSTAAALY | | 758 |
| HPV31 | E1 | 293 | 9 | RSTAAALYW | | 759 |
| HPV31 | E1 | 293 | 10 | RSTAAALYWY | | 760 |
| HPV31 | E1 | 303 | 11 | RTGMSNISDVY | | 761 |
| HPV31 | E1 | 40 | 11 | SSDTGEDMVDF | | 762 |
| HPV31 | E1 | 294 | 8 | STAAALYW | | 763 |
| HPV31 | E1 | 294 | 9 | STAAALYWY | | 764 |
| HPV31 | E1 | 211 | 11 | STCTDWCVAAF | | 765 |
| HPV31 | E1 | 233 | 9 | TLLQPYCLY | | 766 |
| HPV31 | E1 | 333 | 11 | TTFDLSQMVQW | | 767 |
| HPV31 | E1 | 505 | 11 | TTPCWHYIDNY | | 768 |
| HPV31 | E1 | 325 | 11 | VLQHSFNDTTF | | 769 |

TABLE VII-continued

A01 Supermotif Peptides

| Type | Protein | Position | No. of Amino Acids | Sequence | A*0101 | Seq. Id. No. |
|---|---|---|---|---|---|---|
| HPV31 | E1 | 349 | 9 | VMDDSEIAY | | 770 |
| HPV31 | E1 | 349 | 11 | VMDDSEIAYKY | | 771 |
| HPV31 | E1 | 254 | 8 | VMLMLVRF | | 772 |
| HPV31 | E1 | 434 | 10 | VSFLSALKLF | | 773 |
| HPV31 | E1 | 197 | 10 | VSFMELIRPF | | 774 |
| HPV31 | E1 | 223 | 9 | VTGTVAEGF | | 775 |
| HPV31 | E1 | 564 | 9 | VVFTFPNPF | | 776 |
| HPV31 | E1 | 564 | 11 | VVFTFPNPFPF | | 777 |
| HPV31 | E1 | 558 | 9 | YLHSRLVVF | | 778 |
| HPV31 | E1 | 558 | 11 | YLHSRLVVFTF | | 779 |
| HPV31 | E2 | 307 | 9 | CLRYRLSKY | | 780 |
| HPV31 | E2 | 22 | 11 | DSKRLCDHIDY | | 781 |
| HPV31 | E2 | 124 | 8 | DVHNTMHY | | 782 |
| HPV31 | E2 | 124 | 11 | DVHNTMHYTNW | | 783 |
| HPV31 | E2 | 197 | 11 | ESVFSSDEISF | | 784 |
| HPV31 | E2 | 80 | 8 | ETLNNTEY | | 785 |
| HPV31 | E2 | 185 | 11 | EVHAGGQVIVF | | 786 |
| HPV31 | E2 | 200 | 8 | FSSDEISF | | 787 |
| HPV31 | E2 | 171 | 8 | FTEEAKKY | | 788 |
| HPV31 | E2 | 168 | 11 | FVNFTEEAKKY | | 789 |
| HPV31 | E2 | 35 | 10 | HIRLECVLMY | | 790 |
| HPV31 | E2 | 164 | 8 | HITYFVNF | | 791 |
| HPV31 | E2 | 345 | 9 | ISTSQRDDF | | 792 |
| HPV31 | E2 | 193 | 8 | IVFPESVF | | 793 |
| HPV31 | E2 | 312 | 8 | LSKYKQLY | | 794 |
| HPV31 | E2 | 78 | 10 | MLETLNNTEY | | 795 |
| HPV31 | E2 | 77 | 11 | MMLETLNNTEY | | 796 |
| HPV31 | E2 | 303 | 8 | NILKCLRY | | 797 |
| HPV31 | E2 | 84 | 9 | NTEYKNEDW | | 798 |
| HPV31 | E2 | 127 | 8 | NTMHYTNW | | 799 |
| HPV31 | E2 | 127 | 10 | NTMHYTNWKF | | 800 |
| HPV31 | E2 | 361 | 9 | NTVSVSTGY | | 801 |
| HPV31 | E2 | 9 | 11 | NVCQDKILEHY | | 802 |
| HPV31 | E2 | 106 | 10 | PTGCLKKHGY | | 803 |
| HPV31 | E2 | 317 | 10 | QLYEQVSSTW | | 804 |
| HPV31 | E2 | 191 | 10 | QVIVFPESVF | | 805 |
| HPV31 | E2 | 151 | 8 | QVNCKGIY | | 806 |
| HPV31 | E2 | 151 | 9 | QVNCKGIYY | | 807 |
| HPV31 | E2 | 321 | 8 | QVSSTWHW | | 808 |
| HPV31 | E2 | 25 | 8 | RLCDHIDY | | 809 |
| HPV31 | E2 | 25 | 9 | RLCDHIDYW | | 810 |
| HPV31 | E2 | 37 | 8 | RLECVLMY | | 811 |
| HPV31 | E2 | 311 | 9 | RLSKYKQLY | | 812 |
| HPV31 | E2 | 346 | 8 | STSQRDDF | | 813 |
| HPV31 | E2 | 198 | 10 | SVFSSDEISF | | 814 |
| HPV31 | E2 | 128 | 9 | TMHYTNWKF | | 815 |
| HPV31 | E2 | 128 | 11 | TMHYTNWKFIY | | 816 |
| HPV31 | E2 | 93 | 10 | TMQQTSLELY | | 817 |
| HPV31 | E2 | 362 | 8 | TVSVSTGY | | 818 |
| HPV31 | E2 | 192 | 9 | VIVFPESVF | | 819 |
| HPV31 | E2 | 92 | 11 | WTMQQTSLELY | | 820 |
| HPV31 | E2 | 344 | 10 | YISTSQRDDF | | 821 |
| HPV31 | E2 | 131 | 8 | YTNWKFIY | | 822 |
| HPV31 | E2 | 159 | 9 | YVHEGHITY | | 823 |
| HPV31 | E2 | 159 | 10 | YVHEGHITYF | | 824 |
| HPV31 | E5 | 40 | 11 | ATLLLLIVILW | | 825 |
| HPV31 | E5 | 53 | 8 | ATSPLRCF | | 826 |
| HPV31 | E5 | 53 | 11 | ATSPLRCFCIY | | 827 |
| HPV31 | E5 | 61 | 8 | CIYVVFIY | | 828 |
| HPV31 | E5 | 15 | 10 | FLLCFCVLLF | | 829 |
| HPV31 | E5 | 72 | 9 | FVIHTHASF | | 830 |
| HPV31 | E5 | 6 | 10 | ISTVSIVLCF | | 831 |
| HPV31 | E5 | 11 | 9 | IVLCFLLCF | | 832 |
| HPV31 | E5 | 16 | 9 | LLCFCVLLF | | 833 |
| HPV31 | E5 | 43 | 8 | LLLIVILW | | 834 |
| HPV31 | E5 | 42 | 9 | LLLLIVILW | | 835 |
| HPV31 | E5 | 32 | 8 | LVLSVSVY | | 836 |
| HPV31 | E5 | 5 | 11 | NISTVSIVLCF | | 837 |
| HPV31 | E5 | 70 | 11 | PLFVIHTHASF | | 838 |
| HPV31 | E5 | 56 | 8 | PLRCFCIY | | 839 |
| HPV31 | E5 | 56 | 11 | PLRCFCIYVVF | | 840 |
| HPV31 | E5 | 31 | 9 | PLVLSVSVY | | 841 |
| HPV31 | E5 | 10 | 10 | SIVLCFLLCF | | 842 |
| HPV31 | E5 | 7 | 9 | STVSIVLCF | | 843 |

TABLE VII-continued

A01 Supermotif Peptides

| Type | Protein | Position | No. of Amino Acids | Sequence | A*0101 | Seq. Id. No. |
|---|---|---|---|---|---|---|
| HPV31 | E5 | 41 | 10 | TLLLLIVILW | | 844 |
| HPV31 | E5 | 54 | 10 | TSPLRCFCIY | | 845 |
| HPV31 | E5 | 8 | 8 | TVSIVLCF | | 846 |
| HPV31 | E5 | 51 | 10 | VIATSPLRCF | | 847 |
| HPV31 | E5 | 73 | 8 | VIHTHASF | | 848 |
| HPV31 | E5 | 12 | 8 | VLCFLLCF | | 849 |
| HPV31 | E5 | 9 | 11 | VSIVLCFLLCF | | 850 |
| HPV31 | E5 | 64 | 9 | VVFIYIPLF | | 851 |
| HPV31 | E5 | 50 | 11 | WVIATSPLRCF | | 852 |
| HPV31 | E5 | 63 | 10 | YVVFIYIPLF | | 853 |
| HPV31 | E6 | 66 | 11 | CLRFYSKVSEF | | 854 |
| HPV31 | E6 | 63 | 8 | CTKCLRFY | | 855 |
| HPV31 | E6 | 25 | 8 | ELRLNCVY | | 856 |
| HPV31 | E6 | 14 | 10 | ELSSALEIPY | | 857 |
| HPV31 | E6 | 39 | 9 | ETEVLDFAF | | 858 |
| HPV31 | E6 | 47 | 8 | FTDLTIVY | | 859 |
| HPV31 | E6 | 61 | 9 | GVCTKCLRF | | 860 |
| HPV31 | E6 | 61 | 10 | GVCTKCLRFY | | 861 |
| HPV31 | E6 | 118 | 8 | HLDKKKRF | | 862 |
| HPV31 | E6 | 72 | 8 | KVSEFRWY | | 863 |
| HPV31 | E6 | 72 | 10 | KVSEFRWYRY | | 864 |
| HPV31 | E6 | 15 | 9 | LSSALEIPY | | 865 |
| HPV31 | E6 | 37 | 9 | LTETEVLDF | | 866 |
| HPV31 | E6 | 37 | 11 | LTETEVLDFAF | | 867 |
| HPV31 | E6 | 36 | 10 | QLTETEVLDF | | 868 |
| HPV31 | E6 | 16 | 8 | SSALEIPY | | 869 |
| HPV31 | E6 | 73 | 9 | VSEFRWYRY | | 870 |
| HPV31 | E6 | 132 | 9 | WTGRCIACW | | 871 |
| HPV31 | E6 | 70 | 9 | YSKVSEFRW | | 872 |
| HPV31 | E6 | 70 | 10 | YSKVSEFRWY | | 873 |
| HPV31 | E7 | 48 | 10 | DTSNYNIVTF | | 874 |
| HPV31 | E7 | 4 | 8 | ETPTLQDY | | 875 |
| HPV31 | E7 | 78 | 10 | ILQELLMGSF | | 876 |
| HPV31 | E7 | 77 | 11 | RILQELLMGSF | | 877 |
| HPV31 | E7 | 49 | 9 | TSNYNIVTF | | 878 |
| HPV31 | L1 | 348 | 9 | AIANSDTTF | | 879 |
| HPV31 | L1 | 398 | 8 | AILEDWNF | | 880 |
| HPV31 | L1 | 285 | 8 | ATLANSTY | | 881 |
| HPV31 | L1 | 285 | 9 | ATLANSTYF | | 882 |
| HPV31 | L1 | 224 | 9 | DICNSICKY | | 883 |
| HPV31 | L1 | 459 | 11 | DLDQFPLGRKF | | 884 |
| HPV31 | L1 | 129 | 8 | DTENSNRY | | 885 |
| HPV31 | L1 | 203 | 9 | DTGFGAMDF | | 886 |
| HPV31 | L1 | 353 | 9 | DTTFKSSNF | | 887 |
| HPV31 | L1 | 270 | 8 | ESVPTDLY | | 888 |
| HPV31 | L1 | 449 | 8 | EVNLKEKF | | 889 |
| HPV31 | L1 | 456 | 8 | FSADLDQF | | 890 |
| HPV31 | L1 | 323 | 9 | GICWGNQLF | | 891 |
| HPV31 | L1 | 117 | 11 | GISGHPLLNKF | | 892 |
| HPV31 | L1 | 413 | 9 | GSLEDTYRF | | 893 |
| HPV31 | L1 | 298 | 11 | GSMVTSDAQIF | | 894 |
| HPV31 | L1 | 282 | 11 | GSTATLANSTY | | 895 |
| HPV31 | L1 | 393 | 11 | HSMNPAILEDW | | 896 |
| HPV31 | L1 | 118 | 10 | ISGHPLLNKF | | 897 |
| HPV31 | L1 | 382 | 10 | ITLSADIMTY | | 898 |
| HPV31 | L1 | 61 | 11 | IVVPKVSGLQY | | 899 |
| HPV31 | L1 | 381 | 11 | KITLSADIMTY | | 900 |
| HPV31 | L1 | 357 | 8 | KSSNFKEY | | 901 |
| HPV31 | L1 | 65 | 10 | KVSGLQYRVF | | 902 |
| HPV31 | L1 | 20 | 8 | KVVSTDEY | | 903 |
| HPV31 | L1 | 42 | 8 | LLTVGHPY | | 904 |
| HPV31 | L1 | 42 | 9 | LLTVGHPYY | | 905 |
| HPV31 | L1 | 384 | 8 | LSADIMTY | | 906 |
| HPV31 | L1 | 43 | 8 | LTVGHPYY | | 907 |
| HPV31 | L1 | 238 | 11 | MVAEPYGDTLF | | 908 |
| HPV31 | L1 | 201 | 11 | MVDTGFGAMDF | | 909 |
| HPV31 | L1 | 300 | 9 | MVTSDAQIF | | 910E |
| HPV31 | L1 | 351 | 11 | NSDTTFKSSNF | | 911 |
| HPV31 | L1 | 227 | 9 | NSICKYPDY | | 912 |
| HPV31 | L1 | 222 | 11 | PLDICNSICKY | | 913 |
| HPV31 | L1 | 411 | 9 | PSGSLEDTY | | 914 |
| HPV31 | L1 | 411 | 11 | PSGSLEDTYRF | | 915 |
| HPV31 | L1 | 17 | 11 | PVSKVVSTDEY | | 916 |
| HPV31 | L1 | 306 | 8 | QIFNKPYW | | 917 |

TABLE VII-continued

A01 Supermotif Peptides

| Type | Protein | Position | No. of Amino Acids | Sequence | A*0101 | Seq. Id. No. |
|---|---|---|---|---|---|---|
| HPV31 | L1 | 255 | 8 | QMFVRHFF | | 918 |
| HPV31 | L1 | 41 | 9 | RLLTVGHPY | | 919 |
| HPV31 | L1 | 41 | 10 | RLLTVGHPYY | | 920 |
| HPV31 | L1 | 77 | 8 | RLPDNKF | | 921 |
| HPV31 | L1 | 77 | 10 | RLPDNKFGF | | 922 |
| HPV31 | L1 | 75 | 10 | RVRLPDNKF | | 923 |
| HPV31 | L1 | 228 | 8 | SICKYPDY | | 924 |
| HPV31 | L1 | 414 | 8 | SLEDTYRF | | 925 |
| HPV31 | L1 | 2 | 11 | SLWRPSEATVY | | 926 |
| HPV31 | L1 | 394 | 10 | SMNPAILEDW | | 927 |
| HPV31 | L1 | 299 | 10 | SMVTSDAQIF | | 928 |
| HPV31 | L1 | 283 | 10 | STATLANSTY | | 929 |
| HPV31 | L1 | 283 | 11 | STATLANSTYF | | 930 |
| HPV31 | L1 | 286 | 8 | TLANSTYF | | 931 |
| HPV31 | L1 | 383 | 9 | TLSADIMTY | | 932 |
| HPV31 | L1 | 302 | 11 | TSDAQIFNKPY | | 933 |
| HPV31 | L1 | 354 | 8 | TTFKSSNF | | 934 |
| HPV31 | L1 | 354 | 11 | TTFKSSNFKEY | | 935 |
| HPV31 | L1 | 267 | 11 | TVGESVPTDLY | | 936 |
| HPV31 | L1 | 66 | 9 | VSGLQYRVF | | 937 |
| HPV31 | L1 | 18 | 10 | VSKVVSTDEY | | 938 |
| HPV31 | L1 | 28 | 8 | VTRTNIYY | | 939 |
| HPV31 | L1 | 301 | 8 | VTSDAQIF | | 940 |
| HPV31 | L1 | 62 | 10 | VVPKVSGLQY | | 941 |
| HPV31 | L1 | 235 | 9 | YLKMVAEPY | | 942 |
| HPV31 | L1 | 364 | 8 | YLRHGEEF | | 943 |
| HPV31 | L1 | 250 | 8 | YLRREQMF | | 944 |
| HPV31 | L1 | 27 | 8 | YVTRTNIY | | 945 |
| HPV31 | L1 | 27 | 9 | YVTRTNIYY | | 946 |
| HPV31 | L2 | 286 | 11 | ALTSRRNTVRY | | 947 |
| HPV31 | L2 | 311 | 9 | ATIGARVHY | | 948 |
| HPV31 | L2 | 311 | 10 | ATIGARVHYY | | 949 |
| HPV31 | L2 | 311 | 11 | ATIGARVHYYY | | 950 |
| HPV31 | L2 | 376 | 11 | AVQSTSAVSAY | | 951 |
| HPV31 | L2 | 354 | 8 | DIYADTDF | | 952 |
| HPV31 | L2 | 253 | 10 | ETVNAEESLY | | 953 |
| HPV31 | L2 | 253 | 11 | ETVNAEESLYF | | 954 |
| HPV31 | L2 | 237 | 11 | FLSAPKQLITY | | 955 |
| HPV31 | L2 | 433 | 8 | FVDGGDFY | | 956 |
| HPV31 | L2 | 351 | 11 | GLYDIYADTDF | | 957 |
| HPV31 | L2 | 63 | 10 | GSGTGGRTGY | | 958 |
| HPV31 | L2 | 65 | 8 | GTGGRTGY | | 959 |
| HPV31 | L2 | 213 | 11 | GVRRPARLGLY | | 960 |
| HPV31 | L2 | 38 | 11 | HTTIADQILRY | | 961 |
| HPV31 | L2 | 45 | 10 | ILRYGSMGVF | | 962 |
| HPV31 | L2 | 45 | 11 | ILRYGSMGVFF | | 963 |
| HPV31 | L2 | 245 | 8 | ITYENPAY | | 964 |
| HPV31 | L2 | 244 | 9 | LITYENPAY | | 965 |
| HPV31 | L2 | 238 | 10 | LSAPKQLITY | | 966 |
| HPV31 | L2 | 178 | 11 | LSSSSISTHNY | | 967 |
| HPV31 | L2 | 395 | 10 | LSTGFDIPIF | | 968 |
| HPV31 | L2 | 287 | 10 | LTSRRNTVRY | | 969 |
| HPV31 | L2 | 447 | 11 | MLKRRRKRVSY | | 970 |
| HPV31 | L2 | 269 | 8 | NIAPDPDF | | 971 |
| HPV31 | L2 | 390 | 10 | NTTVPLSTGF | | 972 |
| HPV31 | L2 | 410 | 10 | PIEHAPTQVF | | 973 |
| HPV31 | L2 | 122 | 11 | PIPHPPTTSGF | | 974 |
| HPV31 | L2 | 394 | 11 | PLSTGFDIPIF | | 975 |
| HPV31 | L2 | 425 | 9 | PTTPQVSIF | | 976 |
| HPV31 | L2 | 44 | 11 | QILRYGSMGVF | | 977 |
| HPV31 | L2 | 243 | 10 | QLITYENPAY | | 978 |
| HPV31 | L2 | 378 | 9 | QSTSAVSAY | | 979 |
| HPV31 | L2 | 229 | 9 | QVKVIDPTF | | 980 |
| HPV31 | L2 | 429 | 11 | QVSIFVDGGDF | | 981 |
| HPV31 | L2 | 9 | 11 | RTKRASATQLY | | 982 |
| HPV31 | L2 | 431 | 9 | SIFVDGGDF | | 983 |
| HPV31 | L2 | 431 | 10 | SIFVDGGDFY | | 984 |
| HPV31 | L2 | 181 | 8 | SSISTHNY | | 985- |
| HPV31 | L2 | 180 | 9 | SSSISTHNY | | 986 |
| HPV31 | L2 | 179 | 10 | SSSSISTHNY | | 987 |
| HPV31 | L2 | 396 | 9 | STGFDIPIF | | 988 |
| HPV31 | L2 | 151 | 8 | STHENPTF | | 989 |
| HPV31 | L2 | 346 | 8 | STLNDGLY | | 990 |
| HPV31 | L2 | 346 | 11 | STLNDGLYDIY | | 991 |

TABLE VII-continued

A01 Supermotif Peptides

| Type | Protein | Position | No. of Amino Acids | Sequence | A*0101 | Seq. Id. No. |
|---|---|---|---|---|---|---|
| HPV31 | L2 | 379 | 8 | STSAVSAY | | 992 |
| HPV31 | L2 | 149 | 10 | SVSTHENPTF | | 993 |
| HPV31 | L2 | 40 | 9 | TIADQILRY | | 994 |
| HPV31 | L2 | 312 | 8 | TIGARVHY | | 995 |
| HPV31 | L2 | 312 | 9 | TIGARVHYY | | 996 |
| HPV31 | L2 | 312 | 10 | TIGARVHYYY | | 997 |
| HPV31 | L2 | 347 | 10 | TLNDGLYDIY | | 998 |
| HPV31 | L2 | 266 | 11 | TSHNIAPDPDF | | 999 |
| HPV31 | L2 | 288 | 9 | TSRRNTVRY | | 1000 |
| HPV31 | L2 | 345 | 9 | TSTLNDGLY | | 1001 |
| HPV31 | L2 | 148 | 11 | TSVSTHENPTF | | 1002 |
| HPV31 | L2 | 39 | 10 | TTIADQILRY | | 1003 |
| HPV31 | L2 | 426 | 8 | TTPQVSIF | | 1004 |
| HPV31 | L2 | 344 | 10 | TTSTLNDGLY | | 1005 |
| HPV31 | L2 | 343 | 11 | TTTSTLNDGLY | | 1006 |
| HPV31 | L2 | 391 | 9 | TTVPLSTGF | | 1007 |
| HPV31 | L2 | 254 | 9 | TVNAEESLY | | 1008 |
| HPV31 | L2 | 254 | 10 | TVNAEESLYF | | 1009 |
| HPV31 | L2 | 392 | 8 | TVPLSTGF | | 1010 |
| HPV31 | L2 | 430 | 10 | VSIFVDGGDF | | 1011 |
| HPV31 | L2 | 430 | 11 | VSIFVDGGDFY | | 1012 |
| HPV31 | L2 | 150 | 9 | VSTHENPTF | | 1013 |
| HPV33 | E1 | 596 | 10 | AINDENWKSF | | 1014 |
| HPV33 | E1 | 596 | 11 | AINDENWKSFF | | 1015 |
| HPV33 | E1 | 81 | 9 | AVCALKRKF | | 1016 |
| HPV33 | E1 | 226 | 9 | CTDWCITGY | | 1017 |
| HPV33 | E1 | 494 | 8 | CVNSKSHF | | 1018 |
| HPV33 | E1 | 494 | 9 | CVNSKSHFW | | 1019 |
| HPV33 | E1 | 349 | 8 | DLSEMVQW | | 1020 |
| HPV33 | E1 | 349 | 10 | DLSEMVQWAY | | 1021 |
| HPV33 | E1 | 365 | 8 | DSDIAYYY | | 1022 |
| HPV33 | E1 | 42 | 9 | DSGTDLLEF | | 1023 |
| HPV33 | E1 | 377 | 9 | DSNSNAAAF | | 1024 |
| HPV33 | E1 | 62 | 9 | DTEAARALF | | 1025 |
| HPV33 | E1 | 324 | 9 | DVQGTTPEW | | 1026 |
| HPV33 | E1 | 516 | 9 | DVTPISWTY | | 1027 |
| HPV33 | E1 | 361 | 10 | ELTDDSDIAY | | 1028 |
| HPV33 | E1 | 361 | 11 | ELTDDSDIAYY | | 1029 |
| HPV33 | E1 | 449 | 8 | FLGAFKKF | | 1030 |
| HPV33 | E1 | 212 | 8 | FMELVRPF | | 1031 |
| HPV33 | E1 | 446 | 8 | FTAFLGAF | | 1032 |
| HPV33 | E1 | 446 | 11 | FTAFLGAFKKF | | 1033 |
| HPV33 | E1 | 265 | 10 | GIIILLLIRF | | 1034 |
| HPV33 | E1 | 209 | 11 | GISFMELVRPF | | 1035 |
| HPV33 | E1 | 11 | 8 | GMGCTGWF | | 1036 |
| HPV33 | E1 | 512 | 11 | GMIDDVTPISW | | 1037 |
| HPV33 | E1 | 564 | 8 | GTDSRWPY | | 1038 |
| HPV33 | E1 | 341 | 8 | HSFNDNIF | | 1039 |
| HPV33 | E1 | 573 | 9 | HSRLTVFEF | | 1040 |
| HPV33 | E1 | 192 | 11 | HSSNTKANILY | | 1041 |
| HPV33 | E1 | 266 | 9 | IIILLLIRF | | 1042 |
| HPV33 | E1 | 267 | 8 | IILLLIRF | | 1043 |
| HPV33 | E1 | 200 | 9 | ILYKFKEAY | | 1044 |
| HPV33 | E1 | 492 | 10 | ISCVNSKSHF | | 1045 |
| HPV33 | E1 | 492 | 11 | ISCVNSKSHFW | | 1046 |
| HPV33 | E1 | 322 | 11 | ISDVQGTTPEW | | 1047 |
| HPV33 | E1 | 210 | 10 | ISFMELVRPF | | 1048 |
| HPV33 | E1 | 520 | 9 | ISWTYIDDY | | 1049 |
| HPV33 | E1 | 124 | 10 | KIDELEDSGY | | 1050 |
| HPV33 | E1 | 304 | 10 | KLRSQTCALY | | 1051 |
| HPV33 | E1 | 304 | 11 | KLRSQTCALYW | | 1052 |
| HPV33 | E1 | 220 | 10 | KSDKTSCTDW | | 1053 |
| HPV33 | E1 | 603 | 8 | KSFFSRTW | | 1054 |
| HPV33 | E1 | 476 | 11 | KSYFGMSLIQF | | 1055 |
| HPV33 | E1 | 425 | 8 | KTNDGGNW | | 1056 |
| HPV33 | E1 | 245 | 10 | KVLIKQHSLY | | 1057 |
| HPV33 | E1 | 247 | 8 | LIKQHSLY | | 1058 |
| HPV33 | E1 | 438 | 9 | LLRYQNIEF | | 1059 |
| HPV33 | E1 | 350 | 9 | LSEMVQWAY | | 1060 |
| HPV33 | E1 | 362 | 9 | LTDDSDIAY | | 1061 |
| HPV33 | E1 | 362 | 10 | LTDDSDIAYY | | 1062 |
| HPV33 | E1 | 362 | 11 | LTDDSDIAYYY | | 1063 |
| HPV33 | E1 | 576 | 10 | LTVFEFKNPF | | 1064 |
| HPV33 | E1 | 336 | 8 | LTVLQHSF | | 1065 |

TABLE VII-continued

A01 Supermotif Peptides

| Type | Protein | Position | No. of Amino Acids | Sequence | A*0101 | Seq. Id. No. |
|---|---|---|---|---|---|---|
| HPV33 | E1 | 513 | 10 | MIDDVTPISW | | 1066 |
| HPV33 | E1 | 443 | 11 | NIEFTAFLGAF | | 1067 |
| HPV33 | E1 | 346 | 11 | NIFDLSEMVQW | | 1068 |
| HPV33 | E1 | 199 | 10 | NILYKFKEAY | | 1069 |
| HPV33 | E1 | 195 | 8 | NTKANILY | | 1070 |
| HPV33 | E1 | 195 | 10 | NTKANILYKF | | 1071 |
| HPV33 | E1 | 560 | 10 | NTNAGTDSRW | | 1072 |
| HPV33 | E1 | 519 | 10 | PISWTYIDDY | | 1073 |
| HPV33 | E1 | 434 | 8 | PIVQLLRY | | 1074 |
| HPV33 | E1 | 593 | 10 | PVYAINDENW | | 1075 |
| HPV33 | E1 | 437 | 10 | QLLRYQNIEF | | 1076 |
| HPV33 | E1 | 308 | 8 | QTCALYWF | | 1077 |
| HPV33 | E1 | 575 | 11 | RLTVFEFKNPF | | 1078 |
| HPV33 | E1 | 335 | 9 | RLTVLQHSF | | 1079 |
| HPV33 | E1 | 306 | 8 | RSQTCALY | | 1080 |
| HPV33 | E1 | 306 | 9 | RSQTCALYW | | 1081 |
| HPV33 | E1 | 306 | 10 | RSQTCALYWF | | 1082 |
| HPV33 | E1 | 111 | 10 | SINKNKECTY | | 1083 |
| HPV33 | E1 | 193 | 10 | SSNTKANILY | | 1084 |
| HPV33 | E1 | 224 | 11 | TSCTDWCITGY | | 1085 |
| HPV33 | E1 | 110 | 11 | TSINKNKECTY | | 1086 |
| HPV33 | E1 | 577 | 9 | TVFEFKNPF | | 1087 |
| HPV33 | E1 | 577 | 11 | TVFEFKNPFPF | | 1088 |
| HPV33 | E1 | 491 | 11 | VISCVNSKSHF | | 1089 |
| HPV33 | E1 | 246 | 9 | VLIKQHSLY | | 1090 |
| HPV33 | E1 | 338 | 11 | VLQHSFNDNIF | | 1091 |
| HPV33 | E1 | 517 | 8 | VTPISWTY | | 1092 |
| HPV33 | E1 | 571 | 9 | YLHSRLTVF | | 1093 |
| HPV33 | E1 | 571 | 11 | YLHSRLTVFEF | | 1094 |
| HPV33 | E2 | 78 | 10 | ALETLSKSQY | | 1095 |
| HPV33 | E2 | 41 | 11 | ALLYTAKQMGF | | 1096 |
| HPV33 | E2 | 10 | 10 | AVQEKILDLY | | 1097 |
| HPV33 | E2 | 288 | 9 | CLRYRLKPY | | 1098 |
| HPV33 | E2 | 145 | 10 | CTMVTGKVDY | | 1099 |
| HPV33 | E2 | 25 | 9 | DLPSQIEHW | | 1100 |
| HPV33 | E2 | 235 | 10 | DTAQPLTKLF | | 1101 |
| HPV33 | E2 | 298 | 10 | ELYSSMSSTW | | 1102 |
| HPV33 | E2 | 282 | 10 | ESNSLKCLRY | | 1103 |
| HPV33 | E2 | 80 | 8 | ETLSKSQY | | 1104 |
| HPV33 | E2 | 100 | 11 | EVWLCEPPKCF | | 1105 |
| HPV33 | E2 | 325 | 10 | FVTEQQQQMF | | 1106 |
| HPV33 | E2 | 34 | 11 | KLIRMECALLY | | 1107 |
| HPV33 | E2 | 84 | 9 | KSQYSTSQW | | 1108 |
| HPV33 | E2 | 23 | 11 | KTDLPSQIEHW | | 1109 |
| HPV33 | E2 | 151 | 8 | KVDYIGMY | | 1110 |
| HPV33 | E2 | 151 | 9 | KVDYIGMYY | | 1111 |
| HPV33 | E2 | 35 | 10 | LIRMECALLY | | 1112 |
| HPV33 | E2 | 62 | 9 | LLASKTKAF | | 1113 |
| HPV33 | E2 | 42 | 10 | LLYTAKQMGF | | 1114 |
| HPV33 | E2 | 82 | 11 | LSKSQYSTSQW | | 1115 |
| HPV33 | E2 | 147 | 8 | MVTGKVDY | | 1116 |
| HPV33 | E2 | 315 | 11 | NSKNGIVTVTF | | 1117 |
| HPV33 | E2 | 284 | 8 | NSLKCLRY | | 1118 |
| HPV33 | E2 | 127 | 8 | NTMDYTNW | | 1119 |
| HPV33 | E2 | 60 | 11 | PSLLASKTKAF | | 1120 |
| HPV33 | E2 | 342 | 9 | PTVQISTGF | | 1121 |
| HPV33 | E2 | 292 | 9 | RLKPYKELY | | 1122 |
| HPV33 | E2 | 37 | 8 | RMECALLY | | 1123 |
| HPV33 | E2 | 61 | 10 | SLLASKTKAF | | 1124 |
| HPV33 | F2 | 302 | 8 | SMSSTWHW | | 1125 |
| HPV33 | E2 | 301 | 9 | SSMSSTWHW | | 1126 |
| HPV33 | E2 | 93 | 10 | TLQQTSLEVW | | 1127 |
| HPV33 | E2 | 128 | 11 | TMDYTNWGEIY | | 1128 |
| HPV33 | E2 | 146 | 9 | TMVTGKVDY | | 1129 |
| HPV33 | E2 | 343 | 8 | TVQISTGF | | 1130 |
| HPV33 | E2 | 326 | 9 | VTEQQQQMF | | 1131 |
| HPV33 | E2 | 148 | 11 | VTGKVDYIGMY | | 1132 |
| HPV33 | E2 | 102 | 9 | WLCEPPKCF | | 1133 |
| HPV33 | E2 | 92 | 11 | WTLQQTSLEVW | | 1134 |
| HPV33 | E2 | 159 | 9 | YIHNCEKVY | | 1135 |
| HPV33 | E2 | 159 | 10 | YIHNCEKVYF | | 1136 |
| HPV33 | E2 | 300 | 8 | YSSMSSTW | | 1137 |
| HPV33 | E2 | 300 | 10 | YSSMSSTWHW | | 1138 |
| HPV33 | E2 | 44 | 8 | YTAKQMGF | | 1139 |

TABLE VII-continued

A01 Supermotif Peptides

| Type | Protein | Position | No. of Amino Acids | Sequence | A*0101 Seq. Id. No. |
|---|---|---|---|---|---|
| HPV33 | E2 | 131 | 8 | YTNWGEIY | 1140 |
| HPV33 | E5 | 56 | 11 | FLYLPMMCINF | 1141 |
| HPV33 | E5 | 3 | 10 | FVFVLCFILF | 1142 |
| HPV33 | E5 | 42 | 9 | FVGSPLKIF | 1143 |
| HPV33 | E5 | 42 | 10 | FVGSPLKIFF | 1144 |
| HPV33 | E5 | 5 | 8 | FVLCFILF | 1145 |
| HPV33 | E5 | 44 | 8 | GSPLKIFF | 1146 |
| HPV33 | E5 | 44 | 10 | GSPLKIFFCY | 1147 |
| HPV33 | E5 | 23 | 9 | ILSISTYAW | 1148 |
| HPV33 | E5 | 48 | 9 | KIFFCYLLF | 1149 |
| HPV33 | E5 | 48 | 11 | KIFFCYLLFLY | 1150 |
| HPV33 | E5 | 22 | 8 | LILSISTY | 1151 |
| HPV33 | E5 | 22 | 10 | LILSISTYAW | 1152 |
| HPV33 | E5 | 32 | 9 | LLVLVLLLW | 1153 |
| HPV33 | E5 | 32 | 11 | LLVLVLLLWVF | 1154 |
| HPV33 | E5 | 24 | 8 | LSISTYAW | 1155 |
| HPV33 | E5 | 35 | 8 | LVLLLWVF | 1156 |
| HPV33 | E5 | 33 | 8 | LVLVLLLW | 1157 |
| HPV33 | E5 | 33 | 10 | LVLVLLLWVF | 1158 |
| HPV33 | E5 | 1 | 9 | MIFVFVLCF | 1159 |
| HPV33 | E5 | 21 | 9 | PLILSISTY | 1160 |
| HPV33 | E5 | 21 | 11 | PLILSISTYAW | 1161 |
| HPV33 | E5 | 46 | 8 | PLKIFFCY | 1162 |
| HPV33 | E5 | 46 | 11 | PLKIFFCYLLF | 1163 |
| HPV33 | E5 | 34 | 9 | VLVLLLWVF | 1164 |
| HPV33 | E5 | 31 | 10 | WLLVLVLLLW | 1165 |
| HPV33 | E5 | 40 | 11 | WVFVGSPLKIF | 1166 |
| HPV33 | E5 | 58 | 9 | YLPMMCINF | 1167 |
| HPV33 | E6 | 66 | 11 | CLRFLSKISEY | 1168 |
| HPV33 | E6 | 69 | 8 | FLSKISEY | 1169 |
| HPV33 | E6 | 69 | 11 | FLSKISEYRHY | 1170 |
| HPV33 | E6 | 61 | 9 | GICKLCLRF | 1171 |
| HPV33 | E6 | 118 | 8 | HVDLNKRF | 1172 |
| HPV33 | E6 | 73 | 9 | ISEYRHYNY | 1173 |
| HPV33 | E6 | 72 | 8 | KISEYRHY | 1174 |
| HPV33 | E6 | 72 | 10 | KISEYRHYNY | 1175 |
| HPV33 | E6 | 70 | 10 | LSKISEYRHY | 1176 |
| HPV33 | E6 | 50 | 11 | LTVVYREGNPF | 1177 |
| HPV33 | E6 | 36 | 8 | PLQRSEVY | 1178 |
| HPV33 | E6 | 36 | 10 | PLQRSEVYDF | 1179 |
| HPV33 | E6 | 39 | 9 | RSEVYDFAF | 1180 |
| HPV33 | E6 | 51 | 10 | TVVYREGNPF | 1181 |
| HPV33 | E6 | 52 | 9 | VVYREGNPF | 1182 |
| HPV33 | E7 | 14 | 10 | DLYPEPTDLY | 1183 |
| HPV33 | E7 | 6 | 11 | PTLKEYVLDLY | 1184 |
| HPV33 | E7 | 7 | 10 | TLKEYVLDLY | 1185 |
| HPV33 | L1 | 392 | 10 | AMNPDILEDW | 1186 |
| HPV33 | L1 | 284 | 8 | ASIQSSAF | 1187 |
| HPV33 | L1 | 284 | 9 | ASIQSSAFF | 1188 |
| HPV33 | L1 | 411 | 9 | ASLQDTYRF | 1189 |
| HPV33 | L1 | 345 | 10 | CTQVTSDSTY | 1190 |
| HPV33 | L1 | 223 | 9 | DICGSTCKY | 1191 |
| HPV33 | L1 | 396 | 8 | DILEDWQF | 1192 |
| HPV33 | L1 | 457 | 11 | DLDQFPLGRKF | 1193 |
| HPV33 | L1 | 351 | 9 | DSTYKNENF | 1194 |
| HPV33 | L1 | 129 | 8 | DTETGNKY | 1195 |
| HPV33 | L1 | 202 | 9 | DTGFGCMDF | 1196 |
| HPV33 | L1 | 303 | 9 | ESQLFNKPY | 1197 |
| HPV33 | L1 | 303 | 10 | ESQLFNKPYW | 1198 |
| HPV33 | L1 | 447 | 8 | EVDLKEKF | 1199 |
| HPV33 | L1 | 249 | 8 | FLRREQMF | 1200 |
| HPV33 | L1 | 454 | 8 | FSADLDQF | 1201 |
| HPV33 | L1 | 322 | 9 | GICWGNQVF | 1202 |
| HPV33 | L1 | 117 | 11 | GISGHPLLNKF | 1203 |
| HPV33 | L1 | 297 | 11 | GSMVTSESQLF | 1204 |
| HPV33 | L1 | 226 | 9 | GSTCKYPDY | 1205 |
| HPV33 | L1 | 281 | 11 | GTTASIQSSAF | 1206 |
| HPV33 | L1 | 365 | 9 | HVEEYDLQF | 1207 |
| HPV33 | L1 | 365 | 11 | HVEEYDLQFVF | 1208 |
| HPV33 | L1 | 118 | 10 | ISGHPLLNKF | 1209 |
| HPV33 | L1 | 65 | 10 | KVSGLQYRVF | 1210 |
| HPV33 | L1 | 379 | 11 | KVTLTAEVMTY | 1211 |
| HPV33 | L1 | 20 | 8 | KVVSTDEY | 1212 |
| HPV33 | L1 | 42 | 8 | LLAVGHPY | 1213 |

TABLE VII-continued

A01 Supermotif Peptides

| Type | Protein | Position | No. of Amino Acids | Sequence | A*0101 | Seq. Id. No. |
|---|---|---|---|---|---|---|
| HPV33 | L1 | 42 | 9 | LLAVGHPYF | | 1214 |
| HPV33 | L1 | 61 | 11 | LLVPKVSGLQY | | 1215 |
| HPV33 | L1 | 382 | 8 | LTAEVMTY | | 1216 |
| HPV33 | L1 | 62 | 10 | LVPKVSGLQY | | 1217 |
| HPV33 | L1 | 237 | 11 | MTSEPYGDSLF | | 1218 |
| HPV33 | L1 | 200 | 11 | MVDTGFGCMDF | | 1219 |
| HPV33 | L1 | 299 | 9 | MVTSESQLF | | 1220 |
| HPV33 | L1 | 221 | 11 | PIDICGSTCKY | | 1221 |
| HPV33 | L1 | 439 | 8 | PLGKYTFW | | 1222 |
| HPV33 | L1 | 409 | 9 | PSASLQDTY | | 1223 |
| HPV33 | L1 | 409 | 11 | PSASLQDTYRF | | 1224 |
| HPV33 | L1 | 17 | 11 | PVSKVVSTDEY | | 1225 |
| HPV33 | L1 | 305 | 8 | QLFNKPYW | | 1226 |
| HPV33 | L1 | 254 | 8 | QMFVRHFF | | 1227 |
| HPV33 | L1 | 347 | 8 | QVTSDSTY | | 1228 |
| HPV33 | L1 | 41 | 9 | RLLAVGHPY | | 1229 |
| HPV33 | L1 | 41 | 10 | RLLAVGHPYF | | 1230 |
| HPV33 | L1 | 77 | 8 | RLPDPNKF | | 1231 |
| HPV33 | L1 | 77 | 10 | RLPDPNKFGF | | 1232 |
| HPV33 | L1 | 75 | 10 | RVRLPDPNKF | | 1233 |
| HPV33 | L1 | 285 | 8 | SIQSSAFF | | 1234 |
| HPV33 | L1 | 412 | 8 | SLQDTYRF | | 1235 |
| HPV33 | L1 | 298 | 10 | SMVTSESQLF | | 1236 |
| HPV33 | L1 | 39 | 11 | SSRLLAVGHPY | | 1237 |
| HPV33 | L1 | 227 | 8 | STCKYPDY | | 1238 |
| HPV33 | L1 | 352 | 8 | STYKNENF | | 1239 |
| HPV33 | L1 | 352 | 11 | STYKNENFKEY | | 1240 |
| HPV33 | L1 | 2 | 11 | SVWRPSEATVY | | 1241 |
| HPV33 | L1 | 266 | 11 | TLGEAVPDDLY | | 1242 |
| HPV33 | L1 | 381 | 9 | TLTAEVMTY | | 1243 |
| HPV33 | L1 | 349 | 11 | TSDSTYKNENF | | 1244 |
| HPV33 | L1 | 238 | 10 | TSEPYGDSLF | | 1245 |
| HPV33 | L1 | 238 | 11 | TSEPYGDSLFF | | 1246 |
| HPV33 | L1 | 301 | 11 | TSESQLFNKPY | | 1247 |
| HPV33 | L1 | 282 | 10 | TTASIQSSAF | | 1248 |
| HPV33 | L1 | 282 | 11 | TTASIQSSAFF | | 1249 |
| HPV33 | L1 | 66 | 9 | VSGLQYRVF | | 1250 |
| HPV33 | L1 | 18 | 10 | VSKVVSTDEY | | 1251 |
| HPV33 | L1 | 28 | 8 | VSRTSIYY | | 1252 |
| HPV33 | L1 | 28 | 9 | VSRTSIYYY | | 1253 |
| HPV33 | L1 | 380 | 10 | VTLTAEVMTY | | 1254 |
| HPV33 | L1 | 300 | 8 | VTSESQLF | | 1255 |
| HPV33 | L1 | 362 | 8 | YIRHVEEY | | 1256 |
| HPV33 | L1 | 234 | 9 | YLKMTSEPY | | 1257 |
| HPV33 | L1 | 27 | 8 | YVSRTSIY | | 1258 |
| HPV33 | L1 | 27 | 9 | YVSRTSIYY | | 1259 |
| HPV33 | L1 | 27 | 10 | YVSRTSIYYY | | 1260 |
| HPV33 | L2 | 291 | 11 | AITSRRHTVRF | | 1261 |
| HPV33 | L2 | 272 | 10 | DISPAPDPDF | | 1262 |
| HPV33 | L2 | 431 | 10 | DTIVVDGADF | | 1263 |
| HPV33 | L2 | 258 | 11 | ESFDPEDTLQF | | 1264 |
| HPV33 | L2 | 447 | 10 | FILRRRRKRF | | 1265 |
| HPV33 | L2 | 242 | 11 | FLTSPHKLITY | | 1266 |
| HPV33 | L2 | 183 | 11 | FSSPTVSTQSY | | 1267 |
| HPV33 | L2 | 440 | 8 | FVLHPSYF | | 1268 |
| HPV33 | L2 | 421 | 8 | FVPISPFF | | 1269 |
| HPV33 | L2 | 421 | 10 | FVPISPFFPF | | 1270 |
| HPV33 | L2 | 64 | 8 | GSGGRTGY | | 1271 |
| HPV33 | L2 | 62 | 10 | GSGSGGRTGY | | 1272 |
| HPV33 | L2 | 218 | 11 | GSRPVARLGLY | | 1273 |
| HPV33 | L2 | 37 | 11 | GSTIADQILKY | | 1274 |
| HPV33 | L2 | 374 | 8 | HTPMQHSY | | 1275 |
| HPV33 | L2 | 374 | 11 | HTPMQHSYSTF | | 1276 |
| HPV33 | L2 | 336 | 8 | HTVPNEQY | | 1277 |
| HPV33 | L2 | 44 | 10 | ILKYGSLGVF | | 1278 |
| HPV33 | L2 | 44 | 11 | ILKYGSLGVFF | | 1279 |
| HPV33 | L2 | 448 | 9 | ILRRRRKRF | | 1280 |
| HPV33 | L2 | 448 | 11 | ILRRRRKRFPY | | 1281 |
| HPV33 | L2 | 273 | 9 | ISPAPDPDF | | 1282 |
| HPV33 | L2 | 155 | 9 | ISTHLNPTF | | 1283 |
| HPV33 | L2 | 292 | 10 | ITSRRHTVRF | | 1284 |
| HPV33 | L2 | 250 | 8 | ITYDNPAF | | 1285 |
| HPV33 | L2 | 250 | 11 | ITYDNPAFESF | | 1286 |
| HPV33 | L2 | 104 | 10 | IVSLIEETSF | | 1287 |

TABLE VII-continued

A01 Supermotif Peptides

| Type | Protein | Position | No. of Amino Acids | Sequence | A*0101 | Seq. Id. No. |
|---|---|---|---|---|---|---|
| HPV33 | L2 | 433 | 8 | IVVDGADF | | 1288 |
| HPV33 | L2 | 248 | 10 | KLITYDNPAF | | 1289 |
| HPV33 | L2 | 249 | 9 | LITYDNPAF | | 1290 |
| HPV33 | L2 | 243 | 10 | LTSPHKLITY | | 1291 |
| HPV33 | L2 | 405 | 11 | MSGPDIPSPLF | | 1292 |
| HPV33 | L2 | 372 | 10 | NVHTPMQHSY | | 1293 |
| HPV33 | L2 | 391 | 10 | NVSIPLNTGF | | 1294 |
| HPV33 | L2 | 423 | 8 | PISPFFPF | | 1295 |
| HPV33 | L2 | 333 | 11 | PLDHTVPNEQY | | 1296 |

TABLE VIII

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E1 | AAALYWYKT | 316 | 9 | | | | | 1856 |
| HPV16 | E1 | AAALYWYKTGI | 316 | 11 | | | | | 1857 |
| HPV16 | E1 | AAFGLTPSI | 239 | 9 | 0.0012 | | | | 1858 |
| HPV16 | E1 | AAFGLTPSIA | 239 | 10 | | | | | 1859 |
| HPV16 | E1 | AALYWYKT | 317 | 8 | | | | | 1860 |
| HPV16 | E1 | AALYWYKTGI | 317 | 10 | | | | | 1861 |
| HPV16 | E1 | AAMLAKFKEL | 205 | 10 | | | | | 1862 |
| HPV16 | E1 | AANTGKSL | 478 | 8 | | | | | 1863 |
| HPV16 | E1 | AANTGKSLFGM | 478 | 11 | | | | | 1864 |
| HPV16 | E1 | AICIEKQSRA | 112 | 10 | | | | | 1865 |
| HPV16 | E1 | AICIEKQSRAA | 112 | 11 | | | | | 1866 |
| HPV16 | E1 | ALDGNLVSM | 539 | 9 | 0.027 | | | | 1867 |
| HPV16 | E1 | ALDGNLVSMDV | 539 | 11 | | | | | 1868 |
| HPV16 | E1 | ALFTAQEA | 69 | 8 | | | | | 1869 |
| HPV16 | E1 | ALKRFLQGI | 459 | 9 | 0.0062 | | | | 1870 |
| HPV16 | E1 | ALYWYKTGI | 318 | 9 | 0.0019 | | | | 1871 |
| HPV16 | E1 | AMLAKFKEL | 206 | 9 | 0.015 | | | | 1872 |
| HPV16 | E1 | AQEAKQHRDA | 73 | 10 | | | | | 1873 |
| HPV16 | E1 | AQEAKQHRDAV | 73 | 11 | | | | | 1874 |
| HPV16 | E1 | AQLADTNSNA | 380 | 10 | | | | | 1875 |
| HPV16 | E1 | ATMCRHYKRA | 406 | 10 | | | | | 1876 |
| HPV16 | E1 | ATVPCWNYI | 524 | 9 | | | | | 1877 |
| HPV16 | E1 | AVQVLKRKYL | 82 | 10 | | | | | 1878 |
| HPV16 | E1 | AVQVLKRKYLV | 82 | 11 | | | | | 1879 |
| HPV16 | E1 | AVVEKKTGDA | 23 | 10 | | | | | 1880 |
| HPV16 | E1 | AVVEKKTGDAI | 23 | 11 | | | | | 1881 |
| HPV16 | E1 | CATMCRHYKRA | 405 | 11 | | | | | 1882 |
| HPV16 | E1 | CIAAFGLT | 237 | 8 | | | | | 1883 |
| HPV16 | E1 | CIAAFGLTPSI | 237 | 11 | | | | | 1884 |
| HPV16 | E1 | CIEKQSRA | 114 | 8 | | | | | 1885 |
| HPV16 | E1 | CIEKQSRAA | 114 | 9 | | | | | 1886 |
| HPV16 | E1 | CILLYGAA | 472 | 8 | | | | | 1887 |
| HPV16 | E1 | CILLYGAANT | 472 | 10 | | | | | 1888 |
| HPV16 | E1 | CLYLHIQSL | 259 | 9 | 0.076 | | | | 1889 |
| HPV16 | E1 | CLYLHIQSLA | 259 | 10 | 0.0032 | | | | 1890 |
| HPV16 | E1 | CMMIEPPKL | 304 | 9 | | | | | 1891 |
| HPV16 | E1 | CQTPLTNI | 187 | 8 | | | | | 1892 |
| HPV16 | E1 | CQTPLTNIL | 187 | 9 | | | | | 1893 |
| HPV16 | E1 | CQTPLTNILNV | 187 | 11 | | | | | 1894 |
| HPV16 | E1 | CTFELSQM | 353 | 8 | | | | | 1895 |
| HPV16 | E1 | CTFELSQMV | 353 | 9 | 0.0029 | | | | 1896 |
| HPV16 | E1 | CVDNNISPRL | 101 | 10 | | | | | 1897 |
| HPV16 | E1 | CVSGQNTNT | 640 | 9 | | | | | 1898 |
| HPV16 | E1 | CVSGQNTNTL | 640 | 10 | | | | | 1899 |
| HPV16 | E1 | CVSPMCMM | 299 | 8 | | | | | 1900 |
| HPV16 | E1 | CVSPMCMMI | 299 | 9 | | | | | 1901 |
| HPV16 | E1 | DAKIGMLDDA | 515 | 10 | | | | | 1902 |
| HPV16 | E1 | DAKIGMLDDAT | 515 | 11 | | | | | 1903 |
| HPV16 | E1 | DATVPCWNYI | 523 | 10 | | | | | 1904 |
| HPV16 | E1 | DAVQVLKRKYL | 81 | 11 | | | | | 1905 |
| HPV16 | E1 | DISGCVDNNI | 97 | 10 | | | | | 1906 |
| HPV16 | E1 | DIVDDSEI | 368 | 8 | | | | | 1907 |
| HPV16 | E1 | DIVDDSEIA | 368 | 9 | | | | | 1908 |
| HPV16 | E1 | DTGEDLVDFI | 43 | 10 | | | | | 1909 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E1 | DTGEDLVDFIV | 43 | 11 | | | | | 1910 |
| HPV16 | E1 | DTNSNASA | 384 | 8 | | | | | 1911 |
| HPV16 | E1 | DTNSNASAFL | 384 | 10 | | | | | 1912 |
| HPV16 | E1 | DTPEWIQRQT | 335 | 10 | | | | | 1913 |
| HPV16 | E1 | DTPEWIQRQTV | 335 | 11 | | | | | 1914 |
| HPV16 | E1 | DVKHRPLV | 548 | 8 | | | | | 1915 |
| HPV16 | E1 | DVKHRPLVQL | 548 | 10 | | | | | 1916 |
| HPV16 | E1 | EAKQHRDA | 75 | 8 | | | | | 1917 |
| HPV16 | E1 | EAKQHRDAV | 75 | 9 | | | | | 1918 |
| HPV16 | E1 | EAKQHRDAVQV | 75 | 11 | | | | | 1919 |
| HPV16 | E1 | EAVVEKKT | 22 | 8 | | | | | 1920 |
| HPV16 | E1 | EAVVEKKTGDA | 22 | 11 | | | | | 1921 |
| HPV16 | E1 | EIAYKYAQL | 374 | 9 | | | | | 1922 |
| HPV16 | E1 | EIAYKYAQLA | 374 | 10 | | | | | 1923 |
| HPV16 | E1 | ELSQMVQWA | 356 | 9 | 0.0003 | | | | 1924 |
| HPV16 | E1 | ELYGVSFSEL | 213 | 10 | | | | | 1925 |
| HPV16 | E1 | ELYGVSFSELV | 213 | 11 | | | | | 1926 |
| HPV16 | E1 | ETAHALFT | 65 | 8 | | | | | 1927 |
| HPV16 | E1 | ETAHALFTA | 65 | 9 | | | | | 1928 |
| HPV16 | E1 | ETETAHAL | 63 | 8 | | | | | 1929 |
| HPV16 | E1 | ETETAHALFT | 63 | 10 | | | | | 1930 |
| HPV16 | E1 | ETETAHALFTA | 63 | 11 | | | | | 1931 |
| HPV16 | E1 | ETIEKLLSKL | 288 | 10 | | | | | 1932 |
| HPV16 | E1 | ETIEKLLSKLL | 288 | 11 | | | | | 1933 |
| HPV16 | E1 | ETQQMLQV | 140 | 8 | | | | | 1934 |
| HPV16 | E1 | EVETQQML | 138 | 8 | | | | | 1935 |
| HPV16 | E1 | EVETQQMLQV | 138 | 10 | | | | | 1936 |
| HPV16 | E1 | EVYGDTPEWI | 331 | 10 | | | | | 1937 |
| HPV16 | E1 | FIVNDNDYL | 51 | 9 | | | | | 1938 |
| HPV16 | E1 | FIVNDNDYLT | 51 | 10 | | | | | 1939 |
| HPV16 | E1 | FLKSNSQA | 392 | 8 | | | | | 1940 |
| HPV16 | E1 | FLKSNSQAKI | 392 | 10 | 0.0011 | | | | 1941 |
| HPV16 | E1 | FLKSNSQAKIV | 392 | 11 | | | | | 1942 |
| HPV16 | E1 | FLQGIPKKNCI | 463 | 11 | | | | | 1943 |
| HPV16 | E1 | FLQGSVICFV | 493 | 10 | 0.23 | | | | 1944 |
| HPV16 | E1 | FLRYQGVEFM | 445 | 10 | | | | | 1945 |
| HPV16 | E1 | FLTALKRFL | 456 | 9 | | | | | 1946 |
| HPV16 | E1 | FMSFLTAL | 453 | 8 | | | | | 1947 |
| HPV16 | E1 | FVNSKSHFWL | 501 | 10 | 0.0015 | | | | 1948 |
| HPV16 | E1 | GAANTGKSL | 477 | 9 | 0.0003 | | | | 1949 |
| HPV16 | E1 | GIPKKNCI | 466 | 8 | | | | | 1950 |
| HPV16 | E1 | GIPKKNCIL | 466 | 9 | | | | | 1951 |
| HPV16 | E1 | GJPKKNCILL | 466 | 10 | | | | | 1952 |
| HPV16 | E1 | GISNISEV | 325 | 8 | | | | | 1953 |
| HPV16 | E1 | GLTPSIADSI | 242 | 10 | 0.0002 | | | | 1954 |
| HPV16 | E1 | GMLDDATV | 519 | 8 | | | | | 1955 |
| HPV16 | E1 | GMSLMKFL | 487 | 8 | | | | | 1956 |
| HPV16 | E1 | GMVVLLLV | 272 | 8 | | | | | 1957 |
| HPV16 | E1 | GTDSRWPYL | 571 | 9 | | | | | 1958 |
| HPV16 | E1 | GTGCNGWFYV | 12 | 10 | 0.0006 | | | | 1959 |
| HPV16 | E1 | GTNGEEGT | 6 | 8 | | | | | 1960 |
| HPV16 | E1 | GVEFMSFL | 450 | 8 | | | | | 1961 |
| HPV16 | E1 | GVEFMSFLT | 450 | 9 | | | | | 1962 |
| HPV16 | E1 | GVEFMSFLTA | 450 | 10 | | | | | 1963 |
| HPV16 | E1 | GVEFMSFLTAL | 450 | 11 | | | | | 1964 |
| HPV16 | E1 | GVSERHTI | 179 | 8 | | | | | 1965 |
| HPV16 | E1 | GVSERHTICQT | 179 | 11 | | | | | 1966 |
| HPV16 | E1 | GVSFSELV | 216 | 8 | | | | | 1967 |
| HPV16 | E1 | HALFTAQEA | 68 | 9 | | | | | 1968 |
| HPV16 | E1 | HIQSLACSWGM | 263 | 11 | | | | | 1969 |
| HPV16 | E1 | HTICQTPL | 184 | 8 | | | | | 1970 |
| HPV16 | E1 | HTICQTPLT | 184 | 9 | | | | | 1971 |
| HPV16 | E1 | HTICQTPLTNI | 184 | 11 | | | | | 1972 |
| HPV16 | E1 | IAAFGLTPSI | 238 | 10 | 0.0002 | | | | 1973 |
| HPV16 | E1 | IAAFGLTPSIA | 238 | 11 | | | | | 1974 |
| HPV16 | E1 | IADSIKTL | 247 | 8 | | | | | 1975 |
| HPV16 | E1 | IADSIKTLL | 247 | 9 | | | | | 1976 |
| HPV16 | E1 | IAYKYAQL | 375 | 8 | | | | | 1977 |
| HPV16 | E1 | IAYKYAQLA | 375 | 9 | | | | | 1978 |
| HPV16 | E1 | IAYKYAQLADT | 375 | 11 | | | | | 1979 |
| HPV16 | E1 | ILLYGAANT | 473 | 9 | | | | | 1980 |
| HPV16 | E1 | ILNVLKTSNA | 194 | 10 | | | | | 1981 |
| HPV16 | E1 | IQSLACSWGM | 264 | 10 | | | | | 1982 |
| HPV16 | E1 | IQSLACSWGMV | 264 | 11 | | | | | 1983 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E1 | ITSNINAGT | 564 | 9 | | | | | 1984 |
| HPV16 | E1 | IVDDSEIA | 369 | 8 | | | | | 1985 |
| HPV16 | E1 | IVKDCATM | 401 | 8 | | | | | 1986 |
| HPV16 | E1 | IVMFLRYQGV | 442 | 10 | 0.0024 | | | | 1987 |
| HPV16 | E1 | IVNDNDYL | 52 | 8 | | | | | 1988 |
| HPV16 | E1 | IVNDNDYLT | 52 | 9 | | | | | 1989 |
| HPV16 | E1 | IVNDNDYLTQA | 52 | 11 | | | | | 1990 |
| HPV16 | E1 | KAAMLAKFKEL | 204 | 11 | | | | | 1991 |
| HPV16 | E1 | KAICIEKQSRA | 111 | 11 | | | | | 1992 |
| HPV16 | E1 | KIGMLDDA | 517 | 8 | | | | | 1993 |
| HPV16 | E1 | KIGMLDDAT | 517 | 9 | | | | | 1994 |
| HPV16 | E1 | KIGMLDDATV | 517 | 10 | | | | | 1995 |
| HPV16 | E1 | KIVKDCAT | 400 | 8 | | | | | 1996 |
| HPV16 | E1 | KIVKDCATM | 400 | 9 | | | | | 1997 |
| HPV16 | E1 | KLLCVSPM | 296 | 8 | | | | | 1998 |
| HPV16 | E1 | KLLCVSPMCM | 296 | 10 | 0.013 | | | | 1999 |
| HPV16 | E1 | KLLCVSPMCMM | 296 | 11 | | | | | 2000 |
| HPV16 | E1 | KLLSKLLCV | 292 | 9 | 0.051 | | | | 2001 |
| HPV16 | E1 | KLRSTAAA | 311 | 8 | | | | | 2002 |
| HPV16 | E1 | KLRSTAAAL | 311 | 9 | 0.0003 | | | | 2003 |
| HPV16 | E1 | KQHRDAVQV | 77 | 9 | | | | | 2004 |
| HPV16 | E1 | KQHRDAVQVL | 77 | 10 | | | | | 2005 |
| HPV16 | E1 | KQMSMSQWI | 418 | 9 | | | | | 2006 |
| HPV16 | E1 | KQSRAAKRRL | 117 | 10 | | | | | 2007 |
| HPV16 | E1 | KTGISNISEV | 323 | 10 | | | | | 2008 |
| HPV16 | E1 | KTLLQQYCL | 252 | 9 | | | | | 2009 |
| HPV16 | E1 | KTLLQQYCLYL | 252 | 11 | | | | | 2010 |
| HPV16 | E1 | KTSNAKAA | 199 | 8 | | | | | 2011 |
| HPV16 | E1 | KTSNAKAAM | 199 | 9 | | | | | 2012 |
| HPV16 | E1 | KTSNAKAAML | 199 | 10 | | | | | 2013 |
| HPV16 | E1 | KTSNAKAAMLA | 199 | 11 | | | | | 2014 |
| HPV16 | E1 | LACSWGMV | 267 | 8 | | | | | 2015 |
| HPV16 | E1 | LACSWGMVV | 267 | 9 | 0.0006 | | | | 2016 |
| HPV16 | E1 | LACSWGMVVL | 267 | 10 | | | | | 2017 |
| HPV16 | E1 | LACSWGMVVLL | 267 | 11 | | | | | 2018 |
| HPV16 | E1 | LADAKIGM | 513 | 8 | | | | | 2019 |
| HPV16 | E1 | LADAKIGML | 513 | 9 | | | | | 2020 |
| HPV16 | E1 | LADTNSNA | 382 | 8 | | | | | 2021 |
| HPV16 | E1 | LADTNSNASA | 382 | 10 | | | | | 2022 |
| HPV16 | E1 | LAKFKELYGV | 208 | 10 | | | | | 2023 |
| HPV16 | E1 | LITSNINA | 563 | 8 | | | | | 2024 |
| HPV16 | E1 | LITSNINAGT | 563 | 10 | | | | | 2025 |
| HPV16 | E1 | LLCVSPMCM | 297 | 9 | 0.0008 | | | | 2026 |
| HPV16 | E1 | LLCVSPMCMM | 297 | 10 | | | | | 2027 |
| HPV16 | E1 | LLCVSPMCMMI | 297 | 11 | | | | | 2028 |
| HPV16 | E1 | LLITSNINA | 562 | 9 | 0.0022 | | | | 2029 |
| HPV16 | E1 | LLITSNINAGT | 562 | 11 | | | | | 2030 |
| HPV16 | E1 | LLQQYCLYL | 254 | 9 | 0.1 | | | | 2031 |
| HPV16 | E1 | LLQQYCLYLHI | 254 | 11 | | | | | 2032 |
| HPV16 | E1 | LLSKLLCV | 293 | 8 | | | | | 2033 |
| HPV16 | E1 | LLSKLLCVSPM | 293 | 11 | | | | | 2034 |
| HPV16 | E1 | LLYGAANT | 474 | 8 | | | | | 2035 |
| HPV16 | E1 | LMKFLQGSV | 490 | 9 | 0.0007 | | | | 2036 |
| HPV16 | E1 | LMKFLQGSVI | 490 | 10 | 0.0003 | | | | 2037 |
| HPV16 | E1 | LQGIPKKNCI | 464 | 10 | | | | | 2038 |
| HPV16 | E1 | LQGIPKKNCIL | 464 | 11 | | | | | 2039 |
| HPV16 | E1 | LQGSVICFV | 494 | 9 | | | | | 2040 |
| HPV16 | E1 | LQHSFNDCT | 346 | 9 | | | | | 2041 |
| HPV16 | E1 | LQPLADAKI | 510 | 9 | | | | | 2042 |
| HPV16 | E1 | LQPLADAKIGM | 510 | 11 | | | | | 2043 |
| HPV16 | E1 | LQQYCLYL | 255 | 8 | | | | | 2044 |
| HPV16 | E1 | LQQYCLYLHI | 255 | 10 | | | | | 2045 |
| HPV16 | E1 | LQVEGRHET | 145 | 9 | | | | | 2046 |
| HPV16 | E1 | LQVEGRHETET | 145 | 11 | | | | | 2047 |
| HPV16 | E1 | LTALKRFL | 457 | 8 | | | | | 2048 |
| HPV16 | E1 | LTALKRFLQGI | 457 | 11 | | | | | 2049 |
| HPV16 | E1 | LTNILNVL | 191 | 8 | | | | | 2050 |
| HPV16 | E1 | LTNILNVLKT | 191 | 10 | | | | | 2051 |
| HPV16 | E1 | LTPSIADSI | 243 | 9 | | | | | 2052 |
| HPV16 | E1 | LTPSIADSIKT | 243 | 11 | | | | | 2053 |
| HPV16 | E1 | LTQAETET | 59 | 8 | | | | | 2054 |
| HPV16 | E1 | LTQAETETA | 59 | 9 | | | | | 2055 |
| HPV16 | E1 | LTQAETETAHA | 59 | 11 | | | | | 2056 |
| HPV16 | E1 | LVQLKCPPL | 554 | 9 | 0.0003 | | | | 2057 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E1 | LVQLKCPPLL | 554 | 10 | | | | | 2058 |
| HPV16 | E1 | LVQLKCPPLLI | 554 | 11 | | | | | 2059 |
| HPV16 | E1 | LVRPFKSNKST | 222 | 11 | | | | | 2060 |
| HPV16 | E1 | LVSMDVKHRPL | 544 | 11 | | | | | 2061 |
| HPV16 | E1 | LVSPLSDI | 91 | 8 | | | | | 2062 |
| HPV16 | E1 | MIEPPKLRST | 306 | 10 | | | | | 2063 |
| HPV16 | E1 | MIEPPKLRSTA | 306 | 11 | | | | | 2064 |
| HPV16 | E1 | MLAKFKEL | 207 | 8 | | | | | 2065 |
| HPV16 | E1 | MLAKFKELYGV | 207 | 11 | | | | | 2066 |
| HPV16 | E1 | MLQVEGRHET | 144 | 10 | | | | | 2067 |
| HPV16 | E1 | MMIEPPKL | 305 | 8 | | | | | 2068 |
| HPV16 | E1 | MMIEPPKLRST | 305 | 11 | | | | | 2069 |
| HPV16 | E1 | MVQWAYDNDI | 360 | 10 | 0.0001 | | | | 2070 |
| HPV16 | E1 | MVQWAYDNDIV | 360 | 11 | | | | | 2071 |
| HPV16 | E1 | NAGTDSRWPYL | 569 | 11 | | | | | 2072 |
| HPV16 | E1 | NAKAAMLA | 202 | 8 | | | | | 2073 |
| HPV16 | E1 | NALDGNLV | 538 | 8 | | | | | 2074 |
| HPV16 | E1 | NALDGNLVSM | 538 | 10 | | | | | 2075 |
| HPV16 | E1 | NILNVLKT | 193 | 8 | | | | | 2076 |
| HPV16 | E1 | NILNVLKTSNA | 193 | 11 | | | | | 2077 |
| HPV16 | E1 | NISEVYGDT | 328 | 9 | | | | | 2078 |
| HPV16 | E1 | NISPRLKA | 105 | 8 | | | | | 2079 |
| HPV16 | E1 | NISPRLKAI | 105 | 9 | | | | | 2080 |
| HPV16 | E1 | NISPRLKAICI | 105 | 11 | | | | | 2081 |
| HPV16 | E1 | NLRNALDGNL | 535 | 10 | | | | | 2082 |
| HPV16 | E1 | NLRNALDGNLV | 535 | 11 | | | | | 2083 |
| HPV16 | E1 | NTEVETQQM | 136 | 9 | | | | | 2084 |
| HPV16 | E1 | NTEVETQQML | 136 | 10 | | | | | 2085 |
| HPV16 | E1 | NTGKSLFGM | 480 | 9 | | | | | 2086 |
| HPV16 | E1 | NTGKSLFGMSL | 480 | 11 | | | | | 2087 |
| HPV16 | E1 | NVLKTSNA | 196 | 8 | | | | | 2088 |
| HPV16 | E1 | NVLKTSNAKA | 196 | 10 | | | | | 2089 |
| HPV16 | E1 | NVLKTSNAKAA | 196 | 11 | | | | | 2090 |
| HPV16 | E1 | PAGTNGEEGT | 4 | 10 | | | | | 2091 |
| HPV16 | E1 | PLADAKIGM | 512 | 9 | | | | | 2092 |
| HPV16 | E1 | PLADAKIGML | 512 | 10 | | | | | 2093 |
| HPV16 | E1 | PLLITSNI | 561 | 8 | | | | | 2094 |
| HPV16 | E1 | PLLITSNINA | 561 | 10 | | | | | 2095 |
| HPV16 | E1 | PLSDISGCV | 94 | 9 | | | | | 2096 |
| HPV16 | E1 | PLTNILNV | 190 | 8 | | | | | 2097 |
| HPV16 | E1 | PLTNILNVL | 190 | 9 | | | | | 2098 |
| HPV16 | E1 | PLTNILNVLKT | 190 | 11 | | | | | 2099 |
| HPV16 | E1 | PLVQLKCPPL | 553 | 10 | | | | | 2100 |
| HPV16 | E1 | PLVQLKCPPLL | 553 | 11 | | | | | 2101 |
| HPV16 | E1 | PMCMMIEPPKL | 302 | 11 | | | | | 2102 |
| HPV16 | E1 | PTFKCVSGQNT | 636 | 11 | | | | | 2103 |
| HPV16 | E1 | QAETETAHA | 61 | 9 | | | | | 2104 |
| HPV16 | E1 | QAETETAHAL | 61 | 10 | | | | | 2105 |
| HPV16 | E1 | QAKIVKDCA | 398 | 9 | | | | | 2106 |
| HPV16 | E1 | QAKIVKDCAT | 398 | 10 | | | | | 2107 |
| HPV16 | E1 | QAKIVKDCATM | 398 | 11 | | | | | 2108 |
| HPV16 | E1 | QIVMFLRYQGV | 441 | 11 | | | | | 2109 |
| HPV16 | E1 | QLADTNSNA | 381 | 9 | 0.0003 | | | | 2110 |
| HPV16 | E1 | QLADTNSNASA | 381 | 11 | | | | | 2111 |
| HPV16 | E1 | QLKCPPLL | 556 | 8 | | | | | 2112 |
| HPV16 | E1 | QLKCPPLLI | 556 | 9 | 0.0049 | | | | 2113 |
| HPV16 | E1 | QLKCPPLLIT | 556 | 10 | | | | | 2114 |
| HPV16 | E1 | QMLQVEGRHET | 143 | 11 | | | | | 2115 |
| HPV16 | E1 | QMSMSQWI | 419 | 8 | | | | | 2116 |
| HPV16 | E1 | QMVQWAYDNDI | 359 | 11 | | | | | 2117 |
| HPV16 | E1 | QQYCLYLHI | 256 | 9 | | | | | 2118 |
| HPV16 | E1 | QTPLTNIL | 188 | 8 | | | | | 2119 |
| HPV16 | E1 | QTPLTNILNV | 188 | 10 | 0.0002 | | | | 2120 |
| HPV16 | E1 | QTPLTNILNVL | 188 | 11 | | | | | 2121 |
| HPV16 | E1 | QVEGRHET | 146 | 8 | | | | | 2122 |
| HPV16 | E1 | QVEGRHETET | 146 | 10 | | | | | 2123 |
| HPV16 | E1 | QVLKRKYL | 84 | 8 | | | | | 2124 |
| HPV16 | E1 | QVLKRKYLV | 84 | 9 | 0.0003 | | | | 2125 |
| HPV16 | E1 | RAEKKQMSM | 414 | 9 | | | | | 2126 |
| HPV16 | E1 | RTWSRLSL | 615 | 8 | | | | | 2127 |
| HPV16 | E1 | RVDDGGDWKQI | 432 | 11 | | | | | 2128 |
| HPV16 | E1 | SAFLKSNSQA | 390 | 10 | | | | | 2129 |
| HPV16 | E1 | SIADSIKT | 246 | 8 | | | | | 2130 |
| HPV16 | E1 | SIADSIKTL | 246 | 9 | | | | | 2131 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E1 | SIADSIKTLL | 246 | 10 | | | | | 2132 |
| HPV16 | E1 | SIKTLLQQYCL | 250 | 11 | | | | | 2133 |
| HPV16 | E1 | SLACSWGM | 266 | 8 | | | | | 2134 |
| HPV16 | E1 | SLACSWGMV | 266 | 9 | 0.082 | | | | 2135 |
| HPV16 | E1 | SLACSWGMVV | 266 | 10 | 0.13 | | | | 2136 |
| HPV16 | E1 | SLACSWGMVVL | 266 | 11 | | | | | 2137 |
| HPVI6 | E1 | SLFGMSLM | 484 | 8 | | | | | 2138 |
| HPV16 | E1 | SLFGMSLMKFL | 484 | 11 | | | | | 2139 |
| HPV16 | E1 | SLMKFLQGSV | 489 | 10 | 0.025 | | | | 2140 |
| HPV16 | E1 | SLMKFLQGSVI | 489 | 11 | | | | | 2141 |
| HPV16 | E1 | SLPTFKCV | 634 | 8 | | | | | 2142 |
| HPV16 | E1 | SMDVKHRPL | 546 | 9 | | | | | 2143 |
| HPV16 | E1 | SMDVKHRPLV | 546 | 10 | | | | | 2144 |
| HPV16 | E1 | SQAKIVKDCA | 397 | 10 | | | | | 2145 |
| HPV16 | E1 | SQAKIVKDCAT | 397 | 11 | | | | | 2146 |
| HPV16 | E1 | SQWIKYRCDRV | 423 | 11 | | | | | 2147 |
| HPV16 | E1 | STAAALYWYKT | 314 | 11 | | | | | 2148 |
| HPV16 | E1 | STCCDWCI | 231 | 8 | | | | | 2149 |
| HPV16 | E1 | STCCDWCIA | 231 | 9 | | | | | 2150 |
| HPV16 | E1 | STCCDWCIAA | 231 | 10 | | | | | 2151 |
| HPV16 | E1 | TAAALYWYKT | 315 | 10 | | | | | 2152 |
| HPV16 | E1 | TAHALFTA | 66 | 8 | | | | | 2153 |
| HPV16 | E1 | TAHALFTAQEA | 66 | 11 | | | | | 2154 |
| HPV16 | E1 | TALKRFLQGI | 458 | 10 | | | | | 2155 |
| HPV16 | E1 | TAQEAKQHRDA | 72 | 11 | | | | | 2156 |
| HPV16 | E1 | TICQTPLT | 185 | 8 | | | | | 2157 |
| HPV16 | E1 | TICQTPLTNI | 185 | 10 | | | | | 2158 |
| HPV16 | E1 | TICQTPLTNIL | 185 | 11 | | | | | 2159 |
| HPV16 | E1 | TIEKLLSKL | 289 | 9 | | | | | 2160 |
| HPV16 | E1 | TIEKLLSKLL | 289 | 10 | | | | | 2161 |
| HPV16 | E1 | TLLQQYCL | 253 | 8 | | | | | 2162 |
| HPV16 | E1 | TLLQQYCLYL | 253 | 10 | 0.65 | | | | 2163 |
| HPV16 | E1 | TMCRHYKRA | 407 | 9 | 0.0003 | | | | 2164 |
| HPV16 | E1 | TQAETETA | 60 | 8 | | | | | 2165 |
| HPV16 | E1 | TQAETETAHA | 60 | 10 | | | | | 2166 |
| HPV16 | E1 | TQAETETAHAL | 60 | 11 | | | | | 2167 |
| HPV16 | E1 | TVLQHSFNDCT | 344 | 11 | | | | | 2168 |
| HPV16 | E1 | TVPCWNYI | 525 | 8 | | | | | 2169 |
| HPV16 | E1 | VLKRKYLV | 85 | 8 | | | | | 2170 |
| HPV16 | E1 | VLKRKYLVSPL | 85 | 11 | | | | | 2171 |
| HPV16 | E1 | VLKTSNAKA | 197 | 9 | | | | | 2172 |
| HPV16 | E1 | VLKTSNAKAA | 197 | 10 | | | | | 2173 |
| HPV16 | E1 | VLKTSNAKAAM | 197 | 11 | | | | | 2174 |
| HPV16 | E1 | VLQHSFNDCT | 345 | 10 | | | | | 2175 |
| HPV16 | E1 | VMFLRYQGV | 443 | 9 | 0.014 | | | | 2176 |
| HPV16 | E1 | VQLKCPPL | 555 | 8 | | | | | 2177 |
| HPV16 | E1 | VQLKCPPLL | 555 | 9 | | | | | 2178 |
| HPV16 | E1 | VQLKCPPLLI | 555 | 10 | | | | | 2179 |
| HPV16 | E1 | VQLKCPPLLIT | 555 | 11 | | | | | 2180 |
| HPV16 | E1 | VQVLKRKYL | 83 | 9 | | | | | 2181 |
| HPV16 | E1 | VQVLKRKYLV | 83 | 10 | | | | | 2182 |
| HPV16 | E1 | VQWAYDNDI | 361 | 9 | | | | | 2183 |
| HPV16 | E1 | VQWAYDNDIV | 361 | 10 | | | | | 2184 |
| HPV16 | E1 | VVEKKTGDA | 24 | 9 | | | | | 2185 |
| HPV16 | E1 | VVEKKTGDAI | 24 | 10 | | | | | 2186 |
| HPV16 | E1 | WAYDNDIV | 363 | 8 | | | | | 2187 |
| HPV16 | E1 | WIKYRCDRV | 425 | 9 | 0.0003 | | | | 2188 |
| HPV16 | E1 | WIQRQTVL | 339 | 8 | | | | | 2189 |
| HPV16 | E1 | WLQPLADA | 509 | 8 | | | | | 2190 |
| HPV16 | E1 | WLQPLADAKI | 509 | 10 | | | | | 2191 |
| HPV16 | E1 | YAQLADTNSNA | 379 | 11 | | | | | 2192 |
| HPV16 | E1 | YIDDNLRNA | 531 | 9 | | | | | 2193 |
| HPV16 | E1 | YIDDNLRNAL | 531 | 10 | | | | | 2194 |
| HPV16 | E1 | YLHIQSLA | 261 | 8 | | | | | 2195 |
| HPV16 | E1 | YLHNRLVV | 578 | 8 | | | | | 2196 |
| HPV16 | E1 | YLHNRLVVFT | 578 | 10 | | | | | 2197 |
| HPV16 | E1 | YLTQAETET | 58 | 9 | | | | | 2198 |
| HPV16 | E1 | YLTQAETETA | 58 | 10 | | | | | 2199 |
| HPV16 | E1 | YLVSPLSDI | 90 | 9 | 0.02 | | | | 2200 |
| HPV16 | E1 | YQGVEFMSFL | 448 | 10 | | | | | 2201 |
| HPV16 | E1 | YQGVEFMSFLT | 448 | 11 | | | | | 2202 |
| HPV16 | E1 | YVEAVVEKKT | 20 | 10 | | | | | 2203 |
| HPV16 | E2 | AATHTKAV | 220 | 8 | | | | | 2204 |
| HPV16 | E2 | AATHTKAVA | 220 | 9 | | | | | 2205 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E2 | AATHTKAVAL | 220 | 10 | | | | | 2206 |
| HPV16 | E2 | AIELQLTL | 72 | 8 | | | | | 2207 |
| HPV16 | E2 | AIELQLTLET | 72 | 10 | | | | | 2208 |
| HPV16 | E2 | AIELQLTLETI | 72 | 11 | | | | | 2209 |
| HPV16 | E2 | AIYYKAREM | 41 | 9 | | | | | 2210 |
| HPV16 | E2 | ALGTEETQT | 228 | 9 | | | | | 2211 |
| HPV16 | E2 | ALGTEETQTT | 228 | 10 | | | | | 2212 |
| HPV16 | E2 | ALGTEETQTTI | 228 | 11 | | | | | 2213 |
| HPV16 | E2 | ALQAIELQL | 69 | 9 | | | | | 2214 |
| HPV16 | E2 | ALQAIELQLT | 69 | 10 | | | | | 2215 |
| HPV16 | E2 | ALQAIELQLTL | 69 | 11 | | | | | 2216 |
| HPV16 | E2 | ATHTKAVA | 221 | 8 | | | | | 2217 |
| HPV16 | E2 | ATHTKAVAL | 221 | 9 | | | | | 2218 |
| HPV16 | E2 | ATHTKAVALGT | 221 | 11 | | | | | 2219 |
| HPV16 | E2 | AVALGTEET | 226 | 9 | | | | | 2220 |
| HPV16 | E2 | AVALGTEETQT | 226 | 11 | | | | | 2221 |
| HPV16 | E2 | AVSKNKAL | 63 | 8 | | | | | 2222 |
| HPV16 | E2 | AVSKNKALQA | 63 | 10 | | | | | 2223 |
| HPV16 | E2 | AVSKNKALQAI | 63 | 11 | | | | | 2224 |
| HPV16 | E2 | AVSSTWHWT | 314 | 9 | | | | | 2225 |
| HPV16 | E2 | CAIYYKAREM | 40 | 10 | | | | | 2226 |
| HPV16 | E2 | CIKKHGYT | 109 | 8 | | | | | 2227 |
| HPV16 | E2 | CIKKHGYTV | 109 | 9 | | | | | 2228 |
| HPV16 | E2 | CIKKHGYTVEV | 109 | 11 | | | | | 2229 |
| HPV16 | E2 | CLRYRFKKHCT | 300 | 11 | | | | | 2230 |
| HPV16 | E2 | CQRLNVCQDKI | 5 | 11 | | | | | 2231 |
| HPV16 | E2 | CTLYTAVSST | 309 | 10 | | | | | 2232 |
| HPV16 | E2 | DAEKYSKNKV | 174 | 10 | | | | | 2233 |
| HPV16 | E2 | DANTLKCL | 294 | 8 | | | | | 2234 |
| HPV16 | E2 | DICNTMHYT | 124 | 9 | | | | | 2235 |
| HPV16 | E2 | DQFLSQVKI | 344 | 9 | | | | | 2236 |
| HPV16 | E2 | DTGNPCHT | 246 | 8 | | | | | 2237 |
| HPV16 | E2 | DTGNPCHTT | 246 | 9 | | | | | 2238 |
| HPV16 | E2 | DTGNPCHTTKL | 246 | 11 | | | | | 2239 |
| HPV16 | E2 | DVSLEVYL | 96 | 8 | | | | | 2240 |
| HPV16 | E2 | DVSLEVYLT | 96 | 9 | | | | | 2241 |
| HPV16 | E2 | DVSLEVYLTA | 96 | 10 | | | | | 2242 |
| HPV16 | E2 | EASVTVVEGQV | 142 | 11 | | | | | 2243 |
| HPV16 | E2 | EIIRQHLA | 209 | 8 | | | | | 2244 |
| HPV16 | E2 | ELQLTLET | 74 | 8 | | | | | 2245 |
| HPV16 | E2 | ELQLTLETI | 74 | 9 | | | | | 2246 |
| HPV16 | E2 | EMGFKHINHQV | 48 | 11 | | | | | 2247 |
| HPV16 | E2 | ETLCQRLNV | 2 | 9 | | | | | 2248 |
| HPV16 | E2 | EVHAGGQV | 185 | 8 | | | | | 2249 |
| HPV16 | E2 | EVHAGGQVI | 185 | 9 | | | | | 2250 |
| HPV16 | E2 | EVHAGGQVIL | 185 | 10 | | | | | 2251 |
| HPV16 | E2 | EVQFDGDI | 118 | 8 | | | | | 2252 |
| HPV16 | E2 | EVQFDGDICNT | 118 | 11 | | | | | 2253 |
| HPV16 | E2 | EVSSPEII | 204 | 8 | | | | | 2254 |
| HPV16 | E2 | EVYLTAPT | 100 | 8 | | | | | 2255 |
| HPV16 | E2 | EVYLTAPTGCI | 100 | 11 | | | | | 2256 |
| HPV16 | E2 | FLSQVKIPKT | 346 | 10 | | | | | 2257 |
| HPV16 | E2 | FLSQVKIPKTI | 346 | 11 | | | | | 2258 |
| HPV16 | E2 | FVQFKDDA | 168 | 8 | | | | | 2259 |
| HPV16 | E2 | GLYYVHEGI | 156 | 9 | | | | | 2260 |
| HPV16 | E2 | GLYYVHEGIRT | 156 | 11 | | | | | 2261 |
| HPV16 | E2 | GQVDYYGL | 150 | 8 | | | | | 2262 |
| HPV16 | E2 | GQVDYYGLYYV | 150 | 11 | | | | | 2263 |
| HPV16 | E2 | GQVILCPT | 190 | 8 | | | | | 2264 |
| HPV16 | E2 | GQVILCPTSV | 190 | 10 | | | | | 2265 |
| HPV16 | E2 | GTEETQTT | 230 | 8 | | | | | 2266 |
| HPV16 | E2 | GTEETQTTI | 230 | 9 | | | | | 2267 |
| HPV16 | E2 | HAGGQVIL | 187 | 8 | | | | | 2268 |
| HPV16 | E2 | HAGGQVILCPT | 187 | 11 | | | | | 2269 |
| HPV16 | E2 | HIDYWKHM | 29 | 8 | | | | | 2270 |
| HPV16 | E2 | HIDYWKFIMRL | 29 | 10 | | | | | 2271 |
| HPV16 | E2 | HINHQVVPT | 53 | 9 | | | | | 2272 |
| HPV16 | E2 | HINHQVVPTL | 53 | 10 | | | | | 2273 |
| HPV16 | E2 | HINHQVVPTLA | 53 | 11 | | | | | 2274 |
| HPV16 | E2 | HIYICEEA | 136 | 8 | | | | | 2275 |
| HPV16 | E2 | HIYICEEASV | 136 | 10 | | | | | 2276 |
| HPV16 | E2 | HIYICEEASVT | 136 | 11 | | | | | 2277 |
| HPV16 | E2 | HLANHPAA | 214 | 8 | | | | | 2278 |
| HPV16 | E2 | HLANHPAAT | 214 | 9 | | | | | 2279 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E2 | HLANHPAATHT | 214 | 11 | | | | | 2280 |
| HPV16 | E2 | HLKGDANT | 290 | 8 | | | | | 2281 |
| HPV16 | E2 | HLKGDANTL | 290 | 9 | | | | | 2282 |
| HPV16 | E2 | HMRLECAI | 35 | 8 | | | | | 2283 |
| HPV16 | E2 | HQVVPTLA | 56 | 8 | | | | | 2284 |
| HPV16 | E2 | HQVVPTLAV | 56 | 9 | | | | | 2285 |
| HPV16 | E2 | HTKAVALGT | 223 | 9 | | | | | 2286 |
| HPV16 | E2 | HTTKLLHRDSV | 252 | 11 | | | | | 2287 |
| HPV16 | E2 | IIRQHLANHPA | 210 | 11 | | | | | 2288 |
| HPV16 | E2 | ILTHYENDST | 15 | 10 | | | | | 2289 |
| HPV16 | E2 | IQRPRSEPDT | 238 | 10 | | | | | 2290 |
| HPV16 | E2 | ITVSTGFM | 356 | 8 | | | | | 2291 |
| HPV16 | E2 | ITVSTGFMSI | 356 | 10 | | | | | 2292 |
| HPV16 | E2 | IVHLKGDA | 288 | 8 | | | | | 2293 |
| HPV16 | E2 | IVHLKGDANT | 288 | 10 | | | | | 2294 |
| HPV16 | E2 | IVHLKGDANTL | 288 | 11 | | | | | 2295 |
| HPV16 | E2 | KALQAIEL | 68 | 8 | | | | | 2296 |
| HPV16 | E2 | KALQAIELQL | 68 | 10 | | | | | 2297 |
| HPV16 | E2 | KALQAIELQLT | 68 | 11 | | | | | 2298 |
| HPV16 | E2 | KAREMGFKHI | 45 | 10 | | | | | 2299 |
| HPV16 | E2 | KAVALGTEET | 225 | 10 | | | | | 2300 |
| HPV16 | E2 | KILTHYENDST | 14 | 11 | | | | | 2301 |
| HPV16 | E2 | KIPKTITV | 351 | 8 | | | | | 2302 |
| HPV16 | E2 | KIPKTITVST | 351 | 10 | | | | | 2303 |
| HPV16 | E2 | KLLHRDSV | 255 | 8 | | | | | 2304 |
| HPV16 | E2 | KLLHRDSVDSA | 255 | 11 | | | | | 2305 |
| HPV16 | E2 | KTITVSTGFM | 354 | 10 | | | | | 2306 |
| HPV16 | E2 | KVWEVHAGGQV | 182 | 11 | | | | | 2307 |
| HPV16 | E2 | LANHPAAT | 215 | 8 | | | | | 2308 |
| HPV16 | E2 | LANHPAATHT | 215 | 10 | | | | | 2309 |
| HPV16 | E2 | LAVSKNKA | 62 | 8 | | | | | 2310 |
| HPV16 | E2 | LAVSKNKAL | 62 | 9 | | | | | 2311 |
| HPV16 | E2 | LAVSKNKALQA | 62 | 11 | | | | | 2312 |
| HPV16 | E2 | LLHRDSVDSA | 256 | 10 | | | | | 2313 |
| HPV16 | E2 | LQAIELQL | 70 | 8 | | | | | 2314 |
| HPV16 | E2 | LQAIELQLT | 70 | 9 | | | | | 2315 |
| HPV16 | E2 | LQAIELQLTL | 70 | 10 | | | | | 2316 |
| HPV16 | E2 | LQDVSLEV | 94 | 8 | | | | | 2317 |
| HPV16 | E2 | LQDVSLEVYL | 94 | 10 | | | | | 2318 |
| HPV16 | E2 | LQDVSLEVYLT | 94 | 11 | | | | | 2319 |
| HPY16 | E2 | LQLTLETI | 75 | 8 | | | | | 2320 |
| HPV16 | E2 | LTAPTGCI | 103 | 8 | | | | | 2321 |
| HPV16 | E2 | LTHYENDST | 16 | 9 | | | | | 2322 |
| HPV16 | E2 | LTHYENDSTDL | 16 | 11 | | | | | 2323 |
| HPV16 | E2 | NTMHYTNWT | 127 | 9 | | | | | 2324 |
| HPV16 | E2 | NTMHYTNWTHI | 127 | 11 | | | | | 2325 |
| HPV16 | E2 | NTTPIVHL | 284 | 8 | | | | | 2326 |
| HPV16 | E2 | NVCQDKIL | 9 | 8 | | | | | 2327 |
| HPV16 | E2 | NVCQDKILT | 9 | 9 | | | | | 2328 |
| HPV16 | E2 | NVKHKSAI | 325 | 8 | | | | | 2329 |
| HPV16 | E2 | NVKHKSAIV | 325 | 9 | | | | | 2330 |
| HPV16 | E2 | NVKHKSAIVT | 325 | 10 | | | | | 2331 |
| HPV16 | E2 | NVKHKSAIVTL | 325 | 11 | | | | | 2332 |
| HPV16 | E2 | PAATHTKA | 219 | 8 | | | | | 2333 |
| HPV16 | E2 | PAATHTKAV | 219 | 9 | | | | | 2334 |
| HPV16 | E2 | PAATHTKAVA | 219 | 10 | | | | | 2335 |
| HPV16 | E2 | PAATHTKAVAL | 219 | 11 | | | | | 2336 |
| HPV16 | E2 | PIVHLKGDA | 287 | 9 | | | | | 2337 |
| HPV16 | E2 | PIVHLKGDANT | 287 | 11 | | | | | 2338 |
| HPV16 | E2 | PTGCIKKHGYT | 106 | 11 | | | | | 2339 |
| HPV16 | E2 | PTLAVSKNKA | 60 | 10 | | | | | 2340 |
| HPV16 | E2 | PTLAVSKNKAL | 60 | 11 | | | | | 2341 |
| HPV16 | E2 | PTSVFSSNEV | 196 | 10 | | | | | 2342 |
| HPV16 | E2 | QAIELQLT | 71 | 8 | | | | | 2343 |
| HPV16 | E2 | QAIELQLTL | 71 | 9 | | | | | 2344 |
| HPV16 | E2 | QAIELQLTLET | 71 | 11 | | | | | 2345 |
| HPV16 | E2 | QVDYYGLYYV | 151 | 10 | | | | | 2346 |
| HPV16 | E2 | QVILCPTSV | 191 | 9 | | | | | 2347 |
| HPV16 | E2 | QVKIPKTI | 349 | 8 | | | | | 2348 |
| HPV16 | E2 | QVKIPKTIT | 349 | 9 | | | | | 2349 |
| HPV16 | E2 | QVKIPKTITV | 349 | 10 | | | | | 2350 |
| HPV16 | E2 | QVVPTLAV | 57 | 8 | | | | | 2351 |
| HPV16 | E2 | RINCNSNT | 278 | 8 | | | | | 2352 |
| HPV16 | E2 | RINCNSNTT | 278 | 9 | | | | | 2353 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E2 | RINCNSNTTPI | 278 | 11 | | | | | 2354 |
| HPV16 | E2 | RLECAIYYKA | 37 | 10 | | | | | 2355 |
| HPV16 | E2 | RLNVCQDKI | 7 | 9 | | | | | 2356 |
| HPV16 | E2 | RLNVCQDKIL | 7 | 10 | | | | | 2357 |
| HPV16 | E2 | RLNVCQDKILT | 7 | 11 | | | | | 2358 |
| HPV16 | E2 | RQHLANHPA | 212 | 9 | | | | | 2359 |
| HPV16 | E2 | RQHLANHPAA | 212 | 10 | | | | | 2360 |
| HPV16 | E2 | RQHLANHPAAT | 212 | 11 | | | | | 2361 |
| HPV16 | E2 | RTYFVQFKDDA | 165 | 11 | | | | | 2362 |
| HPV16 | E2 | SLEVYLTA | 98 | 8 | | | | | 2363 |
| HPV16 | E2 | SLEVYLTAPT | 98 | 10 | | | | | 2364 |
| HPV16 | E2 | SQVKIPKT | 348 | 8 | | | | | 2365 |
| HPV16 | E2 | SQVKIPKTI | 348 | 9 | | | | | 2366 |
| HPV16 | E2 | SQVKIPKTIT | 348 | 10 | | | | | 2367 |
| HPV16 | E2 | SQVKIPKTITV | 348 | 11 | | | | | 2368 |
| HPV16 | E2 | SQYSNEKWT | 85 | 9 | | | | | 2369 |
| HPV16 | E2 | SQYSNEKWTL | 85 | 10 | | | | | 2370 |
| HPV16 | E2 | STDLRDHI | 23 | 8 | | | | | 2371 |
| HPV16 | E2 | STWHWTGHNV | 317 | 10 | | | | | 2372 |
| HPV16 | E2 | SVDSAPIL | 261 | 8 | | | | | 2373 |
| HPV16 | E2 | SVDSAPILT | 261 | 9 | | | | | 2374 |
| HPV16 | E2 | SVDSAPILTA | 261 | 10 | | | | | 2375 |
| HPV16 | E2 | SVFSSNEV | 198 | 8 | | | | | 2376 |
| HPV16 | E2 | SVTVVEGQV | 144 | 9 | | | | | 2377 |
| HPV16 | E2 | TAFNSSHKGRI | 269 | 11 | | | | | 2378 |
| HPV16 | E2 | TAVSSTWHWT | 313 | 10 | | | | | 2379 |
| HPV16 | E2 | TIQRPRSEPDT | 237 | 11 | | | | | 2380 |
| HPV16 | E2 | TITVSTGFM | 355 | 9 | | | | | 2381 |
| HPV16 | E2 | TITVSTGFMSI | 355 | 11 | | | | | 2382 |
| HPV16 | E2 | TLAVSKNKA | 61 | 9 | | | | | 2383 |
| HPV16 | E2 | TLAVSKNKAL | 61 | 10 | | | | | 2384 |
| HPV16 | E2 | TLCQRLNV | 3 | 8 | | | | | 2385 |
| HPV16 | E2 | TLQDVSLEV | 93 | 9 | | | | | 2386 |
| HPV16 | E2 | TLQDVSLEVYL | 93 | 11 | | | | | 2387 |
| HPV16 | E2 | TLYTAVSST | 310 | 9 | | | | | 2388 |
| HPV16 | E2 | TMHYTNWT | 128 | 8 | | | | | 2389 |
| HPV16 | E2 | TMHYTNWTHI | 128 | 10 | | | | | 2390 |
| HPV16 | E2 | TTKLLHRDSV | 253 | 10 | | | | | 2391 |
| HPV16 | E2 | TTPIVHLKGDA | 285 | 11 | | | | | 2392 |
| HPV16 | E2 | TVEVQFDGDI | 116 | 10 | | | | | 2393 |
| HPV16 | E2 | TVSTGFMSI | 357 | 9 | | | | | 2394 |
| HPV16 | E2 | VALGTEET | 227 | 8 | | | | | 2395 |
| HPV16 | E2 | VALGTEETQT | 227 | 10 | | | | | 2396 |
| HPV16 | E2 | VALGTEETQTT | 227 | 11 | | | | | 2397 |
| HPV16 | E2 | VILCPTSV | 192 | 8 | | | | | 2398 |
| HPV16 | E2 | VQFDGDICNT | 119 | 10 | | | | | 2399 |
| HPV16 | E2 | VQFDGDICNTM | 119 | 11 | | | | | 2400 |
| HPV16 | E2 | VTVVEGQV | 145 | 8 | | | | | 2401 |
| HPV16 | E2 | VVEGQVDYYGL | 147 | 11 | | | | | 2402 |
| HPV16 | E2 | WQRDQFLSQV | 341 | 10 | | | | | 2403 |
| HPV16 | E2 | WTGHNVKHKSA | 321 | 11 | | | | | 2404 |
| HPV16 | E2 | WTHIYICEEA | 134 | 10 | | | | | 2405 |
| HPV16 | E2 | WTLQDVSL | 92 | 8 | | | | | 2406 |
| HPV16 | E2 | WTLQDVSLEV | 92 | 10 | | | | | 2407 |
| HPV16 | E2 | YICEEASV | 138 | 8 | | | | | 2408 |
| HPV16 | E2 | YICEEASVT | 138 | 9 | | | | | 2409 |
| HPV16 | E2 | YICEEASVTV | 138 | 10 | | | | | 2410 |
| HPV16 | E2 | YICEEASVTVV | 138 | 11 | | | | | 2411 |
| HPV16 | E2 | YLTAPTGCI | 102 | 9 | | | | | 2412 |
| HPV16 | E2 | YTAVSSTWHWT | 312 | 11 | | | | | 2413 |
| HPV16 | E2 | YTNWTHIYI | 131 | 9 | | | | | 2414 |
| HPV16 | E2 | YTVEVQFDGDI | 115 | 11 | | | | | 2415 |
| HPV16 | E2 | YVHEGIRT | 159 | 8 | | | | | 2416 |
| HPV16 | E2 | YVHEGIRTYFV | 159 | 11 | | | | | 2417 |
| HPV16 | E5 | AASAFRCFI | 53 | 9 | | | | | 2418 |
| HPV16 | E5 | AASAFRCFIV | 53 | 10 | | | | | 2419 |
| HPV16 | E5 | CLLIRPLL | 26 | 8 | | | | | 2420 |
| HPV16 | E5 | CLLIRPLLL | 26 | 9 | | | | | 2421 |
| HPV16 | E5 | CLLIRPLLLSV | 26 | 11 | | | | | 2422 |
| HPV16 | E5 | CVCLLIRPL | 24 | 9 | | | | | 2423 |
| HPV16 | E5 | CVCLLIRPLL | 24 | 10 | | | | | 2424 |
| HPV16 | E5 | CVCLLIRPLLL | 24 | 11 | | | | | 2425 |
| HPV16 | E5 | CVLLCVCL | 20 | 8 | | | | | 2426 |
| HPV16 | E5 | CVLLCVCLL | 20 | 9 | | | | | 2427 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E5 | CVLLCVCLLI | 20 | 10 | | | | | 2428 |
| HPV16 | E5 | DTASTTLL | 5 | 8 | | | | | 2429 |
| HPV16 | E5 | DTASTTLLA | 5 | 9 | | | | | 2430 |
| HPV16 | E5 | FIVYIIFV | 60 | 8 | | | | | 2431 |
| HPV16 | E5 | FIVYIIFVYI | 60 | 10 | | | | | 2432 |
| HPV16 | E5 | FLIHTHARFL | 72 | 10 | | | | | 2433 |
| HPV16 | E5 | FLIHTHARFLI | 72 | 11 | | | | | 2434 |
| HPV16 | E5 | FLLCFCVL | 15 | 8 | | | | | 2435 |
| HPV16 | E5 | FLLCFCVLL | 15 | 9 | | | | | 2436 |
| HPV16 | E5 | FLLCFCVLLCV | 15 | 11 | | | | | 2437 |
| HPV16 | E5 | FVYIPLFL | 66 | 8 | | | | | 2438 |
| HPV16 | E5 | FVYIPLFLI | 66 | 9 | | | | | 2439 |
| HPV16 | E5 | FVYIPLFLIHT | 66 | 11 | | | | | 2440 |
| HPV16 | E5 | HTHARFLI | 75 | 8 | | | | | 2441 |
| HPV16 | E5 | HTHARFLIT | 75 | 9 | | | | | 2442 |
| HPV16 | E5 | IIFVYIPL | 64 | 8 | | | | | 2443 |
| HPV16 | E5 | IIFVYIPLFL | 64 | 10 | | | | | 2444 |
| HPV16 | E5 | IIFVYIPLFLI | 64 | 11 | | | | | 2445 |
| HPV16 | E5 | IILVLLLWI | 43 | 9 | | | | | 2446 |
| HPV16 | E5 | IILVLLLWIT | 43 | 10 | | | | | 2447 |
| HPV16 | E5 | IILVLLLWITA | 43 | 11 | | | | | 2448 |
| HPV16 | E5 | ILVLLLWI | 44 | 8 | | | | | 2449 |
| HPV16 | E5 | ILVLLLWIT | 44 | 9 | | | | | 2450 |
| HPV16 | E5 | ILVLLLWITA | 44 | 10 | | | | | 2451 |
| HPV16 | E5 | ILVLLLWITAA | 44 | 11 | | | | | 2452 |
| HPV16 | E5 | ITAASAFRCFI | 51 | 11 | | | | | 2453 |
| HPV16 | E5 | IVYIIFVYI | 61 | 9 | | | | | 2454 |
| HPV16 | E5 | IVYIIFVYIPL | 61 | 11 | | | | | 2455 |
| HPV16 | E5 | LACFLLCFCV | 12 | 10 | | | | | 2456 |
| HPV16 | E5 | LACFLLCFCVL | 12 | 11 | | | | | 2457 |
| HPV16 | E5 | LIHTHARFL | 73 | 9 | | | | | 2458 |
| HPV16 | E5 | LIHTHARFLI | 73 | 10 | | | | | 2459 |
| HPV16 | E5 | LIHTHARFLIT | 73 | 11 | | | | | 2460 |
| HPV16 | E5 | LIILVLLL | 42 | 8 | | | | | 2461 |
| HPV16 | E5 | LIILVLLLWI | 42 | 10 | | | | | 2462 |
| HPV16 | E5 | LIILVLLLWIT | 42 | 11 | | | | | 2463 |
| HPV16 | E5 | LIRPLLLSV | 28 | 9 | | | | | 2464 |
| HPV16 | E5 | LIRPLLLSVST | 28 | 11 | | | | | 2465 |
| HPV16 | E5 | LLACFLLCFCV | 11 | 11 | | | | | 2466 |
| HPV16 | E5 | LLCFCVLL | 16 | 8 | | | | | 2467 |
| HPV16 | E5 | LLCFCVLLCV | 16 | 10 | | | | | 2468 |
| HPV16 | E5 | LLCVCLLI | 22 | 8 | | | | | 2469 |
| HPV16 | E5 | LLCVCLLIRPL | 22 | 11 | | | | | 2470 |
| HPV16 | E5 | LLIRPLLL | 27 | 8 | | | | | 2471 |
| HPV16 | E5 | LLIRPLLLSV | 27 | 10 | | | | | 2472 |
| HPV16 | E5 | LLLSVSTYT | 32 | 9 | | | | | 2473 |
| HPV16 | E5 | LLLSVSTYTSL | 32 | 11 | | | | | 2474 |
| HPV16 | E5 | LLLWITAA | 47 | 8 | | | | | 2475 |
| HPV16 | E5 | LLLWITAASA | 47 | 10 | | | | | 2476 |
| HPV16 | E5 | LLSVSTYT | 33 | 8 | | | | | 2477 |
| HPV16 | E5 | LLSVSTYTSL | 33 | 10 | | | | | 2478 |
| HPV16 | E5 | LLSVSTYTSLI | 33 | 11 | | | | | 2479 |
| HPV16 | E5 | LLWITAASA | 48 | 9 | | | | | 2480 |
| HPV16 | E5 | LVLLLWIT | 45 | 8 | | | | | 2481 |
| HPV16 | E5 | LVLLLWITA | 45 | 9 | | | | | 2482 |
| HPV16 | E5 | LVLLLWITAA | 45 | 10 | | | | | 2483 |
| HPV16 | E5 | MTNLDTAST | 1 | 9 | | | | | 2484 |
| HPV16 | E5 | MTNLDTASTT | 1 | 10 | | | | | 2485 |
| HPV16 | E5 | MTNLDTASTTL | 1 | 11 | | | | | 2486 |
| HPV16 | E5 | NLDTASTT | 3 | 8 | | | | | 2487 |
| HPV16 | E5 | NLDTASTTL | 3 | 9 | | | | | 2488 |
| HPV16 | E5 | NLDTASTTLL | 3 | 10 | | | | | 2489 |
| HPV16 | E5 | NLDTASTTLLA | 3 | 11 | | | | | 2490 |
| HPV16 | E5 | PLFLIHTHA | 70 | 9 | | | | | 2491 |
| HPV16 | E5 | PLLLSVST | 31 | 8 | | | | | 2492 |
| HPV16 | E5 | PLLLSVSTYT | 31 | 10 | | | | | 2493 |
| HPV16 | E5 | SAFRCFIV | 55 | 8 | | | | | 2494 |
| HPV16 | E5 | SAFRCFIVYI | 55 | 10 | | | | | 2495 |
| HPV16 | E5 | SAFRCFIVYII | 55 | 11 | | | | | 2496 |
| HPV16 | E5 | SLIILVLL | 41 | 8 | | | | | 2497 |
| HPV16 | E5 | SLIILVLLL | 41 | 9 | | | | | 2498 |
| HPV16 | E5 | SLIILVLLLWI | 41 | 11 | | | | | 2499 |
| HPV16 | E5 | STTLLACFL | 8 | 9 | | | | | 2500 |
| HPV16 | E5 | STTLLACFLL | 8 | 10 | | | | | 2501 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E5 | STYTSLII | 37 | 8 | | | | | 2502 |
| HPV16 | E5 | STYTSLIIL | 37 | 9 | | | | | 2503 |
| HPV16 | E5 | STYTSLIILV | 37 | 10 | | | | | 2504 |
| HPV16 | E5 | STYTSLIILVL | 37 | 11 | | | | | 2505 |
| HPV16 | E5 | SVSTYTSL | 35 | 8 | | | | | 2506 |
| HPV16 | E5 | SVSTYTSLI | 35 | 9 | | | | | 2507 |
| HPV16 | E5 | SVSTYTSLII | 35 | 10 | | | | | 2508 |
| HPV16 | E5 | SVSTYTSLIIL | 35 | 11 | | | | | 2509 |
| HPV16 | E5 | TAASAFRCFI | 52 | 10 | | | | | 2510 |
| HPV16 | E5 | TAASAFRCFIV | 52 | 11 | | | | | 2511 |
| HPV16 | E5 | TASTTLLA | 6 | 8 | | | | | 2512 |
| HPV16 | E5 | TASTTLLACFL | 6 | 11 | | | | | 2513 |
| HPV16 | E5 | TLLACFLL | 10 | 8 | | | | | 2514 |
| HPV16 | E5 | TTLLACFL | 9 | 8 | | | | | 2515 |
| HPV16 | E5 | TTLLACFLL | 9 | 9 | | | | | 2516 |
| HPV16 | E5 | VLLCVCLL | 21 | 8 | | | | | 2517 |
| HPV16 | E5 | VLLCVCLLI | 21 | 9 | | | | | 2518 |
| HPV16 | E5 | VLLLWITA | 46 | 8 | | | | | 2519 |
| HPV16 | E5 | VLLLWITAA | 46 | 9 | | | | | 2520 |
| HPV16 | E5 | VLLLWITAASA | 46 | 11 | | | | | 2521 |
| HPV16 | E5 | YIIFVYIPL | 63 | 9 | | | | | 2522 |
| HPV16 | E5 | YIIFVYIPLFL | 63 | 11 | | | | | 2523 |
| HPV16 | E5 | YIPLFLIHT | 68 | 9 | | | | | 2524 |
| HPV16 | E5 | YIPLFLIHTHA | 68 | 11 | | | | | 2525 |
| HPV16 | E5 | YTSLIILV | 39 | 8 | | | | | 2526 |
| HPV16 | E5 | YTSLIILVL | 39 | 9 | | | | | 2527 |
| HPV16 | E5 | YTSLIILVLL | 39 | 10 | | | | | 2528 |
| HPV16 | E5 | YTSLIILVLLL | 39 | 11 | | | | | 2529 |
| HPV16 | E6 | CINCQKPL | 110 | 8 | 0.0001 | | | | 2530 |
| HPV16 | E6 | CIVYRDGNPYA | 58 | 11 | | | | | 2531 |
| HPV16 | E6 | CLKFYSKI | 73 | 8 | 0.0001 | | | | 2532 |
| HPV16 | E6 | CMSCCRSSRT | 143 | 10 | 0.0001 | | | | 2533 |
| HPV16 | E6 | CTELQTTI | 23 | 8 | | | | | 2534 |
| HPV16 | E6 | CTELQTTIHDI | 23 | 11 | | | | | 2535 |
| HPV16 | E6 | CVYCKQQL | 37 | 8 | 0.0001 | | | | 2536 |
| HPV16 | E6 | CVYCKQQLL | 37 | 9 | 0.0001 | | | | 2537 |
| HPV16 | E6 | ELQTTIHDI | 25 | 9 | 0.0001 | | | | 2538 |
| HPV16 | E6 | ELQTTIHDII | 25 | 10 | 0.0002 | | | | 2539 |
| HPV16 | E6 | ELQTTIHDIIL | 25 | 11 | 0.0001 | | | | 2540 |
| HPV16 | E6 | EQQYNKPL | 96 | 8 | | | | | 2541 |
| HPV16 | E6 | EQQYNKPLCDL | 96 | 11 | | | | | 2542 |
| HPV16 | E6 | EVYDFAFRDL | 48 | 10 | 0.0001 | | | | 2543 |
| HPV16 | E6 | FAFRDLCI | 52 | 8 | | | | | 2544 |
| HPV16 | E6 | FAFRDLCIV | 52 | 9 | 0.051 | | | | 2545 |
| HPV16 | E6 | FQDPQERPRKL | 9 | 11 | | | | | 2546 |
| HPV16 | E6 | HLDKKQRFHNI | 125 | 11 | | | | | 2547 |
| HPV16 | E6 | ILECVYCKQQL | 34 | 11 | 0.0004 | | | | 2548 |
| HPV16 | E6 | IVYRDGNPYA | 59 | 10 | 0.0002 | | | | 2549 |
| HPV16 | E6 | IVYRDGNPYAV | 59 | 11 | | | | | 2550 |
| HPV16 | E6 | KLPQLCTEL | 18 | 9 | 0.0009 | | | | 2551 |
| HPV16 | E6 | KLPQLCTELQT | 18 | 11 | | | | | 2552 |
| HPV16 | E6 | KQQLLRREV | 41 | 9 | | | | | 2553 |
| HPV16 | E6 | LIRCINCQKPL | 107 | 11 | | | | | 2554 |
| HPV16 | E6 | LLRREVYDFA | 44 | 10 | 0.0003 | | | | 2555 |
| HPV16 | E6 | LQTTIHDI | 26 | 8 | | | | | 2556 |
| HPV16 | E6 | LQTTIHDII | 26 | 9 | 0.0002 | | | | 2557 |
| HPV16 | E6 | LQTTIHDIIL | 26 | 10 | | | | | 2558 |
| HPV16 | E6 | NIRGRWTGRCM | 134 | 11 | | | | | 2559 |
| HPV16 | E6 | PLCDLLIRCI | 102 | 10 | 0.0001 | | | | 2560 |
| HPV16 | E6 | PLCPEEKQRHL | 116 | 11 | 0.0001 | | | | 2561 |
| HPV16 | E6 | PQERPRKL | 12 | 8 | | | | | 2562 |
| HPV16 | E6 | PQERPRKLPQL | 12 | 11 | | | | | 2563 |
| HPV16 | E6 | PQLCTELQT | 20 | 9 | | | | | 2564 |
| HPV16 | E6 | PQLCTELQTT | 20 | 10 | | | | | 2565 |
| HPV16 | E6 | PQLCTELQTTI | 20 | 11 | | | | | 2566 |
| HPV16 | E6 | QLCTELQT | 21 | 8 | | | | | 2567 |
| HPV16 | E6 | QLCTELQTT | 21 | 9 | 0.0001 | | | | 2568 |
| HPV16 | E6 | QLCTELQTTI | 21 | 10 | 0.0012 | | | | 2569 |
| HPV16 | E6 | QLLRREVYDFA | 43 | 11 | | | | | 2570 |
| HPV16 | E6 | QQLLRREV | 42 | 8 | | | | | 2571 |
| HPV16 | E6 | QQYNKPLCDL | 97 | 10 | | | | | 2572 |
| HPV16 | E6 | QQYNKPLCDLL | 97 | 11 | | | | | 2573 |
| HPV16 | E6 | QTTIHDII | 27 | 8 | | | | | 2574 |
| HPV16 | E6 | QTTIHDIIL | 27 | 9 | | | | | 2575 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | E6 | RTRRETQL | 151 | 8 | | | | | 2576 |
| HPV16 | E6 | TIHDIILECV | 29 | 10 | 0.021 | | | | 2577 |
| HPV16 | E6 | TLEQQYNKPL | 94 | 10 | 0.0001 | | | | 2578 |
| HPV16 | E6 | TTIHDIIL | 28 | 8 | | | | | 2579 |
| HPV16 | E6 | TTIHDIILECV | 28 | 11 | | | | | 2580 |
| HPV16 | E6 | TTLEQQYNKPL | 93 | 11 | | | | | 2581 |
| HPV16 | E6 | YAVCDKCL | 67 | 8 | | | | | 2582 |
| HPV16 | E7 | CVQSTHVDI | 68 | 9 | 0.0004 | | | | 2583 |
| HPV16 | E7 | CVQSTHVDIRT | 68 | 11 | | | | | 2584 |
| HPV16 | E7 | DIRTLEDL | 75 | 8 | 0.0001 | | | | 2585 |
| HPV16 | E7 | DIRTLEDLL | 75 | 9 | 0.0003 | | | | 2586 |
| HPV16 | E7 | DIRTLEDLLM | 75 | 10 | | | | | 2587 |
| HPV16 | E7 | DLLMGTLGI | 81 | 9 | 0.0002 | | | | 2588 |
| HPV16 | E7 | DLLMGTLGIV | 81 | 10 | 0.0005 | | | | 2589 |
| HPV16 | E7 | DLQPETTDL | 14 | 9 | 0.0003 | | | | 2590 |
| HPV16 | E7 | DLYCYEQL | 21 | 8 | 0.0001 | | | | 2591 |
| HPV16 | E7 | DTPTLHEYM | 4 | 9 | | | | | 2592 |
| HPV16 | E7 | DTPTLHEYML | 4 | 10 | | | | | 2593 |
| HPV16 | E7 | EIDGPAGQA | 37 | 9 | | | | | 2594 |
| HPV16 | E7 | ETTDLYCYEQL | 18 | 11 | | | | | 2595 |
| HPV16 | E7 | GQAEPDRA | 43 | 8 | | | | | 2596 |
| HPV16 | E7 | GTLGIVCPI | 85 | 9 | 0.021 | | | | 2597 |
| HPV16 | E7 | HVDIRTLEDL | 73 | 10 | 0.0001 | | | | 2598 |
| HPV16 | E7 | HVDIRTLEDLL | 73 | 11 | | | | | 2599 |
| HPV16 | E7 | IVTFCCKCDST | 54 | 11 | | | | | 2600 |
| HPV16 | E7 | LLMGTLGI | 82 | 8 | 0.0008 | | | | 2601 |
| HPV16 | E7 | LLMGTLGIV | 82 | 9 | 0.072 | 0.015 | 5.9 | 0.011 | 2602 |
| HPV16 | E7 | LMGTLGIV | 83 | 8 | 0.0001 | | | | 2603 |
| HPV16 | E7 | LMGTLGIVCPI | 83 | 11 | | | | | 2604 |
| HPV16 | E7 | LQPETTDL | 15 | 8 | | | | | 2605 |
| HPV16 | E7 | MLDLQPET | 12 | 8 | 0.0001 | | | | 2606 |
| HPV16 | E7 | MLDLQPETT | 12 | 9 | 0.0028 | | | | 2607 |
| HPV16 | E7 | MLDLQPETTDL | 12 | 11 | 0.0005 | | | | 2608 |
| HPV16 | E7 | PAGQAEPDRA | 41 | 10 | | | | | 2609 |
| HPV16 | E7 | PTLHEYML | 6 | 8 | | | | | 2610 |
| HPV16 | E7 | PTLHEYMLDL | 6 | 10 | | | | | 2611 |
| HPV16 | E7 | QAEPDRAHYNI | 44 | 11 | | | | | 2612 |
| HPV16 | E7 | RAHYNIVT | 49 | 8 | | | | | 2613 |
| HPV16 | E7 | RLCVQSTHV | 66 | 9 | 0.0003 | | | | 2614 |
| HPV16 | E7 | RLCVQSTHVDI | 66 | 11 | | | | | 2615 |
| HPV16 | E7 | RTLEDLLM | 77 | 8 | | | | | 2616 |
| HPV16 | E7 | RTLEDLLMGT | 77 | 10 | 0.0006 | | | | 2617 |
| HPV16 | E7 | RTLEDLLMGTL | 77 | 11 | | | | | 2618 |
| HPV16 | E7 | STHVDIRT | 71 | 8 | | | | | 2619 |
| HPV16 | E7 | STHVDIRTL | 71 | 9 | | | | | 2620 |
| HPV16 | E7 | STLRLCVQST | 63 | 10 | 0.0012 | | | | 2621 |
| HPV16 | E7 | TLEDLLMGT | 78 | 9 | 0.0002 | | | | 2622 |
| HPV16 | E7 | TLEDLLMGTL | 78 | 10 | 0.0002 | | | | 2623 |
| HPV16 | E7 | TLGIVCPI | 86 | 8 | 0.15 | 0.0005 | 0.54 | 0.0047 | 2624 |
| HPV16 | E7 | TLHEYMLDL | 7 | 9 | 0.007 | | | | 2625 |
| HPV16 | E7 | TLRLCVQST | 64 | 9 | 0.0061 | | | | 2626 |
| HPV16 | E7 | TLRLCVQSTHV | 64 | 11 | 0.0006 | | | | 2627 |
| HPV16 | E7 | TTDLYCYEQL | 19 | 10 | | | | | 2628 |
| HPV16 | E7 | VQSTHVDI | 69 | 8 | | | | | 2629 |
| HPV16 | E7 | VQSTHVDIRT | 69 | 10 | | | | | 2630 |
| HPV16 | E7 | VQSTHVDIRTL | 69 | 11 | | | | | 2631 |
| HPV16 | E7 | VTFCCKCDST | 55 | 10 | 0.0001 | | | | 2632 |
| HPV16 | E7 | VTFCCKCDSTL | 55 | 11 | | | | | 2633 |
| HPV16 | E7 | YMLDLQPET | 11 | 9 | 0.14 | | | | 2634 |
| HPV16 | E7 | YMLDLQPETT | 11 | 10 | 0.15 | 0.0001 | 1.7 | 0.0022 | 2635 |
| HPV16 | L1 | AAISTSET | 372 | 8 | | | | | 2636 |
| HPV16 | L1 | AAISTSETT | 372 | 9 | | | | | 2637 |
| HPV16 | L1 | AIACQKHT | 451 | 8 | | | | | 2638 |
| HPV16 | L1 | AIACQKHTPPA | 451 | 11 | | | | | 2639 |
| HPV16 | L1 | AISTSETT | 373 | 8 | | | | | 2640 |
| HPV16 | L1 | AMDFTTLQA | 233 | 9 | | | | | 2641 |
| HPV16 | L1 | AQGHNNGI | 342 | 8 | | | | | 2642 |
| HPV16 | L1 | AQIFNKPYWL | 330 | 10 | | | | | 2643 |
| HPV16 | L1 | ATPTTSST | 513 | 8 | | | | | 2644 |
| HPV16 | L1 | ATPTTSSTST | 513 | 10 | | | | | 2645 |
| HPV16 | L1 | ATPTTSSTSTT | 513 | 11 | | | | | 2646 |
| HPV16 | L1 | ATVYLPPV | 35 | 8 | | | | | 2647 |
| HPV16 | L1 | ATVYLPPVPV | 35 | 10 | | | | | 2648 |
| HPV16 | L1 | AVGENVPDDL | 292 | 10 | | | | | 2649 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L1 | AVGHPYFPI | 70 | 9 | | | | | 2650 |
| HPV16 | L1 | AVNPGDCPPL | 205 | 10 | | | | | 2651 |
| HPV16 | L1 | CAAISTSET | 371 | 9 | | | | | 2652 |
| HPV16 | L1 | CAAISTSETT | 371 | 10 | | | | | 2653 |
| HPV16 | L1 | CISMDYKQT | 172 | 9 | | | | | 2654 |
| HPV16 | L1 | CISMDYKQTQL | 172 | 11 | | | | | 2655 |
| HPV16 | L1 | CLIGCKPPI | 183 | 9 | | | | | 2656 |
| HPV16 | L1 | CQKHTPPA | 454 | 8 | | | | | 2657 |
| HPV16 | L1 | CTSICKYPDYI | 251 | 11 | | | | | 2658 |
| HPV16 | L1 | DAQIFNKPYWL | 329 | 11 | | | | | 2659 |
| HPV16 | L1 | DLQFIFQL | 397 | 8 | | | | | 2660 |
| HPV16 | L1 | DLQFIFQLCKI | 397 | 11 | | | | | 2661 |
| HPV16 | L1 | DLYIKGSGST | 300 | 10 | | | | | 2662 |
| HPV16 | L1 | DLYIKGSGSTA | 300 | 11 | | | | | 2663 |
| HPV16 | L1 | DMVDTGFGA | 225 | 9 | | | | | 2664 |
| HPV16 | L1 | DMVDTGFGAM | 225 | 10 | | | | | 2665 |
| HPV16 | L1 | DQFPLGRKFL | 486 | 10 | | | | | 2666 |
| HPV16 | L1 | DQFPLGRKFLL | 486 | 11 | | | | | 2667 |
| HPV16 | L1 | DTENASAYA | 154 | 9 | | | | | 2668 |
| HPV16 | L1 | DTENASAYAA | 154 | 10 | | | | | 2669 |
| HPV16 | L1 | DTGFGAMDFT | 228 | 10 | | | | | 2670 |
| HPV16 | L1 | DTGFGAMDFTT | 228 | 11 | | | | | 2671 |
| HPV16 | L1 | DTQRLVWA | 120 | 8 | | | | | 2672 |
| HPV16 | L1 | DTQRLVWACV | 120 | 10 | | | | | 2673 |
| HPV16 | L1 | DTSFYNPDT | 113 | 9 | | | | | 2674 |
| HPV16 | L1 | DTTRSTNM | 361 | 8 | | | | | 2675 |
| HPV16 | L1 | DTTRSTNMSL | 361 | 10 | | | | | 2676 |
| HPV16 | L1 | DTYRFVTSQA | 442 | 10 | | | | | 2677 |
| HPV16 | L1 | DTYRFVTSQAI | 442 | 11 | | | | | 2678 |
| HPV16 | L1 | DVMTYIHSM | 412 | 9 | | | | | 2679 |
| HPV16 | L1 | DVNVYHIFFQM | 17 | 11 | | | | | 2680 |
| HPV16 | L1 | EATVYLPPV | 34 | 9 | | | | | 2681 |
| HPV16 | L1 | EATVYLPPVPV | 34 | 11 | | | | | 2682 |
| HPV16 | L1 | EQMFVRHL | 279 | 8 | | | | | 2683 |
| HPV16 | L1 | EVGRGQPL | 132 | 8 | | | | | 2684 |
| HPV16 | L1 | EVGRGQPLGV | 132 | 10 | | | | | 2685 |
| HPV16 | L1 | EVNLKEKFSA | 474 | 10 | | | | | 2686 |
| HPV16 | L1 | EVPLDICT | 245 | 8 | | | | | 2687 |
| HPV16 | L1 | EVPLDICTSI | 245 | 10 | | | | | 2688 |
| HPV16 | L1 | FIFQLCKI | 400 | 8 | | | | | 2689 |
| HPV16 | L1 | FIFQLCKIT | 400 | 9 | | | | | 2690 |
| HPV16 | L1 | FIFQLCKITL | 400 | 10 | | | | | 2691 |
| HPV16 | L1 | FIFQLCKITLT | 400 | 11 | | | | | 2692 |
| HPV16 | L1 | FIYILVIT | 5 | 8 | | | | | 2693 |
| HPV16 | L1 | FLLQAGLKA | 494 | 9 | | | | | 2694 |
| HPV16 | L1 | FQLCKITL | 402 | 8 | | | | | 2695 |
| HPV16 | L1 | FQLCKITLT | 402 | 9 | | | | | 2696 |
| HPV16 | L1 | FQLCKITLTA | 402 | 10 | | | | | 2697 |
| HPV16 | L1 | FQMSLWLPSEA | 25 | 11 | | | | | 2698 |
| HPV16 | L1 | FTLGKRKA | 506 | 8 | | | | | 2699 |
| HPV16 | L1 | FTLGKRKAT | 506 | 9 | | | | | 2700 |
| HPV16 | L1 | FTLGKRKATPT | 506 | 11 | | | | | 2701 |
| HPV16 | L1 | FTTLQANKSEV | 236 | 11 | | | | | 2702 |
| HPV16 | L1 | FVRHLFNRA | 282 | 9 | | | | | 2703 |
| HPV16 | L1 | FVRHLFNRAGA | 282 | 11 | | | | | 2704 |
| HPV16 | L1 | FVTSQAIA | 446 | 8 | | | | | 2705 |
| HPV16 | L1 | FVTVVDTT | 356 | 8 | | | | | 2706 |
| HPV16 | L1 | FVTVVDTTRST | 356 | 11 | | | | | 2707 |
| HPV16 | L1 | GAMDFTTL | 232 | 8 | | | | | 2708 |
| HPV16 | L1 | GAMDFTTLQA | 232 | 10 | | | | | 2709 |
| HPV16 | L1 | GAVGENVPDDL | 291 | 11 | | | | | 2710 |
| HPV16 | L1 | GICWGNQL | 348 | 8 | | | | | 2711 |
| HPV16 | L1 | GICWGNQLFV | 348 | 10 | | | | | 2712 |
| HPV16 | L1 | GICWGNQLFVT | 348 | 11 | | | | | 2713 |
| HPV16 | L1 | GISGHPLL | 142 | 8 | | | | | 2714 |
| HPV16 | L1 | GISGHPLLNKL | 142 | 11 | | | | | 2715 |
| HPV16 | L1 | GLKAKPKFT | 499 | 9 | | | | | 2716 |
| HPV16 | L1 | GLKAKPKFTL | 499 | 10 | | | | | 2717 |
| HPV16 | L1 | GLQPPPGGT | 431 | 9 | | | | | 2718 |
| HPV16 | L1 | GLQPPPGGTL | 431 | 10 | | | | | 2719 |
| HPV16 | L1 | GLQYRVFRI | 93 | 9 | | | | | 2720 |
| HPV16 | L1 | GLQYRVFRIHL | 93 | 11 | | | | | 2721 |
| HPV16 | L1 | GQPLGVGI | 136 | 8 | | | | | 2722 |
| HPV16 | L1 | GTLEDTYRFV | 438 | 10 | | | | | 2723 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L1 | GTLEDTYRFVT | 438 | 11 | | | | | 2724 |
| HPV16 | L1 | GTSRLLAV | 64 | 8 | | | | | 2725 |
| HPV16 | L1 | GVDNRECI | 166 | 8 | | | | | 2726 |
| HPV16 | L1 | GVDNRECISM | 166 | 10 | | | | | 2727 |
| HPV16 | L1 | GVEVGRGQPL | 130 | 10 | | | | | 2728 |
| HPV16 | L1 | GVGISGHPL | 140 | 9 | | | | | 2729 |
| HPV16 | L1 | GVGISGHPLL | 140 | 10 | | | | | 2730 |
| HPV16 | L1 | HAGTSRLL | 62 | 8 | | | | | 2731 |
| HPV16 | L1 | HAGTSRLLA | 62 | 9 | | | | | 2732 |
| HPV16 | L1 | HAGTSRLLAV | 62 | 10 | | | | | 2733 |
| HPV16 | L1 | HIFFQMSL | 22 | 8 | | | | | 2734 |
| HPV16 | L1 | HIFFQMSLWL | 22 | 10 | | | | | 2735 |
| HPV16 | L1 | HLFNRAGA | 285 | 8 | | | | | 2736 |
| HPV16 | L1 | HLFNRAGAV | 285 | 9 | | | | | 2737 |
| HPV16 | L1 | HTPPAPKEDPL | 457 | 11 | | | | | 2738 |
| HPV16 | L1 | IACQKHTPPA | 452 | 10 | | | | | 2739 |
| HPV16 | L1 | ILEDWNFGL | 424 | 9 | | | | | 2740 |
| HPV16 | L1 | ILVITCYENDV | 8 | 11 | | | | | 2741 |
| HPV16 | L1 | ILVPKVSGL | 86 | 9 | | | | | 2742 |
| HPV16 | L1 | IQDGDMVDT | 221 | 9 | | | | | 2743 |
| HPV16 | L1 | ITCYENDV | 11 | 8 | | | | | 2744 |
| HPV16 | L1 | ITCYENDVNV | 11 | 10 | | | | | 2745 |
| HPV16 | L1 | ITLTADVM | 407 | 8 | | | | | 2746 |
| HPV16 | L1 | ITLTADVMT | 407 | 9 | | | | | 2747 |
| HPV16 | L1 | ITLTADVMTYI | 407 | 11 | | | | | 2748 |
| HPV16 | L1 | KAKPKFTL | 501 | 8 | | | | | 2749 |
| HPV16 | L1 | KATPTTSST | 512 | 9 | | | | | 2750 |
| HPV16 | L1 | KATPTTSSTST | 512 | 11 | | | | | 2751 |
| HPV16 | L1 | KILVPKVSGL | 85 | 10 | | | | | 2752 |
| HPV16 | L1 | KITLTADV | 406 | 8 | | | | | 2753 |
| HPV16 | L1 | KITLTADVM | 406 | 9 | | | | | 2754 |
| HPV16 | L1 | KITLTADVMT | 406 | 10 | | | | | 2755 |
| HPV16 | L1 | KLDDTENA | 151 | 8 | | | | | 2756 |
| HPV16 | L1 | KLDDTENASA | 151 | 10 | | | | | 2757 |
| HPV16 | L1 | KMVSEPYGDSL | 262 | 11 | | | | | 2758 |
| HPV16 | L1 | KQTQLCLI | 178 | 8 | | | | | 2759 |
| HPV16 | L1 | KVSGLQYRV | 90 | 9 | | | | | 2760 |
| HPV16 | L1 | KVVSTDEYV | 46 | 9 | | | | | 2761 |
| HPV16 | L1 | KVVSTDEYVA | 46 | 10 | | | | | 2762 |
| HPV16 | L1 | LASSNYFPT | 312 | 9 | | | | | 2763 |
| HPV16 | L1 | LAVGHPYFPI | 69 | 10 | | | | | 2764 |
| HPV16 | L1 | LIGCKPPI | 184 | 8 | | | | | 2765 |
| HPV16 | L1 | LINTVIQDGDM | 216 | 11 | | | | | 2766 |
| HPV16 | L1 | LLAVGHPYFPI | 68 | 11 | | | | | 2767 |
| HPV16 | L1 | LLNKLDDT | 148 | 8 | | | | | 2768 |
| HPV16 | L1 | LLNKLDDTENA | 148 | 11 | | | | | 2769 |
| HPV16 | L1 | LLQAGLKA | 495 | 8 | | | | | 2770 |
| HPV16 | L1 | LQANKSEV | 239 | 8 | | | | | 2771 |
| HPV16 | L1 | LQANKSEVPL | 239 | 10 | | | | | 2772 |
| HPV16 | L1 | LQFIFQLCKI | 398 | 10 | | | | | 2773 |
| HPV16 | L1 | LQFIFQLCKIT | 398 | 11 | | | | | 2774 |
| HPV16 | L1 | LQPPPGGT | 432 | 8 | | | | | 2775 |
| HPV16 | L1 | LQPPPGGTL | 432 | 9 | | | | | 2776 |
| HPV16 | L1 | LQRAQGHNNGI | 339 | 11 | | | | | 2777 |
| HPV16 | L1 | LQYRVFRI | 94 | 8 | | | | | 2778 |
| HPV16 | L1 | LQYRVFRIHL | 94 | 10 | | | | | 2779 |
| HPV16 | L1 | LTADVMTYI | 409 | 9 | | | | | 2780 |
| HPV16 | L1 | LVITCYENDV | 9 | 10 | | | | | 2781 |
| HPV16 | L1 | LVPKVSGL | 87 | 8 | | | | | 2782 |
| HPV16 | L1 | LVWACVGV | 124 | 8 | | | | | 2783 |
| HPV16 | L1 | LVWACVGVEV | 124 | 10 | | | | | 2784 |
| HPV16 | L1 | MQVTFIYI | 1 | 8 | | | | | 2785 |
| HPV16 | L1 | MQVTFIYIL | 1 | 9 | | | | | 2786 |
| HPV16 | L1 | MQVTFIYILV | 1 | 10 | | | | | 2787 |
| HPV16 | L1 | MQVTFIYILVI | 1 | 11 | | | | | 2788 |
| HPV16 | L1 | MTYIHSMNST | 414 | 10 | | | | | 2789 |
| HPV16 | L1 | MTYIHSMNSTI | 414 | 11 | | | | | 2790 |
| HPV16 | L1 | MVDTGFGA | 226 | 8 | | | | | 2791 |
| HPV16 | L1 | MVDTGFGAM | 226 | 9 | | | | | 2792 |
| HPV16 | L1 | MVSEPYGDSL | 263 | 10 | | | | | 2793 |
| HPV16 | L1 | MVTSDAQI | 325 | 8 | | | | | 2794 |
| HPV16 | L1 | NAGVDNRECI | 164 | 10 | | | | | 2795 |
| HPV16 | L1 | NASAYAANA | 157 | 9 | | | | | 2796 |
| HPV16 | L1 | NASAYAANAGV | 157 | 11 | | | | | 2797 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L1 | NIYYHAGT | 58 | 8 | | | | | 2798 |
| HPV16 | L1 | NIYYHAGTSRL | 58 | 11 | | | | | 2799 |
| HPV16 | L1 | NLASSNYFPT | 311 | 10 | | | | | 2800 |
| HPV16 | L1 | NLKEKFSA | 476 | 8 | | | | | 2801 |
| HPV16 | L1 | NLKEKFSADL | 476 | 10 | | | | | 2802 |
| HPV16 | L1 | NMSLCAAI | 367 | 8 | | | | | 2803 |
| HPV16 | L1 | NMSLCAAIST | 367 | 10 | | | | | 2804 |
| HPV16 | L1 | NQLFVTVV | 353 | 8 | | | | | 2805 |
| HPV16 | L1 | NQLFVTVVDT | 353 | 10 | | | | | 2806 |
| HPV16 | L1 | NQLFVTVVDTT | 353 | 11 | | | | | 2807 |
| HPV16 | L1 | NTNFKEYL | 383 | 8 | | | | | 2808 |
| HPV16 | L1 | NTVIQDGDM | 218 | 9 | | | | | 2809 |
| HPV16 | L1 | NTVIQDGDMV | 218 | 10 | | | | | 2810 |
| HPV16 | L1 | NVPDDLYI | 296 | 8 | | | | | 2811 |
| HPV16 | L1 | NVYHIFFQM | 19 | 9 | | | | | 2812 |
| HPV16 | L1 | NVYHIFFQMSL | 19 | 11 | | | | | 2813 |
| HPV16 | L1 | PAPKEDPL | 460 | 8 | | | | | 2814 |
| HPV16 | L1 | PIKKPNNNKI | 77 | 10 | | | | | 2815 |
| HPV16 | L1 | PIKKPNNNKIL | 77 | 11 | | | | | 2816 |
| HPV16 | L1 | PLDICTSI | 247 | 8 | | | | | 2817 |
| HPV16 | L1 | PLELINTV | 213 | 8 | | | | | 2818 |
| HPV16 | L1 | PLELINTVI | 213 | 9 | | | | | 2819 |
| HPV16 | L1 | PLGRKFLL | 489 | 8 | | | | | 2820 |
| HPV16 | L1 | PLGRKFLLQA | 489 | 10 | | | | | 2821 |
| HPV16 | L1 | PLGVGISGHPL | 138 | 11 | | | | | 2822 |
| HPV16 | L1 | PLKKYTFWEV | 466 | 10 | | | | | 2823 |
| HPV16 | L1 | PLLNKLDDT | 147 | 9 | | | | | 2824 |
| HPV16 | L1 | PTPSGSMV | 319 | 8 | | | | | 2825 |
| HPV16 | L1 | PTPSGSMVT | 319 | 9 | | | | | 2826 |
| HPV16 | L1 | PTTSSTST | 515 | 8 | | | | | 2827 |
| HPV16 | L1 | PTTSSTSTT | 515 | 9 | | | | | 2828 |
| HPV16 | L1 | PTTSSTSTTA | 515 | 10 | | | | | 2829 |
| HPV16 | L1 | PVPVSKVV | 41 | 8 | | | | | 2830 |
| HPV16 | L1 | PVPVSKVVST | 41 | 10 | | | | | 2831 |
| HPV16 | L1 | PVSKVVST | 43 | 8 | | | | | 2832 |
| HPV16 | L1 | QAGLKAKPKFT | 497 | 11 | | | | | 2833 |
| HPV16 | L1 | QAIACQKHT | 450 | 9 | | | | | 2834 |
| HPV16 | L1 | QANKSEVPL | 240 | 9 | | | | | 2835 |
| HPV16 | L1 | QANKSEVPLDI | 240 | 11 | | | | | 2836 |
| HPV16 | L1 | QIFNKPYWL | 331 | 9 | | | | | 2837 |
| HPV16 | L1 | QLCKITLT | 403 | 8 | | | | | 2838 |
| HPV16 | L1 | QLCKITLTA | 403 | 9 | | | | | 2839 |
| HPV16 | L1 | QLCKITLTADV | 403 | 11 | | | | | 2840 |
| HPV16 | L1 | QLCLIGCKPPI | 181 | 11 | | | | | 2841 |
| HPV16 | L1 | QLFVTVVDT | 354 | 9 | | | | | 2842 |
| HPV16 | L1 | QLFVTVVDTT | 354 | 10 | | | | | 2843 |
| HPV16 | L1 | QMFVRHLFNRA | 280 | 11 | | | | | 2844 |
| HPV16 | L1 | QMSLWLPSEA | 26 | 10 | | | | | 2845 |
| HPV16 | L1 | QMSLWLPSEAT | 26 | 11 | | | | | 2846 |
| HPV16 | L1 | QVTFIYIL | 2 | 8 | | | | | 2847 |
| HPV16 | L1 | QVTFIYILV | 2 | 9 | | | | | 2848 |
| HPV16 | L1 | QVTFIYILVI | 2 | 10 | | | | | 2849 |
| HPV16 | L1 | QVTFIYILVIT | 2 | 11 | | | | | 2850 |
| HPV16 | L1 | RAGAVGENV | 289 | 9 | | | | | 2851 |
| HPV16 | L1 | RAQGHNNGI | 341 | 9 | | | | | 2852 |
| HPV16 | L1 | RLVWACVGV | 123 | 9 | | | | | 2853 |
| HPV16 | L1 | RLVWACVGVEV | 123 | 11 | | | | | 2854 |
| HPV16 | L1 | RTNIYYHA | 56 | 8 | | | | | 2855 |
| HPV16 | L1 | RTNIYYHAGT | 56 | 10 | | | | | 2856 |
| HPV16 | L1 | SADLDQFPL | 482 | 9 | | | | | 2857 |
| HPV16 | L1 | SAYAANAGV | 159 | 9 | | | | | 2858 |
| HPV16 | L1 | SICKYPDYI | 253 | 9 | | | | | 2859 |
| HPV16 | L1 | SICKYPDYIKM | 253 | 11 | | | | | 2860 |
| HPV16 | L1 | SLCAAIST | 369 | 8 | | | | | 2861 |
| HPV16 | L1 | SLCAAISTSET | 369 | 11 | | | | | 2862 |
| HPV16 | L1 | SLFFYLRREQM | 271 | 11 | | | | | 2863 |
| HPV16 | L1 | SLWLPSEA | 28 | 8 | | | | | 2864 |
| HPV16 | L1 | SLWLPSEAT | 28 | 9 | | | | | 2865 |
| HPV16 | L1 | SLWLPSEATV | 28 | 10 | | | | | 2866 |
| HPV16 | L1 | SMDYKQTQL | 174 | 9 | | | | | 2867 |
| HPV16 | L1 | SMDYKQTQLCL | 174 | 11 | | | | | 2868 |
| HPV16 | L1 | SMVTSDAQI | 324 | 9 | | | | | 2869 |
| HPV16 | L1 | SQAIACQKHT | 449 | 10 | | | | | 2870 |
| HPV16 | L1 | STDEYVART | 49 | 9 | | | | | 2871 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L1 | STDEYVARTNI | 49 | 11 | | | | | 2872 |
| HPV16 | L1 | STILEDWNFGL | 422 | 11 | | | | | 2873 |
| HPV16 | L1 | STNMSLCA | 365 | 8 | | | | | 2874 |
| HPV16 | L1 | STNMSLCAA | 365 | 9 | | | | | 2875 |
| HPV16 | L1 | STNMSLCAAI | 365 | 10 | | | | | 2876 |
| HPV16 | L1 | STSETTYKNT | 375 | 10 | | | | | 2877 |
| HPV16 | L1 | STTAKRKKRKL | 521 | 11 | | | | | 2878 |
| HPV16 | L1 | TADVMTYI | 410 | 8 | | | | | 2879 |
| HPV16 | L1 | TADVMTYIHSM | 410 | 11 | | | | | 2880 |
| HPV16 | L1 | TAKRKKRKL | 523 | 9 | | | | | 2881 |
| HPV16 | L1 | TILEDWNFGL | 423 | 10 | | | | | 2882 |
| HPV16 | L1 | TLEDTYRFV | 439 | 9 | | | | | 2883 |
| HPV16 | L1 | TLEDTYRFVT | 439 | 10 | | | | | 2884 |
| HPV16 | L1 | TLGKRKAT | 507 | 8 | | | | | 2885 |
| HPV16 | L1 | TLGKRKATPT | 507 | 10 | | | | | 2886 |
| HPV16 | L1 | TLGKRKATPTT | 507 | 11 | | | | | 2887 |
| HPV16 | L1 | TLQANKSEV | 238 | 9 | | | | | 2888 |
| HPV16 | L1 | TLQANKSEVPL | 238 | 11 | | | | | 2889 |
| HPV16 | L1 | TLTADVMT | 408 | 8 | | | | | 2890 |
| HPV16 | L1 | TLTADVMTYI | 408 | 10 | | | | | 2891 |
| HPV16 | L1 | TQRLVWACV | 121 | 9 | | | | | 2892 |
| HPV16 | L1 | TQRLVWACVGV | 121 | 11 | | | | | 2893 |
| HPV16 | L1 | TTAKRKKRKL | 522 | 10 | | | | | 2894 |
| HPV16 | L1 | TTLQANKSEV | 237 | 10 | | | | | 2895 |
| HPV16 | L1 | TTRSTNMSL | 362 | 9 | | | | | 2896 |
| HPV16 | L1 | TTRSTNMSLCA | 362 | 11 | | | | | 2897 |
| HPV16 | L1 | TTSSTSTT | 516 | 8 | | | | | 2898 |
| HPV16 | L1 | TTSSTSTTA | 516 | 9 | | | | | 2899 |
| HPV16 | L1 | TVIQDGDM | 219 | 8 | | | | | 2900 |
| HPV16 | L1 | TVIQDGDMV | 219 | 9 | | | | | 2901 |
| HPV16 | L1 | TVIQDGDMVDT | 219 | 11 | | | | | 2902 |
| HPV16 | L1 | TVVDTTRST | 358 | 9 | | | | | 2903 |
| HPV16 | L1 | TVVDTTRSTNM | 358 | 11 | | | | | 2904 |
| HPV16 | L1 | TVYLPPVPV | 36 | 9 | | | | | 2905 |
| HPV16 | L1 | VARTNIYYHA | 54 | 10 | | | | | 2906 |
| HPV16 | L1 | VAVNPGDCPPL | 204 | 11 | | | | | 2907 |
| HPV16 | L1 | VIQDGDMV | 220 | 8 | | | | | 2908 |
| HPV16 | L1 | VIQDGDMVDT | 220 | 10 | | | | | 2909 |
| HPV16 | L1 | VITCYENDV | 10 | 9 | | | | | 2910 |
| HPV16 | L1 | VITCYENDVNV | 10 | 11 | | | | | 2911 |
| HPV16 | L1 | VMTYIHSM | 413 | 8 | | | | | 2912 |
| HPV16 | L1 | VMTYIHSMNST | 413 | 11 | | | | | 2913 |
| HPV16 | L1 | VTFIYILV | 3 | 8 | | | | | 2914 |
| HPV16 | L1 | VTFIYILVI | 3 | 9 | | | | | 2915 |
| HPV16 | L1 | VTFIYILVIT | 3 | 10 | | | | | 2916 |
| HPV16 | L1 | VTVVDTTRST | 357 | 10 | | | | | 2917 |
| HPV16 | L1 | VVDTTRST | 359 | 8 | | | | | 2918 |
| HPV16 | L1 | VVDTTRSTNM | 359 | 10 | | | | | 2919 |
| HPV16 | L1 | VVSTDEYV | 47 | 8 | | | | | 2920 |
| HPV16 | L1 | VVSTDEYVA | 47 | 9 | | | | | 2921 |
| HPV16 | L1 | VVSTDEYVART | 47 | 11 | | | | | 2922 |
| HPV16 | L1 | WACVGVEV | 126 | 8 | | | | | 2923 |
| HPV16 | L1 | WLPSEATV | 30 | 8 | | | | | 2924 |
| HPV16 | L1 | WLPSEATVYL | 30 | 10 | | | | | 2925 |
| HPV16 | L1 | YIHSMNST | 416 | 8 | | | | | 2926 |
| HPV16 | L1 | YIHSMNSTI | 416 | 9 | | | | | 2927 |
| HPV16 | L1 | YIHSMNSTIL | 416 | 10 | | | | | 2928 |
| HPV16 | L1 | YIKGSGST | 302 | 8 | | | | | 2929 |
| HPV16 | L1 | YIKGSGSTA | 302 | 9 | | | | | 2930 |
| HPV16 | L1 | YIKGSGSTANL | 302 | 11 | | | | | 2931 |
| HPV16 | L1 | YLPPVPVSKV | 38 | 10 | | | | | 2932 |
| HPV16 | L1 | YLPPVPVSKVV | 38 | 11 | | | | | 2933 |
| HPV16 | L1 | YLRHGEEYDL | 389 | 10 | | | | | 2934 |
| HPV16 | L1 | YLRREQMFV | 275 | 9 | | | | | 2935 |
| HPV16 | L1 | YTFWEVNL | 470 | 8 | | | | | 2936 |
| HPV16 | L1 | YVARTNIYYHA | 53 | 11 | | | | | 2937 |
| HPV16 | L2 | AALPTSINNGL | 355 | 11 | | | | | 2938 |
| HPV16 | L2 | AILDINNT | 144 | 8 | | | | | 2939 |
| HPV16 | L2 | AILDINNTV | 144 | 9 | | | | | 2940 |
| HPV16 | L2 | AILDINNTVT | 144 | 10 | | | | | 2941 |
| HPV16 | L2 | AILDINNTVTT | 144 | 11 | | | | | 2942 |
| HPV16 | L2 | ALHRPALT | 288 | 8 | | | | | 2943 |
| HPV16 | L2 | ALPTSINNGL | 356 | 10 | | | | | 2944 |
| HPV16 | L2 | ALTSRRTGI | 293 | 9 | | | | | 2945 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L2 | ATDTLAPV | 82 | 8 | | | | | 2946 |
| HPV16 | L2 | ATQLYKTCKQA | 15 | 11 | | | | | 2947 |
| HPV16 | L2 | DAGAPTSV | 116 | 8 | | | | | 2948 |
| HPV16 | L2 | DAGAPTSVPSI | 116 | 11 | | | | | 2949 |
| HPV16 | L2 | DIIPKVEGKT | 31 | 10 | | | | | 2950 |
| HPV16 | L2 | DIIPKVEGKTI | 31 | 11 | | | | | 2951 |
| HPV16 | L2 | DINNTVTT | 147 | 8 | | | | | 2952 |
| HPV16 | L2 | DINNTVTTV | 147 | 9 | | | | | 2953 |
| HPV16 | L2 | DINNTVTTVT | 147 | 10 | | | | | 2954 |
| HPV16 | L2 | DINNTVTTVTT | 147 | 11 | | | | | 2955 |
| HPV16 | L2 | DIPINITDQA | 415 | 10 | | | | | 2956 |
| HPV16 | L2 | DIVALHRPA | 285 | 9 | | | | | 2957 |
| HPV16 | L2 | DIVALHRPAL | 285 | 10 | | | | | 2958 |
| HPV16 | L2 | DIVALHRPALT | 285 | 11 | | | | | 2959 |
| HPV16 | L2 | DIYADDFI | 367 | 8 | | | | | 2960 |
| HPV16 | L2 | DIYADDFIT | 367 | 9 | | | | | 2961 |
| HPV16 | L2 | DIYADDFITDT | 367 | 11 | | | | | 2962 |
| HPV16 | L2 | DQAPSLIPI | 422 | 9 | | | | | 2963 |
| HPV16 | L2 | DQAPSLIPIV | 422 | 10 | | | | | 2964 |
| HPV16 | L2 | DQILQYGSM | 43 | 9 | | | | | 2965 |
| HPV16 | L2 | DQILQYGSMGV | 43 | 11 | | | | | 2966 |
| HPV16 | L2 | DTFIVSTNPNT | 199 | 11 | | | | | 2967 |
| HPV16 | L2 | DTLAPVRPPL | 84 | 10 | | | | | 2968 |
| HPV16 | L2 | DTLAPVRPPLT | 84 | 11 | | | | | 2969 |
| HPV16 | L2 | DTSTTPVPSV | 376 | 10 | | | | | 2970 |
| HPV16 | L2 | DTTPAILDI | 140 | 9 | | | | | 2971 |
| HPV16 | L2 | DVSGFSIT | 129 | 8 | | | | | 2972 |
| HPV16 | L2 | DVSGFSITT | 129 | 9 | | | | | 2973 |
| HPV16 | L2 | DVSGFSITTST | 129 | 11 | | | | | 2974 |
| HPV16 | L2 | EIELQTIT | 338 | 8 | | | | | 2975 |
| HPV16 | L2 | EIELQTITPST | 338 | 11 | | | | | 2976 |
| HPV16 | L2 | EIPMDTFI | 195 | 8 | | | | | 2977 |
| HPV16 | L2 | EIPMDTFIV | 195 | 9 | | | | | 2978 |
| HPV16 | L2 | EIPMDTFIVST | 195 | 11 | | | | | 2979 |
| HPV16 | L2 | ELQTITPST | 340 | 9 | | | | | 2980 |
| HPV16 | L2 | ELQTITPSTYT | 340 | 11 | | | | | 2981 |
| HPV16 | L2 | ETGGHFTL | 176 | 8 | | | | | 2982 |
| HPV16 | L2 | ETSFIDAGA | 111 | 9 | | | | | 2983 |
| HPV16 | L2 | ETSFIDAGAPT | 111 | 11 | | | | | 2984 |
| HPV16 | L2 | FIDAGAPT | 114 | 8 | | | | | 2985 |
| HPV16 | L2 | FIDAGAPTSV | 114 | 10 | | | | | 2986 |
| HPV16 | L2 | FITDTSTT | 373 | 8 | | | | | 2987 |
| HPV16 | L2 | FITDTSTTPV | 373 | 10 | | | | | 2988 |
| HPV16 | L2 | FITTPTKL | 242 | 8 | | | | | 2989 |
| HPV16 | L2 | FITTPTKLI | 242 | 9 | | | | | 2990 |
| HPV16 | L2 | FITTPTKLIT | 242 | 10 | | | | | 2991 |
| HPV16 | L2 | FIVSTNPNT | 201 | 9 | | | | | 2992 |
| HPV16 | L2 | FIVSTNPNTV | 201 | 10 | | | | | 2993 |
| HPV16 | L2 | FIVSTNPNTVT | 201 | 11 | | | | | 2994 |
| HPV16 | L2 | FLDIVALHRPA | 283 | 11 | | | | | 2995 |
| HPV16 | L2 | FTDPSVLQPPT | 163 | 11 | | | | | 2996 |
| HPV16 | L2 | FTLSSSTI | 181 | 8 | | | | | 2997 |
| HPV16 | L2 | FTLSSSTIST | 181 | 10 | | | | | 2998 |
| HPV16 | L2 | GAPTSVPSI | 118 | 9 | | | | | 2999 |
| HPV16 | L2 | GAYNIPLV | 404 | 8 | | | | | 3000 |
| HPV16 | L2 | GIDVDNTL | 259 | 8 | | | | | 3001 |
| HPV16 | L2 | GIGTGSGT | 59 | 8 | | | | | 3002 |
| HPV16 | L2 | GLGIGTGSGT | 57 | 10 | | | | | 3003 |
| HPV16 | L2 | GLYDIYADDFI | 364 | 11 | | | | | 3004 |
| HPV16 | L2 | GLYSRTTQQV | 226 | 10 | | | | | 3005 |
| HPV16 | L2 | GTCPPDII | 26 | 8 | | | | | 3006 |
| HPV16 | L2 | GTCPPDIIPKV | 26 | 11 | | | | | 3007 |
| HPV16 | L2 | GTGGRTGYI | 65 | 9 | | | | | 3008 |
| HPV16 | L2 | GTGGRTGYIPL | 65 | 11 | | | | | 3009 |
| HPV16 | L2 | GTGSGTGGRT | 61 | 10 | | | | | 3010 |
| HPV16 | L2 | GTRPPTAT | 76 | 8 | | | | | 3011 |
| HPV16 | L2 | GTRPPTATDT | 76 | 10 | | | | | 3012 |
| HPV16 | L2 | GTRPPTATDTL | 76 | 11 | | | | | 3013 |
| HPV16 | L2 | GVFFGGLGI | 52 | 9 | | | | | 3014 |
| HPV16 | L2 | GVFFGGLGIGT | 52 | 11 | | | | | 3015 |
| HPV16 | L2 | HAALPTSI | 354 | 8 | | | | | 3016 |
| HPV16 | L2 | IADAGDFYL | 440 | 9 | | | | | 3017 |
| HPV16 | L2 | IADQILQYGSM | 41 | 11 | | | | | 3018 |
| HPV16 | L2 | IAPDPDFL | 277 | 8 | | | | | 3019 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L2 | IAPDPDFLDI | 277 | 10 | | | | | 3020 |
| HPV16 | L2 | IAPDPDFLDIV | 277 | 11 | | | | | 3021 |
| HPV16 | L2 | IIADAGDFYL | 439 | 10 | | | | | 3022 |
| HPV16 | L2 | IIPKVEGKT | 32 | 9 | | | | | 3023 |
| HPV16 | L2 | IIPKVEGKTI | 32 | 10 | | | | | 3024 |
| HPV16 | L2 | IIPKVEGKTIA | 32 | 11 | | | | | 3025 |
| HPV16 | L2 | ILDINNTV | 145 | 8 | | | | | 3026 |
| HPV16 | L2 | ILDINNTVT | 145 | 9 | | | | | 3027 |
| HPV16 | L2 | ILDINNTVTT | 145 | 10 | | | | | 3028 |
| HPV16 | L2 | ILDINNTVTTV | 145 | 11 | | | | | 3029 |
| HPV16 | L2 | ILQYGSMGV | 45 | 9 | | | | | 3030 |
| HPV16 | L2 | ITDQAPSL | 420 | 8 | | | | | 3031 |
| HPV16 | L2 | ITDQAPSLI | 420 | 9 | | | | | 3032 |
| HPV16 | L2 | ITDQAPSLIPI | 420 | 11 | | | | | 3033 |
| HPV16 | L2 | ITDTSTTPV | 374 | 9 | | | | | 3034 |
| HPV16 | L2 | ITPSTYTT | 344 | 8 | | | | | 3035 |
| HPV16 | L2 | ITPSTYTTT | 344 | 9 | | | | | 3036 |
| HPV16 | L2 | ITTPTKLI | 243 | 8 | | | | | 3037 |
| HPV16 | L2 | ITTPTKLIT | 243 | 9 | | | | | 3038 |
| HPV16 | L2 | ITTSTDTT | 135 | 8 | | | | | 3039 |
| HPV16 | L2 | ITTSTDTTPA | 135 | 10 | | | | | 3040 |
| HPV16 | L2 | ITTSTDTTPAI | 135 | 11 | | | | | 3041 |
| HPV16 | L2 | ITYDNPAYEGI | 250 | 11 | | | | | 3042 |
| HPV16 | L2 | IVALHRPA | 286 | 8 | | | | | 3043 |
| HPV16 | L2 | IVALHRPAL | 286 | 9 | | | | | 3044 |
| HPV16 | L2 | IVALHRPALT | 286 | 10 | | | | | 3045 |
| HPV16 | L2 | IVPGSPQYT | 430 | 9 | | | | | 3046 |
| HPV16 | L2 | IVPGSPQYTI | 430 | 10 | | | | | 3047 |
| HPV16 | L2 | IVPGSPQYTII | 430 | 11 | | | | | 3048 |
| HPV16 | L2 | IVSLVEET | 105 | 8 | | | | | 3049 |
| HPV16 | L2 | IVSLVEETSFI | 105 | 11 | | | | | 3050 |
| HPV16 | L2 | IVSTNPNT | 202 | 8 | | | | | 3051 |
| HPV16 | L2 | IVSTNPNTV | 202 | 9 | | | | | 3052 |
| HPV16 | L2 | IVSTNPNTVT | 202 | 10 | | | | | 3053 |
| HPV16 | L2 | KLITYDNPA | 248 | 9 | | | | | 3054 |
| HPV16 | L2 | KQAGTCPPDI | 23 | 10 | | | | | 3055 |
| HPV16 | L2 | KQAGTCPPDII | 23 | 11 | | | | | 3056 |
| HPV16 | L2 | KTCKQAGT | 20 | 8 | | | | | 3057 |
| HPV16 | L2 | KTIADQIL | 39 | 8 | | | | | 3058 |
| HPV16 | L2 | KVEGKTIA | 35 | 8 | | | | | 3059 |
| HPV16 | L2 | KVEGKTIADQI | 35 | 11 | | | | | 3060 |
| HPV16 | L2 | KVHYYYDFST | 323 | 10 | | | | | 3061 |
| HPV16 | L2 | KVHYYYDFSTI | 323 | 11 | | | | | 3062 |
| HPV16 | L2 | KVVDPAFI | 236 | 8 | | | | | 3063 |
| HPV16 | L2 | KVVDPAFIT | 236 | 9 | | | | | 3064 |
| HPV16 | L2 | KVVDPAFITT | 236 | 10 | | | | | 3065 |
| HPV16 | L2 | LAPVRPPL | 86 | 8 | | | | | 3066 |
| HPV16 | L2 | LAPVRPPLT | 86 | 9 | | | | | 3067 |
| HPV16 | L2 | LAPVRPPLTV | 86 | 10 | | | | | 3068 |
| HPV16 | L2 | LITYDNPA | 249 | 8 | | | | | 3069 |
| HPV16 | L2 | LQPPTPAET | 169 | 9 | | | | | 3070 |
| HPV16 | L2 | LQTITPST | 341 | 8 | | | | | 3071 |
| HPV16 | L2 | LQTITPSTYT | 341 | 10 | | | | | 3072 |
| HPV16 | L2 | LQTITPSTYTT | 341 | 11 | | | | | 3073 |
| HPV16 | L2 | LQYGSMGV | 46 | 8 | | | | | 3074 |
| HPV16 | L2 | LTSRRTGI | 294 | 8 | | | | | 3075 |
| HPV16 | L2 | LVEETSFI | 108 | 8 | | | | | 3076 |
| HPV16 | L2 | LVEETSFIDA | 108 | 10 | | | | | 3077 |
| HPV16 | L2 | LVSGPDIPI | 410 | 9 | | | | | 3078 |
| HPV16 | L2 | LVSGPDIPINI | 410 | 11 | | | | | 3079 |
| HPV16 | L2 | MLRKRRKRL | 454 | 9 | | | | | 3080 |
| HPV16 | L2 | NIAPDPDFL | 276 | 9 | | | | | 3081 |
| HPV16 | L2 | NIAPDPDFLDI | 276 | 11 | | | | | 3082 |
| HPV16 | L2 | NIPLVSGPDI | 407 | 10 | | | | | 3083 |
| HPV16 | L2 | NITDQAPSL | 419 | 9 | | | | | 3084 |
| HPV16 | L2 | NITDQAPSLI | 419 | 10 | | | | | 3085 |
| HPV16 | L2 | NTTIPFGGA | 397 | 9 | | | | | 3086 |
| HPV16 | L2 | NTVTSSTPI | 208 | 9 | | | | | 3087 |
| HPV16 | L2 | NTVTTVTT | 150 | 8 | | | | | 3088 |
| HPV16 | L2 | PAETGGHFT | 174 | 9 | | | | | 3089 |
| HPV16 | L2 | PAETGGHFTL | 174 | 10 | | | | | 3090 |
| HPV16 | L2 | PAFITTPT | 240 | 8 | | | | | 3091 |
| HPV16 | L2 | PAFITTPTKL | 240 | 10 | | | | | 3092 |
| HPV16 | L2 | PAFITTPTKLI | 240 | 11 | | | | | 3093 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L2 | PAILDINNT | 143 | 9 | | | | | 3094 |
| HPV16 | L2 | PAILDINNTV | 143 | 10 | | | | | 3095 |
| HPV16 | L2 | PAILDINNTVT | 143 | 11 | | | | | 3096 |
| HPV16 | L2 | PALTSRRT | 292 | 8 | | | | | 3097 |
| HPV16 | L2 | PALTSRRTGI | 292 | 10 | | | | | 3098 |
| HPV16 | L2 | PANTTIPFGGA | 395 | 11 | | | | | 3099 |
| HPV16 | L2 | PAYEGIDV | 255 | 8 | | | | | 3100 |
| HPV16 | L2 | PAYEGIDVDNT | 255 | 11 | | | | | 3101 |
| HPV16 | L2 | PINITDQA | 417 | 8 | | | | | 3102 |
| HPV16 | L2 | PINITDQAPSL | 417 | 11 | | | | | 3103 |
| HPV16 | L2 | PIPGSRPV | 215 | 8 | | | | | 3104 |
| HPV16 | L2 | PIPGSRPVA | 215 | 9 | | | | | 3105 |
| HPV16 | L2 | PIPGSRPVARL | 215 | 11 | | | | | 3106 |
| HPV16 | L2 | PIVPGSPQYT | 429 | 10 | | | | | 3107 |
| HPV16 | L2 | PIVPGSPQYTI | 429 | 11 | | | | | 3108 |
| HPV16 | L2 | PLGTRPPT | 74 | 8 | | | | | 3109 |
| HPV16 | L2 | PLGTRPPTA | 74 | 9 | | | | | 3110 |
| HPV16 | L2 | PLGTRPPTAT | 74 | 10 | | | | | 3111 |
| HPV16 | L2 | PLVSGPDI | 409 | 8 | | | | | 3112 |
| HPV16 | L2 | PLVSGPDIPI | 409 | 10 | | | | | 3113 |
| HPV16 | L2 | PMDTFIVST | 197 | 9 | | | | | 3114 |
| HPV16 | L2 | PQYTIIADA | 435 | 9 | | | | | 3115 |
| HPV16 | L2 | PTATDTLA | 80 | 8 | | | | | 3116 |
| HPV16 | L2 | PTATDTLAPV | 80 | 10 | | | | | 3117 |
| HPV16 | L2 | PTFTDPSV | 161 | 8 | | | | | 3118 |
| HPV16 | L2 | PTFTDPSVL | 161 | 9 | | | | | 3119 |
| HPV16 | L2 | PTKLITYDNPA | 246 | 11 | | | | | 3120 |
| HPV16 | L2 | PTPAETGGHFT | 172 | 11 | | | | | 3121 |
| HPV16 | L2 | PTSINNGL | 358 | 8 | | | | | 3122 |
| HPV16 | L2 | PTSINNGLYDI | 358 | 11 | | | | | 3123 |
| HPV16 | L2 | PTSVPSIPPDV | 120 | 11 | | | | | 3124 |
| HPV16 | L2 | PVARLGLYSRT | 221 | 11 | | | | | 3125 |
| HPV16 | L2 | PVGPSDPSI | 97 | 9 | | | | | 3126 |
| HPV16 | L2 | PVGPSDPSIV | 97 | 10 | | | | | 3127 |
| HPV16 | L2 | PVPSVPST | 381 | 8 | | | | | 3128 |
| HPV16 | L2 | PVPSVPSTSL | 381 | 10 | | | | | 3129 |
| HPV16 | L2 | PVRPPLTV | 88 | 8 | | | | | 3130 |
| HPV16 | L2 | PVRPPLTVDPV | 88 | 11 | | | | | 3131 |
| HPV16 | L2 | QAGTCPPDI | 24 | 9 | | | | | 3132 |
| HPV16 | L2 | QAGTCPPDII | 24 | 10 | | | | | 3133 |
| HPV16 | L2 | QAPSLIPI | 423 | 8 | | | | | 3134 |
| HPV16 | L2 | QAPSLIPIV | 423 | 9 | | | | | 3135 |
| HPV16 | L2 | QILQYGSM | 44 | 8 | | | | | 3136 |
| HPV16 | L2 | QILQYGSMGV | 44 | 10 | | | | | 3137 |
| HPV16 | L2 | QLYKTCKQA | 17 | 9 | | | | | 3138 |
| HPV16 | L2 | QLYKTCKQAGT | 17 | 11 | | | | | 3139 |
| HPV16 | L2 | QQVKVVDPA | 233 | 9 | | | | | 3140 |
| HPV16 | L2 | QQVKVVDPAFI | 233 | 11 | | | | | 3141 |
| HPV16 | L2 | QTITPSTYT | 342 | 9 | | | | | 3142 |
| HPV16 | L2 | QTITPSTYTT | 342 | 10 | | | | | 3143 |
| HPV16 | L2 | QTITPSTYTTT | 342 | 11 | | | | | 3144 |
| HPV16 | L2 | QTLRTRSGKSI | 310 | 11 | | | | | 3145 |
| HPV16 | L2 | QVKVVDPA | 234 | 8 | | | | | 3146 |
| HPV16 | L2 | QVKVVDPAFI | 234 | 10 | | | | | 3147 |
| HPV16 | L2 | QVKVVDPAFIT | 234 | 11 | | | | | 3148 |
| HPV16 | L2 | RASATQLYKT | 12 | 10 | | | | | 3149 |
| HPV16 | L2 | RIGNKQTL | 305 | 8 | | | | | 3150 |
| HPV16 | L2 | RIGNKQTLRT | 305 | 10 | | | | | 3151 |
| HPV16 | L2 | RLGLYSRT | 224 | 8 | | | | | 3152 |
| HPV16 | L2 | RLGLYSRTT | 224 | 9 | | | | | 3153 |
| HPV16 | L2 | RLPYFFSDV | 461 | 9 | | | | | 3154 |
| HPV16 | L2 | RLPYFFSDVSL | 461 | 11 | | | | | 3155 |
| HPV16 | L2 | RTGIRYSRI | 298 | 9 | | | | | 3156 |
| HPV16 | L2 | RTGYIPLGT | 69 | 9 | | | | | 3157 |
| HPV16 | L2 | RTKRASAT | 9 | 8 | | | | | 3158 |
| HPV16 | L2 | RTKRASATQL | 9 | 10 | | | | | 3159 |
| HPV16 | L2 | RTRSGKSI | 313 | 8 | | | | | 3160 |
| HPV16 | L2 | RTRSGKSIGA | 313 | 10 | | | | | 3161 |
| HPV16 | L2 | RTTQQVKV | 230 | 8 | | | | | 3162 |
| HPV16 | L2 | RTTQQVKVV | 230 | 9 | | | | | 3163 |
| HPV16 | L2 | SAEEIELQT | 335 | 9 | | | | | 3164 |
| HPV16 | L2 | SAEEIELQTI | 335 | 10 | | | | | 3165 |
| HPV16 | L2 | SAEEIELQTIT | 335 | 11 | | | | | 3166 |
| HPV16 | L2 | SAKRTKRA | 6 | 8 | | | | | 3167 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L2 | SAKRTKRASA | 6 | 10 | | | | | 3168 |
| HPV16 | L2 | SAKRTKRASAT | 6 | 11 | | | | | 3169 |
| HPV16 | L2 | SATQLYKT | 14 | 8 | | | | | 3170 |
| HPV16 | L2 | SINIAPDPDFL | 274 | 11 | | | | | 3171 |
| HPV16 | L2 | SINNGLYDI | 360 | 9 | | | | | 3172 |
| HPV16 | L2 | SINNGLYDIYA | 360 | 11 | | | | | 3173 |
| HPV16 | L2 | SIPPDVSGFSI | 125 | 11 | | | | | 3174 |
| HPV16 | L2 | SITTSTDT | 134 | 8 | | | | | 3175 |
| HPV16 | L2 | SITTSTDTT | 134 | 9 | | | | | 3176 |
| HPV16 | L2 | SITTSTDTTPA | 134 | 11 | | | | | 3177 |
| HPV16 | L2 | SIVSLVEET | 104 | 9 | | | | | 3178 |
| HPV16 | L2 | SLSGYIPA | 389 | 8 | | | | | 3179 |
| HPV16 | L2 | SLSGYIPANT | 389 | 10 | | | | | 3180 |
| HPV16 | L2 | SLSGYIPANTT | 389 | 11 | | | | | 3181 |
| HPV16 | L2 | SLVEETSFI | 107 | 9 | | | | | 3182 |
| HPV16 | L2 | SLVEETSFIDA | 107 | 11 | | | | | 3183 |
| HPV16 | L2 | SMGVFFGGL | 50 | 9 | | | | | 3184 |
| HPV16 | L2 | SMGVFFGGLGI | 50 | 11 | | | | | 3185 |
| HPV16 | L2 | STDTTPAI | 138 | 8 | | | | | 3186 |
| HPV16 | L2 | STDTTPAIL | 138 | 9 | | | | | 3187 |
| HPV16 | L2 | STDTTPAILDI | 138 | 11 | | | | | 3188 |
| HPV16 | L2 | STHNYEEI | 189 | 8 | | | | | 3189 |
| HPV16 | L2 | STHNYEEIPM | 189 | 10 | | | | | 3190 |
| HPV16 | L2 | STIDSAEEI | 331 | 9 | | | | | 3191 |
| HPV16 | L2 | STIDSAEEIEL | 331 | 11 | | | | | 3192 |
| HPV16 | L2 | STISTHNYEEI | 186 | 11 | | | | | 3193 |
| HPV16 | L2 | STNPNTVT | 204 | 8 | | | | | 3194 |
| HPV16 | L2 | STNPNTVTSST | 204 | 11 | | | | | 3195 |
| HPV16 | L2 | STPIPGSRPV | 213 | 10 | | | | | 3196 |
| HPV16 | L2 | STPIPGSRPVA | 213 | 11 | | | | | 3197 |
| HPV16 | L2 | STSLSGYI | 387 | 8 | | | | | 3198 |
| HPV16 | L2 | STSLSGYIPA | 387 | 10 | | | | | 3199 |
| HPV16 | L2 | STTPVPSV | 378 | 8 | | | | | 3200 |
| HPV16 | L2 | STTPVPSVPST | 378 | 11 | | | | | 3201 |
| HPV16 | L2 | STYTTTSHA | 347 | 9 | | | | | 3202 |
| HPV16 | L2 | STYTTTSHAA | 347 | 10 | | | | | 3203 |
| HPV16 | L2 | STYTTTSHAAL | 347 | 11 | | | | | 3204 |
| HPV16 | L2 | SVLQPPTPA | 167 | 9 | | | | | 3205 |
| HPV16 | L2 | SVLQPPTPAET | 167 | 11 | | | | | 3206 |
| HPV16 | L2 | SVPSIPPDV | 122 | 9 | | | | | 3207 |
| HPV16 | L2 | SVPSTSLSGYI | 384 | 11 | | | | | 3208 |
| HPV16 | L2 | TATDTLAPV | 81 | 9 | | | | | 3209 |
| HPV16 | L2 | TIDSAEEI | 332 | 8 | | | | | 3210 |
| HPV16 | L2 | TIDSAEEIEL | 332 | 10 | | | | | 3211 |
| HPV16 | L2 | TIIADAGDFYL | 438 | 11 | | | | | 3212 |
| HPV16 | L2 | TIPFGGAYNI | 399 | 10 | | | | | 3213 |
| HPV16 | L2 | TISTHNYEEI | 187 | 10 | | | | | 3214 |
| HPV16 | L2 | TITPSTYT | 343 | 8 | | | | | 3215 |
| HPV16 | L2 | TITPSTYTT | 343 | 9 | | | | | 3216 |
| HPV16 | L2 | TITPSTYTTT | 343 | 10 | | | | | 3217 |
| HPV16 | L2 | TLAPVRPPL | 85 | 9 | | | | | 3218 |
| HPV16 | L2 | TLAPVRPPLT | 85 | 10 | | | | | 3219 |
| HPV16 | L2 | TLAPVRPPLTV | 85 | 11 | | | | | 3220 |
| HPV16 | L2 | TLRTRSGKSI | 311 | 10 | | | | | 3221 |
| HPV16 | L2 | TLSSSTIST | 182 | 9 | | | | | 3222 |
| HPV16 | L2 | TLYFSSNDNSI | 265 | 11 | | | | | 3223 |
| HPV16 | L2 | TQLYKTCKQA | 16 | 10 | | | | | 3224 |
| HPV16 | L2 | TQQVKVVDPA | 232 | 10 | | | | | 3225 |
| HPV16 | L2 | TTHNNPTFT | 156 | 9 | | | | | 3226 |
| HPV16 | L2 | TTIPFGGA | 398 | 8 | | | | | 3227 |
| HPV16 | L2 | TTIPFGGAYNI | 398 | 11 | | | | | 3228 |
| HPV16 | L2 | TTPAILDI | 141 | 8 | | | | | 3229 |
| HPV16 | L2 | TTPAILDINNT | 141 | 11 | | | | | 3230 |
| HPV16 | L2 | TTPTKLIT | 244 | 8 | | | | | 3231 |
| HPV16 | L2 | TTPVPSVPST | 379 | 10 | | | | | 3232 |
| HPV16 | L2 | TTQQVKVV | 231 | 8 | | | | | 3233 |
| HPV16 | L2 | TTQQVKVVDPA | 231 | 11 | | | | | 3234 |
| HPV16 | L2 | TTSHAALPT | 351 | 9 | | | | | 3235 |
| HPV16 | L2 | TTSHAALPTSI | 351 | 11 | | | | | 3236 |
| HPV16 | L2 | TTSTDTTPA | 136 | 9 | | | | | 3237 |
| HPV16 | L2 | TTSTDTTPAI | 136 | 10 | | | | | 3238 |
| HPV16 | L2 | TTSTDTTPAIL | 136 | 11 | | | | | 3239 |
| HPV16 | L2 | TTTSHAAL | 350 | 8 | | | | | 3240 |
| HPV16 | L2 | TTTSHAALPT | 350 | 10 | | | | | 3241 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV16 | L2 | TTVTTHNNPT | 153 | 10 | | | | | 3242 |
| HPV16 | L2 | TVTSSTPI | 209 | 8 | | | | | 3243 |
| HPV16 | L2 | TVTTHNNPT | 154 | 9 | | | | | 3244 |
| HPV16 | L2 | TVTTHNNPTFT | 154 | 11 | | | | | 3245 |
| HPV16 | L2 | VALHRPAL | 287 | 8 | | | | | 3246 |
| HPV16 | L2 | VALHRPALT | 287 | 9 | | | | | 3247 |
| HPV16 | L2 | VARLGLYSRT | 222 | 10 | | | | | 3248 |
| HPV16 | L2 | VARLGLYSRTT | 222 | 11 | | | | | 3249 |
| HPV16 | L2 | VLQPPTPA | 168 | 8 | | | | | 3250 |
| HPV16 | L2 | VLQPPTPAET | 168 | 10 | | | | | 3251 |
| HPV16 | L2 | VTTHNNPT | 155 | 8 | | | | | 3252 |
| HPV16 | L2 | VTTHNNPTFT | 155 | 10 | | | | | 3253 |
| HPV16 | L2 | VTTVTTHNNPT | 152 | 11 | | | | | 3254 |
| HPV16 | L2 | VVDPAFIT | 237 | 8 | | | | | 3255 |
| HPV16 | L2 | VVDPAFITT | 237 | 9 | | | | | 3256 |
| HPV16 | L2 | VVDPAFITTPT | 237 | 11 | | | | | 3257 |
| HPV16 | L2 | YADDFITDT | 369 | 9 | | | | | 3258 |
| HPV16 | L2 | YADDFITDTST | 369 | 11 | | | | | 3259 |
| HPV16 | L2 | YIPANTTI | 393 | 8 | | | | | 3260 |
| HPV16 | L2 | YIPLGTRPPT | 72 | 10 | | | | | 3261 |
| HPV16 | L2 | YIPLGTRPPTA | 72 | 11 | | | | | 3262 |
| HPV16 | L2 | YLHPSYYM | 447 | 8 | | | | | 3263 |
| HPV16 | L2 | YLHPSYYML | 447 | 9 | | | | | 3264 |
| HPV16 | L2 | YMLRKRRKRL | 453 | 10 | | | | | 3265 |
| HPV16 | L2 | YTTTSHAA | 349 | 8 | | | | | 3266 |
| HPV16 | L2 | YTTTSHAAL | 349 | 9 | | | | | 3267 |
| HPV16 | L2 | YTTTSHAALPT | 349 | 11 | | | | | 3268 |
| HPV18 | E1 | AAAFLKSNCQA | 396 | 11 | | | | | 3269 |
| HPV18 | E1 | AAFLKSNCQA | 397 | 10 | | | | | 3270 |
| HPV18 | E1 | AALYWYRT | 324 | 8 | | | | | 3271 |
| HPV18 | E1 | AALYWYRTGI | 324 | 10 | | | | | 3272 |
| HPV18 | E1 | AIFGVNPT | 246 | 8 | | | | | 3273 |
| HPV18 | E1 | AIFGVNPTI | 246 | 9 | 0.0021 | | | | 3274 |
| HPV18 | E1 | AIFGVNPTIA | 246 | 10 | | | | | 3275 |
| HPV18 | E1 | AIVDKKTGDV | 22 | 10 | | | | | 3276 |
| HPV18 | E1 | AIVDKKTGDVI | 22 | 11 | | | | | 3277 |
| HPV18 | E1 | ALDGNPISI | 546 | 9 | 0.021 | | | | 3278 |
| HPV18 | E1 | ALFHAQEV | 68 | 8 | | | | | 3279 |
| HPV18 | E1 | ALKSFLKGT | 466 | 9 | | | | | 3280 |
| HPV18 | E1 | ALLADSNSNA | 387 | 10 | 0.0004 | | | | 3281 |
| HPV18 | E1 | ALLADSNSNAA | 387 | 11 | | | | | 3282 |
| HPV18 | E1 | ALYWYRTGI | 325 | 9 | 0.0032 | | | | 3283 |
| HPV18 | E1 | AMLAVFKDT | 213 | 9 | | | | | 3284 |
| HPV18 | E1 | AMLDDATT | 526 | 8 | | | | | 3285 |
| HPV18 | E1 | AMLDDATTT | 526 | 9 | | | | | 3286 |
| HPV18 | E1 | AQALFHAQEV | 66 | 10 | | | | | 3287 |
| HPV18 | E1 | AQEVHNDA | 72 | 8 | | | | | 3288 |
| HPV18 | E1 | AQEVHNDAQV | 72 | 10 | | | | | 3289 |
| HPV18 | E1 | AQEVHNDAQVL | 72 | 11 | | | | | 3290 |
| HPV18 | E1 | AQKRQMNM | 422 | 8 | | | | | 3291 |
| HPV18 | E1 | AQLKDLLKV | 199 | 9 | | | | | 3292 |
| HPV18 | E1 | ATDTGSDM | 40 | 8 | | | | | 3293 |
| HPV18 | E1 | ATDTGSDMV | 40 | 9 | | | | | 3294 |
| HPV18 | E1 | ATMCKHYRRA | 413 | 10 | | | | | 3295 |
| HPV18 | E1 | ATQIQVTT | 144 | 8 | | | | | 3296 |
| HPV18 | E1 | ATTTCWTYFDT | 531 | 11 | | | | | 3297 |
| HPV18 | E1 | AVFKDTYGL | 216 | 9 | 0.014 | | | | 3298 |
| HPV18 | E1 | AVISFVNST | 504 | 9 | | | | | 3299 |
| HPV18 | E1 | CATMCKHYRRA | 412 | 11 | | | | | 3300 |
| HPV18 | E1 | CLDCKWGV | 273 | 8 | | | | | 3301 |
| HPV18 | E1 | CLDCKWGVL | 273 | 9 | | | | | 3302 |
| HPV18 | E1 | CLDCKWGVLI | 273 | 10 | 0.0002 | | | | 3303 |
| HPV18 | E1 | CLDCKWGVLIL | 273 | 11 | | | | | 3304 |
| HPV18 | E1 | CLVFCGPA | 479 | 8 | | | | | 3305 |
| HPV18 | E1 | CLVFCGPANT | 479 | 10 | | | | | 3306 |
| HPV18 | E1 | CMLIQPPKL | 311 | 9 | | | | | 3307 |
| HPV18 | E1 | CQAKYLKDCA | 404 | 10 | | | | | 3308 |
| HPV18 | E1 | CQAKYLKDCAT | 404 | 11 | | | | | 3309 |
| HPV18 | E1 | CTDWVTAI | 240 | 8 | | | | | 3310 |
| HPV18 | E1 | CTDWVTAIFGV | 240 | 11 | | | | | 3311 |
| HPV18 | E1 | CTIAQLKDL | 196 | 9 | | | | | 3312 |
| HPV18 | E1 | CTIAQLKDLL | 196 | 10 | | | | | 3313 |
| HPV18 | E1 | DADTEGNPFGT | 635 | 11 | | | | | 3314 |
| HPV18 | E1 | DAQVLHVL | 78 | 8 | | | | | 3315 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E1 | DATTTCWT | 530 | 8 | | | | | 3316 |
| HPV18 | E1 | DLHEEEEDA | 628 | 9 | | | | | 3317 |
| HPV18 | E1 | DLHEEEEDADT | 628 | 11 | | | | | 3318 |
| HPV18 | E1 | DLLKVNNKQGA | 203 | 11 | | | | | 3319 |
| HPV18 | E1 | DLSEMVQWA | 363 | 9 | 0.0003 | | | | 3320 |
| HPV18 | E1 | DLVRNFKSDKT | 228 | 11 | | | | | 3321 |
| HPV18 | E1 | DMAFEYAL | 381 | 8 | | | | | 3322 |
| HPV18 | E1 | DMAFEYALL | 381 | 9 | | | | | 3323 |
| HPV18 | E1 | DMAFEYALLA | 381 | 10 | | | | | 3324 |
| HPV18 | E1 | DMVDFIDT | 46 | 8 | | | | | 3325 |
| HPV18 | E1 | DMVDFIDTQGT | 46 | 11 | | | | | 3326 |
| HPV18 | E1 | DTEGNPFGT | 637 | 9 | | | | | 3327 |
| HPV18 | E1 | DTELSPRL | 106 | 8 | | | | | 3328 |
| HPV18 | E1 | DTELSPRLQEI | 106 | 11 | | | | | 3329 |
| HPV18 | E1 | DTGSDMVDFI | 42 | 10 | | | | | 3330 |
| HPV18 | E1 | DTKVAMLDDA | 522 | 10 | | | | | 3331 |
| HPV18 | E1 | DTKVAMLDDAT | 522 | 11 | | | | | 3332 |
| HPV18 | E1 | DTPEWIQRL | 342 | 9 | | | | | 3333 |
| HPV18 | E1 | DTPEWIQRLT | 342 | 10 | | | | | 3334 |
| HPV18 | E1 | DTPEWIQRLTI | 342 | 11 | | | | | 3335 |
| HPV18 | E1 | DTQGTFCEQA | 52 | 10 | | | | | 3336 |
| HPV18 | E1 | DTYGLSFT | 220 | 8 | | | | | 3337 |
| HPV18 | E1 | DTYGLSFTDL | 220 | 10 | | | | | 3338 |
| HPV18 | E1 | DTYGLSFTDLV | 220 | 11 | | | | | 3339 |
| HPV18 | E1 | DTYMRNAL | 540 | 8 | | | | | 3340 |
| HPV18 | E1 | DVISDDEDENA | 30 | 11 | | | | | 3341 |
| HPV18 | E1 | EAIDNGGT | 166 | 8 | | | | | 3342 |
| HPV18 | E1 | EATQIQVT | 143 | 8 | | | | | 3343 |
| HPV18 | E1 | EATQIQVTT | 143 | 9 | | | | | 3344 |
| HPV18 | E1 | EISLNSGQKKA | 115 | 11 | | | | | 3345 |
| HPV18 | E1 | ELETAQAL | 62 | 8 | | | | | 3346 |
| HPV18 | E1 | ELETAQALFHA | 62 | 11 | | | | | 3347 |
| HPV18 | E1 | ELSPRLQEI | 108 | 9 | 0.0004 | | | | 3348 |
| HPV18 | E1 | ELSPRLQEISL | 108 | 11 | | | | | 3349 |
| HPV18 | E1 | ELTDESDM | 375 | 8 | | | | | 3350 |
| HPV18 | E1 | ELTDESDMA | 375 | 9 | | | | | 3351 |
| HPV18 | E1 | EMVQWAFDNEL | 366 | 11 | | | | | 3352 |
| HPV18 | E1 | EQAELETA | 59 | 8 | | | | | 3353 |
| HPV18 | E1 | EQAELETAQA | 59 | 10 | | | | | 3354 |
| HPV18 | E1 | EQAELETAQAL | 59 | 11 | | | | | 3355 |
| HPV18 | E1 | ETAQALFHA | 64 | 9 | | | | | 3356 |
| HPV18 | E1 | ETCMLIQPPKL | 309 | 11 | | | | | 3357 |
| HPV18 | E1 | EVDTELSPRL | 104 | 10 | | | | | 3358 |
| HPV18 | E1 | EVEATQIQV | 141 | 9 | | | | | 3359 |
| HPV18 | E1 | EVEATQIQVT | 141 | 10 | | | | | 3360 |
| HPV18 | E1 | EVEATQIQVTT | 141 | 11 | | | | | 3361 |
| HPV18 | E1 | EVHNDAQV | 74 | 8 | | | | | 3362 |
| HPV18 | E1 | EVHNDAQVL | 74 | 9 | | | | | 3363 |
| HPV18 | E1 | EVHNDAQVLHV | 74 | 11 | | | | | 3364 |
| HPV18 | E1 | EVMGDTPEWI | 338 | 10 | | | | | 3365 |
| HPV18 | E1 | FAGGSTENSPL | 89 | 11 | | | | | 3366 |
| HPV18 | E1 | FIHFIQGA | 497 | 8 | | | | | 3367 |
| HPV18 | E1 | FIHFIQGAV | 497 | 9 | 0.013 | | | | 3368 |
| HPV18 | E1 | FIHFIQGAVI | 497 | 10 | 0.0057 | | | | 3369 |
| HPV18 | E1 | FILYAHIQCL | 265 | 10 | 0.032 | | | | 3370 |
| HPV18 | E1 | FIQGAVISFV | 500 | 10 | 0.046 | | | | 3371 |
| HPV18 | E1 | FITFLGAL | 460 | 8 | | | | | 3372 |
| HPV18 | E1 | FLGALKSFL | 463 | 9 | 0.045 | | | | 3373 |
| HPV18 | E1 | FLKGTPKKNCL | 470 | 11 | | | | | 3374 |
| HPV18 | E1 | FLKSNCQA | 399 | 8 | | | | | 3375 |
| HPV18 | E1 | FLKSNCQAKYL | 399 | 11 | | | | | 3376 |
| HPV18 | E1 | FLRYQQIEFI | 452 | 10 | 0.0025 | | | | 3377 |
| HPV18 | E1 | FLRYQQIEFIT | 452 | 11 | | | | | 3378 |
| HPV18 | E1 | FVNSTSHFWL | 508 | 10 | 0.062 | | | | 3379 |
| HPV18 | E1 | GALKSFLKGT | 465 | 10 | | | | | 3380 |
| HPV18 | E1 | GAMLAVFKDT | 212 | 10 | | | | | 3381 |
| HPV18 | E1 | GAVISFVNST | 503 | 10 | | | | | 3382 |
| HPV18 | E1 | GIDDSNFDL | 356 | 9 | | | | | 3383 |
| HPV18 | E1 | GISNISEV | 332 | 8 | | | | | 3384 |
| HPV18 | E1 | GISNISEVM | 332 | 9 | | | | | 3385 |
| HPV18 | E1 | GLSFTDLV | 223 | 8 | | | | | 3386 |
| HPV18 | E1 | GLSTLLHV | 300 | 8 | | | | | 3387 |
| HPV18 | E1 | GLSTLLHVPET | 300 | 11 | | | | | 3388 |
| HPV18 | E1 | GMSFIHFI | 494 | 8 | | | | | 3389 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E1 | GMSFIHFIQGA | 494 | 11 | | | | | 3390 |
| HPV18 | E1 | GQKKAKRRL | 121 | 9 | | | | | 3391 |
| HPV18 | E1 | GQKKAKRRLFT | 121 | 11 | | | | | 3392 |
| HPV18 | E1 | GTEGNNSSV | 172 | 9 | | | | | 3393 |
| HPV18 | E1 | GTFCEQAEL | 55 | 9 | | | | | 3394 |
| HPV18 | E1 | GTFCEQAELET | 55 | 11 | | | | | 3395 |
| HPV18 | E1 | GTGCNGWFYV | 11 | 10 | 0.0006 | | | | 3396 |
| HPV18 | E1 | GTPKKNCL | 473 | 8 | | | | | 3397 |
| HPV18 | E1 | GTPKKNCLV | 473 | 9 | | | | | 3398 |
| HPV18 | E1 | GTSDNSNI | 182 | 8 | | | | | 3399 |
| HPV18 | E1 | GTSDNSNIENV | 182 | 11 | | | | | 3400 |
| HPV18 | E1 | GVLILALL | 279 | 8 | | | | | 3401 |
| HPV18 | E1 | HAQEVHNDA | 71 | 9 | | | | | 3402 |
| HPV18 | E1 | HAQEVHNDAQV | 71 | 11 | | | | | 3403 |
| HPV18 | E1 | HIQCLDCKWGV | 270 | 11 | | | | | 3404 |
| HPV18 | E1 | HVLKRKFA | 83 | 8 | | | | | 3405 |
| HPV18 | E1 | HVPETCML | 306 | 8 | | | | | 3406 |
| HPV18 | E1 | HVPETCMLI | 306 | 9 | | | | | 3407 |
| HPV18 | E1 | IAEGFKTL | 254 | 8 | | | | | 3408 |
| HPV18 | E1 | IAEGFKTLI | 254 | 9 | 0.0003 | | | | 3409 |
| HPV18 | E1 | IAQLKDLL | 198 | 8 | | | | | 3410 |
| HPV18 | E1 | IAQLKDLLKV | 198 | 10 | | | | | 3411 |
| HPV18 | E1 | ILLTTNIHPA | 569 | 10 | 0.08 | | | | 3412 |
| HPV18 | E1 | ILYAHIQCL | 266 | 9 | 0.081 | | | | 3413 |
| HPV18 | E1 | IQCLDCKWGV | 271 | 10 | | | | | 3414 |
| HPV18 | E1 | IQCLDCKWGVL | 271 | 11 | | | | | 3415 |
| HPV18 | E1 | IQGAVISFV | 501 | 9 | | | | | 3416 |
| HPV18 | E1 | IQLKCPPI | 562 | 8 | | | | | 3417 |
| HPV18 | E1 | IQLKCPPIL | 562 | 9 | | | | | 3418 |
| HPV18 | E1 | IQLKCPPILL | 562 | 10 | | | | | 3419 |
| HPV18 | E1 | IQLKCPPILLT | 562 | 11 | | | | | 3420 |
| HPV18 | E1 | IQPFILYA | 262 | 8 | | | | | 3421 |
| HPV18 | E1 | IQPFILYAHI | 262 | 10 | | | | | 3422 |
| HPV18 | E1 | IQPPKLRSSV | 314 | 10 | | | | | 3423 |
| HPV18 | E1 | IQPPKLRSSVA | 314 | 11 | | | | | 3424 |
| HPV18 | E1 | IQRLTIIQHGI | 347 | 11 | | | | | 3425 |
| HPV18 | E1 | ITFLGALKSFL | 461 | 11 | | | | | 3426 |
| HPV18 | E1 | ITVFEFPNA | 590 | 9 | | | | | 3427 |
| HPV18 | E1 | IVDKKTGDV | 23 | 9 | | | | | 3428 |
| HPV18 | E1 | IVDKKTGDVI | 23 | 10 | | | | | 3429 |
| HPV18 | E1 | IVQFLRYQQI | 449 | 10 | | | | | 3430 |
| HPV18 | E1 | KAKRRLFT | 124 | 8 | | | | | 3431 |
| HPV18 | E1 | KAKRRLFTI | 124 | 9 | | | | | 3432 |
| HPV18 | E1 | KIDEGGDWRPI | 439 | 11 | | | | | 3433 |
| HPV18 | E1 | KLRAGQNHRPL | 647 | 11 | | | | | 3434 |
| HPV18 | E1 | KLRSSVAA | 318 | 8 | | | | | 3435 |
| HPV18 | E1 | KLRSSVAAL | 318 | 9 | 0.0003 | | | | 3436 |
| HPV18 | E1 | KQGAMLAV | 210 | 8 | | | | | 3437 |
| HPV18 | E1 | KTLIQPFI | 259 | 8 | | | | | 3438 |
| HPV18 | E1 | KTLIQPFIL | 259 | 9 | | | | | 3439 |
| HPV18 | E1 | KTLIQPFILYA | 259 | 11 | | | | | 3440 |
| HPV18 | E1 | KTTCTDWV | 237 | 8 | | | | | 3441 |
| HPV18 | E1 | KTTCTDWVT | 237 | 9 | | | | | 3442 |
| HPV18 | E1 | KTTCTDWVTA | 237 | 10 | | | | | 3443 |
| HPV18 | E1 | KTTCTDWVTAI | 237 | 11 | | | | | 3444 |
| HPV18 | E1 | KVAMLDDA | 524 | 8 | | | | | 3445 |
| HPV18 | E1 | KVAMLDDAT | 524 | 9 | | | | | 3446 |
| HPV18 | E1 | KVAMLDDATT | 524 | 10 | | | | | 3447 |
| HPV18 | E1 | KVAMLDDATTT | 524 | 11 | | | | | 3448 |
| HPV18 | E1 | KVNNKQGA | 206 | 8 | | | | | 3449 |
| HPV18 | E1 | KVNNKQGAM | 206 | 9 | | | | | 3450 |
| HPV18 | E1 | KVNNKQGAML | 206 | 10 | | | | | 3451 |
| HPV18 | E1 | KVNNKQGAMLA | 206 | 11 | | | | | 3452 |
| HPV18 | E1 | LADSNSNA | 389 | 8 | | | | | 3453 |
| HPV18 | E1 | LADSNSNAA | 389 | 9 | | | | | 3454 |
| HPV18 | E1 | LADSNSNAAA | 389 | 10 | | | | | 3455 |
| HPV18 | E1 | LAVFKDTYGL | 215 | 10 | | | | | 3456 |
| HPV18 | E1 | LIQLKCPPI | 561 | 9 | 0.0004 | | | | 3457 |
| HPV18 | E1 | LIQLKCPPIL | 561 | 10 | | | | | 3458 |
| HPV18 | E1 | LIQLKCPPILL | 561 | 11 | | | | | 3459 |
| HPV18 | E1 | LIQPFILYA | 261 | 9 | | | | | 3460 |
| HPV18 | E1 | LIQPFILYAHI | 261 | 11 | | | | | 3461 |
| HPV18 | E1 | LIQPPKLRSSV | 313 | 11 | | | | | 3462 |
| HPV18 | E1 | LLADSNSNA | 388 | 9 | | | | | 3463 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E1 | LLADSNSNAA | 388 | 10 | | | | | 3464 |
| HPV18 | E1 | LLADSNSNAAA | 388 | 11 | | | | | 3465 |
| HPV18 | E1 | LLHVPETCM | 304 | 9 | | | | | 3466 |
| HPV18 | E1 | LLHVPETCML | 304 | 10 | | | | | 3467 |
| HPV18 | E1 | LLHVPETCMLI | 304 | 11 | | | | | 3468 |
| HPV18 | E1 | LLKVNNKQGA | 204 | 10 | | | | | 3469 |
| HPV18 | E1 | LLKVNNKQGAM | 204 | 11 | | | | | 3470 |
| HPV18 | E1 | LLRYKCGKSRL | 285 | 11 | | | | | 3471 |
| HPV18 | E1 | LLTTNIHPA | 570 | 9 | 0.18 | | | | 3472 |
| HPV18 | E1 | LTDESDMA | 376 | 8 | | | | | 3473 |
| HPV18 | E1 | LTDTKVAM | 520 | 8 | | | | | 3474 |
| HPV18 | E1 | LTDTKVAML | 520 | 9 | | | | | 3475 |
| HPV18 | E1 | LTIIQHGI | 350 | 8 | | | | | 3476 |
| HPV18 | E1 | LTTNIHPA | 571 | 8 | | | | | 3477 |
| HPV18 | E1 | LTVAKGLST | 295 | 9 | | | | | 3478 |
| HPV18 | E1 | LTVAKGLSTL | 295 | 10 | | | | | 3479 |
| HPV18 | E1 | LTVAKGLSTLL | 295 | 11 | | | | | 3480 |
| HPV18 | E1 | LVFCGPANT | 480 | 9 | | | | | 3481 |
| HPV18 | E1 | LVRNFKSDKT | 229 | 10 | | | | | 3482 |
| HPV18 | E1 | LVRNFKSDKTT | 229 | 11 | | | | | 3483 |
| HPV18 | E1 | MAFEYALL | 382 | 8 | | | | | 3484 |
| HPV18 | E1 | MAFEYALLA | 382 | 9 | | | | | 3485 |
| HPV18 | E1 | MLAVFKDT | 214 | 8 | | | | | 3486 |
| HPV18 | E1 | MLAVFKDTYGL | 214 | 11 | | | | | 3487 |
| HPV18 | E1 | MLDDATTT | 527 | 8 | | | | | 3488 |
| HPV18 | E1 | MLDDATTTCWT | 527 | 11 | | | | | 3489 |
| HPV18 | E1 | MLIQPPKL | 312 | 8 | | | | | 3490 |
| HPV18 | E1 | MVDFIDTQGT | 47 | 10 | | | | | 3491 |
| HPV18 | E1 | MVQWAFDNEL | 367 | 10 | | | | | 3492 |
| HPV18 | E1 | MVQWAFDNELT | 367 | 11 | | | | | 3493 |
| HPV18 | E1 | NALDGNPI | 545 | 8 | | | | | 3494 |
| HPV18 | E1 | NALDGNPISI | 545 | 10 | | | | | 3495 |
| HPV18 | E1 | NATDTGSDM | 39 | 9 | | | | | 3496 |
| HPV18 | E1 | NATDTGSDMV | 39 | 10 | | | | | 3497 |
| HPV18 | E1 | NIENVNPQCT | 188 | 10 | | | | | 3498 |
| HPV18 | E1 | NIENVNPQCTI | 188 | 11 | | | | | 3499 |
| HPV18 | E1 | NISEVMGDT | 335 | 9 | | | | | 3500 |
| HPV18 | E1 | NTGKSYFGM | 487 | 9 | | | | | 3501 |
| HPV18 | E1 | NVCSGGST | 158 | 8 | | | | | 3502 |
| HPV18 | E1 | NVCSGGSTEA | 158 | 10 | | | | | 3503 |
| HPV18 | E1 | NVCSGGSTEAI | 158 | 11 | | | | | 3504 |
| HPV18 | E1 | NVNPQCTI | 191 | 8 | | | | | 3505 |
| HPV18 | E1 | NVNPQCTIA | 191 | 9 | | | | | 3506 |
| HPV18 | E1 | NVNPQCTIAQL | 191 | 11 | | | | | 3507 |
| HPV18 | E1 | PAKDNRWPYL | 577 | 10 | | | | | 3508 |
| HPV18 | E1 | PANTGKSYFGM | 485 | 11 | | | | | 3509 |
| HPV18 | E1 | PILLTTNI | 568 | 8 | | | | | 3510 |
| HPV18 | E1 | PILLTTNIHPA | 568 | 11 | | | | | 3511 |
| HPV18 | E1 | PISIDRKHKPL | 551 | 11 | | | | | 3512 |
| HPV18 | E1 | PIVQFLRYQQI | 448 | 11 | | | | | 3513 |
| HPV18 | E1 | PLGERLEV | 98 | 8 | | | | | 3514 |
| HPV18 | E1 | PLGERLEVDT | 98 | 10 | | | | | 3515 |
| HPV18 | E1 | PLIQLKCPPI | 560 | 10 | | | | | 3516 |
| HPV18 | E1 | PLIQLKCPPIL | 560 | 11 | | | | | 3517 |
| HPV18 | E1 | PLTDTKVA | 519 | 8 | | | | | 3518 |
| HPV18 | E1 | PLTDTKVAM | 519 | 9 | | | | | 3519 |
| HPV18 | E1 | PLTDTKVAML | 519 | 10 | | | | | 3520 |
| HPV18 | E1 | PQCTIAQL | 194 | 8 | | | | | 3521 |
| HPV18 | E1 | PQCTIAQLKDL | 194 | 11 | | | | | 3522 |
| HPV18 | E1 | PTIAEGFKT | 252 | 9 | | | | | 3523 |
| HPV18 | E1 | PTIAEGFKTL | 252 | 10 | | | | | 3524 |
| HPV18 | E1 | PTIAEGFKTLI | 252 | 11 | | | | | 3525 |
| HPV18 | E1 | QAELETAQA | 60 | 9 | | | | | 3526 |
| HPV18 | E1 | QAELETAQAL | 60 | 10 | | | | | 3527 |
| HPV18 | E1 | QAIVDKKT | 21 | 8 | | | | | 3528 |
| HPV18 | E1 | QAIVDKKTGDV | 21 | 11 | | | | | 3529 |
| HPV18 | E1 | QAKYLKDCA | 405 | 9 | | | | | 3530 |
| HPV18 | E1 | QAKYLKDCAT | 405 | 10 | | | | | 3531 |
| HPV18 | E1 | QAKYLKDCATM | 405 | 11 | | | | | 3532 |
| HPV18 | E1 | QALFHAQEV | 67 | 9 | 0.0002 | | | | 3533 |
| HPV18 | E1 | QIEFITFL | 457 | 8 | | | | | 3534 |
| HPV18 | E1 | QIEFITFLGA | 457 | 10 | | | | | 3535 |
| HPV18 | E1 | QIEFITFLGAL | 457 | 11 | | | | | 3536 |
| HPV18 | E1 | QLKCPPIL | 563 | 8 | | | | | 3537 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E1 | QLKCPPILL | 563 | 9 | 0.0003 | | | | 3538 |
| HPV18 | E1 | QLKCPPILLT | 563 | 10 | | | | | 3539 |
| HPV18 | E1 | QLKCPPILLTT | 563 | 11 | | | | | 3540 |
| HPV18 | E1 | QLKDLLKV | 200 | 8 | | | | | 3541 |
| HPV18 | E1 | QMNMSQWI | 426 | 8 | | | | | 3542 |
| HPV18 | E1 | QQIEFITFL | 456 | 9 | | | | | 3543 |
| HPV18 | E1 | QQIEFITFLGA | 456 | 11 | | | | | 3544 |
| HPV18 | E1 | QVLHVLKRKFA | 80 | 11 | | | | | 3545 |
| HPV18 | E1 | RAGQNHRPL | 649 | 9 | | | | | 3546 |
| HPV18 | E1 | RAQKRQMNM | 421 | 9 | | | | | 3547 |
| HPV18 | E1 | RITVFEFPNA | 589 | 10 | | | | | 3548 |
| HPV18 | E1 | RLDLHEEEEDA | 626 | 11 | | | | | 3549 |
| HPV18 | E1 | RLEVDTEL | 102 | 8 | | | | | 3550 |
| HPV18 | E1 | RLTIIQHGI | 349 | 9 | | | | | 3551 |
| HPV18 | E1 | RLTVAKGL | 294 | 8 | | | | | 3552 |
| HPV18 | E1 | RLTVAKGLST | 294 | 10 | | | | | 3553 |
| HPV18 | E1 | RLTVAKGLSTL | 294 | 11 | | | | | 3554 |
| HPV18 | E1 | RQMNMSQWI | 425 | 9 | | | | | 3555 |
| HPV18 | E1 | RTGISNISEV | 330 | 10 | | | | | 3556 |
| HPV18 | E1 | RTGISNISEVM | 330 | 11 | | | | | 3557 |
| HPV18 | E1 | RTWSRLDL | 622 | 8 | | | | | 3558 |
| HPV18 | E1 | SIDRKHKPL | 553 | 9 | | | | | 3559 |
| HPV18 | E1 | SIDRKHKPLI | 553 | 10 | | | | | 3560 |
| HPV18 | E1 | SLNSGQKKA | 117 | 9 | | | | | 3561 |
| HPV18 | E1 | SQWIRFRCSKI | 430 | 11 | | | | | 3562 |
| HPV18 | E1 | STEAIDNGGT | 164 | 10 | | | | | 3563 |
| HPV18 | E1 | STENSPLGERL | 93 | 11 | | | | | 3564 |
| HPV18 | E1 | STLLHVPET | 302 | 9 | | | | | 3565 |
| HPV18 | E1 | STLLHVPETCM | 302 | 11 | | | | | 3566 |
| HPV18 | E1 | STSHFWLEPL | 511 | 10 | | | | | 3567 |
| HPV18 | E1 | STSHFWLEPLT | 511 | 11 | | | | | 3568 |
| HPV18 | E1 | SVAALYWYRT | 322 | 10 | | | | | 3569 |
| HPV18 | E1 | SVDGTSDNSNI | 179 | 11 | | | | | 3570 |
| HPV18 | E1 | TAIFGVNPT | 245 | 9 | | | | | 3571 |
| HPV18 | E1 | TAIFGVNPTI | 245 | 10 | | | | | 3572 |
| HPV18 | E1 | TAIFGVNPTIA | 245 | 11 | | | | | 3573 |
| HPV18 | E1 | TAQALFHA | 65 | 8 | | | | | 3574 |
| HPV18 | E1 | TAQALFHAQEV | 65 | 11 | | | | | 3575 |
| HPV18 | E1 | TIAEGFKT | 253 | 8 | | | | | 3576 |
| HPV18 | E1 | TIAEGFKTL | 253 | 9 | | | | | 3577 |
| HPV18 | E1 | TIAEGFKTLI | 253 | 10 | | | | | 3578 |
| HPV18 | E1 | TIAQLKDL | 197 | 8 | | | | | 3579 |
| HPV18 | E1 | TIAQLKDLL | 197 | 9 | | | | | 3580 |
| HPV18 | E1 | TIAQLKDLLKV | 197 | 11 | | | | | 3581 |
| HPV18 | E1 | TLIQPFIL | 260 | 8 | | | | | 3582 |
| HPV18 | E1 | TLIQPFILYA | 260 | 10 | | | | | 3583 |
| HPV18 | E1 | TLLHVPET | 303 | 8 | | | | | 3584 |
| HPV18 | E1 | TLLHVPETCM | 303 | 10 | | | | | 3585 |
| HPV18 | E1 | TLLHVPETCML | 303 | 11 | | | | | 3586 |
| HPV18 | E1 | TMCKHYRRA | 414 | 9 | | | | | 3587 |
| HPV18 | E1 | TQGTFCEQA | 53 | 9 | | | | | 3588 |
| HPV18 | E1 | TQGTFCEQAEL | 53 | 11 | | | | | 3589 |
| HPV18 | E1 | TTCTDWVT | 238 | 8 | | | | | 3590 |
| HPV18 | E1 | TTCTDWVTA | 238 | 9 | | | | | 3591 |
| HPV18 | E1 | TTCTDWVTAI | 238 | 10 | | | | | 3592 |
| HPV18 | E1 | TTCWTYFDT | 533 | 9 | | | | | 3593 |
| HPV18 | E1 | TTCWTYFDTYM | 533 | 11 | | | | | 3594 |
| HPV18 | E1 | TTNGEHGGNV | 150 | 10 | | | | | 3595 |
| HPV18 | E1 | TTTCWTYFDT | 532 | 10 | | | | | 3596 |
| HPV18 | E1 | TVAKGLST | 296 | 8 | | | | | 3597 |
| HPV18 | E1 | TVAKGLSTL | 296 | 9 | | | | | 3598 |
| HPV18 | E1 | TVAKGLSTLL | 296 | 10 | | | | | 3599 |
| HPV18 | E1 | TVFEFPNA | 591 | 8 | | | | | 3600 |
| HPV18 | E1 | VAALYWYRT | 323 | 9 | | | | | 3601 |
| HPV18 | E1 | VAALYWYRTGI | 323 | 11 | | | | | 3602 |
| HPV18 | E1 | VAKGLSTL | 297 | 8 | | | | | 3603 |
| HPV18 | E1 | VAKGLSTLL | 297 | 9 | | | | | 3604 |
| HPV18 | E1 | VAKGLSTLLHV | 297 | 11 | | | | | 3605 |
| HPV18 | E1 | VAMLDDAT | 525 | 8 | | | | | 3606 |
| HPV18 | E1 | VAMLDDATT | 525 | 9 | | | | | 3607 |
| HPV18 | E1 | VAMLDDATTT | 525 | 10 | | | | | 3608 |
| HPV18 | E1 | VISDDEDENA | 31 | 10 | | | | | 3609 |
| HPV18 | E1 | VISDDEDENAT | 31 | 11 | | | | | 3610 |
| HPV18 | E1 | VISFVNST | 505 | 8 | | | | | 3611 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E1 | VLHVLKRKFA | 81 | 10 | | | | | 3612 |
| HPV18 | E1 | VLKRKFAGGST | 84 | 11 | | | | | 3613 |
| HPV18 | E1 | VMGDTPEWI | 339 | 9 | 0.007 | | | | 3614 |
| HPV18 | E1 | VQAIVDKKT | 20 | 9 | | | | | 3615 |
| HPV18 | E1 | VQFLRYQQI | 450 | 9 | | | | | 3616 |
| HPV18 | E1 | VQWAFDNEL | 368 | 9 | | | | | 3617 |
| HPV18 | E1 | VQWAFDNELT | 368 | 10 | | | | | 3618 |
| HPV18 | E1 | VTAIFGVNPT | 244 | 10 | | | | | 3619 |
| HPV18 | E1 | VTAIFGVNPTI | 244 | 11 | | | | | 3620 |
| HPV18 | E1 | VTTNGEHGGNV | 149 | 11 | | | | | 3621 |
| HPV18 | E1 | WAFDNELT | 370 | 8 | | | | | 3622 |
| HPV18 | E1 | WIQRLTII | 346 | 8 | | | | | 3623 |
| HPV18 | E1 | WIRFRCSKI | 432 | 9 | | | | | 3624 |
| HPV18 | E1 | WLEPLTDT | 516 | 8 | | | | | 3625 |
| HPV18 | E1 | WLEPLTDTKV | 516 | 10 | | | | | 3626 |
| HPV18 | E1 | WLEPLTDTKVA | 516 | 11 | | | | | 3627 |
| HPV18 | E1 | WTYFDTYM | 536 | 8 | | | | | 3628 |
| HPV18 | E1 | WTYFDTYMRNA | 536 | 11 | | | | | 3629 |
| HPV18 | E1 | WVTAIFGV | 243 | 8 | | | | | 3630 |
| HPV18 | E1 | WVTAIFGVNPT | 243 | 11 | | | | | 3631 |
| HPV18 | E1 | YALLADSNSNA | 386 | 11 | | | | | 3632 |
| HPV18 | E1 | YLESRITV | 585 | 8 | | | | | 3633 |
| HPV18 | E1 | YLKDCATM | 408 | 8 | | | | | 3634 |
| HPV18 | E1 | YMRNALDGNPI | 542 | 11 | | | | | 3635 |
| HPV18 | E1 | YQQIEFIT | 455 | 8 | | | | | 3636 |
| HPV18 | E1 | YQQIEFITFL | 455 | 10 | | | | | 3637 |
| HPV18 | E1 | YVQAIVDKKT | 19 | 10 | | | | | 3638 |
| HPV18 | E2 | AAREHGIQT | 49 | 9 | | | | | 3639 |
| HPV18 | E2 | AAREHGIQTL | 49 | 10 | | | | | 3640 |
| HPV18 | E2 | AATRPGHCGL | 245 | 10 | | | | | 3641 |
| HPV18 | E2 | AATRPGHCGLA | 245 | 11 | | | | | 3642 |
| HPV18 | E2 | AIELQMAL | 76 | 8 | | | | | 3643 |
| HPV18 | E2 | AIELQMALQGL | 76 | 11 | | | | | 3644 |
| HPV18 | E2 | AIFFAAREHGI | 45 | 11 | | | | | 3645 |
| HPV18 | E2 | AIPDSVQI | 351 | 8 | | | | | 3646 |
| HPV18 | E2 | AIPDSVQIL | 351 | 9 | | | | | 3647 |
| HPV18 | E2 | AIPDSVQILV | 351 | 10 | | | | | 3648 |
| HPV18 | E2 | AQSRYKTEDWT | 87 | 11 | | | | | 3649 |
| HPV18 | E2 | ATCVSHRGL | 154 | 9 | | | | | 3650 |
| HPV18 | E2 | ATQLVKQL | 214 | 8 | | | | | 3651 |
| HPV18 | E2 | ATQLVKQLQHT | 214 | 11 | | | | | 3652 |
| HPV18 | E2 | ATRPGHCGL | 246 | 9 | | | | | 3653 |
| HPV18 | E2 | ATRPGHCGLA | 246 | 10 | | | | | 3654 |
| HPV18 | E2 | CMTYVAWDSV | 132 | 10 | | | | | 3655 |
| HPV18 | E2 | CVSHRGLYYV | 156 | 10 | | | | | 3656 |
| HPV18 | E2 | DAGTWDKT | 146 | 8 | | | | | 3657 |
| HPV18 | E2 | DAGTWDKTA | 146 | 9 | | | | | 3658 |
| HPV18 | E2 | DAGTWDKTAT | 146 | 10 | | | | | 3659 |
| HPV18 | E2 | DIDSQIQYWQL | 29 | 11 | | | | | 3660 |
| HPV18 | E2 | DISSTWHWT | 315 | 9 | | | | | 3661 |
| HPV18 | E2 | DISSTWHWTGA | 315 | 11 | | | | | 3662 |
| HPV18 | E2 | DTCEELWNT | 100 | 9 | | | | | 3663 |
| HPV18 | E2 | DTVSATQL | 210 | 8 | | | | | 3664 |
| HPV18 | E2 | DTVSATQLV | 210 | 9 | | | | | 3665 |
| HPV18 | E2 | ELQMALQGL | 78 | 9 | | | | | 3666 |
| HPV18 | E2 | ELQMALQGLA | 78 | 10 | | | | | 3667 |
| HPV18 | E2 | ELWNTEPT | 104 | 8 | | | | | 3668 |
| HPV18 | E2 | ETLSERLSCV | 6 | 10 | | | | | 3669 |
| HPV18 | E2 | ETQRTKFL | 340 | 8 | | | | | 3670 |
| HPV18 | E2 | ETQRTKFLNT | 340 | 10 | | | | | 3671 |
| HPV18 | E2 | ETQRTKFLNTV | 340 | 11 | | | | | 3672 |
| HPV18 | E2 | EVHFGNNV | 190 | 8 | | | | | 3673 |
| HPV18 | E2 | EVHFGNNVI | 190 | 9 | | | | | 3674 |
| HPV18 | E2 | FAAREHGI | 48 | 8 | | | | | 3675 |
| HPV18 | E2 | FAAREHGIQT | 48 | 10 | | | | | 3676 |
| HPV18 | E2 | FAAREHGIQTL | 48 | 11 | | | | | 3677 |
| HPV18 | E2 | FLNTVAIPDSV | 346 | 11 | | | | | 3678 |
| HPV18 | E2 | GAGNEKTGI | 324 | 9 | | | | | 3679 |
| HPV18 | E2 | GAGNEKTGIL | 324 | 10 | | | | | 3680 |
| HPV18 | E2 | GAGNEKTGILT | 324 | 11 | | | | | 3681 |
| HPV18 | E2 | GILTVTYHSET | 331 | 11 | | | | | 3682 |
| HPV33 | E2 | GIQTLNHQV | 54 | 9 | | | | | 3683 |
| HPV18 | E2 | GIQTLNHQVV | 54 | 10 | | | | | 3684 |
| HPV18 | E2 | GLAEKQHCGPV | 253 | 11 | | | | | 3685 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E2 | GLAQSRYKT | 85 | 9 | | | | | 3686 |
| HPV18 | E2 | GLYYVKEGYNT | 161 | 11 | | | | | 3687 |
| HPV18 | E2 | GTAKTYGQT | 235 | 9 | | | | | 3688 |
| HPV18 | E2 | GTAKTYGQTSA | 235 | 11 | | | | | 3689 |
| HPV18 | E2 | GTWDKTAT | 148 | 8 | | | | | 3690 |
| HPV18 | E2 | GTWDKTATCV | 148 | 10 | | | | | 3691 |
| HPV18 | E2 | GTWEVHFGNNV | 187 | 11 | | | | | 3692 |
| HPV18 | E2 | HLKGDRNSL | 291 | 9 | | | | | 3693 |
| HPV18 | E2 | HQVVPAYNI | 60 | 9 | | | | | 3694 |
| HPV18 | E2 | HTPSPYSST | 223 | 9 | | | | | 3695 |
| HPV18 | E2 | HTPSPYSSTV | 223 | 10 | | | | | 3696 |
| HPV18 | E2 | IIHLKGDRNSL | 289 | 11 | | | | | 3697 |
| HPV18 | E2 | ILTVTYHSET | 332 | 10 | | | | | 3698 |
| HPV18 | E2 | ILVGYMTM | 358 | 8 | | | | | 3699 |
| HPV18 | E2 | IQTLNHQV | 55 | 8 | | | | | 3700 |
| HPV18 | E2 | IQTLNHQVV | 55 | 9 | | | | | 3701 |
| HPV18 | E2 | IQTLNHQVVPA | 55 | 11 | | | | | 3702 |
| HPV18 | E2 | KAHKAIEL | 72 | 8 | | | | | 3703 |
| HFV33 | E2 | KAHKAIELQM | 72 | 10 | | | | | 3704 |
| HPV18 | E2 | KAHKAIELQMA | 72 | 11 | | | | | 3705 |
| HPV18 | E2 | KAIELQMA | 75 | 8 | | | | | 3706 |
| HPV18 | E2 | KAIELQMAL | 75 | 9 | | | | | 3707 |
| HPV18 | E2 | KLCSGNTT | 280 | 8 | | | | | 3708 |
| HPV18 | E2 | KLCSGNTTPI | 280 | 10 | | | | | 3709 |
| HPV18 | E2 | KLCSGNTTPII | 280 | 11 | | | | | 3710 |
| HPV18 | E2 | KQHCGPVNPL | 257 | 10 | | | | | 3711 |
| HPV18 | E2 | KQHCGPVNPLL | 257 | 11 | | | | | 3712 |
| HPV18 | E2 | KTATCVSHRGL | 152 | 11 | | | | | 3713 |
| HPV18 | E2 | KTEDWTLQDT | 92 | 10 | | | | | 3714 |
| HPV33 | E2 | KTGILTVT | 329 | 8 | | | | | 3715 |
| HPV18 | E2 | KTYGQTSA | 238 | 8 | | | | | 3716 |
| HPV18 | E2 | KTYGQTSAA | 238 | 9 | | | | | 3717 |
| HPV18 | E2 | KTYGQTSAAT | 238 | 10 | | | | | 3718 |
| HPV18 | E2 | LAEKQHCGPV | 254 | 10 | | | | | 3719 |
| HPV18 | E2 | LAQSRYKT | 86 | 8 | | | | | 3720 |
| HPV18 | E2 | LIRWENAI | 39 | 8 | | | | | 3721 |
| HPV18 | E2 | LIRWENAIFFA | 39 | 11 | | | | | 3722 |
| HPV18 | E2 | LLGAATPT | 266 | 8 | | | | | 3723 |
| HPV18 | E2 | LQDTCEEL | 98 | 8 | | | | | 3724 |
| HPV18 | E2 | LQDTCEELWNT | 98 | 11 | | | | | 3725 |
| HPV18 | E2 | LQGLAQSRYKT | 83 | 11 | | | | | 3726 |
| HPV18 | E2 | LQHTPSPYSST | 221 | 11 | | | | | 3727 |
| HPV18 | E2 | LQMALQGL | 79 | 8 | | | | | 3728 |
| HPV18 | E2 | LQMALQGLA | 79 | 9 | | | | | 3729 |
| HFV33 | E2 | LTVTYHSET | 333 | 9 | | | | | 3730 |
| HPV18 | E2 | LVKQLQHT | 217 | 8 | | | | | 3731 |
| HPV18 | E2 | MQTPKETL | 1 | 8 | | | | | 3732 |
| HPV18 | E2 | MTDAGTWDKT | 144 | 10 | | | | | 3733 |
| HPV18 | E2 | MTDAGTWDKTA | 144 | 11 | | | | | 3734 |
| HPV18 | E2 | MTYVAWDSV | 133 | 9 | | | | | 3735 |
| HPV18 | E2 | NISKSKAHKA | 67 | 10 | | | | | 3736 |
| HPV18 | E2 | NISKSKAHKAI | 67 | 11 | | | | | 3737 |
| HPV18 | E2 | NTTPIIHL | 285 | 8 | | | | | 3738 |
| HPV18 | E2 | NTVAIPDSV | 348 | 9 | | | | | 3739 |
| HPV18 | E2 | NTVAIPDSVQI | 348 | 11 | | | | | 3740 |
| HPV18 | E2 | NVIDCNDSM | 196 | 9 | | | | | 3741 |
| HPV18 | E2 | PAYNISKSKA | 64 | 10 | | | | | 3742 |
| HPV18 | E2 | PLLGAATPT | 265 | 9 | | | | | 3743 |
| HPV18 | E2 | PTGNNKRRKL | 272 | 10 | | | | | 3744 |
| HPV18 | E2 | PTHCFKKGGQT | 110 | 11 | | | | | 3745 |
| HPV18 | E2 | PVNPLLGA | 262 | 8 | | | | | 3746 |
| HPV18 | E2 | PVNPLLGAA | 262 | 9 | | | | | 3747 |
| HPV18 | E2 | PVNPLLGAAT | 262 | 10 | | | | | 3748 |
| HPV18 | E2 | QILVGYMT | 357 | 8 | | | | | 3749 |
| HPV18 | E2 | QILVGYMTM | 357 | 9 | | | | | 3750 |
| HPV18 | E2 | QIQYWQLI | 33 | 8 | | | | | 3751 |
| HPV18 | E2 | QLIRWENA | 38 | 8 | | | | | 3752 |
| HPV18 | E2 | QLIRWENAI | 38 | 9 | | | | | 3753 |
| HPV18 | E2 | QLVKQLQHT | 216 | 9 | | | | | 3754 |
| HPV18 | E2 | QMALQGLA | 80 | 8 | | | | | 3755 |
| HPV18 | E2 | QTLNHQVV | 56 | 8 | | | | | 3756 |
| HPV18 | E2 | QTLNHQVVPA | 56 | 10 | | | | | 3757 |
| HPV18 | E2 | QTPKETLSERL | 2 | 11 | | | | | 3758 |
| HPV18 | E2 | QVVPAYNI | 61 | 8 | | | | | 3759 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E2 | RLSCVQDKI | 11 | 9 | | | | | 3760 |
| HPV18 | E2 | RLSCVQDKII | 11 | 10 | | | | | 3761 |
| HPV18 | E2 | RTKFLNTV | 343 | 8 | | | | | 3762 |
| HPV18 | E2 | RTKFLNTVA | 343 | 9 | | | | | 3763 |
| HPV18 | E2 | RTKFLNTVAI | 343 | 10 | | | | | 3764 |
| HPV18 | E2 | SAATRPGHCGL | 244 | 11 | | | | | 3765 |
| HPV18 | E2 | SATQLVKQL | 213 | 9 | | | | | 3766 |
| HPV18 | E2 | SLKCLRYRL | 298 | 9 | | | | | 3767 |
| HPV18 | E2 | SMCSTSDDT | 203 | 9 | | | | | 3768 |
| HPV18 | E2 | SMCSTSDDTV | 203 | 10 | | | | | 3769 |
| HPV18 | E2 | SQIQYWQL | 32 | 8 | | | | | 3770 |
| HPV18 | E2 | SQIQYWQLI | 32 | 9 | | | | | 3771 |
| HPV18 | E2 | STSDDTVSA | 206 | 9 | | | | | 3772 |
| HPV18 | E2 | STSDDTVSAT | 206 | 10 | | | | | 3773 |
| HPV18 | E2 | STVSVGTA | 230 | 8 | | | | | 3774 |
| HPV18 | E2 | STVSVGTAKT | 230 | 10 | | | | | 3775 |
| HPV18 | E2 | STWHWTGA | 318 | 8 | | | | | 3776 |
| HPV18 | E2 | SVGTAKTYGQT | 233 | 11 | | | | | 3777 |
| HPV18 | E2 | SVQILVGYM | 355 | 9 | | | | | 3778 |
| HPV18 | E2 | SVQILVGYMT | 355 | 10 | | | | | 3779 |
| HPV18 | E2 | SVQILVGYMTM | 355 | 11 | | | | | 3780 |
| HPV18 | E2 | SVYYMTDA | 140 | 8 | | | | | 3781 |
| HPV18 | E2 | SVYYMTDAGT | 140 | 10 | | | | | 3782 |
| HPV18 | E2 | TAKTYGQT | 236 | 8 | | | | | 3783 |
| HPV18 | E2 | TAKTYGQTSA | 236 | 10 | | | | | 3784 |
| HPV18 | E2 | TAKTYGQTSAA | 236 | 11 | | | | | 3785 |
| HPV18 | E2 | TATCVSHRGL | 153 | 10 | | | | | 3786 |
| HPV18 | E2 | TLNHQVVPA | 57 | 9 | | | | | 3787 |
| HPV18 | E2 | TLQDTCEEL | 97 | 9 | | | | | 3788 |
| HPV18 | E2 | TLSERLSCV | 7 | 9 | | | | | 3789 |
| HPV18 | E2 | TQLVKQLQHT | 215 | 10 | | | | | 3790 |
| HPV18 | E2 | TQRTKFLNT | 341 | 9 | | | | | 3791 |
| HPV18 | E2 | TQRTKFLNTV | 341 | 10 | | | | | 3792 |
| HPV18 | E2 | TQRTKFLNTVA | 341 | 11 | | | | | 3793 |
| HPV18 | E2 | TVAIPDSV | 349 | 8 | | | | | 3794 |
| HPV18 | E2 | TVAIPDSVQI | 349 | 10 | | | | | 3795 |
| HPV18 | E2 | TVAIPDSVQIL | 349 | 11 | | | | | 3796 |
| HPV18 | E2 | TVSATQLV | 211 | 8 | | | | | 3797 |
| HPV18 | E2 | TVSATQLVKQL | 211 | 11 | | | | | 3798 |
| HPV18 | E2 | TVSVGTAKT | 231 | 9 | | | | | 3799 |
| HPV18 | E2 | TVTYHSET | 334 | 8 | | | | | 3800 |
| HPV18 | E2 | TVTYHSETQRT | 334 | 11 | | | | | 3801 |
| HPV18 | E2 | VAIPDSVQI | 350 | 9 | | | | | 3802 |
| HPV18 | E2 | VAIPDSVQIL | 350 | 10 | | | | | 3803 |
| HPV18 | E2 | VAIPDSVQILV | 350 | 11 | | | | | 3804 |
| HPV18 | E2 | VAWDSVYYM | 136 | 9 | | | | | 3805 |
| HPV18 | E2 | VAWDSVYYMT | 136 | 10 | | | | | 3806 |
| HPV18 | E2 | VIDCNDSM | 197 | 8 | | | | | 3807 |
| HPV18 | E2 | VIDCNDSMCST | 197 | 11 | | | | | 3808 |
| HPV18 | E2 | VQILVGYM | 356 | 8 | | | | | 3809 |
| HPV18 | E2 | VQILVGYMT | 356 | 9 | | | | | 3810 |
| HPV18 | E2 | VQILVGYMTM | 356 | 10 | | | | | 3811 |
| HPV18 | E2 | VTYHSETQRT | 335 | 10 | | | | | 3812 |
| HPV18 | E2 | WQLIRWENA | 37 | 9 | | | | | 3813 |
| HPV18 | E2 | WQLIRWENAI | 37 | 10 | | | | | 3814 |
| HPV18 | E2 | WTGAGNEKT | 322 | 9 | | | | | 3815 |
| HPV18 | E2 | WTGAGNEKTGI | 322 | 11 | | | | | 3816 |
| HPV18 | E2 | WTLQDTCEEL | 96 | 10 | | | | | 3817 |
| HPV18 | E2 | YMTDAGTWDKT | 143 | 11 | | | | | 3818 |
| HPV18 | E2 | YVAWDSVYYM | 135 | 10 | | | | | 3819 |
| HPV18 | E2 | YVAWDSVYYMT | 135 | 11 | | | | | 3820 |
| HPV18 | E2 | YVKEGYNT | 164 | 8 | | | | | 3821 |
| HPV18 | E2 | YVKEGYNTFYI | 164 | 11 | | | | | 3822 |
| HPV18 | E5 | ATAFTVYV | 47 | 8 | | | | | 3823 |
| HPV18 | E5 | CAYAWVLV | 29 | 8 | | | | | 3824 |
| HPV18 | E5 | CAYAWVLVFV | 29 | 10 | | | | | 3825 |
| HPV18 | E5 | CMCAYAWV | 27 | 8 | | | | | 3826 |
| HPV18 | E5 | CMCAYAWVL | 27 | 9 | | | | | 3827 |
| HPV18 | E5 | CMCAYAWVLV | 27 | 10 | | | | | 3828 |
| HPV18 | E5 | CMYVCCHV | 13 | 8 | | | | | 3829 |
| HPV18 | E5 | CMYVCCHVPL | 13 | 10 | | | | | 3830 |
| HPV18 | E5 | CMYVCCHVPLL | 13 | 11 | | | | | 3831 |
| HPV18 | E5 | CVCMYVCCHV | 11 | 10 | | | | | 3832 |
| HPV18 | E5 | FLFCFCVCM | 6 | 9 | | | | | 3833 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E5 | FLFCFCVCMYV | 6 | 11 | | | | | 3834 |
| HPV18 | E5 | FLLPMLLL | 57 | 8 | | | | | 3835 |
| HPV18 | E5 | FLLPMLLLHI | 57 | 10 | | | | | 3836 |
| HPV18 | E5 | FTVYVFCFL | 50 | 9 | | | | | 3837 |
| HPV18 | E5 | FTVYVFCFLL | 50 | 10 | | | | | 3838 |
| HPV18 | E5 | FVYIVVIT | 37 | 8 | | | | | 3839 |
| HPV18 | E5 | FVYIVVITSPA | 37 | 11 | | | | | 3840 |
| HPV18 | E5 | HIHAILSL | 65 | 8 | | | | | 3841 |
| HPV18 | E5 | HVPLLPSV | 19 | 8 | | | | | 3842 |
| HPV18 | E5 | HVPLLPSVCM | 19 | 10 | | | | | 3843 |
| HPV18 | E5 | ITSPATAFT | 43 | 9 | | | | | 3844 |
| HPV18 | E5 | ITSPATAFTV | 43 | 10 | | | | | 3845 |
| HPV18 | E5 | IVVITSPA | 40 | 8 | | | | | 3846 |
| HPV18 | E5 | IVVITSPAT | 40 | 9 | | | | | 3847 |
| HPV18 | E5 | IVVITSPATA | 40 | 10 | | | | | 3848 |
| HPV18 | E5 | LIFLFCFCV | 4 | 9 | | | | | 3849 |
| HPV18 | E5 | LIFLFCFCVCM | 4 | 11 | | | | | 3850 |
| HPV18 | E5 | LLHIHAIL | 63 | 8 | | | | | 3851 |
| HPV18 | E5 | LLHIHAILSL | 63 | 10 | | | | | 3852 |
| HPV18 | E5 | LLLHIHAI | 62 | 8 | | | | | 3853 |
| HPV18 | E5 | LLLHIHAIL | 62 | 9 | | | | | 3854 |
| HPV18 | E5 | LLLHIHAILSL | 62 | 11 | | | | | 3855 |
| HPV18 | E5 | LLPMLLLHI | 58 | 9 | | | | | 3856 |
| HPV18 | E5 | LLPMLLLHIHA | 58 | 11 | | | | | 3857 |
| HPV18 | E5 | LLPSVCMCA | 22 | 9 | | | | | 3858 |
| HPV18 | E5 | LLPSVCMCAYA | 22 | 11 | | | | | 3859 |
| HPV18 | E5 | LVFVYIVV | 35 | 8 | | | | | 3860 |
| HPV18 | E5 | LVFVYIVVI | 35 | 9 | | | | | 3861 |
| HPV18 | E5 | LVFVYIVVIT | 35 | 10 | | | | | 3862 |
| HPV18 | E5 | MLLLHIHA | 61 | 8 | | | | | 3863 |
| HPV18 | E5 | MLLLHIHAI | 61 | 9 | | | | | 3864 |
| HPV18 | E5 | MLLLHIHAIL | 61 | 10 | | | | | 3865 |
| HPV18 | E5 | PATAFTVYV | 46 | 9 | | | | | 3866 |
| HPV18 | E5 | PLLPSVCM | 21 | 8 | | | | | 3867 |
| HPV18 | E5 | PLLPSVCMCA | 21 | 10 | | | | | 3868 |
| HPV18 | E5 | PMLLLHIHA | 60 | 9 | | | | | 3869 |
| HPV18 | E5 | PMLLLHIHAI | 60 | 10 | | | | | 3870 |
| HPV18 | E5 | PMLLLHIHAIL | 60 | 11 | | | | | 3871 |
| HPV18 | E5 | SLIFLFCFCV | 3 | 10 | | | | | 3872 |
| HPV18 | E5 | SVCMCAYA | 25 | 8 | | | | | 3873 |
| HPV18 | E5 | SVCMCAYAWV | 25 | 10 | | | | | 3874 |
| HPV18 | E5 | SVCMCAYAWVL | 25 | 11 | | | | | 3875 |
| HPV18 | E5 | TAFTVYVFCFL | 48 | 11 | | | | | 3876 |
| HPV18 | E5 | TVYVFCFL | 51 | 8 | | | | | 3877 |
| HPV18 | E5 | TVYVFCFLL | 51 | 9 | | | | | 3878 |
| HPV18 | E5 | TVYVFCFLLPM | 51 | 11 | | | | | 3879 |
| HPV18 | E5 | VITSPATA | 42 | 8 | | | | | 3880 |
| HPV18 | E5 | VITSPATAFT | 42 | 10 | | | | | 3881 |
| HPV18 | E5 | VITSPATAFTV | 42 | 11 | | | | | 3882 |
| HPV18 | E5 | VLVFVYIV | 34 | 8 | | | | | 3883 |
| HPV18 | E5 | VLVFVYIVV | 34 | 9 | | | | | 3884 |
| HPV18 | E5 | VLVFVYIVVI | 34 | 10 | | | | | 3885 |
| HPV18 | E5 | VLVFVYIVVIT | 34 | 11 | | | | | 3886 |
| HPV18 | E5 | VVITSPAT | 41 | 8 | | | | | 3887 |
| HPV18 | E5 | VVITSPATA | 41 | 9 | | | | | 3888 |
| HPV18 | E5 | VVITSPATAFT | 41 | 11 | | | | | 3889 |
| HPV18 | E5 | WVLVFVYI | 33 | 8 | | | | | 3890 |
| HPV18 | E5 | WVLVFVYIV | 33 | 9 | | | | | 3891 |
| HPV18 | E5 | WVLVFVYIVV | 33 | 10 | | | | | 3892 |
| HPV18 | E5 | WVLVFVYIVVI | 33 | 11 | | | | | 3893 |
| HPV18 | E5 | YAWVLVFV | 31 | 8 | | | | | 3894 |
| HPV18 | E5 | YAWVLVFVYI | 31 | 10 | | | | | 3895 |
| HPV18 | E5 | YAWVLVFVYIV | 31 | 11 | | | | | 3896 |
| HPV18 | E5 | YIVVITSPA | 39 | 9 | | | | | 3897 |
| HPV18 | E5 | YIVVITSPAT | 39 | 10 | | | | | 3898 |
| HPV18 | E5 | YIVVITSPATA | 39 | 11 | | | | | 3899 |
| HPV18 | E5 | YVCCHVPL | 15 | 8 | | | | | 3900 |
| HPV18 | E5 | YVCCHVPLL | 15 | 9 | | | | | 3901 |
| HPV18 | E5 | YVFCFLLPM | 53 | 9 | | | | | 3902 |
| HPV18 | E5 | YVFCFLLPML | 53 | 10 | | | | | 3903 |
| HPV18 | E5 | YVFCFLLPMLL | 53 | 11 | | | | | 3904 |
| HPV18 | E6 | CIDFYSRI | 68 | 8 | 0.0001 | | | | 3905 |
| HPV18 | E6 | CIDFYSRIREL | 68 | 11 | | | | | 3906 |
| HPV18 | E6 | CLRCQKPL | 105 | 8 | 0.0001 | | | | 3907 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E6 | CLRCQKPLNPA | 105 | 11 | | | | | 3908 |
| HPV18 | E6 | CQKPLNPA | 108 | 8 | | | | | 3909 |
| HPV18 | E6 | CQKPLNPAEKL | 108 | 11 | | | | | 3910 |
| HPV18 | E6 | CTELNTSL | 18 | 8 | | | | | 3911 |
| HPV18 | E6 | CTELNTSLQDI | 18 | 11 | | | | | 3912 |
| HPV18 | E6 | CVYCKTVL | 32 | 8 | 0.0002 | | | | 3913 |
| HPV18 | E6 | CVYCKTVLEL | 32 | 10 | 0.0001 | | | | 3914 |
| HPV18 | E6 | CVYCKTVLELT | 32 | 11 | | | | | 3915 |
| HPV18 | E6 | DIEITCVYCKT | 27 | 11 | | | | | 3916 |
| HPV18 | E6 | DLCTELNT | 16 | 8 | | | | | 3917 |
| HPV18 | E6 | DLCTELNTSL | 16 | 10 | 0.0001 | | | | 3918 |
| HPV18 | E6 | DLFVVYRDSI | 51 | 10 | 0.0001 | | | | 3919 |
| HPV18 | E6 | DTLEKLTNT | 88 | 9 | 0.0001 | | | | 3920 |
| HPV18 | E6 | DTLEKLTNTGL | 88 | 11 | | | | | 3921 |
| HPV18 | E6 | EITCVYCKT | 29 | 9 | 0.0001 | | | | 3922 |
| HPV18 | E6 | EITCVYCKTV | 29 | 10 | 0.0002 | | | | 3923 |
| HPV18 | E6 | EITCVYCKTVL | 29 | 11 | | | | | 3924 |
| HPV18 | E6 | ELNTSLQDI | 20 | 9 | 0.0001 | | | | 3925 |
| HPV18 | E6 | ELNTSLQDIEI | 20 | 11 | | | | | 3926 |
| HPV18 | E6 | ELRHYSDSV | 77 | 9 | 0.0003 | | | | 3927 |
| HPV18 | E6 | ELTEVFEFA | 40 | 9 | 0.0012 | | | | 3928 |
| HPV18 | E6 | EVFEFAFKDL | 43 | 10 | 0.0009 | | | | 3929 |
| HPV18 | E6 | FAFKDLFV | 47 | 8 | | | | | 3930 |
| HPV18 | E6 | FAFKDLFVV | 47 | 9 | 0.085 | | | | 3931 |
| HPV18 | E6 | FVVYRDSI | 53 | 8 | | | | | 3932 |
| HPV18 | E6 | FVVYRDSIPHA | 53 | 11 | | | | | 3933 |
| HPV18 | E6 | GLYNLLIRCL | 97 | 10 | 0.0036 | | | | 3934 |
| HPV18 | E6 | GQCHSCCNRA | 136 | 10 | | | | | 3935 |
| HPV18 | E6 | HAACHKCI | 62 | 8 | | | | | 3936 |
| HPV18 | E6 | HLNEKRRFHNI | 120 | 11 | | | | | 3937 |
| HPV18 | E6 | ITCVYCKT | 30 | 8 | | | | | 3938 |
| HPV18 | E6 | ITCVYCKTV | 30 | 9 | | | | | 3939 |
| HPV18 | E6 | ITCVYCKTVL | 30 | 10 | | | | | 3940 |
| HPV18 | E6 | KLPDLCTEL | 13 | 9 | 0.0035 | | | | 3941 |
| HPV18 | E6 | KLPDLCTELNT | 13 | 11 | | | | | 3942 |
| HPV18 | E6 | KLTNTGLYNL | 92 | 10 | 0.0048 | | | | 3943 |
| HPV18 | E6 | KLTNTGLYNLL | 92 | 11 | 0.0043 | | | | 3944 |
| HPV18 | E6 | KTVLELTEV | 36 | 9 | | | | | 3945 |
| HPV18 | E6 | LIRCLRCQKPL | 102 | 11 | | | | | 3946 |
| HPV18 | E6 | LQDIEITCV | 25 | 9 | | | | | 3947 |
| HPV18 | E6 | LQRRRETQV | 150 | 9 | | | | | 3948 |
| HPV18 | E6 | LTEVFEFA | 41 | 8 | | | | | 3949 |
| HPV18 | E6 | LTNTGLYNL | 93 | 9 | | | | | 3950 |
| HPV18 | E6 | LTNTGLYNLL | 93 | 10 | | | | | 3951 |
| HPV18 | E6 | LTNTGLYNLLI | 93 | 11 | | | | | 3952 |
| HPV18 | E6 | MARFEDPT | 1 | 8 | | | | | 3953 |
| HPV18 | E6 | NTGLYNLL | 95 | 8 | | | | | 3954 |
| HPV18 | E6 | NTGLYNLLI | 95 | 9 | | | | | 3955 |
| HPV18 | E6 | NTSLQDIEI | 22 | 9 | | | | | 3956 |
| HPV18 | E6 | NTSLQDIEIT | 22 | 10 | 0.0001 | | | | 3957 |
| HPV18 | E6 | PAEKLRHL | 114 | 8 | | | | | 3958 |
| HPV18 | E6 | PLNPAEKL | 111 | 8 | 0.0001 | | | | 3959 |
| HPV18 | E6 | PLNPAEKLRHL | 111 | 11 | 0.0001 | | | | 3960 |
| HPV18 | E6 | PTRRPYKL | 7 | 8 | | | | | 3961 |
| HPV18 | E6 | PTRRPYKLPDL | 7 | 11 | | | | | 3962 |
| HPV18 | E6 | RLQRRRET | 149 | 8 | | | | | 3963 |
| HPV18 | E6 | RLQRRRETQV | 149 | 10 | 0.0001 | | | | 3964 |
| HPV18 | E6 | RQERLQRRRET | 146 | 11 | | | | | 3965 |
| HPV18 | E6 | SIPHAACHKCI | 59 | 11 | | | | | 3966 |
| HPV18 | E6 | SLQDIEIT | 24 | 8 | | | | | 3967 |
| HPV18 | E6 | SLQDIEITCV | 24 | 10 | 0.025 | | | | 3968 |
| HPV18 | E6 | SVYGDTLEKL | 84 | 10 | 0.0028 | | | | 3969 |
| HPV18 | E6 | SVYGDTLEKLT | 84 | 11 | | | | | 3970 |
| HPV18 | E6 | TLEKLTNT | 89 | 8 | | | | | 3971 |
| HPV18 | E6 | TLEKLTNTGL | 89 | 10 | 0.0004 | | | | 3972 |
| HPV18 | E6 | TVLELTEV | 37 | 8 | 0.001 | | | | 3973 |
| HPV18 | E6 | VLELTEVFEFA | 38 | 11 | | | | | 3974 |
| HPV18 | E6 | VVYRDSIPHA | 54 | 10 | 0.0003 | | | | 3975 |
| HPV18 | E6 | VVYRDSIPHAA | 54 | 11 | | | | | 3976 |
| HPV18 | E7 | ATLQDIVL | 6 | 8 | | | | | 3977 |
| HPV18 | E7 | ATLQDIVLHL | 6 | 10 | | | | | 3978 |
| HPV18 | E7 | CMCCKCEA | 63 | 8 | 0.0005 | | | | 3979 |
| HPV18 | E7 | CMCCKCEARI | 63 | 10 | 0.002 | | | | 3980 |
| HPV18 | E7 | DLLCHEQL | 24 | 8 | 0.0001 | | | | 3981 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | E7 | DLRAFQQL | 82 | 8 | 0.0001 | | | | 3982 |
| HPV18 | E7 | DLRAFQQLFL | 82 | 10 | 0.001 | | | | 3983 |
| HPV18 | E7 | EARIKLVV | 69 | 8 | | | | | 3984 |
| HPV18 | E7 | EIDGVNHQHL | 40 | 10 | 0.0001 | | | | 3985 |
| HPV18 | E7 | FLNTLSFV | 90 | 8 | 0.0079 | | | | 3986 |
| HPV18 | E7 | FQQLFLNT | 86 | 8 | | | | | 3987 |
| HPV18 | E7 | FQQLFLNTL | 86 | 9 | | | | | 3988 |
| HPV18 | E7 | GVNHQHLPA | 43 | 9 | 0.0001 | | | | 3989 |
| HPV18 | E7 | HLEPQNEI | 14 | 8 | 0.0001 | | | | 3990 |
| HPV18 | E7 | HLEPQNEIPV | 14 | 10 | 0.0001 | | | | 3991 |
| HPV18 | E7 | HQHLPARRA | 46 | 9 | | | | | 3992 |
| HPV18 | E7 | IVLHLEPONEI | 11 | 11 | | | | | 3993 |
| HPV18 | E7 | KATLQDIV | 5 | 8 | | | | | 3994 |
| HPV18 | E7 | KATLQDIVL | 5 | 9 | | | | | 3995 |
| HPV18 | E7 | KATLQDIVLHL | 5 | 11 | | | | | 3996 |
| HPV18 | E7 | KLVVESSA | 73 | 8 | 0.0001 | | | | 3997 |
| HPV18 | E7 | KLVVESSADDL | 73 | 11 | 0.0001 | | | | 3998 |
| HPV18 | E7 | LQDIVLHL | 8 | 8 | | | | | 3999 |
| HPV18 | E7 | LVVESSADDL | 74 | 10 | 0.0001 | | | | 4000 |
| HPV18 | E7 | MLCMCCKCEA | 61 | 10 | 0.0016 | | | | 4001 |
| HPV18 | E7 | NTLSFVCPWCA | 92 | 11 | | | | | 4002 |
| HPV18 | E7 | PARRAEPQRHT | 50 | 11 | | | | | 4003 |
| HPV18 | E7 | PQNEIPVDL | 17 | 9 | | | | | 4004 |
| HPV18 | E7 | PQNEIPVDLL | 17 | 10 | | | | | 4005 |
| HPV18 | E7 | PQRHTMLCM | 56 | 9 | | | | | 4006 |
| HPV18 | E7 | PVDLLCHEQL | 22 | 10 | 0.0001 | | | | 4007 |
| HPV18 | E7 | QLFNTLSFV | 88 | 10 | 0.11 | | | | 4008 |
| HPV18 | E7 | QQLFLNTL | 87 | 8 | | | | | 4009 |
| HPV18 | E7 | QQLFLNTLSFV | 87 | 11 | | | | | 4010 |
| HPV18 | E7 | RAEPQRHT | 53 | 8 | | | | | 4011 |
| HPV18 | E7 | RAEPQRHTM | 53 | 9 | | | | | 4012 |
| HPV18 | E7 | RAEPQRHTML | 53 | 10 | | | | | 4013 |
| HPV18 | E7 | RAFQQLFL | 84 | 8 | | | | | 4014 |
| HPV18 | E7 | RAFQQLFLNT | 84 | 10 | 0.0003 | | | | 4015 |
| HPV18 | E7 | RAFQQLFLNTL | 84 | 11 | | | | | 4016 |
| HPV18 | E7 | RIKLVVESSA | 71 | 10 | | | | | 4017 |
| HPV18 | E7 | SADDLRAFQQL | 79 | 11 | | | | | 4018 |
| HPV18 | E7 | TLQDIVLHL | 7 | 9 | 3 | | | | 4019 |
| HPV18 | E7 | TLSFVCPWCA | 93 | 10 | 0.0027 | | | | 4020 |
| HPV18 | E7 | TMLCMCCKCEA | 60 | 11 | | | | | 4021 |
| HPV18 | E7 | VLHLEPQNEI | 12 | 10 | 0.0001 | | | | 4022 |
| HPV18 | E7 | VVESSADDL | 75 | 9 | 0.0003 | | | | 4023 |
| HPV18 | E7 | VVESSADDLRA | 75 | 11 | | | | | 4024 |
| HPV18 | L1 | AATSNVSEDV | 195 | 10 | | | | | 4025 |
| HPV18 | L1 | AIGEHWAKGT | 225 | 10 | | | | | 4026 |
| HPV18 | L1 | AIGEHWAKGTA | 225 | 11 | | | | | 4027 |
| HPV18 | L1 | AITCQKDA | 487 | 8 | | | | | 4028 |
| HPV18 | L1 | AITCQKDAA | 487 | 9 | | | | | 4029 |
| HPV18 | L1 | AITCQKDAAPA | 487 | 11 | | | | | 4030 |
| HPV18 | L1 | ALWRPSDNT | 63 | 9 | | | | | 4031 |
| HPV18 | L1 | ALWRPSDNTV | 63 | 10 | | | | | 4032 |
| HPV18 | L1 | AMDFSTLQDT | 268 | 10 | | | | | 4033 |
| HPV18 | L1 | AQGHNNGV | 377 | 8 | | | | | 4034 |
| HPV18 | L1 | ATKFKQYSRHV | 419 | 11 | | | | | 4035 |
| HPV18 | L1 | ATSNVSEDV | 196 | 9 | | | | | 4036 |
| HPV18 | L1 | ATTSSKPA | 552 | 8 | | | | | 4037 |
| HPV18 | L1 | ATTSSKPAKRV | 552 | 11 | | | | | 4038 |
| HPV18 | L1 | CAPAIGEHWA | 222 | 10 | | | | | 4039 |
| HPV18 | L1 | CASTQSPV | 406 | 8 | | | | | 4040 |
| HPV18 | L1 | CILGCAPA | 218 | 8 | | | | | 4041 |
| HPV18 | L1 | CILGCAPAI | 218 | 9 | | | | | 4042 |
| HPV18 | L1 | CLRREQLFA | 310 | 9 | | | | | 4043 |
| HPV18 | L1 | CLYTRVLI | 2 | 8 | | | | | 4044 |
| HPV18 | L1 | CLYTRVLIL | 2 | 9 | | | | | 4045 |
| HPV18 | L1 | CQKDAAPA | 490 | 8 | | | | | 4046 |
| HPV18 | L1 | CQSICKYPDYL | 286 | 11 | | | | | 4047 |
| HPV18 | L1 | CTITLTADV | 441 | 9 | | | | | 4048 |
| HPV18 | L1 | CTITLTADVM | 441 | 10 | | | | | 4049 |
| HPV18 | L1 | CVYSPSPSGSI | 350 | 11 | | | | | 4050 |
| HPV18 | L1 | DLKEKFSL | 512 | 8 | | | | | 4051 |
| HPV18 | L1 | DLKEKFSLDL | 512 | 10 | | | | | 4052 |
| HPV18 | L1 | DLQFIFQL | 433 | 8 | | | | | 4053 |
| HPV18 | L1 | DLQFIFQLCT | 433 | 10 | | | | | 4054 |
| HPV18 | L1 | DLQFIFQLCTI | 433 | 11 | | | | | 4055 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | L1 | DMVDTGYGA | 260 | 9 | | | | | 4056 |
| HPV18 | L1 | DMVDTGYGAM | 260 | 10 | | | | | 4057 |
| HPV18 | L1 | DQYPLGRKFL | 522 | 10 | | | | | 4058 |
| HPV18 | L1 | DQYPLGRKFLV | 522 | 11 | | | | | 4059 |
| HPV18 | L1 | DTESSHAA | 189 | 8 | | | | | 4060 |
| HPV18 | L1 | DTESSHAAT | 189 | 9 | | | | | 4061 |
| HPV18 | L1 | DTGYGAMDFST | 263 | 11 | | | | | 4062 |
| HPV18 | L1 | DTKCEVPL | 276 | 8 | | | | | 4063 |
| HPV18 | L1 | DTKCEVPLDI | 276 | 10 | | | | | 4064 |
| HPV18 | L1 | DTSIYNPET | 148 | 9 | | | | | 4065 |
| HPV18 | L1 | DTTPSTNL | 396 | 8 | | | | | 4066 |
| HPV18 | L1 | DTTPSTNLT | 396 | 9 | | | | | 4067 |
| HPV18 | L1 | DTTPSTNLTI | 396 | 10 | | | | | 4068 |
| HPV18 | L1 | DTVPQSLYI | 330 | 9 | | | | | 4069 |
| HPV18 | L1 | DTYRFVQSV | 478 | 9 | | | | | 4070 |
| HPV18 | L1 | DTYRFVQSVA | 478 | 10 | | | | | 4071 |
| HPV18 | L1 | DTYRFVQSVAI | 478 | 11 | | | | | 4072 |
| HPV18 | L1 | DVMSYIHSM | 448 | 9 | | | | | 4073 |
| HPV18 | L1 | DVRDNVSV | 203 | 8 | | | | | 4074 |
| HPV18 | L1 | EIGRGQPL | 167 | 8 | | | | | 4075 |
| HPV18 | L1 | EIGRGQPLGV | 167 | 10 | | | | | 4076 |
| HPV18 | L1 | ETQRLVWA | 155 | 8 | | | | | 4077 |
| HPV18 | L1 | ETQRLVWACA | 155 | 10 | | | | | 4078 |
| HPV18 | L1 | EVPLDICQSI | 280 | 10 | | | | | 4079 |
| HPV18 | L1 | FARHFWNRA | 317 | 9 | | | | | 4080 |
| HPV18 | L1 | FARHFWNRAGT | 317 | 11 | | | | | 4081 |
| HPV18 | L1 | FIFQLCTI | 436 | 8 | | | | | 4082 |
| HPV18 | L1 | FIFQLCTIT | 436 | 9 | | | | | 4083 |
| HPV18 | L1 | FIFQLCTITL | 436 | 10 | | | | | 4084 |
| HPV18 | L1 | FIFQLCTITLT | 436 | 11 | | | | | 4085 |
| HPV18 | L1 | FLRNVNVFPI | 49 | 10 | | | | | 4086 |
| HPV18 | L1 | FQLCTITL | 438 | 8 | | | | | 4087 |
| HPV18 | L1 | FQLCTITLT | 438 | 9 | | | | | 4088 |
| HPV18 | L1 | FQLCTITLTA | 438 | 10 | | | | | 4089 |
| HPV18 | L1 | FVQSVAIT | 482 | 8 | | | | | 4090 |
| HPV18 | L1 | FVTVVDTT | 391 | 8 | | | | | 4091 |
| HPV18 | L1 | FVTVVDTTPST | 391 | 11 | | | | | 4092 |
| HPV18 | L1 | GAMDFSTL | 267 | 8 | | | | | 4093 |
| HPV18 | L1 | GAMDFSTLQDT | 267 | 11 | | | | | 4094 |
| HPV18 | L1 | GLRRKPTI | 535 | 8 | | | | | 4095 |
| HPV18 | L1 | GLSGHPFYNKL | 177 | 11 | | | | | 4096 |
| HPV18 | L1 | GMPASPGSCV | 342 | 10 | | | | | 4097 |
| HPV18 | L1 | GQPLGVGL | 171 | 8 | | | | | 4098 |
| HPV18 | L1 | GTACKSRPL | 233 | 9 | | | | | 4099 |
| HPV18 | L1 | GTMGDTVPQSL | 326 | 11 | | | | | 4100 |
| HPV18 | L1 | GVCWHNQL | 383 | 8 | | | | | 4101 |
| HPV18 | L1 | GVCWHNQLFV | 383 | 10 | | | | | 4102 |
| HPV18 | L1 | GVCWHNQLFVT | 383 | 11 | | | | | 4103 |
| HPV18 | L1 | GVEIGRGQPL | 165 | 10 | | | | | 4104 |
| HPV18 | L1 | GVPPPPTT | 467 | 8 | | | | | 4105 |
| HPV18 | L1 | GVPPPPTTSL | 467 | 10 | | | | | 4106 |
| HPV18 | L1 | GVPPPPTTSLV | 467 | 11 | | | | | 4107 |
| HPV18 | L1 | HAATSNVSEDV | 194 | 11 | | | | | 4108 |
| HPV18 | L1 | HAGSSRLL | 97 | 8 | | | | | 4109 |
| HPV18 | L1 | HAGSSRLLT | 97 | 9 | | | | | 4110 |
| HPV18 | L1 | HAGSSRLLTV | 97 | 10 | | | | | 4111 |
| HPV18 | L1 | HIIICGHYI | 38 | 9 | | | | | 4112 |
| HPV18 | L1 | HIIICGHYII | 38 | 10 | | | | | 4113 |
| HPV18 | L1 | HIIICGHYIIL | 38 | 11 | | | | | 4114 |
| HPV18 | L1 | HLLPLYGPL | 13 | 9 | | | | | 4115 |
| HPV18 | L1 | HVEEYDLQFI | 428 | 10 | | | | | 4116 |
| HPV18 | L1 | IICGHYII | 40 | 8 | | | | | 4117 |
| HPV18 | L1 | IICGHYIIL | 40 | 9 | | | | | 4118 |
| HPV18 | L1 | IICGHYIILFL | 40 | 11 | | | | | 4119 |
| HPV18 | L1 | IIICGHYI | 39 | 8 | | | | | 4120 |
| HPV18 | L1 | IIICGHYII | 39 | 9 | | | | | 4121 |
| HPV18 | L1 | IIICGHYIIL | 39 | 10 | | | | | 4122 |
| HPV18 | L1 | IILFLRNV | 46 | 8 | | | | | 4123 |
| HPV18 | L1 | IILFLRNVNV | 46 | 10 | | | | | 4124 |
| HPV18 | L1 | ILEDWNFGV | 460 | 9 | | | | | 4125 |
| HPV18 | L1 | ILFLRNVNV | 47 | 9 | | | | | 4126 |
| HPV18 | L1 | ILGCAPAI | 219 | 8 | | | | | 4127 |
| HPV18 | L1 | ILHYHLLPL | 9 | 9 | | | | | 4128 |
| HPV18 | L1 | ILVYMVHI | 32 | 8 | | | | | 4129 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | L1 | ILVYMVHII | 32 | 9 | | | | | 4130 |
| HPV18 | L1 | ILVYMVHIII | 32 | 10 | | | | | 4131 |
| HPV18 | L1 | ITCQKDAA | 488 | 8 | | | | | 4132 |
| HPV18 | L1 | ITCQKDAAPA | 488 | 10 | | | | | 4133 |
| HPV18 | L1 | ITLTADVM | 443 | 8 | | | | | 4134 |
| HPV18 | L1 | ITLTADVMSYI | 443 | 11 | | | | | 4135 |
| HPV18 | L1 | IVTSDSQL | 360 | 8 | | | | | 4136 |
| HPV18 | L1 | KAQGHNNGV | 376 | 9 | | | | | 4137 |
| HPV18 | L1 | KLDDTESSHA | 186 | 10 | | | | | 4138 |
| HPV18 | L1 | KLDDTESSHAA | 186 | 11 | | | | | 4139 |
| HPV18 | L1 | KLKFWNVDL | 505 | 9 | | | | | 4140 |
| HPV18 | L1 | KQDIPKVSA | 120 | 9 | | | | | 4141 |
| HPV18 | L1 | KQTQLCIL | 213 | 8 | | | | | 4142 |
| HPV18 | L1 | KQTQLCILGCA | 213 | 11 | | | | | 4143 |
| HPV18 | L1 | KVSAYQYRV | 125 | 9 | | | | | 4144 |
| HPV18 | L1 | LILHYHLL | 8 | 8 | | | | | 4145 |
| HPV18 | L1 | LILHYHLLPL | 8 | 10 | | | | | 4146 |
| HPV18 | L1 | LLPLYGPL | 14 | 8 | | | | | 4147 |
| HPV18 | L1 | LLTVGNPYFRV | 103 | 11 | | | | | 4148 |
| HPV18 | L1 | LQDTKCEV | 274 | 8 | | | | | 4149 |
| HPV18 | L1 | LQDTKCEVPL | 274 | 10 | | | | | 4150 |
| HPV18 | L1 | LQFIFQLCT | 434 | 9 | | | | | 4151 |
| HPV18 | L1 | LQFIFQLCTI | 434 | 10 | | | | | 4152 |
| HPV18 | L1 | LQFIFQLCTIT | 434 | 11 | | | | | 4153 |
| HPV18 | L1 | LTADVMSYI | 445 | 9 | | | | | 4154 |
| HPV18 | L1 | LTICASTQSPV | 403 | 11 | | | | | 4155 |
| HPV18 | L1 | LTVGNPYFRV | 104 | 10 | | | | | 4156 |
| HPV18 | L1 | LVDTYRFV | 476 | 8 | | | | | 4157 |
| HPV18 | L1 | LVDTYRFVQSV | 476 | 11 | | | | | 4158 |
| HPV18 | L1 | LVQAGLRRKPT | 531 | 11 | | | | | 4159 |
| HPV18 | L1 | LVWACAGV | 159 | 8 | | | | | 4160 |
| HPV18 | L1 | LVWACAGVEI | 159 | 10 | | | | | 4161 |
| HPV18 | L1 | LVYMVHII | 33 | 8 | | | | | 4162 |
| HPV18 | L1 | LVYMVHIII | 33 | 9 | | | | | 4163 |
| HPV18 | L1 | MALWRPSDNT | 62 | 10 | | | | | 4164 |
| HPV18 | L1 | MALWRPSDNTV | 62 | 11 | | | | | 4165 |
| HPV18 | L1 | MVDTGYGA | 261 | 8 | | | | | 4166 |
| HPV18 | L1 | MVDTGYGAM | 261 | 9 | | | | | 4167 |
| HPV18 | L1 | MVHIIICGHYI | 36 | 11 | | | | | 4168 |
| HPV18 | L1 | NLTICAST | 402 | 8 | | | | | 4169 |
| HPV18 | L1 | NQLFVTVV | 388 | 8 | | | | | 4170 |
| HPV18 | L1 | NQLFVTVVDT | 388 | 10 | | | | | 4171 |
| HPV18 | L1 | NQLFVTVVDTT | 388 | 11 | | | | | 4172 |
| HPV18 | L1 | NTDDYVTPT | 84 | 9 | | | | | 4173 |
| HPV18 | L1 | NTDDYVTPTSI | 84 | 11 | | | | | 4174 |
| HPV18 | L1 | NTVLEDGDM | 253 | 9 | | | | | 4175 |
| HPV18 | L1 | NTVLEDGDMV | 253 | 10 | | | | | 4176 |
| HPV18 | L1 | NTVYLPPPSV | 70 | 10 | | | | | 4177 |
| HPV18 | L1 | NTVYLPPPSVA | 70 | 11 | | | | | 4178 |
| HPV18 | L1 | NVDLKEKFSL | 510 | 10 | | | | | 4179 |
| HPV18 | L1 | NVFPIFLQM | 54 | 9 | | | | | 4180 |
| HPV18 | L1 | NVFPIFLQMA | 54 | 10 | | | | | 4181 |
| HPV18 | L1 | NVFPIFLQMAL | 54 | 11 | | | | | 4182 |
| HPV18 | L1 | NVNVFPIFL | 52 | 9 | | | | | 4183 |
| HPV18 | L1 | NVNVFPIFLQM | 52 | 11 | | | | | 4184 |
| HPV18 | L1 | NVSEDVRDNV | 199 | 10 | | | | | 4185 |
| HPV18 | L1 | NVSVDYKQT | 207 | 9 | | | | | 4186 |
| HPV18 | L1 | NVSVDYKQTQL | 207 | 11 | | | | | 4187 |
| HPV18 | L1 | PAENKDPYDKL | 496 | 11 | | | | | 4188 |
| HPV18 | L1 | PAGGGNKQDI | 114 | 10 | | | | | 4189 |
| HPV18 | L1 | PAIGEHWA | 224 | 8 | | | | | 4190 |
| HPV18 | L1 | PAIGEHWAKGT | 224 | 11 | | | | | 4191 |
| HPV18 | L1 | PAKRVRVRA | 558 | 9 | | | | | 4192 |
| HPV18 | L1 | PASPGSCV | 344 | 8 | | | | | 4193 |
| HPV18 | L1 | PIFLQMAL | 57 | 8 | | | | | 4194 |
| HPV18 | L1 | PLDICQSI | 282 | 8 | | | | | 4195 |
| HPV18 | L1 | PLELKNTV | 248 | 8 | | | | | 4196 |
| HPV18 | L1 | PLELKNTVL | 248 | 9 | | | | | 4197 |
| HPV18 | L1 | PLGRKFLV | 525 | 8 | | | | | 4198 |
| HPV18 | L1 | PLGRKFLVQA | 525 | 10 | | | | | 4199 |
| HPV18 | L1 | PLHSILVYM | 28 | 9 | | | | | 4200 |
| HPV18 | L1 | PLHSILVYMV | 28 | 10 | | | | | 4201 |
| HPV18 | L1 | PLPLHSIL | 26 | 8 | | | | | 4202 |
| HPV18 | L1 | PLPLHSILV | 26 | 9 | | | | | 4203 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | L1 | PLPLHSILVYM | 26 | 11 | | | | | 4204 |
| HPV18 | L1 | PLSQGDCPPL | 240 | 10 | | | | | 4205 |
| HPV18 | L1 | PLYHPRPL | 20 | 8 | | | | | 4206 |
| HPV18 | L1 | PLYHPRPLPL | 20 | 10 | | | | | 4207 |
| HPV18 | L1 | PQSLYIKGT | 333 | 9 | | | | | 4208 |
| HPV18 | L1 | PQSLYIKGTGM | 333 | 11 | | | | | 4209 |
| HPV18 | L1 | PTIGPRKRSA | 540 | 10 | | | | | 4210 |
| HPV18 | L1 | PTSIFYHA | 91 | 8 | | | | | 4211 |
| HPV18 | L1 | PTTSLVDT | 472 | 8 | | | | | 4212 |
| HPV18 | L1 | PVPGQYDA | 412 | 8 | | | | | 4213 |
| HPV18 | L1 | PVPGQYDAT | 412 | 9 | | | | | 4214 |
| HPV18 | L1 | QAGLRRKPT | 533 | 9 | | | | | 4215 |
| HPV18 | L1 | QAGLRRKPTI | 533 | 10 | | | | | 4216 |
| HPV18 | L1 | QLCILGCA | 216 | 8 | | | | | 4217 |
| HPV18 | L1 | QLCILGCAPA | 216 | 10 | | | | | 4218 |
| HPV18 | L1 | QLCILGCAPAI | 216 | 11 | | | | | 4219 |
| HPV18 | L1 | QLCTITLT | 439 | 8 | | | | | 4220 |
| HPV18 | L1 | QLCTITLTA | 439 | 9 | | | | | 4221 |
| HPV18 | L1 | QLCTITLTADV | 439 | 11 | | | | | 4222 |
| HPV18 | L1 | QLFARHFWNRA | 315 | 11 | | | | | 4223 |
| HPV18 | L1 | QLFNKPYWL | 366 | 9 | | | | | 4224 |
| HPV18 | L1 | QLFVTVVDT | 389 | 9 | | | | | 4225 |
| HPV18 | L1 | QLFVTVVDTT | 389 | 10 | | | | | 4226 |
| HPV18 | L1 | QLPDPNKFGL | 137 | 10 | | | | | 4227 |
| HPV18 | L1 | QMALWRPSDNT | 61 | 11 | | | | | 4228 |
| HPV18 | L1 | QMSADPYGDSM | 297 | 11 | | | | | 4229 |
| HPV18 | L1 | QTQLCILGCA | 214 | 10 | | | | | 4230 |
| HPV18 | L1 | RAGTMGDT | 324 | 8 | | | | | 4231 |
| HPV18 | L1 | RAGTMGDTV | 324 | 9 | | | | | 4232 |
| HPV18 | L1 | RLVWACAGV | 158 | 9 | | | | | 4233 |
| HPV18 | L1 | RLVWACAGVEI | 158 | 11 | | | | | 4234 |
| HPV18 | L1 | RVLILHYHL | 6 | 9 | | | | | 4235 |
| HPV18 | L1 | RVLILHYHLL | 6 | 10 | | | | | 4236 |
| HPV18 | L1 | RVVNTDDYV | 81 | 9 | | | | | 4237 |
| HPV18 | L1 | RVVNTDDYVT | 81 | 10 | | | | | 4238 |
| HPV18 | L1 | SADPYGDSM | 299 | 9 | | | | | 4239 |
| HPV18 | L1 | SATTSSKPA | 551 | 9 | | | | | 4240 |
| HPV18 | L1 | SAYQYRVFRV | 127 | 10 | | | | | 4241 |
| HPV18 | L1 | SICKYPDYL | 288 | 9 | | | | | 4242 |
| HPV18 | L1 | SICKYPPYLQM | 288 | 11 | | | | | 4243 |
| HPV18 | L1 | SIFYHAGSSRL | 93 | 11 | | | | | 4244 |
| HPV18 | L1 | SILEDWNFGV | 459 | 10 | | | | | 4245 |
| HPV18 | L1 | SILVYMVHI | 31 | 9 | | | | | 4246 |
| HPV18 | L1 | SILVYMVHII | 31 | 10 | | | | | 4247 |
| HPV18 | L1 | SILVYMVHIII | 31 | 11 | | | | | 4248 |
| HPV18 | L1 | SIVTSDSQL | 359 | 9 | | | | | 4249 |
| HPV18 | L1 | SIYNPETQRL | 150 | 10 | | | | | 4250 |
| HPV18 | L1 | SIYNPETQRLV | 150 | 11 | | | | | 4251 |
| HPV18 | L1 | SLDLDQYPL | 518 | 9 | | | | | 4252 |
| HPV18 | L1 | SLVDTYRFV | 475 | 9 | | | | | 4253 |
| HPV18 | L1 | SLYIKGTGM | 335 | 9 | | | | | 4254 |
| HPV18 | L1 | SLYIKGTGMPA | 335 | 11 | | | | | 4255 |
| HPV18 | L1 | SMFFCLRREQL | 306 | 11 | | | | | 4256 |
| HPV18 | L1 | SQGDCPPL | 242 | 8 | | | | | 4257 |
| HPV18 | L1 | SQGDCPPLEL | 242 | 10 | | | | | 4258 |
| HPV18 | L1 | SQLFNKPYWL | 365 | 10 | | | | | 4259 |
| HPV18 | L1 | STLQDTKCEV | 272 | 10 | | | | | 4260 |
| HPV18 | L1 | STNLTICA | 400 | 8 | | | | | 4261 |
| HPV18 | L1 | STNLTICAST | 400 | 10 | | | | | 4262 |
| HPV18 | L1 | SVAITCQKDA | 485 | 10 | | | | | 4263 |
| HPV18 | L1 | SVAITCQKDAA | 485 | 11 | | | | | 4264 |
| HPV18 | L1 | SVARVVNT | 78 | 8 | | | | | 4265 |
| HPV18 | L1 | SVDYKQTQL | 209 | 9 | | | | | 4266 |
| HPV18 | L1 | SVDYKQTQLCI | 209 | 11 | | | | | 4267 |
| HPV18 | L1 | TACKSRPL | 234 | 8 | | | | | 4268 |
| HPV18 | L1 | TADVMSYI | 446 | 8 | | | | | 4269 |
| HPV18 | L1 | TADVMSYIHSM | 446 | 11 | | | | | 4270 |
| HPV18 | L1 | TICASTQSPV | 404 | 10 | | | | | 4271 |
| HPV18 | L1 | TIGPRKRSA | 541 | 9 | | | | | 4272 |
| HPV18 | L1 | TITLTADV | 442 | 8 | | | | | 4273 |
| HPV18 | L1 | TITLTADVM | 442 | 9 | | | | | 4274 |
| HPV18 | L1 | TLQDTKCEV | 273 | 9 | | | | | 4275 |
| HPV18 | L1 | TLQDTKCEVPL | 273 | 11 | | | | | 4276 |
| HPV18 | L1 | TLTADVMSYI | 444 | 10 | | | | | 4277 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | L1 | TMGDTVPQSL | 327 | 10 | | | | | 4278 |
| HPV18 | L1 | TQLCILGCA | 215 | 9 | | | | | 4279 |
| HPV18 | L1 | TQLCILGCAPA | 215 | 11 | | | | | 4280 |
| HPV18 | L1 | TQRLVWACA | 156 | 9 | | | | | 4281 |
| HPV18 | L1 | TQRLVWACAGV | 156 | 11 | | | | | 4282 |
| HPV18 | L1 | TQSPVPGQYDA | 409 | 11 | | | | | 4283 |
| HPV18 | L1 | TTPSTNLT | 397 | 8 | | | | | 4284 |
| HPV18 | L1 | TTPSTNLTI | 397 | 9 | | | | | 4285 |
| HPV18 | L1 | TTPSTNLTICA | 397 | 11 | | | | | 4286 |
| HPV18 | L1 | TTSLVDTYRFV | 473 | 11 | | | | | 4287 |
| HPV18 | L1 | TTSSKPAKRV | 553 | 10 | | | | | 4288 |
| HPV18 | L1 | TVGNPYFRV | 105 | 9 | | | | | 4289 |
| HPV18 | L1 | TVGNPYFRVPA | 105 | 11 | | | | | 4290 |
| HPV18 | L1 | TVLEDGDM | 254 | 8 | | | | | 4291 |
| HPV18 | L1 | TVLEDGDMV | 254 | 9 | | | | | 4292 |
| HPV18 | L1 | TVLEDGDMVDT | 254 | 11 | | | | | 4293 |
| HPV18 | L1 | TVPQSLYI | 331 | 8 | | | | | 4294 |
| HPV18 | L1 | TVPQSLYIKGT | 331 | 11 | | | | | 4295 |
| HPV18 | L1 | TVVDTTPST | 393 | 9 | | | | | 4296 |
| HPV18 | L1 | TVVDTTPSTNL | 393 | 11 | | | | | 4297 |
| HPV18 | L1 | TVYLPPPSV | 71 | 9 | | | | | 4298 |
| HPV18 | L1 | TVYLPPPSVA | 71 | 10 | | | | | 4299 |
| HPV18 | L1 | VAITCQKDA | 486 | 9 | | | | | 4300 |
| HPV18 | L1 | VAITCQKDAA | 486 | 10 | | | | | 4301 |
| HPV18 | L1 | VARVVNTDDYV | 79 | 11 | | | | | 4302 |
| HPV18 | L1 | VLEDGDMV | 255 | 8 | | | | | 4303 |
| HPV18 | L1 | VLEDGDMVDT | 255 | 10 | | | | | 4304 |
| HPV18 | L1 | VLILHYHL | 7 | 8 | | | | | 4305 |
| HPV18 | L1 | VLILHYHLL | 7 | 9 | | | | | 4306 |
| HPV18 | L1 | VLILHYHLLPL | 7 | 11 | | | | | 4307 |
| HPV18 | L1 | VMSYIHSM | 449 | 8 | | | | | 4308 |
| HPV18 | L1 | VQAGLRRKPT | 532 | 10 | | | | | 4309 |
| HPV18 | L1 | VQAGLRRKPTI | 532 | 11 | | | | | 4310 |
| HPV18 | L1 | VQLPDNKFGL | 136 | 11 | | | | | 4311 |
| HPV18 | L1 | VTPTSIFYHA | 89 | 10 | | | | | 4312 |
| HPV18 | L1 | VTVVDTTPST | 392 | 10 | | | | | 4313 |
| HPV18 | L1 | VVDTTPST | 394 | 8 | | | | | 4314 |
| HPV18 | L1 | VVDTTPSTNL | 394 | 10 | | | | | 4315 |
| HPV18 | L1 | VVDTTPSTNLT | 394 | 11 | | | | | 4316 |
| HPV18 | L1 | VVNTDDYV | 82 | 8 | | | | | 4317 |
| HPV18 | L1 | VVNTDDYVT | 82 | 9 | | | | | 4318 |
| HPV18 | L1 | VVNTDDYVTPT | 82 | 11 | | | | | 4319 |
| HPV18 | L1 | WACAGVEI | 161 | 8 | | | | | 4320 |
| HPV18 | L1 | YIHSMNSSI | 452 | 9 | | | | | 4321 |
| HPV18 | L1 | YIHSMNSSIL | 452 | 10 | | | | | 4322 |
| HPV18 | L1 | YIILFLRNV | 45 | 9 | | | | | 4323 |
| HPV18 | L1 | YIILFLRNVNV | 45 | 11 | | | | | 4324 |
| HPV18 | L1 | YIKGTGMPA | 337 | 9 | | | | | 4325 |
| HPV18 | L1 | YLPPPSVA | 73 | 8 | | | | | 4326 |
| HPV18 | L1 | YLPPPSVARV | 73 | 10 | | | | | 4327 |
| HPV18 | L1 | YLPPPSVARVV | 73 | 11 | | | | | 4328 |
| HPV18 | L1 | YQYRVFRV | 129 | 8 | | | | | 4329 |
| HPV18 | L1 | YQYRVFRVQL | 129 | 10 | | | | | 4330 |
| HPV18 | L1 | YTRVLILHYL | 4 | 11 | | | | | 4331 |
| HPV18 | L1 | YVTPTSIFYHA | 88 | 11 | | | | | 4332 |
| HPV18 | L2 | AARRKRASV | 6 | 9 | | | | | 4333 |
| HPV18 | L2 | AARRKRASVT | 6 | 10 | | | | | 4334 |
| HPV18 | L2 | ALTSRRGT | 286 | 8 | | | | | 4335 |
| HPV18 | L2 | ALTSRRGTV | 286 | 9 | | | | | 4336 |
| HPV18 | L2 | ATEDNDLFDI | 341 | 10 | | | | | 4337 |
| HPV18 | L2 | ATMFTRSGT | 303 | 9 | | | | | 4338 |
| HPV18 | L2 | ATMFTRSGTQI | 303 | 11 | | | | | 4339 |
| HPV18 | L2 | AVLDITPSST | 139 | 10 | | | | | 4340 |
| HPV18 | L2 | AVPVPSRST | 358 | 9 | | | | | 4341 |
| HPV18 | L2 | AVPVPSRSTT | 358 | 10 | | | | | 4342 |
| HPV18 | L2 | DIIRLHRPA | 278 | 9 | | | | | 4343 |
| HPV18 | L2 | DIIRLHRPAL | 278 | 10 | | | | | 4344 |
| HPV18 | L2 | DIIRLHRPALT | 278 | 11 | | | | | 4345 |
| HPV18 | L2 | DITLPSTT | 404 | 8 | | | | | 4346 |
| HPV18 | L2 | DITLPSTTSV | 404 | 10 | | | | | 4347 |
| HPV18 | L2 | DITPSSTSV | 142 | 9 | | | | | 4348 |
| HPV18 | L2 | DITPSSTSVSI | 142 | 11 | | | | | 4349 |
| HPV18 | L2 | DITSAGTT | 129 | 8 | | | | | 4350 |
| HPV18 | L2 | DITSAGTTT | 129 | 9 | | | | | 4351 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | L2 | DITSAGTTTPA | 129 | 11 | | | | | 4352 |
| HPV18 | L2 | DIYADDMDPA | 349 | 10 | | | | | 4353 |
| HPV18 | L2 | DIYADDMDPAV | 349 | 11 | | | | | 4354 |
| HPV18 | L2 | DLFDIYADDM | 346 | 10 | | | | | 4355 |
| HPV18 | L2 | DLYKTCKQSGT | 16 | 11 | | | | | 4356 |
| HPV18 | L2 | DMDPAVPV | 354 | 8 | | | | | 4357 |
| HPV18 | L2 | DVGTRPPV | 83 | 9 | | | | | 4358 |
| HPV18 | L2 | DVGPTRPPVV | 83 | 10 | | | | | 4359 |
| HPV18 | L2 | DVGPTRPPVVI | 83 | 11 | | | | | 4360 |
| HPV18 | L2 | DVPDSDFM | 270 | 8 | | | | | 4361 |
| HPV18 | L2 | DVPDSDFMDI | 270 | 10 | | | | | 4362 |
| HPV18 | L2 | DVPDSDFMDII | 270 | 11 | | | | | 4363 |
| HPV18 | L2 | DVPVYTGPDI | 396 | 10 | | | | | 4364 |
| HPV18 | L2 | DVPVYTGPDIT | 396 | 11 | | | | | 4365 |
| HPV18 | L2 | DVVPKVEGT | 30 | 9 | | | | | 4366 |
| HPV18 | L2 | DVVPKVEGTT | 30 | 10 | | | | | 4367 |
| HPV18 | L2 | DVVPKVEGTTL | 30 | 11 | | | | | 4368 |
| HPV18 | L2 | EIPLQTFA | 194 | 8 | | | | | 4369 |
| HPV18 | L2 | ELQPLVSA | 334 | 8 | | | | | 4370 |
| HPV18 | L2 | ELQPLVSAT | 334 | 9 | | | | | 4371 |
| HPV18 | L2 | EVAGNVFV | 175 | 8 | | | | | 4372 |
| HPV18 | L2 | EVAGNVFVGT | 175 | 10 | | | | | 4373 |
| HPV18 | L2 | EVPQTGEV | 169 | 8 | | | | | 4374 |
| HPV18 | L2 | EVPQTGEVA | 169 | 9 | | | | | 4375 |
| HPV18 | L2 | FADGFVAA | 455 | 8 | | | | | 4376 |
| HPV18 | L2 | FAFFKYSPT | 369 | 9 | | | | | 4377 |
| HPV18 | L2 | FAFFKYSPTI | 369 | 10 | | | | | 4378 |
| HPV18 | L2 | FASSGTGEEPI | 200 | 11 | | | | | 4379 |
| HPV18 | L2 | FIPKKRKRV | 443 | 9 | | | | | 4380 |
| HPV18 | L2 | FLGGLGIGT | 53 | 9 | | | | | 4381 |
| HPV18 | L2 | FLTRPSSL | 241 | 8 | | | | | 4382 |
| HPV18 | L2 | FLTRPSSLI | 241 | 9 | | | | | 4383 |
| HPV18 | L2 | FLTRPSSLIT | 241 | 10 | | | | | 4384 |
| HPV18 | L2 | FMDIIRLHRPA | 276 | 11 | | | | | 4385 |
| HPV18 | L2 | FTGTSGFDI | 122 | 9 | | | | | 4386 |
| HPV18 | L2 | FTGTSGFDIT | 122 | 10 | | | | | 4387 |
| HPV18 | L2 | FTNPAFSDPSI | 157 | 11 | | | | | 4388 |
| HPV18 | L2 | FTRSGTQI | 306 | 8 | | | | | 4389 |
| HPV18 | L2 | FTRSGTQIGA | 306 | 10 | | | | | 4390 |
| HPV18 | L2 | FVGTPTSGT | 181 | 9 | | | | | 4391 |
| HPV18 | L2 | GAPRPTFT | 116 | 8 | | | | | 4392 |
| HPV18 | L2 | GAPRPTFTGT | 116 | 10 | | | | | 4393 |
| HPV18 | L2 | GARVHFYHDI | 314 | 10 | | | | | 4394 |
| HPV18 | L2 | GIFLGGLGI | 51 | 9 | | | | | 4395 |
| HPV18 | L2 | GIFLGGLGIGT | 51 | 11 | | | | | 4396 |
| HPV18 | L2 | GIGTGSGT | 58 | 8 | | | | | 4397 |
| HPV18 | L2 | GIHGTHYYL | 429 | 9 | | | | | 4398 |
| HPV18 | L2 | GLGIGTGSGT | 56 | 10 | | | | | 4399 |
| HPV18 | L2 | GQRATMFT | 30 | 8 | | | | | 4400 |
| HPV18 | L2 | GTCPPDVV | 25 | 8 | | | | | 4401 |
| HPV18 | L2 | GTCPPDVVPKV | 25 | 11 | | | | | 4402 |
| HPV18 | L2 | GTGEEPISST | 204 | 10 | | | | | 4403 |
| HPV18 | L2 | GTGGRTGYI | 64 | 9 | | | | | 4404 |
| HPV18 | L2 | GTGGRTGYIPL | 64 | 11 | | | | | 4405 |
| HPV18 | L2 | GTGSGTGGRT | 60 | 10 | | | | | 4406 |
| HPV18 | L2 | GTHGYEEI | 188 | 8 | | | | | 4407 |
| HPV18 | L2 | GTHGYEEIPL | 188 | 10 | | | | | 4408 |
| HPV18 | L2 | GTHYYLWPL | 432 | 9 | | | | | 4409 |
| HPV18 | L2 | GTQIGARV | 310 | 8 | | | | | 4410 |
| HPV18 | L2 | GTSGFDIT | 124 | 8 | | | | | 4411 |
| HPV18 | L2 | GTSGFDITSA | 124 | 10 | | | | | 4412 |
| HPV18 | L2 | GTTLADKI | 37 | 8 | | | | | 4413 |
| HPV18 | L2 | GTTLADKIL | 37 | 9 | | | | | 4414 |
| HPV18 | L2 | GTTTPAVL | 134 | 8 | | | | | 4415 |
| HPV18 | L2 | GTTTPAVLDI | 134 | 10 | | | | | 4416 |
| HPV18 | L2 | GTTTPAVLDIT | 134 | 11 | | | | | 4417 |
| HPV18 | L2 | GTVRFSRL | 292 | 8 | | | | | 4418 |
| HPV18 | L2 | IAPSPEYI | 326 | 8 | | | | | 4419 |
| HPV18 | L2 | IAPSPEYIEL | 326 | 10 | | | | | 4420 |
| HPV18 | L2 | IIEVPQTGEV | 167 | 10 | | | | | 4421 |
| HPV18 | L2 | IIEVPQTGEVA | 167 | 11 | | | | | 4422 |
| HPV18 | L2 | IIRLHRPA | 279 | 8 | | | | | 4423 |
| HPV18 | L2 | IIRLHRPAL | 279 | 9 | | | | | 4424 |
| HPV18 | L2 | IIRLHRPALT | 279 | 10 | | | | | 4425 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | L2 | ILQWSSLGI | 44 | 9 | | | | | 4426 |
| HPV18 | L2 | ILQWSSLGIFL | 44 | 11 | | | | | 4427 |
| HPV18 | L2 | ITLPSTTSV | 405 | 9 | | | | | 4428 |
| HPV18 | L2 | ITPSSTSV | 143 | 8 | | | | | 4429 |
| HPV18 | L2 | ITPSSTSVSI | 143 | 10 | | | | | 4430 |
| HPV18 | L2 | ITSAGTTT | 130 | 8 | | | | | 4431 |
| HPV18 | L2 | ITSAGTTTPA | 130 | 10 | | | | | 4432 |
| HPV18 | L2 | ITSAGTTTPAV | 130 | 11 | | | | | 4433 |
| HPV18 | L2 | ITYDNPAFEPV | 249 | 11 | | | | | 4434 |
| HPV18 | L2 | IVSPTAPA | 416 | 8 | | | | | 4435 |
| HPV18 | L2 | IVSPTAPAST | 416 | 10 | | | | | 4436 |
| HPV18 | L2 | IVTLIEDSSV | 103 | 10 | | | | | 4437 |
| HPV18 | L2 | IVTLIEDSSVV | 103 | 11 | | | | | 4438 |
| HPV18 | L2 | KILQWSSL | 43 | 8 | | | | | 4439 |
| HPV18 | L2 | KILQWSSLGI | 43 | 10 | | | | | 4440 |
| HPV18 | L2 | KQSGTCPPDV | 22 | 10 | | | | | 4441 |
| HPV18 | L2 | KQSGTCPPDVV | 22 | 11 | | | | | 4442 |
| HPV18 | L2 | KTCKQSGT | 19 | 8 | | | | | 4443 |
| HPV18 | L2 | KVEGTTLA | 34 | 8 | | | | | 4444 |
| HPV18 | L2 | KVEGTTLADKI | 34 | 11 | | | | | 4445 |
| HPV18 | L2 | LADKILQWSSL | 40 | 11 | | | | | 4446 |
| HPV18 | L2 | LIEDSSVV | 106 | 8 | | | | | 4447 |
| HPV18 | L2 | LIEDSSVVT | 106 | 9 | | | | | 4448 |
| HPV18 | L2 | LITYDNPA | 248 | 8 | | | | | 4449 |
| HPV18 | L2 | LQPLVSAT | 335 | 8 | | | | | 4450 |
| HPV18 | L2 | LQTFASSGT | 197 | 9 | | | | | 4451 |
| HPV18 | L2 | LQWSSLGI | 45 | 8 | | | | | 4452 |
| HPV18 | L2 | LQWSSLGIFL | 45 | 10 | | | | | 4453 |
| HPV18 | L2 | LTFDPRSDV | 263 | 9 | | | | | 4454 |
| HPV18 | L2 | LTRPSSLI | 242 | 8 | | | | | 4455 |
| HPV18 | L2 | LTRPSSLIT | 242 | 9 | | | | | 4456 |
| HPV18 | L2 | LTSRRGTV | 287 | 8 | | | | | 4457 |
| HPV18 | L2 | LTSSWDVPV | 391 | 9 | | | | | 4458 |
| HPV18 | L2 | LTSSWDVPVYT | 391 | 11 | | | | | 4459 |
| HPV18 | L2 | LVSATEDNDL | 338 | 10 | | | | | 4460 |
| HPV18 | L2 | NTVVDVGPT | 79 | 9 | | | | | 4461 |
| HPV18 | L2 | NVFVGTPT | 179 | 8 | | | | | 4462 |
| HPV18 | L2 | NVFVGTPTSGT | 179 | 11 | | | | | 4463 |
| HPV18 | L2 | PAFEPVDT | 254 | 8 | | | | | 4464 |
| HPV18 | L2 | PAFEPVDTT | 254 | 9 | | | | | 4465 |
| HPV18 | L2 | PAFEPVDTTL | 254 | 10 | | | | | 4466 |
| HPV18 | L2 | PAFEPVDTTLT | 254 | 11 | | | | | 4467 |
| HPV18 | L2 | PAFSDPSI | 160 | 8 | | | | | 4468 |
| HPV18 | L2 | PAFSDPSII | 160 | 9 | | | | | 4469 |
| HPV18 | L2 | PAFSDPSIIEV | 160 | 11 | | | | | 4470 |
| HPV18 | L2 | PALTSRRGT | 285 | 9 | | | | | 4471 |
| HPV18 | L2 | PALTSRRGTV | 285 | 10 | | | | | 4472 |
| HPV18 | L2 | PASTQYIGI | 422 | 9 | | | | | 4473 |
| HPV18 | L2 | PAVLDITPSST | 138 | 11 | | | | | 4474 |
| HPV18 | L2 | PAVPVPSRST | 357 | 10 | | | | | 4475 |
| HPV18 | L2 | PAVPVPSRSTT | 357 | 11 | | | | | 4476 |
| HPV18 | L2 | PIAPSPEYI | 325 | 9 | | | | | 4477 |
| HPV18 | L2 | PIAPSPEYIEL | 325 | 11 | | | | | 4478 |
| HPV18 | L2 | PISSTPLPT | 209 | 9 | | | | | 4479 |
| HPV18 | L2 | PISSTPLPTV | 209 | 10 | | | | | 4480 |
| HPV18 | L2 | PIVSPTAPA | 415 | 9 | | | | | 4481 |
| HPV18 | L2 | PIVSPTAPAST | 415 | 11 | | | | | 4482 |
| HPV18 | L2 | PLGGRSNT | 73 | 8 | | | | | 4483 |
| HPV18 | L2 | PLGGRSNTV | 73 | 9 | | | | | 4484 |
| HPV18 | L2 | PLGGRSNTVV | 73 | 10 | | | | | 4485 |
| HPV18 | L2 | PLPTVRRV | 214 | 8 | | | | | 4486 |
| HPV18 | L2 | PLPTVRRVA | 214 | 9 | | | | | 4487 |
| HPV18 | L2 | PLQTFASSGT | 196 | 10 | | | | | 4488 |
| HPV18 | L2 | PLTSSWDV | 390 | 8 | | | | | 4489 |
| HPV18 | L2 | PLTSSWDVPV | 390 | 10 | | | | | 4490 |
| HPV18 | L2 | PLVSATEDNDL | 337 | 11 | | | | | 4491 |
| HPV18 | L2 | PQTGEVAGNV | 171 | 10 | | | | | 4492 |
| HPV18 | L2 | PTAPASTQYI | 419 | 10 | | | | | 4493 |
| HPV18 | L2 | PTDPSIVT | 98 | 8 | | | | | 4494 |
| HPV18 | L2 | PTDPSIVTL | 98 | 9 | | | | | 4495 |
| HPV18 | L2 | PTDPSIVTLI | 98 | 10 | | | | | 4496 |
| HPV18 | L2 | PTFTGTSGFDI | 120 | 11 | | | | | 4497 |
| HPV18 | L2 | PTRPPVVI | 86 | 8 | | | | | 4498 |
| HPV18 | L2 | PTRPPVVIEPV | 86 | 11 | | | | | 4499 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | L2 | PTSGTHGYEEI | 185 | 11 | | | | | 4500 |
| HPV18 | L2 | PTVRRVAGPRL | 216 | 11 | | | | | 4501 |
| HPV18 | L2 | PVGPTDPSI | 95 | 9 | | | | | 4502 |
| HPV18 | L2 | PVGPTDPSIV | 95 | 10 | | | | | 4503 |
| HPV18 | L2 | PVGPTDPSIVT | 95 | 11 | | | | | 4504 |
| HPV18 | L2 | PVPSRSTT | 360 | 8 | | | | | 4505 |
| HPV18 | L2 | PVPSRSTTSFA | 360 | 11 | | | | | 4506 |
| HPV18 | L2 | PVVIEPVGPT | 90 | 10 | | | | | 4507 |
| HPV18 | L2 | PVYTGPDI | 398 | 8 | | | | | 4508 |
| HPV18 | L2 | PVYTGPDIT | 398 | 9 | | | | | 4509 |
| HPV18 | L2 | PVYTGPDITL | 398 | 10 | | | | | 4510 |
| HPV18 | L2 | QQVSVANPEFL | 232 | 11 | | | | | 4511 |
| HPV18 | L2 | QTFASSGT | 198 | 8 | | | | | 4512 |
| HPV18 | L2 | QTGEVAGNV | 172 | 9 | | | | | 4513 |
| HPV18 | L2 | QTGEVAGNVFV | 172 | 11 | | | | | 4514 |
| HPV18 | L2 | QVSVANPEFL | 233 | 10 | | | | | 4515 |
| HPV18 | L2 | QVSVANPEFLT | 233 | 11 | | | | | 4516 |
| HPV18 | L2 | RAARRKRA | 5 | 8 | | | | | 4517 |
| HPV18 | L2 | RAARRKRASV | 5 | 10 | | | | | 4518 |
| HPV18 | L2 | RAARRKRASVT | 5 | 11 | | | | | 4519 |
| HPV18 | L2 | RASVTDLYKT | 11 | 10 | | | | | 4520 |
| HPV18 | L2 | RATMFTRSGT | 302 | 10 | | | | | 4521 |
| HPV18 | L2 | RAYQQVSV | 229 | 8 | | | | | 4522 |
| HPV18 | L2 | RAYQQVSVA | 229 | 9 | | | | | 4523 |
| HPV18 | L2 | RLGQRATM | 298 | 8 | | | | | 4524 |
| HPV18 | L2 | RLGQRATMFT | 298 | 10 | | | | | 4525 |
| HPV18 | L2 | RLHRPALT | 281 | 8 | | | | | 4526 |
| HPV18 | L2 | RLYSRAYQQV | 225 | 10 | | | | | 4527 |
| HPV18 | L2 | RVAGPRLYSRA | 220 | 11 | | | | | 4528 |
| HPV18 | L2 | RVHFYHDI | 316 | 8 | | | | | 4529 |
| HPV18 | L2 | RVHFYHDISPI | 316 | 11 | | | | | 4530 |
| HPV18 | L2 | RVPYFFADGFV | 450 | 11 | | | | | 4531 |
| HPV18 | L2 | SAGTTTPA | 132 | 8 | | | | | 4532 |
| HPV18 | L2 | SAGTTTPAV | 132 | 9 | | | | | 4533 |
| HPV18 | L2 | SAGTTTPAVL | 132 | 10 | | | | | 4534 |
| HPV18 | L2 | SASSYSNV | 380 | 8 | | | | | 4535 |
| HPV18 | L2 | SASSYSNVT | 380 | 9 | | | | | 4536 |
| HPV18 | L2 | SASSYSNVTV | 380 | 10 | | | | | 4537 |
| HPV18 | L2 | SATEDNDL | 340 | 8 | | | | | 4538 |
| HPV18 | L2 | SATEDNDLFDI | 340 | 11 | | | | | 4539 |
| HPV18 | L2 | SIIEVPQT | 166 | 8 | | | | | 4540 |
| HPV18 | L2 | SIIEVPQTGEV | 166 | 11 | | | | | 4541 |
| HPV18 | L2 | SISTTNFT | 151 | 8 | | | | | 4542 |
| HPV18 | L2 | SISTTNFTNPA | 151 | 11 | | | | | 4543 |
| HPV18 | L2 | SIVTLIEDSSV | 102 | 11 | | | | | 4544 |
| HPV18 | L2 | SLGIFLGGL | 49 | 9 | | | | | 4545 |
| HPV18 | L2 | SLGIFLGGLGI | 49 | 11 | | | | | 4546 |
| HPV18 | L2 | SLITYDNPA | 247 | 9 | | | | | 4547 |
| HPV18 | L2 | STPLPTVRRV | 212 | 10 | | | | | 4548 |
| HPV18 | L2 | STPLPTVRRVA | 212 | 11 | | | | | 4549 |
| HPV18 | L2 | STQYIGIHGT | 424 | 10 | | | | | 4550 |
| HPV18 | L2 | STSVSIST | 147 | 8 | | | | | 4551 |
| HPV18 | L2 | STSVSISTT | 147 | 9 | | | | | 4552 |
| HPV18 | L2 | STTNFTNPA | 153 | 9 | | | | | 4553 |
| HPV18 | L2 | STTSVWPI | 409 | 8 | | | | | 4554 |
| HPV18 | L2 | STTSVWPIV | 409 | 9 | | | | | 4555 |
| HPV18 | L2 | SVANPEFL | 235 | 8 | | | | | 4556 |
| HPV18 | L2 | SVANPEFLT | 235 | 9 | | | | | 4557 |
| HPV18 | L2 | SVSISTTNFT | 149 | 10 | | | | | 4558 |
| HPV18 | L2 | SVTDLYKT | 13 | 8 | | | | | 4559 |
| HPV18 | L2 | SVVTSGAPRPT | 111 | 11 | | | | | 4560 |
| HPV18 | L2 | SVWPIVSPT | 412 | 9 | | | | | 4561 |
| HPV18 | L2 | SVWPIVSPTA | 412 | 10 | | | | | 4562 |
| HPV18 | L2 | TAPASTQYI | 420 | 9 | | | | | 4563 |
| HPV18 | L2 | TAPASTQYIGI | 420 | 11 | | | | | 4564 |
| HPV18 | L2 | TISSASSYSNV | 377 | 11 | | | | | 4565 |
| HPV18 | L2 | TLIEDSSV | 105 | 8 | | | | | 4566 |
| HPV18 | L2 | TLIEDSSVV | 105 | 9 | | | | | 4567 |
| HPV18 | L2 | TLIEDSSVVT | 105 | 10 | | | | | 4568 |
| HPV18 | L2 | TLPSTTSV | 406 | 8 | | | | | 4569 |
| HPV18 | L2 | TLPSTTSVWPI | 406 | 11 | | | | | 4570 |
| HPV18 | L2 | TLTFDPRSDV | 262 | 10 | | | | | 4571 |
| HPV18 | L2 | TMFTRSGT | 304 | 8 | | | | | 4572 |
| HPV18 | L2 | TMFTRSGTQI | 304 | 10 | | | | | 4573 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV18 | L2 | TQYIGIHGT | 425 | 9 | | | | | 4574 |
| HPV18 | L2 | TTLADKIL | 38 | 8 | | | | | 4575 |
| HPV18 | L2 | TTLTFDPRSDV | 261 | 11 | | | | | 4576 |
| HPV18 | L2 | TTNFTNPA | 154 | 8 | | | | | 4577 |
| HPV18 | L2 | TTPAVLDI | 136 | 8 | | | | | 4578 |
| HPV18 | L2 | TTPAVLDIT | 136 | 9 | | | | | 4579 |
| HPV18 | L2 | TTSVWPIV | 410 | 8 | | | | | 4580 |
| HPV18 | L2 | TTSVWPIVSPT | 410 | 11 | | | | | 4581 |
| HPV18 | L2 | TTTPAVLDI | 135 | 9 | | | | | 4582 |
| HPV18 | L2 | TTTPAVLDIT | 135 | 10 | | | | | 4583 |
| HPV18 | L2 | TVPLTSSWDV | 388 | 10 | | | | | 4584 |
| HPV18 | L2 | TVRFSRLGQRA | 293 | 11 | | | | | 4585 |
| HPV18 | L2 | TVRRVAGPRL | 217 | 10 | | | | | 4586 |
| HPV18 | L2 | TVVDVGPT | 80 | 8 | | | | | 4587 |
| HPV18 | L2 | VAGNVFVGT | 176 | 9 | | | | | 4588 |
| HPV18 | L2 | VAGNVFVGTPT | 176 | 11 | | | | | 4589 |
| HPV18 | L2 | VAGPRLYSRA | 221 | 10 | | | | | 4590 |
| HPV18 | L2 | VANPEFLT | 236 | 8 | | | | | 4591 |
| HPV18 | L2 | VIEPVGPT | 92 | 8 | | | | | 4592 |
| HPV18 | L2 | VLDITPSST | 140 | 9 | | | | | 4593 |
| HPV18 | L2 | VLDITPSSTSV | 140 | 11 | | | | | 4594 |
| HPV18 | L2 | VTLIEDSSV | 104 | 9 | | | | | 4595 |
| HPV18 | L2 | VTLIEDSSVV | 104 | 10 | | | | | 4596 |
| HPV18 | L2 | VTLIEDSSVVT | 104 | 11 | | | | | 4597 |
| HPV18 | L2 | VTSGAPRPT | 113 | 9 | | | | | 4598 |
| HPV18 | L2 | VTSGAPRPTFT | 113 | 11 | | | | | 4599 |
| HPV18 | L2 | VTVPLTSSWDV | 387 | 11 | | | | | 4600 |
| HPV18 | L2 | VVDVGPTRPPV | 81 | 11 | | | | | 4601 |
| HPV18 | L2 | VVIEPVGPT | 91 | 9 | | | | | 4602 |
| HPV18 | L2 | VVPKVEGT | 31 | 8 | | | | | 4603 |
| HPV18 | L2 | VVPKVEGTT | 31 | 9 | | | | | 4604 |
| HPV18 | L2 | VVPKVEGTTL | 31 | 10 | | | | | 4605 |
| HPV18 | L2 | VVPKVEGTTLA | 31 | 11 | | | | | 4606 |
| HPV18 | L2 | VVTSGAPRPT | 112 | 10 | | | | | 4607 |
| HPV18 | L2 | YADDMDPA | 351 | 8 | | | | | 4608 |
| HPV18 | L2 | YADDMDPAV | 351 | 9 | | | | | 4609 |
| HPV18 | L2 | YADDMDPAVPV | 351 | 11 | | | | | 4610 |
| HPV18 | L2 | YIELQPLV | 332 | 8 | | | | | 4611 |
| HPV18 | L2 | YIELQPLVSA | 332 | 10 | | | | | 4612 |
| HPV18 | L2 | YIELQPLVSAT | 332 | 11 | | | | | 4613 |
| HPV18 | L2 | YIGIHGTHYYL | 427 | 11 | | | | | 4614 |
| HPV18 | L2 | YIPLGGRSNT | 71 | 10 | | | | | 4615 |
| HPV18 | L2 | YIPLGGRSNTV | 71 | 11 | | | | | 4616 |
| HPV18 | L2 | YLWPLYYFI | 436 | 9 | | | | | 4617 |
| HPV18 | L2 | YTGPDITL | 400 | 8 | | | | | 4618 |
| HPV18 | L2 | YTGPDITLPST | 400 | 11 | | | | | 4619 |
| HPV31 | E1 | AAALYWYRT | 296 | 9 | | | | | 4620 |
| HPV31 | E1 | AAALYWYRTGM | 296 | 11 | | | | | 4621 |
| HPV31 | E1 | AAFGVTGT | 219 | 8 | | | | | 4622 |
| HPV31 | E1 | AAFGVTGTV | 219 | 9 | | | | | 4623 |
| HPV31 | E1 | AAFGVTGTVA | 219 | 10 | | | | | 4624 |
| HPV31 | E1 | AALYWYRT | 297 | 8 | | | | | 4625 |
| HPV31 | E1 | AALYWYRTGM | 297 | 10 | | | | | 4626 |
| HPV31 | E1 | AAMLGKFKEL | 185 | 10 | | | | | 4627 |
| HPV31 | E1 | AICIENNSKT | 111 | 10 | | | | | 4628 |
| HPV31 | E1 | AICIENNSKTA | 111 | 11 | | | | | 4629 |
| HPV31 | E1 | ALDGNPVSI | 519 | 9 | | | | | 4630 |
| HPV31 | E1 | ALDGNPVSIDV | 519 | 11 | | | | | 4631 |
| HPV31 | E1 | ALFHAQEA | 68 | 8 | | | | | 4632 |
| HPV31 | E1 | ALKLFLKGV | 439 | 9 | | | | | 4633 |
| HPV31 | E1 | ALMQLKCPPL | 533 | 10 | | | | | 4634 |
| HPV31 | E1 | ALMQLKCPPLL | 533 | 11 | | | | | 4635 |
| HPV31 | E1 | ALYWYRTGM | 298 | 9 | | | | | 4636 |
| HPV31 | E1 | AMLGKFKEL | 186 | 9 | | | | | 4637 |
| HPV31 | E1 | AQALFHAQEA | 66 | 10 | | | | | 4638 |
| HPV31 | E1 | AQEAEEHA | 72 | 8 | | | | | 4639 |
| HPV31 | E1 | AQEAEEHAEA | 72 | 10 | | | | | 4640 |
| HPV31 | E1 | AQEAEEHAEAV | 72 | 11 | | | | | 4641 |
| HPV31 | E1 | AQLADSDSNA | 360 | 10 | | | | | 4642 |
| HPV31 | E1 | ATTPCWHYI | 504 | 9 | | | | | 4643 |
| HPV31 | E1 | AVIDRQTGDNI | 22 | 11 | | | | | 4644 |
| HPV31 | E1 | AVQVLKRKYV | 81 | 10 | | | | | 4645 |
| HPV31 | E1 | CAFLKSNSQA | 370 | 10 | | | | | 4646 |
| HPV31 | E1 | CAKNRITI | 263 | 8 | | | | | 4647 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E1 | CAKNRITIEKL | 263 | 11 | | | | | 4648 |
| HPV31 | E1 | CIENNSKT | 113 | 8 | | | | | 4649 |
| HPV31 | E1 | CIENNSKTA | 113 | 9 | | | | | 4650 |
| HPV31 | E1 | CILIHGAPNT | 452 | 10 | | | | | 4651 |
| HPV31 | E1 | CISTNCML | 279 | 8 | | | | | 4652 |
| HPV31 | E1 | CISTNCMLI | 279 | 9 | | | | | 4653 |
| HPV31 | E1 | CLYCHLQSL | 239 | 9 | | | | | 4654 |
| HPV31 | E1 | CLYCHLQSLA | 239 | 10 | | | | | 4655 |
| HPV31 | E1 | CMLIQPPKL | 284 | 9 | | | | | 4656 |
| HPV31 | E1 | CTDWCVAA | 213 | 8 | | | | | 4657 |
| HPV31 | E1 | CTDWCVAAFGV | 213 | 11 | | | | | 4658 |
| HPV31 | E1 | CVAAFGVT | 217 | 8 | | | | | 4659 |
| HPV31 | E1 | CVAAFGVTGT | 217 | 10 | | | | | 4660 |
| HPV31 | E1 | CVAAFGVTGTV | 217 | 11 | | | | | 4661 |
| HPV31 | E1 | CVDYNISPRL | 100 | 10 | | | | | 4662 |
| HPV31 | E1 | CVSGQNIRT | 620 | 9 | | | | | 4663 |
| HPV31 | E1 | CVSGQNIRTL | 620 | 10 | | | | | 4664 |
| HPV31 | E1 | DAKIGMLDDA | 495 | 10 | | | | | 4665 |
| HPV31 | E1 | DAKIGMLDDAT | 495 | 11 | | | | | 4666 |
| HPV31 | E1 | DATTPCWHYI | 503 | 10 | | | | | 4667 |
| HPV31 | E1 | DISSCVDYNI | 96 | 10 | | | | | 4668 |
| HPV31 | E1 | DIVKFLRYQQI | 421 | 11 | | | | | 4669 |
| HPV31 | E1 | DLSQMVQWA | 336 | 9 | | | | | 4670 |
| HPV31 | E1 | DMVDFIDNCNV | 46 | 11 | | | | | 4671 |
| HPV31 | E1 | DTGEDMVDFI | 42 | 10 | | | | | 4672 |
| HPV31 | E1 | DTTFDLSQM | 332 | 9 | | | | | 4673 |
| HPV31 | E1 | DTTFDLSQMV | 332 | 10 | | | | | 4674 |
| HPV31 | E1 | DVKHKALM | 528 | 8 | | | | | 4675 |
| HPV31 | E1 | DVKHKALMQL | 528 | 10 | | | | | 4676 |
| HPV31 | E1 | DVMDDSEI | 348 | 8 | | | | | 4677 |
| HPV31 | E1 | DVMDDSEIA | 348 | 9 | | | | | 4678 |
| HPV31 | E1 | DVYGETPEWI | 311 | 10 | | | | | 4679 |
| HPV31 | E1 | EAEEHAEA | 74 | 8 | | | | | 4680 |
| HPV31 | E1 | EAEEHAEAV | 74 | 9 | | | | | 4681 |
| HPV31 | E1 | EAEEHAEAVQV | 74 | 11 | | | | | 4682 |
| HPV31 | E1 | EAETAQAL | 62 | 8 | | | | | 4683 |
| HPV31 | E1 | EAETAQALFHA | 62 | 11 | | | | | 4684 |
| HPV31 | E1 | EAVIDRQT | 21 | 8 | | | | | 4685 |
| HPV31 | E1 | EAVQVLKRKYV | 80 | 11 | | | | | 4686 |
| HPV31 | E1 | EIAYKYAQL | 354 | 9 | | | | | 4687 |
| HPV31 | E1 | EIAYKYAQLA | 354 | 10 | | | | | 4688 |
| HPV31 | E1 | ELPDSGYGNT | 127 | 10 | | | | | 4689 |
| HPV31 | E1 | ELYGVSFM | 193 | 8 | | | | | 4690 |
| HPV31 | E1 | ELYGVSFMEL | 193 | 10 | | | | | 4691 |
| HPV31 | E1 | ELYGVSFMELI | 193 | 11 | | | | | 4692 |
| HPV31 | E1 | ETAQALFHA | 64 | 9 | | | | | 4693 |
| HPV31 | E1 | ETPEWIERQT | 315 | 10 | | | | | 4694 |
| HPV31 | E1 | ETPEWIERQTV | 315 | 11 | | | | | 4695 |
| HPV31 | E1 | ETPTRNIL | 168 | 8 | | | | | 4696 |
| HPV31 | E1 | ETPTRNILQV | 168 | 10 | | | | | 4697 |
| HPV31 | E1 | ETPTRNILQVL | 168 | 11 | | | | | 4698 |
| HPV31 | E1 | ETQQMVQV | 139 | 8 | | | | | 4699 |
| HPV31 | E1 | EVETQQMV | 137 | 8 | | | | | 4700 |
| HPV31 | E1 | EVETQQMVQV | 137 | 10 | | | | | 4701 |
| HPV31 | E1 | FLKGVPKKNCI | 443 | 11 | | | | | 4702 |
| HPV31 | E1 | FLKSNSQA | 372 | 8 | | | | | 4703 |
| HPV31 | E1 | FLKSNSQAKI | 372 | 10 | 0.0011 | | | | 4704 |
| HPV31 | E1 | FLKSNSQAKIV | 372 | 11 | | | | | 4705 |
| HPV31 | E1 | FLQGCIISYA | 473 | 10 | | | | | 4706 |
| HPV31 | E1 | FLRYQQIEFV | 425 | 10 | | | | | 4707 |
| HPV31 | E1 | FLSALKLFL | 436 | 9 | | | | | 4708 |
| HPV31 | E1 | FQSNKSTCT | 206 | 9 | | | | | 4709 |
| HPV31 | E1 | FVSFLSAL | 433 | 8 | | | | | 4710 |
| HPV31 | E1 | FVSFLSALKL | 433 | 10 | | | | | 4711 |
| HPV31 | E1 | GMLDDATT | 499 | 8 | | | | | 4712 |
| HPV31 | E1 | GMSLISFL | 467 | 8 | | | | | 4713 |
| HPV31 | E1 | GMSNISDV | 305 | 8 | | | | | 4714 |
| HPV31 | E1 | GMVMLMLV | 252 | 8 | | | | | 4715 |
| HPV31 | E1 | GQWIKSRCDKV | 403 | 11 | | | | | 4716 |
| HPV31 | E1 | GTGCNGWFYV | 11 | 10 | 0.0006 | | | | 4717 |
| HPV31 | E1 | GTHSERENET | 160 | 10 | | | | | 4718 |
| HPV31 | E1 | GTMCRHYKRA | 386 | 10 | | | | | 4719 |
| HPV31 | E1 | GTVAEGFKT | 225 | 9 | | | | | 4720 |
| HPV31 | E1 | GTVAEGFKTL | 225 | 10 | | | | | 4721 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E1 | GTVAEGFKTLL | 225 | 11 | | | | | 4722 |
| HPV31 | E1 | GVPKKNCI | 446 | 8 | | | | | 4723 |
| HPV31 | E1 | GVPKKNCIL | 446 | 9 | | | | | 4724 |
| HPV31 | E1 | GVPKKNCILI | 446 | 10 | | | | | 4725 |
| HPV31 | E1 | GVSFMELI | 196 | 8 | | | | | 4726 |
| HPV31 | E1 | HAEAVQVL | 78 | 8 | | | | | 4727 |
| HPV31 | E1 | HAQEAEEHA | 71 | 9 | | | | | 4728 |
| HPV31 | E1 | HAQEAEEHAEA | 71 | 11 | | | | | 4729 |
| HPV31 | E1 | HLQSLACSWGM | 243 | 11 | | | | | 4730 |
| HPV31 | E1 | IAYKYAQL | 355 | 8 | | | | | 4731 |
| HPV31 | E1 | IAYKYAQLA | 355 | 9 | | | | | 4732 |
| HPV31 | E1 | ILIHGAPNT | 453 | 9 | | | | | 4733 |
| HPV31 | E1 | IQPPKLRST | 287 | 9 | | | | | 4734 |
| HPV31 | E1 | IQPPKLRSTA | 287 | 10 | | | | | 4735 |
| HPV31 | E1 | IQPPKLRSTAA | 287 | 11 | | | | | 4736 |
| HPV31 | E1 | ITIEKLLEKL | 268 | 10 | | | | | 4737 |
| HPV31 | E1 | ITIEKLLEKLL | 268 | 11 | | | | | 4738 |
| HPV31 | E1 | IVKDCGTM | 381 | 8 | | | | | 4739 |
| HPV31 | E1 | IVKFLRYQQI | 422 | 10 | | | | | 4740 |
| HPV31 | E1 | KAAMLGKFKEL | 184 | 11 | | | | | 4741 |
| HPV31 | E1 | KAICIENNSKT | 110 | 11 | | | | | 4742 |
| HPV31 | E1 | KALMQLKCPPL | 532 | 11 | | | | | 4743 |
| HPV31 | E1 | KIGMLDDA | 497 | 8 | | | | | 4744 |
| HPV31 | E1 | KIGMLDDAT | 497 | 9 | | | | | 4745 |
| HPV31 | E1 | KIGMLDDATT | 497 | 10 | | | | | 4746 |
| HPV31 | E1 | KIVKDCGT | 380 | 8 | | | | | 4747 |
| HPV31 | E1 | KIVKDCGTM | 380 | 9 | | | | | 4748 |
| HPV31 | E1 | KLLCISTNCM | 276 | 10 | | | | | 4749 |
| HPV31 | E1 | KLLCISTNCML | 276 | 11 | | | | | 4750 |
| HPV31 | E1 | KLLEKLLCI | 272 | 9 | | | | | 4751 |
| HPV31 | E1 | KLLEKLLCIST | 272 | 11 | | | | | 4752 |
| HPV31 | E1 | KLRSTAAA | 291 | 8 | | | | | 4753 |
| HPV31 | E1 | KLRSTAAAL | 291 | 9 | 0.0003 | | | | 4754 |
| HPV31 | E1 | KTAKRRLFEL | 119 | 10 | | | | | 4755 |
| HPV31 | E1 | KTLLQPYCL | 232 | 9 | | | | | 4756 |
| HPV31 | E1 | KTSNGKAA | 179 | 8 | | | | | 4757 |
| HPV31 | E1 | KTSNGKAAM | 179 | 9 | | | | | 4768 |
| HPV31 | E1 | KTSNGKAAML | 179 | 10 | | | | | 4759 |
| HPV31 | E1 | KVSDEGDWRDI | 412 | 11 | | | | | 4760 |
| HPV31 | E1 | LACSWGMV | 247 | 8 | | | | | 4761 |
| HPV31 | E1 | LACSWGMVM | 247 | 9 | | | | | 4762 |
| HPV31 | E1 | LACSWGMVML | 247 | 10 | | | | | 4763 |
| HPV31 | E1 | LACSWGMVMLM | 247 | 11 | | | | | 4764 |
| HPV31 | E1 | LADAKIGM | 493 | 8 | | | | | 4765 |
| HPV31 | E1 | LADAKIGML | 493 | 9 | | | | | 4766 |
| HPV31 | E1 | LADSDSNA | 362 | 8 | | | | | 4767 |
| HPV31 | E1 | LADSDSNACA | 362 | 10 | | | | | 4768 |
| HPV31 | E1 | LIHGAPNT | 454 | 8 | | | | | 4769 |
| HPV31 | E1 | LIQPPKLRST | 286 | 10 | | | | | 4770 |
| HPV31 | E1 | LIQPPKLRSTA | 286 | 11 | | | | | 4771 |
| HPV31 | E1 | LIRPFQSNKST | 202 | 11 | | | | | 4772 |
| HPV31 | E1 | LISFLQGCI | 470 | 9 | | | | | 4773 |
| HPV31 | E1 | LISFLQGCII | 470 | 10 | | | | | 4774 |
| HPV31 | E1 | LITSNINA | 543 | 8 | | | | | 4775 |
| HPV31 | E1 | LLCISTNCM | 277 | 9 | | | | | 4776 |
| HPV31 | E1 | LLCISTNCML | 277 | 10 | | | | | 4777 |
| HPV31 | E1 | LLCISTNCMLI | 277 | 11 | | | | | 4778 |
| HPV31 | E1 | LLEKLLCI | 273 | 8 | | | | | 4779 |
| HPV31 | E1 | LLEKLLCIST | 273 | 10 | | | | | 4780 |
| HPV31 | E1 | LLITSNINA | 542 | 9 | 0.0022 | | | | 4781 |
| HPV31 | E1 | LLQPYCLYCHL | 234 | 11 | | | | | 4782 |
| HPV31 | E1 | LMLVRFKCA | 256 | 9 | | | | | 4783 |
| HPV31 | E1 | LMQLKCPPL | 534 | 9 | | | | | 4784 |
| HPV31 | E1 | LMQLKCPPLL | 534 | 10 | | | | | 4785 |
| HPV31 | E1 | LMQLKCPPLLI | 534 | 11 | | | | | 4786 |
| HPV31 | E1 | LQGCIISYA | 474 | 9 | | | | | 4787 |
| HPV31 | E1 | LQHSFNDT | 326 | 8 | | | | | 4788 |
| HPV31 | E1 | LQHSFNDTT | 326 | 9 | | | | | 4789 |
| HPV31 | E1 | LQPLADAKI | 490 | 9 | | | | | 4790 |
| HPV31 | E1 | LQPLADAKIGM | 490 | 11 | | | | | 4791 |
| HPV31 | E1 | LQPYCLYCHL | 235 | 10 | | | | | 4792 |
| HPV31 | E1 | LQSLACSWGM | 244 | 10 | | | | | 4793 |
| HPV31 | E1 | LQSLACSWGMV | 244 | 11 | | | | | 4794 |
| HPV31 | E1 | LQVLKTSNGKA | 175 | 11 | | | | | 4795 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E1 | LVRFKCAKNRI | 258 | 11 | | | | | 4796 |
| HPV31 | E1 | MLGKFKEL | 187 | 8 | | | | | 4797 |
| HPV31 | E1 | MLGKFKELYGV | 187 | 11 | | | | | 4798 |
| HPV31 | E1 | MLIQPPKL | 285 | 8 | | | | | 4799 |
| HPV31 | E1 | MLIQPPKLRST | 285 | 11 | | | | | 4800 |
| HPV31 | E1 | MLMLVRFKCA | 255 | 10 | | | | | 4801 |
| HPV31 | E1 | MLVRFKCA | 257 | 8 | | | | | 4802 |
| HPV31 | E1 | MQLKCPPL | 535 | 8 | | | | | 4803 |
| HPV31 | E1 | MQLKCPPLL | 535 | 9 | | | | | 4804 |
| HPV31 | E1 | MQLKCPPLLI | 535 | 10 | | | | | 4805 |
| HPV31 | E1 | MQLKCPPLLIT | 535 | 11 | | | | | 4806 |
| HPV31 | E1 | MVDFIDNCNV | 47 | 10 | | | | | 4807 |
| HPV31 | E1 | MVQVEEQQT | 143 | 9 | | | | | 4808 |
| HPV31 | E1 | MVQVEEQQTT | 143 | 10 | | | | | 4809 |
| HPV31 | E1 | MVQVEEQQTTL | 143 | 11 | | | | | 4810 |
| HPV31 | E1 | MVQWAYDNDV | 340 | 10 | | | | | 4811 |
| HPV31 | E1 | MVQWAYDNDVM | 340 | 11 | | | | | 4812 |
| HPV31 | E1 | NAGKDDRWPYL | 549 | 11 | | | | | 4813 |
| HPV31 | E1 | NALDGNPV | 518 | 8 | | | | | 4814 |
| HPV31 | E1 | NALDGNPVSI | 518 | 10 | | | | | 4815 |
| HPV31 | E1 | NILQVLKT | 173 | 8 | | | | | 4816 |
| HPV31 | E1 | NISDVYGET | 308 | 9 | | | | | 4817 |
| HPV31 | E1 | NISPRLKA | 104 | 8 | | | | | 4818 |
| HPV31 | E1 | NISPRLKAI | 104 | 9 | | | | | 4819 |
| HPV31 | E1 | NISPRLKAICI | 104 | 11 | | | | | 4820 |
| HPV31 | E1 | NQAEAETA | 59 | 8 | | | | | 4821 |
| HPV31 | E1 | NQAEAETAQA | 59 | 10 | | | | | 4822 |
| HPV31 | E1 | NQAEAETAQAL | 59 | 11 | | | | | 4823 |
| HPV31 | E1 | NTEVETQQM | 135 | 9 | | | | | 4824 |
| HPV31 | E1 | NTEVETQQMV | 135 | 10 | | | | | 4825 |
| HPV31 | E1 | NTGKSYFGM | 460 | 9 | | | | | 4826 |
| HPV31 | E1 | NTGKSYFGMSL | 460 | 11 | | | | | 4827 |
| HPV31 | E1 | NVYNNQAEA | 55 | 9 | | | | | 4828 |
| HPV31 | E1 | NVYNNQAEAET | 55 | 11 | | | | | 4829 |
| HPV31 | E1 | PAGTDGEGT | 4 | 9 | | | | | 4830 |
| HPV31 | E1 | PLADAKIGM | 492 | 9 | | | | | 4831 |
| HPV31 | E1 | PLADAKIGML | 492 | 10 | | | | | 4832 |
| HPV31 | E1 | PLLITSNI | 541 | 8 | | | | | 4833 |
| HPV31 | E1 | PLLITSNINA | 541 | 10 | | | | | 4834 |
| HPV31 | E1 | PLSDISSCV | 93 | 9 | | | | | 4835 |
| HPV31 | E1 | PTRNILQV | 170 | 8 | | | | | 4836 |
| HPV31 | E1 | PTRNILQVL | 170 | 9 | | | | | 4837 |
| HPV31 | E1 | PTRNILQVLKT | 170 | 11 | | | | | 4838 |
| HPV31 | E1 | PVSIDVKHKA | 524 | 10 | | | | | 4839 |
| HPV31 | E1 | PVSIDVKHKAL | 524 | 11 | | | | | 4840 |
| HPV31 | E1 | QAEAETAQA | 60 | 9 | | | | | 4841 |
| HPV31 | E1 | QAEAETAQAL | 60 | 10 | | | | | 4842 |
| HPV31 | E1 | QAKIVKDCGT | 378 | 10 | | | | | 4843 |
| HPV31 | E1 | QAKIVKDCGTM | 378 | 11 | | | | | 4844 |
| HPV31 | E1 | QALFHAQEA | 67 | 9 | | | | | 4845 |
| HPV31 | E1 | QIEFVSFL | 430 | 8 | | | | | 4846 |
| HPV31 | E1 | QIEFVSFLSA | 430 | 10 | | | | | 4847 |
| HPV31 | E1 | QIEFVSFLSAL | 430 | 11 | | | | | 4848 |
| HPV31 | E1 | QLADSDSNA | 361 | 9 | | | | | 4849 |
| HPV31 | E1 | QLADSDSNACA | 361 | 11 | | | | | 4850 |
| HPV31 | E1 | QLKCPPLL | 536 | 8 | | | | | 4851 |
| HPV31 | E1 | QLKCPPLLI | 536 | 9 | 0.0049 | | | | 4852 |
| HPV31 | E1 | QLKCPPLLIT | 536 | 10 | | | | | 4853 |
| HPV31 | E1 | QMSMGQWI | 399 | 8 | | | | | 4854 |
| HPV31 | E1 | QMVQVEEQQT | 142 | 10 | | | | | 4855 |
| HPV31 | E1 | QMVQVEEQQTT | 142 | 11 | | | | | 4856 |
| HPV31 | E1 | QMVQWAYDNDV | 339 | 11 | | | | | 4857 |
| HPV31 | E1 | QQIEFVSFL | 429 | 9 | | | | | 4858 |
| HPV31 | E1 | QQIEFVSFLSA | 429 | 11 | | | | | 4859 |
| HPV31 | E1 | QQMVQVEEQQT | 141 | 11 | | | | | 4860 |
| HPV31 | E1 | QTVLQHSFNDT | 323 | 11 | | | | | 4861 |
| HPV31 | E1 | QVEEQQTT | 145 | 8 | | | | | 4862 |
| HPV31 | E1 | QVEEQQTTL | 145 | 9 | | | | | 4863 |
| HPV31 | E1 | QVLKRKYV | 83 | 8 | | | | | 4864 |
| HPV31 | E1 | QVLKTSNGKA | 176 | 10 | | | | | 4865 |
| HPV31 | E1 | QVLKTSNGKAA | 176 | 11 | | | | | 4866 |
| HPV31 | E1 | RAEKRQMSM | 394 | 9 | | | | | 4867 |
| HPV31 | E1 | RITIEKLL | 267 | 8 | | | | | 4868 |
| HPV31 | E1 | RITIEKLLEKL | 267 | 11 | | | | | 4869 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E1 | RQMSMGQWI | 398 | 9 | | | | | 4870 |
| HPV31 | E1 | RTGMSNISDV | 303 | 10 | | | | | 4871 |
| HPV31 | E1 | RTWCRLNL | 595 | 8 | | | | | 4872 |
| HPV31 | E1 | SALKLFLKGV | 438 | 10 | | | | | 4873 |
| HPV31 | E1 | SIDVKHKA | 526 | 8 | | | | | 4874 |
| HPV31 | E1 | SIDVKHKAL | 526 | 9 | | | | | 4875 |
| HPV31 | E1 | SIDVKHKALM | 526 | 10 | | | | | 4876 |
| HPV31 | E1 | SLACSWGM | 246 | 8 | | | | | 4877 |
| HPV31 | E1 | SLACSWGMV | 246 | 9 | 0.082 | | | | 4878 |
| HPV31 | E1 | SLACSWGMVM | 246 | 10 | | | | | 4879 |
| HPV31 | E1 | SLACSWGMVML | 246 | 11 | | | | | 4880 |
| HPV31 | E1 | SLISFLQGCI | 469 | 10 | | | | | 4881 |
| HPV31 | E1 | SLISFLQGCII | 469 | 11 | | | | | 4882 |
| HPV31 | E1 | SQAKIVKDCGT | 377 | 11 | | | | | 4883 |
| HPV31 | E1 | STAAALYWYRT | 294 | 11 | | | | | 4884 |
| HPV31 | E1 | STCTDWCV | 211 | 8 | | | | | 4885 |
| HPV31 | E1 | STCTDWCVA | 211 | 9 | | | | | 4886 |
| HPV31 | E1 | STCTDWCVAA | 211 | 10 | | | | | 4887 |
| HPV31 | E1 | STFKCVSGQNI | 616 | 11 | | | | | 4888 |
| HPV31 | E1 | TAAALYWYRT | 295 | 10 | | | | | 4889 |
| HPV31 | E1 | TAKRRLFEL | 120 | 9 | | | | | 4890 |
| HPV31 | E1 | TAQALFHA | 65 | 8 | | | | | 4891 |
| HPV31 | E1 | TAQALFHAQEA | 65 | 11 | | | | | 4892 |
| HPV31 | E1 | TIEKLLEKL | 269 | 9 | | | | | 4893 |
| HPV31 | E1 | TIEKLLEKLL | 269 | 10 | | | | | 4894 |
| HPV31 | E1 | TLLQPYCL | 233 | 8 | | | | | 4895 |
| HPV31 | E1 | TLSCNGSDGT | 152 | 10 | | | | | 4896 |
| HPV31 | E1 | TMCRHYKRA | 387 | 9 | 0.0003 | | | | 4897 |
| HPV31 | E1 | TTFDLSQM | 333 | 8 | | | | | 4898 |
| HPV31 | E1 | TTFDLSQMV | 333 | 9 | | | | | 4899 |
| HPV31 | E1 | TTLSCNGSDGT | 151 | 11 | | | | | 4900 |
| HPV31 | E1 | TTPCWHYI | 505 | 8 | | | | | 4901 |
| HPV31 | E1 | TVAEGFKT | 226 | 8 | | | | | 4902 |
| HPV31 | E1 | TVAEGFKTL | 226 | 9 | | | | | 4903 |
| HPV31 | E1 | TVAEGFKTLL | 226 | 10 | | | | | 4904 |
| HPV31 | E1 | TVLQHSFNDT | 324 | 10 | | | | | 4905 |
| HPV31 | E1 | TVLQHSFNDTT | 324 | 11 | | | | | 4906 |
| HPV31 | E1 | VAAFGVTGT | 218 | 9 | | | | | 4907 |
| HPV31 | E1 | VAAFGVTGTV | 218 | 10 | | | | | 4908 |
| HPV31 | E1 | VAAFGVTGTVA | 218 | 11 | | | | | 4909 |
| HPV31 | E1 | VAEGFKTL | 227 | 8 | | | | | 4910 |
| HPV31 | E1 | VAEGFKTLL | 227 | 9 | | | | | 4911 |
| HPV31 | E1 | VIDRQTGDNI | 23 | 10 | | | | | 4912 |
| HPV31 | E1 | VLKRKYVGSPL | 84 | 11 | | | | | 4913 |
| HPV31 | E1 | VLKTSNGKA | 177 | 9 | | | | | 4914 |
| HPV31 | E1 | VLKTSNGKAA | 177 | 10 | | | | | 4915 |
| HPV31 | E1 | VLKTSNGKAAM | 177 | 11 | | | | | 4916 |
| HPV31 | E1 | VLQHSFNDT | 325 | 9 | | | | | 4917 |
| HPV31 | E1 | VLQHSFNDTT | 325 | 10 | | | | | 4918 |
| HPV31 | E1 | VMDDSEIA | 349 | 8 | | | | | 4919 |
| HPV31 | E1 | VMLMLVRFKCA | 254 | 11 | | | | | 4920 |
| HPV31 | E1 | VQVEEQQT | 144 | 8 | | | | | 4921 |
| HPV31 | E1 | VQVEEQQTT | 144 | 9 | | | | | 4922 |
| HPV31 | E1 | VQVEEQQTTL | 144 | 10 | | | | | 4923 |
| HPV31 | E1 | VQVLKRKYV | 82 | 9 | | | | | 4924 |
| HPV31 | E1 | VQWAYDNDV | 341 | 9 | | | | | 4925 |
| HPV31 | E1 | VQWAYDNDVM | 341 | 10 | | | | | 4926 |
| HPV31 | E1 | VTGTVAEGFKT | 223 | 11 | | | | | 4927 |
| HPV31 | E1 | WAYDNDVM | 343 | 8 | | | | | 4928 |
| HPV31 | E1 | WIERQTVL | 319 | 8 | | | | | 4929 |
| HPV31 | E1 | WIKSRCDKV | 405 | 9 | | | | | 4930 |
| HPV31 | E1 | WLQPLADA | 489 | 8 | | | | | 4931 |
| HPV31 | E1 | WLQPLADAKI | 489 | 10 | | | | | 4932 |
| HPV31 | E1 | YANSKSHFWL | 481 | 10 | | | | | 4933 |
| HPV31 | E1 | YAQLADSDSNA | 359 | 11 | | | | | 4934 |
| HPV31 | E1 | YIDNYLRNA | 511 | 9 | | | | | 4935 |
| HPV31 | E1 | YIDNYLRNAL | 511 | 10 | | | | | 4936 |
| HPV31 | E1 | YLHSRLVV | 558 | 8 | | | | | 4937 |
| HPV31 | E1 | YLHSRLVVFT | 558 | 10 | | | | | 4938 |
| HPV31 | E1 | YLRNALDGNPV | 515 | 11 | | | | | 4939 |
| HPV31 | E1 | YQQIEFVSFL | 428 | 10 | | | | | 4940 |
| HPV31 | E1 | YVEAVIDRQT | 19 | 10 | | | | | 4941 |
| HPV31 | E1 | YVGSPLSDI | 89 | 9 | | | | | 4942 |
| HPV31 | E2 | AAACTNQT | 277 | 8 | | | | | 4943 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E2 | AAACTNQTRA | 277 | 10 | | | | | 4944 |
| HPV31 | E2 | AAACTNQTRAV | 277 | 11 | | | | | 4945 |
| HPV31 | E2 | AACTNQTRA | 278 | 9 | | | | | 4946 |
| HPV31 | E2 | AACTNQTRAV | 278 | 10 | | | | | 4947 |
| HPV31 | E2 | AIELQMML | 72 | 8 | | | | | 4948 |
| HPV31 | E2 | AIELQMMLET | 72 | 10 | | | | | 4949 |
| HPV31 | E2 | AIELQMMLETL | 72 | 11 | | | | | 4950 |
| HPV31 | E2 | AIVTLTYI | 338 | 8 | | | | | 4951 |
| HPV31 | E2 | AIVTLTYIST | 338 | 10 | | | | | 4952 |
| HPV31 | E2 | ALGTSEGV | 229 | 8 | | | | | 4953 |
| HPV31 | E2 | ALGTSEGVRRA | 229 | 11 | | | | | 4954 |
| HPV31 | E2 | ALQAIELQM | 69 | 9 | | | | | 4955 |
| HPV31 | E2 | ALQAIELQMM | 69 | 10 | | | | | 4956 |
| HPV31 | E2 | ALQAIELQMML | 69 | 11 | | | | | 4957 |
| HPV31 | E2 | ALSVSKAKA | 61 | 9 | | | | | 4958 |
| HPV31 | E2 | ALSVSKAKAL | 61 | 10 | | | | | 4959 |
| HPV31 | E2 | ATTPIIHL | 291 | 8 | | | | | 4960 |
| HPV31 | E2 | ATTSTKRPRT | 239 | 10 | | | | | 4961 |
| HPV31 | E2 | AVSCPATT | 286 | 8 | | | | | 4962 |
| HPV31 | E2 | AVSCPATTPI | 286 | 10 | | | | | 4963 |
| HPV31 | E2 | AVSCPATTPII | 286 | 11 | | | | | 4964 |
| HPV31 | E2 | CALGTSEGV | 228 | 9 | | | | | 4965 |
| HPV31 | E2 | CIDGQCTV | 140 | 8 | | | | | 4966 |
| HPV31 | E2 | CIDGQCTVV | 140 | 9 | | | | | 4967 |
| HPV31 | E2 | CLKKHGYT | 109 | 8 | | | | | 4968 |
| HPV31 | E2 | CLKKHGYTV | 109 | 9 | | | | | 4969 |
| HPV31 | E2 | CLKKHGYTVEV | 109 | 11 | | | | | 4970 |
| HPV31 | E2 | CTDGKHKNA | 330 | 9 | | | | | 4971 |
| HPV31 | E2 | CTDGKHKNAI | 330 | 10 | | | | | 4972 |
| HPV31 | E2 | CTDGKHKNAIV | 330 | 11 | | | | | 4973 |
| HPV31 | E2 | CTNQTRAV | 280 | 8 | | | | | 4974 |
| HPV31 | E2 | CTVVEGQV | 145 | 8 | | | | | 4975 |
| HPV31 | E2 | CVLMYKAREM | 40 | 10 | | | | | 4976 |
| HPV31 | E2 | DANILKCL | 301 | 8 | | | | | 4977 |
| HPV31 | E2 | DVHNTMHYT | 124 | 9 | | | | | 4978 |
| HPV31 | E2 | EISFAGIV | 204 | 8 | | | | | 4979 |
| HPV31 | E2 | EISFAGIVT | 204 | 9 | | | | | 4980 |
| HPV31 | E2 | EISFAGIVTKL | 204 | 11 | | | | | 4981 |
| HPV31 | E2 | ELQMMLET | 74 | 8 | | | | | 4982 |
| HPV31 | E2 | ELQMMLETL | 74 | 9 | | | | | 4983 |
| HPV31 | E2 | ELYLTAPT | 100 | 8 | | | | | 4984 |
| HPV31 | E2 | ELYLTAPTGCL | 100 | 11 | | | | | 4985 |
| HPV31 | E2 | EMGIHSINHQV | 48 | 11 | | | | | 4986 |
| HPV31 | E2 | EQVSSTWHWT | 320 | 10 | | | | | 4987 |
| HPV31 | E2 | ETLSQRLNV | 2 | 9 | | | | | 4988 |
| HPV31 | E2 | EVHAGGQV | 185 | 8 | | | | | 4989 |
| HPV31 | E2 | EVHAGGQVI | 185 | 9 | | | | | 4990 |
| HPV31 | E2 | EVHAGGQVIV | 185 | 10 | | | | | 4991 |
| HPV31 | E2 | EVQFDGDV | 118 | 8 | | | | | 4992 |
| HPV31 | E2 | EVQFDGDVHNT | 118 | 11 | | | | | 4993 |
| HPV31 | E2 | FAGIVTKL | 207 | 8 | | | | | 4994 |
| HPV31 | E2 | FAGIVTKLPT | 207 | 10 | | | | | 4995 |
| HPV31 | E2 | FAGIVTKLPTA | 207 | 11 | | | | | 4996 |
| HPV31 | E2 | FIYLCIDGQCT | 136 | 11 | | | | | 4997 |
| HPV31 | E2 | FLNTVKIPNT | 353 | 10 | | | | | 4998 |
| HPV31 | E2 | FLNTVKIPNTV | 353 | 11 | | | | | 4999 |
| HPV31 | E2 | FTEEAKKYGT | 171 | 10 | | | | | 5000 |
| HPV31 | E2 | FVNFTEEA | 168 | 8 | | | | | 5001 |
| HPV31 | E2 | GIHSINHQV | 50 | 9 | | | | | 5002 |
| HPV31 | E2 | GIHSINHQVV | 50 | 10 | | | | | 5003 |
| HPV31 | E2 | GIVTKLPT | 209 | 8 | | | | | 5004 |
| HPV31 | E2 | GIVTKLPTA | 209 | 9 | | | | | 5005 |
| HPV31 | E2 | GIYYVHEGHI | 156 | 10 | | | | | 5006 |
| HPV31 | E2 | GIYYVHEGHIT | 156 | 11 | | | | | 5007 |
| HPV31 | E2 | GQCTVVEGQV | 143 | 10 | | | | | 5008 |
| HPV31 | E2 | GQVIVFPESV | 190 | 10 | | | | | 5009 |
| HPV31 | E2 | GQVNCKGI | 150 | 8 | | | | | 5010 |
| HPV31 | E2 | GQVNCKGIYYV | 150 | 11 | | | | | 5011 |
| HPV31 | E2 | GTGKKWEV | 179 | 8 | | | | | 5012 |
| HPV31 | E2 | GTGKKWEVHA | 179 | 10 | | | | | 5013 |
| HPV31 | E2 | GTSEGVRRA | 231 | 9 | | | | | 5014 |
| HPV31 | E2 | GTSEGVRRAT | 231 | 10 | | | | | 5015 |
| HPV31 | E2 | GTSEGVRRATT | 231 | 11 | | | | | 5016 |
| HPV31 | E2 | GVISAAACT | 273 | 9 | | | | | 5017 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E2 | GVRRATTST | 235 | 9 | | | | | 5018 |
| HPV31 | E2 | HAGGQVIV | 187 | 8 | | | | | 5019 |
| HPV31 | E2 | HIDYWKHI | 29 | 8 | | | | | 5020 |
| HPV31 | E2 | HIDYWKHIRL | 29 | 10 | | | | | 5021 |
| HPV31 | E2 | HIRLECVL | 35 | 8 | | | | | 5022 |
| HPV31 | E2 | HIRLECVLM | 35 | 9 | | | | | 5023 |
| HPV31 | E2 | HITYFVNFT | 164 | 9 | | | | | 5024 |
| HPV31 | E2 | HLKGDANI | 297 | 8 | | | | | 5025 |
| HPV31 | E2 | HLKGDANIL | 297 | 9 | | | | | 5026 |
| HPV31 | E2 | HQVVPALSV | 56 | 9 | | | | | 5027 |
| HPV31 | E2 | IIHLKGDA | 295 | 8 | | | | | 5028 |
| HPV31 | E2 | IIHLKGDANI | 295 | 10 | | | | | 5029 |
| HPV31 | E2 | IIHLKGDANIL | 295 | 11 | | | | | 5030 |
| HPV31 | E2 | ILKCLRYRL | 304 | 9 | | | | | 5031 |
| HPV31 | E2 | ITYFVNFT | 165 | 8 | | | | | 5032 |
| HPV31 | E2 | ITYFVNFTEEA | 165 | 11 | | | | | 5033 |
| HPV31 | E2 | IVTKLPTA | 210 | 8 | | | | | 5034 |
| HPV31 | E2 | IVTKLPTANNT | 210 | 11 | | | | | 5035 |
| HPV31 | E2 | IVTLTYIST | 339 | 9 | | | | | 5036 |
| HPV31 | E2 | KAKALQAI | 66 | 8 | | | | | 5037 |
| HPV31 | E2 | KAKALQAIEL | 66 | 10 | | | | | 5038 |
| HPV31 | E2 | KALQAIEL | 68 | 8 | | | | | 5039 |
| HPV31 | E2 | KALQAIELQM | 68 | 10 | | | | | 5040 |
| HPV31 | E2 | KALQAIELQMM | 68 | 11 | | | | | 5041 |
| HPV31 | E2 | KAREMGIHSI | 45 | 10 | | | | | 5042 |
| HPV31 | E2 | KIPNTVSV | 358 | 8 | | | | | 5043 |
| HPV31 | E2 | KIPNTVSVST | 358 | 10 | | | | | 5044 |
| HPV31 | E2 | KLLRGDSV | 260 | 8 | | | | | 5045 |
| HPV31 | E2 | KLLRGDSVDSV | 260 | 11 | | | | | 5046 |
| HPV31 | E2 | KLPTANNT | 213 | 8 | | | | | 5047 |
| HPV31 | E2 | KLPTANNTT | 213 | 9 | | | | | 5048 |
| HPV31 | E2 | KLPTANNTTT | 213 | 10 | | | | | 5049 |
| HPV31 | E2 | KQLYEQVSST | 316 | 10 | | | | | 5050 |
| HPV31 | E2 | KTCALGTSEGV | 226 | 11 | | | | | 5051 |
| HPV31 | E2 | LLRGDSVDSV | 261 | 10 | | | | | 5052 |
| HPV31 | E2 | LMYKAREM | 42 | 8 | | | | | 5053 |
| HPV31 | E2 | LMYKAREMGI | 42 | 10 | | | | | 5054 |
| HPV31 | E2 | LQAIELQM | 70 | 8 | | | | | 5055 |
| HPV31 | E2 | LQAIELQMM | 70 | 9 | | | | | 5056 |
| HPV31 | E2 | LQAIELQMML | 70 | 10 | | | | | 5057 |
| HPV31 | E2 | LQMMLETL | 75 | 8 | | | | | 5058 |
| HPV31 | E2 | LQMMLETLNNT | 75 | 11 | | | | | 5059 |
| HPV31 | E2 | LTAPTGCL | 103 | 8 | | | | | 5060 |
| HPV31 | E2 | MLETLNNT | 78 | 8 | | | | | 5061 |
| HPV31 | E2 | MMLETLNNT | 77 | 9 | | | | | 5062 |
| HPV31 | E2 | MQQTSLEL | 94 | 8 | | | | | 5063 |
| HPV31 | E2 | MQQTSLELYL | 94 | 10 | | | | | 5064 |
| HPV31 | E2 | MQQTSLELYLT | 94 | 11 | | | | | 5065 |
| HPV31 | E2 | NAIVTLTYI | 337 | 9 | | | | | 5066 |
| HPV31 | E2 | NAIVTLTYIST | 337 | 11 | | | | | 5067 |
| HPV31 | E2 | NILKCLRYRL | 303 | 10 | | | | | 5068 |
| HPV31 | E2 | NQTRAVSCPA | 282 | 10 | | | | | 5069 |
| HPV31 | E2 | NQTRAVSCPAT | 282 | 11 | | | | | 5070 |
| HPV31 | E2 | NTEYKNEDWT | 84 | 10 | | | | | 5071 |
| HPV31 | E2 | NTEYKNEDWTM | 84 | 11 | | | | | 5072 |
| HPV31 | E2 | NTHHPNKL | 254 | 8 | | | | | 5073 |
| HPV31 | E2 | NTHHPNKLL | 254 | 9 | | | | | 5074 |
| HPV31 | E2 | NTMHYTNWKFI | 127 | 11 | | | | | 5075 |
| HPV31 | E2 | NTTTSNSKT | 219 | 9 | | | | | 5076 |
| HPV31 | E2 | NTTTSNSKTCA | 219 | 11 | | | | | 5077 |
| HPV31 | E2 | NTVKIPNT | 355 | 8 | | | | | 5078 |
| HPV31 | E2 | NTVKIPNTV | 355 | 9 | | | | | 5079 |
| HPV31 | E2 | NTVKIPNTVSV | 355 | 11 | | | | | 5080 |
| HPV31 | E2 | NTVSVSTGYM | 361 | 10 | | | | | 5081 |
| HPV31 | E2 | NTVSVSTGYMT | 361 | 11 | | | | | 5082 |
| HPV31 | E2 | NVCQDKIL | 9 | 8 | | | | | 5083 |
| HPV31 | E2 | PALSVSKA | 60 | 8 | | | | | 5084 |
| HPV31 | E2 | PALSVSKAKA | 60 | 10 | | | | | 5085 |
| HPV31 | E2 | PALSVSKAKAL | 60 | 11 | | | | | 5086 |
| HPV31 | E2 | PATTPIIHL | 290 | 9 | | | | | 5087 |
| HPV31 | E2 | PIIHLKGDA | 294 | 9 | | | | | 5088 |
| HPV31 | E2 | PIIHLKGDANI | 294 | 11 | | | | | 5089 |
| HPV31 | E2 | PTANNTTT | 215 | 8 | | | | | 5090 |
| HPV31 | E2 | PTGCLKKHGYT | 106 | 11 | | | | | 5091 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E2 | QAIELQMM | 71 | 8 | | | | | 5092 |
| HPV31 | E2 | QAIELQMML | 71 | 9 | | | | | 5093 |
| HPV31 | E2 | QAIELQMMLET | 71 | 11 | | | | | 5094 |
| HPV31 | E2 | QLYEQVSST | 317 | 9 | | | | | 5095 |
| HPV31 | E2 | QMMLETLNNT | 76 | 10 | | | | | 5096 |
| HPV31 | E2 | QQTSLELYL | 95 | 9 | | | | | 5097 |
| HPV31 | E2 | QQTSLELYLT | 95 | 10 | | | | | 5098 |
| HPV31 | E2 | QQTSLELYLTA | 95 | 11 | | | | | 5099 |
| HPV31 | E2 | QTRAVSCPA | 283 | 9 | | | | | 5100 |
| HPV31 | E2 | QTRAVSCPAT | 283 | 10 | | | | | 5101 |
| HPV31 | E2 | QTRAVSCPATT | 283 | 11 | | | | | 5102 |
| HPV31 | E2 | QTSLELYL | 96 | 8 | | | | | 5103 |
| HPV31 | E2 | QTSLELYLT | 96 | 9 | | | | | 5104 |
| HPV31 | E2 | QTSLELYLTA | 96 | 10 | | | | | 5105 |
| HPV31 | E2 | QVIVFPESV | 191 | 9 | | | | | 5106 |
| HPV31 | E2 | QVNCKGIYYV | 151 | 10 | | | | | 5107 |
| HPV31 | E2 | QVSSTWHWT | 321 | 9 | | | | | 5108 |
| HPV31 | E2 | QVSSTWHWTCT | 321 | 11 | | | | | 5109 |
| HPV31 | E2 | QVVPALSV | 57 | 8 | | | | | 5110 |
| HPV31 | E2 | QVVPALSVSKA | 57 | 11 | | | | | 5111 |
| HPV31 | E2 | RATTSTKRPRT | 238 | 11 | | | | | 5112 |
| HPV31 | E2 | RAVSCPAT | 285 | 8 | | | | | 5113 |
| HPV31 | E2 | RAVSCPATT | 285 | 9 | | | | | 5114 |
| HPV31 | E2 | RAVSCPATTPI | 285 | 11 | | | | | 5115 |
| HPV31 | E2 | RLECVLMYKA | 37 | 10 | | | | | 5116 |
| HPV31 | E2 | RLNVCQDKI | 7 | 9 | | | | | 5117 |
| HPV31 | E2 | RLNVCQDKIL | 7 | 10 | | | | | 5118 |
| HPV31 | E2 | RLSKYKQL | 311 | 8 | | | | | 5119 |
| HPV31 | E2 | RTEPEHRNT | 247 | 9 | | | | | 5120 |
| HPV31 | E2 | SAAACTNQT | 276 | 9 | | | | | 5121 |
| HPV31 | E2 | SAAACTNQTRA | 276 | 11 | | | | | 5122 |
| HPV31 | E2 | SINHQVVPA | 53 | 9 | | | | | 5123 |
| HPV31 | E2 | SINHQVVPAL | 53 | 10 | | | | | 5124 |
| HPV31 | E2 | SLELYLTA | 98 | 8 | | | | | 5125 |
| HPV31 | E2 | SLELYLTAPT | 98 | 10 | | | | | 5126 |
| HPV31 | E2 | SQRDDFLNT | 348 | 9 | | | | | 5127 |
| HPV31 | E2 | SQRDDFLNTV | 348 | 10 | | | | | 5128 |
| HPV31 | E2 | SQRLNVCQDKI | 5 | 11 | | | | | 5129 |
| HPV31 | E2 | STSQRDDFL | 346 | 9 | | | | | 5130 |
| HPV31 | E2 | STSQRDDFLNT | 346 | 11 | | | | | 5131 |
| HPV31 | E2 | STWHWTCT | 324 | 8 | | | | | 5132 |
| HPV31 | E2 | SVDSVNCGV | 266 | 9 | | | | | 5133 |
| HPV31 | E2 | SVDSVNCGVI | 266 | 10 | | | | | 5134 |
| HPV31 | E2 | SVFSSDEI | 198 | 8 | | | | | 5135 |
| HPV31 | E2 | SVFSSDEISFA | 198 | 11 | | | | | 5136 |
| HPV31 | E2 | SVNCGVISA | 269 | 9 | | | | | 5137 |
| HPV31 | E2 | SVNCGVISAA | 269 | 10 | | | | | 5138 |
| HPV31 | E2 | SVNCGVISAAA | 269 | 11 | | | | | 5139 |
| HPV31 | E2 | SVSKAKAL | 63 | 8 | | | | | 5140 |
| HPV31 | E2 | SVSKAKALQA | 63 | 10 | | | | | 5141 |
| HPV31 | E2 | SVSKAKALQAI | 63 | 11 | | | | | 5142 |
| HPV31 | E2 | SVSTGYMT | 364 | 8 | | | | | 5143 |
| HPV31 | E2 | SVSTGYMTI | 364 | 9 | | | | | 5144 |
| HPV31 | E2 | TLSQRLNV | 3 | 8 | | | | | 5145 |
| HPV31 | E2 | TMHYTNWKFI | 128 | 10 | | | | | 5146 |
| HPV31 | E2 | TMQQTSLEL | 93 | 9 | | | | | 5147 |
| HPV31 | E2 | TMQQTSLELYL | 93 | 11 | | | | | 5148 |
| HPV31 | E2 | TTPIIHLKGDA | 292 | 11 | | | | | 5149 |
| HPV31 | E2 | TTSNSKTCA | 221 | 9 | | | | | 5150 |
| HPV31 | E2 | TTSNSKTCAL | 221 | 10 | | | | | 5151 |
| HPV31 | E2 | TTSTKRPRT | 240 | 9 | | | | | 5152 |
| HPV31 | E2 | TTTSNSKT | 220 | 8 | | | | | 5153 |
| HPV31 | E2 | TTTSNSKTCA | 220 | 10 | | | | | 5154 |
| HPV31 | E2 | TTTSNSKTCAL | 220 | 11 | | | | | 5155 |
| HPV31 | E2 | TVEVQFDGDV | 116 | 10 | | | | | 5156 |
| HPV31 | E2 | TVKIPNTV | 356 | 8 | | | | | 5157 |
| HPV31 | E2 | TVKIPNTVSV | 356 | 10 | | | | | 5158 |
| HPV31 | E2 | TVSVSTGYM | 362 | 9 | | | | | 5159 |
| HPV31 | E2 | TVSVSTGYMT | 362 | 10 | | | | | 5160 |
| HPV31 | E2 | TVSVSTGYMTI | 362 | 11 | | | | | 5161 |
| HPV31 | E2 | VISAAACT | 274 | 8 | | | | | 5162 |
| HPV31 | E2 | VISAAACTNQT | 274 | 11 | | | | | 5163 |
| HPV31 | E2 | VIVFPESV | 192 | 8 | | | | | 5164 |
| HPV31 | E2 | VLMYKAREM | 41 | 9 | | | | | 5165 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E2 | VLMYKAREMGI | 41 | 11 | | | | | 5166 |
| HPV31 | E2 | VQFDGDVHNT | 119 | 10 | | | | | 5167 |
| HPV31 | E2 | VQFDGDVHNTM | 119 | 11 | | | | | 5168 |
| HPV31 | E2 | VTKLPTANNT | 211 | 10 | | | | | 5169 |
| HPV31 | E2 | VTKLPTANNTT | 211 | 11 | | | | | 5170 |
| HPV31 | E2 | VTLTYIST | 340 | 8 | | | | | 5171 |
| HPV31 | E2 | VVEGQVNCKGI | 147 | 11 | | | | | 5172 |
| HPV31 | E2 | VVPALSVSKA | 58 | 10 | | | | | 5173 |
| HPV31 | E2 | WTCTDGKHKNA | 328 | 11 | | | | | 5174 |
| HPV31 | E2 | WTMQQTSL | 92 | 8 | | | | | 5175 |
| HPV31 | E2 | WTMQQTSLEL | 92 | 10 | | | | | 5176 |
| HPV31 | E2 | YISTSQRDDFL | 344 | 11 | | | | | 5177 |
| HPV31 | E2 | YLCIDGQCT | 138 | 9 | | | | | 5178 |
| HPV31 | E2 | YLCIDGQCTV | 138 | 10 | | | | | 5179 |
| HPV31 | E2 | YLCIDGQCTVV | 138 | 11 | | | | | 5180 |
| HPV31 | E2 | YLTAPTGCL | 102 | 9 | | | | | 5181 |
| HPV31 | E2 | YTNWKFIYL | 131 | 9 | | | | | 5182 |
| HPV31 | E2 | YTNWKFIYLCI | 131 | 11 | | | | | 5183 |
| HPV31 | E2 | YTVEVQFDGDV | 115 | 11 | | | | | 5184 |
| HPV31 | E2 | YVHEGHIT | 159 | 8 | | | | | 5185 |
| HPV31 | E2 | YVHEGHITYFV | 159 | 11 | | | | | 5186 |
| HPV31 | E5 | ATLLLLIV | 40 | 8 | | | | | 5187 |
| HPV31 | E5 | ATLLLLIVI | 40 | 9 | | | | | 5188 |
| HPV31 | E5 | ATLLLLIVIL | 40 | 10 | | | | | 5189 |
| HPV31 | E5 | ATSPLRCFCI | 53 | 10 | | | | | 5190 |
| HPV31 | E5 | CIYVVFIYI | 61 | 9 | | | | | 5191 |
| HPV31 | E5 | CIYVVFIYIPL | 61 | 11 | | | | | 5192 |
| HPV31 | E5 | CLVIRPLV | 26 | 8 | | | | | 5193 |
| HPV31 | E5 | CLVIRPLVL | 26 | 9 | | | | | 5194 |
| HPV31 | E5 | CLVIRPLVLSV | 26 | 11 | | | | | 5195 |
| HPV31 | E5 | CVLLFVCL | 20 | 8 | | | | | 5196 |
| HPV31 | E5 | CVLLFVCLV | 20 | 9 | | | | | 5197 |
| HPV31 | E5 | CVLLFVCLVI | 20 | 10 | | | | | 5198 |
| HPV31 | E5 | ELNISTVSI | 3 | 9 | | | | | 5199 |
| HPV31 | E5 | ELNISTVSIV | 3 | 10 | | | | | 5200 |
| HPV31 | E5 | ELNISTVSIVL | 3 | 11 | | | | | 5201 |
| HPV31 | E5 | FIYIPLFV | 66 | 8 | | | | | 5202 |
| HPV31 | E5 | FIYIPLFVI | 66 | 9 | | | | | 5203 |
| HPV31 | E5 | FIYIPLFVIHT | 66 | 11 | | | | | 5204 |
| HPV31 | E5 | FLLCFCVL | 15 | 8 | | | | | 5205 |
| HPV31 | E5 | FLLCFCVLL | 15 | 9 | | | | | 5206 |
| HPV31 | E5 | FLLCFCVLLFV | 15 | 11 | | | | | 5207 |
| HPV31 | E5 | FVCLVIRPL | 24 | 9 | | | | | 5208 |
| HPV31 | E5 | FVCLVIRPLV | 24 | 10 | | | | | 5209 |
| HPV31 | E5 | FVCLVIRPLVL | 24 | 11 | | | | | 5210 |
| HPV31 | E5 | FVIHTHASFL | 72 | 10 | | | | | 5211 |
| HPV31 | E5 | IATSPLRCFCI | 52 | 11 | | | | | 5212 |
| HPV31 | E5 | ILWVIATSPL | 48 | 10 | | | | | 5213 |
| HPV31 | E5 | IVILWVIA | 46 | 8 | | | | | 5214 |
| HPV31 | E5 | IVILWVIAT | 46 | 9 | | | | | 5215 |
| HPV31 | E5 | IVLCFLLCFCV | 11 | 11 | | | | | 5216 |
| HPV31 | E5 | LIVILWVI | 45 | 8 | | | | | 5217 |
| HPV31 | E5 | LIVILWVIA | 45 | 9 | | | | | 5218 |
| HPV31 | E5 | LIVILWVIAT | 45 | 10 | | | | | 5219 |
| HPV31 | E5 | LLCFCVLL | 16 | 8 | | | | | 5220 |
| HPV31 | E5 | LLCFCVLLFV | 16 | 10 | | | | | 5221 |
| HPV31 | E5 | LLFVCLVI | 22 | 8 | | | | | 5222 |
| HPV31 | E5 | LLFVCLVIRPL | 22 | 11 | | | | | 5223 |
| HPV31 | E5 | LLIVILWV | 44 | 8 | | | | | 5224 |
| HPV31 | E5 | LLIVILWVI | 44 | 9 | | | | | 5225 |
| HPV31 | E5 | LLIVILWVIA | 44 | 10 | | | | | 5226 |
| HPV31 | E5 | LLIVILWVIAT | 44 | 11 | | | | | 5227 |
| HPV31 | E5 | LLLIVILWV | 43 | 9 | | | | | 5228 |
| HPV31 | E5 | LLLIVILWVI | 43 | 10 | | | | | 5229 |
| HPV31 | E5 | LLLIVILWVIA | 43 | 11 | | | | | 5230 |
| HPV31 | E5 | LLLLIVIL | 42 | 8 | | | | | 5231 |
| HPV31 | E5 | LLLLIVILWV | 42 | 10 | | | | | 5232 |
| HPV31 | E5 | LLLLIVILWVI | 42 | 11 | | | | | 5233 |
| HPV31 | E5 | LVIRPLVL | 27 | 8 | | | | | 5234 |
| HPV31 | E5 | LVIRPLVLSV | 27 | 10 | | | | | 5235 |
| HPV31 | E5 | LVLSVSVYA | 32 | 9 | | | | | 5236 |
| HPV31 | E5 | LVLSVSVYAT | 32 | 10 | | | | | 5237 |
| HPV31 | E5 | LVLSVSVYATL | 32 | 11 | | | | | 5238 |
| HPV31 | E5 | MIELNIST | 1 | 8 | | | | | 5239 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E5 | MIELNISTV | 1 | 9 | | | | | 5240 |
| HPV31 | E5 | MIELNISTVSI | 1 | 11 | | | | | 5241 |
| HPV31 | E5 | NISTVSIV | 5 | 8 | | | | | 5242 |
| HPV31 | E5 | NISTVSIVL | 5 | 9 | | | | | 5243 |
| HPV31 | E5 | PLFVIHTHA | 70 | 9 | | | | | 5244 |
| HPV31 | E5 | PLRCFCIYV | 56 | 9 | | | | | 5245 |
| HPV31 | E5 | PLRCFCIYVV | 56 | 10 | | | | | 5246 |
| HPV31 | E5 | PLVLSVSV | 31 | 8 | | | | | 5247 |
| HPV31 | E5 | PLVLSVSVYA | 31 | 10 | | | | | 5248 |
| HPV31 | E5 | PLVLSVSVYAT | 31 | 11 | | | | | 5249 |
| HPV31 | E5 | SIVLCFLL | 10 | 8 | | | | | 5250 |
| HPV31 | E5 | STVSIVLCFL | 7 | 10 | | | | | 5251 |
| HPV31 | E5 | STVSIVLCFLL | 7 | 11 | | | | | 5252 |
| HPV31 | E5 | SVSVYATL | 35 | 8 | | | | | 5253 |
| HPV31 | E5 | SVSVYATLL | 35 | 9 | | | | | 5254 |
| HPV31 | E5 | SVSVYATLLL | 35 | 10 | | | | | 5255 |
| HPV31 | E5 | SVSVYATLLLL | 35 | 11 | | | | | 5256 |
| HPV31 | E5 | SVYATLLL | 37 | 8 | | | | | 5257 |
| HPV31 | E5 | SVYATLLLL | 37 | 9 | | | | | 5258 |
| HPV31 | E5 | SVYATLLLLI | 37 | 10 | | | | | 5259 |
| HPV31 | E5 | SVYATLLLLIV | 37 | 11 | | | | | 5260 |
| HPV31 | E5 | TLLLLIVI | 41 | 8 | | | | | 5261 |
| HPV31 | E5 | TLLLLIVIL | 41 | 9 | | | | | 5262 |
| HPV31 | E5 | TLLLLIVILWV | 41 | 11 | | | | | 5263 |
| HPV31 | E5 | TVSIVLCFL | 8 | 9 | | | | | 5264 |
| HPV31 | E5 | TVSIVLCFLL | 8 | 10 | | | | | 5265 |
| HPV31 | E5 | VIHTHASFL | 73 | 9 | | | | | 5266 |
| HPV31 | E5 | VILWVIAT | 47 | 8 | | | | | 5267 |
| HPV31 | E5 | VILWVIATSPL | 47 | 11 | | | | | 5268 |
| HPV31 | E5 | VIRPLVLSV | 28 | 9 | | | | | 5269 |
| HPV31 | E5 | VIRPLVLSVSV | 28 | 11 | | | | | 5270 |
| HPV31 | E5 | VLCFLLCFCV | 12 | 10 | | | | | 5271 |
| HPV31 | E5 | VLCFLLCFCVL | 12 | 11 | | | | | 5272 |
| HPV31 | E5 | VLLFVCLV | 21 | 8 | | | | | 5273 |
| HPV31 | E5 | VLLFVCLVI | 21 | 9 | | | | | 5274 |
| HPV31 | E5 | VLSVSVYA | 33 | 8 | | | | | 5275 |
| HPV31 | E5 | VLSVSVYAT | 33 | 9 | | | | | 5276 |
| HPV31 | E5 | VLSVSVYATL | 33 | 10 | | | | | 5277 |
| HPV31 | E5 | VLSVSVYATLL | 33 | 11 | | | | | 5278 |
| HPV31 | E5 | VVFIYIPL | 64 | 8 | | | | | 5279 |
| HPV31 | E5 | VVFIYIPLFV | 64 | 10 | | | | | 5280 |
| HPV31 | E5 | VVFIYIPLFVI | 64 | 11 | | | | | 5281 |
| HPV31 | E5 | WVIATSPL | 50 | 8 | | | | | 5282 |
| HPV31 | E5 | YATLLLLI | 39 | 8 | | | | | 5283 |
| HPV31 | E5 | YATLLLLIV | 39 | 9 | | | | | 5284 |
| HPV31 | E5 | YATLLLLIVI | 39 | 10 | | | | | 5285 |
| HPV31 | E5 | YATLLLLIVIL | 39 | 11 | | | | | 5286 |
| HPV31 | E5 | YIPLFVIHT | 68 | 9 | | | | | 5287 |
| HPV31 | E5 | YIPLFVIHTHA | 68 | 11 | | | | | 5288 |
| HPV31 | E5 | YVVFIYIPL | 63 | 9 | | | | | 5289 |
| HPV31 | E5 | YVVFIYIPLFV | 63 | 11 | | | | | 5290 |
| HPV31 | E6 | ALEIPYDEL | 18 | 9 | | | | | 5291 |
| HPV31 | E6 | ALEIPYDELRL | 18 | 11 | | | | | 5292 |
| HPV31 | E6 | CIACWRRPRT | 136 | 10 | | | | | 5293 |
| HPV31 | E6 | CITCQRPL | 103 | 8 | | | | | 5294 |
| HPV31 | E6 | CLRFYSKV | 66 | 8 | | | | | 5295 |
| HPV31 | E6 | CTKCLRFYSKV | 63 | 11 | | | | | 5296 |
| HPV31 | E6 | CVYCKGQL | 30 | 8 | | | | | 5297 |
| HPV31 | E6 | CVYCKGQLT | 30 | 9 | | | | | 5298 |
| HPV31 | E6 | CVYCKGQLTET | 30 | 11 | | | | | 5299 |
| HPV31 | E6 | DLLIRCIT | 98 | 8 | | | | | 5300 |
| HPV31 | E6 | DLTIVYRDDT | 49 | 10 | | | | | 5301 |
| HPV31 | E6 | DTPHGVCT | 57 | 8 | | | | | 5302 |
| HPV31 | E6 | DTPHGVCTKCL | 57 | 11 | | | | | 5303 |
| HPV31 | E6 | EIPYDELRL | 20 | 9 | | | | | 5304 |
| HPV31 | E6 | ELSSALEI | 14 | 8 | | | | | 5305 |
| HPV31 | E6 | ETEVLDFA | 39 | 8 | | | | | 5306 |
| HPV31 | E6 | ETEVLDFAFT | 39 | 10 | | | | | 5307 |
| HPV31 | E6 | EVLDFAFT | 41 | 8 | | | | | 5308 |
| HPV31 | E6 | EVLDFAFTDL | 41 | 10 | | | | | 5309 |
| HPV31 | E6 | EVLDFAFTDLT | 41 | 11 | | | | | 5310 |
| HPV31 | E6 | FAFTDLTI | 45 | 8 | | | | | 5311 |
| HPV31 | E6 | FAFTDLTIV | 45 | 9 | | | | | 5312 |
| HPV31 | E6 | GICDLLIRCI | 95 | 10 | | | | | 5313 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E6 | GICDLLIRCIT | 95 | 11 | | | | | 5314 |
| HPV31 | E6 | GQLTETEV | 35 | 8 | | | | | 5315 |
| HPV31 | E6 | GQLTETEVL | 35 | 9 | | | | | 5316 |
| HPV31 | E6 | GTTLEKLT | 85 | 8 | | | | | 5317 |
| HPV31 | E6 | HLDKKKRFHNI | 118 | 11 | | | | | 5318 |
| HPV31 | E6 | IACWRRPRT | 137 | 9 | | | | | 5319 |
| HPV31 | E6 | IACWRRPRTET | 137 | 11 | | | | | 5320 |
| HPV31 | E6 | IVYRDDTPHGV | 52 | 11 | | | | | 5321 |
| HPV31 | E6 | KLHELSSA | 11 | 8 | | | | | 5322 |
| HPV31 | E6 | KLHELSSAL | 11 | 9 | | | | | 5323 |
| HPV31 | E6 | KLHELSSALEI | 11 | 11 | | | | | 5324 |
| HPV31 | E6 | KLTNKGICDL | 90 | 10 | | | | | 5325 |
| HPV31 | E6 | KLTNKGICDLL | 90 | 11 | | | | | 5326 |
| HPV31 | E6 | LIRCITCQRPL | 100 | 11 | | | | | 5327 |
| HPV31 | E6 | LTETEVLDFA | 37 | 10 | | | | | 5328 |
| HPV31 | E6 | LTIVYRDDT | 50 | 9 | | | | | 5329 |
| HPV31 | E6 | LTNKGICDL | 91 | 9 | | | | | 5330 |
| HPV31 | E6 | LTNKGICDLL | 91 | 10 | | | | | 5331 |
| HPV31 | E6 | LTNKGICDLLI | 91 | 11 | | | | | 5332 |
| HPV31 | E6 | NIGGRWTGRCI | 127 | 11 | | | | | 5333 |
| HPV31 | E6 | PAERPRKL | 5 | 8 | | | | | 5334 |
| HPV31 | E6 | PAERPRKLHEL | 5 | 11 | | | | | 5335 |
| HPV31 | E6 | PLCPEEKQRHL | 109 | 11 | 0.0001 | | | | 5336 |
| HPV31 | E6 | QLTETEVL | 36 | 8 | | | | | 5337 |
| HPV31 | E6 | QLTETEVLDFA | 36 | 11 | | | | | 5338 |
| HPV31 | E6 | RLNCVYCKGQL | 27 | 11 | | | | | 5339 |
| HPV31 | E6 | SALEIPYDEL | 17 | 10 | | | | | 5340 |
| HPV31 | E6 | SVYGTTLEKL | 82 | 10 | | | | | 5341 |
| HPV31 | E6 | SVYGTTLEKLT | 82 | 11 | | | | | 5342 |
| HPV31 | E6 | TIVYRDDT | 51 | 8 | | | | | 5343 |
| HPV31 | E6 | TLEKLTNKGI | 87 | 10 | | | | | 5344 |
| HPV31 | E6 | TTLEKLTNKGI | 86 | 11 | | | | | 5345 |
| HPV31 | E6 | VLDFAFTDL | 42 | 9 | | | | | 5346 |
| HPV31 | E6 | VLDFAFTDLT | 42 | 10 | | | | | 5347 |
| HPV31 | E6 | VLDFAFTDLTI | 42 | 11 | | | | | 5348 |
| HPV31 | E7 | ATDLHCYEQL | 19 | 10 | | | | | 5349 |
| HPV31 | E7 | CQCKSTLRL | 59 | 9 | | | | | 5350 |
| HPV31 | E7 | CQCKSTLRLCV | 59 | 11 | | | | | 5351 |
| HPV31 | E7 | CVQSTQVDI | 68 | 9 | | | | | 5352 |
| HPV31 | E7 | CVQSTQVDIRI | 68 | 11 | | | | | 5353 |
| HPV31 | E7 | DIRILQEL | 75 | 8 | | | | | 5354 |
| HPV31 | E7 | DIRILQELL | 75 | 9 | | | | | 5355 |
| HPV31 | E7 | DIRILQELLM | 75 | 10 | | | | | 5356 |
| HPV31 | E7 | DLHCYEQL | 21 | 8 | | | | | 5357 |
| HPV31 | E7 | DLQPEATDL | 14 | 9 | | | | | 5358 |
| HPV31 | E7 | DTSNYNIV | 48 | 8 | | | | | 5359 |
| HPV31 | E7 | DTSNYNIVT | 48 | 9 | | | | | 5360 |
| HPV31 | E7 | DVIDSPAGQA | 36 | 10 | | | | | 5361 |
| HPV31 | E7 | EATDLHCYEQL | 18 | 11 | | | | | 5362 |
| HPV31 | E7 | ELLMGSFGI | 81 | 9 | | | | | 5363 |
| HPV31 | E7 | ELLMGSFGIV | 81 | 10 | | | | | 5364 |
| HPV31 | E7 | ETPTLQDYV | 4 | 9 | | | | | 5365 |
| HPV31 | E7 | ETPTLQDYVL | 4 | 10 | | | | | 5366 |
| HPV31 | E7 | GIVCPNCST | 88 | 9 | | | | | 5367 |
| HPV31 | E7 | GIVCPNCSTRL | 88 | 11 | | | | | 5368 |
| HPV31 | E7 | IVCPNCST | 89 | 8 | | | | | 5369 |
| HPV31 | E7 | IVCPNCSTRL | 89 | 10 | | | | | 5370 |
| HPV31 | E7 | IVTFCCQCKST | 54 | 11 | | | | | 5371 |
| HPV31 | E7 | LLMGSFGI | 82 | 8 | | | | | 5372 |
| HPV31 | E7 | LLMGSFGIV | 82 | 9 | | | | | 5373 |
| HPV31 | E7 | LMGSFGIV | 83 | 8 | | | | | 5374 |
| HPV31 | E7 | LQDYVLDL | 8 | 8 | | | | | 5375 |
| HPV31 | E7 | LQELLMGSFGI | 79 | 11 | | | | | 5376 |
| HPV31 | E7 | LQPEATDL | 15 | 8 | | | | | 5377 |
| HPV31 | E7 | PAGQAEPDT | 41 | 9 | | | | | 5378 |
| HPV31 | E7 | PTLQDYVL | 6 | 8 | | | | | 5379 |
| HPV31 | E7 | PTLQDYVLDL | 6 | 10 | | | | | 5380 |
| HPV31 | E7 | QAEPDTSNYNI | 44 | 11 | | | | | 5381 |
| HPV31 | E7 | QLPDSSEEDV | 27 | 11 | | | | | 5382 |
| HPV31 | E7 | QVDIRILQEL | 73 | 10 | | | | | 5383 |
| HPV31 | E7 | QVDIRILQELL | 73 | 11 | | | | | 5384 |
| HPV31 | E7 | RILQELLM | 77 | 8 | | | | | 5385 |
| HPV31 | E7 | RLCVQSTQV | 66 | 9 | | | | | 5386 |
| HPV31 | E7 | RLCVQSTQVDI | 66 | 11 | | | | | 5387 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | E7 | STLRLCVQST | 63 | 10 | 0.0012 | | | | 5388 |
| HPV31 | E7 | STQVDIRI | 71 | 8 | | | | | 5389 |
| HPV31 | E7 | STQVDIRIL | 71 | 9 | | | | | 5390 |
| HPV31 | E7 | TLQDYVLDL | 7 | 9 | | | | | 5391 |
| HPV31 | E7 | TLRLCVQST | 64 | 9 | 0.0061 | | | | 5392 |
| HPV31 | E7 | TLRLCVQSTQV | 64 | 11 | | | | | 5393 |
| HPV31 | E7 | TQVDIRIL | 72 | 8 | | | | | 5394 |
| HPV31 | E7 | TQVDIRILQEL | 72 | 11 | | | | | 5395 |
| HPV31 | E7 | VIDSPAGQA | 37 | 9 | | | | | 5396 |
| HPV31 | E7 | VLDLQPEA | 12 | 8 | | | | | 5397 |
| HPV31 | E7 | VLDLQPEAT | 12 | 9 | | | | | 5398 |
| HPV31 | E7 | VLDLQPEATDL | 12 | 11 | | | | | 5399 |
| HPV31 | E7 | VQSTQVDI | 69 | 8 | | | | | 5400 |
| HPV31 | E7 | VQSTQVDIRI | 69 | 10 | | | | | 5401 |
| HPV31 | E7 | VQSTQVDIRIL | 69 | 11 | | | | | 5402 |
| HPV31 | E7 | VTFCCQCKST | 55 | 10 | | | | | 5403 |
| HPV31 | E7 | VTFCCQCKSTL | 55 | 11 | | | | | 5404 |
| HPV31 | E7 | YVLDLQPEA | 11 | 9 | | | | | 5405 |
| HPV31 | E7 | YVLDLQPEAT | 11 | 10 | | | | | 5406 |
| HPV31 | L1 | AAIANSDT | 347 | 8 | | | | | 5407 |
| HPV31 | L1 | AAIANSDTT | 347 | 9 | | | | | 5408 |
| HPV31 | L1 | AIANSDTT | 348 | 8 | | | | | 5409 |
| HPV31 | L1 | AILEDWNFGL | 398 | 10 | | | | | 5410 |
| HPV31 | L1 | AILEDWNFGLT | 398 | 11 | | | | | 5411 |
| HPV31 | L1 | AITCQKTA | 426 | 8 | | | | | 5412 |
| HPV31 | L1 | AITPGDCPPL | 180 | 10 | | | | | 5413 |
| HPV31 | L1 | ALQDTKSNV | 213 | 9 | | | | | 5414 |
| HPV31 | L1 | ALQDTKSNVPL | 213 | 11 | | | | | 5415 |
| HPV31 | L1 | AMDFTALQDT | 208 | 10 | | | | | 5416 |
| HPV31 | L1 | AQGHNNGI | 317 | 8 | | | | | 5417 |
| HPV31 | L1 | AQIFNKPYWM | 305 | 10 | | | | | 5418 |
| HPV31 | L1 | ATLANSTYFPT | 285 | 11 | | | | | 5419 |
| HPV31 | L1 | ATVYLPPV | 9 | 8 | | | | | 5420 |
| HPV31 | L1 | ATVYLPPVPV | 9 | 10 | | | | | 5421 |
| HPV31 | L1 | CAAIANSDT | 346 | 9 | | | | | 5422 |
| HPV31 | L1 | CAAIANSDTT | 346 | 10 | | | | | 5423 |
| HPV31 | L1 | CISMDYKQT | 147 | 9 | | | | | 5424 |
| HPV31 | L1 | CISMDYKQTQL | 147 | 11 | | | | | 5425 |
| HPV31 | L1 | CLLGCKPPI | 158 | 9 | | | | | 5426 |
| HPV31 | L1 | DAQIFNKPYWM | 304 | 11 | | | | | 5427 |
| HPV31 | L1 | DIMTYIHSM | 387 | 9 | | | | | 5428 |
| HPV31 | L1 | DLQFIFQL | 372 | 8 | | | | | 5429 |
| HPV31 | L1 | DLQFIFQLCKI | 372 | 11 | | | | | 5430 |
| HPV31 | L1 | DLYIKGSGST | 275 | 10 | | | | | 5431 |
| HPV31 | L1 | DLYIKGSGSTA | 275 | 11 | | | | | 5432 |
| HPV31 | L1 | DMVDTGFGA | 200 | 9 | | | | | 5433 |
| HPV31 | L1 | DMVDTGFGAM | 200 | 10 | | | | | 5434 |
| HPV31 | L1 | DQFPLGRKFL | 461 | 10 | | | | | 5435 |
| HPV31 | L1 | DQFPLGRKFLL | 461 | 11 | | | | | 5436 |
| HPV31 | L1 | DTENSNRYA | 129 | 9 | | | | | 5437 |
| HPV31 | L1 | DTGFGAMDFT | 203 | 10 | | | | | 5438 |
| HPV31 | L1 | DTGFGAMDFTA | 203 | 11 | | | | | 5439 |
| HPV31 | L1 | DTKSNVPL | 216 | 8 | | | | | 5440 |
| HPV31 | L1 | DTKSNVPLDI | 216 | 10 | | | | | 5441 |
| HPV31 | L1 | DTSFYNPET | 88 | 9 | | | | | 5442 |
| HPV31 | L1 | DTTRSTNM | 336 | 8 | | | | | 5443 |
| HPV31 | L1 | DTTRSTNMSV | 336 | 10 | | | | | 5444 |
| HPV31 | L1 | DTYRFVTSQA | 417 | 10 | | | | | 5445 |
| HPV31 | L1 | DTYRFVTSQAI | 417 | 11 | | | | | 5446 |
| HPV31 | L1 | EATVYLPPV | 8 | 9 | | | | | 5447 |
| HPV31 | L1 | EATVYLPPVPV | 8 | 11 | | | | | 5448 |
| HPV31 | L1 | ETQRLVWA | 95 | 8 | | | | | 5449 |
| HPV31 | L1 | ETQRLVWACV | 95 | 10 | | | | | 5450 |
| HPV31 | L1 | EVGRGQPL | 107 | 8 | | | | | 5451 |
| HPV31 | L1 | EVGRGQPLGV | 107 | 10 | | | | | 5452 |
| HPV31 | L1 | EVNLKEKFSA | 449 | 10 | | | | | 5453 |
| HPV31 | L1 | FIFQLCKI | 375 | 8 | | | | | 5454 |
| HPV31 | L1 | FIFQLCKIT | 375 | 9 | | | | | 5455 |
| HPV31 | L1 | FIFQLCKITL | 375 | 10 | | | | | 5456 |
| HPV31 | L1 | FLLQAGYRA | 469 | 9 | | | | | 5457 |
| HPV31 | L1 | FQLCKITL | 377 | 8 | | | | | 5458 |
| HPV31 | L1 | FQLCKITLSA | 377 | 10 | | | | | 5459 |
| HPV31 | L1 | FTALQDTKSNV | 211 | 11 | | | | | 5460 |
| HPV31 | L1 | FVRHFFNRSGT | 257 | 11 | | | | | 5461 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | L1 | FVTSQAIT | 421 | 8 | | | | | 5462 |
| HPV31 | L1 | FVTVVDTT | 331 | 8 | | | | | 5463 |
| HPV31 | L1 | FVTVVDTTRST | 331 | 11 | | | | | 5464 |
| HPV31 | L1 | GAMDFTAL | 207 | 8 | | | | | 5465 |
| HPV31 | L1 | GAMDFTALQDT | 207 | 11 | | | | | 5466 |
| HPV31 | L1 | GICWGNQL | 323 | 8 | | | | | 5467 |
| HPV31 | L1 | GICWGNQLFV | 323 | 10 | | | | | 5468 |
| HPV31 | L1 | GICWGNQLFVT | 323 | 11 | | | | | 5469 |
| HPV31 | L1 | GISGHPLL | 117 | 8 | | | | | 5470 |
| HPV31 | L1 | GLEVGRGQPL | 105 | 10 | | | | | 5471 |
| HPV31 | L1 | GLQYRVFRV | 68 | 9 | | | | | 5472 |
| HPV31 | L1 | GLQYRVFRVRL | 68 | 11 | | | | | 5473 |
| HPV31 | L1 | GLTTPPSGSL | 406 | 10 | | | | | 5474 |
| HPV31 | L1 | GQPLGVGI | 111 | 8 | | | | | 5475 |
| HPV31 | L1 | GTDNRECI | 141 | 8 | | | | | 5476 |
| HPV31 | L1 | GTDNRECISM | 141 | 10 | | | | | 5477 |
| HPV31 | L1 | GTVGESVPT | 266 | 9 | | | | | 5478 |
| HPV31 | L1 | GTVGESVPTDL | 266 | 11 | | | | | 5479 |
| HPV31 | L1 | GVGISGHPL | 115 | 9 | | | | | 5480 |
| HPV31 | L1 | GVGISGHPLL | 115 | 10 | | | | | 5481 |
| HPV31 | L1 | HAGSARLL | 36 | 8 | | | | | 5482 |
| HPV31 | L1 | HAGSARLLT | 36 | 9 | | | | | 5483 |
| HPV31 | L1 | HAGSARLLTV | 36 | 10 | | | | | 5484 |
| HPV31 | L1 | ILEDWNFGL | 399 | 9 | | | | | 5485 |
| HPV31 | L1 | ILEDWNFGLT | 399 | 10 | | | | | 5486 |
| HPV31 | L1 | ILEDWNFGLTT | 399 | 11 | | | | | 5487 |
| HPV31 | L1 | IMTYIHSM | 388 | 8 | | | | | 5488 |
| HPV31 | L1 | IMTYIHSMNPA | 388 | 11 | | | | | 5489 |
| HPV31 | L1 | IQDGDMVDT | 196 | 9 | | | | | 5490 |
| HPV31 | L1 | ITLSADIM | 382 | 8 | | | | | 5491 |
| HPV31 | L1 | ITLSADIMT | 382 | 9 | | | | | 5492 |
| HPV31 | L1 | ITLSADIMTYI | 382 | 11 | | | | | 5493 |
| HPV31 | L1 | ITPGDCPPL | 181 | 9 | | | | | 5494 |
| HPV31 | L1 | ITPGDCPPLEL | 181 | 11 | | | | | 5495 |
| HPV31 | L1 | IVVPKVSGL | 61 | 9 | | | | | 5496 |
| HPV31 | L1 | KAGKRSAPSA | 482 | 10 | | | | | 5497 |
| HPV31 | L1 | KITLSADI | 381 | 8 | | | | | 5498 |
| HPV31 | L1 | KITLSADIM | 381 | 9 | | | | | 5499 |
| HPV31 | L1 | KITLSADIMT | 381 | 10 | | | | | 5500 |
| HPV31 | L1 | KIVVPKVSGL | 60 | 10 | | | | | 5501 |
| HPV31 | L1 | KMVAEPYGDT | 237 | 10 | | | | | 5502 |
| HPV31 | L1 | KMVAEPYGDTL | 237 | 11 | | | | | 5503 |
| HPV31 | L1 | KQTQLCLL | 153 | 8 | | | | | 5504 |
| HPV31 | L1 | KVSGLQYRV | 65 | 9 | | | | | 5505 |
| HPV31 | L1 | KVVSTDEYV | 20 | 9 | | | | | 5506 |
| HPV31 | L1 | KVVSTDEYVT | 20 | 10 | | | | | 5507 |
| HPV31 | L1 | LANSTYFPT | 287 | 9 | | | | | 5508 |
| HPV31 | L1 | LLGCKPPI | 159 | 8 | | | | | 5509 |
| HPV31 | L1 | LLNKFDDT | 123 | 8 | | | | | 5510 |
| HPV31 | L1 | LLQAGYRA | 470 | 8 | | | | | 5511 |
| HPV31 | L1 | LLTVGHPYYSI | 42 | 11 | | | | | 5512 |
| HPV31 | L1 | LQDTKSNV | 214 | 8 | | | | | 5513 |
| HPV31 | L1 | LQDTKSNVPL | 214 | 10 | | | | | 5514 |
| HPV31 | L1 | LQFIFQLCKI | 373 | 10 | | | | | 5515 |
| HPV31 | L1 | LQFIFQLCKIT | 373 | 11 | | | | | 5516 |
| HPV31 | L1 | LQYRVFRV | 69 | 8 | | | | | 5517 |
| HPV31 | L1 | LQYRVFRVRL | 69 | 10 | | | | | 5518 |
| HPV31 | L1 | LTTPPSGSL | 407 | 9 | | | | | 5519 |
| HPV31 | L1 | LTVGHPYYSI | 43 | 10 | | | | | 5520 |
| HPV31 | L1 | LVWACVGL | 99 | 8 | | | | | 5521 |
| HPV31 | L1 | LVWACVGLEV | 99 | 10 | | | | | 5522 |
| HPV31 | L1 | MQRAQGHNNGI | 314 | 11 | | | | | 5523 |
| HPV31 | L1 | MTYIHSMNPA | 389 | 10 | | | | | 5524 |
| HPV31 | L1 | MTYIHSMNPAI | 389 | 11 | | | | | 5525 |
| HPV31 | L1 | MVAEPYGDT | 238 | 9 | | | | | 5526 |
| HPV31 | L1 | MVAEPYGDTL | 238 | 10 | | | | | 5527 |
| HPV31 | L1 | MVDTGFGA | 201 | 8 | | | | | 5528 |
| HPV31 | L1 | MVDTGFGAM | 201 | 9 | | | | | 5529 |
| HPV31 | L1 | MVTSDAQI | 300 | 8 | | | | | 5530 |
| HPV31 | L1 | NAITPGDCPPL | 179 | 11 | | | | | 5531 |
| HPV31 | L1 | NIYYHAGSA | 32 | 9 | | | | | 5532 |
| HPV31 | L1 | NIYYHAGSARL | 32 | 11 | | | | | 5533 |
| HPV31 | L1 | NLKEKFSA | 451 | 8 | | | | | 5534 |
| HPV31 | L1 | NLKEKFSADL | 451 | 10 | | | | | 5535 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | L1 | NMSVCAAI | 342 | 8 | | | | | 5536 |
| HPV31 | L1 | NMSVCAAIA | 342 | 9 | | | | | 5537 |
| HPV31 | L1 | NQLFVTVV | 328 | 8 | | | | | 5538 |
| HPV31 | L1 | NQLFVTVVDT | 328 | 10 | | | | | 5539 |
| HPV31 | L1 | NQLFVTVVDTT | 328 | 11 | | | | | 5540 |
| HPV31 | L1 | NVPLDICNSI | 220 | 10 | | | | | 5541 |
| HPV31 | L1 | PAILEDWNFGL | 397 | 11 | | | | | 5542 |
| HPV31 | L1 | PLDICNSI | 222 | 8 | | | | | 5543 |
| HPV31 | L1 | PLELKNSV | 188 | 8 | | | | | 5544 |
| HPV31 | L1 | PLELKNSVI | 188 | 9 | | | | | 5545 |
| HPV31 | L1 | PLGRKFLL | 464 | 8 | | | | | 5546 |
| HPV31 | L1 | PLGRKFLLQA | 464 | 10 | | | | | 5547 |
| HPV31 | L1 | PLGVGISGHPL | 113 | 11 | | | | | 5548 |
| HPV31 | L1 | PLLNKFDDT | 122 | 9 | | | | | 5549 |
| HPV31 | L1 | PTPSGSMV | 294 | 8 | | | | | 5550 |
| HPV31 | L1 | PTPSGSMVT | 294 | 9 | | | | | 5551 |
| HPV31 | L1 | PVPVSKVV | 15 | 8 | | | | | 5552 |
| HPV31 | L1 | PVPVSKVVST | 15 | 10 | | | | | 5553 |
| HPV31 | L1 | PVSKVVST | 17 | 8 | | | | | 5554 |
| HPV31 | L1 | QAITCQKT | 425 | 8 | | | | | 5555 |
| HPV31 | L1 | QAITCQKTA | 425 | 9 | | | | | 5556 |
| HPV31 | L1 | QIFNKPYWM | 306 | 9 | | | | | 5557 |
| HPV31 | L1 | QLCKITLSA | 378 | 9 | | | | | 5558 |
| HPV31 | L1 | QLCKITLSADI | 378 | 11 | | | | | 5559 |
| HPV31 | L1 | QLCLLGCKPPI | 156 | 11 | | | | | 5560 |
| HPV31 | L1 | QLFVTVVDT | 329 | 9 | | | | | 5561 |
| HPV31 | L1 | QLFVTVVDTT | 329 | 10 | | | | | 5562 |
| HPV31 | L1 | RAQGHNNGI | 316 | 9 | | | | | 5563 |
| HPV31 | L1 | RARPKFKA | 476 | 8 | | | | | 5564 |
| HPV31 | L1 | RLVWACVGL | 98 | 9 | | | | | 5565 |
| HPV31 | L1 | RLVWACVGLEV | 98 | 11 | | | | | 5566 |
| HPV31 | L1 | RTNIYYHA | 30 | 8 | | | | | 5567 |
| HPV31 | L1 | RTNIYYHAGSA | 30 | 11 | | | | | 5568 |
| HPV31 | L1 | SADIMTYI | 385 | 8 | | | | | 5569 |
| HPV31 | L1 | SADIMTYIHSM | 385 | 11 | | | | | 5570 |
| HPV31 | L1 | SADLDQFPL | 457 | 9 | | | | | 5571 |
| HPV31 | L1 | SAPSASTT | 487 | 8 | | | | | 5572 |
| HPV31 | L1 | SAPSASTTT | 487 | 9 | | | | | 5573 |
| HPV31 | L1 | SAPSASTTTPA | 487 | 11 | | | | | 5574 |
| HPV31 | L1 | SASTTTPA | 490 | 8 | | | | | 5575 |
| HPV31 | L1 | SICKYPDYL | 228 | 9 | | | | | 5576 |
| HPV31 | L1 | SICKYPDYLKM | 228 | 11 | | | | | 5577 |
| HPV31 | L1 | SICKSDNPKKI | 51 | 11 | | | | | 5578 |
| HPV31 | L1 | SLEDTYRFV | 414 | 9 | | | | | 5579 |
| HPV31 | L1 | SLEDTYRFVT | 414 | 10 | | | | | 5580 |
| HPV31 | L1 | SLWRPSEA | 2 | 8 | | | | | 5581 |
| HPV31 | L1 | SLWRPSEAT | 2 | 9 | | | | | 5582 |
| HPV31 | L1 | SLWRPSEATV | 2 | 10 | | | | | 5583 |
| HPV31 | L1 | SMDYKQTQL | 149 | 9 | | | | | 5584 |
| HPV31 | L1 | SMDYKQTQLCL | 149 | 11 | | | | | 5585 |
| HPV31 | L1 | SMVTSDAQI | 299 | 9 | | | | | 5586 |
| HPV31 | L1 | SQAITCQKT | 424 | 9 | | | | | 5587 |
| HPV31 | L1 | SQAITCQKTA | 424 | 10 | | | | | 5588 |
| HPV31 | L1 | STATLANST | 283 | 9 | | | | | 5589 |
| HPV31 | L1 | STDEYVTRT | 23 | 9 | | | | | 5590 |
| HPV31 | L1 | STDEYVTRTNI | 23 | 11 | | | | | 5591 |
| HPV31 | L1 | STNMSVCA | 340 | 8 | | | | | 5592 |
| HPV31 | L1 | STNMSVCAA | 340 | 9 | | | | | 5593 |
| HPV31 | L1 | STNMSVCAAI | 340 | 10 | | | | | 5594 |
| HPV31 | L1 | STNMSVCAAIA | 340 | 11 | | | | | 5595 |
| HPV31 | L1 | STTTPAKRKKT | 492 | 11 | | | | | 5596 |
| HPV31 | L1 | STYFPTPSGSM | 290 | 11 | | | | | 5597 |
| HPV31 | L1 | SVCAAIANSDT | 344 | 11 | | | | | 5598 |
| HPV31 | L1 | SVIQDGDM | 194 | 8 | | | | | 5599 |
| HPV31 | L1 | SVIQDGDMV | 194 | 9 | | | | | 5600 |
| HPV31 | L1 | SVIQDGDMVDT | 194 | 11 | | | | | 5601 |
| HPV31 | L1 | SVPTDLYI | 271 | 8 | | | | | 5602 |
| HPV31 | L1 | TALQDTKSNV | 212 | 10 | | | | | 5603 |
| HPV31 | L1 | TATLANST | 284 | 8 | | | | | 5604 |
| HPV31 | L1 | TLANSTYFPT | 286 | 10 | | | | | 5605 |
| HPV31 | L1 | TLFFYLRREQM | 246 | 11 | | | | | 5606 |
| HPV31 | L1 | TLSADIMT | 383 | 8 | | | | | 5607 |
| HPV31 | L1 | TLSADIMTYI | 383 | 10 | | | | | 5608 |
| HPV31 | L1 | TQRLVWACV | 96 | 9 | | | | | 5609 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | L1 | TQRLVWACVGL | 96 | 11 | | | | | 5610 |
| HPV31 | L1 | TTPAKRKKT | 494 | 9 | | | | | 5611 |
| HPV31 | L1 | TTPPSGSL | 408 | 8 | | | | | 5612 |
| HPV31 | L1 | TTPPSGSLEDT | 408 | 11 | | | | | 5613 |
| HPV31 | L1 | TTRSTNMSV | 337 | 9 | | | | | 5614 |
| HPV31 | L1 | TTRSTNMSVCA | 337 | 11 | | | | | 5615 |
| HPV31 | L1 | TTTPAKRKKT | 493 | 10 | | | | | 5616 |
| HPV31 | L1 | TVGESVPT | 267 | 8 | | | | | 5617 |
| HPV31 | L1 | TVGESVPTDL | 267 | 10 | | | | | 5618 |
| HPV31 | L1 | TVGHPYYSI | 44 | 9 | | | | | 5619 |
| HPV31 | L1 | TVVDTTRST | 333 | 9 | | | | | 5620 |
| HPV31 | L1 | TVVDTTRSTNM | 333 | 11 | | | | | 5621 |
| HPV31 | L1 | TVYLPPVPV | 10 | 9 | | | | | 5622 |
| HPV31 | L1 | VAEPYGDT | 239 | 8 | | | | | 5623 |
| HPV31 | L1 | VAEPYGDTL | 239 | 9 | | | | | 5624 |
| HPV31 | L1 | VIQDGDMV | 195 | 8 | | | | | 5625 |
| HPV31 | L1 | VIQDGDMVDT | 195 | 10 | | | | | 5626 |
| HPV31 | L1 | VTRTNIYYHA | 28 | 10 | | | | | 5627 |
| HPV31 | L1 | VTSQAITCQKT | 422 | 11 | | | | | 5628 |
| HPV31 | L1 | VTVVDTTRST | 332 | 10 | | | | | 5629 |
| HPV31 | L1 | VVDTTRST | 334 | 8 | | | | | 5630 |
| HPV31 | L1 | VVDTTRSTNM | 334 | 10 | | | | | 5631 |
| HPV31 | L1 | VVPKVSGL | 62 | 8 | | | | | 5632 |
| HPV31 | L1 | VVSTDEYV | 21 | 8 | | | | | 5633 |
| HPV31 | L1 | VVSTDEYVT | 21 | 9 | | | | | 5634 |
| HPV31 | L1 | VVSTDEYVTRT | 21 | 11 | | | | | 5635 |
| HPV31 | L1 | WACVGLEV | 101 | 8 | | | | | 5636 |
| HPV31 | L1 | YIHSMNPA | 391 | 8 | | | | | 5637 |
| HPV31 | L1 | YIHSMNPAI | 391 | 9 | | | | | 5638 |
| HPV31 | L1 | YIHSMNPAIL | 391 | 10 | | | | | 5639 |
| HPV31 | L1 | YIKGSGST | 277 | 8 | | | | | 5640 |
| HPV31 | L1 | YIKGSGSTA | 277 | 9 | | | | | 5641 |
| HPV31 | L1 | YIKGSGSTAT | 277 | 10 | | | | | 5642 |
| HPV31 | L1 | YIKGSGSTATL | 277 | 11 | | | | | 5643 |
| HPV31 | L1 | YLPPVPVSKV | 12 | 10 | | | | | 5644 |
| HPV31 | L1 | YLPPVPVSKVV | 12 | 11 | | | | | 5645 |
| HPV31 | L1 | YLRHGEEFDL | 364 | 10 | | | | | 5646 |
| HPV31 | L1 | YLRREQMFV | 250 | 9 | | | | | 5647 |
| HPV31 | L1 | YVFWEVNL | 445 | 8 | | | | | 5648 |
| HPV31 | L1 | YVTRTNIYYHA | 27 | 11 | | | | | 5649 |
| HPV31 | L2 | AAGTCPSDV | 24 | 9 | | | | | 5650 |
| HPV31 | L2 | AAGTCPSDVI | 24 | 10 | | | | | 5651 |
| HPV31 | L2 | AILDVTSV | 143 | 8 | | | | | 5652 |
| HPV31 | L2 | AILDVTSVST | 143 | 10 | | | | | 5653 |
| HPV31 | L2 | ALHRPALT | 281 | 8 | | | | | 5654 |
| HPV31 | L2 | ALTSRRNT | 286 | 8 | | | | | 5655 |
| HPV31 | L2 | ALTSRRNTV | 286 | 9 | | | | | 5656 |
| HPV31 | L2 | ATHNVSPST | 367 | 9 | | | | | 5657 |
| HPV31 | L2 | ATHNVSPSTA | 367 | 10 | | | | | 5658 |
| HPV31 | L2 | ATHNVSPSTAV | 367 | 11 | | | | | 5659 |
| HPV31 | L2 | ATQLYQTCKA | 15 | 10 | | | | | 5660 |
| HPV31 | L2 | ATQLYQTCKAA | 15 | 11 | | | | | 5661 |
| HPV31 | L2 | ATQQVKVI | 226 | 8 | | | | | 5662 |
| HPV31 | L2 | ATQQVKVIDPT | 226 | 11 | | | | | 5663 |
| HPV31 | L2 | ATTADTTPA | 135 | 9 | | | | | 5664 |
| HPV31 | L2 | ATTADTTPAI | 135 | 10 | | | | | 5665 |
| HPV31 | L2 | ATTADTTPAIL | 135 | 11 | | | | | 5666 |
| HPV31 | L2 | ATTTSTLNDGL | 342 | 11 | | | | | 5667 |
| HPV31 | L2 | AVQSTSAV | 376 | 8 | | | | | 5668 |
| HPV31 | L2 | AVQSTSAVSA | 376 | 10 | | | | | 5669 |
| HPV31 | L2 | AVSAYVPT | 382 | 8 | | | | | 5670 |
| HPV31 | L2 | AVSAYVPTNT | 382 | 10 | | | | | 5671 |
| HPV31 | L2 | AVSAYVPTNTT | 382 | 11 | | | | | 5672 |
| HPV31 | L2 | DIATTADT | 133 | 8 | | | | | 5673 |
| HPV31 | L2 | DIATTADTT | 133 | 9 | | | | | 5674 |
| HPV31 | L2 | DIATTADTTPA | 133 | 11 | | | | | 5675 |
| HPV31 | L2 | DIIALHRPA | 278 | 9 | | | | | 5676 |
| HPV31 | L2 | DIIALHRPAL | 278 | 10 | | | | | 5677 |
| HPV31 | L2 | DIIALHRPALT | 278 | 11 | | | | | 5678 |
| HPV31 | L2 | DIPIFSGPDV | 400 | 10 | | | | | 5679 |
| HPV31 | L2 | DISSINPA | 322 | 8 | | | | | 5680 |
| HPV31 | L2 | DIYADTDFT | 354 | 9 | | | | | 5681 |
| HPV31 | L2 | DIYADTDFTV | 354 | 10 | | | | | 5682 |
| HPV31 | L2 | DQILRYGSM | 43 | 9 | | | | | 5683 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | L2 | DQILRYGSMGV | 43 | 11 | | | | | 5684 |
| HPV31 | L2 | DTDFTVDT | 358 | 8 | | | | | 5685 |
| HPV31 | L2 | DTDFTVDTPA | 358 | 10 | | | | | 5686 |
| HPV31 | L2 | DTDFTVDTPAT | 358 | 11 | | | | | 5687 |
| HPV31 | L2 | DTPATHNV | 364 | 8 | | | | | 5688 |
| HPV31 | L2 | DTTPAILDV | 139 | 9 | | | | | 5689 |
| HPV31 | L2 | DTTPAILDVT | 139 | 10 | | | | | 5690 |
| HPV31 | L2 | DVGAPAPI | 116 | 8 | | | | | 5691 |
| HPV31 | L2 | DVIPKIEHT | 31 | 9 | | | | | 5692 |
| HPV31 | L2 | DVIPKIEHTT | 31 | 10 | | | | | 5693 |
| HPV31 | L2 | DVIPKIEHTTI | 31 | 11 | | | | | 5694 |
| HPV31 | L2 | DVPIEHAPT | 408 | 9 | | | | | 5695 |
| HPV31 | L2 | DVPIEHAPTQV | 408 | 11 | | | | | 5696 |
| HPV31 | L2 | EASIPIRPPV | 84 | 10 | | | | | 5697 |
| HPV31 | L2 | EIPMDTFI | 190 | 8 | | | | | 5698 |
| HPV31 | L2 | EIPMDTFIV | 190 | 9 | | | | | 5699 |
| HPV31 | L2 | EIPMDTFIVST | 190 | 11 | | | | | 5700 |
| HPV31 | L2 | EMQPLGASA | 334 | 9 | | | | | 5701 |
| HPV31 | L2 | EMQPLGASAT | 334 | 10 | | | | | 5702 |
| HPV31 | L2 | EMQPLGASATT | 334 | 11 | | | | | 5703 |
| HPV31 | L2 | ETSGHLLL | 171 | 8 | | | | | 5704 |
| HPV31 | L2 | ETVNAEESL | 253 | 9 | | | | | 5705 |
| HPV31 | L2 | FIVSTNNENI | 196 | 10 | | | | | 5706 |
| HPV31 | L2 | FIVSTNNENIT | 196 | 11 | | | | | 5707 |
| HPV31 | L2 | FLDIIALHRPA | 276 | 11 | | | | | 5708 |
| HPV31 | L2 | FLSAPKQL | 237 | 8 | | | | | 5709 |
| HPV31 | L2 | FLSAPKQLI | 237 | 9 | | | | | 5710 |
| HPV31 | L2 | FLSAPKQLIT | 237 | 10 | | | | | 5711 |
| HPV31 | L2 | FTDPSVLQPPT | 158 | 11 | | | | | 5712 |
| HPV31 | L2 | FTDVSVAA | 459 | 8 | | | | | 5713 |
| HPV31 | L2 | FTVDTPAT | 361 | 8 | | | | | 5714 |
| HPV31 | L2 | FTVDTPATHNV | 361 | 11 | | | | | 5715 |
| HPV31 | L2 | FVDGGDFYL | 433 | 9 | | | | | 5716 |
| HPV31 | L2 | GAPAPIPHPPT | 118 | 11 | | | | | 5717 |
| HPV31 | L2 | GARVHYYYDI | 314 | 10 | | | | | 5718 |
| HPV31 | L2 | GASATTTST | 339 | 9 | | | | | 5719 |
| HPV31 | L2 | GASATTTSTL | 339 | 10 | | | | | 5720 |
| HPV31 | L2 | GATIGARV | 310 | 8 | | | | | 5721 |
| HPV31 | L2 | GIGSGSGT | 59 | 8 | | | | | 5722 |
| HPV31 | L2 | GIVDVGAPA | 113 | 9 | | | | | 5723 |
| HPV31 | L2 | GIVDVGAPAPI | 113 | 11 | | | | | 5724 |
| HPV31 | L2 | GLGIGSGSGT | 57 | 10 | | | | | 5725 |
| HPV31 | L2 | GLYDIYADT | 351 | 9 | | | | | 5726 |
| HPV31 | L2 | GLYSKATQQV | 221 | 10 | | | | | 5727 |
| HPV31 | L2 | GTCPSDVI | 26 | 8 | | | | | 5728 |
| HPV31 | L2 | GTCPSDVIPKI | 26 | 11 | | | | | 5729 |
| HPV31 | L2 | GTGGRTGYV | 65 | 9 | | | | | 5730 |
| HPV31 | L2 | GTGGRTGYVPL | 65 | 11 | | | | | 5731 |
| HPV31 | L2 | GVFFGGLGI | 52 | 9 | | | | | 5732 |
| HPV31 | L2 | GVRRPARL | 213 | 8 | | | | | 5733 |
| HPV31 | L2 | GVRRPARLGL | 213 | 10 | | | | | 5734 |
| HPV31 | L2 | HAPTQVFPFPL | 413 | 11 | | | | | 5735 |
| HPV31 | L2 | HLLLSSSSI | 175 | 9 | | | | | 5736 |
| HPV31 | L2 | HLLLSSSSIST | 175 | 11 | | | | | 5737 |
| HPV31 | L2 | HTTIADQI | 38 | 8 | | | | | 5738 |
| HPV31 | L2 | HTTIADQIL | 38 | 9 | | | | | 5739 |
| HPV31 | L2 | IADQILRYGSM | 41 | 11 | | | | | 5740 |
| HPV31 | L2 | IALHRPAL | 280 | 8 | | | | | 5741 |
| HPV31 | L2 | IALHRPALT | 280 | 9 | | | | | 5742 |
| HPV31 | L2 | IAPDPDFL | 270 | 8 | | | | | 5743 |
| HPV31 | L2 | IAPDPDFLDI | 270 | 10 | | | | | 5744 |
| HPV31 | L2 | IAPDPDFLDII | 270 | 11 | | | | | 5745 |
| HPV31 | L2 | IATTADTT | 134 | 8 | | | | | 5746 |
| HPV31 | L2 | IATTADTTPA | 134 | 10 | | | | | 5747 |
| HPV31 | L2 | IATTADTTPAI | 134 | 11 | | | | | 5748 |
| HPV31 | L2 | IIALHRPA | 279 | 8 | | | | | 5749 |
| HPV31 | L2 | IIALHRPAL | 279 | 9 | | | | | 5750 |
| HPV31 | L2 | IIALHRPALT | 279 | 10 | | | | | 5751 |
| HPV31 | L2 | ILDVTSVST | 144 | 9 | | | | | 5752 |
| HPV31 | L2 | ILRYGSMGV | 45 | 9 | | | | | 5753 |
| HPV31 | L2 | ITSSTPIPGV | 205 | 10 | | | | | 5754 |
| HPV31 | L2 | ITYENPAYET | 245 | 10 | | | | | 5755 |
| HPV31 | L2 | ITYENPAYETV | 245 | 11 | | | | | 5756 |
| HPV31 | L2 | IVDVGAPA | 114 | 8 | | | | | 5757 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | L2 | IVDVGAPAPI | 114 | 10 | | | | | 5758 |
| HPV31 | L2 | IVSLVEESGI | 105 | 10 | | | | | 5759 |
| HPV31 | L2 | IVSLVEESGIV | 105 | 11 | | | | | 5760 |
| HPV31 | L2 | IVSTNNENI | 197 | 9 | | | | | 5761 |
| HPV31 | L2 | IVSTNNENIT | 197 | 10 | | | | | 5762 |
| HPV31 | L2 | KAAGTCPSDV | 23 | 10 | | | | | 5763 |
| HPV31 | L2 | KAAGTCPSDVI | 23 | 11 | | | | | 5764 |
| HPV31 | L2 | KATQQVKV | 225 | 8 | | | | | 5765 |
| HPV31 | L2 | KATQQVKVI | 225 | 9 | | | | | 5766 |
| HPV31 | L2 | KIEHTTIA | 35 | 8 | | | | | 5767 |
| HPV31 | L2 | KIEHTTIADQI | 35 | 11 | | | | | 5768 |
| HPV31 | L2 | KQLITYENPA | 242 | 10 | | | | | 5769 |
| HPV31 | L2 | KQTLRTRSGA | 302 | 10 | | | | | 5770 |
| HPV31 | L2 | KQTLRTRSGAT | 302 | 11 | | | | | 5771 |
| HPV31 | L2 | KVIDPTFL | 231 | 8 | | | | | 5772 |
| HPV31 | L2 | KVIDPTFLSA | 231 | 10 | | | | | 5773 |
| HPV31 | L2 | LAPTTPQV | 423 | 8 | | | | | 5774 |
| HPV31 | L2 | LAPTTPQVSI | 423 | 10 | | | | | 5775 |
| HPV31 | L2 | LITYENPA | 244 | 8 | | | | | 5776 |
| HPV31 | L2 | LITYENPAYET | 244 | 11 | | | | | 5777 |
| HPV31 | L2 | LLLSSSSI | 176 | 8 | | | | | 5778 |
| HPV31 | L2 | LLLSSSSIST | 176 | 10 | | | | | 5779 |
| HPV31 | L2 | LLSSSSIST | 177 | 9 | | | | | 5780 |
| HPV31 | L2 | LQPPTPAET | 164 | 9 | | | | | 5781 |
| HPV31 | L2 | LTSRRNTV | 287 | 8 | | | | | 5782 |
| HPV31 | L2 | LVEESGIV | 108 | 8 | | | | | 5783 |
| HPV31 | L2 | LVEESGIVDV | 108 | 10 | | | | | 5784 |
| HPV31 | L2 | MLKRRRKRV | 447 | 9 | | | | | 5785 |
| HPV31 | L2 | MQPLGASA | 335 | 8 | | | | | 5786 |
| HPV31 | L2 | MQPLGASAT | 335 | 9 | | | | | 5787 |
| HPV31 | L2 | MQPLGASATT | 335 | 10 | | | | | 5788 |
| HPV31 | L2 | MQPLGASATTT | 335 | 11 | | | | | 5789 |
| HPV31 | L2 | NAEESLYFSNT | 256 | 11 | | | | | 5790 |
| HPV31 | L2 | NIAPDPDFL | 269 | 9 | | | | | 5791 |
| HPV31 | L2 | NIAPDPDFLDI | 269 | 11 | | | | | 5792 |
| HPV31 | L2 | NITSSTPI | 204 | 8 | | | | | 5793 |
| HPV31 | L2 | NITSSTPIPGV | 204 | 11 | | | | | 5794 |
| HPV31 | L2 | NTTVPLST | 390 | 8 | | | | | 5795 |
| HPV31 | L2 | NTVRYSRL | 292 | 8 | | | | | 5796 |
| HPV31 | L2 | NVSPSTAV | 370 | 8 | | | | | 5797 |
| HPV31 | L2 | NVSPSTAVQST | 370 | 11 | | | | | 5798 |
| HPV31 | L2 | PAETSGHL | 169 | 8 | | | | | 5799 |
| HPV31 | L2 | PAETSGHLL | 169 | 9 | | | | | 5800 |
| HPV31 | L2 | PAETSGHLLL | 169 | 10 | | | | | 5801 |
| HPV31 | L2 | PAGESIEM | 328 | 8 | | | | | 5802 |
| HPV31 | L2 | PAGESIEMQPL | 328 | 11 | | | | | 5803 |
| HPV31 | L2 | PAILDVTSV | 142 | 9 | | | | | 5804 |
| HPV31 | L2 | PAILDVTSVST | 142 | 11 | | | | | 5805 |
| HPV31 | L2 | PALTSRRNT | 285 | 9 | | | | | 5806 |
| HPV31 | L2 | PALTSRRNTV | 285 | 10 | | | | | 5807 |
| HPV31 | L2 | PAPIPHPPT | 120 | 9 | | | | | 5808 |
| HPV31 | L2 | PAPIPHPPTT | 120 | 10 | | | | | 5809 |
| HPV31 | L2 | PARLGLYSKA | 217 | 10 | | | | | 5810 |
| HPV31 | L2 | PARLGLYSKAT | 217 | 11 | | | | | 5811 |
| HPV31 | L2 | PATHNVSPST | 366 | 10 | | | | | 5812 |
| HPV31 | L2 | PATHNVSPSTA | 366 | 11 | | | | | 5813 |
| HPV31 | L2 | PAYETVNA | 250 | 8 | | | | | 5814 |
| HPV31 | L2 | PIEHAPTQV | 410 | 9 | | | | | 5815 |
| HPV31 | L2 | PIFSGPDV | 402 | 8 | | | | | 5816 |
| HPV31 | L2 | PIFSGPDVPI | 402 | 10 | | | | | 5817 |
| HPV31 | L2 | PIPGVRRPA | 210 | 9 | | | | | 5818 |
| HPV31 | L2 | PIPGVRRPARL | 210 | 11 | | | | | 5819 |
| HPV31 | L2 | PIPHPPTT | 122 | 8 | | | | | 5820 |
| HPV31 | L2 | PIRPPVSI | 88 | 8 | | | | | 5821 |
| HPV31 | L2 | PIRPPVSIDPV | 88 | 11 | | | | | 5822 |
| HPV31 | L2 | PLAPTTPQV | 422 | 9 | | | | | 5823 |
| HPV31 | L2 | PLAPTTPQVSI | 422 | 11 | | | | | 5824 |
| HPV31 | L2 | PLDPSIVSL | 100 | 9 | | | | | 5825 |
| HPV31 | L2 | PLDPSIVSLV | 100 | 10 | | | | | 5826 |
| HPV31 | L2 | PLGASATT | 337 | 8 | | | | | 5827 |
| HPV31 | L2 | PLGASATTT | 337 | 9 | | | | | 5828 |
| HPV31 | L2 | PLGASATTTST | 337 | 11 | | | | | 5829 |
| HPV31 | L2 | PLSTGFDI | 394 | 8 | | | | | 5830 |
| HPV31 | L2 | PLSTGFDIPI | 394 | 10 | | | | | 5831 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | L2 | PLSTRPST | 74 | 8 | | | | | 5832 |
| HPV31 | L2 | PLSTRPSTV | 74 | 9 | | | | | 5833 |
| HPV31 | L2 | PMDTFIVST | 192 | 9 | | | | | 5834 |
| HPV31 | L2 | PTFLSAPKQL | 235 | 10 | | | | | 5835 |
| HPV31 | L2 | PTFLSAPKQLI | 235 | 11 | | | | | 5836 |
| HPV31 | L2 | PTFTDPSV | 156 | 8 | | | | | 5837 |
| HPV31 | L2 | PTFTDPSVL | 156 | 9 | | | | | 5838 |
| HPV31 | L2 | PTNTTVPL | 388 | 8 | | | | | 5839 |
| HPV31 | L2 | PTNTTVPLST | 388 | 10 | | | | | 5840 |
| HPV31 | L2 | PTPAETSGHL | 167 | 10 | | | | | 5841 |
| HPV31 | L2 | PTPAETSGHLL | 167 | 11 | | | | | 5842 |
| HPV31 | L2 | PTQVFPFPL | 415 | 9 | | | | | 5843 |
| HPV31 | L2 | PTQVFPFPLA | 415 | 10 | | | | | 5844 |
| HPV31 | L2 | PTTPQVSI | 425 | 8 | | | | | 5845 |
| HPV31 | L2 | PTTPQVSIFV | 425 | 10 | | | | | 5846 |
| HPV31 | L2 | PTTSGFDI | 127 | 8 | | | | | 5847 |
| HPV31 | L2 | PTTSGFDIA | 127 | 9 | | | | | 5848 |
| HPV31 | L2 | PTTSGFDIAT | 127 | 10 | | | | | 5849 |
| HPV31 | L2 | PTTSGFDIATT | 127 | 11 | | | | | 5850 |
| HPV31 | L2 | PVGPLDPSI | 97 | 9 | | | | | 5851 |
| HPV31 | L2 | PVGPLDPSIV | 97 | 10 | | | | | 5852 |
| HPV31 | L2 | PVSIDPVGPL | 92 | 10 | | | | | 5853 |
| HPV31 | L2 | QILRYGSM | 44 | 8 | | | | | 5854 |
| HPV31 | L2 | QILRYGSMGV | 44 | 10 | | | | | 5855 |
| HPV31 | L2 | QLITYENPA | 243 | 9 | | | | | 5856 |
| HPV31 | L2 | QLYQTCKA | 17 | 8 | | | | | 5857 |
| HPV31 | L2 | QLYQTCKAA | 17 | 9 | | | | | 5858 |
| HPV31 | L2 | QLYQTCKAAGT | 17 | 11 | | | | | 5859 |
| HPV31 | L2 | QQVKVIDPT | 228 | 9 | | | | | 5860 |
| HPV31 | L2 | QQVKVIDPTFL | 228 | 11 | | | | | 5861 |
| HPV31 | L2 | QTCKAAGT | 20 | 8 | | | | | 5862 |
| HPV31 | L2 | QTLRTRSGA | 303 | 9 | | | | | 5863 |
| HPV31 | L2 | QTLRTRSGAT | 303 | 10 | | | | | 5864 |
| HPV31 | L2 | QTLRTRSGATI | 303 | 11 | | | | | 5865 |
| HPV31 | L2 | QVFPFPLA | 417 | 8 | | | | | 5866 |
| HPV31 | L2 | QVFPFPLAPT | 417 | 10 | | | | | 5867 |
| HPV31 | L2 | QVFPFPLAPTT | 417 | 11 | | | | | 5868 |
| HPV31 | L2 | QVKVIDPT | 229 | 8 | | | | | 5869 |
| HPV31 | L2 | QVKVIDPTFL | 229 | 10 | | | | | 5870 |
| HPV31 | L2 | RASATQLYQT | 12 | 10 | | | | | 5871 |
| HPV31 | L2 | RLGLYSKA | 219 | 8 | | | | | 5872 |
| HPV31 | L2 | RLGLYSKAT | 219 | 9 | | | | | 5873 |
| HPV31 | L2 | RLGNKQTL | 298 | 8 | | | | | 5874 |
| HPV31 | L2 | RLGNKQTLRT | 298 | 10 | | | | | 5875 |
| HPV31 | L2 | RTGYVPLST | 69 | 9 | | | | | 5876 |
| HPV31 | L2 | RTKRASAT | 9 | 8 | | | | | 5877 |
| HPV31 | L2 | RTKRASATQL | 9 | 10 | | | | | 5878 |
| HPV31 | L2 | RTRSGATI | 306 | 8 | | | | | 5879 |
| HPV31 | L2 | RTRSGATIGA | 306 | 10 | | | | | 5880 |
| HPV31 | L2 | RVHYYYDI | 316 | 8 | | | | | 5881 |
| HPV31 | L2 | RVHYYYDISSI | 316 | 11 | | | | | 5882 |
| HPV31 | L2 | RVSYFFTDV | 454 | 9 | | | | | 5883 |
| HPV31 | L2 | RVSYFFTDVSV | 454 | 11 | | | | | 5884 |
| HPV31 | L2 | SAPKQLIT | 239 | 8 | | | | | 5885 |
| HPV31 | L2 | SATQLYQT | 14 | 8 | | | | | 5886 |
| HPV31 | L2 | SATQLYQTCKA | 14 | 11 | | | | | 5887 |
| HPV31 | L2 | SATTTSTL | 341 | 8 | | | | | 5888 |
| HPV31 | L2 | SAVSAYVPT | 381 | 9 | | | | | 5889 |
| HPV31 | L2 | SAVSAYVPTNT | 381 | 11 | | | | | 5890 |
| HPV31 | L2 | SAYVPTNT | 384 | 8 | | | | | 5891 |
| HPV31 | L2 | SAYVPTNTT | 384 | 9 | | | | | 5892 |
| HPV31 | L2 | SAYVPTNTTV | 384 | 10 | | | | | 5893 |
| HPV31 | L2 | SIDPVGPL | 94 | 8 | | | | | 5894 |
| HPV31 | L2 | SIEMQPLGA | 332 | 9 | | | | | 5895 |
| HPV31 | L2 | SIEMQPLGASA | 332 | 11 | | | | | 5896 |
| HPV31 | L2 | SIFVDGGDFYL | 431 | 11 | | | | | 5897 |
| HPV31 | L2 | SINPAGESI | 325 | 9 | | | | | 5898 |
| HPV31 | L2 | SINPAGESIEM | 325 | 11 | | | | | 5899 |
| HPV31 | L2 | SIPIRPPV | 86 | 8 | | | | | 5900 |
| HPV31 | L2 | SIPIRPPVSI | 86 | 10 | | | | | 5901 |
| HPV31 | L2 | SISTHNYEEI | 182 | 10 | | | | | 5902 |
| HPV31 | L2 | SIVSLVEESGI | 104 | 11 | | | | | 5903 |
| HPV31 | L2 | SLVEESGI | 107 | 8 | | | | | 5904 |
| HPV31 | L2 | SLVEESGIV | 107 | 9 | | | | | 5905 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | L2 | SLVEESGIVDV | 107 | 11 | | | | | 5906 |
| HPV31 | L2 | SLYFSNTSHNI | 260 | 11 | | | | | 5907 |
| HPV31 | L2 | SMGVFFGGL | 50 | 9 | | | | | 5908 |
| HPV31 | L2 | SMGVFFGGLGI | 50 | 11 | | | | | 5909 |
| HPV31 | L2 | STAVQSTSA | 374 | 9 | | | | | 5910 |
| HPV31 | L2 | STAVQSTSAV | 374 | 10 | | | | | 5911 |
| HPV31 | L2 | STGFDIPI | 396 | 8 | | | | | 5912 |
| HPV31 | L2 | STHENPTFT | 151 | 9 | | | | | 5913 |
| HPV31 | L2 | STHNYEEI | 184 | 8 | | | | | 5914 |
| HPV31 | L2 | STHNYEEIPM | 184 | 10 | | | | | 5915 |
| HPV31 | L2 | STKRTKRA | 6 | 8 | | | | | 5916 |
| HPV31 | L2 | STKRTKRASA | 6 | 10 | | | | | 5917 |
| HPV31 | L2 | STKRTKRASAT | 6 | 11 | | | | | 5918 |
| HPV31 | L2 | STLNDGLYDI | 346 | 10 | | | | | 5919 |
| HPV31 | L2 | STNNENIT | 199 | 8 | | | | | 5920 |
| HPV31 | L2 | STNNENITSST | 199 | 11 | | | | | 5921 |
| HPV31 | L2 | STPIPGVRRPA | 208 | 11 | | | | | 5922 |
| HPV31 | L2 | STRPSTVSEA | 76 | 10 | | | | | 5923 |
| HPV31 | L2 | STSAVSAYV | 379 | 9 | | | | | 5924 |
| HPV31 | L2 | STSAVSAYVPT | 379 | 11 | | | | | 5925 |
| HPV31 | L2 | STVSEASI | 80 | 8 | | | | | 5926 |
| HPV31 | L2 | STVSEASIPI | 80 | 10 | | | | | 5927 |
| HPV31 | L2 | SVLQPPTPA | 162 | 9 | | | | | 5928 |
| HPV31 | L2 | SVLQPPTPAET | 162 | 11 | | | | | 5929 |
| HPV31 | L2 | SVSTHENPT | 149 | 9 | | | | | 5930 |
| HPV31 | L2 | SVSTHENPTFT | 149 | 11 | | | | | 5931 |
| HPV31 | L2 | TADTTPAI | 137 | 8 | | | | | 5932 |
| HPV31 | L2 | TADTTPAIL | 137 | 9 | | | | | 5933 |
| HPV31 | L2 | TADTTPAILDV | 137 | 11 | | | | | 5934 |
| HPV31 | L2 | TAVQSTSA | 375 | 8 | | | | | 5935 |
| HPV31 | L2 | TAVQSTSAV | 375 | 9 | | | | | 5936 |
| HPV31 | L2 | TAVQSTSAVSA | 375 | 11 | | | | | 5937 |
| HPV31 | L2 | TLNDGLYDI | 347 | 9 | | | | | 5938 |
| HPV31 | L2 | TLNDGLYDIYA | 347 | 11 | | | | | 5939 |
| HPV31 | L2 | TLRTRSGA | 304 | 8 | | | | | 5940 |
| HPV31 | L2 | TLRTRSGAT | 304 | 9 | | | | | 5941 |
| HPV31 | L2 | TLRTRSGATI | 304 | 10 | | | | | 5942 |
| HPV31 | L2 | TQLYQTCKA | 16 | 9 | | | | | 5943 |
| HPV31 | L2 | TQLYQTCKAA | 16 | 10 | | | | | 5944 |
| HPV31 | L2 | TQQVKVIDPT | 227 | 10 | | | | | 5945 |
| HPV31 | L2 | TQVFPFPL | 416 | 8 | | | | | 5946 |
| HPV31 | L2 | TQVFPFPLA | 416 | 9 | | | | | 5947 |
| HPV31 | L2 | TQVFPFPLAPT | 416 | 11 | | | | | 5948 |
| HPV31 | L2 | TTADTTPA | 136 | 8 | | | | | 5949 |
| HPV31 | L2 | TTADTTPAI | 136 | 9 | | | | | 5950 |
| HPV31 | L2 | TTADTTPAIL | 136 | 10 | | | | | 5951 |
| HPV31 | L2 | TTIADQIL | 39 | 8 | | | | | 5952 |
| HPV31 | L2 | TTPAILDV | 140 | 8 | | | | | 5953 |
| HPV31 | L2 | TTPAILDVT | 140 | 9 | | | | | 5954 |
| HPV31 | L2 | TTPAILDVTSV | 140 | 11 | | | | | 5955 |
| HPV31 | L2 | TTPQVSIFV | 426 | 9 | | | | | 5956 |
| HPV31 | L2 | TTSGFDIA | 128 | 8 | | | | | 5957 |
| HPV31 | L2 | TTSGFDIAT | 128 | 9 | | | | | 5958 |
| HPV31 | L2 | TTSGFDIATT | 128 | 10 | | | | | 5959 |
| HPV31 | L2 | TTSGFDIATTA | 128 | 11 | | | | | 5960 |
| HPV31 | L2 | TTSTLNDGL | 344 | 9 | | | | | 5961 |
| HPV31 | L2 | TTTSTLNDGL | 343 | 10 | | | | | 5962 |
| HPV31 | L2 | TTVPLSTGFDI | 391 | 11 | | | | | 5963 |
| HPV31 | L2 | TVDTPATHNV | 362 | 10 | | | | | 5964 |
| HPV31 | L2 | TVNAEESL | 254 | 8 | | | | | 5965 |
| HPV31 | L2 | TVPLSTGFDI | 392 | 10 | | | | | 5966 |
| HPV31 | L2 | TVSEASIPI | 81 | 9 | | | | | 5967 |
| HPV31 | L2 | VIDPTFLSA | 232 | 9 | | | | | 5968 |
| HPV31 | L2 | VIPKIEHT | 32 | 8 | | | | | 5969 |
| HPV31 | L2 | VIPKIEHTT | 32 | 9 | | | | | 5970 |
| HPV31 | L2 | VIPKIEHTTI | 32 | 10 | | | | | 5971 |
| HPV31 | L2 | VIPKIEHTTIA | 32 | 11 | | | | | 5972 |
| HPV31 | L2 | VLQPPTPA | 163 | 8 | | | | | 5973 |
| HPV31 | L2 | VLQPPTPAET | 163 | 10 | | | | | 5974 |
| HPV31 | L2 | VQSTSAVSA | 377 | 9 | | | | | 5975 |
| HPV31 | L2 | VQSTSAVSAYV | 377 | 11 | | | | | 5976 |
| HPV31 | L2 | VTSVSTHENPT | 147 | 11 | | | | | 5977 |
| HPV31 | L2 | YADTDFTV | 356 | 8 | | | | | 5978 |
| HPV31 | L2 | YADTDFTVDT | 356 | 10 | | | | | 5979 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV31 | L2 | YLHPSYYM | 440 | 8 | | | | | 5980 |
| HPV31 | L2 | YLHPSYYML | 440 | 9 | | | | | 5981 |
| HPV31 | L2 | YMLKRRRKRV | 446 | 10 | | | | | 5982 |
| HPV31 | L2 | YQTCKAAGT | 19 | 9 | | | | | 5983 |
| HPV31 | L2 | YVPLSTRPST | 72 | 10 | | | | | 5984 |
| HPV31 | L2 | YVPLSTRPSTV | 72 | 11 | | | | | 5985 |
| HPV31 | L2 | YVPTNTTV | 386 | 8 | | | | | 5986 |
| HPV31 | L2 | YVPTNTTVPL | 386 | 10 | | | | | 5987 |
| HPV33 | E1 | AAAFLKSNSQA | 382 | 11 | | | | | 5988 |
| HPV33 | E1 | AACSQSAA | 90 | 8 | | | | | 5989 |
| HPV33 | E1 | AACSQSAAEDV | 90 | 11 | | | | | 5990 |
| HPV33 | E1 | AAEDVVDRA | 96 | 9 | | | | | 5991 |
| HPV33 | E1 | AAEDVVDRAA | 96 | 10 | | | | | 5992 |
| HPV33 | E1 | AAFLKSNSQA | 383 | 10 | | | | | 5993 |
| HPV33 | E1 | AANPCRTSI | 104 | 9 | | | | | 5994 |
| HPV33 | E1 | AARALFNI | 65 | 8 | | | | | 5995 |
| HPV33 | E1 | ALDGNEISI | 532 | 9 | | | | | 5996 |
| HPV33 | E1 | ALDGNEISIDV | 532 | 11 | | | | | 5997 |
| HPV33 | E1 | ALKRKFAA | 84 | 8 | | | | | 5998 |
| HPV33 | E1 | ALVQLKCPPL | 546 | 10 | | | | | 5999 |
| HPV33 | E1 | ALVQLKCPPLL | 546 | 11 | | | | | 6000 |
| HPV33 | E1 | ALYWFRTA | 311 | 8 | | | | | 6001 |
| HPV33 | E1 | ALYWFRTAM | 311 | 9 | | | | | 6002 |
| HPV33 | E1 | AMSNISDV | 318 | 8 | | | | | 6003 |
| HPV33 | E1 | AMSNISDVQGT | 318 | 11 | | | | | 6004 |
| HPV33 | E1 | AQLADSNSNA | 373 | 10 | | | | | 6005 |
| HPV33 | E1 | AQLADSNSNAA | 373 | 11 | | | | | 6006 |
| HPV33 | E1 | AVCALKRKFA | 81 | 10 | | | | | 6007 |
| HPV33 | E1 | AVCALKRKFAA | 81 | 11 | | | | | 6008 |
| HPV33 | E1 | AVIERRTGDNI | 22 | 11 | | | | | 6009 |
| HPV33 | E1 | CALKRKFA | 83 | 8 | | | | | 6010 |
| HPV33 | E1 | CALKRKFAA | 83 | 9 | | | | | 6011 |
| HPV33 | E1 | CALYWFRT | 310 | 8 | | | | | 6012 |
| HPV33 | E1 | CALYWFRTA | 310 | 9 | | | | | 6013 |
| HPV33 | E1 | CALYWFRTAM | 310 | 10 | | | | | 6014 |
| HPV33 | E1 | CITGYGISPSV | 230 | 11 | | | | | 6015 |
| HPV33 | E1 | CLTCDRGI | 259 | 8 | | | | | 6016 |
| HPV33 | E1 | CLTCDRGII | 259 | 9 | | | | | 6017 |
| HPV33 | E1 | CLTCDRGIII | 259 | 10 | | | | | 6018 |
| HPV33 | E1 | CLTCDRGIIIL | 259 | 11 | | | | | 6019 |
| HPV33 | E1 | CMLICGPA | 465 | 8 | | | | | 6020 |
| HPV33 | E1 | CMLICGPANT | 465 | 10 | | | | | 6021 |
| HPV33 | E1 | CMVIEPPKL | 297 | 9 | | | | | 6022 |
| HPV33 | E1 | CTDWCITGYGI | 226 | 11 | | | | | 6023 |
| HPV33 | E1 | CTGWFEVEA | 14 | 9 | | | | | 6024 |
| HPV33 | E1 | CTGWFEVEAV | 14 | 10 | | | | | 6025 |
| HPV33 | E1 | CTGWFEVEAVI | 14 | 11 | | | | | 6026 |
| HPV33 | E1 | CTYRKRKI | 118 | 8 | | | | | 6027 |
| HPV33 | E1 | CTYRKRKIDEL | 118 | 11 | | | | | 6028 |
| HPV33 | E1 | CVNSKSHFWL | 494 | 10 | | | | | 6029 |
| HPV33 | E1 | DAKIGMIDDV | 508 | 10 | | | | | 6030 |
| HPV33 | E1 | DAKIGMIDDVT | 508 | 11 | | | | | 6031 |
| HPV33 | E1 | DIAYYYAQL | 367 | 9 | | | | | 6032 |
| HPV33 | E1 | DIAYYYAQLA | 367 | 10 | | | | | 6033 |
| HPV33 | E1 | DLLEFIDDSM | 46 | 10 | | | | | 6034 |
| HPV33 | E1 | DLNAVCAL | 78 | 8 | | | | | 6035 |
| HPV33 | E1 | DLSEMVQWA | 349 | 9 | 0.0003 | | | | 6036 |
| HPV33 | E1 | DTEAARAL | 62 | 8 | | | | | 6037 |
| HPV33 | E1 | DTEAARALFNI | 62 | 11 | | | | | 6038 |
| HPV33 | E1 | DVKHRALV | 541 | 8 | | | | | 6039 |
| HPV33 | E1 | DVKHRALVQL | 541 | 10 | | | | | 6040 |
| HPV33 | E1 | DVQGTTPEWI | 324 | 10 | | | | | 6041 |
| HPV33 | E1 | DVTPISWT | 516 | 8 | | | | | 6042 |
| HPV33 | E1 | DVTPISWTYI | 516 | 10 | | | | | 6043 |
| HPV33 | E1 | EAARALFNI | 64 | 9 | | | | | 6044 |
| HPV33 | E1 | EAVIERRT | 21 | 8 | | | | | 6045 |
| HPV33 | E1 | EAYGISFM | 206 | 8 | | | | | 6046 |
| HPV33 | E1 | EAYGISFMEL | 206 | 10 | | | | | 6047 |
| HPV33 | E1 | EAYGISFMELV | 206 | 11 | | | | | 6048 |
| HPV33 | E1 | EISIDVKHRA | 537 | 10 | | | | | 6049 |
| HPV33 | E1 | EISIDVKHRAL | 537 | 11 | | | | | 6050 |
| HPV33 | E1 | EISNVLHSSNT | 186 | 11 | | | | | 6051 |
| HPV33 | E1 | ELEDSGYGNT | 127 | 10 | | | | | 6052 |
| HPV33 | E1 | ELTDDSDI | 361 | 8 | | | | | 6053 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E1 | ELTDDSDIA | 361 | 9 | | | | | 6054 |
| HPV33 | E1 | ELVRPFKSDKT | 214 | 11 | | | | | 6055 |
| HPV33 | E1 | EMVQWAYDNEL | 352 | 11 | | | | | 6056 |
| HPV33 | E1 | ETADDSGT | 38 | 8 | | | | | 6057 |
| HPV33 | E1 | ETADDSGTDL | 38 | 10 | | | | | 6058 |
| HPV33 | E1 | ETADDSGTDLL | 38 | 11 | | | | | 6059 |
| HPV33 | E1 | ETCMVIEPPKL | 295 | 11 | | | | | 6060 |
| HPV33 | E1 | ETNVDSCENV | 173 | 10 | | | | | 6061 |
| HPV33 | E1 | ETNVDSCENVT | 173 | 11 | | | | | 6062 |
| HPV33 | E1 | ETQQMVQQV | 139 | 9 | | | | | 6063 |
| HPV33 | E1 | EVEAVIERRT | 19 | 10 | | | | | 6064 |
| HPV33 | E1 | EVETQQMV | 137 | 8 | | | | | 6065 |
| HPV33 | E1 | EVETQQMVQQV | 137 | 11 | | | | | 6066 |
| HPV33 | E1 | EVSCETNV | 169 | 8 | | | | | 6067 |
| HPV33 | E1 | FAACSQSA | 89 | 8 | | | | | 6068 |
| HPV33 | E1 | FAACSQSAA | 89 | 9 | | | | | 6069 |
| HPV33 | E1 | FIDDSMENSI | 50 | 10 | | | | | 6070 |
| HPV33 | E1 | FLGAFKKFL | 449 | 9 | | | | | 6071 |
| HPV33 | E1 | FLKGCVISCV | 486 | 10 | | | | | 6072 |
| HPV33 | E1 | FLKGIPKKSCM | 456 | 11 | | | | | 6073 |
| HPV33 | E1 | FLKSNSQA | 385 | 8 | | | | | 6074 |
| HPV33 | E1 | FLKSNSQAKI | 385 | 10 | 0.0011 | | | | 6075 |
| HPV33 | E1 | FLKSNSQAKIV | 385 | 11 | | | | | 6076 |
| HPV33 | E1 | GAFKKFLKGI | 451 | 10 | | | | | 6077 |
| HPV33 | E1 | GIIILLLI | 265 | 8 | | | | | 6078 |
| HPV33 | E1 | GIMCRHYKKA | 399 | 10 | | | | | 6079 |
| HPV33 | E1 | GIPKKSCM | 459 | 8 | | | | | 6080 |
| HPV33 | E1 | GIPKKSCML | 459 | 9 | | | | | 6081 |
| HPV33 | E1 | GIPKKSCMLI | 459 | 10 | | | | | 6082 |
| HPV33 | E1 | GISFMELV | 209 | 8 | | | | | 6083 |
| HPV33 | E1 | GISPSVAESL | 235 | 10 | | | | | 6084 |
| HPV33 | E1 | GMGCTGWFEV | 11 | 10 | | | | | 6085 |
| HPV33 | E1 | GMIDDVTPI | 512 | 9 | | | | | 6086 |
| HPV33 | E1 | GMSLIQFL | 480 | 8 | | | | | 6087 |
| HPV33 | E1 | GQWIQSRCEKT | 416 | 11 | | | | | 6088 |
| HPV33 | E1 | GTDLLEFI | 44 | 8 | | | | | 6089 |
| HPV33 | E1 | GTDSRWPYL | 564 | 9 | | | | | 6090 |
| HPV33 | E1 | GTNGAGMGCT | 6 | 10 | | | | | 6091 |
| HPV33 | E1 | GTTPEWIDRL | 327 | 10 | | | | | 6092 |
| HPV33 | E1 | GTTPEWIDRLT | 327 | 11 | | | | | 6093 |
| HPV33 | E1 | GVGDDSEV | 163 | 8 | | | | | 6094 |
| HPV33 | E1 | HLQCLTCDRGI | 256 | 11 | | | | | 6095 |
| HPV33 | E1 | IAYYYAQL | 368 | 8 | | | | | 6096 |
| HPV33 | E1 | IAYYYAQLA | 368 | 9 | | | | | 6097 |
| HPV33 | E1 | ILYKFKEA | 200 | 8 | | | | | 6098 |
| HPV33 | E1 | ILYKFKEAYGI | 200 | 11 | | | | | 6099 |
| HPV33 | E1 | IMCRHYKKA | 400 | 9 | | | | | 6100 |
| HPV33 | E1 | IQADTEAA | 59 | 8 | | | | | 6101 |
| HPV33 | E1 | IQADTEAARA | 59 | 10 | | | | | 6102 |
| HPV33 | E1 | IQADTEAARAL | 59 | 11 | | | | | 6103 |
| HPV33 | E1 | IQEGEDDL | 72 | 8 | | | | | 6104 |
| HPV33 | E1 | IQEGEDDLNA | 72 | 10 | | | | | 6105 |
| HPV33 | E1 | IQEGEDDLNAV | 72 | 11 | | | | | 6106 |
| HPV33 | E1 | IQFLKGCV | 484 | 8 | | | | | 6107 |
| HPV33 | E1 | IQFLKGCVI | 484 | 9 | | | | | 6108 |
| HPV33 | E1 | IQSRCEKT | 419 | 8 | | | | | 6109 |
| HPV33 | E1 | ITGYGISPSV | 231 | 10 | | | | | 6110 |
| HPV33 | E1 | ITGYGISPSVA | 231 | 11 | | | | | 6111 |
| HPV33 | E1 | IVKDCGIM | 394 | 8 | | | | | 6112 |
| HPV33 | E1 | IVQLLRYQNI | 435 | 10 | | | | | 6113 |
| HPV33 | E1 | KAEKRKMSI | 407 | 9 | | | | | 6114 |
| HPV33 | E1 | KANILYKFKEA | 197 | 11 | | | | | 6115 |
| HPV33 | E1 | KIGMIDDV | 510 | 8 | | | | | 6116 |
| HPV33 | E1 | KIGMIDDVT | 510 | 9 | | | | | 6117 |
| HPV33 | E1 | KIGMIDDVTPI | 510 | 11 | | | | | 6118 |
| HPV33 | E1 | KIVKDCGI | 393 | 8 | | | | | 6119 |
| HPV33 | E1 | KIVKDCGIM | 393 | 9 | | | | | 6120 |
| HPV33 | E1 | KLMSNLLSI | 285 | 9 | | | | | 6121 |
| HPV33 | E1 | KLRSQTCA | 304 | 8 | | | | | 6122 |
| HPV33 | E1 | KLRSQTCAL | 304 | 9 | | | | | 6123 |
| HPV33 | E1 | KMSIGQWI | 412 | 8 | | | | | 6124 |
| HPV33 | E1 | KQHSLYTHL | 249 | 9 | | | | | 6125 |
| HPV33 | E1 | KTNDGGNWRPI | 425 | 11 | | | | | 6126 |
| HPV33 | E1 | KTSCTDWCI | 223 | 9 | | | | | 6127 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E1 | KTSCTDWCIT | 223 | 10 | | | | | 6128 |
| HPV33 | E1 | KVLIKQHSL | 245 | 9 | | | | | 6129 |
| HPV33 | E1 | KVLIKQHSLYT | 245 | 11 | | | | | 6130 |
| HPV33 | E1 | LADSNSNA | 375 | 8 | | | | | 6131 |
| HPV33 | E1 | LADSNSNAA | 375 | 9 | | | | | 6132 |
| HPV33 | E1 | LADSNSNAAA | 375 | 10 | | | | | 6133 |
| HPV33 | E1 | LICGPANT | 467 | 8 | | | | | 6134 |
| HPV33 | E1 | LIKQHSLYT | 247 | 9 | | | | | 6135 |
| HPV33 | E1 | LIKQHSLYTHL | 247 | 11 | | | | | 6136 |
| HPV33 | E1 | LIQFLKGCV | 483 | 9 | | | | | 6137 |
| HPV33 | E1 | LIQFLKGCVI | 483 | 10 | | | | | 6138 |
| HPV33 | E1 | LIRFRCSKNRL | 271 | 11 | | | | | 6139 |
| HPV33 | E1 | LLEFIDDSM | 47 | 9 | | | | | 6140 |
| HPV33 | E1 | LLLTSNTNA | 555 | 9 | | | | | 6141 |
| HPV33 | E1 | LLLTSNTNAGT | 555 | 11 | | | | | 6142 |
| HPV33 | E1 | LLRYQNIEFT | 438 | 10 | | | | | 6143 |
| HPV33 | E1 | LLRYQNIEFTA | 438 | 11 | | | | | 6144 |
| HPV33 | E1 | LLSIPETCM | 290 | 9 | | | | | 6145 |
| HPV33 | E1 | LLSIPETCMV | 290 | 10 | | | | | 6146 |
| HPV33 | E1 | LLSIPETCMVI | 290 | 11 | | | | | 6147 |
| HPV33 | E1 | LLTSNTNA | 556 | 8 | | | | | 6148 |
| HPV33 | E1 | LLTSNTNAGT | 556 | 10 | | | | | 6149 |
| HPV33 | E1 | LMSNLLSI | 286 | 8 | | | | | 6150 |
| HPV33 | E1 | LMSNLLSIPET | 286 | 11 | | | | | 6151 |
| HPV33 | E1 | LQCLTCDRGI | 257 | 10 | | | | | 6152 |
| HPV33 | E1 | LQCLTCDRGII | 257 | 11 | | | | | 6153 |
| HPV33 | E1 | LQEISNVL | 184 | 8 | | | | | 6154 |
| HPV33 | E1 | LQHSFNDNI | 339 | 9 | | | | | 6155 |
| HPV33 | E1 | LQPLSDAKI | 503 | 9 | | | | | 6156 |
| HPV33 | E1 | LQPLSDAKIGM | 503 | 11 | | | | | 6157 |
| HPV33 | E1 | LTCDRGII | 260 | 8 | | | | | 6158 |
| HPV33 | E1 | LTCDRGIII | 260 | 9 | | | | | 6159 |
| HPV33 | E1 | LTCDRGIIIL | 260 | 10 | | | | | 6160 |
| HPV33 | E1 | LTCDRGIIILL | 260 | 11 | | | | | 6161 |
| HPV33 | E1 | LTDDSDIA | 362 | 8 | | | | | 6162 |
| HPV33 | E1 | LTSNTNAGT | 557 | 9 | | | | | 6163 |
| HPV33 | E1 | LTVAKLMSNL | 281 | 10 | | | | | 6164 |
| HPV33 | E1 | LTVAKLMSNLL | 281 | 11 | | | | | 6165 |
| HPV33 | E1 | LVQLKCPPL | 547 | 9 | 0.0003 | | | | 6166 |
| HPV33 | E1 | LVQLKCPPLL | 547 | 10 | | | | | 6167 |
| HPV33 | E1 | LVQLKCPPLLL | 547 | 11 | | | | | 6168 |
| HPV33 | E1 | LVRPFKSDKT | 215 | 10 | | | | | 6169 |
| HPV33 | E1 | MADPEGTNGA | 1 | 10 | | | | | 6170 |
| HPV33 | E1 | MIDDVTPI | 513 | 8 | | | | | 6171 |
| HPV33 | E1 | MIDDVTPISWT | 513 | 11 | | | | | 6172 |
| HPV33 | E1 | MLICGPANT | 466 | 9 | | | | | 6173 |
| HPV33 | E1 | MVIEPPKL | 298 | 8 | | | | | 6174 |
| HPV33 | E1 | MVQWAYDNEL | 353 | 10 | | | | | 6175 |
| HPV33 | E1 | MVQWAYDNELT | 353 | 11 | | | | | 6176 |
| HPV33 | E1 | NAGTDSRWPYL | 562 | 11 | | | | | 6177 |
| HPV33 | E1 | NALDGNEI | 531 | 8 | | | | | 6178 |
| HPV33 | E1 | NALDGNEISI | 531 | 10 | | | | | 6179 |
| HPV33 | E1 | NAVCALKRKFA | 80 | 11 | | | | | 6180 |
| HPV33 | E1 | NIEFTAFL | 443 | 8 | | | | | 6181 |
| HPV33 | E1 | NIEFTAFLGA | 443 | 10 | | | | | 6182 |
| HPV33 | E1 | NIFDLSEM | 346 | 8 | | | | | 6183 |
| HPV33 | E1 | NIFDLSEMV | 346 | 9 | | | | | 6184 |
| HPV33 | E1 | NILYKFKEA | 199 | 9 | | | | | 6185 |
| HPV33 | E1 | NIQEGEDDL | 71 | 9 | | | | | 6186 |
| HPV33 | E1 | NIQEGEDDLNA | 71 | 11 | | | | | 6187 |
| HPV33 | E1 | NISDVQGT | 321 | 8 | | | | | 6188 |
| HPV33 | E1 | NISDVQGTT | 321 | 9 | | | | | 6189 |
| HPV33 | E1 | NISEDEDET | 31 | 9 | | | | | 6190 |
| HPV33 | E1 | NISEDEDETA | 31 | 10 | | | | | 6191 |
| HPV33 | E1 | NISTFKCSA | 627 | 9 | | | | | 6192 |
| HPV33 | E1 | NLLSIPET | 289 | 8 | | | | | 6193 |
| HPV33 | E1 | NLLSIPETCM | 289 | 10 | | | | | 6194 |
| HPV33 | E1 | NLLSIPETCMV | 289 | 11 | | | | | 6195 |
| HPV33 | E1 | NLNDLESSGV | 155 | 10 | | | | | 6196 |
| HPV33 | E1 | NTEVETQQM | 135 | 9 | | | | | 6197 |
| HPV33 | E1 | NTEVETQQMV | 135 | 10 | | | | | 6198 |
| HPV33 | E1 | NTGKSYFGM | 473 | 9 | | | | | 6199 |
| HPV33 | E1 | NTGKSYFGMSL | 473 | 11 | | | | | 6200 |
| HPV33 | E1 | NVDSCENV | 175 | 8 | | | | | 6201 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E1 | NVDSCENVT | 175 | 9 | | | | | 6202 |
| HPV33 | E1 | NVDSCENVTL | 175 | 10 | | | | | 6203 |
| HPV33 | E1 | NVLHSSNT | 189 | 8 | | | | | 6204 |
| HPV33 | E1 | NVLHSSNTKA | 189 | 10 | | | | | 6205 |
| HPV33 | E1 | NVTLQEISNV | 181 | 10 | | | | | 6206 |
| HPV33 | E1 | NVTLQEISNVL | 181 | 11 | | | | | 6207 |
| HPV33 | E1 | PANTGKSYFGM | 471 | 11 | | | | | 6208 |
| HPV33 | E1 | PISWTYIDDYM | 519 | 11 | | | | | 6209 |
| HPV33 | E1 | PIVQLLRYQNI | 434 | 11 | | | | | 6210 |
| HPV33 | E1 | PLLLTSNT | 554 | 8 | | | | | 6211 |
| HPV33 | E1 | PLLLTSNTNA | 554 | 10 | | | | | 6212 |
| HPV33 | E1 | PLSDAKIGM | 505 | 9 | | | | | 6213 |
| HPV33 | E1 | PLSDAKIGMI | 505 | 10 | | | | | 6214 |
| HPV33 | E1 | QADTEAARA | 60 | 9 | | | | | 6215 |
| HPV33 | E1 | QADTEAARAL | 60 | 10 | | | | | 6216 |
| HPV33 | E1 | QAKIVKDCGI | 391 | 10 | | | | | 6217 |
| HPV33 | E1 | QAKIVKDCGIM | 391 | 11 | | | | | 6218 |
| HPV33 | E1 | QLADSNSNA | 374 | 9 | | | | | 6219 |
| HPV33 | E1 | QLADSNSNAA | 374 | 10 | | | | | 6220 |
| HPV33 | E1 | QLADSNSNAAA | 374 | 11 | | | | | 6221 |
| HPV33 | E1 | QLKCPPLL | 549 | 8 | | | | | 6222 |
| HPV33 | E1 | QLKCPPLLL | 549 | 9 | | | | | 6223 |
| HPV33 | E1 | QLKCPPLLLT | 549 | 10 | | | | | 6224 |
| HPV33 | E1 | QLLRYQNI | 437 | 8 | | | | | 6225 |
| HPV33 | E1 | QLLRYQNIEFT | 437 | 11 | | | | | 6226 |
| HPV33 | E1 | QQVESQNGDT | 145 | 10 | | | | | 6227 |
| HPV33 | E1 | QTCALYWFRT | 308 | 10 | | | | | 6228 |
| HPV33 | E1 | QTCALYWFRTA | 308 | 11 | | | | | 6229 |
| HPV33 | E1 | QVESQNGDT | 146 | 9 | | | | | 6230 |
| HPV33 | E1 | QVESQNGDTNL | 146 | 11 | | | | | 6231 |
| HPV33 | E1 | RAANPCRT | 103 | 8 | | | | | 6232 |
| HPV33 | E1 | RAANPCRTSI | 103 | 10 | | | | | 6233 |
| HPV33 | E1 | RALVQLKCPPL | 545 | 11 | | | | | 6234 |
| HPV33 | E1 | RLTVAKLM | 280 | 8 | | | | | 6235 |
| HPV33 | E1 | RLTVAKLMSNL | 280 | 11 | | | | | 6236 |
| HPV33 | E1 | RTAMSNISDV | 316 | 10 | | | | | 6237 |
| HPV33 | E1 | RTSINKNKECT | 109 | 11 | | | | | 6238 |
| HPV33 | E1 | RTWCKLDL | 608 | 8 | | | | | 6239 |
| HPV33 | E1 | RTWCKLDLI | 608 | 9 | | | | | 6240 |
| HPV33 | E1 | SAAEDVVDRA | 95 | 10 | | | | | 6241 |
| HPV33 | E1 | SAAEDVVDRAA | 95 | 11 | | | | | 6242 |
| HPV33 | E1 | SAGENTRSL | 634 | 9 | | | | | 6243 |
| HPV33 | E1 | SIDVKHRA | 539 | 8 | | | | | 6244 |
| HPV33 | E1 | SIDVKHRAL | 539 | 9 | | | | | 6245 |
| HPV33 | E1 | SIDVKHRALV | 539 | 10 | | | | | 6246 |
| HPV33 | E1 | SINKNKECT | 111 | 9 | | | | | 6247 |
| HPV33 | E1 | SIPETCMV | 292 | 8 | | | | | 6248 |
| HPV33 | E1 | SIPETCMVI | 292 | 9 | | | | | 6249 |
| HPV33 | E1 | SIQADTEA | 58 | 8 | | | | | 6250 |
| HPV33 | E1 | SIQADTEAA | 58 | 9 | | | | | 6251 |
| HPV33 | E1 | SIQADTEAARA | 58 | 11 | | | | | 6252 |
| HPV33 | E1 | SLIQFLKGCV | 482 | 10 | | | | | 6253 |
| HPV33 | E1 | SLIQFLKGCVI | 482 | 11 | | | | | 6254 |
| HPV33 | E1 | SLKVLIKQHSL | 243 | 11 | | | | | 6255 |
| HPV33 | E1 | SLYTHLQCL | 252 | 9 | | | | | 6256 |
| HPV33 | E1 | SLYTHLQCLT | 252 | 10 | | | | | 6257 |
| HPV33 | E1 | SMENSIQA | 54 | 8 | | | | | 6258 |
| HPV33 | E1 | SMENSIQADT | 54 | 10 | | | | | 6259 |
| HPV33 | E1 | SQAKIVKDCGI | 390 | 11 | | | | | 6260 |
| HPV33 | E1 | SQNGDTNL | 149 | 8 | | | | | 6261 |
| HPV33 | E1 | SQNGDTNLNDL | 149 | 11 | | | | | 6262 |
| HPV33 | E1 | SQSAAEDV | 93 | 8 | | | | | 6263 |
| HPV33 | E1 | SQSAAEDVV | 93 | 9 | | | | | 6264 |
| HPV33 | E1 | SQTCALYWFRT | 307 | 11 | | | | | 6265 |
| HPV33 | E1 | STFKCSAGENT | 629 | 11 | | | | | 6266 |
| HPV33 | E1 | SVAESLKV | 239 | 8 | | | | | 6267 |
| HPV33 | E1 | SVAESLKVL | 239 | 9 | | | | | 6268 |
| HPV33 | E1 | SVAESLKVLI | 239 | 10 | | | | | 6269 |
| HPV33 | E1 | TADDSGTDL | 39 | 9 | | | | | 6270 |
| HPV33 | E1 | TADDSGTDLL | 39 | 10 | | | | | 6271 |
| HPV33 | E1 | TAFLGAFKKFL | 447 | 11 | | | | | 6272 |
| HPV33 | E1 | TAMSNISDV | 317 | 9 | | | | | 6273 |
| HPV33 | E1 | TLQEISNV | 183 | 8 | | | | | 6274 |
| HPV33 | E1 | TLQEISNVL | 183 | 9 | | | | | 6275 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E1 | TQQMVQQV | 140 | 8 | | | | | 6276 |
| HPV33 | E1 | TTPEWIDRL | 328 | 9 | | | | | 6277 |
| HPV33 | E1 | TTPEWIDRLT | 328 | 10 | | | | | 6278 |
| HPV33 | E1 | TTPEWIDRLTV | 328 | 11 | | | | | 6279 |
| HPV33 | E1 | TVAKLMSNL | 282 | 9 | | | | | 6280 |
| HPV33 | E1 | TVAKLMSNLL | 282 | 10 | | | | | 6281 |
| HPV33 | E1 | TVLQHSFNDNI | 337 | 11 | | | | | 6282 |
| HPV33 | E1 | VAESLKVL | 240 | 8 | | | | | 6283 |
| HPV33 | E1 | VAESLKVLI | 240 | 9 | | | | | 6284 |
| HPV33 | E1 | VAKLMSNL | 283 | 8 | | | | | 6285 |
| HPV33 | E1 | VAKLMSNLL | 283 | 9 | | | | | 6286 |
| HPV33 | E1 | VAKLMSNLLSI | 283 | 11 | | | | | 6287 |
| HPV33 | E1 | VIEPPKLRSQT | 299 | 11 | | | | | 6288 |
| HPV33 | E1 | VIERRTGDNI | 23 | 10 | | | | | 6289 |
| HPV33 | E1 | VLHSSNTKA | 190 | 9 | | | | | 6290 |
| HPV33 | E1 | VLHSSNTKANI | 190 | 11 | | | | | 6291 |
| HPV33 | E1 | VLIKQHSL | 246 | 8 | | | | | 6292 |
| HPV33 | E1 | VLIKQHSLYT | 246 | 10 | | | | | 6293 |
| HPV33 | E1 | VLQHSFNDNI | 338 | 10 | | | | | 6294 |
| HPV33 | E1 | VQGTTPEWI | 325 | 9 | | | | | 6295 |
| HPV33 | E1 | VQLKCPPL | 548 | 8 | | | | | 6296 |
| HPV33 | E1 | VQLKCPPLL | 548 | 9 | | | | | 6297 |
| HPV33 | E1 | VQLKCPPLLL | 548 | 10 | | | | | 6298 |
| HPV33 | E1 | VQLKCPPLLLT | 548 | 11 | | | | | 6299 |
| HPV33 | E1 | VQLLRYQNI | 436 | 9 | | | | | 6300 |
| HPV33 | E1 | VQQVESQNGDT | 144 | 11 | | | | | 6301 |
| HPV33 | E1 | VQWAYDNEL | 354 | 9 | | | | | 6302 |
| HPV33 | E1 | VQWAYDNELT | 354 | 10 | | | | | 6303 |
| HPV33 | E1 | VTLQEISNV | 182 | 9 | | | | | 6304 |
| HPV33 | E1 | VTLQEISNVL | 182 | 10 | | | | | 6305 |
| HPV33 | E1 | VTPISWTYI | 517 | 9 | | | | | 6306 |
| HPV33 | E1 | VVDRAANPCRT | 100 | 11 | | | | | 6307 |
| HPV33 | E1 | WAYDNELT | 356 | 8 | | | | | 6308 |
| HPV33 | E1 | WIDRLTVL | 332 | 8 | | | | | 6309 |
| HPV33 | E1 | WIQSRCEKT | 418 | 9 | | | | | 6310 |
| HPV33 | E1 | WLQPLSDA | 502 | 8 | | | | | 6311 |
| HPV33 | E1 | WLQPLSDAKI | 502 | 10 | | | | | 6312 |
| HPV33 | E1 | WTYIDDYM | 522 | 8 | | | | | 6313 |
| HPV33 | E1 | WTYIDDYMRNA | 522 | 11 | | | | | 6314 |
| HPV33 | E1 | YAQLADSNSNA | 372 | 11 | | | | | 6315 |
| HPV33 | E1 | YIDDYMRNA | 524 | 9 | | | | | 6316 |
| HPV33 | E1 | YIDDYMRNAL | 524 | 10 | | | | | 6317 |
| HPV33 | E1 | YLHSRLTV | 571 | 8 | | | | | 6318 |
| HPV33 | E1 | YMRNALDGNEI | 528 | 11 | | | | | 6319 |
| HPV33 | E1 | YQNIEFTA | 441 | 8 | | | | | 6320 |
| HPV33 | E1 | YQNIEFTAFL | 441 | 10 | | | | | 6321 |
| HPV33 | E1 | YTHLQCLT | 254 | 8 | | | | | 6322 |
| HPV33 | E2 | AAAKRRRPA | 223 | 9 | | | | | 6323 |
| HPV33 | E2 | AAAKRRRPADT | 223 | 11 | | | | | 6324 |
| HPV33 | E2 | AAKRRRPA | 224 | 8 | | | | | 6325 |
| HPV33 | E2 | AAKRRRPADT | 224 | 10 | | | | | 6326 |
| HPV33 | E2 | AAKRRRPADTT | 224 | 11 | | | | | 6327 |
| HPV33 | E2 | AAKYSKTQM | 175 | 9 | | | | | 6328 |
| HPV33 | E2 | ALDNRTART | 249 | 9 | | | | | 6329 |
| HPV33 | E2 | ALDNRTARTA | 249 | 10 | | | | | 6330 |
| HPV33 | E2 | ALDNRTARTAT | 249 | 11 | | | | | 6331 |
| HPV33 | E2 | ALLYTAKQM | 41 | 9 | | | | | 6332 |
| HPV33 | E2 | AQPLTKLFCA | 237 | 10 | | | | | 6333 |
| HPV33 | E2 | ATNCTNKQRT | 258 | 10 | | | | | 6334 |
| HPV33 | E2 | ATNCTNKQRTV | 258 | 11 | | | | | 6335 |
| HPV33 | E2 | AVQEKILDL | 10 | 9 | | | | | 6336 |
| HPV33 | E2 | CADPALDNRT | 245 | 10 | | | | | 6337 |
| HPV33 | E2 | CADPALDNRTA | 245 | 11 | | | | | 6338 |
| HPV33 | E2 | CALLYTAKQM | 40 | 10 | | | | | 6339 |
| HPV33 | E2 | CTMVTGKV | 145 | 8 | | | | | 6340 |
| HPV33 | E2 | CTMVTGKVDYI | 145 | 11 | | | | | 6341 |
| HPV33 | E2 | CTNKQRTV | 261 | 8 | | | | | 6342 |
| HPV33 | E2 | DAAKYSKT | 174 | 8 | | | | | 6343 |
| HPV33 | E2 | DAAKYSKTQM | 174 | 10 | | | | | 6344 |
| HPV33 | E2 | DLPSQIEHWKL | 25 | 11 | | | | | 6345 |
| HPV33 | E2 | DLYEADKT | 17 | 8 | | | | | 6346 |
| HPV33 | E2 | DLYEADKTDL | 17 | 10 | | | | | 6347 |
| HPV33 | E2 | DTAQPLTKL | 235 | 9 | | | | | 6348 |
| HPV33 | E2 | DTCTMVTGKV | 143 | 10 | | | | | 6349 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E2 | DTTDTAQPL | 232 | 9 | | | | | 6350 |
| HPV33 | E2 | DTTDTAQPLT | 232 | 10 | | | | | 6351 |
| HPV33 | E2 | EADKTDLPSQI | 20 | 11 | | | | | 6352 |
| HPV33 | E2 | EISARLNA | 3 | 8 | | | | | 6353 |
| HPV33 | E2 | EISARLNAV | 3 | 9 | | | | | 6354 |
| HFV33 | E2 | EIYIIEEDT | 136 | 9 | | | | | 6355 |
| HPV33 | E2 | EIYIIEEDTCT | 136 | 11 | | | | | 6356 |
| HPV33 | E2 | ELQMALET | 74 | 8 | | | | | 6357 |
| HPV33 | E2 | ELQMALETL | 74 | 9 | | | | | 6358 |
| HPV33 | E2 | ELYSSMSST | 298 | 9 | | | | | 6359 |
| HPV33 | E2 | EQQQQMFL | 328 | 8 | | | | | 6360 |
| HPV33 | E2 | EQQQQMFLGT | 328 | 10 | | | | | 6361 |
| HPV33 | E2 | EQQQQMFLGTV | 328 | 11 | | | | | 6362 |
| HPV33 | E2 | ETLSKSQYST | 80 | 10 | | | | | 6363 |
| HPV33 | E2 | EVHVGGQV | 185 | 8 | | | | | 6364 |
| HPV33 | E2 | EVHVGGQVI | 185 | 9 | | | | | 6365 |
| HPV33 | E2 | EVHVGGQVIV | 185 | 10 | | | | | 6366 |
| HPV33 | E2 | FLGTVKIPPT | 334 | 10 | | | | | 6367 |
| HPV33 | E2 | FLGTVKIPPTV | 334 | 11 | | | | | 6368 |
| HPV33 | E2 | FQVIELQM | 70 | 8 | | | | | 6369 |
| HPV33 | E2 | FQVIELQMA | 70 | 9 | | | | | 6370 |
| HPV33 | E2 | FQVIELQMAL | 70 | 10 | | | | | 6371 |
| HPV33 | E2 | FVTEQQQQM | 325 | 9 | | | | | 6372 |
| HPV33 | E2 | FVTEQQQQMFL | 325 | 11 | | | | | 6373 |
| HPV33 | E2 | GIVTVTFV | 319 | 8 | | | | | 6374 |
| HPV33 | E2 | GIVTVTFVT | 319 | 9 | | | | | 6375 |
| HPV33 | E2 | GMYYIHNCEKV | 156 | 11 | | | | | 6376 |
| HPV33 | E2 | GQVIVCPT | 190 | 8 | | | | | 6377 |
| HPV33 | E2 | GQVIVCPTSI | 190 | 10 | | | | | 6378 |
| HPV33 | E2 | GTVKIPPT | 336 | 8 | | | | | 6379 |
| HPV33 | E2 | GTVKIPPTV | 336 | 9 | | | | | 6380 |
| HPV33 | E2 | GTVKIPPTVQI | 336 | 11 | | | | | 6381 |
| HPV33 | E2 | HLCHQVVPSL | 53 | 10 | | | | | 6382 |
| HPV33 | E2 | HLCHQVVPSLL | 53 | 11 | | | | | 6383 |
| HPV33 | E2 | HLKGESNSL | 278 | 9 | | | | | 6384 |
| HPV33 | E2 | HQVVPSLL | 56 | 8 | | | | | 6385 |
| HPV33 | E2 | HQVVPSLLA | 56 | 9 | | | | | 6386 |
| HPV33 | E2 | HVGGQVIV | 187 | 8 | | | | | 6387 |
| HPV33 | E2 | HVGGQVIVCPT | 187 | 11 | | | | | 6388 |
| HPV33 | E2 | IIEEDTCT | 139 | 8 | | | | | 6389 |
| HPV33 | E2 | IIEEDTCTM | 139 | 9 | | | | | 6390 |
| HPV33 | E2 | IIEEDTCTMV | 139 | 10 | | | | | 6391 |
| HPV33 | E2 | IIEEDTCTMVT | 139 | 11 | | | | | 6392 |
| HPV33 | E2 | ILDLYEADKT | 15 | 10 | | | | | 6393 |
| HPV33 | E2 | IVHLKGESNSL | 276 | 11 | | | | | 6394 |
| HPV33 | E2 | IVTVTFVT | 320 | 8 | | | | | 6395 |
| HPV33 | E2 | KAFQVIEL | 68 | 8 | | | | | 6396 |
| HPV33 | E2 | KAFQVIELQM | 68 | 10 | | | | | 6397 |
| HPV33 | E2 | KAFQVIELQMA | 68 | 11 | | | | | 6398 |
| HPV33 | E2 | KILDLYEA | 14 | 8 | | | | | 6399 |
| HPV33 | E2 | KILDLYEADKT | 14 | 11 | | | | | 6400 |
| HPV33 | E2 | KIPPTVQI | 339 | 8 | | | | | 6401 |
| HPV33 | E2 | KIPPTVQIST | 339 | 10 | | | | | 6402 |
| HPV33 | E2 | KLFCADPA | 242 | 8 | | | | | 6403 |
| HPV33 | E2 | KLFCADPAL | 242 | 9 | | | | | 6404 |
| HPV33 | E2 | KLIRMECA | 34 | 8 | | | | | 6405 |
| HPV33 | E2 | KLIRMECAL | 34 | 9 | | | | | 6406 |
| HPV33 | E2 | KLIRMECALL | 34 | 10 | | | | | 6407 |
| HPV33 | E2 | KQGETVTV | 112 | 8 | | | | | 6408 |
| HPV33 | E2 | KQMGFSHL | 47 | 8 | | | | | 6409 |
| HPV33 | E2 | KQRTVCSSNV | 264 | 10 | | | | | 6410 |
| HPV33 | E2 | KQRTVCSSNVA | 264 | 11 | | | | | 6411 |
| HPV33 | E2 | KTDLPSQI | 23 | 8 | | | | | 6412 |
| HPV33 | E2 | KTKAFQVI | 66 | 8 | | | | | 6413 |
| HPV33 | E2 | KTKAFQVIEL | 66 | 10 | | | | | 6414 |
| HPV33 | E2 | KTQMWEVHV | 180 | 9 | | | | | 6415 |
| HPV33 | E2 | KVDYIGMYYI | 151 | 10 | | | | | 6416 |
| HPV33 | E2 | KVYFKYFKEDA | 165 | 11 | | | | | 6417 |
| HPV33 | E2 | LASKTKAFQV | 63 | 10 | | | | | 6418 |
| HPV33 | E2 | LASKTKAFQVI | 63 | 11 | | | | | 6419 |
| HPV33 | E2 | LIRMECAL | 35 | 8 | | | | | 6420 |
| HPV33 | E2 | LIRMECALL | 35 | 9 | | | | | 6421 |
| HPV33 | E2 | LIRMECALLYT | 35 | 11 | | | | | 6422 |
| HPV33 | E2 | LLASKTKA | 62 | 8 | | | | | 6423 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E2 | LLASKTKAFQV | 62 | 11 | | | | | 6424 |
| HPV33 | E2 | LLYTAKQM | 42 | 8 | | | | | 6425 |
| HPV33 | E2 | LQMALETL | 75 | 8 | | | | | 6426 |
| HPV33 | E2 | LQQTSLEV | 94 | 8 | | | | | 6427 |
| HPV33 | E2 | LQQTSLEVWL | 94 | 10 | | | | | 6428 |
| HPV33 | E2 | LTKLFCADPA | 240 | 10 | | | | | 6429 |
| HPV33 | E2 | LTKLFCADPAL | 240 | 11 | | | | | 6430 |
| HPV33 | E2 | MVTGKVDYI | 147 | 9 | | | | | 6431 |
| HPV33 | E2 | MVTGKVDYIGM | 147 | 11 | | | | | 6432 |
| HPV33 | E2 | NAVQEKIL | 9 | 8 | | | | | 6433 |
| HPV33 | E2 | NAVQEKILDL | 9 | 10 | | | | | 6434 |
| HPV33 | E2 | NQISTTET | 202 | 8 | | | | | 6435 |
| HPV33 | E2 | NQISTTETA | 202 | 9 | | | | | 6436 |
| HPV33 | E2 | NQISTTETADI | 202 | 11 | | | | | 6437 |
| HPV33 | E2 | NTMDYTNWGEI | 127 | 11 | | | | | 6438 |
| HPV33 | E2 | NVAPIVHL | 272 | 8 | | | | | 6439 |
| HPV33 | E2 | PADTTDTA | 230 | 8 | | | | | 6440 |
| HPV33 | E2 | PADTTDTAQPL | 230 | 11 | | | | | 6441 |
| HPV33 | E2 | PALDNRTA | 248 | 8 | | | | | 6442 |
| HPV33 | E2 | PALDNRTART | 248 | 10 | | | | | 6443 |
| HPV33 | E2 | PALDNRTARTA | 248 | 11 | | | | | 6444 |
| HPV33 | E2 | PLTKLFCA | 239 | 8 | | | | | 6445 |
| HPV33 | E2 | PLTKLFCADPA | 239 | 11 | | | | | 6446 |
| HPV33 | E2 | PQAAAKRRRPA | 221 | 11 | | | | | 6447 |
| HPV33 | E2 | PTSISSNQI | 196 | 9 | | | | | 6448 |
| HPV33 | E2 | PTSISSNQIST | 196 | 11 | | | | | 6449 |
| HPV33 | E2 | PTVQISTGFM | 342 | 10 | | | | | 6450 |
| HPV33 | E2 | PTVQISTGFMT | 342 | 11 | | | | | 6451 |
| HPV33 | E2 | QAAAKRRRPA | 222 | 10 | | | | | 6452 |
| HPV33 | E2 | QIEHWKLI | 29 | 8 | | | | | 6453 |
| HPV33 | E2 | QIEHWKLIRM | 29 | 10 | | | | | 6454 |
| HPV33 | E2 | QISTGFMT | 345 | 8 | | | | | 6455 |
| HPV33 | E2 | QISTGFMTL | 345 | 9 | | | | | 6456 |
| HPV33 | E2 | QISTTETA | 203 | 8 | | | | | 6457 |
| HPV33 | E2 | QISTTETADI | 203 | 10 | | | | | 6458 |
| HPV33 | E2 | QMFLGTVKI | 332 | 9 | | | | | 6459 |
| HPV33 | E2 | QMGFSHLCHQV | 48 | 11 | | | | | 6460 |
| HPV33 | E2 | QMWEVHVGGQV | 182 | 11 | | | | | 6461 |
| HPV33 | E2 | QQMFLGTV | 331 | 8 | | | | | 6462 |
| HPV33 | E2 | QQMFLGTVKI | 331 | 10 | | | | | 6463 |
| HPV33 | E2 | QQQMFLGT | 330 | 8 | | | | | 6464 |
| HPV33 | E2 | QQQMFLGTV | 330 | 9 | | | | | 6465 |
| HPV33 | E2 | QQQMFLGTVKI | 330 | 11 | | | | | 6466 |
| HPV33 | E2 | QQQQMFLGT | 329 | 9 | | | | | 6467 |
| HPV33 | E2 | QQQQMFLGTV | 329 | 10 | | | | | 6468 |
| HPV33 | E2 | QQTSLEVWL | 95 | 9 | | | | | 6469 |
| HPV33 | E2 | QTDNDNRPPQA | 213 | 11 | | | | | 6470 |
| HPV33 | E2 | QTSLEVWL | 96 | 8 | | | | | 6471 |
| HPV33 | E2 | QVIELQMA | 71 | 8 | | | | | 6472 |
| HPV33 | E2 | QVIELQMAL | 71 | 9 | | | | | 6473 |
| HPV33 | E2 | QVIELQMALET | 71 | 11 | | | | | 6474 |
| HPV33 | E2 | QVIVCPTSI | 191 | 9 | | | | | 6475 |
| HPV33 | E2 | QVVPSLLA | 57 | 8 | | | | | 6476 |
| HPV33 | E2 | QVVPSLLASKT | 57 | 11 | | | | | 6477 |
| HPV33 | E2 | RLKPYKEL | 292 | 8 | | | | | 6478 |
| HPV33 | E2 | RLNAVQEKI | 7 | 9 | | | | | 6479 |
| HPV33 | E2 | RLNAVQEKIL | 7 | 10 | | | | | 6480 |
| HPV33 | E2 | RMECALLYT | 37 | 9 | | | | | 6481 |
| HPV33 | E2 | RMECALLYTA | 37 | 10 | | | | | 6482 |
| HPV33 | E2 | RTARTATNCT | 253 | 10 | | | | | 6483 |
| HPV33 | E2 | RTVCSSNV | 266 | 8 | | | | | 6484 |
| HPV33 | E2 | RTVCSSNVA | 266 | 9 | | | | | 6485 |
| HPV33 | E2 | RTVCSSNVAPI | 266 | 11 | | | | | 6486 |
| HPV33 | E2 | SARLNAVQEKI | 5 | 11 | | | | | 6487 |
| HPV33 | E2 | SISSNQIST | 198 | 9 | | | | | 6488 |
| HPV33 | E2 | SISSNQISTT | 198 | 10 | | | | | 6489 |
| HPV33 | E2 | SLKCLRYRL | 285 | 9 | | | | | 6490 |
| HPV33 | E2 | SLLASKTKA | 61 | 9 | | | | | 6491 |
| HPV33 | E2 | SMSSTWHWT | 302 | 9 | | | | | 6492 |
| HPV33 | E2 | SQIEHWKL | 28 | 8 | | | | | 6493 |
| HPV33 | E2 | SQIEHWKLI | 28 | 9 | | | | | 6494 |
| HPV33 | E2 | SQIEHWKLIRM | 28 | 11 | | | | | 6495 |
| HPV33 | E2 | SQWTLQQT | 90 | 8 | | | | | 6496 |
| HPV33 | E2 | SQWTLQQTSL | 90 | 10 | | | | | 6497 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E2 | SQYSTSQWT | 85 | 9 | | | | | 6498 |
| HPV33 | E2 | SQYSTSQWTL | 85 | 10 | | | | | 6499 |
| HPV33 | E2 | STSQWTLQQT | 88 | 10 | | | | | 6500 |
| HPV33 | E2 | STTETADI | 205 | 8 | | | | | 6501 |
| HPV33 | E2 | STTETADIQT | 205 | 10 | | | | | 6502 |
| HPV33 | E2 | TAKQMGFSHL | 45 | 10 | | | | | 6503 |
| HPV33 | E2 | TAQPLTKL | 236 | 8 | | | | | 6504 |
| HPV33 | E2 | TAQPLTKLFCA | 236 | 11 | | | | | 6505 |
| HPV33 | E2 | TARTATNCT | 254 | 9 | | | | | 6506 |
| HPV33 | E2 | TATNCTNKQRT | 257 | 11 | | | | | 6507 |
| HPV33 | E2 | TLQQTSLEV | 93 | 9 | | | | | 6508 |
| HPV33 | E2 | TLQQTSLEVWL | 93 | 11 | | | | | 6509 |
| HPV33 | E2 | TLSKSQYST | 81 | 9 | | | | | 6510 |
| HPV33 | E2 | TMDYTNWGEI | 128 | 10 | | | | | 6511 |
| HPV33 | E2 | TMVTGKVDYI | 146 | 10 | | | | | 6512 |
| HPV33 | E2 | TQMWEVHV | 181 | 8 | | | | | 6513 |
| HPV33 | E2 | TTDTAQPL | 233 | 8 | | | | | 6514 |
| HPV33 | E2 | TTDTAQPLT | 233 | 9 | | | | | 6515 |
| HPV33 | E2 | TTDTAQPLTKL | 233 | 11 | | | | | 6516 |
| HPV33 | E2 | TTETADIQT | 206 | 9 | | | | | 6517 |
| HPV33 | E2 | TVCSSNVA | 267 | 8 | | | | | 6518 |
| HPV33 | E2 | TVCSSNVAPI | 267 | 10 | | | | | 6519 |
| HPV33 | E2 | TVCSSNVAPIV | 267 | 11 | | | | | 6520 |
| HPV33 | E2 | TVKIPPTV | 337 | 8 | | | | | 6521 |
| HPV33 | E2 | TVKIPPTVQI | 337 | 10 | | | | | 6522 |
| HPV33 | E2 | TVQISTGFM | 343 | 9 | | | | | 6523 |
| HPV33 | E2 | TVQISTGFMT | 343 | 10 | | | | | 6524 |
| HPV33 | E2 | TVQISTGFMTL | 343 | 11 | | | | | 6525 |
| HPV33 | E2 | TVQYDNDKKNT | 118 | 11 | | | | | 6526 |
| HPV33 | E2 | VIELQMAL | 72 | 8 | | | | | 6527 |
| HPV33 | E2 | VIELQMALET | 72 | 10 | | | | | 6528 |
| HPV33 | E2 | VIELQMALETL | 72 | 11 | | | | | 6529 |
| HPV33 | E2 | VIVCPTSI | 192 | 8 | | | | | 6530 |
| HPV33 | E2 | VQEKILDL | 11 | 8 | | | | | 6531 |
| HPV33 | E2 | VQEKILDLYEA | 11 | 11 | | | | | 6532 |
| HPV33 | E2 | VQISTGFM | 344 | 8 | | | | | 6533 |
| HPV33 | E2 | VQISTGFMT | 344 | 9 | | | | | 6534 |
| HPV33 | E2 | VQISTGFMTL | 344 | 10 | | | | | 6535 |
| HPV33 | E2 | VQYDNDKKNT | 119 | 10 | | | | | 6536 |
| HPV33 | E2 | VQYDNDKKNTM | 119 | 11 | | | | | 6537 |
| HPV33 | E2 | VTEQQQQM | 326 | 8 | | | | | 6538 |
| HPV33 | E2 | VTEQQQQMFL | 326 | 10 | | | | | 6539 |
| HPV33 | E2 | VTFVTEQQQQM | 323 | 11 | | | | | 6540 |
| HPV33 | E2 | VTGKVDYI | 148 | 8 | | | | | 6541 |
| HPV33 | E2 | VTGKVDYIGM | 148 | 10 | | | | | 6542 |
| HPV33 | E2 | VVPSLLASKT | 58 | 10 | | | | | 6543 |
| HPV33 | E2 | WTLQQTSL | 92 | 8 | | | | | 6544 |
| HPV33 | E2 | WTLQQTSLEV | 92 | 10 | | | | | 6545 |
| HPV33 | E2 | YIHNCEKV | 159 | 8 | | | | | 6546 |
| HPV33 | E2 | YIIEEDTCT | 138 | 9 | | | | | 6547 |
| HPV33 | E2 | YIIEEDTCTM | 138 | 10 | | | | | 6548 |
| HPV33 | E2 | YIIEEDTCTMV | 138 | 11 | | | | | 6549 |
| HPV33 | E2 | YTAKQMGFSHL | 44 | 11 | | | | | 6550 |
| HPV33 | E2 | YTNWGEIYI | 131 | 9 | | | | | 6551 |
| HPV33 | E2 | YTNWGEIYII | 131 | 10 | | | | | 6552 |
| HPV33 | E5 | CINFHAQHM | 63 | 9 | | | | | 6553 |
| HPV33 | E5 | CTNFHAQHMT | 63 | 10 | | | | | 6554 |
| HPV33 | E5 | CLSLLLRPL | 14 | 9 | | | | | 6555 |
| HPV33 | E5 | CLSLLLRPLI | 14 | 10 | | | | | 6556 |
| HPV33 | E5 | CLSLLLRPLIL | 14 | 11 | | | | | 6557 |
| HPV33 | E5 | FILFLCLSL | 9 | 9 | | | | | 6558 |
| HPV33 | E5 | FILFLCLSLL | 9 | 10 | | | | | 6559 |
| HPV33 | E5 | FILFLCLSLLL | 9 | 11 | | | | | 6560 |
| HPV33 | E5 | FLCLSLLL | 12 | 8 | | | | | 6561 |
| HPV33 | E5 | FLCLSLLLRPL | 12 | 11 | | | | | 6562 |
| HPV33 | E5 | FLYLPMMCI | 56 | 9 | | | | | 6563 |
| HPV33 | E5 | FVFVLCFI | 3 | 8 | | | | | 6564 |
| HPV33 | E5 | FVFVLCFIL | 3 | 9 | | | | | 6565 |
| HPV33 | E5 | FVFVLCFILFL | 3 | 11 | | | | | 6566 |
| HPV33 | E5 | FVGSPLKI | 42 | 8 | | | | | 6567 |
| HPV33 | E5 | FVLCFILFL | 5 | 9 | | | | | 6568 |
| HPV33 | E5 | FVLCFILFLCL | 5 | 11 | | | | | 6569 |
| HPV33 | E5 | ILFLCLSL | 10 | 8 | | | | | 6570 |
| HPV33 | E5 | ILFLCLSLL | 10 | 9 | | | | | 6571 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E5 | ILFLCLSLLL | 10 | 10 | | | | | 6572 |
| HPV33 | E5 | ILSISTYA | 23 | 8 | | | | | 6573 |
| HPV33 | E5 | ILSISTYAWL | 23 | 10 | | | | | 6574 |
| HPV33 | E5 | ILSISTYAWLL | 23 | 11 | | | | | 6575 |
| HPV33 | E5 | KIFFCYLL | 48 | 8 | | | | | 6576 |
| HPV33 | E5 | KIFFCYLLFL | 48 | 10 | | | | | 6577 |
| HPV33 | E5 | LILSISTYA | 22 | 9 | | | | | 6578 |
| HPV33 | E5 | LILSISTYAWL | 22 | 11 | | | | | 6579 |
| HPV33 | E5 | LLFLYLPM | 54 | 8 | | | | | 6580 |
| HPV33 | E5 | LLFLYLPMM | 54 | 9 | | | | | 6581 |
| HPV33 | E5 | LLFLYLPMMCI | 54 | 11 | | | | | 6582 |
| HPV33 | E5 | LLLRPLIL | 17 | 8 | | | | | 6583 |
| HPV33 | E5 | LLLRPLILSI | 17 | 10 | | | | | 6584 |
| HPV33 | E5 | LLLWVFVGSPL | 37 | 11 | | | | | 6585 |
| HPV33 | E5 | LLRPLILSI | 18 | 9 | | | | | 6586 |
| HPV33 | E5 | LLRPLILSIST | 18 | 11 | | | | | 6587 |
| HPV33 | E5 | LLVLVLLL | 32 | 8 | | | | | 6588 |
| HPV33 | E5 | LLVLVLLLWV | 32 | 10 | | | | | 6589 |
| HPV33 | E5 | LLWVFVGSPL | 38 | 10 | | | | | 6590 |
| HPV33 | E5 | LVLLLWVFV | 35 | 9 | | | | | 6591 |
| HPV33 | E5 | LVLVLLLWV | 33 | 9 | | | | | 6592 |
| HPV33 | E5 | LVLVLLLWVFV | 33 | 11 | | | | | 6593 |
| HPV33 | E5 | MIFVFVLCFI | 1 | 10 | | | | | 6594 |
| HPV33 | E5 | MIFVFVLCFIL | 1 | 11 | | | | | 6595 |
| HPV33 | E5 | MMCINFHA | 61 | 8 | | | | | 6596 |
| HPV33 | E5 | MMCINFHAQHM | 61 | 11 | | | | | 6597 |
| HPV33 | E5 | PLILSIST | 21 | 8 | | | | | 6598 |
| HPV33 | E5 | PLILSISTYA | 21 | 10 | | | | | 6599 |
| HPV33 | E5 | PLKIFFCYL | 46 | 9 | | | | | 6600 |
| HPV33 | E5 | PLKIFFCYLL | 46 | 10 | | | | | 6601 |
| HPV33 | E5 | PMMCINFHA | 60 | 9 | | | | | 6602 |
| HPV33 | E5 | SISTYAWL | 25 | 8 | | | | | 6603 |
| HPV33 | E5 | SISTYAWLL | 25 | 9 | | | | | 6604 |
| HPV33 | E5 | SISTYAWLLV | 25 | 10 | | | | | 6605 |
| HPV33 | E5 | SISTYAWLLVL | 25 | 11 | | | | | 6606 |
| HPV33 | E5 | SLLLRPLI | 16 | 8 | | | | | 6607 |
| HPV33 | E5 | SLLLRPLIL | 16 | 9 | | | | | 6608 |
| HPV33 | E5 | SLLLRPLILSI | 16 | 11 | | | | | 6609 |
| HPV33 | E5 | STYAWLLV | 27 | 8 | | | | | 6610 |
| HPV33 | E5 | STYAWLLVL | 27 | 9 | | | | | 6611 |
| HPV33 | E5 | STYAWLLVLV | 27 | 10 | | | | | 6612 |
| HPV33 | E5 | STYAWLLVLVL | 27 | 11 | | | | | 6613 |
| HPV33 | E5 | VLCFILFL | 6 | 8 | | | | | 6614 |
| HPV33 | E5 | VLCFILFLCL | 6 | 10 | | | | | 6615 |
| HPV33 | E5 | VLLLWVFV | 36 | 8 | | | | | 6616 |
| HPV33 | E5 | VLVLLLWV | 34 | 8 | | | | | 6617 |
| HPV33 | E5 | VLVLLLWVFV | 34 | 10 | | | | | 6618 |
| HPV33 | E5 | WLLVLVLL | 31 | 8 | | | | | 6619 |
| HPV33 | E5 | WLLVLVLLL | 31 | 9 | | | | | 6620 |
| HPV33 | E5 | WLLVLVLLLWV | 31 | 11 | | | | | 6621 |
| HPV33 | E5 | WVFVGSPL | 40 | 8 | | | | | 6622 |
| HPV33 | E5 | WVFVGSPLKI | 40 | 10 | | | | | 6623 |
| HPV33 | E5 | YAWLLVLV | 29 | 8 | | | | | 6624 |
| HPV33 | E5 | YAWLLVLVL | 29 | 9 | | | | | 6625 |
| HPV33 | E5 | YAWLLVLVLL | 29 | 10 | | | | | 6626 |
| HPV33 | E5 | YAWLLVLVLLL | 29 | 11 | | | | | 6627 |
| HPV33 | E5 | YLLFLYLPM | 53 | 9 | | | | | 6628 |
| HPV33 | E5 | YLLFLYLPMM | 53 | 10 | | | | | 6629 |
| HPV33 | E5 | YLPMMCINFHA | 58 | 11 | | | | | 6630 |
| HPV33 | E6 | AACWRSRRRET | 137 | 11 | | | | | 6631 |
| HPV33 | E6 | ALETTIHNI | 18 | 9 | | | | | 6632 |
| HPV33 | E6 | ALETTIHNIEL | 18 | 11 | | | | | 6633 |
| HPV33 | E6 | CIICQRPL | 103 | 8 | | | | | 6634 |
| HPV33 | E6 | CLRFLSKI | 66 | 8 | | | | | 6635 |
| HPV33 | E6 | CQALETTI | 16 | 8 | | | | | 6636 |
| HPV33 | E6 | CQALETTIHNI | 16 | 11 | | | | | 6637 |
| HPV33 | E6 | CVECKKPL | 30 | 8 | | | | | 6638 |
| HPV33 | E6 | DLCQALET | 14 | 8 | | | | | 6639 |
| HPV33 | E6 | DLCQALETT | 14 | 9 | | | | | 6640 |
| HPV33 | E6 | DLCQALETTI | 14 | 10 | | | | | 6641 |
| HPV33 | E6 | DLNKRFHNI | 120 | 9 | | | | | 6642 |
| HPV33 | E6 | DTEEKPRT | 4 | 8 | | | | | 6643 |
| HPV33 | E6 | DTEEKPRTL | 4 | 9 | | | | | 6644 |
| HPV33 | E6 | EILIRCII | 98 | 8 | | | | | 6645 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E6 | ELQCVECKKPL | 27 | 11 | | | | | 6646 |
| HPV33 | E6 | EQTVKKPL | 89 | 8 | | | | | 6647 |
| HPV33 | E6 | EQTVKKPLNEI | 89 | 11 | | | | | 6648 |
| HPV33 | E6 | ETTIHNIEL | 20 | 9 | | | | | 6649 |
| HPV33 | E6 | EVYDFAFA | 41 | 8 | | | | | 6650 |
| HPV33 | E6 | EVYDFAFADL | 41 | 10 | | | | | 6651 |
| HPV33 | E6 | EVYDFAFADLT | 41 | 11 | | | | | 6652 |
| HPV33 | E6 | FAFADLTV | 45 | 8 | | | | | 6653 |
| HPV33 | E6 | FAFADLTVV | 45 | 9 | | | | | 6654 |
| HPV33 | E6 | FQDTEEKPRT | 2 | 10 | | | | | 6655 |
| HPV33 | E6 | FQDTEEKPRTL | 2 | 11 | | | | | 6656 |
| HPV33 | E6 | GICKLCLRFL | 61 | 10 | | | | | 6657 |
| HPV33 | E6 | HVDLNKRFHNI | 118 | 11 | | | | | 6658 |
| HPV33 | E6 | KLCLRFLSKI | 64 | 10 | | | | | 6659 |
| HPV33 | E6 | LIRCIICQRPL | 100 | 11 | | | | | 6660 |
| HPV33 | E6 | LQCVECKKPL | 28 | 10 | | | | | 6661 |
| HPV33 | E6 | LQRSEVYDFA | 37 | 10 | | | | | 6662 |
| HPV33 | E6 | NISGRWAGRCA | 127 | 11 | | | | | 6663 |
| HPV33 | E6 | NTLEQTVKKPL | 86 | 11 | | | | | 6664 |
| HPV33 | E6 | PLCPQEKKRHV | 109 | 11 | | | | | 6665 |
| HPV33 | E6 | PLNEILIRCI | 95 | 10 | | | | | 6666 |
| HPV33 | E6 | PLNEILIRCII | 95 | 11 | | | | | 6667 |
| HPV33 | E6 | PLQRSEVYDFA | 36 | 11 | | | | | 6668 |
| HPV33 | E6 | PQEKKRHV | 112 | 8 | | | | | 6669 |
| HPV33 | E6 | PQEKKRHVDL | 112 | 10 | | | | | 6670 |
| HPV33 | E6 | QALETTIHNI | 17 | 10 | | | | | 6671 |
| HPV33 | E6 | QTVKKPLNEI | 90 | 10 | | | | | 6672 |
| HPV33 | E6 | QTVKKPLNEIL | 90 | 11 | | | | | 6673 |
| HPV33 | E6 | RTLHDLCQA | 10 | 9 | | | | | 6674 |
| HPV33 | E6 | RTLHDLCQAL | 10 | 10 | | | | | 6675 |
| HPV33 | E6 | SVYGNTLEQT | 82 | 10 | | | | | 6676 |
| HPV33 | E6 | SVYGNTLEQTV | 82 | 11 | | | | | 6677 |
| HPV33 | E6 | TIHNIELQCV | 22 | 10 | | | | | 6678 |
| HPV33 | E6 | TLEQTVKKPL | 87 | 10 | | | | | 6679 |
| HPV33 | E6 | TLHDLCQA | 11 | 8 | | | | | 6680 |
| HPV33 | E6 | TLHDLCQAL | 11 | 9 | | | | | 6681 |
| HPV33 | E6 | TLHDLCQALET | 11 | 11 | | | | | 6682 |
| HPV33 | E6 | TTIHNIEL | 21 | 8 | | | | | 6683 |
| HPV33 | E6 | TTIHNIELQCV | 21 | 11 | | | | | 6684 |
| HPV33 | E6 | TVKKPLNEI | 91 | 9 | | | | | 6685 |
| HPV33 | E6 | TVKKPLNEIL | 91 | 10 | | | | | 6686 |
| HPV33 | E6 | TVKKPLNEILI | 91 | 11 | | | | | 6687 |
| HPV33 | E6 | VVYREGNPFGI | 52 | 11 | | | | | 6688 |
| HPV33 | E7 | AQPATADYYI | 45 | 10 | | | | | 6689 |
| HPV33 | E7 | AQPATADYYIV | 45 | 11 | | | | | 6690 |
| HPV33 | E7 | ATADYYIV | 48 | 8 | | | | | 6691 |
| HPV33 | E7 | ATADYYIVT | 48 | 9 | | | | | 6692 |
| HPV33 | E7 | CVNSTASDL | 68 | 9 | | | | | 6693 |
| HPV33 | E7 | CVNSTASDLRT | 68 | 11 | | | | | 6694 |
| HPV33 | E7 | DLRTIQQL | 75 | 8 | | | | | 6695 |
| HPV33 | E7 | DLRTIQQLL | 75 | 9 | | | | | 6696 |
| HPV33 | E7 | DLRTIQQLLM | 75 | 10 | | | | | 6697 |
| HPV33 | E7 | DLYCYEQL | 21 | 8 | 0.0001 | | | | 6698 |
| HPV33 | E7 | DLYPEPTDL | 14 | 9 | | | | | 6699 |
| HPV33 | E7 | GLDRPDGQA | 37 | 9 | | | | | 6700 |
| HPV33 | E7 | GQAQPATA | 43 | 8 | | | | | 6701 |
| HPV33 | E7 | GTVNIVCPT | 85 | 9 | | | | | 6702 |
| HPV33 | E7 | GTVNIVCPTCA | 85 | 11 | | | | | 6703 |
| HPV33 | E7 | HTCNTTVRL | 59 | 9 | | | | | 6704 |
| HPV33 | E7 | HTCNTTVRLCV | 59 | 11 | | | | | 6705 |
| HPV33 | E7 | IQQLLMGT | 79 | 8 | | | | | 6706 |
| HPV33 | E7 | IQQLLMGTV | 79 | 9 | | | | | 6707 |
| HPV33 | E7 | IQQLLMGTVNI | 79 | 11 | | | | | 6708 |
| HPV33 | E7 | IVTCCHTCNT | 54 | 10 | | | | | 6709 |
| HPV33 | E7 | IVTCCHTCNTT | 54 | 11 | | | | | 6710 |
| HPV33 | E7 | LLMGTVNI | 82 | 8 | | | | | 6711 |
| HPV33 | E7 | LLMGTVNIV | 82 | 9 | | | | | 6712 |
| HPV33 | E7 | LMGTVNIV | 83 | 8 | | | | | 6713 |
| HPV33 | E7 | LMGTVNIVCPT | 83 | 11 | | | | | 6714 |
| HPV33 | E7 | NIVCPTCA | 88 | 8 | | | | | 6715 |
| HPV33 | E7 | NTTVRLCV | 62 | 8 | | | | | 6716 |
| HPV33 | E7 | NTTVRLCVNST | 62 | 11 | | | | | 6717 |
| HPV33 | E7 | PATADYYI | 47 | 8 | | | | | 6718 |
| HPV33 | E7 | PATADYYIV | 47 | 9 | | | | | 6719 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | E7 | PATADYYIVT | 47 | 10 | | | | | 6720 |
| HPV33 | E7 | PTDLYCYEQL | 19 | 10 | | | | | 6721 |
| HPV33 | E7 | PTLKEYVL | 6 | 8 | | | | | 6722 |
| HPV33 | E7 | PTLKEYVLDL | 6 | 10 | | | | | 6723 |
| HPV33 | E7 | QAQPATADYYI | 44 | 11 | | | | | 6724 |
| HPV33 | E7 | QLLMGTVNI | 81 | 9 | | | | | 6725 |
| HPV33 | E7 | QLLMGTVNIV | 81 | 10 | | | | | 6726 |
| HPV33 | E7 | QQLLMGTV | 80 | 8 | | | | | 6727 |
| HPV33 | E7 | QQLLMGTVNI | 80 | 10 | | | | | 6728 |
| HPV33 | E7 | QQLLMGTVNIV | 80 | 11 | | | | | 6729 |
| HPV33 | E7 | RLCVNSTA | 66 | 8 | | | | | 6730 |
| HPV33 | E7 | RLCVNSTASDL | 66 | 11 | | | | | 6731 |
| HPV33 | E7 | RTIQQLLM | 77 | 8 | | | | | 6732 |
| HPV33 | E7 | RTIQQLLMGT | 77 | 10 | | | | | 6733 |
| HPV33 | E7 | RTIQQLLMGTV | 77 | 11 | | | | | 6734 |
| HPV33 | E7 | STASDLRT | 71 | 8 | | | | | 6735 |
| HPV33 | E7 | STASDLRTI | 71 | 9 | | | | | 6736 |
| HPV33 | E7 | TADYYIVT | 49 | 8 | | | | | 6737 |
| HPV33 | E7 | TASDLRTI | 72 | 8 | | | | | 6738 |
| HPV33 | E7 | TASDLRTIQQL | 72 | 11 | | | | | 6739 |
| HPV33 | E7 | TIQQLLMGT | 78 | 9 | | | | | 6740 |
| HPV33 | E7 | TIQQLLMGTV | 78 | 10 | | | | | 6741 |
| HPV33 | E7 | TLKEYVLDL | 7 | 9 | | | | | 6742 |
| HPV33 | E7 | TTVRLCVNST | 63 | 10 | | | | | 6743 |
| HPV33 | E7 | TTVRLCVNSTA | 63 | 11 | | | | | 6744 |
| HPV33 | E7 | TVNIVCPT | 86 | 8 | | | | | 6745 |
| HPV33 | E7 | TVNIVCPTCA | 86 | 10 | | | | | 6746 |
| HPV33 | E7 | TVRLCVNST | 64 | 9 | | | | | 6747 |
| HPV33 | E7 | TVRLCVNSTA | 64 | 10 | | | | | 6748 |
| HPV33 | E7 | VLDLYPEPT | 12 | 9 | | | | | 6749 |
| HPV33 | E7 | VLDLYPEPTDL | 12 | 11 | | | | | 6750 |
| HPV33 | E7 | VTCCHTCNT | 55 | 9 | | | | | 6751 |
| HPV33 | E7 | VTCCHTCNTT | 55 | 10 | | | | | 6752 |
| HPV33 | E7 | VTCCHTCNTTV | 55 | 11 | | | | | 6753 |
| HPV33 | E7 | YIVTCCHT | 53 | 8 | | | | | 6754 |
| HPV33 | E7 | YIVTCCHTCNT | 53 | 11 | | | | | 6755 |
| HPV33 | E7 | YVLDLYPEPT | 11 | 10 | | | | | 6756 |
| HPV33 | L1 | AAPANDCPPL | 179 | 10 | | | | | 6757 |
| HPV33 | L1 | AAPTSTRT | 482 | 8 | | | | | 6758 |
| HPV33 | L1 | AAPTSTRTSSA | 482 | 11 | | | | | 6759 |
| HPV33 | L1 | AITCQKTV | 424 | 8 | | | | | 6760 |
| HPV33 | L1 | AQGHNNGI | 316 | 8 | | | | | 6761 |
| HPV33 | L1 | ATVYLPPV | 9 | 8 | | | | | 6762 |
| HPV33 | L1 | ATVYLPPVPV | 9 | 10 | | | | | 6763 |
| HPV33 | L1 | AVGHPYFSI | 44 | 9 | | | | | 6764 |
| HPV33 | L1 | AVPDDLYI | 270 | 8 | | | | | 6765 |
| HPV33 | L1 | CLLGCKPPT | 158 | 9 | | | | | 6766 |
| HPV33 | L1 | CLSMDYKQT | 147 | 9 | | | | | 6767 |
| HPV33 | L1 | CLSMDYKQTQL | 147 | 11 | | | | | 6768 |
| HPV33 | L1 | CMDFKTLQA | 207 | 9 | | | | | 6769 |
| HPV33 | L1 | CTQVTSDST | 345 | 9 | | | | | 6770 |
| HPV33 | L1 | DILEDWQFGL | 396 | 10 | | | | | 6771 |
| HPV33 | L1 | DILEDWQFGLT | 396 | 11 | | | | | 6772 |
| HPV33 | L1 | DLKEKFSA | 449 | 8 | | | | | 6773 |
| HPV33 | L1 | DLKEKFSADL | 449 | 10 | | | | | 6774 |
| HPV33 | L1 | DLQFVFQL | 370 | 8 | | | | | 6775 |
| HPV33 | L1 | DLQFVFQLCKV | 370 | 11 | | | | | 6776 |
| HPV33 | L1 | DLYIKGSGT | 274 | 9 | | | | | 6777 |
| HPV33 | L1 | DLYIKGSGTT | 274 | 10 | | | | | 6778 |
| HPV33 | L1 | DLYIKGSGTTA | 274 | 11 | | | | | 6779 |
| HPV33 | L1 | DMVDTGFGCM | 199 | 10 | | | | | 6780 |
| HPV33 | L1 | DQFPLGRKFL | 459 | 10 | | | | | 6781 |
| HPV33 | L1 | DQFPLGRKFLL | 459 | 11 | | | | | 6782 |
| HPV33 | L1 | DTGFGCMDFKT | 202 | 11 | | | | | 6783 |
| HPV33 | L1 | DTQRLVWA | 95 | 8 | | | | | 6784 |
| HPV33 | L1 | DTQRLVWACV | 95 | 10 | | | | | 6785 |
| HPV33 | L1 | DTSFYNPDT | 88 | 9 | | | | | 6786 |
| HPV33 | L1 | DTTRSTNM | 335 | 8 | | | | | 6787 |
| HPV33 | L1 | DTTRSTNMT | 335 | 9 | | | | | 6788 |
| HPV33 | L1 | DTTRSTNMTL | 335 | 10 | | | | | 6789 |
| HPV33 | L1 | DTYRFVTSQA | 415 | 10 | | | | | 6790 |
| HPV33 | L1 | DTYRFVTSQAI | 415 | 11 | | | | | 6791 |
| HPV33 | L1 | DVPIDICGST | 219 | 10 | | | | | 6792 |
| HPV33 | L1 | EATVYLPPV | 8 | 9 | | | | | 6793 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | L1 | EATVYLPPVPV | 8 | 11 | | | | | 6794 |
| HPV33 | L1 | EAVPDDLYI | 269 | 9 | | | | | 6795 |
| HPV33 | L1 | EIGRGQPL | 107 | 8 | | | | | 6796 |
| HPV33 | L1 | EIGRGQPLGV | 107 | 10 | | | | | 6797 |
| HPV33 | L1 | EVDLKEKFSA | 447 | 10 | | | | | 6798 |
| HPV33 | L1 | EVMTYIHA | 385 | 8 | | | | | 6799 |
| HPV33 | L1 | EVMTYIHAM | 385 | 9 | | | | | 6800 |
| HPV33 | L1 | FLLQAGLKA | 467 | 9 | | | | | 6801 |
| HPV33 | L1 | FLRREQMFV | 249 | 9 | | | | | 6802 |
| HPV33 | L1 | FQLCKVTL | 375 | 8 | | | | | 6803 |
| HPV33 | L1 | FQLCKVTLT | 375 | 9 | | | | | 6804 |
| HPV33 | L1 | FQLCKVTLTA | 375 | 10 | | | | | 6805 |
| HPV33 | L1 | FVFQLCKV | 373 | 8 | | | | | 6806 |
| HPV33 | L1 | FVFQLCKVT | 373 | 9 | | | | | 6807 |
| HPV33 | L1 | FVFQLCKVTL | 373 | 10 | | | | | 6808 |
| HPV33 | L1 | FVFQLCKVTLT | 373 | 11 | | | | | 6809 |
| HPV33 | L1 | FVRHFFNRA | 256 | 9 | | | | | 6810 |
| HPV33 | L1 | FVRHFFNRAGT | 256 | 11 | | | | | 6811 |
| HPV33 | L1 | FVTSQAIT | 419 | 8 | | | | | 6812 |
| HPV33 | L1 | FVTVVDTT | 330 | 8 | | | | | 6813 |
| HPV33 | L1 | FVTVVDTTRST | 330 | 11 | | | | | 6814 |
| HPV33 | L1 | GADNRECL | 141 | 8 | | | | | 6815 |
| HPV33 | L1 | GADNRECLSM | 141 | 10 | | | | | 6816 |
| HPV33 | L1 | GICWGNQV | 322 | 8 | | | | | 6817 |
| HPV33 | L1 | GICWGNQVFV | 322 | 10 | | | | | 6818 |
| HPV33 | L1 | GICWGNQVFVT | 322 | 11 | | | | | 6819 |
| HPV33 | L1 | GISGHPLL | 117 | 8 | | | | | 6820 |
| HPV33 | L1 | GLEIGRGQPL | 105 | 10 | | | | | 6821 |
| HPV33 | L1 | GLKAKPKL | 472 | 8 | | | | | 6822 |
| HPV33 | L1 | GLKAKPKLKRA | 472 | 11 | | | | | 6823 |
| HPV33 | L1 | GLQYRVFRV | 68 | 9 | | | | | 6824 |
| HPV33 | L1 | GLQYRVFRVRL | 68 | 11 | | | | | 6825 |
| HPV33 | L1 | GLTPPPSA | 404 | 8 | | | | | 6826 |
| HPV33 | L1 | GLTPPPSASL | 404 | 10 | | | | | 6827 |
| HPV33 | L1 | GQPGADNRECL | 138 | 11 | | | | | 6828 |
| HPV33 | L1 | GQPLGVGI | 111 | 8 | | | | | 6829 |
| HPV33 | L1 | GTLGEAVPDDL | 265 | 11 | | | | | 6830 |
| HPV33 | L1 | GTTASIQSSA | 281 | 10 | | | | | 6831 |
| HPV33 | L1 | GVACTNAA | 173 | 8 | | | | | 6832 |
| HPV33 | L1 | GVACTNAAPA | 173 | 10 | | | | | 6833 |
| HPV33 | L1 | GVGISGHPL | 115 | 9 | | | | | 6834 |
| HPV33 | L1 | GVGISGHPLL | 115 | 10 | | | | | 6835 |
| HPV33 | L1 | HAMNPDIL | 391 | 8 | | | | | 6836 |
| HPV33 | L1 | HVEEYDLQFV | 365 | 10 | | | | | 6837 |
| HPV33 | L1 | IEDGDMV | 194 | 8 | | | | | 6838 |
| HPV33 | L1 | IIEDGDMVDT | 194 | 10 | | | | | 6839 |
| HPV33 | L1 | ILEDWQFGL | 397 | 9 | | | | | 6840 |
| HPV33 | L1 | ILEDWQFGLT | 397 | 10 | | | | | 6841 |
| HPV33 | L1 | IQSSAFFPT | 286 | 9 | | | | | 6842 |
| HPV33 | L1 | KAKPKLKRA | 474 | 9 | | | | | 6843 |
| HPV33 | L1 | KAKPKLKRAA | 474 | 10 | | | | | 6844 |
| HPV33 | L1 | KLKRAAPT | 478 | 8 | | | | | 6845 |
| HPV33 | L1 | KLKRAAPTST | 478 | 10 | | | | | 6846 |
| HPV33 | L1 | KLLVPKVSGL | 60 | 10 | | | | | 6847 |
| HPV33 | L1 | KMTSEPYGDSL | 236 | 11 | | | | | 6848 |
| HPV33 | L1 | KQTQLCLL | 153 | 8 | | | | | 6849 |
| HPV33 | L1 | KTLQANKSDV | 211 | 10 | | | | | 6850 |
| HPV33 | L1 | KVSGLQYRV | 65 | 9 | | | | | 6851 |
| HPV33 | L1 | KVTLTAEV | 379 | 8 | | | | | 6852 |
| HPV33 | L1 | KVTLTAEVM | 379 | 9 | | | | | 6853 |
| HPV33 | L1 | KVTLTAEVMT | 379 | 10 | | | | | 6854 |
| HPV33 | L1 | KVVSTDEYV | 20 | 9 | | | | | 6855 |
| HPV33 | L1 | LAVGHPYFSI | 43 | 10 | | | | | 6856 |
| HPV33 | L1 | LINTIIEDGDM | 190 | 11 | | | | | 6857 |
| HPV33 | L1 | LLAVGHPYFSI | 42 | 11 | | | | | 6858 |
| HPV33 | L1 | LLGCKPPT | 159 | 8 | | | | | 6859 |
| HPV33 | L1 | LLNKFDDT | 123 | 8 | | | | | 6860 |
| HPV33 | L1 | LLNKFDDTET | 123 | 10 | | | | | 6861 |
| HPV33 | L1 | LLQAGLKA | 468 | 8 | | | | | 6862 |
| HPV33 | L1 | LLVPKVSGL | 61 | 9 | | | | | 6863 |
| HPV33 | L1 | LQAGLKAKPKL | 469 | 11 | | | | | 6864 |
| HPV33 | L1 | LQANKSDV | 213 | 8 | | | | | 6865 |
| HPV33 | L1 | LQANKSDVPI | 213 | 10 | | | | | 6866 |
| HPV33 | L1 | LQDTYRFV | 413 | 8 | | | | | 6867 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | L1 | LQDTYRFVT | 413 | 9 | | | | | 6868 |
| HPV33 | L1 | LQFVFQLCKV | 371 | 10 | | | | | 6869 |
| HPV33 | L1 | LQFVFQLCKVT | 371 | 11 | | | | | 6870 |
| HPV33 | L1 | LQRAQGHNNGI | 313 | 11 | | | | | 6871 |
| HPV33 | L1 | LQYRVFRV | 69 | 8 | | | | | 6872 |
| HPV33 | L1 | LQYRVFRVRL | 69 | 10 | | | | | 6873 |
| HPV33 | L1 | LTAEVMTYI | 382 | 9 | | | | | 6874 |
| HPV33 | L1 | LTAEVMTYIHA | 382 | 11 | | | | | 6875 |
| HPV33 | L1 | LTPPPSASL | 405 | 9 | | | | | 6876 |
| HPV33 | L1 | LVPKVSGL | 62 | 8 | | | | | 6877 |
| HPV33 | L1 | LVWACVGL | 99 | 8 | | | | | 6878 |
| HPV33 | L1 | LVWACVGLEI | 99 | 10 | | | | | 6879 |
| HPV33 | L1 | MTLCTQVT | 342 | 8 | | | | | 6880 |
| HPV33 | L1 | MTSEPYGDSL | 237 | 10 | | | | | 6881 |
| HPV33 | L1 | MTYIHAMNPDI | 387 | 11 | | | | | 6882 |
| HPV33 | L1 | MVDTGFGCM | 200 | 9 | | | | | 6883 |
| HPV33 | L1 | MVTSESQL | 299 | 8 | | | | | 6884 |
| HPV33 | L1 | NAAPANDCPPL | 178 | 11 | | | | | 6885 |
| HPV33 | L1 | NAKKLLVPKV | 57 | 10 | | | | | 6886 |
| HPV33 | L1 | NMTLCTQV | 341 | 8 | | | | | 6887 |
| HPV33 | L1 | NMTLCTQVT | 341 | 9 | | | | | 6888 |
| HPV33 | L1 | NQVFVTVV | 327 | 8 | | | | | 6889 |
| HPV33 | L1 | NQVFVTVVDT | 327 | 10 | | | | | 6890 |
| HPV33 | L1 | NQVFVTVVDTT | 327 | 11 | | | | | 6891 |
| HPV33 | L1 | NTIIEDGDM | 192 | 9 | | | | | 6892 |
| HPV33 | L1 | NTIIEDGDMV | 192 | 10 | | | | | 6893 |
| HPV33 | L1 | PANDCPPL | 181 | 8 | | | | | 6894 |
| HPV33 | L1 | PANDCPPLEL | 181 | 10 | | | | | 6895 |
| HPV33 | L1 | PANDCPPLELI | 181 | 11 | | | | | 6896 |
| HPV33 | L1 | PIDICGST | 221 | 8 | | | | | 6897 |
| HPV33 | L1 | PLELINTI | 187 | 8 | | | | | 6898 |
| HPV33 | L1 | PLELINTII | 187 | 9 | | | | | 6899 |
| HPV33 | L1 | PLGKYTFWEV | 439 | 10 | | | | | 6900 |
| HPV33 | L1 | PLGRKFLL | 462 | 8 | | | | | 6901 |
| HPV33 | L1 | PLGRKFLLQA | 462 | 10 | | | | | 6902 |
| HPV33 | L1 | PLGVGISGHPL | 113 | 11 | | | | | 6903 |
| HPV33 | L1 | PLLNKFDDT | 122 | 9 | | | | | 6904 |
| HPV33 | L1 | PLLNKFDDTET | 122 | 11 | | | | | 6905 |
| HPV33 | L1 | PTGEHWGKGV | 165 | 10 | | | | | 6906 |
| HPV33 | L1 | PTGEHWGKGVA | 165 | 11 | | | | | 6907 |
| HPV33 | L1 | PTNAKKLL | 55 | 8 | | | | | 6908 |
| HPV33 | L1 | PTNAKKLLV | 55 | 9 | | | | | 6909 |
| HPV33 | L1 | PTPSGSMV | 293 | 8 | | | | | 6910 |
| HPV33 | L1 | PTPSGSMVT | 293 | 9 | | | | | 6911 |
| HPV33 | L1 | PTSTRTSSA | 484 | 9 | | | | | 6912 |
| HPV33 | L1 | PVPVSKVV | 15 | 8 | | | | | 6913 |
| HPV33 | L1 | PVPVSKVVST | 15 | 10 | | | | | 6914 |
| HPV33 | L1 | PVSKVVST | 17 | 8 | | | | | 6915 |
| HPV33 | L1 | QAGLKAKPKL | 470 | 10 | | | | | 6916 |
| HPV33 | L1 | QAITCQKT | 423 | 8 | | | | | 6917 |
| HPV33 | L1 | QAITCQKTV | 423 | 9 | | | | | 6918 |
| HPV33 | L1 | QANKSDVPI | 214 | 9 | | | | | 6919 |
| HPV33 | L1 | QANKSDVPIDI | 214 | 11 | | | | | 6920 |
| HPV33 | L1 | QLCKVTLT | 376 | 8 | | | | | 6921 |
| HPV33 | L1 | QLCKVTLTA | 376 | 9 | | | | | 6922 |
| HPV33 | L1 | QLCKVTLTAEV | 376 | 11 | | | | | 6923 |
| HPV33 | L1 | QLCLLGCKPPT | 156 | 11 | | | | | 6924 |
| HPV33 | L1 | QLFNKPYWL | 305 | 9 | | | | | 6925 |
| HPV33 | L1 | QMFVRHFFNRA | 254 | 11 | | | | | 6926 |
| HPV33 | L1 | QVFVTVVDT | 328 | 9 | | | | | 6927 |
| HPV33 | L1 | QVFVTVVDTT | 328 | 10 | | | | | 6928 |
| HPV33 | L1 | RAAPTSTRT | 481 | 9 | | | | | 6929 |
| HPV33 | L1 | RAGTLGEA | 263 | 8 | | | | | 6930 |
| HPV33 | L1 | RAGTLGEAV | 263 | 9 | | | | | 6931 |
| HPV33 | L1 | RAQGHNNGI | 315 | 9 | | | | | 6932 |
| HPV33 | L1 | RLVWACVGL | 98 | 9 | | | | | 6933 |
| HPV33 | L1 | RLVWACVGLEI | 98 | 11 | | | | | 6934 |
| HPV33 | L1 | RTSIYYA | 30 | 8 | | | | | 6935 |
| HPV33 | L1 | RTSSAKRKKV | 488 | 10 | | | | | 6936 |
| HPV33 | L1 | SADLDQFPL | 455 | 9 | | | | | 6937 |
| HPV33 | L1 | SAFFPTPSGSM | 289 | 11 | | | | | 6938 |
| HPV33 | L1 | SASLQDTYRFV | 410 | 11 | | | | | 6939 |
| HPV33 | L1 | SIKNPTNA | 51 | 8 | | | | | 6940 |
| HPV33 | L1 | SIKNPTNAKKL | 51 | 11 | | | | | 6941 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | L1 | SIQSSAFFPT | 285 | 10 | | | | | 6942 |
| HPV33 | L1 | SIYYYAGSSRL | 32 | 11 | | | | | 6943 |
| HPV33 | L1 | SLFFFLRREQM | 245 | 11 | | | | | 6944 |
| HPV33 | L1 | SLQDTYRFV | 412 | 9 | | | | | 6945 |
| HPV33 | L1 | SLQDTYRFVT | 412 | 10 | | | | | 6946 |
| HPV33 | L1 | SMDYKQTQL | 149 | 9 | | | | | 6947 |
| HPV33 | L1 | SMDYKQTQLCL | 149 | 11 | | | | | 6948 |
| HPV33 | L1 | SMVTSESQL | 298 | 9 | | | | | 6949 |
| HPV33 | L1 | SQAITCQKT | 422 | 9 | | | | | 6950 |
| HPV33 | L1 | SQITCQKTV | 422 | 10 | | | | | 6951 |
| HPV33 | L1 | SQLFNKPYWL | 304 | 10 | | | | | 6952 |
| HPV33 | L1 | STCKYPDYL | 227 | 9 | | | | | 6953 |
| HPV33 | L1 | STCKYPDYLKM | 227 | 11 | | | | | 6954 |
| HPV33 | L1 | STDEYVSRT | 23 | 9 | | | | | 6955 |
| HPV33 | L1 | STDEYVSRTSI | 23 | 11 | | | | | 6956 |
| HPV33 | L1 | STNMTLCT | 339 | 8 | | | | | 6957 |
| HPV33 | L1 | STNMTLCTQV | 339 | 10 | | | | | 6958 |
| HPV33 | L1 | STNMTLCTQVT | 339 | 11 | | | | | 6959 |
| HPV33 | L1 | SVWRPSEA | 2 | 8 | | | | | 6960 |
| HPV33 | L1 | SVWRPSEAT | 2 | 9 | | | | | 6961 |
| HPV33 | L1 | SVWRPSEATV | 2 | 10 | | | | | 6962 |
| HPV33 | L1 | TAEVMTYI | 383 | 8 | | | | | 6963 |
| HPV33 | L1 | TAEVMTYIHA | 383 | 10 | | | | | 6964 |
| HPV33 | L1 | TAEVMTYIHAM | 383 | 11 | | | | | 6965 |
| HPV33 | L1 | TASIQSSA | 283 | 8 | | | | | 6966 |
| HPV33 | L1 | TIIEDGDM | 193 | 8 | | | | | 6967 |
| HPV33 | L1 | TIIEDGDMV | 193 | 9 | | | | | 6968 |
| HPV33 | L1 | TIIEDGDMVDT | 193 | 11 | | | | | 6969 |
| HPV33 | L1 | TLCTQVTSDST | 343 | 11 | | | | | 6970 |
| HPV33 | L1 | TLGEAVPDDL | 266 | 10 | | | | | 6971 |
| HPV33 | L1 | TLQANKSDV | 212 | 9 | | | | | 6972 |
| HPV33 | L1 | TLQANKSDVPI | 212 | 11 | | | | | 6973 |
| HPV33 | L1 | TLTAEVMT | 381 | 8 | | | | | 6974 |
| HPV33 | L1 | TLTAEVMTYI | 381 | 10 | | | | | 6975 |
| HPV33 | L1 | TQRLVWACV | 96 | 9 | | | | | 6976 |
| HPV33 | L1 | TQRLVWACVGL | 96 | 11 | | | | | 6977 |
| HPV33 | L1 | TQVTSDST | 346 | 8 | | | | | 6978 |
| HPV33 | L1 | TTASIQSSA | 282 | 9 | | | | | 6979 |
| HPV33 | L1 | TTRSTNMT | 336 | 8 | | | | | 6980 |
| HPV33 | L1 | TTRSTNMTL | 336 | 9 | | | | | 6981 |
| HPV33 | L1 | TTRSTNMTLCT | 336 | 11 | | | | | 6982 |
| HPV33 | L1 | TVPPKEKEDPL | 430 | 11 | | | | | 6983 |
| HPV33 | L1 | TVVDTTRST | 332 | 9 | | | | | 6984 |
| HPV33 | L1 | TVVDTTRSTNM | 332 | 11 | | | | | 6985 |
| HPV33 | L1 | TVYLPPVPV | 10 | 9 | | | | | 6986 |
| HPV33 | L1 | VACTNAAPA | 174 | 9 | | | | | 6987 |
| HPV33 | L1 | VMTYIHAM | 386 | 8 | | | | | 6988 |
| HPV33 | L1 | VTLTAEVM | 380 | 8 | | | | | 6989 |
| HPV33 | L1 | VTLAEVMT | 380 | 9 | | | | | 6990 |
| HPV33 | L1 | VTLTAEVMTYI | 380 | 11 | | | | | 6991 |
| HPV33 | L1 | VTSQAITCQKT | 420 | 11 | | | | | 6992 |
| HPV33 | L1 | VTVVDTTRST | 331 | 10 | | | | | 6993 |
| HPV33 | L1 | VVDTTRST | 333 | 8 | | | | | 6994 |
| HPV33 | L1 | VVDTTRSTNM | 333 | 10 | | | | | 6995 |
| HPV33 | L1 | VVDTTRSTNMT | 333 | 11 | | | | | 6996 |
| HPV33 | L1 | VVSTDEYV | 21 | 8 | | | | | 6997 |
| HPV33 | L1 | VVSTDEYVSRT | 21 | 11 | | | | | 6998 |
| HPV33 | L1 | WACVGLEI | 101 | 8 | | | | | 6999 |
| HPV33 | L1 | WQFGLTPPPSA | 401 | 11 | | | | | 7000 |
| HPV33 | L1 | YAGSSRLL | 36 | 8 | | | | | 7001 |
| HPV33 | L1 | YAGSSRLLA | 36 | 9 | | | | | 7002 |
| HPV33 | L1 | YAGSSRLLAV | 36 | 10 | | | | | 7003 |
| HPV33 | L1 | YIHAMNPDI | 389 | 9 | | | | | 7004 |
| HPV33 | L1 | YIHAMNPDIL | 389 | 10 | | | | | 7005 |
| HPV33 | L1 | YIKGSGTT | 276 | 8 | | | | | 7006 |
| HPV33 | L1 | YIKGSGTTA | 276 | 9 | | | | | 7007 |
| HPV33 | L1 | YIKGSGTTASI | 276 | 11 | | | | | 7008 |
| HPV33 | L1 | YIRHVEEYDL | 362 | 10 | | | | | 7009 |
| HPV33 | L1 | YLPPVPVSKV | 12 | 10 | | | | | 7010 |
| HPV33 | L1 | YLPPVPVSKVV | 12 | 11 | | | | | 7011 |
| HPV33 | L1 | YTFWEVDL | 443 | 8 | | | | | 7012 |
| HPV33 | L1 | YVSRTSIYYA | 27 | 11 | | | | | 7013 |
| HPV33 | L2 | AAIPLQPI | 81 | 8 | | | | | 7014 |
| HPV33 | L2 | AIINVSSV | 140 | 8 | | | | | 7015 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | L2 | AIPLQPIRPPV | 82 | 11 | | | | | 7016 |
| HPV33 | L2 | AITSRRHT | 291 | 8 | | | | | 7017 |
| HPV33 | L2 | AITSRRHTV | 291 | 9 | | | | | 7018 |
| HPV33 | L2 | ALHRPAIT | 286 | 8 | | | | | 7019 |
| HPV33 | L2 | ATGTCPPDV | 23 | 9 | | | | | 7020 |
| HPV33 | L2 | ATGTCPPDVI | 23 | 10 | | | | | 7021 |
| HPV33 | L2 | ATLKTRSGKQI | 308 | 11 | | | | | 7022 |
| HPV33 | L2 | ATQLYQTCKA | 14 | 10 | | | | | 7023 |
| HPV33 | L2 | ATQLYQYCKAT | 14 | 11 | | | | | 7024 |
| HPV33 | L2 | ATTRTSNV | 385 | 8 | | | | | 7025 |
| HPV33 | L2 | ATTRTSNVSI | 385 | 10 | | | | | 7026 |
| HPV33 | L2 | DIIALHRPA | 283 | 9 | | | | | 7027 |
| HPV33 | L2 | DIIALHRPAI | 283 | 10 | | | | | 7028 |
| HPV33 | L2 | DIIALHRPAIT | 283 | 11 | | | | | 7029 |
| HPV33 | L2 | DIPSPLFPT | 409 | 9 | | | | | 7030 |
| HPV33 | L2 | DISPAPDPDFL | 272 | 11 | | | | | 7031 |
| HPV33 | L2 | DLSPIVPL | 327 | 8 | | | | | 7032 |
| HPV33 | L2 | DLSPIVPLDHT | 327 | 11 | | | | | 7033 |
| HPV33 | L2 | DQILKYGSL | 42 | 9 | | | | | 7034 |
| HPV33 | L2 | DQILKYGSLGV | 42 | 11 | | | | | 7035 |
| HPV33 | L2 | DTIVVDGA | 431 | 8 | | | | | 7036 |
| HPV33 | L2 | DTIVVDGAGFV | 431 | 11 | | | | | 7037 |
| HPV33 | L2 | DTLQFQHSDI | 264 | 10 | | | | | 7038 |
| HPV33 | L2 | DTPVMSGPDI | 401 | 10 | | | | | 7039 |
| HPV33 | L2 | DTSTSSYSI | 350 | 9 | | | | | 7040 |
| HPV33 | L2 | DTTPAIINV | 136 | 9 | | | | | 7041 |
| HPV33 | L2 | DTVGPLDSSI | 95 | 10 | | | | | 7042 |
| HPV33 | L2 | DTVGPLDSSIV | 95 | 11 | | | | | 7043 |
| HPV33 | L2 | DVDNVHTPM | 369 | 9 | | | | | 7044 |
| HPV33 | L2 | DVIPKVEGST | 30 | 10 | | | | | 7045 |
| HPV33 | L2 | DVIPKVEGSTI | 30 | 11 | | | | | 7046 |
| HPV33 | L2 | DVTTSADT | 130 | 8 | | | | | 7047 |
| HPV33 | L2 | DVTTSADTT | 130 | 9 | | | | | 7048 |
| HPV33 | L2 | DVTTSADTTPA | 130 | 11 | | | | | 7049 |
| HPV33 | L2 | DVYADDVDNV | 364 | 10 | | | | | 7050 |
| HPV33 | L2 | EAGAPAPSI | 115 | 9 | | | | | 7051 |
| HPV33 | L2 | EAGAPAPSIPT | 115 | 11 | | | | | 7052 |
| HPV33 | L2 | ELQPLHDT | 344 | 8 | | | | | 7053 |
| HPV33 | L2 | ELQPLHDTST | 344 | 10 | | | | | 7054 |
| HPV33 | L2 | EQYELQPL | 341 | 8 | | | | | 7055 |
| HPV33 | L2 | EQYELQPLHDT | 341 | 11 | | | | | 7056 |
| HPV33 | L2 | ETSFIEAGA | 110 | 9 | | | | | 7057 |
| HPV33 | L2 | ETSFIEAGAPA | 110 | 11 | | | | | 7058 |
| HPV33 | L2 | FATTRTSNV | 384 | 9 | | | | | 7059 |
| HPV33 | L2 | FATTRTSNVSI | 384 | 11 | | | | | 7060 |
| HPV33 | L2 | FIEAGAPA | 113 | 8 | | | | | 7061 |
| HPV33 | L2 | FIEAGPAPSI | 113 | 11 | | | | | 7062 |
| HPV33 | L2 | FIFSSPTV | 181 | 8 | | | | | 7063 |
| HPV33 | L2 | FIFSSPTVST | 181 | 10 | | | | | 7064 |
| HPV33 | L2 | FLDIIALHRPA | 281 | 11 | | | | | 7065 |
| HPV33 | L2 | FLTSPHKL | 242 | 8 | | | | | 7066 |
| HPV33 | L2 | FLTSPHKLI | 242 | 9 | | | | | 7067 |
| HPV33 | L2 | FLTSPHKLIT | 242 | 10 | | | | | 7068 |
| HPV33 | L2 | FQHSDISPA | 268 | 9 | | | | | 7069 |
| HPV33 | L2 | FTDVRVAA | 460 | 8 | | | | | 7070 |
| HPV33 | L2 | FTEPSVLHPPA | 163 | 11 | | | | | 7071 |
| HPV33 | L2 | FVLHPSYFI | 440 | 9 | | | | | 7072 |
| HPV33 | L2 | FVLHPSYFIL | 440 | 10 | | | | | 7073 |
| HPV33 | L2 | FVVSTDSSNV | 201 | 10 | | | | | 7074 |
| HPV33 | L2 | FVVSTDSSNVT | 201 | 11 | | | | | 7075 |
| HPV33 | L2 | GAPAPSIPT | 117 | 9 | | | | | 7076 |
| HPV33 | L2 | GARIHYYQDL | 319 | 10 | | | | | 7077 |
| HPV33 | L2 | GLYDVYADDV | 361 | 10 | | | | | 7078 |
| HPV33 | L2 | GLYSRNTQQV | 226 | 10 | | | | | 7079 |
| HPV33 | L2 | GQKATLKT | 305 | 8 | | | | | 7080 |
| HPV33 | L2 | GTCPPDVI | 25 | 8 | | | | | 7081 |
| HPV33 | L2 | GTCPPDVIPKV | 25 | 11 | | | | | 7082 |
| HPV33 | L2 | GTDPPTAA | 75 | 8 | | | | | 7083 |
| HPV33 | L2 | GTDPPTAAI | 75 | 9 | | | | | 7084 |
| HPV33 | L2 | GTDPPTAAIPL | 75 | 11 | | | | | 7085 |
| HPV33 | L2 | GTGSGSGGRT | 60 | 10 | | | | | 7086 |
| HPV33 | L2 | GVFFGGLGI | 51 | 9 | | | | | 7087 |
| HPV33 | L2 | GVFFGGLGIGT | 51 | 11 | | | | | 7088 |
| HPV33 | L2 | HLNPTFTEPSV | 158 | 11 | | | | | 7089 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | L2 | HTPMQHSYST | 374 | 10 | | | | | 7090 |
| HPV33 | L2 | HTVPNEQYEL | 336 | 10 | | | | | 7091 |
| HPV33 | L2 | HTVRFSRV | 297 | 8 | | | | | 7092 |
| HPV33 | L2 | IADQILKYGSL | 40 | 11 | | | | | 7093 |
| HPV33 | L2 | IALHRPAI | 285 | 8 | | | | | 7094 |
| HPV33 | L2 | IALHRPAIT | 285 | 9 | | | | | 7095 |
| HPV33 | L2 | IIALHRPA | 284 | 8 | | | | | 7096 |
| HPV33 | L2 | IIALHRPAI | 284 | 9 | | | | | 7097 |
| HPV33 | L2 | IIALHRPAIT | 284 | 10 | | | | | 7098 |
| HPV33 | L2 | ILKYGSLSV | 44 | 9 | | | | | 7099 |
| HPV33 | L2 | IQTISTHL | 152 | 8 | | | | | 7100 |
| HPV33 | L2 | IQTISTHLNPT | 152 | 11 | | | | | 7101 |
| HPV33 | L2 | ITSRRHTV | 292 | 8 | | | | | 7102 |
| HPV33 | L2 | IVPLDHTV | 331 | 8 | | | | | 7103 |
| HPV33 | L2 | IVSLIEET | 104 | 8 | | | | | 7104 |
| HPV33 | L2 | IVSLIEETSFI | 104 | 11 | | | | | 7105 |
| HPV33 | L2 | IVVDGADFV | 433 | 9 | | | | | 7106 |
| HPV33 | L2 | IVVDGADFVL | 433 | 10 | | | | | 7107 |
| HPV33 | L2 | KATGTCPPDV | 22 | 10 | | | | | 7108 |
| HPV33 | L2 | KATCTCPPDVI | 22 | 11 | | | | | 7109 |
| HPV33 | L2 | KLITYDNPA | 248 | 9 | | | | | 7110 |
| HPV33 | L2 | KTRSGKQI | 311 | 8 | | | | | 7111 |
| HPV33 | L2 | KTRSGKQIGA | 311 | 10 | | | | | 7112 |
| HPV33 | L2 | KVEGSTIA | 34 | 8 | | | | | 7113 |
| HPV33 | L2 | KVEGSTIADQI | 34 | 11 | | | | | 7114 |
| HPV33 | L2 | KVVDPAFL | 236 | 8 | | | | | 7115 |
| HPV33 | L2 | KVVDPAFLT | 236 | 9 | | | | | 7116 |
| HPV33 | L2 | LIEETSFI | 107 | 8 | | | | | 7117 |
| HPV33 | L2 | LIEETSFIEA | 107 | 10 | | | | | 7118 |
| HPV33 | L2 | LITYDNPA | 249 | 8 | | | | | 7119 |
| HPV33 | L2 | LQFQHSDI | 266 | 8 | | | | | 7120 |
| HPV33 | L2 | LQFQHSDISPA | 266 | 11 | | | | | 7121 |
| HPV33 | L2 | LQPIRPPV | 85 | 8 | | | | | 7122 |
| HPV33 | L2 | LQPIRPPVT | 85 | 9 | | | | | 7123 |
| HPV33 | L2 | LQPIRPPVTV | 85 | 10 | | | | | 7124 |
| HPV33 | L2 | LQPLHDTST | 345 | 9 | | | | | 7125 |
| HPV33 | L2 | LTSPHKLI | 243 | 8 | | | | | 7126 |
| HPV33 | L2 | LTSPHKLIT | 243 | 9 | | | | | 7127 |
| HPV33 | L2 | MQHSYSTFA | 377 | 9 | | | | | 7128 |
| HPV33 | L2 | MQHSYSTFAT | 377 | 10 | | | | | 7129 |
| HPV33 | L2 | MQHSYSTFATT | 377 | 11 | | | | | 7130 |
| HPV33 | L2 | NIPMDTFV | 195 | 8 | | | | | 7131 |
| HPV33 | L2 | NIPMDTFVV | 195 | 9 | | | | | 7132 |
| HPV33 | L2 | NIPMDTFVVST | 195 | 11 | | | | | 7133 |
| HPV33 | L2 | NTGFDTPV | 397 | 8 | | | | | 7134 |
| HPV33 | L2 | NTGFDTPVM | 397 | 9 | | | | | 7135 |
| HPV33 | L2 | NTQQVKVV | 231 | 8 | | | | | 7136 |
| HPV33 | L2 | NTQQVKVVDPA | 231 | 11 | | | | | 7137 |
| HPV33 | L2 | NVSIPLNT | 391 | 8 | | | | | 7138 |
| HPV33 | L2 | NVSSVGESSI | 143 | 10 | | | | | 7139 |
| HPV33 | L2 | NVTSSTPI | 209 | 8 | | | | | 7140 |
| HPV33 | L2 | PAEASGHFI | 174 | 9 | | | | | 7141 |
| HPV33 | L2 | PAFESFDPEDT | 255 | 11 | | | | | 7142 |
| HPV33 | L2 | PAFLTSPHKL | 240 | 10 | | | | | 7143 |
| HPV33 | L2 | PAFLTSPHKLI | 240 | 11 | | | | | 7144 |
| HPV33 | L2 | PAIINVSSV | 139 | 9 | | | | | 7145 |
| HPV33 | L2 | PAITSRRHT | 290 | 9 | | | | | 7146 |
| HPV33 | L2 | PAITSRRHTV | 290 | 10 | | | | | 7147 |
| HPV33 | L2 | PAPAEASGHFI | 172 | 11 | | | | | 7148 |
| HPV33 | L2 | PAPDPDFL | 275 | 8 | | | | | 7149 |
| HPV33 | L2 | PAPDPDFLDI | 275 | 10 | | | | | 7150 |
| HPV33 | L2 | PAPDPDFLDII | 275 | 11 | | | | | 7151 |
| HPV33 | L2 | PIGTDPPT | 73 | 8 | | | | | 7152 |
| HPV33 | L2 | PIGTDPPTA | 73 | 9 | | | | | 7153 |
| HPV33 | L2 | PIGTDPPTAA | 73 | 10 | | | | | 7154 |
| HPV33 | L2 | PIGTDPPTAAI | 73 | 11 | | | | | 7155 |
| HPV33 | L2 | PIPGSRPV | 215 | 8 | | | | | 7156 |
| HPV33 | L2 | PIPGSRPVA | 215 | 9 | | | | | 7157 |
| HPV33 | L2 | PIPGSRPVARL | 215 | 11 | | | | | 7158 |
| HPV33 | L2 | PIRPPVTV | 87 | 8 | | | | | 7159 |
| HPV33 | L2 | PIRPPVTVDT | 87 | 10 | | | | | 7160 |
| HPV33 | L2 | PIRPPVTVDTV | 87 | 11 | | | | | 7161 |
| HPV33 | L2 | PISPFFPFDT | 423 | 10 | | | | | 7162 |
| HPV33 | L2 | PISPFFPFDTI | 423 | 11 | | | | | 7163 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | L2 | PIVPLDHT | 330 | 8 | | | | | 7164 |
| HPV33 | L2 | PIVPLDHTV | 330 | 9 | | | | | 7165 |
| HPV33 | L2 | PLDSSIVSL | 99 | 9 | | | | | 7166 |
| HPV33 | L2 | PLDSSIVSLI | 99 | 10 | | | | | 7167 |
| HPV33 | L2 | PLFPTSSPFV | 413 | 10 | | | | | 7168 |
| HPV33 | L2 | PLNTGFDT | 395 | 8 | | | | | 7169 |
| HPV33 | L2 | PLNTGFDTPV | 395 | 10 | | | | | 7170 |
| HPV33 | L2 | PLNTGFDTPVM | 395 | 11 | | | | | 7171 |
| HPV33 | L2 | PLQPIRPPV | 84 | 9 | | | | | 7172 |
| HPV33 | L2 | PLQPIRPPVT | 84 | 10 | | | | | 7173 |
| HPV33 | L2 | PLQPIRPPVTV | 84 | 11 | | | | | 7174 |
| HPV33 | L2 | PMDTFVVST | 197 | 9 | | | | | 7175 |
| HPV33 | L2 | PMQHSYST | 376 | 8 | | | | | 7176 |
| HPV33 | L2 | PMQHSYSTFA | 376 | 10 | | | | | 7177 |
| HPV33 | L2 | PMQHSYSTFAT | 376 | 11 | | | | | 7178 |
| HPV33 | L2 | PTAAIPLQPI | 79 | 10 | | | | | 7179 |
| HPV33 | L2 | PTFTEPSV | 161 | 8 | | | | | 7180 |
| HPV33 | L2 | PTFTEPSVL | 161 | 9 | | | | | 7181 |
| HPV33 | L2 | PTPSGFDV | 124 | 8 | | | | | 7182 |
| HPV33 | L2 | PTPSGFDVT | 124 | 9 | | | | | 7183 |
| HPV33 | L2 | PTPSGFDVTT | 124 | 10 | | | | | 7184 |
| HPV33 | L2 | PTSSPFVPI | 416 | 9 | | | | | 7185 |
| HPV33 | L2 | PTVSTQSYENI | 186 | 11 | | | | | 7186 |
| HPV33 | L2 | PVMSGPDI | 403 | 8 | | | | | 7187 |
| HPV33 | L2 | PVTVDTVGPL | 91 | 10 | | | | | 7188 |
| HPV33 | L2 | QILKYGSL | 43 | 8 | | | | | 7189 |
| HPV33 | L2 | QILKYGSLGV | 43 | 10 | | | | | 7190 |
| HPV33 | L2 | QLYQTCKA | 16 | 8 | | | | | 7191 |
| HPV33 | L2 | QLYQTCKAT | 16 | 9 | | | | | 7192 |
| HPV33 | L2 | QLYQTCKATGT | 16 | 11 | | | | | 7193 |
| HPV33 | L2 | QQVKVVDPA | 233 | 9 | | | | | 7194 |
| HPV33 | L2 | QQVKVVDPAFL | 233 | 11 | | | | | 7195 |
| HPV33 | L2 | QTCKATGT | 19 | 8 | | | | | 7196 |
| HPV33 | L2 | QTISTHLNPT | 153 | 10 | | | | | 7197 |
| HPV33 | L2 | QVKVVDPA | 234 | 8 | | | | | 7198 |
| HPV33 | L2 | QVKVVDPAFL | 234 | 10 | | | | | 7199 |
| HPV33 | L2 | QVKVVDPAFLT | 234 | 11 | | | | | 7200 |
| HPV33 | L2 | RASATQLYQT | 11 | 10 | | | | | 7201 |
| HPV33 | L2 | RIHYYQDL | 321 | 8 | | | | | 7202 |
| HPV33 | L2 | RIHYYQDLSPI | 321 | 11 | | | | | 7203 |
| HPV33 | L2 | RLGLYSRNT | 224 | 9 | | | | | 7204 |
| HPV33 | L2 | RTGYVPIGT | 68 | 9 | | | | | 7205 |
| HPV33 | L2 | RTSNVSIPL | 388 | 9 | | | | | 7206 |
| HPV33 | L2 | RTSNVSIPLNT | 388 | 11 | | | | | 7207 |
| HPV33 | L2 | RVGQKATL | 303 | 8 | | | | | 7208 |
| HPV33 | L2 | RVGQKATLKT | 303 | 10 | | | | | 7209 |
| HPV33 | L2 | SADTTPAI | 134 | 8 | | | | | 7210 |
| HPV33 | L2 | SADTTPAII | 134 | 9 | | | | | 7211 |
| HPV33 | L2 | SADTTPAIINV | 134 | 11 | | | | | 7212 |
| HPV33 | L2 | SATQLYQT | 13 | 8 | | | | | 7213 |
| HPV33 | L2 | SATQLYATCKA | 13 | 11 | | | | | 7214 |
| HPV33 | L2 | SINDGLYDV | 357 | 9 | | | | | 7215 |
| HPV33 | L2 | SINDGLYDVYA | 357 | 11 | | | | | 7216 |
| HPV33 | L2 | SIPLNTGFDT | 393 | 10 | | | | | 7217 |
| HPV33 | L2 | SIPTPSGFDV | 122 | 10 | | | | | 7218 |
| HPV33 | L2 | SIPTPSGFDVT | 122 | 11 | | | | | 7219 |
| HPV33 | L2 | SIQTISTHL | 151 | 9 | | | | | 7220 |
| HPV33 | L2 | SIVSLIEET | 103 | 9 | | | | | 7221 |
| HPV33 | L2 | SLGVFFGGL | 49 | 9 | | | | | 7222 |
| HPV33 | L2 | SLGVFFGGLGI | 49 | 11 | | | | | 7223 |
| HPV33 | L2 | SLIEETSFI | 106 | 9 | | | | | 7224 |
| HPV33 | L2 | SLIEETSFIEA | 106 | 11 | | | | | 7225 |
| HPV33 | L2 | STDSSNVT | 204 | 8 | | | | | 7226 |
| HPV33 | L2 | STDSSNVTSST | 204 | 11 | | | | | 7227 |
| HPV33 | L2 | STFATTRT | 382 | 8 | | | | | 7228 |
| HPV33 | L2 | STFATTRTSNV | 382 | 11 | | | | | 7229 |
| HPV33 | L2 | STHLNPTFT | 156 | 9 | | | | | 7230 |
| HPV33 | L2 | STIADQIL | 38 | 8 | | | | | 7231 |
| HPV33 | L2 | STPIPGSRPV | 213 | 10 | | | | | 7232 |
| HPV33 | L2 | STPIPGSRPVA | 213 | 11 | | | | | 7233 |
| HPV33 | L2 | STQSYENI | 189 | 8 | | | | | 7234 |
| HPV33 | L2 | STQSYENIPM | 189 | 10 | | | | | 7235 |
| HPV33 | L2 | STRRKRASA | 6 | 9 | | | | | 7236 |
| HPV33 | L2 | STRRKRASAT | 6 | 10 | | | | | 7237 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV33 | L2 | STSSYSINDGL | 352 | 11 | | | | | 7238 |
| HPV33 | L2 | SVGEESSIQT | 146 | 9 | | | | | 7239 |
| HPV33 | L2 | SVGESSIQTI | 146 | 10 | | | | | 7240 |
| HPV33 | L2 | SVLHPPAPA | 167 | 9 | | | | | 7241 |
| HPV33 | L2 | SVLHPPAPAEA | 167 | 11 | | | | | 7242 |
| HPV33 | L2 | TAAIPLQPI | 80 | 9 | | | | | 7243 |
| HPV33 | L2 | TISTHLNPT | 154 | 9 | | | | | 7244 |
| HPV33 | L2 | TISTHLNPTFT | 154 | 11 | | | | | 7245 |
| HPV33 | L2 | TIVVDGADFV | 432 | 10 | | | | | 7246 |
| HPV33 | L2 | TIVVDGADFVL | 432 | 11 | | | | | 7247 |
| HPV33 | L2 | TLKTRSGKQI | 309 | 10 | | | | | 7248 |
| HPV33 | L2 | TLQFQHSDI | 265 | 9 | | | | | 7249 |
| HPV33 | L2 | TQLYQTCKA | 15 | 9 | | | | | 7250 |
| HPV33 | L2 | TQLYQTCKAT | 15 | 10 | | | | | 7251 |
| HPV33 | L2 | TQQVKVVDPA | 232 | 10 | | | | | 7252 |
| HPV33 | L2 | TQSYENIPM | 190 | 9 | | | | | 7253 |
| HPV33 | L2 | TQSYENIPMDT | 190 | 11 | | | | | 7254 |
| HPV33 | L2 | TTPAIINV | 137 | 8 | | | | | 7255 |
| HPV33 | L2 | TTPAIINVSSV | 137 | 11 | | | | | 7256 |
| HPV33 | L2 | TTRTSNVSI | 386 | 9 | | | | | 7257 |
| HPV33 | L2 | TTRTSNVSIPL | 386 | 11 | | | | | 7258 |
| HPV33 | L2 | TTSADTTPA | 132 | 9 | | | | | 7259 |
| HPV33 | L2 | TTSADTTPAI | 132 | 10 | | | | | 7260 |
| HPV33 | L2 | TTSADTTPAII | 132 | 11 | | | | | 7261 |
| HPV33 | L2 | TVDTVGPL | 93 | 8 | | | | | 7262 |
| HPV33 | L2 | TVGPLDSSI | 96 | 9 | | | | | 7263 |
| HPV33 | L2 | TVGPLDSSIV | 96 | 10 | | | | | 7264 |
| HPV33 | L2 | TVPNEQYEL | 337 | 9 | | | | | 7265 |
| HPV33 | L2 | TVRFSRVGQKA | 298 | 11 | | | | | 7266 |
| HPV33 | L2 | TVSTQSYENI | 187 | 10 | | | | | 7267 |
| HPV33 | L2 | VARLGLYSRNT | 222 | 11 | | | | | 7268 |
| HPV33 | L2 | VIPKVEGST | 31 | 9 | | | | | 7269 |
| HPV33 | L2 | VIPKVEGSTI | 31 | 10 | | | | | 7270 |
| HPV33 | L2 | VIPKVEGSTIA | 31 | 11 | | | | | 7271 |
| HPV33 | L2 | VLHPPAPA | 168 | 8 | | | | | 7272 |
| HPV33 | L2 | VLHPPAPAEA | 168 | 10 | | | | | 7273 |
| HPV33 | L2 | VLHPSYFI | 441 | 8 | | | | | 7274 |
| HPV33 | L2 | VLHPSYFIL | 441 | 9 | | | | | 7275 |
| HPV33 | L2 | VMSGPDIPSPL | 404 | 11 | | | | | 7276 |
| HPV33 | L2 | VTTSADTT | 131 | 8 | | | | | 7277 |
| HPV33 | L2 | VTTSADTTPA | 131 | 10 | | | | | 7278 |
| HPV33 | L2 | VTTSADTTPAI | 131 | 11 | | | | | 7279 |
| HPV33 | L2 | VTVDTVGPL | 92 | 9 | | | | | 7280 |
| HPV33 | L2 | VVDGADFV | 434 | 8 | | | | | 7281 |
| HPV33 | L2 | VVDGADFVL | 434 | 9 | | | | | 7282 |
| HPV33 | L2 | VVDPAFLT | 237 | 8 | | | | | 7283 |
| HPV33 | L2 | VVSTDSSNV | 202 | 9 | | | | | 7284 |
| HPV33 | L2 | VVSTDSSNVT | 202 | 10 | | | | | 7285 |
| HPV33 | L2 | YADDVDNV | 366 | 8 | | | | | 7286 |
| HPV33 | L2 | YADDVDNVHT | 366 | 10 | | | | | 7287 |
| HPV33 | L2 | YQDLSPIV | 325 | 8 | | | | | 7288 |
| HPV33 | L2 | YQDLSPIVPL | 325 | 10 | | | | | 7289 |
| HPV33 | L2 | YQTCKATGT | 18 | 9 | | | | | 7290 |
| HPV33 | L2 | YVPIGTDPPT | 71 | 10 | | | | | 7291 |
| HPV33 | L2 | YVPIGTDPPTA | 71 | 11 | | | | | 7292 |
| HPV45 | E1 | AAAFLKSNCQA | 382 | 11 | | | | | 7293 |
| HPV45 | E1 | AAETQVTV | 144 | 8 | | | | | 7294 |
| HPV45 | E1 | AAETQVTVNT | 144 | 10 | | | | | 7295 |
| HPV45 | E1 | AAFLKSNCQA | 383 | 10 | | | | | 7296 |
| HPV45 | E1 | AALYWYRT | 310 | 8 | | | | | 7297 |
| HPV45 | E1 | AALYWYRTGI | 310 | 10 | | | | | 7298 |
| HPV45 | E1 | AAMLAVFKDI | 198 | 10 | | | | | 7299 |
| HPV45 | E1 | AIFGVNPT | 232 | 8 | | | | | 7300 |
| HPV45 | E1 | AIFGVNPTV | 232 | 9 | | | | | 7301 |
| HPV45 | E1 | AIFGVNPTVA | 232 | 10 | | | | | 7302 |
| HPV45 | E1 | ALDGNPISI | 532 | 9 | 0.021 | | | | 7303 |
| HPV45 | E1 | ALFHAQEV | 68 | 8 | | | | | 7304 |
| HPV45 | E1 | ALKEFLKGT | 452 | 9 | | | | | 7305 |
| HPV45 | E1 | ALYWYRTGI | 311 | 9 | 0.0032 | | | | 7306 |
| HPV45 | E1 | AMLAVFKDI | 199 | 9 | | | | | 7307 |
| HPV45 | E1 | AMLDDATHT | 512 | 9 | | | | | 7308 |
| HPV45 | E1 | AQALFHAQEV | 66 | 10 | | | | | 7309 |
| HPV45 | E1 | AQEVQNDA | 72 | 8 | | | | | 7310 |
| HPV45 | E1 | AQEVQNDAQV | 72 | 10 | | | | | 7311 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E1 | AQEVQNDAQVL | 72 | 11 | | | | | 7312 |
| HPV45 | E1 | AQKRQMNM | 408 | 8 | | | | | 7313 |
| HPV45 | E1 | AQLADCNSNA | 373 | 10 | | | | | 7314 |
| HPV45 | E1 | AQLADCNSNAA | 373 | 11 | | | | | 7315 |
| HPV45 | E1 | ATDTGSDM | 40 | 8 | | | | | 7316 |
| HPV45 | E1 | ATDTGSDMV | 40 | 9 | | | | | 7317 |
| HPV45 | E1 | ATLYAHIQCL | 251 | 10 | | | | | 7318 |
| HPV45 | E1 | AVFKDIYGL | 202 | 9 | | | | | 7319 |
| HPV45 | E1 | AVMCRHYKRA | 399 | 10 | | | | | 7320 |
| HPV45 | E1 | CAVMCRHYKRA | 398 | 11 | | | | | 7321 |
| HPV45 | E1 | CILLYGPA | 465 | 8 | | | | | 7322 |
| HPV45 | E1 | CILLYGPANT | 465 | 10 | | | | | 7323 |
| HPV45 | E1 | CLDCKWGV | 259 | 8 | | | | | 7324 |
| HPV45 | E1 | CLDCKWGVL | 259 | 9 | | | | | 7325 |
| HPV45 | E1 | CLDCKWGVLI | 259 | 10 | 0.0002 | | | | 7326 |
| HPV45 | E1 | CLDCKWGVLIL | 259 | 11 | | | | | 7327 |
| HPV45 | E1 | CMLIEPPKL | 297 | 9 | | | | | 7328 |
| HPV45 | E1 | CQAKYLKDCA | 390 | 10 | | | | | 7329 |
| HPV45 | E1 | CQAKYLKDCAV | 390 | 11 | | | | | 7330 |
| HPV45 | E1 | CTDWVMAI | 226 | 8 | | | | | 7331 |
| HPV45 | E1 | CTDWVMAIFGV | 226 | 11 | | | | | 7332 |
| HPV45 | E1 | CVTGQNTRPL | 634 | 10 | | | | | 7333 |
| HPV45 | E1 | DADTEGIPFGT | 621 | 11 | | | | | 7334 |
| HPV45 | E1 | DAQVLHLL | 78 | 8 | | | | | 7335 |
| HPV45 | E1 | DATHTCWT | 516 | 8 | | | | | 7336 |
| HPV45 | E1 | DIYGLSFT | 206 | 8 | | | | | 7337 |
| HPV45 | E1 | DIYGLSFTDL | 206 | 10 | | | | | 7338 |
| HPV45 | E1 | DIYGLSFTDLV | 206 | 11 | | | | | 7339 |
| HPV45 | E1 | DLHEDDEDA | 614 | 9 | | | | | 7340 |
| HPV45 | E1 | DLHEDDEDADT | 614 | 11 | | | | | 7341 |
| HPV45 | E1 | DLSDMVQWA | 349 | 9 | | | | | 7342 |
| HPV45 | E1 | DLSPRLQEI | 108 | 9 | | | | | 7343 |
| HPV45 | E1 | DLSPRLQEISL | 108 | 11 | | | | | 7344 |
| HPV45 | E1 | DLTDESDM | 361 | 8 | | | | | 7345 |
| HPV45 | E1 | DLTDESDMA | 361 | 9 | | | | | 7346 |
| HPV45 | E1 | DLVRNFKSDKT | 214 | 11 | | | | | 7347 |
| HPV45 | E1 | DMAFQYAQL | 367 | 9 | | | | | 7348 |
| HPV45 | E1 | DMAFQYAQLA | 367 | 10 | | | | | 7349 |
| HPV45 | E1 | DMVDFIDT | 46 | 8 | | | | | 7350 |
| HPV45 | E1 | DMVDFIDTQL | 46 | 10 | | | | | 7351 |
| HPV45 | E1 | DMVQWAFDNDL | 352 | 11 | | | | | 7352 |
| HPV45 | E1 | DTDLSPRL | 106 | 8 | | | | | 7353 |
| HPV45 | E1 | DTDLSPRLQEI | 106 | 11 | | | | | 7354 |
| HPV45 | E1 | DTEGIPFGT | 623 | 9 | | | | | 7355 |
| HPV45 | E1 | DTGSDMVDFI | 42 | 10 | | | | | 7356 |
| HPV45 | E1 | DTKVAMLDDA | 508 | 10 | | | | | 7357 |
| HPV45 | E1 | DTKVAMLDDAT | 508 | 11 | | | | | 7358 |
| HPV45 | E1 | DTPEWIQRL | 328 | 9 | | | | | 7359 |
| HPV45 | E1 | DTPEWIQRLT | 328 | 10 | | | | | 7360 |
| HPV45 | E1 | DTPEWIQRLTI | 328 | 11 | | | | | 7361 |
| HPV45 | E1 | DTQLSICEQA | 52 | 10 | | | | | 7362 |
| HPV45 | E1 | DVISDDEDET | 30 | 10 | | | | | 7363 |
| HPV45 | E1 | DVISDDEDETA | 30 | 11 | | | | | 7364 |
| HPV45 | E1 | EAAETQVT | 143 | 8 | | | | | 7365 |
| HPV45 | E1 | EAAETQVTV | 143 | 9 | | | | | 7366 |
| HPV45 | E1 | EAAETQVTVNT | 143 | 11 | | | | | 7367 |
| HPV45 | E1 | EISLNSGHKKA | 115 | 11 | | | | | 7368 |
| HPV45 | E1 | ELKEKKQA | 186 | 8 | | | | | 7369 |
| HPV45 | E1 | ELLQASNKKA | 189 | 10 | | | | | 7370 |
| HPV45 | E1 | ELLQASNKKAA | 189 | 11 | | | | | 7371 |
| HPV45 | E1 | EQAEQETA | 59 | 8 | | | | | 7372 |
| HPV45 | E1 | EQAEQETAQA | 59 | 10 | | | | | 7373 |
| HPV45 | E1 | EQAEQETAQAL | 59 | 11 | | | | | 7374 |
| HPV45 | E1 | EQETAQAL | 62 | 8 | | | | | 7375 |
| HPV45 | E1 | EQETAQALFHA | 62 | 11 | | | | | 7376 |
| HPV45 | E1 | EQLSVDTDL | 101 | 9 | | | | | 7377 |
| HPV45 | E1 | ETAQALFHA | 64 | 9 | | | | | 7378 |
| HPV45 | E1 | ETATDTGSDM | 38 | 10 | | | | | 7379 |
| HPV45 | E1 | ETATDTGSDMV | 38 | 11 | | | | | 7380 |
| HPV45 | E1 | ETCMLIEPPKL | 295 | 11 | | | | | 7381 |
| HPV45 | E1 | ETIVEKKT | 21 | 8 | | | | | 7382 |
| HPV45 | E1 | ETIVEKKTGDV | 21 | 11 | | | | | 7383 |
| HPV45 | E1 | ETQVTVNT | 146 | 8 | | | | | 7384 |
| HPV45 | E1 | ETQVTVNTNA | 146 | 10 | | | | | 7385 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E1 | EVEAAETQV | 141 | 9 | | | | | 7386 |
| HPV45 | E1 | EVEAAETQVT | 141 | 10 | | | | | 7387 |
| HPV45 | E1 | EVEAAETQVTV | 141 | 11 | | | | | 7388 |
| HPV45 | E1 | EVQNDAQV | 74 | 8 | | | | | 7389 |
| HPV45 | E1 | EVQNDAQVL | 74 | 9 | | | | | 7390 |
| HPV45 | E1 | EVQNDAQVLHL | 74 | 11 | | | | | 7391 |
| HPV45 | E1 | EVSGDTPEWI | 324 | 10 | | | | | 7392 |
| HPV45 | E1 | FAGGSKENSPL | 89 | 11 | | | | | 7393 |
| HPV45 | E1 | FIDTQLSI | 50 | 8 | | | | | 7394 |
| HPV45 | E1 | FIHFLQGA | 483 | 8 | | | | | 7395 |
| HPV45 | E1 | FIHFLQGAI | 483 | 9 | | | | | 7396 |
| HPV45 | E1 | FIHFLQGAII | 483 | 10 | | | | | 7397 |
| HPV45 | E1 | FISFLRAL | 446 | 8 | | | | | 7398 |
| HPV45 | E1 | FLKGTPKKNCI | 456 | 11 | | | | | 7399 |
| HPV45 | E1 | FLKSNCQA | 385 | 8 | | | | | 7400 |
| HPV45 | E1 | FLKNCQAKYL | 385 | 11 | | | | | 7401 |
| HPV45 | E1 | FLQGAIISFV | 486 | 10 | | | | | 7402 |
| HPV45 | E1 | FLRALKEFL | 449 | 9 | | | | | 7403 |
| HPV45 | E1 | FLRYQGVEFI | 438 | 10 | | | | | 7404 |
| HPV45 | E1 | FVETIVEKKT | 19 | 10 | | | | | 7405 |
| HPV45 | E1 | FVNSNSHFWL | 494 | 10 | | | | | 7406 |
| HPV45 | E1 | GIDDSNFDL | 342 | 9 | | | | | 7407 |
| HPV45 | E1 | GIPFGTFKCV | 626 | 10 | | | | | 7408 |
| HPV45 | E1 | GIPFGTFKCVT | 626 | 11 | | | | | 7409 |
| HPV45 | E1 | GISNISEV | 318 | 8 | | | | | 7410 |
| HPV45 | E1 | GLSFTDLV | 209 | 8 | | | | | 7411 |
| HPV45 | E1 | GLSTLLHV | 286 | 8 | | | | | 7412 |
| HPV45 | E1 | GLSTLLHVPET | 286 | 11 | | | | | 7413 |
| HPV45 | E1 | GMSFIHFL | 480 | 8 | | | | | 7414 |
| HPV45 | E1 | GMSFIHFLQGA | 480 | 11 | | | | | 7415 |
| HPV45 | E1 | GTFKCVTGQNT | 630 | 11 | | | | | 7416 |
| HPV45 | E1 | GTGCNGWFFV | 11 | 10 | | | | | 7417 |
| HPV45 | E1 | GTPKKNCI | 459 | 8 | | | | | 7418 |
| HPV45 | E1 | GTPKKNCIL | 459 | 9 | | | | | 7419 |
| HPV45 | E1 | GTPKKNCILL | 459 | 10 | | | | | 7420 |
| HPV45 | E1 | GVEFISFL | 443 | 8 | | | | | 7421 |
| HPV45 | E1 | GVEFISFLRA | 443 | 10 | | | | | 7422 |
| HPV45 | E1 | GVEFISFLRAL | 443 | 11 | | | | | 7423 |
| HPV45 | E1 | GVLILALL | 265 | 8 | | | | | 7424 |
| HPV45 | E1 | HAQEVQNDA | 71 | 9 | | | | | 7425 |
| HPV45 | E1 | HAQEVQNDAQV | 71 | 11 | | | | | 7426 |
| HPV45 | E1 | HIQCLDCKWGV | 256 | 11 | | | | | 7427 |
| HPV45 | E1 | HLLKRKFA | 83 | 8 | | | | | 7428 |
| HPV45 | E1 | HTCWTYFDNYM | 519 | 11 | | | | | 7429 |
| HPV45 | E1 | HVPETCML | 292 | 8 | | | | | 7430 |
| HPV45 | E1 | HVPETCMLI | 292 | 9 | | | | | 7431 |
| HPV45 | E1 | ILLTSNIDPA | 555 | 10 | | | | | 7432 |
| HPV45 | E1 | ILLYGPANT | 466 | 9 | | | | | 7433 |
| HPV45 | E1 | IQCLDCKWGV | 257 | 10 | | | | | 7434 |
| HPV45 | E1 | IQCLDCKWGVL | 257 | 11 | | | | | 7435 |
| HPV45 | E1 | IQRLTIIQHGI | 333 | 11 | | | | | 7436 |
| HPV45 | E1 | ITELKELL | 184 | 8 | | | | | 7437 |
| HPV45 | E1 | IRELKELLQA | 184 | 10 | | | | | 7438 |
| HPV45 | E1 | IVEKKTGDV | 23 | 9 | | | | | 7439 |
| HPV45 | E1 | IVEKKTGDVI | 23 | 10 | | | | | 7440 |
| HPV45 | E1 | IVQFLRYQGV | 435 | 10 | | | | | 7441 |
| HPV45 | E1 | KAAMLAVFKDI | 197 | 11 | | | | | 7442 |
| HPV45 | E1 | KAKRRLFT | 124 | 8 | | | | | 7443 |
| HPV45 | E1 | KAKRRLFTI | 124 | 9 | | | | | 7444 |
| HPV45 | E1 | KIDEGGDWRPI | 425 | 11 | | | | | 7445 |
| HPV45 | E1 | KLRSSVAA | 304 | 8 | | | | | 7446 |
| HPV45 | E1 | KLRSSVAAL | 304 | 9 | 0.0003 | | | | 7447 |
| HPV45 | E1 | KTLIKPAT | 245 | 8 | | | | | 7448 |
| HPV45 | E1 | KTLIKPATL | 245 | 9 | | | | | 7449 |
| HPV45 | E1 | KTLIKPATLYA | 245 | 11 | | | | | 7450 |
| HPV45 | E1 | KTTCTDWV | 223 | 8 | | | | | 7451 |
| HPV45 | E1 | KTTCTDWVM | 223 | 9 | | | | | 7452 |
| HPV45 | E1 | KTTCTDWVMA | 223 | 10 | | | | | 7453 |
| HPV45 | E1 | KTTCTDWVMAI | 223 | 11 | | | | | 7454 |
| HPV45 | E1 | KVAMLDDA | 510 | 8 | | | | | 7455 |
| HPV45 | E1 | KVAMLDDAT | 510 | 9 | | | | | 7456 |
| HPV45 | E1 | KVAMLDDATHT | 510 | 11 | | | | | 7457 |
| HPV45 | E1 | LADCNSNA | 375 | 8 | | | | | 7458 |
| HPV45 | E1 | LADCNSNAA | 375 | 9 | | | | | 7459 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E1 | LADCNCNAAA | 375 | 10 | | | | | 7460 |
| HPV45 | E1 | LADTKVAM | 506 | 8 | | | | | 7461 |
| HPV45 | E1 | LADTKVAML | 506 | 9 | | | | | 7462 |
| HPV45 | E1 | LAVFKDIYGL | 201 | 10 | | | | | 7463 |
| HPV45 | E1 | LIEPPKLRSSV | 299 | 11 | | | | | 7464 |
| HPV45 | E1 | LIKPATLYA | 247 | 9 | | | | | 7465 |
| HPV45 | E1 | LIKPATLYAHI | 247 | 11 | | | | | 7466 |
| HPV45 | E1 | LLHVPETCM | 290 | 9 | | | | | 7467 |
| HPV45 | E1 | LLHVPETCML | 290 | 10 | | | | | 7468 |
| HPV45 | E1 | LLHVPETCMLI | 290 | 11 | | | | | 7469 |
| HPV45 | E1 | LLQASNKKA | 190 | 9 | | | | | 7470 |
| HPV45 | E1 | LLQASNKKAA | 190 | 10 | | | | | 7471 |
| HPV45 | E1 | LLQASNKKAAM | 190 | 11 | | | | | 7472 |
| HPV45 | E1 | LLQLKCPPI | 547 | 9 | | | | | 7473 |
| HPV45 | E1 | LLQLKCPPIL | 547 | 10 | | | | | 7474 |
| HPV45 | E1 | LLQLKCPPILL | 547 | 11 | | | | | 7475 |
| HPV45 | E1 | LLRYKCGKNRL | 271 | 11 | | | | | 7476 |
| HPV45 | E1 | LLTSNIDPA | 556 | 9 | | | | | 7477 |
| HPV45 | E1 | LLYGPANT | 467 | 8 | | | | | 7478 |
| HPV45 | E1 | LQASNKKA | 191 | 8 | | | | | 7479 |
| HPV45 | E1 | LQASNKKAA | 191 | 9 | | | | | 7480 |
| HPV45 | E1 | LQASNKKAAM | 191 | 10 | | | | | 7481 |
| HPV45 | E1 | LQASNKKAAML | 191 | 11 | | | | | 7482 |
| HPV45 | E1 | LQGAIISFV | 487 | 9 | | | | | 7483 |
| HPV45 | E1 | LQLKCPPI | 548 | 8 | | | | | 7484 |
| HPV45 | E1 | LQLKCPPIL | 548 | 9 | | | | | 7485 |
| HPV45 | E1 | LQLKCPPILL | 548 | 10 | | | | | 7486 |
| HPV45 | E1 | LQLKCPPILLT | 548 | 11 | | | | | 7487 |
| HPV45 | E1 | LTDESDMA | 362 | 8 | | | | | 7488 |
| HPV45 | E1 | LTIIQHGI | 336 | 8 | | | | | 7489 |
| HPV45 | E1 | LTSNIDPA | 557 | 8 | | | | | 7490 |
| HPV45 | E1 | LTVAKGLST | 281 | 9 | | | | | 7491 |
| HPV45 | E1 | LTVAKGLSTL | 281 | 10 | | | | | 7492 |
| HPV45 | E1 | LTVAKGLSTLL | 281 | 11 | | | | | 7493 |
| HPV45 | E1 | LVRNFKSDKT | 215 | 10 | | | | | 7494 |
| HPV45 | E1 | LVRNFKSDKTT | 215 | 11 | | | | | 7495 |
| HPV45 | E1 | MAFQYAQL | 368 | 8 | | | | | 7496 |
| HPV45 | E1 | MAFQYAQLA | 368 | 9 | | | | | 7497 |
| HPV45 | E1 | MAIFGVNPT | 231 | 9 | | | | | 7498 |
| HPV45 | E1 | MAIFGVNPTV | 231 | 10 | | | | | 7499 |
| HPV45 | E1 | MAIFGVNPTVA | 231 | 11 | | | | | 7500 |
| HPV45 | E1 | MLAVFKDI | 200 | 8 | | | | | 7501 |
| HPV45 | E1 | MLAVFKDIYGL | 200 | 11 | | | | | 7502 |
| HPV45 | E1 | MLDDATHT | 513 | 8 | | | | | 7503 |
| HPV45 | E1 | MLDDATHCWT | 513 | 11 | | | | | 7504 |
| HPV45 | E1 | MLIEPPKL | 298 | 8 | | | | | 7505 |
| HPV45 | E1 | MVDFIDTQL | 47 | 9 | | | | | 7506 |
| HPV45 | E1 | MVDFIDTQLSI | 47 | 11 | | | | | 7507 |
| HPV45 | E1 | MVQWAFDNDL | 353 | 10 | | | | | 7508 |
| HPV45 | E1 | MVQWAFDNDLT | 353 | 11 | | | | | 7509 |
| HPV45 | E1 | NAENGGSV | 154 | 8 | | | | | 7510 |
| HPV45 | E1 | NAENGGSVHST | 154 | 11 | | | | | 7511 |
| HPV45 | E1 | NAENVDPHCSI | 174 | 11 | | | | | 7512 |
| HPV45 | E1 | NALDGNPI | 531 | 8 | | | | | 7513 |
| HPV45 | E1 | NALDGNPISI | 531 | 10 | | | | | 7514 |
| HPV45 | E1 | NISEVSGDT | 321 | 9 | | | | | 7515 |
| HPV45 | E1 | NTGKSYFGM | 473 | 9 | | | | | 7516 |
| HPV45 | E1 | NTNAENGGSV | 152 | 10 | | | | | 7517 |
| HPV45 | E1 | NVDPHCSI | 177 | 8 | | | | | 7518 |
| HPV45 | E1 | NVDPHCSIT | 177 | 9 | | | | | 7519 |
| HPV45 | E1 | NVDPHCSITEL | 177 | 11 | | | | | 7520 |
| HPV45 | E1 | PAKDNKWPYL | 563 | 10 | | | | | 7521 |
| HPV45 | E1 | PANTGKSYFGM | 471 | 11 | | | | | 7522 |
| HPV45 | E1 | PATLYAHI | 250 | 8 | | | | | 7523 |
| HPV45 | E1 | PATLYAHIQCL | 250 | 11 | | | | | 7524 |
| HPV45 | E1 | PILLTSNI | 554 | 8 | | | | | 7525 |
| HPV45 | E1 | PILLTSNIDPA | 554 | 11 | | | | | 7526 |
| HPV45 | E1 | PISIDRKHKPL | 537 | 11 | | | | | 7527 |
| HPV45 | E1 | PIVQFLRYQGV | 434 | 11 | | | | | 7528 |
| HPV45 | E1 | PLADTKVA | 505 | 8 | | | | | 7529 |
| HPV45 | E1 | PLADTKVAM | 505 | 9 | | | | | 7530 |
| HPV45 | E1 | PLADTKVAML | 505 | 10 | | | | | 7531 |
| HPV45 | E1 | PLGEQLSV | 98 | 8 | | | | | 7532 |
| HPV45 | E1 | PLGEQLSVDT | 98 | 10 | | | | | 7533 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E1 | PLLQLKCPPI | 546 | 10 | | | | | 7534 |
| HPV45 | E1 | PLLQLKCPPIL | 546 | 11 | | | | | 7535 |
| HPV45 | E1 | PTVAEGFKT | 238 | 9 | | | | | 7536 |
| HPV45 | E1 | PTVAEGFKTL | 238 | 10 | | | | | 7537 |
| HPV45 | E1 | PTVAEGFKTLI | 238 | 11 | | | | | 7538 |
| HPV45 | E1 | QAEQETAQA | 60 | 9 | | | | | 7539 |
| HPV45 | E1 | QAEQETAQAL | 60 | 10 | | | | | 7540 |
| HPV45 | E1 | QAKYLKDCA | 391 | 9 | | | | | 7541 |
| HPV45 | E1 | QAKYLKDCAV | 391 | 10 | | | | | 7542 |
| HPV45 | E1 | QAKYLKDCAVM | 391 | 11 | | | | | 7543 |
| HPV45 | E1 | QALFHAQEV | 67 | 9 | 0.0002 | | | | 7544 |
| HPV45 | E1 | QASNKKAA | 192 | 8 | | | | | 7545 |
| HPV45 | E1 | QASNKKAAM | 192 | 9 | | | | | 7546 |
| HPV45 | E1 | QASNKKAAML | 192 | 10 | | | | | 7547 |
| HPV45 | E1 | QASNKKAAMLA | 192 | 11 | | | | | 7548 |
| HPV45 | E1 | QLADCNSNA | 374 | 9 | | | | | 7549 |
| HPV45 | E1 | QLADCNCNAA | 374 | 10 | | | | | 7550 |
| HPV45 | E1 | QLADCNSNAAA | 374 | 11 | | | | | 7551 |
| HPV45 | E1 | QLKCPPIL | 549 | 8 | | | | | 7552 |
| HPV45 | E1 | QLKCPPILL | 549 | 9 | 0.0003 | | | | 7553 |
| HPV45 | E1 | QLKCPPILLT | 549 | 10 | | | | | 7554 |
| HPV45 | E1 | QLSICEQA | 54 | 8 | | | | | 7555 |
| HPV45 | E1 | QLSVDTDL | 102 | 8 | | | | | 7556 |
| HPV45 | E1 | QMNMSQWI | 412 | 8 | | | | | 7557 |
| HPV45 | E1 | QVLHLLRKFA | 80 | 11 | | | | | 7558 |
| HPV45 | E1 | QVTVNTNA | 148 | 8 | | | | | 7559 |
| HPV45 | E1 | RALKEFLKGT | 451 | 10 | | | | | 7560 |
| HPV45 | E1 | RAQKRQMNM | 407 | 9 | | | | | 7561 |
| HPV45 | E1 | RLDLHEDDEDA | 612 | 11 | | | | | 7562 |
| HPV45 | E1 | RLTIIQHGI | 335 | 9 | | | | | 7563 |
| HPV45 | E1 | RLTVAKGL | 280 | 8 | | | | | 7564 |
| HPV45 | E1 | RLTVAKGLST | 280 | 10 | | | | | 7565 |
| HPV45 | E1 | RLTVAKGLSTL | 280 | 11 | | | | | 7566 |
| HPV45 | E1 | RQMNMSQWI | 411 | 9 | | | | | 7567 |
| HPV45 | E1 | RTGISNISEV | 316 | 10 | | | | | 7568 |
| HPV45 | E1 | RTWSRLDL | 608 | 8 | | | | | 7569 |
| HPV45 | E1 | RVTVFTFPHA | 575 | 10 | | | | | 7570 |
| HPV45 | E1 | SICEQAEQET | 56 | 10 | | | | | 7571 |
| HPV45 | E1 | SICEQAEQETA | 56 | 11 | | | | | 7572 |
| HPV45 | E1 | SIDRKHKPL | 539 | 9 | | | | | 7573 |
| HPV45 | E1 | SIDRKHKPLL | 539 | 10 | | | | | 7574 |
| HPV45 | E1 | SITELKEL | 183 | 8 | | | | | 7575 |
| HPV45 | E1 | SITELKELL | 183 | 9 | | | | | 7576 |
| HPV45 | E1 | SITELKELLQA | 183 | 11 | | | | | 7577 |
| HPV45 | E1 | SLNSGHKKA | 117 | 9 | | | | | 7578 |
| HPV45 | E1 | SQWIKYRCSKI | 416 | 11 | | | | | 7579 |
| HPV45 | E1 | STLLHVPET | 288 | 9 | | | | | 7580 |
| HPV45 | E1 | STLLHVPETCM | 288 | 11 | | | | | 7581 |
| HPV45 | E1 | SVAALYWYRT | 308 | 10 | | | | | 7582 |
| HPV45 | E1 | SVDTDLSPRL | 104 | 10 | | | | | 7583 |
| HPV45 | E1 | TAQALFHA | 65 | 8 | | | | | 7584 |
| HPV45 | E1 | TAQALFHAQEV | 65 | 11 | | | | | 7585 |
| HPV45 | E1 | TATDTGSDM | 39 | 9 | | | | | 7586 |
| HPV45 | E1 | TATDTGSDMV | 39 | 10 | | | | | 7587 |
| HPV45 | E1 | TIVEKKTGDV | 22 | 10 | | | | | 7588 |
| HPV45 | E1 | TIVEKKTGDVI | 22 | 11 | | | | | 7589 |
| HPV45 | E1 | TLIKPATL | 246 | 8 | | | | | 7590 |
| HPV45 | E1 | TLIKPATLYA | 246 | 10 | | | | | 7591 |
| HPV45 | E1 | TLLHVPET | 289 | 8 | | | | | 7592 |
| HPV45 | E1 | TLLHVPETCM | 289 | 10 | | | | | 7593 |
| HPV45 | E1 | TLLHVPETCML | 289 | 11 | | | | | 7594 |
| HPV45 | E1 | TLYAHIQCL | 252 | 9 | | | | | 7595 |
| HPV45 | E1 | TQLSICEQA | 53 | 9 | | | | | 7596 |
| HPV45 | E1 | TQVTVNTNA | 147 | 9 | | | | | 7597 |
| HPV45 | E1 | TTCTDWVW | 224 | 8 | | | | | 7598 |
| HPV45 | E1 | TTCTDWVMA | 224 | 9 | | | | | 7599 |
| HPV45 | E1 | TTCTDWVMAI | 224 | 10 | | | | | 7600 |
| HPV45 | E1 | TVAEGFKT | 239 | 8 | | | | | 7601 |
| HPV45 | E1 | TVAEGFKTL | 239 | 9 | | | | | 7602 |
| HPV45 | E1 | TVAEGFKTLI | 239 | 10 | | | | | 7603 |
| HPV45 | E1 | TVAKGLST | 282 | 8 | | | | | 7604 |
| HPV45 | E1 | TVAKGLSTL | 282 | 9 | | | | | 7605 |
| HPV45 | E1 | TVAKGLSTLL | 282 | 10 | | | | | 7606 |
| HPV45 | E1 | TVFTFPHA | 577 | 8 | | | | | 7607 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E1 | VAALYWYRT | 309 | 9 | | | | | 7608 |
| HPV45 | E1 | VAALYWYRTGI | 309 | 11 | | | | | 7609 |
| HPV45 | E1 | VAEGFKTL | 240 | 8 | | | | | 7610 |
| HPV45 | E1 | VAEGFKTLI | 240 | 9 | | | | | 7611 |
| HPV45 | E1 | VAKGLSTL | 283 | 8 | | | | | 7612 |
| HPV45 | E1 | VAKGLSTLL | 283 | 9 | | | | | 7613 |
| HPV45 | E1 | VAKGLSTLLHV | 283 | 11 | | | | | 7614 |
| HPV45 | E1 | VAMLDDAT | 511 | 8 | | | | | 7615 |
| HPV45 | E1 | VAMLDDATHT | 511 | 10 | | | | | 7616 |
| HPV45 | E1 | VISDDEDET | 31 | 9 | | | | | 7617 |
| HPV45 | E1 | VISDDEDETA | 31 | 10 | | | | | 7618 |
| HPV45 | E1 | VISDDEDETAT | 31 | 11 | | | | | 7619 |
| HPV45 | E1 | VLHLLKRKFA | 81 | 10 | | | | | 7620 |
| HPV45 | E1 | VMAIFGVNPT | 230 | 10 | | | | | 7621 |
| HPV45 | E1 | VMAIFGVNPTV | 230 | 11 | | | | | 7622 |
| HPV45 | E1 | VMCRHYKRA | 400 | 9 | | | | | 7623 |
| HPV45 | E1 | VQFLRYQGV | 436 | 9 | | | | | 7624 |
| HPV45 | E1 | VQNDAQVL | 75 | 8 | | | | | 7625 |
| HPV45 | E1 | VQNDAQVLHL | 75 | 10 | | | | | 7626 |
| HPV45 | E1 | VQNDAQVLHLL | 75 | 11 | | | | | 7627 |
| HPV45 | E1 | VQWAFDNDL | 354 | 9 | | | | | 7628 |
| HPV45 | E1 | VQWAFDNDLT | 354 | 10 | | | | | 7629 |
| HPV45 | E1 | VTGQNTRPL | 635 | 9 | | | | | 7630 |
| HPV45 | E1 | VTVFTFPHA | 576 | 9 | | | | | 7631 |
| HPV45 | E1 | WAFDNDLT | 356 | 8 | | | | | 7632 |
| HPV45 | E1 | WIKYRCSKI | 418 | 9 | | | | | 7633 |
| HPV45 | E1 | WIQRLTII | 332 | 8 | | | | | 7634 |
| HPV45 | E1 | WLEPLADT | 502 | 8 | | | | | 7635 |
| HPV45 | E1 | WLEPLADTKV | 502 | 10 | | | | | 7636 |
| HPV45 | E1 | WLEPLADTKVA | 502 | 11 | | | | | 7637 |
| HPV45 | E1 | WTYFDNYM | 522 | 8 | | | | | 7638 |
| HPV45 | E1 | WTYFDNYMRNA | 522 | 11 | | | | | 7639 |
| HPV45 | E1 | WVMAIFGV | 229 | 8 | | | | | 7640 |
| HPV45 | E1 | WVMAIFGVNPT | 229 | 11 | | | | | 7641 |
| HPV45 | E1 | YAQLADCNSNA | 372 | 11 | | | | | 7642 |
| HPV45 | E1 | YLESRVTV | 571 | 8 | | | | | 7643 |
| HPV45 | E1 | YLESRVTVFT | 571 | 10 | | | | | 7644 |
| HPV45 | E1 | YLKDCAVM | 394 | 8 | | | | | 7645 |
| HPV45 | E1 | YMRNALDGNPI | 528 | 11 | | | | | 7646 |
| HPV45 | E1 | YQGVEFISFL | 441 | 10 | | | | | 7647 |
| HPV45 | E2 | AACVSYWGV | 156 | 9 | | | | | 7648 |
| HPV45 | E2 | AIELQMAL | 78 | 8 | | | | | 7649 |
| HPV45 | E2 | AIELQMALKGL | 78 | 11 | | | | | 7650 |
| HPV45 | E2 | AILFTAREHGI | 47 | 11 | | | | | 7651 |
| HPV45 | E2 | AQSKYNNEEWT | 89 | 11 | | | | | 7652 |
| HPV45 | E2 | ATKRPRQCGL | 247 | 10 | | | | | 7653 |
| HPV45 | E2 | ATKRPRQCGLT | 247 | 11 | | | | | 7654 |
| HPV45 | E2 | ATQIVRQL | 216 | 8 | | | | | 7655 |
| HPV45 | E2 | ATQIVRQLQHA | 216 | 11 | | | | | 7656 |
| HPV45 | E2 | CLRYRLRKYA | 305 | 10 | | | | | 7657 |
| HPV45 | E2 | CMNYVVWDSI | 134 | 10 | | | | | 7658 |
| HPV45 | E2 | CVSYWGVYYI | 158 | 10 | | | | | 7659 |
| HPV45 | E2 | DINSQISYWQL | 31 | 11 | | | | | 7660 |
| HPV45 | E2 | DTCEELWNT | 102 | 9 | | | | | 7661 |
| HPV45 | E2 | DTVSATQI | 212 | 8 | | | | | 7662 |
| HPV45 | E2 | DTVSATQIV | 212 | 9 | | | | | 7663 |
| HPV45 | E2 | DVVTIPNSV | 351 | 9 | | | | | 7664 |
| HPV45 | E2 | DVVTIPNSVQI | 351 | 11 | | | | | 7665 |
| HPV45 | E2 | EISSTWHWT | 319 | 9 | | | | | 7666 |
| HPV45 | E2 | ELQMALKGL | 80 | 9 | | | | | 7667 |
| HPV45 | E2 | ELQMALKGLA | 80 | 10 | | | | | 7668 |
| HPV45 | E2 | EQHHGRVNT | 258 | 9 | | | | | 7669 |
| HPV45 | E2 | EQHHGRVNTHV | 258 | 11 | | | | | 7670 |
| HPV45 | E2 | ETGIWDKT | 148 | 8 | | | | | 7671 |
| HPV45 | E2 | ETGIWDKTA | 148 | 9 | | | | | 7672 |
| HPV45 | E2 | ETGIWDKTAA | 148 | 10 | | | | | 7673 |
| HPV45 | E2 | EVQRNTFL | 343 | 8 | | | | | 7674 |
| HPV45 | E2 | EVQRNTFLDV | 343 | 10 | | | | | 7675 |
| HPV45 | E2 | EVQRNTFLDVV | 343 | 11 | | | | | 7676 |
| HPV45 | E2 | EVQYGGNV | 192 | 8 | | | | | 7677 |
| HPV45 | E2 | EVQYGGNVI | 192 | 9 | | | | | 7678 |
| HPV45 | E2 | FLDVVTIPNSV | 349 | 11 | | | | | 7679 |
| HPV45 | E2 | FTAREHGI | 50 | 8 | | | | | 7680 |
| HPV45 | E2 | FTAREHGIT | 50 | 9 | | | | | 7681 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E2 | FTAREHGITKL | 50 | 11 | | | | | 7682 |
| HPV45 | E2 | GILTVTYNSEV | 334 | 11 | | | | | 7683 |
| HPV45 | E2 | GITKLNHQV | 56 | 9 | | | | | 7684 |
| HPV45 | E2 | GITKLNHQVV | 56 | 10 | | | | | 7685 |
| HPV45 | E2 | GIWDKTAA | 150 | 8 | | | | | 7686 |
| HPV45 | E2 | GIWDKTAACV | 150 | 10 | | | | | 7687 |
| HPV45 | E2 | GLTEQHHGRV | 255 | 10 | | | | | 7688 |
| HPV45 | E2 | GTPKPHIQT | 237 | 9 | | | | | 7689 |
| HPV45 | E2 | GTPKPHIQTPA | 237 | 11 | | | | | 7690 |
| HPV45 | E2 | GVYYIKDGDT | 163 | 10 | | | | | 7691 |
| HPV45 | E2 | GVYYIKDGDTT | 163 | 11 | | | | | 7692 |
| HPV45 | E2 | HASTSTPKT | 225 | 9 | | | | | 7693 |
| HPV45 | E2 | HASTSTPKTA | 225 | 10 | | | | | 7694 |
| HPV45 | E2 | HLKGDKNSL | 295 | 9 | | | | | 7695 |
| HPV45 | E2 | HQVVPPINI | 62 | 9 | | | | | 7696 |
| HPV45 | E2 | HVHNPLLCSST | 267 | 11 | | | | | 7697 |
| HPV45 | E2 | IIHLKGDKNSL | 293 | 11 | | | | | 7698 |
| HPV45 | E2 | ILFTAREHGI | 48 | 10 | | | | | 7699 |
| HPV45 | E2 | ILFTAREHGIT | 48 | 11 | | | | | 7700 |
| HPV45 | E2 | ILTVTYNSEV | 335 | 10 | | | | | 7701 |
| HPV45 | E2 | ITETGIWDKT | 146 | 10 | | | | | 7702 |
| HPV45 | E2 | ITETGIWDKTA | 146 | 11 | | | | | 7703 |
| HPV45 | E2 | ITKLNHQV | 57 | 8 | | | | | 7704 |
| HPV45 | E2 | ITKLNHQVV | 57 | 9 | | | | | 7705 |
| HPV45 | E2 | IVRQLQHA | 219 | 8 | | | | | 7706 |
| HPV45 | E2 | IVRQLQHAST | 219 | 10 | | | | | 7707 |
| HPV45 | E2 | KAHKAIEL | 74 | 8 | | | | | 7708 |
| HPV45 | E2 | KAHKAIELQM | 74 | 10 | | | | | 7709 |
| HPV45 | E2 | KAHKAIELQMA | 74 | 11 | | | | | 7710 |
| HPV45 | E2 | KAIELQMA | 77 | 8 | | | | | 7711 |
| HPV45 | E2 | KAIELQMAL | 77 | 9 | | | | | 7712 |
| HPV45 | E2 | KLNHQVVPPI | 59 | 10 | | | | | 7713 |
| HPV45 | E2 | KMQTPKESL | 2 | 9 | | | | | 7714 |
| HPV45 | E2 | KTAACVSYWGV | 154 | 11 | | | | | 7715 |
| HPV45 | E2 | KVCSGNTT | 284 | 8 | | | | | 7716 |
| HPV45 | E2 | KVCSGNTTPI | 284 | 10 | | | | | 7717 |
| HPV45 | E2 | KVCSGNTTPII | 284 | 11 | | | | | 7718 |
| HPV45 | E2 | LIRLENAI | 41 | 8 | | | | | 7719 |
| HPV45 | E2 | LIRLENAIL | 41 | 9 | | | | | 7720 |
| HPV45 | E2 | LIRLENAILFT | 41 | 11 | | | | | 7721 |
| HPV45 | E2 | LQDTCEEL | 100 | 8 | | | | | 7722 |
| HPV45 | E2 | LQDTCEELWNT | 100 | 11 | | | | | 7723 |
| HPV45 | E2 | LQHASTST | 223 | 8 | | | | | 7724 |
| HPV45 | E2 | LQHASTSTPKT | 223 | 11 | | | | | 7725 |
| HPV45 | E2 | LQMALKGL | 81 | 8 | | | | | 7726 |
| HPV45 | E2 | LQMALKGLA | 81 | 9 | | | | | 7727 |
| HPV45 | E2 | LTEQHHGRV | 256 | 9 | | | | | 7728 |
| HPV45 | E2 | LTEQHHGRVNT | 256 | 11 | | | | | 7729 |
| HPV45 | E2 | LTVTYNSEV | 336 | 9 | | | | | 7730 |
| HPV45 | E2 | MQTPKESL | 3 | 8 | | | | | 7731 |
| HPV45 | E2 | NISKSKAHKA | 69 | 10 | | | | | 7732 |
| HPV45 | E2 | NISKSKAHKAI | 69 | 11 | | | | | 7733 |
| HPV45 | E2 | NTFLDVVT | 347 | 8 | | | | | 7734 |
| HPV45 | E2 | NTFLDVVTI | 347 | 9 | | | | | 7735 |
| HPV45 | E2 | NTGILTVT | 332 | 8 | | | | | 7736 |
| HPV45 | E2 | NTHVHNPL | 265 | 8 | | | | | 7737 |
| HPV45 | E2 | NTHVHNPLL | 265 | 9 | | | | | 7738 |
| HPV45 | E2 | NTTPIIHL | 289 | 8 | | | | | 7739 |
| HPV45 | E2 | NTWEVQYGGNV | 189 | 11 | | | | | 7740 |
| HPV45 | E2 | NVIDCNDSM | 198 | 9 | | | | | 7741 |
| HPV45 | E2 | PATKRPRQCGL | 246 | 11 | | | | | 7742 |
| HPV45 | E2 | PINISKSKA | 67 | 9 | | | | | 7743 |
| HPV45 | E2 | QISVGYMT | 360 | 8 | | | | | 7744 |
| HPV45 | E2 | QISVGYMTI | 360 | 9 | | | | | 7745 |
| HPV45 | E2 | QISYWQLI | 35 | 8 | | | | | 7746 |
| HPV45 | E2 | QISYWQLIRL | 35 | 10 | | | | | 7747 |
| HPV45 | E2 | QIVRQLQHA | 218 | 9 | | | | | 7748 |
| HPV45 | E2 | QIVRQLQHAST | 218 | 11 | | | | | 7749 |
| HPV45 | E2 | QLIRLENA | 40 | 8 | | | | | 7750 |
| HPV45 | E2 | QLIRLENAI | 40 | 9 | | | | | 7751 |
| HPV45 | E2 | QLIRLENAIL | 40 | 10 | | | | | 7752 |
| HPV45 | E2 | QLQHASTST | 222 | 9 | | | | | 7753 |
| HPV45 | E2 | QMALKGLA | 82 | 8 | | | | | 7754 |
| HPV45 | E2 | QTPKESLSERL | 4 | 11 | | | | | 7755 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E2 | QVVPPINI | 63 | 8 | | | | | 7756 |
| HPV45 | E2 | RLENAILFT | 43 | 9 | | | | | 7757 |
| HPV45 | E2 | RLENAILFTA | 43 | 10 | | | | | 7758 |
| HPV45 | E2 | RLSALQDKI | 13 | 9 | | | | | 7759 |
| HPV45 | E2 | RLSALQDKIL | 13 | 10 | | | | | 7760 |
| HPV45 | E2 | RQLQHAST | 221 | 8 | | | | | 7761 |
| HPV45 | E2 | RQLQHASTST | 221 | 10 | | | | | 7762 |
| HPV45 | E2 | RVNTHVHNPL | 263 | 10 | | | | | 7763 |
| HPV45 | E2 | RVNTHVHNPLL | 263 | 11 | | | | | 7764 |
| HPV45 | E2 | SALQDKIL | 15 | 8 | | | | | 7765 |
| HPV45 | E2 | SATQIVRQL | 215 | 9 | | | | | 7766 |
| HPV45 | E2 | SIYYITET | 142 | 8 | | | | | 7767 |
| HPV45 | E2 | SIYYITETGI | 142 | 10 | | | | | 7768 |
| HPV45 | E2 | SLKCLRYRL | 302 | 9 | | | | | 7769 |
| HPV45 | E2 | SLSERLSA | 9 | 8 | | | | | 7770 |
| HPV45 | E2 | SLSERLSAL | 9 | 9 | | | | | 7771 |
| HPV45 | E2 | SMCSTSDDT | 205 | 9 | | | | | 7772 |
| HPV45 | E2 | SMCSTSDDTV | 205 | 10 | | | | | 7773 |
| HPV45 | E2 | SQCFKKGGKT | 113 | 10 | | | | | 7774 |
| HPV45 | E2 | SQCFKKGGKTV | 113 | 11 | | | | | 7775 |
| HPV45 | E2 | SQISYWQL | 34 | 8 | | | | | 7776 |
| HPV45 | E2 | SQISYWQLI | 34 | 9 | | | | | 7777 |
| HPV45 | E2 | SQISYWQLIRL | 34 | 11 | | | | | 7778 |
| HPV45 | E2 | STPKTASV | 229 | 8 | | | | | 7779 |
| HPV45 | E2 | STPKTASVGT | 229 | 10 | | | | | 7780 |
| HPV45 | E2 | STSDDTVSA | 208 | 9 | | | | | 7781 |
| HPV45 | E2 | STSDDTVSAT | 208 | 10 | | | | | 7782 |
| HPV45 | E2 | STSNNKRRKV | 276 | 10 | | | | | 7783 |
| HPV45 | E2 | STSTPKTA | 227 | 8 | | | | | 7784 |
| HPV45 | E2 | STSTPKTASV | 227 | 10 | | | | | 7785 |
| HPV45 | E2 | SVGTPKPHI | 235 | 9 | | | | | 7786 |
| HPV45 | E2 | SVGTPKPHIQT | 235 | 11 | | | | | 7787 |
| HPV45 | E2 | SVQISVGYM | 358 | 9 | | | | | 7788 |
| HPV45 | E2 | SVQISVGYMT | 358 | 10 | | | | | 7789 |
| HPV45 | E2 | SVQISVGYMTI | 358 | 11 | | | | | 7790 |
| HPV45 | E2 | TAACVSYWGV | 155 | 10 | | | | | 7791 |
| HPV45 | E2 | TAREHGIT | 51 | 8 | | | | | 7792 |
| HPV45 | E2 | TAREHGITKL | 51 | 10 | | | | | 7793 |
| HPV45 | E2 | TASVGTPKPHI | 233 | 11 | | | | | 7794 |
| HPV45 | E2 | TIPNSVQI | 354 | 8 | | | | | 7795 |
| HPV45 | E2 | TIPNSVQISV | 354 | 10 | | | | | 7796 |
| HPV45 | E2 | TLQDTCEEL | 99 | 9 | | | | | 7797 |
| HPV45 | E2 | TQIVRQLQHA | 217 | 10 | | | | | 7798 |
| HPV45 | E2 | TVSATQIV | 213 | 8 | | | | | 7799 |
| HPV45 | E2 | TVSATQIVRQL | 213 | 11 | | | | | 7800 |
| HPV45 | E2 | TVTYNSEV | 337 | 8 | | | | | 7801 |
| HPV45 | E2 | VIDCNDSM | 199 | 8 | | | | | 7802 |
| HPV45 | E2 | VIDCNDSMCST | 199 | 11 | | | | | 7803 |
| HPV45 | E2 | VQISVGYM | 359 | 8 | | | | | 7804 |
| HPV45 | E2 | VQISVGYMT | 359 | 9 | | | | | 7805 |
| HPV45 | E2 | VQISVGYMTI | 359 | 10 | | | | | 7806 |
| HPV45 | E2 | VQRNTFLDV | 344 | 9 | | | | | 7807 |
| HPV45 | E2 | VQRNTFLDVV | 344 | 10 | | | | | 7808 |
| HPV45 | E2 | VQRNTFLDVVT | 344 | 11 | | | | | 7809 |
| HPV45 | E2 | VQYGGNVI | 193 | 8 | | | | | 7810 |
| HPV45 | E2 | VTIPNSVQI | 353 | 9 | | | | | 7811 |
| HPV45 | E2 | VTIPNSVQISV | 353 | 11 | | | | | 7812 |
| HPV45 | E2 | VTYNSEVQRNT | 338 | 11 | | | | | 7813 |
| HPV45 | E2 | VVTIPNSV | 352 | 8 | | | | | 7814 |
| HPV45 | E2 | VVTIPNSVQI | 352 | 10 | | | | | 7815 |
| HPV45 | E2 | VVWDSIYYI | 138 | 9 | | | | | 7816 |
| HPV45 | E2 | VVWDSIYYIT | 138 | 10 | | | | | 7817 |
| HPV45 | E2 | WQLIRLENA | 39 | 9 | | | | | 7818 |
| HPV45 | E2 | WQLIRLENAI | 39 | 10 | | | | | 7819 |
| HPV45 | E2 | WQLIRLENAIL | 39 | 11 | | | | | 7820 |
| HPV45 | E2 | WTGCNKNT | 326 | 8 | | | | | 7821 |
| HPV45 | E2 | WTGCNKNTGI | 326 | 10 | | | | | 7822 |
| HPV45 | E2 | WTGCNKNTGIL | 326 | 11 | | | | | 7823 |
| HPV45 | E2 | WTLQDTCEEL | 98 | 10 | | | | | 7824 |
| HPV45 | E2 | YADHYSEI | 313 | 8 | | | | | 7825 |
| HPV45 | E2 | YADHYSEISST | 313 | 11 | | | | | 7826 |
| HPV45 | E2 | YIKDGDTT | 166 | 8 | | | | | 7827 |
| HPV45 | E2 | YIKDGDTTYYV | 166 | 11 | | | | | 7828 |
| HPV45 | E2 | YITETGIWDKT | 145 | 11 | | | | | 7829 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E2 | YVVWDSIYYI | 137 | 10 | | | | | 7830 |
| HPV45 | E2 | YVVWDSIYYIT | 137 | 11 | | | | | 7831 |
| HPV45 | E6 | ATLERTEV | 37 | 8 | | | | | 7832 |
| HPV45 | E6 | CIAYAACHKCI | 59 | 11 | | | | | 7833 |
| HPV45 | E6 | CIDFYSRI | 68 | 8 | 0.0001 | | | | 7834 |
| HPV45 | E6 | CIDFYSRIREL | 68 | 11 | | | | | 7835 |
| HPV45 | E6 | CLRCQKPL | 105 | 8 | 0.0001 | | | | 7836 |
| HPV45 | E6 | CLRCQKPLNPA | 105 | 11 | | | | | 7837 |
| HPV45 | E6 | CQKPLNPA | 108 | 8 | | | | | 7838 |
| HPV45 | E6 | CTELNTSL | 18 | 8 | | | | | 7839 |
| HPV45 | E6 | CTELNTSLQDV | 18 | 11 | | | | | 7840 |
| HPV45 | E6 | CVYCKATL | 32 | 8 | | | | | 7841 |
| HPV45 | E6 | CVYCKATLERT | 32 | 11 | | | | | 7842 |
| HPV45 | E6 | DLCTELNT | 16 | 8 | | | | | 7843 |
| HPV45 | E6 | DLCTELNTSL | 16 | 10 | 0.0001 | | | | 7844 |
| HPV45 | E6 | DLFIVYRDCI | 51 | 10 | | | | | 7845 |
| HPV45 | E6 | DLFIVYRDCIA | 51 | 11 | | | | | 7846 |
| HPV45 | E6 | DQARQERL | 143 | 8 | | | | | 7847 |
| HPV45 | E6 | DVSIACVYCKA | 27 | 11 | | | | | 7848 |
| HPV45 | E6 | ELNTSLQDV | 20 | 9 | | | | | 7849 |
| HPV45 | E6 | ELNTSLQDVSI | 20 | 11 | | | | | 7850 |
| HPV45 | E6 | ELRYYSNSV | 77 | 9 | | | | | 7851 |
| HPV45 | E6 | ELYNLLIRCL | 97 | 10 | | | | | 7852 |
| HPV45 | E6 | ETLEKITNT | 88 | 9 | | | | | 7853 |
| HPV45 | E6 | ETLEKITNTEL | 88 | 11 | | | | | 7854 |
| HPV45 | E6 | EVYQFAFKDL | 43 | 10 | | | | | 7855 |
| HPV45 | E6 | FAFKDLFI | 47 | 8 | | | | | 7856 |
| HPV45 | E6 | FAFKDLFIV | 47 | 9 | | | | | 7857 |
| HPV45 | E6 | FIVYRDCI | 53 | 8 | | | | | 7858 |
| HPV45 | E6 | FIVYRDCIA | 53 | 9 | | | | | 7859 |
| HPV45 | E6 | FIVYRDCIAYA | 53 | 11 | | | | | 7860 |
| HPV45 | E6 | GQCNTCCDQA | 136 | 10 | | | | | 7861 |
| HPV45 | E6 | GQYRGQCNT | 132 | 9 | | | | | 7862 |
| HPV45 | E6 | HLKDKRRFHSI | 120 | 11 | | | | | 7863 |
| HPV45 | E6 | IACVYCKA | 30 | 8 | | | | | 7864 |
| HPV45 | E6 | IACVYCKAT | 30 | 9 | | | | | 7865 |
| HPV45 | E6 | IACVYCKATL | 30 | 10 | | | | | 7866 |
| HPV45 | E6 | IAGQYRGQCNT | 130 | 11 | | | | | 7867 |
| HPV45 | E6 | IAYAACHKCI | 60 | 10 | | | | | 7868 |
| HPV45 | E6 | ITNTELYNL | 93 | 9 | | | | | 7869 |
| HPV45 | E6 | ITNTELYNLL | 93 | 10 | | | | | 7870 |
| HPV45 | E6 | ITNTELYNLLI | 93 | 11 | | | | | 7871 |
| HPV45 | E6 | IVYRDCIA | 54 | 8 | | | | | 7872 |
| HPV45 | E6 | IVYRDCIAYA | 54 | 10 | | | | | 7873 |
| HPV45 | E6 | IVYRDCIAYAA | 54 | 11 | | | | | 7874 |
| HPV45 | E6 | KATLERTEV | 36 | 9 | | | | | 7875 |
| HPV45 | E6 | KITNTELYNL | 92 | 10 | | | | | 7876 |
| HPV45 | E6 | KITNTELYNLL | 92 | 11 | | | | | 7877 |
| HPV45 | E6 | KLPDLCTEL | 13 | 9 | 0.0035 | | | | 7878 |
| HPV45 | E6 | KLPDLCTELNT | 13 | 11 | | | | | 7879 |
| HPV45 | E6 | LIRCLRCQKPL | 102 | 11 | | | | | 7880 |
| HPV45 | E6 | LQDVSIACV | 25 | 9 | | | | | 7881 |
| HPV45 | E6 | MARFDDPT | 1 | 8 | | | | | 7882 |
| HPV45 | E6 | NTELYNLL | 95 | 8 | | | | | 7883 |
| HPV45 | E6 | NTELYNLLI | 95 | 9 | | | | | 7884 |
| HPV45 | E6 | NTSLQDVSI | 22 | 9 | | | | | 7885 |
| HPV45 | E6 | NTSLQDVSIA | 22 | 10 | | | | | 7886 |
| HPV45 | E6 | PAEKRRHL | 114 | 8 | | | | | 7887 |
| HPV45 | E6 | PLNPAEKRRHL | 111 | 11 | | | | | 7888 |
| HPV45 | E6 | PTQRPYKL | 7 | 8 | | | | | 7889 |
| HPV45 | E6 | PTQRPYKLPDL | 7 | 11 | | | | | 7890 |
| HPV45 | E6 | RLRRRRET | 149 | 8 | | | | | 7891 |
| HPV45 | E6 | RLRRRRETQV | 149 | 10 | | | | | 7892 |
| HPV45 | E6 | RQERLRRRRET | 146 | 11 | | | | | 7893 |
| HPV45 | E6 | RTEVYQFA | 41 | 8 | | | | | 7894 |
| HPV45 | E6 | SIACVYCKA | 29 | 9 | | | | | 7895 |
| HPV45 | E6 | SIACVYCKAT | 29 | 10 | | | | | 7896 |
| HPV45 | E6 | SIACVYCKATL | 29 | 11 | | | | | 7897 |
| HPV45 | E6 | SLQDVSIA | 24 | 8 | | | | | 7898 |
| HPV45 | E6 | SLQDVSIACV | 24 | 10 | | | | | 7899 |
| HPV45 | E6 | SVYGETLEKI | 84 | 10 | | | | | 7900 |
| HPV45 | E6 | SVYGETLEKIT | 84 | 11 | | | | | 7901 |
| HPV45 | E6 | TLEKITNT | 89 | 8 | | | | | 7902 |
| HPV45 | E6 | TLEKITNTEL | 89 | 10 | | | | | 7903 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | E6 | TLERTEVYQFA | 38 | 11 | | | | | 7904 |
| HPV45 | E6 | TQRPYKLPDL | 8 | 10 | | | | | 7905 |
| HPV45 | E6 | YAACHKCI | 62 | 8 | | | | | 7906 |
| HPV45 | E6 | YQFAFKDL | 45 | 8 | | | | | 7907 |
| HPV45 | E6 | YQFAFKDLFI | 45 | 10 | | | | | 7908 |
| HPV45 | E6 | YQFAFKDLFIV | 45 | 11 | | | | | 7909 |
| HPV45 | E7 | AQLPARRA | 48 | 8 | | | | | 7910 |
| HPV45 | E7 | ATLQEIVL | 6 | 8 | | | | | 7911 |
| HPV45 | E7 | ATLQEIVLHL | 6 | 10 | | | | | 7912 |
| HPV45 | E7 | CVCCKCDGRI | 64 | 10 | | | | | 7913 |
| HPV45 | E7 | DLLCYEQL | 25 | 8 | | | | | 7914 |
| HPV45 | E7 | DLRTLQQL | 83 | 8 | | | | | 7915 |
| HPV45 | E7 | DLRTLQQLFL | 83 | 10 | | | | | 7916 |
| HPV45 | E7 | EADGVSHA | 41 | 8 | | | | | 7917 |
| HPV45 | E7 | EADGVSHAQL | 41 | 10 | | | | | 7918 |
| HPV45 | E7 | ELDPVDLL | 20 | 8 | | | | | 7919 |
| HPV45 | E7 | ELTVESSA | 74 | 8 | | | | | 7920 |
| HPV45 | E7 | ELTVESSADDL | 74 | 11 | | | | | 7921 |
| HPV45 | E7 | FLSTLSFV | 91 | 8 | | | | | 7922 |
| HPV45 | E7 | FVCPWCAT | 97 | 8 | | | | | 7923 |
| HPV45 | E7 | GVSHAQLPA | 44 | 9 | | | | | 7924 |
| HPV45 | E7 | HAQLPARRA | 47 | 9 | | | | | 7925 |
| HPV45 | E7 | HLEPQNEL | 14 | 8 | | | | | 7926 |
| HPV45 | E7 | HLEPQNELDPV | 14 | 11 | | | | | 7927 |
| HPV45 | E7 | IVLHLEPQNEL | 11 | 11 | | | | | 7928 |
| HPV45 | E7 | LQEIVLHL | 8 | 8 | | | | | 7929 |
| HPV45 | E7 | LQQLFLST | 87 | 8 | | | | | 7930 |
| HPV45 | E7 | LQQLFLSTL | 87 | 9 | | | | | 7931 |
| HPV45 | E7 | LTVESSADDL | 75 | 10 | | | | | 7932 |
| HPV45 | E7 | PQNELDPV | 17 | 8 | | | | | 7933 |
| HPV45 | E7 | PQNELDPVDL | 17 | 10 | | | | | 7934 |
| HPV45 | E7 | PQNELDPVDLL | 17 | 11 | | | | | 7935 |
| HPV45 | E7 | PQRHKILCV | 57 | 9 | | | | | 7936 |
| HPV45 | E7 | PVDLLCYEQL | 23 | 10 | | | | | 7937 |
| HPV45 | E7 | QLFLSTLSFV | 89 | 10 | | | | | 7938 |
| HPV45 | E7 | QQLFLSTL | 88 | 8 | | | | | 7939 |
| HPV45 | E7 | QQLFLSTLSFV | 88 | 11 | | | | | 7940 |
| HPV45 | E7 | RAEPQRHKI | 54 | 9 | | | | | 7941 |
| HPV45 | E7 | RAEPQRHKIL | 54 | 10 | | | | | 7942 |
| HPV45 | E7 | RATLQEIV | 5 | 8 | | | | | 7943 |
| HPV45 | E7 | RATLQEIVL | 5 | 9 | | | | | 7944 |
| HPV45 | E7 | RATLQEIVLHL | 5 | 11 | | | | | 7945 |
| HPV45 | E7 | RIELTVESSA | 72 | 10 | | | | | 7946 |
| HPV45 | E7 | RTLQQLFL | 85 | 8 | | | | | 7947 |
| HPV45 | E7 | RTLQQLFLST | 85 | 10 | | | | | 7948 |
| HPV45 | E7 | RTLQQLFLSTL | 85 | 11 | | | | | 7949 |
| HPV45 | E7 | SADDLRTL | 80 | 8 | | | | | 7950 |
| HPV45 | E7 | SADDLRTLQQL | 80 | 11 | | | | | 7951 |
| HPV45 | E7 | STLSFVCPWCA | 93 | 11 | | | | | 7952 |
| HPV45 | E7 | TLQEIVLHL | 7 | 9 | | | | | 7953 |
| HPV45 | E7 | TLQQLFLST | 86 | 9 | | | | | 7954 |
| HPV45 | E7 | TLQQLFLSTL | 86 | 10 | | | | | 7955 |
| HPV45 | E7 | TLSFVCPWCA | 94 | 10 | 0.0027 | | | | 7956 |
| HPV45 | E7 | TLSFVCPWCAT | 94 | 11 | | | | | 7957 |
| HPV45 | E7 | TVESSADDL | 76 | 9 | | | | | 7958 |
| HPV45 | E7 | TVESSADDLRT | 76 | 11 | | | | | 7959 |
| HPV45 | E7 | VLHLEPQNEL | 12 | 10 | | | | | 7960 |
| HPV45 | L1 | AASTSTASRPA | 517 | 11 | | | | | 7961 |
| HPV45 | L1 | AATAVITQDV | 161 | 10 | | | | | 7962 |
| HPV45 | L1 | AIGEHWAKGT | 191 | 10 | | | | | 7963 |
| HPV45 | L1 | AIGEHWAKGTL | 191 | 11 | | | | | 7964 |
| HPV45 | L1 | ALPDPNKFGL | 103 | 10 | | | | | 7965 |
| HPV45 | L1 | ALWRPSDST | 28 | 9 | | | | | 7966 |
| HPV45 | L1 | ALWRPSDSTV | 28 | 10 | | | | | 7967 |
| HPV45 | L1 | AMDFSTLQDT | 234 | 10 | | | | | 7968 |
| HPV45 | L1 | AQGHNNGI | 345 | 8 | | | | | 7969 |
| HPV45 | L1 | AQLQPGDCPPL | 205 | 11 | | | | | 7970 |
| HPV45 | L1 | ATAVITQDV | 162 | 9 | | | | | 7971 |
| HPV45 | L1 | AVITQDVRDNV | 164 | 11 | | | | | 7972 |
| HPV45 | L1 | AVTCQKDT | 455 | 8 | | | | | 7973 |
| HPV45 | L1 | AVTCQKDTT | 455 | 9 | | | | | 7974 |
| HPV45 | L1 | CASTQNPV | 374 | 8 | | | | | 7975 |
| HPV45 | L1 | CASTQNPVPNT | 374 | 11 | | | | | 7976 |
| HPV45 | L1 | CILGCVPA | 184 | 8 | | | | | 7977 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | L1 | CILGCVPAI | 184 | 9 | | | | | 7978 |
| HPV45 | L1 | CLRREQLFA | 276 | 9 | | | | | 7979 |
| HPV45 | L1 | CQSICKYPDYL | 252 | 11 | | | | | 7980 |
| HPV45 | L1 | CTITLTAEV | 409 | 9 | | | | | 7981 |
| HPV45 | L1 | CTITLTAEVM | 409 | 10 | | | | | 7982 |
| HPV45 | L1 | CVPAIGEHWA | 188 | 10 | | | | | 7983 |
| HPV45 | L1 | CVYSPSPSGSI | 318 | 11 | | | | | 7984 |
| HPV45 | L1 | DLKEKFSSDL | 480 | 10 | | | | | 7985 |
| HPV45 | L1 | DLQFIFQL | 401 | 8 | | | | | 7986 |
| HPV45 | L1 | DLQFIFQLCT | 401 | 10 | | | | | 7987 |
| HPV45 | L1 | DLQFIFQLCTI | 401 | 11 | | | | | 7988 |
| HPV45 | L1 | DLYIKGTSA | 301 | 9 | | | | | 7989 |
| HPV45 | L1 | DLYIKGTSANM | 301 | 11 | | | | | 7990 |
| HPV45 | L1 | DMVDTGYGA | 226 | 9 | | | | | 7991 |
| HPV45 | L1 | DMVDTGYGAM | 226 | 10 | | | | | 7992 |
| HPV45 | L1 | DQYPLGRKFL | 490 | 10 | | | | | 7993 |
| HPV45 | L1 | DQYPLGRKFLV | 490 | 11 | | | | | 7994 |
| HPV45 | L1 | DTESAHAA | 155 | 8 | | | | | 7995 |
| HPV45 | L1 | DTESAHAAT | 155 | 9 | | | | | 7996 |
| HPV45 | L1 | DTESAHAATA | 155 | 10 | | | | | 7997 |
| HPV45 | L1 | DTESAHAATAV | 155 | 11 | | | | | 7998 |
| HPV45 | L1 | DTGYGAMDFST | 229 | 11 | | | | | 7999 |
| HPV45 | L1 | DTKCEVPL | 242 | 8 | | | | | 8000 |
| HPV45 | L1 | DTKCEVPLDI | 242 | 10 | | | | | 8001 |
| HPV45 | L1 | DTTRSTNL | 364 | 8 | | | | | 8002 |
| HPV45 | L1 | DTTRSTNLT | 364 | 9 | | | | | 8003 |
| HPV45 | L1 | DTTRSTNLTL | 364 | 10 | | | | | 8004 |
| HPV45 | L1 | DTVPTDLYI | 296 | 9 | | | | | 8005 |
| HPV45 | L1 | DTYRFVQSV | 446 | 9 | | | | | 8006 |
| HPV45 | L1 | DTYRFVQSVA | 446 | 10 | | | | | 8007 |
| HPV45 | L1 | DTYRFVQSVAV | 446 | 11 | | | | | 8008 |
| HPV45 | L1 | DVRDNVSV | 169 | 8 | | | | | 8009 |
| HPV45 | L1 | EIGRGQPL | 133 | 8 | | | | | 8010 |
| HPV45 | L1 | EIGRGQPLGI | 133 | 10 | | | | | 8011 |
| HPV45 | L1 | ETQRLVWA | 121 | 8 | | | | | 8012 |
| HPV45 | L1 | ETQRLVWACV | 121 | 10 | | | | | 8013 |
| HPV45 | L1 | EVMSYIHSM | 416 | 9 | | | | | 8014 |
| HPV45 | L1 | EVPLDICQSI | 246 | 10 | | | | | 8015 |
| HPV45 | L1 | FARHFWNRA | 283 | 9 | | | | | 8016 |
| HPV45 | L1 | FARHFWNRAGV | 283 | 11 | | | | | 8017 |
| HPV45 | L1 | FIFQLCTI | 404 | 8 | | | | | 8018 |
| HPV45 | L1 | FIFQLCTIT | 404 | 9 | | | | | 8019 |
| HPV45 | L1 | FIFQLCTITL | 404 | 10 | | | | | 8020 |
| HPV45 | L1 | FIFQLCTITLT | 404 | 11 | | | | | 8021 |
| HPV45 | L1 | FLKNVNVFPI | 14 | 10 | | | | | 8022 |
| HPV45 | L1 | FQLCTITL | 406 | 8 | | | | | 8023 |
| HPV45 | L1 | FQLCTITLT | 406 | 9 | | | | | 8024 |
| HPV45 | L1 | FQLCTITLTA | 406 | 10 | | | | | 8025 |
| HPV45 | L1 | FVQSVAVT | 450 | 8 | | | | | 8026 |
| HPV45 | L1 | FVTVVDTT | 359 | 8 | | | | | 8027 |
| HPV45 | L1 | FVTVVDTTRST | 359 | 11 | | | | | 8028 |
| HPV45 | L1 | GAGNKQAV | 82 | 8 | | | | | 8029 |
| HPV45 | L1 | GAGNKQAVPKV | 82 | 11 | | | | | 8030 |
| HPV45 | L1 | GAMDFSTL | 233 | 8 | | | | | 8031 |
| HPV45 | L1 | GAMDFSTLQDT | 233 | 11 | | | | | 8032 |
| HPV45 | L1 | GICWHNQL | 351 | 8 | | | | | 8033 |
| HPV45 | L1 | GICWHNQLFV | 351 | 10 | | | | | 8034 |
| HPV45 | L1 | GICWHNQLFVT | 351 | 11 | | | | | 8035 |
| HPV45 | L1 | GIIIFLKNV | 10 | 9 | | | | | 8036 |
| HPV45 | L1 | GIIIFLKNVNV | 10 | 11 | | | | | 8037 |
| HPV45 | L1 | GLRRRPTI | 503 | 8 | | | | | 8038 |
| HPV45 | L1 | GLSGHPFYNKL | 143 | 11 | | | | | 8039 |
| HPV45 | L1 | GMEIGRGQPL | 131 | 10 | | | | | 8040 |
| HPV45 | L1 | GQPLGIGL | 137 | 8 | | | | | 8041 |
| HPV45 | L1 | GTLCKPAQL | 199 | 9 | | | | | 8042 |
| HPV45 | L1 | GTSANMRET | 306 | 9 | | | | | 8043 |
| HPV45 | L1 | GVMGDTVPT | 292 | 9 | | | | | 8044 |
| HPV45 | L1 | GVMGDTVPTDL | 292 | 11 | | | | | 8045 |
| HPV45 | L1 | GVPPPPTT | 435 | 8 | | | | | 8046 |
| HPV45 | L1 | GVPPPPTTSL | 435 | 10 | | | | | 8047 |
| HPV45 | L1 | GVPPPPTTSLV | 435 | 11 | | | | | 8048 |
| HPV45 | L1 | HAATAVIT | 160 | 8 | | | | | 8049 |
| HPV45 | L1 | HAATAVITQDV | 160 | 11 | | | | | 8050 |
| HPV45 | L1 | HAGSSRLL | 62 | 8 | | | | | 8051 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | L1 | HAGSSRLLT | 62 | 9 | | | | | 8052 |
| HPV45 | L1 | HAGSSRLLTV | 62 | 10 | | | | | 8053 |
| HPV45 | L1 | HVEEYDLQFI | 396 | 10 | | | | | 8054 |
| HPV45 | L1 | IIEDGDMV | 221 | 8 | | | | | 8055 |
| HPV45 | L1 | IIEDGDMVDT | 221 | 10 | | | | | 8056 |
| HPV45 | L1 | IIFLKNVNV | 12 | 9 | | | | | 8057 |
| HPV45 | L1 | IIIFLKNV | 11 | 8 | | | | | 8058 |
| HPV45 | L1 | IIIFLKNVNV | 11 | 10 | | | | | 8059 |
| HPV45 | L1 | IIYGHGII | 5 | 8 | | | | | 8060 |
| HPV45 | L1 | IIYGHGIII | 5 | 9 | | | | | 8061 |
| HPV45 | L1 | IIYGHGIIIFL | 5 | 11 | | | | | 8062 |
| HPV45 | L1 | ILENWNFGV | 428 | 9 | | | | | 8063 |
| HPV45 | L1 | ILGCVPAI | 185 | 8 | | | | | 8064 |
| HPV45 | L1 | ITLTAEVM | 411 | 8 | | | | | 8065 |
| HPV45 | L1 | ITLTAEVMSYI | 411 | 11 | | | | | 8066 |
| HPV45 | L1 | ITQDVRDNV | 166 | 9 | | | | | 8067 |
| HPV45 | L1 | ITQDVRDNVSV | 166 | 11 | | | | | 8068 |
| HPV45 | L1 | ITTSDSQL | 328 | 8 | | | | | 8069 |
| HPV45 | L1 | KAQGHNNGI | 344 | 9 | | | | | 8070 |
| HPV45 | L1 | KLDDTESA | 152 | 8 | | | | | 8071 |
| HPV45 | L1 | KLDDTESAHA | 152 | 10 | | | | | 8072 |
| HPV45 | L1 | KLDDTESAHAA | 152 | 11 | | | | | 8073 |
| HPV45 | L1 | KLKFWTVDL | 473 | 9 | | | | | 8074 |
| HPV45 | L1 | KQAVPKVSA | 86 | 9 | | | | | 8075 |
| HPV45 | L1 | KQDPYDKL | 467 | 8 | | | | | 8076 |
| HPV45 | L1 | KQTQLCIL | 179 | 8 | | | | | 8077 |
| HPV45 | L1 | KQTQLCILGCV | 179 | 11 | | | | | 8078 |
| HPV45 | L1 | KVSAYQYRV | 91 | 9 | | | | | 8079 |
| HPV45 | L1 | LLTVGNPYFRV | 68 | 11 | | | | | 8080 |
| HPV45 | L1 | LQDTKCEV | 240 | 8 | | | | | 8081 |
| HPV45 | L1 | LQDTKCEVPL | 240 | 10 | | | | | 8082 |
| HPV45 | L1 | LQFIFQLCT | 402 | 9 | | | | | 8083 |
| HPV45 | L1 | LQFIFQLCTI | 402 | 10 | | | | | 8084 |
| HPV45 | L1 | LQFIFQLCTIT | 402 | 11 | | | | | 8085 |
| HPV45 | L1 | LQPGDCPPL | 207 | 9 | | | | | 8086 |
| HPV45 | L1 | LQPGDCPPLEL | 207 | 11 | | | | | 8087 |
| HPV45 | L1 | LTAEVMSYI | 413 | 9 | | | | | 8088 |
| HPV45 | L1 | LTLCASTQNPV | 371 | 11 | | | | | 8089 |
| HPV45 | L1 | LTVGNPYFRV | 69 | 10 | | | | | 8090 |
| HPV45 | L1 | LTVGNPYFRVV | 69 | 11 | | | | | 8091 |
| HPV45 | L1 | LVDTYRFV | 444 | 8 | | | | | 8092 |
| HPV45 | L1 | LVDTYRFVQSV | 444 | 11 | | | | | 8093 |
| HPV45 | L1 | LVQAGLRRRPT | 499 | 11 | | | | | 8094 |
| HPV45 | L1 | LVWACVGM | 125 | 8 | | | | | 8095 |
| HPV45 | L1 | LVWACVGMEI | 125 | 10 | | | | | 8096 |
| HPV45 | L1 | MAHNIIYGHGI | 1 | 11 | | | | | 8097 |
| HPV45 | L1 | MALWRPSDST | 27 | 10 | | | | | 8098 |
| HPV45 | L1 | MALWRPSDSTV | 27 | 11 | | | | | 8099 |
| HPV45 | L1 | MVDTGYGA | 227 | 8 | | | | | 8100 |
| HPV45 | L1 | MVDTGYGAM | 227 | 9 | | | | | 8101 |
| HPV45 | L1 | NIIYGHGI | 4 | 8 | | | | | 8102 |
| HPV45 | L1 | NIIYGHGII | 4 | 9 | | | | | 8103 |
| HPV45 | L1 | NIIYGHGIII | 4 | 10 | | | | | 8104 |
| HPV45 | L1 | NLTLCAST | 370 | 8 | | | | | 8105 |
| HPV45 | L1 | NMRETPGSCV | 310 | 10 | | | | | 8106 |
| HPV45 | L1 | NQLFVTVV | 356 | 8 | | | | | 8107 |
| HPV45 | L1 | NQLFVTVVDT | 356 | 10 | | | | | 8108 |
| HPV45 | L1 | NQLFVTVVDTT | 356 | 11 | | | | | 8109 |
| HPV45 | L1 | NTDDYVSRT | 49 | 9 | | | | | 8110 |
| HPV45 | L1 | NTDDYVSRTSI | 49 | 11 | | | | | 8111 |
| HPV45 | L1 | NTIIEDGDM | 219 | 9 | | | | | 8112 |
| HPV45 | L1 | NTIIEDGDMV | 219 | 10 | | | | | 8113 |
| HPV45 | L1 | NVFPIFLQM | 19 | 9 | | | | | 8114 |
| HPV45 | L1 | NVFPIFLQMA | 19 | 10 | | | | | 8115 |
| HPV45 | L1 | NVFPIFLQMAL | 19 | 11 | | | | | 8116 |
| HPV45 | L1 | NVNVFPIFL | 17 | 9 | | | | | 8117 |
| HPV45 | L1 | NVNVFPIFLQM | 17 | 11 | | | | | 8118 |
| HPV45 | L1 | NVSVDYKQT | 173 | 9 | | | | | 8119 |
| HPV45 | L1 | NVSVDYKQTQL | 173 | 11 | | | | | 8120 |
| HPV45 | L1 | PAASTSTA | 516 | 8 | | | | | 8121 |
| HPV45 | L1 | PAIGEHWA | 190 | 8 | | | | | 8122 |
| HPV45 | L1 | PAIGEHWAKGT | 190 | 11 | | | | | 8123 |
| HPV45 | L1 | PIFLQMAL | 22 | 8 | | | | | 8124 |
| HPV45 | L1 | PLDICQSI | 248 | 8 | | | | | 8125 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | L1 | PLELKNTI | 214 | 8 | | | | | 8126 |
| HPV45 | L1 | PLELKNTII | 214 | 9 | | | | | 8127 |
| HPV45 | L1 | PLGRKFLV | 493 | 8 | | | | | 8128 |
| HPV45 | L1 | PLGRKFLVQA | 493 | 10 | | | | | 8129 |
| HPV45 | L1 | PTDLYIKGT | 299 | 9 | | | | | 8130 |
| HPV45 | L1 | PTDLYIKGTSA | 299 | 11 | | | | | 8131 |
| HPV45 | L1 | PTIGPRKRPA | 508 | 10 | | | | | 8132 |
| HPV45 | L1 | PTIGPRKRPAA | 508 | 11 | | | | | 8133 |
| HPV45 | L1 | PTKFKHYSRHV | 387 | 11 | | | | | 8134 |
| HPV45 | L1 | PTTSLVDT | 440 | 8 | | | | | 8135 |
| HPV45 | L1 | PVPNTYDPT | 380 | 9 | | | | | 8136 |
| HPV45 | L1 | QAGLRRRPT | 501 | 9 | | | | | 8137 |
| HPV45 | L1 | QAGLRRRPTI | 501 | 10 | | | | | 8138 |
| HPV45 | L1 | QAVPKVSA | 87 | 8 | | | | | 8139 |
| HPV45 | L1 | QLCILGCV | 182 | 8 | | | | | 8140 |
| HPV45 | L1 | QLCILGCVPA | 182 | 10 | | | | | 8141 |
| HPV45 | L1 | QLCILGCVPAI | 182 | 11 | | | | | 8142 |
| HPV45 | L1 | QLCTITLT | 407 | 8 | | | | | 8143 |
| HPV45 | L1 | QLCTITLTA | 407 | 9 | | | | | 8144 |
| HPV45 | L1 | QLCTITLTAEV | 407 | 11 | | | | | 8145 |
| HPV45 | L1 | QLFARHFWNRA | 281 | 11 | | | | | 8146 |
| HPV45 | L1 | QLFNKPYWL | 334 | 9 | | | | | 8147 |
| HPV45 | L1 | QLFVTVVDT | 357 | 9 | | | | | 8148 |
| HPV45 | L1 | QLFVTVVDTT | 357 | 10 | | | | | 8149 |
| HPV45 | L1 | QLQPGDCPPL | 206 | 10 | | | | | 8150 |
| HPV45 | L1 | QMALWRPSDST | 26 | 11 | | | | | 8151 |
| HPV45 | L1 | QMSADPYGDSM | 263 | 11 | | | | | 8152 |
| HPV45 | L1 | QTQLCILGCV | 180 | 10 | | | | | 8153 |
| HPV45 | L1 | RAGVMGDT | 290 | 8 | | | | | 8154 |
| HPV45 | L1 | RAGVMGDTV | 290 | 9 | | | | | 8155 |
| HPV45 | L1 | RAGVMGDTVPT | 290 | 11 | | | | | 8156 |
| HPV45 | L1 | RLVWACVGM | 124 | 9 | | | | | 8157 |
| HPV45 | L1 | RLVWACVGMEI | 124 | 11 | | | | | 8158 |
| HPV45 | L1 | RTSIFYHA | 56 | 8 | | | | | 8159 |
| HPV45 | L1 | RVVNTDDYV | 46 | 9 | | | | | 8160 |
| HPV45 | L1 | SADPYGDSM | 265 | 9 | | | | | 8161 |
| HPV45 | L1 | SAHAATAV | 158 | 8 | | | | | 8162 |
| HPV45 | L1 | SAHAATAVI | 158 | 9 | | | | | 8163 |
| HPV45 | L1 | SAHAATAVIT | 158 | 10 | | | | | 8164 |
| HPV45 | L1 | SAYQYRVFRV | 93 | 10 | | | | | 8165 |
| HPV45 | L1 | SAYQYRVFRVA | 93 | 11 | | | | | 8166 |
| HPV45 | L1 | SICKYPDYL | 254 | 9 | | | | | 8167 |
| HPV45 | L1 | SICKYPDYLQM | 254 | 11 | | | | | 8168 |
| HPV45 | L1 | SIFYHAGSSRL | 58 | 11 | | | | | 8169 |
| HPV45 | L1 | SILENWNFGV | 427 | 10 | | | | | 8170 |
| HPV45 | L1 | SITTSDSQL | 327 | 9 | | | | | 8171 |
| HPV45 | L1 | SLVDTYRFV | 443 | 9 | | | | | 8172 |
| HPV45 | L1 | SMFFCLRREQL | 272 | 11 | | | | | 8173 |
| HPV45 | L1 | SQLFNKPYWL | 333 | 10 | | | | | 8174 |
| HPV45 | L1 | STASRPAKRV | 521 | 10 | | | | | 8175 |
| HPV45 | L1 | STIYNPET | 115 | 8 | | | | | 8176 |
| HPV45 | L1 | STIYNPETQRL | 115 | 11 | | | | | 8177 |
| HPV45 | L1 | STLQDTKCEV | 238 | 10 | | | | | 8178 |
| HPV45 | L1 | STNLTLCA | 368 | 8 | | | | | 8179 |
| HPV45 | L1 | STNLTLCAST | 368 | 10 | | | | | 8180 |
| HPV45 | L1 | STQNPVPNT | 376 | 9 | | | | | 8181 |
| HPV45 | L1 | STSTASRPA | 519 | 9 | | | | | 8182 |
| HPV45 | L1 | STVYLPPPSV | 35 | 10 | | | | | 8183 |
| HPV45 | L1 | STVYLPPPSVA | 35 | 11 | | | | | 8184 |
| HPV45 | L1 | SVARVVNT | 43 | 8 | | | | | 8185 |
| HPV45 | L1 | SVAVTCQKDT | 453 | 10 | | | | | 8186 |
| HPV45 | L1 | SVAVTCQKDTT | 453 | 11 | | | | | 8187 |
| HPV45 | L1 | SVDYKQTQL | 175 | 9 | | | | | 8188 |
| HPV45 | L1 | SVDYKQTQLCI | 175 | 11 | | | | | 8189 |
| HPV45 | L1 | TAEVMSYI | 414 | 8 | | | | | 8190 |
| HPV45 | L1 | TAEVMSYIHSM | 414 | 11 | | | | | 8191 |
| HPV45 | L1 | TASRPAKRV | 522 | 9 | | | | | 8192 |
| HPV45 | L1 | TASRPAKRVRI | 522 | 11 | | | | | 8193 |
| HPV45 | L1 | TAVITQDV | 163 | 8 | | | | | 8194 |
| HPV45 | L1 | TIGPRKRPA | 509 | 9 | | | | | 8195 |
| HPV45 | L1 | TIGPRKRPAA | 509 | 10 | | | | | 8196 |
| HPV45 | L1 | TIIEDGDM | 220 | 8 | | | | | 8197 |
| HPV45 | L1 | TIIEDGDMV | 220 | 9 | | | | | 8198 |
| HPV45 | L1 | TIIEDGDMVDT | 220 | 11 | | | | | 8199 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | L1 | TITLTAEV | 410 | 8 | | | | | 8200 |
| HPV45 | L1 | TITLTAEVM | 410 | 9 | | | | | 8201 |
| HPV45 | L1 | TIYNPETQRL | 116 | 10 | | | | | 8202 |
| HPV45 | L1 | TIYNPETQRLV | 116 | 11 | | | | | 8203 |
| HPV45 | L1 | TLCASTQNPV | 372 | 10 | | | | | 8204 |
| HPV45 | L1 | TLCKPAQL | 200 | 8 | | | | | 8205 |
| HPV45 | L1 | TLQDTKCEV | 239 | 9 | | | | | 8206 |
| HPV45 | L1 | TLQDTKCEVPL | 239 | 11 | | | | | 8207 |
| HPV45 | L1 | TLTAEVMSYI | 412 | 10 | | | | | 8208 |
| HPV45 | L1 | TQDVRDNV | 167 | 8 | | | | | 8209 |
| HPV45 | L1 | TQDVRDNVSV | 167 | 10 | | | | | 8210 |
| HPV45 | L1 | TQLCILGCV | 181 | 9 | | | | | 8211 |
| HPV45 | L1 | TQLCILGCVPA | 181 | 11 | | | | | 8212 |
| HPV45 | L1 | TQNPVPNT | 377 | 8 | | | | | 8213 |
| HPV45 | L1 | TQRLVWACV | 122 | 9 | | | | | 8214 |
| HPV45 | L1 | TQRLVWACVGM | 122 | 11 | | | | | 8215 |
| HPV45 | L1 | TTRSTNLT | 365 | 8 | | | | | 8216 |
| HPV45 | L1 | TTRSTNLTL | 365 | 9 | | | | | 8217 |
| HPV45 | L1 | TTRSTNLTLCA | 365 | 11 | | | | | 8218 |
| HPV45 | L1 | TTSLVDTYRFV | 441 | 11 | | | | | 8219 |
| HPV45 | L1 | TVGNPYFRV | 70 | 9 | | | | | 8220 |
| HPV45 | L1 | TVGNPYFRVV | 70 | 10 | | | | | 8221 |
| HPV45 | L1 | TVPTDLYI | 297 | 8 | | | | | 8222 |
| HPV45 | L1 | TVPTDLYIKGT | 297 | 11 | | | | | 8223 |
| HPV45 | L1 | TVVDTTRST | 361 | 9 | | | | | 8224 |
| HPV45 | L1 | TVVDTTRSTNL | 361 | 11 | | | | | 8225 |
| HPV45 | L1 | TVYLPPPSV | 36 | 9 | | | | | 8226 |
| HPV45 | L1 | TVYLPPPSVA | 36 | 10 | | | | | 8227 |
| HPV45 | L1 | VALPDPNKFGL | 102 | 11 | | | | | 8228 |
| HPV45 | L1 | VARVVNTDDYV | 44 | 11 | | | | | 8229 |
| HPV45 | L1 | VAVTCQKDT | 454 | 9 | | | | | 8230 |
| HPV45 | L1 | VAVTCQKDTT | 454 | 10 | | | | | 8231 |
| HPV45 | L1 | VITQDVRDNV | 165 | 10 | | | | | 8232 |
| HPV45 | L1 | VMGDTVPT | 293 | 8 | | | | | 8233 |
| HPV45 | L1 | VMGDTVPTDL | 293 | 10 | | | | | 8234 |
| HPV45 | L1 | VMSYIHSM | 417 | 8 | | | | | 8235 |
| HPV45 | L1 | VQAGLRRRPT | 500 | 10 | | | | | 8236 |
| HPV45 | L1 | VQAGLRRRPTI | 500 | 11 | | | | | 8237 |
| HPV45 | L1 | VTCQKDTT | 456 | 8 | | | | | 8238 |
| HPV45 | L1 | VTVVDTTRST | 360 | 10 | | | | | 8239 |
| HPV45 | L1 | VVDTTRST | 362 | 8 | | | | | 8240 |
| HPV45 | L1 | VVDTTRSTNL | 362 | 10 | | | | | 8241 |
| HPV45 | L1 | VVDTTRSTNLT | 362 | 11 | | | | | 8342 |
| HPV45 | L1 | VVNTDDYV | 47 | 8 | | | | | 8243 |
| HPV45 | L1 | VVNTDDYVSRT | 47 | 11 | | | | | 8244 |
| HPV45 | L1 | VVPSGAGNKQA | 78 | 11 | | | | | 8245 |
| HPV45 | L1 | WACVGMEI | 127 | 8 | | | | | 8246 |
| HPV45 | L1 | WAKGTLCKPA | 196 | 10 | | | | | 8247 |
| HPV45 | L1 | YIHSMNSSI | 420 | 9 | | | | | 8248 |
| HPV45 | L1 | YIHSMNSSIL | 420 | 10 | | | | | 8249 |
| HPV45 | L1 | YIKGTSANM | 303 | 9 | | | | | 8250 |
| HPV45 | L1 | YLPPPSVA | 38 | 8 | | | | | 8251 |
| HPV45 | L1 | YLPPPSVARV | 38 | 10 | | | | | 8252 |
| HPV45 | L1 | YLPPPSVARVV | 38 | 11 | | | | | 8253 |
| HPV45 | L1 | YQYRVFRV | 95 | 8 | | | | | 8254 |
| HPV45 | L1 | YQYRVFRVA | 95 | 9 | | | | | 8255 |
| HPV45 | L1 | YQYRVFRVAL | 95 | 10 | | | | | 8256 |
| HPV45 | L1 | YVSRTSIFYHA | 53 | 11 | | | | | 8257 |
| HPV45 | L2 | AARRKRASA | 6 | 9 | | | | | 8258 |
| HPV45 | L2 | AARRKRASAT | 6 | 10 | | | | | 8259 |
| HPV45 | L2 | AASSYSNV | 381 | 8 | | | | | 8260 |
| HPV45 | L2 | AASSYSNVT | 381 | 9 | | | | | 8261 |
| HPV45 | L2 | AASSYSNVTV | 381 | 10 | | | | | 8262 |
| HPV45 | L2 | AATEEIEL | 327 | 8 | | | | | 8263 |
| HPV45 | L2 | AATEEIELQPL | 327 | 11 | | | | | 8264 |
| HPV45 | L2 | ALSSRRGT | 286 | 8 | | | | | 8265 |
| HPV45 | L2 | ALSSRRGTV | 286 | 9 | | | | | 8266 |
| HPV45 | L2 | ATEEIELQPL | 328 | 10 | | | | | 8267 |
| HPV45 | L2 | ATEEIELQPLI | 328 | 11 | | | | | 8268 |
| HPV45 | L2 | ATMFTRSGKQI | 303 | 11 | | | | | 8269 |
| HPV45 | L2 | ATNDSDLFDV | 340 | 10 | | | | | 8270 |
| HPV45 | L2 | AVLDITPT | 139 | 8 | | | | | 8271 |
| HPV45 | L2 | AVLDITPTV | 139 | 9 | | | | | 8272 |
| HPV45 | L2 | DIILPSHT | 405 | 8 | | | | | 8273 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | L2 | DIILPSHTPM | 405 | 10 | | | | | 8274 |
| HPV45 | L2 | DIIRLHRPA | 278 | 9 | | | | | 8275 |
| HPV45 | L2 | DIIRLHRPAL | 278 | 10 | | | | | 8276 |
| HPV45 | L2 | DISPIAAT | 322 | 8 | | | | | 8277 |
| HPV45 | L2 | DISPIAATEEI | 322 | 11 | | | | | 8278 |
| HPV45 | L2 | DITPTVDSV | 142 | 9 | | | | | 8279 |
| HPV45 | L2 | DITPTVDSVSI | 142 | 11 | | | | | 8280 |
| HPV45 | L2 | DLYRTCKQSGT | 16 | 11 | | | | | 8281 |
| HPV45 | L2 | DTTLSFEPT | 260 | 9 | | | | | 8282 |
| HPV45 | L2 | DVGPTRPPV | 83 | 9 | | | | | 8283 |
| HPV45 | L2 | DVGPTRPPVV | 83 | 10 | | | | | 8284 |
| HPV45 | L2 | DVGPTRPPVVI | 83 | 11 | | | | | 8285 |
| HPV45 | L2 | DVINKVEGT | 30 | 9 | | | | | 8286 |
| HPV45 | L2 | DVINKVEGTT | 30 | 10 | | | | | 8287 |
| HPV45 | L2 | DVINKVEGTTL | 30 | 11 | | | | | 8288 |
| HPV45 | L2 | DVPIYTGPDI | 397 | 10 | | | | | 8289 |
| HPV45 | L2 | DVPIYTGPDII | 397 | 11 | | | | | 8390 |
| HPV45 | L2 | DVYADFPPPA | 348 | 10 | | | | | 8291 |
| HPV45 | L2 | EIELQPLI | 331 | 8 | | | | | 8292 |
| HPV45 | L2 | EIELQPLISA | 331 | 10 | | | | | 8293 |
| HPV45 | L2 | EIELQPLISAT | 331 | 11 | | | | | 8294 |
| HPV45 | L2 | EIPLQTFA | 194 | 8 | | | | | 8295 |
| HPV45 | L2 | EITSSGTT | 129 | 8 | | | | | 8296 |
| HPV45 | L2 | EITSSGTTT | 129 | 9 | | | | | 8297 |
| HPV45 | L2 | EITSSGTTTPA | 129 | 11 | | | | | 8298 |
| HPV45 | L2 | ELQPLISA | 333 | 8 | | | | | 8299 |
| HPV45 | L2 | ELQPLISAT | 333 | 9 | | | | | 8300 |
| HPV45 | L2 | EVPQTGEV | 169 | 8 | | | | | 8301 |
| HPV45 | L2 | EVSGNIFV | 175 | 8 | | | | | 8302 |
| HPV45 | L2 | EVSGNIFVGT | 175 | 10 | | | | | 8303 |
| HPV45 | L2 | FADGFVAA | 456 | 8 | | | | | 8304 |
| HPV45 | L2 | FASSGSGT | 200 | 8 | | | | | 8305 |
| HPV45 | L2 | FASSGSGTEPI | 200 | 11 | | | | | 8306 |
| HPV45 | L2 | FLGGLGIGT | 53 | 9 | | | | | 8307 |
| HPV45 | L2 | FLTHPSSL | 241 | 8 | | | | | 8308 |
| HPV45 | L2 | FLTHPSSLV | 241 | 9 | | | | | 8309 |
| HPV45 | L2 | FLTHPSSLVT | 241 | 10 | | | | | 8310 |
| HPV45 | L2 | FMDIIRLHRPA | 276 | 11 | | | | | 8311 |
| HPV45 | L2 | FTGTSGFEI | 122 | 9 | | | | | 8312 |
| HPV45 | L2 | FTGTSGFEIT | 122 | 10 | | | | | 8313 |
| HPV45 | L2 | FTNPAFSDPSI | 157 | 11 | | | | | 8314 |
| HPV45 | L2 | FTRSGKQI | 306 | 8 | | | | | 8315 |
| HPV45 | L2 | FTYPKYSL | 368 | 8 | | | | | 8316 |
| HPV45 | L2 | FTYPKYSLT | 368 | 9 | | | | | 8317 |
| HPV45 | L2 | FTYPKYSLTM | 368 | 10 | | | | | 8318 |
| HPV45 | L2 | GAPVPTFT | 116 | 8 | | | | | 8319 |
| HPV45 | L2 | GAPVPTFTGT | 116 | 10 | | | | | 8320 |
| HPV45 | L2 | GIFLGGLGI | 51 | 9 | | | | | 8321 |
| HPV45 | L2 | GIFLGGLGIGT | 51 | 11 | | | | | 8322 |
| HPV45 | L2 | GIHGTQYYL | 430 | 9 | | | | | 8323 |
| HPV45 | L2 | GQRATMFT | 300 | 8 | | | | | 8324 |
| HPV45 | L2 | GTCPPDVI | 25 | 8 | | | | | 8325 |
| HPV45 | L2 | GTCPPDVINKV | 25 | 11 | | | | | 8326 |
| HPV45 | L2 | GTEPISST | 206 | 8 | | | | | 8327 |
| HPV45 | L2 | GTEPISSTPL | 206 | 10 | | | | | 8328 |
| HPV45 | L2 | GTGSGSGGRT | 60 | 10 | | | | | 8329 |
| HPV45 | L2 | GTSGFEIT | 124 | 8 | | | | | 8330 |
| HPV45 | L2 | GTTLADKI | 37 | 8 | | | | | 8331 |
| HPV45 | L2 | GTTLADKIL | 37 | 9 | | | | | 8332 |
| HPV45 | L2 | GTTTPAVL | 134 | 8 | | | | | 8333 |
| HPV45 | L2 | GTTTPAVLDI | 134 | 10 | | | | | 8334 |
| HPV45 | L2 | GTTTPAVLDIT | 134 | 11 | | | | | 8335 |
| HPV45 | L2 | GTVRFSRL | 292 | 8 | | | | | 8336 |
| HPV45 | L2 | HTPMWPST | 411 | 8 | | | | | 8337 |
| HPV45 | L2 | HTPMWPSTSPT | 411 | 11 | | | | | 8338 |
| HPV45 | L2 | IAATEEIEL | 326 | 9 | | | | | 8339 |
| HPV45 | L2 | IIEVPQTGEV | 167 | 10 | | | | | 8340 |
| HPV45 | L2 | IILPSHTPM | 406 | 9 | | | | | 8341 |
| HPV45 | L2 | IIRLHRPA | 279 | 8 | | | | | 8342 |
| HPV45 | L2 | IIRLHRPAL | 279 | 9 | | | | | 8343 |
| HPV45 | L2 | ILPSHTPM | 407 | 8 | | | | | 8344 |
| HPV45 | L2 | ILQWSSLGI | 44 | 9 | | | | | 8345 |
| HPV45 | L2 | ILQWSSLGIFL | 44 | 11 | | | | | 8346 |
| HPV45 | L2 | ITPTVDSV | 143 | 8 | | | | | 8347 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | L2 | ITPTVDSVSI | 143 | 10 | | | | | 8348 |
| HPV45 | L2 | ITSSGTTT | 130 | 8 | | | | | 8349 |
| HPV45 | L2 | ITSSGTTTPA | 130 | 10 | | | | | 8350 |
| HPV45 | L2 | ITSSGTTTPAV | 130 | 11 | | | | | 8351 |
| HPV45 | L2 | IVTLVEDSSV | 103 | 10 | | | | | 8352 |
| HPV45 | L2 | IVTLVEDSSVV | 103 | 11 | | | | | 8353 |
| HPV45 | L2 | KILQWSSL | 43 | 8 | | | | | 8354 |
| HPV45 | L2 | KILQWSSLGI | 43 | 10 | | | | | 8355 |
| HPV45 | L2 | KQSGTCPPDV | 22 | 10 | | | | | 8356 |
| HPV45 | L2 | KQSGTCPPDVI | 22 | 11 | | | | | 8357 |
| HPV45 | L2 | KVEGTTLA | 34 | 8 | | | | | 8358 |
| HPV45 | L2 | KVEGTTLADKI | 34 | 11 | | | | | 8359 |
| HPV45 | L2 | LADKILQWSSL | 40 | 11 | | | | | 8360 |
| HPV45 | L2 | LISATNDSDL | 337 | 10 | | | | | 8361 |
| HPV45 | L2 | LQPLISAT | 334 | 8 | | | | | 8362 |
| HPV45 | L2 | LQTFASSGSGT | 197 | 11 | | | | | 8363 |
| HPV45 | L2 | LQWSSLGI | 45 | 8 | | | | | 8364 |
| HPV45 | L2 | LQWSSLGIFL | 45 | 10 | | | | | 8365 |
| HPV45 | L2 | LTHPSSLV | 242 | 8 | | | | | 8366 |
| HPV45 | L2 | LTHPSSLVT | 242 | 9 | | | | | 8367 |
| HPV45 | L2 | LTMPSTAA | 375 | 8 | | | | | 8368 |
| HPV45 | L2 | LTSAWDVPI | 392 | 9 | | | | | 8369 |
| HPV45 | L2 | LTSAWDVPIYT | 392 | 11 | | | | | 8370 |
| HPV45 | L2 | LVEDSSVV | 106 | 8 | | | | | 8371 |
| HPV45 | L2 | LVEDSSVVA | 106 | 9 | | | | | 8372 |
| HPV45 | L2 | LVTFDNPA | 248 | 8 | | | | | 8373 |
| HPV45 | L2 | NASTTTYI | 422 | 8 | | | | | 8374 |
| HPV45 | L2 | NASTTTYIGI | 422 | 10 | | | | | 8375 |
| HPV45 | L2 | NIFVGTPT | 179 | 8 | | | | | 8376 |
| HPV45 | L2 | NQQVRVST | 231 | 8 | | | | | 8377 |
| HPV45 | L2 | NTVVDVGPT | 79 | 9 | | | | | 8378 |
| HPV45 | L2 | NVPDSDFM | 270 | 8 | | | | | 8379 |
| HPV45 | L2 | NVPDSDFMDI | 270 | 10 | | | | | 8380 |
| HPV45 | L2 | NVPDSDFMDII | 270 | 11 | | | | | 8381 |
| HPV45 | L2 | NVTVPLTSA | 387 | 9 | | | | | 8382 |
| HPV45 | L2 | PAFSDPSI | 160 | 8 | | | | | 8383 |
| HPV45 | L2 | PAFSDPSII | 160 | 9 | | | | | 8384 |
| HPV45 | L2 | PAFSDPSIIEV | 160 | 11 | | | | | 8385 |
| HPV45 | L2 | PALSSRRGT | 285 | 9 | | | | | 8386 |
| HPV45 | L2 | PALSSRRGTV | 285 | 10 | | | | | 8387 |
| HPV45 | L2 | PASTTPST | 356 | 8 | | | | | 8388 |
| HPV45 | L2 | PASTTPSTI | 356 | 9 | | | | | 8389 |
| HPV45 | L2 | PAVLDITPT | 138 | 9 | | | | | 8390 |
| HPV45 | L2 | PAVLDITPTV | 138 | 10 | | | | | 8391 |
| HPV45 | L2 | PAYEPLDT | 254 | 8 | | | | | 8392 |
| HPV45 | L2 | PAYEPLDTT | 254 | 9 | | | | | 8393 |
| HPV45 | L2 | PAYEPLDTTL | 254 | 10 | | | | | 8394 |
| HPV45 | L2 | PIAATEEI | 325 | 8 | | | | | 8395 |
| HPV45 | L2 | PIAATEEIEL | 325 | 10 | | | | | 8396 |
| HPV45 | L2 | PISSTPLPT | 209 | 9 | | | | | 8397 |
| HPV45 | L2 | PISSTPLPTV | 209 | 10 | | | | | 8398 |
| HPV45 | L2 | PIYTGPDI | 399 | 8 | | | | | 8399 |
| HPV45 | L2 | PIYTGPDII | 399 | 9 | | | | | 8400 |
| HPV45 | L2 | PIYTGPDIIL | 399 | 10 | | | | | 8401 |
| HPV45 | L2 | PLDTTLSFEPT | 258 | 11 | | | | | 8402 |
| HPV45 | L2 | PLGGRSNT | 73 | 8 | | | | | 8403 |
| HPV45 | L2 | PLGGRSNTV | 73 | 9 | | | | | 8404 |
| HPV45 | L2 | PLGGRSNTVV | 73 | 10 | | | | | 8405 |
| HPV45 | L2 | PLISATNDSDL | 336 | 11 | | | | | 8406 |
| HPV45 | L2 | PLPTVRRV | 214 | 8 | | | | | 8407 |
| HPV45 | L2 | PLTSAWDV | 391 | 8 | | | | | 8408 |
| HPV45 | L2 | PLTSAWDVPI | 391 | 10 | | | | | 8409 |
| HPV45 | L2 | PMWPSTSPT | 413 | 9 | | | | | 8410 |
| HPV45 | L2 | PMWPSTSPTNA | 413 | 11 | | | | | 8411 |
| HPV45 | L2 | PQTGEVSGNI | 171 | 10 | | | | | 8412 |
| HPV45 | L2 | PTDPSIVT | 98 | 8 | | | | | 8413 |
| HPV45 | L2 | PTDPSIVTL | 98 | 9 | | | | | 8414 |
| HPV45 | L2 | PTDPSIVTLV | 98 | 10 | | | | | 8415 |
| HPV45 | L2 | PTFTGTSGFEI | 120 | 11 | | | | | 8416 |
| HPV45 | L2 | PTNASTTT | 420 | 8 | | | | | 8417 |
| HPV45 | L2 | PTNASTTTYI | 420 | 10 | | | | | 8418 |
| HPV45 | L2 | PTRPPVVI | 86 | 8 | | | | | 8419 |
| HPV45 | L2 | PTRPPVVIEPV | 86 | 11 | | | | | 8420 |
| HPV45 | L2 | PTSGSHGYEEI | 185 | 11 | | | | | 8421 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | L2 | PTSNVPDSDFM | 267 | 11 | | | | | 8422 |
| HPV45 | L2 | PTVDSVSI | 145 | 8 | | | | | 8423 |
| HPV45 | L2 | PTVDSVSISST | 145 | 11 | | | | | 8424 |
| HPV45 | L2 | PTVRRVRGPRL | 216 | 11 | | | | | 8425 |
| HPV45 | L2 | PVGPTDPSI | 95 | 9 | | | | | 8426 |
| HPV45 | L2 | PVGPTDPSIV | 95 | 10 | | | | | 8427 |
| HPV45 | L2 | PVGPTDPSIVT | 95 | 11 | | | | | 8428 |
| HPV45 | L2 | PVPTFTGT | 118 | 8 | | | | | 8429 |
| HPV45 | L2 | PVVIEPVGPT | 90 | 10 | | | | | 8430 |
| HPV45 | L2 | QQVRVSTSQFL | 232 | 11 | | | | | 8431 |
| HPV45 | L2 | QTFASSGSGT | 198 | 10 | | | | | 8432 |
| HPV45 | L2 | QTGEVSGNI | 172 | 9 | | | | | 8433 |
| HPV45 | L2 | QTGEVSGNIFV | 172 | 11 | | | | | 8434 |
| HPV45 | L2 | QVRVSTSQFL | 233 | 10 | | | | | 8435 |
| HPV45 | L2 | QVRVSTSQFLT | 233 | 11 | | | | | 8436 |
| HPV45 | L2 | RAARRKRA | 5 | 8 | | | | | 8437 |
| HPV45 | L2 | RAARRKRASA | 5 | 10 | | | | | 8438 |
| HPV45 | L2 | RAARRKRASAT | 5 | 11 | | | | | 8439 |
| HPV45 | L2 | RANQQVRV | 229 | 8 | | | | | 8440 |
| HPV45 | L2 | RANQQVRVST | 229 | 10 | | | | | 8441 |
| HPV45 | L2 | RASATDLYRT | 11 | 10 | | | | | 8442 |
| HPV45 | L2 | RIPYFFADGFV | 451 | 11 | | | | | 8443 |
| HPV45 | L2 | RLGQRATM | 298 | 8 | | | | | 8444 |
| HPV45 | L2 | RLGQRATMFT | 298 | 10 | | | | | 8445 |
| HPV45 | L2 | RLYSRANQQV | 225 | 10 | | | | | 8446 |
| HPV45 | L2 | RTCKQSGT | 19 | 8 | | | | | 8447 |
| HPV45 | L2 | RVHFYHDI | 316 | 8 | | | | | 8448 |
| HPV45 | L2 | RVHFYHDISPI | 316 | 11 | | | | | 8449 |
| HPV45 | L2 | RVRGPRLYSRA | 220 | 11 | | | | | 8450 |
| HPV45 | L2 | RVSTSQFL | 235 | 8 | | | | | 8451 |
| HPV45 | L2 | RVSTSQFLT | 235 | 9 | | | | | 8452 |
| HPV45 | L2 | SATDLYRT | 13 | 8 | | | | | 8453 |
| HPV45 | L2 | SATNDSDL | 339 | 8 | | | | | 8454 |
| HPV45 | L2 | SATNDSDLFDV | 339 | 11 | | | | | 8455 |
| HPV45 | L2 | SAWDVPIYT | 394 | 9 | | | | | 8456 |
| HPV45 | L2 | SIIEVPQT | 166 | 8 | | | | | 8457 |
| HPV45 | L2 | SIIEVPQTGEV | 166 | 11 | | | | | 8458 |
| HPV45 | L2 | SISSTSFT | 151 | 8 | | | | | 8459 |
| HPV45 | L2 | SISSTSFTNPA | 151 | 11 | | | | | 8460 |
| HPV45 | L2 | SIVTLVEDSSV | 102 | 11 | | | | | 8461 |
| HPV45 | L2 | SLGIFLGGL | 49 | 9 | | | | | 8462 |
| HPV45 | L2 | SLGIFLGGLGI | 49 | 11 | | | | | 8463 |
| HPV45 | L2 | SLTMPSTA | 374 | 8 | | | | | 8464 |
| HPV45 | L2 | SLTMPSTAA | 374 | 9 | | | | | 8465 |
| HPV45 | L2 | SLVTFDNPA | 247 | 9 | | | | | 8466 |
| HPV45 | L2 | SQFLTHPSSL | 239 | 10 | | | | | 8467 |
| HPV45 | L2 | SQFLTHPSSLV | 239 | 11 | | | | | 8468 |
| HPV45 | L2 | STAASSYSNV | 379 | 10 | | | | | 8469 |
| HPV45 | L2 | STAASSYSNVT | 379 | 11 | | | | | 8470 |
| HPV45 | L2 | STIHKSFT | 362 | 8 | | | | | 8471 |
| HPV45 | L2 | STPLPTVRRV | 212 | 10 | | | | | 8472 |
| HPV45 | L2 | STSFTNPA | 154 | 8 | | | | | 8473 |
| HPV45 | L2 | STSPTNAST | 417 | 9 | | | | | 8474 |
| HPV45 | L2 | STSPTNASTT | 417 | 10 | | | | | 8475 |
| HPV45 | L2 | STSPTNASTTT | 417 | 11 | | | | | 8476 |
| HPV45 | L2 | STTTYIGI | 424 | 8 | | | | | 8477 |
| HPV45 | L2 | STTTYIGIHGT | 424 | 11 | | | | | 8478 |
| HPV45 | L2 | SVSISSTSFT | 149 | 10 | | | | | 8479 |
| HPV45 | L2 | SVVASGAPV | 111 | 9 | | | | | 8480 |
| HPV45 | L2 | SVVASGAPVPT | 111 | 11 | | | | | 8481 |
| HPV45 | L2 | TAASSYSNV | 380 | 9 | | | | | 8482 |
| HPV45 | L2 | TAASSYSNVT | 380 | 10 | | | | | 8483 |
| HPV45 | L2 | TAASSYSNVTV | 380 | 11 | | | | | 8484 |
| HPV45 | L2 | TLSFEPTSNV | 262 | 10 | | | | | 8485 |
| HPV45 | L2 | TLVEDSSV | 105 | 8 | | | | | 8486 |
| HPV45 | L2 | TLVEDSSVV | 105 | 9 | | | | | 8487 |
| HPV45 | L2 | TLVEDSSVVA | 105 | 10 | | | | | 8488 |
| HPV45 | L2 | TMFTRSGKQI | 304 | 10 | | | | | 8489 |
| HPV45 | L2 | TTLADKIL | 38 | 8 | | | | | 8490 |
| HPV45 | L2 | TTLSFEPT | 261 | 8 | | | | | 8491 |
| HPV45 | L2 | TTLSFEPTSNV | 261 | 11 | | | | | 8492 |
| HPV45 | L2 | TTPAVLDI | 136 | 8 | | | | | 8493 |
| HPV45 | L2 | TTPAVLDIT | 136 | 9 | | | | | 8494 |
| HPV45 | L2 | TTPAVLDITPT | 136 | 11 | | | | | 8495 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV45 | L2 | TTPSTIHKSFT | 359 | 11 | | | | | 8496 |
| HPV45 | L2 | TTTPAVLDI | 135 | 9 | | | | | 8497 |
| HPV45 | L2 | TTTPAVLDIT | 135 | 10 | | | | | 8498 |
| HPV45 | L2 | TTTYIGIHGT | 425 | 10 | | | | | 8499 |
| HPV45 | L2 | TTYIGIHGT | 426 | 9 | | | | | 8500 |
| HPV45 | L2 | TVDSVSISST | 146 | 10 | | | | | 8501 |
| HPV45 | L2 | TVPLTSAWDV | 389 | 10 | | | | | 8502 |
| HPV45 | L2 | TVRFSRLGQRA | 293 | 11 | | | | | 8503 |
| HPV45 | L2 | TVRRVRGPRL | 217 | 10 | | | | | 8504 |
| HPV45 | L2 | TVVDVGPT | 80 | 8 | | | | | 8505 |
| HPV45 | L2 | VASGAPVPT | 113 | 9 | | | | | 8506 |
| HPV45 | L2 | VASGAPVPTFT | 113 | 11 | | | | | 8507 |
| HPV45 | L2 | VIEPVGPT | 92 | 8 | | | | | 8508 |
| HPV45 | L2 | VINKVEGT | 31 | 8 | | | | | 8509 |
| HPV45 | L2 | VINKVEGTT | 31 | 9 | | | | | 8510 |
| HPV45 | L2 | VINKVEGTTL | 31 | 10 | | | | | 8511 |
| HPV45 | L2 | VINKVEGTTLA | 31 | 11 | | | | | 8512 |
| HPV45 | L2 | VLDITPTV | 140 | 8 | | | | | 8513 |
| HPV45 | L2 | VLDITPTVDSV | 140 | 11 | | | | | 8514 |
| HPV45 | L2 | VTFDNPAYEPL | 249 | 11 | | | | | 8515 |
| HPV45 | L2 | VTLVEDSSV | 104 | 9 | | | | | 8516 |
| HPV45 | L2 | VTLVEDSSVV | 104 | 10 | | | | | 8517 |
| HPV45 | L2 | VTLVEDSSVVA | 104 | 11 | | | | | 8518 |
| HPV45 | L2 | VTVPLTSA | 388 | 8 | | | | | 8519 |
| HPV45 | L2 | VTVPLTSAWDV | 388 | 11 | | | | | 8520 |
| HPV45 | L2 | VVASGAPV | 112 | 8 | | | | | 8521 |
| HPV45 | L2 | VVASGAPVPT | 112 | 10 | | | | | 8522 |
| HPV45 | L2 | VVDVGPTRPPV | 81 | 11 | | | | | 8523 |
| HPV45 | L2 | VVIEPVGPT | 91 | 9 | | | | | 8524 |
| HPV45 | L2 | YADFPPPA | 350 | 8 | | | | | 8525 |
| HPV45 | L2 | YADFPPPAST | 350 | 10 | | | | | 8526 |
| HPV45 | L2 | YADFPPPASTT | 350 | 11 | | | | | 8527 |
| HPV45 | L2 | YIGIHGTQYYL | 428 | 11 | | | | | 8528 |
| HPV45 | L2 | YTGPDIIL | 401 | 8 | | | | | 8529 |
| HPV45 | L2 | YVPLGGRSNT | 71 | 10 | | | | | 8530 |
| HPV45 | L2 | YVPLGGRSNTV | 71 | 11 | | | | | 8531 |
| HPV56 | E2 | AIEVQIAL | 15 | 8 | | | | | 8532 |
| HPV56 | E2 | AIEVQIALESL | 15 | 11 | | | | | 8533 |
| HPV56 | E2 | ALESLSTT | 21 | 8 | | | | | 8534 |
| HPV56 | E2 | ALESLSTTI | 21 | 9 | | | | | 8535 |
| HPV56 | E2 | CLQVCKAKA | 4 | 9 | | | | | 8536 |
| HPV56 | E2 | CMQYVAWKYI | 71 | 10 | | | | | 8537 |
| HPV56 | E2 | CVTTHTHI | 204 | 8 | | | | | 8538 |
| HPV56 | E2 | CVTTHTHISDT | 204 | 11 | | | | | 8539 |
| HPV56 | E2 | DTCEELWL | 39 | 8 | | | | | 8540 |
| HPV56 | E2 | DTCEELWLT | 39 | 9 | | | | | 8541 |
| HPV56 | E2 | DVTSTYHWT | 263 | 9 | | | | | 8542 |
| HPV56 | E2 | DVTSTYHWTST | 263 | 11 | | | | | 8543 |
| HPV56 | E2 | EAKKFGCKNI | 117 | 10 | | | | | 8544 |
| HPV56 | E2 | ETQRNSFL | 288 | 8 | | | | | 8545 |
| HPV56 | E2 | ETQRNSFLSHV | 288 | 11 | | | | | 8546 |
| HPV56 | E2 | ETVNEYNT | 154 | 8 | | | | | 8547 |
| HPV56 | E2 | ETVNEYNTHKT | 154 | 11 | | | | | 8548 |
| HPV56 | E2 | EVHMENESI | 128 | 9 | | | | | 8549 |
| HPV56 | E2 | EVQIALESL | 17 | 9 | | | | | 8550 |
| HPV56 | E2 | EVQIALESLST | 17 | 11 | | | | | 8551 |
| HPV56 | E2 | FLSHVKIPV | 294 | 9 | | | | | 8552 |
| HPV56 | E2 | FLSHVKIPVV | 294 | 10 | | | | | 8553 |
| HPV56 | E2 | FQKYKTLFV | 254 | 9 | | | | | 8554 |
| HPV56 | E2 | FQKYKTLFVDV | 254 | 11 | | | | | 8555 |
| HPV56 | E2 | FVDVTSTYHWT | 261 | 11 | | | | | 8556 |
| HPV56 | E2 | GIYYVHDGHKT | 99 | 11 | | | | | 8557 |
| HPV56 | E2 | GVDYRGIYYV | 94 | 10 | | | | | 8558 |
| HPV56 | E2 | HAKCVTTHT | 201 | 9 | | | | | 8559 |
| HPV56 | E2 | HAKCVTTHTHI | 201 | 11 | | | | | 8560 |
| HPV56 | E2 | HISDTDNT | 210 | 8 | | | | | 8561 |
| HPV56 | E2 | HLKGEPNRL | 239 | 9 | | | | | 8562 |
| HPV56 | E2 | HTHISDTDNT | 208 | 10 | | | | | 8563 |
| HPV56 | E2 | HVKIPVVYRL | 297 | 10 | | | | | 8564 |
| HPV56 | E2 | HVKIPVVYRLV | 297 | 11 | | | | | 8565 |
| HPV56 | E2 | IALESLST | 20 | 8 | | | | | 8566 |
| HPV56 | E2 | IALESLSTT | 20 | 9 | | | | | 8567 |
| HPV56 | E2 | IALESLSTTI | 20 | 10 | | | | | 8568 |
| HPV56 | E2 | IITIIYKDET | 280 | 10 | | | | | 8569 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | E2 | ITIIYKDET | 281 | 9 | | | | | 8570 |
| HPV56 | E2 | KACSAIEV | 11 | 8 | | | | | 8571 |
| HPV56 | E2 | KACSAIEVQI | 11 | 10 | | | | | 8572 |
| HPV56 | E2 | KACSAIEVQIA | 11 | 11 | | | | | 8573 |
| HPV56 | E2 | KAKACSAI | 9 | 8 | | | | | 8574 |
| HPV56 | E2 | KAKACSAIEV | 9 | 10 | | | | | 8575 |
| HPV56 | E2 | KIPVVYRL | 299 | 8 | | | | | 8576 |
| HPV56 | E2 | KIPVVYRLV | 299 | 9 | | | | | 8577 |
| HPV56 | E2 | KTLFVDVT | 258 | 8 | | | | | 8578 |
| HPV56 | E2 | KTLFVDVTST | 258 | 10 | | | | | 8579 |
| HPV56 | E2 | KTTPVVHL | 233 | 8 | | | | | 8580 |
| HPV56 | E2 | KTTTTTST | 163 | 8 | | | | | 8581 |
| HPV56 | E2 | KTTTTTSTSV | 163 | 10 | | | | | 8582 |
| HPV56 | E2 | KTYYTDFEQEA | 108 | 11 | | | | | 8583 |
| HPV56 | E2 | KVCSGVDYRGI | 90 | 11 | | | | | 8584 |
| HPV56 | E2 | LQVCKAKA | 5 | 8 | | | | | 8585 |
| HPV56 | E2 | LQVCKAKACSA | 5 | 11 | | | | | 8586 |
| HPV56 | E2 | MQYVAWKYI | 72 | 9 | | | | | 8587 |
| HPV56 | E2 | MVPCLQVCKA | 1 | 10 | | | | | 8588 |
| HPV56 | E2 | NTDSRSRSI | 216 | 9 | | | | | 8589 |
| HPV56 | E2 | NTHKTTTT | 160 | 8 | | | | | 8590 |
| HPV56 | E2 | NTHKTTTTT | 160 | 9 | | | | | 8591 |
| HPV56 | E2 | NTHKTTTTTST | 160 | 11 | | | | | 8592 |
| HPV56 | E2 | NVSPVETV | 149 | 8 | | | | | 8593 |
| HPV56 | E2 | PVETVNEYNT | 152 | 10 | | | | | 8594 |
| HPV56 | E2 | QIALESLST | 19 | 9 | | | | | 8595 |
| HPV56 | E2 | QIALESLSTT | 19 | 10 | | | | | 8596 |
| HPV56 | E2 | QIALESLSTTI | 19 | 11 | | | | | 8597 |
| HPV56 | E2 | QVCKAKACSA | 6 | 10 | | | | | 8598 |
| HPV56 | E2 | QVCKAKACSAI | 6 | 11 | | | | | 8599 |
| HPV56 | E2 | SAIEVQIA | 14 | 8 | | | | | 8600 |
| HPV56 | E2 | SAIEVQIAL | 14 | 9 | | | | | 8601 |
| HPV56 | E2 | SIITIIYKDET | 279 | 11 | | | | | 8602 |
| HPV56 | E2 | SIYCPDSV | 135 | 8 | | | | | 8603 |
| HPV56 | E2 | SIYCPDSVSST | 135 | 11 | | | | | 8604 |
| HPV56 | E2 | STCRYNVSPV | 144 | 10 | | | | | 8605 |
| HPV56 | E2 | STDNKNYSI | 272 | 9 | | | | | 8606 |
| HPV56 | E2 | STDNKNYSII | 272 | 10 | | | | | 8607 |
| HPV56 | E2 | STDNKNYSIIT | 272 | 11 | | | | | 8608 |
| HPV56 | E2 | STSVGNQDA | 169 | 9 | | | | | 8609 |
| HPV56 | E2 | STSVGNQDAA | 169 | 10 | | | | | 8610 |
| HPV56 | E2 | STSVGNQDAAV | 169 | 11 | | | | | 8611 |
| HPV56 | E2 | STTIYNNEEWT | 26 | 11 | | | | | 8612 |
| HPV56 | E2 | STYHWTST | 266 | 8 | | | | | 8613 |
| HPV56 | E2 | SVGNQDAA | 171 | 8 | | | | | 8614 |
| HPV56 | E2 | SVGNQDAAV | 171 | 9 | | | | | 8615 |
| HPV56 | E2 | SVSSTCRYNV | 141 | 10 | | | | | 8616 |
| HPV56 | E2 | TIIYKDET | 282 | 8 | | | | | 8617 |
| HPV56 | E2 | TIYNNEEWT | 28 | 9 | | | | | 8618 |
| HPV56 | E2 | TIYNNEEWTL | 28 | 10 | | | | | 8619 |
| HPV56 | E2 | TLFVDVTST | 259 | 9 | | | | | 8620 |
| HPV56 | E2 | TLRDTCEEL | 36 | 9 | | | | | 8621 |
| HPV56 | E2 | TLRDTCEELWL | 36 | 11 | | | | | 8622 |
| HPV56 | E2 | TQRNSFLSHV | 289 | 10 | | | | | 8623 |
| HPV56 | E2 | TTHTHISDT | 206 | 9 | | | | | 8624 |
| HPV56 | E2 | TTIYNNEEWT | 27 | 10 | | | | | 8625 |
| HPV56 | E2 | TTIYNNEEWTL | 27 | 11 | | | | | 8626 |
| HPV56 | E2 | TTSTSVGNQDA | 167 | 11 | | | | | 8627 |
| HPV56 | E2 | TTTTSTSV | 165 | 8 | | | | | 8628 |
| HPV56 | E2 | TTTTTSTSV | 164 | 9 | | | | | 8629 |
| HPV56 | E2 | TVNEYNTHKT | 155 | 10 | | | | | 8630 |
| HPV56 | E2 | TVNEYNTHKTT | 155 | 11 | | | | | 8631 |
| HPV56 | E2 | VQIALESL | 18 | 8 | | | | | 8632 |
| HPV56 | E2 | VQIALESLST | 18 | 10 | | | | | 8633 |
| HPV56 | E2 | VQIALESLSTT | 18 | 11 | | | | | 8634 |
| HPV56 | E2 | VTSTYHWT | 264 | 8 | | | | | 8635 |
| HPV56 | E2 | VTSTYHWTST | 264 | 10 | | | | | 8636 |
| HPV56 | E2 | VTTHTHISDT | 205 | 10 | | | | | 8637 |
| HPV56 | E2 | VVHLKGEPNRL | 237 | 11 | | | | | 8638 |
| HPV56 | E2 | WQKVCSGV | 88 | 8 | | | | | 8639 |
| HPV56 | E2 | WTLRDTCEEL | 35 | 10 | | | | | 8640 |
| HPV56 | E2 | WTSTDNKNYSI | 270 | 11 | | | | | 8641 |
| HPV56 | E2 | YTDFEQEA | 111 | 8 | | | | | 8642 |
| HPV56 | E2 | YVHDGHKT | 102 | 8 | | | | | 8643 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | E2 | YVHDGHKTYYT | 102 | 11 | | | | | 8644 |
| HPV56 | E6 | ATLESITKKQL | 89 | 11 | | | | | 8645 |
| HPV56 | E6 | AVCRVCLL | 64 | 8 | | | | | 8646 |
| HPV56 | E6 | CLGCWRQT | 139 | 8 | | | | | 8547 |
| HPV56 | E6 | CLLFYSKV | 69 | 8 | | | | | 8648 |
| HPV56 | E6 | CVYCKKEL | 33 | 8 | | | | | 8649 |
| HPV56 | E6 | CVYCKKELT | 33 | 9 | | | | | 8650 |
| HPV56 | E6 | CVYCKKELTRA | 33 | 11 | | | | | 8651 |
| HPV56 | E6 | EIPLIDLRL | 23 | 9 | | | | | 8652 |
| HPV56 | E6 | ELTRAEVYNFA | 39 | 11 | | | | | 8653 |
| HPV56 | E6 | EVLEIPLI | 20 | 8 | | | | | 8654 |
| HPV56 | E6 | EVLEIPLIDL | 20 | 10 | | | | | 8655 |
| HPV56 | E6 | EVYNFACT | 44 | 8 | | | | | 8656 |
| HPV56 | E6 | EVYNFACTEL | 44 | 10 | | | | | 8657 |
| HPV56 | E6 | FACTELKL | 48 | 8 | | | | | 8658 |
| HPV56 | E6 | FACTELKLV | 48 | 9 | | | | | 8659 |
| HPV56 | E6 | GATLESIT | 88 | 8 | | | | | 8660 |
| HPV56 | E6 | HLIAHGWT | 129 | 8 | | | | | 8661 |
| HPV56 | E6 | HLSEVLEI | 17 | 8 | | | | | 8662 |
| HPV56 | E6 | HLSEVLEIPL | 17 | 10 | | | | | 8663 |
| HPV56 | E6 | HLSEVLEIPLI | 17 | 11 | | | | | 8664 |
| HPV56 | E6 | IAHGWTGSCL | 131 | 10 | | | | | 8665 |
| HPV56 | E6 | ITKKQLCDL | 94 | 9 | | | | | 8666 |
| HPV56 | E6 | ITKKQLCDLL | 94 | 10 | | | | | 8667 |
| HPV56 | E6 | ITKKQLCDLLI | 94 | 11 | | | | | 8668 |
| HPV56 | E6 | KLVYRDDFPYA | 54 | 11 | | | | | 8669 |
| HPV56 | E6 | KQLCDLLI | 97 | 8 | | | | | 8670 |
| HPV56 | E6 | LIAHGWTGSCL | 130 | 11 | | | | | 8671 |
| HPV56 | E6 | LIDLRLSCV | 26 | 9 | | | | | 8672 |
| HPV56 | E6 | LIRCYRCQSPL | 103 | 11 | | | | | 8673 |
| HPV56 | E6 | LTPEEKQL | 113 | 8 | | | | | 8674 |
| HPV56 | E6 | LTRAEVYNFA | 40 | 10 | | | | | 8675 |
| HPV56 | E6 | LVYRDDFPYA | 55 | 10 | | | | | 8676 |
| HPV56 | E6 | LVYRDDFPYAV | 55 | 11 | | | | | 8677 |
| HPV56 | E6 | PLIDLRLSCV | 25 | 10 | | | | | 8678 |
| HPV56 | E6 | PLTPEEKQL | 112 | 9 | | | | | 8679 |
| HPV56 | E6 | PQERPRSL | 8 | 8 | | | | | 8680 |
| HPV56 | E6 | PQERPRSLHHL | 8 | 11 | | | | | 8681 |
| HPV56 | E6 | QTSREPREST | 145 | 10 | | | | | 8682 |
| HPV56 | E6 | QTSREPRESTV | 145 | 11 | | | | | 8683 |
| HPV56 | E6 | RAEVYNFA | 42 | 8 | | | | | 8684 |
| HPV56 | E6 | RAEVYNFACT | 42 | 10 | | | | | 8685 |
| HPV56 | E6 | RLSCVYCKKEL | 30 | 11 | | | | | 8686 |
| HPV56 | E6 | RQTSREPREST | 144 | 11 | | | | | 8687 |
| HPV56 | E6 | RVCLLFYSKV | 67 | 10 | | | | | 8688 |
| HPV56 | E6 | SITKKQLCDL | 93 | 10 | | | | | 8689 |
| HPV56 | E6 | SITKKQLCDLL | 93 | 11 | | | | | 8690 |
| HPV56 | E6 | SLHHLSEV | 14 | 8 | | | | | 8691 |
| HPV56 | E6 | SLHHLSEVL | 14 | 9 | | | | | 8692 |
| HPV56 | E6 | SLHHLSEVLEI | 14 | 11 | | | | | 8693 |
| HPV56 | E6 | SVYGATLESI | 85 | 10 | | | | | 8694 |
| HPV56 | E6 | SVYGATLESIT | 85 | 11 | | | | | 8695 |
| HPV56 | E6 | TLESITKKQL | 90 | 10 | | | | | 8696 |
| HPV56 | E6 | VLEIPLIDL | 21 | 9 | | | | | 8697 |
| HPV56 | E6 | VLEIPLIDLRL | 21 | 11 | | | | | 8698 |
| HPV56 | E6 | YAVCRVCL | 63 | 8 | | | | | 8699 |
| HPV56 | E6 | YAVCRVCLL | 63 | 9 | | | | | 8700 |
| HPV56 | E7 | ALTVTCPL | 93 | 8 | | | | | 8701 |
| HPV56 | E7 | ALTVTCPLCA | 93 | 10 | | | | | 8702 |
| HPV56 | E7 | DIQSTKEDL | 75 | 9 | | | | | 8703 |
| HPV56 | E7 | DIQSTKEDLRV | 75 | 11 | | | | | 8704 |
| HPV56 | E7 | DLQCNEQL | 22 | 8 | | | | | 8705 |
| HPV56 | E7 | DLRVVQQL | 82 | 8 | | | | | 8706 |
| HPV56 | E7 | DLRVVQQLL | 82 | 9 | | | | | 8707 |
| HPV56 | E7 | DLRVVQQLLM | 82 | 10 | | | | | 8708 |
| HPV56 | E7 | DVVLELTPQT | 10 | 10 | | | | | 8709 |
| HPV56 | E7 | EIDLQCNEQL | 20 | 10 | | | | | 8710 |
| HPV56 | E7 | ELTPQTEI | 14 | 8 | | | | | 8711 |
| HPV56 | E7 | ELTPQTEIDL | 14 | 10 | | | | | 8712 |
| HPV56 | E7 | FVVQLDIQST | 70 | 10 | | | | | 8713 |
| HPV56 | E7 | GALTVTCPL | 92 | 9 | | | | | 8714 |
| HPV56 | E7 | GALTVTCPLCA | 92 | 11 | | | | | 8715 |
| HPV56 | E7 | HLQERPQQA | 42 | 9 | | | | | 8716 |
| HPV56 | E7 | HTCYLIHV | 56 | 8 | | | | | 8717 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | E7 | HVPCCECKFV | 62 | 10 | | | | | 8718 |
| HPV56 | E7 | HVPCCECKFVV | 62 | 11 | | | | | 8719 |
| HPV56 | E7 | IQSTKEDL | 76 | 8 | | | | | 8720 |
| HPV56 | E7 | IQSTKEDLRV | 76 | 10 | | | | | 8721 |
| HPV56 | E7 | IQSTKEDLRVV | 76 | 11 | | | | | 8722 |
| HPV56 | E7 | KQHTCYLI | 54 | 8 | | | | | 8723 |
| HPV56 | E7 | KQHTCYLIHV | 54 | 10 | | | | | 8724 |
| HPV56 | E7 | KVPTLQDV | 4 | 8 | | | | | 8725 |
| HPV56 | E7 | KVPTLQDVV | 4 | 9 | | | | | 8726 |
| HPV56 | E7 | KVPTLQDVVL | 4 | 10 | | | | | 8727 |
| HPV56 | E7 | LLMGALTV | 89 | 8 | | | | | 8728 |
| HPV56 | E7 | LLMGALTVT | 89 | 9 | | | | | 8729 |
| HPV56 | E7 | LMGALTVT | 90 | 8 | | | | | 8730 |
| HPV56 | E7 | LMGALTVTCPL | 90 | 11 | | | | | 8731 |
| HPV56 | E7 | LQDVVLEL | 8 | 8 | | | | | 8732 |
| HPV56 | E7 | LQDVVLELT | 8 | 9 | | | | | 8733 |
| HPV56 | E7 | LQERPQQA | 43 | 8 | | | | | 8734 |
| HPV56 | E7 | LQERPQQARQA | 43 | 11 | | | | | 8735 |
| HPV56 | E7 | LTPQTEIDL | 15 | 9 | | | | | 8736 |
| HPV56 | E7 | LTVTCPLCA | 94 | 9 | | | | | 8737 |
| HPV56 | E7 | PQQARQAKQHT | 47 | 11 | | | | | 8738 |
| HPV56 | E7 | PTLQDVVL | 6 | 8 | | | | | 8739 |
| HPV56 | E7 | PTLQDVVLEL | 6 | 10 | | | | | 8740 |
| HPV56 | E7 | PTLQDVVLELT | 6 | 11 | | | | | 8741 |
| HPV56 | E7 | QAKQHTCYL | 52 | 9 | | | | | 8742 |
| HPV56 | E7 | QAKQHTCYLI | 52 | 10 | | | | | 8743 |
| HPV56 | E7 | QARQAKQHT | 49 | 9 | | | | | 8744 |
| HPV56 | E7 | QLDIQSTKEDL | 73 | 11 | | | | | 8745 |
| HPV56 | E7 | QLLMGALT | 88 | 8 | | | | | 8746 |
| HPV56 | E7 | QLLMGALTV | 88 | 9 | | | | | 8747 |
| HPV56 | E7 | QLLMGALTVT | 88 | 10 | | | | | 8748 |
| HPV56 | E7 | QQARQAKQHT | 48 | 10 | | | | | 8749 |
| HPV56 | E7 | QQLLMGAL | 87 | 8 | | | | | 8750 |
| HPV56 | E7 | QQLLMGALT | 87 | 9 | | | | | 8751 |
| HPV56 | E7 | QQLLMGALTV | 87 | 10 | | | | | 8752 |
| HPV56 | E7 | QQLLMGALTVT | 87 | 11 | | | | | 8753 |
| HPV56 | E7 | RQAKQHTCYL | 51 | 10 | | | | | 8754 |
| HPV56 | E7 | RQAKQHTCYLI | 51 | 11 | | | | | 8755 |
| HPV56 | E7 | RVVQQLLM | 84 | 8 | | | | | 8756 |
| HPV56 | E7 | RVVQQLLMGA | 84 | 10 | | | | | 8757 |
| HPV56 | E7 | RVVQQLLMGAL | 84 | 11 | | | | | 8758 |
| HPV56 | E7 | STKEDLRV | 78 | 8 | | | | | 8759 |
| HPV56 | E7 | STKEDLRVV | 78 | 9 | | | | | 8760 |
| HPV56 | E7 | TLQDVVLEL | 7 | 9 | | | | | 8761 |
| HPV56 | E7 | TLQDVVLELT | 7 | 10 | | | | | 8762 |
| HPV56 | E7 | TVTCPLCA | 95 | 8 | | | | | 8763 |
| HPV56 | E7 | VLELTPQT | 12 | 8 | | | | | 8764 |
| HPV56 | E7 | VLELTPQTEI | 12 | 10 | | | | | 8765 |
| HPV56 | E7 | VQLDIQST | 72 | 8 | | | | | 8766 |
| HPV56 | E7 | VQQLLMGA | 86 | 8 | | | | | 8767 |
| HPV56 | E7 | VQQLLMGAL | 86 | 9 | | | | | 8768 |
| HPV56 | E7 | VQQLLMGALT | 86 | 10 | | | | | 8769 |
| HPV56 | E7 | VQQLLMGALTV | 86 | 11 | | | | | 8770 |
| HPV56 | E7 | VVLELTPQT | 11 | 9 | | | | | 8771 |
| HPV56 | E7 | VVLELTPQTEI | 11 | 11 | | | | | 8772 |
| HPV56 | E7 | VVQLDIQST | 71 | 9 | | | | | 8773 |
| HPV56 | E7 | VVQQLLMGA | 85 | 9 | | | | | 8774 |
| HPV56 | E7 | VVQQLLMGAL | 85 | 10 | | | | | 8775 |
| HPV56 | E7 | VVQQLLMGALT | 85 | 11 | | | | | 8776 |
| HPV56 | L1 | AITCQREQPPT | 458 | 11 | | | | | 8777 |
| HPV56 | L1 | AMGEHWTKGA | 198 | 10 | | | | | 8778 |
| HPV56 | L1 | AMGEHWTKGAV | 198 | 11 | | | | | 8779 |
| HPV56 | L1 | AQGHNNGI | 350 | 8 | | | | | 8780 |
| HPV56 | L1 | AQLFNKPYWL | 338 | 10 | | | | | 8781 |
| HPV56 | L1 | ATDSYVKRT | 58 | 9 | | | | | 8782 |
| HPV56 | L1 | ATDSYVKRTSI | 58 | 11 | | | | | 8783 |
| HPV56 | L1 | ATEQLSKYDA | 381 | 10 | | | | | 8784 |
| HPV56 | L1 | ATPSGSMI | 327 | 8 | | | | | 8785 |
| HPV56 | L1 | ATPSGSMIT | 327 | 9 | | | | | 8786 |
| HPV56 | L1 | ATSKKRSA | 514 | 8 | | | | | 8787 |
| HPV56 | L1 | ATSKKRSAPT | 514 | 10 | | | | | 8788 |
| HPV56 | L1 | ATSLEDKYRYV | 444 | 11 | | | | | 8789 |
| HPV56 | L1 | ATWRPSENKV | 37 | 10 | | | | | 8790 |
| HPV56 | L1 | AVATSKKRSA | 512 | 10 | | | | | 8791 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | L1 | AVCKSTQV | 207 | 8 | | | | | 8792 |
| HPV56 | L1 | AVCKSTQVT | 207 | 9 | | | | | 8793 |
| HPV56 | L1 | AVCKSTQVTT | 207 | 10 | | | | | 8794 |
| HPV56 | L1 | AVGHPYYSV | 79 | 9 | | | | | 8795 |
| HPV56 | L1 | AVGHPYYSVT | 79 | 10 | | | | | 8796 |
| HPV56 | L1 | AVNVFPIFL | 26 | 9 | | | | | 8797 |
| HPV56 | L1 | AVNVFPIFLQM | 26 | 11 | | | | | 8798 |
| HPV56 | L1 | CIFLDVGA | 19 | 8 | | | | | 8799 |
| HPV56 | L1 | CIFLDVGAV | 19 | 9 | | | | | 8800 |
| HPV56 | L1 | CIFLDVGAVNV | 19 | 11 | | | | | 8801 |
| HPV56 | L1 | CIVGCTPA | 191 | 8 | | | | | 8802 |
| HPV56 | L1 | CIVGCTPAM | 191 | 9 | | | | | 8803 |
| HPV56 | L1 | CQREQPPT | 461 | 8 | | | | | 8804 |
| HPV56 | L1 | CTPAMGEHWT | 195 | 10 | | | | | 8805 |
| HPV56 | L1 | DARKINQYL | 389 | 9 | | | | | 8806 |
| HPV56 | L1 | DAYGDSMWFYL | 274 | 11 | | | | | 8807 |
| HPV56 | L1 | DMIDTGFGA | 233 | 9 | | | | | 8808 |
| HPV56 | L1 | DMIDTGFGAM | 233 | 10 | | | | | 8809 |
| HPV56 | L1 | DQERLVWA | 128 | 8 | | | | | 8810 |
| HPV56 | L1 | DQERLVWACV | 128 | 10 | | | | | 8811 |
| HPV56 | L1 | DQFPLGRKFL | 493 | 10 | | | | | 8812 |
| HPV56 | L1 | DQFPLGRKFLM | 493 | 11 | | | | | 8813 |
| HPV56 | L1 | DTESSNLA | 162 | 8 | | | | | 8814 |
| HPV56 | L1 | DTGFGAMDFKV | 236 | 11 | | | | | 8815 |
| HPV56 | L1 | DTTRSTNM | 369 | 8 | | | | | 8816 |
| HPV56 | L1 | DTTRSTNMT | 369 | 9 | | | | | 8817 |
| HPV56 | L1 | DDTRSTNMTI | 369 | 10 | | | | | 8818 |
| HPV56 | L1 | DVGAVNVFPI | 23 | 10 | | | | | 8819 |
| HPV56 | L1 | DVNLQDSFST | 481 | 10 | | | | | 8820 |
| HPV56 | L1 | EAQLFNKPYWL | 337 | 11 | | | | | 8821 |
| HPV56 | L1 | ELQFVFQL | 404 | 8 | | | | | 8822 |
| HPV56 | L1 | ELQFVFQLCKI | 404 | 11 | | | | | 8823 |
| HPV56 | L1 | EQLSKYDA | 383 | 8 | | | | | 8824 |
| HPV56 | L1 | EQLSKYDARKI | 383 | 11 | | | | | 8825 |
| HPV56 | L1 | EQPPTEKQDPL | 464 | 11 | | | | | 8826 |
| HPV56 | L1 | ETIPAELYL | 303 | 9 | | | | | 8827 |
| HPV56 | L1 | EVGRGQPL | 140 | 8 | | | | | 8828 |
| HPV56 | L1 | EVGRGQPLGA | 140 | 10 | | | | | 8829 |
| HPV56 | L1 | EVMAYLHNM | 419 | 9 | | | | | 8830 |
| HPV56 | L1 | EVMAYLHNMNA | 419 | 11 | | | | | 8831 |
| HPV56 | L1 | EVPLDIVQST | 253 | 10 | | | | | 8832 |
| HPV56 | L1 | FARHYFNRA | 290 | 9 | | | | | 8833 |
| HPV56 | L1 | FLDVGAVNV | 21 | 9 | | | | | 8834 |
| HPV56 | L1 | FQLCKITL | 409 | 8 | | | | | 8835 |
| HPV56 | L1 | FQLCKITLSA | 409 | 10 | | | | | 8836 |
| HPV56 | L1 | FVFQLCKI | 407 | 8 | | | | | 8837 |
| HPV56 | L1 | FVFQLCKIT | 407 | 9 | | | | | 8838 |
| HPV56 | L1 | FVFQLCKITL | 407 | 10 | | | | | 8839 |
| HPV56 | L1 | FVTVVDTT | 364 | 8 | | | | | 8840 |
| HPV56 | L1 | FVTVVDTTRST | 364 | 11 | | | | | 8841 |
| HPV56 | L1 | GAGLSGHPL | 148 | 9 | | | | | 8842 |
| HPV56 | L1 | GAMDFKVL | 240 | 8 | | | | | 8843 |
| HPV56 | L1 | GAVCKSTQV | 206 | 9 | | | | | 8844 |
| HPV56 | L1 | GAVCKSTQVT | 206 | 10 | | | | | 8845 |
| HPV56 | L1 | GAVCKSTQVTT | 206 | 11 | | | | | 8846 |
| HPV56 | L1 | GAVNVFPI | 25 | 8 | | | | | 8847 |
| HPV56 | L1 | GAVNVFPIFL | 25 | 10 | | | | | 8848 |
| HPV56 | L1 | GICWGNQL | 356 | 8 | | | | | 8849 |
| HPV56 | L1 | GICWGNQLFV | 356 | 10 | | | | | 8850 |
| HPV56 | L1 | GICWGNQLFVT | 356 | 11 | | | | | 8851 |
| HPV56 | L1 | GLCIFLDV | 17 | 8 | | | | | 8852 |
| HPV56 | L1 | GLCIFLDVGA | 17 | 10 | | | | | 8853 |
| HPV56 | L1 | GLCIFLDVGAV | 17 | 11 | | | | | 8854 |
| HPV56 | L1 | GLEVGRGQPL | 138 | 10 | | | | | 8855 |
| HPV56 | L1 | GLSGHPLFNRL | 150 | 11 | | | | | 8856 |
| HPV56 | L1 | GLSPPVAT | 438 | 8 | | | | | 8857 |
| HPV56 | L1 | GLSPPVATSL | 438 | 10 | | | | | 8858 |
| HPV56 | L1 | GQPLGAGL | 144 | 8 | | | | | 8859 |
| HPV56 | L1 | GTRSKPAV | 506 | 8 | | | | | 8860 |
| HPV56 | L1 | GTRSKPAVA | 506 | 9 | | | | | 8861 |
| HPV56 | L1 | GTRSKPAVAT | 506 | 10 | | | | | 8862 |
| HPV56 | L1 | HAGSSRLL | 71 | 8 | | | | | 8863 |
| HPV56 | L1 | HAGSSRLLA | 71 | 9 | | | | | 8864 |
| HPV56 | L1 | HAGSSRLLAV | 71 | 10 | | | | | 8865 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | L1 | HVEEYELQFV | 399 | 10 | | | | | 8866 |
| HPV56 | L1 | ITCQREQPPT | 459 | 10 | | | | | 8867 |
| HPV56 | L1 | ITLSAEVM | 414 | 8 | | | | | 8868 |
| HPV56 | L1 | ITLSAEVMA | 414 | 9 | | | | | 8869 |
| HPV56 | L1 | ITLSAEVMAYL | 414 | 11 | | | | | 8870 |
| HPV56 | L1 | IVGCTPAM | 192 | 8 | | | | | 8871 |
| HPV56 | L1 | KAEVPLDI | 251 | 8 | | | | | 8872 |
| HPV56 | L1 | KAEVPLDIV | 251 | 9 | | | | | 8873 |
| HPV56 | L1 | KINQYLRHV | 392 | 9 | | | | | 8874 |
| HPV56 | L1 | KITLSAEV | 413 | 8 | | | | | 8875 |
| HPV56 | L1 | KITLSAEVM | 413 | 9 | | | | | 8876 |
| HPV56 | L1 | KITLSAEVMA | 413 | 10 | | | | | 8877 |
| HPV56 | L1 | KMSADAYGDSM | 270 | 11 | | | | | 8878 |
| HPV56 | L1 | KQTQLCIV | 186 | 8 | | | | | 8879 |
| HPV56 | L1 | KQTQLCIVGCT | 186 | 11 | | | | | 8880 |
| HPV56 | L1 | KTNIPKVSA | 93 | 9 | | | | | 8881 |
| HPV56 | L1 | KVGETIPA | 300 | 8 | | | | | 8882 |
| HPV56 | L1 | KVGETIPAEL | 300 | 10 | | | | | 8883 |
| HPV56 | L1 | KVLQESKA | 245 | 8 | | | | | 8884 |
| HPV56 | L1 | KVLQESKAEV | 245 | 10 | | | | | 8885 |
| HPV56 | L1 | KVSAYQYRV | 98 | 9 | | | | | 8886 |
| HPV56 | L1 | KVVATDSYV | 55 | 9 | | | | | 8887 |
| HPV56 | L1 | KVYLPPTPV | 45 | 9 | | | | | 8888 |
| HPV56 | L1 | LAKYKFWDV | 474 | 9 | | | | | 8889 |
| HPV56 | L1 | LAKYKFWDVNL | 474 | 11 | | | | | 8890 |
| HPV56 | L1 | LALINTPI | 222 | 8 | | | | | 8891 |
| HPV56 | L1 | LAVGHPYYSV | 78 | 10 | | | | | 8892 |
| HPV56 | L1 | LAVGHPYYSVT | 78 | 11 | | | | | 8893 |
| HPV56 | L1 | LINTPIEDGDM | 224 | 11 | | | | | 8894 |
| HPV56 | L1 | LLAVGHPYYSV | 77 | 11 | | | | | 8895 |
| HPV56 | L1 | LLEDWNIGL | 431 | 9 | | | | | 8896 |
| HPV56 | L1 | LMQLGTRSKPA | 502 | 11 | | | | | 8897 |
| HPV56 | L1 | LQDSFSTDL | 484 | 9 | | | | | 8898 |
| HPV56 | L1 | LQESKAEV | 247 | 8 | | | | | 8899 |
| HPV56 | L1 | LQESKAEVPL | 247 | 10 | | | | | 8900 |
| HPV56 | L1 | LQFVFQLCKI | 405 | 10 | | | | | 8901 |
| HPV56 | L1 | LQFVFQLCKIT | 405 | 11 | | | | | 8902 |
| HPV56 | L1 | LQRAQGHNNGI | 347 | 11 | | | | | 8903 |
| HPV56 | L1 | LVWACVGL | 132 | 8 | | | | | 8904 |
| HPV56 | L1 | LVWACVGLEV | 132 | 10 | | | | | 8905 |
| HPV56 | L1 | MATWRPSENKV | 36 | 11 | | | | | 8906 |
| HPV56 | L1 | MAYLHNMNA | 421 | 9 | | | | | 8907 |
| HPV56 | L1 | MAYLHNMNANL | 421 | 11 | | | | | 8908 |
| HPV56 | L1 | MIDTGFGA | 234 | 8 | | | | | 8909 |
| HPV56 | L1 | MIDTGFGAM | 234 | 9 | | | | | 8910 |
| HPV56 | L1 | MITSEAQL | 333 | 8 | | | | | 8911 |
| HPV56 | L1 | MMLPMMYI | 1 | 8 | | | | | 8912 |
| HPV56 | L1 | MMYIYRDPPL | 5 | 10 | | | | | 8913 |
| HPV56 | L1 | MQLGTRSKPA | 503 | 10 | | | | | 8914 |
| HPV56 | L1 | MQLGTRSKPAV | 503 | 11 | | | | | 8915 |
| HPV56 | L1 | MTISTATEQL | 376 | 10 | | | | | 8916 |
| HPV56 | L1 | NANLLEDWNI | 428 | 10 | | | | | 8917 |
| HPV56 | L1 | NIGLSPPV | 436 | 8 | | | | | 8918 |
| HPV56 | L1 | NIGLSPPVA | 436 | 9 | | | | | 8919 |
| HPV56 | L1 | NIGLSPPVAT | 436 | 10 | | | | | 8920 |
| HPV56 | L1 | NISVDGKQT | 180 | 9 | | | | | 8921 |
| HPV56 | L1 | NISVDGKQTQL | 180 | 11 | | | | | 8922 |
| HPV56 | L1 | NIYNPDQERL | 123 | 10 | | | | | 8923 |
| HPV56 | L1 | NIYNPDQERLV | 123 | 11 | | | | | 8924 |
| HPV56 | L1 | NLANNNVI | 167 | 8 | | | | | 8925 |
| HPV56 | L1 | NLLEDWNI | 430 | 8 | | | | | 8926 |
| HPV56 | L1 | NLLEDWNIGL | 430 | 10 | | | | | 8927 |
| HPV56 | L1 | NLQDSFST | 483 | 8 | 28 | | | | 8928 |
| HPV56 | L1 | NLQDSFSTDL | 483 | 10 | | | | | 8929 |
| HPV56 | L1 | NMTISTAT | 375 | 8 | | | | | 8930 |
| HPV56 | L1 | NMTISTATEQL | 375 | 11 | | | | | 8931 |
| HPV56 | L1 | NQLFVTVV | 361 | 8 | | | | | 8932 |
| HPV56 | L1 | NQLFVTVVDT | 361 | 10 | | | | | 8933 |
| HPV56 | L1 | NQLFVTVVDTT | 361 | 11 | | | | | 8934 |
| HPV56 | L1 | NTKTNIPKV | 91 | 9 | | | | | 8935 |
| HPV56 | L1 | NTKTNIPKVSA | 91 | 11 | | | | | 8936 |
| HPV56 | L1 | NTPIEDGDM | 226 | 9 | | | | | 8937 |
| HPV56 | L1 | NTPIEDGDMI | 226 | 10 | | | | | 8938 |
| HPV56 | L1 | NVFPIFLQM | 28 | 9 | | | | | 8939 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | L1 | NVFPIFLQMA | 28 | 10 | | | | | 8940 |
| HPV56 | L1 | NVFPIFLQMAT | 28 | 11 | | | | | 8941 |
| HPV56 | L1 | NVIEDSRDNI | 172 | 10 | | | | | 8942 |
| HPV56 | L1 | PAMGEHWT | 197 | 8 | | | | | 8943 |
| HPV56 | L1 | PAMGEHWTKGA | 197 | 11 | | | | | 8944 |
| HPV56 | L1 | PAVATSKKRSA | 511 | 11 | | | | | 8945 |
| HPV56 | L1 | PIEDGDMI | 228 | 8 | | | | | 8946 |
| HPV56 | L1 | PIEDGDMIDT | 228 | 10 | | | | | 8947 |
| HPV56 | L1 | PIFLQMAT | 31 | 8 | | | | | 8948 |
| HPV56 | L1 | PLAKYKFWDV | 473 | 10 | | | | | 8949 |
| HPV56 | L1 | PLALINTPI | 221 | 9 | | | | | 8950 |
| HPV56 | L1 | PLDIVQST | 255 | 8 | | | | | 8951 |
| HPV56 | L1 | PLFNRLDDT | 155 | 9 | | | | | 8952 |
| HPV56 | L1 | PLGAGLSGHPL | 146 | 11 | | | | | 8953 |
| HPV56 | L1 | PLGRKFLM | 496 | 8 | | | | | 8954 |
| HPV56 | L1 | PLGRKFLMQL | 496 | 10 | | | | | 8955 |
| HPV56 | L1 | PLHYGLCI | 13 | 8 | | | | | 8956 |
| HPV56 | L1 | PLHYGLCIFL | 13 | 10 | | | | | 8957 |
| HPV56 | L1 | PMMYIYRDPPL | 4 | 11 | | | | | 8958 |
| HPV56 | L1 | PTEKQDPL | 467 | 8 | | | | | 8959 |
| HPV56 | L1 | PTEKQDPLA | 467 | 9 | | | | | 8960 |
| HPV56 | L1 | PTPVSKVV | 50 | 8 | | | | | 8961 |
| HPV56 | L1 | PTPVSKVVA | 50 | 9 | | | | | 8962 |
| HPV56 | L1 | PTPVSKVVAT | 50 | 10 | | | | | 8963 |
| HPV56 | L1 | PTSTSTPA | 522 | 8 | | | | | 8964 |
| HPV56 | L1 | PVSKVVAT | 52 | 8 | | | | | 8965 |
| HPV56 | L1 | QLCIVGCT | 189 | 8 | | | | | 8966 |
| HPV56 | L1 | QLCIVGCTPA | 189 | 10 | | | | | 8967 |
| HPV56 | L1 | QLCIVGCTPAM | 189 | 11 | | | | | 8968 |
| HPV56 | L1 | QLCKITLSA | 410 | 9 | | | | | 8969 |
| HPV56 | L1 | QLCKITLSAEV | 410 | 11 | | | | | 8970 |
| HPV56 | L1 | QLFARHYFNRA | 288 | 11 | | | | | 8971 |
| HPV56 | L1 | QLFNKPYWL | 339 | 9 | | | | | 8972 |
| HPV56 | L1 | QLFVTVVDT | 362 | 9 | | | | | 8973 |
| HPV56 | L1 | QLFVTVVDTT | 362 | 10 | | | | | 8974 |
| HPV56 | L1 | QLGTRSKPA | 504 | 9 | | | | | 8975 |
| HPV56 | L1 | QLGTRSKPAV | 504 | 10 | | | | | 8976 |
| HPV56 | L1 | QLGTRSKPAVA | 504 | 11 | | | | | 8977 |
| HPV56 | L1 | QLSKYDARKI | 384 | 10 | | | | | 8978 |
| HPV56 | L1 | QTQLCIVGCT | 187 | 10 | | | | | 8979 |
| HPV56 | L1 | QVTTGDCPPL | 213 | 10 | | | | | 8980 |
| HPV56 | L1 | QVTTGDCPPLA | 213 | 11 | | | | | 8981 |
| HPV56 | L1 | RAGKVGET | 297 | 8 | | | | | 8982 |
| HPV56 | L1 | RAGKVGETI | 297 | 9 | | | | | 8983 |
| HPV56 | L1 | RAGKVGETIPA | 297 | 11 | | | | | 8984 |
| HPV56 | L1 | RAQGHNNGI | 349 | 9 | | | | | 8985 |
| HPV56 | L1 | RLDDTESSNL | 159 | 10 | | | | | 8986 |
| HPV56 | L1 | RLDDTESSNLA | 159 | 11 | | | | | 8987 |
| HPV56 | L1 | RLPDPNKFGL | 110 | 10 | | | | | 8988 |
| HPV56 | L1 | RLVWACVGL | 131 | 9 | | | | | 8989 |
| HPV56 | L1 | RLVWACVGLEV | 131 | 11 | | | | | 8990 |
| HPV56 | L1 | RTSIFYHA | 65 | 8 | | | | | 8991 |
| HPV56 | L1 | SADAYGDSM | 272 | 9 | | | | | 8992 |
| HPV56 | L1 | SAEVMAYL | 417 | 8 | | | | | 8993 |
| HPV56 | L1 | SAEVMAYLHNM | 417 | 11 | | | | | 8994 |
| HPV56 | L1 | SAPTSTST | 520 | 8 | | | | | 8995 |
| HPV56 | L1 | SAPTSTSTPA | 520 | 10 | | | | | 8996 |
| HPV56 | L1 | SAYQYRVFRV | 100 | 10 | | | | | 8997 |
| HPV56 | L1 | SIFYHAGSSRL | 67 | 11 | | | | | 8998 |
| HPV56 | L1 | SLEDKYRYV | 446 | 9 | | | | | 8999 |
| HPV56 | L1 | SMITSEAQL | 332 | 9 | | | | | 9000 |
| HPV56 | L1 | SMWFYLRREQL | 279 | 11 | | | | | 9001 |
| HPV56 | L1 | STCKYPDYL | 261 | 9 | | | | | 9002 |
| HPV56 | L1 | STCKYPDYLKM | 261 | 11 | | | | | 9003 |
| HPV56 | L1 | STDLDQFPL | 489 | 9 | | | | | 9004 |
| HPV56 | L1 | STNMTIST | 373 | 8 | | | | | 9005 |
| HPV56 | L1 | STNMTISTA | 373 | 9 | | | | | 9006 |
| HPV56 | L1 | STNMTISTAT | 373 | 10 | | | | | 9007 |
| HPV56 | L1 | SVDGKQTQL | 182 | 9 | | | | | 9008 |
| HPV56 | L1 | SVDGKQTQLCI | 182 | 11 | | | | | 9009 |
| HPV56 | L1 | SVTKDNTKT | 86 | 9 | | | | | 9010 |
| HPV56 | L1 | SVTKDNTKTNI | 86 | 11 | | | | | 9011 |
| HPV56 | L1 | SVYVATPSGSM | 323 | 11 | | | | | 9012 |
| HPV56 | L1 | TATEQLSKYDA | 380 | 11 | | | | | 9013 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | L1 | TIPAELYL | 304 | 8 | | | | | 9014 |
| HPV56 | L1 | TISTATEQL | 377 | 9 | | | | | 9015 |
| HPV56 | L1 | TLSAEVMA | 415 | 8 | | | | | 9016 |
| HPV56 | L1 | TLSAEVMAYL | 415 | 10 | | | | | 9017 |
| HPV56 | L1 | TQLCIVGCT | 188 | 9 | | | | | 9018 |
| HPV56 | L1 | TQLCIVGCTPA | 188 | 11 | | | | | 9019 |
| HPV56 | L1 | TQVTTGDCPPL | 212 | 11 | | | | | 9020 |
| HPV56 | L1 | TTGDCPPL | 215 | 8 | | | | | 9021 |
| HPV56 | L1 | TTGDCPPLA | 215 | 9 | | | | | 9022 |
| HPV56 | L1 | TTGDCPPLAL | 215 | 10 | | | | | 9023 |
| HPV56 | L1 | TTGDCPPLALI | 215 | 11 | | | | | 9024 |
| HPV56 | L1 | TTRSTNMT | 370 | 8 | | | | | 9025 |
| HPV56 | L1 | TTRSTNMTI | 370 | 9 | | | | | 9026 |
| HPV56 | L1 | TTRSTNMTIST | 370 | 11 | | | | | 9027 |
| HPV56 | L1 | TVVDTTRST | 366 | 9 | | | | | 9028 |
| HPV56 | L1 | TVVDTTRSTNM | 366 | 11 | | | | | 9029 |
| HPV56 | L1 | VATDSYVKRT | 57 | 10 | | | | | 9030 |
| HPV56 | L1 | VATPSGSM | 326 | 8 | | | | | 9031 |
| HPV56 | L1 | VATPSGSMI | 326 | 9 | | | | | 9032 |
| HPV56 | L1 | VATPSGSMIT | 326 | 10 | | | | | 9033 |
| HPV56 | L1 | VATSKKRSA | 513 | 9 | | | | | 9034 |
| HPV56 | L1 | VATSKKRSAPT | 513 | 11 | | | | | 9035 |
| HPV56 | L1 | VIEDSRDNI | 173 | 9 | | | | | 9036 |
| HPV56 | L1 | VIEDSRDNISV | 173 | 11 | | | | | 9037 |
| HPV56 | L1 | VLQESKAEV | 246 | 9 | | | | | 9038 |
| HPV56 | L1 | VLQESKAEVPL | 246 | 11 | | | | | 9039 |
| HPV56 | L1 | VMAYLHNM | 420 | 8 | | | | | 9040 |
| HPV56 | L1 | VMAYLHNMNA | 420 | 10 | | | | | 9041 |
| HPV56 | L1 | VQSTCKYPDYL | 259 | 11 | | | | | 9042 |
| HPV56 | L1 | VTKDNTKT | 87 | 8 | | | | | 9043 |
| HPV56 | L1 | VTKDNTKTNI | 87 | 10 | | | | | 9044 |
| HPV56 | L1 | VTTGDCPPL | 214 | 9 | | | | | 9045 |
| HPV56 | L1 | VTTGDCPPLA | 214 | 10 | | | | | 9046 |
| HPV56 | L1 | VTTGDCPPLAL | 214 | 11 | | | | | 9047 |
| HPV56 | L1 | VTVVDTFRST | 365 | 10 | | | | | 9048 |
| HPV56 | L1 | VVATDSYV | 56 | 8 | | | | | 9049 |
| HPV56 | L1 | VVATDSYVKRT | 56 | 11 | | | | | 9050 |
| HPV56 | L1 | VVDTTRST | 367 | 8 | | | | | 9051 |
| HPV56 | L1 | VVDTTRSTNM | 367 | 10 | | | | | 9052 |
| HPV56 | L1 | VVDTTRSTNMT | 367 | 11 | | | | | 9053 |
| HPV56 | L1 | WACVGLEV | 134 | 8 | | | | | 9054 |
| HPV56 | L1 | WTKGAVCKST | 203 | 10 | | | | | 9055 |
| HPV56 | L1 | YIYRDPPL | 7 | 8 | | | | | 9056 |
| HPV56 | L1 | YLHNMNANL | 423 | 9 | | | | | 9057 |
| HPV56 | L1 | YLHNMNANLL | 423 | 10 | | | | | 9058 |
| HPV56 | L1 | YLKMSADA | 268 | 8 | | | | | 9059 |
| HPV56 | L1 | YLPPTPVSKV | 47 | 10 | | | | | 9060 |
| HPV56 | L1 | YLPPTPVSKVV | 47 | 11 | | | | | 9061 |
| HPV56 | L1 | YLRHVEEYEL | 396 | 10 | | | | | 9062 |
| HPV56 | L1 | YLRREQLFA | 283 | 9 | | | | | 9063 |
| HPV56 | L1 | YQYRVFRV | 102 | 8 | | | | | 9064 |
| HPV56 | L1 | YQYRVFRVRL | 102 | 10 | | | | | 9065 |
| HPV56 | L1 | YVATPSGSM | 325 | 9 | | | | | 9066 |
| HPV56 | L1 | YVATPSGSMI | 325 | 10 | | | | | 9067 |
| HPV56 | L1 | YVATPSGSMIT | 325 | 11 | | | | | 9068 |
| HPV56 | L1 | YVKRTSIFYHA | 62 | 11 | | | | | 9069 |
| HPV56 | L1 | YVRSTAIT | 453 | 8 | | | | | 9070 |
| HPV56 | L2 | AAPRLYRKA | 222 | 9 | | | | | 9071 |
| HPV56 | L2 | ALHRPAFT | 281 | 8 | | | | | 9072 |
| HPV56 | L2 | ALHRPAFTT | 281 | 9 | | | | | 9073 |
| HPV56 | L2 | AQAEEIEM | 327 | 8 | | | | | 9074 |
| HPV56 | L2 | AQAEEIEMQPL | 327 | 11 | | | | | 9075 |
| HPV56 | L2 | ATIQTRRGT | 303 | 9 | | | | | 9076 |
| HPV56 | L2 | ATIQTRRGTQI | 303 | 11 | | | | | 9077 |
| HPV56 | L2 | ATLVSADNPL | 246 | 10 | | | | | 9078 |
| HPV56 | L2 | ATPSAHLPI | 367 | 9 | | | | | 9079 |
| HPV56 | L2 | ATQLYKTCKL | 14 | 10 | | | | | 9080 |
| HPV56 | L2 | ATRRKRASA | 6 | 9 | | | | | 9081 |
| HPV56 | L2 | ATRRKRASAT | 6 | 10 | | | | | 9082 |
| HPV56 | L2 | AVHGSGTEPI | 201 | 10 | | | | | 9083 |
| HPV56 | L2 | AVLDITPT | 139 | 8 | | | | | 9084 |
| HPV56 | L2 | AVLDITPTSST | 139 | 11 | | | | | 9085 |
| HPV56 | L2 | DISPIAQA | 322 | 8 | | | | | 9086 |
| HPV56 | L2 | DISPIAQAEEI | 322 | 11 | | | | | 9087 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | L2 | DITPTSST | 142 | 8 | | | | | 9088 |
| HPV56 | L2 | DITPTSSTV | 142 | 9 | | | | | 9089 |
| HPV56 | L2 | DITPTSSTVHV | 142 | 11 | | | | | 9090 |
| HPV56 | L2 | DIVLPTGPST | 406 | 10 | | | | | 9091 |
| HPV56 | L2 | DIYANIDDEA | 349 | 10 | | | | | 9092 |
| HPV56 | L2 | DTSLAFSPSGV | 260 | 11 | | | | | 9093 |
| HPV56 | L2 | DVTHDVYI | 425 | 8 | | | | | 9094 |
| HPV56 | L2 | DVTPARPPI | 83 | 9 | | | | | 9095 |
| HPV56 | L2 | DVTPARPPIV | 83 | 10 | | | | | 9096 |
| HPV56 | L2 | DVTPARPPIVV | 83 | 11 | | | | | 9097 |
| HPV56 | L2 | DVVNKIEQKT | 30 | 10 | | | | | 9098 |
| HPV56 | L2 | DVYIQGSSFA | 429 | 10 | | | | | 9099 |
| HPV56 | L2 | DVYIQGSSFAL | 429 | 11 | | | | | 9100 |
| HPV56 | L2 | EAPGLSSQSV | 357 | 10 | | | | | 9101 |
| HPV56 | L2 | EAPGLSSQSVA | 357 | 11 | | | | | 9102 |
| HPV56 | L2 | EAPQTGEV | 169 | 8 | | | | | 9103 |
| HPV56 | L2 | EIEMQPLL | 331 | 8 | | | | | 9104 |
| HPV56 | L2 | EIEMQPLLSA | 331 | 10 | | | | | 9105 |
| HPV56 | L2 | EIPMQTFA | 194 | 8 | | | | | 9106 |
| HPV56 | L2 | EIPMQTFAV | 194 | 9 | | | | | 9107 |
| HPV56 | L2 | EITSSSTT | 129 | 8 | | | | | 9108 |
| HPV56 | L2 | EITSSSTTT | 129 | 9 | | | | | 9109 |
| HPV56 | L2 | EITSSSTTTPA | 129 | 11 | | | | | 9110 |
| HPV56 | L2 | EMQPLLSA | 333 | 8 | | | | | 9111 |
| HPV56 | L2 | EQKTWADKI | 36 | 9 | | | | | 9112 |
| HPV56 | L2 | EQKTWADKIL | 36 | 10 | | | | | 9113 |
| HPV56 | L2 | ETPFYSGPDI | 398 | 10 | | | | | 9114 |
| HPV56 | L2 | ETPFYSGPDIV | 398 | 11 | | | | | 9115 |
| HPV56 | L2 | EVSGNILI | 175 | 8 | | | | | 9116 |
| HPV56 | L2 | EVSGNILIST | 175 | 10 | | | | | 9117 |
| HPV56 | L2 | FADGDVAA | 457 | 8 | | | | | 9118 |
| HPV56 | L2 | FASNTTNV | 382 | 8 | | | | | 9119 |
| HPV56 | L2 | FASNTTNVT | 382 | 9 | | | | | 9120 |
| HPV56 | L2 | FASNTTNVTA | 382 | 10 | | | | | 9121 |
| HPV56 | L2 | FAVHGSGT | 200 | 8 | | | | | 9122 |
| HPV56 | L2 | FAVHGSGTEPI | 200 | 11 | | | | | 9123 |
| HPV56 | L2 | FIDPPVIEA | 162 | 9 | | | | | 9124 |
| HPV56 | L2 | FLDRPATL | 241 | 8 | | | | | 9125 |
| HPV56 | L2 | FLDRPATLV | 241 | 9 | | | | | 9126 |
| HPV56 | L2 | FLDRPATLVSA | 241 | 11 | | | | | 9127 |
| HPV56 | L2 | FMNIVALHRPA | 276 | 11 | | | | | 9128 |
| HPV56 | L2 | FQQVKVTDPA | 231 | 10 | | | | | 9129 |
| HPV56 | L2 | FTGSGGFEI | 122 | 9 | | | | | 9130 |
| HPV56 | L2 | FTGSGGFEIT | 122 | 10 | | | | | 9131 |
| HPV56 | L2 | FTTRRGGV | 287 | 8 | | | | | 9132 |
| HPV56 | L2 | FTYFGGLGI | 51 | 9 | | | | | 9133 |
| HPV56 | L2 | FTYFGGLGIGT | 51 | 11 | | | | | 9134 |
| HPV56 | L2 | FVPQSPYDV | 418 | 9 | | | | | 9135 |
| HPV56 | L2 | FVPQSPYDVT | 418 | 10 | | | | | 9136 |
| HPV56 | L2 | GAGIPNFT | 116 | 8 | | | | | 9137 |
| HPV56 | L2 | GARVHYYYDI | 314 | 10 | | | | | 9138 |
| HPV56 | L2 | GIHSYEEI | 188 | 8 | | | | | 9139 |
| HPV56 | L2 | GIHSYEEIPM | 188 | 10 | | | | | 9140 |
| HPV56 | L2 | GLGIGTGT | 56 | 8 | | | | | 9141 |
| HPV56 | L2 | GLSSQSVA | 360 | 8 | | | | | 9142 |
| HPV56 | L2 | GLSSQSVAT | 360 | 9 | | | | | 9143 |
| HPV56 | L2 | GLYDIYANI | 346 | 9 | | | | | 9144 |
| HPV56 | L2 | GTCPEDVV | 25 | 8 | | | | | 9145 |
| HPV56 | L2 | GTCPEDVVNKI | 25 | 11 | | | | | 9146 |
| HPV56 | L2 | GTEPISST | 206 | 8 | | | | | 9147 |
| HPV56 | L2 | GTEPISSTPI | 206 | 10 | | | | | 9148 |
| HPV56 | L2 | GTGSGGRA | 62 | 8 | | | | | 9149 |
| HPV56 | L2 | GTGSGGRAGYV | 62 | 11 | | | | | 9150 |
| HPV56 | L2 | GTGTGSGGRA | 60 | 10 | | | | | 9151 |
| HPV56 | L2 | GTQIGARV | 310 | 8 | | | | | 9152 |
| HPV56 | L2 | GVAPDPDFM | 269 | 9 | | | | | 9153 |
| HPV56 | L2 | GVAPDPDFMNI | 269 | 11 | | | | | 9154 |
| HPV56 | L2 | GVRFSRLGRKA | 293 | 11 | | | | | 9155 |
| HPV56 | L2 | HITNPLFI | 156 | 8 | | | | | 9156 |
| HPV56 | L2 | HLPIKPST | 372 | 8 | | | | | 9157 |
| HPV56 | L2 | HLPIKPSTL | 372 | 9 | | | | | 9158 |
| HPV56 | L2 | HVSSTHIT | 151 | 8 | | | | | 9159 |
| HPV56 | L2 | HVSSTHITNPL | 151 | 11 | | | | | 9160 |
| HPV56 | L2 | IAAPRLYRKA | 221 | 10 | | | | | 9161 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | L2 | IAQAEEIEM | 326 | 9 | | | | | 9162 |
| HPV56 | L2 | ILISTPTSGI | 180 | 10 | | | | | 9163 |
| HPV56 | L2 | ILQWGSLFT | 44 | 9 | | | | | 9164 |
| HPV56 | L2 | IQGSSFAL | 432 | 8 | | | | | 9165 |
| HPV56 | L2 | IQGSSFALWPV | 432 | 11 | | | | | 9166 |
| HPV56 | L2 | IQTRRGTQI | 305 | 9 | | | | | 9167 |
| HPV56 | L2 | IQTRRGTQIGA | 305 | 11 | | | | | 9168 |
| HPV56 | L2 | ITNPLFIDPPV | 157 | 11 | | | | | 9169 |
| HPV56 | L2 | ITPTSSTV | 143 | 8 | | | | | 9170 |
| HPV56 | L2 | ITPTSSTVHV | 143 | 10 | | | | | 9171 |
| HPV56 | L2 | ITSSSTTT | 130 | 8 | | | | | 9172 |
| HPV56 | L2 | ITSSSTTTPA | 130 | 10 | | | | | 9173 |
| HPV56 | L2 | ITSSSTTTPAV | 130 | 11 | | | | | 9174 |
| HPV56 | L2 | IVALHRPA | 279 | 8 | | | | | 9175 |
| HPV56 | L2 | IVALHRPAFT | 279 | 10 | | | | | 9176 |
| HPV56 | L2 | IVALHRPAFTT | 279 | 11 | | | | | 9177 |
| HPV56 | L2 | IVDVTPARPPI | 81 | 11 | | | | | 9178 |
| HPV56 | L2 | IVLPTGPST | 407 | 9 | | | | | 9179 |
| HPV56 | L2 | IVTLVEESSV | 103 | 10 | | | | | 9180 |
| HPV56 | L2 | IVTLVEESSVI | 103 | 11 | | | | | 9181 |
| HPV56 | L2 | IVVESVGPT | 91 | 9 | | | | | 9182 |
| HPV56 | L2 | KAFQQVKV | 229 | 8 | | | | | 9183 |
| HPV56 | L2 | KAFQQVKVT | 229 | 9 | | | | | 9184 |
| HPV56 | L2 | KATIQTRRGT | 302 | 10 | | | | | 9185 |
| HPV56 | L2 | KIEQKTWA | 34 | 8 | | | | | 9186 |
| HPV56 | L2 | KIEQKTWADKI | 34 | 11 | | | | | 9187 |
| HPV56 | L2 | KILQWGSL | 43 | 8 | | | | | 9188 |
| HPV56 | L2 | KILQWGSLFT | 43 | 10 | | | | | 9189 |
| HPV56 | L2 | KLSGTCPEDV | 22 | 10 | | | | | 9190 |
| HPV56 | L2 | KLSGTCPEDVV | 22 | 11 | | | | | 9191 |
| HPV56 | L2 | KTCKLSGT | 19 | 8 | | | | | 9192 |
| HPV56 | L2 | KTWADKIL | 38 | 8 | | | | | 9193 |
| HPV56 | L2 | KVTDPAFL | 235 | 8 | | | | | 9194 |
| HPV56 | L2 | LAFSPSGV | 263 | 8 | | | | | 9195 |
| HPV56 | L2 | LAFSPSGVA | 263 | 9 | | | | | 9196 |
| HPV56 | L2 | LISTPTSGI | 181 | 9 | | | | | 9197 |
| HPV56 | L2 | LLSANNSFDGL | 337 | 11 | | | | | 9198 |
| HPV56 | L2 | LQWGSLFT | 45 | 8 | | | | | 9199 |
| HPV56 | L2 | LVEESSVI | 106 | 8 | | | | | 9200 |
| HPV56 | L2 | LVSADNPL | 248 | 8 | | | | | 9201 |
| HPV56 | L2 | MQTFAVHGSGT | 197 | 11 | | | | | 9202 |
| HPV56 | L2 | NIDDEAPGL | 353 | 9 | | | | | 9203 |
| HPV56 | L2 | NILISTPT | 179 | 8 | | | | | 9204 |
| HPV56 | L2 | NILISTPTSGI | 179 | 11 | | | | | 9205 |
| HPV56 | L2 | NIVALHRPA | 278 | 9 | | | | | 9206 |
| HPV56 | L2 | NIVALHRPAFT | 278 | 11 | | | | | 9207 |
| HPV56 | L2 | NTTNVTAPL | 385 | 9 | | | | | 9208 |
| HPV56 | L2 | NVTAPLGNV | 388 | 9 | | | | | 9209 |
| HPV56 | L2 | PAFLDRPA | 239 | 8 | | | | | 9210 |
| HPV56 | L2 | PAFLDRPAT | 239 | 9 | | | | | 9211 |
| HPV56 | L2 | PAFLDRPATL | 239 | 10 | | | | | 9212 |
| HPV56 | L2 | PAFLDRPATLV | 239 | 11 | | | | | 9213 |
| HPV56 | L2 | PAFTTRRGGV | 285 | 10 | | | | | 9214 |
| HPV56 | L2 | PARPPIVV | 86 | 8 | | | | | 9215 |
| HPV56 | L2 | PARPPIVVESV | 86 | 11 | | | | | 9216 |
| HPV56 | L2 | PATLVSADNPL | 245 | 11 | | | | | 9217 |
| HPV56 | L2 | PAVLDITPT | 138 | 9 | | | | | 9218 |
| HPV56 | L2 | PIAQAEEI | 325 | 8 | | | | | 9219 |
| HPV56 | L2 | PIAQAEEIEM | 325 | 10 | | | | | 9220 |
| HPV56 | L2 | PIKPSTLSFA | 374 | 10 | | | | | 9221 |
| HPV56 | L2 | PIPGFRRI | 214 | 8 | | | | | 9222 |
| HPV56 | L2 | PIPGFRRIA | 214 | 9 | | | | | 9223 |
| HPV56 | L2 | PIPGFRRIAA | 214 | 10 | | | | | 9224 |
| HPV56 | L2 | PIVVESVGPT | 90 | 10 | | | | | 9225 |
| HPV56 | L2 | PLFEGTDT | 254 | 8 | | | | | 9226 |
| HPV56 | L2 | PLFEGTDTSL | 254 | 10 | | | | | 9227 |
| HPV56 | L2 | PLFEGTDTSLA | 254 | 11 | | | | | 9228 |
| HPV56 | L2 | PLFIDPPV | 160 | 8 | | | | | 9229 |
| HPV56 | L2 | PLFIDPPVI | 160 | 9 | | | | | 9230 |
| HPV56 | L2 | PLFIDPPVIEA | 160 | 11 | | | | | 9231 |
| HPV56 | L2 | PLGNVWET | 392 | 8 | | | | | 9232 |
| HPV56 | L2 | PLGSRPST | 73 | 8 | | | | | 9233 |
| HPV56 | L2 | PLGSRPSTI | 73 | 9 | | | | | 9234 |
| HPV56 | L2 | PLGSRPSTIV | 73 | 10 | | | | | 9235 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | L2 | PQSPYDVT | 420 | 8 | | | | | 9236 |
| HPV56 | L2 | PQSPYDVTHDV | 420 | 11 | | | | | 9237 |
| HPV56 | L2 | PQTGEVSGNI | 171 | 10 | | | | | 9238 |
| HPV56 | L2 | PQTGEVSGNIL | 171 | 11 | | | | | 9239 |
| HPV56 | L2 | PTDPSIVT | 98 | 8 | | | | | 9240 |
| HPV56 | L2 | PTDPSIVTL | 98 | 9 | | | | | 9241 |
| HPV56 | L2 | PTDPSIVTLV | 98 | 10 | | | | | 9242 |
| HPV56 | L2 | PTGPSTWPFV | 410 | 10 | | | | | 9243 |
| HPV56 | L2 | PTSGIHSYEEI | 185 | 11 | | | | | 9244 |
| HPV56 | L2 | PTSSTVHV | 145 | 8 | | | | | 9245 |
| HPV56 | L2 | PTSSTVHVSST | 145 | 11 | | | | | 9246 |
| HPV56 | L2 | PVIEAPQT | 166 | 8 | | | | | 9247 |
| HPV56 | L2 | PVIEAPQTGEV | 166 | 11 | | | | | 9248 |
| HPV56 | L2 | QAEEIEMQPL | 328 | 10 | | | | | 9249 |
| HPV56 | L2 | QAEEIEMQPLL | 328 | 11 | | | | | 9250 |
| HPV56 | L2 | QLYKTCKL | 16 | 8 | | | | | 9251 |
| HPV56 | L2 | QLYKTCKLSGT | 16 | 11 | | | | | 9252 |
| HPV56 | L2 | QQVKVTDPA | 232 | 9 | | | | | 9253 |
| HPV56 | L2 | QQVKVTDPAFL | 232 | 11 | | | | | 9254 |
| HPV56 | L2 | QTFAVHGSGT | 198 | 10 | | | | | 9255 |
| HPV56 | L2 | QTGEVSGNI | 172 | 9 | | | | | 9256 |
| HPV56 | L2 | QTGEVSGNIL | 172 | 10 | | | | | 9257 |
| HPV56 | L2 | QTGEVSGNILI | 172 | 11 | | | | | 9258 |
| HPV56 | L2 | QTRRGTQI | 306 | 8 | | | | | 9259 |
| HPV56 | L2 | QTRRGTQIGA | 306 | 10 | | | | | 9260 |
| HPV56 | L2 | QVKVTDPA | 233 | 8 | | | | | 9261 |
| HPV56 | L2 | QVKVTDPAFL | 233 | 10 | | | | | 9262 |
| HPV56 | L2 | RASATQLYKT | 11 | 10 | | | | | 9263 |
| HPV56 | L2 | RATRRKRA | 5 | 8 | | | | | 9264 |
| HPV56 | L2 | RATRRKRASA | 5 | 10 | | | | | 9265 |
| HPV56 | L2 | RATRRKRASAT | 5 | 11 | | | | | 9266 |
| HPV56 | L2 | RIAAPRLYRKA | 220 | 11 | | | | | 9267 |
| HPV56 | L2 | RIPYFFADGDV | 452 | 11 | | | | | 9268 |
| HPV56 | L2 | RLGRKATI | 298 | 8 | | | | | 9269 |
| HPV56 | L2 | RLGRKATIQT | 298 | 10 | | | | | 9270 |
| HPV56 | L2 | RLYRKAFQQV | 225 | 10 | | | | | 9271 |
| HPV56 | L2 | RVHYYYDI | 316 | 8 | | | | | 9272 |
| HPV56 | L2 | RVHYYYDISPI | 316 | 11 | | | | | 9273 |
| HPV56 | L2 | SADNPLFEGT | 250 | 10 | | | | | 9274 |
| HPV56 | L2 | SAHLPIKPST | 370 | 10 | | | | | 9275 |
| HPV56 | L2 | SAHLPIKPSTL | 370 | 11 | | | | | 9276 |
| HPV56 | L2 | SANNSFDGL | 339 | 9 | | | | | 9277 |
| HPV56 | L2 | SATQLYKT | 13 | 8 | | | | | 9278 |
| HPV56 | L2 | SATQLYKTCKL | 13 | 11 | | | | | 9279 |
| HPV56 | L2 | SIVTLVEESSV | 102 | 11 | | | | | 9280 |
| HPV56 | L2 | SLAFSPSGV | 262 | 9 | | | | | 9281 |
| HPV56 | L2 | SLAFSPSGVA | 262 | 10 | | | | | 9282 |
| HPV56 | L2 | SLFTYFGGL | 49 | 9 | | | | | 9283 |
| HPV56 | L2 | SLFTYFGGLGI | 49 | 11 | | | | | 9284 |
| HPV56 | L2 | SQSVATPSA | 363 | 9 | | | | | 9285 |
| HPV56 | L2 | SQSVATPSAHL | 363 | 11 | | | | | 9286 |
| HPV56 | L2 | STHITNPL | 154 | 8 | | | | | 9287 |
| HPV56 | L2 | STHITNPLFI | 154 | 10 | | | | | 9288 |
| HPV56 | L2 | STIVDVTPA | 79 | 9 | | | | | 9289 |
| HPV56 | L2 | STLSFASNT | 378 | 9 | | | | | 9290 |
| HFV56 | L2 | STLSFASNTT | 378 | 10 | | | | | 9291 |
| HPV56 | L2 | STPIPGFRRI | 212 | 10 | | | | | 9292 |
| HPV56 | L2 | STPIPGFRRIA | 212 | 11 | | | | | 9293 |
| HPV56 | L2 | STTTPAVL | 134 | 8 | | | | | 9294 |
| HPV56 | L2 | STTTPAVLDI | 134 | 10 | | | | | 9295 |
| HPV56 | L2 | STTTPAVLDIT | 134 | 11 | | | | | 9296 |
| HPV56 | L2 | STVHVSST | 148 | 8 | | | | | 9297 |
| HPV56 | L2 | STVHVSSTHI | 148 | 10 | | | | | 9298 |
| HPV56 | L2 | STVHVSSTHIT | 148 | 11 | | | | | 9299 |
| HPV56 | L2 | SVATPSAHL | 365 | 9 | | | | | 9300 |
| HPV56 | L2 | SVATPSAHLPI | 365 | 11 | | | | | 9301 |
| HPV56 | L2 | SVGPTDPSI | 95 | 9 | | | | | 9302 |
| HPV56 | L2 | SVGPTDPSIV | 95 | 10 | | | | | 9303 |
| HPV56 | L2 | SVGPTDPSIVT | 95 | 11 | | | | | 9304 |
| HPV56 | L2 | SVIESGAGI | 111 | 9 | | | | | 9305 |
| HPV56 | L2 | TAPLGNVWET | 390 | 10 | | | | | 9306 |
| HPV56 | L2 | TIQTRRGT | 304 | 8 | | | | | 9307 |
| HPV56 | L2 | TIQTRRGTQI | 304 | 10 | | | | | 9308 |
| HPV56 | L2 | TIVDVTPA | 80 | 8 | | | | | 9309 |

TABLE VIII-continued

A02 Supermotif Peptides with Binding Information

| Type | Protein | Sequence | Position | No. of Amino Acids | A*0201 | A*0203 | A*0206 | A*6802 | Seq. Id. No. |
|---|---|---|---|---|---|---|---|---|---|
| HPV56 | L2 | TLSFASNT | 379 | 8 | | | | | 9310 |
| HPV56 | L2 | TLSFASNTT | 379 | 9 | | | | | 9311 |
| HPV56 | L2 | TLSFASNTTNV | 379 | 11 | | | | | 9312 |
| HPV56 | L2 | TLVEESSV | 105 | 8 | | | | | 9313 |
| HPV56 | L2 | TLVEESSVI | 105 | 9 | | | | | 9314 |
| HPV56 | L2 | TLVSADNPL | 247 | 9 | | | | | 9315 |
| HPV56 | L2 | TQLYKTCKL | 15 | 9 | | | | | 9316 |
| HPV56 | L2 | TTNVTAPL | 386 | 8 | | | | | 9317 |
| HPV56 | L2 | TTNVTAPLGNV | 386 | 11 | | | | | 9318 |
| HPV56 | L2 | TTPAVLDI | 136 | 8 | | | | | 9319 |
| HPV56 | L2 | TTPAVLDIT | 136 | 9 | | | | | 9320 |
| HPV56 | L2 | TTPAVLDITPT | 136 | 11 | | | | | 9321 |
| HPV56 | L2 | TTTPAVLDI | 135 | 9 | | | | | 9322 |
| HPV56 | L2 | TTTPAVLDIT | 135 | 10 | | | | | 9323 |
| HPV56 | L2 | TVHVSSTHI | 149 | 9 | | | | | 9324 |
| HPV56 | L2 | TVHVSSTHIT | 149 | 10 | | | | | 9325 |
| HPV56 | L2 | VAHRATRRKRA | 2 | 11 | | | | | 9326 |
| HPV56 | L2 | VALHRPAFT | 280 | 9 | | | | | 9327 |
| HPV56 | L2 | VALHRPAFTT | 280 | 10 | | | | | 9328 |
| HPV56 | L2 | VAPDPDFM | 270 | 8 | | | | | 9329 |
| HPV56 | L2 | VAPDPDFMNI | 270 | 10 | | | | | 9330 |
| HPV56 | L2 | VAPDPDFMNIV | 270 | 11 | | | | | 9331 |
| HPV56 | L2 | VATPSAHL | 366 | 8 | | | | | 9332 |
| HPV56 | L2 | VATPSAHLPI | 366 | 10 | | | | | 9333 |
| HPV56 | L2 | VIEAPQTGEV | 167 | 10 | | | | | 9334 |
| HPV56 | L2 | VIESGAGI | 112 | 8 | | | | | 9335 |
| HPV56 | L2 | VLDITPTSST | 140 | 10 | | | | | 9336 |
| HPV56 | L2 | VLDITPTSSTV | 140 | 11 | | | | | 9337 |
| HPV56 | L2 | VLPTGPST | 408 | 8 | | | | | 9338 |
| HPV56 | L2 | VTAPLGNV | 389 | 8 | | | | | 9339 |
| HPV56 | L2 | VTAPLGNVWET | 389 | 11 | | | | | 9340 |
| HPV56 | L2 | VTDPAFLDRPA | 236 | 11 | | | | | 9341 |
| HPV56 | L2 | VTLVEESSV | 104 | 9 | | | | | 9342 |
| HPV56 | L2 | VTLVEESSVI | 104 | 10 | | | | | 9343 |
| HPV56 | L2 | VTPARPPI | 84 | 8 | | | | | 9344 |
| HPV56 | L2 | VTPARPPIV | 84 | 9 | | | | | 9345 |
| HPV56 | L2 | VTPARPPIVV | 84 | 10 | | | | | 9346 |
| HPV56 | L2 | VVESVGPT | 92 | 8 | | | | | 9347 |
| HPV56 | L2 | VVNKIEQKT | 31 | 9 | | | | | 9348 |
| HPV56 | L2 | VVNKIEQKTWA | 31 | 11 | | | | | 9349 |
| HPV56 | L2 | WADKILQWGSL | 40 | 11 | | | | | 9350 |
| HPV56 | L2 | YANIDDEA | 351 | 8 | | | | | 9351 |
| HPV56 | L2 | YANIDDEAPGL | 351 | 11 | | | | | 9352 |
| HPV56 | L2 | YIQGSSFA | 431 | 8 | | | | | 9353 |
| HPV56 | L2 | YIQGSSFAL | 431 | 9 | | | | | 9354 |
| HPV56 | L2 | YVPLGSRPST | 71 | 10 | | | | | 9355 |
| HPV56 | L2 | YVPLGSRPSTI | 71 | 11 | | | | | 9356 |

TABLE IX

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV16 | E1 | AAALYWYK | 316 | 8 | | | | | | 9357 |
| HPV16 | E1 | AAMLAKFK | 205 | 8 | | | | | | 9358 |
| HPV16 | E1 | AICIEKQSR | 112 | 9 | 0.0010 | 0.0057 | | | | 9359 |
| HPV16 | E1 | ALFTAQEAK | 69 | 9 | 0.2400 | 0.4000 | | | | 9360 |
| HPV16 | E1 | ALKRFLQGIPK | 459 | 11 | | | | | | 9361 |
| HPV16 | E1 | ATMCRHYK | 406 | 8 | | | | | | 9362 |
| HPV16 | E1 | ATMCRHYKR | 406 | 9 | 0.0660 | 1.5000 | | | | 9363 |
| HPV16 | E1 | AVQVLKRK | 82 | 8 | | | | | | 9364 |
| HPV16 | E1 | CATMCRHYK | 405 | 9 | 0.0012 | 0.0098 | 0.0077 | 0.0100 | 0.0056 | 9365 |
| HPV16 | E1 | CATMCRHYKR | 405 | 10 | | | | | | 9366 |
| HPV16 | E1 | CIEKQSRAAK | 114 | 10 | | | | | | 9367 |
| HPV16 | E1 | CIEKQSRAAKR | 114 | 11 | | | | | | 9368 |
| HPV16 | E1 | CMMIEPPK | 304 | 8 | | | | | | 9369 |
| HPV16 | E1 | CMMIEPPKLR | 304 | 10 | | | | | | 9370 |
| HPV16 | E1 | CVDNNISPR | 101 | 9 | | | | | | 9371 |
| HPV16 | E1 | CVDNNISPRLK | 101 | 11 | | | | | | 9372 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV16 | E1 | DAVQVLKR | 81 | 8 | | | | | | 9373 |
| HPV16 | E1 | DAVQVLKRK | 81 | 9 | | | | | | 9374 |
| HPV16 | E1 | DIVDDSEIAYK | 368 | 11 | | | | | | 9375 |
| HPV16 | E1 | DSRWPYLHNR | 573 | 10 | | | | | | 9376 |
| HPV16 | E1 | DTNSNASAFLK | 384 | 11 | | | | | | 9377 |
| HPV16 | E1 | DTPEWIQR | 335 | 8 | | | | | | 9378 |
| HPV16 | E1 | DVKHRPLVQLK | 548 | 11 | | | | | | 9379 |
| HPV16 | E1 | ELNDKNWK | 603 | 8 | | | | | | 9380 |
| HPV16 | E1 | ELVRPFKSNK | 221 | 10 | | | | | | 9381 |
| HPV16 | E1 | ETIEKLLSK | 288 | 9 | | | | | | 9382 |
| HPV16 | E1 | ETQQMLQVEGR | 140 | 11 | | | | | | 9383 |
| HPV16 | E1 | FLKSNSQAK | 392 | 9 | 0.0013 | 0.0002 | | | | 9384 |
| HPV16 | E1 | FLQGIPKK | 463 | 8 | | | | | | 9385 |
| HPV16 | E1 | FMSFLTALK | 453 | 9 | 0.1300 | 0.2100 | | | | 9386 |
| HPV16 | E1 | FMSFLTALKR | 453 | 10 | | | | | | 9387 |
| HPV16 | E1 | FSELVRPFK | 219 | 9 | | | | | | 9388 |
| HPV16 | E1 | FTAQEAKQHR | 71 | 10 | | | | | | 9389 |
| HPV16 | E1 | GLTPSIADSIK | 242 | 11 | | | | | | 9390 |
| HPV16 | E1 | GMVVLLLVR | 272 | 9 | 0.0036 | 0.0082 | | | | 9391 |
| HPV16 | E1 | GMVVLLLVRYK | 272 | 11 | | | | | | 9392 |
| HPV16 | E1 | GSGGEGVSER | 174 | 10 | | | | | | 9393 |
| HPV16 | E1 | GSVICFVNSK | 496 | 10 | | | | | | 9394 |
| HPV16 | E1 | GVSFSELVR | 216 | 9 | 0.0011 | 0.0180 | | | | 9395 |
| HPV16 | E1 | HALFTAQEAK | 68 | 10 | | | | | | 9396 |
| HPV16 | E1 | ILLYGAANTGK | 473 | 11 | | | | | | 9397 |
| HPV16 | E1 | ILNVLKTSNAK | 194 | 11 | | | | | | 9398 |
| HPV16 | E1 | IVDDSEIAYK | 369 | 10 | | | | | | 9399 |
| HPV16 | E1 | IVKDCATMCR | 401 | 10 | | | | | | 9400 |
| HPV16 | E1 | KAAMLAKFK | 204 | 9 | 0.1100 | 0.1800 | | | | 9401 |
| HPV16 | E1 | KAICIEKQSR | 111 | 10 | | | | | | 9402 |
| HPV16 | E1 | KIVKDCATMCR | 400 | 11 | | | | | | 9403 |
| HPV16 | E1 | KSFFSRTWSR | 610 | 10 | | | | | | 9404 |
| HPV16 | E1 | KSLFGMSLMK | 483 | 10 | | | | | | 9405 |
| HPV16 | E1 | KSNSQAKIVK | 394 | 10 | | | | | | 9406 |
| HPV16 | E1 | LLLVRYKCGK | 276 | 10 | | | | | | 9407 |
| HPV16 | E1 | LLVRYKCGK | 277 | 9 | 0.0043 | 0.0033 | | | | 9408 |
| HPV16 | E1 | LLVRYKCGKNR | 277 | 11 | | | | | | 9409 |
| HPV16 | E1 | LLYGAANTGK | 474 | 10 | | | | | | 9410 |
| HPV16 | E1 | LSLHEDEDK | 620 | 9 | 0.0005 | 0.0002 | | | | 9411 |
| HPV16 | E1 | LTNILNVLK | 191 | 9 | 0.0086 | 0.4200 | | | | 9412 |
| HPV16 | E1 | LTPSIADSIK | 243 | 10 | | | | | | 9413 |
| HPV16 | E1 | LVRPFKSNK | 222 | 9 | 0.0700 | 1.8000 | | | | 9414 |
| HPV16 | E1 | LVRYKCGK | 278 | 8 | | | | | | 9415 |
| HPV16 | E1 | LVRYKCGKNR | 278 | 10 | | | | | | 9416 |
| HPV16 | E1 | LVSMDVKHR | 544 | 9 | 0.0005 | 0.0089 | | | | 9417 |
| HPV16 | E1 | MIEPPKLR | 306 | 8 | | | | | | 9418 |
| HPV16 | E1 | MMIEPPKLR | 305 | 9 | 0.0010 | 0.0086 | | | | 9419 |
| HPV16 | E1 | MSFLTALK | 454 | 8 | | | | | | 9420 |
| HPV16 | E1 | MSFLTALKR | 454 | 9 | 0.0870 | 0.0980 | | | | 9421 |
| HPV16 | E1 | MSMSQWIK | 420 | 8 | | | | | | 9422 |
| HPV16 | E1 | MSMSQWIKYR | 420 | 10 | | | | | | 9423 |
| HPV16 | E1 | MSQWIKYR | 422 | 8 | | | | | | 9424 |
| HPV16 | E1 | MSQWIKYRCDR | 422 | 11 | | | | | | 9425 |
| HPV16 | E1 | MVVLLLVR | 273 | 8 | | | | | | 9426 |
| HPV16 | E1 | MVVLLLVRYK | 273 | 10 | | | | | | 9427 |
| HPV16 | E1 | NAKAAMLAK | 202 | 9 | 0.0005 | 0.0031 | | | | 9428 |
| HPV16 | E1 | NAKAAMLAKFK | 202 | 11 | | | | | | 9429 |
| HPV16 | E1 | NINAGTDSR | 567 | 9 | 0.0005 | 0.0002 | | | | 9430 |
| HPV16 | E1 | NLVSMDVK | 543 | 8 | | | | | | 9431 |
| HPV16 | E1 | NLVSMDVKHR | 543 | 10 | | | | | | 9432 |
| HPV16 | E1 | NSNASAFLK | 386 | 9 | 0.0005 | 0.0110 | | | | 9433 |
| HPV16 | E1 | NSQAKIVK | 396 | 8 | | | | | | 9434 |
| HPV16 | E1 | NVLKTSNAK | 196 | 9 | 0.0005 | 0.0015 | | | | 9435 |
| HPV16 | E1 | PLTNILNVLK | 190 | 10 | | | | | | 9436 |
| HPV16 | E1 | PMCMMIEPPK | 302 | 10 | | | | | | 9437 |
| HPV16 | E1 | PSIADSIK | 245 | 8 | | | | | | 9438 |
| HPV16 | E1 | PVYELNDK | 600 | 8 | | | | | | 9439 |
| HPV16 | E1 | PVYELNDKNWK | 600 | 11 | | | | | | 9440 |
| HPV16 | E1 | QMLQVEGR | 143 | 8 | | | | | | 9441 |
| HPV16 | E1 | QMSMSQWIK | 419 | 9 | 0.0023 | 0.0260 | | | | 9442 |
| HPV16 | E1 | QMSMSQWIKYR | 419 | 11 | | | | | | 9443 |
| HPV16 | E1 | QSRAAKRR | 118 | 8 | | | | | | 9444 |
| HPV16 | E1 | RLKAICIEK | 109 | 9 | 0.0840 | 0.0510 | | | | 9445 |
| HPV16 | E1 | RLSLHEDEDK | 619 | 10 | | | | | | 9446 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV16 | E1 | RSTAAALYWYK | 313 | 11 | | | | | | 9447 |
| HPV16 | E1 | RVDDGGDWK | 432 | 9 | | | | | | 9448 |
| HPV16 | E1 | SAFLKSNSQAK | 390 | 11 | | | | | | 9449 |
| HPV16 | E1 | SLFGMSLMK | 484 | 9 | 0.7200 | 7.1000 | | | | 9450 |
| HPV16 | E1 | SLHEDEDK | 621 | 8 | | | | | | 9451 |
| HPV16 | E1 | SMSQWIKYR | 421 | 9 | 0.6900 | 0.0280 | | | | 9452 |
| HPV16 | E1 | STAAALYWYK | 314 | 10 | | | | | | 9453 |
| HPV16 | E1 | SVICFVNSK | 497 | 9 | 0.0005 | 0.0002 | | | | 9454 |
| HPV16 | E1 | TAAALYWYK | 315 | 9 | 0.7800 | ##### | | | | 9455 |
| HPV16 | E1 | TAQEAKQHR | 72 | 9 | 0.0005 | 0.0025 | | | | 9456 |
| HPV16 | E1 | TIEKLLSK | 289 | 8 | | | | | | 9457 |
| HPV16 | E1 | TMCRHYKR | 407 | 8 | | | | | | 9458 |
| HPV16 | E1 | TMCRHYKRAEK | 407 | 11 | | | | | | 9459 |
| HPV16 | E1 | TSNAKAAMLAK | 200 | 11 | | | | | | 9460 |
| HPV16 | E1 | TSNINAGTDSR | 565 | 11 | | | | | | 9461 |
| HPV16 | E1 | VICFVNSK | 498 | 8 | | | | | | 9462 |
| HPV16 | E1 | VLKTSNAK | 197 | 8 | | | | | | 9463 |
| HPV16 | E1 | VLLLVRYK | 275 | 8 | | | | | | 9464 |
| HPV16 | E1 | VLLLVRYKCGK | 275 | 11 | | | | | | 9465 |
| HPV16 | E1 | VSFSELVR | 217 | 8 | | | | | | 9466 |
| HPV16 | E1 | VSFSELVRPFK | 217 | 11 | | | | | | 9467 |
| HPV16 | E1 | VSMDVKHR | 545 | 8 | | | | | | 9468 |
| HPV16 | E1 | VVLLLVRYK | 274 | 9 | 1.0000 | 0.3600 | | | | 9469 |
| HPV16 | E1 | WIKYRCDR | 425 | 8 | | | | | | 9470 |
| HPV16 | E1 | WLQPLADAK | 509 | 9 | 0.0005 | 0.0002 | | | | 9471 |
| HPV16 | E1 | YVEAVVEK | 20 | 8 | | | | | | 9472 |
| HPV16 | E1 | YVEAVVEKK | 20 | 9 | | | | | | 9473 |
| HPV16 | E2 | CAIYYKAR | 40 | 8 | | | | | | 9474 |
| HPV16 | E2 | CLRYRFKK | 300 | 8 | | | | | | 9475 |
| HPV16 | E2 | DAEKYSKNK | 174 | 9 | | | | | | 9476 |
| HPV16 | E2 | DANTLKCLR | 294 | 9 | | | | | | 9477 |
| HPV16 | E2 | DANTLKCLRYR | 294 | 11 | | | | | | 9478 |
| HPV16 | E2 | DLRDHIDYWK | 25 | 10 | | | | | | 9479 |
| HPV16 | E2 | DTGNPCHTTK | 246 | 10 | | | | | | 9480 |
| HPV16 | E2 | ETQTTIQR | 233 | 8 | | | | | | 9481 |
| HPV16 | E2 | ETQTTIQRPR | 233 | 10 | | | | | | 9482 |
| HPV16 | E2 | EVSSPEIIR | 204 | 9 | | | | | | 9483 |
| HPV16 | E2 | FLSQVKIPK | 346 | 9 | | | | | | 9484 |
| HPV16 | E2 | FVQFKDDAEK | 168 | 10 | | | | | | 9485 |
| HPV16 | E2 | GIRTYFVQFK | 163 | 10 | | | | | | 9486 |
| HPV16 | E2 | GLYYVHEGIR | 156 | 10 | | | | | | 9487 |
| RPV16 | E2 | GTEETQTTIQR | 230 | 11 | | | | | | 9488 |
| HPV16 | E2 | HIDYWKHMR | 29 | 9 | | | | | | 9489 |
| HPV16 | E2 | HLKGDANTLK | 290 | 10 | | | | | | 9490 |
| HPV16 | E2 | HMRLECAIYYK | 35 | 11 | | | | | | 9491 |
| HPV16 | E2 | HTTKLLHR | 252 | 8 | | | | | | 9492 |
| HPV16 | E2 | ILTAFNSSHK | 267 | 10 | | | | | | 9493 |
| HPV16 | E2 | KAREMGFK | 45 | 8 | | | | | | 9494 |
| HPV16 | E2 | LANHPAATHTK | 215 | 11 | | | | | | 9495 |
| HPV16 | E2 | LSQVKIPK | 347 | 8 | | | | | | 9496 |
| HPV16 | E2 | LTAFNSSHK | 268 | 9 | | | | | | 9497 |
| HPV16 | E2 | LTAFNSSHKGR | 268 | 11 | | | | | | 9498 |
| HPV16 | E2 | LTAPTGCIK | 103 | 9 | | | | | | 9499 |
| HPV16 | E2 | LTAPTGCIKK | 103 | 10 | | | | | | 9500 |
| HPV16 | E2 | LTYDSEWQR | 335 | 9 | | | | | | 9501 |
| HPV16 | E2 | NSNTTPIVHLK | 282 | 11 | | | | | | 9502 |
| HPV16 | E2 | NSQYSNEK | 84 | 8 | | | | | | 9503 |
| HPV16 | E2 | NTLKCLRYR | 296 | 9 | | | | | | 9504 |
| HPV16 | E2 | NTLKCLRYRFK | 296 | 11 | | | | | | 9505 |
| HPV16 | E2 | NTTPIVHLK | 284 | 9 | | | | | | 9506 |
| HPV16 | E2 | PILTAFNSSHK | 266 | 11 | | | | | | 9507 |
| HPV16 | E2 | PTLAVSKNK | 60 | 9 | | | | | | 9508 |
| HPV16 | E2 | QTTIQRPR | 235 | 8 | | | | | | 9509 |
| HPV16 | E2 | QVVPTLAVSK | 57 | 10 | | | | | | 9510 |
| HPV16 | E2 | RLECAIYYK | 37 | 9 | | | | | | 9511 |
| HPV16 | E2 | RLECAIYYKAR | 37 | 11 | | | | | | 9512 |
| HPV16 | E2 | RLNVCQDK | 7 | 8 | | | | | | 9513 |
| HPV16 | E2 | RTYFVQFK | 165 | 8 | | | | | | 9514 |
| HPV16 | E2 | STWHWTGHNVK | 317 | 11 | | | | | | 9515 |
| HPV16 | E2 | TAFNSSHK | 269 | 8 | | | | | | 9516 |
| HPV16 | E2 | TAFNSSHKGR | 269 | 10 | | | | | | 9517 |
| HPV16 | E2 | TAPTGCIK | 104 | 8 | | | | | | 9518 |
| HPV16 | E2 | TAPTGCIKK | 104 | 9 | | | | | | 9519 |
| HPV16 | E2 | TIYNSQYSNEK | 81 | 11 | | | | | | 9520 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV16 | E2 | TLAVSKNK | 61 | 8 | | | | | | 9521 |
| HPV16 | E2 | TLKCLRYR | 297 | 8 | | | | | | 9522 |
| HPV16 | E2 | TLKCLRYRFK | 297 | 10 | | | | | | 9523 |
| HPV16 | E2 | TLKCLRYRFKK | 297 | 11 | | | | | | 9524 |
| HPV16 | E2 | TLTYDSEWQR | 334 | 10 | | | | | | 9525 |
| HPV16 | E2 | TTPIVHLK | 285 | 8 | | | | | | 9526 |
| HPV16 | E2 | VSSPEIIR | 205 | 8 | | | | | | 9527 |
| HPV16 | E2 | VTLTYDSEWQR | 333 | 11 | | | | | | 9528 |
| HPV16 | E2 | VVPTLAVSK | 58 | 9 | | | | | | 9529 |
| HPV16 | E2 | VVPTLAVSKNK | 58 | 11 | | | | | | 9530 |
| HPV16 | E2 | WTGHNVKHK | 321 | 9 | | | | | | 9531 |
| HPV16 | E2 | YLTAPTGCIK | 102 | 10 | | | | | | 9532 |
| HPV16 | E2 | YLTAPTGCIKK | 102 | 11 | | | | | | 9533 |
| HPV16 | E5 | CVLLCVCLLIR | 20 | 11 | | | | | | 9534 |
| HPV16 | E5 | FLIHTHAR | 72 | 8 | | | | | | 9535 |
| HPV16 | E5 | ITAASAFR | 51 | 8 | | | | | | 9536 |
| HPV16 | E5 | LLCVCLLIR | 22 | 9 | | | | | | 9537 |
| HPV16 | E5 | LLWITAASAFR | 48 | 11 | | | | | | 9538 |
| HPV16 | E5 | PLFLIHTHAR | 70 | 10 | | | | | | 9539 |
| HPV16 | E5 | VLLCVCLLIR | 21 | 10 | | | | | | 9540 |
| HPV16 | E5 | WITAASAFR | 50 | 9 | | | | | | 9541 |
| HPV16 | E6 | AMFQDPQER | 7 | 9 | 0.0170 | 0.0320 | | | | 9542 |
| HPV16 | E6 | AMFQDPQERPR | 7 | 11 | | | | | | 9543 |
| HPV16 | E6 | AVCDKCLK | 68 | 8 | 0.0053 | 0.0110 | | | | 9544 |
| HPV16 | E6 | CMSCCRSSR | 143 | 9 | 0.0033 | 0.0001 | 0.0820 | 0.1200 | 0.0011 | 9545 |
| HPV16 | E6 | CMSCCRSSRTR | 143 | 11 | | | | | | 9546 |
| HPV16 | E6 | CVYCKQQLLR | 37 | 10 | 0.0001 | 0.0005 | | | | 9547 |
| HPV16 | E6 | CVYCKQQLLRR | 37 | 11 | | | | | | 9548 |
| HPV16 | E6 | DIILECVYCK | 32 | 10 | 0.0065 | 0.0210 | | | | 9549 |
| HPV16 | E6 | DLLIRCINCQK | 105 | 11 | | | | | | 9550 |
| HPV16 | E6 | EVYDFAFR | 48 | 8 | 0.0004 | 0.0025 | | | | 9551 |
| HPV16 | E6 | FAFRDLCIVYR | 52 | 11 | | | | | | 9552 |
| HPV16 | E6 | GTTLEQQYNK | 92 | 10 | 0.0002 | 0.0700 | | | | 9553 |
| HPV16 | E6 | IILECVYCK | 33 | 9 | 0.0016 | 0.0190 | | | | 9554 |
| HPV16 | E6 | ILECVYCK | 34 | 8 | | | | | | 9555 |
| HPV16 | E6 | LIRCINCQK | 107 | 9 | 0.0025 | 0.0009 | 0.0012 | 0.0041 | 0.0021 | 9556 |
| HPV16 | E6 | LLIRCINCQK | 106 | 10 | 0.0210 | 0.1800 | | | | 9557 |
| HPV16 | E6 | MSCCRSSR | 144 | 8 | | | | | | 9558 |
| HPV16 | E6 | MSCCRSSRTR | 144 | 10 | | | | | | 9559 |
| HPV16 | E6 | MSCCRSSRTRR | 144 | 11 | | | | | | 9560 |
| HPV16 | E6 | NIRGRWTGR | 134 | 9 | 0.0014 | 0.0005 | | | | 9561 |
| HPV16 | E6 | PLCDLLIR | 102 | 8 | | | | | | 9562 |
| HPV16 | E6 | PLCPEEKQR | 116 | 9 | 0.0002 | 0.0005 | | | | 9563 |
| HPV16 | E6 | RTAMFQDPQER | 5 | 11 | | | | | | 9564 |
| HPV16 | E6 | TAMFQDPQER | 6 | 10 | | | | | | 9565 |
| HPV16 | E6 | TLEQQYNK | 94 | 8 | | | | | | 9566 |
| HPV16 | E6 | TTLEQQYNK | 93 | 9 | 0.0100 | 0.2900 | | 0.0660 | 0.3000 | 9567 |
| HPV16 | E6 | WTGRCMSCCR | 139 | 10 | 0.0003 | 0.0008 | | | | 9568 |
| HPV16 | E6 | YAVCDKCLK | 67 | 9 | 0.0003 | 0.0010 | 0.0015 | 0.0024 | 0.0120 | 9569 |
| HPV16 | E6 | YSKJSEYR | 77 | 8 | | | | | | 9570 |
| HPV16 | E7 | CVQSTHVDIR | 68 | 10 | 0.0049 | 0.0001 | | | | 9571 |
| HPV16 | E7 | GIVCPICSQK | 88 | 10 | 0.0003 | 0.0670 | | | | 9572 |
| HPV16 | E7 | IVCPICSQK | 89 | 9 | 0.0077 | 0.0065 | | 0.0016 | 0.0100 | 9573 |
| HPV16 | E7 | NIVTFCCK | 53 | 8 | | | | | | 9574 |
| HPV16 | E7 | PAGQAEPDR | 41 | 9 | | | | | | 9575 |
| HPV16 | E7 | QSTHVDIR | 70 | 8 | | | | | | 9576 |
| HPV16 | L1 | AAISTSETTYK | 372 | 11 | | | | | | 9577 |
| HPV16 | L1 | AANAGVDNR | 162 | 9 | | | | | | 9578 |
| HPV16 | L1 | AISTSETTYK | 373 | 10 | | | | | | 9579 |
| HPV16 | L1 | AMDFTTLQANK | 233 | 11 | | | | | | 9580 |
| HPV16 | L1 | AVGHPYFPIK | 70 | 10 | | | | | | 9581 |
| HPV16 | L1 | AVGHPYFPIKK | 70 | 11 | | | | | | 9582 |
| HPV16 | L1 | CVGVEVGR | 128 | 8 | | | | | | 9583 |
| HPV16 | L1 | DICTSICK | 249 | 8 | | | | | | 9584 |
| HPV16 | L1 | DLDQFPLGR | 484 | 9 | | | | | | 9585 |
| HPV16 | L1 | DLDQFPLGRK | 484 | 10 | | | | | | 9586 |
| HPV16 | L1 | DLQFIFQLCK | 397 | 10 | | | | | | 9587 |
| HPV16 | L1 | DSLFFYLR | 270 | 8 | | | | | | 9588 |
| HPV16 | L1 | DSLFFYLRR | 270 | 9 | | | | | | 9589 |
| HPV16 | L1 | DTSFYNPDTQR | 113 | 11 | | | | | | 9590 |
| HPV16 | L1 | ETTYKNTNFK | 378 | 10 | | | | | | 9591 |
| HPV16 | L1 | FLLQAGLK | 494 | 8 | | | | | | 9592 |
| HPV16 | L1 | FLLQAGLKAK | 494 | 10 | | | | | | 9593 |
| HPV16 | L1 | FTTLQANK | 236 | 8 | | | | | | 9594 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV16 | L1 | FVRHLFNR | 282 | 8 | | | | | | 9595 |
| HPV16 | L1 | FVTSQAIACQK | 446 | 11 | | | | | | 9596 |
| HPV16 | L1 | FVTVVDTTR | 356 | 9 | | | | | | 9597 |
| HPV16 | L1 | GISGHPLLNK | 142 | 10 | | | | | | 9598 |
| HPV16 | L1 | GLQYRVFR | 93 | 8 | | | | | | 9599 |
| HPV16 | L1 | GTLEDTYR | 438 | 8 | | | | | | 9600 |
| HPV16 | L1 | ISGHPLLNK | 143 | 9 | | | | | | 9601 |
| HPV16 | L1 | ISTSETTYK | 374 | 9 | | | | | | 9602 |
| HPV16 | L1 | KAKPKFTLGK | 501 | 10 | | | | | | 9603 |
| HPV16 | L1 | KAKPKFTLGKR | 501 | 11 | | | | | | 9604 |
| HPV16 | L1 | KVSGLQYR | 90 | 8 | | | | | | 9605 |
| HPV16 | L1 | KVSGLQYRVFR | 90 | 11 | | | | | | 9606 |
| HPV16 | L1 | KVVSTDEYVAR | 46 | 11 | | | | | | 9607 |
| HPV16 | L1 | LAVGHPYFPIK | 69 | 11 | | | | | | 9608 |
| HPV16 | L1 | LLQAGLKAK | 495 | 9 | | | | | | 9609 |
| HPV16 | L1 | LLQAGLKAKPK | 495 | 11 | | | | | | 9610 |
| HPV16 | L1 | LVPKVSGLQYR | 87 | 11 | | | | | | 9611 |
| HPV16 | L1 | MVTSDAQIFNK | 325 | 11 | | | | | | 9612 |
| HPV16 | L1 | NIYYHAGTSR | 58 | 10 | | | | | | 9613 |
| HPV16 | L1 | NTNFKEYLR | 383 | 9 | | | | | | 9614 |
| HPV16 | L1 | NVPDDLYIK | 296 | 9 | | | | | | 9615 |
| HPV16 | L1 | PAPKEDPLK | 460 | 9 | | | | | | 9616 |
| HPV16 | L1 | PAPKEDPLKK | 460 | 10 | | | | | | 9617 |
| HPV16 | L1 | PIGEHWGK | 190 | 8 | | | | | | 9618 |
| HPV16 | L1 | PIKKPNNNK | 77 | 9 | | | | | | 9619 |
| HPV16 | L1 | PLDICTSICK | 247 | 10 | | | | | | 9620 |
| HPV16 | L1 | PTTSSTSTTAK | 515 | 11 | | | | | | 9621 |
| HPV16 | L1 | QAGLKAKPK | 497 | 9 | | | | | | 9622 |
| HPV16 | L1 | QIFNKPYWLQR | 331 | 11 | | | | | | 9623 |
| HPV16 | L1 | QLCLIGCK | 181 | 8 | | | | | | 9624 |
| HPV16 | L1 | QLFVTVVDTTR | 354 | 11 | | | | | | 9625 |
| HPV16 | L1 | QMFVRHLFNR | 280 | 10 | | | | | | 9626 |
| HPV16 | L1 | QTQLCLIGCK | 179 | 10 | | | | | | 9627 |
| HPV16 | L1 | RIHLPDPNK | 100 | 9 | | | | | | 9628 |
| HPV16 | L1 | SADLDQFPLGR | 482 | 11 | | | | | | 9629 |
| HPV16 | L1 | SICKYPDYIK | 253 | 10 | | | | | | 9630 |
| HPV16 | L1 | SLFFYLRR | 271 | 8 | | | | | | 9631 |
| HPV16 | L1 | SSTSTTAK | 518 | 8 | | | | | | 9632 |
| HPV16 | L1 | SSTSTTAKR | 518 | 9 | | | | | | 9633 |
| HPV16 | L1 | SSTSTTAKRK | 518 | 10 | | | | | | 9634 |
| HPV16 | L1 | SSTSTTAKRKK | 518 | 11 | | | | | | 9635 |
| HPV16 | L1 | STDEYVAR | 49 | 8 | | | | | | 9636 |
| HPV16 | L1 | STSETTYK | 375 | 8 | | | | | | 9637 |
| HPV16 | L1 | STSTTAKR | 519 | 8 | | | | | | 9638 |
| HPV16 | L1 | STSTTAKRK | 519 | 9 | | | | | | 9639 |
| HPV16 | L1 | STSTTAKRKK | 519 | 10 | | | | | | 9640 |
| HPV16 | L1 | STSTTAKRKKR | 519 | 11 | | | | | | 9641 |
| HPV16 | L1 | STTAKRKK | 521 | 8 | | | | | | 9642 |
| HPV16 | L1 | STTAKRKKR | 521 | 9 | | | | | | 9643 |
| HPV16 | L1 | STTAKRKKRK | 521 | 10 | | | | | | 9644 |
| HPV16 | L1 | TAKRKKRK | 523 | 8 | | | | | | 9645 |
| HPV16 | L1 | TSDAQIFNK | 327 | 9 | | | | | | 9646 |
| HPV16 | L1 | TSFYNPDTQR | 114 | 10 | | | | | | 9647 |
| HPV16 | L1 | TSICKYPDYIK | 252 | 11 | | | | | | 9648 |
| HPV16 | L1 | TSQAIACQK | 448 | 9 | | | | | | 9649 |
| HPV16 | L1 | TSSTSTTAK | 517 | 9 | | | | | | 9650 |
| HPV16 | L1 | TSSTSTTAKR | 517 | 10 | | | | | | 9651 |
| HPV16 | L1 | TSSTSTTAKRK | 517 | 11 | | | | | | 9652 |
| HPV16 | L1 | TSTTAKRK | 520 | 8 | | | | | | 9653 |
| HPV16 | L1 | TSTTAKRKK | 520 | 9 | | | | | | 9654 |
| HPV16 | L1 | TSTTAKRKKR | 520 | 10 | | | | | | 9655 |
| HPV16 | L1 | TSTTAKRKKRK | 520 | 11 | | | | | | 9656 |
| HPV16 | L1 | TTAKRKKR | 522 | 8 | | | | | | 9657 |
| HPV16 | L1 | TTAKRKKRK | 522 | 9 | | | | | | 9658 |
| HPV16 | L1 | TTSSTSTTAK | 516 | 10 | | | | | | 9659 |
| HPV16 | L1 | TTSSTSTTAKR | 516 | 11 | | | | | | 9660 |
| HPV16 | L1 | TTYKNTNFK | 379 | 9 | | | | | | 9661 |
| HPV16 | L1 | TVYLPPVPVSK | 36 | 11 | | | | | | 9662 |
| HPV16 | L1 | VSGLQYRVFR | 91 | 10 | | | | | | 9663 |
| HPV16 | L1 | VSTDEYVAR | 48 | 9 | | | | | | 9664 |
| HPV16 | L1 | VTSDAQIFNK | 326 | 10 | | | | | | 9665 |
| HPV16 | L1 | VTSQAIACQK | 447 | 10 | | | | | | 9666 |
| HPV16 | L1 | VTVVDTTR | 357 | 8 | | | | | | 9667 |
| HPV16 | L1 | VVSTDEYVAR | 47 | 10 | | | | | | 9668 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV16 | L1 | WACVGVEVGR | 126 | 10 | | | | | | 9669 |
| HPV16 | L1 | YAANAGVDNR | 161 | 10 | | | | | | 9670 |
| HPV16 | L1 | YLPPVPVSK | 38 | 9 | | | | | | 9671 |
| HPV16 | L1 | YLRREQMFVR | 275 | 10 | | | | | | 9672 |
| HPV16 | L1 | YTFWEVNLK | 470 | 9 | | | | | | 9673 |
| HPV16 | L1 | YTFWEVNLKEK | 470 | 11 | | | | | | 9674 |
| HPV16 | L2 | ALHRPALTSR | 288 | 10 | | | | | | 9675 |
| HPV16 | L2 | ALHRPALTSRR | 288 | 11 | | | | | | 9676 |
| HPV16 | L2 | ALTSRRTGIR | 293 | 10 | | | | | | 9677 |
| HPV16 | L2 | ASATQLYK | 13 | 8 | | | | | | 9678 |
| HPV16 | L2 | ASATQLYKTCK | 13 | 11 | | | | | | 9679 |
| HPV16 | L2 | ATDTLAPVR | 82 | 9 | | | | | | 9680 |
| HPV16 | L2 | ATQLYKTCK | 15 | 9 | | | | | | 9681 |
| HPV16 | L2 | DIIPKVEGK | 31 | 9 | | | | | | 9682 |
| HPV16 | L2 | FLDIVALHR | 283 | 9 | | | | | | 9683 |
| HPV16 | L2 | GIGTGSGTGGR | 59 | 11 | | | | | | 9684 |
| HPV16 | L2 | GIRYSRIGNK | 300 | 10 | | | | | | 9685 |
| HPV16 | L2 | GLYSRTTQQVK | 226 | 11 | | | | | | 9686 |
| HPV16 | L2 | GTCPPDIIPK | 26 | 10 | | | | | | 9687 |
| HPV16 | L2 | GTGSGTGGR | 61 | 9 | | | | | | 9688 |
| HPV16 | L2 | IIPKVEGK | 32 | 8 | | | | | | 9689 |
| HPV16 | L2 | LTSRRTGIR | 294 | 9 | | | | | | 9690 |
| HPV16 | L2 | MLRKRRKR | 454 | 8 | | | | | | 9691 |
| HPV16 | L2 | PAFITTPTK | 240 | 9 | | | | | | 9692 |
| HPV16 | L2 | PALTSRRTGIR | 292 | 11 | | | | | | 9693 |
| HPV16 | L2 | PIPGSRPVAR | 215 | 10 | | | | | | 9694 |
| HPV16 | L2 | PSYYMLRK | 450 | 8 | | | | | | 9695 |
| HPV16 | L2 | PSYYMLRKR | 450 | 9 | | | | | | 9696 |
| HPV16 | L2 | PSYYMLRKRR | 450 | 10 | | | | | | 9697 |
| HPV16 | L2 | PSYYMLRKRRK | 450 | 11 | | | | | | 9698 |
| HPV16 | L2 | PTATDTLAPVR | 80 | 11 | | | | | | 9699 |
| HPV16 | L2 | PVARLGLYSR | 221 | 10 | | | | | | 9700 |
| HPV16 | L2 | QTLRTRSGK | 310 | 9 | | | | | | 9701 |
| HPV16 | L2 | RASATQLYK | 12 | 9 | | | | | | 9702 |
| HPV16 | L2 | RIGNKQTLR | 305 | 9 | | | | | | 9703 |
| HPV16 | L2 | RIGNKQTLRTR | 305 | 11 | | | | | | 9704 |
| HPV16 | L2 | RSAKRTKR | 5 | 8 | | | | | | 9705 |
| HPV16 | L2 | RSGKSIGAK | 315 | 9 | | | | | | 9706 |
| HPV16 | L2 | RTGIRYSR | 298 | 8 | | | | | | 9707 |
| HPV16 | L2 | RTGYIPLGTR | 69 | 10 | | | | | | 9708 |
| HPV16 | L2 | RTRSGKSIGAK | 313 | 11 | | | | | | 9709 |
| HPV16 | L2 | SATQLYKTCK | 14 | 10 | | | | | | 9710 |
| HPV16 | L2 | SSTPIPGSR | 212 | 9 | | | | | | 9711 |
| HPV16 | L2 | STPIPGSR | 213 | 8 | | | | | | 9712 |
| HPV16 | L2 | TATDTLAPVR | 81 | 10 | | | | | | 9713 |
| HPV16 | L2 | TLRTRSGK | 311 | 8 | | | | | | 9714 |
| HPV16 | L2 | TSRRTGIR | 295 | 8 | | | | | | 9715 |
| HPV16 | L2 | TSRRTGIRYSR | 295 | 11 | | | | | | 9716 |
| HPV16 | L2 | TSSTPIPGSR | 211 | 10 | | | | | | 9717 |
| HPV16 | L2 | VALHRPALTSR | 287 | 11 | | | | | | 9718 |
| HPV16 | L2 | VARLGLYSR | 222 | 9 | | | | | | 9719 |
| HPV16 | L2 | VTSSTPIPGSR | 210 | 11 | | | | | | 9720 |
| HPV16 | L2 | YLHPSYYMLR | 447 | 10 | | | | | | 9721 |
| HPV16 | L2 | YLHPSYYMLRK | 447 | 11 | | | | | | 9722 |
| HPV16 | L2 | YMLRKRRK | 453 | 8 | | | | | | 9723 |
| HPV16 | L2 | YMLRKRRKR | 453 | 9 | | | | | | 9724 |
| HPV16 | L2 | YSRIGNKQTLR | 303 | 11 | | | | | | 9725 |
| HPV16 | L2 | YSRTTQQVK | 228 | 9 | | | | | | 9726 |
| HPV18 | E1 | AAFLKSNCQAK | 397 | 11 | | | | | | 9727 |
| HPV18 | E1 | ALDGNPISIDR | 546 | 11 | | | | | | 9728 |
| HPV18 | E1 | ALKSFLKGTPK | 466 | 11 | | | | | | 9729 |
| HPV18 | E1 | ALLRYKCGK | 284 | 9 | 0.0900 | 0.1400 | | | | 9730 |
| HPV18 | E1 | ALLRYKCGKSR | 284 | 11 | | | | | | 9731 |
| HPV18 | E1 | ATMCKHYR | 413 | 8 | | | | | | 9732 |
| HPV18 | E1 | ATMCKHYRR | 413 | 9 | 0.0300 | 0.2800 | | | | 9733 |
| HPV18 | E1 | CATMCKHYR | 412 | 9 | 0.0012 | 0.0110 | | | | 9734 |
| HPV18 | E1 | CATMCKHYRR | 412 | 10 | | | | | | 9735 |
| HPV18 | E1 | CMLIQPPK | 311 | 8 | | | | | | 9736 |
| HPV18 | E1 | CMLIQPPKLR | 311 | 10 | | | | | | 9737 |
| HPV18 | E1 | CSKIDEGGDWR | 437 | 11 | | | | | | 9738 |
| HPV18 | E1 | CTIAQLKDLLK | 196 | 11 | | | | | | 9739 |
| HPV18 | E1 | DAQVLHVLK | 78 | 9 | | | | | | 9740 |
| HPV18 | E1 | DAQVLHVLKR | 78 | 10 | | | | | | 9741 |
| HPV18 | E1 | DAQVLHVLKRK | 78 | 11 | | | | | | 9742 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV18 | E1 | DLLKVNNK | 203 | 8 | | | | | | 9743 |
| HPV18 | E1 | DLVRNFKSDK | 228 | 10 | | | | | | 9744 |
| HPV18 | E1 | DSNSNAAAFLK | 391 | 11 | | | | | | 9745 |
| HPV18 | E1 | DTEGNPFGTFK | 637 | 11 | | | | | | 9746 |
| HPV18 | E1 | DTPEWIQR | 342 | 8 | | | | | | 9747 |
| HPV18 | E1 | EINDKNWK | 610 | 8 | | | | | | 9748 |
| HPV18 | E1 | EISLNSGQK | 115 | 9 | | | | | | 9749 |
| HPV18 | E1 | EISLNSGQKK | 115 | 10 | | | | | | 9750 |
| HPV18 | E1 | ETCMLIQPPK | 309 | 10 | | | | | | 9751 |
| HPV18 | E1 | EVDTELSPR | 104 | 9 | | | | | | 9752 |
| HPV18 | E1 | FITFLGALK | 460 | 9 | 0.0320 | 0.0370 | | | | 9753 |
| HPV18 | E1 | FLGALKSFLK | 463 | 10 | | | | | | 9754 |
| HPV18 | E1 | FLKGTPKK | 470 | 8 | | | | | | 9755 |
| HPV18 | E1 | FLKSNCQAK | 399 | 9 | 0.0035 | 0.0007 | | | | 9756 |
| HPV18 | E1 | FTDLVRNFK | 226 | 9 | | | | | | 9757 |
| HPV18 | E1 | GALKSFLK | 465 | 8 | | | | | | 9758 |
| HPV18 | E1 | GAMLAVFK | 212 | 8 | | | | | | 9759 |
| HPV18 | E1 | GLSFTDLVR | 223 | 9 | 0.0009 | 0.0025 | | | | 9760 |
| HPV18 | E1 | GSTENSPLGER | 92 | 11 | | | | | | 9761 |
| HPV18 | E1 | GVLILALLR | 279 | 9 | 0.0058 | 0.1400 | | | | 9762 |
| HPV18 | E1 | GVLILALLRYK | 279 | 11 | | | | | | 9763 |
| HPV18 | E1 | GVNPTIAEGFK | 249 | 11 | | | | | | 9764 |
| HPV18 | E1 | HIQCLDCK | 270 | 8 | | | | | | 9765 |
| HPV18 | E1 | IAQLKDLLK | 198 | 9 | 0.0003 | 0.0027 | | | | 9766 |
| HPV18 | E1 | ILALLRYK | 282 | 8 | | | | | | 9767 |
| HPV18 | E1 | ILALLRYKCGK | 282 | 11 | | | | | | 9768 |
| HPV18 | E1 | ILLTTNIHPAK | 569 | 11 | | | | | | 9769 |
| HPV18 | E1 | ISIDRKHK | 552 | 8 | | | | | | 9770 |
| HPV18 | E1 | ISLNSGQK | 116 | 8 | | | | | | 9771 |
| HPV18 | E1 | ISLNSGQKK | 116 | 9 | 0.0003 | 0.0026 | | | | 9772 |
| HPV18 | E1 | ISLNSGQKKAK | 116 | 11 | | | | | | 9773 |
| HPV18 | E1 | ITFLGALK | 461 | 8 | | | | | | 9774 |
| HPV18 | E1 | KIDEGGDWR | 439 | 9 | | | | | | 9775 |
| HPV18 | E1 | KLRAGQNHR | 647 | 9 | 0.3000 | 0.0013 | | | | 9776 |
| HPV18 | E1 | KSFLKGTPK | 468 | 9 | 0.0003 | 0.0015 | | | | 9777 |
| HPV18 | E1 | KSFLKGTPKK | 468 | 10 | | | | | | 9778 |
| HPV18 | E1 | KSNCQAKYLK | 401 | 10 | | | | | | 9779 |
| HPV18 | E1 | KSRLTVAK | 292 | 8 | | | | | | 9780 |
| HPV18 | E1 | LALLRYKCGK | 283 | 10 | | | | | | 9781 |
| HPV18 | E1 | LILALLRYK | 281 | 9 | 0.2700 | 0.1800 | | | | 9782 |
| HPV18 | E1 | LIQPPKLR | 313 | 8 | | | | | | 9783 |
| HPV18 | E1 | LLRYKCGK | 285 | 8 | | | | | | 9784 |
| HPV18 | E1 | LLRYKCGKSR | 285 | 10 | | | | | | 9785 |
| HPV18 | E1 | LLTTNIHPAK | 570 | 10 | | | | | | 9786 |
| HPV18 | E1 | LSFTDLVR | 224 | 8 | | | | | | 9787 |
| HPV18 | E1 | LSFTDLVRNFK | 224 | 11 | | | | | | 9788 |
| HPV18 | E1 | LTTNIHPAK | 571 | 9 | 0.0910 | 0.1200 | | | | 9789 |
| HPV18 | E1 | LVFCGPANTGK | 480 | 11 | | | | | | 9790 |
| HPV18 | E1 | LVRNFKSDK | 229 | 9 | 0.0005 | 0.0002 | | | | 9791 |
| HPV18 | E1 | MLIQPPKLR | 312 | 9 | 0.0005 | 0.0014 | | | | 9792 |
| HPV18 | E1 | MSQWIRFR | 429 | 8 | | | | | | 9793 |
| HPV18 | E1 | MSQWIRFRCSK | 429 | 11 | | | | | | 9794 |
| HPV18 | E1 | NIHPAKDNR | 574 | 9 | 0.0005 | 0.0002 | | | | 9795 |
| HPV18 | E1 | NMSQWIRFR | 428 | 9 | 0.0540 | 0.0012 | | | | 9796 |
| HPV18 | E1 | NSGQKKAK | 119 | 8 | | | | | | 9797 |
| HPV18 | E1 | NSGQKKAKR | 119 | 9 | 0.0005 | 0.0002 | | | | 9798 |
| HPV18 | E1 | NSGQKKAKRR | 119 | 10 | | | | | | 9799 |
| HPV18 | E1 | NSNAAAFLK | 393 | 9 | 0.0057 | 0.3700 | | | | 9800 |
| HPV18 | E1 | PISIDRKHK | 551 | 9 | | | | | | 9801 |
| HPV18 | E1 | PTIAEGFK | 252 | 8 | | | | | | 9802 |
| HPV18 | E1 | PVYEINDK | 607 | 8 | | | | | | 9803 |
| HPV18 | E1 | PVYEINDKNWK | 607 | 11 | | | | | | 9804 |
| HPV18 | E1 | QLKDLLKVNNK | 200 | 11 | | | | | | 9805 |
| HPV18 | E1 | QMNMSQWIR | 426 | 9 | 0.0011 | 0.0023 | | | | 9806 |
| HPV18 | E1 | QMNMSQWIRFR | 426 | 11 | | | | | | 9807 |
| HPV18 | E1 | QVLHVLKR | 80 | 8 | | | | | | 9808 |
| HPV18 | E1 | QVLHVLKRK | 80 | 9 | 0.0028 | 0.0020 | | | | 9809 |
| HPV18 | E1 | RLEVDTELSPR | 102 | 11 | | | | | | 9810 |
| HPV18 | E1 | RSSVAALYWYR | 320 | 11 | | | | | | 9811 |
| HPV18 | E1 | SLNSGQKK | 117 | 8 | | | | | | 9812 |
| HPV18 | E1 | SLNSGQKKAK | 117 | 10 | | | | | | 9813 |
| HPV18 | E1 | SLNSGQKKAKR | 117 | 11 | | | | | | 9814 |
| HPV18 | E1 | SSVAALYWYR | 321 | 10 | | | | | | 9815 |
| HPV18 | E1 | STENSPLGER | 93 | 10 | | | | | | 9816 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV18 | E1 | SVAALYWYR | 322 | 9 | 2.9000 | 8.8000 | | | | 9817 |
| HPV18 | E1 | TIAQLKDLLK | 197 | 10 | | | | | | 9818 |
| HPV18 | E1 | TMCKHYRR | 414 | 8 | | | | | | 9819 |
| HPV18 | E1 | TMCKHYRRAQK | 414 | 11 | | | | | | 9820 |
| HPV18 | E1 | TTNIHPAK | 572 | 8 | | | | | | 9821 |
| HPV18 | E1 | TTNIHPAKDNR | 572 | 11 | | | | | | 9822 |
| HPV18 | E1 | VAALYWYR | 323 | 8 | | | | | | 9823 |
| HPV18 | E1 | VLHVLKRK | 81 | 8 | | | | | | 9824 |
| HPV18 | E1 | VLILALLR | 280 | 8 | | | | | | 9825 |
| HPV18 | E1 | VLILALLRYK | 280 | 10 | | | | | | 9826 |
| HPV18 | E1 | VMGDTPEWIQR | 339 | 11 | | | | | | 9827 |
| HPV18 | E1 | WIRFRCSK | 432 | 8 | | | | | | 9828 |
| HPV18 | E1 | WLEPLTDTK | 516 | 9 | | | | | | 9829 |
| HPV18 | E1 | WTYFDTYMR | 536 | 9 | 0.0005 | 0.0120 | | | | 9830 |
| HPV18 | E1 | YAHIQCLDCK | 268 | 10 | | | | | | 9831 |
| HPV18 | E1 | YLKDCATMCK | 408 | 10 | | | | | | 9832 |
| HPV18 | E1 | YVQAIVDK | 19 | 8 | | | | | | 9833 |
| HPV18 | E1 | YVQAIVDKK | 19 | 9 | 0.0005 | 0.0290 | | | | 9834 |
| HPV18 | E2 | AATPTGNNK | 269 | 9 | | | | | | 9835 |
| HPV18 | E2 | AATPTGNNKR | 269 | 10 | | | | | | 9836 |
| HPV18 | E2 | AATPTGNNKRR | 269 | 11 | | | | | | 9837 |
| HPV18 | E2 | ALQGLAQSR | 82 | 9 | | | | | | 9838 |
| HPV18 | E2 | ALQGLAQSRYK | 82 | 11 | | | | | | 9839 |
| HPV18 | E2 | ATPTGNNK | 270 | 8 | | | | | | 9840 |
| HPV18 | E2 | ATPTGNNKR | 270 | 9 | | | | | | 9841 |
| HPV18 | E2 | ATPTGNNKRR | 270 | 10 | | | | | | 9842 |
| HPV18 | E2 | ATPTGNNKRRK | 270 | 11 | | | | | | 9843 |
| HPV18 | E2 | CLRYRLRK | 301 | 8 | | | | | | 9844 |
| HPV18 | E2 | CVSHRGLYYVK | 156 | 11 | | | | | | 9845 |
| HPV18 | E2 | DSQIQYWQLIR | 31 | 11 | | | | | | 9846 |
| HPV18 | E2 | DTVSATQLVK | 210 | 10 | | | | | | 9847 |
| HPV18 | E2 | GAATPTGNNK | 268 | 10 | | | | | | 9848 |
| HPV18 | E2 | GAATPTGNNKR | 268 | 11 | | | | | | 9849 |
| HPV18 | E2 | GLAQSRYK | 85 | 8 | | | | | | 9850 |
| HPV18 | E2 | HLKGDRNSLK | 291 | 10 | | | | | | 9851 |
| HPV18 | E2 | HSETQRTK | 338 | 8 | | | | | | 9852 |
| HPV18 | E2 | IIDHYENDSK | 19 | 10 | | | | | | 9853 |
| HPV18 | E2 | IIHLKGDR | 289 | 8 | | | | | | 9854 |
| HPV18 | E2 | ISKSKAHK | 68 | 8 | | | | | | 9855 |
| HPV18 | E2 | KIIDHYENDSK | 18 | 11 | | | | | | 9856 |
| HPV18 | E2 | KTATCVSHR | 152 | 9 | | | | | | 9857 |
| HPV18 | E2 | KTYGQTSAATR | 238 | 11 | | | | | | 9858 |
| HPV18 | E2 | LSERLSCVQDK | 8 | 11 | | | | | | 9859 |
| HPV18 | E2 | LTVTYHSETQR | 333 | 11 | | | | | | 9860 |
| HPV18 | E2 | MALQGLAQSR | 81 | 10 | | | | | | 9861 |
| HPV18 | E2 | MTDAGTWDK | 144 | 9 | | | | | | 9862 |
| HPV18 | E2 | NAIFFAAR | 44 | 8 | | | | | | 9863 |
| HPV18 | E2 | NISKSKAHK | 67 | 9 | | | | | | 9864 |
| HPV18 | E2 | NSLKCLRYR | 297 | 9 | | | | | | 9865 |
| HPV18 | E2 | NSLKCLRYRLR | 297 | 11 | | | | | | 9866 |
| HPV18 | E2 | NTEPTHCFK | 107 | 9 | | | | | | 9867 |
| HPV18 | E2 | NTEPTHCFKK | 107 | 10 | | | | | | 9868 |
| HPV18 | E2 | NTFYIEFK | 170 | 8 | | | | | | 9869 |
| HPV18 | E2 | NTTPIIHLK | 285 | 9 | | | | | | 9870 |
| HPV18 | E2 | PAYNISKSK | 64 | 9 | | | | | | 9871 |
| HPV18 | E2 | PIIHLKGDR | 288 | 9 | | | | | | 9872 |
| HPV18 | E2 | PTGNNKRR | 272 | 8 | | | | | | 9873 |
| HPV18 | E2 | PTGNNKRRK | 272 | 9 | | | | | | 9874 |
| HPV18 | E2 | QIQYWQLIR | 33 | 9 | | | | | | 9875 |
| HPV18 | E2 | QMALQGLAQSR | 80 | 11 | | | | | | 9876 |
| HPV18 | E2 | QTPKETLSER | 2 | 10 | | | | | | 9877 |
| HPV18 | E2 | QTVQVYFDGNK | 119 | 11 | | | | | | 9878 |
| HPV18 | E2 | QVVPAYNISK | 61 | 10 | | | | | | 9879 |
| HPV18 | E2 | QVYFDGNK | 122 | 8 | | | | | | 9880 |
| HPV18 | E2 | RLRKHSDHYR | 305 | 10 | | | | | | 9881 |
| HPV18 | E2 | RLSCVQDK | 11 | 8 | | | | | | 9882 |
| HPV18 | E2 | SLKCLRYR | 298 | 8 | | | | | | 9883 |
| HPV18 | E2 | SLKCLRYRLR | 298 | 10 | | | | | | 9884 |
| HPV18 | E2 | SLKCLRYRLRK | 298 | 11 | | | | | | 9885 |
| HPV18 | E2 | SSTVSVGTAK | 229 | 10 | | | | | | 9886 |
| HPV18 | E2 | STVSVGTAK | 230 | 9 | | | | | | 9887 |
| HPV18 | E2 | TATCVSHR | 153 | 8 | | | | | | 9888 |
| HPV18 | E2 | TTPIIHLK | 286 | 8 | | | | | | 9889 |
| HPV18 | E2 | TTPIIHLKGDR | 286 | 11 | | | | | | 9890 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV18 | E2 | TVQVYFDGNK | 120 | 10 | | | | | | 9891 |
| HPV18 | E2 | TVSATQLVK | 211 | 9 | | | | | | 9892 |
| HPV18 | E2 | TVSVGTAK | 231 | 8 | | | | | | 9893 |
| HPV18 | E2 | TVTYHSETQR | 334 | 10 | | | | | | 9894 |
| HPV18 | E2 | VSATQLVK | 212 | 8 | | | | | | 9895 |
| HPV18 | E2 | VSHRGLYYVK | 157 | 10 | | | | | | 9896 |
| HPV18 | E2 | VTYHSETQR | 335 | 9 | | | | | | 9897 |
| HPV18 | E2 | VTYHSETQRTK | 335 | 11 | | | | | | 9898 |
| HPV18 | E2 | VVPAYNISK | 62 | 9 | | | | | | 9899 |
| HPV18 | E2 | VVPAYNISKSK | 62 | 11 | | | | | | 9900 |
| HPV18 | E2 | WTGAGNEK | 322 | 8 | | | | | | 9901 |
| HPV18 | E2 | YIEFKSECEK | 173 | 10 | | | | | | 9902 |
| HPV18 | E2 | YMTDAGTWDK | 143 | 10 | | | | | | 9903 |
| HPV18 | E2 | YSSTVSVGTAK | 228 | 11 | | | | | | 9904 |
| HPV18 | E6 | CIDFYSRIR | 68 | 9 | 0.0001 | 0.0001 | | | | 9905 |
| HPV18 | E6 | DIEIITCVYCK | 27 | 10 | 0.0089 | 0.0021 | | | | 9906 |
| HPV18 | E6 | DSIPHAACHK | 58 | 10 | | | | | | 9907 |
| HPV18 | E6 | SDVYGDTLEK | 83 | 10 | 0.0005 | 0.0051 | | | | 9908 |
| HPV18 | E6 | EITCVYCK | 29 | 8 | | | | | | 9909 |
| HPV18 | E6 | ELTEVFEFAFK | 40 | 11 | | | | | | 9910 |
| HPV18 | E6 | EVFEFAFK | 43 | 8 | 0.0025 | 0.0180 | | | | 9911 |
| HPV18 | E6 | FAFKDLFVVYR | 47 | 11 | | | | | | 9912 |
| HPV18 | E6 | GLYNLLIR | 97 | 8 | | | | | | 9913 |
| HPV18 | E6 | GLYNLLIRCLR | 97 | 11 | | | | | | 9914 |
| HPV18 | E6 | HSCCNRAR | 139 | 8 | | | | | | 9915 |
| HPV18 | E6 | HSCCNRARQER | 139 | 11 | | | | | | 9916 |
| HPV18 | E6 | KLRHLNEK | 117 | 8 | | | | | | 9917 |
| HPV18 | E6 | KLRHLNEKR | 117 | 9 | 0.0250 | 0.0005 | | | | 9918 |
| HPV18 | E6 | KLRHLNEKRR | 117 | 10 | 0.0130 | 0.0001 | | | | 9919 |
| HPV18 | E6 | LIRCLRCQK | 102 | 9 | 0.0190 | 0.0012 | | | | 9920 |
| HPV18 | E6 | LLIRCLRCQK | 101 | 10 | 0.0470 | 0.1200 | | | | 9921 |
| HPV18 | E6 | LTEVFEFAFK | 41 | 10 | 0.0001 | 0.0360 | | | | 9922 |
| HPV18 | E6 | MARFEDPTR | 1 | 9 | | | | | | 9923 |
| HPV18 | E6 | MARFEDPTRR | 1 | 10 | | | | | | 9924 |
| HPV18 | E6 | NLLIRCLR | 100 | 8 | | | | | | 9925 |
| HPV18 | E6 | NLLIRCLRCQK | 100 | 11 | | | | | | 9926 |
| HPV18 | E6 | NTGLYNLLIR | 95 | 10 | 0.0002 | 0.0013 | | | | 9927 |
| HPV18 | E6 | PAEKLRHLNEK | 114 | 11 | | | | | | 9928 |
| HPV18 | E6 | PLNPAEKLR | 111 | 9 | 0.0002 | 0.0005 | | | | 9929 |
| HPV18 | E6 | RARQERLQR | 144 | 9 | 0.0007 | 0.0002 | | | | 9930 |
| HPV18 | E6 | RARQERLQRR | 144 | 10 | | | | | | 9931 |
| HPV18 | E6 | RARQERLQRRR | 144 | 11 | | | | | | 9932 |
| HPV18 | E6 | SIPHAACHK | 59 | 9 | 0.0170 | 0.1200 | | | | 9933 |
| HPV18 | E6 | SVYGDTLEK | 84 | 9 | 0.0800 | 0.2300 | | | | 9934 |
| HPV18 | E6 | YSRIRELR | 72 | 8 | | | | | | 9935 |
| HPV18 | E7 | CMCCKCEAR | 63 | 9 | | | | | | 9936 |
| HPV18 | E7 | CMCCKCEARIK | 63 | 11 | 0.0014 | 0.0002 | | | | 9937 |
| HPV18 | E7 | ESSADDLR | 77 | 8 | | | | | | 9938 |
| HPV18 | E7 | GVNHQHLPAR | 43 | 10 | | | | | | 9939 |
| HPV18 | E7 | GVNHQHLPARR | 43 | 11 | | | | | | 9940 |
| HPV18 | E7 | HLPARRAEPQR | 48 | 11 | | | | | | 9941 |
| HPV18 | E7 | HTMLCMCCK | 59 | 9 | 0.0640 | 0.0940 | | | | 9942 |
| HPV18 | E7 | LVVESSADDLR | 74 | 11 | | | | | | 9943 |
| HPV18 | E7 | MLCMCCKCEAR | 61 | 11 | | | | | | 9944 |
| HPV18 | E7 | PARRAEPQR | 50 | 9 | | | | | | 9945 |
| HPV18 | E7 | TMLCMCCK | 60 | 8 | 0.0240 | 0.0240 | | | | 9946 |
| HPV18 | E7 | VVESSADDLR | 75 | 10 | | | | | | 9947 |
| HPV18 | L1 | AATSNVSEDVR | 195 | 11 | | | | | | 9948 |
| HPV18 | L1 | AIGEHWAK | 225 | 8 | | | | | | 9949 |
| HPV18 | L1 | AMDFSTLQDTK | 268 | 11 | | | | | | 9950 |
| HPV18 | L1 | ATKFKQYSR | 419 | 9 | | | | | | 9951 |
| HPV18 | L1 | ATSNVSEDVR | 196 | 10 | | | | | | 9952 |
| HPV18 | L1 | ATTSSKPAK | 552 | 9 | | | | | | 9953 |
| HPV18 | L1 | ATTSSKPAKR | 552 | 10 | | | | | | 9954 |
| HPV18 | L1 | CAGVEIGR | 163 | 8 | | | | | | 9955 |
| HPV18 | L1 | CAPAIGEHWAK | 222 | 11 | | | | | | 9956 |
| HPV18 | L1 | CLRREQLFAR | 310 | 10 | | | | | | 9957 |
| HPV18 | L1 | DAAPAENK | 493 | 8 | | | | | | 9958 |
| HPV18 | L1 | DATKFKQYSR | 418 | 10 | | | | | | 9959 |
| HPV18 | L1 | DICQSICK | 284 | 8 | | | | | | 9960 |
| HPV18 | L1 | DIPKVSAYQYR | 122 | 11 | | | | | | 9961 |
| HPV18 | L1 | DLDQYPLGR | 520 | 9 | | | | | | 9962 |
| HPV18 | L1 | DLDQYPLGRK | 520 | 10 | | | | | | 9963 |
| HPV18 | L1 | DSMFFCLR | 305 | 8 | | | | | | 9964 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV18 | L1 | DSMFFCLRR | 305 | 9 | | | | | | 9965 |
| HPV18 | L1 | DTSIYNPETQR | 148 | 11 | | | | | | 9966 |
| HPV18 | L1 | DTVPQSLYIK | 330 | 10 | | | | | | 9967 |
| HPV18 | L1 | DVRDNVSVDYK | 203 | 11 | | | | | | 9968 |
| HPV18 | L1 | FARHFWNR | 317 | 8 | | | | | | 9969 |
| HPV18 | L1 | FLQMALWR | 59 | 8 | | | | | | 9970 |
| HPV18 | L1 | FLVQAGLR | 530 | 8 | | | | | | 9971 |
| HPV18 | L1 | FLVQAGLRR | 530 | 9 | | | | | | 9972 |
| HPV18 | L1 | FLVQAGLRRK | 530 | 10 | | | | | | 9973 |
| HPV18 | L1 | FSTLQDTK | 271 | 8 | | | | | | 9974 |
| HPV18 | L1 | FVQSVAITCQK | 482 | 11 | | | | | | 9975 |
| HPV18 | L1 | GLRRKPTIGPR | 535 | 11 | | | | | | 9976 |
| HPV18 | L1 | GLSGHPFYNK | 177 | 10 | | | | | | 9977 |
| HPV18 | L1 | IVTSDSQLFNK | 360 | 11 | | | | | | 9978 |
| HPV18 | L1 | KLKFWNVDLK | 505 | 10 | | | | | | 9979 |
| HPV18 | L1 | KVSAYQYR | 125 | 8 | | | | | | 9980 |
| HPV18 | L1 | KVSAYQYRVFR | 125 | 11 | | | | | | 9981 |
| HPV18 | L1 | LLTVGNPYFR | 103 | 10 | | | | | | 9982 |
| HPV18 | L1 | LSGHPFYNK | 178 | 9 | | | | | | 9983 |
| HPV18 | L1 | LTVGNPYFR | 104 | 9 | | | | | | 9984 |
| HPV18 | L1 | LVQAGLRR | 531 | 8 | | | | | | 9985 |
| HPV18 | L1 | LVQAGLRRK | 531 | 9 | | | | | | 9986 |
| HPV18 | L1 | PAENKDPYDK | 496 | 10 | | | | | | 9987 |
| HPV18 | L1 | PAIGEHWAK | 224 | 9 | | | | | | 9988 |
| HPV18 | L1 | PAKRVRVR | 558 | 8 | | | | | | 9989 |
| HPV18 | L1 | PAKRVRVRAR | 558 | 10 | | | | | | 9990 |
| HPV18 | L1 | PAKRVRVRARK | 558 | 11 | | | | | | 9991 |
| HPV18 | L1 | PIFLQMALWR | 57 | 10 | | | | | | 9992 |
| HPV18 | L1 | PLDICQSICK | 282 | 10 | | | | | | 9993 |
| HPV18 | L1 | PLYGPLYHPR | 16 | 10 | | | | | | 9994 |
| HPV18 | L1 | PSATTSSK | 550 | 8 | | | | | | 9995 |
| HPV18 | L1 | PSATTSSKPAK | 550 | 11 | | | | | | 9996 |
| HPV18 | L1 | PTIGPRKR | 540 | 8 | | | | | | 9997 |
| HPV18 | L1 | PTTSLVDTYR | 472 | 10 | | | | | | 9998 |
| HPV18 | L1 | PVPGQYDATK | 412 | 10 | | | | | | 9999 |
| HPV18 | L1 | QLFARHFWNR | 315 | 10 | | | | | | 10000 |
| HPV18 | L1 | QLFNKPYWLHK | 366 | 11 | | | | | | 10001 |
| HPV18 | L1 | QSVAITCQK | 484 | 9 | | | | | | 10002 |
| HPV18 | L1 | RLLTVGNPYFR | 102 | 11 | | | | | | 10003 |
| HPV18 | L1 | RSAPSATTSSK | 547 | 11 | | | | | | 10004 |
| HPV18 | L1 | RVPAGGGNK | 112 | 9 | | | | | | 10005 |
| HPV18 | L1 | RVQLPDPNK | 135 | 9 | | | | | | 10006 |
| HPV18 | L1 | RVRVRARK | 561 | 8 | | | | | | 10007 |
| HPV18 | L1 | SAPSATTSSK | 548 | 10 | | | | | | 10008 |
| HPV18 | L1 | SATTSSKPAK | 551 | 10 | | | | | | 10009 |
| HPV18 | L1 | SATTSSKPAKR | 551 | 11 | | | | | | 10010 |
| HPV18 | L1 | SAYQYRVFR | 127 | 9 | | | | | | 10011 |
| HPV18 | L1 | SIFYHAGSSR | 93 | 10 | | | | | | 10012 |
| HPV18 | L1 | SIYNPETQR | 150 | 9 | | | | | | 10013 |
| HPV18 | L1 | SLDLDQYPLGR | 518 | 11 | | | | | | 10014 |
| HPV18 | L1 | SMFFCLRR | 306 | 8 | | | | | | 10015 |
| HPV18 | L1 | SSKPAKRVR | 555 | 9 | | | | | | 10016 |
| HPV18 | L1 | SSKPAKRVRVR | 555 | 11 | | | | | | 10017 |
| HPV18 | L1 | SVAITCQK | 485 | 8 | | | | | | 10018 |
| HPV18 | L1 | TSDSQLFNK | 362 | 9 | | | | | | 10019 |
| HPV18 | L1 | TSIFYHAGSSR | 92 | 11 | | | | | | 10020 |
| HPV18 | L1 | TSIYNPETQR | 149 | 10 | | | | | | 10021 |
| HPV18 | L1 | TSLVDTYR | 474 | 8 | | | | | | 10022 |
| HPV18 | L1 | TSNVSEDVR | 197 | 9 | | | | | | 10023 |
| HPV18 | L1 | TSSKPAKR | 554 | 8 | | | | | | 10024 |
| HPV18 | L1 | TSSKPAKRVR | 554 | 10 | | | | | | 10025 |
| HPV18 | L1 | TTSLVDTYR | 473 | 9 | | | | | | 10026 |
| HPV18 | L1 | TTSSKPAK | 553 | 8 | | | | | | 10027 |
| HPV18 | L1 | TTSSKPAKR | 553 | 9 | | | | | | 10028 |
| HPV18 | L1 | TTSSKPAKRVR | 553 | 11 | | | | | | 10029 |
| HPV18 | L1 | TVGNPYFR | 105 | 8 | | | | | | 10030 |
| HPV18 | L1 | TVPQSLYIK | 331 | 9 | | | | | | 10031 |
| HPV18 | L1 | TVYLPPPSVAR | 71 | 11 | | | | | | 10032 |
| HPV18 | L1 | VSAYQYRVFR | 126 | 10 | | | | | | 10033 |
| HPV18 | L1 | VTSDSQLFNK | 361 | 10 | | | | | | 10034 |
| HPV18 | L1 | WACAGVEIGR | 161 | 10 | | | | | | 10035 |
| HPV18 | L1 | WAKGTACK | 230 | 8 | | | | | | 10036 |
| HPV18 | L1 | WAKGTACKSR | 230 | 10 | | | | | | 10037 |
| HPV18 | L1 | YLPPPSVAR | 73 | 9 | | | | | | 10038 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV18 | L2 | ALTSRRGTVR | 286 | 10 | | | | | | 10039 |
| HPV18 | L2 | ASVTDLYK | 12 | 8 | | | | | | 10040 |
| HPV18 | L2 | ASVTDLYKTCK | 12 | 11 | | | | | | 10041 |
| HPV18 | L2 | DMDPAVPVPSR | 354 | 11 | | | | | | 10042 |
| HPV18 | L2 | DSDFMDIIR | 273 | 9 | | | | | | 10043 |
| HPV18 | L2 | DSVVTSGAPR | 109 | 11 | | | | | | 10044 |
| HPV18 | L2 | DTTLTFDPR | 260 | 9 | | | | | | 10045 |
| HPV18 | L2 | FIPKKRKR | 443 | 8 | | | | | | 10046 |
| HPV18 | L2 | FMDIIRLHR | 276 | 9 | | | | | | 10047 |
| HPV18 | L2 | FTRSGTQIGAR | 306 | 11 | | | | | | 10048 |
| HPV18 | L2 | GIGTGSGTGGR | 58 | 11 | | | | | | 10049 |
| HPV18 | L2 | GTCPPDVVPK | 25 | 10 | | | | | | 10050 |
| HPV18 | L2 | GTGSGTGGR | 60 | 9 | | | | | | 10051 |
| HPV18 | L2 | GTVRFSRLGQR | 292 | 11 | | | | | | 10052 |
| HPV18 | L2 | ISSTPLPTVR | 210 | 10 | | | | | | 10053 |
| HPV18 | L2 | ISSTPLPTVRR | 210 | 11 | | | | | | 10054 |
| HPV18 | L2 | KVEGTTLADK | 34 | 10 | | | | | | 10055 |
| HPV18 | L2 | LTSRRGTVR | 287 | 9 | | | | | | 10056 |
| HPV18 | L2 | MVSHRAAR | 1 | 8 | | | | | | 10057 |
| HPV18 | L2 | MVSHRAARR | 1 | 9 | | | | | | 10058 |
| HPV18 | L2 | MVSHRAARRK | 1 | 10 | | | | | | 10059 |
| HPV18 | L2 | MVSHRAARRKR | 1 | 11 | | | | | | 10060 |
| HPV18 | L2 | NTVVDVGPTR | 79 | 10 | | | | | | 10061 |
| HPV18 | L2 | PALTSRRGTVR | 285 | 11 | | | | | | 10062 |
| HPV18 | L2 | PAVPVPSR | 357 | 8 | | | | | | 10063 |
| HPV18 | L2 | PISSTPLPTVR | 209 | 11 | | | | | | 10064 |
| HPV18 | L2 | PLYYFIPK | 439 | 8 | | | | | | 10065 |
| HPV18 | L2 | PLYYFIPKK | 439 | 9 | | | | | | 10066 |
| HPV18 | L2 | PLYYFIPKKR | 439 | 10 | | | | | | 10067 |
| HPV18 | L2 | PLYYFIPKKRK | 439 | 11 | | | | | | 10068 |
| HPV18 | L2 | PTVRRVAGPR | 216 | 10 | | | | | | 10069 |
| HPV18 | L2 | PVDTTLTFDPR | 258 | 11 | | | | | | 10070 |
| HPV18 | L2 | RASVTDLYK | 11 | 9 | | | | | | 10071 |
| HPV18 | L2 | RLGQRATMFTR | 298 | 11 | | | | | | 10072 |
| HPV18 | L2 | RLHRPALTSR | 281 | 10 | | | | | | 10073 |
| HPV18 | L2 | RLHRPALTSRR | 281 | 11 | | | | | | 10074 |
| HPV18 | L2 | RSGTQIGAR | 308 | 9 | | | | | | 10075 |
| HPV18 | L2 | RSTTSFAFFK | 364 | 10 | | | | | | 10076 |
| HPV18 | L2 | RTGYIPLGGR | 68 | 10 | | | | | | 10077 |
| HPV18 | L2 | RVAGPRLYSR | 220 | 10 | | | | | | 10078 |
| HPV18 | L2 | SSTPLPTVR | 211 | 9 | | | | | | 10079 |
| HPV18 | L2 | SSTPLPTVRR | 211 | 10 | | | | | | 10080 |
| HPV18 | L2 | SSVVTSGAPR | 110 | 10 | | | | | | 10081 |
| HPV18 | L2 | STPLPTVR | 212 | 8 | | | | | | 10082 |
| HPV18 | L2 | STPLPTVRR | 212 | 9 | | | | | | 10083 |
| HPV18 | L2 | STTSFAFFK | 365 | 9 | | | | | | 10084 |
| HPV18 | L2 | SVANPEFLTR | 235 | 10 | | | | | | 10085 |
| HPV18 | L2 | SVTDLYKTCK | 13 | 10 | | | | | | 10086 |
| HPV18 | L2 | SVVTSGAPR | 111 | 9 | | | | | | 10087 |
| HPV18 | L2 | TSRRGTVR | 288 | 8 | | | | | | 10088 |
| HPV18 | L2 | TSRRGTVRFSR | 288 | 11 | | | | | | 10089 |
| HPV18 | L2 | TTLTFDPR | 261 | 8 | | | | | | 10090 |
| HPV18 | L2 | TTSFAFFK | 366 | 8 | | | | | | 10091 |
| HPV18 | L2 | TVRFSRLGQR | 293 | 10 | | | | | | 10092 |
| HPV18 | L2 | TVRRVAGPR | 217 | 9 | | | | | | 10093 |
| HPV18 | L2 | TVVDVGPTR | 80 | 9 | | | | | | 10094 |
| HPV18 | L2 | VAGPRLYSR | 221 | 9 | | | | | | 10095 |
| HPV18 | L2 | VANPEFLTR | 236 | 9 | | | | | | 10096 |
| HPV18 | L2 | VSHRAARR | 2 | 8 | | | | | | 10097 |
| HPV18 | L2 | VSHRAARRK | 2 | 9 | | | | | | 10098 |
| HPV18 | L2 | VSHRAARRKR | 2 | 10 | | | | | | 10099 |
| HPV18 | L2 | VSVANPEFLTR | 234 | 11 | | | | | | 10100 |
| HPV18 | L2 | VTDLYKTCK | 14 | 9 | | | | | | 10101 |
| HPV18 | L2 | VVDVGPTR | 81 | 8 | | | | | | 10102 |
| HPV18 | L2 | VVTSGAPR | 112 | 8 | | | | | | 10103 |
| HPV18 | L2 | YLWPLYYFIPK | 436 | 11 | | | | | | 10104 |
| HPV31 | E1 | AAALYWYR | 296 | 8 | | | | | | 10105 |
| HPV31 | E1 | AAMLGKFK | 185 | 8 | | | | | | 10106 |
| HPV31 | E1 | AICIENNSK | 111 | 9 | | | | | | 10107 |
| HPV31 | E1 | ALKLFLKGVPK | 439 | 11 | | | | | | 10108 |
| HPV31 | E1 | AVQVLKRK | 81 | 8 | | | | | | 10109 |
| HPV31 | E1 | CAFLKSNSQAK | 370 | 11 | | | | | | 10110 |
| HPV31 | E1 | CAKNRITIEK | 263 | 10 | | | | | | 10111 |
| HPV31 | E1 | CIENNSKTAK | 113 | 10 | | | | | | 10112 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV31 | E1 | CIENNSKTAKR | 113 | 11 | | | | | | 10113 |
| HPV31 | E1 | CIISYANSK | 477 | 9 | | | | | | 10114 |
| HPV31 | E1 | CMLIQPPK | 284 | 8 | | | | | | 10115 |
| HPV31 | E1 | CMLIQPPKLR | 284 | 10 | | | | | | 10116 |
| HPV31 | E1 | CVDYNISPR | 100 | 9 | | | | | | 10117 |
| HPV31 | E1 | CVDYNISPRLK | 100 | 11 | | | | | | 10118 |
| HPV31 | E1 | CVSGQNIR | 620 | 8 | | | | | | 10119 |
| HPV31 | E1 | DSDSNACAFLK | 364 | 11 | | | | | | 10120 |
| HPV31 | E1 | DSNACAFLK | 366 | 9 | | | | | | 10121 |
| HPV31 | E1 | DVKHKALMQLK | 528 | 11 | | | | | | 10122 |
| HPV31 | E1 | DVMDDSEIAYK | 348 | 11 | | | | | | 10123 |
| HPV31 | E1 | EAVQVLKR | 80 | 8 | | | | | | 10124 |
| HPV31 | E1 | EAVQVLKRK | 80 | 9 | | | | | | 10125 |
| HPV31 | E1 | ELIRPFQSNK | 201 | 10 | | | | | | 10126 |
| HPV31 | E1 | ELSDKNWK | 583 | 8 | | | | | | 10127 |
| HPV31 | E1 | ETPEWIER | 315 | 8 | | | | | | 10128 |
| HPV31 | E1 | FLKGVPKK | 443 | 8 | | | | | | 10129 |
| HPV31 | E1 | FLKSNSQAK | 372 | 9 | 0.0013 | 0.0002 | | | | 10130 |
| HPV31 | E1 | FLSALKLFLK | 436 | 10 | | | | | | 10131 |
| HPV31 | E1 | FTFPNPFPFDK | 566 | 11 | | | | | | 10132 |
| HPV31 | E1 | FVSFLSALK | 433 | 9 | | | | | | 10133 |
| HPV31 | E1 | GMVMLMLVR | 252 | 9 | | | | | | 10134 |
| HPV31 | E1 | GMVMLMLVRFK | 252 | 11 | | | | | | 10135 |
| HPV31 | E1 | GSDGTHSER | 157 | 9 | | | | | | 10136 |
| HPV31 | E1 | GTMCRHYK | 386 | 8 | | | | | | 10137 |
| HPV31 | E1 | GTMCRHYKR | 386 | 9 | | | | | | 10138 |
| HPV31 | E1 | GTVAEGFK | 225 | 8 | | | | | | 10139 |
| HPV31 | E1 | GVSFMELIR | 196 | 9 | | | | | | 10140 |
| HPV31 | E1 | GVTGTVAEGFK | 222 | 11 | | | | | | 10141 |
| HPV31 | E1 | HAEAVQVLK | 78 | 9 | | | | | | 10142 |
| HPV31 | E1 | HAEAVQVLKR | 78 | 10 | | | | | | 10143 |
| HPV31 | E1 | HAEAVQVLKRK | 78 | 11 | | | | | | 10144 |
| HPV31 | E1 | HSERENETPTR | 162 | 11 | | | | | | 10145 |
| HPV31 | E1 | IISYANSK | 478 | 8 | | | | | | 10146 |
| HPV31 | E1 | ILIHGAPNTGK | 453 | 11 | | | | | | 10147 |
| HPV31 | E1 | ILQVLKTSNGK | 174 | 11 | | | | | | 10148 |
| HPV31 | E1 | ITIEKLLEK | 268 | 9 | | | | | | 10149 |
| HPV31 | E1 | ITSNINAGK | 544 | 9 | | | | | | 10150 |
| HPV31 | E1 | IVKDCGTMCR | 381 | 10 | | | | | | 10151 |
| HPV31 | E1 | KAAMLGKFK | 184 | 9 | | | | | | 10152 |
| HPV31 | E1 | KAICIENNSK | 110 | 10 | | | | | | 10153 |
| HPV31 | E1 | KIVKDCGTMCR | 380 | 11 | | | | | | 10154 |
| HPV31 | E1 | KLFLKGVPK | 441 | 9 | | | | | | 10155 |
| HPV31 | E1 | KLFLKGVPKK | 441 | 10 | | | | | | 10156 |
| HPV31 | E1 | KSFFSRTWCR | 590 | 10 | | | | | | 10157 |
| HPV31 | E1 | KSNSQAKIVK | 374 | 10 | | | | | | 10158 |
| HPV31 | E1 | KVSDEGDWR | 412 | 9 | | | | | | 10159 |
| HPV31 | E1 | LIHGAPNTGK | 454 | 10 | | | | | | 10160 |
| HPV31 | E1 | LIQPPKLR | 286 | 8 | | | | | | 10161 |
| HPV31 | E1 | LIRPFQSNK | 202 | 9 | | | | | | 10162 |
| HPV31 | E1 | LITSNINAGK | 543 | 10 | | | | | | 10163 |
| HPV31 | E1 | LLITSNINAGK | 542 | 11 | | | | | | 10164 |
| HPV31 | E1 | LMLVRFKCAK | 256 | 10 | | | | | | 10165 |
| HPV31 | E1 | LSALKLFLK | 437 | 9 | | | | | | 10166 |
| HPV31 | E1 | LVRFKCAK | 258 | 8 | | | | | | 10167 |
| HPV31 | E1 | LVRFKCAKNR | 258 | 10 | | | | | | 10168 |
| HPV31 | E1 | MLIQPPKLR | 285 | 9 | 0.0005 | 0.0014 | | | | 10169 |
| HPV31 | E1 | MLMLVRFK | 255 | 8 | | | | | | 10170 |
| HPV31 | E1 | MLMLVRFKCAK | 255 | 11 | | | | | | 10171 |
| HPV31 | E1 | MLVRFKCAK | 257 | 9 | | | | | | 10172 |
| HPV31 | E1 | MLVRFKCAKNR | 257 | 11 | | | | | | 10173 |
| HPV31 | E1 | MSMGQWIK | 400 | 8 | | | | | | 10174 |
| HPV31 | E1 | MSMGQWIKSR | 400 | 10 | | | | | | 10175 |
| HPV31 | E1 | MVMLMLVR | 253 | 8 | | | | | | 10176 |
| HPV31 | E1 | MVMLMLVRFK | 253 | 10 | | | | | | 10177 |
| HPV31 | E1 | NINAGKDDR | 547 | 9 | | | | | | 10178 |
| HPV31 | E1 | NLHEEEDK | 601 | 8 | | | | | | 10179 |
| HPV31 | E1 | NSKTAKRR | 117 | 8 | | | | | | 10180 |
| HPV31 | E1 | NSQAKIVK | 376 | 8 | | | | | | 10181 |
| HPV31 | E1 | PTRNILQVLK | 170 | 10 | | | | | | 10182 |
| HPV31 | E1 | PVSIDVKHK | 524 | 9 | | | | | | 10183 |
| HPV31 | E1 | PVYELSDK | 580 | 8 | | | | | | 10184 |
| HPV31 | E1 | PVYELSDKNWK | 580 | 11 | | | | | | 10185 |
| HPV31 | E1 | QMSMGQWIK | 399 | 9 | | | | | | 10186 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV31 | E1 | QMSMGQWIKSR | 399 | 11 | | | | | | 10187 |
| HPV31 | E1 | QVLKTSNGK | 176 | 9 | | | | | | 10188 |
| HPV31 | E1 | RITIEKLLEK | 267 | 10 | | | | | | 10189 |
| HPV31 | E1 | RLNLHEEEDK | 599 | 10 | | | | | | 10190 |
| HPV31 | E1 | RSTAAALYWYR | 293 | 11 | | | | | | 10191 |
| HPV31 | E1 | SALKLFLK | 438 | 8 | | | | | | 10192 |
| HPV31 | E1 | SMGQWIKSR | 401 | 9 | | | | | | 10193 |
| HPV31 | E1 | SSCVDYNISPR | 98 | 11 | | | | | | 10194 |
| HPV31 | E1 | STAAALYWYR | 294 | 10 | | | | | | 10195 |
| HPV31 | E1 | STNCMLIQPPK | 281 | 11 | | | | | | 10196 |
| HPV31 | E1 | TAAALYWYR | 295 | 9 | | | | | | 10197 |
| HPV31 | E1 | TIEKLLEK | 269 | 8 | | | | | | 10198 |
| HPV31 | E1 | TMCRHYKR | 387 | 8 | | | | | | 10199 |
| HPV31 | E1 | TMCRHYKRAEK | 387 | 11 | | | | | | 10200 |
| HPV31 | E1 | TSNGKAAMLGK | 180 | 11 | | | | | | 10201 |
| HPV31 | E1 | TSNINAGK | 545 | 8 | | | | | | 10202 |
| HPV31 | E1 | TSNINAGKDDR | 545 | 11 | | | | | | 10203 |
| HPV31 | E1 | VLKTSNGK | 177 | 8 | | | | | | 10204 |
| HPV31 | E1 | VMDDSEIAYK | 349 | 10 | | | | | | 10205 |
| HPV31 | E1 | VMLMLVRFK | 254 | 9 | | | | | | 10206 |
| HPV31 | E1 | VSDEGDWR | 413 | 8 | | | | | | 10207 |
| HPV31 | E1 | VSFLSALK | 434 | 8 | | | | | | 10208 |
| HPV31 | E1 | VSFMELIR | 197 | 8 | | | | | | 10209 |
| HPV31 | E1 | VSIDVKHK | 525 | 8 | | | | | | 10210 |
| HPV31 | E1 | VTGTVAEGFK | 223 | 10 | | | | | | 10211 |
| HPV31 | E1 | WIKSRCDK | 405 | 8 | | | | | | 10212 |
| HPV31 | E1 | WLQPLADAK | 489 | 9 | 0.0005 | 0.0002 | | | | 10213 |
| HPV31 | E1 | YVEAVIDR | 19 | 8 | | | | | | 10214 |
| HPV31 | E2 | AAACTNQTR | 277 | 9 | | | | | | 10215 |
| HPV31 | E2 | AACTNQTR | 278 | 8 | | | | | | 10216 |
| HPV31 | E2 | ALGTSEGVR | 229 | 9 | | | | | | 10217 |
| HPV31 | E2 | ALGTSEGVRR | 229 | 10 | | | | | | 10218 |
| HPV31 | E2 | ALSVSKAK | 61 | 8 | | | | | | 10219 |
| HPV31 | E2 | ATTPIIHLK | 291 | 9 | | | | | | 10220 |
| HPV31 | E2 | ATTSTKRPR | 239 | 9 | | | | | | 10221 |
| HPV31 | E2 | CALGTSEGVR | 228 | 10 | | | | | | 10222 |
| HPV31 | E2 | CALGTSEGVRR | 228 | 11 | | | | | | 10223 |
| HPV31 | E2 | CLRYRLSK | 307 | 8 | | | | | | 10224 |
| HPV31 | E2 | CLRYRLSKYK | 307 | 10 | | | | | | 10225 |
| HPV31 | E2 | CTVVEGQVNCK | 145 | 11 | | | | | | 10226 |
| HPV31 | E2 | CVLMYKAR | 40 | 8 | | | | | | 10227 |
| HPV31 | E2 | DANILKCLR | 301 | 9 | | | | | | 10228 |
| HPV31 | E2 | DANILKCLRYR | 301 | 11 | | | | | | 10229 |
| HPV31 | E2 | EAKKYGTGK | 174 | 9 | | | | | | 10230 |
| HPV31 | E2 | EAKKYGTGKK | 174 | 10 | | | | | | 10231 |
| HPV31 | E2 | EISFAGIVTK | 204 | 10 | | | | | | 10232 |
| HPV31 | E2 | ETLNNTEYK | 80 | 9 | | | | | | 10233 |
| HPV31 | E2 | FVNFTEEAK | 168 | 9 | | | | | | 10234 |
| HPV31 | E2 | FVNFTEEAKK | 168 | 10 | | | | | | 10235 |
| HPV31 | E2 | GTSEGVRR | 231 | 8 | | | | | | 10236 |
| HPV31 | E2 | GVRRATTSTK | 235 | 10 | | | | | | 10237 |
| HPV31 | E2 | GVRRATTSTKR | 235 | 11 | | | | | | 10238 |
| HPV31 | E2 | HIDYWKHIR | 29 | 9 | | | | | | 10239 |
| HPV31 | E2 | HIRLECVLMYK | 35 | 11 | | | | | | 10240 |
| HPV31 | E2 | HLKGDANILK | 297 | 10 | | | | | | 10241 |
| HPV31 | E2 | ILEHYENDSK | 15 | 10 | | | | | | 10242 |
| HPV31 | E2 | ILEHYENDSKR | 15 | 11 | | | | | | 10243 |
| HPV31 | E2 | ILKCLRYR | 304 | 8 | | | | | | 10244 |
| HPV31 | E2 | ILKCLRYRLSK | 304 | 11 | | | | | | 10245 |
| HPV31 | E2 | ISAAACTNQTR | 275 | 11 | | | | | | 10246 |
| HPV31 | E2 | ISFAGIVTK | 205 | 9 | | | | | | 10247 |
| HPV31 | E2 | KILEHYENDSK | 14 | 11 | | | | | | 10248 |
| HPV31 | E2 | LSQRLNVCQDK | 4 | 11 | | | | | | 10249 |
| HPV31 | E2 | LTAPTGCLK | 103 | 9 | | | | | | 10250 |
| HPV31 | E2 | LTAPTGCLKK | 103 | 10 | | | | | | 10251 |
| HPV31 | E2 | LTYISTSQR | 342 | 9 | | | | | | 10252 |
| HPV31 | E2 | MLETLNNTEYK | 78 | 11 | | | | | | 10253 |
| HPV31 | E2 | NILKCLRYR | 303 | 9 | | | | | | 10254 |
| HPV31 | E2 | NTHHPNKLLR | 254 | 10 | | | | | | 10255 |
| HPV31 | E2 | NTMHYTNWK | 127 | 9 | | | | | | 10256 |
| HPV31 | E2 | NTTTSNSK | 219 | 8 | | | | | | 10257 |
| HPV31 | E2 | PALSVSKAK | 60 | 9 | | | | | | 10258 |
| HPV31 | E2 | PATTPIIHLK | 290 | 10 | | | | | | 10259 |
| HPV31 | E2 | QVVPALSVSK | 57 | 10 | | | | | | 10260 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV31 | E2 | RATTSTKR | 238 | 8 | | | | | | 10261 |
| HPV31 | E2 | RATTSTKRPR | 238 | 10 | | | | | | 10262 |
| HPV31 | E2 | RLCDHIDYWK | 25 | 10 | | | | | | 10263 |
| HPV31 | E2 | RLECVLMYK | 37 | 9 | | | | | | 10264 |
| HPV31 | E2 | RLECVLMYKAR | 37 | 11 | | | | | | 10265 |
| HPV31 | E2 | RLNVCQDK | 7 | 8 | | | | | | 10266 |
| HPV31 | E2 | SAAACTNQTR | 276 | 10 | | | | | | 10267 |
| HPV31 | E2 | STWHWTCTDGK | 324 | 11 | | | | | | 10268 |
| HPV31 | E2 | TANNTTTSNSK | 216 | 11 | | | | | | 10269 |
| HPV31 | E2 | TAPTGCLK | 104 | 8 | | | | | | 10270 |
| HPV31 | E2 | TAPTGCLKK | 104 | 9 | | | | | | 10271 |
| HPV31 | E2 | TLNNTEYK | 81 | 8 | | | | | | 10272 |
| HPV31 | E2 | TLTYISTSQR | 341 | 10 | | | | | | 10273 |
| HPV31 | E2 | TMHYTNWK | 128 | 8 | | | | | | 10274 |
| HPV31 | E2 | TTPIIHLK | 292 | 8 | | | | | | 10275 |
| HPV31 | E2 | TTSTKRPR | 240 | 8 | | | | | | 10276 |
| HPV31 | E2 | TVVEGQVNCK | 146 | 10 | | | | | | 10277 |
| HPV31 | E2 | VTLTYISTSQR | 340 | 11 | | | | | | 10278 |
| HPV31 | E2 | VVEGQVNCK | 147 | 9 | | | | | | 10279 |
| HPV31 | E2 | VVPALSVSK | 58 | 9 | | | | | | 10280 |
| HPV31 | E2 | VVPALSVSKAK | 58 | 11 | | | | | | 10281 |
| HPV31 | E2 | WTCTDGKHK | 328 | 9 | | | | | | 10282 |
| HPV31 | E2 | YLTAPTGCLK | 102 | 10 | | | | | | 10283 |
| HPV31 | E2 | YLTAPTGCLKK | 102 | 11 | | | | | | 10284 |
| HPV31 | E5 | CVLLFVCLVIR | 20 | 11 | | | | | | 10285 |
| HPV31 | E5 | ILWVIATSPLR | 48 | 11 | | | | | | 10286 |
| HPV31 | E5 | LLFVCLVIR | 22 | 9 | | | | | | 10287 |
| HPV31 | E5 | VIATSPLR | 51 | 8 | | | | | | 10288 |
| HPV31 | E5 | VLLFVCLVIR | 21 | 10 | | | | | | 10289 |
| HPV31 | E5 | WVIATSPLR | 50 | 9 | | | | | | 10290 |
| HPV31 | E6 | ALEIPYDELR | 18 | 10 | | | | | | 10291 |
| HPV31 | E6 | CIACWRRPR | 136 | 9 | | | | | | 10292 |
| HPV31 | E6 | CTKCLRFYSK | 63 | 10 | | | | | | 10293 |
| HPV31 | E6 | DLLIRCITCQR | 98 | 11 | | | | | | 10294 |
| HPV31 | E6 | DTPHGVCTK | 57 | 9 | | | | | | 10295 |
| HPV31 | E6 | EIPYDELR | 20 | 8 | | | | | | 10296 |
| HPV31 | E6 | ELRLNCVYCK | 25 | 10 | | | | | | 10297 |
| HPV31 | E6 | FAFTDLTIVYR | 45 | 11 | | | | | | 10298 |
| HPV31 | E6 | FTDLTIVYR | 47 | 9 | | | | | | 10299 |
| HPV31 | E6 | GICDLLIR | 95 | 8 | | | | | | 10300 |
| HPV31 | E6 | GTTLEKLTNK | 85 | 10 | | | | | | 10301 |
| HPV31 | E6 | GVCTKCLR | 61 | 8 | | | | | | 10302 |
| HPV31 | E6 | IACWRRPR | 137 | 8 | | | | | | 10303 |
| HPV31 | E6 | KVSEFRWYR | 72 | 9 | | | | | | 10304 |
| HPV31 | E6 | LIRCITCQR | 100 | 9 | | | | | | 10305 |
| HPV31 | E6 | LLIRCITCQR | 99 | 10 | | | | | | 10306 |
| HPV31 | E6 | NIGGRWTGR | 127 | 9 | | | | | | 10307 |
| HPV31 | E6 | PLCPEEKQR | 109 | 9 | 0.0002 | 0.0005 | | | | 10308 |
| HPV31 | E6 | RLNCVYCK | 27 | 8 | | | | | | 10309 |
| HPV31 | E6 | SALEIPYDELR | 17 | 11 | | | | | | 10310 |
| HPV31 | E6 | SVYGTTLEK | 82 | 9 | | | | | | 10311 |
| HPV31 | E6 | TLEKLTNK | 87 | 8 | | | | | | 10312 |
| HPV31 | E6 | TTLEKLTNK | 86 | 9 | | | | | | 10313 |
| HPV31 | E6 | VSEFRWYR | 73 | 8 | | | | | | 10314 |
| HPV31 | E6 | WTGRCIACWR | 132 | 10 | | | | | | 10315 |
| HPV31 | E6 | WTGRCIACWRR | 132 | 11 | | | | | | 10316 |
| HPV31 | E6 | YSKVSEFR | 70 | 8 | | | | | | 10317 |
| HPV31 | E6 | YSKVSEFRWYR | 70 | 11 | | | | | | 10318 |
| HPV31 | E6 | YSVYGTTLEK | 81 | 10 | | | | | | 10319 |
| HPV31 | E7 | CVQSTQVDIR | 68 | 10 | | | | | | 10320 |
| HPV31 | E7 | GIVCPNCSTR | 88 | 10 | | | | | | 10321 |
| HPV31 | E7 | IVCPNCSTR | 89 | 9 | | | | | | 10322 |
| HPV31 | E7 | IVTFCCQCK | 54 | 9 | | | | | | 10323 |
| HPV31 | E7 | NIVTFCCQCK | 53 | 10 | | | | | | 10324 |
| HPV31 | E7 | QSTQVDIR | 70 | 8 | | | | | | 10325 |
| HPV31 | E7 | VTFCCQCK | 55 | 8 | | | | | | 10326 |
| HPV31 | L1 | AAIANSDTTFK | 347 | 11 | | | | | | 10327 |
| HPV31 | L1 | AIANSDTTFK | 348 | 10 | | | | | | 10328 |
| HPV31 | L1 | AITCQKTAPQK | 426 | 11 | | | | | | 10329 |
| HPV31 | L1 | AMDFTALQDTK | 208 | 11 | | | | | | 10330 |
| HPV31 | L1 | ASTTTPAK | 491 | 8 | | | | | | 10331 |
| HPV31 | L1 | ASTTTPAKR | 491 | 9 | | | | | | 10332 |
| HPV31 | L1 | ASTTTPAKRK | 491 | 10 | | | | | | 10333 |
| HPV31 | L1 | ASTTTPAKRKK | 491 | 11 | | | | | | 10334 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV31 | L1 | CVGLEVGR | 103 | 8 | | | | | | 10335 |
| HPV31 | L1 | DICNSICK | 224 | 8 | | | | | | 10336 |
| HPV31 | L1 | DLDQFPLGR | 459 | 9 | | | | | | 10337 |
| HPV31 | L1 | DLDQFPLGRK | 459 | 10 | | | | | | 10338 |
| HPV31 | L1 | DLQFIFQLCK | 372 | 10 | | | | | | 10339 |
| HPV31 | L1 | DTLFFYLR | 245 | 8 | | | | | | 10340 |
| HPV31 | L1 | DTLFFYLRR | 245 | 9 | | | | | | 10341 |
| HPV31 | L1 | DTSFYNPETQR | 88 | 11 | | | | | | 10342 |
| HPV31 | L1 | DTTFKSSNFK | 353 | 10 | | | | | | 10343 |
| HPV31 | L1 | ESVPTDLYIK | 270 | 10 | | | | | | 10344 |
| HPV31 | L1 | FLLQAGYR | 469 | 8 | | | | | | 10345 |
| HPV31 | L1 | FLLQAGYRAR | 469 | 10 | | | | | | 10346 |
| HPV31 | L1 | FTALQDTK | 211 | 8 | | | | | | 10347 |
| HPV31 | L1 | FVRHFFNR | 257 | 8 | | | | | | 10348 |
| HPV31 | L1 | FVTSQAITCQK | 421 | 11 | | | | | | 10349 |
| HPV31 | L1 | FVTVVDTTR | 331 | 9 | | | | | | 10350 |
| HPV31 | L1 | GISGHPLLNK | 117 | 10 | | | | | | 10351 |
| HPV31 | L1 | GLQYRVFR | 68 | 8 | | | | | | 10352 |
| HPV31 | L1 | GLQYRVFRVR | 68 | 10 | | | | | | 10353 |
| HPV31 | L1 | GSLEDTYR | 413 | 8 | | | | | | 10354 |
| HPV31 | L1 | IANSDTTFK | 349 | 9 | | | | | | 10355 |
| HPV31 | L1 | ISGHPLLNK | 118 | 9 | | | | | | 10356 |
| HPV31 | L1 | ITCQKTAPQK | 427 | 10 | | | | | | 10357 |
| HPV31 | L1 | KSSNFKEYLR | 357 | 10 | | | | | | 10358 |
| HPV31 | L1 | KTAPQKPK | 431 | 8 | | | | | | 10359 |
| HPV31 | L1 | KVSGLQYR | 65 | 8 | | | | | | 10360 |
| HPV31 | L1 | KVSGLQYRVFR | 65 | 11 | | | | | | 10361 |
| HPV31 | L1 | KVVSTDEYVTR | 20 | 11 | | | | | | 10362 |
| HPV31 | L1 | LLQAGYRAR | 470 | 9 | | | | | | 10363 |
| HPV31 | L1 | LLQAGYRARPK | 470 | 11 | | | | | | 10364 |
| HPV31 | L1 | MVTSDAQIFNK | 300 | 11 | | | | | | 10365 |
| HPV31 | L1 | NIYYHAGSAR | 32 | 10 | | | | | | 10366 |
| HPV31 | L1 | NSICKYPDYLK | 227 | 11 | | | | | | 10367 |
| HPV31 | L1 | PAKRKKTK | 496 | 8 | | | | | | 10368 |
| HPV31 | L1 | PAKRKKTKK | 496 | 9 | | | | | | 10369 |
| HPV31 | L1 | PIGEHWGK | 165 | 8 | | | | | | 10370 |
| HPV31 | L1 | PLDICNSICK | 222 | 10 | | | | | | 10371 |
| HPV31 | L1 | PSASTTTPAK | 489 | 10 | | | | | | 10372 |
| HPV31 | L1 | PSASTTTPAKR | 489 | 11 | | | | | | 10373 |
| HPV31 | L1 | PSGSLEDTYR | 411 | 10 | | | | | | 10374 |
| HPV31 | L1 | QAGYRARPK | 472 | 9 | | | | | | 10375 |
| HPV31 | L1 | QAGYRARPKFK | 472 | 11 | | | | | | 10376 |
| HPV31 | L1 | QIFNKPYWMQR | 306 | 11 | | | | | | 10377 |
| HPV31 | L1 | QLCLLGCK | 156 | 8 | | | | | | 10378 |
| HPV31 | L1 | QLFVTVVDTTR | 329 | 11 | | | | | | 10379 |
| HPV31 | L1 | QMFVRHFFNR | 255 | 10 | | | | | | 10380 |
| HPV31 | L1 | QTQLCLLGCK | 154 | 10 | | | | | | 10381 |
| HPV31 | L1 | RARPKFKAGK | 476 | 10 | | | | | | 10382 |
| HPV31 | L1 | RARPKFKAGKR | 476 | 11 | | | | | | 10383 |
| HPV31 | L1 | RVRLPDPNK | 75 | 9 | | | | | | 10384 |
| HPV31 | L1 | SADLDQFPLGR | 457 | 11 | | | | | | 10385 |
| HPV31 | L1 | SASTTTPAK | 490 | 9 | | | | | | 10386 |
| HPV31 | L1 | SASTTTPAKR | 490 | 10 | | | | | | 10387 |
| HPV31 | L1 | SASTTTPAKRK | 490 | 11 | | | | | | 10388 |
| HPV31 | L1 | SICKYPDYLK | 228 | 10 | | | | | | 10389 |
| HPV31 | L1 | SIPKSDNPK | 51 | 9 | | | | | | 10390 |
| HPV31 | L1 | SIPKSDNPKK | 51 | 10 | | | | | | 10391 |
| HPV31 | L1 | SSNFKEYLR | 358 | 9 | | | | | | 10392 |
| HPV31 | L1 | STDEYVTR | 23 | 8 | | | | | | 10393 |
| HPV31 | L1 | STTTPAKR | 492 | 8 | | | | | | 10394 |
| HPV31 | L1 | STTTPAKRK | 492 | 9 | | | | | | 10395 |
| HPV31 | L1 | STTTPAKRKK | 492 | 10 | | | | | | 10396 |
| HPV31 | L1 | SVPTDLYIK | 271 | 9 | | | | | | 10397 |
| HPV31 | L1 | TLFFYLRR | 246 | 8 | | | | | | 10398 |
| HPV31 | L1 | TSDAQIFNK | 302 | 9 | | | | | | 10399 |
| HPV31 | L1 | TSFYNPETQR | 89 | 10 | | | | | | 10400 |
| HPV31 | L1 | TSQAITCQK | 423 | 9 | | | | | | 10401 |
| HPV31 | L1 | TTFKSSNFK | 354 | 9 | | | | | | 10402 |
| HPV31 | L1 | TTPAKRKK | 494 | 8 | | | | | | 10403 |
| HPV31 | L1 | TTPAKRKKTK | 494 | 10 | | | | | | 10404 |
| HPV31 | L1 | TTPAKRKKTKK | 494 | 11 | | | | | | 10405 |
| HPV31 | L1 | TTTPAKRK | 493 | 8 | | | | | | 10406 |
| HPV31 | L1 | TTTPAKRKK | 493 | 9 | | | | | | 10407 |
| HPV31 | L1 | TTTPAKRKKTK | 493 | 11 | | | | | | 10408 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV31 | L1 | TVGHPYYSIPK | 44 | 11 | | | | | | 10409 |
| HPV31 | L1 | TVYLPPVPVSK | 10 | 11 | | | | | | 10410 |
| HPV31 | L1 | VSGLQYRVFR | 66 | 10 | | | | | | 10411 |
| HPV31 | L1 | VSTDEYVTR | 22 | 9 | | | | | | 10412 |
| HPV31 | L1 | VTSDAQIFNK | 301 | 10 | | | | | | 10413 |
| HPV31 | L1 | VTSQAITCQK | 422 | 10 | | | | | | 10414 |
| HPV31 | L1 | VTVVDTTR | 332 | 8 | | | | | | 10415 |
| HPV31 | L1 | VVPKVSGLQYR | 62 | 11 | | | | | | 10416 |
| HPV31 | L1 | VVSTDEYVTR | 21 | 10 | | | | | | 10417 |
| HPV31 | L1 | WACVGLEVGR | 101 | 10 | | | | | | 10418 |
| HPV31 | L1 | YAGGPGTDNR | 136 | 10 | | | | | | 10419 |
| HPV31 | L1 | YLPPVPVSK | 12 | 9 | | | | | | 10420 |
| HPV31 | L1 | YLRREQMFVR | 250 | 10 | | | | | | 10421 |
| HPV31 | L1 | YSIPKSDNPK | 50 | 10 | | | | | | 10422 |
| HPV31 | L1 | YSIPKSDNPKK | 50 | 11 | | | | | | 10423 |
| HPV31 | L1 | YVFWEVNLK | 445 | 9 | | | | | | 10424 |
| HPV31 | L1 | YVFWEVNLKEK | 445 | 11 | | | | | | 10425 |
| HPV31 | L2 | ALHRPALTSR | 281 | 10 | | | | | | 10426 |
| HPV31 | L2 | ALHRPALTSRR | 281 | 11 | | | | | | 10427 |
| HPV31 | L2 | ALTSRRNTVR | 286 | 10 | | | | | | 10428 |
| HPV31 | L2 | ASATQLYQTCK | 13 | 11 | | | | | | 10429 |
| HPV31 | L2 | ATQLYQTCK | 15 | 9 | | | | | | 10430 |
| HPV31 | L2 | FLDIIALHR | 276 | 9 | | | | | | 10431 |
| HPV31 | L2 | GIGSGSGTGGR | 59 | 11 | | | | | | 10432 |
| HPV31 | L2 | GLYSKATQQVK | 221 | 11 | | | | | | 10433 |
| HPV31 | L2 | GSGSGTGGR | 61 | 9 | | | | | | 10434 |
| HPV31 | L2 | GTCPSDVIPK | 26 | 10 | | | | | | 10435 |
| HPV31 | L2 | HTTIADQILR | 38 | 10 | | | | | | 10436 |
| HPV31 | L2 | IALHRPALTSR | 280 | 11 | | | | | | 10437 |
| HPV31 | L2 | ITSSTPIPGVR | 205 | 11 | | | | | | 10438 |
| HPV31 | L2 | LTSRRNTVR | 287 | 9 | | | | | | 10439 |
| HPV31 | L2 | MLKRRRKR | 447 | 8 | | | | | | 10440 |
| HPV31 | L2 | NTVRYSRLGNK | 292 | 11 | | | | | | 10441 |
| HPV31 | L2 | PALTSRRNTVR | 285 | 11 | | | | | | 10442 |
| HPV31 | L2 | PARLGLYSK | 217 | 9 | | | | | | 10443 |
| HPV31 | L2 | PIPGVRRPAR | 210 | 10 | | | | | | 10444 |
| HPV31 | L2 | PSYYMLKR | 443 | 8 | | | | | | 10445 |
| HPV31 | L2 | PSYYMLKRR | 443 | 9 | | | | | | 10446 |
| HPV31 | L2 | PSYYMLKRRR | 443 | 10 | | | | | | 10447 |
| HPV31 | L2 | PSYYMLKRRRK | 443 | 11 | | | | | | 10448 |
| HPV31 | L2 | PTFLSAPK | 235 | 8 | | | | | | 10449 |
| HPV31 | L2 | RLGNKQTLR | 298 | 9 | | | | | | 10450 |
| HPV31 | L2 | RLGNKQTLRTR | 298 | 11 | | | | | | 10451 |
| HPV31 | L2 | RSGATIGAR | 308 | 9 | | | | | | 10452 |
| HPV31 | L2 | RSKRSTKR | 2 | 8 | | | | | | 10453 |
| HPV31 | L2 | RSKRSTKRTK | 2 | 10 | | | | | | 10454 |
| HPV31 | L2 | RSKRSTKRTKR | 2 | 11 | | | | | | 10455 |
| HPV31 | L2 | RSTKRTKR | 5 | 8 | | | | | | 10456 |
| HPV31 | L2 | RTGYVPLSTR | 69 | 10 | | | | | | 10457 |
| HPV31 | L2 | RTRSGATIGAR | 306 | 11 | | | | | | 10458 |
| HPV31 | L2 | SATQLYQTCK | 14 | 10 | | | | | | 10459 |
| HPV31 | L2 | SSTPIPGVR | 207 | 9 | | | | | | 10460 |
| HPV31 | L2 | SSTPIPGVRR | 207 | 10 | | | | | | 10461 |
| HPV31 | L2 | STPIPGVR | 208 | 8 | | | | | | 10462 |
| HPV31 | L2 | STPIPGVRR | 208 | 9 | | | | | | 10463 |
| HPV31 | L2 | STVSEASIPIR | 80 | 11 | | | | | | 10464 |
| HPV31 | L2 | TIADQILR | 40 | 8 | | | | | | 10465 |
| HPV31 | L2 | TSRRNTVR | 288 | 8 | | | | | | 10466 |
| HPV31 | L2 | TSRRNTVRYSR | 288 | 11 | | | | | | 10467 |
| HPV31 | L2 | TSSTPIPGVR | 206 | 10 | | | | | | 10468 |
| HPV31 | L2 | TSSTPIPGVRR | 206 | 11 | | | | | | 10469 |
| HPV31 | L2 | TTIADQILR | 39 | 9 | | | | | | 10470 |
| HPV31 | L2 | TVRYSRLGNK | 293 | 10 | | | | | | 10471 |
| HPV31 | L2 | TVSEASIPIR | 81 | 10 | | | | | | 10472 |
| HPV31 | L2 | VIDPTFLSAPK | 232 | 11 | | | | | | 10473 |
| HPV31 | L2 | VSEASIPIR | 82 | 9 | | | | | | 10474 |
| HPV31 | L2 | YLHPSYYMLK | 440 | 10 | | | | | | 10475 |
| HPV31 | L2 | YLHPSYYMLKR | 440 | 11 | | | | | | 10476 |
| HPV31 | L2 | YMLKRRRK | 446 | 8 | | | | | | 10477 |
| HPV31 | L2 | YMLKRRRKR | 446 | 9 | | | | | | 10478 |
| HPV31 | L2 | YSKATQQVK | 223 | 9 | | | | | | 10479 |
| HPV31 | L2 | YSRLGNKQTLR | 296 | 11 | | | | | | 10480 |
| HPV33 | E1 | AAEDVVDR | 96 | 8 | | | | | | 10481 |
| HPV33 | E1 | AAFLKSNSQAK | 383 | 11 | | | | | | 10482 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV33 | E1 | AANPCRTSINK | 104 | 11 | | | | | | 10483 |
| HPV33 | E1 | AINDENWK | 596 | 8 | | | | | | 10484 |
| HPV33 | E1 | AVCALKRK | 81 | 8 | | | | | | 10485 |
| HPV33 | E1 | CMVIEPPK | 297 | 8 | | | | | | 10486 |
| HPV33 | E1 | CMVIEPPKLR | 297 | 10 | | | | | | 10487 |
| HPV33 | E1 | CSAGENTR | 633 | 8 | | | | | | 10488 |
| HPV33 | E1 | CSAGENTRSLR | 633 | 11 | | | | | | 10489 |
| HPV33 | E1 | CSKNRLTVAK | 276 | 10 | | | | | | 10490 |
| HPV33 | E1 | CVISCVNSK | 490 | 9 | | | | | | 10491 |
| HPV33 | E1 | DLIEEEDK | 614 | 8 | | | | | | 10492 |
| HPV33 | E1 | DLNAVCALK | 78 | 9 | | | | | | 10493 |
| HPV33 | E1 | DLNAVCALKR | 78 | 10 | | | | | | 10494 |
| HPV33 | E1 | DLNAVCALKRK | 78 | 11 | | | | | | 10495 |
| HPV33 | E1 | DSNSNAAAFLK | 377 | 11 | | | | | | 10496 |
| HPV33 | E1 | DSRWPYLHSR | 566 | 10 | | | | | | 10497 |
| HPV33 | E1 | DVKHRALVQLK | 541 | 11 | | | | | | 10498 |
| HPV33 | E1 | DVVDRAANPCR | 99 | 11 | | | | | | 10499 |
| HPV33 | E1 | EISIDVKHR | 537 | 9 | | | | | | 10500 |
| HPV33 | E1 | ELVRPFKSDK | 214 | 10 | | | | | | 10501 |
| HPV33 | E1 | ESLKVLIK | 242 | 8 | | | | | | 10502 |
| HPV33 | E1 | ETCMVIEPPK | 295 | 10 | | | | | | 10503 |
| HPV33 | E1 | EVEAVIER | 19 | 8 | | | | | | 10504 |
| HPV33 | E1 | EVEAVIERR | 19 | 9 | | | | | | 10505 |
| HPV33 | E1 | FLGAFKKFLK | 449 | 10 | | | | | | 10506 |
| HPV33 | E1 | FLKGIPKK | 456 | 8 | | | | | | 10507 |
| HPV33 | E1 | FLKSNSQAK | 385 | 9 | 0.0013 | 0.0002 | | | | 10508 |
| HPV33 | E1 | FMELVRPFK | 212 | 9 | | | | | | 10509 |
| HPV33 | E1 | FTAFLGAFK | 446 | 9 | | | | | | 10510 |
| HPV33 | E1 | FTAFLGAFKK | 446 | 10 | | | | | | 10511 |
| HPV33 | E1 | GAFKKFLK | 451 | 8 | | | | | | 10512 |
| HPV33 | E1 | GIIILLIR | 265 | 9 | | | | | | 10513 |
| HPV33 | E1 | GIIILLLIRFR | 265 | 11 | | | | | | 10514 |
| HPV33 | E1 | GIMCRHYK | 399 | 8 | | | | | | 10515 |
| HPV33 | E1 | GIMCRHYKK | 399 | 9 | | | | | | 10516 |
| HPV33 | E1 | GISFMELVR | 209 | 9 | | | | | | 10517 |
| HPV33 | E1 | GISPSVAESLK | 235 | 11 | | | | | | 10518 |
| HPV33 | E1 | GMSLIQFLK | 480 | 9 | | | | | | 10519 |
| HPV33 | E1 | GTTPEWIDR | 327 | 9 | | | | | | 10520 |
| HPV33 | E1 | HLQCLTCDR | 256 | 9 | | | | | | 10521 |
| HPV33 | E1 | HSRLTVFEFK | 573 | 10 | | | | | | 10522 |
| HPV33 | E1 | IIILLIR | 266 | 8 | | | | | | 10523 |
| HPV33 | E1 | IIILLLIRFR | 266 | 10 | | | | | | 10524 |
| HPV33 | E1 | IILLLIRFR | 267 | 9 | | | | | | 10525 |
| HPV33 | E1 | ILLLIRFR | 268 | 8 | | | | | | 10526 |
| HPV33 | E1 | ILLLIRFRCSK | 268 | 11 | | | | | | 10527 |
| HPV33 | E1 | IMCRHYKK | 400 | 8 | | | | | | 10528 |
| HPV33 | E1 | IMCRHYKKAEK | 400 | 11 | | | | | | 10529 |
| HPV33 | E1 | ISFMELVR | 210 | 8 | | | | | | 10530 |
| HPV33 | E1 | ISFMELVRPFK | 210 | 11 | | | | | | 10531 |
| HPV33 | E1 | ISIDVKHR | 538 | 8 | | | | | | 10532 |
| HPV33 | E1 | ISNVLHSSNTK | 187 | 11 | | | | | | 10533 |
| HPV33 | E1 | ISPSVAESLK | 236 | 10 | | | | | | 10534 |
| HPV33 | E1 | ISWTYIDDYMR | 520 | 11 | | | | | | 10535 |
| HPV33 | E1 | IVKDCGIMCR | 394 | 10 | | | | | | 10536 |
| HPV33 | E1 | KANILYKFK | 197 | 9 | | | | | | 10537 |
| HPV33 | E1 | KIVKDCGIMCR | 393 | 11 | | | | | | 10538 |
| HPV33 | E1 | KLDLIEEEDK | 612 | 10 | | | | | | 10539 |
| HPV33 | E1 | KMSIGQWIQSR | 412 | 11 | | | | | | 10540 |
| HPV33 | E1 | KSFFSRTWCK | 603 | 10 | | | | | | 10541 |
| HPV33 | E1 | KSNSQAKIVK | 387 | 10 | | | | | | 10542 |
| HPV33 | E1 | KTNDGGNWR | 425 | 9 | | | | | | 10543 |
| HPV33 | E1 | LICGPANTGK | 467 | 10 | | | | | | 10544 |
| HPV33 | E1 | LIRFRCSK | 271 | 8 | | | | | | 10545 |
| HPV33 | E1 | LIRFRCSKNR | 271 | 10 | | | | | | 10546 |
| HPV33 | E1 | LLIRFRCSK | 270 | 9 | | | | | | 10547 |
| HPV33 | E1 | LLIRFRCSKNR | 270 | 11 | | | | | | 10548 |
| HPV33 | E1 | LLLIRFRCSK | 269 | 10 | | | | | | 10549 |
| HPV33 | E1 | LVRPFKSDK | 215 | 9 | | | | | | 10550 |
| HPV33 | E1 | MLICGPANTGK | 466 | 11 | | | | | | 10551 |
| HPV33 | E1 | MSIGQWIQSR | 413 | 10 | | | | | | 10552 |
| HPV33 | E1 | MSLIQFLK | 481 | 8 | | | | | | 10553 |
| HPV33 | E1 | MVIEPPKLR | 298 | 9 | | | | | | 10554 |
| HPV33 | E1 | NAVCALKR | 80 | 8 | | | | | | 10555 |
| HPV33 | E1 | NAVCALKRK | 80 | 9 | | | | | | 10556 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV33 | E1 | NSIQADTEAAR | 57 | 11 | | | | | | 10557 |
| HPV33 | E1 | NSNAAAFLK | 379 | 9 | 0.0057 | 0.3700 | | | | 10558 |
| HPV33 | E1 | NSQAKIVK | 389 | 8 | | | | | | 10559 |
| HPV33 | E1 | NTKANILYK | 195 | 9 | | | | | | 10560 |
| HPV33 | E1 | NTKANILYKFK | 195 | 11 | | | | | | 10561 |
| HPV33 | E1 | NTNAGTDSR | 560 | 9 | | | | | | 10562 |
| HPV33 | E1 | NVLHSSNTK | 189 | 9 | | | | | | 10563 |
| HPV33 | E1 | PSVAESLK | 238 | 8 | | | | | | 10564 |
| HPV33 | E1 | PVYAINDENWK | 593 | 11 | | | | | | 10565 |
| HPV33 | E1 | QADTEAAR | 60 | 8 | | | | | | 10566 |
| HPV33 | E1 | QSAAEDVVDR | 94 | 10 | | | | | | 10567 |
| HPV33 | E1 | QTCALYWFR | 308 | 9 | | | | | | 10568 |
| HPV33 | E1 | RLTVFEFK | 575 | 8 | | | | | | 10569 |
| HPV33 | E1 | RSQTCALYWFR | 306 | 11 | | | | | | 10570 |
| HPV33 | E1 | RTSINKNK | 109 | 8 | | | | | | 10571 |
| HPV33 | E1 | SAAEDVVDR | 95 | 9 | | | | | | 10572 |
| HPV33 | E1 | SAGENTRSLR | 634 | 10 | | | | | | 10573 |
| HPV33 | E1 | SIGQWIQSR | 414 | 9 | | | | | | 10574 |
| HPV33 | E1 | SINKNKECTYR | 111 | 11 | | | | | | 10575 |
| HPV33 | E1 | SIQADTEAAR | 58 | 10 | | | | | | 10576 |
| HPV33 | E1 | SSNTKANILYK | 193 | 11 | | | | | | 10577 |
| HPV33 | E1 | SVAESLKVLIK | 239 | 11 | | | | | | 10578 |
| HPV33 | E1 | TAFLGAFK | 447 | 8 | | | | | | 10579 |
| HPV33 | E1 | TAFLGAFKK | 447 | 9 | | | | | | 10580 |
| HPV33 | E1 | TSNTNAGTDSR | 558 | 11 | | | | | | 10581 |
| HPV33 | E1 | TTPEWIDR | 328 | 8 | | | | | | 10582 |
| HPV33 | E1 | VAESLKVLIK | 240 | 10 | | | | | | 10583 |
| HPV33 | E1 | VIEPPKLR | 299 | 8 | | | | | | 10584 |
| HPV33 | E1 | VISCVNSK | 491 | 8 | | | | | | 10585 |
| HPV33 | E1 | VLHSSNTK | 190 | 8 | | | | | | 10586 |
| HPV33 | E1 | VVDRAANPCR | 100 | 10 | | | | | | 10587 |
| HPV33 | E1 | WIQSRCEK | 418 | 8 | | | | | | 10588 |
| HPV33 | E1 | WLQPLSDAK | 502 | 9 | | | | | | 10589 |
| HPV33 | E1 | WTYIDDYMR | 522 | 9 | | | | | | 10590 |
| HPV33 | E1 | YAINDENWK | 595 | 9 | | | | | | 10591 |
| HPV33 | E1 | YTHLQCLTCDR | 254 | 11 | | | | | | 10592 |
| HPV33 | E2 | ALDNRTAR | 249 | 8 | | | | | | 10593 |
| HPV33 | E2 | ATNCTNKQR | 258 | 9 | | | | | | 10594 |
| HPV33 | E2 | CADPALDNR | 245 | 9 | | | | | | 10595 |
| HPV33 | E2 | CALLYTAK | 40 | 8 | | | | | | 10596 |
| HPV33 | E2 | CLRYRLKPYK | 288 | 10 | | | | | | 10597 |
| HPV33 | E2 | DIQTDNDNR | 211 | 9 | | | | | | 10598 |
| HPV33 | E2 | DLPSQIEHWK | 25 | 10 | | | | | | 10599 |
| HPV33 | E2 | DTAQPLTK | 235 | 8 | | | | | | 10600 |
| HPV33 | E2 | DTCTMVTGK | 143 | 9 | | | | | | 10601 |
| HPV33 | E2 | DTTDTAQPLTK | 232 | 11 | | | | | | 10602 |
| HPV33 | E2 | ELQMALETLSK | 74 | 11 | | | | | | 10603 |
| HPV33 | E2 | ESNSLKCLRYR | 282 | 9 | | | | | | 10604 |
| HPV33 | E2 | ESNSLKCLRYR | 282 | 11 | | | | | | 10605 |
| HPV33 | E2 | ETVTVQYDNDK | 115 | 11 | | | | | | 10606 |
| HPV33 | E2 | EVWLCEPPK | 100 | 9 | | | | | | 10607 |
| HPV33 | E2 | GMYYIHNCEK | 156 | 10 | | | | | | 10608 |
| HPV33 | E2 | HLKGESNSLK | 278 | 10 | | | | | | 10609 |
| HPV33 | E2 | ILDLYEADK | 15 | 9 | | | | | | 10610 |
| HPV33 | E2 | ISARLNAVQEK | 4 | 11 | | | | | | 10611 |
| HPV33 | E2 | KILDLYEADK | 14 | 10 | | | | | | 10612 |
| HPV33 | E2 | KVYFKYFK | 165 | 8 | | | | | | 10613 |
| HPV33 | E2 | MALETLSK | 77 | 8 | | | | | | 10614 |
| HPV33 | E2 | NSLKCLRYR | 284 | 9 | | | | | | 10615 |
| HPV33 | E2 | NSLKCLRYRLK | 284 | 11 | | | | | | 10616 |
| HPV33 | E2 | NVAPIVHLK | 272 | 9 | | | | | | 10617 |
| HPV33 | E2 | PALDNRTAR | 248 | 9 | | | | | | 10618 |
| HPV33 | E2 | PSLLASKTK | 60 | 9 | | | | | | 10619 |
| HPV33 | E2 | PSQIEHWK | 27 | 8 | | | | | | 10620 |
| HPV33 | E2 | PSQIEHWKLIR | 27 | 11 | | | | | | 10621 |
| HPV33 | E2 | QAAAKRRR | 222 | 8 | | | | | | 10622 |
| HPV33 | E2 | QIEHWKLIR | 29 | 9 | | | | | | 10623 |
| HPV33 | E2 | QMALETLSK | 76 | 9 | | | | | | 10624 |
| HPV33 | E2 | QMFLGTVK | 332 | 8 | | | | | | 10625 |
| HPV33 | E2 | QVVPSLLASK | 57 | 10 | | | | | | 10626 |
| HPV33 | E2 | RLNAVQEK | 7 | 8 | | | | | | 10627 |
| HPV33 | E2 | RMECALLYTAK | 37 | 11 | | | | | | 10628 |
| HPV33 | E2 | RTATNCTNK | 256 | 9 | | | | | | 10629 |
| HPV33 | E2 | RTATNCTNKQR | 256 | 11 | | | | | | 10630 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV33 | E2 | SARLNAVQEK | 5 | 10 | | | | | | 10631 |
| HPV33 | E2 | SLEVWLCEPPK | 98 | 11 | | | | | | 10632 |
| HPV33 | E2 | SLKCLRYR | 285 | 8 | | | | | | 10633 |
| HPV33 | E2 | SLKCLRYRLK | 285 | 10 | | | | | | 10634 |
| HPV33 | E2 | SLLASKTK | 61 | 8 | | | | | | 10635 |
| HPV33 | E2 | SSNVAPIVHLK | 270 | 11 | | | | | | 10636 |
| HPV33 | E2 | SSTWHWTSDNK | 304 | 11 | | | | | | 10637 |
| HPV33 | E2 | STWHWTSDNK | 305 | 10 | | | | | | 10638 |
| HPV33 | E2 | TADIQTDNDNR | 209 | 11 | | | | | | 10639 |
| HPV33 | E2 | TARTATNCTNK | 254 | 11 | | | | | | 10640 |
| HPV33 | E2 | TATNCTNK | 257 | 8 | | | | | | 10641 |
| HPV33 | E2 | TATNCTNKQR | 257 | 10 | | | | | | 10642 |
| HPV33 | E2 | TSDNKNSK | 310 | 8 | | | | | | 10643 |
| HPV33 | E2 | TTDTAQPLTK | 233 | 10 | | | | | | 10644 |
| HPV33 | E2 | TVQYDNDK | 118 | 8 | | | | | | 10645 |
| HPV33 | E2 | TVQYDNDKK | 118 | 9 | | | | | | 10646 |
| HPV33 | E2 | TVTVQYDNDK | 116 | 10 | | | | | | 10647 |
| HPV33 | E2 | TVTVQYDNDKK | 116 | 11 | | | | | | 10648 |
| HPV33 | E2 | VAPIVHLK | 273 | 8 | | | | | | 10649 |
| HPV33 | E2 | VTVQYDNDK | 117 | 9 | | | | | | 10650 |
| HPV33 | E2 | VTVQYDNDKK | 117 | 10 | | | | | | 10651 |
| HPV33 | E2 | VVPSLLASK | 58 | 9 | | | | | | 10652 |
| HPV33 | E2 | VVPSLLASKTK | 58 | 11 | | | | | | 10653 |
| HPV33 | E2 | WLCEPPKCFK | 102 | 10 | | | | | | 10654 |
| HPV33 | E2 | WLCEPPKCFKK | 102 | 11 | | | | | | 10655 |
| HPV33 | E2 | WTSDNKNSK | 309 | 9 | | | | | | 10656 |
| HPV33 | E2 | YIHNCEKVYFK | 159 | 11 | | | | | | 10657 |
| HPV33 | E5 | FLCLSLLLR | 12 | 9 | | | | | | 10658 |
| HPV33 | E5 | ILFLCLSLLLR | 10 | 11 | | | | | | 10659 |
| HPV33 | E5 | LLWVFVGSPLK | 38 | 11 | | | | | | 10660 |
| HPV33 | E5 | WVFVGSPLK | 40 | 9 | | | | | | 10661 |
| HPV33 | E6 | AACWRSRR | 137 | 8 | | | | | | 10662 |
| HPV33 | E6 | AACWRSRRR | 137 | 9 | | | | | | 10663 |
| HPV33 | E6 | CAACWRSR | 136 | 8 | | | | | | 10664 |
| HPV33 | E6 | CAACWRSRR | 136 | 9 | | | | | | 10665 |
| HPV33 | E6 | CAACWRSRRR | 136 | 10 | | | | | | 10666 |
| HPV33 | E6 | CVECKKPLQR | 30 | 10 | | | | | | 10667 |
| HPV33 | E6 | EILIRCIICQR | 98 | 11 | | | | | | 10668 |
| HPV33 | E6 | ELQCVECK | 27 | 8 | | | | | | 10669 |
| HPV33 | E6 | ELQCVECKK | 27 | 9 | | | | | | 10670 |
| HPV33 | E6 | FADLTVVYR | 47 | 9 | | | | | | 10671 |
| HPV33 | E6 | FAFADLTVVYR | 45 | 11 | | | | | | 10672 |
| HPV33 | E6 | FLSKISEYR | 69 | 9 | | | | | | 10673 |
| HPV33 | E6 | GICKLCLR | 61 | 8 | | | | | | 10674 |
| HPV33 | E6 | ILIRCIICQR | 99 | 10 | | | | | | 10675 |
| HPV33 | E6 | ISGRWAGR | 128 | 8 | | | | | | 10676 |
| HPV33 | E6 | KLCLRFLSK | 64 | 9 | | | | | | 10677 |
| HPV33 | E6 | LIRCIICQR | 100 | 9 | | | | | | 10678 |
| HPV33 | E6 | LSKISEYR | 70 | 8 | | | | | | 10679 |
| HPV33 | E6 | NIELQCVECK | 25 | 10 | | | | | | 10680 |
| HPV33 | E6 | NIELQCVECKK | 25 | 11 | | | | | | 10681 |
| HPV33 | E6 | NISGRWAGR | 127 | 9 | | | | | | 10682 |
| HPV33 | E6 | NTLEQTVK | 86 | 8 | | | | | | 10683 |
| HPV33 | E6 | NTLEQTVKK | 86 | 9 | | | | | | 10684 |
| HPV33 | E6 | PLCPQEKK | 109 | 8 | | | | | | 10685 |
| HPV33 | E6 | PLCPQEKKR | 109 | 9 | | | | | | 10686 |
| HPV33 | E6 | PLNEILIR | 95 | 8 | | | | | | 10687 |
| HPV33 | E6 | TLEQTVKK | 87 | 8 | | | | | | 10688 |
| HPV33 | E6 | WAGRCAACWR | 132 | 10 | | | | | | 10689 |
| HPV33 | E7 | CVNSTASDLR | 68 | 10 | | | | | | 10690 |
| HPV33 | E7 | DSSDEDEGLDR | 30 | 11 | | | | | | 10691 |
| HPV33 | E7 | HTCNTTVR | 59 | 8 | | | | | | 10692 |
| HPV33 | E7 | NSTASDLR | 70 | 8 | | | | | | 10693 |
| HPV33 | E7 | SSDEDEGLDR | 31 | 10 | | | | | | 10694 |
| HPV33 | L1 | AITCQKTVPPK | 424 | 11 | | | | | | 10695 |
| HPV33 | L1 | ASLQDTYR | 411 | 8 | | | | | | 10696 |
| HPV33 | L1 | AVGHPYFSIK | 44 | 10 | | | | | | 10697 |
| HPV33 | L1 | AVPDDLYIK | 270 | 9 | | | | | | 10698 |
| HPV33 | L1 | CMDFKTLQANK | 207 | 11 | | | | | | 10699 |
| HPV33 | L1 | CTQVTSDSTYK | 345 | 11 | | | | | | 10700 |
| HPV33 | L1 | CVGLEIGR | 103 | 8 | | | | | | 10701 |
| HPV33 | L1 | DICGSTCK | 223 | 8 | | | | | | 10702 |
| HPV33 | L1 | DLDQFPLGR | 457 | 9 | | | | | | 10703 |
| HPV33 | L1 | DLDQFPLGRK | 457 | 10 | | | | | | 10704 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV33 | L1 | DLQFVFQLCK | 370 | 10 | | | | | | 10705 |
| HPV33 | L1 | DSLFFFLR | 244 | 8 | | | | | | 10706 |
| HPV33 | L1 | DSLFFFLRR | 244 | 9 | | | | | | 10707 |
| HPV33 | L1 | DSTYKNENFK | 351 | 10 | | | | | | 10708 |
| HPV33 | L1 | DTGFGCMDFK | 202 | 10 | | | | | | 10709 |
| HPV33 | L1 | DTSFYNPDTQR | 88 | 11 | | | | | | 10710 |
| HPV33 | L1 | EAVPDDLYIK | 269 | 10 | | | | | | 10711 |
| HPV33 | L1 | FLLQAGLK | 467 | 8 | | | | | | 10712 |
| HPV33 | L1 | FLLQAGLKAK | 467 | 10 | | | | | | 10713 |
| HPV33 | L1 | FLRREQMFVR | 249 | 10 | | | | | | 10714 |
| HPV33 | L1 | FSIKNPTNAK | 50 | 10 | | | | | | 10715 |
| HPV33 | L1 | FSIKNPTNAKK | 50 | 11 | | | | | | 10716 |
| HPV33 | L1 | FVRHFFNR | 256 | 8 | | | | | | 10717 |
| HPV33 | L1 | FVTSQAITCQK | 419 | 11 | | | | | | 10718 |
| HPV33 | L1 | FVTVVDTTR | 330 | 9 | | | | | | 10719 |
| HPV33 | L1 | GISGHPLLNK | 117 | 10 | | | | | | 10720 |
| HPV33 | L1 | GLKAKPKLK | 472 | 9 | | | | | | 10721 |
| HPV33 | L1 | GLKAKPKLKR | 472 | 10 | | | | | | 10722 |
| HPV33 | L1 | GLQYRVFR | 68 | 8 | | | | | | 10723 |
| HPV33 | L1 | GLQYRVFRVR | 68 | 10 | | | | | | 10724 |
| HPV33 | L1 | GSTCKYPDYLK | 226 | 11 | | | | | | 10725 |
| HPV33 | L1 | ISGHPLLNK | 118 | 9 | | | | | | 10726 |
| HPV33 | L1 | ITCQKTVPPK | 425 | 10 | | | | | | 10727 |
| HPV33 | L1 | KAKPKLKR | 474 | 8 | | | | | | 10728 |
| HPV33 | L1 | KLKRAAPTSTR | 478 | 11 | | | | | | 10729 |
| HPV33 | L1 | KTVPPKEK | 429 | 8 | | | | | | 10730 |
| HPV33 | L1 | KVSGLQYR | 65 | 8 | | | | | | 10731 |
| HPV33 | L1 | KVSGLQYRVFR | 65 | 11 | | | | | | 10732 |
| HPV33 | L1 | KVVSTDEYVSR | 20 | 11 | | | | | | 10733 |
| HPV33 | L1 | LAVGHPYFSIK | 43 | 11 | | | | | | 10734 |
| HPV33 | L1 | LLQAGLKAK | 468 | 9 | | | | | | 10735 |
| HPV33 | L1 | LLQAGLKAKPK | 468 | 11 | | | | | | 10736 |
| HPV33 | L1 | LVPKVSGLQYR | 62 | 11 | | | | | | 10737 |
| HPV33 | L1 | MVTSESQLFNK | 299 | 11 | | | | | | 10738 |
| HPV33 | L1 | NAKKLLVPK | 57 | 9 | | | | | | 10739 |
| HPV33 | L1 | PIDICGSTCK | 221 | 10 | | | | | | 10740 |
| HPV33 | L1 | PSASLQDTYR | 409 | 10 | | | | | | 10741 |
| HPV33 | L1 | PTGEHWGK | 165 | 8 | | | | | | 10742 |
| HPV33 | L1 | PTNAKKLLVPK | 55 | 11 | | | | | | 10743 |
| HPV33 | L1 | PTSTRTSSAK | 484 | 10 | | | | | | 10744 |
| HPV33 | L1 | PTSTRTSSAKR | 484 | 11 | | | | | | 10745 |
| HPV33 | L1 | QAGLKAKPK | 470 | 9 | | | | | | 10746 |
| HPV33 | L1 | QAGLKAKPKLK | 470 | 11 | | | | | | 10747 |
| HPV33 | L1 | QLCLLGCK | 156 | 8 | | | | | | 10748 |
| HPV33 | L1 | QLFNKPYWLQR | 305 | 11 | | | | | | 10749 |
| HPV33 | L1 | QMFVRHFFNR | 254 | 10 | | | | | | 10750 |
| HPV33 | L1 | QTQLCLLGCK | 154 | 10 | | | | | | 10751 |
| HPV33 | L1 | QVFVTVVDTTR | 328 | 11 | | | | | | 10752 |
| HPV33 | L1 | QVTSDSTYK | 347 | 9 | | | | | | 10753 |
| HPV33 | L1 | RAAPTSTR | 481 | 8 | | | | | | 10754 |
| HPV33 | L1 | RTSSAKRK | 488 | 8 | | | | | | 10755 |
| HPV33 | L1 | RTSSAKRKK | 488 | 9 | | | | | | 10756 |
| HPV33 | L1 | RTSSAKRKKVK | 488 | 11 | | | | | | 10757 |
| HPV33 | L1 | RVRLPDPNK | 75 | 9 | | | | | | 10758 |
| HPV33 | L1 | SADLDQFPLGR | 455 | 11 | | | | | | 10759 |
| HPV33 | L1 | SAKRKKVK | 491 | 8 | | | | | | 10760 |
| HPV33 | L1 | SAKRKKVKK | 491 | 9 | | | | | | 10761 |
| HPV33 | L1 | SASLQDTYR | 410 | 9 | | | | | | 10762 |
| HPV33 | L1 | SIKNPTNAK | 51 | 9 | | | | | | 10763 |
| HPV33 | L1 | SIKNPTNAKK | 51 | 10 | | | | | | 10764 |
| HPV33 | L1 | SIYYYAGSSR | 32 | 10 | | | | | | 10765 |
| HPV33 | L1 | SLFFFLRR | 245 | 8 | | | | | | 10766 |
| HPV33 | L1 | SSAKRKKVK | 490 | 9 | | | | | | 10767 |
| HPV33 | L1 | SSAKRKKVKK | 490 | 10 | | | | | | 10768 |
| HPV33 | L1 | STCKYPDYLK | 227 | 10 | | | | | | 10769 |
| HPV33 | L1 | STDEYVSR | 23 | 8 | | | | | | 10770 |
| HPV33 | L1 | STRTSSAK | 486 | 8 | | | | | | 10771 |
| HPV33 | L1 | STRTSSAKR | 486 | 9 | | | | | | 10772 |
| HPV33 | L1 | STRTSSAKRK | 486 | 10 | | | | | | 10773 |
| HPV33 | L1 | STRTSSAKRKK | 486 | 11 | | | | | | 10774 |
| HPV33 | L1 | STYKNENFK | 352 | 9 | | | | | | 10775 |
| HPV33 | L1 | TSESQLFNK | 301 | 9 | | | | | | 10776 |
| HPV33 | L1 | TSFYNPDTQR | 89 | 10 | | | | | | 10777 |
| HPV33 | L1 | TSIYYYAGSSR | 31 | 11 | | | | | | 10778 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV33 | L1 | TSQAITCQK | 421 | 9 | | | | | | 10779 |
| HPV33 | L1 | TSSAKRKK | 489 | 8 | | | | | | 10780 |
| HPV33 | L1 | TSSAKRKKVK | 489 | 10 | | | | | | 10781 |
| HPV33 | L1 | TSSAKRKKVKK | 489 | 11 | | | | | | 10782 |
| HPV33 | L1 | TSTRTSSAK | 485 | 9 | | | | | | 10783 |
| HPV33 | L1 | TSTRTSSAKR | 485 | 10 | | | | | | 10784 |
| HPV33 | L1 | TSTRTSSAKRK | 485 | 11 | | | | | | 10785 |
| HPV33 | L1 | TVYLPPVPVSK | 10 | 11 | | | | | | 10786 |
| HPV33 | L1 | VSGLQYRVFR | 66 | 10 | | | | | | 10787 |
| HPV33 | L1 | VSTDEYVSR | 22 | 9 | | | | | | 10788 |
| HPV33 | L1 | VTSDSTYK | 348 | 8 | | | | | | 10789 |
| HPV33 | L1 | VTSESQLFNK | 300 | 10 | | | | | | 10790 |
| HPV33 | L1 | VTSQAITCQK | 420 | 10 | | | | | | 10791 |
| HPV33 | L1 | VTVVDTTR | 331 | 8 | | | | | | 10792 |
| HPV33 | L1 | VVSTDEYVSR | 21 | 10 | | | | | | 10793 |
| HPV33 | L1 | WACVGLEIGR | 101 | 10 | | | | | | 10794 |
| HPV33 | L1 | YLPPVPVSK | 12 | 9 | | | | | | 10795 |
| HPV33 | L1 | YTFWEVDLK | 443 | 9 | | | | | | 10796 |
| HPV33 | L1 | YTFWEVDLKEK | 443 | 11 | | | | | | 10797 |
| HPV33 | L2 | AAIPLQPIR | 81 | 9 | | | | | | 10798 |
| HPV33 | L2 | AIPLQPIR | 82 | 8 | | | | | | 10799 |
| HPV33 | L2 | AITSRRHTVR | 291 | 10 | | | | | | 10800 |
| HPV33 | L2 | ALHRPAITSR | 286 | 10 | | | | | | 10801 |
| HPV33 | L2 | ALHRPAITSRR | 286 | 11 | | | | | | 10802 |
| HPV33 | L2 | ASATQLYQTCK | 12 | 11 | | | | | | 10803 |
| HPV33 | L2 | ATLKTRSGK | 308 | 9 | | | | | | 10804 |
| HPV33 | L2 | ATQLYQTCK | 14 | 9 | | | | | | 10805 |
| HPV33 | L2 | FILRRRRK | 447 | 8 | | | | | | 10806 |
| HPV33 | L2 | FILRRRRKR | 447 | 9 | | | | | | 10807 |
| HPV33 | L2 | FLDIIALHR | 281 | 9 | | | | | | 10808 |
| HPV33 | L2 | FSRVGQKATLK | 301 | 11 | | | | | | 10809 |
| HPV33 | L2 | FVLHPSYFILR | 440 | 11 | | | | | | 10810 |
| HPV33 | L2 | GIGTGSGSGGR | 58 | 11 | | | | | | 10811 |
| HPV33 | L2 | GLYSRNTQQVK | 226 | 11 | | | | | | 10812 |
| HPV33 | L2 | GSTIADQILK | 37 | 10 | | | | | | 10813 |
| HPV33 | L2 | GTCPPDVIPK | 25 | 10 | | | | | | 10814 |
| HPV33 | L2 | GTGSGSGGR | 60 | 9 | | | | | | 10815 |
| HPV33 | L2 | HSYSTFATTR | 379 | 10 | | | | | | 10816 |
| HPV33 | L2 | HTVRFSRVGQK | 297 | 11 | | | | | | 10817 |
| HPV33 | L2 | IALHRPAITSR | 285 | 11 | | | | | | 10818 |
| HPV33 | L2 | ILRRRRKR | 448 | 8 | | | | | | 10819 |
| HPV33 | L2 | ITSRRHTVR | 292 | 9 | | | | | | 10820 |
| HPV33 | L2 | KATLKTRSGK | 307 | 10 | | | | | | 10821 |
| HPV33 | L2 | KTRSGKQIGAR | 311 | 11 | | | | | | 10822 |
| HPV33 | L2 | PAFLTSPHK | 240 | 9 | | | | | | 10823 |
| HPV33 | L2 | PAITSRRHTVR | 290 | 11 | | | | | | 10824 |
| HPV33 | L2 | PIPGSRPVAR | 215 | 10 | | | | | | 10825 |
| HPV33 | L2 | PSYFILRR | 444 | 8 | | | | | | 10826 |
| HPV33 | L2 | PSYFILRRR | 444 | 9 | | | | | | 10827 |
| HPV33 | L2 | PSYFILRRRR | 444 | 10 | | | | | | 10828 |
| HPV33 | L2 | PSYFILRRRRK | 444 | 11 | | | | | | 10829 |
| HPV33 | L2 | PTAAIPLQPIR | 79 | 11 | | | | | | 10830 |
| HPV33 | L2 | PVARLGLYSR | 221 | 10 | | | | | | 10831 |
| HPV33 | L2 | RSGKQIGAR | 313 | 9 | | | | | | 10832 |
| HPV33 | L2 | RVGQKATLK | 303 | 9 | | | | | | 10833 |
| HPV33 | L2 | RVGQKATLKTR | 303 | 11 | | | | | | 10834 |
| HPV33 | L2 | SATQLYQTCK | 13 | 10 | | | | | | 10835 |
| HPV33 | L2 | SSTPIPGSR | 212 | 9 | | | | | | 10836 |
| HPV33 | L2 | STIADQILK | 38 | 9 | | | | | | 10837 |
| HPV33 | L2 | STPIPGSR | 213 | 8 | | | | | | 10838 |
| HPV33 | L2 | TAAIPLQPIR | 80 | 10 | | | | | | 10839 |
| HPV33 | L2 | TIADQILK | 39 | 8 | | | | | | 10840 |
| HPV33 | L2 | TLKTRSGK | 309 | 8 | | | | | | 10841 |
| HPV33 | L2 | TSRRHTVR | 293 | 8 | | | | | | 10842 |
| HPV33 | L2 | TSRRHTVRFSR | 293 | 11 | | | | | | 10843 |
| HPV33 | L2 | TSSTPIPGSR | 211 | 10 | | | | | | 10844 |
| HPV33 | L2 | TVRFSRVGQK | 298 | 10 | | | | | | 10845 |
| HPV33 | L2 | VARLGLYSR | 222 | 9 | | | | | | 10846 |
| HPV33 | L2 | VLHPSYFILR | 441 | 10 | | | | | | 10847 |
| HPV33 | L2 | VLHPSYFILRR | 441 | 11 | | | | | | 10848 |
| HPV33 | L2 | VTSSTPIPGSR | 210 | 11 | | | | | | 10849 |
| HPV33 | L2 | YSRNTQQVK | 228 | 9 | | | | | | 10850 |
| HPV33 | L2 | YSTFATTR | 381 | 8 | | | | | | 10851 |
| HPV45 | E1 | AAFLKSNCQAK | 383 | 11 | | | | | | 10852 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV45 | E1 | AAMLAVFK | 198 | 8 | | | | | | 10853 |
| HPV45 | E1 | ALDGNPISIDR | 532 | 11 | | | | | | 10854 |
| HPV45 | E1 | ALKEFLKGTPK | 452 | 11 | | | | | | 10855 |
| HPV45 | E1 | ALLRYKCGK | 270 | 9 | 0.0900 | 0.1400 | | | | 10856 |
| HPV45 | E1 | ALLRYKCGKNR | 270 | 11 | | | | | | 10857 |
| HPV45 | E1 | AVMCRHYK | 399 | 8 | | | | | | 10858 |
| HPV45 | E1 | AVMCRHYKR | 399 | 9 | | | | | | 10859 |
| HPV45 | E1 | CAVMCRHYK | 398 | 9 | | | | | | 10860 |
| HPV45 | E1 | CAVMCRHYKR | 398 | 10 | | | | | | 10861 |
| HPV45 | E1 | CMLIEPPK | 297 | 8 | | | | | | 10862 |
| HPV45 | E1 | CMLIEPPKLR | 297 | 10 | | | | | | 10863 |
| HPV45 | E1 | CSKIDEGGDWR | 423 | 11 | | | | | | 10864 |
| HPV45 | E1 | CVTGQNTR | 634 | 8 | | | | | | 10865 |
| HPV45 | E1 | DAQVLHLLK | 78 | 9 | | | | | | 10866 |
| HPV45 | E1 | DAQVLHLLKR | 78 | 10 | | | | | | 10867 |
| HPV45 | E1 | DAQVLHLLKRK | 78 | 11 | | | | | | 10868 |
| HPV45 | E1 | DLVRNFKSDK | 214 | 10 | | | | | | 10869 |
| HPV45 | E1 | DTEGIPFGTFK | 623 | 11 | | | | | | 10870 |
| HPV45 | E1 | DTPEWIQR | 328 | 8 | | | | | | 10871 |
| HPV45 | E1 | EINDKNWK | 596 | 8 | | | | | | 10872 |
| HPV45 | E1 | EISLNSGHK | 115 | 9 | | | | | | 10873 |
| HPV45 | E1 | EISLNSGHKK | 115 | 10 | | | | | | 10874 |
| HPV45 | E1 | ELKELLQASNK | 186 | 11 | | | | | | 10875 |
| HPV45 | E1 | ELLQASNK | 189 | 8 | | | | | | 10876 |
| HPV45 | E1 | ELLQASNKK | 189 | 9 | | | | | | 10877 |
| HPV45 | E1 | ETCMLIEPPK | 295 | 10 | | | | | | 10878 |
| HPV45 | E1 | FISFLRALK | 446 | 9 | | | | | | 10879 |
| HPV45 | E1 | FLKGTPKK | 456 | 8 | | | | | | 10880 |
| HPV45 | E1 | FLKSNCQAK | 385 | 9 | 0.0035 | 0.0007 | | | | 10881 |
| HPV45 | E1 | FLRALKEFLK | 449 | 10 | | | | | | 10882 |
| HPV45 | E1 | FTDLVRNFK | 212 | 9 | | | | | | 10883 |
| HPV45 | E1 | FTFPHAFPFDK | 579 | 11 | | | | | | 10884 |
| HPV45 | E1 | FVETIVEK | 19 | 8 | | | | | | 10885 |
| HPV45 | E1 | FVETIVEKK | 19 | 9 | | | | | | 10886 |
| HPV45 | E1 | GIPFGTFK | 626 | 8 | | | | | | 10887 |
| HPV45 | E1 | GLSFTDLVR | 209 | 9 | 0.0009 | 0.0025 | | | | 10888 |
| HPV45 | E1 | GVEFISFLR | 443 | 9 | | | | | | 10889 |
| HPV45 | E1 | GVLILARLLR | 265 | 9 | 0.0058 | 0.1400 | | | | 10890 |
| HPV45 | E1 | GVLILALLRYK | 265 | 11 | | | | | | 10891 |
| HPV45 | E1 | GVNPTVAEGFK | 235 | 11 | | | | | | 10892 |
| HPV45 | E1 | HIQCLDCK | 256 | 8 | | | | | | 10893 |
| HPV45 | E1 | ILALLRYK | 268 | 8 | | | | | | 10894 |
| HPV45 | E1 | ILALLRYKCGK | 268 | 11 | | | | | | 10895 |
| HPV45 | E1 | ILLTSNIDPAK | 555 | 11 | | | | | | 10896 |
| HPV45 | E1 | ILLYGPANTGK | 466 | 11 | | | | | | 10897 |
| HPV45 | E1 | ISFLRALK | 447 | 8 | | | | | | 10898 |
| HPV45 | E1 | ISIDRKHK | 538 | 8 | | | | | | 10899 |
| HPV45 | E1 | ISLNSGHK | 116 | 8 | | | | | | 10900 |
| HPV45 | E1 | ISLNSGHKK | 116 | 9 | | | | | | 10901 |
| HPV45 | E1 | ISLNSGHKKAK | 116 | 11 | | | | | | 10902 |
| HPV45 | E1 | KAAMLAVFK | 197 | 9 | | | | | | 10903 |
| HPV45 | E1 | KIDEGGDWR | 425 | 9 | | | | | | 10904 |
| HPV45 | E1 | KSNCQAKYLK | 387 | 10 | | | | | | 10905 |
| HPV45 | E1 | LALLRYKCGK | 269 | 10 | | | | | | 10906 |
| HPV45 | E1 | LIEPPKLR | 299 | 8 | | | | | | 10907 |
| HPV45 | E1 | LILALLRYK | 267 | 9 | 0.2700 | 0.1800 | | | | 10908 |
| HPV45 | E1 | LLKRKFAGGSK | 84 | 11 | | | | | | 10909 |
| HPV45 | E1 | LLQASNKK | 190 | 8 | | | | | | 10910 |
| HPV45 | E1 | LLRKCGK | 271 | 8 | | | | | | 10911 |
| HPV45 | E1 | LLRYKCGKNR | 271 | 10 | | | | | | 10912 |
| HPV45 | E1 | LLTSNIDPAK | 556 | 10 | | | | | | 10913 |
| HPV45 | E1 | LLYGPANTGK | 467 | 10 | | | | | | 10914 |
| HPV45 | E1 | LSFTDLVR | 210 | 8 | | | | | | 10915 |
| HPV45 | E1 | LSFTDLVRNFK | 210 | 11 | | | | | | 10916 |
| HPV45 | E1 | LSVDTDLSPR | 103 | 10 | | | | | | 10917 |
| HPV45 | E1 | LTSNIDPAK | 557 | 9 | | | | | | 10918 |
| HPV45 | E1 | LVRNFKSDK | 215 | 9 | 0.0005 | 0.0002 | | | | 10919 |
| HPV45 | E1 | MLIEPPKLR | 298 | 9 | | | | | | 10920 |
| HPV45 | E1 | MSQWIKYR | 415 | 8 | | | | | | 10921 |
| HPV45 | E1 | MSQWIKYRCSK | 415 | 11 | | | | | | 10922 |
| HPV45 | E1 | NIDPAKDNK | 560 | 9 | | | | | | 10923 |
| HPV45 | E1 | NMSQWIKYR | 414 | 9 | | | | | | 10924 |
| HPV45 | E1 | NSGHKKAK | 119 | 8 | | | | | | 10925 |
| HPV45 | E1 | NSGHKKAKR | 119 | 9 | | | | | | 10926 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV45 | E1 | NSGHKKAKRR | 119 | 10 | | | | | | 10927 |
| HPV45 | E1 | NSNAAAFLK | 379 | 9 | 0.0057 | 0.3700 | | | | 10928 |
| HPV45 | E1 | PISIDRKHK | 537 | 9 | | | | | | 10929 |
| HPV45 | E1 | PTVAEGFK | 238 | 8 | | | | | | 10930 |
| HPV45 | E1 | PVYEINDK | 593 | 8 | | | | | | 10931 |
| HPV45 | E1 | PVYEINDKNWK | 593 | 11 | | | | | | 10932 |
| HPV45 | E1 | QLSVDTDLSPR | 102 | 11 | | | | | | 10933 |
| HPV45 | E1 | QMNMSQWIK | 412 | 9 | | | | | | 10934 |
| HPV45 | E1 | QMNMSQWIKYR | 412 | 11 | | | | | | 10935 |
| HPV45 | E1 | QVLHLLKR | 80 | 8 | | | | | | 10936 |
| HPV45 | E1 | QVLHLLKRK | 80 | 9 | | | | | | 10937 |
| HPV45 | E1 | RALKEFLK | 451 | 8 | | | | | | 10938 |
| HPV45 | E1 | RSSVAALYWYR | 306 | 11 | | | | | | 10939 |
| HPV45 | E1 | SLNSGHKK | 117 | 8 | | | | | | 10940 |
| HPV45 | E1 | SLNSGHKKAK | 117 | 10 | | | | | | 10941 |
| HPV45 | E1 | SLNSGHKKAKR | 117 | 11 | | | | | | 10942 |
| HPV45 | E1 | SSVAALYWYR | 307 | 10 | | | | | | 10943 |
| HPV45 | E1 | SVAALYWYR | 308 | 9 | 2.9000 | 8.8000 | | | | 10944 |
| HPV45 | E1 | SVDTDLSPR | 104 | 9 | | | | | | 10945 |
| HPV45 | E1 | TSNIDPAK | 558 | 8 | | | | | | 10946 |
| HPV45 | E1 | TSNIDPAKDNK | 558 | 11 | | | | | | 10947 |
| HPV45 | E1 | TVAEGFKTLIK | 239 | 11 | | | | | | 10948 |
| HPV45 | E1 | VAALYWYR | 309 | 8 | | | | | | 10949 |
| HPV45 | E1 | VAEGFKTLIK | 240 | 10 | | | | | | 10950 |
| HPV45 | E1 | VLHLLKRK | 81 | 8 | | | | | | 10951 |
| HPV45 | E1 | VLILALLR | 266 | 8 | | | | | | 10952 |
| HPV45 | E1 | VLILALLRYK | 266 | 10 | | | | | | 10953 |
| HPV45 | E1 | VMCRHYKR | 400 | 8 | | | | | | 10954 |
| HPV45 | E1 | VMCRHYKRAQK | 400 | 11 | | | | | | 10955 |
| HPV45 | E1 | VSGDTPEWIQR | 325 | 11 | | | | | | 10956 |
| HPV45 | E1 | WIKYRCSK | 418 | 8 | | | | | | 10957 |
| HPV45 | E1 | WLEPLADTK | 502 | 9 | | | | | | 10958 |
| HPV45 | E1 | WTYFDNYMR | 522 | 9 | | | | | | 10959 |
| HPV45 | E1 | YAHIQCLDCK | 254 | 10 | | | | | | 10960 |
| HPV45 | E1 | YLKDCAVMCR | 394 | 10 | | | | | | 10961 |
| HPV45 | E2 | AIELQMALK | 78 | 9 | | | | | | 10962 |
| HPV45 | E2 | ALKGLAQSK | 84 | 9 | | | | | | 10963 |
| HPV45 | E2 | CLRYRLRK | 305 | 8 | | | | | | 10964 |
| HPV45 | E2 | CSSTSNNK | 274 | 8 | | | | | | 10965 |
| HPV45 | E2 | CSSTSNNKR | 274 | 9 | | | | | | 10966 |
| HPV45 | E2 | CSSTSNNKRR | 274 | 10 | | | | | | 10967 |
| HPV45 | E2 | CSSTSNNKRRK | 274 | 11 | | | | | | 10968 |
| HPV45 | E2 | CVSYWGVYYIK | 158 | 11 | | | | | | 10969 |
| HPV45 | E2 | DTTYYVQFK | 171 | 9 | | | | | | 10970 |
| HPV45 | E2 | DTVSATQIVR | 212 | 10 | | | | | | 10971 |
| HPV45 | E2 | FTAREHGITK | 50 | 10 | | | | | | 10972 |
| HPV45 | E2 | GLTEQHHGR | 255 | 9 | | | | | | 10973 |
| HPV45 | E2 | HASTSTPK | 225 | 8 | | | | | | 10974 |
| HPV45 | E2 | HIQTPATK | 242 | 8 | | | | | | 10975 |
| HPV45 | E2 | HIQTPATKR | 242 | 9 | | | | | | 10976 |
| HPV45 | E2 | HIQTPATKRPR | 242 | 11 | | | | | | 10977 |
| HPV45 | E2 | HLKGDKNSLK | 295 | 10 | | | | | | 10978 |
| HPV45 | E2 | HVYFDGNK | 124 | 8 | | | | | | 10979 |
| HPV45 | E2 | IIHLKGDK | 293 | 8 | | | | | | 10980 |
| HPV45 | E2 | ILDHYENDSK | 21 | 10 | | | | | | 10981 |
| HPV45 | E2 | ISKSKAHK | 70 | 8 | | | | | | 10982 |
| HPV45 | E2 | ISYWQLIR | 36 | 8 | | | | | | 10983 |
| HPV45 | E2 | ITETGIWDK | 146 | 9 | | | | | | 10984 |
| HPV45 | E2 | KAIELQMALK | 77 | 10 | | | | | | 10985 |
| HPV45 | E2 | KILDHYENDSK | 20 | 11 | | | | | | 10986 |
| HPV45 | E2 | KTASVGTPK | 232 | 9 | | | | | | 10987 |
| HPV45 | E2 | KTVHVYFDGNK | 121 | 11 | | | | | | 10988 |
| HPV45 | E2 | LLCSSTSNNK | 272 | 10 | | | | | | 10989 |
| HPV45 | E2 | LLCSSTSNNKR | 272 | 11 | | | | | | 10990 |
| HPV45 | E2 | LSERLSALQDK | 10 | 11 | | | | | | 10991 |
| HPV45 | E2 | LTEQHHGR | 256 | 8 | | | | | | 10992 |
| HPV45 | E2 | LTVTYNSEVQR | 336 | 11 | | | | | | 10993 |
| HPV45 | E2 | MALKGLAQSK | 83 | 10 | | | | | | 10994 |
| HPV45 | E2 | NAILFTAR | 46 | 8 | | | | | | 10995 |
| HPV45 | E2 | NISKSKAHK | 69 | 9 | | | | | | 10996 |
| HPV45 | E2 | NSLKCLRYR | 301 | 9 | | | | | | 10997 |
| HPV45 | E2 | NSLKCLRYRLR | 301 | 11 | | | | | | 10998 |
| HPV45 | E2 | NSQISYWQLIR | 33 | 11 | | | | | | 10999 |
| HPV45 | E2 | NTEPSQCFK | 109 | 9 | | | | | | 11000 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV45 | E2 | NTEPSQCFKK | 109 | 10 | | | | | | 11001 |
| HPV45 | E2 | NTTPIIHLK | 289 | 9 | | | | | | 11002 |
| HPV45 | E2 | PIIHLKGDK | 292 | 9 | | | | | | 11003 |
| HPV45 | E2 | PINISKSK | 67 | 8 | | | | | | 11004 |
| HPV45 | E2 | PINISKSKAHK | 67 | 11 | | | | | | 11005 |
| HPV45 | E2 | PLLCSSTSNNK | 271 | 11 | | | | | | 11006 |
| HPV45 | E2 | PSQCFKKGGK | 112 | 10 | | | | | | 11007 |
| HPV45 | E2 | QISYWQLIR | 35 | 9 | | | | | | 11008 |
| HPV45 | E2 | QLQHASTSTPK | 222 | 11 | | | | | | 11009 |
| HPV45 | E2 | QMALKGLAQSK | 82 | 11 | | | | | | 11010 |
| HPV45 | E2 | QTPATKRPR | 244 | 9 | | | | | | 11011 |
| HPV45 | E2 | QTPKESLSER | 4 | 10 | | | | | | 11012 |
| HPV45 | E2 | QVVPPINISK | 63 | 10 | | | | | | 11013 |
| HPV45 | E2 | RLENAILFTAR | 43 | 11 | | | | | | 11014 |
| HPV45 | E2 | RLSALQDK | 13 | 8 | | | | | | 11015 |
| HPV45 | E2 | SLKCLRYR | 302 | 8 | | | | | | 11016 |
| HPV45 | E2 | SLKCLRYRLR | 302 | 10 | | | | | | 11017 |
| HPV45 | E2 | SLKCLRYRLRK | 302 | 11 | | | | | | 11018 |
| HPV45 | E2 | SSTSNNKR | 275 | 8 | | | | | | 11019 |
| HPV45 | E2 | SSTSNNKRR | 275 | 9 | | | | | | 11020 |
| HPV45 | E2 | SSTSNNKRRK | 275 | 10 | | | | | | 11021 |
| HPV45 | E2 | SSTWHWTGCNK | 321 | 11 | | | | | | 11022 |
| HPV45 | E2 | STSNNKRR | 276 | 8 | | | | | | 11023 |
| HPV45 | E2 | STSNNKRRK | 276 | 9 | | | | | | 11024 |
| HPV45 | E2 | STWHWTGCNK | 322 | 10 | | | | | | 11025 |
| HPV45 | E2 | TAREHGITK | 51 | 9 | | | | | | 11026 |
| HPV45 | E2 | TASVGTPK | 233 | 8 | | | | | | 11027 |
| HPV45 | E2 | TSNNKRRK | 277 | 8 | | | | | | 11028 |
| HPV45 | E2 | TTPIIHLK | 290 | 8 | | | | | | 11029 |
| HPV45 | E2 | TTPIIHLKGDK | 290 | 11 | | | | | | 11030 |
| HPV45 | E2 | TTYYVQFK | 172 | 8 | | | | | | 11031 |
| HPV45 | E2 | TVHVYFDGNK | 122 | 10 | | | | | | 11032 |
| HPV45 | E2 | TVSATQIVR | 213 | 9 | | | | | | 11033 |
| HPV45 | E2 | TVTYNSEVQR | 337 | 10 | | | | | | 11034 |
| HPV45 | E2 | VSATQIVR | 214 | 8 | | | | | | 11035 |
| HPV45 | E2 | VSYWGVYYIK | 159 | 10 | | | | | | 11036 |
| HPV45 | E2 | VTYNSEVQR | 338 | 9 | | | | | | 11037 |
| HPV45 | E2 | VVPPINISK | 64 | 9 | | | | | | 11038 |
| HPV45 | E2 | VVPPINISKSK | 64 | 11 | | | | | | 11039 |
| HPV45 | E2 | YITETGIWDK | 145 | 10 | | | | | | 11040 |
| HPV45 | E2 | YVQFKSECEK | 175 | 10 | | | | | | 11041 |
| HPV45 | E6 | CIAYAACHK | 59 | 9 | | | | | | 11042 |
| HPV45 | E6 | CIDFYSRIR | 68 | 9 | 0.0001 | 0.0001 | | | | 11043 |
| HPV45 | E6 | CVYCKATLER | 32 | 10 | | | | | | 11044 |
| HPV45 | E6 | DVSIACVYCK | 27 | 10 | | | | | | 11045 |
| HPV45 | E6 | ELYNLLIR | 97 | 8 | | | | | | 11046 |
| HPV45 | E6 | ELYNLLIRCLR | 97 | 11 | | | | | | 11047 |
| HPV45 | E6 | EVYQFAFK | 43 | 8 | | | | | | 11048 |
| HPV45 | E6 | FAFKDLFIVYR | 47 | 11 | | | | | | 11049 |
| HPV45 | E6 | HSIAGQYR | 128 | 8 | | | | | | 11050 |
| HPV45 | E6 | IAYAACHK | 60 | 8 | | | | | | 11051 |
| HPV45 | E6 | LIRCLRCQK | 102 | 9 | 0.0190 | 0.0012 | | | | 11052 |
| HPV45 | E6 | LLIRCLRCQK | 101 | 10 | 0.0470 | 0.1200 | | | | 11053 |
| HPV45 | E6 | MARFDDPTQR | 1 | 10 | | | | | | 11054 |
| HPV45 | E6 | NLLIRCLR | 100 | 8 | | | | | | 11055 |
| HPV45 | E6 | NLLIRCLRCQK | 100 | 11 | | | | | | 11056 |
| HPV45 | E6 | NSVYGETLEK | 83 | 10 | | | | | | 11057 |
| HPV45 | E6 | NTCCDQAR | 139 | 8 | | | | | | 11058 |
| HPV45 | E6 | NTCCDQARQER | 139 | 11 | | | | | | 11059 |
| HPV45 | E6 | NTELYNLLIR | 95 | 10 | | | | | | 11060 |
| HPV45 | E6 | PAEKRRHLK | 114 | 9 | | | | | | 11061 |
| HPV45 | E6 | PAEKRRHLKDK | 114 | 11 | | | | | | 11062 |
| HPV45 | E6 | PLNPAEKR | 111 | 8 | | | | | | 11063 |
| HPV45 | E6 | PLNPAEKRR | 111 | 9 | | | | | | 11064 |
| HPV45 | E6 | QARQERLR | 144 | 8 | | | | | | 11065 |
| HPV45 | E6 | QARQERLRR | 144 | 9 | | | | | | 11066 |
| HPV45 | E6 | QARQERLRRR | 144 | 10 | | | | | | 11067 |
| HPV45 | E6 | QARQERLRRRR | 144 | 11 | | | | | | 11068 |
| HPV45 | E6 | RTEVYQFAFK | 41 | 10 | | | | | | 11069 |
| HPV45 | E6 | SIACVYCK | 29 | 8 | | | | | | 11070 |
| HPV45 | E6 | SVYGETLEK | 84 | 9 | | | | | | 11071 |
| HPV45 | E6 | VSIACVYCK | 28 | 9 | | | | | | 11072 |
| HPV45 | E6 | YSRIRELR | 72 | 8 | | | | | | 11073 |
| HPV45 | E7 | CVCCKCDGR | 64 | 9 | | | | | | 11074 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV45 | E7 | ESSADDLR | 78 | 8 | | | | | | 11075 |
| HPV45 | E7 | GVSHAQLPAR | 44 | 10 | | | | | | 11076 |
| HPV45 | E7 | GVSHAQLPARR | 44 | 11 | | | | | | 11077 |
| HPV45 | E7 | HAQLPARR | 47 | 8 | | | | | | 11078 |
| HPV45 | E7 | ILCVCCKCDGR | 62 | 11 | | | | | | 11079 |
| HPV45 | E7 | KILCVCCK | 61 | 8 | | | | | | 11080 |
| HPV45 | E7 | LTVESSADDLR | 75 | 11 | | | | | | 11081 |
| HPV45 | E7 | PARRAEPQR | 51 | 9 | | | | | | 11082 |
| HPV45 | E7 | PARRAEPQRHK | 51 | 11 | | | | | | 11083 |
| HPV45 | E7 | QLPARRAEPQR | 49 | 11 | | | | | | 11084 |
| HPV45 | E7 | RAEPQRHK | 54 | 8 | | | | | | 11085 |
| HPV45 | E7 | TVESSADDLR | 76 | 10 | | | | | | 11086 |
| HPV45 | E7 | VSHAQLPAR | 45 | 9 | | | | | | 11087 |
| HPV45 | E7 | VSHAQLPARR | 45 | 10 | | | | | | 11088 |
| HPV45 | L1 | AASTSTASR | 517 | 9 | | | | | | 11089 |
| HPV45 | L1 | AATAVITQDVR | 161 | 11 | | | | | | 11090 |
| HPV45 | L1 | AIGEHWAK | 191 | 8 | | | | | | 11091 |
| HPV45 | L1 | AMDFSTLQDTK | 234 | 11 | | | | | | 11092 |
| HPV45 | L1 | ASRPAKRVR | 523 | 9 | | | | | | 11093 |
| HPV45 | L1 | ASRPAKRVRIR | 523 | 11 | | | | | | 11094 |
| HPV45 | L1 | ASTSTASR | 518 | 8 | | | | | | 11095 |
| HPV45 | L1 | ASTSTASRPAK | 518 | 11 | | | | | | 11096 |
| HPV45 | L1 | ATAVITQDVR | 162 | 10 | | | | | | 11097 |
| HPV45 | L1 | AVITQDVR | 164 | 8 | | | | | | 11098 |
| HPV45 | L1 | AVPKVSAYQYR | 88 | 11 | | | | | | 11099 |
| HPV45 | L1 | CLRREQLFAR | 276 | 10 | | | | | | 11100 |
| HPV45 | L1 | CVGMEIGR | 129 | 8 | | | | | | 11101 |
| HPV45 | L1 | CVPAIGEHWAK | 188 | 11 | | | | | | 11102 |
| HPV45 | L1 | DICQSICK | 250 | 8 | | | | | | 11103 |
| HPV45 | L1 | DLDQYPLGR | 488 | 9 | | | | | | 11104 |
| HPV45 | L1 | DLDQYPLGRK | 488 | 10 | | | | | | 11105 |
| HPV45 | L1 | DSMFFCLR | 271 | 8 | | | | | | 11106 |
| HPV45 | L1 | DSMFFCLRR | 271 | 9 | | | | | | 11107 |
| HPV45 | L1 | DSTIYNPETQR | 114 | 11 | | | | | | 11108 |
| HPV45 | L1 | DTVPTDLYIK | 296 | 10 | | | | | | 11109 |
| HPV45 | L1 | DVRDNVSVDYK | 169 | 11 | | | | | | 11110 |
| HPV45 | L1 | FARHFWNR | 283 | 8 | | | | | | 11111 |
| HPV45 | L1 | FLQMALWR | 24 | 8 | | | | | | 11112 |
| HPV45 | L1 | FLVQAGLR | 498 | 8 | | | | | | 11113 |
| HPV45 | L1 | FLVQAGLRR | 498 | 9 | | | | | | 11114 |
| HPV45 | L1 | FLVQAGLRRR | 498 | 10 | | | | | | 11115 |
| HPV45 | L1 | FSTLQDTK | 237 | 8 | | | | | | 11116 |
| HPV45 | L1 | FVQSVAVTCQK | 450 | 11 | | | | | | 11117 |
| HPV45 | L1 | FVTVVDTTR | 359 | 9 | | | | | | 11118 |
| HPV45 | L1 | GAGNKQAVPK | 82 | 10 | | | | | | 11119 |
| HPV45 | L1 | GLRRRPTIGPR | 503 | 11 | | | | | | 11120 |
| HPV45 | L1 | GLSGHPFYNK | 143 | 10 | | | | | | 11121 |
| HPV45 | L1 | ITTSDSQLFNK | 328 | 11 | | | | | | 11122 |
| HPV45 | L1 | KLKFWTVDLK | 473 | 10 | | | | | | 11123 |
| HPV45 | L1 | KVSAYQYR | 91 | 8 | | | | | | 11124 |
| HPV45 | L1 | KVSAYQYRVFR | 91 | 11 | | | | | | 11125 |
| HPV45 | L1 | LLTVGNPYFR | 68 | 10 | | | | | | 11126 |
| HPV45 | L1 | LSGHPFYNK | 144 | 9 | | | | | | 11127 |
| HPV45 | L1 | LTVGNPYFR | 69 | 9 | | | | | | 11128 |
| HPV45 | L1 | LVQAGLRR | 499 | 8 | | | | | | 11129 |
| HPV45 | L1 | LVQAGLRRR | 499 | 9 | | | | | | 11130 |
| HPV45 | L1 | NTDDYVSR | 49 | 8 | | | | | | 11131 |
| HPV45 | L1 | NTYDPTKFK | 383 | 9 | | | | | | 11132 |
| HPV45 | L1 | PAASTSTASR | 516 | 10 | | | | | | 11133 |
| HPV45 | L1 | PAIGEHWAK | 190 | 9 | | | | | | 11134 |
| HPV45 | L1 | PAKRVRIR | 526 | 8 | | | | | | 11135 |
| HPV45 | L1 | PAKRVRIRSK | 526 | 10 | | | | | | 11136 |
| HPV45 | L1 | PAKRVRIRSKK | 526 | 11 | | | | | | 11137 |
| HPV45 | L1 | PIFLQMALWR | 22 | 10 | | | | | | 11138 |
| HPV45 | L1 | PLDICQSICK | 248 | 10 | | | | | | 11139 |
| HPV45 | L1 | PTIGPRKR | 508 | 8 | | | | | | 11140 |
| HPV45 | L1 | PTKFKHYSR | 387 | 9 | | | | | | 11141 |
| HPV45 | L1 | PTTSLVDTYR | 440 | 10 | | | | | | 11142 |
| HPV45 | L1 | PVPNTYDPTK | 380 | 10 | | | | | | 11143 |
| HPV45 | L1 | QLFARHFWNR | 281 | 10 | | | | | | 11144 |
| HPV45 | L1 | QLFNKPYWLHK | 334 | 11 | | | | | | 11145 |
| HPV45 | L1 | QLFVTVVDTTR | 357 | 11 | | | | | | 11146 |
| HPV45 | L1 | QSVAVTCQK | 452 | 9 | | | | | | 11147 |
| HPV45 | L1 | RLLTVGNPYFR | 67 | 11 | | | | | | 11148 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV45 | L1 | RVALPDPNK | 101 | 9 | | | | | | 11149 |
| HPV45 | L1 | RVRIRSKK | 529 | 8 | | | | | | 11150 |
| HPV45 | L1 | RVVNTDDYVSR | 46 | 11 | | | | | | 11151 |
| HPV45 | L1 | RVVPSGAGNK | 77 | 10 | | | | | | 11152 |
| HPV45 | L1 | SAYQYRVFR | 93 | 9 | | | | | | 11153 |
| HPV45 | L1 | SIFYHAGSSR | 58 | 10 | | | | | | 11154 |
| HPV45 | L1 | SMFFCLRR | 272 | 8 | | | | | | 11155 |
| HPV45 | L1 | SSDLDQYPLGR | 486 | 11 | | | | | | 11156 |
| HPV45 | L1 | STASRPAK | 521 | 8 | | | | | | 11157 |
| HPV45 | L1 | STASRPAKR | 521 | 9 | | | | | | 11158 |
| HPV45 | L1 | STASRPAKRVR | 521 | 11 | | | | | | 11159 |
| HPV45 | L1 | STIYNPETQR | 115 | 10 | | | | | | 11160 |
| HPV45 | L1 | STSASRPAK | 519 | 10 | | | | | | 11161 |
| HPV45 | L1 | STSASRPAKR | 519 | 11 | | | | | | 11162 |
| HPV45 | L1 | SVAVTCQK | 453 | 8 | | | | | | 11163 |
| HPV45 | L1 | TASRPAKR | 522 | 8 | | | | | | 11164 |
| HPV45 | L1 | TASRPAKRVR | 522 | 10 | | | | | | 11165 |
| HPV45 | L1 | TAVITQDVR | 163 | 9 | | | | | | 11166 |
| HPV45 | L1 | TIYNPETQR | 116 | 9 | | | | | | 11167 |
| HPV45 | L1 | TSDSQLFNK | 330 | 9 | | | | | | 11168 |
| HPV45 | L1 | TSIFYHAGSSR | 57 | 11 | | | | | | 11169 |
| HPV45 | L1 | TSLVDTYR | 442 | 8 | | | | | | 11170 |
| HPV45 | L1 | TSTASRPAK | 520 | 9 | | | | | | 11171 |
| HPV45 | L1 | TSTASRPAKR | 520 | 10 | | | | | | 11172 |
| HPV45 | L1 | TTSDSQLFNK | 329 | 10 | | | | | | 11173 |
| HPV45 | L1 | TTSLVDTYR | 441 | 9 | | | | | | 11174 |
| HPV45 | L1 | TVGNPYFR | 70 | 8 | | | | | | 11175 |
| HPV45 | L1 | TVPTDLYIK | 297 | 9 | | | | | | 11176 |
| HPV45 | L1 | TVYLPPPSVAR | 36 | 11 | | | | | | 11177 |
| HPV45 | L1 | VALPDPNK | 102 | 8 | | | | | | 11178 |
| HPV45 | L1 | VSAYQYRVFR | 92 | 10 | | | | | | 11179 |
| HPV45 | L1 | VTVVDTTR | 360 | 8 | | | | | | 11180 |
| HPV45 | L1 | VVNTDDYVSR | 47 | 10 | | | | | | 11181 |
| HPV45 | L1 | VVPSGAGNK | 78 | 9 | | | | | | 11182 |
| HPV45 | L1 | WACVGMEIGR | 127 | 10 | | | | | | 11183 |
| HPV45 | L1 | WAKGTLCK | 196 | 8 | | | | | | 11184 |
| HPV45 | L1 | WTVDLKEK | 477 | 8 | | | | | | 11185 |
| HPV45 | L1 | YIKGTSANMR | 303 | 10 | | | | | | 11186 |
| HPV45 | L1 | YLPPPSVAR | 38 | 9 | | | | | | 11187 |
| HPV45 | L2 | ALSSRRGTVR | 286 | 10 | | | | | | 11188 |
| HPV45 | L2 | ASATDLYR | 12 | 8 | | | | | | 11189 |
| HPV45 | L2 | ASATDLYRTCK | 12 | 11 | | | | | | 11190 |
| HPV45 | L2 | ASTTPSTIHK | 357 | 10 | | | | | | 11191 |
| HPV45 | L2 | ATDLYRTCK | 14 | 9 | | | | | | 11192 |
| HPV45 | L2 | ATMFTRSGK | 303 | 9 | | | | | | 11193 |
| HPV45 | L2 | DSDFMDIIR | 273 | 9 | | | | | | 11194 |
| HPV45 | L2 | FMDIIRLHR | 276 | 9 | | | | | | 11195 |
| HPV45 | L2 | FTRSGKQIGGR | 306 | 11 | | | | | | 11196 |
| HPV45 | L2 | GIGTGSGSGGR | 58 | 11 | | | | | | 11197 |
| HPV45 | L2 | GTCPPDVINK | 25 | 10 | | | | | | 11198 |
| HPV45 | L2 | GTGSGSGGR | 60 | 9 | | | | | | 11199 |
| HPV45 | L2 | GTVRFSRLGQR | 292 | 11 | | | | | | 11200 |
| HPV45 | L2 | ISSTPLPTVR | 210 | 10 | | | | | | 11201 |
| HPV45 | L2 | ISSTPLPTVRR | 210 | 11 | | | | | | 11202 |
| HPV45 | L2 | KVEGTTLADK | 34 | 10 | | | | | | 11203 |
| HPV45 | L2 | LSSRRGTVR | 287 | 9 | | | | | | 11204 |
| HPV45 | L2 | MVSHRAAR | 1 | 8 | | | | | | 11205 |
| HPV45 | L2 | MVSHRAARR | 1 | 9 | | | | | | 11206 |
| HPV45 | L2 | MVSHRAARRK | 1 | 10 | | | | | | 11207 |
| HPV45 | L2 | MVSHRAARRKR | 1 | 11 | | | | | | 11208 |
| HPV45 | L2 | NTVVDVGPTR | 79 | 10 | | | | | | 11209 |
| HPV45 | L2 | PALSSRRGTVR | 285 | 11 | | | | | | 11210 |
| HPV45 | L2 | PASTTPSTIHK | 356 | 11 | | | | | | 11211 |
| HPV45 | L2 | PISSTPLPTVR | 209 | 11 | | | | | | 11212 |
| HPV45 | L2 | PLPTVRRVR | 214 | 9 | | | | | | 11213 |
| HPV45 | L2 | PTVRRVRGPR | 216 | 10 | | | | | | 11214 |
| HPV45 | L2 | RASATDLYR | 11 | 9 | | | | | | 11215 |
| HPV45 | L2 | RATMFTRSGK | 302 | 10 | | | | | | 11216 |
| HPV45 | L2 | RLGQRATMFTR | 298 | 11 | | | | | | 11217 |
| HPV45 | L2 | RLHRPALSSR | 281 | 10 | | | | | | 11218 |
| HPV45 | L2 | RLHRPALSSRR | 281 | 11 | | | | | | 11219 |
| HPV45 | L2 | RLYSRANQQVR | 225 | 11 | | | | | | 11220 |
| HPV45 | L2 | RSGKQIGGR | 308 | 9 | | | | | | 11221 |
| HPV45 | L2 | RTGYVPLGGR | 68 | 10 | | | | | | 11222 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV45 | L2 | RVRGPRLYSR | 220 | 10 | | | | | | 11223 |
| HPV45 | L2 | SATDLYRTCK | 13 | 10 | | | | | | 11224 |
| HPV45 | L2 | SSRRGTVR | 288 | 8 | | | | | | 11225 |
| HPV45 | L2 | SSRRGTVRFSR | 288 | 11 | | | | | | 11226 |
| HPV45 | L2 | SSTPLPTVR | 211 | 9 | | | | | | 11227 |
| HPV45 | L2 | SSTPLPTVRR | 211 | 10 | | | | | | 11228 |
| HPV45 | L2 | STIHKSFTYPK | 362 | 11 | | | | | | 11229 |
| HPV45 | L2 | STPLPTVR | 212 | 8 | | | | | | 11230 |
| HPV45 | L2 | STPLPTVRR | 212 | 9 | | | | | | 11231 |
| HPV45 | L2 | STPLPTVRRVR | 212 | 11 | | | | | | 11232 |
| HPV45 | L2 | STTPSTIHK | 358 | 9 | | | | | | 11233 |
| HPV45 | L2 | TIHKSFTYPK | 363 | 10 | | | | | | 11234 |
| HPV45 | L2 | TMFTRSGK | 304 | 8 | | | | | | 11235 |
| HPV45 | L2 | TTPSTIHK | 359 | 8 | | | | | | 11236 |
| HPV45 | L2 | TVRFSRLGQR | 293 | 10 | | | | | | 11237 |
| HPV45 | L2 | TVRRVRGPR | 217 | 9 | | | | | | 11238 |
| HPV45 | L2 | TVVDVGPTR | 80 | 9 | | | | | | 11239 |
| HPV45 | L2 | VSHRAARR | 2 | 8 | | | | | | 11240 |
| HPV45 | L2 | VSHRAARRK | 2 | 9 | | | | | | 11241 |
| HPV45 | L2 | VSHRAARRKR | 2 | 10 | | | | | | 11242 |
| HPV45 | L2 | VVDVGPTR | 81 | 8 | | | | | | 11243 |
| HPV45 | L2 | YLWPWYYYFPK | 437 | 11 | | | | | | 11244 |
| HPV45 | L2 | YSRANQQVR | 227 | 9 | | | | | | 11245 |
| HPV56 | E2 | AAVSHRPGK | 177 | 9 | | | | | | 11246 |
| HPV56 | E2 | AAVSHRPGKR | 177 | 10 | | | | | | 11247 |
| HPV56 | E2 | AVSHRPGK | 178 | 8 | | | | | | 11248 |
| HPV56 | E2 | AVSHRPGKR | 178 | 9 | | | | | | 11249 |
| HPV56 | E2 | AVSHRPGKRPR | 178 | 11 | | | | | | 11250 |
| HPV56 | E2 | CLQVCKAK | 4 | 8 | | | | | | 11251 |
| HPV56 | E2 | CMQYVAWK | 71 | 8 | | | | | | 11252 |
| HPV56 | E2 | DAAVSHRPGK | 176 | 10 | | | | | | 11253 |
| HPV56 | E2 | DAAVSHRPGKR | 176 | 11 | | | | | | 11254 |
| HPV56 | E2 | DSSRESHAK | 195 | 9 | | | | | | 11255 |
| HPV56 | E2 | DSVSSTCR | 140 | 8 | | | | | | 11256 |
| HPV56 | E2 | DTDNTDSR | 213 | 8 | | | | | | 11257 |
| HPV56 | E2 | DTDNTDSRSR | 213 | 10 | | | | | | 11258 |
| HPV56 | E2 | EAKKFGCK | 117 | 8 | | | | | | 11259 |
| HPV56 | E2 | ELWLTEPK | 43 | 8 | | | | | | 11260 |
| HPV56 | E2 | ELWLTEPKK | 43 | 9 | | | | | | 11261 |
| HPV56 | E2 | ESEFDSSR | 191 | 8 | | | | | | 11262 |
| HPV56 | E2 | ETVNEYNTHK | 154 | 10 | | | | | | 11263 |
| HPV56 | E2 | EVWFDGSK | 61 | 8 | | | | | | 11264 |
| HPV56 | E2 | GIYYVHDGHK | 99 | 10 | | | | | | 11265 |
| HPV56 | E2 | HIEVWFDGSK | 59 | 10 | | | | | | 11266 |
| HPV56 | E2 | HISDTDNTDSR | 210 | 11 | | | | | | 11267 |
| HPV56 | E2 | HLKGEPNR | 239 | 8 | | | | | | 11268 |
| HPV56 | E2 | HLKGEPNRLK | 239 | 10 | | | | | | 11269 |
| HPV56 | E2 | HVKIPVVYR | 297 | 9 | | | | | | 11270 |
| HPV56 | E2 | IIYKDETQR | 283 | 9 | | | | | | 11271 |
| HPV56 | E2 | ISDTDNTDSR | 211 | 10 | | | | | | 11272 |
| HPV56 | E2 | ITIIYKDETQR | 281 | 11 | | | | | | 11273 |
| HPV56 | E2 | KTTPVVHLK | 233 | 9 | | | | | | 11274 |
| HPV56 | E2 | KVCSGVDYR | 90 | 9 | | | | | | 11275 |
| HPV56 | E2 | LSHVKIPVVYR | 295 | 11 | | | | | | 11276 |
| HPV56 | E2 | LTEPKKCFK | 46 | 9 | | | | | | 11277 |
| HPV56 | E2 | LTEPKKCFKK | 46 | 10 | | | | | | 11278 |
| HPV56 | E2 | MVPCLQVCK | 1 | 9 | | | | | | 11279 |
| HPV56 | E2 | MVPCLQVCKAK | 1 | 11 | | | | | | 11280 |
| HPV56 | E2 | NSFLSHVK | 292 | 8 | | | | | | 11281 |
| HPV56 | E2 | PVVHLKGEPNR | 236 | 11 | | | | | | 11282 |
| HPV56 | E2 | PVVYRLVWDK | 301 | 10 | | | | | | 11283 |
| HPV56 | E2 | RLKCCRYR | 246 | 8 | | | | | | 11284 |
| HPV56 | E2 | RLKCCRYRFQK | 246 | 11 | | | | | | 11285 |
| HPV56 | E2 | RLRESEFDSSR | 188 | 11 | | | | | | 11286 |
| HPV56 | E2 | SIITIIYK | 279 | 8 | | | | | | 11287 |
| HPV56 | E2 | SINNNNHPGDK | 223 | 11 | | | | | | 11288 |
| HPV56 | E2 | SSRESHAK | 196 | 8 | | | | | | 11289 |
| HPV56 | E2 | STYHWTSTDNK | 266 | 11 | | | | | | 11290 |
| HPV56 | E2 | TIIYKDETQR | 282 | 10 | | | | | | 11291 |
| HPV56 | E2 | TIYNNEEWTLR | 28 | 11 | | | | | | 11292 |
| HPV56 | E2 | TTPVVHLK | 234 | 8 | | | | | | 11293 |
| HPV56 | E2 | TVNEYNTHK | 155 | 9 | | | | | | 11294 |
| HPV56 | E2 | VSHRPGKR | 179 | 8 | | | | | | 11295 |
| HPV56 | E2 | VSHRPGKRPR | 179 | 10 | | | | | | 11296 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV56 | E2 | VVHLKGEPNR | 237 | 10 | | | | | | 11297 |
| HPV56 | E2 | VVYRLVWDK | 302 | 9 | | | | | | 11298 |
| HPV56 | E2 | WLTEPKKCFK | 45 | 10 | | | | | | 11299 |
| HPV56 | E2 | WLTEPKKCFKK | 45 | 11 | | | | | | 11300 |
| HPV56 | E2 | YSIITIIYK | 278 | 9 | | | | | | 11301 |
| HPV56 | E2 | YTDFEQEAK | 111 | 9 | | | | | | 11302 |
| HPV56 | E2 | YTDFEQEAKK | 111 | 10 | | | | | | 11303 |
| HPV56 | E6 | ATLESITK | 89 | 8 | | | | | | 11304 |
| HPV56 | E6 | ATLESITKK | 89 | 9 | | | | | | 11305 |
| HPV56 | E6 | CLGCWRQTSR | 139 | 10 | | | | | | 11306 |
| HPV56 | E6 | CLLFYSKVR | 69 | 9 | | | | | | 11307 |
| HPV56 | E6 | CLLFYSKVRK | 69 | 10 | | | | | | 11308 |
| HPV56 | E6 | CTELKLVYR | 50 | 9 | | | | | | 11309 |
| HPV56 | E6 | CVYCKKELTR | 33 | 10 | | | | | | 11310 |
| HPV56 | E6 | DLLIRCYR | 101 | 8 | | | | | | 11311 |
| HPV56 | E6 | DLRLSCVYCK | 28 | 10 | | | | | | 11312 |
| HPV56 | E6 | DLRLSCVYCKK | 28 | 11 | | | | | | 11313 |
| HPV56 | E6 | EIPLIDLR | 23 | 8 | | | | | | 11314 |
| HPV56 | E6 | EVLEIPLIDLR | 20 | 11 | | | | | | 11315 |
| HPV56 | E6 | EVYNFACTELK | 44 | 11 | | | | | | 11316 |
| HPV56 | E6 | FACTELKLVYR | 48 | 11 | | | | | | 11317 |
| HPV56 | E6 | GATLESITK | 88 | 9 | | | | | | 11318 |
| HPV56 | E6 | GATLESITKK | 88 | 10 | | | | | | 11319 |
| HPV56 | E6 | GSCLGCWR | 137 | 8 | | | | | | 11320 |
| HPV56 | E6 | LLFYSKVR | 70 | 8 | | | | | | 11321 |
| HPV56 | E6 | LLFYSKVRK | 70 | 9 | | | | | | 11322 |
| HPV56 | E6 | LLFYSKVRKYR | 70 | 11 | | | | | | 11323 |
| HPV56 | E6 | LSCVYCKK | 31 | 8 | | | | | | 11324 |
| HPV56 | E6 | QLCDLLIR | 98 | 8 | | | | | | 11325 |
| HPV56 | E6 | QLCDLLIRCYR | 98 | 11 | | | | | | 11326 |
| HPV56 | E6 | QLHCDRKR | 119 | 8 | | | | | | 11327 |
| HPV56 | E6 | QLHCDRKRR | 119 | 9 | | | | | | 11328 |
| HPV56 | E6 | QSPLTPEEK | 110 | 9 | | | | | | 11329 |
| HPV56 | E6 | RLSCVYCK | 30 | 8 | | | | | | 11330 |
| HPV56 | E6 | RLSCVYCKK | 30 | 9 | | | | | | 11331 |
| HPV56 | E6 | RVCLLFYSK | 67 | 9 | | | | | | 11332 |
| HPV56 | E6 | RVCLLFYSKVR | 67 | 11 | | | | | | 11333 |
| HPV56 | E6 | TLESITKK | 90 | 8 | | | | | | 11334 |
| HPV56 | E6 | VLEIPLIDLR | 21 | 10 | | | | | | 11335 |
| HPV56 | E6 | WTGSCLGCWR | 135 | 10 | | | | | | 11336 |
| HPV56 | E6 | YSKVRKYR | 73 | 8 | | | | | | 11337 |
| HPV56 | E7 | DIQSTKEDLR | 75 | 10 | | | | | | 11338 |
| HPV56 | E7 | EVDHLQER | 39 | 8 | | | | | | 11339 |
| HPV56 | E7 | FVVQLDIQSTK | 70 | 11 | | | | | | 11340 |
| HPV56 | E7 | HLQERPQQAR | 42 | 10 | | | | | | 11341 |
| HPV56 | E7 | HVPCCECK | 62 | 8 | | | | | | 11342 |
| HPV56 | E7 | LIHVPCCECK | 60 | 10 | | | | | | 11343 |
| HPV56 | E7 | QLDIQSTK | 73 | 8 | | | | | | 11344 |
| HPV56 | E7 | QSTKEDLR | 77 | 8 | | | | | | 11345 |
| HPV56 | E7 | VVQLDIQSTK | 71 | 10 | | | | | | 11346 |
| HPV56 | E7 | YLIHVPCCECK | 59 | 11 | | | | | | 11347 |
| HPV56 | L1 | AMDFKVLQESK | 241 | 11 | | | | | | 11348 |
| HPV56 | L1 | AMGEHWTK | 198 | 8 | | | | | | 11349 |
| HPV56 | L1 | ATDSYVKR | 58 | 8 | | | | | | 11350 |
| HPV56 | L1 | ATEQLSKYDAR | 381 | 11 | | | | | | 11351 |
| HPV56 | L1 | ATSLEDKYR | 444 | 9 | | | | | | 11352 |
| HPV56 | L1 | ATWRPSENK | 37 | 9 | | | | | | 11353 |
| HPV56 | L1 | AVATSKKR | 512 | 8 | | | | | | 11354 |
| HPV56 | L1 | AVGHPYYSVTK | 79 | 11 | | | | | | 11355 |
| HPV56 | L1 | CTPAMGEHWTK | 195 | 11 | | | | | | 11356 |
| HPV56 | L1 | CVGLEVGR | 136 | 8 | | | | | | 11357 |
| HPV56 | L1 | DARKINQYLR | 389 | 10 | | | | | | 11358 |
| HPV56 | L1 | DIVQSTCK | 257 | 8 | | | | | | 11359 |
| HPV56 | L1 | DLDQFPLGR | 491 | 9 | | | | | | 11360 |
| HPV56 | L1 | DLDQFPLGRK | 491 | 10 | | | | | | 11361 |
| HPV56 | L1 | DSMWFYLR | 278 | 8 | | | | | | 11362 |
| HPV56 | L1 | DSMWFYLRR | 278 | 9 | | | | | | 11363 |
| HPV56 | L1 | DSRDNISVDGK | 176 | 11 | | | | | | 11364 |
| HPV56 | L1 | DTGFGAMDFK | 236 | 10 | | | | | | 11365 |
| HPV56 | L1 | DTNIYNPDQER | 121 | 11 | | | | | | 11366 |
| HPV56 | L1 | ELQFVFQLCK | 404 | 10 | | | | | | 11367 |
| HPV56 | L1 | ELYLKGSNGR | 308 | 10 | | | | | | 11368 |
| HPV56 | L1 | ETIPAELYLK | 303 | 10 | | | | | | 11369 |
| HPV56 | L1 | FARHYFNR | 290 | 8 | | | | | | 11370 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV56 | L1 | FARHYFNRAGK | 290 | 11 | | | | | | 11371 |
| HPV56 | L1 | FLMQLGTR | 501 | 8 | | | | | | 11372 |
| HPV56 | L1 | FLMQLGTRSK | 501 | 10 | | | | | | 11373 |
| HPV56 | L1 | FLQMATWR | 33 | 8 | | | | | | 11374 |
| HPV56 | L1 | FVTVVDTTR | 364 | 9 | | | | | | 11375 |
| HPV56 | L1 | GLSGHPLFNR | 150 | 10 | | | | | | 11376 |
| HPV56 | L1 | ISTATEQLSK | 378 | 10 | | | | | | 11377 |
| HPV56 | L1 | ITSEAQLFNK | 334 | 10 | | | | | | 11378 |
| HPV56 | L1 | KVSAYQYR | 98 | 8 | | | | | | 11379 |
| HPV56 | L1 | KVSAYQYRVFR | 98 | 11 | | | | | | 11380 |
| HPV56 | L1 | KVVATDSYVK | 55 | 10 | | | | | | 11381 |
| HPV56 | L1 | KVVATDSYVKR | 55 | 11 | | | | | | 11382 |
| HPV56 | L1 | KFYLPPTPVSK | 45 | 11 | | | | | | 11383 |
| HPV56 | L1 | LANNNVIEDSR | 168 | 11 | | | | | | 11384 |
| HPV56 | L1 | LMQLGTRSK | 502 | 9 | | | | | | 11385 |
| HPV56 | L1 | LSGHPLFNR | 151 | 9 | | | | | | 11386 |
| HPV56 | L1 | LSKYDARK | 385 | 8 | | | | | | 11387 |
| HPV56 | L1 | MATWRPSENK | 36 | 10 | | | | | | 11388 |
| HPV56 | L1 | MITSEAQLFNK | 333 | 11 | | | | | | 11389 |
| HPV56 | L1 | MLPMMYIYR | 2 | 9 | | | | | | 11390 |
| HPV56 | L1 | MMLPMMYIYR | 1 | 10 | | | | | | 11391 |
| HPV56 | L1 | NIPKVSAYQYR | 95 | 11 | | | | | | 11392 |
| HPV56 | L1 | NIYNPDQER | 123 | 9 | | | | | | 11393 |
| HPV56 | L1 | NTKTNIPK | 91 | 8 | | | | | | 11394 |
| HPV56 | L1 | PAMGEHWTK | 197 | 9 | | | | | | 11395 |
| HPV56 | L1 | PAVATSKK | 511 | 8 | | | | | | 11396 |
| HPV56 | L1 | PAVATSKKR | 511 | 9 | | | | | | 11397 |
| HPV56 | L1 | PIFLQMATWR | 31 | 10 | | | | | | 11398 |
| HPV56 | L1 | PLDIVQSTCK | 255 | 10 | | | | | | 11399 |
| HPV56 | L1 | PTEKQDPLAK | 467 | 10 | | | | | | 11400 |
| HPV56 | L1 | PTSTSTPAK | 522 | 9 | | | | | | 11401 |
| HPV56 | L1 | PTSTSTPAKR | 522 | 10 | | | | | | 11402 |
| HPV56 | L1 | PTSTSTPAKRK | 522 | 11 | | | | | | 11403 |
| HPV56 | L1 | PVATSLEDK | 442 | 9 | | | | | | 11404 |
| HPV56 | L1 | PVATSLEDKYR | 442 | 11 | | | | | | 11405 |
| HPV56 | L1 | QLFARHYFNR | 288 | 10 | | | | | | 11406 |
| HPV56 | L1 | QLFNKPYWLQR | 339 | 11 | | | | | | 11407 |
| HPV56 | L1 | QLFVTVVDTTR | 362 | 11 | | | | | | 11408 |
| HPV56 | L1 | QLSKYDAR | 384 | 8 | | | | | | 11409 |
| HPV56 | L1 | QLSKYDARK | 384 | 9 | | | | | | 11410 |
| HPV56 | L1 | QMATWRPSENK | 35 | 11 | | | | | | 11411 |
| HPV56 | L1 | QSTCKYPDYLK | 260 | 11 | | | | | | 11412 |
| HPV56 | L1 | RSKPAVATSK | 508 | 10 | | | | | | 11413 |
| HPV56 | L1 | RSKPAVATSKK | 508 | 11 | | | | | | 11414 |
| HPV56 | L1 | RSTAITCQR | 455 | 9 | | | | | | 11415 |
| HPV56 | L1 | RVRLPDPNK | 108 | 9 | | | | | | 11416 |
| HPV56 | L1 | SAPTSTSTPAK | 520 | 11 | | | | | | 11417 |
| HPV56 | L1 | SAYQYRVFR | 100 | 9 | | | | | | 11418 |
| HPV56 | L1 | SAYQYRVFRVR | 100 | 11 | | | | | | 11419 |
| HPV56 | L1 | SIFYHAGSSR | 67 | 10 | | | | | | 11420 |
| HPV56 | L1 | SLEDKYRYVR | 446 | 10 | | | | | | 11421 |
| HPV56 | L1 | SMWFYLRR | 279 | 8 | | | | | | 11422 |
| HPV56 | L1 | STAITCQR | 456 | 8 | | | | | | 11423 |
| HPV56 | L1 | STATEQLSK | 379 | 9 | | | | | | 11424 |
| HPV56 | L1 | STCKYPDYLK | 261 | 10 | | | | | | 11425 |
| HPV56 | L1 | STDLDQFPLGR | 489 | 11 | | | | | | 11426 |
| HPV56 | L1 | STPAKRKR | 526 | 8 | | | | | | 11427 |
| HPV56 | L1 | STPAKRKRR | 526 | 9 | | | | | | 11428 |
| HPV56 | L1 | STSTPAKR | 524 | 8 | | | | | | 11429 |
| HPV56 | L1 | STSPAKRK | 524 | 9 | | | | | | 11430 |
| HPV56 | L1 | STSPAKRKR | 524 | 10 | | | | | | 11431 |
| HPV56 | L1 | STSPAKRKRR | 524 | 11 | | | | | | 11432 |
| HPV56 | L1 | SVTKDNTK | 86 | 8 | | | | | | 11433 |
| HPV56 | L1 | TATEQLSK | 380 | 8 | | | | | | 11434 |
| HPV56 | L1 | TIPAELYLK | 304 | 9 | | | | | | 11435 |
| HPV56 | L1 | TISTATEQLSK | 377 | 11 | | | | | | 11436 |
| HPV56 | L1 | TSEAQLFNK | 335 | 9 | | | | | | 11437 |
| HPV56 | L1 | TSIFYHAGSSR | 66 | 11 | | | | | | 11438 |
| HPV56 | L1 | TSLEDKYR | 445 | 8 | | | | | | 11439 |
| HPV56 | L1 | TSLEDKYRYVR | 445 | 11 | | | | | | 11440 |
| HPV56 | L1 | TSTPAKRK | 525 | 8 | | | | | | 11441 |
| HPV56 | L1 | TSTPAKRKR | 525 | 9 | | | | | | 11442 |
| HPV56 | L1 | TSTPAKRKRR | 525 | 10 | | | | | | 11443 |
| HPV56 | L1 | TSTSTPAK | 523 | 8 | | | | | | 11444 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV56 | L1 | TSTSTPAKR | 523 | 9 | | | | | | 11445 |
| HPV56 | L1 | TSTSTPAKRK | 523 | 10 | | | | | | 11446 |
| HPV56 | L1 | TSTSTPAKRKR | 523 | 11 | | | | | | 11447 |
| HPV56 | L1 | VATDSYVK | 57 | 8 | | | | | | 11448 |
| HPV56 | L1 | VATDSYVKR | 57 | 9 | | | | | | 11449 |
| HPV56 | L1 | VATSLEDK | 443 | 8 | | | | | | 11450 |
| HPV56 | L1 | VATSLEDKYR | 443 | 10 | | | | | | 11451 |
| HPV56 | L1 | VSAYQYRVFR | 99 | 10 | | | | | | 11452 |
| HPV56 | L1 | VTVVDTTR | 365 | 8 | | | | | | 11453 |
| HPV56 | L1 | VVATDSYVK | 56 | 9 | | | | | | 11454 |
| HPV56 | L1 | VVATDSYVKR | 56 | 10 | | | | | | 11455 |
| HPV56 | L1 | WACVGLEVGR | 134 | 10 | | | | | | 11456 |
| HPV56 | L1 | WTKGAVCK | 203 | 8 | | | | | | 11457 |
| HPV56 | L1 | YLKGSNGR | 310 | 8 | | | | | | 11458 |
| HPV56 | L1 | YLPPTPVSK | 47 | 9 | | | | | | 11459 |
| HPV56 | L1 | YLRREQLFAR | 283 | 10 | | | | | | 11460 |
| HPV56 | L1 | YSVTKDNTK | 85 | 9 | | | | | | 11461 |
| HPV56 | L1 | YVRSTAITCQR | 453 | 11 | | | | | | 11462 |
| HPV56 | L2 | AAPRLYRK | 222 | 8 | | | | | | 11463 |
| HPV56 | L2 | ALHRPAFTTR | 281 | 10 | | | | | | 11464 |
| HPV56 | L2 | ALHRPAFTTRR | 281 | 11 | | | | | | 11465 |
| HPV56 | L2 | ALWPVYFFR | 438 | 9 | | | | | | 11466 |
| HPV56 | L2 | ALWPVYFFRR | 438 | 10 | | | | | | 11467 |
| HPV56 | L2 | ALWPVYFFRRR | 438 | 11 | | | | | | 11468 |
| HPV56 | L2 | ASATQLYK | 12 | 8 | | | | | | 11469 |
| HPV56 | L2 | ASATQLYKTCK | 12 | 11 | | | | | | 11470 |
| HPV56 | L2 | ATPSAHLPIK | 367 | 10 | | | | | | 11471 |
| HPV56 | L2 | ATQLYKTCK | 14 | 9 | | | | | | 11472 |
| HPV56 | L2 | DVVNKIEQK | 30 | 9 | | | | | | 11473 |
| HPV56 | L2 | FALWPVYFFR | 437 | 10 | | | | | | 11474 |
| HPV56 | L2 | FALWPVYFFRR | 437 | 11 | | | | | | 11475 |
| HPV56 | L2 | FMNIVALHR | 276 | 9 | | | | | | 11476 |
| HPV56 | L2 | FTTRRGGVR | 287 | 9 | | | | | | 11477 |
| HPV56 | L2 | GIGTGTGSGGR | 58 | 11 | | | | | | 11478 |
| HPV56 | L2 | GTCPEDVVNK | 25 | 10 | | | | | | 11479 |
| HPV56 | L2 | GTGTGSGGR | 60 | 9 | | | | | | 11480 |
| HPV56 | L2 | GVRFSRLGR | 293 | 9 | | | | | | 11481 |
| HPV56 | L2 | GVRFSRLGRK | 293 | 10 | | | | | | 11482 |
| HPV56 | L2 | IAAPRLYR | 221 | 8 | | | | | | 11483 |
| HPV56 | L2 | IAAPRLYRK | 221 | 9 | | | | | | 11484 |
| HPV56 | L2 | ISSTPIPGFR | 210 | 10 | | | | | | 11485 |
| HPV56 | L2 | ISSTPIPGFRR | 210 | 11 | | | | | | 11486 |
| HPV56 | L2 | IVDVTPAR | 81 | 8 | | | | | | 11487 |
| HPV56 | L2 | KATIQTRR | 302 | 8 | | | | | | 11488 |
| HPV56 | L2 | KIEQKTWADK | 34 | 10 | | | | | | 11489 |
| HPV56 | L2 | KVTDPAFLDR | 235 | 10 | | | | | | 11490 |
| HPV56 | L2 | MVAHRATR | 1 | 8 | | | | | | 11491 |
| HPV56 | L2 | MVAHRATRR | 1 | 9 | | | | | | 11492 |
| HPV56 | L2 | MVAHRATRRK | 1 | 10 | | | | | | 11493 |
| HPV56 | L2 | MVAHRATRRKR | 1 | 11 | | | | | | 11494 |
| HPV56 | L2 | PAFTTRRGGVR | 285 | 11 | | | | | | 11495 |
| HPV56 | L2 | PISSTPIPGFR | 209 | 11 | | | | | | 11496 |
| HPV56 | L2 | PSAHLPIK | 369 | 8 | | | | | | 11497 |
| HPV56 | L2 | PSTIVDVTPAR | 78 | 11 | | | | | | 11498 |
| HPV56 | L2 | PVYFFRRR | 441 | 8 | | | | | | 11499 |
| HPV56 | L2 | PVYFFRRRR | 441 | 9 | | | | | | 11500 |
| HPV56 | L2 | PVYFFRRRRR | 441 | 10 | | | | | | 11501 |
| HPV56 | L2 | PVYFFRRRRRK | 441 | 11 | | | | | | 11502 |
| HPV56 | L2 | QTRRGTQIGAR | 306 | 11 | | | | | | 11503 |
| HPV56 | L2 | RAGYVPLGSR | 68 | 10 | | | | | | 11504 |
| HPV56 | L2 | RASATQLYK | 11 | 9 | | | | | | 11505 |
| HPV56 | L2 | RIAAPRLYR | 220 | 9 | | | | | | 11506 |
| HPV56 | L2 | RIAAPRLYRK | 220 | 10 | | | | | | 11507 |
| HPV56 | L2 | RLGRKATIQTR | 298 | 11 | | | | | | 11508 |
| HPV56 | L2 | RLYRKAFQQVK | 225 | 11 | | | | | | 11509 |
| HPV56 | L2 | SATQLYKTCK | 13 | 10 | | | | | | 11510 |
| HPV56 | L2 | SSTPIPGFR | 211 | 9 | | | | | | 11511 |
| HPV56 | L2 | SSTPIPGFRR | 211 | 10 | | | | | | 11512 |
| HPV56 | L2 | STIVDVTPAR | 79 | 10 | | | | | | 11513 |
| HPV56 | L2 | STPIPGFR | 212 | 8 | | | | | | 11514 |
| HPV56 | L2 | STPIPGFRR | 212 | 9 | | | | | | 11515 |
| HPV56 | L2 | TIVDVTPAR | 80 | 9 | | | | | | 11516 |
| HPV56 | L2 | TTRRGGVR | 288 | 8 | | | | | | 11517 |
| HPV56 | L2 | TTRRGGVRFSR | 288 | 11 | | | | | | 11518 |

TABLE IX-continued

A03 Supermotif Peptides with Binding Data

| Type | Protein | Sequence | Position | No. of Amino Acids | A*0301 | A*1101 | A*3101 | A*3301 | A*6801 | Seq. Id. No. |
|---|---|---|---|---|---|---|---|---|---|---|
| HPV56 | L2 | VAHRATRR | 2 | 8 | | | | | | 11519 |
| HPV56 | L2 | VAHRATRRK | 2 | 9 | | | | | | 11520 |
| HPV56 | L2 | VAHRATRRKR | 2 | 10 | | | | | | 11521 |
| HPV56 | L2 | VALHRPAFTTR | 280 | 11 | | | | | | 11522 |
| HPV56 | L2 | VATPSAHLPIK | 366 | 11 | | | | | | 11523 |
| HPV56 | L2 | VTDPAFLDR | 236 | 9 | | | | | | 11524 |
| HPV56 | L2 | VVNKIEQK | 31 | 8 | | | | | | 11525 |

TABLE X

A24 Supermotif Peptides

| Type | Protein | Position | No. of Amino Acids | Sequence | A*2402 | Seq. Id. No. |
|---|---|---|---|---|---|---|
| HPV16 | E1 | 240 | 8 | AFGLTPSI | | 11526 |
| HPV16 | E1 | 391 | 11 | AFLKSNSQAKI | | 11527 |
| HPV16 | E1 | 539 | 9 | ALDGNLVSM | | 11528 |
| HPV16 | E1 | 459 | 9 | ALKRFLQGI | | 11529 |
| HPV16 | E1 | 318 | 9 | ALYWYKTGI | | 11530 |
| HPV16 | E1 | 206 | 9 | AMLAKFKEL | | 11531 |
| HPV16 | E1 | 206 | 10 | AMLAKFKELY | | 11532 |
| HPV16 | E1 | 524 | 8 | ATVPCWNY | | 11533 |
| HPV16 | E1 | 524 | 9 | ATVPCWNYI | | 11534 |
| HPV16 | E1 | 82 | 9 | AVQVLKRKY | | 11535 |
| HPV16 | E1 | 82 | 10 | AVQVLKRKYL | | 11536 |
| HPV16 | E1 | 23 | 11 | AVVEKKTGDAI | | 11537 |
| HPV16 | E1 | 500 | 9 | CFVNSKSHF | | 11538 |
| HPV16 | E1 | 500 | 10 | CFVNSKSHFW | | 11539 |
| HPV16 | E1 | 500 | 11 | CFVNSKSHFWL | | 11540 |
| HPV16 | E1 | 237 | 11 | CIAAFGLTPSI | | 11541 |
| HPV16 | E1 | 259 | 9 | CLYLHIQSL | | 11542 |
| HPV16 | E1 | 304 | 9 | CMMIEPPKL | | 11543 |
| HPV16 | E1 | 353 | 8 | CTFELSQM | | 11544 |
| HPV16 | E1 | 353 | 11 | CTFELSQMVQW | | 11545 |
| HPV16 | E1 | 101 | 10 | CVDNNISPRL | | 11546 |
| HPV16 | E1 | 640 | 10 | CVSGQNTNTL | | 11547 |
| HPV16 | E1 | 299 | 8 | CVSPMCMM | | 11548 |
| HPV16 | E1 | 299 | 9 | CVSPMCMMI | | 11549 |
| HPV16 | E1 | 528 | 9 | CWNYIDDNL | | 11550 |
| HPV16 | E1 | 50 | 9 | DFIVNDNDY | | 11551 |
| HPV16 | E1 | 50 | 10 | DFIVNDNDYL | | 11552 |
| HPV16 | E1 | 97 | 10 | DISGCVDNNI | | 11553 |
| HPV16 | E1 | 368 | 8 | DIVDDSEI | | 11554 |
| HPV16 | E1 | 368 | 10 | DIVDDSEIAY | | 11555 |
| HPV16 | E1 | 43 | 9 | DTGEDLVDF | | 11556 |
| HPV16 | E1 | 43 | 10 | DTGEDLVDFI | | 11557 |
| HPV16 | E1 | 384 | 9 | DTNSNASAF | | 11558 |
| HPV16 | E1 | 384 | 10 | DTNSNASAFL | | 11559 |
| HPV16 | E1 | 548 | 10 | DVKHRPLVQL | | 11560 |
| HPV16 | E1 | 235 | 9 | DWCIAAFGL | | 11561 |
| RPV16 | E1 | 438 | 8 | DWKQIVMF | | 11562 |
| HPV16 | E1 | 438 | 9 | DWKQIVMFL | | 11563 |
| HPV16 | E1 | 438 | 11 | DWKQIVMFLRY | | 11564 |
| HPV16 | E1 | 452 | 9 | EFMSFLTAL | | 11565 |
| HPV16 | E1 | 374 | 9 | EIAYKYAQL | | 11566 |
| HPV16 | E1 | 603 | 10 | ELNDKNWKSF | | 11567 |
| HPV16 | E1 | 603 | 11 | ELNDKNWKSFF | | 11568 |
| HPV16 | E1 | 356 | 8 | ELSQMVQW | | 11569 |
| HPV16 | E1 | 356 | 10 | ELSQMVQWAY | | 11570 |
| HPV16 | E1 | 213 | 10 | ELYGVSFSEL | | 11571 |
| HPV16 | E1 | 63 | 8 | ETETAHAL | | 11572 |
| HPV16 | E1 | 63 | 9 | ETETAHALF | | 11573 |
| HPV16 | E1 | 152 | 9 | ETETPCSQY | | 11574 |
| HPV16 | E1 | 288 | 10 | ETIEKLLSKL | | 11575 |
| HPV16 | E1 | 288 | 11 | ETIEKLLSKLL | | 11576 |
| HPV16 | E1 | 138 | 8 | EVETQQML | | 11577 |
| HPV16 | E1 | 331 | 9 | EVYGDTPEW | | 11578 |
| HPV16 | E1 | 331 | 10 | EVYGDTPEWI | | 11579 |
| HPV16 | E1 | 338 | 9 | EWIQRQTVL | | 11580 |
| HPV16 | E1 | 612 | 9 | FFSRTWSRL | | 11581 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | E1 | 612 | 11 | FFSRTWSRLSL | | 11582 |
| HPV16 | E1 | 51 | 8 | FIVNDNDY | | 11583 |
| HPV16 | E1 | 51 | 9 | FIVNDNDYL | | 11584 |
| HPV16 | E1 | 392 | 10 | FLKSNSQAKI | | 11585 |
| HPV16 | E1 | 463 | 11 | FLQGIPKKNCI | | 11586 |
| HPV16 | E1 | 493 | 9 | FLQGSVICF | | 11587 |
| HPV16 | E1 | 445 | 9 | FLRYQGVEF | | 11588 |
| HPV16 | E1 | 445 | 10 | FLRYQGVEFM | | 11589 |
| HPV16 | E1 | 456 | 8 | FLTALKRF | | 11590 |
| HPV16 | E1 | 456 | 9 | FLTALKRFL | | 11591 |
| HPV16 | E1 | 453 | 8 | FMSFLTAL | | 11592 |
| HPV16 | E1 | 453 | 11 | FMSFLTALKRF | | 11593 |
| HPV16 | E1 | 586 | 9 | FTFPNEFPF | | 11594 |
| HPV16 | E1 | 501 | 8 | FVNSKSHF | | 11595 |
| HPV16 | E1 | 501 | 9 | FVNSKSHFW | | 11596 |
| HPV16 | E1 | 501 | 10 | FVNSKSHFWL | | 11597 |
| HPV16 | E1 | 508 | 11 | FWLQPLADAKI | | 11598 |
| HPV16 | E1 | 466 | 8 | GIPKKNCI | | 11599 |
| HPV16 | E1 | 466 | 9 | GIPKKNCIL | | 11600 |
| HPV16 | E1 | 466 | 10 | GIPKKNCILL | | 11601 |
| HPV16 | E1 | 466 | 11 | GIPKKNCILLY | | 11602 |
| HPV16 | E1 | 325 | 9 | GISNISEVY | | 11603 |
| HPV16 | E1 | 242 | 10 | GLTPSIADSI | | 11604 |
| HPV16 | E1 | 519 | 11 | GMLDDATVPCW | | 11605 |
| HPV16 | E1 | 487 | 8 | GMSLMKFL | | 11606 |
| HPV16 | E1 | 272 | 10 | GMVVLLLVRY | | 11607 |
| HPV16 | E1 | 571 | 8 | GTDSRWPY | | 11608 |
| HPV16 | E1 | 571 | 9 | GTDSRWPYL | | 11609 |
| HPV16 | E1 | 12 | 8 | GTGCNGWF | | 11610 |
| HPV16 | E1 | 12 | 9 | GTGCNGWFY | | 11611 |
| HPV16 | E1 | 450 | 8 | GVEFMSFL | | 11612 |
| HPV16 | E1 | 450 | 11 | GVEFMSFLTAL | | 11613 |
| HPV16 | E1 | 179 | 8 | GVSERHTI | | 11614 |
| HPV16 | E1 | 216 | 11 | GVSFSELVRPF | | 11615 |
| HPV16 | E1 | 263 | 9 | HIQSLACSW | | 11616 |
| HPV16 | E1 | 263 | 11 | HIQSLACSWGM | | 11617 |
| HPV16 | E1 | 184 | 8 | HTICQTPL | | 11618 |
| HPV16 | E1 | 184 | 11 | HTICQTPLTNI | | 11619 |
| HPV16 | E1 | 411 | 10 | HYKRAEKKQM | | 11620 |
| HPV16 | E1 | 369 | 9 | IVDDSEIAY | | 11621 |
| HPV16 | E1 | 369 | 11 | IVDDSEIAYKY | | 11622 |
| HPV16 | E1 | 401 | 8 | IVKDCATM | | 11623 |
| HPV16 | E1 | 52 | 8 | IVNDNDYL | | 11624 |
| HPV16 | E1 | 210 | 10 | KFKELYGVSF | | 11625 |
| HPV16 | E1 | 492 | 8 | KFLQGSVI | | 11626 |
| HPV16 | E1 | 492 | 10 | KFLQGSVICF | | 11627 |
| HPV16 | E1 | 400 | 9 | KIVKDCATM | | 11628 |
| HPV16 | E1 | 296 | 8 | KLLCVSPM | | 11629 |
| HPV16 | E1 | 296 | 10 | KLLCVSPMCM | | 11630 |
| HPV16 | E1 | 296 | 11 | KLLCVSPMCMM | | 11631 |
| HPV16 | E1 | 311 | 9 | KLRSTAAAL | | 11632 |
| HPV16 | E1 | 311 | 10 | KLRSTAAALY | | 11633 |
| HPV16 | E1 | 311 | 11 | KLRSTAAALYW | | 11634 |
| HPV16 | E1 | 323 | 11 | KTGISNISEVY | | 11635 |
| HPV16 | E1 | 252 | 9 | KTLLQQYCL | | 11636 |
| HPV16 | E1 | 252 | 10 | KTLLQQYCLY | | 11637 |
| HPV16 | E1 | 252 | 11 | KTLLQQYCLYL | | 11638 |
| HPV16 | E1 | 199 | 9 | KTSNAKAAM | | 11639 |
| HPV16 | E1 | 199 | 10 | KTSNAKAAML | | 11640 |
| HPV16 | E1 | 89 | 10 | KYLVSPLSDI | | 11641 |
| HPV16 | E1 | 126 | 9 | LFESEDSGY | | 11642 |
| HPV16 | E1 | 485 | 9 | LFGMSLMKF | | 11643 |
| HPV16 | E1 | 485 | 10 | LFGMSLMKFL | | 11644 |
| HPV16 | E1 | 297 | 9 | LLCVSPMCM | | 11645 |
| HPV16 | E1 | 297 | 10 | LLCVSPMCMM | | 11646 |
| HPV16 | E1 | 297 | 11 | LLCVSPMCMMI | | 11647 |
| HPV16 | E1 | 254 | 8 | LLQQYCLY | | 11648 |
| HPV16 | E1 | 254 | 9 | LLQQYCLYL | | 11649 |
| HPV16 | E1 | 254 | 11 | LLQQYCLYLHI | | 11650 |
| HPV16 | E1 | 293 | 11 | LLSKLLCVSPM | | 11651 |
| HPV16 | E1 | 490 | 10 | LMKFLQGSVI | | 11652 |
| HPV16 | E1 | 457 | 8 | LTALKRFL | | 11653 |
| HPV16 | E1 | 457 | 11 | LTALKRFLQGI | | 11654 |
| HPV16 | E1 | 191 | 8 | LTNILNVL | | 11655 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | E1 | 243 | 9 | LTPSIADSI | | 11656 |
| HPV16 | E1 | 48 | 11 | LVDFIVNDNDY | | 11657 |
| HPV16 | E1 | 554 | 9 | LVQLKCPPL | | 11658 |
| HPV16 | E1 | 554 | 10 | LVQLKCPPLL | | 11659 |
| HPV16 | E1 | 554 | 11 | LVQLKCPPLLI | | 11660 |
| HPV16 | E1 | 544 | 11 | LVSMDVKHRPL | | 11661 |
| HPV16 | E1 | 91 | 8 | LVSPLSDI | | 11662 |
| HPV16 | E1 | 583 | 10 | LVVFTFPNEF | | 11663 |
| HPV16 | E1 | 475 | 11 | LYGAANTGKSL | | 11664 |
| HPV16 | E1 | 214 | 9 | LYGVSFSEL | | 11665 |
| HPV16 | E1 | 260 | 8 | LYLHIQSL | | 11666 |
| HPV16 | E1 | 319 | 8 | LYWYKTGI | | 11667 |
| HPV16 | E1 | 319 | 11 | LYWYKTGISNI | | 11668 |
| HPV16 | E1 | 444 | 10 | MFLRYQGVEF | | 11669 |
| HPV16 | E1 | 444 | 11 | MFLRYQGVEFM | | 11670 |
| HPV16 | E1 | 207 | 8 | MLAKFKEL | | 11671 |
| HPV16 | E1 | 207 | 9 | MLAKFKELY | | 11672 |
| HPV16 | E1 | 520 | 10 | MLDDATVPCW | | 11673 |
| HPV16 | E1 | 305 | 8 | MMIEPPKL | | 11674 |
| HPV16 | E1 | 360 | 10 | MVQWAYDNDI | | 11675 |
| HPV16 | E1 | 273 | 9 | MVVLLLVRY | | 11676 |
| HPV16 | E1 | 567 | 10 | NINAGTDSRW | | 11677 |
| HPV16 | E1 | 105 | 9 | NISPRLKAI | | 11678 |
| HPV16 | E1 | 105 | 11 | NISPRLKAICI | | 11679 |
| HPV16 | E1 | 535 | 10 | NLRNALDGNL | | 11680 |
| HPV16 | E1 | 136 | 9 | NTEVETQQM | | 11681 |
| HPV16 | E1 | 136 | 10 | NTEVETQQML | | 11682 |
| HPV16 | E1 | 480 | 9 | NTGKSLFGM | | 11683 |
| HPV16 | E1 | 480 | 11 | NTGKSLFGMSL | | 11684 |
| HPV16 | E1 | 608 | 10 | NWKSFFSRTW | | 11685 |
| HPV16 | E1 | 530 | 11 | NYIDDNLRNAL | | 11686 |
| HPV16 | E1 | 593 | 10 | PFDENGNPVY | | 11687 |
| HPV16 | E1 | 512 | 9 | PLADAKIGM | | 11688 |
| HPV16 | E1 | 512 | 10 | PLADAKIGML | | 11689 |
| HPV16 | E1 | 561 | 8 | PLLITSNI | | 11690 |
| HPV16 | E1 | 190 | 9 | PLTNILNVL | | 11691 |
| HPV16 | E1 | 553 | 10 | PLVQLKCPPL | | 11692 |
| HPV16 | E1 | 553 | 11 | PLVQLKCPPLL | | 11693 |
| HPV16 | E1 | 302 | 11 | PMCMMIEPPKL | | 11694 |
| HPV16 | E1 | 600 | 10 | PVYELNDKNW | | 11695 |
| HPV16 | E1 | 577 | 10 | PYLHNRLVVF | | 11696 |
| HPV16 | E1 | 441 | 8 | QIVMFLRY | | 11697 |
| HPV16 | E1 | 556 | 8 | QLKCPPLL | | 11698 |
| HPV16 | E1 | 556 | 9 | QLKCPPLLI | | 11699 |
| HPV16 | E1 | 419 | 8 | QMSMSQWI | | 11700 |
| HPV16 | E1 | 419 | 10 | QMSMSQWIKY | | 11701 |
| HPV16 | E1 | 359 | 11 | QMVQWAYDNDI | | 11702 |
| HPV16 | E1 | 188 | 8 | QTPLTNIL | | 11703 |
| HPV16 | E1 | 188 | 11 | QTPLTNILNVL | | 11704 |
| HPV16 | E1 | 343 | 8 | QTVLQHSF | | 11705 |
| HPV16 | E1 | 84 | 8 | QVLKRKYL | | 11706 |
| HPV16 | E1 | 362 | 8 | QWAYDNDI | | 11707 |
| HPV16 | E1 | 257 | 8 | QYCLYLHI | | 11708 |
| HPV16 | E1 | 257 | 11 | QYCLYLHIQSL | | 11709 |
| HPV16 | E1 | 125 | 10 | RLFESEDSGY | | 11710 |
| HPV16 | E1 | 582 | 11 | RLVVFTFPNEF | | 11711 |
| HPV16 | E1 | 615 | 8 | RTWSRLSL | | 11712 |
| HPV16 | E1 | 432 | 8 | RVDDGGDW | | 11713 |
| HPV16 | E1 | 432 | 11 | RVDDGGDWKQI | | 11714 |
| HPV16 | E1 | 575 | 9 | RWPYLHNRL | | 11715 |
| HPV16 | E1 | 280 | 11 | RYKCGKNRETI | | 11716 |
| HPV16 | E1 | 447 | 8 | RYQGVEFM | | 11717 |
| HPV16 | E1 | 447 | 10 | RYQGVEFMSF | | 11718 |
| HPV16 | E1 | 447 | 11 | RYQGVEFMSFL | | 11719 |
| HPV16 | E1 | 611 | 10 | SFFSRTWSRL | | 11720 |
| HPV16 | E1 | 455 | 9 | SFLTALKRF | | 11721 |
| HPV16 | E1 | 455 | 10 | SFLTALKRFL | | 11722 |
| HPV16 | E1 | 349 | 9 | SFNDCTFEL | | 11723 |
| HPV16 | E1 | 218 | 9 | SFSELVRPF | | 11724 |
| RPV16 | E1 | 246 | 9 | SIADSIKTL | | 11725 |
| HPV16 | E1 | 246 | 10 | SIADSIKTLL | | 11726 |
| HPV16 | E1 | 250 | 9 | SIKTLLQQY | | 11727 |
| HPV16 | E1 | 250 | 11 | SIKTLLQQYCL | | 11728 |
| HPV16 | E1 | 266 | 8 | SLACSWGM | | 11729 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | E1 | 266 | 11 | SLACSWGMVVL | | 11730 |
| HPV16 | E1 | 484 | 8 | SLFGMSLM | | 11731 |
| HPV16 | E1 | 484 | 10 | SLFGMSLMKF | | 11732 |
| HPV16 | E1 | 484 | 11 | SLFGMSLMKFL | | 11733 |
| HPV16 | E1 | 489 | 11 | SLMKFLQGSVI | | 11734 |
| HPV16 | E1 | 546 | 9 | SMDVKHRPL | | 11735 |
| HPV16 | E1 | 421 | 8 | SMSQWIKY | | 11736 |
| HPV16 | E1 | 314 | 8 | STAAALYW | | 11737 |
| HPV16 | E1 | 314 | 9 | STAAALYWY | | 11738 |
| HPV16 | E1 | 231 | 8 | STCCDWCI | | 11739 |
| HPV16 | E1 | 231 | 11 | STCCDWCIAAF | | 11740 |
| HPV16 | E1 | 270 | 8 | SWGMVVLL | | 11741 |
| HPV16 | E1 | 270 | 9 | SWGMVVLLL | | 11742 |
| HPV16 | E1 | 354 | 10 | TFELSQMVQW | | 11743 |
| HPV16 | E1 | 587 | 8 | TFPNEFPF | | 11744 |
| HPV16 | E1 | 185 | 10 | TICQTPLTNI | | 11745 |
| HPV16 | E1 | 185 | 11 | TICQTPLTNIL | | 11746 |
| HPV16 | E1 | 289 | 9 | TIEKLLSKL | | 11747 |
| HPV16 | E1 | 289 | 10 | TIEKLLSKLL | | 11748 |
| HPV16 | E1 | 253 | 8 | TLLQQYCL | | 11749 |
| HPV16 | E1 | 253 | 9 | TLLQQYCLY | | 11750 |
| HPV16 | E1 | 253 | 10 | TLLQQYCLYL | | 11751 |
| HPV16 | E1 | 525 | 8 | TVPCWNYI | | 11752 |
| HPV16 | E1 | 585 | 8 | VFTFPNEF | | 11753 |
| HPV16 | E1 | 585 | 10 | VFTFPNEFPF | | 11754 |
| HPV16 | E1 | 498 | 11 | VICFVNSKSHF | | 11755 |
| HPV16 | E1 | 85 | 11 | VLKRKYLVSPL | | 11756 |
| HPV16 | E1 | 197 | 11 | VLKTSNAKAAM | | 11757 |
| HPV16 | E1 | 345 | 11 | VLQHSFNDCTF | | 11758 |
| HPV16 | E1 | 443 | 11 | VMFLRYQGVEF | | 11759 |
| HPV16 | E1 | 24 | 10 | VVEKKTGDAI | | 11760 |
| HPV16 | E1 | 584 | 9 | VVFTFPNEF | | 11761 |
| HPV16 | E1 | 584 | 11 | VVFTFPNEFPF | | 11762 |
| HPV16 | E1 | 274 | 8 | VVLLLVRY | | 11763 |
| HPV16 | E1 | 601 | 9 | VYELNDKNW | | 11764 |
| HPV16 | E1 | 332 | 8 | VYGDTPEW | | 11765 |
| HPV16 | E1 | 332 | 9 | VYGDTPEWI | | 11766 |
| HPV16 | E1 | 339 | 8 | WIQRQTVL | | 11767 |
| HPV16 | E1 | 509 | 10 | WLQPLADAKI | | 11768 |
| HPV16 | E1 | 321 | 9 | WYKTGISNI | | 11769 |
| HPV16 | E1 | 531 | 10 | YIDDNLRNAL | | 11770 |
| HPV16 | E1 | 261 | 11 | YLHIQSLACSW | | 11771 |
| HPV16 | E1 | 578 | 9 | YLHNRLVVF | | 11772 |
| HPV16 | E1 | 578 | 11 | YLHNRLVVFTF | | 11773 |
| HPV16 | E1 | 90 | 9 | YLVSPLSDI | | 11774 |
| HPV16 | E1 | 320 | 10 | YWYKTGISNI | | 11775 |
| HPV16 | E2 | 270 | 10 | AFNSSHKGRI | | 11776 |
| HPV16 | E2 | 72 | 8 | AIELQLTL | | 11777 |
| HPV16 | E2 | 72 | 11 | AIELQLTLETI | | 11778 |
| HPV16 | E2 | 331 | 11 | AIVTLTYDSEW | | 11779 |
| HPV16 | E2 | 41 | 9 | AIYYKAREM | | 11780 |
| HPV16 | E2 | 41 | 11 | AIYYKAREMGF | | 11781 |
| HPV16 | E2 | 228 | 11 | ALGTEETQTTI | | 11782 |
| HPV16 | E2 | 69 | 9 | ALQAIELQL | | 11783 |
| HPV16 | E2 | 69 | 11 | ALQAIELQLTL | | 11784 |
| HPV16 | E2 | 221 | 9 | ATHTKAVAL | | 11785 |
| HPV16 | E2 | 63 | 8 | AVSKNKAL | | 11786 |
| HPV16 | E2 | 63 | 11 | AVSKNKALQAI | | 11787 |
| HPV16 | E2 | 314 | 8 | AVSSTWHW | | 11788 |
| HPV16 | E2 | 309 | 11 | CTLYTAVSSTW | | 11789 |
| HPV16 | E2 | 124 | 8 | DICNTMHY | | 11790 |
| HPV16 | E2 | 124 | 11 | DICNTMHYTNW | | 11791 |
| HPV16 | E2 | 25 | 8 | DLRDHIDY | | 11792 |
| HPV16 | E2 | 25 | 9 | DLRDHIDYW | | 11793 |
| HPV16 | E2 | 246 | 11 | DTGNPCHTTKL | | 11794 |
| HPV16 | E2 | 96 | 8 | DVSLEVYL | | 11795 |
| HPV16 | E2 | 31 | 8 | DYWKHMRL | | 11796 |
| HPV16 | E2 | 74 | 9 | ELQLTLETI | | 11797 |
| HPV16 | E2 | 74 | 10 | ELQLTLETIY | | 11798 |
| HPV16 | E2 | 80 | 8 | ETIYNSQY | | 11799 |
| HPV16 | E2 | 185 | 9 | EVHAGGQVI | | 11800 |
| HPV16 | E2 | 185 | 10 | EVHAGGQVIL | | 11801 |
| HPV16 | E2 | 118 | 8 | EVQFDGDI | | 11802 |
| HPV16 | E2 | 204 | 8 | EVSSPEII | | 11803 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | E2 | 100 | 11 | EVYLTAPTGCI | | 11804 |
| HPV16 | E2 | 340 | 8 | EWQRDQFL | | 11805 |
| HPV16 | E2 | 346 | 11 | FLSQVKIPKTI | | 11806 |
| HPV16 | E2 | 168 | 11 | FVQFKDDAEKY | | 11807 |
| HPV16 | E2 | 163 | 9 | GIRTYFVQF | | 11808 |
| HPV16 | E2 | 156 | 9 | GLYYVHEGI | | 11809 |
| HPV16 | E2 | 230 | 9 | GTEETQTTI | | 11810 |
| HPV16 | E2 | 114 | 8 | GYTVEVQF | | 11811 |
| HPV16 | E2 | 29 | 8 | HIDYWKHM | | 11812 |
| HPV16 | E2 | 29 | 10 | HIDYWKHMRL | | 11813 |
| HPV16 | E2 | 53 | 10 | HINHQVVPTL | | 11814 |
| HPV16 | E2 | 290 | 9 | HLKGDANTL | | 11815 |
| HPV16 | E2 | 35 | 8 | HMRLECAI | | 11816 |
| HPV16 | E2 | 35 | 9 | HMRLECAIY | | 11817 |
| HPV16 | E2 | 35 | 10 | HMRLECAIYY | | 11818 |
| HPV16 | E2 | 18 | 9 | HYENDSTDL | | 11819 |
| HPV16 | E2 | 130 | 8 | HYTNWTHI | | 11820 |
| HPV16 | E2 | 130 | 9 | HYTNWTHIY | | 11821 |
| HPV16 | E2 | 130 | 10 | HYINWTHIYI | | 11822 |
| HPV16 | E2 | 193 | 8 | ILCPTSVF | | 11823 |
| HPV16 | E2 | 356 | 8 | ITVSTGFM | | 11824 |
| HPV16 | E2 | 356 | 10 | ITVSTGFMSI | | 11825 |
| HPV16 | E2 | 288 | 11 | IVHLKGDANTL | | 11826 |
| HPV16 | E2 | 332 | 10 | IVTLTYDSEW | | 11827 |
| HPV16 | E2 | 82 | 11 | IYNSQYSNEKW | | 11828 |
| HPV16 | E2 | 42 | 8 | IYYKAREM | | 11829 |
| HPV16 | E2 | 42 | 10 | IYYKAREMGF | | 11830 |
| HPV16 | E2 | 354 | 9 | KTITVSTGF | | 11831 |
| HPV16 | E2 | 354 | 10 | KTITVSTGFM | | 11832 |
| HPV16 | E2 | 91 | 9 | KWTLQDVSL | | 11833 |
| HPV16 | E2 | 177 | 8 | KYSKNKVW | | 11834 |
| HPV16 | E2 | 103 | 8 | LTAPTGCI | | 11835 |
| HPV16 | E2 | 16 | 11 | LTHYENDSTDL | | 11836 |
| HPV16 | E2 | 77 | 11 | LTLETIYNSQY | | 11837 |
| HPV16 | E2 | 311 | 9 | LYTAVSSTW | | 11838 |
| HPV16 | E2 | 311 | 11 | LYTAVSSTWHW | | 11839 |
| HPV16 | E2 | 157 | 8 | LYYVHEGI | | 11840 |
| HPV16 | E2 | 157 | 11 | LYYVHEGIRTY | | 11841 |
| HPV16 | E2 | 296 | 8 | NTLKCLRY | | 11842 |
| HPV16 | E2 | 296 | 10 | NTLKCLRYRF | | 11843 |
| HPV16 | E2 | 127 | 8 | NTMHYTNW | | 11844 |
| HPV16 | E2 | 127 | 11 | NTMHYTNWTHI | | 11845 |
| HPV16 | E2 | 284 | 8 | NTTPIVHL | | 11846 |
| HPV16 | E2 | 9 | 8 | NVCQDKIL | | 11847 |
| HPV16 | E2 | 9 | 11 | NVCQDKILTHY | | 11848 |
| HPV16 | E2 | 325 | 8 | NVKHKSAI | | 11849 |
| HPV16 | E2 | 325 | 11 | NVKHKSAIVTL | | 11850 |
| HPV16 | E2 | 106 | 10 | PTGCIKKHGY | | 11851 |
| HPV16 | E2 | 60 | 11 | PTLAVSKNKAL | | 11852 |
| HPV16 | E2 | 120 | 10 | QFDGDICNTM | | 11853 |
| HPV16 | E2 | 170 | 9 | QFKDDAEKY | | 11854 |
| HPV16 | E2 | 345 | 8 | QFLSQVKI | | 11855 |
| HPV16 | E2 | 76 | 8 | QLTLETIY | | 11856 |
| HPV16 | E2 | 151 | 8 | QVDYYGLY | | 11857 |
| HPV16 | E2 | 151 | 9 | QVDYYGLYY | | 11858 |
| HPV16 | E2 | 191 | 10 | QVILCPTSVF | | 11859 |
| HPV16 | E2 | 349 | 8 | QVKIPKTI | | 11860 |
| HPV16 | E2 | 86 | 9 | QYSNEKWTL | | 11861 |
| HPV16 | E2 | 304 | 8 | RFKKHCTL | | 11862 |
| HPV16 | E2 | 304 | 9 | RFKKHCTLY | | 11863 |
| HPV16 | E2 | 278 | 11 | RINCNSNTTPI | | 11864 |
| HPV16 | E2 | 37 | 8 | RLECAIYY | | 11865 |
| HPV16 | E2 | 7 | 9 | RLNVCQDKI | | 11866 |
| HPV16 | E2 | 7 | 10 | RLNVCQDKIL | | 11867 |
| HPV16 | E2 | 302 | 10 | RYRFKKHCTL | | 11868 |
| HPV16 | E2 | 302 | 11 | RYRFKKHCTLY | | 11869 |
| HPV16 | E2 | 23 | 8 | STDLRDHI | | 11870 |
| HPV16 | E2 | 23 | 10 | STDLRDHIDY | | 11871 |
| HPV16 | E2 | 23 | 11 | STDLRDHIDYW | | 11872 |
| HPV16 | E2 | 261 | 8 | SVDSAPIL | | 11873 |
| HPV16 | E2 | 261 | 11 | SVDSAPILTAF | | 11874 |
| HPV16 | E2 | 144 | 11 | SVTVVEGQVDY | | 11875 |
| HPV16 | E2 | 355 | 8 | TITVSTGF | | 11876 |
| HPV16 | E2 | 355 | 9 | TITVSTGFM | | 11877 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | E2 | 355 | 11 | TITVSTGFMSI | | 11878 |
| HPV16 | E2 | 61 | 10 | TLAVSKNKAL | | 11879 |
| HPV16 | E2 | 78 | 10 | TLETIYNSQY | | 11880 |
| HPV16 | E2 | 297 | 9 | TLKCLRYRF | | 11881 |
| HPV16 | E2 | 93 | 10 | TLQDVSLEVY | | 11882 |
| HPV16 | E2 | 93 | 11 | TLQDVSLEVYL | | 11883 |
| HPV16 | E2 | 334 | 8 | TLTYDSEW | | 11884 |
| HPV16 | E2 | 310 | 10 | TLYTAVSSTW | | 11885 |
| HPV16 | E2 | 128 | 10 | TMHYTNWTHI | | 11886 |
| HPV16 | E2 | 128 | 11 | TMHYTNWTHIY | | 11887 |
| HPV16 | E2 | 116 | 10 | TVEVQFDGDI | | 11888 |
| HPV16 | E2 | 357 | 9 | TVSTGFMSI | | 11889 |
| HPV16 | E2 | 146 | 9 | TVVEGQVDY | | 11890 |
| HPV16 | E2 | 146 | 10 | TVVEGQVDYY | | 11891 |
| HPV16 | E2 | 336 | 11 | TYDSEWQRDQF | | 11892 |
| HPV16 | E2 | 192 | 9 | VILCPTSVF | | 11893 |
| HPV16 | E2 | 333 | 9 | VTLTYDSEW | | 11894 |
| HPV16 | E2 | 145 | 10 | VTVVEGQVDY | | 11895 |
| HPV16 | E2 | 145 | 11 | VTVVEGQVDYY | | 11896 |
| HPV16 | E2 | 147 | 8 | VVEGQVDY | | 11897 |
| HPV16 | E2 | 147 | 9 | VVEGQVDYY | | 11898 |
| HPV16 | E2 | 147 | 11 | VVEGQVDYYGL | | 11899 |
| HPV16 | E2 | 183 | 11 | VWEVHAGGQVI | | 11900 |
| HPV16 | E2 | 101 | 10 | VYLTAPTGCI | | 11901 |
| HPV16 | E2 | 92 | 8 | WTLQDVSL | | 11902 |
| HPV16 | E2 | 92 | 11 | WTLQDVSLEVY | | 11903 |
| HPV16 | E2 | 102 | 9 | YLTAPTGCI | | 11904 |
| HPV16 | E2 | 312 | 8 | YTAVSSTW | | 11905 |
| HPV16 | E2 | 312 | 10 | YTAVSSTWHW | | 11906 |
| HPV16 | E2 | 131 | 8 | YTNWTHIY | | 11907 |
| HPV16 | E2 | 131 | 9 | YTNWTHIYI | | 11908 |
| HPV16 | E2 | 115 | 11 | YTVEVQFDGDI | | 11909 |
| HPV16 | E2 | 159 | 9 | YVHEGIRTY | | 11910 |
| HPV16 | E2 | 159 | 10 | YVHEGIRTYF | | 11911 |
| HPV16 | E2 | 32 | 11 | YWKHMRLECAI | | 11912 |
| HPV16 | E2 | 154 | 11 | YYGLYYVHEGI | | 11913 |
| HPV16 | E2 | 43 | 9 | YYKAREMGF | | 11914 |
| HPV16 | E2 | 158 | 10 | YYVHEGIRTY | | 11915 |
| HPV16 | E2 | 158 | 11 | YYVHEGIRTYF | | 11916 |
| HPV16 | E5 | 56 | 8 | AFRCFIVY | | 11917 |
| HPV16 | E5 | 56 | 9 | AFRCFIVYI | | 11918 |
| HPV16 | E5 | 56 | 10 | AFRCFIVYII | | 11919 |
| HPV16 | E5 | 56 | 11 | AFRCFIVYIIF | | 11920 |
| HPV16 | E5 | 18 | 10 | CFCVLLCVCL | | 11921 |
| HPV16 | E5 | 18 | 11 | CFCVLLCVCLL | | 11922 |
| HPV16 | E5 | 59 | 8 | CFIVYIIF | | 11923 |
| HPV16 | E5 | 59 | 10 | CFIVYIIFVY | | 11924 |
| HPV16 | E5 | 59 | 11 | CFIVYIIFVYI | | 11925 |
| HPV16 | E5 | 14 | 9 | CFLLCFCVL | | 11926 |
| HPV16 | E5 | 14 | 10 | CFLLCFCVLL | | 11927 |
| HPV16 | E5 | 26 | 8 | CLLIRPLL | | 11928 |
| HPV16 | E5 | 26 | 9 | CLLIRPLLL | | 11929 |
| HPV16 | E5 | 24 | 9 | CVCLLIRPL | | 11930 |
| HPV16 | E5 | 24 | 10 | CVCLLIRPLL | | 11931 |
| HPV16 | E5 | 24 | 11 | CVCLLIRPLLL | | 11932 |
| HPV16 | E5 | 20 | 8 | CVLLCVCL | | 11933 |
| HPV16 | E5 | 20 | 9 | CVLLCVCLL | | 11934 |
| HPV16 | E5 | 20 | 10 | CVLLCVCLLI | | 11935 |
| HPV16 | E5 | 5 | 8 | DTASTTLL | | 11936 |
| HPV16 | E5 | 5 | 11 | DTASTTLLACF | | 11937 |
| HPV16 | E5 | 60 | 9 | FIVYIIFVY | | 11938 |
| HPV16 | E5 | 60 | 10 | FIVYIIFVYI | | 11939 |
| HPV16 | E5 | 72 | 9 | FLIHTHARF | | 11940 |
| HPV16 | E5 | 72 | 10 | FLIHTHARFL | | 11941 |
| HPV16 | E5 | 72 | 11 | FLIHTHARFLI | | 11942 |
| HPV16 | E5 | 15 | 8 | FLLCFCVL | | 11943 |
| HPV16 | E5 | 15 | 9 | FLLCFCVLL | | 11944 |
| HPV16 | E5 | 66 | 8 | FVYIPLFL | | 11945 |
| HPV16 | E5 | 66 | 9 | FVYIPLFLI | | 11946 |
| HPV16 | E5 | 75 | 8 | HTHARFLI | | 11947 |
| HPV16 | E5 | 65 | 8 | IFVYIPLF | | 11948 |
| HPV16 | E5 | 65 | 9 | IFVYIPLFL | | 11949 |
| HPV16 | E5 | 65 | 10 | IFVYIPLFLI | | 11950 |
| HPV16 | E5 | 64 | 8 | IIFVYIPL | | 11951 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | E5 | 64 | 9 | IIFVYIPLF | | 11952 |
| HPV16 | E5 | 64 | 10 | IIFVYIPLFL | | 11953 |
| HPV16 | E5 | 64 | 11 | IIFVYIPLFLI | | 11954 |
| HPV16 | E5 | 43 | 8 | IILVLLLW | | 11955 |
| HPV16 | E5 | 43 | 9 | IILVLLLWI | | 11956 |
| HPV16 | E5 | 44 | 8 | ILVLLLWI | | 11957 |
| HPV16 | E5 | 51 | 10 | ITAASAFRCF | | 11958 |
| HPV16 | E5 | 51 | 11 | ITAASAFRCFI | | 11959 |
| HPV16 | E5 | 61 | 8 | IVYIIFVY | | 11960 |
| HPV16 | E5 | 61 | 9 | IVYIIFVYI | | 11961 |
| HPV16 | E5 | 61 | 11 | IVYIIFVYIPL | | 11962 |
| HPV16 | E5 | 71 | 10 | LFLIHTHARF | | 11963 |
| HPV16 | E5 | 71 | 11 | LFLIHTHARFL | | 11964 |
| HPV16 | E5 | 73 | 8 | LIHTHARF | | 11965 |
| HPV16 | E5 | 73 | 9 | LIHTHARFL | | 11966 |
| HPV16 | E5 | 73 | 10 | LIHTHARFLI | | 11967 |
| HPV16 | E5 | 42 | 8 | LIILVLLL | | 11968 |
| HPV16 | E5 | 42 | 9 | LIILVLLLW | | 11969 |
| HPV16 | E5 | 42 | 10 | LIILVLLLWI | | 11970 |
| HPV16 | E5 | 11 | 9 | LLACFLLCF | | 11971 |
| HPV16 | E5 | 16 | 8 | LLCFCVLL | | 11972 |
| HPV16 | E5 | 22 | 8 | LLCVCLLI | | 11973 |
| HPV16 | E5 | 22 | 11 | LLCVCLLIRPL | | 11974 |
| HPV16 | E5 | 27 | 8 | LLIRPLLL | | 11975 |
| HPV16 | E5 | 32 | 8 | LLLSVSTY | | 11976 |
| HPV16 | E5 | 32 | 11 | LLLSVSTYTSL | | 11977 |
| HPV16 | E5 | 47 | 11 | LLLWITAASAF | | 11978 |
| HPV16 | E5 | 33 | 10 | LLSVSTYTSL | | 11979 |
| HPV16 | E5 | 33 | 11 | LLSVSTYTSLI | | 11980 |
| HPV16 | E5 | 48 | 10 | LLWITAASAF | | 11981 |
| HPV16 | E5 | 49 | 9 | LWITAASAF | | 11982 |
| HPV16 | E5 | 1 | 11 | MTNLDTASTTL | | 11983 |
| HPV16 | E5 | 3 | 9 | NLDTASTTL | | 11984 |
| HPV16 | E5 | 3 | 10 | NLDTASTTLL | | 11985 |
| HPV16 | E5 | 70 | 11 | PLFLIHTHARF | | 11986 |
| HPV16 | E5 | 31 | 9 | PLLLSVSTY | | 11987 |
| HPV16 | E5 | 41 | 8 | SLIILVLL | | 11988 |
| HPV16 | E5 | 41 | 9 | SLIILVLLL | | 11989 |
| HPV16 | E5 | 41 | 10 | SLIILVLLLW | | 11990 |
| HPV16 | E5 | 41 | 11 | SLIILVLLLWI | | 11991 |
| HPV16 | E5 | 8 | 8 | STTLLACF | | 11992 |
| HPV16 | E5 | 8 | 9 | STTLLACFL | | 11993 |
| HPV16 | E5 | 8 | 10 | STTLLACFLL | | 11994 |
| HPV16 | E5 | 37 | 8 | STYTSLII | | 11995 |
| HPV16 | E5 | 37 | 9 | STYTSLIIL | | 11996 |
| HPV16 | E5 | 37 | 11 | STYTSLIILVL | | 11997 |
| HPV16 | E5 | 35 | 8 | SVSTYTSL | | 11998 |
| HPV16 | E5 | 35 | 9 | SVSTYTSLI | | 11999 |
| HPV16 | E5 | 35 | 10 | SVSTYTSLII | | 12000 |
| HPV16 | E5 | 35 | 11 | SVSTYTSLIIL | | 12001 |
| HPV16 | E5 | 10 | 8 | TLLACFLL | | 12002 |
| HPV16 | E5 | 10 | 10 | TLLACFLLCF | | 12003 |
| HPV16 | E5 | 9 | 8 | TTLLACFL | | 12004 |
| HPV16 | E5 | 9 | 9 | TTLLACFLL | | 12005 |
| HPV16 | E5 | 9 | 11 | TTLLACFLLCF | | 12006 |
| HPV16 | E5 | 38 | 8 | TYTSLIIL | | 12007 |
| HPV16 | E5 | 38 | 10 | TYTSLIILVL | | 12008 |
| HPV16 | E5 | 38 | 11 | TYTSLIILVLL | | 12009 |
| HPV16 | E5 | 21 | 8 | VLLCVCLL | | 12010 |
| HPV16 | E5 | 21 | 9 | VLLCVCLLI | | 12011 |
| HPV16 | E5 | 62 | 8 | VYIIFVYI | | 12012 |
| HPV16 | E5 | 62 | 10 | VYIIFVYIPL | | 12013 |
| HPV16 | E5 | 62 | 11 | VYIIFVYIPLF | | 12014 |
| HPV16 | E5 | 67 | 8 | VYIPLFLI | | 12015 |
| HPV16 | E5 | 50 | 8 | WITAASAF | | 12016 |
| HPV16 | E5 | 50 | 11 | WITAASAFRCF | | 12017 |
| HPV16 | E5 | 63 | 9 | YIIFVYIPL | | 12018 |
| HPV16 | E5 | 63 | 10 | YIIFVYIPLF | | 12019 |
| HPV16 | E5 | 63 | 11 | YIIFVYIPLFL | | 12020 |
| HPV16 | E5 | 39 | 9 | YTSLIILVL | | 12021 |
| HPV16 | E5 | 39 | 10 | YTSLIILVLL | | 12022 |
| HPV16 | E5 | 39 | 11 | YTSLIILVLLL | | 12023 |
| HPV16 | E6 | 53 | 9 | AFRDLCIVY | | 12024 |
| HPV16 | E6 | 68 | 9 | AVCDKCLKF | | 12025 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | E6 | 68 | 10 | AVCDKCLKFY | | 12026 |
| HPV16 | E6 | 110 | 8 | CINCQKPL | | 12027 |
| HPV16 | E6 | 58 | 10 | CIVYRDGNPY | | 12028 |
| HPV16 | E6 | 73 | 8 | CLKFYSKI | | 12029 |
| HPV16 | E6 | 73 | 11 | CLKFYSKISEY | | 12030 |
| HPV16 | E6 | 23 | 8 | CTELQTTI | | 12031 |
| HPV16 | E6 | 23 | 11 | CTELQTTIHDI | | 12032 |
| HPV16 | E6 | 37 | 8 | CVYCKQQL | | 12033 |
| HPV16 | E6 | 37 | 9 | CVYCKQQLL | | 12034 |
| HPV16 | E6 | 87 | 9 | CYSLYGTTL | 0.046 | 12035 |
| HPV16 | E6 | 51 | 9 | DFAFRDLCI | 0.0003 | 12036 |
| HPV16 | E6 | 51 | 11 | DFAFRDLCIVY | | 12037 |
| HPV16 | E6 | 32 | 8 | DIILECVY | | 12038 |
| HPV16 | E6 | 25 | 9 | ELQTTIHDI | | 12039 |
| HPV16 | E6 | 25 | 10 | ELQTTIHDII | | 12040 |
| HPV16 | E6 | 25 | 11 | ELQTTIHDIIL | | 12041 |
| HPV16 | E6 | 48 | 10 | EVYDFAFRDL | | 12042 |
| HPV16 | E6 | 82 | 9 | EYRHYCYSL | 0.0051 | 12043 |
| HPV16 | E6 | 82 | 10 | EYRHYCYSLY | | 12044 |
| HPV16 | E6 | 76 | 8 | FYSKISEY | 0.0007 | 12045 |
| HPV16 | E6 | 76 | 11 | FYSKISEYRHY | 0.0004 | 12046 |
| HPV16 | E6 | 92 | 8 | GTTLEQQY | | 12047 |
| HPV16 | E6 | 125 | 8 | HLDKKQRF | | 12048 |
| HPV16 | E6 | 125 | 11 | HLDKKQRFHNI | | 12049 |
| HPV16 | E6 | 85 | 11 | HYCYSLYGTTL | 0.065 | 12050 |
| HPV16 | E6 | 34 | 11 | ILECVYCKQQL | | 12051 |
| HPV16 | E6 | 59 | 9 | IVYRDGNPY | 0.0001 | 12052 |
| HPV16 | E6 | 75 | 9 | KFYSKISEY | | 12053 |
| HPV16 | E6 | 79 | 8 | KISEYRHY | | 12054 |
| HPV16 | E6 | 79 | 10 | KISEYRHYCY | | 12055 |
| HPV16 | E6 | 18 | 9 | KLPQLCTEL | | 12056 |
| HPV16 | E6 | 107 | 11 | LIRCINCQKPL | | 12057 |
| HPV16 | E6 | 44 | 9 | LLRREVYDF | | 12058 |
| HPV16 | E6 | 44 | 11 | LLRREVYDFAF | | 12059 |
| HPV16 | E6 | 90 | 10 | LYGTTLEQQY | | 12060 |
| HPV16 | E6 | 134 | 11 | NIRGRWTGRCM | | 12061 |
| HPV16 | E6 | 102 | 10 | PLCDLLIRCI | | 12062 |
| HPV16 | E6 | 116 | 11 | PLCPEEKQRHL | | 12063 |
| HPV16 | E6 | 66 | 9 | PYAVCDKCL | 0.0078 | 12064 |
| HPV16 | E6 | 66 | 11 | PYAVCDKCLKF | 0.11 | 12065 |
| HPV16 | E6 | 21 | 10 | QLCTELQTTI | | 12066 |
| HPV16 | E6 | 43 | 8 | QLLRREVY | | 12067 |
| HPV16 | E6 | 43 | 10 | QLLRREVYDF | | 12068 |
| HPV16 | E6 | 27 | 8 | QTTIHDII | | 12069 |
| HPV16 | E6 | 27 | 9 | QTTIHDIIL | | 12070 |
| HPV16 | E6 | 98 | 9 | QYNKPLCDL | 0.0001 | 12071 |
| HPV16 | E6 | 98 | 10 | QYNKPLCDLL | 0.0015 | 12072 |
| HPV16 | E6 | 98 | 1 | QYNKPLCDLLI | | 12073 |
| HPV16 | E6 | 131 | 9 | RFHNIRGRW | 0.022 | 12074 |
| HPV16 | E6 | 151 | 8 | RTRRETQL | | 12075 |
| HPV16 | E6 | 89 | 11 | SLYGTTLEQQY | | 12076 |
| HPV16 | E6 | 29 | 11 | TIHDIILECVY | | 12077 |
| HPV16 | E6 | 94 | 10 | TLEQQYNKPL | | 12078 |
| HPV16 | E6 | 28 | 8 | TTIHDIIL | | 12079 |
| HPV16 | E6 | 93 | 11 | TTLEQQYNKPL | | 12080 |
| HPV16 | E6 | 38 | 8 | VYCKQQLL | 0.0069 | 12081 |
| HPV16 | E6 | 49 | 9 | VYDFAFRDL | 0.015 | 12082 |
| HPV16 | E6 | 49 | 11 | VYDFAFRDLCI | | 12083 |
| HPV16 | E6 | 60 | 8 | VYRDGNPY | 0.0001 | 12084 |
| HPV16 | E7 | 68 | 9 | CVQSTHVDI | | 12085 |
| HPV16 | E7 | 75 | 8 | DIRTLEDL | | 12086 |
| HPV16 | E7 | 75 | 9 | DIRTLEDLL | | 12087 |
| HPV16 | E7 | 75 | 10 | DIRTLEDLLM | | 12088 |
| HPV16 | E7 | 81 | 9 | DLLMGTLGI | | 12089 |
| HPV16 | E7 | 14 | 9 | DLQPETTDL | | 12090 |
| HPV16 | E7 | 14 | 10 | DLQPETTDLY | | 12091 |
| HPV16 | E7 | 21 | 8 | DLYCYEQL | | 12092 |
| HPV16 | E7 | 4 | 8 | DTPTLHEY | | 12093 |
| HPV16 | E7 | 4 | 9 | DTPTLHEYM | | 12094 |
| HPV16 | E7 | 4 | 10 | DTPTLHEYML | | 12095 |
| HPV16 | E7 | 18 | 8 | ETTDLYCY | 0.0001 | 12096 |
| HPV16 | E7 | 18 | 11 | ETTDLYCYEQL | | 12097 |
| HPV16 | E7 | 85 | 9 | GTLGIVCPI | | 12098 |
| HPV16 | E7 | 73 | 10 | HVDIRTLEDL | | 12099 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | E7 | 73 | 11 | HVDIRTLEDLL | | 12100 |
| HPV16 | E7 | 82 | 8 | LLMGTLGI | | 12101 |
| HPV16 | E7 | 83 | 11 | LMGTLGIVCPI | | 12102 |
| HPV16 | E7 | 12 | 11 | MLDLQPETTDL | | 12103 |
| HPV16 | E7 | 6 | 8 | PTLHEYML | | 12104 |
| HPV16 | E7 | 6 | 10 | PTLHEYMLDL | | 12105 |
| HPV16 | E7 | 66 | 11 | RLCVQSTHVDI | | 12106 |
| HPV16 | E7 | 77 | 8 | RTLEDLLM | | 12107 |
| HPV16 | E7 | 77 | 11 | RTLEDLLMGTL | | 12108 |
| HPV16 | E7 | 71 | 9 | STHVDIRTL | | 12109 |
| HPV16 | E7 | 56 | 10 | TFCCKCDSTL | | 12110 |
| HPV16 | E7 | 78 | 10 | TLEDLLMGTL | | 12111 |
| HPV16 | E7 | 86 | 8 | TLGIVCPI | | 12112 |
| HPV16 | E7 | 7 | 9 | TLHEYMLDL | | 12113 |
| HPV16 | E7 | 19 | 10 | TTDLYCYEQL | | 12114 |
| HPV16 | E7 | 55 | 11 | VTFCCKCDSTL | | 12115 |
| HPV16 | L1 | 373 | 9 | AISTSETTY | | 12116 |
| HPV16 | L1 | 292 | 10 | AVGENVPDDL | | 12117 |
| HPV16 | L1 | 292 | 11 | AVGENVPDDLY | | 12118 |
| HPV16 | L1 | 70 | 9 | AVGHPYFPI | | 12119 |
| HPV16 | L1 | 205 | 10 | AVNPGDCPPL | | 12120 |
| HPV16 | L1 | 172 | 11 | CISMDYKQTQL | | 12121 |
| HPV16 | L1 | 183 | 9 | CLIGCKPPI | | 12122 |
| HPV16 | L1 | 251 | 10 | CTSICKYPDY | | 12123 |
| HPV16 | L1 | 251 | 11 | CTSICKYPDYI | | 12124 |
| HPV16 | L1 | 13 | 9 | CYENDVNVY | | 12125 |
| HPV16 | L1 | 13 | 11 | CYENDVNVYHI | | 12126 |
| HPV16 | L1 | 249 | 9 | DICTSICKY | | 12127 |
| HPV16 | L1 | 484 | 11 | DLDQFPLGRKF | | 12128 |
| HPV16 | L1 | 397 | 8 | DLQFIFQL | | 12129 |
| HPV16 | L1 | 397 | 11 | DLQFIFQLCKI | | 12130 |
| HPV16 | L1 | 225 | 10 | DMVDTGFGAM | | 12131 |
| HPV16 | L1 | 154 | 8 | DTENASAY | | 12132 |
| HPV16 | L1 | 228 | 9 | DTGFGAMDF | | 12133 |
| HPV16 | L1 | 361 | 8 | DTTRSTNM | | 12134 |
| HPV16 | L1 | 361 | 10 | DTTRSTNMSL | | 12135 |
| HPV16 | L1 | 442 | 11 | DTYRFVTSQAI | | 12136 |
| HPV16 | L1 | 412 | 9 | DVMTYIHSM | | 12137 |
| HPV16 | L1 | 17 | 8 | DVNVYHIF | | 12138 |
| HPV16 | L1 | 17 | 9 | DVNVYHIFF | | 12139 |
| HPV16 | L1 | 17 | 11 | DVNVYHIFFQM | | 12140 |
| HPV16 | L1 | 259 | 10 | DYIKMVSEPY | | 12141 |
| HPV16 | L1 | 176 | 9 | DYKQTQLCL | | 12142 |
| HPV16 | L1 | 176 | 10 | DYKQTQLCLI | | 12143 |
| HPV16 | L1 | 378 | 9 | ETTYKNTNF | | 12144 |
| HPV16 | L1 | 132 | 8 | EVGRGQPL | | 12145 |
| HPV16 | L1 | 474 | 8 | EVNLKEKF | | 12146 |
| HPV16 | L1 | 245 | 10 | EVPLDICTSI | | 12147 |
| HPV16 | L1 | 395 | 8 | EYDLQFIF | | 12148 |
| HPV16 | L1 | 395 | 10 | EYDLQFIFQL | | 12149 |
| HPV16 | L1 | 388 | 9 | EYLRHGEEY | | 12150 |
| HPV16 | L1 | 388 | 11 | EYLRHGEEYDL | | 12151 |
| HPV16 | L1 | 52 | 8 | EYVATRNI | | 12152 |
| HPV16 | L1 | 52 | 9 | EYVATRNIY | | 12153 |
| HPV16 | L1 | 52 | 10 | EYVATRNIYY | | 12154 |
| HPV16 | L1 | 24 | 8 | FFQMSLWL | | 12155 |
| HPV16 | L1 | 273 | 9 | FFYLRREQM | | 12156 |
| HPV16 | L1 | 273 | 10 | FFYLRREQMF | | 12157 |
| HPV16 | L1 | 400 | 8 | FIFQLCKI | | 12158 |
| HPV16 | L1 | 400 | 10 | FIFQLCKITL | | 12159 |
| HPV16 | L1 | 5 | 10 | FIYILVITCY | | 12160 |
| HPV16 | L1 | 472 | 10 | FWEVNLKEKF | | 12161 |
| HPV16 | L1 | 274 | 8 | FYLRREQM | | 12162 |
| HPV16 | L1 | 274 | 9 | FYLRREQMF | | 12163 |
| HPV16 | L1 | 116 | 9 | FYNPDTQRL | | 12164 |
| HPV16 | L1 | 116 | 11 | FYNPDTQRLVW | | 12165 |
| HPV16 | L1 | 230 | 10 | GFGAMDFTTL | | 12166 |
| HPV16 | L1 | 110 | 8 | FGPDTSFY | | 12167 |
| HPV16 | L1 | 348 | 8 | GICWGNQL | | 12168 |
| HPV16 | L1 | 348 | 9 | GICWGNQLF | | 12169 |
| HPV16 | L1 | 142 | 8 | GISGHPLL | | 12170 |
| HPV16 | L1 | 142 | 11 | GISGHPLLNKL | | 12171 |
| HPV16 | L1 | 499 | 8 | GLKAKPKF | | 12172 |
| HPV16 | L1 | 499 | 10 | GLKAKPKFTL | | 12173 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | L1 | 431 | 10 | GLQPPPGGTL | | 12174 |
| HPV16 | L1 | 93 | 9 | GLQYRVFRI | | 12175 |
| HPV16 | L1 | 93 | 11 | GLQYRVFRIHL | | 12176 |
| HPV16 | L1 | 438 | 9 | GTLEDTYRF | | 12177 |
| HPV16 | L1 | 166 | 8 | GVDNRECI | | 12178 |
| HPV16 | L1 | 166 | 10 | GVDNRECISM | | 12179 |
| HPV16 | L1 | 130 | 10 | GVEVGRGQPL | | 12180 |
| HPV16 | L1 | 140 | 9 | GVGISGHPL | | 12181 |
| HPV16 | L1 | 140 | 10 | GVGISGHPLL | | 12182 |
| HPV16 | L1 | 22 | 8 | HIFFQMSL | | 12183 |
| HPV16 | L1 | 22 | 9 | HIFFQMSLW | | 12184 |
| HPV16 | L1 | 22 | 10 | HIFFQMSLWL | | 12185 |
| HPV16 | L1 | 102 | 8 | HLPDPNKF | | 12186 |
| HPV16 | L1 | 102 | 10 | HLPDPNKFGF | | 12187 |
| HPV16 | L1 | 457 | 11 | HTPPAPKEDPL | | 12188 |
| HPV16 | L1 | 23 | 8 | IFFQMSLW | | 12189 |
| HPV16 | L1 | 23 | 9 | IFFQMSLWL | | 12190 |
| HPV16 | L1 | 332 | 8 | IFNKPYWL | | 12191 |
| HPV16 | L1 | 401 | 9 | IFQLCKITL | | 12192 |
| HPV16 | L1 | 424 | 9 | ILEDWNFGL | | 12193 |
| HPV16 | L1 | 86 | 9 | ILVPKVSGL | | 12194 |
| HPV16 | L1 | 86 | 11 | ILVPKVSGLQY | | 12195 |
| HPV16 | L1 | 11 | 11 | ITCYENDVNVY | | 12196 |
| HPV16 | L1 | 407 | 8 | ITLTADVM | | 12197 |
| HPV16 | L1 | 407 | 10 | ITLTADVMTY | | 12198 |
| HPV16 | L1 | 407 | 11 | ITLTADVMTYI | | 12199 |
| HPV16 | L1 | 6 | 9 | IYILVITCY | | 12200 |
| HPV16 | L1 | 59 | 10 | IYYHAGTSRL | | 12201 |
| HPV16 | L1 | 59 | 11 | IYYHAGTSRLL | | 12202 |
| HPV16 | L1 | 108 | 9 | KFGFPDTSF | | 12203 |
| HPV16 | L1 | 108 | 10 | KFGFPDTSFY | | 12204 |
| HPV16 | L1 | 493 | 8 | KFLLQAGL | | 12205 |
| HPV16 | L1 | 480 | 9 | KFSADLDQF | | 12206 |
| HPV16 | L1 | 480 | 11 | KFSADLDQFPL | | 12207 |
| HPV16 | L1 | 85 | 10 | KILVPKVSGL | | 12208 |
| HPV16 | L1 | 406 | 9 | KITLTADVM | | 12209 |
| HPV16 | L1 | 406 | 11 | KITLTADVMTY | | 12210 |
| HPV16 | L1 | 151 | 11 | KLDDTENASAY | | 12211 |
| HPV16 | L1 | 262 | 11 | KMVSEPYGDSL | | 12212 |
| HPV16 | L1 | 90 | 10 | KVSGLQYRVF | | 12213 |
| HPV16 | L1 | 46 | 8 | KVVSTDEY | | 12214 |
| HPV16 | L1 | 256 | 8 | KYPDYIKM | | 12215 |
| HPV16 | L1 | 469 | 9 | KYTFWEVNL | | 12216 |
| HPV16 | L1 | 272 | 10 | LFFYLRREQM | | 12217 |
| HPV16 | L1 | 272 | 11 | LFFYLRREQMF | | 12218 |
| HPV16 | L1 | 184 | 8 | LIGCKPPI | | 12219 |
| HPV16 | L1 | 216 | 11 | LINTVIQDGDM | | 12220 |
| HPV16 | L1 | 68 | 8 | LLAVGHPY | | 12221 |
| HPV16 | L1 | 68 | 9 | LLAVGHPYF | | 12222 |
| HPV16 | L1 | 68 | 11 | LLAVGHPYFPI | | 12223 |
| HPV16 | L1 | 409 | 8 | LTADVMTY | | 12224 |
| HPV16 | L1 | 409 | 9 | LTADVMTYI | | 12225 |
| HPV16 | L1 | 87 | 8 | LVPKVSGL | | 12226 |
| HPV16 | L1 | 87 | 10 | LVPKVSGLQY | | 12227 |
| HPV16 | L1 | 29 | 10 | LWLPSEATVY | | 12228 |
| HPV16 | L1 | 29 | 11 | LWLPSEATVYL | | 12229 |
| HPV16 | L1 | 414 | 11 | MTYIHSMNSTI | | 12230 |
| HPV16 | L1 | 226 | 9 | MVDTGFGAM | | 12231 |
| HPV16 | L1 | 226 | 11 | MVDTGFGAMDF | | 12232 |
| HPV16 | L1 | 263 | 10 | MVSEPYGDSL | | 12233 |
| HPV16 | L1 | 263 | 11 | MVSEPYGDSLF | | 12234 |
| HPV16 | L1 | 325 | 8 | MVTSDAQI | | 12235 |
| HPV16 | L1 | 325 | 9 | MVTSDAQIF | | 12236 |
| HPV16 | L1 | 58 | 11 | NIYYHAGTSRL | | 12237 |
| HPV16 | L1 | 311 | 8 | NLASSNYF | | 12238 |
| HPV16 | L1 | 476 | 10 | NLKEKFSADL | | 12239 |
| HPV16 | L1 | 367 | 8 | NMSLCAAI | | 12240 |
| HPV16 | L1 | 383 | 8 | NTNFKEYL | | 12241 |
| HPV16 | L1 | 218 | 9 | NTVIQDGDM | | 12242 |
| HPV16 | L1 | 296 | 8 | NVPDDLYI | | 12243 |
| HPV16 | L1 | 19 | 9 | NVYHIFFQM | | 12244 |
| HPV16 | L1 | 19 | 11 | NVYHIFFQMSL | | 12245 |
| HPV16 | L1 | 316 | 10 | NYFPTPSGSM | | 12246 |
| HPV16 | L1 | 77 | 10 | PIKKPNNNKI | | 12247 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | L1 | 77 | 11 | PIKKPNNNKIL | | 12248 |
| HPV16 | L1 | 247 | 8 | PLDICTSI | | 12249 |
| HPV16 | L1 | 247 | 11 | PLDICTSICKY | | 12250 |
| HPV16 | L1 | 213 | 9 | PLELINTVI | | 12251 |
| HPV16 | L1 | 489 | 8 | PLGRKFLL | | 12252 |
| HPV16 | L1 | 138 | 11 | PLGVGISGHPL | | 12253 |
| HPV16 | L1 | 466 | 8 | PLKKYTFW | | 12254 |
| HPV16 | L1 | 43 | 11 | PVSKVVSTDEY | | 12255 |
| HPV16 | L1 | 267 | 8 | PYGDSLFF | | 12256 |
| HPV16 | L1 | 267 | 9 | PYGDSLFFY | | 12257 |
| HPV16 | L1 | 267 | 10 | PYGDSLFFYL | | 12258 |
| HPV16 | L1 | 399 | 9 | QFIFQLCKI | | 12259 |
| HPV16 | L1 | 399 | 11 | QFIFQLCKITL | | 12260 |
| HPV16 | L1 | 487 | 8 | QFPLGRKF | | 12261 |
| HPV16 | L1 | 487 | 9 | QFPLGRKFL | | 12262 |
| HPV16 | L1 | 487 | 10 | QFPLGRKFLL | | 12263 |
| HPV16 | L1 | 331 | 8 | QIFNKPYW | | 12264 |
| HPV16 | L1 | 331 | 9 | QIFNKPYWL | | 12265 |
| HPV16 | L1 | 181 | 11 | QLCLIGCKPPI | | 12266 |
| HPV16 | L1 | 280 | 8 | QMFVRHLF | | 12267 |
| HPV16 | L1 | 2 | 8 | QVTFIYIL | | 12268 |
| HPV16 | L1 | 2 | 10 | QVTFIYILVI | | 12269 |
| HPV16 | L1 | 95 | 9 | QYRVFRIHL | | 12270 |
| HPV16 | L1 | 445 | 8 | RFVTSQAI | | 12271 |
| HPV16 | L1 | 100 | 10 | RIHLPDPNKF | | 12272 |
| HPV16 | L1 | 67 | 9 | RLLAVGHPY | | 12273 |
| HPV16 | L1 | 67 | 10 | RLLAVGHPYF | | 12274 |
| HPV16 | L1 | 115 | 10 | SFYNPDTQRL | | 12275 |
| HPV16 | L1 | 253 | 8 | SICKYPDY | | 12276 |
| HPV16 | L1 | 253 | 9 | SICKYPDYI | | 12277 |
| HPV16 | L1 | 253 | 11 | SICKYPDYIKM | | 12278 |
| HPV16 | L1 | 271 | 11 | SLFFYLRREQM | | 12279 |
| HPV16 | L1 | 28 | 11 | SLWLPSEATVY | | 12280 |
| HPV16 | L1 | 174 | 9 | SMDYKQTQL | | 12281 |
| HPV16 | L1 | 174 | 11 | SMDYKQTQLCL | | 12282 |
| HPV16 | L1 | 419 | 10 | SMNSTILEDW | | 12283 |
| HPV16 | L1 | 324 | 9 | SMVTSDAQI | | 12284 |
| HPV16 | L1 | 324 | 10 | SMVTSDAQIF | | 12285 |
| HPV16 | L1 | 308 | 10 | STANLASSNY | | 12286 |
| HPV16 | L1 | 308 | 11 | STANLASSNYF | | 12287 |
| HPV16 | L1 | 49 | 11 | STDEYVARTNI | | 12288 |
| HPV16 | L1 | 422 | 9 | STILEDWNF | | 12289 |
| HPV16 | L1 | 422 | 11 | STILEDWNFGL | | 12290 |
| HPV16 | L1 | 365 | 10 | STNMSLCAAI | | 12291 |
| HPV16 | L1 | 521 | 11 | STTAKRKKRKL | | 12292 |
| HPV16 | L1 | 4 | 8 | TFIYILVI | | 12293 |
| HPV16 | L1 | 4 | 11 | TFIYILVITCY | | 12294 |
| HPV16 | L1 | 471 | 11 | TFWEVNLKEKF | | 12295 |
| HPV16 | L1 | 423 | 8 | TILEDWNF | | 12296 |
| HPV16 | L1 | 423 | 10 | TILEDWNFGL | | 12297 |
| HPV16 | L1 | 439 | 8 | TLEDTYRF | | 12298 |
| HPV16 | L1 | 238 | 11 | TLQANKSEVPL | | 12299 |
| HPV16 | L1 | 408 | 9 | TLTADVMTY | | 12300 |
| HPV16 | L1 | 408 | 10 | TLTADVMTYI | | 12301 |
| HPV16 | L1 | 522 | 10 | TTAKRKKRKL | | 12302 |
| HPV16 | L1 | 362 | 9 | TTRSTNMSL | | 12303 |
| HPV16 | L1 | 379 | 8 | TTYKNTNF | | 12304 |
| HPV16 | L1 | 379 | 11 | TTYKNTNFKEY | | 12305 |
| HPV16 | L1 | 219 | 8 | TVIQDGDM | | 12306 |
| HPV16 | L1 | 358 | 11 | TVVDTTRSTNM | | 12307 |
| HPV16 | L1 | 415 | 10 | TYIHSMNSTI | | 12308 |
| HPV16 | L1 | 415 | 11 | TYIHSMNSTIL | | 12309 |
| HPV16 | L1 | 380 | 10 | TYKNTNFKEY | | 12310 |
| HPV16 | L1 | 380 | 11 | TYKNTNFKEYL | | 12311 |
| HPV16 | L1 | 443 | 10 | TYRFVTSQAI | | 12312 |
| HPV16 | L1 | 413 | 8 | VMTYIHSM | | 12313 |
| HPV16 | L1 | 3 | 9 | VTFIYILVI | | 12314 |
| HPV16 | L1 | 326 | 8 | VTSDAQIF | | 12315 |
| HPV16 | L1 | 359 | 10 | VVDTTRSTNM | | 12316 |
| HPV16 | L1 | 20 | 8 | VYHIFFQM | | 12317 |
| HPV16 | L1 | 20 | 10 | VYHIFFQMSL | | 12318 |
| HPV16 | L1 | 20 | 11 | VYHIFFQMSLW | | 12319 |
| HPV16 | L1 | 30 | 9 | WLPSEATVY | | 12320 |
| HPV16 | L1 | 30 | 10 | WLPSEATVYL | | 12321 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | L1 | 317 | 9 | YFPTPSGSM | | 12322 |
| HPV16 | L1 | 416 | 9 | YIHSMNSTI | | 12323 |
| HPV16 | L1 | 416 | 10 | YIHSMNSTIL | | 12324 |
| HPV16 | L1 | 302 | 11 | YIKGSGSTANL | | 12325 |
| HPV16 | L1 | 260 | 9 | YIKMVSEPY | | 12326 |
| HPV16 | L1 | 7 | 8 | YILVITCY | | 12327 |
| HPV16 | L1 | 389 | 8 | YLRHGEEY | | 12328 |
| HPV16 | L1 | 389 | 10 | YLRHGEEYDL | | 12329 |
| HPV16 | L1 | 275 | 8 | YLRREQMF | | 12330 |
| HPV16 | L1 | 470 | 8 | YTFWEVNL | | 12331 |
| HPV16 | L1 | 53 | 8 | YVARTNIY | | 12332 |
| HPV16 | L1 | 53 | 9 | YVARTNIYY | | 12333 |
| HPV16 | L1 | 60 | 9 | YYHAGTSRL | | 12334 |
| HPV16 | L1 | 60 | 10 | YYHAGTSRLL | | 12335 |
| HPV16 | L2 | 241 | 9 | AFITTPTKL | | 12336 |
| HPV16 | L2 | 241 | 10 | AFITTPTKLI | | 12337 |
| HPV16 | L2 | 356 | 10 | ALPTSINNGL | | 12338 |
| HPV16 | L2 | 356 | 11 | ALPTSINNGLY | | 12339 |
| HPV16 | L2 | 293 | 9 | ALTSRRTGI | | 12340 |
| HPV16 | L2 | 293 | 11 | ALTSRRTGIRY | | 12341 |
| HPV16 | L2 | 256 | 11 | AYEGIDVDNTL | | 12342 |
| HPV16 | L2 | 282 | 8 | DFLDIVAL | | 12343 |
| HPV16 | L2 | 329 | 11 | DFSTIDSAEEI | | 12344 |
| HPV16 | L2 | 445 | 8 | DFYLHPSY | | 12345 |
| HPV16 | L2 | 445 | 9 | DFYLHPSYY | | 12346 |
| HPV16 | L2 | 445 | 10 | DFYLHPSYYM | | 12347 |
| HPV16 | L2 | 445 | 11 | DFYLHPSYYML | | 12348 |
| HPV16 | L2 | 31 | 11 | DIIPKVEGKTI | | 12349 |
| HPV16 | L2 | 285 | 10 | DIVALHRPAL | | 12350 |
| HPV16 | L2 | 367 | 8 | DIYADDFI | | 12351 |
| HPV16 | L2 | 84 | 10 | DTLAPVRPPL | | 12352 |
| HPV16 | L2 | 140 | 9 | DTTPAILDI | | 12353 |
| HPV16 | L2 | 261 | 8 | DVDNTLYF | | 12354 |
| HPV16 | L2 | 195 | 8 | EIPMDTFI | | 12355 |
| HPV16 | L2 | 340 | 10 | ELQTITPSTY | | 12356 |
| HPV16 | L2 | 176 | 8 | ETGGHFTL | | 12357 |
| HPV16 | L2 | 242 | 8 | FITTPTKL | | 12358 |
| HPV16 | L2 | 242 | 9 | FITTPTKLI | | 12359 |
| HPV16 | L2 | 242 | 11 | FITTPTKLITY | | 12360 |
| HPV16 | L2 | 181 | 8 | FTLSSSTI | | 12361 |
| HPV16 | L2 | 446 | 8 | FYLHPSYY | | 12362 |
| HPV16 | L2 | 446 | 9 | FYLHPSYYM | | 12363 |
| HPV16 | L2 | 446 | 10 | FYLHPSYYML | | 12364 |
| HPV16 | L2 | 259 | 8 | GIDVDNTL | | 12365 |
| HPV16 | L2 | 259 | 9 | GIDVDNTLY | | 12366 |
| HPV16 | L2 | 259 | 10 | GIDVDNTLYF | | 12367 |
| HPV16 | L2 | 364 | 10 | GLYDIYADDF | | 12368 |
| HPV16 | L2 | 364 | 11 | GLYDIYADDFI | | 12369 |
| HPV16 | L2 | 26 | 8 | GTCPPDII | | 12370 |
| HPV16 | L2 | 65 | 8 | GTGGRTGY | | 12371 |
| HPV16 | L2 | 65 | 9 | GTGGRTGYI | | 12372 |
| HPV16 | L2 | 65 | 11 | GTGGRTGYIPL | | 12373 |
| HPV16 | L2 | 76 | 11 | GTRPPTATDTL | | 12374 |
| HPV16 | L2 | 52 | 9 | GVFFGGLGI | | 12375 |
| HPV16 | L2 | 392 | 9 | GYIPANTTI | | 12376 |
| HPV16 | L2 | 392 | 11 | GYIPANTTIPF | | 12377 |
| HPV16 | L2 | 180 | 9 | HFTLSSSTI | | 12378 |
| HPV16 | L2 | 325 | 9 | HYYYDFSTI | | 12379 |
| HPV16 | L2 | 439 | 8 | IIADAGDF | | 12380 |
| HPV16 | L2 | 439 | 9 | IIADAGDFY | | 12381 |
| HPV16 | L2 | 439 | 10 | IIADAGDFYL | | 12382 |
| HPV16 | L2 | 32 | 10 | IIPKVEGKTI | | 12383 |
| HPV16 | L2 | 45 | 10 | ILQYGSMGVF | | 12384 |
| HPV16 | L2 | 45 | 11 | ILQYGSMGVFF | | 12385 |
| HPV16 | L2 | 420 | 8 | ITDQAPSL | | 12386 |
| HPV16 | L2 | 420 | 9 | ITDQAPSLI | | 12387 |
| HPV16 | L2 | 420 | 11 | ITDQAPSLIPI | | 12388 |
| HPV16 | L2 | 243 | 8 | ITTPTKLI | | 12389 |
| HPV16 | L2 | 243 | 10 | ITTPTKLITY | | 12390 |
| HPV16 | L2 | 135 | 11 | ITTSTDTTPAI | | 12391 |
| HPV16 | L2 | 250 | 8 | ITYDNPAY | | 12392 |
| HPV16 | L2 | 250 | 11 | ITYDNPAYEGI | | 12393 |
| HPV16 | L2 | 286 | 9 | IVALHRPAL | | 12394 |
| HPV16 | L2 | 430 | 8 | IVPGSPQY | | 12395 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | L2 | 430 | 10 | IVPGSPQYTI | | 12396 |
| HPV16 | L2 | 430 | 11 | IVPGSPQYTII | | 12397 |
| HPV16 | L2 | 105 | 10 | IVSLVEETSF | | 12398 |
| HPV16 | L2 | 105 | 11 | IVSLVEETSFI | | 12399 |
| HPV16 | L2 | 248 | 10 | KLITYDNPAY | | 12400 |
| HPV16 | L2 | 39 | 8 | KTIADQIL | | 12401 |
| HPV16 | L2 | 39 | 10 | KTIADQILQY | | 12402 |
| HPV16 | L2 | 35 | 11 | KVEGKTIADQI | | 12403 |
| HPV16 | L2 | 323 | 8 | KVHYYYDF | | 12404 |
| HPV16 | L2 | 323 | 11 | KVHYYYDFSTI | | 12405 |
| HPV16 | L2 | 236 | 8 | KVVDPAFI | | 12406 |
| HPV16 | L2 | 427 | 11 | LIPIVPGSPQY | | 12407 |
| HPV16 | L2 | 249 | 9 | LITYDNPAY | | 12408 |
| HPV16 | L2 | 294 | 8 | LTSRRTGI | | 12409 |
| HPV16 | L2 | 294 | 10 | LTSRRTGIRY | | 12410 |
| HPV16 | L2 | 108 | 8 | LVEETSFI | | 12411 |
| HPV16 | L2 | 410 | 9 | LVSGPDIPI | | 12412 |
| HPV16 | L2 | 410 | 11 | LVSGPDIPINI | | 12413 |
| HPV16 | L2 | 365 | 9 | LYDIYADDF | | 12414 |
| HPV16 | L2 | 365 | 10 | LYDIYADDFI | | 12415 |
| HPV16 | L2 | 266 | 10 | LYFSSNDNSI | | 12416 |
| HPV16 | L2 | 454 | 9 | MLRKRRKRL | | 12417 |
| HPV16 | L2 | 454 | 11 | MLRKRRKRLPY | | 12418 |
| HPV16 | L2 | 276 | 8 | NIAPDPDF | | 12419 |
| HPV16 | L2 | 276 | 9 | NIAPDPDFL | | 12420 |
| HPV16 | L2 | 276 | 11 | NIAPDPDFLDI | | 12421 |
| HPV16 | L2 | 407 | 10 | NIPLVSGPDI | | 12422 |
| HPV16 | L2 | 419 | 9 | NITDQAPSL | | 12423 |
| HPV16 | L2 | 419 | 10 | NITDQAPSLI | | 12424 |
| HPV16 | L2 | 397 | 10 | NTTIPFGGAY | | 12425 |
| HPV16 | L2 | 208 | 9 | NTVTSSTPI | | 12426 |
| HPV16 | L2 | 192 | 10 | NYEEIPMDTF | | 12427 |
| HPV16 | L2 | 192 | 11 | NYEEIPMDTFI | | 12428 |
| HPV16 | L2 | 401 | 8 | PFGGAYNI | | 12429 |
| HPV16 | L2 | 401 | 10 | PFGGAYNIPL | | 12430 |
| HPV16 | L2 | 417 | 11 | PINITDQAPSL | | 12431 |
| HPV16 | L2 | 215 | 11 | PIPGSRPVARL | | 12432 |
| HPV16 | L2 | 429 | 9 | PIVPGSPQY | | 12433 |
| HPV16 | L2 | 429 | 11 | PIVPGSPQYTI | | 12434 |
| HPV16 | L2 | 409 | 8 | PLVSGPDI | | 12435 |
| HPV16 | L2 | 409 | 10 | PLVSGPDIPI | | 12436 |
| HPV16 | L2 | 161 | 9 | PTFTDPSVL | | 12437 |
| HPV16 | L2 | 172 | 10 | PTPAETGGHF | | 12438 |
| HPV16 | L2 | 358 | 8 | PTSINNGL | | 12439 |
| HPV16 | L2 | 358 | 9 | PTSINNGLY | | 12440 |
| HPV16 | L2 | 358 | 11 | PTSINNGLYDI | | 12441 |
| HPV16 | L2 | 221 | 8 | PVARLGLY | | 12442 |
| HPV16 | L2 | 97 | 9 | PVGPSDPSI | | 12443 |
| HPV16 | L2 | 381 | 10 | PVPSVPSTSL | | 12444 |
| HPV16 | L2 | 463 | 9 | PYFFSDVSL | | 12445 |
| HPV16 | L2 | 44 | 8 | QILQYGSM | | 12446 |
| HPV16 | L2 | 44 | 11 | QILQYGSMGVF | | 12447 |
| HPV16 | L2 | 342 | 8 | QTITPSTY | | 12448 |
| HPV16 | L2 | 310 | 11 | QTLRTRSGKSI | | 12449 |
| HPV16 | L2 | 234 | 9 | QVKVVDPAF | | 12450 |
| HPV16 | L2 | 234 | 10 | QVKVVDPAFI | | 12451 |
| HPV16 | L2 | 47 | 8 | QYGSMGVF | | 12452 |
| HPV16 | L2 | 47 | 9 | QYGSMGVFF | | 12453 |
| HPV16 | L2 | 436 | 11 | QYTIIADAGDF | | 12454 |
| HPV16 | L2 | 305 | 8 | RIGNKQTL | | 12455 |
| HPV16 | L2 | 461 | 11 | RLPYFFSDVSL | | 12456 |
| HPV16 | L2 | 298 | 9 | RTGIRYSRI | | 12457 |
| HPV16 | L2 | 9 | 10 | RTKRASATQL | | 12458 |
| HPV16 | L2 | 9 | 11 | RTKRASATQLY | | 12459 |
| HPV16 | L2 | 313 | 8 | RTRSGKSI | | 12460 |
| HPV16 | L2 | 302 | 11 | RYSRIGNKQTL | | 12461 |
| HPV16 | L2 | 319 | 8 | SIGAKVHY | | 12462 |
| HPV16 | L2 | 319 | 9 | SIGAKVHYY | | 12463 |
| HPV16 | L2 | 319 | 10 | SIGAKVHYYY | | 12464 |
| HPV16 | L2 | 274 | 10 | SINIAPDPDF | | 12465 |
| HPV16 | L2 | 274 | 11 | SINIAPDPDFL | | 12466 |
| HPV16 | L2 | 360 | 9 | SINNGLYDI | | 12467 |
| HPV16 | L2 | 360 | 10 | SINNGLYDIY | | 12468 |
| HPV16 | L2 | 125 | 9 | SIPPDVSGF | | 12469 |

TABLE X-continued

A24 Supermotif Peptides

| Type | Protein | Position | No. of Amino Acids | Sequence | A*2402 | Seq. Id. No. |
|---|---|---|---|---|---|---|
| HPV16 | L2 | 125 | 11 | SIPPDVSGFSI | | 12470 |
| HPV16 | L2 | 104 | 11 | SIVSLVEETSF | | 12471 |
| HPV16 | L2 | 107 | 8 | SLVEETSF | | 12472 |
| HPV16 | L2 | 107 | 9 | SLVEETSFI | | 12473 |
| HPV16 | L2 | 50 | 9 | SMGVFFGGL | | 12474 |
| HPV16 | L2 | 50 | 11 | SMGVFFGGLGI | | 12475 |
| HPV16 | L2 | 138 | 8 | STDTTPAI | | 12476 |
| HPV16 | L2 | 138 | 9 | STDTTPAIL | | 12477 |
| HPV16 | L2 | 138 | 11 | STDTTPAILDI | | 12478 |
| HPV16 | L2 | 189 | 8 | STHNYEEI | | 12479 |
| HPV16 | L2 | 189 | 10 | STHNYEEIPM | | 12480 |
| HPV16 | L2 | 331 | 9 | STIDSAEEI | | 12481 |
| HPV16 | L2 | 331 | 11 | STIDSAEEIEL | | 12482 |
| HPV16 | L2 | 186 | 8 | STISTHNY | | 12483 |
| HPV16 | L2 | 186 | 11 | STISTHNYEEI | | 12484 |
| HPV16 | L2 | 387 | 8 | STSLSGYI | | 12485 |
| HPV16 | L2 | 347 | 11 | STYTTTSHAAL | | 12486 |
| HPV16 | L2 | 384 | 10 | SVPSTSLSGY | | 12487 |
| HPV16 | L2 | 384 | 11 | SVPSTSLSGYI | | 12488 |
| HPV16 | L2 | 162 | 8 | TFTDPSVL | | 12489 |
| HPV16 | L2 | 40 | 9 | TIADQILQY | | 12490 |
| HPV16 | L2 | 332 | 8 | TIDSAEEI | | 12491 |
| HPV16 | L2 | 332 | 10 | TIDSAEEIEL | | 12492 |
| HPV16 | L2 | 438 | 9 | TIIADAGDF | | 12493 |
| HPV16 | L2 | 438 | 10 | TIIADAGDFY | | 12494 |
| HPV16 | L2 | 438 | 11 | TIIADAGDFYL | | 12495 |
| HPV16 | L2 | 399 | 8 | TIPFGGAY | | 12496 |
| HPV16 | L2 | 399 | 10 | TIPFGGAYNI | | 12497 |
| HPV16 | L2 | 187 | 10 | TISTHNYEEI | | 12498 |
| HPV16 | L2 | 85 | 9 | TLAPVRPPL | | 12499 |
| HPV16 | L2 | 311 | 10 | TLRTRSGKSI | | 12500 |
| HPV16 | L2 | 265 | 11 | TLYFSSNDNSI | | 12501 |
| HPV16 | L2 | 156 | 8 | TTHNNPTF | | 12502 |
| HPV16 | L2 | 398 | 9 | TTIPFGGAY | | 12503 |
| HPV16 | L2 | 398 | 11 | TTIPFGGAYNI | | 12504 |
| HPV16 | L2 | 141 | 8 | TTPAILDI | | 12505 |
| HPV16 | L2 | 244 | 9 | TTPTKLITY | | 12506 |
| HPV16 | L2 | 351 | 11 | TTSHAALPTSI | | 12507 |
| HPV16 | L2 | 136 | 10 | TTSTDTTPAI | | 12508 |
| HPV16 | L2 | 136 | 11 | TTSTDTTPAIL | | 12509 |
| HPV16 | L2 | 350 | 8 | TTTSHAAL | | 12510 |
| HPV16 | L2 | 153 | 11 | TTVTTHNNPTF | | 12511 |
| HPV16 | L2 | 209 | 8 | TVTSSTPI | | 12512 |
| HPV16 | L2 | 154 | 10 | TVTTHNNPTF | | 12513 |
| HPV16 | L2 | 251 | 10 | TYDNPAYEGI | | 12514 |
| HPV16 | L2 | 348 | 10 | TYTTSHAAL | | 12515 |
| HPV16 | L2 | 53 | 8 | VFFGGLGI | | 12516 |
| HPV16 | L2 | 155 | 9 | VTTHNNPTF | | 12517 |
| HPV16 | L2 | 464 | 8 | YFFSDVSL | | 12518 |
| HPV16 | L2 | 267 | 9 | YFSSNDNSI | | 12519 |
| HPV16 | L2 | 267 | 11 | YFSSNDNSINI | | 12520 |
| HPV16 | L2 | 393 | 8 | YIPANTTI | | 12521 |
| HPV16 | L2 | 393 | 10 | YIPANTTIPF | | 12522 |
| HPV16 | L2 | 447 | 8 | YLHPSYYM | | 12523 |
| HPV16 | L2 | 447 | 9 | YLHPSYYML | | 12524 |
| HPV16 | L2 | 453 | 10 | YMLRKRRKRL | | 12525 |
| HPV16 | L2 | 437 | 10 | YTIIADAGDF | | 12526 |
| HPV16 | L2 | 437 | 11 | YTIIADAGDFY | | 12527 |
| HPV16 | L2 | 349 | 9 | YTTTSHAAL | | 12528 |
| HPV16 | L2 | 452 | 11 | YYMLRKRRKRL | | 12529 |
| HPV16 | L2 | 326 | 8 | YYYDFSTI | | 12530 |
| HPV18 | E1 | 398 | 11 | AFLKSNCQAKY | | 12531 |
| HPV18 | E1 | 246 | 9 | AIFGVNPTI | | 12532 |
| HPV18 | E1 | 22 | 11 | AIVDKKTGDVI | | 12533 |
| HPV18 | E1 | 546 | 9 | ALDGNPISI | | 12534 |
| HPV18 | E1 | 325 | 9 | ALYWYRTGI | | 12535 |
| HPV18 | E1 | 213 | 10 | AMLAVFKDTY | | 12536 |
| HPV18 | E1 | 526 | 11 | AMLDDATTTCW | | 12537 |
| HPV18 | E1 | 40 | 8 | ATDTGSDM | | 12538 |
| HPV18 | E1 | 40 | 11 | ATDTGSDMVDF | | 12539 |
| HPV18 | E1 | 531 | 8 | ATTCWTY | | 12540 |
| HPV18 | E1 | 531 | 9 | ATTCWTYF | | 12541 |
| HPV18 | E1 | 216 | 9 | AVFKDTYGL | | 12542 |
| HPV18 | E1 | 216 | 11 | AVFKDTYGLSF | | 12543 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | E1 | 618 | 10 | CFFERTWSRL | | 12544 |
| HPV18 | E1 | 273 | 9 | CLDCKWGVL | | 12545 |
| HPV18 | E1 | 273 | 10 | CLDCKWGVLI | | 12546 |
| HPV18 | E1 | 273 | 11 | CLDCKWGVLIL | | 12547 |
| HPV18 | E1 | 311 | 9 | CMLIQPPKL | | 12548 |
| HPV18 | E1 | 240 | 8 | CTDWVTAI | | 12549 |
| HPV18 | E1 | 240 | 9 | CTDWVTAIF | | 12550 |
| HPV18 | E1 | 196 | 9 | CTIAQLKDL | | 12551 |
| HPV18 | E1 | 196 | 10 | CTIAQLKDLL | | 12552 |
| HPV18 | E1 | 535 | 8 | CWTYFDTY | | 12553 |
| HPV18 | E1 | 535 | 9 | CWTYFDTYM | | 12554 |
| HPV18 | E1 | 49 | 9 | DFIDTQGTF | | 12555 |
| HPV18 | E1 | 363 | 8 | DLSEMVQW | | 12556 |
| HPV18 | E1 | 363 | 10 | DLSEMVQWAF | | 12557 |
| HPV18 | E1 | 381 | 8 | DMAFEYAL | | 12558 |
| HPV18 | E1 | 381 | 9 | DMAFEYALL | | 12559 |
| HPV18 | E1 | 637 | 10 | DTEGNPFGTF | | 12560 |
| HPV18 | E1 | 106 | 8 | DTELSPRL | | 12561 |
| HPV18 | E1 | 106 | 11 | DTELSPRLQEI | | 12562 |
| HPV18 | E1 | 42 | 9 | DTGSDMVDF | | 12563 |
| HPV18 | E1 | 42 | 10 | DTGSDMVDFI | | 12564 |
| HPV18 | E1 | 342 | 9 | DTPEWIQRL | | 12565 |
| HPV18 | E1 | 342 | 11 | DTPEWIQRLTI | | 12566 |
| HPV18 | E1 | 220 | 10 | DTYGLSFTDL | | 12567 |
| HPV18 | E1 | 540 | 8 | DTYMRNAL | | 12568 |
| HPV18 | E1 | 445 | 8 | DWRPIVQF | | 12569 |
| HPV18 | E1 | 445 | 9 | DWRPIVQFL | | 12570 |
| HPV18 | E1 | 445 | 11 | DWRPIVQFLRY | | 12571 |
| HPV18 | E1 | 459 | 9 | EFITFLGAL | | 12572 |
| HPV18 | E1 | 594 | 8 | EFPNAFPF | | 12573 |
| HPV18 | E1 | 610 | 10 | EINDKNWKCF | | 12574 |
| HPV18 | E1 | 610 | 11 | EINDKNWKCFF | | 12575 |
| HPV18 | E1 | 62 | 8 | ELETAQAL | | 12576 |
| HPV18 | E1 | 62 | 9 | ELETAQALF | | 12577 |
| HPV18 | E1 | 108 | 9 | ELSPRLQEI | | 12578 |
| HPV18 | E1 | 108 | 11 | ELSPRLQEISL | | 12579 |
| HPV18 | E1 | 375 | 8 | ELTDESDM | | 12580 |
| HPV18 | E1 | 375 | 10 | ELTDESDMAF | | 12581 |
| HPV18 | E1 | 366 | 11 | EMVQWAFDNEL | | 12582 |
| HPV18 | E1 | 309 | 11 | ETCMLIQPPKL | | 12583 |
| HPV18 | E1 | 104 | 10 | EVDTELSPRL | | 12584 |
| HPV18 | E1 | 74 | 9 | EVHNDAQVL | | 12585 |
| HPV18 | E1 | 338 | 9 | EVMGDTPEW | | 12586 |
| HPV18 | E1 | 338 | 10 | EVMGDTPEWI | | 12587 |
| HPV18 | E1 | 345 | 8 | EWIQRLTI | | 12588 |
| HPV18 | E1 | 345 | 9 | EWIQRLTII | | 12589 |
| HPV18 | E1 | 619 | 9 | FFERTWSRL | | 12590 |
| HPV18 | E1 | 619 | 11 | FFERTWSRLDL | | 12591 |
| HPV18 | E1 | 50 | 8 | FIDTQGTF | | 12592 |
| HPV18 | E1 | 497 | 10 | FIHFIQGAVI | | 12593 |
| HPV18 | E1 | 265 | 10 | FILYAHIQCL | | 12594 |
| HPV18 | E1 | 500 | 9 | FIQGAVISF | | 12595 |
| HPV18 | E1 | 460 | 8 | FITFLGAL | | 12596 |
| HPV18 | E1 | 460 | 11 | FITFLGALKSF | | 12597 |
| HPV18 | E1 | 463 | 8 | FLGALKSF | | 12598 |
| HPV18 | E1 | 463 | 9 | FLGALKSFL | | 12599 |
| HPV18 | E1 | 470 | 11 | FLKGTPKKNCL | | 12600 |
| HPV18 | E1 | 399 | 10 | FLKSNCQAKY | | 12601 |
| HPV18 | E1 | 399 | 11 | FLKSNCQAKYL | | 12602 |
| HPV18 | E1 | 452 | 9 | FLRYQQIEF | | 12603 |
| HPV18 | E1 | 452 | 10 | FLRYQQIEFI | | 12604 |
| HPV18 | E1 | 226 | 8 | FTDLVRNF | | 12605 |
| HPV18 | E1 | 130 | 8 | FTISDSGY | | 12606 |
| HPV18 | E1 | 508 | 8 | FVNSTSHF | | 12607 |
| HPV18 | E1 | 508 | 9 | FVNSTSHFW | | 12608 |
| HPV18 | E1 | 508 | 10 | FVNSTSHFWL | | 12609 |
| HPV18 | E1 | 257 | 9 | GFKTLIQPF | | 12610 |
| HPV18 | E1 | 257 | 10 | GFKTLIQPFI | | 12611 |
| HPV18 | E1 | 257 | 11 | GFKTLIQPFIL | | 12612 |
| HPV18 | E1 | 356 | 9 | GIDDSNFDL | | 12613 |
| HPV18 | E1 | 332 | 9 | GISNISEVM | | 12614 |
| HPV18 | E1 | 223 | 11 | GLSFTDLVRNF | | 12615 |
| HPV18 | E1 | 494 | 8 | GMSFIHFI | | 12616 |
| HPV18 | E1 | 55 | 9 | GTFCEQAEL | | 12617 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | E1 | 11 | 8 | GTGCNGWF | | 12618 |
| HPV18 | E1 | 11 | 9 | GTGCNGWFY | | 12619 |
| HPV18 | E1 | 473 | 8 | GTPKKNCL | | 12620 |
| HPV18 | E1 | 473 | 10 | GTPKKNCLVF | | 12621 |
| HPV18 | E1 | 182 | 8 | GTSDNSNI | | 12622 |
| HPV18 | E1 | 279 | 8 | GVLILALL | | 12623 |
| HPV18 | E1 | 279 | 10 | GVLILALLRY | | 12624 |
| HPV18 | E1 | 249 | 10 | GVNPTIAEGF | | 12625 |
| HPV18 | E1 | 16 | 8 | GWFYVQAI | | 12626 |
| HPV18 | E1 | 499 | 8 | HFIQGAVI | | 12627 |
| HPV18 | E1 | 499 | 10 | HFIQGAVISF | | 12628 |
| HPV18 | E1 | 270 | 9 | HIQCLDCKW | | 12629 |
| HPV18 | E1 | 306 | 8 | HVPETCML | | 12630 |
| HPV18 | E1 | 306 | 9 | HVPETCMLI | | 12631 |
| HPV18 | E1 | 418 | 10 | HYRRAQKRQM | | 12632 |
| HPV18 | E1 | 247 | 8 | IFGVNPTI | | 12633 |
| HPV18 | E1 | 352 | 11 | IIQHGIDDSNF | | 12634 |
| HPV18 | E1 | 266 | 9 | ILYAHIQCL | | 12635 |
| HPV18 | E1 | 461 | 10 | ITFLGALKSF | | 12636 |
| HPV18 | E1 | 461 | 11 | ITFLGALKSFL | | 12637 |
| HPV18 | E1 | 590 | 10 | ITVFEFPNAF | | 12638 |
| HPV18 | E1 | 23 | 10 | IVDKKTGDVI | | 12639 |
| HPV18 | E1 | 449 | 10 | IVQFLRYQQI | | 12640 |
| HPV18 | E1 | 439 | 8 | KIDEGGDW | | 12641 |
| HPV18 | E1 | 439 | 11 | KIDEGGDWRPI | | 12642 |
| HPV18 | E1 | 647 | 11 | KLRAGQNHRPL | | 12643 |
| HPV18 | E1 | 318 | 9 | KLRSSVAAL | | 12644 |
| HPV18 | E1 | 318 | 10 | KLRSSVAALY | | 12645 |
| HPV18 | E1 | 318 | 11 | KLRSSVAALYW | | 12646 |
| HPV18 | E1 | 259 | 8 | KTLIQPFI | | 12647 |
| HPV18 | E1 | 259 | 9 | KTLIQPFIL | | 12648 |
| HPV18 | E1 | 259 | 10 | KTLIQPFILY | | 12649 |
| HPV18 | E1 | 237 | 11 | KTTCTDWVTAI | | 12650 |
| HPV18 | E1 | 206 | 9 | KVNNKQGAM | | 12651 |
| HPV18 | E1 | 206 | 10 | KVNNKQGAML | | 12652 |
| HPV18 | E1 | 277 | 9 | KWGVLILAL | | 12653 |
| HPV18 | E1 | 277 | 10 | KWGVLILALL | | 12654 |
| HPV18 | E1 | 407 | 9 | KYLKDCATM | | 12655 |
| HPV18 | E1 | 129 | 9 | LFTISDSGY | | 12656 |
| HPV18 | E1 | 281 | 8 | LILALLRY | | 12657 |
| HPV18 | E1 | 561 | 9 | LIQLKCPPI | | 12658 |
| HPV18 | E1 | 561 | 10 | LIQLKCPPIL | | 12659 |
| HPV18 | E1 | 561 | 11 | LIQLKCPPILL | | 12660 |
| HPV18 | E1 | 261 | 8 | LIQPFILY | | 12661 |
| HPV18 | E1 | 261 | 11 | LIQPFILYAHI | | 12662 |
| HPV18 | E1 | 304 | 9 | LLHVPETCM | | 12663 |
| HPV18 | E1 | 304 | 10 | LLHVPETCML | | 12664 |
| HPV18 | E1 | 304 | 11 | LLHVPETCMLI | | 12665 |
| HPV18 | E1 | 204 | 11 | LLKVNNKQGAM | | 12666 |
| HPV18 | E1 | 285 | 11 | LLRYKCGKSRL | | 12667 |
| HPV18 | E1 | 376 | 9 | LTDESDMAF | | 12668 |
| HPV18 | E1 | 376 | 11 | LTDESDMAFEY | | 12669 |
| HPV18 | E1 | 520 | 8 | LTDTKVAM | | 12670 |
| HPV18 | E1 | 520 | 9 | LTDTKVAML | | 12671 |
| HPV18 | E1 | 350 | 8 | LTIIQHGI | | 12672 |
| HPV18 | E1 | 295 | 10 | LTVAKGLSTL | | 12673 |
| HPV18 | E1 | 295 | 11 | LTVAKGLSTLL | | 12674 |
| HPV18 | E1 | 267 | 8 | LYAHIQCL | | 12675 |
| HPV18 | E1 | 326 | 8 | LYWYRTGI | | 12676 |
| HPV18 | E1 | 326 | 11 | LYWYRTGISNI | | 12677 |
| HPV18 | E1 | 214 | 9 | MLAVFKDTY | | 12678 |
| HPV18 | E1 | 214 | 11 | MLAVFKDTYGL | | 12679 |
| HPV18 | E1 | 527 | 10 | MLDDATTTCW | | 12680 |
| HPV18 | E1 | 312 | 8 | MLIQPPKL | | 12681 |
| HPV18 | E1 | 47 | 11 | MVDFIDTQGTF | | 12682 |
| HPV18 | E1 | 367 | 10 | MVQWAFDNEL | | 12683 |
| HPV18 | E1 | 361 | 10 | NFDLSEMVQW | | 12684 |
| HPV18 | E1 | 188 | 11 | NIENVNPQCTI | | 12685 |
| HPV18 | E1 | 574 | 10 | NIHPAKDNRW | | 12686 |
| HPV18 | E1 | 428 | 8 | NMSQWIRF | | 12687 |
| HPV18 | E1 | 487 | 9 | NTGKSYFGM | | 12688 |
| HPV18 | E1 | 487 | 11 | NTGKSYFGMSF | | 12689 |
| HPV18 | E1 | 158 | 11 | NVCSGGSTEAI | | 12690 |
| HPV18 | E1 | 191 | 8 | NVNPQCTI | | 12691 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | E1 | 191 | 11 | NVNPQCTIAQL | | 12692 |
| HPV18 | E1 | 615 | 10 | NWKCFFERTW | | 12693 |
| HPV18 | E1 | 600 | 10 | PFDKNGNPVY | | 12694 |
| HPV18 | E1 | 264 | 8 | PFILYAHI | | 12695 |
| HPV18 | E1 | 264 | 11 | PFILYAHIQCL | | 12696 |
| HPV18 | E1 | 568 | 8 | PILLTTNI | | 12697 |
| HPV18 | E1 | 551 | 11 | PISIDRKHKPL | | 12698 |
| HPV18 | E1 | 448 | 8 | PIVQFLRY | | 12699 |
| HPV18 | E1 | 448 | 11 | PIVQFLRYQQI | | 12700 |
| HPV18 | E1 | 560 | 10 | PLIQLKCPPI | | 12701 |
| HPV18 | E1 | 560 | 11 | PLIQLKCPPIL | | 12702 |
| HPV18 | E1 | 519 | 9 | PLTDTKVAM | | 12703 |
| HPV18 | E1 | 519 | 10 | PLTDTKVAML | | 12704 |
| HPV18 | E1 | 252 | 10 | PTIAEGFKTL | | 12705 |
| HPV18 | E1 | 252 | 11 | PTIAEGFKTLI | | 12706 |
| HPV18 | E1 | 607 | 10 | PVYEINDKNW | | 12707 |
| HPV18 | E1 | 584 | 10 | PYLESRITVF | | 12708 |
| HPV18 | E1 | 451 | 8 | QFLRYQQI | | 12709 |
| HPV18 | E1 | 451 | 10 | QFLRYQQIEF | | 12710 |
| HPV18 | E1 | 451 | 11 | QFLRYQQIEFI | | 12711 |
| HPV18 | E1 | 457 | 8 | QIEFITFL | | 12712 |
| HPV18 | E1 | 457 | 11 | QIEFITFLGAL | | 12713 |
| HPV18 | E1 | 563 | 8 | QLKCPPIL | | 12714 |
| HPV18 | E1 | 563 | 9 | QLKCPPILL | | 12715 |
| HPV18 | E1 | 426 | 8 | QMNMSQWI | | 12716 |
| HPV18 | E1 | 426 | 10 | QMNMSQWIRF | | 12717 |
| HPV18 | E1 | 80 | 10 | QVLHVLRKF | | 12718 |
| HPV18 | E1 | 369 | 8 | QWAFDNEL | | 12719 |
| HPV18 | E1 | 431 | 10 | QWIRFRCSKI | | 12720 |
| HPV18 | E1 | 589 | 11 | RITVFEFPNAF | | 12721 |
| HPV18 | E1 | 102 | 8 | RLEVDTEL | | 12722 |
| HPV18 | E1 | 128 | 10 | RLFTISDSGY | | 12723 |
| HPV18 | E1 | 349 | 9 | RLTIIQHGI | | 12724 |
| HPV18 | E1 | 294 | 8 | RLTVAKGL | | 12725 |
| HPV18 | E1 | 294 | 11 | TLTVAKGLSTL | | 12726 |
| HPV18 | E1 | 330 | 11 | RTGISNISEVM | | 12727 |
| HPV18 | E1 | 622 | 8 | RTWSRLDL | | 12728 |
| HPV18 | E1 | 582 | 9 | RWPYLESRI | | 12729 |
| HPV18 | E1 | 287 | 9 | RYKCGKSRL | | 12730 |
| HPV18 | E1 | 454 | 8 | RYQQIEFI | | 12731 |
| HPV18 | E1 | 454 | 10 | RYQQIEFITF | | 12732 |
| HPV18 | E1 | 454 | 11 | RYQQIEFITFL | | 12733 |
| HPV18 | E1 | 496 | 11 | SFIHFIQGAVI | | 12734 |
| HPV18 | E1 | 225 | 9 | SFTDLVRNF | | 12735 |
| HPV18 | E1 | 507 | 9 | SFVNSTSHF | | 12736 |
| HPV18 | E1 | 507 | 10 | SFVNSTSHFW | | 12737 |
| HPV18 | E1 | 507 | 11 | SFVNSTSHFWL | | 12738 |
| HPV18 | E1 | 553 | 9 | SIDRKHKPL | | 12739 |
| HPV18 | E1 | 553 | 10 | SIDRKHKPLI | | 12740 |
| HPV18 | E1 | 93 | 11 | STENSPLGERL | | 12741 |
| HPV18 | E1 | 302 | 11 | STLLHVPETCM | | 12742 |
| HPV18 | E1 | 511 | 10 | STSHFWLEPL | | 12743 |
| HPV18 | E1 | 322 | 8 | SVAALYWY | | 12744 |
| HPV18 | E1 | 179 | 11 | SVDGTSDNSNI | | 12745 |
| HPV18 | E1 | 491 | 8 | SYFGMSFI | | 12746 |
| HPV18 | E1 | 491 | 10 | SYFGMSFIHF | | 12747 |
| HPV18 | E1 | 491 | 11 | SYFGMSFIHFI | | 12748 |
| HPV18 | E1 | 56 | 8 | TFCEQAEL | | 12749 |
| HPV18 | E1 | 462 | 9 | TFLGALKSF | | 12750 |
| HPV18 | E1 | 462 | 10 | TFLGALKSFL | | 12751 |
| HPV18 | E1 | 253 | 9 | TIAEGFKTL | | 12752 |
| HPV18 | E1 | 253 | 10 | TIAEGFKTLI | | 12753 |
| HPV18 | E1 | 197 | 8 | TIAQLKDL | | 12754 |
| HPV18 | E1 | 197 | 9 | TIAQLKDLL | | 12755 |
| HPV18 | E1 | 260 | 8 | TLIQPFIL | | 12756 |
| HPV18 | E1 | 260 | 9 | TLIQPFILY | | 12757 |
| HPV18 | E1 | 303 | 10 | TLLHVPETCM | | 12758 |
| HPV18 | E1 | 303 | 11 | TLLHVPETCML | | 12759 |
| HPV18 | E1 | 238 | 10 | TTCTDWVTAI | | 12760 |
| HPV18 | E1 | 238 | 11 | TTCTDWVTAIF | | 12761 |
| HPV18 | E1 | 533 | 10 | TTCWTYFDTY | | 12762 |
| HPV18 | E1 | 533 | 11 | TTCWTYFDTYM | | 12763 |
| HPV18 | E1 | 532 | 8 | TTCWTYF | | 12764 |
| HPV18 | E1 | 532 | 11 | TTCWTYFDTY | | 12765 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | E1 | 296 | 9 | TVAKGLSTL | | 12766 |
| HPV18 | E1 | 296 | 10 | TVAKGLSTLL | | 12767 |
| HPV18 | E1 | 591 | 9 | TVFEFPNAF | | 12768 |
| HPV18 | E1 | 591 | 11 | TVFEFPNAFPF | | 12769 |
| HPV18 | E1 | 537 | 11 | TYFDTYMRNAL | | 12770 |
| HPV18 | E1 | 221 | 9 | TYGLSFTDL | | 12771 |
| HPV18 | E1 | 592 | 8 | VFEFPNAF | | 12772 |
| HPV18 | E1 | 592 | 10 | VFEFPNAFPF | | 12773 |
| HPV18 | E1 | 217 | 8 | VFKDTYGL | | 12774 |
| HPV18 | E1 | 217 | 10 | VFKDTYGLSF | | 12775 |
| HPV18 | E1 | 505 | 11 | VISFVNSTSHF | | 12776 |
| HPV18 | E1 | 81 | 9 | VLHVLKRKF | | 12777 |
| HPV18 | E1 | 280 | 9 | VLILALLRY | | 12778 |
| HPV18 | E1 | 339 | 8 | VMGDTPEW | | 12779 |
| HPV18 | E1 | 339 | 9 | VMGDTPEWI | | 12780 |
| HPV18 | E1 | 244 | 11 | VTAIFGVNPTI | | 12781 |
| HPV18 | E1 | 608 | 9 | VYEINDKNW | | 12782 |
| HPV18 | E1 | 346 | 8 | WIQRLTII | | 12783 |
| HPV18 | E1 | 432 | 9 | WIRFRCSKI | | 12784 |
| HPV18 | E1 | 536 | 8 | WTYFDTYM | | 12785 |
| HPV18 | E1 | 328 | 9 | WYRTGISNI | | 12786 |
| HPV18 | E1 | 538 | 10 | YFDTYMRNAL | | 12787 |
| HPV18 | E1 | 492 | 9 | YFGMSFIHF | | 12788 |
| HPV18 | E1 | 492 | 10 | YFGMSFIHFI | | 12789 |
| HPV18 | E1 | 585 | 9 | YLESRITVF | | 12790 |
| HPV18 | E1 | 585 | 11 | YLESRITVFEF | | 12791 |
| HPV18 | E1 | 408 | 8 | YLKDCATM | | 12792 |
| HPV18 | E1 | 542 | 11 | YMRNALDGNPI | | 12793 |
| HPV18 | E1 | 327 | 10 | YWYRTGISNI | | 12794 |
| HPV18 | E2 | 76 | 8 | AIELQMAL | | 12795 |
| HPV18 | E2 | 76 | 11 | AIELQMALQGL | | 12796 |
| HPV18 | E2 | 45 | 11 | AIFFAAREHGI | | 12797 |
| HPV18 | E2 | 351 | 8 | AIPDSVQI | | 12798 |
| HPV18 | E2 | 351 | 9 | AIPDSVQIL | | 12799 |
| HPV18 | E2 | 82 | 10 | ALQGLAQSRY | | 12800 |
| HPV18 | E2 | 154 | 9 | ATCVSHRGL | | 12801 |
| HPV18 | E2 | 154 | 10 | ATCVSHRGLY | | 12802 |
| HPV18 | E2 | 154 | 11 | ATCVSHRGLYY | | 12803 |
| HPV18 | E2 | 214 | 8 | ATQLVKQL | | 12804 |
| HPV18 | E2 | 246 | 9 | ATRPGHCGL | | 12805 |
| HPV18 | E2 | 137 | 8 | AWDSVYYM | | 12806 |
| HPV18 | E2 | 132 | 11 | CMTYVAWDSVY | | 12807 |
| HPV18 | E2 | 14 | 10 | CVQDKIIDHY | | 12808 |
| HPV18 | E2 | 156 | 8 | CVSHRGLY | | 12809 |
| HPV18 | E2 | 156 | 9 | CVSHRGLYY | | 12810 |
| HPV18 | E2 | 29 | 8 | DIDSQIQY | | 12811 |
| HPV18 | E2 | 29 | 9 | DIDSQIQYW | | 12812 |
| HPV18 | E2 | 29 | 11 | DIDSQIQYWQL | | 12813 |
| HPV18 | E2 | 315 | 8 | DISSTWHW | | 12814 |
| HPV18 | E2 | 210 | 8 | DTVSATQL | | 12815 |
| HPV18 | E2 | 95 | 11 | DWTLQDTCEEL | | 12816 |
| HPV18 | E2 | 175 | 9 | EFKSECEKY | | 12817 |
| HPV18 | E2 | 78 | 9 | ELQMALQGL | | 12818 |
| HPV18 | E2 | 104 | 11 | ELWNTEPTHCF | | 12819 |
| HPV18 | E2 | 340 | 8 | ETQRTKFL | | 12820 |
| HPV18 | E2 | 190 | 9 | EVHFGNNVI | | 12821 |
| HPV18 | E2 | 47 | 9 | FFAAREHGI | | 12822 |
| HPV18 | E2 | 161 | 9 | GLYYVKEGY | | 12823 |
| HPV18 | E2 | 168 | 9 | GYNTFYIEF | | 12824 |
| HPV18 | E2 | 291 | 9 | HLKGDRNSL | | 12825 |
| HPV18 | E2 | 22 | 9 | HYENDSKDI | | 12826 |
| HPV18 | E2 | 312 | 9 | HYRDISSTW | | 12827 |
| HPV18 | E2 | 312 | 11 | HYRDISSTWHW | | 12828 |
| HPV18 | E2 | 46 | 10 | IFFAAREHGI | | 12829 |
| HPV18 | E2 | 289 | 11 | IIHLKGDRNSL | | 12830 |
| HPV18 | E2 | 358 | 8 | ILVGYMTM | | 12831 |
| HPV18 | E2 | 345 | 8 | KFLNTVAI | | 12832 |
| HPV18 | E2 | 280 | 10 | KLCSGNTTPI | | 12833 |
| HPV18 | E2 | 280 | 11 | KLCSGNTTPII | | 12834 |
| HPV18 | E2 | 152 | 11 | KTATCVSHRGL | | 12835 |
| HPV18 | E2 | 329 | 9 | KTGILTVTY | | 12836 |
| HPV18 | E2 | 182 | 8 | KYGNTGTW | | 12837 |
| HPV18 | E2 | 39 | 8 | LIRWENAI | | 12838 |
| HPV18 | E2 | 39 | 9 | LIRWENAIF | | 12839 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | E2 | 39 | 10 | LIRWENAIFF | | 12840 |
| HPV18 | E2 | 105 | 10 | LWNTEPTHCF | | 12841 |
| HPV18 | E2 | 162 | 8 | LYYVKEGY | | 12842 |
| HPV18 | E2 | 162 | 11 | LYYVKEGYNTF | | 12843 |
| HPV18 | E2 | 133 | 10 | MTYVAWDSVY | | 12844 |
| HPV18 | E2 | 133 | 11 | MTYVAWDSVYY | | 12845 |
| HPV18 | E2 | 67 | 11 | NISKSKAHKAI | | 12846 |
| HPV18 | E2 | 107 | 8 | NTEPTHCF | | 12847 |
| HPV18 | E2 | 185 | 9 | NTGTWEVHF | | 12848 |
| HPV18 | E2 | 285 | 8 | NTTPIIHL | | 12849 |
| HPV18 | E2 | 348 | 11 | NTVAIPDSVQI | | 12850 |
| HPV18 | E2 | 196 | 9 | NVIDCNDSM | | 12851 |
| HPV18 | E2 | 272 | 10 | PTGNNKRRKL | | 12852 |
| HPV18 | E2 | 357 | 9 | QILVGYMTM | | 12853 |
| HPV18 | E2 | 33 | 8 | QIQYWQLI | | 12854 |
| HPV18 | E2 | 33 | 10 | QIQYWQLIRW | | 12855 |
| HPV18 | E2 | 38 | 9 | QLIRWENAI | | 12856 |
| HPV18 | E2 | 38 | 10 | QLIRWENAIF | | 12857 |
| HPV18 | E2 | 38 | 11 | QLIRWENAIFF | | 12858 |
| HPV18 | E2 | 220 | 9 | QLQHTPSPY | | 12859 |
| HPV18 | E2 | 56 | 11 | QTLNHQVVPAY | | 12860 |
| HPV18 | E2 | 2 | 11 | QTPKETLSERL | | 12861 |
| HPV18 | E2 | 61 | 8 | QVVPAYNI | | 12862 |
| HPV18 | E2 | 35 | 8 | QYWQLIRW | | 12863 |
| HPV18 | E2 | 305 | 9 | RLRKHSDHY | | 12864 |
| HPV18 | E2 | 11 | 9 | RLSCVQDKI | | 12865 |
| HPV18 | E2 | 11 | 10 | RLSCVQDKII | | 12866 |
| HPV18 | E2 | 343 | 10 | RTKFLNTVAI | | 12867 |
| HPV18 | E2 | 41 | 8 | RWENAIFF | | 12868 |
| HPV18 | E2 | 90 | 9 | RYKTEDWTL | | 12869 |
| HPV18 | E2 | 303 | 11 | RYRLRKHSDHY | | 12870 |
| HPV18 | E2 | 298 | 9 | SLKCLRYRL | | 12871 |
| HPV18 | E2 | 230 | 11 | STVSVGTAKTY | | 12872 |
| HPV18 | E2 | 233 | 8 | SVGTAKTY | | 12873 |
| HPV18 | E2 | 355 | 8 | SVQILVGY | | 12874 |
| HPV18 | E2 | 355 | 9 | SVQILVGYM | | 12875 |
| HPV18 | E2 | 355 | 11 | SVQILVGYMTM | | 12876 |
| HPV18 | E2 | 140 | 11 | SVYYMTDAGTW | | 12877 |
| HPV18 | E2 | 57 | 10 | TLNHQVVPAY | | 12878 |
| HPV18 | E2 | 97 | 9 | TLQDTCEEL | | 12879 |
| HPV18 | E2 | 97 | 10 | TLQDTCEELW | | 12880 |
| HPV18 | E2 | 349 | 10 | TVAIPDSVQI | | 12881 |
| HPV18 | E2 | 349 | 11 | TVAIPDSVQIL | | 12882 |
| HPV18 | E2 | 211 | 11 | TVSATQLVKQL | | 12883 |
| HPV18 | E2 | 231 | 10 | TVSVGTAKTY | | 12884 |
| HPV18 | E2 | 188 | 11 | TWEVHFGNNVI | | 12885 |
| HPV18 | E2 | 336 | 11 | TYHSETQRTKF | | 12886 |
| HPV18 | E2 | 134 | 9 | TYVAWDSVY | | 12887 |
| HPV18 | E2 | 134 | 10 | TYVAWDSVYY | | 12888 |
| HPV18 | E2 | 134 | 11 | TYVAWDSVYYM | | 12889 |
| HPV18 | E2 | 197 | 8 | VIDCNDSM | | 12890 |
| HPV18 | E2 | 123 | 11 | VYFDGNKDNCM | | 12891 |
| HPV18 | E2 | 141 | 10 | VYYMTDAGTW | | 12892 |
| HPV18 | E2 | 322 | 11 | WTGAGNEKTGI | | 12893 |
| HPV18 | E2 | 96 | 10 | WTLQDTCEEL | | 12894 |
| HPV18 | E2 | 96 | 11 | WTLQDTCEELW | | 12895 |
| HPV18 | E2 | 124 | 10 | YFDGNKDNCM | | 12896 |
| HPV18 | E2 | 173 | 11 | YIEFKSECEKY | | 12897 |
| HPV18 | E2 | 143 | 8 | YMTDAGTW | | 12898 |
| HPV18 | E2 | 135 | 8 | YVAWDSVY | | 12899 |
| HPV18 | E2 | 135 | 9 | YVAWDSVYY | | 12900 |
| HPV18 | E2 | 135 | 10 | YVAWDSVYYM | | 12901 |
| HPV18 | E2 | 164 | 9 | YVKEGYNTF | | 12902 |
| HPV18 | E2 | 164 | 10 | YVKEGYNTFY | | 12903 |
| HPV18 | E2 | 164 | 11 | YVKEGYNTFYI | | 12904 |
| HPV18 | E2 | 36 | 11 | YWQLIRWENAI | | 12905 |
| HPV18 | E2 | 142 | 9 | YYMTDAGTW | | 12906 |
| HPV18 | E2 | 163 | 10 | YYVKEGYNTF | | 12907 |
| HPV18 | E2 | 163 | 11 | YYVKEGYNTFY | | 12908 |
| HPV18 | E5 | 49 | 9 | AFTVYVFCF | | 12909 |
| HPV18 | E5 | 49 | 10 | AFTVYVFCFL | | 12910 |
| HPV18 | E5 | 49 | 11 | AFTVYVFCFLL | | 12911 |
| HPV18 | E5 | 47 | 9 | ATAFTVYVF | | 12912 |
| HPV18 | E5 | 47 | 11 | ATAFTVYVFCF | | 12913 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | E5 | 32 | 8 | AWVLVFVY | | 12914 |
| HPV18 | E5 | 32 | 9 | AWVLVFVYI | | 12915 |
| HPV18 | E5 | 30 | 8 | AYAWVLVF | | 12916 |
| HPV18 | E5 | 30 | 10 | AYAWVLVFVY | | 12917 |
| HPV18 | E5 | 30 | 11 | AYAWVLVFVYI | | 12918 |
| HPV18 | E5 | 56 | 8 | CFLLPMLL | | 12919 |
| HPV18 | E5 | 56 | 9 | CFLLPMLLL | | 12920 |
| HPV18 | E5 | 56 | 11 | CFLLPMLLLHI | | 12921 |
| HPV18 | E5 | 27 | 9 | CMCAYAWVL | | 12922 |
| HPV18 | E5 | 27 | 11 | CMCAYAWVLVF | | 12923 |
| HPV18 | E5 | 13 | 10 | CMYVCCHVPL | | 12924 |
| HPV18 | E5 | 13 | 11 | CMYVCCHVPLL | | 12925 |
| HPV18 | E5 | 6 | 9 | FLFCFCVCM | | 12926 |
| HPV18 | E5 | 6 | 10 | FLFCFCVCMY | | 12927 |
| HPV18 | E5 | 57 | 8 | FLLPMLLL | | 12928 |
| HPV18 | E5 | 57 | 10 | FLLPMLLLHI | | 12929 |
| HPV18 | E5 | 50 | 8 | FTVYVFCF | | 12930 |
| HPV18 | E5 | 50 | 9 | FTVYVFCFL | | 12931 |
| HPV18 | E5 | 50 | 10 | FTVYVFCFLL | | 12932 |
| HPV18 | E5 | 65 | 8 | HIHAILSL | | 12933 |
| HPV18 | E5 | 19 | 10 | HVPLLPSVCM | | 12934 |
| HPV18 | E5 | 5 | 10 | IFLFCFCVCM | | 12935 |
| HPV18 | E5 | 5 | 11 | IFLFCFCVCMY | | 12936 |
| HPV18 | E5 | 43 | 8 | ITSPATAF | | 12937 |
| HPV18 | E5 | 43 | 11 | ITSPATAFTVY | | 12938 |
| HPV18 | E5 | 40 | 11 | IVVITSPATAF | | 12939 |
| HPV18 | E5 | 7 | 8 | LFCFCVCM | | 12940 |
| HPV18 | E5 | 7 | 9 | LFCFCVCMY | | 12941 |
| HPV18 | E5 | 4 | 11 | LIFLFCFCVCM | | 12942 |
| HPV18 | E5 | 63 | 8 | LLHIHAIL | | 12943 |
| HPV18 | E5 | 63 | 10 | LLHIHAILSL | | 12944 |
| HPV18 | E5 | 62 | 8 | LLLHIHAI | | 12945 |
| HPV18 | E5 | 62 | 9 | LLLHIHAIL | | 12946 |
| HPV18 | E5 | 62 | 11 | LLLHIHAILSL | | 12947 |
| HPV18 | E5 | 58 | 9 | LLPMLLLHI | | 12948 |
| HPV18 | E5 | 22 | 10 | LLPSVCMCAY | | 12949 |
| HPV18 | E5 | 35 | 9 | LVFVYIVVI | | 12950 |
| HPV18 | E5 | 61 | 9 | MLLLHIHAI | | 12951 |
| HPV18 | E5 | 61 | 10 | MLLLHIHAIL | | 12952 |
| HPV18 | E5 | 1 | 8 | MLSLIFLF | | 12953 |
| HPV18 | E5 | 1 | 10 | MLSLIFLFCF | | 12954 |
| HPV18 | E5 | 14 | 9 | MYVCCHVPL | | 12955 |
| HPV18 | E5 | 14 | 10 | MYVCCHVPLL | | 12956 |
| HPV18 | E5 | 21 | 8 | PLLPSVCM | | 12957 |
| HPV18 | E5 | 21 | 11 | PLLPSVCMCAY | | 12958 |
| HPV18 | E5 | 60 | 10 | PMLLLHIHAI | | 12959 |
| HPV18 | E5 | 60 | 11 | PMLLLHIHAIL | | 12960 |
| HPV18 | E5 | 3 | 8 | SLIFLFCF | | 12961 |
| HPV18 | E5 | 25 | 9 | SVCMCAYAW | | 12962 |
| HPV18 | E5 | 25 | 11 | SVCMCAYAWVL | | 12963 |
| HPV18 | E5 | 51 | 8 | TVYVFCFL | | 12964 |
| HPV18 | E5 | 51 | 9 | TVYVFCFLL | | 12965 |
| HPV18 | E5 | 51 | 11 | TVYVFCFLLPM | | 12966 |
| HPV18 | E5 | 54 | 8 | VFCFLLPM | | 12967 |
| HPV18 | E5 | 54 | 9 | VFCFLLPML | | 12968 |
| HPV18 | E5 | 54 | 10 | VFCFLLPMLL | | 12969 |
| HPV18 | E5 | 54 | 11 | VFCFLLPMLLL | | 12970 |
| HPV18 | E5 | 36 | 8 | VFVYIVVI | | 12971 |
| HPV18 | E5 | 42 | 9 | VITSPATAF | | 12972 |
| HPV18 | E5 | 34 | 10 | VLVFVYIVVI | | 12973 |
| HPV18 | E5 | 41 | 10 | VVITSPATAF | | 12974 |
| HPV18 | E5 | 52 | 8 | VYVFCFLL | | 12975 |
| HPV18 | E5 | 52 | 10 | VYVFCFLLPM | | 12976 |
| HPV18 | E5 | 52 | 11 | VYVFCFLLPML | | 12977 |
| HPV18 | E5 | 33 | 8 | WVLVFVYI | | 12978 |
| HPV18 | E5 | 33 | 11 | WVLVFVYIVVI | | 12979 |
| HPV18 | E5 | 15 | 8 | YVCCHVPL | | 12980 |
| HPV18 | E5 | 15 | 9 | YVCCHVPLL | | 12981 |
| HPV18 | E5 | 53 | 9 | YVFCFLLPM | | 12982 |
| HPV18 | E5 | 53 | 10 | YVFCFLLPML | | 12983 |
| HPV18 | E5 | 53 | 11 | YVFCFLLPMLL | | 12984 |
| HPV18 | E6 | 48 | 9 | AFKDLFVVY | | 12985 |
| HPV18 | E6 | 68 | 8 | CIDFYSRI | | 12986 |
| HPV18 | E6 | 68 | 11 | CIDFYSRIREL | | 12987 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | E6 | 105 | 8 | CLRCQKPL | | 12988 |
| HPV18 | E6 | 18 | 8 | CTELNTSL | | 12989 |
| HPV18 | E6 | 18 | 11 | CTELNTSLQDI | | 12990 |
| HPV18 | E6 | 32 | 8 | CVYCKTVL | | 12991 |
| HPV18 | E6 | 32 | 10 | CVYCKTVLEL | | 12992 |
| HPV18 | E6 | 70 | 9 | DFYSRIREL | | 12993 |
| HPV18 | E6 | 27 | 8 | DIEITCVY | | 12994 |
| HPV18 | E6 | 16 | 10 | DLCTELNTSL | | 12995 |
| HPV18 | E6 | 51 | 10 | DLFVVYRDSI | | 12996 |
| HPV18 | E6 | 88 | 11 | DTLEKLTNTGL | | 12997 |
| HPV18 | E6 | 46 | 8 | EFAFKDLF | | 12998 |
| HPV18 | E6 | 46 | 11 | EFAFKDLFVVY | | 12999 |
| HPV18 | E6 | 29 | 11 | EITCVYCKTVL | | 13000 |
| HPV18 | E6 | 20 | 9 | ELNTSLQDI | | 13001 |
| HPV18 | E6 | 20 | 11 | ELNTSLQDIEI | | 13002 |
| HPV18 | E6 | 77 | 10 | ELRHYSDSVY | | 13003 |
| HPV18 | E6 | 40 | 8 | ELTEVFEF | | 13004 |
| HPV18 | E6 | 40 | 10 | ELTEVFEFAF | | 13005 |
| HPV18 | E6 | 43 | 10 | EVFEFAFKDL | | 13006 |
| HPV18 | E6 | 43 | 11 | EVFEFAFKDLF | | 13007 |
| HPV18 | E6 | 53 | 8 | FVVYRDSI | | 13008 |
| HPV18 | E6 | 71 | 8 | FYSRIREL | 0.026 | 13009 |
| HPV18 | E6 | 71 | 11 | FYSRIRELRHY | 0.0052 | 13010 |
| HPV18 | E6 | 97 | 10 | GLYNLLIRCL | | 13011 |
| HPV18 | E6 | 120 | 8 | HLNEKRRF | | 13012 |
| HPV18 | E6 | 120 | 11 | HLNEKRRFHNI | | 13013 |
| HPV18 | E6 | 80 | 11 | HYSDSVYGDTL | 0.0069 | 13014 |
| HPV18 | E6 | 30 | 10 | ITCVYCKTVL | | 13015 |
| HPV18 | E6 | 13 | 9 | KLPDLCTEL | 0.0013 | 13016 |
| HPV18 | E6 | 117 | 11 | KLRHLNEKRRF | | 13017 |
| HPV18 | E6 | 92 | 8 | KLTNTGLY | | 13018 |
| HPV18 | E6 | 92 | 10 | KLTNTGLYNL | 0.0001 | 13019 |
| HPV18 | E6 | 92 | 11 | KLTNTGLYNLL | | 13020 |
| HPV18 | E6 | 36 | 10 | KTVLELTEVF | | 13021 |
| HPV18 | E6 | 52 | 9 | LFVVYRDSI | | 13022 |
| HPV18 | E6 | 102 | 11 | LIRCLRCQKPL | | 13023 |
| HPV18 | E6 | 41 | 9 | LTEVFEFAF | | 13024 |
| HPV18 | E6 | 93 | 9 | LTNTGLYNL | | 13025 |
| HPV18 | E6 | 93 | 10 | LTNTGLYNLL | | 13026 |
| HPV18 | E6 | 93 | 11 | LTNTGLYNLLI | | 13027 |
| HPV18 | E6 | 98 | 9 | LYNLLIRCL | 0.0001 | 13028 |
| HPV18 | E6 | 95 | 8 | NTGLYNLL | | 13029 |
| HPV18 | E6 | 95 | 9 | NTGLYNLLI | | 13030 |
| HPV18 | E6 | 22 | 9 | NTSLQDIEI | | 13031 |
| HPV18 | E6 | 111 | 8 | PLNPAEKL | | 13032 |
| HPV18 | E6 | 111 | 11 | PLNPAEKLRHL | | 13033 |
| HPV18 | E6 | 7 | 8 | PTRRPYKL | | 13034 |
| HPV18 | E6 | 7 | 11 | PTRRPYKLPDL | | 13035 |
| HPV18 | E6 | 11 | 11 | PYKLPDLCTEL | 0.0064 | 13036 |
| HPV18 | E6 | 3 | 10 | RFEDPTRRPY | | 13037 |
| HPV18 | E6 | 126 | 9 | RFHNIAGHY | | 13038 |
| HPV18 | E6 | 74 | 8 | RIRELRHY | | 13039 |
| HPV18 | E6 | 59 | 11 | SIPHAACHKCI | | 13040 |
| HPV18 | E6 | 24 | 11 | SLQDIEITCVY | | 13041 |
| HPV18 | E6 | 84 | 10 | SVYGDTLEKL | | 13042 |
| HPV18 | E6 | 89 | 10 | TLEKLTNTGL | | 13043 |
| HPV18 | E6 | 89 | 11 | TLEKLTNTGLY | 0.0001 | 13044 |
| HPV18 | E6 | 37 | 9 | TVLELTEVF | | 13045 |
| HPV18 | E6 | 37 | 11 | TVLELTEVFEF | | 13046 |
| HPV18 | E6 | 44 | 9 | VFEFAFKDL | | 13047 |
| HPV18 | E6 | 44 | 10 | VFEFAFKDLF | 0.036 | 13048 |
| HPV18 | E6 | 38 | 8 | VLELTEVF | | 13049 |
| HPV18 | E6 | 38 | 10 | VLELTEVFEF | | 13050 |
| HPV18 | E6 | 33 | 9 | VYCKTVLEL | 0.022 | 13051 |
| HPV18 | E6 | 85 | 9 | VYGDTLEKL | 0.015 | 13052 |
| HPV18 | E7 | 85 | 10 | AFQQLFLNTL | | 13053 |
| HPV18 | E7 | 6 | 8 | ATLQDIVL | | 13054 |
| HPV18 | E7 | 6 | 10 | ATLQDIVLHL | | 13055 |
| HPV18 | E7 | 63 | 10 | CMCCKCEARI | 0.0001 | 13056 |
| HPV18 | E7 | 24 | 8 | DLLCHEQL | | 13057 |
| HPV18 | E7 | 82 | 8 | DLRAFQQL | | 13058 |
| HPV18 | E7 | 82 | 9 | DLRAFQQLF | | 13059 |
| HPV18 | E7 | 82 | 10 | DLRAFQQLFL | | 13060 |
| HPV18 | E7 | 40 | 10 | EIDGVNHQHL | | 13061 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | E7 | 90 | 11 | FLNTLSFVCPW | | 13062 |
| HPV18 | E7 | 14 | 8 | HLEPQNEI | | 13063 |
| HPV18 | E7 | 11 | 11 | IVLHLEPQNEI | | 13064 |
| HPV18 | E7 | 73 | 11 | KLVVESSADDL | | 13065 |
| HPV18 | E7 | 89 | 8 | LFLNTLSF | | 13066 |
| HPV18 | E7 | 74 | 10 | LVVESSADDL | | 13067 |
| HPV18 | E7 | 92 | 9 | NTLSFVCPW | | 13068 |
| HPV18 | E7 | 22 | 10 | PVDLLCHEQL | | 13069 |
| HPV18 | E7 | 88 | 9 | QLFLNTLSF | | 13070 |
| HPV18 | E7 | 7 | 9 | TLQDIVLHL | | 13071 |
| HPV18 | E7 | 93 | 8 | TLSFVCPW | | 13072 |
| HPV18 | E7 | 12 | 10 | VLHLEPQNEI | | 13073 |
| HPV18 | E7 | 75 | 9 | VVESSADDL | | 13074 |
| HPV18 | L1 | 63 | 11 | ALWRPSDNTVY | | 13075 |
| HPV18 | L1 | 128 | 11 | AYQYRVFRVQL | | 13076 |
| HPV18 | L1 | 218 | 9 | CILGCAPAI | | 13077 |
| HPV18 | L1 | 310 | 8 | CLRREQLF | | 13078 |
| HPV18 | L1 | 2 | 8 | CLYTRVLI | | 13079 |
| HPV18 | L1 | 2 | 9 | CLYTRVLIL | | 13080 |
| HPV18 | L1 | 2 | 11 | CLYTRVLILHY | | 13081 |
| HPV18 | L1 | 441 | 10 | CTITLTADVM | | 13082 |
| HPV18 | L1 | 350 | 11 | CVYSPSPSGSI | | 13083 |
| HPV18 | L1 | 284 | 9 | DICQSICKY | | 13084 |
| HPV18 | L1 | 122 | 8 | DIPKVSAY | | 13085 |
| HPV18 | L1 | 122 | 10 | DIPKVSAYQY | | 13086 |
| HPV18 | L1 | 520 | 11 | DLDQYPLGRKF | | 13087 |
| HPV18 | L1 | 512 | 8 | DLKEKFSL | | 13088 |
| HPV18 | L1 | 512 | 10 | DLKEKFSLDL | | 13089 |
| HPV18 | L1 | 433 | 8 | DLQFIFQL | | 13090 |
| HPV18 | L1 | 433 | 11 | DLQFIFQLCTI | | 13091 |
| HPV18 | L1 | 260 | 10 | DMVDTGYGAM | | 13092 |
| HPV18 | L1 | 263 | 9 | DTGYGAMDF | | 13093 |
| HPV18 | L1 | 276 | 8 | DTKCEVPL | | 13094 |
| HPV18 | L1 | 276 | 10 | DTKCEVPLDI | | 13095 |
| HPV18 | L1 | 396 | 8 | DTTPSTNL | | 13096 |
| HPV18 | L1 | 396 | 10 | DTTPSTNLTI | | 13097 |
| HPV18 | L1 | 330 | 8 | DTVPQSLY | | 13098 |
| HPV18 | L1 | 330 | 9 | DTVPQSLYI | | 13099 |
| HPV18 | L1 | 478 | 11 | DTYRFVQSVAI | | 13100 |
| HPV18 | L1 | 448 | 9 | DVMSYIHSM | | 13101 |
| HPV18 | L1 | 203 | 10 | DVRDNVSVDY | | 13102 |
| HPV18 | L1 | 211 | 9 | DYKQTQLCI | | 13103 |
| HPV18 | L1 | 211 | 10 | DYKQTQLCIL | | 13104 |
| HPV18 | L1 | 294 | 10 | DYLQMSADPY | | 13105 |
| HPV18 | L1 | 87 | 8 | DYVTPTSI | | 13106 |
| HPV18 | L1 | 87 | 9 | DYVTPTSIF | | 13107 |
| HPV18 | L1 | 87 | 10 | DYVTPTSIFY | | 13108 |
| HPV18 | L1 | 167 | 8 | EIGRGQPL | | 13109 |
| HPV18 | L1 | 280 | 10 | EVPLDICQSI | | 13110 |
| HPV18 | L1 | 431 | 8 | EYDLQFIF | | 13111 |
| HPV18 | L1 | 431 | 10 | EYDLQFIFQL | | 13112 |
| HPV18 | L1 | 308 | 9 | FFCLRREQL | | 13113 |
| HPV18 | L1 | 308 | 10 | FFCLRREQLF | | 13114 |
| HPV18 | L1 | 436 | 8 | FIFQLCTI | | 13115 |
| HPV18 | L1 | 436 | 10 | FIFQLCTITL | | 13116 |
| HPV18 | L1 | 49 | 8 | FLRNVNVF | | 13117 |
| HPV18 | L1 | 49 | 10 | FLRNVNVFPI | | 13118 |
| HPV18 | L1 | 49 | 11 | FLRNVNVFPIF | | 13119 |
| HPV18 | L1 | 321 | 8 | FWNRAGTM | | 13120 |
| HPV18 | L1 | 508 | 10 | FWNVDLKEKF | | 13121 |
| HPV18 | L1 | 95 | 9 | FYHAGSSRL | | 13122 |
| HPV18 | L1 | 95 | 10 | FYHAGSSRLL | | 13123 |
| HPV18 | L1 | 145 | 8 | GLPDTSIY | | 13124 |
| HPV18 | L1 | 535 | 8 | GLRRKPTI | | 13125 |
| HPV18 | L1 | 177 | 8 | GLSGHPFY | | 13126 |
| HPV18 | L1 | 177 | 11 | GLSGHPFYNKL | | 13127 |
| HPV18 | L1 | 342 | 11 | GMPASPGSCVY | | 13128 |
| HPV18 | L1 | 233 | 9 | GTACKSRPL | | 13129 |
| HPV18 | L1 | 326 | 11 | GTMGDTVPQSL | | 13130 |
| HPV18 | L1 | 383 | 8 | GVCWHNQL | | 13131 |
| HPV18 | L1 | 383 | 9 | GVCWHNQLF | | 13132 |
| HPV18 | L1 | 165 | 10 | GVEIGRGQPL | | 13133 |
| HPV18 | L1 | 175 | 9 | GVGLSGHPF | | 13134 |
| HPV18 | L1 | 175 | 10 | GVGLSGHPFY | | 13135 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | L1 | 467 | 10 | GVPPPPTTSL | | 13136 |
| HPV18 | L1 | 265 | 10 | GYGAMDFSTL | | 13137 |
| HPV18 | L1 | 320 | 9 | HFWNRAGTM | | 13138 |
| HPV18 | L1 | 38 | 8 | HIIICGHY | | 13139 |
| HPV18 | L1 | 38 | 9 | HIIICGHYI | | 13140 |
| HPV18 | L1 | 38 | 10 | HIIICGHYII | | 13141 |
| HPV18 | L1 | 38 | 11 | HIIICGHYIIL | | 13142 |
| HPV18 | L1 | 13 | 9 | HLLPLYGPL | | 13143 |
| HPV18 | L1 | 13 | 10 | HLLPLYGPLY | | 13144 |
| HPV18 | L1 | 428 | 9 | HVEEYDLQF | | 13145 |
| HPV18 | L1 | 428 | 10 | HVEEYDLQFI | | 13146 |
| HPV18 | L1 | 428 | 11 | HVEEYDLQFIF | | 13147 |
| HPV18 | L1 | 11 | 8 | HYHLLPLY | | 13148 |
| HPV18 | L1 | 11 | 11 | HYHLLPLYGPL | | 13149 |
| HPV18 | L1 | 58 | 8 | IFLQMALW | | 13150 |
| HPV18 | L1 | 437 | 9 | IFQLCTITL | | 13151 |
| HPV18 | L1 | 94 | 10 | IFYHAGSSRL | | 13152 |
| HPV18 | L1 | 94 | 11 | IFYHAGSSRLL | | 13153 |
| HPV18 | L1 | 40 | 8 | IICGHYII | | 13154 |
| HPV18 | L1 | 40 | 9 | IICGHYIIL | | 13155 |
| HPV18 | L1 | 40 | 10 | IICGHYIILF | | 13156 |
| HPV18 | L1 | 40 | 11 | IICGHYIILFL | | 13157 |
| HPV18 | L1 | 39 | 8 | IIICGHYI | | 13158 |
| HPV18 | L1 | 39 | 9 | IIICGHYII | | 13159 |
| HPV18 | L1 | 39 | 10 | IIICGHYIIL | | 13160 |
| HPV18 | L1 | 39 | 11 | IIICGHYIILF | | 13161 |
| HPV18 | L1 | 46 | 11 | IILFLRNVNVF | | 13162 |
| HPV18 | L1 | 47 | 10 | ILFLRNVNVF | | 13163 |
| HPV18 | L1 | 219 | 8 | ILGCAPAI | | 13164 |
| HPV18 | L1 | 9 | 9 | ILHYHLLPL | | 13165 |
| HPV18 | L1 | 9 | 10 | ILHYHLLPLY | | 13166 |
| HPV18 | L1 | 32 | 8 | ILVYMVHI | | 13167 |
| HPV18 | L1 | 32 | 9 | ILVYMVHII | | 13168 |
| HPV18 | L1 | 32 | 10 | ILVYMVHIII | | 13169 |
| HPV18 | L1 | 443 | 8 | ITLTADVM | | 13170 |
| HPV18 | L1 | 443 | 10 | ITLTADVMSY | | 13171 |
| HPV18 | L1 | 443 | 11 | ITLTADVMSYI | | 13172 |
| HPV18 | L1 | 360 | 8 | IVTSDSQL | | 13173 |
| HPV18 | L1 | 360 | 9 | IVTSDSQLF | | 13174 |
| HPV18 | L1 | 151 | 9 | IYNPETQRL | | 13175 |
| HPV18 | L1 | 151 | 11 | IYNPETQRLVW | | 13176 |
| HPV18 | L1 | 143 | 9 | KFGLPDTSI | | 13177 |
| HPV18 | L1 | 143 | 10 | KFGLPDTSIY | | 13178 |
| HPV18 | L1 | 529 | 8 | KFLVQAGL | | 13179 |
| HPV18 | L1 | 516 | 9 | KFSLDLDQY | | 13180 |
| HPV18 | L1 | 516 | 11 | KFSLDLDQYPL | | 13181 |
| HPV18 | L1 | 507 | 11 | KFWNVDLKEKF | | 13182 |
| HPV18 | L1 | 505 | 9 | KLKFWNVDL | | 13183 |
| HPV18 | L1 | 125 | 10 | KVSAYQYRVF | | 13184 |
| HPV18 | L1 | 291 | 8 | KYPDYLQM | | 13185 |
| HPV18 | L1 | 48 | 9 | LFLRNVNVF | | 13186 |
| HPV18 | L1 | 48 | 11 | LFLRNVNVFPI | | 13187 |
| HPV18 | L1 | 367 | 8 | LFNKPYWL | | 13188 |
| HPV18 | L1 | 8 | 8 | LILHYHLL | | 13189 |
| HPV18 | L1 | 8 | 10 | LILHYHLLPL | | 13190 |
| HPV18 | L1 | 8 | 11 | LILHYHLLPLY | | 13191 |
| HPV18 | L1 | 14 | 8 | LLPLYGPL | | 13192 |
| HPV18 | L1 | 14 | 9 | LLPLYGPLY | | 13193 |
| HPV18 | L1 | 103 | 8 | LLTVGNPY | | 13194 |
| HPV18 | L1 | 103 | 9 | LLTVGNPYF | | 13195 |
| HPV18 | L1 | 445 | 8 | LTADVMSY | | 13196 |
| HPV18 | L1 | 445 | 9 | LTADVMSYI | | 13197 |
| HPV18 | L1 | 104 | 8 | LTVGNPYF | | 13198 |
| HPV18 | L1 | 159 | 10 | LVWACAGVEI | | 13199 |
| HPV18 | L1 | 33 | 8 | LVYMVHII | | 13200 |
| HPV18 | L1 | 33 | 9 | LVYMVHIII | | 13201 |
| HPV18 | L1 | 64 | 10 | LWRPSDNTVY | | 13202 |
| HPV18 | L1 | 64 | 11 | LWRPSDNTVYL | | 13203 |
| HPV18 | L1 | 17 | 11 | LYGPLYHPRPL | | 13204 |
| HPV18 | L1 | 21 | 9 | LYHPRPLPL | | 13205 |
| HPV18 | L1 | 336 | 8 | LYIKGTGM | | 13206 |
| HPV18 | L1 | 3 | 8 | LYTRVLIL | | 13207 |
| HPV18 | L1 | 3 | 10 | LYTRVLILHY | | 13208 |
| HPV18 | L1 | 307 | 10 | MFFCLRREQL | | 13209 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | L1 | 307 | 11 | MFFCLRREQLF | | 13210 |
| HPV18 | L1 | 261 | 9 | MVDTGYGAM | | 13211 |
| HPV18 | L1 | 261 | 11 | MVDTGYGAMDF | | 13212 |
| HPV18 | L1 | 36 | 10 | MVHIIICGHY | | 13213 |
| HPV18 | L1 | 36 | 11 | MVHIIICGHYI | | 13214 |
| HPV18 | L1 | 84 | 11 | NTDDYVTPTSI | | 13215 |
| HPV18 | L1 | 253 | 9 | NTVLEDGDM | | 13216 |
| HPV18 | L1 | 510 | 8 | NVDLKEKF | | 13217 |
| HPV18 | L1 | 510 | 10 | NVDLKEKFSL | | 13218 |
| HPV18 | L1 | 54 | 9 | NVFPIFLQM | | 13219 |
| HPV18 | L1 | 54 | 11 | NVFPIFLQMAL | | 13220 |
| HPV18 | L1 | 52 | 8 | NVNVFPIF | | 13221 |
| HPV18 | L1 | 52 | 9 | NVNVFPIFL | | 13222 |
| HPV18 | L1 | 52 | 11 | NVNVFPIFLQM | | 13223 |
| HPV18 | L1 | 207 | 11 | NVSVDYKQTQL | | 13224 |
| HPV18 | L1 | 57 | 8 | PIFLQMAL | | 13225 |
| HPV18 | L1 | 57 | 9 | PIFLQMALW | | 13226 |
| HPV18 | L1 | 282 | 8 | PLDICQSI | | 13227 |
| HPV18 | L1 | 282 | 11 | PLDICQSICKY | | 13228 |
| HPV18 | L1 | 248 | 9 | PLELKNTVL | | 13229 |
| HPV18 | L1 | 173 | 11 | PLGVGLSGHPF | | 13230 |
| HPV18 | L1 | 28 | 8 | PLHSILVY | | 13231 |
| HPV18 | L1 | 28 | 9 | PLHSILVYM | | 13232 |
| HPV18 | L1 | 26 | 8 | PLPLHSIL | | 13233 |
| HPV18 | L1 | 26 | 10 | PLPLHSILVY | | 13234 |
| HPV18 | L1 | 26 | 11 | PLPLHSILVYM | | 13235 |
| HPV18 | L1 | 240 | 10 | PLSQGDCPPL | | 13236 |
| HPV18 | L1 | 20 | 8 | PLYHPRPL | | 13237 |
| HPV18 | L1 | 20 | 10 | PLYHPRPLPL | | 13238 |
| HPV18 | L1 | 472 | 9 | PTTSLVDTY | | 13239 |
| HPV18 | L1 | 472 | 11 | PTTSLVDTYRF | | 13240 |
| HPV18 | L1 | 412 | 11 | PVPGQYDATKF | | 13241 |
| HPV18 | L1 | 502 | 8 | PYDKLKFW | | 13242 |
| HPV18 | L1 | 302 | 8 | PYGDSMFF | | 13243 |
| HPV18 | L1 | 302 | 10 | PYGDSMFFCL | | 13244 |
| HPV18 | L1 | 435 | 9 | QFIFQLCTI | | 13245 |
| HPV18 | L1 | 435 | 11 | QFIFQLCTITL | | 13246 |
| HPV18 | L1 | 216 | 11 | QLCILGCAPAI | | 13247 |
| HPV18 | L1 | 315 | 8 | QLFARHFW | | 13248 |
| HPV18 | L1 | 366 | 8 | QLFNKPYW | | 13249 |
| HPV18 | L1 | 366 | 9 | QLFNKPYWL | | 13250 |
| HPV18 | L1 | 137 | 8 | QLPDPNKF | | 13251 |
| HPV18 | L1 | 137 | 10 | QLPDPNKFGL | | 13252 |
| HPV18 | L1 | 297 | 11 | QMSADPYGDSM | | 13253 |
| HPV18 | L1 | 416 | 10 | QYDATKFKQY | | 13254 |
| HPV18 | L1 | 523 | 8 | QYPLGRKF | | 13255 |
| HPV18 | L1 | 523 | 9 | QYPLGRKFL | | 13256 |
| HPV18 | L1 | 130 | 9 | QYRVFRVQL | | 13257 |
| HPV18 | L1 | 424 | 9 | QYSRHVEEY | | 13258 |
| HPV18 | L1 | 424 | 11 | QYSRHVEEYDL | | 13259 |
| HPV18 | L1 | 481 | 8 | RFVQSVAI | | 13260 |
| HPV18 | L1 | 102 | 9 | RLLTVGNPY | | 13261 |
| HPV18 | L1 | 102 | 10 | RLLTVGNPYF | | 13262 |
| HPV18 | L1 | 158 | 11 | RLVWACAGVEI | | 13263 |
| HPV18 | L1 | 6 | 9 | RVLILHYHL | | 13264 |
| HPV18 | L1 | 6 | 10 | RVLILHYHLL | | 13265 |
| HPV18 | L1 | 135 | 10 | RVQLPDPNKF | | 13266 |
| HPV18 | L1 | 81 | 8 | RVVNTDDY | | 13267 |
| HPV18 | L1 | 288 | 8 | SICKYPDY | | 13268 |
| HPV18 | L1 | 288 | 9 | SICKYPDYL | | 13269 |
| HPV18 | L1 | 288 | 11 | SICKYPDYLQM | | 13270 |
| HPV18 | L1 | 93 | 11 | SIFYHAGSSRL | | 13271 |
| HPV18 | L1 | 459 | 8 | SILEDWNF | | 13272 |
| HPV18 | L1 | 31 | 9 | SILVYMVHI | | 13273 |
| HPV18 | L1 | 31 | 10 | SILVYMVHII | | 13274 |
| HPV18 | L1 | 31 | 11 | SILVYMVHIII | | 13275 |
| HPV18 | L1 | 359 | 9 | SIVTSDSQL | | 13276 |
| HPV18 | L1 | 359 | 10 | SIVTSDSQLF | | 13277 |
| HPV18 | L1 | 150 | 10 | SIYNPETQRL | | 13278 |
| HPV18 | L1 | 518 | 9 | SLDLDQYPL | | 13279 |
| HPV18 | L1 | 475 | 8 | SLVDTYRF | | 13280 |
| HPV18 | L1 | 335 | 9 | SLYIKGTGM | | 13281 |
| HPV18 | L1 | 306 | 11 | SMFFCLRREQL | | 13282 |
| HPV18 | L1 | 455 | 10 | SMNSSILEDW | | 13283 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | L1 | 408 | 10 | STQSPVPGQY | | 13284 |
| HPV18 | L1 | 78 | 11 | SVARVVNTDDY | | 13285 |
| HPV18 | L1 | 209 | 9 | SVDYKQTQL | | 13286 |
| HPV18 | L1 | 209 | 11 | SVDYKQTQLCI | | 13287 |
| HPV18 | L1 | 451 | 10 | SYIHSMNSSI | | 13288 |
| HPV18 | L1 | 451 | 11 | SYIHSMNSSIL | | 13289 |
| HPV18 | L1 | 442 | 9 | TITLTADVM | | 13290 |
| HPV18 | L1 | 442 | 11 | TITLTADVMSY | | 13291 |
| HPV18 | L1 | 273 | 11 | TLQDTKCEVPL | | 13292 |
| HPV18 | L1 | 444 | 9 | TLTADVMSY | | 13293 |
| HPV18 | L1 | 444 | 10 | TLTADVMSYI | | 13294 |
| HPV18 | L1 | 327 | 10 | TMGDTVPQSL | | 13295 |
| HPV18 | L1 | 327 | 11 | TMGDTVPQSLY | | 13296 |
| HPV18 | L1 | 397 | 9 | TTPSTNLTI | | 13297 |
| HPV18 | L1 | 473 | 8 | TTSLVDTY | | 13298 |
| HPV18 | L1 | 473 | 10 | TTSLVDTYRF | | 13299 |
| HPV18 | L1 | 254 | 8 | TVLEDGDM | | 13300 |
| HPV18 | L1 | 331 | 8 | TVPQSLYI | | 13301 |
| HPV18 | L1 | 393 | 11 | TVVDTTPSTNL | | 13302 |
| HPV18 | L1 | 479 | 10 | TYRFVQSVAI | | 13303 |
| HPV18 | L1 | 55 | 8 | VFPIFLQM | | 13304 |
| HPV18 | L1 | 55 | 10 | VFPIFLQMAL | | 13305 |
| HPV18 | L1 | 55 | 11 | VFPIFLQMALW | | 13306 |
| HPV18 | L1 | 7 | 8 | VLILHYHL | | 13307 |
| HPV18 | L1 | 7 | 9 | VLILHYHLL | | 13308 |
| HPV18 | L1 | 7 | 11 | VLILHYHLLPL | | 13309 |
| HPV18 | L1 | 449 | 8 | VMSYIHSM | | 13310 |
| HPV18 | L1 | 89 | 8 | VTPTSIFY | | 13311 |
| HPV18 | L1 | 361 | 8 | VTSDSQLF | | 13312 |
| HPV18 | L1 | 394 | 10 | VVDTTPSTNL | | 13313 |
| HPV18 | L1 | 160 | 9 | VWACAGVEI | | 13314 |
| HPV18 | L1 | 34 | 8 | VYMVHIII | | 13315 |
| HPV18 | L1 | 351 | 10 | VYSPSPSGSI | | 13316 |
| HPV18 | L1 | 452 | 9 | YIHSMNSSI | | 13317 |
| HPV18 | L1 | 452 | 10 | YIHSMNSSIL | | 13318 |
| HPV18 | L1 | 295 | 9 | YLQMSADPY | | 13319 |
| HPV18 | L1 | 35 | 11 | YMVHIICGHY | | 13320 |
| HPV18 | L1 | 4 | 9 | YTRVLILHY | | 13321 |
| HPV18 | L1 | 4 | 11 | YTRVLILHYHL | | 13322 |
| HPV18 | L1 | 88 | 8 | YVTPTSIF | | 13323 |
| HPV18 | L1 | 88 | 9 | YVTPTSIFY | | 13324 |
| HPV18 | L2 | 255 | 9 | AFEPVDTTL | | 13325 |
| HPV18 | L2 | 255 | 11 | AFEPVDTTLTF | | 13326 |
| HPV18 | L2 | 370 | 9 | AFFKYSPTI | | 13327 |
| HPV18 | L2 | 161 | 8 | AFSDPSII | | 13328 |
| HPV18 | L2 | 286 | 11 | ALTSRRGTVRF | | 13329 |
| HPV18 | L2 | 341 | 8 | ATEDNDLF | | 13330 |
| HPV18 | L2 | 341 | 10 | ATEDNDLFDI | | 13331 |
| HPV18 | L2 | 341 | 11 | ATEDNDLFDIY | | 13332 |
| HPV18 | L2 | 303 | 11 | ATMFTRSGTQI | | 13333 |
| HPV18 | L2 | 275 | 8 | DFMDIIRL | | 13334 |
| HPV18 | L2 | 278 | 10 | DIIRLHRPAL | | 13335 |
| HPV18 | L2 | 322 | 11 | DISPIAPSPEY | | 13336 |
| HPV18 | L2 | 404 | 11 | DITLPSTTSVW | | 13337 |
| HPV18 | L2 | 142 | 11 | DITPSSTSVSI | | 13338 |
| HPV18 | L2 | 346 | 10 | DLFDIYADDM | | 13339 |
| HPV18 | L2 | 83 | 11 | DVGPTRPPVVI | | 13340 |
| HPV18 | L2 | 270 | 8 | DVPDSDFM | | 13341 |
| HPV18 | L2 | 270 | 10 | DVPDSDFMDI | | 13342 |
| HPV18 | L2 | 270 | 11 | DVPDSDFMDII | | 13343 |
| HPV18 | L2 | 396 | 10 | DVPVYTGPDI | | 13344 |
| HPV18 | L2 | 30 | 11 | DVVPKVEGTTL | | 13345 |
| HPV18 | L2 | 240 | 9 | EFLTRPSSL | | 13346 |
| HPV18 | L2 | 240 | 10 | EFLTRPSSLI | | 13347 |
| HPV18 | L2 | 331 | 8 | EYIELQPL | | 13348 |
| HPV18 | L2 | 371 | 8 | FFKYSPTI | | 13349 |
| HPV18 | L2 | 443 | 11 | FIPKKRKRVPY | | 13350 |
| HPV18 | L2 | 241 | 8 | FLTRPSSL | | 13351 |
| HPV18 | L2 | 241 | 9 | FLTRPSSLI | | 13352 |
| HPV18 | L2 | 241 | 11 | FLTRPSSLITY | | 13353 |
| HPV18 | L2 | 122 | 9 | FTGTSGFDI | | 13354 |
| HPV18 | L2 | 157 | 11 | FTNPAFSDPSI | | 13355 |
| HPV18 | L2 | 306 | 8 | FTRSGTQI | | 13356 |
| HPV18 | L2 | 319 | 8 | FYHDISPI | | 13357 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | L2 | 51 | 9 | GIFLGGLGI | | 13358 |
| HPV18 | L2 | 429 | 8 | GIHGTHYY | | 13359 |
| HPV18 | L2 | 429 | 9 | GIHGTHYYL | | 13360 |
| HPV18 | L2 | 429 | 10 | GIHGTHYYLW | | 13361 |
| HPV18 | L2 | 64 | 8 | GTGGRTGY | | 13362 |
| HPV18 | L2 | 64 | 9 | GTGGRTGYI | | 13363 |
| HPV18 | L2 | 64 | 11 | GTGGRTGYIPL | | 13364 |
| HPV18 | L2 | 188 | 8 | GTHGYEEI | | 13365 |
| HPV18 | L2 | 188 | 10 | GTHGYEEIPL | | 13366 |
| HPV18 | L2 | 432 | 9 | GTHYYLWPL | | 13367 |
| HPV18 | L2 | 432 | 10 | GTHYYLWPLY | | 13368 |
| HPV18 | L2 | 432 | 11 | GTHYYLWPLYY | | 13369 |
| HPV18 | L2 | 183 | 10 | GTPTSGTHGY | | 13370 |
| HPV18 | L2 | 310 | 10 | GTQIGARVHF | | 13371 |
| HPV18 | L2 | 310 | 11 | GTQIGARVHFY | | 13372 |
| HPV18 | L2 | 37 | 8 | GTTLADKI | | 13373 |
| HPV18 | L2 | 37 | 9 | GTTLADKIL | | 13374 |
| HPV18 | L2 | 37 | 11 | GTTLADKILQW | | 13375 |
| HPV18 | L2 | 134 | 8 | GTTTPAVL | | 13376 |
| HPV18 | L2 | 134 | 10 | GTTTPAVLDI | | 13377 |
| HPV18 | L2 | 292 | 8 | GTVRFSRL | | 13378 |
| HPV18 | L2 | 191 | 10 | GYEEIPLQTF | | 13379 |
| HPV18 | L2 | 318 | 9 | HFYHDISPI | | 13380 |
| HPV18 | L2 | 434 | 8 | HYYLWPLY | | 13381 |
| HPV18 | L2 | 434 | 9 | HYYLWPLYY | | 13382 |
| HPV18 | L2 | 434 | 10 | HYYLWPLYYF | | 13383 |
| HPV18 | L2 | 434 | 11 | HYYLWPLYYFI | | 13384 |
| HPV18 | L2 | 52 | 8 | IFLGGLGI | | 13385 |
| HPV18 | L2 | 279 | 9 | IIRLHRPAL | | 13386 |
| HPV18 | L2 | 44 | 9 | ILQWSSLGI | | 13387 |
| HPV18 | L2 | 44 | 10 | ILQWSSLGIF | | 13388 |
| HPV18 | L2 | 44 | 11 | ILQWSSLGIFL | | 13389 |
| HPV18 | L2 | 405 | 10 | ITLPSTTSVW | | 13390 |
| HPV18 | L2 | 143 | 10 | ITPSSTSVSI | | 13391 |
| HPV18 | L2 | 249 | 8 | ITYDNPAF | | 13392 |
| HPV18 | L2 | 43 | 8 | KILQWSSL | | 13393 |
| HPV18 | L2 | 43 | 10 | KILQWSSLGI | | 13394 |
| HPV18 | L2 | 43 | 11 | KILQWSSLGIF | | 13395 |
| HPV18 | L2 | 34 | 11 | KVEGTTLADKI | | 13396 |
| HPV18 | L2 | 347 | 9 | LFDIYADDM | | 13397 |
| HPV18 | L2 | 248 | 9 | LITYDNPAF | | 13398 |
| HPV18 | L2 | 242 | 8 | LTRPSSLI | | 13399 |
| HPV18 | L2 | 242 | 10 | LTRPSSLITY | | 13400 |
| HPV18 | L2 | 287 | 10 | LTSRRGTVRF | | 13401 |
| HPV18 | L2 | 391 | 10 | LTSSWDVPVY | | 13402 |
| HPV18 | L2 | 338 | 10 | LVSATEDNDL | | 13403 |
| HPV18 | L2 | 338 | 11 | LVSATEDNDLF | | 13404 |
| HPV18 | L2 | 437 | 8 | LWPLYYFI | | 13405 |
| HPV18 | L2 | 305 | 9 | MFTRSGTQI | | 13406 |
| HPV18 | L2 | 386 | 10 | NVTVPLTSSW | | 13407 |
| HPV18 | L2 | 325 | 8 | PIAPSPEY | | 13408 |
| HPV18 | L2 | 325 | 9 | PIAPSPEYI | | 13409 |
| HPV18 | L2 | 325 | 11 | PIAPSPEYIEL | | 13410 |
| HPV18 | L2 | 390 | 11 | PLTSSWDVPVY | | 13411 |
| HPV18 | L2 | 337 | 11 | PLVSATEDNDL | | 13412 |
| HPV18 | L2 | 419 | 9 | PTAPASTQY | | 13413 |
| HPV18 | L2 | 419 | 10 | PTAPASTQYI | | 13414 |
| HPV18 | L2 | 98 | 9 | PTDPSIVTL | | 13415 |
| HPV18 | L2 | 98 | 10 | PTDPSIVTLI | | 13416 |
| HPV18 | L2 | 120 | 9 | PTFTGTSGF | | 13417 |
| HPV18 | L2 | 120 | 11 | PTFTGTSGFDI | | 13418 |
| HPV18 | L2 | 376 | 9 | PTISSASSY | | 13419 |
| HPV18 | L2 | 86 | 8 | PTRPPVVI | | 13420 |
| HPV18 | L2 | 185 | 8 | PTSGTHGY | | 13421 |
| HPV18 | L2 | 185 | 11 | PTSGTHGYEEI | | 13422 |
| HPV18 | L2 | 216 | 11 | PTVRRVAGPRL | | 13423 |
| HPV18 | L2 | 258 | 8 | PVDTTLTF | | 13424 |
| HPV18 | L2 | 95 | 9 | PVGPTDPSI | | 13425 |
| HPV18 | L2 | 360 | 10 | PVPSRSTTSF | | 13426 |
| HPV18 | L2 | 398 | 8 | PVYTGPDI | | 13427 |
| HPV18 | L2 | 398 | 10 | PVYTGPDITL | | 13428 |
| HPV18 | L2 | 452 | 8 | PYFFADGF | | 13429 |
| HPV18 | L2 | 312 | 8 | QIGARVHF | | 13430 |
| HPV18 | L2 | 312 | 9 | QIGARVHFY | | 13431 |

TABLE X-continued

A24 Supermotif Peptides

| Type | Protein | Position | No. of Amino Acids | Sequence | A*2402 | Seq. Id. No. |
|---|---|---|---|---|---|---|
| HPV18 | L2 | 172 | 10 | QTGEVAGNVF | | 13432 |
| HPV18 | L2 | 233 | 9 | QVSVANPEF | | 13433 |
| HPV18 | L2 | 233 | 10 | QVSVANPEFL | | 13434 |
| HPV18 | L2 | 46 | 8 | QWSSLGIF | | 13435 |
| HPV18 | L2 | 46 | 9 | QWSSLGIFL | | 13436 |
| HPV18 | L2 | 426 | 10 | QYIGIHGTHY | | 13437 |
| HPV18 | L2 | 426 | 11 | QYIGIHGTHYY | | 13438 |
| HPV18 | L2 | 295 | 11 | RFSRLGQRATM | | 13439 |
| HPV18 | L2 | 298 | 8 | RLGQRATM | | 13440 |
| HPV18 | L2 | 298 | 9 | RLGQRATMF | | 13441 |
| HPV18 | L2 | 220 | 8 | RVAGPRLY | | 13442 |
| HPV18 | L2 | 316 | 8 | RVHFYHDI | | 13443 |
| HPV18 | L2 | 316 | 11 | RVHFYHDISPI | | 13444 |
| HPV18 | L2 | 450 | 10 | RVPYFFADGF | | 13445 |
| HPV18 | L2 | 368 | 11 | SFAFKYSPTI | | 13446 |
| HPV18 | L2 | 49 | 9 | SLGIFLGGL | | 13447 |
| HPV18 | L2 | 49 | 11 | SLGIFLGGLGI | | 13448 |
| HPV18 | L2 | 247 | 10 | SLITYDNPAF | | 13449 |
| HPV18 | L2 | 147 | 11 | STSVSISTTNF | | 13450 |
| HPV18 | L2 | 153 | 10 | STTNFTNPAF | | 13451 |
| HPV18 | L2 | 365 | 8 | STTSFAFF | | 13452 |
| HPV18 | L2 | 365 | 10 | STTSFAFFKY | | 13453 |
| HPV18 | L2 | 409 | 8 | STTSVWPI | | 13454 |
| HPV18 | L2 | 235 | 8 | SVANPEFL | | 13455 |
| HPV18 | L2 | 149 | 9 | SVSISTTNF | | 13456 |
| HPV18 | L2 | 383 | 9 | SYSNVTVPL | | 13457 |
| HPV18 | L2 | 121 | 8 | TFTGTSGF | | 13458 |
| HPV18 | L2 | 121 | 10 | TFTGTSGFDI | | 13459 |
| HPV18 | L2 | 377 | 8 | TISSASSY | | 13460 |
| HPV18 | L2 | 39 | 9 | TLADKILQW | | 13461 |
| HPV18 | L2 | 406 | 9 | TLPSTTSVW | | 13462 |
| HPV18 | L2 | 406 | 11 | TLPSTTSVWPI | | 13463 |
| HPV18 | L2 | 304 | 10 | TMFTRSGTQI | | 13464 |
| HPV18 | L2 | 38 | 8 | TTLADKIL | | 13465 |
| HPV18 | L2 | 38 | 10 | TTLADKILQW | | 13466 |
| HPV18 | L2 | 154 | 9 | TTNFTNPAF | | 13467 |
| HPV18 | L2 | 136 | 8 | TTPAVLDI | | 13468 |
| HPV18 | L2 | 366 | 9 | TTSFAFFKY | | 13469 |
| HPV18 | L2 | 135 | 9 | TTTPAVLDI | | 13470 |
| HPV18 | L2 | 388 | 8 | TVPLTSSW | | 13471 |
| HPV18 | L2 | 217 | 10 | TVRRVAGPRL | | 13472 |
| HPV18 | L2 | 217 | 11 | TVRRVAGPRLY | | 13473 |
| HPV18 | L2 | 113 | 10 | VTSGAPRPTF | | 13474 |
| HPV18 | L2 | 387 | 9 | VTVPLTSSW | | 13475 |
| HPV18 | L2 | 31 | 10 | VVPKVEGTTL | | 13476 |
| HPV18 | L2 | 112 | 11 | VVTSGAPRPTF | | 13477 |
| HPV18 | L2 | 399 | 9 | VYTGPDITL | | 13478 |
| HPV18 | L2 | 427 | 9 | YIGIHGTHY | | 13479 |
| HPV18 | L2 | 427 | 10 | YIGIHGTHYY | | 13480 |
| HPV18 | L2 | 427 | 11 | YIGIHGTHYYL | | 13481 |
| HPV18 | L2 | 436 | 8 | YLWPLYYF | | 13482 |
| HPV18 | L2 | 436 | 9 | YLWPLYYFI | | 13483 |
| HPV18 | L2 | 400 | 8 | YTGPDITL | | 13484 |
| HPV18 | L2 | 435 | 8 | YYLWPLYY | | 13485 |
| HPV18 | L2 | 435 | 9 | YYLWPLYYF | | 13486 |
| HPV18 | L2 | 435 | 10 | YYLWPLYYFI | | 13487 |
| HPV31 | E1 | 371 | 11 | AFLKSNSQAKI | | 13488 |
| HPV31 | E1 | 519 | 9 | ALDGNPVSI | | 13489 |
| HPV31 | E1 | 533 | 10 | ALMQLKCPPL | | 13490 |
| HPV31 | E1 | 533 | 11 | ALMQLKCPPLL | | 13491 |
| HPV31 | E1 | 298 | 9 | ALYWYRTGM | | 13492 |
| HPV31 | E1 | 186 | 9 | AMLGKFKEL | | 13493 |
| HPV31 | E1 | 186 | 10 | AMLGKFKELY | | 13494 |
| HPV31 | E1 | 504 | 8 | ATTPCWHY | | 13495 |
| HPV31 | E1 | 504 | 9 | ATTPCWHYI | | 13496 |
| HPV31 | E1 | 22 | 11 | AVIDRQTGDNI | | 13497 |
| HPV31 | E1 | 81 | 9 | AVQVLKRKY | | 13498 |
| HPV31 | E1 | 279 | 8 | CISTNCML | | 13499 |
| HPV31 | E1 | 279 | 9 | CISTNCMLI | | 13500 |
| HPV31 | E1 | 239 | 9 | CLYCHLQSL | | 13501 |
| HPV31 | E1 | 284 | 9 | CMLIQPPKL | | 13502 |
| HPV31 | E1 | 213 | 9 | CTDWCVAAF | | 13503 |
| HPV31 | E1 | 100 | 10 | CVDYNISPRL | | 13504 |
| HPV31 | E1 | 620 | 10 | CVSGQNIRTL | | 13505 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | E1 | 508 | 8 | CWHYIDNY | | 13506 |
| HPV31 | E1 | 508 | 9 | CWHYIDNYL | | 13507 |
| HPV31 | E1 | 49 | 9 | DFIDNCNVY | | 13508 |
| HPV31 | E1 | 96 | 8 | DISSCVDY | | 13509 |
| HPV31 | E1 | 96 | 10 | DISSCVDYNI | | 13510 |
| HPV31 | E1 | 421 | 8 | DIVKFLRY | | 13511 |
| HPV31 | E1 | 421 | 11 | DIVKFLRYQQI | | 13512 |
| HPV31 | E1 | 336 | 8 | DLSQMVQW | | 13513 |
| HPV31 | E1 | 336 | 10 | DLSQMVQWAY | | 13514 |
| HPV31 | E1 | 42 | 9 | DTGEDMVDF | | 13515 |
| HPV31 | E1 | 42 | 10 | DTGEDMVDFI | | 13516 |
| HPV31 | E1 | 332 | 9 | DTTFDLSQM | | 13517 |
| HPV31 | E1 | 528 | 8 | DVKHKALM | | 13518 |
| HPV31 | E1 | 528 | 10 | DVKHKALMQL | | 13519 |
| HPV31 | E1 | 348 | 8 | DVMDDSEI | | 13520 |
| HPV31 | E1 | 348 | 10 | DVMDDSEIAY | | 13521 |
| HPV31 | E1 | 311 | 9 | DVYGETPEW | | 13522 |
| HPV31 | E1 | 311 | 10 | DVYGETPEWI | | 13523 |
| HPV31 | E1 | 418 | 8 | DWRDIVKF | | 13524 |
| HPV31 | E1 | 418 | 9 | DWRDIVKFL | | 13525 |
| HPV31 | E1 | 418 | 11 | DWRDIVKFLRY | | 13526 |
| HPV31 | E1 | 102 | 8 | DYNISPRL | | 13527 |
| HPV31 | E1 | 102 | 11 | DYNISPRLKAI | | 13528 |
| HPV31 | E1 | 432 | 9 | EFVSFLSAL | | 13529 |
| HPV31 | E1 | 432 | 11 | EFVSFLSALKL | | 13530 |
| HPV31 | E1 | 354 | 9 | EIAYKYAQL | | 13531 |
| HPV31 | E1 | 583 | 10 | ELSDKNWKSF | | 13532 |
| HPV31 | E1 | 583 | 11 | ELSDKNWKSFF | | 13533 |
| HPV31 | E1 | 193 | 8 | ELYGVSFM | | 13534 |
| HPV31 | E1 | 193 | 10 | ELYGVSFMEL | | 13535 |
| HPV31 | E1 | 193 | 11 | ELYGVSFMELI | | 13536 |
| HPV31 | E1 | 168 | 8 | ETPTRNIL | | 13537 |
| HPV31 | E1 | 168 | 11 | ETPTRNILQVL | | 13538 |
| HPV31 | E1 | 318 | 9 | EWIERQTVL | | 13539 |
| HPV31 | E1 | 592 | 9 | FFSRTWCRL | | 13540 |
| HPV31 | E1 | 592 | 11 | FFSRTWCRLNL | | 13541 |
| HPV31 | E1 | 50 | 8 | FIDNCNVY | | 13542 |
| HPV31 | E1 | 443 | 11 | FLKGVPKKNCI | | 13543 |
| HPV31 | E1 | 372 | 10 | FLKSNSQAKI | | 13544 |
| HPV31 | E1 | 473 | 9 | FLQGCIISY | | 13545 |
| HPV31 | E1 | 425 | 9 | FLRYQQIEF | | 13546 |
| HPV31 | E1 | 436 | 8 | FLSALKLF | | 13547 |
| HPV31 | E1 | 436 | 9 | FLSALKLFL | | 13548 |
| HPV31 | E1 | 199 | 8 | FMELIRPF | | 13549 |
| HPV31 | E1 | 566 | 9 | FTFPNPFPF | | 13550 |
| HPV31 | E1 | 433 | 8 | FVSFLSAL | | 13551 |
| HPV31 | E1 | 433 | 10 | FVSFLSALKL | | 13552 |
| HPV31 | E1 | 433 | 11 | FVSFLSALKLF | | 13553 |
| HPV31 | E1 | 488 | 11 | FWLQPLADAKI | | 13554 |
| HPV31 | E1 | 230 | 9 | GFKTLLQPY | | 13555 |
| HPV31 | E1 | 230 | 11 | GFKTLLQPYCL | | 13556 |
| HPV31 | E1 | 499 | 11 | GMLDDATTPCW | | 13557 |
| HPV31 | E1 | 467 | 8 | GMSLISFL | | 13558 |
| HPV31 | E1 | 305 | 9 | GMSNISDVY | | 13559 |
| HPV31 | E1 | 252 | 10 | GMVMLMLVRF | | 13560 |
| HPV31 | E1 | 11 | 8 | GTGCNGWF | | 13561 |
| HPV31 | E1 | 11 | 9 | GTGCNGWFY | | 13562 |
| HPV31 | E1 | 225 | 10 | GTVAEGFKTL | | 13563 |
| HPV31 | E1 | 225 | 11 | GTVAEGFKTLL | | 13564 |
| HPV31 | E1 | 446 | 8 | GVPKKNCI | | 13565 |
| HPV31 | E1 | 446 | 9 | GVPKKNCIL | | 13566 |
| HPV31 | E1 | 446 | 10 | GVPKKNCILI | | 13567 |
| HPV31 | E1 | 196 | 8 | GVSFMELI | | 13568 |
| HPV31 | E1 | 196 | 11 | GVSFMELIRPF | | 13569 |
| HPV31 | E1 | 222 | 10 | GVTGTVAEGF | | 13570 |
| HPV31 | E1 | 16 | 9 | GWFYVEAVI | | 13571 |
| HPV31 | E1 | 243 | 9 | HLQSLACSW | | 13572 |
| HPV31 | E1 | 243 | 11 | HLQSLACSWGM | | 13573 |
| HPV31 | E1 | 510 | 11 | HYIDNYLRNAL | | 13574 |
| HPV31 | E1 | 391 | 10 | HYKRAEKRQM | | 13575 |
| HPV31 | E1 | 478 | 11 | IISYANSKSHF | | 13576 |
| HPV31 | E1 | 268 | 10 | ITIEKLLEKL | | 13577 |
| HPV31 | E1 | 268 | 11 | ITIEKLLEKLL | | 13578 |
| HPV31 | E1 | 381 | 8 | IVKDCGTM | | 13579 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | E1 | 422 | 10 | IVKFLRYQQI | | 13580 |
| HPV31 | E1 | 190 | 10 | KFKELYGVSF | | 13581 |
| HPV31 | E1 | 190 | 11 | KFKELYGVSFM | | 13582 |
| HPV31 | E1 | 424 | 8 | KFLRYQQI | | 13583 |
| HPV31 | E1 | 424 | 10 | KFLRYQQIEF | | 13584 |
| HPV31 | E1 | 380 | 9 | KIVKDCGTM | | 13585 |
| HPV31 | E1 | 276 | 10 | KLLCISTNCM | | 13586 |
| HPV31 | E1 | 276 | 11 | KLLCISTNCML | | 13587 |
| HPV31 | E1 | 272 | 9 | KLLEKLLCI | | 13588 |
| HPV31 | E1 | 291 | 9 | KLRSTAAAL | | 13589 |
| HPV31 | E1 | 291 | 10 | KLRSTAAALY | | 13590 |
| HPV31 | E1 | 291 | 11 | KLRSTAAALYW | | 13591 |
| HPV31 | E1 | 119 | 8 | KTAKRRLF | | 13592 |
| HPV31 | E1 | 119 | 10 | KTAKRRLFEL | | 13593 |
| HPV31 | E1 | 232 | 9 | KTLLQPYCL | | 13594 |
| HPV31 | E1 | 232 | 10 | KTLLQPYCLY | | 13595 |
| HPV31 | E1 | 179 | 9 | KTSNGKAAM | | 13596 |
| HPV31 | E1 | 179 | 10 | KTSNGKAAML | | 13597 |
| HPV31 | E1 | 412 | 8 | KVSDEGDW | | 13598 |
| HPV31 | E1 | 412 | 11 | KVSDEGDWRDI | | 13599 |
| HPV31 | E1 | 88 | 10 | KYVGSPLSDI | | 13600 |
| HPV31 | E1 | 125 | 9 | LFELPDSGY | | 13601 |
| HPV31 | E1 | 470 | 9 | LISFLQGCI | | 13602 |
| HPV31 | E1 | 470 | 10 | LISFLQGCII | | 13603 |
| HPV31 | E1 | 277 | 9 | LLCISTNCM | | 13604 |
| HPV31 | E1 | 277 | 10 | LLCISTNCML | | 13605 |
| HPV31 | E1 | 277 | 11 | LLCISTNCMLI | | 13606 |
| HPV31 | E1 | 273 | 8 | LLEKLLCI | | 13607 |
| HPV31 | E1 | 234 | 8 | LLQPYCLY | | 13608 |
| HPV31 | E1 | 234 | 11 | LLQPYCLYCHL | | 13609 |
| HPV31 | E1 | 534 | 9 | LMQLKCPPL | | 13610 |
| HPV31 | E1 | 534 | 10 | LMQLKCPPLL | | 13611 |
| HPV31 | E1 | 534 | 11 | LMQLKCPPLLI | | 13612 |
| HPV31 | E1 | 258 | 11 | LVRFKCAKNRI | | 13613 |
| HPV31 | E1 | 563 | 10 | LVVFTFPNPF | | 13614 |
| HPV31 | E1 | 240 | 8 | LYCHLQSL | | 13615 |
| HPV31 | E1 | 194 | 9 | LYGVSFMEL | | 13616 |
| HPV31 | E1 | 194 | 10 | LYGVSFMELI | | 13617 |
| HPV31 | E1 | 299 | 8 | LYWYRTGM | | 13618 |
| HPV31 | E1 | 299 | 11 | LYWYRTGMSNI | | 13619 |
| HPV31 | E1 | 500 | 10 | MLDDATTPCW | | 13620 |
| HPV31 | E1 | 187 | 8 | MLGKFKEL | | 13621 |
| HPV31 | E1 | 187 | 9 | MLGKFKELY | | 13622 |
| HPV31 | E1 | 285 | 8 | MLIQPPKL | | 13623 |
| HPV31 | E1 | 47 | 11 | MVDFIDNCNVY | | 13624 |
| HPV31 | E1 | 253 | 9 | MVMLMLVRF | | 13625 |
| HPV31 | E1 | 143 | 11 | MVQVEEQQTTL | | 13626 |
| HPV31 | E1 | 340 | 11 | MVQWAYDNDVM | | 13627 |
| HPV31 | E1 | 547 | 10 | NINAGKDDRW | | 13628 |
| HPV31 | E1 | 104 | 9 | NISPRLKAI | | 13629 |
| HPV31 | E1 | 104 | 11 | NISPRLKAICI | | 13630 |
| HPV31 | E1 | 135 | 9 | NTEVETQQM | | 13631 |
| HPV31 | E1 | 460 | 9 | NTGKSYFGM | | 13632 |
| HPV31 | E1 | 460 | 11 | NTGKSYFGMSL | | 13633 |
| HPV31 | E1 | 588 | 10 | NWKSFFSRTW | | 13634 |
| HPV31 | E1 | 573 | 10 | PFDKNGNPVY | | 13635 |
| HPV31 | E1 | 492 | 9 | PLADAKIGM | | 13636 |
| HPV31 | E1 | 492 | 10 | PLADAKIGML | | 13637 |
| HPV31 | E1 | 541 | 8 | PLLITSNI | | 13638 |
| HPV31 | E1 | 93 | 11 | PLSDISSCVDY | | 13639 |
| HPV31 | E1 | 170 | 9 | PTRNILQVL | | 13640 |
| HPV31 | E1 | 524 | 11 | PVSIDVKHKAL | | 13641 |
| HPV31 | E1 | 580 | 10 | PVYELSDKNW | | 13642 |
| HPV31 | E1 | 237 | 8 | PYCLYCHL | | 13643 |
| HPV31 | E1 | 237 | 11 | PYCLYCHLQSL | | 13644 |
| HPV31 | E1 | 557 | 10 | PYLHSRLVVF | | 13645 |
| HPV31 | E1 | 430 | 8 | QIEFVSFL | | 13646 |
| HPV31 | E1 | 430 | 11 | QIEFVSFLSAL | | 13647 |
| HPV31 | E1 | 536 | 8 | QLKCPPLL | | 13648 |
| HPV31 | E1 | 536 | 9 | QLKCPPLLI | | 13649 |
| HPV31 | E1 | 399 | 8 | QMSMGQWI | | 13650 |
| HPV31 | E1 | 323 | 8 | QTVLQHSF | | 13651 |
| HPV31 | E1 | 145 | 9 | QVEEQQTTL | | 13652 |
| HPV31 | E1 | 342 | 9 | QWAYDNDVM | | 13653 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | E1 | 260 | 9 | RFKCAKNRI | | 13654 |
| HPV31 | E1 | 260 | 11 | RFKCAKNRITI | | 13655 |
| HPV31 | E1 | 267 | 8 | RITIEKLL | | 13656 |
| HPV31 | E1 | 267 | 11 | RITIEKLLEKL | | 13657 |
| HPV31 | E1 | 124 | 10 | RLFELPDSGY | | 13658 |
| HPV31 | E1 | 562 | 11 | RLVVFTFPNPF | | 13659 |
| HPV31 | E1 | 303 | 11 | RTGMSNISDVY | | 13660 |
| HPV31 | E1 | 595 | 8 | RTWCRLNL | | 13661 |
| HPV31 | E1 | 555 | 9 | RWPYLHSRL | | 13662 |
| HPV31 | E1 | 427 | 10 | RYQQIEFVSF | | 13663 |
| HPV31 | E1 | 427 | 11 | RYQQIEFVSFL | | 13664 |
| HPV31 | E1 | 591 | 10 | SFFSRTWCRL | | 13665 |
| HPV31 | E1 | 472 | 8 | SFLQGCII | | 13666 |
| HPV31 | E1 | 472 | 10 | SFLQGCIISY | | 13667 |
| HPV31 | E1 | 435 | 8 | SFLSALKL | | 13668 |
| HPV31 | E1 | 435 | 9 | SFLSALKLF | | 13669 |
| HPV31 | E1 | 435 | 10 | SFLSALKLFL | | 13670 |
| HPV31 | E1 | 198 | 9 | SFMELIRPF | | 13671 |
| HPV31 | E1 | 329 | 9 | SFNDTTFDL | | 13672 |
| HPV31 | E1 | 526 | 9 | SIDVKHKAL | | 13673 |
| HPV31 | E1 | 526 | 10 | SIDVKHKALM | | 13674 |
| HPV31 | E1 | 246 | 8 | SLACSWGM | | 13675 |
| HPV31 | E1 | 246 | 10 | SLACSWGMVM | | 13676 |
| HPV31 | E1 | 246 | 11 | SLACSWGMVML | | 13677 |
| HPV31 | E1 | 469 | 10 | SLISFLQGCI | | 13678 |
| HPV31 | E1 | 469 | 11 | SLISFLQGCII | | 13679 |
| HPV31 | E1 | 294 | 8 | STAAALYW | | 13680 |
| HPV31 | E1 | 294 | 9 | STAAALYWY | | 13681 |
| HPV31 | E1 | 211 | 11 | STCTDWCVAAF | | 13682 |
| HPV31 | E1 | 616 | 11 | STFKCVSGQNI | | 13683 |
| HPV31 | E1 | 250 | 8 | SWGMVMLM | | 13684 |
| HPV31 | E1 | 250 | 9 | SWGMVMLML | | 13685 |
| HPV31 | E1 | 480 | 9 | SYANSKSHF | | 13686 |
| HPV31 | E1 | 480 | 10 | SYANSKSHFW | | 13687 |
| HPV31 | E1 | 480 | 11 | SYANSKSHFWL | | 13688 |
| HPV31 | E1 | 464 | 8 | SYFGMSLI | | 13689 |
| HPV31 | E1 | 464 | 10 | SYFGMSLISF | | 13690 |
| HPV31 | E1 | 464 | 11 | SYFGMSLISFL | | 13691 |
| HPV31 | E1 | 334 | 10 | TFDLSQMVQW | | 13692 |
| HPV31 | E1 | 617 | 10 | TFKCVSGQNI | | 13693 |
| HPV31 | E1 | 567 | 8 | TFPNPFPF | | 13694 |
| HPV31 | E1 | 269 | 9 | TIEKLLEKL | | 13695 |
| HPV31 | E1 | 269 | 10 | TIEKLLEKLL | | 13696 |
| HPV31 | E1 | 233 | 8 | TLLQPYCL | | 13697 |
| HPV31 | E1 | 233 | 9 | TLLQPYCLY | | 13698 |
| HPV31 | E1 | 333 | 8 | TTFDLSQM | | 13699 |
| HPV31 | E1 | 333 | 11 | TTFDLSQMVQW | | 13700 |
| HPV31 | E1 | 505 | 8 | TTPCWHYI | | 13701 |
| HPV31 | E1 | 505 | 11 | TTPCWHYIDNY | | 13702 |
| HPV31 | E1 | 226 | 9 | TVAEGFKTL | | 13703 |
| HPV31 | E1 | 226 | 10 | TVAEGFKTLL | | 13704 |
| HPV31 | E1 | 565 | 8 | VFTFPNPF | | 13705 |
| HPV31 | E1 | 565 | 10 | VFTFPNPFPF | | 13706 |
| HPV31 | E1 | 23 | 10 | VIDRQTGDNI | | 13707 |
| HPV31 | E1 | 84 | 11 | VLKRKYVGSPL | | 13708 |
| HPV31 | E1 | 177 | 11 | VLKTSNGKAAM | | 13709 |
| HPV31 | E1 | 325 | 11 | VLQHSFNDTTF | | 13710 |
| HPV31 | E1 | 349 | 9 | VMDDSEIAY | | 13711 |
| HPV31 | E1 | 349 | 11 | VMDDSEIAYKY | | 13712 |
| HPV31 | E1 | 254 | 8 | VMLMLVRF | | 13713 |
| HPV31 | E1 | 223 | 9 | VTGTVAEGF | | 13714 |
| HPV31 | E1 | 564 | 9 | VVFTFPNPF | | 13715 |
| HPV31 | E1 | 564 | 11 | VVFTFPNPFPF | | 13716 |
| HPV31 | E1 | 581 | 9 | VYELSDKNW | | 13717 |
| HPV31 | E1 | 312 | 8 | VYGETPEW | | 13718 |
| HPV31 | E1 | 312 | 9 | VYGETPEWI | | 13719 |
| HPV31 | E1 | 17 | 8 | WFYVEAVI | | 13720 |
| HPV31 | E1 | 319 | 8 | WIERQTVL | | 13721 |
| HPV31 | E1 | 489 | 10 | WLQPLADAKI | | 13722 |
| HPV31 | E1 | 301 | 9 | WYRTGMSNI | | 13723 |
| HPV31 | E1 | 465 | 9 | YFGMSLISF | | 13724 |
| HPV31 | E1 | 465 | 10 | YFGMSLISFL | | 13725 |
| HPV31 | E1 | 511 | 10 | YIDNYLRNAL | | 13726 |
| HPV31 | E1 | 558 | 9 | YLHSRLVVF | | 13727 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | E1 | 558 | 11 | YLHSRLVVFTF | | 13728 |
| HPV31 | E1 | 89 | 9 | YVGSPLSDI | | 13729 |
| HPV31 | E1 | 300 | 10 | YWYRTGMSNI | | 13730 |
| HPV31 | E2 | 72 | 8 | AIELQMML | | 13731 |
| HPV31 | E2 | 72 | 11 | AIELQMMLETL | | 13732 |
| HPV31 | E2 | 338 | 8 | AIVTLTYI | | 13733 |
| HPV31 | E2 | 69 | 9 | ALQAIELQM | | 13734 |
| HPV31 | E2 | 69 | 10 | ALQAIELQMM | | 13735 |
| HPV31 | E2 | 69 | 11 | ALQAIELQMML | | 13736 |
| HPV31 | E2 | 61 | 10 | ALSVSKAKAL | | 13737 |
| HPV31 | E2 | 291 | 8 | ATTPIIHL | | 13738 |
| HPV31 | E2 | 286 | 10 | AVSCPATTPI | | 13739 |
| HPV31 | E2 | 286 | 11 | AVSCPATTPII | | 13740 |
| HPV31 | E2 | 307 | 9 | CLRYRLSKY | | 13741 |
| HPV31 | E2 | 330 | 10 | CTDGKHKNAI | | 13742 |
| HPV31 | E2 | 40 | 10 | CVLMYKAREM | | 13743 |
| HPV31 | E2 | 352 | 8 | DFLNTVKI | | 13744 |
| HPV31 | E2 | 124 | 8 | DVHNTMHY | | 13745 |
| HPV31 | E2 | 124 | 11 | DVHNTMHYTNW | | 13746 |
| HPV31 | E2 | 91 | 9 | DWTMQQTSL | | 13747 |
| HPV31 | E2 | 91 | 11 | DWTMQQTSLEL | | 13748 |
| HPV31 | E2 | 31 | 8 | DYWKHIRL | | 13749 |
| HPV31 | E2 | 204 | 11 | EISFAGIVTKL | | 13750 |
| HPV31 | E2 | 74 | 9 | ELQMMLETL | | 13751 |
| HPV31 | E2 | 100 | 11 | ELYLTAPTGCL | | 13752 |
| HPV31 | E2 | 80 | 8 | ETLNNTEY | | 13753 |
| HPV31 | E2 | 185 | 9 | EVHAGGQVI | | 13754 |
| HPV31 | E2 | 185 | 11 | EVHAGGQVIVF | | 13755 |
| HPV31 | E2 | 86 | 9 | EYKNEDWTM | | 13756 |
| HPV31 | E2 | 171 | 8 | FTEEAKKY | | 13757 |
| HPV31 | E2 | 168 | 11 | FVNFTEEAKKY | | 13758 |
| HPV31 | E2 | 156 | 10 | GIYYVHEGHI | | 13759 |
| HPV31 | E2 | 114 | 8 | GYTVEVQF | | 13760 |
| HPV31 | E2 | 29 | 8 | HIDYWKHI | | 13761 |
| HPV31 | E2 | 29 | 10 | HIDYWKHIRL | | 13762 |
| HPV31 | E2 | 35 | 8 | HIRLECVL | | 13763 |
| HPV31 | E2 | 35 | 9 | HIRLECVLM | | 13764 |
| HPV31 | E2 | 35 | 10 | HIRLECVLMY | | 13765 |
| HPV31 | E2 | 164 | 8 | HITYFVNF | | 13766 |
| HPV31 | E2 | 297 | 8 | HLKGDANI | | 13767 |
| HPV31 | E2 | 297 | 9 | HLKGDANIL | | 13768 |
| HPV31 | E2 | 18 | 9 | HYENDSKRL | | 13769 |
| HPV31 | E2 | 130 | 8 | HYTNWKFI | | 13770 |
| HPV31 | E2 | 130 | 9 | HYTNWKFIY | | 13771 |
| HPV31 | E2 | 130 | 10 | HYTNWKFIYL | | 13772 |
| HPV31 | E2 | 295 | 10 | IIHLKGDANI | | 13773 |
| HPV31 | E2 | 295 | 11 | IIHLKGDANIL | | 13774 |
| HPV31 | E2 | 304 | 9 | ILKCLRYRL | | 13775 |
| HPV31 | E2 | 193 | 8 | IVFPESVF | | 13776 |
| HPV31 | E2 | 157 | 9 | IYYVHEGHI | | 13777 |
| HPV31 | E2 | 157 | 11 | IYYVHEGHITY | | 13778 |
| HPV31 | E2 | 183 | 11 | KWEVHAGGQVI | | 13779 |
| HPV31 | E2 | 177 | 8 | KYGTGKKW | | 13780 |
| HPV31 | E2 | 42 | 8 | LMYKAREM | | 13781 |
| HPV31 | E2 | 42 | 10 | LMYKAREMGI | | 13782 |
| HPV31 | E2 | 103 | 8 | LTAPTGCL | | 13783 |
| HPV31 | E2 | 318 | 9 | LYEQVSSTW | | 13784 |
| HPV31 | E2 | 318 | 11 | LYEQVSSTWHW | | 13785 |
| HPV31 | E2 | 101 | 10 | LYLTAPTGCL | | 13786 |
| HPV31 | E2 | 78 | 10 | MLETLNNTEY | | 13787 |
| HPV31 | E2 | 77 | 11 | MMLETLNNTEY | | 13788 |
| HPV31 | E2 | 43 | 9 | MYKAREMGI | | 13789 |
| HPV31 | E2 | 170 | 9 | NFTEEAKKY | | 13790 |
| HPV31 | E2 | 303 | 8 | NILKCLRY | | 13791 |
| HPV31 | E2 | 303 | 10 | NILKCLRYRL | | 13792 |
| HPV31 | E2 | 84 | 9 | NTEYKNEDW | | 13793 |
| HPV31 | E2 | 84 | 11 | NTEYKNEDWTM | | 13794 |
| HPV31 | E2 | 254 | 8 | NTHHPNKL | | 13795 |
| HPV31 | E2 | 254 | 9 | NTHHPNKLL | | 13796 |
| HPV31 | E2 | 127 | 8 | NTMHYTNW | | 13797 |
| HPV31 | E2 | 127 | 10 | NTMHYTNWKF | | 13798 |
| HPV31 | E2 | 127 | 11 | NTMHYTNWKFI | | 13799 |
| HPV31 | E2 | 361 | 9 | NTVSVSTGY | | 13800 |
| HPV31 | E2 | 361 | 10 | NTVSVSTGYM | | 13801 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | E2 | 9 | 8 | NVCQDKIL | | 13802 |
| HPV31 | E2 | 9 | 11 | NVCQDKILEHY | | 13803 |
| HPV31 | E2 | 133 | 9 | NWKFIYLCI | | 13804 |
| HPV31 | E2 | 294 | 11 | PIIHLKGDANI | | 13805 |
| HPV31 | E2 | 106 | 10 | PTGCLKKHGY | | 13806 |
| HPV31 | E2 | 120 | 10 | QFDGDVHNTM | | 13807 |
| HPV31 | E2 | 317 | 10 | QLYEQVSSTW | | 13808 |
| HPV31 | E2 | 96 | 8 | QTSLELYL | | 13809 |
| HPV31 | E2 | 191 | 10 | QVIVFPESVF | | 13810 |
| HPV31 | E2 | 151 | 8 | QVNCKGIY | | 13811 |
| HPV31 | E2 | 151 | 9 | QVNCKGIYY | | 13812 |
| HPV31 | E2 | 321 | 8 | QVSSTWHW | | 13813 |
| HPV31 | E2 | 25 | 8 | RLCDHIDY | | 13814 |
| HPV31 | E2 | 25 | 9 | RLCDHIDYW | | 13815 |
| HPV31 | E2 | 37 | 8 | RLECVLMY | | 13816 |
| HPV31 | E2 | 7 | 9 | RLNVCQDKI | | 13817 |
| HPV31 | E2 | 7 | 10 | RLNVCQDKIL | | 13818 |
| HPV31 | E2 | 311 | 8 | RLSKYKQL | | 13819 |
| HPV31 | E2 | 311 | 9 | RLSKYKQLY | | 13820 |
| HPV31 | E2 | 309 | 10 | RYRLSKYKQL | | 13821 |
| HPV31 | E2 | 309 | 11 | RYRLSKYKQLY | | 13822 |
| HPV31 | E2 | 206 | 9 | SFAGIVTKL | | 13823 |
| HPV31 | E2 | 53 | 10 | SINHQVVPAL | | 13824 |
| HPV31 | E2 | 346 | 8 | STSQRDDF | | 13825 |
| HPV31 | E2 | 346 | 9 | STSQRDDFL | | 13826 |
| HPV31 | E2 | 266 | 10 | SVDSVNCGVI | | 13827 |
| HPV31 | E2 | 198 | 8 | SVFSSDEI | | 13828 |
| HPV31 | E2 | 198 | 10 | SVFSSDEISF | | 13829 |
| HPV31 | E2 | 63 | 8 | SVSKAKAL | | 13830 |
| HPV31 | E2 | 63 | 11 | SVSKAKALQAI | | 13831 |
| HPV31 | E2 | 364 | 9 | SVSTGYMTI | | 13832 |
| HPV31 | E2 | 128 | 9 | TMHYTNWKF | | 13833 |
| HPV31 | E2 | 128 | 10 | TMHYTNWKFI | | 13834 |
| HPV31 | E2 | 128 | 11 | TMHYTNWKFIY | | 13835 |
| HPV31 | E2 | 93 | 9 | TMQQTSLEL | | 13836 |
| HPV31 | E2 | 93 | 10 | TMQQTSLELY | | 13837 |
| HPV31 | E2 | 93 | 11 | TMQQTSLELYL | | 13838 |
| HPV31 | E2 | 221 | 10 | TTSNSKTCAL | | 13839 |
| HPV31 | E2 | 220 | 11 | TTTSNSKTCAL | | 13840 |
| HPV31 | E2 | 362 | 8 | TVSVSTGY | | 13841 |
| HPV31 | E2 | 362 | 9 | TVSVSTGYM | | 13842 |
| HPV31 | E2 | 362 | 11 | TVSVSTGYMTI | | 13843 |
| HPV31 | E2 | 343 | 11 | TYISTSQRDDF | | 13844 |
| HPV31 | E2 | 199 | 9 | VFSSDEISF | | 13845 |
| HPV31 | E2 | 192 | 9 | VIVFPESVF | | 13846 |
| HPV31 | E2 | 41 | 9 | VLMYKAREM | | 13847 |
| HPV31 | E2 | 41 | 11 | VLMYKAREMGI | | 13848 |
| HPV31 | E2 | 147 | 11 | VVEGQVNCKGI | | 13849 |
| HPV31 | E2 | 92 | 8 | WTMQQTSL | | 13850 |
| HPV31 | E2 | 92 | 10 | WTMQQTSLEL | | 13851 |
| HPV31 | E2 | 92 | 11 | WTMQQTSLELY | | 13852 |
| HPV31 | E2 | 344 | 10 | YISTSQRDDF | | 13853 |
| HPV31 | E2 | 344 | 11 | YISTSQRDDFL | | 13854 |
| HPV31 | E2 | 102 | 9 | YLTAPTGCL | | 13855 |
| HPV31 | E2 | 131 | 8 | YTNWKFIY | | 13856 |
| HPV31 | E2 | 131 | 9 | YTNWKFIYL | | 13857 |
| HPV31 | E2 | 131 | 11 | YTNWKFIYLCI | | 13858 |
| HPV31 | E2 | 159 | 9 | YVHEGHITY | | 13859 |
| HPV31 | E2 | 159 | 10 | YVHEGHITYF | | 13860 |
| HPV31 | E2 | 32 | 11 | YWKHIRLECVL | | 13861 |
| HPV31 | E2 | 158 | 8 | YYVHEGHI | | 13862 |
| HPV31 | E2 | 158 | 10 | YYVHEGHITY | | 13863 |
| HPV31 | E2 | 158 | 11 | YYVHEGHITYF | | 13864 |
| HPV31 | E5 | 40 | 9 | ATLLLLIVI | | 13865 |
| HPV31 | E5 | 40 | 10 | ATLLLLIVIL | | 13866 |
| HPV31 | E5 | 40 | 11 | ATLLLLIVILW | | 13867 |
| HPV31 | E5 | 53 | 8 | ATSPLRCF | | 13868 |
| HPV31 | E5 | 53 | 10 | ATSPLRCFCI | | 13869 |
| HPV31 | E5 | 53 | 11 | ATSPLRCFCIY | | 13870 |
| HPV31 | E5 | 59 | 8 | CFCIYVVF | | 13871 |
| HPV31 | E5 | 59 | 9 | CFCIYVVFI | | 13872 |
| HPV31 | E5 | 59 | 10 | CFCIYVVFIY | | 13873 |
| HPV31 | E5 | 59 | 11 | CFCIYVVFIYI | | 13874 |
| HPV31 | E5 | 18 | 10 | CFCVLLFVCL | | 13875 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | E5 | 14 | 9 | CFLLCFCVL | | 13876 |
| HPV31 | E5 | 14 | 10 | CFLLCFCVLL | | 13877 |
| HPV31 | E5 | 14 | 11 | CFLLCFCVLLF | | 13878 |
| HPV31 | E5 | 61 | 8 | CIYVVFIY | | 13879 |
| HPV31 | E5 | 61 | 9 | CIYVVFIYI | | 13880 |
| HPV31 | E5 | 61 | 11 | CIYVVFIYIPL | | 13881 |
| HPV31 | E5 | 26 | 9 | CLVIRPLVL | | 13882 |
| HPV31 | E5 | 20 | 8 | CVLLFVCL | | 13883 |
| HPV31 | E5 | 20 | 10 | CVLLFVCLVI | | 13884 |
| HPV31 | E5 | 3 | 9 | ELNISTVSI | | 13885 |
| HPV31 | E5 | 3 | 11 | ELNISTVSIVL | | 13886 |
| HPV31 | E5 | 66 | 9 | FIYIPLFVI | | 13887 |
| HPV31 | E5 | 15 | 8 | FLLCFCVL | | 13888 |
| HPV31 | E5 | 15 | 9 | FLLCFCVLL | | 13889 |
| HPV31 | E5 | 15 | 10 | FLLCFCVLLF | | 13890 |
| HPV31 | E5 | 24 | 9 | FVCLVIRPL | | 13891 |
| HPV31 | E5 | 24 | 11 | FVCLVIRPLVL | | 13892 |
| HPV31 | E5 | 72 | 9 | FVIHTHASF | | 13893 |
| HPV31 | E5 | 72 | 10 | FVIHTHASFL | | 13894 |
| HPV31 | E5 | 48 | 10 | ILWVIATSPL | | 13895 |
| HPV31 | E5 | 11 | 9 | IVLCFLLCF | | 13896 |
| HPV31 | E5 | 67 | 8 | IYIPLFVI | | 13897 |
| HPV31 | E5 | 62 | 8 | IYVVFIYI | | 13898 |
| HPV31 | E5 | 62 | 10 | IYVVFIYIPL | | 13899 |
| HPV31 | E5 | 62 | 11 | IYVVFIYIPLF | | 13900 |
| HPV31 | E5 | 23 | 10 | LFVCLVIRPL | | 13901 |
| HPV31 | E5 | 71 | 10 | LFVIHTHASF | | 13902 |
| HPV31 | E5 | 71 | 11 | LFVIHTHASFL | | 13903 |
| HPV31 | E5 | 45 | 8 | LIVILWVI | | 13904 |
| HPV31 | E5 | 16 | 8 | LLCFCVLL | | 13905 |
| HPV31 | E5 | 16 | 9 | LLCFCVLLF | | 13906 |
| HPV31 | E5 | 22 | 8 | LLFVCLVI | | 13907 |
| HPV31 | E5 | 22 | 11 | LLFVCLVIRPL | | 13908 |
| HPV31 | E5 | 44 | 9 | LLIVILWVI | | 13909 |
| HPV31 | E5 | 43 | 8 | LLLIVILW | | 13910 |
| HPV31 | E5 | 43 | 10 | LLLIVILWVI | | 13911 |
| HPV31 | E5 | 42 | 8 | LLLLIVIL | | 13912 |
| HPV31 | E5 | 42 | 9 | LLLLIVILW | | 13913 |
| HPV31 | E5 | 42 | 11 | LLLLIVILWVI | | 13914 |
| HPV31 | E5 | 27 | 8 | LVIRPLVL | | 13915 |
| HPV31 | E5 | 32 | 8 | LVLSVSVY | | 13916 |
| HPV31 | E5 | 32 | 11 | LVLSVSVYATL | | 13917 |
| HPV31 | E5 | 49 | 9 | LWVIATSPL | | 13918 |
| HPV31 | E5 | 1 | 11 | MIELNISTVSI | | 13919 |
| HPV31 | E5 | 5 | 9 | NISTVSIVL | | 13920 |
| HPV31 | E5 | 5 | 11 | NISTVSIVLCF | | 13921 |
| HPV31 | E5 | 70 | 11 | PLFVIHTHASF | | 13922 |
| HPV31 | E5 | 56 | 8 | PLRCFCIY | | 13923 |
| HPV31 | E5 | 56 | 11 | PLRCFCIYVVF | | 13924 |
| HPV31 | E5 | 31 | 9 | PLVLSVSVY | | 13925 |
| HPV31 | E5 | 10 | 8 | SIVLCFLL | | 13926 |
| HPV31 | E5 | 10 | 10 | SIVLCFLLCF | | 13927 |
| HPV31 | E5 | 7 | 9 | STVSIVLCF | | 13928 |
| HPV31 | E5 | 7 | 10 | STVSIVLCFL | | 13929 |
| HPV31 | E5 | 7 | 11 | STVSIVLCFLL | | 13930 |
| HPV31 | E5 | 35 | 8 | SVSVYATL | | 13931 |
| HPV31 | E5 | 35 | 9 | SVSVYATLL | | 13932 |
| HPV31 | E5 | 35 | 10 | SVSVYATLLL | | 13933 |
| HPV31 | E5 | 35 | 11 | SVSVYATLLLL | | 13934 |
| HPV31 | E5 | 37 | 8 | SVYATLLL | | 13935 |
| HPV31 | E5 | 37 | 9 | SVYATLLLL | | 13936 |
| HPV31 | E5 | 37 | 10 | SVYATLLLLI | | 13937 |
| HPV31 | E5 | 41 | 8 | TLLLLIVI | | 13938 |
| HPV31 | E5 | 41 | 9 | TLLLLIVIL | | 13939 |
| HPV31 | E5 | 41 | 10 | TLLLLIVILW | | 13940 |
| HPV31 | E5 | 8 | 8 | TVSIVLCF | | 13941 |
| HPV31 | E5 | 8 | 9 | TVSIVLCFL | | 13942 |
| HPV31 | E5 | 8 | 10 | TVSIVLCFLL | | 13943 |
| HPV31 | E5 | 65 | 8 | VFIYIPLF | | 13944 |
| HPV31 | E5 | 65 | 10 | VFIYIPLFVI | | 13945 |
| HPV31 | E5 | 51 | 10 | VIATSPLRCF | | 13946 |
| HPV31 | E5 | 73 | 8 | VIHTHASF | | 13947 |
| HPV31 | E5 | 73 | 9 | VIHTHASFL | | 13948 |
| HPV31 | E5 | 47 | 11 | VILWVIATSPL | | 13949 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | E5 | 12 | 8 | VLCFLLCF | | 13950 |
| HPV31 | E5 | 12 | 11 | VLCFLLCFCVL | | 13951 |
| HPV31 | E5 | 21 | 9 | VLLFVCLVI | | 13952 |
| HPV31 | E5 | 33 | 10 | VLSVSVYATL | | 13953 |
| HPV31 | E5 | 33 | 11 | VLSVSVYATLL | | 13954 |
| HPV31 | E5 | 64 | 8 | VVFIYIPL | | 13955 |
| HPV31 | E5 | 64 | 9 | VVFIYIPLF | | 13956 |
| HPV31 | E5 | 64 | 11 | VVFIYIPLFVI | | 13957 |
| HPV31 | E5 | 38 | 8 | VYATLLLL | | 13958 |
| HPV31 | E5 | 38 | 9 | VYATLLLLI | | 13959 |
| HPV31 | E5 | 38 | 11 | VYATLLLLIVI | | 13960 |
| HPV31 | E5 | 50 | 8 | WVIATSPL | | 13961 |
| HPV31 | E5 | 50 | 11 | WVIATSPLRCF | | 13962 |
| HPV31 | E5 | 63 | 9 | YVVFIYIPL | | 13963 |
| HPV31 | E5 | 63 | 10 | YVVFIYIPLF | | 13964 |
| HPV31 | E6 | 46 | 9 | AFTDLTIVY | | 13965 |
| HPV31 | E6 | 18 | 9 | ALEIPYDEL | | 13966 |
| HPV31 | E6 | 18 | 11 | ALEIPYDELRL | | 13967 |
| HPV31 | E6 | 103 | 8 | CITCQRPL | | 13968 |
| HPV31 | E6 | 66 | 11 | CLRFYSKVSEF | | 13969 |
| HPV31 | E6 | 63 | 8 | CTKCLRFY | | 13970 |
| HPV31 | E6 | 30 | 8 | CVYCKGQL | | 13971 |
| HPV31 | E6 | 44 | 9 | DFAFTDLTI | | 13972 |
| HPV31 | E6 | 44 | 11 | DFAFTDLTIVY | | 13973 |
| HPV31 | E6 | 57 | 11 | DTPHGVCTKCL | | 13974 |
| HPV31 | E6 | 75 | 10 | EFRWYRYSVY | | 13975 |
| HPV31 | E6 | 20 | 9 | EIPYDELRL | | 13976 |
| HPV31 | E6 | 25 | 8 | ELRLNCVY | | 13977 |
| HPV31 | E6 | 14 | 8 | ELSSALEI | | 13978 |
| HPV31 | E6 | 14 | 10 | ELSSALEIPY | | 13979 |
| HPV31 | E6 | 39 | 9 | ETEVLDFAF | | 13980 |
| HPV31 | E6 | 41 | 10 | EVLDFAFTDL | | 13981 |
| HPV31 | E6 | 47 | 8 | FTDLTIVY | | 13982 |
| HPV31 | E6 | 69 | 8 | FYSKVSEF | | 13983 |
| HPV31 | E6 | 69 | 10 | FYSKVSEFRW | | 13984 |
| HPV31 | E6 | 69 | 11 | FYSKVSEFRWY | | 13985 |
| HPV31 | E6 | 95 | 10 | GICDLLIRCI | | 13986 |
| HPV31 | E6 | 61 | 9 | GVCTKCLRF | | 13987 |
| HPV31 | E6 | 61 | 10 | GVCTKCLRFY | | 13988 |
| HPV31 | E6 | 118 | 8 | HLDKKKRF | | 13989 |
| HPV31 | E6 | 118 | 11 | HLDKKKRFHNI | | 13990 |
| HPV31 | E6 | 11 | 9 | KLHELSSAL | | 13991 |
| HPV31 | E6 | 11 | 11 | KLHELSSALEI | | 13992 |
| HPV31 | E6 | 90 | 10 | KLTNKGICDL | | 13993 |
| HPV31 | E6 | 90 | 11 | KLTNKGICDLL | | 13994 |
| HPV31 | E6 | 72 | 8 | KVSEFRWY | | 13995 |
| HPV31 | E6 | 72 | 10 | KVSEFRWYRY | | 13996 |
| HPV31 | E6 | 100 | 11 | LIRCITCQRPL | | 13997 |
| HPV31 | E6 | 37 | 9 | LTETEVLDF | | 13998 |
| HPV31 | E6 | 37 | 11 | LTETEVLDFAF | | 13999 |
| HPV31 | E6 | 91 | 9 | LTNKGICDL | | 14000 |
| HPV31 | E6 | 91 | 10 | LTNKGICDLL | | 14001 |
| HPV31 | E6 | 91 | 11 | LTNKGICDLLI | | 14002 |
| HPV31 | E6 | 127 | 11 | NIGGRWTGRCI | | 14003 |
| HPV31 | E6 | 109 | 11 | PLCPEEKQRHL | | 14004 |
| HPV31 | E6 | 22 | 11 | PYDELRLNCVY | | 14005 |
| HPV31 | E6 | 36 | 8 | QLTETEVL | | 14006 |
| HPV31 | E6 | 36 | 10 | QLTETEVLDF | | 14007 |
| HPV31 | E6 | 124 | 9 | RFHNIGGRW | | 14008 |
| HPV31 | E6 | 68 | 9 | RFYSKVSEF | | 14009 |
| HPV31 | E6 | 68 | 11 | RFYSKVSEFRW | | 14010 |
| HPV31 | E6 | 27 | 11 | RLNCVYCKGQL | | 14011 |
| HPV31 | E6 | 131 | 10 | RWTGRCIACW | | 14012 |
| HPV31 | E6 | 77 | 8 | RWYRYSVY | | 14013 |
| HPV31 | E6 | 80 | 9 | RYSVYGTTL | | 14014 |
| HPV31 | E6 | 82 | 10 | SVYGTTLEKL | | 14015 |
| HPV31 | E6 | 87 | 10 | TLEKLTNKGI | | 14016 |
| HPV31 | E6 | 86 | 11 | TTLEKLTNKGI | | 14017 |
| HPV31 | E6 | 42 | 9 | VLDFAFTDL | | 14018 |
| HPV31 | E6 | 42 | 11 | VLDFAFTDLTI | | 14019 |
| HPV31 | E6 | 83 | 9 | VYGTTLEKL | | 14020 |
| HPV31 | E6 | 132 | 9 | WTGRCIACW | | 14021 |
| HPV31 | E6 | 78 | 11 | WYRYSVYGTTL | | 14022 |
| HPV31 | E7 | 19 | 10 | ATDLHCYEQL | | 14023 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | E7 | 68 | 9 | CVQSTQVDI | | 14024 |
| HPV31 | E7 | 68 | 11 | CVQSTQVDIRI | | 14025 |
| HPV31 | E7 | 75 | 8 | DIRILQEL | | 14026 |
| HPV31 | E7 | 75 | 9 | DIRILQELL | | 14027 |
| HPV31 | E7 | 75 | 10 | DIRILQELLM | | 14028 |
| HPV31 | E7 | 21 | 8 | DLHCYEQL | | 14029 |
| HPV31 | E7 | 14 | 9 | DLQPEATDL | | 14030 |
| HPV31 | E7 | 48 | 10 | DTSNYNIVTF | | 14031 |
| HPV31 | E7 | 81 | 9 | ELLMGSFGI | | 14032 |
| HPV31 | E7 | 4 | 8 | ETPTLQDY | | 14033 |
| HPV31 | E7 | 4 | 10 | ETPTLQDYVL | | 14034 |
| HPV31 | E7 | 88 | 11 | GIVCPNCSTRL | | 14035 |
| HPV31 | E7 | 78 | 10 | ILQELLMGSF | | 14036 |
| HPV31 | E7 | 89 | 10 | IVCPNCSTRL | | 14037 |
| HPV31 | E7 | 82 | 8 | LLMGSFGI | | 14038 |
| HPV31 | E7 | 6 | 8 | PTLQDYVL | | 14039 |
| HPV31 | E7 | 6 | 10 | PTLQDYVLDL | | 14040 |
| HPV31 | E7 | 73 | 10 | QVDIRILQEL | | 14041 |
| HPV31 | E7 | 73 | 11 | QVDIRILQELL | | 14042 |
| HPV31 | E7 | 77 | 8 | RILQELLM | | 14043 |
| HPV31 | E7 | 77 | 11 | RILQELLMGSF | | 14044 |
| HPV31 | E7 | 66 | 11 | RLCVQSTQVDI | | 14045 |
| HPV31 | E7 | 71 | 8 | STQVDIRI | | 14046 |
| HPV31 | E7 | 71 | 9 | STQVDIRIL | | 14047 |
| HPV31 | E7 | 56 | 10 | TFCCQCKSTL | | 14048 |
| HPV31 | E7 | 7 | 9 | TLQDYVLDL | | 14049 |
| HPV31 | E7 | 12 | 11 | VLDLQPEATDL | | 14050 |
| HPV31 | E7 | 55 | 11 | VTFCCQCKSTL | | 14051 |
| HPV31 | L1 | 348 | 9 | AIANSDTTF | | 14052 |
| HPV31 | L1 | 398 | 8 | AILEDWNF | | 14053 |
| HPV31 | L1 | 398 | 10 | AILEDWNFGL | | 14054 |
| HPV31 | L1 | 180 | 10 | AITPGDCPPL | | 14055 |
| HPV31 | L1 | 213 | 11 | ALQDTKSNVPL | | 14056 |
| HPV31 | L1 | 285 | 8 | ATLANSTY | | 14057 |
| HPV31 | L1 | 285 | 9 | ATLANSTYF | | 14058 |
| HPV31 | L1 | 147 | 11 | CISMDYKQTQL | | 14059 |
| HPV31 | L1 | 158 | 9 | CLLGCKPPI | | 14060 |
| HPV31 | L1 | 224 | 9 | DICNSICKY | | 14061 |
| HPV31 | L1 | 387 | 9 | DIMTYIHSM | | 14062 |
| HPV31 | L1 | 459 | 11 | DLDQFPLGRKF | | 14063 |
| HPV31 | L1 | 372 | 8 | DLQFIFQL | | 14064 |
| HPV31 | L1 | 372 | 11 | DLQFIFQLCKI | | 14065 |
| HPV31 | L1 | 200 | 10 | DMVDTGFGAM | | 14066 |
| HPV31 | L1 | 129 | 8 | DTENSNRY | | 14067 |
| HPV31 | L1 | 203 | 9 | DTGFGAMDF | | 14068 |
| HPV31 | L1 | 216 | 8 | DTKSNVPL | | 14069 |
| HPV31 | L1 | 216 | 10 | DTKSNVPLDI | | 14070 |
| HPV31 | L1 | 353 | 9 | DTTFKSSNF | | 14071 |
| HPV31 | L1 | 336 | 8 | DTTRSTNM | | 14072 |
| HPV31 | L1 | 417 | 11 | DTYRFVTSQAI | | 14073 |
| HPV31 | L1 | 151 | 9 | DYKQTQLCL | | 14074 |
| HPV31 | L1 | 151 | 10 | DYKQTQLCLL | | 14075 |
| HPV31 | L1 | 234 | 10 | DYLKMVAEPY | | 14076 |
| HPV31 | L1 | 444 | 9 | DYVFWEVNL | | 14077 |
| HPV31 | L1 | 370 | 8 | EFDLQFIF | | 14078 |
| HPV31 | L1 | 370 | 10 | EFDLQFIFQL | | 14079 |
| HPV31 | L1 | 107 | 8 | EVGRGQPL | | 14080 |
| HPV31 | L1 | 449 | 8 | EVNLKEKF | | 14081 |
| HPV31 | L1 | 363 | 9 | EYLRHGEEF | | 14082 |
| HPV31 | L1 | 363 | 11 | EYLRHGEEFDL | | 14083 |
| HPV31 | L1 | 26 | 8 | EYVTRTNI | | 14084 |
| HPV31 | L1 | 26 | 9 | EYVTRTNIY | | 14085 |
| HPV31 | L1 | 26 | 10 | EYVTRTNIYY | | 14086 |
| HPV31 | L1 | 248 | 9 | FFYLRREQM | | 14087 |
| HPV31 | L1 | 248 | 10 | FFYLRREQMF | | 14088 |
| HPV31 | L1 | 375 | 8 | FIFQLCKI | | 14089 |
| HPV31 | L1 | 375 | 10 | FIFQLCKITL | | 14090 |
| HPV31 | L1 | 447 | 10 | FWEVNLKEKF | | 14091 |
| HPV31 | L1 | 249 | 8 | FYLRREQM | | 14092 |
| HPV31 | L1 | 249 | 9 | FYLRREQMF | | 14093 |
| HPV31 | L1 | 91 | 9 | FYNPETQRL | | 14094 |
| HPV31 | L1 | 91 | 11 | FYNPETQRLVW | | 14095 |
| HPV31 | L1 | 205 | 10 | GFGAMDFTAL | | 14096 |
| HPV31 | L1 | 85 | 8 | GFPDTSFY | | 14097 |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | L1 | 323 | 8 | GICWGNQL | | 14098 |
| HPV31 | L1 | 323 | 9 | GICWGNQLF | | 14099 |
| HPV31 | L1 | 117 | 8 | GISGHPLL | | 14100 |
| HPV31 | L1 | 117 | 11 | GISGHPLLNKF | | 14101 |
| HPV31 | L1 | 105 | 10 | GLEVGRGQPL | | 14102 |
| HPV31 | L1 | 68 | 11 | GLQYRVFRVRL | | 14103 |
| HPV31 | L1 | 406 | 10 | GLTTPPSGSL | | 14104 |
| HPV31 | L1 | 141 | 8 | GTDNRECI | | 14105 |
| HPV31 | L1 | 141 | 10 | GTDNRECISM | | 14106 |
| HPV31 | L1 | 266 | 11 | GTVGESVPTDL | | 14107 |
| HPV31 | L1 | 115 | 9 | GVGISGHPL | | 14108 |
| HPV31 | L1 | 115 | 10 | GVGISGHPLL | | 14109 |
| HPV31 | L1 | 474 | 8 | GYRARPKF | | 14110 |
| HPV31 | L1 | 307 | 8 | IFNKPYWM | | 14111 |
| HPV31 | L1 | 376 | 9 | IFQLCKITL | | 14112 |
| HPV31 | L1 | 399 | 9 | ILEDWNFGL | | 14113 |
| HPV31 | L1 | 388 | 8 | IMTYIHSM | | 14114 |
| HPV31 | L1 | 382 | 8 | ITLSADIM | | 14115 |
| HPV31 | L1 | 382 | 10 | ITLSADIMTY | | 14116 |
| HPV31 | L1 | 382 | 11 | ITLSADIMTYI | | 14117 |
| HPV31 | L1 | 181 | 9 | ITPGDCPPL | | 14118 |
| HPV31 | L1 | 181 | 11 | ITPGDCPPLEL | | 14119 |
| HPV31 | L1 | 61 | 9 | IVVPKVSGL | | 14120 |
| HPV31 | L1 | 61 | 11 | IVVPKVSGLQY | | 14121 |
| HPV31 | L1 | 33 | 10 | IYYHAGSARL | | 14122 |
| HPV31 | L1 | 33 | 11 | IYYHAGSARLL | | 14123 |
| HPV31 | L1 | 126 | 11 | KFDDTENSNRY | | 14124 |
| HPV31 | L1 | 83 | 9 | KFGFPDTSF | | 14125 |
| HPV31 | L1 | 83 | 10 | KFGFPDTSFY | 14126 | |
| HPV31 | L1 | 468 | 8 | KFLLQAGY | 14127 | |
| HPV31 | L1 | 455 | 9 | KFSADLDQF | 14128 | |
| HPV31 | L1 | 455 | 11 | KFSADLDQFPL | 14129 | |
| HPV31 | L1 | 381 | 8 | KITLSADI | 14130 | |
| HPV31 | L1 | 381 | 9 | KITLSADIM | 14131 | |
| HPV31 | L1 | 381 | 11 | KITLSADIMTY | 14132 | |
| HPV31 | L1 | 60 | 10 | KIVVPKVSGL | 14133 | |
| HPV31 | L1 | 237 | 11 | KMVAEPYGDTL | 14134 | |
| HPV31 | L1 | 65 | 10 | KVSGLQYRVF | 14135 | |
| HPV31 | L1 | 20 | 8 | KVVSTDEY | 14136 | |
| HPV31 | L1 | 231 | 8 | KYPDYLKM | 14137 | |
| HPV31 | L1 | 247 | 10 | LFFYLRREQM | 14138 | |
| HPV31 | L1 | 247 | 11 | LFFYLRREQMF | 14139 | |
| HPV31 | L1 | 159 | 8 | LLGCKPPI | 14140 | |
| HPV31 | L1 | 42 | 8 | LLTVGHPY | 14141 | |
| HPV31 | L1 | 42 | 9 | LLTVGHPYY | 14142 | |
| HPV31 | L1 | 42 | 11 | LLTVGHPYYSI | 14143 | |
| HPV31 | L1 | 407 | 9 | LTTPPSGSL | 14144 | |
| HPV31 | L1 | 43 | 8 | LTVGHPYY | 14145 | |
| HPV31 | L1 | 43 | 10 | LTVGHPYYSI | 14146 | |
| HPV31 | L1 | 99 | 8 | LVWACVGL | 14147 | |
| HPV31 | L1 | 3 | 10 | LWRPSEATVY | 14148 | |
| HPV31 | L1 | 3 | 11 | LWRPSEATVYL | 14149 | |
| HPV31 | L1 | 389 | 11 | MTYIHSMNPAI | 14150 | |
| HPV31 | L1 | 238 | 10 | MVAEPYGDTL | 14151 | |
| HPV31 | L1 | 238 | 11 | MVAEPYGDTLF | 14152 | |
| HPV31 | L1 | 201 | 9 | MVDTGFGAM | 14153 | |
| HPV31 | L1 | 201 | 11 | MVDTGFGAMDF | 14154 | |
| HPV31 | L1 | 300 | 8 | MVTSDAQI | 14155 | |
| HPV31 | L1 | 300 | 9 | MVTSDAQIF | 14156 | |
| HPV31 | L1 | 32 | 11 | NIYYHAGSARL | 14157 | |
| HPV31 | L1 | 451 | 10 | NLKEKFSADL | 14158 | |
| HPV31 | L1 | 342 | 8 | NMSVCAAI | 14159 | |
| HPV31 | L1 | 220 | 10 | NVPLDICNSI | 14160 | |
| HPV31 | L1 | 441 | 8 | PFKDYVFW | 14161 | |
| HPV31 | L1 | 222 | 8 | PLDICNSI | 14162 | |
| HPV31 | L1 | 222 | 11 | PLDICNSICKY | 14163 | |
| HPV31 | L1 | 188 | 9 | PLELKNSVI | 14164 | |
| HPV31 | L1 | 464 | 8 | PLGRKFLL | 14165 | |
| HPV31 | L1 | 113 | 11 | PLGVGISGHPL | 14166 | |
| HPV31 | L1 | 17 | 11 | PVSKVVSTDEY | 14167 | |
| HPV31 | L1 | 242 | 8 | PYGDTLFF | 14168 | |
| HPV31 | L1 | 242 | 9 | PYGDTLFFY | 14169 | |
| HPV31 | L1 | 242 | 10 | PYGDTLFFYL | 14170 | |
| HPV31 | L1 | 374 | 9 | QFIFQLCKI | 14171 | |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | L1 | 374 | 11 | QFIFQLCKITL | 14172 | |
| HPV31 | L1 | 462 | 8 | QFPLGRKF | 14173 | |
| HPV31 | L1 | 462 | 9 | QFPLGRKFL | 14174 | |
| HPV31 | L1 | 462 | 10 | QFPLGRKFLL | 14175 | |
| HPV31 | L1 | 306 | 8 | QIFNKPYW | 14176 | |
| HPV31 | L1 | 306 | 9 | QIFNKPYWM | 14177 | |
| HPV31 | L1 | 378 | 11 | QLCKITLSADI | 14178 | |
| HPV31 | L1 | 156 | 11 | QLCLLGCKPPI | 14179 | |
| HPV31 | L1 | 255 | 8 | QMFVRHFF | 14180 | |
| HPV31 | L1 | 70 | 9 | QYRVFRVRL | 14181 | |
| HPV31 | L1 | 420 | 8 | RFVTSQAI | 14182 | |
| HPV31 | L1 | 41 | 9 | RLLTVGHPY | 14183 | |
| HPV31 | L1 | 41 | 10 | RLLTVGHPYY | 14184 | |
| HPV31 | L1 | 77 | 8 | RLPDPNKF | 14185 | |
| HPV31 | L1 | 77 | 10 | RLPDPNKFGF | 14186 | |
| HPV31 | L1 | 98 | 9 | RLVWACVGL | 14187 | |
| HPV31 | L1 | 75 | 10 | RVRLPDPNKF | 14188 | |
| HPV31 | L1 | 90 | 10 | SFYNPETQRL | 14189 | |
| HPV31 | L1 | 228 | 8 | SICKYPDY | 14190 | |
| HPV31 | L1 | 228 | 9 | SICKYPDYL | 14191 | |
| HPV31 | L1 | 228 | 11 | SICKYPDYLKM | 14192 | |
| HPV31 | L1 | 51 | 11 | SIPKSDNPKKI | 14193 | |
| HPV31 | L1 | 414 | 8 | SLEDTYRF | 14194 | |
| HPV31 | L1 | 2 | 11 | SLWRPSEATVY | 14195 | |
| HPV31 | L1 | 149 | 9 | SMDYKQTQL | 14196 | |
| HPV31 | L1 | 149 | 11 | SMDYKQTQLCL | 14197 | |
| HPV31 | L1 | 394 | 10 | SMNPAILEDW | 14198 | |
| HPV31 | L1 | 299 | 9 | SMVTSDAQI | 14199 | |
| HPV31 | L1 | 299 | 10 | SMVTSDAQIF | 14200 | |
| HPV31 | L1 | 283 | 10 | STATLANSTY | 14201 | |
| HPV31 | L1 | 283 | 11 | STATLANSTYF | 14202 | |
| HPV31 | L1 | 23 | 11 | STDEYVTRTNI | 14203 | |
| HPV31 | L1 | 340 | 10 | STNMSVCAAI | 14204 | |
| HPV31 | L1 | 290 | 11 | STYFPTPSGSM | 14205 | |
| HPV31 | L1 | 194 | 8 | SVIQDGDM | 14206 | |
| HPV31 | L1 | 271 | 8 | SVPTDLYI | 14207 | |
| HPV31 | L1 | 355 | 10 | TFKSSNFKEY | 14208 | |
| HPV31 | L1 | 355 | 11 | TFKSSNFKEYL | 14209 | |
| HPV31 | L1 | 286 | 8 | TLANSTYF | 14210 | |
| HPV31 | L1 | 246 | 11 | TLFFYLRREQM | 14211 | |
| HPV31 | L1 | 383 | 9 | TLSADIMTY | 14212 | |
| HPV31 | L1 | 383 | 10 | TLSADIMTYI | 14213 | |
| HPV31 | L1 | 354 | 8 | TTFKSSNF | 14214 | |
| HPV31 | L1 | 354 | 11 | TTFKSSNFKEY | 14215 | |
| HPV31 | L1 | 408 | 8 | TTPPSGSL | 14216 | |
| HPV31 | L1 | 267 | 10 | TVGESVPTDL | 14217 | |
| HPV31 | L1 | 267 | 11 | TVGESVPTDLY | 14218 | |
| HPV31 | L1 | 44 | 9 | TVGHPYYSI | 14219 | |
| HPV31 | L1 | 333 | 11 | TVVDTTRSTNM | 14220 | |
| HPV31 | L1 | 291 | 10 | TYFPTPSGSM | 14221 | |
| HPV31 | L1 | 390 | 10 | TYIHSMNPAI | 14222 | |
| HPV31 | L1 | 390 | 11 | TYIHSMNPAIL | 14223 | |
| HPV31 | L1 | 418 | 10 | TYRFVTSQAI | 14224 | |
| HPV31 | L1 | 446 | 11 | VFWEVNLKEKF | 14225 | |
| HPV31 | L1 | 28 | 8 | VTRTNIYY | 14226 | |
| HPV31 | L1 | 301 | 8 | VTSDAQIF | 14227 | |
| HPV31 | L1 | 334 | 10 | VVDTTRSTNM | 14228 | |
| HPV31 | L1 | 62 | 8 | VVPKVSGL | 14229 | |
| HPV31 | L1 | 62 | 10 | VVPKVSGLQY | 14230 | |
| HPV31 | L1 | 292 | 9 | YFPTPSGSM | 14231 | |
| HPV31 | L1 | 391 | 9 | YIHSMNPAI | 14232 | |
| HPV31 | L1 | 391 | 10 | YIHSMNPAIL | 14233 | |
| HPV31 | L1 | 277 | 11 | YIKGSGSTATL | 14234 | |
| HPV31 | L1 | 235 | 9 | YLKMVAEPY | 14235 | |
| HPV31 | L1 | 364 | 8 | YLRHGEEF | 14236 | |
| HPV31 | L1 | 364 | 10 | YLRHGEEFDL | 14237 | |
| HPV31 | L1 | 250 | 8 | YLRREQMF | 14238 | |
| HPV31 | L1 | 445 | 8 | YVFWEVNL | 14239 | |
| HPV31 | L1 | 27 | 8 | YVTRTNIY | 14240 | |
| HPV31 | L1 | 27 | 9 | YVTRTNIYY | 14241 | |
| HPV31 | L1 | 34 | 9 | YYHAGSARL | 14242 | |
| HPV31 | L1 | 34 | 10 | YYHAGSARLL | 14243 | |
| HPV31 | L2 | 286 | 11 | ALTSRRNTVRY | 14244 | |
| HPV31 | L2 | 311 | 9 | ATIGARVHY | 14245 | |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | L2 | 311 | 10 | ATIGARVHYY | 14246 | |
| HPV31 | L2 | 311 | 11 | ATIGARVHYYY | 14247 | |
| HPV31 | L2 | 226 | 8 | ATQQVKVI | 14248 | |
| HPV31 | L2 | 135 | 10 | ATTADTTPAI | 14249 | |
| HPV31 | L2 | 135 | 11 | ATTADTTPAIL | 14250 | |
| HPV31 | L2 | 342 | 11 | ATTTSTLNDGL | 14251 | |
| HPV31 | L2 | 376 | 11 | AVQSTSAVSAY | 14252 | |
| HPV31 | L2 | 251 | 11 | AYETVNAEESL | 14253 | |
| HPV31 | L2 | 385 | 11 | AYVPTNTTVPL | 14254 | |
| HPV31 | L2 | 275 | 8 | DFLDIIAL | 14255 | |
| HPV31 | L2 | 438 | 8 | DFYLHPSY | 14256 | |
| HPV31 | L2 | 438 | 9 | DFYLHPSYY | 14257 | |
| HPV31 | L2 | 438 | 10 | DFYLHPSYYM | 14258 | |
| HPV31 | L2 | 438 | 11 | DFYLHPSYYML | 14259 | |
| HPV31 | L2 | 278 | 10 | DIIALHRPAL | 14260 | |
| HPV31 | L2 | 354 | 8 | DIYADTDF | 14261 | |
| HPV31 | L2 | 116 | 8 | DVGAPAPI | 14262 | |
| HPV31 | L2 | 31 | 11 | DVIPKIEHTTI | 14263 | |
| HPV31 | L2 | 190 | 8 | EIPMDTFI | 14264 | |
| HPV31 | L2 | 171 | 8 | ETSGHLLL | 14265 | |
| HPV31 | L2 | 253 | 9 | ETVNAEESL | 14266 | |
| HPV31 | L2 | 253 | 10 | ETVNAEESLY | 14267 | |
| HPV31 | L2 | 253 | 11 | ETVNAEESLYF | 14268 | |
| HPV31 | L2 | 196 | 10 | FIVSTNNENI | 14269 | |
| HPV31 | L2 | 237 | 8 | FLSAPKQL | 14270 | |
| HPV31 | L2 | 237 | 9 | FLSAPKQLI | 14271 | |
| HPV31 | L2 | 237 | 11 | FLSAPKQLITY | 14272 | |
| HPV31 | L2 | 433 | 8 | FVDGGDFY | 14273 | |
| HPV31 | L2 | 433 | 9 | FVDGGDFYL | 14274 | |
| HPV31 | L2 | 439 | 8 | FYLHPSYY | 14275 | |
| HPV31 | L2 | 439 | 9 | FYLHPSYYM | 14276 | |
| HPV31 | L2 | 439 | 10 | FYLHPSYYML | 14277 | |
| HPV31 | L2 | 113 | 11 | GIVDVGAPAPI | 14278 | |
| HPV31 | L2 | 351 | 11 | GLYDIYADTDF | 14279 | |
| HPV31 | L2 | 26 | 8 | GTCPSDVI | 14280 | |
| HPV31 | L2 | 26 | 11 | GTCPSDVIPKI | 14281 | |
| HPV31 | L2 | 65 | 8 | GTGGRTGY | 14282 | |
| HPV31 | L2 | 65 | 11 | GTGGRTGYVPL | 14283 | |
| HPV31 | L2 | 52 | 9 | GVFFGGLGI | 14284 | |
| HPV31 | L2 | 213 | 8 | GVRRPARL | 14285 | |
| HPV31 | L2 | 213 | 10 | GVRRPARLGL | 14286 | |
| HPV31 | L2 | 213 | 11 | GVRRPARLGLY | 14287 | |
| HPV31 | L2 | 175 | 9 | HLLLSSSSI | 14288 | |
| HPV31 | L2 | 38 | 8 | HTTIADQI | 14289 | |
| HPV31 | L2 | 38 | 9 | HTTIADQIL | 14290 | |
| HPV31 | L2 | 38 | 11 | HTTIADQILRY | 14291 | |
| HPV31 | L2 | 318 | 9 | HYYYDISSI | 14292 | |
| HPV31 | L2 | 403 | 9 | IFSGPDVPI | 14293 | |
| HPV31 | L2 | 432 | 8 | IFVDGGDF | 14294 | |
| HPV31 | L2 | 432 | 9 | IFVDGGDFY | 14295 | |
| HPV31 | L2 | 432 | 10 | IFVDGGDFYL | 14296 | |
| HPV31 | L2 | 279 | 9 | IIALHRPAL | 14297 | |
| HPV31 | L2 | 45 | 10 | ILRYGSMGVF | 14298 | |
| HPV31 | L2 | 45 | 11 | ILRYGSMGVFF | 14299 | |
| HPV31 | L2 | 245 | 8 | ITYENPAY | 14300 | |
| HPV31 | L2 | 114 | 10 | IVDVGAPAPI | 14301 | |
| HPV31 | L2 | 105 | 10 | IVSLVEESGI | 14302 | |
| HPV31 | L2 | 197 | 9 | IVSTNNENI | 14303 | |
| HPV31 | L2 | 35 | 11 | KIEHTTIADQI | 14304 | |
| HPV31 | L2 | 231 | 8 | KVIDPTFL | 14305 | |
| HPV31 | L2 | 244 | 9 | LITYENPAY | 14306 | |
| HPV31 | L2 | 176 | 8 | LLLSSSSI | 14307 | |
| HPV31 | L2 | 287 | 10 | LTSRRNTVRY | 14308 | |
| HPV31 | L2 | 352 | 10 | LYDIYADTDF | 14309 | |
| HPV31 | L2 | 261 | 10 | LYFSNTSHNI | 14310 | |
| HPV31 | L2 | 447 | 11 | MLKRRRKRVSY | 14311 | |
| HPV31 | L2 | 269 | 8 | NIAPDPDF | 14312 | |
| HPV31 | L2 | 269 | 9 | NIAPDPDFL | 14313 | |
| HPV31 | L2 | 269 | 11 | NIAPDPDFLDI | 14314 | |
| HPV31 | L2 | 204 | 8 | NITSSTPI | 14315 | |
| HPV31 | L2 | 390 | 10 | NTTVPLSTGF | 14316 | |
| HPV31 | L2 | 292 | 8 | NTVRYSRL | 14317 | |
| HPV31 | L2 | 187 | 10 | NYEEIPMDTF | 14318 | |
| HPV31 | L2 | 187 | 11 | NYEEIPMDTFI | 14319 | |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | L2 | 410 | 10 | PIEHAPTQVF | 14320 | |
| HPV31 | L2 | 402 | 10 | PIFSGPDVPI | 14321 | |
| HPV31 | L2 | 210 | 11 | PIPGVRRPARL | 14322 | |
| HPV31 | L2 | 122 | 11 | PIPHPPTTSGF | 14323 | |
| HPV31 | L2 | 88 | 8 | PIRPPVSI | 14324 | |
| HPV31 | L2 | 422 | 11 | PLAPTTPQVSI | 14325 | |
| HPV31 | L2 | 100 | 9 | PLDPSIVSL | 14326 | |
| HPV31 | L2 | 394 | 8 | PLSTGFDI | 14327 | |
| HPV31 | L2 | 394 | 10 | PLSTGFDIPI | 14328 | |
| HPV31 | L2 | 394 | 11 | PLSTGFDIPIF | 14329 | |
| HPV31 | L2 | 235 | 10 | PTFLSAPKQL | 14330 | |
| HPV31 | L2 | 235 | 11 | PTFLSAPKQLI | 14331 | |
| HPV31 | L2 | 156 | 9 | PTFTDPSVL | 14332 | |
| HPV31 | L2 | 388 | 8 | PTNTTVPL | 14333 | |
| HPV31 | L2 | 167 | 10 | PTPAETSGHL | 14334 | |
| HPV31 | L2 | 167 | 11 | PTPAETSGHLL | 14335 | |
| HPV31 | L2 | 415 | 9 | PTQVFPFPL | 14336 | |
| HPV31 | L2 | 425 | 8 | PTTPQVSI | 14337 | |
| HPV31 | L2 | 425 | 9 | PTTPQVSIF | 14338 | |
| HPV31 | L2 | 127 | 8 | PTTSGFDI | 14339 | |
| HPV31 | L2 | 97 | 9 | PVGPLDPSI | 14340 | |
| HPV31 | L2 | 92 | 10 | PVSIDPVGPL | 14341 | |
| HPV31 | L2 | 44 | 8 | QILRYGSM | 14342 | |
| HPV31 | L2 | 44 | 11 | QILRYGSMGVF | 14343 | |
| HPV31 | L2 | 243 | 10 | QLITYENPAY | 14344 | |
| HPV31 | L2 | 303 | 11 | QTLRTRSGATI | 14345 | |
| HPV31 | L2 | 229 | 9 | QVKVIDPTF | 14346 | |
| HPV31 | L2 | 229 | 10 | QVKVIDPTFL | 14347 | |
| HPV31 | L2 | 429 | 11 | QVSIFVDGGDF | 14348 | |
| HPV31 | L2 | 298 | 8 | RLGNKQTL | 14349 | |
| HPV31 | L2 | 9 | 10 | RTKRASATQL | 14350 | |
| HPV31 | L2 | 9 | 11 | RTKRASATQLY | 14351 | |
| HPV31 | L2 | 306 | 8 | RTRSGATI | 14352 | |
| HPV31 | L2 | 316 | 8 | RVHYYYDI | 14353 | |
| HPV31 | L2 | 316 | 11 | RVHYYYDISSI | 14354 | |
| HPV31 | L2 | 47 | 8 | RYGSMGVF | 14355 | |
| HPV31 | L2 | 47 | 9 | RYGSMGVFF | 14356 | |
| HPV31 | L2 | 295 | 11 | RYSRLGNKQTL | 14357 | |
| HPV31 | L2 | 94 | 8 | SIDPVGPL | 14358 | |
| HPV31 | L2 | 431 | 9 | SIFVDGGDF | 14359 | |
| HPV31 | L2 | 431 | 10 | SIFVDGGDFY | 14360 | |
| HPV31 | L2 | 431 | 11 | SIFVDGGDFYL | 14361 | |
| HPV31 | L2 | 325 | 9 | SINPAGESI | 14362 | |
| HPV31 | L2 | 325 | 11 | SINPAGESIEM | 14363 | |
| HPV31 | L2 | 86 | 10 | SIPIRPPVSI | 14364 | |
| HPV31 | L2 | 182 | 10 | SISTHNYEEI | 14365 | |
| HPV31 | L2 | 104 | 11 | SIVSLVEESGI | 14366 | |
| HPV31 | L2 | 107 | 8 | SLVEESGI | 14367 | |
| HPV31 | L2 | 260 | 11 | SLYFSNTSHNI | 14368 | |
| HPV31 | L2 | 50 | 9 | SMGVFFGGL | 14369 | |
| HPV31 | L2 | 50 | 11 | SMGVFFGGLGI | 14370 | |
| HPV31 | L2 | 396 | 8 | STGFDIPI | 14371 | |
| HPV31 | L2 | 396 | 9 | STGFDIPIF | 14372 | |
| HPV31 | L2 | 151 | 8 | STHENPTF | 14373 | |
| HPV31 | L2 | 184 | 8 | STHNYEEI | 14374 | |
| HPV31 | L2 | 184 | 10 | STHNYEEIPM | 14375 | |
| HPV31 | L2 | 346 | 8 | STLNDGLY | 14376 | |
| HPV31 | L2 | 346 | 10 | STLNDGLYDI | 14377 | |
| HPV31 | L2 | 346 | 11 | STLNDGLYDIY | 14378 | |
| HPV31 | L2 | 379 | 8 | STSAVSAY | 14379 | |
| HPV31 | L2 | 80 | 8 | STVSEASI | 14380 | |
| HPV31 | L2 | 80 | 10 | STVSEASIPI | 14381 | |
| HPV31 | L2 | 149 | 10 | SVSTHENPTF | 14382 | |
| HPV31 | L2 | 195 | 11 | TFIVSTNNENI | 14383 | |
| HPV31 | L2 | 236 | 9 | TFLSAPKQL | 14384 | |
| HPV31 | L2 | 236 | 10 | TFLSAPKQLI | 14385 | |
| HPV31 | L2 | 157 | 8 | TFTDPSVL | 14386 | |
| HPV31 | L2 | 40 | 9 | TIADQILRY | 14387 | |
| HPV31 | L2 | 312 | 8 | TIGARVHY | 14388 | |
| HPV31 | L2 | 312 | 9 | TIGARVHYY | 14389 | |
| HPV31 | L2 | 312 | 10 | TIGARVHYYY | 14390 | |
| HPV31 | L2 | 347 | 9 | TLNDGLYDI | 14391 | |
| HPV31 | L2 | 347 | 10 | TLNDGLYDIY | 14392 | |
| HPV31 | L2 | 304 | 10 | TLRTRSGATI | 14393 | |

TABLE X-continued

A24 Supermotif Peptides

| Type | Protein | Position | No. of Amino Acids | Sequence | A*2402 | Seq. Id. No. |
|---|---|---|---|---|---|---|
| HPV31 | L2 | 136 | 9 | TTADTTPAI | 14394 | |
| HPV31 | L2 | 136 | 10 | TTADTTPAIL | 14395 | |
| HPV31 | L2 | 39 | 8 | TTIADQIL | 14396 | |
| HPV31 | L2 | 39 | 10 | TTIADQILRY | 14397 | |
| HPV31 | L2 | 426 | 8 | TTPQVSIF | 14398 | |
| HPV3t | L2 | 344 | 9 | TTSTLNDGL | 14399 | |
| HPV31 | L2 | 344 | 10 | TTSTLNDGLY | 14400 | |
| HPV31 | L2 | 343 | 10 | TTTSTLNDGL | 14401 | |
| HPV31 | L2 | 343 | 11 | TTTSTLNDGLY | 14402 | |
| HPV31 | L2 | 391 | 9 | TTVPLSTGF | 14403 | |
| HPV31 | L2 | 391 | 11 | TTVPLSTGFDI | 14404 | |
| HPV31 | L2 | 254 | 8 | TVNAEESL | 14405 | |
| HPV31 | L2 | 254 | 9 | TVNAEESLY | 14406 | |
| HPV31 | L2 | 254 | 10 | TVNAEESLYF | 14407 | |
| HPV31 | L2 | 392 | 8 | TVPLSTGF | 14408 | |
| HPV31 | L2 | 392 | 10 | TVPLSTGFDI | 14409 | |
| HPV31 | L2 | 81 | 9 | TVSEASIPI | 14410 | |
| HPV31 | L2 | 53 | 8 | VFFGGLGI | 14411 | |
| HPV31 | L2 | 32 | 10 | VIPKIEHTTI | 14412 | |
| HPV31 | L2 | 262 | 9 | YFSNTSHNI | 14413 | |
| HPV31 | L2 | 440 | 8 | YLHPSYYM | 14414 | |
| HPV31 | L2 | 440 | 9 | YLHPSYYML | 14415 | |
| HPV31 | L2 | 386 | 10 | YVPTNTTVPL | 14416 | |
| HPV31 | L2 | 319 | 8 | YYYDISSI | 14417 | |
| HPV33 | E1 | 452 | 9 | AFKKFLKGI | 14418 | |
| HPV33 | E1 | 448 | 9 | AFLGAFKKF | 14419 | |
| HPV33 | E1 | 448 | 10 | AFLGAFKKFL | 14420 | |
| HPV33 | E1 | 384 | 11 | AFLKSNSQAKI | 14421 | |
| HPV33 | E1 | 596 | 10 | AINDENWKSF | 14422 | |
| HPV33 | E1 | 596 | 11 | AINDENWKSFF | 14423 | |
| HPV33 | E1 | 532 | 9 | ALDGNEISI | 14424 | |
| HPV33 | E1 | 546 | 10 | ALVQLKCPPL | 14425 | |
| HPV33 | E1 | 546 | 11 | ALVQLKCPPLL | 14426 | |
| HPV33 | E1 | 311 | 9 | ALYWFRTAM | 14427 | |
| HPV33 | E1 | 81 | 9 | AVCALKRKF | 14428 | |
| HPV33 | E1 | 22 | 11 | AVIERRTGDNI | 14429 | |
| HPV33 | E1 | 207 | 9 | AYGISFMEL | 14430 | |
| HPV33 | E1 | 259 | 8 | CLTCDRGI | 14431 | |
| HPV33 | E1 | 259 | 9 | CLTCDRGII | 14432 | |
| HPV33 | E1 | 259 | 10 | CLTCDRGIII | 14433 | |
| HPV33 | E1 | 259 | 11 | CLTCDRGIIIL | 14434 | |
| HPV33 | E1 | 297 | 9 | CMVIEPPKL | 14435 | |
| HPV33 | E1 | 226 | 9 | CTDWCITGY | 14436 | |
| HPV33 | E1 | 226 | 11 | CTDWCITGYGI | 14437 | |
| HPV33 | E1 | 14 | 11 | CTGWFEVEAVI | 14438 | |
| HPV33 | E1 | 118 | 8 | CTYRKRKI | 14439 | |
| HPV33 | E1 | 118 | 11 | CTYRKRKIDEL | 14440 | |
| HPV33 | E1 | 494 | 8 | CVNSKSHF | 14441 | |
| HPV33 | E1 | 494 | 9 | CVNSKSHFW | 14442 | |
| HPV33 | E1 | 494 | 10 | CVNSKSHFWL | 14443 | |
| HPV33 | E1 | 367 | 9 | DIAYYYAQL | 14444 | |
| HPV33 | E1 | 46 | 10 | DLLEFIDDSM | 14445 | |
| HPV33 | E1 | 78 | 8 | DLNAVCAL | 14446 | |
| HPV33 | E1 | 349 | 8 | DLSEMVQW | 14447 | |
| HPV33 | E1 | 349 | 10 | DLSEMVQWAY | 14448 | |
| HPV33 | E1 | 62 | 8 | DTEAARAL | 14449 | |
| HPV33 | E1 | 62 | 9 | DTEAARALF | 14450 | |
| HPV33 | E1 | 62 | 11 | DTEAARALFNI | 14451 | |
| HPV33 | E1 | 541 | 10 | DVKHRALVQL | 14452 | |
| HPV33 | E1 | 324 | 9 | DVQGTTPEW | 14453 | |
| HPV33 | E1 | 324 | 10 | DVQGTTPEWI | 14454 | |
| HPV33 | E1 | 516 | 9 | DVTPISWTY | 14455 | |
| HPV33 | E1 | 516 | 10 | DVTPISWTYI | 14456 | |
| HPV33 | E1 | 228 | 9 | DWCITGYGI | 14457 | |
| HPV33 | E1 | 49 | 11 | EFIDDSMENSI | 14458 | |
| HPV33 | E1 | 580 | 8 | EFKNPFPF | 14459 | |
| HPV33 | E1 | 445 | 9 | EFTAFLGAF | 14460 | |
| HPV33 | E1 | 537 | 11 | EISIDVKHRAL | 14461 | |
| HPV33 | E1 | 361 | 8 | ELTDDSDI | 14462 | |
| HPV33 | E1 | 361 | 10 | ELTDDSDIAY | 14463 | |
| HPV33 | E1 | 361 | 11 | ELTDDSDIAYY | 14464 | |
| HPV33 | E1 | 352 | 11 | EMVQWAYDNEL | 14465 | |
| HPV33 | E1 | 38 | 10 | ETADDSGTDL | 14466 | |
| HPV33 | E1 | 38 | 11 | ETADDSGTDLL | 14467 | |

TABLE X-continued

A24 Supermotif Peptides

| Type | Protein | Position | No. of Amino Acids | Sequence | A*2402 Seq. Id. No. |
|---|---|---|---|---|---|
| HPV33 | E1 | 295 | 11 | ETCMVIEPPKL | 14468 |
| HPV33 | E1 | 331 | 9 | EWIDRLTVL | 14469 |
| HPV33 | E1 | 605 | 9 | FFSRTWCKL | 14470 |
| HPV33 | E1 | 605 | 11 | FFSRTWCKLDL | 14471 |
| HPV33 | E1 | 50 | 10 | FIDDSMENSI | 14472 |
| HPV33 | E1 | 449 | 8 | FLGAFKKF | 14473 |
| HPV33 | E1 | 449 | 9 | FLGAFKKFL | 14474 |
| HPV33 | E1 | 456 | 11 | FLKGIPKKSCM | 14475 |
| HPV33 | E1 | 385 | 10 | FLKSNSQAKI | 14476 |
| HPV33 | E1 | 212 | 8 | FMELVRPF | 14477 |
| HPV33 | E1 | 446 | 8 | FTAFLGAF | 14478 |
| HPV33 | E1 | 446 | 11 | FTAFLGAFKKF | 14479 |
| HPV33 | E1 | 501 | 11 | FWLQPLSDAKI | 14480 |
| HPV33 | E1 | 265 | 8 | GIIILLLI | 14481 |
| HPV33 | E1 | 265 | 10 | GIIILLLIRF | 14482 |
| HPV33 | E1 | 459 | 8 | GIPKKSCM | 14483 |
| HPV33 | E1 | 459 | 9 | GIPKKSCML | 14484 |
| HPV33 | E1 | 459 | 10 | GIPKKSCMLI | 14485 |
| HPV33 | E1 | 209 | 11 | GISFMELVRPF | 14486 |
| HPV33 | E1 | 235 | 10 | GISPSVAESL | 14487 |
| HPV33 | E1 | 11 | 8 | GMGCTGWF | 14488 |
| HPV33 | E1 | 512 | 9 | GMIDDVTPI | 14489 |
| HPV33 | E1 | 512 | 11 | GMIDDVTPISW | 14490 |
| HPV33 | E1 | 480 | 8 | GMSLIQFL | 14491 |
| HPV33 | E1 | 44 | 8 | GTDLLEFI | 14492 |
| HPV33 | E1 | 564 | 8 | GTDSRWPY | 14493 |
| HPV33 | E1 | 564 | 9 | GTDSRWPYL | 14494 |
| HPV33 | E1 | 327 | 10 | GTTPEWIDRL | 14495 |
| HPV33 | E1 | 16 | 9 | GWFEVEAVI | 14496 |
| HPV33 | E1 | 256 | 11 | HLQCLTCDRGI | 14497 |
| HPV33 | E1 | 404 | 10 | HYKKAEKRKM | 14498 |
| HPV33 | E1 | 347 | 10 | IFDLSEMVQW | 14499 |
| HPV33 | E1 | 266 | 9 | IIILLLIRF | 14500 |
| HPV33 | E1 | 267 | 8 | IILLLIRF | 14501 |
| HPV33 | E1 | 200 | 9 | ILYKFKEAY | 14502 |
| HPV33 | E1 | 200 | 11 | ILYKFKEAYGI | 14503 |
| HPV33 | E1 | 394 | 8 | IVKDCGIM | 14504 |
| HPV33 | E1 | 435 | 10 | IVQLLRYQNI | 14505 |
| HPV33 | E1 | 203 | 8 | KFKEAYGI | 14506 |
| HPV33 | E1 | 203 | 10 | KFKEAYGISF | 14507 |
| HPV33 | E1 | 203 | 11 | KFKEAYGISFM | 14508 |
| HPV33 | E1 | 124 | 10 | KIDELEDSGY | 14509 |
| HPV33 | E1 | 510 | 11 | KIGMIDDVTPI | 14510 |
| HPV33 | E1 | 393 | 8 | KIVKDCGI | 14511 |
| HPV33 | E1 | 393 | 9 | KIVKDCGIM | 14512 |
| HPV33 | E1 | 285 | 9 | KLMSNLLSI | 14513 |
| HPV33 | E1 | 304 | 9 | KLRSQTCAL | 14514 |
| HPV33 | E1 | 304 | 10 | KLRSQTCALY | 14515 |
| HPV33 | E1 | 304 | 11 | KLRSQTCALYW | 14516 |
| HPV33 | E1 | 412 | 8 | KMSIGQWI | 14517 |
| HPV33 | E1 | 425 | 8 | KTNDGGNW | 14518 |
| HPV33 | E1 | 425 | 11 | KTNDGGNWRPI | 14519 |
| HPV33 | E1 | 223 | 9 | KTSCTDWCI | 14520 |
| HPV33 | E1 | 245 | 9 | KVLIKQHSL | 14521 |
| HPV33 | E1 | 245 | 10 | KVLIKQHSLY | 14522 |
| HPV33 | E1 | 69 | 11 | LFNIQEGEDDL | 14523 |
| HPV33 | E1 | 247 | 8 | LIKQHSLY | 14524 |
| HPV33 | E1 | 247 | 11 | LIKQHSLYTHL | 14525 |
| HPV33 | E1 | 483 | 10 | LIQFLKGCVI | 14526 |
| HPV33 | E1 | 271 | 11 | LIRFRCSKNRL | 14527 |
| HPV33 | E1 | 47 | 9 | LLEFIDDSM | 14528 |
| HPV33 | E1 | 438 | 9 | LLRYQNIEF | 14529 |
| HPV33 | E1 | 290 | 9 | LLSIPETCM | 14530 |
| HPV33 | E1 | 290 | 11 | LLSIPETCMVI | 14531 |
| HPV33 | E1 | 286 | 8 | LMSNLLSI | 14532 |
| HPV33 | E1 | 260 | 8 | LTCDRGII | 14533 |
| HPV33 | E1 | 260 | 9 | LTCDRGIII | 14534 |
| HPV33 | E1 | 260 | 10 | LTCDRGIIIL | 14535 |
| HPV33 | E1 | 260 | 11 | LTCDRGIIILL | 14536 |
| HPV33 | E1 | 362 | 9 | LTDDSDIAY | 14537 |
| HPV33 | E1 | 362 | 10 | LTDDSDIAYY | 14538 |
| HPV33 | E1 | 362 | 11 | LTDDSDIAYYY | 14539 |
| HPV33 | E1 | 281 | 10 | LTVAKLMSNL | 14540 |
| HPV33 | E1 | 281 | 11 | LTVAKLMSNLL | 14541 |

TABLE X-continued

A24 Supermotif Peptides

| Type | Protein | Position | No. of Amino Acids | Sequence | A*2402 | Seq. Id. No. |
|---|---|---|---|---|---|---|
| HPV33 | E1 | 576 | 10 | LTVFEFKNPF | 14542 | |
| HPV33 | E1 | 336 | 8 | LTVLQHSF | 14543 | |
| HPV33 | E1 | 547 | 9 | LVQLKCPPL | 14544 | |
| HPV33 | E1 | 547 | 10 | LVQLKCPPLL | 14545 | |
| HPV33 | E1 | 547 | 11 | LVQLKCPPLLL | 14546 | |
| HPV33 | E1 | 201 | 8 | LYKFKEAY | 14547 | |
| HPV33 | E1 | 201 | 10 | LYKFKEAYGI | 14548 | |
| HPV33 | E1 | 253 | 8 | LYTHLQCL | 14549 | |
| HPV33 | E1 | 312 | 8 | LYWFRTAM | 14550 | |
| HPV33 | E1 | 312 | 11 | LYWFRTAMSNI | 14551 | |
| HPV33 | E1 | 513 | 8 | MIDDVTPI | 14552 | |
| HPV33 | E1 | 513 | 10 | MIDDVTPISW | 14553 | |
| HPV33 | E1 | 298 | 8 | MVIEPPKL | 14554 | |
| HPV33 | E1 | 353 | 10 | MVQWAYDNEL | 14555 | |
| HPV33 | E1 | 443 | 8 | NIEFTAFL | 14556 | |
| HPV33 | E1 | 443 | 11 | NIEFTAFLGAF | 14557 | |
| HPV33 | E1 | 346 | 8 | NIFDLSEM | 14558 | |
| HPV33 | E1 | 346 | 11 | NIFDLSEMVQW | 14559 | |
| HPV33 | E1 | 199 | 10 | NILYKFKEAY | 14560 | |
| HPV33 | E1 | 71 | 9 | NIQEGEDDL | 14561 | |
| HPV33 | E1 | 289 | 10 | NLLSIPETCM | 14562 | |
| HPV33 | E1 | 135 | 9 | NTEVETQQM | 14563 | |
| HPV33 | E1 | 473 | 9 | NTGKSYFGM | 14564 | |
| HPV33 | E1 | 473 | 11 | NTGKSYFGMSL | 14565 | |
| HPV33 | E1 | 195 | 8 | NTKANILY | 14566 | |
| HPV33 | E1 | 195 | 10 | NTKANILYKF | 14567 | |
| HPV33 | E1 | 560 | 10 | NTNAGTDSRW | 14568 | |
| HPV33 | E1 | 175 | 10 | NVDSCENVTL | 14569 | |
| HPV33 | E1 | 181 | 11 | NVTLQEISNVL | 14570 | |
| HPV33 | E1 | 601 | 10 | NWKSFFSRTW | 14571 | |
| HPV33 | E1 | 431 | 8 | NWRPIVQL | 14572 | |
| HPV33 | E1 | 431 | 9 | NWRPIVQLL | 14573 | |
| HPV33 | E1 | 431 | 11 | NWRPIVQLLRY | 14574 | |
| HPV33 | E1 | 586 | 10 | PFDENGNPVY | 14575 | |
| HPV33 | E1 | 519 | 10 | PISWTYIDDY | 14576 | |
| HPV33 | E1 | 519 | 11 | PISWTYIDDYM | 14577 | |
| HPV33 | E1 | 434 | 8 | PIVQLLRY | 14578 | |
| HPV33 | E1 | 434 | 11 | PIVQLLRYQNI | 14579 | |
| HPV33 | E1 | 505 | 9 | PLSDAKIGM | 14580 | |
| HPV33 | E1 | 505 | 10 | PLSDAKIGMI | 14581 | |
| HPV33 | E1 | 593 | 10 | PVYAINDENW | 14582 | |
| HPV33 | E1 | 570 | 10 | PYLHSRLTVF | 14583 | |
| HPV33 | E1 | 485 | 8 | QFLKGCVI | 14584 | |
| HPV33 | E1 | 549 | 8 | QLKCPPLL | 14585 | |
| HPV33 | E1 | 549 | 9 | QLKCPPLLL | 14586 | |
| HPV33 | E1 | 437 | 8 | QLLRYQNI | 14587 | |
| HPV33 | E1 | 437 | 10 | QLLRYQNIEF | 14588 | |
| HPV33 | E1 | 308 | 8 | QTCALYWF | 14589 | |
| HPV33 | E1 | 146 | 11 | QVESQNGDTNL | 14590 | |
| HPV33 | E1 | 355 | 8 | QWAYDNEL | 14591 | |
| HPV33 | E1 | 273 | 9 | RFRCSKNRL | 14592 | |
| HPV33 | E1 | 280 | 8 | RLTVAKLM | 14593 | |
| HPV33 | E1 | 280 | 11 | RLTVAKLMSNL | 14594 | |
| HPV33 | E1 | 575 | 11 | RLTVFEFKNPF | 14595 | |
| HPV33 | E1 | 335 | 9 | RLTVLQHSF | 14596 | |
| HPV33 | E1 | 608 | 8 | RTWCKLDL | 14597 | |
| HPV33 | E1 | 608 | 9 | RTWCKLDLI | 14598 | |
| HPV33 | E1 | 568 | 9 | RWPYLHSRL | 14599 | |
| HPV33 | E1 | 440 | 10 | RYQNIEFTAF | 14600 | |
| HPV33 | E1 | 440 | 11 | RYQNIEFTAFL | 14601 | |
| HPV33 | E1 | 604 | 10 | SFFSRTWCKL | 14602 | |
| HPV33 | E1 | 211 | 9 | SFMELVRPF | 14603 | |
| HPV33 | E1 | 342 | 9 | SFNDNIFDL | 14604 | |
| HPV33 | E1 | 539 | 9 | SIDVKHRAL | 14605 | |
| HPV33 | E1 | 111 | 10 | SINKNKECTY | 14606 | |
| HPV33 | E1 | 292 | 9 | SIPETCMVI | 14607 | |
| HPV33 | E1 | 482 | 11 | SLIQFLKGCVI | 14608 | |
| HPV33 | E1 | 243 | 11 | SLKVLIKQHSL | 14609 | |
| HPV33 | E1 | 252 | 9 | SLYTHLQCL | 14610 | |
| HPV33 | E1 | 239 | 9 | SVAESLKVL | 14611 | |
| HPV33 | E1 | 239 | 10 | SVAESLKVLI | 14612 | |
| HPV33 | E1 | 521 | 8 | SWTYIDDY | 14613 | |
| HPV33 | E1 | 521 | 9 | SWTYIDDYM | 14614 | |
| HPV33 | E1 | 477 | 8 | SYFGMSLI | 14615 | |

TABLE X-continued

A24 Supermotif Peptides

| Type | Protein | Position | No. of Amino Acids | Sequence | A*2402 | Seq. Id. No. |
|---|---|---|---|---|---|---|
| HPV33 | E1 | 477 | 10 | SYFGMSLIQF | 14616 | |
| HPV33 | E1 | 477 | 11 | SYFGMSLIQFL | 14617 | |
| HPV33 | E1 | 183 | 9 | TLQEISNVL | 14618 | |
| HPV33 | E1 | 328 | 9 | TTPEWIDRL | 14619 | |
| HPV33 | E1 | 282 | 9 | TVAKLMSNL | 14620 | |
| HPV33 | E1 | 282 | 10 | TVAKLMSNLL | 14621 | |
| HPV33 | E1 | 577 | 9 | TVFEFKNPF | 14622 | |
| HPV33 | E1 | 577 | 11 | TVFEFKNPFPF | 14623 | |
| HPV33 | E1 | 337 | 11 | TVLQHSFNDNI | 14624 | |
| HPV33 | E1 | 609 | 8 | TWCKLDLI | 14625 | |
| HPV33 | E1 | 523 | 11 | TYIDDYMRNAL | 14626 | |
| HPV33 | E1 | 119 | 10 | TYRKRKIDEL | 14627 | |
| HPV33 | E1 | 578 | 8 | VFEFKNPF | 14628 | |
| HPV33 | E1 | 578 | 10 | VFEFKNPFPF | 14629 | |
| HPV33 | E1 | 23 | 10 | VIERRTGDNI | 14630 | |
| HPV33 | E1 | 491 | 11 | VISCVNSKSHF | 14631 | |
| HPV33 | E1 | 190 | 11 | VLHSSNTKANI | 14632 | |
| HPV33 | E1 | 246 | 8 | VLIKQHSL | 14633 | |
| HPV33 | E1 | 246 | 9 | VLIKQHSLY | 14634 | |
| HPV33 | E1 | 338 | 10 | VLQHSFNDNI | 14635 | |
| HPV33 | E1 | 338 | 11 | VLQHSFNDNIF | 14636 | |
| HPV33 | E1 | 182 | 10 | VTLQEISNVL | 14637 | |
| HPV33 | E1 | 517 | 8 | VTPISWTY | 14638 | |
| HPV33 | E1 | 517 | 9 | VTPISWTYI | 14639 | |
| HPV33 | E1 | 594 | 9 | VYAINDENW | 14640 | |
| HPV33 | E1 | 17 | 8 | WFEVEAVI | 14641 | |
| HPV33 | E1 | 314 | 9 | WFRTAMSNI | 14642 | |
| HPV33 | E1 | 332 | 8 | WIDRLTVL | 14643 | |
| HPV33 | E1 | 502 | 10 | WLQPLSDAKI | 14644 | |
| HPV33 | E1 | 522 | 8 | WTYIDDYM | 14645 | |
| HPV33 | E1 | 478 | 9 | YFGMSLIQF | 14646 | |
| HPV33 | E1 | 478 | 10 | YFGMSLIQFL | 14647 | |
| HPV33 | E1 | 524 | 10 | YIDDYMRNAL | 14648 | |
| HPV33 | E1 | 571 | 9 | YLHSRLTVF | 14649 | |
| HPV33 | E1 | 571 | 11 | YLHSRLTVFEF | 14650 | |
| HPV33 | E1 | 528 | 11 | YMRNALDGNEI | 14651 | |
| HPV33 | E1 | 313 | 10 | YWFRTAMSNI | 14652 | |
| HPV33 | E2 | 69 | 9 | AFQVIELQM | 14653 | |
| HPV33 | E2 | 69 | 11 | AFQVIELQMAL | 14654 | |
| HPV33 | E2 | 78 | 10 | ALETLSKSQY | 14655 | |
| HPV33 | E2 | 41 | 9 | ALLYTAKQM | 14656 | |
| HPV33 | E2 | 41 | 11 | ALLYTAKQMGF | 14657 | |
| HPV33 | E2 | 10 | 9 | AVQEKILDL | 14658 | |
| HPV33 | E2 | 10 | 10 | AVQEKILDLY | 14659 | |
| HPV33 | E2 | 288 | 9 | CLRYRLKPY | 14660 | |
| HPV33 | E2 | 145 | 10 | CTMVTGKVDY | 14661 | |
| HPV33 | E2 | 145 | 11 | CTMVTGKVDYI | 14662 | |
| HPV33 | E2 | 25 | 9 | DLPSQIEHW | 14663 | |
| HPV33 | E2 | 25 | 11 | DLPSQIEHWKL | 14664 | |
| HPV33 | E2 | 17 | 10 | DLYEADKTDL | 14665 | |
| HPV33 | E2 | 235 | 9 | DTAQPLTKL | 14666 | |
| HPV33 | E2 | 235 | 10 | DTAQPLTKLF | 14667 | |
| HPV33 | E2 | 232 | 9 | DTTDTAQPL | 14668 | |
| HPV33 | E2 | 153 | 8 | DYIGMYYI | 14669 | |
| HPV33 | E2 | 130 | 8 | DYTNWGEI | 14670 | |
| HPV33 | E2 | 130 | 9 | DYTNWGEIY | 14671 | |
| HPV33 | E2 | 130 | 10 | DYTNWGEIYI | 14672 | |
| HPV33 | E2 | 130 | 11 | DYTNWGEIYII | 14673 | |
| HPV33 | E2 | 74 | 9 | ELQMALETL | 14674 | |
| HPV33 | E2 | 298 | 10 | ELYSSMSSTW | 14675 | |
| HPV33 | E2 | 80 | 8 | ETLSKSQY | 14676 | |
| HPV33 | E2 | 185 | 9 | EVHVGGQVI | 14677 | |
| HPV33 | E2 | 100 | 11 | EVWLCEPPKCF | 14678 | |
| HPV33 | E2 | 325 | 9 | FVTEQQQQM | 14679 | |
| HPV33 | E2 | 325 | 10 | FVTEQQQQMF | 14680 | |
| HPV33 | E2 | 325 | 11 | FVTEQQQQMFL | 14681 | |
| HPV33 | E2 | 336 | 11 | GTVKIPPTVQI | 14682 | |
| HPV33 | E2 | 53 | 10 | HLCHQVVPSL | 14683 | |
| HPV33 | E2 | 53 | 11 | HLCHQVVPSLL | 14684 | |
| HPV33 | E2 | 278 | 9 | HLKGESNSL | 14685 | |
| HPV33 | E2 | 32 | 11 | HWKLIRMECAL | 14686 | |
| HPV33 | E2 | 139 | 9 | IIEEDTCTM | 14687 | |
| HPV33 | E2 | 276 | 11 | IVHLKGESNSL | 14688 | |
| HPV33 | E2 | 137 | 11 | IYIIEEDTCTM | 14689 | |

TABLE X-continued

A24 Supermotif Peptides

| Type | Protein | Position | No. of Amino Acids | Sequence | A*2402 | Seq. Id. No. |
|---|---|---|---|---|---|---|
| HPV33 | E2 | 339 | 8 | KIPPIVQI | 14690 | |
| HPV33 | E2 | 242 | 9 | KLFCADPAL | 14691 | |
| HPV33 | E2 | 34 | 9 | KLIRMECAL | 14692 | |
| HPV33 | E2 | 34 | 10 | KLIRMECALL | 14693 | |
| HPV33 | E2 | 34 | 11 | KLIRMECALLY | 14694 | |
| HPV33 | E2 | 23 | 8 | KTDLPSQI | 14695 | |
| HPV33 | E2 | 23 | 11 | KTDLPSQIEHW | 14696 | |
| HPV33 | E2 | 66 | 8 | KTKAFQVI | 14697 | |
| HPV33 | E2 | 66 | 10 | KTKAFQVIEL | 14698 | |
| HPV33 | E2 | 151 | 8 | KVDYIGMY | 14699 | |
| HPV33 | E2 | 151 | 9 | KVDYIGMYY | 14700 | |
| HPV33 | E2 | 151 | 10 | KVDYIGMYYI | 14701 | |
| HPV33 | E2 | 169 | 10 | KYFKEDAAKY | 14702 | |
| HPV33 | E2 | 177 | 8 | KYSKTQMW | 14703 | |
| HPV33 | E2 | 243 | 8 | LFCADPAL | 14704 | |
| HPV33 | E2 | 35 | 8 | LIRMECAL | 14705 | |
| HPV33 | E2 | 35 | 9 | LIRMECALL | 14706 | |
| HPV33 | E2 | 35 | 10 | LIRMECALLY | 14707 | |
| HPV33 | E2 | 62 | 9 | LLASKTKAF | 14708 | |
| HPV33 | E2 | 42 | 8 | LLYTAKQM | 14709 | |
| HPV33 | E2 | 42 | 10 | LLYTAKQMGF | 14710 | |
| HPV33 | E2 | 240 | 11 | LTKLFCADPAL | 14711 | |
| HPV33 | E2 | 18 | 9 | LYEADKTDL | 14712 | |
| HPV33 | E2 | 299 | 9 | LYSSMSSTW | 14713 | |
| HPV33 | E2 | 299 | 11 | LYSSMSSTWHW | 14714 | |
| HPV33 | E2 | 43 | 9 | LYTAKQMGF | 14715 | |
| HPV33 | E2 | 333 | 8 | MFLGTVKI | 14716 | |
| HPV33 | E2 | 147 | 8 | MVTGKVDY | 14717 | |
| HPV33 | E2 | 147 | 9 | MVTGKVDYI | 14718 | |
| HPV33 | E2 | 147 | 11 | MVTGKVDYIGM | 14179 | |
| HPV33 | E2 | 183 | 11 | MWEVHVGGQVI | 14720 | |
| HPV33 | E2 | 157 | 11 | MYYIHNCEKVY | 14721 | |
| HPV33 | E2 | 127 | 8 | NTMDYTNW | 14722 | |
| HPV33 | E2 | 127 | 11 | NTMDYTNWGEI | 14723 | |
| HPV33 | E2 | 272 | 8 | NVAPIVHL | 14724 | |
| HPV33 | E2 | 133 | 8 | NWGEIYII | 14725 | |
| HPV33 | E2 | 196 | 9 | PTSISSNQI | 14726 | |
| HPV33 | E2 | 342 | 9 | PTVQISTGF | 14727 | |
| HPV33 | E2 | 342 | 10 | PTVQISTGFM | 14728 | |
| HPV33 | E2 | 295 | 9 | PYKELYSSM | 14729 | |
| HPV33 | E2 | 29 | 8 | QIEHWKLI | 14730 | |
| HPV33 | E2 | 29 | 10 | QIEHWKLIRM | 14731 | |
| HPV33 | E2 | 345 | 9 | QISTGFMTL | 14732 | |
| HPV33 | E2 | 203 | 10 | QISTTETADI | 14733 | |
| HPV33 | E2 | 332 | 9 | QMFLGTVKI | 14734 | |
| HPV33 | E2 | 96 | 8 | QTSLEVWL | 14735 | |
| HPV33 | E2 | 71 | 9 | QVIELQMAL | 14736 | |
| HPV33 | E2 | 191 | 9 | QVIVCPTSI | 14737 | |
| HPV33 | E2 | 91 | 9 | QWTLQQTSL | 14738 | |
| HPV33 | E2 | 120 | 10 | QYDNDKKNTM | 14739 | |
| HPV33 | E2 | 86 | 9 | QYSTSQWTL | 14740 | |
| HPV33 | E2 | 292 | 8 | RLKPYKEL | 14741 | |
| HPV33 | E2 | 292 | 9 | RLKPYKELY | 14742 | |
| HPV33 | E2 | 7 | 9 | RLNAVQEKI | 14743 | |
| HPV33 | E2 | 7 | 10 | RLNAVQEKIL | 14744 | |
| HPV33 | E2 | 37 | 8 | RMECALLY | 14745 | |
| HPV33 | E2 | 266 | 11 | RTVCSSNVAPI | 14746 | |
| HPV33 | E2 | 290 | 10 | RYRLKPYKEL | 14747 | |
| HPV33 | E2 | 290 | 11 | RYRLKPYKELY | 14748 | |
| HPV33 | E2 | 285 | 9 | SLKCLRYRL | 14749 | |
| HPV33 | E2 | 61 | 10 | SLLASKTKAF | 14750 | |
| HPV33 | E2 | 302 | 8 | SMSSTWHW | 14751 | |
| HPV33 | E2 | 205 | 8 | STTETADI | 14752 | |
| HPV33 | E2 | 324 | 10 | TFVTEQQQQM | 14753 | |
| HPV33 | E2 | 324 | 11 | TFVTEQQQQMF | 14754 | |
| HPV33 | E2 | 93 | 10 | TLQQTSLEVW | 14755 | |
| HPV33 | E2 | 93 | 11 | TLQQTSLEVWL | 14756 | |
| HPV33 | E2 | 128 | 10 | TMDYTNWGEI | 14757 | |
| HPV33 | E2 | 128 | 11 | TMDYTNWGEIY | 14758 | |
| HPV33 | E2 | 146 | 9 | TMVTGKVDY | 14759 | |
| HPV33 | E2 | 146 | 10 | TMVTGKVDYI | 14760 | |
| HPV33 | E2 | 233 | 8 | TTDTAQPL | 14761 | |
| HPV33 | E2 | 233 | 11 | TTDTAQPLTKL | 14762 | |
| HPV33 | E2 | 267 | 10 | TVCSSNVAPI | 14763 | |

TABLE X-continued

A24 Supermotif Peptides

| Type | Protein | Position | No. of Amino Acids | Sequence | A*2402 | Seq. Id. No. |
|---|---|---|---|---|---|---|
| HPV33 | E2 | 337 | 10 | TVKIPPTVQI | 14764 | |
| HPV33 | E2 | 343 | 8 | TVQISTGF | 14765 | |
| HPV33 | E2 | 343 | 9 | TVQISTGFM | 14766 | |
| HPV33 | E2 | 343 | 11 | TVQISTGFMTL | 14767 | |
| HPV33 | E2 | 72 | 8 | VIELQMAL | 14768 | |
| HPV33 | E2 | 72 | 11 | VIELQMALETL | 14769 | |
| HPV33 | E2 | 192 | 8 | VIVCPTSI | 14770 | |
| HPV33 | E2 | 326 | 8 | VTEQQQQM | 14771 | |
| HPV33 | E2 | 326 | 9 | VTEQQQQMF | 14772 | |
| HPV33 | E2 | 326 | 10 | VTEQQQQMFL | 14773 | |
| HPV33 | E2 | 323 | 11 | VTFVTEQQQQM | 14774 | |
| HPV33 | E2 | 148 | 8 | VTGKVDYI | 14775 | |
| HPV33 | E2 | 148 | 10 | VTGKVDYIGM | 14776 | |
| HPV33 | E2 | 148 | 11 | VTGKVDYIGMY | 14777 | |
| HPV33 | E2 | 101 | 10 | VWLCEPPKCF | 14778 | |
| HPV33 | E2 | 102 | 9 | WLCEPPKCF | 14779 | |
| HPV33 | E2 | 92 | 8 | WTLQQTSL | 14780 | |
| HPV33 | E2 | 92 | 11 | WTLQQTSLEVW | 14781 | |
| HPV33 | E2 | 170 | 9 | YFKEDAAKY | 14782 | |
| HPV33 | E2 | 159 | 9 | YIHNCEKVY | 14783 | |
| HPV33 | E2 | 159 | 10 | YIHNCEKVYF | 14784 | |
| HPV33 | E2 | 138 | 10 | YIIEEDTCTM | 14785 | |
| HPV33 | E2 | 44 | 8 | YTAKQMGF | 14786 | |
| HPV33 | E2 | 44 | 11 | YTAKQMGFSHL | 14787 | |
| HPV33 | E2 | 131 | 8 | YTNWGEIY | 14788 | |
| HPV33 | E2 | 131 | 9 | YTNWGEIYI | 14789 | |
| HPV33 | E2 | 131 | 10 | YTNWGEIYII | 14790 | |
| HPV33 | E2 | 158 | 10 | YYIHNCEKVY | 14791 | |
| HPV33 | E2 | 158 | 11 | YYIHNCEKVYF | 14792 | |
| HPV33 | E5 | 30 | 8 | AWLLVLVL | 14793 | |
| HPV33 | E5 | 30 | 9 | AWLLVLVLL | 14794 | |
| HPV33 | E5 | 30 | 10 | AWLLVLVLLL | 14795 | |
| HPV33 | E5 | 30 | 11 | AWLLVLVLLLW | 14796 | |
| HPV33 | E5 | 8 | 8 | CFILFLCL | 14797 | |
| HPV33 | E5 | 8 | 10 | CFILFLCLSL | 14798 | |
| HPV33 | E5 | 8 | 11 | CFILFLCLSLL | 14799 | |
| HPV33 | E5 | 63 | 9 | CINFHAQHM | 14800 | |
| HPV33 | E5 | 14 | 9 | CLSLLLRPL | 14801 | |
| HPV33 | E5 | 14 | 10 | CLSLLLRPLI | 14802 | |
| HPV33 | E5 | 14 | 11 | CLSLLLRRLIL | 14803 | |
| HPV33 | E5 | 52 | 8 | CYLLFLYL | 14804 | |
| HPV33 | E5 | 52 | 10 | CYLLFLYLPM | 14805 | |
| HPV33 | E5 | 52 | 11 | CYLLFLYLPMM | 14806 | |
| HPV33 | E5 | 50 | 8 | FFCYLLFL | 14807 | |
| HPV33 | E5 | 50 | 9 | FFCYLLFLY | 14808 | |
| HPV33 | E5 | 50 | 10 | FFCYLLFLYL | 14809 | |
| HPV33 | E5 | 9 | 9 | FILFLCLSL | 14810 | |
| HPV33 | E5 | 9 | 10 | FILFLCLSLL | 14811 | |
| HPV33 | E5 | 9 | 11 | FILFLCLSLLL | 14812 | |
| HPV33 | E5 | 12 | 8 | FLCLSLLL | 14813 | |
| HPV33 | E5 | 12 | 11 | FLCLSLLLRPL | 14814 | |
| HPV33 | E5 | 56 | 9 | FLYLPMMCI | 14815 | |
| HPV33 | E5 | 56 | 11 | FLYLPMMCINF | 14816 | |
| HPV33 | E5 | 3 | 8 | FVFVLCFI | 14817 | |
| HPV33 | E5 | 3 | 9 | FVFVLCFIL | 14818 | |
| HPV33 | E5 | 3 | 10 | FVFVLCFILF | 14819 | |
| HPV33 | E5 | 3 | 11 | FVFVLCFILFL | 14820 | |
| HPV33 | E5 | 42 | 8 | FVGSPLKI | 14821 | |
| HPV33 | E5 | 42 | 9 | FVGSPLKIF | 14822 | |
| HPV33 | E5 | 42 | 10 | FVGSPLKIFF | 14823 | |
| HPV33 | E5 | 5 | 8 | FVLCFILF | 14824 | |
| HPV33 | E5 | 5 | 9 | FVLCFILFL | 14825 | |
| HPV33 | E5 | 5 | 11 | FVLCFILFLCL | 14826 | |
| HPV33 | E5 | 49 | 8 | IFFCYLLF | 14827 | |
| HPV33 | E5 | 49 | 9 | IFFCYLLFL | 14828 | |
| HPV33 | E5 | 49 | 10 | IFFCYLLFLY | 14829 | |
| HPV33 | E5 | 49 | 11 | IFFCYLLFLYL | 14830 | |
| HPV33 | E5 | 2 | 8 | IFVFVLCF | 14831 | |
| HPV33 | E5 | 2 | 9 | IFVFVLCFI | 14832 | |
| HPV33 | E5 | 2 | 10 | IFVFVLCFIL | 14833 | |
| HPV33 | E5 | 2 | 11 | IFVFVLCFILF | 14834 | |
| HPV33 | E5 | 10 | 8 | ILFLCLSL | 14835 | |
| HPV33 | E5 | 10 | 9 | ILFLCLSLL | 14836 | |
| HPV33 | E5 | 10 | 10 | ILFLCLSLLL | 14837 | |

TABLE X-continued

A24 Supermotif Peptides

| Type | Protein | Position | No. of Amino Acids | Sequence | A*2402 Seq. Id. No. |
|---|---|---|---|---|---|
| HPV33 | E5 | 23 | 9 | ILSISTYAW | 14838 |
| HPV33 | E5 | 23 | 10 | ILSISTYAWL | 14839 |
| HPV33 | E5 | 23 | 11 | ILSISTYAWLL | 14840 |
| HPV33 | E5 | 48 | 8 | KIFFCYLL | 14841 |
| HPV33 | E5 | 48 | 9 | KIFFCYLLF | 14842 |
| HPV33 | E5 | 48 | 10 | KIFFCYLLFL | 14843 |
| HPV33 | E5 | 48 | 11 | KIFFCYLLFLY | 14844 |
| HPV33 | E5 | 11 | 8 | LFLCLSLL | 14845 |
| HPV33 | E5 | 11 | 9 | LFLCLSLLL | 14846 |
| HPV33 | E5 | 55 | 8 | LFLYLPMM | 14847 |
| HPV33 | E5 | 55 | 10 | LFLYLPMMCI | 14848 |
| HPV33 | E5 | 22 | 8 | LILSISTY | 14849 |
| HPV33 | E5 | 22 | 10 | LILSISTYAW | 14850 |
| HPV33 | E5 | 22 | 11 | LILSISTYAWL | 14851 |
| HPV33 | E5 | 54 | 8 | LLFLYLPM | 14852 |
| HPV33 | E5 | 54 | 9 | LLFLYLPMM | 14853 |
| HPV33 | E5 | 54 | 11 | LLFLYLPMMCI | 14854 |
| HPV33 | E5 | 17 | 8 | LLLRPLIL | 14855 |
| HPV33 | E5 | 17 | 10 | LLLRPLILSI | 14856 |
| HPV33 | E5 | 37 | 11 | LLLWVFVGSPL | 14857 |
| HPV33 | E5 | 18 | 9 | LLRPLILSI | 14858 |
| HPV33 | E5 | 32 | 8 | LLVLVLLL | 14859 |
| HPV33 | E5 | 32 | 9 | LLVLVLLLW | 14860 |
| HPV33 | E5 | 32 | 11 | LLVLVLLLWVF | 14861 |
| HPV33 | E5 | 38 | 10 | LLWVFVGSPL | 14862 |
| HPV33 | E5 | 35 | 8 | LVLLLWVF | 14863 |
| HPV33 | E5 | 33 | 8 | LVLVLLLW | 14864 |
| HPV33 | E5 | 33 | 10 | LVLVLLLWVF | 14865 |
| HPV33 | E5 | 39 | 9 | LWVFVGSPL | 14866 |
| HPV33 | E5 | 39 | 11 | LWVFVGSPLKI | 14867 |
| HPV33 | E5 | 57 | 8 | LYLPMMCI | 14868 |
| HPV33 | E5 | 57 | 10 | LYLPMMCINF | 14869 |
| HPV33 | E5 | 1 | 9 | MIFVFVLCF | 14870 |
| HPV33 | E5 | 1 | 10 | MIFVFVLCFI | 14871 |
| HPV33 | E5 | 1 | 11 | MIFVFVLCFIL | 14872 |
| HPV33 | E5 | 61 | 11 | MMCINFHAQHM | 14873 |
| HPV33 | E5 | 21 | 9 | PLILSISTY | 14874 |
| HPV33 | E5 | 21 | 11 | PLILSISTYAW | 14875 |
| HPV33 | E5 | 46 | 8 | PLKIFFCY | 14876 |
| HPV33 | E5 | 46 | 9 | PLKIFFCYL | 14877 |
| HPV33 | E5 | 46 | 10 | PLKIFFCYLL | 14878 |
| HPV33 | E5 | 46 | 11 | PLKIFFCYLLF | 14879 |
| HPV33 | E5 | 25 | 8 | SISTYAWL | 14880 |
| HPV33 | E5 | 25 | 9 | SISTYAWLL | 14881 |
| HPV33 | E5 | 25 | 11 | SISTYAWLLVL | 14882 |
| HPV33 | E5 | 16 | 8 | SLLLRPLI | 14883 |
| HPV33 | E5 | 16 | 9 | SLLLRPLIL | 14884 |
| HPV33 | E5 | 16 | 11 | SLLLRPLILSI | 14885 |
| HPV33 | E5 | 27 | 9 | STYAWLLVL | 14886 |
| HPV33 | E5 | 27 | 11 | STYAWLLVLVL | 14887 |
| HPV33 | E5 | 28 | 8 | TYAWLLVL | 14888 |
| HPV33 | E5 | 28 | 10 | TYAWLLVLVL | 14889 |
| HPV33 | E5 | 28 | 11 | TYAWLLVLVLL | 14890 |
| HPV33 | E5 | 41 | 9 | VFVGSPLKI | 14891 |
| HPV33 | E5 | 41 | 10 | VFVGSPLKIF | 14892 |
| HPV33 | E5 | 41 | 11 | VFVGSPLKIFF | 14893 |
| HPV33 | E5 | 4 | 8 | VFVLCFIL | 14894 |
| HPV33 | E5 | 4 | 9 | VFVLCFILF | 14895 |
| HPV33 | E5 | 4 | 10 | VFVLCFILFL | 14896 |
| HPV33 | E5 | 6 | 8 | VLCFILFL | 14897 |
| HPV33 | E5 | 6 | 10 | VLCFILFLCL | 14898 |
| HPV33 | E5 | 34 | 9 | VLVLLLWVF | 14899 |
| HPV33 | E5 | 31 | 8 | WLLVLVLL | 14900 |
| HPV33 | E5 | 31 | 9 | WLLVLVLLL | 14901 |
| HPV33 | E5 | 31 | 10 | WLLVLVLLLW | 14902 |
| HPV33 | E5 | 40 | 8 | WVFVGSPL | 14903 |
| HPV33 | E5 | 40 | 10 | WVFVGSPLKI | 14904 |
| HPV33 | E5 | 40 | 11 | WVFVGSPLKIF | 14905 |
| HPV33 | E5 | 53 | 9 | YLLFLYLPM | 14906 |
| HPV33 | E5 | 53 | 10 | YLLFLYLPMM | 14907 |
| HPV33 | E5 | 58 | 9 | YLPMMCINF | 14908 |
| HPV33 | E6 | 46 | 9 | AFADLTVVY | 14909 |
| HPV33 | E6 | 18 | 9 | ALETTIHNI | 14910 |
| HPV33 | E6 | 18 | 11 | ALETTIHNIEL | 14911 |

TABLE X-continued

A24 Supermotif Peptides

| Type | Protein | Position | No. of Amino Acids | Sequence | A*2402 | Seq. Id. No. |
|---|---|---|---|---|---|---|
| HPV33 | E6 | 103 | 8 | CIICQRPL | 14912 | |
| HPV33 | E6 | 66 | 8 | CLRFLSKI | 14913 | |
| HPV33 | E6 | 66 | 11 | CLRFLSKISEY | 14914 | |
| HPV33 | E6 | 30 | 8 | CVECKKPL | 14915 | |
| HPV33 | E6 | 139 | 11 | CWRSRRRETAL | 14916 | |
| HPV33 | E6 | 44 | 11 | DFAFADLTVVY | 14917 | |
| HPV33 | E6 | 14 | 10 | DLCQALETTI | 14918 | |
| HPV33 | E6 | 120 | 9 | DLNKRFHNI | 14919 | |
| HPV33 | E6 | 4 | 9 | DTEEKPRTL | 14920 | |
| HPV33 | E6 | 98 | 8 | EILIRCII | 14921 | |
| HPV33 | E6 | 27 | 11 | ELQCVECKKPL | 14922 | |
| HPV33 | E6 | 20 | 9 | ETTIHNIEL | 14923 | |
| HPV33 | E6 | 41 | 10 | EVYDFAFADL | 14924 | |
| HPV33 | E6 | 75 | 10 | EYRHYNYSVY | 14925 | |
| HPV33 | E6 | 69 | 8 | FLSKISEY | 14926 | |
| HPV33 | E6 | 69 | 11 | FLSKISEYRHY | 14927 | |
| HPV33 | E6 | 61 | 9 | GICKLCLRF | 14928 | |
| HPV33 | E6 | 61 | 10 | GICKLCLRFL | 14929 | |
| HPV33 | E6 | 118 | 8 | HVDLNKRF | 14930 | |
| HPV33 | E6 | 118 | 11 | HVDLNKRFHNI | 14931 | |
| HPV33 | E6 | 78 | 11 | HYNYSVYGNTL | 14932 | |
| HPV33 | E6 | 72 | 8 | KISEYRHY | 14933 | |
| HPV33 | E6 | 72 | 10 | KISEYRHYNY | 14934 | |
| HPV33 | E6 | 64 | 10 | KLCLRFLSKI | 14935 | |
| HPV33 | E6 | 100 | 11 | LIRCIICQRPL | 14936 | |
| HPV33 | E6 | 50 | 11 | LTVVYREGNPF | 14937 | |
| HPV33 | E6 | 86 | 11 | NTLEQTVKKPL | 14938 | |
| HPV33 | E6 | 80 | 9 | NYSVYGNTL | 14939 | |
| HPV33 | E6 | 59 | 9 | PFGICKLCL | 14940 | |
| HPV33 | E6 | 59 | 11 | PFGICKLCLRF | 14941 | |
| HPV33 | E6 | 95 | 10 | PLNEILIRCI | 14942 | |
| HPV33 | E6 | 95 | 11 | PLNEILIRCII | 14943 | |
| HPV33 | E6 | 36 | 8 | PLQRSEVY | 14944 | |
| HPV33 | E6 | 36 | 10 | PLQRSEVYDF | 14945 | |
| HPV33 | E6 | 90 | 10 | QTVKKPLNEI | 14946 | |
| HPV33 | E6 | 90 | 11 | QTVKKPLNEIL | 14947 | |
| HPV33 | E6 | 124 | 9 | RFHNISGRW | 14948 | |
| HPV33 | E6 | 68 | 9 | RFLSKISEY | 14949 | |
| HPV33 | E6 | 10 | 10 | RTLHDLCQAL | 14950 | |
| HPV33 | E6 | 131 | 10 | RWAGRCAACW | 14951 | |
| HPV33 | E6 | 87 | 10 | TLEQTVKKPL | 14952 | |
| HPV33 | E6 | 11 | 9 | TLHDLCQAL | 14953 | |
| HPV33 | E6 | 21 | 8 | TTIHNIEL | 14954 | |
| HPV33 | E6 | 91 | 9 | TVKKPLNEI | 14955 | |
| HPV33 | E6 | 91 | 10 | TVKKPLNEIL | 14956 | |
| HPV33 | E6 | 91 | 11 | TVKKPLNEILI | 14957 | |
| HPV33 | E6 | 51 | 10 | TVVYREGNPF | 14958 | |
| HPV33 | E6 | 52 | 9 | VVYREGNPF | 14959 | |
| HPV33 | E6 | 52 | 11 | VVYREGNPFGI | 14960 | |
| HPV33 | E6 | 42 | 9 | VYDFAFADL | 14961 | |
| HPV33 | E6 | 53 | 8 | VYREGNPF | 14962 | |
| HPV33 | E6 | 53 | 10 | VYREGNPFGI | 14963 | |
| HPV33 | E7 | 68 | 9 | CVNSTASDL | 14964 | |
| HPV33 | E7 | 75 | 8 | DLRTIQQL | 14965 | |
| HPV33 | E7 | 75 | 9 | DLRTIQQLL | 14966 | |
| HPV33 | E7 | 75 | 10 | DLRTIQQLLM | 14967 | |
| HPV33 | E7 | 21 | 8 | DLYCYEQL | 14968 | |
| HPV33 | E7 | 14 | 9 | DLYPEPTDL | 14969 | |
| HPV33 | E7 | 14 | 10 | DLYPEPTDLY | 14970 | |
| HPV33 | E7 | 59 | 9 | HTCNTTVRL | 14971 | |
| HPV33 | E7 | 82 | 8 | LLMGTVNI | 14972 | |
| HPV33 | E7 | 15 | 8 | LYPEPTDL | 14973 | |
| HPV33 | E7 | 15 | 9 | LYPEPTDLY | 14974 | |
| HPV33 | E7 | 15 | 11 | LYPEPTDLYCY | 14975 | |
| HPV33 | E7 | 19 | 10 | PTDLYCYEQL | 14976 | |
| HPV33 | E7 | 6 | 8 | PTLKEYVL | 14977 | |
| HPV33 | E7 | 6 | 10 | PTLKEYVLDL | 14978 | |
| HPV33 | E7 | 6 | 11 | PTLKEYVLDLY | 14979 | |
| HPV33 | E7 | 81 | 9 | QLLMGTVNI | 14980 | |
| HPV33 | E7 | 66 | 11 | RLCVNSTASDL | 14981 | |
| HPV33 | E7 | 77 | 8 | RTIQQLLM | 14982 | |
| HPV33 | E7 | 71 | 9 | STASDLRTI | 14983 | |
| HPV33 | E7 | 7 | 9 | TLKEYVLDL | 14984 | |
| HPV33 | E7 | 7 | 10 | TLKEYVLDLY | 14985 | |

TABLE X-continued

A24 Supermotif Peptides

| Type | Protein | Position | No. of Amino Acids | Sequence | A*2402 | Seq. Id. No. |
|---|---|---|---|---|---|---|
| HPV33 | E7 | 12 | 11 | VLDLYPEPTDL | 14986 | |
| HPV33 | L1 | 290 | 10 | AFFPTPSGSM | 14987 | |
| HPV33 | L1 | 392 | 10 | AMNPDILEDW | 14988 | |
| HPV33 | L1 | 44 | 9 | AVGHPYFSI | 14989 | |
| HPV33 | L1 | 270 | 8 | AVPDDLYI | 14990 | |
| HPV33 | L1 | 147 | 11 | CLSMDYKQTQL | 14991 | |
| HPV33 | L1 | 345 | 10 | CTQVTSDSTY | 14992 | |
| HPV33 | L1 | 223 | 9 | DICGSTCKY | 14993 | |
| HPV33 | L1 | 396 | 8 | DILEDWQF | 14994 | |
| HPV33 | L1 | 396 | 10 | DILEDWQFGL | 14995 | |
| HPV33 | L1 | 457 | 11 | DLDQFPLGRKF | 14996 | |
| HPV33 | L1 | 449 | 10 | DLKEKFSADL | 14997 | |
| HPV33 | L1 | 370 | 8 | DLQFVFQL | 14998 | |
| HPV33 | L1 | 199 | 10 | DMVDTGFGCM | 14999 | |
| HPV33 | L1 | 129 | 8 | DTETGNKY | 15000 | |
| HPV33 | L1 | 202 | 9 | DTGFGCMDF | 15001 | |
| HPV33 | L1 | 335 | 8 | DTTRSTNM | 15002 | |
| HPV33 | L1 | 335 | 10 | DTTRSTNMTL | 15003 | |
| HPV33 | L1 | 415 | 11 | DTYRFVTSQAI | 15004 | |
| HPV33 | L1 | 151 | 9 | DYKQTQLCL | 15005 | |
| HPV33 | L1 | 151 | 10 | DYKQTQLCLL | 15006 | |
| HPV33 | L1 | 233 | 10 | DYLKMTSEPY | 15007 | |
| HPV33 | L1 | 107 | 8 | EIGRGQPL | 15008 | |
| HPV33 | L1 | 447 | 8 | EVDLKEKF | 15009 | |
| HPV33 | L1 | 385 | 9 | EVMTYIHAM | 15010 | |
| HPV33 | L1 | 368 | 8 | EYDLQFVF | 15011 | |
| HPV33 | L1 | 368 | 10 | EYDLQFVFQL | 15012 | |
| HPV33 | L1 | 361 | 9 | EYIRHVEEY | 15013 | |
| HPV33 | L1 | 361 | 11 | EYIRHVEEYDL | 15014 | |
| HPV33 | L1 | 26 | 8 | EYVSTRSI | 15015 | |
| HPV33 | L1 | 26 | 9 | EYVSRTSIY | 15016 | |
| HPV33 | L1 | 26 | 10 | EYVSRTSIYY | 15017 | |
| HPV33 | L1 | 26 | 11 | EYVSRTSIYYY | 15018 | |
| HPV33 | L1 | 247 | 9 | FFFLRREQM | 15019 | |
| HPV33 | L1 | 247 | 10 | FFFLRREQMF | 15020 | |
| HPV33 | L1 | 248 | 8 | FFLRREQM | 15021 | |
| HPV33 | L1 | 248 | 9 | FFLRREQMF | 15022 | |
| HPV33 | L1 | 260 | 8 | FFNRAGTL | 15023 | |
| HPV33 | L1 | 291 | 9 | FFPTPSGSM | 15024 | |
| HPV33 | L1 | 249 | 8 | FLRREQMF | 15025 | |
| HPV33 | L1 | 373 | 10 | FVFQLCKVTL | 15026 | |
| HPV33 | L1 | 445 | 10 | FWEVDLKEKF | 15027 | |
| HPV33 | L1 | 91 | 9 | FYNPDTQRL | 15028 | |
| HPV33 | L1 | 91 | 11 | FYNPDTQRLVW | 15029 | |
| HPV33 | L1 | 204 | 10 | GFGCMDFKTL | 15030 | |
| HPV33 | L1 | 85 | 8 | GFPDTSFY | 15031 | |
| HPV33 | L1 | 322 | 9 | GICWGNQVF | 15032 | |
| HPV33 | L1 | 117 | 8 | GISGHPLL | 15033 | |
| HPV33 | L1 | 117 | 11 | GISGHPLLNKF | 15034 | |
| HPV33 | L1 | 105 | 10 | GLEIGRGQPL | 15035 | |
| HPV33 | L1 | 472 | 8 | GLKAKPKL | 15036 | |
| HPV33 | L1 | 68 | 11 | GLQYRVFRVRL | 15037 | |
| HPV33 | L1 | 404 | 10 | GLTPPPSASL | 15038 | |
| HPV33 | L1 | 265 | 11 | GTLGEAVPDDL | 15039 | |
| HPV33 | L1 | 281 | 11 | GTTASIQSSAF | 15040 | |
| HPV33 | L1 | 115 | 9 | GVGISGHPL | 15041 | |
| HPV33 | L1 | 115 | 10 | GVGISGHPLL | 15042 | |
| HPV33 | L1 | 259 | 9 | HFFNRAGTL | 15043 | |
| HPV33 | L1 | 365 | 9 | HVEEYDLQF | 15044 | |
| HPV33 | L1 | 365 | 11 | HVEEYDLQFVF | 15045 | |
| HPV33 | L1 | 397 | 9 | ILEDWQFGL | 15046 | |
| HPV33 | L1 | 33 | 10 | IYYYAGSSRL | 15047 | |
| HPV33 | L1 | 33 | 11 | IYYYAGSSRLL | 15048 | |
| HPV33 | L1 | 126 | 11 | KFDDTETGNKY | 15049 | |
| HPV33 | L1 | 83 | 9 | KFGFPDTSF | 15050 | |
| HPV33 | L1 | 83 | 10 | KFGFPDTSFY | 15051 | |
| HPV33 | L1 | 466 | 8 | KFLLQAGL | 15052 | |
| HPV33 | L1 | 453 | 9 | KFSADLDQF | 15053 | |
| HPV33 | L1 | 453 | 11 | KFSADLDQFPL | 15054 | |
| HPV33 | L1 | 60 | 10 | KLLVPKVSGL | 15055 | |
| HPV33 | L1 | 236 | 11 | KMTSEPYGDSL | 15056 | |
| HPV33 | L1 | 65 | 10 | KVSGLQYRVF | 15057 | |
| HPV33 | L1 | 379 | 9 | KVTLTAEVM | 15058 | |
| HPV33 | L1 | 379 | 11 | KVTLTAEVMTY | 15059 | |

TABLE X-continued

A24 Supermotif Peptides

| Type | Protein | Position | No. of Amino Acids | Sequence | A*2402 Seq. Id. No. |
|---|---|---|---|---|---|
| HPV33 | L1 | 20 | 8 | KVVSTDEY | 15060 |
| HPV33 | L1 | 230 | 8 | KYPDYLKM | 15061 |
| HPV33 | L1 | 442 | 9 | KYTFWEVDL | 15062 |
| HPV33 | L1 | 246 | 10 | LFFFLRREQM | 15063 |
| HPV33 | L1 | 246 | 11 | LFFFLRREQMF | 15064 |
| HPV33 | L1 | 306 | 8 | LFNKPYWL | 15065 |
| HPV33 | L1 | 190 | 11 | LINTIIEDGDM | 15066 |
| HPV33 | L1 | 42 | 8 | LLAVGHPY | 15067 |
| HPV33 | L1 | 42 | 9 | LLAVGHPYF | 15068 |
| HPV33 | L1 | 42 | 11 | LLAVGHPYFSI | 15069 |
| HPV33 | L1 | 61 | 9 | LLVPKVSGL | 15070 |
| HPV33 | L1 | 61 | 11 | LLVPKVSGLQY | 15071 |
| HPV33 | L1 | 382 | 8 | LTAEVMTY | 15072 |
| HPV33 | L1 | 382 | 9 | LTAEVMTYI | 15073 |
| HPV33 | L1 | 405 | 9 | LTPPPSASL | 15074 |
| HPV33 | L1 | 62 | 8 | LVPKVSGL | 15075 |
| HPV33 | L1 | 62 | 10 | LVPKVSGLQY | 15076 |
| HPV33 | L1 | 99 | 8 | LVWACVGL | 15077 |
| HPV33 | L1 | 99 | 10 | LVWACVGLEI | 15078 |
| HPV33 | L1 | 237 | 10 | MTSEPYGDSL | 15079 |
| HPV33 | L1 | 237 | 11 | MTSEPYGDSLF | 15080 |
| HPV33 | L1 | 387 | 11 | MTYIHAMNPDI | 15081 |
| HPV33 | L1 | 200 | 9 | MVDTGFGCM | 15082 |
| HPV33 | L1 | 200 | 11 | MVDTGFGCMDF | 15083 |
| HPV33 | L1 | 299 | 8 | MVTSESQL | 15084 |
| HPV33 | L1 | 299 | 9 | MVTSESQLF | 15085 |
| HPV33 | L1 | 192 | 9 | NTIIEDGDM | 15086 |
| HPV33 | L1 | 221 | 11 | PIDICGSTCKY | 15087 |
| HPV33 | L1 | 187 | 8 | PLELINTI | 15088 |
| HPV33 | L1 | 187 | 9 | PLELINTII | 15089 |
| HPV33 | L1 | 439 | 8 | PLGKYTFW | 15090 |
| HPV33 | L1 | 462 | 8 | PLGRKFLL | 15091 |
| HPV33 | L1 | 113 | 11 | PLGVGISGHPL | 15092 |
| HPV33 | L1 | 55 | 8 | PTNAKKLL | 15093 |
| HPV33 | L1 | 17 | 11 | PVSKVVSTDEY | 15094 |
| HPV33 | L1 | 241 | 8 | PYGDSLFF | 15095 |
| HPV33 | L1 | 241 | 9 | PYGDSLFFF | 15096 |
| HPV33 | L1 | 241 | 10 | PYGDSLFFFL | 15097 |
| HPV33 | L1 | 460 | 8 | QFPLGRKF | 15098 |
| HPV33 | L1 | 460 | 9 | QFPLGRKFL | 15099 |
| HPV33 | L1 | 460 | 10 | QFPLGRKFLL | 15100 |
| HPV33 | L1 | 372 | 11 | QFVFQLCKVTL | 15101 |
| HPV33 | L1 | 305 | 8 | QLFNKPYW | 15102 |
| HPV33 | L1 | 305 | 9 | QLFNKPYWL | 15103 |
| HPV33 | L1 | 254 | 8 | QMFVRHFF | 15104 |
| HPV33 | L1 | 347 | 8 | QVTSDSTY | 15105 |
| HPV33 | L1 | 70 | 9 | QYRVFRVRL | 15016 |
| HPV33 | L1 | 418 | 8 | RFVTSQAI | 15107 |
| HPV33 | L1 | 41 | 9 | RLLAVGHPY | 15018 |
| HPV33 | L1 | 41 | 10 | RLLAVGHPYF | 15019 |
| HPV33 | L1 | 77 | 8 | RLPDPNKF | 15110 |
| HPV33 | L1 | 77 | 10 | RLPDPNKFGF | 15111 |
| HPV33 | L1 | 98 | 9 | RLVWACVGL | 15112 |
| HPV33 | L1 | 98 | 11 | RLVWACVGLEI | 15113 |
| HPV33 | L1 | 75 | 10 | RVRLPDPNKF | 15114 |
| HPV33 | L1 | 90 | 10 | SKYNPDTQRL | 15115 |
| HPV33 | L1 | 51 | 11 | SIKNPTNAKKL | 15116 |
| HPV33 | L1 | 285 | 8 | SIQSSAFF | 15117 |
| HPV33 | L1 | 32 | 11 | SIYYYAGSSRL | 15118 |
| HPV33 | L1 | 245 | 11 | SLFFFLRREQM | 15119 |
| HPV33 | L1 | 412 | 8 | SLQDTYRF | 15120 |
| HPV33 | L1 | 149 | 9 | SMDYKQTQL | 15121 |
| HPV33 | L1 | 149 | 11 | SMDYKQTQLCL | 15122 |
| HPV33 | L1 | 298 | 9 | SMVTSESQL | 15123 |
| HPV33 | L1 | 298 | 10 | SMVTSESQLF | 15124 |
| HPV33 | L1 | 227 | 8 | STCKYPDY | 15125 |
| HPV33 | L1 | 227 | 9 | STCKYPDYL | 15126 |
| HPV33 | L1 | 227 | 11 | STCKYPDYLKM | 15127 |
| HPV33 | L1 | 23 | 11 | STDEYVSRTSI | 15128 |
| HPV33 | L1 | 352 | 8 | STYKNENF | 15129 |
| HPV33 | L1 | 352 | 11 | STYKNENFKEY | 15130 |
| HPV33 | L1 | 2 | 11 | SVWRPSEATVY | 15131 |
| HPV33 | L1 | 444 | 11 | TFWEVDLKEKF | 15132 |
| HPV33 | L1 | 193 | 8 | TIIEDGDM | 15133 |

TABLE X-continued

A24 Supermotif Peptides

| Type | Protein | Position | No. of Amino Acids | Sequence | A*2402 | Seq. Id. No. |
|---|---|---|---|---|---|---|
| HPV33 | L1 | 266 | 10 | TLGEAVPDDL | 15134 | |
| HPV33 | L1 | 266 | 11 | TLGEAVPDDLY | 15135 | |
| HPV33 | L1 | 212 | 11 | TLQANKSDVPI | 15136 | |
| HPV33 | L1 | 381 | 9 | TLTAEVMTY | 15137 | |
| HPV33 | L1 | 381 | 10 | TLTAEVMTYI | 15138 | |
| HPV33 | L1 | 282 | 10 | TTASIQSSAF | 15139 | |
| HPV33 | L1 | 282 | 11 | TTASIQSSAFF | 15140 | |
| HPV33 | L1 | 336 | 9 | TTRSTNMTL | 15141 | |
| HPV33 | L1 | 430 | 11 | TVPPKEKEDPL | 15142 | |
| HPV33 | L1 | 332 | 11 | TVVDTTRSTNM | 15143 | |
| HPV33 | L1 | 388 | 10 | TYIHAMNPDI | 15144 | |
| HPV33 | L1 | 388 | 11 | TYIHAMNPDIL | 15145 | |
| HPV33 | L1 | 353 | 10 | TYKNENFKEY | 15146 | |
| HPV33 | L1 | 353 | 11 | TYKNENFKEYI | 15147 | |
| HPV33 | L1 | 416 | 10 | TYRFVTSQAI | 15148 | |
| HPV33 | L1 | 374 | 9 | VFQLCKVTL | 15149 | |
| HPV33 | L1 | 386 | 8 | VMTYIHAM | 15150 | |
| HPV33 | L1 | 380 | 8 | VTLTAEVM | 15151 | |
| HPV33 | L1 | 380 | 10 | VTLTAEVMTY | 15152 | |
| HPV33 | L1 | 380 | 11 | VTLTAEVMTYI | 15153 | |
| HPV33 | L1 | 300 | 8 | VTSESQLF | 15154 | |
| HPV33 | L1 | 333 | 10 | VVDTTRSTNM | 15155 | |
| HPV33 | L1 | 100 | 9 | VWACVGLEI | 15156 | |
| HPV33 | L1 | 3 | 10 | VWRPSEATVY | 15157 | |
| HPV33 | L1 | 3 | 11 | VWRPSEATVYL | 15158 | |
| HPV33 | L1 | 389 | 9 | YIHAMNPDI | 15159 | |
| HPV33 | L1 | 389 | 10 | YIHAMNPDIL | 15160 | |
| HPV33 | L1 | 276 | 11 | YIKGSGTTASI | 15161 | |
| HPV33 | L1 | 362 | 8 | YIRHVEEY | 15162 | |
| HPV33 | L1 | 362 | 10 | YIRHVEEYDL | 15163 | |
| HPV33 | L1 | 234 | 9 | YLKMTSEPY | 15164 | |
| HPV33 | L1 | 443 | 8 | YTFWEVDL | 15165 | |
| HPV33 | L1 | 27 | 8 | YVSRTSIY | 15166 | |
| HPV33 | L1 | 27 | 9 | YVSRTSIYY | 15167 | |
| HPV33 | L1 | 27 | 10 | YVSRTSIYYY | 15168 | |
| HPV33 | L1 | 35 | 8 | YYAGSSRL | 15169 | |
| HPV33 | L1 | 35 | 9 | YYAGSSRLL | 15170 | |
| HPV33 | L1 | 34 | 9 | YYYAGSSRL | 15171 | |
| HPV33 | L1 | 34 | 10 | YYYAGSSRLL | 15172 | |
| HPV33 | L2 | 256 | 11 | AFESFDPEDTL | 15173 | |
| HPV33 | L2 | 241 | 9 | AFLTSPHKL | 15174 | |
| HPV33 | L2 | 241 | 10 | AFLTSPHKLI | 15175 | |
| HPV33 | L2 | 291 | 11 | AITSRRHTVRF | 15176 | |
| HPV33 | L2 | 23 | 10 | ATGTCPPDVI | 15177 | |
| HPV33 | L2 | 308 | 11 | ATLKTRSGKQI | 15178 | |
| HPV33 | L2 | 385 | 10 | ATTRTSNVSI | 15179 | |
| HPV33 | L2 | 280 | 8 | DFLDIIAL | 15180 | |
| HPV33 | L2 | 439 | 8 | DFVLHPSY | 15181 | |
| HPV33 | L2 | 439 | 9 | DFVLHPSYF | 15182 | |
| HPV33 | L2 | 439 | 10 | DFVLHPSYFI | 15183 | |
| HPV33 | L2 | 439 | 11 | DFVLHPSYFIL | 15184 | |
| HPV33 | L2 | 283 | 10 | DILALHRPAI | 15185 | |
| HPV33 | L2 | 272 | 10 | DISPAPDPDF | 15186 | |
| HPV33 | L2 | 272 | 11 | DISPAPDPDFL | 15187 | |
| HPV33 | L2 | 327 | 8 | DLSPIVPL | 15188 | |
| HPV33 | L2 | 431 | 10 | DTIVVDGADF | 15189 | |
| HPV33 | L2 | 264 | 10 | DTLQFQHSDI | 15190 | |
| HPV33 | L2 | 401 | 10 | DTPVMSGPDI | 15191 | |
| HPV33 | L2 | 350 | 9 | DTSTSSYSI | 15192 | |
| HPV33 | L2 | 95 | 10 | DTVGPLDSSI | 15193 | |
| HPV33 | L2 | 369 | 9 | DVDNVHTPM | 15194 | |
| HPV33 | L2 | 30 | 11 | DVIPKVEGSTI | 15195 | |
| HPV33 | L2 | 113 | 11 | FIEAGAPAPSI | 15196 | |
| HPV33 | L2 | 447 | 10 | FILRRRRKRF | 15197 | |
| HPV33 | L2 | 242 | 8 | FLTSPHKL | 15198 | |
| HPV33 | L2 | 242 | 9 | FLTSPHKLI | 15199 | |
| HPV33 | L2 | 242 | 11 | FLTSPHKLITY | 15200 | |
| HPV33 | L2 | 440 | 8 | FVLHPSYF | 15201 | |
| HPV33 | L2 | 440 | 9 | FVLHPSYFI | 15202 | |
| HPV33 | L2 | 440 | 10 | FVLHPSYFIL | 15203 | |
| HPV33 | L2 | 421 | 8 | FVPISPFF | 15204 | |
| HPV33 | L2 | 421 | 10 | FVPISPFFPF | 15205 | |
| HPV33 | L2 | 25 | 8 | GTCPPDVI | 15206 | |
| HPV33 | L2 | 75 | 9 | GTDPPTAAI | 15207 | |

TABLE X-continued

A24 Supermotif Peptides

| Type | Protein | Position | No. of Amino Acids | Sequence | A*2402 | Seq. Id. No. |
|---|---|---|---|---|---|---|
| HPV33 | L2 | 75 | 11 | GTDPPTAAIPL | 15208 | |
| HPV33 | L2 | 51 | 9 | GVFFGGLGI | 15209 | |
| HPV33 | L2 | 374 | 8 | HTPMQHSY | 15210 | |
| HPV33 | L2 | 374 | 11 | HTPMQHSYSTF | 15211 | |
| HPV33 | L2 | 336 | 8 | HTVPNEQY | 15212 | |
| HPV33 | L2 | 336 | 10 | HTVPNEQYEL | 15213 | |
| HPV33 | L2 | 323 | 9 | HYYQDLSPI | 15214 | |
| HPV33 | L2 | 284 | 9 | IIALHRPAI | 15215 | |
| HPV33 | L2 | 44 | 10 | ILKYGSLGVF | 15216 | |
| HPV33 | L2 | 44 | 11 | ILKYGSLGVFF | 15217 | |
| HPV33 | L2 | 448 | 9 | ILRRRKRF | 15218 | |
| HPV33 | L2 | 448 | 11 | ILRRRKRFPY | 15219 | |
| HPV33 | L2 | 292 | 10 | ITSRRHTVRF | 15220 | |
| HPV33 | L2 | 250 | 8 | ITYDNPAF | 15221 | |
| HPV33 | L2 | 250 | 11 | ITYDNPAFESF | 15222 | |
| HPV33 | L2 | 104 | 10 | IVSLIEETSF | 15223 | |
| HPV33 | L2 | 104 | 11 | IVSLIEETSFI | 15224 | |
| HPV33 | L2 | 433 | 8 | IVVDGADF | 15225 | |
| HPV33 | L2 | 433 | 10 | IVVDGADFVL | 15226 | |
| HPV33 | L2 | 248 | 10 | KLITYDNPAF | 15227 | |
| HPV33 | L2 | 311 | 8 | KTRSGKQI | 15228 | |
| HPV33 | L2 | 34 | 11 | KVEGSTIADQI | 15229 | |
| HPV33 | L2 | 236 | 8 | KVVDPAFL | 15230 | |
| HPV33 | L2 | 46 | 8 | KYGSLGVF | 15231 | |
| HPV33 | L2 | 46 | 9 | KYGSLGVFF | 15232 | |
| HPV33 | L2 | 414 | 8 | LFPTSSPF | 15233 | |
| HPV33 | L2 | 414 | 11 | LFPTSSPFVPI | 15234 | |
| HPV33 | L2 | 107 | 8 | LIEETSFI | 15235 | |
| HPV33 | L2 | 249 | 9 | LITYDNPAF | 15236 | |
| HPV33 | L2 | 243 | 8 | LTSPHKLI | 15237 | |
| HPV33 | L2 | 243 | 10 | LTSPHKLITY | 15238 | |
| HPV33 | L2 | 397 | 9 | NTGFDTPVM | 15239 | |
| HPV33 | L2 | 372 | 10 | NVHTPMQHSY | 15240 | |
| HPV33 | L2 | 391 | 10 | NVSIPLNTGF | 15241 | |
| HPV33 | L2 | 143 | 10 | NVSSVGESSI | 15242 | |
| HPV33 | L2 | 209 | 8 | NVTSSTPI | 15243 | |
| HPV33 | L2 | 426 | 8 | PFFPFDTI | 15244 | |
| HPV33 | L2 | 420 | 8 | PFVPISPF | 15245 | |
| HPV33 | L2 | 420 | 9 | PFVPISPFF | 15246 | |
| HPV33 | L2 | 420 | 11 | PFVPISPFFPF | 15247 | |
| HPV33 | L2 | 73 | 11 | PIGTDPPTAAI | 15248 | |
| HPV33 | L2 | 215 | 11 | PIPGSRPVARL | 15249 | |
| HPV33 | L2 | 423 | 8 | PISPFFPF | 15250 | |
| HPV33 | L2 | 423 | 11 | PISPFFPFDTI | 15251 | |
| HPV33 | L2 | 333 | 11 | PLDHTVPNEQY | 15252 | |
| HPV33 | L2 | 99 | 9 | PLDSSIVSL | 15253 | |
| HPV33 | L2 | 99 | 10 | PLDSSIVSLI | 15254 | |
| HPV33 | L2 | 413 | 9 | PLFPTSSPF | 15255 | |
| HPV33 | L2 | 347 | 10 | PLHDTSTSSY | 15256 | |
| HPV33 | L2 | 395 | 11 | PLNTGFDTPVM | 15257 | |
| HPV33 | L2 | 376 | 9 | PMQHSYSTF | 15258 | |
| HPV33 | L2 | 79 | 10 | PTAAIPLQPI | 15259 | |
| HPV33 | L2 | 161 | 9 | PTFTEPSVL | 15260 | |
| HPV33 | L2 | 416 | 9 | PTSSPFVPI | 15261 | |
| HPV33 | L2 | 186 | 8 | PTVSTQSY | 15262 | |
| HPV33 | L2 | 186 | 11 | PTVSTQSYENI | 15263 | |
| HPV33 | L2 | 221 | 8 | PVARLGLY | 15264 | |
| HPV33 | L2 | 403 | 8 | PVMSGPDI | 15265 | |
| HPV33 | L2 | 91 | 10 | PVTVDTVGPL | 15266 | |
| HPV33 | L2 | 317 | 8 | QIGARIHY | 15267 | |
| HPV33 | L2 | 317 | 9 | QIGARIHYY | 15268 | |
| HPV33 | L2 | 43 | 8 | QILKYGSL | 15269 | |
| HPV33 | L2 | 43 | 11 | QILKYGSLGVF | 15270 | |
| HPV33 | L2 | 153 | 11 | QTISTHLNPTF | 15271 | |
| HPV33 | L2 | 234 | 9 | QVKVVDPAF | 15272 | |
| HPV33 | L2 | 234 | 10 | QVKVVDPAFL | 15273 | |
| HPV33 | L2 | 300 | 11 | RFSRVGQKATL | 15274 | |
| HPV33 | L2 | 321 | 8 | RIHYYQDL | 15275 | |
| HPV33 | L2 | 321 | 11 | RIHYYQDLSPI | 15276 | |
| HPV33 | L2 | 388 | 9 | RTSNVSIPL | 15277 | |
| HPV33 | L2 | 303 | 8 | RVGQKATL | 15278 | |
| HPV33 | L2 | 259 | 8 | SFDPEDTL | 15279 | |
| HPV33 | L2 | 259 | 10 | SFDPEDTLQF | 15280 | |
| HPV33 | L2 | 357 | 10 | SINDGLYDVY | 15281 | |

TABLE X-continued

A24 Supermotif Peptides

| Type | Protein | Position | No. of Amino Acids | Sequence | A*2402 Seq. Id. No. |
|---|---|---|---|---|---|
| HPV33 | L2 | 393 | 8 | SIPLNTGF | 15282 |
| HPV33 | L2 | 122 | 8 | SIPTPSGF | 15283 |
| HPV33 | L2 | 151 | 9 | SIQTISTHL | 15284 |
| HPV33 | L2 | 103 | 11 | SIVSLIEETSF | 15285 |
| HPV33 | L2 | 49 | 9 | SLGVFFGGL | 15286 |
| HPV33 | L2 | 49 | 11 | SLGVFFGGLGI | 15287 |
| HPV33 | L2 | 106 | 8 | SLIEETSF | 15288 |
| HPV33 | L2 | 106 | 9 | SLIEETSFI | 15289 |
| HPV33 | L2 | 156 | 8 | STHLNPTF | 15290 |
| HPV33 | L2 | 38 | 8 | STIADQIL | 15291 |
| HPV33 | L2 | 38 | 10 | STIADQILKY | 15292 |
| HPV33 | L2 | 189 | 8 | STQSYENI | 15293 |
| HPV33 | L2 | 189 | 10 | STQSYENIPM | 15294 |
| HPV33 | L2 | 352 | 11 | STSSYSINDGL | 15295 |
| HPV33 | L2 | 146 | 10 | SVGESSIQTI | 15296 |
| HPV33 | L2 | 192 | 10 | SYENIPMDTF | 15297 |
| HPV33 | L2 | 355 | 8 | SYSINDGL | 15298 |
| HPV33 | L2 | 355 | 9 | SYSINDGLY | 15299 |
| HPV33 | L2 | 162 | 8 | TFTEPSVL | 15300 |
| HPV33 | L2 | 39 | 9 | TIADQILKY | 15301 |
| HPV33 | L2 | 154 | 10 | TISTHLNPTF | 15302 |
| HPV33 | L2 | 432 | 9 | TIVVDGADF | 15303 |
| HPV33 | L2 | 432 | 11 | TIVVDGADFVL | 15304 |
| HPV33 | L2 | 309 | 10 | TLKTRSGKQI | 15305 |
| HPV33 | L2 | 265 | 9 | TLQFQHSDI | 15306 |
| HPV33 | L2 | 386 | 9 | TTRTSNVSI | 15307 |
| HPV33 | L2 | 386 | 11 | TTRTSNVSIPL | 15308 |
| HPV33 | L2 | 132 | 10 | TTSADTTPAI | 15309 |
| HPV33 | L2 | 132 | 11 | TTSADTTPAII | 15310 |
| HPV33 | L2 | 93 | 8 | TVDTVGPL | 15311 |
| HPV33 | L2 | 96 | 9 | TVGPLDSSI | 15312 |
| HPV33 | L2 | 337 | 9 | TVPENQYEL | 15313 |
| HPV33 | L2 | 187 | 10 | TVSTQSYENI | 15314 |
| HPV33 | L2 | 251 | 10 | TYDNPAFESF | 15315 |
| HPV33 | L2 | 52 | 8 | VFFGGLGI | 15316 |
| HPV33 | L2 | 31 | 10 | VIPKVEGSTI | 15317 |
| HPV33 | L2 | 441 | 8 | VLHPSYFI | 15318 |
| HPV33 | L2 | 441 | 9 | VLHPSYFIL | 15319 |
| HPV33 | L2 | 404 | 11 | VMSGPDIPSPL | 15320 |
| HPV33 | L2 | 131 | 11 | VTTSADTTPAI | 15321 |
| HPV33 | L2 | 92 | 9 | VTVDTVGPL | 15322 |
| HPV33 | L2 | 434 | 9 | VVDGADFVL | 15323 |
| HPV33 | L2 | 446 | 11 | YFILRRRKRF | 15324 |
| HPV33 | L2 | 324 | 8 | YYQDLSPI | 15325 |
| HPV33 | L2 | 324 | 11 | YYQDLSPIVPL | 15326 |
| HPV45 | E1 | 384 | 11 | AFLKSNCQAKY | 15327 |
| HPV45 | E1 | 532 | 9 | ALDGNPISI | 15328 |
| HPV45 | E1 | 311 | 9 | ALYWYRTGI | 15329 |
| HPV45 | E1 | 199 | 9 | AMLAVFKDI | 15330 |
| HPV45 | E1 | 199 | 10 | AMLAVFKDIY | 15331 |
| HPV45 | E1 | 512 | 11 | AMLDDATHTCW | 15332 |
| HPV45 | E1 | 40 | 8 | ATDTGSDM | 15333 |
| HPV45 | E1 | 40 | 11 | ATDTGSDMVDF | 15334 |
| HPV45 | E1 | 517 | 8 | ATHTCWTY | 15335 |
| HPV45 | E1 | 517 | 9 | ATHTCWTYF | 15336 |
| HPV45 | E1 | 251 | 10 | ATLYAHIQCL | 15337 |
| HPV45 | E1 | 202 | 9 | AVFKDIYGL | 15338 |
| HPV45 | E1 | 202 | 11 | AVFKDIYGLSF | 15339 |
| HPV45 | E1 | 604 | 10 | CFFERTWSRL | 15340 |
| HPV45 | E1 | 259 | 9 | CLDCKWGVL | 15341 |
| HPV45 | E1 | 259 | 10 | CLDCKWGVLI | 15342 |
| HPV45 | E1 | 259 | 11 | CLDCKWGVLIL | 15343 |
| HPV45 | E1 | 297 | 9 | CMLIEPPKL | 15344 |
| HPV45 | E1 | 226 | 8 | CTDWVMAI | 15345 |
| HPV45 | E1 | 226 | 9 | CTDWVMAIF | 15346 |
| HPV45 | E1 | 634 | 10 | CVTGQNTRPL | 15347 |
| HPV45 | E1 | 521 | 8 | CWTYFDNY | 15348 |
| HPV45 | E1 | 521 | 9 | CWTYFDNYM | 15349 |
| HPV45 | E1 | 49 | 9 | DFIDTQLSI | 15350 |
| HPV45 | E1 | 206 | 10 | DIYGLSFTDL | 15351 |
| HPV45 | E1 | 349 | 8 | DLSDMVQW | 15352 |
| HPV45 | E1 | 349 | 10 | DLSDMVQWAF | 15353 |
| HPV45 | E1 | 108 | 9 | DLSPRLQEI | 15354 |
| HPV45 | E1 | 108 | 11 | DLSPRLQEISL | 15355 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | E1 | 361 | 8 | DLTDESDM | 15356 | |
| HPV45 | E1 | 361 | 10 | DLTDESDMAF | 15357 | |
| HPV45 | E1 | 367 | 9 | DMAFQYAQL | 15358 | |
| HPV45 | E1 | 46 | 10 | DMVDFIDTQL | 15359 | |
| HPV45 | E1 | 352 | 11 | DMVQWAFDNDL | 15360 | |
| HPV45 | E1 | 106 | 8 | DTDLSPRL | 15361 | |
| HPV45 | E1 | 106 | 11 | DTDLSPRLQEI | 15362 | |
| HPV45 | E1 | 623 | 10 | DTEGIPFGTF | 15363 | |
| HPV45 | E1 | 42 | 9 | DTGSDMVDF | 15364 | |
| HPV45 | E1 | 42 | 10 | DTGSDMVDFI | 15365 | |
| HPV45 | E1 | 328 | 9 | DTPEWIQRL | 15366 | |
| HPV45 | E1 | 328 | 11 | DTPEWIQRLTI | 15367 | |
| HPV45 | E1 | 431 | 8 | DWRPIVQF | 15368 | |
| HPV45 | E1 | 431 | 9 | DWRPIVQFL | 15369 | |
| HPV45 | E1 | 431 | 11 | DWRPIVQFLRY | 15370 | |
| HPV45 | E1 | 445 | 9 | EFISFLRAL | 15371 | |
| HPV45 | E1 | 596 | 10 | EINDKNWKCF | 15372 | |
| HPV45 | E1 | 596 | 11 | EINDKNWKCFF | 15373 | |
| HPV45 | E1 | 38 | 10 | ETATDTGSDM | 15374 | |
| HPV45 | E1 | 295 | 11 | ETCMLIEPPKL | 15375 | |
| HPV45 | E1 | 74 | 9 | EVQNDAQVL | 15376 | |
| HPV45 | E1 | 74 | 11 | EVQNDAQVLHL | 15377 | |
| HPV45 | E1 | 324 | 9 | EVSGDTPEW | 15378 | |
| HPV45 | E1 | 324 | 10 | EVSGDTPEWI | 15379 | |
| HPV45 | E1 | 331 | 8 | EWIQRLTI | 15380 | |
| HPV45 | E1 | 331 | 9 | EWIQRLTII | 15381 | |
| HPV45 | E1 | 605 | 9 | FFERTWSRL | 15382 | |
| HPV45 | E1 | 605 | 11 | FFERTWSRLDL | 15383 | |
| HPV45 | E1 | 50 | 8 | FIDTQLSI | 15384 | |
| HPV45 | E1 | 483 | 9 | FIHFLQGAI | 15385 | |
| HPV45 | E1 | 483 | 10 | FIHFLQGAII | 15386 | |
| HPV45 | E1 | 446 | 8 | FISFLRAL | 15387 | |
| HPV45 | E1 | 446 | 11 | FISFLRALKEF | 15388 | |
| HPV45 | E1 | 456 | 11 | FLKGTPKKNCI | 15389 | |
| HPV45 | E1 | 385 | 10 | FLKSNCQAKY | 15390 | |
| HPV45 | E1 | 385 | 11 | FLKSNCQAKYL | 15391 | |
| HPV45 | E1 | 486 | 9 | FLQGAIISF | 15392 | |
| HPV45 | E1 | 449 | 8 | FLRALKEF | 15393 | |
| HPV45 | E1 | 449 | 9 | FLRALKEFL | 15394 | |
| HPV45 | E1 | 438 | 9 | FLRYQGVEF | 15395 | |
| HPV45 | E1 | 438 | 10 | FLRYQGVEFI | 15396 | |
| HPV45 | E1 | 212 | 8 | FTDLVRNF | 15397 | |
| HPV45 | E1 | 579 | 9 | FTFPHAFPF | 15398 | |
| HPV45 | E1 | 130 | 8 | FTISDSGY | 15399 | |
| HPV45 | E1 | 494 | 8 | FVNSNSHF | 15400 | |
| HPV45 | E1 | 494 | 9 | FVNSNSHFW | 15401 | |
| HPV45 | E1 | 494 | 10 | FVNSNSHFWL | 15402 | |
| HPV45 | E1 | 243 | 11 | GFKTLIKPATL | 15403 | |
| HPV45 | E1 | 342 | 9 | GIDDSNFDL | 15404 | |
| HPV45 | E1 | 209 | 11 | GLSFTDLVRNF | 15405 | |
| HPV45 | E1 | 480 | 8 | GMSFIHFL | 15406 | |
| HPV45 | E1 | 11 | 8 | GTGCNGWF | 15407 | |
| HPV45 | E1 | 11 | 9 | GTGCNGWFF | 15408 | |
| HPV45 | E1 | 459 | 8 | GTPKKNCI | 15409 | |
| HPV45 | E1 | 459 | 9 | GTPKKNCIL | 15410 | |
| HPV45 | E1 | 459 | 10 | GTPKKNCILL | 15411 | |
| HPV45 | E1 | 459 | 11 | GTPKKNCILLY | 15412 | |
| HPV45 | E1 | 443 | 8 | GVEFISFL | 15413 | |
| HPV45 | E1 | 443 | 11 | GVEFISFLRAL | 15414 | |
| HPV45 | E1 | 265 | 8 | GVLILALL | 15415 | |
| HPV45 | E1 | 265 | 10 | GVLILALLRY | 15416 | |
| HPV45 | E1 | 235 | 10 | GVNPTVAEGF | 15417 | |
| HPV45 | E1 | 16 | 8 | GWFFVETI | 15418 | |
| HPV45 | E1 | 485 | 8 | HFLQGAII | 15419 | |
| HPV45 | E1 | 485 | 10 | HFLQGAIISF | 15420 | |
| HPV45 | E1 | 256 | 9 | HIQCLDCKW | 15421 | |
| HPV45 | E1 | 519 | 10 | HTCWTYFDNY | 15422 | |
| HPV45 | E1 | 519 | 11 | HTCWTYFDNYM | 15423 | |
| HPV45 | E1 | 292 | 8 | HVPETCML | 15424 | |
| HPV45 | E1 | 292 | 9 | HVPETCMLI | 15425 | |
| HPV45 | E1 | 404 | 10 | HYKRAQKRQM | | 15426 |
| HPV45 | E1 | 338 | 11 | IIQHGIDDSNF | | 15427 |
| HPV45 | E1 | 491 | 11 | IISFVNSNSHF | | 15428 |
| HPV45 | E1 | 184 | 8 | ITELKELL | | 15429 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | E1 | 23 | 10 | IVEKKTGDVI | | 15430 |
| HPV45 | E1 | 207 | 9 | IYGLSFTDL | | 15431 |
| HPV45 | E1 | 425 | 8 | KIDEGGDW | | 15432 |
| HPV45 | E1 | 425 | 11 | KIDEGGDWRPI | | 15433 |
| HPV45 | E1 | 304 | 9 | KLRSSVAAL | | 15434 |
| HPV45 | E1 | 304 | 10 | KLRSSVAALY | | 15435 |
| HPV45 | E1 | 304 | 11 | KLRSSVAALYW | | 15436 |
| HPV45 | E1 | 245 | 9 | KTLIKPATL | | 15437 |
| HPV45 | E1 | 245 | 10 | KTLIKPATLY | | 15438 |
| HPV45 | E1 | 223 | 9 | KTTCTDWVM | | 15439 |
| HPV45 | E1 | 223 | 11 | KTTCTDWVMAI | | 15440 |
| HPV45 | E1 | 263 | 9 | KWGVLILAL | | 15441 |
| HPV45 | E1 | 263 | 10 | KWGVLILALL | | 15442 |
| HPV45 | E1 | 393 | 9 | KYLKDCAVM | | 15443 |
| HPV45 | E1 | 129 | 9 | LFTISDSGY | | 15444 |
| HPV45 | E1 | 247 | 8 | LIKPATLY | | 15445 |
| HPV45 | E1 | 247 | 11 | LIKPATLYAHI | | 15446 |
| HPV45 | E1 | 267 | 8 | LILALLRY | | 15447 |
| HPV45 | E1 | 290 | 9 | LLHVPETCM | | 15448 |
| HPV45 | E1 | 290 | 10 | LLHVPETCML | | 15449 |
| HPV45 | E1 | 290 | 11 | LLHVPETCMLI | | 15450 |
| HPV45 | E1 | 190 | 11 | LLQASNKKAAM | | 15451 |
| HPV45 | E1 | 547 | 9 | LLQLKCPPI | | 15452 |
| HPV45 | E1 | 547 | 10 | LLQLKCPPIL | | 15453 |
| HPV45 | E1 | 547 | 11 | LLQLKCPPILL | | 15454 |
| HPV45 | E1 | 271 | 11 | LLRYKCGKNRL | | 15455 |
| HPV45 | E1 | 362 | 9 | LTDESDMAF | | 15456 |
| HPV45 | E1 | 362 | 11 | LTDESDMAFQY | | 15457 |
| HPV45 | E1 | 336 | 8 | LTIIQHGI | | 15458 |
| HPV45 | E1 | 281 | 10 | LTVAKGLSTL | | 15459 |
| HPV45 | E1 | 281 | 11 | LTVAKGLSTLL | | 15460 |
| HPV45 | E1 | 253 | 8 | LYAHIQCL | | 15461 |
| HPV45 | E1 | 468 | 11 | LYGPANTGKSY | | 15462 |
| HPV45 | E1 | 312 | 8 | LYWYRTGI | | 15463 |
| HPV45 | E1 | 312 | 11 | LYWYRTGISNI | | 15464 |
| HPV45 | E1 | 200 | 8 | MLAVFKDI | | 15465 |
| HPV45 | E1 | 200 | 9 | MLAVFKDIY | | 15466 |
| HPV45 | E1 | 200 | 11 | MLAVFKDIYGL | | 15467 |
| HPV45 | E1 | 513 | 10 | MLDDATHTCW | | 15468 |
| HPV45 | E1 | 298 | 8 | MLIEPPKL | | 15469 |
| HPV45 | E1 | 47 | 9 | MVDFIDTQL | | 15470 |
| HPV45 | E1 | 47 | 11 | MVDFIDTQLSI | | 15471 |
| HPV45 | E1 | 353 | 10 | MVQWAFDNDL | | 15472 |
| HPV45 | E1 | 347 | 10 | NFDLSDMVQW | | 15473 |
| HPV45 | E1 | 560 | 10 | NIDPAKDNKW | | 15474 |
| HPV45 | E1 | 414 | 8 | NMSQWIKY | | 15475 |
| HPV45 | E1 | 473 | 9 | NTGKSYFGM | | 15476 |
| HPV45 | E1 | 473 | 11 | NTGKSYFGMSF | | 15477 |
| HPV45 | E1 | 177 | 8 | NVDPHCSI | | 15478 |
| HPV45 | E1 | 177 | 11 | NVDPHCSITEL | | 15479 |
| HPV45 | E1 | 601 | 10 | NWKCFFERTW | | 15480 |
| HPV45 | E1 | 586 | 10 | PFDKNGNPVY | | 15481 |
| HPV45 | E1 | 554 | 8 | PILLTSNI | | 15482 |
| HPV45 | E1 | 537 | 11 | PISIDRKHKPL | | 15483 |
| HPV45 | E1 | 434 | 8 | PIVQFLRY | | 15484 |
| HPV45 | E1 | 505 | 9 | PLADTKVAM | | 15485 |
| HPV45 | E1 | 505 | 10 | PLADTKVAML | | 15486 |
| HPV45 | E1 | 546 | 10 | PLLQLKCPPI | | 15487 |
| HPV45 | E1 | 546 | 11 | PLLQLKCPPIL | | 15488 |
| HPV45 | E1 | 238 | 10 | PTVAEGFKTL | | 15489 |
| HPV45 | E1 | 238 | 11 | PTVAEGFKTLI | | 15490 |
| HPV45 | E1 | 593 | 10 | PVYEINDKNW | | 15491 |
| HPV45 | E1 | 570 | 10 | PYLESRVTVF | | 15492 |
| HPV45 | E1 | 437 | 10 | QFLRYQGVEF | | 15493 |
| HPV45 | E1 | 437 | 11 | QFLRYQGVEFI | | 15494 |
| HPV45 | E1 | 549 | 8 | QLKCPPIL | | 15495 |
| HPV45 | E1 | 549 | 9 | QLKCPPILL | | 15496 |
| HPV45 | E1 | 102 | 8 | QLSVDTDL | | 15497 |
| HPV45 | E1 | 412 | 8 | QMNMSQWI | | 15498 |
| HPV45 | E1 | 412 | 10 | QMNMSQWIKY | | 15499 |
| HPV45 | E1 | 80 | 10 | QVLHLLKRKF | | 15500 |
| HPV45 | E1 | 355 | 8 | QWAFDNDL | | 15501 |
| HPV45 | E1 | 417 | 10 | QWIKYRCSKI | | 15502 |
| HPV45 | E1 | 128 | 10 | RLFTISDSGY | | 15503 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | E1 | 335 | 9 | RLTIIQHGI | | 15504 |
| HPV45 | E1 | 280 | 8 | RLTVAKGL | | 15505 |
| HPV45 | E1 | 280 | 11 | RLTVAKGLSTL | | 15506 |
| HPV45 | E1 | 608 | 8 | RTWSRLDL | | 15507 |
| HPV45 | E1 | 575 | 11 | RVTVFTFPHAF | | 15508 |
| HPV45 | E1 | 273 | 9 | RYKCGKNRL | | 15509 |
| HPV45 | E1 | 440 | 8 | RYQGVEFI | | 15510 |
| HPV45 | E1 | 440 | 10 | RYQGVEFISF | | 15511 |
| HPV45 | E1 | 440 | 11 | RYQGVEFISFL | | 15512 |
| HPV45 | E1 | 482 | 10 | SFIHFLQGAI | | 15513 |
| HPV45 | E1 | 482 | 11 | SFIHFLQGAII | | 15514 |
| HPV45 | E1 | 448 | 9 | SFLRALKEF | | 15515 |
| HPV45 | E1 | 448 | 10 | SFLRALKEFL | | 15516 |
| HPV45 | E1 | 211 | 9 | SFTDLVRNF | | 15517 |
| HPV45 | E1 | 493 | 9 | SFVNSNSHF | | 15518 |
| HPV45 | E1 | 493 | 10 | SFVNSNSHFW | | 15519 |
| HPV45 | E1 | 493 | 11 | SFVNSNSHFWL | | 15520 |
| HPV45 | E1 | 539 | 9 | SIDRKHKPL | | 15521 |
| HPV45 | E1 | 539 | 10 | SIDRKHKPLL | | 15522 |
| HPV45 | E1 | 183 | 8 | SITELKEL | | 15523 |
| HPV45 | E1 | 183 | 9 | SITELKELL | | 15524 |
| HPV45 | E1 | 288 | 11 | STLLHVPETCM | | 15525 |
| HPV45 | E1 | 308 | 8 | SVAALYWY | | 15526 |
| HPV45 | E1 | 104 | 10 | SVDTDLSPRL | | 15527 |
| HPV45 | E1 | 477 | 8 | SYFGMSFI | | 15528 |
| HPV45 | E1 | 477 | 10 | SYFGMSFIHF | | 15529 |
| HPV45 | E1 | 477 | 11 | SYFGMSFIHFL | | 15530 |
| HPV45 | E1 | 580 | 8 | TFPHAFPF | | 15531 |
| HPV45 | E1 | 22 | 11 | TIVEKKTGDVI | | 15532 |
| HPV45 | E1 | 246 | 8 | TLIKPATL | | 15533 |
| HPV45 | E1 | 246 | 9 | TLIKPATLY | | 15534 |
| HPV45 | E1 | 289 | 10 | TLLHVPETCM | | 15535 |
| HPV45 | E1 | 289 | 11 | TLLHVPETCML | | 15536 |
| HPV45 | E1 | 252 | 9 | TLYAHIQCL | | 15537 |
| HPV45 | E1 | 224 | 8 | TTCTDWVM | | 15538 |
| HPV45 | E1 | 224 | 10 | TTCTDWVMAI | | 15539 |
| HPV45 | E1 | 224 | 11 | TTCTDWVMAIF | | 15540 |
| HPV45 | E1 | 239 | 9 | TVAEGFKTL | | 15541 |
| HPV45 | E1 | 239 | 10 | TVAEGFKTLI | | 15542 |
| HPV45 | E1 | 282 | 9 | TVAKGLSTL | | 15543 |
| HPV45 | E1 | 282 | 10 | TVAKGLSTLL | | 15544 |
| HPV45 | E1 | 577 | 9 | TVFTFPHAF | | 15545 |
| HPV45 | E1 | 577 | 11 | TVFTFPHAFPF | | 15546 |
| HPV45 | E1 | 523 | 11 | TYFDNYMRNAL | | 15547 |
| HPV45 | E1 | 203 | 8 | VFKDIYGL | | 15548 |
| HPV45 | E1 | 203 | 10 | VFKDIYGLSF | | 15549 |
| HPV45 | E1 | 578 | 8 | VFTFPHAF | | 15550 |
| HPV45 | E1 | 578 | 10 | VFTFPHAFPF | | 15551 |
| HPV45 | E1 | 81 | 9 | VLHLLKRKF | | 15552 |
| HPV45 | E1 | 266 | 9 | VLILALLRY | | 15553 |
| HPV45 | E1 | 635 | 9 | VTGQNTRPL | | 15554 |
| HPV45 | E1 | 576 | 10 | VTVFTFPHAF | | 15555 |
| HPV45 | E1 | 594 | 9 | VYEINDKNW | | 15556 |
| HPV45 | E1 | 418 | 9 | WIKYRCSKI | | 15557 |
| HPV45 | E1 | 332 | 8 | WIQRLTII | | 15558 |
| HPV45 | E1 | 522 | 8 | WTYFDNYM | | 15559 |
| HPV45 | E1 | 314 | 9 | WYRTGISNI | | 15560 |
| HPV45 | E1 | 524 | 10 | YFDNYMRNAL | | 15561 |
| HPV45 | E1 | 478 | 9 | YFGMSFIHF | | 15562 |
| HPV45 | E1 | 478 | 10 | YFGMSFIHFL | | 15563 |
| HPV45 | E1 | 571 | 9 | YLESRVTVF | | 15564 |
| HPV45 | E1 | 571 | 11 | YLESRVTVFTF | | 15565 |
| HPV45 | E1 | 394 | 8 | YLKDCAVM | | 15566 |
| HPV45 | E1 | 528 | 11 | YMRNALDGNPI | | 15567 |
| HPV45 | E1 | 313 | 10 | YWYRTGISNI | | 15568 |
| HPV45 | E2 | 78 | 8 | AIELQMAL | | 15569 |
| HPV45 | E2 | 78 | 11 | AIELQMALKGL | | 15570 |
| HPV45 | E2 | 47 | 11 | AILFTAREHGI | | 15571 |
| HPV45 | E2 | 84 | 10 | ALKGLAQSKY | | 15572 |
| HPV45 | E2 | 16 | 10 | ALQDKILDHY | | 15573 |
| HPV45 | E2 | 247 | 10 | ATKRPRQCGL | | 15574 |
| HPV45 | E2 | 216 | 8 | ATQIVRQL | | 15575 |
| HPV45 | E2 | 305 | 9 | CLRYRLRKY | | 15576 |
| HPV45 | E2 | 134 | 10 | CMNYVVWDSI | | 15577 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | E2 | 134 | 11 | CMNYVVWDSIY | | 15578 |
| HPV45 | E2 | 158 | 8 | CVSYWGVY | | 15579 |
| HPV45 | E2 | 158 | 9 | CVSYWGVYY | | 15580 |
| HPV45 | E2 | 158 | 10 | CVSYWGVYYI | | 15581 |
| HPV45 | E2 | 31 | 8 | DINSQISY | | 15582 |
| HPV45 | E2 | 31 | 9 | DINSQISYW | | 15583 |
| HPV45 | E2 | 31 | 11 | DINSQISYWQL | | 15584 |
| HPV45 | E2 | 171 | 8 | DTTYYVQF | | 15585 |
| HPV45 | E2 | 212 | 8 | DTVSATQI | | 15586 |
| HPV45 | E2 | 351 | 11 | DVVTIPNSVQI | | 15587 |
| HPV45 | E2 | 319 | 8 | EISSTWHW | | 15588 |
| HPV45 | E2 | 80 | 9 | ELQMALKGL | | 15589 |
| HPV45 | E2 | 106 | 11 | ELWNTEPSQCF | | 15590 |
| HPV45 | E2 | 343 | 8 | EVQRNTFL | | 15591 |
| HPV45 | E2 | 192 | 9 | EVQYGGNVI | | 15592 |
| HPV45 | E2 | 97 | 11 | EWTLQDTCEEL | | 15593 |
| HPV45 | E2 | 50 | 8 | FTAREHGI | | 15594 |
| HPV45 | E2 | 50 | 11 | FTAREHGITKL | | 15595 |
| HPV45 | E2 | 295 | 9 | HLKGDKNSL | | 15596 |
| HPV45 | E2 | 325 | 11 | HWTGCNKNTGI | | 15597 |
| HPV45 | E2 | 24 | 9 | HYENDSKDI | | 15598 |
| HPV45 | E2 | 316 | 9 | HYSEISSTW | | 15599 |
| HPV45 | E2 | 316 | 11 | HYSEISSTWHW | | 15600 |
| HPV45 | E2 | 293 | 11 | IIHLKGDKNSL | | 15601 |
| HPV45 | E2 | 48 | 10 | ILFTAREHGI | | 15602 |
| HPV45 | E2 | 151 | 11 | IWDKTAACVSY | | 15603 |
| HPV45 | E2 | 143 | 9 | IYYITETGI | | 15604 |
| HPV45 | E2 | 143 | 10 | IYYITETGIW | | 15605 |
| HPV45 | E2 | 59 | 10 | KLNHQVVPPI | | 15606 |
| HPV45 | E2 | 2 | 9 | KMQTPKESL | | 15607 |
| HPV45 | E2 | 154 | 8 | KTAACVSY | | 15608 |
| HPV45 | E2 | 154 | 9 | KTAACVSYW | | 15609 |
| HPV45 | E2 | 284 | 10 | KVCSGNTTPI | | 15610 |
| HPV45 | E2 | 284 | 11 | KVCSGNTTPII | | 15611 |
| HPV45 | E2 | 312 | 9 | KYADHYSEI | | 15612 |
| HPV45 | E2 | 184 | 8 | KYGNSNTW | | 15613 |
| HPV45 | E2 | 92 | 9 | KYNNEEWTL | | 15614 |
| HPV45 | E2 | 49 | 9 | LFTAREHGI | | 15615 |
| HPV45 | E2 | 41 | 8 | LIRLENAI | | 15616 |
| HPV45 | E2 | 41 | 9 | LIRLENAIL | | 15617 |
| HPV45 | E2 | 41 | 10 | LIRLENAILF | | 15618 |
| HPV45 | E2 | 107 | 10 | LWNTEPSQCF | | 15619 |
| HPV45 | E2 | 69 | 11 | NISKSKAHKAI | | 15620 |
| HPV45 | E2 | 109 | 8 | NTEPSQCF | | 15621 |
| HPV45 | E2 | 347 | 9 | NTFLDVVTI | | 15622 |
| HPV45 | E2 | 332 | 9 | NTGILTVTY | | 15623 |
| HPV45 | E2 | 265 | 8 | NTHVHNPL | | 15624 |
| HPV45 | E2 | 265 | 9 | NTHVHNPLL | | 15625 |
| HPV45 | E2 | 289 | 8 | NTTPIIHL | | 15626 |
| HPV45 | E2 | 198 | 9 | NVIDCNDSM | | 15627 |
| HPV45 | E2 | 136 | 8 | NYVVWDSI | | 15628 |
| HPV45 | E2 | 136 | 9 | NYVVWDSIY | | 15629 |
| HPV45 | E2 | 136 | 10 | NYVVWDSIYY | | 15630 |
| HPV45 | E2 | 136 | 11 | NYVVWDSIYYI | | 15631 |
| HPV45 | E2 | 177 | 9 | QFKSECEKY | | 15632 |
| HPV45 | E2 | 360 | 9 | QISVGYMTI | | 15633 |
| HPV45 | E2 | 35 | 8 | QISYWQLI | | 15634 |
| HPV45 | E2 | 35 | 10 | QISYWQLIRL | | 15635 |
| HPV45 | E2 | 40 | 9 | QLIRLENAI | | 15636 |
| HPV45 | E2 | 40 | 10 | QLIRLENAIL | | 15637 |
| HPV45 | E2 | 40 | 11 | QLIRLENAILF | | 15638 |
| HPV45 | E2 | 4 | 11 | QTPKESLSERL | | 15639 |
| HPV45 | E2 | 63 | 8 | QVVPPINI | | 15640 |
| HPV45 | E2 | 43 | 8 | RLENAILF | | 15641 |
| HPV45 | E2 | 309 | 9 | RLRKYADHY | | 15642 |
| HPV45 | E2 | 13 | 9 | RLSALQDKI | | 15643 |
| HPV45 | E2 | 13 | 10 | RLSALQDKIL | | 15644 |
| HPV45 | E2 | 263 | 10 | RVNTHVHNPL | | 15645 |
| HPV45 | E2 | 263 | 11 | RVNTHVHNPLL | | 15646 |
| HPV45 | E2 | 307 | 11 | RYRLRKYADHY | | 15647 |
| HPV45 | E2 | 142 | 10 | SIYYITETGI | | 15648 |
| HPV45 | E2 | 142 | 11 | SIYYITETGIW | | 15649 |
| HPV45 | E2 | 302 | 9 | SLKCLRYRL | | 15650 |
| HPV45 | E2 | 9 | 9 | SLSERLSAL | | 15651 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | E2 | 235 | 9 | SVGTPKPHI | | 15652 |
| HPV45 | E2 | 358 | 8 | SVQISVGY | | 15653 |
| HPV45 | E2 | 358 | 9 | SVQISVGYM | | 15654 |
| HPV45 | E2 | 358 | 11 | SVQISVGYMTI | | 15655 |
| HPV45 | E2 | 160 | 8 | SYWGVYYI | | 15656 |
| HPV45 | E2 | 37 | 8 | SYWQLIRL | | 15657 |
| HPV45 | E2 | 348 | 8 | TFLDVVTI | | 15658 |
| HPV45 | E2 | 354 | 8 | TIPNSVQI | | 15659 |
| HPV45 | E2 | 99 | 9 | TLQDTCEEL | | 15660 |
| HPV45 | E2 | 99 | 10 | TLQDTCEELW | | 15661 |
| HPV45 | E2 | 213 | 11 | TVSATQIVRQL | | 15662 |
| HPV45 | E2 | 190 | 11 | TWEVQYGGNVI | | 15663 |
| HPV45 | E2 | 339 | 11 | TYNSEVQRNTF | | 15664 |
| HPV45 | E2 | 199 | 8 | VIDCNDSM | | 15665 |
| HPV45 | E2 | 353 | 9 | VTIPNSVQI | | 15666 |
| HPV45 | E2 | 352 | 10 | VVTIPNSVQI | | 15667 |
| HPV45 | E2 | 138 | 8 | VVWDSIYY | | 15668 |
| HPV45 | E2 | 138 | 9 | VVWDSIYYI | | 15669 |
| HPV45 | E2 | 139 | 8 | VWDSIYYI | | 15670 |
| HPV45 | E2 | 125 | 11 | VYFDGNKDNCM | | 15671 |
| HPV45 | E2 | 164 | 11 | VYYIKDGDTTY | | 15672 |
| HPV45 | E2 | 326 | 10 | WTGCNKNTGI | | 15673 |
| HPV45 | E2 | 326 | 11 | WTGCNKNTGIL | | 15674 |
| HPV45 | E2 | 98 | 10 | WTLQDTCEEL | | 15675 |
| HPV45 | E2 | 98 | 11 | WTLQDTCEELW | | 15676 |
| HPV45 | E2 | 126 | 10 | YFDGNKDNCM | | 15677 |
| HPV45 | E2 | 166 | 9 | YIKDGDTTY | | 15678 |
| HPV45 | E2 | 166 | 10 | YIKDGDTTYY | | 15679 |
| HPV45 | E2 | 145 | 8 | YITETGIW | | 15680 |
| HPV45 | E2 | 175 | 11 | YVQFKSECEKY | | 15681 |
| HPV45 | E2 | 137 | 8 | YVVWDSIY | | 15682 |
| HPV45 | E2 | 137 | 9 | YVVWDSIYY | | 15683 |
| HPV45 | E2 | 137 | 10 | YVVWDSIYYI | | 15684 |
| HPV45 | E2 | 38 | 11 | YWQLIRLENAI | | 15685 |
| HPV45 | E2 | 165 | 10 | YYIKDGDTTY | | 15686 |
| HPV45 | E2 | 165 | 11 | YYIKDGDTTYY | | 15687 |
| HPV45 | E2 | 144 | 8 | YYITETGI | | 15688 |
| HPV45 | E2 | 144 | 9 | YYITETGIW | | 15689 |
| HPV45 | E6 | 48 | 9 | AFKDLFIVY | | 15690 |
| HPV45 | E6 | 37 | 9 | ATLERTEVY | | 15691 |
| HPV45 | E6 | 37 | 11 | ATLERTEVYQF | | 15692 |
| HPV45 | E6 | 61 | 9 | AYAACHKCI | | 15693 |
| HPV45 | E6 | 61 | 11 | AYAACHKCIDF | | 15694 |
| HPV45 | E6 | 59 | 11 | CIAYAACHKCI | | 15695 |
| HPV45 | E6 | 68 | 8 | CIDFYSRI | | 15696 |
| HPV45 | E6 | 68 | 11 | CIDFYSRIREL | | 15697 |
| HPV45 | E6 | 105 | 8 | CLRCQKPL | | 15698 |
| HPV45 | E6 | 18 | 8 | CTELNTSL | | 15699 |
| HPV45 | E6 | 32 | 8 | CVYCKATL | | 15700 |
| HPV45 | E6 | 70 | 9 | DFYSRIREL | | 15701 |
| HPV45 | E6 | 70 | 11 | DFYSRIRELRY | | 15702 |
| HPV45 | E6 | 16 | 10 | DLCTELNTSL | | 15703 |
| HPV45 | E6 | 51 | 10 | DLFIVYRDCI | | 15704 |
| HPV45 | E6 | 27 | 8 | DVSIACVY | | 15705 |
| HPV45 | E6 | 20 | 11 | ELNTSLQDVSI | | 15706 |
| HPV45 | E6 | 77 | 10 | ELRYYSNSVY | | 15707 |
| HPV45 | E6 | 97 | 10 | ELYNLLIRCL | | 15708 |
| HPV45 | E6 | 88 | 11 | ETLEKITNTEL | | 15709 |
| HPV45 | E6 | 43 | 10 | EVYQFAFKDL | | 15710 |
| HPV45 | E6 | 43 | 11 | EVYQFAFKDLF | | 15711 |
| HPV45 | E6 | 53 | 8 | FIVYRDCI | | 15712 |
| HPV45 | E6 | 53 | 10 | FIVYRDCIAY | | 15713 |
| HPV45 | E6 | 71 | 8 | FYSRIREL | 0.026 | 15714 |
| HPV45 | E6 | 71 | 10 | FYSRIRELRY | | 15715 |
| HPV45 | E6 | 71 | 11 | FYSRIRELRYY | | 15716 |
| HPV45 | E6 | 120 | 8 | HLKDKRRF | | 15717 |
| HPV45 | E6 | 120 | 11 | HLKDKRRFHSI | | 15718 |
| HPV45 | E6 | 93 | 9 | ITNTELYNL | | 15719 |
| HPV45 | E6 | 93 | 10 | ITNTELYNLL | | 15720 |
| HPV45 | E6 | 93 | 11 | ITNTELYNLLI | | 15721 |
| HPV45 | E6 | 54 | 9 | IVYRDCIAY | | 15722 |
| HPV45 | E6 | 92 | 8 | KITNTELY | | 15723 |
| HPV45 | E6 | 92 | 10 | KITNTELYNL | | 15724 |
| HPV45 | E6 | 92 | 11 | KITNTELYNLL | | 15725 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | E6 | 13 | 9 | KLPDLCTEL | 0.0013 | 15726 |
| HPV45 | E6 | 52 | 9 | LFIVYRDCI | | 15727 |
| HPV45 | E6 | 52 | 11 | LFIVYRDCIAY | | 15728 |
| HPV45 | E6 | 102 | 11 | LIRCLRCQKPL | | 15729 |
| HPV45 | E6 | 98 | 9 | LYNLLIRCL | 0.0001 | 15730 |
| HPV45 | E6 | 95 | 8 | NTELYNLL | | 15731 |
| HPV45 | E6 | 95 | 9 | NTELYNLLI | | 15732 |
| HPV45 | E6 | 22 | 9 | NTSLQDVSI | | 15733 |
| HPV45 | E6 | 111 | 11 | PLNPAEKRRHL | | 15734 |
| HPV45 | E6 | 7 | 8 | PTQRPYKL | | 15735 |
| HPV45 | E6 | 7 | 11 | PTQRPYKLPDL | | 15736 |
| HPV45 | E6 | 11 | 11 | PYKLPDLCTEL | 0.0064 | 15737 |
| HPV45 | E6 | 46 | 8 | QFAFKDLF | | 15738 |
| HPV45 | E6 | 46 | 9 | QFAFKDLFI | | 15739 |
| HPV45 | E6 | 46 | 11 | QFAFKDLFIVY | | 15740 |
| HPV45 | E6 | 3 | 10 | RFDDPTQRPY | | 15741 |
| HPV45 | E6 | 126 | 9 | RFHSIAGQY | | 15742 |
| HPV45 | E6 | 74 | 8 | RIRELRYY | | 15743 |
| HPV45 | E6 | 41 | 9 | RTEVYQFAF | | 15744 |
| HPV45 | E6 | 79 | 8 | RYYSNSVY | | 15745 |
| HPV45 | E6 | 29 | 11 | SIACVYCKATL | | 15746 |
| HPV45 | E6 | 24 | 11 | SLQDVSIACVY | | 15747 |
| HPV45 | E6 | 84 | 10 | SVYGETLEKI | | 15748 |
| HPV45 | E6 | 89 | 10 | TLEKITNTEL | | 15749 |
| HPV45 | E6 | 89 | 11 | TLEKITNTELY | | 15750 |
| HPV45 | E6 | 38 | 8 | TLERTEVY | | 15751 |
| HPV45 | E6 | 38 | 10 | TLERTEVYQF | | 15752 |
| HPV45 | E6 | 85 | 9 | VYGETLEKI | | 15753 |
| HPV45 | E6 | 44 | 9 | VYQFAFKDL | | 15754 |
| HPV45 | E6 | 44 | 10 | VYQFAFKDLF | | 15755 |
| HPV45 | E6 | 44 | 11 | VYQFAFKDLFI | | 15756 |
| HPV45 | E6 | 55 | 8 | VYRDCIAY | | 15757 |
| HPV45 | E6 | 80 | 11 | YYSNSVYGETL | | 15758 |
| HPV45 | E7 | 6 | 8 | ATLQEIVL | | 15759 |
| HPV45 | E7 | 6 | 10 | ATLQEIVLHL | | 15760 |
| HPV45 | E7 | 64 | 10 | CVCCKCDGRI | | 15761 |
| HPV45 | E7 | 25 | 8 | DLLCYEQL | | 15762 |
| HPV45 | E7 | 83 | 8 | DLRTLQQL | | 15763 |
| HPV45 | E7 | 83 | 9 | DLRTLQQLF | | 15764 |
| HPV45 | E7 | 83 | 10 | DLRTLQQLFL | | 15765 |
| HPV45 | E7 | 20 | 8 | ELDPVDLL | | 15766 |
| HPV45 | E7 | 20 | 10 | ELDPVDLLCY | | 15767 |
| HPV45 | E7 | 74 | 11 | ELTVESSADDL | | 15768 |
| HPV45 | E7 | 91 | 11 | FLSTLSFVCPW | | 15769 |
| HPV45 | E7 | 14 | 8 | HLEPQNEL | | 15770 |
| HPV45 | E7 | 11 | 11 | IVLHLEPQNEL | | 15771 |
| HPV45 | E7 | 90 | 8 | LFLSTLSF | | 15772 |
| HPV45 | E7 | 75 | 10 | LTVESSADDL | | 15773 |
| HPV45 | E7 | 23 | 10 | PVDLLCYEQL | | 15774 |
| HPV45 | E7 | 89 | 9 | QLFLSTLSF | | 15775 |
| HPV45 | E7 | 85 | 8 | RTLQQLFL | | 15776 |
| HPV45 | E7 | 85 | 11 | RTLQQLFLSTL | | 15777 |
| HPV45 | E7 | 93 | 9 | STLSFVCPW | | 15778 |
| HPV45 | E7 | 7 | 9 | TLQEIVLHL | | 15779 |
| HPV45 | E7 | 86 | 10 | TLQQLFLSTL | | 15780 |
| HPV45 | E7 | 94 | 8 | TLSFVCPW | | 15781 |
| HPV45 | E7 | 76 | 9 | TVESSADDL | | 15782 |
| HPV45 | E7 | 12 | 10 | VLHLEPQNEL | | 15783 |
| HPV45 | L1 | 191 | 11 | AIGEHWAKGTL | | 15784 |
| HPV45 | L1 | 103 | 8 | ALPDPNKF | | 15785 |
| HPV45 | L1 | 103 | 10 | ALPDPNKFGL | | 15786 |
| HPV45 | L1 | 28 | 11 | ALWRPSDSTVY | | 15787 |
| HPV45 | L1 | 88 | 8 | AVPKVSAY | | 15788 |
| HPV45 | L1 | 88 | 10 | AVPKVSAYQY | | 15789 |
| HPV45 | L1 | 94 | 11 | AYQYRVFRVAL | | 15790 |
| HPV45 | L1 | 184 | 9 | CILGCVPAI | | 15791 |
| HPV45 | L1 | 276 | 8 | CLRREQLF | | 15792 |
| HPV45 | L1 | 409 | 10 | CTITLTAEVM | | 15793 |
| HPV45 | L1 | 188 | 9 | CVPAIGEHW | | 15794 |
| HPV45 | L1 | 318 | 11 | CVYSPSPSGSI | | 15795 |
| HPV45 | L1 | 250 | 9 | DICQSICKY | | 15796 |
| HPV45 | L1 | 488 | 11 | DLDQYPLGRKF | | 15797 |
| HPV45 | L1 | 480 | 10 | DLKEKFSSDL | | 15798 |
| HPV45 | L1 | 401 | 8 | DLQFIFQL | | 15799 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | L1 | 401 | 11 | DLQFIFQLCTI | | 15800 |
| HPV45 | L1 | 301 | 11 | DLYIKGTSANM | | 15801 |
| HPV45 | L1 | 226 | 10 | DMVDTGYGAM | | 15802 |
| HPV45 | L1 | 229 | 9 | DTGYGAMDF | | 15803 |
| HPV45 | L1 | 242 | 8 | DTKCEVPL | | 15804 |
| HPV45 | L1 | 242 | 10 | DTKCEVPLDI | | 15805 |
| HPV45 | L1 | 461 | 11 | DTTPPEKQDPY | | 15806 |
| HPV45 | L1 | 364 | 8 | DTTRSTNL | | 15807 |
| HPV45 | L1 | 364 | 10 | DTTRSTNLTL | | 15808 |
| HPV45 | L1 | 296 | 8 | DTVPTDLY | | 15809 |
| HPV45 | L1 | 296 | 9 | DTVPTDLYI | | 15810 |
| HPV45 | L1 | 169 | 10 | DVRDNVSVDY | | 15811 |
| HPV45 | L1 | 177 | 9 | DYKQTQLCI | | 15812 |
| HPV45 | L1 | 177 | 10 | DYKQTQLCIL | | 15813 |
| HPV45 | L1 | 260 | 10 | DYLQMSADPY | | 15814 |
| HPV45 | L1 | 52 | 8 | DYVSRTSI | | 15815 |
| HPV45 | L1 | 52 | 9 | DYVSRTSIF | | 15816 |
| HPV45 | L1 | 52 | 10 | DYVSRTSIFY | | 15817 |
| HPV45 | L1 | 133 | 8 | EIGRGQPL | | 15818 |
| HPV45 | L1 | 133 | 10 | EIGRGQPLGI | | 15819 |
| HPV45 | L1 | 313 | 8 | ETPGSCVY | | 15820 |
| HPV45 | L1 | 416 | 9 | EVMSYIHSM | | 15821 |
| HPV45 | L1 | 246 | 10 | EVPLDICQSI | | 15822 |
| HPV45 | L1 | 399 | 8 | EYDLQFIF | | 15823 |
| HPV45 | L1 | 399 | 10 | EYDLQFIFQL | | 15824 |
| HPV45 | L1 | 274 | 9 | FFCLRREQL | | 15825 |
| HPV45 | L1 | 274 | 10 | FFCLRREQLF | | 15826 |
| HPV45 | L1 | 404 | 8 | FIFQLCTI | | 15827 |
| HPV45 | L1 | 404 | 10 | FIFQLCTITL | | 15828 |
| HPV45 | L1 | 14 | 8 | FLKNVNVF | | 15829 |
| HPV45 | L1 | 14 | 10 | FLKNVNVFPI | | 15830 |
| HPV45 | L1 | 14 | 11 | FLKNVNVFPIF | | 15831 |
| HPV45 | L1 | 287 | 8 | FWNRAGVM | | 15832 |
| HPV45 | L1 | 476 | 10 | FWTVDLKEKF | | 15833 |
| HPV45 | L1 | 60 | 9 | FYHAGSSRL | | 15834 |
| HPV45 | L1 | 60 | 10 | FYHAGSSRLL | | 15835 |
| HPV45 | L1 | 351 | 8 | GICWHNQL | | 15836 |
| HPV45 | L1 | 351 | 9 | GICWHNQLF | | 15837 |
| HPV45 | L1 | 141 | 9 | GIGLSGHPF | | 15838 |
| HPV45 | L1 | 141 | 10 | GIGLSGHPFY | | 15839 |
| HPV45 | L1 | 111 | 8 | GLPDSTIY | | 15840 |
| HPV45 | L1 | 503 | 8 | GLRRRPTI | | 15841 |
| HPV45 | L1 | 143 | 8 | GLSGHPFY | | 15842 |
| HPV45 | L1 | 143 | 11 | GLSGHPFYNKL | | 15843 |
| HPV45 | L1 | 131 | 10 | GMEIGRGQPL | | 15844 |
| HPV45 | L1 | 199 | 9 | GTLCKPAQL | | 15845 |
| HPV45 | L1 | 292 | 11 | GVMGDTVPTDL | | 15846 |
| HPV45 | L1 | 435 | 10 | GVPPPPTTSL | | 15847 |
| HPV45 | L1 | 231 | 10 | GYGAMDFSTL | | 15848 |
| HPV45 | L1 | 286 | 9 | HFWNRAGVM | | 15849 |
| HPV45 | L1 | 396 | 9 | HVEEYDLQF | | 15850 |
| HPV45 | L1 | 396 | 10 | HVEEYDLQFI | | 15851 |
| HPV45 | L1 | 396 | 11 | HVEEYDLQFIF | | 15852 |
| HPV45 | L1 | 392 | 9 | HYSRHVEEY | | 15853 |
| HPV45 | L1 | 392 | 11 | HYSRHVEEYDL | | 15854 |
| HPV45 | L1 | 13 | 9 | IFLKNVNVF | | 15855 |
| HPV45 | L1 | 13 | 11 | IFLKNVNVFPI | | 15856 |
| HPV45 | L1 | 23 | 8 | IFLQMALW | | 15857 |
| HPV45 | L1 | 405 | 9 | IFQLCTITL | | 15858 |
| HPV45 | L1 | 59 | 10 | IFYHAGSSRL | | 15859 |
| HPV45 | L1 | 59 | 11 | IFYHAGSSRLL | | 15860 |
| HPV45 | L1 | 12 | 10 | IIFLKNVNVF | | 15861 |
| HPV45 | L1 | 11 | 11 | IIIFLKNVNVF | | 15862 |
| HPV45 | L1 | 5 | 8 | IIYGHGII | | 15863 |
| HPV45 | L1 | 5 | 9 | IIYGHGIII | | 15864 |
| HPV45 | L1 | 5 | 10 | IIYGHGIIIF | | 15865 |
| HPV45 | L1 | 5 | 11 | IIYGHGIIIFL | | 15866 |
| HPV45 | L1 | 185 | 8 | ILGCVPAI | | 15867 |
| HPV45 | L1 | 411 | 8 | ITLTAEVM | | 15868 |
| HPV45 | L1 | 411 | 10 | ITLTAEVMSY | | 15869 |
| HPV45 | L1 | 411 | 11 | ITLTAEVMSYI | | 15870 |
| HPV45 | L1 | 328 | 8 | ITTSDSQL | | 15871 |
| HPV45 | L1 | 328 | 9 | ITTSDSQLF | | 15872 |
| HPV45 | L1 | 6 | 8 | IYGHGIII | | 15873 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | L1 | 6 | 9 | IYGHGIIIF | | 15874 |
| HPV45 | L1 | 6 | 10 | IYGHGIIIFL | | 15875 |
| HPV45 | L1 | 117 | 9 | IYNPETQRL | | 15876 |
| HPV45 | L1 | 117 | 11 | IYNPETQRLVW | | 15877 |
| HPV45 | L1 | 109 | 9 | KFGLPDSTI | | 15878 |
| HPV45 | L1 | 109 | 10 | KFGLPDSTIY | | 15879 |
| HPV45 | L1 | 497 | 8 | KFLVQAGL | | 15880 |
| HPV45 | L1 | 484 | 9 | KFSSDLDQY | | 15881 |
| HPV45 | L1 | 484 | 11 | KFSSDLDQYPL | | 15882 |
| HPV45 | L1 | 475 | 11 | KFWTVDLKEKF | | 15883 |
| HPV45 | L1 | 473 | 9 | KLKFWTVDL | | 15884 |
| HPV45 | L1 | 91 | 10 | KVSAYQYRVF | | 15885 |
| HPV45 | L1 | 257 | 8 | KYPDYLQM | | 15886 |
| HPV45 | L1 | 335 | 8 | LFNKPYWL | | 15887 |
| HPV45 | L1 | 68 | 8 | LLTVGNPY | | 15888 |
| HPV45 | L1 | 68 | 9 | LLTVGNPYF | | 15889 |
| HPV45 | L1 | 413 | 8 | LTAEVMSY | | 15890 |
| HPV45 | L1 | 413 | 9 | LTAEVMSYI | | 15891 |
| HPV45 | L1 | 69 | 8 | LTVGNPYF | | 15892 |
| HPV45 | L1 | 125 | 8 | LVWACVGM | | 15893 |
| HPV45 | L1 | 125 | 10 | LVWACVGMEI | | 15894 |
| HPV45 | L1 | 29 | 10 | LWRPSDSTVY | | 15895 |
| HPV45 | L1 | 29 | 11 | LWRPSDSTVYL | | 15896 |
| HPV45 | L1 | 302 | 10 | LYIKGTSANM | | 15897 |
| HPV45 | L1 | 273 | 10 | MFFCLRREQL | | 15898 |
| HPV45 | L1 | 273 | 11 | MFFCLRREQLF | | 15899 |
| HPV45 | L1 | 227 | 9 | MVDTGYGAM | | 15900 |
| HPV45 | L1 | 227 | 11 | MVDTGYGAMDF | | 15901 |
| HPV45 | L1 | 4 | 8 | NIIYGHGI | | 15902 |
| HPV45 | L1 | 4 | 9 | NIIYGHGII | | 15903 |
| HPV45 | L1 | 4 | 10 | NIIYGHGIII | | 15904 |
| HPV45 | L1 | 4 | 11 | NIIYGHGIIIF | | 15905 |
| HPV45 | L1 | 310 | 11 | NMRETPGSCVY | | 15906 |
| HPV45 | L1 | 49 | 11 | NTDDYVSRTSI | | 15907 |
| HPV45 | L1 | 219 | 9 | NTIIEDGDM | | 15908 |
| HPV45 | L1 | 383 | 8 | NTYDPTKF | | 15909 |
| HPV45 | L1 | 383 | 11 | NTYDPTKFKHY | | 15910 |
| HPV45 | L1 | 19 | 9 | NVFPIFLQM | | 15911 |
| HPV45 | L1 | 19 | 11 | NVFPIFLQMAL | | 15912 |
| HPV45 | L1 | 17 | 8 | NVNVFPIF | | 15913 |
| HPV45 | L1 | 17 | 9 | NVNVFPIFL | | 15914 |
| HPV45 | L1 | 17 | 11 | NVNVFPIFLQM | | 15915 |
| HPV45 | L1 | 173 | 11 | NVSVDYKQTQL | | 15916 |
| HPV45 | L1 | 22 | 8 | PIFLQMAL | | 15917 |
| HPV45 | L1 | 22 | 9 | PIFLQMALW | | 15918 |
| HPV45 | L1 | 248 | 8 | PLDICQSI | | 15919 |
| HPV45 | L1 | 248 | 11 | PLDICQSICKY | | 15920 |
| HPV45 | L1 | 214 | 8 | PLELKNTI | | 15921 |
| HPV45 | L1 | 214 | 9 | PLELKNTII | | 15922 |
| HPV45 | L1 | 139 | 11 | PLGIGLSGHPF | | 15923 |
| HPV45 | L1 | 440 | 9 | PTTSLVDTY | | 15924 |
| HPV45 | L1 | 440 | 11 | PTTSLVDTYRF | | 15925 |
| HPV45 | L1 | 380 | 11 | PVPNTYDPTKF | | 15926 |
| HPV45 | L1 | 470 | 8 | PYDKLKFW | | 15927 |
| HPV45 | L1 | 268 | 8 | PYGDSMFF | | 15928 |
| HPV45 | L1 | 268 | 10 | PYGDSMFFCL | | 15929 |
| HPV45 | L1 | 403 | 9 | QFIFQLCTI | | 15930 |
| HPV45 | L1 | 403 | 11 | QFIFQLCTITL | | 15931 |
| HPV45 | L1 | 182 | 11 | QLCILGCVPAI | | 15932 |
| HPV45 | L1 | 281 | 8 | QLFARHFW | | 15933 |
| HPV45 | L1 | 334 | 8 | QLFNKPYW | | 15934 |
| HPV45 | L1 | 334 | 9 | QLFNKPYWL | | 15935 |
| HPV45 | L1 | 206 | 10 | QLQPGDCPPL | | 15936 |
| HPV45 | L1 | 263 | 11 | QMSADPYGDSM | | 15937 |
| HPV45 | L1 | 491 | 8 | QYPLGRKF | | 15938 |
| HPV45 | L1 | 491 | 9 | QYPLGRKFL | | 15939 |
| HPV45 | L1 | 96 | 9 | QYRVFRVAL | | 15940 |
| HPV45 | L1 | 67 | 9 | RLLTVGNPY | | 15941 |
| HPV45 | L1 | 67 | 10 | RLLTVGNPYF | | 15942 |
| HPV45 | L1 | 124 | 9 | RLVWACVGM | | 15943 |
| HPV45 | L1 | 124 | 11 | RLVWACVGMEI | | 15944 |
| HPV45 | L1 | 101 | 10 | RVALPDPNKF | | 15945 |
| HPV45 | L1 | 46 | 8 | RVVNTDDY | | 15946 |
| HPV45 | L1 | 254 | 8 | SICKYPDY | | 15947 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | L1 | 254 | 9 | SICKYPDYL | | 15948 |
| HPV45 | L1 | 254 | 11 | SICKYPDYLQM | | 15949 |
| HPV45 | L1 | 58 | 11 | SIFYHAGSSRL | | 15950 |
| HPV45 | L1 | 427 | 8 | SILENWNF | | 15951 |
| HPV45 | L1 | 327 | 9 | SITTSDSQL | | 15952 |
| HPV45 | L1 | 327 | 10 | SITFSDSQLF | | 15953 |
| HPV45 | L1 | 443 | 8 | SLVDTYRF | | 15954 |
| HPV45 | L1 | 272 | 11 | SMFFCLRREQL | | 15955 |
| HPV45 | L1 | 423 | 10 | SMNSSILENW | | 15956 |
| HPV45 | L1 | 115 | 11 | STIYNPETQRL | | 15957 |
| HPV45 | L1 | 376 | 10 | STQNPVPNTY | | 15958 |
| HPV45 | L1 | 43 | 11 | SVARVVNTDDY | | 15959 |
| HPV45 | L1 | 175 | 9 | SVDYKQTQL | | 15960 |
| HPV45 | L1 | 175 | 11 | SVDYKQTQLCI | | 15961 |
| HPV45 | L1 | 419 | 10 | SYIHSMNSSI | | 15962 |
| HPV45 | L1 | 419 | 11 | SYIHSMNSSIL | | 15963 |
| HPV45 | L1 | 220 | 8 | TIIEDGDM | | 15964 |
| HPV45 | L1 | 410 | 9 | TITLTAEVM | | 15965 |
| HPV45 | L1 | 410 | 11 | TITLTAEVMSY | | 15966 |
| HPV45 | L1 | 116 | 10 | TIYNPETQRL | | 15967 |
| HPV45 | L1 | 200 | 8 | TLCKPAQL | | 15968 |
| HPV45 | L1 | 239 | 11 | TLQDTKCEVPL | | 15969 |
| HPV45 | L1 | 412 | 9 | TLTAEVMSY | | 15970 |
| HPV45 | L1 | 412 | 10 | TLTAEVMSYI | | 15971 |
| HPV45 | L1 | 462 | 10 | TTPPEKQDPY | | 15972 |
| HPV45 | L1 | 365 | 9 | TTRSTNLTL | | 15973 |
| HPV45 | L1 | 329 | 8 | TTSDSQLF | | 15974 |
| HPV45 | L1 | 441 | 8 | TTSLVDTY | | 15975 |
| HPV45 | L1 | 441 | 10 | TTSLVDTYRF | | 15976 |
| HPV45 | L1 | 478 | 8 | TVDLKEKF | | 15977 |
| HPV45 | L1 | 297 | 8 | TVPTDLYI | | 15978 |
| HPV45 | L1 | 361 | 11 | TVVDTTRSTNL | | 15979 |
| HPV45 | L1 | 384 | 10 | TYDPTKFKHY | | 15980 |
| HPV45 | L1 | 20 | 8 | VFPIFLQM | | 15981 |
| HPV45 | L1 | 20 | 10 | VFPIFLQMAL | | 15982 |
| HPV45 | L1 | 20 | 11 | VFPIFLQMALW | | 15983 |
| HPV45 | L1 | 293 | 10 | VMGDTVPTDL | | 15984 |
| HPV45 | L1 | 293 | 11 | VMGDTVPTDLY | | 15985 |
| HPV45 | L1 | 417 | 8 | VMSYIHSM | | 15986 |
| HPV45 | L1 | 362 | 10 | VVDTTRSTNL | | 15987 |
| HPV45 | L1 | 126 | 9 | VWACVGMEI | | 15988 |
| HPV45 | L1 | 319 | 10 | VYSPSPSGSI | | 15989 |
| HPV45 | L1 | 477 | 9 | WTVDLKEKF | | 15990 |
| HPV45 | L1 | 420 | 9 | YIHSMNSSI | | 15991 |
| HPV45 | L1 | 420 | 10 | YIHSMNSSIL | | 15992 |
| HPV45 | L1 | 303 | 9 | YIKGTSANM | | 15993 |
| HPV45 | L1 | 261 | 9 | YLQMSADPY | | 15994 |
| HPV45 | L1 | 53 | 8 | YVSRTSIF | | 15995 |
| HPV45 | L1 | 53 | 9 | YVSRTSIFY | | 15996 |
| HPV45 | L2 | 161 | 8 | AFSDPSII | | 15997 |
| HPV45 | L2 | 286 | 11 | ALSSRRGTVRF | | 15998 |
| HPV45 | L2 | 328 | 10 | ATEEIELQPL | | 15999 |
| HPV45 | L2 | 328 | 11 | ATEEIELQPLI | | 16000 |
| HPV45 | L2 | 303 | 11 | ATMFTRSGKQI | | 16001 |
| HPV45 | L2 | 340 | 8 | ATNDSDLF | | 16002 |
| HPV45 | L2 | 340 | 11 | ATNDSDLFDVY | | 16003 |
| HPV45 | L2 | 255 | 9 | AYEPLDTTL | | 16004 |
| HPV45 | L2 | 255 | 11 | AYEPLDTTLSF | | 16005 |
| HPV45 | L2 | 275 | 8 | DFMDIIRL | | 16006 |
| HPV45 | L2 | 405 | 10 | DIILPSHTPM | | 16007 |
| HPV45 | L2 | 405 | 11 | DIILPSHTPMW | | 16008 |
| HPV45 | L2 | 278 | 10 | DIIRLHRPAL | | 16009 |
| HPV45 | L2 | 322 | 11 | DISPIAATEEI | | 16010 |
| HPV45 | L2 | 142 | 11 | DITPTVDSVSI | | 16011 |
| HPV45 | L2 | 345 | 9 | DLFDVYADF | | 16012 |
| HPV45 | L2 | 83 | 11 | DVGPTRPPVVI | | 16013 |
| HPV45 | L2 | 30 | 11 | DVINKVEGTTL | | 16014 |
| HPV45 | L2 | 397 | 10 | DVPIYTGPDI | | 16015 |
| HPV45 | L2 | 397 | 11 | DVPIYTGPDII | | 16016 |
| HPV45 | L2 | 331 | 8 | EIELQPLI | | 16017 |
| HPV45 | L2 | 241 | 8 | FLTHPSSL | | 16018 |
| HPV45 | L2 | 241 | 11 | FLTHPSSLVTF | | 16019 |
| HPV45 | L2 | 122 | 9 | FTGTSGFEI | | 16020 |
| HPV45 | L2 | 157 | 11 | FTNPAFSDPSI | | 16021 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | L2 | 306 | 8 | FTRSGKQI | | 16022 |
| HPV45 | L2 | 368 | 8 | FTYPKYSL | | 16023 |
| HPV45 | L2 | 368 | 10 | FTYPKYSLTM | | 16024 |
| HPV45 | L2 | 319 | 8 | FYHDISPI | | 16025 |
| HPV45 | L2 | 51 | 9 | GIFLGGLGI | | 16026 |
| HPV45 | L2 | 430 | 8 | GIHGTQYY | | 16027 |
| HPV45 | L2 | 430 | 9 | GIHGTQYYL | | 16028 |
| HPV45 | L2 | 430 | 10 | GIHGTQYYLW | | 16029 |
| HPV45 | L2 | 25 | 8 | GTCPPDVI | | 16030 |
| HPV45 | L2 | 206 | 10 | GTEPISSTPL | | 16031 |
| HPV45 | L2 | 183 | 10 | GTPTSGSHGY | | 16032 |
| HPV45 | L2 | 433 | 9 | GTQYYLWPW | | 16033 |
| HPV45 | L2 | 433 | 10 | GTQYYLWPWY | | 16034 |
| HPV45 | L2 | 433 | 11 | GTQYYLWPWYY | | 16035 |
| HPV45 | L2 | 37 | 8 | GTTLADKI | | 16036 |
| HPV45 | L2 | 37 | 9 | GTTLADKIL | | 16037 |
| HPV45 | L2 | 37 | 11 | GTTLADKILQW | | 16038 |
| HPV45 | L2 | 134 | 8 | GTTTPAVL | | 16039 |
| HPV45 | L2 | 134 | 10 | GTTTPAVLDI | 16040 | |
| HPV45 | L2 | 292 | 8 | GTVRFSRL | | 16041 |
| HPV45 | L2 | 191 | 10 | GYEEIPLQTF | | 16042 |
| HPV45 | L2 | 318 | 9 | HFYHDISPI | | 16043 |
| HPV45 | L2 | 52 | 8 | IFLGGLGI | | 16044 |
| HPV45 | L2 | 406 | 9 | IILPSHTPM | | 16045 |
| HPV45 | L2 | 406 | 10 | IILPSHTPMW | | 16046 |
| HPV45 | L2 | 279 | 9 | IIRLHRPAL | | 16047 |
| HPV45 | L2 | 407 | 8 | ILPSHTPM | | 16048 |
| HPV45 | L2 | 407 | 9 | ILPSHTPMW | | 16049 |
| HPV45 | L2 | 44 | 9 | ILQWSSLGI | | 16050 |
| HPV45 | L2 | 44 | 10 | ILQWSSLGIF | | 16051 |
| HPV45 | L2 | 44 | 11 | ILQWSSLGIFL | | 16052 |
| HPV45 | L2 | 143 | 10 | ITPTVDSVSI | | 16053 |
| HPV45 | L2 | 400 | 8 | IYTGPDII | | 16054 |
| HPV45 | L2 | 400 | 9 | IYTGPDIIL | | 16055 |
| HPV45 | L2 | 43 | 8 | KILQWSSL | | 16056 |
| HPV45 | L2 | 43 | 10 | KILQWSSLGI | | 16057 |
| HPV45 | L2 | 43 | 11 | KILQWSSLGIF | | 16058 |
| HPV45 | L2 | 34 | 11 | KVEGTTLADKI | | 16059 |
| HPV45 | L2 | 346 | 8 | LFDVYADF | | 16060 |
| HPV45 | L2 | 337 | 10 | LISATNDSDL | | 16061 |
| HPV45 | L2 | 337 | 11 | LISATNDSDLF | | 16062 |
| HPV45 | L2 | 242 | 10 | LTHPSSLVTF | | 16063 |
| HPV45 | L2 | 375 | 11 | LTMPSTAASSY | | 16064 |
| HPV45 | L2 | 392 | 9 | LTSAWDVPI | | 16065 |
| HPV45 | L2 | 392 | 10 | LTSAWDVPIY | | 16066 |
| HPV45 | L2 | 248 | 9 | LVTFDNPAY | | 16067 |
| HPV45 | L2 | 438 | 8 | LWPWYYYF | | 16068 |
| HPV45 | L2 | 305 | 9 | MFTRSGKQI | | 16069 |
| HPV45 | L2 | 270 | 8 | NVPDSDFM | | 16070 |
| HPV45 | L2 | 270 | 10 | NVPDSDFMDI | | 16071 |
| HPV45 | L2 | 270 | 11 | NVPDSDFMDII | | 16072 |
| HPV45 | L2 | 387 | 10 | NVTVPLTSAW | | 16073 |
| HPV45 | L2 | 325 | 8 | PIAATEEI | | 16074 |
| HPV45 | L2 | 325 | 10 | PIAATEEIEL | | 16075 |
| HPV45 | L2 | 399 | 8 | PIYTGPDI | | 16076 |
| HPV45 | L2 | 399 | 9 | PIYTGPDII | | 16077 |
| HPV45 | L2 | 399 | 10 | PIYTGPDIIL | | 16078 |
| HPV45 | L2 | 258 | 8 | PLDTTLSF | | 16079 |
| HPV45 | L2 | 336 | 11 | PLISATNDSDL | | 16080 |
| HPV45 | L2 | 391 | 10 | PLTSAWDVPI | | 16081 |
| HPV45 | L2 | 391 | 11 | PLTSAWDVPIY | | 16082 |
| HPV45 | L2 | 98 | 9 | PTDPSIVTL | | 16083 |
| HPV45 | L2 | 120 | 9 | PTFTGTSGF | | 16084 |
| HPV45 | L2 | 120 | 11 | PTFTGTSGFEI | | 16085 |
| HPV45 | L2 | 420 | 9 | PTNASTTTY | | 16086 |
| HPV45 | L2 | 420 | 10 | PTNASTTTYI | | 16087 |
| HPV45 | L2 | 86 | 8 | PTRPPVVI | | 16088 |
| HPV45 | L2 | 185 | 8 | PTSGSHGY | | 16089 |
| HPV45 | L2 | 185 | 11 | PTSGSHGYEEI | | 16090 |
| HPV45 | L2 | 267 | 10 | PTSNVPDSDF | | 16091 |
| HPV45 | L2 | 267 | 11 | PTSNVPDSDFM | | 16092 |
| HPV45 | L2 | 145 | 8 | PTVDSVSI | | 16093 |
| HPV45 | L2 | 216 | 11 | PTVRRVRGPRL | | 16094 |
| HPV45 | L2 | 95 | 9 | PVGPTDPSI | | 16095 |

TABLE X-continued

A24 Supermotif Peptides

| Type | Protein | Position | No. of Amino Acids | Sequence | A*2402 | Seq. Id. No. |
|---|---|---|---|---|---|---|
| HPV45 | L2 | 118 | 11 | PVPTFTGTSGF | | 16096 |
| HPV45 | L2 | 453 | 8 | PYFFADGF | | 16097 |
| HPV45 | L2 | 240 | 9 | QFLTHPSSL | | 16098 |
| HPV45 | L2 | 312 | 8 | QIGGRVHF | | 16099 |
| HPV45 | L2 | 312 | 9 | QIGGRVHFY | | 16100 |
| HPV45 | L2 | 172 | 9 | QTGEVSGNI | | 16101 |
| HPV45 | L2 | 172 | 10 | QTGEVSGNIF | | 16102 |
| HPV45 | L2 | 233 | 9 | QVRVSTSQF | | 16103 |
| HPV45 | L2 | 233 | 10 | QVRVSTSQFL | | 16104 |
| HPV45 | L2 | 46 | 8 | QWSSLGIF | | 16105 |
| HPV45 | L2 | 46 | 9 | QWSSLGIFL | | 16106 |
| HPV45 | L2 | 435 | 8 | QYYLWPWY | | 16107 |
| HPV45 | L2 | 435 | 9 | QYYLWPWYY | | 16108 |
| HPV45 | L2 | 435 | 10 | QYYLWPWYYY | | 16109 |
| HPV45 | L2 | 435 | 11 | QYYLWPWYYYF | | 16110 |
| HPV45 | L2 | 295 | 11 | RFSRLGQRATM | | 16111 |
| HPV45 | L2 | 451 | 10 | RIPYFFADGF | | 16112 |
| HPV45 | L2 | 298 | 8 | RLGQRATM | | 16113 |
| HPV45 | L2 | 298 | 9 | RLGQRATMF | | 16114 |
| HPV45 | L2 | 316 | 8 | RVHFYHDI | | 16115 |
| HPV45 | L2 | 316 | 11 | RVHFYHDISPI | | 16116 |
| HPV45 | L2 | 220 | 8 | RVRGPRLY | | 16117 |
| HPV45 | L2 | 235 | 8 | RVSTSQFL | | 16118 |
| HPV45 | L2 | 367 | 9 | SFTYPKYSL | | 16119 |
| HPV45 | L2 | 367 | 11 | SFTYPKYSLTM | | 16120 |
| HPV45 | L2 | 49 | 9 | SLGIFLGGL | | 16121 |
| HPV45 | L2 | 49 | 11 | SLGIFLGGLGI | | 16122 |
| HPV45 | L2 | 247 | 10 | SLVTFDNPAY | | 16123 |
| HPV45 | L2 | 362 | 9 | STIHKSFTY | | 16124 |
| HPV45 | L2 | 154 | 9 | STSFTNPAF | | 16125 |
| HPV45 | L2 | 358 | 11 | STTPSTIHKSF | | 16126 |
| HPV45 | L2 | 424 | 8 | STTTYIGI | | 16127 |
| HPV45 | L2 | 149 | 9 | SVSISSTSF | | 16128 |
| HPV45 | L2 | 384 | 9 | SYSNVTVPL | | 16129 |
| HPV45 | L2 | 250 | 10 | TFDNPAYEPL | | 16130 |
| HPV45 | L2 | 121 | 8 | TFTGTSGF | | 16131 |
| HPV45 | L2 | 121 | 10 | TFTGTSGFEI | | 16132 |
| HPV45 | L2 | 363 | 8 | TIHKSFTY | | 16133 |
| HPV45 | L2 | 363 | 11 | TIHKSFTYPKY | | 16134 |
| HPV45 | L2 | 39 | 9 | TLADKILQW | | 16135 |
| HPV45 | L2 | 304 | 10 | TMFTRSGKQI | | 16136 |
| HPV45 | L2 | 376 | 10 | TMPSTAASSY | | 16137 |
| HPV45 | L2 | 38 | 8 | TTLADKIL | | 16138 |
| HPV45 | L2 | 38 | 10 | TTLADKILQW | | 16139 |
| HPV45 | L2 | 136 | 8 | TTPAVLDI | | 16140 |
| HPV45 | L2 | 359 | 10 | TTPSTIHKSF | | 16141 |
| HPV45 | L2 | 135 | 9 | TTTPAVLDI | | 16142 |
| HPV45 | L2 | 426 | 11 | TTYIGIHGTQY | | 16143 |
| HPV45 | L2 | 389 | 8 | TVPLTSAW | | 16144 |
| HPV45 | L2 | 217 | 10 | TVRRVRGPRL | | 16145 |
| HPV45 | L2 | 217 | 11 | TVRRVRGPRLY | | 16146 |
| HPV45 | L2 | 427 | 10 | TYIGIHGTQY | | 16147 |
| HPV45 | L2 | 427 | 11 | TYIGIHGTQYY | | 16148 |
| HPV45 | L2 | 369 | 9 | TYPKYSLTM | | 16149 |
| HPV45 | L2 | 31 | 10 | VINKVEGTTL | | 16150 |
| HPV45 | L2 | 249 | 8 | VTFDNPAY | | 16151 |
| HPV45 | L2 | 249 | 11 | VTFDNPAYEPL | | 16152 |
| HPV45 | L2 | 388 | 9 | VTVPLTSAW | | 16153 |
| HPV45 | L2 | 112 | 11 | VVASGAPVPTF | | 16154 |
| HPV45 | L2 | 444 | 9 | YFPKKRKRI | | 16155 |
| HPV45 | L2 | 444 | 11 | YFPKKRKRIPY | | 16156 |
| HPV45 | L2 | 428 | 9 | YIGIHGTQY | | 16157 |
| HPV45 | L2 | 428 | 10 | YIGIHGTQYY | | 16158 |
| HPV45 | L2 | 428 | 11 | YIGIHGTQYYL | | 16159 |
| HPV45 | L2 | 437 | 8 | YLWPWYYY | | 16160 |
| HPV45 | L2 | 437 | 9 | YLWPWYYYF | | 16161 |
| HPV45 | L2 | 401 | 8 | YTGPDIIL | | 16162 |
| HPV45 | L2 | 443 | 10 | YYFPKKRKRI | | 16163 |
| HPV45 | L2 | 436 | 8 | YYLWPWYY | | 16164 |
| HPV45 | L2 | 436 | 9 | YYLWPWYYY | | 16165 |
| HPV45 | L2 | 436 | 10 | YYLWPWYYYF | | 16166 |
| HPV45 | L2 | 442 | 11 | YYYFPKKRKRI | | 16167 |
| HPV56 | E2 | 15 | 8 | AIEVQIAL | | 16168 |
| HPV56 | E2 | 15 | 11 | AIEVQIALESL | | 16169 |

TABLE X-continued

A24 Supermotif Peptides

| Type | Protein | Position | No. of Amino Acids | Sequence | A*2402 | Seq. Id. No. |
|---|---|---|---|---|---|---|
| HPV56 | E2 | 21 | 9 | ALESLSTTI | | 16170 |
| HPV56 | E2 | 21 | 10 | ALESLSTTIY | | 16171 |
| HPV56 | E2 | 52 | 9 | CFKKEGQHI | | 16172 |
| HPV56 | E2 | 71 | 9 | CMQYVAWKY | | 16173 |
| HPV56 | E2 | 71 | 10 | CMQYVAWKYI | | 16174 |
| HPV56 | E2 | 71 | 11 | CMQYVAWKYIY | | 16175 |
| HPV56 | E2 | 204 | 8 | CVTTHTHI | | 16176 |
| HPV56 | E2 | 113 | 9 | DFEQEAKKF | | 16177 |
| HPV56 | E2 | 39 | 8 | DTCEELWL | | 16178 |
| HPV56 | E2 | 263 | 8 | DVTSTYHW | | 16179 |
| HPV56 | E2 | 43 | 11 | ELWLTEPKKCF | | 16180 |
| HPV56 | E2 | 288 | 8 | ETQRNSFL | | 16181 |
| HPV56 | E2 | 128 | 9 | EVHMENESI | | 16182 |
| HPV56 | E2 | 128 | 10 | EVHMENESIY | | 16183 |
| HPV56 | E2 | 17 | 9 | EVQIALESL | | 16184 |
| HPV56 | E2 | 34 | 11 | EWTLRDTCEEL | | 16185 |
| HPV56 | E2 | 294 | 11 | FLSHVKIPVVY | | 16186 |
| HPV56 | E2 | 261 | 8 | FVDVTSTY | | 16187 |
| HPV56 | E2 | 261 | 10 | FVDVTSTYHW | | 16188 |
| HPV56 | E2 | 94 | 8 | GVDYRGIY | | 16189 |
| HPV56 | E2 | 94 | 9 | GVDYRGIYY | | 16190 |
| HPV56 | E2 | 87 | 11 | GWQKVCSGVDY | | 16191 |
| HPV56 | E2 | 239 | 9 | HLKGEPNRL | | 16192 |
| HPV56 | E2 | 130 | 8 | HMENESIY | | 16193 |
| HPV56 | E2 | 297 | 8 | HVKIPVVY | | 16194 |
| HPV56 | E2 | 297 | 10 | HVKIPVVYRL | | 16195 |
| HPV56 | E2 | 269 | 10 | HWTSTDNKNY | | 16196 |
| HPV56 | E2 | 126 | 11 | IWEVHMENESI | | 16197 |
| HPV56 | E2 | 284 | 11 | IYKDETQRNSF | | 16198 |
| HPV56 | E2 | 29 | 9 | IYNNEEWTL | | 16199 |
| HPV56 | E2 | 80 | 9 | IYYNGDCGW | | 16200 |
| HPV56 | E2 | 100 | 11 | IYYVHDGHKTY | | 16201 |
| HPV56 | E2 | 120 | 8 | KFGCKNIW | | 16202 |
| HPV56 | E2 | 299 | 8 | KIPVVYRL | | 16203 |
| HPV56 | E2 | 299 | 10 | KIPVVYRLVW | | 16204 |
| HPV56 | E2 | 258 | 11 | KTLFVDVTSTY | | 16205 |
| HPV56 | E2 | 233 | 8 | KTTPVVHL | | 16206 |
| HPV56 | E2 | 90 | 8 | KVCSGVDY | | 16207 |
| HPV56 | E2 | 90 | 11 | KVCSGVDYRGI | | 16208 |
| HPV56 | E2 | 78 | 11 | KYIYYNGDCGW | | 16209 |
| HPV56 | E2 | 260 | 9 | LFVDVTSTY | | 16210 |
| HPV56 | E2 | 260 | 11 | LFVDVTSTYHW | | 16211 |
| HPV56 | E2 | 46 | 8 | LTEPKKCF | | 16212 |
| HPV56 | E2 | 44 | 10 | LWLTEPKKCF | | 16213 |
| HPV56 | E2 | 216 | 9 | NTDSRSRSI | | 16214 |
| HPV56 | E2 | 149 | 11 | NVSPVETVNEY | | 16215 |
| HPV56 | E2 | 277 | 8 | NYSIITII | | 16216 |
| HPV56 | E2 | 277 | 9 | NYSIITIIY | | 16217 |
| HPV56 | E2 | 152 | 8 | PVETVNEY | | 16218 |
| HPV56 | E2 | 301 | 8 | PVVYRLVW | | 16219 |
| HPV56 | E2 | 19 | 11 | QIALESLSTTI | | 16220 |
| HPV56 | E2 | 6 | 11 | QVCKAKACSAI | | 16221 |
| HPV56 | E2 | 73 | 8 | QYVAWKYI | | 16222 |
| HPV56 | E2 | 73 | 9 | QYVAWKYIY | | 16223 |
| HPV56 | E2 | 73 | 10 | QYVAWKYIYY | | 16224 |
| HPV56 | E2 | 253 | 8 | RFQKYKTL | | 16225 |
| HPV56 | E2 | 253 | 9 | RFQKYKTLF | | 16226 |
| HPV56 | E2 | 246 | 9 | RLKCCRYRF | | 16227 |
| HPV56 | E2 | 251 | 10 | RYRFQKYKTL | | 16228 |
| HPV56 | E2 | 251 | 11 | RYRFQKYKTLF | | 16229 |
| HPV56 | E2 | 293 | 8 | SFLSHVKI | | 16230 |
| HPV56 | E2 | 272 | 9 | STDNKNYSI | | 16231 |
| HPV56 | E2 | 272 | 10 | STDNKNYSII | | 16232 |
| HPV56 | E2 | 26 | 10 | STTIYNNEEW | | 16233 |
| HPV56 | E2 | 141 | 8 | SVSSTCRY | | 16234 |
| HPV56 | E2 | 28 | 8 | TIYNNEEW | | 16235 |
| HPV56 | E2 | 28 | 10 | TIYNNEEWTL | | 16236 |
| HPV56 | E2 | 259 | 10 | TLFVDVTSTY | | 16237 |
| HPV56 | E2 | 36 | 9 | TLRDTCEEL | | 16238 |
| HPV56 | E2 | 36 | 10 | TLRDTCEELW | | 16239 |
| HPV56 | E2 | 36 | 11 | TLRDTCEELWL | | 16240 |
| HPV56 | E2 | 27 | 9 | TTIYNNEEW | | 16241 |
| HPV56 | E2 | 27 | 11 | TTIYNNEEWTL | | 16242 |
| HPV56 | E2 | 237 | 11 | VVHLKGEPNRL | | 16243 |

TABLE X-continued

A24 Supermotif Peptides

| Type | Protein | Position | No. of Amino Acids | Sequence | A*2402 | Seq. Id. No. |
|---|---|---|---|---|---|---|
| HPV56 | E2 | 62 | 11 | VWFDGSKNNCM | | 16244 |
| HPV56 | E2 | 63 | 10 | WFDGSKNNCM | | 16245 |
| HPV56 | E2 | 45 | 9 | WLTEPKKCF | | 16246 |
| HPV56 | E2 | 35 | 10 | WTLRDTCEEL | | 16247 |
| HPV56 | E2 | 35 | 11 | WTLRDTCEELW | | 16248 |
| HPV56 | E2 | 270 | 9 | WTSTDNKNY | | 16249 |
| HPV56 | E2 | 270 | 11 | WTSTDNKNYSI | | 16250 |
| HPV56 | E2 | 79 | 10 | YIYYNGDCGW | | 16251 |
| HPV56 | E2 | 111 | 11 | YTDFEQEAKKF | | 16252 |
| HPV56 | E2 | 74 | 8 | YVAWKYIY | | 16253 |
| HPV56 | E2 | 74 | 9 | YVAWKYIYY | | 16254 |
| HPV56 | E2 | 102 | 9 | YVHDGHKTY | | 16255 |
| HPV56 | E2 | 102 | 10 | YVHDGHKTYY | | 16256 |
| HPV56 | E2 | 81 | 8 | YYNGDCGW | | 16257 |
| HPV56 | E2 | 101 | 10 | YYVHDGHKTY | | 16258 |
| HPV56 | E2 | 101 | 11 | YYVHDGHKTYY | | 16259 |
| HPV56 | E6 | 89 | 11 | ATLESITKKQL | | 16260 |
| HPV56 | E6 | 64 | 8 | AVCRVCLL | | 16261 |
| HPV56 | E6 | 64 | 9 | AVCRVCLLF | | 16262 |
| HPV56 | E6 | 64 | 10 | AVCRVCLLFY | | 16263 |
| HPV56 | E6 | 69 | 11 | CLLFYSKVRKY | | 16264 |
| HPV56 | E6 | 50 | 8 | CTELKLVY | | 16265 |
| HPV56 | E6 | 33 | 8 | CVYCKKEL | | 16266 |
| HPV56 | E6 | 106 | 8 | CYRCQSPL | | 16267 |
| HPV56 | E6 | 60 | 11 | DFPYAVCRVCL | | 16268 |
| HPV56 | E6 | 28 | 8 | DLRLSCVY | | 16269 |
| HPV56 | E6 | 83 | 9 | DYSVYGATL | | 16270 |
| HPV56 | E6 | 23 | 9 | EIPLIDLRL | | 16271 |
| HPV56 | E6 | 52 | 10 | ELKLVYRDDF | | 16272 |
| HPV56 | E6 | 39 | 8 | ELTRAEVY | | 16273 |
| HPV56 | E6 | 39 | 10 | ELTRAEVYNF | | 16274 |
| HPV56 | E6 | 20 | 8 | EVLEIPLI | | 16275 |
| HPV56 | E6 | 20 | 10 | EVLEIPLIDL | | 16276 |
| HPV56 | E6 | 44 | 10 | EVYNFACTEL | | 16277 |
| HPV56 | E6 | 72 | 8 | FYSKVRKY | | 16278 |
| HPV56 | E6 | 72 | 10 | FYSKVRKYRY | | 16279 |
| HPV56 | E6 | 72 | 11 | FYSKVRKYRYY | | 16280 |
| HPV56 | E6 | 134 | 10 | GWTGSCLGCW | | 16281 |
| HPV56 | E6 | 17 | 8 | HLSEVLEI | | 16282 |
| HPV56 | E6 | 17 | 10 | HLSEVLEIPL | | 16283 |
| HPV56 | E6 | 17 | 11 | HLSEVLEIPLI | | 16284 |
| HPV56 | E6 | 94 | 9 | ITKKQLCDL | | 16285 |
| HPV56 | E6 | 94 | 10 | ITKKQLCDLL | | 16286 |
| HPV56 | E6 | 94 | 11 | ITKKQLCDLLI | | 16287 |
| HPV56 | E6 | 54 | 8 | KLVYRDDF | | 16288 |
| HPV56 | E6 | 54 | 10 | KLVYRDDFPY | | 16289 |
| HPV56 | E6 | 75 | 8 | KVRKYRYY | | 16290 |
| HPV56 | E6 | 75 | 10 | KVRKYRYYDY | | 16291 |
| HPV56 | E6 | 78 | 10 | KYRYYDYSVY | | 16292 |
| HPV56 | E6 | 71 | 9 | LFYSKVRKY | | 16293 |
| HPV56 | E6 | 71 | 11 | LFYSKVRKYRY | | 16294 |
| HPV56 | E6 | 130 | 11 | LIAHGWTGSCL | | 16295 |
| HPV56 | E6 | 26 | 10 | LIDLRLSCVY | | 16296 |
| HPV56 | E6 | 103 | 11 | LICYRCQSPL | | 16297 |
| HPV56 | E6 | 70 | 10 | LLFYSKVRKY | | 16298 |
| HPV56 | E6 | 113 | 8 | LTPEEKQL | | 16299 |
| HPV56 | E6 | 40 | 9 | LTRAEVYNF | | 16300 |
| HPV56 | E6 | 55 | 9 | LVYRDDFPY | | 16301 |
| HPV56 | E6 | 47 | 9 | NFACTELKL | | 16302 |
| HPV56 | E6 | 47 | 11 | NFACTELKLVY | | 16303 |
| HPV56 | E6 | 25 | 11 | PLIDLRLSCVY | | 16304 |
| HPV56 | E6 | 112 | 9 | PLTPEEKQL | | 16305 |
| HPV56 | E6 | 62 | 9 | PYAVCRVCL | | 16306 |
| HPV56 | E6 | 62 | 10 | PYAVCRVCLL | | 16307 |
| HPV56 | E6 | 62 | 11 | PYAVCRVCLLF | | 16308 |
| HPV56 | E6 | 98 | 10 | QLCDLLIRCY | | 16309 |
| HPV56 | E6 | 119 | 10 | QLHCDRKRRF | | 16310 |
| HPV56 | E6 | 127 | 9 | RFHLIAHGW | | 16311 |
| HPV56 | E6 | 30 | 11 | RLSCVYCKKEL | | 16312 |
| HPV56 | E6 | 80 | 8 | RYYDYSVY | | 16313 |
| HPV56 | E6 | 93 | 10 | SITKKQLCDL | | 16314 |
| HPV56 | E6 | 93 | 11 | SITKKQLCDLL | | 16315 |
| HPV56 | E6 | 14 | 9 | SLHHLSEVL | | 16316 |
| HPV56 | E6 | 14 | 11 | SLHHLSEVLEI | | 16317 |

TABLE X-continued

A24 Supermotif Peptides

| Type | Protein | Position | No. of Amino Acids | Sequence | A*2402 | Seq. Id. No. |
|---|---|---|---|---|---|---|
| HPV56 | E6 | 85 | 10 | SVYGATLESI | | 16318 |
| HPV56 | E6 | 90 | 10 | TLESITKKQL | | 16319 |
| HPV56 | E6 | 21 | 9 | VLEIPLIDL | | 16320 |
| HPV56 | E6 | 21 | 11 | VLEIPLIDLRL | | 16321 |
| HPV56 | E6 | 86 | 9 | VYGATLESI | | 16322 |
| HPV56 | E6 | 45 | 9 | VYNFACTEL | | 16323 |
| HPV56 | E6 | 45 | 11 | VYNFACTELKL | | 16324 |
| HPV56 | E6 | 56 | 8 | VYRDDFPY | | 16325 |
| HPV56 | E6 | 135 | 9 | WTGSCLGCW | | 16326 |
| HPV56 | E6 | 81 | 11 | YYDYSVYGATL | | 16327 |
| HPV56 | E7 | 93 | 8 | ALTVTCPL | | 16328 |
| HPV56 | E7 | 75 | 9 | DIQSTKEDL | | 16329 |
| HPV56 | E7 | 22 | 8 | DLQCNEQL | | 16330 |
| HPV56 | E7 | 82 | 8 | DLRVVQQL | | 16331 |
| HPV56 | E7 | 82 | 9 | DLRVVQQLL | | 16332 |
| HPV56 | E7 | 82 | 10 | DLRVVQQLLM | | 16333 |
| HPV56 | E7 | 20 | 10 | EIDLQCNEQL | | 16334 |
| HPV56 | E7 | 14 | 8 | ELTPQTEI | | 16335 |
| HPV56 | E7 | 14 | 10 | ELTPQTEIDL | | 16336 |
| HPV56 | E7 | 62 | 9 | HVPCCECKF | | 16337 |
| HPV56 | E7 | 69 | 8 | KFVVQLDI | | 16338 |
| HPV56 | E7 | 4 | 10 | KVPTLQDVVL | | 16339 |
| HPV56 | E7 | 60 | 11 | LIHVPCCECKF | | 16340 |
| HPV56 | E7 | 90 | 11 | LMGALTVTCPL | | 16341 |
| HPV56 | E7 | 15 | 9 | LTPQTEIDL | | 16342 |
| HPV56 | E7 | 6 | 8 | PTLQDVVL | | 16343 |
| HPV56 | E7 | 6 | 10 | PTLQDVVLEL | | 16344 |
| HPV56 | E7 | 73 | 11 | QLDIQSTKEDL | | 16345 |
| HPV56 | E7 | 84 | 8 | RVVQQLLM | | 16346 |
| HPV56 | E7 | 84 | 11 | RVVQQLLMGAL | | 16347 |
| HPV56 | E7 | 7 | 9 | TLQDVVLEL | | 16348 |
| HPV56 | E7 | 12 | 10 | VLELTPQTEI | | 16349 |
| HPV56 | E7 | 11 | 11 | VVLELTPQTEI | | 16350 |
| HPV56 | E7 | 85 | 10 | VVQQLLMGAL | | 16351 |
| HPV56 | L1 | 58 | 11 | ATDSYVKRTSI | | 16352 |
| HPV56 | L1 | 381 | 8 | ATEQLSKY | | 16353 |
| HPV56 | L1 | 327 | 8 | ATPSGSMI | | 16354 |
| HPV56 | L1 | 444 | 8 | ATSLEDKY | | 16355 |
| HPV56 | L1 | 444 | 10 | ATSLEDKYRY | | 16356 |
| HPV56 | L1 | 37 | 11 | ATWRPSENKVY | | 16357 |
| HPV56 | L1 | 26 | 8 | AVNVFPIF | | 16358 |
| HPV56 | L1 | 26 | 9 | AVNVFPIFL | | 16359 |
| HPV56 | L1 | 26 | 11 | AVNVFPIFLQM | | 16360 |
| HPV56 | L1 | 275 | 8 | AYGDSMWF | | 16361 |
| HPV56 | L1 | 275 | 9 | AYGDSMWFY | | 16362 |
| HPV56 | L1 | 275 | 10 | AYGDSMWFYL | | 16363 |
| HPV56 | L1 | 422 | 10 | AYLHNMNANL | | 16364 |
| HPV56 | L1 | 422 | 11 | AYLHNMNANLL | | 16365 |
| HPV56 | L1 | 101 | 11 | AYQYRVFRVRL | | 16366 |
| HPV56 | L1 | 191 | 9 | CIVGCTPAM | | 16367 |
| HPV56 | L1 | 195 | 9 | CTPAMGEHW | | 16368 |
| HPV56 | L1 | 257 | 9 | DIVQSTCKY | | 16369 |
| HPV56 | L1 | 491 | 11 | DLDQFPLGRKF | | 16370 |
| HPV56 | L1 | 233 | 10 | DMIDTGFGAM | | 16371 |
| HPV56 | L1 | 236 | 9 | DTGFGAMDF | | 16372 |
| HPV56 | L1 | 369 | 8 | DTTRSTNM | | 16373 |
| HPV56 | L1 | 369 | 10 | DTTRSTNMTI | | 16374 |
| HPV56 | L1 | 23 | 8 | DVGAVNVF | | 16375 |
| HPV56 | L1 | 23 | 10 | DVGAVNVFPI | | 16376 |
| HPV56 | L1 | 23 | 11 | DVGAVNVFPIF | | 16377 |
| HPV56 | L1 | 481 | 8 | DVNLQDSF | | 16378 |
| HPV56 | L1 | 267 | 10 | DYLKMSADAY | | 16379 |
| HPV56 | L1 | 404 | 8 | ELQFVFQL | | 16380 |
| HPV56 | L1 | 404 | 11 | ELQFVFQLCKI | | 16381 |
| HPV56 | L1 | 303 | 8 | ETIPAELY | | 16382 |
| HPV56 | L1 | 303 | 9 | ETIPAELYL | | 16383 |
| HPV56 | L1 | 140 | 8 | EVGRGQPL | | 16384 |
| HPV56 | L1 | 419 | 9 | EVMAYLHNM | | 16385 |
| HPV56 | L1 | 402 | 8 | EYELQFVF | | 16386 |
| HPV56 | L1 | 402 | 10 | EYELQFVFQL | | 16387 |
| HPV56 | L1 | 21 | 10 | FLDVGAVNVF | | 16388 |
| HPV56 | L1 | 407 | 8 | FVFQLCKI | | 16389 |
| HPV56 | L1 | 407 | 10 | FVFQLCKITL | | 16390 |
| HPV56 | L1 | 479 | 10 | FWDVNLQDSF | | 16391 |

TABLE X-continued

A24 Supermotif Peptides

| Type | Protein | Position | No. of Amino Acids | Sequence | A*2402 | Seq. Id. No. |
|---|---|---|---|---|---|---|
| HPV56 | L1 | 69 | 9 | FYHAGSSRL | | 16392 |
| HPV56 | L1 | 69 | 10 | FYHAGSSRLL | | 16393 |
| HPV56 | L1 | 282 | 8 | FYLRREQL | | 16394 |
| HPV56 | L1 | 282 | 9 | FYLRREQLF | | 16395 |
| HPV56 | L1 | 238 | 10 | GFGAMDFKVL | | 16396 |
| HPV56 | L1 | 356 | 8 | GICWGNQL | | 16397 |
| HPV56 | L1 | 356 | 9 | GICWGNQLF | | 16398 |
| HPV56 | L1 | 138 | 10 | GLEVGRGQPL | | 16399 |
| HPV56 | L1 | 118 | 8 | GLPDTNIY | | 16400 |
| HPV56 | L1 | 150 | 8 | GLSGHPLF | | 16401 |
| HPV56 | L1 | 150 | 11 | GLSGHPLFNRL | | 16402 |
| HPV56 | L1 | 438 | 10 | GLSPPVATSL | | 16403 |
| HPV56 | L1 | 399 | 9 | HVEEYELQF | | 16404 |
| HPV56 | L1 | 399 | 11 | HVEEYELQFVF | | 16405 |
| HPV56 | L1 | 15 | 8 | HYGLCIFL | | 16406 |
| HPV56 | L1 | 20 | 11 | IFLDVGAVNVF | | 16407 |
| HPV56 | L1 | 32 | 8 | IFLQMATW | | 16408 |
| HPV56 | L1 | 68 | 10 | IFYHAGSSRL | | 16409 |
| HPV56 | L1 | 68 | 11 | IFYHAGSSRLL | | 16410 |
| HPV56 | L1 | 414 | 8 | ITLSAEVM | | 16411 |
| HPV56 | L1 | 414 | 10 | ITLSAEVMAY | | 16412 |
| HPV56 | L1 | 414 | 11 | ITLSAEVMAYL | | 16413 |
| HPV56 | L1 | 334 | 8 | ITSEAQLF | | 16414 |
| HPV56 | L1 | 192 | 8 | IVGCTPAM | | 16415 |
| HPV56 | L1 | 258 | 8 | IVQSTCKY | | 16416 |
| HPV56 | L1 | 258 | 11 | IVQSTCKYPDY | | 16417 |
| HPV56 | L1 | 124 | 9 | IYNPDQERL | | 16418 |
| HPV56 | L1 | 124 | 11 | IYNPDQERLVW | | 16419 |
| HPV56 | L1 | 8 | 9 | IYRDPPLHY | | 16420 |
| HPV56 | L1 | 8 | 11 | IYRDPPLHYGL | | 16421 |
| HPV56 | L1 | 116 | 9 | KFGLPDTNI | | 16422 |
| HPV56 | L1 | 116 | 10 | KFGLPDTNIY | | 16423 |
| HPV56 | L1 | 478 | 11 | KFWDVNLQDSF | | 16424 |
| HPV56 | L1 | 413 | 9 | KITLSAEVM | | 16425 |
| HPV56 | L1 | 413 | 11 | KITLSAEVMAY | | 16426 |
| HPV56 | L1 | 270 | 11 | KMSADAYGDSM | | 16427 |
| HPV56 | L1 | 93 | 10 | KTNIPKVSAY | | 16428 |
| HPV56 | L1 | 300 | 10 | KVGETIPAEL | | 16429 |
| HPV56 | L1 | 300 | 11 | KVGETIPAELY | | 16430 |
| HPV56 | L1 | 98 | 10 | KVSAYQYRVF | | 16431 |
| HPV56 | L1 | 55 | 8 | KVVATDSY | | 16432 |
| HPV56 | L1 | 387 | 10 | KYDARKINQY | | 16433 |
| HPV56 | L1 | 387 | 11 | KYDARKINQYL | | 16434 |
| HPV56 | L1 | 476 | 9 | KYKFWDVNL | | 16435 |
| HPV56 | L1 | 264 | 8 | KYPDYLKM | | 16436 |
| HPV56 | L1 | 450 | 10 | KYRYVRSTAI | | 16437 |
| HPV56 | L1 | 340 | 8 | LFNKPYWL | | 16438 |
| HPV56 | L1 | 224 | 11 | LINTPIEDGDM | | 16439 |
| HPV56 | L1 | 77 | 8 | LLAVGHPY | | 16440 |
| HPV56 | L1 | 77 | 9 | LLAVGHPYY | | 16441 |
| HPV56 | L1 | 431 | 9 | LLEDWNIGL | | 16442 |
| HPV56 | L1 | 132 | 8 | LVWACVGL | | 16443 |
| HPV56 | L1 | 234 | 9 | MIDTGFGAM | | 16444 |
| HPV56 | L1 | 234 | 11 | MIDTGFGAMDF | | 16445 |
| HPV56 | L1 | 333 | 8 | MITSEAQL | | 16446 |
| HPV56 | L1 | 333 | 9 | MITSEAQLF | | 16447 |
| HPV56 | L1 | 2 | 8 | MLPMMYIY | | 16448 |
| HPV56 | L1 | 1 | 8 | MMLPMMYI | | 16449 |
| HPV56 | L1 | 1 | 9 | MMLPMMYIY | | 16450 |
| HPV56 | L1 | 5 | 10 | MMYIYRDPPL | | 16451 |
| HPV56 | L1 | 376 | 10 | MTISTATEQL | | 16452 |
| HPV56 | L1 | 280 | 10 | MWFYLRREQL | | 16453 |
| HPV56 | L1 | 280 | 11 | MWFYLRREQLF | | 16454 |
| HPV56 | L1 | 6 | 9 | MYIYRDPPL | | 16455 |
| HPV56 | L1 | 6 | 11 | MYIYRDPPLHY | | 16456 |
| HPV56 | L1 | 95 | 8 | NIPKVSAY | | 16457 |
| HPV56 | L1 | 95 | 10 | NIPKVSAYQY | | 16458 |
| HPV56 | L1 | 180 | 11 | NISVDGKQTQL | | 16459 |
| HPV56 | L1 | 123 | 10 | NIYNPDQERL | | 16460 |
| HPV56 | L1 | 167 | 8 | NLANNNVI | | 16461 |
| HPV56 | L1 | 430 | 8 | NLLEDWNI | | 16462 |
| HPV56 | L1 | 430 | 10 | NLLEDWNIGL | | 16463 |
| HPV56 | L1 | 483 | 10 | NLQDSFSTDL | | 16464 |
| HPV56 | L1 | 426 | 10 | NMNANLLEDW | | 16465 |

TABLE X-continued

A24 Supermotif Peptides

| Type | Protein | Position | No. of Amino Acids | Sequence | A*2402 | Seq. Id. No. |
|---|---|---|---|---|---|---|
| HPV56 | L1 | 375 | 11 | NMTISTATEQL | | 16466 |
| HPV56 | L1 | 226 | 9 | NTPIEDGDM | | 16467 |
| HPV56 | L1 | 226 | 10 | NTPIEDGDMI | | 16468 |
| HPV56 | L1 | 28 | 9 | NVFPIFLQM | | 16469 |
| HPV56 | L1 | 172 | 10 | NVIEDSRDNI | | 16470 |
| HPV56 | L1 | 228 | 8 | PIEDGDMI | | 16471 |
| HPV56 | L1 | 31 | 9 | PIFLQMATW | | 16472 |
| HPV56 | L1 | 473 | 8 | PLAKYKFW | | 16473 |
| HPV56 | L1 | 221 | 9 | PLALINTPI | | 16474 |
| HPV56 | L1 | 255 | 11 | PLDIVQSTCKY | | 16475 |
| HPV56 | L1 | 146 | 11 | PLGAGLSGHPL | | 16476 |
| HPV56 | L1 | 496 | 8 | PLGRKFLM | | 16477 |
| HPV56 | L1 | 496 | 10 | PLGRKFLMQL | | 16478 |
| HPV56 | L1 | 13 | 8 | PLHYGLCI | | 16479 |
| HPV56 | L1 | 13 | 9 | PLHYGLCIF | | 16480 |
| HPV56 | L1 | 13 | 10 | PLHYGLCIFL | | 16481 |
| HPV56 | L1 | 4 | 11 | PMMYIYRDPPL | | 16482 |
| HPV56 | L1 | 467 | 8 | PTEKQDPL | | 16483 |
| HPV56 | L1 | 467 | 11 | PTEKQDPLAKY | | 16484 |
| HPV56 | L1 | 442 | 10 | PVATSLEDKY | | 16485 |
| HPV56 | L1 | 52 | 11 | PVSKVVATDSY | | 16486 |
| HPV56 | L1 | 494 | 8 | QFPLGRKF | | 16487 |
| HPV56 | L1 | 494 | 9 | QFPLGRKFL | | 16488 |
| HPV56 | L1 | 494 | 10 | QFPLGRKFLM | | 16489 |
| HPV56 | L1 | 406 | 9 | QFVFQLCKI | | 16490 |
| HPV56 | L1 | 406 | 11 | QFVFQLCKITL | | 16491 |
| HPV56 | L1 | 189 | 11 | QLCIVGCTPAM | | 16492 |
| HPV56 | L1 | 288 | 8 | QLFARHYF | | 16493 |
| HPV56 | L1 | 339 | 8 | QLFNKPYW | | 16494 |
| HPV56 | L1 | 339 | 9 | QLFNKPYWL | | 16495 |
| HPV56 | L1 | 384 | 10 | QLSKYDARKI | | 16496 |
| HPV56 | L1 | 213 | 10 | QVTTGDCPPL | | 16497 |
| HPV56 | L1 | 395 | 9 | QYLRHVEEY | | 16498 |
| HPV56 | L1 | 395 | 11 | QYLRHVEEYEL | | 16499 |
| HPV56 | L1 | 103 | 9 | QYRVFRVRL | | 16500 |
| HPV56 | L1 | 159 | 10 | RLDDTESSNL | | 16501 |
| HPV56 | L1 | 76 | 9 | RLLAVGHPY | | 16502 |
| HPV56 | L1 | 76 | 10 | RLLAVGHPYY | | 16503 |
| HPV56 | L1 | 110 | 8 | RLPDPNKF | | 16504 |
| HPV56 | L1 | 110 | 10 | RLPDPNKFGL | | 16505 |
| HPV56 | L1 | 131 | 9 | RLVWACVGL | | 16506 |
| HPV56 | L1 | 108 | 10 | RVRLPDPNKF | | 16507 |
| HPV56 | L1 | 452 | 8 | RYVRSTAI | | 16508 |
| HPV56 | L1 | 487 | 9 | SFSTDLDQF | | 16509 |
| HPV56 | L1 | 487 | 11 | SFSTDLDQFPL | | 16510 |
| HPV56 | L1 | 67 | 11 | SIFYHAGSSRL | | 16511 |
| HPV56 | L1 | 446 | 8 | SLEDKYRY | | 16512 |
| HPV56 | L1 | 332 | 9 | SMITSEAQL | | 16513 |
| HPV56 | L1 | 332 | 10 | SMITSEAQLF | | 16514 |
| HPV56 | L1 | 279 | 11 | SMWFYLRREQL | | 16515 |
| HPV56 | L1 | 379 | 10 | STATEQLSKY | | 16516 |
| HPV56 | L1 | 261 | 8 | STCKYPDY | | 16517 |
| HPV56 | L1 | 261 | 9 | STCKYPDYL | | 16518 |
| HPV56 | L1 | 261 | 11 | STCKYPDYLKM | | 16519 |
| HPV56 | L1 | 489 | 9 | STDLDQFPL | | 16520 |
| HPV56 | L1 | 182 | 9 | SVDGKQTQL | | 16521 |
| HPV56 | L1 | 182 | 11 | SVDGKQTQLCI | | 16522 |
| HPV56 | L1 | 86 | 11 | SVTKDNTKTNI | | 16523 |
| HPV56 | L1 | 323 | 11 | SVYVATPSGSM | | 16524 |
| HPV56 | L1 | 61 | 8 | SYVKRTSI | | 16525 |
| HPV56 | L1 | 61 | 9 | SYVKRTSIF | | 16526 |
| HPV56 | L1 | 61 | 10 | SYVKRTSIFY | | 16527 |
| HPV56 | L1 | 304 | 8 | TIPAELYL | | 16528 |
| HPV56 | L1 | 377 | 9 | TISTATEQL | | 16529 |
| HPV56 | L1 | 415 | 9 | TLSAEVMAY | | 16530 |
| HPV56 | L1 | 415 | 10 | TLSAEVMAYL | | 16531 |
| HPV56 | L1 | 215 | 8 | TTGDCPPL | | 16532 |
| HPV56 | L1 | 215 | 10 | TTGDCPPLAL | | 16533 |
| HPV56 | L1 | 215 | 11 | TTGDCPPLALI | | 16534 |
| HPV56 | L1 | 370 | 9 | TTRSTNMTI | | 16535 |
| HPV56 | L1 | 366 | 11 | TVVDTTRSTNM | | 16536 |
| HPV56 | L1 | 38 | 10 | TWRPSENKVY | | 16537 |
| HPV56 | L1 | 38 | 11 | TWRPSENKVYL | | 16538 |
| HPV56 | L1 | 29 | 8 | VFPIFLQM | | 16539 |

TABLE X-continued

A24 Supermotif Peptides

| Type | Protein | Position | No. of Amino Acids | Sequence | A*2402 | Seq. Id. No. |
|---|---|---|---|---|---|---|
| HPV56 | L1 | 29 | 11 | VFPIFLQMATW | | 16540 |
| HPV56 | L1 | 408 | 9 | VFQLCKITL | | 16541 |
| HPV56 | L1 | 173 | 9 | VIEDSRDNI | | 16542 |
| HPV56 | L1 | 246 | 11 | VLQESKAEVPL | | 16543 |
| HPV56 | L1 | 420 | 8 | VMAYLHNM | | 16544 |
| HPV56 | L1 | 87 | 10 | VTKDNTKTNI | | 16545 |
| HPV56 | L1 | 214 | 9 | VTTGDCPPL | | 16546 |
| HPV56 | L1 | 214 | 11 | VTTGDCPPLAL | | 16547 |
| HPV56 | L1 | 367 | 10 | VVDTTRSTNM | | 16548 |
| HPV56 | L1 | 324 | 10 | VYVATPSGSM | | 16549 |
| HPV56 | L1 | 324 | 11 | VYVATPSGSMI | | 16550 |
| HPV56 | L1 | 281 | 9 | WFYLRREQL | | 16551 |
| HPV56 | L1 | 281 | 10 | WFYLRREQLF | | 16552 |
| HPV56 | L1 | 7 | 8 | YIYRDPPL | | 16553 |
| HPV56 | L1 | 7 | 10 | YIYRDPPLHY | | 16554 |
| HPV56 | L1 | 423 | 9 | YLHNMNANL | | 16555 |
| HPV56 | L1 | 423 | 10 | YLHNMNANLL | | 16556 |
| HPV56 | L1 | 268 | 9 | YLKMSADAY | | 16557 |
| HPV56 | L1 | 396 | 8 | YLRHVEEY | | 16558 |
| HPV56 | L1 | 396 | 10 | YLRHVEEYEL | | 16559 |
| HPV56 | L1 | 283 | 8 | YLRREQLF | | 16560 |
| HPV56 | L1 | 325 | 9 | YVATPSGSM | | 16561 |
| HPV56 | L1 | 325 | 10 | YVATPSGSMI | | 16562 |
| HPV56 | L1 | 62 | 8 | YVKRTSIF | | 16563 |
| HPV56 | L1 | 62 | 9 | YVKRTSIFY | | 16564 |
| HPV56 | L2 | 240 | 9 | AFLDRPATL | | 16565 |
| HPV56 | L2 | 286 | 11 | AFTTRRGGVRF | | 16566 |
| HPV56 | L2 | 438 | 8 | ALWPVYFF | | 16567 |
| HPV56 | L2 | 303 | 11 | ATIQTRRGTQI | | 16568 |
| HPV56 | L2 | 246 | 10 | ATLVSADNPL | | 16569 |
| HPV56 | L2 | 246 | 11 | ATLVSADNPLF | | 16570 |
| HPV56 | L2 | 367 | 9 | ATPSAHLPI | | 16571 |
| HPV56 | L2 | 14 | 10 | ATQLYKTCKL | | 16572 |
| HPV56 | L2 | 201 | 10 | AVHGSGTEPI | | 16573 |
| HPV56 | L2 | 275 | 8 | DFMNIVAL | | 16574 |
| HPV56 | L2 | 322 | 11 | DISPIAQAEEI | | 16575 |
| HPV56 | L2 | 406 | 11 | DIVLPTGPSTW | | 16576 |
| HPV56 | L2 | 425 | 8 | DVTHDVYI | | 16577 |
| HPV56 | L2 | 83 | 9 | DVTPARPPI | | 16578 |
| HPV56 | L2 | 30 | 11 | DVVNKIEQKTW | | 16579 |
| HPV56 | L2 | 429 | 9 | DVYIQGSSF | | 16580 |
| HPV56 | L2 | 429 | 11 | DVYIQGSSFAL | | 16581 |
| HPV56 | L2 | 331 | 8 | EIEMQPLL | | 16582 |
| HPV56 | L2 | 398 | 10 | ETPFYSGPDI | | 16583 |
| HPV56 | L2 | 175 | 8 | EVSGNILI | | 16584 |
| HPV56 | L2 | 444 | 10 | FFRRRRRKRI | | 16585 |
| HPV56 | L2 | 241 | 8 | FLDRPATL | | 16586 |
| HPV56 | L2 | 122 | 9 | FTGSGGFEI | | 16587 |
| HPV56 | L2 | 287 | 10 | FTTRRGGVRF | | 16588 |
| HPV56 | L2 | 51 | 9 | FTYFGGLGI | | 16589 |
| HPV56 | L2 | 401 | 9 | FYSGPDIVL | | 16590 |
| HPV56 | L2 | 217 | 10 | GFRRIAAPRL | | 16591 |
| HPV56 | L2 | 217 | 11 | GFRRIAAPRLY | | 16592 |
| HPV56 | L2 | 188 | 8 | GIHSYEEI | | 16593 |
| HPV56 | L2 | 188 | 10 | GIHSYEEIPM | | 16594 |
| HPV56 | L2 | 118 | 11 | GIPNFTGSGGF | | 16595 |
| HPV56 | L2 | 346 | 9 | GLYDIYANI | | 16596 |
| HPV56 | L2 | 25 | 11 | GTCPEDVVNKI | | 16597 |
| HPV56 | L2 | 258 | 8 | GTDTSLAF | | 16598 |
| HPV56 | L2 | 206 | 10 | GTEPISSTPI | | 16599 |
| HPV56 | L2 | 62 | 10 | GTGSGGRAGY | | 16600 |
| HPV56 | L2 | 310 | 10 | GTQIGARVHY | | 16601 |
| HPV56 | L2 | 310 | 11 | GTQIGARVHYY | | 16602 |
| HPV56 | L2 | 269 | 8 | GVAPDPDF | | 16603 |
| HPV56 | L2 | 269 | 9 | GVAPDPDFM | | 16604 |
| HPV56 | L2 | 269 | 11 | GVAPDPDFMNI | | 16605 |
| HPV56 | L2 | 156 | 8 | HITNPLFI | | 16606 |
| HPV56 | L2 | 372 | 9 | HLPIKPSTL | | 16607 |
| HPV56 | L2 | 372 | 11 | HLPIKPSTLSF | | 16608 |
| HPV56 | L2 | 151 | 11 | HVSSTHITNPL | | 16609 |
| HPV56 | L2 | 318 | 9 | HYYYDISPI | | 16610 |
| HPV56 | L2 | 180 | 10 | ILISTPTSGI | | 16611 |
| HPV56 | L2 | 44 | 8 | ILQWGSLF | | 16612 |
| HPV56 | L2 | 44 | 10 | ILQWGSLFTY | | 16613 |

TABLE X-continued

A24 Supermotif Peptides

| Type | Protein | Position | No. of Amino Acids | Sequence | A*2402 | Seq. Id. No. |
|---|---|---|---|---|---|---|
| HPV56 | L2 | 44 | 11 | ILQWGSLFTYF | | 16614 |
| HPV56 | L2 | 279 | 9 | IVALHRPAF | | 16615 |
| HPV56 | L2 | 81 | 11 | IVDVTPARPPI | | 16616 |
| HPV56 | L2 | 407 | 10 | IVLPTGPSTW | | 16617 |
| HPV56 | L2 | 103 | 11 | IVTLVEESSVI | | 16618 |
| HPV56 | L2 | 34 | 11 | KIEQKTWADKI | | 16619 |
| HPV56 | L2 | 43 | 8 | KILQWGSL | | 16620 |
| HPV56 | L2 | 43 | 9 | KILQWGSLF | | 16621 |
| HPV56 | L2 | 43 | 11 | KILQWGSLFTY | | 16622 |
| HPV56 | L2 | 38 | 8 | KTWADKIL | | 16623 |
| HPV56 | L2 | 38 | 10 | KTWADKILQW | | 16624 |
| HPV56 | L2 | 235 | 8 | KVTDPAFL | | 16625 |
| HPV56 | L2 | 255 | 9 | LFEGTDTSL | | 16626 |
| HPV56 | L2 | 255 | 11 | LFEGTDTSLAF | | 16627 |
| HPV56 | L2 | 161 | 8 | LFIDPPVI | | 16628 |
| HPV56 | L2 | 50 | 8 | LFTYFGGL | | 16629 |
| HPV56 | L2 | 50 | 10 | LFTYFGGLGI | | 16630 |
| HPV56 | L2 | 181 | 9 | LISTPTSGI | | 16631 |
| HPV56 | L2 | 337 | 8 | LLSANNSF | | 16632 |
| HPV56 | L2 | 337 | 11 | LLSANNSFDGL | | 16633 |
| HPV56 | L2 | 106 | 8 | LVEESSVI | | 16634 |
| HPV56 | L2 | 248 | 8 | LVSADNPL | | 16635 |
| HPV56 | L2 | 248 | 9 | LVSADNPLF | | 16636 |
| HPV56 | L2 | 347 | 8 | LYDIYANI | | 16637 |
| HPV56 | L2 | 121 | 8 | NFTGSGGF | | 16638 |
| HPV56 | L2 | 121 | 10 | NFTGSGGFEI | | 16639 |
| HPV56 | L2 | 353 | 9 | NIDDEAPGL | | 16640 |
| HPV56 | L2 | 179 | 11 | NILISTPTSGI | | 16641 |
| HPV56 | L2 | 278 | 10 | NIVALHRPAF | | 16642 |
| HPV56 | L2 | 385 | 9 | NTTNVTAPL | | 16643 |
| HPV56 | L2 | 388 | 10 | NVTAPLGNVW | | 16644 |
| HPV56 | L2 | 395 | 8 | NVWETPFY | | 16645 |
| HPV56 | L2 | 417 | 8 | PFVPQSPY | | 16646 |
| HPV56 | L2 | 400 | 8 | PFYSGPDI | | 16647 |
| HPV56 | L2 | 400 | 10 | PFYSGPDIVL | | 16648 |
| HPV56 | L2 | 325 | 8 | PIAQAEEI | | 16649 |
| HPV56 | L2 | 325 | 10 | PIAQAEEIEM | | 16650 |
| HPV56 | L2 | 374 | 9 | PIKPSTLSF | | 16651 |
| HPV56 | L2 | 214 | 8 | PIPGFRRI | | 16652 |
| HPV56 | L2 | 209 | 10 | PISSTPIPGF | | 16653 |
| HPV56 | L2 | 254 | 10 | PLFEGTDTSL | | 16654 |
| HPV56 | L2 | 160 | 9 | PLFIDPPVI | | 16655 |
| HPV56 | L2 | 392 | 10 | PLGNVWETPF | | 16656 |
| HPV56 | L2 | 392 | 11 | PLGNVWETPFY | | 16657 |
| HPV56 | L2 | 73 | 9 | PLGSRPSTI | | 16658 |
| HPV56 | L2 | 336 | 9 | PLLSANNSF | | 16659 |
| HPV56 | L2 | 98 | 9 | PTDPSIVTL | | 16660 |
| HPV56 | L2 | 410 | 9 | PTGPSTWPF | | 16661 |
| HPV56 | L2 | 185 | 8 | PTSGIHSY | | 16662 |
| HPV56 | L2 | 185 | 11 | PTSGIHSYEEI | | 16663 |
| HPV56 | L2 | 423 | 9 | PYDVTHDVY | | 16664 |
| HPV56 | L2 | 423 | 10 | PYDVTHDVYI | | 16665 |
| HPV56 | L2 | 312 | 8 | QIGARVHY | | 16666 |
| HPV56 | L2 | 312 | 9 | QIGARVHYY | | 16667 |
| HPV56 | L2 | 312 | 10 | QIGARVHYYY | | 16668 |
| HPV56 | L2 | 16 | 8 | QLYKTCKL | | 16669 |
| HPV56 | L2 | 172 | 9 | QTGEVSGNI | | 16670 |
| HPV56 | L2 | 172 | 10 | QTGEVSGNIL | | 16671 |
| HPV56 | L2 | 172 | 11 | QTGEVSGNILI | | 16672 |
| HPV56 | L2 | 306 | 8 | QTRRGTQI | | 16673 |
| HPV56 | L2 | 233 | 9 | QVKVTDPAF | | 16674 |
| HPV56 | L2 | 233 | 10 | QVKVTDPAFL | | 16675 |
| HPV56 | L2 | 46 | 8 | QWGSLFTY | | 16676 |
| HPV56 | L2 | 46 | 9 | QWGSLFTYF | | 16677 |
| HPV56 | L2 | 295 | 11 | RFSRLGRKATI | | 16678 |
| HPV56 | L2 | 220 | 8 | RIAAPRLY | | 16679 |
| HPV56 | L2 | 298 | 8 | RLGRKATI | | 16680 |
| HPV56 | L2 | 316 | 8 | RVHYYYDI | | 16681 |
| HPV56 | L2 | 316 | 11 | RVHYYYDISPI | | 16682 |
| HPV56 | L2 | 436 | 8 | SFALWPVY | | 16683 |
| HPV56 | L2 | 436 | 9 | SFALWPVYF | | 16684 |
| HPV56 | L2 | 436 | 10 | SFALWPVYFF | | 16685 |
| HPV56 | L2 | 343 | 8 | SFDGLYDI | | 16686 |
| HPV56 | L2 | 343 | 9 | SFDGLYDIY | | 16687 |

TABLE X-continued

A24 Supermotif Peptides

| Type | Protein | Position | No. of Amino Acids | Sequence | A*2402 | Seq. Id. No. |
|---|---|---|---|---|---|---|
| HPV56 | L2 | 49 | 9 | SLFTYFGGL | | 16688 |
| HPV56 | L2 | 49 | 11 | SLFTYFGGLGI | | 16689 |
| HPV56 | L2 | 154 | 8 | STHITNPL | | 16690 |
| HPV56 | L2 | 154 | 9 | STHITNPLF | | 16691 |
| HPV56 | L2 | 154 | 10 | STHITNPLFI | | 16692 |
| HPV56 | L2 | 212 | 10 | STPIPGFRRI | | 16693 |
| HPV56 | L2 | 183 | 10 | STPTSGIHSY | | 16694 |
| HPV56 | L2 | 134 | 8 | STTTPAVL | | 16695 |
| HPV56 | L2 | 134 | 10 | STTTPAVLDI | | 16696 |
| HPV56 | L2 | 148 | 10 | STVHVSSTHI | | 16697 |
| HPV56 | L2 | 414 | 11 | STWPFVPQSPY | | 16698 |
| HPV56 | L2 | 365 | 9 | SVATPSAHL | | 16699 |
| HPV56 | L2 | 365 | 11 | SVATPSAHLPI | | 16700 |
| HPV56 | L2 | 95 | 9 | SVGPTDPSI | | 16701 |
| HPV56 | L2 | 111 | 9 | SVIESGAGI | | 16702 |
| HPV56 | L2 | 191 | 10 | SYEEIPMQTF | | 16703 |
| HPV56 | L2 | 304 | 10 | TIQTRRGTQI | | 16704 |
| HPV56 | L2 | 105 | 9 | TLVEESSVI | | 16705 |
| HPV56 | L2 | 247 | 9 | TLVSADNPL | | 16706 |
| HPV56 | L2 | 247 | 10 | TLVSADNPLF | | 16707 |
| HPV56 | L2 | 386 | 8 | TTNVTAPL | | 16708 |
| HPV56 | L2 | 136 | 8 | TTPAVLDI | | 16709 |
| HPV56 | L2 | 288 | 9 | TTRRGGVRF | | 16710 |
| HPV56 | L2 | 135 | 9 | TTTPAVLDI | | 16711 |
| HPV56 | L2 | 149 | 9 | TVHVSSTHI | | 16712 |
| HPV56 | L2 | 39 | 9 | TWADKILQW | | 16713 |
| HPV56 | L2 | 415 | 10 | TWPFVPQSPY | | 16714 |
| HPV56 | L2 | 52 | 8 | TYFGGLGI | | 16715 |
| HPV56 | L2 | 112 | 8 | VIESGAGI | | 16716 |
| HPV56 | L2 | 112 | 11 | VIESGAGIPNF | | 16717 |
| HPV56 | L2 | 408 | 9 | VLPTGPSTW | | 16718 |
| HPV56 | L2 | 408 | 11 | VLPTGPSTWPF | | 16719 |
| HPV56 | L2 | 389 | 9 | VTAPLGNVW | | 16720 |
| HPV56 | L2 | 104 | 10 | VTLVEESSVI | | 16721 |
| HPV56 | L2 | 84 | 8 | VTPARPPI | | 16722 |
| HPV56 | L2 | 31 | 10 | VVNKIEQKTW | | 16723 |
| HPV56 | L2 | 430 | 8 | VYIQGSSF | | 16724 |
| HPV56 | L2 | 430 | 10 | VYIQGSSFAL | | 16725 |
| HPV56 | L2 | 430 | 11 | VYIQGSSFALW | | 16726 |
| HPV56 | L2 | 443 | 11 | YFFRRRRRKRI | | 16727 |
| HPV56 | L2 | 431 | 9 | YIQGSSFAL | | 16728 |
| HPV56 | L2 | 431 | 10 | YIQGSSFALW | | 16729 |
| HPV56 | L2 | 71 | 11 | YVPLGSRPSTI | | 16730 |
| HPV56 | L2 | 319 | 8 | YYYDISPI | | 16731 |

TABLE XI

B07 Supermotif Peptides

| Type | Protein | Position | No. of Amino Acids | Sequence | B*0702 | B*3501 | B*5101 | B*5301 | B*5401 | Seq. Id. No. |
|---|---|---|---|---|---|---|---|---|---|---|
| HPV16 | E1 | 559 | 10 | CPPLLITSNI | | | | | | 16732 |
| HPV16 | E1 | 308 | 9 | EPPKLRSTA | | | | | | 16733 |
| HPV16 | E1 | 308 | 10 | EPPKLRSTAA | 0.0002 | 0.0003 | 0.0002 | 0.0002 | 0.0200 | 16734 |
| HPV16 | E1 | 308 | 11 | EPPKLRSTAAA | | | | | | 16735 |
| HPV16 | E1 | 592 | 10 | FPFDENGNPV | | | | | | 16736 |
| HPV16 | E1 | 592 | 11 | FPFDENGNPVY | | | | | | 16737 |
| HPV16 | E1 | 467 | 8 | IPKKNCIL | | | | | | 16738 |
| HPV16 | E1 | 467 | 9 | IPKKNCILL | | | | | | 16739 |
| HPV16 | E1 | 467 | 10 | IPKKNCILLY | | | | | | 16740 |
| HPV16 | E1 | 599 | 11 | NPVYELNDKNW | | | | | | 16741 |
| HPV16 | E1 | 309 | 8 | PPKLRSTA | | | | | | 16742 |
| HPV16 | E1 | 309 | 9 | PPKLRSTAA | 0.0014 | 0.0003 | 0.0002 | 0.0002 | 0.0024 | 16743 |
| HPV16 | E1 | 309 | 10 | PPKLRSTAAA | | | | | | 16744 |
| HPV16 | E1 | 309 | 11 | PPKLRSTAAAL | | | | | | 16745 |
| HPV16 | E1 | 560 | 9 | PPLLITSNI | | | | | | 16746 |
| HPV16 | E1 | 560 | 11 | PPLLITSNINA | | | | | | 16747 |
| HPV16 | E1 | 511 | 8 | QPLADAKI | | | | | | 16748 |
| HPV16 | E1 | 511 | 10 | QPLADAKIGM | | | | | | 16749 |
| HPV16 | E1 | 511 | 11 | QPLADAKIGML | | | | | | 16750 |

TABLE XI-continued

| | | | | | | | | | | | |
|---|---|---|---|---|---|---|---|---|---|---|---|
| HPV16 | E1 | 552 | 11 | RPLVQLKCPPL | | | | | | | 16751 |
| HPV16 | E1 | 93 | 10 | SPLSDISGCV | | | | | | | 16752 |
| HPV16 | EI | 107 | 9 | SPRLKAICI | 0.4700 | 0.0003 | 0.0004 | 0.0002 | 0.0004 | | 16753 |
| HPV16 | E1 | 336 | 10 | TPEWIQRQTV | | | | | | | 16754 |
| HPV16 | E1 | 336 | 11 | TPEWIQRQTVL | | | | | | | 16755 |
| HPV16 | E1 | 189 | 9 | TPLTNILNV | | | | | | | 16756 |
| HPV16 | E1 | 189 | 10 | TPLTNILNVL | | | | | | | 16757 |
| HPV16 | E1 | 244 | 8 | TPSIADSI | | | | | | | 16758 |
| HPV16 | E1 | 244 | 11 | TPSIADSIKTL | | | | | | | 16759 |
| HPV16 | E1 | 526 | 11 | VPCWNYIDDNL | | | | | | | 16760 |
| HPV16 | E1 | 576 | 8 | WPYLHNRL | | | | | | | 16761 |
| HPV16 | E1 | 576 | 9 | WPYLHNRLV | 0.0520 | 0.0003 | 0.1100 | 0.0002 | 0.1800 | | 16762 |
| HPV16 | E1 | 576 | 10 | WPYLHNRLVV | 0.0950 | 0.0012 | 0.0740 | 0.0002 | 0.0760 | | 16763 |
| HPV16 | E1 | 576 | 11 | WPYLHNRLVVF | | | | | | | 16764 |
| HPV16 | E2 | 105 | 11 | APTGCIKKHGY | | | | | | | 16765 |
| HPV16 | E2 | 195 | 11 | CPTSVFSSNEV | | | | | | | 16766 |
| HPV16 | E2 | 218 | 9 | HPAATHTKA | | | | | | | 16767 |
| HPV16 | E2 | 218 | 10 | HPAATHTKAV | | | | | | | 16768 |
| HPV16 | E2 | 218 | 11 | HPAATHTKAVA | | | | | | | 16769 |
| HPV16 | E2 | 352 | 11 | IPKTITVSTGF | | | | | | | 16770 |
| HPV16 | E2 | 249 | 8 | NPCHTTKL | | | | | | | 16771 |
| HPV16 | E2 | 249 | 9 | NPCHTTKLL | | | | | | | 16772 |
| HPV16 | E2 | 207 | 9 | SPEIIRQHL | | | | | | | 16773 |
| HPV16 | E2 | 207 | 10 | SPEIIRQHLA | | | | | | | 16774 |
| HPV16 | E2 | 286 | 10 | TPIVHLKGDA | | | | | | | 16775 |
| HPV16 | E2 | 59 | 11 | VPTLAVSKNKA | | | | | | | 16776 |
| HPV16 | E5 | 69 | 10 | IPLFLIHTHA | | | | | | | 16777 |
| HPV16 | E5 | 30 | 10 | RPLLLSVSTY | | | | | | | 16778 |
| HPV16 | E6 | 118 | 9 | CPEEKQRHL | 0.0003 | 0.0002 | 0.0074 | 0.0006 | 0.0002 | | 16779 |
| HPV16 | E6 | 11 | 9 | DPQERPRKL | 0.0001 | 0.0001 | 0.0001 | 0.0001 | 0.0002 | | 16780 |
| HPV16 | E6 | 101 | 8 | KPLCDLLI | | | | | | | 16781 |
| HPV16 | E6 | 101 | 11 | KPLCDLLIRCI | | | | | | | 16782 |
| HPV16 | E6 | 19 | 8 | LPQLCTEL | 0.0055 | | | | | | 16783 |
| HPV16 | E6 | 65 | 10 | NPYAVCDKCL | 0.0001 | 0.0001 | 0.0001 | 0.0001 | 0.0001 | | 16784 |
| HPV16 | E6 | 15 | 8 | RPRKLPQL | | | | | | | 16785 |
| HPV16 | E7 | 46 | 9 | EPDRAHYNI | 0.0001 | 0.0001 | 0.0031 | 0.0017 | 0.0002 | | 16786 |
| HPV16 | E7 | 46 | 10 | EPDRAHYNIV | 0.0001 | 0.0001 | 0.0001 | 0.0001 | 0.0001 | | 16787 |
| HPV16 | E7 | 40 | 11 | GPAGQAEPDRA | | | | | | | 16788 |
| HPV16 | E7 | 16 | 8 | QPETTDLY | | | | | | | 16789 |
| HPV16 | E7 | 16 | 10 | QPETTDLYCY | | | | | | | 16790 |
| HPV16 | E7 | 5 | 8 | TPTLHEYM | | | | | | | 16791 |
| HPV16 | E7 | 5 | 9 | TPTLHEYML | 0.1100 | 0.0001 | 0.0001 | 0.0001 | 0.0002 | | 16792 |
| HPV16 | E7 | 5 | 11 | TPTLHEYMLDL | | | | | | | 16793 |
| HPV16 | L1 | 461 | 10 | APKEDPLKKY | | | | | | | 16794 |
| HPV16 | L1 | 211 | 10 | CPPLELINTV | | | | | | | 16795 |
| HPV16 | L1 | 211 | 11 | CPPLELINTVI | | | | | | | 16796 |
| HPV16 | L1 | 465 | 8 | DPLKKYTF | | | | | | | 16797 |
| HPV16 | L1 | 465 | 9 | DPLKKYTFW | | | | | | | 16798 |
| HPV16 | L1 | 465 | 11 | DPLKKYTFWEV | | | | | | | 16799 |
| HPV16 | L1 | 266 | 8 | EPYGDSLF | | | | | | | 16800 |
| HPV16 | L1 | 266 | 9 | EPYGDSLFF | | | | | | | 16801 |
| HPV16 | L1 | 266 | 10 | EPYGDSLFFY | | | | | | | 16802 |
| HPV16 | L1 | 266 | 11 | EPYGDSLFFYL | | | | | | | 16803 |
| HPV16 | L1 | 76 | 11 | FPIKKPNNNKI | | | | | | | 16804 |
| HPV16 | L1 | 488 | 8 | FPLGRKFL | | | | | | | 16805 |
| HPV16 | L1 | 488 | 9 | FPLGRKFLL | | | | | | | 16806 |
| HPV16 | L1 | 488 | 11 | FPLGRKFLLQA | | | | | | | 16807 |
| HPV16 | L1 | 318 | 8 | FPTPSGSM | | | | | | | 16808 |
| HPV16 | L1 | 318 | 9 | FPTPSGSMV | | | | | | | 16809 |
| HPV16 | L1 | 503 | 11 | KPKFTLGKRKA | | | | | | | 16810 |
| HPV16 | L1 | 80 | 8 | KPNNNKIL | | | | | | | 16811 |
| HPV16 | L1 | 80 | 9 | KPNNNKILV | | | | | | | 16812 |
| HPV16 | L1 | 188 | 8 | KPPIGEHW | | | | | | | 16813 |
| HPV16 | L1 | 335 | 8 | KPYWLQRA | | | | | | | 16814 |
| HPV16 | L1 | 103 | 9 | LPDPNKFGF | | | | | | | 16815 |
| HPV16 | L1 | 39 | 9 | LPPVPVSKV | | | | | | | 16816 |
| HPV16 | L1 | 39 | 10 | LPPVPVSKVV | | | | | | | 16817 |
| HPV16 | L1 | 31 | 8 | LPSEATVY | | | | | | | 16818 |
| HPV16 | L1 | 31 | 9 | LPSEATVYL | | | | | | | 16819 |
| HPV16 | L1 | 118 | 8 | NPDTQRLV | | | | | | | 16820 |
| HPV16 | L1 | 118 | 9 | NPDTQRLVW | | | | | | | 16821 |
| HPV16 | L1 | 118 | 10 | NPDTQRLVWA | | | | | | | 16822 |
| HPV16 | L1 | 207 | 8 | NPGDCPPL | | | | | | | 16823 |
| HPV16 | L1 | 207 | 10 | NPGDCPPLEL | | | | | | | 16824 |
| HPV16 | L1 | 207 | 11 | NPGDCPPLELI | | | | | | | 16825 |
| HPV16 | L1 | 459 | 9 | PPAPKEDPL | | | | | | | 16826 |
| HPV16 | L1 | 435 | 10 | PPGGTLEDTY | | | | | | | 16827 |
| HPV16 | L1 | 212 | 9 | PPLELINTV | | | | | | | 16828 |
| HPV16 | L1 | 212 | 10 | PPLELINTVI | | | | | | | 16829 |

TABLE XI-continued

| | | | | | | |
|---|---|---|---|---|---|---|
| HPV16 | L1 | 434 | 11 | PPPGGTLEDTY | | 16830 |
| HPV16 | L1 | 40 | 8 | PPVPVSKV | | 16831 |
| HPV16 | L1 | 40 | 9 | PPVPVSKVV | | 16832 |
| HPV16 | L1 | 433 | 8 | QPPPGGTL | | 16833 |
| HPV16 | L1 | 199 | 8 | SPCTNVAV | | 16834 |
| HPV16 | L1 | 458 | 10 | TPPAPKEDPL | | 16835 |
| HPV16 | L1 | 320 | 11 | TPSGSMVTSDA | | 16836 |
| HPV16 | L1 | 514 | 11 | TPTFSSTSTTA | | 16837 |
| HPV16 | L1 | 88 | 9 | VPKVSGLQY | | 16838 |
| HPV16 | L1 | 88 | 11 | VPKVSGLQYRV | | 16839 |
| HPV16 | L1 | 246 | 9 | VPLDICTSI | | 16840 |
| HPV16 | L1 | 257 | 8 | YPDYIKMV | | 16841 |
| HPV16 | L2 | 278 | 9 | APDPDFLDI | | 16842 |
| HPV16 | L2 | 278 | 10 | APDPDFLDIV | | 16843 |
| HPV16 | L2 | 278 | 11 | APDPDFLDIVA | | 16844 |
| HPV16 | L2 | 424 | 8 | APSLIPIV | | 16845 |
| HPV16 | L2 | 119 | 8 | APTSVPSI | | 16846 |
| HPV16 | L2 | 87 | 9 | APVRPPLTV | | 16847 |
| HPV16 | L2 | 28 | 9 | CPPDIIPKV | | 16848 |
| HPV16 | L2 | 239 | 11 | DPAFITTPTKL | | 16849 |
| HPV16 | L2 | 280 | 8 | DPDFLDIV | | 16850 |
| HPV16 | L2 | 280 | 9 | DPDFLDIVA | | 16851 |
| HPV16 | L2 | 280 | 10 | DPDFLDIVAL | | 16852 |
| HPV16 | L2 | 102 | 8 | DPSIVSLV | | 16853 |
| HPV16 | L2 | 165 | 11 | DPSVLQPPTPA | | 16854 |
| HPV16 | L2 | 96 | 10 | DPVGPSDPSI | | 16855 |
| HPV16 | L2 | 96 | 11 | DPVGPSDPSIV | | 16856 |
| HPV16 | L2 | 413 | 8 | GPDIPINI | | 16857 |
| HPV16 | L2 | 99 | 8 | GPSDPSIV | | 16858 |
| HPV16 | L2 | 99 | 10 | GPSDPSIVSL | | 16859 |
| HPV16 | L2 | 99 | 11 | GPSDPSIVSLV | | 16860 |
| HPV16 | L2 | 394 | 9 | IPANTTIPF | | 16861 |
| HPV16 | L2 | 400 | 9 | IPFGGAYNI | | 16862 |
| HPV16 | L2 | 400 | 11 | IPFGGAYNIPL | | 16863 |
| HPV16 | L2 | 216 | 8 | IPGSRPVA | | 16864 |
| HPV16 | L2 | 216 | 10 | IPGSRPVARL | | 16865 |
| HPV16 | L2 | 416 | 9 | IPINITDQA | | 16866 |
| HPV16 | L2 | 428 | 10 | IPIVPGSPQY | | 16867 |
| HPV16 | L2 | 33 | 9 | IPKVEGKTI | | 16868 |
| HPV16 | L2 | 33 | 10 | IPKVEGKTIA | | 16869 |
| HPV16 | L2 | 73 | 10 | IPLGTRPPTA | | 16870 |
| HPV16 | L2 | 408 | 9 | IPLVSGPDI | | 16871 |
| HPV16 | L2 | 408 | 11 | IPLVSGPDIPI | | 16872 |
| HPV16 | L2 | 196 | 8 | IPMDTFIV | | 16873 |
| HPV16 | L2 | 126 | 8 | IPPDVSGF | | 16874 |
| HPV16 | L2 | 126 | 10 | IPPDVSGFSI | | 16875 |
| HPV16 | L2 | 357 | 9 | LPTSINNGL | | 16876 |
| HPV16 | L2 | 357 | 10 | LPTSINNGLY | | 16877 |
| HPV16 | L2 | 462 | 8 | LPYFFSDV | | 16878 |
| HPV16 | L2 | 462 | 10 | LPYFFSDVSL | | 16879 |
| HPV16 | L2 | 462 | 11 | LPYFFSDVSLA | | 16880 |
| HPV16 | L2 | 254 | 9 | NPAYEGIDV | | 16881 |
| HPV16 | L2 | 206 | 11 | NPNTVTSSTPI | | 16882 |
| HPV16 | L2 | 160 | 9 | NPTFTDPSV | | 16883 |
| HPV16 | L2 | 160 | 10 | NPTFTDPSVL | | 16884 |
| HPV16 | L2 | 29 | 8 | PPDIIPKV | | 16885 |
| HPV16 | L2 | 127 | 9 | PPDVSGFSI | | 16886 |
| HPV16 | L2 | 91 | 8 | PPLTVDPV | | 16887 |
| HPV16 | L2 | 79 | 8 | PPTATDTL | | 16888 |
| HPV16 | L2 | 79 | 9 | PPTATDTLA | | 16889 |
| HPV16 | L2 | 79 | 11 | PPTATDTLAPV | | 16890 |
| HPV16 | L2 | 171 | 11 | PPTPAETGGHF | | 16891 |
| HPV16 | L2 | 291 | 11 | RPALTSRRTGI | | 16892 |
| HPV16 | L2 | 90 | 9 | RPPLTVDPV | | 16893 |
| HPV16 | L2 | 78 | 9 | RPPTATDTL | | 16894 |
| HPV16 | L2 | 78 | 10 | RPPTATDTLA | | 16895 |
| HPV16 | L2 | 220 | 8 | RPVARLGL | | 16896 |
| HPV16 | L2 | 220 | 9 | RPVARLGLY | | 16897 |
| HPV16 | L2 | 434 | 8 | SPQYTIIA | | 16898 |
| HPV16 | L2 | 434 | 10 | SPQYTIIADA | | 16899 |
| HPV16 | L2 | 173 | 9 | TPAETGGHF | | 16900 |
| HPV16 | L2 | 173 | 11 | TPAETGGHFTL | | 16901 |
| HPV16 | L2 | 142 | 11 | TPAILDINNTV | | 16902 |
| HPV16 | L2 | 214 | 9 | TPIPGSRPV | | 16903 |
| HPV16 | L2 | 214 | 10 | TPIPGSRPVA | | 16904 |
| HPV16 | L2 | 345 | 11 | TPSTYTTTSHA | | 16905 |
| HPV16 | L2 | 245 | 8 | TPTKLITY | | 16906 |
| HPV16 | L2 | 380 | 11 | TPVPSVPSTSL | | 16907 |
| HPV16 | L2 | 431 | 9 | VPGSPQYTI | | 16908 |

TABLE XI-continued

| | | | | | | | | | | | |
|---|---|---|---|---|---|---|---|---|---|---|---|
| HPV16 | L2 | 431 | 10 | VPGSPQYTII | | | | | | | 16909 |
| HPV16 | L2 | 431 | 11 | VPGSPQYTIIA | | | | | | | 16910 |
| HPV16 | L2 | 123 | 8 | VPSIPPDV | | | | | | | 16911 |
| HPV16 | L2 | 123 | 11 | VPSIPPDVSGF | | | | | | | 16912 |
| HPV16 | L2 | 385 | 9 | VPSTSLSGY | | | | | | | 16913 |
| HPV16 | L2 | 385 | 10 | VPSTSLSGYI | | | | | | | 16914 |
| HPV16 | L2 | 382 | 9 | VPSVPSTSL | | | | | | | 16915 |
| HPV18 | E1 | 566 | 10 | CPPILLTTNI | | | | | | | 16916 |
| HPV18 | E1 | 518 | 8 | EPLTDTKV | | | | | | | 16917 |
| HPV18 | E1 | 518 | 9 | EPLTDTKVA | | | | | | | 16918 |
| HPV18 | E1 | 518 | 10 | EPLTDTKVAM | | | | | | | 16919 |
| HPV18 | E1 | 518 | 11 | EPLTDTKVAML | | | | | | | 16920 |
| HPV18 | E1 | 599 | 10 | FPFDKNGNPV | | | | | | | 16921 |
| HPV18 | E1 | 599 | 11 | FPFDKNGNPVY | | | | | | | 16922 |
| HPV18 | E1 | 484 | 9 | GPANTGKSY | | | | | | | 16923 |
| HPV18 | E1 | 484 | 10 | GPANTGKSYF | | | | | | | 16924 |
| HPV18 | E1 | 576 | 8 | HPAKDNRW | | | | | | | 16925 |
| HPV18 | E1 | 576 | 10 | HPAKDNRWPY | | | | | | | 16926 |
| HPV18 | E1 | 576 | 11 | HPAKDNRWPYL | | | | | | | 16927 |
| HPV18 | E1 | 559 | 11 | KPLIQLKCPPI | | | | | | | 16928 |
| HPV18 | E1 | 641 | 8 | NPFGTFKL | | | | | | | 16929 |
| HPV18 | E1 | 641 | 10 | NPFGTFKLRA | | | | | | | 16930 |
| HPV18 | E1 | 193 | 9 | NPQCTIAQL | | | | | | | 16931 |
| HPV18 | E1 | 251 | 8 | NPTIAEGF | | | | | | | 16932 |
| HPV18 | E1 | 251 | 11 | NPTIAEGFKTL | | | | | | | 16933 |
| HPV18 | E1 | 606 | 11 | NPVYEINDKNW | | | | | | | 16934 |
| HPV18 | E1 | 567 | 9 | PPILLTTNI | | | | | | | 16935 |
| HPV18 | E1 | 316 | 8 | PPKLRSSV | | | | | | | 16936 |
| HPV18 | E1 | 316 | 9 | PPKLRSSVA | | | | | | | 16937 |
| HPV18 | E1 | 316 | 10 | PPKLRSSVAA | | | | | | | 16938 |
| HPV18 | E1 | 316 | 11 | PPKLRSSVAAL | | | | | | | 16939 |
| HPV18 | E1 | 263 | 9 | QPFILYAHI | 0.0002 | 0.0003 | 0.2100 | 0.0017 | 0.0034 | | 16940 |
| HPV18 | E1 | 315 | 9 | QPPKLRSSV | 0.0004 | 0.0003 | 0.0002 | 0.0002 | 0.0004 | | 16941 |
| HPV18 | E1 | 315 | 10 | QPPKLRSSVA | 0.0004 | 0.0003 | 0.0002 | 0.0002 | 0.0390 | | 16942 |
| HPV18 | E1 | 315 | 11 | QPPKLRSSVAA | | | | | | | 16943 |
| HPV18 | E1 | 447 | 9 | RPIVQFLRY | 0.0033 | 0.0400 | 0.0002 | 0.0230 | 0.0004 | | 16944 |
| HPV18 | E1 | 97 | 9 | SPLGERLEV | 0.1300 | 0.0003 | 0.0002 | 0.0002 | 0.0011 | | 16945 |
| HPV18 | E1 | 110 | 9 | SPRLQEISL | 0.6200 | 0.0008 | 0.0005 | 0.0002 | 0.0004 | | 16946 |
| HPV18 | E1 | 343 | 8 | TPEWIQRL | | | | | | | 16947 |
| HPV18 | E1 | 343 | 10 | TPEWIQRLTI | | | | | | | 16948 |
| HPV18 | E1 | 343 | 11 | TPEWIQRLTII | | | | | | | 16949 |
| HPV18 | E1 | 474 | 8 | TPKKNCLV | | | | | | | 16950 |
| HPV18 | E1 | 474 | 9 | TPKKNCLVF | | | | | | | 16951 |
| HPV18 | E1 | 307 | 8 | VPETCMLI | | | | | | | 16952 |
| HPV18 | E1 | 583 | 8 | WPYLESRI | | | | | | | 16953 |
| HPV18 | E1 | 583 | 10 | WPYLESRITV | 0.0067 | 0.0066 | 0.0550 | 0.0140 | 0.0240 | | 16954 |
| HPV18 | E1 | 583 | 11 | WPYLESRITVF | | | | | | | 16955 |
| HPV18 | E2 | 261 | 9 | GPVNPLLGA | | | | | | | 16956 |
| HPV18 | E2 | 261 | 10 | GPVNPLLGAA | | | | | | | 16957 |
| HPV18 | E2 | 352 | 8 | IPDSVQIL | | | | | | | 16958 |
| HPV18 | E2 | 352 | 9 | IPDSVQILV | | | | | | | 16959 |
| HPV18 | E2 | 352 | 11 | IPDSVQILVGY | | | | | | | 16960 |
| HPV18 | E2 | 248 | 8 | RPGHCGLA | | | | | | | 16961 |
| HPV18 | E2 | 226 | 9 | SPYSSTVSV | | | | | | | 16962 |
| HPV18 | E2 | 3 | 10 | TPKETLSERL | | | | | | | 16963 |
| HPV18 | E2 | 224 | 9 | TPSPYSSTV | | | | | | | 16964 |
| HPV18 | E2 | 224 | 11 | TPSPYSSTVSV | | | | | | | 16965 |
| HPV18 | E2 | 271 | 11 | TPTGNNKRRKL | | | | | | | 16966 |
| HPV18 | E2 | 63 | 11 | VPAYNISKSKA | | | | | | | 16967 |
| HPV18 | E5 | 59 | 8 | LPMLLLHI | | | | | | | 16968 |
| HPV18 | E5 | 59 | 10 | LPMLLLHIHA | | | | | | | 16969 |
| HPV18 | E5 | 59 | 11 | LPMLLLHIHAI | | | | | | | 16970 |
| HPV18 | E5 | 23 | 8 | LPSVCMCA | | | | | | | 16971 |
| HPV18 | E5 | 23 | 9 | LPSVCMCAY | | | | | | | 16972 |
| HPV18 | E5 | 23 | 10 | LPSVCMCAYA | | | | | | | 16973 |
| HPV18 | E5 | 23 | 11 | LPSVCMCAYAW | | | | | | | 16974 |
| HPV18 | E5 | 45 | 8 | SPATAFTV | | | | | | | 16975 |
| HPV18 | E5 | 45 | 9 | SPATAFTVY | | | | | | | 16976 |
| HPV18 | E5 | 45 | 10 | SPATAFTVYV | | | | | | | 16977 |
| HPV18 | E5 | 45 | 11 | SPATAFTVYVF | | | | | | | 16978 |
| HPV18 | E5 | 20 | 9 | VPLLPSVCM | | | | | | | 16979 |
| HPV18 | E5 | 20 | 11 | VPLLPSVCMCA | | | | | | | 16980 |
| HPV18 | E6 | 6 | 9 | DPTRRPYKL | 0.0001 | 0.0001 | 0.0001 | 0.0001 | 0.0002 | | 16981 |
| HPV18 | E6 | 60 | 10 | IPHAACHKCI | 0.0065 | 0.0001 | 0.0046 | 0.0001 | 0.0005 | | 16982 |
| HPV18 | E6 | 110 | 9 | KPLNPAEKL | 0.0350 | 0.0001 | 0.0001 | 0.0001 | 0.0002 | | 16983 |
| HPV18 | E6 | 14 | 8 | LPDLCTEL | | | | | | | 16984 |
| HPV18 | E6 | 113 | 9 | NPAEKLRHL | 0.0110 | 0.0001 | 0.0001 | 0.0001 | 0.0002 | | 16985 |
| HPV18 | E6 | 10 | 8 | RPYKLPDL | | | | | | | 16986 |
| HPV18 | E7 | 16 | 8 | EPQNEIPV | | | | | | | 16987 |

TABLE XI-continued

| | | | | | | | | | | | |
|---|---|---|---|---|---|---|---|---|---|---|---|
| HPV18 | E7 | 16 | 10 | EPQNEIPVDL | 0.0001 | 0.0005 | 0.0001 | 0.0001 | 0.0001 | | 16988 |
| HPV18 | E7 | 16 | 11 | EPQNEIPVDLL | | | | | | | 16989 |
| HPV18 | E7 | 55 | 8 | EPQRHTML | | | | | | | 16990 |
| HPV18 | E7 | 55 | 10 | EPQRHTMLCM | 0.0026 | 0.0002 | 0.0003 | 0.0043 | 0.0001 | | 16991 |
| HPV18 | E7 | 3 | 9 | GPKATLQDI | 0.0004 | 0.0001 | 0.0001 | 0.0001 | 0.0002 | | 16992 |
| HPV18 | E7 | 3 | 10 | GPKATLQDIV | 0.0001 | 0.0001 | 0.0001 | 0.0001 | 0.0001 | | 16993 |
| HPV18 | E7 | 3 | 11 | GPKATLQDIVL | | | | | | | 16994 |
| HPV18 | E7 | 21 | 11 | IPVDLLCHEQL | | | | | | | 16995 |
| HPV18 | L1 | 495 | 9 | APAENKDPY | | | | | | | 16996 |
| HPV18 | L1 | 223 | 8 | APAIGEHW | | | | | | | 16997 |
| HPV18 | L1 | 223 | 9 | APAIGEHWA | | | | | | | 16998 |
| HPV18 | L1 | 549 | 11 | APSATTSSKPA | | | | | | | 16999 |
| HPV18 | L1 | 246 | 10 | CPPLELKNTV | | | | | | | 17000 |
| HPV18 | L1 | 246 | 11 | CPPLELKNTVL | | | | | | | 17001 |
| HPV18 | L1 | 501 | 8 | DPYDKLKF | | | | | | | 17002 |
| HPV18 | L1 | 501 | 9 | DPYDKLKFW | | | | | | | 17003 |
| HPV18 | L1 | 501 | 11 | DPYDKLKFWNV | | | | | | | 17004 |
| HPV18 | L1 | 301 | 8 | DPYGDSMF | | | | | | | 17005 |
| HPV18 | L1 | 301 | 9 | DPYGDSMFF | | | | | | | 17006 |
| HPV18 | L1 | 301 | 11 | DPYGDSMFFCL | | | | | | | 17007 |
| HPV18 | L1 | 56 | 8 | FPIFLQMA | | | | | | | 17008 |
| HPV18 | L1 | 56 | 9 | FPIFLQMAL | | | | | | | 17009 |
| HPV18 | L1 | 56 | 10 | FPIFLQMALW | | | | | | | 17010 |
| HPV18 | L1 | 19 | 9 | GPLYHPRPL | | | | | | | 17011 |
| HPV18 | L1 | 19 | 11 | GPLYHPRPLPL | | | | | | | 17012 |
| HPV18 | L1 | 543 | 10 | GPRKRSAPSA | | | | | | | 17013 |
| HPV18 | L1 | 23 | 10 | HPRPLPLHSI | | | | | | | 17014 |
| HPV18 | L1 | 23 | 11 | HPRPLPLHSIL | | | | | | | 17015 |
| HPV18 | L1 | 123 | 9 | IPKVSAYQY | | | | | | | 17016 |
| HPV18 | L1 | 123 | 11 | IPKVSAYQYRV | | | | | | | 17017 |
| HPV18 | L1 | 557 | 8 | KPAKRVRV | | | | | | | 17018 |
| HPV18 | L1 | 557 | 10 | KPAKRVRVRA | | | | | | | 17019 |
| HPV18 | L1 | 539 | 11 | KPTIGPRKRSA | | | | | | | 17020 |
| HPV18 | L1 | 370 | 8 | KPYWLHKA | | | | | | | 17021 |
| HPV18 | L1 | 138 | 9 | LPDPNKFGL | | | | | | | 17022 |
| HPV18 | L1 | 27 | 8 | LPLHSILV | | | | | | | 17023 |
| HPV18 | L1 | 27 | 9 | LPLHSILVY | | | | | | | 17024 |
| HPV18 | L1 | 27 | 10 | LPLHSILVYM | | | | | | | 17025 |
| HPV18 | L1 | 27 | 11 | LPLHSILVYMV | | | | | | | 17026 |
| HPV18 | L1 | 15 | 8 | LPLYGPLY | | | | | | | 17027 |
| HPV18 | L1 | 74 | 9 | LPPPSVARV | | | | | | | 17028 |
| HPV18 | L1 | 74 | 10 | LPPPSVARVV | | | | | | | 17029 |
| HPV18 | L1 | 343 | 9 | MPASPGSCV | | | | | | | 17030 |
| HPV18 | L1 | 343 | 10 | MPASPGSCVY | | | | | | | 17031 |
| HPV18 | L1 | 153 | 8 | NPETQRLV | | | | | | | 17032 |
| HPV18 | L1 | 153 | 9 | NPETQRLVW | | | | | | | 17033 |
| HPV18 | L1 | 153 | 10 | NPETQRLVWA | | | | | | | 17034 |
| HPV18 | L1 | 108 | 8 | NPYFRVPA | | | | | | | 17035 |
| HPV18 | L1 | 247 | 9 | PPLELKNTV | | | | | | | 17036 |
| HPV18 | L1 | 247 | 10 | PPLELKNTVL | | | | | | | 17037 |
| HPV18 | L1 | 469 | 8 | PPPPTTSL | | | | | | | 17038 |
| HPV18 | L1 | 469 | 9 | PPPPTTSLV | | | | | | | 17039 |
| HPV18 | L1 | 75 | 8 | PPPSVARV | | | | | | | 17040 |
| HPV18 | L1 | 75 | 9 | PPPSVARVV | | | | | | | 17041 |
| HPV18 | L1 | 470 | 8 | PPPTTSLV | | | | | | | 17042 |
| HPV18 | L1 | 470 | 11 | PPPTTSLVDTY | | | | | | | 17043 |
| HPV18 | L1 | 76 | 8 | PPSVARVV | | | | | | | 17044 |
| HPV18 | L1 | 471 | 10 | PPTTSLVDTY | | | | | | | 17045 |
| HPV18 | L1 | 25 | 8 | RPLPLHSI | | | | | | | 17046 |
| HPV18 | L1 | 25 | 9 | RPLPLHSIL | | | | | | | 17047 |
| HPV18 | L1 | 25 | 10 | RPLPLHSILV | | | | | | | 17048 |
| HPV18 | L1 | 25 | 11 | RPLPLHSILVY | | | | | | | 17049 |
| HPV18 | L1 | 239 | 11 | RPLSQGDCPPL | | | | | | | 17050 |
| HPV18 | L1 | 66 | 8 | RPSDNTVY | | | | | | | 17051 |
| HPV18 | L1 | 66 | 9 | RPSDNTVYL | | | | | | | 17052 |
| HPV18 | L1 | 353 | 8 | SPSPSGSI | | | | | | | 17053 |
| HPV18 | L1 | 353 | 9 | SPSPSGSIV | | | | | | | 17054 |
| HPV18 | L1 | 411 | 9 | SPVPGQYDA | | | | | | | 17055 |
| HPV18 | L1 | 398 | 8 | TPSTNLTI | | | | | | | 17056 |
| HPV18 | L1 | 398 | 10 | TPSTNLTICA | | | | | | | 17057 |
| HPV18 | L1 | 90 | 9 | TPTSIFYHA | | | | | | | 17058 |
| HPV18 | L1 | 113 | 11 | VPAGGGNKQDI | | | | | | | 17059 |
| HPV18 | L1 | 413 | 10 | VPGQYDATKF | | | | | | | 17060 |
| HPV18 | L1 | 281 | 9 | VPLDICQSI | | | | | | | 17061 |
| HPV18 | L1 | 468 | 9 | VPPPPTTSL | | | | | | | 17062 |
| HPV18 | L1 | 468 | 10 | VPPPPTTSLV | | | | | | | 17063 |
| HPV18 | L1 | 292 | 9 | YPDYLQMSA | | | | | | | 17064 |
| HPV18 | L1 | 524 | 8 | YPLGRKFL | | | | | | | 17065 |
| HPV18 | L1 | 524 | 9 | YPLGRKFLV | | | | | | | 17066 |

TABLE XI-continued

| | | | | | | | | | | | |
|---|---|---|---|---|---|---|---|---|---|---|---|
| HPV18 | L1 | 524 | 11 | YPLGRKFLVQA | | | | | | | 17067 |
| HPV18 | L2 | 421 | 8 | APASTQYI | | | | | | | 17068 |
| HPV18 | L2 | 421 | 10 | APASTQYIGI | | | | | | | 17069 |
| HPV18 | L2 | 327 | 9 | APSPEYIEL | | | | | | | 17070 |
| HPV18 | L2 | 27 | 9 | CPPDVVPKV | | | | | | | 17071 |
| HPV18 | L2 | 266 | 11 | DPRSDVPDSDF | | | | | | | 17072 |
| HPV18 | L2 | 100 | 8 | DPSIVTLI | | | | | | | 17073 |
| HPV18 | L2 | 208 | 8 | EPISSTPL | | | | | | | 17074 |
| HPV18 | L2 | 208 | 11 | EPISSTPLPTV | | | | | | | 17075 |
| HPV18 | L2 | 257 | 9 | EPVDTTLTF | | | | | | | 17076 |
| HPV18 | L2 | 94 | 10 | EPVGPTDPSI | | | | | | | 17077 |
| HPV18 | L2 | 94 | 11 | EPVGPTDPSIV | | | | | | | 17078 |
| HPV18 | L2 | 223 | 8 | GPRLYSRA | | | | | | | 17079 |
| HPV18 | L2 | 223 | 9 | GPRLYSRAY | | | | | | | 17080 |
| HPV18 | L2 | 97 | 8 | GPTDPSIV | | | | | | | 17081 |
| HPV18 | L2 | 97 | 10 | GPTDPSIVTL | | | | | | | 17082 |
| HPV18 | L2 | 97 | 11 | GPTDPSIVTLI | | | | | | | 17083 |
| HPV18 | L2 | 85 | 8 | GPTRPPVV | | | | | | | 17084 |
| HPV18 | L2 | 85 | 9 | GPTRPPVVI | | | | | | | 17085 |
| HPV18 | L2 | 444 | 8 | IPKKRKRV | | | | | | | 17086 |
| HPV18 | L2 | 444 | 10 | IPKKRKRVPY | | | | | | | 17087 |
| HPV18 | L2 | 444 | 11 | IPKKRKRVPYF | | | | | | | 17088 |
| HPV18 | L2 | 72 | 10 | IPLGGRSNTV | | | | | | | 17089 |
| HPV18 | L2 | 72 | 11 | IPLGGRSNTVV | | | | | | | 17090 |
| HPV18 | L2 | 407 | 8 | LPSTTSVW | | | | | | | 17091 |
| HPV18 | L2 | 407 | 10 | LPSTTSVWPI | | | | | | | 17092 |
| HPV18 | L2 | 407 | 11 | LPSTTSVWPIV | | | | | | | 17093 |
| HPV18 | L2 | 215 | 8 | LPTVRRVA | | | | | | | 17094 |
| HPV18 | L2 | 253 | 11 | NPAFEPVDTTL | | | | | | | 17095 |
| HPV18 | L2 | 159 | 9 | NPAFSDPSI | | | | | | | 17096 |
| HPV18 | L2 | 159 | 10 | NPAFSDPSII | | | | | | | 17097 |
| HPV18 | L2 | 238 | 11 | NPEFLTRPSSL | | | | | | | 17098 |
| HPV18 | L2 | 28 | 8 | PPDVVPKV | | | | | | | 17099 |
| HPV18 | L2 | 89 | 8 | PPVVIEPV | | | | | | | 17100 |
| HPV18 | L2 | 284 | 11 | RPALTSRRGTV | | | | | | | 17101 |
| HPV18 | L2 | 88 | 9 | RPPVVIEPV | | | | | | | 17102 |
| HPV18 | L2 | 244 | 8 | RPSSLITY | | | | | | | 17103 |
| HPV18 | L2 | 119 | 10 | RPTFTGTSGF | | | | | | | 17104 |
| HPV18 | L2 | 329 | 10 | SPEYIELQPL | | | | | | | 17105 |
| HPV18 | L2 | 329 | 11 | SPEYIELQPLV | | | | | | | 17106 |
| HPV18 | L2 | 324 | 9 | SPIAPSPEY | | | | | | | 17107 |
| HPV18 | L2 | 324 | 10 | SPIAPSPEYI | | | | | | | 17108 |
| HPV18 | L2 | 418 | 10 | SPTAPASTQY | | | | | | | 17109 |
| HPV18 | L2 | 418 | 11 | SPTAPASTQYI | | | | | | | 17110 |
| HPV18 | L2 | 375 | 10 | SPTISSASSY | | | | | | | 17111 |
| HPV18 | L2 | 213 | 9 | TPLPTVRRV | | | | | | | 17112 |
| HPV18 | L2 | 213 | 10 | TPLPTVRRVA | | | | | | | 17113 |
| HPV18 | L2 | 144 | 9 | TPSSTSVSI | | | | | | | 17114 |
| HPV18 | L2 | 184 | 9 | TPTSGTHGY | | | | | | | 17115 |
| HPV18 | L2 | 271 | 9 | VPDSDFMDI | | | | | | | 17116 |
| HPV18 | L2 | 271 | 10 | VPDSDFMDII | | | | | | | 17117 |
| HPV18 | L2 | 32 | 9 | VPKVEGTTL | | | | | | | 17118 |
| HPV18 | L2 | 32 | 10 | VPKVEGTTLA | | | | | | | 17119 |
| HPV18 | L2 | 389 | 9 | VPLTSSWDV | | | | | | | 17120 |
| HPV18 | L2 | 389 | 11 | VPLTSSWDVPV | | | | | | | 17121 |
| HPV18 | L2 | 170 | 8 | VPQTGEVA | | | | | | | 17122 |
| HPV18 | L2 | 170 | 11 | VPQTGEVAGNV | | | | | | | 17123 |
| HPV18 | L2 | 361 | 9 | VPSRSTTSF | | | | | | | 17124 |
| HPV18 | L2 | 361 | 10 | VPSRSTTSFA | | | | | | | 17125 |
| HPV18 | L2 | 361 | 11 | VPSRSTTSFAF | | | | | | | 17126 |
| HPV18 | L2 | 359 | 11 | VPVPSRSTTSF | | | | | | | 17127 |
| HPV18 | L2 | 397 | 9 | VPVYTGPDI | | | | | | | 17128 |
| HPV18 | L2 | 397 | 11 | VPVYTGPDITL | | | | | | | 17129 |
| HPV18 | L2 | 451 | 9 | VPYFFADGF | | | | | | | 17130 |
| HPV18 | L2 | 451 | 10 | VPYFFADGFV | | | | | | | 17131 |
| HPV18 | L2 | 451 | 11 | VPYFFADGFVA | | | | | | | 17132 |
| HPV18 | L2 | 414 | 8 | WPIVSPTA | | | | | | | 17133 |
| HPV18 | L2 | 414 | 10 | WPIVSPTAPA | | | | | | | 17134 |
| HPV31 | E1 | 458 | 8 | APNTGKSY | | | | | | | 17135 |
| HPV31 | E1 | 458 | 9 | APNTGKSYF | | | | | | | 17136 |
| HPV31 | E1 | 458 | 11 | APNTGKSYFGM | | | | | | | 17137 |
| HPV31 | E1 | 539 | 10 | CPPLLITSNI | | | | | | | 17138 |
| HPV31 | E1 | 572 | 10 | FPFDKNGNPV | | | | | | | 17139 |
| HPV31 | E1 | 572 | 11 | FPFDKNGNPVY | | | | | | | 17140 |
| HPV31 | E1 | 128 | 11 | LPDSGYGNTEV | | | | | | | 17141 |
| HPV31 | E1 | 523 | 11 | NPVSIDVKHKA | | | | | | | 17142 |
| HPV31 | E1 | 579 | 11 | NPVYELSDKNW | | | | | | | 17143 |
| HPV31 | E1 | 289 | 8 | PPKLRSTA | | | | | | | 17144 |
| HPV31 | E1 | 289 | 9 | PPKLRSTAA | 0.0014 | 0.0003 | 0.0002 | 0.0002 | 0.0024 | | 17145 |

TABLE XI-continued

| | | | | | | | | | | | |
|---|---|---|---|---|---|---|---|---|---|---|---|
| HPV31 | E1 | 289 | 10 | PPKLRSTAAA | | | | | | | 17146 |
| HPV31 | E1 | 289 | 11 | PPKLRSTAAAL | | | | | | | 17147 |
| HPV31 | E1 | 540 | 9 | PPLLITSNI | | | | | | | 17148 |
| HPV31 | E1 | 540 | 11 | PPLLITSNINA | | | | | | | 17149 |
| HPV31 | E1 | 491 | 8 | QPLADAKI | | | | | | | 17150 |
| HPV31 | E1 | 491 | 10 | QPLADAKIGM | | | | | | | 17151 |
| HPV31 | E1 | 491 | 11 | QPLADAKIGML | | | | | | | 17152 |
| HPV31 | E1 | 288 | 9 | QPPKLRSTA | | | | | | | 17153 |
| HPV31 | E1 | 288 | 10 | QPPKLRSTAA | | | | | | | 17154 |
| HPV31 | E1 | 288 | 11 | QPPKLRSTAAA | | | | | | | 17155 |
| HPV31 | E1 | 236 | 9 | QPYCLYCHL | | | | | | | 17156 |
| HPV31 | E1 | 92 | 10 | SPLSDISSCV | | | | | | | 17157 |
| HPV31 | E1 | 106 | 9 | SPRLKAICI | 0.4700 | 0.0003 | 0.0004 | 0.0002 | 0.0004 | | 17158 |
| HPV31 | E1 | 506 | 10 | TPCWHYIDNY | | | | | | | 17159 |
| HPV31 | E1 | 506 | 11 | TPCWHYIDNYL | | | | | | | 17160 |
| HPV31 | E1 | 316 | 10 | TPEWIERQTV | | | | | | | 17161 |
| HPV31 | E1 | 316 | 11 | TPEWIERQTVL | | | | | | | 17162 |
| HPV31 | E1 | 169 | 9 | TPTRNILQV | | | | | | | 17163 |
| HPV31 | E1 | 169 | 10 | TPTRNILQVL | | | | | | | 17164 |
| HPV31 | E1 | 447 | 8 | VPKKNCIL | | | | | | | 17165 |
| HPV31 | E1 | 447 | 9 | VPKKNCILI | | | | | | | 17166 |
| HPV31 | E1 | 556 | 8 | WPYLHSRL | | | | | | | 17167 |
| HPV31 | E1 | 556 | 9 | WPYLHSRLV | | | | | | | 17168 |
| HPV31 | E1 | 556 | 10 | WPYLHSPLVV | | | | | | | 17169 |
| HPV31 | E1 | 556 | 11 | WPYLHSRLVVF | | | | | | | 17170 |
| HPV31 | E2 | 105 | 11 | APTGCLKKHGY | | | | | | | 17171 |
| HPV31 | E2 | 289 | 8 | CPATTPII | | | | | | | 17172 |
| HPV31 | E2 | 289 | 10 | CPATTPIIHL | | | | | | | 17173 |
| HPV31 | E2 | 195 | 11 | FPESVFSSDEI | | | | | | | 17174 |
| HPV31 | E2 | 257 | 11 | HPNKLLRGDSV | | | | | | | 17175 |
| HPV31 | E2 | 359 | 11 | IPNTVSVSTGY | | | | | | | 17176 |
| HPV31 | E2 | 293 | 10 | TPIIHLKGDA | | | | | | | 17177 |
| HPV31 | E2 | 59 | 9 | VPALSVSKA | | | | | | | 17178 |
| HPV31 | E2 | 59 | 11 | VPALSVSKAKA | | | | | | | 17179 |
| HPV31 | E5 | 69 | 10 | IPLFVIHTHA | | | | | | | 17180 |
| HPV31 | E5 | 30 | 9 | RPLVLSVSV | | | | | | | 17181 |
| HPV31 | E5 | 30 | 10 | RPLVLSVSVY | | | | | | | 17182 |
| HPV31 | E5 | 30 | 11 | RPLVLSVSVYA | | | | | | | 17183 |
| HPV31 | E5 | 55 | 8 | SPLRCFCI | | | | | | | 17184 |
| HPV31 | E5 | 55 | 9 | SPLRCFCIY | | | | | | | 17185 |
| HPV31 | E5 | 55 | 10 | SPLRCFCIYV | | | | | | | 17186 |
| HPV31 | E5 | 55 | 11 | SPLRCFCIYVV | | | | | | | 17187 |
| HPV31 | E6 | 111 | 9 | CPEEKQRHL | 0.0003 | 0.0002 | 0.0074 | 0.0006 | 0.0002 | | 17188 |
| HPV31 | E6 | 21 | 8 | IPYDELRL | | | | | | | 17189 |
| HPV31 | E6 | 21 | 11 | IPYDELRLNCV | | | | | | | 17190 |
| HPV31 | E6 | 4 | 9 | NPAERPRKL | | | | | | | 17191 |
| HPV31 | E6 | 8 | 8 | RPRKLHEL | | | | | | | 17192 |
| HPV31 | E6 | 8 | 11 | RPRKLHELSSA | | | | | | | 17193 |
| HPV31 | E6 | 142 | 8 | RPRTETQV | | | | | | | 17194 |
| HPV31 | E6 | 58 | 10 | TPHGVCTKCL | | | | | | | 17195 |
| HPV31 | E7 | 91 | 8 | CPNCSTRL | | | | | | | 17196 |
| HPV31 | E7 | 46 | 9 | EPDTSNYNI | | | | | | | 17197 |
| HPV31 | E7 | 46 | 10 | EPDTSNYNIV | | | | | | | 17198 |
| HPV31 | E7 | 28 | 10 | LPDSSDEEDV | | | | | | | 17199 |
| HPV31 | E7 | 28 | 11 | LPDSSDEEDVI | | | | | | | 17200 |
| HPV31 | E7 | 16 | 10 | QPEATDLHCY | | | | | | | 17201 |
| HPV31 | E7 | 5 | 8 | TPTLQDYV | | | | | | | 17202 |
| HPV31 | E7 | 5 | 9 | TPTLQDYVL | | | | | | | 17203 |
| HPV31 | E7 | 5 | 11 | TPTLQDYVLDL | | | | | | | 17204 |
| HPV31 | L1 | 433 | 10 | APQKPKEDPF | | | | | | | 17205 |
| HPV31 | L1 | 488 | 10 | APSASTTTPA | | | | | | | 17206 |
| HPV31 | L1 | 186 | 10 | CPPLELKNSV | | | | | | | 17207 |
| HPV31 | L1 | 186 | 11 | CPPLELKNSVI | | | | | | | 17208 |
| HPV31 | L1 | 440 | 8 | DPFKDYVF | | | | | | | 17209 |
| HPV31 | L1 | 440 | 9 | DPFKDYVFW | | | | | | | 17210 |
| HPV31 | L1 | 440 | 11 | DPFKDYVFWEV | | | | | | | 17211 |
| HPV31 | L1 | 241 | 8 | EPYGDTLF | | | | | | | 17212 |
| HPV31 | L1 | 241 | 9 | EPYGDTLFF | | | | | | | 17213 |
| HPV31 | L1 | 241 | 10 | EPYGDTLFFY | | | | | | | 17214 |
| HPV31 | L1 | 241 | 11 | EPYGDTLFFYL | | | | | | | 17215 |
| HPV31 | L1 | 463 | 8 | FPLGRKFL | | | | | | | 17216 |
| HPV31 | L1 | 463 | 9 | FPLGRKFLL | | | | | | | 17217 |
| HPV31 | L1 | 463 | 11 | FPLGRKFLLQA | | | | | | | 17218 |
| HPV31 | L1 | 293 | 8 | FPTPSGSM | | | | | | | 17219 |
| HPV31 | L1 | 293 | 9 | FPTPSGSMV | | | | | | | 17220 |
| HPV31 | L1 | 139 | 10 | GPGTDNRECI | | | | | | | 17221 |
| HPV31 | L1 | 52 | 10 | IPKSDNPKKI | | | | | | | 17222 |
| HPV31 | L1 | 52 | 11 | IPKSDNPKKIV | | | | | | | 17223 |
| HPV31 | L1 | 436 | 10 | KPKEDPFKDY | | | | | | | 17224 |

TABLE XI-continued

| | | | | | |
|---|---|---|---|---|---|
| HPV31 | L1 | 436 | 11 | KPKEDPFKDYV | 17225 |
| HPV31 | L1 | 163 | 8 | KPPIGEHW | 17226 |
| HPV31 | L1 | 310 | 8 | KPYWMQRA | 17227 |
| HPV31 | L1 | 78 | 9 | LPDPNKFGF | 17228 |
| HPV31 | L1 | 13 | 9 | LPPVPVSKV | 17229 |
| HPV31 | L1 | 13 | 10 | LPPVPVSKVV | 17230 |
| HPV31 | L1 | 396 | 8 | NPAILEDW | 17231 |
| HPV31 | L1 | 396 | 10 | NPAILEDWNF | 17232 |
| HPV31 | L1 | 93 | 8 | NPETQRLV | 17233 |
| HPV31 | L1 | 93 | 9 | NPETQRLVW | 17234 |
| HPV31 | L1 | 93 | 10 | NPETQRLVWA | 17235 |
| HPV31 | L1 | 57 | 10 | NPKKIVVPKV | 17236 |
| HPV31 | L1 | 187 | 9 | PPLELKNSV | 17237 |
| HPV31 | L1 | 187 | 10 | PPLELKNSVI | 17238 |
| HPV31 | L1 | 410 | 10 | PPSGSLEDTY | 17239 |
| HPV31 | L1 | 14 | 8 | PPVPVSKV | 17240 |
| HPV31 | L1 | 14 | 9 | PPVPVSKVV | 17241 |
| HPV31 | L1 | 478 | 11 | RPKFKAGKRSA | 17242 |
| HPV31 | L1 | 5 | 8 | RPSEATVY | 17243 |
| HPV31 | L1 | 5 | 9 | RPSEATVYL | 17244 |
| HPV31 | L1 | 174 | 8 | SPCSNNAI | 17245 |
| HPV31 | L1 | 182 | 8 | TPGDCPPL | 17246 |
| HPV31 | L1 | 182 | 10 | TPGDCPPLEL | 17247 |
| HPV31 | L1 | 409 | 11 | TPPSGSLEDTY | 17248 |
| HPV31 | L1 | 295 | 11 | TPSGSMVTSDA | 17249 |
| HPV31 | L1 | 63 | 9 | VPKVSGLQY | 17250 |
| HPV31 | L1 | 63 | 11 | VPKVSGLQYRV | 17251 |
| HPV31 | L1 | 221 | 9 | VPLDICNSI | 17252 |
| HPV31 | L1 | 232 | 8 | YPDYLKMV | 17253 |
| HPV31 | L1 | 232 | 9 | YPDYLKMVA | 17254 |
| HPV31 | L2 | 271 | 9 | APDPDFLDI | 17255 |
| HPV31 | L2 | 271 | 10 | APDPDFLDII | 17256 |
| HPV31 | L2 | 271 | 11 | APDPDFLDIIA | 17257 |
| HPV31 | L2 | 240 | 8 | APKQLITY | 17258 |
| HPV31 | L2 | 414 | 8 | APTQVFPF | 17259 |
| HPV31 | L2 | 414 | 10 | APTQVFPFPL | 17260 |
| HPV31 | L2 | 414 | 11 | APTQVFPFPLA | 17261 |
| HPV31 | L2 | 424 | 9 | APTTPQVSI | 17262 |
| HPV31 | L2 | 424 | 10 | APTTPQVSIF | 17263 |
| HPV31 | L2 | 424 | 11 | APTTPQVSIFV | 17264 |
| HPV31 | L2 | 28 | 9 | CPSDVIPKI | 17265 |
| HPV31 | L2 | 273 | 8 | DPDFLDII | 17266 |
| HPV31 | L2 | 273 | 9 | DPDFLDIIA | 17267 |
| HPV31 | L2 | 273 | 10 | DPDFLDIIAL | 17268 |
| HPV31 | L2 | 102 | 8 | DPSIVSLV | 17269 |
| HPV31 | L2 | 160 | 11 | DPSVLQPPTPA | 17270 |
| HPV31 | L2 | 234 | 11 | DPTFLSAPKQL | 17271 |
| HPV31 | L2 | 96 | 10 | DPVGPLDPSI | 17272 |
| HPV31 | L2 | 96 | 11 | DPVGPLDPSIV | 17273 |
| HPV31 | L2 | 421 | 10 | FPLAPTTPQV | 17274 |
| HPV31 | L2 | 406 | 9 | GPDVPIEHA | 17275 |
| HPV31 | L2 | 99 | 8 | GPLDPSIV | 17276 |
| HPV31 | L2 | 99 | 10 | GPLDPSIVSL | 17277 |
| HPV31 | L2 | 99 | 11 | GPLDPSIVSLV | 17278 |
| HPV31 | L2 | 125 | 8 | HPPTTSGF | 17279 |
| HPV31 | L2 | 125 | 10 | HPPTTSGFDI | 17280 |
| HPV31 | L2 | 125 | 11 | HPPTTSGFDIA | 17281 |
| HPV31 | L2 | 211 | 8 | IPGVRRPA | 17282 |
| HPV31 | L2 | 211 | 10 | IPGVRRPARL | 17283 |
| HPV31 | L2 | 123 | 10 | IPHPPTTSGF | 17284 |
| HPV31 | L2 | 401 | 9 | IPIFSGPDV | 17285 |
| HPV31 | L2 | 401 | 11 | IPIFSGPDVPI | 17286 |
| HPV31 | L2 | 87 | 9 | IPIRPPVSI | 17287 |
| HPV31 | L2 | 33 | 9 | IPKIEHTTI | 17288 |
| HPV31 | L2 | 33 | 10 | IPKIEHTTIA | 17289 |
| HPV31 | L2 | 191 | 8 | IPMDTFIV | 17290 |
| HPV31 | L2 | 327 | 9 | NPAGESIEM | 17291 |
| HPV31 | L2 | 249 | 9 | NPAYETVNA | 17292 |
| HPV31 | L2 | 155 | 9 | NPTFTDPSV | 17293 |
| HPV31 | L2 | 155 | 10 | NPTFTDPSVL | 17294 |
| HPV31 | L2 | 166 | 11 | PPTPAETSGHL | 17295 |
| HPV31 | L2 | 126 | 9 | PPTTSGFDI | 17296 |
| HPV31 | L2 | 126 | 10 | PPTTSGFDIA | 17297 |
| HPV31 | L2 | 91 | 8 | PPVSIDPV | 17298 |
| HPV31 | L2 | 91 | 11 | PPVSIDPVGPL | 17299 |
| HPV31 | L2 | 284 | 11 | RPALTSRRNTV | 17300 |
| HPV31 | L2 | 216 | 8 | RPARLGLY | 17301 |
| HPV31 | L2 | 216 | 11 | RPARLGLYSKA | 17302 |
| HPV31 | L2 | 90 | 9 | RPPVSIDPV | 17303 |

TABLE XI-continued

| | | | | | |
|---|---|---|---|---|---|
| HPV31 | L2 | 78 | 8 | RPSTVSEA | 17304 |
| HPV31 | L2 | 78 | 10 | RPSTVSEASI | 17305 |
| HPV31 | L2 | 372 | 11 | SPSTAVQSTSA | 17306 |
| HPV31 | L2 | 168 | 9 | TPAETSGHL | 17307 |
| HPV31 | L2 | 168 | 10 | TPAETSGHLL | 17308 |
| HPV31 | L2 | 168 | 11 | TPAETSGHLLL | 17309 |
| HPV31 | L2 | 141 | 10 | TPAILDVTSV | 17310 |
| HPV31 | L2 | 209 | 10 | TPIPGVRRPA | 17311 |
| HPV31 | L2 | 427 | 8 | TPQVSIFV | 17312 |
| HPV31 | L2 | 409 | 10 | VPIEHAPTQV | 17313 |
| HPV31 | L2 | 409 | 11 | VPIEHAPTQVF | 17314 |
| HPV31 | L2 | 393 | 9 | VPLSTGFDI | 17315 |
| HPV31 | L2 | 393 | 11 | VPLSTGFDIPI | 17316 |
| HPV31 | L2 | 73 | 10 | VPLSTRPSTV | 17317 |
| HPV31 | L2 | 387 | 9 | VPTNTTVPL | 17318 |
| HPV33 | E1 | 3 | 8 | DPEGTNGA | 17319 |
| HPV33 | E1 | 3 | 10 | DPEGTNGAGM | 17320 |
| HPV33 | E1 | 301 | 11 | EPPKLRSQTCA | 17321 |
| HPV33 | E1 | 585 | 10 | FPFDENGNPV | 17322 |
| HPV33 | E1 | 585 | 11 | FPFDENGNPVY | 17323 |
| HPV33 | E1 | 470 | 9 | GPANTGKSY | 17324 |
| HPV33 | E1 | 470 | 10 | GPANTGKSYF | 17325 |
| HPV33 | E1 | 293 | 8 | IPETCMVI | 17326 |
| HPV33 | E1 | 460 | 8 | IPKKSCML | 17327 |
| HPV33 | E1 | 460 | 9 | IPKKSCMLI | 17328 |
| HPV33 | E1 | 592 | 11 | NPVYAINDENW | 17329 |
| HPV33 | E1 | 302 | 10 | PPKLRSQTCA | 17330 |
| HPV33 | E1 | 302 | 11 | PPKLRSQTCAL | 17331 |
| HPV33 | E1 | 553 | 11 | PPLLLTSNTNA | 17332 |
| HPV33 | E1 | 504 | 8 | QPLSDAKI | 17333 |
| HPV33 | E1 | 504 | 10 | QPLSDAKIGM | 17334 |
| HPV33 | E1 | 504 | 11 | QPLSDAKIGMI | 17335 |
| HPV33 | E1 | 433 | 9 | RPIVQLLRY | 17336 |
| HPV33 | E1 | 237 | 8 | SPSVAESL | 17337 |
| HPV33 | E1 | 237 | 10 | SPSVAESLKV | 17338 |
| HPV33 | E1 | 237 | 11 | SPSVAESLKVL | 17339 |
| HPV33 | E1 | 329 | 8 | TPEWIDRL | 17340 |
| HPV33 | E1 | 329 | 10 | TPEWIDRLTV | 17341 |
| HPV33 | E1 | 329 | 11 | TPEWIDRLTVL | 17342 |
| HPV33 | E1 | 518 | 8 | TPISWTYI | 17343 |
| HPV33 | E1 | 518 | 11 | TPISWTYIDDY | 17344 |
| HPV33 | E1 | 569 | 8 | WPYLHSRL | 17345 |
| HPV33 | E1 | 569 | 10 | WPYLHSRLTV | 17346 |
| HPV33 | E1 | 569 | 11 | WPYLHSRLTVF | 17347 |
| HPV33 | E2 | 195 | 10 | CPTSISSNQI | 17348 |
| HPV33 | E2 | 247 | 9 | DPALDNRTA | 17349 |
| HPV33 | E2 | 340 | 11 | IPPTVQISTGF | 17350 |
| HPV33 | E2 | 294 | 10 | KPYKELYSSM | 17351 |
| HPV33 | E2 | 26 | 8 | LPSQIEHW | 17352 |
| HPV33 | E2 | 26 | 10 | LPSQIEHWKL | 17353 |
| HPV33 | E2 | 26 | 11 | LPSQIEHWKLI | 17354 |
| HPV33 | E2 | 341 | 10 | PPTVQISTGF | 17355 |
| HPV33 | E2 | 341 | 11 | PPTVQISTGFM | 17356 |
| HPV33 | E2 | 238 | 9 | QPLTKLFCA | 17357 |
| HPV33 | E2 | 229 | 9 | RPADTTDTA | 17358 |
| HPV33 | E2 | 59 | 11 | VPSLLASKTKA | 17359 |
| HPV33 | E5 | 59 | 8 | LPMMCINF | 17360 |
| HPV33 | E5 | 59 | 10 | LPMMCINFHA | 17361 |
| HPV33 | E5 | 20 | 10 | RPLILSISTY | 17362 |
| HPV33 | E5 | 20 | 11 | RPLILSISTYA | 17363 |
| HPV33 | E5 | 45 | 9 | SPLKIFFCY | 17364 |
| HPV33 | E5 | 45 | 10 | SPLKIFFCYL | 17365 |
| HPV33 | E5 | 45 | 11 | SPLKIFFCYLL | 17366 |
| HPV33 | E6 | 111 | 9 | CPQEKKRHV | 17367 |
| HPV33 | E6 | 111 | 11 | CPQEKKRHVDL | 17368 |
| HPV33 | E6 | 94 | 8 | KPLNEILI | 17369 |
| HPV33 | E6 | 94 | 11 | KPLNEILIRCI | 17370 |
| HPV33 | E6 | 35 | 8 | KPLQRSEV | 17371 |
| HPV33 | E6 | 35 | 9 | KPLQRSEVY | 17372 |
| HPV33 | E6 | 35 | 11 | KPLQRSEVYDF | 17373 |
| HPV33 | E6 | 8 | 8 | KPRTLHDL | 17374 |
| HPV33 | E6 | 8 | 11 | KPRTLHDLCQA | 17375 |
| HPV33 | E6 | 58 | 8 | NPFGICKL | 17376 |
| HPV33 | E6 | 58 | 10 | NPFGICKLCL | 17377 |
| HPV33 | E7 | 18 | 8 | EPTDLYCY | 17378 |
| HPV33 | E7 | 18 | 11 | EPTDLYCYEQL | 17379 |
| HPV33 | E7 | 5 | 8 | KPTLKEYV | 17380 |
| HPV33 | E7 | 5 | 9 | KPTLKEYVL | 17381 |
| HPV33 | E7 | 5 | 11 | KPTLKEYVLDL | 17382 |

TABLE XI-continued

| | | | | | |
|---|---|---|---|---|---|
| HPV33 | E7 | 46 | 8 | QPATADYY | 17383 |
| HPV33 | E7 | 46 | 9 | QPATADYYI | 17384 |
| HPV33 | E7 | 46 | 10 | QPATADYYIV | 17385 |
| HPV33 | E7 | 40 | 9 | RPDGQAQPA | 17386 |
| HPV33 | E7 | 40 | 11 | RPDGQAQPATA | 17387 |
| HPV33 | E7 | 16 | 8 | YPEPTDLY | 17388 |
| HPV33 | E7 | 16 | 10 | YPEPTDLYCY | 17389 |
| HPV33 | L1 | 180 | 9 | APANDCPPL | 17390 |
| HPV33 | L1 | 180 | 11 | APANDCPPLEL | 17391 |
| HPV33 | L1 | 483 | 10 | APTSTRTSSA | 17392 |
| HPV33 | L1 | 185 | 10 | CPPLELINTI | 17393 |
| HPV33 | L1 | 185 | 11 | CPPLELINTII | 17394 |
| HPV33 | L1 | 438 | 8 | DPLGKYTF | 17395 |
| HPV33 | L1 | 438 | 9 | DPLGKYTFW | 17396 |
| HPV33 | L1 | 438 | 11 | DPLGKYTFWEV | 17397 |
| HPV33 | L1 | 240 | 8 | EPYGDSLF | 17398 |
| HPV33 | L1 | 240 | 9 | EPYGDSLFF | 17399 |
| HPV33 | L1 | 240 | 10 | EPYGDSLFFF | 17400 |
| HPV33 | L1 | 240 | 11 | EPYGDSLFFFL | 17401 |
| HPV33 | L1 | 461 | 8 | FPLGRKFL | 17402 |
| HPV33 | L1 | 461 | 9 | FPLGRKFLL | 17403 |
| HPV33 | L1 | 461 | 11 | FPLGRKFLLQA | 17404 |
| HPV33 | L1 | 292 | 8 | FPTPSGSM | 17405 |
| HPV33 | L1 | 292 | 9 | FPTPSGSMV | 17406 |
| HPV33 | L1 | 476 | 8 | KPKLKRAA | 17407 |
| HPV33 | L1 | 163 | 8 | KPPTGEHW | 17408 |
| HPV33 | L1 | 309 | 8 | KPYWLQRA | 17409 |
| HPV33 | L1 | 78 | 9 | LPDPNKFGF | 17410 |
| HPV33 | L1 | 13 | 9 | LPPVPVSKV | 17411 |
| HPV33 | L1 | 13 | 10 | LPPVPVSKVV | 17412 |
| HPV33 | L1 | 394 | 8 | NPDILEDW | 17413 |
| HPV33 | L1 | 394 | 10 | NPDILEDWQF | 17414 |
| HPV33 | L1 | 93 | 8 | NPDTQRLV | 17415 |
| HPV33 | L1 | 93 | 9 | NPDTQRLVW | 17416 |
| HPV33 | L1 | 93 | 10 | NPDTQRLVWA | 17417 |
| HPV33 | L1 | 54 | 8 | NPTNAKKL | 17418 |
| HPV33 | L1 | 54 | 9 | NPTNAKKLL | 17419 |
| HPV33 | L1 | 54 | 10 | NPTNAKKLLV | 17420 |
| HPV33 | L1 | 432 | 9 | PPKEKEDPL | 17421 |
| HPV33 | L1 | 186 | 9 | PPLELINTI | 17422 |
| HPV33 | L1 | 186 | 10 | PPLELINTII | 17423 |
| HPV33 | L1 | 407 | 11 | PPPSASLQDTY | 17424 |
| HPV33 | L1 | 408 | 10 | PPSASLQDTY | 17425 |
| HPV33 | L1 | 164 | 11 | PPTGEHWGKGV | 17426 |
| HPV33 | L1 | 14 | 8 | PPVPVSKV | 17427 |
| HPV33 | L1 | 14 | 9 | PPVPVSKVV | 17428 |
| HPV33 | L1 | 139 | 10 | QPGADNRECL | 17429 |
| HPV33 | L1 | 5 | 8 | RPSEATVY | 17430 |
| HPV33 | L1 | 5 | 9 | RPSEATVYL | 17431 |
| HPV33 | L1 | 406 | 8 | TPPPSASL | 17432 |
| HPV33 | L1 | 63 | 9 | VPKVSGLQY | 17433 |
| HPV33 | L1 | 63 | 11 | VPKVSGLQYRV | 17434 |
| HPV33 | L1 | 431 | 10 | VPPKEKEDPL | 17435 |
| HPV33 | L2 | 173 | 9 | APAEASGHF | 17436 |
| HPV33 | L2 | 173 | 10 | APAEASGHFI | 17437 |
| HPV33 | L2 | 173 | 11 | APAEASGHFIF | 17438 |
| HPV33 | L2 | 276 | 9 | APDPDFLDI | 17439 |
| HPV33 | L2 | 276 | 10 | APDPDFLDII | 17440 |
| HPV33 | L2 | 276 | 11 | APDPDFLDIIA | 17441 |
| HPV33 | L2 | 120 | 10 | APSIPTPSGF | 17442 |
| HPV33 | L2 | 27 | 9 | CPPDVIPKV | 17443 |
| HPV33 | L2 | 239 | 11 | DPAFLTSPHKL | 17444 |
| HPV33 | L2 | 278 | 8 | DPDFLDII | 17445 |
| HPV33 | L2 | 278 | 9 | DPDFLDIIA | 17446 |
| HPV33 | L2 | 278 | 10 | DPDFLDIIAL | 17447 |
| HPV33 | L2 | 261 | 8 | DPEDTLQF | 17448 |
| HPV33 | L2 | 77 | 9 | DPPTAAIPL | 17449 |
| HPV33 | L2 | 165 | 9 | EPSVLHPPA | 17450 |
| HPV33 | L2 | 165 | 11 | EPSVLHPPAPA | 17451 |
| HPV33 | L2 | 428 | 8 | FPFDTIVV | 17452 |
| HPV33 | L2 | 428 | 11 | FPFDTIVVDGA | 17453 |
| HPV33 | L2 | 415 | 8 | FPTSSPFV | 17454 |
| HPV33 | L2 | 415 | 10 | FPTSSPFVPI | 17455 |
| HPV33 | L2 | 456 | 8 | FPYFFTDV | 17456 |
| HPV33 | L2 | 456 | 10 | FPYFFTDVRV | 17457 |
| HPV33 | L2 | 456 | 11 | FPYFFTDVRVA | 17458 |
| HPV33 | L2 | 407 | 8 | GPDIPSPL | 17459 |
| HPV33 | L2 | 407 | 9 | GPDIPSPLF | 17460 |
| HPV33 | L2 | 98 | 8 | GPLDSSIV | 17461 |

TABLE XI-continued

| | | | | | | | | | | | |
|---|---|---|---|---|---|---|---|---|---|---|---|
| HPV33 | L2 | 98 | 10 | GPLDSSIVSL | | | | | | | 17462 |
| HPV33 | L2 | 98 | 11 | GPLDSSIVSLI | | | | | | | 17463 |
| HPV33 | L2 | 170 | 8 | HPPAPAEA | | | | | | | 17464 |
| HPV33 | L2 | 216 | 8 | IPGSRPVA | | | | | | | 17465 |
| HPV33 | L2 | 216 | 10 | IPGSRPVARL | | | | | | | 17466 |
| HPV33 | L2 | 32 | 9 | IPKVEGSTI | | | | | | | 17467 |
| HPV33 | L2 | 32 | 10 | IPKVEGSTIA | | | | | | | 17468 |
| HPV33 | L2 | 394 | 11 | IPLNTGFDTPV | | | | | | | 17469 |
| HPV33 | L2 | 83 | 10 | IPLQPIRPPV | | | | | | | 17470 |
| HPV33 | L2 | 196 | 8 | IPMDTFVV | | | | | | | 17471 |
| HPV33 | L2 | 123 | 9 | IPTPSGFDV | | | | | | | 17472 |
| HPV33 | L2 | 160 | 9 | NPTFTEPSV | | | | | | | 17473 |
| HPV33 | L2 | 160 | 10 | NPTFTEPSVL | | | | | | | 17474 |
| HPV33 | L2 | 171 | 11 | PPAPAEASGHF | | | | | | | 17475 |
| HPV33 | L2 | 28 | 8 | PPDVIPKV | | | | | | | 17476 |
| HPV33 | L2 | 78 | 8 | PPTAAIPL | | | | | | | 17477 |
| HPV33 | L2 | 78 | 11 | PPTAAIPLQPI | | | | | | | 17478 |
| HPV33 | L2 | 90 | 8 | PPVTVDTV | | | | | | | 17479 |
| HPV33 | L2 | 90 | 11 | PPVTVDTVGPL | | | | | | | 17480 |
| HPV33 | L2 | 86 | 9 | QPIRPPVTV | | | | | | | 17481 |
| HPV33 | L2 | 346 | 11 | QPLHDTSTSSY | | | | | | | 17482 |
| HPV33 | L2 | 289 | 11 | RPAITSRRHTV | | | | | | | 17483 |
| HPV33 | L2 | 89 | 9 | RPPVTVDTV | | | | | | | 17484 |
| HPV33 | L2 | 220 | 8 | RPVARLGL | | | | | | | 17485 |
| HPV33 | L2 | 220 | 9 | RPVARLGLY | | | | | | | 17486 |
| HPV33 | L2 | 274 | 8 | SPAPDPDF | | | | | | | 17487 |
| HPV33 | L2 | 274 | 9 | SPAPDPDFL | | | | | | | 17488 |
| HPV33 | L2 | 274 | 11 | SPAPDPDFLDI | | | | | | | 17489 |
| HPV33 | L2 | 425 | 9 | SPFFPFDTI | | | | | | | 17490 |
| HPV33 | L2 | 425 | 10 | SPFFPFDTIV | | | | | | | 17491 |
| HPV33 | L2 | 425 | 11 | SPFFPFDTIVV | | | | | | | 17492 |
| HPV33 | L2 | 419 | 9 | SPFVPISPF | | | | | | | 17493 |
| HPV33 | L2 | 419 | 10 | SPFVPISPFF | | | | | | | 17494 |
| HPV33 | L2 | 245 | 8 | SPHKLITY | | | | | | | 17495 |
| HPV33 | L2 | 329 | 10 | SPIVPLDHTV | | | | | | | 17496 |
| HPV33 | L2 | 412 | 10 | SPLFPTSSPF | | | | | | | 17497 |
| HPV33 | L2 | 412 | 11 | SPLFPTSSPFV | | | | | | | 17498 |
| HPV33 | L2 | 185 | 9 | SPTVSTQSY | | | | | | | 17499 |
| HPV33 | L2 | 138 | 10 | TPAIINVSSV | | | | | | | 17500 |
| HPV33 | L2 | 214 | 9 | TPIPGSRPV | | | | | | | 17501 |
| HPV33 | L2 | 214 | 10 | TPIPGSRPVA | | | | | | | 17502 |
| HPV33 | L2 | 375 | 10 | TPMQHSYSTF | | | | | | | 17503 |
| HPV33 | L2 | 375 | 11 | TPMQHSYSTFA | | | | | | | 17504 |
| HPV33 | L2 | 125 | 11 | TPSGFDVTTSA | | | | | | | 17505 |
| HPV33 | L2 | 402 | 9 | TPVMSGPDI | | | | | | | 17506 |
| HPV33 | L2 | 72 | 10 | VPIGTDPPTA | | | | | | | 17507 |
| HPV33 | L2 | 72 | 11 | VPIGTDPPTAA | | | | | | | 17508 |
| HPV33 | L2 | 422 | 9 | VPISPFFPF | | | | | | | 17509 |
| HPV33 | L2 | 338 | 8 | VPNEQYEL | | | | | | | 17510 |
| HPV33 | L2 | 338 | 11 | VPNEQYELQPL | | | | | | | 17511 |
| HPV45 | E1 | 552 | 10 | CPPILLTSNI | | | | | | | 17512 |
| HPV45 | E1 | 562 | 8 | DPAKDNKW | | | | | | | 17513 |
| HPV45 | E1 | 562 | 10 | DPAKDNKWPY | | | | | | | 17514 |
| HPV45 | E1 | 562 | 11 | DPAKDNKWPYL | | | | | | | 17515 |
| HPV45 | E1 | 179 | 9 | DPHCSITEL | | | | | | | 17516 |
| HPV45 | E1 | 504 | 8 | EPLADTKV | | | | | | | 17517 |
| HPV45 | E1 | 504 | 9 | EPLADTKVA | | | | | | | 17518 |
| HPV45 | E1 | 504 | 10 | EPLADTKVAM | | | | | | | 17519 |
| HPV45 | E1 | 504 | 11 | EPLADTKVAML | | | | | | | 17520 |
| HPV45 | E1 | 301 | 9 | EPPKLRSSV | | | | | | | 17521 |
| HPV45 | E1 | 301 | 10 | EPPKLRSSVA | | | | | | | 17522 |
| HPV45 | E1 | 301 | 11 | EPPKLRSSVAA | | | | | | | 17523 |
| HPV45 | E1 | 585 | 10 | FPFDKNGNPV | | | | | | | 17524 |
| HPV45 | E1 | 585 | 11 | FPFDKNGNPVY | | | | | | | 17525 |
| HPV45 | E1 | 470 | 9 | GPANTGKSY | | | | | | | 17526 |
| HPV45 | E1 | 470 | 10 | GPANTGKSYF | | | | | | | 17527 |
| HPV45 | E1 | 627 | 9 | IPFGTFKCV | | | | | | | 17528 |
| HPV45 | E1 | 249 | 9 | KPATLYAHI | | | | | | | 17529 |
| HPV45 | E1 | 545 | 11 | KPLLQLKCPPI | | | | | | | 17530 |
| HPV45 | E1 | 237 | 8 | NPTVAEGF | | | | | | | 17531 |
| HPV45 | E1 | 237 | 11 | NPTVAEGFKTL | | | | | | | 17532 |
| HPV45 | E1 | 592 | 11 | NPVYEINDKNW | | | | | | | 17533 |
| HPV45 | E1 | 553 | 9 | PPILLTSNI | | | | | | | 17534 |
| HPV45 | E1 | 302 | 8 | PPKLRSSV | | | | | | | 17535 |
| HPV45 | E1 | 302 | 9 | PPKLRSSVA | | | | | | | 17536 |
| HPV45 | E1 | 302 | 10 | PPKLRSSVAA | | | | | | | 17537 |
| HPV45 | E1 | 302 | 11 | PPKLRSSVAAL | | | | | | | 17538 |
| HPV45 | E1 | 433 | 9 | RPIVQFLRY | 0.0033 | 0.0400 | 0.0002 | 0.0230 | 0.0004 | | 17539 |
| HPV45 | E1 | 97 | 9 | SPLGEQLSV | | | | | | | 17540 |

TABLE XI-continued

| | | | | | | | | | | | |
|---|---|---|---|---|---|---|---|---|---|---|---|
| HPV45 | E1 | 110 | 9 | SPRLQEISL | 0.6200 | 0.0008 | 0.0005 | 0.0002 | 0.0004 | | 17541 |
| HPV45 | E1 | 329 | 8 | TPEWIQRL | | | | | | | 17542 |
| HPV45 | E1 | 329 | 10 | TPEWIQRLTI | | | | | | | 17543 |
| HPV45 | E1 | 329 | 11 | TPEWIQRLTII | | | | | | | 17544 |
| HPV45 | E1 | 460 | 8 | TPKKNCIL | | | | | | | 17545 |
| HPV45 | E1 | 460 | 9 | TPKKNCILL | | | | | | | 17546 |
| HPV45 | E1 | 460 | 10 | TPKKNCILLY | | | | | | | 17547 |
| HPV45 | E1 | 293 | 8 | VPETCMLI | | | | | | | 17548 |
| HPV45 | E1 | 569 | 8 | WPYLESRV | | | | | | | 17549 |
| HPV45 | E1 | 569 | 10 | WPYLESRVTV | | | | | | | 17550 |
| HPV45 | E1 | 569 | 11 | WPYLESRVTVF | | | | | | | 17551 |
| HPV45 | E2 | 355 | 9 | IPNSVQISV | | | | | | | 17552 |
| HPV45 | E2 | 355 | 11 | IPNSVQISVGY | | | | | | | 17553 |
| HPV45 | E2 | 240 | 8 | KPHIQTPA | | | | | | | 17554 |
| HPV45 | E2 | 66 | 10 | PPINISKSKA | | | | | | | 17555 |
| HPV45 | E2 | 5 | 10 | TPKESLSERL | | | | | | | 17556 |
| HPV45 | E2 | 238 | 10 | TPKPHIQTPA | | | | | | | 17557 |
| HPV45 | E2 | 65 | 11 | VPPINISKSKA | | | | | | | 17558 |
| HPV45 | E6 | 6 | 9 | DPTQRPYKL | | | | | | | 17559 |
| HPV45 | E6 | 14 | 8 | LPDLCTEL | | | | | | | 17560 |
| HPV45 | E6 | 113 | 9 | NPAEKRRHL | | | | | | | 17561 |
| HPV45 | E6 | 10 | 8 | RPYKLPDL | | | | | | | 17562 |
| HPV45 | E7 | 22 | 8 | DPVDLLCY | | | | | | | 17563 |
| HPV45 | E7 | 22 | 11 | DPVDLLCYEQL | | | | | | | 17564 |
| HPV45 | E7 | 16 | 9 | EPQNELDPV | | | | | | | 17565 |
| HPV45 | E7 | 16 | 11 | EPQNELDPVDL | | | | | | | 17566 |
| HPV45 | E7 | 56 | 8 | EPQRHKIL | | | | | | | 17567 |
| HPV45 | E7 | 56 | 10 | EPQRHKILCV | | | | | | | 17568 |
| HPV45 | E7 | 3 | 9 | GPRATLQEI | | | | | | | 17569 |
| HPV45 | E7 | 3 | 10 | GPRATLQEIV | | | | | | | 17570 |
| HPV45 | E7 | 3 | 11 | GPRATLQEIVL | | | | | | | 17571 |
| HPV45 | L1 | 212 | 10 | CPPLELKNTI | | | | | | | 17572 |
| HPV45 | L1 | 212 | 11 | CPPLELKNTII | | | | | | | 17573 |
| HPV45 | L1 | 386 | 8 | DPTKFKHY | | | | | | | 17574 |
| HPV45 | L1 | 469 | 8 | DPYDKLKF | | | | | | | 17575 |
| HPV45 | L1 | 469 | 9 | DPYDKLKFW | | | | | | | 17576 |
| HPV45 | L1 | 469 | 11 | DPYDKLKFWTV | | | | | | | 17577 |
| HPV45 | L1 | 267 | 8 | DPYGDSMF | | | | | | | 17578 |
| HPV45 | L1 | 267 | 9 | DPYGDSMFF | | | | | | | 17579 |
| HPV45 | L1 | 267 | 11 | DPYGDSMFFCL | | | | | | | 17580 |
| HPV45 | L1 | 21 | 8 | FPIFLQMA | | | | | | | 17581 |
| HPV45 | L1 | 21 | 9 | FPIFLQMAL | | | | | | | 17582 |
| HPV45 | L1 | 21 | 10 | FPIFLQMALW | | | | | | | 17583 |
| HPV45 | L1 | 511 | 8 | GPRKRPAA | | | | | | | 17584 |
| HPV45 | L1 | 338 | 8 | KPYWLHKA | | | | | | | 17585 |
| HPV45 | L1 | 104 | 9 | LPDNKFGL | | | | | | | 17586 |
| HPV45 | L1 | 39 | 9 | LPPPSVARV | | | | | | | 17587 |
| HPV45 | L1 | 39 | 10 | LPPPSVARVV | | | | | | | 17588 |
| HPV45 | L1 | 119 | 8 | NPETQRLV | | | | | | | 17589 |
| HPV45 | L1 | 119 | 9 | NPETQRLVW | | | | | | | 17590 |
| HPV45 | L1 | 119 | 10 | NPETQRLVWA | | | | | | | 17591 |
| HPV45 | L1 | 73 | 11 | NPYFRVVPSGA | | | | | | | 17592 |
| HPV45 | L1 | 464 | 8 | PPEKQDPY | | | | | | | 17593 |
| HPV45 | L1 | 464 | 11 | PPEKQDPYDKL | | | | | | | 17594 |
| HPV45 | L1 | 213 | 9 | PPLELKNTI | | | | | | | 17595 |
| HPV45 | L1 | 213 | 10 | PPLELKNTII | | | | | | | 17596 |
| HPV45 | L1 | 437 | 8 | PPPPTTSL | | | | | | | 17597 |
| HPV45 | L1 | 437 | 9 | PPPPTTSLV | | | | | | | 17598 |
| HPV45 | L1 | 40 | 8 | PPPSVARV | | | | | | | 17599 |
| HPV45 | L1 | 40 | 9 | PPPSVARVV | | | | | | | 17600 |
| HPV45 | L1 | 438 | 8 | PPPTTSLV | | | | | | | 17601 |
| HPV45 | L1 | 438 | 11 | PPPTTSLVDTY | | | | | | | 17602 |
| HPV45 | L1 | 41 | 8 | PPSVARVV | | | | | | | 17603 |
| HPV45 | L1 | 439 | 10 | PPTTSLVDTY | | | | | | | 17604 |
| HPV45 | L1 | 208 | 8 | QPGDCPPL | | | | | | | 17605 |
| HPV45 | L1 | 208 | 10 | QPGDCPPLEL | | | | | | | 17606 |
| HPV45 | L1 | 515 | 9 | RPAASTSTA | | | | | | | 17607 |
| HPV45 | L1 | 525 | 8 | RPAKRVRI | | | | | | | 17608 |
| HPV45 | L1 | 31 | 8 | RPSDSTVY | | | | | | | 17609 |
| HPV45 | L1 | 31 | 9 | RPSDSTVYL | | | | | | | 17610 |
| HPV45 | L1 | 507 | 11 | RPTIGPRKRPA | | | | | | | 17611 |
| HPV45 | L1 | 321 | 8 | SPSPSGSI | | | | | | | 17612 |
| HPV45 | L1 | 463 | 9 | TPPEKQDPY | | | | | | | 17613 |
| HPV45 | L1 | 189 | 8 | VPAIGEHW | | | | | | | 17614 |
| HPV45 | L1 | 189 | 9 | VPAIGEHWA | | | | | | | 17615 |
| HPV45 | L1 | 89 | 9 | VPKVSAYQY | | | | | | | 17616 |
| HPV45 | L1 | 89 | 11 | VPKVSAYQYRV | | | | | | | 17617 |
| HPV45 | L1 | 247 | 9 | VPLDICQSI | | | | | | | 17618 |
| HPV45 | L1 | 381 | 10 | VPNTYDPTKF | | | | | | | 17619 |

TABLE XI-continued

| | | | | | |
|---|---|---|---|---|---|
| HPV45 | L1 | 436 | 9 | VPPPPTTSL | 17620 |
| HPV45 | L1 | 436 | 10 | VPPPPTTSLV | 17621 |
| HPV45 | L1 | 79 | 10 | VPSGAGNKQA | 17622 |
| HPV45 | L1 | 79 | 11 | VPSGAGNKQAV | 17623 |
| HPV45 | L1 | 258 | 9 | YPDYLQMSA | 17624 |
| HPV45 | L1 | 492 | 8 | YPLGRKFL | 17625 |
| HPV45 | L1 | 492 | 9 | YPLGRKFLV | 17626 |
| HPV45 | L1 | 492 | 11 | YPLGRKFLVQA | 17627 |
| HPV45 | L2 | 27 | 9 | CPPDVINKV | 17628 |
| HPV45 | L2 | 100 | 8 | DPSIVTLV | 17629 |
| HPV45 | L2 | 208 | 8 | EPISSTPL | 17630 |
| HPV45 | L2 | 208 | 11 | EPISSTPLPTV | 17631 |
| HPV45 | L2 | 257 | 9 | EPLDTTLSF | 17632 |
| HPV45 | L2 | 266 | 11 | EPTSNVPDSDF | 17633 |
| HPV45 | L2 | 94 | 10 | EPVGPTDPSI | 17634 |
| HPV45 | L2 | 94 | 11 | EPVGPTDPSIV | 17635 |
| HPV45 | L2 | 445 | 8 | FPKKRKRI | 17636 |
| HPV45 | L2 | 445 | 10 | FPKKRKRIPY | 17637 |
| HPV45 | L2 | 445 | 11 | FPKKRKRIPYF | 17638 |
| HPV45 | L2 | 223 | 8 | GPRLYSRA | 17639 |
| HPV45 | L2 | 97 | 8 | GPTDPSIV | 17640 |
| HPV45 | L2 | 97 | 10 | GPTDPSIVTL | 17641 |
| HPV45 | L2 | 97 | 11 | GPTDPSIVTLV | 17642 |
| HPV45 | L2 | 85 | 8 | GPTRPPVV | 17643 |
| HPV45 | L2 | 85 | 9 | GPTRPPVVI | 17644 |
| HPV45 | L2 | 244 | 8 | HPSSLVTF | 17645 |
| HPV45 | L2 | 452 | 9 | IPYFFADGF | 17646 |
| HPV45 | L2 | 452 | 10 | IPYFFADGFV | 17647 |
| HPV45 | L2 | 452 | 11 | IPYFFADGFVA | 17648 |
| HPV45 | L2 | 408 | 8 | LPSHTPMW | 17649 |
| HPV45 | L2 | 377 | 9 | MPSTAASSY | 17650 |
| HPV45 | L2 | 159 | 9 | NPAFSDPSI | 17651 |
| HPV45 | L2 | 159 | 10 | NPAFSDPSII | 17652 |
| HPV45 | L2 | 253 | 11 | NPAYEPLDTTL | 17653 |
| HPV45 | L2 | 355 | 10 | PPASTTPSTI | 17654 |
| HPV45 | L2 | 28 | 8 | PPDVINKV | 17655 |
| HPV45 | L2 | 354 | 11 | PPPASTTPSTI | 17656 |
| HPV45 | L2 | 89 | 8 | PPVVIEPV | 17657 |
| HPV45 | L2 | 284 | 11 | RPALSSRRGTV | 17658 |
| HPV45 | L2 | 88 | 9 | RPPVVIEPV | 17659 |
| HPV45 | L2 | 324 | 9 | SPIAATEEI | 17660 |
| HPV45 | L2 | 324 | 11 | SPIAATEEIEL | 17661 |
| HPV45 | L2 | 419 | 10 | SPTNASTTTY | 17662 |
| HPV45 | L2 | 419 | 11 | SPTNASTTTYI | 17663 |
| HPV45 | L2 | 137 | 11 | TPAVLDITPTV | 17664 |
| HPV45 | L2 | 213 | 9 | TPLPTVRRV | 17665 |
| HPV45 | L2 | 360 | 9 | TPSTIHKSF | 17666 |
| HPV45 | L2 | 360 | 11 | TPSTIHKSFTY | 17667 |
| HPV45 | L2 | 184 | 9 | TPTSGSHGY | 17668 |
| HPV45 | L2 | 144 | 9 | TPTVDSVSI | 17669 |
| HPV45 | L2 | 271 | 9 | VPDSDFMDI | 17670 |
| HPV45 | L2 | 271 | 10 | VPDSDFMDII | 17671 |
| HPV45 | L2 | 398 | 9 | VPIYTGPDI | 17672 |
| HPV45 | L2 | 398 | 10 | VPIYTGPDII | 17673 |
| HPV45 | L2 | 398 | 11 | VPIYTGPDIIL | 17674 |
| HPV45 | L2 | 72 | 10 | VPLGGRSNTV | 17675 |
| HPV45 | L2 | 72 | 11 | VPLGGRSNTVV | 17676 |
| HPV45 | L2 | 390 | 9 | VPLTSAWDV | 17677 |
| HPV45 | L2 | 390 | 11 | VPLTSAWDVPI | 17678 |
| HPV45 | L2 | 170 | 11 | VPQTGEVSGNI | 17679 |
| HPV45 | L2 | 119 | 10 | VPTFTGTSGF | 17680 |
| HPV45 | L2 | 415 | 9 | WPSTSPTNA | 17681 |
| HPV45 | L2 | 370 | 8 | YPKYSLTM | 17682 |
| HPV56 | E2 | 138 | 11 | CPDSVSSTCRY | 17683 |
| HPV56 | E2 | 243 | 10 | EPNRLKCCRY | 17684 |
| HPV56 | E2 | 229 | 9 | HPGDKTTPV | 17685 |
| HPV56 | E2 | 229 | 10 | HPGDKTTPVV | 17686 |
| HPV56 | E2 | 300 | 8 | IPVVYRLV | 17687 |
| HPV56 | E2 | 300 | 9 | IPVVYRLVW | 17688 |
| HPV56 | E2 | 182 | 8 | RPGKRPRL | 17689 |
| HPV56 | E2 | 186 | 9 | RPRLRESEF | 17690 |
| HPV56 | E2 | 151 | 9 | SPVETVNEY | 17691 |
| HPV56 | E2 | 2 | 9 | VPCLQVCKA | 17692 |
| HPV56 | E2 | 2 | 11 | VPCLQVCKAKA | 17693 |
| HPV56 | E6 | 61 | 8 | FPYAVCRV | 17694 |
| HPV56 | E6 | 61 | 10 | FPYAVCRVCL | 17695 |
| HPV56 | E6 | 61 | 11 | FPYAVCRVCLL | 17696 |
| HPV56 | E6 | 24 | 8 | IPLIDLRL | 17697 |
| HPV56 | E6 | 24 | 11 | IPLIDLRLSCV | 17698 |

TABLE XI-continued

| | | | | | |
|---|---|---|---|---|---|
| HPV56 | E6 | 7 | 9 | NPQERPRSL | 17699 |
| HPV56 | E6 | 11 | 8 | RPRSLHHL | 17700 |
| HPV56 | E6 | 11 | 11 | RPRSLHHLSEV | 17701 |
| HPV56 | E6 | 111 | 10 | SPLTPEEKQL | 17702 |
| HPV56 | E7 | 46 | 8 | RPQQARQA | 17703 |
| HPV56 | E7 | 16 | 8 | TPQTEIDL | 17704 |
| HPV56 | E7 | 63 | 8 | VPCCECKF | 17705 |
| HPV56 | E7 | 63 | 9 | VPCCECKFV | 17706 |
| HPV56 | E7 | 63 | 10 | VPCCECKFVV | 17707 |
| HPV56 | E7 | 5 | 8 | VPTLQDVV | 17708 |
| HPV56 | E7 | 5 | 9 | VPTLQDVVL | 17709 |
| HPV56 | E7 | 5 | 11 | VPTLQDVVLEL | 17710 |
| HPV56 | L1 | 521 | 9 | APTSTSTPA | 17711 |
| HPV56 | L1 | 219 | 11 | CPPLALINTPI | 17712 |
| HPV56 | L1 | 472 | 8 | DPLAKYKF | 17713 |
| HPV56 | L1 | 472 | 9 | DPLAKYKFW | 17714 |
| HPV56 | L1 | 472 | 11 | DPLAKYKFWDV | 17715 |
| HPV56 | L1 | 11 | 8 | DPPLHYGL | 17716 |
| HPV56 | L1 | 11 | 10 | DPPLHYGLCI | 17717 |
| HPV56 | L1 | 11 | 11 | DPPLHYGLCIF | 17718 |
| HPV56 | L1 | 318 | 8 | EPPPSSVY | 17719 |
| HPV56 | L1 | 318 | 9 | EPPPSSVYV | 17720 |
| HPV56 | L1 | 318 | 10 | EPPPSSVYVA | 17721 |
| HPV56 | L1 | 30 | 8 | FPIFLQMA | 17722 |
| HPV56 | L1 | 30 | 10 | FPIFLQMATW | 17723 |
| HPV56 | L1 | 495 | 8 | FPLGRKFL | 17724 |
| HPV56 | L1 | 495 | 9 | FPLGRKFLM | 17725 |
| HPV56 | L1 | 495 | 11 | FPLGRKFLMQL | 17726 |
| HPV56 | L1 | 96 | 9 | IPKVSAYQY | 17727 |
| HPV56 | L1 | 96 | 11 | IPKVSAYQYRV | 17728 |
| HPV56 | L1 | 343 | 8 | KPYWLQRA | 17729 |
| HPV56 | L1 | 111 | 9 | LPDPNKFGL | 17730 |
| HPV56 | L1 | 48 | 9 | LPPTPVSKV | 17731 |
| HPV56 | L1 | 48 | 10 | LPPTPVSKVV | 17732 |
| HPV56 | L1 | 48 | 11 | LPPTPVSKVVA | 17733 |
| HPV56 | L1 | 126 | 8 | NPDQERLV | 17734 |
| HPV56 | L1 | 126 | 9 | NPDQERLVW | 17735 |
| HPV56 | L1 | 126 | 10 | NPDQERLVWA | 17736 |
| HPV56 | L1 | 220 | 10 | PPLALINTPI | 17737 |
| HPV56 | L1 | 12 | 9 | PPLHYGLCI | 17738 |
| HPV56 | L1 | 12 | 10 | PPLHYGLCIF | 17739 |
| HPV56 | L1 | 12 | 11 | PPLHYGLCIFL | 17740 |
| HPV56 | L1 | 319 | 8 | PPPSSVYV | 17741 |
| HPV56 | L1 | 319 | 9 | PPPSSVYVA | 17742 |
| HPV56 | L1 | 320 | 8 | PPSSVYVA | 17743 |
| HPV56 | L1 | 466 | 9 | PPTEKQDPL | 17744 |
| HPV56 | L1 | 466 | 10 | PPTEKQDPLA | 17745 |
| HPV56 | L1 | 49 | 8 | PPTPVSKV | 17746 |
| HPV56 | L1 | 49 | 9 | PPTPVSKVV | 17747 |
| HPV56 | L1 | 49 | 10 | PPTPVSKVVA | 17748 |
| HPV56 | L1 | 441 | 11 | PPVATSLEDKY | 17749 |
| HPV56 | L1 | 465 | 10 | QPPTEKQDPL | 17750 |
| HPV56 | L1 | 465 | 11 | QPPTEKQDPLA | 17751 |
| HPV56 | L1 | 40 | 8 | RPSENKVY | 17752 |
| HPV56 | L1 | 40 | 9 | RPSENKVYL | 17753 |
| HPV56 | L1 | 440 | 8 | SPPVATSL | 17754 |
| HPV56 | L1 | 196 | 8 | TPAMGEHW | 17755 |
| HPV56 | L1 | 227 | 8 | TPIEDGDM | 17756 |
| HPV56 | L1 | 227 | 9 | TPIEDGDMI | 17757 |
| HPV56 | L1 | 328 | 11 | TPSGSMITSEA | 17758 |
| HPV56 | L1 | 51 | 8 | TPVSKVVA | 17759 |
| HPV56 | L1 | 265 | 9 | YPDYLKMSA | 17760 |
| HPV56 | L1 | 265 | 11 | YPDYLKMSADA | 17761 |
| HPV56 | L2 | 271 | 9 | APDPDFMNI | 17762 |
| HPV56 | L2 | 271 | 10 | APDPDFMNIV | 17763 |
| HPV56 | L2 | 271 | 11 | APDPDFMNIVA | 17764 |
| HPV56 | L2 | 358 | 9 | APGLSSQSV | 17765 |
| HPV56 | L2 | 358 | 10 | APGLSSQSVA | 17766 |
| HPV56 | L2 | 391 | 11 | APLGNVWETPF | 17767 |
| HPV56 | L2 | 170 | 11 | APQTGEVSGNI | 17768 |
| HPV56 | L2 | 223 | 8 | APRLYRKA | 17769 |
| HPV56 | L2 | 223 | 9 | APRLYRKAF | 17770 |
| HPV56 | L2 | 27 | 9 | CPEDVVNKI | 17771 |
| HPV56 | L2 | 238 | 9 | DPAFLDRPA | 17772 |
| HPV56 | L2 | 238 | 11 | DPAFLDRPATL | 17773 |
| HPV56 | L2 | 273 | 8 | DPDFMNIV | 17774 |
| HPV56 | L2 | 273 | 9 | DPDFMNIVA | 17775 |
| HPV56 | L2 | 273 | 10 | DPDFMNIVAL | 17776 |
| HPV56 | L2 | 100 | 8 | DPSIVTLV | 17777 |

TABLE XI-continued

| | | | | | |
|---|---|---|---|---|---|
| HPV56 | L2 | 208 | 8 | EPISSTPI | 17778 |
| HPV56 | L2 | 208 | 11 | EPISSTPIPGF | 17779 |
| HPV56 | L2 | 412 | 8 | GPSTWPFV | 17780 |
| HPV56 | L2 | 97 | 8 | GPTDPSIV | 17781 |
| HPV56 | L2 | 97 | 10 | GPTDPSIVTL | 17782 |
| HPV56 | L2 | 97 | 11 | GPTDPSIVTLV | 17783 |
| HPV56 | L2 | 215 | 8 | IPGFRRIA | 17784 |
| HPV56 | L2 | 215 | 9 | IPGFRRIAA | 17785 |
| HPV56 | L2 | 195 | 8 | IPMQTFAV | 17786 |
| HPV56 | L2 | 119 | 10 | IPNFTGSGGF | 17787 |
| HPV56 | L2 | 453 | 10 | IPYFFADGDV | 17788 |
| HPV56 | L2 | 453 | 11 | IPYFFADGDVA | 17789 |
| HPV56 | L2 | 376 | 8 | KPSTLSFA | 17790 |
| HPV56 | L2 | 373 | 8 | LPIKPSTL | 17791 |
| HPV56 | L2 | 373 | 10 | LPIKPSTLSF | 17792 |
| HPV56 | L2 | 373 | 11 | LPIKPSTLSFA | 17793 |
| HPV56 | L2 | 409 | 8 | LPTGPSTW | 17794 |
| HPV56 | L2 | 409 | 10 | LPTGPSTWPF | 17795 |
| HPV56 | L2 | 409 | 11 | LPTGPSTWPFV | 17796 |
| HPV56 | L2 | 253 | 11 | NPLFEGTDTSL | 17797 |
| HPV56 | L2 | 159 | 9 | NPLFIDPPV | 17798 |
| HPV56 | L2 | 159 | 10 | NPLFIDPPVI | 17799 |
| HPV56 | L2 | 89 | 8 | PPIVVESV | 17800 |
| HPV56 | L2 | 335 | 10 | QPLLSANNSF | 17801 |
| HPV56 | L2 | 284 | 11 | RPAFTTRRGGV | 17802 |
| HPV56 | L2 | 244 | 8 | RPATLVSA | 17803 |
| HPV56 | L2 | 88 | 9 | RPPIVVESV | 17804 |
| HPV56 | L2 | 77 | 8 | RPSTIVDV | 17805 |
| HPV56 | L2 | 77 | 11 | RPSTIVDVTPA | 17806 |
| HPV56 | L2 | 324 | 9 | SPIAQAEEI | 17807 |
| HPV56 | L2 | 324 | 11 | SPIAQAEEIEM | 17808 |
| HPV56 | L2 | 266 | 11 | SPSGVAPDPDF | 17809 |
| HPV56 | L2 | 422 | 9 | SPYDVTHDV | 17810 |
| HPV56 | L2 | 422 | 10 | SPYDVTHDVY | 17811 |
| HPV56 | L2 | 422 | 11 | SPYDVTHDVYI | 17812 |
| HPV56 | L2 | 85 | 8 | TPARPPIV | 17813 |
| HPV56 | L2 | 85 | 9 | TPARPPIVV | 17814 |
| HPV56 | L2 | 399 | 9 | TPFYSGPDI | 17815 |
| HPV56 | L2 | 399 | 10 | TPFYSGPDIV | 17816 |
| HPV56 | L2 | 399 | 11 | TPFYSGPDIVL | 17817 |
| HPV56 | L2 | 213 | 9 | TPIPGFRRI | 17818 |
| HPV56 | L2 | 213 | 10 | TPIPGFRRIA | 17819 |
| HPV56 | L2 | 213 | 11 | TPIPGFRRIAA | 17820 |
| HPV56 | L2 | 368 | 8 | TPSAHLPI | 17821 |
| HPV56 | L2 | 184 | 9 | TPTSGIHSY | 17822 |
| HPV56 | L2 | 144 | 9 | TPTSSTVHV | 17823 |
| HPV56 | L2 | 72 | 10 | VPLGSRPSTI | 17824 |
| HPV56 | L2 | 72 | 11 | VPLGSRPSTIV | 17825 |
| HPV56 | L2 | 419 | 8 | VPQSPYDV | 17826 |
| HPV56 | L2 | 416 | 9 | WPFVPQSPY | 17827 |
| HPV56 | L2 | 416 | 11 | WPFVPQSPYDV | 17828 |

B27 Supermotif Peptides

| Type | Protein | No. of Amino Acids | Position | Sequence | Seq. Id. No. |
|---|---|---|---|---|---|
| HPV16 | E1 | 10 | 67 | AHALFTAQEA | 17829 |
| HPV16 | E1 | 9 | 203 | AKAAMLAKF | 17830 |
| HPV16 | E1 | 9 | 209 | AKFKELYGV | 17831 |
| HPV16 | E1 | 11 | 209 | AKFKELYGVSF | 17832 |
| HPV16 | E1 | 9 | 516 | AKIGMLDDA | 17833 |
| HPV16 | E1 | 11 | 516 | AKIGMLDDATV | 17834 |
| HPV16 | E1 | 8 | 399 | AKIVKDCA | 17835 |
| HPV16 | E1 | 10 | 399 | AKIVKDCATM | 17836 |
| HPV16 | E1 | 8 | 76 | AKQHRDAV | 17837 |
| HPV16 | E1 | 10 | 76 | AKQHRDAVQV | 17838 |
| HPV16 | E1 | 11 | 76 | AKQHRDAVQVL | 17839 |
| HPV16 | E1 | 9 | 627 | DKENDGDSL | 17840 |
| HPV16 | E1 | 8 | 606 | DKNWKSFF | 17841 |
| HPV16 | E1 | 9 | 431 | DRVDDGGDW | 17842 |
| HPV16 | E1 | 10 | 416 | EKKQMSMSQW | 17843 |
| HPV16 | E1 | 11 | 416 | EKKQMSMSQWI | 17844 |
| HPV16 | E1 | 8 | 26 | EKKTGDAI | 17845 |
| HPV16 | E1 | 8 | 291 | EKLLSKLL | 17846 |
| HPV16 | E1 | 10 | 291 | EKLLSKLLCV | 17847 |
| HPV16 | E1 | 11 | 116 | EKQSRAAKRRL | 17848 |
| HPV16 | E1 | 10 | 182 | ERHTICQTPL | 17849 |
| HPV16 | E1 | 9 | 211 | FKELYGVSF | 17850 |

TABLE XI-continued

| | | | | | |
|---|---|---|---|---|---|
| HPV16 | E1 | 11 | 226 | FKSNKSTCCDW | 17851 |
| HPV16 | E1 | 10 | 284 | GKNRETIEKL | 17852 |
| HPV16 | E1 | 11 | 284 | GKNRETIEKLL | 17853 |
| HPV16 | E1 | 9 | 482 | GKSLFGMSL | 17854 |
| HPV16 | E1 | 10 | 482 | GKSLFGMSLM | 17855 |
| HPV16 | E1 | 8 | 79 | HRDAVQVL | 17856 |
| HPV16 | E1 | 8 | 251 | IKTLLQQY | 17857 |
| HPV16 | E1 | 10 | 251 | IKTLLQQYCL | 17858 |
| HPV16 | E1 | 11 | 251 | IKTLLQQYCLY | 17859 |
| HPV16 | E1 | 8 | 426 | IKYRCDRV | 17860 |
| HPV16 | E1 | 8 | 550 | KHRPLVQL | 17861 |
| HPV16 | E1 | 8 | 469 | KKNCILLY | 17862 |
| HPV16 | E1 | 10 | 469 | KKNCILLYGA | 17863 |
| HPV16 | E1 | 11 | 469 | KKNCILLYGAA | 17864 |
| HPV16 | E1 | 9 | 417 | KKQMSMSQW | 17865 |
| HPV16 | E1 | 10 | 417 | KKQMSMSQWI | 17866 |
| HPV16 | E1 | 8 | 413 | KRAEKKQM | 17867 |
| HPV16 | E1 | 10 | 413 | KRAEKKQMSM | 17868 |
| HPV16 | E1 | 9 | 87 | KRKYLVSPL | 17869 |
| HPV16 | E1 | 10 | 262 | LHIQSLACSW | 17870 |
| HPV16 | E1 | 8 | 579 | LHNRLVVF | 17871 |
| HPV16 | E1 | 10 | 579 | LHNRLVVFTF | 17872 |
| HPV16 | E1 | 8 | 557 | LKCPPLLI | 17873 |
| HPV16 | E1 | 8 | 460 | LKRFLQGI | 17874 |
| HPV16 | E1 | 10 | 86 | LKRKYLVSPL | 17875 |
| HPV16 | E1 | 9 | 393 | LKSNSQAKI | 17876 |
| HPV16 | E1 | 10 | 393 | LKSNSQAKIV | 17877 |
| HPV16 | E1 | 8 | 198 | LKTSNAKA | 17878 |
| HPV16 | E1 | 9 | 198 | LKTSNAKAA | 17879 |
| HPV16 | E1 | 10 | 198 | LKTSNAKAAM | 17880 |
| HPV16 | E1 | 11 | 198 | LKTSNAKAAML | 17881 |
| HPV16 | E1 | 9 | 536 | LRNALDGNL | 17882 |
| HPV16 | E1 | 10 | 536 | LRNALDGNLV | 17883 |
| HPV16 | E1 | 8 | 312 | LRSTAAAL | 17884 |
| HPV16 | E1 | 9 | 312 | LRSTAAALY | 17885 |
| HPV16 | E1 | 10 | 312 | LRSTAAALYW | 17886 |
| HPV16 | E1 | 11 | 312 | LRSTAAALYWY | 17887 |
| HPV16 | E1 | 8 | 446 | LRYQGVEF | 17888 |
| HPV16 | E1 | 9 | 446 | LRYQGVEFM | 17889 |
| HPV16 | E1 | 11 | 446 | LRYQGVEFMSF | 17890 |
| HPV16 | E1 | 8 | 491 | MKFLQGSV | 17891 |
| HPV16 | E1 | 9 | 491 | MKFLQGSVI | 17892 |
| HPV16 | E1 | 11 | 491 | MKFLQGSVICF | 17893 |
| HPV16 | E1 | 8 | 229 | NKSTCCDW | 17894 |
| HPV16 | E1 | 10 | 229 | NKSTCCDWCI | 17895 |
| HPV16 | E1 | 11 | 229 | NKSTCCDWCIA | 17896 |
| HPV16 | E1 | 8 | 286 | NRETIEKL | 17897 |
| HPV16 | E1 | 9 | 286 | NRETIEKLL | 17898 |
| HPV16 | E1 | 8 | 581 | NRLVVFTF | 17899 |
| HPV16 | E1 | 8 | 468 | PKKNCILL | 17900 |
| HPV16 | E1 | 9 | 468 | PKKNCILLY | 17901 |
| HPV16 | E1 | 11 | 468 | PKKNCILLYGA | 17902 |
| HPV16 | E1 | 8 | 310 | PKLRSTAA | 17903 |
| HPV16 | E1 | 9 | 310 | PKLRSTAAA | 17904 |
| HPV16 | E1 | 10 | 310 | PKLRSTAAAL | 17905 |
| HPV16 | E1 | 11 | 310 | PKLRSTAAALY | 17906 |
| HPV16 | E1 | 8 | 108 | PRLKAICI | 17907 |
| HPV16 | E1 | 8 | 78 | QHRDAVQV | 17908 |
| HPV16 | E1 | 9 | 78 | QHRDAVQVL | 17909 |
| HPV16 | E1 | 9 | 347 | QHSFNDCTF | 17910 |
| HPV16 | E1 | 11 | 347 | QHSFNDCTFEL | 17911 |
| HPV16 | E1 | 10 | 341 | QRQTVLQHSF | 17912 |
| HPV16 | E1 | 11 | 150 | RHETETPCSQY | 17913 |
| HPV16 | E1 | 9 | 183 | RHTICQTPL | 17914 |
| HPV16 | E1 | 11 | 410 | RHYKRAEKKQM | 17915 |
| HPV16 | E1 | 8 | 88 | RKYLVSPL | 17916 |
| HPV16 | E1 | 11 | 88 | RKYLVSPLSDI | 17917 |
| HPV16 | E1 | 11 | 124 | RRLFESEDSGY | 17918 |
| HPV16 | E1 | 8 | 506 | SHFWLQPL | 17919 |
| HPV16 | E1 | 9 | 506 | SHFWLQPLA | 17920 |
| HPV16 | E1 | 11 | 506 | SHFWLQPLADA | 17921 |
| HPV16 | E1 | 9 | 295 | SKLLCVSPM | 17922 |
| HPV16 | E1 | 11 | 295 | SKLLCVSPMCM | 17923 |
| HPV16 | E1 | 10 | 504 | SKSHFWLQPL | 17924 |
| HPV16 | E1 | 11 | 504 | SKSHFWLQPLA | 17925 |
| HPV16 | E1 | 8 | 119 | SRAAKRRL | 17926 |
| HPV16 | E1 | 9 | 119 | SRAAKRRLF | 17927 |
| HPV16 | E1 | 9 | 614 | SRTWSRLSL | 17928 |
| HPV16 | E1 | 10 | 574 | SRWPYLHNRL | 17929 |

TABLE XI-continued

| | | | | | |
|---|---|---|---|---|---|
| HPV16 | E1 | 11 | 574 | SRWPYLHNRLV | 17930 |
| HPV16 | E1 | 11 | 402 | VKDCATMCRHY | 17931 |
| HPV16 | E1 | 9 | 549 | VKHRPLVQL | 17932 |
| HPV16 | E1 | 8 | 439 | WKQIVMFL | 17933 |
| HPV16 | E1 | 10 | 439 | WKQIVMFLRY | 17934 |
| HPV16 | E1 | 9 | 609 | WKSFFSRTW | 17935 |
| HPV16 | E1 | 10 | 281 | YKCGKNRETI | 17936 |
| HPV16 | E1 | 9 | 412 | YKRAEKKQM | 17937 |
| HPV16 | E1 | 11 | 412 | YKRAEKKQMSM | 17938 |
| HPV16 | E1 | 8 | 322 | YKTGISNI | 17939 |
| HPV16 | E1 | 11 | 322 | YKTGISNISEV | 17940 |
| HPV16 | E2 | 9 | 46 | AREMGFKHI | 17941 |
| HPV16 | E2 | 9 | 28 | DHIDYWKHM | 17942 |
| HPV16 | E2 | 11 | 28 | DHIDYWKHMRL | 17943 |
| HPV16 | E2 | 8 | 90 | EKWTLQDV | 17944 |
| HPV16 | E2 | 10 | 90 | EKWTLQDVSL | 17945 |
| HPV16 | E2 | 8 | 176 | EKYSKNKV | 17946 |
| HPV16 | E2 | 9 | 176 | EKYSKNKVW | 17947 |
| HPV16 | E2 | 11 | 176 | EKYSKNKVWEV | 17948 |
| HPV16 | E2 | 8 | 171 | FKDDAEKY | 17949 |
| HPV16 | E2 | 8 | 51 | FKHINHQV | 17950 |
| HPV16 | E2 | 9 | 51 | FKHINHQVV | 17951 |
| HPV16 | E2 | 8 | 305 | FKKHCTLY | 17952 |
| HPV16 | E2 | 10 | 305 | FKKHCTLYTA | 17953 |
| HPV16 | E2 | 11 | 305 | FKKHCTLYTAV | 17954 |
| HPV16 | E2 | 9 | 323 | GHNVKHKSA | 17955 |
| HPV16 | E2 | 10 | 323 | GHNVKHKSAI | 17956 |
| HPV16 | E2 | 11 | 323 | GHNVKHKSAIV | 17957 |
| HPV16 | E2 | 8 | 328 | HKSAIVTL | 17958 |
| HPV16 | E2 | 10 | 328 | HKSAIVTLTY | 17959 |
| HPV16 | E2 | 8 | 258 | HRDSVDSA | 17960 |
| HPV16 | E2 | 10 | 258 | HRDSVDSAPI | 17961 |
| HPV16 | E2 | 11 | 258 | HRDSVDSAPIL | 17962 |
| HPV16 | E2 | 8 | 110 | IKKHGYTV | 17963 |
| HPV16 | E2 | 10 | 110 | IKKHGYTVEV | 17964 |
| HPV16 | E2 | 10 | 211 | IRQHLANHPA | 17965 |
| HPV16 | E2 | 11 | 211 | IRQHLANHPAA | 17966 |
| HPV16 | E2 | 8 | 164 | IRTYFVQF | 17967 |
| HPV16 | E2 | 8 | 307 | KHCTLYTA | 17968 |
| HPV16 | E2 | 9 | 307 | KHCTLYTAV | 17969 |
| HPV16 | E2 | 8 | 112 | KHGYTVEV | 17970 |
| HPV16 | E2 | 10 | 112 | KHGYTVEVQF | 17971 |
| HPV16 | E2 | 8 | 52 | KHINHQVV | 17972 |
| HPV16 | E2 | 11 | 52 | KHINHQVVPTL | 17973 |
| HPV16 | E2 | 9 | 327 | KHKSAIVTL | 17974 |
| HPV16 | E2 | 11 | 327 | KHKSAIVTLTY | 17975 |
| HPV16 | E2 | 8 | 34 | KHMRLECA | 17976 |
| HPV16 | E2 | 9 | 34 | KHMRLECAI | 17977 |
| HPV16 | E2 | 10 | 34 | KHMRLECAIY | 17978 |
| HPV16 | E2 | 11 | 34 | KHMRLECAIYY | 17979 |
| HPV16 | E2 | 9 | 306 | KKHCTLYTA | 17980 |
| HPV16 | E2 | 10 | 306 | KKHCTLYTAV | 17981 |
| HPV16 | E2 | 9 | 111 | KKHGYTVEV | 17982 |
| HPV16 | E2 | 11 | 111 | KKHGYTVEVQF | 17983 |
| HPV16 | E2 | 9 | 257 | LHRDSVDSA | 17984 |
| HPV16 | E2 | 11 | 257 | LHRDSVDSAPI | 17985 |
| HPV16 | E2 | 8 | 298 | LKCLRYRF | 17986 |
| HPV16 | E2 | 8 | 291 | LKGDANTL | 17987 |
| HPV16 | E2 | 11 | 291 | LKGDANTLKCL | 17988 |
| HPV16 | E2 | 8 | 26 | LRDHIDYW | 17989 |
| HPV16 | E2 | 11 | 26 | LRDHIDYWKHM | 17990 |
| HPV16 | E2 | 11 | 301 | LRYRFKKHCTL | 17991 |
| HPV16 | E2 | 9 | 129 | MHYTNWTHI | 17992 |
| HPV16 | E2 | 10 | 129 | MHYTNWTHIY | 17993 |
| HPV16 | E2 | 11 | 129 | MHYTNWTHIYI | 17994 |
| HPV16 | E2 | 8 | 36 | MRLECAIY | 17995 |
| HPV16 | E2 | 9 | 36 | MRLECAIYY | 17996 |
| HPV16 | E2 | 11 | 36 | MRLECAIYYKA | 17997 |
| HPV16 | E2 | 10 | 217 | NHPAATHTKA | 17998 |
| HPV16 | E2 | 11 | 217 | NHPAATHTKAV | 17999 |
| HPV16 | E2 | 8 | 55 | NHQVVPTL | 18000 |
| HPV16 | E2 | 9 | 55 | NHQVVPTLA | 18001 |
| HPV16 | E2 | 10 | 55 | NHQVVPTLAV | 18002 |
| HPV16 | E2 | 9 | 67 | NKALQAIEL | 18003 |
| HPV16 | E2 | 11 | 67 | NKALQAIELQL | 18004 |
| HPV16 | E2 | 8 | 181 | NKVWEVHA | 18005 |
| HPV16 | E2 | 10 | 353 | PKTITVSTGF | 18006 |
| HPV16 | E2 | 11 | 353 | PKTITVSTGFM | 18007 |
| HPV16 | E2 | 8 | 213 | QHLANHPA | 18008 |

TABLE XI-continued

| | | | | | |
|---|---|---|---|---|---|
| HPV16 | E2 | 9 | 213 | QHLANHPAA | 18009 |
| HPV16 | E2 | 9 | 342 | QRDQFLSQV | 18010 |
| HPV16 | E2 | 11 | 342 | QRDQFLSQVKI | 18011 |
| HPV16 | E2 | 10 | 6 | QRLNVCQDKI | 18012 |
| HPV16 | E2 | 11 | 6 | QRLNVCQDKIL | 18013 |
| HPV16 | E2 | 8 | 65 | SKNKALQA | 18014 |
| HPV16 | E2 | 9 | 65 | SKNKALQAI | 18015 |
| HPV16 | E2 | 11 | 65 | SKNKALQAIEL | 18016 |
| HPV16 | E2 | 8 | 179 | SKNKVWEV | 18017 |
| HPV16 | E2 | 10 | 179 | SKNKVWEVHA | 18018 |
| HPV16 | E2 | 9 | 135 | THIYICEEA | 18019 |
| HPV16 | E2 | 11 | 135 | THIYICEEASV | 18020 |
| HPV16 | E2 | 8 | 222 | THTKAVAL | 18021 |
| HPV16 | E2 | 10 | 17 | THYENDSTDL | 18022 |
| HPV16 | E2 | 9 | 254 | TKLLHRDSV | 18023 |
| HPV16 | E2 | 8 | 186 | VHAGGQVI | 18024 |
| HPV16 | E2 | 9 | 186 | VHAGGQVIL | 18025 |
| HPV16 | E2 | 8 | 160 | VHEGIRTY | 18026 |
| HPV16 | E2 | 9 | 160 | VHEGIRTYF | 18027 |
| HPV16 | E2 | 10 | 160 | VHEGIRTYFV | 18028 |
| HPV16 | E2 | 10 | 289 | VHLKGDANTL | 18029 |
| HPV16 | E2 | 8 | 326 | VKHKSAIV | 18030 |
| HPV16 | E2 | 10 | 326 | VKHKSMVTL | 18031 |
| HPV16 | E2 | 9 | 350 | VKIPKTITV | 18032 |
| HPV16 | E2 | 8 | 319 | WHWTGHNV | 18033 |
| HPV16 | E2 | 9 | 33 | WKHMRLECA | 18034 |
| HPV16 | E2 | 10 | 33 | WKHMRLECAI | 18035 |
| HPV16 | E2 | 11 | 33 | WKHMRLECAIY | 18036 |
| HPV16 | E2 | 8 | 44 | YKAREMGF | 18037 |
| HPV16 | E2 | 11 | 44 | YKAREMGFKHI | 18038 |
| HPV16 | E2 | 9 | 303 | YRFKKHCTL | 18039 |
| HPV16 | E2 | 10 | 303 | YRFKKHCTLY | 18040 |
| HPV16 | E5 | 8 | 57 | FRCFIVYI | 18041 |
| HPV16 | E5 | 9 | 57 | FRCFIVYII | 18042 |
| HPV16 | E5 | 10 | 57 | FRCFIVYIIF | 18043 |
| HPV16 | E5 | 11 | 57 | FRCFIVYIIFV | 18044 |
| HPV16 | E5 | 8 | 74 | IHTHARFL | 18045 |
| HPV16 | E5 | 9 | 74 | IHTHARFLI | 18046 |
| HPV16 | E5 | 8 | 29 | IRPLLLSV | 18047 |
| HPV16 | E5 | 11 | 29 | IRPLLLSVSTY | 18048 |
| HPV16 | E6 | 10 | 40 | CKQQLLRREV | 18049 |
| HPV16 | E6 | 11 | 40 | CKQQLLRREVY | 18050 |
| HPV16 | E6 | 10 | 71 | DKCLKFYSKI | 18051 |
| HPV16 | E6 | 9 | 127 | DKKQRFHNI | 18052 |
| HPV16 | E6 | 9 | 14 | ERPRKLPQL | 18053 |
| HPV16 | E6 | 8 | 132 | FHNIRGRW | 18054 |
| HPV16 | E6 | 8 | 54 | FRDLCIVY | 18055 |
| HPV16 | E6 | 8 | 137 | GRWTGRCM | 18056 |
| HPV16 | E6 | 9 | 30 | IHDIILECV | 18057 |
| HPV16 | E6 | 10 | 30 | IHDIILECVY | 18058 |
| HPV16 | E6 | 10 | 108 | IRCINCQKPL | 18059 |
| HPV16 | E6 | 10 | 135 | IRGRWTGRCM | 18060 |
| HPV16 | E6 | 8 | 128 | KKQRFHNI | 18061 |
| HPV16 | E6 | 10 | 74 | LKFYSKISEY | 18062 |
| HPV16 | E6 | 8 | 45 | LRREVYDF | 18063 |
| HPV16 | E6 | 9 | 45 | LRREVYDFA | 18064 |
| HPV16 | E6 | 10 | 45 | LRREVYDFAF | 18065 |
| HPV16 | E6 | 8 | 1 | MHQKRTAM | 18066 |
| HPV16 | E6 | 9 | 1 | MHQKRTAMF | 18067 |
| HPV16 | E6 | 8 | 100 | NKPLCDLL | 18068 |
| HPV16 | E6 | 9 | 100 | NKPLCDLLI | 18069 |
| HPV16 | E6 | 11 | 16 | PRKLPQLCTEL | 18070 |
| HPV16 | E6 | 10 | 130 | QRFHNIRGRW | 18071 |
| HPV16 | E6 | 10 | 123 | QRHLDKKQRF | 18072 |
| HPV16 | E6 | 9 | 124 | RHLDKKQRF | 18073 |
| HPV16 | E6 | 8 | 84 | RHYCYSLY | 18074 |
| HPV16 | E6 | 10 | 17 | RKLPQLCTEL | 18075 |
| HPV16 | E6 | 8 | 46 | RREVYDFA | 18076 |
| HPV16 | E6 | 9 | 46 | RREVYDFAF | 18077 |
| HPV16 | E6 | 9 | 78 | SKISEYRHY | 18078 |
| HPV16 | E6 | 11 | 78 | SKISEYRHYCY | 18079 |
| HPV16 | E6 | 9 | 150 | SRTRRETQL | 18080 |
| HPV16 | E6 | 8 | 61 | YRDGNPYA | 18081 |
| HPV16 | E6 | 9 | 61 | YRDGNPYAV | 18082 |
| HPV16 | E6 | 8 | 83 | YRHYCYSL | 18083 |
| HPV16 | E6 | 9 | 83 | YRHYCYSLY | 18084 |
| HPV16 | E7 | 8 | 50 | AHYNIVTF | 18085 |
| HPV16 | E7 | 9 | 59 | CKCDSTLRL | 18086 |
| HPV16 | E7 | 11 | 59 | CKCDSTLRLCV | 18087 |

TABLE XI-continued

| | | | | | |
|---|---|---|---|---|---|
| HPV16 | E7 | 8 | 48 | DRAHYNIV | 18088 |
| HPV16 | E7 | 10 | 48 | DRAHYNIVTF | 18089 |
| HPV16 | E7 | 8 | 76 | IRTLEDLL | 18090 |
| HPV16 | E7 | 9 | 76 | IRTLEDLLM | 18091 |
| HPV16 | E7 | 8 | 8 | LHEYMLDL | 18092 |
| HPV16 | E7 | 10 | 65 | LRLCVQSTHV | 18093 |
| HPV16 | E7 | 8 | 1 | MHGDTPTL | 18094 |
| HPV16 | E7 | 11 | 1 | MHGDTPTLHEY | 18095 |
| HPV16 | E7 | 8 | 72 | THVDIRTL | 18096 |
| HPV16 | E7 | 11 | 72 | THVDIRTLEDL | 18097 |
| HPV16 | L1 | 8 | 524 | AKRKKRKL | 18098 |
| HPV16 | L1 | 9 | 55 | ARTNIYYHA | 18099 |
| HPV16 | L1 | 9 | 405 | CKITLTADV | 18100 |
| HPV16 | L1 | 10 | 405 | CKITLTADVM | 18101 |
| HPV16 | L1 | 9 | 187 | CKPPIGEHW | 18102 |
| HPV16 | L1 | 9 | 255 | CKYPDYIKM | 18103 |
| HPV16 | L1 | 10 | 255 | CKYPDYIKMV | 18104 |
| HPV16 | L1 | 10 | 479 | EKFSADLDQF | 18105 |
| HPV16 | L1 | 11 | 386 | FKEYLRHGEEY | 18106 |
| HPV16 | L1 | 11 | 99 | FRIHLPDPNKF | 18107 |
| HPV16 | L1 | 8 | 344 | GHNNGICW | 18108 |
| HPV16 | L1 | 8 | 145 | GHPLLNKL | 18109 |
| HPV16 | L1 | 9 | 196 | GKGSPCTNV | 18110 |
| HPV16 | L1 | 10 | 196 | GKGSPCTNVA | 18111 |
| HPV16 | L1 | 11 | 196 | GKGSPCTNVAV | 18112 |
| HPV16 | L1 | 8 | 134 | GRGQPLGV | 18113 |
| HPV16 | L1 | 10 | 134 | GRGQPLGVGI | 18114 |
| HPV16 | L1 | 8 | 491 | GRKFLLQA | 18115 |
| HPV16 | L1 | 10 | 491 | GRKFLLQAGL | 18116 |
| HPV16 | Li | 9 | 101 | IHLPDPNKF | 18117 |
| HPV16 | L1 | 11 | 101 | IHLPDPNKFGF | 18118 |
| HPV16 | L1 | 8 | 417 | IHSMNSTI | 18119 |
| HPV16 | L1 | 9 | 417 | IHSMNSTIL | 18120 |
| HPV16 | L1 | 8 | 303 | IKGSGSTA | 18121 |
| HPV16 | L1 | 10 | 303 | IKGSGSTANL | 18122 |
| HPV16 | L1 | 11 | 303 | IKGSGSTANLA | 18123 |
| HPV16 | L1 | 9 | 78 | IKKPNNNKI | 18124 |
| HPV16 | L1 | 10 | 78 | IKKPNNNKIL | 18125 |
| HPV16 | L1 | 11 | 78 | IKKPNNNKILV | 18126 |
| HPV16 | L1 | 8 | 261 | IKMVSEPY | 18127 |
| HPV16 | L1 | 8 | 79 | KKPNNNKI | 18128 |
| HPV16 | L1 | 9 | 79 | KKPNNNKIL | 18129 |
| HPV16 | L1 | 10 | 79 | KKPNNNKILV | 18130 |
| HPV16 | L1 | 8 | 468 | KKYTFWEV | 18131 |
| HPV16 | L1 | 10 | 468 | KKYTFWEVNL | 18132 |
| HPV16 | L1 | 9 | 500 | LKAKPKFTL | 18133 |
| HPV16 | L1 | 9 | 477 | LKEKFSADL | 18134 |
| HPV16 | L1 | 9 | 467 | LKKYTFWEV | 18135 |
| HPV16 | L1 | 11 | 467 | LKKYTFWEVNL | 18136 |
| HPV16 | L1 | 9 | 390 | LRHGEEYDL | 18137 |
| HPV16 | L1 | 11 | 390 | LRHGEEYDLQF | 18138 |
| HPV16 | L1 | 8 | 276 | LRREQMFV | 18139 |
| HPV16 | L1 | 11 | 276 | LRREQMFVRHL | 18140 |
| HPV16 | L1 | 10 | 107 | NKFGFPDTSF | 18141 |
| HPV16 | L1 | 11 | 107 | NKFGFPDTSFY | 18142 |
| HPV16 | L1 | 8 | 84 | NKILVPKV | 18143 |
| HPV16 | L1 | 11 | 84 | NKILVPKVSGL | 18144 |
| HPV16 | L1 | 9 | 150 | NKLDDTENA | 18145 |
| HPV16 | L1 | 11 | 150 | NKLDDTENASA | 18146 |
| HPV16 | L1 | 9 | 334 | NKPYWLQRA | 18147 |
| HPV16 | L1 | 9 | 242 | NKSEVPLDI | 18148 |
| HPV16 | L1 | 10 | 288 | NRAGAVGENV | 18149 |
| HPV16 | L1 | 9 | 169 | NRECISMDY | 18150 |
| HPV16 | L1 | 9 | 462 | PKEDPLKKY | 18151 |
| HPV16 | L1 | 11 | 462 | PKEDPLKKYTF | 18152 |
| HPV16 | L1 | 10 | 504 | PKFTLGKRKA | 18153 |
| HPV16 | L1 | 8 | 89 | PKVSGLQY | 18154 |
| HPV16 | L1 | 10 | 89 | PKVSGLQYRV | 18155 |
| HPV16 | L1 | 11 | 89 | PKVSGLQYRVF | 18156 |
| HPV16 | L1 | 10 | 340 | QRAQGHNNGI | 18157 |
| HPV16 | L1 | 8 | 122 | QRLVWACV | 18158 |
| HPV16 | L1 | 10 | 122 | QRLVWACVGV | 18159 |
| HPV16 | L1 | 8 | 391 | RHGEEYDL | 18160 |
| HPV16 | L1 | 10 | 391 | RHGEEYDLQF | 18161 |
| HPV16 | L1 | 11 | 391 | RHGEEYDLQFI | 18162 |
| HPV16 | L1 | 9 | 284 | RHLFNRAGA | 18163 |
| HPV16 | L1 | 10 | 284 | RHLFNRAGAV | 18164 |
| HPV16 | L1 | 9 | 492 | RKFLLQAGL | 18165 |
| HPV16 | L1 | 11 | 492 | RKFLLQAGLKA | 18166 |

TABLE XI-continued

| | | | | | |
|---|---|---|---|---|---|
| HPV16 | L1 | 10 | 277 | RREQMFVRHL | 18167 |
| HPV16 | L1 | 11 | 277 | RREQMFVRHLF | 18168 |
| HPV16 | L1 | 9 | 45 | SKVVSTDEY | 18169 |
| HPV16 | L1 | 10 | 45 | SKVVSTDEYV | 18170 |
| HPV16 | L1 | 11 | 45 | SKVVSTDEYVA | 18171 |
| HPV16 | L1 | 10 | 66 | SRLLAVGHPY | 18172 |
| HPV16 | L1 | 11 | 66 | SRLLAVGHPYF | 18173 |
| HPV16 | L1 | 8 | 363 | TRSTNMSL | 18174 |
| HPV16 | L1 | 10 | 363 | TRSTNMSLCA | 18175 |
| HPV16 | L1 | 11 | 363 | TRSTNMSLCAA | 18176 |
| HPV16 | L1 | 8 | 283 | VRHLFNRA | 18177 |
| HPV16 | L1 | 10 | 283 | VRHLFNRAGA | 18178 |
| HPV16 | L1 | 11 | 283 | VRHLFNRAGAV | 18179 |
| HPV16 | L1 | 8 | 61 | YHAGTSRL | 18180 |
| HPV16 | L1 | 9 | 61 | YHAGTSRLL | 18181 |
| HPV16 | L1 | 10 | 61 | YHAGTSRLLA | 18182 |
| HPV16 | L1 | 11 | 61 | YHAGTSRLLAV | 18183 |
| HPV16 | L1 | 9 | 21 | YHIFFQMSL | 18184 |
| HPV16 | L1 | 10 | 21 | YHIFFQMSLW | 18185 |
| HPV16 | L1 | 11 | 21 | YHIFFQMSLWL | 18186 |
| HPV16 | L1 | 9 | 381 | YKNTNFKEY | 18187 |
| HPV16 | L1 | 10 | 381 | YKNTNFKEYL | 18188 |
| HPV16 | L1 | 8 | 177 | YKQTQLCL | 18189 |
| HPV16 | L1 | 9 | 177 | YKQTQLCLI | 18190 |
| HPV16 | L1 | 8 | 444 | YRFVTSQA | 18191 |
| HPV16 | L1 | 9 | 444 | YRFVTSQAI | 18192 |
| HPV16 | L1 | 10 | 444 | YRFVTSQAIA | 18193 |
| HPV16 | L1 | 8 | 96 | YRVFRIHL | 18194 |
| HPV16 | L2 | 9 | 7 | AKRTKRASA | 18195 |
| HPV16 | L2 | 9 | 322 | AKVHYYYDF | 18196 |
| HPV16 | L2 | 11 | 22 | CKQAGTCPPDI | 18197 |
| HPV16 | L2 | 10 | 179 | GHFTLSSSTI | 18198 |
| HPV16 | L2 | 8 | 317 | GKSIGAKV | 18199 |
| HPV16 | L2 | 10 | 317 | GKSIGAKVHY | 18200 |
| HPV16 | L2 | 11 | 317 | GKSIGAKVHYY | 18201 |
| HPV16 | L2 | 8 | 38 | GKTIADQI | 18202 |
| HPV16 | L2 | 9 | 38 | GKTIADQIL | 18203 |
| HPV16 | L2 | 11 | 38 | GKTIADQILQY | 18204 |
| HPV16 | L2 | 8 | 68 | GRTGYIPL | 18205 |
| HPV16 | L2 | 11 | 3 | HKRSAKRTKRA | 18206 |
| HPV16 | L2 | 8 | 11 | KRASATQL | 18207 |
| HPV16 | L2 | 9 | 11 | KRASATQLY | 18208 |
| HPV16 | L2 | 10 | 460 | KRLPYFFSDV | 18209 |
| HPV16 | L2 | 8 | 457 | KRRKRLPY | 18210 |
| HPV16 | L2 | 9 | 457 | KRRKRLPYF | 18211 |
| HPV16 | L2 | 10 | 457 | KRRKRLPYFF | 18212 |
| HPV16 | L2 | 10 | 4 | KRSAKRTKRA | 18213 |
| HPV16 | L2 | 8 | 8 | KRTKRASA | 18214 |
| HPV16 | L2 | 11 | 8 | KRTKRASATQL | 18215 |
| HPV16 | L2 | 8 | 448 | LHPSYYML | 18216 |
| HPV16 | L2 | 8 | 455 | LRKRRKRL | 18217 |
| HPV16 | L2 | 10 | 455 | LRKRRKRLPY | 18218 |
| HPV16 | L2 | 11 | 455 | LRKRRKRLPYF | 18219 |
| HPV16 | L2 | 9 | 312 | LRTRSGKSI | 18220 |
| HPV16 | L2 | 11 | 312 | LRTRSGKSIGA | 18221 |
| HPV16 | L2 | 8 | 34 | PKVEGKTI | 18222 |
| HPV16 | L2 | 9 | 34 | PKVEGKTIA | 18223 |
| HPV16 | L2 | 8 | 459 | RKRLPYFF | 18224 |
| HPV16 | L2 | 11 | 459 | RKRLPYFFSDV | 18225 |
| HPV16 | L2 | 9 | 456 | RKRRKRLPY | 18226 |
| HPV16 | L2 | 10 | 456 | RKRRKRLPYF | 18227 |
| HPV16 | L2 | 11 | 456 | RKRRKRLPYFF | 18228 |
| HPV16 | L2 | 8 | 458 | RRKRLPYF | 18229 |
| HPV16 | L2 | 9 | 458 | RRKRLPYFF | 18230 |
| HPV16 | L2 | 10 | 297 | RRTGIRYSRI | 18231 |
| HPV16 | L2 | 9 | 353 | SHAALPTSI | 18232 |
| HPV16 | L2 | 9 | 304 | SRIGNKQTL | 18233 |
| HPV16 | L2 | 9 | 219 | SRPVARLGL | 18234 |
| HPV16 | L2 | 10 | 219 | SRPVARLGLY | 18235 |
| HPV16 | L2 | 8 | 296 | SRRTGIRY | 18236 |
| HPV16 | L2 | 11 | 296 | SRRTGIRYSRI | 18237 |
| HPV16 | L2 | 9 | 229 | SRTTQQVKV | 18238 |
| HPV16 | L2 | 10 | 229 | SRTTQQVKVV | 18239 |
| HPV16 | L2 | 9 | 190 | THNYEEIPM | 18240 |
| HPV16 | L2 | 10 | 247 | TKLITYDNPA | 18241 |
| HPV16 | L2 | 11 | 247 | TKLITYDNPAY | 18242 |
| HPV16 | L2 | 9 | 10 | TKRASATQL | 18243 |
| HPV16 | L2 | 10 | 10 | TKRASATQLY | 18244 |
| HPV16 | L2 | 10 | 77 | TRPPTATDTL | 18245 |

TABLE XI-continued

| | | | | | |
|---|---|---|---|---|---|
| HPV16 | L2 | 11 | 77 | TRPPTATDTLA | 18246 |
| HPV16 | L2 | 9 | 314 | TRSGKSIGA | 18247 |
| HPV16 | L2 | 11 | 314 | TRSGKSIGAKV | 18248 |
| HPV16 | L2 | 10 | 324 | VHYYYDFSTI | 18249 |
| HPV16 | L2 | 8 | 235 | VKVVDPAF | 18250 |
| HPV16 | L2 | 9 | 235 | VKVVDPAFI | 18251 |
| HPV16 | L2 | 10 | 89 | VRPPLTVDPV | 18252 |
| HPV18 | E1 | 10 | 269 | AHIQCLDCKW | 18253 |
| HPV18 | E1 | 8 | 578 | AKDNRWPY | 18254 |
| HPV18 | E1 | 9 | 578 | AKDNRWPYL | 18255 |
| HPV18 | E1 | 8 | 298 | AKGLSTLL | 18256 |
| HPV18 | E1 | 10 | 298 | AKGLSTLLHV | 18257 |
| HPV18 | E1 | 8 | 125 | AKRRLFTI | 18258 |
| HPV18 | E1 | 8 | 406 | AKYLKDCA | 18259 |
| HPV18 | E1 | 10 | 406 | AKYLKDCATM | 18260 |
| HPV18 | E1 | 8 | 276 | CKWGVLIL | 18261 |
| HPV18 | E1 | 9 | 276 | CKWGVLILA | 18262 |
| HPV18 | E1 | 10 | 276 | CKWGVLILAL | 18263 |
| HPV18 | E1 | 11 | 276 | CKWGVLILALL | 18264 |
| HPV18 | E1 | 8 | 25 | DKKTGDVI | 18265 |
| HPV18 | E1 | 8 | 602 | DKNGNPVY | 18266 |
| HPV18 | E1 | 10 | 602 | DKNGNPVYEI | 18267 |
| HPV18 | E1 | 8 | 613 | DKNWKCFF | 18268 |
| HPV18 | E1 | 8 | 236 | DKTTCTDW | 18269 |
| HPV18 | E1 | 9 | 236 | DKTTCTDWV | 18270 |
| HPV18 | E1 | 11 | 236 | DKTTCTDWVTA | 18271 |
| HPV18 | E1 | 8 | 555 | DRKHKPLI | 18272 |
| HPV18 | E1 | 10 | 555 | DRKHKPLIQL | 18273 |
| HPV18 | E1 | 9 | 101 | ERLEVDTEL | 18274 |
| HPV18 | E1 | 9 | 621 | ERTWSRLDL | 18275 |
| HPV18 | E1 | 10 | 70 | FHAQEVHNDA | 18276 |
| HPV18 | E1 | 9 | 218 | FKDTYGLSF | 18277 |
| HPV18 | E1 | 11 | 233 | FKSDKTTCTDW | 18278 |
| HPV18 | E1 | 8 | 258 | FKTLIQPF | 18279 |
| HPV18 | E1 | 9 | 258 | FKTLIQPFI | 18280 |
| HPV18 | E1 | 10 | 258 | FKTLIQPFIL | 18281 |
| HPV18 | E1 | 11 | 258 | FKTLIQPFILY | 18282 |
| HPV18 | E1 | 8 | 291 | GKSRLTVA | 18283 |
| HPV18 | E1 | 11 | 291 | GKSRLTVAKGL | 18284 |
| HPV18 | E1 | 9 | 489 | GKSYFGMSF | 18285 |
| HPV18 | E1 | 10 | 489 | GKSYFGMSFI | 18286 |
| HPV18 | E1 | 8 | 498 | IHFIQGAV | 18287 |
| HPV18 | E1 | 9 | 498 | IHFIQGAVI | 18288 |
| HPV18 | E1 | 11 | 498 | IHFIQGAVISF | 18289 |
| HPV18 | E1 | 9 | 575 | IHPAKDNRW | 18290 |
| HPV18 | E1 | 11 | 575 | IHPAKDNRWPY | 18291 |
| HPV18 | E1 | 8 | 433 | IRFRCSKI | 18292 |
| HPV18 | E1 | 8 | 557 | KHKPLIQL | 18293 |
| HPV18 | E1 | 11 | 417 | KHYRRAQKRQM | 18294 |
| HPV18 | E1 | 8 | 123 | KKAKRRLF | 18295 |
| HPV18 | E1 | 10 | 123 | KKAKRRLFTI | 18296 |
| HPV18 | E1 | 11 | 476 | KKNCLVFCGPA | 18297 |
| HPV18 | E1 | 9 | 424 | KRQMNMSQW | 18298 |
| HPV18 | E1 | 10 | 424 | KRQMNMSQWI | 18299 |
| HPV18 | E1 | 8 | 629 | LHEEEEDA | 18300 |
| HPV18 | E1 | 8 | 82 | LHVLKRKF | 18301 |
| HPV18 | E1 | 9 | 82 | LHVLKRKFA | 18302 |
| HPV18 | E1 | 8 | 305 | LHVPETCM | 18303 |
| HPV18 | E1 | 9 | 305 | LHVPETCML | 18304 |
| HPV18 | E1 | 10 | 305 | LHVPETCMLI | 18305 |
| HPV18 | E1 | 8 | 564 | LKCPPILL | 18306 |
| HPV18 | E1 | 11 | 409 | LKDCATMCKHY | 18307 |
| HPV18 | E1 | 10 | 471 | LKGTPKKNCL | 18308 |
| HPV18 | E1 | 11 | 471 | LKGTPKKNCLV | 18309 |
| HPV18 | E1 | 9 | 400 | LKSNCQAKY | 18310 |
| HPV18 | E1 | 10 | 400 | LKSNCQAKYL | 18311 |
| HPV18 | E1 | 9 | 205 | LKVNNKQGA | 18312 |
| HPV18 | E1 | 10 | 205 | LKVNNKQGAM | 18313 |
| HPV18 | E1 | 11 | 205 | LKVNNKQGAML | 18314 |
| HPV18 | E1 | 10 | 648 | LRAGQNHRPL | 18315 |
| HPV18 | E1 | 8 | 319 | LRSSVAAL | 18316 |
| HPV18 | E1 | 9 | 319 | LRSSVAALY | 18317 |
| HPV18 | E1 | 10 | 319 | LRSSVAALYW | 18318 |
| HPV18 | E1 | 11 | 319 | LRSSVAALYWY | 18319 |
| HPV18 | E1 | 10 | 286 | LRYKCGKSRL | 18320 |
| HPV18 | E1 | 8 | 453 | LRYQQIEF | 18321 |
| HPV18 | E1 | 9 | 453 | LRYQQIEFI | 18322 |
| HPV18 | E1 | 11 | 453 | LRYQQIEFITF | 18323 |
| HPV18 | E1 | 10 | 543 | MRNALDGNPI | 18324 |

TABLE XI-continued

| | | | | | |
|---|---|---|---|---|---|
| HPV18 | E1 | 8 | 209 | NKQGAMLA | 18325 |
| HPV18 | E1 | 9 | 209 | NKQGAMLAV | 18326 |
| HPV18 | E1 | 10 | 209 | NKQGAMLAVF | 18327 |
| HPV18 | E1 | 10 | 581 | NRWPYLESRI | 18328 |
| HPV18 | E1 | 8 | 475 | PKKNCLVF | 18329 |
| HPV18 | E1 | 8 | 317 | PKLRSSVA | 18330 |
| HPV18 | E1 | 9 | 317 | PKLRSSVAA | 18331 |
| HPV18 | E1 | 10 | 317 | PKLRSSVAAL | 18332 |
| HPV18 | E1 | 11 | 317 | PKLRSSVAALY | 18333 |
| HPV18 | E1 | 8 | 111 | PRLQEISL | 18334 |
| HPV18 | E1 | 9 | 354 | QHGIDDSNF | 18335 |
| HPV18 | E1 | 11 | 354 | QHGIDDSNFDL | 18336 |
| HPV18 | E1 | 8 | 122 | QKKAKRRL | 18337 |
| HPV18 | E1 | 9 | 122 | QKKAKRRLF | 18338 |
| HPV18 | E1 | 11 | 122 | QKKAKRRLFTI | 18339 |
| HPV18 | E1 | 10 | 423 | QKRQMNMSQW | 18340 |
| HPV18 | E1 | 11 | 423 | QKRQMNMSQWI | 18341 |
| HPV18 | E1 | 10 | 348 | QRLTIIQHGI | 18342 |
| HPV18 | E1 | 9 | 556 | RKHKPLIQL | 18343 |
| HPV18 | E1 | 8 | 420 | RRAQKRQM | 18344 |
| HPV18 | E1 | 10 | 420 | RRAQKRQMNM | 18345 |
| HPV18 | E1 | 11 | 127 | RRLFTISDSGY | 18346 |
| HPV18 | E1 | 8 | 513 | SHFWLEPL | 18347 |
| HPV18 | E1 | 9 | 438 | SKIDEGGDW | 18348 |
| HPV18 | E1 | 8 | 588 | SRITVFEF | 18349 |
| HPV18 | E1 | 11 | 588 | SRITVFEFPNA | 18350 |
| HPV18 | E1 | 9 | 293 | SRLTVAKGL | 18351 |
| HPV18 | E1 | 9 | 523 | TKVAMLDDA | 18352 |
| HPV18 | E1 | 8 | 75 | VHNDAQVL | 18353 |
| HPV18 | E1 | 10 | 75 | VHNDAQVLHV | 18354 |
| HPV18 | E1 | 11 | 75 | VHNDAQVLHVL | 18355 |
| HPV18 | E1 | 9 | 616 | WKCFFERTW | 18356 |
| HPV18 | E1 | 8 | 446 | WRPIVQFL | 18357 |
| HPV18 | E1 | 10 | 446 | WRPIVQFLRY | 18358 |
| HPV18 | E1 | 8 | 288 | YKCGKSRL | 18359 |
| HPV18 | E1 | 10 | 288 | YKCGKSRLTV | 18360 |
| HPV18 | E1 | 11 | 288 | YKCGKSRLTVA | 18361 |
| HPV18 | E1 | 9 | 419 | YRRAQKRQM | 18362 |
| HPV18 | E1 | 11 | 419 | YRRAQKRQMNM | 18363 |
| HPV18 | E1 | 8 | 329 | YRTGISNI | 18364 |
| HPV18 | E1 | 11 | 329 | YRTGISNISEV | 18365 |
| HPV18 | E2 | 9 | 73 | AHKAIELQM | 18366 |
| HPV18 | E2 | 10 | 73 | AHKAIELQMA | 18367 |
| HPV18 | E2 | 11 | 73 | AHKAIELQMAL | 18368 |
| HPV18 | E2 | 9 | 237 | AKTYGQTSA | 18369 |
| HPV18 | E2 | 10 | 237 | AKTYGQTSAA | 18370 |
| HPV18 | E2 | 9 | 50 | AREHGIQTL | 18371 |
| HPV18 | E2 | 10 | 21 | DHYENDSKDI | 18372 |
| HPV18 | E2 | 10 | 311 | DHYRDISSTW | 18373 |
| HPV18 | E2 | 8 | 295 | DRNSLKCL | 18374 |
| HPV18 | E2 | 10 | 295 | DRNSLKCLRY | 18375 |
| HPV18 | E2 | 11 | 52 | EHGIQTLNHQV | 18376 |
| HPV18 | E2 | 8 | 256 | EKQHCGPV | 18377 |
| HPV18 | E2 | 11 | 256 | EKQHCGPVNPL | 18378 |
| HPV18 | E2 | 8 | 328 | EKTGILTV | 18379 |
| HPV18 | E2 | 10 | 328 | EKTGILTVTY | 18380 |
| HPV18 | E2 | 9 | 181 | EKYGNTGTW | 18381 |
| HPV18 | E2 | 11 | 181 | EKYGNTGTWEV | 18382 |
| HPV18 | E2 | 10 | 10 | ERLSCVQDKI | 18383 |
| HPV18 | E2 | 11 | 10 | ERLSCVQDKII | 18384 |
| HPV18 | E2 | 8 | 114 | FKKGGQTV | 18385 |
| HPV18 | E2 | 10 | 114 | FKKGGQTVQV | 18386 |
| HPV18 | E2 | 11 | 114 | FKKGGQTVQVY | 18387 |
| HPV18 | E2 | 8 | 176 | FKSECEKY | 18388 |
| HPV18 | E2 | 8 | 74 | HKAIELQM | 18389 |
| HPV18 | E2 | 9 | 74 | HKAIELQMA | 18390 |
| HPV18 | E2 | 10 | 74 | HKAIELQMAL | 18391 |
| HPV18 | E2 | 11 | 159 | HRGLYYVKEGY | 18392 |
| HPV18 | E2 | 10 | 290 | IHLKGDRNSL | 18393 |
| HPV18 | E2 | 8 | 40 | IRWENAIF | 18394 |
| HPV18 | E2 | 9 | 40 | IRWENAIFF | 18395 |
| HPV18 | E2 | 10 | 40 | IRWENAIFFA | 18396 |
| HPV18 | E2 | 11 | 40 | IRWENAIFFAA | 18397 |
| HPV18 | E2 | 9 | 308 | KHSDHYRDI | 18398 |
| HPV18 | E2 | 9 | 115 | KKGGQTVQV | 18399 |
| HPV18 | E2 | 10 | 115 | KKGGQTVQVY | 18400 |
| HPV18 | E2 | 11 | 115 | KKGGQTVQVYF | 18401 |
| HPV18 | E2 | 8 | 299 | LKCLRYRL | 18402 |
| HPV18 | E2 | 8 | 292 | LKGDRNSL | 18403 |

TABLE XI-continued

| | | | | | |
|---|---|---|---|---|---|
| HPV18 | E2 | 11 | 292 | LKGDRNSLKCL | 18404 |
| HPV18 | E2 | 8 | 306 | LRKHSDHY | 18405 |
| HPV18 | E2 | 11 | 306 | LRKHSDHYRDI | 18406 |
| HPV18 | E2 | 8 | 59 | NHQVVPAY | 18407 |
| HPV18 | E2 | 10 | 59 | NHQVVPAYNI | 18408 |
| HPV18 | E2 | 8 | 128 | NKDNCMTY | 18409 |
| HPV18 | E2 | 9 | 128 | NKDNCMTYV | 18410 |
| HPV18 | E2 | 10 | 128 | NKDNCMTYVA | 18411 |
| HPV18 | E2 | 11 | 128 | NKDNCMTYVAW | 18412 |
| HPV18 | E2 | 9 | 4 | PKETLSERL | 18413 |
| HPV18 | E2 | 9 | 258 | QHCGPVNPL | 18414 |
| HPV18 | E2 | 10 | 258 | QHCGPVNPLL | 18415 |
| HPV18 | E2 | Ii | 222 | QHTPSPYSSTV | 18416 |
| HPV18 | E2 | 9 | 342 | QRTKFLNTV | 18417 |
| HPV18 | E2 | 10 | 342 | QRTKFLNTVA | 18418 |
| HPV18 | E2 | 11 | 342 | QRTKFLNTVAI | 18419 |
| HPV18 | E2 | 10 | 307 | RKHSDHYRDI | 18420 |
| HPV18 | E2 | 11 | 279 | RKLCSGNTTPI | 18421 |
| HPV18 | E2 | 8 | 158 | SHRGLYYV | 18422 |
| HPV18 | E2 | 9 | 71 | SKAHKAIEL | 18423 |
| HPV18 | E2 | 11 | 71 | SKAHKAIELQM | 18424 |
| HPV18 | E2 | 8 | 27 | SKDIDSQI | 18425 |
| HPV18 | E2 | 10 | 27 | SKDIDSQIQY | 18426 |
| HPV18 | E2 | 11 | 27 | SKDIDSQIQYW | 18427 |
| HPV18 | E2 | 8 | 69 | SKSKAHKA | 18428 |
| HPV18 | E2 | 9 | 69 | SKSKAHKAI | 18429 |
| HPV18 | E2 | 11 | 69 | SKSKAHKAIEL | 18430 |
| HPV18 | E2 | 8 | 89 | SRYKTEDW | 18431 |
| HPV18 | E2 | 10 | 89 | SRYKTEDWTL | 18432 |
| HPV18 | E2 | 11 | 111 | THCFKKGGQTV | 18433 |
| HPV18 | E2 | 8 | 344 | TKFLNTVA | 18434 |
| HPV18 | E2 | 9 | 344 | TKFLNTVAI | 18435 |
| HPV18 | E2 | 8 | 247 | TRPGHCGL | 18436 |
| HPV18 | E2 | 9 | 247 | TRPGHCGLA | 18437 |
| HPV18 | E2 | 8 | 191 | VHFGNNVI | 18438 |
| HPV18 | E2 | 8 | 165 | VKEGYNTF | 18439 |
| HPV18 | E2 | 9 | 165 | VKEGYNTFY | 18440 |
| HPV18 | E2 | 10 | 165 | VKEGYNTFYI | 18441 |
| HPV18 | E2 | 11 | 218 | VKQLQHTPSPY | 18442 |
| HPV18 | E2 | 10 | 337 | YHSETQRTKF | 18443 |
| HPV18 | E2 | 11 | 337 | YHSETQRTKFL | 18444 |
| HPV18 | E2 | 8 | 91 | YKTEDWTL | 18445 |
| HPV18 | E2 | 8 | 313 | YRDISSTW | 18446 |
| HPV18 | E2 | 10 | 313 | YRDISSTWHW | 18447 |
| HPV18 | E2 | 10 | 304 | YRLRKHSDHY | 18448 |
| HPV18 | E5 | 9 | 18 | CHVPLLPSV | 18449 |
| HPV18 | E5 | 11 | 18 | CHVPLLPSVCM | 18450 |
| HPV18 | E5 | 9 | 64 | LHIHAILSL | 18451 |
| HPV18 | E6 | 11 | 2 | ARFEDPTRRPY | 18452 |
| HPV18 | E6 | 8 | 65 | CHKCIDFY | 18453 |
| HPV18 | E6 | 11 | 65 | CHKCIDFYSRI | 18454 |
| HPV18 | E6 | 8 | 138 | CHSCCNRA | 18455 |
| HPV18 | E6 | 10 | 35 | CKTVLELTEV | 18456 |
| HPV18 | E6 | 11 | 35 | CKTVLELTEVF | 18457 |
| HPV18 | E6 | 8 | 91 | EKLTNTGL | 18458 |
| HPV18 | E6 | 9 | 91 | EKLTNTGLY | 18459 |
| HPV18 | E6 | 11 | 91 | EKLTNTGLYNL | 18460 |
| HPV18 | E6 | 8 | 123 | EKRRFHNI | 18461 |
| HPV18 | E6 | 9 | 123 | EKRRFHNIA | 18462 |
| HPV18 | E6 | 11 | 148 | ERLQRRRETQV | 18463 |
| HPV18 | E6 | 8 | 127 | FHNIAGHY | 18464 |
| HPV18 | E6 | 8 | 49 | FKDLFVVY | 18465 |
| HPV18 | E6 | 10 | 66 | HKCIDFYSRI | 18466 |
| HPV18 | E6 | 10 | 103 | IRCLRCQKPL | 18467 |
| HPV18 | E6 | 11 | 75 | IRELRHYSDSV | 18468 |
| HPV18 | E6 | 8 | 124 | KRRFHNIA | 18469 |
| HPV18 | E6 | 11 | 124 | KRRFHNIAGHY | 18470 |
| HPV18 | E6 | 10 | 106 | LRCQKPLNPA | 18471 |
| HPV18 | E6 | 10 | 118 | LRHLNEKRRF | 18472 |
| HPV18 | E6 | 8 | 78 | LRHYSDSV | 18473 |
| HPV18 | E6 | 9 | 78 | LRHYSDSVY | 18474 |
| HPV18 | E6 | 8 | 143 | NRARQERL | 18475 |
| HPV18 | E6 | 9 | 61 | PHAACHKCI | 18476 |
| HPV18 | E6 | 11 | 61 | PHAACHKCIDF | 18477 |
| HPV18 | E6 | 10 | 109 | QKPLNPAEKL | 18478 |
| HPV18 | E6 | 8 | 151 | QRRRETQV | 18479 |
| HPV18 | E6 | 9 | 119 | RHLNEKRRF | 18480 |
| HPV18 | E6 | 8 | 79 | RHYSDSVY | 18481 |
| HPV18 | E6 | 10 | 125 | RRFHNIAGHY | 18482 |

TABLE XI-continued

| | | | | | |
|---|---|---|---|---|---|
| HPV18 | E6 | 9 | 9 | RRPYKLPDL | 18483 |
| HPV18 | E6 | 9 | 73 | SRIRELRHY | 18484 |
| HPV18 | E6 | 10 | 8 | TRRPYKLPDL | 18485 |
| HPV18 | E6 | 10 | 12 | YKLPDLCTEL | 18486 |
| HPV18 | E6 | 8 | 56 | YRDSIPHA | 18487 |
| HPV18 | E6 | 9 | 56 | YRDSIPHAA | 18488 |
| HPV18 | E7 | 11 | 70 | ARIKLVVESSA | 18489 |
| HPV18 | E7 | 11 | 51 | ARRAEPQRHTM | 18490 |
| HPV18 | E7 | 9 | 66 | CKCEARIKL | 18491 |
| HPV18 | E7 | 10 | 66 | CKCEARIKLV | 18492 |
| HPV18 | E7 | 11 | 66 | CKCEARIKLVV | 18493 |
| HPV18 | E7 | 9 | 72 | IKLVVESSA | 18494 |
| HPV18 | E7 | 9 | 13 | LHLEPQNEI | 18495 |
| HPV18 | E7 | 11 | 13 | LHLEPQNEIPV | 18496 |
| HPV18 | E7 | 8 | 83 | LRAFQQLF | 18497 |
| HPV18 | E7 | 9 | 83 | LRAFQQLFL | 18498 |
| HPV18 | E7 | 8 | 1 | MHGPKATL | 18499 |
| HPV18 | E7 | 11 | 1 | MHGPKATLQDI | 18500 |
| HPV18 | E7 | 10 | 45 | NHQHLPARRA | 18501 |
| HPV18 | E7 | 8 | 4 | PKATLQDI | 18502 |
| HPV18 | E7 | 9 | 4 | PKATLQDIV | 18503 |
| HPV18 | E7 | 10 | 4 | PKATLQDIVL | 18504 |
| HPV18 | E7 | 8 | 47 | QHLPARRA | 18505 |
| HPV18 | E7 | 8 | 57 | QRHTMLCM | 18506 |
| HPV18 | E7 | 10 | 52 | RRAEPQRHTM | 18507 |
| HPV18 | E7 | 11 | 52 | RRAEPQRHTML | 18508 |
| HPV18 | L1 | 11 | 231 | AKGTACKSRPL | 18509 |
| HPV18 | L1 | 8 | 559 | AKRVRVRA | 18510 |
| HPV18 | L1 | 8 | 318 | ARHFWNRA | 18511 |
| HPV18 | L1 | 11 | 318 | ARHFWNRAGTM | 18512 |
| HPV18 | L1 | 9 | 80 | ARVVNTDDY | 18513 |
| HPV18 | L1 | 10 | 80 | ARVVNTDDYV | 18514 |
| HPV18 | L1 | 9 | 290 | CKYPDYLQM | 18515 |
| HPV18 | L1 | 11 | 290 | CKYPDYLQMSA | 18516 |
| HPV18 | L1 | 8 | 504 | DKLKFWNV | 18517 |
| HPV18 | L1 | 10 | 504 | DKLKFWNVDL | 18518 |
| HPV18 | L1 | 8 | 228 | EHWAKGTA | 18519 |
| HPV18 | L1 | 10 | 515 | EKFSLDLDQY | 18520 |
| HPV18 | L1 | 8 | 422 | FKQYSRHV | 18521 |
| HPV18 | L1 | 11 | 422 | FKQYSRHVEEY | 18522 |
| HPV18 | L1 | 11 | 134 | FRVQLPDPNKF | 18523 |
| HPV18 | L1 | 8 | 379 | GHNNGVCW | 18524 |
| HPV18 | L1 | 8 | 180 | GHPFYKKL | 18525 |
| HPV18 | L1 | 8 | 43 | GHYIILFL | 18526 |
| HPV18 | L1 | 11 | 43 | GHYIILFLRNV | 18527 |
| HPV18 | L1 | 8 | 169 | GRGQPLGV | 18528 |
| HPV18 | L1 | 10 | 169 | GRGQPLGVGL | 18529 |
| HPV18 | L1 | 8 | 527 | GRKFLVQA | 18530 |
| HPV18 | L1 | 10 | 527 | GRKFLVQAGL | 18531 |
| HPV18 | L1 | 10 | 375 | HKAQGHNNGV | 18532 |
| HPV18 | L1 | 8 | 453 | IHSMNSSI | 18533 |
| HPV18 | L1 | 9 | 453 | IHSMNSSIL | 18534 |
| HPV18 | L1 | 8 | 338 | IKGTGMPA | 18535 |
| HPV18 | L1 | 11 | 374 | LHKAQGHNNGV | 18536 |
| HPV18 | L1 | 8 | 29 | LHSILVYM | 18537 |
| HPV18 | L1 | 9 | 29 | LHSILVYMV | 18538 |
| HPV18 | L1 | tI | 29 | LHSILVYMVHI | 18539 |
| HPV18 | L1 | 8 | 10 | LHYHLLPL | 18540 |
| HPV18 | L1 | 9 | 10 | LHYHLLPLY | 18541 |
| HPV18 | L1 | 9 | 513 | LKEKFSLDL | 18542 |
| HPV18 | L1 | 8 | 506 | LKFWNVDL | 18543 |
| HPV18 | L1 | 11 | 251 | LKNTVLEDGDM | 18544 |
| HPV18 | L1 | 9 | 50 | LRNVNVFPI | 18545 |
| HPV18 | L1 | 10 | 50 | LRNVNVFPIF | 18546 |
| HPV18 | L1 | 11 | 50 | LRNVNVFPIFL | 18547 |
| HPV18 | L1 | 8 | 311 | LRREQLFA | 18548 |
| HPV18 | L1 | 11 | 311 | LRREQLFARHF | 18549 |
| HPV18 | L1 | 8 | 499 | NKDPYDKL | 18550 |
| HPV18 | L1 | 10 | 499 | NKDPYDKLKF | 18551 |
| HPV18 | L1 | 11 | 499 | NKDPYDKLKFW | 18552 |
| HPV18 | L1 | 10 | 142 | NKFGLPDTSI | 18553 |
| HPV18 | L1 | 11 | 142 | NKFGLPDTSIY | 18554 |
| HPV18 | L1 | 11 | 185 | NKLDDTESSHA | 18555 |
| HPV18 | L1 | 9 | 369 | NKPYWLHKA | 18556 |
| HPV18 | L1 | 8 | 119 | NKQDIPKV | 18557 |
| HPV18 | L1 | 10 | 119 | NKQDIPKVSA | 18558 |
| HPV18 | L1 | 11 | 119 | NKQDIPKVSAY | 18559 |
| HPV18 | L1 | 10 | 323 | NRAGTMGDTV | 18560 |
| HPV18 | L1 | 8 | 124 | PKVSAYQY | 18561 |

TABLE XI-continued

| | | | | | |
|---|---|---|---|---|---|
| HPV18 | L1 | 10 | 124 | PKVSAYQYRV | 18562 |
| HPV18 | L1 | 11 | 124 | PKVSAYQYRVF | 18563 |
| HPV18 | L1 | 9 | 544 | PRKRSAPSA | 18564 |
| HPV18 | L1 | 9 | 24 | PRPLPLHSI | 18565 |
| HPV18 | L1 | 10 | 24 | PRPLPLHSIL | 18566 |
| HPV18 | L1 | 11 | 24 | PRPLPLHSILV | 18567 |
| HPV18 | L1 | 8 | 157 | QRLVWACA | 18568 |
| HPV18 | L1 | 10 | 157 | QRLVWACAGV | 18569 |
| HPV18 | L1 | 10 | 319 | RHFWNRAGTM | 18570 |
| HPV18 | L1 | 8 | 427 | RHVEEYDL | 18571 |
| HPV18 | L1 | 10 | 427 | RHVEEYDLQF | 18572 |
| HPV18 | L1 | 11 | 427 | RHVEEYDLQFI | 18573 |
| HPV18 | L1 | 9 | 528 | RKFLVQAGL | 18574 |
| HPV18 | L1 | 8 | 545 | RKRSAPSA | 18575 |
| HPV18 | L1 | 10 | 312 | RREQLFARHF | 18576 |
| HPV18 | L1 | 11 | 312 | RREQLFARHFW | 18577 |
| HPV18 | L1 | 8 | 193 | SHAATSNV | 18578 |
| HPV18 | L1 | 9 | 556 | SKPAKRVRV | 18579 |
| HPV18 | L1 | 11 | 556 | SKPAKRVRVRA | 18580 |
| HPV18 | L1 | 9 | 426 | SRHVEEYDL | 18581 |
| HPV18 | L1 | 11 | 426 | SRHVEEYDLQF | 18582 |
| HPV18 | L1 | 10 | 101 | SRLLTVGNPY | 18583 |
| HPV18 | L1 | 11 | 101 | SRLLTVGNPYF | 18584 |
| HPV18 | L1 | 9 | 277 | TKCEVPLDI | 18585 |
| HPV18 | L1 | 10 | 420 | TKFKQYSRHV | 18586 |
| HPV18 | L1 | 8 | 5 | TRVLILHY | 18587 |
| HPV18 | L1 | 10 | 5 | TRVLILHYHL | 18588 |
| HPV18 | L1 | 11 | 5 | TRVLILHYHLL | 18589 |
| HPV18 | L1 | 9 | 37 | VHIIICGHY | 18590 |
| HPV18 | L1 | 10 | 37 | VHIIICGHYI | 18591 |
| HPV18 | L1 | 11 | 37 | VHIIICGHYII | 18592 |
| HPV18 | L1 | 9 | 204 | VRDNVSVDY | 18593 |
| HPV18 | L1 | 9 | 386 | WHNQLFVTV | 18594 |
| HPV18 | L1 | 10 | 386 | WHNQLFVTVV | 18595 |
| HPV18 | L1 | 8 | 65 | WRPSDNTV | 18596 |
| HPV18 | L1 | 9 | 65 | WRPSDNTVY | 18597 |
| HPV18 | L1 | 10 | 65 | WRPSDNTVYL | 18598 |
| HPV18 | L1 | 8 | 96 | YHAGSSRL | 18599 |
| HPV18 | L1 | 9 | 96 | YHAGSSRLL | 18600 |
| HPV18 | L1 | 11 | 96 | YHAGSSRLLTV | 18601 |
| HPV18 | L1 | 10 | 12 | YHLLPLYGPL | 18602 |
| HPV18 | L1 | 11 | 12 | YHLLPLYGPLY | 18603 |
| HPV18 | L1 | 8 | 22 | YHPRPLPL | 18604 |
| HPV18 | L1 | 11 | 22 | YHPRPLPLHSI | 18605 |
| HPV18 | L1 | 8 | 212 | YKQTQLCI | 18606 |
| HPV18 | L1 | 9 | 212 | YKQTQLCIL | 18607 |
| HPV18 | L1 | 8 | 480 | YRFVQSVA | 18608 |
| HPV18 | L1 | 9 | 480 | YRFVQSVAI | 18609 |
| HPV18 | L1 | 8 | 131 | YRVFRVQL | 18610 |
| HPV18 | L2 | 8 | 7 | ARRKRASV | 18611 |
| HPV18 | L2 | 11 | 7 | ARRKRASVTDL | 18612 |
| HPV18 | L2 | 9 | 315 | ARVHFYHDI | 18613 |
| HPV18 | L2 | 11 | 21 | CKQSGTCPPDV | 18614 |
| HPV18 | L2 | 9 | 42 | DKILQWSSL | 18615 |
| HPV18 | L2 | 11 | 42 | DKILQWSSLGI | 18616 |
| HPV18 | L2 | 10 | 372 | FKYSPTISSA | 18617 |
| HPV18 | L2 | 9 | 76 | GRSNTVVDV | 18618 |
| HPV18 | L2 | 8 | 67 | GRTGYIPL | 18619 |
| HPV18 | L2 | 9 | 4 | HRAARRKRA | 18620 |
| HPV18 | L2 | 11 | 4 | HRAARRKRASV | 18621 |
| HPV18 | L2 | 8 | 430 | IHGTHYYL | 18622 |
| HPV18 | L2 | 9 | 430 | IHGTHYYLW | 18623 |
| HPV18 | L2 | 11 | 430 | IHGTHYYLWPL | 18624 |
| HPV18 | L2 | 8 | 280 | IRLHRPAL | 18625 |
| HPV18 | L2 | 8 | 446 | KKRKRVPY | 18626 |
| HPV18 | L2 | 9 | 446 | KKRKRVPYF | 18627 |
| HPV18 | L2 | 10 | 446 | KKRKRVPYFF | 18628 |
| HPV18 | L2 | 11 | 446 | KKRKRVPYFFA | 18629 |
| HPV18 | L2 | 8 | 10 | KRASVTDL | 18630 |
| HPV18 | L2 | 9 | 10 | KRASVTDLY | 18631 |
| HPV18 | L2 | 8 | 447 | KRKRVPYF | 18632 |
| HPV18 | L2 | 9 | 447 | KRKRVPYFF | 18633 |
| HPV18 | L2 | 10 | 447 | KRKRVPYFFA | 18634 |
| HPV18 | L2 | 8 | 449 | KRVPYFFA | 18635 |
| HPV18 | L2 | 11 | 449 | KRVPYFFADGF | 18636 |
| HPV18 | L2 | 9 | 445 | PKKRKRVPY | 18637 |
| HPV18 | L2 | 10 | 445 | PKKRKRVPYF | 18638 |
| HPV18 | L2 | 11 | 445 | PKKRKRVPYFF | 18639 |
| HPV18 | L2 | 8 | 33 | PKVEGTTL | 18640 |

TABLE XI-continued

| | | | | | |
|---|---|---|---|---|---|
| HPV18 | L2 | 9 | 33 | PKVEGTTLA | 18641 |
| HPV18 | L2 | 8 | 224 | PRLYSRAY | 18642 |
| HPV18 | L2 | 11 | 224 | PRLYSRAYQQV | 18643 |
| HPV18 | L2 | 11 | 118 | PRPTFTGTSGF | 18644 |
| HPV18 | L2 | 10 | 267 | PRSDVPDSDF | 18645 |
| HPV18 | L2 | 11 | 267 | PRSDVPDSDFM | 18646 |
| HPV18 | L2 | 9 | 9 | RKRASVTDL | 18647 |
| HPV18 | L2 | 10 | 9 | RKRASVTDLY | 18648 |
| HPV18 | L2 | 8 | 448 | RKRVPYFF | 18649 |
| HPV18 | L2 | 9 | 448 | RKRVPYFFA | 18650 |
| HPV18 | L2 | 10 | 290 | RRGTVRFSRL | 18651 |
| HPV18 | L2 | 10 | 8 | RRKRASVTDL | 18652 |
| HPV18 | L2 | 11 | 8 | RRKRASVTDLY | 18653 |
| HPV18 | L2 | 8 | 219 | RRVAGPRL | 18654 |
| HPV18 | L2 | 9 | 219 | RRVAGPRLY | 18655 |
| HPV18 | L2 | 10 | 3 | SHRAARRKRA | 18656 |
| HPV18 | L2 | 9 | 228 | SRAYQQVSV | 18657 |
| HPV18 | L2 | 10 | 228 | SRAYQQVSVA | 18658 |
| HPV18 | L2 | 9 | 297 | SRLGQRATM | 18659 |
| HPV18 | L2 | 10 | 297 | SRLGQRATMF | 18660 |
| HPV18 | L2 | 8 | 289 | SRRGTVRF | 18661 |
| HPV18 | L2 | 11 | 289 | SRRGTVRFSRL | 18662 |
| HPV18 | L2 | 8 | 363 | SRSTTSFA | 18663 |
| HPV18 | L2 | 9 | 363 | SRSTTSFAF | 18664 |
| HPV18 | L2 | 10 | 363 | SRSTTSFAFF | 18665 |
| HPV18 | L2 | 9 | 189 | THGYEEIPL | 18666 |
| HPV18 | L2 | 8 | 433 | THYYLWPL | 18667 |
| HPV18 | L2 | 9 | 433 | THYYLWPLY | 18668 |
| HPV18 | L2 | 10 | 433 | THYYLWPLYY | 18669 |
| HPV18 | L2 | 11 | 433 | THYYLWPLYYF | 18670 |
| HPV18 | L2 | 10 | 87 | TRPPVVIEPV | 18671 |
| HPV18 | L2 | 9 | 243 | TRPSSLITY | 18672 |
| HPV18 | L2 | 9 | 307 | TRSGTQIGA | 18673 |
| HPV18 | L2 | 11 | 307 | TRSGTQIGARV | 18674 |
| HPV18 | L2 | 10 | 317 | VHFYHDISPI | 18675 |
| HPV18 | L2 | 11 | 317 | VHFYHDISPIA | 18676 |
| HPV18 | L2 | 10 | 294 | VRFSRLGQRA | 18677 |
| HPV18 | L2 | 9 | 218 | VRRVAGPRL | 18678 |
| HPV18 | L2 | 10 | 218 | VRRVAGPRLY | 18679 |
| HPV18 | L2 | 8 | 320 | YHDISPIA | 18680 |
| HPV31 | E1 | 9 | 496 | AKIGMLDDA | 18681 |
| HPV31 | E1 | 10 | 379 | AKIVKDCGTM | 18682 |
| HPV31 | E1 | 10 | 264 | AKNRITIEKL | 18683 |
| HPV31 | E1 | 11 | 264 | AKNRITIEKLL | 18684 |
| HPV31 | E1 | 8 | 121 | AKRRLFEL | 18685 |
| HPV31 | E1 | 10 | 242 | CHLQSLACSW | 18686 |
| HPV31 | E1 | 9 | 607 | DKENDGDSF | 18687 |
| HPV31 | E1 | 8 | 575 | DKNGNPVY | 18688 |
| HPV31 | E1 | 10 | 575 | DKNGNPVYEL | 18689 |
| HPV31 | E1 | 8 | 586 | DKNWKSFF | 18690 |
| HPV31 | E1 | 9 | 411 | DKVSDEGDW | 18691 |
| HPV31 | E1 | 8 | 25 | DRQTGDNI | 18692 |
| HPV31 | E1 | 10 | 554 | DRWFYLHSRL | 18693 |
| HPV31 | E1 | 11 | 554 | DRWPYLHSRLV | 18694 |
| HPV31 | E1 | 8 | 77 | EHAEAVQV | 18695 |
| HPV31 | E1 | 9 | 77 | EHAEAVQVL | 18696 |
| HPV31 | E1 | 11 | 275 | EKLLCISTNCM | 18697 |
| HPV31 | E1 | 8 | 271 | EKLLEKLL | 18698 |
| HPV31 | E1 | 10 | 271 | EKLLEKLLCI | 18699 |
| HPV31 | E1 | 10 | 396 | EKRQMSMGQW | 18700 |
| HPV31 | E1 | 11 | 396 | EKRQMSMGQWI | 18701 |
| HPV31 | E1 | 11 | 164 | ERENETPTRNI | 18702 |
| HPV31 | E1 | 10 | 321 | ERQTVLQHSF | 18703 |
| HPV31 | E1 | 10 | 70 | FHAQEAEEHA | 18704 |
| HPV31 | E1 | 8 | 261 | FKCAKNRI | 18705 |
| HPV31 | E1 | 10 | 261 | FKCAKNRITI | 18706 |
| HPV31 | E1 | 9 | 618 | FKCVSGQNI | 18707 |
| HPV31 | E1 | 9 | 191 | FKELYGVSF | 18708 |
| HPV31 | E1 | 10 | 191 | FKELYGVSFM | 18709 |
| HPV31 | E1 | 8 | 231 | FKTLLQPY | 18710 |
| HPV31 | E1 | 10 | 231 | FKTLLQPYCL | 18711 |
| HPV31 | E1 | 11 | 231 | FKTLLQPYCLY | 18712 |
| HPV31 | E1 | 9 | 183 | GKAAMLGKF | 18713 |
| HPV31 | E1 | 8 | 551 | GKDDRWPY | 18714 |
| HPV31 | E1 | 9 | 551 | GKDDRWPYL | 18715 |
| HPV31 | E1 | 9 | 189 | GKFKELYGV | 18716 |
| HPV31 | E1 | 11 | 189 | GKFKELYGVSF | 18717 |
| HPV31 | E1 | 9 | 462 | GKSYFGMSL | 18718 |
| HPV31 | E1 | 10 | 462 | GKSYFGMSLI | 18719 |

TABLE XI-continued

| | | | | | |
|---|---|---|---|---|---|
| HPV31 | E1 | 11 | 455 | IHGAPNTGKSY | 18720 |
| HPV31 | E1 | 8 | 406 | IKSRCDKV | 18721 |
| HPV31 | E1 | 8 | 530 | KHKALMQL | 18722 |
| HPV31 | E1 | 10 | 449 | KKNCILIHGA | 18723 |
| HPV31 | E1 | 8 | 393 | KRAEKRQM | 18724 |
| HPV31 | E1 | 10 | 393 | KRAEKRQMSM | 18725 |
| HPV31 | E1 | 9 | 86 | KRKYVGSPL | 18726 |
| HPV31 | Ei | 9 | 397 | KRQMSMGQW | 18727 |
| HPV31 | E1 | 10 | 397 | KRQMSMGQWI | 18728 |
| HPV31 | E1 | 8 | 559 | LHSRLVVF | 18729 |
| HPV31 | E1 | 10 | 559 | LHSRLVVFTF | 18730 |
| HPV31 | E1 | 8 | 537 | LKCPPLL1 | 18731 |
| HPV31 | E1 | 10 | 444 | LKGVPKKNCI | 18732 |
| HPV31 | E1 | 11 | 444 | LKGVPKKNCIL | 18733 |
| HPV31 | E1 | 8 | 440 | LKLFLKGV | 18734 |
| HPV31 | E1 | 10 | 85 | LKRKYVGSPL | 18735 |
| HPV31 | E1 | 9 | 373 | LKSNSQAKI | 18736 |
| HPV31 | E1 | 10 | 373 | LKSNSQAKIV | 18737 |
| HPV31 | E1 | 8 | 178 | LKTSNGKA | 18738 |
| HPV31 | E1 | 9 | 178 | LKTSNGKAA | 18739 |
| HPV31 | E1 | 10 | 178 | LKTSNGKAAM | 18740 |
| HPV31 | E1 | 11 | 178 | LKTSNGKAAML | 18741 |
| HPV31 | E1 | 10 | 516 | LRNALDGNPV | 18742 |
| HPV31 | E1 | 8 | 292 | LRSTAAAL | 18743 |
| HPV31 | E1 | 9 | 292 | LRSTAAALY | 18744 |
| HPV31 | E1 | 10 | 292 | LRSTAAALYW | 18745 |
| HPV31 | E1 | 11 | 292 | LRSTAAALYWY | 18746 |
| HPV31 | E1 | 8 | 426 | LRYQQIEF | 18747 |
| HPV31 | E1 | 9 | 426 | LRYQQIEFV | 18748 |
| HPV31 | E1 | 11 | 426 | LRYQQIEFVSF | 18749 |
| HPV31 | E1 | 8 | 209 | NKSTCTDW | 18750 |
| HPV31 | E1 | 10 | 209 | NKSTCTDWCV | 18751 |
| HPV31 | E1 | 11 | 209 | NKSTCTDWCVA | 18752 |
| HPV31 | E1 | 8 | 266 | NRITIEKL | 18753 |
| HPV31 | E1 | 9 | 266 | NRITIEKLL | 18754 |
| HPV31 | E1 | 8 | 448 | PKKNCILI | 18755 |
| HPV31 | E1 | 11 | 448 | PKKNCILIHGA | 18756 |
| HPV31 | E1 | 8 | 290 | PKLRSTAA | 18757 |
| HPV31 | E1 | 9 | 290 | PKLRSTAAA | 18758 |
| HPV31 | E1 | 10 | 290 | PKLRSTAAAL | 18759 |
| HPV31 | E1 | 11 | 290 | PKLRSTAAALY | 18760 |
| HPV31 | E1 | 8 | 107 | PRLKAICI | 18761 |
| HPV31 | E1 | 9 | 327 | QHSFNDTTF | 18762 |
| HPV31 | E1 | 11 | 327 | QHSFNDTTFDL | 18763 |
| HPV31 | E1 | 11 | 390 | RHYKRAEKRQM | 18764 |
| HPV31 | E1 | 8 | 87 | RKYVGSPL | 18765 |
| HPV31 | E1 | 11 | 87 | RKYVGSPLSDI | 18766 |
| HPV31 | E1 | 11 | 123 | RRLFELPDSGY | 18767 |
| HPV31 | E1 | 8 | 486 | SHFWLQPL | 18768 |
| HPV31 | E1 | 9 | 486 | SHFWLQPLA | 18769 |
| HPV31 | E1 | 11 | 486 | SHFWLQPLADA | 18770 |
| HPV31 | E1 | 10 | 484 | SKSHFWLQPL | 18771 |
| HPV31 | E1 | 11 | 484 | SKSHFWLQPLA | 18772 |
| HPV31 | E1 | 8 | 118 | SKTAKRRL | 18773 |
| HPV31 | E1 | 9 | 118 | SKTAKRRLF | 18774 |
| HPV31 | E1 | 11 | 118 | SKTAKRRLFEL | 18775 |
| HPV31 | E1 | 8 | 561 | SRLVVFTF | 18776 |
| HPV31 | E1 | 9 | 594 | SRTWCRLNL | 18777 |
| HPV31 | E1 | 8 | 171 | TRNILQVL | 18778 |
| HPV31 | E1 | 11 | 382 | VKDCGTMCRHY | 18779 |
| HPV31 | E1 | 9 | 423 | VKFLRYQQI | 18780 |
| HPV31 | E1 | 11 | 423 | VKFLRYQQIEF | 18781 |
| HPV31 | E1 | 9 | 529 | VKHALMQL | 18782 |
| HPV31 | E1 | 10 | 259 | VRFKCAKNRI | 18783 |
| HPV31 | E1 | 8 | 509 | WHYIDNYL | 18784 |
| HPV31 | E1 | 11 | 509 | WHYIDNYLRNA | 18785 |
| HPV31 | E1 | 9 | 589 | WKSFFSRTW | 18786 |
| HPV31 | E1 | 8 | 419 | WRDIVKFL | 18787 |
| HPV31 | E1 | 10 | 419 | WRDIVKFLRY | 18788 |
| HPV31 | E1 | 9 | 392 | YKRAEKRQM | 18789 |
| HPV31 | E1 | 11 | 392 | YKRAEKRQMSM | 18790 |
| HPV31 | E1 | 8 | 302 | YRTGMSNI | 18791 |
| HPV31 | E1 | 11 | 302 | YRTGMSNISDV | 18792 |
| HPV31 | E2 | 9 | 67 | AKALQAIEL | 18793 |
| HPV31 | E2 | 11 | 67 | AKALQAIELQM | 18794 |
| HPV31 | E2 | 10 | 175 | AKKYGTGKKW | 18795 |
| HPV31 | E2 | 9 | 46 | AREMGIHSI | 18796 |
| HPV31 | E2 | 9 | 28 | DHIDYWKHI | 18797 |
| HPV31 | E2 | 11 | 28 | DHIDYWKHIRL | 18798 |

TABLE XI-continued

| | | | | | |
|---|---|---|---|---|---|
| HPV31 | E2 | 11 | 251 | EHRNTHHPNKL | 18799 |
| HPV31 | E2 | 10 | 17 | EHYENDSKRL | 18800 |
| HPV31 | E2 | 9 | 163 | GHITYFVNF | 18801 |
| HPV31 | E2 | 8 | 333 | GKHKNAIV | 18802 |
| HPV31 | E2 | 10 | 333 | GKHKNAIVTL | 18803 |
| HPV31 | E2 | 8 | 181 | GKKWEVHA | 18804 |
| HPV31 | E2 | 8 | 335 | HKNAIVTL | 18805 |
| HPV31 | E2 | 10 | 335 | HKNAIVTLTY | 18806 |
| HPV31 | E2 | 11 | 335 | HKNAIVTLTYI | 18807 |
| HPV31 | E2 | 10 | 252 | HRNTHHPNKL | 18808 |
| HPV31 | E2 | 11 | 252 | HRNTHHPNKLL | 18809 |
| HPV31 | E2 | 9 | 296 | IHLKGDANI | 18810 |
| HPV31 | E2 | 10 | 296 | IHLKGDANIL | 18811 |
| HPV31 | E2 | 8 | 51 | IHSINHQV | 18812 |
| HPV31 | E2 | 9 | 51 | IHSINHQVV | 18813 |
| HPV31 | E2 | 11 | 51 | IHSINHQVVPA | 18814 |
| HPV31 | E2 | 8 | 36 | IRLECVLM | 18815 |
| HPV31 | E2 | 9 | 36 | IRLECVLMY | 18816 |
| HPV31 | E2 | 11 | 36 | IRLECVLMYKA | 18817 |
| HPV31 | E2 | 8 | 112 | KHGYTVEV | 18818 |
| HPV31 | E2 | 10 | 112 | KHGYTVEVQF | 18819 |
| HPV31 | E2 | 8 | 34 | KHIRLECV | 18820 |
| HPV31 | E2 | 9 | 34 | KHIRLECVL | 18821 |
| HPV31 | E2 | 10 | 34 | KHIRLECVLM | 18822 |
| HPV31 | E2 | 11 | 34 | KHIRLECVLMY | 18823 |
| HPV31 | E2 | 9 | 334 | KHKNAIVTL | 18824 |
| HPV31 | E2 | 11 | 334 | KHKNAIVTLTY | 18825 |
| HPV31 | E2 | 9 | 111 | KKHGYTVEV | 18826 |
| HPV31 | E2 | 11 | 111 | KKHGYTVEVQF | 18827 |
| HPV31 | E2 | 11 | 182 | KKWEVHAGGQV | 18828 |
| HPV31 | E2 | 9 | 176 | KKYGTGKKW | 18829 |
| HPV31 | E2 | 11 | 176 | KKYGTGKKWEV | 18830 |
| HPV31 | E2 | 9 | 24 | KRLCDHIDY | 18831 |
| HPV31 | E2 | 10 | 24 | KRLCDHIDYW | 18832 |
| HPV31 | E2 | 8 | 305 | LKCLRYRL | 18833 |
| HPV31 | E2 | 11 | 305 | LKCLRYRLSKY | 18834 |
| HPV31 | E2 | 8 | 298 | LKGDANIL | 18835 |
| HPV31 | E2 | 11 | 298 | LKGDANILKCL | 18836 |
| HPV31 | E2 | 8 | 110 | LKKHGYTV | 18837 |
| HPV31 | E2 | 10 | 110 | LKKHGYTVEV | 18838 |
| HPV31 | E2 | 9 | 262 | LRGDSVDSV | 18839 |
| HPV31 | E2 | 8 | 308 | LRVRLSKY | 18840 |
| HPV31 | E2 | 11 | 308 | LRYRLSKYKQL | 18841 |
| HPV31 | E2 | 8 | 129 | MHYTNWKF | 18842 |
| HPV31 | E2 | 9 | 129 | MHYTNWKFI | 18843 |
| HPV31 | E2 | 10 | 129 | MHYTNWKFIY | 18844 |
| HPV31 | E2 | 11 | 129 | MHYTNWKFIYL | 18845 |
| HPV31 | E2 | 8 | 55 | NHQVVPAL | 18846 |
| HPV31 | E2 | 10 | 55 | NHQVVPALSV | 18847 |
| HPV31 | E2 | 9 | 259 | NKLLRGDSV | 18848 |
| HPV31 | E2 | 9 | 349 | QRDDFLNTV | 18849 |
| HPV31 | E2 | 11 | 349 | QRDDFLNTVKI | 18850 |
| HPV31 | E2 | 10 | 6 | QRLNVCQDKI | 18851 |
| HPV31 | E2 | 11 | 6 | QRLNVCQDKIL | 18852 |
| HPV31 | E2 | 8 | 65 | SKAKALQA | 18853 |
| HPV31 | E2 | 9 | 65 | SKAKALQAI | 18854 |
| HPV31 | E2 | 11 | 65 | SKAKALQAIEL | 18855 |
| HPV31 | E2 | 8 | 23 | SKRLCDHI | 18856 |
| HPV31 | E2 | 10 | 23 | SKRLCDHIDY | 18857 |
| HPV31 | E2 | 11 | 23 | SKRLCDHIDYW | 18858 |
| HPV31 | E2 | 10 | 313 | SKYKQLYEQV | 18859 |
| HPV31 | E2 | 8 | 255 | THHPNKLL | 18860 |
| HPV31 | E2 | 8 | 284 | TRAVSCPA | 18861 |
| HPV31 | E2 | 8 | 186 | VHAGGQVI | 18862 |
| HPV31 | E2 | 9 | 186 | VHAGGQVIV | 18863 |
| HPV31 | E2 | 10 | 186 | VHAGGQVIVF | 18864 |
| HPV31 | E2 | 8 | 160 | VHEGHITY | 18865 |
| HPV31 | E2 | 9 | 160 | VHEGHITYF | 18866 |
| HPV31 | E2 | 10 | 160 | VHEGHITYFV | 18867 |
| HPV31 | E2 | 10 | 125 | VHNTMHYTNW | 18868 |
| HPV31 | E2 | 9 | 357 | VKIPNTVSV | 18869 |
| HPV31 | E2 | 8 | 134 | WKFIYLCI | 18870 |
| HPV31 | E2 | 9 | 33 | WKHIRLECV | 18871 |
| HPV31 | E2 | 10 | 33 | WKHIRLECVL | 18872 |
| HPV31 | E2 | 11 | 33 | WKHIRLECVLM | 18873 |
| HPV31 | E2 | 8 | 44 | YKAREMGI | 18874 |
| HPV31 | E2 | 11 | 44 | YKAREMGIHSI | 18875 |
| HPV31 | E2 | 8 | 87 | YKNEDWTM | 18876 |
| HPV31 | E2 | 8 | 315 | YKQLYEQV | 18877 |

TABLE XI-continued

| | | | | | |
|---|---|---|---|---|---|
| HPV31 | E2 | 9 | 310 | YRLSKYKQL | 18878 |
| HPV31 | E2 | 10 | 310 | YRLSKYKQLY | 18879 |
| HPV31 | E5 | 8 | 74 | IHTHASFL | 18880 |
| HPV31 | E5 | 8 | 29 | IRPLVLSV | 18881 |
| HPV31 | E5 | 10 | 29 | IRPLVLSVSV | 18882 |
| HPV31 | E5 | 11 | 29 | IRPLVLSVSVY | 18883 |
| HPV31 | E5 | 8 | 57 | LRCFCIYV | 18884 |
| HPV31 | E5 | 9 | 57 | LRCFCIYVV | 18885 |
| HPV31 | E5 | 10 | 57 | LRCFCIYVVF | 18886 |
| HPV31 | E5 | 11 | 57 | LRCFCIYVVFI | 18887 |
| HPV31 | E6 | 10 | 33 | CKGQLTETEV | 18888 |
| HPV31 | E6 | 11 | 33 | CKGQLTETEVL | 18889 |
| HPV31 | E6 | 9 | 120 | DKKKRFHNI | 18890 |
| HPV31 | E6 | 8 | 89 | EKLTNKGI | 18891 |
| HPV31 | E6 | 11 | 89 | EKLTNKGICDL | 18892 |
| HPV31 | E6 | 9 | 7 | ERPRKLHEL | 18893 |
| HPV31 | E6 | 8 | 125 | FHNIGGRW | 18894 |
| HPV31 | E6 | 11 | 2 | FKNPAERPRKL | 18895 |
| HPV31 | E6 | 8 | 76 | FRWYRYSV | 18896 |
| HPV31 | E6 | 9 | 76 | FRWYRYSVY | 18897 |
| HPV31 | E6 | 8 | 130 | GRWTGRCI | 18898 |
| HPV31 | E6 | 9 | 130 | GRWTGRCIA | 18899 |
| HPV31 | E6 | 11 | 130 | GRWTGRCIACW | 18900 |
| HPV31 | E6 | 10 | 101 | IRCITCQRPL | 18901 |
| HPV31 | E6 | 8 | 121 | KKKRFHNI | 18902 |
| HPV31 | E6 | 11 | 122 | KKRFHNIGGRW | 18903 |
| HPV31 | E6 | 10 | 123 | KRFHNIGGRW | 18904 |
| HPV31 | E6 | 8 | 12 | LHELSSAL | 18905 |
| HPV31 | E6 | 10 | 12 | LHELSSALEI | 18906 |
| HPV31 | E6 | 10 | 67 | LRFYSKVSEF | 18907 |
| HPV31 | E6 | 8 | 93 | NKGICDLL | 18908 |
| HPV31 | E6 | 9 | 93 | NKGICDLLI | 18909 |
| HPV31 | E6 | 9 | 59 | PHGVCTKCL | 18910 |
| HPV31 | E6 | 11 | 59 | PHGVCTKCLRF | 18911 |
| HPV31 | E6 | 10 | 9 | PRKLHELSSA | 18912 |
| HPV31 | E6 | 11 | 9 | PRKLHELSSAL | 18913 |
| HPV31 | E6 | 10 | 116 | QRHLDKKKRF | 18914 |
| HPV31 | E6 | 9 | 117 | RHLDKKKRF | 18915 |
| HPV31 | E6 | 9 | 10 | RKLHELSSA | 18916 |
| HPV31 | E6 | 10 | 10 | RKLHELSSAL | 18917 |
| HPV31 | E6 | 9 | 141 | RRPRTETQV | 18918 |
| HPV31 | E6 | 8 | 71 | SKVSEFRW | 18919 |
| HPV31 | E6 | 9 | 71 | SKVSEFRWY | 18920 |
| HPV31 | E6 | 11 | 71 | SKVSEFRWYRY | 18921 |
| HPV31 | E6 | 10 | 64 | TKCLRFYSKV | 18922 |
| HPV31 | E6 | 10 | 140 | WRRPRTETQV | 18923 |
| HPV31 | E6 | 9 | 54 | YRDDTPHGV | 18924 |
| HPV31 | E6 | 10 | 79 | YRYSVYGTTL | 18925 |
| HPV31 | E7 | 9 | 61 | CKSTLRLCV | 18926 |
| HPV31 | E7 | 8 | 76 | IRILQELL | 18927 |
| HPV31 | E7 | 9 | 76 | IRILQELLM | 18928 |
| HPV31 | E7 | 10 | 65 | LRLCVQSTQV | 18929 |
| HPV31 | E7 | 8 | 1 | MRGETPTL | 18930 |
| HPV31 | E7 | 11 | 1 | MRGETPTLQDY | 18931 |
| HPV31 | L1 | 10 | 40 | ARLLTVGHPY | 18932 |
| HPV31 | L1 | 11 | 40 | ARLLTVGHPYY | 18933 |
| HPV31 | L1 | 9 | 380 | CKITLSADI | 18934 |
| HPV31 | L1 | 10 | 380 | CKITLSADIM | 18935 |
| HPV31 | L1 | 9 | 162 | CKPPIGEHW | 18936 |
| HPV31 | L1 | 9 | 230 | CKYPDYLKM | 18937 |
| HPV31 | L1 | 10 | 230 | CKYPDYLKMV | 18938 |
| HPV31 | L1 | 11 | 230 | CKYPDYLKMVA | 18939 |
| HPV31 | L1 | 10 | 454 | EKFSADLDQF | 18940 |
| HPV31 | L1 | 8 | 481 | FKAGKRSA | 18941 |
| HPV31 | L1 | 11 | 481 | FKAGKRSAPSA | 18942 |
| HPV31 | L1 | 9 | 442 | FKDYVFWEV | 18943 |
| HPV31 | L1 | 11 | 442 | FKDYVFWEVNL | 18944 |
| HPV31 | L1 | 11 | 361 | FKEYLRHGEEF | 18945 |
| HPV31 | L1 | 9 | 356 | FKSSNFKEY | 18946 |
| HPV31 | L1 | 10 | 356 | FKSSNFKEYL | 18947 |
| HPV31 | L1 | 11 | 74 | FRVRLPDPNKF | 18948 |
| HPV31 | L1 | 8 | 319 | GHNNGICW | 18949 |
| HPV31 | L1 | 8 | 120 | GHPLLNKF | 18950 |
| HPV31 | L1 | 10 | 171 | GKGSPCSNNA | 18951 |
| HPV31 | L1 | 11 | 171 | GKGSPCSNNAI | 18952 |
| HPV31 | L1 | 8 | 484 | GKRSAPSA | 18953 |
| HPV31 | L1 | 8 | 109 | GRGQPLGV | 18954 |
| HPV31 | L1 | 10 | 109 | GRGQPLGVGI | 18955 |
| HPV31 | L1 | 8 | 466 | GRKFLLQA | 18956 |

TABLE XI-continued

| | | | | | |
|---|---|---|---|---|---|
| HPV31 | L1 | 10 | 466 | GRKFLLQAGY | 18957 |
| HPV31 | L1 | 8 | 392 | IHSMNPM | 18958 |
| HPV31 | L1 | 9 | 392 | IHSMNPML | 18959 |
| HPV31 | L1 | 8 | 278 | IKGSGSTA | 18960 |
| HPV31 | L1 | 10 | 278 | IKGSGSTATL | 18961 |
| HPV31 | L1 | 11 | 278 | IKGSGSTATLA | 18962 |
| HPV31 | L1 | 8 | 59 | KKIVVPKV | 18963 |
| HPV31 | L1 | 11 | 59 | KKIVVPKVSGL | 18964 |
| HPV31 | L1 | 9 | 452 | LKEKFSADL | 18965 |
| HPV31 | L1 | 8 | 236 | LKMVAEPY | 18966 |
| HPV31 | L1 | 11 | 191 | LKNSVIQDGDM | 18967 |
| HPV31 | L1 | 9 | 365 | LRHGEEFDL | 18968 |
| HPV31 | L1 | 11 | 365 | LRHGEEFDLQF | 18969 |
| HPV31 | L1 | 8 | 251 | LRREQMFV | 18970 |
| HPV31 | L1 | 11 | 251 | LRREQMFVRHF | 18971 |
| HPV31 | L1 | 10 | 82 | NKFGFPDTSF | 18972 |
| HPV31 | L1 | 11 | 82 | NKFGFPDTSFY | 18973 |
| HPV31 | L1 | 9 | 309 | NKPYWMQRA | 18974 |
| HPV31 | L1 | 9 | 144 | NRECISMDY | 18975 |
| HPV31 | L1 | 10 | 263 | NRSGTVGESV | 18976 |
| HPV31 | L1 | 9 | 437 | PKEDPFKDY | 18977 |
| HPV31 | L1 | 10 | 437 | PKEDPFKDYV | 18978 |
| HPV31 | L1 | 11 | 437 | PKEDPFKDYVF | 18979 |
| HPV31 | L1 | 10 | 479 | PKFKAGKRSA | 18980 |
| HPV31 | L1 | 9 | 58 | PKKIVVPKV | 18981 |
| HPV31 | L1 | 9 | 53 | PKSDNPKKI | 18982 |
| HPV31 | L1 | 10 | 53 | PKSDNPKKIV | 18983 |
| HPV31 | L1 | 11 | 53 | PKSDNPKKIVV | 18984 |
| HPV31 | L1 | 8 | 64 | PKVSGLQY | 18985 |
| HPV31 | L1 | 10 | 64 | PKVSGLQYRV | 18986 |
| HPV31 | L1 | 11 | 64 | PKVSGLQYRVF | 18987 |
| HPV31 | L1 | 8 | 435 | QKPKEDPF | 18988 |
| HPV31 | L1 | 11 | 435 | QKPKEDPFKDY | 18989 |
| HPV31 | L1 | 10 | 315 | QRAQGHNNGI | 18990 |
| HPV31 | L1 | 8 | 97 | QRLVWACV | 18991 |
| HPV31 | L1 | 10 | 97 | QRLVWACVGL | 18992 |
| HPV31 | L1 | 10 | 259 | RHFFNRSGTV | 18993 |
| HPV31 | L1 | 8 | 366 | RHGEEFDL | 18994 |
| HPV31 | L1 | 10 | 366 | RHGEEFDLQF | 18995 |
| HPV31 | L1 | 11 | 366 | RHGEEFDLQFI | 18996 |
| HPV31 | L1 | 9 | 467 | RKFLLQAGY | 18997 |
| HPV31 | L1 | 11 | 467 | RKFLLQAGYRA | 18998 |
| HPV31 | L1 | 10 | 252 | RREQMFVRHF | 18999 |
| HPV31 | L1 | 11 | 252 | RREQMFVRHFF | 19000 |
| HPV31 | L1 | 9 | 19 | SKVVSTDEY | 19001 |
| HPV31 | L1 | 10 | 19 | SKVVSTDEYV | 19002 |
| HPV31 | L1 | 9 | 217 | TKSNVPLDI | 19003 |
| HPV31 | L1 | 8 | 338 | TRSTNMSV | 19004 |
| HPV31 | L1 | 10 | 338 | TRSTNMSVCA | 19005 |
| HPV31 | L1 | 11 | 338 | TRSTNMSVCAA | 19006 |
| HPV31 | L1 | 9 | 29 | TRTNIYYHA | 19007 |
| HPV31 | L1 | 11 | 253 | VRHFFNRSGTV | 19008 |
| HPV31 | L1 | 9 | 76 | VRLPDPNKF | 19009 |
| HPV31 | L1 | 11 | 76 | VRLPDPNKFGF | 19010 |
| HPV31 | L1 | 8 | 4 | WRPSEATV | 19011 |
| HPV31 | L1 | 9 | 4 | WRPSEATVY | 19012 |
| HPV31 | L1 | 10 | 4 | WRPSEATVYL | 19013 |
| HPV31 | L1 | 8 | 35 | YHAGSARL | 19014 |
| HPV31 | L1 | 9 | 35 | YHAGSARLL | 19015 |
| HPV31 | L1 | 11 | 35 | YHAGSARLLTV | 19016 |
| HPV31 | L1 | 8 | 152 | YKQTQLCL | 19017 |
| HPV31 | L1 | 9 | 152 | YKQTQLCLL | 19018 |
| HPV31 | L1 | 9 | 475 | YRARPKFKA | 19019 |
| HPV31 | L1 | 8 | 419 | YRFVTSQA | 19020 |
| HPV31 | L1 | 9 | 419 | YRFVTSQAI | 19021 |
| HPV31 | L1 | 8 | 71 | YRVFRVRL | 19022 |
| HPV31 | L2 | 9 | 218 | ARLGLYSKA | 19023 |
| HPV31 | L2 | 9 | 315 | ARVHYYYDI | 19024 |
| HPV31 | L2 | 11 | 22 | CKAAGTCPSDV | 19025 |
| HPV31 | L2 | 8 | 412 | EHAPTQVF | 19026 |
| HPV31 | L2 | 10 | 412 | EHAPTQVFPF | 19027 |
| HPV31 | L2 | 9 | 37 | EHTTIADQI | 19028 |
| HPV31 | L2 | 10 | 37 | EHTTIADQIL | 19029 |
| HPV31 | L2 | 10 | 174 | GHLLLSSSSI | 19030 |
| HPV31 | L2 | 8 | 68 | GRTGYVPL | 19031 |
| HPV31 | L2 | 10 | 89 | IRPPVSIDPV | 19032 |
| HPV31 | L2 | 8 | 11 | KRASATQL | 19033 |
| HPV31 | L2 | 9 | 11 | KRASATQLY | 19034 |
| HPV31 | L2 | 9 | 449 | KRRRKRVSY | 19035 |

TABLE XI-continued

| | | | | | |
|---|---|---|---|---|---|
| HPV31 | L2 | 10 | 449 | KRRRKRVSYF | 19036 |
| HPV31 | L2 | 11 | 449 | KRRRKRVSYFF | 19037 |
| HPV31 | L2 | 10 | 4 | KRSTKRTKRA | 19038 |
| HPV31 | L2 | 8 | 8 | KRTKRASA | 19039 |
| HPV31 | L2 | 11 | 8 | KRTKRASATQL | 19040 |
| HPV31 | L2 | 10 | 453 | KRVSYFFTDV | 19041 |
| HPV31 | L2 | 8 | 441 | LHPSYYML | 19042 |
| HPV31 | L2 | 8 | 448 | LKRRRKRV | 19043 |
| HPV31 | L2 | 10 | 448 | LKRRRKRVSY | 19044 |
| HPV31 | L2 | 11 | 448 | LKRRRKRVSYF | 19045 |
| HPV31 | L2 | 9 | 305 | LRTRSGATI | 19046 |
| HPV31 | L2 | 11 | 305 | LRTRSGATIGA | 19047 |
| HPV31 | L2 | 8 | 46 | LRYGSMGV | 19048 |
| HPV31 | L2 | 9 | 46 | LRYGSMGVF | 19049 |
| HPV31 | L2 | 10 | 46 | LRYGSMGVFF | 19050 |
| HPV31 | L2 | 11 | 301 | NKQTLRTRSGA | 19051 |
| HPV31 | L2 | 9 | 124 | PHPPTTSGF | 19052 |
| HPV31 | L2 | 11 | 124 | PHPPTTSGFDI | 19053 |
| HPV31 | L2 | 8 | 34 | PKIEHTFI | 19054 |
| HPV31 | L2 | 9 | 34 | PKIEHTFIA | 19055 |
| HPV31 | L2 | 11 | 241 | PKQLITYENPA | 19056 |
| HPV31 | L2 | 8 | 452 | RKRVSYFF | 19057 |
| HPV31 | L2 | 11 | 452 | RKRVSYFFTDV | 19058 |
| HPV31 | L2 | 8 | 451 | RRKRVSYF | 19059 |
| HPV31 | L2 | 9 | 451 | RRKRVSYFF | 19060 |
| HPV31 | L2 | 10 | 290 | RRNTVRYSRL | 19061 |
| HPV31 | L2 | 8 | 215 | RRPARLGL | 19062 |
| HPV31 | L2 | 9 | 215 | RRPARLGLY | 19063 |
| HPV31 | L2 | 8 | 450 | RRRKRVSY | 19064 |
| HPV31 | L2 | 9 | 450 | RRRKRVSYF | 19065 |
| HPV31 | L2 | 10 | 450 | RRRKRVSYFF | 19066 |
| HPV31 | L2 | 10 | 267 | SHNIAPDPDF | 19067 |
| HPV31 | L2 | 11 | 267 | SHNIAPDPDFL | 19068 |
| HPV31 | L2 | 9 | 224 | SKATQQVKV | 19069 |
| HPV31 | L2 | 10 | 224 | SKATQQVKVI | 19070 |
| HPV31 | L2 | 11 | 3 | SKRSTKRTKRA | 19071 |
| HPV31 | L2 | 9 | 297 | SRLGNKQTL | 19072 |
| HPV31 | L2 | 8 | 289 | SRRNTVRY | 19073 |
| HPV31 | L2 | 11 | 289 | SRRNTVRYSRL | 19074 |
| HPV31 | L2 | 9 | 368 | THNVSPSTA | 19075 |
| HPV31 | L2 | 10 | 368 | THNVSPSTAV | 19076 |
| HPV31 | L2 | 9 | 185 | THNYEEIPM | 19077 |
| HPV31 | L2 | 9 | 10 | TKRASATQL | 19078 |
| HPV31 | L2 | 10 | 10 | TKRASATQLY | 19079 |
| HPV31 | L2 | 9 | 7 | TKRTKRASA | 19080 |
| HPV31 | L2 | 9 | 77 | TRPSTVSEA | 19081 |
| HPV31 | L2 | 11 | 77 | TRPSTVSEASI | 19082 |
| HPV31 | L2 | 9 | 307 | TRSGATIGA | 19083 |
| HPV31 | L2 | 11 | 307 | TRSGATIGARV | 19084 |
| HPV31 | L2 | 10 | 317 | VHYYYDISSI | 19085 |
| HPV31 | L2 | 8 | 230 | VKVIDPTF | 19086 |
| HPV31 | L2 | 9 | 230 | VKVIDPTFL | 19087 |
| HPV31 | L2 | 11 | 230 | VKVIDPTFLSA | 19088 |
| HPV31 | L2 | 9 | 214 | VRRPARLGL | 19089 |
| HPV31 | L2 | 10 | 214 | VRRPARLGLY | 19090 |
| HPV33 | E1 | 9 | 509 | AKIGMIDDV | 19091 |
| HPV33 | E1 | 9 | 392 | AKIVKDCGI | 19092 |
| HPV33 | E1 | 10 | 392 | AKIVKDCGIM | 19093 |
| HPV33 | E1 | 8 | 284 | AKLMSNLL | 19094 |
| HPV33 | E1 | 10 | 284 | AKLMSNLLSI | 19095 |
| HPV33 | E1 | 9 | 620 | DKENHGGNI | 19096 |
| HPV33 | E1 | 8 | 222 | DKTSCTDW | 19097 |
| HPV33 | E1 | 10 | 222 | DKTSCTDWCI | 19098 |
| HPV33 | E1 | 11 | 102 | DRAANPCRTSI | 19099 |
| HPV33 | E1 | 8 | 263 | DRGIIILL | 19100 |
| HPV33 | E1 | 9 | 263 | DRGIIILLL | 19101 |
| HPV33 | E1 | 10 | 263 | DRGIIILLLI | 19102 |
| HPV33 | E1 | 10 | 334 | DRLTVLQHSF | 19103 |
| HPV33 | E1 | 10 | 409 | EKRKMSIGQW | 19104 |
| HPV33 | E1 | 11 | 409 | EKRKMSIGQWI | 19105 |
| HPV33 | E1 | 9 | 424 | EKTNDGGNW | 19106 |
| HPV33 | E1 | 8 | 25 | ERRTGDNI | 19107 |
| HPV33 | E1 | 9 | 204 | FKEAYGISF | 19108 |
| HPV33 | E1 | 10 | 204 | FKEAYGISFM | 19109 |
| HPV33 | E1 | 8 | 453 | FKKFLKGI | 19110 |
| HPV33 | E1 | 11 | 219 | FKSDKTSCTDW | 19111 |
| HPV33 | E1 | 8 | 274 | FRCSKNRL | 19112 |
| HPV33 | E1 | 10 | 274 | FRCSKNRLTV | 19113 |
| HPV33 | E1 | 11 | 274 | FRCSKNRLTVA | 19114 |

TABLE XI-continued

| | | | | | |
|---|---|---|---|---|---|
| HPV33 | E1 | 8 | 315 | FRTAMSNI | 19115 |
| HPV33 | E1 | 11 | 315 | FRTAMSMSDV | 19116 |
| HPV33 | E1 | 9 | 475 | GKSYFGMSL | 19117 |
| HPV33 | E1 | 10 | 475 | GKSYFGMSLI | 19118 |
| HPV33 | E1 | 10 | 248 | IKQHSLYTHL | 19119 |
| HPV33 | E1 | 10 | 272 | IRFRCSKNRL | 19120 |
| HPV33 | E1 | 8 | 543 | KHRALVQL | 19121 |
| HPV33 | E1 | 8 | 406 | KKAEKRKM | 19122 |
| HPV33 | E1 | 10 | 406 | KKAEKRKMSI | 19123 |
| HPV33 | E1 | 11 | 462 | KKSCMLICGPA | 19124 |
| HPV33 | E1 | 11 | 86 | KKKFAACSQSA | 19125 |
| HPV33 | E1 | 9 | 410 | KKKMSIGQW | 19126 |
| HPV33 | E1 | 10 | 410 | KRKMSIGQWI | 19127 |
| HPV33 | E1 | 8 | 572 | LHSRLTVF | 19128 |
| HPV33 | E1 | 10 | 572 | LHSRLTVFEF | 19129 |
| HPV33 | E1 | 8 | 191 | LHSSNTKA | 19130 |
| HPV33 | E1 | 10 | 191 | LHSSNTKANI | 19131 |
| HPV33 | E1 | 11 | 191 | LHSSNTKANIL | 19132 |
| HPV33 | E1 | 8 | 550 | LKCPPLLL | 19133 |
| HPV33 | E1 | 9 | 487 | LKGCVISCV | 19134 |
| HPV33 | E1 | 10 | 457 | LKGIPKKSCM | 19135 |
| HPV33 | E1 | 11 | 457 | LKGIPKKSCML | 19136 |
| HPV33 | E1 | 9 | 386 | LKSNSQAKI | 19137 |
| HPV33 | E1 | 10 | 386 | LKSNSQAKIV | 19138 |
| HPV33 | E1 | 10 | 244 | LKVLIKQHSL | 19139 |
| HPV33 | E1 | 11 | 244 | LKVLIKQHSLY | 19140 |
| HPV33 | E1 | 8 | 305 | LRSQTCAL | 19141 |
| HPV33 | E1 | 9 | 305 | LRSQTCALY | 19142 |
| HPV33 | E1 | 10 | 305 | LRSQTCALYW | 19143 |
| HPV33 | E1 | 11 | 305 | LRSQTCALYWF | 19144 |
| HPV33 | E1 | 8 | 439 | LRYQNIEF | 19145 |
| HPV33 | E1 | 10 | 439 | LRYQNIEFTA | 19146 |
| HPV33 | E1 | 11 | 439 | LRYQNIEFTAF | 19147 |
| HPV33 | E1 | 10 | 529 | MRNALDGNE1 | 19148 |
| HPV33 | E1 | 9 | 623 | NHGGNISTF | 19149 |
| HPV33 | E1 | 11 | 115 | NKECTYRKRKI | 19150 |
| HPV33 | E1 | 8 | 113 | NKNKECTY | 19151 |
| HPV33 | E1 | 8 | 279 | NRLTVAKL | 19152 |
| HPV33 | E1 | 9 | 279 | NRLTVAKLM | 19153 |
| HPV33 | E1 | 8 | 461 | PKKSCMLI | 19154 |
| HPV33 | E1 | 9 | 303 | PKLRSQTCA | 19155 |
| HPV33 | E1 | 10 | 303 | PKLRSQTCAL | 19156 |
| HPV33 | E1 | 11 | 303 | PKLRSQTCALY | 19157 |
| HPV33 | E1 | 8 | 340 | QHSFNDNI | 19158 |
| HPV33 | E1 | 9 | 340 | QHSFNDNIF | 19159 |
| HPV33 | E1 | 11 | 340 | QHSFNDNIFDL | 19160 |
| HPV33 | E1 | 8 | 250 | QHSLYTHL | 19161 |
| HPV33 | E1 | 11 | 250 | QHSLYTHLQCL | 19162 |
| HPV33 | E1 | 11 | 403 | RHYKKAEKRKM | 19163 |
| HPV33 | E1 | 10 | 87 | RKFAACSQSA | 19164 |
| HPV33 | E1 | 11 | 87 | RKFAACSQSAA | 19165 |
| HPV33 | E1 | 11 | 123 | RKIDELEDSGY | 19166 |
| HPV33 | E1 | 8 | 411 | RKMSIGQW | 19167 |
| HPV33 | E1 | 9 | 411 | RKMSIGQWI | 19168 |
| HPV33 | E1 | 8 | 121 | RKRKIDEL | 19169 |
| HPV33 | E1 | 8 | 499 | SHFWLQPL | 19170 |
| HPV33 | E1 | 11 | 499 | SHFWLQPLSDA | 19171 |
| HPV33 | E1 | 8 | 277 | SKNRLTVA | 19172 |
| HPV33 | E1 | 10 | 277 | SKNRLTVAKL | 19173 |
| HPV33 | E1 | 11 | 277 | SKNRLTVAKLM | 19174 |
| HPV33 | E1 | 10 | 497 | SKSHFWLQPL | 19175 |
| HPV33 | E1 | 8 | 574 | SRLTVFEF | 19176 |
| HPV33 | E1 | 9 | 607 | SRTWCKLDL | 19177 |
| HPV33 | E1 | 10 | 607 | SRTWCKLDLI | 19178 |
| HPV33 | E1 | 10 | 567 | SRWPYLHSRL | 19179 |
| HPV33 | E1 | 9 | 196 | TKANILYKF | 19180 |
| HPV33 | E1 | 11 | 395 | VKDCGIMCRHY | 19181 |
| HPV33 | E1 | 9 | 542 | VKHRALVQL | 19182 |
| HPV33 | E1 | 9 | 602 | WKSFFSRTW | 19183 |
| HPV33 | E1 | 8 | 432 | WRPIVQLL | 19184 |
| HPV33 | E1 | 10 | 432 | WRPIVQLLRY | 19185 |
| HPV33 | E1 | 9 | 202 | YKFKEAYGI | 19186 |
| HPV33 | E1 | 11 | 202 | YKFKEAYGISF | 19187 |
| HPV33 | E1 | 9 | 405 | YKKAEKRKM | 19188 |
| HPV33 | E1 | 11 | 405 | YKKAEKRKMSI | 19189 |
| HPV33 | E1 | 9 | 120 | YRKRKIDEL | 19190 |
| HPV33 | E2 | 9 | 46 | AKQMGFSHL | 19191 |
| HPV33 | E2 | 8 | 176 | AKYSKTQM | 19192 |
| HPV33 | E2 | 9 | 176 | AKYSKTQMW | 19193 |

TABLE XI-continued

| | | | | | |
|---|---|---|---|---|---|
| HPV33 | E2 | 11 | 176 | AKYSKTQMWEV | 19194 |
| HPV33 | E2 | 10 | 6 | ARLNAVQEKI | 19195 |
| HPV33 | E2 | 11 | 6 | ARLNAVQEKIL | 19196 |
| HPV33 | E2 | 8 | 55 | CHQVVPSL | 19197 |
| HPV33 | E2 | 9 | 55 | CHQVVPSLL | 19198 |
| HPV33 | E2 | 10 | 55 | CHQVVPSLLA | 19199 |
| HPV33 | E2 | 8 | 124 | DKKNTMDY | 19200 |
| HPV33 | E2 | 11 | 124 | DKKNTMDYTNW | 19201 |
| HPV33 | E2 | 9 | 22 | DKTDLPSQI | 19202 |
| HPV33 | E2 | 8 | 31 | EHWKLIRM | 19203 |
| HPV33 | E2 | 11 | 31 | EHWKLIRMECA | 19204 |
| HPV33 | E2 | 9 | 13 | EKILDLYEA | 19205 |
| HPV33 | E2 | 8 | 164 | EKVYFKYF | 19206 |
| HPV33 | E2 | 8 | 171 | FKEDAAKY | 19207 |
| HPV33 | E2 | 8 | 110 | FKKQGETV | 19208 |
| HPV33 | E2 | 10 | 110 | FKKQGETVTV | 19209 |
| HPV33 | E2 | 8 | 168 | FKYFKEDA | 19210 |
| HPV33 | E2 | 9 | 168 | FKYFKEDAA | 19211 |
| HPV33 | E2 | 11 | 168 | FKYFKEDAAKY | 19212 |
| HPV33 | E2 | 8 | 150 | GKVDYIGM | 19213 |
| HPV33 | E2 | 9 | 150 | GKVDYIGMY | 19214 |
| HPV33 | E2 | 10 | 150 | GKVDYIGMYY | 19215 |
| HPV33 | E2 | 11 | 150 | GKVDYIGMYYI | 19216 |
| HPV33 | E2 | 8 | 160 | IHNCEKVY | 19217 |
| HPV33 | E2 | 9 | 160 | IHNCEKVYF | 19218 |
| HPV33 | E2 | 11 | 160 | IHNCEKVYFKY | 19219 |
| HPV33 | E2 | 8 | 36 | IRMECALL | 19220 |
| HPV33 | E2 | 9 | 36 | IRMECALLY | 19221 |
| HPV33 | E2 | 11 | 36 | IRMECALLYTA | 19222 |
| HPV33 | E2 | 10 | 125 | KKNTMDYTNW | 19223 |
| HPV33 | E2 | 9 | 111 | KKQGETVTV | 19224 |
| HPV33 | E2 | 11 | 111 | KKQGETVTVQY | 19225 |
| HPV33 | E2 | 8 | 286 | LKCLRYRL | 19226 |
| HPV33 | E2 | 11 | 286 | LKCLRYRLKPY | 19227 |
| HPV33 | E2 | 8 | 279 | LKGESNSL | 19228 |
| HPV33 | E2 | 11 | 279 | LKGESNSLKCL | 19229 |
| HPV33 | E2 | 8 | 293 | LKPYKELY | 19230 |
| HPV33 | E2 | 11 | 293 | LKPYKELYSSM | 19231 |
| HPV33 | E2 | 8 | 289 | LRYRLKPY | 19232 |
| HPV33 | E2 | 11 | 289 | LRYRLKPYKEL | 19233 |
| HPV33 | E2 | 8 | 313 | NKNSKNGI | 19234 |
| HPV33 | E2 | 9 | 313 | NKNSKNGIV | 19235 |
| HPV33 | E2 | 11 | 313 | NKNSKNGIVTV | 19236 |
| HPV33 | E2 | 11 | 263 | NKQRTVCSSNV | 19237 |
| HPV33 | E2 | 8 | 218 | NRPPQAAA | 19238 |
| HPV33 | E2 | 11 | 107 | PKCFKKQGETV | 19239 |
| HPV33 | E2 | 9 | 265 | QRTVCSSNV | 19240 |
| HPV33 | E2 | 10 | 265 | QRTVCSSNVA | 19241 |
| HPV33 | E2 | 10 | 228 | RRPADTTDTA | 19242 |
| HPV33 | E2 | 11 | 227 | RRRPADTTDTA | 19243 |
| HPV33 | E2 | 8 | 52 | SHLCHQVV | 19244 |
| HPV33 | E2 | 11 | 52 | SHLCHQVVPSL | 19245 |
| HPV33 | E2 | 8 | 316 | SKNGIVTV | 19246 |
| HPV33 | E2 | 10 | 316 | SKNGIVTVTF | 19247 |
| HPV33 | E2 | 11 | 316 | SKNGIVTVTFV | 19248 |
| HPV33 | E2 | 10 | 83 | SKSQYSTSQW | 19249 |
| HPV33 | E2 | 8 | 65 | SKTKAFQV | 19250 |
| HPV33 | E2 | 9 | 65 | SKTKAFQVI | 19251 |
| HPV33 | E2 | 11 | 65 | SKTKAFQVIEL | 19252 |
| HPV33 | E2 | 8 | 179 | SKTQMWEV | 19253 |
| HPV33 | E2 | 10 | 179 | SKTQMWEVHV | 19254 |
| HPV33 | E2 | 9 | 67 | TKAFQVIEL | 19255 |
| HPV33 | E2 | 11 | 67 | TKAFQVIELQM | 19256 |
| HPV33 | E2 | 9 | 241 | TKLFCADPA | 19257 |
| HPV33 | E2 | 10 | 241 | TKLFCADPAL | 19258 |
| HPV33 | E2 | 10 | 277 | VHLKGESNSL | 19259 |
| HPV33 | E2 | 8 | 186 | VHVGGQVI | 19260 |
| HPV33 | E2 | 9 | 186 | VHVGGQVIW | 19261 |
| HPV33 | E2 | 9 | 338 | VKIPPTVQI | 19262 |
| HPV33 | E2 | 9 | 33 | WKLIRMECA | 19263 |
| HPV33 | E2 | 10 | 33 | WKLIRMECAL | 19264 |
| HPV33 | E2 | 11 | 33 | WKLIRMECALL | 19265 |
| HPV33 | E2 | 8 | 296 | YKELYSSM | 19266 |
| HPV33 | E2 | 9 | 291 | YRLKPYKEL | 19267 |
| HPV33 | E2 | 10 | 291 | YRLKPYKELY | 19268 |
| HPV33 | E5 | 8 | 47 | LKIFFCYL | 19269 |
| HPV33 | E5 | 9 | 47 | LKIFFCYLL | 19270 |
| HPV33 | E5 | 10 | 47 | LKIFFCYLLF | 19271 |
| HPV33 | E5 | 11 | 47 | LKIFFCYLLFL | 19272 |

TABLE XI-continued

| | | | | | |
|---|---|---|---|---|---|
| HPV33 | E5 | 8 | 19 | LRPLILSI | 19273 |
| HPV33 | E5 | 11 | 19 | LRPLILSISTY | 19274 |
| HPV33 | E6 | 10 | 33 | CKKPLQRSEV | 19275 |
| HPV33 | E6 | 11 | 33 | CKKPLQRSEVY | 19276 |
| HPV33 | E6 | 8 | 63 | CKLCLRFL | 19277 |
| HPV33 | E6 | 11 | 63 | CKLCLRFLSKI | 19278 |
| HPV33 | E6 | 8 | 114 | EKKRHVDL | 19279 |
| HPV33 | E6 | 9 | 7 | EKPRTLHDL | 19280 |
| HPV33 | E6 | 8 | 125 | FHNISGRW | 19281 |
| HPV33 | E6 | 9 | 125 | FHNISGRWA | 19282 |
| HPV33 | E6 | 8 | 130 | GRWAGRCA | 19283 |
| HPV33 | E6 | 9 | 130 | GRWAGRCAA | 19284 |
| HPV33 | E6 | 11 | 130 | GRWAGRCAACW | 19285 |
| HPV33 | E6 | 9 | 23 | IHNIELQCV | 19286 |
| HPV33 | E6 | 10 | 101 | IRCIICQRPL | 19287 |
| HPV33 | E6 | 8 | 93 | KKPLNEIL | 19288 |
| HPV33 | E6 | 9 | 93 | KKPLNEILI | 19289 |
| HPV33 | E6 | 9 | 34 | KKPLQRSEV | 19290 |
| HPV33 | E6 | 10 | 34 | KKPLQRSEVY | 19291 |
| HPV33 | E6 | 11 | 115 | KKRHVDLNKRF | 19292 |
| HPV33 | E6 | 10 | 123 | KRFHNISGRW | 19293 |
| HPV33 | E6 | 11 | 123 | KRFHNISGRWA | 19294 |
| HPV33 | E6 | 10 | 116 | KRHVDLNKRF | 19295 |
| HPV33 | E6 | 8 | 12 | LHDLCQAL | 19296 |
| HPV33 | E6 | 10 | 67 | LRFLSKISEY | 19297 |
| HPV33 | E6 | 11 | 122 | NKRFHMSGRW | 19298 |
| HPV33 | E6 | 10 | 9 | PRTLHDLCQA | 19299 |
| HPV33 | E6 | 11 | 9 | PRTLHDLCQAL | 19300 |
| HPV33 | E6 | 8 | 38 | QRSEVYDF | 19301 |
| HPV33 | E6 | 9 | 38 | QRSEVYDFA | 19302 |
| HPV33 | E6 | 10 | 38 | QRSEVYDFAF | 19303 |
| HPV33 | E6 | 11 | 38 | QRSEVYDFAFA | 19304 |
| HPV33 | E6 | 9 | 117 | RHVDLNKRF | 19305 |
| HPV33 | E6 | 8 | 77 | RHYNYSVY | 19306 |
| HPV33 | E6 | 9 | 71 | SKISEYRHY | 19307 |
| HPV33 | E6 | 11 | 71 | SKISEYRHYNY | 19308 |
| HPV33 | E6 | 8 | 142 | SRRRETAL | 19309 |
| HPV33 | E6 | 8 | 92 | VKKPLNEI | 19310 |
| HPV33 | E6 | 9 | 92 | VKKPLNEIL | 19311 |
| HPV33 | E6 | 10 | 92 | VKKPLNEILI | 19312 |
| HPV33 | E6 | 9 | 140 | WRSRRRETA | 19313 |
| HPV33 | E6 | 10 | 140 | WRSRRRETAL | 19314 |
| HPV33 | E6 | 9 | 54 | YREGNPFGI | 19315 |
| HPV33 | E6 | 8 | 76 | YRHYNYSV | 19316 |
| HPV33 | E6 | 9 | 76 | YRHYNYSVY | 19317 |
| HPV33 | E7 | 8 | 58 | CHTCNTYV | 19318 |
| HPV33 | E7 | 10 | 58 | CHTCNTUVRL | 19319 |
| HPV33 | E7 | 10 | 39 | DRPDGQAQPA | 19320 |
| HPV33 | E7 | 9 | 3 | GHKPTLKEY | 19321 |
| HPV33 | E7 | 10 | 3 | GHKPTLKEYV | 19322 |
| HPV33 | E7 | 11 | 3 | GHKPTLKEYVL | 19323 |
| HPV33 | E7 | 8 | 4 | HKPTLKEY | 19324 |
| HPV33 | E7 | 9 | 4 | HKPTLKEYV | 19325 |
| HPV33 | E7 | 10 | 4 | HKPTLKEYVL | 19326 |
| HPV33 | E7 | 8 | 8 | LKEYVLDL | 19327 |
| HPV33 | E7 | 9 | 8 | LKEYVLDLY | 19328 |
| HPV33 | E7 | 8 | 76 | LRTIQQLL | 19329 |
| HPV33 | E7 | 9 | 76 | LRTIQQLLM | 19330 |
| HPV33 | E7 | 8 | 1 | MRGHKPTL | 19331 |
| HPV33 | E7 | 11 | 1 | MRGHKPTLKEY | 19332 |
| HPV33 | E7 | 9 | 65 | VRLCVNSTA | 19333 |
| HPV33 | L1 | 9 | 58 | AKKLLVPKV | 19334 |
| HPV33 | L1 | 8 | 475 | AKPKLKRA | 19335 |
| HPV33 | L1 | 9 | 475 | AKPKLKRAA | 19336 |
| HPV33 | L1 | 9 | 162 | CKPPTGEHW | 19337 |
| HPV33 | L1 | 9 | 378 | CKVTLTAEV | 19338 |
| HPV33 | L1 | 10 | 378 | CKVTLTAEVM | 19339 |
| HPV33 | L1 | 9 | 229 | CKYPDYLKM | 19340 |
| HPV33 | L1 | 8 | 168 | EHWGKGVA | 19341 |
| HPV33 | L1 | 9 | 435 | EKEDPLGKY | 19342 |
| HPV33 | L1 | 11 | 435 | EKEDPLGKYUF | 19343 |
| HPV33 | L1 | 10 | 452 | EKFSADLDQF | 19344 |
| HPV33 | L1 | 8 | 359 | FKEYIRHV | 19345 |
| HPV33 | L1 | 11 | 359 | FKEYIRHVEEY | 19346 |
| HPV33 | L1 | t1 | 210 | FKTLQANKSDV | 19347 |
| HPV33 | L1 | 11 | 74 | FRVRLPDPNKF | 19348 |
| HPV33 | L1 | 8 | 318 | GHNNGICW | 19349 |
| HPV33 | L1 | 8 | 120 | GHPLLNKF | 19350 |
| HPV33 | L1 | 9 | 171 | GKGVACTNA | 19351 |

TABLE XI-continued

| | | | | | |
|---|---|---|---|---|---|
| HPV33 | L1 | 10 | 171 | GKGVACTNAA | 19352 |
| HPV33 | L1 | 8 | 441 | GKYTFWEV | 19353 |
| HPV33 | L1 | 10 | 441 | GKYTFWEVDL | 19354 |
| HPV33 | L1 | 8 | 109 | GRGQPLGV | 19355 |
| HPV33 | L1 | 10 | 109 | GRGQPLGVGI | 19356 |
| HPV33 | L1 | 8 | 464 | GRKFLLQA | 19357 |
| HPV33 | L1 | 10 | 464 | GRKFLLQAGL | 19358 |
| HPV33 | L1 | 8 | 390 | IHAMNPDI | 19359 |
| HPV33 | L1 | 9 | 390 | IHAMNPDIL | 19360 |
| HPV33 | L1 | 8 | 277 | IKGSGTTA | 19361 |
| HPV33 | L1 | 10 | 277 | IKGSGTTASI | 19362 |
| HPV33 | L1 | 10 | 52 | IKNPTNAKKL | 19363 |
| HPV33 | L1 | 11 | 52 | IKNPTNAKKLL | 19364 |
| HPV33 | L1 | 9 | 363 | IRHVEEYDL | 19365 |
| HPV33 | L1 | 11 | 363 | IRHVEEYDLQF | 19366 |
| HPV33 | L1 | 8 | 59 | KKLLVPKV | 19367 |
| HPV33 | L1 | 11 | 59 | KKLLVPKVSGL | 19368 |
| HPV33 | L1 | 10 | 473 | LKAKPKLKRA | 19369 |
| HPV33 | L1 | 11 | 473 | LKAKPKLKRAA | 19370 |
| HPV33 | L1 | 9 | 450 | LKEKFSADL | 19371 |
| HPV33 | L1 | 8 | 235 | LKMTSEPY | 19372 |
| HPV33 | L1 | 8 | 250 | LRREQMFV | 19373 |
| HPV33 | L1 | 11 | 250 | LRREQMFVRHF | 19374 |
| HPV33 | L1 | 10 | 82 | NKFGFPDTSF | 19375 |
| HPV33 | L1 | 11 | 82 | NKFGFPDTSFY | 19376 |
| HPV33 | L1 | 9 | 308 | NKPYWLQRA | 19377 |
| HPV33 | L1 | 9 | 216 | NKSDVPIDI | 19378 |
| HPV33 | L1 | 9 | 134 | NKYPGQPGA | 19379 |
| HPV33 | L1 | 9 | 262 | NRAGTLGEA | 19380 |
| HPV33 | L1 | 10 | 262 | NRAGTLGEAV | 19381 |
| HPV33 | L1 | 9 | 144 | NRECLSMDY | 19382 |
| HPV33 | L1 | 8 | 433 | PKEKEDPL | 19383 |
| HPV33 | L1 | 11 | 433 | PKEKEDPLGKY | 19384 |
| HPV33 | L1 | 8 | 64 | PKVSGLQY | 19385 |
| HPV33 | L1 | 10 | 64 | PKVSGLQYRV | 19386 |
| HPV33 | L1 | 11 | 64 | PKVSGLQYRVF | 19387 |
| HPV33 | L1 | 10 | 314 | QRAQGHNNGI | 19388 |
| HPV33 | L1 | 8 | 97 | QRLVWACV | 19389 |
| HPV33 | L1 | 10 | 97 | QRLVWACVGL | 19390 |
| HPV33 | L1 | 10 | 258 | RIIFFNRAGTL | 19391 |
| HPV33 | L1 | 8 | 364 | RHVEEYDL | 19392 |
| HPV33 | L1 | 10 | 364 | RHVEEYDLQF | 19393 |
| HPV33 | L1 | 11 | 364 | RHVEEYDLQFV | 19394 |
| HPV33 | L1 | 9 | 465 | RKFLLQAGL | 19395 |
| HPV33 | L1 | 11 | 465 | RKFLLQAGLKA | 19396 |
| HPV33 | L1 | 10 | 251 | RREQMFVRIIF | 19397 |
| HPV33 | L1 | 11 | 251 | RREQMFVRIIFF | 19398 |
| HPV33 | L1 | 9 | 19 | SKVVSTDEY | 19399 |
| HPV33 | L1 | 10 | 19 | SKVVSTDEYV | 19400 |
| HPV33 | L1 | 10 | 40 | SRLLAVGHPY | 19401 |
| HPV33 | L1 | 11 | 40 | SRLLAVGHPYF | 19402 |
| HPV33 | L1 | 8 | 29 | SRTSIYYY | 19403 |
| HPV33 | L1 | 9 | 29 | SRTSIYYYA | 19404 |
| HPV33 | L1 | 8 | 337 | TRSTNMTL | 19405 |
| HPV33 | L1 | 11 | 487 | TRTSSAKRKKV | 19406 |
| HPV33 | L1 | 8 | 257 | VRHFFNRA | 19407 |
| HPV33 | L1 | 11 | 257 | VRHFFNRAGTL | 19408 |
| HPV33 | L1 | 9 | 76 | VRLPDPNKF | 19409 |
| HPV33 | L1 | 11 | 76 | VRLPDPNKFGF | 19410 |
| HPV33 | L1 | 8 | 4 | WRPSEATV | 19411 |
| HPV33 | L1 | 9 | 4 | WRPSEATVY | 19412 |
| HPV33 | L1 | 10 | 4 | WRPSEATVYL | 19413 |
| HPV33 | L1 | 9 | 354 | YKNENFKEY | 19414 |
| HPV33 | L1 | 10 | 354 | YKNENFKEYI | 19415 |
| HPV33 | L1 | 8 | 152 | YKQTQLCL | 19416 |
| HPV33 | L1 | 9 | 152 | YKQTQLCLL | 19417 |
| HPV33 | L1 | 8 | 417 | YRFVTSQA | 19418 |
| HPV33 | L1 | 9 | 417 | YRFVTSQAI | 19419 |
| HPV33 | L1 | 8 | 71 | YRVFRVRL | 19420 |
| HPV33 | L2 | 9 | 320 | ARIHYYQDL | 19421 |
| HPV33 | L2 | 11 | 21 | CKATGTCPPDV | 19422 |
| HPV33 | L2 | 9 | 335 | DHTVPNEQY | 19423 |
| HPV33 | L2 | 11 | 335 | DHTVPNEQYEL | 19424 |
| HPV33 | L2 | 10 | 179 | GHFIFSSPTV | 19425 |
| HPV33 | L2 | 8 | 315 | GKQIGARI | 19426 |
| HPV33 | L2 | 10 | 315 | GKQIGARIHY | 19427 |
| HPV33 | L2 | 11 | 315 | GKQIGARIHYY | 19428 |
| HPV33 | L2 | 8 | 67 | GRTGYVPI | 19429 |
| HPV33 | L2 | 10 | 247 | HKLITYDNPA | 19430 |

TABLE XI-continued

| | | | | | |
|---|---|---|---|---|---|
| HPV33 | L2 | 11 | 247 | HKLITYDNPAF | 19431 |
| HPV33 | L2 | 10 | 3 | HKRSTRRKRA | 19432 |
| HPV33 | L2 | 10 | 322 | IHYYQDLSPI | 19433 |
| HPV33 | L2 | 11 | 322 | IHYYQDLSPIV | 19434 |
| HPV33 | L2 | 10 | 88 | IRPPVTVDTV | 19435 |
| HPV33 | L2 | 8 | 10 | KRASATQL | 19436 |
| HPV33 | L2 | 9 | 10 | KRASATQLY | 19437 |
| HPV33 | L2 | 10 | 454 | KRFPYFFTDV | 19438 |
| HPV33 | L2 | 9 | 4 | KRSTRRRRA | 19439 |
| HPV33 | L2 | 11 | 4 | KRSTRRKRASA | 19440 |
| HPV33 | L2 | 9 | 348 | LHDTSTSSY | 19441 |
| HPV33 | L2 | 11 | 348 | LHDTSTSSYSI | 19442 |
| HPV33 | L2 | 9 | 169 | LHPPAPAEA | 19443 |
| HPV33 | L2 | 8 | 442 | LHPSYFIL | 19444 |
| HPV33 | L2 | 9 | 310 | LKTRSGKQI | 19445 |
| HPV33 | L2 | 11 | 310 | LKTRSGKQIGA | 19446 |
| HPV33 | L2 | 8 | 45 | LKYGSLGV | 19447 |
| HPV33 | L2 | 9 | 45 | LKYGSLGVF | 19448 |
| HPV33 | L2 | 10 | 45 | LKYGSLGVFF | 19449 |
| HPV33 | L2 | 8 | 449 | LRRRRKRF | 19450 |
| HPV33 | L2 | 10 | 449 | LRRRRKRFPY | 19451 |
| HPV33 | L2 | 11 | 449 | LRRRRKRFPYF | 19452 |
| HPV33 | L2 | 11 | 246 | PHKLITYDNPA | 19453 |
| HPV33 | L2 | 8 | 33 | PKVEGSTI | 19454 |
| HPV33 | L2 | 9 | 33 | PKVEGSTIA | 19455 |
| HPV33 | L2 | 8 | 269 | QHSDISPA | 19456 |
| HPV33 | L2 | 8 | 378 | QHSYSTFA | 19457 |
| HPV33 | L2 | 11 | 2 | RHKRSTRRRRA | 19458 |
| HPV33 | L2 | 9 | 296 | RHTVRFSRV | 19459 |
| HPV33 | L2 | 9 | 9 | RKRASATQL | 19460 |
| HPV33 | L2 | 10 | 9 | RKRASATQLY | 19461 |
| HPV33 | L2 | 8 | 453 | RKRFPYFF | 19462 |
| HPV33 | L2 | 11 | 453 | RKRFPYFFTDV | 19463 |
| HPV33 | L2 | 10 | 295 | RRHTVRFSRV | 19464 |
| HPV33 | L2 | 10 | 8 | RRKRASATQL | 19465 |
| HPV33 | L2 | 11 | 8 | RRKRASATQLY | 19466 |
| HPV33 | L2 | 8 | 452 | RRKRFPYF | 19467 |
| HPV33 | L2 | 9 | 452 | RRKRFPYFF | 19468 |
| HPV33 | L2 | 8 | 451 | RRRKRFPY | 19469 |
| HPV33 | L2 | 9 | 451 | RRRKRFPYF | 19470 |
| HPV33 | L2 | 10 | 451 | RRRKRFPYFF | 19471 |
| HPV33 | L2 | 9 | 450 | RRRRKRFPY | 19472 |
| HPV33 | L2 | 10 | 450 | RRRRKRFPYF | 19473 |
| HPV33 | L2 | 11 | 450 | RRRRKRFPYFF | 19474 |
| HPV33 | L2 | 9 | 229 | SRNTQQVKV | 19475 |
| HPV33 | L2 | 10 | 229 | SRNTQQVKVV | 19476 |
| HPV33 | L2 | 9 | 219 | SHPVARLGL | 19477 |
| HPV33 | L2 | 10 | 219 | SHPVARLGLY | 19478 |
| HPV33 | L2 | 8 | 294 | SRRHTVRF | 19479 |
| HPV33 | L2 | 11 | 294 | SRRHTVRFSRV | 19480 |
| HPV33 | L2 | 9 | 302 | SRVGQKATL | 19481 |
| HPV33 | L2 | 8 | 7 | TRRKRASA | 19482 |
| HPV33 | L2 | 11 | 7 | TRRKRASATQL | 19483 |
| HPV33 | L2 | 9 | 312 | TRSGKQIGA | 19484 |
| HPV33 | L2 | 11 | 312 | TRSGKQIGARI | 19485 |
| HPV33 | L2 | 8 | 387 | TRTSNVSI | 19486 |
| HPV33 | L2 | 10 | 387 | TRTSNVSIPL | 19487 |
| HPV33 | L2 | 9 | 373 | VHTPMQHSY | 19488 |
| HPV33 | L2 | 8 | 235 | VKVVDPAF | 19489 |
| HPV33 | L2 | 9 | 235 | VKVVDPAFL | 19490 |
| HPV33 | L2 | 10 | 299 | VRFSRVGQKA | 19491 |
| HPV45 | E1 | 10 | 255 | AHIQCLDCKW | 19492 |
| HPV45 | E1 | 8 | 564 | AKDNKWPY | 19493 |
| HPV45 | E1 | 9 | 564 | AKDNKWPYL | 19494 |
| HPV45 | E1 | 8 | 284 | AKGLSTLL | 19495 |
| HPV45 | E1 | 10 | 284 | AKGLSTLLHV | 19496 |
| HPV45 | E1 | 8 | 125 | AKRRLFTI | 19497 |
| HPV45 | E1 | 8 | 392 | AKYLKDCA | 19498 |
| HPV45 | E1 | 9 | 392 | AKYLKDCAV | 19499 |
| HPV45 | E1 | 10 | 392 | AKYLKDCAVM | 19500 |
| HPV45 | E1 | 8 | 262 | CKWGVLIL | 19501 |
| HPV45 | E1 | 9 | 262 | CKWGVLILA | 19502 |
| HPV45 | E1 | 10 | 262 | CKWGVLILAL | 19503 |
| HPV45 | E1 | 11 | 262 | CKWGVLILALL | 19504 |
| HPV45 | E1 | 8 | 588 | DKNGNPVY | 19505 |
| HPV45 | E1 | 10 | 588 | DKNGNPVYEI | 19506 |
| HPV45 | E1 | 8 | 599 | DKNWKCFF | 19507 |
| HPV45 | E1 | 8 | 222 | DKTTCTDW | 19508 |
| HPV45 | E1 | 9 | 222 | DKTFCTDWV | 19509 |

TABLE XI-continued

| | | | | | |
|---|---|---|---|---|---|
| HPV45 | E1 | 10 | 222 | DKTTCTDWVM | 19510 |
| HPV45 | E1 | 11 | 222 | DKTTCTDWVMA | 19511 |
| HPV45 | E1 | 8 | 541 | DRKHKPLL | 19512 |
| HPV45 | E1 | 10 | 541 | DRKHKPLLQL | 19513 |
| HPV45 | E1 | 8 | 25 | EKKTGDVI | 19514 |
| HPV45 | E1 | 9 | 607 | ERTWSRLDL | 19515 |
| HPV45 | E1 | 10 | 70 | FHAQEVQNDA | 19516 |
| HPV45 | E1 | 9 | 204 | FKDIYGLSF | 19517 |
| HPV45 | E1 | 11 | 219 | FKSDKTTCTDW | 19518 |
| HPV45 | E1 | 8 | 244 | FKTLIKPA | 19519 |
| HPV45 | E1 | 10 | 244 | FKTLIKPATL | 19520 |
| HPV45 | E1 | 11 | 244 | FKTLIKPATLY | 19521 |
| HPV45 | E1 | 9 | 121 | GHKKAKRRL | 19522 |
| HPV45 | E1 | 10 | 121 | GHKKARRRLF | 19523 |
| HPV45 | E1 | 8 | 277 | GKNRLTVA | 19524 |
| HPV45 | E1 | 11 | 277 | GKNRLTVAKGL | 19525 |
| HPV45 | E1 | 9 | 475 | GKSYFGMSF | 19526 |
| HPV45 | E1 | 10 | 475 | GKSYFGMSFI | 19527 |
| HPV45 | E1 | 8 | 122 | HKKAKRRL | 19528 |
| HPV45 | E1 | 9 | 122 | RKKAKRRLF | 19529 |
| HPV45 | E1 | 11 | 122 | HKKAKRRLFFI | 19530 |
| HPV45 | E1 | 8 | 484 | IHFLQGAI | 19531 |
| HPV45 | E1 | 9 | 484 | IHFLQGAII | 19532 |
| HPV45 | E1 | 11 | 484 | IHFLQGMISF | 19533 |
| HPV45 | E1 | 8 | 248 | IKPATLYA | 19534 |
| HPV45 | E1 | 10 | 248 | IKPATLYAHI | 19535 |
| HPV45 | E1 | 8 | 419 | IKYRCSKI | 19536 |
| HPV45 | E1 | 8 | 543 | KIIKPLLQL | 19537 |
| HPV45 | E1 | 8 | 196 | KAAAMLAV | 19538 |
| HPV45 | E1 | 9 | 196 | KKAAMLAVF | 19539 |
| HPV45 | E1 | 8 | 123 | KKAKRRLF | 19540 |
| HPV45 | E1 | 10 | 123 | KAAKRRLFTI | 19541 |
| HPV45 | E1 | 8 | 462 | KKNCILLY | 19542 |
| HPV45 | E1 | 11 | 462 | KKNCWLYGPA | 19543 |
| HPV45 | E1 | 8 | 406 | KRAQKRQM | 19544 |
| HPV45 | E1 | 10 | 406 | KRAQKRQMNM | 19545 |
| HPV45 | E1 | 9 | 410 | KRQMNMSQW | 19546 |
| HPV45 | E1 | 10 | 410 | KRQMNMSQWI | 19547 |
| HPV45 | E1 | 8 | 615 | LHEDDEDA | 19548 |
| HPV45 | E1 | 8 | 82 | LHLLKRKF | 19549 |
| HPV45 | E1 | 9 | 82 | LHLLKRKPA | 19550 |
| HPV45 | E1 | 8 | 291 | LHVPETCM | 19551 |
| HPV45 | E1 | 9 | 291 | LHVPETCML | 19552 |
| HPV45 | E1 | 10 | 291 | LHVPETCMLI | 19553 |
| HPV45 | E1 | 8 | 550 | LKCPPWL | 19554 |
| HPV45 | E1 | 11 | 395 | LKDCAVMCRHY | 19555 |
| HPV45 | E1 | 10 | 457 | LKGTPKKNCI | 19556 |
| HPV45 | E1 | 11 | 457 | LKGTPKKNCIL | 19557 |
| HPV45 | E1 | 9 | 386 | LKSNCQAKY | 19558 |
| HPV45 | E1 | 10 | 386 | LKSNCQAKYL | 19559 |
| HPV45 | E1 | 8 | 450 | LRALKEFL | 19560 |
| HPV45 | E1 | 8 | 305 | LRSSVAAL | 19561 |
| HPV45 | E1 | 9 | 305 | LRSSVAALY | 19562 |
| HPV45 | E1 | 10 | 305 | LRSSVAALYW | 19563 |
| HPV45 | E1 | 11 | 305 | LRSSVAALYWY | 19564 |
| HPV45 | E1 | 10 | 272 | LRYKCGKNRL | 19565 |
| HPV45 | E1 | 8 | 439 | LRYQGVEF | 19566 |
| HPV45 | E1 | 9 | 439 | LRYQGVEFI | 19567 |
| HPV45 | E1 | 11 | 439 | LRYQGVEPISF | 19568 |
| HPV45 | E1 | 10 | 529 | MRNALDGNPI | 19569 |
| HPV45 | E1 | 8 | 195 | NKKAAMLA | 19570 |
| HPV45 | E1 | 9 | 195 | NKKAAMLAV | 19571 |
| HPV45 | E1 | 10 | 195 | NKKAAMLAVF | 19572 |
| HPV45 | E1 | 10 | 567 | NKWPYLESRV | 19573 |
| HPV45 | E1 | 9 | 279 | NRLTVAKGL | 19574 |
| HPV45 | E1 | 8 | 180 | PHCSITEL | 19575 |
| HPV45 | E1 | 11 | 180 | PHCSITELKEL | 19576 |
| HPV45 | E1 | 8 | 461 | PKKNCILL | 19577 |
| HPV45 | E1 | 9 | 461 | PKKNCILLY | 19578 |
| HPV45 | E1 | 8 | 303 | PKLRSSVA | 19579 |
| HPV45 | E1 | 9 | 303 | PKLRSSVAA | 19580 |
| HPV45 | E1 | 10 | 303 | PKLRSSVAAL | 19581 |
| HPV45 | E1 | 11 | 303 | PKLRSSVAALY | 19582 |
| HPV45 | E1 | 8 | 111 | PRLQEISL | 19583 |
| HPV45 | E1 | 9 | 340 | QHGIDDSNF | 19584 |
| HPV45 | E1 | 11 | 340 | QHGIDDSNFDL | 19585 |
| HPV45 | E1 | 10 | 409 | QKRQMNMSQW | 19586 |
| HPV45 | E1 | 11 | 409 | QKRQMNMSQWI | 19587 |
| HPV45 | E1 | 10 | 334 | QRLTIIQHGI | 19588 |

TABLE XI-continued

| | | | | | |
|---|---|---|---|---|---|
| HPV45 | E1 | 11 | 403 | RHYKRAQKRQM | 19589 |
| HPV45 | E1 | 9 | 542 | RKHKPLLQL | 19590 |
| HPV45 | E1 | 11 | 127 | RRLFTISDSGY | 19591 |
| HPV45 | E1 | 8 | 499 | SHFWLEPL | 19592 |
| HPV45 | E1 | 9 | 499 | SHFWLEPLA | 19593 |
| HPV45 | E1 | 11 | 93 | SKENSPLGEQL | 19594 |
| HPV45 | E1 | 9 | 424 | SKIDEGGDW | 19595 |
| HPV45 | E1 | 8 | 574 | SRVTVFTF | 19596 |
| HPV45 | E1 | 11 | 574 | SRVTVFTFPHA | 19597 |
| HPV45 | E1 | 8 | 518 | THTCWTYF | 19598 |
| HPV45 | E1 | 11 | 518 | THTCWTYFDNY | 19599 |
| HPV45 | E1 | 9 | 509 | TKVAMLDDA | 19600 |
| HPV45 | E1 | 9 | 602 | WKCFFERTW | 19601 |
| HPV45 | E1 | 8 | 432 | WRPIVQFL | 19602 |
| HPV45 | E1 | 10 | 432 | WRPIVQFLRY | 19603 |
| HPV45 | E1 | 8 | 274 | YKCGKNRL | 19604 |
| HPV45 | E1 | 10 | 274 | YKCGKNRLTV | 19605 |
| HPV45 | E1 | 11 | 274 | YKCGKNRLTVA | 19606 |
| HPV45 | E1 | 9 | 405 | YKRAQKRQM | 19607 |
| HPV45 | E1 | 11 | 405 | YKRAQKRQMNM | 19608 |
| HPV45 | E1 | 8 | 315 | YRTGISNI | 19609 |
| HPV45 | E1 | 11 | 315 | YRTGISNISEV | 19610 |
| HPV45 | E2 | 9 | 75 | AHKAIELQM | 19611 |
| HPV45 | E2 | 10 | 75 | AHKMELQMA | 19612 |
| HPV45 | E2 | 11 | 75 | AHKMELQMAL | 19613 |
| HPV45 | E2 | 9 | 52 | AREHGITKL | 19614 |
| HPV45 | E2 | 10 | 23 | DHYENDSKDI | 19615 |
| HPV45 | E2 | 10 | 315 | DHYSEISSTW | 19616 |
| HPV45 | E2 | 8 | 299 | DKNSLKCL | 19617 |
| HPV45 | E2 | 10 | 299 | DKNSLKCLRY | 19618 |
| HPV45 | E2 | 9 | 153 | DKTAACVSY | 19619 |
| HPV45 | E2 | 10 | 153 | DKTAACVSYW | 19620 |
| HPV45 | E2 | 11 | 54 | EHGITKLNHQV | 19621 |
| HPV45 | E2 | 9 | 183 | EKYGNSNTW | 19622 |
| HPV45 | E2 | 11 | 183 | EKYGNSNTWEV | 19623 |
| HPV45 | E2 | 10 | 12 | ERLSALQDKI | 19624 |
| HPV45 | E2 | 11 | 12 | ERLSALQDKIL | 19625 |
| HPV45 | E2 | 8 | 116 | FKKGGKTV | 19626 |
| HPV45 | E2 | 10 | 116 | FKKGGKTVHV | 19627 |
| HPV45 | E2 | 11 | 116 | FKKGGKTVHVY | 19628 |
| HPV45 | E2 | 8 | 178 | FKSECEKY | 19629 |
| HPV45 | E2 | 8 | 120 | GKTVHVYF | 19630 |
| HPV45 | E2 | 11 | 262 | GRVNTHVHNPL | 19631 |
| HPV45 | E2 | 9 | 260 | HHGRVNTHV | 19632 |
| HPV45 | E2 | 8 | 76 | HKAIELQM | 19633 |
| HPV45 | E2 | 9 | 76 | HKAIELQMA | 19634 |
| HPV45 | E2 | 10 | 76 | HKAIELQMAL | 19635 |
| HPV45 | E2 | 10 | 294 | IHLKGDKNSL | 19636 |
| HPV45 | E2 | 8 | 167 | IKDGDTTY | 19637 |
| HPV45 | E2 | 9 | 167 | IKDGDTTYY | 19638 |
| HPV45 | E2 | 10 | 167 | IKDGDTTYYV | 19639 |
| HPV45 | E2 | 8 | 42 | IRLENAIL | 19640 |
| HPV45 | E2 | 9 | 42 | IRLENAILF | 19641 |
| HPV45 | E2 | 11 | 42 | IRLENAILFTA | 19642 |
| HPV45 | E2 | 9 | 117 | KKGGKTVHV | 19643 |
| HPV45 | E2 | 10 | 117 | KKGGKTVHVY | 19644 |
| HPV45 | E2 | 11 | 117 | KKGGKTVHVYF | 19645 |
| HPV45 | E2 | 8 | 249 | KRPRQCGL | 19646 |
| HPV45 | E2 | 8 | 303 | LKCLRYRL | 19647 |
| HPV45 | E2 | 11 | 303 | LKCLRYRLRKY | 19648 |
| HPV45 | E2 | 8 | 296 | LKGDKNSL | 19649 |
| HPV45 | E2 | 11 | 296 | LKGDKNSLKCL | 19650 |
| HPV45 | E2 | 9 | 85 | LKGLAQSKY | 19651 |
| HPV45 | E2 | 8 | 310 | LRKYADHY | 19652 |
| HPV45 | E2 | 11 | 310 | LRKYADHYSEI | 19653 |
| HPV45 | E2 | 8 | 306 | LRYRLRKY | 19654 |
| HPV45 | E2 | 9 | 306 | LRYRLRKYA | 19655 |
| HPV45 | E2 | 10 | 1 | MKMQTPKESL | 19656 |
| HPV45 | E2 | 8 | 61 | NHQVVPPI | 19657 |
| HPV45 | E2 | 10 | 61 | NHQVVPPINI | 19658 |
| HPV45 | E2 | 8 | 130 | NKDNCMNY | 19659 |
| HPV45 | E2 | 9 | 130 | NKDNCMNYV | 19660 |
| HPV45 | E2 | 10 | 130 | NKDNCMNYVV | 19661 |
| HPV45 | E2 | 11 | 130 | NKDNCMYYVVW | 19662 |
| HPV45 | E2 | 9 | 330 | NKNTGILTV | 19663 |
| HPV45 | E2 | 11 | 330 | NKNTGILTVTY | 19664 |
| HPV45 | E2 | 9 | 6 | PKESLSERL | 19665 |
| HPV45 | E2 | 11 | 6 | PKESLSERLSA | 19666 |
| HPV45 | E2 | 9 | 239 | PKPHIQTPA | 19667 |

TABLE XI-continued

| | | | | | |
|---|---|---|---|---|---|
| HPV45 | E2 | 11 | 224 | QHASTSTPKTA | 19668 |
| HPV45 | E2 | 10 | 259 | QHHGRVNTHV | 19669 |
| HPV45 | E2 | 8 | 345 | QRNTFLDV | 19670 |
| HPV45 | E2 | 9 | 345 | QRNTFLDVV | 19671 |
| HPV45 | E2 | 11 | 345 | QRNTFLDVVTI | 19672 |
| HPV45 | E2 | 11 | 283 | RKVCSGNTTPI | 19673 |
| HPV45 | E2 | 10 | 311 | RKYADHYSEI | 19674 |
| HPV45 | E2 | 9 | 73 | SKAHKAIEL | 19675 |
| HPV45 | E2 | 11 | 73 | SKAHKAIELQM | 19676 |
| HPV45 | E2 | 8 | 29 | SKDINSQI | 19677 |
| HPV45 | E2 | 10 | 29 | SKDINSQISY | 19678 |
| HPV45 | E2 | 11 | 29 | SKDINSQISYW | 19679 |
| HPV45 | E2 | 8 | 71 | SKSKAHKA | 19680 |
| HPV45 | E2 | 9 | 71 | SKSKAHKAI | 19681 |
| HPV45 | E2 | 11 | 71 | SKSKAHKAIEL | 19682 |
| HPV45 | E2 | 8 | 91 | SKYNNEEW | 19683 |
| HPV45 | E2 | 10 | 91 | SKYNNEEWTL | 19684 |
| HPV45 | E2 | 8 | 266 | THVHNPLL | 19685 |
| HPV45 | E2 | 8 | 58 | TKLNHQVV | 19686 |
| HPV45 | E2 | 11 | 58 | TKLNHQVVPPI | 19687 |
| HPV45 | E2 | 9 | 248 | TKRPRQCGL | 19688 |
| HPV45 | E2 | 10 | 308 | YRLRKYADHY | 19689 |
| HPV45 | E6 | 11 | 2 | ARFDDPTQRPY | 19690 |
| HPV45 | E6 | 8 | 65 | CHKCIDFY | 19691 |
| HPV45 | E6 | 11 | 65 | CHKCIDFYSRI | 19692 |
| HPV45 | E6 | 10 | 35 | CKATLERTEV | 19693 |
| HPV45 | E6 | 11 | 35 | CKATLERTEVY | 19694 |
| HPV45 | E6 | 8 | 123 | DKRRFHSI | 19695 |
| HPV45 | E6 | 9 | 123 | DKRRFHSIA | 19696 |
| HPV45 | E6 | 8 | 91 | EKITNTEL | 19697 |
| HPV45 | E6 | 9 | 91 | EKITNTELY | 19698 |
| HPV45 | E6 | 11 | 91 | EKITNTELYNL | 19699 |
| HPV45 | E6 | 11 | 148 | ERLRRRETQV | 19700 |
| HPV45 | E6 | 8 | 40 | ERTEVYQF | 19701 |
| HPV45 | E6 | 9 | 40 | ERTEVYQFA | 19702 |
| HPV45 | E6 | 10 | 40 | ERTEVYQFAF | 19703 |
| HPV45 | E6 | 8 | 127 | FHSIAGQY | 19704 |
| HPV45 | E6 | 8 | 49 | FKDLFIVY | 19705 |
| HPV45 | E6 | 10 | 66 | HKCIDFYSRI | 19706 |
| HPV45 | E6 | 10 | 103 | IRCLRCQKPL | 19707 |
| HPV45 | E6 | 11 | 75 | IRELRYYSNSV | 19708 |
| HPV45 | E6 | 8 | 124 | KRRFHSIA | 19709 |
| HPV45 | E6 | 11 | 124 | KRRFHSIAGQY | 19710 |
| HPV45 | E6 | 11 | 117 | KRRHLKDKRRF | 19711 |
| HPV45 | E6 | 10 | 121 | LKDKRRFHSI | 19712 |
| HPV45 | E6 | 11 | 121 | LKDKRRFHSIA | 19713 |
| HPV45 | E6 | 10 | 106 | LRCQKPLNPA | 19714 |
| HPV45 | E6 | 9 | 150 | LRRRRETQV | 19715 |
| HPV45 | E6 | 8 | 78 | LRYYSNSV | 19716 |
| HPV45 | E6 | 9 | 78 | LRYYSNSVY | 19717 |
| HPV45 | E6 | 9 | 9 | QRPYKLPDL | 19718 |
| HPV45 | E6 | 9 | 119 | RHLKDKRRF | 19719 |
| HPV45 | E6 | 10 | 125 | RRFHSIAGQY | 19720 |
| HPV45 | E6 | 10 | 118 | RRHLKDKRRF | 19721 |
| HPV45 | E6 | 8 | 151 | RRRRETQV | 19722 |
| HPV45 | E6 | 8 | 73 | SRIRELRY | 19723 |
| HPV45 | E6 | 9 | 73 | SRIRELRYY | 19724 |
| HPV45 | E6 | 10 | 12 | YKLPDLGFLL | 19725 |
| HPV45 | E6 | 8 | 56 | YRDCIAYA | 19726 |
| HPV45 | E6 | 9 | 56 | YRDCIAYAA | 19727 |
| HPV45 | E7 | 11 | 52 | ARRAEPQRRKI | 19728 |
| HPV45 | E7 | 9 | 67 | CKCDGRIEL | 19729 |
| HPV45 | E7 | 11 | 67 | CKCDGRIELTV | 19730 |
| HPV45 | E7 | 11 | 71 | GRIELTVESSA | 19731 |
| HPV45 | E7 | 9 | 13 | LHLEPQNEL | 19732 |
| HPV45 | E7 | 8 | 84 | LRTLQQLF | 19733 |
| HPV45 | E7 | 9 | 84 | LRTLQQLFL | 19734 |
| HPV45 | E7 | 8 | 1 | MHGPRATL | 19735 |
| HPV45 | E7 | 11 | 1 | MHGPRATLQEI | 19736 |
| HPV45 | E7 | 8 | 4 | PRATLQEI | 19737 |
| HPV45 | E7 | 9 | 4 | PRATLQEIV | 19738 |
| HPV45 | E7 | 10 | 4 | PRATLQEIVL | 19739 |
| HPV45 | E7 | 8 | 58 | QRHKILCV | 19740 |
| HPV45 | E7 | 10 | 53 | RRAEPQRHKI | 19741 |
| HPV45 | E7 | 11 | 53 | RRAEPQRHKIL | 19742 |
| HPV45 | E7 | 10 | 46 | SHAQLPARRA | 19743 |
| HPV45 | L1 | 8 | 159 | AHAATAVI | 19744 |
| HPV45 | L1 | 10 | 2 | AHNIIYGHGI | 19745 |
| HPV45 | L1 | 11 | 2 | AHNIIYGRGII | 19746 |

TABLE XI-continued

| | | | | | |
|---|---|---|---|---|---|
| HPV45 | L1 | 9 | 197 | AKGTLCKPA | 19747 |
| HPV45 | L1 | 11 | 197 | AKGTLCKPAQL | 19748 |
| HPV45 | L1 | 8 | 284 | ARHFWNRA | 19749 |
| HPV45 | L1 | 10 | 284 | ARHFWNRAGV | 19750 |
| HPV45 | L1 | 11 | 284 | ARHFWNRAGVM | 19751 |
| HPV45 | L1 | 9 | 45 | ARVVNTDDY | 19752 |
| HPV45 | L1 | 10 | 45 | ARVVNTDDYV | 19753 |
| HPV45 | L1 | 9 | 256 | CKYPDYLQM | 19754 |
| HPV45 | L1 | 11 | 256 | CKYPDYLQMSA | 19755 |
| HPV45 | L1 | 8 | 472 | DKLKFWTV | 19756 |
| HPV45 | L1 | 10 | 472 | DKLKFWTVDL | 19757 |
| HPV45 | L1 | 8 | 194 | EHWAKGTL | 19758 |
| HPV45 | L1 | 10 | 483 | EKFSSDLDQY | 19759 |
| HPV45 | L1 | 9 | 466 | EKQDPYDKL | 19760 |
| HPV45 | L1 | 11 | 466 | EKQDPYDKLKF | 19761 |
| HPV45 | L1 | 8 | 390 | FKHYSRHV | 19762 |
| HPV45 | L1 | 11 | 390 | FKHYSRHVEEY | 19763 |
| HPV45 | L1 | 11 | 100 | FRVALPDPNKF | 19764 |
| HPV45 | L1 | 8 | 76 | FRVVPSGA | 19765 |
| HPV45 | L1 | 8 | 8 | GHGIIIFL | 19766 |
| HPV45 | L1 | 11 | 8 | GHGIIIFLKNV | 19767 |
| HPV45 | L1 | 8 | 347 | GHNNGICW | 19768 |
| HPV45 | L1 | 8 | 146 | GHPFYNKL | 19769 |
| HPV45 | L1 | 8 | 135 | GRGQPLGI | 19770 |
| HPV45 | L1 | 10 | 135 | GRGQPLGIGL | 19771 |
| HPV45 | L1 | 8 | 495 | GRKFLVQA | 19772 |
| HPV45 | L1 | 10 | 495 | GRKFLVQAGL | 19773 |
| HPV45 | L1 | 10 | 343 | HKAQGHNNGI | 19774 |
| HPV45 | L1 | 8 | 421 | IHSMNSSI | 19775 |
| HPV45 | L1 | 9 | 421 | IHSMNSSIL | 19776 |
| HPV45 | L1 | 8 | 304 | IKGTSANM | 19777 |
| HPV45 | L1 | 10 | 391 | KHYSRHVEEY | 19778 |
| HPV45 | L1 | 10 | 514 | KRPAASTSTA | 19779 |
| HPV45 | L1 | 11 | 342 | LHKAQGHNNGI | 19780 |
| HPV45 | L1 | 9 | 481 | LKEKFSSDL | 19781 |
| HPV45 | L1 | 8 | 474 | LKFWTVDL | 19782 |
| HPV45 | L1 | 11 | 217 | LKNTIIEDGDM | 19783 |
| HPV45 | L1 | 9 | 15 | LKNVNVFPI | 19784 |
| HPV45 | L1 | 10 | 15 | LKNVNVFPIF | 19785 |
| HPV45 | L1 | 11 | 15 | LKNVNVFPIFL | 19786 |
| HPV45 | L1 | 8 | 277 | LRREQLFA | 19787 |
| HPV45 | L1 | 11 | 277 | LRREQLFARIIF | 19788 |
| HPV45 | L1 | 9 | 311 | MRETPGSCV | 19789 |
| HPV45 | L1 | 10 | 311 | MRETPGSCVY | 19790 |
| HPV45 | L1 | 10 | 108 | NKFGLPDSTI | 19791 |
| HPV45 | L1 | 11 | 108 | NKFGLPDSTIY | 19792 |
| HPV45 | L1 | 9 | 151 | NKLDDTESA | 19793 |
| HPV45 | L1 | 11 | 151 | NKLDDTESAHA | 19794 |
| HPV45 | L1 | 9 | 337 | NKPYWLHKA | 19795 |
| HPV45 | L1 | 8 | 85 | NKQAVPKV | 19796 |
| HPV45 | L1 | 10 | 85 | NKQAVPKVSA | 19797 |
| HPV45 | L1 | 11 | 85 | NKQAVPKVSAY | 19798 |
| HPV45 | L1 | 10 | 289 | NRAGVMGDTV | 19799 |
| HPV45 | L1 | 8 | 90 | PKVSAYQY | 19800 |
| HPV45 | L1 | 10 | 90 | PKVSAYQYRV | 19801 |
| HPV45 | L1 | 11 | 90 | PKVSAYQYRVF | 19802 |
| HPV45 | L1 | 8 | 123 | QRLVWACV | 19803 |
| HPV45 | L1 | 10 | 123 | QRLVWACVGM | 19804 |
| HPV45 | L1 | 9 | 285 | RHFWNRAGV | 19805 |
| HPV45 | L1 | 10 | 285 | RHFWNRAGVM | 19806 |
| HPV45 | L1 | 8 | 395 | RHVEEYDL | 19807 |
| HPV45 | L1 | 10 | 395 | RHVEEYDLQF | 19808 |
| HPV45 | L1 | 11 | 395 | RHVEEYDLQFI | 19809 |
| HPV45 | L1 | 9 | 496 | RKFLVQAGL | 19810 |
| HPV45 | L1 | 11 | 513 | RKRPAASTSTA | 19811 |
| HPV45 | L1 | 10 | 278 | RREQLFARHF | 19812 |
| HPV45 | L1 | 11 | 278 | RREQLFARHFW | 19813 |
| HPV45 | L1 | 9 | 394 | SRHVEEYDL | 19814 |
| HPV45 | L1 | 11 | 394 | SRHVEEYDLQF | 19815 |
| HPV45 | L1 | 10 | 66 | SRLLTVGNPY | 19816 |
| HPV45 | L1 | 11 | 66 | SRLLTVGNPYF | 19817 |
| HPV45 | L1 | 9 | 524 | SRPAKRVRI | 19818 |
| HPV45 | L1 | 9 | 55 | SRTSIFYHA | 19819 |
| HPV45 | L1 | 9 | 243 | TKCEVPLDI | 19820 |
| HPV45 | L1 | 10 | 388 | TKFKHYSRHV | 19821 |
| HPV45 | L1 | 8 | 366 | TRSTNLTL | 19822 |
| HPV45 | L1 | 10 | 366 | TRSTNLTLCA | 19823 |
| HPV45 | L1 | 9 | 170 | VRDNVSVDY | 19824 |
| HPV45 | L1 | 9 | 354 | WHNQLFVTV | 19825 |

TABLE XI-continued

| | | | | | |
|---|---|---|---|---|---|
| HPV45 | L1 | 10 | 354 | WHNQLFVTVV | 19826 |
| HPV45 | L1 | 8 | 30 | WRPSDSTV | 19827 |
| HPV45 | L1 | 9 | 30 | WRPSDSTVY | 19828 |
| HPV45 | L1 | 10 | 30 | WRPSDSTVYL | 19829 |
| HPV45 | L1 | 8 | 61 | YHAGSSRL | 19830 |
| HPV45 | L1 | 9 | 61 | YHAGSSRLL | 19831 |
| HPV45 | L1 | 11 | 61 | YHAGSSRLLTV | 19832 |
| HPV45 | L1 | 8 | 178 | YKQTQLCI | 19833 |
| HPV45 | L1 | 9 | 178 | YKQTQLCIL | 19834 |
| HPV45 | L1 | 8 | 448 | YRFVQSVA | 19835 |
| HPV45 | L1 | 9 | 448 | YRFVQSVAV | 19836 |
| HPV45 | L1 | 8 | 97 | YRVFRVAL | 19837 |
| HPV45 | L2 | 8 | 7 | ARRKRASA | 19838 |
| HPV45 | L2 | 11 | 7 | ARRKRASATDL | 19839 |
| HPV45 | L2 | 11 | 21 | CKQSGTCPPDV | 19840 |
| HPV45 | L2 | 9 | 42 | DKILQWSSL | 19841 |
| HPV45 | L2 | 11 | 42 | DKILQWSSLGI | 19842 |
| HPV45 | L2 | 8 | 310 | GKQIGGRV | 19843 |
| HPV45 | L2 | 10 | 310 | GKQIGGRVHF | 19844 |
| HPV45 | L2 | 11 | 310 | GKQIGGRVHFY | 19845 |
| HPV45 | L2 | 9 | 76 | GRSNTVVDV | 19846 |
| HPV45 | L2 | 8 | 67 | GRTGYVPL | 19847 |
| HPV45 | L2 | 9 | 315 | GRVIIFYHDI | 19848 |
| HPV45 | L2 | 9 | 365 | HKSFYYPKY | 19849 |
| HPV45 | L2 | 11 | 365 | HKSFYYPKYSL | 19850 |
| HPV45 | L2 | 9 | 4 | HRAARRKRA | 19851 |
| HPV45 | L2 | 11 | 4 | HRAARRKRASA | 19852 |
| HPV45 | L2 | 8 | 431 | IHGTQYYL | 19853 |
| HPV45 | L2 | 9 | 431 | IHGTQYYLW | 19854 |
| HPV45 | L2 | 11 | 431 | IHGTQYYLWPW | 19855 |
| HPV45 | L2 | 10 | 364 | IHKSFTYPKY | 19856 |
| HPV45 | L2 | 8 | 280 | IRLHRPAL | 19857 |
| HPV45 | L2 | 8 | 447 | KKRKRIPY | 19858 |
| HPV45 | L2 | 9 | 447 | KKRKRIPYF | 19859 |
| HPV45 | L2 | 10 | 447 | KKRKRIPYFF | 19860 |
| HPV45 | L2 | 11 | 447 | KKRKRIPYFFA | 19861 |
| HPV45 | L2 | 8 | 10 | KRASATDL | 19862 |
| HPV45 | L2 | 9 | 10 | KRASATDLY | 19863 |
| HPV45 | L2 | 8 | 450 | KRIPYFFA | 19864 |
| HPV45 | L2 | 11 | 450 | KRIPYFFADGF | 19865 |
| HPV45 | L2 | 8 | 448 | KRKRIPYF | 19866 |
| HPV45 | L2 | 9 | 448 | KRKRIPYFF | 19867 |
| HPV45 | L2 | 10 | 448 | KRKRIPYFFA | 19868 |
| HPV45 | L2 | 8 | 33 | NKVEGTTL | 19869 |
| HPV45 | L2 | 9 | 33 | NKVEGTTLA | 19870 |
| HPV45 | L2 | 9 | 446 | PKKRKRIPY | 19871 |
| HPV45 | L2 | 10 | 446 | PKKRKRIPYF | 19872 |
| HPV45 | L2 | 11 | 446 | PKKRKRIPYFF | 19873 |
| HPV45 | L2 | 11 | 371 | PKYSLTMPSTA | 19874 |
| HPV45 | L2 | 11 | 224 | PRLYSRANQQV | 19875 |
| HPV45 | L2 | 9 | 9 | RRRASATDL | 19876 |
| HPV45 | L2 | 10 | 9 | RRRASATDLY | 19877 |
| HPV45 | L2 | 8 | 449 | RKRIPYFF | 19878 |
| HPV45 | L2 | 9 | 449 | RKRIPYFFA | 19879 |
| HPV45 | L2 | 10 | 290 | RRGTVRFSRL | 19880 |
| HPV45 | L2 | 10 | 8 | RRRRASATDL | 19881 |
| HPV45 | L2 | 11 | 8 | RRKRASATDLY | 19882 |
| HPV45 | L2 | 8 | 219 | RRVRGPRL | 19883 |
| HPV45 | L2 | 9 | 219 | RRVRGPRLY | 19884 |
| HPV45 | L2 | 9 | 189 | SHGYEEIPL | 19885 |
| HPV45 | L2 | 10 | 3 | SHRAARRKRA | 19886 |
| HPV45 | L2 | 9 | 228 | SRANQQVRV | 19887 |
| HPV45 | L2 | 9 | 297 | SRLGQRATM | 19888 |
| HPV45 | L2 | 10 | 297 | SRLGQRATMF | 19889 |
| HPV45 | L2 | 8 | 289 | SRRGTVRF | 19890 |
| HPV45 | L2 | 11 | 289 | SRRGTVRFSRL | 19891 |
| HPV45 | L2 | 9 | 243 | THPSSLVTF | 19892 |
| HPV45 | L2 | 10 | 87 | TRPPVVIEPV | 19893 |
| HPV45 | L2 | 11 | 307 | TRSGKQIGGRV | 19894 |
| HPV45 | L2 | 10 | 317 | VHFYHDISPI | 19895 |
| HPV45 | L2 | 11 | 317 | VHFYHDISPIA | 19896 |
| HPV45 | L2 | 10 | 294 | VRFSRLGQRA | 19897 |
| HPV45 | L2 | 10 | 221 | VRGPRLYSRA | 19898 |
| HPV45 | L2 | 9 | 218 | VRRVRGPRL | 19899 |
| HPV45 | L2 | 10 | 218 | VRRVRGPRLY | 19900 |
| HPV45 | L2 | 8 | 234 | VRVSTSQF | 19901 |
| HPV45 | L2 | 9 | 234 | VRVSTSQFL | 19902 |
| HPV45 | L2 | 8 | 320 | YHDISPIA | 19903 |
| HPV45 | L2 | 9 | 320 | YHDISPIAA | 19904 |

TABLE XI-continued

| | | | | | |
|---|---|---|---|---|---|
| HPV56 | E2 | 9 | 10 | AKACSAIEV | 19905 |
| HPV56 | E2 | 11 | 10 | AKACSAIEVQI | 19906 |
| HPV56 | E2 | 10 | 202 | AKCVTFHTHI | 19907 |
| HPV56 | E2 | 9 | 118 | AKKFGCKNI | 19908 |
| HPV56 | E2 | 10 | 118 | AKKFGCKNIW | 19909 |
| HPV56 | E2 | 8 | 8 | CKAKACSA | 19910 |
| HPV56 | E2 | 9 | 8 | CKAKACSAI | 19911 |
| HPV56 | E2 | 11 | 8 | CKAKACSAIEV | 19912 |
| HPV56 | E2 | 9 | 123 | CKNIWEVHM | 19913 |
| HPV56 | E2 | 8 | 146 | CRYNVSPV | 19914 |
| HPV56 | E2 | 11 | 146 | CRYNVSPVETV | 19915 |
| HPV56 | E2 | 8 | 250 | CRYRFQKY | 19916 |
| HPV56 | E2 | 11 | 250 | CRYRFQKYKTL | 19917 |
| HPV56 | E2 | 9 | 232 | DKTTPVVHL | 19918 |
| HPV56 | E2 | 8 | 53 | FKKEGQHI | 19919 |
| HPV56 | E2 | 10 | 53 | FKKEGQHIEV | 19920 |
| HPV56 | E2 | 11 | 53 | FKKEGQHIEVW | 19921 |
| HPV56 | E2 | 9 | 106 | GHKTYYTDF | 19922 |
| HPV56 | E2 | 11 | 184 | GKRPRLRESEF | 19923 |
| HPV56 | E2 | 11 | 162 | HKTTTTTSTSV | 19924 |
| HPV56 | E2 | 8 | 107 | HKTYYTDF | 19925 |
| HPV56 | E2 | 9 | 181 | HRPGKRPRL | 19926 |
| HPV56 | E2 | 11 | 50 | KKCFKKEGQHI | 19927 |
| HPV56 | E2 | 9 | 54 | KKEGQHIEV | 19928 |
| HPV56 | E2 | 10 | 54 | KKEGQHIEVW | 19929 |
| HPV56 | E2 | 11 | 54 | KKEGQHIEVWF | 19930 |
| HPV56 | E2 | 8 | 119 | KKFGCKNI | 19931 |
| HPV56 | E2 | 9 | 119 | KKFGCKNIW | 19932 |
| HPV56 | E2 | 11 | 119 | KKFGCKNIWEV | 19933 |
| HPV56 | E2 | 10 | 185 | KRPRLRESEF | 19934 |
| HPV56 | E2 | 8 | 247 | LKCCRYRF | 19935 |
| HPV56 | E2 | 11 | 247 | LKCCRYRFQKY | 19936 |
| HPV56 | E2 | 8 | 240 | LKGEPNRL | 19937 |
| HPV56 | E2 | 8 | 37 | LRDTCEEL | 19938 |
| HPV56 | E2 | 9 | 37 | LRDTCEELW | 19939 |
| HPV56 | E2 | 10 | 37 | LRDTCEELWL | 19940 |
| HPV56 | E2 | 10 | 228 | NHPGDKTTPV | 19941 |
| HPV56 | E2 | 11 | 228 | NHPGDKTTPVV | 19942 |
| HPV56 | E2 | 9 | 275 | NKNYSHTI | 19943 |
| HPV56 | E2 | 10 | 275 | NKNYSHTII | 19944 |
| HPV56 | E2 | 11 | 275 | NKNYSHTIIY | 19945 |
| HPV56 | E2 | 8 | 245 | NRLKCCRY | 19946 |
| HPV56 | E2 | 10 | 245 | NRLKCCRYRF | 19947 |
| HPV56 | E2 | 8 | 187 | PRLRESEF | 19948 |
| HPV56 | E2 | 9 | 89 | QKVCSGVDY | 19949 |
| HPV56 | E2 | 8 | 255 | QKYKTLFV | 19950 |
| HPV56 | E2 | 10 | 255 | QKYKTLFVDV | 19951 |
| HPV56 | E2 | 9 | 290 | QRNSFLSHV | 19952 |
| HPV56 | E2 | 11 | 290 | QRNSFLSHVKI | 19953 |
| HPV56 | E2 | 10 | 180 | SHRPGKRPRL | 19954 |
| HPV56 | E2 | 8 | 296 | SHVKIPVV | 19955 |
| HPV56 | E2 | 9 | 296 | SHVKIPVVY | 19956 |
| HPV56 | E2 | 11 | 296 | SHVKIPVVYRL | 19957 |
| HPV56 | E2 | 8 | 67 | SKNNCMQY | 19958 |
| HPV56 | E2 | 9 | 67 | SKNNCMQYV | 19959 |
| HPV56 | E2 | 10 | 67 | SKNNCMQYVA | 19960 |
| HPV56 | E2 | 11 | 67 | SKNNCMQYVAW | 19961 |
| HPV56 | E2 | 9 | 197 | SRESHAKCV | 19962 |
| HPV56 | E2 | 8 | 103 | VHDGHKTY | 19963 |
| HPV56 | E2 | 9 | 103 | VHDGHKTYY | 19964 |
| HPV56 | E2 | 10 | 238 | VHLKGEFNRL | 19965 |
| HPV56 | E2 | 8 | 129 | VHMENEST | 19966 |
| HPV56 | E2 | 9 | 129 | VHMENESTY | 19967 |
| HPV56 | E2 | 9 | 298 | VKIPVVYRL | 19968 |
| HPV56 | E2 | 10 | 298 | VKIPVVYRLV | 19969 |
| HPV56 | E2 | 11 | 298 | VKIPVVYRLVW | 19970 |
| HPV56 | E2 | 11 | 268 | YHWTSTDNKNY | 19971 |
| HPV56 | E2 | 10 | 285 | YKDETQRNSF | 19972 |
| HPV56 | E2 | 11 | 285 | YKDETQRNSFL | 19973 |
| HPV56 | E2 | 8 | 257 | YKTLFVDV | 19974 |
| HPV56 | E2 | 9 | 252 | YRFQKYKTL | 19975 |
| HPV56 | E2 | 10 | 252 | YRFQKYKTLF | 19976 |
| HPV56 | E2 | 11 | 252 | YRFQKYKTLFV | 19977 |
| HPV56 | E6 | 9 | 132 | AHGWTGSCL | 19978 |
| HPV56 | E6 | 8 | 36 | CKKELTRA | 19979 |
| HPV56 | E6 | 10 | 36 | CKKELTRAEV | 19980 |
| HPV56 | E6 | 11 | 36 | CKKELTRAEVY | 19981 |
| HPV56 | E6 | 8 | 66 | CRVCLLFY | 19982 |
| HPV56 | E6 | 11 | 66 | CRVCLLFYSKV | 19983 |

TABLE XI-continued

| | | | | | |
|---|---|---|---|---|---|
| HPV56 | E6 | 8 | 123 | DRKRRFHL | 19984 |
| HPV56 | E6 | 9 | 123 | DRKRRFHLI | 19985 |
| HPV56 | E6 | 10 | 123 | DRKRRFHLIA | 19986 |
| HPV56 | E6 | 9 | 10 | ERPRSLHHL | 19987 |
| HPV56 | E6 | 8 | 128 | FHLIAHGW | 19988 |
| HPV56 | E6 | 9 | 16 | HHLSEVLEI | 19989 |
| HPV56 | E6 | 11 | 16 | HHLSEVLEIPL | 19990 |
| HPV56 | E6 | 10 | 104 | IRCYRCQSPL | 19991 |
| HPV56 | E6 | 9 | 37 | KKELTRAEV | 19992 |
| HPV56 | E6 | 10 | 37 | KKELTRAEVY | 19993 |
| HPV56 | E6 | 8 | 96 | KKQLCDLL | 19994 |
| HPV56 | E6 | 9 | 96 | KKQLCDLLI | 19995 |
| HPV56 | E6 | 8 | 125 | KRRFHLIA | 19996 |
| HPV56 | E6 | 11 | 125 | KRRFHLIAHGW | 19997 |
| HPV56 | E6 | 9 | 120 | LHCDRKRRF | 19998 |
| HPV56 | E6 | 11 | 120 | LHCDRKRRFHL | 19999 |
| HPV56 | E6 | 8 | 15 | LHHLSEVL | 20000 |
| HPV56 | E6 | 10 | 15 | LHHLSEVLEI | 20001 |
| HPV56 | E6 | 9 | 53 | LKLVYRDDF | 20002 |
| HPV56 | E6 | 11 | 53 | LKLVRRDDFPY | 20003 |
| HPV56 | E6 | 10 | 12 | PRSLHHLSEV | 20004 |
| HPV56 | E6 | 11 | 12 | PRSLHHLSEVL | 20005 |
| HPV56 | E6 | 8 | 124 | RKRRFHLI | 20006 |
| HPV56 | E6 | 9 | 124 | RKRRFHLIA | 20007 |
| HPV56 | E6 | 8 | 77 | RKYRYYDY | 20008 |
| HPV56 | E6 | 10 | 77 | RKYRYYDYSV | 20009 |
| HPV56 | E6 | 11 | 77 | RKYRYYDYSVY | 20010 |
| HPV56 | E6 | 10 | 126 | RRFHLIAHGW | 20011 |
| HPV56 | E6 | 8 | 74 | SKVRKYRY | 20012 |
| HPV56 | E6 | 9 | 74 | SKVRKYRYY | 20013 |
| HPV56 | E6 | 11 | 74 | SKVRKYRYYDY | 20014 |
| HPV56 | E6 | 9 | 147 | SREPRESTV | 20015 |
| HPV56 | E6 | 8 | 95 | TKKQLCDL | 20016 |
| HPV56 | E6 | 9 | 95 | TKKQLCDLL | 20017 |
| HPV56 | E6 | 10 | 95 | TKKQLCDLLI | 20018 |
| HPV56 | E6 | 8 | 41 | TRAEVYNF | 20019 |
| HPV56 | E6 | 9 | 41 | TRAEVYNFA | 20020 |
| HPV56 | E6 | 9 | 76 | VRKYRYYDY | 20021 |
| HPV56 | E6 | 11 | 76 | VRKYRYYDYSV | 20022 |
| HPV56 | E6 | 8 | 57 | YRDDFPYA | 20023 |
| HPV56 | E6 | 9 | 57 | YRDDFPYAV | 20024 |
| HPV56 | E6 | 8 | 79 | YRYYDYSV | 20025 |
| HPV56 | E6 | 9 | 79 | YRYYDYSVY | 20026 |
| HPV56 | E6 | 11 | 79 | YRYYDYSVYGA | 20027 |
| HPV56 | E7 | 8 | 53 | AKQHTCYL | 20028 |
| HPV56 | E7 | 9 | 53 | AKQHTCYLI | 20029 |
| HPV56 | E7 | 11 | 53 | AKQHTCYLIHV | 20030 |
| HPV56 | E7 | 10 | 50 | ARQAKQHTCY | 20031 |
| HPV56 | E7 | 11 | 50 | ARQAKQHTCYL | 20032 |
| HPV56 | E7 | 9 | 68 | CKFVVQLDI | 20033 |
| HPV56 | E7 | 10 | 41 | DHLQERPQQA | 20034 |
| HPV56 | E7 | 9 | 45 | ERPQQARQA | 20035 |
| HPV56 | E7 | 9 | 3 | GKVPTLQDV | 20036 |
| HPV56 | E7 | 10 | 3 | GKVPTLQDVV | 20037 |
| HPV56 | E7 | 11 | 3 | GKVPTLQDVVL | 20038 |
| HPV56 | E7 | 10 | 61 | IHVPCCECKF | 20039 |
| HPV56 | E7 | 11 | 61 | IHVPCCECKFV | 20040 |
| HPV56 | E7 | 8 | 83 | LRVVQQLL | 20041 |
| HPV56 | E7 | 9 | 83 | LRVVQQLLM | 20042 |
| HPV56 | E7 | 11 | 83 | LRVVQQLLMGA | 20043 |
| HPV56 | E7 | 8 | 1 | MHGKVPTL | 20044 |
| HPV56 | E7 | 11 | 1 | MHGKVPTLQDV | 20045 |
| HPV56 | E7 | 9 | 55 | QHTCYLIHV | 20046 |
| HPV56 | E7 | 8 | 79 | TKEDLRVV | 20047 |
| HPV56 | E7 | 11 | 79 | TKEDLRVVQQL | 20048 |
| HPV56 | L1 | 8 | 475 | AKYKFWDV | 20049 |
| HPV56 | L1 | 10 | 475 | AKYKFWDVNL | 20050 |
| HPV56 | L1 | 8 | 291 | ARHYFNRA | 20051 |
| HPV56 | L1 | 11 | 291 | ARHYFNRAGKV | 20052 |
| HPV56 | L1 | 8 | 390 | ARKINQYL | 20053 |
| HPV56 | L1 | 11 | 390 | ARKINQYLRHV | 20054 |
| HPV56 | L1 | 9 | 412 | CKITLSAEV | 20055 |
| HPV56 | L1 | 10 | 412 | CKITLSAEVM | 20056 |
| HPV56 | L1 | 11 | 412 | CKITLSAEVMA | 20057 |
| HPV56 | L1 | 9 | 263 | CKYPDYLKM | 20058 |
| HPV56 | L1 | 11 | 263 | CKYPDYLKMSA | 20059 |
| HPV56 | L1 | 10 | 449 | DKYRYVRSTA | 20060 |
| HPV56 | L1 | 11 | 449 | DKYRYVRSTAI | 20061 |
| HPV56 | L1 | 8 | 201 | EHWTKGAV | 20062 |

TABLE XI-continued

| | | | | | |
|---|---|---|---|---|---|
| HPV56 | L1 | 9 | 469 | EKQDPLAKY | 20063 |
| HPV56 | L1 | 11 | 469 | EKQDPLAKYKF | 20064 |
| HPV56 | L1 | 8 | 130 | ERLVWACV | 20065 |
| HPV56 | L1 | 10 | 130 | ERLVWACVGL | 20066 |
| HPV56 | L1 | 9 | 244 | FKVLQESKA | 20067 |
| HPV56 | L1 | 11 | 244 | FKVLQESKAEV | 20068 |
| HPV56 | L1 | 11 | 107 | FRVRLPDPNKF | 20069 |
| HPV56 | L1 | 8 | 352 | GHNNGICW | 20070 |
| HPV56 | L1 | 8 | 153 | GHPLFNRL | 20071 |
| HPV56 | L1 | 8 | 185 | GKQTQLCI | 20072 |
| HPV56 | L1 | 9 | 185 | GKQTQLCIV | 20073 |
| HPV56 | L1 | 9 | 299 | GKVGETIPA | 20074 |
| HPV56 | L1 | 11 | 299 | GKVGETIPAEL | 20075 |
| HPV56 | L1 | 9 | 316 | GREPPPSSV | 20076 |
| HPV56 | L1 | 10 | 316 | GREPPPSSVY | 20077 |
| HPV56 | L1 | 11 | 316 | GREPPPSSVYV | 20078 |
| HPV56 | L1 | 8 | 142 | GRGQPLGA | 20079 |
| HPV56 | L1 | 10 | 142 | GRGQPLGAGL | 20080 |
| HPV56 | L1 | 8 | 498 | GRKFLMQL | 20081 |
| HPV56 | L1 | 9 | 64 | KRTSIFYHA | 20082 |
| HPV56 | L1 | 8 | 424 | LHNMNANL | 20083 |
| HPV56 | L1 | 9 | 424 | LHNMNANLL | 20084 |
| HPV56 | L1 | 8 | 14 | LHYGLCIF | 20085 |
| HPV56 | L1 | 9 | 14 | LHYGLCWL | 20086 |
| HPV56 | L1 | 11 | 14 | LHYGLCIFLDV | 20087 |
| HPV56 | L1 | 8 | 269 | LKMSADAY | 20088 |
| HPV56 | L1 | 9 | 397 | LRHVEEYEL | 20089 |
| HPV56 | L1 | 11 | 397 | LRHVEEYELQF | 20090 |
| HPV56 | L1 | 8 | 284 | LRREQLFA | 20091 |
| HPV56 | L1 | 11 | 284 | LRREQLFARHY | 20092 |
| HPV56 | L1 | 10 | 115 | NKFGLPDTNI | 20093 |
| HPV56 | L1 | 11 | 115 | NKFGLPDTNIY | 20094 |
| HPV56 | L1 | 9 | 342 | NKPYWLQRA | 20095 |
| HPV56 | L1 | 10 | 44 | NKVYLPPTPV | 20096 |
| HPV56 | L1 | 10 | 296 | NRAGKVGETI | 20097 |
| HPV56 | L1 | 11 | 158 | NRLDDTESSNL | 20098 |
| HPV56 | L1 | 8 | 97 | PKVSAYQY | 20099 |
| HPV56 | L1 | 10 | 97 | PKVSAYQYRV | 20100 |
| HPV56 | L1 | 11 | 97 | PKVSAYQYRVF | 20101 |
| HPV56 | L1 | 10 | 348 | QRAQGHNNGI | 20102 |
| HPV56 | L1 | 8 | 398 | RHVEEYEL | 20103 |
| HPV56 | L1 | 10 | 398 | RHVEEYELQF | 20104 |
| HPV56 | L1 | 11 | 398 | RHVEEYELQFV | 20105 |
| HPV56 | L1 | 10 | 292 | RHYFNRAGKV | 20106 |
| HPV56 | L1 | 10 | 391 | RKINQYLRHV | 20107 |
| HPV56 | L1 | 10 | 285 | RREQLFARHY | 20108 |
| HPV56 | L1 | 11 | 285 | RREQLFARHYF | 20109 |
| HPV56 | L1 | 9 | 250 | SKAEVPLDI | 20110 |
| HPV56 | L1 | 10 | 250 | SKAEVPLDIV | 20111 |
| HPV56 | L1 | 9 | 54 | SKVVATDSY | 20112 |
| HPV56 | L1 | 10 | 54 | SKVVATDSYV | 20113 |
| HPV56 | L1 | 8 | 386 | SKYDARKI | 20114 |
| HPV56 | L1 | 11 | 386 | SKYDARKINQY | 20115 |
| HPV56 | L1 | 10 | 75 | SRLLAVGHPY | 20116 |
| HPV56 | L1 | 11 | 75 | SRLLAVGHPYY | 20117 |
| HPV56 | L1 | 9 | 88 | TKDNTKTNI | 20118 |
| HPV56 | L1 | 11 | 204 | TKGAVCKSTQV | 20119 |
| HPV56 | L1 | 8 | 92 | TKTNIPKV | 20120 |
| HPV56 | L1 | 10 | 92 | TKTNIPKVSA | 20121 |
| HPV56 | L1 | 11 | 92 | TKTNIPKVSAY | 20122 |
| HPV56 | L1 | 8 | 507 | TRSKPAVA | 20123 |
| HPV56 | L1 | 8 | 371 | TRSTNMTI | 20124 |
| HPV56 | L1 | 11 | 371 | TRSTNMTISTA | 20125 |
| HPV56 | L1 | 8 | 63 | VKRTSWY | 20126 |
| HPV56 | L1 | 10 | 63 | VKRTSWYHA | 20127 |
| HPV56 | L1 | 9 | 109 | VRLPDPNKF | 20128 |
| HPV56 | L1 | 11 | 109 | VRLPDPNKFGL | 20129 |
| HPV56 | L1 | 8 | 39 | WRPSENKV | 20130 |
| HPV56 | L1 | 9 | 39 | WRPSENKVY | 20131 |
| HPV56 | L1 | 10 | 39 | WRPSENKVYL | 20132 |
| HPV56 | L1 | 8 | 70 | YHAGSSRL | 20133 |
| HPV56 | L1 | 9 | 70 | YHAGSSRLL | 20134 |
| HPV56 | L1 | 10 | 70 | YHAGSSRLLA | 20135 |
| HPV56 | L1 | 11 | 70 | YHAGSSRLLAV | 20136 |
| HPV56 | L1 | 8 | 477 | YKFWDVNL | 20137 |
| HPV56 | L1 | 8 | 9 | YRDPPLHY | 20138 |
| HPV56 | L1 | 10 | 9 | YRDPPLHYGL | 20139 |
| HPV56 | L1 | 8 | 104 | YRVFRVRL | 20140 |
| HPV56 | L1 | 8 | 451 | YRYVRSTA | 20141 |

TABLE XI-continued

| | | | | | |
|---|---|---|---|---|---|
| HPV56 | L1 | 9 | 451 | YRYVRSTAI | 20142 |
| HPV56 | L2 | 10 | 371 | AHLPIKPSTL | 20143 |
| HPV56 | L2 | 10 | 3 | AHRATRRKRA | 20144 |
| HPV56 | L2 | 10 | 87 | ARPPIVVESV | 20145 |
| HPV56 | L2 | 9 | 315 | ARVHYYYDI | 20146 |
| HPV56 | L2 | 11 | 21 | CKLSGTCPEDV | 20147 |
| HPV56 | L2 | 9 | 42 | DKILQWGSL | 20148 |
| HPV56 | L2 | 10 | 42 | DKILQWGSLF | 20149 |
| HPV56 | L2 | 9 | 243 | DRPATLVSA | 20150 |
| HPV56 | L2 | 9 | 218 | FRRIAAPRL | 20151 |
| HPV56 | L2 | 10 | 218 | FRRIAAPRLY | 20152 |
| HPV56 | L2 | 9 | 445 | FRRRRRKRI | 20153 |
| HPV56 | L2 | 11 | 445 | FRRRRRKRIPY | 20154 |
| HPV56 | L2 | 8 | 67 | GRAGYVPL | 20155 |
| HPV56 | L2 | 9 | 4 | HRATRRKRA | 20156 |
| HPV56 | L2 | 11 | 4 | HRATRRKRASA | 20157 |
| HPV56 | L2 | 9 | 189 | IHSYEEIPM | 20158 |
| HPV56 | L2 | 8 | 375 | IKPSTLSF | 20159 |
| HPV56 | L2 | 9 | 375 | IKPSTLSFA | 20160 |
| HPV56 | L2 | 8 | 10 | KRASATQL | 20161 |
| HPV56 | L2 | 9 | 10 | KRASATQLY | 20162 |
| HPV56 | L2 | 8 | 451 | KRIPYFFA | 20163 |
| HPV56 | L2 | 8 | 33 | NKIEQKTW | 20164 |
| HPV56 | L2 | 9 | 33 | NKIEQKTWA | 20165 |
| HPV56 | L2 | 8 | 224 | PRLYRKAF | 20166 |
| HPV56 | L2 | 11 | 224 | PRLYRKAFQQV | 20167 |
| HPV56 | L2 | 8 | 37 | QKTWADKI | 20168 |
| HPV56 | L2 | 9 | 37 | QKTWADKIL | 20169 |
| HPV56 | L2 | 11 | 37 | QKTWADKILQW | 20170 |
| HPV56 | L2 | 9 | 228 | RKAPQQVKV | 20171 |
| HPV56 | L2 | 9 | 9 | RKRASATQL | 20172 |
| HPV56 | L2 | 10 | 9 | RKRASATQLY | 20173 |
| HPV56 | L2 | 8 | 450 | RKRIPYFF | 20174 |
| HPV56 | L2 | 9 | 450 | RKRIPYFFA | 20175 |
| HPV56 | L2 | 10 | 290 | RRGGVRFSRL | 20176 |
| HPV56 | L2 | 8 | 308 | RRGTQIGA | 20177 |
| HPV56 | L2 | 10 | 308 | RRGTQIGARV | 20178 |
| HPV56 | L2 | 8 | 219 | RRIAAPRL | 20179 |
| HPV56 | L2 | 9 | 219 | RRIAAPRLY | 20180 |
| HPV56 | L2 | 10 | 8 | RRKRASATQL | 20181 |
| HPV56 | L2 | 11 | 8 | RRKRASATQLY | 20182 |
| HPV56 | L2 | 8 | 449 | RRKRIPYF | 20183 |
| HPV56 | L2 | 9 | 449 | RRKRIPYFF | 20184 |
| HPV56 | L2 | 10 | 449 | RRKRIPYFFA | 20185 |
| HPV56 | L2 | 8 | 448 | RRRKRIPY | 20186 |
| HPV56 | L2 | 9 | 448 | RRRKRIPYF | 20187 |
| HPV56 | L2 | 10 | 448 | RRRKRIPYFF | 20188 |
| HPV56 | L2 | 11 | 448 | RRRKRIPYFFA | 20189 |
| HPV56 | L2 | 9 | 447 | RRRRKRIPY | 20190 |
| HPV56 | L2 | 10 | 447 | RRRRKRIPYF | 20191 |
| HPV56 | L2 | 11 | 447 | RRRRKRIPYFF | 20192 |
| HPV56 | L2 | 8 | 446 | RRRRRKRI | 20193 |
| HPV56 | L2 | 10 | 446 | RRRRRKRIPY | 20194 |
| HPV56 | L2 | 11 | 446 | RRRRRKRIPYF | 20195 |
| HPV56 | L2 | 9 | 297 | SRLGRKATI | 20196 |
| HPV56 | L2 | 9 | 76 | SRPSTIVDV | 20197 |
| HPV56 | L2 | 11 | 427 | THDVYIQGSSF | 20198 |
| HPV56 | L2 | 8 | 155 | THITNPLF | 20199 |
| HPV56 | L2 | 9 | 155 | THITNPLFI | 20200 |
| HPV56 | L2 | 8 | 289 | TRRGGVRF | 20201 |
| HPV56 | L2 | 11 | 289 | TRRGGVRFSRL | 20202 |
| HPV56 | L2 | 9 | 307 | TRRGTQIGA | 20203 |
| HPV56 | L2 | 11 | 307 | TRRGTQIGARV | 20204 |
| HPV56 | L2 | 8 | 7 | TRRKRASA | 20205 |
| HPV56 | L2 | 11 | 7 | TRRKRASATQL | 20206 |
| HPV56 | L2 | 9 | 202 | VHGSGTEPI | 20207 |
| HPV56 | L2 | 8 | 150 | VHVSSTHI | 20208 |
| HPV56 | L2 | 10 | 317 | VHYYYDISPI | 20209 |
| HPV56 | L2 | 11 | 317 | VHYYYDISPIA | 20210 |
| HPV56 | L2 | 8 | 234 | VKVTDPAF | 20211 |
| HPV56 | L2 | 9 | 234 | VKVTDPAFL | 20212 |
| HPV56 | L2 | 10 | 294 | VRFSRLGRKA | 20213 |
| HPV56 | L2 | 8 | 227 | YRKAFQQV | 20214 |
| HPV56 | L2 | 10 | 227 | YRKAFQQVKV | 20215 |

TABLE XIII

B58 Supermotif Peptides

| Type | Protein | No. of Amino Acids | Position | Sequence | Seq. Id. No. |
|---|---|---|---|---|---|
| HPV16 | E1 | 11 | 316 | AAALYWYKTGI | 20216 |
| HPV16 | E1 | 9 | 239 | AAFGLTPSI | 20217 |
| HPV16 | E1 | 10 | 239 | AAFGLTPSIA | 20218 |
| HPV16 | E1 | 10 | 317 | AALYWYKTGI | 20219 |
| HPV16 | E1 | 10 | 205 | AAMLAKFKEL | 20220 |
| HPV16 | E1 | 11 | 205 | AAMLAKFKELY | 20221 |
| HPV16 | E1 | 8 | 478 | AANTGKSL | 20222 |
| HPV16 | E1 | 9 | 478 | AANTGKSLF | 20223 |
| HPV16 | E1 | 11 | 478 | AANTGKSLFGM | 20224 |
| HPV16 | E1 | 11 | 389 | ASAFLKSNSQA | 20225 |
| HPV16 | E1 | 10 | 406 | ATMCRHYKRA | 20226 |
| HPV16 | E1 | 8 | 524 | ATVPCWNY | 20227 |
| HPV16 | E1 | 9 | 524 | ATVPCWNYI | 20228 |
| HPV16 | E1 | 8 | 405 | CATMCRHY | 20229 |
| HPV16 | E1 | 11 | 405 | CATMCRHYKRA | 20230 |
| HPV16 | E1 | 8 | 269 | CSWGMVVL | 20231 |
| HPV16 | E1 | 9 | 269 | CSWGMVVLL | 20232 |
| HPV16 | E1 | 10 | 269 | CSWGMVVLLL | 20233 |
| HPV16 | E1 | 11 | 269 | CSWGMVVLLLV | 20234 |
| HPV16 | E1 | 8 | 353 | CTFELSQM | 20235 |
| HPV16 | E1 | 9 | 353 | CTFELSQMV | 20236 |
| HPV16 | E1 | 11 | 353 | CTFELSQMVQW | 20237 |
| HPV16 | E1 | 10 | 515 | DAKIGMLDDA | 20238 |
| HPV16 | E1 | 9 | 523 | DATVPCWNY | 20239 |
| HPV16 | E1 | 10 | 523 | DATVPCWNYI | 20240 |
| HPV16 | E1 | 10 | 81 | DAVQVLKRKY | 20241 |
| HPV16 | E1 | 11 | 81 | DAVQVLKRKYL | 20242 |
| HPV16 | E1 | 8 | 41 | DSDTGEDL | 20243 |
| HPV16 | E1 | 9 | 41 | DSDTGEDLV | 20244 |
| HPV16 | E1 | 11 | 41 | DSDTGEDLVDF | 20245 |
| HPV16 | E1 | 8 | 372 | DSEIAYKY | 20246 |
| HPV16 | E1 | 9 | 372 | DSEIAYKYA | 20247 |
| HPV16 | E1 | 11 | 372 | DSEIAYKYAQL | 20248 |
| HPV16 | E1 | 9 | 131 | DSGYGNTEV | 20249 |
| HPV16 | E1 | 10 | 249 | DSIKTLLQQY | 20250 |
| HPV16 | E1 | 9 | 633 | DSLPTFKCV | 20251 |
| HPV16 | E1 | 11 | 573 | DSRWPYLHNRL | 20252 |
| HPV16 | E1 | 9 | 43 | DTGEDLVDF | 20253 |
| HPV16 | E1 | 10 | 43 | DTGEDLVDFI | 20254 |
| HPV16 | E1 | 11 | 43 | DTGEDLVDFIV | 20255 |
| HPV16 | E1 | 8 | 384 | DTNSNASA | 20256 |
| HPV16 | E1 | 9 | 384 | DTNSNASAF | 20257 |
| HPV16 | E1 | 10 | 384 | DTNSNASAFL | 20258 |
| HPV16 | E1 | 11 | 335 | DTPEWIQRQTV | 20259 |
| HPV16 | E1 | 8 | 75 | EAKQHRDA | 20260 |
| HPV16 | E1 | 9 | 75 | EAKQHRDAV | 20261 |
| HPV16 | E1 | 11 | 75 | EAKQHRDAVQV | 20262 |
| HPV16 | E1 | 11 | 22 | EAVVEKKTGDA | 20263 |
| HPV16 | E1 | 9 | 65 | ETAHALFTA | 20264 |
| HPV16 | E1 | 8 | 63 | ETETAHAL | 20265 |
| HPV16 | E1 | 9 | 63 | ETETAHALF | 20266 |
| HPV16 | E1 | 11 | 63 | ETETAHALFTA | 20267 |
| HPV16 | E1 | 9 | 152 | ETETPCSQY | 20268 |
| HPV16 | E1 | 10 | 288 | ETIEKLLSKL | 20269 |
| HPV16 | E1 | 11 | 288 | ETIEKLLSKLL | 20270 |
| HPV16 | E1 | 8 | 140 | ETQQMLQV | 20271 |
| HPV16 | E1 | 8 | 219 | FSELVRPF | 20272 |
| HPV16 | E1 | 8 | 613 | FSRTWSRL | 20273 |
| HPV16 | E1 | 10 | 613 | FSRTWSRLSL | 20274 |
| HPV16 | E1 | 9 | 586 | FTFPNEPF | 20275 |
| HPV16 | E1 | 9 | 477 | GAANTGKSL | 20276 |
| HPV16 | E1 | 10 | 477 | GAANTGKSLF | 20277 |
| HPV16 | E1 | 9 | 163 | GSGGGCSQY | 20278 |
| HPV16 | E1 | 8 | 571 | GTDSRWPY | 20279 |
| HPV16 | E1 | 9 | 571 | GTDSRWPYL | 20280 |
| HPV16 | E1 | 8 | 12 | GTGCNGWF | 20281 |
| HPV16 | E1 | 9 | 12 | GTGCNGWFY | 20282 |
| HPV16 | E1 | 10 | 12 | GTGCNGWFYV | 20283 |
| HPV16 | E1 | 9 | 68 | HALFTAQEA | 20284 |
| HPV16 | E1 | 8 | 348 | HSFNDCTF | 20285 |
| HPV16 | E1 | 10 | 348 | HSFNDCTFEL | 20286 |
| HPV16 | E1 | 8 | 184 | HTICQTPL | 20287 |
| HPV16 | E1 | 11 | 184 | HTICQTPLTNI | 20288 |
| HPV16 | E1 | 10 | 238 | IAAFGLTPSI | 20289 |
| HPV16 | E1 | 11 | 238 | IAAFGLTPSIA | 20290 |
| HPV16 | E1 | 8 | 247 | IADSIKTL | 20291 |

TABLE XIII-continued

B58 Supermotif Peptides

| Type | Protein | No. of Amino Acids | Position | Sequence | Seq. Id. No. |
|---|---|---|---|---|---|
| HPV16 | E1 | 9 | 247 | IADSIKTLL | 20292 |
| HPV16 | E1 | 8 | 375 | IAYKYAQL | 20293 |
| HPV16 | E1 | 9 | 375 | IAYKYAQLA | 20294 |
| HPV16 | E1 | 11 | 329 | ISEVYGDTPEW | 20295 |
| HPV16 | E1 | 9 | 98 | ISGCVDNNI | 20296 |
| HPV16 | E1 | 8 | 326 | ISNISEVY | 20297 |
| HPV16 | E1 | 8 | 106 | ISPRLKAI | 20298 |
| HPV16 | E1 | 10 | 106 | ISPRLKAICI | 20299 |
| HPV16 | E1 | 8 | 204 | KAAMLAKF | 20300 |
| HPV16 | E1 | 11 | 204 | KAAMLAKFKEL | 20301 |
| HPV16 | E1 | 11 | 111 | KAICIEKQSRA | 20302 |
| HPV16 | E1 | 8 | 610 | KSFFSRTW | 20303 |
| HPV16 | E1 | 11 | 610 | KSFFSRTWSRL | 20304 |
| HPV16 | E1 | 9 | 505 | KSHFWLQPL | 20305 |
| HPV16 | E1 | 10 | 505 | KSHFWLQPLA | 20306 |
| HPV16 | E1 | 8 | 483 | KSLFGMSL | 20307 |
| HPV16 | E1 | 9 | 483 | KSLFGMSLM | 20308 |
| HPV16 | E1 | 11 | 483 | KSLFGMSLMKF | 20309 |
| HPV16 | E1 | 10 | 227 | KSNKSTCCDW | 20310 |
| HPV16 | E1 | 8 | 394 | KSNSQAKI | 20311 |
| HPV16 | E1 | 9 | 394 | KSNSQAKIV | 20312 |
| HPV16 | E1 | 9 | 230 | KSTCCDWCI | 20313 |
| HPV16 | E1 | 10 | 230 | KSTCCDWCIA | 20314 |
| HPV16 | E1 | 11 | 230 | KSTCCDWCIAA | 20315 |
| HPV16 | E1 | 10 | 323 | KTGISNISEV | 20316 |
| HPV16 | E1 | 11 | 323 | KTGISNISEVY | 20317 |
| HPV16 | E1 | 9 | 252 | KTLLQQYCL | 20318 |
| HPV16 | E1 | 10 | 252 | KTLLQQYCLY | 20319 |
| HPV16 | E1 | 11 | 252 | KTLLQQYCLYL | 20320 |
| HPV16 | E1 | 8 | 199 | KTSNAKAA | 20321 |
| HPV16 | E1 | 9 | 199 | KTSNAKAAM | 20322 |
| HPV16 | E1 | 10 | 199 | KTSNAKAAML | 20323 |
| HPV16 | E1 | 11 | 199 | KTSNAKAAMLA | 20324 |
| HPV16 | E1 | 8 | 267 | LACSWGMV | 20325 |
| HPV16 | E1 | 9 | 267 | LACSWGMVV | 20326 |
| HPV16 | E1 | 10 | 267 | LACSWGMVVL | 20327 |
| HPV16 | E1 | 11 | 267 | LACSWGMVVLL | 20328 |
| HPV16 | E1 | 8 | 513 | LADAKIGM | 20329 |
| HPV16 | E1 | 9 | 513 | LADAKIGML | 20330 |
| HPV16 | E1 | 8 | 382 | LADTNSNA | 20331 |
| HPV16 | E1 | 10 | 382 | LADTNSNASA | 20332 |
| HPV16 | E1 | 11 | 382 | LADTNSNASAF | 20333 |
| HPV16 | E1 | 8 | 208 | LAKFKELY | 20334 |
| HPV16 | E1 | 10 | 208 | LAKFKELYGV | 20335 |
| HPV16 | E1 | 8 | 95 | LSDISGCV | 20336 |
| HPV16 | E1 | 10 | 294 | LSKLLCVSPM | 20337 |
| HPV16 | E1 | 8 | 357 | LSQMVQWA | 20338 |
| HPV16 | E1 | 9 | 357 | LSQMVQWAY | 20339 |
| HPV16 | E1 | 8 | 457 | LTALKRFL | 20340 |
| HPV16 | E1 | 11 | 457 | LTALKRFLQGI | 20341 |
| HPV16 | E1 | 8 | 191 | LTNILNVL | 20342 |
| HPV16 | E1 | 9 | 243 | LTPSIADSI | 20343 |
| HPV16 | E1 | 9 | 59 | LTQAETETA | 20344 |
| HPV16 | E1 | 11 | 59 | LTQAETETAHA | 20345 |
| HPV16 | E1 | 10 | 454 | MSFLTALKRF | 20346 |
| HPV16 | E1 | 11 | 454 | MSFLTALKRFL | 20347 |
| HPV16 | E1 | 11 | 488 | MSLMKFLQGSV | 20348 |
| HPV16 | E1 | 9 | 420 | MSMSQWIKY | 20349 |
| HPV16 | E1 | 8 | 569 | NAGTDSRW | 20350 |
| HPV16 | E1 | 10 | 569 | NAGTDSRWPY | 20351 |
| HPV16 | E1 | 11 | 569 | NAGTDSRWPYL | 20352 |
| HPV16 | E1 | 8 | 202 | NAKAAMLA | 20353 |
| HPV16 | E1 | 10 | 202 | NAKAAMLAKF | 20354 |
| HPV16 | E1 | 8 | 538 | NALDGNLV | 20355 |
| HPV16 | E1 | 10 | 538 | NALDGNLVSM | 20356 |
| HPV16 | E1 | 8 | 503 | NSKSHFWL | 20357 |
| HPV16 | E1 | 11 | 503 | NSKSHFWLQPL | 20358 |
| HPV16 | E1 | 8 | 386 | NSNASAFL | 20359 |
| HPV16 | E1 | 11 | 396 | NSQAKIVKDCA | 20360 |
| HPV16 | E1 | 9 | 136 | NTEVETQQM | 20361 |
| HPV16 | E1 | 10 | 136 | NTEVETQQML | 20362 |
| HPV16 | E1 | 9 | 480 | NTGKSLFGM | 20363 |
| HPV16 | E1 | 11 | 480 | NTGKSLFGMSL | 20364 |
| HPV16 | E1 | 10 | 245 | PSIADSIKTL | 20365 |
| HPV16 | E1 | 11 | 245 | PSIADSIKTLL | 20366 |
| HPV16 | E1 | 9 | 61 | QAETETAHA | 20367 |

TABLE XIII-continued

B58 Supermotif Peptides

| Type | Protein | No. of Amino Acids | Position | Sequence | Seq. Id. No. |
|---|---|---|---|---|---|
| HPV16 | E1 | 10 | 61 | QAETETAHAL | 20368 |
| HPV16 | E1 | 11 | 61 | QAETETAHALF | 20369 |
| HPV16 | E1 | 9 | 398 | QAKIVKDCA | 20370 |
| HPV16 | E1 | 11 | 398 | QAKIVKDCATM | 20371 |
| HPV16 | E1 | 9 | 265 | QSLACSWGM | 20372 |
| HPV16 | E1 | 10 | 265 | QSLACSWGMV | 20373 |
| HPV16 | E1 | 11 | 265 | QSLACSWGMVV | 20374 |
| HPV16 | E1 | 9 | 118 | QSRAAKRRL | 20375 |
| HPV16 | E1 | 10 | 118 | QSRAAKRRLF | 20376 |
| HPV16 | E1 | 8 | 188 | QTPLTNIL | 20377 |
| HPV16 | E1 | 10 | 188 | QTPLTNILNV | 20378 |
| HPV16 | E1 | 11 | 188 | QTPLTNILNVL | 20379 |
| HPV16 | E1 | 8 | 343 | QTVLQHSF | 20380 |
| HPV16 | E1 | 8 | 120 | RAAKRRLF | 20381 |
| HPV16 | E1 | 9 | 414 | RAEKKQMSM | 20382 |
| HPV16 | E1 | 8 | 313 | RSTAAALY | 20383 |
| HPV16 | E1 | 9 | 313 | RSTAAALYW | 20384 |
| HPV16 | E1 | 10 | 313 | RSTAAALYWY | 20385 |
| HPV16 | E1 | 8 | 615 | RTWSRLSL | 20386 |
| HPV16 | E1 | 10 | 390 | SAFLKSNSQA | 20387 |
| HPV16 | E1 | 9 | 172 | SSGSGGEGV | 20388 |
| HPV16 | E1 | 8 | 314 | STAAALYW | 20389 |
| HPV16 | E1 | 9 | 314 | STAAALYWY | 20390 |
| HPV16 | E1 | 8 | 231 | STCCDWCI | 20391 |
| HPV16 | E1 | 9 | 231 | STCCDWCIA | 20392 |
| HPV16 | E1 | 10 | 231 | STCCDWCIAA | 20393 |
| HPV16 | E1 | 11 | 231 | STCCDWCIAAF | 20394 |
| HPV16 | E1 | 8 | 315 | TAAALYWY | 20395 |
| HPV16 | E1 | 8 | 66 | TAHALFTA | 20396 |
| HPV16 | E1 | 11 | 66 | TAHALFTAQEA | 20397 |
| HPV16 | E1 | 10 | 458 | TALKRFLQGI | 20398 |
| HPV16 | E1 | 11 | 72 | TAQEAKQHRDA | 20399 |
| HPV16 | E1 | 8 | 200 | TSNAKAAM | 20400 |
| HPV16 | E1 | 9 | 200 | TSNAKAAML | 20401 |
| HPV16 | E1 | 10 | 200 | TSNAKAAMLA | 20402 |
| HPV16 | E1 | 10 | 217 | VSFSELVRPF | 20403 |
| HPV16 | E1 | 9 | 641 | VSGQNTNTL | 20404 |
| HPV16 | E1 | 10 | 545 | VSMDVKHRPL | 20405 |
| HPV16 | E1 | 11 | 545 | VSMDVKHRPLV | 20406 |
| HPV16 | E1 | 11 | 92 | VSPLSDISGCV | 20407 |
| HPV16 | E1 | 8 | 300 | VSPMCMMI | 20408 |
| HPV16 | E1 | 8 | 363 | WAYDNDIV | 20409 |
| HPV16 | E1 | 11 | 379 | YAQLADTNSNA | 20410 |
| HPV16 | E1 | 10 | 171 | YSSGSGGEGV | 20411 |
| HPV16 | E2 | 8 | 220 | AATHTKAV | 20412 |
| HPV16 | E2 | 9 | 220 | AATHTKAVA | 20413 |
| HPV16 | E2 | 10 | 220 | AATHTKAVAL | 20414 |
| HPV16 | E2 | 10 | 143 | ASVTVVEGQV | 20415 |
| HPV16 | E2 | 8 | 221 | ATHTKAVA | 20416 |
| HPV16 | E2 | 9 | 221 | ATHTKAVAL | 20417 |
| HPV16 | E2 | 10 | 40 | CAIYYKAREM | 20418 |
| HPV16 | E2 | 11 | 309 | CTLYTAVSSTW | 20419 |
| HPV16 | E2 | 10 | 174 | DAEKYSKNKV | 20420 |
| HPV16 | E2 | 11 | 174 | DAEKYSKNKVW | 20421 |
| HPV16 | E2 | 8 | 294 | DANTLKCL | 20422 |
| HPV16 | E2 | 10 | 294 | DANTLKCLRY | 20423 |
| HPV16 | E2 | 8 | 263 | DSAPILTA | 20424 |
| HPV16 | E2 | 9 | 263 | DSAPILTAF | 20425 |
| HPV16 | E2 | 9 | 338 | DSEWQRDQF | 20426 |
| HPV16 | E2 | 10 | 338 | DSEWQRDQFL | 20427 |
| HPV16 | E2 | 9 | 22 | DSTDLRDHI | 20428 |
| HPV16 | E2 | 11 | 22 | DSTDLRDHIDY | 20429 |
| HPV16 | E2 | 8 | 260 | DSVDSAPI | 20430 |
| HPV16 | E2 | 9 | 260 | DSVDSAPIL | 20431 |
| HPV16 | E2 | 11 | 260 | DSVDSAPILTA | 20432 |
| HPV16 | E2 | 11 | 246 | DTGNPCHTTKL | 20433 |
| HPV16 | E2 | 11 | 142 | EASVTVVEGQV | 20434 |
| HPV16 | E2 | 8 | 80 | ETIYNSQY | 20435 |
| HPV16 | E2 | 9 | 2 | ETLCQRLNV | 20436 |
| HPV16 | E2 | 11 | 200 | FSSNEVSSPEI | 20437 |
| HPV16 | E2 | 9 | 230 | GTEETQTTI | 20438 |
| HPV16 | E2 | 8 | 187 | HAGGQVIL | 20439 |
| HPV16 | E2 | 11 | 252 | HTTKLLHRDSV | 20440 |
| HPV16 | E2 | 8 | 356 | ITVSTGFM | 20441 |
| HPV16 | E2 | 10 | 356 | ITVSTGFMSI | 20442 |
| HPV16 | E2 | 8 | 68 | KALQAIEL | 20443 |

TABLE XIII-continued

B58 Supermotif Peptides

| Type | Protein | No. of Amino Acids | Position | Sequence | Seq. Id. No. |
|---|---|---|---|---|---|
| HPV16 | E2 | 10 | 68 | KALQAIELQL | 20444 |
| HPV16 | E2 | 10 | 45 | KAREMGFKHI | 20445 |
| HPV16 | E2 | 9 | 329 | KSAIVTLTY | 20446 |
| HPV16 | E2 | 9 | 354 | KTITVSTGF | 20447 |
| HPV16 | E2 | 10 | 354 | KTITVSTGFM | 20448 |
| HPV16 | E2 | 8 | 62 | LAVSKNKA | 20449 |
| HPV16 | E2 | 9 | 62 | LAVSKNKAL | 20450 |
| HPV16 | E2 | 11 | 62 | LAVSKNKALQA | 20451 |
| HPV16 | E2 | 10 | 347 | LSQVKIPKTI | 20452 |
| HPV16 | E2 | 8 | 103 | LTAPTGCI | 20453 |
| HPV16 | E2 | 11 | 16 | LTHYENDSTDL | 20454 |
| HPV16 | E2 | 11 | 77 | LTLETIYNSQY | 20455 |
| HPV16 | E2 | 8 | 282 | NSNTTPIV | 20456 |
| HPV16 | E2 | 10 | 282 | NSNTTPIVHL | 20457 |
| HPV16 | E2 | 9 | 84 | NSQYSNEKW | 20458 |
| HPV16 | E2 | 11 | 84 | NSQYSNEKWTL | 20459 |
| HPV16 | E2 | 8 | 272 | NSSHKGRI | 20460 |
| HPV16 | E2 | 8 | 296 | NTLKCLRY | 20461 |
| HPV16 | E2 | 10 | 296 | NTLKCLRYRF | 20462 |
| HPV16 | E2 | 8 | 127 | NTMHYTNW | 20463 |
| HPV16 | E2 | 11 | 127 | NTMHYTNWTHI | 20464 |
| HPV16 | E2 | 8 | 284 | NTTPIVHL | 20465 |
| HPV16 | E2 | 8 | 219 | PAATHTKA | 20466 |
| HPV16 | E2 | 9 | 219 | PAATHTKAV | 20467 |
| HPV16 | E2 | 10 | 219 | PAATHTKAVA | 20468 |
| HPV16 | E2 | 11 | 219 | PAATHTKAVAL | 20469 |
| HPV16 | E2 | 10 | 106 | PTGCIKKHGY | 20470 |
| HPV16 | E2 | 10 | 60 | PTLAVSKNKA | 20471 |
| HPV16 | E2 | 11 | 60 | PTLAVSKNKAL | 20472 |
| HPV16 | E2 | 10 | 196 | PTSVFSSNEV | 20473 |
| HPV16 | E2 | 9 | 71 | QAIELQLTL | 20474 |
| HPV16 | E2 | 11 | 165 | RTYFVQFKDDA | 20475 |
| HPV16 | E2 | 8 | 330 | SAIVTLTY | 20476 |
| HPV16 | E2 | 8 | 264 | SAPILTAF | 20477 |
| HPV16 | E2 | 10 | 201 | SSNEVSSPEI | 20478 |
| HPV16 | E2 | 11 | 201 | SSNEVSSPEII | 20479 |
| HPV16 | E2 | 10 | 206 | SSPEIIRQHL | 20480 |
| HPV16 | E2 | 11 | 206 | SSPEIIRQHLA | 20481 |
| HPV16 | E2 | 11 | 316 | SSTWHWTGHNV | 20482 |
| HPV16 | E2 | 8 | 23 | STDLRDHI | 20483 |
| HPV16 | E2 | 10 | 23 | STDLRDHIDY | 20484 |
| HPV16 | E2 | 11 | 23 | STDLRDHIDYW | 20485 |
| HPV16 | E2 | 10 | 317 | STWHWTGHNV | 20486 |
| HPV16 | E2 | 11 | 269 | TAFNSSHKGRI | 20487 |
| HPV16 | E2 | 9 | 313 | TAVSSTWHW | 20488 |
| HPV16 | E2 | 9 | 197 | TSVFSSNEV | 20489 |
| HPV16 | E2 | 10 | 253 | TTKLLHRDSV | 20490 |
| HPV16 | E2 | 11 | 285 | TTPIVHLKGDA | 20491 |
| HPV16 | E2 | 9 | 64 | VSKNKALQA | 20492 |
| HPV16 | E2 | 10 | 64 | VSKNKALQAI | 20493 |
| HPV16 | E2 | 9 | 97 | VSLEVYLTA | 20494 |
| HPV16 | E2 | 11 | 205 | VSSPEIIRQHL | 20495 |
| HPV16 | E2 | 8 | 358 | VSTGFMSI | 20496 |
| HPV16 | E2 | 9 | 333 | VTLTYDSEW | 20497 |
| HPV16 | E2 | 8 | 145 | VTVVEGQV | 20498 |
| HPV16 | E2 | 10 | 145 | VTVVEGQVDY | 20499 |
| HPV16 | E2 | 11 | 145 | VTVVEGQVDYY | 20500 |
| HPV16 | E2 | 11 | 321 | WTGHNVKHKSA | 20501 |
| HPV16 | E2 | 10 | 134 | WTHIYICEEA | 20502 |
| HPV16 | E2 | 8 | 92 | WTLQDVSL | 20503 |
| HPV16 | E2 | 10 | 92 | WTLQDVSLEV | 20504 |
| HPV16 | E2 | 11 | 92 | WTLQDVSLEVY | 20505 |
| HPV16 | E2 | 9 | 178 | YSKNKVWEV | 20506 |
| HPV16 | E2 | 11 | 178 | YSKNKVWEVHA | 20507 |
| HPV16 | E2 | 8 | 87 | YSNEKWTL | 20508 |
| HPV16 | E2 | 11 | 87 | YSNEKWTLQDV | 20509 |
| HPV16 | E2 | 8 | 312 | YTAVSSTW | 20510 |
| HPV16 | E2 | 10 | 312 | YTAVSSTWHW | 20511 |
| HPV16 | E2 | 8 | 131 | YTNWTHIY | 20512 |
| HPV16 | E2 | 9 | 131 | YTNWTHIYI | 20513 |
| HPV16 | E2 | 11 | 115 | YTVEVQFDGDI | 20514 |
| HPV16 | E5 | 8 | 53 | AASAFRCF | 20515 |
| HPV16 | E5 | 9 | 53 | AASAFRCFI | 20516 |
| HPV16 | E5 | 10 | 53 | AASAFRCFIV | 20517 |
| HPV16 | E5 | 11 | 53 | AASAFRCFIVY | 20518 |
| HPV16 | E5 | 8 | 54 | ASAFRCFI | 20519 |

TABLE XIII-continued

B58 Supermotif Peptides

| Type | Protein | No. of Amino Acids | Position | Sequence | Seq. Id. No. |
|---|---|---|---|---|---|
| HPV16 | E5 | 9 | 54 | ASAFRCFIV | 20520 |
| HPV16 | E5 | 10 | 54 | ASAFRCFIVY | 20521 |
| HPV16 | E5 | 11 | 54 | ASAFRCFIVYI | 20522 |
| HPV16 | E5 | 9 | 7 | ASTTLLACF | 20523 |
| HPV16 | E5 | 10 | 7 | ASTTLLACFL | 20524 |
| HPV16 | E5 | 11 | 7 | ASTTLLACFLL | 20525 |
| HPV16 | E5 | 8 | 5 | DTASTTLL | 20526 |
| HPV16 | E5 | 9 | 5 | DTASTTLLA | 20527 |
| HPV16 | E5 | 11 | 5 | DTASTTLLACF | 20528 |
| HPV16 | E5 | 8 | 75 | HTHARFLI | 20529 |
| HPV16 | E5 | 10 | 51 | ITAASAFRCF | 20530 |
| HPV16 | E5 | 11 | 51 | ITAASAFRCFI | 20531 |
| HPV16 | E5 | 8 | 12 | LACFLLCF | 20532 |
| HPV16 | E5 | 10 | 12 | LACFLLCFCV | 20533 |
| HPV16 | E5 | 11 | 12 | LACFLLCFCVL | 20534 |
| HPV16 | E5 | 9 | 34 | LSVSTYTSL | 20535 |
| HPV16 | E5 | 10 | 34 | LSVSTYTSLI | 20536 |
| HPV16 | E5 | 11 | 34 | LSVSTYTSLII | 20537 |
| HPV16 | E5 | 11 | 1 | MTNLDTASTTL | 20538 |
| HPV16 | E5 | 8 | 55 | SAFRCFIV | 20539 |
| HPV16 | E5 | 9 | 55 | SAFRCFIVY | 20540 |
| HPV16 | E5 | 10 | 55 | SAFRCFIVYI | 20541 |
| HPV16 | E5 | 11 | 55 | SAFRCFIVYII | 20542 |
| HPV16 | E5 | 8 | 8 | STTLLACF | 20543 |
| HPV16 | E5 | 9 | 8 | STTLLACFL | 20544 |
| HPV16 | E5 | 10 | 8 | STTLLACFLL | 20545 |
| HPV16 | E5 | 8 | 37 | STYTSLII | 20546 |
| HPV16 | E5 | 9 | 37 | STYTSLIIL | 20547 |
| HPV16 | E5 | 10 | 37 | STYTSLIILV | 20548 |
| HPV16 | E5 | 11 | 37 | STYTSLIILVL | 20549 |
| HPV16 | E5 | 9 | 52 | TAASAFRCF | 20550 |
| HPV16 | E5 | 10 | 52 | TAASAFRCFI | 20551 |
| HPV16 | E5 | 11 | 52 | TAASAFRCFIV | 20552 |
| HPV16 | E5 | 8 | 6 | TASTTLLA | 20553 |
| HPV16 | E5 | 10 | 6 | TASTTLLACF | 20554 |
| HPV16 | E5 | 11 | 6 | TASTTLLACFL | 20555 |
| HPV16 | E5 | 8 | 40 | TSLIILVL | 20556 |
| HPV16 | E5 | 9 | 40 | TSLIILVLL | 20557 |
| HPV16 | E5 | 10 | 40 | TSLIILVLLL | 20558 |
| HPV16 | E5 | 11 | 40 | TSLIILVLLLW | 20559 |
| HPV16 | E5 | 8 | 9 | TTLLACFL | 20560 |
| HPV16 | E5 | 9 | 9 | TTLLACFLL | 20561 |
| HPV16 | E5 | 11 | 9 | TTLLACFLLCF | 20562 |
| HPV16 | E5 | 8 | 36 | VSTYTSLI | 20563 |
| HPV16 | E5 | 9 | 36 | VSTYTSLII | 20564 |
| HPV16 | E5 | 10 | 36 | VSTYTSLIIL | 20565 |
| HPV16 | E5 | 11 | 36 | VSTYTSLIILV | 20566 |
| HPV16 | E5 | 8 | 39 | YTSLIILV | 20567 |
| HPV16 | E5 | 9 | 39 | YTSLIILVL | 20568 |
| HPV16 | E5 | 10 | 39 | YTSLIILVLL | 20569 |
| HPV16 | E5 | 11 | 39 | YTSLIILVLLL | 20570 |
| HPV16 | E6 | 8 | 23 | CTELQTTI | 20571 |
| HPV16 | E6 | 11 | 23 | CTELQTTIHDI | 20572 |
| HPV16 | E6 | 8 | 52 | FAFRDLCI | 20573 |
| HPV16 | E6 | 9 | 52 | FAFRDLCIV | 20574 |
| HPV16 | E6 | 10 | 52 | FAFRDLCIVY | 20575 |
| HPV16 | E6 | 8 | 92 | GTTLEQQY | 20576 |
| HPV16 | E6 | 9 | 80 | ISEYRHYCY | 20577 |
| HPV16 | E6 | 11 | 80 | ISEYRHYCYSL | 20578 |
| HPV16 | E6 | 8 | 27 | QTTIHDII | 20579 |
| HPV16 | E6 | 9 | 27 | QTTIHDIIL | 20580 |
| HPV16 | E6 | 11 | 148 | RSSRTRRETQL | 20581 |
| HPV16 | E6 | 8 | 151 | RTRRETQL | 20582 |
| HPV16 | E6 | 10 | 149 | SSRTRRETQL | 20583 |
| HPV16 | E6 | 8 | 28 | TTIHDIIL | 20584 |
| HPV16 | E6 | 11 | 28 | TTIHDIILECV | 20585 |
| HPV16 | E6 | 11 | 93 | TTLEQQYNKPL | 20586 |
| HPV16 | E6 | 8 | 67 | YAVCDKCL | 20587 |
| HPV16 | E6 | 10 | 67 | YAVCDKCLKF | 20588 |
| HPV16 | E6 | 11 | 67 | YAVCDKCLKFY | 20589 |
| HPV16 | E6 | 10 | 77 | YSKISEYRHY | 20590 |
| HPV16 | E6 | 8 | 88 | YSLYGTTL | 20591 |
| HPV16 | E7 | 9 | 30 | DSSEEEDEI | 20592 |
| HPV16 | E7 | 8 | 62 | DSTLRLCV | 20593 |
| HPV16 | E7 | 8 | 4 | DTPTLHEY | 20594 |
| HPV16 | E7 | 9 | 4 | DTPTLHEYM | 20595 |

TABLE XIII-continued

B58 Supermotif Peptides

| Type | Protein | No. of Amino Acids | Position | Sequence | Seq. Id. No. |
|---|---|---|---|---|---|
| HPV16 | E7 | 10 | 4 | DTPTLHEYML | 20596 |
| HPV16 | E7 | 8 | 18 | ETTDLYCY | 20597 |
| HPV16 | E7 | 11 | 18 | ETTDLYCYEQL | 20598 |
| HPV16 | E7 | 9 | 85 | GTLGIVCPI | 20599 |
| HPV16 | E7 | 10 | 41 | PAGQAEPDRA | 20600 |
| HPV16 | E7 | 8 | 6 | PTLHEYML | 20601 |
| HPV16 | E7 | 10 | 6 | PTLHEYMLDL | 20602 |
| HPV16 | E7 | 9 | 44 | QAEPDRAHY | 20603 |
| HPV16 | E7 | 11 | 44 | QAEPDRAHYNI | 20604 |
| HPV16 | E7 | 10 | 70 | QSTHVDIRTL | 20605 |
| HPV16 | E7 | 9 | 49 | RAHYNIVTF | 20606 |
| HPV16 | E7 | 8 | 77 | RTLEDLLM | 20607 |
| HPV16 | E7 | 11 | 77 | RTLEDLLMGTL | 20608 |
| HPV16 | E7 | 8 | 31 | SSEEEDEI | 20609 |
| HPV16 | E7 | 9 | 71 | STHVDIRTL | 20610 |
| HPV16 | E7 | 10 | 19 | TTDLYCYEQL | 20611 |
| HPV16 | E7 | 11 | 55 | VTFCCKCDSTL | 20612 |
| HPV16 | L1 | 10 | 372 | AAISTSETTY | 20613 |
| HPV16 | L1 | 8 | 158 | ASAYAANA | 20614 |
| HPV16 | L1 | 10 | 158 | ASAYAANAGV | 20615 |
| HPV16 | L1 | 8 | 35 | ATVYLPPV | 20616 |
| HPV16 | L1 | 10 | 35 | ATVYLPPVPV | 20617 |
| HPV16 | L1 | 11 | 371 | CAAISTSETTY | 20618 |
| HPV16 | L1 | 10 | 251 | CTSICKYPDY | 20619 |
| HPV16 | L1 | 11 | 251 | CTSICKYPDYI | 20620 |
| HPV16 | L1 | 9 | 329 | DAQIFNKPY | 20621 |
| HPV16 | L1 | 10 | 329 | DAQIFNKPYW | 20622 |
| HPV16 | L1 | 11 | 329 | DAQIFNKPYWL | 20623 |
| HPV16 | L1 | 8 | 154 | DTENASAY | 20624 |
| HPV16 | L1 | 9 | 154 | DTENASAYA | 20625 |
| HPV16 | L1 | 10 | 154 | DTENASAYAA | 20626 |
| HPV16 | L1 | 9 | 228 | DTGFGAMDF | 20627 |
| HPV16 | L1 | 8 | 120 | DTQRLVWA | 20628 |
| HPV16 | L1 | 10 | 120 | DTQRLVWACV | 20629 |
| HPV16 | L1 | 8 | 361 | DTTRSTNM | 20630 |
| HPV16 | L1 | 10 | 361 | DTTRSTNMSL | 20631 |
| HPV16 | L1 | 10 | 442 | DTYRFVTSQA | 20632 |
| HPV16 | L1 | 11 | 442 | DTYRFVTSQAI | 20633 |
| HPV16 | L1 | 9 | 34 | EATVYLPPV | 20634 |
| HPV16 | L1 | 11 | 34 | EATVYLPPVPV | 20635 |
| HPV16 | L1 | 9 | 378 | ETTYKNTNF | 20636 |
| HPV16 | L1 | 8 | 481 | FSADLDQF | 20637 |
| HPV16 | L1 | 10 | 481 | FSADLDQFPL | 20638 |
| HPV16 | L1 | 8 | 506 | FTLGKRKA | 20639 |
| HPV16 | L1 | 11 | 236 | FTTLQANKSEV | 20640 |
| HPV16 | L1 | 8 | 232 | GAMDFTTL | 20641 |
| HPV16 | L1 | 10 | 232 | GAMDFTTLQA | 20642 |
| HPV16 | L1 | 11 | 291 | GAVGENVPDDL | 20643 |
| HPV16 | L1 | 8 | 305 | GSGSTANL | 20644 |
| HPV16 | L1 | 9 | 305 | GSGSTANLA | 20645 |
| HPV16 | L1 | 8 | 323 | GSMVTSDA | 20646 |
| HPV16 | L1 | 10 | 323 | GSMVTSDAQI | 20647 |
| HPV16 | L1 | 11 | 323 | GSMVTSDAQIF | 20648 |
| HPV16 | L1 | 8 | 198 | GSPCTNVA | 20649 |
| HPV16 | L1 | 9 | 198 | GSPCTNVAV | 20650 |
| HPV16 | L1 | 11 | 307 | GSTANLASSNY | 20651 |
| HPV16 | L1 | 9 | 438 | GTLEDTYRF | 20652 |
| HPV16 | L1 | 10 | 438 | GTLEDTYRFV | 20653 |
| HPV16 | L1 | 8 | 64 | GTSRLLAV | 20654 |
| HPV16 | L1 | 8 | 62 | HAGTSRLL | 20655 |
| HPV16 | L1 | 9 | 62 | HAGTSRLLA | 20656 |
| HPV16 | L1 | 10 | 62 | HAGTSRLLAV | 20657 |
| HPV16 | L1 | 8 | 418 | HSMNSTIL | 20658 |
| HPV16 | L1 | 11 | 418 | HSMNSTILEDW | 20659 |
| HPV16 | L1 | 11 | 457 | HTPPAPKEDPL | 20660 |
| HPV16 | L1 | 10 | 452 | IACQKHTPPA | 20661 |
| HPV16 | L1 | 10 | 143 | ISGHPLLNKL | 20662 |
| HPV16 | L1 | 10 | 173 | ISMDYKQTQL | 20663 |
| HPV16 | L1 | 8 | 374 | ISTSETTY | 20664 |
| HPV16 | L1 | 8 | 11 | ITCYENDV | 20665 |
| HPV16 | L1 | 10 | 11 | ITCYENDVNV | 20666 |
| HPV16 | L1 | 11 | 11 | ITCYENDVNVY | 20667 |
| HPV16 | L1 | 8 | 407 | ITLTADVM | 20668 |
| HPV16 | L1 | 10 | 407 | ITLTADVMTY | 20669 |
| HPV16 | L1 | 11 | 407 | ITLTADVMTYI | 20670 |
| HPV16 | L1 | 8 | 501 | KAKPKFTL | 20671 |

TABLE XIII-continued

B58 Supermotif Peptides

| Type | Protein | No. of Amino Acids | Position | Sequence | Seq. Id. No. |
|---|---|---|---|---|---|
| HPV16 | L1 | 8 | 243 | KSEVPLDI | 20672 |
| HPV16 | L1 | 8 | 69 | LAVGHPYF | 20673 |
| HPV16 | L1 | 10 | 69 | LAVGHPYFPI | 20674 |
| HPV16 | L1 | 8 | 409 | LTADVMTY | 20675 |
| HPV16 | L1 | 9 | 409 | LTADVMTYI | 20676 |
| HPV16 | L1 | 9 | 27 | MSLWLPSEA | 20677 |
| HPV16 | L1 | 11 | 27 | MSLWLPSEATV | 20678 |
| HPV16 | L1 | 11 | 414 | MTYIHSMNSTI | 20679 |
| HPV16 | L1 | 10 | 164 | NAGVDNRECI | 20680 |
| HPV16 | L1 | 9 | 157 | NASAYAANA | 20681 |
| HPV16 | L1 | 11 | 157 | NASAYAANAGV | 20682 |
| HPV16 | L1 | 8 | 421 | NSTILEDW | 20683 |
| HPV16 | L1 | 10 | 421 | NSTILEDWNF | 20684 |
| HPV16 | L1 | 8 | 383 | NTNFKEYL | 20685 |
| HPV16 | L1 | 9 | 218 | NTVIQDGDM | 20686 |
| HPV16 | L1 | 10 | 218 | NTVIQDGDMV | 20687 |
| HPV16 | L1 | 8 | 460 | PAPKEDPL | 20688 |
| HPV16 | L1 | 11 | 460 | PAPKEDPLKKY | 20689 |
| HPV16 | L1 | 8 | 32 | PSEATVYL | 20690 |
| HPV16 | L1 | 11 | 32 | PSEATVYLPPV | 20691 |
| HPV16 | L1 | 10 | 321 | PSGSMVTSDA | 20692 |
| HPV16 | L1 | 8 | 319 | PTPSGSMV | 20693 |
| HPV16 | L1 | 10 | 515 | PTTSSTSTTA | 20694 |
| HPV16 | L1 | 10 | 497 | QAGLKAKPKF | 20695 |
| HPV16 | L1 | 9 | 240 | QANKSEVPL | 20696 |
| HPV16 | L1 | 11 | 240 | QANKSEVPLDI | 20697 |
| HPV16 | L1 | 9 | 289 | RAGAVGENV | 20698 |
| HPV16 | L1 | 9 | 341 | RAQGHNNGI | 20699 |
| HPV16 | L1 | 11 | 341 | RAQGHNNGICW | 20700 |
| HPV16 | L1 | 9 | 364 | RSTNMSLCA | 20701 |
| HPV16 | L1 | 10 | 364 | RSTNMSLCAA | 20702 |
| HPV16 | L1 | 11 | 364 | RSTNMSLCAAI | 20703 |
| HPV16 | L1 | 8 | 56 | RTNIYYHA | 20704 |
| HPV16 | L1 | 9 | 482 | SADLDQFPL | 20705 |
| HPV16 | L1 | 9 | 159 | SAYAANAGV | 20706 |
| HPV16 | L1 | 10 | 308 | STANLASSNY | 20707 |
| HPV16 | L1 | 11 | 308 | STANLASSNYF | 20708 |
| HPV16 | L1 | 11 | 49 | STDEYVARTNI | 20709 |
| HPV16 | L1 | 9 | 422 | STILEDWNF | 20710 |
| HPV16 | L1 | 11 | 422 | STILEDWNFGL | 20711 |
| HPV16 | L1 | 8 | 365 | STNMSLCA | 20712 |
| HPV16 | L1 | 9 | 365 | STNMSLCAA | 20713 |
| HPV16 | L1 | 10 | 365 | STNMSLCAAI | 20714 |
| HPV16 | L1 | 11 | 521 | STTAKRKKRKL | 20715 |
| HPV16 | L1 | 8 | 410 | TADVMTYI | 20716 |
| HPV16 | L1 | 11 | 410 | TADVMTYIHSM | 20717 |
| HPV16 | L1 | 9 | 523 | TAKRKKRKL | 20718 |
| HPV16 | L1 | 9 | 309 | TANLASSNY | 20719 |
| HPV16 | L1 | 10 | 309 | TANLASSNYF | 20720 |
| HPV16 | L1 | 11 | 327 | TSDAQIFNKPY | 20721 |
| HPV16 | L1 | 11 | 376 | TSETTYKNTNF | 20722 |
| HPV16 | L1 | 11 | 114 | TSFYNPDTQRL | 20723 |
| HPV16 | L1 | 9 | 252 | TSICKYPDY | 20724 |
| HPV16 | L1 | 10 | 252 | TSICKYPDYI | 20725 |
| HPV16 | L1 | 11 | 65 | TSRLLAVGHPY | 20726 |
| HPV16 | L1 | 8 | 517 | TSSTSTTA | 20727 |
| HPV16 | L1 | 10 | 522 | TTAKRKKRKL | 20728 |
| HPV16 | L1 | 10 | 237 | TTLQANKSEV | 20729 |
| HPV16 | L1 | 9 | 362 | TTRSTNMSL | 20730 |
| HPV16 | L1 | 11 | 362 | TTRSTNMSLCA | 20731 |
| HPV16 | L1 | 9 | 516 | TTSSTSTTA | 20732 |
| HPV16 | L1 | 8 | 379 | TTYKNTNF | 20733 |
| HPV16 | L1 | 11 | 379 | TTYKNTNFKEY | 20734 |
| HPV16 | L1 | 8 | 54 | VARTNIYY | 20735 |
| HPV16 | L1 | 10 | 54 | VARTNIYYHA | 20736 |
| HPV16 | L1 | 11 | 204 | VAVNPGDCPPL | 20737 |
| HPV16 | L1 | 9 | 264 | VSEPYGDSL | 20738 |
| HPV16 | L1 | 10 | 264 | VSEPYGDSLF | 20739 |
| HPV16 | L1 | 11 | 264 | VSEPYGDSLFF | 20740 |
| HPV16 | L1 | 8 | 91 | VSGLQYRV | 20741 |
| HPV16 | L1 | 9 | 91 | VSGLQYRVF | 20742 |
| HPV16 | L1 | 11 | 91 | VSGLQYRVFRI | 20743 |
| HPV16 | L1 | 10 | 44 | VSKVVSTDEY | 20744 |
| HPV16 | L1 | 11 | 44 | VSKVVSTDEYV | 20745 |
| HPV16 | L1 | 8 | 48 | VSTDEYVA | 20746 |
| HPV16 | L1 | 8 | 3 | VTFIYILV | 20747 |

TABLE XIII-continued

B58 Supermotif Peptides

| Type | Protein | No. of Amino Acids | Position | Sequence | Seq. Id. No. |
|---|---|---|---|---|---|
| HPV16 | L1 | 9 | 3 | VTFIYILVI | 20748 |
| HPV16 | L1 | 8 | 326 | VTSDAQIF | 20749 |
| HPV16 | L1 | 8 | 126 | WACVGVEV | 20750 |
| HPV16 | L1 | 8 | 470 | YTFWEVNL | 20751 |
| HPV16 | L2 | 11 | 355 | AALPTSINNGL | 20752 |
| HPV16 | L2 | 8 | 82 | ATDTLAPV | 20753 |
| HPV16 | L2 | 11 | 15 | ATQLYKTCKQA | 20754 |
| HPV16 | L2 | 8 | 116 | DAGAPTSV | 20755 |
| HPV16 | L2 | 11 | 116 | DAGAPTSVPSI | 20756 |
| HPV16 | L2 | 11 | 442 | DAGDFYLHPSY | 20757 |
| HPV16 | L2 | 8 | 334 | DSAEEIEL | 20758 |
| HPV16 | L2 | 11 | 334 | DSAEEIELQTI | 20759 |
| HPV16 | L2 | 10 | 84 | DTLAPVRPPL | 20760 |
| HPV16 | L2 | 10 | 376 | DTSTTPVPSV | 20761 |
| HPV16 | L2 | 9 | 140 | DTTPAILDI | 20762 |
| HPV16 | L2 | 8 | 176 | ETGGHFTL | 20763 |
| HPV16 | L2 | 9 | 111 | ETSFIDAGA | 20764 |
| HPV16 | L2 | 8 | 466 | FSDVSLAA | 20765 |
| HPV16 | L2 | 8 | 268 | FSSNDNSI | 20766 |
| HPV16 | L2 | 10 | 268 | FSSNDNSINI | 20767 |
| HPV16 | L2 | 11 | 268 | FSSNDNSINIA | 20768 |
| HPV16 | L2 | 10 | 330 | FSTIDSAEEI | 20769 |
| HPV16 | L2 | 8 | 181 | FTLSSSTI | 20770 |
| HPV16 | L2 | 8 | 321 | GAKVHYYY | 20771 |
| HPV16 | L2 | 10 | 321 | GAKVHYYYDF | 20772 |
| HPV16 | L2 | 9 | 118 | GAPTSVPSI | 20773 |
| HPV16 | L2 | 8 | 404 | GAYNIPLV | 20774 |
| HPV16 | L2 | 10 | 63 | GSGTGGRTGY | 20775 |
| HPV16 | L2 | 11 | 63 | GSGTGGRTGYI | 20776 |
| HPV16 | L2 | 10 | 49 | GSMGVFFGGL | 20777 |
| HPV16 | L2 | 8 | 433 | GSPQYTII | 20778 |
| HPV16 | L2 | 9 | 433 | GSPQYTIIA | 20779 |
| HPV16 | L2 | 11 | 433 | GSPQYTIIADA | 20780 |
| HPV16 | L2 | 8 | 218 | GSRPVARL | 20781 |
| HPV16 | L2 | 10 | 218 | GSRPVARLGL | 20782 |
| HPV16 | L2 | 11 | 218 | GSRPVARLGLY | 20783 |
| HPV16 | L2 | 8 | 26 | GTCPPDII | 20784 |
| HPV16 | L2 | 11 | 26 | GTCPPDIIPKV | 20785 |
| HPV16 | L2 | 8 | 65 | GTGGRTGY | 20786 |
| HPV16 | L2 | 9 | 65 | GTGGRTGYI | 20787 |
| HPV16 | L2 | 11 | 65 | GTGGRTGYIPL | 20788 |
| HPV16 | L2 | 11 | 76 | GTRPPTATDTL | 20789 |
| HPV16 | L2 | 8 | 354 | HAALPTSI | 20790 |
| HPV16 | L2 | 8 | 440 | IADAGDFY | 20791 |
| HPV16 | L2 | 9 | 440 | IADAGDFYL | 20792 |
| HPV16 | L2 | 8 | 41 | IADQILQY | 20793 |
| HPV16 | L2 | 11 | 41 | IADQILQYGSM | 20794 |
| HPV16 | L2 | 8 | 277 | IAPDPDFL | 20795 |
| HPV16 | L2 | 10 | 277 | IAPDPDFLDI | 20796 |
| HPV16 | L2 | 11 | 277 | IAPDPDFLDIV | 20797 |
| HPV16 | L2 | 9 | 188 | ISTHNYEEI | 20798 |
| HPV16 | L2 | 11 | 188 | ISTHNYEEIPM | 20799 |
| HPV16 | L2 | 8 | 420 | ITDQAPSL | 20800 |
| HPV16 | L2 | 9 | 420 | ITDQAPSLI | 20801 |
| HPV16 | L2 | 11 | 420 | ITDQAPSLIPI | 20802 |
| HPV16 | L2 | 9 | 374 | ITDTSTTPV | 20803 |
| HPV16 | L2 | 8 | 243 | ITTPTKLI | 20804 |
| HPV16 | L2 | 10 | 243 | ITTPTKLITY | 20805 |
| HPV16 | L2 | 10 | 135 | ITTSTDTTPA | 20806 |
| HPV16 | L2 | 11 | 135 | ITTSTDTTPAI | 20807 |
| HPV16 | L2 | 8 | 250 | ITYDNPAY | 20808 |
| HPV16 | L2 | 11 | 250 | ITYDNPAYEGI | 20809 |
| HPV16 | L2 | 9 | 318 | KSIGAKVHY | 20810 |
| HPV16 | L2 | 10 | 318 | KSIGAKVHYY | 20811 |
| HPV16 | L2 | 11 | 318 | KSIGAKVHYYY | 20812 |
| HPV16 | L2 | 8 | 39 | KTIADQIL | 20813 |
| HPV16 | L2 | 10 | 39 | KTIADQILQY | 20814 |
| HPV16 | L2 | 8 | 86 | LAPVRPPL | 20815 |
| HPV16 | L2 | 10 | 86 | LAPVRPPLTV | 20816 |
| HPV16 | L2 | 11 | 390 | LSGYIPANTTI | 20817 |
| HPV16 | L2 | 11 | 183 | LSSSTISTHNY | 20818 |
| HPV16 | L2 | 8 | 294 | LTSRRTGI | 20819 |
| HPV16 | L2 | 10 | 294 | LTSRRTGIRY | 20820 |
| HPV16 | L2 | 11 | 273 | NSINIAPDPDF | 20821 |
| HPV16 | L2 | 9 | 397 | NTTIPFGGA | 20822 |
| HPV16 | L2 | 10 | 397 | NTTIPFGGAY | 20823 |

TABLE XIII-continued

B58 Supermotif Peptides

| Type | Protein | No. of Amino Acids | Position | Sequence | Seq. Id. No. |
|---|---|---|---|---|---|
| HPV16 | L2 | 9 | 208 | NTVTSSTPI | 20824 |
| HPV16 | L2 | 8 | 174 | PAETGGHF | 20825 |
| HPV16 | L2 | 10 | 174 | PAETGGHFTL | 20826 |
| HPV16 | L2 | 10 | 240 | PAFITTPTKL | 20827 |
| HPV16 | L2 | 11 | 240 | PAFITTPTKLI | 20828 |
| HPV16 | L2 | 10 | 143 | PAILDINNTV | 20829 |
| HPV16 | L2 | 10 | 292 | PALTSRRTGI | 20830 |
| HPV16 | L2 | 8 | 395 | PANTTIPF | 20831 |
| HPV16 | L2 | 11 | 395 | PANTTIPFGGA | 20832 |
| HPV16 | L2 | 8 | 255 | PAYEGIDV | 20833 |
| HPV16 | L2 | 9 | 100 | PSDPSIVSL | 20834 |
| HPV16 | L2 | 10 | 100 | PSDPSIVSLV | 20835 |
| HPV16 | L2 | 10 | 124 | PSIPPDVSGF | 20836 |
| HPV16 | L2 | 8 | 386 | PSTSLSGY | 20837 |
| HPV16 | L2 | 9 | 386 | PSTSLSGYI | 20838 |
| HPV16 | L2 | 11 | 386 | PSTSLSGYIPA | 20839 |
| HPV16 | L2 | 10 | 346 | PSTYTTTSHA | 20840 |
| HPV16 | L2 | 11 | 346 | PSTYTTTSHAA | 20841 |
| HPV16 | L2 | 10 | 166 | PSVLQPPTPA | 20842 |
| HPV16 | L2 | 8 | 383 | PSVPSTSL | 20843 |
| HPV16 | L2 | 11 | 383 | PSVPSTSLSGY | 20844 |
| HPV16 | L2 | 8 | 80 | PTATDTLA | 20845 |
| HPV16 | L2 | 10 | 80 | PTATDTLAPV | 20846 |
| HPV16 | L2 | 8 | 161 | PTFTDPSV | 20847 |
| HPV16 | L2 | 9 | 161 | PTFTDPSVL | 20848 |
| HPV16 | L2 | 11 | 246 | PTKLITYDNPA | 20849 |
| HPV16 | L2 | 10 | 172 | PTPAETGGHF | 20850 |
| HPV16 | L2 | 8 | 358 | PTSINNGL | 20851 |
| HPV16 | L2 | 9 | 358 | PTSINNGLY | 20852 |
| HPV16 | L2 | 11 | 358 | PTSINNGLYDI | 20853 |
| HPV16 | L2 | 11 | 120 | PTSVPSIPPDV | 20854 |
| HPV16 | L2 | 9 | 24 | QAGTCPPDI | 20855 |
| HPV16 | L2 | 10 | 24 | QAGTCPPDII | 20856 |
| HPV16 | L2 | 8 | 423 | QAPSLIPI | 20857 |
| HPV16 | L2 | 9 | 423 | QAPSLIPIV | 20858 |
| HPV16 | L2 | 8 | 342 | QTITPSTY | 20859 |
| HPV16 | L2 | 11 | 310 | QTLRTRSGKSI | 20860 |
| HPV16 | L2 | 8 | 12 | RASATQLY | 20861 |
| HPV16 | L2 | 9 | 5 | RSAKRTKRA | 20862 |
| HPV16 | L2 | 11 | 5 | RSAKRTKRASA | 20863 |
| HPV16 | L2 | 8 | 315 | RSGKSIGA | 20864 |
| HPV16 | L2 | 10 | 315 | RSGKSIGAKV | 20865 |
| HPV16 | L2 | 9 | 298 | RTGIRYSRI | 20866 |
| HPV16 | L2 | 10 | 9 | RTKRASATQL | 20867 |
| HPV16 | L2 | 11 | 9 | RTKRASATQLY | 20868 |
| HPV16 | L2 | 8 | 313 | RTRSGKSI | 20869 |
| HPV16 | L2 | 10 | 313 | RTRSGKSIGA | 20870 |
| HPV16 | L2 | 8 | 230 | RTTQQVKV | 20871 |
| HPV16 | L2 | 9 | 230 | RTTQQVKVV | 20872 |
| HPV16 | L2 | 10 | 335 | SAEEIELQTI | 20873 |
| HPV16 | L2 | 8 | 6 | SAKRTKRA | 20874 |
| HPV16 | L2 | 10 | 6 | SAKRTKRASA | 20875 |
| HPV16 | L2 | 9 | 269 | SSNDNSINI | 20876 |
| HPV16 | L2 | 10 | 269 | SSNDNSINIA | 20877 |
| HPV16 | L2 | 10 | 184 | SSSTISTHNY | 20878 |
| HPV16 | L2 | 9 | 185 | SSTISTHNY | 20879 |
| HPV16 | L2 | 11 | 212 | SSTPIPGSRPV | 20880 |
| HPV16 | L2 | 8 | 138 | STDTTPAI | 20881 |
| HPV16 | L2 | 9 | 138 | STDTTPAIL | 20882 |
| HPV16 | L2 | 11 | 138 | STDTTPAILDI | 20883 |
| HPV16 | L2 | 8 | 189 | STHNYEEI | 20884 |
| HPV16 | L2 | 10 | 189 | STHNYEEIPM | 20885 |
| HPV16 | L2 | 9 | 331 | STIDSAEEI | 20886 |
| HPV16 | L2 | 11 | 331 | STIDSAEEIEL | 20887 |
| HPV16 | L2 | 8 | 186 | STISTHNY | 20888 |
| HPV16 | L2 | 11 | 186 | STISTHNYEEI | 20889 |
| HPV16 | L2 | 10 | 213 | STPIPGSRPV | 20890 |
| HPV16 | L2 | 11 | 213 | STPIPGSRPVA | 20891 |
| HPV16 | L2 | 8 | 387 | STSLSGYI | 20892 |
| HPV16 | L2 | 10 | 387 | STSLSGYIPA | 20893 |
| HPV16 | L2 | 8 | 378 | STTPVPSV | 20894 |
| HPV16 | L2 | 9 | 347 | STYTTTSHA | 20895 |
| HPV16 | L2 | 10 | 347 | STYTTTSHAA | 20896 |
| HPV16 | L2 | 11 | 347 | STYTTTSHAAL | 20897 |
| HPV16 | L2 | 9 | 81 | TATDTLAPV | 20898 |
| HPV16 | L2 | 8 | 112 | TSFIDAGA | 20899 |

TABLE XIII-continued

B58 Supermotif Peptides

| Type | Protein | No. of Amino Acids | Position | Sequence | Seq. Id. No. |
|---|---|---|---|---|---|
| HPV16 | L2 | 10 | 352 | TSHAALPTSI | 20900 |
| HPV16 | L2 | 8 | 359 | TSINNGLY | 20901 |
| HPV16 | L2 | 10 | 359 | TSINNGLYDI | 20902 |
| HPV16 | L2 | 11 | 359 | TSINNGLYDIY | 20903 |
| HPV16 | L2 | 9 | 388 | TSLSGYIPA | 20904 |
| HPV16 | L2 | 9 | 295 | TSRRTGIRY | 20905 |
| HPV16 | L2 | 8 | 137 | TSTDTTPA | 20906 |
| HPV16 | L2 | 9 | 137 | TSTDTTPAI | 20907 |
| HPV16 | L2 | 10 | 137 | TSTDTTPAIL | 20908 |
| HPV16 | L2 | 9 | 377 | TSTTPVPSV | 20909 |
| HPV16 | L2 | 10 | 121 | TSVPSIPPDV | 20910 |
| HPV16 | L2 | 8 | 156 | TTHNNPTF | 20911 |
| HPV16 | L2 | 8 | 398 | TTIPFGGA | 20912 |
| HPV16 | L2 | 9 | 398 | TTIPFGGAY | 20913 |
| HPV16 | L2 | 11 | 398 | TTIPFGGAYNI | 20914 |
| HPV16 | L2 | 8 | 141 | TTPAILDI | 20915 |
| HPV16 | L2 | 9 | 244 | TTPTKLITY | 20916 |
| HPV16 | L2 | 8 | 231 | TTQQVKVV | 20917 |
| HPV16 | L2 | 11 | 231 | TTQQVKVVDPA | 20918 |
| HPV16 | L2 | 11 | 351 | TTSHAALPTSI | 20919 |
| HPV16 | L2 | 9 | 136 | TTSTDTTPA | 20920 |
| HPV16 | L2 | 10 | 136 | TTSTDTTPAI | 20921 |
| HPV16 | L2 | 11 | 136 | TTSTDTTPAIL | 20922 |
| HPV16 | L2 | 8 | 350 | TTTSHAAL | 20923 |
| HPV16 | L2 | 11 | 153 | TTVTTHNNPTF | 20924 |
| HPV16 | L2 | 8 | 287 | VALHRPAL | 20925 |
| HPV16 | L2 | 8 | 411 | VSGPDIPI | 20926 |
| HPV16 | L2 | 10 | 411 | VSGPDIPINI | 20927 |
| HPV16 | L2 | 9 | 106 | VSLVEETSF | 20928 |
| HPV16 | L2 | 10 | 106 | VSLVEETSFI | 20929 |
| HPV16 | L2 | 8 | 203 | VSTNPNTV | 20930 |
| HPV16 | L2 | 9 | 155 | VTTHNNPTF | 20931 |
| HPV16 | L2 | 10 | 303 | YSRIGNKQTL | 20932 |
| HPV16 | L2 | 8 | 228 | YSRTTQQV | 20933 |
| HPV16 | L2 | 10 | 228 | YSRTTQQVKV | 20934 |
| HPV16 | L2 | 11 | 228 | YSRTTQQVKVV | 20935 |
| HPV16 | L2 | 10 | 437 | YTIIADAGDF | 20936 |
| HPV16 | L2 | 11 | 437 | YTIIADAGDFY | 20937 |
| HPV16 | L2 | 8 | 349 | YTTTSHAA | 20938 |
| HPV16 | L2 | 9 | 349 | YTTTSHAAL | 20939 |
| HPV18 | E1 | 11 | 396 | AAAFLKSNCQA | 20940 |
| HPV18 | E1 | 10 | 397 | AAFLKSNCQA | 20941 |
| HPV18 | E1 | 10 | 324 | AALYWYRTGI | 20942 |
| HPV18 | E1 | 8 | 40 | ATDTGSDM | 20943 |
| HPV18 | E1 | 9 | 40 | ATDTGSDMV | 20944 |
| HPV18 | E1 | 11 | 40 | ATDTGSDMVDF | 20945 |
| HPV18 | E1 | 10 | 413 | ATMCKHYRRA | 20946 |
| HPV18 | E1 | 8 | 531 | ATTTCWTY | 20947 |
| HPV18 | E1 | 9 | 531 | ATTTCWTYF | 20948 |
| HPV18 | E1 | 8 | 412 | CATMCKHY | 20949 |
| HPV18 | E1 | 11 | 412 | CATMCKHYRRA | 20950 |
| HPV18 | E1 | 9 | 139 | CSEVEATQI | 20951 |
| HPV18 | E1 | 11 | 139 | CSEVEATQIQV | 20952 |
| HPV18 | E1 | 8 | 160 | CSGGSTEA | 20953 |
| HPV18 | E1 | 9 | 160 | CSGGSTEAI | 20954 |
| HPV18 | E1 | 10 | 437 | CSKIDEGGDW | 20955 |
| HPV18 | E1 | 8 | 240 | CTDWVTAI | 20956 |
| HPV18 | E1 | 9 | 240 | CTDWVTAIF | 20957 |
| HPV18 | E1 | 11 | 240 | CTDWVTAIFGV | 20958 |
| HPV18 | E1 | 9 | 196 | CTIAQLKDL | 20959 |
| HPV18 | E1 | 10 | 196 | CTIAQLKDLL | 20960 |
| HPV18 | E1 | 9 | 635 | DADTEGNPF | 20961 |
| HPV18 | E1 | 8 | 78 | DAQVLHVL | 20962 |
| HPV18 | E1 | 9 | 530 | DATTTCWTY | 20963 |
| HPV18 | E1 | 10 | 530 | DATTTCWTYF | 20964 |
| HPV18 | E1 | 9 | 134 | DSGYGCSEV | 20965 |
| HPV18 | E1 | 11 | 134 | DSGYGCSEVEA | 20966 |
| HPV18 | E1 | 9 | 359 | DSNFDLSEM | 20967 |
| HPV18 | E1 | 10 | 359 | DSNFDLSEMV | 20968 |
| HPV18 | E1 | 8 | 391 | DSNSNAAA | 20969 |
| HPV18 | E1 | 9 | 391 | DSNSNAAAF | 20970 |
| HPV18 | E1 | 10 | 391 | DSNSNAAAFL | 20971 |
| HPV18 | E1 | 10 | 637 | DTEGNPFGTF | 20972 |
| HPV18 | E1 | 8 | 106 | DTELSPRL | 20973 |
| HPV18 | E1 | 11 | 106 | DTELSPRLQEI | 20974 |
| HPV18 | E1 | 9 | 42 | DTGSDMVDF | 20975 |

TABLE XIII-continued

B58 Supermotif Peptides

| Type | Protein | No. of Amino Acids | Position | Sequence | Seq. Id. No. |
|---|---|---|---|---|---|
| HPV18 | E1 | 10 | 42 | DTGSDMVDFI | 20976 |
| HPV18 | E1 | 10 | 522 | DTKVAMLDDA | 20977 |
| HPV18 | E1 | 9 | 342 | DTPEWIQRL | 20978 |
| HPV18 | E1 | 11 | 342 | DTPEWIQRLTI | 20979 |
| HPV18 | E1 | 10 | 52 | DTQGTFCEQA | 20980 |
| HPV18 | E1 | 10 | 220 | DTYGLSFTDL | 20981 |
| HPV18 | E1 | 11 | 220 | DTYGLSFTDLV | 20982 |
| HPV18 | E1 | 8 | 540 | DTYMRNAL | 20983 |
| HPV18 | E1 | 8 | 379 | EDSMAFEY | 20984 |
| HPV18 | E1 | 9 | 379 | EDSMAFEYA | 20985 |
| HPV18 | E1 | 10 | 379 | EDSMAFEYAL | 20986 |
| HPV18 | E1 | 11 | 379 | EDSMAFEYALL | 20987 |
| HPV18 | E1 | 9 | 587 | ESRITVFEF | 20988 |
| HPV18 | E1 | 9 | 64 | ETAQALFHA | 20989 |
| HPV18 | E1 | 11 | 309 | ETCMLIQPPKL | 20990 |
| HPV18 | E1 | 11 | 89 | FAGGSTENSPL | 20991 |
| HPV18 | E1 | 8 | 226 | FTDLVRNF | 20992 |
| HPV18 | E1 | 8 | 130 | FTISDSGY | 20993 |
| HPV18 | E1 | 11 | 212 | GAMLAVFKDTY | 20994 |
| HPV18 | E1 | 8 | 44 | GSDMVDFI | 20995 |
| HPV18 | E1 | 8 | 92 | GSTENSPL | 20996 |
| HPV18 | E1 | 9 | 172 | GTEGNNSSV | 20997 |
| HPV18 | E1 | 9 | 55 | GTFCEQAEL | 20998 |
| HPV18 | E1 | 8 | 11 | GTGCNGWF | 20999 |
| HPV18 | E1 | 9 | 11 | GTGCNGWFY | 21000 |
| HPV18 | E1 | 10 | 11 | GTGCNGWFYV | 21001 |
| HPV18 | E1 | 8 | 473 | GTPKKNCL | 21002 |
| HPV18 | E1 | 9 | 473 | GTPKKNCLV | 21003 |
| HPV18 | E1 | 10 | 473 | GTPKKNCLVF | 21004 |
| HPV18 | E1 | 8 | 182 | GTSDNSNI | 21005 |
| HPV18 | E1 | 11 | 182 | GTSDNSNIENV | 21006 |
| HPV18 | E1 | 9 | 71 | HAQEVHNDA | 21007 |
| HPV18 | E1 | 11 | 71 | HAQEVHNDAQV | 21008 |
| HPV18 | E1 | 8 | 254 | IAEGFKTL | 21009 |
| HPV18 | E1 | 9 | 254 | IAEGFKTLI | 21010 |
| HPV18 | E1 | 8 | 198 | IAQLKDLL | 21011 |
| HPV18 | E1 | 10 | 198 | IAQLKDLLKV | 21012 |
| HPV18 | E1 | 9 | 32 | ISDDEDENA | 21013 |
| HPV18 | E1 | 11 | 132 | ISDSGYGCSEV | 21014 |
| HPV18 | E1 | 11 | 336 | ISEVMGDTPEW | 21015 |
| HPV18 | E1 | 10 | 506 | ISFVNSTSHF | 21016 |
| HPV18 | E1 | 11 | 506 | ISFVNSTSHFW | 21017 |
| HPV18 | E1 | 10 | 552 | ISIDRKHKPL | 21018 |
| HPV18 | E1 | 11 | 552 | ISIDRKHKPLI | 21019 |
| HPV18 | E1 | 10 | 116 | ISLNSGQKKA | 21020 |
| HPV18 | E1 | 8 | 333 | ISNISEVM | 21021 |
| HPV18 | E1 | 10 | 461 | ITFLGALKSF | 21022 |
| HPV18 | E1 | 11 | 461 | ITFLGALKSFL | 21023 |
| HPV18 | E1 | 9 | 590 | ITVFEFPNA | 21024 |
| HPV18 | E1 | 10 | 590 | ITVFEFPNAF | 21025 |
| HPV18 | E1 | 9 | 124 | KAKRRLFTI | 21026 |
| HPV18 | E1 | 10 | 234 | KSDKTTCTDW | 21027 |
| HPV18 | E1 | 11 | 234 | KSDKTTCTDWV | 21028 |
| HPV18 | E1 | 8 | 401 | KSNCQAKY | 21029 |
| HPV18 | E1 | 9 | 401 | KSNCQAKYL | 21030 |
| HPV18 | E1 | 10 | 292 | KSRLTVAKGL | 21031 |
| HPV18 | E1 | 8 | 490 | KSYFGMSF | 21032 |
| HPV18 | E1 | 9 | 490 | KSYFGMSFI | 21033 |
| HPV18 | E1 | 11 | 490 | KSYFGMSFIHF | 21034 |
| HPV18 | E1 | 8 | 259 | KTLIQPFI | 21035 |
| HPV18 | E1 | 9 | 259 | KTLIQPFIL | 21036 |
| HPV18 | E1 | 10 | 259 | KTLIQPFILY | 21037 |
| HPV18 | E1 | 11 | 259 | KTLIQPFILYA | 21038 |
| HPV18 | E1 | 8 | 237 | KTTCTDWV | 21039 |
| HPV18 | E1 | 10 | 237 | KTTCTDWVTA | 21040 |
| HPV18 | E1 | 11 | 237 | KTTCTDWVTAI | 21041 |
| HPV18 | E1 | 8 | 389 | LADSNSNA | 21042 |
| HPV18 | E1 | 9 | 389 | LADSNSNAA | 21043 |
| HPV18 | E1 | 10 | 389 | LADSNSNAAA | 21044 |
| HPV18 | E1 | 11 | 389 | LADSNSNAAAF | 21045 |
| HPV18 | E1 | 8 | 215 | LAVFKDTY | 21046 |
| HPV18 | E1 | 10 | 215 | LAVFKDTYGL | 21047 |
| HPV18 | E1 | 8 | 364 | LSEMVQWA | 21048 |
| HPV18 | E1 | 9 | 364 | LSEMVQWAF | 21049 |
| HPV18 | E1 | 10 | 224 | LSFTDLVRNF | 21050 |
| HPV18 | E1 | 8 | 109 | LSPRLQEI | 21051 |

TABLE XIII-continued

B58 Supermotif Peptides

| Type | Protein | No. of Amino Acids | Position | Sequence | Seq. Id. No. |
|---|---|---|---|---|---|
| HPV18 | E1 | 10 | 109 | LSPRLQEISL | 21052 |
| HPV18 | E1 | 8 | 376 | LTDESDMA | 21053 |
| HPV18 | E1 | 9 | 376 | LTDESDMAF | 21054 |
| HPV18 | E1 | 11 | 376 | LTDESDMAFEY | 21055 |
| HPV18 | E1 | 8 | 520 | LTDTKVAM | 21056 |
| HPV18 | E1 | 9 | 520 | LTDTKVAML | 21057 |
| HPV18 | E1 | 8 | 350 | LTIIQHGI | 21058 |
| HPV18 | E1 | 8 | 571 | LTTNIHPA | 21059 |
| HPV18 | E1 | 10 | 295 | LTVAKGLSTL | 21060 |
| HPV18 | E1 | 11 | 295 | LTVAKGLSTLL | 21061 |
| HPV18 | E1 | 8 | 382 | MAFEYALL | 21062 |
| HPV18 | E1 | 9 | 382 | MAFEYALLA | 21063 |
| HPV18 | E1 | 10 | 495 | MSFIHFIQGA | 21064 |
| HPV18 | E1 | 11 | 495 | MSFIHFIQGAV | 21065 |
| HPV18 | E1 | 8 | 545 | NALDGNPI | 21066 |
| HPV18 | E1 | 10 | 545 | NALDGNPISI | 21067 |
| HPV18 | E1 | 9 | 39 | NATDTGSDM | 21068 |
| HPV18 | E1 | 10 | 39 | NATDTGSDMV | 21069 |
| HPV18 | E1 | 11 | 119 | NSGQKKAKRRL | 21070 |
| HPV18 | E1 | 8 | 393 | NSNAAAFL | 21071 |
| HPV18 | E1 | 8 | 96 | NSPLGERL | 21072 |
| HPV18 | E1 | 10 | 96 | NSPLGERLEV | 21073 |
| HPV18 | E1 | 8 | 510 | NSTSHFWL | 21074 |
| HPV18 | E1 | 11 | 510 | NSTSHFWLEPL | 21075 |
| HPV18 | E1 | 9 | 487 | NTGKSYFGM | 21076 |
| HPV18 | E1 | 11 | 487 | NTGKSYFGMSF | 21077 |
| HPV18 | E1 | 9 | 577 | PAKDNRWPY | 21078 |
| HPV18 | E1 | 10 | 577 | PAKDNRWPYL | 21079 |
| HPV18 | E1 | 8 | 485 | PANTGKSY | 21080 |
| HPV18 | E1 | 9 | 485 | PANTGKSYF | 21081 |
| HPV18 | E1 | 11 | 485 | PANTGKSYFGM | 21082 |
| HPV18 | E1 | 10 | 252 | PTIAEGFKTL | 21083 |
| HPV18 | E1 | 11 | 252 | PTIAEGFKTLI | 21084 |
| HPV18 | E1 | 9 | 60 | QAELETAQA | 21085 |
| HPV18 | E1 | 10 | 60 | QAELETAQAL | 21086 |
| HPV18 | E1 | 11 | 60 | QAELETAQALF | 21087 |
| HPV18 | E1 | 11 | 21 | QAIVDKKTGDV | 21088 |
| HPV18 | E1 | 9 | 405 | QAKYLKDCA | 21089 |
| HPV18 | E1 | 11 | 405 | QAKYLKDCATM | 21090 |
| HPV18 | E1 | 9 | 67 | QALFHAQEV | 21091 |
| HPV18 | E1 | 9 | 649 | RAGQNHRPL | 21092 |
| HPV18 | E1 | 9 | 421 | RAQKRQMNM | 21093 |
| HPV18 | E1 | 8 | 320 | RSSVAALY | 21094 |
| HPV18 | E1 | 9 | 320 | RSSVAALYW | 21095 |
| HPV18 | E1 | 10 | 320 | RSSVAALYWY | 21096 |
| HPV18 | E1 | 10 | 330 | RTGISNISEV | 21097 |
| HPV18 | E1 | 11 | 330 | RTGISNISEVM | 21098 |
| HPV18 | E1 | 8 | 622 | RTWSRLDL | 21099 |
| HPV18 | E1 | 8 | 321 | SSVAALYW | 21100 |
| HPV18 | E1 | 9 | 321 | SSVAALYWY | 21101 |
| HPV18 | E1 | 11 | 93 | STENSPLGERL | 21102 |
| HPV18 | E1 | 11 | 302 | STLLHVPETCM | 21103 |
| HPV18 | E1 | 10 | 511 | STSHFWLEPL | 21104 |
| HPV18 | E1 | 10 | 245 | TAIFGVNPTI | 21105 |
| HPV18 | E1 | 11 | 245 | TAIFGVNPTIA | 21106 |
| HPV18 | E1 | 8 | 65 | TAQALFHA | 21107 |
| HPV18 | E1 | 11 | 65 | TAQALFHAQEV | 21108 |
| HPV18 | E1 | 10 | 183 | TSDNSNIENV | 21109 |
| HPV18 | E1 | 9 | 512 | TSHFWLEPL | 21110 |
| HPV18 | E1 | 9 | 238 | TTCTDWVTA | 21111 |
| HPV18 | E1 | 10 | 238 | TTCTDWVTAI | 21112 |
| HPV18 | E1 | 11 | 238 | TTCTDWVTAIF | 21113 |
| HPV18 | E1 | 10 | 533 | TTCWTYFDTY | 21114 |
| HPV18 | E1 | 11 | 533 | TTCWTYFDTYM | 21115 |
| HPV18 | E1 | 10 | 150 | TTNGEHGGNV | 21116 |
| HPV18 | E1 | 8 | 532 | TTTCWTYF | 21117 |
| HPV18 | E1 | 11 | 532 | TTTCWTYFDTY | 21118 |
| HPV18 | E1 | 11 | 323 | VAALYWYRTGI | 21119 |
| HPV18 | E1 | 8 | 297 | VAKGLSTL | 21120 |
| HPV18 | E1 | 9 | 297 | VAKGLSTLL | 21121 |
| HPV18 | E1 | 11 | 297 | VAKGLSTLLHV | 21122 |
| HPV18 | E1 | 11 | 244 | VTAIFGVNPTI | 21123 |
| HPV18 | E1 | 11 | 149 | VTTNGEHGGNV | 21124 |
| HPV18 | E1 | 8 | 536 | WTYFDTYM | 21125 |
| HPV18 | E1 | 11 | 536 | WTYFDTYMRNA | 21126 |
| HPV18 | E1 | 11 | 268 | YAHIQCLDCKW | 21127 |

TABLE XIII-continued

B58 Supermotif Peptides

| Type | Protein | No. of Amino Acids | Position | Sequence | Seq. Id. No. |
|---|---|---|---|---|---|
| HPV18 | E1 | 11 | 386 | YALLADSNSNA | 21128 |
| HPV18 | E2 | 10 | 49 | AAREHGIQTL | 21129 |
| HPV18 | E2 | 10 | 245 | AATRPGHCGL | 21130 |
| HPV18 | E2 | 11 | 245 | AATRPGHCGLA | 21131 |
| HPV18 | E2 | 9 | 154 | ATCVSHRGL | 21132 |
| HPV18 | E2 | 10 | 154 | ATCVSHRGLY | 21133 |
| HPV18 | E2 | 11 | 154 | ATCVSHRGLYY | 21134 |
| HPV18 | E2 | 8 | 214 | ATQLVKQL | 21135 |
| HPV18 | E2 | 9 | 246 | ATRPGHCGL | 21136 |
| HPV18 | E2 | 10 | 246 | ATRPGHCGLA | 21137 |
| HPV18 | E2 | 8 | 282 | CSGNTTPI | 21138 |
| HPV18 | E2 | 9 | 282 | CSGNTTPII | 21139 |
| HPV18 | E2 | 11 | 282 | CSGNTTPIIHL | 21140 |
| HPV18 | E2 | 8 | 205 | CSTSDDTV | 21141 |
| HPV18 | E2 | 10 | 205 | CSTSDDTVSA | 21142 |
| HPV18 | E2 | 9 | 146 | DAGTWDKTA | 21143 |
| HPV18 | E2 | 9 | 26 | DSKDIDSQI | 21144 |
| HPV18 | E2 | 11 | 26 | DSKDIDSQIQY | 21145 |
| HPV18 | E2 | 11 | 202 | DSMCSTSDDTV | 21146 |
| HPV18 | E2 | 9 | 31 | DSQIQYWQL | 21147 |
| HPV18 | E2 | 10 | 31 | DSQIQYWQLI | 21148 |
| HPV18 | E2 | 9 | 354 | DSVQILVGY | 21149 |
| HPV18 | E2 | 10 | 354 | DSVQILVGYM | 21150 |
| HPV18 | E2 | 9 | 139 | DSVYYMTDA | 21151 |
| HPV18 | E2 | 8 | 210 | DTVSATQL | 21152 |
| HPV18 | E2 | 9 | 210 | DTVSATQLV | 21153 |
| HPV18 | E2 | 10 | 6 | ETLSERLSCV | 21154 |
| HPV18 | E2 | 8 | 340 | ETQRTKFL | 21155 |
| HPV18 | E2 | 11 | 340 | ETQRTKFLNTV | 21156 |
| HPV18 | E2 | 8 | 48 | FAAREHGI | 21157 |
| HPV18 | E2 | 11 | 48 | FAAREHGIQTL | 21158 |
| HPV18 | E2 | 9 | 324 | GAGNEKTGI | 21159 |
| HPV18 | E2 | 10 | 324 | GAGNEKTGIL | 21160 |
| HPV18 | E2 | 11 | 235 | GTAKTYGQTSA | 21161 |
| HPV18 | E2 | 10 | 148 | GTWDKTATCV | 21162 |
| HPV18 | E2 | 11 | 187 | GTWEVHFGNNV | 21163 |
| HPV18 | E2 | 8 | 309 | HSDHYRDI | 21164 |
| HPV18 | E2 | 9 | 338 | HSETQRTKF | 21165 |
| HPV18 | E2 | 10 | 338 | HSETQRTKFL | 21166 |
| HPV18 | E2 | 10 | 223 | HTPSPYSSTV | 21167 |
| HPV18 | E2 | 9 | 68 | ISKSKAHKA | 21168 |
| HPV18 | E2 | 10 | 68 | ISKSKAHKAI | 21169 |
| HPV18 | E2 | 10 | 316 | ISSTWHWTGA | 21170 |
| HPV18 | E2 | 8 | 72 | KAHKAIEL | 21171 |
| HPV18 | E2 | 10 | 72 | KAHKAIELQM | 21172 |
| HPV18 | E2 | 11 | 72 | KAHKAIELQMA | 21173 |
| HPV18 | E2 | 8 | 75 | KAIELQMA | 21174 |
| HPV18 | E2 | 9 | 75 | KAIELQMAL | 21175 |
| HPV18 | E2 | 8 | 70 | KSKAHKAI | 21176 |
| HPV18 | E2 | 10 | 70 | KSKAHKAIEL | 21177 |
| HPV18 | E2 | 11 | 152 | KTATCVSHRGL | 21178 |
| HPV18 | E2 | 9 | 329 | KTGILTVTY | 21179 |
| HPV18 | E2 | 8 | 238 | KTYGQTSA | 21180 |
| HPV18 | E2 | 9 | 238 | KTYGQTSAA | 21181 |
| HPV18 | E2 | 10 | 254 | LAEKQHCGPV | 21182 |
| HPV18 | E2 | 11 | 86 | LAQSRYKTEDW | 21183 |
| HPV18 | E2 | 8 | 12 | LSCVQDKI | 21184 |
| HPV18 | E2 | 9 | 12 | LSCVQDKII | 21185 |
| HPV18 | E2 | 8 | 8 | LSERLSCV | 21186 |
| HPV18 | E2 | 11 | 81 | MALQGLAQSRY | 21187 |
| HPV18 | E2 | 11 | 144 | MTDAGTWDKTA | 21188 |
| HPV18 | E2 | 9 | 133 | MTYVAWDSV | 21189 |
| HPV18 | E2 | 10 | 133 | MTYVAWDSVY | 21190 |
| HPV18 | E2 | 11 | 133 | MTYVAWDSVYY | 21191 |
| HPV18 | E2 | 8 | 297 | NSLKCLRY | 21192 |
| HPV18 | E2 | 10 | 297 | NSLKCLRYRL | 21193 |
| HPV18 | E2 | 8 | 107 | NTEPTHCF | 21194 |
| HPV18 | E2 | 9 | 185 | NTGTWEVHF | 21195 |
| HPV18 | E2 | 8 | 285 | NTTPIIHL | 21196 |
| HPV18 | E2 | 9 | 348 | NTVAIPDSV | 21197 |
| HPV18 | E2 | 11 | 348 | NTVAIPDSVQI | 21198 |
| HPV18 | E2 | 10 | 64 | PAYNISKSKA | 21199 |
| HPV18 | E2 | 8 | 225 | PSPYSSTV | 21200 |
| HPV18 | E2 | 10 | 225 | PSPYSSTVSV | 21201 |
| HPV18 | E2 | 10 | 272 | PTGNNKRRKL | 21202 |
| HPV18 | E2 | 9 | 88 | QSRYKTEDW | 21203 |

TABLE XIII-continued

B58 Supermotif Peptides

| Type | Protein | No. of Amino Acids | Position | Sequence | Seq. Id. No. |
|---|---|---|---|---|---|
| HPV18 | E2 | 11 | 88 | QSRYKTEDWTL | 21204 |
| HPV18 | E2 | 8 | 56 | QTLNHQVV | 21205 |
| HPV18 | E2 | 10 | 56 | QTLNHQVVPA | 21206 |
| HPV18 | E2 | 11 | 56 | QTLNHQVVPAY | 21207 |
| HPV18 | E2 | 11 | 2 | QTPKETLSERL | 21208 |
| HPV18 | E2 | 8 | 343 | RTKFLNTV | 21209 |
| HPV18 | E2 | 9 | 343 | RTKFLNTVA | 21210 |
| HPV18 | E2 | 10 | 343 | RTKFLNTVAI | 21211 |
| HPV18 | E2 | 11 | 244 | SAATRPGHCGL | 21212 |
| HPV18 | E2 | 9 | 213 | SATQLVKQL | 21213 |
| HPV18 | E2 | 9 | 229 | SSTVSVGTA | 21214 |
| HPV18 | E2 | 9 | 317 | SSTWHWTGA | 21215 |
| HPV18 | E2 | 9 | 206 | STSDDTVSA | 21216 |
| HPV18 | E2 | 8 | 230 | STVSVGTA | 21217 |
| HPV18 | E2 | 11 | 230 | STVSVGTAKTY | 21218 |
| HPV18 | E2 | 8 | 318 | STWHWTGA | 21219 |
| HPV18 | E2 | 10 | 236 | TAKTYGQTSA | 21220 |
| HPV18 | E2 | 11 | 236 | TAKTYGQTSAA | 21221 |
| HPV18 | E2 | 10 | 153 | TATCVSHRGL | 21222 |
| HPV18 | E2 | 11 | 153 | TATCVSHRGLY | 21223 |
| HPV18 | E2 | 8 | 207 | TSDDTVSA | 21224 |
| HPV18 | E2 | 11 | 207 | TSDDTVSATQL | 21225 |
| HPV18 | E2 | 9 | 350 | VAIPDSVQI | 21226 |
| HPV18 | E2 | 10 | 350 | VAIPDSVQIL | 21227 |
| HPV18 | E2 | 11 | 350 | VAIPDSVQILV | 21228 |
| HPV18 | E2 | 8 | 136 | VAWDSVYY | 21229 |
| HPV18 | E2 | 9 | 136 | VAWDSVYYM | 21230 |
| HPV18 | E2 | 10 | 212 | VSATQLVKQL | 21231 |
| HPV18 | E2 | 8 | 157 | VSHRGLYY | 21232 |
| HPV18 | E2 | 9 | 157 | VSHRGLYYV | 21233 |
| HPV18 | E2 | 9 | 232 | VSVGTAKTY | 21234 |
| HPV18 | E2 | 11 | 322 | WTGAGNEKTGI | 21235 |
| HPV18 | E2 | 10 | 96 | WTLQDTCEEL | 21236 |
| HPV18 | E2 | 11 | 96 | WTLQDTCEELW | 21237 |
| HPV18 | E2 | 10 | 228 | YSSTVSVGTA | 21238 |
| HPV18 | E5 | 8 | 47 | ATAFTVYV | 21239 |
| HPV18 | E5 | 9 | 47 | ATAFTVYVF | 21240 |
| HPV18 | E5 | 11 | 47 | ATAFTVYVFCF | 21241 |
| HPV18 | E5 | 8 | 29 | CAYAWVLV | 21242 |
| HPV18 | E5 | 9 | 29 | CAYAWVLVF | 21243 |
| HPV18 | E5 | 10 | 29 | CAYAWVLVFV | 21244 |
| HPV18 | E5 | 11 | 29 | CAYAWVLVFVY | 21245 |
| HPV18 | E5 | 8 | 50 | FTVYVFCF | 21246 |
| HPV18 | E5 | 9 | 50 | FTVYVFCFL | 21247 |
| HPV18 | E5 | 10 | 50 | FTVYVFCFLL | 21248 |
| HPV18 | E5 | 8 | 43 | ITSPATAF | 21249 |
| HPV18 | E5 | 10 | 43 | ITSPATAFTV | 21250 |
| HPV18 | E5 | 11 | 43 | ITSPATAFTVY | 21251 |
| HPV18 | E5 | 9 | 2 | LSLIFLFCF | 21252 |
| HPV18 | E5 | 11 | 2 | LSLIFLFCFCV | 21253 |
| HPV18 | E5 | 8 | 46 | PATAFTVY | 21254 |
| HPV18 | E5 | 9 | 46 | PATAFTVYV | 21255 |
| HPV18 | E5 | 10 | 46 | PATAFTVYVF | 21256 |
| HPV18 | E5 | 8 | 24 | PSVCMCAY | 21257 |
| HPV18 | E5 | 9 | 24 | PSVCMCAYA | 21258 |
| HPV18 | E5 | 10 | 24 | PSVCMCAYAW | 21259 |
| HPV18 | E5 | 11 | 24 | PSVCMCAYAWV | 21260 |
| HPV18 | E5 | 8 | 48 | TAFTVYVF | 21261 |
| HPV18 | E5 | 10 | 48 | TAFTVYVFCF | 21262 |
| HPV18 | E5 | 11 | 48 | TAFTVYVFCFL | 21263 |
| HPV18 | E5 | 9 | 44 | TSPATAFTV | 21264 |
| HPV18 | E5 | 10 | 44 | TSPATAFTVY | 21265 |
| HPV18 | E5 | 11 | 44 | TSPATAFTVYV | 21266 |
| HPV18 | E5 | 8 | 31 | YAWVLVFV | 21267 |
| HPV18 | E5 | 9 | 31 | YAWVLVFVY | 21268 |
| HPV18 | E5 | 10 | 31 | YAWVLVFVYI | 21269 |
| HPV18 | E5 | 11 | 31 | YAWVLVFVYIV | 21270 |
| HPV18 | E6 | 9 | 63 | AACHKCIDF | 21271 |
| HPV18 | E6 | 10 | 63 | AACHKCIDFY | 21272 |
| HPV18 | E6 | 8 | 18 | CTELNTSL | 21273 |
| HPV18 | E6 | 11 | 18 | CTELNTSLQDI | 21274 |
| HPV18 | E6 | 8 | 83 | DSVYGDTL | 21275 |
| HPV18 | E6 | 11 | 83 | DSVYGDTLEKL | 21276 |
| HPV18 | E6 | 11 | 88 | DTLEKLTNTGL | 21277 |
| HPV18 | E6 | 8 | 47 | FAFKDLFV | 21278 |
| HPV18 | E6 | 9 | 47 | FAFKDLFVV | 21279 |

TABLE XIII-continued

B58 Supermotif Peptides

| Type | Protein | No. of Amino Acids | Position | Sequence | Seq. Id. No. |
|---|---|---|---|---|---|
| HPV18 | E6 | 10 | 47 | FAFKDLFVVY | 21280 |
| HPV18 | E6 | 8 | 62 | HAACHKCI | 21281 |
| HPV18 | E6 | 10 | 62 | HAACHKCIDF | 21282 |
| HPV18 | E6 | 11 | 62 | HAACHKCIDFY | 21283 |
| HPV18 | E6 | 9 | 30 | ITCVYCKTV | 21284 |
| HPV18 | E6 | 10 | 30 | ITCVYCKTVL | 21285 |
| HPV18 | E6 | 9 | 36 | KTVLELTEV | 21286 |
| HPV18 | E6 | 10 | 36 | KTVLELTEVF | 21287 |
| HPV18 | E6 | 8 | 41 | LTEVFEFA | 21288 |
| HPV18 | E6 | 9 | 41 | LTEVFEFAF | 21289 |
| HPV18 | E6 | 9 | 93 | LTNTGLYNL | 21290 |
| HPV18 | E6 | 10 | 93 | LTNTGLYNLL | 21291 |
| HPV18 | E6 | 11 | 93 | LTNTGLYNLLI | 21292 |
| HPV18 | E6 | 8 | 95 | NTGLYNLL | 21293 |
| HPV18 | E6 | 9 | 95 | NTGLYNLLI | 21294 |
| HPV18 | E6 | 9 | 22 | NTSLQDIEI | 21295 |
| HPV18 | E6 | 8 | 114 | PAEKLRHL | 21296 |
| HPV18 | E6 | 8 | 7 | PTRRPYKL | 21297 |
| HPV18 | E6 | 11 | 7 | PTRRPYKLPDL | 21298 |
| HPV18 | E6 | 8 | 23 | TSLQDIEI | 21299 |
| HPV18 | E6 | 11 | 23 | TSLQDIEITCV | 21300 |
| HPV18 | E6 | 10 | 81 | YSDSVYGDTL | 21301 |
| HPV18 | E6 | 10 | 72 | YSRIRELRHY | 21302 |
| HPV18 | E7 | 8 | 6 | ATLQDIVL | 21303 |
| HPV18 | E7 | 10 | 6 | ATLQDIVLHL | 21304 |
| HPV18 | E7 | 9 | 33 | DSEEENDEI | 21305 |
| HPV18 | E7 | 8 | 69 | EARIKLVV | 21306 |
| HPV18 | E7 | 9 | 77 | ESSADDLRA | 21307 |
| HPV18 | E7 | 10 | 77 | ESSADDLRAF | 21308 |
| HPV18 | E7 | 8 | 5 | KATLQDIV | 21309 |
| HPV18 | E7 | 9 | 5 | KATLQDIVL | 21310 |
| HPV18 | E7 | 11 | 5 | KATLQDIVLHL | 21311 |
| HPV18 | E7 | 11 | 31 | LSDSEEENDEI | 21312 |
| HPV18 | E7 | 9 | 94 | LSFVCPWCA | 21313 |
| HPV18 | E7 | 9 | 92 | NTLSFVCPW | 21314 |
| HPV18 | E7 | 11 | 92 | NTLSFVCPWCA | 21315 |
| HPV18 | E7 | 9 | 53 | RAEPQRHTM | 21316 |
| HPV18 | E7 | 10 | 53 | RAEPQRHTML | 21317 |
| HPV18 | E7 | 8 | 84 | RAFQQLFL | 21318 |
| HPV18 | E7 | 11 | 84 | RAFQQLFLNTL | 21319 |
| HPV18 | E7 | 8 | 79 | SADDLRAF | 21320 |
| HPV18 | E7 | 11 | 79 | SADDLRAFQQL | 21321 |
| HPV18 | E7 | 8 | 78 | SSADDLRA | 21322 |
| HPV18 | E7 | 9 | 78 | SSADDLRAF | 21323 |
| HPV18 | L1 | 10 | 494 | AAPAENKDPY | 21324 |
| HPV18 | L1 | 10 | 195 | AATSNVSEDV | 21325 |
| HPV18 | L1 | 8 | 345 | ASPGSCVY | 21326 |
| HPV18 | L1 | 11 | 407 | ASTQSPVPGQY | 21327 |
| HPV18 | L1 | 11 | 419 | ATKFKQYSRHV | 21328 |
| HPV18 | L1 | 9 | 196 | ATSNVSEDV | 21329 |
| HPV18 | L1 | 8 | 552 | ATTSSKPA | 21330 |
| HPV18 | L1 | 11 | 552 | ATTSSKPAKRV | 21331 |
| HPV18 | L1 | 9 | 222 | CAPAIGEHW | 21332 |
| HPV18 | L1 | 10 | 222 | CAPAIGEHWA | 21333 |
| HPV18 | L1 | 8 | 406 | CASTQSPV | 21334 |
| HPV18 | L1 | 9 | 441 | CTITLTADV | 21335 |
| HPV18 | L1 | 10 | 441 | CTITLTADVM | 21336 |
| HPV18 | L1 | 11 | 493 | DAAPAENKDPY | 21337 |
| HPV18 | L1 | 8 | 418 | DATKFKQY | 21338 |
| HPV18 | L1 | 9 | 364 | DSQLFNKPY | 21339 |
| HPV18 | L1 | 10 | 364 | DSQLFNKPYW | 21340 |
| HPV18 | L1 | 11 | 364 | DSQLFNKPYWL | 21341 |
| HPV18 | L1 | 8 | 189 | DTESSHAA | 21342 |
| HPV18 | L1 | 9 | 263 | DTGYGAMDF | 21343 |
| HPV18 | L1 | 8 | 276 | DTKCEVPL | 21344 |
| HPV18 | L1 | 10 | 276 | DTKCEVPLDI | 21345 |
| HPV18 | L1 | 8 | 396 | DTTPSTNL | 21346 |
| HPV18 | L1 | 10 | 396 | DTTPSTNLTI | 21347 |
| HPV18 | L1 | 8 | 330 | DTVPQSLY | 21348 |
| HPV18 | L1 | 9 | 330 | DTVPQSLYI | 21349 |
| HPV18 | L1 | 9 | 478 | DTYRFVQSV | 21350 |
| HPV18 | L1 | 10 | 478 | DTYRFVQSVA | 21351 |
| HPV18 | L1 | 11 | 478 | DTYRFVQSVAI | 21352 |
| HPV18 | L1 | 10 | 191 | ESSHAATSNV | 21353 |
| HPV18 | L1 | 8 | 155 | ETQRLVWA | 21354 |
| HPV18 | L1 | 10 | 155 | ETQRLVWACA | 21355 |

TABLE XIII-continued

B58 Supermotif Peptides

| Type | Protein | No. of Amino Acids | Position | Sequence | Seq. Id. No. |
|---|---|---|---|---|---|
| HPV18 | L1 | 9 | 317 | FARHFWNRA | 21356 |
| HPV18 | L1 | 8 | 517 | FSLDLDQY | 21357 |
| HPV18 | L1 | 10 | 517 | FSLDLDQYPL | 21358 |
| HPV18 | L1 | 11 | 271 | FSTLQDTKCEV | 21359 |
| HPV18 | L1 | 8 | 267 | GAMDFSTL | 21360 |
| HPV18 | L1 | 10 | 358 | GSIVTSDSQL | 21361 |
| HPV18 | L1 | 11 | 358 | GSIVTSDSQLF | 21362 |
| HPV18 | L1 | 8 | 99 | GSSRLLTV | 21363 |
| HPV18 | L1 | 9 | 233 | GTACKSRPL | 21364 |
| HPV18 | L1 | 11 | 326 | GTMGDTVPQSL | 21365 |
| HPV18 | L1 | 11 | 194 | HAATSNVSEDV | 21366 |
| HPV18 | L1 | 8 | 97 | HAGSSRLL | 21367 |
| HPV18 | L1 | 10 | 97 | HAGSSRLLTV | 21368 |
| HPV18 | L1 | 8 | 30 | HSILVYMV | 21369 |
| HPV18 | L1 | 10 | 30 | HSILVYMVHI | 21370 |
| HPV18 | L1 | 11 | 30 | HSILVYMVHII | 21371 |
| HPV18 | L1 | 8 | 454 | HSMNSSIL | 21372 |
| HPV18 | L1 | 11 | 454 | HSMNSSILEDW | 21373 |
| HPV18 | L1 | 8 | 488 | ITCQKDAA | 21374 |
| HPV18 | L1 | 10 | 488 | ITCQKDAAPA | 21375 |
| HPV18 | L1 | 8 | 443 | ITLTADVM | 21376 |
| HPV18 | L1 | 10 | 443 | ITLTADVMSY | 21377 |
| HPV18 | L1 | 11 | 443 | ITLTADVMSYI | 21378 |
| HPV18 | L1 | 9 | 376 | KAQGHNNGV | 21379 |
| HPV18 | L1 | 11 | 376 | KAQGHNNGVCW | 21380 |
| HPV18 | L1 | 10 | 178 | LSGHPFYNKL | 21381 |
| HPV18 | L1 | 9 | 241 | LSQGDCPPL | 21382 |
| HPV18 | L1 | 11 | 241 | LSQGDCPPLEL | 21383 |
| HPV18 | L1 | 8 | 445 | LTADVMSY | 21384 |
| HPV18 | L1 | 9 | 445 | LTADVMSYI | 21385 |
| HPV18 | L1 | 11 | 403 | LTICASTQSPV | 21386 |
| HPV18 | L1 | 8 | 104 | LTVGNPYF | 21387 |
| HPV18 | L1 | 10 | 104 | LTVGNPYFRV | 21388 |
| HPV18 | L1 | 11 | 62 | MALWRPSDNTV | 21389 |
| HPV18 | L1 | 10 | 298 | MSADPYGDSM | 21390 |
| HPV18 | L1 | 11 | 298 | MSADPYGDSMF | 21391 |
| HPV18 | L1 | 11 | 450 | MSYIHSMNSSI | 21392 |
| HPV18 | L1 | 8 | 457 | NSSILEDW | 21393 |
| HPV18 | L1 | 10 | 457 | NSSILEDWNF | 21394 |
| HPV18 | L1 | 11 | 84 | NTDDYVTPTSI | 21395 |
| HPV18 | L1 | 9 | 253 | NTVLEDGDM | 21396 |
| HPV18 | L1 | 10 | 253 | NTVLEDGDMV | 21397 |
| HPV18 | L1 | 10 | 70 | NTVYLPPPSV | 21398 |
| HPV18 | L1 | 11 | 70 | NTVYLPPPSVA | 21399 |
| HPV18 | L1 | 8 | 496 | PAENKDPY | 21400 |
| HPV18 | L1 | 11 | 496 | PAENKDPYDKL | 21401 |
| HPV18 | L1 | 10 | 114 | PAGGGNKQDI | 21402 |
| HPV18 | L1 | 8 | 224 | PAIGEHWA | 21403 |
| HPV18 | L1 | 9 | 558 | PAKRVRVRA | 21404 |
| HPV18 | L1 | 8 | 344 | PASPGSCV | 21405 |
| HPV18 | L1 | 9 | 344 | PASPGSCVY | 21406 |
| HPV18 | L1 | 10 | 550 | PSATTSSKPA | 21407 |
| HPV18 | L1 | 8 | 67 | PSDNTVYL | 21408 |
| HPV18 | L1 | 8 | 354 | PSPSGSIV | 21409 |
| HPV18 | L1 | 9 | 399 | PSTNLTICA | 21410 |
| HPV18 | L1 | 10 | 540 | PTIGPRKRSA | 21411 |
| HPV18 | L1 | 8 | 91 | PTSIFYHA | 21412 |
| HPV18 | L1 | 9 | 472 | PTTSLVDTY | 21413 |
| HPV18 | L1 | 11 | 472 | PTTSLVDTYRF | 21414 |
| HPV18 | L1 | 10 | 533 | QAGLRRKPTI | 21415 |
| HPV18 | L1 | 9 | 287 | QSICKYPDY | 21416 |
| HPV18 | L1 | 10 | 287 | QSICKYPDYL | 21417 |
| HPV18 | L1 | 10 | 334 | QSLYIKGTGM | 21418 |
| HPV18 | L1 | 8 | 410 | QSPVPGQY | 21419 |
| HPV18 | L1 | 10 | 410 | QSPVPGQYDA | 21420 |
| HPV18 | L1 | 11 | 484 | QSVAITCQKDA | 21421 |
| HPV18 | L1 | 10 | 214 | QTQLCILGCA | 21422 |
| HPV18 | L1 | 9 | 324 | RAGTMGDTV | 21423 |
| HPV18 | L1 | 9 | 299 | SADPYGDSM | 21424 |
| HPV18 | L1 | 10 | 299 | SADPYGDSMF | 21425 |
| HPV18 | L1 | 11 | 299 | SADPYGDSMFF | 21426 |
| HPV18 | L1 | 9 | 551 | SATTSSKPA | 21427 |
| HPV18 | L1 | 8 | 127 | SAYQYRVF | 21428 |
| HPV18 | L1 | 10 | 127 | SAYQYRVFV | 21429 |
| HPV18 | L1 | 9 | 192 | SSHAATSNV | 21430 |
| HPV18 | L1 | 9 | 458 | SSILEDWNF | 21431 |

TABLE XIII-continued

B58 Supermotif Peptides

| Type | Protein | No. of Amino Acids | Position | Sequence | Seq. Id. No. |
|---|---|---|---|---|---|
| HPV18 | L1 | 11 | 458 | SSILEDWNFGV | 21432 |
| HPV18 | L1 | 8 | 555 | SSKPAKRV | 21433 |
| HPV18 | L1 | 10 | 555 | SSKPAKRVRV | 21434 |
| HPV18 | L1 | 11 | 100 | SSRLLTVGNPY | 21435 |
| HPV18 | L1 | 10 | 272 | STLQDTKCEV | 21436 |
| HPV18 | L1 | 8 | 400 | STNLTICA | 21437 |
| HPV18 | L1 | 10 | 408 | STQSPVPGQY | 21438 |
| HPV18 | L1 | 8 | 234 | TACKSRPL | 21439 |
| HPV18 | L1 | 8 | 446 | TADVMSYI | 21440 |
| HPV18 | L1 | 11 | 446 | TADVMSYIHSM | 21441 |
| HPV18 | L1 | 11 | 362 | TSDSQLFNKPY | 21442 |
| HPV18 | L1 | 11 | 149 | TSIYNPETQRL | 21443 |
| HPV18 | L1 | 9 | 474 | TSLVDTYRF | 21444 |
| HPV18 | L1 | 10 | 474 | TSLVDTYRFV | 21445 |
| HPV18 | L1 | 8 | 197 | TSNVSEDV | 21446 |
| HPV18 | L1 | 9 | 554 | TSSKPAKRV | 21447 |
| HPV18 | L1 | 11 | 554 | TSSKPAKRVRV | 21448 |
| HPV18 | L1 | 9 | 397 | TTPSTNLTI | 21449 |
| HPV18 | L1 | 11 | 397 | TTPSTNLTICA | 21450 |
| HPV18 | L1 | 8 | 473 | TTSLVDTY | 21451 |
| HPV18 | L1 | 10 | 473 | TTSLVDTYRF | 21452 |
| HPV18 | L1 | 11 | 473 | TTSLVDTYRFV | 21453 |
| HPV18 | L1 | 10 | 553 | TTSSKPAKRV | 21454 |
| HPV18 | L1 | 9 | 486 | VAITCQKDA | 21455 |
| HPV18 | L1 | 10 | 486 | VAITCQKDAA | 21456 |
| HPV18 | L1 | 10 | 79 | VARVVNTDDY | 21457 |
| HPV18 | L1 | 11 | 79 | VARVVNTDDYV | 21458 |
| HPV18 | L1 | 8 | 126 | VSAYQYRV | 21459 |
| HPV18 | L1 | 9 | 126 | VSAYQYRVF | 21460 |
| HPV18 | L1 | 11 | 126 | VSAYQYRVFRV | 21461 |
| HPV18 | L1 | 9 | 200 | VSEDVRDNV | 21462 |
| HPV18 | L1 | 11 | 200 | VSEDVRDNVSV | 21463 |
| HPV18 | L1 | 10 | 208 | VSVDYKQTQL | 21464 |
| HPV18 | L1 | 8 | 89 | VTPTSIFY | 21465 |
| HPV18 | L1 | 10 | 89 | VTPTSIFYHA | 21466 |
| HPV18 | L1 | 8 | 361 | VTSDSQLF | 21467 |
| HPV18 | L1 | 8 | 161 | WACAGVEI | 21468 |
| HPV18 | L1 | 9 | 352 | YSPSPSGSI | 21469 |
| HPV18 | L1 | 10 | 352 | YSPSPSGSIV | 21470 |
| HPV18 | L1 | 8 | 425 | YSRHVEEY | 21471 |
| HPV18 | L1 | 10 | 425 | YSRHVEEYDL | 21472 |
| HPV18 | L1 | 9 | 4 | YTRVLILHY | 21473 |
| HPV18 | L1 | 11 | 4 | YTRVLILHYHL | 21474 |
| HPV18 | L2 | 9 | 6 | AARRKRASV | 21475 |
| HPV18 | L2 | 10 | 201 | ASSGTGEEPI | 21476 |
| HPV18 | L2 | 9 | 381 | ASSYSNVTV | 21477 |
| HPV18 | L2 | 11 | 381 | ASSYSNVTVPL | 21478 |
| HPV18 | L2 | 8 | 423 | ASTQYIGI | 21479 |
| HPV18 | L2 | 8 | 341 | ATEDNDLF | 21480 |
| HPV18 | L2 | 10 | 341 | ATEDNDLFDI | 21481 |
| HPV18 | L2 | 11 | 341 | ATEDNDLFDIY | 21482 |
| HPV18 | L2 | 11 | 303 | ATMFTRSGTQI | 21483 |
| HPV18 | L2 | 8 | 273 | DSDFMDII | 21484 |
| HPV18 | L2 | 10 | 273 | DSDFMDIIRL | 21485 |
| HPV18 | L2 | 9 | 109 | DSSVVTSGA | 21486 |
| HPV18 | L2 | 8 | 455 | FADGFVAA | 21487 |
| HPV18 | L2 | 10 | 369 | FAFFKYSPTI | 21488 |
| HPV18 | L2 | 11 | 200 | FASSGTGEEPI | 21489 |
| HPV18 | L2 | 9 | 162 | FSDPSIIEV | 21490 |
| HPV18 | L2 | 8 | 296 | FSRLGQRA | 21491 |
| HPV18 | L2 | 10 | 296 | FSRLGQRATM | 21492 |
| HPV18 | L2 | 11 | 296 | FSRLGQRATMF | 21493 |
| HPV18 | L2 | 9 | 122 | FTGTSGFDI | 21494 |
| HPV18 | L2 | 11 | 157 | FTNPAFSDPSI | 21495 |
| HPV18 | L2 | 8 | 306 | FTRSGTQI | 21496 |
| HPV18 | L2 | 10 | 306 | FTRSGTQIGA | 21497 |
| HPV18 | L2 | 10 | 314 | GARVHFYHDI | 21498 |
| HPV18 | L2 | 10 | 62 | GSGTGGRTGY | 21499 |
| HPV18 | L2 | 11 | 62 | GSGTGGRTGYI | 21500 |
| HPV18 | L2 | 8 | 25 | GTCPPDVV | 21501 |
| HPV18 | L2 | 11 | 25 | GTCPPDVVPKV | 21502 |
| HPV18 | L2 | 8 | 64 | GTGGRTGY | 21503 |
| HPV18 | L2 | 9 | 64 | GTGGRTGYI | 21504 |
| HPV18 | L2 | 11 | 64 | GTGGRTGYIPL | 21505 |
| HPV18 | L2 | 8 | 188 | GTHGYEEI | 21506 |
| HPV18 | L2 | 10 | 188 | GTHGYEEIPL | 21507 |

TABLE XIII-continued

B58 Supermotif Peptides

| Type | Protein | No. of Amino Acids | Position | Sequence | Seq. Id. No. |
|---|---|---|---|---|---|
| HPV18 | L2 | 9 | 432 | GTHYYLWPL | 21508 |
| HPV18 | L2 | 10 | 432 | GTHYYLWPLY | 21509 |
| HPV18 | L2 | 11 | 432 | GTHYYLWPLYY | 21510 |
| HPV18 | L2 | 10 | 183 | GTPTSGTHGY | 21511 |
| HPV18 | L2 | 8 | 310 | GTQIGARV | 21512 |
| HPV18 | L2 | 10 | 310 | GTQIGARVHF | 21513 |
| HPV18 | L2 | 11 | 310 | GTQIGARVHFY | 21514 |
| HPV18 | L2 | 10 | 124 | GTSGFDITSA | 21515 |
| HPV18 | L2 | 8 | 37 | GTTLADKI | 21516 |
| HPV18 | L2 | 9 | 37 | GTTLADKIL | 21517 |
| HPV18 | L2 | 11 | 37 | GTTLADKILQW | 21518 |
| HPV18 | L2 | 8 | 134 | GTTTPAVL | 21519 |
| HPV18 | L2 | 10 | 134 | GTTTPAVLDI | 21520 |
| HPV18 | L2 | 8 | 292 | GTVRFSRL | 21521 |
| HPV18 | L2 | 8 | 326 | IAPSPEYI | 21522 |
| HPV18 | L2 | 10 | 326 | IAPSPEYIEL | 21523 |
| HPV18 | L2 | 10 | 323 | ISPIAPSPEY | 21524 |
| HPV18 | L2 | 11 | 323 | ISPIAPSPEYI | 21525 |
| HPV18 | L2 | 10 | 378 | ISSASSYSNV | 21526 |
| HPV18 | L2 | 9 | 210 | ISSTPLPTV | 21527 |
| HPV18 | L2 | 10 | 152 | ISTTNFTNPA | 21528 |
| HPV18 | L2 | 11 | 152 | ISTTNFTNPAF | 21529 |
| HPV18 | L2 | 9 | 405 | ITLPSTTSV | 21530 |
| HPV18 | L2 | 10 | 405 | ITLPSTTSVW | 21531 |
| HPV18 | L2 | 8 | 143 | ITPSSTSV | 21532 |
| HPV18 | L2 | 10 | 143 | ITPSSTSVSI | 21533 |
| HPV18 | L2 | 10 | 130 | ITSAGTTTPA | 21534 |
| HPV18 | L2 | 11 | 130 | ITSAGTTTPAV | 21535 |
| HPV18 | L2 | 8 | 249 | ITYDNPAF | 21536 |
| HPV18 | L2 | 11 | 249 | ITYDNPAFEPV | 21537 |
| HPV18 | L2 | 8 | 40 | LADKILQW | 21538 |
| HPV18 | L2 | 11 | 40 | LADKILQWSSL | 21539 |
| HPV18 | L2 | 9 | 263 | LTFDPRSDV | 21540 |
| HPV18 | L2 | 8 | 242 | LTRPSSLI | 21541 |
| HPV18 | L2 | 10 | 242 | LTRPSSLITY | 21542 |
| HPV18 | L2 | 8 | 287 | LTSRRGTV | 21543 |
| HPV18 | L2 | 10 | 287 | LTSRRGTVRF | 21544 |
| HPV18 | L2 | 9 | 391 | LTSSWDVPV | 21545 |
| HPV18 | L2 | 10 | 391 | LTSSWDVPVY | 21546 |
| HPV18 | L2 | 10 | 254 | PAFEPVDTTL | 21547 |
| HPV18 | L2 | 8 | 160 | PAFSDPSI | 21548 |
| HPV18 | L2 | 9 | 160 | PAFSDPSII | 21549 |
| HPV18 | L2 | 11 | 160 | PAFSDPSIIEV | 21550 |
| HPV18 | L2 | 10 | 285 | PALTSRRGTV | 21551 |
| HPV18 | L2 | 9 | 422 | PASTQYIGI | 21552 |
| HPV18 | L2 | 8 | 328 | PSPEYIEL | 21553 |
| HPV18 | L2 | 11 | 328 | PSPEYIELQPL | 21554 |
| HPV18 | L2 | 8 | 362 | PSRTTSF | 21555 |
| HPV18 | L2 | 9 | 362 | PSRTTSFA | 21556 |
| HPV18 | L2 | 10 | 362 | PSRTTSFAF | 21557 |
| HPV18 | L2 | 11 | 362 | PSRTTSFAFF | 21558 |
| HPV18 | L2 | 11 | 245 | PSSLITYDNPA | 21559 |
| HPV18 | L2 | 8 | 145 | PSSTSVSI | 21560 |
| HPV18 | L2 | 9 | 408 | PSTTSVWPI | 21561 |
| HPV18 | L2 | 10 | 408 | PSTTSVWPIV | 21562 |
| HPV18 | L2 | 9 | 419 | PTAPASTQY | 21563 |
| HPV18 | L2 | 10 | 419 | PTAPASTQYI | 21564 |
| HPV18 | L2 | 9 | 98 | PTDPSIVTL | 21565 |
| HPV18 | L2 | 10 | 98 | PTDPSIVTLI | 21566 |
| HPV18 | L2 | 9 | 120 | PTFTGTSGF | 21567 |
| HPV18 | L2 | 11 | 120 | PTFTGTSGFDI | 21568 |
| HPV18 | L2 | 9 | 376 | PTISSASSY | 21569 |
| HPV18 | L2 | 8 | 86 | PTRPPVVI | 21570 |
| HPV18 | L2 | 11 | 86 | PTRPPVVIEPV | 21571 |
| HPV18 | L2 | 8 | 185 | PTSGTHGY | 21572 |
| HPV18 | L2 | 11 | 185 | PTSGTHGYEEI | 21573 |
| HPV18 | L2 | 11 | 216 | PTVRRVAGPRL | 21574 |
| HPV18 | L2 | 9 | 23 | QSGTCPPDV | 21575 |
| HPV18 | L2 | 10 | 23 | QSGTCPPDVV | 21576 |
| HPV18 | L2 | 9 | 172 | QTGEVAGNV | 21577 |
| HPV18 | L2 | 10 | 172 | QTGEVAGNVF | 21578 |
| HPV18 | L2 | 11 | 172 | QTGEVAGNVFV | 21579 |
| HPV18 | L2 | 8 | 5 | RAARRKRA | 21580 |
| HPV18 | L2 | 10 | 5 | RAARRKRASV | 21581 |
| HPV18 | L2 | 8 | 11 | RASVTDLY | 21582 |
| HPV18 | L2 | 8 | 229 | RAYQQVSV | 21583 |

TABLE XIII-continued

B58 Supermotif Peptides

| Type | Protein | No. of Amino Acids | Position | Sequence | Seq. Id. No. |
|---|---|---|---|---|---|
| HPV18 | L2 | 9 | 229 | RAYQQVSVA | 21584 |
| HPV18 | L2 | 9 | 268 | RSDVPDSDF | 21585 |
| HPV18 | L2 | 10 | 268 | RSDVPDSDFM | 21586 |
| HPV18 | L2 | 8 | 308 | RSGTQIGA | 21587 |
| HPV18 | L2 | 10 | 308 | RSGTQIGARV | 21588 |
| HPV18 | L2 | 8 | 77 | RSNTVVDV | 21589 |
| HPV18 | L2 | 8 | 364 | RSTTSFAF | 21590 |
| HPV18 | L2 | 9 | 364 | RSTTSFAFF | 21591 |
| HPV18 | L2 | 11 | 364 | RSTTSFAFFKY | 21592 |
| HPV18 | L2 | 8 | 132 | SAGTTTPA | 21593 |
| HPV18 | L2 | 9 | 132 | SAGTTTPAV | 21594 |
| HPV18 | L2 | 10 | 132 | SAGTTTPAVL | 21595 |
| HPV18 | L2 | 8 | 380 | SASSYSNV | 21596 |
| HPV18 | L2 | 10 | 380 | SASSYSNVTV | 21597 |
| HPV18 | L2 | 8 | 340 | SATEDNDL | 21598 |
| HPV18 | L2 | 9 | 340 | SATEDNDLF | 21599 |
| HPV18 | L2 | 11 | 340 | SATEDNDLFDI | 21600 |
| HPV18 | L2 | 9 | 379 | SSASSYSNV | 21601 |
| HPV18 | L2 | 11 | 379 | SSASSYSNVTV | 21602 |
| HPV18 | L2 | 9 | 202 | SSGTGEEPI | 21603 |
| HPV18 | L2 | 10 | 48 | SSLGIFLGGL | 21604 |
| HPV18 | L2 | 10 | 246 | SSLITYDNPA | 21605 |
| HPV18 | L2 | 11 | 246 | SSLITYDNPAF | 21606 |
| HPV18 | L2 | 8 | 211 | SSTPLPTV | 21607 |
| HPV18 | L2 | 11 | 211 | SSTPLPTVRRV | 21608 |
| HPV18 | L2 | 8 | 110 | SSVVTSGA | 21609 |
| HPV18 | L2 | 8 | 393 | SSWDVPVY | 21610 |
| HPV18 | L2 | 8 | 382 | SSYSNVTV | 21611 |
| HPV18 | L2 | 10 | 382 | SSYSNVTVPL | 21612 |
| HPV18 | L2 | 10 | 212 | STPLPTVRRV | 21613 |
| HPV18 | L2 | 11 | 212 | STPLPTVRRVA | 21614 |
| HPV18 | L2 | 11 | 147 | STSVSISTTNF | 21615 |
| HPV18 | L2 | 9 | 153 | STTNFTNPA | 21616 |
| HPV18 | L2 | 10 | 153 | STTNFTNPAF | 21617 |
| HPV18 | L2 | 8 | 365 | STTSFAFF | 21618 |
| HPV18 | L2 | 10 | 365 | STTSFAFFKY | 21619 |
| HPV18 | L2 | 8 | 409 | STTSVWPI | 21620 |
| HPV18 | L2 | 9 | 409 | STTSVWPIV | 21621 |
| HPV18 | L2 | 8 | 420 | TAPASTQY | 21622 |
| HPV18 | L2 | 9 | 420 | TAPASTQYI | 21623 |
| HPV18 | L2 | 11 | 420 | TAPASTQYIGI | 21624 |
| HPV18 | L2 | 9 | 131 | TSAGTTTPA | 21625 |
| HPV18 | L2 | 10 | 131 | TSAGTTTPAV | 21626 |
| HPV18 | L2 | 11 | 131 | TSAGTTTPAVL | 21627 |
| HPV18 | L2 | 8 | 367 | TSFAFFKY | 21628 |
| HPV18 | L2 | 9 | 114 | TSGAPRPTF | 21629 |
| HPV18 | L2 | 9 | 125 | TSGFDITSA | 21630 |
| HPV18 | L2 | 10 | 186 | TSGTHGYEEI | 21631 |
| HPV18 | L2 | 9 | 288 | TSRRGTVRF | 21632 |
| HPV18 | L2 | 8 | 392 | TSSWDVPV | 21633 |
| HPV18 | L2 | 9 | 392 | TSSWDVPVY | 21634 |
| HPV18 | L2 | 10 | 148 | TSVSISTTNF | 21635 |
| HPV18 | L2 | 11 | 411 | TSVWPIVSPTA | 21636 |
| HPV18 | L2 | 8 | 38 | TTLADKIL | 21637 |
| HPV18 | L2 | 10 | 38 | TTLADKILQW | 21638 |
| HPV18 | L2 | 11 | 261 | TTLTFDPRSDV | 21639 |
| HPV18 | L2 | 8 | 154 | TTNFTNPA | 21640 |
| HPV18 | L2 | 9 | 154 | TTNFTNPAF | 21641 |
| HPV18 | L2 | 8 | 136 | TPAVLDI | 21642 |
| HPV18 | L2 | 9 | 366 | TTSFAFFKY | 21643 |
| HPV18 | L2 | 8 | 410 | TTSVWPIV | 21644 |
| HPV18 | L2 | 9 | 135 | TTTPAVLDI | 21645 |
| HPV18 | L2 | 10 | 221 | VAGPRLYSRA | 21646 |
| HPV18 | L2 | 11 | 221 | VAGPRLYSRAY | 21647 |
| HPV18 | L2 | 9 | 339 | VSATEDNDL | 21648 |
| HPV18 | L2 | 10 | 339 | VSATEDNDLF | 21649 |
| HPV18 | L2 | 11 | 2 | VSHRAARRKRA | 21650 |
| HPV18 | L2 | 8 | 150 | VSISTTNF | 21651 |
| HPV18 | L2 | 11 | 417 | VSPTAPASTQY | 21652 |
| HPV18 | L2 | 8 | 234 | VSVANPEF | 21653 |
| HPV18 | L2 | 9 | 234 | VSVANPEFL | 21654 |
| HPV18 | L2 | 9 | 104 | VTLIEDSSV | 21655 |
| HPV18 | L2 | 10 | 104 | VTLIEDSSVV | 21656 |
| HPV18 | L2 | 10 | 113 | VTSGAPRPTF | 21657 |
| HPV18 | L2 | 9 | 387 | VTVPLTSSW | 21658 |
| HPV18 | L2 | 11 | 387 | VTVPLTSSWDV | 21659 |

TABLE XIII-continued

B58 Supermotif Peptides

| Type | Protein | No. of Amino Acids | Position | Sequence | Seq. Id. No. |
|---|---|---|---|---|---|
| HPV18 | L2 | 8 | 47 | WSSLGIFL | 21660 |
| HPV18 | L2 | 11 | 47 | WSSLGIFLGGL | 21661 |
| HPV18 | L2 | 8 | 351 | YADDMDPA | 21662 |
| HPV18 | L2 | 9 | 351 | YADDMDPAV | 21663 |
| HPV18 | L2 | 11 | 351 | YADDMDPAVPV | 21664 |
| HPV18 | L2 | 8 | 384 | YSNVTVPL | 21665 |
| HPV18 | L2 | 8 | 374 | YSPTISSA | 21666 |
| HPV18 | L2 | 11 | 374 | YSPTISSASSY | 21667 |
| HPV18 | L2 | 8 | 227 | YSRAYQQV | 21668 |
| HPV18 | L2 | 10 | 227 | YSRAYQQVSV | 21669 |
| HPV18 | L2 | 11 | 227 | YSRAYQQVSVA | 21670 |
| HPV18 | L2 | 8 | 400 | YTGPDITL | 21671 |
| HPV31 | E1 | 11 | 296 | AAALYWYRTGM | 21672 |
| HPV31 | E1 | 9 | 219 | AAFGVTGTV | 21673 |
| HPV31 | E1 | 10 | 219 | AAFGVTGTVA | 21674 |
| HPV31 | E1 | 10 | 297 | AALYWYRTGM | 21675 |
| HPV31 | E1 | 10 | 185 | AAMLGKFKEL | 21676 |
| HPV31 | E1 | 11 | 185 | AAMLGKFKELY | 21677 |
| HPV31 | E1 | 8 | 504 | ATTPCWHY | 21678 |
| HPV31 | E1 | 9 | 504 | ATTPCWHYI | 21679 |
| HPV31 | E1 | 10 | 370 | CAFLKSNSQA | 21680 |
| HPV31 | E1 | 8 | 263 | CAKNRITI | 21681 |
| HPV31 | E1 | 11 | 263 | CAKNRITIEKL | 21682 |
| HPV31 | E1 | 8 | 249 | CSWGMVML | 21683 |
| HPV31 | E1 | 9 | 249 | CSWGMVMLM | 21684 |
| HPV31 | E1 | 10 | 249 | CSWGMVMLML | 21685 |
| HPV31 | E1 | 11 | 249 | CSWGMVMLMLV | 21686 |
| HPV31 | E1 | 8 | 213 | CTDWCVAA | 21687 |
| HPV31 | E1 | 9 | 213 | CTDWCVAAF | 21688 |
| HPV31 | E1 | 11 | 213 | CTDWCVAAFGV | 21689 |
| HPV31 | E1 | 10 | 495 | DAKIGMLDDA | 21690 |
| HPV31 | E1 | 9 | 503 | DATTPCWHY | 21691 |
| HPV31 | E1 | 10 | 503 | DATTPCWHYI | 21692 |
| HPV31 | E1 | 8 | 364 | DSDSNACA | 21693 |
| HPV31 | E1 | 9 | 364 | DSDSNACAF | 21694 |
| HPV31 | E1 | 10 | 364 | DSDSNACAFL | 21695 |
| HPV31 | E1 | 8 | 352 | DSEIAYKY | 21696 |
| HPV31 | E1 | 9 | 352 | DSEIAYKYA | 21697 |
| HPV31 | E1 | 11 | 352 | DSEIAYKYAQL | 21698 |
| HPV31 | E1 | 9 | 613 | DSFSTFKCV | 21699 |
| HPV31 | E1 | 9 | 130 | DSGYGNTEV | 21700 |
| HPV31 | E1 | 8 | 366 | DSNACAFL | 21701 |
| HPV31 | E1 | 9 | 39 | DSSDTGEDM | 21702 |
| HPV31 | E1 | 10 | 39 | DSSDTGEDMV | 21703 |
| HPV31 | E1 | 9 | 42 | DTGEDMVDF | 21704 |
| HPV31 | E1 | 10 | 42 | DTGEDMVDFI | 21705 |
| HPV31 | E1 | 9 | 332 | DTTFDLSQM | 21706 |
| HPV31 | E1 | 10 | 332 | DTTFDLSQMV | 21707 |
| HPV31 | E1 | 8 | 74 | EAEEHAEA | 21708 |
| HPV31 | E1 | 9 | 74 | EAEEHAEAV | 21709 |
| HPV31 | E1 | 11 | 74 | EAEEHAEAVQV | 21710 |
| HPV31 | E1 | 8 | 62 | EAETAQAL | 21711 |
| HPV31 | E1 | 9 | 62 | EAETAQALF | 21712 |
| HPV31 | E1 | 11 | 62 | EAETAQALFHA | 21713 |
| HPV31 | E1 | 10 | 80 | EAVQVLKRKY | 21714 |
| HPV31 | E1 | 11 | 80 | EAVQVLKRKYV | 21715 |
| HPV31 | E1 | 9 | 64 | ETAQALFHA | 21716 |
| HPV31 | E1 | 11 | 315 | ETPEWIERQTV | 21717 |
| HPV31 | E1 | 8 | 168 | ETPTRNIL | 21718 |
| HPV31 | E1 | 10 | 168 | ETPTRNILQV | 21719 |
| HPV31 | E1 | 11 | 168 | ETPTRNILQVL | 21720 |
| HPV31 | E1 | 8 | 139 | ETQQMVQV | 21721 |
| HPV31 | E1 | 8 | 593 | FSRTWCRL | 21722 |
| HPV31 | E1 | 10 | 593 | FSRTWCRLNL | 21723 |
| HPV31 | E1 | 9 | 566 | FTFPNPFPF | 21724 |
| HPV31 | E1 | 9 | 457 | GAPNTGKSY | 21725 |
| HPV31 | E1 | 10 | 457 | GAPNTGKSYF | 21726 |
| HPV31 | E1 | 11 | 91 | GSPLSDISSCV | 21727 |
| HPV31 | E1 | 8 | 11 | GTGCNGWF | 21728 |
| HPV31 | E1 | 9 | 11 | GTGCNGWFY | 21729 |
| HPV31 | E1 | 10 | 11 | GTGCNGWFYV | 21730 |
| HPV31 | E1 | 10 | 386 | GTMCRHYKRA | 21731 |
| HPV31 | E1 | 10 | 225 | GTVAEGFKTL | 21732 |
| HPV31 | E1 | 11 | 225 | GTVAEGFKTLL | 21733 |
| HPV31 | E1 | 8 | 78 | HAEAVQVL | 21734 |
| HPV31 | E1 | 9 | 71 | HAQEAEEHA | 21735 |

TABLE XIII-continued

B58 Supermotif Peptides

| Type | Protein | No. of Amino Acids | Position | Sequence | Seq. Id. No. |
|---|---|---|---|---|---|
| HPV31 | E1 | 11 | 71 | HAQEAEEHAEA | 21736 |
| HPV31 | E1 | 8 | 328 | HSFNDTTF | 21737 |
| HPV31 | E1 | 10 | 328 | HSFNDTTFDL | 21738 |
| HPV31 | E1 | 9 | 560 | HSRLVVFTF | 21739 |
| HPV31 | E1 | 8 | 355 | IAYKYAQL | 21740 |
| HPV31 | E1 | 9 | 355 | IAYKYAQLA | 21741 |
| HPV31 | E1 | 11 | 309 | ISDVYGETPEW | 21742 |
| HPV31 | E1 | 8 | 471 | ISFLQGCI | 21743 |
| HPV31 | E1 | 9 | 471 | ISFLQGCII | 21744 |
| HPV31 | E1 | 11 | 471 | ISFLQGCIISY | 21745 |
| HPV31 | E1 | 8 | 105 | ISPRLKAI | 21746 |
| HPV31 | E1 | 10 | 105 | ISPRLKAICI | 21747 |
| HPV31 | E1 | 9 | 97 | ISSCVDYNI | 21748 |
| HPV31 | E1 | 8 | 280 | ISTNCMLI | 21749 |
| HPV31 | E1 | 10 | 479 | ISYANSKSHF | 21750 |
| HPV31 | E1 | 11 | 479 | ISYANSKSHFW | 21751 |
| HPV31 | E1 | 10 | 268 | ITIEKLLEKL | 21752 |
| HPV31 | E1 | 11 | 268 | ITIEKLLEKLL | 21753 |
| HPV31 | E1 | 8 | 184 | KAAMLGKF | 21754 |
| HPV31 | E1 | 11 | 184 | KAAMLGKFKEL | 21755 |
| HPV31 | E1 | 11 | 532 | KALMQLKCPPL | 21756 |
| HPV31 | E1 | 8 | 590 | KSFFSRTW | 21757 |
| HPV31 | E1 | 11 | 590 | KSFFSRTWCRL | 21758 |
| HPV31 | E1 | 9 | 485 | KSHFWLQPL | 21759 |
| HPV31 | E1 | 10 | 485 | KSHFWLQPLA | 21760 |
| HPV31 | E1 | 8 | 374 | KSNSQAKI | 21761 |
| HPV31 | E1 | 9 | 374 | KSNSQAKIV | 21762 |
| HPV31 | E1 | 9 | 210 | KSTCTDWCV | 21763 |
| HPV31 | E1 | 10 | 210 | KSTCTDWCVA | 21764 |
| HPV31 | E1 | 11 | 210 | KSTCTDWCVAA | 21765 |
| HPV31 | E1 | 8 | 463 | KSYFGMSL | 21766 |
| HPV31 | E1 | 9 | 463 | KSYFGMSLI | 21767 |
| HPV31 | E1 | 11 | 463 | KSYFGMSLISF | 21768 |
| HPV31 | E1 | 8 | 119 | KTAKRRLF | 21769 |
| HPV31 | E1 | 10 | 119 | KTAKRRLFEL | 21770 |
| HPV31 | E1 | 9 | 232 | KTLLQPYCL | 21771 |
| HPV31 | E1 | 10 | 232 | KTLLQPYCLY | 21772 |
| HPV31 | E1 | 8 | 179 | KTSNGKAA | 21773 |
| HPV31 | E1 | 9 | 179 | KTSNGKAAM | 21774 |
| HPV31 | E1 | 10 | 179 | KTSNGKAAML | 21775 |
| HPV31 | E1 | 8 | 247 | LACSWGMV | 21776 |
| HPV31 | E1 | 9 | 247 | LACSWGMVM | 21777 |
| HPV31 | E1 | 10 | 247 | LACSWGMVML | 21778 |
| HPV31 | E1 | 11 | 247 | LACSWGMVMLM | 21779 |
| HPV31 | E1 | 8 | 493 | LADAKIGM | 21780 |
| HPV31 | E1 | 9 | 493 | LADAKIGML | 21781 |
| HPV31 | E1 | 8 | 362 | LADSDSNA | 21782 |
| HPV31 | E1 | 10 | 362 | LADSDSNACA | 21783 |
| HPV31 | E1 | 11 | 362 | LADSDSNACAF | 21784 |
| HPV31 | E1 | 8 | 437 | LSALKLFL | 21785 |
| HPV31 | E1 | 11 | 437 | LSALKLFLKGV | 21786 |
| HPV31 | E1 | 8 | 94 | LSDISSCV | 21787 |
| HPV31 | E1 | 10 | 94 | LSDISSCVDY | 21788 |
| HPV31 | E1 | 9 | 584 | LSDKNWKSF | 21789 |
| HPV31 | E1 | 10 | 584 | LSDKNWKSFF | 21790 |
| HPV31 | E1 | 8 | 337 | LSQMVQWA | 21791 |
| HPV31 | E1 | 9 | 337 | LSQMVQWAY | 21792 |
| HPV31 | E1 | 11 | 468 | MSLISFLQGCI | 21793 |
| HPV31 | E1 | 8 | 306 | MSNISDVY | 21794 |
| HPV31 | E1 | 8 | 549 | NAGKDDRW | 21795 |
| HPV31 | E1 | 10 | 549 | NAGKDDRWPY | 21796 |
| HPV31 | E1 | 11 | 549 | NAGKDDRWPYL | 21797 |
| HPV31 | E1 | 8 | 518 | NALDGNPV | 21798 |
| HPV31 | E1 | 10 | 518 | NALDGNPVSI | 21799 |
| HPV31 | E1 | 8 | 483 | NSKSHFWL | 21800 |
| HPV31 | E1 | 11 | 483 | NSKSHFWLQPL | 21801 |
| HPV31 | E1 | 9 | 117 | NSKTAKRRL | 21802 |
| HPV31 | E1 | 10 | 117 | NSKTAKRRLF | 21803 |
| HPV31 | E1 | 9 | 135 | NTEVETQQM | 21804 |
| HPV31 | E1 | 10 | 135 | NTEVETQQMV | 21805 |
| HPV31 | E1 | 9 | 460 | NTGKSYFGM | 21806 |
| HPV31 | E1 | 11 | 460 | NTGKSYFGMSL | 21807 |
| HPV31 | E1 | 8 | 170 | PTRNILQV | 21808 |
| HPV31 | E1 | 9 | 170 | PTRNILQVL | 21809 |
| HPV31 | E1 | 9 | 60 | QAEAETAQA | 21810 |
| HPV31 | E1 | 10 | 60 | QAEAETAQAL | 21811 |

TABLE XIII-continued

B58 Supermotif Peptides

| Type | Protein | No. of Amino Acids | Position | Sequence | Seq. Id. No. |
|---|---|---|---|---|---|
| HPV31 | E1 | 11 | 60 | QAEAETAQALF | 21812 |
| HPV31 | E1 | 11 | 378 | QAKIVKDCGTM | 21813 |
| HPV31 | E1 | 9 | 67 | QALFHAQEA | 21814 |
| HPV31 | E1 | 9 | 245 | QSLACSWGM | 21815 |
| HPV31 | E1 | 10 | 245 | QSLACSWGMV | 21816 |
| HPV31 | E1 | 11 | 245 | QSLACSWGMVM | 21817 |
| HPV31 | E1 | 10 | 207 | QSNKSTCTDW | 21818 |
| HPV31 | E1 | 8 | 323 | QTVLQHSF | 21819 |
| HPV31 | E1 | 9 | 394 | RAEKRQMSM | 21820 |
| HPV31 | E1 | 8 | 293 | RSTAAALY | 21821 |
| HPV31 | E1 | 9 | 293 | RSTAAALYW | 21822 |
| HPV31 | E1 | 10 | 293 | RSTAAALYWY | 21823 |
| HPV31 | E1 | 10 | 303 | RTGMSNISDV | 21824 |
| HPV31 | E1 | 11 | 303 | RTGMSNISDVY | 21825 |
| HPV31 | E1 | 8 | 595 | RTWCRLNL | 21826 |
| HPV31 | E1 | 10 | 438 | SALKLFLKGV | 21827 |
| HPV31 | E1 | 8 | 98 | SSCVDYNI | 21828 |
| HPV31 | E1 | 8 | 40 | SSDTGEDM | 21829 |
| HPV31 | E1 | 9 | 40 | SSDTGEDMV | 21830 |
| HPV31 | E1 | 11 | 40 | SSDTGEDMVDF | 21831 |
| HPV31 | E1 | 8 | 294 | STAAALYW | 21832 |
| HPV31 | E1 | 9 | 294 | STAAALYWY | 21833 |
| HPV31 | E1 | 8 | 211 | STCTDWCV | 21834 |
| HPV31 | E1 | 9 | 211 | STCTDWCVA | 21835 |
| HPV31 | E1 | 10 | 211 | STCTDWCVAA | 21836 |
| HPV31 | E1 | 11 | 211 | STCTDWCVAAF | 21837 |
| HPV31 | E1 | 11 | 616 | STFKCVSGQNI | 21838 |
| HPV31 | E1 | 8 | 295 | TAAALYWY | 21839 |
| HPV31 | E1 | 9 | 120 | TAKRRLFEL | 21840 |
| HPV31 | E1 | 8 | 65 | TAQALFHA | 21841 |
| HPV31 | E1 | 11 | 65 | TAQALFHAQEA | 21842 |
| HPV31 | E1 | 8 | 180 | TSNGKAAM | 21843 |
| HPV31 | E1 | 9 | 180 | TSNGKAAML | 21844 |
| HPV31 | E1 | 8 | 333 | TTFLDSQM | 21845 |
| HPV31 | E1 | 9 | 333 | TTFLDSQMV | 21846 |
| HPV31 | E1 | 11 | 333 | TTFLDSQMVQW | 21847 |
| HPV31 | E1 | 8 | 505 | TTPCWHYI | 21848 |
| HPV31 | E1 | 11 | 505 | TTPCWHYIDNY | 21849 |
| HPV31 | E1 | 10 | 218 | VAAFGVTGTV | 21850 |
| HPV31 | E1 | 11 | 218 | VAAFGVTGTVA | 21851 |
| HPV31 | E1 | 8 | 227 | VAEGFKTL | 21852 |
| HPV31 | E1 | 9 | 227 | VAEGFKTLL | 21853 |
| HPV31 | E1 | 10 | 413 | VSDEGDWRDI | 21854 |
| HPV31 | E1 | 11 | 413 | VSDEGDWRDIV | 21855 |
| HPV31 | E1 | 9 | 434 | VSFLSALKL | 21856 |
| HPV31 | E1 | 10 | 434 | VSFLSALKLF | 21857 |
| HPV31 | E1 | 11 | 434 | VSFLSALKLFL | 21858 |
| HPV31 | E1 | 10 | 197 | VSFMELIRPF | 21859 |
| HPV31 | E1 | 9 | 621 | VSGQNIRTL | 21860 |
| HPV31 | E1 | 9 | 525 | VSIDVKHKA | 21861 |
| HPV31 | E1 | 10 | 525 | VSIDVKHKAL | 21862 |
| HPV31 | E1 | 11 | 525 | VSIDVKHKALM | 21863 |
| HPV31 | E1 | 9 | 223 | VTGTVAEGF | 21864 |
| HPV31 | E1 | 8 | 343 | WAYDNDVM | 21865 |
| HPV31 | E1 | 8 | 481 | YANSKSHF | 21866 |
| HPV31 | E1 | 9 | 481 | YANSKSHFW | 21867 |
| HPV31 | E1 | 10 | 481 | YANSKSHFWL | 21868 |
| HPV31 | E1 | 11 | 359 | YAQLADSDSNA | 21869 |
| HPV31 | E2 | 10 | 277 | AAACTNQTRA | 21870 |
| HPV31 | E2 | 11 | 277 | AAACTNQTRAV | 21871 |
| HPV31 | E2 | 9 | 278 | AACTNQTRA | 21872 |
| HPV31 | E2 | 10 | 278 | AACTNQTRAV | 21873 |
| HPV31 | E2 | 8 | 291 | ATTPIIHL | 21874 |
| HPV31 | E2 | 9 | 228 | CALGTSEGV | 21875 |
| HPV31 | E2 | 9 | 330 | CTDGKHKNA | 21876 |
| HPV31 | E2 | 10 | 330 | CTDGKHKNAI | 21877 |
| HPV31 | E2 | 11 | 330 | CTDGKHKNAIV | 21878 |
| HPV31 | E2 | 8 | 280 | CTNQTRAV | 21879 |
| HPV31 | E2 | 8 | 145 | CTVVEGQV | 21880 |
| HPV31 | E2 | 8 | 301 | DANILKCL | 21881 |
| HPV31 | E2 | 10 | 301 | DANILKCLRY | 21882 |
| HPV31 | E2 | 9 | 22 | DSKRLCDHI | 21883 |
| HPV31 | E2 | 11 | 22 | DSKRLCDHIDY | 21884 |
| HPV31 | E2 | 10 | 265 | DSVDSVNCGV | 21885 |
| HPV31 | E2 | 11 | 265 | DSVDSVNCGVI | 21886 |
| HPV31 | E2 | 8 | 268 | DSVNCGVI | 21887 |

TABLE XIII-continued

B58 Supermotif Peptides

| Type | Protein | No. of Amino Acids | Position | Sequence | Seq. Id. No. |
|---|---|---|---|---|---|
| HPV31 | E2 | 10 | 268 | DSVNCGVISA | 21888 |
| HPV31 | E2 | 11 | 268 | DSVNCGVISAA | 21889 |
| HPV31 | E2 | 11 | 174 | EAKKYGTGKKW | 21890 |
| HPV31 | E2 | 9 | 197 | ESVFSSDEI | 21891 |
| HPV31 | E2 | 11 | 197 | ESVFSSDEISF | 21892 |
| HPV31 | E2 | 8 | 80 | ETLNNTEY | 21893 |
| HPV31 | E2 | 9 | 2 | ETLSQRLNV | 21894 |
| HPV31 | E2 | 8 | 207 | FAGIVTKL | 21895 |
| HPV31 | E2 | 11 | 207 | FAGIVTKLPTA | 21896 |
| HPV31 | E2 | 8 | 200 | FSSDEISF | 21897 |
| HPV31 | E2 | 9 | 200 | FSSDEISFA | 21898 |
| HPV31 | E2 | 11 | 200 | FSSDEISFAGI | 21899 |
| HPV31 | E2 | 8 | 171 | FTEEAKKY | 21900 |
| HPV31 | E2 | 8 | 179 | GTGKKWEV | 21901 |
| HPV31 | E2 | 10 | 179 | GTGKKWEVHA | 21902 |
| HPV31 | E2 | 9 | 231 | GTSEGVRRA | 21903 |
| HPV31 | E2 | 8 | 187 | HAGGQVIV | 21904 |
| HPV31 | E2 | 9 | 187 | HAGGQVIVF | 21905 |
| HPV31 | E2 | 8 | 52 | HSINHQVV | 21906 |
| HPV31 | E2 | 10 | 52 | HSINHQVVPA | 21907 |
| HPV31 | E2 | 11 | 52 | HSINHQVVPAL | 21908 |
| HPV31 | E2 | 10 | 205 | ISFAGIVTKL | 21909 |
| HPV31 | E2 | 9 | 345 | ISTSQRDDF | 21910 |
| HPV31 | E2 | 10 | 345 | ISTSQRDDFL | 21911 |
| HPV31 | E2 | 11 | 165 | ITYFVNFTEEA | 21912 |
| HPV31 | E2 | 8 | 66 | KAKALQAI | 21913 |
| HPV31 | E2 | 10 | 66 | KAKALQAIEL | 21914 |
| HPV31 | E2 | 8 | 68 | KALQAIEL | 21915 |
| HPV31 | E2 | 10 | 68 | KALQAIELQM | 21916 |
| HPV31 | E2 | 11 | 68 | KALQAIELQMM | 21917 |
| HPV31 | E2 | 10 | 45 | KAREMGIHSI | 21918 |
| HPV31 | E2 | 11 | 226 | KTCALGTSEGV | 21919 |
| HPV31 | E2 | 8 | 312 | LSKYKQLY | 21920 |
| HPV31 | E2 | 11 | 312 | LSKYKQLYEQV | 21921 |
| HPV31 | E2 | 8 | 62 | LSVSKAKA | 21922 |
| HPV31 | E2 | 9 | 62 | LSVSKAKAL | 21923 |
| HPV31 | E2 | 11 | 62 | LSVSKAKALQA | 21924 |
| HPV31 | E2 | 8 | 103 | LTAPTGCL | 21925 |
| HPV31 | E2 | 8 | 337 | NAIVTLTY | 21926 |
| HPV31 | E2 | 9 | 337 | NAIVTLTYI | 21927 |
| HPV31 | E2 | 9 | 84 | NTEYKNEDW | 21928 |
| HPV31 | E2 | 11 | 84 | NTEYKNEDWTM | 21929 |
| HPV31 | E2 | 8 | 254 | NTHHPNKL | 21930 |
| HPV31 | E2 | 9 | 254 | NTHHPNKLL | 21931 |
| HPV31 | E2 | 8 | 127 | NTMHYTNW | 21932 |
| HPV31 | E2 | 10 | 127 | NTMHYTNWKF | 21933 |
| HPV31 | E2 | 11 | 127 | NTMHYTNWKFI | 21934 |
| HPV31 | E2 | 11 | 219 | NTTTSNSKTCA | 21935 |
| HPV31 | E2 | 9 | 355 | NTVKIPNTV | 21936 |
| HPV31 | E2 | 11 | 355 | NTVKIPNTVSV | 21937 |
| HPV31 | E2 | 9 | 361 | NTVSVSTGY | 21938 |
| HPV31 | E2 | 10 | 361 | NTVSVSTGYM | 21939 |
| HPV31 | E2 | 8 | 60 | PALSVSKA | 21940 |
| HPV31 | E2 | 10 | 60 | PALSVSKAKA | 21941 |
| HPV31 | E2 | 11 | 60 | PALSVSKAKAL | 21942 |
| HPV31 | E2 | 9 | 290 | PATTPIIHL | 21943 |
| HPV31 | E2 | 10 | 106 | PTGCLKKHGY | 21944 |
| HPV31 | E2 | 8 | 71 | QAIELQMM | 21945 |
| HPV31 | E2 | 9 | 71 | QAIELQMML | 21946 |
| HPV31 | E2 | 9 | 283 | QTRAVSCPA | 21947 |
| HPV31 | E2 | 8 | 96 | QTSLELYL | 21948 |
| HPV31 | E2 | 10 | 96 | QTSLELYLTA | 21949 |
| HPV31 | E2 | 11 | 285 | RAVSCPATTPI | 21950 |
| HPV31 | E2 | 11 | 276 | SAAACTNQTRA | 21951 |
| HPV31 | E2 | 8 | 201 | SSDEISFA | 21952 |
| HPV31 | E2 | 10 | 201 | SSDEISFAGI | 21953 |
| HPV31 | E2 | 11 | 201 | SSDEISFAGIV | 21954 |
| HPV31 | E2 | 8 | 346 | STSQRDDF | 21955 |
| HPV31 | E2 | 9 | 346 | STSQRDDFL | 21956 |
| HPV31 | E2 | 8 | 232 | TSEGVRRA | 21957 |
| HPV31 | E2 | 9 | 97 | TSLELYLTA | 21958 |
| HPV31 | E2 | 8 | 222 | TSNSKTCA | 21959 |
| HPV31 | E2 | 9 | 222 | TSNSKTCAL | 21960 |
| HPV31 | E2 | 8 | 347 | TSQRDDFL | 21961 |
| HPV31 | E2 | 11 | 347 | TSQRDDFLNTV | 21962 |
| HPV31 | E2 | 11 | 292 | TTPIIHLKGDA | 21963 |

TABLE XIII-continued

B58 Supermotif Peptides

| Type | Protein | No. of Amino Acids | Position | Sequence | Seq. Id. No. |
|---|---|---|---|---|---|
| HPV31 | E2 | 9 | 221 | TTSNSKTCA | 21964 |
| HPV31 | E2 | 10 | 221 | TTSNSKTCAL | 21965 |
| HPV31 | E2 | 10 | 220 | TTTSNSKTCA | 21966 |
| HPV31 | E2 | 11 | 220 | TTTSNSKTCAL | 21967 |
| HPV31 | E2 | 9 | 287 | VSCPATTPI | 21968 |
| HPV31 | E2 | 10 | 287 | VSCPATTPII | 21969 |
| HPV31 | E2 | 9 | 64 | VSKAKALQA | 21970 |
| HPV31 | E2 | 10 | 64 | VSKAKALQAI | 21971 |
| HPV31 | E2 | 8 | 365 | VSTGYMTI | 21972 |
| HPV31 | E2 | 8 | 363 | VSVSTGYM | 21973 |
| HPV31 | E2 | 10 | 363 | VSVSTGYMTI | 21974 |
| HPV31 | E2 | 11 | 328 | WTCTDGKHKNA | 21975 |
| HPV31 | E2 | 8 | 92 | WTMQQTSL | 21976 |
| HPV31 | E2 | 10 | 92 | WTMQQTSLEL | 21977 |
| HPV31 | E2 | 11 | 92 | WTMQQTSLELY | 21978 |
| HPV31 | E2 | 8 | 131 | YTNWKFIY | 21979 |
| HPV31 | E2 | 9 | 131 | YTNWKFIYL | 21980 |
| HPV31 | E2 | 11 | 131 | YTNWKFIYLCI | 21981 |
| HPV31 | E2 | 11 | 115 | YTVEVQFDGDV | 21982 |
| HPV31 | E5 | 8 | 40 | ATLLLLIV | 21983 |
| HPV31 | E5 | 9 | 40 | ATLLLLIVI | 21984 |
| HPV31 | E5 | 10 | 40 | ATLLLLIVIL | 21985 |
| HPV31 | E5 | 11 | 40 | ATLLLLIVILW | 21986 |
| HPV31 | E5 | 8 | 53 | ATSPLRCF | 21987 |
| HPV31 | E5 | 10 | 53 | ATSPLRCFCI | 21988 |
| HPV31 | E5 | 11 | 53 | ATSPLRCFCIY | 21989 |
| HPV31 | E5 | 9 | 52 | IATSPLRCF | 21990 |
| HPV31 | E5 | 11 | 52 | IATSPLRCFCI | 21991 |
| HPV31 | E5 | 8 | 6 | ISTVSIVL | 21992 |
| HPV31 | E5 | 10 | 6 | ISTVSIVLCF | 21993 |
| HPV31 | E5 | 11 | 6 | ISTVSIVLCFL | 21994 |
| HPV31 | E5 | 9 | 34 | LSVSVYATL | 21995 |
| HPV31 | E5 | 10 | 34 | LSVSVYATLL | 21996 |
| HPV31 | E5 | 11 | 34 | LSVSVYATLLL | 21997 |
| HPV31 | E5 | 9 | 7 | STVSIVLCF | 21998 |
| HPV31 | E5 | 10 | 7 | STVSIVLCFL | 21999 |
| HPV31 | E5 | 11 | 7 | STVSIVLCFLL | 22000 |
| HPV31 | E5 | 9 | 54 | TSPLRCFCI | 22001 |
| HPV31 | E5 | 10 | 54 | TSPLRCFCIY | 22002 |
| HPV31 | E5 | 11 | 54 | TSPLRCFCIYV | 22003 |
| HPV31 | E5 | 8 | 9 | VSIVLCFL | 22004 |
| HPV31 | E5 | 9 | 9 | VSIVLCFLL | 22005 |
| HPV31 | E5 | 11 | 9 | VSIVLCFLLCF | 22006 |
| HPV31 | E5 | 8 | 36 | VSVYATLL | 22007 |
| HPV31 | E5 | 9 | 36 | VSVYATLLL | 22008 |
| HPV31 | E5 | 10 | 36 | VSVYATLLLL | 22009 |
| HPV31 | E5 | 11 | 36 | VSVYATLLLLI | 22010 |
| HPV31 | E5 | 8 | 39 | YATLLLLI | 22011 |
| HPV31 | E5 | 9 | 39 | YATLLLLIV | 22012 |
| HPV31 | E5 | 10 | 39 | YATLLLLIVI | 22013 |
| HPV31 | E5 | 11 | 39 | YATLLLLIVIL | 22014 |
| HPV31 | E6 | 8 | 63 | CTKCLRFY | 22015 |
| HPV31 | E6 | 11 | 63 | CTKCLRFYSKV | 22016 |
| HPV31 | E6 | 11 | 57 | DTPHGVCTKCL | 22017 |
| HPV31 | E6 | 8 | 39 | ETEVLDFA | 22018 |
| HPV31 | E6 | 9 | 39 | ETEVLDFAF | 22019 |
| HPV31 | E6 | 8 | 45 | FAFTDLTI | 22020 |
| HPV31 | E6 | 9 | 45 | FAFTDLTIV | 22021 |
| HPV31 | E6 | 10 | 45 | FAFTDLTIVY | 22022 |
| HPV31 | E6 | 8 | 47 | FTDLTIVY | 22023 |
| HPV31 | E6 | 9 | 15 | LSSALEIPY | 22024 |
| HPV31 | E6 | 9 | 37 | LTETEVLDF | 22025 |
| HPV31 | E6 | 10 | 37 | LTETEVLDFA | 22026 |
| HPV31 | E6 | 11 | 37 | LTETEVLDFAF | 22027 |
| HPV31 | E6 | 9 | 91 | LTNKGICDL | 22028 |
| HPV31 | E6 | 10 | 91 | LTNKGICDLL | 22029 |
| HPV31 | E6 | 11 | 91 | LTNKGICDLLI | 22030 |
| HPV31 | E6 | 8 | 5 | PAERPRKL | 22031 |
| HPV31 | E6 | 11 | 5 | PAERPRKLHEL | 22032 |
| HPV31 | E6 | 10 | 17 | SALEIPYDEL | 22033 |
| HPV31 | E6 | 8 | 16 | SSALEIPY | 22034 |
| HPV31 | E6 | 11 | 16 | SSALEIPYDEL | 22035 |
| HPV31 | E6 | 11 | 86 | TTLEKLTNKGI | 22036 |
| HPV31 | E6 | 9 | 73 | VSEFRWYRY | 22037 |
| HPV31 | E6 | 11 | 73 | VSEFRWYRYSV | 22038 |
| HPV31 | E6 | 9 | 132 | WTGRCIACW | 22039 |

TABLE XIII-continued

B58 Supermotif Peptides

| Type | Protein | No. of Amino Acids | Position | Sequence | Seq. Id. No. |
|---|---|---|---|---|---|
| HPV31 | E6 | 9 | 70 | YSKVSEFRW | 22040 |
| HPV31 | E6 | 10 | 70 | YSKVSEFRWY | 22041 |
| HPV31 | E6 | 8 | 81 | YSVYGTTL | 22042 |
| HPV31 | E6 | 11 | 81 | YSVYGTTLEKL | 22043 |
| HPV31 | E7 | 10 | 19 | ATDLHCYEQL | 22044 |
| HPV31 | E7 | 8 | 30 | DSSDEEDV | 22045 |
| HPV31 | E7 | 9 | 30 | DSSDEEDVI | 22046 |
| HPV31 | E7 | 8 | 48 | DTSNYNIV | 22047 |
| HPV31 | E7 | 10 | 48 | DTSNYNIVTF | 22048 |
| HPV31 | E7 | 8 | 18 | EATDLHCY | 22049 |
| HPV31 | E7 | 11 | 18 | EATDLHCYEQL | 22050 |
| HPV31 | E7 | 8 | 4 | ETPTLQDY | 22051 |
| HPV31 | E7 | 9 | 4 | ETPTLQDYV | 22052 |
| HPV31 | E7 | 10 | 4 | ETPTLQDYVL | 22053 |
| HPV31 | E7 | 8 | 62 | KSTLRLCV | 22054 |
| HPV31 | E7 | 8 | 6 | PTLQDYVL | 22055 |
| HPV31 | E7 | 10 | 6 | PTLQDYVLDL | 22056 |
| HPV31 | E7 | 9 | 44 | QAEPDTSNY | 22057 |
| HPV31 | E7 | 11 | 44 | QAEPDTSNYNI | 22058 |
| HPV31 | E7 | 9 | 70 | QSTQVDIRI | 22059 |
| HPV31 | E7 | 10 | 70 | QSTQVDIRIL | 22060 |
| HPV31 | E7 | 8 | 31 | SSDEEDVI | 22061 |
| HPV31 | E7 | 8 | 71 | STQVDIRI | 22062 |
| HPV31 | E7 | 9 | 71 | STQVDIRIL | 22063 |
| HPV31 | E7 | 9 | 49 | TSNYNIVTF | 22064 |
| HPV31 | E7 | 11 | 55 | VTFCCQCKSTL | 22065 |
| HPV31 | L1 | 10 | 347 | AAIANSDTTF | 22066 |
| HPV31 | L1 | 8 | 285 | ATLANSTY | 22067 |
| HPV31 | L1 | 9 | 285 | ATLANSTYF | 22068 |
| HPV31 | L1 | 8 | 9 | ATVYLPPV | 22069 |
| HPV31 | L1 | 10 | 9 | ATVYLPPVPV | 22070 |
| HPV31 | L1 | 11 | 346 | CAAIANSDTTF | 22071 |
| HPV31 | L1 | 9 | 304 | DAQIFNKPY | 22072 |
| HPV31 | L1 | 10 | 304 | DAQIFNKPYW | 22073 |
| HPV31 | L1 | 11 | 304 | DAQIFNKPYWM | 22074 |
| HPV31 | L1 | 8 | 129 | DTENSNRY | 22075 |
| HPV31 | L1 | 9 | 129 | DTENSNRYA | 22076 |
| HPV31 | L1 | 9 | 203 | DTGFGAMDF | 22077 |
| HPV31 | L1 | 11 | 203 | DTGFGAMDFTA | 22078 |
| HPV31 | L1 | 8 | 216 | DTKSNVPL | 22079 |
| HPV31 | L1 | 10 | 216 | DTKSNVPLDI | 22080 |
| HPV31 | L1 | 9 | 353 | DTTFKSSNF | 22081 |
| HPV31 | L1 | 8 | 336 | DTTRSTNM | 22082 |
| HPV31 | L1 | 10 | 336 | DTTRSTNMSV | 22083 |
| HPV31 | L1 | 10 | 417 | DTYRFVTSQA | 22084 |
| HPV31 | L1 | 11 | 417 | DTYRFVTSQAI | 22085 |
| HPV31 | L1 | 9 | 8 | EATVYLPPV | 22086 |
| HPV31 | L1 | 11 | 8 | EATVYLPPVPV | 22087 |
| HPV31 | L1 | 8 | 270 | ESVPTDLY | 22088 |
| HPV31 | L1 | 9 | 270 | ESVPTDLYI | 22089 |
| HPV31 | L1 | 8 | 95 | ETQRLVWA | 22090 |
| HPV31 | L1 | 10 | 95 | ETQRLVWACV | 22091 |
| HPV31 | L1 | 8 | 456 | FSADLDQF | 22092 |
| HPV31 | L1 | 10 | 456 | FSADLDQFPL | 22093 |
| HPV31 | L1 | 11 | 211 | FTALQDTKSNV | 22094 |
| HPV31 | L1 | 8 | 207 | GAMDFTAL | 22095 |
| HPV31 | L1 | 8 | 38 | GSARLLTV | 22096 |
| HPV31 | L1 | 8 | 280 | GSGSTATL | 22097 |
| HPV31 | L1 | 9 | 280 | GSGSTATLA | 22098 |
| HPV31 | L1 | 9 | 413 | GSLEDTYRF | 22099 |
| HPV31 | L1 | 10 | 413 | GSLEDTYRFV | 22100 |
| HPV31 | L1 | 8 | 298 | GSMVTSDA | 22101 |
| HPV31 | L1 | 10 | 298 | GSMVTSDAQI | 22102 |
| HPV31 | L1 | 11 | 298 | GSMVTSDAQIF | 22103 |
| HPV31 | L1 | 8 | 173 | GSPCSNNA | 22104 |
| HPV31 | L1 | 9 | 173 | GSPCSNNAI | 22105 |
| HPV31 | L1 | 11 | 282 | GSTATLANSTY | 22106 |
| HPV31 | L1 | 8 | 141 | GTDNRECI | 22107 |
| HPV31 | L1 | 10 | 141 | GTDNRECISM | 22108 |
| HPV31 | L1 | 11 | 266 | GTVGESVPTDL | 22109 |
| HPV31 | L1 | 8 | 36 | HAGSARLL | 22110 |
| HPV31 | L1 | 10 | 36 | HAGSARLLTV | 22111 |
| HPV31 | L1 | 8 | 393 | HSMNPAIL | 22112 |
| HPV31 | L1 | 11 | 393 | HSMNPAILEDW | 22113 |
| HPV31 | L1 | 8 | 349 | IANSDTTF | 22114 |
| HPV31 | L1 | 10 | 118 | ISGHPLLNKF | 22115 |

TABLE XIII-continued

B58 Supermotif Peptides

| Type | Protein | No. of Amino Acids | Position | Sequence | Seq. Id. No. |
|---|---|---|---|---|---|
| HPV31 | L1 | 10 | 148 | ISMDYKQTQL | 22116 |
| HPV31 | L1 | 8 | 382 | ITLSADIM | 22117 |
| HPV31 | L1 | 10 | 382 | ITLSADIMTY | 22118 |
| HPV31 | L1 | 11 | 382 | ITLSADIMTYI | 22119 |
| HPV31 | L1 | 9 | 181 | ITPGDCPPL | 22120 |
| HPV31 | L1 | 11 | 181 | ITPGDCPPLEL | 22121 |
| HPV31 | L1 | 10 | 482 | KAGKRSAPSA | 22122 |
| HPV31 | L1 | 8 | 54 | KSDNPKKI | 22123 |
| HPV31 | L1 | 9 | 54 | KSDNPKKIV | 22124 |
| HPV31 | L1 | 10 | 54 | KSDNPKKIVV | 22125 |
| HPV31 | L1 | 8 | 218 | KSNVPLDI | 22126 |
| HPV31 | L1 | 8 | 357 | KSSNFKEY | 22127 |
| HPV31 | L1 | 9 | 357 | KSSNFKEYL | 22128 |
| HPV31 | L1 | 8 | 384 | LSADIMTY | 22129 |
| HPV31 | L1 | 9 | 384 | LSADIMTYI | 22130 |
| HPV31 | L1 | 9 | 407 | LTTPPSGSL | 22131 |
| HPV31 | L1 | 8 | 43 | LTVGHPYY | 22132 |
| HPV31 | L1 | 10 | 43 | LTVGHPYYSI | 22133 |
| HPV31 | L1 | 9 | 1 | MSLWRPSEA | 22134 |
| HPV31 | L1 | 11 | 1 | MSLWRPSEATV | 22135 |
| HPV31 | L1 | 8 | 343 | MSVCAAIA | 22136 |
| HPV31 | L1 | 10 | 389 | MTYIHSMNPA | 22137 |
| HPV31 | L1 | 11 | 389 | MTYIHSMNPAI | 22138 |
| HPV31 | L1 | 11 | 179 | NAITPGDCPPL | 22139 |
| HPV31 | L1 | 11 | 351 | NSDTTFKSSNF | 22140 |
| HPV31 | L1 | 9 | 227 | NSICKYPDY | 22141 |
| HPV31 | L1 | 10 | 227 | NSICKYPDYL | 22142 |
| HPV31 | L1 | 9 | 193 | NSVIQDGDM | 22143 |
| HPV31 | L1 | 10 | 193 | NSVIQDGDMV | 22144 |
| HPV31 | L1 | 9 | 397 | PAILEDWNF | 22145 |
| HPV31 | L1 | 11 | 397 | PAILEDWNFGL | 22146 |
| HPV31 | L1 | 9 | 489 | PSASTTTPA | 22147 |
| HPV31 | L1 | 8 | 6 | PSEATVYL | 22148 |
| HPV31 | L1 | 11 | 6 | PSEATVYLPPV | 22149 |
| HPV31 | L1 | 9 | 411 | PSGSLEDTY | 22150 |
| HPV31 | L1 | 11 | 411 | PSGSLEDTYRF | 22151 |
| HPV31 | L1 | 10 | 296 | PSGSMVTSDA | 22152 |
| HPV31 | L1 | 8 | 294 | PTPSGSMV | 22153 |
| HPV31 | L1 | 10 | 472 | QAGYRARPKF | 22154 |
| HPV31 | L1 | 9 | 425 | QAITCQKTA | 22155 |
| HPV31 | L1 | 9 | 316 | RAQGHNNGI | 22156 |
| HPV31 | L1 | 11 | 316 | RAQGHNNGICW | 22157 |
| HPV31 | L1 | 8 | 476 | RARPKFKA | 22158 |
| HPV31 | L1 | 9 | 264 | RSGTVGESV | 22159 |
| HPV31 | L1 | 9 | 339 | RSTNMSVCA | 22160 |
| HPV31 | L1 | 10 | 339 | RSTNMSVCAA | 22161 |
| HPV31 | L1 | 11 | 339 | RSTNMSVCAAI | 22162 |
| HPV31 | L1 | 8 | 30 | RTNIYYHA | 22163 |
| HPV31 | L1 | 11 | 30 | RTNIYYHAGSA | 22164 |
| HPV31 | L1 | 8 | 385 | SADIMTYI | 22165 |
| HPV31 | L1 | 11 | 385 | SADIMTYIHSM | 22166 |
| HPV31 | L1 | 9 | 457 | SADLDQFPL | 22167 |
| HPV31 | L1 | 11 | 487 | SAPSASTTTPA | 22168 |
| HPV31 | L1 | 11 | 39 | SARLLTVGHPY | 22169 |
| HPV31 | L1 | 8 | 490 | SASTTTPA | 22170 |
| HPV31 | L1 | 8 | 358 | SSNFKEYL | 22171 |
| HPV31 | L1 | 10 | 283 | STATLANSTY | 22172 |
| HPV31 | L1 | 11 | 283 | STATLANSTYF | 22173 |
| HPV31 | L1 | 11 | 23 | STDEYVTRTNI | 22174 |
| HPV31 | L1 | 8 | 340 | STNMSVCA | 22175 |
| HPV31 | L1 | 9 | 340 | STNMSVCAA | 22176 |
| HPV31 | L1 | 10 | 340 | STNMSVCAAI | 22177 |
| HPV31 | L1 | 11 | 340 | STNMSVCAAIA | 22178 |
| HPV31 | L1 | 11 | 290 | STYFPTPSGSM | 22179 |
| HPV31 | L1 | 10 | 212 | TALQDTKSNV | 22180 |
| HPV31 | L1 | 11 | 432 | TAPQKPKEDPF | 22181 |
| HPV31 | L1 | 9 | 284 | TATLANSTY | 22182 |
| HPV31 | L1 | 10 | 284 | TATLANSTYF | 22183 |
| HPV31 | L1 | 11 | 302 | TSDAQIFNKPY | 22184 |
| HPV31 | L1 | 11 | 89 | TSFYNPETQRL | 22185 |
| HPV31 | L1 | 11 | 423 | TSQAITCQKTA | 22186 |
| HPV31 | L1 | 8 | 354 | TTFKSSNF | 22187 |
| HPV31 | L1 | 11 | 354 | TTFKSSNFKEY | 22188 |
| HPV31 | L1 | 8 | 408 | TTPPSGSL | 22189 |
| HPV31 | L1 | 9 | 337 | TTRSTNMSV | 22190 |
| HPV31 | L1 | 11 | 337 | TTRSTNMSVCA | 22191 |

TABLE XIII-continued

B58 Supermotif Peptides

| Type | Protein | No. of Amino Acids | Position | Sequence | Seq. Id. No. |
|---|---|---|---|---|---|
| HPV31 | L1 | 9 | 239 | VAEPYGDTL | 22192 |
| HPV31 | L1 | 10 | 239 | VAEPYGDTLF | 22193 |
| HPV31 | L1 | 11 | 239 | VAEPYGDTLFF | 22194 |
| HPV31 | L1 | 8 | 66 | VSGLQYRV | 22195 |
| HPV31 | L1 | 9 | 66 | VSGLQYRVF | 22196 |
| HPV31 | L1 | 11 | 66 | VSGLQYRVFRV | 22197 |
| HPV31 | L1 | 10 | 18 | VSKVVSTDEY | 22198 |
| HPV31 | L1 | 11 | 18 | VSKVVSTDEYV | 22199 |
| HPV31 | L1 | 8 | 28 | VTRTNIYY | 22200 |
| HPV31 | L1 | 10 | 28 | VTRTNIYYHA | 22201 |
| HPV31 | L1 | 8 | 301 | VTSDAQIF | 22202 |
| HPV31 | L1 | 8 | 101 | WACVGLEV | 22203 |
| HPV31 | L2 | 9 | 24 | AAGTCPSDV | 22204 |
| HPV31 | L2 | 10 | 24 | AAGTCPSDVI | 22205 |
| HPV31 | L2 | 9 | 340 | ASATTTSTL | 22206 |
| HPV31 | L2 | 9 | 85 | ASIPIRPPV | 22207 |
| HPV31 | L2 | 11 | 85 | ASIPIRPPVSI | 22208 |
| HPV31 | L2 | 10 | 367 | ATHNVSPSTA | 22209 |
| HPV31 | L2 | 11 | 367 | ATHNVSPSTAV | 22210 |
| HPV31 | L2 | 9 | 311 | ATIGARVHY | 22211 |
| HPV31 | L2 | 10 | 311 | ATIGARVHYY | 22212 |
| HPV31 | L2 | 11 | 311 | ATIGARVHYYY | 22213 |
| HPV31 | L2 | 10 | 15 | ATQLYQTCKA | 22214 |
| HPV31 | L2 | 11 | 15 | ATQLYQTCKAA | 22215 |
| HPV31 | L2 | 8 | 226 | ATQQVKVI | 22216 |
| HPV31 | L2 | 9 | 135 | ATTADTTPA | 22217 |
| HPV31 | L2 | 10 | 135 | ATTADTTPAI | 22218 |
| HPV31 | L2 | 11 | 135 | ATTADTTPAIL | 22219 |
| HPV31 | L2 | 11 | 342 | ATTTSTLNDGL | 22220 |
| HPV31 | L2 | 10 | 358 | DTDFTVDTPA | 22221 |
| HPV31 | L2 | 8 | 364 | DTPATHNV | 22222 |
| HPV31 | L2 | 9 | 139 | DTTPAILDV | 22223 |
| HPV31 | L2 | 10 | 84 | EASIPIRPPV | 22224 |
| HPV31 | L2 | 9 | 111 | ESGIVDVGA | 22225 |
| HPV31 | L2 | 11 | 111 | ESGIVDVGAPA | 22226 |
| HPV31 | L2 | 8 | 331 | ESIEMQPL | 22227 |
| HPV31 | L2 | 10 | 331 | ESIEMQPLGA | 22228 |
| HPV31 | L2 | 8 | 171 | ETSGHLLL | 22229 |
| HPV31 | L2 | 9 | 253 | ETVNAEESL | 22230 |
| HPV31 | L2 | 10 | 253 | ETVNAEESLY | 22231 |
| HPV31 | L2 | 11 | 253 | ETVNAEESLYF | 22232 |
| HPV31 | L2 | 8 | 404 | FSGPDVPI | 22233 |
| HPV31 | L2 | 11 | 404 | FSGPDVPIEHA | 22234 |
| HPV31 | L2 | 8 | 263 | FSNTSHNI | 22235 |
| HPV31 | L2 | 9 | 263 | FSNTSHNIA | 22236 |
| HPV31 | L2 | 8 | 459 | FTDVSVAA | 22237 |
| HPV31 | L2 | 11 | 361 | FTVDTPATHNV | 22238 |
| HPV31 | L2 | 8 | 314 | GARVHYYY | 22239 |
| HPV31 | L2 | 10 | 314 | GARVHYYYDI | 22240 |
| HPV31 | L2 | 10 | 339 | GASATTTSTL | 22241 |
| HPV31 | L2 | 8 | 310 | GATIGARV | 22242 |
| HPV31 | L2 | 10 | 310 | GATIGARVHY | 22243 |
| HPV31 | L2 | 11 | 310 | GATIGARVHYY | 22244 |
| HPV31 | L2 | 10 | 63 | GSGTGGRTGY | 22245 |
| HPV31 | L2 | 11 | 63 | GSGTGGRTGYV | 22246 |
| HPV31 | L2 | 10 | 49 | GSMGVFFGGL | 22247 |
| HPV31 | L2 | 8 | 26 | GTCPSDVI | 22248 |
| HPV31 | L2 | 11 | 26 | GTCPSDVIPKI | 22249 |
| HPV31 | L2 | 8 | 65 | GTGGRTGY | 22250 |
| HPV31 | L2 | 9 | 65 | GTGGRTGYV | 22251 |
| HPV31 | L2 | 11 | 65 | GTGGRTGYVPL | 22252 |
| HPV31 | L2 | 9 | 413 | HAPTQVFPF | 22253 |
| HPV31 | L2 | 11 | 413 | HAPTQVFPFPL | 22254 |
| HPV31 | L2 | 8 | 38 | HTTIADQI | 22255 |
| HPV31 | L2 | 9 | 38 | HTTIADQIL | 22256 |
| HPV31 | L2 | 11 | 38 | HTTIADQILRY | 22257 |
| HPV31 | L2 | 8 | 41 | IADQILRY | 22258 |
| HPV31 | L2 | 11 | 41 | IADQILRYGSM | 22259 |
| HPV31 | L2 | 8 | 280 | IALHRPAL | 22260 |
| HPV31 | L2 | 8 | 270 | IAPDPDFL | 22261 |
| HPV31 | L2 | 10 | 270 | IAPDPDFLDI | 22262 |
| HPV31 | L2 | 11 | 270 | IAPDPDFLDII | 22263 |
| HPV31 | L2 | 10 | 134 | IATTADTTPA | 22264 |
| HPV31 | L2 | 11 | 134 | IATTADTTPAI | 22265 |
| HPV31 | L2 | 11 | 323 | ISSINPAGESI | 22266 |
| HPV31 | L2 | 9 | 183 | ISTHNYEEI | 22267 |

TABLE XIII-continued

B58 Supermotif Peptides

| Type | Protein | No. of Amino Acids | Position | Sequence | Seq. Id. No. |
|---|---|---|---|---|---|
| HPV31 | L2 | 11 | 183 | ISTHNYEEIPM | 22268 |
| HPV31 | L2 | 10 | 205 | ITSSTPIPGV | 22269 |
| HPV31 | L2 | 8 | 245 | ITYENPAY | 22270 |
| HPV31 | L2 | 11 | 245 | ITYENPAYETV | 22271 |
| HPV31 | L2 | 10 | 23 | KAAGTCPSDV | 22272 |
| HPV31 | L2 | 11 | 23 | KAAGTCPSDVI | 22273 |
| HPV31 | L2 | 8 | 225 | KATQQVKV | 22274 |
| HPV31 | L2 | 9 | 225 | KATQQVKVI | 22275 |
| HPV31 | L2 | 8 | 423 | LAPTTPQV | 22276 |
| HPV31 | L2 | 10 | 423 | LAPTTPQVSI | 22277 |
| HPV31 | L2 | 11 | 423 | LAPTTPQVSIF | 22278 |
| HPV31 | L2 | 8 | 238 | LSAPKQLI | 22279 |
| HPV31 | L2 | 10 | 238 | LSAPKQLITY | 22280 |
| HPV31 | L2 | 11 | 178 | LSSSSISTHNY | 22281 |
| HPV31 | L2 | 9 | 395 | LSTGFDIPI | 22282 |
| HPV31 | L2 | 10 | 395 | LSTGFDIPIF | 22283 |
| HPV31 | L2 | 8 | 75 | LSTRPSTV | 22284 |
| HPV31 | L2 | 11 | 75 | LSTRPSTVSEA | 22285 |
| HPV31 | L2 | 8 | 287 | LTSRRNTV | 22286 |
| HPV31 | L2 | 10 | 287 | LTSRRNTVRY | 22287 |
| HPV31 | L2 | 8 | 256 | NAEESLYF | 22288 |
| HPV31 | L2 | 10 | 390 | NTTVPLSTGF | 22289 |
| HPV31 | L2 | 8 | 292 | NTVRYSRL | 22290 |
| HPV31 | L2 | 8 | 169 | PAETSGHL | 22291 |
| HPV31 | L2 | 9 | 169 | PAETSGHLL | 22292 |
| HPV31 | L2 | 10 | 169 | PAETSGHLLL | 22293 |
| HPV31 | L2 | 8 | 328 | PAGESIEM | 22294 |
| HPV31 | L2 | 11 | 328 | PAGESIEMQPL | 22295 |
| HPV31 | L2 | 9 | 142 | PAILDVTSV | 22296 |
| HPV31 | L2 | 10 | 285 | PALTSRRNTV | 22297 |
| HPV31 | L2 | 10 | 217 | PARLGLYSKA | 22298 |
| HPV31 | L2 | 11 | 366 | PATHNVSPSTA | 22299 |
| HPV31 | L2 | 8 | 250 | PAYETVNA | 22300 |
| HPV31 | L2 | 8 | 29 | PSDVIPKI | 22301 |
| HPV31 | L2 | 10 | 373 | PSTAVQSTSA | 22302 |
| HPV31 | L2 | 11 | 373 | PSTAVQSTSAV | 22303 |
| HPV31 | L2 | 9 | 79 | PSTVSEASI | 22304 |
| HPV31 | L2 | 11 | 79 | PSTVSEASIPI | 22305 |
| HPV31 | L2 | 10 | 161 | PSVLQPPTPA | 22306 |
| HPV31 | L2 | 10 | 235 | PTFLSAPKQL | 22307 |
| HPV31 | L2 | 11 | 235 | PTFLSAPKQLI | 22308 |
| HPV31 | L2 | 8 | 156 | PTFTDPSV | 22309 |
| HPV31 | L2 | 9 | 156 | PTFTDPSVL | 22310 |
| HPV31 | L2 | 8 | 388 | PTNTTVPL | 22311 |
| HPV31 | L2 | 10 | 167 | PTPAETSGHL | 22312 |
| HPV31 | L2 | 11 | 167 | PTPAETSGHLL | 22313 |
| HPV31 | L2 | 9 | 415 | PTQVFPFPL | 22314 |
| HPV31 | L2 | 10 | 415 | PTQVFPFPLA | 22315 |
| HPV31 | L2 | 8 | 425 | PTTPQVSI | 22316 |
| HPV31 | L2 | 9 | 425 | PTTPQVSIF | 22317 |
| HPV31 | L2 | 10 | 425 | PTTPQVSIFV | 22318 |
| HPV31 | L2 | 8 | 127 | PTTSGFDI | 22319 |
| HPV31 | L2 | 9 | 127 | PTTSGFDIA | 22320 |
| HPV31 | L2 | 8 | 378 | QSTSAVSA | 22321 |
| HPV31 | L2 | 9 | 378 | QSTSAVSAY | 22322 |
| HPV31 | L2 | 10 | 378 | QSTSAVSAYV | 22323 |
| HPV31 | L2 | 9 | 303 | QTLRTRSGA | 22324 |
| HPV31 | L2 | 11 | 303 | QTLRTRSGATI | 22325 |
| HPV31 | L2 | 8 | 12 | RASATQLY | 22326 |
| HPV31 | L2 | 8 | 308 | RSGATIGA | 22327 |
| HPV31 | L2 | 10 | 308 | RSGATIGARV | 22328 |
| HPV31 | L2 | 9 | 5 | RSTKRTKRA | 22329 |
| HPV31 | L2 | 11 | 5 | RSTKRTKRASA | 22330 |
| HPV31 | L2 | 10 | 9 | RTKRASATQL | 22331 |
| HPV31 | L2 | 11 | 9 | RTKRASATQLY | 22332 |
| HPV31 | L2 | 8 | 306 | RTRSGATI | 22333 |
| HPV31 | L2 | 10 | 306 | RTRSGATIGA | 22334 |
| HPV31 | L2 | 9 | 239 | SAPKQLITY | 22335 |
| HPV31 | L2 | 11 | 14 | SATQLYQTCKA | 22336 |
| HPV31 | L2 | 8 | 341 | SATTTSTL | 22337 |
| HPV31 | L2 | 10 | 384 | SAYVPTNTTV | 22338 |
| HPV31 | L2 | 10 | 324 | SSINPAGESI | 22339 |
| HPV31 | L2 | 8 | 181 | SSISTHNY | 22340 |
| HPV31 | L2 | 11 | 181 | SSISTHNYEEI | 22341 |
| HPV31 | L2 | 9 | 180 | SSSISTHNY | 22342 |
| HPV31 | L2 | 10 | 179 | SSSSISTHNY | 22343 |

TABLE XIII-continued

B58 Supermotif Peptides

| Type | Protein | No. of Amino Acids | Position | Sequence | Seq. Id. No. |
|---|---|---|---|---|---|
| HPV31 | L2 | 8 | 207 | SSTPIPGV | 22344 |
| HPV31 | L2 | 9 | 374 | STAVQSTSA | 22345 |
| HPV31 | L2 | 10 | 374 | STAVQSTSAV | 22346 |
| HPV31 | L2 | 8 | 396 | STGFDIPI | 22347 |
| HPV31 | L2 | 9 | 396 | STGFDIPIF | 22348 |
| HPV31 | L2 | 8 | 151 | STHENPTF | 22349 |
| HPV31 | L2 | 8 | 184 | STHNYEEI | 22350 |
| HPV31 | L2 | 10 | 184 | STHNYEEIPM | 22351 |
| HPV31 | L2 | 8 | 6 | STKRTKRA | 22352 |
| HPV31 | L2 | 10 | 6 | STKRTKRASA | 22353 |
| HPV31 | L2 | 8 | 346 | STLNDGLY | 22354 |
| HPV31 | L2 | 10 | 346 | STLNDGLYDI | 22355 |
| HPV31 | L2 | 11 | 346 | STLNDGLYDIY | 22356 |
| HPV31 | L2 | 11 | 208 | STPIPGVRRPA | 22357 |
| HPV31 | L2 | 10 | 76 | STRPSTVSEA | 22358 |
| HPV31 | L2 | 8 | 379 | STSAVSAY | 22359 |
| HPV31 | L2 | 9 | 379 | STSAVSAYV | 22360 |
| HPV31 | L2 | 8 | 80 | STVSEASI | 22361 |
| HPV31 | L2 | 10 | 80 | STVSEASIPI | 22362 |
| HPV31 | L2 | 8 | 137 | TADTTPAI | 22363 |
| HPV31 | L2 | 9 | 137 | TADTTPAIL | 22364 |
| HPV31 | L2 | 11 | 137 | TADTTPAILDV | 22365 |
| HPV31 | L2 | 8 | 375 | TAVQSTSA | 22366 |
| HPV31 | L2 | 9 | 375 | TAVQSTSAV | 22367 |
| HPV31 | L2 | 11 | 375 | TAVQSTSAVSA | 22368 |
| HPV31 | L2 | 8 | 380 | TSAVSAYV | 22369 |
| HPV31 | L2 | 10 | 129 | TSGFDIATTA | 22370 |
| HPV31 | L2 | 11 | 266 | TSHNIAPDPDF | 22371 |
| HPV31 | L2 | 9 | 288 | TSRRNTVRY | 22372 |
| HPV31 | L2 | 9 | 206 | TSSTPIPGV | 22373 |
| HPV31 | L2 | 8 | 345 | TSTLNDGL | 22374 |
| HPV31 | L2 | 9 | 345 | TSTLNDGLY | 22375 |
| HPV31 | L2 | 11 | 345 | TSTLNDGLYDI | 22376 |
| HPV31 | L2 | 11 | 148 | TSVSTHENPTF | 22377 |
| HPV31 | L2 | 8 | 136 | TTADTTPA | 22378 |
| HPV31 | L2 | 9 | 136 | TTADTTPAI | 22379 |
| HPV31 | L2 | 10 | 136 | TTADTTPAIL | 22380 |
| HPV31 | L2 | 8 | 39 | TTIADQIL | 22381 |
| HPV31 | L2 | 10 | 39 | TTIADQILRY | 22382 |
| HPV31 | L2 | 8 | 140 | TTPAILDV | 22383 |
| HPV31 | L2 | 11 | 140 | TTPAILDVTSV | 22384 |
| HPV31 | L2 | 8 | 426 | TTPQVSIF | 22385 |
| HPV31 | L2 | 9 | 426 | TTPQVSIFV | 22386 |
| HPV31 | L2 | 8 | 128 | TTSGFDIA | 22387 |
| HPV31 | L2 | 11 | 128 | TTSGFDIATTA | 22388 |
| HPV31 | L2 | 9 | 344 | TTSTLNDGL | 22389 |
| HPV31 | L2 | 10 | 344 | TTSTLNDGLY | 22390 |
| HPV31 | L2 | 10 | 343 | TTTSTLNDGL | 22391 |
| HPV31 | L2 | 11 | 343 | TTTSTLNDGLY | 22392 |
| HPV31 | L2 | 9 | 391 | TTVPLSTGF | 22393 |
| HPV31 | L2 | 11 | 391 | TTVPLSTGFDI | 22394 |
| HPV31 | L2 | 11 | 383 | VSAYVPTNTTV | 22395 |
| HPV31 | L2 | 8 | 82 | VSEASIPI | 22396 |
| HPV31 | L2 | 9 | 93 | VSIDPVGPL | 22397 |
| HPV31 | L2 | 10 | 430 | VSIFVDGGDF | 22398 |
| HPV31 | L2 | 11 | 430 | VSIFVDGGDFY | 22399 |
| HPV31 | L2 | 9 | 106 | VSLVEESGI | 22400 |
| HPV31 | L2 | 10 | 106 | VSLVEESGIV | 22401 |
| HPV31 | L2 | 9 | 150 | VSTHENPTF | 22402 |
| HPV31 | L2 | 8 | 198 | VSTNNENI | 22403 |
| HPV31 | L2 | 8 | 455 | VSYFFTDV | 22404 |
| HPV31 | L2 | 10 | 455 | VSYFFTDVSV | 22405 |
| HPV31 | L2 | 11 | 455 | VSYFFTDVSVA | 22406 |
| HPV31 | L2 | 8 | 356 | YADTDFTV | 22407 |
| HPV31 | L2 | 8 | 223 | YSKATQQV | 22408 |
| HPV31 | L2 | 10 | 223 | YSKATQQVKV | 22409 |
| HPV31 | L2 | 11 | 223 | YSKATQQVKVI | 22410 |
| HPV31 | L2 | 10 | 296 | YSRLGNKQTL | 22411 |
| HPV33 | E1 | 11 | 382 | AAAFLKSNSQA | 22412 |
| HPV33 | E1 | 8 | 90 | AACSQSAA | 22413 |
| HPV33 | E1 | 11 | 90 | AACSQSAAEDV | 22414 |
| HPV33 | E1 | 9 | 96 | AAEDVVDRA | 22415 |
| HPV33 | E1 | 10 | 96 | AAEDVVDRAA | 22416 |
| HPV33 | E1 | 10 | 383 | AAFLKSNSQA | 22417 |
| HPV33 | E1 | 9 | 104 | AANPCRTSI | 22418 |
| HPV33 | E1 | 8 | 65 | AARALFNI | 22419 |

TABLE XIII-continued

B58 Supermotif Peptides

| Type | Protein | No. of Amino Acids | Position | Sequence | Seq. Id. No. |
|---|---|---|---|---|---|
| HPV33 | E1 | 8 | 83 | CALKRKFA | 22420 |
| HPV33 | E1 | 9 | 83 | CALKRKFAA | 22421 |
| HPV33 | E1 | 9 | 310 | CALYWFRTA | 22422 |
| HPV33 | E1 | 10 | 310 | CALYWFRTAM | 22423 |
| HPV33 | E1 | 10 | 633 | CSAGENTRSL | 22424 |
| HPV33 | E1 | 8 | 276 | CSKNRLTV | 22425 |
| HPV33 | E1 | 9 | 276 | CSKNRLTVA | 22426 |
| HPV33 | E1 | 11 | 276 | CSKNRLTVAKL | 22427 |
| HPV33 | E1 | 9 | 92 | CSQSAAEDV | 22428 |
| HPV33 | E1 | 10 | 92 | CSQSAAEDVV | 22429 |
| HPV33 | E1 | 9 | 226 | CTDWCITGY | 22430 |
| HPV33 | E1 | 11 | 226 | CTDWCITGYGI | 22431 |
| HPV33 | E1 | 9 | 14 | CTGWFEVEA | 22432 |
| HPV33 | E1 | 10 | 14 | CTGWFEVEAV | 22433 |
| HPV33 | E1 | 11 | 14 | CTGWFEVEAVI | 22434 |
| HPV33 | E1 | 8 | 118 | CTYRKRKI | 22435 |
| HPV33 | E1 | 11 | 118 | CTYRKRKIDEL | 22436 |
| HPV33 | E1 | 10 | 508 | DAKIGMIDDV | 22437 |
| HPV33 | E1 | 8 | 177 | DSCENVTL | 22438 |
| HPV33 | E1 | 11 | 177 | DSCENVTLQEI | 22439 |
| HPV33 | E1 | 8 | 365 | DSDIAYYY | 22440 |
| HPV33 | E1 | 9 | 365 | DSDIAYYYA | 22441 |
| HPV33 | E1 | 11 | 365 | DSDIAYYYAQL | 22442 |
| HPV33 | E1 | 10 | 167 | DSEVSCETNV | 22443 |
| HPV33 | E1 | 9 | 42 | DSGTDLLEF | 22444 |
| HPV33 | E1 | 10 | 42 | DSGTDLLEFI | 22445 |
| HPV33 | E1 | 9 | 130 | DSGYGNTEV | 22446 |
| HPV33 | E1 | 9 | 53 | DSMENSIQA | 22447 |
| HPV33 | E1 | 8 | 377 | DSNSNAAA | 22448 |
| HPV33 | E1 | 9 | 377 | DSNSNAAAF | 22449 |
| HPV33 | E1 | 10 | 377 | DSNSNAAAFL | 22450 |
| HPV33 | E1 | 11 | 566 | DSRWPYLHSRL | 22451 |
| HPV33 | E1 | 8 | 62 | DTEAARAL | 22452 |
| HPV33 | E1 | 9 | 62 | DTEAARALF | 22453 |
| HPV33 | E1 | 11 | 62 | DTEAARALFNI | 22454 |
| HPV33 | E1 | 9 | 64 | EAARALFNI | 22455 |
| HPV33 | E1 | 8 | 206 | EAYGISFM | 22456 |
| HPV33 | E1 | 10 | 206 | EAYGISFMEL | 22457 |
| HPV33 | E1 | 11 | 206 | EAYGISFMELV | 22458 |
| HPV33 | E1 | 9 | 148 | ESQNGDTNL | 22459 |
| HPV33 | E1 | 11 | 160 | ESSGVGDDSEV | 22460 |
| HPV33 | E1 | 10 | 38 | ETADDSGTDL | 22461 |
| HPV33 | E1 | 11 | 38 | ETADDSGTDLL | 22462 |
| HPV33 | E1 | 11 | 295 | ETCMVIEPPKL | 22463 |
| HPV33 | E1 | 10 | 173 | ETNVDSCENV | 22464 |
| HPV33 | E1 | 9 | 139 | ETQQMVQQV | 22465 |
| HPV33 | E1 | 8 | 89 | FAACSQSA | 22466 |
| HPV33 | E1 | 9 | 89 | FAACSQSAA | 22467 |
| HPV33 | E1 | 8 | 606 | FSRTWCKL | 22468 |
| HPV33 | E1 | 10 | 606 | FSRTWCKLDL | 22469 |
| HPV33 | E1 | 11 | 606 | FSRTWCKLDLI | 22470 |
| HPV33 | E1 | 8 | 446 | FTAFLGAF | 22471 |
| HPV33 | E1 | 11 | 446 | FTAFLGAFKKF | 22472 |
| HPV33 | E1 | 10 | 451 | GAFKKFLKGI | 22473 |
| HPV33 | E1 | 9 | 9 | GAGMGCTGW | 22474 |
| HPV33 | E1 | 10 | 9 | GAGMGCTGWF | 22475 |
| HPV33 | E1 | 8 | 44 | GTDLLEFI | 22476 |
| HPV33 | E1 | 8 | 564 | GTDSRWPY | 22477 |
| HPV33 | E1 | 9 | 564 | GTDSRWPYL | 22478 |
| HPV33 | E1 | 10 | 327 | GTTPEWIDRL | 22479 |
| HPV33 | E1 | 8 | 341 | HSFNDNIF | 22480 |
| HPV33 | E1 | 10 | 341 | HSFNDNIFDL | 22481 |
| HPV33 | E1 | 10 | 251 | HSLYTHLQCL | 22482 |
| HPV33 | E1 | 9 | 573 | HSRLTVFEF | 22483 |
| HPV33 | E1 | 9 | 192 | HSSNTKANI | 22484 |
| HPV33 | E1 | 10 | 192 | HSSNTKANIL | 22485 |
| HPV33 | E1 | 11 | 192 | HSSNTKANILY | 22486 |
| HPV33 | E1 | 8 | 368 | IAYYYAQL | 22487 |
| HPV33 | E1 | 9 | 368 | IAYYYAQLA | 22488 |
| HPV33 | E1 | 10 | 492 | ISCVNSKSHF | 22489 |
| HPV33 | E1 | 11 | 492 | ISCVNSKSHFW | 22490 |
| HPV33 | E1 | 11 | 322 | ISDVQGTTPEW | 22491 |
| HPV33 | E1 | 9 | 32 | ISEDEDETA | 22492 |
| HPV33 | E1 | 10 | 210 | ISFMELVRPF | 22493 |
| HPV33 | E1 | 9 | 538 | ISIDVKHRA | 22494 |
| HPV33 | E1 | 10 | 538 | ISIDVKHRAL | 22495 |

TABLE XIII-continued

B58 Supermotif Peptides

| Type | Protein | No. of Amino Acids | Position | Sequence | Seq. Id. No. |
|---|---|---|---|---|---|
| HPV33 | E1 | 11 | 538 | ISIDVKHRALV | 22496 |
| HPV33 | E1 | 9 | 236 | ISPSVAESL | 22497 |
| HPV33 | E1 | 11 | 236 | ISPSVAESLKV | 22498 |
| HPV33 | E1 | 8 | 628 | ISTFKCSA | 22499 |
| HPV33 | E1 | 9 | 520 | ISWTYIDDY | 22500 |
| HPV33 | E1 | 10 | 520 | ISWTYIDDYM | 22501 |
| HPV33 | E1 | 10 | 231 | ITGYGISPSV | 22502 |
| HPV33 | E1 | 11 | 231 | ITGYGISPSVA | 22503 |
| HPV33 | E1 | 9 | 407 | KAEKRKMSI | 22504 |
| HPV33 | E1 | 8 | 197 | KANILYKF | 22505 |
| HPV33 | E1 | 11 | 197 | KANILYKFKEA | 22506 |
| HPV33 | E1 | 10 | 463 | KSCMLICGPA | 22507 |
| HPV33 | E1 | 10 | 220 | KSDKTSCTDW | 22508 |
| HPV33 | E1 | 8 | 603 | KSFFSRTW | 22509 |
| HPV33 | E1 | 11 | 603 | KSFFSRTWCKL | 22510 |
| HPV33 | E1 | 9 | 498 | KSHFWLQPL | 22511 |
| HPV33 | E1 | 8 | 387 | KSNSQAKI | 22512 |
| HPV33 | E1 | 9 | 387 | KSNSQAKIV | 22513 |
| HPV33 | E1 | 8 | 476 | KSYFGMSL | 22514 |
| HPV33 | E1 | 9 | 476 | KSYFGMSLI | 22515 |
| HPV33 | E1 | 11 | 476 | KSYFGMSLIQF | 22516 |
| HPV33 | E1 | 8 | 425 | KTNDGGNW | 22517 |
| HPV33 | E1 | 11 | 425 | KTNDGGNWRPI | 22518 |
| HPV33 | E1 | 9 | 223 | KTSCTDWCI | 22519 |
| HPV33 | E1 | 8 | 375 | LADSNSNA | 22520 |
| HPV33 | E1 | 9 | 375 | LADSNSNAA | 22521 |
| HPV33 | E1 | 10 | 375 | LADSNSNAAA | 22522 |
| HPV33 | E1 | 11 | 375 | LADSNSNAAAF | 22523 |
| HPV33 | E1 | 8 | 506 | LSDAKIGM | 22524 |
| HPV33 | E1 | 9 | 506 | LSDAKIGMI | 22525 |
| HPV33 | E1 | 8 | 350 | LSEMVQWA | 22526 |
| HPV33 | E1 | 9 | 350 | LSEMVQWAY | 22527 |
| HPV33 | E1 | 8 | 291 | LSIPETCM | 22528 |
| HPV33 | E1 | 9 | 291 | LSIPETCMV | 22529 |
| HPV33 | E1 | 10 | 291 | LSIPETCMVI | 22530 |
| HPV33 | E1 | 8 | 260 | LTCDRGII | 22531 |
| HPV33 | E1 | 9 | 260 | LTCDRGIII | 22532 |
| HPV33 | E1 | 10 | 260 | LTCDRGIIIL | 22533 |
| HPV33 | E1 | 11 | 260 | LTCDRGIIILL | 22534 |
| HPV33 | E1 | 8 | 362 | LTDDSDIA | 22535 |
| HPV33 | E1 | 9 | 362 | LTDDSDIAY | 22536 |
| HPV33 | E1 | 10 | 362 | LTDDSDIAYY | 22537 |
| HPV33 | E1 | 11 | 362 | LTDDSDIAYYY | 22538 |
| HPV33 | E1 | 10 | 281 | LTVAKLMSNL | 22539 |
| HPV33 | E1 | 11 | 281 | LTVAKLMSNLL | 22540 |
| HPV33 | E1 | 10 | 576 | LTVFEFKNPF | 22541 |
| HPV33 | E1 | 8 | 336 | LTVLQHSF | 22542 |
| HPV33 | E1 | 10 | 1 | MADPEGTNGA | 22543 |
| HPV33 | E1 | 11 | 481 | MSLIQFLKGCV | 22544 |
| HPV33 | E1 | 8 | 562 | NAGTDSRW | 22545 |
| HPV33 | E1 | 10 | 562 | NAGTDSRWPY | 22546 |
| HPV33 | E1 | 11 | 562 | NAGTDSRWPYL | 22547 |
| HPV33 | E1 | 8 | 531 | NALDGNEI | 22548 |
| HPV33 | E1 | 10 | 531 | NALDGNEISI | 22549 |
| HPV33 | E1 | 10 | 80 | NAVCALKRKF | 22550 |
| HPV33 | E1 | 11 | 80 | NAVCALKRKFA | 22551 |
| HPV33 | E1 | 9 | 57 | NSIQADTEA | 22552 |
| HPV33 | E1 | 10 | 57 | NSIQADTEAA | 22553 |
| HPV33 | E1 | 8 | 496 | NSKSHFWL | 22554 |
| HPV33 | E1 | 11 | 496 | NSKSHFWLQPL | 22555 |
| HPV33 | E1 | 8 | 379 | NSNAAAFL | 22556 |
| HPV33 | E1 | 9 | 135 | NTEVETQQM | 22557 |
| HPV33 | E1 | 10 | 135 | NTEVETQQMV | 22558 |
| HPV33 | E1 | 9 | 473 | NTGKSYFGM | 22559 |
| HPV33 | E1 | 11 | 473 | NTGKSYFGMSL | 22560 |
| HPV33 | E1 | 8 | 195 | NTKANILY | 22561 |
| HPV33 | E1 | 10 | 195 | NTKANILYKF | 22562 |
| HPV33 | E1 | 10 | 560 | NTNAGTDSRW | 22563 |
| HPV33 | E1 | 8 | 471 | PANTGKSY | 22564 |
| HPV33 | E1 | 9 | 471 | PANTGKSYF | 22565 |
| HPV33 | E1 | 11 | 471 | PANTGKSYFGM | 22566 |
| HPV33 | E1 | 9 | 238 | PSVAESLKV | 22567 |
| HPV33 | E1 | 10 | 238 | PSVAESLKVL | 22568 |
| HPV33 | E1 | 11 | 238 | PSVAESLKVLI | 22569 |
| HPV33 | E1 | 9 | 60 | QADTEAARA | 22570 |
| HPV33 | E1 | 10 | 60 | QADTEAARAL | 22571 |

TABLE XIII-continued

B58 Supermotif Peptides

| Type | Protein | No. of Amino Acids | Position | Sequence | Seq. Id. No. |
|---|---|---|---|---|---|
| HPV33 | E1 | 11 | 60 | QADTEAARALF | 22572 |
| HPV33 | E1 | 10 | 391 | QAKIVKDCGI | 22573 |
| HPV33 | E1 | 11 | 391 | QAKIVKDCGIM | 22574 |
| HPV33 | E1 | 8 | 94 | QSAAEDVV | 22575 |
| HPV33 | E1 | 11 | 94 | QSAAEDVVDRA | 22576 |
| HPV33 | E1 | 8 | 308 | QTCALYWF | 22577 |
| HPV33 | E1 | 11 | 308 | QTCALYWFRTA | 22578 |
| HPV33 | E1 | 10 | 103 | RAANPCRTSI | 22579 |
| HPV33 | E1 | 11 | 545 | RALVQLKCPPL | 22580 |
| HPV33 | E1 | 8 | 306 | RSQTCALY | 22581 |
| HPV33 | E1 | 9 | 306 | RSQTCALYW | 22582 |
| HPV33 | E1 | 10 | 306 | RSQTCALYWF | 22583 |
| HPV33 | E1 | 10 | 316 | RTAMSNISDV | 22584 |
| HPV33 | E1 | 8 | 608 | RTWCKLDL | 22585 |
| HPV33 | E1 | 9 | 608 | RTWCKLDLI | 22586 |
| HPV33 | E1 | 10 | 95 | SAAEDVVDRA | 22587 |
| HPV33 | E1 | 11 | 95 | SAAEDVVDRAA | 22588 |
| HPV33 | E1 | 9 | 634 | SAGENTRSL | 22589 |
| HPV33 | E1 | 10 | 161 | SSGVGDDSEV | 22590 |
| HPV33 | E1 | 8 | 193 | SSNTKANI | 22591 |
| HPV33 | E1 | 9 | 193 | SSNTKANIL | 22592 |
| HPV33 | E1 | 10 | 193 | SSNTKANILY | 22593 |
| HPV33 | E1 | 9 | 39 | TADDSGTDL | 22594 |
| HPV33 | E1 | 10 | 39 | TADDSGTDLL | 22595 |
| HPV33 | E1 | 10 | 447 | TAFLGAFKKF | 22596 |
| HPV33 | E1 | 11 | 447 | TAFLGAFKKFL | 22597 |
| HPV33 | E1 | 9 | 317 | TAMSNISDV | 22598 |
| HPV33 | E1 | 8 | 224 | TSCTDWCI | 22599 |
| HPV33 | E1 | 11 | 224 | TSCTDWCITGY | 22600 |
| HPV33 | E1 | 11 | 110 | TSINKNKECTY | 22601 |
| HPV33 | E1 | 9 | 328 | TTPEWIDRL | 22602 |
| HPV33 | E1 | 11 | 328 | TTPEWIDRLTV | 22603 |
| HPV33 | E1 | 8 | 240 | VAESLKVL | 22604 |
| HPV33 | E1 | 9 | 240 | VAESLKVLI | 22605 |
| HPV33 | E1 | 8 | 283 | VAKLMSNL | 22606 |
| HPV33 | E1 | 9 | 283 | VAKLMSNLL | 22607 |
| HPV33 | E1 | 11 | 283 | VAKLMSNLLSI | 22608 |
| HPV33 | E1 | 9 | 182 | VTLQEISNV | 22609 |
| HPV33 | E1 | 10 | 182 | VTLQEISNVL | 22610 |
| HPV33 | E1 | 8 | 517 | VTPISWTY | 22611 |
| HPV33 | E1 | 9 | 517 | VTPISWTYI | 22612 |
| HPV33 | E1 | 8 | 522 | WTYIDDYM | 22613 |
| HPV33 | E1 | 11 | 522 | WTYIDDYMRNA | 22614 |
| HPV33 | E1 | 8 | 595 | YAINDENW | 22615 |
| HPV33 | E1 | 11 | 595 | YAINDENWKSF | 22616 |
| HPV33 | E1 | 11 | 372 | YAQLADSNSNA | 22617 |
| HPV33 | E2 | 9 | 223 | AAAKRRRPA | 22618 |
| HPV33 | E2 | 8 | 224 | AAKRRRPA | 22619 |
| HPV33 | E2 | 9 | 175 | AAKYSKTQM | 22620 |
| HPV33 | E2 | 10 | 175 | AAKYSKTQMW | 22621 |
| HPV33 | E2 | 9 | 64 | ASKTKAFQV | 22622 |
| HPV33 | E2 | 10 | 64 | ASKTKAFQVI | 22623 |
| HPV33 | E2 | 11 | 258 | ATNCTNKQRTV | 22624 |
| HPV33 | E2 | 11 | 245 | CADPALDNRTA | 22625 |
| HPV33 | E2 | 10 | 40 | CALLYTAKQM | 22626 |
| HPV33 | E2 | 8 | 269 | CSSNVAPI | 22627 |
| HPV33 | E2 | 9 | 269 | CSSNVAPIV | 22628 |
| HPV33 | E2 | 11 | 269 | CSSNVAPIVHL | 22629 |
| HPV33 | E2 | 8 | 145 | CTMVTGKV | 22630 |
| HPV33 | E2 | 10 | 145 | CTMVTGKVDY | 22631 |
| HPV33 | E2 | 11 | 145 | CTMVTGKVDYI | 22632 |
| HPV33 | E2 | 8 | 261 | CTNKQRTV | 22633 |
| HPV33 | E2 | 10 | 174 | DAAKYSKTQM | 22634 |
| HPV33 | E2 | 11 | 174 | DAAKYSKTQMW | 22635 |
| HPV33 | E2 | 9 | 235 | DTAQPLTKL | 22636 |
| HPV33 | E2 | 10 | 235 | DTAQPLTKLF | 22637 |
| HPV33 | E2 | 10 | 143 | DTCTMVTGKV | 22638 |
| HPV33 | E2 | 9 | 232 | DTTDTAQPL | 22639 |
| HPV33 | E2 | 11 | 20 | EADKTDLPSQI | 22640 |
| HPV33 | E2 | 8 | 282 | ESNSLKCL | 22641 |
| HPV33 | E2 | 10 | 282 | ESNSLKCLRY | 22642 |
| HPV33 | E2 | 8 | 80 | ETLSKSQY | 22643 |
| HPV33 | E2 | 8 | 51 | FSHLCHQV | 22644 |
| HPV33 | E2 | 9 | 51 | FSHLCHQVV | 22645 |
| HPV33 | E2 | 9 | 336 | GTVKIPPTV | 22646 |
| HPV33 | E2 | 11 | 336 | GTVKIPPTVQI | 22647 |

TABLE XIII-continued

B58 Supermotif Peptides

| Type | Protein | No. of Amino Acids | Position | Sequence | Seq. Id. No. |
|---|---|---|---|---|---|
| HPV33 | E2 | 8 | 4 | ISARLNAV | 22648 |
| HPV33 | E2 | 8 | 346 | ISTGFMTL | 22649 |
| HPV33 | E2 | 9 | 204 | ISTTETADI | 22650 |
| HPV33 | E2 | 8 | 68 | KAFQVIEL | 22651 |
| HPV33 | E2 | 10 | 68 | KAFQVIELQM | 22652 |
| HPV33 | E2 | 11 | 68 | KAFQVIELQMA | 22653 |
| HPV33 | E2 | 9 | 84 | KSQYSTSQW | 22654 |
| HPV33 | E2 | 11 | 84 | KSQYSTSQWTL | 22655 |
| HPV33 | E2 | 8 | 23 | KTDLPSQI | 22656 |
| HPV33 | E2 | 11 | 23 | KTDLPSQIEHW | 22657 |
| HPV33 | E2 | 8 | 66 | KTKAFQVI | 22658 |
| HPV33 | E2 | 10 | 66 | KTKAFQVIEL | 22659 |
| HPV33 | E2 | 9 | 180 | KTQMWEVHV | 22660 |
| HPV33 | E2 | 8 | 63 | LASKTKAF | 22661 |
| HPV33 | E2 | 10 | 63 | LASKTKAFQV | 22662 |
| HPV33 | E2 | 11 | 63 | LASKTKAFQVI | 22663 |
| HPV33 | E2 | 11 | 82 | LSKSQYSTSQW | 22664 |
| HPV33 | E2 | 10 | 240 | LTKLFCADPA | 22665 |
| HPV33 | E2 | 11 | 240 | LTKLFCADPAL | 22666 |
| HPV33 | E2 | 11 | 77 | MALETLSKSQY | 22667 |
| HPV33 | E2 | 8 | 9 | NAVQEKIL | 22668 |
| HPV33 | E2 | 10 | 9 | NAVQEKILDL | 22669 |
| HPV33 | E2 | 11 | 9 | NAVQEKILDLY | 22670 |
| HPV33 | E2 | 9 | 315 | NSKNGIVTV | 22671 |
| HPV33 | E2 | 11 | 315 | NSKNGIVTVTF | 22672 |
| HPV33 | E2 | 8 | 284 | NSLKCLRY | 22673 |
| HPV33 | E2 | 10 | 284 | NSLKCLRYRL | 22674 |
| HPV33 | E2 | 8 | 127 | NTMDYTNW | 22675 |
| HPV33 | E2 | 11 | 127 | NTMDYTNWGEI | 22676 |
| HPV33 | E2 | 8 | 230 | PADTTDTA | 22677 |
| HPV33 | E2 | 11 | 230 | PADTTDTAQPL | 22678 |
| HPV33 | E2 | 8 | 248 | PALDNRTA | 22679 |
| HPV33 | E2 | 11 | 248 | PALDNRTARTA | 22680 |
| HPV33 | E2 | 10 | 60 | PSLLASKTKA | 22681 |
| HPV33 | E2 | 11 | 60 | PSLLASKTKAF | 22682 |
| HPV33 | E2 | 9 | 27 | PSQIEHWKL | 22683 |
| HPV33 | E2 | 10 | 27 | PSQIEHWKLI | 22684 |
| HPV33 | E2 | 9 | 196 | PTSISSNQI | 22685 |
| HPV33 | E2 | 9 | 342 | PTVQISTGF | 22686 |
| HPV33 | E2 | 10 | 342 | PTVQISTGFM | 22687 |
| HPV33 | E2 | 10 | 222 | QAAAKRRRPA | 22688 |
| HPV33 | E2 | 11 | 213 | QTDNDNRPPQA | 22689 |
| HPV33 | E2 | 8 | 96 | QTSLEVWL | 22690 |
| HPV33 | E2 | 8 | 266 | RTVCSSNV | 22691 |
| HPV33 | E2 | 9 | 266 | RTVCSSNVA | 22692 |
| HPV33 | E2 | 11 | 266 | RTVCSSNVAPI | 22693 |
| HPV33 | E2 | 11 | 5 | SARLNAVQEKI | 22694 |
| HPV33 | E2 | 9 | 301 | SSMSSTWHW | 22695 |
| HPV33 | E2 | 11 | 200 | SSNQISTTETA | 22696 |
| HPV33 | E2 | 8 | 270 | SSNVAPIV | 22697 |
| HPV33 | E2 | 10 | 270 | SSNVAPIVHL | 22698 |
| HPV33 | E2 | 8 | 205 | STTETADI | 22699 |
| HPV33 | E2 | 10 | 45 | TAKQMGFSHL | 22700 |
| HPV33 | E2 | 8 | 236 | TAQPLTKL | 22701 |
| HPV33 | E2 | 9 | 236 | TAQPLTKLF | 22702 |
| HPV33 | E2 | 11 | 236 | TAQPLTKLFCA | 22703 |
| HPV33 | E2 | 11 | 310 | TSDNKSKNGI | 22704 |
| HPV33 | E2 | 8 | 197 | TSISSNQI | 22705 |
| HPV33 | E2 | 11 | 89 | TSQWTLQQTSL | 22706 |
| HPV33 | E2 | 8 | 233 | TTDTAQPL | 22707 |
| HPV33 | E2 | 11 | 233 | TTDTAQPLTKL | 22708 |
| HPV33 | E2 | 8 | 326 | VTEQQQQM | 22709 |
| HPV33 | E2 | 9 | 326 | VTEQQQQMF | 22710 |
| HPV33 | E2 | 10 | 326 | VTEQQQQMFL | 22711 |
| HPV33 | E2 | 11 | 323 | VTFVTEQQQQM | 22712 |
| HPV33 | E2 | 8 | 148 | VTGKVDYI | 22713 |
| HPV33 | E2 | 10 | 148 | VTGKVDYIGM | 22714 |
| HPV33 | E2 | 11 | 148 | VTGKVDYIGMY | 22715 |
| HPV33 | E2 | 8 | 92 | WTLQQTSL | 22716 |
| HPV33 | E2 | 10 | 92 | WTLQQTSLEV | 22717 |
| HPV33 | E2 | 11 | 92 | WTLQQTSLEVW | 22718 |
| HPV33 | E2 | 9 | 178 | YSKTQMWEV | 22719 |
| HPV33 | E2 | 11 | 178 | YSKTQMWEVHV | 22720 |
| HPV33 | E2 | 8 | 300 | YSSMSSTW | 22721 |
| HPV33 | E2 | 10 | 300 | YSSMSSTWHW | 22722 |
| HPV33 | E2 | 8 | 87 | YSTSQWTL | 22723 |

TABLE XIII-continued

B58 Supermotif Peptides

| Type | Protein | No. of Amino Acids | Position | Sequence | Seq. Id. No. |
|---|---|---|---|---|---|
| HPV33 | E2 | 8 | 44 | YTAKQMGF | 22724 |
| HPV33 | E2 | 11 | 44 | YTAKQMGFSHL | 22725 |
| HPV33 | E2 | 8 | 131 | YTNWGEIY | 22726 |
| HPV33 | E2 | 9 | 131 | YTNWGEIYI | 22727 |
| HPV33 | E2 | 10 | 131 | YTNWGEIYII | 22728 |
| HPV33 | E5 | 8 | 44 | GSPLKIFF | 22729 |
| HPV33 | E5 | 10 | 44 | GSPLKIFFCY | 22730 |
| HPV33 | E5 | 11 | 44 | GSPLKIFFCYL | 22731 |
| HPV33 | E5 | 8 | 26 | ISTYAWLL | 22732 |
| HPV33 | E5 | 9 | 26 | ISTYAWLLV | 22733 |
| HPV33 | E5 | 10 | 26 | ISTYAWLLVL | 22734 |
| HPV33 | E5 | 11 | 26 | ISTYAWLLVLV | 22735 |
| HPV33 | E5 | 8 | 24 | LSISTYAW | 22736 |
| HPV33 | E5 | 9 | 24 | LSISTYAWL | 22737 |
| HPV33 | E5 | 10 | 24 | LSISTYAWLL | 22738 |
| HPV33 | E5 | 11 | 24 | LSISTYAWLLV | 22739 |
| HPV33 | E5 | 8 | 15 | LSLLLRPL | 22740 |
| HPV33 | E5 | 9 | 15 | LSLLLRPLI | 22741 |
| HPV33 | E5 | 10 | 15 | LSLLLRPLIL | 22742 |
| HPV33 | E5 | 8 | 27 | STYAWLLV | 22743 |
| HPV33 | E5 | 9 | 27 | STYAWLLVL | 22744 |
| HPV33 | E5 | 10 | 27 | STYAWLLVLV | 22745 |
| HPV33 | E5 | 11 | 27 | STYAWLLVLVL | 22746 |
| HPV33 | E5 | 8 | 29 | YAWLLVLV | 22747 |
| HPV33 | E5 | 9 | 29 | YAWLLVLVL | 22748 |
| HPV33 | E5 | 10 | 29 | YAWLLVLVLL | 22749 |
| HPV33 | E5 | 11 | 29 | YAWLLVLVLLL | 22750 |
| HPV33 | E6 | 9 | 4 | DTEEKPRTL | 22751 |
| HPV33 | E6 | 9 | 20 | ETTIHNIEL | 22752 |
| HPV33 | E6 | 8 | 47 | FADLTVVY | 22753 |
| HPV33 | E6 | 8 | 45 | FAFADLTV | 22754 |
| HPV33 | E6 | 9 | 45 | FAFADLTVV | 22755 |
| HPV33 | E6 | 10 | 45 | FAFADLTVVY | 22756 |
| HPV33 | E6 | 9 | 73 | ISEYRHYNY | 22757 |
| HPV33 | E6 | 11 | 73 | ISEYRHYNYSV | 22758 |
| HPV33 | E6 | 10 | 128 | ISGRWAGRCA | 22759 |
| HPV33 | E6 | 11 | 128 | ISGRWAGRCAA | 22760 |
| HPV33 | E6 | 10 | 70 | LSKISEYRHY | 22761 |
| HPV33 | E6 | 11 | 50 | LTVVYREGNPF | 22762 |
| HPV33 | E6 | 11 | 86 | NTLEQTVKKPL | 22763 |
| HPV33 | E6 | 10 | 17 | QALETTIHNI | 22764 |
| HPV33 | E6 | 10 | 90 | QTVKKPLNEI | 22765 |
| HPV33 | E6 | 11 | 90 | QTVKKPLNEIL | 22766 |
| HPV33 | E6 | 8 | 39 | RSEVYDFA | 22767 |
| HPV33 | E6 | 9 | 39 | RSEVYDFAF | 22768 |
| HPV33 | E6 | 10 | 39 | RSEVYDFAFA | 22769 |
| HPV33 | E6 | 8 | 141 | RSRRRETA | 22770 |
| HPV33 | E6 | 9 | 141 | RSRRRETAL | 22771 |
| HPV33 | E6 | 9 | 10 | RTLHDLCQA | 22772 |
| HPV33 | E6 | 10 | 10 | RTLHDLCQAL | 22773 |
| HPV33 | E6 | 8 | 21 | TTIHNIEL | 22774 |
| HPV33 | E6 | 11 | 21 | TTIHNIELQCV | 22775 |
| HPV33 | E6 | 9 | 132 | WAGRCAACW | 22776 |
| HPV33 | E6 | 8 | 81 | YSVYGNTL | 22777 |
| HPV33 | E7 | 10 | 73 | ASDLRTIQQL | 22778 |
| HPV33 | E7 | 11 | 73 | ASDLRTIQQLL | 22779 |
| HPV33 | E7 | 8 | 48 | ATADYYIV | 22780 |
| HPV33 | E7 | 9 | 30 | DSSDEDEGL | 22781 |
| HPV33 | E7 | 11 | 85 | GTVNIVCPTCA | 22782 |
| HPV33 | E7 | 9 | 59 | HTCNTTVRL | 22783 |
| HPV33 | E7 | 11 | 59 | HTCNTTVRLCV | 22784 |
| HPV33 | E7 | 11 | 28 | LSDSSDEDEGL | 22785 |
| HPV33 | E7 | 10 | 70 | NSTASDLRTI | 22786 |
| HPV33 | E7 | 8 | 62 | NTTVRLCV | 22787 |
| HPV33 | E7 | 8 | 47 | PATADYYI | 22788 |
| HPV33 | E7 | 9 | 47 | PATADYYIV | 22789 |
| HPV33 | E7 | 10 | 19 | PTDLYCYEQL | 22790 |
| HPV33 | E7 | 8 | 6 | PTLKEYVL | 22791 |
| HPV33 | E7 | 10 | 6 | PTLKEYVLDL | 22792 |
| HPV33 | E7 | 11 | 6 | PTLKEYVLDLY | 22793 |
| HPV33 | E7 | 9 | 44 | QAQPATADY | 22794 |
| HPV33 | E7 | 10 | 44 | QAQPATADYY | 22795 |
| HPV33 | E7 | 11 | 44 | QAQPATADYYI | 22796 |
| HPV33 | E7 | 8 | 77 | RTIQQLLM | 22797 |
| HPV33 | E7 | 11 | 77 | RTIQQLLMGTV | 22798 |
| HPV33 | E7 | 8 | 31 | SSDEDEGL | 22799 |

TABLE XIII-continued

B58 Supermotif Peptides

| Type | Protein | No. of Amino Acids | Position | Sequence | Seq. Id. No. |
|---|---|---|---|---|---|
| HPV33 | E7 | 9 | 71 | STASDLRTI | 22800 |
| HPV33 | E7 | 8 | 72 | TASDLRTI | 22801 |
| HPV33 | E7 | 11 | 72 | TASDLRTIQQL | 22802 |
| HPV33 | E7 | 11 | 63 | TTVRLCVNSTA | 22803 |
| HPV33 | E7 | 11 | 55 | VTCCHTCNTTV | 22804 |
| HPV33 | L1 | 10 | 179 | AAPANDCPPL | 22805 |
| HPV33 | L1 | 11 | 482 | AAPTSTRTSSA | 22806 |
| HPV33 | L1 | 8 | 284 | ASIQSSAF | 22807 |
| HPV33 | L1 | 9 | 284 | ASIQSSAFF | 22808 |
| HPV33 | L1 | 9 | 411 | ASLQDTYRF | 22809 |
| HPV33 | L1 | 10 | 411 | ASLQDTYRFV | 22810 |
| HPV33 | L1 | 8 | 9 | ATVYLPPV | 22811 |
| HPV33 | L1 | 10 | 9 | ATVYLPPVPV | 22812 |
| HPV33 | L1 | 10 | 345 | CTQVTSDSTY | 22813 |
| HPV33 | L1 | 9 | 351 | DSTYKNENF | 22814 |
| HPV33 | L1 | 8 | 129 | DTETGNKY | 22815 |
| HPV33 | L1 | 9 | 202 | DTGFGCMDF | 22816 |
| HPV33 | L1 | 8 | 95 | DTQRLVWA | 22817 |
| HPV33 | L1 | 10 | 95 | DTQRLVWACV | 22818 |
| HPV33 | L1 | 8 | 335 | DTTRSTNM | 22819 |
| HPV33 | L1 | 10 | 335 | DTTRSTNMTL | 22820 |
| HPV33 | L1 | 10 | 415 | DTYRFVTSQA | 22821 |
| HPV33 | L1 | 11 | 415 | DTYRFVTSQAI | 22822 |
| HPV33 | L1 | 9 | 8 | EATVYLPPV | 22823 |
| HPV33 | L1 | 11 | 8 | EATVYLPPVPV | 22824 |
| HPV33 | L1 | 8 | 269 | EAVPDDLY | 22825 |
| HPV33 | L1 | 9 | 269 | EAVPDDLYI | 22826 |
| HPV33 | L1 | 9 | 303 | ESQLFNKPY | 22827 |
| HPV33 | L1 | 10 | 303 | ESQLFNKPYW | 22828 |
| HPV33 | L1 | 11 | 303 | ESQLFNKPYWL | 22829 |
| HPV33 | L1 | 8 | 454 | FSADLDQF | 22830 |
| HPV33 | L1 | 10 | 454 | FSADLDQFPL | 22831 |
| HPV33 | L1 | 9 | 50 | FSIKNPTNA | 22832 |
| HPV33 | L1 | 8 | 141 | GADNRECL | 22833 |
| HPV33 | L1 | 10 | 141 | GADNRECLSM | 22834 |
| HPV33 | L1 | 8 | 279 | GSGTTASI | 22835 |
| HPV33 | L1 | 10 | 297 | GSMVTSESQL | 22836 |
| HPV33 | L1 | 11 | 297 | GSMVTSESQLF | 22837 |
| HPV33 | L1 | 8 | 38 | GSSRLLAV | 22838 |
| HPV33 | L1 | 9 | 226 | GSTCKYPDY | 22839 |
| HPV33 | L1 | 10 | 226 | GSTCKYPDYL | 22840 |
| HPV33 | L1 | 11 | 265 | GTLGEAVPDDL | 22841 |
| HPV33 | L1 | 10 | 281 | GTTASIQSSA | 22842 |
| HPV33 | L1 | 11 | 281 | GTTASIQSSAF | 22843 |
| HPV33 | L1 | 8 | 391 | HAMNPDIL | 22844 |
| HPV33 | L1 | 11 | 391 | HAMNPDILEDW | 22845 |
| HPV33 | L1 | 10 | 118 | ISGHPLLNKF | 22846 |
| HPV33 | L1 | 9 | 474 | KAKPKLKRA | 22847 |
| HPV33 | L1 | 10 | 474 | KAKPKLKRAA | 22848 |
| HPV33 | L1 | 8 | 217 | KSDVPIDI | 22849 |
| HPV33 | L1 | 10 | 211 | KTLQANKSDV | 22850 |
| HPV33 | L1 | 8 | 43 | LAVGHPYF | 22851 |
| HPV33 | L1 | 10 | 43 | LAVGHPYFSI | 22852 |
| HPV33 | L1 | 10 | 148 | LSMDYKQTQL | 22853 |
| HPV33 | L1 | 8 | 382 | LTAEVMTY | 22854 |
| HPV33 | L1 | 9 | 382 | LTAEVMTYI | 22855 |
| HPV33 | L1 | 11 | 382 | LTAEVMTYIHA | 22856 |
| HPV33 | L1 | 9 | 405 | LTPPPSASL | 22857 |
| HPV33 | L1 | 9 | 1 | MSVWRPSEA | 22858 |
| HPV33 | L1 | 11 | 1 | MSVWRPSEATV | 22859 |
| HPV33 | L1 | 10 | 237 | MTSEPYGDSL | 22860 |
| HPV33 | L1 | 11 | 237 | MTSEPYGDSLF | 22861 |
| HPV33 | L1 | 11 | 387 | MTYIHAMNPDI | 22862 |
| HPV33 | L1 | 11 | 178 | NAAPANDCPPL | 22863 |
| HPV33 | L1 | 10 | 57 | NAKKLLVPKV | 22864 |
| HPV33 | L1 | 9 | 192 | NTIIEDGDM | 22865 |
| HPV33 | L1 | 10 | 192 | NTIIEDGDMV | 22866 |
| HPV33 | L1 | 8 | 181 | PANDCPPL | 22867 |
| HPV33 | L1 | 10 | 181 | PANDCPPLEL | 22868 |
| HPV33 | L1 | 11 | 181 | PANDCPPLELI | 22869 |
| HPV33 | L1 | 9 | 409 | PSASLQDTY | 22870 |
| HPV33 | L1 | 11 | 409 | PSASLQDTYRF | 22871 |
| HPV33 | L1 | 8 | 6 | PSEATVYL | 22872 |
| HPV33 | L1 | 11 | 6 | PSEATVYLPPV | 22873 |
| HPV33 | L1 | 10 | 165 | PTGEHWGKGV | 22874 |
| HPV33 | L1 | 11 | 165 | PTGEHWGKGVA | 22875 |

TABLE XIII-continued

B58 Supermotif Peptides

| Type | Protein | No. of Amino Acids | Position | Sequence | Seq. Id. No. |
|---|---|---|---|---|---|
| HPV33 | L1 | 8 | 55 | PTNAKKLL | 22876 |
| HPV33 | L1 | 9 | 55 | PTNAKKLLV | 22877 |
| HPV33 | L1 | 8 | 293 | PTPSGSMV | 22878 |
| HPV33 | L1 | 9 | 484 | PTSTRTSSA | 22879 |
| HPV33 | L1 | 10 | 470 | QAGLKAKPKL | 22880 |
| HPV33 | L1 | 9 | 423 | QAITCQKTV | 22881 |
| HPV33 | L1 | 9 | 214 | QANKSDVPI | 22882 |
| HPV33 | L1 | 11 | 214 | QANKSDVPIDI | 22883 |
| HPV33 | L1 | 8 | 263 | RAGTLGEA | 22884 |
| HPV33 | L1 | 9 | 263 | RAGTLGEAV | 22885 |
| HPV33 | L1 | 9 | 315 | RAQGHNNGI | 22886 |
| HPV33 | L1 | 11 | 315 | RAQGHNNGICW | 22887 |
| HPV33 | L1 | 11 | 338 | RSTNMTLCTQV | 22888 |
| HPV33 | L1 | 8 | 30 | RTSIYYYA | 22889 |
| HPV33 | L1 | 10 | 488 | RTSSAKRKKV | 22890 |
| HPV33 | L1 | 9 | 455 | SADLDQFPL | 22891 |
| HPV33 | L1 | 11 | 289 | SAFFPTPSGSM | 22892 |
| HPV33 | L1 | 8 | 410 | SASLQDTY | 22893 |
| HPV33 | L1 | 10 | 410 | SASLQDTYRF | 22894 |
| HPV33 | L1 | 11 | 410 | SASLQDTYRFV | 22895 |
| HPV33 | L1 | 8 | 490 | SSAKRKKV | 22896 |
| HPV33 | L1 | 11 | 39 | SSRLLAVGHPY | 22897 |
| HPV33 | L1 | 8 | 227 | STCKYPDY | 22898 |
| HPV33 | L1 | 9 | 227 | STCKYPDYL | 22899 |
| HPV33 | L1 | 11 | 227 | STCKYPDYLKM | 22900 |
| HPV33 | L1 | 11 | 23 | STDEYVSRTSI | 22901 |
| HPV33 | L1 | 10 | 339 | STNMTLCTQV | 22902 |
| HPV33 | L1 | 8 | 352 | STYKNENF | 22903 |
| HPV33 | L1 | 11 | 352 | STYKNENFKEY | 22904 |
| HPV33 | L1 | 8 | 383 | TAEVMTYI | 22905 |
| HPV33 | L1 | 10 | 383 | TAEVMTYIHA | 22906 |
| HPV33 | L1 | 11 | 383 | TAEVMTYIHAM | 22907 |
| HPV33 | L1 | 8 | 283 | TASIQSSA | 22908 |
| HPV33 | L1 | 9 | 283 | TASIQSSAF | 22909 |
| HPV33 | L1 | 10 | 283 | TASIQSSAFF | 22910 |
| HPV33 | L1 | 11 | 349 | TSDSTYKNENF | 22911 |
| HPV33 | L1 | 9 | 238 | TSEPYGDSL | 22912 |
| HPV33 | L1 | 10 | 238 | TSEPYGDSLF | 22913 |
| HPV33 | L1 | 11 | 238 | TSEPYGDSLFF | 22914 |
| HPV33 | L1 | 11 | 301 | TSESQLFNKPY | 22915 |
| HPV33 | L1 | 11 | 89 | TSFYNPDTQRL | 22916 |
| HPV33 | L1 | 11 | 421 | TSQAITCQKTV | 22917 |
| HPV33 | L1 | 9 | 489 | TSSAKRKKV | 22918 |
| HPV33 | L1 | 8 | 485 | TSTRTSSA | 22919 |
| HPV33 | L1 | 9 | 282 | TTASIQSSA | 22920 |
| HPV33 | L1 | 10 | 282 | TTASIQSSAF | 22921 |
| HPV33 | L1 | 11 | 282 | TTASIQSSAFF | 22922 |
| HPV33 | L1 | 9 | 336 | TTRSTNMTL | 22923 |
| HPV33 | L1 | 9 | 174 | VACTNAAPA | 22924 |
| HPV33 | L1 | 8 | 66 | VSGLQYRV | 22925 |
| HPV33 | L1 | 9 | 66 | VSGLQYRVF | 22926 |
| HPV33 | L1 | 11 | 66 | VSGLQYRVFRV | 22927 |
| HPV33 | L1 | 10 | 18 | VSKVVSTDEY | 22928 |
| HPV33 | L1 | 11 | 18 | VSKVVSTDEYV | 22929 |
| HPV33 | L1 | 8 | 28 | VSRTSIYY | 22930 |
| HPV33 | L1 | 9 | 28 | VSRTSIYYY | 22931 |
| HPV33 | L1 | 10 | 28 | VSRTSIYYYA | 22932 |
| HPV33 | L1 | 8 | 380 | VTLTAEVM | 22933 |
| HPV33 | L1 | 10 | 380 | VTLTAEVMTY | 22934 |
| HPV33 | L1 | 11 | 380 | VTLTAEVMTYI | 22935 |
| HPV33 | L1 | 8 | 300 | VTSESQLF | 22936 |
| HPV33 | L1 | 8 | 101 | WACVGLEI | 22937 |
| HPV33 | L1 | 8 | 36 | YAGSSRLL | 22938 |
| HPV33 | L1 | 9 | 36 | YAGSSRLLA | 22939 |
| HPV33 | L1 | 10 | 36 | YAGSSRLLAV | 22940 |
| HPV33 | L1 | 8 | 443 | YTFWEVDL | 22941 |
| HPV33 | L2 | 8 | 81 | AAIPLQPI | 22942 |
| HPV33 | L2 | 9 | 23 | ATGTCPPDV | 22943 |
| HPV33 | L2 | 10 | 23 | ATGTCPPDVI | 22944 |
| HPV33 | L2 | 11 | 308 | ATLKTRSGKQI | 22945 |
| HPV33 | L2 | 10 | 14 | ATQLYQTCKA | 22946 |
| HPV33 | L2 | 8 | 385 | ATTRTSNV | 22947 |
| HPV33 | L2 | 10 | 385 | ATTRTSNVSI | 22948 |
| HPV33 | L2 | 8 | 101 | DSSIVSLI | 22949 |
| HPV33 | L2 | 11 | 206 | DSSNVTSSTPI | 22950 |
| HPV33 | L2 | 8 | 431 | DTIVVDGA | 22951 |

TABLE XIII-continued

B58 Supermotif Peptides

| Type | Protein | No. of Amino Acids | Position | Sequence | Seq. Id. No. |
|---|---|---|---|---|---|
| HPV33 | L2 | 10 | 431 | DTIVVDGADF | 22952 |
| HPV33 | L2 | 11 | 431 | DTIVVDGADFV | 22953 |
| HPV33 | L2 | 10 | 264 | DTLQFQHSDI | 22954 |
| HPV33 | L2 | 10 | 401 | DTPVMSGPDI | 22955 |
| HPV33 | L2 | 9 | 350 | DTSTSSYSI | 22956 |
| HPV33 | L2 | 9 | 136 | DTTPAIINV | 22957 |
| HPV33 | L2 | 10 | 95 | DTVGPLDSSI | 22958 |
| HPV33 | L2 | 11 | 95 | DTVGPLDSSIV | 22959 |
| HPV33 | L2 | 9 | 115 | EAGAPAPSI | 22960 |
| HPV33 | L2 | 8 | 176 | EASGHFIF | 22961 |
| HPV33 | L2 | 9 | 258 | ESFDPEDTL | 22962 |
| HPV33 | L2 | 11 | 258 | ESFDPEDTLQF | 22963 |
| HPV33 | L2 | 11 | 149 | ESSIQTISTHL | 22964 |
| HPV33 | L2 | 9 | 110 | ETSFIEAGA | 22965 |
| HPV33 | L2 | 11 | 110 | ETSFIEAGAPA | 22966 |
| HPV33 | L2 | 9 | 384 | FATTRTSNV | 22967 |
| HPV33 | L2 | 11 | 384 | FATTRTSNVSI | 22968 |
| HPV33 | L2 | 8 | 301 | FSRVGQKA | 22969 |
| HPV33 | L2 | 10 | 301 | FSRVGQKATL | 22970 |
| HPV33 | L2 | 11 | 183 | FSSPTVSTQSY | 22971 |
| HPV33 | L2 | 8 | 460 | FTDVRVAA | 22972 |
| HPV33 | L2 | 11 | 163 | FTEPSVLHPPA | 22973 |
| HPV33 | L2 | 10 | 437 | GADFVLHPSY | 22974 |
| HPV33 | L2 | 11 | 437 | GADFVLHPSYF | 22975 |
| HPV33 | L2 | 10 | 319 | GARIHYYQDL | 22976 |
| HPV33 | L2 | 8 | 64 | GSGGRTGY | 22977 |
| HPV33 | L2 | 9 | 64 | GSGGRTGYV | 22978 |
| HPV33 | L2 | 11 | 64 | GSGGRTGYVPI | 22979 |
| HPV33 | L2 | 10 | 62 | GSGSGGRTGY | 22980 |
| HPV33 | L2 | 11 | 62 | GSGSGGRTGYV | 22981 |
| HPV33 | L2 | 10 | 48 | GSLGVFFGGL | 22982 |
| HPV33 | L2 | 8 | 218 | GSRPVARL | 22983 |
| HPV33 | L2 | 10 | 218 | GSRPVARLGL | 22984 |
| HPV33 | L2 | 11 | 218 | GSRPVARLGLY | 22985 |
| HPV33 | L2 | 8 | 37 | GSTIADQI | 22986 |
| HPV33 | L2 | 9 | 37 | GSTIADQIL | 22987 |
| HPV33 | L2 | 11 | 37 | GSTIADQILKY | 22988 |
| HPV33 | L2 | 8 | 25 | GTCPPDVI | 22989 |
| HPV33 | L2 | 11 | 25 | GTCPPDVIPKV | 22990 |
| HPV33 | L2 | 8 | 75 | GTDPPTAA | 22991 |
| HPV33 | L2 | 9 | 75 | GTDPPTAAI | 22992 |
| HPV33 | L2 | 11 | 75 | GTDPPTAAIPL | 22993 |
| HPV33 | L2 | 8 | 374 | HTPMQHSY | 22994 |
| HPV33 | L2 | 11 | 374 | HTPMQHSYSTF | 22995 |
| HPV33 | L2 | 8 | 336 | HTVPNEQY | 22996 |
| HPV33 | L2 | 10 | 336 | HTVPNEQYEL | 22997 |
| HPV33 | L2 | 8 | 297 | HTVRFSRV | 22998 |
| HPV33 | L2 | 8 | 40 | IADQILKY | 22999 |
| HPV33 | L2 | 11 | 40 | IADQILKYGSL | 23000 |
| HPV33 | L2 | 8 | 285 | IALHRPAI | 23001 |
| HPV33 | L2 | 9 | 273 | ISPAPDPDF | 23002 |
| HPV33 | L2 | 10 | 273 | ISPAPDPDFL | 23003 |
| HPV33 | L2 | 10 | 424 | ISPFFPFDTI | 23004 |
| HPV33 | L2 | 11 | 424 | ISPFFPFDTIV | 23005 |
| HPV33 | L2 | 9 | 155 | ISTHLNPTF | 23006 |
| HPV33 | L2 | 8 | 292 | ITSRRHTV | 23007 |
| HPV33 | L2 | 10 | 292 | ITSRRHTVRF | 23008 |
| HPV33 | L2 | 8 | 250 | ITYDNPAF | 23009 |
| HPV33 | L2 | 11 | 250 | ITYDNPAFESF | 23010 |
| HPV33 | L2 | 10 | 22 | KATGTCPPDV | 23011 |
| HPV33 | L2 | 11 | 22 | KATGTCPPDVI | 23012 |
| HPV33 | L2 | 8 | 311 | KTRSGKQI | 23013 |
| HPV33 | L2 | 10 | 311 | KTRSGKQIGA | 23014 |
| HPV33 | L2 | 11 | 328 | LSPIVPLDHTV | 23015 |
| HPV33 | L2 | 8 | 243 | LTSPHKLI | 23016 |
| HPV33 | L2 | 10 | 243 | LTSPHKLITY | 23017 |
| HPV33 | L2 | 10 | 405 | MSGPDIPSPL | 23018 |
| HPV33 | L2 | 11 | 405 | MSGPDIPSPLF | 23019 |
| HPV33 | L2 | 8 | 397 | NTGFDTPV | 23020 |
| HPV33 | L2 | 9 | 397 | NTGFDTPVM | 23021 |
| HPV33 | L2 | 8 | 231 | NTQQVKVV | 23022 |
| HPV33 | L2 | 11 | 231 | NTQQVKVVDPA | 23023 |
| HPV33 | L2 | 8 | 174 | PAEASGHF | 23024 |
| HPV33 | L2 | 9 | 174 | PAEASGHFI | 23025 |
| HPV33 | L2 | 10 | 174 | PAEASGHFIF | 23026 |
| HPV33 | L2 | 10 | 240 | PAFLTSPHKL | 23027 |

TABLE XIII-continued

B58 Supermotif Peptides

| Type | Protein | No. of Amino Acids | Position | Sequence | Seq. Id. No. |
|---|---|---|---|---|---|
| HPV33 | L2 | 11 | 240 | PAFLTSPHKLI | 23028 |
| HPV33 | L2 | 9 | 139 | PAIINVSSV | 23029 |
| HPV33 | L2 | 10 | 290 | PAITSRRHTV | 23030 |
| HPV33 | L2 | 10 | 172 | PAPAEASGHF | 23031 |
| HPV33 | L2 | 11 | 172 | PAPAEASGHFI | 23032 |
| HPV33 | L2 | 8 | 275 | PAPDPDFL | 23033 |
| HPV33 | L2 | 10 | 275 | PAPDPDFLDI | 23034 |
| HPV33 | L2 | 11 | 275 | PAPDPDFLDII | 23035 |
| HPV33 | L2 | 11 | 119 | PAPSIPTPSGF | 23036 |
| HPV33 | L2 | 10 | 126 | PSGFDVTTSA | 23037 |
| HPV33 | L2 | 9 | 121 | PSIPTPSGF | 23038 |
| HPV33 | L2 | 11 | 121 | PSIPTPSGFDV | 23039 |
| HPV33 | L2 | 11 | 411 | PSPLFPTSSPF | 23040 |
| HPV33 | L2 | 8 | 166 | PSVLHPPA | 23041 |
| HPV33 | L2 | 10 | 166 | PSVLHPPAPA | 23042 |
| HPV33 | L2 | 10 | 79 | PTAAIPLQPI | 23043 |
| HPV33 | L2 | 8 | 161 | PTFTEPSV | 23044 |
| HPV33 | L2 | 9 | 161 | PTFTEPSVL | 23045 |
| HPV33 | L2 | 8 | 124 | PTPSGFDV | 23046 |
| HPV33 | L2 | 9 | 416 | PTSSPFVPI | 23047 |
| HPV33 | L2 | 8 | 186 | PTVSTQSY | 23048 |
| HPV33 | L2 | 11 | 186 | PTVSTQSYENI | 23049 |
| HPV33 | L2 | 8 | 191 | QSYENIPM | 23050 |
| HPV33 | L2 | 11 | 191 | QSYENIPMDTF | 23051 |
| HPV33 | L2 | 11 | 153 | QTISTHLNPTF | 23052 |
| HPV33 | L2 | 8 | 11 | RASATQLY | 23053 |
| HPV33 | L2 | 8 | 313 | RSGKQIGA | 23054 |
| HPV33 | L2 | 10 | 313 | RSGKQIGARI | 23055 |
| HPV33 | L2 | 8 | 5 | RSTRRKRA | 23056 |
| HPV33 | L2 | 10 | 5 | RSTRRKRASA | 23057 |
| HPV33 | L2 | 9 | 388 | RTSNVSIPL | 23058 |
| HPV33 | L2 | 8 | 134 | SADTTPAI | 23059 |
| HPV33 | L2 | 9 | 134 | SADTTPAII | 23060 |
| HPV33 | L2 | 11 | 134 | SADTTPAIINV | 23061 |
| HPV33 | L2 | 11 | 13 | SATQLYQTCKA | 23062 |
| HPV33 | L2 | 10 | 150 | SSIQTISTHL | 23063 |
| HPV33 | L2 | 10 | 207 | SSNVTSSTPI | 23064 |
| HPV33 | L2 | 10 | 418 | SSPFVPISPF | 23065 |
| HPV33 | L2 | 11 | 418 | SSPFVPISPFF | 23066 |
| HPV33 | L2 | 10 | 184 | SSPTVSTQSY | 23067 |
| HPV33 | L2 | 11 | 212 | SSTPIPGSRPV | 23068 |
| HPV33 | L2 | 8 | 145 | SSVGESSI | 23069 |
| HPV33 | L2 | 11 | 145 | SSVGESSIQTI | 23070 |
| HPV33 | L2 | 9 | 354 | SSYSINDGL | 23071 |
| HPV33 | L2 | 10 | 354 | SSYSINDGLY | 23072 |
| HPV33 | L2 | 11 | 382 | STFATTRTSNV | 23073 |
| HPV33 | L2 | 8 | 156 | STHLNPTF | 23074 |
| HPV33 | L2 | 8 | 38 | STIADQIL | 23075 |
| HPV33 | L2 | 10 | 38 | STIADQILKY | 23076 |
| HPV33 | L2 | 10 | 213 | STPIPGSRPV | 23077 |
| HPV33 | L2 | 11 | 213 | STPIPGSRPVA | 23078 |
| HPV33 | L2 | 8 | 189 | STQSYENI | 23079 |
| HPV33 | L2 | 10 | 189 | STQSYENIPM | 23080 |
| HPV33 | L2 | 9 | 6 | STRRKRASA | 23081 |
| HPV33 | L2 | 11 | 352 | STSSYSINDGL | 23082 |
| HPV33 | L2 | 9 | 80 | TAAIPLQPI | 23083 |
| HPV33 | L2 | 8 | 133 | TSADTTPA | 23084 |
| HPV33 | L2 | 9 | 133 | TSADTTPAI | 23085 |
| HPV33 | L2 | 10 | 133 | TSADTTPAII | 23086 |
| HPV33 | L2 | 8 | 111 | TSFIEAGA | 23087 |
| HPV33 | L2 | 10 | 111 | TSFIEAGAPA | 23088 |
| HPV33 | L2 | 8 | 389 | TSNVSIPL | 23089 |
| HPV33 | L2 | 9 | 244 | TSPHKLITY | 23090 |
| HPV33 | L2 | 9 | 293 | TSRRHTVRF | 23091 |
| HPV33 | L2 | 8 | 417 | TSSPFVPI | 23092 |
| HPV33 | L2 | 11 | 417 | TSSPFVPISPF | 23093 |
| HPV33 | L2 | 10 | 353 | TSSYSINDGL | 23094 |
| HPV33 | L2 | 11 | 353 | TSSYSINDGLY | 23095 |
| HPV33 | L2 | 8 | 351 | TSTSSYSI | 23096 |
| HPV33 | L2 | 8 | 137 | TTPAIINV | 23097 |
| HPV33 | L2 | 11 | 137 | TTPAIINVSSV | 23098 |
| HPV33 | L2 | 9 | 386 | TTRTSNVSI | 23099 |
| HPV33 | L2 | 11 | 386 | TTRTSNVSIPL | 23100 |
| HPV33 | L2 | 9 | 132 | TTSADTTPA | 23101 |
| HPV33 | L2 | 10 | 132 | TTSADTTPAI | 23102 |
| HPV33 | L2 | 11 | 132 | TTSADTTPAII | 23103 |

TABLE XIII-continued

B58 Supermotif Peptides

| Type | Protein | No. of Amino Acids | Position | Sequence | Seq. Id. No. |
|---|---|---|---|---|---|
| HPV33 | L2 | 9 | 392 | VSIPLNTGF | 23104 |
| HPV33 | L2 | 9 | 105 | VSLIEETSF | 23105 |
| HPV33 | L2 | 10 | 105 | VSLIEETSFI | 23106 |
| HPV33 | L2 | 9 | 144 | VSSVGESSI | 23107 |
| HPV33 | L2 | 8 | 203 | VSTDSSNV | 23108 |
| HPV33 | L2 | 9 | 188 | VSTQSYENI | 23109 |
| HPV33 | L2 | 11 | 188 | VSTQSYENIPM | 23110 |
| HPV33 | L2 | 10 | 131 | VTTSADTTPA | 23111 |
| HPV33 | L2 | 11 | 131 | VTTSADTTPAI | 23112 |
| HPV33 | L2 | 9 | 92 | VTVDTVGPL | 23113 |
| HPV33 | L2 | 8 | 366 | YADDVDNV | 23114 |
| HPV33 | L2 | 8 | 356 | YSINDGLY | 23115 |
| HPV33 | L2 | 10 | 356 | YSINDGLYDV | 23116 |
| HPV33 | L2 | 11 | 356 | YSINDGLYDVY | 23117 |
| HPV33 | L2 | 8 | 228 | YSRNTQQV | 23118 |
| HPV33 | L2 | 10 | 228 | YSRNTQQVKV | 23119 |
| HPV33 | L2 | 11 | 228 | YSRNTQQVKVV | 23120 |
| HPV45 | E1 | 11 | 382 | AAAFLKSNCQA | 23121 |
| HPV45 | E1 | 8 | 144 | AAETQVTV | 23122 |
| HPV45 | E1 | 10 | 383 | AAFLKSNCQA | 23123 |
| HPV45 | E1 | 10 | 310 | AALYWYRTGI | 23124 |
| HPV45 | E1 | 10 | 198 | AAMLAVFKDI | 23125 |
| HPV45 | E1 | 11 | 198 | AAMLAVFKDIY | 23126 |
| HPV45 | E1 | 8 | 193 | ASNKKAAM | 23127 |
| HPV45 | E1 | 9 | 193 | ASNKKAAML | 23128 |
| HPV45 | E1 | 10 | 193 | ASNKKAAMLA | 23129 |
| HPV45 | E1 | 11 | 193 | ASNKKAAMLAV | 23130 |
| HPV45 | E1 | 8 | 40 | ATDTGSDM | 23131 |
| HPV45 | E1 | 9 | 40 | ATDTGSDMV | 23132 |
| HPV45 | E1 | 11 | 40 | ATDTGSDMVDF | 23133 |
| HPV45 | E1 | 8 | 517 | ATHTCWTY | 23134 |
| HPV45 | E1 | 9 | 517 | ATHTCWTYF | 23135 |
| HPV45 | E1 | 10 | 251 | ATLYAHIQCL | 23136 |
| HPV45 | E1 | 8 | 398 | CAVMCRHY | 23137 |
| HPV45 | E1 | 11 | 398 | CAVMCRHYKRA | 23138 |
| HPV45 | E1 | 11 | 139 | CSEVEAAETQV | 23139 |
| HPV45 | E1 | 9 | 182 | CSITELKEL | 23140 |
| HPV45 | E1 | 10 | 182 | CSITELKELL | 23141 |
| HPV45 | E1 | 10 | 423 | CSKIDEGGDW | 23142 |
| HPV45 | E1 | 8 | 226 | CTDWVMAI | 23143 |
| HPV45 | E1 | 9 | 226 | CTDWVMAIF | 23144 |
| HPV45 | E1 | 11 | 226 | CTDWVMAIFGV | 23145 |
| HPV45 | E1 | 9 | 621 | DADTEGIPF | 23146 |
| HPV45 | E1 | 8 | 78 | DAQVLHLL | 23147 |
| HPV45 | E1 | 9 | 516 | DATHTCWTY | 23148 |
| HPV45 | E1 | 10 | 516 | DATHTCWTYF | 23149 |
| HPV45 | E1 | 9 | 134 | DSGYGCSEV | 23150 |
| HPV45 | E1 | 11 | 134 | DSGYGCSEVEA | 23151 |
| HPV45 | E1 | 9 | 345 | DSNFDLSDM | 23152 |
| HPV45 | E1 | 10 | 345 | DSNFDLSDMV | 23153 |
| HPV45 | E1 | 9 | 170 | DSSDNAENV | 23154 |
| HPV45 | E1 | 8 | 106 | DTDLSPRL | 23155 |
| HPV45 | E1 | 11 | 106 | DTDLSPRLQEI | 23156 |
| HPV45 | E1 | 10 | 623 | DTEGIPFGTF | 23157 |
| HPV45 | E1 | 9 | 42 | DTGSDMVDF | 23158 |
| HPV45 | E1 | 10 | 42 | DTGSDMVDFI | 23159 |
| HPV45 | E1 | 10 | 508 | DTKVAMLDDA | 23160 |
| HPV45 | E1 | 9 | 328 | DTPEWIQRL | 23161 |
| HPV45 | E1 | 11 | 328 | DTPEWIQRLTI | 23162 |
| HPV45 | E1 | 10 | 52 | DTQLSICEQA | 23163 |
| HPV45 | E1 | 9 | 143 | EAAETQVTV | 23164 |
| HPV45 | E1 | 8 | 365 | ESDMAFQY | 23165 |
| HPV45 | E1 | 9 | 365 | ESDMAFQYA | 23166 |
| HPV45 | E1 | 11 | 365 | ESDMAFQYAQL | 23167 |
| HPV45 | E1 | 9 | 573 | ESRVTVFTF | 23168 |
| HPV45 | E1 | 9 | 64 | ETAQALFHA | 23169 |
| HPV45 | E1 | 10 | 38 | ETATDTGSDM | 23170 |
| HPV45 | E1 | 11 | 38 | ETATDTGSDMV | 23171 |
| HPV45 | E1 | 11 | 295 | ETCMLIEPPKL | 23172 |
| HPV45 | E1 | 11 | 21 | ETIVEKKTGDV | 23173 |
| HPV45 | E1 | 10 | 146 | ETQVTVNTNA | 23174 |
| HPV45 | E1 | 11 | 89 | FAGGSKENSPL | 23175 |
| HPV45 | E1 | 8 | 212 | FTDLVRNF | 23176 |
| HPV45 | E1 | 9 | 579 | FTFPHAFPF | 23177 |
| HPV45 | E1 | 8 | 130 | FTISDSGY | 23178 |
| HPV45 | E1 | 8 | 44 | GSDMVDFI | 23179 |

TABLE XIII-continued

B58 Supermotif Peptides

| Type | Protein | No. of Amino Acids | Position | Sequence | Seq. Id. No. |
|---|---|---|---|---|---|
| HPV45 | E1 | 8 | 92 | GSKENSPL | 23180 |
| HPV45 | E1 | 8 | 11 | GTGCNGWF | 23181 |
| HPV45 | E1 | 9 | 11 | GTGCNGWFF | 23182 |
| HPV45 | E1 | 10 | 11 | GTGCNGWFFV | 23183 |
| HPV45 | E1 | 8 | 459 | GTPKKNCI | 23184 |
| HPV45 | E1 | 9 | 459 | GTPKKNCIL | 23185 |
| HPV45 | E1 | 10 | 459 | GTPKKNCILL | 23186 |
| HPV45 | E1 | 11 | 459 | GTPKKNCILLY | 23187 |
| HPV45 | E1 | 9 | 71 | HAQEVQNDA | 23188 |
| HPV45 | E1 | 11 | 71 | HAQEVQNDAQV | 23189 |
| HPV45 | E1 | 10 | 519 | HTCWTYFDNY | 23190 |
| HPV45 | E1 | 11 | 519 | HTCWTYFDNYM | 23191 |
| HPV45 | E1 | 9 | 32 | ISDDEDETA | 23192 |
| HPV45 | E1 | 11 | 132 | ISDSGYGCSEV | 23193 |
| HPV45 | E1 | 11 | 322 | ISEVSGDTPEW | 23194 |
| HPV45 | E1 | 10 | 447 | ISFLRALKEF | 23195 |
| HPV45 | E1 | 11 | 447 | ISFLRALKEFL | 23196 |
| HPV45 | E1 | 10 | 492 | ISFVNSNSHF | 23197 |
| HPV45 | E1 | 11 | 492 | ISFVNSNSHFW | 23198 |
| HPV45 | E1 | 10 | 538 | ISIDRKHKPL | 23199 |
| HPV45 | E1 | 11 | 538 | ISIDRKHKPLL | 23200 |
| HPV45 | E1 | 10 | 116 | ISLNSGHKKA | 23201 |
| HPV45 | E1 | 8 | 184 | ITELKELL | 23202 |
| HPV45 | E1 | 10 | 184 | ITELKELLQA | 23203 |
| HPV45 | E1 | 8 | 197 | KAAMLAVF | 23204 |
| HPV45 | E1 | 11 | 197 | KAAMLAVFKDI | 23205 |
| HPV45 | E1 | 9 | 124 | KAKRRLFTI | 23206 |
| HPV45 | E1 | 10 | 220 | KSDKTTCTDW | 23207 |
| HPV45 | E1 | 11 | 220 | KSDKTTCTDWV | 23208 |
| HPV45 | E1 | 8 | 387 | KSNCQAKY | 23209 |
| HPV45 | E1 | 9 | 387 | KSNCQAKYL | 23210 |
| HPV45 | E1 | 8 | 476 | KSYFGMSF | 23211 |
| HPV45 | E1 | 9 | 476 | KSYFGMSFI | 23212 |
| HPV45 | E1 | 11 | 476 | KSYFGMSFIHF | 23213 |
| HPV45 | E1 | 9 | 245 | KTLIKPATL | 23214 |
| HPV45 | E1 | 10 | 245 | KTLIKPATLY | 23215 |
| HPV45 | E1 | 11 | 245 | KTLIKPATLYA | 23216 |
| HPV45 | E1 | 8 | 223 | KTTCTDWV | 23217 |
| HPV45 | E1 | 9 | 223 | KTTCTDWVM | 23218 |
| HPV45 | E1 | 10 | 223 | KTTCTDWVMA | 23219 |
| HPV45 | E1 | 11 | 223 | KTTCTDWVMAI | 23220 |
| HPV45 | E1 | 8 | 375 | LADCNSNA | 23221 |
| HPV45 | E1 | 9 | 375 | LADCNSNAA | 23222 |
| HPV45 | E1 | 10 | 375 | LADCNSNAAA | 23223 |
| HPV45 | E1 | 11 | 375 | LADCNSNAAAF | 23224 |
| HPV45 | E1 | 8 | 506 | LADTKVAM | 23225 |
| HPV45 | E1 | 9 | 506 | LADTKVAML | 23226 |
| HPV45 | E1 | 8 | 201 | LAVFKDIY | 23227 |
| HPV45 | E1 | 10 | 201 | LAVFKDIYGL | 23228 |
| HPV45 | E1 | 8 | 350 | LSDMVQWA | 23229 |
| HPV45 | E1 | 9 | 350 | LSDMVQWAF | 23230 |
| HPV45 | E1 | 10 | 210 | LSFTDLVRNF | 23231 |
| HPV45 | E1 | 8 | 109 | LSPRLQEI | 23232 |
| HPV45 | E1 | 10 | 109 | LSPRLQEISL | 23233 |
| HPV45 | E1 | 11 | 103 | LSVDTDLSPRL | 23234 |
| HPV45 | E1 | 8 | 362 | LTDESDMA | 23235 |
| HPV45 | E1 | 9 | 362 | LTDESDMAF | 23236 |
| HPV45 | E1 | 11 | 362 | LTDESDMAFQY | 23237 |
| HPV45 | E1 | 8 | 336 | LTIIQHGI | 23238 |
| HPV45 | E1 | 8 | 557 | LTSNIDPA | 23239 |
| HPV45 | E1 | 10 | 281 | LTVAKGLSTL | 23240 |
| HPV45 | E1 | 11 | 281 | LTVAKGLSTLL | 23241 |
| HPV45 | E1 | 8 | 368 | MAFQYAQL | 23242 |
| HPV45 | E1 | 9 | 368 | MAFQYAQLA | 23243 |
| HPV45 | E1 | 10 | 231 | MAIFGVNPTV | 23244 |
| HPV45 | E1 | 11 | 231 | MAIFGVNPTVA | 23245 |
| HPV45 | E1 | 10 | 481 | MSFIHFLQGA | 23246 |
| HPV45 | E1 | 11 | 481 | MSFIHFLQGAI | 23247 |
| HPV45 | E1 | 8 | 154 | NAENGGSV | 23248 |
| HPV45 | E1 | 11 | 174 | NAENVDPHCSI | 23249 |
| HPV45 | E1 | 8 | 531 | NALDGNPI | 23250 |
| HPV45 | E1 | 10 | 531 | NALDGNPISI | 23251 |
| HPV45 | E1 | 11 | 119 | NSGHKKAKRRL | 23252 |
| HPV45 | E1 | 9 | 498 | NSHFWLEPL | 23253 |
| HPV45 | E1 | 10 | 498 | NSHFWLEPLA | 23254 |
| HPV45 | E1 | 8 | 376 | NSNAAAFL | 23255 |

TABLE XIII-continued

B58 Supermotif Peptides

| Type | Protein | No. of Amino Acids | Position | Sequence | Seq. Id. No. |
|---|---|---|---|---|---|
| HPV45 | E1 | 8 | 496 | NSNSHFWL | 23256 |
| HPV45 | E1 | 11 | 496 | NSNSHFWLEPL | 23257 |
| HPV45 | E1 | 8 | 96 | NSPLGEQL | 23258 |
| HPV45 | E1 | 10 | 96 | NSPLGEQLSV | 23259 |
| HPV45 | E1 | 9 | 473 | NTGKSYFGM | 23260 |
| HPV45 | E1 | 11 | 473 | NTGKSYFGMSF | 23261 |
| HPV45 | E1 | 10 | 152 | NTNAENGGSV | 23262 |
| HPV45 | E1 | 9 | 563 | PAKDNKWPY | 23263 |
| HPV45 | E1 | 10 | 563 | PAKDNKWPYL | 23264 |
| HPV45 | E1 | 8 | 471 | PANTGKSY | 23265 |
| HPV45 | E1 | 9 | 471 | PANTGKSYF | 23266 |
| HPV45 | E1 | 11 | 471 | PANTGKSYFGM | 23267 |
| HPV45 | E1 | 8 | 250 | PATLYAHI | 23268 |
| HPV45 | E1 | 11 | 250 | PATLYAHIQCL | 23269 |
| HPV45 | E1 | 10 | 238 | PTVAEGFKTL | 23270 |
| HPV45 | E1 | 11 | 238 | PTVAEGFKTLI | 23271 |
| HPV45 | E1 | 9 | 60 | QAEQETAQA | 23272 |
| HPV45 | E1 | 10 | 60 | QAEQETAQAL | 23273 |
| HPV45 | E1 | 11 | 60 | QAEQETAQALF | 23274 |
| HPV45 | E1 | 9 | 391 | QAKYLKDCA | 23275 |
| HPV45 | E1 | 10 | 391 | QAKYLKDCAV | 23276 |
| HPV45 | E1 | 11 | 391 | QAKYLKDCAVM | 23277 |
| HPV45 | E1 | 9 | 67 | QALFHAQEV | 23278 |
| HPV45 | E1 | 8 | 192 | QASNKKAA | 23279 |
| HPV45 | E1 | 9 | 192 | QASNKKAAM | 23280 |
| HPV45 | E1 | 10 | 192 | QASNKKAAML | 23281 |
| HPV45 | E1 | 11 | 192 | QASNKKAAMLA | 23282 |
| HPV45 | E1 | 11 | 165 | QSSGGDSSDNA | 23283 |
| HPV45 | E1 | 9 | 407 | RAQKRQMNM | 23284 |
| HPV45 | E1 | 8 | 306 | RSSVAALY | 23285 |
| HPV45 | E1 | 9 | 306 | RSSVAALYW | 23286 |
| HPV45 | E1 | 10 | 306 | RSSVAALYWY | 23287 |
| HPV45 | E1 | 10 | 316 | RTGISNISEV | 23288 |
| HPV45 | E1 | 8 | 608 | RTWSRLDL | 23289 |
| HPV45 | E1 | 8 | 171 | SSDNAENV | 23290 |
| HPV45 | E1 | 10 | 166 | SSGGDSSDNA | 23291 |
| HPV45 | E1 | 8 | 307 | SSVAALYW | 23292 |
| HPV45 | E1 | 9 | 307 | SSVAALYWY | 23293 |
| HPV45 | E1 | 11 | 288 | STLLHVPETCM | 23294 |
| HPV45 | E1 | 8 | 65 | TAQALFHA | 23295 |
| HPV45 | E1 | 11 | 65 | TAQALFHAQEV | 23296 |
| HPV45 | E1 | 9 | 39 | TATDTGSDM | 23297 |
| HPV45 | E1 | 10 | 39 | TATDTGSDMV | 23298 |
| HPV45 | E1 | 8 | 224 | TTCTDWVM | 23299 |
| HPV45 | E1 | 9 | 224 | TTCTDWVMA | 23300 |
| HPV45 | E1 | 10 | 224 | TTCTDWVMAI | 23301 |
| HPV45 | E1 | 11 | 224 | TTCTDWVMAIF | 23302 |
| HPV45 | E1 | 11 | 309 | VAALYWYRTGI | 23303 |
| HPV45 | E1 | 8 | 240 | VAEGFKTL | 23304 |
| HPV45 | E1 | 9 | 240 | VAEGFKTLI | 23305 |
| HPV45 | E1 | 8 | 283 | VAKGLSTL | 23306 |
| HPV45 | E1 | 9 | 283 | VAKGLSTLL | 23307 |
| HPV45 | E1 | 11 | 283 | VAKGLSTLLHV | 23308 |
| HPV45 | E1 | 8 | 325 | VSGDTPEW | 23309 |
| HPV45 | E1 | 9 | 325 | VSGDTPEWI | 23310 |
| HPV45 | E1 | 9 | 635 | VTGQNTRPL | 23311 |
| HPV45 | E1 | 9 | 576 | VTVFTFPHA | 23312 |
| HPV45 | E1 | 10 | 576 | VTVFTFPHAF | 23313 |
| HPV45 | E1 | 8 | 522 | WTYFDNYM | 23314 |
| HPV45 | E1 | 11 | 522 | WTYFDNYMRNA | 23315 |
| HPV45 | E1 | 11 | 254 | YAHIQCLDCKW | 23316 |
| HPV45 | E1 | 11 | 372 | YAQLADCNSNA | 23317 |
| HPV45 | E2 | 9 | 156 | AACVSYWGV | 23318 |
| HPV45 | E2 | 10 | 156 | AACVSYWGVY | 23319 |
| HPV45 | E2 | 11 | 156 | AACVSYWGVYY | 23320 |
| HPV45 | E2 | 9 | 226 | ASTSTPKTA | 23321 |
| HPV45 | E2 | 11 | 226 | ASTSTPKTASV | 23322 |
| HPV45 | E2 | 10 | 234 | ASVGTPKPHI | 23323 |
| HPV45 | E2 | 10 | 247 | ATKRPRQCGL | 23324 |
| HPV45 | E2 | 8 | 216 | ATQIVRQL | 23325 |
| HPV45 | E2 | 11 | 216 | ATQIVRQLQHA | 23326 |
| HPV45 | E2 | 8 | 286 | CSGNTTPI | 23327 |
| HPV45 | E2 | 9 | 286 | CSGNTTPII | 23328 |
| HPV45 | E2 | 11 | 286 | CSGNTTPIIHL | 23329 |
| HPV45 | E2 | 8 | 207 | CSTSDDTV | 23330 |
| HPV45 | E2 | 10 | 207 | CSTSDDTVSA | 23331 |

TABLE XIII-continued

B58 Supermotif Peptides

| Type | Protein | No. of Amino Acids | Position | Sequence | Seq. Id. No. |
|---|---|---|---|---|---|
| HPV45 | E2 | 11 | 141 | DSIYYITETGI | 23332 |
| HPV45 | E2 | 9 | 28 | DSKDINSQI | 23333 |
| HPV45 | E2 | 11 | 28 | DSKDINSQISY | 23334 |
| HPV45 | E2 | 11 | 204 | DSMCSTSDDTV | 23335 |
| HPV45 | E2 | 8 | 171 | DTTYYVQF | 23336 |
| HPV45 | E2 | 8 | 212 | DTVSATQI | 23337 |
| HPV45 | E2 | 9 | 212 | DTVSATQIV | 23338 |
| HPV45 | E2 | 9 | 8 | ESLSERLSA | 23339 |
| HPV45 | E2 | 10 | 8 | ESLSERLSAL | 23340 |
| HPV45 | E2 | 9 | 148 | ETGIWDKTA | 23341 |
| HPV45 | E2 | 10 | 148 | ETGIWDKTAA | 23342 |
| HPV45 | E2 | 8 | 50 | FTAREHGI | 23343 |
| HPV45 | E2 | 11 | 50 | FTAREHGITKL | 23344 |
| HPV45 | E2 | 11 | 237 | GTPKPHIQTPA | 23345 |
| HPV45 | E2 | 10 | 225 | HASTSTPKTA | 23346 |
| HPV45 | E2 | 9 | 70 | ISKSKAHKA | 23347 |
| HPV45 | E2 | 10 | 70 | ISKSKAHKAI | 23348 |
| HPV45 | E2 | 8 | 361 | ISVGYMTI | 23349 |
| HPV45 | E2 | 9 | 36 | ISYWQLIRL | 23350 |
| HPV45 | E2 | 11 | 146 | ITETGIWDKTA | 23351 |
| HPV45 | E2 | 8 | 57 | ITKLNHQV | 23352 |
| HPV45 | E2 | 9 | 57 | ITKLNHQVV | 23353 |
| HPV45 | E2 | 8 | 74 | KAHKAIEL | 23354 |
| HPV45 | E2 | 10 | 74 | KAHKAIELQM | 23355 |
| HPV45 | E2 | 11 | 74 | KAHKAIELQMA | 23356 |
| HPV45 | E2 | 8 | 77 | KAIELQMA | 23357 |
| HPV45 | E2 | 9 | 77 | KAIELQMAL | 23358 |
| HPV45 | E2 | 8 | 72 | KSKAHKAI | 23359 |
| HPV45 | E2 | 10 | 72 | KSKAHKAIEL | 23360 |
| HPV45 | E2 | 8 | 154 | KTAACVSY | 23361 |
| HPV45 | E2 | 9 | 154 | KTAACVSYW | 23362 |
| HPV45 | E2 | 11 | 154 | KTAACVSYWGV | 23363 |
| HPV45 | E2 | 11 | 88 | LAQSKYNNEEW | 23364 |
| HPV45 | E2 | 8 | 14 | LSALQDKI | 23365 |
| HPV45 | E2 | 9 | 14 | LSALQDKIL | 23366 |
| HPV45 | E2 | 8 | 10 | LSERLSAL | 23367 |
| HPV45 | E2 | 9 | 256 | LTEQHHGRV | 23368 |
| HPV45 | E2 | 9 | 336 | LTVTYNSEV | 23369 |
| HPV45 | E2 | 11 | 83 | MALKGLAQSKY | 23370 |
| HPV45 | E2 | 9 | 341 | NSEVQRNTF | 23371 |
| HPV45 | E2 | 10 | 341 | NSEVQRNTFL | 23372 |
| HPV45 | E2 | 8 | 301 | NSLKCLRY | 23373 |
| HPV45 | E2 | 10 | 301 | NSLKCLRYRL | 23374 |
| HPV45 | E2 | 9 | 187 | NSNTWEVQY | 23375 |
| HPV45 | E2 | 9 | 33 | NSQISYWQL | 23376 |
| HPV45 | E2 | 10 | 33 | NSQISYWQLI | 23377 |
| HPV45 | E2 | 9 | 357 | NSVQISVGY | 23378 |
| HPV45 | E2 | 10 | 357 | NSVQISVGYM | 23379 |
| HPV45 | E2 | 8 | 109 | NTEPSQCF | 23380 |
| HPV45 | E2 | 9 | 347 | NTFLDVVTI | 23381 |
| HPV45 | E2 | 9 | 332 | NTGILTVTY | 23382 |
| HPV45 | E2 | 8 | 265 | NTHVHNPL | 23383 |
| HPV45 | E2 | 9 | 265 | NTHVHNPLL | 23384 |
| HPV45 | E2 | 8 | 289 | NTTPIIHL | 23385 |
| HPV45 | E2 | 11 | 189 | NTWEVQYGGNV | 23386 |
| HPV45 | E2 | 11 | 246 | PATKRPRQCGL | 23387 |
| HPV45 | E2 | 9 | 90 | QSKYNNEEW | 23388 |
| HPV45 | E2 | 11 | 90 | QSKYNNEEWTL | 23389 |
| HPV45 | E2 | 11 | 4 | QTPKESLSERL | 23390 |
| HPV45 | E2 | 8 | 15 | SALQDKIL | 23391 |
| HPV45 | E2 | 11 | 15 | SALQDKILDHY | 23392 |
| HPV45 | E2 | 9 | 215 | SATQIVRQL | 23393 |
| HPV45 | E2 | 11 | 275 | SSTSNNKRRKV | 23394 |
| HPV45 | E2 | 8 | 229 | STPKTASV | 23395 |
| HPV45 | E2 | 9 | 208 | STSDDTVSA | 23396 |
| HPV45 | E2 | 10 | 276 | STSNNKRRKV | 23397 |
| HPV45 | E2 | 8 | 227 | STSTPKTA | 23398 |
| HPV45 | E2 | 10 | 227 | STSTPKTASV | 23399 |
| HPV45 | E2 | 8 | 155 | TAACVSYW | 23400 |
| HPV45 | E2 | 10 | 155 | TAACVSYWGV | 23401 |
| HPV45 | E2 | 11 | 155 | TAACVSYWGVY | 23402 |
| HPV45 | E2 | 10 | 51 | TAREHGITKL | 23403 |
| HPV45 | E2 | 11 | 233 | TASVGTPKPHI | 23404 |
| HPV45 | E2 | 8 | 209 | TSDDTVSA | 23405 |
| HPV45 | E2 | 11 | 209 | TSDDTVSATQI | 23406 |
| HPV45 | E2 | 9 | 277 | TSNNKRRKV | 23407 |

TABLE XIII-continued

B58 Supermotif Peptides

| Type | Protein | No. of Amino Acids | Position | Sequence | Seq. Id. No. |
|---|---|---|---|---|---|
| HPV45 | E2 | 9 | 228 | TSTPKTASV | 23408 |
| HPV45 | E2 | 10 | 214 | VSATQIVRQL | 23409 |
| HPV45 | E2 | 8 | 159 | VSYWGVYY | 23410 |
| HPV45 | E2 | 9 | 159 | VSYWGVYYI | 23411 |
| HPV45 | E2 | 9 | 353 | VTIPNSVQI | 23412 |
| HPV45 | E2 | 11 | 353 | VTIPNSVQISV | 23413 |
| HPV45 | E2 | 10 | 326 | WTGCNKNTGI | 23414 |
| HPV45 | E2 | 11 | 326 | WTGCNKNTGIL | 23415 |
| HPV45 | E2 | 10 | 98 | WTLQDTCEEL | 23416 |
| HPV45 | E2 | 11 | 98 | WTLQDTCEELW | 23417 |
| HPV45 | E2 | 8 | 313 | YADHYSEI | 23418 |
| HPV45 | E2 | 8 | 317 | YSEISSTW | 23419 |
| HPV45 | E2 | 10 | 317 | YSEISSTWHW | 23420 |
| HPV45 | E6 | 9 | 63 | AACHKCIDF | 23421 |
| HPV45 | E6 | 10 | 63 | AACHKCIDFY | 23422 |
| HPV45 | E6 | 8 | 37 | ATLERTEV | 23423 |
| HPV45 | E6 | 9 | 37 | ATLERTEVY | 23424 |
| HPV45 | E6 | 11 | 37 | ATLERTEVYQF | 23425 |
| HPV45 | E6 | 8 | 18 | CTELNTSL | 23426 |
| HPV45 | E6 | 11 | 18 | CTELNTSLQDV | 23427 |
| HPV45 | E6 | 11 | 88 | ETLEKITNTEL | 23428 |
| HPV45 | E6 | 8 | 47 | FAFKDLFI | 23429 |
| HPV45 | E6 | 9 | 47 | FAFKDLFIV | 23430 |
| HPV45 | E6 | 10 | 47 | FAFKDLFIVY | 23431 |
| HPV45 | E6 | 8 | 30 | IACVYCKA | 23432 |
| HPV45 | E6 | 10 | 30 | IACVYCKATL | 23433 |
| HPV45 | E6 | 10 | 60 | IAYAACHKCI | 23434 |
| HPV45 | E6 | 9 | 93 | ITNTELYNL | 23435 |
| HPV45 | E6 | 10 | 93 | ITNTELYNLL | 23436 |
| HPV45 | E6 | 11 | 93 | ITNTELYNLLI | 23437 |
| HPV45 | E6 | 9 | 36 | KATLERTEV | 23438 |
| HPV45 | E6 | 10 | 36 | KATLERTEVY | 23439 |
| HPV45 | E6 | 8 | 83 | NSVYGETL | 23440 |
| HPV45 | E6 | 11 | 83 | NSVYGETLEKI | 23441 |
| HPV45 | E6 | 8 | 95 | NTELYNLL | 23442 |
| HPV45 | E6 | 9 | 95 | NTELYNLLI | 23443 |
| HPV45 | E6 | 9 | 22 | NTSLQDVSI | 23444 |
| HPV45 | E6 | 10 | 22 | NTSLQDVSIA | 23445 |
| HPV45 | E6 | 8 | 114 | PAEKRRHL | 23446 |
| HPV45 | E6 | 8 | 7 | PTQRPYKL | 23447 |
| HPV45 | E6 | 11 | 7 | PTQRPYKLPDL | 23448 |
| HPV45 | E6 | 8 | 41 | RTEVYQFA | 23449 |
| HPV45 | E6 | 9 | 41 | RTEVYQFAF | 23450 |
| HPV45 | E6 | 8 | 23 | TSLQDVSI | 23451 |
| HPV45 | E6 | 9 | 23 | TSLQDVSIA | 23452 |
| HPV45 | E6 | 11 | 23 | TSLQDVSIACV | 23453 |
| HPV45 | E6 | 10 | 28 | VSIACVYCKA | 23454 |
| HPV45 | E6 | 8 | 62 | YAACHKCI | 23455 |
| HPV45 | E6 | 10 | 62 | YAACHKCIDF | 23456 |
| HPV45 | E6 | 11 | 62 | YAACHKCIDFY | 23457 |
| HPV45 | E6 | 10 | 81 | YSNSVYGETL | 23458 |
| HPV45 | E6 | 9 | 72 | YSRIRELRY | 23459 |
| HPV45 | E6 | 10 | 72 | YSRIRELRYY | 23460 |
| HPV45 | E7 | 8 | 6 | ATLQEIVL | 23461 |
| HPV45 | E7 | 10 | 6 | ATLQEIVLHL | 23462 |
| HPV45 | E7 | 8 | 41 | EADGVSHA | 23463 |
| HPV45 | E7 | 10 | 41 | EADGVSHAQL | 23464 |
| HPV45 | E7 | 9 | 34 | ESEEENDEA | 23465 |
| HPV45 | E7 | 10 | 78 | ESSADDLRTL | 23466 |
| HPV45 | E7 | 9 | 47 | HAQLPARRA | 23467 |
| HPV45 | E7 | 11 | 32 | LSESEEENDEA | 23468 |
| HPV45 | E7 | 9 | 95 | LSFVCPWCA | 23469 |
| HPV45 | E7 | 10 | 92 | LSTLSFVCPW | 23470 |
| HPV45 | E7 | 10 | 75 | LTVESSADDL | 23471 |
| HPV45 | E7 | 9 | 54 | RAEPQRHKI | 23472 |
| HPV45 | E7 | 10 | 54 | RAEPQRHKIL | 23473 |
| HPV45 | E7 | 8 | 5 | RATLQEIV | 23474 |
| HPV45 | E7 | 9 | 5 | RATLQEIVL | 23475 |
| HPV45 | E7 | 11 | 5 | RATLQEIVLHL | 23476 |
| HPV45 | E7 | 8 | 85 | RTLQQLFL | 23477 |
| HPV45 | E7 | 11 | 85 | RTLQQLFLSTL | 23478 |
| HPV45 | E7 | 8 | 80 | SADDLRTL | 23479 |
| HPV45 | E7 | 11 | 80 | SADDLRTLQQL | 23480 |
| HPV45 | E7 | 9 | 79 | SSADDLRTL | 23481 |
| HPV45 | E7 | 9 | 93 | STLSFVCPW | 23482 |
| HPV45 | E7 | 11 | 93 | STLSFVCPWCA | 23483 |

TABLE XIII-continued

B58 Supermotif Peptides

| Type | Protein | No. of Amino Acids | Position | Sequence | Seq. Id. No. |
|---|---|---|---|---|---|
| HPV45 | E7 | 8 | 45 | VSHAQLPA | 23484 |
| HPV45 | E7 | 11 | 45 | VSHAQLPARRA | 23485 |
| HPV45 | L1 | 11 | 517 | AASTSTASRPA | 23486 |
| HPV45 | L1 | 10 | 161 | AATAVITQDV | 23487 |
| HPV45 | L1 | 8 | 523 | ASRPAKRV | 23488 |
| HPV45 | L1 | 10 | 523 | ASRPAKRVRI | 23489 |
| HPV45 | L1 | 11 | 375 | ASTQNPVPNTY | 23490 |
| HPV45 | L1 | 10 | 518 | ASTSTASRPA | 23491 |
| HPV45 | L1 | 9 | 162 | ATAVITQDV | 23492 |
| HPV45 | L1 | 8 | 374 | CASTQNPV | 23493 |
| HPV45 | L1 | 9 | 409 | CTITLTAEV | 23494 |
| HPV45 | L1 | 10 | 409 | CTITLTAEVM | 23495 |
| HPV45 | L1 | 9 | 332 | DSQLFNKPY | 23496 |
| HPV45 | L1 | 10 | 332 | DSQLFNKPYW | 23497 |
| HPV45 | L1 | 11 | 332 | DSQLFNKPYWL | 23498 |
| HPV45 | L1 | 11 | 34 | DSTVYLPPPSV | 23499 |
| HPV45 | L1 | 8 | 155 | DTESAHAA | 23500 |
| HPV45 | L1 | 10 | 155 | DTESAHAATA | 23501 |
| HPV45 | L1 | 11 | 155 | DTESAHAATAV | 23502 |
| HPV45 | L1 | 9 | 229 | DTGYGAMDF | 23503 |
| HPV45 | L1 | 8 | 242 | DTKCEVPL | 23504 |
| HPV45 | L1 | 10 | 242 | DTKCEVPLDI | 23505 |
| HPV45 | L1 | 11 | 461 | DTTPPEKQDPY | 23506 |
| HPV45 | L1 | 8 | 364 | DTTRSTNL | 23507 |
| HPV45 | L1 | 10 | 364 | DTTRSTNLTL | 23508 |
| HPV45 | L1 | 8 | 296 | DTVPTDLY | 23509 |
| HPV45 | L1 | 9 | 296 | DTVPTDLYI | 23510 |
| HPV45 | L1 | 9 | 446 | DTYRFVQSV | 23511 |
| HPV45 | L1 | 10 | 446 | DTYRFVQSVA | 23512 |
| HPV45 | L1 | 11 | 446 | DTYRFVQSVAV | 23513 |
| HPV45 | L1 | 8 | 157 | ESAHAATA | 23514 |
| HPV45 | L1 | 9 | 157 | ESAHAATAV | 23515 |
| HPV45 | L1 | 10 | 157 | ESAHAATAVI | 23516 |
| HPV45 | L1 | 8 | 313 | ETPGSCVY | 23517 |
| HPV45 | L1 | 8 | 121 | ETQRLVWA | 23518 |
| HPV45 | L1 | 10 | 121 | ETQRLVWACV | 23519 |
| HPV45 | L1 | 9 | 283 | FARHFWNRA | 23520 |
| HPV45 | L1 | 11 | 283 | FARHFWNRAGV | 23521 |
| HPV45 | L1 | 8 | 485 | FSSDLDQY | 23522 |
| HPV45 | L1 | 10 | 485 | FSSDLDQYPL | 23523 |
| HPV45 | L1 | 11 | 237 | FSTLQDTKCEV | 23524 |
| HPV45 | L1 | 8 | 82 | GAGNKQAV | 23525 |
| HPV45 | L1 | 11 | 82 | GAGNKQAVPKV | 23526 |
| HPV45 | L1 | 8 | 233 | GAMDFSTL | 23527 |
| HPV45 | L1 | 10 | 326 | GSITTSDSQL | 23528 |
| HPV45 | L1 | 11 | 326 | GSITTSDSQLF | 23529 |
| HPV45 | L1 | 8 | 64 | GSSRLLTV | 23530 |
| HPV45 | L1 | 9 | 199 | GTLCKPAQL | 23531 |
| HPV45 | L1 | 11 | 160 | HAATAVITQDV | 23532 |
| HPV45 | L1 | 8 | 62 | HAGSSRLL | 23533 |
| HPV45 | L1 | 10 | 62 | HAGSSRLLTV | 23534 |
| HPV45 | L1 | 8 | 422 | HSMNSSIL | 23535 |
| HPV45 | L1 | 11 | 422 | HSMNSSILENW | 23536 |
| HPV45 | L1 | 8 | 411 | ITLTAEVM | 23537 |
| HPV45 | L1 | 10 | 411 | ITLTAEVMSY | 23538 |
| HPV45 | L1 | 11 | 411 | ITLTAEVMSYI | 23539 |
| HPV45 | L1 | 9 | 166 | ITQDVRDNV | 23540 |
| HPV45 | L1 | 11 | 166 | ITQDVRDNVSV | 23541 |
| HPV45 | L1 | 8 | 328 | ITTSDSQL | 23542 |
| HPV45 | L1 | 9 | 328 | ITTSDSQLF | 23543 |
| HPV45 | L1 | 9 | 344 | KAQGHNNGI | 23544 |
| HPV45 | L1 | 11 | 344 | KAQGHNNGICW | 23545 |
| HPV45 | L1 | 10 | 144 | LSGHPFYNKL | 23546 |
| HPV45 | L1 | 8 | 413 | LTAEVMSY | 23547 |
| HPV45 | L1 | 9 | 413 | LTAEVMSYI | 23548 |
| HPV45 | L1 | 11 | 371 | LTLCASTQNPV | 23549 |
| HPV45 | L1 | 8 | 69 | LTVGNPYF | 23550 |
| HPV45 | L1 | 10 | 69 | LTVGNPYFRV | 23551 |
| HPV45 | L1 | 11 | 69 | LTVGNPYFRVV | 23552 |
| HPV45 | L1 | 11 | 1 | MAHNIIYGHGI | 23553 |
| HPV45 | L1 | 11 | 27 | MALWRPSDSTV | 23554 |
| HPV45 | L1 | 10 | 264 | MSADPYGDSM | 23555 |
| HPV45 | L1 | 11 | 264 | MSADPYGDSMF | 23556 |
| HPV45 | L1 | 11 | 418 | MSYIHSMNSSI | 23557 |
| HPV45 | L1 | 8 | 425 | NSSILENW | 23558 |
| HPV45 | L1 | 10 | 425 | NSSILENWNF | 23559 |

TABLE XIII-continued

B58 Supermotif Peptides

| Type | Protein | No. of Amino Acids | Position | Sequence | Seq. Id. No. |
|---|---|---|---|---|---|
| HPV45 | L1 | 11 | 49 | NTDDYVSRTSI | 23560 |
| HPV45 | L1 | 9 | 219 | NTIIEDGDM | 23561 |
| HPV45 | L1 | 10 | 219 | NTIIEDGDMV | 23562 |
| HPV45 | L1 | 8 | 383 | NTYDPTKF | 23563 |
| HPV45 | L1 | 11 | 383 | NTYDPTKFHY | 23564 |
| HPV45 | L1 | 8 | 516 | PAASTSTA | 23565 |
| HPV45 | L1 | 8 | 190 | PAIGEHWA | 23566 |
| HPV45 | L1 | 8 | 32 | PSDSTVYL | 23567 |
| HPV45 | L1 | 9 | 80 | PSGAGNKQA | 23568 |
| HPV45 | L1 | 10 | 80 | PSGAGNKQAV | 23569 |
| HPV45 | L1 | 11 | 299 | PTDLYIKGTSA | 23570 |
| HPV45 | L1 | 10 | 508 | PTIGPRKRPA | 23571 |
| HPV45 | L1 | 11 | 508 | PTIGPRKRPAA | 23572 |
| HPV45 | L1 | 11 | 387 | PTKFKHYSRHV | 23573 |
| HPV45 | L1 | 9 | 440 | PTTSLVDTY | 23574 |
| HPV45 | L1 | 11 | 440 | PTTSLVDTYRF | 23575 |
| HPV45 | L1 | 10 | 501 | QAGLRRRPTI | 23576 |
| HPV45 | L1 | 8 | 87 | QAVPKVSA | 23577 |
| HPV45 | L1 | 9 | 87 | QAVPKVSAY | 23578 |
| HPV45 | L1 | 11 | 87 | QAVPKVSAYQY | 23579 |
| HPV45 | L1 | 9 | 253 | QSICKYPDY | 23580 |
| HPV45 | L1 | 10 | 253 | QSICKYPDYL | 23581 |
| HPV45 | L1 | 10 | 180 | QTQLCILGCV | 23582 |
| HPV45 | L1 | 9 | 290 | RAGVMGDTV | 23583 |
| HPV45 | L1 | 9 | 367 | RSTNLTLCA | 23584 |
| HPV45 | L1 | 8 | 56 | RTSIFYHA | 23585 |
| HPV45 | L1 | 9 | 265 | SADPYGDSM | 23586 |
| HPV45 | L1 | 10 | 265 | SADPYGDSMF | 23587 |
| HPV45 | L1 | 11 | 265 | SADPYGDSMFF | 23588 |
| HPV45 | L1 | 8 | 158 | SAHAATAV | 23589 |
| HPV45 | L1 | 9 | 158 | SAHAATAVI | 23590 |
| HPV45 | L1 | 8 | 93 | SAYQYRVF | 23591 |
| HPV45 | L1 | 10 | 93 | SAYQYRVFRV | 23592 |
| HPV45 | L1 | 11 | 93 | SAYQYRVFRVA | 23593 |
| HPV45 | L1 | 9 | 486 | SSDLDQYPL | 23594 |
| HPV45 | L1 | 9 | 426 | SSILENWNF | 23595 |
| HPV45 | L1 | 11 | 426 | SSILENWNFGV | 23596 |
| HPV45 | L1 | 11 | 65 | SSRLLTVGNPY | 23597 |
| HPV45 | L1 | 10 | 521 | STASRPAKRV | 23598 |
| HPV45 | L1 | 11 | 115 | STIYNPETQRL | 23599 |
| HPV45 | L1 | 10 | 238 | STLQDTKCEV | 23600 |
| HPV45 | L1 | 8 | 368 | STNLTLCA | 23601 |
| HPV45 | L1 | 10 | 376 | STQNPVPNTY | 23602 |
| HPV45 | L1 | 9 | 519 | STSTASRPA | 23603 |
| HPV45 | L1 | 10 | 35 | STVYLPPPSV | 23604 |
| HPV45 | L1 | 11 | 35 | STVYLPPPSVA | 23605 |
| HPV45 | L1 | 8 | 414 | TAEVMSYI | 23606 |
| HPV45 | L1 | 11 | 414 | TAEVMSYIHSM | 23607 |
| HPV45 | L1 | 9 | 522 | TASRPAKRV | 23608 |
| HPV45 | L1 | 11 | 522 | TASRPAKRVRI | 23609 |
| HPV45 | L1 | 8 | 163 | TAVITQDV | 23610 |
| HPV45 | L1 | 11 | 330 | ISDSQLFNKPY | 23611 |
| HPV45 | L1 | 9 | 442 | TSLVDTYRF | 23612 |
| HPV45 | L1 | 10 | 442 | TSLVDTYRFV | 23613 |
| HPV45 | L1 | 8 | 520 | TSTASRPA | 23614 |
| HPV45 | L1 | 11 | 520 | TSTASRPAKRV | 23615 |
| HPV45 | L1 | 10 | 462 | TTPPEKQDPY | 23616 |
| HPV45 | L1 | 9 | 365 | TTRSTNLTL | 23617 |
| HPV45 | L1 | 11 | 365 | TTRSTNLTLCA | 23618 |
| HPV45 | L1 | 8 | 329 | TTSDSQLF | 23619 |
| HPV45 | L1 | 8 | 441 | TTSLVDTY | 23620 |
| HPV45 | L1 | 10 | 441 | TTSLVDTYRF | 23621 |
| HPV45 | L1 | 11 | 441 | TTSLVDTYRFV | 23622 |
| HPV45 | L1 | 9 | 102 | VALPDPNKF | 23623 |
| HPV45 | L1 | 11 | 102 | VALPDPNKFGL | 23624 |
| HPV45 | L1 | 10 | 44 | VARVVNTDDY | 23625 |
| HPV45 | L1 | 11 | 44 | VARVVNTDDYV | 23626 |
| HPV45 | L1 | 8 | 92 | VSAYQYRV | 23627 |
| HPV45 | L1 | 9 | 92 | VSAYQYRVF | 23628 |
| HPV45 | L1 | 11 | 92 | VSAYQYRVFRV | 23629 |
| HPV45 | L1 | 8 | 54 | VSRTSIFY | 23630 |
| HPV45 | L1 | 10 | 54 | VSRTSIFYHA | 23631 |
| HPV45 | L1 | 10 | 174 | VSVDYKQTQL | 23632 |
| HPV45 | L1 | 8 | 127 | WACVGMEI | 23633 |
| HPV45 | L1 | 10 | 196 | WAKGTLCKPA | 23634 |
| HPV45 | L1 | 9 | 477 | WTVDLKEKF | 23635 |

TABLE XIII-continued

B58 Supermotif Peptides

| Type | Protein | No. of Amino Acids | Position | Sequence | Seq. Id. No. |
|---|---|---|---|---|---|
| HPV45 | L1 | 9 | 320 | YSPSPSGSI | 23636 |
| HPV45 | L1 | 8 | 393 | YSRHVEEY | 23637 |
| HPV45 | L1 | 10 | 393 | YSRHVEEYDL | 23638 |
| HPV45 | L2 | 9 | 6 | AARRKRASA | 23639 |
| HPV45 | L2 | 8 | 381 | AASSYSNV | 23640 |
| HPV45 | L2 | 10 | 381 | AASSYSNVTV | 23641 |
| HPV45 | L2 | 8 | 327 | AATEEIEL | 23642 |
| HPV45 | L2 | 11 | 327 | AATEEIELQPL | 23643 |
| HPV45 | L2 | 9 | 114 | ASGAPVPTF | 23644 |
| HPV45 | L2 | 10 | 201 | ASSGSGTEPI | 23645 |
| HPV45 | L2 | 9 | 382 | ASSYSNVTV | 23646 |
| HPV45 | L2 | 11 | 382 | ASSYSNVTVPL | 23647 |
| HPV45 | L2 | 8 | 357 | ASTTPSTI | 23648 |
| HPV45 | L2 | 9 | 423 | ASTTTYIGI | 23649 |
| HPV45 | L2 | 10 | 328 | ATEEIELQPL | 23650 |
| HPV45 | L2 | 11 | 328 | ATEEIELQPLI | 23651 |
| HPV45 | L2 | 11 | 303 | ATMFTRSGKQI | 23652 |
| HPV45 | L2 | 8 | 340 | ATNDSDLF | 23653 |
| HPV45 | L2 | 10 | 340 | ATNDSDLFDV | 23654 |
| HPV45 | L2 | 11 | 340 | ATNDSDLFDVY | 23655 |
| HPV45 | L2 | 8 | 273 | DSDFMDII | 23656 |
| HPV45 | L2 | 10 | 273 | DSDFMDIIRL | 23657 |
| HPV45 | L2 | 8 | 343 | DSDLFDVY | 23658 |
| HPV45 | L2 | 9 | 343 | DSDLFDVYA | 23659 |
| HPV45 | L2 | 11 | 343 | DSDLFDVYADF | 23660 |
| HPV45 | L2 | 9 | 109 | DSSVVASGA | 23661 |
| HPV45 | L2 | 11 | 109 | DSSVVASGAPV | 23662 |
| HPV45 | L2 | 10 | 148 | DSVSISSTSF | 23663 |
| HPV45 | L2 | 8 | 456 | FADGFVAA | 23664 |
| HPV45 | L2 | 11 | 200 | FASSGSGTEPI | 23665 |
| HPV45 | L2 | 9 | 162 | FSDPSIIEV | 23666 |
| HPV45 | L2 | 8 | 296 | FSRLGQRA | 23667 |
| HPV45 | L2 | 10 | 296 | FSRLGQRATM | 23668 |
| HPV45 | L2 | 11 | 296 | FSRLGQRATMF | 23669 |
| HPV45 | L2 | 9 | 122 | FTGTSGFEI | 23670 |
| HPV45 | L2 | 11 | 157 | FTNPAFSDPSI | 23671 |
| HPV45 | L2 | 8 | 306 | FTRSGKQI | 23672 |
| HPV45 | L2 | 8 | 368 | FTYPKYSL | 23673 |
| HPV45 | L2 | 10 | 368 | FTYPKYSLTM | 23674 |
| HPV45 | L2 | 8 | 64 | GSGGRTGY | 23675 |
| HPV45 | L2 | 9 | 64 | GSGGRTGYV | 23676 |
| HPV45 | L2 | 11 | 64 | GSGGRTGYVPL | 23677 |
| HPV45 | L2 | 10 | 62 | GSGSGGRTGY | 23678 |
| HPV45 | L2 | 11 | 62 | GSGSGGRTGYV | 23679 |
| HPV45 | L2 | 8 | 188 | GSHGYEEI | 23680 |
| HPV45 | L2 | 10 | 188 | GSHGYEEIPL | 23681 |
| HPV45 | L2 | 8 | 25 | GTCPPDVI | 23682 |
| HPV45 | L2 | 11 | 25 | GTCPPDVINKV | 23683 |
| HPV45 | L2 | 10 | 206 | GTEPISSTPL | 23684 |
| HPV45 | L2 | 10 | 183 | GTPTSGSHGY | 23685 |
| HPV45 | L2 | 9 | 433 | GTQYYLWPW | 23686 |
| HPV45 | L2 | 10 | 433 | GTQYYLWPWY | 23687 |
| HPV45 | L2 | 11 | 433 | GTQYYLWPWYY | 23688 |
| HPV45 | L2 | 8 | 37 | GTTLADKI | 23689 |
| HPV45 | L2 | 9 | 37 | GTTLADKIL | 23690 |
| HPV45 | L2 | 11 | 37 | GTTLADKILQW | 23691 |
| HPV45 | L2 | 8 | 134 | GTTTPAVL | 23692 |
| HPV45 | L2 | 10 | 134 | GTTTPAVLDI | 23693 |
| HPV45 | L2 | 8 | 292 | GTVRFSRL | 23694 |
| HPV45 | L2 | 9 | 326 | IAATEEIEL | 23695 |
| HPV45 | L2 | 9 | 338 | ISATNDSDL | 23696 |
| HPV45 | L2 | 10 | 338 | ISATNDSDLF | 23697 |
| HPV45 | L2 | 10 | 323 | ISPIAATEEI | 23698 |
| HPV45 | L2 | 9 | 210 | ISSTPLPTV | 23699 |
| HPV45 | L2 | 10 | 152 | ISSTSFTNPA | 23700 |
| HPV45 | L2 | 11 | 152 | ISSTSFTNPAF | 23701 |
| HPV45 | L2 | 8 | 143 | ITPTVDSV | 23702 |
| HPV45 | L2 | 10 | 143 | ITPTVDSVSI | 23703 |
| HPV45 | L2 | 10 | 130 | ITSSGTTTPA | 23704 |
| HPV45 | L2 | 11 | 130 | ITSSGTTTPAV | 23705 |
| HPV45 | L2 | 8 | 366 | KSFTYPKY | 23706 |
| HPV45 | L2 | 10 | 366 | KSFTYPKYSL | 23707 |
| HPV45 | L2 | 8 | 40 | LADKILQW | 23708 |
| HPV45 | L2 | 11 | 40 | LADKILQWSSL | 23709 |
| HPV45 | L2 | 9 | 263 | LSFEPTSNV | 23710 |
| HPV45 | L2 | 8 | 287 | LSSRRGTV | 23711 |

TABLE XIII-continued

B58 Supermotif Peptides

| Type | Protein | No. of Amino Acids | Position | Sequence | Seq. Id. No. |
|---|---|---|---|---|---|
| HPV45 | L2 | 10 | 287 | LSSRRGTVRF | 23712 |
| HPV45 | L2 | 8 | 242 | LTHPSSLV | 23713 |
| HPV45 | L2 | 10 | 242 | LTHPSSLVTF | 23714 |
| HPV45 | L2 | 8 | 375 | LTMPSTAA | 23715 |
| HPV45 | L2 | 11 | 375 | LTMPSTAASSY | 23716 |
| HPV45 | L2 | 9 | 392 | LTSAWDVPI | 23717 |
| HPV45 | L2 | 10 | 392 | LTSAWDVPIY | 23718 |
| HPV45 | L2 | 8 | 422 | NASTTTYI | 23719 |
| HPV45 | L2 | 10 | 422 | NASTTTYIGI | 23720 |
| HPV45 | L2 | 8 | 160 | PAFSDPSI | 23721 |
| HPV45 | L2 | 9 | 160 | PAFSDPSII | 23722 |
| HPV45 | L2 | 11 | 160 | PAFSDPSIIEV | 23723 |
| HPV45 | L2 | 10 | 285 | PALSSRRGTV | 23724 |
| HPV45 | L2 | 9 | 356 | PASTTPSTI | 23725 |
| HPV45 | L2 | 10 | 138 | PAVLDITPTV | 23726 |
| HPV45 | L2 | 10 | 254 | PAYEPLDTTL | 23727 |
| HPV45 | L2 | 11 | 245 | PSSLVTFDNPA | 23728 |
| HPV45 | L2 | 8 | 378 | PSTAASSY | 23729 |
| HPV45 | L2 | 11 | 378 | PSTAASSYSNV | 23730 |
| HPV45 | L2 | 8 | 361 | PSTIHKSF | 23731 |
| HPV45 | L2 | 10 | 361 | PSTIHKSFTY | 23732 |
| HPV45 | L2 | 8 | 416 | PSTSPTNA | 23733 |
| HPV45 | L2 | 9 | 98 | PTDPSIVTL | 23734 |
| HPV45 | L2 | 10 | 98 | PTDPSIVTLV | 23735 |
| HPV45 | L2 | 9 | 120 | PTFTGTSGF | 23736 |
| HPV45 | L2 | 11 | 120 | PTFTGTSGFEI | 23737 |
| HPV45 | L2 | 9 | 420 | PTNASTTTY | 23738 |
| HPV45 | L2 | 10 | 420 | PTNASTTTYI | 23739 |
| HPV45 | L2 | 8 | 86 | PTRPPVVI | 23740 |
| HPV45 | L2 | 11 | 86 | PTRPPVVIEPV | 23741 |
| HPV45 | L2 | 8 | 185 | PTSGSHGY | 23742 |
| HPV45 | L2 | 11 | 185 | PTSGSHGYEEI | 23743 |
| HPV45 | L2 | 10 | 267 | PTSNVPDSDF | 23744 |
| HPV45 | L2 | 11 | 267 | PTSNVPDSDFM | 23745 |
| HPV45 | L2 | 8 | 145 | PTVDSVSI | 23746 |
| HPV45 | L2 | 11 | 216 | PTVRRVRGPRL | 23747 |
| HPV45 | L2 | 9 | 23 | QSGTCPPDV | 23748 |
| HPV45 | L2 | 10 | 23 | QSGTCPPDVI | 23749 |
| HPV45 | L2 | 9 | 172 | QTGEVSGNI | 23750 |
| HPV45 | L2 | 10 | 172 | QTGEVSGNIF | 23751 |
| HPV45 | L2 | 11 | 172 | QTGEVSGNIFV | 23752 |
| HPV45 | L2 | 8 | 5 | RAARRKRA | 23753 |
| HPV45 | L2 | 10 | 5 | RAARRKRASA | 23754 |
| HPV45 | L2 | 8 | 229 | RANQQVRV | 23755 |
| HPV45 | L2 | 8 | 11 | RASATDLY | 23756 |
| HPV45 | L2 | 10 | 308 | RSGKQIGGRV | 23757 |
| HPV45 | L2 | 8 | 77 | RSNTVVDV | 23758 |
| HPV45 | L2 | 8 | 339 | SATNDSDL | 23759 |
| HPV45 | L2 | 9 | 339 | SATNDSDLF | 23760 |
| HPV45 | L2 | 11 | 339 | SATNDSDLFDV | 23761 |
| HPV45 | L2 | 8 | 394 | SAWDVPIY | 23762 |
| HPV45 | L2 | 9 | 202 | SSGSGTEPI | 23763 |
| HPV45 | L2 | 8 | 132 | SSGTTTPA | 23764 |
| HPV45 | L2 | 9 | 132 | SSGTTTPAV | 23765 |
| HPV45 | L2 | 10 | 132 | SSGTTTPAVL | 23766 |
| HPV45 | L2 | 10 | 48 | SSLGIFLGGL | 23767 |
| HPV45 | L2 | 10 | 246 | SSLVTFDNPA | 23768 |
| HPV45 | L2 | 11 | 246 | SSLVTFDNPAY | 23769 |
| HPV45 | L2 | 9 | 288 | SSRRGTVRF | 23770 |
| HPV45 | L2 | 8 | 211 | SSTPLPTV | 23771 |
| HPV45 | L2 | 11 | 211 | SSTPLPTVRRV | 23772 |
| HPV45 | L2 | 9 | 153 | SSTSFTNPA | 23773 |
| HPV45 | L2 | 10 | 153 | SSTSFTNPAF | 23774 |
| HPV45 | L2 | 8 | 110 | SSVVASGA | 23775 |
| HPV45 | L2 | 10 | 110 | SSVVASGAPV | 23776 |
| HPV45 | L2 | 8 | 383 | SSYSNVTV | 23777 |
| HPV45 | L2 | 10 | 383 | SSYSNVTVPL | 23778 |
| HPV45 | L2 | 10 | 379 | STAASSYSNV | 23779 |
| HPV45 | L2 | 9 | 362 | STIHKSFTY | 23780 |
| HPV45 | L2 | 10 | 212 | STPLPTVRRV | 23781 |
| HPV45 | L2 | 8 | 154 | STSFTNPA | 23782 |
| HPV45 | L2 | 9 | 154 | STSFTNPAF | 23783 |
| HPV45 | L2 | 11 | 358 | STTPSTIHKSF | 23784 |
| HPV45 | L2 | 8 | 424 | STTTYIGI | 23785 |
| HPV45 | L2 | 9 | 380 | TAASSYSNV | 23786 |
| HPV45 | L2 | 11 | 380 | TAASSYSNVTV | 23787 |

TABLE XIII-continued

B58 Supermotif Peptides

| Type | Protein | No. of Amino Acids | Position | Sequence | Seq. Id. No. |
|---|---|---|---|---|---|
| HPV45 | L2 | 8 | 393 | TSAWDVPI | 23788 |
| HPV45 | L2 | 9 | 393 | TSAWDVPIY | 23789 |
| HPV45 | L2 | 8 | 155 | TSFTNPAF | 23790 |
| HPV45 | L2 | 10 | 186 | TSGSHGYEEI | 23791 |
| HPV45 | L2 | 9 | 268 | TSNVPDSDF | 23792 |
| HPV45 | L2 | 10 | 268 | TSNVPDSDFM | 23793 |
| HPV45 | L2 | 11 | 418 | TSPTNASTTTY | 23794 |
| HPV45 | L2 | 11 | 238 | TSQFLTHPSSL | 23795 |
| HPV45 | L2 | 9 | 131 | TSSGTTTPA | 23796 |
| HPV45 | L2 | 10 | 131 | TSSGTTTPAV | 23797 |
| HPV45 | L2 | 11 | 131 | TSSGTTTPAVL | 23798 |
| HPV45 | L2 | 8 | 38 | TTLADKIL | 23799 |
| HPV45 | L2 | 10 | 38 | TTLADKILQW | 23800 |
| HPV45 | L2 | 11 | 261 | TTLSFEPTSNV | 23801 |
| HPV45 | L2 | 8 | 136 | TTPAVLDI | 23802 |
| HPV45 | L2 | 10 | 359 | TTPSTIHKSF | 23803 |
| HPV45 | L2 | 9 | 135 | TTTPAVLDI | 23804 |
| HPV45 | L2 | 11 | 426 | TTYIGIHGTQY | 23805 |
| HPV45 | L2 | 10 | 113 | VASGAPVPTF | 23806 |
| HPV45 | L2 | 11 | 2 | VSHRAARRKRA | 23807 |
| HPV45 | L2 | 8 | 150 | VSISSTSF | 23808 |
| HPV45 | L2 | 8 | 249 | VTFDNPAY | 23809 |
| HPV45 | L2 | 11 | 249 | VTFDNPAYEPL | 23810 |
| HPV45 | L2 | 9 | 104 | VTLVEDSSV | 23811 |
| HPV45 | L2 | 10 | 104 | VTLVEDSSVV | 23812 |
| HPV45 | L2 | 11 | 104 | VTLVEDSSVVA | 23813 |
| HPV45 | L2 | 8 | 388 | VTVPLTSA | 23814 |
| HPV45 | L2 | 9 | 388 | VTVPLTSAW | 23815 |
| HPV45 | L2 | 11 | 388 | VTVPLTSAWDV | 23816 |
| HPV45 | L2 | 8 | 47 | WSSLGIFL | 23817 |
| HPV45 | L2 | 11 | 47 | WSSLGIFLGGL | 23818 |
| HPV45 | L2 | 8 | 350 | YADFPPPA | 23819 |
| HPV45 | L2 | 9 | 373 | YSLTMPSTA | 23820 |
| HPV45 | L2 | 10 | 373 | YSLTMPSTAA | 23821 |
| HPV45 | L2 | 8 | 385 | YSNVTVPL | 23822 |
| HPV45 | L2 | 11 | 385 | YSNVTVPLTSA | 23823 |
| HPV45 | L2 | 8 | 227 | YSRANQQV | 23824 |
| HPV45 | L2 | 10 | 227 | YSRANQQVRV | 23825 |
| HPV45 | L2 | 8 | 401 | YTGPDIIL | 23826 |
| HPV56 | E2 | 8 | 13 | CSAIEVQI | 23827 |
| HPV56 | E2 | 9 | 13 | CSAIEVQIA | 23828 |
| HPV56 | E2 | 10 | 13 | CSAIEVQIAL | 23829 |
| HPV56 | E2 | 9 | 92 | CSGVDYRGI | 23830 |
| HPV56 | E2 | 10 | 92 | CSGVDYRGIY | 23831 |
| HPV56 | E2 | 11 | 92 | CSGVDYRGIYY | 23832 |
| HPV56 | E2 | 8 | 195 | DSSRESHA | 23833 |
| HPV56 | E2 | 11 | 195 | DSSRESHAKCV | 23834 |
| HPV56 | E2 | 9 | 140 | DSVSSTCRY | 23835 |
| HPV56 | E2 | 11 | 140 | DSVSSTCRYNV | 23836 |
| HPV56 | E2 | 8 | 39 | DTCEELWL | 23837 |
| HPV56 | E2 | 10 | 117 | EAKKFGCKNI | 23838 |
| HPV56 | E2 | 11 | 117 | EAKKFGCKNIW | 23839 |
| HPV56 | E2 | 9 | 134 | ESIYCPDSV | 23840 |
| HPV56 | E2 | 8 | 23 | ESLSTTIY | 23841 |
| HPV56 | E2 | 8 | 288 | ETQRNSFL | 23842 |
| HPV56 | E2 | 11 | 288 | ETQRNSFLSHV | 23843 |
| HPV56 | E2 | 9 | 66 | GSKNNCMQY | 23844 |
| HPV56 | E2 | 10 | 66 | GSKNNCMQYV | 23845 |
| HPV56 | E2 | 11 | 66 | GSKNNCMQYVA | 23846 |
| HPV56 | E2 | 11 | 201 | HAKCVTTHTHI | 23847 |
| HPV56 | E2 | 10 | 20 | IALESLSTTI | 23848 |
| HPV56 | E2 | 11 | 20 | IALESLSTTIY | 23849 |
| HPV56 | E2 | 8 | 11 | KACSAIEV | 23850 |
| HPV56 | E2 | 10 | 11 | KACSAIEVQI | 23851 |
| HPV56 | E2 | 11 | 11 | KACSAIEVQIA | 23852 |
| HPV56 | E2 | 8 | 9 | KAKACSAI | 23853 |
| HPV56 | E2 | 10 | 9 | KAKACSAIEV | 23854 |
| HPV56 | E2 | 11 | 258 | KTLFVDVTSTY | 23855 |
| HPV56 | E2 | 8 | 233 | KTTPVVHL | 23856 |
| HPV56 | E2 | 10 | 163 | KTTTTTSTSV | 23857 |
| HPV56 | E2 | 11 | 108 | KTYYTDFEQEA | 23858 |
| HPV56 | E2 | 8 | 295 | LSHVKIPV | 23859 |
| HPV56 | E2 | 9 | 295 | LSHVKIPVV | 23860 |
| HPV56 | E2 | 10 | 295 | LSHVKIPVVY | 23861 |
| HPV56 | E2 | 11 | 25 | LSTTIYNNEEW | 23862 |
| HPV56 | E2 | 8 | 46 | LTEPKKCF | 23863 |

TABLE XIII-continued

B58 Supermotif Peptides

| Type | Protein | No. of Amino Acids | Position | Sequence | Seq. Id. No. |
|---|---|---|---|---|---|
| HPV56 | E2 | 9 | 292 | NSFLSHVKI | 23864 |
| HPV56 | E2 | 11 | 292 | NSFLSHVKIPV | 23865 |
| HPV56 | E2 | 9 | 216 | NTDSRSRSI | 23866 |
| HPV56 | E2 | 8 | 14 | SAIEVQIA | 23867 |
| HPV56 | E2 | 9 | 14 | SAIEVQIAL | 23868 |
| HPV56 | E2 | 10 | 196 | SSRESHAKCV | 23869 |
| HPV56 | E2 | 8 | 143 | SSTCRYNV | 23870 |
| HPV56 | E2 | 11 | 143 | SSTCRYNVSPV | 23871 |
| HPV56 | E2 | 10 | 144 | STCRYNVSPV | 23872 |
| HPV56 | E2 | 9 | 272 | STDNKNYSI | 23873 |
| HPV56 | E2 | 10 | 272 | STDNKNYSII | 23874 |
| HPV56 | E2 | 9 | 169 | STSVGNQDA | 23875 |
| HPV56 | E2 | 10 | 169 | STSVGNQDAA | 23876 |
| HPV56 | E2 | 11 | 169 | STSVGNQDAAV | 23877 |
| HPV56 | E2 | 10 | 26 | STTIYNNEEW | 23878 |
| HPV56 | E2 | 8 | 271 | TSTDNKNY | 23879 |
| HPV56 | E2 | 10 | 271 | TSTDNKNYSI | 23880 |
| HPV56 | E2 | 11 | 271 | TSTDNKNYSII | 23881 |
| HPV56 | E2 | 10 | 168 | TSTSVGNQDA | 23882 |
| HPV56 | E2 | 11 | 168 | TSTSVGNQDAA | 23883 |
| HPV56 | E2 | 8 | 170 | TSVGNQDA | 23884 |
| HPV56 | E2 | 9 | 170 | TSVGNQDAA | 23885 |
| HPV56 | E2 | 10 | 170 | TSVGNQDAAV | 23886 |
| HPV56 | E2 | 9 | 27 | TTIYNNEEW | 23887 |
| HPV56 | E2 | 11 | 27 | TTIYNNEEWTL | 23888 |
| HPV56 | E2 | 11 | 167 | TTSTSVGNQDA | 23889 |
| HPV56 | E2 | 8 | 165 | TTTTSTSV | 23890 |
| HPV56 | E2 | 9 | 164 | TTTTTSTSV | 23891 |
| HPV56 | E2 | 8 | 75 | VAWKYIYY | 23892 |
| HPV56 | E2 | 11 | 179 | YSHRPGKRPRL | 23893 |
| HPV56 | E2 | 10 | 150 | VSPVETVNEY | 23894 |
| HPV56 | E2 | 9 | 142 | VSSTCRYNV | 23895 |
| HPV56 | E2 | 10 | 35 | WTLRDTCEEL | 23896 |
| HPV56 | E2 | 11 | 35 | WTLRDTCEELW | 23897 |
| HPV56 | E2 | 9 | 270 | WTSTDNKNY | 23898 |
| HPV56 | E2 | 11 | 270 | WTSTDNKNYSI | 23899 |
| HPV56 | E2 | 8 | 278 | YSIITIIY | 23900 |
| HPV56 | E2 | 8 | 111 | YTDFEQEA | 23901 |
| HPV56 | E2 | 11 | 111 | YTDFEQEAKKF | 23902 |
| HPV56 | E6 | 11 | 89 | ATLESITKKQL | 23903 |
| HPV56 | E6 | 8 | 50 | CTELKLVY | 23904 |
| HPV56 | E6 | 8 | 92 | ESITKKQL | 23905 |
| HPV56 | E6 | 11 | 92 | ESITKKQLCDL | 23906 |
| HPV56 | E6 | 8 | 48 | FACTELKL | 23907 |
| HPV56 | E6 | 9 | 48 | FACTELKLV | 23908 |
| HPV56 | E6 | 10 | 48 | FACTELKLVY | 23909 |
| HPV56 | E6 | 10 | 131 | IAHGWTGSCL | 23910 |
| HPV56 | E6 | 9 | 94 | ITKKQLCDL | 23911 |
| HPV56 | E6 | 10 | 94 | ITKKQLCDLL | 23912 |
| HPV56 | E6 | 11 | 94 | ITKKQLCDLLI | 23913 |
| HPV56 | E6 | 10 | 31 | LSCVYCKKEL | 23914 |
| HPV56 | E6 | 9 | 18 | LSEVLEIPL | 23915 |
| HPV56 | E6 | 10 | 18 | LSEVLEIPLI | 23916 |
| HPV56 | E6 | 8 | 113 | LTPEEKQL | 23917 |
| HPV56 | E6 | 9 | 40 | LTRAEVYNF | 23918 |
| HPV56 | E6 | 10 | 40 | LTRAEVYNFA | 23919 |
| HPV56 | E6 | 11 | 110 | QSPLTPEEKQL | 23920 |
| HPV56 | E6 | 11 | 145 | QTSREPRESTV | 23921 |
| HPV56 | E6 | 8 | 42 | RAEVYNFA | 23922 |
| HPV56 | E6 | 9 | 13 | RSLHHLSEV | 23923 |
| HPV56 | E6 | 10 | 13 | RSLHHLSEVL | 23924 |
| HPV56 | E6 | 10 | 146 | TSREPRESTV | 23925 |
| HPV56 | E6 | 9 | 135 | WTGSCLGCW | 23926 |
| HPV56 | E6 | 8 | 63 | YAVCRVCL | 23927 |
| HPV56 | E6 | 9 | 63 | YAVCRVCLL | 23928 |
| HPV56 | E6 | 10 | 63 | YAVCRVCLLF | 23929 |
| HPV56 | E6 | 11 | 63 | YAVCRVCLLFY | 23930 |
| HPV56 | E6 | 9 | 73 | YSKVRKYRY | 23931 |
| HPV56 | E6 | 10 | 73 | YSKVRKYRYY | 23932 |
| HPV56 | E6 | 8 | 84 | YSVYGATL | 23933 |
| HPV56 | E6 | 11 | 84 | YSVYGATLESI | 23934 |
| HPV56 | E7 | 11 | 30 | DSSEDEDEDEV | 23935 |
| HPV56 | E7 | 9 | 92 | GALTVTCPL | 23936 |
| HPV56 | E7 | 11 | 92 | GALTVTCPLCA | 23937 |
| HPV56 | E7 | 8 | 56 | HTCYLIHV | 23938 |
| HPV56 | E7 | 9 | 15 | LTPQTEIDL | 23939 |

TABLE XIII-continued

B58 Supermotif Peptides

| Type | Protein | No. of Amino Acids | Position | Sequence | Seq. Id. No. |
|---|---|---|---|---|---|
| HPV56 | E7 | 9 | 94 | LTVTCPLCA | 23940 |
| HPV56 | E7 | 8 | 6 | PTLQDVVL | 23941 |
| HPV56 | E7 | 10 | 6 | PTLQDVVLEL | 23942 |
| HPV56 | E7 | 8 | 52 | QAKQHTCY | 23943 |
| HPV56 | E7 | 9 | 52 | QAKQHTCYL | 23944 |
| HPV56 | E7 | 10 | 52 | QAKQHTCYLI | 23945 |
| HPV56 | E7 | 11 | 49 | QARQAKQHTCY | 23946 |
| HPV56 | E7 | 9 | 77 | QSTKEDLRV | 23947 |
| HPV56 | E7 | 10 | 77 | QSTKEDLRVV | 23948 |
| HPV56 | E7 | 10 | 31 | SSEDEDEDEV | 23949 |
| HPV56 | E7 | 8 | 78 | STKEDLRV | 23950 |
| HPV56 | E7 | 9 | 78 | STKEDLRVV | 23951 |
| HPV56 | L1 | 11 | 58 | ATDSYVKRTSI | 23952 |
| HPV56 | L1 | 8 | 381 | ATEQLSKY | 23953 |
| HPV56 | L1 | 10 | 381 | ATEQLSKYDA | 23954 |
| HPV56 | L1 | 8 | 327 | ATPSGSMI | 23955 |
| HPV56 | L1 | 8 | 514 | ATSKKRSA | 23956 |
| HPV56 | L1 | 8 | 444 | ATSLEDKY | 23957 |
| HPV56 | L1 | 10 | 444 | ATSLEDKYRY | 23958 |
| HPV56 | L1 | 11 | 444 | ATSLEDKYRYV | 23959 |
| HPV56 | L1 | 10 | 37 | ATWRPSENKV | 23960 |
| HPV56 | L1 | 11 | 37 | ATWRPSENKVY | 23961 |
| HPV56 | L1 | 9 | 195 | CTPAMGEHW | 23962 |
| HPV56 | L1 | 8 | 389 | DARKINQY | 23963 |
| HPV56 | L1 | 9 | 389 | DARKINQYL | 23964 |
| HPV56 | L1 | 8 | 274 | DAYGDSMW | 23965 |
| HPV56 | L1 | 9 | 274 | DAYGDSMWF | 23966 |
| HPV56 | L1 | 10 | 274 | DAYGDSMWFY | 23967 |
| HPV56 | L1 | 11 | 274 | DAYGDSMWFYL | 23968 |
| HPV56 | L1 | 10 | 486 | DSFSTDLDQF | 23969 |
| HPV56 | L1 | 8 | 176 | DSRDNISV | 23970 |
| HPV56 | L1 | 9 | 60 | DSYVKRTSI | 23971 |
| HPV56 | L1 | 10 | 60 | DSYVKRTSIF | 23972 |
| HPV56 | L1 | 11 | 60 | DSYVKRTSIFY | 23973 |
| HPV56 | L1 | 8 | 162 | DTESSNLA | 23974 |
| HPV56 | L1 | 9 | 236 | DTGFGAMDF | 23975 |
| HPV56 | L1 | 11 | 236 | DTGFGAMDFKV | 23976 |
| HPV56 | L1 | 8 | 369 | DTTRSTNM | 23977 |
| HPV56 | L1 | 10 | 369 | DTTRSTNMTI | 23978 |
| HPV56 | L1 | 9 | 337 | EAQLFNKPY | 23979 |
| HPV56 | L1 | 10 | 337 | EAQLFNKPYW | 23980 |
| HPV56 | L1 | 11 | 337 | EAQLFNKPYWL | 23981 |
| HPV56 | L1 | 8 | 249 | ESKAEVPL | 23982 |
| HPV56 | L1 | 10 | 249 | ESKAEVPLDI | 23983 |
| HPV56 | L1 | 11 | 249 | ESKAEVPLDIV | 23984 |
| HPV56 | L1 | 10 | 164 | ESSNLANNNV | 23985 |
| HPV56 | L1 | 11 | 164 | ESSNLANNNVI | 23986 |
| HPV56 | L1 | 8 | 303 | ETIPAELY | 23987 |
| HPV56 | L1 | 9 | 303 | ETIPAELYL | 23988 |
| HPV56 | L1 | 9 | 290 | FARHYFNRA | 23989 |
| HPV56 | L1 | 8 | 488 | FSTDLDQF | 23990 |
| HPV56 | L1 | 10 | 488 | FSTDLDQFPL | 23991 |
| HPV56 | L1 | 9 | 148 | GAGLSGHPL | 23992 |
| HPV56 | L1 | 10 | 148 | GAGLSGHPLF | 23993 |
| HPV56 | L1 | 8 | 240 | GAMDFKVL | 23994 |
| HPV56 | L1 | 9 | 206 | GAVCKSTQV | 23995 |
| HPV56 | L1 | 8 | 25 | GAVNVFPI | 23996 |
| HPV56 | L1 | 9 | 25 | GAVNVFPIF | 23997 |
| HPV56 | L1 | 10 | 25 | GAVNVFPIFL | 23998 |
| HPV56 | L1 | 8 | 331 | GSMITSEA | 23999 |
| HPV56 | L1 | 10 | 331 | GSMITSEAQL | 24000 |
| HPV56 | L1 | 11 | 331 | GSMITSEAQLF | 24001 |
| HPV56 | L1 | 8 | 73 | GSSRLLAV | 24002 |
| HPV56 | L1 | 8 | 506 | GTRSKPAV | 24003 |
| HPV56 | L1 | 9 | 506 | GTRSKPAVA | 24004 |
| HPV56 | L1 | 8 | 71 | HAGSSRLL | 24005 |
| HPV56 | L1 | 9 | 71 | HAGSSRLLA | 24006 |
| HPV56 | L1 | 10 | 71 | HAGSSRLLAV | 24007 |
| HPV56 | L1 | 8 | 378 | ISTATEQL | 24008 |
| HPV56 | L1 | 11 | 378 | ISTATEQLSKY | 24009 |
| HPV56 | L1 | 10 | 181 | ISVDGKQTQL | 24010 |
| HPV56 | L1 | 8 | 414 | ITLSAEVM | 24011 |
| HPV56 | L1 | 9 | 414 | ITLSAEVMA | 24012 |
| HPV56 | L1 | 10 | 414 | ITLSAEVMAY | 24013 |
| HPV56 | L1 | 11 | 414 | ITLSAEVMAYL | 24014 |
| HPV56 | L1 | 8 | 334 | ITSEAQLF | 24015 |

TABLE XIII-continued

B58 Supermotif Peptides

| Type | Protein | No. of Amino Acids | Position | Sequence | Seq. Id. No. |
|---|---|---|---|---|---|
| HPV56 | L1 | 8 | 251 | KAEVPLDI | 24016 |
| HPV56 | L1 | 9 | 251 | KAEVPLDIV | 24017 |
| HPV56 | L1 | 9 | 93 | KTNIPKVSA | 24018 |
| HPV56 | L1 | 10 | 93 | KTNIPKVSAY | 24019 |
| HPV56 | L1 | 9 | 474 | LAKYKFWDV | 24020 |
| HPV56 | L1 | 11 | 474 | LAKYKFWDVNL | 24021 |
| HPV56 | L1 | 8 | 222 | LALINTPI | 24022 |
| HPV56 | L1 | 8 | 78 | LAVGHPYY | 24023 |
| HPV56 | L1 | 10 | 78 | LAVGHPYYSV | 24024 |
| HPV56 | L1 | 8 | 416 | LSAEVMAY | 24025 |
| HPV56 | L1 | 9 | 416 | LSAEVMAYL | 24026 |
| HPV56 | L1 | 10 | 151 | LSGHPLFNRL | 24027 |
| HPV56 | L1 | 9 | 385 | LSKYDARKI | 24028 |
| HPV56 | L1 | 9 | 439 | LSPPVATSL | 24029 |
| HPV56 | L1 | 11 | 36 | MATWRPSENKV | 24030 |
| HPV56 | L1 | 9 | 421 | MAYLHNMNA | 24031 |
| HPV56 | L1 | 11 | 421 | MAYLHNMNANL | 24032 |
| HPV56 | L1 | 10 | 271 | MSADAYGDSM | 24033 |
| HPV56 | L1 | 11 | 271 | MSADAYGDSMW | 24034 |
| HPV56 | L1 | 10 | 376 | MTISTATEQL | 24035 |
| HPV56 | L1 | 8 | 428 | NANLLEDW | 24036 |
| HPV56 | L1 | 10 | 428 | NANLLEDWNI | 24037 |
| HPV56 | L1 | 9 | 91 | NTKTNIPKV | 24038 |
| HPV56 | L1 | 11 | 91 | NTKTNIPKVSA | 24039 |
| HPV56 | L1 | 9 | 226 | NTPIEDGDM | 24040 |
| HPV56 | L1 | 10 | 226 | NTPIEDGDMI | 24041 |
| HPV56 | L1 | 11 | 197 | PAMGEHWTKGA | 24042 |
| HPV56 | L1 | 11 | 511 | PAVATSKKRSA | 24043 |
| HPV56 | L1 | 8 | 41 | PSENKVYL | 24044 |
| HPV56 | L1 | 10 | 329 | PSGSMITSEA | 24045 |
| HPV56 | L1 | 8 | 467 | PTEKQDPL | 24046 |
| HPV56 | L1 | 9 | 467 | PTEKQDPLA | 24047 |
| HPV56 | L1 | 11 | 467 | PTEKQDPLAKY | 24048 |
| HPV56 | L1 | 8 | 50 | PTPVSKVV | 24049 |
| HPV56 | L1 | 9 | 50 | PTPVSKVVA | 24050 |
| HPV56 | L1 | 8 | 522 | PTSTSTPA | 24051 |
| HPV56 | L1 | 9 | 260 | QSTCKYPDY | 24052 |
| HPV56 | L1 | 10 | 260 | QSTCKYPDYL | 24053 |
| HPV56 | L1 | 9 | 297 | RAGKVGETI | 24054 |
| HPV56 | L1 | 11 | 297 | RAGKVGETIPA | 24055 |
| HPV56 | L1 | 9 | 349 | RAQGHNNGI | 24056 |
| HPV56 | L1 | 11 | 349 | RAQGHNNGICW | 24057 |
| HPV56 | L1 | 11 | 519 | RSAPTSTSTPA | 24058 |
| HPV56 | L1 | 10 | 372 | RSTNMTISTA | 24059 |
| HPV56 | L1 | 8 | 65 | RTSIFYHA | 24060 |
| HPV56 | L1 | 9 | 272 | SADAYGDSM | 24061 |
| HPV56 | L1 | 10 | 272 | SADAYGDSMW | 24062 |
| HPV56 | L1 | 11 | 272 | SADAYGDSMWF | 24063 |
| HPV56 | L1 | 8 | 417 | SAEVMAYL | 24064 |
| HPV56 | L1 | 11 | 417 | SAEVMAYLHNM | 24065 |
| HPV56 | L1 | 10 | 520 | SAPTSTSTPA | 24066 |
| HPV56 | L1 | 8 | 100 | SAYQYRVF | 24067 |
| HPV56 | L1 | 10 | 100 | SAYQYRVFRV | 24068 |
| HPV56 | L1 | 9 | 165 | SSNLANNNV | 24069 |
| HPV56 | L1 | 10 | 165 | SSNLANNNVI | 24070 |
| HPV56 | L1 | 11 | 74 | SSRLLAVGHPY | 24071 |
| HPV56 | L1 | 10 | 379 | STATEQLSKY | 24072 |
| HPV56 | L1 | 8 | 261 | STCKYPDY | 24073 |
| HPV56 | L1 | 9 | 261 | STCKYPDYL | 24074 |
| HPV56 | L1 | 11 | 261 | STCKYPDYLKM | 24075 |
| HPV56 | L1 | 9 | 489 | STDLDQFPL | 24076 |
| HPV56 | L1 | 9 | 373 | STNMTISTA | 24077 |
| HPV56 | L1 | 9 | 380 | TATEQLSKY | 24078 |
| HPV56 | L1 | 11 | 380 | TATEQLSKYDA | 24079 |
| HPV56 | L1 | 11 | 335 | TSEAQLFNKPY | 24080 |
| HPV56 | L1 | 9 | 445 | TSLEDKYRY | 24081 |
| HPV56 | L1 | 10 | 445 | TSLEDKYRYV | 24082 |
| HPV56 | L1 | 8 | 215 | TTGDCPPL | 24083 |
| HPV56 | L1 | 9 | 215 | TTGDCPPLA | 24084 |
| HPV56 | L1 | 10 | 215 | TTGDCPPLAL | 24085 |
| HPV56 | L1 | 11 | 215 | TTGDCPPLALI | 24086 |
| HPV56 | L1 | 9 | 370 | TTRSTNMTI | 24087 |
| HPV56 | L1 | 8 | 326 | VATPSGSM | 24088 |
| HPV56 | L1 | 9 | 326 | VATPSGSMI | 24089 |
| HPV56 | L1 | 9 | 513 | VATSKKRSA | 24090 |
| HPV56 | L1 | 9 | 443 | VATSLEDKY | 24091 |

TABLE XIII-continued

B58 Supermotif Peptides

| Type | Protein | No. of Amino Acids | Position | Sequence | Seq. Id. No. |
|---|---|---|---|---|---|
| HPV56 | L1 | 11 | 443 | VATSLEDKYRY | 24092 |
| HPV56 | L1 | 8 | 99 | VSAYQYRV | 24093 |
| HPV56 | L1 | 9 | 99 | VSAYQYRVF | 24094 |
| HPV56 | L1 | 11 | 99 | VSAYQYRVFRV | 24095 |
| HPV56 | L1 | 10 | 53 | VSKVVATDSY | 24096 |
| HPV56 | L1 | 11 | 53 | VSKVVATDSYV | 24097 |
| HPV56 | L1 | 10 | 87 | VTKDNTKTNI | 24098 |
| HPV56 | L1 | 9 | 214 | VTTGDCPPL | 24099 |
| HPV56 | L1 | 10 | 214 | VTTGDCPPLA | 24100 |
| HPV56 | L1 | 11 | 214 | VTTGDCPPLAL | 24101 |
| HPV56 | L1 | 8 | 134 | WACVGLEV | 24102 |
| HPV56 | L2 | 9 | 222 | AAPRLYRKA | 24103 |
| HPV56 | L2 | 10 | 222 | AAPRLYRKAF | 24104 |
| HPV56 | L2 | 9 | 383 | ASNTTNVTA | 24105 |
| HPV56 | L2 | 11 | 383 | ASNTTNVTAPL | 24106 |
| HPV56 | L2 | 11 | 303 | ATIQTRRGTQI | 24107 |
| HPV56 | L2 | 10 | 246 | ATLVSADNPL | 24108 |
| HPV56 | L2 | 11 | 246 | ATLVSADNPLF | 24109 |
| HPV56 | L2 | 9 | 367 | ATPSAHLPI | 24110 |
| HPV56 | L2 | 10 | 14 | ATQLYKTCKL | 24111 |
| HPV56 | L2 | 9 | 6 | ATRRKRASA | 24112 |
| HPV56 | L2 | 11 | 260 | DTSLAFSPSGV | 24113 |
| HPV56 | L2 | 10 | 357 | EAPGLSSQSV | 24114 |
| HPV56 | L2 | 11 | 357 | EAPGLSSQSVA | 24115 |
| HPV56 | L2 | 8 | 169 | EAPQTGEV | 24116 |
| HPV56 | L2 | 9 | 114 | ESGAGIPNF | 24117 |
| HPV56 | L2 | 9 | 109 | ESSVIESGA | 24118 |
| HPV56 | L2 | 11 | 109 | ESSVIESGAGI | 24119 |
| HPV56 | L2 | 10 | 94 | ESVGPTDPSI | 24120 |
| HPV56 | L2 | 11 | 94 | ESVGPTDPSIV | 24121 |
| HPV56 | L2 | 10 | 398 | ETPFYSGPDI | 24122 |
| HPV56 | L2 | 11 | 398 | ETPFYSGPDIV | 24123 |
| HPV56 | L2 | 8 | 457 | FADGDVAA | 24124 |
| HPV56 | L2 | 8 | 437 | FALWPVYF | 24125 |
| HPV56 | L2 | 9 | 437 | FALWPVYFF | 24126 |
| HPV56 | L2 | 8 | 382 | FASNTTNV | 24127 |
| HPV56 | L2 | 10 | 382 | FASNTTNVTA | 24128 |
| HPV56 | L2 | 11 | 200 | FAVHGSGTEPI | 24129 |
| HPV56 | L2 | 8 | 296 | FSRLGRKA | 24130 |
| HPV56 | L2 | 10 | 296 | FSRLGRKATI | 24131 |
| HPV56 | L2 | 9 | 122 | FTGSGGFEI | 24132 |
| HPV56 | L2 | 8 | 287 | FTTRRGGV | 24133 |
| HPV56 | L2 | 10 | 287 | FTTRRGGVRF | 24134 |
| HPV56 | L2 | 9 | 51 | FTYFGGLGI | 24135 |
| HPV56 | L2 | 8 | 314 | GARVHYYY | 24136 |
| HPV56 | L2 | 10 | 314 | GARVHYYYDI | 24137 |
| HPV56 | L2 | 8 | 64 | GSGGRAGY | 24138 |
| HPV56 | L2 | 9 | 64 | GSGGRAGYV | 24139 |
| HPV56 | L2 | 11 | 64 | GSGGRAGYVPL | 24140 |
| HPV56 | L2 | 10 | 48 | GSLFTYFGGL | 24141 |
| HPV56 | L2 | 8 | 75 | GSRPSTIV | 24142 |
| HPV56 | L2 | 10 | 75 | GSRPSTIVDV | 24143 |
| HPV56 | L2 | 9 | 434 | GSSFALWPV | 24144 |
| HPV56 | L2 | 10 | 434 | GSSFALWPVY | 24145 |
| HPV56 | L2 | 11 | 434 | GSSFALWPVYF | 24146 |
| HPV56 | L2 | 8 | 25 | GTCPEDVV | 24147 |
| HPV56 | L2 | 11 | 25 | GTCPEDVVNKI | 24148 |
| HPV56 | L2 | 8 | 258 | GTDTSLAF | 24149 |
| HPV56 | L2 | 10 | 206 | GTEPISSTPI | 24150 |
| HPV56 | L2 | 8 | 62 | GTGSGGRA | 24151 |
| HPV56 | L2 | 10 | 62 | GTGSGGRAGY | 24152 |
| HPV56 | L2 | 11 | 62 | GTGSGGRAGYV | 24153 |
| HPV56 | L2 | 10 | 60 | GTGTGSGGRA | 24154 |
| HPV56 | L2 | 8 | 310 | GTQIGARV | 24155 |
| HPV56 | L2 | 10 | 310 | GTQIGARVHY | 24156 |
| HPV56 | L2 | 11 | 310 | GTQIGARVHYY | 24157 |
| HPV56 | L2 | 8 | 190 | HSYEEIPM | 24158 |
| HPV56 | L2 | 11 | 190 | HSYEEIPMQTF | 24159 |
| HPV56 | L2 | 10 | 221 | IAAPRLYRKA | 24160 |
| HPV56 | L2 | 11 | 221 | IAAPRLYRKAF | 24161 |
| HPV56 | L2 | 9 | 326 | IAQAEEIEM | 24162 |
| HPV56 | L2 | 10 | 323 | ISPIAQAEEI | 24163 |
| HPV56 | L2 | 9 | 210 | ISSTPIPGF | 24164 |
| HPV56 | L2 | 8 | 182 | ISTPTSGI | 24165 |
| HPV56 | L2 | 11 | 182 | ISTPTSGIHSY | 24166 |
| HPV56 | L2 | 11 | 157 | ITNPLFIDPPV | 24167 |

TABLE XIII-continued

B58 Supermotif Peptides

| Type | Protein | No. of Amino Acids | Position | Sequence | Seq. Id. No. |
|---|---|---|---|---|---|
| HPV56 | L2 | 8 | 143 | ITPTSSTV | 24168 |
| HPV56 | L2 | 10 | 143 | ITPTSSTVHV | 24169 |
| HPV56 | L2 | 10 | 130 | ITSSSTTTPA | 24170 |
| HPV56 | L2 | 11 | 130 | ITSSSTTTPAV | 24171 |
| HPV56 | L2 | 8 | 229 | KAFQQVKV | 24172 |
| HPV56 | L2 | 8 | 38 | KTWADKIL | 24173 |
| HPV56 | L2 | 10 | 38 | KTWADKILQW | 24174 |
| HPV56 | L2 | 8 | 263 | LAFSPSGV | 24175 |
| HPV56 | L2 | 9 | 263 | LAFSPSGVA | 24176 |
| HPV56 | L2 | 10 | 338 | LSANNSFDGL | 24177 |
| HPV56 | L2 | 11 | 338 | LSANNSFDGLY | 24178 |
| HPV56 | L2 | 10 | 380 | LSFASNTTNV | 24179 |
| HPV56 | L2 | 9 | 23 | LSGTCPEDV | 24180 |
| HPV56 | L2 | 10 | 23 | LSGTCPEDVV | 24181 |
| HPV56 | L2 | 11 | 361 | LSSQSVATPSA | 24182 |
| HPV56 | L2 | 9 | 342 | NSFDGLYDI | 24183 |
| HPV56 | L2 | 10 | 342 | NSFDGLYDIY | 24184 |
| HPV56 | L2 | 11 | 342 | NSFDGLYDIYA | 24185 |
| HPV56 | L2 | 9 | 385 | NTTNVTAPL | 24186 |
| HPV56 | L2 | 8 | 239 | PAFLDRPA | 24187 |
| HPV56 | L2 | 10 | 239 | PAFLDRPATL | 24188 |
| HPV56 | L2 | 11 | 239 | PAFLDRPATLV | 24189 |
| HPV56 | L2 | 10 | 285 | PAFTTRRGGV | 24190 |
| HPV56 | L2 | 8 | 86 | PARPPIVV | 24191 |
| HPV56 | L2 | 11 | 86 | PARPPIVVESV | 24192 |
| HPV56 | L2 | 11 | 245 | PATLVSADNPL | 24193 |
| HPV56 | L2 | 10 | 267 | PSGVAPDPDF | 24194 |
| HPV56 | L2 | 11 | 267 | PSGVAPDPDFM | 24195 |
| HPV56 | L2 | 10 | 78 | PSTIVDVTPA | 24196 |
| HPV56 | L2 | 9 | 98 | PTDPSIVTL | 24197 |
| HPV56 | L2 | 10 | 98 | PTDPSIVTLV | 24198 |
| HPV56 | L2 | 9 | 410 | PTGPSTWPF | 24199 |
| HPV56 | L2 | 10 | 410 | PTGPSTWPFV | 24200 |
| HPV56 | L2 | 8 | 185 | PTSGIHSY | 24201 |
| HPV56 | L2 | 11 | 185 | PTSGIHSYEEI | 24202 |
| HPV56 | L2 | 8 | 145 | PTSSTVHV | 24203 |
| HPV56 | L2 | 10 | 328 | QAEEIEMQPL | 24204 |
| HPV56 | L2 | 11 | 328 | QAEEIEMQPLL | 24205 |
| HPV56 | L2 | 10 | 421 | QSPYDVTHDV | 24206 |
| HPV56 | L2 | 11 | 421 | QSPYDVTHDVY | 24207 |
| HPV56 | L2 | 8 | 364 | QSVATPSA | 24208 |
| HPV56 | L2 | 10 | 364 | QSVATPSAHL | 24209 |
| HPV56 | L2 | 9 | 172 | QTGEVSGNI | 24210 |
| HPV56 | L2 | 10 | 172 | QTGEVSGNIL | 24211 |
| HPV56 | L2 | 11 | 172 | QTGEVSGNILI | 24212 |
| HPV56 | L2 | 8 | 306 | QTRRGTQI | 24213 |
| HPV56 | L2 | 10 | 306 | QTRRGTQIGA | 24214 |
| HPV56 | L2 | 8 | 11 | RASATQLY | 24215 |
| HPV56 | L2 | 8 | 5 | RATRRKRA | 24216 |
| HPV56 | L2 | 10 | 5 | RATRRKRASA | 24217 |
| HPV56 | L2 | 11 | 370 | SAHLPIKPSTL | 24218 |
| HPV56 | L2 | 9 | 339 | SANNSFDGL | 24219 |
| HPV56 | L2 | 10 | 339 | SANNSFDGLY | 24220 |
| HPV56 | L2 | 11 | 13 | SATQLYKTCKL | 24221 |
| HPV56 | L2 | 8 | 435 | SSFALWPV | 24222 |
| HPV56 | L2 | 9 | 435 | SSFALWPVY | 24223 |
| HPV56 | L2 | 10 | 435 | SSFALWPVYF | 24224 |
| HPV56 | L2 | 11 | 435 | SSFALWPVYFF | 24225 |
| HPV56 | L2 | 10 | 362 | SSQSVATPSA | 24226 |
| HPV56 | L2 | 8 | 132 | SSSTTTPA | 24227 |
| HPV56 | L2 | 9 | 132 | SSSTTTPAV | 24228 |
| HPV56 | L2 | 10 | 132 | SSSTTTPAVL | 24229 |
| HPV56 | L2 | 9 | 153 | SSTHITNPL | 24230 |
| HPV56 | L2 | 10 | 153 | SSTHITNPLF | 24231 |
| HPV56 | L2 | 11 | 153 | SSTHITNPLFI | 24232 |
| HPV56 | L2 | 8 | 211 | SSTPIPGF | 24233 |
| HPV56 | L2 | 11 | 211 | SSTPIPGFRRI | 24234 |
| HPV56 | L2 | 8 | 133 | SSTTPAV | 24235 |
| HPV56 | L2 | 9 | 133 | SSTTTPAVL | 24236 |
| HPV56 | L2 | 11 | 133 | SSTTTPAVLDI | 24237 |
| HPV56 | L2 | 11 | 147 | SSTVHVSSTHI | 24238 |
| HPV56 | L2 | 8 | 110 | SSVIESGA | 24239 |
| HPV56 | L2 | 10 | 110 | SSVIESGAGI | 24240 |
| HPV56 | L2 | 8 | 154 | STHITNPL | 24241 |
| HPV56 | L2 | 9 | 154 | STHITNPLF | 24242 |
| HPV56 | L2 | 10 | 154 | STHITNPLFI | 24243 |

TABLE XIII-continued

B58 Supermotif Peptides

| Type | Protein | No. of Amino Acids | Position | Sequence | Seq. Id. No. |
|---|---|---|---|---|---|
| HPV56 | L2 | 9 | 79 | STIVDVTPA | 24244 |
| HPV56 | L2 | 10 | 212 | STPIPGFRRI | 24245 |
| HPV56 | L2 | 11 | 212 | STPIPGFRRIA | 24246 |
| HPV56 | L2 | 10 | 183 | STPTSGIHSY | 24247 |
| HPV56 | L2 | 8 | 134 | STTTPAVL | 24248 |
| HPV56 | L2 | 10 | 134 | STTTPAVLDI | 24249 |
| HPV56 | L2 | 10 | 148 | STVHVSSTHI | 24250 |
| HPV56 | L2 | 11 | 414 | STWPFVPQSPY | 24251 |
| HPV56 | L2 | 8 | 390 | TAPLGNVW | 24252 |
| HPV56 | L2 | 10 | 186 | TSGIHSYEEI | 24253 |
| HPV56 | L2 | 10 | 261 | TSLAFSPSGV | 24254 |
| HPV56 | L2 | 11 | 261 | TSLAFSPSGVA | 24255 |
| HPV56 | L2 | 9 | 131 | TSSSTTPA | 24256 |
| HPV56 | L2 | 10 | 131 | TSSSTTTPAV | 24257 |
| HPV56 | L2 | 11 | 131 | TSSSTTTPAVL | 24258 |
| HPV56 | L2 | 8 | 386 | TTNVTAPL | 24259 |
| HPV56 | L2 | 11 | 386 | TTNVTAPLGNV | 24260 |
| HPV56 | L2 | 8 | 136 | TTPAVLDI | 24261 |
| HPV56 | L2 | 9 | 288 | TTRRGGVRF | 24262 |
| HPV56 | L2 | 9 | 135 | TTTPAVLDI | 24263 |
| HPV56 | L2 | 11 | 2 | VAHRATRRKRA | 24264 |
| HPV56 | L2 | 8 | 280 | VALHRPAF | 24265 |
| HPV56 | L2 | 8 | 270 | VAPDPDFM | 24266 |
| HPV56 | L2 | 10 | 270 | VAPDPDFMNI | 24267 |
| HPV56 | L2 | 11 | 270 | VAPDPDFMNIV | 24268 |
| HPV56 | L2 | 8 | 366 | VATPSAHL | 24269 |
| HPV56 | L2 | 10 | 366 | VATPSAHLPI | 24270 |
| HPV56 | L2 | 8 | 249 | VSADNPLF | 24271 |
| HPV56 | L2 | 10 | 152 | VSSTHITNPL | 24272 |
| HPV56 | L2 | 11 | 152 | VSSTHITNPLF | 24273 |
| HPV56 | L2 | 8 | 389 | VTAPLGNV | 24274 |
| HPV56 | L2 | 9 | 389 | VTAPLGNVW | 24275 |
| HPV56 | L2 | 11 | 236 | VTDPAFLDRPA | 24276 |
| HPV56 | L2 | 9 | 104 | VTLVEESSV | 24277 |
| HPV56 | L2 | 10 | 104 | VTLVEESSVI | 24278 |
| HPV56 | L2 | 8 | 84 | VTPARPPI | 24279 |
| HPV56 | L2 | 9 | 84 | VTPARPPIV | 24280 |
| HPV56 | L2 | 10 | 84 | VTPARPPIVV | 24281 |
| HPV56 | L2 | 8 | 40 | WADKILQW | 24282 |
| HPV56 | L2 | 11 | 40 | WADKILQWGSL | 24283 |
| HPV56 | L2 | 8 | 351 | YANIDDEA | 24284 |
| HPV56 | L2 | 11 | 351 | YANIDDEAPGL | 24285 |
| HPV56 | L2 | 8 | 402 | YSGPDIVL | 24286 |

TABLE XIV

B62 Supermotif Peptides

| Type | Protein | No. of Amino Acid | Position | Sequence | Seq. Id. No. |
|---|---|---|---|---|---|
| HPV16 | E1 | 10 | 112 | AICIEKQSRA | 24287 |
| HPV16 | E1 | 11 | 112 | AICIEKQSRAA | 24288 |
| HPV16 | E1 | 9 | 539 | ALDGNLVSM | 24289 |
| HPV16 | E1 | 11 | 539 | ALDGNLVSMDV | 24290 |
| HPV16 | E1 | 8 | 69 | ALFTAQEA | 24291 |
| HPV16 | E1 | 9 | 459 | ALKRFLQGI | 24292 |
| HPV16 | E1 | 9 | 318 | ALYWYKTGI | 24293 |
| HPV16 | E1 | 9 | 206 | AMLAKFKEL | 24294 |
| HPV16 | E1 | 10 | 206 | AMLAKFKELY | 24295 |
| HPV16 | E1 | 10 | 73 | AQEAKQHRDA | 24296 |
| HPV16 | E1 | 11 | 73 | AQEAKQHRDAV | 24297 |
| HPV16 | E1 | 10 | 380 | AQLADTNSNA | 24298 |
| HPV16 | E1 | 9 | 82 | AVQVLKRKY | 24299 |
| HPV16 | E1 | 10 | 82 | AVQVLKRKYL | 24300 |
| HPV16 | E1 | 11 | 82 | AVQVLKRKYLV | 24301 |
| HPV16 | E1 | 10 | 23 | AVVEKKTGDA | 24302 |
| HPV16 | E1 | 11 | 23 | AVVEKKTGDAI | 24303 |
| HPV16 | E1 | 11 | 237 | CIAAFGLTPSI | 24304 |
| HPV16 | E1 | 8 | 114 | CIEKQSRA | 24305 |
| HPV16 | E1 | 9 | 114 | CIEKQSRAA | 24306 |
| HPV16 | E1 | 8 | 472 | CILLYGAA | 24307 |
| HPV16 | E1 | 9 | 259 | CLYLHIQSL | 24308 |
| HPV16 | E1 | 10 | 259 | CLYLHIQSLA | 24309 |

TABLE XIV-continued

B62 Supermotif Peptides

| Type | Protein | No. of Amino Acid | Position | Sequence | Seq. Id. No. |
|---|---|---|---|---|---|
| HPV16 | E1 | 9 | 304 | CMMIEPPKL | 24310 |
| HPV16 | E1 | 10 | 559 | CPPLLITSNI | 24311 |
| HPV16 | E1 | 8 | 187 | CQTPLTNI | 24312 |
| HPV16 | E1 | 9 | 187 | CQTPLTNIL | 24313 |
| HPV16 | E1 | 11 | 187 | CQTPLTNILNV | 24314 |
| HPV16 | E1 | 10 | 101 | CVDNNISPRL | 24315 |
| HPV16 | E1 | 10 | 640 | CVSGQNTNTL | 24316 |
| HPV16 | E1 | 8 | 299 | CVSPMCMM | 24317 |
| HPV16 | E1 | 9 | 299 | CVSPMCMMI | 24318 |
| HPV16 | E1 | 10 | 97 | DISGCVDNNI | 24319 |
| HPV16 | E1 | 8 | 368 | DIVDDSEI | 24320 |
| HPV16 | E1 | 9 | 368 | DIVDDSEIA | 24321 |
| HPV16 | E1 | 10 | 368 | DIVDDSEIAY | 24322 |
| HPV16 | E1 | 8 | 548 | DVKHRPLV | 24323 |
| HPV16 | E1 | 10 | 548 | DVKHRPLVQL | 24324 |
| HPV16 | E1 | 9 | 374 | EIAYKYAQL | 24325 |
| HPV16 | E1 | 10 | 374 | EIAYKYAQLA | 24326 |
| HPV16 | E1 | 10 | 603 | ELNDKNWKSF | 24327 |
| HPV16 | E1 | 11 | 603 | ELNDKNWKSFF | 24328 |
| HPV16 | E1 | 8 | 356 | ELSQMVQW | 24329 |
| HPV16 | E1 | 9 | 356 | ELSQMVQWA | 24330 |
| HPV16 | E1 | 10 | 356 | ELSQMVQWAY | 24331 |
| HPV16 | E1 | 10 | 213 | ELYGVSFSEL | 24332 |
| HPV16 | E1 | 11 | 213 | ELYGVSFSELV | 24333 |
| HPV16 | E1 | 9 | 308 | EPPKLRSTA | 24334 |
| HPV16 | E1 | 10 | 308 | EPPKLRSTAA | 24335 |
| HPV16 | E1 | 11 | 308 | EPPKLRSTAAA | 24336 |
| HPV16 | E1 | 8 | 138 | EVETQQML | 24337 |
| HPV16 | E1 | 10 | 138 | EVETQQMLQV | 24338 |
| HPV16 | E1 | 9 | 331 | EVYGDTPEW | 24339 |
| HPV16 | E1 | 10 | 331 | EVYGDTPEWI | 24340 |
| HPV16 | E1 | 8 | 51 | FIVNDNDY | 24341 |
| HPV16 | E1 | 9 | 51 | FIVNDNDYL | 24342 |
| HPV16 | E1 | 8 | 392 | FLKSNSQA | 24343 |
| HPV16 | E1 | 10 | 392 | FLKSNSQAKI | 24344 |
| HPV16 | E1 | 11 | 392 | FLKSNSQAKIV | 24345 |
| HPV16 | E1 | 11 | 463 | FLQGIPKKNCI | 24346 |
| HPV16 | E1 | 9 | 493 | FLQGSVICF | 24347 |
| HPV16 | E1 | 10 | 493 | FLQGSVICFV | 24348 |
| HPV16 | E1 | 9 | 445 | FLRYQGVEF | 24349 |
| HPV16 | E1 | 10 | 445 | FLRYQGVEFM | 24350 |
| HPV16 | E1 | 8 | 456 | FLTALKRF | 24351 |
| HPV16 | E1 | 9 | 456 | FLTALKRFL | 24352 |
| HPV16 | E1 | 8 | 453 | FMSFLTAL | 24353 |
| HPV16 | E1 | 11 | 453 | FMSFLTALKRF | 24354 |
| HPV16 | E1 | 10 | 592 | FPFDENGNPV | 24355 |
| HPV16 | E1 | 11 | 592 | FPFDENGNPVY | 24356 |
| HPV16 | E1 | 8 | 501 | FVNSKSHF | 24357 |
| HPV16 | E1 | 9 | 501 | FVNSKSHFW | 24358 |
| HPV16 | E1 | 10 | 501 | FVNSKSHFWL | 24359 |
| HPV16 | E1 | 8 | 466 | GIPKKNCI | 24360 |
| HPV16 | E1 | 9 | 466 | GIPKKNCIL | 24361 |
| HPV16 | E1 | 10 | 466 | GIPKKNCILL | 24362 |
| HPV16 | E1 | 11 | 466 | GIPKKNCILLY | 24363 |
| HPV16 | E1 | 8 | 325 | GISNISEV | 24364 |
| HPV16 | E1 | 9 | 325 | GISNISEVY | 24365 |
| HPV16 | E1 | 10 | 242 | GLTPSIADSI | 24366 |
| HPV16 | E1 | 8 | 519 | GMLDDATV | 24367 |
| HPV16 | E1 | 11 | 519 | GMLDDATVPCW | 24368 |
| HPV16 | E1 | 8 | 487 | GMSLMKFL | 24369 |
| HPV16 | E1 | 8 | 272 | GMVVLLLV | 24370 |
| HPV16 | E1 | 10 | 272 | GMVVLLLVRY | 24371 |
| HPV16 | E1 | 8 | 450 | GVEFMSFL | 24372 |
| HPV16 | E1 | 10 | 450 | GVEFMSFLTA | 24373 |
| HPV16 | E1 | 11 | 450 | GVEFMSFLTAL | 24374 |
| HPV16 | E1 | 8 | 179 | GVSERHTI | 24375 |
| HPV16 | E1 | 8 | 216 | GVSFSELV | 24376 |
| HPV16 | E1 | 11 | 216 | GVSFSELVRPF | 24377 |
| HPV16 | E1 | 9 | 263 | HIQSLACSW | 24378 |
| HPV16 | E1 | 11 | 263 | HIQSLACSWGM | 24379 |
| HPV16 | E1 | 10 | 194 | ILNVLKTSNA | 24380 |
| HPV16 | E1 | 8 | 467 | IPKKNCIL | 24381 |
| HPV16 | E1 | 9 | 467 | IPKKNCILL | 24382 |
| HPV16 | E1 | 10 | 467 | IPKKNCILLY | 24383 |
| HPV16 | E1 | 11 | 340 | IQRQTVLQHSF | 24384 |

TABLE XIV-continued

B62 Supermotif Peptides

| Type | Protein | No. of Amino Acid | Position | Sequence | Seq. Id. No. |
|---|---|---|---|---|---|
| HPV16 | E1 | 8 | 264 | IQSLACSW | 24385 |
| HPV16 | E1 | 10 | 264 | IQSLACSWGM | 24386 |
| HPV16 | E1 | 11 | 264 | IQSLACSWGMV | 24387 |
| HPV16 | E1 | 8 | 369 | IVDDSEIA | 24388 |
| HPV16 | E1 | 9 | 369 | IVDDSEIAY | 24389 |
| HPV16 | E1 | 11 | 369 | IVDDSEIAYKY | 24390 |
| HPV16 | E1 | 8 | 401 | IVKDCATM | 24391 |
| HPV16 | E1 | 10 | 442 | IVMFLRYQGV | 24392 |
| HPV16 | E1 | 8 | 52 | IVNDNDYL | 24393 |
| HPV16 | E1 | 11 | 52 | IVNDNDYLTQA | 24394 |
| HPV16 | E1 | 8 | 517 | KIGMLDDA | 24395 |
| HPV16 | E1 | 10 | 517 | KIGMLDDATV | 24396 |
| HPV16 | E1 | 9 | 400 | KIVKDCATM | 24397 |
| HPV16 | E1 | 8 | 296 | KLLCVSPM | 24398 |
| HPV16 | E1 | 10 | 296 | KLLCVSPMCM | 24399 |
| HPV16 | E1 | 11 | 296 | KLLCVSPMCMM | 24400 |
| HPV16 | E1 | 9 | 292 | KLLSKLLCV | 24401 |
| HPV16 | E1 | 8 | 311 | KLRSTAAA | 24402 |
| HPV16 | E1 | 9 | 311 | KLRSTAAAL | 24403 |
| HPV16 | E1 | 10 | 311 | KLRSTAAALY | 24404 |
| HPV16 | E1 | 11 | 311 | KLRSTAAALYW | 24405 |
| HPV16 | E1 | 9 | 77 | KQHRDAVQV | 24406 |
| HPV16 | E1 | 10 | 77 | KQHRDAVQVL | 24407 |
| HPV16 | E1 | 9 | 440 | KQIVMFLRY | 24408 |
| HPV16 | E1 | 8 | 418 | KQMSMSQW | 24409 |
| HPV16 | E1 | 9 | 418 | KQMSMSQWI | 24410 |
| HPV16 | E1 | 11 | 418 | KQMSMSQWIKY | 24411 |
| HPV16 | E1 | 10 | 117 | KQSRAAKRRL | 24412 |
| HPV16 | E1 | 11 | 117 | KQSRAAKRRLF | 24413 |
| HPV16 | E1 | 8 | 563 | LITSNINA | 24414 |
| HPV16 | E1 | 9 | 297 | LLCVSPMCM | 24415 |
| HPV16 | E1 | 10 | 297 | LLCVSPMCMM | 24416 |
| HPV16 | E1 | 11 | 297 | LLCVSPMCMMI | 24417 |
| HPV16 | E1 | 9 | 562 | LLITSNINA | 24418 |
| HPV16 | E1 | 8 | 254 | LLQQYCLY | 24419 |
| HPV16 | E1 | 9 | 254 | LLQQYCLYL | 24420 |
| HPV16 | E1 | 11 | 254 | LLQQYCLYLHI | 24421 |
| HPV16 | E1 | 8 | 293 | LLSKLLCV | 24422 |
| HPV16 | E1 | 11 | 293 | LLSKLLCVSPM | 24423 |
| HPV16 | E1 | 9 | 490 | LMKFLQGSV | 24424 |
| HPV16 | E1 | 10 | 490 | LMKFLQGSVI | 24425 |
| HPV16 | E1 | 10 | 464 | LQGIPKKNCI | 24426 |
| HPV16 | E1 | 11 | 464 | LQGIPKKNCIL | 24427 |
| HPV16 | E1 | 8 | 494 | LQGSVICF | 24428 |
| HPV16 | E1 | 9 | 494 | LQGSVICFV | 24429 |
| HPV16 | E1 | 10 | 346 | LQHSFNDCTF | 24430 |
| HPV16 | E1 | 9 | 510 | LQPLADAKI | 24431 |
| HPV16 | E1 | 11 | 510 | LQPLADAKIGM | 24432 |
| HPV16 | E1 | 8 | 255 | LQQYCLYL | 24433 |
| HPV16 | E1 | 10 | 255 | LQQYCLYLHI | 24434 |
| HPV16 | E1 | 11 | 48 | LVDFIVNDNDY | 24435 |
| HPV16 | E1 | 9 | 554 | LVQLKCPPL | 24436 |
| HPV16 | E1 | 10 | 554 | LVQLKCPPLL | 24437 |
| HPV16 | E1 | 11 | 554 | LVQLKCPPLLI | 24438 |
| HPV16 | E1 | 11 | 544 | LVSMDVKHRPL | 24439 |
| HPV16 | E1 | 8 | 91 | LVSPLSDI | 24440 |
| HPV16 | E1 | 10 | 583 | LVVFTFPNEF | 24441 |
| HPV16 | E1 | 11 | 306 | MIEPPKLRSTA | 24442 |
| HPV16 | E1 | 8 | 207 | MLAKFKEL | 24443 |
| HPV16 | E1 | 9 | 207 | MLAKFKELY | 24444 |
| HPV16 | E1 | 11 | 207 | MLAKFKELYGV | 24445 |
| HPV16 | E1 | 10 | 520 | MLDDATVPCW | 24446 |
| HPV16 | E1 | 8 | 305 | MMIEPPKL | 24447 |
| HPV16 | E1 | 10 | 360 | MVQWAYDNDI | 24448 |
| HPV16 | E1 | 11 | 360 | MVQWAYDNDIV | 24449 |
| HPV16 | E1 | 9 | 273 | MVVLLLVRY | 24450 |
| HPV16 | E1 | 11 | 193 | NILNVLKTSNA | 24451 |
| HPV16 | E1 | 10 | 567 | NINAGTDSRW | 24452 |
| HPV16 | E1 | 8 | 105 | NISPRLKA | 24453 |
| HPV16 | E1 | 9 | 105 | NISPRLKAI | 24454 |
| HPV16 | E1 | 11 | 105 | NISPRLKAICI | 24455 |
| HPV16 | E1 | 10 | 535 | NLRNALDGNL | 24456 |
| HPV16 | E1 | 11 | 535 | NLRNALDGNLV | 24457 |
| HPV16 | E1 | 11 | 599 | NPVYELNDKNW | 24458 |
| HPV16 | E1 | 8 | 196 | NVLKTSNA | 24459 |

TABLE XIV-continued

B62 Supermotif Peptides

| Type | Protein | No. of Amino Acid | Position | Sequence | Seq. Id. No. |
|---|---|---|---|---|---|
| HPV16 | E1 | 10 | 196 | NVLKTSNAKA | 24460 |
| HPV16 | E1 | 11 | 196 | NVLKTSNAKAA | 24461 |
| HPV16 | E1 | 9 | 512 | PLADAKIGM | 24462 |
| HPV16 | E1 | 10 | 512 | PLADAKIGML | 24463 |
| HPV16 | E1 | 8 | 561 | PLLITSNI | 24464 |
| HPV16 | E1 | 10 | 561 | PLLITSNINA | 24465 |
| HPV16 | E1 | 9 | 94 | PLSDISGCV | 24466 |
| HPV16 | E1 | 8 | 190 | PLTNILNV | 24467 |
| HPV16 | E1 | 9 | 190 | PLTNILNVL | 24468 |
| HPV16 | E1 | 10 | 553 | PLVQLKCPPL | 24469 |
| HPV16 | E1 | 11 | 553 | PLVQLKCPPLL | 24470 |
| HPV16 | E1 | 11 | 302 | PMCMMIEPPKL | 24471 |
| HPV16 | E1 | 8 | 309 | PPKLRSTA | 24472 |
| HPV16 | E1 | 9 | 309 | PPKLRSTAA | 24473 |
| HPV16 | E1 | 10 | 309 | PPKLRSTAAA | 24474 |
| HPV16 | E1 | 11 | 309 | PPKLRSTAAAL | 24475 |
| HPV16 | E1 | 9 | 560 | PPLLITSNI | 24476 |
| HPV16 | E1 | 11 | 560 | PPLLITSNINA | 24477 |
| HPV16 | E1 | 10 | 600 | PVYELNDKNW | 24478 |
| HPV16 | E1 | 8 | 441 | QIVMFLRY | 24479 |
| HPV16 | E1 | 11 | 441 | QIVMFLRYQGV | 24480 |
| HPV16 | E1 | 9 | 381 | QLADTNSNA | 24481 |
| HPV16 | E1 | 11 | 381 | QLADTNSNASA | 24482 |
| HPV16 | E1 | 8 | 556 | QLKCPPLL | 24483 |
| HPV16 | E1 | 9 | 556 | QLKCPPLLI | 24484 |
| HPV16 | E1 | 8 | 419 | QMSMSQWI | 24485 |
| HPV16 | E1 | 10 | 419 | QMSMSQWIKY | 24486 |
| HPV16 | E1 | 11 | 359 | QMVQWAYDNDI | 24487 |
| HPV16 | E1 | 8 | 511 | QPLADAKI | 24488 |
| HPV16 | E1 | 10 | 511 | QPLADAKIGM | 24489 |
| HPV16 | E1 | 11 | 511 | QPLADAKIGML | 24490 |
| HPV16 | E1 | 9 | 256 | QQYCLYLHI | 24491 |
| HPV16 | E1 | 8 | 84 | QVLKRKYL | 24492 |
| HPV16 | E1 | 9 | 84 | QVLKRKYLV | 24493 |
| HPV16 | E1 | 10 | 125 | RLFESEDSGY | 24494 |
| HPV16 | E1 | 11 | 582 | RLVVFTFPNEF | 24495 |
| HPV16 | E1 | 11 | 552 | RPLVQLKCPPL | 24496 |
| HPV16 | E1 | 9 | 342 | RQTVLQHSF | 24497 |
| HPV16 | E1 | 8 | 432 | RVDDGGDW | 24498 |
| HPV16 | E1 | 11 | 432 | RVDDGGDWKQI | 24499 |
| HPV16 | E1 | 9 | 246 | SIADSIKTL | 24500 |
| HPV16 | E1 | 10 | 246 | SIADSIKTLL | 24501 |
| HPV16 | E1 | 9 | 250 | SIKTLLQQY | 24502 |
| HPV16 | E1 | 11 | 250 | SIKTLLQQYCL | 24503 |
| HPV16 | E1 | 8 | 266 | SLACSWGM | 24504 |
| HPV16 | E1 | 9 | 266 | SLACSWGMV | 24505 |
| HPV16 | E1 | 10 | 266 | SLACSWGMVV | 24506 |
| HPV16 | E1 | 11 | 266 | SLACSWGMVVL | 24507 |
| HPV16 | E1 | 8 | 484 | SLFGMSLM | 24508 |
| HPV16 | E1 | 10 | 484 | SLFGMSLMKF | 24509 |
| HPV16 | E1 | 11 | 484 | SLFGMSLMKFL | 24510 |
| HPV16 | E1 | 10 | 489 | SLMKFLQGSV | 24511 |
| HPV16 | E1 | 11 | 489 | SLMKFLQGSVI | 24512 |
| HPV16 | E1 | 8 | 634 | SLPTFKCV | 24513 |
| HPV16 | E1 | 9 | 546 | SMDVKHRPL | 24514 |
| HPV16 | E1 | 10 | 546 | SMDVKIHRPLV | 24515 |
| HPV16 | E1 | 8 | 421 | SMSQWIKY | 24516 |
| HPV16 | E1 | 10 | 93 | SPLSDISGCV | 24517 |
| HPV16 | E1 | 9 | 107 | SPRLKAICI | 24518 |
| HPV16 | E1 | 10 | 397 | SQAKIVKDCA | 24519 |
| HPV16 | E1 | 8 | 358 | SQMVQWAY | 24520 |
| HPV16 | E1 | 11 | 423 | SQWIKYRCDRV | 24521 |
| HPV16 | E1 | 10 | 185 | TICQTPLTNI | 24522 |
| HPV16 | E1 | 11 | 185 | TICQTPLTNIL | 24523 |
| HPV16 | E1 | 9 | 289 | TIEKLLSKL | 24524 |
| HPV16 | E1 | 10 | 289 | TIEKLLSKLL | 24525 |
| HPV16 | E1 | 8 | 253 | TLLQQYCL | 24526 |
| HPV16 | E1 | 9 | 253 | TLLQQYCLY | 24527 |
| HPV16 | E1 | 10 | 253 | TLLQQYCLYL | 24528 |
| HPV16 | E1 | 9 | 407 | TMCRHYKRA | 24529 |
| HPV16 | E1 | 10 | 336 | TPEWIQRQTV | 24530 |
| HPV16 | E1 | 11 | 336 | TPEWIQRQTVL | 24531 |
| HPV16 | E1 | 9 | 189 | TPLTNILNV | 24532 |
| HPV16 | E1 | 10 | 189 | TPLTNILNVL | 24533 |
| HPV16 | E1 | 8 | 244 | TPSIADSI | 24534 |

TABLE XIV-continued

B62 Supermotif Peptides

| Type | Protein | No. of Amino Acid | Position | Sequence | Seq. Id. No. |
|---|---|---|---|---|---|
| HPV16 | E1 | 11 | 244 | TPSIADSIKTL | 24535 |
| HPV16 | E1 | 8 | 60 | TQAETETA | 24536 |
| HPV16 | E1 | 10 | 60 | TQAETETAHA | 24537 |
| HPV16 | E1 | 11 | 60 | TQAETETAHAL | 24538 |
| HPV16 | E1 | 8 | 525 | TVPCWNYI | 24539 |
| HPV16 | E1 | 11 | 498 | VICFVNSKSHF | 24540 |
| HPV16 | E1 | 8 | 85 | VLKRKYLV | 24541 |
| HPV16 | E1 | 11 | 85 | VLKRKYLVSPL | 24542 |
| HPV16 | E1 | 9 | 197 | VLKTSNAKA | 24543 |
| HPV16 | E1 | 10 | 197 | VLKTSNAKAA | 24544 |
| HPV16 | E1 | 11 | 197 | VLKTSNAKAAM | 24545 |
| HPV16 | E1 | 11 | 345 | VLQHSFNDCTF | 24546 |
| HPV16 | E1 | 9 | 443 | VMFLRYQGV | 24547 |
| HPV16 | E1 | 11 | 443 | VMFLRYQGVEF | 24548 |
| HPV16 | E1 | 11 | 526 | VPCWNYIDDNL | 24549 |
| HPV16 | E1 | 8 | 555 | VQLKCPPL | 24550 |
| HPV16 | E1 | 9 | 555 | VQLKCPPLL | 24551 |
| HPV16 | E1 | 10 | 555 | VQLKCPPLLI | 24552 |
| HPV16 | E1 | 8 | 83 | VQVLKRKY | 24553 |
| HPV16 | E1 | 9 | 83 | VQVLKRKYL | 24554 |
| HPV16 | E1 | 10 | 83 | VQVLKRKYLV | 24555 |
| HPV16 | E1 | 9 | 361 | VQWAYDNDI | 24556 |
| HPV16 | E1 | 10 | 361 | VQWAYDNDIV | 24557 |
| HPV16 | E1 | 9 | 24 | VVEKKTGDA | 24558 |
| HPV16 | E1 | 10 | 24 | VVEKKTGDAI | 24559 |
| HPV16 | E1 | 9 | 584 | VVFTFPNEF | 24560 |
| HPV16 | E1 | 11 | 584 | VVFTFPNEFPF | 24561 |
| HPV16 | E1 | 8 | 274 | VVLLLVRY | 24562 |
| HPV16 | E1 | 9 | 425 | WIKYRCDRV | 24563 |
| HPV16 | E1 | 8 | 339 | WIQRQTVL | 24564 |
| HPV16 | E1 | 8 | 509 | WLQPLADA | 24565 |
| HPV16 | E1 | 10 | 509 | WLQPLADAKI | 24566 |
| HPV16 | E1 | 8 | 576 | WPYLHNRL | 24567 |
| HPV16 | E1 | 9 | 576 | WPYLHNRLV | 24568 |
| HPV16 | E1 | 10 | 576 | WPYLHNRLVV | 24569 |
| HPV16 | E1 | 11 | 576 | WPYLHNRLVVF | 24570 |
| HPV16 | E1 | 9 | 531 | YIDDNLRNA | 24571 |
| HPV16 | E1 | 10 | 531 | YIDDNLRNAL | 24572 |
| HPV16 | E1 | 8 | 261 | YLHIQSLA | 24573 |
| HPV16 | E1 | 11 | 261 | YLHIQSLACSW | 24574 |
| HPV16 | E1 | 8 | 578 | YLHNRLVV | 24575 |
| HPV16 | E1 | 9 | 578 | YLHNRLVVF | 24576 |
| HPV16 | E1 | 11 | 578 | YLHNRLVVFTF | 24577 |
| HPV16 | E1 | 10 | 58 | YLTQAETETA | 24578 |
| HPV16 | E1 | 9 | 90 | YLVSPLSDI | 24579 |
| HPV16 | E1 | 9 | 448 | YQGVEFMSF | 24580 |
| HPV16 | E1 | 10 | 448 | YQGVEFMSFL | 24581 |
| HPV16 | E2 | 8 | 72 | AIELQLTL | 24582 |
| HPV16 | E2 | 11 | 72 | AIELQLTLETI | 24583 |
| HPV16 | E2 | 11 | 331 | AIVTLTYDSEW | 24584 |
| HPV16 | E2 | 9 | 41 | AIYYKAREM | 24585 |
| HPV16 | E2 | 11 | 41 | AIYYKAREMGF | 24586 |
| HPV16 | E2 | 11 | 228 | ALGTEETQTTI | 24587 |
| HPV16 | E2 | 9 | 69 | ALQAIELQL | 24588 |
| HPV16 | E2 | 11 | 69 | ALQAIELQLTL | 24589 |
| HPV16 | E2 | 11 | 105 | APTGCIKKHGY | 24590 |
| HPV16 | E2 | 8 | 63 | AVSKNKAL | 24591 |
| HPV16 | E2 | 10 | 63 | AVSKNKALQA | 24592 |
| HPV16 | E2 | 11 | 63 | AVSKAAALQAI | 24593 |
| HPV16 | E2 | 8 | 314 | AVSSTWHW | 24594 |
| HPV16 | E2 | 9 | 109 | CIKKHGYTV | 24595 |
| HPV16 | E2 | 11 | 109 | CIKKHGYTVEV | 24596 |
| HPV16 | E2 | 11 | 195 | CPTSVFSSNEV | 24597 |
| HPV16 | E2 | 9 | 11 | CQDKILTHY | 24598 |
| HPV16 | E2 | 11 | 5 | CQRLNVCQDKI | 24599 |
| HPV16 | E2 | 8 | 124 | DICNTMHY | 24600 |
| HPV16 | E2 | 11 | 124 | DICNTMHYTNW | 24601 |
| HPV16 | E2 | 8 | 25 | DLRDHIDY | 24602 |
| HPV16 | E2 | 9 | 25 | DLRDHIDYW | 24603 |
| HPV16 | E2 | 9 | 344 | DQFLSQVKI | 24604 |
| HPV16 | E2 | 8 | 96 | DVSLEVYL | 24605 |
| HPV16 | E2 | 10 | 96 | DVSLEVYLTA | 24606 |
| HPV16 | E2 | 8 | 209 | EIIRQHLA | 24607 |
| HPV16 | E2 | 9 | 74 | ELQLTLETI | 24608 |
| HPV16 | E2 | 10 | 74 | ELQLTLETIY | 24609 |

TABLE XIV-continued

B62 Supermotif Peptides

| Type | Protein | No. of Amino Acid | Position | Sequence | Seq. Id. No. |
|---|---|---|---|---|---|
| HPV16 | E2 | 11 | 48 | EMGFKHINHQV | 24610 |
| HPV16 | E2 | 8 | 185 | EVHAGGQV | 24611 |
| HPV16 | E2 | 9 | 185 | EVHAGGQVI | 24612 |
| HPV16 | E2 | 10 | 185 | EVHAGGQVIL | 24613 |
| HPV16 | E2 | 8 | 118 | EVQFDGDI | 24614 |
| HPV16 | E2 | 8 | 204 | EVSSPEII | 24615 |
| HPV16 | E2 | 11 | 100 | EVYLTAPTGCI | 24616 |
| HPV16 | E2 | 11 | 346 | FLSQVKLPKTI | 24617 |
| HPV16 | E2 | 8 | 168 | FVQFKDDA | 24618 |
| HPV16 | E2 | 11 | 168 | FVQFKDDAEKY | 24619 |
| HPV16 | E2 | 9 | 163 | GIRTYFVQF | 24620 |
| HPV16 | E2 | 9 | 156 | GLYYVHEGI | 24621 |
| HPV16 | E2 | 8 | 150 | GQVDYYGL | 24622 |
| HPV16 | E2 | 9 | 150 | GQVDYYGLY | 24623 |
| HPV16 | E2 | 10 | 150 | GQVDYYGLYY | 24624 |
| HPV16 | E2 | 11 | 150 | GQVDYYGLYYV | 24625 |
| HPV16 | E2 | 10 | 190 | GQVILCPTSV | 24626 |
| HPV16 | E2 | 11 | 190 | GQVILCPTSVF | 24627 |
| HPV16 | E2 | 8 | 29 | HIDYWKHM | 24628 |
| HPV16 | E2 | 10 | 29 | HIDYWKHMRL | 24629 |
| HPV16 | E2 | 10 | 53 | HINHQVVPTL | 24630 |
| HPV16 | E2 | 11 | 53 | HINHQVVPTLA | 24631 |
| HPV16 | E2 | 8 | 136 | HIYICEEA | 24632 |
| HPV16 | E2 | 10 | 136 | HIYICEEASV | 24633 |
| HPV16 | E2 | 8 | 214 | HLANHPAA | 24634 |
| HPV16 | E2 | 9 | 290 | HLKGDANTL | 24635 |
| HPV16 | E2 | 8 | 35 | HMRLECAI | 24636 |
| HPV16 | E2 | 9 | 35 | HMRLECAIY | 24637 |
| HPV16 | E2 | 10 | 35 | HMRLECAIYY | 24638 |
| HPV16 | E2 | 9 | 218 | HPAATHTKA | 24639 |
| HPV16 | E2 | 10 | 218 | HPAATHTKAV | 24640 |
| HPV16 | E2 | 11 | 218 | HPAATHTKAVA | 24641 |
| HPV16 | E2 | 8 | 56 | HQVVPTLA | 24642 |
| HPV16 | E2 | 9 | 56 | HQVVPTLAV | 24643 |
| HPV16 | E2 | 11 | 210 | IIRQHLANHPA | 24644 |
| HPV16 | E2 | 8 | 193 | ILCPTSVF | 24645 |
| HPV16 | E2 | 11 | 352 | IPKTITVSTGF | 24646 |
| HPV16 | E2 | 8 | 288 | IVHLKGDA | 24647 |
| HPV16 | E2 | 11 | 288 | IVHLKGDANTL | 24648 |
| HPV16 | E2 | 10 | 332 | IVTLTYDSEW | 24649 |
| HPV16 | E2 | 8 | 351 | KIPKTITV | 24650 |
| HPV16 | E2 | 8 | 255 | KLLHRDSV | 24651 |
| HPV16 | E2 | 11 | 255 | KLLHRDSVDSA | 24652 |
| HPV16 | E2 | 11 | 182 | KVWEVHAGGQV | 24653 |
| HPV16 | E2 | 10 | 256 | LLHRDSVDSA | 24654 |
| HPV16 | E2 | 8 | 70 | LQAIELQL | 24655 |
| HPV16 | E2 | 10 | 70 | LQAIELQLTL | 24656 |
| HPV16 | E2 | 8 | 94 | LQDVSLEV | 24657 |
| HPV16 | E2 | 9 | 94 | LQDVSLEVY | 24658 |
| HPV16 | E2 | 10 | 94 | LQDVSLEVYL | 24659 |
| HPV16 | E2 | 8 | 75 | LQLTLETI | 24660 |
| HPV16 | E2 | 9 | 75 | LQLTLETIY | 24661 |
| HPV16 | E2 | 8 | 249 | NPCHTTKL | 24662 |
| HPV16 | E2 | 9 | 249 | NPCHTTKLL | 24663 |
| HPV16 | E2 | 8 | 9 | NVCQDKIL | 24664 |
| HPV16 | E2 | 11 | 9 | NVCQDKILTHY | 24665 |
| HPV16 | E2 | 8 | 325 | NVKHKSAI | 24666 |
| HPV16 | E2 | 9 | 325 | NVKHKSAIV | 24667 |
| HPV16 | E2 | 11 | 325 | NVKHKSAIVTL | 24668 |
| HPV16 | E2 | 9 | 287 | PIVHLKGDA | 24669 |
| HPV16 | E2 | 8 | 76 | QLTLETIY | 24670 |
| HPV16 | E2 | 8 | 151 | QVDYYGLY | 24671 |
| HPV16 | E2 | 9 | 151 | QVDYYGLYY | 24672 |
| HPV16 | E2 | 10 | 151 | QVDYYGLYYV | 24673 |
| HPV16 | E2 | 9 | 191 | QVILCPTSV | 24674 |
| HPV16 | E2 | 10 | 191 | QVILCPTSVF | 24675 |
| HPV16 | E2 | 8 | 349 | QVKIPKTI | 24676 |
| HPV16 | E2 | 10 | 349 | QVKIPKTITV | 24677 |
| HPV16 | E2 | 8 | 57 | QVVPTLAV | 24678 |
| HPV16 | E2 | 11 | 278 | RINCNSNTTPI | 24679 |
| HPV16 | E2 | 8 | 37 | RLECAIYY | 24680 |
| HPV16 | E2 | 10 | 37 | RLECAIYYKA | 24681 |
| HPV16 | E2 | 9 | 7 | RLNVCQDKI | 24682 |
| HPV16 | E2 | 10 | 7 | RLNVCQDKIL | 24683 |
| HPV16 | E2 | 9 | 212 | RQHLANHPA | 24684 |

TABLE XIV-continued

B62 Supermotif Peptides

| Type | Protein | No. of Amino Acid | Position | Sequence | Seq. Id. No. |
|---|---|---|---|---|---|
| HPV16 | E2 | 10 | 212 | RQHLANHPAA | 24685 |
| HPV16 | E2 | 8 | 98 | SLEVYLTA | 24686 |
| HPV16 | E2 | 9 | 207 | SPEIIRQHL | 24687 |
| HPV16 | E2 | 10 | 207 | SPEIIRQHLA | 24688 |
| HPV16 | E2 | 9 | 348 | SQVKIPKTI | 24689 |
| HPV16 | E2 | 11 | 348 | SQVKIPKTITV | 24690 |
| HPV16 | E2 | 8 | 85 | SQYSNEKW | 24691 |
| HPV16 | E2 | 10 | 85 | SQYSNEKWTL | 24692 |
| HPV16 | E2 | 8 | 261 | SVDSAPIL | 24693 |
| HPV16 | E2 | 10 | 261 | SVDSAPILTA | 24694 |
| HPV16 | E2 | 11 | 261 | SVDSAPILTAF | 24695 |
| HPV16 | E2 | 8 | 198 | SVFSSNEV | 24696 |
| HPV16 | E2 | 9 | 144 | SVTVVEGQV | 24697 |
| HPV16 | E2 | 11 | 144 | SVTVVEGQVDY | 24698 |
| HPV16 | E2 | 8 | 355 | TITVSTGF | 24699 |
| HPV16 | E2 | 9 | 355 | TITVSTGFM | 24700 |
| HPV16 | E2 | 11 | 355 | TITVSTGFMSI | 24701 |
| HPV16 | E2 | 9 | 61 | TLAVSKNKA | 24702 |
| HPV16 | E2 | 10 | 61 | TLAVSKNKAL | 24703 |
| HPV16 | E2 | 8 | 3 | TLCQRLNV | 24704 |
| HPV16 | E2 | 10 | 78 | TLETIYNSQY | 24705 |
| HPV16 | E2 | 9 | 297 | TLKCLRYRF | 24706 |
| HPV16 | E2 | 9 | 93 | TLQDVSLEV | 24707 |
| HPV16 | E2 | 10 | 93 | TLQDVSLEVY | 24708 |
| HPV16 | E2 | 11 | 93 | TLQDVSLEVYL | 24709 |
| HPV16 | E2 | 8 | 334 | TLTYDSEW | 24710 |
| HPV16 | E2 | 10 | 310 | TLYTAVSSTW | 24711 |
| HPV16 | E2 | 10 | 128 | TMHYTNWTHI | 24712 |
| HPV16 | E2 | 11 | 128 | TMHYTNWTHIY | 24713 |
| HPV16 | E2 | 10 | 286 | TPIVHLKGDA | 24714 |
| HPV16 | E2 | 10 | 116 | TVEVQFDGDI | 24715 |
| HPV16 | E2 | 9 | 357 | TVSTGFMSI | 24716 |
| HPV16 | E2 | 9 | 146 | TVVEGQVDY | 24717 |
| HPV16 | E2 | 10 | 146 | TVVEGQVDYY | 24718 |
| HPV16 | E2 | 8 | 192 | VILCPTSV | 24719 |
| HPV16 | E2 | 9 | 192 | VILCPTSVF | 24720 |
| HPV16 | E2 | 11 | 59 | VPTLAVSKNKA | 24721 |
| HPV16 | E2 | 11 | 119 | VQFDGDICNTM | 24722 |
| HPV16 | E2 | 10 | 169 | VQFKDDAEKY | 24723 |
| HPV16 | E2 | 8 | 147 | VVEGQVDY | 24724 |
| HPV16 | E2 | 9 | 147 | VVEGQVDYY | 24725 |
| HPV16 | E2 | 11 | 147 | VVEGQVDYYGL | 24726 |
| HPV16 | E2 | 10 | 341 | WQRDQFLSQV | 24727 |
| HPV16 | E2 | 8 | 138 | YICEEASV | 24728 |
| HPV16 | E2 | 10 | 138 | YICEEASVTV | 24729 |
| HPV16 | E2 | 11 | 138 | YICEEASVTVV | 24730 |
| HPV16 | E2 | 9 | 102 | YLTAPTGCI | 24731 |
| HPV16 | E2 | 9 | 159 | YVHEGIRTY | 24732 |
| HPV16 | E2 | 10 | 159 | YVHEGIRTYF | 24733 |
| HPV16 | E2 | 11 | 159 | YVHEGIRTYFV | 24734 |
| HPV16 | E5 | 8 | 26 | CLLIRPLL | 24735 |
| HPV16 | E5 | 9 | 26 | CLLIRPLLL | 24736 |
| HPV16 | E5 | 11 | 26 | CLLIRPLLLSV | 24737 |
| HPV16 | E5 | 9 | 24 | CVCLLIRPL | 24738 |
| HPV16 | E5 | 10 | 24 | CVCLLIRPLL | 24739 |
| HPV16 | E5 | 11 | 24 | CVCLLIRPLLL | 24740 |
| HPV16 | E5 | 8 | 20 | CVLLCVCL | 24741 |
| HPV16 | E5 | 9 | 20 | CVLLCVCLL | 24742 |
| HPV16 | E5 | 10 | 20 | CVLLCVCLLI | 24743 |
| HPV16 | E5 | 8 | 60 | FIVYIIFV | 24744 |
| HPV16 | E5 | 9 | 60 | FIVYIIFVY | 24745 |
| HPV16 | E5 | 10 | 60 | FIVYIIFVYI | 24746 |
| HPV16 | E5 | 9 | 72 | FLIHTHARF | 24747 |
| HPV16 | E5 | 10 | 72 | FLIHTHARFL | 24748 |
| HPV16 | E5 | 11 | 72 | FLIRTHARFLI | 24749 |
| HPV16 | E5 | 8 | 15 | FLLCFCVL | 24750 |
| HPV16 | E5 | 9 | 15 | FLLCFCVLL | 24751 |
| HPV16 | E5 | 11 | 15 | FLLCFCVLLCV | 24752 |
| HPV16 | E5 | 8 | 66 | FVYIPLFL | 24753 |
| HPV16 | E5 | 9 | 66 | FVYIPLFLI | 24754 |
| HPV16 | E5 | 8 | 64 | IIFVYIPL | 24755 |
| HPV16 | E5 | 9 | 64 | IIFVYIPLF | 24756 |
| HPV16 | E5 | 10 | 64 | IIFVYIPLFL | 24757 |
| HPV16 | E5 | 11 | 64 | IIFVYIPLFLI | 24758 |
| HPV16 | E5 | 8 | 43 | IILVLLLW | 24759 |

TABLE XIV-continued

B62 Supermotif Peptides

| Type | Protein | No. of Amino Acid | Position | Sequence | Seq. Id. No. |
|---|---|---|---|---|---|
| HPV16 | E5 | 9 | 43 | IILVLLLWI | 24760 |
| HPV16 | E5 | 11 | 43 | IILVLLLWITA | 24761 |
| HPV16 | E5 | 8 | 44 | ILVLLLWI | 24762 |
| HPV16 | E5 | 10 | 44 | ILVLLLWITA | 24763 |
| HPV16 | E5 | 11 | 44 | ILVLLLWITAA | 24764 |
| HPV16 | E5 | 10 | 69 | IPLFLIHTHA | 24765 |
| HPV16 | E5 | 8 | 61 | IVYIIFVY | 24766 |
| HPV16 | E5 | 9 | 61 | IVYIIFVYI | 24767 |
| HPV16 | E5 | 11 | 61 | IVYIIFVYIPL | 24768 |
| HPV16 | E5 | 8 | 73 | LIHTHARF | 24769 |
| HPV16 | E5 | 9 | 73 | LIHTHARFL | 24770 |
| HPV16 | E5 | 10 | 73 | LIHTHARFLI | 24771 |
| HPV16 | E5 | 8 | 42 | LIILVLLL | 24772 |
| HPV16 | E5 | 9 | 42 | LIILVLLLW | 24773 |
| HPV16 | E5 | 10 | 42 | LIILVLLLWI | 24774 |
| HPV16 | E5 | 9 | 28 | LIRPLLLSV | 24775 |
| HPV16 | E5 | 9 | 11 | LLACFLLCF | 24776 |
| HPV16 | E5 | 11 | 11 | LLACFLLCFCV | 24777 |
| HPV16 | E5 | 8 | 16 | LLCFCVLL | 24778 |
| HPV16 | E5 | 10 | 16 | LLCFCVLLCV | 24779 |
| HPV16 | E5 | 8 | 22 | LLCVCLLI | 24780 |
| HPV16 | E5 | 11 | 22 | LLCVCLLIRPL | 24781 |
| HPV16 | E5 | 8 | 27 | LLIRPLLL | 24782 |
| HPV16 | E5 | 10 | 27 | LLIRPLLLSV | 24783 |
| HPV16 | E5 | 8 | 32 | LLLSVSTY | 24784 |
| HPV16 | E5 | 11 | 32 | LLLSVSTYTSL | 24785 |
| HPV16 | E5 | 8 | 47 | LLLWITAA | 24786 |
| HPV16 | E5 | 10 | 47 | LLLWITAASA | 24787 |
| HPV16 | E5 | 11 | 47 | LLLWITAASAF | 24788 |
| HPV16 | E5 | 10 | 33 | LLSVSTYTSL | 24789 |
| HPV16 | E5 | 11 | 33 | LLSVSTYTSLI | 24790 |
| HPV16 | E5 | 9 | 48 | LLWITAASA | 24791 |
| HPV16 | E5 | 10 | 48 | LLWITAASAF | 24792 |
| HPV16 | E5 | 9 | 45 | LVLLLWITA | 24793 |
| HPV16 | E5 | 10 | 45 | LVLLLWITAA | 24794 |
| HPV16 | E5 | 9 | 3 | NLDTASTTL | 24795 |
| HPV16 | E5 | 10 | 3 | NLDTASTTLL | 24796 |
| HPV16 | E5 | 11 | 3 | NLDTASTTLLA | 24797 |
| HPV16 | E5 | 9 | 70 | PLFLIHTHA | 24798 |
| HPV16 | E5 | 11 | 70 | PLFLIHTHARF | 24799 |
| HPV16 | E5 | 9 | 31 | PLLLSVSTY | 24800 |
| HPV16 | E5 | 10 | 30 | RPLLLSVSTY | 24801 |
| HPV16 | E5 | 8 | 41 | SLIILVLL | 24802 |
| HPV16 | E5 | 9 | 41 | SLIILVLLL | 24803 |
| HPV16 | E5 | 10 | 41 | SLIILVLLLW | 24804 |
| HPV16 | E5 | 11 | 41 | SLIILVLLLWI | 24805 |
| HPV16 | E5 | 8 | 35 | SVSTYTSL | 24806 |
| HPV16 | E5 | 9 | 35 | SVSTYTSLI | 24807 |
| HPV16 | E5 | 10 | 35 | SVSTYTSLII | 24808 |
| HPV16 | E5 | 11 | 35 | SVSTYTSLIIL | 24809 |
| HPV16 | E5 | 8 | 10 | TLLACFLL | 24810 |
| HPV16 | E5 | 10 | 10 | TLLACFLLCF | 24811 |
| HPV16 | E5 | 8 | 21 | VLLCVCLL | 24812 |
| HPV16 | E5 | 9 | 21 | VLLCVCLLI | 24813 |
| HPV16 | E5 | 8 | 46 | VLLLWITA | 24814 |
| HPV16 | E5 | 9 | 46 | VLLLWITAA | 24815 |
| HPV16 | E5 | 11 | 46 | VLLLWITAASA | 24816 |
| HPV16 | E5 | 8 | 50 | WITAASAF | 24817 |
| HPV16 | E5 | 11 | 50 | WITAASAFRCF | 24818 |
| HPV16 | E5 | 9 | 63 | YIIFVYIPL | 24819 |
| HPV16 | E5 | 10 | 63 | YIIFVYIPLF | 24820 |
| HPV16 | E5 | 11 | 63 | YIIFVYIPLFL | 24821 |
| HPV16 | E5 | 11 | 68 | YIPLFLIHTHA | 24822 |
| HPV16 | E6 | 9 | 68 | AVCDKCLKF | 24823 |
| HPV16 | E6 | 10 | 68 | AVCDKCLKFY | 24824 |
| HPV16 | E6 | 8 | 110 | CINCQKPL | 24825 |
| HPV16 | E6 | 10 | 58 | CIVYRDGNPY | 24826 |
| HPV16 | E6 | 11 | 58 | CIVYRDGNPYA | 24827 |
| HPV16 | E6 | 8 | 73 | CLKFYSKI | 24828 |
| HPV16 | E6 | 11 | 73 | CLKFYSKISEY | 24829 |
| HPV16 | E6 | 9 | 118 | CPEEKQRHL | 24830 |
| HPV16 | E6 | 8 | 37 | CVYCKQQL | 24831 |
| HPV16 | E6 | 9 | 37 | CVYCKQQLL | 24832 |
| HPV16 | E6 | 8 | 32 | DIILECVY | 24833 |
| HPV16 | E6 | 9 | 11 | DPQERPRKL | 24834 |

TABLE XIV-continued

B62 Supermotif Peptides

| Type | Protein | No. of Amino Acid | Position | Sequence | Seq. Id. No. |
|---|---|---|---|---|---|
| HPV16 | E6 | 9 | 25 | ELQTTIHDI | 24835 |
| HPV16 | E6 | 10 | 25 | ELQTTIHDII | 24836 |
| HPV16 | E6 | 11 | 25 | ELQTTIHDIIL | 24837 |
| HPV16 | E6 | 8 | 96 | EQQYNKPL | 24838 |
| HPV16 | E6 | 11 | 96 | EQQYNKPLCDL | 24839 |
| HPV16 | E6 | 10 | 48 | EVYDFAFRDL | 24840 |
| HPV16 | E6 | 11 | 9 | FQDPQERPRKL | 24841 |
| HPV16 | E6 | 8 | 125 | HLDKKQRF | 24842 |
| HPV16 | E6 | 11 | 125 | HLDKKQRFHNI | 24843 |
| HPV16 | E6 | 8 | 2 | HQKRTAMF | 24844 |
| HPV16 | E6 | 11 | 34 | ILECVYCKQQL | 24845 |
| HPV16 | E6 | 9 | 59 | IVYRDGNPY | 24846 |
| HPV16 | E6 | 10 | 59 | IVYRDGNPYA | 24847 |
| HPV16 | E6 | 11 | 59 | IVYRDGNPYAV | 24848 |
| HPV16 | E6 | 8 | 79 | KISEYRHY | 24849 |
| HPV16 | E6 | 10 | 79 | KISEYRHYCY | 24850 |
| HPV16 | E6 | 9 | 18 | KLPQLCTEL | 24851 |
| HPV16 | E6 | 8 | 101 | KPLCDLLI | 24852 |
| HPV16 | E6 | 11 | 101 | KPLCDLLIRCI | 24853 |
| HPV16 | E6 | 9 | 41 | KQQLLRREV | 24854 |
| HPV16 | E6 | 10 | 41 | KQQLLRREVY | 24855 |
| HPV16 | E6 | 11 | 129 | KQRFHNIRGRW | 24856 |
| HPV16 | E6 | 11 | 122 | KQRHLDKKQRF | 24857 |
| HPV16 | E6 | 11 | 107 | LIRCINCQKPL | 24858 |
| HPV16 | E6 | 9 | 44 | LLRREVYDF | 24859 |
| HPV16 | E6 | 10 | 44 | LLRREVYDFA | 24860 |
| HPV16 | E6 | 11 | 44 | LLRREVYDFAF | 24861 |
| HPV16 | E6 | 8 | 19 | LPQLCTEL | 24862 |
| HPV16 | E6 | 8 | 26 | LQTTIHDI | 24863 |
| HPV16 | E6 | 9 | 26 | LQTTIHDII | 24864 |
| HPV16 | E6 | 10 | 26 | LQTTIHDIIL | 24865 |
| HPV16 | E6 | 11 | 134 | NIRGRWTGRCM | 24866 |
| HPV16 | E6 | 10 | 65 | NPYAVCDKCL | 24867 |
| HPV16 | E6 | 10 | 102 | PLCDLLIRCI | 24868 |
| HPV16 | E6 | 11 | 116 | PLCPEEKQRHL | 24869 |
| HPV16 | E6 | 8 | 12 | PQERPRKL | 24870 |
| HPV16 | E6 | 11 | 12 | PQERPRKLPQL | 24871 |
| HPV16 | E6 | 11 | 20 | PQLCTELQTTI | 24872 |
| HPV16 | E6 | 10 | 21 | QLCTELQTTI | 24873 |
| HPV16 | E6 | 8 | 43 | QLLRREVY | 24874 |
| HPV16 | E6 | 10 | 43 | QLLRREVYDF | 24875 |
| HPV16 | E6 | 11 | 43 | QLLRREVYDFA | 24876 |
| HPV16 | E6 | 8 | 42 | QQLLRREV | 24877 |
| HPV16 | E6 | 9 | 42 | QQLLRREVY | 24878 |
| HPV16 | E6 | 11 | 42 | QQLLRREVYDF | 24879 |
| HPV16 | E6 | 10 | 97 | QQYNKPLCDL | 24880 |
| HPV16 | E6 | 11 | 97 | QQYNKPLCDLL | 24881 |
| HPV16 | E6 | 8 | 15 | RPRKLPQL | 24882 |
| HPV16 | E6 | 11 | 89 | SLYGTTLEQQY | 24883 |
| HPV16 | E6 | 10 | 29 | TIHDIILECV | 24884 |
| HPV16 | E6 | 11 | 29 | TIHDIILECVY | 24885 |
| HPV16 | E6 | 10 | 94 | TLEQQYNKPL | 24886 |
| HPV16 | E7 | 9 | 68 | CVQSTHVDI | 24887 |
| HPV16 | E7 | 8 | 75 | DIRTLEDL | 24888 |
| HPV16 | E7 | 9 | 75 | DIRTLEDLL | 24889 |
| HPV16 | E7 | 10 | 75 | DIRTLEDLLM | 24890 |
| HPV16 | E7 | 9 | 81 | DLLMGTLGI | 24891 |
| HPV16 | E7 | 10 | 81 | DLLMGTLGIV | 24892 |
| HPV16 | E7 | 9 | 14 | DLQPETTDL | 24893 |
| HPV16 | E7 | 10 | 14 | DLQPETTDLY | 24894 |
| HPV16 | E7 | 8 | 21 | DLYCYEQL | 24895 |
| HPV16 | E7 | 9 | 37 | EIDGPAGQA | 24896 |
| HPV16 | E7 | 9 | 46 | EPDRAHYNI | 24897 |
| HPV16 | E7 | 10 | 46 | EPDRAHYNIV | 24898 |
| HPV16 | E7 | 11 | 40 | GPAGQAEPDRA | 24899 |
| HPV16 | E7 | 8 | 43 | GQAEPDRA | 24900 |
| HPV16 | E7 | 10 | 43 | GQAEPDRAHY | 24901 |
| HPV16 | E7 | 10 | 73 | HVDIRTLEDL | 24902 |
| HPV16 | E7 | 11 | 73 | HVDIRTLEDLL | 24903 |
| HPV16 | E7 | 8 | 82 | LLMGTLGI | 24904 |
| HPV16 | E7 | 9 | 82 | LLMGTLGIV | 24905 |
| HPV16 | E7 | 8 | 83 | LMGTLGIV | 24906 |
| HPV16 | E7 | 11 | 83 | LMGTLGIVCPI | 24907 |
| HPV16 | E7 | 8 | 15 | LQPETTDL | 24908 |
| HPV16 | E7 | 9 | 15 | LQPETTDLY | 24909 |

TABLE XIV-continued

B62 Supermotif Peptides

| Type | Protein | No. of Amino Acid | Position | Sequence | Seq. Id. No. |
|---|---|---|---|---|---|
| HPV16 | E7 | 11 | 15 | LQPETTDLYCY | 24910 |
| HPV16 | E7 | 11 | 12 | MLDLQPETTDL | 24911 |
| HPV16 | E7 | 8 | 16 | QPETTDLY | 24912 |
| HPV16 | E7 | 10 | 16 | QPETTDLYCY | 24913 |
| HPV16 | E7 | 9 | 66 | RLCVQSTHV | 24914 |
| HPV16 | E7 | 11 | 66 | RLCVQSTHVDI | 24915 |
| HPV16 | E7 | 10 | 78 | TLEDLLMGTL | 24916 |
| HPV16 | E7 | 8 | 86 | TLGIVCPI | 24917 |
| HPV16 | E7 | 9 | 7 | TLHEYMLDL | 24918 |
| HPV16 | E7 | 11 | 64 | TLRLCVQSTHV | 24919 |
| HPV16 | E7 | 8 | 5 | TPTLHEYM | 24920 |
| HPV16 | E7 | 9 | 5 | TPTLHEYML | 24921 |
| HPV16 | E7 | 11 | 5 | TPTLHEYMLDL | 24922 |
| HPV16 | E7 | 8 | 69 | VQSTHVDI | 24923 |
| HPV16 | E7 | 11 | 69 | VQSTHVDIRTL | 24924 |
| HPV16 | L1 | 11 | 451 | AIACQKHTPPA | 24925 |
| HPV16 | L1 | 9 | 373 | AISTSETTY | 24926 |
| HPV16 | L1 | 9 | 233 | AMDFTTLQA | 24927 |
| HPV16 | L1 | 10 | 461 | APKEDPLKKY | 24928 |
| HPV16 | L1 | 8 | 342 | AQGHNNGI | 24929 |
| HPV16 | L1 | 10 | 342 | AQGHNNGICW | 24930 |
| HPV16 | L1 | 8 | 330 | AQIFNKPY | 24931 |
| HPV16 | L1 | 9 | 330 | AQIFNKPYW | 24932 |
| HPV16 | L1 | 10 | 330 | AQIFNKPYWL | 24933 |
| HPV16 | L1 | 10 | 292 | AVGENVPDDL | 24934 |
| HPV16 | L1 | 11 | 292 | AVGENVPDDLY | 24935 |
| HPV16 | L1 | 9 | 70 | AVGHPYFPI | 24936 |
| HPV16 | L1 | 10 | 205 | AVNPGDCPPL | 24937 |
| HPV16 | L1 | 11 | 172 | CISMDYKQTQL | 24938 |
| HPV16 | L1 | 9 | 183 | CLIGCKPPI | 24939 |
| HPV16 | L1 | 10 | 211 | CPPLELINTV | 24940 |
| HPV16 | L1 | 11 | 211 | CPPLELINTVI | 24941 |
| HPV16 | L1 | 8 | 454 | CQKHTPPA | 24942 |
| HPV16 | L1 | 9 | 249 | DICTSICKY | 24943 |
| HPV16 | L1 | 11 | 484 | DLDQFPLGRKF | 24944 |
| HPV16 | L1 | 8 | 397 | DLQFIFQL | 24945 |
| HPV16 | L1 | 11 | 397 | DLQFIFQLCKI | 24946 |
| HPV16 | L1 | 11 | 300 | DLYIKGSGSTA | 24947 |
| HPV16 | L1 | 9 | 225 | DMVDTGFGA | 24948 |
| HPV16 | L1 | 10 | 225 | DMVDTGFGAM | 24949 |
| HPV16 | L1 | 8 | 465 | DPLKKYTF | 24950 |
| HPV16 | L1 | 9 | 465 | KPLKKYTFW | 24951 |
| HPV16 | L1 | 11 | 465 | DPLKKYTFWEV | 24952 |
| HPV16 | L1 | 9 | 486 | DQFPLGRKF | 24953 |
| HPV16 | L1 | 10 | 486 | DQFPLGRKFL | 24954 |
| HPV16 | L1 | 11 | 486 | DQFPLGRKFLL | 24955 |
| HPV16 | L1 | 9 | 412 | DVMTYIHSM | 24956 |
| HPV16 | L1 | 8 | 17 | DVNVYHIF | 24957 |
| HPV16 | L1 | 9 | 17 | DVNVYHIFF | 24958 |
| HPV16 | L1 | 11 | 17 | DVNVYHIFFQM | 24959 |
| HPV16 | L1 | 8 | 266 | EPYGDSLF | 24960 |
| HPV16 | L1 | 9 | 266 | EPYGDSLFF | 24961 |
| HPV16 | L1 | 10 | 266 | EPYGDSLFFY | 24962 |
| HPV16 | L1 | 11 | 266 | EPYGDSLFFYL | 24963 |
| HPV16 | L1 | 8 | 279 | EQMFVRHL | 24964 |
| HPV16 | L1 | 9 | 279 | EQMFVRHLF | 24965 |
| HPV16 | L1 | 8 | 132 | EVGRGQPL | 24966 |
| HPV16 | L1 | 10 | 132 | EVGRGQPLGV | 24967 |
| HPV16 | L1 | 8 | 474 | EVNLKEKF | 24968 |
| HPV16 | L1 | 10 | 474 | EVNLKEKFSA | 24969 |
| HPV16 | L1 | 10 | 245 | EVPLDICTSI | 24970 |
| HPV16 | L1 | 8 | 400 | FIFQLCKI | 24971 |
| HPV16 | L1 | 10 | 400 | FIFQLCKITL | 24972 |
| HPV16 | L1 | 10 | 5 | FIYILVITCY | 24973 |
| HPV16 | L1 | 9 | 494 | FLLQAGLKA | 24974 |
| HPV16 | L1 | 11 | 76 | FPIKKPNNNKI | 24975 |
| HPV16 | L1 | 8 | 488 | FPLGRKFL | 24976 |
| HPV16 | L1 | 9 | 488 | FPLGRKFLL | 24977 |
| HPV16 | L1 | 11 | 488 | FPLGRKFLLQA | 24978 |
| HPV16 | L1 | 8 | 318 | FPTPSGSM | 24979 |
| HPV16 | L1 | 9 | 318 | FPTPSGSMV | 24980 |
| HPV16 | L1 | 8 | 402 | FQLCKITL | 24981 |
| HPV16 | L1 | 10 | 402 | FQLCKITLTA | 24982 |
| HPV16 | L1 | 11 | 25 | FQMSLWLPSEA | 24983 |
| HPV16 | L1 | 9 | 282 | FVRHLFNRA | 24984 |

TABLE XIV-continued

B62 Supermotif Peptides

| Type | Protein | No. of Amino Acid | Position | Sequence | Seq. Id. No. |
|---|---|---|---|---|---|
| HPV16 | L1 | 11 | 282 | FVRHLFNRAGA | 24985 |
| HPV16 | L1 | 8 | 446 | FVTSQAIA | 24986 |
| HPV16 | L1 | 8 | 348 | GICWGNQL | 24987 |
| HPV16 | L1 | 9 | 348 | GICWGNQLF | 24988 |
| HPV16 | L1 | 10 | 348 | GICWGNQLFV | 24989 |
| HPV16 | L1 | 8 | 142 | GISGHPLL | 24990 |
| HPV16 | L1 | 11 | 142 | GISGHPLLNKL | 24991 |
| HPV16 | L1 | 8 | 499 | GLKAKPKF | 24992 |
| HPV16 | L1 | 10 | 499 | GLKAKPKFTL | 24993 |
| HPV16 | L1 | 10 | 431 | GLQPPPGGTL | 24994 |
| HPV16 | L1 | 9 | 93 | GLQYRVFRI | 24995 |
| HPV16 | L1 | 11 | 93 | GLQYRVFRIHL | 24996 |
| HPV16 | L1 | 8 | 136 | GQPLGVGI | 24997 |
| HPV16 | L1 | 8 | 166 | GVDNRECI | 24998 |
| HPV16 | L1 | 10 | 166 | GVDNRECISM | 24999 |
| HPV16 | L1 | 10 | 130 | GVEVGRGQPL | 25000 |
| HPV16 | L1 | 9 | 140 | GVGISGHPL | 25001 |
| HPV16 | L1 | 10 | 140 | GVGISGHPLL | 25002 |
| HPV16 | L1 | 8 | 22 | HIFFQMSL | 25003 |
| HPV16 | L1 | 9 | 22 | HIFFQMSLW | 25004 |
| HPV16 | L1 | 10 | 22 | HIFFQMSLWL | 25005 |
| HPV16 | L1 | 8 | 285 | HLFNRAGA | 25006 |
| HPV16 | L1 | 9 | 285 | HLFNRAGAV | 25007 |
| HPV16 | L1 | 8 | 102 | HLPDPNKF | 25008 |
| HPV16 | L1 | 10 | 102 | HLPDPNKFGF | 25009 |
| HPV16 | L1 | 9 | 424 | ILEDWNFGL | 25010 |
| HPV16 | L1 | 11 | 8 | ILVITCYENDV | 25011 |
| HPV16 | L1 | 9 | 86 | ILVPKVSGL | 25012 |
| HPV16 | L1 | 11 | 86 | ILVPKVSGLQY | 25013 |
| HPV16 | L1 | 11 | 221 | IQDGDMVDTGF | 25014 |
| HPV16 | L1 | 10 | 85 | KILVPKVSGL | 25015 |
| HPV16 | L1 | 8 | 406 | KITLTADV | 25016 |
| HPV16 | L1 | 9 | 406 | KITLTADVM | 25017 |
| HPV16 | L1 | 11 | 406 | KITLTADVMTY | 25018 |
| HPV16 | L1 | 8 | 151 | KLDDTENA | 25019 |
| HPV16 | L1 | 10 | 151 | KLDDTENASA | 25020 |
| HPV16 | L1 | 11 | 151 | KLDDTENASAY | 25021 |
| HPV16 | L1 | 11 | 262 | KMVSEPYGDSL | 25022 |
| HPV16 | L1 | 11 | 503 | KPKFTLGKRKA | 25023 |
| HPV16 | L1 | 8 | 80 | KPNNNKIL | 25024 |
| HPV16 | L1 | 9 | 80 | KPNNNKILV | 25025 |
| HPV16 | L1 | 8 | 188 | KPPIGEHW | 25026 |
| HPV16 | L1 | 8 | 335 | KPYWLQRA | 25027 |
| HPV16 | L1 | 8 | 178 | KQTQLCLI | 25028 |
| HPV16 | L1 | 9 | 90 | KVSGLQYRV | 25029 |
| HPV16 | L1 | 10 | 90 | KVSGLQYRVF | 25030 |
| HPV16 | L1 | 8 | 46 | KVVSTDEY | 25031 |
| HPV16 | L1 | 9 | 46 | KVVSTDEYV | 25032 |
| HPV16 | L1 | 10 | 46 | KVVSTDEYVA | 25033 |
| HPV16 | L1 | 8 | 184 | LIGCKPPI | 25034 |
| HPV16 | L1 | 11 | 216 | LINTVIQDGDM | 25035 |
| HPV16 | L1 | 8 | 68 | LLAVGHPY | 25036 |
| HPV16 | L1 | 9 | 68 | LLAVGHPYF | 25037 |
| HPV16 | L1 | 11 | 68 | LLAVGHPYFPI | 25038 |
| HPV16 | L1 | 11 | 148 | LLNKLDDTENA | 25039 |
| HPV16 | L1 | 8 | 495 | LLQAGLKA | 25040 |
| HPV16 | L1 | 9 | 103 | LPDPNKFGF | 25041 |
| HPV16 | L1 | 9 | 39 | LPPVPVSKV | 25042 |
| HPV16 | L1 | 10 | 39 | LPPVPVSKVV | 25043 |
| HPV16 | L1 | 8 | 31 | LPSEATVY | 25044 |
| HPV16 | L1 | 9 | 31 | LPSEATVYL | 25045 |
| HPV16 | L1 | 11 | 496 | LQAGLKAKPKF | 25046 |
| HPV16 | L1 | 8 | 239 | LQANKSEV | 25047 |
| HPV16 | L1 | 10 | 239 | LQANKSEVPL | 25048 |
| HPV16 | L1 | 10 | 398 | LQFIFQLCKI | 25049 |
| HPV16 | L1 | 9 | 432 | LQPPPGGTL | 25050 |
| HPV16 | L1 | 11 | 339 | LQRAQGHNNGI | 25051 |
| HPV16 | L1 | 8 | 94 | LQYRVFRI | 25052 |
| HPV16 | L1 | 10 | 94 | LQYRVFRIHL | 25053 |
| HPV16 | L1 | 10 | 9 | LVITCYENDV | 25054 |
| HPV16 | L1 | 8 | 87 | LVPKVSGL | 25055 |
| HPV16 | L1 | 10 | 87 | LVPKVSGLQY | 25056 |
| HPV16 | L1 | 8 | 124 | LVWACVGV | 25057 |
| HPV16 | L1 | 10 | 124 | LVWACVGVEV | 25058 |
| HPV16 | L1 | 8 | 1 | MQVTFIYI | 25059 |

TABLE XIV-continued

B62 Supermotif Peptides

| Type | Protein | No. of Amino Acid | Position | Sequence | Seq. Id. No. |
|---|---|---|---|---|---|
| HPV16 | L1 | 9 | 1 | MQVTFIYIL | 25060 |
| HPV16 | L1 | 10 | 1 | MQVTFIYILV | 25061 |
| HPV16 | L1 | 11 | 1 | MQVTFIYILVI | 25062 |
| HPV16 | L1 | 8 | 226 | MVDTGFGA | 25063 |
| HPV16 | L1 | 9 | 226 | MVDTGFGAM | 25064 |
| HPV16 | L1 | 11 | 226 | MVDTGFGAMDF | 25065 |
| HPV16 | L1 | 10 | 263 | MVSEPYGDSL | 25066 |
| HPV16 | L1 | 11 | 263 | MVSEPYGDSLF | 25067 |
| HPV16 | L1 | 8 | 325 | MVTSDAQI | 25068 |
| HPV16 | L1 | 9 | 325 | MVTSDAQIF | 25069 |
| HPV16 | L1 | 11 | 58 | NIYYHAGTSRL | 25070 |
| HPV16 | L1 | 8 | 311 | NLASSNYF | 25071 |
| HPV16 | L1 | 8 | 476 | NLKEKFSA | 25072 |
| HPV16 | L1 | 10 | 476 | NLKEKFSADL | 25073 |
| HPV16 | L1 | 8 | 367 | NMSLCAAI | 25074 |
| HPV16 | L1 | 8 | 118 | NPDTQRLV | 25075 |
| HPV16 | L1 | 9 | 118 | NPDTQRLVW | 25076 |
| HPV16 | L1 | 10 | 118 | NPDTQRLVWA | 25077 |
| HPV16 | L1 | 8 | 207 | NPGDCPPL | 25078 |
| HPV16 | L1 | 10 | 207 | NPGDCPPLEL | 25079 |
| HPV16 | L1 | 11 | 207 | NPGDCPPLELI | 25080 |
| HPV16 | L1 | 8 | 353 | NQLFVTVV | 25081 |
| HPV16 | L1 | 8 | 296 | NVPDDLYI | 25082 |
| HPV16 | L1 | 9 | 19 | NVYHIFFQM | 25083 |
| HPV16 | L1 | 11 | 19 | NVYHIFFQMSL | 25084 |
| HPV16 | L1 | 10 | 77 | PIKKPNNNKI | 25085 |
| HPV16 | L1 | 11 | 77 | PIKKPNNNKIL | 25086 |
| HPV16 | L1 | 8 | 247 | PLDICTSI | 25087 |
| HPV16 | L1 | 11 | 247 | PLDICTSICKY | 25088 |
| HPV16 | L1 | 8 | 213 | PLELINTV | 25089 |
| HPV16 | L1 | 9 | 213 | PLELINTVI | 25090 |
| HPV16 | L1 | 8 | 489 | PLGRKFLL | 25091 |
| HPV16 | L1 | 10 | 489 | PLGRKFLLQA | 25092 |
| HPV16 | L1 | 11 | 138 | PLGVGISGHPL | 25093 |
| HPV16 | L1 | 8 | 466 | PLKKYTFW | 25094 |
| HPV16 | L1 | 10 | 466 | PLKKYTFWEV | 25095 |
| HPV16 | L1 | 9 | 459 | PPAPKEDPL | 25096 |
| HPV16 | L1 | 10 | 435 | PPGGTLEDTY | 25097 |
| HPV16 | L1 | 9 | 212 | PPLELINTV | 25098 |
| HPV16 | L1 | 10 | 212 | PPLELINTVI | 25099 |
| HPV16 | L1 | 11 | 434 | PPPGGTLEDTY | 25100 |
| HPV16 | L1 | 8 | 40 | PPVPVSKV | 25101 |
| HPV16 | L1 | 9 | 40 | PPVPVSKVV | 25102 |
| HPV16 | L1 | 8 | 41 | PVPVSKVV | 25103 |
| HPV16 | L1 | 11 | 43 | PVSKVVSTDEY | 25104 |
| HPV16 | L1 | 8 | 331 | QIFNKPYW | 25105 |
| HPV16 | L1 | 9 | 331 | QIFNKPYWL | 25106 |
| HPV16 | L1 | 9 | 403 | QLCKITLTA | 25107 |
| HPV16 | L1 | 11 | 403 | QLCKITLTADV | 25108 |
| HPV16 | L1 | 11 | 181 | QLCLIGCKPPI | 25109 |
| HPV16 | L1 | 8 | 280 | QMFVRHLF | 25110 |
| HPV16 | L1 | 11 | 280 | QMFVRHLFNRA | 25111 |
| HPV16 | L1 | 10 | 26 | QMSLWLPSEA | 25112 |
| HPV16 | L1 | 8 | 433 | QPPPGGTL | 25113 |
| HPV16 | L1 | 8 | 2 | QVTFIYIL | 25114 |
| HPV16 | L1 | 9 | 2 | QVTFIYILV | 25115 |
| HPV16 | L1 | 10 | 2 | QVTFIYILVI | 25116 |
| HPV16 | L1 | 10 | 100 | RIHLPDPNKF | 25117 |
| HPV16 | L1 | 9 | 67 | RLLAVGHPY | 25118 |
| HPV16 | L1 | 10 | 67 | RLLAVGHPYF | 25119 |
| HPV16 | L1 | 9 | 123 | RLVWACVGV | 25120 |
| HPV16 | L1 | 11 | 123 | RLVWACVGVEV | 25121 |
| HPV16 | L1 | 8 | 253 | SICKYPDY | 25122 |
| HPV16 | L1 | 9 | 253 | SICKYPDYI | 25123 |
| HPV16 | L1 | 11 | 253 | SICKYPDYIKM | 25124 |
| HPV16 | L1 | 11 | 271 | SLFFYLRREQM | 25125 |
| HPV16 | L1 | 8 | 28 | SLWLPSEA | 25126 |
| HPV16 | L1 | 10 | 28 | SLWLPSEATV | 25127 |
| HPV16 | L1 | 11 | 28 | SLWLPSEATVY | 25128 |
| HPV16 | L1 | 9 | 174 | SMDYKQTQL | 25129 |
| HPV16 | L1 | 11 | 174 | SMDYKQTQLCL | 25130 |
| HPV16 | L1 | 10 | 419 | SMNSTILEDW | 25131 |
| HPV16 | L1 | 9 | 324 | SMVTSDAQI | 25132 |
| HPV16 | L1 | 10 | 324 | SMVTSDAQIF | 25133 |
| HPV16 | L1 | 8 | 199 | SPCTNVAV | 25134 |

TABLE XIV-continued

B62 Supermotif Peptides

| Type | Protein | No. of Amino Acid | Position | Sequence | Seq. Id. No. |
|---|---|---|---|---|---|
| HPV16 | L1 | 8 | 423 | TILEDWNF | 25135 |
| HPV16 | L1 | 10 | 423 | TILEDWNFGL | 25136 |
| HPV16 | L1 | 8 | 439 | TLEDTYRF | 25137 |
| HPV16 | L1 | 9 | 439 | TLEDTYRFV | 25138 |
| HPV16 | L1 | 9 | 238 | TLQANKSEV | 25139 |
| HPV16 | L1 | 11 | 238 | TLQANKSEVPL | 25140 |
| HPV16 | L1 | 9 | 408 | TLTADVMTY | 25141 |
| HPV16 | L1 | 10 | 408 | TLTADVMTYI | 25142 |
| HPV16 | L1 | 10 | 458 | TPPAPKEDPL | 25143 |
| HPV16 | L1 | 11 | 320 | TPSGSMVTSDA | 25144 |
| HPV16 | L1 | 11 | 514 | TPTTSSTSTTA | 25145 |
| HPV16 | L1 | 9 | 121 | TQRLVWACV | 25146 |
| HPV16 | L1 | 11 | 121 | TQRLVWACVGV | 25147 |
| HPV16 | L1 | 8 | 219 | TVIQDGDM | 25148 |
| HPV16 | L1 | 9 | 219 | TVIQDGDMV | 25149 |
| HPV16 | L1 | 11 | 358 | TVVDTTRSTNM | 25150 |
| HPV16 | L1 | 9 | 36 | TVYLPPVPV | 25151 |
| HPV16 | L1 | 8 | 220 | VIQDGDMV | 25152 |
| HPV16 | L1 | 9 | 10 | VITCYENDV | 25153 |
| HPV16 | L1 | 11 | 10 | VITCYENDVNV | 25154 |
| HPV16 | L1 | 8 | 413 | VMTYIHSM | 25155 |
| HPV16 | L1 | 9 | 88 | VPKVSGLQY | 25156 |
| HPV16 | L1 | 11 | 88 | VPKVSGLQYRV | 25157 |
| HPV16 | L1 | 9 | 246 | VPLDICTSI | 25158 |
| HPV16 | L1 | 10 | 359 | VVDTTRSTNM | 25159 |
| HPV16 | L1 | 8 | 47 | VVSTDEYV | 25160 |
| HPV16 | L1 | 9 | 47 | VVSTDEYVA | 25161 |
| HPV16 | L1 | 8 | 30 | WLPSEATV | 25162 |
| HPV16 | L1 | 9 | 30 | WLPSEATVY | 25163 |
| HPV16 | L1 | 10 | 30 | WLPSEATVYL | 25164 |
| HPV16 | L1 | 9 | 416 | YIHSMNSTI | 25165 |
| HPV16 | L1 | 10 | 416 | YIHSMNSTIL | 25166 |
| HPV16 | L1 | 9 | 302 | YIKGSGSTA | 25167 |
| HPV16 | L1 | 11 | 302 | YIKGSGSTANL | 25168 |
| HPV16 | L1 | 9 | 260 | YIKMVSEPY | 25169 |
| HPV16 | L1 | 8 | 7 | YILVITCY | 25170 |
| HPV16 | L1 | 10 | 38 | YLPPVPSKV | 25171 |
| HPV16 | L1 | 11 | 38 | YLPPVPSKVV | 25172 |
| HPV16 | L1 | 8 | 389 | YLRHGEEY | 25173 |
| HPV16 | L1 | 10 | 389 | YLRHGEEYDL | 25174 |
| HPV16 | L1 | 8 | 275 | YLRREQMF | 25175 |
| HPV16 | L1 | 9 | 275 | YLRREQMFV | 25176 |
| HPV16 | L1 | 8 | 257 | YPDYIKMV | 25177 |
| HPV16 | L1 | 8 | 53 | YVARTNIY | 25178 |
| HPV16 | L1 | 9 | 53 | YVARTNIYY | 25179 |
| HPV16 | L1 | 11 | 53 | YVARTNIYYHA | 25180 |
| HPV16 | L2 | 9 | 144 | AILDINNTV | 25181 |
| HPV16 | L2 | 10 | 356 | ALPTSINNGL | 25182 |
| HPV16 | L2 | 11 | 356 | ALPTSINNGLY | 25183 |
| HPV16 | L2 | 9 | 293 | ALTSRRTGI | 25184 |
| HPV16 | L2 | 11 | 293 | ALTSRRTGIRY | 25185 |
| HPV16 | L2 | 9 | 278 | APDPDFLDI | 25186 |
| HPV16 | L2 | 10 | 278 | APDPDFLDIV | 25187 |
| HPV16 | L2 | 11 | 278 | APDPDFLDIVA | 25188 |
| HPV16 | L2 | 8 | 424 | APSLIPIV | 25189 |
| HPV16 | L2 | 8 | 119 | APTSVPSI | 25190 |
| HPV16 | L2 | 9 | 87 | APVRPPLTV | 25191 |
| HPV16 | L2 | 9 | 28 | CPPDIIPKV | 25192 |
| HPV16 | L2 | 11 | 31 | DIIPKVEGKTI | 25193 |
| HPV16 | L2 | 9 | 147 | DINNTVTTV | 25194 |
| HPV16 | L2 | 10 | 415 | DIPINITDQA | 25195 |
| HPV16 | L2 | 9 | 285 | DIVALHRPA | 25196 |
| HPV16 | L2 | 10 | 285 | DIVALHRPAL | 25197 |
| HPV16 | L2 | 8 | 367 | DIYADDFI | 25198 |
| HPV16 | L2 | 11 | 239 | DPAFITTPTKL | 25199 |
| HPV16 | L2 | 8 | 280 | DPDFLDIV | 25200 |
| HPV16 | L2 | 9 | 280 | DPDFLDIVA | 25201 |
| HPV16 | L2 | 10 | 280 | DPDFLDIVAL | 25202 |
| HPV16 | L2 | 8 | 102 | DPSIVSLV | 25203 |
| HPV16 | L2 | 11 | 165 | DPSVLQPPTPA | 25204 |
| HPV16 | L2 | 10 | 96 | DPVGPSDPSI | 25205 |
| HPV16 | L2 | 11 | 96 | DPVGPSDPSIV | 25206 |
| HPV16 | L2 | 9 | 422 | DQAPSLIPI | 25207 |
| HPV16 | L2 | 10 | 422 | DQAPSLIPIV | 25208 |
| HPV16 | L2 | 9 | 43 | DQILQYGSM | 25209 |

TABLE XIV-continued

B62 Supermotif Peptides

| Type | Protein | No. of Amino Acid | Position | Sequence | Seq. Id. No. |
|---|---|---|---|---|---|
| HPV16 | L2 | 11 | 43 | DQILQYGSMGV | 25210 |
| HPV16 | L2 | 8 | 261 | DVDNTLYF | 25211 |
| HPV16 | L2 | 8 | 195 | EIPMDTFI | 25212 |
| HPV16 | L2 | 9 | 195 | EIPMDTFIV | 25213 |
| HPV16 | L2 | 10 | 340 | ELQTITPSTY | 25214 |
| HPV16 | L2 | 10 | 114 | FIDAGAPTSV | 25215 |
| HPV16 | L2 | 10 | 373 | FITDTSTTPV | 25216 |
| HPV16 | L2 | 8 | 242 | FITTPTKL | 25217 |
| HPV16 | L2 | 9 | 242 | FITTPTKLI | 25218 |
| HPV16 | L2 | 11 | 242 | FITTPTKLITY | 25219 |
| HPV16 | L2 | 10 | 201 | FIVSTNPNTV | 25220 |
| HPV16 | L2 | 11 | 283 | FLDIVALHRPA | 25221 |
| HPV16 | L2 | 8 | 259 | GIDVDNTL | 25222 |
| HPV16 | L2 | 9 | 259 | GIDVDNTLY | 25223 |
| HPV16 | L2 | 10 | 259 | GIDVDNTLYF | 25224 |
| HPV16 | L2 | 10 | 364 | GLYDIYADDF | 25225 |
| HPV16 | L2 | 11 | 364 | GLYDIYADDFI | 25226 |
| HPV16 | L2 | 10 | 226 | GLYSRTTQQV | 25227 |
| HPV16 | L2 | 8 | 413 | GPDIPINI | 25228 |
| HPV16 | L2 | 8 | 99 | GPSDPSIV | 25229 |
| HPV16 | L2 | 10 | 99 | GPSDPSIVSL | 25230 |
| HPV16 | L2 | 11 | 99 | GPSDPSIVSLV | 25231 |
| HPV16 | L2 | 9 | 52 | GVFFGGLGI | 25232 |
| HPV16 | L2 | 8 | 439 | IIADAGDF | 25233 |
| HPV16 | L2 | 9 | 439 | IIADAGDFY | 25234 |
| HPV16 | L2 | 10 | 439 | IIADAGDFYL | 25235 |
| HPV16 | L2 | 10 | 32 | IIPKVEGKTI | 25236 |
| HPV16 | L2 | 11 | 32 | IIPKVEGKTIA | 25237 |
| HPV16 | L2 | 8 | 145 | ILDINNTV | 25238 |
| HPV16 | L2 | 11 | 145 | ILDINNTVTTV | 25239 |
| HPV16 | L2 | 9 | 45 | ILQYGSMGV | 25240 |
| HPV16 | L2 | 10 | 45 | ILQYGSMGVF | 25241 |
| HPV16 | L2 | 11 | 45 | ILQYGSMGVFF | 25242 |
| HPV16 | L2 | 9 | 394 | IPANTTIPF | 25243 |
| HPV16 | L2 | 9 | 400 | IPFGGAYNI | 25244 |
| HPV16 | L2 | 11 | 400 | IPFGGAYNIPL | 25245 |
| HPV16 | L2 | 8 | 216 | IPGSRPVA | 25246 |
| HPV16 | L2 | 10 | 216 | IPGSRPVARL | 25247 |
| HPV16 | L2 | 9 | 416 | IPINITDQA | 25248 |
| HPV16 | L2 | 10 | 428 | IPIVPGSPQY | 25249 |
| HPV16 | L2 | 9 | 33 | IPKVEGKTI | 25250 |
| HPV16 | L2 | 10 | 33 | IPKVEGKTIA | 25251 |
| HPV16 | L2 | 10 | 73 | IPLGTRPPTA | 25252 |
| HPV16 | L2 | 9 | 408 | IPLVSGPDI | 25253 |
| HPV16 | L2 | 11 | 408 | IPLVSGPDIPI | 25254 |
| HPV16 | L2 | 8 | 196 | IPMDTFIV | 25255 |
| HPV16 | L2 | 8 | 126 | IPPDVSGF | 25256 |
| HPV16 | L2 | 10 | 126 | IPPDVSGFSI | 25257 |
| HPV16 | L2 | 8 | 286 | IVALHRPA | 25258 |
| HPV16 | L2 | 9 | 286 | IVALHRPAL | 25259 |
| HPV16 | L2 | 8 | 430 | IVPGSPQY | 25260 |
| HPV16 | L2 | 10 | 430 | IVPGSPQYTI | 25261 |
| HPV16 | L2 | 11 | 430 | IVPGSPQYTII | 25262 |
| HPV16 | L2 | 10 | 105 | IVSLVEETSF | 25263 |
| HPV16 | L2 | 11 | 105 | IVSLVEETSFI | 25264 |
| HPV16 | L2 | 9 | 202 | IVSTNPNTV | 25265 |
| HPV16 | L2 | 9 | 248 | KLITYDNPA | 25266 |
| HPV16 | L2 | 10 | 248 | KLITYDNPAY | 25267 |
| HPV16 | L2 | 10 | 23 | KQAGTCPPDI | 25268 |
| HPV16 | L2 | 11 | 23 | KQAGTCPPDII | 25269 |
| HPV16 | L2 | 8 | 35 | KVEGKTIA | 25270 |
| HPV16 | L2 | 11 | 35 | KVEGKTIADQI | 25271 |
| HPV16 | L2 | 8 | 323 | KVHYYYDF | 25272 |
| HPV16 | L2 | 11 | 323 | KVHYYYDFSTI | 25273 |
| HPV16 | L2 | 8 | 236 | KVVDPAFI | 25274 |
| HPV16 | L2 | 11 | 427 | LIPIVPGSPQY | 25275 |
| HPV16 | L2 | 8 | 249 | LITYDNPA | 25276 |
| HPV16 | L2 | 9 | 249 | LITYDNPAY | 25277 |
| HPV16 | L2 | 9 | 357 | LPTSINNGL | 25278 |
| HPV16 | L2 | 10 | 357 | LPTSINNGLY | 25279 |
| HPV16 | L2 | 8 | 462 | LPYFFSDV | 25280 |
| HPV16 | L2 | 10 | 462 | LPYFFSDVSL | 25281 |
| HPV16 | L2 | 11 | 462 | LPYFFSDVSLA | 25282 |
| HPV16 | L2 | 9 | 341 | LQTITPSTY | 25283 |
| HPV16 | L2 | 8 | 46 | LQYGSMGV | 25284 |

TABLE XIV-continued

B62 Supermotif Peptides

| Type | Protein | No. of Amino Acid | Position | Sequence | Seq. Id. No. |
|---|---|---|---|---|---|
| HPV16 | L2 | 9 | 46 | LQYGSMGVF | 25285 |
| HPV16 | L2 | 10 | 46 | LQYGSMGVFF | 25286 |
| HPV16 | L2 | 8 | 108 | LVEETSFI | 25287 |
| HPV16 | L2 | 10 | 108 | LVEETSFIDA | 25288 |
| HPV16 | L2 | 9 | 410 | LVSGPDIPI | 25289 |
| HPV16 | L2 | 11 | 410 | LVSGPDIPINI | 25290 |
| HPV16 | L2 | 9 | 454 | MLRKRRKRL | 25291 |
| HPV16 | L2 | 11 | 454 | MLRKRRKRLPY | 25292 |
| HPV16 | L2 | 8 | 276 | NIAPDPDF | 25293 |
| HPV16 | L2 | 9 | 276 | NIAPDPDFL | 25294 |
| HPV16 | L2 | 11 | 276 | NIAPDPDFLDI | 25295 |
| HPV16 | L2 | 10 | 407 | NIPLVSGPDI | 25296 |
| HPV16 | L2 | 9 | 419 | NITDQAPSL | 25297 |
| HPV16 | L2 | 10 | 419 | NITDQAPSLI | 25298 |
| HPV16 | L2 | 9 | 254 | NPAYEGIDV | 25299 |
| HPV16 | L2 | 11 | 206 | NPNTVTSSTPI | 25300 |
| HPV16 | L2 | 9 | 160 | NPTFTDPSV | 25301 |
| HPV16 | L2 | 10 | 160 | NPTFTDPSVL | 25302 |
| HPV16 | L2 | 8 | 417 | PINITDQA | 25303 |
| HPV16 | L2 | 11 | 417 | PINITDQAPSL | 25304 |
| HPV16 | L2 | 8 | 215 | PIPGSRPV | 25305 |
| HPV16 | L2 | 9 | 215 | PIPGSRPVA | 25306 |
| HPV16 | L2 | 11 | 215 | PIPGSRPVARL | 25307 |
| HPV16 | L2 | 9 | 429 | PIVPGSPQY | 25308 |
| HPV16 | L2 | 11 | 429 | PIVPGSPQYTI | 25309 |
| HPV16 | L2 | 9 | 74 | PLGTRPPTA | 25310 |
| HPV16 | L2 | 8 | 409 | PLVSGPDI | 25311 |
| HPV16 | L2 | 10 | 409 | PLVSGPDIPI | 25312 |
| HPV16 | L2 | 8 | 29 | PPDIIPKV | 25313 |
| HPV16 | L2 | 9 | 127 | PPDVSGFSI | 25314 |
| HPV16 | L2 | 8 | 91 | PPLTVDPV | 25315 |
| HPV16 | L2 | 8 | 79 | PPTATDTL | 25316 |
| HPV16 | L2 | 9 | 79 | PPTATDTLA | 25317 |
| HPV16 | L2 | 11 | 79 | PPTATDTLAPV | 25318 |
| HPV16 | L2 | 11 | 171 | PPTPAETGGHF | 25319 |
| HPV16 | L2 | 9 | 435 | PQYTIIADA | 25320 |
| HPV16 | L2 | 8 | 221 | PVARLGLY | 25321 |
| HPV16 | L2 | 9 | 97 | PVGPSDPSI | 25322 |
| HPV16 | L2 | 10 | 97 | PVGPSDPSIV | 25323 |
| HPV16 | L2 | 10 | 381 | PVPSVPSTSL | 25324 |
| HPV16 | L2 | 8 | 88 | PVRPPLTV | 25325 |
| HPV16 | L2 | 11 | 88 | PVRPPLTVDPV | 25326 |
| HPV16 | L2 | 8 | 44 | QILQYGSM | 25327 |
| HPV16 | L2 | 10 | 44 | QILQYGSMGV | 25328 |
| HPV16 | L2 | 11 | 44 | QILQYGSMGVF | 25329 |
| HPV16 | L2 | 9 | 17 | QLYKTCKQA | 25330 |
| HPV16 | L2 | 9 | 233 | QQVKVVDPA | 25331 |
| HPV16 | L2 | 10 | 233 | QQVKVVDPAF | 25332 |
| HPV16 | L2 | 11 | 233 | QQVKVVDPAFI | 25333 |
| HPV16 | L2 | 8 | 234 | QVKVVDPA | 25334 |
| HPV16 | L2 | 9 | 234 | QVKVVDPAF | 25335 |
| HPV16 | L2 | 10 | 234 | QVKVVDPAFI | 25336 |
| HPV16 | L2 | 8 | 305 | RIGNKQTL | 25337 |
| HPV16 | L2 | 9 | 461 | RLPYFFSDV | 25338 |
| HPV16 | L2 | 11 | 461 | RLPYFFSDVSL | 25339 |
| HPV16 | L2 | 11 | 291 | RPALTSRRTGI | 25340 |
| HPV16 | L2 | 9 | 90 | RPPLTVDPV | 25341 |
| HPV16 | L2 | 9 | 78 | RPPTATDTL | 25342 |
| HPV16 | L2 | 10 | 78 | RPPTATDTLA | 25343 |
| HPV16 | L2 | 8 | 220 | RPVARLGL | 25344 |
| HPV16 | L2 | 9 | 220 | RPVARLGLY | 25345 |
| HPV16 | L2 | 8 | 319 | SIGAKVHY | 25346 |
| HPV16 | L2 | 9 | 319 | SIGAKVHYY | 25347 |
| HPV16 | L2 | 10 | 319 | SIGAKVHYYY | 25348 |
| HPV16 | L2 | 10 | 274 | SINIAPDPDF | 25349 |
| HPV16 | L2 | 11 | 274 | SINIAPDPDFL | 25350 |
| HPV16 | L2 | 9 | 360 | SINNGLYDI | 25351 |
| HPV16 | L2 | 10 | 360 | SINNGLYDIY | 25352 |
| HPV16 | L2 | 11 | 360 | SINNGLYDIYA | 25353 |
| HPV16 | L2 | 9 | 125 | SIPPDVSGF | 25354 |
| HPV16 | L2 | 11 | 125 | SIPPDVSGFSI | 25355 |
| HPV16 | L2 | 11 | 134 | SITTSTDTTPA | 25356 |
| HPV16 | L2 | 11 | 104 | SIVSLVEETSF | 25357 |
| HPV16 | L2 | 8 | 389 | SLSGYIPA | 25358 |
| HPV16 | L2 | 8 | 107 | SLVEETSF | 25359 |

TABLE XIV-continued

B62 Supermotif Peptides

| Type | Protein | No. of Amino Acid | Position | Sequence | Seq. Id. No. |
|---|---|---|---|---|---|
| HPV16 | L2 | 9 | 107 | SLVEETSFI | 25360 |
| HPV16 | L2 | 11 | 107 | SLVEETSFIDA | 25361 |
| HPV16 | L2 | 9 | 50 | SMGVFFGGL | 25362 |
| HPV16 | L2 | 11 | 50 | SMGVFFGGLGI | 25363 |
| HPV16 | L2 | 8 | 434 | SPQYTIIA | 25364 |
| HPV16 | L2 | 10 | 434 | SPQYTIIADA | 25365 |
| HPV16 | L2 | 9 | 167 | SVLQPPTPA | 25366 |
| HPV16 | L2 | 9 | 122 | SVPSIPPDV | 25367 |
| HPV16 | L2 | 10 | 384 | SVPSTSLSGY | 25368 |
| HPV16 | L2 | 11 | 384 | SVPSTSLSGYI | 25369 |
| HPV16 | L2 | 9 | 40 | TIADQILQY | 25370 |
| HPV16 | L2 | 8 | 332 | TIDSAEEI | 25371 |
| HPV16 | L2 | 10 | 332 | TIDSAEEIEL | 25372 |
| HPV16 | L2 | 9 | 438 | TIIADAGDF | 25373 |
| HPV16 | L2 | 10 | 438 | TIIADAGDFY | 25374 |
| HPV16 | L2 | 11 | 438 | TIIADAGDFYL | 25375 |
| HPV16 | L2 | 8 | 399 | TIPFGGAY | 25376 |
| HPV16 | L2 | 10 | 399 | TIPFGGAYNI | 25377 |
| HPV16 | L2 | 10 | 187 | TISTHNYEEI | 25378 |
| HPV16 | L2 | 9 | 85 | TLAPVRPPL | 25379 |
| HPV16 | L2 | 11 | 85 | TLAPVRPPLTV | 25380 |
| HPV16 | L2 | 10 | 311 | TLRTRSGKSI | 25381 |
| HPV16 | L2 | 11 | 265 | TLYFSSNDNSI | 25382 |
| HPV16 | L2 | 9 | 173 | TPAETGGHF | 25383 |
| HPV16 | L2 | 11 | 173 | TPAETGGHFTL | 25384 |
| HPV16 | L2 | 11 | 142 | TPAILDINNTV | 25385 |
| HPV16 | L2 | 9 | 214 | TPIPGSRPV | 25386 |
| HPV16 | L2 | 10 | 214 | TPIPGSRPVA | 25387 |
| HPV16 | L2 | 11 | 345 | TPSTYTTTSHA | 25388 |
| HPV16 | L2 | 8 | 245 | TPTKLITY | 25389 |
| HPV16 | L2 | 11 | 380 | TPVPSVPSTSL | 25390 |
| HPV16 | L2 | 10 | 16 | TQLYKTCKQA | 25391 |
| HPV16 | L2 | 10 | 232 | TQQVKVVDPA | 25392 |
| HPV16 | L2 | 11 | 232 | TQQVKVVDPAF | 25393 |
| HPV16 | L2 | 8 | 209 | TVTSSTPI | 25394 |
| HPV16 | L2 | 10 | 154 | TVTTHNNPTF | 25395 |
| HPV16 | L2 | 8 | 168 | VLQPPTPA | 25396 |
| HPV16 | L2 | 9 | 431 | VPGSPQYTI | 25397 |
| HPV16 | L2 | 10 | 431 | VPGSPQYTII | 25398 |
| HPV16 | L2 | 11 | 431 | VPGSPQYTIIA | 25399 |
| HPV16 | L2 | 8 | 123 | VPSIPPDV | 25400 |
| HPV16 | L2 | 11 | 123 | VPSIPPDVSGF | 25401 |
| HPV16 | L2 | 9 | 385 | VPSTSLSGY | 25402 |
| HPV16 | L2 | 10 | 385 | VPSTSLSGYI | 25403 |
| HPV16 | L2 | 9 | 382 | VPSVPSTSL | 25404 |
| HPV16 | L2 | 8 | 393 | YIPANTTI | 25405 |
| HPV16 | L2 | 10 | 393 | YIPANTTIPF | 25406 |
| HPV16 | L2 | 11 | 72 | YIPLGTRPPTA | 25407 |
| HPV16 | L2 | 8 | 447 | YLHPSYYM | 25408 |
| HPV16 | L2 | 9 | 447 | YLHPSYYML | 25409 |
| HPV16 | L2 | 10 | 453 | YMLRKRRKRL | 25410 |
| HPV18 | E1 | 9 | 246 | AIFGVNPTI | 25411 |
| HPV18 | E1 | 10 | 246 | AIFGVNPTIA | 25412 |
| HPV18 | E1 | 10 | 22 | AIVDKKTGDV | 25413 |
| HPV18 | E1 | 11 | 22 | AIVDKKTGDVI | 25414 |
| HPV18 | E1 | 9 | 546 | ALDGNPISI | 25415 |
| HPV18 | E1 | 8 | 68 | ALFHAQEV | 25416 |
| HPV18 | E1 | 10 | 387 | ALLADSNSNA | 25417 |
| HPV18 | E1 | 11 | 387 | ALLADSNSNAA | 25418 |
| HPV18 | E1 | 9 | 325 | ALYWYRTGI | 25419 |
| HPV18 | E1 | 10 | 213 | AMLAVFKDTY | 25420 |
| HPV18 | E1 | 11 | 526 | AMLDDATTTCW | 25421 |
| HPV18 | E1 | 10 | 66 | AQALFHAQEV | 25422 |
| HPV18 | E1 | 8 | 72 | AQEVHNDA | 25423 |
| HPV18 | E1 | 10 | 72 | AQEVHNDAQV | 25424 |
| HPV18 | E1 | 11 | 72 | AQEVHNDAQVL | 25425 |
| HPV18 | E1 | 8 | 422 | AQKRQMNM | 25426 |
| HPV18 | E1 | 11 | 422 | AQKRQMNMSQW | 25427 |
| HPV18 | E1 | 9 | 199 | AQLKDLLKV | 25428 |
| HPV18 | E1 | 11 | 79 | AQVLHVLKRKF | 25429 |
| HPV18 | E1 | 9 | 216 | AVFKDTYGL | 25430 |
| HPV18 | E1 | 11 | 216 | AVFKDTYGLSF | 25431 |
| HPV18 | E1 | 8 | 273 | CLDCKWGV | 25432 |
| HPV18 | E1 | 9 | 273 | CLDCKWGVL | 25433 |
| HPV18 | E1 | 10 | 273 | CLDCKWGVLI | 25434 |

TABLE XIV-continued

B62 Supermotif Peptides

| Type | Protein | No. of Amino Acid | Position | Sequence | Seq. Id. No. |
|---|---|---|---|---|---|
| HPV18 | E1 | 11 | 273 | CLDCKWGVLIL | 25435 |
| HPV18 | E1 | 8 | 479 | CLVFCGPA | 25436 |
| HPV18 | E1 | 9 | 311 | CMLIQPPKL | 25437 |
| HPV18 | E1 | 10 | 566 | CPPILLTTNI | 25438 |
| HPV18 | E1 | 10 | 404 | CQAKYLKDCA | 25439 |
| HPV18 | E1 | 9 | 628 | DLHEEEDA | 25440 |
| HPV18 | E1 | 11 | 203 | DLLKVNNKQGA | 25441 |
| HPV18 | E1 | 8 | 363 | DLSEMVQW | 25442 |
| HPV18 | E1 | 9 | 363 | DLSEMVQWA | 25443 |
| HPV18 | E1 | 10 | 363 | DLSEMVQWAF | 25444 |
| HPV18 | E1 | 8 | 381 | DMAFEYAL | 25445 |
| HPV18 | E1 | 9 | 381 | DMAFEYALL | 25446 |
| HPV18 | E1 | 10 | 381 | DMAFEYALLA | 25447 |
| HPV18 | E1 | 11 | 30 | DVISDDEDENA | 25448 |
| HPV18 | E1 | 10 | 610 | EINDKNWKCF | 25449 |
| HPV18 | E1 | 11 | 610 | EINDKNWKCFF | 25450 |
| HPV18 | E1 | 11 | 115 | EISLNSGQKKA | 25451 |
| HPV18 | E1 | 8 | 62 | ELETAQAL | 25452 |
| HPV18 | E1 | 9 | 62 | ELETAQALF | 25453 |
| HPV18 | E1 | 11 | 62 | ELETAQALFHA | 25454 |
| HPV18 | E1 | 9 | 108 | ELSPRLQEI | 25455 |
| HPV18 | E1 | 11 | 108 | ELSPRLQEISL | 25456 |
| HPV18 | E1 | 8 | 375 | ELTDESDM | 25457 |
| HPV18 | E1 | 9 | 375 | ELTDESDMA | 25458 |
| HPV18 | E1 | 10 | 375 | ELTDESDMAF | 25459 |
| HPV18 | E1 | 11 | 366 | EMVQWAFDNEL | 25460 |
| HPV18 | E1 | 8 | 518 | EPLTDTKV | 25461 |
| HPV18 | E1 | 9 | 518 | EPLTDTKVA | 25462 |
| HPV18 | E1 | 10 | 518 | EPLTDTKVAM | 25463 |
| HPV18 | E1 | 11 | 518 | EPLTDTKVAML | 25464 |
| HPV18 | E1 | 8 | 59 | EQAELETA | 25465 |
| HPV18 | E1 | 10 | 59 | EQAELETAQA | 25466 |
| HPV18 | E1 | 11 | 59 | EQAELETAQAL | 25467 |
| HPV18 | E1 | 10 | 104 | EVDTELSPRL | 25468 |
| HPV18 | E1 | 9 | 141 | EVEATQIQV | 25469 |
| HPV18 | E1 | 8 | 74 | EVHNDAQV | 25470 |
| HPV18 | E1 | 9 | 74 | EVHNDAQVL | 25471 |
| HPV18 | E1 | 11 | 74 | EVHNDAQVLHV | 25472 |
| HPV18 | E1 | 9 | 338 | EVMGDTPEW | 25473 |
| HPV18 | E1 | 10 | 338 | EVMGDTPEWI | 25474 |
| HPV18 | E1 | 8 | 50 | FIDTQGTF | 25475 |
| HPV18 | E1 | 8 | 497 | FIHFIQGA | 25476 |
| HPV18 | E1 | 9 | 497 | FIHFIQGAV | 25477 |
| HPV18 | E1 | 10 | 497 | FIHFIQGAVI | 25478 |
| HPV18 | E1 | 10 | 265 | FILYAHIQCL | 25479 |
| HPV18 | E1 | 9 | 500 | FIQGAVISF | 25480 |
| HPV18 | E1 | 10 | 500 | FIQGAVISFV | 25481 |
| HPV18 | E1 | 8 | 460 | FITFLGAL | 25482 |
| HPV18 | E1 | 11 | 460 | FITFLGALKSF | 25483 |
| HPV18 | E1 | 8 | 463 | FLGALKSF | 25484 |
| HPV18 | E1 | 9 | 463 | FLGALKSFL | 25485 |
| HPV18 | E1 | 11 | 470 | FLKGTPKKNCL | 25486 |
| HPV18 | E1 | 8 | 399 | FLKSNCQA | 25487 |
| HPV18 | E1 | 10 | 399 | FLKSNCQAKY | 25488 |
| HPV18 | E1 | 11 | 399 | FLKSNCQAKYL | 25489 |
| HPV18 | E1 | 9 | 452 | FLRYQQIEF | 25490 |
| HPV18 | E1 | 10 | 452 | FLRYQQIEFI | 25491 |
| HPV18 | E1 | 10 | 599 | FPFDKNGNPV | 25492 |
| HPV18 | E1 | 11 | 599 | FPFDKNGNPVY | 25493 |
| HPV18 | E1 | 8 | 508 | FVNSTSHF | 25494 |
| HPV18 | E1 | 9 | 508 | FVNSTSHFW | 25495 |
| HPV18 | E1 | 10 | 508 | FVNSTSHFWL | 25496 |
| HPV18 | E1 | 9 | 356 | GIDDSNFDL | 25497 |
| HPV18 | E1 | 8 | 332 | GISNISEV | 25498 |
| HPV18 | E1 | 9 | 332 | GISNISEVM | 25499 |
| HPV18 | E1 | 8 | 223 | GLSFTDLV | 25500 |
| HPV18 | E1 | 11 | 223 | GLSFTDLVRNF | 25501 |
| HPV18 | E1 | 8 | 300 | GLSTLLHV | 25502 |
| HPV18 | E1 | 8 | 494 | GMSFIHFI | 25503 |
| HPV18 | E1 | 11 | 494 | GMSFIHFIQGA | 25504 |
| HPV18 | E1 | 9 | 484 | GPANTGKSY | 25505 |
| HPV18 | E1 | 10 | 484 | GPANTGKSYF | 25506 |
| HPV18 | E1 | 9 | 121 | GQKKAKRRL | 25507 |
| HPV18 | E1 | 10 | 121 | GQKKAKRRLF | 25508 |
| HPV18 | E1 | 8 | 279 | GVLILALL | 25509 |

TABLE XIV-continued

B62 Supermotif Peptides

| Type | Protein | No. of Amino Acid | Position | Sequence | Seq. Id. No. |
|---|---|---|---|---|---|
| HPV18 | E1 | 10 | 279 | GVLILALLRY | 25510 |
| HPV18 | E1 | 10 | 249 | GVNPTIAEGF | 25511 |
| HPV18 | E1 | 9 | 270 | HIQCLDCKW | 25512 |
| HPV18 | E1 | 11 | 270 | HIQCLDCKWGV | 25513 |
| HPV18 | E1 | 8 | 576 | HPAKDNRW | 25514 |
| HPV18 | E1 | 10 | 576 | HPAKDNRWPY | 25515 |
| HPV18 | E1 | 11 | 576 | HPAKDNRWPYL | 25516 |
| HPV18 | E1 | 8 | 83 | HVLKRKFA | 25517 |
| HPV18 | E1 | 8 | 306 | HVPETCML | 25518 |
| HPV18 | E1 | 9 | 306 | HVPETCMLI | 25519 |
| HPV18 | E1 | 11 | 352 | IIQHGIDDSNF | 25520 |
| HPV18 | E1 | 10 | 569 | ILLTTNIHPA | 25521 |
| HPV18 | E1 | 9 | 266 | ILYAHIQCL | 25522 |
| HPV18 | E1 | 8 | 271 | IQCLDCKW | 25523 |
| HPV18 | E1 | 10 | 271 | IQCLDCKWGV | 25524 |
| HPV18 | E1 | 11 | 271 | IQCLDCKWGVL | 25525 |
| HPV18 | E1 | 8 | 501 | IQGAVISF | 25526 |
| HPV18 | E1 | 9 | 501 | IQGAVISFV | 25527 |
| HPV18 | E1 | 10 | 353 | IQHGIDDSNF | 25528 |
| HPV18 | E1 | 8 | 562 | IQLKCPPI | 25529 |
| HPV18 | E1 | 9 | 562 | IQLKCPPIL | 25530 |
| HPV18 | E1 | 10 | 562 | IQLKCPPILL | 25531 |
| HPV18 | E1 | 8 | 262 | IQPFILYA | 25532 |
| HPV18 | E1 | 10 | 262 | IQPFILYAHI | 25533 |
| HPV18 | E1 | 10 | 314 | IQPPKLRSSV | 25534 |
| HPV18 | E1 | 11 | 314 | IQPPKLRSSVA | 25535 |
| HPV18 | E1 | 11 | 347 | IQRLTIIQHGI | 25536 |
| HPV18 | E1 | 9 | 23 | IVDKKTGDV | 25537 |
| HPV18 | E1 | 10 | 23 | IVDKKTGDVI | 25538 |
| HPV18 | E1 | 10 | 449 | IVQFLRYQQI | 25539 |
| HPV18 | E1 | 8 | 439 | KIDEGGDW | 25540 |
| HPV18 | E1 | 11 | 439 | KIDEGGDWRPI | 25541 |
| HPV18 | E1 | 11 | 647 | KLRAGQNHRPL | 25542 |
| HPV18 | E1 | 8 | 318 | KLRSSVAA | 25543 |
| HPV18 | E1 | 9 | 318 | KLRSSVAAL | 25544 |
| HPV18 | E1 | 10 | 318 | KLRSSVAALY | 25545 |
| HPV18 | E1 | 11 | 318 | KLRSSVAALYW | 25546 |
| HPV18 | E1 | 11 | 559 | KPLIQLKCPPI | 25547 |
| HPV18 | E1 | 8 | 210 | KQGAMLAV | 25548 |
| HPV18 | E1 | 9 | 210 | KQGAMLAVF | 25549 |
| HPV18 | E1 | 8 | 524 | KVAMLDDA | 25550 |
| HPV18 | E1 | 8 | 206 | KVNNKQGA | 25551 |
| HPV18 | E1 | 9 | 206 | KVNNKQGAM | 25552 |
| HPV18 | E1 | 10 | 206 | KVNNKQGAML | 25553 |
| HPV18 | E1 | 11 | 206 | KVNNKQGAMLA | 25554 |
| HPV18 | E1 | 8 | 281 | LILALLRY | 25555 |
| HPV18 | E1 | 9 | 561 | LIQLKCPPI | 25556 |
| HPV18 | E1 | 10 | 561 | LIQLKCPPIL | 25557 |
| HPV18 | E1 | 11 | 561 | LIQLKCPPILL | 25558 |
| HPV18 | E1 | 8 | 261 | LIQPFILY | 25559 |
| HPV18 | E1 | 9 | 261 | LIQPFILYA | 25560 |
| HPV18 | E1 | 11 | 261 | LIQPFILYAHI | 25561 |
| HPV18 | E1 | 11 | 313 | LIQPPKLRSSV | 25562 |
| HPV18 | E1 | 9 | 388 | LLADSNSNA | 25563 |
| HPV18 | E1 | 10 | 388 | LLADSNSNAA | 25564 |
| HPV18 | E1 | 11 | 388 | LLADSNSNAAA | 25565 |
| HPV18 | E1 | 9 | 304 | LLHVPETCM | 25566 |
| HPV18 | E1 | 10 | 304 | LLHVPETCML | 25567 |
| HPV18 | E1 | 11 | 304 | LLHVPETCMLI | 25568 |
| HPV18 | E1 | 10 | 204 | LLKVNNKQGA | 25569 |
| HPV18 | E1 | 11 | 204 | LLKVNNKQGAM | 25570 |
| HPV18 | E1 | 11 | 285 | LLRYKCGKSRL | 25571 |
| HPV18 | E1 | 9 | 570 | LLTTNIHPA | 25572 |
| HPV18 | E1 | 9 | 214 | MLAVFKDTY | 25573 |
| HPV18 | E1 | 11 | 214 | MLAVFKDTYGL | 25574 |
| HPV18 | E1 | 10 | 527 | MLDDATTTCW | 25575 |
| HPV18 | E1 | 8 | 312 | MLIQPPKL | 25576 |
| HPV18 | E1 | 11 | 47 | MVDFIDTQGTF | 25577 |
| HPV18 | E1 | 10 | 367 | MVQWAFDNEL | 25578 |
| HPV18 | E1 | 11 | 188 | NIENVNPQCTI | 25579 |
| HPV18 | E1 | 10 | 574 | NIHPAKDNRW | 25580 |
| HPV18 | E1 | 8 | 428 | NMSQWIRF | 25581 |
| HPV18 | E1 | 8 | 641 | NPFGTFKL | 25582 |
| HPV18 | E1 | 10 | 641 | NPFGTFKLRA | 25583 |
| HPV18 | E1 | 9 | 193 | NPQCTIAQL | 25584 |

TABLE XIV-continued

B62 Supermotif Peptides

| Type | Protein | No. of Amino Acid | Position | Sequence | Seq. Id. No. |
|---|---|---|---|---|---|
| HPV18 | E1 | 8 | 251 | NPTIAEGF | 25585 |
| HPV18 | E1 | 11 | 251 | NPTIAEGFKTL | 25586 |
| HPV18 | E1 | 11 | 606 | NPVYEINDKNW | 25587 |
| HPV18 | E1 | 10 | 158 | NVCSGGSTEA | 25588 |
| HPV18 | E1 | 11 | 158 | NVCSGGSTEAI | 25589 |
| HPV18 | E1 | 8 | 191 | NVNPQCTI | 25590 |
| HPV18 | E1 | 9 | 191 | NVNPQCTIA | 25591 |
| HPV18 | E1 | 11 | 191 | NVNPQCTIAQL | 25592 |
| HPV18 | E1 | 8 | 568 | PILLTTNI | 25593 |
| HPV18 | E1 | 11 | 568 | PILLTTNIHPA | 25594 |
| HPV18 | E1 | 11 | 551 | PISIDRKHKPL | 25595 |
| HPV18 | E1 | 8 | 448 | PIVQFLRY | 25596 |
| HPV18 | E1 | 11 | 448 | PIVQFLRYQQI | 25597 |
| HPV18 | E1 | 8 | 98 | PLGERLEV | 25598 |
| HPV18 | E1 | 10 | 560 | PLIQLKCPPI | 25599 |
| HPV18 | E1 | 11 | 560 | PLIQLKCPPIL | 25600 |
| HPV18 | E1 | 8 | 519 | PLTDTKVA | 25601 |
| HPV18 | E1 | 9 | 519 | PLTDTKVAM | 25602 |
| HPV18 | E1 | 10 | 519 | PLTDTKVAML | 25603 |
| HPV18 | E1 | 9 | 567 | PPILLTTNI | 25604 |
| HPV18 | E1 | 8 | 316 | PPKLRSSV | 25605 |
| HPV18 | E1 | 9 | 316 | PPKLRSSVA | 25606 |
| HPV18 | E1 | 10 | 316 | PPKLRSSVAA | 25607 |
| HPV18 | E1 | 11 | 316 | PPKLRSSVAAL | 25608 |
| HPV18 | E1 | 8 | 194 | PQCTIAQL | 25609 |
| HPV18 | E1 | 11 | 194 | PQCTIAQLKDL | 25610 |
| HPV18 | E1 | 10 | 607 | PVYEINDKNW | 25611 |
| HPV18 | E1 | 8 | 457 | QIEFITFL | 25612 |
| HPV18 | E1 | 10 | 457 | QIEFITFLGA | 25613 |
| HPV18 | E1 | 11 | 457 | QIEFITFLGAL | 25614 |
| HPV18 | E1 | 8 | 563 | QLKCPPIL | 25615 |
| HPV18 | E1 | 9 | 563 | QLKCPPILL | 25616 |
| HPV18 | E1 | 8 | 200 | QLKDLLKV | 25617 |
| HPV18 | E1 | 8 | 426 | QMNMSQWI | 25618 |
| HPV18 | E1 | 10 | 426 | QMNMSQWIRF | 25619 |
| HPV18 | E1 | 9 | 263 | QPFILYAHI | 25620 |
| HPV18 | E1 | 9 | 315 | QPPKLRSSV | 25621 |
| HPV18 | E1 | 10 | 315 | QPPKLRSSVA | 25622 |
| HPV18 | E1 | 11 | 315 | QPPKLRSSVAA | 25623 |
| HPV18 | E1 | 8 | 456 | QQIEFITF | 25624 |
| HPV18 | E1 | 9 | 456 | QQIEFITFL | 25625 |
| HPV18 | E1 | 11 | 456 | QQIEFITFLGA | 25626 |
| HPV18 | E1 | 10 | 80 | QVLHVLKRKF | 25627 |
| HPV18 | E1 | 11 | 80 | QVLHVLKRKFA | 25628 |
| HPV18 | E1 | 10 | 589 | RITVFEFPNA | 25629 |
| HPV18 | E1 | 11 | 589 | RITVFEFPNAF | 25630 |
| HPV18 | E1 | 11 | 626 | RLDLHEEEEDA | 25631 |
| HPV18 | E1 | 8 | 102 | RLEVDTEL | 25632 |
| HPV18 | E1 | 10 | 128 | RLFTISDSGY | 25633 |
| HPV18 | E1 | 9 | 349 | RLTIIQHGI | 25634 |
| HPV18 | E1 | 8 | 294 | RLTVAKGL | 25635 |
| HPV18 | E1 | 11 | 294 | RLTVAKGLSTL | 25636 |
| HPV18 | E1 | 9 | 447 | RPIVQFLRY | 25637 |
| HPV18 | E1 | 8 | 425 | RQMNMSQW | 25638 |
| HPV18 | E1 | 9 | 425 | RQMNMSQWI | 25639 |
| HPV18 | E1 | 11 | 425 | RQMNMSQWIRF | 25640 |
| HPV18 | E1 | 9 | 553 | SIDRKHKPL | 25641 |
| HPV18 | E1 | 10 | 553 | SIDRKHKPLI | 25642 |
| HPV18 | E1 | 9 | 117 | SLNSGQKKA | 25643 |
| HPV18 | E1 | 9 | 97 | SPLGERLEV | 25644 |
| HPV18 | E1 | 9 | 110 | SPRLQEISL | 25645 |
| HPV18 | E1 | 11 | 430 | SQWIRFRCSKI | 25646 |
| HPV18 | E1 | 8 | 322 | SVAALYWY | 25647 |
| HPV18 | E1 | 11 | 179 | SVDGTSDNSNI | 25648 |
| HPV18 | E1 | 9 | 253 | TIAEGFKTL | 25649 |
| HPV18 | E1 | 10 | 253 | TIAEGFKTLI | 25650 |
| HPV18 | E1 | 8 | 197 | TIAQLKDL | 25651 |
| HPV18 | E1 | 9 | 197 | TIAQLKDLL | 25652 |
| HPV18 | E1 | 11 | 197 | TIAQLKDLLKV | 25653 |
| HPV18 | E1 | 8 | 260 | TLIQPFIL | 25654 |
| HPV18 | E1 | 9 | 260 | TLIQPFILY | 25655 |
| HPV18 | E1 | 10 | 260 | TLIQPFILYA | 25656 |
| HPV18 | E1 | 10 | 303 | TLLHVPETCM | 25657 |
| HPV18 | E1 | 11 | 303 | TLLHVPETCML | 25658 |
| HPV18 | E1 | 9 | 414 | TMCKHYRRA | 25659 |

TABLE XIV-continued

B62 Supermotif Peptides

| Type | Protein | No. of Amino Acid | Position | Sequence | Seq. Id. No. |
|---|---|---|---|---|---|
| HPV18 | E1 | 8 | 343 | TPEWIQRL | 25660 |
| HPV18 | E1 | 10 | 343 | TPEWIQRLTI | 25661 |
| HPV18 | E1 | 11 | 343 | TPEWIQRLTII | 25662 |
| HPV18 | E1 | 8 | 474 | TPKKNCLV | 25663 |
| HPV18 | E1 | 9 | 474 | TPKKNCLVF | 25664 |
| HPV18 | E1 | 9 | 53 | TQGTFCEQA | 25665 |
| HPV18 | E1 | 11 | 53 | TQGTFCEQAEL | 25666 |
| HPV18 | E1 | 9 | 296 | TVAKGLSTL | 25667 |
| HPV18 | E1 | 10 | 296 | TVAKGLSTLL | 25668 |
| HPV18 | E1 | 8 | 591 | TVFEFPNA | 25669 |
| HPV18 | E1 | 9 | 591 | TVFEFPNAF | 25670 |
| HPV18 | E1 | 11 | 591 | TVFEFPNAFPF | 25671 |
| HPV18 | E1 | 10 | 31 | VISDDEDENA | 25672 |
| HPV18 | E1 | 11 | 505 | VISFVNSTSHF | 25673 |
| HPV18 | E1 | 9 | 81 | VLHVLKRKF | 25674 |
| HPV18 | E1 | 10 | 81 | VLHVLKRKFA | 25675 |
| HPV18 | E1 | 9 | 280 | VLILALLRY | 25676 |
| HPV18 | E1 | 8 | 339 | VMGDTPEW | 25677 |
| HPV18 | E1 | 9 | 339 | VMGDTPEWI | 25678 |
| HPV18 | E1 | 8 | 307 | VPETCMLI | 25679 |
| HPV18 | E1 | 9 | 450 | VQFLRYQQI | 25680 |
| HPV18 | E1 | 11 | 450 | VQFLRYQQIEF | 25681 |
| HPV18 | E1 | 9 | 368 | VQWAFDNEL | 25682 |
| HPV18 | E1 | 8 | 346 | WIQRLTII | 25683 |
| HPV18 | E1 | 9 | 432 | WIRFRCSKI | 25684 |
| HPV18 | E1 | 10 | 516 | WLEPLTDTKV | 25685 |
| HPV18 | E1 | 11 | 516 | WLEPLTDTKVA | 25686 |
| HPV18 | E1 | 8 | 583 | WPYLESRI | 25687 |
| HPV18 | E1 | 10 | 583 | WPYLESRITV | 25688 |
| HPV18 | E1 | 11 | 583 | WPYLESRITVF | 25689 |
| HPV18 | E1 | 8 | 243 | WVTAIFGV | 25690 |
| HPV18 | E1 | 8 | 585 | YLESRITV | 25691 |
| HPV18 | E1 | 9 | 585 | YLESRITVF | 25692 |
| HPV18 | E1 | 11 | 585 | YLESRITVFEF | 25693 |
| HPV18 | E1 | 8 | 408 | YLKDCATM | 25694 |
| HPV18 | E1 | 11 | 542 | YMRNALDGNPI | 25695 |
| HPV18 | E1 | 9 | 455 | YQQIEFITF | 25696 |
| HPV18 | E1 | 10 | 455 | YQQIEFITFL | 25697 |
| HPV18 | E2 | 8 | 76 | AIELQMAL | 25698 |
| HPV18 | E2 | 11 | 76 | AIELQMALOGL | 25699 |
| HPV18 | E2 | 11 | 45 | AIFFAAREHGI | 25700 |
| HPV18 | E2 | 8 | 351 | AIPDSVQI | 25701 |
| HPV18 | E2 | 9 | 351 | AIPDSVQIL | 25702 |
| HPV18 | E2 | 10 | 351 | AIPDSVQILV | 25703 |
| HPV18 | E2 | 10 | 82 | ALQGLAQSRY | 25704 |
| HPV18 | E2 | 10 | 87 | AQSRYKTEDW | 25705 |
| HPV18 | E2 | 10 | 132 | CMTYVAWDSV | 25706 |
| HPV18 | E2 | 11 | 132 | CMTYVAWDSVY | 25707 |
| HPV18 | E2 | 10 | 14 | CVQDKIIDHY | 25708 |
| HPV18 | E2 | 8 | 156 | CVSHRGLY | 25709 |
| HPV18 | E2 | 9 | 156 | CVSHRGLYY | 25710 |
| HPV18 | E2 | 10 | 156 | CVSHRGYYV | 25711 |
| HPV18 | E2 | 8 | 29 | DIDSQIQY | 25712 |
| HPV18 | E2 | 9 | 29 | DIDSQIQYW | 25713 |
| HPV18 | E2 | 11 | 29 | DIDSQIQYWQL | 25714 |
| HPV18 | E2 | 8 | 315 | DISSTWHW | 25715 |
| HPV18 | E2 | 11 | 315 | DISSTWHWTGA | 25716 |
| HPV18 | E2 | 9 | 78 | ELQMALQGL | 25717 |
| HPV18 | E2 | 10 | 78 | ELQMALQGLA | 25718 |
| HPV18 | E2 | 11 | 104 | ELWNTEPTHCF | 25719 |
| HPV18 | E2 | 8 | 190 | EVHFGNNV | 25720 |
| HPV18 | E2 | 9 | 190 | EVHFGNNVI | 25721 |
| HPV18 | E2 | 11 | 346 | FLNTVAIPDSV | 25722 |
| HPV18 | E2 | 9 | 54 | GIQTLNHQV | 25723 |
| HPV18 | E2 | 10 | 54 | GIQTLNHQVV | 25724 |
| HPV18 | E2 | 11 | 253 | GLAEKQHCGPV | 25725 |
| HPV18 | E2 | 9 | 161 | GLYYVKEGY | 25726 |
| HPV18 | E2 | 9 | 261 | GPVNPLLGA | 25727 |
| HPV18 | E2 | 10 | 261 | GPVNPLLGAA | 25728 |
| HPV18 | E2 | 8 | 118 | GQTVQVYF | 25729 |
| HPV18 | E2 | 9 | 291 | HLKGDRNSL | 25730 |
| HPV18 | E2 | 9 | 60 | HQVVPAYNI | 25731 |
| HPV18 | E2 | 11 | 289 | IIHLKGDRNSL | 25732 |
| HPV18 | E2 | 8 | 358 | ILVGYMTM | 25733 |
| HPV18 | E2 | 8 | 352 | IPDSVQIL | 25734 |

TABLE XIV-continued

B62 Supermotif Peptides

| Type | Protein | No. of Amino Acid | Position | Sequence | Seq. Id. No. |
|---|---|---|---|---|---|
| HPV18 | E2 | 9 | 352 | IPDSVQILV | 25735 |
| HPV18 | E2 | 11 | 352 | IPDSVQILVGY | 25736 |
| HPV18 | E2 | 8 | 55 | IQTLNHQV | 25737 |
| HPV18 | E2 | 9 | 55 | IQTLNHQVV | 25738 |
| HPV18 | E2 | 11 | 55 | IQTLNHQVVPA | 25739 |
| HPV18 | E2 | 9 | 34 | IQYWQLIRW | 25740 |
| HPV18 | E2 | 10 | 280 | KLCSGNTTPI | 25741 |
| HPV18 | E2 | 11 | 280 | KLCSGNTTPII | 25742 |
| HPV18 | E2 | 10 | 257 | KQHCGPVNPL | 25743 |
| HPV18 | E2 | 11 | 257 | KQHCGPVNPLL | 25744 |
| HPV18 | E2 | 10 | 219 | KQLQHTPSPY | 25745 |
| HPV18 | E2 | 8 | 39 | LIRWENAI | 25746 |
| HPV18 | E2 | 9 | 39 | LIRWENAIF | 25747 |
| HPV18 | E2 | 10 | 39 | LIRWENAIFF | 25748 |
| HPV18 | E2 | 11 | 39 | LIRWENAIFFA | 25749 |
| HPV18 | E2 | 8 | 98 | LQDTCEEL | 25750 |
| HPV18 | E2 | 9 | 98 | LQDTCEELW | 25751 |
| HPV18 | E2 | 9 | 83 | LQGLAQSRY | 25752 |
| HPV18 | E2 | 8 | 221 | LQHTPSPY | 25753 |
| HPV18 | E2 | 8 | 79 | LQMALQGL | 25754 |
| HPV18 | E2 | 9 | 79 | LQMALQGLA | 25755 |
| HPV18 | E2 | 8 | 1 | MQTPKETL | 25756 |
| HPV18 | E2 | 10 | 67 | NISKSKAHKA | 25757 |
| HPV18 | E2 | 11 | 67 | NISKSKAHKAI | 25758 |
| HPV18 | E2 | 9 | 196 | NVIDCNDSM | 25759 |
| HPV18 | E2 | 8 | 262 | PVNPLLGA | 25760 |
| HPV18 | E2 | 9 | 262 | PVNPLLGAA | 25761 |
| HPV18 | E2 | 9 | 357 | QILVGYMTM | 25762 |
| HPV18 | E2 | 8 | 33 | QIQYWQLI | 25763 |
| HPV18 | E2 | 10 | 33 | QIQYWQLIRW | 25764 |
| HPV18 | E2 | 8 | 38 | QLIRWENA | 25765 |
| HPV18 | E2 | 9 | 38 | QLIRWENAI | 25766 |
| HPV18 | E2 | 10 | 38 | QLIRWENAIF | 25767 |
| HPV18 | E2 | 11 | 38 | QLIRWENAIFF | 25768 |
| HPV18 | E2 | 9 | 220 | QLQHTPSPY | 25769 |
| HPV18 | E2 | 8 | 80 | QMALQGLA | 25770 |
| HPV18 | E2 | 8 | 61 | QVVPAYNI | 25771 |
| HPV18 | E2 | 9 | 305 | RLRKHSDHY | 25772 |
| HPV18 | E2 | 9 | 11 | RLSCVQDKI | 25773 |
| HPV18 | E2 | 10 | 11 | RLSCVQDKII | 25774 |
| HPV18 | E2 | 8 | 248 | RPGHCGLA | 25775 |
| HPV18 | E2 | 9 | 298 | SLKCLRYRL | 25776 |
| HPV18 | E2 | 10 | 203 | SMCSTSDDTV | 25777 |
| HPV18 | E2 | 9 | 226 | SPYSSTVSV | 25778 |
| HPV18 | E2 | 8 | 32 | SQIQYWQL | 25779 |
| HPV18 | E2 | 9 | 32 | SQIQYWQLI | 25780 |
| HPV18 | E2 | 11 | 32 | SQIQYWQLIRW | 25781 |
| HPV18 | E2 | 8 | 233 | SVGTAKTY | 25782 |
| HPV18 | E2 | 8 | 355 | SVQILVGY | 25783 |
| HPV18 | E2 | 9 | 355 | SVQILVGYM | 25784 |
| HPV18 | E2 | 11 | 355 | SVQILVGYMTM | 25785 |
| HPV18 | E2 | 8 | 140 | SVYYMTDA | 25786 |
| HPV18 | E2 | 11 | 140 | SVYYMTDAGTW | 25787 |
| HPV18 | E2 | 9 | 57 | TLNHQVVPA | 25788 |
| HPV18 | E2 | 10 | 57 | TLNHQVVPAY | 25789 |
| HPV18 | E2 | 9 | 97 | TLQDTCEEL | 25790 |
| HPV18 | E2 | 10 | 97 | TLQDTCEELW | 25791 |
| HPV18 | E2 | 9 | 7 | TLSERLSCV | 25792 |
| HPV18 | E2 | 10 | 3 | TPKETLSERL | 25793 |
| HPV18 | E2 | 9 | 224 | TPSPYSSTV | 25794 |
| HPV18 | E2 | 11 | 224 | TPSPYSSTVSV | 25795 |
| HPV18 | E2 | 11 | 271 | TPTGNNKRRKL | 25796 |
| HPV18 | E2 | 10 | 341 | TQRTKFLNTV | 25797 |
| HPV18 | E2 | 11 | 341 | TQRTKFLNTVA | 25798 |
| HPV18 | E2 | 8 | 349 | TVAIPDSV | 25799 |
| HPV18 | E2 | 10 | 349 | TVAIPDSVQI | 25800 |
| HPV18 | E2 | 11 | 349 | TVAIPDSVQIL | 25801 |
| HPV18 | E2 | 8 | 211 | TVSATQLV | 25802 |
| HPV18 | E2 | 11 | 211 | TVSATQLVKQL | 25803 |
| HPV18 | E2 | 10 | 231 | TVSVGTAKTY | 25804 |
| HPV18 | E2 | 8 | 197 | VIDCNDSM | 25805 |
| HPV18 | E2 | 11 | 63 | VPAYNISKSKA | 25806 |
| HPV18 | E2 | 9 | 15 | VQDKIIDHY | 25807 |
| HPV18 | E2 | 8 | 356 | VQILVGYM | 25808 |
| HPV18 | E2 | 10 | 356 | VQILVGYMTM | 25809 |

TABLE XIV-continued

B62 Supermotif Peptides

| Type | Protein | No. of Amino Acid | Position | Sequence | Seq. Id. No. |
|---|---|---|---|---|---|
| HPV18 | E2 | 9 | 37 | WQLIRWENA | 25810 |
| HPV18 | E2 | 10 | 37 | WQLIRWENAI | 25811 |
| HPV18 | E2 | 11 | 37 | WQLIRWENAIF | 25812 |
| HPV18 | E2 | 11 | 173 | YIEFKSECEKY | 25813 |
| HPV18 | E2 | 8 | 143 | YMTDAGTW | 25814 |
| HPV18 | E2 | 8 | 135 | YVAWDSVY | 25815 |
| HPV18 | E2 | 9 | 135 | YVAWDSVYY | 25816 |
| HPV18 | E2 | 10 | 135 | YVAWDSVYYM | 25817 |
| HPV18 | E2 | 9 | 164 | YVKEGYNTF | 25818 |
| HPV18 | E2 | 10 | 164 | YVKEGYNTFY | 25819 |
| HPV18 | E2 | 11 | 164 | YVKEGYNTFYI | 25820 |
| HPV18 | E5 | 8 | 27 | CMCAYAWV | 25821 |
| HPV18 | E5 | 9 | 27 | CMCAYAWVL | 25822 |
| HPV18 | E5 | 10 | 27 | CMCAYAWVLV | 25823 |
| HPV18 | E5 | 11 | 27 | CMCAYAWVLVF | 25824 |
| HPV18 | E5 | 8 | 13 | CMYVCCHV | 25825 |
| HPV18 | E5 | 10 | 13 | CMYVCCHVPL | 25826 |
| HPV18 | E5 | 11 | 13 | CMYVCCHVPLL | 25827 |
| HPV18 | E5 | 10 | 11 | CVCMYVCCHV | 25828 |
| HPV18 | E5 | 9 | 6 | FLFCFCVCM | 25829 |
| HPV18 | E5 | 10 | 6 | FLFCFCVCMY | 25830 |
| HPV18 | E5 | 11 | 6 | FLFCFCVCMYV | 25831 |
| HPV18 | E5 | 8 | 57 | FLLPMLLL | 25832 |
| HPV18 | E5 | 10 | 57 | FLLPMLLLHI | 25833 |
| HPV18 | E5 | 11 | 37 | FVYIVVITSPA | 25834 |
| HPV18 | E5 | 8 | 65 | HIHAILSL | 25835 |
| HPV18 | E5 | 8 | 19 | HVPLLPSV | 25836 |
| HPV18 | E5 | 10 | 19 | HVPLLPSVCM | 25837 |
| HPV18 | E5 | 8 | 40 | IVVITSPA | 25838 |
| HPV18 | E5 | 10 | 40 | IVVITSPATA | 25839 |
| HPV18 | E5 | 11 | 40 | IVVITSPATAF | 25840 |
| HPV18 | E5 | 9 | 4 | LIFLFCFCV | 25841 |
| HPV18 | E5 | 11 | 4 | LIFLFCFCVCM | 25842 |
| HPV18 | E5 | 8 | 63 | LLHIHAIL | 25843 |
| HPV18 | E5 | 10 | 63 | LLHIHAILSL | 25844 |
| HPV18 | E5 | 8 | 62 | LLLHIHAI | 25845 |
| HPV18 | E5 | 9 | 62 | LLLHIHAIL | 25846 |
| HPV18 | E5 | 11 | 62 | LLLHIHAILSL | 25847 |
| HPV18 | E5 | 9 | 58 | LLPMLLLHI | 25848 |
| HPV18 | E5 | 11 | 58 | LLPMLLLHIHA | 25849 |
| HPV18 | E5 | 9 | 22 | LLPSVCMCA | 25850 |
| HPV18 | E5 | 10 | 22 | LLPSVCMCAY | 25851 |
| HPV18 | E5 | 11 | 22 | LLPSVCMCAYA | 25852 |
| HPV18 | E5 | 8 | 59 | LPMLLLHI | 25853 |
| HPV18 | E5 | 10 | 59 | LPMLLLHIHA | 25854 |
| HPV18 | E5 | 11 | 59 | LPMLLLHIHAI | 25855 |
| HPV18 | E5 | 8 | 23 | LPSVCMCA | 25856 |
| HPV18 | E5 | 9 | 23 | LPSVCMCAY | 25857 |
| HPV18 | E5 | 10 | 23 | LPSVCMCAYA | 25858 |
| HPV18 | E5 | 11 | 23 | LPSVCMCAYAW | 25859 |
| HPV18 | E5 | 8 | 35 | LVFVYIVV | 25860 |
| HPV18 | E5 | 9 | 35 | LVFVYIVVI | 25861 |
| HPV18 | E5 | 8 | 61 | MLLLHIHA | 25862 |
| HPV18 | E5 | 9 | 61 | MLLLHIHAI | 25863 |
| HPV18 | E5 | 10 | 61 | MLLLHIHAIL | 25864 |
| HPV18 | E5 | 8 | 1 | MLSLIFLF | 25865 |
| HPV18 | E5 | 10 | 1 | MLSLIFLCF | 25866 |
| HPV18 | E5 | 8 | 21 | PLLPSVCM | 25867 |
| HPV18 | E5 | 10 | 21 | PLLPSVCMCA | 25868 |
| HPV18 | E5 | 11 | 21 | PLLPSVCMCAY | 25869 |
| HPV18 | E5 | 9 | 60 | PMLLLHIHA | 25870 |
| HPV18 | E5 | 10 | 60 | PMLLLHIHAI | 25871 |
| HPV18 | E5 | 11 | 60 | PMLLLHIHAIL | 25872 |
| HPV18 | E5 | 8 | 3 | SLIFLFCF | 25873 |
| HPV18 | E5 | 10 | 3 | SLIFLFCFCV | 25874 |
| HPV18 | E5 | 8 | 45 | SPATAFTV | 25875 |
| HPV18 | E5 | 9 | 45 | SPATAFTVY | 25876 |
| HPV18 | E5 | 10 | 45 | SPATAFTVYV | 25877 |
| HPV18 | E5 | 11 | 45 | SPATAFTVYVF | 25878 |
| HPV18 | E5 | 8 | 25 | SVCMCAYA | 25879 |
| HPV18 | E5 | 9 | 25 | SVCMCAYAW | 25880 |
| HPV18 | E5 | 10 | 25 | SVCMCAYAWV | 25881 |
| HPV18 | E5 | 11 | 25 | SVCMCAYAWVL | 25882 |
| HPV18 | E5 | 8 | 51 | TVYVFCFL | 25883 |
| HPV18 | E5 | 9 | 51 | TVYVFCFLL | 25884 |

TABLE XIV-continued

B62 Supermotif Peptides

| Type | Protein | No. of Amino Acid | Position | Sequence | Seq. Id. No. |
|---|---|---|---|---|---|
| HPV18 | E5 | 11 | 51 | TVYVFCFLLPM | 25885 |
| HPV18 | E5 | 8 | 42 | VITSPATA | 25886 |
| HPV18 | E5 | 9 | 42 | VITSPATAF | 25887 |
| HPV18 | E5 | 11 | 42 | VITSPATAFTV | 25888 |
| HPV18 | E5 | 8 | 34 | VLVFVYIV | 25889 |
| HPV18 | E5 | 9 | 34 | VLVFVYIVV | 25890 |
| HPV18 | E5 | 10 | 34 | VLVFVYIVVI | 25891 |
| HPV18 | E5 | 9 | 20 | VPLLPSVCM | 25892 |
| HPV18 | E5 | 11 | 20 | VPLLPSVCMCA | 25893 |
| HPV18 | E5 | 9 | 41 | VVITSPATA | 25894 |
| HPV18 | E5 | 10 | 41 | VVITSPATAF | 25895 |
| HPV18 | E5 | 8 | 33 | WVLVFVYI | 25896 |
| HPV18 | E5 | 9 | 33 | WVLVFVYIV | 25897 |
| HPV18 | E5 | 10 | 33 | WVLVFVYIVV | 25898 |
| HPV18 | E5 | 11 | 33 | WVLVFVYIVVI | 25899 |
| HPV18 | E5 | 9 | 39 | YIVVITSPA | 25900 |
| HPV18 | E5 | 11 | 39 | YIVVITSPATA | 25901 |
| HPV18 | E5 | 8 | 15 | YVCCHVPL | 25902 |
| HPV18 | E5 | 9 | 15 | YVCCHVPLL | 25903 |
| HPV18 | E5 | 9 | 53 | YVFCFLLPM | 25904 |
| HPV18 | E5 | 10 | 53 | YVFCFLLPML | 25905 |
| HPV18 | E5 | 11 | 53 | YVFCFLLPMLL | 25906 |
| HPV18 | E6 | 8 | 68 | CIDFYSRI | 25907 |
| HPV18 | E6 | 11 | 68 | CIDFYSRIREL | 25908 |
| HPV18 | E6 | 8 | 105 | CLRCQKPL | 25909 |
| HPV18 | E6 | 11 | 105 | CLRCQKPLNPA | 25910 |
| HPV18 | E6 | 8 | 108 | CQKPLNPA | 25911 |
| HPV18 | E6 | 11 | 108 | CQKPLNPAEKL | 25912 |
| HPV18 | E6 | 8 | 32 | CVYCKTVL | 25913 |
| HPV18 | E6 | 10 | 32 | CVYCKTVLEL | 25914 |
| HPV18 | E6 | 8 | 27 | DIEITCVY | 25915 |
| HPV18 | E6 | 10 | 16 | DLCTELNTSL | 25916 |
| HPV18 | E6 | 10 | 51 | DLFVVYRDSI | 25917 |
| HPV18 | E6 | 9 | 6 | DPTRRPYKL | 25918 |
| HPV18 | E6 | 10 | 29 | EITCVYCKTV | 25919 |
| HPV18 | E6 | 11 | 29 | EITCVYCKTVL | 25920 |
| HPV18 | E6 | 9 | 20 | ELNTSLQDI | 25921 |
| HPV18 | E6 | 11 | 20 | ELNTSLQDIEI | 25922 |
| HPV18 | E6 | 9 | 77 | ELRHYSDSV | 25923 |
| HPV18 | E6 | 10 | 77 | ELRHYSDSVY | 25924 |
| HPV18 | E6 | 8 | 40 | ELTEVFEF | 25925 |
| HPV18 | E6 | 9 | 40 | ELTEVFEFA | 25926 |
| HPV18 | E6 | 10 | 40 | ELTEVFEFAF | 25927 |
| HPV18 | E6 | 10 | 43 | EVFEFAFKDL | 25928 |
| HPV18 | E6 | 11 | 43 | EVFEFAFKDLF | 25929 |
| HPV18 | E6 | 8 | 53 | FVVYRDSI | 25930 |
| HPV18 | E6 | 11 | 53 | FVVYRDSIPHA | 25931 |
| HPV18 | E6 | 10 | 97 | GLYNLLIRCL | 25932 |
| HPV18 | E6 | 10 | 136 | GQCHSCCNRA | 25933 |
| HPV18 | E6 | 8 | 120 | HLNEKRRF | 25934 |
| HPV18 | E6 | 11 | 120 | HLNEKRRFHNI | 25935 |
| HPV18 | E6 | 10 | 60 | IPHAACHKCI | 25936 |
| HPV18 | E6 | 9 | 13 | KLPDLCTEL | 25937 |
| HPV18 | E6 | 11 | 117 | KLRHLNEKRRF | 25938 |
| HPV18 | E6 | 8 | 92 | KLTNTGLY | 25939 |
| HPV18 | E6 | 10 | 92 | KLTNTGLYNL | 25940 |
| HPV18 | E6 | 11 | 92 | KLTNTGLYNLL | 25941 |
| HPV18 | E6 | 9 | 110 | KPLNPAEKL | 25942 |
| HPV18 | E6 | 11 | 102 | LIRCLRCQKPL | 25943 |
| HPV18 | E6 | 8 | 14 | LPDLCTEL | 25944 |
| HPV18 | E6 | 9 | 25 | LQDIEITCV | 25945 |
| HPV18 | E6 | 10 | 25 | LQDIEITCVY | 25946 |
| HPV18 | E6 | 9 | 150 | LQRRRETQV | 25947 |
| HPV18 | E6 | 9 | 113 | NPAEKLRHL | 25948 |
| HPV18 | E6 | 8 | 111 | PLNPAEKL | 25949 |
| HPV18 | E6 | 11 | 111 | PLNPAEKLRHL | 25950 |
| HPV18 | E6 | 8 | 74 | RIRELRHY | 25951 |
| HPV18 | E6 | 10 | 149 | RLQRRRETQV | 25952 |
| HPV18 | E6 | 8 | 10 | RPYKLPDL | 25953 |
| HPV18 | E6 | 11 | 59 | SIPHAACHKCI | 25954 |
| HPV18 | E6 | 10 | 24 | SLQDIEITCV | 25955 |
| HPV18 | E6 | 11 | 24 | SLQDIEITCVY | 25956 |
| HPV18 | E6 | 10 | 84 | SVYGDTLEKL | 25957 |
| HPV18 | E6 | 10 | 89 | TLEKLTNTGL | 25958 |
| HPV18 | E6 | 11 | 89 | TLEKLTNTGLY | 25959 |

TABLE XIV-continued

B62 Supermotif Peptides

| Type | Protein | No. of Amino Acid | Position | Sequence | Seq. Id. No. |
|---|---|---|---|---|---|
| HPV18 | E6 | 8 | 37 | TVLELTEV | 25960 |
| HPV18 | E6 | 9 | 37 | TVLELTEVF | 25961 |
| HPV18 | E6 | 11 | 37 | TVLELTEVFEF | 25962 |
| HPV18 | E6 | 8 | 38 | VLELTEVF | 25963 |
| HPV18 | E6 | 10 | 38 | VLELTEVFEF | 25964 |
| HPV18 | E6 | 11 | 38 | VLELTEVFEFA | 25965 |
| HPV18 | E6 | 10 | 54 | VVYRDSIPHA | 25966 |
| HPV18 | E6 | 11 | 54 | VVYRDSIPHAA | 25967 |
| HPV18 | E7 | 8 | 63 | CMCCKCEA | 25968 |
| HPV18 | E7 | 10 | 63 | CMCCKCEARI | 25969 |
| HPV18 | E7 | 8 | 24 | DLLCHEQL | 25970 |
| HPV18 | E7 | 8 | 82 | DLRAFQQL | 25971 |
| HPV18 | E7 | 9 | 82 | DLRAFQQLF | 25972 |
| HPV18 | E7 | 10 | 82 | DLRAFQQLFL | 25973 |
| HPV18 | E7 | 10 | 40 | EIDGVNHQHL | 25974 |
| HPV18 | E7 | 8 | 16 | EPQNEIPV | 25975 |
| HPV18 | E7 | 10 | 16 | EPQNEIPVDL | 25976 |
| HPV18 | E7 | 11 | 16 | EPQNEIPVDLL | 25977 |
| HPV18 | E7 | 8 | 55 | EPQRHTML | 25978 |
| HPV18 | E7 | 10 | 55 | EPQRHTMLCM | 25979 |
| HPV18 | E7 | 8 | 90 | FLNTLSFV | 25980 |
| HPV18 | E7 | 11 | 90 | FLNTLSFVCPW | 25981 |
| HPV18 | E7 | 9 | 86 | FQQLFLNTL | 25982 |
| HPV18 | E7 | 11 | 86 | FQQLFLNTLSF | 25983 |
| HPV18 | E7 | 9 | 3 | GPKATLQDI | 25984 |
| HPV18 | E7 | 10 | 3 | GPKATLQDIV | 25985 |
| HPV18 | E7 | 11 | 3 | GPKATLQDIVL | 25986 |
| HPV18 | E7 | 9 | 43 | GVNHQHLPA | 25987 |
| HPV18 | E7 | 8 | 14 | HLEPQNEI | 25988 |
| HPV18 | E7 | 10 | 14 | HLEPQNEIPV | 25989 |
| HPV18 | E7 | 9 | 46 | HQHLPARRA | 25990 |
| HPV18 | E7 | 11 | 21 | IPVDLLCHEQL | 25991 |
| HPV18 | E7 | 11 | 11 | IVLHLEPQNEI | 25992 |
| HPV18 | E7 | 8 | 73 | KLVVESSA | 25993 |
| HPV18 | E7 | 11 | 73 | KLVVESSADDL | 25994 |
| HPV18 | E7 | 8 | 8 | LQDIVLHL | 25995 |
| HPV18 | E7 | 10 | 74 | LVVESSADDL | 25996 |
| HPV18 | E7 | 10 | 61 | MLCMCCKCEA | 25997 |
| HPV18 | E7 | 9 | 17 | PQNEIPVDL | 25998 |
| HPV18 | E7 | 10 | 17 | PQNEIPVDLL | 25999 |
| HPV18 | E7 | 9 | 56 | PQRHTMLCM | 26000 |
| HPV18 | E7 | 10 | 22 | PVDLLCHEQL | 26001 |
| HPV18 | E7 | 9 | 88 | QLFLNTLSF | 26002 |
| HPV18 | E7 | 10 | 88 | QLFLNTLSFV | 26003 |
| HPV18 | E7 | 8 | 87 | QQLFLNTL | 26004 |
| HPV18 | E7 | 10 | 87 | QQLFLNTLSF | 26005 |
| HPV18 | E7 | 11 | 87 | QQLFLNTLSFV | 26006 |
| HPV18 | E7 | 10 | 71 | RIKLVVESSA | 26007 |
| HPV18 | E7 | 9 | 7 | TLQDIVLHL | 26008 |
| HPV18 | E7 | 8 | 93 | TLSFVCPW | 26009 |
| HPV18 | E7 | 10 | 93 | TLSFVCPWCA | 26010 |
| HPV18 | E7 | 11 | 60 | TMLCMCCKCEA | 26011 |
| HPV18 | E7 | 10 | 12 | VLHLEPQNEI | 26012 |
| HPV18 | E7 | 9 | 75 | VVESSADDL | 26013 |
| HPV18 | E7 | 11 | 75 | VVESSADDLRA | 26014 |
| HPV18 | L1 | 11 | 225 | AIGEHWAKGTA | 26015 |
| HPV18 | L1 | 8 | 487 | AITCQKDA | 26016 |
| HPV18 | L1 | 9 | 487 | AITCQKDAA | 26017 |
| HPV18 | L1 | 11 | 487 | AITCQKDAAPA | 26018 |
| HPV18 | L1 | 10 | 63 | ALWRPSDNTV | 26019 |
| HPV18 | L1 | 11 | 63 | ALWRPSDNTVY | 26020 |
| HPV18 | L1 | 9 | 495 | APAENKDPY | 26021 |
| HPV18 | L1 | 8 | 223 | APAIGEHW | 26022 |
| HPV18 | L1 | 9 | 223 | APAIGEHWA | 26023 |
| HPV18 | L1 | 11 | 549 | APSATTSSKPA | 26024 |
| HPV18 | L1 | 8 | 377 | AQGHNNGV | 26025 |
| HPV18 | L1 | 10 | 377 | AQGHNNGVCW | 26026 |
| HPV18 | L1 | 8 | 218 | CILGCAPA | 26027 |
| HPV18 | L1 | 9 | 218 | CILGCAPAI | 26028 |
| HPV18 | L1 | 8 | 310 | CLRREQLF | 26029 |
| HPV18 | L1 | 9 | 310 | CLRREQLFA | 26030 |
| HPV18 | L1 | 8 | 2 | CLYTRVLI | 26031 |
| HPV18 | L1 | 9 | 2 | CLYTRVLIL | 26032 |
| HPV18 | L1 | 11 | 2 | CLYTRVLILHY | 26033 |
| HPV18 | L1 | 10 | 246 | CPPLELKNTV | 26034 |

TABLE XIV-continued

B62 Supermotif Peptides

| Type | Protein | No. of Amino Acid | Position | Sequence | Seq. Id. No. |
|---|---|---|---|---|---|
| HPV18 | L1 | 11 | 246 | CPPLELKNTVL | 26035 |
| HPV18 | L1 | 8 | 490 | CQKDAAPA | 26036 |
| HPV18 | L1 | 10 | 286 | CQSICKYPDY | 26037 |
| HPV18 | L1 | 11 | 286 | CQSICKYPDYL | 26038 |
| HPV18 | L1 | 11 | 350 | CVYSPSPSGSI | 26039 |
| HPV18 | L1 | 9 | 284 | DICQSICKY | 26040 |
| HPV18 | L1 | 8 | 122 | DIPKVSAY | 26041 |
| HPV18 | L1 | 10 | 122 | DIPKVSAYQY | 26042 |
| HPV18 | L1 | 11 | 520 | DLDQYPLGRKF | 26043 |
| HPV18 | L1 | 8 | 512 | DLKEKFSL | 26044 |
| HPV18 | L1 | 10 | 512 | DLKEKFSLDL | 26045 |
| HPV18 | L1 | 8 | 433 | DLQFIFQL | 26046 |
| HPV18 | L1 | 11 | 433 | DLQFIFQLCTI | 26047 |
| HPV18 | L1 | 9 | 260 | DMVDTGYGA | 26048 |
| HPV18 | L1 | 10 | 260 | DMVDTGYGAM | 26049 |
| HPV18 | L1 | 8 | 501 | DPYDKLKF | 26050 |
| HPV18 | L1 | 9 | 501 | DPYDKLKFW | 26051 |
| HPV18 | L1 | 11 | 501 | DPYDKLKFWNV | 26052 |
| HPV18 | L1 | 8 | 301 | DPYGDSMF | 26053 |
| HPV18 | L1 | 9 | 301 | DPYGDSMFF | 26054 |
| HPV18 | L1 | 11 | 301 | DPYGDSMFFCL | 26055 |
| HPV18 | L1 | 9 | 522 | DQYPLGRKF | 26056 |
| HPV18 | L1 | 10 | 522 | DQYPLGRKFL | 26057 |
| HPV18 | L1 | 11 | 522 | DQYPLGRKFLV | 26058 |
| HPV18 | L1 | 9 | 448 | DVMSYIHSM | 26059 |
| HPV18 | L1 | 8 | 203 | DVRDNVSV | 26060 |
| HPV18 | L1 | 10 | 203 | DVRDNVSVDY | 26061 |
| HPV18 | L1 | 8 | 167 | EIGRGQPL | 26062 |
| HPV18 | L1 | 10 | 167 | EIGRGQPLGV | 26063 |
| HPV18 | L1 | 8 | 314 | EQLFARHF | 26064 |
| HPV18 | L1 | 9 | 314 | EQLFARHFW | 26065 |
| HPV18 | L1 | 10 | 280 | EVPLDICQSI | 26066 |
| HPV18 | L1 | 8 | 436 | FIFQLCTI | 26067 |
| HPV18 | L1 | 10 | 436 | FIFQLCTITL | 26068 |
| HPV18 | L1 | 8 | 49 | FLRNVNVF | 26069 |
| HPV18 | L1 | 10 | 49 | FLRNVNVFPI | 26070 |
| HPV18 | L1 | 11 | 49 | FLRNVNVFPIF | 26071 |
| HPV18 | L1 | 8 | 56 | FPIFLQMA | 26072 |
| HPV18 | L1 | 9 | 56 | FPIFLQMAL | 26073 |
| HPV18 | L1 | 10 | 56 | FPIFLQMALW | 26074 |
| HPV18 | L1 | 8 | 438 | FQLCTITL | 26075 |
| HPV18 | L1 | 10 | 438 | FQLCTITLTA | 26076 |
| HPV18 | L1 | 8 | 145 | GLPDTSIY | 26077 |
| HPV18 | L1 | 8 | 535 | GLRRKPTI | 26078 |
| HPV18 | L1 | 8 | 177 | GLSGHPFY | 26079 |
| HPV18 | L1 | 11 | 177 | GLSGHPFYNKL | 26080 |
| HPV18 | L1 | 10 | 342 | GMPASPGSCV | 26081 |
| HPV18 | L1 | 11 | 342 | GMPASPGSCVY | 26082 |
| HPV18 | L1 | 9 | 19 | GPLYHPRPL | 26083 |
| HPV18 | L1 | 11 | 19 | GPLYHPRPLPL | 26084 |
| HPV18 | L1 | 10 | 543 | GPRKRSAPSA | 26085 |
| HPV18 | L1 | 8 | 171 | GQPLGVGL | 26086 |
| HPV18 | L1 | 8 | 415 | GQYDATKF | 26087 |
| HPV18 | L1 | 11 | 415 | GQYDATKFKQY | 26088 |
| HPV18 | L1 | 8 | 383 | GVCWHNQL | 26089 |
| HPV18 | L1 | 9 | 383 | GVCWHNQLF | 26090 |
| HPV18 | L1 | 10 | 383 | GVCWHNQLFV | 26091 |
| HPV18 | L1 | 10 | 165 | GVEIGRGQPL | 26092 |
| HPV18 | L1 | 9 | 175 | GVGLSGHPF | 26093 |
| HPV18 | L1 | 10 | 175 | GVGLSGHPFY | 26094 |
| HPV18 | L1 | 10 | 467 | GVPPPPTTSL | 26095 |
| HPV18 | L1 | 11 | 467 | GVPPPPTTSLV | 26096 |
| HPV18 | L1 | 8 | 38 | HIIICGHY | 26097 |
| HPV18 | L1 | 9 | 38 | HIIICGHYI | 26098 |
| HPV18 | L1 | 10 | 38 | HIIICGHYII | 26099 |
| HPV18 | L1 | 11 | 38 | HIIICGHYIIL | 26100 |
| HPV18 | L1 | 9 | 13 | HLLPLYGPL | 26101 |
| HPV18 | L1 | 10 | 13 | HLLPLYGPLY | 26102 |
| HPV18 | L1 | 10 | 23 | HPRPLPLHSI | 26103 |
| HPV18 | L1 | 11 | 23 | HPRPLPLHSIL | 26104 |
| HPV18 | L1 | 9 | 428 | HVEEYDLQF | 26105 |
| HPV18 | L1 | 10 | 428 | HVEEYDLQFI | 26106 |
| HPV18 | L1 | 11 | 428 | HVEEYDLQFIF | 26107 |
| HPV18 | L1 | 8 | 40 | IICGHYII | 26108 |
| HPV18 | L1 | 9 | 40 | IICGHYIIL | 26109 |

TABLE XIV-continued

B62 Supermotif Peptides

| Type | Protein | No. of Amino Acid | Position | Sequence | Seq. Id. No. |
|---|---|---|---|---|---|
| HPV18 | L1 | 10 | 40 | IICGHYIILP | 26110 |
| HPV18 | L1 | 11 | 40 | IICGHYIILFL | 26111 |
| HPV18 | L1 | 8 | 39 | IIICGHYI | 26112 |
| HPV18 | L1 | 9 | 39 | IIICGHYII | 26113 |
| HPV18 | L1 | 10 | 39 | IIICGHYIIL | 26114 |
| HPV18 | L1 | 11 | 39 | IIICGHYIILF | 26115 |
| HPV18 | L1 | 8 | 46 | IILFLRNV | 26116 |
| HPV18 | L1 | 10 | 46 | IILFLRNVNV | 26117 |
| HPV18 | L1 | 11 | 46 | IILFLRNVNVF | 26118 |
| HPV18 | L1 | 9 | 460 | ILEDWNFGV | 26119 |
| HPV18 | L1 | 9 | 47 | ILFLRNVNV | 26120 |
| HPV18 | L1 | 10 | 47 | ILFLRNVNVF | 26121 |
| HPV18 | L1 | 8 | 219 | ILGCAPAI | 26122 |
| HPV18 | L1 | 9 | 9 | ILHYHLLPL | 26123 |
| HPV18 | L1 | 10 | 9 | ILHYHLLPLY | 26124 |
| HPV18 | L1 | 8 | 32 | ILVYMVHI | 26125 |
| HPV18 | L1 | 9 | 32 | ILVYMVHII | 26126 |
| HPV18 | L1 | 10 | 32 | ILVYMVHIII | 26127 |
| HPV18 | L1 | 9 | 123 | IPKVSAYQY | 26128 |
| HPV18 | L1 | 11 | 123 | IPKVSAYQYRV | 26129 |
| HPV18 | L1 | 8 | 360 | IVTSDSQL | 26130 |
| HPV18 | L1 | 9 | 360 | IVTSDSQLF | 26131 |
| HPV18 | L1 | 10 | 186 | KLDDTESSHA | 26132 |
| HPV18 | L1 | 11 | 186 | KLDDTESSHAA | 26133 |
| HPV18 | L1 | 9 | 505 | KLKFWNVDL | 26134 |
| HPV18 | L1 | 8 | 557 | KPAKRVRV | 26135 |
| HPV18 | L1 | 10 | 557 | KPAKRVRVRA | 26136 |
| HPV18 | L1 | 11 | 539 | KPTIGPRKRSA | 26137 |
| HPV18 | L1 | 8 | 370 | KPYWLHKA | 26138 |
| HPV18 | L1 | 9 | 120 | KQDIPKVSA | 26139 |
| HPV18 | L1 | 10 | 120 | KQDIPKVSAY | 26140 |
| HPV18 | L1 | 8 | 213 | KQTQLCIL | 26141 |
| HPV18 | L1 | 11 | 213 | KQTQLCILGCA | 26142 |
| HPV18 | L1 | 10 | 423 | KQYSRHVEEY | 26143 |
| HPV18 | L1 | 9 | 125 | KVSAYQYRV | 26144 |
| HPV18 | L1 | 10 | 125 | KVSAYQYRVF | 26145 |
| HPV18 | L1 | 8 | 8 | LILHYHLL | 26146 |
| HPV18 | L1 | 10 | 8 | LILHYHLLPL | 26147 |
| HPV18 | L1 | 11 | 8 | LILHYHLLPLY | 26148 |
| HPV18 | L1 | 8 | 14 | LLPLYGPL | 26149 |
| HPV18 | L1 | 9 | 14 | LLPLYGPLY | 26150 |
| HPV18 | L1 | 8 | 103 | LLTVGNPY | 26151 |
| HPV18 | L1 | 9 | 103 | LLTVGNPYF | 26152 |
| HPV18 | L1 | 11 | 103 | LLTVGNPYFRV | 26153 |
| HPV18 | L1 | 9 | 138 | LPDPNKFGL | 26154 |
| HPV18 | L1 | 8 | 27 | LPLHSILV | 26155 |
| HPV18 | L1 | 9 | 27 | LPLHSILVY | 26156 |
| HPV18 | L1 | 10 | 27 | LPLHSILVYM | 26157 |
| HPV18 | L1 | 11 | 27 | LPLHSILVYMV | 26158 |
| HPV18 | L1 | 8 | 15 | LPLYGPLY | 26159 |
| HPV18 | L1 | 9 | 74 | LPPPSVARV | 26160 |
| HPV18 | L1 | 10 | 74 | LPPPSVARVV | 26161 |
| HPV18 | L1 | 8 | 274 | LQDTKCEV | 26162 |
| HPV18 | L1 | 10 | 274 | LQDTKCEVPL | 26163 |
| HPV18 | L1 | 10 | 434 | LQFIFQLCTI | 26164 |
| HPV18 | L1 | 8 | 296 | LQMSADPY | 26165 |
| HPV18 | L1 | 8 | 476 | LVDTYRFV | 26166 |
| HPV18 | L1 | 11 | 476 | LVDTYRFVQSV | 26167 |
| HPV18 | L1 | 8 | 159 | LVWACAGV | 26168 |
| HPV18 | L1 | 10 | 159 | LVWACAGVEI | 26169 |
| HPV18 | L1 | 8 | 33 | LVYMVHII | 26170 |
| HPV18 | L1 | 9 | 33 | LVYMVHIII | 26171 |
| HPV18 | L1 | 9 | 343 | MPASPGSCV | 26172 |
| HPV18 | L1 | 10 | 343 | MPASPGSCVY | 26173 |
| HPV18 | L1 | 8 | 261 | MVDTGYGA | 26174 |
| HPV18 | L1 | 9 | 261 | MVDTGYGAM | 26175 |
| HPV18 | L1 | 11 | 261 | MVDTGYGAMDF | 26176 |
| HPV18 | L1 | 10 | 36 | MVHIIICGHY | 26177 |
| HPV18 | L1 | 11 | 36 | MVHIIICGHYI | 26178 |
| HPV18 | L1 | 8 | 153 | NPETQRLV | 26179 |
| HPV18 | L1 | 9 | 153 | NPETQRLVW | 26180 |
| HPV18 | L1 | 10 | 153 | NPETQRLVWA | 26181 |
| HPV18 | L1 | 8 | 108 | NPYFRVPA | 26182 |
| HPV18 | L1 | 8 | 388 | NQLFVTVV | 26183 |
| HPV18 | L1 | 8 | 510 | NVDLKEKF | 26184 |

TABLE XIV-continued

B62 Supermotif Peptides

| Type | Protein | No. of Amino Acid | Position | Sequence | Seq. Id. No. |
|---|---|---|---|---|---|
| HPV18 | L1 | 10 | 510 | NVDLKEKFSL | 26185 |
| HPV18 | L1 | 9 | 54 | NVFPIFLQM | 26186 |
| HPV18 | L1 | 10 | 54 | NVFPIFLQMA | 26187 |
| HPV18 | L1 | 11 | 54 | NVFPIFLQMAL | 26188 |
| HPV18 | L1 | 8 | 52 | NVNVFPIF | 26189 |
| HPV18 | L1 | 9 | 52 | NVNVFPIFL | 26190 |
| HPV18 | L1 | 11 | 52 | NVNVFPIFLQM | 26191 |
| HPV18 | L1 | 10 | 199 | NVSEDVRDNV | 26192 |
| HPV18 | L1 | 11 | 207 | NVSVDYKQTQL | 26193 |
| HPV18 | L1 | 8 | 57 | PIFLQMAL | 26194 |
| HPV18 | L1 | 9 | 57 | PIFLQMALW | 26195 |
| HPV18 | L1 | 8 | 282 | PLDICQSI | 26196 |
| HPV18 | L1 | 11 | 282 | PLDICQSICKY | 26197 |
| HPV18 | L1 | 8 | 248 | PLELKNTV | 26198 |
| HPV18 | L1 | 9 | 248 | PLELKNTVL | 26199 |
| HPV18 | L1 | 8 | 525 | PLGRKFLV | 26200 |
| HPV18 | L1 | 10 | 525 | PLGRKFLVQA | 26201 |
| HPV18 | L1 | 11 | 173 | PLGVGLSGHPF | 26202 |
| HPV18 | L1 | 8 | 28 | PLHSILVY | 26203 |
| HPV18 | L1 | 9 | 28 | PLHSILVYM | 26204 |
| HPV18 | L1 | 10 | 28 | PLHSILVYMV | 26205 |
| HPV18 | L1 | 8 | 26 | PLPLHSIL | 26206 |
| HPV18 | L1 | 9 | 26 | PLPLHSILV | 26207 |
| HPV18 | L1 | 10 | 26 | PLPLHSILVY | 26208 |
| HPV18 | L1 | 11 | 26 | PLPLHSILVYM | 26209 |
| HPV18 | L1 | 10 | 240 | PLSQGDCPPL | 26210 |
| HPV18 | L1 | 8 | 20 | PLYHPRPL | 26211 |
| HPV18 | L1 | 10 | 20 | PLYHPRPLPL | 26212 |
| HPV18 | L1 | 9 | 247 | PPLELKNTV | 26213 |
| HPV18 | L1 | 10 | 247 | PPLELKNTVL | 26214 |
| HPV18 | L1 | 8 | 469 | PPPPTTSL | 26215 |
| HPV18 | L1 | 9 | 469 | PPPPTTSLV | 26216 |
| HPV18 | L1 | 8 | 75 | PPPSVARV | 26217 |
| HPV18 | L1 | 9 | 75 | PPPSVARVV | 26218 |
| HPV18 | L1 | 8 | 470 | PPPTTSLV | 26219 |
| HPV18 | L1 | 11 | 470 | PPPTTSLVDTY | 26220 |
| HPV18 | L1 | 8 | 76 | PPSVARVV | 26221 |
| HPV18 | L1 | 10 | 471 | PPTTSLVDTY | 26222 |
| HPV18 | L1 | 11 | 333 | PQSLYIKGTGM | 26223 |
| HPV18 | L1 | 8 | 412 | PVPGQYDA | 26224 |
| HPV18 | L1 | 11 | 412 | PVPGQYDATKF | 26225 |
| HPV18 | L1 | 8 | 216 | QLCILGCA | 26226 |
| HPV18 | L1 | 10 | 216 | QLCILGCAPA | 26227 |
| HPV18 | L1 | 11 | 216 | QLCILGCAPAI | 26228 |
| HPV18 | L1 | 9 | 439 | QLCTITLTA | 26229 |
| HPV18 | L1 | 11 | 439 | QLCTITLTADV | 26230 |
| HPV18 | L1 | 8 | 315 | QLFARHFW | 26231 |
| HPV18 | L1 | 11 | 315 | QLFARHFWNRA | 26232 |
| HPV18 | L1 | 8 | 366 | QLFNKPYW | 26233 |
| HPV18 | L1 | 9 | 366 | QLFNKPYWL | 26234 |
| HPV18 | L1 | 8 | 137 | QLPDPNKF | 26235 |
| HPV18 | L1 | 10 | 137 | QLPDPNKFGL | 26236 |
| HPV18 | L1 | 11 | 297 | QMSADPYGDSM | 26237 |
| HPV18 | L1 | 9 | 102 | RLLTVGNPY | 26238 |
| HPV18 | L1 | 10 | 102 | RLLTVGNPYF | 26239 |
| HPV18 | L1 | 9 | 158 | RLVWACAGV | 26240 |
| HPV18 | L1 | 11 | 158 | RLVWACAGVEI | 26241 |
| HPV18 | L1 | 8 | 25 | RPLPLHSI | 26242 |
| HPV18 | L1 | 9 | 25 | RPLPLHSIL | 26243 |
| HPV18 | L1 | 10 | 25 | RPLPLHSILV | 26244 |
| HPV18 | L1 | 11 | 25 | RPLPLHSILVY | 26245 |
| HPV18 | L1 | 11 | 239 | RPLSQGDCPPL | 26246 |
| HPV18 | L1 | 8 | 66 | RPSDNTVY | 26247 |
| HPV18 | L1 | 9 | 66 | RPSDNTVYL | 26248 |
| HPV18 | L1 | 9 | 6 | RVLILHYHL | 26249 |
| HPV18 | L1 | 10 | 6 | RVLILHYHLL | 26250 |
| HPV18 | L1 | 10 | 135 | RVQLPDPNKF | 26251 |
| HPV18 | L1 | 8 | 81 | RVVNTDDY | 26252 |
| HPV18 | L1 | 9 | 81 | RVVNTDDYV | 26253 |
| HPV18 | L1 | 8 | 288 | SICKYPDY | 26254 |
| HPV18 | L1 | 9 | 288 | SICKYPDYL | 26255 |
| HPV18 | L1 | 11 | 288 | SICKYPDYLQM | 26256 |
| HPV18 | L1 | 11 | 93 | SIFYHAGSSRL | 26257 |
| HPV18 | L1 | 8 | 459 | SILEDWNF | 26258 |
| HPV18 | L1 | 10 | 459 | SILEDWNFGV | 26259 |

TABLE XIV-continued

B62 Supermotif Peptides

| Type | Protein | No. of Amino Acid | Position | Sequence | Seq. Id. No. |
|---|---|---|---|---|---|
| HPV18 | L1 | 9 | 31 | SILVYMVHI | 26260 |
| HPV18 | L1 | 10 | 31 | SILVYMVHII | 26261 |
| HPV18 | L1 | 11 | 31 | SILVYMVHIII | 26262 |
| HPV18 | L1 | 9 | 359 | SIVTSDSQL | 26263 |
| HPV18 | L1 | 10 | 359 | SIVTSDSQLF | 26264 |
| HPV18 | L1 | 10 | 150 | SIYNPETQRL | 26265 |
| HPV18 | L1 | 11 | 150 | SIYNPETQRLV | 26266 |
| HPV18 | L1 | 9 | 518 | SLDLDQYPL | 26267 |
| HPV18 | L1 | 8 | 475 | SLVDTYRF | 26268 |
| HPV18 | L1 | 9 | 475 | SLVDTYRFV | 26269 |
| HPV18 | L1 | 9 | 335 | SLYIKGTGM | 26270 |
| HPV18 | L1 | 11 | 335 | SLYIKGTGMPA | 26271 |
| HPV18 | L1 | 11 | 306 | SMFFCLRREQL | 26272 |
| HPV18 | L1 | 10 | 455 | SMNSSILEDW | 26273 |
| HPV18 | L1 | 8 | 353 | SPSPSGSI | 26274 |
| HPV18 | L1 | 9 | 353 | SPSPSGSIV | 26275 |
| HPV18 | L1 | 9 | 411 | SPVPGQYDA | 26276 |
| HPV18 | L1 | 8 | 242 | SQGDCPPL | 26277 |
| HPV18 | L1 | 10 | 242 | SQGDCPPLEL | 26278 |
| HPV18 | L1 | 8 | 365 | SQLFNKPY | 26279 |
| HPV18 | L1 | 9 | 365 | SQLFNKPYW | 26280 |
| HPV18 | L1 | 10 | 365 | SQLFNKPYWL | 26281 |
| HPV18 | L1 | 10 | 485 | SVAITCQKDA | 26282 |
| HPV18 | L1 | 11 | 485 | SVAITCQKDAA | 26283 |
| HPV18 | L1 | 11 | 78 | SVARVVNTDDY | 26284 |
| HPV18 | L1 | 9 | 209 | SVDYKQTQL | 26285 |
| HPV18 | L1 | 11 | 209 | SVDYKQTQLCI | 26286 |
| HPV18 | L1 | 10 | 404 | TICASTQSPV | 26287 |
| HPV18 | L1 | 9 | 541 | TIGPRKRSA | 26288 |
| HPV18 | L1 | 8 | 442 | TITLTADV | 26289 |
| HPV18 | L1 | 9 | 442 | TITLTADVM | 26290 |
| HPV18 | L1 | 11 | 442 | TITLTADVMSY | 26291 |
| HPV18 | L1 | 9 | 273 | TLQDTKCEV | 26292 |
| HPV18 | L1 | 11 | 273 | TLQDTKCEVPL | 26293 |
| HPV18 | L1 | 9 | 444 | TLTADVMSY | 26294 |
| HPV18 | L1 | 10 | 444 | TLTADVMSYI | 26295 |
| HPV18 | L1 | 10 | 327 | TMGDTVPQSL | 26296 |
| HPV18 | L1 | 11 | 327 | TMGDTVPQSLY | 26297 |
| HPV18 | L1 | 8 | 398 | TPSTNLTI | 26298 |
| HPV18 | L1 | 10 | 398 | TPSTNLTICA | 26299 |
| HPV18 | L1 | 9 | 90 | TPTSIFYHA | 26300 |
| HPV18 | L1 | 9 | 215 | TQLCILGCA | 26301 |
| HPV18 | L1 | 11 | 215 | TQLCILGCAPA | 26302 |
| HPV18 | L1 | 9 | 156 | TQRLVWACA | 26303 |
| HPV18 | L1 | 11 | 156 | TQRLVWACAGV | 26304 |
| HPV18 | L1 | 9 | 409 | TQSPVPGQY | 26305 |
| HPV18 | L1 | 11 | 409 | TQSPVPGQYDA | 26306 |
| HPV18 | L1 | 9 | 105 | TVGNPYFRV | 26307 |
| HPV18 | L1 | 11 | 105 | TVGNPYFRVPA | 26308 |
| HPV18 | L1 | 8 | 254 | TVLEDGDM | 26309 |
| HPV18 | L1 | 9 | 254 | TVLEDGDMV | 26310 |
| HPV18 | L1 | 8 | 331 | TVPQSLYI | 26311 |
| HPV18 | L1 | 11 | 393 | TVVDTTPSTNL | 26312 |
| HPV18 | L1 | 9 | 71 | TVYLPPPSV | 26313 |
| HPV18 | L1 | 10 | 71 | TVYLPPPSVA | 26314 |
| HPV18 | L1 | 8 | 255 | VLEDGDMV | 26315 |
| HPV18 | L1 | 8 | 7 | VLILHYHL | 26316 |
| HPV18 | L1 | 9 | 7 | VLILHYHLL | 26317 |
| HPV18 | L1 | 11 | 7 | VLILHYHLLPL | 26318 |
| HPV18 | L1 | 8 | 449 | VMSYIHSM | 26319 |
| HPV18 | L1 | 11 | 113 | VPAGGGNKQDI | 26320 |
| HPV18 | L1 | 10 | 113 | VPGQYDATKF | 26321 |
| HPV18 | L1 | 9 | 281 | VPLDICQSI | 26322 |
| HPV18 | L1 | 9 | 468 | VPPPPTTSL | 26323 |
| HPV18 | L1 | 10 | 468 | VPPPPTTSLV | 26324 |
| HPV18 | L1 | 11 | 532 | VQAGLRRKPTI | 26325 |
| HPV18 | L1 | 9 | 136 | VQLPDPNKF | 26326 |
| HPV18 | L1 | 11 | 136 | VQLPDPNKFGL | 26327 |
| HPV18 | L1 | 10 | 394 | VVDTTPSTNL | 26328 |
| HPV18 | L1 | 8 | 82 | VVNTDDYV | 26329 |
| HPV18 | L1 | 9 | 452 | YIHSMNSSI | 26330 |
| HPV18 | L1 | 10 | 452 | YIHSMNSSIL | 26331 |
| HPV18 | L1 | 9 | 45 | YIILFLRNV | 26332 |
| HPV18 | L1 | 11 | 45 | YIILFLRNVNV | 26333 |
| HPV18 | L1 | 9 | 337 | YIKGTGMPA | 26334 |

TABLE XIV-continued

B62 Supermotif Peptides

| Type | Protein | No. of Amino Acid | Position | Sequence | Seq. Id. No. |
|---|---|---|---|---|---|
| HPV18 | L1 | 8 | 73 | YLPPPSVA | 26335 |
| HPV18 | L1 | 10 | 73 | YLPPPSVARV | 26336 |
| HPV18 | L1 | 11 | 73 | YLPPPSVARVV | 26337 |
| HPV18 | L1 | 9 | 295 | YLQMSADPY | 26338 |
| HPV18 | L1 | 11 | 35 | YMVHIIICGHY | 26339 |
| HPV18 | L1 | 9 | 292 | YPDYLQMSA | 26340 |
| HPV18 | L1 | 8 | 524 | YPLGRKFL | 26341 |
| HPV18 | L1 | 9 | 524 | YPLGRKFLV | 26342 |
| HPV18 | L1 | 11 | 524 | YPLGRKFLVQA | 26343 |
| HPV18 | L1 | 8 | 129 | YQYRVFRV | 26344 |
| HPV18 | L1 | 10 | 129 | YQYRVFRVQL | 26345 |
| HPV18 | L1 | 8 | 88 | YVTPTSIF | 26346 |
| HPV18 | L1 | 9 | 88 | YVTPTSIFY | 26347 |
| HPV18 | L1 | 11 | 88 | YVTPTSIFYHA | 26348 |
| HPV18 | L2 | 9 | 286 | ALTSRRGTV | 26349 |
| HPV18 | L2 | 11 | 286 | ALTSRRGTVRF | 26350 |
| HPV18 | L2 | 8 | 421 | APASTQYI | 26351 |
| HPV18 | L2 | 10 | 421 | APASTQYIGI | 26352 |
| HPV18 | L2 | 9 | 327 | APSPEYIEL | 26353 |
| HPV18 | L2 | 9 | 27 | CPPDVVPKV | 26354 |
| HPV18 | L2 | 9 | 278 | DIIRLHRPA | 26355 |
| HPV18 | L2 | 10 | 278 | DIIRLHRPAL | 26356 |
| HPV18 | L2 | 11 | 322 | DISPIAPSPEY | 26357 |
| HPV18 | L2 | 10 | 404 | DITLPSTTSV | 26358 |
| HPV18 | L2 | 11 | 404 | DITLPSTTSVW | 26359 |
| HPV18 | L2 | 9 | 142 | DITPSSTSV | 26360 |
| HPV18 | L2 | 11 | 142 | DITPSSTSVSI | 26361 |
| HPV18 | L2 | 11 | 129 | DITSAGTTTPA | 26362 |
| HPV18 | L2 | 10 | 349 | DIYADDMDPA | 26363 |
| HPV18 | L2 | 11 | 349 | DIYADDMDPAV | 26364 |
| HPV18 | L2 | 10 | 346 | DLFDIYADDM | 26365 |
| HPV18 | L2 | 8 | 354 | DMDPAVPV | 26366 |
| HPV18 | L2 | 11 | 266 | DPRSDVPDSDF | 26367 |
| HPV18 | L2 | 8 | 100 | DPSIVTLI | 26368 |
| HPV18 | L2 | 9 | 83 | DVGPTRPPV | 26369 |
| HPV18 | L2 | 10 | 83 | DVGPTRPPVV | 26370 |
| HPV18 | L2 | 11 | 83 | DVGPTRPPVVI | 26371 |
| HPV18 | L2 | 8 | 270 | DVPDSDFM | 26372 |
| HPV18 | L2 | 10 | 270 | DVPDSDFMDI | 26373 |
| HPV18 | L2 | 11 | 270 | DVPDSDFMDII | 26374 |
| HPV18 | L2 | 10 | 396 | DVPVYTGPDI | 26375 |
| HPV18 | L2 | 11 | 30 | DVVPKVEGTTL | 26376 |
| HPV18 | L2 | 8 | 194 | EIPLQTFA | 26377 |
| HPV18 | L2 | 8 | 334 | ELQPLVSA | 26378 |
| HPV18 | L2 | 8 | 208 | EPISSTPL | 26379 |
| HPV18 | L2 | 11 | 208 | EPISSTPLPTV | 26380 |
| HPV18 | L2 | 9 | 257 | EPVDTTLTF | 26381 |
| HPV18 | L2 | 10 | 94 | EPVGPTDPSI | 26382 |
| HPV18 | L2 | 11 | 94 | EPVGPTDPSIV | 26383 |
| HPV18 | L2 | 8 | 175 | EVAGNVFV | 26384 |
| HPV18 | L2 | 8 | 169 | EVPQTGEV | 26385 |
| HPV18 | L2 | 9 | 169 | EVPQTGEVA | 26386 |
| HPV18 | L2 | 9 | 443 | FIPKKRKRV | 26387 |
| HPV18 | L2 | 11 | 443 | FIPKKRKRVPY | 26388 |
| HPV18 | L2 | 8 | 241 | FLTRPSSL | 26389 |
| HPV18 | L2 | 9 | 241 | FLTRPSSLI | 26390 |
| HPV18 | L2 | 11 | 241 | FLTRPSSLITY | 26391 |
| HPV18 | L2 | 11 | 276 | FMDIIRLHRPA | 26392 |
| HPV18 | L2 | 9 | 51 | GIFLGGLGI | 26393 |
| HPV18 | L2 | 8 | 429 | GIHGTHYY | 26394 |
| HPV18 | L2 | 9 | 429 | GIHGTHYYL | 26395 |
| HPV18 | L2 | 10 | 429 | GIHGTHYYLW | 26396 |
| HPV18 | L2 | 8 | 223 | GPRLYSRA | 26397 |
| HPV18 | L2 | 9 | 223 | GPRLYSRAY | 26398 |
| HPV18 | L2 | 8 | 97 | GPTDPSIV | 26399 |
| HPV18 | L2 | 10 | 97 | GPTDPSIVTL | 26400 |
| HPV18 | L2 | 11 | 97 | GPTDPSIVTLI | 26401 |
| HPV18 | L2 | 8 | 85 | GPTRPPVV | 26402 |
| HPV18 | L2 | 9 | 85 | GPTRPPVVI | 26403 |
| HPV18 | L2 | 10 | 167 | IIEVPQTGEV | 26404 |
| HPV18 | L2 | 11 | 167 | IIEVPQTGEVA | 26405 |
| HPV18 | L2 | 8 | 279 | IIRLHRPA | 26406 |
| HPV18 | L2 | 9 | 279 | IIRLHRPAL | 26407 |
| HPV18 | L2 | 9 | 44 | ILQWSSLGI | 26408 |
| HPV18 | L2 | 10 | 44 | ILQWSSLGIF | 26409 |

TABLE XIV-continued

B62 Supermotif Peptides

| Type | Protein | No. of Amino Acid | Position | Sequence | Seq. Id. No. |
|---|---|---|---|---|---|
| HPV18 | L2 | 11 | 44 | ILQWSSLGIFL | 26410 |
| HPV18 | L2 | 8 | 444 | IPKKRKRV | 26411 |
| HPV18 | L2 | 10 | 444 | IPKKRKRVPY | 26412 |
| HPV18 | L2 | 11 | 444 | IPKKRKRVPYF | 26413 |
| HPV18 | L2 | 10 | 72 | IPLGGRSNTV | 26414 |
| HPV18 | L2 | 11 | 72 | IPLGGRSNTVV | 26415 |
| HPV18 | L2 | 8 | 416 | IVSPTAPA | 26416 |
| HPV18 | L2 | 10 | 103 | IVTLIEDSSV | 26417 |
| HPV18 | L2 | 11 | 103 | IVTLIEDSSVV | 26418 |
| HPV18 | L2 | 8 | 43 | KILQWSSL | 26419 |
| HPV18 | L2 | 10 | 43 | KILQWSSLGI | 26420 |
| HPV18 | L2 | 11 | 43 | KILQWSSLGIF | 26421 |
| HPV18 | L2 | 10 | 22 | KQSGTCPPDV | 26422 |
| HPV18 | L2 | 11 | 22 | KQSGTCPPDVV | 26423 |
| HPV18 | L2 | 8 | 34 | KVEGTTLA | 26424 |
| HPV18 | L2 | 11 | 34 | KVEGTTLADKI | 26425 |
| HPV18 | L2 | 8 | 106 | LIEDSSVV | 26426 |
| HPV18 | L2 | 8 | 248 | LITYDNPA | 26427 |
| HPV18 | L2 | 9 | 248 | LITYDNPAF | 26428 |
| HPV18 | L2 | 8 | 407 | LPSTTSVW | 26429 |
| HPV18 | L2 | 10 | 407 | LPSTTSVWPI | 26430 |
| HPV18 | L2 | 11 | 407 | LPSTTSVWPIV | 26431 |
| HPV18 | L2 | 8 | 215 | LPTVRRVA | 26432 |
| HPV18 | L2 | 8 | 45 | LQWSSLGI | 26433 |
| HPV18 | L2 | 9 | 45 | LQWSSLGIF | 26434 |
| HPV18 | L2 | 10 | 45 | LQWSSLGIFL | 26435 |
| HPV18 | L2 | 10 | 338 | LVSATEDNDL | 26436 |
| HPV18 | L2 | 11 | 338 | LVSATEDNDLF | 26437 |
| HPV18 | L2 | 11 | 253 | NPAFEPVDTTL | 26438 |
| HPV18 | L2 | 9 | 159 | NPAFSDPSI | 26439 |
| HPV18 | L2 | 10 | 159 | NPAFSDPSII | 26440 |
| HPV18 | L2 | 11 | 238 | NPEFLTRPSSL | 26441 |
| HPV18 | L2 | 10 | 386 | NVTVPLTSSW | 26442 |
| HPV18 | L2 | 8 | 325 | PIAPSPEY | 26443 |
| HPV18 | L2 | 9 | 325 | PIAPSPEYI | 26444 |
| HPV18 | L2 | 11 | 325 | PIAPSPEYIEL | 26445 |
| HPV18 | L2 | 10 | 209 | PISSTPLPTV | 26446 |
| HPV18 | L2 | 9 | 415 | PIVSPTAPA | 26447 |
| HPV18 | L2 | 9 | 73 | PLGGRSNTV | 26448 |
| HPV18 | L2 | 10 | 73 | PLGGRSNTVV | 26449 |
| HPV18 | L2 | 8 | 214 | PLPTVRRV | 26450 |
| HPV18 | L2 | 9 | 214 | PLPTVRRVA | 26451 |
| HPV18 | L2 | 8 | 390 | PLTSSWDV | 26452 |
| HPV18 | L2 | 10 | 390 | PLTSSWDVPV | 26453 |
| HPV18 | L2 | 11 | 390 | PLTSSWDVPVY | 26454 |
| HPV18 | L2 | 11 | 337 | PLVSATEDNDL | 26455 |
| HPV18 | L2 | 8 | 28 | PPDVVPKV | 26456 |
| HPV18 | L2 | 8 | 89 | PPVVIEPV | 26457 |
| HPV18 | L2 | 10 | 171 | PQTGEVAGNV | 26458 |
| HPV18 | L2 | 11 | 171 | PQTGEVAGNVF | 26459 |
| HPV18 | L2 | 8 | 258 | PVDTTLTF | 26460 |
| HPV18 | L2 | 9 | 95 | PVGPTDPSI | 26461 |
| HPV18 | L2 | 10 | 95 | PVGPTDPSIV | 26462 |
| HPV18 | L2 | 10 | 360 | PVPSRSTTSF | 26463 |
| HPV18 | L2 | 11 | 360 | PVPSRSTTSFA | 26464 |
| HPV18 | L2 | 8 | 398 | PVYTGPDI | 26465 |
| HPV18 | L2 | 10 | 398 | PVYTGPDITL | 26466 |
| HPV18 | L2 | 8 | 312 | QIGARVHF | 26467 |
| HPV18 | L2 | 9 | 312 | QIGARVHFY | 26468 |
| HPV18 | L2 | 10 | 232 | QQVSVANPEF | 26469 |
| HPV18 | L2 | 11 | 232 | QQVSVANPEFL | 26470 |
| HPV18 | L2 | 9 | 233 | QVSVANPEF | 26471 |
| HPV18 | L2 | 10 | 233 | QVSVANPEFL | 26472 |
| HPV18 | L2 | 8 | 298 | RLGQRATM | 26473 |
| HPV18 | L2 | 9 | 298 | RLGQRATMF | 26474 |
| HPV18 | L2 | 10 | 225 | RLYSRAYQQV | 26475 |
| HPV18 | L2 | 11 | 284 | RPALTSRRGTV | 26476 |
| HPV18 | L2 | 9 | 88 | RPPVVIEPV | 26477 |
| HPV18 | L2 | 8 | 244 | RPSSLITY | 26478 |
| HPV18 | L2 | 10 | 119 | RPTFTGTSGF | 26479 |
| HPV18 | L2 | 8 | 220 | RVAGPRLY | 26480 |
| HPV18 | L2 | 11 | 220 | RVAGPRLYSRA | 26481 |
| HPV18 | L2 | 8 | 316 | RVHFYHDI | 26482 |
| HPV18 | L2 | 11 | 316 | RVHFYHDISPI | 26483 |
| HPV18 | L2 | 10 | 450 | RVPYFFADGF | 26484 |

TABLE XIV-continued

B62 Supermotif Peptides

| Type | Protein | No. of Amino Acid | Position | Sequence | Seq. Id. No. |
|---|---|---|---|---|---|
| HPV18 | L2 | 11 | 450 | RVPYFFADGFV | 26485 |
| HPV18 | L2 | 11 | 166 | SIIEVPQTGEV | 26486 |
| HPV18 | L2 | 11 | 151 | SISTTNFTNPA | 26487 |
| HPV18 | L2 | 11 | 102 | SIVTLIEDSSV | 26488 |
| HPV18 | L2 | 9 | 49 | SLGIFLGGL | 26489 |
| HPV18 | L2 | 11 | 49 | SLGIFLGGLGI | 26490 |
| HPV18 | L2 | 9 | 247 | SLITYDNPA | 26491 |
| HPV18 | L2 | 10 | 247 | SLITYDNPAF | 26492 |
| HPV18 | L2 | 10 | 329 | SPEYIELQPL | 26493 |
| HPV18 | L2 | 11 | 329 | SPEYIELQPLV | 26494 |
| HPV18 | L2 | 9 | 324 | SPIAPSPEY | 26495 |
| HPV18 | L2 | 10 | 324 | SPIAPSPEYI | 26496 |
| HPV18 | L2 | 10 | 418 | SPTAPASTQY | 26497 |
| HPV18 | L2 | 11 | 418 | SPTAPASTQYI | 26498 |
| HPV18 | L2 | 10 | 375 | SPTISSASSY | 26499 |
| HPV18 | L2 | 8 | 235 | SVANPEFL | 26500 |
| HPV18 | L2 | 9 | 149 | SVSISTTNF | 26501 |
| HPV18 | L2 | 10 | 412 | SVWPIVSPTA | 26502 |
| HPV18 | L2 | 8 | 377 | TISSASSY | 26503 |
| HPV18 | L2 | 11 | 377 | TISSASSYSNV | 26504 |
| HPV18 | L2 | 9 | 39 | TLADKILQW | 26505 |
| HPV18 | L2 | 8 | 105 | TLIEDSSV | 26506 |
| HPV18 | L2 | 9 | 105 | TLIEDSSVV | 26507 |
| HPV18 | L2 | 8 | 406 | TLPSTTSV | 26508 |
| HPV18 | L2 | 9 | 406 | TLPSTTSVW | 26509 |
| HPV18 | L2 | 11 | 406 | TLPSTTSVWPI | 26510 |
| HPV18 | L2 | 10 | 262 | TLTFDPRSDV | 26511 |
| HPV18 | L2 | 10 | 304 | TMFTRSGTQI | 26512 |
| HPV18 | L2 | 9 | 213 | TPLPTVRRV | 26513 |
| HPV18 | L2 | 10 | 213 | TPLPTVRRVA | 26514 |
| HPV18 | L2 | 9 | 144 | TPSSTSVSI | 26515 |
| HPV18 | L2 | 9 | 184 | TPTSGTHGY | 26516 |
| HPV18 | L2 | 9 | 311 | TQIGARVHF | 26517 |
| HPV18 | L2 | 10 | 311 | TQIGARVHFY | 26518 |
| HPV18 | L2 | 11 | 425 | TQYIGIHGTHY | 26519 |
| HPV18 | L2 | 8 | 388 | TVPLTSSW | 26520 |
| HPV18 | L2 | 10 | 388 | TVPLTSSWDV | 26521 |
| HPV18 | L2 | 11 | 293 | TVRFSRLGQRA | 26522 |
| HPV18 | L2 | 10 | 217 | TVRRVAGPRL | 26523 |
| HPV18 | L2 | 11 | 217 | TVRRVAGPRLY | 26524 |
| HPV18 | L2 | 11 | 140 | VLDITPSSTSV | 26525 |
| HPV18 | L2 | 9 | 271 | VPDSDFMDI | 26526 |
| HPV18 | L2 | 10 | 271 | VPDSDFMDII | 26527 |
| HPV18 | L2 | 9 | 32 | VPKVEGTTL | 26528 |
| HPV18 | L2 | 10 | 32 | VPKVEGTTLA | 26529 |
| HPV18 | L2 | 9 | 389 | VPLTSSWDV | 26530 |
| HPV18 | L2 | 11 | 389 | VPLTSSWDVPV | 26531 |
| HPV18 | L2 | 8 | 170 | VPQTGEVA | 26532 |
| HPV18 | L2 | 11 | 170 | VPQTGEVAGNV | 26533 |
| HPV18 | L2 | 9 | 361 | VPSRSTTSF | 26534 |
| HPV18 | L2 | 10 | 361 | VPSRSTTSFA | 26535 |
| HPV18 | L2 | 11 | 361 | VPSRSTTSFAF | 26536 |
| HPV18 | L2 | 11 | 359 | VPVPSRSTTSF | 26537 |
| HPV18 | L2 | 9 | 397 | VPVYTGPDI | 26538 |
| HPV18 | L2 | 11 | 397 | VPVYTGPDITL | 26539 |
| HPV18 | L2 | 9 | 451 | VPYFFADGF | 26540 |
| HPV18 | L2 | 10 | 451 | VPYFFADGFV | 26541 |
| HPV18 | L2 | 11 | 451 | VPYFFADGFVA | 26542 |
| HPV18 | L2 | 11 | 81 | VVDVGPTRPPV | 26543 |
| HPV18 | L2 | 10 | 31 | VVPKVEGTTL | 26544 |
| HPV18 | L2 | 11 | 31 | VVPKVEGTTLA | 26545 |
| HPV18 | L2 | 11 | 112 | VVTSGAPRPTF | 26546 |
| HPV18 | L2 | 8 | 414 | WPIVSPTA | 26547 |
| HPV18 | L2 | 10 | 414 | WPIVSPTAPA | 26548 |
| HPV18 | L2 | 8 | 332 | YIELQPLV | 26549 |
| HPV18 | L2 | 10 | 332 | YIELQPLVSA | 26550 |
| HPV18 | L2 | 9 | 427 | YIGIHGTHY | 26551 |
| HPV18 | L2 | 10 | 427 | YIGIHGTHYY | 26552 |
| HPV18 | L2 | 11 | 427 | YIGIHGTHYYL | 26553 |
| HPV18 | L2 | 11 | 71 | YIPLGGRSNTV | 26554 |
| HPV18 | L2 | 8 | 436 | YLWPLYYF | 26555 |
| HPV18 | L2 | 9 | 436 | YLWPLYYFI | 26556 |
| HPV18 | L2 | 11 | 231 | YQQVSVANPEF | 26557 |
| HPV31 | E1 | 11 | 111 | AICIENNSKTA | 26558 |
| HPV31 | E1 | 9 | 519 | ALDGNPVSI | 26559 |

TABLE XIV-continued

B62 Supermotif Peptides

| Type | Protein | No. of Amino Acid | Position | Sequence | Seq. Id. No. |
|---|---|---|---|---|---|
| HPV31 | E1 | 11 | 519 | ALDGNPVSIDV | 26560 |
| HPV31 | E1 | 8 | 68 | ALFHAQEA | 26561 |
| HPV31 | E1 | 9 | 439 | ALKLFLKGV | 26562 |
| HPV31 | E1 | 10 | 533 | ALMQLKCPPL | 26563 |
| HPV31 | E1 | 11 | 533 | ALMQLKCPPLL | 26564 |
| HPV31 | E1 | 9 | 298 | ALYWYRTGM | 26565 |
| HPV31 | E1 | 9 | 186 | AMLGKFKEL | 26566 |
| HPV31 | E1 | 10 | 186 | AMLGKFKELY | 26567 |
| HPV31 | E1 | 8 | 458 | APNTGKSY | 26568 |
| HPV31 | E1 | 9 | 458 | APNTGKSYF | 26569 |
| HPV31 | E1 | 11 | 458 | APNTGKSYFGM | 26570 |
| HPV31 | E1 | 10 | 66 | AQALFHAQEA | 26571 |
| HPV31 | E1 | 8 | 72 | AQEAEEHA | 26572 |
| HPV31 | E1 | 10 | 72 | AQEAEEHAEA | 26573 |
| HPV31 | E1 | 11 | 72 | AQEAEEHAEAV | 26574 |
| HPV31 | E1 | 10 | 360 | AQLADSDSNA | 26575 |
| HPV31 | E1 | 11 | 22 | AVIDRQTGDNI | 26576 |
| HPV31 | E1 | 9 | 81 | AVQVLKRKY | 26577 |
| HPV31 | E1 | 10 | 81 | AVQVLKRKYV | 26578 |
| HPV31 | E1 | 9 | 113 | CIENNSKTA | 26579 |
| HPV31 | E1 | 8 | 279 | CISTNCML | 26580 |
| HPV31 | E1 | 9 | 279 | CISTNCMLI | 26581 |
| HPV31 | E1 | 9 | 239 | CLYCHLQSL | 26582 |
| HPV31 | E1 | 10 | 239 | CLYCHLQSLA | 26583 |
| HPV31 | E1 | 9 | 284 | CMLIQPPKL | 26584 |
| HPV31 | E1 | 10 | 539 | CPPLLITSNI | 26585 |
| HPV31 | E1 | 11 | 217 | CVAAFGVTGTV | 26586 |
| HPV31 | E1 | 10 | 100 | CVDYNISPRL | 26587 |
| HPV31 | E1 | 10 | 620 | CVSGQNIRTL | 26588 |
| HPV31 | E1 | 8 | 96 | DISSCVDY | 26589 |
| HPV31 | E1 | 10 | 96 | DISSCVDYNI | 26590 |
| HPV31 | E1 | 8 | 421 | DIVKFLRY | 26591 |
| HPV31 | E1 | 11 | 421 | DIVKFLRYQQI | 26592 |
| HPV31 | E1 | 8 | 336 | DLSQMVQW | 26593 |
| HPV31 | E1 | 9 | 336 | DLSQMVQWA | 26594 |
| HPV31 | E1 | 10 | 336 | DLSQMVQWAY | 26595 |
| HPV31 | E1 | 11 | 46 | DMVDFIDNCNV | 26596 |
| HPV31 | E1 | 8 | 528 | DVKHKALM | 26597 |
| HPV31 | E1 | 10 | 528 | DVKHKALMQL | 26598 |
| HPV31 | E1 | 8 | 348 | DVMDDSEI | 26599 |
| HPV31 | E1 | 9 | 348 | DVMDDSEIA | 26600 |
| HPV31 | E1 | 10 | 348 | DVMDDSEIAY | 26601 |
| HPV31 | E1 | 9 | 311 | DVYGETPEW | 26602 |
| HPV31 | E1 | 10 | 311 | DVYGETPEWI | 26603 |
| HPV31 | E1 | 9 | 354 | EIAYKYAQL | 26604 |
| HPV31 | E1 | 10 | 354 | EIAYKYAQLA | 26605 |
| HPV31 | E1 | 10 | 583 | ELSDKNWKSF | 26606 |
| HPV31 | E1 | 11 | 583 | ELSDKNWKSFF | 26607 |
| HPV31 | E1 | 8 | 193 | ELYGVSFM | 26608 |
| HPV31 | E1 | 10 | 193 | ELYGVSFMEL | 26609 |
| HPV31 | E1 | 11 | 193 | ELYGVSFMELI | 26610 |
| HPV31 | E1 | 8 | 137 | EVETQQMV | 26611 |
| HPV31 | E1 | 10 | 137 | EVETQQMVQV | 26612 |
| HPV31 | E1 | 8 | 50 | FIDNCNVY | 26613 |
| HPV31 | E1 | 11 | 443 | FLKGVPKKNCI | 26614 |
| HPV31 | E1 | 8 | 372 | FLKSNSQA | 26615 |
| HPV31 | E1 | 10 | 372 | FLKSNSQAKI | 26616 |
| HPV31 | E1 | 11 | 372 | FLKSNSQAKIV | 26617 |
| HPV31 | E1 | 9 | 473 | FLQGCIISY | 26618 |
| HPV31 | E1 | 10 | 473 | FLQGCIISYA | 26619 |
| HPV31 | E1 | 9 | 425 | FLRYQQIEF | 26620 |
| HPV31 | E1 | 10 | 425 | FLRYQQIEFV | 26621 |
| HPV31 | E1 | 8 | 436 | FLSALKLF | 26622 |
| HPV31 | E1 | 9 | 436 | FLSALKLFL | 26623 |
| HPV31 | E1 | 8 | 199 | FMELIRPF | 26624 |
| HPV31 | E1 | 10 | 572 | FPFDKNGNPV | 26625 |
| HPV31 | E1 | 11 | 572 | FPFDKNGNPVY | 26626 |
| HPV31 | E1 | 11 | 206 | FQSNKSTCTDW | 26627 |
| HPV31 | E1 | 8 | 433 | FVSFLSAL | 26628 |
| HPV31 | E1 | 10 | 433 | FVSFLSALKL | 26629 |
| HPV31 | E1 | 11 | 433 | FVSFLSALKLF | 26630 |
| HPV31 | E1 | 11 | 499 | GMLDDATTPCW | 26631 |
| HPV31 | E1 | 8 | 467 | GMSLISFL | 26632 |
| HPV31 | E1 | 8 | 305 | GMSNISDV | 26633 |
| HPV31 | E1 | 9 | 305 | GMSNISDVY | 26634 |

TABLE XIV-continued

B62 Supermotif Peptides

| Type | Protein | No. of Amino Acid | Position | Sequence | Seq. Id. No. |
|---|---|---|---|---|---|
| HPV31 | E1 | 8 | 252 | GMVMLMLV | 26635 |
| HPV31 | E1 | 10 | 252 | GMVMLMLVRF | 26636 |
| HPV31 | E1 | 11 | 403 | GQWIKSRCDKV | 26637 |
| HPV31 | E1 | 8 | 446 | GVPKKNCI | 26638 |
| HPV31 | E1 | 9 | 446 | GVPKKNCIL | 26639 |
| HPV31 | E1 | 10 | 446 | GVPKKNCILI | 26640 |
| HPV31 | E1 | 8 | 196 | GVSFMELI | 26641 |
| HPV31 | E1 | 11 | 196 | GVSFMELIRPF | 26642 |
| HPV31 | E1 | 10 | 222 | GVTGTVAEGF | 26643 |
| HPV31 | E1 | 9 | 243 | HLQSLACSW | 26644 |
| HPV31 | E1 | 11 | 243 | HLQSLACSWGM | 26645 |
| HPV31 | E1 | 11 | 478 | IISYANSKSHF | 26646 |
| HPV31 | E1 | 10 | 287 | IQPPKLRSTA | 26647 |
| HPV31 | E1 | 11 | 287 | IQPPKLRSTAA | 26648 |
| HPV31 | E1 | 8 | 381 | IVKDCGTM | 26649 |
| HPV31 | E1 | 10 | 422 | IVKFLRYQQI | 26650 |
| HPV31 | E1 | 8 | 497 | KIGMLDDA | 26651 |
| HPV31 | E1 | 9 | 380 | KIVKDCGTM | 26652 |
| HPV31 | E1 | 10 | 276 | KLLCISTNCM | 26653 |
| HPV31 | E1 | 11 | 276 | KLLCISTNCML | 26654 |
| HPV31 | E1 | 9 | 272 | KLLEKLLCI | 26655 |
| HPV31 | E1 | 8 | 291 | KLRSTAAA | 26656 |
| HPV31 | E1 | 9 | 291 | KLRSTAAAL | 26657 |
| HPV31 | E1 | 10 | 291 | KLRSTAAALY | 26658 |
| HPV31 | E1 | 11 | 291 | KLRSTAAALYW | 26659 |
| HPV31 | E1 | 8 | 412 | KVSDEGDW | 26660 |
| HPV31 | E1 | 11 | 412 | KVSDEGDWRDI | 26661 |
| HPV31 | E1 | 11 | 286 | LIQPPKLRSTA | 26662 |
| HPV31 | E1 | 9 | 470 | LISFLQGCI | 26663 |
| HPV31 | E1 | 10 | 470 | LISFLQGCII | 26664 |
| HPV31 | E1 | 8 | 543 | LITSNINA | 26665 |
| HPV31 | E1 | 9 | 277 | LLCISTNCM | 26666 |
| HPV31 | E1 | 10 | 277 | LLCISTNCML | 26667 |
| HPV31 | E1 | 11 | 277 | LLCISTNCMLI | 26668 |
| HPV31 | E1 | 8 | 273 | LLEKLLCI | 26669 |
| HPV31 | E1 | 9 | 542 | LLITSNINA | 26670 |
| HPV31 | E1 | 8 | 234 | LLQPYCLY | 26671 |
| HPV31 | E1 | 11 | 234 | LLQPYCLYCHL | 26672 |
| HPV31 | E1 | 9 | 256 | LMLVRFKCA | 26673 |
| HPV31 | E1 | 9 | 534 | LMQLKCPPL | 26674 |
| HPV31 | E1 | 10 | 534 | LMQLKCPPLL | 26675 |
| HPV31 | E1 | 11 | 534 | LMQLKCPPLLI | 26676 |
| HPV31 | E1 | 11 | 128 | LPDSGYGNTEV | 26677 |
| HPV31 | E1 | 8 | 474 | LQGCIISY | 26678 |
| HPV31 | E1 | 9 | 474 | LQGCIISYA | 26679 |
| HPV31 | E1 | 10 | 326 | LQHSFNDTTF | 26680 |
| HPV31 | E1 | 9 | 490 | LQPLADAKI | 26681 |
| HPV31 | E1 | 11 | 490 | LQPLADAKIGM | 26682 |
| HPV31 | E1 | 10 | 235 | LQPYCLYCHL | 26683 |
| HPV31 | E1 | 8 | 244 | LQSLACSW | 26684 |
| HPV31 | E1 | 10 | 244 | LQSLACSWGM | 26685 |
| HPV31 | E1 | 11 | 244 | LQSLACSWGMV | 26686 |
| HPV31 | E1 | 11 | 175 | LQVLKTSNGKA | 26687 |
| HPV31 | E1 | 11 | 258 | LVRFKCAKNRI | 26688 |
| HPV31 | E1 | 10 | 563 | LVVFTFPNPF | 26689 |
| HPV31 | E1 | 10 | 500 | MLDDATTPCW | 26690 |
| HPV31 | E1 | 8 | 187 | MLGKFKEL | 26691 |
| HPV31 | E1 | 9 | 187 | MLGKFKELY | 26692 |
| HPV31 | E1 | 11 | 187 | MLGKFKELYGV | 26693 |
| HPV31 | E1 | 8 | 285 | MLIQPPKL | 26694 |
| HPV31 | E1 | 10 | 255 | MLMLVRFKCA | 26695 |
| HPV31 | E1 | 8 | 257 | MLVRFKCA | 26696 |
| HPV31 | E1 | 8 | 535 | MQLKCPPL | 26697 |
| HPV31 | E1 | 9 | 535 | MQLKCPPLL | 26698 |
| HPV31 | E1 | 10 | 535 | MQLKCPPLLI | 26699 |
| HPV31 | E1 | 10 | 47 | MVDFIDNCNV | 26700 |
| HPV31 | E1 | 11 | 47 | MVDFIDNCNVY | 26701 |
| HPV31 | E1 | 9 | 253 | MVMLMLVRF | 26702 |
| HPV31 | E1 | 11 | 143 | MVQVEEQQTTL | 26703 |
| HPV31 | E1 | 10 | 340 | MVQWAYDNDV | 26704 |
| HPV31 | E1 | 11 | 340 | MVQWAYDNDVM | 26705 |
| HPV31 | E1 | 10 | 547 | NINAGKDDRW | 26706 |
| HPV31 | E1 | 8 | 104 | NISPRLKA | 26707 |
| HPV31 | E1 | 9 | 104 | NISPRLKAI | 26708 |
| HPV31 | E1 | 11 | 104 | NISPRLKAICI | 26709 |

TABLE XIV-continued

B62 Supermotif Peptides

| Type | Protein | No. of Amino Acid | Position | Sequence | Seq. Id. No. |
|---|---|---|---|---|---|
| HPV31 | E1 | 11 | 523 | NPVSIDVKHKA | 26710 |
| HPV31 | E1 | 11 | 579 | NPVYELSDKNW | 26711 |
| HPV31 | E1 | 8 | 59 | NQAEAETA | 26712 |
| HPV31 | E1 | 10 | 59 | NQAEAETAQA | 26713 |
| HPV31 | E1 | 11 | 59 | NQAEAETAQAL | 26714 |
| HPV31 | E1 | 9 | 55 | NVYNNQAEA | 26715 |
| HPV31 | E1 | 9 | 492 | PLADAKIGM | 26716 |
| HPV31 | E1 | 10 | 492 | PLADAKIGML | 26717 |
| HPV31 | E1 | 8 | 541 | PLLITSNI | 26718 |
| HPV31 | E1 | 10 | 541 | PLLITSNINA | 26719 |
| HPV31 | E1 | 9 | 93 | PLSDISSCV | 26720 |
| HPV31 | E1 | 11 | 93 | PLSDISSCVDY | 26721 |
| HPV31 | E1 | 8 | 289 | PPKLRSTA | 26722 |
| HPV31 | E1 | 9 | 289 | PPKLRSTAA | 26723 |
| HPV31 | E1 | 10 | 289 | PPKLRSTAAA | 26724 |
| HPV31 | E1 | 11 | 289 | PPKLRSTAAAL | 26725 |
| HPV31 | E1 | 9 | 540 | PPLLITSNI | 26726 |
| HPV31 | E1 | 11 | 540 | PPLLITSNINA | 26727 |
| HPV31 | E1 | 10 | 524 | PVSIDVKHKA | 26728 |
| HPV31 | E1 | 11 | 524 | PVSIDVKHKAL | 26729 |
| HPV31 | E1 | 10 | 580 | PVYELSDKNW | 26730 |
| HPV31 | E1 | 8 | 430 | QIEFVSFL | 26731 |
| HPV31 | E1 | 10 | 430 | QIEFVSFLSA | 26732 |
| HPV31 | E1 | 11 | 430 | QIEFVSFLSAL | 26733 |
| HPV31 | E1 | 9 | 361 | QLADSDSNA | 26734 |
| HPV31 | E1 | 11 | 361 | QLADSDSNACA | 26735 |
| HPV31 | E1 | 8 | 536 | QLKCPPLL | 26736 |
| HPV31 | E1 | 9 | 536 | QLKCPPLLI | 26737 |
| HPV31 | E1 | 8 | 399 | QMSMGQWI | 26738 |
| HPV31 | E1 | 11 | 339 | QMVQWAYDNDV | 26739 |
| HPV31 | E1 | 8 | 491 | QPLADAKI | 26740 |
| HPV31 | E1 | 10 | 491 | QPLADAKIGM | 26741 |
| HPV31 | E1 | 11 | 491 | QPLADAKIGML | 26742 |
| HPV31 | E1 | 9 | 288 | QPPKLRSTA | 26743 |
| HPV31 | E1 | 10 | 288 | QPPKLRSTAA | 26744 |
| HPV31 | E1 | 11 | 288 | QPPKLRSTAAA | 26745 |
| HPV31 | E1 | 9 | 236 | QPYCLYCHL | 26746 |
| HPV31 | E1 | 8 | 429 | QQIEFVSF | 26747 |
| HPV31 | E1 | 9 | 429 | QQIEFVSFL | 26748 |
| HPV31 | E1 | 11 | 429 | QQIEFVSFLSA | 26749 |
| HPV31 | E1 | 9 | 145 | QVEEQQTTL | 26750 |
| HPV31 | E1 | 8 | 83 | QVLKRKYV | 26751 |
| HPV31 | E1 | 10 | 176 | QVLKTSNGKA | 26752 |
| HPV31 | E1 | 11 | 176 | QVLKTSNGKAA | 26753 |
| HPV31 | E1 | 8 | 267 | RITIEKLL | 26754 |
| HPV31 | E1 | 11 | 267 | RITIEKLLEKL | 26755 |
| HPV31 | E1 | 10 | 124 | RLFELPDSGY | 26756 |
| HPV31 | E1 | 11 | 562 | RLVVFTFPNPF | 26757 |
| HPV31 | E1 | 8 | 398 | RQMSMGQW | 26758 |
| HPV31 | E1 | 9 | 398 | RQMSMGQWI | 26759 |
| HPV31 | E1 | 9 | 322 | RQTVLQHSF | 26760 |
| HPV31 | E1 | 8 | 526 | SIDVKHKA | 26761 |
| HPV31 | E1 | 9 | 526 | SIDVKHKAL | 26762 |
| HPV31 | E1 | 10 | 526 | SIDVKHKALM | 26763 |
| HPV31 | E1 | 8 | 246 | SLACSWGM | 26764 |
| HPV31 | E1 | 9 | 246 | SLACSWGMV | 26765 |
| HPV31 | E1 | 10 | 246 | SLACSWGMVM | 26766 |
| HPV31 | E1 | 11 | 246 | SLACSWGMVML | 26767 |
| HPV31 | E1 | 10 | 469 | SLISFLQGCI | 26768 |
| HPV31 | E1 | 11 | 469 | SLISFLQGCII | 26769 |
| HPV31 | E1 | 10 | 92 | SPLSDISSCV | 26770 |
| HPV31 | E1 | 9 | 106 | SPRLKAICI | 26771 |
| HPV31 | E1 | 8 | 338 | SQMVQWAY | 26772 |
| HPV31 | E1 | 9 | 269 | TIEKLLEKL | 26773 |
| HPV31 | E1 | 10 | 269 | TIEKLLEKLL | 26774 |
| HPV31 | E1 | 8 | 233 | TLLQPYCL | 26775 |
| HPV31 | E1 | 9 | 233 | TLLQPYCLY | 26776 |
| HPV31 | E1 | 9 | 387 | TMCRHYKRA | 26777 |
| HPV31 | E1 | 10 | 506 | TPCWHYIDNY | 26778 |
| HPV31 | E1 | 11 | 506 | TPCWHYIDNYL | 26779 |
| HPV31 | E1 | 10 | 316 | TPEWIERQTV | 26780 |
| HPV31 | E1 | 11 | 316 | TPEWIERQTVL | 26781 |
| HPV31 | E1 | 9 | 169 | TPTRNILQV | 26782 |
| HPV31 | E1 | 10 | 169 | TPTRNILQVL | 26783 |
| HPV31 | E1 | 9 | 226 | TVAEGFKTL | 26784 |

TABLE XIV-continued

B62 Supermotif Peptides

| Type | Protein | No. of Amino Acid | Position | Sequence | Seq. Id. No. |
|---|---|---|---|---|---|
| HPV31 | E1 | 10 | 226 | TVAEGFKTLL | 26785 |
| HPV31 | E1 | 10 | 23 | VIDRQTGDNI | 26786 |
| HPV31 | E1 | 11 | 84 | VLRKYVGSPL | 26787 |
| HPV31 | E1 | 9 | 177 | VLKTSNGKA | 26788 |
| HPV31 | E1 | 10 | 177 | VLKTSNGKAA | 26789 |
| HPV31 | E1 | 11 | 177 | VLKTSNGKAAM | 26790 |
| HPV31 | E1 | 11 | 325 | VLQHSFNDTTF | 26791 |
| HPV31 | E1 | 8 | 349 | VMDDSEIA | 26792 |
| HPV31 | E1 | 9 | 349 | VMDDSEIAY | 26793 |
| HPV31 | E1 | 11 | 349 | VMDDSEIAYKY | 26794 |
| HPV31 | E1 | 8 | 254 | VMLMLVRF | 26795 |
| HPV31 | E1 | 11 | 254 | VMLMLVRFKCA | 26796 |
| HPV31 | E1 | 8 | 447 | VPKKNCIL | 26797 |
| HPV31 | E1 | 9 | 447 | VPKKNCILI | 26798 |
| HPV31 | E1 | 10 | 144 | VQVEEQQTTL | 26799 |
| HPV31 | E1 | 8 | 82 | VQVLKRKY | 26800 |
| HPV31 | E1 | 9 | 82 | VQVLKRKYV | 26801 |
| HPV31 | E1 | 9 | 341 | VQWAYDNDV | 26802 |
| HPV31 | E1 | 10 | 341 | VQWAYDNDVM | 26803 |
| HPV31 | E1 | 9 | 564 | VVFTFPNPF | 26804 |
| HPV31 | E1 | 11 | 564 | VVFTFPNPFPF | 26805 |
| HPV31 | E1 | 8 | 319 | WIERQTVL | 26806 |
| HPV31 | E1 | 9 | 405 | WIKSRCDKV | 26807 |
| HPV31 | E1 | 8 | 489 | WLQPLADA | 26808 |
| HPV31 | E1 | 10 | 489 | WLQPLADAKI | 26809 |
| HPV31 | E1 | 8 | 556 | WPYLHSRL | 26810 |
| HPV31 | E1 | 9 | 556 | WPYLHSRLV | 26811 |
| HPV31 | E1 | 10 | 556 | WPYLHSRLVV | 26812 |
| HPV31 | E1 | 11 | 556 | WPYLHSRLVVF | 26813 |
| HPV31 | E1 | 9 | 511 | YIDNYLRNA | 26814 |
| HPV31 | E1 | 10 | 511 | YIDNYLRNAL | 26815 |
| HPV31 | E1 | 8 | 558 | YLHSRLVV | 26816 |
| HPV31 | E1 | 9 | 558 | YLHSRLVVF | 26817 |
| HPV31 | E1 | 11 | 558 | YLHSRLVVFTF | 26818 |
| HPV31 | E1 | 11 | 515 | YLRNALDGNPV | 26819 |
| HPV31 | E1 | 9 | 428 | YQQIEFVSF | 26820 |
| HPV31 | E1 | 10 | 428 | YQQIEFVSFL | 26821 |
| HPV31 | E1 | 9 | 89 | YVGSPLSDI | 26822 |
| HPV31 | E2 | 8 | 72 | AIELQMML | 26823 |
| HPV31 | E2 | 11 | 72 | AIELQMMLETL | 26824 |
| HPV31 | E2 | 8 | 338 | AIVTLTYI | 26825 |
| HPV31 | E2 | 8 | 229 | ALGTSEGV | 26826 |
| HPV31 | E2 | 11 | 229 | ALGTSEGVRRA | 26827 |
| HPV31 | E2 | 9 | 69 | ALQAIELQM | 26828 |
| HPV31 | E2 | 10 | 69 | ALQAIELQMM | 26829 |
| HPV31 | E2 | 11 | 69 | ALQAIELQMML | 26830 |
| HPV31 | E2 | 9 | 61 | ALSVSKAKA | 26831 |
| HPV31 | E2 | 10 | 61 | ALSVSKAKAL | 26832 |
| HPV31 | E2 | 11 | 105 | APTGCLKKHGY | 26833 |
| HPV31 | E2 | 10 | 286 | AVSCPATTPI | 26834 |
| HPV31 | E2 | 11 | 286 | AVSCPATTPII | 26835 |
| HPV31 | E2 | 8 | 140 | CIDGQCTV | 26836 |
| HPV31 | E2 | 9 | 140 | CIDGQCTVV | 26837 |
| HPV31 | E2 | 9 | 109 | CLKKHGYTV | 26838 |
| HPV31 | E2 | 11 | 109 | CLKKHGYTVEV | 26839 |
| HPV31 | E2 | 9 | 307 | CLRYRLSKY | 26840 |
| HPV31 | E2 | 8 | 289 | CPATTPII | 26841 |
| HPV31 | E2 | 10 | 289 | CPATTPIIHL | 26842 |
| HPV31 | E2 | 9 | 11 | CQDKILEHY | 26843 |
| HPV31 | E2 | 10 | 40 | CVLMYKAREM | 26844 |
| HPV31 | E2 | 8 | 124 | DVHNTMHY | 26845 |
| HPV31 | E2 | 11 | 124 | DVHNTMHYTNW | 26846 |
| HPV31 | E2 | 8 | 204 | EISFAGIV | 26847 |
| HPV31 | E2 | 11 | 204 | EISFAGIVTKL | 26848 |
| HPV31 | E2 | 9 | 74 | ELQMMLETL | 26849 |
| HPV31 | E2 | 11 | 100 | ELYLTAPTGCL | 26850 |
| HPV31 | E2 | 11 | 48 | EMGIHSINHQV | 26851 |
| HPV31 | E2 | 9 | 320 | EQVSSTWHW | 26852 |
| HPV31 | E2 | 8 | 185 | EVHAGGQV | 26853 |
| HPV31 | E2 | 9 | 185 | EVHAGGQVI | 26854 |
| HPV31 | E2 | 10 | 185 | EVHAGGQVIV | 26855 |
| HPV31 | E2 | 11 | 185 | EVHAGGQVIVF | 26856 |
| HPV31 | E2 | 8 | 118 | EVQFDGDV | 26857 |
| HPV31 | E2 | 11 | 353 | FLNTVKIPNTV | 26858 |
| HPV31 | E2 | 11 | 195 | FPESVFSSDEI | 26859 |

TABLE XIV-continued

B62 Supermotif Peptides

| Type | Protein | No. of Amino Acid | Position | Sequence | Seq. Id. No. |
|---|---|---|---|---|---|
| HPV31 | E2 | 8 | 168 | FVNFTEEA | 26860 |
| HPV31 | E2 | 11 | 168 | FVNFTEEAKKY | 26861 |
| HPV31 | E2 | 9 | 50 | GIHSINHQV | 26862 |
| HPV31 | E2 | 10 | 50 | GIHSINHQVV | 26863 |
| HPV31 | E2 | 9 | 209 | GITVKLPTA | 26864 |
| HPV31 | E2 | 10 | 156 | GIYYVHEGHI | 26865 |
| HPV31 | E2 | 10 | 143 | GQCTVVEGQV | 26866 |
| HPV31 | E2 | 10 | 190 | GQVIVFPESV | 26867 |
| HPV31 | E2 | 11 | 190 | GQVIVFPESVF | 26868 |
| HPV31 | E2 | 8 | 150 | GQVNCKGI | 26869 |
| HPV31 | E2 | 9 | 150 | GQVNCKGIY | 26870 |
| HPV31 | E2 | 10 | 150 | GQVNCKGIYY | 26871 |
| HPV31 | E2 | 11 | 150 | GQVNCKGIYYV | 26872 |
| HPV31 | E2 | 8 | 29 | HIDYWKHI | 26873 |
| HPV31 | E2 | 10 | 29 | HIDYWKHIRL | 26874 |
| HPV31 | E2 | 8 | 35 | HIRLECVL | 26875 |
| HPV31 | E2 | 9 | 35 | HIRLECVLM | 26876 |
| HPV31 | E2 | 10 | 35 | HIRLECVLMY | 26877 |
| HPV31 | E2 | 8 | 164 | HITYFVNF | 26878 |
| HPV31 | E2 | 8 | 297 | HLKGDANI | 26879 |
| HPV31 | E2 | 9 | 297 | HLKGDANIL | 26880 |
| HPV31 | E2 | 11 | 257 | HPNKLLRGDSV | 26881 |
| HPV31 | E2 | 9 | 56 | HQVVPALSV | 26882 |
| HPV31 | E2 | 8 | 295 | IIHLKGDA | 26883 |
| HPV31 | E2 | 10 | 295 | IIHLKGDANI | 26884 |
| HPV31 | E2 | 11 | 295 | IIHLKGDANIL | 26885 |
| HPV31 | E2 | 9 | 304 | ILKCLRYRL | 26886 |
| HPV31 | E2 | 11 | 359 | IPNTVSVSTGY | 26887 |
| HPV31 | E2 | 8 | 193 | IVFPESVF | 26888 |
| HPV31 | E2 | 8 | 210 | IVTKLPTA | 26889 |
| HPV31 | E2 | 8 | 358 | KIPNTVSV | 26890 |
| HPV31 | E2 | 8 | 260 | KLLRGDSV | 26891 |
| HPV31 | E2 | 11 | 260 | KLLRGDSVDSV | 26892 |
| HPV31 | E2 | 11 | 316 | KQLYEQVSSTW | 26893 |
| HPV31 | E2 | 10 | 261 | LLRGDSVDSV | 26894 |
| HPV31 | E2 | 8 | 42 | LMYKAREM | 26895 |
| HPV31 | E2 | 10 | 42 | LMYKAREMGI | 26896 |
| HPV31 | E2 | 8 | 70 | LQAIELQM | 26897 |
| HPV31 | E2 | 9 | 70 | LQAIELQMM | 26898 |
| HPV31 | E2 | 10 | 70 | LQAIELQMML | 26899 |
| HPV31 | E2 | 8 | 75 | LQMMLETL | 26900 |
| HPV31 | E2 | 10 | 78 | MLETLNNTEY | 26901 |
| HPV31 | E2 | 11 | 77 | MMLETLNNTEY | 26902 |
| HPV31 | E2 | 8 | 94 | MQQTSLEL | 26903 |
| HPV31 | E2 | 9 | 94 | MQQTSLELY | 26904 |
| HPV31 | E2 | 10 | 94 | MQQTSLELYL | 26905 |
| HPV31 | E2 | 8 | 303 | NILKCLRY | 26906 |
| HPV31 | E2 | 10 | 303 | NILKCLRYRL | 26907 |
| HPV31 | E2 | 10 | 282 | NQTRAVSCPA | 26908 |
| HPV31 | E2 | 8 | 9 | NVCQDKIL | 26909 |
| HPV31 | E2 | 11 | 9 | NVCQDKILEHY | 26910 |
| HPV31 | E2 | 9 | 294 | PIIHLKGDA | 26911 |
| HPV31 | E2 | 11 | 294 | PIIHLKGDANI | 26912 |
| HPV31 | E2 | 10 | 317 | QLYEQVSSTW | 26913 |
| HPV31 | E2 | 8 | 95 | QQTSLELY | 26914 |
| HPV31 | E2 | 9 | 95 | QQTSLELYL | 26915 |
| HPV31 | E2 | 11 | 95 | QQTSLELYLTA | 26916 |
| HPV31 | E2 | 9 | 191 | QVIVFPESV | 26917 |
| HPV31 | E2 | 10 | 191 | QVIVFPESVF | 26918 |
| HPV31 | E2 | 8 | 151 | QVNCKGIY | 26919 |
| HPV31 | E2 | 9 | 151 | QVNCKGIYY | 26920 |
| HPV31 | E2 | 10 | 151 | QVNCKGIYYV | 26921 |
| HPV31 | E2 | 8 | 321 | QVSSTWHW | 26922 |
| HPV31 | E2 | 8 | 57 | QVVPALSV | 26923 |
| HPV31 | E2 | 11 | 57 | QVVPALSVSKA | 26924 |
| HPV31 | E2 | 8 | 25 | RLCDHIDY | 26925 |
| HPV31 | E2 | 9 | 25 | RLCDHIDYW | 26926 |
| HPV31 | E2 | 8 | 37 | RLECVLMY | 26927 |
| HPV31 | E2 | 10 | 37 | RLECVLMYKA | 26928 |
| HPV31 | E2 | 9 | 7 | RLNVCQDKI | 26929 |
| HPV31 | E2 | 10 | 7 | RLNVCQDKIL | 26930 |
| HPV31 | E2 | 8 | 311 | RLSKYKQL | 26931 |
| HPV31 | E2 | 9 | 311 | RLSKYKQLY | 26932 |
| HPV31 | E2 | 9 | 53 | SINHQVVPA | 26933 |
| HPV31 | E2 | 10 | 53 | SINHQVVPAL | 26934 |

TABLE XIV-continued

B62 Supermotif Peptides

| Type | Protein | No. of Amino Acid | Position | Sequence | Seq. Id. No. |
|---|---|---|---|---|---|
| HPV31 | E2 | 8 | 98 | SLELYLTA | 26935 |
| HPV31 | E2 | 10 | 348 | SQRDDFLNTV | 26936 |
| HPV31 | E2 | 11 | 5 | SQRLNVCQDKI | 26937 |
| HPV31 | E2 | 9 | 266 | SVDSVNCGV | 26938 |
| HPV31 | E2 | 10 | 266 | SVDSVNCGVI | 26939 |
| HPV31 | E2 | 8 | 198 | SVFSSDEI | 26940 |
| HPV31 | E2 | 10 | 198 | SVFSSDEISF | 26941 |
| HPV31 | E2 | 11 | 198 | SVFSSDEISFA | 26942 |
| HPV31 | E2 | 9 | 269 | SVNCGVISA | 26943 |
| HPV31 | E2 | 10 | 269 | SVNCGVISAA | 26944 |
| HPV31 | E2 | 11 | 269 | SVNCGVISAAA | 26945 |
| HPV31 | E2 | 8 | 63 | SVSKAKAL | 26946 |
| HPV31 | E2 | 10 | 63 | SVSKAKALQA | 26947 |
| HPV31 | E2 | 11 | 63 | SVSKAKALQAI | 26948 |
| HPV31 | E2 | 9 | 364 | SVSTGYMTI | 26949 |
| HPV31 | E2 | 8 | 3 | TLSQRLNV | 26950 |
| HPV31 | E2 | 9 | 128 | TMHYTNWKF | 26951 |
| HPV31 | E2 | 10 | 128 | TMHYTNWKFI | 26952 |
| HPV31 | E2 | 11 | 128 | TMHYTNWKFIY | 26953 |
| HPV31 | E2 | 9 | 93 | TMQQTSLEL | 26954 |
| HPV31 | E2 | 10 | 93 | TMQQTSLELY | 26955 |
| HPV31 | E2 | 11 | 93 | TMQQTSLELYL | 26956 |
| HPV31 | E2 | 10 | 293 | TPIIHLKGDA | 26957 |
| HPV31 | E2 | 10 | 116 | TVEVQFDGDV | 26958 |
| HPV31 | E2 | 8 | 356 | TVKIPNTV | 26959 |
| HPV31 | E2 | 10 | 356 | TVKIPNTVSV | 26960 |
| HPV31 | E2 | 8 | 362 | TVSVSTGY | 26961 |
| HPV31 | E2 | 9 | 362 | TVSVSTGYM | 26962 |
| HPV31 | E2 | 11 | 362 | TVSVSTGYMTI | 26963 |
| HPV31 | E2 | 8 | 192 | VIVFPESV | 26964 |
| HPV31 | E2 | 9 | 192 | VIVFPESVF | 26965 |
| HPV31 | E2 | 9 | 41 | VLMYKAREM | 26966 |
| HPV31 | E2 | 11 | 41 | VLMYKAREMGI | 26967 |
| HPV31 | E2 | 9 | 59 | VPALSVSKA | 26968 |
| HPV31 | E2 | 11 | 59 | VPALSVSKAKA | 26969 |
| HPV31 | E2 | 11 | 119 | VQFDGDVHNTM | 26970 |
| HPV31 | E2 | 11 | 147 | VVEGQVNCKGI | 26971 |
| HPV31 | E2 | 10 | 58 | VVPALSVSKA | 26972 |
| HPV31 | E2 | 10 | 344 | YISTSQRDDF | 26973 |
| HPV31 | E2 | 11 | 344 | YISTSQRDDFL | 26974 |
| HPV31 | E2 | 10 | 138 | YLCIDGQCTV | 26975 |
| HPV31 | E2 | 11 | 138 | YLCIDGQCTVV | 26976 |
| HPV31 | E2 | 9 | 102 | YLTAPTGCL | 26977 |
| HPV31 | E2 | 9 | 159 | YVHEGHITY | 26978 |
| HPV31 | E2 | 10 | 159 | YVHEGHITYF | 26979 |
| HPV31 | E2 | 11 | 159 | YVHEGHITYFV | 26980 |
| HPV31 | E5 | 8 | 61 | CIYVVFIY | 26981 |
| HPV31 | E5 | 9 | 61 | CIYVVFIYI | 26982 |
| HPV31 | E5 | 11 | 61 | CIYVVFIYIPL | 26983 |
| HPV31 | E5 | 8 | 26 | CLVIRPLV | 26984 |
| HPV31 | E5 | 9 | 26 | CLVIRPLVL | 26985 |
| HPV31 | E5 | 11 | 26 | CLVIRPLVLSV | 26986 |
| HPV31 | E5 | 8 | 20 | CVLLFVCL | 26987 |
| HPV31 | E5 | 9 | 20 | CVLLFVCLV | 26988 |
| HPV31 | E5 | 10 | 20 | CVLLFVCLVI | 26989 |
| HPV31 | E5 | 9 | 3 | ELNISTVSI | 26990 |
| HPV31 | E5 | 10 | 3 | ELNISTVSIV | 26991 |
| HPV31 | E5 | 11 | 3 | ELNISTVSIVL | 26992 |
| HPV31 | E5 | 8 | 66 | FIYIPLFV | 26993 |
| HPV31 | E5 | 9 | 66 | FIYIPLFVI | 26994 |
| HPV31 | E5 | 8 | 15 | FLLCFCVL | 26995 |
| HPV31 | E5 | 9 | 15 | FLLCFCVLL | 26996 |
| HPV31 | E5 | 10 | 15 | FLLCFCVLLF | 26997 |
| HPV31 | E5 | 11 | 15 | FLLCFCVLLFV | 26998 |
| HPV31 | E5 | 9 | 24 | FVCLVIRPL | 26999 |
| HPV31 | E5 | 10 | 24 | FVCLVIRPLV | 27000 |
| HPV31 | E5 | 11 | 24 | FVCLVIRPLVL | 27001 |
| HPV31 | E5 | 9 | 72 | FVIHTHASF | 27002 |
| HPV31 | E5 | 10 | 72 | FVIHTHASFL | 27003 |
| HPV31 | E5 | 10 | 48 | ILWVIATSPL | 27004 |
| HPV31 | E5 | 10 | 69 | IPLFVIHTHA | 27005 |
| HPV31 | E5 | 8 | 46 | IVILWVIA | 27006 |
| HPV31 | E5 | 9 | 11 | IVLCFLLCF | 27007 |
| HPV31 | E5 | 11 | 11 | IVLCFLLCFCV | 27008 |
| HPV31 | E5 | 8 | 45 | LIVILWVI | 27009 |

TABLE XIV-continued

B62 Supermotif Peptides

| Type | Protein | No. of Amino Acid | Position | Sequence | Seq. Id. No. |
|---|---|---|---|---|---|
| HPV31 | E5 | 9 | 45 | LIVILWVIA | 27010 |
| HPV31 | E5 | 8 | 16 | LLCFCVLL | 27011 |
| HPV31 | E5 | 9 | 16 | LLCFCVLLF | 27012 |
| HPV31 | E5 | 10 | 16 | LLCFCVLLFV | 27013 |
| HPV31 | E5 | 8 | 22 | LLFVCLVI | 27014 |
| HPV31 | E5 | 11 | 22 | LLFVCLVIRPL | 27015 |
| HPV31 | E5 | 8 | 44 | LLIVILWV | 27016 |
| HPV31 | E5 | 9 | 44 | LLIVILWVI | 27017 |
| HPV31 | E5 | 10 | 44 | LLIVILWVIA | 27018 |
| HPV31 | E5 | 8 | 43 | LLLIVILW | 27019 |
| HPV31 | E5 | 9 | 43 | LLLIVILWV | 27020 |
| HPV31 | E5 | 10 | 43 | LLLIVILWVI | 27021 |
| HPV31 | E5 | 11 | 43 | LLLIVILWVIA | 27022 |
| HPV31 | E5 | 8 | 42 | LLLLIVIL | 27023 |
| HPV31 | E5 | 9 | 42 | LLLLIVILW | 27024 |
| HPV31 | E5 | 10 | 42 | LLLLIVILWV | 27025 |
| HPV31 | E5 | 11 | 42 | LLLLIVILWVI | 27026 |
| HPV31 | E5 | 8 | 27 | LVIRPLVL | 27027 |
| HPV31 | E5 | 10 | 27 | LVIRPLVLSV | 27028 |
| HPV31 | E5 | 8 | 32 | LVLSVSVY | 27029 |
| HPV31 | E5 | 9 | 32 | LVLSVSVYA | 27030 |
| HPV31 | E5 | 11 | 32 | LVLSVSVYATL | 27031 |
| HPV31 | E5 | 9 | 1 | MIELNISTV | 27032 |
| HPV31 | E5 | 11 | 1 | MIELNISTVSI | 27033 |
| HPV31 | E5 | 8 | 5 | NISTVSIV | 27034 |
| HPV31 | E5 | 9 | 5 | NISTVSIVL | 27035 |
| HPV31 | E5 | 11 | 5 | NISTVSIVLCF | 27036 |
| HPV31 | E5 | 9 | 70 | PLFVIHTHA | 27037 |
| HPV31 | E5 | 11 | 70 | PLFVIHTHASF | 27038 |
| HPV31 | E5 | 8 | 56 | PLRCFCIY | 27039 |
| HPV31 | E5 | 9 | 56 | PLRCFCIYV | 27040 |
| HPV31 | E5 | 10 | 56 | PLRCFCIYVV | 27041 |
| HPV31 | E5 | 11 | 56 | PLRCFCIYVVF | 27042 |
| HPV31 | E5 | 8 | 31 | PLVLSVSV | 27043 |
| HPV31 | E5 | 9 | 31 | PLVLSVSVY | 27044 |
| HPV31 | E5 | 10 | 31 | PLVLSVSVYA | 27045 |
| HPV31 | E5 | 9 | 30 | RPLVLSVSV | 27046 |
| HPV31 | E5 | 10 | 30 | RPLVLSVSVY | 27047 |
| HPV31 | E5 | 11 | 30 | RPLVLSVSVYA | 27048 |
| HPV31 | E5 | 8 | 10 | SIVLCFLL | 27049 |
| HPV31 | E5 | 10 | 10 | SIVLCFLLCF | 27050 |
| HPV31 | E5 | 8 | 55 | SPLRCFCI | 27051 |
| HPV31 | E5 | 9 | 55 | SPLRCFCIY | 27052 |
| HPV31 | E5 | 10 | 55 | SPLRCFCIYV | 27053 |
| HPV31 | E5 | 11 | 55 | SPLRCFCIYVV | 27054 |
| HPV31 | E5 | 8 | 35 | SVSVYATL | 27055 |
| HPV31 | E5 | 9 | 35 | SVSVYATLL | 27056 |
| HPV31 | E5 | 10 | 35 | SVSVYATLLL | 27057 |
| HPV31 | E5 | 11 | 35 | SVSVYATLLLL | 27058 |
| HPV31 | E5 | 8 | 37 | SVYATLLL | 27059 |
| HPV31 | E5 | 9 | 37 | SVYATLLLL | 27060 |
| HPV31 | E5 | 10 | 37 | SYVATLLLLI | 27061 |
| HPV31 | E5 | 11 | 37 | SVYATLLLLIV | 27062 |
| HPV31 | E5 | 8 | 41 | TLLLLIVI | 27063 |
| HPV31 | E5 | 9 | 41 | TLLLLIVIL | 27064 |
| HPV31 | E5 | 10 | 41 | TLLLLIVILW | 27065 |
| HPV31 | E5 | 11 | 41 | TLLLLIVILWV | 27066 |
| HPV31 | E5 | 8 | 8 | TVSIVLCF | 27067 |
| HPV31 | E5 | 9 | 8 | TVSIVLCFL | 27068 |
| HPV31 | E5 | 10 | 8 | TVSIVLCFLL | 27069 |
| HPV31 | E5 | 10 | 51 | VIATSPLRCF | 27070 |
| HPV31 | E5 | 8 | 73 | VIHTHASF | 27071 |
| HPV31 | E5 | 9 | 73 | VIHTHASFL | 27072 |
| HPV31 | E5 | 11 | 47 | VILWVIATSPL | 27073 |
| HPV31 | E5 | 9 | 28 | VIRPLVLSV | 27074 |
| HPV31 | E5 | 11 | 28 | VIRPLVLSVSV | 27075 |
| HPV31 | E5 | 8 | 12 | VLCFLLCF | 27076 |
| HPV31 | E5 | 10 | 12 | VLCFLLCFCV | 27077 |
| HPV31 | E5 | 11 | 12 | VLCFLLCFCVL | 27078 |
| HPV31 | E5 | 8 | 21 | VLLFVCLV | 27079 |
| HPV31 | E5 | 9 | 21 | VLLFVCLVI | 27080 |
| HPV31 | E5 | 8 | 33 | VLSVSVYA | 27081 |
| HPV31 | E5 | 10 | 33 | VLSVSVYATL | 27082 |
| HPV31 | E5 | 11 | 33 | VLSVSVYATLL | 27083 |
| HPV31 | E5 | 8 | 64 | VVFIYIPL | 27084 |

TABLE XIV-continued

B62 Supermotif Peptides

| Type | Protein | No. of Amino Acid | Position | Sequence | Seq. Id. No. |
|---|---|---|---|---|---|
| HPV31 | E5 | 9 | 64 | VVFIYIPLF | 27085 |
| HPV31 | E5 | 10 | 64 | VVFIYIPLFV | 27086 |
| HPV31 | E5 | 11 | 64 | VVFIYIPLFVI | 27087 |
| HPV31 | E5 | 8 | 50 | WVIATSPL | 27088 |
| HPV31 | E5 | 11 | 50 | WVIATSPLRCF | 27089 |
| HPV31 | E5 | 11 | 68 | YIPLFVIHTHA | 27090 |
| HPV31 | E5 | 9 | 63 | YVVFIYIPL | 27091 |
| HPV31 | E5 | 10 | 63 | YVVFIYIPLF | 27092 |
| HPV31 | E5 | 11 | 63 | YVVFIYIPLFV | 27093 |
| HPV31 | E6 | 9 | 18 | ALEIPYDEL | 27094 |
| HPV31 | E6 | 11 | 18 | ALEIPYDELRL | 27095 |
| HPV31 | E6 | 8 | 103 | CITCQRPL | 27096 |
| HPV31 | E6 | 8 | 66 | CLRFYSKV | 27097 |
| HPV31 | E6 | 11 | 66 | CLRFYSKVSEF | 27098 |
| HPV31 | E6 | 9 | 111 | CPEEKQRHL | 27099 |
| HPV31 | E6 | 8 | 30 | CVYCKGQL | 27100 |
| HPV31 | E6 | 9 | 20 | EIPYDELRL | 27101 |
| HPV31 | E6 | 8 | 25 | ELRLNCVY | 27102 |
| HPV31 | E6 | 8 | 14 | ELSSALEI | 27103 |
| HPV31 | E6 | 10 | 14 | ELSSALEIPY | 27104 |
| HPV31 | E6 | 10 | 41 | EVLDFAFTDL | 27105 |
| HPV31 | E6 | 10 | 95 | GICDLLIRCI | 27106 |
| HPV31 | E6 | 8 | 35 | GQLTETEV | 27107 |
| HPV31 | E6 | 9 | 35 | GQLTETEVL | 27108 |
| HPV31 | E6 | 11 | 35 | GQLTETEVLDF | 27109 |
| HPV31 | E6 | 9 | 61 | GVCTKCLRF | 27110 |
| HPV31 | E6 | 10 | 61 | GVCTKCLRFY | 27111 |
| HPV31 | E6 | 8 | 118 | HLDKKKRF | 27112 |
| HPV31 | E6 | 11 | 118 | HLDKKKRFHNI | 27113 |
| HPV31 | E6 | 8 | 21 | IPYDELRL | 27114 |
| HPV31 | E6 | 11 | 21 | IPYDELRLNCV | 27115 |
| HPV31 | E6 | 11 | 52 | IVYRDDTPHGV | 27116 |
| HPV31 | E6 | 8 | 11 | KLHELSSA | 27117 |
| HPV31 | E6 | 9 | 11 | KLHELSSAL | 27118 |
| HPV31 | E6 | 11 | 11 | KLHELSSALEI | 27119 |
| HPV31 | E6 | 10 | 90 | KLTNKGICDL | 27120 |
| HPV31 | E6 | 11 | 90 | KLTNKGICDLL | 27121 |
| HPV31 | E6 | 11 | 115 | KQRHLDKKKRF | 27122 |
| HPV31 | E6 | 8 | 72 | KVSEFRWY | 27123 |
| HPV31 | E6 | 10 | 72 | KVSEFRWYRY | 27124 |
| HPV31 | E6 | 11 | 100 | LIRCITCQRPL | 27125 |
| HPV31 | E6 | 11 | 127 | NIGGRWTGRCI | 27126 |
| HPV31 | E6 | 9 | 4 | NPAERPRKL | 27127 |
| HPV31 | E6 | 11 | 109 | PLCPEEKQRHL | 27128 |
| HPV31 | E6 | 8 | 36 | QLTETEVL | 27129 |
| HPV31 | E6 | 10 | 36 | QLTETEVLDF | 27130 |
| HPV31 | E6 | 11 | 36 | QLTETEVLDFA | 27131 |
| HPV31 | E6 | 11 | 27 | RLNCVYCKGQL | 27132 |
| HPV31 | E6 | 8 | 8 | RPRKLHEL | 27133 |
| HPV31 | E6 | 11 | 8 | RPRKLHELSSA | 27134 |
| HPV31 | E6 | 8 | 142 | RPRTETQV | 27135 |
| HPV31 | E6 | 10 | 82 | SVYGTTLEKL | 27136 |
| HPV31 | E6 | 10 | 87 | TLEKLTNKGI | 27137 |
| HPV31 | E6 | 10 | 58 | TPHGVCTKCL | 27138 |
| HPV31 | E6 | 9 | 42 | VLDFAFTDL | 27139 |
| HPV31 | E6 | 11 | 42 | VLDFAFTDLTI | 27140 |
| HPV31 | E7 | 8 | 91 | CPNCSTRL | 27141 |
| HPV31 | E7 | 9 | 59 | CQCKSTLRL | 27142 |
| HPV31 | E7 | 11 | 59 | CQCKSTLRLCV | 27143 |
| HPV31 | E7 | 9 | 68 | CVQSTQVDI | 27144 |
| HPV31 | E7 | 11 | 68 | CVQSTQVDIRI | 27145 |
| HPV31 | E7 | 8 | 75 | DIRILQEL | 27146 |
| HPV31 | E7 | 9 | 75 | DIRILQELL | 27147 |
| HPV31 | E7 | 10 | 75 | DIRILQELLM | 27148 |
| HPV31 | E7 | 8 | 21 | DLHCYEQL | 27149 |
| HPV31 | E7 | 9 | 14 | DLQPEATDL | 27150 |
| HPV31 | E7 | 10 | 36 | DVIDSPAGQA | 27151 |
| HPV31 | E7 | 9 | 81 | ELLMGSFGI | 27152 |
| HPV31 | E7 | 10 | 81 | ELLMGSFGIV | 27153 |
| HPV31 | E7 | 9 | 46 | EPDTSNYNI | 27154 |
| HPV31 | E7 | 10 | 46 | EPDTSNYNIV | 27155 |
| HPV31 | E7 | 11 | 88 | GIVCPNCSTRL | 27156 |
| HPV31 | E7 | 10 | 43 | GQAEPDTSNY | 27157 |
| HPV31 | E7 | 10 | 78 | ILQELLMGSF | 27158 |
| HPV31 | E7 | 10 | 89 | IVCPNCSTRL | 27159 |

TABLE XIV-continued

B62 Supermotif Peptides

| Type | Protein | No. of Amino Acid | Position | Sequence | Seq. Id. No. |
|---|---|---|---|---|---|
| HPV31 | E7 | 8 | 82 | LLMGSFGI | 27160 |
| HPV31 | E7 | 9 | 82 | LLMGSFGIV | 27161 |
| HPV31 | E7 | 8 | 83 | LMGSFGIV | 27162 |
| HPV31 | E7 | 10 | 28 | LPDSSDEEDV | 27163 |
| HPV31 | E7 | 11 | 28 | LPDSSDEEDVI | 27164 |
| HPV31 | E7 | 8 | 8 | LQDYVLDL | 27165 |
| HPV31 | E7 | 9 | 79 | LQELLMGSF | 27166 |
| HPV31 | E7 | 11 | 79 | LQELLMGSFGI | 27167 |
| HPV31 | E7 | 8 | 15 | LQPEATDL | 27168 |
| HPV31 | E7 | 11 | 15 | LQPEATDLHCY | 27169 |
| HPV31 | E7 | 11 | 27 | QLPDSSDEEDV | 27170 |
| HPV31 | E7 | 10 | 16 | QPEATDLHCY | 27171 |
| HPV31 | E7 | 10 | 73 | QVDIRILQEL | 27172 |
| HPV31 | E7 | 11 | 73 | QVDIRILQELL | 27173 |
| HPV31 | E7 | 8 | 77 | RILQELLM | 27174 |
| HPV31 | E7 | 11 | 77 | RILQELLMGSF | 27175 |
| HPV31 | E7 | 9 | 66 | RLCVQSTQV | 27176 |
| HPV31 | E7 | 11 | 66 | RLCVQSTQVDI | 27177 |
| HPV31 | E7 | 9 | 7 | TLQDYVLDL | 27178 |
| HPV31 | E7 | 11 | 64 | TLRLCVQSTQV | 27179 |
| HPV31 | E7 | 8 | 5 | TPTLQDYV | 27180 |
| HPV31 | E7 | 9 | 5 | TPTLQDYVL | 27181 |
| HPV31 | E7 | 11 | 5 | TPTLQDYVLDL | 27182 |
| HPV31 | E7 | 8 | 72 | TQVDIRIL | 27183 |
| HPV31 | E7 | 11 | 72 | TQVDIRILQEL | 27184 |
| HPV31 | E7 | 9 | 37 | VIDSPAGQA | 27185 |
| HPV31 | E7 | 8 | 12 | VLDLQPEA | 27186 |
| HPV31 | E7 | 11 | 12 | VLDLQPEATDL | 27187 |
| HPV31 | E7 | 8 | 69 | VQSTQVDI | 27188 |
| HPV31 | E7 | 10 | 69 | VQSTQVDIRI | 27189 |
| HPV31 | E7 | 11 | 69 | VQSTQVDIRIL | 27190 |
| HPV31 | E7 | 9 | 11 | YVLDLQPEA | 27191 |
| HPV31 | L1 | 9 | 348 | AIANSDTTF | 27192 |
| HPV31 | L1 | 8 | 398 | AILEDWNF | 27193 |
| HPV31 | L1 | 10 | 398 | AILEDWNFGL | 27194 |
| HPV31 | L1 | 8 | 426 | AITCQKTA | 27195 |
| HPV31 | L1 | 10 | 180 | AITPGDCPPL | 27196 |
| HPV31 | L1 | 9 | 213 | ALQDTKSNV | 27197 |
| HPV31 | L1 | 11 | 213 | ALQDTKSNVPL | 27198 |
| HPV31 | L1 | 10 | 433 | APQKPKEDPF | 27199 |
| HPV31 | L1 | 10 | 488 | APSASTTTPA | 27200 |
| HPV31 | L1 | 8 | 317 | AQGHNNGI | 27201 |
| HPV31 | L1 | 10 | 317 | AQGHNNGICW | 27202 |
| HPV31 | L1 | 8 | 305 | AQIFNKPY | 27203 |
| HPV31 | L1 | 9 | 305 | AQIFNKPYW | 27204 |
| HPV31 | L1 | 10 | 305 | AQIFNKPYWM | 27205 |
| HPV31 | L1 | 11 | 147 | CISMDYKQTQL | 27206 |
| HPV31 | L1 | 9 | 158 | CLLGCKPPI | 27207 |
| HPV31 | L1 | 10 | 186 | CPPLELKNSV | 27208 |
| HPV31 | L1 | 11 | 186 | CPPLELKNSVI | 27209 |
| HPV31 | L1 | 9 | 224 | DICNSICKY | 27210 |
| HPV31 | L1 | 9 | 387 | DIMTYIHSM | 27211 |
| HPV31 | L1 | 11 | 459 | DLDQFPLGRKF | 27212 |
| HPV31 | L1 | 8 | 372 | DLQFIFQL | 27213 |
| HPV31 | L1 | 11 | 372 | DLQFIFQLCKI | 27214 |
| HPV31 | L1 | 11 | 275 | DLYIKGSGSTA | 27215 |
| HPV31 | L1 | 9 | 200 | DMVDTGFGA | 27216 |
| HPV31 | L1 | 10 | 200 | DMVDTGFGAM | 27217 |
| HPV31 | L1 | 8 | 440 | DPFKDYVF | 27218 |
| HPV31 | L1 | 9 | 440 | DPFKDYVFW | 27219 |
| HPV31 | L1 | 11 | 440 | DPFKDYVFWEV | 27220 |
| HPV31 | L1 | 9 | 461 | DQFPLGRKF | 27221 |
| HPV31 | L1 | 10 | 461 | DQFPLGRKFL | 27222 |
| HPV31 | L1 | 11 | 461 | DQFPLGRKFLL | 27223 |
| HPV31 | L1 | 8 | 241 | EPYGDTLF | 27224 |
| HPV31 | L1 | 9 | 241 | EPYGDTLFF | 27225 |
| HPV31 | L1 | 10 | 241 | EPYGDTLFFY | 27226 |
| HPV31 | L1 | 11 | 241 | EPYGDTLFFYL | 27227 |
| HPV31 | L1 | 8 | 254 | EQMFVRHF | 27228 |
| HPV31 | L1 | 9 | 254 | EQMFVRHFF | 27229 |
| HPV31 | L1 | 8 | 107 | EVGRGQPL | 27230 |
| HPV31 | L1 | 10 | 107 | EVGRGQPLGV | 27231 |
| HPV31 | L1 | 8 | 449 | EVNLKEKF | 27232 |
| HPV31 | L1 | 10 | 449 | EVNLKEKFSA | 27233 |
| HPV31 | L1 | 8 | 375 | FIFQLCKI | 27234 |

TABLE XIV-continued

B62 Supermotif Peptides

| Type | Protein | No. of Amino Acid | Position | Sequence | Seq. Id. No. |
|---|---|---|---|---|---|
| HPV31 | L1 | 10 | 375 | FIFQLCKITL | 27235 |
| HPV31 | L1 | 9 | 469 | FLLQAGYRA | 27236 |
| HPV31 | L1 | 8 | 463 | FPLGRKFL | 27237 |
| HPV31 | L1 | 9 | 463 | FPLGRKFLL | 27238 |
| HPV31 | L1 | 11 | 463 | FPLGRKFLLQA | 27239 |
| HPV31 | L1 | 8 | 293 | FPTPSGSM | 27240 |
| HPV31 | L1 | 9 | 293 | FPTPSGSMV | 27241 |
| HPV31 | L1 | 8 | 377 | FQLCKITL | 27242 |
| HPV31 | L1 | 10 | 377 | FQLCKITLSA | 27243 |
| HPV31 | L1 | 8 | 323 | GICWGNQL | 27244 |
| HPV31 | L1 | 9 | 323 | GICWGNQLF | 27245 |
| HPV31 | L1 | 10 | 323 | GICWGNQLFV | 27246 |
| HPV31 | L1 | 8 | 117 | GISGHPLL | 27247 |
| HPV31 | L1 | 11 | 117 | GISGHPLLNKF | 27248 |
| HPV31 | L1 | 10 | 105 | GLEVGRGQPL | 27249 |
| HPV31 | L1 | 9 | 68 | GLQYRVFRV | 27250 |
| HPV31 | L1 | 11 | 68 | GLQYRVFRVRL | 27251 |
| HPV31 | L1 | 10 | 406 | GLTTPPSGSL | 27252 |
| HPV31 | L1 | 10 | 139 | GPGTDNRECI | 27253 |
| HPV31 | L1 | 8 | 111 | GQPLGVGI | 27254 |
| HPV31 | L1 | 9 | 115 | GVGISGHPL | 27255 |
| HPV31 | L1 | 10 | 115 | GVGISGHPLL | 27256 |
| HPV31 | L1 | 9 | 399 | ILEDWNFGL | 27257 |
| HPV31 | L1 | 8 | 388 | IMTYIHSM | 27258 |
| HPV31 | L1 | 11 | 388 | IMTYIHSMNPA | 27259 |
| HPV31 | L1 | 10 | 52 | IPKSDNPKKI | 27260 |
| HPV31 | L1 | 11 | 52 | IPKSDNPKKIV | 27261 |
| HPV31 | L1 | 11 | 196 | IQDGDMVDTGF | 27262 |
| HPV31 | L1 | 9 | 61 | IVVPKVSGL | 27263 |
| HPV31 | L1 | 11 | 61 | IVVPKVSGLQY | 27264 |
| HPV31 | L1 | 8 | 381 | KITLSADI | 27265 |
| HPV31 | L1 | 9 | 381 | KITLSADIM | 27266 |
| HPV31 | L1 | 11 | 381 | KITLSADIMTY | 27267 |
| HPV31 | L1 | 10 | 60 | KIVVPKVSGL | 27268 |
| HPV31 | L1 | 11 | 237 | KMVAEPYGDTL | 27269 |
| HPV31 | L1 | 10 | 436 | KPKEDPFKDY | 27270 |
| HPV31 | L1 | 11 | 436 | KPKEDPFKDYV | 27271 |
| HPV31 | L1 | 8 | 163 | KPPIGEHW | 27272 |
| HPV31 | L1 | 8 | 310 | KPYWMQRA | 27273 |
| HPV31 | L1 | 8 | 153 | KQTQLCLL | 27274 |
| HPV31 | L1 | 9 | 65 | KVSGLQYRV | 27275 |
| HPV31 | L1 | 10 | 65 | KVSGLQYRVF | 27276 |
| HPV31 | L1 | 8 | 20 | KVVSTDEY | 27277 |
| HPV31 | L1 | 9 | 20 | KVVSTDEYV | 27278 |
| HPV31 | L1 | 8 | 159 | LLGCKPPI | 27279 |
| HPV31 | L1 | 8 | 470 | LLQAGYRA | 27280 |
| HPV31 | L1 | 8 | 42 | LLTVGHPY | 27281 |
| HPV31 | L1 | 9 | 42 | LLTVGHPYY | 27282 |
| HPV31 | L1 | 11 | 42 | LLTVGHPYYSI | 27283 |
| HPV31 | L1 | 9 | 78 | LPDPNKFGF | 27284 |
| HPV31 | L1 | 9 | 13 | LPPVPVSKV | 27285 |
| HPV31 | L1 | 10 | 13 | LPPVPVSKVV | 27286 |
| HPV31 | L1 | 11 | 471 | LQAGYRARPKF | 27287 |
| HPV31 | L1 | 8 | 214 | LQDTKSNV | 27288 |
| HPV31 | L1 | 10 | 214 | LQDTKSNVPL | 27289 |
| HPV31 | L1 | 10 | 373 | LQFIFQLCKI | 27290 |
| HPV31 | L1 | 8 | 69 | LQYRVFRV | 27291 |
| HPV31 | L1 | 10 | 69 | LQYRVFRVRL | 27292 |
| HPV31 | L1 | 8 | 99 | LVWACVGL | 27293 |
| HPV31 | L1 | 10 | 99 | LVWACVGLEV | 27294 |
| HPV31 | L1 | 11 | 314 | MQRAQGHNNGI | 27295 |
| HPV31 | L1 | 10 | 238 | MVAEPYGDTL | 27296 |
| HPV31 | L1 | 11 | 238 | MVAEPYGDTLF | 27297 |
| HPV31 | L1 | 8 | 201 | MVDTGFGA | 27298 |
| HPV31 | L1 | 9 | 201 | MVDTGFGAM | 27299 |
| HPV31 | L1 | 11 | 201 | MVDTGFGAMDF | 27300 |
| HPV31 | L1 | 8 | 300 | MVTSDAQI | 27301 |
| HPV31 | L1 | 9 | 300 | MVTSDAQIF | 27302 |
| HPV31 | L1 | 9 | 32 | NIYYHAGSA | 27303 |
| HPV31 | L1 | 11 | 32 | NIYYHAGSARL | 27304 |
| HPV31 | L1 | 8 | 451 | NLKEKFSA | 27305 |
| HPV31 | L1 | 10 | 451 | NLKEKFSADL | 27306 |
| HPV31 | L1 | 8 | 342 | NMSVCAAI | 27307 |
| HPV31 | L1 | 9 | 342 | NMSVCAAIA | 27308 |
| HPV31 | L1 | 8 | 396 | NPAILEDW | 27309 |

TABLE XIV-continued

B62 Supermotif Peptides

| Type | Protein | No. of Amino Acid | Position | Sequence | Seq. Id. No. |
|---|---|---|---|---|---|
| HPV31 | L1 | 10 | 396 | NPAILEDWNF | 27310 |
| HPV31 | L1 | 8 | 93 | NPETQRLV | 27311 |
| HPV31 | L1 | 9 | 93 | NPETQRLVW | 27312 |
| HPV31 | L1 | 10 | 93 | NPETQRLVWA | 27313 |
| HPV31 | L1 | 10 | 57 | NPKKIVVPKV | 27314 |
| HPV31 | L1 | 8 | 328 | NQLFVTVV | 27315 |
| HPV31 | L1 | 10 | 220 | NVPLDICNSI | 27316 |
| HPV31 | L1 | 8 | 222 | PLDICNSI | 27317 |
| HPV31 | L1 | 11 | 222 | PLDICNSICKY | 27318 |
| HPV31 | L1 | 8 | 188 | PLELKNSV | 27319 |
| HPV31 | L1 | 9 | 188 | PLELKNSVI | 27320 |
| HPV31 | L1 | 8 | 464 | PLGRKFLL | 27321 |
| HPV31 | L1 | 10 | 464 | PLGRKFLLQA | 27322 |
| HPV31 | L1 | 11 | 113 | PLGVGISGHPL | 27323 |
| HPV31 | L1 | 9 | 187 | PPLELKNSV | 27324 |
| HPV31 | L1 | 10 | 187 | PPLELKNSVI | 27325 |
| HPV31 | L1 | 10 | 410 | PPSGSLEDTY | 27326 |
| HPV31 | L1 | 8 | 14 | PPVPVSKV | 27327 |
| HPV31 | L1 | 9 | 14 | PPVPVSKVV | 27328 |
| HPV31 | L1 | 9 | 434 | PQKPKEDPF | 27329 |
| HPV31 | L1 | 8 | 15 | PVPVSKVV | 27330 |
| HPV31 | L1 | 11 | 17 | PVSKVVSTDEY | 27331 |
| HPV31 | L1 | 8 | 306 | QIFNKPYW | 27332 |
| HPV31 | L1 | 9 | 306 | QIFNKPYWM | 27333 |
| HPV31 | L1 | 9 | 378 | QLCKITLSA | 27334 |
| HPV31 | L1 | 11 | 378 | QLCKITLSADI | 27335 |
| HPV31 | L1 | 11 | 156 | QLCLLGCKPPI | 27336 |
| HPV31 | L1 | 8 | 255 | QMFVRHFF | 27337 |
| HPV31 | L1 | 9 | 41 | RLLTVGHPY | 27338 |
| HPV31 | L1 | 10 | 41 | RLLTVGHPYY | 27339 |
| HPV31 | L1 | 8 | 77 | RLPDPNKF | 27340 |
| HPV31 | L1 | 10 | 77 | RLPDPNKFGF | 27341 |
| HPV31 | L1 | 9 | 98 | RLVWACVGL | 27342 |
| HPV31 | L1 | 11 | 98 | RLVWACVGLEV | 27343 |
| HPV31 | L1 | 11 | 478 | RPKFKAGKRSA | 27344 |
| HPV31 | L1 | 8 | 5 | RPSEATVY | 27345 |
| HPV31 | L1 | 9 | 5 | RPSEATVYL | 27346 |
| HPV31 | L1 | 10 | 75 | RVRLPDPNKF | 27347 |
| HPV31 | L1 | 8 | 228 | SICKYPDY | 27348 |
| HPV31 | L1 | 9 | 228 | SICKYPDYL | 27349 |
| HPV31 | L1 | 11 | 228 | SICKYPDYLKM | 27350 |
| HPV31 | L1 | 11 | 51 | SIPKSDNPKKI | 27351 |
| HPV31 | L1 | 8 | 414 | SLEDTYRF | 27352 |
| HPV31 | L1 | 9 | 414 | SLEDTYRFV | 27353 |
| HPV31 | L1 | 8 | 2 | SLWRPSEA | 27354 |
| HPV31 | L1 | 10 | 2 | SLWRPSEATV | 27355 |
| HPV31 | L1 | 11 | 2 | SLWRPSEATVY | 27356 |
| HPV31 | L1 | 9 | 149 | SMDYKQTQL | 27357 |
| HPV31 | L1 | 11 | 149 | SMDYKQTQLCL | 27358 |
| HPV31 | L1 | 10 | 394 | SMNPAILEDW | 27359 |
| HPV31 | L1 | 9 | 299 | SMVTSDAQI | 27360 |
| HPV31 | L1 | 10 | 299 | SMVTSDAQIF | 27361 |
| HPV31 | L1 | 8 | 174 | SPCSNNAI | 27362 |
| HPV31 | L1 | 10 | 424 | SQAITCQKTA | 27363 |
| HPV31 | L1 | 8 | 194 | SVIQDGDM | 27364 |
| HPV31 | L1 | 9 | 194 | SVIQDGDMV | 27365 |
| HPV31 | L1 | 8 | 271 | SVPTDLYI | 27366 |
| HPV31 | L1 | 8 | 286 | TLANSTYF | 27367 |
| HPV31 | L1 | 11 | 246 | TLFFYLRREQM | 27368 |
| HPV31 | L1 | 9 | 383 | TLSADIMTY | 27369 |
| HPV31 | L1 | 10 | 383 | TLSADIMTYI | 27370 |
| HPV31 | L1 | 8 | 182 | TPGDCPPL | 27371 |
| HPV31 | L1 | 10 | 182 | TPGDCPPLEL | 27372 |
| HPV31 | L1 | 11 | 409 | TPPSGSLEDTY | 27373 |
| HPV31 | L1 | 11 | 295 | TPSGSMVTSDA | 27374 |
| HPV31 | L1 | 9 | 96 | TQRLVWACV | 27375 |
| HPV31 | L1 | 11 | 96 | TQRLVWACVGL | 27376 |
| HPV31 | L1 | 10 | 267 | TVGESVPTDL | 27377 |
| HPV31 | L1 | 11 | 267 | TVGESVPTDLY | 27378 |
| HPV31 | L1 | 9 | 44 | TVGHPYYSI | 27379 |
| HPV31 | L1 | 11 | 333 | TVVDTTRSTNM | 27380 |
| HPV31 | L1 | 9 | 10 | TVYLPPVPV | 27381 |
| HPV31 | L1 | 8 | 195 | VIQDGDMV | 27382 |
| HPV31 | L1 | 9 | 63 | VPKVSGLQY | 27383 |
| HPV31 | L1 | 11 | 63 | VPKVSGLQYRV | 27384 |

TABLE XIV-continued

B62 Supermotif Peptides

| Type | Protein | No. of Amino Acid | Position | Sequence | Seq. Id. No. |
|---|---|---|---|---|---|
| HPV31 | L1 | 9 | 221 | VPLDICNSI | 27385 |
| HPV31 | L1 | 10 | 334 | VVDTTRSTNM | 27386 |
| HPV31 | L1 | 8 | 62 | VVPKVSGL | 27387 |
| HPV31 | L1 | 10 | 62 | VVPKVSGLQY | 27388 |
| HPV31 | L1 | 8 | 21 | VVSTDEYV | 27389 |
| HPV31 | L1 | 8 | 391 | YIHSMNPA | 27390 |
| HPV31 | L1 | 9 | 391 | YIHSMNPAI | 27391 |
| HPV31 | L1 | 10 | 391 | YIHSMNPAIL | 27392 |
| HPV31 | L1 | 9 | 277 | YIKGSGSTA | 27393 |
| HPV31 | L1 | 11 | 277 | YIKGSGSTATL | 27394 |
| HPV31 | L1 | 9 | 235 | YLKMVAEPY | 27395 |
| HPV31 | L1 | 10 | 12 | YLPPVPVSKV | 27396 |
| HPV31 | L1 | 11 | 12 | YLPPVPVSKVV | 27397 |
| HPV31 | L1 | 8 | 364 | YLRHGEEF | 27398 |
| HPV31 | L1 | 10 | 364 | YLRHGEEFDL | 27399 |
| HPV31 | L1 | 8 | 250 | YLRREQMF | 27400 |
| HPV31 | L1 | 9 | 250 | YLRREQMFV | 27401 |
| HPV31 | L1 | 8 | 232 | YPDYLKMV | 27402 |
| HPV31 | L1 | 9 | 232 | YPDYLKMVA | 27403 |
| HPV31 | L1 | 8 | 445 | YVFWEVNL | 27404 |
| HPV31 | L1 | 8 | 27 | YVTRTNIY | 27405 |
| HPV31 | L1 | 9 | 27 | YVTRTNIYY | 27406 |
| HPV31 | L1 | 11 | 27 | YVTRTNIYYHA | 27407 |
| HPV31 | L2 | 8 | 143 | AILDVTSV | 27408 |
| HPV31 | L2 | 9 | 286 | ALTSRRNTV | 27409 |
| HPV31 | L2 | 11 | 286 | ALTSRRNTVRY | 27410 |
| HPV31 | L2 | 9 | 271 | APDPDFLDI | 27411 |
| HPV31 | L2 | 10 | 271 | APDPDFLDII | 27412 |
| HPV31 | L2 | 11 | 271 | APDPDFLDIIA | 27413 |
| HPV31 | L2 | 8 | 240 | APKQLITY | 27414 |
| HPV31 | L2 | 8 | 414 | APTQVFPF | 27415 |
| HPV31 | L2 | 10 | 414 | APTQVFPFPL | 27416 |
| HPV31 | L2 | 11 | 414 | APTQVFPFPLA | 27417 |
| HPV31 | L2 | 9 | 424 | APTTPQVSI | 27418 |
| HPV31 | L2 | 10 | 424 | APTTPQVSIF | 27419 |
| HPV31 | L2 | 11 | 424 | APTTPQVSIFV | 27420 |
| HPV31 | L2 | 8 | 376 | AVQSTSAV | 27421 |
| HPV31 | L2 | 10 | 376 | AVQSTSAVSA | 27422 |
| HPV31 | L2 | 11 | 376 | AVQSTSAVSAY | 27423 |
| HPV31 | L2 | 9 | 28 | CPSDVIPKI | 27424 |
| HPV31 | L2 | 11 | 133 | DIATTADTTPA | 27425 |
| HPV31 | L2 | 9 | 278 | DIIALHRPA | 27426 |
| HPV31 | L2 | 10 | 278 | DIIALHRPAL | 27427 |
| HPV31 | L2 | 10 | 400 | DIPIFSGPDV | 27428 |
| HPV31 | L2 | 8 | 322 | DISSINPA | 27429 |
| HPV31 | L2 | 8 | 354 | DIYADTDF | 27430 |
| HPV31 | L2 | 10 | 354 | DIYADTDFTV | 27431 |
| HPV31 | L2 | 8 | 273 | DPDFLDII | 27432 |
| HPV31 | L2 | 9 | 273 | DPDFLDIIA | 27433 |
| HPV31 | L2 | 10 | 273 | DPDFLDIIAL | 27434 |
| HPV31 | L2 | 8 | 102 | DPSIVSLV | 27435 |
| HPV31 | L2 | 11 | 160 | DPSVLQPPTPA | 27436 |
| HPV31 | L2 | 11 | 234 | DPTFLSAPKQL | 27437 |
| HPV31 | L2 | 10 | 96 | DPVGPLDPSI | 27438 |
| HPV31 | L2 | 11 | 96 | DPVGPLDPSIV | 27439 |
| HPV31 | L2 | 9 | 43 | DQILRYGSM | 27440 |
| HPV31 | L2 | 11 | 43 | DQILRYGSMGV | 27441 |
| HPV31 | L2 | 8 | 116 | DVGAPAPI | 27442 |
| HPV31 | L2 | 11 | 31 | DVIPKIEHTTI | 27443 |
| HPV31 | L2 | 11 | 408 | DVPIEHAPTQV | 27444 |
| HPV31 | L2 | 8 | 190 | EIPMDTFI | 27445 |
| HPV31 | L2 | 9 | 190 | EIPMDTFIV | 27446 |
| HPV31 | L2 | 9 | 334 | EMQPLGASA | 27447 |
| HPV31 | L2 | 10 | 196 | FIVSTNNENI | 27448 |
| HPV31 | L2 | 11 | 276 | FLDIIALHRPA | 27449 |
| HPV31 | L2 | 8 | 237 | FLSAPKQL | 27450 |
| HPV31 | L2 | 9 | 237 | FLSAPKQLI | 27451 |
| HPV31 | L2 | 11 | 237 | FLSAPKQLITY | 27452 |
| HPV31 | L2 | 10 | 421 | FPLAPTTPQV | 27453 |
| HPV31 | L2 | 8 | 433 | FVDGGDFY | 27454 |
| HPV31 | L2 | 9 | 433 | FVDGGDFYL | 27455 |
| HPV31 | L2 | 9 | 113 | GIVDVGAPA | 27456 |
| HPV31 | L2 | 11 | 113 | GIVDVGAPAPI | 27457 |
| HPV31 | L2 | 11 | 351 | GLYDIYADTDF | 27458 |
| HPV31 | L2 | 10 | 221 | GLYSKATQQV | 27459 |

TABLE XIV-continued

B62 Supermotif Peptides

| Type | Protein | No. of Amino Acid | Position | Sequence | Seq. Id. No. |
|---|---|---|---|---|---|
| HPV31 | L2 | 9 | 406 | GPDVPIEHA | 27460 |
| HPV31 | L2 | 8 | 99 | GPLDPSIV | 27461 |
| HPV31 | L2 | 10 | 99 | GPLDPSIVSL | 27462 |
| HPV31 | L2 | 11 | 99 | GPLDPSIVSLV | 27463 |
| HPV31 | L2 | 9 | 52 | GVFFGGLGI | 27464 |
| HPV31 | L2 | 8 | 213 | GVRRPARL | 27465 |
| HPV31 | L2 | 10 | 213 | GVRRPARLGL | 27466 |
| HPV31 | L2 | 11 | 213 | GVRRPARLGLY | 27467 |
| HPV31 | L2 | 9 | 175 | HLLLSSSSI | 27468 |
| HPV31 | L2 | 8 | 125 | HPPTTSGF | 27469 |
| HPV31 | L2 | 10 | 125 | HPPTTSGFDI | 27470 |
| HPV31 | L2 | 11 | 125 | HPPTTSGFDIA | 27471 |
| HPV31 | L2 | 8 | 279 | IIALHRPA | 27472 |
| HPV31 | L2 | 9 | 279 | IIALHRPAL | 27473 |
| HPV31 | L2 | 9 | 45 | ILRYGSMGV | 27474 |
| HPV31 | L2 | 10 | 45 | ILRYGSMGVF | 27475 |
| HPV31 | L2 | 11 | 45 | ILRYGSMGVFF | 27476 |
| HPV31 | L2 | 8 | 211 | IPGVRRPA | 27477 |
| HPV31 | L2 | 10 | 211 | IPGVRRPARL | 27478 |
| HPV31 | L2 | 10 | 123 | IPHPPTTSGF | 27479 |
| HPV31 | L2 | 9 | 401 | IPIFSGPDV | 27480 |
| HPV31 | L2 | 11 | 401 | IPIFSGPDVPI | 27481 |
| HPV31 | L2 | 9 | 87 | IPIRPPVSI | 27482 |
| HPV31 | L2 | 9 | 33 | IPKIEHTTI | 27483 |
| HPV31 | L2 | 10 | 33 | IPKIEHTTIA | 27484 |
| HPV31 | L2 | 8 | 191 | IPMDTFIV | 27485 |
| HPV31 | L2 | 8 | 114 | IVDVGAPA | 27486 |
| HPV31 | L2 | 10 | 114 | IVDVGAPAPI | 27487 |
| HPV31 | L2 | 10 | 105 | IVSLVEESGI | 27488 |
| HPV31 | L2 | 11 | 105 | IVSLVEESGIV | 27489 |
| HPV31 | L2 | 9 | 197 | IVSTNNENI | 27490 |
| HPV31 | L2 | 8 | 35 | KIEHTTIA | 27491 |
| HPV31 | L2 | 11 | 35 | KIEHTTIADQI | 27492 |
| HPV31 | L2 | 10 | 242 | KQLITYENPA | 27493 |
| HPV31 | L2 | 11 | 242 | KQLITYENPAY | 27494 |
| HPV31 | L2 | 10 | 302 | KQTLRTRSGA | 27495 |
| HPV31 | L2 | 8 | 231 | KVIDPTFL | 27496 |
| HPV31 | L2 | 10 | 231 | KVIDPTFLSA | 27497 |
| HPV31 | L2 | 8 | 244 | LITYENPA | 27498 |
| HPV31 | L2 | 9 | 244 | LITYENPAY | 27499 |
| HPV31 | L2 | 8 | 176 | LLLSSSSI | 27500 |
| HPV31 | L2 | 8 | 108 | LVEESGIV | 27501 |
| HPV31 | L2 | 10 | 108 | LVEESGIVDV | 27502 |
| HPV31 | L2 | 9 | 447 | MLKRRRKRV | 27503 |
| HPV31 | L2 | 11 | 447 | MLKRRRKRVSY | 27504 |
| HPV31 | L2 | 8 | 335 | MQPLGASA | 27505 |
| HPV31 | L2 | 8 | 269 | NIAPDPDF | 27506 |
| HPV31 | L2 | 9 | 269 | NIAPDPDFL | 27507 |
| HPV31 | L2 | 11 | 269 | NIAPDPDFLDI | 27508 |
| HPV31 | L2 | 8 | 204 | NITSSTPI | 27509 |
| HPV31 | L2 | 11 | 204 | NITSSTPIPGV | 27510 |
| HPV31 | L2 | 9 | 327 | NPAGESIEM | 27511 |
| HPV31 | L2 | 9 | 249 | NPAYETVNA | 27512 |
| HPV31 | L2 | 9 | 155 | NPTFTDPSV | 27513 |
| HPV31 | L2 | 10 | 155 | NPTFTDPSVL | 27514 |
| HPV31 | L2 | 8 | 370 | NVSPSTAV | 27515 |
| HPV31 | L2 | 9 | 410 | PIEHAPTQV | 27516 |
| HPV31 | L2 | 10 | 410 | PIEHAPTQVF | 27517 |
| HPV31 | L2 | 8 | 402 | PIFSGPDV | 27518 |
| HPV31 | L2 | 10 | 402 | PIFSGPDVPI | 27519 |
| HPV31 | L2 | 9 | 210 | PIPGVRRPA | 27520 |
| HPV31 | L2 | 11 | 210 | PIPGVRRPARL | 27521 |
| HPV31 | L2 | 11 | 122 | PIPHPPTTSGF | 27522 |
| HPV31 | L2 | 8 | 88 | PIRPPVSI | 27523 |
| HPV31 | L2 | 11 | 88 | PIRPPVSIDPV | 27524 |
| HPV31 | L2 | 9 | 422 | PLAPTTPQV | 27525 |
| HPV31 | L2 | 11 | 422 | PLAPTTPQVSI | 27526 |
| HPV31 | L2 | 9 | 100 | PLDPSIVSL | 27527 |
| HPV31 | L2 | 10 | 100 | PLDPSIVSLV | 27528 |
| HPV31 | L2 | 8 | 394 | PLSTGFDI | 27529 |
| HPV31 | L2 | 10 | 394 | PLSTGFDIPI | 27530 |
| HPV31 | L2 | 11 | 394 | PLSTGFDIPIF | 27531 |
| HPV31 | L2 | 9 | 74 | PLSTRPSTV | 27532 |
| HPV31 | L2 | 11 | 166 | PPTPAETSGHL | 27533 |
| HPV31 | L2 | 9 | 126 | PPTTSGFDI | 27534 |

TABLE XIV-continued

B62 Supermotif Peptides

| Type | Protein | No. of Amino Acid | Position | Sequence | Seq. Id. No. |
|---|---|---|---|---|---|
| HPV31 | L2 | 10 | 126 | PPTTSGFDIA | 27535 |
| HPV31 | L2 | 8 | 91 | PPVSIDPV | 27536 |
| HPV31 | L2 | 11 | 91 | PPVSIDPVGPL | 27537 |
| HPV31 | L2 | 9 | 97 | PVGPLDPSI | 27538 |
| HPV31 | L2 | 10 | 97 | PVGPLDPSIV | 27539 |
| HPV31 | L2 | 10 | 92 | PVSIDPVGPL | 27540 |
| HPV31 | L2 | 8 | 44 | QILRYGSM | 27541 |
| HPV31 | L2 | 10 | 44 | QILRYGSMGV | 27542 |
| HPV31 | L2 | 11 | 44 | QILRYGSMGVF | 27543 |
| HPV31 | L2 | 9 | 243 | QLITYENPA | 27544 |
| HPV31 | L2 | 10 | 243 | QLITYENPAY | 27545 |
| HPV31 | L2 | 8 | 17 | QLYQTCKA | 27546 |
| HPV31 | L2 | 9 | 17 | QLYQTCKAA | 27547 |
| HPV31 | L2 | 10 | 228 | QQVKVIDPTF | 27548 |
| HPV31 | L2 | 11 | 228 | QQVKVIDPTFL | 27549 |
| HPV31 | L2 | 8 | 417 | QVFPFPLA | 27550 |
| HPV31 | L2 | 9 | 229 | QVKVIDPTF | 27551 |
| HPV31 | L2 | 10 | 229 | QVKVIDPTFL | 27552 |
| HPV31 | L2 | 11 | 429 | QVSIFVDGGDF | 27553 |
| HPV31 | L2 | 8 | 219 | RLGLYSKA | 27554 |
| HPV31 | L2 | 8 | 298 | RLGNKQTL | 27555 |
| HPV31 | L2 | 11 | 284 | RPALTSRRNTV | 27556 |
| HPV31 | L2 | 8 | 216 | RPARLGLY | 27557 |
| HPV31 | L2 | 11 | 216 | RPARLGLYSKA | 27558 |
| HPV31 | L2 | 9 | 90 | RPPVSIDPV | 27559 |
| HPV31 | L2 | 8 | 78 | RPSTVSEA | 27560 |
| HPV31 | L2 | 10 | 78 | RPSTVSEASI | 27561 |
| HPV31 | L2 | 8 | 316 | RVHYYYDI | 27562 |
| HPV31 | L2 | 11 | 316 | RVHYYYDISSI | 27563 |
| HPV31 | L2 | 9 | 454 | RVSYFFTDV | 27564 |
| HPV31 | L2 | 11 | 454 | RVSYFFTDVSV | 27565 |
| HPV31 | L2 | 8 | 94 | SIDPVGPL | 27566 |
| HPV31 | L2 | 9 | 332 | SIEMQPLGA | 27567 |
| HPV31 | L2 | 11 | 332 | SIEMQPLGASA | 27568 |
| HPV31 | L2 | 9 | 431 | SIFVDGGDF | 27569 |
| HPV31 | L2 | 10 | 431 | SIFVDGGDFY | 27570 |
| HPV31 | L2 | 11 | 431 | SIFVDGGDFYL | 27571 |
| HPV31 | L2 | 9 | 325 | SINPAGESI | 27572 |
| HPV31 | L2 | 11 | 325 | SINPAGESIEM | 27573 |
| HPV31 | L2 | 8 | 86 | SIPIRPPV | 27574 |
| HPV31 | L2 | 10 | 86 | SIPIRPPVSI | 27575 |
| HPV31 | L2 | 10 | 182 | SISTHNYEEI | 27576 |
| HPV31 | L2 | 11 | 104 | SIVSLVEESGI | 27577 |
| HPV31 | L2 | 8 | 107 | SLVEESGI | 27578 |
| HPV31 | L2 | 9 | 107 | SLVEESGIV | 27579 |
| HPV31 | L2 | 11 | 107 | SLVEESGIVDV | 27580 |
| HPV31 | L2 | 11 | 260 | SLYFSNTSHNI | 27581 |
| HPV31 | L2 | 9 | 50 | SMGVFFGGL | 27582 |
| HPV31 | L2 | 11 | 50 | SMGVFFGGLGI | 27583 |
| HPV31 | L2 | 11 | 372 | SPSTAVQSTSA | 27584 |
| HPV31 | L2 | 9 | 162 | SVLQPPTPA | 27585 |
| HPV31 | L2 | 10 | 149 | SVSTHENPTF | 27586 |
| HPV31 | L2 | 9 | 40 | TIADQILRY | 27587 |
| HPV31 | L2 | 8 | 312 | TIGARVHY | 27588 |
| HPV31 | L2 | 9 | 312 | TIGARVHYY | 27589 |
| HPV31 | L2 | 10 | 312 | TIGARVHYYY | 27590 |
| HPV31 | L2 | 9 | 347 | TLNDGLYDI | 27591 |
| HPV31 | L2 | 10 | 347 | TLNDGLYDIY | 27592 |
| HPV31 | L2 | 11 | 347 | TLNDGLYDIYA | 27593 |
| HPV31 | L2 | 8 | 304 | TLRTRSGA | 27594 |
| HPV31 | L2 | 10 | 304 | TLRTRSGATI | 27595 |
| HPV31 | L2 | 9 | 168 | TPAETSGHL | 27596 |
| HPV31 | L2 | 10 | 168 | TPAETSGHLL | 27597 |
| HPV31 | L2 | 11 | 168 | TPAETSGHLLL | 27598 |
| HPV31 | L2 | 10 | 141 | TPAILDVTSV | 27599 |
| HPV31 | L2 | 10 | 209 | TPIPGVRRPA | 27600 |
| HPV31 | L2 | 8 | 427 | TPQVSIFV | 27601 |
| HPV31 | L2 | 9 | 16 | TQLYQTCKA | 27602 |
| HPV31 | L2 | 10 | 16 | TQLYQTCKAA | 27603 |
| HPV31 | L2 | 11 | 227 | TQQVKVIDPTF | 27604 |
| HPV31 | L2 | 8 | 416 | TQVFPFPL | 27605 |
| HPV31 | L2 | 9 | 416 | TQVFPFPLA | 27606 |
| HPV31 | L2 | 10 | 362 | TVDTPATHNV | 27607 |
| HPV31 | L2 | 8 | 254 | TVNAEESL | 27608 |
| HPV31 | L2 | 9 | 254 | TVNAEESLY | 27609 |

TABLE XIV-continued

B62 Supermotif Peptides

| Type | Protein | No. of Amino Acid | Position | Sequence | Seq. Id. No. |
|---|---|---|---|---|---|
| HPV31 | L2 | 10 | 254 | TVNAEESLYF | 27610 |
| HPV31 | L2 | 8 | 392 | TVPLSTGF | 27611 |
| HPV31 | L2 | 10 | 392 | TVPLSTGFDI | 27612 |
| HPV31 | L2 | 9 | 81 | TVSEASIPI | 27613 |
| HPV31 | L2 | 9 | 232 | VIDPTFLSA | 27614 |
| HPV31 | L2 | 10 | 32 | VIPKIEHTTI | 27615 |
| HPV31 | L2 | 11 | 32 | VIPKIEHTTIA | 27616 |
| HPV31 | L2 | 8 | 163 | VLQPPTPA | 27617 |
| HPV31 | L2 | 10 | 409 | VPIEHAPTQV | 27618 |
| HPV31 | L2 | 11 | 409 | VPIEHAPTQVF | 27619 |
| HPV31 | L2 | 9 | 393 | VPLSTGFDI | 27620 |
| HPV31 | L2 | 11 | 393 | VPLSTGFDIPI | 27621 |
| HPV31 | L2 | 10 | 73 | VPLSTRPSTV | 27622 |
| HPV31 | L2 | 9 | 387 | VPTNTTVPL | 27623 |
| HPV31 | L2 | 9 | 377 | VQSTSAVSA | 27624 |
| HPV31 | L2 | 10 | 377 | VQSTSAVSAY | 27625 |
| HPV31 | L2 | 11 | 377 | VQSTSAVSAYV | 27626 |
| HPV31 | L2 | 8 | 440 | YLHPSYYM | 27627 |
| HPV31 | L2 | 9 | 440 | YLHPSYYML | 27628 |
| HPV31 | L2 | 10 | 446 | YMLKRRRKRV | 27629 |
| HPV31 | L2 | 11 | 72 | YVPLSTRPSTV | 27630 |
| HPV31 | L2 | 8 | 386 | YVPTNTTV | 27631 |
| HPV31 | L2 | 10 | 386 | YVPTNTTVPL | 27632 |
| HPV33 | E1 | 10 | 596 | AINDENWKSF | 27633 |
| HPV33 | E1 | 11 | 596 | AINDENWKSFF | 27634 |
| HPV33 | E1 | 9 | 532 | ALDGNEISI | 27635 |
| HPV33 | E1 | 11 | 532 | ALDGNEISIDV | 27636 |
| HPV33 | E1 | 8 | 84 | ALKRKFAA | 27637 |
| HPV33 | E1 | 10 | 546 | ALVQLKCPPL | 27638 |
| HPV33 | E1 | 11 | 546 | ALVQLKCPPLL | 27639 |
| HPV33 | E1 | 8 | 311 | ALYWFRTA | 27640 |
| HPV33 | E1 | 9 | 311 | ALYWFRTAM | 27641 |
| HPV33 | E1 | 8 | 318 | AMSNISDV | 27642 |
| HPV33 | E1 | 10 | 373 | AQLADSNSNA | 27643 |
| HPV33 | E1 | 11 | 373 | AQLADSNSNAA | 27644 |
| HPV33 | E1 | 9 | 81 | AVCALKRKF | 27645 |
| HPV33 | E1 | 10 | 81 | AVCALKRKFA | 27646 |
| HPV33 | E1 | 11 | 81 | AVCALKRKFAA | 27647 |
| HPV33 | E1 | 11 | 22 | AVIERRTGDNI | 27648 |
| HPV33 | E1 | 11 | 230 | CITGYGISPSV | 27649 |
| HPV33 | E1 | 8 | 259 | CLTCDRGI | 27650 |
| HPV33 | E1 | 9 | 259 | CLTCDRGII | 27651 |
| HPV33 | E1 | 10 | 259 | CLTCDRGIII | 27652 |
| HPV33 | E1 | 11 | 259 | CLTCDRGIIIL | 27653 |
| HPV33 | E1 | 8 | 465 | CMLICGPA | 27654 |
| HPV33 | E1 | 9 | 297 | CMVIEPPKL | 27655 |
| HPV33 | E1 | 8 | 494 | CVNSKSHF | 27656 |
| HPV33 | E1 | 9 | 494 | CVNSKSHFW | 27657 |
| HPV33 | E1 | 10 | 494 | CVNSKSHFWL | 27658 |
| HPV33 | E1 | 9 | 367 | DIAYYYAQL | 27659 |
| HPV33 | E1 | 10 | 367 | DIAYYYAQLA | 27660 |
| HPV33 | E1 | 10 | 46 | DLLEFIDDSM | 27661 |
| HPV33 | E1 | 8 | 78 | DLNAVCAL | 27662 |
| HPV33 | E1 | 8 | 349 | DLSEMVQW | 27663 |
| HPV33 | E1 | 9 | 349 | DLSEMVQWA | 27664 |
| HPV33 | E1 | 10 | 349 | DLSEMVQWAY | 27665 |
| HPV33 | E1 | 8 | 3 | DPEGTNGA | 27666 |
| HPV33 | E1 | 10 | 3 | DPEGTNGAGM | 27667 |
| HPV33 | E1 | 8 | 541 | DVKHRALV | 27668 |
| HPV33 | E1 | 10 | 541 | DVKHRALVQL | 27669 |
| HPV33 | E1 | 9 | 324 | DVQGTTPEW | 27670 |
| HPV33 | E1 | 10 | 324 | DVQGTTPEWI | 27671 |
| HPV33 | E1 | 9 | 516 | DVTPISWTY | 27672 |
| HPV33 | E1 | 10 | 516 | DVTPISWTYI | 27673 |
| HPV33 | E1 | 10 | 537 | EISIDVKHRA | 27674 |
| HPV33 | E1 | 11 | 537 | EISIDVKHRAL | 27675 |
| HPV33 | E1 | 8 | 361 | ELTDDSDI | 27676 |
| HPV33 | E1 | 9 | 361 | ELTDDSDIA | 27677 |
| HPV33 | E1 | 10 | 361 | ELTDDSDIAY | 27678 |
| HPV33 | E1 | 11 | 361 | ELTDDSDIAYY | 27679 |
| HPV33 | E1 | 11 | 352 | EMVQWAYDNEL | 27680 |
| HPV33 | E1 | 11 | 301 | EPPKLRSQTCA | 27681 |
| HPV33 | E1 | 8 | 137 | EVETQQMV | 27682 |
| HPV33 | E1 | 11 | 137 | EVETQQMVQQV | 27683 |
| HPV33 | E1 | 8 | 169 | EVSCETNV | 27684 |

TABLE XIV-continued

B62 Supermotif Peptides

| Type | Protein | No. of Amino Acid | Position | Sequence | Seq. Id. No. |
|---|---|---|---|---|---|
| HPV33 | E1 | 10 | 50 | FIDDSMENSI | 27685 |
| HPV33 | E1 | 8 | 449 | FLGAFKKF | 27686 |
| HPV33 | E1 | 9 | 449 | FLGAFKKFL | 27687 |
| HPV33 | E1 | 10 | 486 | FLKGCVISCV | 27688 |
| HPV33 | E1 | 11 | 456 | FLKGIPKKSCM | 27689 |
| HPV33 | E1 | 8 | 385 | FLKSNSQA | 27690 |
| HPV33 | E1 | 10 | 385 | FLKSNSQAKI | 27691 |
| HPV33 | E1 | 11 | 385 | FLKSNSQAKIV | 27692 |
| HPV33 | E1 | 8 | 212 | FMELVRPF | 27693 |
| HPV33 | E1 | 10 | 585 | FPFDENGNPV | 27694 |
| HPV33 | E1 | 11 | 585 | FPFDENGNPVY | 27695 |
| HPV33 | E1 | 8 | 265 | GIIILLLI | 27696 |
| HPV33 | E1 | 10 | 265 | GIIILLLIRF | 27697 |
| HPV33 | E1 | 10 | 399 | GIMCRHYKKA | 27698 |
| HPV33 | E1 | 8 | 459 | GIPKKSCM | 27699 |
| HPV33 | E1 | 9 | 459 | GIPKKSCML | 27700 |
| HPV33 | E1 | 10 | 459 | GIPKKSCMLI | 27701 |
| HPV33 | E1 | 8 | 209 | GISFMELV | 27702 |
| HPV33 | E1 | 11 | 209 | GISFMELVRPF | 27703 |
| HPV33 | E1 | 10 | 235 | GISPSVAESL | 27704 |
| HPV33 | E1 | 8 | 11 | GMGCTGWF | 27705 |
| HPV33 | E1 | 10 | 11 | GMGCTGWFEV | 27706 |
| HPV33 | E1 | 9 | 512 | GMIDDVTPI | 27707 |
| HPV33 | E1 | 11 | 512 | GMIDDVTPISW | 27708 |
| HPV33 | E1 | 8 | 480 | GMSLIQFL | 27709 |
| HPV33 | E1 | 9 | 470 | GPANTGKSY | 27710 |
| HPV33 | E1 | 10 | 470 | GPANTGKSYF | 27711 |
| HPV33 | E1 | 8 | 163 | GVGDDSEV | 27712 |
| HPV33 | E1 | 11 | 256 | HLQCLTCDRGI | 27713 |
| HPV33 | E1 | 9 | 266 | IIILLLIRF | 27714 |
| HPV33 | E1 | 8 | 267 | IILLLIRF | 27715 |
| HPV33 | E1 | 8 | 200 | ILYKFKEA | 27716 |
| HPV33 | E1 | 9 | 200 | ILYKFKEAY | 27717 |
| HPV33 | E1 | 11 | 200 | ILYKFKEAYGI | 27718 |
| HPV33 | E1 | 9 | 400 | IMCRHYKKA | 27719 |
| HPV33 | E1 | 8 | 293 | IPETCMVI | 27720 |
| HPV33 | E1 | 8 | 460 | IPKKSCML | 27721 |
| HPV33 | E1 | 9 | 460 | IPKKSCMLI | 27722 |
| HPV33 | E1 | 8 | 59 | IQADTEAA | 27723 |
| HPV33 | E1 | 10 | 59 | IQADTEAARA | 27724 |
| HPV33 | E1 | 11 | 59 | IQADTEAARAL | 27725 |
| HPV33 | E1 | 8 | 72 | IQEDEDDL | 27726 |
| HPV33 | E1 | 10 | 72 | IQEGEDDLNA | 27727 |
| HPV33 | E1 | 11 | 72 | IQEGEDDLNAV | 27728 |
| HPV33 | E1 | 8 | 484 | IQFLKGCV | 27729 |
| HPV33 | E1 | 9 | 484 | IQFLKGCVI | 27730 |
| HPV33 | E1 | 8 | 394 | IVKDCGIM | 27731 |
| HPV33 | E1 | 10 | 435 | IVQLLRYQNI | 27732 |
| HPV33 | E1 | 10 | 124 | KIDELEDSGY | 27733 |
| HPV33 | E1 | 8 | 510 | KIGMIDDV | 27734 |
| HPV33 | E1 | 11 | 510 | KIGMIDDVTPI | 27735 |
| HPV33 | E1 | 8 | 393 | KIVKDCGI | 27736 |
| HPV33 | E1 | 9 | 393 | KIVKDCGIM | 27737 |
| HPV33 | E1 | 9 | 285 | KLMSNLLSI | 27738 |
| HPV33 | E1 | 8 | 304 | KLRSQTCA | 27739 |
| HPV33 | E1 | 9 | 304 | KLRSQTCAL | 27740 |
| HPV33 | E1 | 10 | 304 | KLRSQTCALY | 27741 |
| HPV33 | E1 | 11 | 304 | KLRSQTCALYW | 27742 |
| HPV33 | E1 | 8 | 412 | KMSIGQWI | 27743 |
| HPV33 | E1 | 9 | 249 | KQHSLYTHL | 27744 |
| HPV33 | E1 | 9 | 245 | KVLIKQHSL | 27745 |
| HPV33 | E1 | 10 | 245 | KVLIKQHSLY | 27746 |
| HPV33 | E1 | 8 | 247 | LIKQHSLY | 27747 |
| HPV33 | E1 | 11 | 247 | LIKQHSLYTHL | 27748 |
| HPV33 | E1 | 9 | 483 | LIQFLKGCV | 27749 |
| HPV33 | E1 | 10 | 483 | LIQFLKGCVI | 27750 |
| HPV33 | E1 | 11 | 271 | LIRFRCSKNRL | 27751 |
| HPV33 | E1 | 9 | 47 | LLEFIDDSM | 27752 |
| HPV33 | E1 | 9 | 555 | LLLTSNTNA | 27753 |
| HPV33 | E1 | 9 | 438 | LLRYQNIEF | 27754 |
| HPV33 | E1 | 11 | 438 | LLRYQNIEFTA | 27755 |
| HPV33 | E1 | 9 | 290 | LLSIPETCM | 27756 |
| HPV33 | E1 | 10 | 290 | LLSIPETCMV | 27757 |
| HPV33 | E1 | 11 | 290 | LLSIPETCMVI | 27758 |
| HPV33 | E1 | 8 | 556 | LLTSNTNA | 27759 |

TABLE XIV-continued

B62 Supermotif Peptides

| Type | Protein | No. of Amino Acid | Position | Sequence | Seq. Id. No. |
|---|---|---|---|---|---|
| HPV33 | E1 | 8 | 286 | LMSNLLSI | 27760 |
| HPV33 | E1 | 10 | 257 | LQCLTCDRGI | 27761 |
| HPV33 | E1 | 11 | 257 | LQCLTCDRGII | 27762 |
| HPV33 | E1 | 8 | 184 | LQEISNVL | 27763 |
| HPV33 | E1 | 9 | 339 | LQHSFNDNI | 27764 |
| HPV33 | E1 | 10 | 339 | LQHSFNDNIF | 27765 |
| HPV33 | E1 | 9 | 503 | LQPLSDAKI | 27766 |
| HPV33 | E1 | 11 | 503 | LQPLSDAKIGM | 27767 |
| HPV33 | E1 | 9 | 547 | LVQLKCPPL | 27768 |
| HPV33 | E1 | 10 | 547 | LVQLKCPPLL | 27769 |
| HPV33 | E1 | 11 | 547 | LVQLKCPPLLL | 27770 |
| HPV33 | E1 | 8 | 513 | MIDDVTPI | 27771 |
| HPV33 | E1 | 10 | 513 | MIDDVTPISW | 27772 |
| HPV33 | E1 | 8 | 298 | MVIEPPKL | 27773 |
| HPV33 | E1 | 10 | 353 | MVQWAYDNEL | 27774 |
| HPV33 | E1 | 8 | 443 | NIEFTAFL | 27775 |
| HPV33 | E1 | 10 | 443 | NIEFTAFLGA | 27776 |
| HPV33 | E1 | 11 | 443 | NIEFTAFLGAF | 27777 |
| HPV33 | E1 | 8 | 346 | NIFDLSEM | 27778 |
| HPV33 | E1 | 9 | 346 | NIFDLSEMV | 27779 |
| HPV33 | E1 | 11 | 346 | NIFDLSEMVQW | 27780 |
| HPV33 | E1 | 9 | 199 | NILYKFKEA | 27781 |
| HPV33 | E1 | 10 | 199 | NILYKFKEAY | 27782 |
| HPV33 | E1 | 9 | 71 | NIQEGEDDL | 27783 |
| HPV33 | E1 | 11 | 71 | NIQEGEDDLNA | 27784 |
| HPV33 | E1 | 10 | 31 | NISEDEDETA | 27785 |
| HPV33 | E1 | 9 | 627 | NISTFKCSA | 27786 |
| HPV33 | E1 | 10 | 289 | NLLSIPETCM | 27787 |
| HPV33 | E1 | 11 | 289 | NLLSIPETCMV | 27788 |
| HPV33 | E1 | 10 | 155 | NLNDLESSGV | 27789 |
| HPV33 | E1 | 11 | 592 | NPVYAINDENW | 27790 |
| HPV33 | E1 | 8 | 175 | NVDSCENV | 27791 |
| HPV33 | E1 | 10 | 175 | NVDSCENVTL | 27792 |
| HPV33 | E1 | 10 | 189 | NVLHSSNTKA | 27793 |
| HPV33 | E1 | 10 | 181 | NVTLQEISNV | 27794 |
| HPV33 | E1 | 11 | 181 | NVTLQEISNVL | 27795 |
| HPV33 | E1 | 10 | 519 | PISWTYIDDY | 27796 |
| HPV33 | E1 | 11 | 519 | PISWTYIDDYM | 27797 |
| HPV33 | E1 | 8 | 434 | PIVQLLRY | 27798 |
| HPV33 | E1 | 11 | 434 | PIVQLLRYQNI | 27799 |
| HPV33 | E1 | 10 | 554 | PLLLTSNTNA | 27800 |
| HPV33 | E1 | 9 | 505 | PLSDAKIGM | 27801 |
| HPV33 | E1 | 10 | 505 | PLSDAKIGMI | 27802 |
| HPV33 | E1 | 10 | 302 | PPKLRSQTCA | 27803 |
| HPV33 | E1 | 11 | 302 | PPKLRSQTCAL | 27804 |
| HPV33 | E1 | 11 | 553 | PPLLLTSNTNA | 27805 |
| HPV33 | E1 | 10 | 593 | PVYAINDENW | 27806 |
| HPV33 | E1 | 9 | 374 | QLADSNSNA | 27807 |
| HPV33 | E1 | 10 | 374 | QLADSNSNAA | 27808 |
| HPV33 | E1 | 11 | 374 | QLADSNSNAAA | 27809 |
| HPV33 | E1 | 8 | 549 | QLKCPPLL | 27810 |
| HPV33 | E1 | 9 | 549 | QLKCPPLLL | 27811 |
| HPV33 | E1 | 8 | 437 | QLLRYQNI | 27812 |
| HPV33 | E1 | 10 | 437 | QLLRYQNIEF | 27813 |
| HPV33 | E1 | 8 | 504 | QPLSDAKI | 27814 |
| HPV33 | E1 | 10 | 504 | QPLSDAKIGM | 27815 |
| HPV33 | E1 | 11 | 504 | QPLSDAKIGMI | 27816 |
| HPV33 | E1 | 11 | 146 | QVESQNGDTNL | 27817 |
| HPV33 | E1 | 8 | 280 | RLTVAKLM | 27818 |
| HPV33 | E1 | 11 | 280 | RLTVAKLMSNL | 27819 |
| HPV33 | E1 | 11 | 575 | RLTVFEFKNPF | 27820 |
| HPV33 | E1 | 9 | 335 | RLTVLQHSF | 27821 |
| HPV33 | E1 | 9 | 433 | RPIVQLLRY | 27822 |
| HPV33 | E1 | 8 | 539 | SIDVKHRA | 27823 |
| HPV33 | E1 | 9 | 539 | SIDVKHRAL | 27824 |
| HPV33 | E1 | 10 | 539 | SIDVKHRALV | 27825 |
| HPV33 | E1 | 10 | 111 | SINKNKECTY | 27826 |
| HPV33 | E1 | 8 | 292 | SIPETCMV | 27827 |
| HPV33 | E1 | 9 | 292 | SIPETCMVI | 27828 |
| HPV33 | E1 | 8 | 58 | SIQADTEA | 27829 |
| HPV33 | E1 | 9 | 58 | SIQADTEAA | 27830 |
| HPV33 | E1 | 11 | 58 | SIQADTEAARA | 27831 |
| HPV33 | E1 | 10 | 482 | SLIQFLKGCV | 27832 |
| HPV33 | E1 | 11 | 482 | SLIQFLKGCVI | 27833 |
| HPV33 | E1 | 11 | 243 | SLKVLIKQHSL | 27834 |

TABLE XIV-continued

B62 Supermotif Peptides

| Type | Protein | No. of Amino Acid | Position | Sequence | Seq. Id. No. |
|---|---|---|---|---|---|
| HPV33 | E1 | 9 | 252 | SLYTHLQCL | 27835 |
| HPV33 | E1 | 8 | 54 | SMENSIQA | 27836 |
| HPV33 | E1 | 8 | 237 | SPSVAESL | 27837 |
| HPV33 | E1 | 10 | 237 | SPSVAESLKV | 27838 |
| HPV33 | E1 | 11 | 237 | SPSVAESLKVL | 27839 |
| HPV33 | E1 | 11 | 390 | SQAKIVKDCGI | 27840 |
| HPV33 | E1 | 8 | 149 | SQNGDTNL | 27841 |
| HPV33 | E1 | 11 | 149 | SQNGDTNLNDL | 27842 |
| HPV33 | E1 | 8 | 93 | SQSAAEDV | 27843 |
| HPV33 | E1 | 9 | 93 | SQSAAEDVV | 27844 |
| HPV33 | E1 | 8 | 307 | SQTCALYW | 27845 |
| HPV33 | E1 | 9 | 307 | SQTCALYWF | 27846 |
| HPV33 | E1 | 8 | 239 | SVAESLKV | 27847 |
| HPV33 | E1 | 9 | 239 | SVAESLKVL | 27848 |
| HPV33 | E1 | 10 | 239 | SVAESLKVLI | 27849 |
| HPV33 | E1 | 8 | 183 | TLQEISNV | 27850 |
| HPV33 | E1 | 9 | 183 | TLQEISNVL | 27851 |
| HPV33 | E1 | 8 | 329 | TPEWIDRL | 27852 |
| HPV33 | E1 | 10 | 329 | TPEWIDRLTV | 27853 |
| HPV33 | E1 | 11 | 329 | TPEWIDRLTVL | 27854 |
| HPV33 | E1 | 8 | 518 | TPISWTYI | 27855 |
| HPV33 | E1 | 11 | 518 | TPISWTYIDDY | 27856 |
| HPV33 | E1 | 8 | 140 | TQQMVQQV | 27857 |
| HPV33 | E1 | 9 | 282 | TVAKLMSNL | 27858 |
| HPV33 | E1 | 10 | 282 | TVAKLMSNLL | 27859 |
| HPV33 | E1 | 9 | 577 | TVFEFKNPF | 27860 |
| HPV33 | E1 | 11 | 577 | TVFEFKNPFPF | 27861 |
| HPV33 | E1 | 11 | 337 | TVLQHSFNDNI | 27862 |
| HPV33 | E1 | 10 | 23 | VIERRTGDNI | 27863 |
| HPV33 | E1 | 11 | 491 | VISCVNSKSHF | 27864 |
| HPV33 | E1 | 9 | 190 | VLHSSNTKA | 27865 |
| HPV33 | E1 | 11 | 190 | VLHSSNTKANI | 27866 |
| HPV33 | E1 | 8 | 246 | VLIKQHSL | 27867 |
| HPV33 | E1 | 9 | 246 | VLIKQHSLY | 27868 |
| HPV33 | E1 | 10 | 338 | VLQHSFNDNI | 27869 |
| HPV33 | E1 | 11 | 338 | VLQHSFNDNIF | 27870 |
| HPV33 | E1 | 8 | 325 | VQGTTPEW | 27871 |
| HPV33 | E1 | 9 | 325 | VQGTTPEWI | 27872 |
| HPV33 | E1 | 8 | 548 | VQLKCPPL | 27873 |
| HPV33 | E1 | 9 | 548 | VQLKCPPLL | 27874 |
| HPV33 | E1 | 10 | 548 | VQLKCPPLLL | 27875 |
| HPV33 | E1 | 9 | 436 | VQLLRYQNI | 27876 |
| HPV33 | E1 | 11 | 436 | VQLLRYQNIEF | 27877 |
| HPV33 | E1 | 9 | 354 | VQWAYDNEL | 27878 |
| HPV33 | E1 | 8 | 332 | WIDRLTVL | 27879 |
| HPV33 | E1 | 8 | 502 | WLQPLSDA | 27880 |
| HPV33 | E1 | 10 | 502 | WLQPLSDAKI | 27881 |
| HPV33 | E1 | 8 | 569 | WPYLHSRL | 27882 |
| HPV33 | E1 | 10 | 569 | WPYLHSRLTV | 27883 |
| HPV33 | E1 | 11 | 569 | WPYLHSRLTVF | 27884 |
| HPV33 | E1 | 9 | 524 | YIDDYMRNA | 27885 |
| HPV33 | E1 | 10 | 524 | YIDDYMRNAL | 27886 |
| HPV33 | E1 | 8 | 571 | YLHSRLTV | 27887 |
| HPV33 | E1 | 9 | 571 | YLHSRLTVF | 27888 |
| HPV33 | E1 | 11 | 571 | YLHSRLTVFEF | 27889 |
| HPV33 | E1 | 11 | 528 | YMRNALDGNEI | 27890 |
| HPV33 | E1 | 8 | 441 | YQNIEFTA | 27891 |
| HPV33 | E1 | 9 | 441 | YQNIEFTAF | 27892 |
| HPV33 | E1 | 10 | 441 | YQNIEFTAFL | 27893 |
| HPV33 | E2 | 10 | 249 | ALDNRTARTA | 27894 |
| HPV33 | E2 | 10 | 78 | ALETLSKSQY | 27895 |
| HPV33 | E2 | 9 | 41 | ALLYTAKQM | 27896 |
| HPV33 | E2 | 11 | 41 | ALLYTAKQMGF | 27897 |
| HPV33 | E2 | 8 | 237 | AQPLTKLF | 27898 |
| HPV33 | E2 | 10 | 237 | AQPLTKLFCA | 27899 |
| HPV33 | E2 | 9 | 10 | AVQEKILDL | 27900 |
| HPV33 | E2 | 10 | 10 | AVQEKILDLY | 27901 |
| HPV33 | E2 | 9 | 288 | CLRYRLKPY | 27902 |
| HPV33 | E2 | 10 | 195 | CPTSISSNQI | 27903 |
| HPV33 | E2 | 9 | 25 | DLPSQIEHW | 27904 |
| HPV33 | E2 | 11 | 25 | DLPSQIEHWKL | 27905 |
| HPV33 | E2 | 10 | 17 | DLYEADKTDL | 27906 |
| HPV33 | E2 | 9 | 247 | DPALDNRTA | 27907 |
| HPV33 | E2 | 8 | 3 | EISARLNA | 27908 |
| HPV33 | E2 | 9 | 3 | EISARLNAV | 27909 |

TABLE XIV-continued

B62 Supermotif Peptides

| Type | Protein | No. of Amino Acid | Position | Sequence | Seq. Id. No. |
|---|---|---|---|---|---|
| HPV33 | E2 | 9 | 74 | ELQMALETL | 27910 |
| HPV33 | E2 | 10 | 298 | ELYSSMSSTW | 27911 |
| HPV33 | E2 | 8 | 328 | EQQQQMFL | 27912 |
| HPV33 | E2 | 11 | 328 | EQQQQMFLGTV | 27913 |
| HPV33 | E2 | 8 | 185 | EVHVGGQV | 27914 |
| HPV33 | E2 | 9 | 185 | EVHVGGQVI | 27915 |
| HPV33 | E2 | 10 | 185 | EVHVGGQVIV | 27916 |
| HPV33 | E2 | 11 | 100 | EVWLCEPPKCF | 27917 |
| HPV33 | E2 | 11 | 334 | FLGTVKIPPTV | 27918 |
| HPV33 | E2 | 8 | 70 | FQVIELQM | 27919 |
| HPV33 | E2 | 9 | 70 | FQVIELQMA | 27920 |
| HPV33 | E2 | 10 | 70 | FQVIELQMAL | 27921 |
| HPV33 | E2 | 9 | 325 | FVTEQQQM | 27922 |
| HPV33 | E2 | 10 | 325 | FVTEQQQQMF | 27923 |
| HPV33 | E2 | 11 | 325 | FVTEQQQQMFL | 27924 |
| HPV33 | E2 | 8 | 319 | GIVTVTFV | 27925 |
| HPV33 | E2 | 11 | 156 | GMYYIHNCEKV | 27926 |
| HPV33 | E2 | 10 | 190 | GQVIVCPTSI | 27927 |
| HPV33 | E2 | 10 | 53 | HLCHQVVPSL | 27928 |
| HPV33 | E2 | 11 | 53 | HLCHQVVPSLL | 27929 |
| HPV33 | E2 | 9 | 278 | HLKGESNSL | 27930 |
| HPV33 | E2 | 8 | 56 | HQVVPSLL | 27931 |
| HPV33 | E2 | 9 | 56 | HQVVPSLLA | 27932 |
| HPV33 | E2 | 8 | 187 | HVGGQVIV | 27933 |
| HPV33 | E2 | 9 | 139 | IIEEDTCTM | 27934 |
| HPV33 | E2 | 10 | 139 | IIEEDTCTMV | 27935 |
| HPV33 | E2 | 11 | 340 | IPPTVQISTGF | 27936 |
| HPV33 | E2 | 11 | 276 | IVHLKGESNSL | 27937 |
| HPV33 | E2 | 8 | 14 | KILDLYEA | 27938 |
| HPV33 | E2 | 8 | 339 | KIPPTVQI | 27939 |
| HPV33 | E2 | 8 | 242 | KLFCADPA | 27940 |
| HPV33 | E2 | 9 | 242 | KLFCADPAL | 27941 |
| HPV33 | E2 | 8 | 34 | KLIRMECA | 27942 |
| HPV33 | E2 | 9 | 34 | KLIRMECAL | 27943 |
| HPV33 | E2 | 10 | 34 | KLIRMECALL | 27944 |
| HPV33 | E2 | 11 | 34 | KLIRMECALLY | 27945 |
| HPV33 | E2 | 10 | 294 | KPYKELYSSM | 27946 |
| HPV33 | E2 | 8 | 112 | KQGETVTV | 27947 |
| HPV33 | E2 | 10 | 112 | KQGETVTVQY | 27948 |
| HPV33 | E2 | 8 | 47 | KQMGFSHL | 27949 |
| HPV33 | E2 | 10 | 264 | KQRTVCSSNV | 27950 |
| HPV33 | E2 | 11 | 264 | KQRTVCSSNVA | 27951 |
| HPV33 | E2 | 8 | 151 | KVDYIGMY | 27952 |
| HPV33 | E2 | 9 | 151 | KVDYIGMYY | 27953 |
| HPV33 | E2 | 10 | 151 | KVDYIGMYYI | 27954 |
| HPV33 | E2 | 11 | 165 | KVYFKYFKEDA | 27955 |
| HPV33 | E2 | 8 | 35 | LIRMECAL | 27956 |
| HPV33 | E2 | 9 | 35 | LIRMECALL | 27957 |
| HPV33 | E2 | 10 | 35 | LIRMECALLY | 27958 |
| HPV33 | E2 | 8 | 62 | LLASKTKA | 27959 |
| HPV33 | E2 | 9 | 62 | LLASKTKAF | 27960 |
| HPV33 | E2 | 11 | 62 | LLASKTKAFQV | 27961 |
| HPV33 | E2 | 8 | 42 | LLYTAKQM | 27962 |
| HPV33 | E2 | 10 | 42 | LLYTAKQMGF | 27963 |
| HPV33 | E2 | 8 | 26 | LPSQIEHW | 27964 |
| HPV33 | E2 | 10 | 26 | LPSQIEHWKL | 27965 |
| HPV33 | E2 | 11 | 26 | LPSQIEHWKLI | 27966 |
| HPV33 | E2 | 8 | 75 | LQMALETL | 27967 |
| HPV33 | E2 | 8 | 94 | LQQTSLEV | 27968 |
| HPV33 | E2 | 9 | 94 | LQQTSLEVW | 27969 |
| HPV33 | E2 | 10 | 94 | LQQTSLEVWL | 27970 |
| HPV33 | E2 | 8 | 147 | MVTGKVDY | 27971 |
| HPV33 | E2 | 9 | 147 | MVTGKVDYI | 27972 |
| HPV33 | E2 | 11 | 147 | MVTGKVDYIGM | 27973 |
| HPV33 | E2 | 9 | 202 | NQISTTETA | 27974 |
| HPV33 | E2 | 11 | 202 | NQISTTETADI | 27975 |
| HPV33 | E2 | 8 | 272 | NVAPIVHL | 27976 |
| HPV33 | E2 | 8 | 239 | PLTKLFCA | 27977 |
| HPV33 | E2 | 11 | 239 | PLTKLFCADPA | 27978 |
| HPV33 | E2 | 10 | 341 | PPTVQISTGF | 27979 |
| HPV33 | E2 | 11 | 341 | PPTVQISTGFM | 27980 |
| HPV33 | E2 | 11 | 221 | PQAAAKRRRPA | 27981 |
| HPV33 | E2 | 8 | 29 | QIEHWKLI | 27982 |
| HPV33 | E2 | 10 | 29 | QIEHWKLIRM | 27983 |
| HPV33 | E2 | 9 | 345 | QISTGFMTL | 27984 |

TABLE XIV-continued

B62 Supermotif Peptides

| Type | Protein | No. of Amino Acid | Position | Sequence | Seq. Id. No. |
|---|---|---|---|---|---|
| HPV33 | E2 | 8 | 203 | QISTTETA | 27985 |
| HPV33 | E2 | 10 | 203 | QISTTETADI | 27986 |
| HPV33 | E2 | 9 | 332 | QMFLGTVKI | 27987 |
| HPV33 | E2 | 11 | 48 | QMGFSHLCHQV | 27988 |
| HPV33 | E2 | 11 | 182 | QMWEVHVGGQV | 27989 |
| HPV33 | E2 | 9 | 238 | QPLTKLFCA | 27990 |
| HPV33 | E2 | 8 | 331 | QQMFLGTV | 27991 |
| HPV33 | E2 | 10 | 331 | QQMFLGTVKI | 27992 |
| HPV33 | E2 | 9 | 330 | QQQMFLGTV | 27993 |
| HPV33 | E2 | 11 | 330 | QQQMFLGTVKI | 27994 |
| HPV33 | E2 | 10 | 329 | QQQQMFLGTV | 27995 |
| HPV33 | E2 | 8 | 95 | QQTSLEVW | 27996 |
| HPV33 | E2 | 9 | 95 | QQTSLEVWL | 27997 |
| HPV33 | E2 | 8 | 71 | QVIELQMA | 27998 |
| HPV33 | E2 | 9 | 71 | QVIELQMAL | 27999 |
| HPV33 | E2 | 9 | 191 | QVIVCPTSI | 28000 |
| HPV33 | E2 | 8 | 57 | QVVPSLLA | 28001 |
| HPV33 | E2 | 8 | 292 | RLKPYKEL | 28002 |
| HPV33 | E2 | 9 | 292 | RLKPYKELY | 28003 |
| HPV33 | E2 | 9 | 7 | RLNAVQEKI | 28004 |
| HPV33 | E2 | 10 | 7 | RLNAVQEKIL | 28005 |
| HPV33 | E2 | 8 | 37 | RMECALLY | 28006 |
| HPV33 | E2 | 10 | 37 | RMECALLYTA | 28007 |
| HPV33 | E2 | 9 | 229 | RPADTTDTA | 28008 |
| HPV33 | E2 | 9 | 285 | SLKCLRYRL | 28009 |
| HPV33 | E2 | 9 | 61 | SLLASKTKA | 28010 |
| HPV33 | E2 | 10 | 61 | SLLASKTKAF | 28011 |
| HPV33 | E2 | 8 | 302 | SMSSTWHW | 28012 |
| HPV33 | E2 | 8 | 28 | SQIEHWKL | 28013 |
| HPV33 | E2 | 9 | 28 | SQIEHWKLI | 28014 |
| HPV33 | E2 | 11 | 28 | SQIEHWKLIRM | 28015 |
| HPV33 | E2 | 10 | 90 | SQWTLQQTSL | 28016 |
| HPV33 | E2 | 8 | 85 | SQYSTSQW | 28017 |
| HPV33 | E2 | 10 | 85 | SQYSTSQWTL | 28018 |
| HPV33 | E2 | 9 | 93 | TLQQTSLEV | 28019 |
| HPV33 | E2 | 10 | 93 | TLQQTSLEVW | 28020 |
| HPV33 | E2 | 11 | 93 | TLQQTSLEVWL | 28021 |
| HPV33 | E2 | 10 | 128 | TMDYTNWGEI | 28022 |
| HPV33 | E2 | 11 | 128 | TMDYTNWGEIY | 28023 |
| HPV33 | E2 | 9 | 146 | TMVTGKVDY | 28024 |
| HPV33 | E2 | 10 | 146 | TMVTGKVDYI | 28025 |
| HPV33 | E2 | 8 | 181 | TQMWEVHV | 28026 |
| HPV33 | E2 | 8 | 267 | TVCSSNVA | 28027 |
| HPV33 | E2 | 10 | 267 | TVCSSNVAPI | 28028 |
| HPV33 | E2 | 11 | 267 | TVCSSNVAPIV | 28029 |
| HPV33 | E2 | 8 | 337 | TVKIPPTV | 28030 |
| HPV33 | E2 | 10 | 337 | TVKIPPTVQI | 28031 |
| HPV33 | E2 | 8 | 343 | TVQISTGF | 28032 |
| HPV33 | E2 | 9 | 343 | TVQISTGFM | 28033 |
| HPV33 | E2 | 11 | 343 | TVQISTGFMTL | 28034 |
| HPV33 | E2 | 8 | 72 | VIELQMAL | 28035 |
| HPV33 | E2 | 11 | 72 | VIELQMALETL | 28036 |
| HPV33 | E2 | 8 | 192 | VIVCPTSI | 28037 |
| HPV33 | E2 | 11 | 59 | VPSLLASKTKA | 28038 |
| HPV33 | E2 | 8 | 11 | VQEKILDL | 28039 |
| HPV33 | E2 | 9 | 11 | VQEKILDLY | 28040 |
| HPV33 | E2 | 11 | 11 | VQEKILDLYEA | 28041 |
| HPV33 | E2 | 8 | 344 | VQISTGFM | 28042 |
| HPV33 | E2 | 10 | 344 | VQISTGFMTL | 28043 |
| HPV33 | E2 | 11 | 119 | VQYDNDKKNTM | 28044 |
| HPV33 | E2 | 9 | 102 | WLCEPPKCF | 28045 |
| HPV33 | E2 | 8 | 159 | YIHNCEKV | 28046 |
| HPV33 | E2 | 9 | 159 | YIHNCEKVY | 28047 |
| HPV33 | E2 | 10 | 159 | YIHNCEKVYF | 28048 |
| HPV33 | E2 | 10 | 138 | YIIEEDTCTM | 28049 |
| HPV33 | E2 | 11 | 138 | YIIEEDTCTMV | 28050 |
| HPV33 | E5 | 9 | 63 | CINFHAQHM | 28051 |
| HPV33 | E5 | 9 | 14 | CLSLLLRPL | 28052 |
| HPV33 | E5 | 10 | 14 | CLSLLLRPLI | 28053 |
| HPV33 | E5 | 11 | 14 | CLSLLLRPLIL | 28054 |
| HPV33 | E5 | 9 | 9 | FILFLCLSL | 28055 |
| HPV33 | E5 | 10 | 9 | FILFLCLSLL | 28056 |
| HPV33 | E5 | 11 | 9 | FILFLCLSLLL | 28057 |
| HPV33 | E5 | 8 | 12 | FLCLSLLL | 28058 |
| HPV33 | E5 | 11 | 12 | FLCLSLLLRPL | 28059 |

TABLE XIV-continued

B62 Supermotif Peptides

| Type | Protein | No. of Amino Acid | Position | Sequence | Seq. Id. No. |
|---|---|---|---|---|---|
| HPV33 | E5 | 9 | 56 | FLYLPMMCI | 28060 |
| HPV33 | E5 | 11 | 56 | FLYLPMMCINF | 28061 |
| HPV33 | E5 | 8 | 3 | FVFVLCFI | 28062 |
| HPV33 | E5 | 9 | 3 | FVFVLCFIL | 28063 |
| HPV33 | E5 | 10 | 3 | FVFVLCFILF | 28064 |
| HPV33 | E5 | 11 | 3 | FVFVLCFILFL | 28065 |
| HPV33 | E5 | 8 | 42 | FVGSPLKI | 28066 |
| HPV33 | E5 | 9 | 42 | FVGSPLKIF | 28067 |
| HPV33 | E5 | 10 | 42 | FVGSPLKIFF | 28068 |
| HPV33 | E5 | 8 | 5 | FVLCFILF | 28069 |
| HPV33 | E5 | 9 | 5 | FVLCFILFL | 28070 |
| HPV33 | E5 | 11 | 5 | FVLCFILFLCL | 28071 |
| HPV33 | E5 | 8 | 10 | ILFLCLSL | 28072 |
| HPV33 | E5 | 9 | 10 | ILFLCLSLL | 28073 |
| HPV33 | E5 | 10 | 10 | ILFLCLSLLL | 28074 |
| HPV33 | E5 | 8 | 23 | ILSISTYA | 28075 |
| HPV33 | E5 | 9 | 23 | ILSISTYAW | 28076 |
| HPV33 | E5 | 10 | 23 | ILSISTYAWL | 28077 |
| HPV33 | E5 | 11 | 23 | ILSISTYAWLL | 28078 |
| HPV33 | E5 | 8 | 48 | KIFFCYLL | 28079 |
| HPV33 | E5 | 9 | 48 | KIFFCYLLF | 28080 |
| HPV33 | E5 | 10 | 48 | KIFFCYLLFL | 28081 |
| HPV33 | E5 | 11 | 48 | KIFFCYLLFLY | 28082 |
| HPV33 | E5 | 8 | 22 | LILSISTY | 28083 |
| HPV33 | E5 | 9 | 22 | LILSISTYA | 28084 |
| HPV33 | E5 | 10 | 22 | LILSISTYAW | 28085 |
| HPV33 | E5 | 11 | 22 | LILSISTYAWL | 28086 |
| HPV33 | E5 | 8 | 54 | LLFLYLPM | 28087 |
| HPV33 | E5 | 9 | 54 | LLFLYLPMM | 28088 |
| HPV33 | E5 | 11 | 54 | LLFLYLPMMCI | 28089 |
| HPV33 | E5 | 8 | 17 | LLLRPLIL | 28090 |
| HPV33 | E5 | 10 | 17 | LLLRPLILSI | 28091 |
| HPV33 | E5 | 11 | 37 | LLLWVFVGSPL | 28092 |
| HPV33 | E5 | 9 | 18 | LLRPLILSI | 28093 |
| HPV33 | E5 | 8 | 32 | LLVLVLLL | 28094 |
| HPV33 | E5 | 9 | 32 | LLVLVLLLW | 28095 |
| HPV33 | E5 | 10 | 32 | LLVLVLLLWV | 28096 |
| HPV33 | E5 | 11 | 32 | LLVLVLLLWVF | 28097 |
| HPV33 | E5 | 10 | 38 | LLWVFVGSPL | 28098 |
| HPV33 | E5 | 8 | 59 | LPMMCINF | 28099 |
| HPV33 | E5 | 10 | 59 | LPMMCINFHA | 28100 |
| HPV33 | E5 | 8 | 35 | LVLLLWVF | 28101 |
| HPV33 | E5 | 9 | 35 | LVLLLWVFV | 28102 |
| HPV33 | E5 | 8 | 33 | LVLVLLLW | 28103 |
| HPV33 | E5 | 9 | 33 | LVLVLLLWV | 28104 |
| HPV33 | E5 | 10 | 33 | LVLVLLLWVF | 28105 |
| HPV33 | E5 | 11 | 33 | LVLVLLLWVFV | 28106 |
| HPV33 | E5 | 9 | 1 | MIFVFVLCF | 28107 |
| HPV33 | E5 | 10 | 1 | MIFVFVLCFI | 28108 |
| HPV33 | E5 | 11 | 1 | MIFVFVLCFIL | 28109 |
| HPV33 | E5 | 8 | 61 | MMCINFHA | 28110 |
| HPV33 | E5 | 11 | 61 | MMCINFHAQHM | 28111 |
| HPV33 | E5 | 9 | 21 | PLILSISTY | 28112 |
| HPV33 | E5 | 10 | 21 | PLILSISTYA | 28113 |
| HPV33 | E5 | 11 | 21 | PLILSISTYAW | 28114 |
| HPV33 | E5 | 8 | 46 | PLKIFFCY | 28115 |
| HPV33 | E5 | 9 | 46 | PLKIFFCYL | 28116 |
| HPV33 | E5 | 10 | 46 | PLKIFFCYLL | 28117 |
| HPV33 | E5 | 11 | 46 | PLKIFFCYLLF | 28118 |
| HPV33 | E5 | 9 | 60 | PMMCINFHA | 28119 |
| HPV33 | E5 | 10 | 20 | RPLILSISTY | 28120 |
| HPV33 | E5 | 11 | 20 | RPLILSISTYA | 28121 |
| HPV33 | E5 | 8 | 25 | SISTYAWL | 28122 |
| HPV33 | E5 | 9 | 25 | SISTYAWLL | 28123 |
| HPV33 | E5 | 10 | 25 | SISTYAWLLV | 28124 |
| HPV33 | E5 | 11 | 25 | SISTYAWLLVL | 28125 |
| HPV33 | E5 | 8 | 16 | SLLRPLI | 28126 |
| HPV33 | E5 | 9 | 16 | SLLLRPLIL | 28127 |
| HPV33 | E5 | 11 | 16 | SLLLRPLILSI | 28128 |
| HPV33 | E5 | 9 | 45 | SPLKIFFCY | 28129 |
| HPV33 | E5 | 10 | 45 | SPLKIFFCYL | 28130 |
| HPV33 | E5 | 11 | 45 | SPLKIFFCYLL | 28131 |
| HPV33 | E5 | 8 | 6 | VLCFILFL | 28132 |
| HPV33 | E5 | 10 | 6 | VLCFILFLCL | 28133 |
| HPV33 | E5 | 8 | 36 | VLLLWVFV | 28134 |

TABLE XIV-continued

B62 Supermotif Peptides

| Type | Protein | No. of Amino Acid | Position | Sequence | Seq. Id. No. |
|---|---|---|---|---|---|
| HPV33 | E5 | 8 | 34 | VLVLLLWV | 28135 |
| HPV33 | E5 | 9 | 34 | VLVLLLWVF | 28136 |
| HPV33 | E5 | 10 | 34 | VLVLLLWVFV | 28137 |
| HPV33 | E5 | 8 | 31 | WLLVLVLL | 28138 |
| HPV33 | E5 | 9 | 31 | WLLVLVLLL | 28139 |
| HPV33 | E5 | 10 | 31 | WLLVLVLLLW | 28140 |
| HPV33 | E5 | 11 | 31 | WLLVLVLLLWV | 28141 |
| HPV33 | E5 | 8 | 40 | WVFVGSPL | 28142 |
| HPV33 | E5 | 10 | 40 | WVFVGSPLKI | 28143 |
| HPV33 | E5 | 11 | 40 | WVFVGSPLKIF | 28144 |
| HPV33 | E5 | 9 | 53 | YLLFLYLPM | 28145 |
| HPV33 | E5 | 10 | 53 | YLLFLYLPMM | 28146 |
| HPV33 | E5 | 9 | 58 | YLPMMCINF | 28147 |
| HPV33 | E5 | 11 | 58 | YLPMMCINFHA | 28148 |
| HPV33 | E6 | 9 | 18 | ALETTIHNI | 28149 |
| HPV33 | E6 | 11 | 18 | ALETTIHNIEL | 28150 |
| HPV33 | E6 | 8 | 103 | CIICQRPL | 28151 |
| HPV33 | E6 | 8 | 66 | CLRFLSKI | 28152 |
| HPV33 | E6 | 11 | 66 | CLRFLSKISEY | 28153 |
| HPV33 | E6 | 9 | 111 | CPQEKKRHV | 28154 |
| HPV33 | E6 | 11 | 111 | CPQEKKRHVDL | 28155 |
| HPV33 | E6 | 8 | 16 | CQALETTI | 28156 |
| HPV33 | E6 | 11 | 16 | CQALETTIHNI | 28157 |
| HPV33 | E6 | 8 | 30 | CVECKKPL | 28158 |
| HPV33 | E6 | 10 | 14 | DLCQALETTI | 28159 |
| HPV33 | E6 | 9 | 120 | DLNKRFHNI | 28160 |
| HPV33 | E6 | 8 | 98 | EILIRCII | 28161 |
| HPV33 | E6 | 11 | 27 | ELQCVECKKPL | 28162 |
| HPV33 | E6 | 8 | 89 | EQTVKKPL | 28163 |
| HPV33 | E6 | 11 | 89 | EQTVKKPLNEI | 28164 |
| HPV33 | E6 | 8 | 41 | EVYDFAFA | 28165 |
| HPV33 | E6 | 10 | 41 | EVYDFAFADL | 28166 |
| HPV33 | E6 | 8 | 69 | FLSKISEY | 28167 |
| HPV33 | E6 | 11 | 69 | FLSKISEYRHY | 28168 |
| HPV33 | E6 | 11 | 2 | FQDTEEKPRTL | 28169 |
| HPV33 | E6 | 9 | 61 | GICKLCLRF | 28170 |
| HPV33 | E6 | 10 | 61 | GICKLCLRFL | 28171 |
| HPV33 | E6 | 8 | 118 | HVDLNKRF | 28172 |
| HPV33 | E6 | 11 | 118 | HVDLNKRFHNI | 28173 |
| HPV33 | E6 | 8 | 72 | KISEYRHY | 28174 |
| HPV33 | E6 | 10 | 72 | KISEYRHYNY | 28175 |
| HPV33 | E6 | 10 | 64 | KLCLRFLSKI | 28176 |
| HPV33 | E6 | 8 | 94 | KPLNEILI | 28177 |
| HPV33 | E6 | 11 | 94 | KPLNEILIRCI | 28178 |
| HPV33 | E6 | 8 | 35 | KPLQRSEV | 28179 |
| HPV33 | E6 | 9 | 35 | KPLQRSEVY | 28180 |
| HPV33 | E6 | 11 | 35 | KPLQRSEVYDF | 28181 |
| HPV33 | E6 | 8 | 8 | KPRTLHDL | 28182 |
| HPV33 | E6 | 11 | 8 | KPRTLHDLCQA | 28183 |
| HPV33 | E6 | 11 | 100 | LIRCIICQRPL | 28184 |
| HPV33 | E6 | 10 | 28 | LQCVECKKPL | 28185 |
| HPV33 | E6 | 9 | 37 | LQRSEVYDF | 28186 |
| HPV33 | E6 | 10 | 37 | LQRSEVYDFA | 28187 |
| HPV33 | E6 | 11 | 37 | LQRSEVYDFAF | 28188 |
| HPV33 | E6 | 11 | 127 | NISGRWAGRCA | 28189 |
| HPV33 | E6 | 8 | 58 | NPFGICKL | 28190 |
| HPV33 | E6 | 10 | 58 | NPFGICKLCL | 28191 |
| HPV33 | E6 | 11 | 109 | PLCPQEKKRHV | 28192 |
| HPV33 | E6 | 10 | 95 | PLNEILIRCI | 28193 |
| HPV33 | E6 | 11 | 95 | PLNEILIRCII | 28194 |
| HPV33 | E6 | 8 | 36 | PLQRSEVY | 28195 |
| HPV33 | E6 | 10 | 36 | PLQRSEVYDF | 28196 |
| HPV33 | E6 | 11 | 36 | PLQRSEVYDFA | 28197 |
| HPV33 | E6 | 8 | 112 | PQEKKRHV | 28198 |
| HPV33 | E6 | 10 | 112 | PQEKKRHVDL | 28199 |
| HPV33 | E6 | 11 | 82 | SVYGNTLEQTV | 28200 |
| HPV33 | E6 | 10 | 22 | TIHNIELQCV | 28201 |
| HPV33 | E6 | 10 | 87 | TLEQTVKKPL | 28202 |
| HPV33 | E6 | 8 | 11 | TLHDLCQA | 28203 |
| HPV33 | E6 | 9 | 11 | TLHDLCQAL | 28204 |
| HPV33 | E6 | 9 | 91 | TVKKPLNEI | 28205 |
| HPV33 | E6 | 10 | 91 | TVKKPLNEIL | 28206 |
| HPV33 | E6 | 11 | 91 | TVKKPLNEILI | 28207 |
| HPV33 | E6 | 10 | 51 | TVVYREGNPF | 28208 |
| HPV33 | E6 | 9 | 52 | VVYREGNPF | 28209 |

TABLE XIV-continued

B62 Supermotif Peptides

| Type | Protein | No. of Amino Acid | Position | Sequence | Seq. Id. No. |
|---|---|---|---|---|---|
| HPV33 | E6 | 11 | 52 | VVYREGNPFGI | 28210 |
| HPV33 | E7 | 8 | 45 | AQPATADY | 28211 |
| HPV33 | E7 | 9 | 45 | AQPATADYY | 28212 |
| HPV33 | E7 | 10 | 45 | AQPATADYYI | 28213 |
| HPV33 | E7 | 11 | 45 | AQPATADYYIV | 28214 |
| HPV33 | E7 | 9 | 68 | CVNSTASDL | 28215 |
| HPV33 | E7 | 8 | 75 | DLRTIQQL | 28216 |
| HPV33 | E7 | 9 | 75 | DLRTIQQLL | 28217 |
| HPV33 | E7 | 10 | 75 | DLRTIQQLLM | 28218 |
| HPV33 | E7 | 8 | 21 | DLYCYEQL | 28219 |
| HPV33 | E7 | 9 | 14 | DLYPEPTDL | 28220 |
| HPV33 | E7 | 10 | 14 | DLYPEPTDLY | 28221 |
| HPV33 | E7 | 8 | 18 | EPTDLYCY | 28222 |
| HPV33 | E7 | 11 | 18 | EPTDLYCYEQL | 28223 |
| HPV33 | E7 | 9 | 37 | GLDRPDGQA | 28224 |
| HPV33 | E7 | 8 | 43 | GQAQPATA | 28225 |
| HPV33 | E7 | 10 | 43 | GQAQPATADY | 28226 |
| HPV33 | E7 | 11 | 43 | GQAQPATADYY | 28227 |
| HPV33 | E7 | 9 | 79 | IQQLLMGTV | 28228 |
| HPV33 | E7 | 11 | 79 | IQQLLMGTVNI | 28229 |
| HPV33 | E7 | 8 | 5 | KPTLKEYV | 28230 |
| HPV33 | E7 | 9 | 5 | KPTLKEYVL | 28231 |
| HPV33 | E7 | 11 | 5 | KPTLKEYVLDL | 28232 |
| HPV33 | E7 | 8 | 82 | LLMGTVNI | 28233 |
| HPV33 | E7 | 9 | 82 | LLMGTVNIV | 28234 |
| HPV33 | E7 | 8 | 83 | LMGTVNIV | 28235 |
| HPV33 | E7 | 8 | 88 | NIVCPTCA | 28236 |
| HPV33 | E7 | 9 | 81 | QLLMGTVNI | 28237 |
| HPV33 | E7 | 10 | 81 | QLLMGTVNIV | 28238 |
| HPV33 | E7 | 8 | 46 | QPATADYY | 28239 |
| HPV33 | E7 | 9 | 46 | QPATADYYI | 28240 |
| HPV33 | E7 | 10 | 46 | QPATADYYIV | 28241 |
| HPV33 | E7 | 8 | 80 | QQLLMGTV | 28242 |
| HPV33 | E7 | 10 | 80 | QQLLMGTVNI | 28243 |
| HPV33 | E7 | 11 | 80 | QQLLMGTVNIV | 28244 |
| HPV33 | E7 | 8 | 66 | RLCVNSTA | 28245 |
| HPV33 | E7 | 11 | 66 | RLCVNSTASDL | 28246 |
| HPV33 | E7 | 9 | 40 | RPDGQAQPA | 28247 |
| HPV33 | E7 | 11 | 40 | RPDGQAQPATA | 28248 |
| HPV33 | E7 | 10 | 78 | TIQQLLMGTV | 28249 |
| HPV33 | E7 | 9 | 7 | TLKEYVLDL | 28250 |
| HPV33 | E7 | 10 | 7 | TLKEYVLDLY | 28251 |
| HPV33 | E7 | 10 | 86 | TVNIVCPTCA | 28252 |
| HPV33 | E7 | 10 | 64 | TVRLCVNSTA | 28253 |
| HPV33 | E7 | 11 | 12 | VLDLYPEPTDL | 28254 |
| HPV33 | E7 | 8 | 16 | YPEPTDLY | 28255 |
| HPV33 | E7 | 10 | 16 | YPEPTDLYCY | 28256 |
| HPV33 | L1 | 8 | 424 | AITCQKTV | 28257 |
| HPV33 | L1 | 10 | 392 | AMNPDILEDW | 28258 |
| HPV33 | L1 | 9 | 180 | APANDCPPL | 28259 |
| HPV33 | L1 | 11 | 180 | APANDCPPLEL | 28260 |
| HPV33 | L1 | 10 | 483 | APTSTRTSSA | 28261 |
| HPV33 | L1 | 8 | 316 | AQGHNNGI | 28262 |
| HPV33 | L1 | 10 | 316 | AQGHNNGICW | 28263 |
| HPV33 | L1 | 9 | 44 | AVGHPYFSI | 28264 |
| HPV33 | L1 | 8 | 270 | AVPDDLYI | 28265 |
| HPV33 | L1 | 11 | 147 | CLSMDYKQTQL | 28266 |
| HPV33 | L1 | 9 | 207 | CMDFKTLQA | 28267 |
| HPV33 | L1 | 10 | 185 | CPPLELINTI | 28268 |
| HPV33 | L1 | 11 | 185 | CPPLELINTII | 28269 |
| HPV33 | L1 | 9 | 223 | DICGSTCKY | 28270 |
| HPV33 | L1 | 8 | 396 | DILEDWQF | 28271 |
| HPV33 | L1 | 10 | 396 | DILEDWQFGL | 28272 |
| HPV33 | L1 | 11 | 457 | DLDQFPLGRKF | 28273 |
| HPV33 | L1 | 8 | 449 | DLKEKFSA | 28274 |
| HPV33 | L1 | 10 | 449 | DLKEKFSADL | 28275 |
| HPV33 | L1 | 8 | 370 | DLQFVFQL | 28276 |
| HPV33 | L1 | 11 | 370 | DLQFVFQLCKV | 28277 |
| HPV33 | L1 | 11 | 274 | DLYIKGSGTTA | 28278 |
| HPV33 | L1 | 10 | 199 | DMVDTGFGCM | 28279 |
| HPV33 | L1 | 8 | 438 | DPLGKYTF | 28280 |
| HPV33 | L1 | 9 | 438 | DPLGKYTFW | 28281 |
| HPV33 | L1 | 11 | 438 | DPLGKYTFWEV | 28282 |
| HPV33 | L1 | 9 | 459 | DQFPLGRKF | 28283 |
| HPV33 | L1 | 10 | 459 | DQFPLGRKFL | 28284 |

TABLE XIV-continued

B62 Supermotif Peptides

| Type | Protein | No. of Amino Acid | Position | Sequence | Seq. Id. No. |
|---|---|---|---|---|---|
| HPV33 | L1 | 11 | 459 | DQFPLGRKFLL | 28285 |
| HPV33 | L1 | 8 | 107 | EIGRGQPL | 28286 |
| HPV33 | L1 | 10 | 107 | EIGRGQPLGV | 28287 |
| HPV33 | L1 | 8 | 240 | EPYGDSLF | 28288 |
| HPV33 | L1 | 9 | 240 | EPYGDSLFF | 28289 |
| HPV33 | L1 | 10 | 240 | EPYGDSLFFF | 28290 |
| HPV33 | L1 | 11 | 240 | EPYGDSLFFFL | 28291 |
| HPV33 | L1 | 8 | 253 | EQMFVRHF | 28292 |
| HPV33 | L1 | 9 | 253 | EQMFVRHFF | 28293 |
| HPV33 | L1 | 8 | 447 | EVDLKEKF | 28294 |
| HPV33 | L1 | 10 | 447 | EVDLKEKFSA | 28295 |
| HPV33 | L1 | 8 | 385 | EVMTYIHA | 28296 |
| HPV33 | L1 | 9 | 385 | EVMTYIHAM | 28297 |
| HPV33 | L1 | 9 | 467 | FLLQAGLKA | 28298 |
| HPV33 | L1 | 8 | 249 | FLRREQMF | 28299 |
| HPV33 | L1 | 9 | 249 | FLRREQMFV | 28300 |
| HPV33 | L1 | 8 | 461 | FPLGRKFL | 28301 |
| HPV33 | L1 | 9 | 461 | FPLGRKFLL | 28302 |
| HPV33 | L1 | 11 | 461 | FPLGRKFLLQA | 28303 |
| HPV33 | L1 | 8 | 292 | FPTPSGSM | 28304 |
| HPV33 | L1 | 9 | 292 | FPTPSGSMV | 28305 |
| HPV33 | L1 | 8 | 375 | FQLCKVTL | 28306 |
| HPV33 | L1 | 10 | 375 | FQLCKVTLTA | 28307 |
| HPV33 | L1 | 8 | 373 | FVFQLCKV | 28308 |
| HPV33 | L1 | 10 | 373 | FVFQLCKVTL | 28309 |
| HPV33 | L1 | 9 | 256 | FVRHFFNRA | 28310 |
| HPV33 | L1 | 8 | 322 | GICWGNQV | 28311 |
| HPV33 | L1 | 9 | 322 | GICWGNQVF | 28312 |
| HPV33 | L1 | 10 | 322 | GICWGNQVFV | 28313 |
| HPV33 | L1 | 8 | 117 | GISGHPLL | 28314 |
| HPV33 | L1 | 11 | 117 | GISGHPLLNKF | 28315 |
| HPV33 | L1 | 10 | 105 | GLEIGRGQPL | 28316 |
| HPV33 | L1 | 8 | 472 | GLKAKPKL | 28317 |
| HPV33 | L1 | 11 | 472 | GLKAKPKLKRA | 28318 |
| HPV33 | L1 | 9 | 68 | GLQYRVFRV | 28319 |
| HPV33 | L1 | 11 | 68 | GLQYRVFRVRL | 28320 |
| HPV33 | L1 | 8 | 404 | GLTPPPSA | 28321 |
| HPV33 | L1 | 10 | 404 | GLTPPPSASL | 28322 |
| HPV33 | L1 | 11 | 138 | GQPGADNRECL | 28323 |
| HPV33 | L1 | 8 | 111 | GQPLGVGI | 28324 |
| HPV33 | L1 | 8 | 173 | GVACTNAA | 28325 |
| HPV33 | L1 | 10 | 173 | GVACTNAAPA | 28326 |
| HPV33 | L1 | 9 | 115 | GVGISGHPL | 28327 |
| HPV33 | L1 | 10 | 115 | GVGISGHPLL | 28328 |
| HPV33 | L1 | 9 | 365 | HVEEYDLQF | 28329 |
| HPV33 | L1 | 10 | 365 | HVEEYDLQFV | 28330 |
| HPV33 | L1 | 11 | 365 | HVEEYDLQFVF | 28331 |
| HPV33 | L1 | 8 | 194 | IIEDGDMV | 28332 |
| HPV33 | L1 | 9 | 397 | ILEDWQFGL | 28333 |
| HPV33 | L1 | 10 | 60 | KLLVPKVSGL | 28334 |
| HPV33 | L1 | 11 | 236 | KMTSEPYGDSL | 28335 |
| HPV33 | L1 | 8 | 476 | KPKLKRAA | 28336 |
| HPV33 | L1 | 8 | 163 | KPPTGEHW | 28337 |
| HPV33 | L1 | 8 | 309 | KPYWLQRA | 28338 |
| HPV33 | L1 | 8 | 153 | KQTQLCLL | 28339 |
| HPV33 | L1 | 9 | 65 | KVSGLQYRV | 28340 |
| HPV33 | L1 | 10 | 65 | KVSGLQYRVF | 28341 |
| HPV33 | L1 | 8 | 379 | KVTLTAEV | 28342 |
| HPV33 | L1 | 9 | 379 | KVTLTAEVM | 28343 |
| HPV33 | L1 | 11 | 379 | KVTLTAEVMTY | 28344 |
| HPV33 | L1 | 8 | 20 | KVVSTDEY | 28345 |
| HPV33 | L1 | 9 | 20 | KVVSTDEYV | 28346 |
| HPV33 | L1 | 11 | 190 | LINTIIEDGDM | 28347 |
| HPV33 | L1 | 8 | 42 | LLAVGHPY | 28348 |
| HPV33 | L1 | 9 | 42 | LLAVGHPYF | 28349 |
| HPV33 | L1 | 11 | 42 | LLAVGHPYFSI | 28350 |
| HPV33 | L1 | 8 | 468 | LLQAGLKA | 28351 |
| HPV33 | L1 | 9 | 61 | LLVPKVSGL | 28352 |
| HPV33 | L1 | 11 | 61 | LLVPKVSGLQY | 28353 |
| HPV33 | L1 | 9 | 78 | LPDPNKFGF | 28354 |
| HPV33 | L1 | 9 | 13 | LPPVPVSKV | 28355 |
| HPV33 | L1 | 10 | 13 | LPPVPVSKVV | 28356 |
| HPV33 | L1 | 11 | 469 | LQAGLKAKPKL | 28357 |
| HPV33 | L1 | 8 | 213 | LQANKSDV | 28358 |
| HPV33 | L1 | 10 | 213 | LQANKSDVPI | 28359 |

TABLE XIV-continued

B62 Supermotif Peptides

| Type | Protein | No. of Amino Acid | Position | Sequence | Seq. Id. No. |
|---|---|---|---|---|---|
| HPV33 | L1 | 8 | 413 | LQDTYRFV | 28360 |
| HPV33 | L1 | 10 | 371 | LQFVFQLCKV | 28361 |
| HPV33 | L1 | 11 | 313 | LQRAQGHNNGI | 28362 |
| HPV33 | L1 | 8 | 69 | LQYRVFRV | 28363 |
| HPV33 | L1 | 10 | 69 | LQYRVFRVRL | 28364 |
| HPV33 | L1 | 8 | 62 | LVPKVSGL | 28365 |
| HPV33 | L1 | 10 | 62 | LVPKVSGLQY | 28366 |
| HPV33 | L1 | 8 | 99 | LVWACVGL | 28367 |
| HPV33 | L1 | 10 | 99 | LVWACVGLEI | 28368 |
| HPV33 | L1 | 9 | 200 | MVDTGFGCM | 28369 |
| HPV33 | L1 | 11 | 200 | MVDTGFGCMDF | 28370 |
| HPV33 | L1 | 8 | 299 | MVTSESQL | 28371 |
| HPV33 | L1 | 9 | 299 | MVTSESQLF | 28372 |
| HPV33 | L1 | 8 | 341 | NMTLCTQV | 28373 |
| HPV33 | L1 | 8 | 394 | NPDILEDW | 28374 |
| HPV33 | L1 | 10 | 394 | NPDILEDWQF | 28375 |
| HPV33 | L1 | 8 | 93 | NPDTQRLV | 28376 |
| HPV33 | L1 | 9 | 93 | NPDTQRLVW | 28377 |
| HPV33 | L1 | 10 | 93 | NPDTQRLVWA | 28378 |
| HPV33 | L1 | 8 | 54 | NPTNAKKL | 28379 |
| HPV33 | L1 | 9 | 54 | NPTNAKKLL | 28380 |
| HPV33 | L1 | 10 | 54 | NPTNAKKLLV | 28381 |
| HPV33 | L1 | 8 | 327 | NQVFVTVV | 28382 |
| HPV33 | L1 | 11 | 221 | PIDICGSTCKY | 28383 |
| HPV33 | L1 | 8 | 187 | PLELINTI | 28384 |
| HPV33 | L1 | 9 | 187 | PLELINTII | 28385 |
| HPV33 | L1 | 8 | 439 | PLGKYTFW | 28386 |
| HPV33 | L1 | 10 | 439 | PLGKYTFWEV | 28387 |
| HPV33 | L1 | 8 | 462 | PLGRKFLL | 28388 |
| HPV33 | L1 | 10 | 462 | PLGRKFLLQA | 28389 |
| HPV33 | L1 | 11 | 113 | PLGVGISGHPL | 28390 |
| HPV33 | L1 | 9 | 432 | PPKEKEDPL | 28391 |
| HPV33 | L1 | 9 | 186 | PPLELINTI | 28392 |
| HPV33 | L1 | 10 | 186 | PPLELINTII | 28393 |
| HPV33 | L1 | 11 | 407 | PPPSASLQDTY | 28394 |
| HPV33 | L1 | 10 | 408 | PPSASLQDTY | 28395 |
| HPV33 | L1 | 11 | 164 | PPTGEHWGKGV | 28396 |
| HPV33 | L1 | 8 | 14 | PPVPVSKV | 28397 |
| HPV33 | L1 | 9 | 14 | PPVPVSKVV | 28398 |
| HPV33 | L1 | 8 | 15 | PVPVSKVV | 28399 |
| HPV33 | L1 | 11 | 17 | PVSKVVSTDEY | 28400 |
| HPV33 | L1 | 9 | 376 | QLCKVTLTA | 28401 |
| HPV33 | L1 | 11 | 376 | QLCKVTLTAEV | 28402 |
| HPV33 | L1 | 8 | 305 | QLFNKPYW | 28403 |
| HPV33 | L1 | 9 | 305 | QLFNKPYWL | 28404 |
| HPV33 | L1 | 8 | 254 | QMFVRHFF | 28405 |
| HPV33 | L1 | 11 | 254 | QMFVRHFFNRA | 28406 |
| HPV33 | L1 | 10 | 139 | QPGADNRECL | 28407 |
| HPV33 | L1 | 8 | 347 | QVTSDSTY | 28408 |
| HPV33 | L1 | 9 | 41 | RLLAVGHPY | 28409 |
| HPV33 | L1 | 10 | 41 | RLLAVGHPYF | 28410 |
| HPV33 | L1 | 8 | 77 | RLPDPNKF | 28411 |
| HPV33 | L1 | 10 | 77 | RLPDPNKFGF | 28412 |
| HPV33 | L1 | 9 | 98 | RLVWACVGL | 28413 |
| HPV33 | L1 | 11 | 98 | RLVWACVGLEI | 28414 |
| HPV33 | L1 | 8 | 5 | RPSEATVY | 28415 |
| HPV33 | L1 | 9 | 5 | RPSEATVYL | 28416 |
| HPV33 | L1 | 10 | 75 | RVRLPDPNKF | 28417 |
| HPV33 | L1 | 8 | 51 | SIKNPTNA | 28418 |
| HPV33 | L1 | 11 | 51 | SIKNPTNAKKL | 28419 |
| HPV33 | L1 | 8 | 285 | SIQSSAFF | 28420 |
| HPV33 | L1 | 11 | 32 | SIYYYAGSSRL | 28421 |
| HPV33 | L1 | 11 | 245 | SLFFFLRREQM | 28422 |
| HPV33 | L1 | 8 | 412 | SLQDTYRF | 28423 |
| HPV33 | L1 | 9 | 412 | SLQDTYRFV | 28424 |
| HPV33 | L1 | 9 | 149 | SMDYKQTQL | 28425 |
| HPV33 | L1 | 11 | 149 | SMDYKQTQLCL | 28426 |
| HPV33 | L1 | 9 | 298 | SMVTSESQL | 28427 |
| HPV33 | L1 | 10 | 298 | SMVTSESQLF | 28428 |
| HPV33 | L1 | 10 | 422 | SQAITCQKTV | 28429 |
| HPV33 | L1 | 8 | 304 | SQLFNKPY | 28430 |
| HPV33 | L1 | 9 | 304 | SQLFNKPYW | 28431 |
| HPV33 | L1 | 10 | 304 | SQLFNKPYWL | 28432 |
| HPV33 | L1 | 8 | 2 | SVWRPSEA | 28433 |
| HPV33 | L1 | 10 | 2 | SVWRPSEATV | 28434 |

TABLE XIV-continued

B62 Supermotif Peptides

| Type | Protein | No. of Amino Acid | Position | Sequence | Seq. Id. No. |
|---|---|---|---|---|---|
| HPV33 | L1 | 11 | 2 | SVWRPSEATVY | 28435 |
| HPV33 | L1 | 8 | 193 | TIIEDGDM | 28436 |
| HPV33 | L1 | 9 | 193 | TIIEDGDMV | 28437 |
| HPV33 | L1 | 10 | 266 | TLGEAVPDDL | 28438 |
| HPV33 | L1 | 11 | 266 | TLGEAVPDDLY | 28439 |
| HPV33 | L1 | 9 | 212 | TLQANKSDV | 28440 |
| HPV33 | L1 | 11 | 212 | TLQANKSDVPI | 28441 |
| HPV33 | L1 | 9 | 381 | TLTAEVMTY | 28442 |
| HPV33 | L1 | 10 | 381 | TLTAEVMTYI | 28443 |
| HPV33 | L1 | 8 | 406 | TPPPSASL | 28444 |
| HPV33 | L1 | 9 | 96 | TQRLVWACV | 28445 |
| HPV33 | L1 | 11 | 96 | TQRLVWACVGL | 28446 |
| HPV33 | L1 | 9 | 346 | TQVTSDSTY | 28447 |
| HPV33 | L1 | 11 | 430 | TVPPKEKEDPL | 28448 |
| HPV33 | L1 | 11 | 332 | TVVDTTRSTNM | 28449 |
| HPV33 | L1 | 9 | 10 | TVYLPPVPV | 28450 |
| HPV33 | L1 | 8 | 386 | VMTYIHAM | 28451 |
| HPV33 | L1 | 9 | 63 | VPKVSGLQY | 28452 |
| HPV33 | L1 | 11 | 63 | VPKVSGLQYRV | 28453 |
| HPV33 | L1 | 10 | 431 | VPPKEKEDPL | 28454 |
| HPV33 | L1 | 10 | 333 | VVDTTRSTNM | 28455 |
| HPV33 | L1 | 8 | 21 | VVSTDEYV | 28456 |
| HPV33 | L1 | 11 | 401 | WQFGLTPPPSA | 28457 |
| HPV33 | L1 | 9 | 389 | YIHAMNPDI | 28458 |
| HPV33 | L1 | 10 | 389 | YIHAMNPDIL | 28459 |
| HPV33 | L1 | 9 | 276 | YIKGSGTTA | 28460 |
| HPV33 | L1 | 11 | 276 | YIKGSGTTASI | 28461 |
| HPV33 | L1 | 8 | 362 | YIRHVEEY | 28462 |
| HPV33 | L1 | 10 | 362 | YIRHVEEYDL | 28463 |
| HPV33 | L1 | 9 | 234 | YLKMTSEPY | 28464 |
| HPV33 | L1 | 10 | 12 | YLPPVPVSKV | 28465 |
| HPV33 | L1 | 11 | 12 | YLPPVPVSKVV | 28466 |
| HPV33 | L1 | 8 | 27 | YVSRTSIY | 28467 |
| HPV33 | L1 | 9 | 27 | YVSRTSIYY | 28468 |
| HPV33 | L1 | 10 | 27 | YVSRTSIYYY | 28469 |
| HPV33 | L1 | 11 | 27 | YVSRTSIYYYA | 28470 |
| HPV33 | L2 | 8 | 140 | AIINVSSV | 28471 |
| HPV33 | L2 | 11 | 82 | AIPLQPIRPPV | 28472 |
| HPV33 | L2 | 9 | 291 | AITSRRHTV | 28473 |
| HPV33 | L2 | 11 | 291 | AITSRRHTVRF | 28474 |
| HPV33 | L2 | 9 | 173 | APAEASGHF | 28475 |
| HPV33 | L2 | 10 | 173 | APAEASGHFI | 28476 |
| HPV33 | L2 | 11 | 173 | APAEASGHFIF | 28477 |
| HPV33 | L2 | 9 | 276 | APDPDFLDI | 28478 |
| HPV33 | L2 | 10 | 276 | APDPDFLDII | 28479 |
| HPV33 | L2 | 11 | 276 | APDPDFLDIIA | 28480 |
| HPV33 | L2 | 10 | 120 | APSIPTPSGF | 28481 |
| HPV33 | L2 | 9 | 27 | CPPDVIPKV | 28482 |
| HPV33 | L2 | 9 | 283 | DIIALHRPA | 28483 |
| HPV33 | L2 | 10 | 283 | DIIALHRPAI | 28484 |
| HPV33 | L2 | 10 | 272 | DISPAPDPDF | 28485 |
| HPV33 | L2 | 11 | 272 | DISPAPDPDFL | 28486 |
| HPV33 | L2 | 8 | 327 | DLSPIVPL | 28487 |
| HPV33 | L2 | 11 | 239 | DPAFLTSPHKL | 28488 |
| HPV33 | L2 | 8 | 278 | DPDFLDII | 28489 |
| HPV33 | L2 | 9 | 278 | DPDFLDIIA | 28490 |
| HPV33 | L2 | 10 | 278 | DPDFLDIIAL | 28491 |
| HPV33 | L2 | 8 | 261 | DPEDTLQF | 28492 |
| HPV33 | L2 | 9 | 77 | DPPTAAIPL | 28493 |
| HPV33 | L2 | 9 | 42 | DQILKYGSL | 28494 |
| HPV33 | L2 | 11 | 42 | DQILKYGSLGV | 28495 |
| HPV33 | L2 | 9 | 369 | DVDNVHTPM | 28496 |
| HPV33 | L2 | 11 | 30 | DVIPKVEGSTI | 28497 |
| HPV33 | L2 | 11 | 130 | DVTTSADTTPA | 28498 |
| HPV33 | L2 | 10 | 364 | DVYADDVDNV | 28499 |
| HPV33 | L2 | 9 | 165 | EPSVLHPPA | 28500 |
| HPV33 | L2 | 11 | 165 | EPSVLHPPAPA | 28501 |
| HPV33 | L2 | 8 | 341 | EQYELQPL | 28502 |
| HPV33 | L2 | 8 | 113 | FIEAGAPA | 28503 |
| HPV33 | L2 | 11 | 113 | FIEAGAPAPSI | 28504 |
| HPV33 | L2 | 8 | 181 | FIFSSPTV | 28505 |
| HPV33 | L2 | 10 | 447 | FILRRRKRF | 28506 |
| HPV33 | L2 | 11 | 281 | FLDIIALHRPA | 28507 |
| HPV33 | L2 | 8 | 242 | FLTSPHKL | 28508 |
| HPV33 | L2 | 9 | 242 | FLTSPHKLI | 28509 |

TABLE XIV-continued

B62 Supermotif Peptides

| Type | Protein | No. of Amino Acid | Position | Sequence | Seq. Id. No. |
|---|---|---|---|---|---|
| HPV33 | L2 | 11 | 242 | FLTSPHKLITY | 28510 |
| HPV33 | L2 | 8 | 428 | FPFDTIVV | 28511 |
| HPV33 | L2 | 11 | 428 | FPFDTIVVDGA | 28512 |
| HPV33 | L2 | 8 | 415 | FPTSSPFV | 28513 |
| HPV33 | L2 | 10 | 415 | FPTSSPFVPI | 28514 |
| HPV33 | L2 | 8 | 456 | FPYFFTDV | 28515 |
| HPV33 | L2 | 10 | 456 | FPYFFTDVRV | 28516 |
| HPV33 | L2 | 11 | 456 | FPYFFTDVRVA | 28517 |
| HPV33 | L2 | 9 | 268 | FQHSDISPA | 28518 |
| HPV33 | L2 | 8 | 440 | FVLHPSYF | 28519 |
| HPV33 | L2 | 9 | 440 | FVLHPSYFI | 28520 |
| HPV33 | L2 | 10 | 440 | FVLHPSYFIL | 28521 |
| HPV33 | L2 | 8 | 421 | FVPISPFF | 28522 |
| HPV33 | L2 | 10 | 421 | FVPISPFFPF | 28523 |
| HPV33 | L2 | 10 | 201 | FVVSTDSSNV | 28524 |
| HPV33 | L2 | 10 | 361 | GLYDVYADDV | 28525 |
| HPV33 | L2 | 10 | 226 | GLYSRNTQQV | 28526 |
| HPV33 | L2 | 8 | 407 | GPDIPSPL | 28527 |
| HPV33 | L2 | 9 | 407 | GPDIPSPLF | 28528 |
| HPV33 | L2 | 8 | 98 | GPLDSSIV | 28529 |
| HPV33 | L2 | 10 | 98 | GPLDSSIVSL | 28530 |
| HPV33 | L2 | 11 | 98 | GPLDSSIVSLI | 28531 |
| HPV33 | L2 | 9 | 51 | GVFFGGLGI | 28532 |
| HPV33 | L2 | 11 | 158 | HLNPTFTEPSV | 28533 |
| HPV33 | L2 | 8 | 170 | HPPAPAEA | 28534 |
| HPV33 | L2 | 8 | 284 | IIALHRPA | 28535 |
| HPV33 | L2 | 9 | 284 | IIALHRPAI | 28536 |
| HPV33 | L2 | 9 | 44 | ILKYGSLGV | 28537 |
| HPV33 | L2 | 10 | 44 | ILKYGSLGVF | 28538 |
| HPV33 | L2 | 11 | 44 | ILKYGSLGVFF | 28539 |
| HPV33 | L2 | 9 | 448 | ILRRRKRF | 28540 |
| HPV33 | L2 | 11 | 448 | ILRRRRKRFPY | 28541 |
| HPV33 | L2 | 8 | 216 | IPGSRPVA | 28542 |
| HPV33 | L2 | 10 | 216 | IPGSRPVARL | 28543 |
| HPV33 | L2 | 9 | 32 | IPKVEGSTI | 28544 |
| HPV33 | L2 | 10 | 32 | IPKVEGSTIA | 28545 |
| HPV33 | L2 | 11 | 394 | IPLNTGFDTPV | 28546 |
| HPV33 | L2 | 10 | 83 | IPLQPIRPPV | 28547 |
| HPV33 | L2 | 8 | 196 | IPMDTFVV | 28548 |
| HPV33 | L2 | 9 | 123 | IPTPSGFDV | 28549 |
| HPV33 | L2 | 8 | 152 | IQTISTHL | 28550 |
| HPV33 | L2 | 8 | 331 | IVPLDHTV | 28551 |
| HPV33 | L2 | 10 | 104 | IVSLIEETSF | 28552 |
| HPV33 | L2 | 11 | 104 | IVSLIEETSFI | 28553 |
| HPV33 | L2 | 8 | 433 | IVVDGADF | 28554 |
| HPV33 | L2 | 9 | 433 | IVVDGADFV | 28555 |
| HPV33 | L2 | 10 | 433 | IVVDGADFVL | 28556 |
| HPV33 | L2 | 9 | 248 | KLITYDNPA | 28557 |
| HPV33 | L2 | 10 | 248 | KLITYDNPAF | 28558 |
| HPV33 | L2 | 9 | 316 | KQIGARIHY | 28559 |
| HPV33 | L2 | 10 | 316 | KQIGARIHYY | 28560 |
| HPV33 | L2 | 8 | 34 | KVEGSTIA | 28561 |
| HPV33 | L2 | 11 | 34 | KVEGSTIADQI | 28562 |
| HPV33 | L2 | 8 | 236 | KVVDPAFL | 28563 |
| HPV33 | L2 | 8 | 107 | LIEETSFI | 28564 |
| HPV33 | L2 | 10 | 107 | LIEETSFIEA | 28565 |
| HPV33 | L2 | 8 | 249 | LITYDNPA | 28566 |
| HPV33 | L2 | 9 | 249 | LITYDNPAF | 28567 |
| HPV33 | L2 | 8 | 266 | LQFQHSDI | 28568 |
| HPV33 | L2 | 11 | 266 | LQFQHSDISPA | 28569 |
| HPV33 | L2 | 8 | 85 | LQPIRPPV | 28570 |
| HPV33 | L2 | 10 | 85 | LQPIRPPVTV | 28571 |
| HPV33 | L2 | 8 | 377 | MQHSYSTF | 28572 |
| HPV33 | L2 | 9 | 377 | MQHSYSTFA | 28573 |
| HPV33 | L2 | 8 | 195 | NIPMDTFV | 28574 |
| HPV33 | L2 | 9 | 195 | NIPMDTFVV | 28575 |
| HPV33 | L2 | 9 | 160 | NPTFTEPSV | 28576 |
| HPV33 | L2 | 10 | 160 | NPTFTEPSVL | 28577 |
| HPV33 | L2 | 10 | 372 | NVHTPMQHSY | 28578 |
| HPV33 | L2 | 10 | 391 | NVSIPLNTGF | 28579 |
| HPV33 | L2 | 10 | 143 | NVSSVGESSI | 28580 |
| HPV33 | L2 | 8 | 209 | NVTSSTPI | 28581 |
| HPV33 | L2 | 9 | 73 | PIGTDPPTA | 28582 |
| HPV33 | L2 | 10 | 73 | PIGTDPPTAA | 28583 |
| HPV33 | L2 | 11 | 73 | PIGTDPPTAAI | 28584 |

TABLE XIV-continued

B62 Supermotif Peptides

| Type | Protein | No. of Amino Acid | Position | Sequence | Seq. Id. No. |
|---|---|---|---|---|---|
| HPV33 | L2 | 8 | 215 | PIPGSRPV | 28585 |
| HPV33 | L2 | 9 | 215 | PIPGSRPVA | 28586 |
| HPV33 | L2 | 11 | 215 | PIPGSRPVARL | 28587 |
| HPV33 | L2 | 8 | 87 | PIRPPVTV | 28588 |
| HPV33 | L2 | 11 | 87 | PIRPPVTVDTV | 28589 |
| HPV33 | L2 | 8 | 423 | PISPFFPF | 28590 |
| HPV33 | L2 | 11 | 423 | PISPFFPFDTI | 28591 |
| HPV33 | L2 | 9 | 330 | PIVPLDHTV | 28592 |
| HPV33 | L2 | 11 | 333 | PLDHTVPNEQY | 28593 |
| HPV33 | L2 | 9 | 99 | PLDSSIVSL | 28594 |
| HPV33 | L2 | 10 | 99 | PLDSSIVSLI | 28595 |
| HPV33 | L2 | 9 | 413 | PLFPTSSPF | 28596 |
| HPV33 | L2 | 10 | 413 | PLFPTSSPFV | 28597 |
| HPV33 | L2 | 10 | 347 | PLHDTSTSSY | 28598 |
| HPV33 | L2 | 10 | 395 | PLNTGFDTPV | 28599 |
| HPV33 | L2 | 11 | 395 | PLNTGFDTPVM | 28600 |
| HPV33 | L2 | 9 | 84 | PLQPIRPPV | 28601 |
| HPV33 | L2 | 11 | 84 | PLQPIRPPVTV | 28602 |
| HPV33 | L2 | 9 | 376 | PMQHSYSTF | 28603 |
| HPV33 | L2 | 10 | 376 | PMQHSYSTFA | 28604 |
| HPV33 | L2 | 11 | 171 | PPAPAEASGHF | 28605 |
| HPV33 | L2 | 8 | 28 | PPDVIPKV | 28606 |
| HPV33 | L2 | 8 | 78 | PPTAAIPL | 28607 |
| HPV33 | L2 | 11 | 78 | PPTAAIPLQPI | 28608 |
| HPV33 | L2 | 8 | 90 | PPVTVDTV | 28609 |
| HPV33 | L2 | 11 | 90 | PPVTVDTVGPL | 28610 |
| HPV33 | L2 | 8 | 221 | PVARLGLY | 28611 |
| HPV33 | L2 | 8 | 403 | PVMSGPDI | 28612 |
| HPV33 | L2 | 10 | 91 | PVTVDTVGPL | 28613 |
| HPV33 | L2 | 8 | 317 | QIGARIHY | 28614 |
| HPV33 | L2 | 9 | 317 | QIGARIHYY | 28615 |
| HPV33 | L2 | 8 | 43 | QILKYGSL | 28616 |
| HPV33 | L2 | 10 | 43 | QILKYGSLGV | 28617 |
| HPV33 | L2 | 11 | 43 | QILKYGSLGVF | 28618 |
| HPV33 | L2 | 8 | 16 | QLYQTCKA | 28619 |
| HPV33 | L2 | 9 | 86 | QPIRPPVTV | 28620 |
| HPV33 | L2 | 11 | 346 | QPLHDTSTSSY | 28621 |
| HPV33 | L2 | 9 | 233 | QQVKVVDPA | 28622 |
| HPV33 | L2 | 10 | 233 | QQVKVVDPAF | 28623 |
| HPV33 | L2 | 11 | 233 | QQVKVVDPAFL | 28624 |
| HPV33 | L2 | 8 | 234 | QVKVVDPA | 28625 |
| HPV33 | L2 | 9 | 234 | QVKVVDPAF | 28626 |
| HPV33 | L2 | 10 | 234 | QVKVVDPAFL | 28627 |
| HPV33 | L2 | 8 | 321 | RIHYYQDL | 28628 |
| HPV33 | L2 | 11 | 321 | RIHYYQDLSPI | 28629 |
| HPV33 | L2 | 11 | 289 | RPAITSRRHTV | 28630 |
| HPV33 | L2 | 9 | 89 | RPPVTVDTV | 28631 |
| HPV33 | L2 | 8 | 220 | RPVARLGL | 28632 |
| HPV33 | L2 | 9 | 220 | RPVARLGLY | 28633 |
| HPV33 | L2 | 8 | 303 | RVGQKATL | 28634 |
| HPV33 | L2 | 9 | 357 | SINDGLYDV | 28635 |
| HPV33 | L2 | 10 | 357 | SINDGLYDVY | 28636 |
| HPV33 | L2 | 11 | 357 | SINDGLYDVYA | 28637 |
| HPV33 | L2 | 8 | 393 | SIPLNTGF | 28638 |
| HPV33 | L2 | 8 | 122 | SIPTPSGF | 28639 |
| HPV33 | L2 | 10 | 122 | SIPTPSGFDV | 28640 |
| HPV33 | L2 | 9 | 151 | SIQTISTHL | 28641 |
| HPV33 | L2 | 11 | 103 | SIVSLIEETSF | 28642 |
| HPV33 | L2 | 9 | 49 | SLGVFFGGL | 28643 |
| HPV33 | L2 | 11 | 49 | SLGVFFGGLGI | 28644 |
| HPV33 | L2 | 8 | 106 | SLIEETSF | 28645 |
| HPV33 | L2 | 9 | 106 | SLIEETSFI | 28646 |
| HPV33 | L2 | 11 | 106 | SLIEETSFIEA | 28647 |
| HPV33 | L2 | 8 | 274 | SPAPDPDF | 28648 |
| HPV33 | L2 | 9 | 274 | SPAPDPDFL | 28649 |
| HPV33 | L2 | 11 | 274 | SPAPDPDFLDI | 28650 |
| HPV33 | L2 | 9 | 425 | SPFFPFDTI | 28651 |
| HPV33 | L2 | 10 | 425 | SPFFPFDTIV | 28652 |
| HPV33 | L2 | 11 | 425 | SPFFPFDTIVV | 28653 |
| HPV33 | L2 | 9 | 419 | SPFVPISPF | 28654 |
| HPV33 | L2 | 10 | 419 | SPFVPISPFF | 28655 |
| HPV33 | L2 | 8 | 245 | SPHKLITY | 28656 |
| HPV33 | L2 | 10 | 329 | SPIVPLDHTV | 28657 |
| HPV33 | L2 | 10 | 412 | SPLFPTSSPF | 28658 |
| HPV33 | L2 | 11 | 412 | SPLFPTSSPFV | 28659 |

TABLE XIV-continued

B62 Supermotif Peptides

| Type | Protein | No. of Amino Acid | Position | Sequence | Seq. Id. No. |
|---|---|---|---|---|---|
| HPV33 | L2 | 9 | 185 | SPTVSTQSY | 28660 |
| HPV33 | L2 | 10 | 146 | SVGESSIQTI | 28661 |
| HPV33 | L2 | 9 | 167 | SVLHPPAPA | 28662 |
| HPV33 | L2 | 11 | 167 | SVLHPPAPAEA | 28663 |
| HPV33 | L2 | 9 | 39 | TIADQILKY | 28664 |
| HPV33 | L2 | 10 | 154 | TISTHLNPTF | 28665 |
| HPV33 | L2 | 9 | 432 | TIVVDGADF | 28666 |
| HPV33 | L2 | 10 | 432 | TIVVDGADFV | 28667 |
| HPV33 | L2 | 11 | 432 | TIVVDGADFVL | 28668 |
| HPV33 | L2 | 10 | 309 | TLKTRSGKQI | 28669 |
| HPV33 | L2 | 9 | 265 | TLQFQHSDI | 28670 |
| HPV33 | L2 | 10 | 138 | TPAIINVSSV | 28671 |
| HPV33 | L2 | 9 | 214 | TPIPGSRPV | 28672 |
| HPV33 | L2 | 10 | 214 | TPIPGSRPVA | 28673 |
| HPV33 | L2 | 10 | 375 | TPMQHSYSTF | 28674 |
| HPV33 | L2 | 11 | 375 | TPMQHSYSTFA | 28675 |
| HPV33 | L2 | 11 | 125 | TPSGFDVTTSA | 28676 |
| HPV33 | L2 | 9 | 402 | TPVMSGPDI | 28677 |
| HPV33 | L2 | 9 | 15 | TQLYQTCKA | 28678 |
| HPV33 | L2 | 10 | 232 | TQQVKVVDPA | 28679 |
| HPV33 | L2 | 11 | 232 | TQQVKVVDPAF | 28680 |
| HPV33 | L2 | 9 | 190 | TQSYENIPM | 28681 |
| HPV33 | L2 | 8 | 93 | TVDTVGPL | 28682 |
| HPV33 | L2 | 9 | 96 | TVGPLDSSI | 28683 |
| HPV33 | L2 | 10 | 96 | TVGPLDSSIV | 28684 |
| HPV33 | L2 | 9 | 337 | TVPNEQYEL | 28685 |
| HPV33 | L2 | 11 | 298 | TVRFSRVGQKA | 28686 |
| HPV33 | L2 | 10 | 187 | TVSTQSYENI | 28687 |
| HPV33 | L2 | 10 | 31 | VIPKVEGSTI | 28688 |
| HPV33 | L2 | 11 | 31 | VIPKVEGSTIA | 28689 |
| HPV33 | L2 | 8 | 168 | VLHPPAPA | 28690 |
| HPV33 | L2 | 10 | 168 | VLHPPAPAEA | 28691 |
| HPV33 | L2 | 8 | 441 | VLHPSYFI | 28692 |
| HPV33 | L2 | 9 | 441 | VLHPSYFIL | 28693 |
| HPV33 | L2 | 11 | 404 | VMSGPDIPSPL | 28694 |
| HPV33 | L2 | 10 | 72 | VPIGTDPPTA | 28695 |
| HPV33 | L2 | 11 | 72 | VPIGTDPPTAA | 28696 |
| HPV33 | L2 | 9 | 422 | VPISPFFPF | 28697 |
| HPV33 | L2 | 8 | 338 | VPNEQYEL | 28698 |
| HPV33 | L2 | 11 | 338 | VPNEQYELQPL | 28699 |
| HPV33 | L2 | 8 | 434 | VVDGADFV | 28700 |
| HPV33 | L2 | 9 | 434 | VVDGADFVL | 28701 |
| HPV33 | L2 | 9 | 202 | VVSTDSSNV | 28702 |
| HPV33 | L2 | 8 | 325 | YQDLSPIV | 28703 |
| HPV33 | L2 | 10 | 325 | YQDLSPIVPL | 28704 |
| HPV33 | L2 | 11 | 71 | YVPIGTDPPTA | 28705 |
| HPV45 | E1 | 9 | 232 | AIFGVNPTV | 28706 |
| HPV45 | E1 | 10 | 232 | AIFGVNPTVA | 28707 |
| HPV45 | E1 | 9 | 532 | ALDGNPISI | 28708 |
| HPV45 | E1 | 8 | 68 | ALFHAQEV | 28709 |
| HPV45 | E1 | 9 | 311 | ALYWYRTGI | 28710 |
| HPV45 | E1 | 9 | 199 | AMLAVFKDI | 28711 |
| HPV45 | E1 | 10 | 199 | AMLAVFKDIY | 28712 |
| HPV45 | E1 | 11 | 512 | AMLDDATHTCW | 28713 |
| HPV45 | E1 | 10 | 66 | AQALFHAQEV | 28714 |
| HPV45 | E1 | 8 | 72 | AQEVQNDA | 28715 |
| HPV45 | E1 | 10 | 72 | AQEVQNDAQV | 28716 |
| HPV45 | E1 | 11 | 72 | AQEVQNDAQVL | 28717 |
| HPV45 | E1 | 8 | 408 | AQKRQMNM | 28718 |
| HPV45 | E1 | 11 | 408 | AQKRQMNMSQW | 28719 |
| HPV45 | E1 | 10 | 373 | AQLADCNSNA | 28720 |
| HPV45 | E1 | 11 | 373 | AQLADCNSNAA | 28721 |
| HPV45 | E1 | 11 | 79 | AQVLHLLKRKF | 28722 |
| HPV45 | E1 | 9 | 202 | AVFKDIYGL | 28723 |
| HPV45 | E1 | 11 | 202 | AVFKDIYGLSF | 28724 |
| HPV45 | E1 | 10 | 399 | AVMCRHYKRA | 28725 |
| HPV45 | E1 | 8 | 465 | CILLYGPA | 28726 |
| HPV45 | E1 | 8 | 259 | CLDCKWGV | 28727 |
| HPV45 | E1 | 9 | 259 | CLDCKWGVL | 28728 |
| HPV45 | E1 | 10 | 259 | CLDCKWGVLI | 28729 |
| HPV45 | E1 | 11 | 259 | CLDCKWGVLIL | 28730 |
| HPV45 | E1 | 9 | 297 | CMLIEPPKL | 28731 |
| HPV45 | E1 | 10 | 552 | CPPILLTSNI | 28732 |
| HPV45 | E1 | 10 | 390 | CQAKYLKDCA | 28733 |
| HPV45 | E1 | 11 | 390 | CQAKYLKDCAV | 28734 |

TABLE XIV-continued

B62 Supermotif Peptides

| Type | Protein | No. of Amino Acid | Position | Sequence | Seq. Id. No. |
|---|---|---|---|---|---|
| HPV45 | E1 | 10 | 634 | CVTGQNTRPL | 28735 |
| HPV45 | E1 | 10 | 206 | DIYGLSFTDL | 28736 |
| HPV45 | E1 | 11 | 206 | DIYGLSFTDLV | 28737 |
| HPV45 | E1 | 9 | 614 | DLHEDDEDA | 28738 |
| HPV45 | E1 | 8 | 349 | DLSDMVQW | 28739 |
| HPV45 | E1 | 9 | 349 | DLSDMVQWA | 28740 |
| HPV45 | E1 | 10 | 349 | DLSDMVQWAF | 28741 |
| HPV45 | E1 | 9 | 108 | DLSPRLQEI | 28742 |
| HPV45 | E1 | 11 | 108 | DLSPRLQEISL | 28743 |
| HPV45 | E1 | 8 | 361 | DLTDESDM | 28744 |
| HPV45 | E1 | 9 | 361 | DLTDESDMA | 28745 |
| HPV45 | E1 | 10 | 361 | DLTDESDMAF | 28746 |
| HPV45 | E1 | 9 | 367 | DMAFQYAQL | 28747 |
| HPV45 | E1 | 10 | 367 | DMAFQYAQLA | 28748 |
| HPV45 | E1 | 10 | 46 | DMVDFIDTQL | 28749 |
| HPV45 | E1 | 11 | 352 | DMVQWAFDNDL | 28750 |
| HPV45 | E1 | 8 | 562 | DPAKDNKW | 28751 |
| HPV45 | E1 | 10 | 562 | DPAKDNKWPY | 28752 |
| HPV45 | E1 | 11 | 562 | DPAKDNKWPYL | 28753 |
| HPV45 | E1 | 9 | 179 | DPHCSITEL | 28754 |
| HPV45 | E1 | 11 | 30 | DVISDDEDETA | 28755 |
| HPV45 | E1 | 10 | 596 | EINDKNWKCF | 28756 |
| HPV45 | E1 | 11 | 596 | EINDKNWKCFF | 28757 |
| HPV45 | E1 | 11 | 115 | EISLNSGHKKA | 28758 |
| HPV45 | E1 | 8 | 186 | ELKELLQA | 28759 |
| HPV45 | E1 | 10 | 189 | ELLQASNKKA | 28760 |
| HPV45 | E1 | 11 | 189 | ELLQASNKKAA | 28761 |
| HPV45 | E1 | 8 | 504 | EPLADTKV | 28762 |
| HPV45 | E1 | 9 | 504 | EPLADTKVA | 28763 |
| HPV45 | E1 | 10 | 504 | EPLADTKVAM | 28764 |
| HPV45 | E1 | 11 | 504 | EPLADTKVAML | 28765 |
| HPV45 | E1 | 9 | 301 | EPPKLRSSV | 28766 |
| HPV45 | E1 | 10 | 301 | EPPKLRSSVA | 28767 |
| HPV45 | E1 | 11 | 301 | EPPKLRSSVAA | 28768 |
| HPV45 | E1 | 8 | 59 | EQAEQETA | 28769 |
| HPV45 | E1 | 10 | 59 | EQAEQETAQA | 28770 |
| HPV45 | E1 | 11 | 59 | EQAEQETAQAL | 28771 |
| HPV45 | E1 | 8 | 62 | EQETAQAL | 28772 |
| HPV45 | E1 | 9 | 62 | EQETAQALF | 28773 |
| HPV45 | E1 | 11 | 62 | EQETAQALFHA | 28774 |
| HPV45 | E1 | 9 | 101 | EQLSVDTDL | 28775 |
| HPV45 | E1 | 9 | 141 | EVEAAETQV | 28776 |
| HPV45 | E1 | 11 | 141 | EVEAAETQVTV | 28777 |
| HPV45 | E1 | 8 | 74 | EVQNDAQV | 28778 |
| HPV45 | E1 | 9 | 74 | EVQNDAQVL | 28779 |
| HPV45 | E1 | 11 | 74 | EVQNDAQVLHL | 28780 |
| HPV45 | E1 | 9 | 324 | EVSGDTPEW | 28781 |
| HPV45 | E1 | 10 | 324 | EVSGDTPEWI | 28782 |
| HPV45 | E1 | 8 | 50 | FIDTQLSI | 28783 |
| HPV45 | E1 | 8 | 483 | FIHFLQGA | 28784 |
| HPV45 | E1 | 9 | 483 | FIHFLQGAI | 28785 |
| HPV45 | E1 | 10 | 483 | FIHFLQGAII | 28786 |
| HPV45 | E1 | 8 | 446 | FISFLRAL | 28787 |
| HPV45 | E1 | 11 | 446 | FISFLRALKEF | 28788 |
| HPV45 | E1 | 11 | 456 | FLKGTPKKNCI | 28789 |
| HPV45 | E1 | 8 | 385 | FLKSNCQA | 28790 |
| HPV45 | E1 | 10 | 385 | FLKSNCQAKY | 28791 |
| HPV45 | E1 | 11 | 385 | FLKSNCQAKYL | 28792 |
| HPV45 | E1 | 9 | 486 | FLQGAIISF | 28793 |
| HPV45 | E1 | 10 | 486 | FLQGAIISFV | 28794 |
| HPV45 | E1 | 8 | 449 | FLRALKEF | 28795 |
| HPV45 | E1 | 9 | 449 | FLRALKEFL | 28796 |
| HPV45 | E1 | 9 | 438 | FLRYQGVEF | 28797 |
| HPV45 | E1 | 10 | 438 | FLRYQGVEFI | 28798 |
| HPV45 | E1 | 10 | 585 | FPFDKNGNPV | 28799 |
| HPV45 | E1 | 11 | 585 | FPFDKNGNPVY | 28800 |
| HPV45 | E1 | 8 | 494 | FVNSNSHF | 28801 |
| HPV45 | E1 | 9 | 494 | FVNSNSHFW | 28802 |
| HPV45 | E1 | 10 | 494 | FVNSNSHFWL | 28803 |
| HPV45 | E1 | 9 | 342 | GIDDSNFDL | 28804 |
| HPV45 | E1 | 10 | 626 | GIPFGTFKCV | 28805 |
| HPV45 | E1 | 8 | 318 | GISNISEV | 28806 |
| HPV45 | E1 | 8 | 209 | GLSFTDLV | 28807 |
| HPV45 | E1 | 11 | 209 | GLSFTDLVRNF | 28808 |
| HPV45 | E1 | 8 | 286 | GLSTLLHV | 28809 |

TABLE XIV-continued

B62 Supermotif Peptides

| Type | Protein | No. of Amino Acid | Position | Sequence | Seq. Id. No. |
|---|---|---|---|---|---|
| HPV45 | E1 | 8 | 480 | GMSFIHFL | 28810 |
| HPV45 | E1 | 11 | 480 | GMSFIHFLQGA | 28811 |
| HPV45 | E1 | 9 | 470 | GPANTGKSY | 28812 |
| HPV45 | E1 | 10 | 470 | GPANTGKSYF | 28813 |
| HPV45 | E1 | 8 | 443 | GVEFISFL | 28814 |
| HPV45 | E1 | 10 | 443 | GVEFISFLRA | 28815 |
| HPV45 | E1 | 11 | 443 | GVEFISFLRAL | 28816 |
| HPV45 | E1 | 8 | 265 | GVLILALL | 28817 |
| HPV45 | E1 | 10 | 265 | GVLILALLRY | 28818 |
| HPV45 | E1 | 10 | 235 | GVNPTVAEGF | 28819 |
| HPV45 | E1 | 9 | 256 | HIQCLDCKW | 28820 |
| HPV45 | E1 | 11 | 256 | HIQCLDCKWGV | 28821 |
| HPV45 | E1 | 8 | 83 | HLLKRKFA | 28822 |
| HPV45 | E1 | 8 | 292 | HVPETCML | 28823 |
| HPV45 | E1 | 9 | 292 | HVPETCMLI | 28824 |
| HPV45 | E1 | 11 | 338 | IIQHGIDDSNF | 28825 |
| HPV45 | E1 | 11 | 491 | IISFVNSNSHF | 28826 |
| HPV45 | E1 | 10 | 555 | ILLTSNIDPA | 28827 |
| HPV45 | E1 | 9 | 627 | IPFGTFKCV | 28828 |
| HPV45 | E1 | 8 | 257 | IQCLDCKW | 28829 |
| HPV45 | E1 | 10 | 257 | IQCLDCKWGV | 28830 |
| HPV45 | E1 | 11 | 257 | IQCLDCKWGVL | 28831 |
| HPV45 | E1 | 10 | 339 | IQHGIDDSNF | 28832 |
| HPV45 | E1 | 11 | 333 | IQRLTIIQHGI | 28833 |
| HPV45 | E1 | 9 | 23 | IVEKKTGDV | 28834 |
| HPV45 | E1 | 10 | 23 | IVEKKTGDVI | 28835 |
| HPV45 | E1 | 10 | 435 | IVQFLRYQGV | 28836 |
| HPV45 | E1 | 8 | 425 | KIDEGGDW | 28837 |
| HPV45 | E1 | 11 | 425 | KIDEGGDWRPI | 28838 |
| HPV45 | E1 | 8 | 304 | KLRSSVAA | 28839 |
| HPV45 | E1 | 9 | 304 | KLRSSVAAL | 28840 |
| HPV45 | E1 | 10 | 304 | KLRSSVAALY | 28841 |
| HPV45 | E1 | 11 | 304 | KLRSSVAALYW | 28842 |
| HPV45 | E1 | 9 | 249 | KPATLYAHI | 28843 |
| HPV45 | E1 | 11 | 545 | KPLLQLKCPPI | 28844 |
| HPV45 | E1 | 8 | 510 | KVAMLDDA | 28845 |
| HPV45 | E1 | 11 | 299 | LIEPPKLRSSV | 28846 |
| HPV45 | E1 | 8 | 247 | LIKPATLY | 28847 |
| HPV45 | E1 | 9 | 247 | LIKPATLYA | 28848 |
| HPV45 | E1 | 11 | 247 | LIKPATLYAHI | 28849 |
| HPV45 | E1 | 8 | 267 | LILALLRY | 28850 |
| HPV45 | E1 | 9 | 290 | LLHVPETCM | 28851 |
| HPV45 | E1 | 10 | 290 | LLHVPETCML | 28852 |
| HPV45 | E1 | 11 | 290 | LLHVPETCMLI | 28853 |
| HPV45 | E1 | 9 | 190 | LLQASNKKA | 28854 |
| HPV45 | E1 | 10 | 190 | LLQASNKKAA | 28855 |
| HPV45 | E1 | 11 | 190 | LLQASNKKAAM | 28856 |
| HPV45 | E1 | 9 | 547 | LLQLKCPPI | 28857 |
| HPV45 | E1 | 10 | 547 | LLQLKCPPIL | 28858 |
| HPV45 | E1 | 11 | 547 | LLQLKCPPILL | 28859 |
| HPV45 | E1 | 11 | 271 | LLRYKCGKNRL | 28860 |
| HPV45 | E1 | 9 | 556 | LLTSNIDPA | 28861 |
| HPV45 | E1 | 8 | 191 | LQASNKKA | 28862 |
| HPV45 | E1 | 9 | 191 | LQASNKKAA | 28863 |
| HPV45 | E1 | 10 | 191 | LQASNKKAAM | 28864 |
| HPV45 | E1 | 11 | 191 | LQASNKKAAML | 28865 |
| HPV45 | E1 | 8 | 487 | LQGAIISF | 28866 |
| HPV45 | E1 | 9 | 487 | LQGAIISFV | 28867 |
| HPV45 | E1 | 8 | 548 | LQLKCPPI | 28868 |
| HPV45 | E1 | 9 | 548 | LQLKCPPIL | 28869 |
| HPV45 | E1 | 10 | 548 | LQLKCPPILL | 28870 |
| HPV45 | E1 | 8 | 200 | MLAVFKDI | 28871 |
| HPV45 | E1 | 9 | 200 | MLAVFKDIY | 28872 |
| HPV45 | E1 | 11 | 200 | MLAVFKDIYGL | 28873 |
| HPV45 | E1 | 10 | 513 | MLDDATHTCW | 28874 |
| HPV45 | E1 | 8 | 298 | MLIEPPKL | 28875 |
| HPV45 | E1 | 9 | 47 | MVDFIDTQL | 28876 |
| HPV45 | E1 | 11 | 47 | MVDFIDTQLSI | 28877 |
| HPV45 | E1 | 10 | 353 | MVQWAFDNDL | 28878 |
| HPV45 | E1 | 10 | 560 | NIDPAKDNKW | 28879 |
| HPV45 | E1 | 8 | 414 | NMSQWIKY | 28880 |
| HPV45 | E1 | 8 | 237 | NPTVAEGF | 28881 |
| HPV45 | E1 | 11 | 237 | NPTVAEGFKTL | 28882 |
| HPV45 | E1 | 11 | 592 | NPVYEINDKNW | 28883 |
| HPV45 | E1 | 8 | 177 | NVDPHCSI | 28884 |

TABLE XIV-continued

B62 Supermotif Peptides

| Type | Protein | No. of Amino Acid | Position | Sequence | Seq. Id. No. |
|---|---|---|---|---|---|
| HPV45 | E1 | 11 | 177 | NVDPHCSITEL | 28885 |
| HPV45 | E1 | 8 | 554 | PILLTSNI | 28886 |
| HPV45 | E1 | 11 | 554 | PILLTSNIDPA | 28887 |
| HPV45 | E1 | 11 | 537 | PISIDRKHKPL | 28888 |
| HPV45 | E1 | 8 | 434 | PIVQFLRY | 28889 |
| HPV45 | E1 | 11 | 434 | PIVQFLRYQGV | 28890 |
| HPV45 | E1 | 8 | 505 | PLADTKVA | 28891 |
| HPV45 | E1 | 9 | 505 | PLADTKVAM | 28892 |
| HPV45 | E1 | 10 | 505 | PLADTKVAML | 28893 |
| HPV45 | E1 | 8 | 98 | PLGEQLSV | 28894 |
| HPV45 | E1 | 10 | 546 | PLLQLKCPPI | 28895 |
| HPV45 | E1 | 11 | 546 | PLLQLKCPPIL | 28896 |
| HPV45 | E1 | 9 | 553 | PPILLTSNI | 28897 |
| HPV45 | E1 | 8 | 302 | PPKLRSSV | 28898 |
| HPV45 | E1 | 9 | 302 | PPKLRSSVA | 28899 |
| HPV45 | E1 | 10 | 302 | PPKLRSSVAA | 28900 |
| HPV45 | E1 | 11 | 302 | PPKLRSSVAAL | 28901 |
| HPV45 | E1 | 10 | 593 | PVYEINDKNW | 28902 |
| HPV45 | E1 | 9 | 374 | QLADCNSNA | 28903 |
| HPV45 | E1 | 10 | 374 | QLADCNSNAA | 28904 |
| HPV45 | E1 | 11 | 374 | QLADCNSNAAA | 28905 |
| HPV45 | E1 | 8 | 549 | QLKCPPIL | 28906 |
| HPV45 | E1 | 9 | 549 | QLKCPPILL | 28907 |
| HPV45 | E1 | 8 | 54 | QLSICEQA | 28908 |
| HPV45 | E1 | 8 | 102 | QLSVDTDL | 28909 |
| HPV45 | E1 | 8 | 412 | QMNMSQWI | 28910 |
| HPV45 | E1 | 10 | 412 | QMNMSQWIKY | 28911 |
| HPV45 | E1 | 10 | 80 | QVLHLLRKF | 28912 |
| HPV45 | E1 | 11 | 80 | QVLHLLRKFA | 28913 |
| HPV45 | E1 | 8 | 148 | QVTVNTNA | 28914 |
| HPV45 | E1 | 11 | 612 | RLDLHEDDEDA | 28915 |
| HPV45 | E1 | 10 | 128 | RLFTISDSGY | 28916 |
| HPV45 | E1 | 9 | 335 | RLTIIQHGI | 28917 |
| HPV45 | E1 | 8 | 280 | RLTVAKGL | 28918 |
| HPV45 | E1 | 11 | 280 | RLTVAKGLSTL | 28919 |
| HPV45 | E1 | 9 | 433 | RPIVQFLRY | 28920 |
| HPV45 | E1 | 8 | 411 | RQMNMSQW | 28921 |
| HPV45 | E1 | 9 | 411 | RQMNMSQWI | 28922 |
| HPV45 | E1 | 11 | 411 | RQMNMSQWIKY | 28923 |
| HPV45 | E1 | 10 | 575 | RVTVFTFPHA | 28924 |
| HPV45 | E1 | 11 | 575 | RVTVFTFPHAF | 28925 |
| HPV45 | E1 | 11 | 56 | SICEQAEQETA | 28926 |
| HPV45 | E1 | 9 | 539 | SIDRKHKPL | 28927 |
| HPV45 | E1 | 10 | 539 | SIDRKHKPLL | 28928 |
| HPV45 | E1 | 8 | 183 | SITELKEL | 28929 |
| HPV45 | E1 | 9 | 183 | SITELKELL | 28930 |
| HPV45 | E1 | 11 | 183 | SITELKELLQA | 28931 |
| HPV45 | E1 | 9 | 117 | SLNSGHKKA | 28932 |
| HPV45 | E1 | 9 | 97 | SPLGEQLSV | 28933 |
| HPV45 | E1 | 9 | 110 | SPRLQEISL | 28934 |
| HPV45 | E1 | 11 | 416 | SQWIKYRCSKI | 28935 |
| HPV45 | E1 | 8 | 308 | SVAALYWY | 28936 |
| HPV45 | E1 | 10 | 104 | SVDTDLSPRL | 28937 |
| HPV45 | E1 | 10 | 22 | TIVEKKTGDV | 28938 |
| HPV45 | E1 | 11 | 22 | TIVEKKTGDVI | 28939 |
| HPV45 | E1 | 8 | 246 | TLIKPATL | 28940 |
| HPV45 | E1 | 9 | 246 | TLIKPATLY | 28941 |
| HPV45 | E1 | 10 | 246 | TLIKPATLYA | 28942 |
| HPV45 | E1 | 10 | 289 | TLLHVPETCM | 28943 |
| HPV45 | E1 | 11 | 289 | TLLHVPETCML | 28944 |
| HPV45 | E1 | 9 | 252 | TLYAHIQCL | 28945 |
| HPV45 | E1 | 8 | 329 | TPEWIQRL | 28946 |
| HPV45 | E1 | 10 | 329 | TPEWIQRLTI | 28947 |
| HPV45 | E1 | 11 | 329 | TPEWIQRLTII | 28948 |
| HPV45 | E1 | 8 | 460 | TPKKNCIL | 28949 |
| HPV45 | E1 | 9 | 460 | TPKKNCILL | 28950 |
| HPV45 | E1 | 10 | 460 | TPKKNCILLY | 28951 |
| HPV45 | E1 | 9 | 53 | TQLSICEQA | 28952 |
| HPV45 | E1 | 9 | 147 | TQVTVNTNA | 28953 |
| HPV45 | E1 | 9 | 239 | TVAEGFKTL | 28954 |
| HPV45 | E1 | 10 | 239 | TVAEGFKTLI | 28955 |
| HPV45 | E1 | 9 | 282 | TVAKGLSTL | 28956 |
| HPV45 | E1 | 10 | 282 | TVAKGLSTLL | 28957 |
| HPV45 | E1 | 8 | 577 | TVFTFPHA | 28958 |
| HPV45 | E1 | 9 | 577 | TVFTFPHAF | 28959 |

TABLE XIV-continued

B62 Supermotif Peptides

| Type | Protein | No. of Amino Acid | Position | Sequence | Seq. Id. No. |
|---|---|---|---|---|---|
| HPV45 | E1 | 11 | 577 | TVFTFPHAFPF | 28960 |
| HPV45 | E1 | 10 | 31 | VISDDEDETA | 28961 |
| HPV45 | E1 | 9 | 81 | VLHLLKRKF | 28962 |
| HPV45 | E1 | 10 | 81 | VLHLLKRKFA | 28963 |
| HPV45 | E1 | 9 | 266 | VLILALLRY | 28964 |
| HPV45 | E1 | 11 | 230 | VMAIFGVNPTV | 28965 |
| HPV45 | E1 | 9 | 400 | VMCRHYKRA | 28966 |
| HPV45 | E1 | 8 | 293 | VPETCMLI | 28967 |
| HPV45 | E1 | 9 | 436 | VQFLRYQGV | 28968 |
| HPV45 | E1 | 11 | 436 | VQFLRYQGVEF | 28969 |
| HPV45 | E1 | 8 | 75 | VQNDAQVL | 28970 |
| HPV45 | E1 | 10 | 75 | VQNDAQVLHL | 28971 |
| HPV45 | E1 | 11 | 75 | VQNDAQVLHLL | 28972 |
| HPV45 | E1 | 9 | 354 | VQWAFDNDL | 28973 |
| HPV45 | E1 | 9 | 418 | WIKYRCSKI | 28974 |
| HPV45 | E1 | 8 | 332 | WIQRLTII | 28975 |
| HPV45 | E1 | 10 | 502 | WLEPLADTKV | 28976 |
| HPV45 | E1 | 11 | 502 | WLEPLADTKVA | 28977 |
| HPV45 | E1 | 8 | 569 | WPYLESRV | 28978 |
| HPV45 | E1 | 10 | 569 | WPYLESRVTV | 28979 |
| HPV45 | E1 | 11 | 569 | WPYLESRVTVF | 28980 |
| HPV45 | E1 | 8 | 229 | WVMAIFGV | 28981 |
| HPV45 | E1 | 8 | 571 | YLESRVTV | 28982 |
| HPV45 | E1 | 9 | 571 | YLESRVTVF | 28983 |
| HPV45 | E1 | 11 | 571 | YLESRVTVFTF | 28984 |
| HPV45 | E1 | 8 | 394 | YLKDCAVM | 28985 |
| HPV45 | E1 | 11 | 528 | YMRNALDGNPI | 28986 |
| HPV45 | E1 | 9 | 441 | YQGVEFISF | 28987 |
| HPV45 | E1 | 10 | 441 | YQGVEFISFL | 28988 |
| HPV45 | E2 | 8 | 78 | AIELQMAL | 28989 |
| HPV45 | E2 | 11 | 78 | AIELQMALKGL | 28990 |
| HPV45 | E2 | 11 | 47 | AILFTAREHGI | 28991 |
| HPV45 | E2 | 10 | 84 | ALKGLAQSKY | 28992 |
| HPV45 | E2 | 10 | 16 | ALQDKILDHY | 28993 |
| HPV45 | E2 | 10 | 89 | AQSKYNNEEW | 28994 |
| HPV45 | E2 | 9 | 305 | CLRYRLRKY | 28995 |
| HPV45 | E2 | 10 | 305 | CLRYRLRKYA | 28996 |
| HPV45 | E2 | 10 | 134 | CMNYVVWDSI | 28997 |
| HPV45 | E2 | 11 | 134 | CMNYVVWDSIY | 28998 |
| HPV45 | E2 | 8 | 158 | CVSYWGVY | 28999 |
| HPV45 | E2 | 9 | 158 | CVSYWGVYY | 29000 |
| HPV45 | E2 | 10 | 158 | CVSYWGVYYI | 29001 |
| HPV45 | E2 | 8 | 31 | DINSQISY | 29002 |
| HPV45 | E2 | 9 | 31 | DINSQISYW | 29003 |
| HPV45 | E2 | 11 | 31 | DINSQISYWQL | 29004 |
| HPV45 | E2 | 9 | 351 | DVVTIPNSV | 29005 |
| HPV45 | E2 | 11 | 351 | DVVTIPNSVQI | 29006 |
| HPV45 | E2 | 8 | 319 | EISSTWHW | 29007 |
| HPV45 | E2 | 9 | 80 | ELQMALKGL | 29008 |
| HPV45 | E2 | 10 | 80 | ELQMALKGLA | 29009 |
| HPV45 | E2 | 11 | 106 | ELWNTEPSQCF | 29010 |
| HPV45 | E2 | 11 | 258 | EQHHGRVNTHV | 29011 |
| HPV45 | E2 | 8 | 343 | EVQRNTFL | 29012 |
| HPV45 | E2 | 10 | 343 | EVQRNTFLDV | 29013 |
| HPV45 | E2 | 11 | 343 | EVQRNTFLDVV | 29014 |
| HPV45 | E2 | 8 | 192 | EVQYGGNV | 29015 |
| HPV45 | E2 | 9 | 192 | EVQYGGNVI | 29016 |
| HPV45 | E2 | 11 | 349 | FLDVVTIPNSV | 29017 |
| HPV45 | E2 | 11 | 334 | GILTVTYNSEV | 29018 |
| HPV45 | E2 | 9 | 56 | GITKLNHQV | 29019 |
| HPV45 | E2 | 10 | 56 | GITKLNHQVV | 29020 |
| HPV45 | E2 | 8 | 150 | GIWDKTAA | 29021 |
| HPV45 | E2 | 10 | 150 | GIWDKTAACV | 29022 |
| HPV45 | E2 | 10 | 255 | GLTEQHHGRV | 29023 |
| HPV45 | E2 | 9 | 295 | HLKGDKNSL | 29024 |
| HPV45 | E2 | 9 | 62 | HQVVPPINI | 29025 |
| HPV45 | E2 | 11 | 293 | IIHLKGDKNSL | 29026 |
| HPV45 | E2 | 10 | 48 | ILFTAREHGI | 29027 |
| HPV45 | E2 | 10 | 335 | ILTVTYNSEV | 29028 |
| HPV45 | E2 | 9 | 355 | IPNSVQISV | 29029 |
| HPV45 | E2 | 11 | 355 | IPNSVQISVGY | 29030 |
| HPV45 | E2 | 8 | 219 | IVRQLQHA | 29031 |
| HPV45 | E2 | 10 | 59 | KLNHQVVPPI | 29032 |
| HPV45 | E2 | 9 | 2 | KMQTPKESL | 29033 |
| HPV45 | E2 | 8 | 240 | KPHIQTPA | 29034 |

TABLE XIV-continued

B62 Supermotif Peptides

| Type | Protein | No. of Amino Acid | Position | Sequence | Seq. Id. No. |
|---|---|---|---|---|---|
| HPV45 | E2 | 10 | 284 | KVCSGNTTPI | 29035 |
| HPV45 | E2 | 11 | 284 | KVCSGNTTPII | 29036 |
| HPV45 | E2 | 8 | 41 | LIRLENAI | 29037 |
| HPV45 | E2 | 9 | 41 | LIRLENAIL | 29038 |
| HPV45 | E2 | 10 | 41 | LIRLENAILF | 29039 |
| HPV45 | E2 | 9 | 17 | LQDKILDHY | 29040 |
| HPV45 | E2 | 8 | 100 | LQDTCEEL | 29041 |
| HPV45 | E2 | 9 | 100 | LQDTCEELW | 29042 |
| HPV45 | E2 | 8 | 81 | LQMALKGL | 29043 |
| HPV45 | E2 | 9 | 81 | LQMALKGLA | 29044 |
| HPV45 | E2 | 8 | 3 | MQTPKESL | 29045 |
| HPV45 | E2 | 10 | 69 | NISKSKAHKA | 29046 |
| HPV45 | E2 | 11 | 69 | NISKSKAHKAI | 29047 |
| HPV45 | E2 | 9 | 198 | NVIDCNDSM | 29048 |
| HPV45 | E2 | 9 | 67 | PINISKSKA | 29049 |
| HPV45 | E2 | 10 | 66 | PPINISKSKA | 29050 |
| HPV45 | E2 | 9 | 360 | QISVGYMTI | 29051 |
| HPV45 | E2 | 8 | 35 | QISYWQLI | 29052 |
| HPV45 | E2 | 10 | 35 | QISYWQLIRL | 29053 |
| HPV45 | E2 | 9 | 218 | QIVRQLQHA | 29054 |
| HPV45 | E2 | 8 | 40 | QLIRLENA | 29055 |
| HPV45 | E2 | 9 | 40 | QLIRLENAI | 29056 |
| HPV45 | E2 | 10 | 40 | QLIRLENAIL | 29057 |
| HPV45 | E2 | 11 | 40 | QLIRLENAILF | 29058 |
| HPV45 | E2 | 8 | 82 | QMALKGLA | 29059 |
| HPV45 | E2 | 8 | 63 | QVVPPINI | 29060 |
| HPV45 | E2 | 8 | 43 | RLENAILF | 29061 |
| HPV45 | E2 | 10 | 43 | RLENAILFTA | 29062 |
| HPV45 | E2 | 9 | 309 | RLRKYADHY | 29063 |
| HPV45 | E2 | 9 | 13 | RLSALQDKI | 29064 |
| HPV45 | E2 | 10 | 13 | RLSALQDKIL | 29065 |
| HPV45 | E2 | 10 | 263 | RVNTHVHNPL | 29066 |
| HPV45 | E2 | 11 | 263 | RVNTHVHNPLL | 29067 |
| HPV45 | E2 | 10 | 142 | SIYYITETGI | 29068 |
| HPV45 | E2 | 11 | 142 | SIYYITETGIW | 29069 |
| HPV45 | E2 | 9 | 302 | SLKCLRYRL | 29070 |
| HPV45 | E2 | 8 | 9 | SLSERLSA | 29071 |
| HPV45 | E2 | 9 | 9 | SLSERLSAL | 29072 |
| HPV45 | E2 | 10 | 205 | SMCSTSDDTV | 29073 |
| HPV45 | E2 | 11 | 113 | SQCFKKGGKTV | 29074 |
| HPV45 | E2 | 8 | 34 | SQISYWQL | 29075 |
| HPV45 | E2 | 9 | 34 | SQISYWQLI | 29076 |
| HPV45 | E2 | 11 | 34 | SQISYWQLIRL | 29077 |
| HPV45 | E2 | 9 | 235 | SVGTPKPHI | 29078 |
| HPV45 | E2 | 8 | 358 | SVQISVGY | 29079 |
| HPV45 | E2 | 9 | 358 | SVQISVGYM | 29080 |
| HPV45 | E2 | 11 | 358 | SVQISVGYMTI | 29081 |
| HPV45 | E2 | 8 | 354 | TIPNSVQI | 29082 |
| HPV45 | E2 | 10 | 354 | TIPNSVQISV | 29083 |
| HPV45 | E2 | 9 | 99 | TLQDTCEEL | 29084 |
| HPV45 | E2 | 10 | 99 | TLQDTCEELW | 29085 |
| HPV45 | E2 | 10 | 5 | TPKESLSERL | 29086 |
| HPV45 | E2 | 10 | 238 | TPKPHIQTPA | 29087 |
| HPV45 | E2 | 10 | 217 | TQIVRQLQHA | 29088 |
| HPV45 | E2 | 8 | 213 | TVSATQIV | 29089 |
| HPV45 | E2 | 11 | 213 | TVSATQIVRQL | 29090 |
| HPV45 | E2 | 8 | 337 | TVTYNSEV | 29091 |
| HPV45 | E2 | 8 | 199 | VIDCNDSM | 29092 |
| HPV45 | E2 | 11 | 65 | VPPINISKSKA | 29093 |
| HPV45 | E2 | 10 | 176 | VQFKSECEKY | 29094 |
| HPV45 | E2 | 8 | 359 | VQISVGYM | 29095 |
| HPV45 | E2 | 10 | 359 | VQISVGYMTI | 29096 |
| HPV45 | E2 | 9 | 344 | VQRNTFLDV | 29097 |
| HPV45 | E2 | 10 | 344 | VQRNTFLDVV | 29098 |
| HPV45 | E2 | 8 | 193 | VQYGGNVI | 29099 |
| HPV45 | E2 | 8 | 352 | VVTIPNSV | 29100 |
| HPV45 | E2 | 10 | 352 | VVTIPNSVQI | 29101 |
| HPV45 | E2 | 8 | 138 | VVWDSIYY | 29102 |
| HPV45 | E2 | 9 | 138 | VVWDSIYYI | 29103 |
| HPV45 | E2 | 9 | 39 | WQLIRLENA | 29104 |
| HPV45 | E2 | 10 | 39 | WQLIRLENAI | 29105 |
| HPV45 | E2 | 11 | 39 | WQLIRLENAIL | 29106 |
| HPV45 | E2 | 9 | 166 | YIKDGDTTY | 29107 |
| HPV45 | E2 | 10 | 166 | YIKDGDTTYY | 29108 |
| HPV45 | E2 | 11 | 166 | YIKDGDTTYYV | 29109 |

TABLE XIV-continued

B62 Supermotif Peptides

| Type | Protein | No. of Amino Acid | Position | Sequence | Seq. Id. No. |
|---|---|---|---|---|---|
| HPV45 | E2 | 8 | 145 | YITETGIW | 29110 |
| HPV45 | E2 | 11 | 175 | YVQFKSECEKY | 29111 |
| HPV45 | E2 | 8 | 137 | YVVWDSIY | 29112 |
| HPV45 | E2 | 9 | 137 | YVVWDSIYY | 29113 |
| HPV45 | E2 | 10 | 137 | YVVWDSIYYI | 29114 |
| HPV45 | E6 | 11 | 59 | CIAYAACHKCI | 29115 |
| HPV45 | E6 | 8 | 68 | CIDFYSRI | 29116 |
| HPV45 | E6 | 11 | 68 | CIDFYSRIREL | 29117 |
| HPV45 | E6 | 8 | 105 | CLRCQKPL | 29118 |
| HPV45 | E6 | 11 | 105 | CLRCQKPLNPA | 29119 |
| HPV45 | E6 | 8 | 108 | CQKPLNPA | 29120 |
| HPV45 | E6 | 8 | 32 | CVYCKATL | 29121 |
| HPV45 | E6 | 10 | 16 | DLCTELNTSL | 29122 |
| HPV45 | E6 | 10 | 51 | DLFIVYRDCI | 29123 |
| HPV45 | E6 | 11 | 51 | DLFIVYRDCIA | 29124 |
| HPV45 | E6 | 9 | 6 | DPTQRPYKL | 29125 |
| HPV45 | E6 | 8 | 143 | DQARQERL | 29126 |
| HPV45 | E6 | 8 | 27 | DVSIACVY | 29127 |
| HPV45 | E6 | 11 | 27 | DVSIACVYCKA | 29128 |
| HPV45 | E6 | 9 | 20 | ELNTSLQDV | 29129 |
| HPV45 | E6 | 11 | 20 | ELNTSLQDVSI | 29130 |
| HPV45 | E6 | 9 | 77 | ELRYYSNSV | 29131 |
| HPV45 | E6 | 10 | 77 | ELRYYSNSVY | 29132 |
| HPV45 | E6 | 10 | 97 | ELYNLLIRCL | 29133 |
| HPV45 | E6 | 10 | 43 | EVYQFAFKDL | 29134 |
| HPV45 | E6 | 11 | 43 | EVYQFAFKDLF | 29135 |
| HPV45 | E6 | 8 | 53 | FIVYRDCI | 29136 |
| HPV45 | E6 | 9 | 53 | FIVYRDCIA | 29137 |
| HPV45 | E6 | 10 | 53 | FIVYRDCIAY | 29138 |
| HPV45 | E6 | 11 | 53 | FIVYRDCIAYA | 29139 |
| HPV45 | E6 | 10 | 136 | GQCNTCCDQA | 29140 |
| HPV45 | E6 | 8 | 120 | HLKDKRRF | 29141 |
| HPV45 | E6 | 11 | 120 | HLKDKRRFHSI | 29142 |
| HPV45 | E6 | 8 | 54 | IVYRDCIA | 29143 |
| HPV45 | E6 | 9 | 54 | IVYRDCIAY | 29144 |
| HPV45 | E6 | 10 | 54 | IVYRDCIAYA | 29145 |
| HPV45 | E6 | 11 | 54 | IVYRDCIAYAA | 29146 |
| HPV45 | E6 | 8 | 92 | KITNTELY | 29147 |
| HPV45 | E6 | 10 | 92 | KITNTELYNL | 29148 |
| HPV45 | E6 | 11 | 92 | KITNTELYNLL | 29149 |
| HPV45 | E6 | 9 | 13 | KLPDLCTEL | 29150 |
| HPV45 | E6 | 11 | 102 | LIRCLRCQKPL | 29151 |
| HPV45 | E6 | 8 | 14 | LPDLCTEL | 29152 |
| HPV45 | E6 | 9 | 25 | LQDVSIACV | 29153 |
| HPV45 | E6 | 10 | 25 | LQDVSIACVY | 29154 |
| HPV45 | E6 | 9 | 113 | NPAEKRRHL | 29155 |
| HPV45 | E6 | 11 | 111 | PLNPAEKRRHL | 29156 |
| HPV45 | E6 | 8 | 74 | RIRELRYY | 29157 |
| HPV45 | E6 | 10 | 149 | RLRRRRETQV | 29158 |
| HPV45 | E6 | 8 | 10 | RPYKLPDL | 29159 |
| HPV45 | E6 | 9 | 29 | SIACVYCKA | 29160 |
| HPV45 | E6 | 11 | 29 | SIACVYCKATL | 29161 |
| HPV45 | E6 | 8 | 24 | SLQDVSIA | 29162 |
| HPV45 | E6 | 10 | 24 | SLQDVSIACV | 29163 |
| HPV45 | E6 | 11 | 24 | SLQDVSIACVY | 29164 |
| HPV45 | E6 | 10 | 84 | SVYGETLEKI | 29165 |
| HPV45 | E6 | 10 | 89 | TLEKITNTEL | 29166 |
| HPV45 | E6 | 11 | 89 | TLEKITNTELY | 29167 |
| HPV45 | E6 | 8 | 38 | TLERTEVY | 29168 |
| HPV45 | E6 | 10 | 38 | TLERTEVYQF | 29169 |
| HPV45 | E6 | 11 | 38 | TLERTEVYQFA | 29170 |
| HPV45 | E6 | 10 | 8 | TQRPYKLPDL | 29171 |
| HPV45 | E6 | 8 | 45 | YQFAFKDL | 29172 |
| HPV45 | E6 | 9 | 45 | YQFAFKDLF | 29173 |
| HPV45 | E6 | 10 | 45 | YQFAFKDLFI | 29174 |
| HPV45 | E6 | 11 | 45 | YQFAFKDLFIV | 29175 |
| HPV45 | E7 | 8 | 48 | AQLPARRA | 29176 |
| HPV45 | E7 | 10 | 64 | CVCCKCDGRI | 29177 |
| HPV45 | E7 | 8 | 25 | DLLCYEQL | 29178 |
| HPV45 | E7 | 8 | 83 | DLRTLQQL | 29179 |
| HPV45 | E7 | 9 | 83 | DLRTLQQLF | 29180 |
| HPV45 | E7 | 10 | 83 | DLRTLQQLFL | 29181 |
| HPV45 | E7 | 8 | 22 | DPVDLLCY | 29182 |
| HPV45 | E7 | 11 | 22 | DPVDLLCYEQL | 29183 |
| HPV45 | E7 | 8 | 20 | ELDPVDLL | 29184 |

TABLE XIV-continued

B62 Supermotif Peptides

| Type | Protein | No. of Amino Acid | Position | Sequence | Seq. Id. No. |
|---|---|---|---|---|---|
| HPV45 | E7 | 10 | 20 | ELDPVDLLCY | 29185 |
| HPV45 | E7 | 8 | 74 | ELTVESSA | 29186 |
| HPV45 | E7 | 11 | 74 | ELTVESSADDL | 29187 |
| HPV45 | E7 | 9 | 16 | EPQNELDPV | 29188 |
| HPV45 | E7 | 11 | 16 | EPQNELDPVDL | 29189 |
| HPV45 | E7 | 8 | 56 | EPQRHKIL | 29190 |
| HPV45 | E7 | 10 | 56 | EPQPHKILCV | 29191 |
| HPV45 | E7 | 8 | 91 | FLSTLSFV | 29192 |
| HPV45 | E7 | 11 | 91 | FLSTLSFVCPW | 29193 |
| HPV45 | E7 | 9 | 3 | GPRATLQEI | 29194 |
| HPV45 | E7 | 10 | 3 | GPRATLQEIV | 29195 |
| HPV45 | E7 | 11 | 3 | GPRATLQEIVL | 29196 |
| HPV45 | E7 | 9 | 44 | GVSHAQLPA | 29197 |
| HPV45 | E7 | 8 | 14 | HLEPQNEL | 29198 |
| HPV45 | E7 | 11 | 14 | HLEPQNELDPV | 29199 |
| HPV45 | E7 | 11 | 11 | IVLHLEPQNEL | 29200 |
| HPV45 | E7 | 8 | 8 | LQEIVLHL | 29201 |
| HPV45 | E7 | 9 | 87 | LQQLFLSTL | 29202 |
| HPV45 | E7 | 11 | 87 | LQQLFLSTLSF | 29203 |
| HPV45 | E7 | 8 | 17 | PQNELDPV | 29204 |
| HPV45 | E7 | 10 | 17 | PQNELDPVDL | 29205 |
| HPV45 | E7 | 11 | 17 | PQNELDPVDLL | 29206 |
| HPV45 | E7 | 9 | 57 | PQRHKILCV | 29207 |
| HPV45 | E7 | 10 | 23 | PVDLLCYEQL | 29208 |
| HPV45 | E7 | 9 | 89 | QLFLSTLSF | 29209 |
| HPV45 | E7 | 10 | 89 | QLFLSTLSFV | 29210 |
| HPV45 | E7 | 8 | 88 | QQLFLSTL | 29211 |
| HPV45 | E7 | 10 | 88 | QQLFLSTLSF | 29212 |
| HPV45 | E7 | 11 | 88 | QQLFLSTLSFV | 29213 |
| HPV45 | E7 | 10 | 72 | RIELTVESSA | 29214 |
| HPV45 | E7 | 9 | 7 | TLQEIVLHL | 29215 |
| HPV45 | E7 | 10 | 86 | TLQQLFLSTL | 29216 |
| HPV45 | E7 | 8 | 94 | TLSFVCPW | 29217 |
| HPV45 | E7 | 10 | 94 | TLSFVCPWCA | 29218 |
| HPV45 | E7 | 9 | 76 | TVESSADDL | 29219 |
| HPV45 | E7 | 10 | 12 | VLHLEPQNEL | 29220 |
| HPV45 | L1 | 11 | 191 | AIGEHWAKGTL | 29221 |
| HPV45 | L1 | 8 | 103 | ALPDPNKF | 29222 |
| HPV45 | L1 | 10 | 103 | ALPDPNKFGL | 29223 |
| HPV45 | L1 | 10 | 28 | ALWRPSDSTV | 29224 |
| HPV45 | L1 | 11 | 28 | ALWRPSDSTVY | 29225 |
| HPV45 | L1 | 8 | 345 | AQGHNNGI | 29226 |
| HPV45 | L1 | 10 | 345 | AQGHNNGICW | 29227 |
| HPV45 | L1 | 11 | 205 | AQLQPGDCPPL | 29228 |
| HPV45 | L1 | 11 | 164 | AVITQDVRDNV | 29229 |
| HPV45 | L1 | 8 | 88 | AVPKVSAY | 29230 |
| HPV45 | L1 | 10 | 88 | AVPKVSAYQY | 29231 |
| HPV45 | L1 | 8 | 184 | CILGCVPA | 29232 |
| HPV45 | L1 | 9 | 184 | CILGCVPAI | 29233 |
| HPV45 | L1 | 8 | 276 | CLRREQLF | 29234 |
| HPV45 | L1 | 9 | 276 | CLRREQLFA | 29235 |
| HPV45 | L1 | 10 | 212 | CPPLELKNTI | 29236 |
| HPV45 | L1 | 11 | 212 | CPPLELKNTII | 29237 |
| HPV45 | L1 | 10 | 252 | CQSICKYPDY | 29238 |
| HPV45 | L1 | 11 | 252 | CQSICKYPDYL | 29239 |
| HPV45 | L1 | 9 | 188 | CVPAIGEHW | 29240 |
| HPV45 | L1 | 10 | 188 | CVPAIGEHWA | 29241 |
| HPV45 | L1 | 11 | 318 | CVYSPSPSGSI | 29242 |
| HPV45 | L1 | 9 | 250 | DICQSICKY | 29243 |
| HPV45 | L1 | 11 | 488 | DLDQYPLGRKF | 29244 |
| HPV45 | L1 | 10 | 480 | DLKEKFSSDL | 29245 |
| HPV45 | L1 | 8 | 401 | DLQFIFQL | 29246 |
| HPV45 | L1 | 11 | 401 | DLQFIFQLCTI | 29247 |
| HPV45 | L1 | 9 | 301 | DLYIKGTSA | 29248 |
| HPV45 | L1 | 11 | 301 | DLYIKGTSANM | 29249 |
| HPV45 | L1 | 9 | 226 | DMVDTGYGA | 29250 |
| HPV45 | L1 | 10 | 226 | DMVDTGYGAM | 29251 |
| HPV45 | L1 | 8 | 386 | DPTKFKHY | 29252 |
| HPV45 | L1 | 8 | 469 | DPYDKLKF | 29253 |
| HPV45 | L1 | 9 | 469 | DPYDKLKFW | 29254 |
| HPV45 | L1 | 11 | 469 | DPYDKLKFWTV | 29255 |
| HPV45 | L1 | 8 | 267 | DPYGDSMF | 29256 |
| HPV45 | L1 | 9 | 267 | DPYGDSMFF | 29257 |
| HPV45 | L1 | 11 | 267 | DPYGDSMFFCL | 29258 |
| HPV45 | L1 | 9 | 490 | DQYPLGRKF | 29259 |

TABLE XIV-continued

B62 Supermotif Peptides

| Type | Protein | No. of Amino Acid | Position | Sequence | Seq. Id. No. |
|---|---|---|---|---|---|
| HPV45 | L1 | 10 | 490 | DQYPLGRKFL | 29260 |
| HPV45 | L1 | 11 | 490 | DQYPLGRKFLV | 29261 |
| HPV45 | L1 | 8 | 169 | DVRDNVSV | 29262 |
| HPV45 | L1 | 10 | 169 | DVRDNVSVDY | 29263 |
| HPV45 | L1 | 8 | 133 | EIGRGQPL | 29264 |
| HPV45 | L1 | 10 | 133 | EIGRGQPLGI | 29265 |
| HPV45 | L1 | 8 | 280 | EQLFARHF | 29266 |
| HPV45 | L1 | 9 | 280 | EQLFARHFW | 29267 |
| HPV45 | L1 | 9 | 416 | EVMSYIHSM | 29268 |
| HPV45 | L1 | 10 | 246 | EVPLDICQSI | 29269 |
| HPV45 | L1 | 8 | 404 | FIFQLCTI | 29270 |
| HPV45 | L1 | 10 | 404 | FIFQLCTITL | 29271 |
| HPV45 | L1 | 8 | 14 | FLKNVNVF | 29272 |
| HPV45 | L1 | 10 | 14 | FLKNVNVFPI | 29273 |
| HPV45 | L1 | 11 | 14 | FLKNVNVFPIF | 29274 |
| HPV45 | L1 | 8 | 21 | FPIFLQMA | 29275 |
| HPV45 | L1 | 9 | 21 | FPIFLQMAL | 29276 |
| HPV45 | L1 | 10 | 21 | FPIFLQMALW | 29277 |
| HPV45 | L1 | 8 | 406 | FQLCTITL | 29278 |
| HPV45 | L1 | 10 | 406 | FQLCTITLTA | 29279 |
| HPV45 | L1 | 8 | 351 | GICWHNQL | 29280 |
| HPV45 | L1 | 9 | 351 | GICWHNQLF | 29281 |
| HPV45 | L1 | 10 | 351 | GICWHNQLFV | 29282 |
| HPV45 | L1 | 9 | 141 | GIGLSGHPF | 29283 |
| HPV45 | L1 | 10 | 141 | GIGLSGHPFY | 29284 |
| HPV45 | L1 | 9 | 10 | GIIIFLKNV | 29285 |
| HPV45 | L1 | 11 | 10 | GIIIFLKNVNV | 29286 |
| HPV45 | L1 | 8 | 111 | GLPDSTIY | 29287 |
| HPV45 | L1 | 8 | 503 | GLRRRPTI | 29288 |
| HPV45 | L1 | 8 | 143 | GLSGHPFY | 29289 |
| HPV45 | L1 | 11 | 143 | GLSGHPFYNKL | 29290 |
| HPV45 | L1 | 10 | 131 | GMEIGRGQPL | 29291 |
| HPV45 | L1 | 8 | 511 | GPRKRPAA | 29292 |
| HPV45 | L1 | 8 | 137 | GQPLGIGL | 29293 |
| HPV45 | L1 | 11 | 292 | GVMGDTVPTDL | 29294 |
| HPV45 | L1 | 10 | 435 | GVPPPPTTSL | 29295 |
| HPV45 | L1 | 11 | 435 | GVPPPPTTSLV | 29296 |
| HPV45 | L1 | 9 | 396 | HVEEYDLQF | 29297 |
| HPV45 | L1 | 10 | 396 | HVEEYDLQFI | 29298 |
| HPV45 | L1 | 11 | 396 | HVEEYDLQFIF | 29299 |
| HPV45 | L1 | 8 | 221 | IIEDGDMV | 29300 |
| HPV45 | L1 | 9 | 12 | IIFLKNVNV | 29301 |
| HPV45 | L1 | 10 | 12 | IIFLKNVNVF | 29302 |
| HPV45 | L1 | 8 | 11 | IIIFLKNV | 29303 |
| HPV45 | L1 | 10 | 11 | IIIFLKNVNV | 29304 |
| HPV45 | L1 | 11 | 11 | IIIFLKNVNVF | 29305 |
| HPV45 | L1 | 8 | 5 | IIYGHGII | 29306 |
| HPV45 | L1 | 9 | 5 | IIYGHGIII | 29307 |
| HPV45 | L1 | 10 | 5 | IIYGHGIIIF | 29308 |
| HPV45 | L1 | 11 | 5 | IIYGHGIIIFL | 29309 |
| HPV45 | L1 | 9 | 428 | ILENWNFGV | 29310 |
| HPV45 | L1 | 8 | 185 | ILGCVPAI | 29311 |
| HPV45 | L1 | 8 | 152 | KLDDTESA | 29312 |
| HPV45 | L1 | 10 | 152 | KLDDTESAHA | 29313 |
| HPV45 | L1 | 11 | 152 | KLDDTESAHAA | 29314 |
| HPV45 | L1 | 9 | 473 | KLKFWTVDL | 29315 |
| HPV45 | L1 | 8 | 338 | KPYWLHKA | 29316 |
| HPV45 | L1 | 9 | 86 | KQAVPKVSA | 29317 |
| HPV45 | L1 | 10 | 86 | KQAVPKVSAY | 29318 |
| HPV45 | L1 | 8 | 467 | KQDPYDKL | 29319 |
| HPV45 | L1 | 10 | 467 | KQDPYDKLKF | 29320 |
| HPV45 | L1 | 11 | 467 | KQDPYDKLKFW | 29321 |
| HPV45 | L1 | 8 | 179 | KQTQLCIL | 29322 |
| HPV45 | L1 | 11 | 179 | KQTQLCILGCV | 29323 |
| HPV45 | L1 | 9 | 91 | KVSAYQYRV | 29324 |
| HPV45 | L1 | 10 | 91 | KVSAYQYRVF | 29325 |
| HPV45 | L1 | 8 | 68 | LLTVGNPY | 29326 |
| HPV45 | L1 | 9 | 68 | LLTVGNPYF | 29327 |
| HPV45 | L1 | 11 | 68 | LLTVGNPYFRV | 29328 |
| HPV45 | L1 | 9 | 104 | LPDPNKFGL | 29329 |
| HPV45 | L1 | 9 | 39 | LPPPSVARV | 29330 |
| HPV45 | L1 | 10 | 39 | LPPPSVARVV | 29331 |
| HPV45 | L1 | 8 | 240 | LQDTKCEV | 29332 |
| HPV45 | L1 | 10 | 240 | LQDTKCEVPL | 29333 |
| HPV45 | L1 | 10 | 402 | LQFIFQLCTI | 29334 |

TABLE XIV-continued

B62 Supermotif Peptides

| Type | Protein | No. of Amino Acid | Position | Sequence | Seq. Id. No. |
|---|---|---|---|---|---|
| HPV45 | L1 | 8 | 262 | LQMSADPY | 29335 |
| HPV45 | L1 | 9 | 207 | LQPGDCPPL | 29336 |
| HPV45 | L1 | 11 | 207 | LQPGDCPPLEL | 29337 |
| HPV45 | L1 | 8 | 444 | LVDTYRFV | 29338 |
| HPV45 | L1 | 11 | 444 | LVDTYRFVQSV | 29339 |
| HPV45 | L1 | 8 | 125 | LVWACVGM | 29340 |
| HPV45 | L1 | 10 | 125 | LVWACVGMEI | 29341 |
| HPV45 | L1 | 8 | 227 | MVDTGYGA | 29342 |
| HPV45 | L1 | 9 | 227 | MVDTGYGAM | 29343 |
| HPV45 | L1 | 11 | 227 | MVDTGYGAMDF | 29344 |
| HPV45 | L1 | 8 | 4 | NIIYGHGI | 29345 |
| HPV45 | L1 | 9 | 4 | NIIYGHGII | 29346 |
| HPV45 | L1 | 10 | 4 | NIIYGHGIII | 29347 |
| HPV45 | L1 | 11 | 4 | NIIYGHGIIIF | 29348 |
| HPV45 | L1 | 10 | 310 | NMRETPGSCV | 29349 |
| HPV45 | L1 | 11 | 310 | NMRETPGSCVY | 29350 |
| HPV45 | L1 | 8 | 119 | NPETQRLV | 29351 |
| HPV45 | L1 | 9 | 119 | NPETQRLVW | 29352 |
| HPV45 | L1 | 10 | 119 | NPETQRLVWA | 29353 |
| HPV45 | L1 | 11 | 73 | NPYFRVVPSGA | 29354 |
| HPV45 | L1 | 8 | 356 | NQLFVTVV | 29355 |
| HPV45 | L1 | 9 | 19 | NVFPIFLQM | 29356 |
| HPV45 | L1 | 10 | 19 | NVFPIFLQMA | 29357 |
| HPV45 | L1 | 11 | 19 | NVFPIFLQMAL | 29358 |
| HPV45 | L1 | 8 | 17 | NVNVFPIF | 29359 |
| HPV45 | L1 | 9 | 17 | NVNVFPIFL | 29360 |
| HPV45 | L1 | 11 | 17 | NVNVFPIFLQM | 29361 |
| HPV45 | L1 | 11 | 173 | NVSVDYKQTQL | 29362 |
| HPV45 | L1 | 8 | 22 | PIFLQMAL | 29363 |
| HPV45 | L1 | 9 | 22 | PIFLQMALW | 29364 |
| HPV45 | L1 | 8 | 248 | PLDICQSI | 29365 |
| HPV45 | L1 | 11 | 248 | PLDICQSICKY | 29366 |
| HPV45 | L1 | 8 | 214 | PLELKNTI | 29367 |
| HPV45 | L1 | 9 | 214 | PLELKNTII | 29368 |
| HPV45 | L1 | 11 | 139 | PLGIGLSGHPF | 29369 |
| HPV45 | L1 | 8 | 493 | PLGRKFLV | 29370 |
| HPV45 | L1 | 10 | 493 | PLGRKFLVQA | 29371 |
| HPV45 | L1 | 8 | 464 | PPEKQDPY | 29372 |
| HPV45 | L1 | 11 | 464 | PPEKQDPYDKL | 29373 |
| HPV45 | L1 | 9 | 213 | PPLELKNTI | 29374 |
| HPV45 | L1 | 10 | 213 | PPLELKNTII | 29375 |
| HPV45 | L1 | 8 | 437 | PPPPTTSL | 29376 |
| HPV45 | L1 | 9 | 437 | PPPPTTSLV | 29377 |
| HPV45 | L1 | 8 | 40 | PPPSVARV | 29378 |
| HPV45 | L1 | 9 | 40 | PPPSVARVV | 29379 |
| HPV45 | L1 | 8 | 438 | PPPTTSLV | 29380 |
| HPV45 | L1 | 11 | 438 | PPPTTSLVDTY | 29381 |
| HPV45 | L1 | 8 | 41 | PPSVARVV | 29382 |
| HPV45 | L1 | 10 | 439 | PPTTSLVDTY | 29383 |
| HPV45 | L1 | 11 | 380 | PVPNTYDPTKF | 29384 |
| HPV45 | L1 | 8 | 182 | QLCILGCV | 29385 |
| HPV45 | L1 | 10 | 182 | QLCILGCVPA | 29386 |
| HPV45 | L1 | 11 | 182 | QLCILGCVPAI | 29387 |
| HPV45 | L1 | 9 | 407 | QLCTITLTA | 29388 |
| HPV45 | L1 | 11 | 407 | QLCTITLTAEV | 29389 |
| HPV45 | L1 | 8 | 281 | QLFARHFW | 29390 |
| HPV45 | L1 | 11 | 281 | QLFARHFWNRA | 29391 |
| HPV45 | L1 | 8 | 334 | QLFNKPYW | 29392 |
| HPV45 | L1 | 9 | 334 | QLFNKPYWL | 29393 |
| HPV45 | L1 | 10 | 206 | QLQPGDCPPL | 29394 |
| HPV45 | L1 | 11 | 263 | QMSADPYGDSM | 29395 |
| HPV45 | L1 | 8 | 208 | QPGDCPPL | 29396 |
| HPV45 | L1 | 10 | 208 | QPGDCPPLEL | 29397 |
| HPV45 | L1 | 9 | 67 | RLLTVGNPY | 29398 |
| HPV45 | L1 | 10 | 67 | RLLTVGNPYF | 29399 |
| HPV45 | L1 | 9 | 124 | RLVWACVGM | 29400 |
| HPV45 | L1 | 11 | 124 | RLVWACVGMEI | 29401 |
| HPV45 | L1 | 9 | 515 | RPAASTSTA | 29402 |
| HPV45 | L1 | 8 | 525 | RPAKRVRI | 29403 |
| HPV45 | L1 | 8 | 31 | RPSDSTVY | 29404 |
| HPV45 | L1 | 9 | 31 | RPSDSTVYL | 29405 |
| HPV45 | L1 | 11 | 507 | RPTIGPRKRPA | 29406 |
| HPV45 | L1 | 10 | 101 | RVALPDPNKF | 29407 |
| HPV45 | L1 | 8 | 46 | RVVNTDDY | 29408 |
| HPV45 | L1 | 9 | 46 | RVVNTDDYV | 29409 |

TABLE XIV-continued

B62 Supermotif Peptides

| Type | Protein | No. of Amino Acid | Position | Sequence | Seq. Id. No. |
|---|---|---|---|---|---|
| HPV45 | L1 | 8 | 254 | SICKYPDY | 29410 |
| HPV45 | L1 | 9 | 254 | SICKYPDYL | 29411 |
| HPV45 | L1 | 11 | 254 | SICKYPDYLQM | 29412 |
| HPV45 | L1 | 11 | 58 | SIFYHAGSSRL | 29413 |
| HPV45 | L1 | 8 | 427 | SILENWNF | 29414 |
| HPV45 | L1 | 10 | 427 | SILENWNFGV | 29415 |
| HPV45 | L1 | 9 | 327 | SITTSDSQL | 29416 |
| HPV45 | L1 | 10 | 327 | SITUSDSQLF | 29417 |
| HPV45 | L1 | 8 | 443 | SLVDTYRF | 29418 |
| HPV45 | L1 | 9 | 443 | SLVDTYRFV | 29419 |
| HPV45 | L1 | 11 | 272 | SMFFCLRREQL | 29420 |
| HPV45 | L1 | 10 | 423 | SMNSSILENW | 29421 |
| HPV45 | L1 | 8 | 321 | SPSPSGSI | 29422 |
| HPV45 | L1 | 8 | 333 | SQLFNKPY | 29423 |
| HPV45 | L1 | 9 | 333 | SQLFNKPYW | 29424 |
| HPV45 | L1 | 10 | 333 | SQLFNKPYWL | 29425 |
| HPV45 | L1 | 11 | 43 | SVARVVNTDDY | 29426 |
| HPV45 | L1 | 9 | 175 | SVDYKQTQL | 29427 |
| HPV45 | L1 | 11 | 175 | SVDYKQTQLCI | 29428 |
| HPV45 | L1 | 9 | 509 | TIGPRKRPA | 29429 |
| HPV45 | L1 | 10 | 509 | TIGPRKRPAA | 29430 |
| HPV45 | L1 | 8 | 220 | TIIEDGDM | 29431 |
| HPV45 | L1 | 9 | 220 | TIIEDGDMV | 29432 |
| HPV45 | L1 | 8 | 410 | TITLTAEV | 29433 |
| HPV45 | L1 | 9 | 410 | TITLTAEVM | 29434 |
| HPV45 | L1 | 11 | 410 | TITLTAEVMSY | 29435 |
| HPV45 | L1 | 10 | 116 | TIYNPETQRL | 29436 |
| HPV45 | L1 | 11 | 116 | TIYNPETQRLV | 29437 |
| HPV45 | L1 | 10 | 372 | TLCASTQNPV | 29438 |
| HPV45 | L1 | 8 | 200 | TLCKPAQL | 29439 |
| HPV45 | L1 | 9 | 239 | TLQDTKCEV | 29440 |
| HPV45 | L1 | 11 | 239 | TLQDTKCEVPL | 29441 |
| HPV45 | L1 | 9 | 412 | TLTAEVMSY | 29442 |
| HPV45 | L1 | 10 | 412 | TLTAEVMSYI | 29443 |
| HPV45 | L1 | 9 | 463 | TPPEKQDPY | 29444 |
| HPV45 | L1 | 8 | 167 | TQDVRDNV | 29445 |
| HPV45 | L1 | 10 | 167 | TQDVRDNVSV | 29446 |
| HPV45 | L1 | 9 | 181 | TQLCILGCV | 29447 |
| HPV45 | L1 | 11 | 181 | TQLCILGCVPA | 29448 |
| HPV45 | L1 | 9 | 377 | TQNPVPNTY | 29449 |
| HPV45 | L1 | 9 | 122 | TQRLVWACV | 29450 |
| HPV45 | L1 | 11 | 122 | TQRLVWACVGM | 29451 |
| HPV45 | L1 | 8 | 478 | TVDLKEKF | 29452 |
| HPV45 | L1 | 9 | 70 | TVGNPYFRV | 29453 |
| HPV45 | L1 | 10 | 70 | TVGNPYFRVV | 29454 |
| HPV45 | L1 | 8 | 297 | TVPTDLYI | 29455 |
| HPV45 | L1 | 11 | 361 | TVVDTTRSTNL | 29456 |
| HPV45 | L1 | 9 | 36 | TVYLPPPSV | 29457 |
| HPV45 | L1 | 10 | 36 | TVYLPPPSVA | 29458 |
| HPV45 | L1 | 10 | 165 | VITQDVRDNV | 29459 |
| HPV45 | L1 | 10 | 293 | VMGDTVPTDL | 29460 |
| HPV45 | L1 | 11 | 293 | VMGDTVPTDLY | 29461 |
| HPV45 | L1 | 8 | 417 | VMSYIHSM | 29462 |
| HPV45 | L1 | 8 | 189 | VPAIGEHW | 29463 |
| HPV45 | L1 | 9 | 189 | VPAIGEHWA | 29464 |
| HPV45 | L1 | 9 | 89 | VPKVSAYQY | 29465 |
| HPV45 | L1 | 11 | 89 | VPKVSAYQYRV | 29466 |
| HPV45 | L1 | 9 | 247 | VPLDICQSI | 29467 |
| HPV45 | L1 | 10 | 381 | VPNTYDPTKF | 29468 |
| HPV45 | L1 | 9 | 436 | VPPPPTTSL | 29469 |
| HPV45 | L1 | 10 | 436 | VPPPPTTSLV | 29470 |
| HPV45 | L1 | 10 | 79 | VPSGAGNKQA | 29471 |
| HPV45 | L1 | 11 | 79 | VPSGAGNKQAV | 29472 |
| HPV45 | L1 | 11 | 500 | VQAGLRRRPTI | 29473 |
| HPV45 | L1 | 10 | 362 | VVDTTRSTNL | 29474 |
| HPV45 | L1 | 8 | 47 | VVNTDDYV | 29475 |
| HPV45 | L1 | 11 | 78 | VVPSGAGNKQA | 29476 |
| HPV45 | L1 | 9 | 420 | YIHSMNSSI | 29477 |
| HPV45 | L1 | 10 | 420 | YIHSMNSSIL | 29478 |
| HPV45 | L1 | 9 | 303 | YIKGTSANM | 29479 |
| HPV45 | L1 | 8 | 38 | YLPPPSVA | 29480 |
| HPV45 | L1 | 10 | 38 | YLPPPSVARV | 29481 |
| HPV45 | L1 | 11 | 38 | YLPPPSVARVV | 29482 |
| HPV45 | L1 | 9 | 261 | YLQMSADPY | 29483 |
| HPV45 | L1 | 9 | 258 | YPDYLQMSA | 29484 |

TABLE XIV-continued

B62 Supermotif Peptides

| Type | Protein | No. of Amino Acid | Position | Sequence | Seq. Id. No. |
|---|---|---|---|---|---|
| HPV45 | L1 | 8 | 492 | YPLGRKFL | 29485 |
| HPV45 | L1 | 9 | 492 | YPLGRKFLV | 29486 |
| HPV45 | L1 | 11 | 492 | YPLGRKFLVQA | 29487 |
| HPV45 | L1 | 8 | 95 | YQYRVFRV | 29488 |
| HPV45 | L1 | 9 | 95 | YQYRVFRVA | 29489 |
| HPV45 | L1 | 10 | 95 | YQYRVFRVAL | 29490 |
| HPV45 | L1 | 8 | 53 | YVSRTSIF | 29491 |
| HPV45 | L1 | 9 | 53 | YVSRTSIFY | 29492 |
| HPV45 | L1 | 11 | 53 | YVSRTSIFYHA | 29493 |
| HPV45 | L2 | 9 | 286 | ALSSRRGTV | 29494 |
| HPV45 | L2 | 11 | 286 | ALSSRRGTVRF | 29495 |
| HPV45 | L2 | 9 | 139 | AVLDITPTV | 29496 |
| HPV45 | L2 | 9 | 27 | CPPDVINKV | 29497 |
| HPV45 | L2 | 10 | 405 | DIILPSHTPM | 29498 |
| HPV45 | L2 | 11 | 405 | DIILPSHTPMW | 29499 |
| HPV45 | L2 | 9 | 278 | DIIRLHRPA | 29500 |
| HPV45 | L2 | 10 | 278 | DIIRLHRPAL | 29501 |
| HPV45 | L2 | 11 | 322 | DISPIAATEEI | 29502 |
| HPV45 | L2 | 9 | 142 | DITPTVDSV | 29503 |
| HPV45 | L2 | 11 | 142 | DITPTVDSVSI | 29504 |
| HPV45 | L2 | 9 | 345 | DLFDVYADF | 29505 |
| HPV45 | L2 | 8 | 100 | DPSIVTLV | 29506 |
| HPV45 | L2 | 9 | 83 | DVGPTRPPV | 29507 |
| HPV45 | L2 | 10 | 83 | DVGPTRPPVV | 29508 |
| HPV45 | L2 | 11 | 83 | DVGPTRPPVVI | 29509 |
| HPV45 | L2 | 11 | 30 | DVINKVEGTTL | 29510 |
| HPV45 | L2 | 10 | 397 | DVPIYTGPDI | 29511 |
| HPV45 | L2 | 11 | 397 | DVPIYTGPDII | 29512 |
| HPV45 | L2 | 10 | 348 | DVYADFPPPA | 29513 |
| HPV45 | L2 | 8 | 331 | EIELQPLI | 29514 |
| HPV45 | L2 | 10 | 331 | EIELQPLISA | 29515 |
| HPV45 | L2 | 8 | 194 | EIPLQTFA | 29516 |
| HPV45 | L2 | 11 | 129 | EITSSGTTTPA | 29517 |
| HPV45 | L2 | 8 | 333 | ELQPLISA | 29518 |
| HPV45 | L2 | 8 | 208 | EPISSTPL | 29519 |
| HPV45 | L2 | 11 | 208 | EPISSTPLPTV | 29520 |
| HPV45 | L2 | 9 | 257 | EPLDTTLSF | 29521 |
| HPV45 | L2 | 11 | 266 | EPTSNVPDSDF | 29522 |
| HPV45 | L2 | 10 | 94 | EPVGPTDPSI | 29523 |
| HPV45 | L2 | 11 | 94 | EPVGPTDPSIV | 29524 |
| HPV45 | L2 | 8 | 169 | EVPQTGEV | 29525 |
| HPV45 | L2 | 8 | 175 | EVSGNIFV | 29526 |
| HPV45 | L2 | 8 | 241 | FLTHPSSL | 29527 |
| HPV45 | L2 | 9 | 241 | FLTHPSSLV | 29528 |
| HPV45 | L2 | 11 | 241 | FLTHPSSLVTF | 29529 |
| HPV45 | L2 | 11 | 276 | FMDIIRLHRPA | 29530 |
| HPV45 | L2 | 8 | 445 | FPKKRKRI | 29531 |
| HPV45 | L2 | 10 | 445 | FPKKRKRIPY | 29532 |
| HPV45 | L2 | 11 | 445 | FPKKRKRIPYF | 29533 |
| HPV45 | L2 | 9 | 51 | GIFLGGLGI | 29534 |
| HPV45 | L2 | 8 | 430 | GIHGTQYY | 29535 |
| HPV45 | L2 | 9 | 430 | GIHGTQYYL | 29536 |
| HPV45 | L2 | 10 | 430 | GIHGTQYYLW | 29537 |
| HPV45 | L2 | 8 | 223 | GPRLYSRA | 29538 |
| HPV45 | L2 | 8 | 97 | GPTDPSIV | 29539 |
| HPV45 | L2 | 10 | 97 | GPTDPSIVTL | 29540 |
| HPV45 | L2 | 11 | 97 | GPTDPSIVTLV | 29541 |
| HPV45 | L2 | 8 | 85 | GPTRPPVV | 29542 |
| HPV45 | L2 | 9 | 85 | GPTRPPVVI | 29543 |
| HPV45 | L2 | 8 | 244 | HPSSLVTF | 29544 |
| HPV45 | L2 | 10 | 167 | IIEVPQTGEV | 29545 |
| HPV45 | L2 | 9 | 406 | IILPSHTPM | 29546 |
| HPV45 | L2 | 10 | 406 | IILPSHTPMW | 29547 |
| HPV45 | L2 | 8 | 279 | IIRLHRPA | 29548 |
| HPV45 | L2 | 9 | 279 | IIRLHRPAL | 29549 |
| HPV45 | L2 | 8 | 407 | ILPSHTPM | 29550 |
| HPV45 | L2 | 9 | 407 | ILPSHTPMW | 29551 |
| HPV45 | L2 | 9 | 44 | ILQWSSLGI | 29552 |
| HPV45 | L2 | 10 | 44 | ILQWSSLGIF | 29553 |
| HPV45 | L2 | 11 | 44 | ILQWSSLGIFL | 29554 |
| HPV45 | L2 | 9 | 452 | IPYFFADGF | 29555 |
| HPV45 | L2 | 10 | 452 | IPYFFADGFV | 29556 |
| HPV45 | L2 | 11 | 452 | IPYFFADGFVA | 29557 |
| HPV45 | L2 | 10 | 103 | IVTLVEDSSV | 29558 |
| HPV45 | L2 | 11 | 103 | IVTLVEDSSVV | 29559 |

TABLE XIV-continued

B62 Supermotif Peptides

| Type | Protein | No. of Amino Acid | Position | Sequence | Seq. Id. No. |
|---|---|---|---|---|---|
| HPV45 | L2 | 8 | 43 | KILQWSSL | 29560 |
| HPV45 | L2 | 10 | 43 | KILQWSSLGI | 29561 |
| HPV45 | L2 | 11 | 43 | KILQWSSLGIF | 29562 |
| HPV45 | L2 | 9 | 311 | KQIGGRVHF | 29563 |
| HPV45 | L2 | 10 | 311 | KQIGGRVHFY | 29564 |
| HPV45 | L2 | 10 | 22 | KQSGTCPPDV | 29565 |
| HPV45 | L2 | 11 | 22 | KQSGTCPPDVI | 29566 |
| HPV45 | L2 | 8 | 34 | KVEGTTLA | 29567 |
| HPV45 | L2 | 11 | 34 | KVEGTTLADKI | 29568 |
| HPV45 | L2 | 10 | 337 | LISATNDSDL | 29569 |
| HPV45 | L2 | 11 | 337 | LISATNDSDLF | 29570 |
| HPV45 | L2 | 8 | 408 | LPSHTPMW | 29571 |
| HPV45 | L2 | 8 | 45 | LQWSSLGI | 29572 |
| HPV45 | L2 | 9 | 45 | LQWSSLGIF | 29573 |
| HPV45 | L2 | 10 | 45 | LQWSSLGIFL | 29574 |
| HPV45 | L2 | 8 | 106 | LVEDSSVV | 29575 |
| HPV45 | L2 | 9 | 106 | LVEDSSVVA | 29576 |
| HPV45 | L2 | 8 | 248 | LVTFDNPA | 29577 |
| HPV45 | L2 | 9 | 248 | LVTFDNPAY | 29578 |
| HPV45 | L2 | 9 | 377 | MPSTAASSY | 29579 |
| HPV45 | L2 | 9 | 159 | NPAFSDPSI | 29580 |
| HPV45 | L2 | 10 | 159 | NPAFSDPSII | 29581 |
| HPV45 | L2 | 11 | 253 | NPAYEPLDTTL | 29582 |
| HPV45 | L2 | 11 | 231 | NQQVRVSTSQF | 29583 |
| HPV45 | L2 | 8 | 270 | NVPDSDFM | 29584 |
| HPV45 | L2 | 10 | 270 | NVPDSDFMDI | 29585 |
| HPV45 | L2 | 11 | 270 | NVPDSDFMDII | 29586 |
| HPV45 | L2 | 9 | 387 | NVTVPLTSA | 29587 |
| HPV45 | L2 | 10 | 387 | NVTVPLTSAW | 29588 |
| HPV45 | L2 | 8 | 325 | PIAATEEI | 29589 |
| HPV45 | L2 | 10 | 325 | PIAATEEIEL | 29590 |
| HPV45 | L2 | 10 | 209 | PISSTPLPTV | 29591 |
| HPV45 | L2 | 8 | 399 | PIYTGPDI | 29592 |
| HPV45 | L2 | 9 | 399 | PIYTGPDII | 29593 |
| HPV45 | L2 | 10 | 399 | PIYTGPDIIL | 29594 |
| HPV45 | L2 | 8 | 258 | PLDTTLSF | 29595 |
| HPV45 | L2 | 9 | 73 | PLGGRSNTV | 29596 |
| HPV45 | L2 | 10 | 73 | PLGGRSNTVV | 29597 |
| HPV45 | L2 | 11 | 336 | PLISATNDSDL | 29598 |
| HPV45 | L2 | 8 | 214 | PLPTVRRV | 29599 |
| HPV45 | L2 | 8 | 391 | PLTSAWDV | 29600 |
| HPV45 | L2 | 10 | 391 | PLTSAWDVPI | 29601 |
| HPV45 | L2 | 11 | 391 | PLTSAWDVPIY | 29602 |
| HPV45 | L2 | 11 | 413 | PMWPSTSPTNA | 29603 |
| HPV45 | L2 | 10 | 355 | PPASTTPSTI | 29604 |
| HPV45 | L2 | 8 | 28 | PPDVINKV | 29605 |
| HPV45 | L2 | 11 | 354 | PPPASTTPSTI | 29606 |
| HPV45 | L2 | 8 | 89 | PPVVIEPV | 29607 |
| HPV45 | L2 | 10 | 171 | PQTGEVSGNI | 29608 |
| HPV45 | L2 | 11 | 171 | PQTGEVSGNIF | 29609 |
| HPV45 | L2 | 9 | 95 | PVGPTDPSI | 29610 |
| HPV45 | L2 | 10 | 95 | PVGPTDPSIV | 29611 |
| HPV45 | L2 | 11 | 118 | PVPTFTGTSGF | 29612 |
| HPV45 | L2 | 8 | 312 | QIGGRVHF | 29613 |
| HPV45 | L2 | 9 | 312 | QIGGRVHFY | 29614 |
| HPV45 | L2 | 10 | 232 | QQVRVSTSQF | 29615 |
| HPV45 | L2 | 11 | 232 | QQVRVSTSQFL | 29616 |
| HPV45 | L2 | 9 | 233 | QVRVSTSQF | 29617 |
| HPV45 | L2 | 10 | 233 | QVRVSTSQFL | 29618 |
| HPV45 | L2 | 10 | 451 | RIPYFFADGF | 29619 |
| HPV45 | L2 | 11 | 451 | RIPYFFADGFV | 29620 |
| HPV45 | L2 | 8 | 298 | RLGQRATM | 29621 |
| HPV45 | L2 | 9 | 298 | RLGQRATMF | 29622 |
| HPV45 | L2 | 10 | 225 | RLYSRANQQV | 29623 |
| HPV45 | L2 | 11 | 284 | RPALSSRRGTV | 29624 |
| HPV45 | L2 | 9 | 88 | RPPVVIEPV | 29625 |
| HPV45 | L2 | 8 | 316 | RVHFYHDI | 29626 |
| HPV45 | L2 | 11 | 316 | RVHFYHDISPI | 29627 |
| HPV45 | L2 | 8 | 220 | RVRGPRLY | 29628 |
| HPV45 | L2 | 11 | 220 | RVRGPRLYSRA | 29629 |
| HPV45 | L2 | 8 | 235 | RVSTSQFL | 29630 |
| HPV45 | L2 | 11 | 166 | SIIEVPQTGEV | 29631 |
| HPV45 | L2 | 11 | 151 | SISSTSFTNPA | 29632 |
| HPV45 | L2 | 11 | 102 | SIVTLVEDSSV | 29633 |
| HPV45 | L2 | 9 | 49 | SLGIFLGGL | 29634 |

TABLE XIV-continued

B62 Supermotif Peptides

| Type | Protein | No. of Amino Acid | Position | Sequence | Seq. Id. No. |
|---|---|---|---|---|---|
| HPV45 | L2 | 11 | 49 | SLGIFLGGLGI | 29635 |
| HPV45 | L2 | 8 | 374 | SLTMPSTA | 29636 |
| HPV45 | L2 | 9 | 374 | SLTMPSTAA | 29637 |
| HPV45 | L2 | 9 | 247 | SLVTFDNPA | 29638 |
| HPV45 | L2 | 10 | 247 | SLVTFDNPAY | 29639 |
| HPV45 | L2 | 9 | 324 | SPIAATEEI | 29640 |
| HPV45 | L2 | 11 | 324 | SPIAATEEIEL | 29641 |
| HPV45 | L2 | 10 | 419 | SPTNASTTTY | 29642 |
| HPV45 | L2 | 11 | 419 | SPTNASTTTYI | 29643 |
| HPV45 | L2 | 10 | 239 | SQFLTHPSSL | 29644 |
| HPV45 | L2 | 11 | 239 | SQFLTHPSSLV | 29645 |
| HPV45 | L2 | 9 | 149 | SVSISSTSF | 29646 |
| HPV45 | L2 | 9 | 111 | SVVASGAPV | 29647 |
| HPV45 | L2 | 8 | 363 | TIHKSFTY | 29648 |
| HPV45 | L2 | 11 | 363 | TIHKSFTYPKY | 29649 |
| HPV45 | L2 | 9 | 39 | TLADKILQW | 29650 |
| HPV45 | L2 | 10 | 262 | TLSFEPTSNV | 29651 |
| HPV45 | L2 | 8 | 105 | TLVEDSSV | 29652 |
| HPV45 | L2 | 9 | 105 | TLVEDSSVV | 29653 |
| HPV45 | L2 | 10 | 105 | TLVEDSSVVA | 29654 |
| HPV45 | L2 | 10 | 304 | TMFTRSGKQI | 29655 |
| HPV45 | L2 | 10 | 376 | TMPSTAASSY | 29656 |
| HPV45 | L2 | 11 | 137 | TPAVLDITPTV | 29657 |
| HPV45 | L2 | 9 | 213 | TPLPTVRRV | 29658 |
| HPV45 | L2 | 9 | 360 | TPSTIHKSF | 29659 |
| HPV45 | L2 | 11 | 360 | TPSTIHKSFTY | 29660 |
| HPV45 | L2 | 9 | 184 | TPTSGSHGY | 29661 |
| HPV45 | L2 | 9 | 144 | TPTVDSVSI | 29662 |
| HPV45 | L2 | 8 | 434 | TQYYLWPW | 29663 |
| HPV45 | L2 | 9 | 434 | TQYYLWPWY | 29664 |
| HPV45 | L2 | 10 | 434 | TQYYLWPWYY | 29665 |
| HPV45 | L2 | 11 | 434 | TQYYLWPWYYY | 29666 |
| HPV45 | L2 | 8 | 389 | TVPLTSAW | 29667 |
| HPV45 | L2 | 10 | 389 | TVPLTSAWDV | 29668 |
| HPV45 | L2 | 11 | 293 | TVRFSRLGQRA | 29669 |
| HPV45 | L2 | 10 | 217 | TVRRVRGPRL | 29670 |
| HPV45 | L2 | 11 | 217 | TVRRVRGPRLY | 29671 |
| HPV45 | L2 | 10 | 31 | VINKVEGTTL | 29672 |
| HPV45 | L2 | 11 | 31 | VINKVEGTTLA | 29673 |
| HPV45 | L2 | 8 | 140 | VLDITPTV | 29674 |
| HPV45 | L2 | 11 | 140 | VLDITPTVDSV | 29675 |
| HPV45 | L2 | 9 | 271 | VPDSDFMDI | 29676 |
| HPV45 | L2 | 10 | 271 | VPDSDFMDII | 29677 |
| HPV45 | L2 | 9 | 398 | VPIYTGPDI | 29678 |
| HPV45 | L2 | 10 | 398 | VPIYTGPDII | 29679 |
| HPV45 | L2 | 11 | 398 | VPIYTGPDIIL | 29680 |
| HPV45 | L2 | 10 | 72 | VPLGGRSNTV | 29681 |
| HPV45 | L2 | 11 | 72 | VPLGGRSNTVV | 29682 |
| HPV45 | L2 | 9 | 390 | VPLTSAWDV | 29683 |
| HPV45 | L2 | 11 | 390 | VPLTSAWDVPI | 29684 |
| HPV45 | L2 | 11 | 170 | VPQTGEVSGNI | 29685 |
| HPV45 | L2 | 10 | 119 | VPTFTGTSGF | 29686 |
| HPV45 | L2 | 8 | 112 | VVASGAPV | 29687 |
| HPV45 | L2 | 11 | 112 | VVASGAPVPTF | 29688 |
| HPV45 | L2 | 11 | 81 | VVDVGPTRPPV | 29689 |
| HPV45 | L2 | 9 | 415 | WPSTSPTNA | 29690 |
| HPV45 | L2 | 9 | 428 | YIGIHGTQY | 29691 |
| HPV45 | L2 | 10 | 428 | YIGIHGTQYY | 29692 |
| HPV45 | L2 | 11 | 428 | YIGIHGTQYYL | 29693 |
| HPV45 | L2 | 8 | 437 | YLWPWYYY | 29694 |
| HPV45 | L2 | 9 | 437 | YLWPWYYYF | 29695 |
| HPV45 | L2 | 8 | 370 | YPKYSLTM | 29696 |
| HPV45 | L2 | 11 | 71 | YVPLGGRSNTV | 29697 |
| HPV56 | E2 | 8 | 15 | AIEVQIAL | 29698 |
| HPV56 | E2 | 11 | 15 | AIEVQIALESL | 29699 |
| HPV56 | E2 | 9 | 21 | ALESLSTTI | 29700 |
| HPV56 | E2 | 10 | 21 | ALESLSTTIY | 29701 |
| HPV56 | E2 | 9 | 4 | CLQVCKAKA | 29702 |
| HPV56 | E2 | 9 | 71 | CMQYVAWKY | 29703 |
| HPV56 | E2 | 10 | 71 | CMQYVAWKYI | 29704 |
| HPV56 | E2 | 11 | 71 | CMQYVAWKYIY | 29705 |
| HPV56 | E2 | 11 | 138 | CPDSVSSTCRY | 29706 |
| HPV56 | E2 | 8 | 204 | CVTTHTHI | 29707 |
| HPV56 | E2 | 8 | 263 | DVTSTYHW | 29708 |
| HPV56 | E2 | 11 | 43 | ELWLTEPKKCF | 29709 |

TABLE XIV-continued

B62 Supermotif Peptides

| Type | Protein | No. of Amino Acid | Position | Sequence | Seq. Id. No. |
|---|---|---|---|---|---|
| HPV56 | E2 | 10 | 243 | EPNRLKCCRY | 29710 |
| HPV56 | E2 | 9 | 128 | EVHMENESI | 29711 |
| HPV56 | E2 | 10 | 128 | EVHMENESIY | 29712 |
| HPV56 | E2 | 9 | 17 | EVQIALESL | 29713 |
| HPV56 | E2 | 9 | 294 | FLSHVKIPV | 29714 |
| HPV56 | E2 | 10 | 294 | FLSHVKIPVV | 29715 |
| HPV56 | E2 | 11 | 294 | FLSHVKIPVVY | 29716 |
| HPV56 | E2 | 8 | 254 | FQKYKTLF | 29717 |
| HPV56 | E2 | 9 | 254 | FQKYKTLFV | 29718 |
| HPV56 | E2 | 11 | 254 | FQKYKTLFVDV | 29719 |
| HPV56 | E2 | 8 | 261 | FVDVTSTY | 29720 |
| HPV56 | E2 | 10 | 261 | FVDVTSTYHW | 29721 |
| HPV56 | E2 | 8 | 57 | GQHIEVWF | 29722 |
| HPV56 | E2 | 8 | 94 | GVDYRGIY | 29723 |
| HPV56 | E2 | 9 | 94 | GVDYRGIYY | 29724 |
| HPV56 | E2 | 10 | 94 | GVDYRGIYYV | 29725 |
| HPV56 | E2 | 9 | 239 | HLKGEPNRL | 29726 |
| HPV56 | E2 | 8 | 130 | HMENESIY | 29727 |
| HPV56 | E2 | 9 | 229 | HPGDKTTPV | 29728 |
| HPV56 | E2 | 10 | 229 | HPGDKTTPVV | 29729 |
| HPV56 | E2 | 8 | 297 | HVKIPVVY | 29730 |
| HPV56 | E2 | 10 | 297 | HVKIPVVYRL | 29731 |
| HPV56 | E2 | 11 | 297 | HVKIPVVYRLV | 29732 |
| HPV56 | E2 | 8 | 300 | IPVVYRLV | 29733 |
| HPV56 | E2 | 9 | 300 | IPVVYRLVW | 29734 |
| HPV56 | E2 | 8 | 299 | KIPVVYRL | 29735 |
| HPV56 | E2 | 9 | 299 | KIPVVYRLV | 29736 |
| HPV56 | E2 | 10 | 299 | KIPVVYRLVW | 29737 |
| HPV56 | E2 | 8 | 90 | KVCSGVDY | 29738 |
| HPV56 | E2 | 11 | 90 | KVCSGVDYRGI | 29739 |
| HPV56 | E2 | 8 | 5 | LQVCKAKA | 29740 |
| HPV56 | E2 | 11 | 5 | LQVCKAKACSA | 29741 |
| HPV56 | E2 | 8 | 72 | MQYVAWKY | 29742 |
| HPV56 | E2 | 9 | 72 | MQYVAWKYI | 29743 |
| HPV56 | E2 | 10 | 72 | MQYVAWKYIY | 29744 |
| HPV56 | E2 | 11 | 72 | MQYVAWKYIYY | 29745 |
| HPV56 | E2 | 10 | 1 | MVPCLQVCKA | 29746 |
| HPV56 | E2 | 8 | 149 | NVSPVETV | 29747 |
| HPV56 | E2 | 11 | 149 | NVSPVETVNEY | 29748 |
| HPV56 | E2 | 8 | 152 | PVETVNEY | 29749 |
| HPV56 | E2 | 8 | 301 | PVVYRLVW | 29750 |
| HPV56 | E2 | 11 | 19 | QIALESLSTTI | 29751 |
| HPV56 | E2 | 10 | 6 | QVCKAKACSA | 29752 |
| HPV56 | E2 | 11 | 6 | QVCKAKACSAI | 29753 |
| HPV56 | E2 | 9 | 246 | RLKCCRYRF | 29754 |
| HPV56 | E2 | 8 | 182 | RPGKRPRL | 29755 |
| HPV56 | E2 | 9 | 186 | RPRLRESEF | 29756 |
| HPV56 | E2 | 8 | 135 | SIYCPDSV | 29757 |
| HPV56 | E2 | 9 | 151 | SPVETVNEY | 29758 |
| HPV56 | E2 | 8 | 171 | SVGNQDAA | 29759 |
| HPV56 | E2 | 9 | 171 | SVGNQDAAV | 29760 |
| HPV56 | E2 | 8 | 141 | SVSSTCRY | 29761 |
| HPV56 | E2 | 10 | 141 | SVSSTCRYNV | 29762 |
| HPV56 | E2 | 8 | 28 | TIYNNEEW | 29763 |
| HPV56 | E2 | 10 | 28 | TIYNNEEWTL | 29764 |
| HPV56 | E2 | 10 | 259 | TLFVDVTSTY | 29765 |
| HPV56 | E2 | 9 | 36 | TLRDTCEEL | 29766 |
| HPV56 | E2 | 10 | 36 | TLRDTCEELW | 29767 |
| HPV56 | E2 | 11 | 36 | TLRDTCEELWL | 29768 |
| HPV56 | E2 | 10 | 289 | TQRNSFLSHV | 29769 |
| HPV56 | E2 | 9 | 2 | VPCLQVCKA | 29770 |
| HPV56 | E2 | 11 | 2 | VPCLQVCKAKA | 29771 |
| HPV56 | E2 | 8 | 18 | VQIALESL | 29772 |
| HPV56 | E2 | 11 | 237 | VVHLKGEPNRL | 29773 |
| HPV56 | E2 | 9 | 45 | WLTEPKKCF | 29774 |
| HPV56 | E2 | 8 | 88 | WQKVCSGV | 29775 |
| HPV56 | E2 | 10 | 88 | WQKVCSGVDY | 29776 |
| HPV56 | E2 | 10 | 79 | YIYYNGDCGW | 29777 |
| HPV56 | E2 | 8 | 74 | YVAWKYIY | 29778 |
| HPV56 | E2 | 9 | 74 | YVAWKYIYY | 29779 |
| HPV56 | E2 | 9 | 102 | YVHDGHKTY | 29780 |
| HPV56 | E2 | 10 | 102 | YVHDGHKTYY | 29781 |
| HPV56 | E6 | 8 | 64 | AVCRVCLL | 29782 |
| HPV56 | E6 | 9 | 64 | AVCRVCLLF | 29783 |
| HPV56 | E6 | 10 | 64 | AVCRVCLLFY | 29784 |

TABLE XIV-continued

B62 Supermotif Peptides

| Type | Protein | No. of Amino Acid | Position | Sequence | Seq. Id. No. |
|---|---|---|---|---|---|
| HPV56 | E6 | 8 | 69 | CLLFYSKV | 29785 |
| HPV56 | E6 | 11 | 69 | CLLFYSKVRKY | 29786 |
| HPV56 | E6 | 8 | 33 | CVYCKKEL | 29787 |
| HPV56 | E6 | 11 | 33 | CVYCKKELTRA | 29788 |
| HPV56 | E6 | 8 | 28 | DLRLSCVY | 29789 |
| HPV56 | E6 | 9 | 23 | EIPLIDLRL | 29790 |
| HPV56 | E6 | 10 | 52 | ELKLVYRDDF | 29791 |
| HPV56 | E6 | 8 | 39 | ELTRAEVY | 29792 |
| HPV56 | E6 | 10 | 39 | ELTRAEVYNF | 29793 |
| HPV56 | E6 | 11 | 39 | ELTRAEVYNFA | 29794 |
| HPV56 | E6 | 8 | 20 | EVLEIPLI | 29795 |
| HPV56 | E6 | 10 | 20 | EVLEIPLIDL | 29796 |
| HPV56 | E6 | 10 | 44 | EVYNFACTEL | 29797 |
| HPV56 | E6 | 8 | 61 | FPYAVCRV | 29798 |
| HPV56 | E6 | 10 | 61 | FPYAVCRVCL | 29799 |
| HPV56 | E6 | 11 | 61 | FPYAVCRVCLL | 29800 |
| HPV56 | E6 | 8 | 17 | HLSEVLEI | 29801 |
| HPV56 | E6 | 10 | 17 | HLSEVLEIPL | 29802 |
| HPV56 | E6 | 11 | 17 | HLSEVLEIPLI | 29803 |
| HPV56 | E6 | 8 | 24 | IPLIDLRL | 29804 |
| HPV56 | E6 | 11 | 24 | IPLIDLRLSCV | 29805 |
| HPV56 | E6 | 8 | 54 | KLVYRDDF | 29806 |
| HPV56 | E6 | 10 | 54 | KLVYRDDFPY | 29807 |
| HPV56 | E6 | 11 | 54 | KLVYRDDFPYA | 29808 |
| HPV56 | E6 | 8 | 97 | KQLCDLLI | 29809 |
| HPV56 | E6 | 11 | 97 | KQLCDLLIRCY | 29810 |
| HPV56 | E6 | 11 | 118 | KQLHCDRKRRF | 29811 |
| HPV56 | E6 | 8 | 75 | KVRKYRYY | 29812 |
| HPV56 | E6 | 10 | 75 | KVRKYRYYDY | 29813 |
| HPV56 | E6 | 11 | 130 | LIAHGWTGSCL | 29814 |
| HPV56 | E6 | 9 | 26 | LIDLRLSCV | 29815 |
| HPV56 | E6 | 10 | 26 | LIDLRLSCVY | 29816 |
| HPV56 | E6 | 11 | 103 | LIRCYRCQSPL | 29817 |
| HPV56 | E6 | 10 | 70 | LLFYSKVRKY | 29818 |
| HPV56 | E6 | 9 | 55 | LVYRDDFPY | 29819 |
| HPV56 | E6 | 10 | 55 | LVYRDDFPYA | 29820 |
| HPV56 | E6 | 11 | 55 | LVYRDDFPYAV | 29821 |
| HPV56 | E6 | 9 | 7 | NPQERPRSL | 29822 |
| HPV56 | E6 | 10 | 25 | PLIDLRLSCV | 29823 |
| HPV56 | E6 | 11 | 25 | PLIDLRLSCVY | 29824 |
| HPV56 | E6 | 9 | 112 | PLTPEEKQL | 29825 |
| HPV56 | E6 | 8 | 8 | PQERPRSL | 29826 |
| HPV56 | E6 | 11 | 8 | PQERPRSLHHL | 29827 |
| HPV56 | E6 | 10 | 98 | QLCDLLIRCY | 29828 |
| HPV56 | E6 | 10 | 119 | QLHCDRKRRF | 29829 |
| HPV56 | E6 | 11 | 30 | RLSCVYCKKEL | 29830 |
| HPV56 | E6 | 8 | 11 | RPRSLHHL | 29831 |
| HPV56 | E6 | 11 | 11 | RPRSLHHLSEV | 29832 |
| HPV56 | E6 | 10 | 67 | RVCLLFYSKV | 29833 |
| HPV56 | E6 | 10 | 93 | SITKKQLCDL | 29834 |
| HPV56 | E6 | 11 | 93 | SITKKQLCDLL | 29835 |
| HPV56 | E6 | 8 | 14 | SLHHLSEV | 29836 |
| HPV56 | E6 | 9 | 14 | SLHHLSEVL | 29837 |
| HPV56 | E6 | 11 | 14 | SLHHLSEVLEI | 29838 |
| HPV56 | E6 | 10 | 111 | SPLTPEEKQL | 29839 |
| HPV56 | E6 | 10 | 85 | SVYGATLESI | 29840 |
| HPV56 | E6 | 10 | 90 | TLESITKKQL | 29841 |
| HPV56 | E6 | 9 | 21 | VLEIPLIDL | 29842 |
| HPV56 | E6 | 11 | 21 | VLEIPLIDLRL | 29843 |
| HPV56 | E7 | 8 | 93 | ALTVTCPL | 29844 |
| HPV56 | E7 | 10 | 93 | ALTVTCPLCA | 29845 |
| HPV56 | E7 | 9 | 75 | DIQSTKEDL | 29846 |
| HPV56 | E7 | 11 | 75 | DIQSTKEDLRV | 29847 |
| HPV56 | E7 | 8 | 22 | DLQCNEQL | 29848 |
| HPV56 | E7 | 8 | 82 | DLRVVQQL | 29849 |
| HPV56 | E7 | 9 | 82 | DLRVVQQLL | 29850 |
| HPV56 | E7 | 10 | 82 | DLRVVQQLLM | 29851 |
| HPV56 | E7 | 10 | 20 | EIDLQCNEQL | 29852 |
| HPV56 | E7 | 8 | 14 | ELTPQTEI | 29853 |
| HPV56 | E7 | 10 | 14 | ELTPQTEIDL | 29854 |
| HPV56 | E7 | 9 | 42 | HLQERPQQA | 29855 |
| HPV56 | E7 | 9 | 62 | HVPCCECKF | 29856 |
| HPV56 | E7 | 10 | 62 | HVPCCECKFV | 29857 |
| HPV56 | E7 | 11 | 62 | HVPCCECKFVV | 29858 |
| HPV56 | E7 | 8 | 76 | IQSTKEDL | 29859 |

TABLE XIV-continued

B62 Supermotif Peptides

| Type | Protein | No. of Amino Acid | Position | Sequence | Seq. Id. No. |
|---|---|---|---|---|---|
| HPV56 | E7 | 10 | 76 | IQSTKEDLRV | 29860 |
| HPV56 | E7 | 11 | 76 | IQSTKEDLRVV | 29861 |
| HPV56 | E7 | 8 | 54 | KQHTCYLI | 29862 |
| HPV56 | E7 | 10 | 54 | KQHTCYLIHV | 29863 |
| HPV56 | E7 | 8 | 4 | KVPTLQDV | 29864 |
| HPV56 | E7 | 9 | 4 | KVPTLQDVV | 29865 |
| HPV56 | E7 | 10 | 4 | KVPTLQDVVL | 29866 |
| HPV56 | E7 | 11 | 60 | LIHVPCCECKF | 29867 |
| HPV56 | E7 | 8 | 89 | LLMGALTV | 29868 |
| HPV56 | E7 | 11 | 90 | LMGALTVTCPL | 29869 |
| HPV56 | E7 | 8 | 8 | LQDVVLEL | 29870 |
| HPV56 | E7 | 8 | 43 | LQERPQQA | 29871 |
| HPV56 | E7 | 11 | 43 | LQERPQQARQA | 29872 |
| HPV56 | E7 | 11 | 73 | QLDIQSTKEDL | 29873 |
| HPV56 | E7 | 9 | 88 | QLLMGALTV | 29874 |
| HPV56 | E7 | 8 | 87 | QQLLMGAL | 29875 |
| HPV56 | E7 | 10 | 87 | QQLLMGALTV | 29876 |
| HPV56 | E7 | 8 | 46 | RPQQARQA | 29877 |
| HPV56 | E7 | 9 | 51 | RQAKQHTCY | 29878 |
| HPV56 | E7 | 10 | 51 | RQAKQHTCYL | 29879 |
| HPV56 | E7 | 11 | 51 | RQAKQHTCYLI | 29880 |
| HPV56 | E7 | 8 | 84 | RVVQQLLM | 29881 |
| HPV56 | E7 | 10 | 84 | RVVQQLLMGA | 29882 |
| HPV56 | E7 | 11 | 84 | RVVQQLLMGAL | 29883 |
| HPV56 | E7 | 9 | 7 | TLQDVVLEL | 29884 |
| HPV56 | E7 | 8 | 16 | TPQTEIDL | 29885 |
| HPV56 | E7 | 8 | 95 | TVTCPLCA | 29886 |
| HPV56 | E7 | 10 | 12 | VLELTPQTEI | 29887 |
| HPV56 | E7 | 8 | 63 | VPCCECKF | 29888 |
| HPV56 | E7 | 9 | 63 | VPCCECKFV | 29889 |
| HPV56 | E7 | 10 | 63 | VPCCECKFVV | 29890 |
| HPV56 | E7 | 8 | 5 | VPTLQDVV | 29891 |
| HPV56 | E7 | 9 | 5 | VPTLQDVVL | 29892 |
| HPV56 | E7 | 11 | 5 | VPTLQDVVLEL | 29893 |
| HPV56 | E7 | 8 | 86 | VQQLLMGA | 29894 |
| HPV56 | E7 | 9 | 86 | VQQLLMGAL | 29895 |
| HPV56 | E7 | 11 | 86 | VQQLLMGALTV | 29896 |
| HPV56 | E7 | 11 | 11 | VVLELTPQTEI | 29897 |
| HPV56 | E7 | 9 | 85 | VVQQLLMGA | 29898 |
| HPV56 | E7 | 10 | 85 | VVQQLLMGAL | 29899 |
| HPV56 | L1 | 10 | 198 | AMGEHWTKGA | 29900 |
| HPV56 | L1 | 11 | 198 | AMGEHWTKGAV | 29901 |
| HPV56 | L1 | 9 | 521 | APTSTSTPA | 29902 |
| HPV56 | L1 | 8 | 350 | AQGHNNGI | 29903 |
| HPV56 | L1 | 10 | 350 | AQGHNNGICW | 29904 |
| HPV56 | L1 | 8 | 338 | AQLFNKPY | 29905 |
| HPV56 | L1 | 9 | 338 | AQLFNKPYW | 29906 |
| HPV56 | L1 | 10 | 338 | AQLFNKPYWL | 29907 |
| HPV56 | L1 | 10 | 512 | AVATSKKRSA | 29908 |
| HPV56 | L1 | 8 | 207 | AVCKSTQV | 29909 |
| HPV56 | L1 | 9 | 79 | AVGHPYYSV | 29910 |
| HPV56 | L1 | 8 | 26 | AVNVFPIF | 29911 |
| HPV56 | L1 | 9 | 26 | AVNVFPIFL | 29912 |
| HPV56 | L1 | 11 | 26 | AVNVFPIFLQM | 29913 |
| HPV56 | L1 | 8 | 19 | CIFLDVGA | 29914 |
| HPV56 | L1 | 9 | 19 | CIFLDVGAV | 29915 |
| HPV56 | L1 | 11 | 19 | CIFLDVGAVNV | 29916 |
| HPV56 | L1 | 8 | 191 | CIVGCTPA | 29917 |
| HPV56 | L1 | 9 | 191 | CIVGCTPAM | 29918 |
| HPV56 | L1 | 11 | 219 | CPPLALINTPI | 29919 |
| HPV56 | L1 | 9 | 257 | DIVQSTCKY | 29920 |
| HPV56 | L1 | 11 | 491 | DLDQFPLGRKF | 29921 |
| HPV56 | L1 | 9 | 233 | DMIDTGFGA | 29922 |
| HPV56 | L1 | 10 | 233 | DMIDTGFGAM | 29923 |
| HPV56 | L1 | 8 | 472 | DPLAKYKF | 29924 |
| HPV56 | L1 | 9 | 472 | DPLAKYKFW | 29925 |
| HPV56 | L1 | 11 | 472 | DPLAKYKFWDV | 29926 |
| HPV56 | L1 | 8 | 11 | DPPLHYGL | 29927 |
| HPV56 | L1 | 10 | 11 | DPPLHYGLCI | 29928 |
| HPV56 | L1 | 11 | 11 | DPPLHYGLCIF | 29929 |
| HPV56 | L1 | 8 | 128 | DQERLVWA | 29930 |
| HPV56 | L1 | 10 | 128 | DQERLVWACV | 29931 |
| HPV56 | L1 | 9 | 493 | DQFPLGRKF | 29932 |
| HPV56 | L1 | 10 | 493 | DQFPLGRKFL | 29933 |
| HPV56 | L1 | 11 | 493 | DQFPLGRKFLM | 29934 |

TABLE XIV-continued

B62 Supermotif Peptides

| Type | Protein | No. of Amino Acid | Position | Sequence | Seq. Id. No. |
|---|---|---|---|---|---|
| HPV56 | L1 | 8 | 23 | DVGAVNVF | 29935 |
| HPV56 | L1 | 10 | 23 | DVGAVNVFPI | 29936 |
| HPV56 | L1 | 11 | 23 | DVGAVNVFPIF | 29937 |
| HPV56 | L1 | 8 | 481 | DVNLQDSF | 29938 |
| HPV56 | L1 | 8 | 404 | ELQFVFQL | 29939 |
| HPV56 | L1 | 11 | 404 | ELQFVFQLCKI | 29940 |
| HPV56 | L1 | 8 | 318 | EPPPSSVY | 29941 |
| HPV56 | L1 | 9 | 318 | EPPPSSVYV | 29942 |
| HPV56 | L1 | 10 | 318 | EPPPSSVYVA | 29943 |
| HPV56 | L1 | 8 | 287 | EQLFARHY | 29944 |
| HPV56 | L1 | 9 | 287 | EQLFARHYF | 29945 |
| HPV56 | L1 | 8 | 383 | EQLSKYDA | 29946 |
| HPV56 | L1 | 11 | 383 | EQLSKYDARKI | 29947 |
| HPV56 | L1 | 11 | 464 | EQPPTEKQDPL | 29948 |
| HPV56 | L1 | 8 | 140 | EVGRGQPL | 29949 |
| HPV56 | L1 | 10 | 140 | EVGRGQPLGA | 29950 |
| HPV56 | L1 | 9 | 419 | EVMAYLHNM | 29951 |
| HPV56 | L1 | 11 | 419 | EVMAYLHNMNA | 29952 |
| HPV56 | L1 | 9 | 21 | FLDVGAVNV | 29953 |
| HPV56 | L1 | 10 | 21 | FLDVGAVNVF | 29954 |
| HPV56 | L1 | 8 | 30 | FPIFLQMA | 29955 |
| HPV56 | L1 | 10 | 30 | FPIFLQMATW | 29956 |
| HPV56 | L1 | 8 | 495 | FPLGRKFL | 29957 |
| HPV56 | L1 | 9 | 495 | FPLGRKFLM | 29958 |
| HPV56 | L1 | 11 | 495 | FPLGRKFLMQL | 29959 |
| HPV56 | L1 | 8 | 409 | FQLCKITL | 29960 |
| HPV56 | L1 | 10 | 409 | FQLCKITLSA | 29961 |
| HPV56 | L1 | 8 | 407 | FVFQLCKI | 29962 |
| HPV56 | L1 | 10 | 407 | FVFQLCKITL | 29963 |
| HPV56 | L1 | 8 | 356 | GICWGNQL | 29964 |
| HPV56 | L1 | 9 | 356 | GICWGNQLF | 29965 |
| HPV56 | L1 | 10 | 356 | GICWGNQLFV | 29966 |
| HPV56 | L1 | 8 | 17 | GLCIFLDV | 29967 |
| HPV56 | L1 | 10 | 17 | GLCIFLDVGA | 29968 |
| HPV56 | L1 | 11 | 17 | GLCIFLDVGAV | 29969 |
| HPV56 | L1 | 10 | 138 | GLEVGRGQPL | 29970 |
| HPV56 | L1 | 8 | 118 | GLPDTNIY | 29971 |
| HPV56 | L1 | 8 | 150 | GLSGHPLF | 29972 |
| HPV56 | L1 | 11 | 150 | GLSGHPLFNRL | 29973 |
| HPV56 | L1 | 10 | 438 | GLSPPVATSL | 29974 |
| HPV56 | L1 | 8 | 144 | GQPLGAGL | 29975 |
| HPV56 | L1 | 9 | 399 | HVEEYELQF | 29976 |
| HPV56 | L1 | 10 | 399 | HVEEYELQFV | 29977 |
| HPV56 | L1 | 11 | 399 | HVEEYELQFVF | 29978 |
| HPV56 | L1 | 9 | 96 | IPKVSAYQY | 29979 |
| HPV56 | L1 | 11 | 96 | IPKVSAYQYRV | 29980 |
| HPV56 | L1 | 8 | 192 | IVGCTPAM | 29981 |
| HPV56 | L1 | 8 | 258 | IVQSTCKY | 29982 |
| HPV56 | L1 | 11 | 258 | IVQSTCKYPDY | 29983 |
| HPV56 | L1 | 9 | 392 | KINQYLRHV | 29984 |
| HPV56 | L1 | 8 | 413 | KITLSAEV | 29985 |
| HPV56 | L1 | 9 | 413 | KITLSAEVM | 29986 |
| HPV56 | L1 | 10 | 413 | KITLSAEVMA | 29987 |
| HPV56 | L1 | 11 | 413 | KITLSAEVMAY | 29988 |
| HPV56 | L1 | 11 | 270 | KMSADAYGDSM | 29989 |
| HPV56 | L1 | 8 | 343 | KPYWLQRA | 29990 |
| HPV56 | L1 | 8 | 470 | KQDPLAKY | 29991 |
| HPV56 | L1 | 10 | 470 | RQDPLAKYKF | 29992 |
| HPV56 | L1 | 11 | 470 | KQDPLAKYKFW | 29993 |
| HPV56 | L1 | 8 | 186 | KQTQLCIV | 29994 |
| HPV56 | L1 | 8 | 300 | KVGETIPA | 29995 |
| HPV56 | L1 | 10 | 300 | KVGETIPAEL | 29996 |
| HPV56 | L1 | 11 | 300 | KVGETIPAELY | 29997 |
| HPV56 | L1 | 8 | 245 | KVLQESKA | 29998 |
| HPV56 | L1 | 10 | 245 | KVLQESKAEV | 29999 |
| HPV56 | L1 | 9 | 98 | KVSAYQYRV | 30000 |
| HPV56 | L1 | 10 | 98 | KVSAYQYRVF | 30001 |
| HPV56 | L1 | 8 | 55 | KVVATDSY | 30002 |
| HPV56 | L1 | 9 | 55 | KVVATDSYV | 30003 |
| HPV56 | L1 | 9 | 45 | KVYLPPTPV | 30004 |
| HPV56 | L1 | 11 | 224 | LINTPIEDGDM | 30005 |
| HPV56 | L1 | 8 | 77 | LLAVGHPY | 30006 |
| HPV56 | L1 | 9 | 77 | LLAVGHPYY | 30007 |
| HPV56 | L1 | 11 | 77 | LLAVGHPYYSV | 30008 |
| HPV56 | L1 | 9 | 431 | LLEDWNIGL | 30009 |

TABLE XIV-continued

B62 Supermotif Peptides

| Type | Protein | No. of Amino Acid | Position | Sequence | Seq. Id. No. |
|---|---|---|---|---|---|
| HPV56 | L1 | 11 | 502 | LMQLGTRSKPA | 30010 |
| HPV56 | L1 | 9 | 111 | LPDPNKFGL | 30011 |
| HPV56 | L1 | 9 | 48 | LPPTPVSKV | 30012 |
| HPV56 | L1 | 10 | 48 | LPPTPVSKVV | 30013 |
| HPV56 | L1 | 11 | 48 | LPPTPVSKVVA | 30014 |
| HPV56 | L1 | 9 | 484 | LQDSFSTDL | 30015 |
| HPV56 | L1 | 8 | 247 | LQESKAEV | 30016 |
| HPV56 | L1 | 10 | 247 | LQESKAEVPL | 30017 |
| HPV56 | L1 | 10 | 405 | LQFVFQLCKI | 30018 |
| HPV56 | L1 | 11 | 347 | LQRAQGHNNGI | 30019 |
| HPV56 | L1 | 8 | 132 | LVWACVGL | 30020 |
| HPV56 | L1 | 10 | 132 | LVWACVGLEV | 30021 |
| HPV56 | L1 | 8 | 234 | MIDTGFGA | 30022 |
| HPV56 | L1 | 9 | 234 | MIDTGFGAM | 30023 |
| HPV56 | L1 | 11 | 234 | MIDTGFGAMDF | 30024 |
| HPV56 | L1 | 8 | 333 | MITSEAQL | 30025 |
| HPV56 | L1 | 9 | 333 | MITSEAQLF | 30026 |
| HPV56 | L1 | 8 | 2 | MLPMMYIY | 30027 |
| HPV56 | L1 | 8 | 1 | MMLPMMYI | 30028 |
| HPV56 | L1 | 9 | 1 | MMLPMMYIY | 30029 |
| HPV56 | L1 | 10 | 5 | MMYIYRDPPL | 30030 |
| HPV56 | L1 | 10 | 503 | MQLGTRSKPA | 30031 |
| HPV56 | L1 | 11 | 503 | MQLGTRSKPAV | 30032 |
| HPV56 | L1 | 8 | 436 | NIGLSPPV | 30033 |
| HPV56 | L1 | 9 | 436 | NIGLSPPVA | 30034 |
| HPV56 | L1 | 8 | 95 | NIPKVSAY | 30035 |
| HPV56 | L1 | 10 | 95 | NIPKVSAYQY | 30036 |
| HPV56 | L1 | 11 | 180 | NISVDGKQTQL | 30037 |
| HPV56 | L1 | 10 | 123 | NIYNPDQERL | 30038 |
| HPV56 | L1 | 11 | 123 | NIYNPDQERLV | 30039 |
| HPV56 | L1 | 8 | 167 | NLANNNVI | 30040 |
| HPV56 | L1 | 8 | 430 | NLLEDWNI | 30041 |
| HPV56 | L1 | 10 | 430 | NLLEDWNIGL | 30042 |
| HPV56 | L1 | 10 | 483 | NLQDSFSTDL | 30043 |
| HPV56 | L1 | 10 | 426 | NMNANLLEDW | 30044 |
| HPV56 | L1 | 11 | 375 | NMTISTATEQL | 30045 |
| HPV56 | L1 | 8 | 126 | NPDQERLV | 30046 |
| HPV56 | L1 | 9 | 126 | NPDQERLVW | 30047 |
| HPV56 | L1 | 10 | 126 | NPDQERLVWA | 30048 |
| HPV56 | L1 | 8 | 361 | NQLFVTVV | 30049 |
| HPV56 | L1 | 10 | 394 | NQYLRHVEEY | 30050 |
| HPV56 | L1 | 9 | 28 | NVFPIFLQM | 30051 |
| HPV56 | L1 | 10 | 28 | NVFPIFLQMA | 30052 |
| HPV56 | L1 | 10 | 172 | NVIEDSRDNI | 30053 |
| HPV56 | L1 | 8 | 228 | PIEDGDMI | 30054 |
| HPV56 | L1 | 9 | 31 | PIFLQMATW | 30055 |
| HPV56 | L1 | 8 | 473 | PLAKYKFW | 30056 |
| HPV56 | L1 | 10 | 473 | PLAKYKFWDV | 30057 |
| HPV56 | L1 | 9 | 221 | PLALINTPI | 30058 |
| HPV56 | L1 | 11 | 255 | PLDIVQSTCKY | 30059 |
| HPV56 | L1 | 11 | 146 | PLGAGLSGHPL | 30060 |
| HPV56 | L1 | 8 | 496 | PLGRKFLM | 30061 |
| HPV56 | L1 | 10 | 496 | PLGRKFLMQL | 30062 |
| HPV56 | L1 | 8 | 13 | PLHYGLCI | 30063 |
| HPV56 | L1 | 9 | 13 | PLHYGLCIF | 30064 |
| HPV56 | L1 | 10 | 13 | PLHYGLCIFL | 30065 |
| HPV56 | L1 | 11 | 4 | PMMYIYRDPPL | 30066 |
| HPV56 | L1 | 10 | 220 | PPLALINTPI | 30067 |
| HPV56 | L1 | 9 | 12 | PPLHYGLCI | 30068 |
| HPV56 | L1 | 10 | 12 | PPLHYGLCIF | 30069 |
| HPV56 | L1 | 11 | 12 | PPLHYGLCIFL | 30070 |
| HPV56 | L1 | 8 | 319 | PPPSSVYV | 30071 |
| HPV56 | L1 | 9 | 319 | PPPSSVYVA | 30072 |
| HPV56 | L1 | 8 | 320 | PPSSVYVA | 30073 |
| HPV56 | L1 | 9 | 466 | PPTEKQDPL | 30074 |
| HPV56 | L1 | 10 | 466 | PPTEKQDPLA | 30075 |
| HPV56 | L1 | 8 | 49 | PPTPVSKV | 30076 |
| HPV56 | L1 | 9 | 49 | PPTPVSKVV | 30077 |
| HPV56 | L1 | 10 | 49 | PPTPVSKVVA | 30078 |
| HPV56 | L1 | 11 | 441 | PPVATSLEDKY | 30079 |
| HPV56 | L1 | 10 | 442 | PVATSLEDKY | 30080 |
| HPV56 | L1 | 11 | 52 | PVSKVVATDSY | 30081 |
| HPV56 | L1 | 10 | 189 | QLCIVGCTPA | 30082 |
| HPV56 | L1 | 11 | 189 | QLCIVGCTPAM | 30083 |
| HPV56 | L1 | 9 | 410 | QLCKITLSA | 30084 |

TABLE XIV-continued

B62 Supermotif Peptides

| Type | Protein | No. of Amino Acid | Position | Sequence | Seq. Id. No. |
|---|---|---|---|---|---|
| HPV56 | L1 | 11 | 410 | QLCKITLSAEV | 30085 |
| HPV56 | L1 | 8 | 288 | QLFARHYF | 30086 |
| HPV56 | L1 | 11 | 288 | QLFARHYFNRA | 30087 |
| HPV56 | L1 | 8 | 339 | QLFNKPYW | 30088 |
| HPV56 | L1 | 9 | 339 | QLFNKPYWL | 30089 |
| HPV56 | L1 | 9 | 504 | QLGTRSKPA | 30090 |
| HPV56 | L1 | 10 | 504 | QLGTRSKPAV | 30091 |
| HPV56 | L1 | 11 | 504 | QLGTRSKPAVA | 30092 |
| HPV56 | L1 | 10 | 384 | QLSKYDARKI | 30093 |
| HPV56 | L1 | 10 | 465 | QPPTEKQDPL | 30094 |
| HPV56 | L1 | 11 | 465 | QPPTEKQDPLA | 30095 |
| HPV56 | L1 | 10 | 213 | QVTTGDCPPL | 30096 |
| HPV56 | L1 | 11 | 213 | QVTTGDCPPLA | 30097 |
| HPV56 | L1 | 10 | 159 | RLDDTESSNL | 30098 |
| HPV56 | L1 | 11 | 159 | RLDDTESSNLA | 30099 |
| HPV56 | L1 | 9 | 76 | RLLAVGHPY | 30100 |
| HPV56 | L1 | 10 | 76 | RLLAVGHPYY | 30101 |
| HPV56 | L1 | 8 | 110 | RLPDPNKF | 30102 |
| HPV56 | L1 | 10 | 110 | RLPDPNKFGL | 30103 |
| HPV56 | L1 | 9 | 131 | RLVWACVGL | 30104 |
| HPV56 | L1 | 11 | 131 | RLVWACVGLEV | 30105 |
| HPV56 | L1 | 8 | 40 | RPSENKVY | 30106 |
| HPV56 | L1 | 9 | 40 | RPSENKVYL | 30107 |
| HPV56 | L1 | 10 | 108 | RVRLPDPNKF | 30108 |
| HPV56 | L1 | 11 | 67 | SIFYHAGSSRL | 30109 |
| HPV56 | L1 | 8 | 446 | SLEDKYRY | 30110 |
| HPV56 | L1 | 9 | 446 | SLEDKYRYV | 30111 |
| HPV56 | L1 | 9 | 332 | SMITSEAQL | 30112 |
| HPV56 | L1 | 10 | 332 | SMITSEAQLF | 30113 |
| HPV56 | L1 | 11 | 279 | SMWFYLRREQL | 30114 |
| HPV56 | L1 | 8 | 440 | SPPVATSL | 30115 |
| HPV56 | L1 | 9 | 182 | SVDGKQTQL | 30116 |
| HPV56 | L1 | 11 | 182 | SVDGKQTQLCI | 30117 |
| HPV56 | L1 | 11 | 86 | SVTKDNTKTNI | 30118 |
| HPV56 | L1 | 11 | 323 | SVYVATPSGSM | 30119 |
| HPV56 | L1 | 8 | 304 | TIPAELYL | 30120 |
| HPV56 | L1 | 9 | 377 | TISTATEQL | 30121 |
| HPV56 | L1 | 8 | 415 | TLSAEVMA | 30122 |
| HPV56 | L1 | 9 | 415 | TLSAEVMAY | 30123 |
| HPV56 | L1 | 10 | 415 | TLSAEVMAYL | 30124 |
| HPV56 | L1 | 8 | 196 | TPAMGEHW | 30125 |
| HPV56 | L1 | 8 | 227 | TPIEDGDM | 30126 |
| HPV56 | L1 | 9 | 227 | TPIEDGDMI | 30127 |
| HPV56 | L1 | 11 | 328 | TPSGSMITSEA | 30128 |
| HPV56 | L1 | 8 | 51 | TPVSKVVA | 30129 |
| HPV56 | L1 | 11 | 188 | TQLCIVGCTPA | 30130 |
| HPV56 | L1 | 11 | 212 | TQVTTGDCPPL | 30131 |
| HPV56 | L1 | 11 | 366 | TVVDTTRSTNM | 30132 |
| HPV56 | L1 | 9 | 173 | VIEDSRDNI | 30133 |
| HPV56 | L1 | 11 | 173 | VIEDSRDNISV | 30134 |
| HPV56 | L1 | 9 | 246 | VLQESKAEV | 30135 |
| HPV56 | L1 | 11 | 246 | VLQESKAEVPL | 30136 |
| HPV56 | L1 | 8 | 420 | VMAYLHNM | 30137 |
| HPV56 | L1 | 10 | 420 | VMAYLHNMNA | 30138 |
| HPV56 | L1 | 10 | 259 | VQSTCKYPDY | 30139 |
| HPV56 | L1 | 11 | 259 | VQSTCKYPDYL | 30140 |
| HPV56 | L1 | 8 | 56 | VVATDSYV | 30141 |
| HPV56 | L1 | 10 | 367 | VVDTTRSTNM | 30142 |
| HPV56 | L1 | 8 | 7 | YIYRDPPL | 30143 |
| HPV56 | L1 | 10 | 7 | YIYRDPPLHY | 30144 |
| HPV56 | L1 | 9 | 423 | YLHNMNANL | 30145 |
| HPV56 | L1 | 10 | 423 | YLHNMNANLL | 30146 |
| HPV56 | L1 | 8 | 268 | YLKMSADA | 30147 |
| HPV56 | L1 | 9 | 268 | YLKMSADAY | 30148 |
| HPV56 | L1 | 10 | 47 | YLPPTPVSKV | 30149 |
| HPV56 | L1 | 11 | 47 | YLPPTPVSKVV | 30150 |
| HPV56 | L1 | 8 | 396 | YLRHVEEY | 30151 |
| HPV56 | L1 | 10 | 396 | YLRHVEEYEL | 30152 |
| HPV56 | L1 | 8 | 283 | YLRREQLF | 30153 |
| HPV56 | L1 | 9 | 283 | YLRREQLFA | 30154 |
| HPV56 | L1 | 9 | 265 | YPDYLKMSA | 30155 |
| HPV56 | L1 | 11 | 265 | YPDYLKMSADA | 30156 |
| HPV56 | L1 | 8 | 102 | YQYRVFRV | 30157 |
| HPV56 | L1 | 10 | 102 | YQYRVFRVRL | 30158 |
| HPV56 | L1 | 9 | 325 | YVATPSGSM | 30159 |

TABLE XIV-continued

B62 Supermotif Peptides

| Type | Protein | No. of Amino Acid | Position | Sequence | Seq. Id. No. |
|---|---|---|---|---|---|
| HPV56 | L1 | 10 | 325 | YVATPSGSMI | 30160 |
| HPV56 | L1 | 8 | 62 | YVKRTSIF | 30161 |
| HPV56 | L1 | 9 | 62 | YVKRTSIFY | 30162 |
| HPV56 | L1 | 11 | 62 | YVKRTSIFYHA | 30163 |
| HPV56 | L2 | 8 | 438 | ALWPVYFF | 30164 |
| HPV56 | L2 | 9 | 271 | APDPDFMNI | 30165 |
| HPV56 | L2 | 10 | 271 | APDPDFMNIV | 30166 |
| HPV56 | L2 | 11 | 271 | APDPDFMNIVA | 30167 |
| HPV56 | L2 | 9 | 358 | APGLSSQSV | 30168 |
| HPV56 | L2 | 10 | 358 | APGLSSQSVA | 30169 |
| HPV56 | L2 | 11 | 391 | APLGNVWETPF | 30170 |
| HPV56 | L2 | 11 | 170 | APQTGEVSGNI | 30171 |
| HPV56 | L2 | 8 | 223 | APRLYRKA | 30172 |
| HPV56 | L2 | 9 | 223 | APRLYRKAF | 30173 |
| HPV56 | L2 | 8 | 327 | AQAEEIEM | 30174 |
| HPV56 | L2 | 11 | 327 | AQAEEIEMQPL | 30175 |
| HPV56 | L2 | 10 | 201 | AVHGSGTEPI | 30176 |
| HPV56 | L2 | 9 | 27 | CPEDVVNKI | 30177 |
| HPV56 | L2 | 8 | 322 | DISPIAQA | 30178 |
| HPV56 | L2 | 11 | 322 | DISPIAQAEEI | 30179 |
| HPV56 | L2 | 9 | 142 | DITPTSSTV | 30180 |
| HPV56 | L2 | 11 | 142 | DITPTSSTVHV | 30181 |
| HPV56 | L2 | 11 | 406 | DIVLPTGPSTW | 30182 |
| HPV56 | L2 | 10 | 349 | DIYANIDDEA | 30183 |
| HPV56 | L2 | 9 | 238 | DPAFLDRPA | 30184 |
| HPV56 | L2 | 11 | 238 | DPAFLDRPATL | 30185 |
| HPV56 | L2 | 8 | 273 | DPDFMNIV | 30186 |
| HPV56 | L2 | 9 | 273 | DPDFMNIVA | 30187 |
| HPV56 | L2 | 10 | 273 | DPDFMNIVAL | 30188 |
| HPV56 | L2 | 8 | 100 | DPSIVTLV | 30189 |
| HPV56 | L2 | 8 | 425 | DVTHDVYI | 30190 |
| HPV56 | L2 | 9 | 83 | DVTPARPPI | 30191 |
| HPV56 | L2 | 10 | 83 | DVTPARPPIV | 30192 |
| HPV56 | L2 | 11 | 83 | DVTPARPPIVV | 30193 |
| HPV56 | L2 | 11 | 30 | DVVNKIEQKTW | 30194 |
| HPV56 | L2 | 9 | 429 | DVYIQGSSF | 30195 |
| HPV56 | L2 | 10 | 429 | DVYIQGSSFA | 30196 |
| HPV56 | L2 | 11 | 429 | DVYIQGSSFAL | 30197 |
| HPV56 | L2 | 8 | 331 | EIEMQPLL | 30198 |
| HPV56 | L2 | 10 | 331 | EIEMQPLLSA | 30199 |
| HPV56 | L2 | 8 | 194 | EIPMQTFA | 30200 |
| HPV56 | L2 | 9 | 194 | EIPMQTFAV | 30201 |
| HPV56 | L2 | 11 | 129 | EITSSSTTTPA | 30202 |
| HPV56 | L2 | 8 | 333 | EMQPLLSA | 30203 |
| HPV56 | L2 | 8 | 208 | EPISSTPI | 30204 |
| HPV56 | L2 | 11 | 208 | EPISSTPIPGF | 30205 |
| HPV56 | L2 | 9 | 36 | EQKTWADKI | 30206 |
| HPV56 | L2 | 10 | 36 | EQKTWADKIL | 30207 |
| HPV56 | L2 | 8 | 175 | EVSGNILI | 30208 |
| HPV56 | L2 | 9 | 162 | FIDPPVIEA | 30209 |
| HPV56 | L2 | 8 | 241 | FLDRPATL | 30210 |
| HPV56 | L2 | 9 | 241 | FLDRPATLV | 30211 |
| HPV56 | L2 | 11 | 241 | FLDRPATLVSA | 30212 |
| HPV56 | L2 | 11 | 276 | FMNIVALHRPA | 30213 |
| HPV56 | L2 | 10 | 231 | FQQVKVTDPA | 30214 |
| HPV56 | L2 | 11 | 231 | FQQVKVTDPAF | 30215 |
| HPV56 | L2 | 9 | 418 | FVPQSPYDV | 30216 |
| HPV56 | L2 | 8 | 188 | GIHSYEEI | 30217 |
| HPV56 | L2 | 10 | 188 | GIHSYEEIPM | 30218 |
| HPV56 | L2 | 11 | 118 | GIPNFTGSGGF | 30219 |
| HPV56 | L2 | 8 | 360 | GLSSQSVA | 30220 |
| HPV56 | L2 | 9 | 346 | GLYDIYANI | 30221 |
| HPV56 | L2 | 8 | 412 | GPSTWPFV | 30222 |
| HPV56 | L2 | 8 | 97 | GPTDPSIV | 30223 |
| HPV56 | L2 | 10 | 97 | GPTDPSIVTL | 30224 |
| HPV56 | L2 | 11 | 97 | GPTDPSIVTLV | 30225 |
| HPV56 | L2 | 8 | 269 | GVAPDPDF | 30226 |
| HPV56 | L2 | 9 | 269 | GVAPDPDFM | 30227 |
| HPV56 | L2 | 11 | 269 | GVAPDPDFMNI | 30228 |
| HPV56 | L2 | 11 | 293 | GVRFSRLGRKA | 30229 |
| HPV56 | L2 | 8 | 156 | HITNPLFI | 30230 |
| HPV56 | L2 | 9 | 372 | HLPIKPSTL | 30231 |
| HPV56 | L2 | 11 | 372 | HLPIKPSTLSF | 30232 |
| HPV56 | L2 | 11 | 151 | HVSSTHITNPL | 30233 |
| HPV56 | L2 | 10 | 180 | ILISTPTSGI | 30234 |

TABLE XIV-continued

B62 Supermotif Peptides

| Type | Protein | No. of Amino Acid | Position | Sequence | Seq. Id. No. |
|---|---|---|---|---|---|
| HPV56 | L2 | 8 | 44 | ILQWGSLF | 30235 |
| HPV56 | L2 | 10 | 44 | ILQWGSLFTY | 30236 |
| HPV56 | L2 | 11 | 44 | ILQWGSLFTYF | 30237 |
| HPV56 | L2 | 8 | 215 | IPGFRRIA | 30238 |
| HPV56 | L2 | 9 | 215 | IPGFRRIAA | 30239 |
| HPV56 | L2 | 8 | 195 | IPMQTFAV | 30240 |
| HPV56 | L2 | 10 | 119 | IPNFTGSGGF | 30241 |
| HPV56 | L2 | 10 | 453 | IPYFFADGDV | 30242 |
| HPV56 | L2 | 11 | 453 | IPYFFADGDVA | 30243 |
| HPV56 | L2 | 8 | 432 | IQGSSFAL | 30244 |
| HPV56 | L2 | 9 | 432 | IQGSSFALW | 30245 |
| HPV56 | L2 | 11 | 432 | IQGSSFALWPV | 30246 |
| HPV56 | L2 | 9 | 305 | IQTRRGTQI | 30247 |
| HPV56 | L2 | 11 | 305 | IQTRRGTQIGA | 30248 |
| HPV56 | L2 | 8 | 279 | IVALHRPA | 30249 |
| HPV56 | L2 | 9 | 279 | IVALHRPAF | 30250 |
| HPV56 | L2 | 11 | 81 | IVDVTPARPPI | 30251 |
| HPV56 | L2 | 10 | 407 | IVLPTGPSTW | 30252 |
| HPV56 | L2 | 10 | 103 | IVTLVEESSV | 30253 |
| HPV56 | L2 | 11 | 103 | IVTLVEESSVI | 30254 |
| HPV56 | L2 | 8 | 34 | KIEQKTWA | 30255 |
| HPV56 | L2 | 11 | 34 | KIEQKTWADKI | 30256 |
| HPV56 | L2 | 8 | 43 | KILQWGSL | 30257 |
| HPV56 | L2 | 9 | 43 | KILQWGSLF | 30258 |
| HPV56 | L2 | 11 | 43 | KILQWGSLFTY | 30259 |
| HPV56 | L2 | 10 | 22 | KLSGTCPEDV | 30260 |
| HPV56 | L2 | 11 | 22 | KLSGTCPEDVV | 30261 |
| HPV56 | L2 | 8 | 376 | KPSTLSFA | 30262 |
| HPV56 | L2 | 8 | 235 | KVTDPAFL | 30263 |
| HPV56 | L2 | 9 | 181 | LISTPTSGI | 30264 |
| HPV56 | L2 | 8 | 337 | LLSANNSF | 30265 |
| HPV56 | L2 | 11 | 337 | LLSANNSFDGL | 30266 |
| HPV56 | L2 | 8 | 373 | LPIKPSTL | 30267 |
| HPV56 | L2 | 10 | 373 | LPIKPSTLSF | 30268 |
| HPV56 | L2 | 11 | 373 | LPIKPSTLSFA | 30269 |
| HPV56 | L2 | 8 | 409 | LPTGPSTW | 30270 |
| HPV56 | L2 | 10 | 409 | LPTGPSTWPF | 30271 |
| HPV56 | L2 | 11 | 409 | LPTGPSTWPFV | 30272 |
| HPV56 | L2 | 9 | 45 | LQWGSLFTY | 30273 |
| HPV56 | L2 | 10 | 45 | LQWGSLFTYF | 30274 |
| HPV56 | L2 | 8 | 106 | LVEESSVI | 30275 |
| HPV56 | L2 | 8 | 248 | LVSADNPL | 30276 |
| HPV56 | L2 | 9 | 248 | LVSADNPLF | 30277 |
| HPV56 | L2 | 11 | 334 | MQPLLSANNSF | 30278 |
| HPV56 | L2 | 9 | 353 | NIDDEAPGL | 30279 |
| HPV56 | L2 | 11 | 179 | NILISTPTSGI | 30280 |
| HPV56 | L2 | 9 | 278 | NIVALHRPA | 30281 |
| HPV56 | L2 | 10 | 278 | NIVALHRPAF | 30282 |
| HPV56 | L2 | 11 | 253 | NPLFEGTDTSL | 30283 |
| HPV56 | L2 | 9 | 159 | NPLFIDPPV | 30284 |
| HPV56 | L2 | 10 | 159 | NPLFIDPPVI | 30285 |
| HPV56 | L2 | 9 | 388 | NVTAPLGNV | 30286 |
| HPV56 | L2 | 10 | 388 | NVTAPLGNVW | 30287 |
| HPV56 | L2 | 8 | 395 | NVWETPFY | 30288 |
| HPV56 | L2 | 8 | 325 | PIAQQEEI | 30289 |
| HPV56 | L2 | 10 | 325 | PIAQAEEIEM | 30290 |
| HPV56 | L2 | 9 | 374 | PIKPSTLSF | 30291 |
| HPV56 | L2 | 10 | 374 | PIKPSTLSFA | 30292 |
| HPV56 | L2 | 8 | 214 | PIPGFRRI | 30293 |
| HPV56 | L2 | 9 | 214 | PIPGFRRIA | 30294 |
| HPV56 | L2 | 10 | 214 | PIPGFRRIAA | 30295 |
| HPV56 | L2 | 10 | 209 | PISSTPIPGF | 30296 |
| HPV56 | L2 | 10 | 254 | PLFEGTDTSL | 30297 |
| HPV56 | L2 | 11 | 254 | PLFEGTDTSLA | 30298 |
| HPV56 | L2 | 8 | 160 | PLFIDPPV | 30299 |
| HPV56 | L2 | 9 | 160 | PLFIDPPVI | 30300 |
| HPV56 | L2 | 11 | 160 | PLFIDPPVIEA | 30301 |
| HPV56 | L2 | 10 | 392 | PLGNVWETPF | 30302 |
| HPV56 | L2 | 11 | 392 | PLGNVWETPFY | 30303 |
| HPV56 | L2 | 9 | 73 | PLGSRPSTI | 30304 |
| HPV56 | L2 | 10 | 73 | PLGSRPSTIV | 30305 |
| HPV56 | L2 | 9 | 336 | PLLSANNSF | 30306 |
| HPV56 | L2 | 8 | 89 | PPIVVESV | 30307 |
| HPV56 | L2 | 11 | 420 | PQSPYDVTHDV | 30308 |
| HPV56 | L2 | 10 | 171 | PQTGEVSGNI | 30309 |

TABLE XIV-continued

B62 Supermotif Peptides

| Type | Protein | No. of Amino Acid | Position | Sequence | Seq. Id. No. |
|---|---|---|---|---|---|
| HPV56 | L2 | 11 | 171 | PQTGEVSGNIL | 30310 |
| HPV56 | L2 | 11 | 166 | PVIEAPQTGEV | 30311 |
| HPV56 | L2 | 8 | 312 | QIGARVHY | 30312 |
| HPV56 | L2 | 9 | 312 | QIGARVHYY | 30313 |
| HPV56 | L2 | 10 | 312 | QIGARVHYYY | 30314 |
| HPV56 | L2 | 8 | 16 | QLYKTCKL | 30315 |
| HPV56 | L2 | 10 | 335 | QPLLSANNSF | 30316 |
| HPV56 | L2 | 9 | 232 | QQVKVTDPA | 30317 |
| HPV56 | L2 | 10 | 232 | QQVKVTDPAF | 30318 |
| HPV56 | L2 | 11 | 232 | QQVKVTDPAFL | 30319 |
| HPV56 | L2 | 8 | 233 | QVKVTDPA | 30320 |
| HPV56 | L2 | 9 | 233 | QVKVTDPAF | 30321 |
| HPV56 | L2 | 10 | 233 | QVKVTDPAFL | 30322 |
| HPV56 | L2 | 8 | 220 | RIAAPRLY | 30323 |
| HPV56 | L2 | 11 | 220 | RIAAPRLYRKA | 30324 |
| HPV56 | L2 | 11 | 452 | RIPYFFADGDV | 30325 |
| HPV56 | L2 | 8 | 298 | RLGRKATI | 30326 |
| HPV56 | L2 | 10 | 225 | RLYRKAFQQV | 30327 |
| HPV56 | L2 | 11 | 284 | RPAFTTRRGGV | 30328 |
| HPV56 | L2 | 8 | 244 | RPATLVSA | 30329 |
| HPV56 | L2 | 9 | 88 | RPPIVVESV | 30330 |
| HPV56 | L2 | 8 | 77 | RPSTIVDV | 30331 |
| HPV56 | L2 | 11 | 77 | RPSTIVDVTPA | 30332 |
| HPV56 | L2 | 8 | 316 | RVHYYYDI | 30333 |
| HPV56 | L2 | 11 | 316 | RVHYYYDISPI | 30334 |
| HPV56 | L2 | 11 | 102 | SIVTLVEESSV | 30335 |
| HPV56 | L2 | 9 | 262 | SLAFSPSGV | 30336 |
| HPV56 | L2 | 10 | 262 | SLAFSPSGVA | 30337 |
| HPV56 | L2 | 9 | 49 | SLFTYFGGL | 30338 |
| HPV56 | L2 | 11 | 49 | SLFTYFGGLGI | 30339 |
| HPV56 | L2 | 9 | 324 | SPIAQAEEI | 30340 |
| HPV56 | L2 | 11 | 324 | SPIAQAEEIEM | 30341 |
| HPV56 | L2 | 11 | 266 | SPSGVAPDPDF | 30342 |
| HPV56 | L2 | 9 | 422 | SPYDVTHDV | 30343 |
| HPV56 | L2 | 10 | 422 | SPYDVTHDVY | 30344 |
| HPV56 | L2 | 11 | 422 | SPYDVTHDVYI | 30345 |
| HPV56 | L2 | 9 | 363 | SQSVATPSA | 30346 |
| HPV56 | L2 | 11 | 363 | SQSVATPSAHL | 30347 |
| HPV56 | L2 | 9 | 365 | SVATPSAHL | 30348 |
| HPV56 | L2 | 11 | 365 | SVATPSAHLPI | 30349 |
| HPV56 | L2 | 9 | 95 | SVGPTDPSI | 30350 |
| HPV56 | L2 | 10 | 95 | SVGPTDPSIV | 30351 |
| HPV56 | L2 | 9 | 111 | SVIESGAGI | 30352 |
| HPV56 | L2 | 10 | 304 | TIQTRRGTQI | 30353 |
| HPV56 | L2 | 8 | 80 | TIVDVTPA | 30354 |
| HPV56 | L2 | 11 | 379 | TLSFASNTTNV | 30355 |
| HPV56 | L2 | 8 | 105 | TLVEESSV | 30356 |
| HPV56 | L2 | 9 | 105 | TLVEESSVI | 30357 |
| HPV56 | L2 | 9 | 247 | TLVSADNPL | 30358 |
| HPV56 | L2 | 10 | 247 | TLVSADNPLF | 30359 |
| HPV56 | L2 | 8 | 85 | TPARPPIV | 30360 |
| HPV56 | L2 | 9 | 85 | TPARPPIVV | 30361 |
| HPV56 | L2 | 9 | 399 | TPFYSGPDI | 30362 |
| HPV56 | L2 | 10 | 399 | TPFYSGPDIV | 30363 |
| HPV56 | L2 | 11 | 399 | TPFYSGPDIVL | 30364 |
| HPV56 | L2 | 9 | 213 | TPIPGFRRI | 30365 |
| HPV56 | L2 | 10 | 213 | TPIPGFRRIA | 30366 |
| HPV56 | L2 | 11 | 213 | TPIPGFRRIAA | 30367 |
| HPV56 | L2 | 8 | 368 | TPSAHLPI | 30368 |
| HPV56 | L2 | 9 | 184 | TPTSGIHSY | 30369 |
| HPV56 | L2 | 9 | 144 | TPTSSTVHV | 30370 |
| HPV56 | L2 | 9 | 311 | TQIGARVHY | 30371 |
| HPV56 | L2 | 10 | 311 | TQIGARVHYY | 30372 |
| HPV56 | L2 | 11 | 311 | TQIGARVHYYY | 30373 |
| HPV56 | L2 | 9 | 15 | TQLYKTCKL | 30374 |
| HPV56 | L2 | 9 | 149 | TVHVSSTHI | 30375 |
| HPV56 | L2 | 10 | 167 | VIEAPQTGEV | 30376 |
| HPV56 | L2 | 8 | 112 | VIESGAGI | 30377 |
| HPV56 | L2 | 11 | 112 | VIESGAGIPNF | 30378 |
| HPV56 | L2 | 11 | 140 | VLDITPTSSTV | 30379 |
| HPV56 | L2 | 9 | 408 | VLPTGPSTW | 30380 |
| HPV56 | L2 | 11 | 408 | VLPTGPSTWPF | 30381 |
| HPV56 | L2 | 10 | 72 | VPLGSRPSTI | 30382 |
| HPV56 | L2 | 11 | 72 | VPLGSRPSTIV | 30383 |
| HPV56 | L2 | 8 | 419 | VPQSPYDV | 30384 |

TABLE XIV-continued

B62 Supermotif Peptides

| Type | Protein | No. of Amino Acid | Position | Sequence | Seq. Id. No. |
|---|---|---|---|---|---|
| HPV56 | L2 | 10 | 31 | VVNKIEQKTW | 30385 |
| HPV56 | L2 | 11 | 31 | VVNKIEQKTWA | 30386 |
| HPV56 | L2 | 9 | 416 | WPFVPQSPY | 30387 |
| HPV56 | L2 | 11 | 416 | WPFVPQSPYDV | 30388 |
| HPV56 | L2 | 8 | 431 | YIQGSSFA | 30389 |
| HPV56 | L2 | 9 | 431 | YIQGSSFAL | 30390 |
| HPV56 | L2 | 10 | 431 | YIQGSSFALW | 30391 |
| HPV56 | L2 | 11 | 71 | YVPLGSRPSTI | 30392 |

TABLE XV

A01 Motif Peptides

| Type | Protein | No. of Amino Acids | Position | Sequence | A*0101 | Seq. Id. No. |
|---|---|---|---|---|---|---|
| HPV16 | E1 | 11 | 248 | ADSIKTLLQQY | | 30393 |
| HPV16 | E1 | 10 | 206 | AMLAKFKELY | | 30394 |
| HPV16 | E1 | 8 | 524 | ATVPCWNY | | 30395 |
| HPV16 | E1 | 9 | 404 | DCATMCRHY | 0.0011 | 30396 |
| HPV16 | E1 | 10 | 522 | DDATVPCWNY | | 30397 |
| HPV16 | E1 | 9 | 371 | DDSEIAYKY | | 30398 |
| HPV16 | E1 | 8 | 372 | DSEIAYKY | | 30399 |
| HPV16 | E1 | 10 | 249 | DSIKTLLQQY | | 30400 |
| HPV16 | E1 | 10 | 356 | ELSQMVQWAY | | 30401 |
| HPV16 | E1 | 9 | 152 | ETETPCSQY | | 30402 |
| HPV16 | E1 | 9 | 594 | FDENGNPVY | | 30403 |
| HPV16 | E1 | 8 | 127 | FESEDSGY | | 30404 |
| HPV16 | E1 | 10 | 162 | GGSGGGCSQY | | 30405 |
| HPV16 | E1 | 9 | 325 | GISNISEVY | | 30406 |
| HPV16 | E1 | 10 | 272 | GMVVLLLVRY | | 30407 |
| HPV16 | E1 | 9 | 163 | GSGGGCSQY | | 30408 |
| HPV16 | E1 | 8 | 571 | GTDSRWPY | | 30409 |
| HPV16 | E1 | 9 | 12 | GTGCNGWFY | 3.9 | 30410 |
| HPV16 | E1 | 11 | 568 | INAGTDSRWPY | | 30411 |
| HPV16 | E1 | 8 | 326 | ISNISEVY | | 30412 |
| HPV16 | E1 | 9 | 369 | IVDDSEIAY | | 30413 |
| HPV16 | E1 | 11 | 369 | IVDDSEIAYKY | | 30414 |
| HPV16 | E1 | 11 | 323 | KTGISNISEVY | | 30415 |
| HPV16 | E1 | 10 | 252 | KTLLQQYCLY | | 30416 |
| HPV16 | E1 | 11 | 521 | LDDATVPCWNY | | 30417 |
| HPV16 | E1 | 9 | 126 | LFESEDSGY | | 30418 |
| HPV16 | E1 | 9 | 312 | LRSTAAALY | | 30419 |
| HPV16 | E1 | 11 | 312 | LRSTAAALYWY | | 30420 |
| HPV16 | E1 | 9 | 357 | LSQMVQWAY | | 30421 |
| HPV16 | E1 | 11 | 48 | LVDFIVNDNDY | | 30422 |
| HPV16 | E1 | 9 | 207 | MLAKFKELY | | 30423 |
| HPV16 | E1 | 9 | 420 | MSMSQWIKY | | 30424 |
| HPV16 | E1 | 10 | 593 | PFDENGNPVY | | 30425 |
| HPV16 | E1 | 10 | 419 | QMSMSQWIKY | | 30426 |
| HPV16 | E1 | 11 | 80 | RDAVQVLKRKY | | 30427 |
| HPV16 | E1 | 11 | 150 | RHETETPCSQY | | 30428 |
| HPV16 | E1 | 8 | 313 | RSTAAALY | | 30429 |
| HPV16 | E1 | 10 | 313 | RSTAAALYWY | | 30430 |
| HPV16 | E1 | 8 | 421 | SMSQWIKY | | 30431 |
| HPV16 | E1 | 9 | 314 | STAAALYWY | | 30432 |
| HPV16 | E1 | 8 | 315 | TAAALYWY | | 30433 |
| HPV16 | E1 | 8 | 370 | VDDSEIAY | | 30434 |
| HPV16 | E1 | 10 | 370 | VDDSEIAYKY | | 30435 |
| HPV16 | E1 | 11 | 402 | VKDCATMCRHY | | 30436 |
| HPV16 | E2 | 9 | 11 | CQDKILTHY | | 30437 |
| HPV16 | E2 | 10 | 122 | DGDICNTMHY | | 30438 |
| HPV16 | E2 | 11 | 22 | DSTDLRDHIDY | | 30439 |
| HPV16 | E2 | 8 | 80 | ETIYNSQY | | 30440 |
| HPV16 | E2 | 8 | 171 | FKDDAEKY | | 30441 |
| HPV16 | E2 | 11 | 293 | GDANTLKCLRY | | 30442 |
| HPV16 | E2 | 10 | 328 | HKSAIVTLTY | | 30443 |
| HPV16 | E2 | 9 | 35 | HMRLECAIY | | 30444 |
| HPV16 | E2 | 10 | 35 | HMRLECAIYY | | 30445 |
| HPV16 | E2 | 9 | 329 | KSAIVTLTY | | 30446 |
| HPV16 | E2 | 9 | 94 | LQDVSLEVY | | 30447 |
| HPV16 | E2 | 11 | 77 | LTLETIYNSQY | | 30448 |
| HPV16 | E2 | 8 | 296 | NTLKCLRY | | 30449 |

TABLE XV-continued

A01 Motif Peptides

| Type | Protein | No. of Amino Acids | Position | Sequence | A*0101 | Seq. Id. No. |
|---|---|---|---|---|---|---|
| HPV16 | E2 | 10 | 106 | PTGCIKKHGY | | 30450 |
| HPV16 | E2 | 8 | 151 | QVDYYGLY | | 30451 |
| HPV16 | E2 | 9 | 151 | QVDYYGLYY | | 30452 |
| HPV16 | E2 | 8 | 37 | RLECAIYY | | 30453 |
| HPV16 | E2 | 10 | 23 | STDLRDHIDY | | 30454 |
| HPV16 | E2 | 10 | 78 | TLETIYNSQY | | 30455 |
| HPV16 | E2 | 11 | 128 | TMHYTNWTHIY | | 30456 |
| HPV16 | E2 | 8 | 160 | VHEGIRTY | | 30457 |
| HPV16 | E2 | 10 | 145 | VTVVEGQVDY | | 30458 |
| HPV16 | E2 | 11 | 145 | VTVVEGQVDYY | | 30459 |
| HPV16 | E2 | 8 | 147 | VVEGQVDY | | 30460 |
| HPV16 | E2 | 9 | 147 | VVEGQVDYY | | 30461 |
| HPV16 | E2 | 11 | 92 | WTLQDVSLEVY | | 30462 |
| HPV16 | E2 | 8 | 131 | YTNWTHIY | | 30463 |
| HPV16 | E5 | 11 | 53 | AASAFRCFIVY | | 30464 |
| HPV16 | E5 | 10 | 54 | ASAFRCFIVY | | 30465 |
| HPV16 | E6 | 11 | 51 | DFAFRDLCIVY | | 30466 |
| HPV16 | E6 | 8 | 54 | FRDLCIVY | | 30467 |
| HPV16 | E6 | 8 | 76 | FYSKISEY | | 30468 |
| HPV16 | E6 | 11 | 76 | FYSKISEYRHY | | 30469 |
| HPV16 | E6 | 8 | 92 | GTTLEQQY | 0.0006 | 30470 |
| HPV16 | E6 | 10 | 30 | IHDIILECVY | 0.028 | 30471 |
| HPV16 | E6 | 9 | 80 | ISEYRHYCY | 0.31 | 30472 |
| HPV16 | E6 | 8 | 79 | KISEYRHY | | 30473 |
| HPV16 | E6 | 10 | 79 | KISEYRHYCY | 0.009 | 30474 |
| HPV16 | E6 | 9 | 69 | VCDKCLKFY | 0.0017 | 30475 |
| HPV16 | E6 | 10 | 77 | YSKISEYRHY | 0.015 | 30476 |
| HPV16 | E7 | 8 | 4 | DTPTLHEY | 0.0002 | 30477 |
| HPV16 | E7 | 8 | 18 | ETTDLYCY | 0.078 | 30478 |
| HPV16 | E7 | 10 | 43 | GQAEPDRAHY | | 30479 |
| HPV16 | E7 | 10 | 2 | HGDTPTLHEY | 0.003 | 30480 |
| HPV16 | E7 | 9 | 44 | QAEPDRAHY | 0.021 | 30481 |
| HPV16 | E7 | 8 | 16 | QPETTDLY | 0.001 | 30482 |
| HPV16 | E7 | 10 | 16 | QPETTDLYCY | 0.033 | 30483 |
| HPV16 | L1 | 9 | 373 | AISTSETTY | | 30484 |
| HPV16 | L1 | 11 | 371 | CAAISTSETTY | | 30485 |
| HPV16 | L1 | 10 | 251 | CTSICKYPDY | | 30486 |
| HPV16 | L1 | 9 | 13 | CYENDVNVY | | 30487 |
| HPV16 | L1 | 8 | 154 | DTENASAY | | 30488 |
| HPV16 | L1 | 11 | 386 | FKEYLRRGEEY | | 30489 |
| HPV16 | L1 | 11 | 307 | GSTANLASSNY | | 30490 |
| HPV16 | L1 | 8 | 374 | ISTSETTY | | 30491 |
| HPV16 | L1 | 11 | 11 | ITCYENDVNVY | | 30492 |
| HPV16 | L1 | 10 | 407 | ITLTADVMTY | | 30493 |
| HPV16 | L1 | 8 | 463 | KEDPLKKY | | 30494 |
| HPV16 | L1 | 11 | 151 | KLDDTENASAY | | 30495 |
| HPV16 | L1 | 10 | 152 | LDDTENASAY | | 30496 |
| HPV16 | L1 | 8 | 68 | LLAVGHPY | | 30497 |
| HPV16 | L1 | 8 | 31 | LPSEATVY | | 30498 |
| HPV16 | L1 | 8 | 409 | LTADVMTY | | 30499 |
| HPV16 | L1 | 9 | 169 | NRECISMDY | | 30500 |
| HPV16 | L1 | 9 | 462 | PKEDPLKKY | | 30501 |
| HPV16 | L1 | 11 | 247 | PLDICTSICKY | | 30502 |
| HPV16 | L1 | 11 | 43 | PVSKVVSTDEY | | 30503 |
| HPV16 | L1 | 10 | 328 | SDAQIFNKPY | | 30504 |
| HPV16 | L1 | 10 | 308 | STANLASSNY | | 30505 |
| HPV16 | L1 | 11 | 50 | TDEYVARTNIY | | 30506 |
| HPV16 | L1 | 11 | 327 | TSDAQIFNKPY | | 30507 |
| HPV16 | L1 | 9 | 252 | TSICKYPDY | | 30508 |
| HPV16 | L1 | 11 | 65 | TSRLLAVGHPY | | 30509 |
| HPV16 | L1 | 11 | 379 | TTYKNTNFKEY | | 30510 |
| HPV16 | L1 | 10 | 293 | VGENVPDDLY | | 30511 |
| HPV16 | L1 | 10 | 44 | VSKVVSTDEY | | 30512 |
| HPV16 | L1 | 8 | 268 | YGDSLFFY | | 30513 |
| HPV16 | L1 | 8 | 53 | YVARTNY | | 30514 |
| HPV16 | L1 | 9 | 53 | YVARTNIYY | | 30515 |
| HPV16 | L2 | 10 | 443 | AGDFYLHPSY | | 30516 |
| HPV16 | L2 | 11 | 443 | AGDFYLHPSYY | | 30517 |
| HPV16 | L2 | 9 | 259 | GIDVDNTLY | | 30518 |
| HPV16 | L2 | 10 | 317 | GKSIGAKVHY | | 30519 |
| HPV16 | L2 | 11 | 317 | GKSIGAKVHYY | | 30520 |
| HPV16 | L2 | 10 | 63 | GSGTGGRTGY | | 30521 |
| HPV16 | L2 | 11 | 218 | GSRPVARLGLY | | 30522 |
| HPV16 | L2 | 8 | 65 | GTGGRTGY | | 30523 |
| HPV16 | L2 | 8 | 440 | IADAGDFY | | 30524 |

TABLE XV-continued

A01 Motif Peptides

| Type | Protein | No. of Amino Acids | Position | Sequence | A*0101 | Seq. Id. No. |
|---|---|---|---|---|---|---|
| HPV16 | L2 | 8 | 41 | IADQILQY | | 30525 |
| HPV16 | L2 | 8 | 320 | IGAKVHYY | | 30526 |
| HPV16 | L2 | 9 | 320 | IGAKVHYYY | | 30527 |
| HPV16 | L2 | 9 | 439 | IIADAGDFY | | 30528 |
| HPV16 | L2 | 10 | 243 | ITTPTKLITY | | 30529 |
| HPV16 | L2 | 8 | 250 | ITYDNPAY | | 30530 |
| HPV16 | L2 | 9 | 11 | KRASATQLY | | 30531 |
| HPV16 | L2 | 9 | 318 | KSIGAKVHY | | 30532 |
| HPV16 | L2 | 10 | 318 | KSIGAKVHYY | | 30533 |
| HPV16 | L2 | 11 | 318 | KSIGAKVHYYY | | 30534 |
| HPV16 | L2 | 10 | 39 | KTIADQILQY | | 30535 |
| HPV16 | L2 | 11 | 183 | LSSSTISTHNY | | 30536 |
| HPV16 | L2 | 10 | 294 | LTSRRTGIRY | | 30537 |
| HPV16 | L2 | 10 | 397 | NTTIPFGGAY | | 30538 |
| HPV16 | L2 | 8 | 386 | PSTSLSGY | | 30539 |
| HPV16 | L2 | 11 | 383 | PSVPSTSLSGY | | 30540 |
| HPV16 | L2 | 9 | 358 | PTSINNGLY | | 36541 |
| HPV16 | L2 | 8 | 221 | PVARLGLY | | 30542 |
| HPV16 | L2 | 8 | 342 | QTITPSTY | | 30543 |
| HPV16 | L2 | 8 | 12 | RASATQLY | | 30544 |
| HPV16 | L2 | 11 | 9 | RTKRASATQLY | | 30545 |
| HPV16 | L2 | 10 | 184 | SSSTISTHNY | | 30546 |
| HPV16 | L2 | 9 | 185 | SSTISTHNY | | 30547 |
| HPV16 | L2 | 8 | 186 | STISTHNY | | 30548 |
| HPV16 | L2 | 11 | 62 | TGSGTGGRTGY | | 30549 |
| HPV16 | L2 | 9 | 40 | TIADQILQY | | 30550 |
| HPV16 | L2 | 8 | 359 | TSINNGLY | | 30551 |
| HPV16 | L2 | 11 | 359 | TSINNGLYDIY | | 30552 |
| HPV16 | L2 | 9 | 295 | TSRRTGIRY | | 30553 |
| HPV16 | L2 | 9 | 398 | TTIPFGGAY | | 30554 |
| HPV16 | L2 | 9 | 244 | TTPTKLITY | | 30555 |
| HPV16 | L2 | 9 | 385 | VPSTSLSGY | | 30556 |
| HPV16 | L2 | 11 | 437 | YTIIADAGDFY | | 30557 |
| HPV18 | E1 | 8 | 578 | AKDNRWPY | | 30558 |
| HPV18 | E1 | 10 | 213 | AMLAVFKDTY | | 30559 |
| HPV18 | E1 | 8 | 531 | ATTTCWTY | | 30560 |
| HPV18 | E1 | 9 | 411 | DCATMCKHY | | 30561 |
| HPV18 | E1 | 10 | 529 | DDATTTCWTY | | 30562 |
| HPV18 | E1 | 9 | 378 | DESDMAFEY | | 30563 |
| HPV18 | E1 | 8 | 379 | ESDMAFEY | | 30564 |
| HPV18 | E1 | 8 | 130 | FTISDSGY | | 30565 |
| HPV18 | E1 | 9 | 484 | GPANTGKSY | | 30566 |
| HPV18 | E1 | 9 | 11 | GTGCNGWFY | 3.9 | 30567 |
| HPV18 | E1 | 10 | 576 | HPAKDNRWPY | | 30568 |
| HPV18 | E1 | 8 | 401 | KSNCQAKY | | 30569 |
| HPV18 | E1 | 10 | 259 | KTLIQPFILY | | 30570 |
| HPV18 | E1 | 11 | 528 | LDDATTTCWTY | | 30571 |
| HPV18 | E1 | 11 | 409 | LKDCATMCKHY | | 30572 |
| HPV18 | E1 | 9 | 400 | LKSNCQAKY | | 30573 |
| HPV18 | E1 | 9 | 319 | LRSSVAALY | | 30574 |
| HPV18 | E1 | 11 | 319 | LRSSVAALYWY | | 30575 |
| HPV18 | E1 | 11 | 376 | LTDESDMAFEY | | 30576 |
| HPV18 | E1 | 9 | 214 | MLAVFKDTY | | 30577 |
| HPV18 | E1 | 10 | 600 | PFDKNGNPVY | | 30578 |
| HPV18 | E1 | 8 | 320 | RSSVAALY | | 30579 |
| HPV18 | E1 | 10 | 320 | RSSVAALYWY | | 30580 |
| HPV18 | E1 | 9 | 321 | SSVAALYWY | | 30581 |
| HPV18 | E1 | 8 | 322 | SVAALYWY | | 30582 |
| HPV18 | E1 | 10 | 377 | TDESDMAFEY | | 30583 |
| HPV18 | E1 | 10 | 533 | TTCWTYFDTY | | 30584 |
| HPV18 | E1 | 11 | 532 | TTTCWTYFDTY | | 30585 |
| HPV18 | E2 | 10 | 154 | ATCVSHRGLY | | 30586 |
| HPV18 | E2 | 11 | 154 | ATCVSHRGLYY | | 30587 |
| HPV18 | E2 | 11 | 132 | CMTYVAWDSVY | | 30588 |
| HPV18 | E2 | 8 | 156 | CVSHRGLY | | 30589 |
| HPV18 | E2 | 9 | 156 | CVSHRGLYY | | 30590 |
| HPV18 | E2 | 8 | 29 | DIDSQIQY | | 30591 |
| HPV18 | E2 | 11 | 26 | DSKDIDSQIQY | | 30592 |
| HPV18 | E2 | 9 | 354 | DSVQILVGY | | 30593 |
| HPV18 | E2 | 8 | 176 | FKSECEKY | | 30594 |
| HPV18 | E2 | 11 | 352 | IPDSVQILVGY | | 30595 |
| HPV18 | E2 | 9 | 329 | KTGILTVTY | | 30596 |
| HPV18 | E2 | 10 | 133 | MTYVAWDSVY | | 30597 |
| HPV18 | E2 | 11 | 133 | MTYVAWDSVYY | | 30598 |
| HPV18 | E2 | 8 | 128 | NKDNCMTY | | 30599 |

TABLE XV-continued

A01 Motif Peptides

| Type | Protein | No. of Amino Acids | Position | Sequence | A*0101 | Seq. Id. No. |
|---|---|---|---|---|---|---|
| HPV18 | E2 | 8 | 297 | NSLKCLRY | | 30600 |
| HPV18 | E2 | 10 | 353 | PDSVQILVGY | | 30601 |
| HPV18 | E2 | 11 | 56 | QTLNHQVVPAY | | 30602 |
| HPV18 | E2 | 9 | 296 | RNSLKCLRY | | 30603 |
| HPV18 | E2 | 10 | 27 | SKDIDSQIQY | | 30604 |
| HPV18 | E2 | 11 | 230 | STVSVGTAKTY | | 30605 |
| HPV18 | E2 | 10 | 231 | TVSVGTAKTY | | 30606 |
| HPV18 | E2 | 9 | 165 | VKEGYNTFY | | 30607 |
| HPV18 | E2 | 9 | 15 | VQDKIIDHY | | 30608 |
| HPV18 | E2 | 8 | 157 | VSHRGLYY | | 30609 |
| HPV18 | E2 | 9 | 232 | VSVGTAKTY | | 30610 |
| HPV18 | E2 | 11 | 173 | YIEFKSECEKY | | 30611 |
| HPV18 | E2 | 8 | 135 | YVAWDSVY | | 30612 |
| HPV18 | E2 | 9 | 135 | YVAWDSVYY | | 30613 |
| HPV18 | E5 | 10 | 30 | AYAWVLVFVY | | 30614 |
| HPV18 | E5 | 11 | 43 | ITSPATAFTVY | | 30615 |
| HPV18 | E5 | 9 | 23 | LPSVCMCAY | | 30616 |
| HPV18 | E5 | 8 | 24 | PSVCMCAY | | 30617 |
| HPV18 | E5 | 9 | 45 | SPATAFTVY | | 30618 |
| HPV18 | E5 | 10 | 44 | TSPATAFTVY | | 30619 |
| HPV18 | E6 | 8 | 27 | DIEITCVY | 0.0025 | 30620 |
| HPV18 | E6 | 11 | 46 | EPAFKDLFVVY | | 30621 |
| HPV18 | E6 | 9 | 4 | FEDPTRRPY | 0.0017 | 30622 |
| HPV18 | E6 | 8 | 49 | FKDLFVVY | | 30623 |
| HPV18 | E6 | 11 | 71 | FYSRIRELRHY | | 30624 |
| HPV18 | E6 | 11 | 62 | HAACHKCIDFY | | 30625 |
| HPV18 | E6 | 10 | 25 | LQDIEITCVY | 0.0023 | 30626 |
| HPV18 | E6 | 10 | 3 | RFEDPTRRPY | 0.0015 | 30627 |
| HPV18 | E6 | 11 | 89 | TLEKLTNTGLY | 5.9 | 30628 |
| HPV18 | E6 | 10 | 72 | YSRIRELRHY | 0.0008 | 30629 |
| HPV18 | L1 | 9 | 495 | APAENKDPY | | 30630 |
| HPV18 | L1 | 8 | 345 | ASPGSCVY | | 30631 |
| HPV18 | L1 | 11 | 407 | ASTQSPVPGQY | | 30632 |
| HPV18 | L1 | 10 | 286 | CQSICKYPDY | | 30633 |
| HPV18 | L1 | 11 | 493 | DAAPAENKDPY | | 30634 |
| HPV18 | L1 | 9 | 258 | DGDMVDTGY | | 30635 |
| HPV18 | L1 | 9 | 364 | DSQLFNKPY | | 30636 |
| HPV18 | L1 | 8 | 330 | DTVPQSLY | | 30637 |
| HPV18 | L1 | 8 | 517 | FSLDLDQY | | 30638 |
| HPV18 | L1 | 8 | 177 | GLSGHPFY | | 30639 |
| HPV18 | L1 | 11 | 342 | GMPASPGSCVY | | 30640 |
| HPV18 | L1 | 10 | 443 | ITLTADVMSY | | 30641 |
| HPV18 | L1 | 9 | 516 | KFSLDLDQY | | 30642 |
| HPV18 | L1 | 10 | 120 | KQDIPKVSAY | | 30643 |
| HPV18 | L1 | 11 | 256 | LEDGDMVDTGY | | 30644 |
| HPV18 | L1 | 8 | 445 | LTADVMSY | | 30645 |
| HPV18 | L1 | 10 | 328 | MGDTVPQSLY | | 30646 |
| HPV18 | L1 | 10 | 343 | MPASPGSCVY | | 30647 |
| HPV18 | L1 | 8 | 496 | PAENKDPY | | 30648 |
| HPV18 | L1 | 9 | 344 | PASPGSCVY | | 30649 |
| HPV18 | L1 | 11 | 282 | PLDICQSICKY | | 30650 |
| HPV18 | L1 | 9 | 472 | PTTSLVDTY | | 30651 |
| HPV18 | L1 | 9 | 287 | QSICKYPDY | | 30652 |
| HPV18 | L1 | 8 | 410 | QSPVPGQY | | 30653 |
| HPV18 | L1 | 10 | 416 | QYDATKFKQY | | 30654 |
| HPV18 | L1 | 9 | 424 | QYSRHVEEY | | 30655 |
| HPV18 | L1 | 8 | 66 | RPSDNTVY | | 30656 |
| HPV18 | L1 | 10 | 363 | SDSQLFNKPY | | 30657 |
| HPV18 | L1 | 11 | 100 | SSRLLTVGNPY | | 30658 |
| HPV18 | L1 | 10 | 408 | STQSPVPGQY | | 30659 |
| HPV18 | L1 | 11 | 78 | SVARVVNTDDY | | 30660 |
| HPV18 | L1 | 11 | 327 | TMGDTVPQSLY | | 30661 |
| HPV18 | L1 | 9 | 409 | TQSPVPGQY | | 30662 |
| HPV18 | L1 | 11 | 362 | TSDSQLFNKPY | | 30663 |
| HPV18 | L1 | 8 | 473 | TTSLVDTY | | 30664 |
| HPV18 | L1 | 9 | 204 | VRDNVSVDY | | 30665 |
| HPV18 | L1 | 8 | 89 | VTPTSIFY | | 30666 |
| HPV18 | L1 | 9 | 417 | YDATKFKQY | | 30667 |
| HPV18 | L1 | 11 | 35 | YMVHIIICGHY | | 30668 |
| HPV18 | L1 | 8 | 425 | YSRHVEEY | | 30669 |
| HPV18 | L1 | 9 | 4 | YTRVLILHY | | 30670 |
| HPV18 | L2 | 11 | 341 | ATEDNDLFDIY | | 30671 |
| HPV18 | L2 | 11 | 322 | DISPIAPSPEY | | 30672 |
| HPV18 | L2 | 8 | 344 | DNDLFDIY | | 30673 |
| HPV18 | L2 | 10 | 62 | GSGTGGRTGY | | 30674 |

TABLE XV-continued

A01 Motif Peptides

| Type | Protein | No. of Amino Acids | Position | Sequence | A*0101 | Seq. Id. No. |
|---|---|---|---|---|---|---|
| HPV18 | L2 | 8 | 64 | GTGGRTGY | | 30675 |
| HPV18 | L2 | 10 | 432 | GTHYYLWPLY | | 30676 |
| HPV18 | L2 | 11 | 432 | GTHYYLWPLYY | | 30677 |
| HPV18 | L2 | 10 | 183 | GTPTSGTHGY | | 30678 |
| HPV18 | L2 | 11 | 310 | GTQIGARVHFY | | 30679 |
| HPV18 | L2 | 8 | 313 | IGARVHFY | | 30680 |
| HPV18 | L2 | 10 | 323 | ISPIAPSPEY | | 30681 |
| HPV18 | L2 | 9 | 10 | KRASVTDLY | | 30682 |
| HPV18 | L2 | 10 | 242 | LTRPSSLITY | | 30683 |
| HPV18 | L2 | 10 | 391 | LTSSWDVPVY | | 30684 |
| HPV18 | L2 | 8 | 325 | PIAPSPEY | | 30685 |
| HPV18 | L2 | 9 | 419 | PTAPASTQY | | 30686 |
| HPV18 | L2 | 9 | 376 | PTISSASSY | | 30687 |
| HPV18 | L2 | 8 | 185 | PTSGTHGY | | 30688 |
| HPV18 | L2 | 8 | 11 | RASVTDLY | | 30689 |
| HPV18 | L2 | 8 | 244 | RPSSLITY | | 30690 |
| HPV18 | L2 | 11 | 364 | RSTTSFAFFKY | | 30691 |
| HPV18 | L2 | 8 | 220 | RVAGPRLY | | 30692 |
| HPV18 | L2 | 8 | 393 | SSWDVPVY | | 30693 |
| HPV18 | L2 | 10 | 365 | STTSFAFFKY | | 30694 |
| HPV18 | L2 | 10 | 342 | TEDNDLFDIY | | 30695 |
| HPV18 | L2 | 11 | 61 | TGSGTGGRTGY | | 30696 |
| HPV18 | L2 | 8 | 377 | TISSASSY | | 30697 |
| HPV18 | L2 | 8 | 367 | TSFAFFKY | | 30698 |
| HPV18 | L2 | 9 | 392 | TSSWDVPVY | | 30699 |
| HPV18 | L2 | 9 | 366 | TFSFAFFKY | | 30700 |
| HPV18 | L2 | 11 | 417 | VSPTAPASTQY | | 30701 |
| HPV18 | L2 | 11 | 374 | YSPTISSASSY | | 30702 |
| HPV31 | E1 | 11 | 79 | AEAVQVLKRKY | | 30703 |
| HPV31 | E1 | 10 | 186 | AMLGKFKELY | | 30704 |
| HPV31 | E1 | 8 | 504 | ATTPCWHY | | 30705 |
| HPV31 | E1 | 10 | 502 | DDATTPCWHY | | 30706 |
| HPV31 | E1 | 9 | 351 | DDSEIAYKY | | 30707 |
| HPV31 | E1 | 8 | 96 | DISSCVDY | | 30708 |
| HPV31 | E1 | 10 | 336 | DLSQMVQWAY | | 30709 |
| HPV31 | E1 | 8 | 352 | DSEIAYKY | | 30710 |
| HPV31 | E1 | 8 | 50 | FIDNCNVY | | 30711 |
| HPV31 | E1 | 8 | 551 | GKDDRWPY | | 30712 |
| HPV31 | E1 | 9 | 305 | GMSNISDVY | | 30713 |
| HPV31 | E1 | 9 | 11 | GTGCNGWFY | 3.9 | 30714 |
| HPV31 | E1 | 10 | 456 | HGAPNTGKSY | | 30715 |
| HPV31 | E1 | 11 | 548 | INAGKDDRWPY | | 30716 |
| HPV31 | E1 | 11 | 471 | ISFLQGCIISY | | 30717 |
| HPV31 | E1 | 10 | 232 | KTLLQPYCLY | | 30718 |
| HPV31 | E1 | 11 | 501 | LDDATTPCWHY | | 30719 |
| HPV31 | E1 | 9 | 125 | LFELPDSGY | | 30720 |
| HPV31 | E1 | 9 | 292 | LRSTAAALY | | 30721 |
| HPV31 | E1 | 11 | 292 | LRSTAAALYWY | | 30722 |
| HPV31 | E1 | 10 | 94 | LSDISSCVDY | | 30723 |
| HPV31 | E1 | 9 | 337 | LSQMVQWAY | | 30724 |
| HPV31 | E1 | 8 | 350 | MDDSEIAY | | 30725 |
| HPV31 | E1 | 10 | 350 | MDDSEIAYKY | | 30726 |
| HPV31 | E1 | 8 | 306 | MSNISDVY | | 30727 |
| HPV31 | E1 | 11 | 47 | MVDFIDNCNVY | | 30728 |
| HPV31 | E1 | 10 | 573 | PFDKNGNPVY | | 30729 |
| HPV31 | E1 | 11 | 93 | PLSDISSCVDY | | 30730 |
| HPV31 | E1 | 8 | 293 | RSTAAALY | | 30731 |
| HPV31 | E1 | 10 | 293 | RSTAAALYWY | | 30732 |
| HPV31 | E1 | 11 | 303 | RTGMSNISDVY | | 30733 |
| HPV31 | E1 | 9 | 294 | STAAALYWY | | 30734 |
| HPV31 | E1 | 8 | 295 | TAAALYWY | | 30735 |
| HPV31 | E1 | 11 | 505 | TTPCWHYIDNY | | 30736 |
| HPV31 | E1 | 11 | 382 | VKDCGTMCRHY | | 30737 |
| HPV31 | E1 | 9 | 349 | VMDDSEIAY | | 30738 |
| HPV31 | E1 | 11 | 349 | VMDDSEIAYKY | | 30739 |
| HPV31 | E1 | 10 | 419 | WRDIVKFLRY | | 30740 |
| HPV31 | E2 | 9 | 11 | CQDKILEHY | | 30741 |
| HPV31 | E2 | 10 | 122 | DGDVHNTMHY | | 30742 |
| HPV31 | E2 | 11 | 22 | DSKRLCDHIDY | | 30743 |
| HPV31 | E2 | 8 | 80 | ETLNNTEY | | 30744 |
| HPV31 | E2 | 8 | 171 | FTEEAKKY | | 30745 |
| HPV31 | E2 | 11 | 300 | GDANILKCLRY | | 30746 |
| HPV31 | E2 | 9 | 336 | KNAIVTLTY | | 30747 |
| HPV31 | E2 | 8 | 312 | LSKYKQLY | | 30748 |
| HPV31 | E2 | 10 | 78 | MLETLNNTEY | | 30749 |

TABLE XV-continued

A01 Motif Peptides

| Type | Protein | No. of Amino Acids | Position | Sequence | A*0101 | Seq. Id. No. |
|---|---|---|---|---|---|---|
| HPV31 | E2 | 11 | 77 | MMLETLNNTEY | | 30750 |
| HPV31 | E2 | 9 | 361 | NTVSVSTGY | | 30751 |
| HPV31 | E2 | 10 | 106 | PTGCLKKHGY | | 30752 |
| HPV31 | E2 | 8 | 37 | RLECVLMY | | 30753 |
| HPV31 | E2 | 9 | 311 | RLSKYKQLY | | 30754 |
| HPV31 | E2 | 11 | 128 | TMHYTNWKFIY | | 30755 |
| HPV31 | E2 | 10 | 93 | TMQQTSLELY | | 30756 |
| HPV31 | E2 | 8 | 362 | TVSVSTGY | | 30757 |
| HPV31 | E2 | 8 | 160 | VHEGHITY | | 30758 |
| HPV31 | E2 | 11 | 92 | WTMQQTSLELY | | 30759 |
| HPV31 | E2 | 8 | 131 | YTNWKFIY | | 30760 |
| HPV31 | E5 | 11 | 53 | ATSPLRCFCIY | | 30761 |
| HPV31 | E5 | 10 | 54 | TSPLRCFCIY | | 30762 |
| HPV31 | E6 | 8 | 63 | CTKCLRFY | | 30763 |
| HPV31 | E6 | 11 | 44 | DFAFTDLTIVY | | 30764 |
| HPV31 | E6 | 10 | 14 | ELSSALEIPY | | 30765 |
| HPV31 | E6 | 8 | 47 | FTDLTIVY | | 30766 |
| HPV31 | E6 | 11 | 69 | FYSKVSEFRWY | | 30767 |
| HPV31 | E6 | 8 | 72 | KVSEFRWY | | 30768 |
| HPV31 | E6 | 10 | 72 | KVSEFRWYRY | | 30769 |
| HPV31 | E6 | 9 | 15 | LSSALEIPY | | 30770 |
| HPV31 | E6 | 11 | 22 | PYDELRLNCVY | | 30771 |
| HPV31 | E6 | 8 | 16 | SSALEIPY | | 30772 |
| HPV31 | E6 | 9 | 73 | VSEFRWYRY | | 30773 |
| HPV31 | E6 | 10 | 23 | YDELRLNCVY | | 30774 |
| HPV31 | E6 | 10 | 70 | YSKVSEFRWY | | 30775 |
| HPV31 | E7 | 8 | 4 | ETPTLQDY | | 30776 |
| HPV31 | E7 | 10 | 43 | GQAEPDTSNY | | 30777 |
| HPV31 | E7 | 9 | 17 | PEATDLHCY | | 30778 |
| HPV31 | E7 | 9 | 44 | QAEPDTSNY | | 30779 |
| HPV31 | E7 | 10 | 16 | QPEATDLHCY | | 30780 |
| HPV31 | E7 | 10 | 2 | RGETPTLQDY | | 30781 |
| HPV31 | L1 | 8 | 285 | ATLANSTY | | 30782 |
| HPV31 | L1 | 10 | 226 | CNSICKYPDY | | 30783 |
| HPV31 | L1 | 8 | 129 | DTENSNRY | | 30784 |
| HPV31 | L1 | 8 | 270 | ESVPTDLY | | 30785 |
| HPV31 | L1 | 10 | 127 | FDDTENSNRY | | 30786 |
| HPV31 | L1 | 9 | 356 | FKSSNFKEY | | 30787 |
| HPV31 | L1 | 9 | 269 | GESVPTDLY | | 30788 |
| HPV31 | L1 | 11 | 282 | GSTATLANSTY | | 30789 |
| HPV31 | L1 | 10 | 382 | ITLSADIMTY | | 30790 |
| HPV31 | L1 | 8 | 438 | KEDPFKDY | | 30791 |
| HPV31 | L1 | 11 | 126 | KFDDTENSNRY | | 30792 |
| HPV31 | L1 | 8 | 357 | KSSNFKEY | | 30793 |
| HPV31 | L1 | 8 | 384 | LSADIMTY | | 30794 |
| HPV31 | L1 | 8 | 43 | LTVGHPYY | | 30795 |
| HPV31 | L1 | 9 | 144 | NRECISMDY | | 30796 |
| HPV31 | L1 | 9 | 227 | NSICKYPDY | | 30797 |
| HPV31 | L1 | 9 | 437 | PKEDPFKDY | | 30798 |
| HPV31 | L1 | 11 | 222 | PLDICNSICKY | | 30799 |
| HPV31 | L1 | 10 | 410 | PPSGSLEDTY | | 30800 |
| HPV31 | L1 | 9 | 411 | PSGSLEDTY | | 30801 |
| HPV31 | L1 | 11 | 17 | PVSKVVSTDEY | | 30802 |
| HPV31 | L1 | 8 | 5 | RPSEATVY | | 30803 |
| HPV31 | L1 | 10 | 303 | SDAQIFNKPY | | 30804 |
| HPV31 | L1 | 8 | 412 | SGSLEDTY | | 30805 |
| HPV31 | L1 | 10 | 283 | STATLANSTY | | 30806 |
| HPV31 | L1 | 11 | 24 | TDEYVTRTNIY | | 30807 |
| HPV31 | L1 | 9 | 383 | TLSADIMTY | | 30808 |
| HPV31 | L1 | 11 | 302 | TSDAQIFNKPY | | 30809 |
| HPV31 | L1 | 11 | 354 | TTFKSSNFKEY | | 30810 |
| HPV31 | L1 | 10 | 268 | VGESVPTDLY | | 30811 |
| HPV31 | L1 | 10 | 18 | VSKVVSTDEY | | 30812 |
| HPV31 | L1 | 8 | 28 | VTRTNIYY | | 30813 |
| HPV31 | L1 | 8 | 243 | YGDTLFFY | | 30814 |
| HPV31 | L2 | 9 | 311 | ATIGARVHY | | 30815 |
| HPV31 | L2 | 10 | 311 | ATIGARVHYY | | 30816 |
| HPV31 | L2 | 11 | 311 | ATIGARVHYYY | | 30817 |
| HPV31 | L2 | 10 | 253 | ETVNAEESLY | | 30818 |
| HPV31 | L2 | 11 | 237 | FLSAPKQLITY | | 30819 |
| HPV31 | L2 | 8 | 433 | FVDGGDFY | | 30820 |
| HPV31 | L2 | 10 | 436 | GGDFYLHPSY | | 30821 |
| HPV31 | L2 | 11 | 436 | GGDFYLHPSYY | | 30822 |
| HPV31 | L2 | 10 | 63 | GSGTGGRTGY | | 30823 |
| HPV31 | L2 | 8 | 65 | GTGGRTGY | | 30824 |

TABLE XV-continued

A01 Motif Peptides

| Type | Protein | No. of Amino Acids | Position | Sequence | A*0101 | Seq. Id. No. |
|---|---|---|---|---|---|---|
| HPV31 | L2 | 11 | 38 | HTTIADQILRY | | 30825 |
| HPV31 | L2 | 8 | 41 | IADQILRY | | 30826 |
| HPV3I | L2 | 8 | 313 | IGARVHYY | | 30827 |
| HPV31 | L2 | 9 | 313 | IGARVHYYY | | 30828 |
| HPV31 | L2 | 8 | 245 | ITYENPAY | | 30829 |
| HPV31 | L2 | 9 | 11 | KRASATQLY | | 30830 |
| HPV31 | L2 | 9 | 348 | LNDGLYDIY | | 30831 |
| HPV31 | L2 | 10 | 238 | LSAPKQLITY | | 30832 |
| HPV31 | L2 | 11 | 178 | LSSSSISTHNY | | 30833 |
| HPV31 | L2 | 10 | 287 | LTSRRNTVRY | | 30834 |
| HPV31 | L2 | 9 | 378 | QSTSAVSAY | | 30835 |
| HPV31 | L2 | 8 | 12 | RASATQLY | | 30836 |
| HPV31 | L2 | 8 | 216 | RPARLGLY | | 30837 |
| HPV31 | L2 | 11 | 9 | RTKRASATQLY | | 30838 |
| HPV31 | L2 | 11 | 309 | SGATIGARVHY | | 30839 |
| HPV31 | L2 | 11 | 62 | SGSGTGGRTGY | | 30840 |
| HPV31 | L2 | 8 | 181 | SSISTHNY | | 30841 |
| HPV31 | L2 | 9 | 180 | SSSISTHNY | | 30842 |
| HPV31 | L2 | 10 | 179 | SSSSISTHNY | | 30843 |
| HPV31 | L2 | 8 | 346 | STLNDGLY | | 30844 |
| HPV31 | L2 | 11 | 346 | STLNDGLYDIY | | 30845 |
| HPV31 | L2 | 8 | 379 | STSAVSAY | | 30846 |
| HPV31 | L2 | 9 | 40 | TIADQILRY | | 30847 |
| HPV31 | L2 | 9 | 288 | TSRRNTVRY | | 30848 |
| HPV31 | L2 | 9 | 345 | TSTLNDGLY | | 30849 |
| HPV31 | L2 | 10 | 39 | TTIADQILRY | | 30850 |
| HPV31 | L2 | 10 | 344 | TTSTLNDGLY | | 30851 |
| HPV31 | L2 | 11 | 343 | TTTSTLNDGLY | | 30852 |
| HPV31 | L2 | 8 | 255 | VNAEESLY | | 30853 |
| HPV31 | L2 | 10 | 377 | VQSTSAVSAY | | 30854 |
| HPV31 | L2 | 11 | 430 | VSIFVDGGDFY | | 30855 |
| HPV33 | E1 | 9 | 226 | CTDWCITGY | | 30856 |
| HPV33 | E1 | 8 | 364 | DDSDIAYY | | 30857 |
| HPV33 | E1 | 9 | 364 | DDSDIAYYY | | 30858 |
| HPV33 | E1 | 10 | 349 | DLSEMVQWAY | | 30859 |
| HPV33 | E1 | 8 | 365 | DSDIAYYY | | 30860 |
| HPV33 | E1 | 9 | 587 | FDENGNPVY | | 30861 |
| HPV33 | E1 | 9 | 470 | GPANTGKSY | | 30862 |
| HPV33 | E1 | 8 | 564 | GTDSRWPY | | 30863 |
| HPV33 | E1 | 11 | 192 | HSSNTKANILY | | 30864 |
| HPV33 | E1 | 11 | 514 | IDDVTPISWTY | | 30865 |
| HPV33 | E1 | 9 | 125 | IDELEDSGY | | 30866 |
| HPV33 | E1 | 9 | 520 | ISWTYIDDY | | 30867 |
| HPV33 | E1 | 10 | 124 | KIDELEDSGY | | 30868 |
| HPV33 | E1 | 9 | 305 | LRSQTCALY | | 30869 |
| HPV33 | E1 | 9 | 350 | LSEMVQWAY | | 30870 |
| HPV33 | E1 | 9 | 362 | LTDDSDIAY | | 30871 |
| HPV33 | E1 | 10 | 362 | LTDDSDIAYY | | 30872 |
| HPV33 | E1 | 11 | 362 | LTDDSDIAYYY | | 30873 |
| HPV33 | E1 | 8 | 195 | NTKANILY | | 30874 |
| HPV33 | E1 | 10 | 586 | PFDENGNPVY | | 30875 |
| HPV33 | E1 | 10 | 519 | PISWTYIDDY | | 30876 |
| HPV33 | E1 | 8 | 306 | RSQTCALY | | 30877 |
| HPV33 | E1 | 10 | 193 | SSNTKANILY | | 30878 |
| HPV33 | E1 | 8 | 363 | TDDSDIAY | | 30879 |
| HPV33 | E1 | 9 | 363 | TDDSDIAYY | | 30880 |
| HPV33 | E1 | 10 | 363 | TDDSDIAYYY | | 30881 |
| HPV33 | E1 | 11 | 561 | TNAGTDSRWPY | | 30882 |
| HPV33 | E1 | 11 | 224 | TSCTDWCITGY | | 30883 |
| HPV33 | E1 | 11 | 110 | TSINKNKECTY | | 30884 |
| HPV33 | E1 | 11 | 395 | VKDCGIMCRHY | | 30885 |
| HPV33 | E1 | 8 | 517 | VTPISWTY | | 30886 |
| HPV33 | E2 | 10 | 78 | ALETLSKSQY | | 30887 |
| HPV33 | E2 | 10 | 145 | CTMVTGKVDY | | 30888 |
| HPV33 | E2 | 10 | 122 | DNDKKNTMDY | | 30889 |
| HPV33 | E2 | 10 | 282 | ESNSLKCLRY | | 30890 |
| HPV33 | E2 | 8 | 80 | ETLSKSQY | | 30891 |
| HPV33 | E2 | 8 | 171 | FKEDAAKY | | 30892 |
| HPV33 | E2 | 11 | 281 | GESNSLKCLRY | | 30893 |
| HPV33 | E2 | 8 | 151 | KVDYIGMY | | 30894 |
| HPV33 | E2 | 9 | 151 | KVDYIGMYY | | 30895 |
| HPV33 | E2 | 9 | 162 | NCEKVYFKY | | 30896 |
| HPV33 | E2 | 8 | 284 | NSLKCLRY | | 30897 |
| HPV33 | E2 | 9 | 113 | QGETVTVQY | | 30898 |
| HPV33 | E2 | 8 | 37 | RMECALLY | | 30899 |

TABLE XV-continued

A01 Motif Peptides

| Type | Protein | No. of Amino Acids | Position | Sequence | A*0101 | Seq. Id. No. |
|---|---|---|---|---|---|---|
| HPV33 | E2 | 9 | 283 | SNSLKCLRY | | 30900 |
| HPV33 | E2 | 11 | 128 | TMDYTNWGEIY | | 30901 |
| HPV33 | E2 | 9 | 146 | TMVTGKVDY | | 30902 |
| HPV33 | E2 | 9 | 11 | VQEKILDLY | | 30903 |
| HPV33 | E2 | 11 | 148 | VTGKVDYIGMY | | 30904 |
| HPV33 | E2 | 8 | 131 | YTNWGEIY | | 30905 |
| HPV33 | E5 | 10 | 44 | GSPLKIFFCY | | 30906 |
| HPV33 | E5 | 11 | 43 | VGSPLKIFFCY | | 30907 |
| HPV33 | E6 | 9 | 46 | AFADLTVVY | | 30908 |
| HPV33 | E6 | 11 | 44 | DFAFADLTVVY | | 30909 |
| HPV33 | E6 | 8 | 47 | FADLTVVY | | 30910 |
| HPV33 | E6 | 8 | 69 | FLSKISEY | | 30911 |
| HPV33 | E6 | 11 | 69 | FLSKISEYRHY | | 30912 |
| HPV33 | E6 | 9 | 73 | ISEYRHYNY | | 30913 |
| HPV33 | E6 | 8 | 72 | KISEYRHY | | 30914 |
| HPV33 | E6 | 10 | 72 | KISEYRHYNY | | 30915 |
| HPV33 | E6 | 10 | 70 | LSKISEYRHY | | 30916 |
| HPV33 | E7 | 10 | 43 | GQAQPATADY | | 30917 |
| HPV33 | E7 | 11 | 43 | GQAQPATADYY | | 30918 |
| HPV33 | E7 | 9 | 8 | LKEYVLDLY | | 30919 |
| HPV33 | E7 | 11 | 6 | PTLKEYVLDLY | | 30920 |
| HPV33 | E7 | 8 | 46 | QPATADYY | | 30921 |
| HPV33 | E7 | 8 | 16 | YPEPTDLY | | 30922 |
| HPV33 | E7 | 10 | 16 | YPEPTDLYCY | | 30923 |
| HPV33 | L1 | 10 | 225 | CGSTCKYPDY | | 30924 |
| HPV33 | L1 | 10 | 345 | CTQVTSDSTY | | 30925 |
| HPV33 | L1 | 8 | 129 | DTETGNKY | | 30926 |
| HPV33 | L1 | 9 | 435 | EKEDPLGKY | | 30927 |
| HPV33 | L1 | 9 | 303 | ESQLFNKPY | | 30928 |
| HPV33 | L1 | 10 | 127 | FDDTETGNKY | | 30929 |
| HPV33 | L1 | 11 | 359 | FKEYIRHVEEY | | 30930 |
| HPV33 | L1 | 9 | 268 | GEAVPDDLY | | 30931 |
| HPV33 | L1 | 9 | 226 | GSTCKYPDY | | 30932 |
| HPV33 | L1 | 8 | 436 | KEDPLGKY | | 30933 |
| HPV33 | L1 | 11 | 126 | KFDDTETGNKY | | 30934 |
| HPV33 | L1 | 8 | 355 | KNENFKEY | | 30935 |
| HPV33 | L1 | 10 | 267 | LGEAVPDDLY | | 30936 |
| HPV33 | L1 | 8 | 42 | LLAVGHPY | | 30937 |
| HPV33 | L1 | 8 | 382 | LTAEVMTY | | 30938 |
| HPV33 | L1 | 9 | 144 | NRECLSMDY | | 30939 |
| HPV33 | L1 | 11 | 221 | PIDICGSTCKY | | 30940 |
| HPV33 | L1 | 11 | 433 | PKEKEDPLGKY | | 30941 |
| HPV33 | L1 | 10 | 408 | PPSASLQDTY | | 30942 |
| HPV33 | L1 | 9 | 409 | PSASLQDTY | | 30943 |
| HPV33 | L1 | 11 | 17 | PVSKVVSTDEY | | 30944 |
| HPV33 | L1 | 8 | 5 | RPSEATVY | | 30945 |
| HPV33 | L1 | 8 | 410 | SASLQDTY | | 30946 |
| HPV33 | L1 | 10 | 302 | SESQLFNKPY | | 30947 |
| HPV33 | L1 | 11 | 39 | SSRLLAVGHPY | | 30948 |
| HPV33 | L1 | 8 | 227 | STCKYPDY | | 30949 |
| HPV33 | L1 | 11 | 352 | STYKNENFKEY | | 30950 |
| HPV33 | L1 | 11 | 24 | TDEYVSRTSIY | | 30951 |
| HPV33 | L1 | 11 | 301 | TSESQLFNKPY | | 30952 |
| HPV33 | L1 | 10 | 18 | VSKVVSTDEY | | 30953 |
| HPV33 | L1 | 8 | 28 | VSRTSIYY | | 30954 |
| HPV33 | L1 | 9 | 28 | VSRTSIYYY | | 30955 |
| HPV33 | L1 | 10 | 380 | VTLTAEVMTY | | 30956 |
| HPV33 | L1 | 8 | 27 | YVSRTSIY | | 30957 |
| HPV33 | L1 | 9 | 27 | YVSRTSIYY | | 30958 |
| HPV33 | L1 | 10 | 27 | YVSRTSIYYY | | 30959 |
| HPV33 | L2 | 11 | 436 | DGADFVLHPSY | | 30960 |
| HPV33 | L2 | 11 | 183 | FSSPTVSTQSY | | 30961 |
| HPV33 | L2 | 10 | 437 | GADFVLHPSY | | 30962 |
| HPV33 | L2 | 8 | 64 | GSGGRTGY | | 30963 |
| HPV33 | L2 | 10 | 62 | GSGSGGRTGY | | 30964 |
| HPV33 | L2 | 11 | 218 | GSRPVARLGLY | | 30965 |
| HPV33 | L2 | 11 | 37 | GSTIADQILKY | | 30966 |
| HPV33 | L2 | 8 | 374 | HTPMQHSY | | 30967 |
| HPV33 | L2 | 8 | 336 | HTVPNEQY | | 30968 |
| HPV33 | L2 | 8 | 40 | IADQILKY | | 30969 |
| HPV33 | L2 | 8 | 318 | IGARIHYY | | 30970 |
| HPV33 | L2 | 9 | 358 | INDGLYDVY | | 30971 |
| HPV33 | L2 | 9 | 10 | KRASATQLY | | 30972 |
| HPV33 | L2 | 9 | 348 | LHDTSTSSY | | 30973 |
| HPV33 | L2 | 10 | 243 | LTSPHKLITY | | 30974 |

TABLE XV-continued

A01 Motif Peptides

| Type | Protein | No. of Amino Acids | Position | Sequence | A*0101 | Seq. Id. No. |
|---|---|---|---|---|---|---|
| HPV33 | L2 | 11 | 333 | PLDHTVPNEQY | | 30975 |
| HPV33 | L2 | 8 | 186 | PTVSTQSY | | 30976 |
| HPV33 | L2 | 8 | 221 | PVARLGLY | | 30977 |
| HPV33 | L2 | 8 | 11 | RASATQLY | | 30978 |
| HPV33 | L2 | 9 | 63 | SGSGGRTGY | | 30979 |
| HPV33 | L2 | 10 | 184 | SSPTVSTQSY | | 30980 |
| HPV33 | L2 | 10 | 354 | SSYSINDGLY | | 30981 |
| HPV33 | L2 | 10 | 38 | STIADQILKY | | 30982 |
| HPV33 | L2 | 9 | 355 | SYSINDGLY | | 30983 |
| HPV33 | L2 | 11 | 61 | TGSGSGGRTGY | | 30984 |
| HPV33 | L2 | 9 | 39 | TIADQILKY | | 30985 |
| HPV33 | L2 | 9 | 244 | TSPHKLITY | | 30986 |
| HPV33 | L2 | 11 | 353 | TSSYSINDGLY | | 30987 |
| HPV33 | L2 | 8 | 356 | YSINDGLY | | 30988 |
| HPV33 | L2 | 11 | 356 | YSINDGLYDVY | | 30989 |
| HPV45 | E1 | 8 | 564 | AKDNKWPY | | 30990 |
| HPV45 | E1 | 10 | 199 | AMLAVFKDIY | | 30991 |
| HPV45 | E1 | 8 | 517 | ATHTCWTY | | 30992 |
| HPV45 | E1 | 9 | 397 | DCAVMCRHY | | 30993 |
| HPV45 | E1 | 10 | 515 | DDATHTCWTY | | 30994 |
| HPV45 | E1 | 9 | 364 | DESDMAFQY | | 30995 |
| HPV45 | E1 | 10 | 562 | DPAKDNKWPY | | 30996 |
| HPV45 | E1 | 8 | 365 | ESDMAFQY | | 30997 |
| HPV45 | E1 | 8 | 130 | FTISDSGY | | 30998 |
| HPV45 | E1 | 9 | 470 | GPANTGKSY | | 30999 |
| HPV45 | E1 | 11 | 459 | GTPKKNCILLY | | 31000 |
| HPV45 | E1 | 10 | 519 | HTCWTYFDNY | | 31001 |
| HPV45 | E1 | 8 | 378 | KSNCQAKY | | 31002 |
| HPV45 | E1 | 10 | 245 | KTLIKPATLY | | 31003 |
| HPV45 | E1 | 11 | 514 | LDDATHTCWTY | | 31004 |
| HPV45 | E1 | 11 | 395 | LKDCAVMCRHY | | 31005 |
| HPV45 | E1 | 9 | 386 | LKSNCQAKY | | 31006 |
| HPV45 | E1 | 9 | 305 | LRSSVAALY | | 31007 |
| HPV45 | E1 | 11 | 305 | LRSSVAALYWY | | 31008 |
| HPV45 | E1 | 11 | 362 | LTDESDMAFQY | | 31009 |
| HPV45 | E1 | 9 | 200 | MLAVFKDIY | | 31010 |
| HPV45 | E1 | 8 | 414 | NMSQWIKY | | 31011 |
| HPV45 | E1 | 10 | 586 | PFDKNGNPVY | | 31012 |
| HPV45 | E1 | 10 | 412 | QMNMSQWIKY | | 31013 |
| HPV45 | E1 | 8 | 306 | RSSVAALY | | 31014 |
| HPV45 | E1 | 10 | 306 | RSSVAALYWY | | 31015 |
| HPV45 | E1 | 9 | 307 | SSVAALYWY | | 31016 |
| HPV45 | E1 | 8 | 308 | SVAALYWY | | 31017 |
| HPV45 | E1 | 10 | 363 | TDESDMAFQY | | 31018 |
| HPV45 | E2 | 11 | 134 | CMNYVVWDSIY | | 31019 |
| HPV45 | E2 | 8 | 158 | CVSYWGVY | | 31020 |
| HPV45 | E2 | 9 | 158 | CVSYWGVYY | | 31021 |
| HPV45 | E2 | 11 | 28 | DSKDINSQISY | | 31022 |
| HPV45 | E2 | 8 | 178 | FKSECEKY | | 31023 |
| HPV45 | E2 | 10 | 186 | GNSNTWEVQY | | 31024 |
| HPV45 | E2 | 8 | 167 | IKDGDTTY | | 31025 |
| HPV45 | E2 | 9 | 167 | IKDGDTTYY | | 31026 |
| HPV45 | E2 | 11 | 151 | IWDKTAACVSY | | 31027 |
| HPV45 | E2 | 9 | 300 | KNSLKCLRY | | 31028 |
| HPV45 | E2 | 8 | 154 | KTAACVSY | | 31029 |
| HPV45 | E2 | 9 | 17 | LQDKILDHY | | 31030 |
| HPV45 | E2 | 8 | 130 | NKDNCMNY | | 31031 |
| HPV45 | E2 | 8 | 301 | NSLKCLRY | | 31032 |
| HPV45 | E2 | 9 | 187 | NSNTWEVQY | | 31033 |
| HPV45 | E2 | 9 | 357 | NSVQISVGY | | 31034 |
| HPV45 | E2 | 9 | 332 | NTGILTVTY | | 31035 |
| HPV45 | E2 | 10 | 356 | PNSVQISVGY | | 31036 |
| HPV45 | E2 | 10 | 29 | SKDINSQISY | | 31037 |
| HPV45 | E2 | 11 | 155 | TAACVSYWGVY | | 31038 |
| HPV45 | E2 | 8 | 159 | VSYWGVYY | | 31039 |
| HPV45 | E6 | 9 | 37 | ATLERTEVY | | 31040 |
| HPV45 | E6 | 11 | 35 | CKATLERTEVY | | 31041 |
| HPV45 | E6 | 8 | 27 | DVSIACVY | | 31042 |
| HPV45 | E6 | 9 | 4 | FDDPTQRPY | | 31043 |
| HPV45 | E6 | 8 | 127 | FHSIAGQY | | 31044 |
| HPV45 | E6 | 8 | 49 | FKDLFIVY | | 31045 |
| HPV45 | E6 | 10 | 71 | FYSRIRELRY | | 31046 |
| HPV45 | E6 | 11 | 71 | FYSRIRELRYY | | 31047 |
| HPV45 | E6 | 10 | 25 | LQDVSIACVY | | 31048 |
| HPV45 | E6 | 11 | 46 | QFAFKDLFIVY | | 31049 |

TABLE XV-continued

A01 Motif Peptides

| Type | Protein | No. of Amino Acids | Position | Sequence | A*0101 | Seq. Id. No. |
|---|---|---|---|---|---|---|
| HPV45 | E6 | 10 | 3 | RFDDPTQRPY | | 31050 |
| HPV45 | E6 | 11 | 89 | TLEKITNTELY | | 31051 |
| HPV45 | E6 | 8 | 38 | TLERTEVY | | 31052 |
| HPV45 | E6 | 11 | 62 | YAACHKCIDFY | | 31053 |
| HPV45 | E6 | 9 | 72 | YSRIRELRY | | 31054 |
| HPV45 | E6 | 10 | 72 | YSRIRELRYY | | 31055 |
| HPV45 | E7 | 10 | 20 | ELDPVDLLCY | | 31056 |
| HPV45 | L1 | 11 | 375 | ASTQNPVPNTY | | 31057 |
| HPV45 | L1 | 10 | 252 | CQSICKYPDY | | 31058 |
| HPV45 | L1 | 9 | 224 | DGDMVDTGY | | 31059 |
| HPV45 | L1 | 9 | 332 | DSQLFNKPY | | 31060 |
| HPV45 | L1 | 11 | 461 | DTTPPEKQDPY | | 31061 |
| HPV45 | L1 | 8 | 296 | DTVPTDLY | | 31062 |
| HPV45 | L1 | 8 | 313 | ETPGSCVY | | 31063 |
| HPV45 | L1 | 8 | 485 | FSSDLDQY | | 31064 |
| HPV45 | L1 | 8 | 143 | GLSGHPFY | | 31065 |
| HPV45 | L1 | 9 | 392 | HYSRHVEEY | | 31066 |
| HPV45 | L1 | 11 | 222 | IEDGDMVDTGY | | 31067 |
| HPV45 | L1 | 10 | 411 | ITLTAEVMSY | | 31068 |
| HPV45 | L1 | 9 | 484 | KFSSDLDQY | | 31069 |
| HPV45 | L1 | 10 | 86 | KQAVPKVSAY | | 31070 |
| HPV45 | L1 | 8 | 413 | LTAEVMSY | | 31071 |
| HPV45 | L1 | 10 | 294 | MGDTVPTDLY | | 31072 |
| HPV45 | L1 | 10 | 311 | MRETPGSCVY | | 31073 |
| HPV45 | L1 | 11 | 310 | NMRETPGSCVY | | 31074 |
| HPV45 | L1 | 11 | 383 | NTYDPTKFKHY | | 31075 |
| HPV45 | L1 | 11 | 248 | PLDICQSICKY | | 31076 |
| HPV45 | L1 | 8 | 464 | PPEKQDPY | | 31077 |
| HPV45 | L1 | 9 | 440 | PTTSLVDTY | | 31078 |
| HPV45 | L1 | 9 | 253 | QSICKYPDY | | 31079 |
| HPV45 | L1 | 8 | 31 | RPSDSTVY | | 31080 |
| HPV45 | L1 | 10 | 331 | SDSQLFNKPY | | 31081 |
| HPV45 | L1 | 11 | 65 | SSRLLTVGNPY | | 31082 |
| HPV45 | L1 | 10 | 376 | STQNPVPNTY | | 31083 |
| HPV45 | L1 | 11 | 43 | SVARVVNTDDY | | 31084 |
| HPV45 | L1 | 11 | 330 | TSDSQLFNKPY | | 31085 |
| HPV45 | L1 | 10 | 462 | TTPPEKQDPY | | 31086 |
| HPV45 | L1 | 8 | 441 | TTSLVDTY | | 31087 |
| HPV45 | L1 | 10 | 384 | TYDPTKFKHY | | 31088 |
| HPV45 | L1 | 11 | 293 | VMGDTVPTDLY | | 31089 |
| HPV45 | L1 | 9 | 170 | VRDNVSVDY | | 31090 |
| HPV45 | L1 | 8 | 54 | VSRTSIFY | | 31091 |
| HPV45 | L1 | 8 | 393 | YSRHVEEY | | 31092 |
| HPV45 | L1 | 9 | 53 | TVSRTSIFY | | 31093 |
| HPV45 | L2 | 11 | 340 | ATNDSDLFDVY | | 31094 |
| HPV45 | L2 | 8 | 343 | DSDLFDVY | | 31095 |
| HPV45 | L2 | 8 | 64 | GSGGRTGY | | 31096 |
| HPV45 | L2 | 10 | 62 | GSGSGGRTGY | | 31097 |
| HPV45 | L2 | 10 | 183 | GTPTSGSHGY | | 31098 |
| HPV45 | L2 | 10 | 433 | GTQYYLWPWY | | 31099 |
| HPV45 | L2 | 11 | 433 | GTQYYLWPWYY | | 31100 |
| HPV45 | L2 | 9 | 365 | HKSFTYPKY | | 31101 |
| HPV45 | L2 | 9 | 10 | KRASATDLY | | 31102 |
| HPV45 | L2 | 8 | 366 | KSFTYPKY | | 31103 |
| HPV45 | L2 | 11 | 375 | LTMPSTAASSY | | 31104 |
| HPV45 | L2 | 10 | 392 | LTSAWDVPIY | | 31105 |
| HPV45 | L2 | 9 | 377 | MPSTAASSY | | 31106 |
| HPV45 | L2 | 9 | 342 | NDSDLFDVY | | 31107 |
| HPV45 | L2 | 8 | 378 | PSTAASSY | | 31108 |
| HPV45 | L2 | 10 | 361 | PSTIHKSFTY | | 31109 |
| HPV45 | L2 | 9 | 420 | PTNASTTTY | | 31110 |
| HPV45 | L2 | 8 | 185 | PTSGSHGY | | 31111 |
| HPV45 | L2 | 8 | 11 | RASATDLY | | 31112 |
| HPV45 | L2 | 9 | 63 | SGSGGRTGY | | 31113 |
| HPV45 | L2 | 11 | 246 | SSLVTFDNPAY | | 31114 |
| HPV45 | L2 | 9 | 362 | STIHKSFTY | | 31115 |
| HPV45 | L2 | 11 | 61 | TGSGSGGRTGY | | 31116 |
| HPV45 | L2 | 10 | 376 | TMPSTAASSY | | 31117 |
| HPV45 | L2 | 8 | 421 | TNASTTTY | | 31118 |
| HPV45 | L2 | 10 | 341 | TNDSDLFDVY | | 31119 |
| HPV45 | L2 | 11 | 360 | TPSTIHKSFTY | | 31120 |
| HPV45 | L2 | 9 | 393 | TSAWDVPIY | | 31121 |
| HPV45 | L2 | 11 | 418 | TSPTNASTTTY | | 31122 |
| HPV45 | L2 | 11 | 426 | TTYIGIHGTQY | | 31123 |
| HPV45 | L2 | 8 | 249 | VTFDNPAY | | 31124 |

TABLE XV-continued

A01 Motif Peptides

| Type | Protein | No. of Amino Acids | Position | Sequence | A*0101 | Seq. Id. No. |
|---|---|---|---|---|---|---|
| HPV56 | E2 | 10 | 21 | ALESLSTTIY | | 31125 |
| HPV56 | E2 | 9 | 71 | CMQYVAWKY | | 31126 |
| HPV56 | E2 | 11 | 71 | CMQYVAWKYIY | | 31127 |
| HPV56 | E2 | 11 | 138 | CPDSVSSTCRY | | 31128 |
| HPV56 | E2 | 10 | 92 | CSGVDYRGIY | | 31129 |
| HPV56 | E2 | 11 | 92 | CSGVDYRGIYY | | 31130 |
| HPV56 | E2 | 10 | 65 | DGSKNNCMQY | | 31131 |
| HPV56 | E2 | 9 | 140 | DSVSSTCRY | | 31132 |
| HPV56 | E2 | 8 | 23 | ESLSTTIY | | 31133 |
| HPV56 | E2 | 11 | 294 | FLSHVKIPVVY | | 31134 |
| HPV56 | E2 | 8 | 261 | FVDVTSTY | | 31135 |
| HPV56 | E2 | 9 | 66 | GSKNNCMQY | | 31136 |
| HPV56 | E2 | 8 | 94 | GVDYRGIY | | 31137 |
| HPV56 | E2 | 9 | 94 | GVDYRGIYY | | 31138 |
| HPV56 | E2 | 8 | 130 | HMENESIY | | 31139 |
| HPV56 | E2 | 11 | 258 | KTLFVDVTSTY | | 31140 |
| HPV56 | E2 | 9 | 22 | LESLSTTIY | | 31141 |
| HPV56 | E2 | 10 | 295 | LSHVKIPVVY | | 31142 |
| HPV56 | E2 | 11 | 149 | NVSPVETVNEY | | 31143 |
| HPV56 | E2 | 9 | 277 | NYSIITIIY | | 31144 |
| HPV56 | E2 | 10 | 139 | PDSVSSTCRY | | 31145 |
| HPV56 | E2 | 8 | 152 | PVETVNEY | | 31146 |
| HPV56 | E2 | 8 | 141 | SVSSTCRY | | 31147 |
| HPV56 | E2 | 8 | 271 | TSTDNKNY | | 31148 |
| HPV56 | E2 | 11 | 91 | VCSGVDYRGIY | | 31149 |
| HPV56 | E2 | 8 | 103 | VHDGHKTY | | 31150 |
| HPV56 | E2 | 9 | 103 | VHDGHKTYY | | 31151 |
| HPV56 | E2 | 10 | 150 | VSPVETVNEY | | 31152 |
| HPV56 | E2 | 9 | 270 | WTSTDNKNY | | 31153 |
| HPV56 | E2 | 8 | 278 | YSIITIIY | | 31154 |
| HPV56 | E2 | 8 | 74 | YVAWKYIY | | 31155 |
| HPV56 | E2 | 9 | 74 | YVAWKYIYY | | 31156 |
| HPV56 | E6 | 8 | 50 | CTELKLVY | | 31157 |
| HPV56 | E6 | 8 | 72 | FYSKVRKY | | 31158 |
| HPV56 | E6 | 10 | 72 | FYSKVRKYRY | | 31159 |
| HPV56 | E6 | 11 | 72 | FYSKVRKYRYY | | 31160 |
| HPV56 | E6 | 10 | 37 | KKELTRAEVY | | 31161 |
| HPV56 | E6 | 9 | 99 | LCDLLIRCY | | 31162 |
| HPV56 | E6 | 10 | 26 | LIDLRLSCVY | | 31163 |
| HPV56 | E6 | 11 | 47 | NFACTELKLVY | | 31164 |
| HPV56 | E6 | 9 | 73 | YSKVRKYRY | | 31165 |
| HPV56 | E6 | 10 | 73 | YSKVRKYRYY | | 31166 |
| HPV56 | E7 | 9 | 51 | RQAKQHTCY | | 31167 |
| HPV56 | L1 | 11 | 273 | ADAYGDSMWFY | | 31168 |
| HPV56 | L1 | 8 | 381 | ATEQLSKY | | 31169 |
| HPV56 | L1 | 8 | 444 | ATSLEDKY | | 31170 |
| HPV56 | L1 | 10 | 444 | ATSLEDKYRY | | 31171 |
| HPV56 | L1 | 11 | 37 | ATWRPSENKVY | | 31172 |
| HPV56 | L1 | 11 | 60 | DSYVKRTSIFY | | 31173 |
| HPV56 | L1 | 8 | 303 | ETIPAELY | | 31174 |
| HPV56 | L1 | 10 | 316 | GREPPPSSVY | | 31175 |
| HPV56 | L1 | 11 | 378 | ISTATEQLSKY | | 31176 |
| HPV56 | L1 | 10 | 414 | ITLSAEVMAY | | 31177 |
| HPV56 | L1 | 8 | 470 | KQDPLAKY | | 31178 |
| HPV56 | L1 | 10 | 93 | KTNIPKVSAY | | 31179 |
| HPV56 | L1 | 10 | 387 | KYDARKINQY | | 31180 |
| HPV56 | L1 | 8 | 77 | LLAVGHPY | | 31181 |
| HPV56 | L1 | 9 | 77 | LLAVGHPYY | | 31182 |
| HPV56 | L1 | 8 | 416 | LSAEVMAY | | 31183 |
| HPV56 | L1 | 9 | 1 | MMLPMMYIY | | 31184 |
| HPV56 | L1 | 11 | 255 | PLDIVQSTCKY | | 31185 |
| HPV56 | L1 | 11 | 467 | PTEKQDPLAKY | | 31186 |
| HPV56 | L1 | 10 | 442 | PVATSLEDKY | | 31187 |
| HPV56 | L1 | 11 | 52 | PVSKVVATDSY | | 31188 |
| HPV56 | L1 | 9 | 260 | QSTCKYPDY | | 31189 |
| HPV56 | L1 | 8 | 40 | RPSENKVY | | 31190 |
| HPV56 | L1 | 10 | 285 | RREQLFARHY | | 31191 |
| HPV56 | L1 | 10 | 336 | SEAQLFNKPY | | 31192 |
| HPV56 | L1 | 8 | 446 | SLEDKYRY | | 31193 |
| HPV56 | L1 | 11 | 74 | SSRLLAVGHPY | | 31194 |
| HPV56 | L1 | 10 | 379 | STATEQLSKY | | 31195 |
| HPV56 | L1 | 8 | 261 | STCKYPDY | | 31196 |
| HPV56 | L1 | 9 | 415 | TLSAEVMAY | | 31197 |
| HPV56 | L1 | 11 | 335 | TSEAQLFNKPY | | 31198 |
| HPV56 | L1 | 9 | 445 | TSLEDKYRY | | 31199 |

TABLE XV-continued

A01 Motif Peptides

| Type | Protein | No. of Amino Acids | Position | Sequence | A*0101 | Seq. Id. No. |
|---|---|---|---|---|---|---|
| HPV56 | L1 | 10 | 301 | VGETIPAELY | | 31200 |
| HPV56 | L1 | 10 | 259 | VQSTCKYPDY | | 31201 |
| HPV56 | L1 | 10 | 53 | VSKVVATDSY | | 31202 |
| HPV56 | L1 | 9 | 388 | YDARKINQY | | 31203 |
| HPV56 | L1 | 8 | 276 | YGDSMWFY | | 31204 |
| HPV56 | L1 | 8 | 9 | YRDPPLHY | | 31205 |
| HPV56 | L2 | 8 | 64 | GSGGRAGY | | 31206 |
| HPV56 | L2 | 10 | 434 | GSSFALWPVY | | 31207 |
| HPV56 | L2 | 10 | 62 | GTGSGGRAGY | | 31208 |
| HPV56 | L2 | 10 | 310 | GTQIGARVHY | | 31209 |
| HPV56 | L2 | 11 | 310 | GTQIGARVHYY | | 31210 |
| HPV56 | L2 | 8 | 313 | IGARVHYY | | 31211 |
| HPV56 | L2 | 9 | 313 | IGARVHYYY | | 31212 |
| HPV56 | L2 | 11 | 182 | ISTPTSGIHSY | | 31213 |
| HPV56 | L2 | 9 | 10 | KRASATQLY | | 31214 |
| HPV56 | L2 | 11 | 338 | LSANNSFDGLY | | 31215 |
| HPV56 | L2 | 8 | 341 | NNSFDGLY | | 31216 |
| HPV56 | L2 | 11 | 341 | NNSFDGLYDIY | | 31217 |
| HPV56 | L2 | 10 | 342 | NSFDGLYDIY | | 31218 |
| HPV56 | L2 | 8 | 185 | PTSGIHSY | | 31219 |
| HPV56 | L2 | 9 | 423 | PYDVTHDVY | | 31220 |
| HPV56 | L2 | 11 | 433 | QGSSFALWPVY | | 31221 |
| HPV56 | L2 | 11 | 421 | QSPYDVTHDVY | | 31222 |
| HPV56 | L2 | 8 | 11 | RASATQLY | | 31223 |
| HPV56 | L2 | 8 | 220 | RIAAPRLY | | 31224 |
| HPV56 | L2 | 8 | 436 | SFALWPVY | | 31225 |
| HPV56 | L2 | 9 | 343 | SFDGLYDIY | | 31226 |
| HPV56 | L2 | 9 | 435 | SSFALWPVY | | 31227 |
| HPV56 | L2 | 10 | 183 | STPTSGIHSY | | 31228 |
| HPV56 | L2 | 11 | 414 | STWPFVPQSPY | | 31229 |
| HPV56 | L2 | 9 | 63 | TGSGGRAGY | | 31230 |

TABLE XVI

A03 Motif Peptides with Binding Data

| Type | Protein | Sequence | Position | No. of Amino Acids | A*0301 | Seq. Id. No. |
|---|---|---|---|---|---|---|
| HPV16 | E1 | AAALYWYK | 316 | 8 | | 31231 |
| HPV16 | E1 | AAFGLTPSIA | 239 | 10 | | 31232 |
| HPV16 | E1 | AAMLAKFK | 205 | 8 | | 31233 |
| HPV16 | E1 | AAMLAKFKELY | 205 | 11 | | 31234 |
| HPV16 | E1 | AANTGKSLF | 478 | 9 | | 31235 |
| HPV16 | E1 | ADAKIGMLDDA | 514 | 11 | | 31236 |
| HPV16 | E1 | ADSIKTLLQQY | 248 | 11 | | 31237 |
| HPV16 | E1 | ADTNSNASA | 383 | 9 | | 31238 |
| HPV16 | E1 | ADTNSNASAF | 383 | 10 | | 31239 |
| HPV16 | E1 | AFGLTPSIA | 240 | 9 | | 31240 |
| HPV16 | E1 | AFLKSNSQA | 391 | 9 | | 31241 |
| HPV16 | E1 | AFLKSNSQAK | 391 | 10 | | 31242 |
| HPV16 | E1 | AGTDSRWPY | 570 | 9 | | 31243 |
| HPV16 | E1 | AGTDSRWPYLH | 570 | 11 | | 31244 |
| HPV16 | E1 | AICIEKQSR | 112 | 9 | 0.0010 | 31245 |
| HPV16 | E1 | AICIEKQSRA | 112 | 10 | | 31246 |
| HPV16 | E1 | AICIEKQSRAA | 112 | 11 | | 31247 |
| HPV16 | E1 | ALFTAQEA | 69 | 8 | | 31248 |
| HPV16 | E1 | ALFTAQEAK | 69 | 9 | 0.2400 | 31249 |
| HPV16 | E1 | ALFTAQEAKQH | 69 | 11 | | 31250 |
| HPV16 | E1 | ALKRFLQGIPK | 459 | 11 | | 31251 |
| HPV16 | E1 | AMLAKFKELY | 206 | 10 | | 31252 |
| HPV16 | E1 | ASAFLKSNSQA | 389 | 11 | | 31253 |
| HPV16 | E1 | ATMCRHYK | 406 | 8 | | 31254 |
| HPV16 | E1 | ATMCRHYKR | 406 | 9 | 0.0660 | 31255 |
| HPV16 | E1 | ATMCRHYKRA | 406 | 10 | | 31256 |
| HPV16 | E1 | ATVPCWNY | 524 | 8 | | 31257 |
| HPV16 | E1 | AVQVLKRK | 82 | 8 | | 31258 |
| HPV16 | E1 | AVQVLKRKY | 82 | 9 | | 31259 |
| HPV16 | E1 | AVVEKKTGDA | 23 | 10 | | 31260 |
| HPV16 | E1 | CATMCRHY | 405 | 8 | | 31261 |
| HPV16 | E1 | CATMCRHYK | 405 | 9 | 0.0012 | 31262 |
| HPV16 | E1 | CATMCRHYKR | 405 | 10 | | 31263 |
| HPV16 | E1 | CATMCRHYKRA | 405 | 11 | | 31264 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E1 | CCDWCIAA | 233 | 8 | | 31265 |
| HPV16 | E1 | CCDWCIAAF | 233 | 9 | | 31266 |
| HPV16 | E1 | CDRVDDGGDWK | 430 | 11 | | 31267 |
| HPV16 | E1 | CDWCIAAF | 234 | 8 | | 31268 |
| HPV16 | E1 | CFVNSKSH | 500 | 8 | | 31269 |
| HPV16 | E1 | CFVNSKSHF | 500 | 9 | | 31270 |
| HPV16 | E1 | CGKNRETIEK | 283 | 10 | | 31271 |
| HPV16 | E1 | CIEKQSRA | 114 | 8 | | 31272 |
| HPV16 | E1 | CIEKQSRAA | 114 | 9 | | 31273 |
| HPV16 | E1 | CIEKQSRAAK | 114 | 10 | | 31274 |
| HPV16 | E1 | CIEKQSRAAKR | 114 | 11 | | 31275 |
| HPV16 | E1 | CILLYGAA | 472 | 8 | | 31276 |
| HPV16 | E1 | CLYLHIQSLA | 259 | 10 | | 31277 |
| HPV16 | E1 | CMMIEPPK | 304 | 8 | | 31278 |
| HPV16 | E1 | CMMIEPPKLR | 304 | 10 | | 31279 |
| HPV16 | E1 | CVDNNISPR | 101 | 9 | | 31280 |
| HPV16 | E1 | CVDNNISPRLK | 101 | 11 | | 31281 |
| HPV16 | E1 | DAKIGMLDDA | 515 | 10 | | 31282 |
| HPV16 | E1 | DATVPCWNY | 523 | 9 | | 31283 |
| HPV16 | E1 | DAVQVLKR | 81 | 8 | | 31284 |
| HPV16 | E1 | DAVQVLKRK | 81 | 9 | | 31285 |
| HPV16 | E1 | DAVQVLKRKY | 81 | 10 | | 31286 |
| HPV16 | E1 | DCATMCRH | 404 | 8 | | 31287 |
| HPV16 | E1 | DCATMCRHY | 404 | 9 | 0.0001 | 31288 |
| HPV16 | E1 | DCATMCRHYK | 404 | 10 | 0.0044 | 31289 |
| HPV16 | E1 | DCATMCRHYKR | 404 | 11 | | 31290 |
| HPV16 | E1 | DDATVPCWNY | 522 | 10 | | 31291 |
| HPV16 | E1 | DDSEIAYK | 371 | 8 | | 31292 |
| HPV16 | E1 | DDSEIAYKY | 371 | 9 | | 31293 |
| HPV16 | E1 | DDSEIAYKYA | 371 | 10 | | 31294 |
| HPV16 | E1 | DFIVNDNDY | 50 | 9 | | 31295 |
| HPV16 | E1 | DGDSLPTF | 631 | 8 | | 31296 |
| HPV16 | E1 | DGDSLPTFK | 631 | 9 | | 31297 |
| HPV16 | E1 | DGGDWKQIVMF | 435 | 11 | | 31298 |
| HPV16 | E1 | DGNLVSMDVK | 541 | 10 | | 31299 |
| HPV16 | E1 | DGNLVSMDVKH | 541 | 11 | | 31300 |
| HPV16 | E1 | DIVDDSEIA | 368 | 9 | | 31301 |
| HPV16 | E1 | DIVDDSEIAY | 368 | 10 | | 31302 |
| HPV16 | E1 | DIVDDSEIAYK | 368 | 11 | | 31303 |
| HPV16 | E1 | DSDTGEDLVDF | 41 | 11 | | 31304 |
| HPV16 | E1 | DSEIAYKY | 372 | 8 | | 31305 |
| HPV16 | E1 | DSEIAYKYA | 372 | 9 | | 31306 |
| HPV16 | E1 | DSIKTLLQQY | 249 | 10 | | 31307 |
| HPV16 | E1 | DSRWPYLH | 573 | 8 | | 31308 |
| HPV16 | E1 | DSRWPYLHNR | 573 | 10 | | 31309 |
| HPV16 | E1 | DTGEDLVDF | 43 | 9 | | 31310 |
| HPV16 | E1 | DTNSNASA | 384 | 8 | | 31311 |
| HPV16 | E1 | DTNSNASAF | 384 | 9 | | 31312 |
| HPV16 | E1 | DTNSNASAFLK | 384 | 11 | | 31313 |
| HPV16 | E1 | DTPEWIQR | 335 | 8 | | 31314 |
| HPV16 | E1 | DVKHRPLVQLK | 548 | 11 | | 31315 |
| HPV16 | E1 | EAKQHRDA | 75 | 8 | | 31316 |
| HPV16 | E1 | EAVVEKKTGDA | 22 | 11 | | 31317 |
| HPV16 | E1 | EFMSFLTA | 452 | 8 | | 31318 |
| HPV16 | E1 | EFMSFLTALK | 452 | 10 | | 31319 |
| HPV16 | E1 | EFMSFLTALKR | 452 | 11 | | 31320 |
| HPV16 | E1 | EGTGCNGWF | 11 | 9 | 0.0008 | 31321 |
| HPV16 | E1 | EGTGCNGWFY | 11 | 10 | 0.0005 | 31322 |
| HPV16 | E1 | EIAYKYAQLA | 374 | 10 | | 31323 |
| HPV16 | E1 | ELNDKNWK | 603 | 8 | | 31324 |
| HPV16 | E1 | ELNDKNWKSF | 603 | 10 | | 31325 |
| HPV16 | E1 | ELNDKNWKSFF | 603 | 11 | | 31326 |
| HPV16 | E1 | ELSQMVQWA | 356 | 9 | | 31327 |
| HPV16 | E1 | ELSQMVQWAY | 356 | 10 | | 31328 |
| HPV16 | E1 | ELVRPFKSNK | 221 | 10 | | 31329 |
| HPV16 | E1 | ETAHALFTA | 65 | 9 | | 31330 |
| HPV16 | E1 | ETETAHALF | 63 | 9 | | 31331 |
| HPV16 | E1 | ETETAHALFTA | 63 | 11 | | 31332 |
| HPV16 | E1 | ETETPCSQY | 152 | 9 | | 31333 |
| HPV16 | E1 | ETIEKLLSK | 288 | 9 | | 31334 |
| HPV16 | E1 | ETQQMLQVEGR | 140 | 11 | | 31335 |
| HPV16 | E1 | FDENGNPVY | 594 | 9 | | 31336 |
| HPV16 | E1 | FFSRTWSR | 612 | 8 | | 31337 |
| HPV16 | E1 | FGLTPSIA | 241 | 8 | | 31338 |
| HPV16 | E1 | FGMSLMKF | 486 | 8 | | 31339 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E1 | FIVNDNDY | 51 | 8 | | 31340 |
| HPV16 | E1 | FLKSNSQA | 392 | 8 | | 31341 |
| HPV16 | E1 | FLKSNSQAK | 392 | 9 | 0.0013 | 31342 |
| HPV16 | E1 | FLQGIPKK | 463 | 8 | | 31343 |
| HPV16 | E1 | FLQGSVICF | 493 | 9 | | 31344 |
| HPV16 | E1 | FLRYQGVEF | 445 | 9 | | 31345 |
| HPV16 | E1 | FLTALKRF | 456 | 8 | | 31346 |
| HPV16 | E1 | FMSFLTALK | 453 | 9 | 0.1300 | 31347 |
| HPV16 | E1 | FMSFLTALKR | 453 | 10 | | 31348 |
| HPV16 | E1 | FMSFLTALKRF | 453 | 11 | | 31349 |
| HPV16 | E1 | FSELVRPF | 219 | 8 | | 31350 |
| HPV16 | E1 | FSELVRPFK | 219 | 9 | | 31351 |
| HPV16 | E1 | FSRTWSRLSLH | 613 | 11 | | 31352 |
| HPV16 | E1 | FTAQEAKQH | 71 | 9 | | 31353 |
| HPV16 | E1 | FTAQEAKQHR | 71 | 10 | | 31354 |
| HPV16 | E1 | FTFPNEFPF | 586 | 9 | | 31355 |
| HPV16 | E1 | FVNSKSHF | 501 | 8 | | 31356 |
| HPV16 | E1 | GAANTGKSLF | 477 | 10 | | 31357 |
| HPV16 | E1 | GCNGWFYVEA | 14 | 10 | | 31358 |
| HPV16 | E1 | GCVDNNISPR | 100 | 10 | | 31359 |
| HPV16 | E1 | GDSLPTFK | 632 | 8 | | 31360 |
| HPV16 | E1 | GDTPEWIQR | 334 | 9 | 0.0008 | 31361 |
| HPV16 | E1 | GDWKQIVMF | 437 | 9 | | 31362 |
| HPV16 | E1 | GDWKQIVMFLR | 437 | 11 | | 31363 |
| HPV16 | E1 | GGDWKQIVMF | 436 | 10 | | 31364 |
| HPV16 | E1 | GGEGVSER | 176 | 8 | | 31365 |
| HPV16 | E1 | GGEGVSERH | 176 | 9 | | 31366 |
| HPV16 | E1 | GGSGGGCSQY | 162 | 10 | | 31367 |
| HPV16 | E1 | GIPKKNCILLY | 466 | 11 | | 31368 |
| HPV16 | E1 | GISNISEVY | 325 | 9 | | 31369 |
| HPV16 | E1 | GLTPSIADSIK | 242 | 11 | | 31370 |
| HPV16 | E1 | GMVVLLLVR | 272 | 9 | 0.0036 | 31371 |
| HPV16 | E1 | GMVVLLLVRY | 272 | 10 | | 31372 |
| HPV16 | E1 | GMVVLLLVRYK | 272 | 11 | | 31373 |
| HPV16 | E1 | GSGGEGVSER | 174 | 10 | | 31374 |
| HPV16 | E1 | GSGGEGVSERH | 174 | 11 | | 31375 |
| HPV16 | E1 | GSGGGCSQY | 163 | 9 | | 31376 |
| HPV16 | E1 | GSVICFVNSK | 496 | 10 | | 31377 |
| HPV16 | E1 | GTDSRWPY | 571 | 8 | | 31378 |
| HPV16 | E1 | GTDSRWPYLH | 571 | 10 | | 31379 |
| HPV16 | E1 | GTGCNGWF | 12 | 8 | | 31380 |
| HPV16 | E1 | GTGCNGWFY | 12 | 9 | 0.0004 | 31381 |
| HPV16 | E1 | GVEFMSFLTA | 450 | 10 | | 31382 |
| HPV16 | E1 | GVSFSELVR | 216 | 9 | 0.0011 | 31383 |
| HPV16 | E1 | GVSFSELVRPF | 216 | 11 | | 31384 |
| HPV16 | E1 | HALFTAQEA | 68 | 9 | | 31385 |
| HPV16 | E1 | HALFTAQEAK | 68 | 10 | | 31386 |
| HPV16 | E1 | HFWLQPLA | 507 | 8 | | 31387 |
| HPV16 | E1 | HFWLQPLADA | 507 | 10 | | 31388 |
| HPV16 | E1 | HFWLQPLADAK | 507 | 11 | | 31389 |
| HPV16 | E1 | HSFNDCTF | 348 | 8 | | 31390 |
| HPV16 | E1 | IAAFGLTPSIA | 238 | 11 | | 31391 |
| HPV16 | E1 | IAYKYAQLA | 375 | 9 | | 31392 |
| HPV16 | E1 | ICFVNSKSH | 499 | 9 | | 31393 |
| HPV16 | E1 | ICFVNSKSHF | 499 | 10 | | 31394 |
| HPV16 | E1 | ICIEKQSR | 113 | 8 | | 31395 |
| HPV16 | E1 | ICIEKQSRA | 113 | 9 | | 31396 |
| HPV16 | E1 | ICIEKQSRAA | 113 | 10 | | 31397 |
| HPV16 | E1 | ICIEKQSRAAK | 113 | 11 | | 31398 |
| HPV16 | E1 | IDDNLRNA | 532 | 8 | | 31399 |
| HPV16 | E1 | ILLYGAANTGK | 473 | 11 | | 31400 |
| HPV16 | E1 | ILNVLKTSNA | 194 | 10 | | 31401 |
| HPV16 | E1 | ILNVLKTSNAK | 194 | 11 | | 31402 |
| HPV16 | E1 | ISNISEVY | 326 | 8 | | 31403 |
| HPV16 | E1 | IVDDSEIA | 369 | 8 | | 31404 |
| HPV16 | E1 | IVDDSEIAY | 369 | 9 | | 31405 |
| HPV16 | E1 | IVDDSEIAYK | 369 | 10 | | 31406 |
| HPV16 | E1 | IVDDSEIAYKY | 369 | 11 | | 31407 |
| HPV16 | E1 | IVKDCATMCR | 401 | 10 | | 31408 |
| HPV16 | E1 | IVKDCATMCRH | 401 | 11 | | 31409 |
| HPV16 | E1 | IVNDNDYLTQA | 52 | 11 | | 31410 |
| HPV16 | E1 | KAAMLAKF | 204 | 8 | | 31411 |
| HPV16 | E1 | KAAMLAKFK | 204 | 9 | 0.1100 | 31412 |
| HPV16 | E1 | KAICIEKQSR | 111 | 10 | | 31413 |
| HPV16 | E1 | KAICIEKQSRA | 111 | 11 | | 31414 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E1 | KCGKNRETIEK | 282 | 11 | | 31415 |
| HPV16 | E1 | KDCATMCR | 403 | 8 | | 31416 |
| HPV16 | E1 | KDCATMCRH | 403 | 9 | 0.0011 | 31417 |
| HPV16 | E1 | KDCATMCRHY | 403 | 10 | 0.0005 | 31418 |
| HPV16 | E1 | KDCATMCRHYK | 403 | 11 | | 31419 |
| HPV16 | E1 | KFKELYGVSF | 210 | 10 | | 31420 |
| HPV16 | E1 | KFLQGSVICF | 492 | 10 | | 31421 |
| HPV16 | E1 | KIGMLDDA | 517 | 8 | | 31422 |
| HPV16 | E1 | KIVKDCATMCR | 400 | 11 | | 31423 |
| HPV16 | E1 | KLRSTAAA | 311 | 8 | | 31424 |
| HPV16 | E1 | KLRSTAAALY | 311 | 10 | | 31425 |
| HPV16 | E1 | KSFFSRTWSR | 610 | 10 | | 31426 |
| HPV16 | E1 | KSHFWLQPLA | 505 | 10 | | 31427 |
| HPV16 | E1 | KSLFGMSLMK | 483 | 10 | | 31428 |
| HPV16 | E1 | KSLFGMSLMKF | 483 | 11 | | 31429 |
| HPV16 | E1 | KSNSQAKIVK | 394 | 10 | | 31430 |
| HPV16 | E1 | KSTCCDWCIA | 230 | 10 | | 31431 |
| HPV16 | E1 | KSTCCDWCIAA | 230 | 11 | | 31432 |
| HPV16 | E1 | KTGISNISEVY | 323 | 11 | | 31433 |
| HPV16 | E1 | KTLLQQYCLY | 252 | 10 | | 31434 |
| HPV16 | E1 | KTSNAKAA | 199 | 8 | | 31435 |
| HPV16 | E1 | KTSNAKAAMLA | 199 | 11 | | 31436 |
| HPV16 | E1 | LADTNSNA | 382 | 8 | | 31437 |
| HPV16 | E1 | LADTNSNASA | 382 | 10 | | 31438 |
| HPV16 | E1 | LADTNSNASAF | 382 | 11 | | 31439 |
| HPV16 | E1 | LAKFKELY | 208 | 8 | | 31440 |
| HPV16 | E1 | LDDATVPCWNY | 521 | 11 | | 31441 |
| HPV16 | E1 | LDGNLVSMDVK | 540 | 11 | | 31442 |
| HPV16 | E1 | LFESEDSGY | 126 | 9 | | 31443 |
| HPV16 | E1 | LFGMSLMK | 485 | 8 | | 31444 |
| HPV16 | E1 | LFGMSLMKF | 485 | 9 | | 31445 |
| HPV16 | E1 | LFTAQEAK | 70 | 8 | | 31446 |
| HPV16 | E1 | LFTAQEAKQH | 70 | 10 | | 31447 |
| HPV16 | E1 | LFTAQEAKQHR | 70 | 11 | | 31448 |
| HPV16 | E1 | LITSNINA | 563 | 8 | | 31449 |
| HPV16 | E1 | LLITSNINA | 562 | 9 | | 31450 |
| HPV16 | E1 | LLLVRYKCGK | 276 | 10 | | 31451 |
| HPV16 | E1 | LLQQYCLY | 254 | 8 | | 31452 |
| HPV16 | E1 | LLQQYCLYLH | 254 | 10 | | 31453 |
| HPV16 | E1 | LLVRYKCGK | 277 | 9 | 0.0043 | 31454 |
| HPV16 | E1 | LLVRYKCGKNR | 277 | 11 | | 31455 |
| HPV16 | E1 | LLYGAANTGK | 474 | 10 | | 31456 |
| HPV16 | E1 | LSLHEDEDK | 620 | 9 | 0.0005 | 31457 |
| HPV16 | E1 | LSQMVQWA | 357 | 8 | | 31458 |
| HPV16 | E1 | LSQMVQWAY | 357 | 9 | | 31459 |
| HPV16 | E1 | LTNILNVLK | 191 | 9 | 0.0086 | 31460 |
| HPV16 | E1 | LTPSIADSIK | 243 | 10 | | 31461 |
| HPV16 | E1 | LTQAETETA | 59 | 9 | | 31462 |
| HPV16 | E1 | LTQAETETAH | 59 | 10 | | 31463 |
| HPV16 | E1 | LTQAETETAHA | 59 | 11 | | 31464 |
| HPV16 | E1 | LVDFIVNDNDY | 48 | 11 | | 31465 |
| HPV16 | E1 | LVRPFKSNK | 222 | 9 | 0.0700 | 31466 |
| HPV16 | E1 | LVRYKCGK | 278 | 8 | | 31467 |
| HPV16 | E1 | LVRYKCGKNR | 278 | 10 | | 31468 |
| HPV16 | E1 | LVSMDVKH | 544 | 8 | | 31469 |
| HPV16 | E1 | LVSMDVKHR | 544 | 9 | 0.0005 | 31470 |
| HPV16 | E1 | LVVFTFPNEF | 583 | 10 | | 31471 |
| HPV16 | E1 | MCMMIEPPK | 303 | 9 | | 31472 |
| HPV16 | E1 | MCMMIEPPKLR | 303 | 11 | | 31473 |
| HPV16 | E1 | MCRHYKRA | 408 | 8 | | 31474 |
| HPV16 | E1 | MCRHYKRAEK | 408 | 10 | | 31475 |
| HPV16 | E1 | MCRHYKRAEKK | 408 | 11 | | 31476 |
| HPV16 | E1 | MFLRYQGVEF | 444 | 10 | | 31477 |
| HPV16 | E1 | MIEPPKLR | 306 | 8 | | 31478 |
| HPV16 | E1 | MIEPPKLRSTA | 306 | 11 | | 31479 |
| HPV16 | E1 | MLAKFKELY | 207 | 9 | | 31480 |
| HPV16 | E1 | MLQVEGRH | 144 | 8 | | 31481 |
| HPV16 | E1 | MMIEPPKLR | 305 | 9 | 0.0010 | 31482 |
| HPV16 | E1 | MSFLTALK | 454 | 8 | | 31483 |
| HPV16 | E1 | MSFLTALKR | 454 | 9 | 0.0870 | 31484 |
| HPV16 | E1 | MSFLTALKRF | 454 | 10 | | 31485 |
| HPV16 | E1 | MSMSQWIK | 420 | 8 | | 31486 |
| HPV16 | E1 | MSMSQWIKY | 420 | 9 | | 31487 |
| HPV16 | E1 | MSMSQWIKYR | 420 | 10 | | 31488 |
| HPV16 | E1 | MSQWIKYR | 422 | 8 | | 31489 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E1 | MSQWIKYRCDR | 422 | 11 | | 31490 |
| HPV16 | E1 | MVVLLLVR | 273 | 8 | | 31491 |
| HPV16 | E1 | MVVLLLVRY | 273 | 9 | | 31492 |
| HPV16 | E1 | MVVLLLVRYK | 273 | 10 | | 31493 |
| HPV16 | E1 | NAGTDSRWPY | 569 | 10 | | 31494 |
| HPV16 | E1 | NAKAAMLA | 202 | 8 | | 31495 |
| HPV16 | E1 | NAKAAMLAK | 202 | 9 | 0.0005 | 31496 |
| HPV16 | E1 | NAKAAMLAKF | 202 | 10 | | 31497 |
| HPV16 | E1 | NAKAAMLAKFK | 202 | 11 | | 31498 |
| HPV16 | E1 | NCILLYGA | 471 | 8 | | 31499 |
| HPV16 | E1 | NCILLYGAA | 471 | 9 | | 31500 |
| HPV16 | E1 | NDGDSLPTF | 630 | 9 | | 31501 |
| HPV16 | E1 | NDGDSLPTFK | 630 | 10 | | 31502 |
| HPV16 | E1 | NDIVDDSEIA | 367 | 10 | | 31503 |
| HPV16 | E1 | NDIVDDSEIAY | 367 | 11 | | 31504 |
| HPV16 | E1 | NDKNWKSF | 605 | 8 | | 31505 |
| HPV16 | E1 | NDKNWKSFF | 605 | 9 | | 31506 |
| HPV16 | E1 | NDKNWKSFFSR | 605 | 11 | | 31507 |
| HPV16 | E1 | NDNDYLTQA | 54 | 9 | | 31508 |
| HPV16 | E1 | NGNPVYELNDK | 597 | 11 | | 31509 |
| HPV16 | E1 | NGWFYVEA | 16 | 8 | | 31510 |
| HPV16 | E1 | NILNVLKTSNA | 193 | 11 | | 31511 |
| HPV16 | E1 | NINAGTDSR | 567 | 9 | 0.0005 | 31512 |
| HPV16 | E1 | NISPRLKA | 105 | 8 | | 31513 |
| HPV16 | E1 | NLVSMDVK | 543 | 8 | | 31514 |
| HPV16 | E1 | NLVSMDVKH | 543 | 9 | | 31515 |
| HPV16 | E1 | NLVSMDVKHR | 543 | 10 | | 31516 |
| HPV16 | E1 | NSNASAFLK | 386 | 9 | 0.0005 | 31517 |
| HPV16 | E1 | NSQAKIVK | 396 | 8 | | 31518 |
| HPV16 | E1 | NSQAKIVKDCA | 396 | 11 | | 31519 |
| HPV16 | E1 | NVLKTSNA | 196 | 8 | | 31520 |
| HPV16 | E1 | NVLKTSNAK | 196 | 9 | 0.0005 | 31521 |
| HPV16 | E1 | NVLKTSNAKA | 196 | 10 | | 31522 |
| HPV16 | E1 | NVLKTSNAKAA | 196 | 11 | | 31523 |
| HPV16 | E1 | PCWNYIDDNLR | 527 | 11 | | 31524 |
| HPV16 | E1 | PFDENGNPVY | 593 | 10 | | 31525 |
| HPV16 | E1 | PLLITSNINA | 561 | 10 | | 31526 |
| HPV16 | E1 | PLTNILNVLK | 190 | 10 | | 31527 |
| HPV16 | E1 | PMCMMIEPPK | 302 | 10 | | 31528 |
| HPV16 | E1 | PSIADSIK | 245 | 8 | | 31529 |
| HPV16 | E1 | PVYELNDK | 600 | 8 | | 31530 |
| HPV16 | E1 | PVYELNDKNWK | 600 | 11 | | 31531 |
| HPV16 | E1 | QAETETAH | 61 | 8 | | 31532 |
| HPV16 | E1 | QAETETAHA | 61 | 9 | | 31533 |
| HPV16 | E1 | QAETETAHALF | 61 | 11 | | 31534 |
| HPV16 | E1 | QAKIVKDCA | 398 | 9 | | 31535 |
| HPV16 | E1 | QGSVICFVNSK | 495 | 11 | | 31536 |
| HPV16 | E1 | QGVEFMSF | 449 | 8 | | 31537 |
| HPV16 | E1 | QGVEFMSFLTA | 449 | 11 | | 31538 |
| HPV16 | E1 | QIVMFLRY | 441 | 8 | | 31539 |
| HPV16 | E1 | QLADTNSNA | 381 | 9 | | 31540 |
| HPV16 | E1 | QLADTNSNASA | 381 | 11 | | 31541 |
| HPV16 | E1 | QMLQVEGR | 143 | 8 | | 31542 |
| HPV16 | E1 | QMLQVEGRH | 143 | 9 | | 31543 |
| HPV16 | E1 | QMSMSQWIK | 419 | 9 | 0.0023 | 31544 |
| HPV16 | E1 | QMSMSQWIKY | 419 | 10 | | 31545 |
| HPV16 | E1 | QMSMSQWIKYR | 419 | 11 | | 31546 |
| HPV16 | E1 | QSRAAKRR | 118 | 8 | | 31547 |
| HPV16 | E1 | QSRAAKRRLF | 118 | 10 | | 31548 |
| HPV16 | E1 | QTVLQHSF | 343 | 8 | | 31549 |
| HPV16 | E1 | RAAKRRLF | 120 | 8 | | 31550 |
| HPV16 | E1 | RDAVQVLK | 80 | 8 | | 31551 |
| HPV16 | E1 | RDAVQVLKR | 80 | 9 | | 31552 |
| HPV16 | E1 | RDAVQVLKRK | 80 | 10 | | 31553 |
| HPV16 | E1 | RDAVQVLKRKY | 80 | 11 | | 31554 |
| HPV16 | E1 | RFLQGIPK | 462 | 8 | | 31555 |
| HPV16 | E1 | RFLQGIPKK | 462 | 9 | | 31556 |
| HPV16 | E1 | RLFESEDSGY | 125 | 10 | | 31557 |
| HPV16 | E1 | RLKAICIEK | 109 | 9 | 0.0840 | 31558 |
| HPV16 | E1 | RLSLHEDEDK | 619 | 10 | | 31559 |
| HPV16 | E1 | RLVVFTFPNEF | 582 | 11 | | 31560 |
| HPV16 | E1 | RSTAAALY | 313 | 8 | | 31561 |
| HPV16 | E1 | RSTAAALYWY | 313 | 10 | | 31562 |
| HPV16 | E1 | RSTAAALYWYK | 313 | 11 | | 31563 |
| HPV16 | E1 | RTWSRLSLH | 615 | 9 | | 31564 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E1 | RVDDGGDWK | 432 | 9 | | 31565 |
| HPV16 | E1 | SAFLKSNSQA | 390 | 10 | | 31566 |
| HPV16 | E1 | SAFLKSNSQAK | 390 | 11 | | 31567 |
| HPV16 | E1 | SDTGEDLVDF | 42 | 10 | | 31568 |
| HPV16 | E1 | SFFSRTWSR | 611 | 9 | | 31569 |
| HPV16 | E1 | SFLTALKR | 455 | 8 | | 31570 |
| HPV16 | E1 | SFLTALKRF | 455 | 9 | | 31571 |
| HPV16 | E1 | SFSELVRPF | 218 | 9 | | 31572 |
| HPV16 | E1 | SFSELVRPFK | 218 | 10 | | 31573 |
| HPV16 | E1 | SGCVDNNISPR | 99 | 11 | | 31574 |
| HPV16 | E1 | SGGEGVSER | 175 | 9 | | 31575 |
| HPV16 | E1 | SGGEGVSERH | 175 | 10 | | 31576 |
| HPV16 | E1 | SGGGCSQY | 164 | 8 | | 31577 |
| HPV16 | E1 | SGGSGGGCSQY | 161 | 11 | | 31578 |
| HPV16 | E1 | SGSGGEGVSER | 173 | 11 | | 31579 |
| HPV16 | E1 | SIKTLLQQY | 250 | 9 | | 31580 |
| HPV16 | E1 | SLFGMSLMK | 484 | 9 | 0.7200 | 31581 |
| HPV16 | E1 | SLFGMSLMKF | 484 | 10 | | 31582 |
| HPV16 | E1 | SLHEDEDK | 621 | 8 | | 31583 |
| HPV16 | E1 | SMSQWIKY | 421 | 8 | | 31584 |
| HPV16 | E1 | SMSQWIKYR | 421 | 9 | 0.6900 | 31585 |
| HPV16 | E1 | STAAALYWY | 314 | 9 | | 31586 |
| HPV16 | E1 | STAAALYWYK | 314 | 10 | | 31587 |
| HPV16 | E1 | STCCDWCIA | 231 | 9 | | 31588 |
| HPV16 | E1 | STCCDWCIAA | 231 | 10 | | 31589 |
| HPV16 | E1 | STCCDWCIAAF | 231 | 11 | | 31590 |
| HPV16 | E1 | SVICFVNSK | 497 | 9 | 0.0005 | 31591 |
| HPV16 | E1 | SVICFVNSKSH | 497 | 11 | | 31592 |
| HPV16 | E1 | TAAALYWY | 315 | 8 | | 31593 |
| HPV16 | E1 | TAAALYWYK | 315 | 9 | 0.7800 | 31594 |
| HPV16 | E1 | TAHALFTA | 66 | 8 | | 31595 |
| HPV16 | E1 | TAHALFTAQEA | 66 | 11 | | 31596 |
| HPV16 | E1 | TAQEAKQH | 72 | 8 | | 31597 |
| HPV16 | E1 | TAQEAKQHR | 72 | 9 | 0.0005 | 31598 |
| HPV16 | E1 | TAQEAKQHRDA | 72 | 11 | | 31599 |
| HPV16 | E1 | TCCDWCIA | 232 | 8 | | 31600 |
| HPV16 | E1 | TCCDWCIAA | 232 | 9 | | 31601 |
| HPV16 | E1 | TCCDWCIAAF | 232 | 10 | | 31602 |
| HPV16 | E1 | TDSRWPYLH | 572 | 9 | | 31603 |
| HPV16 | E1 | TDSRWPYLHNR | 572 | 11 | | 31604 |
| HPV16 | E1 | TFELSQMVQWA | 354 | 11 | | 31605 |
| HPV16 | E1 | TFPNEFPF | 587 | 8 | | 31606 |
| HPV16 | E1 | TGCNGWFY | 13 | 8 | | 31607 |
| HPV16 | E1 | TGCNGWFYVEA | 13 | 11 | | 31608 |
| HPV16 | E1 | TGEDLVDF | 44 | 8 | | 31609 |
| HPV16 | E1 | TGISNISEVY | 324 | 10 | | 31610 |
| HPV16 | E1 | TIEKLLSK | 289 | 8 | | 31611 |
| HPV16 | E1 | TLLQQYCLY | 253 | 9 | | 31612 |
| HPV16 | E1 | TLLQQYCLYH | 253 | 11 | | 31613 |
| HPV16 | E1 | TMCRHYKR | 407 | 8 | | 31614 |
| HPV16 | E1 | TMCRHYKRA | 407 | 9 | | 31615 |
| HPV16 | E1 | TMCRHYKRAEK | 407 | 11 | | 31616 |
| HPV16 | E1 | TSNAKAAMLA | 200 | 10 | | 31617 |
| HPV16 | E1 | TSNAKAAMLAK | 200 | 11 | | 31618 |
| HPV16 | E1 | TSNINAGTDSR | 565 | 11 | | 31619 |
| HPV16 | E1 | VDDGGDWK | 433 | 8 | | 31620 |
| HPV16 | E1 | VDDSEIAY | 370 | 8 | | 31621 |
| HPV16 | E1 | VDDSEIAYK | 370 | 9 | | 31622 |
| HPV16 | E1 | VDDSEIAYKY | 370 | 10 | | 31623 |
| HPV16 | E1 | VDDSEIAYKYA | 370 | 11 | | 31624 |
| HPV16 | E1 | VDFIVNDNDY | 49 | 10 | | 31625 |
| HPV16 | E1 | VDNNISPR | 102 | 8 | | 31626 |
| HPV16 | E1 | VDNNISPRLK | 102 | 10 | | 31627 |
| HPV16 | E1 | VDNNISPRLKA | 102 | 11 | | 31628 |
| HPV16 | E1 | VFTFPNEF | 585 | 8 | | 31629 |
| HPV16 | E1 | VFTFPNEFPF | 585 | 10 | | 31630 |
| HPV16 | E1 | VICFVNSK | 498 | 8 | | 31631 |
| HPV16 | E1 | VICFVNSKSH | 498 | 10 | | 31632 |
| HPV16 | E1 | VICFVNSKSHF | 498 | 11 | | 31633 |
| HPV16 | E1 | VLKTSNAK | 197 | 8 | | 31634 |
| HPV16 | E1 | VLKTSNAKA | 197 | 9 | | 31635 |
| HPV16 | E1 | VLKTSNAKAA | 197 | 10 | | 31636 |
| HPV16 | E1 | VLLLVRYK | 275 | 8 | | 31637 |
| HPV16 | E1 | VLLLVRYKCGK | 275 | 11 | | 31638 |
| HPV16 | E1 | VLQHSFNDCTF | 345 | 11 | | 31639 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E1 | VMFLRYQGVEF | 443 | 11 | | 31640 |
| HPV16 | E1 | VSFSELVR | 217 | 8 | | 31641 |
| HPV16 | E1 | VSFSELVRPF | 217 | 10 | | 31642 |
| HPV16 | E1 | VSFSELVRPFK | 217 | 11 | | 31643 |
| HPV16 | E1 | VSMDVKHR | 545 | 8 | | 31644 |
| HPV16 | E1 | VVEKKTGDA | 24 | 9 | | 31645 |
| HPV16 | E1 | VVFTFPNEF | 584 | 9 | | 31646 |
| HPV16 | E1 | VVFTFPNEFPF | 584 | 11 | | 31647 |
| HPV16 | E1 | VVLLLVRY | 274 | 8 | | 31648 |
| HPV16 | E1 | VVLLLVRYK | 274 | 9 | 1.0000 | 31649 |
| HPV16 | E1 | WFYVEAVVEK | 18 | 10 | | 31650 |
| HPV16 | E1 | WFYVEAVVEKK | 18 | 11 | | 31651 |
| HPV16 | E1 | WGMVVLLLVR | 271 | 10 | | 31652 |
| HPV16 | E1 | WGMVVLLLVRY | 271 | 11 | | 31653 |
| HPV16 | E1 | WIKYRCDR | 425 | 8 | | 31654 |
| HPV16 | E1 | WIQRQTVLQH | 339 | 10 | | 31655 |
| HPV16 | E1 | WLQPLADA | 509 | 8 | | 31656 |
| HPV16 | E1 | WLQPLADAK | 509 | 9 | 0.0005 | 31657 |
| HPV16 | E1 | YAQLADTNSNA | 379 | 11 | | 31658 |
| HPV16 | E1 | YCLYLHIQSLA | 258 | 11 | | 31659 |
| HPV16 | E1 | YGAANTGK | 476 | 8 | | 31660 |
| HPV16 | E1 | YGAANTGKSLF | 476 | 11 | | 31661 |
| HPV16 | E1 | YGDTPEWIQR | 333 | 10 | | 31662 |
| HPV16 | E1 | YGVSFSELVR | 215 | 10 | | 31663 |
| HPV16 | E1 | YIDDNLRNA | 531 | 9 | | 31664 |
| HPV16 | E1 | YLHIQSLA | 261 | 8 | | 31665 |
| HPV16 | E1 | YLHNRLVVF | 578 | 9 | | 31666 |
| HPV16 | E1 | YLHNRLVVFTF | 578 | 11 | | 31667 |
| HPV16 | E1 | YLTQAETETA | 58 | 10 | | 31668 |
| HPV16 | E1 | YLTQAETETAH | 58 | 11 | | 31669 |
| HPV16 | E1 | YVEAVVEK | 20 | 8 | | 31670 |
| HPV16 | E1 | YVEAVVEKK | 20 | 9 | | 31671 |
| HPV16 | E2 | AATHTKAVA | 220 | 9 | | 31672 |
| HPV16 | E2 | AFNSSHKGR | 270 | 9 | | 31673 |
| HPV16 | E2 | AIYYKAREMGF | 41 | 11 | | 31674 |
| HPV16 | E2 | ATHTKAVA | 221 | 8 | | 31675 |
| HPV16 | E2 | AVSKNKALQA | 63 | 10 | | 31676 |
| HPV16 | E2 | AVSSTWHWTGH | 314 | 11 | | 31677 |
| HPV16 | E2 | CAIYYKAR | 40 | 8 | | 31678 |
| HPV16 | E2 | CLRYRFKK | 300 | 8 | | 31679 |
| HPV16 | E2 | CLRYRFKKH | 300 | 9 | | 31680 |
| HPV16 | E2 | DAEKYSKNK | 174 | 9 | | 31681 |
| HPV16 | E2 | DANTLKCLR | 294 | 9 | | 31682 |
| HPV16 | E2 | DANTLKCLRY | 294 | 10 | | 31683 |
| HPV16 | E2 | DANTLKCLRYR | 294 | 11 | | 31684 |
| HPV16 | E2 | DDAEKYSK | 173 | 8 | | 31685 |
| HPV16 | E2 | DDAEKYSKNK | 173 | 10 | | 31686 |
| HPV16 | E2 | DGDICNTMH | 122 | 9 | | 31687 |
| HPV16 | E2 | DGDICNTMHY | 122 | 10 | | 31688 |
| HPV16 | E2 | DICNTMHY | 124 | 8 | | 31689 |
| HPV16 | E2 | DLRDHIDY | 25 | 8 | | 31690 |
| HPV16 | E2 | DLRDHIDYWK | 25 | 10 | | 31691 |
| HPV16 | E2 | DLRDHIDYWKH | 25 | 11 | | 31692 |
| HPV16 | E2 | DSAPILTA | 263 | 8 | | 31693 |
| HPV16 | E2 | DSAPILTAF | 263 | 9 | | 31694 |
| HPV16 | E2 | DSEWQRDQF | 338 | 9 | | 31695 |
| HPV16 | E2 | DSTDLRDH | 22 | 8 | | 31696 |
| HPV16 | E2 | DSTDLRDHIDY | 22 | 11 | | 31697 |
| HPV16 | E2 | DSVDSAPILTA | 260 | 11 | | 31698 |
| HPV16 | E2 | DTGNPCHTTK | 246 | 10 | | 31699 |
| HPV16 | E2 | DVSLEVYLTA | 96 | 10 | | 31700 |
| HPV16 | E2 | ECAIYYKA | 39 | 8 | | 31701 |
| HPV16 | E2 | ECAIYYKAR | 39 | 9 | | 31702 |
| HPV16 | E2 | EGIRTYFVQF | 162 | 10 | | 31703 |
| HPV16 | E2 | EGIRTYFVQFK | 162 | 11 | | 31704 |
| HPV16 | E2 | EGQVDYYGLY | 149 | 10 | | 31705 |
| HPV16 | E2 | EGQVDYYGLYY | 149 | 11 | | 31706 |
| HPV16 | E2 | EIIRQHLA | 209 | 8 | | 31707 |
| HPV16 | E2 | EIIRQHLANH | 209 | 10 | | 31708 |
| HPV16 | E2 | ELQLTLETIY | 74 | 10 | | 31709 |
| HPV16 | E2 | EMGFKHINH | 48 | 9 | | 31710 |
| HPV16 | E2 | ETIYNSQY | 80 | 8 | | 31711 |
| HPV16 | E2 | ETQTTIQR | 233 | 8 | | 31712 |
| HPV16 | E2 | ETQTTIQRPR | 233 | 10 | | 31713 |
| HPV16 | E2 | EVSSPEIIR | 204 | 9 | | 31714 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E2 | EVSSPEIIRQH | 204 | 11 | | 31715 |
| HPV16 | E2 | FDGDICNTMH | 121 | 10 | | 31716 |
| HPV16 | E2 | FDGDICNTMHY | 121 | 11 | | 31717 |
| HPV16 | E2 | FLSQVKIPK | 346 | 9 | | 31718 |
| HPV16 | E2 | FVQFKDDA | 168 | 8 | | 31719 |
| HPV16 | E2 | FVQFKDDAEK | 168 | 10 | | 31720 |
| HPV16 | E2 | FVQFKDDAEKY | 168 | 11 | | 31721 |
| HPV16 | E2 | GCIKKHGY | 108 | 8 | | 31722 |
| HPV16 | E2 | GDANTLKCLR | 293 | 10 | | 31723 |
| HPV16 | E2 | GDANTLKCLRY | 293 | 11 | | 31724 |
| HPV16 | E2 | GDICNTMH | 123 | 8 | | 31725 |
| HPV16 | E2 | GDICNTMHY | 123 | 9 | | 31726 |
| HPV16 | E2 | GIRTYFVQF | 163 | 9 | | 31727 |
| HPV16 | E2 | GIRTYFVQFK | 163 | 10 | | 31728 |
| HPV16 | E2 | GLYYVHEGIR | 156 | 10 | | 31729 |
| HPV16 | E2 | GTEETQTTIQR | 230 | 11 | | 31730 |
| HPV16 | E2 | HGYTVEVQF | 113 | 9 | | 31731 |
| HPV16 | E2 | HIDYWKHMR | 29 | 9 | | 31732 |
| HPV16 | E2 | HINHQVVPTLA | 53 | 11 | | 31733 |
| HPV16 | E2 | HIYICEEA | 136 | 8 | | 31734 |
| HPV16 | E2 | HLANHPAA | 214 | 8 | | 31735 |
| HPV16 | E2 | HLANHPAATH | 214 | 10 | | 31736 |
| HPV16 | E2 | HLKGDANTLK | 290 | 10 | | 31737 |
| HPV16 | E2 | HMRLECAIY | 35 | 9 | | 31738 |
| HPV16 | E2 | HMRLECAIYY | 35 | 10 | | 31739 |
| HPV16 | E2 | HMRLECAIYYK | 35 | 11 | | 31740 |
| HPV16 | E2 | HTTKLLHR | 252 | 8 | | 31741 |
| HPV16 | E2 | IDYWKHMR | 30 | 8 | | 31742 |
| HPV16 | E2 | IIRQHLANH | 210 | 9 | | 31743 |
| HPV16 | E2 | IIRQHLANRPA | 210 | 11 | | 31744 |
| HPV16 | E2 | ILCPTSVF | 193 | 8 | | 31745 |
| HPV16 | E2 | ILTAFNSSH | 267 | 9 | | 31746 |
| HPV16 | E2 | ILTAFNSSHK | 267 | 10 | | 31747 |
| HPV16 | E2 | IVHLKGDA | 288 | 8 | | 31748 |
| HPV16 | E2 | KAREMGFK | 45 | 8 | | 31749 |
| HPV16 | E2 | KAREMGFKH | 45 | 9 | | 31750 |
| HPV16 | E2 | KCLRYFK | 299 | 8 | | 31751 |
| HPV16 | E2 | KCLRYFKK | 299 | 9 | | 31752 |
| HPV16 | E2 | KCLRYFKKH | 299 | 10 | | 31753 |
| HPV16 | E2 | KDDAEKYSK | 172 | 9 | | 31754 |
| HPV16 | E2 | KDDAEKYSKNK | 172 | 11 | | 31755 |
| HPV16 | E2 | KGDANTLK | 292 | 8 | | 31756 |
| HPV16 | E2 | KGDANTLKCLR | 292 | 11 | | 31757 |
| HPV16 | E2 | KLLHRDSVDSA | 255 | 11 | | 31758 |
| HPV16 | E2 | KSAIVTLTY | 329 | 9 | | 31759 |
| HPV16 | E2 | KTITVSTGF | 354 | 9 | | 31760 |
| HPV16 | E2 | LANHPAATH | 215 | 9 | | 31761 |
| HPV16 | E2 | LANHPAATHTK | 215 | 11 | | 31762 |
| HPV16 | E2 | LAVSKNKA | 62 | 8 | | 31763 |
| HPV16 | E2 | LAVSKNKALQA | 62 | 11 | | 31764 |
| HPV16 | E2 | LCQRLNVCQDK | 4 | 11 | | 31765 |
| HPV16 | E2 | LLHRDSVDSA | 256 | 10 | | 31766 |
| HPV16 | E2 | LSQVKIPK | 347 | 8 | | 31767 |
| HPV16 | E2 | LTAFNSSH | 268 | 8 | | 31768 |
| HPV16 | E2 | LTAFNSSHK | 268 | 9 | | 31769 |
| HPV16 | E2 | LTAFNSSHKGR | 268 | 11 | | 31770 |
| HPV16 | E2 | LTAPTGCIK | 103 | 9 | | 31771 |
| HPV16 | E2 | LTAPTGCIKK | 103 | 10 | | 31772 |
| HPV16 | E2 | LTAPTGCIKKH | 103 | 11 | | 31773 |
| HPV16 | E2 | LTLETIYNSQY | 77 | 11 | | 31774 |
| HPV16 | E2 | LTYDSEWQR | 335 | 9 | | 31775 |
| HPV16 | E2 | MGFKHINH | 49 | 8 | | 31776 |
| HPV16 | E2 | NCNSNTTPIVH | 280 | 11 | | 31777 |
| HPV16 | E2 | NDSTDLRDH | 21 | 9 | | 31778 |
| HPV16 | E2 | NSNTTPIVH | 282 | 9 | | 31779 |
| HPV16 | E2 | NSNTTPIVHLK | 282 | 11 | | 31780 |
| HPV16 | E2 | NSQYSNEK | 84 | 8 | | 31781 |
| HPV16 | E2 | NTLKCLRY | 296 | 8 | | 31782 |
| HPV16 | E2 | NTLKCLRYR | 296 | 9 | | 31783 |
| HPV16 | E2 | NTLKCLRYRF | 296 | 10 | | 31784 |
| HPV16 | E2 | NTLKCLRYRFK | 296 | 11 | | 31785 |
| HPV16 | E2 | NTMHYTNWTH | 127 | 10 | | 31786 |
| HPV16 | E2 | NTTPIVHLK | 284 | 9 | | 31787 |
| HPV16 | E2 | NVCQDKILTH | 9 | 10 | | 31788 |
| HPV16 | E2 | NVCQDKILTHY | 9 | 11 | | 31789 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E2 | PAATHTKA | 219 | 8 | | 31790 |
| HPV16 | E2 | PAATHTKAVA | 219 | 10 | | 31791 |
| HPV16 | E2 | PCHTTKLLH | 250 | 9 | | 31792 |
| HPV16 | E2 | PCHTTKLLHR | 250 | 10 | | 31793 |
| HPV16 | E2 | PDTGNPCH | 245 | 8 | | 31794 |
| HPV16 | E2 | PDTGNPCHTTK | 245 | 11 | | 31795 |
| HPV16 | E2 | PILTAFNSSH | 266 | 10 | | 31796 |
| HPV16 | E2 | PILTAFNSSHK | 266 | 11 | | 31797 |
| HPV16 | E2 | PIVHLKGDA | 287 | 9 | | 31798 |
| HPV16 | E2 | PTGCIKKH | 106 | 8 | | 31799 |
| HPV16 | E2 | PTGCIKKHGY | 106 | 10 | | 31800 |
| HPV16 | E2 | PTLAVSKNK | 60 | 9 | | 31801 |
| HPV16 | E2 | PTLAVSKNKA | 60 | 10 | | 31802 |
| HPV16 | E2 | QDKILTHY | 12 | 8 | | 31803 |
| HPV16 | E2 | QDVSLEVY | 95 | 8 | | 31804 |
| HPV16 | E2 | QDVSLEVYLTA | 95 | 11 | | 31805 |
| HPV16 | E2 | QFDGDICNTMH | 120 | 11 | | 31806 |
| HPV16 | E2 | QFKDDAEK | 170 | 8 | | 31807 |
| HPV16 | E2 | QFKDDAEKY | 170 | 9 | | 31808 |
| HPV16 | E2 | QFKDDAEKYSK | 170 | 11 | | 31809 |
| HPV16 | E2 | QFLSQVKIPK | 345 | 10 | | 31810 |
| HPV16 | E2 | QLTLETIY | 76 | 8 | | 31811 |
| HPV16 | E2 | QTTIQRPR | 235 | 8 | | 31812 |
| HPV16 | E2 | QVDYYGLY | 151 | 8 | | 31813 |
| HPV16 | E2 | QVDYYGLYY | 151 | 9 | | 31814 |
| HPV16 | E2 | QVDYYGLYYVH | 151 | 11 | | 31815 |
| HPV16 | E2 | QVILCPTSVF | 191 | 10 | | 31816 |
| HPV16 | E2 | QVVPTLAVSK | 57 | 10 | | 31817 |
| HPV16 | E2 | RDHIDYWK | 27 | 8 | | 31818 |
| HPV16 | E2 | RDHIDYWKH | 27 | 9 | | 31819 |
| HPV16 | E2 | RDHIDYWKHMR | 27 | 11 | | 31820 |
| HPV16 | E2 | RDQFLSQVK | 343 | 9 | | 31821 |
| HPV16 | E2 | RFKKHCTLY | 304 | 9 | | 31822 |
| HPV16 | E2 | RFKKHCTLYTA | 304 | 11 | | 31823 |
| HPV16 | E2 | RLECAIYY | 37 | 8 | | 31824 |
| HPV16 | E2 | RLECAIYYK | 37 | 9 | | 31825 |
| HPV16 | E2 | RLECAIYYKA | 37 | 10 | | 31826 |
| HPV16 | E2 | RLECAIYYKAR | 37 | 11 | | 31827 |
| HPV16 | E2 | RLNVCQDK | 7 | 8 | | 31828 |
| HPV16 | E2 | RSEPDTGNPCH | 242 | 11 | | 31829 |
| HPV16 | E2 | RTYFVQFK | 165 | 8 | | 31830 |
| HPV16 | E2 | RTYFVQFKDDA | 165 | 11 | | 31831 |
| HPV16 | E2 | SAIVTLTY | 330 | 8 | | 31832 |
| HPV16 | E2 | SAPILTAF | 264 | 8 | | 31833 |
| HPV16 | E2 | SLEVYLTA | 98 | 8 | | 31834 |
| HPV16 | E2 | SSPEIIRQH | 206 | 9 | | 31835 |
| HPV16 | E2 | SSPEIIRQHLA | 206 | 11 | | 31836 |
| HPV16 | E2 | SSTWHWTGH | 316 | 9 | | 31837 |
| HPV16 | E2 | STDLRDHIDY | 23 | 10 | | 31838 |
| HPV16 | E2 | STWHWTGH | 317 | 8 | | 31839 |
| HPV16 | E2 | STWHWTGHNVK | 317 | 11 | | 31840 |
| HPV16 | E2 | SVDSAPILTA | 261 | 10 | | 31841 |
| HPV16 | E2 | SVDSAPILTAF | 261 | 11 | | 31842 |
| HPV16 | E2 | SVTVVEGQVDY | 144 | 11 | | 31843 |
| HPV16 | E2 | TAFNSSHK | 269 | 8 | | 31844 |
| HPV16 | E2 | TAFNSSHKGR | 269 | 10 | | 31845 |
| HPV16 | E2 | TAPTGCIK | 104 | 8 | | 31846 |
| HPV16 | E2 | TAPTGCIKK | 104 | 9 | | 31847 |
| HPV16 | E2 | TAPTGCIKKH | 104 | 10 | | 31848 |
| HPV16 | E2 | TAVSSTWH | 313 | 8 | | 31849 |
| HPV16 | E2 | TDLRDHIDY | 24 | 9 | | 31850 |
| HPV16 | E2 | TDLRDHIDYWK | 24 | 11 | | 31851 |
| HPV16 | E2 | TGCIKKHGY | 107 | 9 | | 31852 |
| HPV16 | E2 | TGHNVKHK | 322 | 8 | | 31853 |
| HPV16 | E2 | TGHNVKHKSA | 322 | 10 | | 31854 |
| HPV16 | E2 | TGNPCHTTK | 247 | 9 | | 31855 |
| HPV16 | E2 | TITVSTGF | 355 | 8 | | 31856 |
| HPV16 | E2 | TIYNSQYSNEK | 81 | 11 | | 31857 |
| HPV16 | E2 | TLAVSKNK | 61 | 8 | | 31858 |
| HPV16 | E2 | TLAVSKNKA | 61 | 9 | | 31859 |
| HPV16 | E2 | TLETIYNSQY | 78 | 10 | | 31860 |
| HPV16 | E2 | TLKCLRYR | 297 | 8 | | 31861 |
| HPV16 | E2 | TLKCLRYRF | 297 | 9 | | 31862 |
| HPV16 | E2 | TLKCLRYRFK | 297 | 10 | | 31863 |
| HPV16 | E2 | TLKCLRYRFKK | 297 | 11 | | 31864 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E2 | TLQDVSLEVY | 93 | 10 | | 31865 |
| HPV16 | E2 | TLTYDSEWQR | 334 | 10 | | 31866 |
| HPV16 | E2 | TLYTAVSSTWH | 310 | 11 | | 31867 |
| HPV16 | E2 | TMHYTNWTH | 128 | 9 | | 31868 |
| HPV16 | E2 | TMHYTNWTHIY | 128 | 11 | | 31869 |
| HPV16 | E2 | TTPIVHLK | 285 | 8 | | 31870 |
| HPV16 | E2 | TTPIVHLKGDA | 285 | 11 | | 31871 |
| HPV16 | E2 | TVVEGQVDY | 146 | 9 | | 31872 |
| HPV16 | E2 | TVVEGQVDYY | 146 | 10 | | 31873 |
| HPV16 | E2 | VCQDKILTH | 10 | 9 | | 31874 |
| HPV16 | E2 | VCQDKILTHY | 10 | 10 | | 31875 |
| HPV16 | E2 | VDSAPILTA | 262 | 9 | | 31876 |
| HPV16 | E2 | VDSAPILTAF | 262 | 10 | | 31877 |
| HPV16 | E2 | VDYYGLYY | 152 | 8 | | 31878 |
| HPV16 | E2 | VDYYGLYYVH | 152 | 10 | | 31879 |
| HPV16 | E2 | VILCPTSVF | 192 | 9 | | 31880 |
| HPV16 | E2 | VSKNKALQA | 64 | 9 | | 31881 |
| HPV16 | E2 | VSLEVYLTA | 97 | 9 | | 31882 |
| HPV16 | E2 | VSSPEIIR | 205 | 8 | | 31883 |
| HPV16 | E2 | VSSPEIIRQH | 205 | 10 | | 31884 |
| HPV16 | E2 | VSSTWHWTGH | 315 | 10 | | 31885 |
| HPV16 | E2 | VTLTYDSEWQR | 333 | 11 | | 31886 |
| HPV16 | E2 | VTVVEGQVDY | 145 | 10 | | 31887 |
| HPV16 | E2 | VTVVEGQVDYY | 145 | 11 | | 31888 |
| HPV16 | E2 | VVEGQVDY | 147 | 8 | | 31889 |
| HPV16 | E2 | VVEGQVDYY | 147 | 9 | | 31890 |
| HPV16 | E2 | VVPTLAVSK | 58 | 9 | | 31891 |
| HPV16 | E2 | VVPTLAVSKNK | 58 | 11 | | 31892 |
| HPV16 | E2 | WTGHNVKH | 321 | 8 | | 31893 |
| HPV16 | E2 | WTGHNVKHK | 321 | 9 | | 31894 |
| HPV16 | E2 | WTGHNVKHKSA | 321 | 11 | | 31895 |
| HPV16 | E2 | WTHIYICEEA | 134 | 10 | | 31896 |
| HPV16 | E2 | WTLQDVSLEVY | 92 | 11 | | 31897 |
| HPV16 | E2 | YDSEWQRDQF | 337 | 10 | | 31898 |
| HPV16 | E2 | YFVQFKDDA | 167 | 9 | | 31899 |
| HPV16 | E2 | YFVQFKDDAEK | 167 | 11 | | 31900 |
| HPV16 | E2 | YGLYYVHEGIR | 155 | 11 | | 31901 |
| HPV16 | E2 | YLTAPTGCIK | 102 | 10 | | 31902 |
| HPV16 | E2 | YLTAPTGCIKK | 102 | 11 | | 31903 |
| HPV16 | E2 | YSKNKVWEVH | 178 | 10 | | 31904 |
| HPV16 | E2 | YSKNKVWEVHA | 178 | 11 | | 31905 |
| HPV16 | E2 | YTAVSSTWH | 312 | 9 | | 31906 |
| HPV16 | E2 | YTNWTHIY | 131 | 8 | | 31907 |
| HPV16 | E2 | YVHEGIRTY | 159 | 9 | | 31908 |
| HPV16 | E2 | YVHEGIRTYF | 159 | 10 | | 31909 |
| HPV16 | E5 | AASAFRCF | 53 | 8 | | 31910 |
| HPV16 | E5 | AASAFRCFIVY | 53 | 11 | | 31911 |
| HPV16 | E5 | AFRCFIVY | 56 | 8 | | 31912 |
| HPV16 | E5 | AFRCFIVYIIF | 56 | 11 | | 31913 |
| HPV16 | E5 | ASAFRCFIVY | 54 | 10 | | 31914 |
| HPV16 | E5 | ASTTLLACF | 7 | 9 | | 31915 |
| HPV16 | E5 | CFIVYIIF | 59 | 8 | | 31916 |
| HPV16 | E5 | CFIVYIIFVY | 59 | 10 | | 31917 |
| HPV16 | E5 | CVLLCVCLLIR | 20 | 11 | | 31918 |
| HPV16 | E5 | DTASTTLLA | 5 | 9 | | 31919 |
| HPV16 | E5 | DTASTTLLACF | 5 | 11 | | 31920 |
| HPV16 | E5 | FIVYIIFVY | 60 | 9 | | 31921 |
| HPV16 | E5 | FLIHTHAR | 72 | 8 | | 31922 |
| HPV16 | E5 | FLIHTHARF | 72 | 9 | | 31923 |
| HPV16 | E5 | FVYIPLFLIH | 66 | 10 | | 31924 |
| HPV16 | E5 | IFVYIPLF | 65 | 8 | | 31925 |
| HPV16 | E5 | IFVYIPLFLIH | 65 | 11 | | 31926 |
| HPV16 | E5 | IIFVYIPLF | 64 | 9 | | 31927 |
| HPV16 | E5 | IILVLLLWITA | 43 | 11 | | 31928 |
| HPV16 | E5 | ILVLLLWITA | 44 | 10 | | 31929 |
| HPV16 | E5 | ILVLLLWITAA | 44 | 11 | | 31930 |
| HPV16 | E5 | ITAASAFR | 51 | 8 | | 31931 |
| HPV16 | E5 | ITAASAFRCF | 51 | 10 | | 31932 |
| HPV16 | E5 | IVYIIFVY | 61 | 8 | | 31933 |
| HPV16 | E5 | LACFLLCF | 12 | 8 | | 31934 |
| HPV16 | E5 | LCVCLLIR | 23 | 8 | | 31935 |
| HPV16 | E5 | LDTASTTLLA | 4 | 10 | | 31936 |
| HPV16 | E5 | LFLIHTHA | 71 | 8 | | 31937 |
| HPV16 | E5 | LFLIHTHAR | 71 | 9 | | 31938 |
| HPV16 | E5 | LFLIHTHARF | 71 | 10 | | 31939 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E5 | LIHTHARF | 73 | 8 | | 31940 |
| HPV16 | E5 | LLACFLLCF | 11 | 9 | | 31941 |
| HPV16 | E5 | LLCVCLLIR | 22 | 9 | | 31942 |
| HPV16 | E5 | LLLSVSTY | 32 | 8 | | 31943 |
| HPV16 | E5 | LLLWITAA | 47 | 8 | | 31944 |
| HPV16 | E5 | LLLWITAASA | 47 | 10 | | 31945 |
| HPV16 | E5 | LLLWITAASAF | 47 | 11 | | 31946 |
| HPV16 | E5 | LLWITAASA | 48 | 9 | | 31947 |
| HPV16 | E5 | LLWITAASAF | 48 | 10 | | 31948 |
| HPV16 | E5 | LLWITAASAFR | 48 | 11 | | 31949 |
| HPV16 | E5 | LVLLLWITA | 45 | 9 | | 31950 |
| HPV16 | E5 | LVLLLWITAA | 45 | 10 | | 31951 |
| HPV16 | E5 | NLDTASTTLLA | 3 | 11 | | 31952 |
| HPV16 | E5 | PLFLIHTH | 70 | 8 | | 31953 |
| HPV16 | E5 | PLFLIHTHA | 70 | 9 | | 31954 |
| HPV16 | E5 | PLFLIHTHAR | 70 | 10 | | 31955 |
| HPV16 | E5 | PLFLIHTHARF | 70 | 11 | | 31956 |
| HPV16 | E5 | PLLLSVSTY | 31 | 9 | | 31957 |
| HPV16 | E5 | RCFIVYIIF | 58 | 9 | | 31958 |
| HPV16 | E5 | RCFIVYIIFVY | 58 | 11 | | 31959 |
| HPV16 | E5 | SAFRCFIVY | 55 | 9 | | 31960 |
| HPV16 | E5 | STTLLACF | 8 | 8 | | 31961 |
| HPV16 | E5 | TAASAFRCF | 52 | 9 | | 31962 |
| HPV16 | E5 | TASTTLLA | 6 | 8 | | 31963 |
| HPV16 | E5 | TASTTLLACF | 6 | 10 | | 31964 |
| HPV16 | E5 | TLLACFLLCF | 10 | 10 | | 31965 |
| HPV16 | E5 | TTLLACFLLCF | 9 | 11 | | 31966 |
| HPV16 | E5 | VLLCVCLLIR | 21 | 10 | | 31967 |
| HPV16 | E5 | VLLLWITA | 46 | 8 | | 31968 |
| HPV16 | E5 | VLLLWITAA | 46 | 9 | | 31969 |
| HPV16 | E5 | VLLLWITAASA | 46 | 11 | | 31970 |
| HPV16 | E5 | WITAASAF | 50 | 8 | | 31971 |
| HPV16 | E5 | WITAASAFR | 50 | 9 | | 31972 |
| HPV16 | E5 | WITAASAFRCF | 50 | 11 | | 31973 |
| HPV16 | E5 | YIIFVYIPLF | 63 | 10 | | 31974 |
| HPV16 | E5 | YIPLFLIH | 68 | 8 | | 31975 |
| HPV16 | E5 | YIPLFLIHTH | 68 | 10 | | 31976 |
| HPV16 | E5 | YIPLFLIHTHA | 68 | 11 | | 31977 |
| HPV16 | E6 | AFRDLCIVY | 53 | 9 | 0.0052 | 31978 |
| HPV16 | E6 | AFRDLCIVYR | 53 | 10 | | 31979 |
| HPV16 | E6 | AMFQDPQER | 7 | 9 | 0.0170 | 31980 |
| HPV16 | E6 | AMFQDPQERPR | 7 | 11 | | 31981 |
| HPV16 | E6 | AVCDKCLK | 68 | 8 | 0.0053 | 31982 |
| HPV16 | E6 | AVCDKCLKF | 68 | 9 | 0.0002 | 31983 |
| HPV16 | E6 | AVCDKCLKFY | 68 | 10 | 0.0052 | 31984 |
| HPV16 | E6 | CCRSSRTR | 146 | 8 | | 31985 |
| HPV16 | E6 | CCRSSRTRR | 146 | 9 | 0.0003 | 31986 |
| HPV16 | E6 | CDKCLKFY | 70 | 8 | | 31987 |
| HPV16 | E6 | CDKCLKFYSK | 70 | 10 | | 31988 |
| HPV16 | E6 | CIVYRDGNPY | 58 | 10 | 0.0026 | 31989 |
| HPV16 | E6 | CIVYRDGNPYA | 58 | 11 | | 31990 |
| HPV16 | E6 | CLKFYSKISEY | 73 | 11 | | 31991 |
| HPV16 | E6 | CMSCCRSSR | 143 | 9 | 0.0033 | 31992 |
| HPV16 | E6 | CMSCCRSSRTR | 143 | 11 | | 31993 |
| HPV16 | E6 | CTELQTTIH | 23 | 9 | 0.0002 | 31994 |
| HPV16 | E6 | CVYCKQQLLR | 37 | 10 | 0.0001 | 31995 |
| HPV16 | E6 | CVYCKQQLLRR | 37 | 11 | | 31996 |
| HPV16 | E6 | DFAFRDLCIVY | 51 | 11 | | 31997 |
| HPV16 | E6 | DGNPYAVCDK | 63 | 10 | | 31998 |
| HPV16 | E6 | DIILECVY | 32 | 8 | | 31999 |
| HPV16 | E6 | DIILECVYCK | 32 | 10 | 0.0065 | 32000 |
| HPV16 | E6 | DLLIRCINCQK | 105 | 11 | | 32001 |
| HPV16 | E6 | ECVYCKQQLLR | 36 | 11 | | 32002 |
| HPV16 | E6 | EVYDFAFR | 48 | 8 | 0.0004 | 32003 |
| HPV16 | E6 | FAFRDLCIVY | 52 | 10 | | 32004 |
| HPV16 | E6 | FAFRDLCIVYR | 52 | 11 | | 32005 |
| HPV16 | E6 | GTTLEQQY | 92 | 8 | | 32006 |
| HPV16 | E6 | GTTLEQQYNK | 92 | 10 | 0.0002 | 32007 |
| HPV16 | E6 | HDIILECVY | 31 | 9 | 0.0002 | 32008 |
| HPV16 | E6 | HDIILECVYCK | 31 | 11 | | 32009 |
| HPV16 | E6 | HLDKKQRF | 125 | 8 | | 32010 |
| HPV16 | E6 | HLDKKQRFH | 125 | 9 | 0.0009 | 32011 |
| HPV16 | E6 | IILECVYCK | 33 | 9 | 0.0016 | 32012 |
| HPV16 | E6 | ILECVYCK | 34 | 8 | | 32013 |
| HPV16 | E6 | ISEYRHYCY | 80 | 9 | 0.0001 | 32014 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E6 | IVYRDGNPY | 59 | 9 | 0.1500 | 32015 |
| HPV16 | E6 | IVYRDGNPYA | 59 | 10 | | 32016 |
| HPV16 | E6 | KCLKFYSK | 72 | 8 | | 32017 |
| HPV16 | E6 | KFYSKISEY | 75 | 9 | 0.0015 | 32018 |
| HPV16 | E6 | KFYSKISEYR | 75 | 10 | 0.0067 | 32019 |
| HPV16 | E6 | KFYSKISEYRH | 75 | 11 | | 32020 |
| HPV16 | E6 | KISEYRHY | 79 | 8 | | 32021 |
| HPV16 | E6 | KISEYRHYCY | 79 | 10 | 0.0043 | 32022 |
| HPV16 | E6 | LCIVYRDGNPY | 57 | 11 | | 32023 |
| HPV16 | E6 | LCPEEKQR | 117 | 8 | | 32024 |
| HPV16 | E6 | LCPEEKQRH | 117 | 9 | 0.0003 | 32025 |
| HPV16 | E6 | LCTELQTTIH | 22 | 10 | | 32026 |
| HPV16 | E6 | LDKKQRFH | 126 | 8 | | 32027 |
| HPV16 | E6 | LDKKQRFHNIR | 126 | 11 | | 32028 |
| HPV16 | E6 | LIRCINCQK | 107 | 9 | 0.0025 | 32029 |
| HPV16 | E6 | LLIRCINCQK | 106 | 10 | 0.0210 | 32030 |
| HPV16 | E6 | LLRREVYDF | 44 | 9 | | 32031 |
| HPV16 | E6 | LLRREVYDFA | 44 | 10 | | 32032 |
| HPV16 | E6 | LLRREVYDFAF | 44 | 11 | | 32033 |
| HPV16 | E6 | MFQDPQER | 8 | 8 | | 32034 |
| HPV16 | E6 | MFQDPQERPR | 8 | 10 | | 32035 |
| HPV16 | E6 | MFQDPQERPRK | 8 | 11 | | 32036 |
| HPV16 | E6 | MSCCRSSR | 144 | 8 | | 32037 |
| HPV16 | E6 | MSCCRSSRTR | 144 | 10 | | 32038 |
| HPV16 | E6 | MSCCRSSRTRR | 144 | 11 | | 32039 |
| HPV16 | E6 | NCQKPLCPEEK | 112 | 11 | | 32040 |
| HPV16 | E6 | NIRGRWTGR | 134 | 9 | 0.0014 | 32041 |
| HPV16 | E6 | PLCDLLIR | 102 | 8 | | 32042 |
| HPV16 | E6 | PLCPEEKQR | 116 | 9 | 0.0002 | 32043 |
| HPV16 | E6 | PLCPEEKQRH | 116 | 10 | | 32044 |
| HPV16 | E6 | QDPQERPR | 10 | 8 | | 32045 |
| HPV16 | E6 | QDPQERPRK | 10 | 9 | | 32046 |
| HPV16 | E6 | QLCTELQTTIH | 21 | 11 | | 32047 |
| HPV16 | E6 | QLLRREVY | 43 | 8 | | 32048 |
| HPV16 | E6 | QLLRREVYDF | 43 | 10 | | 32049 |
| HPV16 | E6 | QLLRREVYDFA | 43 | 11 | | 32050 |
| HPV16 | E6 | RCMSCCRSSR | 142 | 10 | | 32051 |
| HPV16 | E6 | RDGNPYAVCDK | 62 | 11 | | 32052 |
| HPV16 | E6 | RDLCIVYR | 55 | 8 | | 32053 |
| HPV16 | E6 | RFHNIRGR | 131 | 8 | | 32054 |
| HPV16 | E6 | RTAMFQDPQER | 5 | 11 | | 32055 |
| HPV16 | E6 | SCCRSSRTR | 145 | 9 | 0.0003 | 32056 |
| HPV16 | E6 | SCCRSSRTRR | 145 | 10 | | 32057 |
| HPV16 | E6 | SLYGTTLEQQY | 89 | 11 | | 32058 |
| HPV16 | E6 | TAMFQDPQER | 6 | 10 | | 32059 |
| HPV16 | E6 | TGRCMSCCR | 140 | 9 | 0.0003 | 32060 |
| HPV16 | E6 | TIHDIILECVY | 29 | 11 | | 32061 |
| HPV16 | E6 | TLEQQYNK | 94 | 8 | | 32062 |
| HPV16 | E6 | TTLEQQYNK | 93 | 9 | 0.0100 | 32063 |
| HPV16 | E6 | VCDKCLKF | 69 | 8 | | 32064 |
| HPV16 | E6 | VCDKCLKFY | 69 | 9 | 0.0002 | 32065 |
| HPV16 | E6 | VCDKCLKFYSK | 69 | 11 | | 32066 |
| HPV16 | E6 | WTGRCMSCCR | 139 | 10 | 0.0003 | 32067 |
| HPV16 | E6 | YAVCDKCLK | 67 | 9 | 0.0003 | 32068 |
| HPV16 | E6 | YAVCDKCLKF | 67 | 10 | | 32069 |
| HPV16 | E6 | YAVCDKCLKFY | 67 | 11 | | 32070 |
| HPV16 | E6 | YCKQQLLR | 39 | 8 | | 32071 |
| HPV16 | E6 | YCKQQLLRR | 39 | 9 | 0.0003 | 32072 |
| HPV16 | E6 | YGTTLEQQY | 91 | 9 | | 32073 |
| HPV16 | E6 | YGTTLEQQYNK | 91 | 11 | | 32074 |
| HPV16 | E6 | YSKISEYR | 77 | 8 | | 32075 |
| HPV16 | E6 | YSKISEYRH | 77 | 9 | | 32076 |
| HPV16 | E6 | YSKISEYRHY | 77 | 10 | 0.0001 | 32077 |
| HPV16 | E7 | AGQAEPDR | 42 | 8 | | 32078 |
| HPV16 | E7 | AGQAEPDRA | 42 | 9 | | 32079 |
| HPV16 | E7 | AGQAEPDRAH | 42 | 10 | | 32080 |
| HPV16 | E7 | AGQAEPDRAHY | 42 | 11 | | 32081 |
| HPV16 | E7 | CCKCDSTLR | 58 | 9 | 0.0003 | 32082 |
| HPV16 | E7 | CVQSTHVDIR | 68 | 10 | 0.0049 | 32083 |
| HPV16 | E7 | DGPAGQAEPDR | 39 | 11 | | 32084 |
| HPV16 | E7 | DLQPETTDLY | 14 | 10 | 0.0002 | 32085 |
| HPV16 | E7 | DTPTLHEY | 4 | 8 | | 32086 |
| HPV16 | E7 | EDEIDGPA | 35 | 8 | | 32087 |
| HPV16 | E7 | EDEIDGPAGQA | 35 | 11 | | 32088 |
| HPV16 | E7 | EIDGPAGQA | 37 | 9 | | 32089 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | E7 | ETTDLYCY | 18 | 8 | 0.0002 | 32090 |
| HPV16 | E7 | FCCKCDSTLR | 57 | 10 | | 32091 |
| HPV16 | E7 | GDTPTLHEY | 3 | 9 | | 32092 |
| HPV16 | E7 | GIVCPICSQK | 88 | 10 | 0.0003 | 32093 |
| HPV16 | E7 | HGDTPTLH | 2 | 8 | | 32094 |
| HPV16 | E7 | HGDTPTLHEY | 2 | 10 | 0.0001 | 32095 |
| HPV16 | E7 | IDGPAGQA | 38 | 8 | | 32096 |
| HPV16 | E7 | IVCPICSQK | 89 | 9 | 0.0077 | 32097 |
| HPV16 | E7 | LCVQSTHVDIR | 67 | 11 | | 32098 |
| HPV16 | E7 | LDLQPETTDLY | 13 | 11 | | 32099 |
| HPV16 | E7 | LGIVCPICSQK | 87 | 11 | | 32100 |
| HPV16 | E7 | NIVTFCCK | 53 | 8 | | 32101 |
| HPV16 | E7 | PAGQAEPDR | 41 | 9 | | 32102 |
| HPV16 | E7 | PAGQAEPDRA | 41 | 10 | | 32103 |
| HPV16 | E7 | PAGQAEPDRAH | 41 | 11 | | 32104 |
| HPV16 | E7 | PDRAHYNIVTF | 47 | 11 | | 32105 |
| HPV16 | E7 | QAEPDRAH | 44 | 8 | | 32106 |
| HPV16 | E7 | QAEPDRAHY | 44 | 9 | 0.0002 | 32107 |
| HPV16 | E7 | QSTHVDIR | 70 | 8 | | 32108 |
| HPV16 | E7 | RAHYNIVTF | 49 | 9 | | 32109 |
| HPV16 | E7 | RLCVQSTH | 66 | 8 | | 32110 |
| HPV16 | E7 | STLRLCVQSTH | 63 | 11 | | 32111 |
| HPV16 | E7 | TFCCKCDSTLR | 56 | 11 | | 32112 |
| HPV16 | E7 | TLRLCVQSTH | 64 | 10 | | 32113 |
| HPV16 | E7 | VCPICSQK | 90 | 8 | | 32114 |
| HPV16 | L1 | AAISTSETTY | 372 | 10 | | 32115 |
| HPV16 | L1 | AAISTSETTYK | 372 | 11 | | 32116 |
| HPV16 | L1 | AANAGVDNR | 162 | 9 | | 32117 |
| HPV16 | L1 | ACQKHTPPA | 453 | 9 | | 32118 |
| HPV16 | L1 | ACQKHTPPAPK | 453 | 11 | | 32119 |
| HPV16 | L1 | ACVGVEVGR | 127 | 9 | | 32120 |
| HPV16 | L1 | ADLDQFPLGR | 483 | 10 | | 32121 |
| HPV16 | L1 | ADLDQFPLGRK | 483 | 11 | | 32122 |
| HPV16 | L1 | ADVMTYIH | 411 | 8 | | 32123 |
| HPV16 | L1 | AGLKAKPK | 498 | 8 | | 32124 |
| HPV16 | L1 | AGLKAKPKF | 498 | 9 | | 32125 |
| HPV16 | L1 | AGTSRLLA | 63 | 8 | | 32126 |
| HPV16 | L1 | AGTSRLLAVGH | 63 | 11 | | 32127 |
| HPV16 | L1 | AIACQKHTPPA | 451 | 11 | | 32128 |
| HPV16 | L1 | AISTSETTY | 373 | 9 | | 32129 |
| HPV16 | L1 | AISTSETTYK | 373 | 10 | | 32130 |
| HPV16 | L1 | AMDFTTLQA | 233 | 9 | | 32131 |
| HPV16 | L1 | AMDFTTLQANK | 233 | 11 | | 32132 |
| HPV16 | L1 | ASAYAANA | 158 | 8 | | 32133 |
| HPV16 | L1 | AVGENVPDDLY | 292 | 11 | | 32134 |
| HPV16 | L1 | AVGHPYFPIK | 70 | 10 | | 32135 |
| HPV16 | L1 | AVGHPYFPIKK | 70 | 11 | | 32136 |
| HPV16 | L1 | CAAISTSETTY | 371 | 11 | | 32137 |
| HPV16 | L1 | CTSICKYPDY | 251 | 10 | | 32138 |
| HPV16 | L1 | CVGVEVGR | 128 | 8 | | 32139 |
| HPV16 | L1 | DAQIFNKPY | 329 | 9 | | 32140 |
| HPV16 | L1 | DDTENASA | 153 | 8 | | 32141 |
| HPV16 | L1 | DDTENASAY | 153 | 9 | | 32142 |
| HPV16 | L1 | DDTENASAYA | 153 | 10 | | 32143 |
| HPV16 | L1 | DDTENASAYAA | 153 | 11 | | 32144 |
| HPV16 | L1 | DFTTLQANK | 235 | 9 | | 32145 |
| HPV16 | L1 | DGDMVDTGF | 223 | 9 | | 32146 |
| HPV16 | L1 | DGDMVDTGFGA | 223 | 11 | | 32147 |
| HPV16 | L1 | DICTSICK | 249 | 8 | | 32148 |
| HPV16 | L1 | DICTSICKY | 249 | 9 | | 32149 |
| HPV16 | L1 | DLDQFPLGR | 484 | 9 | | 32150 |
| HPV16 | L1 | DLDQFPLGRK | 484 | 10 | | 32151 |
| HPV16 | L1 | DLDQFPLGRKF | 484 | 11 | | 32152 |
| HPV16 | L1 | DLQFIFQLCK | 397 | 10 | | 32153 |
| HPV16 | L1 | DLYIKGSGSTA | 300 | 11 | | 32154 |
| HPV16 | L1 | DMVDTGFGA | 225 | 9 | | 32155 |
| HPV16 | L1 | DSLFFYLR | 270 | 8 | | 32156 |
| HPV16 | L1 | DSLFFYLRR | 270 | 9 | | 32157 |
| HPV16 | L1 | DTENASAY | 154 | 8 | | 32158 |
| HPV16 | L1 | DTENASAYA | 154 | 9 | | 32159 |
| HPV16 | L1 | DTENASAYAA | 154 | 10 | | 32160 |
| HPV16 | L1 | DTGFGAMDF | 228 | 9 | | 32161 |
| HPV16 | L1 | DTQRLVWA | 120 | 8 | | 32162 |
| HPV16 | L1 | DTSFYNPDTQR | 113 | 11 | | 32163 |
| HPV16 | L1 | DTYRFVTSQA | 442 | 10 | | 32164 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | L1 | DVNVYHIF | 17 | 8 | | 32165 |
| HPV16 | L1 | DVNVYHIFF | 17 | 9 | | 32166 |
| HPV16 | L1 | ECISMDYK | 171 | 8 | | 32167 |
| HPV16 | L1 | EDPLKKYTF | 464 | 9 | | 32168 |
| HPV16 | L1 | EDTYRFVTSQA | 441 | 11 | | 32169 |
| HPV16 | L1 | ETTYKNTNF | 378 | 9 | | 32170 |
| HPV16 | L1 | ETTYKNTNFK | 378 | 10 | | 32171 |
| HPV16 | L1 | EVNLKEKF | 474 | 8 | | 32172 |
| HPV16 | L1 | EVNLKEKFSA | 474 | 10 | | 32173 |
| HPV16 | L1 | FFYLRREQMF | 273 | 10 | | 32174 |
| HPV16 | L1 | FGAMDFTTLQA | 231 | 11 | | 32175 |
| HPV16 | L1 | FGFPDTSF | 109 | 8 | | 32176 |
| HPV16 | L1 | FGFPDTSFY | 109 | 9 | | 32177 |
| HPV16 | L1 | FIYILVITCY | 5 | 10 | | 32178 |
| HPV16 | L1 | FLLQAGLK | 494 | 8 | | 32179 |
| HPV16 | L1 | FLLQAGLKA | 494 | 9 | | 32180 |
| HPV16 | L1 | FLLQAGLKAK | 494 | 10 | | 32181 |
| HPV16 | L1 | FSADLDQF | 481 | 8 | | 32182 |
| HPV16 | L1 | FTLGKRKA | 506 | 8 | | 32183 |
| HPV16 | L1 | FTTLQANK | 236 | 8 | | 32184 |
| HPV16 | L1 | FVRHLFNR | 282 | 8 | | 32185 |
| HPV16 | L1 | FVRHLFNRA | 282 | 9 | | 32186 |
| HPV16 | L1 | FVRHLFNRAGA | 282 | 11 | | 32187 |
| HPV16 | L1 | FVTSQAIA | 446 | 8 | | 32188 |
| HPV16 | L1 | FVTSQAIACQK | 446 | 11 | | 32189 |
| HPV16 | L1 | FVTVVDTTR | 356 | 9 | | 32190 |
| HPV16 | L1 | GAMDFTTLQA | 232 | 10 | | 32191 |
| HPV16 | L1 | GCKPPIGEH | 186 | 9 | | 32192 |
| HPV16 | L1 | GDMVDTGF | 224 | 8 | | 32193 |
| HPV16 | L1 | GDMVDTGFGA | 224 | 10 | | 32194 |
| HPV16 | L1 | GDSLFFYLR | 269 | 9 | | 32195 |
| HPV16 | L1 | GDSLFFYLRR | 269 | 10 | | 32196 |
| HPV16 | L1 | GFPDTSFY | 110 | 8 | | 32197 |
| HPV16 | L1 | GGTLEDTY | 437 | 8 | | 32198 |
| HPV16 | L1 | GGTLEDTYR | 437 | 9 | | 32199 |
| HPV16 | L1 | GGTLEDTYRF | 437 | 10 | | 32200 |
| HPV16 | L1 | GICWGNQLF | 348 | 9 | | 32201 |
| HPV16 | L1 | GISGHPLLNK | 142 | 10 | | 32202 |
| HPV16 | L1 | GLKAKPKF | 499 | 8 | | 32203 |
| HPV16 | L1 | GLQYRVFR | 93 | 8 | | 32204 |
| HPV16 | L1 | GLQYRVFRIH | 93 | 10 | | 32205 |
| HPV16 | L1 | GSGSTANLA | 305 | 9 | | 32206 |
| HPV16 | L1 | GSMVTSDA | 323 | 8 | | 32207 |
| HPV16 | L1 | GSMVTSDAQIF | 323 | 11 | | 32208 |
| HPV16 | L1 | GSPCTNVA | 198 | 8 | | 32209 |
| HPV16 | L1 | GSTANLASSNY | 307 | 11 | | 32210 |
| HPV16 | L1 | GTLEDTYR | 438 | 8 | | 32211 |
| HPV16 | L1 | GTLEDTYRF | 438 | 9 | | 32212 |
| HPV16 | L1 | GTSRLLAVGH | 64 | 10 | | 32213 |
| HPV16 | L1 | HAGTSRLLA | 62 | 9 | | 32214 |
| HPV16 | L1 | HGEEYDLQF | 392 | 9 | | 32215 |
| HPV16 | L1 | HGEEYDLQFIF | 392 | 11 | | 32216 |
| HPV16 | L1 | HLFNRAGA | 285 | 8 | | 32217 |
| HPV16 | L1 | HLPDPNKF | 102 | 8 | | 32218 |
| HPV16 | L1 | HLPDPNKFGF | 102 | 10 | | 32219 |
| HPV16 | L1 | IACQKHTPPA | 452 | 10 | | 32220 |
| HPV16 | L1 | ICKYPDYIK | 254 | 9 | | 32221 |
| HPV16 | L1 | ICTSICKY | 250 | 8 | | 32222 |
| HPV16 | L1 | ICTSICKYPDY | 250 | 11 | | 32223 |
| HPV16 | L1 | ICWGNQLF | 349 | 8 | | 32224 |
| HPV16 | L1 | IFNKPYWLQR | 332 | 10 | | 32225 |
| HPV16 | L1 | IFNKPYWLQRA | 332 | 11 | | 32226 |
| HPV16 | L1 | IFQLCKITLTA | 401 | 11 | | 32227 |
| HPV16 | L1 | IGCKPPIGEH | 185 | 10 | | 32228 |
| HPV16 | L1 | ILVPKVSGLQY | 86 | 11 | | 32229 |
| HPV16 | L1 | ISGHPLLNK | 143 | 9 | | 32230 |
| HPV16 | L1 | ISTSETTY | 374 | 8 | | 32231 |
| HPV16 | L1 | ISTSETTYK | 374 | 9 | | 32232 |
| HPV16 | L1 | ITCYENDVNVY | 11 | 11 | | 32233 |
| HPV16 | L1 | ITLTADVMTY | 407 | 10 | | 32234 |
| HPV16 | L1 | KAKPKFTLGK | 501 | 10 | | 32235 |
| HPV16 | L1 | KAKPKFTLGKR | 501 | 11 | | 32236 |
| HPV16 | L1 | KFGFPDTSF | 108 | 9 | | 32237 |
| HPV16 | L1 | KFGFPDTSFY | 108 | 10 | | 32238 |
| HPV16 | L1 | KFLLQAGLK | 493 | 9 | | 32239 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | L1 | KFLLQAGLKA | 493 | 10 | | 32240 |
| HPV16 | L1 | KFLLQAGLKAK | 493 | 11 | | 32241 |
| HPV16 | L1 | KFSADLDQF | 480 | 9 | | 32242 |
| HPV16 | L1 | KFTLGKRK | 505 | 8 | | 32243 |
| HPV16 | L1 | KFTLGKRKA | 505 | 9 | | 32244 |
| HPV16 | L1 | KGSGSTANLA | 304 | 10 | | 32245 |
| HPV16 | L1 | KGSPCTNVA | 197 | 9 | | 32246 |
| HPV16 | L1 | KITLTADVMTY | 406 | 11 | | 32247 |
| HPV16 | L1 | KLDDTENA | 151 | 8 | | 32248 |
| HPV16 | L1 | KLDDTENASA | 151 | 10 | | 32249 |
| HPV16 | L1 | KLDDTENASAY | 151 | 11 | | 32250 |
| HPV16 | L1 | KVSGLQYR | 90 | 8 | | 32251 |
| HPV16 | L1 | KVSGLQYRVF | 90 | 10 | | 32252 |
| HPV16 | L1 | KVSGLQYRVFR | 90 | 11 | | 32253 |
| HPV16 | L1 | KVVSTDEY | 46 | 8 | | 32254 |
| HPV16 | L1 | KVVSTDEYVA | 46 | 10 | | 32255 |
| HPV16 | L1 | KVVSTDEYVAR | 46 | 11 | | 32256 |
| HPV16 | L1 | LAVGHPYF | 69 | 8 | | 32257 |
| HPV16 | L1 | LAVGHPYFPIK | 69 | 11 | | 32258 |
| HPV16 | L1 | LCKITLTA | 404 | 8 | | 32259 |
| HPV16 | L1 | LDDTENASA | 152 | 9 | | 32260 |
| HPV16 | L1 | LDDTENASAY | 152 | 10 | | 32261 |
| HPV16 | L1 | LDDTENASAYA | 152 | 11 | | 32262 |
| HPV16 | L1 | LDICTSICK | 248 | 9 | | 32263 |
| HPV16 | L1 | LDICTSICKY | 248 | 10 | | 32264 |
| HPV16 | L1 | LDQFPLGR | 485 | 8 | | 32265 |
| HPV16 | L1 | LDQFPLGRK | 485 | 9 | | 32266 |
| HPV16 | L1 | LDQFPLGRKF | 485 | 10 | | 32267 |
| HPV16 | L1 | LFFYLRREQMF | 272 | 11 | | 32268 |
| HPV16 | L1 | LFVTVVDTTR | 355 | 10 | | 32269 |
| HPV16 | L1 | LGRKFLLQA | 490 | 9 | | 32270 |
| HPV16 | L1 | LGVGISGH | 139 | 8 | | 32271 |
| HPV16 | L1 | LIGCKPPIGEH | 184 | 11 | | 32272 |
| HPV16 | L1 | LLAVGHPY | 68 | 8 | | 32273 |
| HPV16 | L1 | LLAVGHPYF | 68 | 9 | | 32274 |
| HPV16 | L1 | LLNKLDDTENA | 148 | 11 | | 32275 |
| HPV16 | L1 | LLQAGLKA | 495 | 8 | | 32276 |
| HPV16 | L1 | LLQAGLKAK | 495 | 9 | | 32277 |
| HPV16 | L1 | LLQAGLKAKPK | 495 | 11 | | 32278 |
| HPV16 | L1 | LTADVMTY | 409 | 8 | | 32279 |
| HPV16 | L1 | LTADVMTYIH | 409 | 10 | | 32280 |
| HPV16 | L1 | LVPKVSGLQY | 87 | 10 | | 32281 |
| HPV16 | L1 | LVPKVSGLQYR | 87 | 11 | | 32282 |
| HPV16 | L1 | MDFTTLQA | 234 | 8 | | 32283 |
| HPV16 | L1 | MDFTTLQANK | 234 | 10 | | 32284 |
| HPV16 | L1 | MFVRHLFNR | 281 | 9 | | 32285 |
| HPV16 | L1 | MFVRHLFNRA | 281 | 10 | | 32286 |
| HPV16 | L1 | MSLWLPSEA | 27 | 9 | | 32287 |
| HPV16 | L1 | MVDTGFGA | 226 | 8 | | 32288 |
| HPV16 | L1 | MVDTGFGAMDF | 226 | 11 | | 32289 |
| HPV16 | L1 | MVSEPYGDSLF | 263 | 11 | | 32290 |
| HPV16 | L1 | MVTSDAQIF | 325 | 9 | | 32291 |
| HPV16 | L1 | MVTSDAQIFNK | 325 | 11 | | 32292 |
| HPV16 | L1 | NASAYAANA | 157 | 9 | | 32293 |
| HPV16 | L1 | NDVNVYHIF | 16 | 9 | | 32294 |
| HPV16 | L1 | NDVNVYHIFF | 16 | 10 | | 32295 |
| HPV16 | L1 | NFKEYLRH | 385 | 8 | | 32296 |
| HPV16 | L1 | NGICWGNQLF | 347 | 10 | | 32297 |
| HPV16 | L1 | NIYYHAGTSR | 58 | 10 | | 32298 |
| HPV16 | L1 | NLASSNYF | 311 | 8 | | 32299 |
| HPV16 | L1 | NLKEKFSA | 476 | 8 | | 32300 |
| HPV16 | L1 | NSTILEDWNF | 421 | 10 | | 32301 |
| HPV16 | L1 | NTNFKEYLR | 383 | 9 | | 32302 |
| HPV16 | L1 | NTNFKEYLRH | 383 | 10 | | 32303 |
| HPV16 | L1 | NVPDDLYIK | 296 | 9 | | 32304 |
| HPV16 | L1 | PAPKEDPLK | 460 | 9 | | 32305 |
| HPV16 | L1 | PAPKEDPLKK | 460 | 10 | | 32306 |
| HPV16 | L1 | PAPKEDPLKKY | 460 | 11 | | 32307 |
| HPV16 | L1 | PDPNKFGF | 104 | 8 | | 32308 |
| HPV16 | L1 | PDTQRLVWA | 119 | 9 | | 32309 |
| HPV16 | L1 | PDYIKMVSEPY | 258 | 11 | | 32310 |
| HPV16 | L1 | PGGTLEDTY | 436 | 9 | | 32311 |
| HPV16 | L1 | PGGTLEDTYR | 436 | 10 | | 32312 |
| HPV16 | L1 | PGGTLEDTYRF | 436 | 11 | | 32313 |
| HPV16 | L1 | PIGEHWGK | 190 | 8 | | 32314 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | L1 | PIKKPNNNK | 77 | 9 | | 32315 |
| HPV16 | L1 | PLDICTSICK | 247 | 10 | | 32316 |
| HPV16 | L1 | PLDICTSICKY | 247 | 11 | | 32317 |
| HPV16 | L1 | PLGRKFLLQA | 489 | 10 | | 32318 |
| HPV16 | L1 | PLGVGISGH | 138 | 9 | | 32319 |
| HPV16 | L1 | PSGSMVTSDA | 321 | 10 | | 32320 |
| HPV16 | L1 | PTTSSTSTTA | 515 | 10 | | 32321 |
| HPV16 | L1 | PTTSSTSTTAK | 515 | 11 | | 32322 |
| HPV16 | L1 | PVSKVVSTDEY | 43 | 11 | | 32323 |
| HPV16 | L1 | QAGLKAKPK | 497 | 9 | | 32324 |
| HPV16 | L1 | QAGLKAKPKF | 497 | 10 | | 32325 |
| HPV16 | L1 | QAIACQKH | 450 | 8 | | 32326 |
| HPV16 | L1 | QDGDMVDTGF | 222 | 10 | | 32327 |
| HPV16 | L1 | QFIFQLCK | 399 | 8 | | 32328 |
| HPV16 | L1 | QFPLGRKF | 487 | 8 | | 32329 |
| HPV16 | L1 | QIFNKPYWLQR | 331 | 11 | | 32330 |
| HPV16 | L1 | QLCKITLTA | 403 | 9 | | 32331 |
| HPV16 | L1 | QLCLIGCK | 181 | 8 | | 32332 |
| HPV16 | L1 | QLFVTVVDTTR | 354 | 11 | | 32333 |
| HPV16 | L1 | QMFVRHLF | 280 | 8 | | 32334 |
| HPV16 | L1 | QMFVRHLFNR | 280 | 10 | | 32335 |
| HPV16 | L1 | QMFVRHLFNRA | 280 | 11 | | 32336 |
| HPV16 | L1 | QMSLWLPSEA | 26 | 10 | | 32337 |
| HPV16 | L1 | QTQLCLIGCK | 179 | 10 | | 32338 |
| HPV16 | L1 | RFVTSQAIA | 445 | 9 | | 32339 |
| HPV16 | L1 | RIHLPDPNK | 100 | 9 | | 32340 |
| HPV16 | L1 | RIHLPDPNKF | 100 | 10 | | 32341 |
| HPV16 | L1 | RLLAVGHPY | 67 | 9 | | 32342 |
| HPV16 | L1 | RLLAVGHPYF | 67 | 10 | | 32343 |
| HPV16 | L1 | RSTNMSLCA | 364 | 9 | | 32344 |
| HPV16 | L1 | RSTNMSLCAA | 364 | 10 | | 32345 |
| HPV16 | L1 | RTNIYYHA | 56 | 8 | | 32346 |
| HPV16 | L1 | SADLDQFPLGR | 482 | 11 | | 32347 |
| HPV16 | L1 | SDAQIFNK | 328 | 8 | | 32348 |
| HPV16 | L1 | SDAQIFNKPY | 328 | 10 | | 32349 |
| HPV16 | L1 | SFYNPDTQR | 115 | 9 | | 32350 |
| HPV16 | L1 | SGHPLLNK | 144 | 8 | | 32351 |
| HPV16 | L1 | SGLQYRVF | 92 | 8 | | 32352 |
| HPV16 | L1 | SGLQYRVFR | 92 | 9 | | 32353 |
| HPV16 | L1 | SGLQYRVFRIH | 92 | 11 | | 32354 |
| HPV16 | L1 | SGSMVTSDA | 322 | 9 | | 32355 |
| HPV16 | L1 | SGSTANLA | 306 | 8 | | 32356 |
| HPV16 | L1 | SICKYPDY | 253 | 8 | | 32357 |
| HPV16 | L1 | SICKYPDYIK | 253 | 10 | | 32358 |
| HPV16 | L1 | SLFFYLRR | 271 | 8 | | 32359 |
| HPV16 | L1 | SLWLPSEA | 28 | 8 | | 32360 |
| HPV16 | L1 | SLWLPSEATVY | 28 | 11 | | 32361 |
| HPV16 | L1 | SMVTSDAQIF | 324 | 10 | | 32362 |
| HPV16 | L1 | SSTSTTAK | 518 | 8 | | 32363 |
| HPV16 | L1 | SSTSTTAKR | 518 | 9 | | 32364 |
| HPV16 | L1 | SSTSTTAKRK | 518 | 10 | | 32365 |
| HPV16 | L1 | SSTSTTAKRKK | 518 | 11 | | 32366 |
| HPV16 | L1 | STANLASSNY | 308 | 10 | | 32367 |
| HPV16 | L1 | STANLASSNYF | 308 | 11 | | 32368 |
| HPV16 | L1 | STDEYVAR | 49 | 8 | | 32369 |
| HPV16 | L1 | STILEDWNF | 422 | 9 | | 32370 |
| HPV16 | L1 | STNMSLCA | 365 | 8 | | 32371 |
| HPV16 | L1 | STNMSLCAA | 365 | 9 | | 32372 |
| HPV16 | L1 | STSETTYK | 375 | 8 | | 32373 |
| HPV16 | L1 | STSTTAKR | 519 | 8 | | 32374 |
| HPV16 | L1 | STSTTAKRK | 519 | 9 | | 32375 |
| HPV16 | L1 | STSTTAKRKK | 519 | 10 | | 32376 |
| HPV16 | L1 | STSTTAKRKKR | 519 | 11 | | 32377 |
| HPV16 | L1 | STTAKRKK | 521 | 8 | | 32378 |
| HPV16 | L1 | STTAKRKKR | 521 | 9 | | 32379 |
| HPV16 | L1 | STTAKRKKRK | 521 | 10 | | 32380 |
| HPV16 | L1 | TADVMTYIH | 410 | 9 | | 32381 |
| HPV16 | L1 | TAKRKKRK | 523 | 8 | | 32382 |
| HPV16 | L1 | TANLASSNY | 309 | 9 | | 32383 |
| HPV16 | L1 | TANLASSNYF | 309 | 10 | | 32384 |
| HPV16 | L1 | TCYENDVNVY | 12 | 10 | | 32385 |
| HPV16 | L1 | TCYENDVNVYH | 12 | 11 | | 32386 |
| HPV16 | L1 | TDEYVARTNIY | 50 | 11 | | 32387 |
| HPV16 | L1 | TFIYILVITCY | 4 | 11 | | 32388 |
| HPV16 | L1 | TFWEVNLK | 471 | 8 | | 32389 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | L1 | TFWEVNLKEK | 471 | 10 | | 32390 |
| HPV16 | L1 | TFWEVNLKEKF | 471 | 11 | | 32391 |
| HPV16 | L1 | TGFGAMDF | 229 | 8 | | 32392 |
| HPV16 | L1 | TILEDWNF | 423 | 8 | | 32393 |
| HPV16 | L1 | TLEDTYRF | 439 | 8 | | 32394 |
| HPV16 | L1 | TLTADVMTY | 408 | 9 | | 32395 |
| HPV16 | L1 | TLTADVMTYIH | 408 | 11 | | 32396 |
| HPV16 | L1 | TSDAQIFNK | 327 | 9 | | 32397 |
| HPV16 | L1 | TSDAQIFNKPY | 327 | 11 | | 32398 |
| HPV16 | L1 | TSETTYKNTNF | 376 | 11 | | 32399 |
| HPV16 | L1 | TSFYNPDTQR | 114 | 10 | | 32400 |
| HPV16 | L1 | TSICKYPDY | 252 | 9 | | 32401 |
| HPV16 | L1 | TSICKYPDYIK | 252 | 11 | | 32402 |
| HPV16 | L1 | TSQAIACQK | 448 | 9 | | 32403 |
| HPV16 | L1 | TSQAIACQKH | 448 | 10 | | 32404 |
| HPV16 | L1 | TSRLLAVGH | 65 | 9 | | 32405 |
| HPV16 | L1 | TSRLLAVGHPY | 65 | 11 | | 32406 |
| HPV16 | L1 | TSSTSTTA | 517 | 8 | | 32407 |
| HPV16 | L1 | TSSTSTTAK | 517 | 9 | | 32408 |
| HPV16 | L1 | TSSTSTTAKR | 517 | 10 | | 32409 |
| HPV16 | L1 | TSSTSTTAKRK | 517 | 11 | | 32410 |
| HPV16 | L1 | TSTTAKRK | 520 | 8 | | 32411 |
| HPV16 | L1 | TSTTAKRKK | 520 | 9 | | 32412 |
| HPV16 | L1 | TSTTAKRKKR | 520 | 10 | | 32413 |
| HPV16 | L1 | TSTTAKRKKRK | 520 | 11 | | 32414 |
| HPV16 | L1 | TTAKRKKR | 522 | 8 | | 32415 |
| HPV16 | L1 | TTAKRKKRK | 522 | 9 | | 32416 |
| HPV16 | L1 | TTRSTNMSLCA | 362 | 11 | | 32417 |
| HPV16 | L1 | TTSSTSTTA | 516 | 9 | | 32418 |
| HPV16 | L1 | TTSSTSTTAK | 516 | 10 | | 32419 |
| HPV16 | L1 | TTSSTSTTAKR | 516 | 11 | | 32420 |
| HPV16 | L1 | TTYKNTNF | 379 | 8 | | 32421 |
| HPV16 | L1 | TTYKNTNFK | 379 | 9 | | 32422 |
| HPV16 | L1 | TTYKNTNFKEY | 379 | 11 | | 32423 |
| HPV16 | L1 | TVYLPPVPVSK | 36 | 11 | | 32424 |
| HPV16 | L1 | VARTNIYY | 54 | 8 | | 32425 |
| HPV16 | L1 | VARTNIYYH | 54 | 9 | | 32426 |
| HPV16 | L1 | VARTNIYYHA | 54 | 10 | | 32427 |
| HPV16 | L1 | VDNRECISMDY | 167 | 11 | | 32428 |
| HPV16 | L1 | VDTGFGAMDF | 227 | 10 | | 32429 |
| HPV16 | L1 | VFRIHLPDPNK | 98 | 11 | | 32430 |
| HPV16 | L1 | VGENVPDDLY | 293 | 10 | | 32431 |
| HPV16 | L1 | VGHPYFPIK | 71 | 9 | | 32432 |
| HPV16 | L1 | VGHPYFPIKK | 71 | 10 | | 32433 |
| HPV16 | L1 | VGISGHPLLNK | 141 | 11 | | 32434 |
| HPV16 | L1 | VSEPYGDSLF | 264 | 10 | | 32435 |
| HPV16 | L1 | VSEPYGDSLFF | 264 | 11 | | 32436 |
| HPV16 | L1 | VSGLQYRVF | 91 | 9 | | 32437 |
| HPV16 | L1 | VSGLQYRVFR | 91 | 10 | | 32438 |
| HPV16 | L1 | VSKVVSTDEY | 44 | 10 | | 32439 |
| HPV16 | L1 | VSTDEYVA | 48 | 8 | | 32440 |
| HPV16 | L1 | VSTDEYVAR | 48 | 9 | | 32441 |
| HPV16 | L1 | VTSDAQIF | 326 | 8 | | 32442 |
| HPV16 | L1 | VTSDAQIFNK | 326 | 10 | | 32443 |
| HPV16 | L1 | VTSQAIACQK | 447 | 10 | | 32444 |
| HPV16 | L1 | VTSQAIACQKH | 447 | 11 | | 32445 |
| HPV16 | L1 | VTVVDTTR | 357 | 8 | | 32446 |
| HPV16 | L1 | VVSTDEYVA | 47 | 9 | | 32447 |
| HPV16 | L1 | VVSTDEYVAR | 47 | 10 | | 32448 |
| HPV16 | L1 | WACVGVEVGR | 126 | 10 | | 32449 |
| HPV16 | L1 | WGKGSPCTNVA | 195 | 11 | | 32450 |
| HPV16 | L1 | WLPSEATVY | 30 | 9 | | 32451 |
| HPV16 | L1 | WLQRAQGH | 338 | 8 | | 32452 |
| HPV16 | L1 | YAANAGVDNR | 161 | 10 | | 32453 |
| HPV16 | L1 | YDLQFIFQLCK | 396 | 11 | | 32454 |
| HPV16 | L1 | YFPIKKPNNNK | 75 | 11 | | 32455 |
| HPV16 | L1 | YGDSLFFY | 268 | 8 | | 32456 |
| HPV16 | L1 | YGDSLFFYLR | 268 | 10 | | 32457 |
| HPV16 | L1 | YGDSLFFYLRR | 268 | 11 | | 32458 |
| HPV16 | L1 | YIKGSGSTA | 302 | 9 | | 32459 |
| HPV16 | L1 | YIKMVSEPY | 260 | 9 | | 32460 |
| HPV16 | L1 | YILVITCY | 7 | 8 | | 32461 |
| HPV16 | L1 | YLPPVPVSK | 38 | 9 | | 32462 |
| HPV16 | L1 | YLRHGEEY | 389 | 8 | | 32463 |
| HPV16 | L1 | YLRREQMF | 275 | 8 | | 32464 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | L1 | YLRREQMFVR | 275 | 10 | | 32465 |
| HPV16 | L1 | YLRREQMFVRH | 275 | 11 | | 32466 |
| HPV16 | L1 | YTFWEVNLK | 470 | 9 | | 32467 |
| HPV16 | L1 | YTFWEVNLKEK | 470 | 11 | | 32468 |
| HPV16 | L1 | YVARTNIY | 53 | 8 | | 32469 |
| HPV16 | L1 | YVARTNIYY | 53 | 9 | | 32470 |
| HPV16 | L1 | YVARTNIYYH | 53 | 10 | | 32471 |
| HPV16 | L1 | YVARTNIYYHA | 53 | 11 | | 32472 |
| HPV16 | L2 | ADAGDFYLH | 441 | 9 | | 32473 |
| HPV16 | L2 | AFITTPTK | 241 | 8 | | 32474 |
| HPV16 | L2 | AGDFYLHPSY | 443 | 10 | | 32475 |
| HPV16 | L2 | AGDFYLHPSYY | 443 | 11 | | 32476 |
| HPV16 | L2 | AGTCPPDIIPK | 25 | 11 | | 32477 |
| HPV16 | L2 | ALHRPALTSR | 288 | 10 | | 32478 |
| HPV16 | L2 | ALHRPALTSRR | 288 | 11 | | 32479 |
| HPV16 | L2 | ALPTSINNGLY | 356 | 11 | | 32480 |
| HPV16 | L2 | ALTSRRTGIR | 293 | 10 | | 32481 |
| HPV16 | L2 | ALTSRRTGIRY | 293 | 11 | | 32482 |
| HPV16 | L2 | ASATQLYK | 13 | 8 | | 32483 |
| HPV16 | L2 | ASATQLYKTCK | 13 | 11 | | 32484 |
| HPV16 | L2 | ATDTLAPVR | 82 | 9 | | 32485 |
| HPV16 | L2 | ATQLYKTCK | 15 | 9 | | 32486 |
| HPV16 | L2 | ATQLYKTCKQA | 15 | 11 | | 32487 |
| HPV16 | L2 | DAGDFYLH | 442 | 8 | | 32488 |
| HPV16 | L2 | DAGDFYLHPSY | 442 | 11 | | 32489 |
| HPV16 | L2 | DFLDIVALH | 282 | 9 | | 32490 |
| HPV16 | L2 | DFLDIVALHR | 282 | 10 | | 32491 |
| HPV16 | L2 | DFSTIDSA | 329 | 8 | | 32492 |
| HPV16 | L2 | DFYLHPSY | 445 | 8 | | 32493 |
| HPV16 | L2 | DFYLHPSYY | 445 | 9 | | 32494 |
| HPV16 | L2 | DIIPKVEGK | 31 | 9 | | 32495 |
| HPV16 | L2 | DIPINITDQA | 415 | 10 | | 32496 |
| HPV16 | L2 | DIVALHRPA | 285 | 9 | | 32497 |
| HPV16 | L2 | DVDNTLYF | 261 | 8 | | 32498 |
| HPV16 | L2 | EGIDVDNTLY | 258 | 10 | | 32499 |
| HPV16 | L2 | EGIDVDNTLYF | 258 | 11 | | 32500 |
| HPV16 | L2 | ELQTITPSTY | 340 | 10 | | 32501 |
| HPV16 | L2 | ETSFIDAGA | 111 | 9 | | 32502 |
| HPV16 | L2 | FFSDVSLA | 465 | 8 | | 32503 |
| HPV16 | L2 | FFSDVSLAA | 465 | 9 | | 32504 |
| HPV16 | L2 | FITTPTKLITY | 242 | 11 | | 32505 |
| HPV16 | L2 | FLDIVALH | 283 | 8 | | 32506 |
| HPV16 | L2 | FLDIVALHR | 283 | 9 | | 32507 |
| HPV16 | L2 | FLDIVALHRPA | 283 | 11 | | 32508 |
| HPV16 | L2 | FSDVSLAA | 466 | 8 | | 32509 |
| HPV16 | L2 | FSSNDNSINIA | 268 | 11 | | 32510 |
| HPV16 | L2 | FTLSSSTISTH | 181 | 11 | | 32511 |
| HPV16 | L2 | GAKVHYYY | 321 | 8 | | 32512 |
| HPV16 | L2 | GAKVHYYYDF | 321 | 10 | | 32513 |
| HPV16 | L2 | GDFYLHPSY | 444 | 9 | | 32514 |
| HPV16 | L2 | GDFYLHPSYY | 444 | 10 | | 32515 |
| HPV16 | L2 | GIDVDNTLY | 259 | 9 | | 32516 |
| HPV16 | L2 | GIDVDNTLYF | 259 | 10 | | 32517 |
| HPV16 | L2 | GIGTGSGTGGR | 59 | 11 | | 32518 |
| HPV16 | L2 | GIRYSRIGNK | 300 | 10 | | 32519 |
| HPV16 | L2 | GLYDIYADDF | 364 | 10 | | 32520 |
| HPV16 | L2 | GLYSRTTQQVK | 226 | 11 | | 32521 |
| HPV16 | L2 | GSGTGGRTGY | 63 | 10 | | 32522 |
| HPV16 | L2 | GSPQYTIIA | 433 | 9 | | 32523 |
| HPV16 | L2 | GSPQYTIIADA | 433 | 11 | | 32524 |
| HPV16 | L2 | GSRPVARLGLY | 218 | 11 | | 32525 |
| HPV16 | L2 | GTCPPDIIPK | 26 | 10 | | 32526 |
| HPV16 | L2 | GTGGRTGY | 65 | 8 | | 32527 |
| HPV16 | L2 | GTGSGTGGR | 61 | 9 | | 32528 |
| HPV16 | L2 | IADAGDFY | 440 | 8 | | 32529 |
| HPV16 | L2 | IADAGDFYLH | 440 | 10 | | 32530 |
| HPV16 | L2 | IADQILQY | 41 | 8 | | 32531 |
| HPV16 | L2 | IDVDNTLY | 260 | 8 | | 32532 |
| HPV16 | L2 | IDVDNTLYF | 260 | 9 | | 32533 |
| HPV16 | L2 | IGAKVHYY | 320 | 8 | | 32534 |
| HPV16 | L2 | IGAKVHYYY | 320 | 9 | | 32535 |
| HPV16 | L2 | IGAKVHYYYDF | 320 | 11 | | 32536 |
| HPV16 | L2 | IGNKQTLR | 306 | 8 | | 32537 |
| HPV16 | L2 | IGNKQTLRTR | 306 | 10 | | 32538 |
| HPV16 | L2 | IGTGSGTGGR | 60 | 10 | | 32539 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | L2 | IIADAGDF | 439 | 8 | | 32540 |
| HPV16 | L2 | IIADAGDFY | 439 | 9 | | 32541 |
| HPV16 | L2 | IIADAGDFYLH | 439 | 11 | | 32542 |
| HPV16 | L2 | IIPKVEGK | 32 | 8 | | 32543 |
| HPV16 | L2 | IIPKVEGKTIA | 32 | 11 | | 32544 |
| HPV16 | L2 | ILQYGSMGVF | 45 | 10 | | 32545 |
| HPV16 | L2 | ILQYGSMGVFF | 45 | 11 | | 32546 |
| HPV16 | L2 | ITPSTYTTTSH | 344 | 11 | | 32547 |
| HPV16 | L2 | ITTPTKLITY | 243 | 10 | | 32548 |
| HPV16 | L2 | ITTSTDTTPA | 135 | 10 | | 32549 |
| HPV16 | L2 | ITYDNPAY | 250 | 8 | | 32550 |
| HPV16 | L2 | IVALHRPA | 286 | 8 | | 32551 |
| HPV16 | L2 | IVPGSPQY | 430 | 8 | | 32552 |
| HPV16 | L2 | IVSLVEETSF | 105 | 10 | | 32553 |
| HPV16 | L2 | KLITYDNPA | 248 | 9 | | 32554 |
| HPV16 | L2 | KLITYDNPAY | 248 | 10 | | 32555 |
| HPV16 | L2 | KSIGAKVH | 318 | 8 | | 32556 |
| HPV16 | L2 | KSIGAKVHY | 318 | 9 | | 32557 |
| HPV16 | L2 | KSIGAKVHYY | 318 | 10 | | 32558 |
| HPV16 | L2 | KSIGAKVHYYY | 318 | 11 | | 32559 |
| HPV16 | L2 | KTIADQILQY | 39 | 10 | | 32560 |
| HPV16 | L2 | KVEGKTIA | 35 | 8 | | 32561 |
| HPV16 | L2 | KVHYYYDF | 323 | 8 | | 32562 |
| HPV16 | L2 | LDIVALHR | 284 | 8 | | 32563 |
| HPV16 | L2 | LDIVALHRPA | 284 | 10 | | 32564 |
| HPV16 | L2 | LGTRPPTA | 75 | 8 | | 32565 |
| HPV16 | L2 | LIPVPGSPQY | 427 | 11 | | 32566 |
| HPV16 | L2 | LITYDNPA | 249 | 8 | | 32567 |
| HPV16 | L2 | LITYDNPAY | 249 | 9 | | 32568 |
| HPV16 | L2 | LSSSTISTH | 183 | 9 | | 32569 |
| HPV16 | L2 | LSSSTISTHNY | 183 | 11 | | 32570 |
| HPV16 | L2 | LTSRRTGIR | 294 | 9 | | 32571 |
| HPV16 | L2 | LTSRRTGIRY | 294 | 10 | | 32572 |
| HPV16 | L2 | LVEETSFIDA | 108 | 10 | | 32573 |
| HPV16 | L2 | MLRKRRKR | 454 | 8 | | 32574 |
| HPV16 | L2 | MLRKRRKRLPY | 454 | 11 | | 32575 |
| HPV16 | L2 | NDNSINIA | 271 | 8 | | 32576 |
| HPV16 | L2 | NGLYDIYA | 363 | 8 | | 32577 |
| HPV16 | L2 | NGLYDIYADDF | 363 | 11 | | 32578 |
| HPV16 | L2 | NIAPDPDF | 276 | 8 | | 32579 |
| HPV16 | L2 | NSINIAPDPDF | 273 | 11 | | 32580 |
| HPV16 | L2 | NTTIPFGGA | 397 | 9 | | 32581 |
| HPV16 | L2 | NTTIPFGGAY | 397 | 10 | | 32582 |
| HPV16 | L2 | NTVTTVTTH | 150 | 9 | | 32583 |
| HPV16 | L2 | PAETGGHF | 174 | 8 | | 32584 |
| HPV16 | L2 | PAFITTPTK | 240 | 9 | | 32585 |
| HPV16 | L2 | PALTSRRTGIR | 292 | 11 | | 32586 |
| HPV16 | L2 | PANTTIPF | 395 | 8 | | 32587 |
| HPV16 | L2 | PANTTIPFGGA | 395 | 11 | | 32588 |
| HPV16 | L2 | PDFLDIVA | 281 | 8 | | 32589 |
| HPV16 | L2 | PDFLDIVALH | 281 | 10 | | 32590 |
| HPV16 | L2 | PDFLDIVALHR | 281 | 11 | | 32591 |
| HPV16 | L2 | PDIIPKVEGK | 30 | 10 | | 32592 |
| HPV16 | L2 | PDIPINITDQA | 414 | 11 | | 32593 |
| HPV16 | L2 | PDPDFLDIVA | 279 | 10 | | 32594 |
| HPV16 | L2 | PGSPQYTIIA | 432 | 10 | | 32595 |
| HPV16 | L2 | PGSRPVAR | 217 | 8 | | 32596 |
| HPV16 | L2 | PINITDQA | 417 | 8 | | 32597 |
| HPV16 | L2 | PIPGSRPVA | 215 | 9 | | 32598 |
| HPV16 | L2 | PIPGSRPVAR | 215 | 10 | | 32599 |
| HPV16 | L2 | PIVPGSPQY | 429 | 9 | | 32600 |
| HPV16 | L2 | PLGTRPPTA | 74 | 9 | | 32601 |
| HPV16 | L2 | PSIPPDVSGF | 124 | 10 | | 32602 |
| HPV16 | L2 | PSTSLSGY | 386 | 8 | | 32603 |
| HPV16 | L2 | PSTSLSGYIPA | 386 | 11 | | 32604 |
| HPV16 | L2 | PSTYTTTSH | 346 | 9 | | 32605 |
| HPV16 | L2 | PSTYTTTSHA | 346 | 10 | | 32606 |
| HPV16 | L2 | PSTYTTTSHAA | 346 | 11 | | 32607 |
| HPV16 | L2 | PSVLQPPTPA | 166 | 10 | | 32608 |
| HPV16 | L2 | PSVPSTSLSGY | 383 | 11 | | 32609 |
| HPV16 | L2 | PSYYMLRK | 450 | 8 | | 32610 |
| HPV16 | L2 | PSYYMLRKR | 450 | 9 | | 32611 |
| HPV16 | L2 | PSYYMLRKRR | 450 | 10 | | 32612 |
| HPV16 | L2 | PSYYMLRKRRK | 450 | 11 | | 32613 |
| HPV16 | L2 | PTATDTLA | 80 | 8 | | 32614 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | L2 | PTATDTLAPVR | 80 | 11 | | 32615 |
| HPV16 | L2 | PTKLITYDNPA | 246 | 11 | | 32616 |
| HPV16 | L2 | PTPAETGGH | 172 | 9 | | 32617 |
| HPV16 | L2 | PTPAETGGHF | 172 | 10 | | 32618 |
| HPV16 | L2 | PTSINNGLY | 358 | 9 | | 32619 |
| HPV16 | L2 | PVARLGLY | 221 | 8 | | 32620 |
| HPV16 | L2 | PVARLGLYSR | 221 | 10 | | 32621 |
| HPV16 | L2 | QILQYGSMGVF | 44 | 11 | | 32622 |
| HPV16 | L2 | QLYKTCKQA | 17 | 9 | | 32623 |
| HPV16 | L2 | QTITPSTY | 342 | 8 | | 32624 |
| HPV16 | L2 | QTLRTRSGK | 310 | 9 | | 32625 |
| HPV16 | L2 | QVKVVDPA | 234 | 8 | | 32626 |
| HPV16 | L2 | QVKVVDPAF | 234 | 9 | | 32627 |
| HPV16 | L2 | RASATQLY | 12 | 8 | | 32628 |
| HPV16 | L2 | RASATQLYK | 12 | 9 | | 32629 |
| HPV16 | L2 | RIGNKQTLR | 305 | 9 | | 32630 |
| HPV16 | L2 | RIGNKQTLRTR | 305 | 11 | | 32631 |
| HPV16 | L2 | RSAKRTKR | 5 | 8 | | 32632 |
| HPV16 | L2 | RSAKRTKRA | 5 | 9 | | 32633 |
| HPV16 | L2 | RSAKRTKRASA | 5 | 11 | | 32634 |
| HPV16 | L2 | RSGKSIGA | 315 | 8 | | 32635 |
| HPV16 | L2 | RSGKSIGAK | 315 | 9 | | 32636 |
| HPV16 | L2 | RSGKSIGAKVH | 315 | 11 | | 32637 |
| HPV16 | L2 | RTGIRYSR | 298 | 8 | | 32638 |
| HPV16 | L2 | RTGYIPLGTR | 69 | 10 | | 32639 |
| HPV16 | L2 | RTKRASATQLY | 9 | 11 | | 32640 |
| HPV16 | L2 | RTRSGKSIGA | 313 | 10 | | 32641 |
| HPV16 | L2 | RTRSGKSIGAK | 313 | 11 | | 32642 |
| HPV16 | L2 | SAKRTKRA | 6 | 8 | | 32643 |
| HPV16 | L2 | SAKRTKRASA | 6 | 10 | | 32644 |
| HPV16 | L2 | SATQLYKTCK | 14 | 10 | | 32645 |
| HPV16 | L2 | SGKSIGAK | 316 | 8 | | 32646 |
| HPV16 | L2 | SGKSGAKVH | 316 | 10 | | 32647 |
| HPV16 | L2 | SGKSIGAKVHY | 316 | 11 | | 32648 |
| HPV16 | L2 | SGTGGRTGY | 64 | 9 | | 32649 |
| HPV16 | L2 | SIGAKVHY | 319 | 8 | | 32650 |
| HPV16 | L2 | SIGAKVHYY | 319 | 9 | | 32651 |
| HPV16 | L2 | SIGAKVHYYY | 319 | 10 | | 32652 |
| HPV16 | L2 | SINIAPDPDF | 274 | 10 | | 32653 |
| HPV16 | L2 | SINNGLYDIY | 360 | 10 | | 32654 |
| HPV16 | L2 | SINNGLYDIYA | 360 | 11 | | 32655 |
| HPV16 | L2 | SIPPDVSGF | 125 | 9 | | 32656 |
| HPV16 | L2 | SITTSTDTTPA | 134 | 11 | | 32657 |
| HPV16 | L2 | SIVSLVEETSF | 104 | 11 | | 32658 |
| HPV16 | L2 | SLSGYIPA | 389 | 8 | | 32659 |
| HPV16 | L2 | SLVEETSF | 107 | 8 | | 32660 |
| HPV16 | L2 | SLVEETSFIDA | 107 | 11 | | 32661 |
| HPV16 | L2 | SSNDNSINIA | 269 | 10 | | 32662 |
| HPV16 | L2 | SSSTISTH | 184 | 8 | | 32663 |
| HPV16 | L2 | SSSTISTHNY | 184 | 10 | | 32664 |
| HPV16 | L2 | SSTISTHNY | 185 | 9 | | 32665 |
| HPV16 | L2 | SSTPIPGSR | 212 | 9 | | 32666 |
| HPV16 | L2 | STISTHNY | 186 | 8 | | 32667 |
| HPV16 | L2 | STPIPGSR | 213 | 8 | | 32668 |
| HPV16 | L2 | STPIPGSRPVA | 213 | 11 | | 32669 |
| HPV16 | L2 | STSLSGYIPA | 387 | 10 | | 32670 |
| HPV16 | L2 | STYTTTSH | 347 | 8 | | 32671 |
| HPV16 | L2 | STYTTTSHA | 347 | 9 | | 32672 |
| HPV16 | L2 | STYTTTSHAA | 347 | 10 | | 32673 |
| HPV16 | L2 | SVLQPPTPA | 167 | 9 | | 32674 |
| HPV16 | L2 | SVPSTSLSGY | 384 | 10 | | 32675 |
| HPV16 | L2 | TATDTLAPVR | 81 | 10 | | 32676 |
| HPV16 | L2 | TCPPDIIPK | 27 | 9 | | 32677 |
| HPV16 | L2 | TDTLAPVR | 83 | 8 | | 32678 |
| HPV16 | L2 | TGIRYSRIGNK | 299 | 11 | | 32679 |
| HPV16 | L2 | TGSGTGGR | 62 | 8 | | 32680 |
| HPV16 | L2 | TGSGTGGRTGY | 62 | 11 | | 32681 |
| HPV16 | L2 | TGYIPLGTR | 70 | 9 | | 32682 |
| HPV16 | L2 | TIADQILQY | 40 | 9 | | 32683 |
| HPV16 | L2 | TIIADAGDF | 438 | 9 | | 32684 |
| HPV16 | L2 | TIIADAGDFY | 438 | 10 | | 32685 |
| HPV16 | L2 | TIPFGGAY | 399 | 8 | | 32686 |
| HPV16 | L2 | TLRTRSGK | 311 | 8 | | 32687 |
| HPV16 | L2 | TLSSSTISTH | 182 | 10 | | 32688 |
| HPV16 | L2 | TSFIDAGA | 112 | 8 | | 32689 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV16 | L2 | TSINNGLY | 359 | 8 | | 32690 |
| HPV16 | L2 | TSINNGLYDIY | 359 | 11 | | 32691 |
| HPV16 | L2 | TSLSGYIPA | 388 | 9 | | 32692 |
| HPV16 | L2 | TSRRTGIR | 295 | 8 | | 32693 |
| HPV16 | L2 | TSRRTGIRY | 295 | 9 | | 32694 |
| HPV16 | L2 | TSRRTGIRYSR | 295 | 11 | | 32695 |
| HPV16 | L2 | TSSTPIPGSR | 211 | 10 | | 32696 |
| HPV16 | L2 | TSTDTTPA | 137 | 8 | | 32697 |
| HPV16 | L2 | TTHNNPTF | 156 | 8 | | 32698 |
| HPV16 | L2 | TTIPFGGA | 398 | 8 | | 32699 |
| HPV16 | L2 | TTIPFGGAY | 398 | 9 | | 32700 |
| HPV16 | L2 | TTPTKLITY | 244 | 9 | | 32701 |
| HPV16 | L2 | TTQQVKVVDPA | 231 | 11 | | 32702 |
| HPV16 | L2 | TTSTDTTPA | 136 | 9 | | 32703 |
| HPV16 | L2 | TTVTTHNNPTF | 153 | 11 | | 32704 |
| HPV16 | L2 | TVTTHNNPTF | 154 | 10 | | 32705 |
| HPV16 | L2 | TVTTVTTH | 151 | 8 | | 32706 |
| HPV16 | L2 | VALHRPALTSR | 287 | 11 | | 32707 |
| HPV16 | L2 | VARLGLYSR | 222 | 9 | | 32708 |
| HPV16 | L2 | VDPAFITTPTK | 238 | 11 | | 32709 |
| HPV16 | L2 | VLQPPTPA | 168 | 8 | | 32710 |
| HPV16 | L2 | VSLVEETSF | 106 | 9 | | 32711 |
| HPV16 | L2 | VTSSTPIPGSR | 210 | 11 | | 32712 |
| HPV16 | L2 | VTTHNNPTF | 155 | 9 | | 32713 |
| HPV16 | L2 | YDFSTIDSA | 328 | 9 | | 32714 |
| HPV16 | L2 | YDIYADDF | 366 | 8 | | 32715 |
| HPV16 | L2 | YFFSDVSLA | 464 | 9 | | 32716 |
| HPV16 | L2 | YFFSDVSLAA | 464 | 10 | | 32717 |
| HPV16 | L2 | YGSMGVFF | 48 | 8 | | 32718 |
| HPV16 | L2 | YIPANTTIPF | 393 | 10 | | 32719 |
| HPV16 | L2 | YIPLGTRPPTA | 72 | 11 | | 32720 |
| HPV16 | L2 | YLHPSYYMLR | 447 | 10 | | 32721 |
| HPV16 | L2 | YLHPSYYMLRK | 447 | 11 | | 32722 |
| HPV16 | L2 | YMLRKRRK | 453 | 8 | | 32723 |
| HPV16 | L2 | YMLRKRRKR | 453 | 9 | | 32724 |
| HPV16 | L2 | YSRIGNKQTLR | 303 | 11 | | 32725 |
| HPV16 | L2 | YSRTTQQVK | 228 | 9 | | 32726 |
| HPV16 | L2 | YTIIADAGDF | 437 | 10 | | 32727 |
| HPV16 | L2 | YTIIADAGDFY | 437 | 11 | | 32728 |
| HPV16 | L2 | YTTTSHAA | 349 | 8 | | 32729 |
| HPV18 | E1 | AAAFLKSNCQA | 396 | 11 | | 32730 |
| HPV18 | E1 | AAFLKSNCQA | 397 | 10 | | 32731 |
| HPV18 | E1 | AAFLKSNCQAK | 397 | 11 | | 32732 |
| HPV18 | E1 | ADSNSNAA | 390 | 8 | | 32733 |
| HPV18 | E1 | ADSNSNAAA | 390 | 9 | | 32734 |
| HPV18 | E1 | ADSNSNAAAF | 390 | 10 | | 32735 |
| HPV18 | E1 | ADTEGNPF | 636 | 8 | | 32736 |
| HPV18 | E1 | ADTEGNPFGTF | 636 | 11 | | 32737 |
| HPV18 | E1 | AFEYALLA | 383 | 8 | | 32738 |
| HPV18 | E1 | AFLKSNCQA | 398 | 9 | | 32739 |
| HPV18 | E1 | AFLKSNCQAK | 398 | 10 | | 32740 |
| HPV18 | E1 | AFLKSNCQAKY | 398 | 11 | | 32741 |
| HPV18 | E1 | AIFGVNPTIA | 246 | 10 | | 32742 |
| HPV18 | E1 | ALDGNPISIDR | 546 | 11 | | 32743 |
| HPV18 | E1 | ALFHAQEVH | 68 | 9 | | 32744 |
| HPV18 | E1 | ALKSFLKGTPK | 466 | 11 | | 32745 |
| HPV18 | E1 | ALLADSNSNA | 387 | 10 | | 32746 |
| HPV18 | E1 | ALLADSNSNAA | 387 | 11 | | 32747 |
| HPV18 | E1 | ALLRYKCGK | 284 | 9 | 0.0900 | 32748 |
| HPV18 | E1 | ALLRYKCGKSR | 284 | 11 | | 32749 |
| HPV18 | E1 | AMLAVFKDTY | 213 | 10 | | 32750 |
| HPV18 | E1 | ATDTGSDMVDF | 40 | 11 | | 32751 |
| HPV18 | E1 | ATMCKHYR | 413 | 8 | | 32752 |
| HPV18 | E1 | ATMCKHYRR | 413 | 9 | 0.0300 | 32753 |
| HPV18 | E1 | ATMCKHYRRA | 413 | 10 | | 32754 |
| HPV18 | E1 | ATTTCWTY | 531 | 8 | | 32755 |
| HPV18 | E1 | ATTTCWTYF | 531 | 9 | | 32756 |
| HPV18 | E1 | AVFKDTYGLSF | 216 | 11 | | 32757 |
| HPV18 | E1 | AVISFVNSTSH | 504 | 11 | | 32758 |
| HPV18 | E1 | CATMCKHY | 412 | 8 | | 32759 |
| HPV18 | E1 | CATMCKHYR | 412 | 9 | 0.0012 | 32760 |
| HPV18 | E1 | CATMCKHYRR | 412 | 10 | | 32761 |
| HPV18 | E1 | CATMCKHYRRA | 412 | 11 | | 32762 |
| HPV18 | E1 | CFFERTWSR | 618 | 9 | | 32763 |
| HPV18 | E1 | CGKSRLTVA | 290 | 9 | | 32764 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E1 | CGKSRLTVAK | 290 | 10 | | 32765 |
| HPV18 | E1 | CGPANTGK | 483 | 8 | | 32766 |
| HPV18 | E1 | CGPANTGKSY | 483 | 10 | | 32767 |
| HPV18 | E1 | CGPANTGKSYF | 483 | 11 | | 32768 |
| HPV18 | E1 | CLVFCGPA | 479 | 8 | | 32769 |
| HPV18 | E1 | CMLIQPPK | 311 | 8 | | 32770 |
| HPV18 | E1 | CMLIQPPKLR | 311 | 10 | | 32771 |
| HPV18 | E1 | CSGGSTEA | 160 | 8 | | 32772 |
| HPV18 | E1 | CSKIDEGGDWR | 437 | 11 | | 32773 |
| HPV18 | E1 | CTDWVTAIF | 240 | 9 | | 32774 |
| HPV18 | E1 | CTIAQLKDLLK | 196 | 11 | | 32775 |
| HPV18 | E1 | DADTEGNPF | 635 | 9 | | 32776 |
| HPV18 | E1 | DAQVLHVLK | 78 | 9 | | 32777 |
| HPV18 | E1 | DAQVLHVLKR | 78 | 10 | | 32778 |
| HPV18 | E1 | DAQVLHVLKRK | 78 | 11 | | 32779 |
| HPV18 | E1 | DATTTCWTY | 530 | 9 | | 32780 |
| HPV18 | E1 | DATTTCWTYF | 530 | 10 | | 32781 |
| HPV18 | E1 | DCATMCKH | 411 | 8 | | 32782 |
| HPV18 | E1 | DCATMCKHY | 411 | 9 | | 32783 |
| HPV18 | E1 | DCATMCKHYR | 411 | 10 | | 32784 |
| HPV18 | E1 | DCATMCKHYRR | 411 | 11 | | 32785 |
| HPV18 | E1 | DCKWGVLILA | 275 | 10 | | 32786 |
| HPV18 | E1 | DDATTTCWTY | 529 | 10 | | 32787 |
| HPV18 | E1 | DDATTTCWTYF | 529 | 11 | | 32788 |
| HPV18 | E1 | DFIDTQGTF | 49 | 9 | | 32789 |
| HPV18 | E1 | DGEGTGCNGWF | 8 | 11 | | 32790 |
| HPV18 | E1 | DGNPISIDR | 548 | 9 | | 32791 |
| HPV18 | E1 | DGNPISIDRK | 548 | 10 | | 32792 |
| HPV18 | E1 | DGNPISIDRKH | 548 | 11 | | 32793 |
| HPV18 | E1 | DLHEEEEDA | 628 | 9 | | 32794 |
| HPV18 | E1 | DLLKVNNK | 203 | 8 | | 32795 |
| HPV18 | E1 | DLLKVNNKQGA | 203 | 11 | | 32796 |
| HPV18 | E1 | DLSEMVQWA | 363 | 9 | | 32797 |
| HPV18 | E1 | DLSEMVQWAF | 363 | 10 | | 32798 |
| HPV18 | E1 | DLVRNFKSDK | 228 | 10 | | 32799 |
| HPV18 | E1 | DMAFEYALLA | 381 | 10 | | 32800 |
| HPV18 | E1 | DSGYGCSEVEA | 134 | 11 | | 32801 |
| HPV18 | E1 | DSNSNAAA | 391 | 8 | | 32802 |
| HPV18 | E1 | DSNSNAAAF | 391 | 9 | | 32803 |
| HPV18 | E1 | DSNSNAAAFLK | 391 | 11 | | 32804 |
| HPV18 | E1 | DTEGNPFGTF | 637 | 10 | | 32805 |
| HPV18 | E1 | DTEGNPFGTFK | 637 | 11 | | 32806 |
| HPV18 | E1 | DTGSDMVDF | 42 | 9 | | 32807 |
| HPV18 | E1 | DTKVAMLDDA | 522 | 10 | | 32808 |
| HPV18 | E1 | DTPEWIQR | 342 | 8 | | 32809 |
| HPV18 | E1 | DTQGTFCEQA | 52 | 10 | | 32810 |
| HPV18 | E1 | DVISDDEDENA | 30 | 11 | | 32811 |
| HPV18 | E1 | EDADTEGNPF | 634 | 10 | | 32812 |
| HPV18 | E1 | EFITFLGA | 459 | 8 | | 32813 |
| HPV18 | E1 | EFITFLGALK | 459 | 10 | | 32814 |
| HPV18 | E1 | EFPNAFPF | 594 | 8 | | 32815 |
| HPV18 | E1 | EFPNAFPFDK | 594 | 10 | | 32816 |
| HPV18 | E1 | EGFKTLIQPF | 256 | 10 | | 32817 |
| HPV18 | E1 | EGGDWRPIVQF | 442 | 11 | | 32818 |
| HPV18 | E1 | EGNPFGTF | 639 | 8 | | 32819 |
| HPV18 | E1 | EGNPFGTFK | 639 | 9 | | 32820 |
| HPV18 | E1 | EGNPFGTFKLR | 639 | 11 | | 32821 |
| HPV18 | E1 | EGTGCNGWF | 10 | 9 | 0.0008 | 32822 |
| HPV18 | E1 | EGTGCNGWFY | 10 | 10 | 0.0005 | 32823 |
| HPV18 | E1 | EINDKNWK | 610 | 8 | | 32824 |
| HPV18 | E1 | EINDKNWKCF | 610 | 10 | | 32825 |
| HPV18 | E1 | EINDKNWKCFF | 610 | 11 | | 32826 |
| HPV18 | E1 | EISLNSGQK | 115 | 9 | | 32827 |
| HPV18 | E1 | EISLNSGQKK | 115 | 10 | | 32828 |
| HPV18 | E1 | EISLNSGQKKA | 115 | 11 | | 32829 |
| HPV18 | E1 | ELETAQALF | 62 | 9 | | 32830 |
| HPV18 | E1 | ELETAQALFH | 62 | 10 | | 32831 |
| HPV18 | E1 | ELETAQALFHA | 62 | 11 | | 32832 |
| HPV18 | E1 | ELTDESDMA | 375 | 9 | | 32833 |
| HPV18 | E1 | ELTDESDMAF | 375 | 10 | | 32834 |
| HPV18 | E1 | ESDMAFEY | 379 | 8 | | 32835 |
| HPV18 | E1 | ESDMAFEYA | 379 | 9 | | 32836 |
| HPV18 | E1 | ESRITVFEF | 587 | 9 | | 32837 |
| HPV18 | E1 | ETAQALFH | 64 | 8 | | 32838 |
| HPV18 | E1 | ETAQALFHA | 64 | 9 | | 32839 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E1 | ETCMLIQPPK | 309 | 10 | | 32840 |
| HPV18 | E1 | EVDTELSPR | 104 | 9 | | 32841 |
| HPV18 | E1 | EVHNDAQVLH | 74 | 10 | | 32842 |
| HPV18 | E1 | FCEQAELETA | 57 | 10 | | 32843 |
| HPV18 | E1 | FCGPANTGK | 482 | 9 | | 32844 |
| HPV18 | E1 | FCGPANTGKSY | 482 | 11 | | 32845 |
| HPV18 | E1 | FDKNGNPVY | 601 | 9 | | 32846 |
| HPV18 | E1 | FDLSEMVQWA | 362 | 10 | | 32847 |
| HPV18 | E1 | FDLSEMVQWAF | 362 | 11 | | 32848 |
| HPV18 | E1 | FDTYMRNA | 539 | 8 | | 32849 |
| HPV18 | E1 | FFERTWSR | 619 | 8 | | 32850 |
| HPV18 | E1 | FGMSFIHF | 493 | 8 | | 32851 |
| HPV18 | E1 | FGTFKLRA | 643 | 8 | | 32852 |
| HPV18 | E1 | FGVNPTIA | 248 | 8 | | 32853 |
| HPV18 | E1 | FGVNPTIAEGF | 248 | 11 | | 32854 |
| HPV18 | E1 | FIDTQGTF | 50 | 8 | | 32855 |
| HPV18 | E1 | FIHFIQGA | 497 | 8 | | 32856 |
| HPV18 | E1 | FIQGAVISF | 500 | 9 | | 32857 |
| HPV18 | E1 | FITFLGALK | 460 | 9 | 0.0320 | 32858 |
| HPV18 | E1 | FITFLGALKSF | 460 | 11 | | 32859 |
| HPV18 | E1 | FLGALKSF | 463 | 8 | | 32860 |
| HPV18 | E1 | FLGALKSFLK | 463 | 10 | | 32861 |
| HPV18 | E1 | FLKGTPKK | 470 | 8 | | 32862 |
| HPV18 | E1 | FLKSNCQA | 399 | 8 | | 32863 |
| HPV18 | E1 | FLKSNCQAK | 399 | 9 | 0.0035 | 32864 |
| HPV18 | E1 | FLKSNCQAKY | 399 | 10 | | 32865 |
| HPV18 | E1 | FLRYQQIEF | 452 | 9 | | 32866 |
| HPV18 | E1 | FTDLVRNF | 226 | 8 | | 32867 |
| HPV18 | E1 | FTDLVRNFK | 226 | 9 | | 32868 |
| HPV18 | E1 | FTISDSGY | 130 | 8 | | 32869 |
| HPV18 | E1 | FVNSTSHF | 508 | 8 | | 32870 |
| HPV18 | E1 | GALKSFLK | 465 | 8 | | 32871 |
| HPV18 | E1 | GAMLAVFK | 212 | 8 | | 32872 |
| HPV18 | E1 | GAMLAVFKDTY | 212 | 11 | | 32873 |
| HPV18 | E1 | GCNGWFYVQA | 13 | 10 | | 32874 |
| HPV18 | E1 | GDTPEWIQR | 341 | 9 | 0.0008 | 32875 |
| HPV18 | E1 | GDWRPIVQF | 444 | 9 | | 32876 |
| HPV18 | E1 | GDWRPIVQFLR | 444 | 11 | | 32877 |
| HPV18 | E1 | GFKTLIQPF | 257 | 9 | | 32878 |
| HPV18 | E1 | GGDWRPIVQF | 443 | 10 | | 32879 |
| HPV18 | E1 | GLSFTDLVR | 223 | 9 | 0.0009 | 32880 |
| HPV18 | E1 | GLSFTDLVRNF | 223 | 11 | | 32881 |
| HPV18 | E1 | GMSFIHFIQGA | 494 | 11 | | 32882 |
| HPV18 | E1 | GSTENSPLGER | 92 | 11 | | 32883 |
| HPV18 | E1 | GTFKLRAGQNH | 644 | 11 | | 32884 |
| HPV18 | E1 | GTGCNGWF | 11 | 8 | | 32885 |
| HPV18 | E1 | GTGCNGWFY | 11 | 9 | 0.0004 | 32886 |
| HPV18 | E1 | GTPKKNCLVF | 473 | 10 | | 32887 |
| HPV18 | E1 | GVLILALLR | 279 | 9 | 0.0058 | 32888 |
| HPV18 | E1 | GVLILALLRY | 279 | 10 | | 32889 |
| HPV18 | E1 | GVLILALLRYK | 279 | 11 | | 32890 |
| HPV18 | E1 | GVNPTIAEGF | 249 | 10 | | 32891 |
| HPV18 | E1 | GVNPTIAEGFK | 249 | 11 | | 32892 |
| HPV18 | E1 | HAQEVHNDA | 71 | 9 | | 32893 |
| HPV18 | E1 | HFIQGAVISF | 499 | 10 | | 32894 |
| HPV18 | E1 | HFWLEPLTDTK | 514 | 11 | | 32895 |
| HPV18 | E1 | HGIDDSNF | 355 | 8 | | 32896 |
| HPV18 | E1 | HIQCLDCK | 270 | 8 | | 32897 |
| HPV18 | E1 | HVLKRKFA | 83 | 8 | | 32898 |
| HPV18 | E1 | IAQLKDLLK | 198 | 9 | 0.0003 | 32899 |
| HPV18 | E1 | IDEGGDWR | 440 | 8 | | 32900 |
| HPV18 | E1 | IDTQGTFCEQA | 51 | 11 | | 32901 |
| HPV18 | E1 | IFGVNPTIA | 247 | 9 | | 32902 |
| HPV18 | E1 | IIQHGIDDSNF | 352 | 11 | | 32903 |
| HPV18 | E1 | ILALLRYK | 282 | 8 | | 32904 |
| HPV18 | E1 | ILALLRYKCGK | 282 | 11 | | 32905 |
| HPV18 | E1 | ILLTTNIH | 569 | 8 | | 32906 |
| HPV18 | E1 | ILLTTNIHPA | 569 | 10 | | 32907 |
| HPV18 | E1 | ILLTTNIHPAK | 569 | 11 | | 32908 |
| HPV18 | E1 | ISDDEDENA | 32 | 9 | | 32909 |
| HPV18 | E1 | ISFVNSTSH | 506 | 9 | | 32910 |
| HPV18 | E1 | ISFVNSTSHF | 506 | 10 | | 32911 |
| HPV18 | E1 | ISIDRKHK | 552 | 8 | | 32912 |
| HPV18 | E1 | ISLNSGQK | 116 | 8 | | 32913 |
| HPV18 | E1 | ISLNSGQKK | 116 | 9 | 0.0003 | 32914 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E1 | ISLNSGQKKA | 116 | 10 | | 32915 |
| HPV18 | E1 | ISLNSGQKKAK | 116 | 11 | | 32916 |
| HPV18 | E1 | ITFLGALK | 461 | 8 | | 32917 |
| HPV18 | E1 | ITFLGALKSF | 461 | 10 | | 32918 |
| HPV18 | E1 | ITVFEFPNA | 590 | 9 | | 32919 |
| HPV18 | E1 | ITVFEFPNAF | 590 | 10 | | 32920 |
| HPV18 | E1 | KCFFERTWSR | 617 | 10 | | 32921 |
| HPV18 | E1 | KCGKSRLTVA | 289 | 10 | | 32922 |
| HPV18 | E1 | KCGKSRLTVAK | 289 | 11 | | 32923 |
| HPV18 | E1 | KDCATMCK | 410 | 8 | | 32924 |
| HPV18 | E1 | KDCATMCKH | 410 | 9 | | 32925 |
| HPV18 | E1 | KDCATMCKHY | 410 | 10 | | 32926 |
| HPV18 | E1 | KDCATMCKHYR | 410 | 11 | | 32927 |
| HPV18 | E1 | KDLLKVNNK | 202 | 9 | | 32928 |
| HPV18 | E1 | KDNRWPYLESR | 579 | 11 | | 32929 |
| HPV18 | E1 | KDTYGLSF | 219 | 8 | | 32930 |
| HPV18 | E1 | KGLSTLLH | 299 | 8 | | 32931 |
| HPV18 | E1 | KGTPKKNCLVF | 472 | 11 | | 32932 |
| HPV18 | E1 | KIDEGGDWR | 439 | 9 | | 32933 |
| HPV18 | E1 | KLRAGQNH | 647 | 8 | | 32934 |
| HPV18 | E1 | KLRAGQNHR | 647 | 9 | 0.3000 | 32935 |
| HPV18 | E1 | KLRSSVAA | 318 | 8 | | 32936 |
| HPV18 | E1 | KLRSSVAALY | 318 | 10 | | 32937 |
| HPV18 | E1 | KSFLKGTPK | 468 | 9 | 0.0003 | 32938 |
| HPV18 | E1 | KSFLKGTPKK | 468 | 10 | | 32939 |
| HPV18 | E1 | KSNCQAKY | 401 | 8 | | 32940 |
| HPV18 | E1 | KSNCQAKYLK | 401 | 10 | | 32941 |
| HPV18 | E1 | KSRLTVAK | 292 | 8 | | 32942 |
| HPV18 | E1 | KSYFGMSF | 490 | 8 | | 32943 |
| HPV18 | E1 | KSYFGMSFIH | 490 | 10 | | 32944 |
| HPV18 | E1 | KSYFGMSFIHF | 490 | 11 | | 32945 |
| HPV18 | E1 | KTLIQPFILY | 259 | 10 | | 32946 |
| HPV18 | E1 | KTLIQPFILYA | 259 | 11 | | 32947 |
| HPV18 | E1 | KTTCTDWVTA | 237 | 10 | | 32948 |
| HPV18 | E1 | KVAMLDDA | 524 | 8 | | 32949 |
| HPV18 | E1 | KVNNKQGA | 206 | 8 | | 32950 |
| HPV18 | E1 | KVNNKQGAMLA | 206 | 11 | | 32951 |
| HPV18 | E1 | LADSNSNA | 389 | 8 | | 32952 |
| HPV18 | E1 | LADSNSNAA | 389 | 9 | | 32953 |
| HPV18 | E1 | LADSNSNAAA | 389 | 10 | | 32954 |
| HPV18 | E1 | LADSNSNAAAF | 389 | 11 | | 32955 |
| HPV18 | E1 | LALLRYKCGK | 283 | 10 | | 32956 |
| HPV18 | E1 | LAVFKDTY | 215 | 8 | | 32957 |
| HPV18 | E1 | LDCKWGVLILA | 274 | 11 | | 32958 |
| HPV18 | E1 | LDDATTTCWTY | 528 | 11 | | 32959 |
| HPV18 | E1 | LDGNPISIDR | 547 | 10 | | 32960 |
| HPV18 | E1 | LDGNPISIDRK | 547 | 11 | | 32961 |
| HPV18 | E1 | LDLHEEEEDA | 627 | 10 | | 32962 |
| HPV18 | E1 | LFHAQEVH | 69 | 8 | | 32963 |
| HPV18 | E1 | LFHAQEVHNDA | 69 | 11 | | 32964 |
| HPV18 | E1 | LFTISDSGY | 129 | 9 | | 32965 |
| HPV18 | E1 | LGALKSFLK | 464 | 9 | | 32966 |
| HPV18 | E1 | LILALLRY | 281 | 8 | | 32967 |
| HPV18 | E1 | LILALLRYK | 281 | 9 | 0.2700 | 32968 |
| HPV18 | E1 | LIQPFILY | 261 | 8 | | 32969 |
| HPV18 | E1 | LIQPFILYA | 261 | 9 | | 32970 |
| HPV18 | E1 | LIQPFILYAH | 261 | 10 | | 32971 |
| HPV18 | E1 | LIQPPKLR | 313 | 8 | | 32972 |
| HPV18 | E1 | LLADSNSNA | 388 | 9 | | 32973 |
| HPV18 | E1 | LLADSNSNAA | 388 | 10 | | 32974 |
| HPV18 | E1 | LLADSNSNAAA | 388 | 11 | | 32975 |
| HPV18 | E1 | LLKVNNKQGA | 204 | 10 | | 32976 |
| HPV18 | E1 | LLRYKCGK | 285 | 8 | | 32977 |
| HPV18 | E1 | LLRYKCGKSR | 285 | 10 | | 32978 |
| HPV18 | E1 | LLTTNIHPA | 570 | 9 | | 32979 |
| HPV18 | E1 | LLTTNIHPAK | 570 | 10 | | 32980 |
| HPV18 | E1 | LSEMVQWA | 364 | 8 | | 32981 |
| HPV18 | E1 | LSEMVQWAF | 364 | 9 | | 32982 |
| HPV18 | E1 | LSFTDLVR | 224 | 8 | | 32983 |
| HPV18 | E1 | LSFTDLVRNF | 224 | 10 | | 32984 |
| HPV18 | E1 | LSFTDLVRNFK | 224 | 11 | | 32985 |
| HPV18 | E1 | LTDESDMA | 376 | 8 | | 32986 |
| HPV18 | E1 | LTDESDMAF | 376 | 9 | | 32987 |
| HPV18 | E1 | LTDESDMAFEY | 376 | 11 | | 32988 |
| HPV18 | E1 | LTTNIHPA | 571 | 8 | | 32989 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E1 | LTTNIHPAK | 571 | 9 | 0.0910 | 32990 |
| HPV18 | E1 | LVFCGPANTGK | 480 | 11 | | 32991 |
| HPV18 | E1 | LVRNFKSDK | 229 | 9 | 0.0005 | 32992 |
| HPV18 | E1 | MAFEYALLA | 382 | 9 | | 32993 |
| HPV18 | E1 | MCKHYRRA | 415 | 8 | | 32994 |
| HPV18 | E1 | MCKHYRRAQK | 415 | 10 | | 32995 |
| HPV18 | E1 | MCKHYRRAQKR | 415 | 11 | | 32996 |
| HPV18 | E1 | MGDTPEWIQR | 340 | 10 | | 32997 |
| HPV18 | E1 | MLAVFKDTY | 214 | 9 | | 32998 |
| HPV18 | E1 | MLIQPPKLR | 312 | 9 | 0.0005 | 32999 |
| HPV18 | E1 | MSFIHFIQGA | 495 | 10 | | 33000 |
| HPV18 | E1 | MSQWIRFR | 429 | 8 | | 33001 |
| HPV18 | E1 | MSQWIRFRCSK | 429 | 11 | | 33002 |
| HPV18 | E1 | MVDFIDTQGTF | 47 | 11 | | 33003 |
| HPV18 | E1 | NCLVFCGPA | 478 | 9 | | 33004 |
| HPV18 | E1 | NCQAKYLK | 403 | 8 | | 33005 |
| HPV18 | E1 | NCQAKYLKDCA | 403 | 11 | | 33006 |
| HPV18 | E1 | NDAQVLHVLK | 77 | 10 | | 33007 |
| HPV18 | E1 | NDAQVLHVLKR | 77 | 11 | | 33008 |
| HPV18 | E1 | NDKNWKCF | 612 | 8 | | 33009 |
| HPV18 | E1 | NDKNWKCFF | 612 | 9 | | 33010 |
| HPV18 | E1 | NDKNWKCFFER | 612 | 11 | | 33011 |
| HPV18 | E1 | NFDLSEMVQWA | 361 | 11 | | 33012 |
| HPV18 | E1 | NGNPVYEINDK | 604 | 11 | | 33013 |
| HPV18 | E1 | NGWFYVQA | 15 | 8 | | 33014 |
| HPV18 | E1 | NIHPAKDNR | 574 | 9 | 0.0005 | 33015 |
| HPV18 | E1 | NMSQWIRF | 428 | 8 | | 33016 |
| HPV18 | E1 | NMSQWIRFR | 428 | 9 | 0.0540 | 33017 |
| HPV18 | E1 | NSGQKKAK | 119 | 8 | | 33018 |
| HPV18 | E1 | NSGQKKAKR | 119 | 9 | 0.0005 | 33019 |
| HPV18 | E1 | NSGQKKAKRR | 119 | 10 | | 33020 |
| HPV18 | E1 | NSNAAAFLK | 393 | 9 | 0.0057 | 33021 |
| HPV18 | E1 | NTGKSYFGMSF | 487 | 11 | | 33022 |
| HPV18 | E1 | NVCSGGSTEA | 158 | 10 | | 33023 |
| HPV18 | E1 | NVNPQCTIA | 191 | 9 | | 33024 |
| HPV18 | E1 | PAKDNRWPY | 577 | 9 | | 33025 |
| HPV18 | E1 | PANTGKSY | 485 | 8 | | 33026 |
| HPV18 | E1 | PANTGKSYF | 485 | 9 | | 33027 |
| HPV18 | E1 | PFDKNGNPVY | 600 | 10 | | 33028 |
| HPV18 | E1 | PFGTFKLR | 642 | 8 | | 33029 |
| HPV18 | E1 | PFGTFKLRA | 652 | 9 | | 33030 |
| HPV18 | E1 | PILLTTNIH | 568 | 9 | | 33031 |
| HPV18 | E1 | PILLTTNIHPA | 568 | 11 | | 33032 |
| HPV18 | E1 | PISIDRKH | 551 | 8 | | 33033 |
| HPV18 | E1 | PISIDRKHK | 551 | 9 | | 33034 |
| HPV18 | E1 | PIVQFLRY | 448 | 8 | | 33035 |
| HPV18 | E1 | PLTDTKVA | 519 | 8 | | 33036 |
| HPV18 | E1 | PTIAEGFK | 252 | 8 | | 33037 |
| HPV18 | E1 | PVYEINDK | 607 | 8 | | 33038 |
| HPV18 | E1 | PVYEINDKNWK | 607 | 11 | | 33039 |
| HPV18 | E1 | QAELETAQA | 60 | 9 | | 33040 |
| HPV18 | E1 | QAELETAQALF | 60 | 11 | | 33041 |
| HPV18 | E1 | QAKYLKDCA | 405 | 9 | | 33042 |
| HPV18 | E1 | QALFHAQEVH | 67 | 10 | | 33043 |
| HPV18 | E1 | QCTIAQLK | 195 | 8 | | 33044 |
| HPV18 | E1 | QFLRYQQIEF | 451 | 10 | | 33045 |
| HPV18 | E1 | QGAMLAVF | 211 | 8 | | 33046 |
| HPV18 | E1 | QGAMLAVFK | 211 | 9 | | 33047 |
| HPV18 | E1 | QGTFCEQA | 54 | 8 | | 33048 |
| HPV18 | E1 | QIEFITFLGA | 457 | 10 | | 33049 |
| HPV18 | E1 | QIQVTTNGEH | 146 | 10 | | 33050 |
| HPV18 | E1 | QLKDLLKVNNK | 200 | 11 | | 33051 |
| HPV18 | E1 | QMNMSQWIR | 426 | 9 | 0.0011 | 33052 |
| HPV18 | E1 | QMNMSQWIRF | 426 | 10 | | 33053 |
| HPV18 | E1 | QMNMSQWIRFR | 426 | 11 | | 33054 |
| HPV18 | E1 | QVLHVLKR | 80 | 8 | | 33055 |
| HPV18 | E1 | QVLHVLKRK | 80 | 9 | 0.0028 | 33056 |
| HPV18 | E1 | QVLHVLKRKF | 80 | 10 | | 33057 |
| HPV18 | E1 | QVLHVLKRKFA | 80 | 11 | | 33058 |
| HPV18 | E1 | QVTTNGEH | 148 | 8 | | 33059 |
| HPV18 | E1 | RITVFEFPNA | 589 | 10 | | 33060 |
| HPV18 | E1 | RITVFEFPNAF | 589 | 11 | | 33061 |
| HPV18 | E1 | RLDLHEEEDA | 626 | 11 | | 33062 |
| HPV18 | E1 | RLEVDTELSPR | 102 | 11 | | 33063 |
| HPV18 | E1 | RLFTISDSGY | 128 | 10 | | 33064 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E1 | RSSVAALY | 320 | 8 | | 33065 |
| HPV18 | E1 | RSSVAALYWY | 320 | 10 | | 33066 |
| HPV18 | E1 | RSSVAALYWYR | 320 | 11 | | 33067 |
| HPV18 | E1 | RTWSRLDLH | 622 | 9 | | 33068 |
| HPV18 | E1 | SDDEDENA | 33 | 8 | | 33069 |
| HPV18 | E1 | SDMAFEYA | 380 | 8 | | 33070 |
| HPV18 | E1 | SDMAFEYALLA | 380 | 11 | | 33071 |
| HPV18 | E1 | SFIHFIQGA | 496 | 9 | | 33072 |
| HPV18 | E1 | SFLKGTPK | 469 | 8 | | 33073 |
| HPV18 | E1 | SFLKGTPKK | 469 | 9 | | 33074 |
| HPV18 | E1 | SFTDLVRNF | 225 | 9 | | 33075 |
| HPV18 | E1 | SFTDLVRNFK | 225 | 10 | | 33076 |
| HPV18 | E1 | SFVNSTSH | 507 | 8 | | 33077 |
| HPV18 | E1 | SFVNSTSHF | 507 | 9 | | 33078 |
| HPV18 | E1 | SGQKKAKR | 120 | 8 | | 33079 |
| HPV18 | E1 | SGQKKAKRR | 120 | 9 | | 33080 |
| HPV18 | E1 | SGQKKAKRRLF | 120 | 11 | | 33081 |
| HPV18 | E1 | SGYGCSEVEA | 135 | 10 | | 33082 |
| HPV18 | E1 | SLNSGQKK | 117 | 8 | | 33083 |
| HPV18 | E1 | SLNSGQKKA | 117 | 9 | | 33084 |
| HPV18 | E1 | SLNSGQKKAK | 117 | 10 | | 33085 |
| HPV18 | E1 | SLNSGQKKAKR | 117 | 11 | | 33086 |
| HPV18 | E1 | SSVAALYWY | 321 | 9 | | 33087 |
| HPV18 | E1 | SSVAALYWYR | 321 | 10 | | 33088 |
| HPV18 | E1 | STENSPLGER | 93 | 10 | | 33089 |
| HPV18 | E1 | SVAALYWY | 322 | 8 | | 33090 |
| HPV18 | E1 | SVAALYWYR | 322 | 9 | 2.9000 | 33091 |
| HPV18 | E1 | TAIFGVNPTIA | 245 | 11 | | 33092 |
| HPV18 | E1 | TAQALFHA | 65 | 8 | | 33093 |
| HPV18 | E1 | TCMLIQPPK | 310 | 9 | | 33094 |
| HPV18 | E1 | TCMLIQPPKLR | 310 | 11 | | 33095 |
| HPV18 | E1 | TCTDWVTA | 239 | 8 | | 33096 |
| HPV18 | E1 | TCTDWVTAIF | 239 | 10 | | 33097 |
| HPV18 | E1 | TCWTYFDTY | 534 | 9 | | 33098 |
| HPV18 | E1 | TCWTYFDTYMR | 534 | 11 | | 33099 |
| HPV18 | E1 | TDESDMAF | 377 | 8 | | 33100 |
| HPV18 | E1 | TDESDMAFEY | 377 | 10 | | 33101 |
| HPV18 | E1 | TDESDMAFEYA | 377 | 11 | | 33102 |
| HPV18 | E1 | TDLVRNFK | 227 | 8 | | 33103 |
| HPV18 | E1 | TDLVRNFKSDK | 227 | 11 | | 33104 |
| HPV18 | E1 | TDTGSDMVDF | 41 | 10 | | 33105 |
| HPV18 | E1 | TDTKVAMLDDA | 521 | 11 | | 33106 |
| HPV18 | E1 | TDWVTAIF | 241 | 8 | | 33107 |
| HPV18 | E1 | TFCEQAELETA | 56 | 11 | | 33108 |
| HPV18 | E1 | TFKLRAGQNH | 645 | 10 | | 33109 |
| HPV18 | E1 | TFKLRAGQNHR | 645 | 11 | | 33110 |
| HPV18 | E1 | TFLGALKSF | 462 | 9 | | 33111 |
| HPV18 | E1 | TFLGALKSFLK | 462 | 11 | | 33112 |
| HPV18 | E1 | TGCNGWFY | 12 | 8 | | 33113 |
| HPV18 | E1 | TGCNGWFYVQA | 12 | 11 | | 33114 |
| HPV18 | E1 | TGKSYFGMSF | 488 | 10 | | 33115 |
| HPV18 | E1 | TGSDMVDF | 43 | 8 | | 33116 |
| HPV18 | E1 | TIAQLKDLLK | 197 | 10 | | 33117 |
| HPV18 | E1 | TLIQPFILY | 260 | 9 | | 33118 |
| HPV18 | E1 | TLIQPFILYA | 260 | 10 | | 33119 |
| HPV18 | E1 | TLIQPFILYAH | 260 | 11 | | 33120 |
| HPV18 | E1 | TMCKHYRR | 414 | 8 | | 33121 |
| HPV18 | E1 | TMCKHYRRA | 414 | 9 | | 33122 |
| HPV18 | E1 | TMCKHYRRAQK | 414 | 11 | | 33123 |
| HPV18 | E1 | TTCTDWVTA | 238 | 9 | | 33124 |
| HPV18 | E1 | TTCTDWVTAIF | 238 | 11 | | 33125 |
| HPV18 | E1 | TTCWTYFDTY | 533 | 10 | | 33126 |
| HPV18 | E1 | TTNIHPAK | 572 | 8 | | 33127 |
| HPV18 | E1 | TTNIHPAKDNR | 572 | 11 | | 33128 |
| HPV18 | E1 | TTTCWTYF | 532 | 8 | | 33129 |
| HPV18 | E1 | TTTCWTYFDTY | 532 | 11 | | 33130 |
| HPV18 | E1 | TVAKGLSTLLH | 296 | 11 | | 33131 |
| HPV18 | E1 | TVFEFPNA | 591 | 8 | | 33132 |
| HPV18 | E1 | TVFEFPNAF | 591 | 9 | | 33133 |
| HPV18 | E1 | TVFEFPNAFPF | 591 | 11 | | 33134 |
| HPV18 | E1 | VAALYWYR | 323 | 8 | | 33135 |
| HPV18 | E1 | VAKGLSTLLH | 297 | 10 | | 33136 |
| HPV18 | E1 | VCSGGSTEA | 159 | 9 | | 33137 |
| HPV18 | E1 | VDFIDTQGTF | 48 | 10 | | 33138 |
| HPV18 | E1 | VDTELSPR | 105 | 8 | | 33139 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E1 | VFCGPANTGK | 481 | 10 | | 33140 |
| HPV18 | E1 | VFEFPNAF | 592 | 8 | | 33141 |
| HPV18 | E1 | VFEFPNAFPF | 592 | 10 | | 33142 |
| HPV18 | E1 | VFKDTYGLSF | 217 | 10 | | 33143 |
| HPV18 | E1 | VISDDEDENA | 31 | 10 | | 33144 |
| HPV18 | E1 | VISFVNSTSH | 505 | 10 | | 33145 |
| HPV18 | E1 | VISFVNSTSHF | 505 | 11 | | 33146 |
| HPV18 | E1 | VLHVLKRK | 81 | 8 | | 33147 |
| HPV18 | E1 | VLHVLKRKF | 81 | 9 | | 33148 |
| HPV18 | E1 | VLHVLKRKFA | 81 | 10 | | 33149 |
| HPV18 | E1 | VLILALLR | 280 | 8 | | 33150 |
| HPV18 | E1 | VLILALLRY | 280 | 9 | | 33151 |
| HPV18 | E1 | VLILALLRYK | 280 | 10 | | 33152 |
| HPV18 | E1 | VMGDTPEWIQR | 339 | 11 | | 33153 |
| HPV18 | E1 | WFYVQAIVDK | 17 | 10 | | 33154 |
| HPV18 | E1 | WFYVQAIVDKK | 17 | 11 | | 33155 |
| HPV18 | E1 | WGVLILALLR | 278 | 10 | | 33156 |
| HPV18 | E1 | WGVLILALLRY | 278 | 11 | | 33157 |
| HPV18 | E1 | WIQRLTIIQH | 346 | 10 | | 33158 |
| HPV18 | E1 | WIRFRCSK | 432 | 8 | | 33159 |
| HPV18 | E1 | WLEPLTDTK | 516 | 9 | | 33160 |
| HPV18 | E1 | WLEPLTDTKVA | 516 | 11 | | 33161 |
| HPV18 | E1 | WTYFDTYMR | 536 | 9 | 0.0005 | 33162 |
| HPV18 | E1 | WTYFDTYMRNA | 536 | 11 | | 33163 |
| HPV18 | E1 | YAHIQCLDCK | 268 | 10 | | 33164 |
| HPV18 | E1 | YALLADSNSNA | 386 | 11 | | 33165 |
| HPV18 | E1 | YFDTYMRNA | 538 | 9 | | 33166 |
| HPV18 | E1 | YFGMSFIH | 492 | 8 | | 33167 |
| HPV18 | E1 | YFGMSFIHF | 492 | 9 | | 33168 |
| HPV18 | E1 | YGCSEVEA | 137 | 8 | | 33169 |
| HPV18 | E1 | YGLSFTDLVR | 222 | 10 | | 33170 |
| HPV18 | E1 | YLESRITVF | 585 | 9 | | 33171 |
| HPV18 | E1 | YLESRITVFEF | 585 | 11 | | 33172 |
| HPV18 | E1 | YLKDCATMCK | 408 | 10 | | 33173 |
| HPV18 | E1 | YLKDCATMCKH | 408 | 11 | | 33174 |
| HPV18 | E1 | YVQAIVDK | 19 | 8 | | 33175 |
| HPV18 | E1 | YVQAIVDKK | 19 | 9 | 0.0005 | 33176 |
| HPV18 | E2 | AATPTGNNK | 269 | 9 | | 33177 |
| HPV18 | E2 | AATPTGNNKR | 269 | 10 | | 33178 |
| HPV18 | E2 | AATPTGNNKRR | 269 | 11 | | 33179 |
| HPV18 | E2 | AATRPGHCGLA | 245 | 11 | | 33180 |
| HPV18 | E2 | AGTWDKTA | 147 | 8 | | 33181 |
| HPV18 | E2 | AIFFAAREH | 45 | 9 | | 33182 |
| HPV18 | E2 | ALQGLAQSR | 82 | 9 | | 33183 |
| HPV18 | E2 | ALQGLAQSRY | 82 | 10 | | 33184 |
| HPV18 | E2 | ALQGLAQSRYK | 82 | 11 | | 33185 |
| HPV18 | E2 | ATCVSHRGLY | 154 | 10 | | 33186 |
| HPV18 | E2 | ATCVSHRGLYY | 154 | 11 | | 33187 |
| HPV18 | E2 | ATPTGNNK | 270 | 8 | | 33188 |
| HPV18 | E2 | ATPTGNNKR | 270 | 9 | | 33189 |
| HPV18 | E2 | ATPTGNNKRR | 270 | 10 | | 33190 |
| HPV18 | E2 | ATPTGNNKRRK | 270 | 11 | | 33191 |
| HPV18 | E2 | ATQLVKQLQH | 214 | 10 | | 33192 |
| HPV18 | E2 | ATRPGHCGLA | 246 | 10 | | 33193 |
| HPV18 | E2 | CGLAEKQH | 252 | 8 | | 33194 |
| HPV18 | E2 | CGPVNPLLGA | 260 | 10 | | 33195 |
| HPV18 | E2 | CGPVNPLLGAA | 260 | 11 | | 33196 |
| HPV18 | E2 | CLRYRLRK | 301 | 8 | | 33197 |
| HPV18 | E2 | CLRYRLRKH | 301 | 9 | | 33198 |
| HPV18 | E2 | CMTYVAWDSVY | 132 | 11 | | 33199 |
| HPV18 | E2 | CSGNTTPIIH | 282 | 10 | | 33200 |
| HPV18 | E2 | CSTSDDTVSA | 205 | 10 | | 33201 |
| HPV18 | E2 | CVQDKIIDH | 14 | 9 | | 33202 |
| HPV18 | E2 | CVQDKIIDHY | 14 | 10 | | 33203 |
| HPV18 | E2 | CVSHRGLY | 156 | 8 | | 33204 |
| HPV18 | E2 | CVSHRGLYY | 156 | 9 | | 33205 |
| HPV18 | E2 | CVSHRGLYYVK | 156 | 11 | | 33206 |
| HPV18 | E2 | DAGTWDKTA | 146 | 9 | | 33207 |
| HPV18 | E2 | DDTVSATQLVK | 209 | 11 | | 33208 |
| HPV18 | E2 | DGNKDNCMTY | 126 | 10 | | 33209 |
| HPV18 | E2 | DIDSQIQY | 29 | 8 | | 33210 |
| HPV18 | E2 | DISSTWHWTGA | 315 | 11 | | 33211 |
| HPV18 | E2 | DSKDIDSQIQY | 26 | 11 | | 33212 |
| HPV18 | E2 | DSQIQYWQLIR | 31 | 11 | | 33213 |
| HPV18 | E2 | DSVQILVGY | 354 | 9 | | 33214 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E2 | DSVYYMTDA | 139 | 9 | | 33215 |
| HPV18 | E2 | DTVSATQLVK | 210 | 10 | | 33216 |
| HPV18 | E2 | EFKSECEK | 175 | 8 | | 33217 |
| HPV18 | E2 | EFKSECEKY | 175 | 9 | | 33218 |
| HPV18 | E2 | EGYNTFYIEF | 167 | 10 | | 33219 |
| HPV18 | E2 | EGYNTFYIEFK | 167 | 11 | | 33220 |
| HPV18 | E2 | ELQMALQGLA | 78 | 10 | | 33221 |
| HPV18 | E2 | ELWNTEPTH | 104 | 9 | | 33222 |
| HPV18 | E2 | ELWNTEPTHCF | 104 | 11 | | 33223 |
| HPV18 | E2 | FDGNKDNCMTY | 125 | 11 | | 33224 |
| HPV18 | E2 | GAATPTGNNK | 268 | 10 | | 33225 |
| HPV18 | E2 | GAATPTGNNKR | 268 | 11 | | 33226 |
| HPV18 | E2 | GDRNSLKCLR | 294 | 10 | | 33227 |
| HPV18 | E2 | GDRNSLKCLRY | 294 | 11 | | 33228 |
| HPV18 | E2 | GGQTVQVY | 117 | 8 | | 33229 |
| HPV18 | E2 | GGQTVQVYF | 117 | 9 | | 33230 |
| HPV18 | E2 | GILTVTYH | 331 | 8 | | 33231 |
| HPV18 | E2 | GLAQSRYK | 85 | 8 | | 33232 |
| HPV18 | E2 | GLYYVKEGY | 161 | 9 | | 33233 |
| HPV18 | E2 | GTAKTYGQTSA | 235 | 11 | | 33234 |
| HPV18 | E2 | HCGLAEKQH | 251 | 9 | | 33235 |
| HPV18 | E2 | HCGPVNPLLGA | 259 | 11 | | 33236 |
| HPV18 | E2 | HGIQTLNH | 53 | 8 | | 33237 |
| HPV18 | E2 | HLKGDRNSLK | 291 | 10 | | 33238 |
| HPV18 | E2 | HSETQRTK | 338 | 8 | | 33239 |
| HPV18 | E2 | HSETQRTKF | 338 | 9 | | 33240 |
| HPV18 | E2 | IDHYENDSK | 20 | 9 | | 33241 |
| HPV18 | E2 | IFFAAREH | 46 | 8 | | 33242 |
| HPV18 | E2 | IIDHYENDSK | 19 | 10 | | 33243 |
| HPV18 | E2 | IIHLKGDR | 289 | 8 | | 33244 |
| HPV18 | E2 | ISKSKAHK | 68 | 8 | | 33245 |
| HPV18 | E2 | ISKSKAHKA | 68 | 9 | | 33246 |
| HPV18 | E2 | ISSTWHWTGA | 316 | 10 | | 33247 |
| HPV18 | E2 | KAHKAIELQMA | 72 | 11 | | 33248 |
| HPV18 | E2 | KAIELQMA | 75 | 8 | | 33249 |
| HPV18 | E2 | KCLRYRLR | 300 | 8 | | 33250 |
| HPV18 | E2 | KCLRYRLRK | 300 | 9 | | 33251 |
| HPV18 | E2 | KCLRYRLRKH | 300 | 10 | | 33252 |
| HPV18 | E2 | KDIDSQIQY | 28 | 9 | | 33253 |
| HPV18 | E2 | KDNCMTYVA | 129 | 9 | | 33254 |
| HPV18 | E2 | KGDRNSLK | 293 | 8 | | 33255 |
| HPV18 | E2 | KGDRNSLKCLR | 293 | 11 | | 33256 |
| HPV18 | E2 | KGGQTVQVY | 116 | 9 | | 33257 |
| HPV18 | E2 | KGGQTVQVYF | 116 | 10 | | 33258 |
| HPV18 | E2 | KIIDHYENDSK | 18 | 11 | | 33259 |
| HPV18 | E2 | KTATCVSH | 152 | 8 | | 33260 |
| HPV18 | E2 | KTATCVSHR | 152 | 9 | | 33261 |
| HPV18 | E2 | KTGILTVTY | 329 | 9 | | 33262 |
| HPV18 | E2 | KTGILTVTYH | 329 | 10 | | 33263 |
| HPV18 | E2 | KTYGQTSA | 238 | 8 | | 33264 |
| HPV18 | E2 | KTYGQTSAA | 238 | 9 | | 33265 |
| HPV18 | E2 | KTYGQTSAATR | 238 | 11 | | 33266 |
| HPV18 | E2 | LCSGNTTPIIH | 281 | 11 | | 33267 |
| HPV18 | E2 | LGAATPTGNNK | 267 | 11 | | 33268 |
| HPV18 | E2 | LIRWENAIF | 39 | 9 | | 33269 |
| HPV18 | E2 | LIRWENAIFF | 39 | 10 | | 33270 |
| HPV18 | E2 | LIRWENAIFFA | 39 | 11 | | 33271 |
| HPV18 | E2 | LSCVQDKIIDH | 12 | 11 | | 33272 |
| HPV18 | E2 | LSERLSCVQDK | 8 | 11 | | 33273 |
| HPV18 | E2 | LTVTYHSETQR | 333 | 11 | | 33274 |
| HPV18 | E2 | MALQGLAQSR | 81 | 10 | | 33275 |
| HPV18 | E2 | MALQGLAQSRY | 81 | 11 | | 33276 |
| HPV18 | E2 | MCSTSDDTVSA | 204 | 11 | | 33277 |
| HPV18 | E2 | MTDAGTWDK | 144 | 9 | | 33278 |
| HPV18 | E2 | MTDAGTWDKTA | 144 | 11 | | 33279 |
| HPV18 | E2 | MTYVAWDSVY | 133 | 10 | | 33280 |
| HPV18 | E2 | MTYVAWDSVYY | 133 | 11 | | 33281 |
| HPV18 | E2 | NAIFFAAR | 44 | 8 | | 33282 |
| HPV18 | E2 | NAIFFAAREH | 44 | 10 | | 33283 |
| HPV18 | E2 | NISKSKAH | 67 | 8 | | 33284 |
| HPV18 | E2 | NISKSKAHK | 67 | 9 | | 33285 |
| HPV18 | E2 | NISKSKAHKA | 67 | 10 | | 33286 |
| HPV18 | E2 | NSLKCLRY | 297 | 8 | | 33287 |
| HPV18 | E2 | NSLKCLRYR | 297 | 9 | | 33288 |
| HPV18 | E2 | NSLKCLRYRLR | 297 | 11 | | 33289 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E2 | NTEPTHCF | 107 | 8 | | 33290 |
| HPV18 | E2 | NTEPTHCFK | 107 | 9 | | 33291 |
| HPV18 | E2 | NTEPTHCFKK | 107 | 10 | | 33292 |
| HPV18 | E2 | NTFYIEFK | 170 | 8 | | 33293 |
| HPV18 | E2 | NTGTWEVH | 185 | 8 | | 33294 |
| HPV18 | E2 | NTGTWEVHF | 185 | 9 | | 33295 |
| HPV18 | E2 | NTTPIIHLK | 285 | 9 | | 33296 |
| HPV18 | E2 | PAYNISKSK | 64 | 9 | | 33297 |
| HPV18 | E2 | PAYNISKSKA | 64 | 10 | | 33298 |
| HPV18 | E2 | PAYNISKSKAH | 64 | 11 | | 33299 |
| HPV18 | E2 | PDSVQILVGY | 353 | 10 | | 33300 |
| HPV18 | E2 | PGHCGLAEK | 249 | 9 | | 33301 |
| HPV18 | E2 | PGHCGLAEKQH | 249 | 11 | | 33302 |
| HPV18 | E2 | PIIHLKGDR | 288 | 9 | | 33303 |
| HPV18 | E2 | PTGNNKRR | 272 | 8 | | 33304 |
| HPV18 | E2 | PTGNNKRRK | 272 | 9 | | 33305 |
| HPV18 | E2 | PVNPLLGA | 262 | 8 | | 33306 |
| HPV18 | E2 | PVNPLLGAA | 262 | 9 | | 33307 |
| HPV18 | E2 | QDKIIDHY | 16 | 8 | | 33308 |
| HPV18 | E2 | QGLAQSRY | 84 | 8 | | 33309 |
| HPV18 | E2 | QGLAQSRYK | 84 | 9 | | 33310 |
| HPV18 | E2 | QIQYWQLIR | 33 | 9 | | 33311 |
| HPV18 | E2 | QLIRWENA | 38 | 8 | | 33312 |
| HPV18 | E2 | QLIRWENAIF | 38 | 10 | | 33313 |
| HPV18 | E2 | QLIRWENAIFF | 38 | 11 | | 33314 |
| HPV18 | E2 | QLQHTPSPY | 220 | 9 | | 33315 |
| HPV18 | E2 | QLVKQLQH | 216 | 8 | | 33316 |
| HPV18 | E2 | QMALQGLA | 80 | 8 | | 33317 |
| HPV18 | E2 | QMALQGLAQSR | 80 | 11 | | 33318 |
| HPV18 | E2 | QTLNHQVVPA | 56 | 10 | | 33319 |
| HPV18 | E2 | QTLNHQVVPAY | 56 | 11 | | 33320 |
| HPV18 | E2 | QTPKETLSER | 2 | 10 | | 33321 |
| HPV18 | E2 | QTSAATRPGH | 242 | 10 | | 33322 |
| HPV18 | E2 | QTVQVYFDGNK | 119 | 11 | | 33323 |
| HPV18 | E2 | QVVPAYNISK | 61 | 10 | | 33324 |
| HPV18 | E2 | QVYFDGNK | 122 | 8 | | 33325 |
| HPV18 | E2 | RDISSTWH | 314 | 8 | | 33326 |
| HPV18 | E2 | RGLYYVKEGY | 160 | 10 | | 33327 |
| HPV18 | E2 | RLRKHSDH | 305 | 8 | | 33328 |
| HPV18 | E2 | RLRKHSDHY | 305 | 9 | | 33329 |
| HPV18 | E2 | RLRKHSDHYR | 305 | 10 | | 33330 |
| HPV18 | E2 | RLSCVQDK | 11 | 8 | | 33331 |
| HPV18 | E2 | RTKFLNTVA | 343 | 9 | | 33332 |
| HPV18 | E2 | SAATRPGH | 244 | 8 | | 33333 |
| HPV18 | E2 | SATQLVKQLQH | 213 | 11 | | 33334 |
| HPV18 | E2 | SCVQDKIIDH | 13 | 10 | | 33335 |
| HPV18 | E2 | SCVQDKIIDHY | 13 | 11 | | 33336 |
| HPV18 | E2 | SGNTTPIIH | 283 | 9 | | 33337 |
| HPV18 | E2 | SGNTTPIIHLK | 283 | 11 | | 33338 |
| HPV18 | E2 | SLKCLRYR | 298 | 8 | | 33339 |
| HPV18 | E2 | SLKCLRYRLR | 298 | 10 | | 33340 |
| HPV18 | E2 | SLKCLRYRLRK | 298 | 11 | | 33341 |
| HPV18 | E2 | SSTVSVGTA | 229 | 9 | | 33342 |
| HPV18 | E2 | SSTVSVGTAK | 229 | 10 | | 33343 |
| HPV18 | E2 | SSTWHWTGA | 317 | 9 | | 33344 |
| HPV18 | E2 | STSDDTVSA | 206 | 9 | | 33345 |
| HPV18 | E2 | STVSVGTA | 230 | 8 | | 33346 |
| HPV18 | E2 | STVSVGTAK | 230 | 9 | | 33347 |
| HPV18 | E2 | STVSVGTAKTY | 230 | 11 | | 33348 |
| HPV18 | E2 | STWHWTGA | 318 | 8 | | 33349 |
| HPV18 | E2 | SVGTAKTY | 233 | 8 | | 33350 |
| HPV18 | E2 | SVQILVGY | 355 | 8 | | 33351 |
| HPV18 | E2 | SVYYMTDA | 140 | 8 | | 33352 |
| HPV18 | E2 | TAKTYGQTSA | 236 | 10 | | 33353 |
| HPV18 | E2 | TAKTYGQTSAA | 236 | 11 | | 33354 |
| HPV18 | E2 | TATCVSHR | 153 | 8 | | 33355 |
| HPV18 | E2 | TATCVSHRGLY | 153 | 11 | | 33356 |
| HPV18 | E2 | TCVSHRGLY | 155 | 9 | | 33357 |
| HPV18 | E2 | TCVSHRGLYY | 155 | 10 | | 33358 |
| HPV18 | E2 | TDAGTWDK | 145 | 8 | | 33359 |
| HPV18 | E2 | TDAGTWDKTA | 145 | 10 | | 33360 |
| HPV18 | E2 | TGILTVTY | 330 | 8 | | 33361 |
| HPV18 | E2 | TGILTVTYH | 330 | 9 | | 33362 |
| HPV18 | E2 | TGNNKRRK | 273 | 8 | | 33363 |
| HPV18 | E2 | TGTWEVHF | 186 | 8 | | 33364 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E2 | TLNHQVVPA | 57 | 9 | | 33365 |
| HPV18 | E2 | TLNHQVVPAY | 57 | 10 | | 33366 |
| HPV18 | E2 | TSAATRPGH | 243 | 9 | | 33367 |
| HPV18 | E2 | TSDDTVSA | 207 | 8 | | 33368 |
| HPV18 | E2 | TTPIIHLK | 286 | 8 | | 33369 |
| HPV18 | E2 | TTPIIHLKGDR | 286 | 11 | | 33370 |
| HPV18 | E2 | TVQVYFDGNK | 120 | 10 | | 33371 |
| HPV18 | E2 | TVSATQLVK | 211 | 9 | | 33372 |
| HPV18 | E2 | TVSVGTAK | 231 | 8 | | 33373 |
| HPV18 | E2 | TVSVGTAKTY | 231 | 10 | | 33374 |
| HPV18 | E2 | TVTYHSETQR | 334 | 10 | | 33375 |
| HPV18 | E2 | VAWDSVYY | 136 | 8 | | 33376 |
| HPV18 | E2 | VSATQLVK | 212 | 8 | | 33377 |
| HPV18 | E2 | VSHRGLYY | 157 | 8 | | 33378 |
| HPV18 | E2 | VSHRGLYYVK | 157 | 10 | | 33379 |
| HPV18 | E2 | VSVGTAKTY | 232 | 9 | | 33380 |
| HPV18 | E2 | VTYHSETQR | 335 | 9 | | 33381 |
| HPV18 | E2 | VTYHSETQRTK | 335 | 11 | | 33382 |
| HPV18 | E2 | VVPAYNISK | 62 | 9 | | 33383 |
| HPV18 | E2 | VVPAYNISKSK | 62 | 11 | | 33384 |
| HPV18 | E2 | WDKTATCVSH | 150 | 10 | | 33385 |
| HPV18 | E2 | WDKTATCVSHR | 150 | 11 | | 33386 |
| HPV18 | E2 | WDSVYYMTDA | 138 | 10 | | 33387 |
| HPV18 | E2 | WTGAGNEK | 322 | 8 | | 33388 |
| HPV18 | E2 | YGNTGTWEVH | 183 | 10 | | 33389 |
| HPV18 | E2 | YGNTGTWEVHF | 183 | 11 | | 33390 |
| HPV18 | E2 | YGQTSAATR | 240 | 9 | | 33391 |
| HPV18 | E2 | YIEFKSECEK | 173 | 10 | | 33392 |
| HPV18 | E2 | YIEFKSECEKY | 173 | 11 | | 33393 |
| HPV18 | E2 | YMTDAGTWDK | 143 | 10 | | 33394 |
| HPV18 | E2 | YSSTVSVGTA | 228 | 10 | | 33395 |
| HPV18 | E2 | YSSTVSVGTAK | 228 | 11 | | 33396 |
| HPV18 | E2 | YVAWDSVY | 135 | 8 | | 33397 |
| HPV18 | E2 | YVAWDSVYY | 135 | 9 | | 33398 |
| HPV18 | E2 | YVKEGYNTF | 164 | 9 | | 33399 |
| HPV18 | E2 | YVKEGYNTFY | 164 | 10 | | 33400 |
| HPV18 | E5 | AFTVYVFCF | 49 | 9 | | 33401 |
| HPV18 | E5 | ATAFTVYVF | 47 | 9 | | 33402 |
| HPV18 | E5 | ATAFTVYVFCF | 47 | 11 | | 33403 |
| HPV18 | E5 | CAYAWVLVF | 29 | 9 | | 33404 |
| HPV18 | E5 | CAYAWVLVFVY | 29 | 11 | | 33405 |
| HPV18 | E5 | CFCVCMYVCCH | 9 | 11 | | 33406 |
| HPV18 | E5 | CFLLPMLLLH | 56 | 10 | | 33407 |
| HPV18 | E5 | CMCAYAWVLVF | 27 | 11 | | 33408 |
| HPV18 | E5 | CVCMYVCCH | 11 | 9 | | 33409 |
| HPV18 | E5 | FCFCVCMY | 8 | 8 | | 33410 |
| HPV18 | E5 | FCFLLPMLLLH | 55 | 11 | | 33411 |
| HPV18 | E5 | FCVCMYVCCH | 10 | 10 | | 33412 |
| HPV18 | E5 | FLFCFCVCMY | 6 | 10 | | 33413 |
| HPV18 | E5 | FLLPMLLLH | 57 | 9 | | 33414 |
| HPV18 | E5 | FLLPMLLLHIH | 57 | 11 | | 33415 |
| HPV18 | E5 | FTVYVFCF | 50 | 8 | | 33416 |
| HPV18 | E5 | FVYIVVITSPA | 37 | 11 | | 33417 |
| HPV18 | E5 | IFLFCFCVCMY | 5 | 11 | | 33418 |
| HPV18 | E5 | ITSPATAF | 43 | 8 | | 33419 |
| HPV18 | E5 | ITSPATAFTVY | 43 | 11 | | 33420 |
| HPV18 | E5 | IVVITSPA | 40 | 8 | | 33421 |
| HPV18 | E5 | IVVITSPATA | 40 | 10 | | 33422 |
| HPV18 | E5 | IVVITSPATAF | 40 | 11 | | 33423 |
| HPV18 | E5 | LFCFCVCMY | 7 | 9 | | 33424 |
| HPV18 | E5 | LLPMLLLH | 58 | 8 | | 33425 |
| HPV18 | E5 | LLPMLLLHIH | 58 | 10 | | 33426 |
| HPV18 | E5 | LLPMLLLHIHA | 58 | 11 | | 33427 |
| HPV18 | E5 | LLPSVCMCA | 22 | 9 | | 33428 |
| HPV18 | E5 | LLPSVCMCAY | 22 | 10 | | 33429 |
| HPV18 | E5 | LLPSVCMCAYA | 22 | 11 | | 33430 |
| HPV18 | E5 | LSLIFLFCF | 2 | 9 | | 33431 |
| HPV18 | E5 | MCAYAWVLVF | 28 | 10 | | 33432 |
| HPV18 | E5 | MLLLHIHA | 61 | 8 | | 33433 |
| HPV18 | E5 | MLSLIFLF | 1 | 8 | | 33434 |
| HPV18 | E5 | MLSLIFLFCF | 1 | 10 | | 33435 |
| HPV18 | E5 | PATAFTVY | 46 | 8 | | 33436 |
| HPV18 | E5 | PATAFTVYVF | 46 | 10 | | 33437 |
| HPV18 | E5 | PLLPSVCMCA | 21 | 10 | | 33438 |
| HPV18 | E5 | PLLPSVCMCAY | 21 | 11 | | 33439 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E5 | PMLLLHIH | 60 | 8 | | 33440 |
| HPV18 | E5 | PMLLLHIHA | 60 | 9 | | 33441 |
| HPV18 | E5 | PSVCMCAY | 24 | 8 | | 33442 |
| HPV18 | E5 | PSVCMCAYA | 24 | 9 | | 33443 |
| HPV18 | E5 | SLIFLFCF | 3 | 8 | | 33444 |
| HPV18 | E5 | SVCMCAYA | 25 | 8 | | 33445 |
| HPV18 | E5 | TAFTVYVF | 48 | 8 | | 33446 |
| HPV18 | E5 | TAFTVYVFCF | 48 | 10 | | 33447 |
| HPV18 | E5 | TSPATAFTVY | 44 | 10 | | 33448 |
| HPV18 | E5 | VCMYVCCH | 12 | 8 | | 33449 |
| HPV18 | E5 | VITSPATA | 42 | 8 | | 33450 |
| HPV18 | E5 | VITSPATAF | 42 | 9 | | 33451 |
| HPV18 | E5 | VVITSPATA | 41 | 9 | | 33452 |
| HPV18 | E5 | VVITSPATAF | 41 | 10 | | 33453 |
| HPV18 | E5 | YAWVLVFVY | 31 | 9 | | 33454 |
| HPV18 | E5 | YIVVITSPA | 39 | 9 | | 33455 |
| HPV18 | E5 | YIVVITSPATA | 39 | 11 | | 33456 |
| HPV18 | E6 | AACHKCIDF | 63 | 9 | | 33457 |
| HPV18 | E6 | AACHKCIDFY | 63 | 10 | | 33458 |
| HPV18 | E6 | ACHKCIDF | 64 | 8 | | 33459 |
| HPV18 | E6 | ACHKCIDFY | 64 | 9 | | 33460 |
| HPV18 | E6 | ACHKCIDFYSR | 64 | 11 | | 33461 |
| HPV18 | E6 | AFKDLFVVY | 48 | 9 | | 33462 |
| HPV18 | E6 | AFKDLFVVYR | 48 | 10 | | 33463 |
| HPV18 | E6 | AGHYRGQCH | 131 | 9 | 0.0005 | 33464 |
| HPV18 | E6 | CCNRARQER | 141 | 9 | | 33465 |
| HPV18 | E6 | CIDFYSRIR | 68 | 9 | 0.0001 | 33466 |
| HPV18 | E6 | CLRCQKPLNPA | 105 | 11 | | 33467 |
| HPV18 | E6 | DFYSRIRELR | 70 | 10 | 0.0002 | 33468 |
| HPV18 | E6 | DFYSRIRELRH | 70 | 11 | | 33469 |
| HPV18 | E6 | DIEITCVY | 27 | 8 | | 33470 |
| HPV18 | E6 | DIEITCVYCK | 27 | 10 | 0.0089 | 33471 |
| HPV18 | E6 | DSIPHAACH | 58 | 9 | 0.0005 | 33472 |
| HPV18 | E6 | DSIPHAACHK | 58 | 10 | | 33473 |
| HPV18 | E6 | DSVYGDTLEK | 83 | 10 | 0.0005 | 33474 |
| HPV18 | E6 | EDPTRRPY | 5 | 8 | | 33475 |
| HPV18 | E6 | EDPTRRPYK | 5 | 9 | | 33476 |
| HPV18 | E6 | EFAFKDLF | 46 | 8 | | 33477 |
| HPV18 | E6 | EFAFKDLFVVY | 46 | 11 | | 33478 |
| HPV18 | E6 | EITCVYCK | 29 | 8 | | 33479 |
| HPV18 | E6 | ELRHYSDSVY | 77 | 10 | 0.0002 | 33480 |
| HPV18 | E6 | ELTEVFEF | 40 | 8 | | 33481 |
| HPV18 | E6 | ELTEVFEFA | 40 | 9 | | 33482 |
| HPV18 | E6 | ELTEVFEFAF | 40 | 10 | | 33483 |
| HPV18 | E6 | ELTEVFEFAFK | 40 | 11 | | 33484 |
| HPV18 | E6 | EVFEFAFK | 43 | 8 | 0.0025 | 33485 |
| HPV18 | E6 | EVFEFAFKDLF | 43 | 11 | | 33486 |
| HPV18 | E6 | FAFKDLFVVY | 47 | 10 | | 33487 |
| HPV18 | E6 | FAFKDLFVVYR | 47 | 11 | | 33488 |
| HPV18 | E6 | FVVYRDSIPH | 53 | 10 | | 33489 |
| HPV18 | E6 | FVVYRDSIPHA | 53 | 11 | | 33490 |
| HPV18 | E6 | GLYNLLIR | 97 | 8 | | 33491 |
| HPV18 | E6 | GLYNLLIRCLR | 97 | 11 | | 33492 |
| HPV18 | E6 | HAACHKCIDF | 62 | 10 | | 33493 |
| HPV18 | E6 | HAACHKCIDFY | 62 | 11 | | 33494 |
| HPV18 | E6 | HLNEKRRF | 120 | 8 | | 33495 |
| HPV18 | E6 | HLNEKRRFH | 120 | 9 | | 33496 |
| HPV18 | E6 | HSCCNRAR | 139 | 8 | | 33497 |
| HPV18 | E6 | HSCCNRARQER | 139 | 11 | | 33498 |
| HPV18 | E6 | IAGHYRGQCH | 130 | 10 | | 33499 |
| HPV18 | E6 | IDFYSRIR | 69 | 8 | | 33500 |
| HPV18 | E6 | IDFYSRIRELR | 69 | 11 | | 33501 |
| HPV18 | E6 | KCIDFYSR | 67 | 8 | | 33502 |
| HPV18 | E6 | KCIDFYSRIR | 67 | 10 | | 33503 |
| HPV18 | E6 | KDLFVVYR | 50 | 8 | | 33504 |
| HPV18 | E6 | KLRHLNEK | 117 | 8 | | 33505 |
| HPV18 | E6 | KLRHLNEKR | 117 | 9 | 0.0250 | 33506 |
| HPV18 | E6 | KLRHLNEKRR | 117 | 10 | 0.0130 | 33507 |
| HPV18 | E6 | KLRHLNEKRRF | 117 | 11 | | 33508 |
| HPV18 | E6 | KLTNTGLY | 92 | 8 | | 33509 |
| HPV18 | E6 | KTVLELTEVF | 36 | 10 | | 33510 |
| HPV18 | E6 | LFVVYRDSIPH | 52 | 11 | | 33511 |
| HPV18 | E6 | LIRCLRCQK | 102 | 9 | 0.0190 | 33512 |
| HPV18 | E6 | LLIRCLRCQK | 101 | 10 | 0.0470 | 33513 |
| HPV18 | E6 | LTEVFEFA | 41 | 8 | | 33514 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E6 | LTEVFEFAF | 41 | 9 | | 33515 |
| HPV18 | E6 | LTEVFEFAFK | 41 | 10 | 0.0001 | 33516 |
| HPV18 | E6 | MARFEDPTR | 1 | 9 | | 33517 |
| HPV18 | E6 | MARFEDPTRR | 1 | 10 | | 33518 |
| HPV18 | E6 | NIAGHYRGQCH | 129 | 11 | | 33519 |
| HPV18 | E6 | NLLIRCLR | 100 | 8 | | 33520 |
| HPV18 | E6 | NLLIRCLRCQK | 100 | 11 | | 33521 |
| HPV18 | E6 | NTGLYNLLIR | 95 | 10 | 0.0002 | 33522 |
| HPV18 | E6 | PAEKLRHLNEK | 114 | 11 | | 33523 |
| HPV18 | E6 | PLNPAEKLR | 111 | 9 | 0.0002 | 33524 |
| HPV18 | E6 | PLNPAEKLRH | 111 | 10 | | 33525 |
| HPV18 | E6 | QCHSCCNR | 137 | 8 | | 33526 |
| HPV18 | E6 | QCHSCCNRA | 137 | 9 | | 33527 |
| HPV18 | E6 | QCHSCCNRAR | 137 | 10 | | 33528 |
| HPV18 | E6 | QDIEITCVY | 26 | 9 | | 33529 |
| HPV18 | E6 | QDIEITCVYCK | 26 | 11 | | 33530 |
| HPV18 | E6 | RARQERLQR | 144 | 9 | 0.0007 | 33531 |
| HPV18 | E6 | RARQERLQRR | 144 | 10 | | 33532 |
| HPV18 | E6 | RARQERLQRRR | 144 | 11 | | 33533 |
| HPV18 | E6 | RCQKPLNPA | 107 | 9 | | 33534 |
| HPV18 | E6 | RCQKPLNPAEK | 107 | 11 | | 33535 |
| HPV18 | E6 | RDSIPHAA | 57 | 8 | | 33536 |
| HPV18 | E6 | RDSIPHAACH | 57 | 10 | | 33537 |
| HPV18 | E6 | RDSIPHAACHK | 57 | 11 | | 33538 |
| HPV18 | E6 | RFEDPTRR | 3 | 8 | | 33539 |
| HPV18 | E6 | RFEDPTRRPY | 3 | 10 | 0.0002 | 33540 |
| HPV18 | E6 | RFEDPTRRPYK | 3 | 11 | | 33541 |
| HPV18 | E6 | RFHNIAGH | 126 | 8 | | 33542 |
| HPV18 | E6 | RFHNIAGHY | 126 | 9 | 0.0005 | 33543 |
| HPV18 | E6 | RFHNIAGHYR | 126 | 10 | 0.0023 | 33544 |
| HPV18 | E6 | RGQCHSCCNR | 135 | 10 | | 33545 |
| HPV18 | E6 | RGQCHSCCNRA | 135 | 11 | | 33546 |
| HPV18 | E6 | RIRELRHY | 74 | 8 | | 33547 |
| HPV18 | E6 | SCCNRARQER | 140 | 10 | | 33548 |
| HPV18 | E6 | SDSVYGDTLEK | 82 | 11 | | 33549 |
| HPV18 | E6 | SIPHAACH | 59 | 8 | | 33550 |
| HPV18 | E6 | SIPHAACHK | 59 | 9 | 0.0170 | 33551 |
| HPV18 | E6 | SLQDIEITCVY | 24 | 11 | | 33552 |
| HPV18 | E6 | SVYGDTLEK | 84 | 9 | 0.0800 | 33553 |
| HPV18 | E6 | TGLYNLLIR | 96 | 9 | 0.0005 | 33554 |
| HPV18 | E6 | TLEKLTNTGLY | 89 | 11 | 0.0003 | 33555 |
| HPV18 | E6 | TVLELTEVF | 37 | 9 | | 33556 |
| HPV18 | E6 | TVLELTEVFEF | 37 | 11 | | 33557 |
| HPV18 | E6 | VFEFAFKDLF | 44 | 10 | 0.0001 | 33558 |
| HPV18 | E6 | VLELTEVF | 38 | 8 | | 33559 |
| HPV18 | E6 | VLELTEVFEF | 38 | 10 | | 33560 |
| HPV18 | E6 | VLELTEVFEFA | 38 | 11 | | 33561 |
| HPV18 | E6 | VVYRDSIPH | 54 | 9 | 0.1200 | 33562 |
| HPV18 | E6 | VVYRDSIPHA | 54 | 10 | | 33563 |
| HPV18 | E6 | VVYRDSIPHAA | 54 | 11 | | 33564 |
| HPV18 | E6 | YSRIRELR | 72 | 8 | | 33565 |
| HPV18 | E6 | YSRIRELRH | 72 | 9 | | 33566 |
| HPV18 | E6 | YSRIRELRHY | 72 | 10 | 0.0001 | 33567 |
| HPV18 | E7 | ADDLRAFQQLF | 80 | 11 | | 33568 |
| HPV18 | E7 | ATLQDIVLH | 6 | 9 | | 33569 |
| HPV18 | E7 | CCKCEARIK | 65 | 9 | | 33570 |
| HPV18 | E7 | CMCCKCEA | 63 | 8 | | 33571 |
| HPV18 | E7 | CMCCKCEAR | 63 | 9 | | 33572 |
| HPV18 | E7 | CMCCKCEARIK | 63 | 11 | 0.0014 | 33573 |
| HPV18 | E7 | DDLRAFQQLF | 81 | 10 | | 33574 |
| HPV18 | E7 | DGVNHQHLPA | 42 | 10 | | 33575 |
| HPV18 | E7 | DGVNHQHLPAR | 42 | 11 | | 33576 |
| HPV18 | E7 | DLRAFQQLF | 82 | 9 | | 33577 |
| HPV18 | E7 | EIDGVNHQH | 40 | 9 | | 33578 |
| HPV18 | E7 | EIPVDLLCH | 20 | 9 | | 33579 |
| HPV18 | E7 | ESSADDLR | 77 | 8 | | 33580 |
| HPV18 | E7 | ESSADDLRA | 77 | 9 | | 33581 |
| HPV18 | E7 | ESSADDLRAF | 77 | 10 | | 33582 |
| HPV18 | E7 | GVNHQHLPA | 43 | 9 | | 33583 |
| HPV18 | E7 | GVNHQHLPAR | 43 | 10 | | 33584 |
| HPV18 | E7 | GVNHQHLPARR | 43 | 11 | | 33585 |
| HPV18 | E7 | HLPARRAEPQR | 48 | 11 | | 33586 |
| HPV18 | E7 | HTMLCMCCK | 59 | 9 | 0.0640 | 33587 |
| HPV18 | E7 | IDGVNHQH | 41 | 8 | | 33588 |
| HPV18 | E7 | IDGVNHQHLPA | 41 | 11 | | 33589 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | E7 | KATLQDIVLH | 5 | 10 | | 33590 |
| HPV18 | E7 | KLVVESSA | 73 | 8 | | 33591 |
| HPV18 | E7 | LCMCCKCEA | 62 | 9 | | 33592 |
| HPV18 | E7 | LCMCCKCEAR | 62 | 10 | | 33593 |
| HPV18 | E7 | LFLNTLSF | 89 | 8 | | 33594 |
| HPV18 | E7 | LSFVCPWCA | 94 | 9 | 0.0005 | 33595 |
| HPV18 | E7 | LVVESSADDLR | 74 | 11 | | 33596 |
| HPV18 | E7 | MCCKCEAR | 64 | 8 | | 33597 |
| HPV18 | E7 | MCCKCEARIK | 64 | 10 | | 33598 |
| HPV18 | E7 | MLCMCCKCEA | 61 | 10 | | 33599 |
| HPV18 | E7 | MLCMCCKCEAR | 61 | 11 | | 33600 |
| HPV18 | E7 | NDEIDGVNH | 38 | 9 | | 33601 |
| HPV18 | E7 | NDEIDGVNHQH | 38 | 11 | | 33602 |
| HPV18 | E7 | NTLSFVCPWCA | 92 | 11 | | 33603 |
| HPV18 | E7 | PARRAEPQR | 50 | 9 | | 33604 |
| HPV18 | E7 | PARRAEPQRH | 50 | 10 | | 33605 |
| HPV18 | E7 | QLFLNTLSF | 88 | 9 | 0.0005 | 33606 |
| HPV18 | E7 | RIKLVVESSA | 71 | 10 | 0.0005 | 33607 |
| HPV18 | E7 | SADDLRAF | 79 | 8 | | 33608 |
| HPV18 | E7 | SFVCPWCA | 95 | 8 | | 33609 |
| HPV18 | E7 | SSADDLRA | 78 | 8 | | 33610 |
| HPV18 | E7 | SSADDLRAF | 78 | 9 | | 33611 |
| HPV18 | E7 | TLQDIVLH | 7 | 8 | | 33612 |
| HPV18 | E7 | TLSFVCPWCA | 93 | 10 | | 33613 |
| HPV18 | E7 | TMLCMCCK | 60 | 8 | 0.0240 | 33614 |
| HPV18 | E7 | TMLCMCCKCEA | 60 | 11 | | 33615 |
| HPV18 | E7 | VVESSADDLR | 75 | 10 | | 33616 |
| HPV18 | E7 | VVESSADDLRA | 75 | 11 | | 33617 |
| HPV18 | L1 | AAPAENKDPY | 494 | 10 | | 33618 |
| HPV18 | L1 | AATSNVSEDVR | 195 | 11 | | 33619 |
| HPV18 | L1 | ACAGVEIGR | 162 | 9 | | 33620 |
| HPV18 | L1 | ADPYGDSMF | 300 | 9 | | 33621 |
| HPV18 | L1 | ADPYGDSMFF | 300 | 10 | | 33622 |
| HPV18 | L1 | ADVMSYIH | 447 | 8 | | 33623 |
| HPV18 | L1 | AGGGNKQDIPK | 115 | 11 | | 33624 |
| HPV18 | L1 | AIGEHWAK | 225 | 8 | | 33625 |
| HPV18 | L1 | AIGEHWAKGTA | 225 | 11 | | 33626 |
| HPV18 | L1 | AITCQKDA | 487 | 8 | | 33627 |
| HPV18 | L1 | AITCQKDAA | 487 | 9 | | 33628 |
| HPV18 | L1 | AITCQKDAAPA | 487 | 11 | | 33629 |
| HPV18 | L1 | ALWRPSDNTVY | 63 | 11 | | 33630 |
| HPV18 | L1 | AMDFSTLQDTK | 268 | 11 | | 33631 |
| HPV18 | L1 | ASPGSCVY | 345 | 8 | | 33632 |
| HPV18 | L1 | ASTQSPVPGQY | 407 | 11 | | 33633 |
| HPV18 | L1 | ATKFKQYSR | 419 | 9 | | 33634 |
| HPV18 | L1 | ATKFKQYSRH | 419 | 10 | | 33635 |
| HPV18 | L1 | ATSNVSEDVR | 196 | 10 | | 33636 |
| HPV18 | L1 | ATTSSKPA | 552 | 8 | | 33637 |
| HPV18 | L1 | ATTSSKPAK | 552 | 9 | | 33638 |
| HPV18 | L1 | ATTSSKPAKR | 552 | 10 | | 33639 |
| HPV18 | L1 | CAGVEIGR | 163 | 8 | | 33640 |
| HPV18 | L1 | CAPAIGEH | 222 | 8 | | 33641 |
| HPV18 | L1 | CAPAIGEHWA | 222 | 10 | | 33642 |
| HPV18 | L1 | CAPAIGEHWAK | 222 | 11 | | 33643 |
| HPV18 | L1 | CGHYIILF | 42 | 8 | | 33644 |
| HPV18 | L1 | CGHYIILFLR | 42 | 10 | | 33645 |
| HPV18 | L1 | CILGCAPA | 218 | 8 | | 33646 |
| HPV18 | L1 | CLRREQLF | 310 | 8 | | 33647 |
| HPV18 | L1 | CLRREQLFA | 310 | 9 | | 33648 |
| HPV18 | L1 | CLRREQLFAR | 310 | 10 | | 33649 |
| HPV18 | L1 | CLRREQLFARH | 310 | 11 | | 33650 |
| HPV18 | L1 | CLYTRVLILH | 2 | 10 | | 33651 |
| HPV18 | L1 | CLYTRVLILHY | 2 | 11 | | 33652 |
| HPV18 | L1 | DAAPAENK | 493 | 8 | | 33653 |
| HPV18 | L1 | DAAPAENKDPY | 493 | 11 | | 33654 |
| HPV18 | L1 | DATKFKQY | 418 | 8 | | 33655 |
| HPV18 | L1 | DATKFKQYSR | 418 | 10 | | 33656 |
| HPV18 | L1 | DATKFKQYSRH | 418 | 11 | | 33657 |
| HPV18 | L1 | DCPPLELK | 245 | 8 | | 33658 |
| HPV18 | L1 | DDTESSHA | 188 | 8 | | 33659 |
| HPV18 | L1 | DDTESSHAA | 188 | 9 | | 33660 |
| HPV18 | L1 | DDYVTPTSIF | 86 | 10 | | 33661 |
| HPV18 | L1 | DDYVTPTSIFY | 86 | 11 | | 33662 |
| HPV18 | L1 | DFSTLQDTK | 270 | 9 | | 33663 |
| HPV18 | L1 | DGDMVDTGY | 258 | 9 | | 33664 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | L1 | DGDMVDTGYGA | 258 | 11 | | 33665 |
| HPV18 | L1 | DICQSICK | 284 | 8 | | 33666 |
| HPV18 | L1 | DICQSICKY | 284 | 9 | | 33667 |
| HPV18 | L1 | DIPKVSAY | 122 | 8 | | 33668 |
| HPV18 | L1 | DIPKVSAYQY | 122 | 10 | | 33669 |
| HPV18 | L1 | DIPKVSAYQYR | 122 | 11 | | 33670 |
| HPV18 | L1 | DLDQYPLGR | 520 | 9 | | 33671 |
| HPV18 | L1 | DLDQYPLGRK | 520 | 10 | | 33672 |
| HPV18 | L1 | DLDQYPLGRKF | 520 | 11 | | 33673 |
| HPV18 | L1 | DMVDTGYGA | 260 | 9 | | 33674 |
| HPV18 | L1 | DSMFFCLR | 305 | 8 | | 33675 |
| HPV18 | L1 | DSMFFCLRR | 305 | 9 | | 33676 |
| HPV18 | L1 | DSQLFNKPY | 364 | 9 | | 33677 |
| HPV18 | L1 | DTESSHAA | 189 | 8 | | 33678 |
| HPV18 | L1 | DTGYGAMDF | 263 | 9 | | 33679 |
| HPV18 | L1 | DTSIYNPETQR | 148 | 11 | | 33680 |
| HPV18 | L1 | DTVPQSLY | 330 | 8 | | 33681 |
| HPV18 | L1 | DTVPQSLYIK | 330 | 10 | | 33682 |
| HPV18 | L1 | DTYRFVQSVA | 478 | 10 | | 33683 |
| HPV18 | L1 | DVRDNVSVDY | 203 | 10 | | 33684 |
| HPV18 | L1 | DVRDNVSVDYK | 203 | 11 | | 33685 |
| HPV18 | L1 | EDGDMVDTGY | 257 | 10 | | 33686 |
| HPV18 | L1 | EDVRDNVSVDY | 202 | 11 | | 33687 |
| HPV18 | L1 | ETQRLVWA | 155 | 8 | | 33688 |
| HPV18 | L1 | ETQRLVWACA | 155 | 10 | | 33689 |
| HPV18 | L1 | FARHFWNR | 317 | 8 | | 33690 |
| HPV18 | L1 | FARHFWNRA | 317 | 9 | | 33691 |
| HPV18 | L1 | FCLRREQLF | 309 | 9 | | 33692 |
| HPV18 | L1 | FCLRREQLFA | 309 | 10 | | 33693 |
| HPV18 | L1 | FCLRREQLFAR | 309 | 11 | | 33694 |
| HPV18 | L1 | FFCLRREQLF | 308 | 10 | | 33695 |
| HPV18 | L1 | FFCLRREQLFA | 308 | 11 | | 33696 |
| HPV18 | L1 | FGLPDTSIY | 144 | 9 | | 33697 |
| HPV18 | L1 | FLQMALWR | 59 | 8 | | 33698 |
| HPV18 | L1 | FLRNVNVF | 49 | 8 | | 33699 |
| HPV18 | L1 | FLRNVNVFPIF | 49 | 11 | | 33700 |
| HPV18 | L1 | FLVQAGLR | 530 | 8 | | 33701 |
| HPV18 | L1 | FLVQAGLRR | 530 | 9 | | 33702 |
| HPV18 | L1 | FLVQAGLRRK | 530 | 10 | | 33703 |
| HPV18 | L1 | FSLDLDQY | 517 | 8 | | 33704 |
| HPV18 | L1 | FSTLQDTK | 271 | 8 | | 33705 |
| HPV18 | L1 | FVQSVAITCQK | 482 | 11 | | 33706 |
| HPV18 | L1 | GCAPAIGEH | 221 | 9 | | 33707 |
| HPV18 | L1 | GCAPAIGEHWA | 221 | 11 | | 33708 |
| HPV18 | L1 | GDCPPLELK | 244 | 9 | | 33709 |
| HPV18 | L1 | GDMVDTGY | 259 | 8 | | 33710 |
| HPV18 | L1 | QDMVDTGYGA | 259 | 10 | | 33711 |
| HPV18 | L1 | GDSMFFCLR | 304 | 9 | | 33712 |
| HPV18 | L1 | GDSMFFCLRR | 304 | 10 | | 33713 |
| HPV18 | L1 | GDTVPQSLY | 329 | 9 | | 33714 |
| HPV18 | L1 | GDTVPQSLYIK | 329 | 11 | | 33715 |
| HPV18 | L1 | GGGNKQDIPK | 116 | 10 | | 33716 |
| HPV18 | L1 | GGNKQDIPK | 117 | 9 | | 33717 |
| HPV18 | L1 | GLPDTSIY | 145 | 8 | | 33718 |
| HPV18 | L1 | GLRRKPTIGPR | 535 | 11 | | 33719 |
| HPV18 | L1 | GLSGHPFY | 177 | 8 | | 33720 |
| HPV18 | L1 | GLSGHPFYNK | 177 | 10 | | 33721 |
| HPV18 | L1 | GMPASPGSCVY | 342 | 11 | | 33722 |
| HPV18 | L1 | GSIVTSDSQLF | 358 | 11 | | 33723 |
| HPV18 | L1 | GVCWHNQLF | 383 | 9 | | 33724 |
| HPV18 | L1 | GVGLSGHPF | 175 | 9 | | 33725 |
| HPV18 | L1 | GVGLSGHPFY | 175 | 10 | | 33726 |
| HPV18 | L1 | HIIICGHY | 38 | 8 | | 33727 |
| HPV18 | L1 | HLLPLYGPLY | 13 | 10 | | 33728 |
| HPV18 | L1 | HLLPLYGPLYH | 13 | 11 | | 33729 |
| HPV18 | L1 | HSILVYMVH | 30 | 9 | | 33730 |
| HPV18 | L1 | HVEEYDLQF | 428 | 9 | | 33731 |
| HPV18 | L1 | HVEEYDLQFIF | 428 | 11 | | 33732 |
| HPV18 | L1 | ICGHYIILF | 41 | 9 | | 33733 |
| HPV18 | L1 | ICGHYIILFLR | 41 | 11 | | 33734 |
| HPV18 | L1 | ICQSICKY | 285 | 8 | | 33735 |
| HPV18 | L1 | ICQSICKYPDY | 285 | 11 | | 33736 |
| HPV18 | L1 | IFLQMALWR | 58 | 9 | | 33737 |
| HPV18 | L1 | IFQLCTITLTA | 437 | 11 | | 33738 |
| HPV18 | L1 | IFYHAGSSR | 94 | 9 | | 33739 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | L1 | IGEHWAKGTA | 226 | 10 | | 33740 |
| HPV18 | L1 | IGPRKRSA | 542 | 9 | | 33741 |
| HPV18 | L1 | IGPRKRSAPSA | 542 | 11 | | 33742 |
| HPV18 | L1 | IICGHYIILF | 40 | 10 | | 33743 |
| HPV18 | L1 | IIICGHYIILF | 39 | 11 | | 33744 |
| HPV18 | L1 | IILFLRNVNVF | 46 | 11 | | 33745 |
| HPV18 | L1 | ILFLRNVNVF | 47 | 10 | | 33746 |
| HPV18 | L1 | ILGCAPAIGEH | 219 | 11 | | 33747 |
| HPV18 | L1 | ILHYHLLPLY | 9 | 10 | | 33748 |
| HPV18 | L1 | ITCQKDAA | 488 | 8 | | 33749 |
| HPV18 | L1 | ITCQKDAAPA | 488 | 10 | | 33750 |
| HPV18 | L1 | ITLTADVMSY | 443 | 10 | | 33751 |
| HPV18 | L1 | IVTSDSQLF | 360 | 9 | | 33752 |
| HPV18 | L1 | IVTSDSQLFNK | 360 | 11 | | 33753 |
| HPV18 | L1 | KDAAPAENK | 492 | 9 | | 33754 |
| HPV18 | L1 | KDPYDKLK | 500 | 8 | | 33755 |
| HPV18 | L1 | KDPYDKLKF | 500 | 9 | | 33756 |
| HPV18 | L1 | KFGLPDTSIY | 143 | 10 | | 33757 |
| HPV18 | L1 | KFKQYSRH | 421 | 8 | | 33758 |
| HPV18 | L1 | KFLVQAGLR | 529 | 9 | | 33759 |
| HPV18 | L1 | KFLVQAGLRR | 529 | 10 | | 33760 |
| HPV18 | L1 | KFLVQAGLRRK | 529 | 11 | | 33761 |
| HPV18 | L1 | KFSLDLDQY | 516 | 9 | | 33762 |
| HPV18 | L1 | KFWNVDLK | 507 | 8 | | 33763 |
| HPV18 | L1 | KFWNVDLKEK | 507 | 10 | | 33764 |
| HPV18 | L1 | KFWNVDLKEKF | 507 | 11 | | 33765 |
| HPV18 | L1 | KGTACKSR | 232 | 8 | | 33766 |
| HPV18 | L1 | KLDDTESSH | 186 | 9 | | 33767 |
| HPV18 | L1 | KLDDTESSHA | 186 | 10 | | 33768 |
| HPV18 | L1 | KLDDTESSHAA | 186 | 11 | | 33769 |
| HPV18 | L1 | KLKFWNVDLK | 505 | 10 | | 33770 |
| HPV18 | L1 | KVSAYQYR | 125 | 8 | | 33771 |
| HPV18 | L1 | KVSAYQYRVF | 125 | 10 | | 33772 |
| HPV18 | L1 | KVSAYQYRVFR | 125 | 11 | | 33773 |
| HPV18 | L1 | LCILGCAPA | 217 | 9 | | 33774 |
| HPV18 | L1 | LCTITLTA | 440 | 8 | | 33775 |
| HPV18 | L1 | LDDTESSH | 187 | 8 | | 33776 |
| HPV18 | L1 | LDDTESSHA | 187 | 9 | | 33777 |
| HPV18 | L1 | LDDTESSHAA | 187 | 10 | | 33778 |
| HPV18 | L1 | LDICQSICK | 283 | 9 | | 33779 |
| HPV18 | L1 | LDICQSICKY | 283 | 10 | | 33780 |
| HPV18 | L1 | LDLDQYPLGR | 519 | 10 | | 33781 |
| HPV18 | L1 | LDLDQYPLGRK | 519 | 11 | | 33782 |
| HPV18 | L1 | LDQYPLGR | 521 | 8 | | 33783 |
| HPV18 | L1 | LDQYPLGRK | 521 | 9 | | 33784 |
| HPV18 | L1 | LDQYPLGRKF | 521 | 10 | | 33785 |
| HPV18 | L1 | LFARHFWNR | 316 | 9 | | 33786 |
| HPV18 | L1 | LFARHFWNRA | 316 | 10 | | 33787 |
| HPV18 | L1 | LFLRNVNVF | 48 | 9 | | 33788 |
| HPV18 | L1 | LFNKPYWLH | 367 | 9 | | 33789 |
| HPV18 | L1 | LFNKPYWLHK | 367 | 10 | | 33790 |
| HPV18 | L1 | LFNKPYWLHKA | 367 | 11 | | 33791 |
| HPV18 | L1 | LGCAPAIGEH | 220 | 10 | | 33792 |
| HPV18 | L1 | LGRKFLVQA | 526 | 9 | | 33793 |
| HPV18 | L1 | LGVGLSGH | 174 | 8 | | 33794 |
| HPV18 | L1 | LGVGLSGHPF | 174 | 10 | | 33795 |
| HPV18 | L1 | LGVGLSGHPFY | 174 | 11 | | 33796 |
| HPV18 | L1 | LILHYHLLPLY | 8 | 11 | | 33797 |
| HPV18 | L1 | LLPLYGPLY | 14 | 9 | | 33798 |
| HPV18 | L1 | LLPLYGPLYH | 14 | 10 | | 33799 |
| HPV18 | L1 | LLTVGNPY | 103 | 8 | | 33800 |
| HPV18 | L1 | LLTVGNPYF | 103 | 9 | | 33801 |
| HPV18 | L1 | LLTVGNPYFR | 103 | 10 | | 33802 |
| HPV18 | L1 | LSGHPFYNK | 178 | 9 | | 33803 |
| HPV18 | L1 | LTADVMSY | 445 | 8 | | 33804 |
| HPV18 | L1 | LTADVMSYIH | 445 | 10 | | 33805 |
| HPV18 | L1 | LTVGNPYF | 104 | 8 | | 33806 |
| HPV18 | L1 | LTVGNPYFR | 104 | 9 | | 33807 |
| HPV18 | L1 | LVQAGLRR | 531 | 8 | | 33808 |
| HPV18 | L1 | LVQAGLRRK | 531 | 9 | | 33809 |
| HPV18 | L1 | MCLYTRVLILH | 1 | 11 | | 33810 |
| HPV18 | L1 | MDFSTLQDTK | 269 | 10 | | 33811 |
| HPV18 | L1 | MFFCLRREQLF | 307 | 11 | | 33812 |
| HPV18 | L1 | MGDTVPQSLY | 328 | 10 | | 33813 |
| HPV18 | L1 | MSADPYGDSMF | 298 | 11 | | 33814 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | L1 | MVDTGYGA | 261 | 8 | | 33815 |
| HPV18 | L1 | MVDTGYGAMDF | 261 | 11 | | 33816 |
| HPV18 | L1 | MVHIIICGH | 36 | 9 | | 33817 |
| HPV18 | L1 | MVHIIICGHY | 36 | 10 | | 33818 |
| HPV18 | L1 | NGVCWHNQLF | 382 | 10 | | 33819 |
| HPV18 | L1 | NSSILEDWNF | 457 | 10 | | 33820 |
| HPV18 | L1 | NTVYLPPPSVA | 70 | 11 | | 33821 |
| HPV18 | L1 | NVDLKEKF | 510 | 8 | | 33822 |
| HPV18 | L1 | NVFPIFLQMA | 54 | 10 | | 33823 |
| HPV18 | L1 | NVNVFPIF | 52 | 8 | | 33824 |
| HPV18 | L1 | PAENKDPY | 496 | 8 | | 33825 |
| HPV18 | L1 | PAENKDPYDK | 496 | 10 | | 33826 |
| HPV18 | L1 | PAIGEHWA | 224 | 8 | | 33827 |
| HPV18 | L1 | PAIGEHWAK | 224 | 9 | | 33828 |
| HPV18 | L1 | PAKRVRVR | 558 | 8 | | 33829 |
| HPV18 | L1 | PAKRVRVRA | 558 | 9 | | 33830 |
| HPV18 | L1 | PAKRVRVRAR | 558 | 10 | | 33831 |
| HPV18 | L1 | PAKRVRVRARK | 558 | 11 | | 33832 |
| HPV18 | L1 | PASPGSCVY | 344 | 9 | | 33833 |
| HPV18 | L1 | PDYLQMSA | 293 | 8 | | 33834 |
| HPV18 | L1 | PDYLQMSADPY | 293 | 11 | | 33835 |
| HPV18 | L1 | PGQYDATK | 414 | 8 | | 33836 |
| HPV18 | L1 | PGQYDATKF | 414 | 9 | | 33837 |
| HPV18 | L1 | PGQYDATKFK | 414 | 10 | | 33838 |
| HPV18 | L1 | PIFLQMALWR | 57 | 10 | | 33839 |
| HPV18 | L1 | PLDICQSICK | 282 | 10 | | 33840 |
| HPV18 | L1 | PLDICQSICKY | 282 | 11 | | 33841 |
| HPV18 | L1 | PLGRKFLVQA | 525 | 10 | | 33842 |
| HPV18 | L1 | PLGVGLSGH | 173 | 9 | | 33843 |
| HPV18 | L1 | PLGVGLSGHPF | 173 | 11 | | 33844 |
| HPV18 | L1 | PLHSILVY | 28 | 8 | | 33845 |
| HPV18 | L1 | PLHSILVYMVH | 28 | 11 | | 33846 |
| HPV18 | L1 | PLPLHSILVY | 26 | 10 | | 33847 |
| HPV18 | L1 | PLYGPLYH | 16 | 8 | | 33848 |
| HPV18 | L1 | PLYGPLYHPR | 16 | 10 | | 33849 |
| HPV18 | L1 | PLYHPRPLPLH | 20 | 11 | | 33850 |
| HPV18 | L1 | PSATTSSK | 550 | 8 | | 33851 |
| HPV18 | L1 | PSATTSSKPA | 550 | 10 | | 33852 |
| HPV18 | L1 | PSATTSSKPAK | 550 | 11 | | 33853 |
| HPV18 | L1 | PSTNLTICA | 399 | 9 | | 33854 |
| HPV18 | L1 | PTIGPRKR | 540 | 8 | | 33855 |
| HPV18 | L1 | PTIGPRKRSA | 540 | 10 | | 33856 |
| HPV18 | L1 | PTSIFYHA | 91 | 8 | | 33857 |
| HPV18 | L1 | PTTSLVDTY | 472 | 9 | | 33858 |
| HPV18 | L1 | PTTSLVDTYR | 472 | 10 | | 33859 |
| HPV18 | L1 | PTTSLVDTYRF | 472 | 11 | | 33860 |
| HPV18 | L1 | PVPGQYDA | 412 | 8 | | 33861 |
| HPV18 | L1 | PVPGQYDATK | 412 | 10 | | 33862 |
| HPV18 | L1 | PVPGQYDATKF | 412 | 11 | | 33863 |
| HPV18 | L1 | QDIPKVSA | 121 | 8 | | 33864 |
| HPV18 | L1 | QDIPKVSAY | 121 | 9 | | 33865 |
| HPV18 | L1 | QDIPKVSAYQY | 121 | 11 | | 33866 |
| HPV18 | L1 | QGDCPPLELK | 243 | 10 | | 33867 |
| HPV18 | L1 | QGHNNGVCWH | 378 | 10 | | 33868 |
| HPV18 | L1 | QLCILGCA | 216 | 8 | | 33869 |
| HPV18 | L1 | QLCILGCAPA | 216 | 10 | | 33870 |
| HPV18 | L1 | QLCTITLTA | 439 | 9 | | 33871 |
| HPV18 | L1 | QLFARHFWNR | 315 | 10 | | 33872 |
| HPV18 | L1 | QLFARHFWNRA | 315 | 11 | | 33873 |
| HPV18 | L1 | QLFNKPYWLH | 366 | 10 | | 33874 |
| HPV18 | L1 | QLFNKPYWLHK | 366 | 11 | | 33875 |
| HPV18 | L1 | QLPDPNKF | 137 | 8 | | 33876 |
| HPV18 | L1 | QSICKYPDY | 287 | 9 | | 33877 |
| HPV18 | L1 | QSPVPGQY | 410 | 8 | | 33878 |
| HPV18 | L1 | QSPVPGQYDA | 410 | 10 | | 33879 |
| HPV18 | L1 | QSVAITCQK | 484 | 9 | | 33880 |
| HPV18 | L1 | QSVAITCQKDA | 484 | 11 | | 33881 |
| HPV18 | L1 | QTQLCILGCA | 214 | 10 | | 33882 |
| HPV18 | L1 | RDNVSVDY | 205 | 8 | | 33883 |
| HPV18 | L1 | RDNVSVDYK | 205 | 9 | | 33884 |
| HPV18 | L1 | RLLTVGNPY | 102 | 9 | | 33885 |
| HPV18 | L1 | RLLTVGNPYF | 102 | 10 | | 33886 |
| HPV18 | L1 | RLLTVGNPYFR | 102 | 11 | | 33887 |
| HPV18 | L1 | RSAPSATTSSK | 547 | 11 | | 33888 |
| HPV18 | L1 | RVLILHYH | 6 | 8 | | 33889 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | L1 | RVPAGGGNK | 112 | 9 | | 33890 |
| HPV18 | L1 | RVQLPDPNK | 135 | 9 | | 33891 |
| HPV18 | L1 | RVQLPDPNKF | 135 | 10 | | 33892 |
| HPV18 | L1 | RVRVRARK | 561 | 8 | | 33893 |
| HPV18 | L1 | RVVNTDDY | 81 | 8 | | 33894 |
| HPV18 | L1 | SADPYGDSMF | 299 | 10 | | 33895 |
| HPV18 | L1 | SADPYGDSMFF | 299 | 11 | | 33896 |
| HPV18 | L1 | SAPSATTSSK | 548 | 10 | | 33897 |
| HPV18 | L1 | SATTSSKPA | 551 | 9 | | 33898 |
| HPV18 | L1 | SATTSSKPAK | 551 | 10 | | 33899 |
| HPV18 | L1 | SATTSSKPAKR | 551 | 11 | | 33900 |
| HPV18 | L1 | SAYQYRVF | 127 | 8 | | 33901 |
| HPV18 | L1 | SAYQYRVFR | 127 | 9 | | 33902 |
| HPV18 | L1 | SDSQLFNK | 363 | 8 | | 33903 |
| HPV18 | L1 | SDSQLFNKPY | 363 | 10 | | 33904 |
| HPV18 | L1 | SGHPFYNK | 179 | 8 | | 33905 |
| HPV18 | L1 | SICKYPDY | 288 | 8 | | 33906 |
| HPV18 | L1 | SIFYHAGSSR | 93 | 10 | | 33907 |
| HPV18 | L1 | SILEDWNF | 459 | 8 | | 33908 |
| HPV18 | L1 | SILVYMVH | 31 | 8 | | 33909 |
| HPV18 | L1 | SIVTSDSQLF | 359 | 10 | | 33910 |
| HPV18 | L1 | SIYNPETQR | 150 | 9 | | 33911 |
| HPV18 | L1 | SLDLDQYPLGR | 518 | 11 | | 33912 |
| HPV18 | L1 | SLVDTYRF | 475 | 8 | | 33913 |
| HPV18 | L1 | SLYIKGTGMPA | 335 | 11 | | 33914 |
| HPV18 | L1 | SMFFCLRR | 306 | 8 | | 33915 |
| HPV18 | L1 | SSILEDWNF | 458 | 9 | | 33916 |
| HPV18 | L1 | SSKPAKRVR | 555 | 9 | | 33917 |
| HPV18 | L1 | SSKPAKRVRVR | 555 | 11 | | 33918 |
| HPV18 | L1 | SSRLLTVGNPY | 100 | 11 | | 33919 |
| HPV18 | L1 | STNLTICA | 400 | 8 | | 33920 |
| HPV18 | L1 | STQSPVPGQY | 408 | 10 | | 33921 |
| HPV18 | L1 | SVAITCQK | 485 | 8 | | 33922 |
| HPV18 | L1 | SVAITCQKDA | 485 | 10 | | 33923 |
| HPV18 | L1 | SVAITCQKDAA | 485 | 11 | | 33924 |
| HPV18 | L1 | SVARVVNTDDY | 78 | 11 | | 33925 |
| HPV18 | L1 | TADVMSYIH | 446 | 9 | | 33926 |
| HPV18 | L1 | TCQKDAAPA | 489 | 9 | | 33927 |
| HPV18 | L1 | TDDYVTPTSIF | 85 | 11 | | 33928 |
| HPV18 | L1 | TGYGAMDF | 264 | 8 | | 33929 |
| HPV18 | L1 | TIGPRKRSA | 541 | 9 | | 33930 |
| HPV18 | L1 | TITLTADVMSY | 442 | 11 | | 33931 |
| HPV18 | L1 | TLTADVMSY | 444 | 9 | | 33932 |
| HPV18 | L1 | TLTADVMSYIH | 444 | 11 | | 33933 |
| HPV18 | L1 | TMGDTVPQSLY | 327 | 11 | | 33934 |
| HPV18 | L1 | TSDSQLFNK | 362 | 9 | | 33935 |
| HPV18 | L1 | TSDSQLFNKPY | 362 | 11 | | 33936 |
| HPV18 | L1 | TSIFYHAGSSR | 92 | 11 | | 33937 |
| HPV18 | L1 | TSIYNPETQR | 149 | 10 | | 33938 |
| HPV18 | L1 | TSLVDTYR | 474 | 8 | | 33939 |
| HPV18 | L1 | TSLVDTYRF | 474 | 9 | | 33940 |
| HPV18 | L1 | TSNVSEDVR | 197 | 9 | | 33941 |
| HPV18 | L1 | TSSKPAKR | 554 | 8 | | 33942 |
| HPV18 | L1 | TSSKPAKRVR | 554 | 10 | | 33943 |
| HPV18 | L1 | TTPSTNLTICA | 397 | 11 | | 33944 |
| HPV18 | L1 | TTSLVDTY | 473 | 8 | | 33945 |
| HPV18 | L1 | TTSLVDTYR | 473 | 9 | | 33946 |
| HPV18 | L1 | TTSLVDTYRF | 473 | 10 | | 33947 |
| HPV18 | L1 | TTSSKPAK | 553 | 8 | | 33948 |
| HPV18 | L1 | TTSSKPAKR | 553 | 9 | | 33949 |
| HPV18 | L1 | TTSSKPAKRVR | 553 | 11 | | 33950 |
| HPV18 | L1 | TVGNPYFR | 105 | 8 | | 33951 |
| HPV18 | L1 | TVGNPYFRVPA | 105 | 11 | | 33952 |
| HPV18 | L1 | TVPQSLYIK | 331 | 9 | | 33953 |
| HPV18 | L1 | TVYLPPPSVA | 71 | 10 | | 33954 |
| HPV18 | L1 | TVYLPPPSVAR | 71 | 11 | | 33955 |
| HPV18 | L1 | VAITCQKDA | 486 | 9 | | 33956 |
| HPV18 | L1 | VAITCQKDAA | 486 | 10 | | 33957 |
| HPV18 | L1 | VARVVNTDDY | 79 | 10 | | 33958 |
| HPV18 | L1 | VCWHNQLF | 384 | 8 | | 33959 |
| HPV18 | L1 | VDTGYGAMDF | 262 | 10 | | 33960 |
| HPV18 | L1 | VDTYRFVQSVA | 477 | 11 | | 33961 |
| HPV18 | L1 | VFPIFLQMA | 55 | 9 | | 33962 |
| HPV18 | L1 | VFRVQLPDPNK | 133 | 11 | | 33963 |
| HPV18 | L1 | VGLSGHPF | 176 | 8 | | 33964 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | L1 | VGLSGHPFY | 176 | 9 | | 33965 |
| HPV18 | L1 | VGLSGHPFYNK | 176 | 11 | | 33966 |
| HPV18 | L1 | VGNPYFRVPA | 106 | 10 | | 33967 |
| HPV18 | L1 | VSAYQYRVF | 126 | 9 | | 33968 |
| HPV18 | L1 | VSAYQYRVFR | 126 | 10 | | 33969 |
| HPV18 | L1 | VTPTSIFY | 89 | 8 | | 33970 |
| HPV18 | L1 | VTPTSIFYH | 89 | 9 | | 33971 |
| HPV18 | L1 | VTPTSIFYHA | 89 | 10 | | 33972 |
| HPV18 | L1 | VTSDSQLF | 361 | 8 | | 33973 |
| HPV18 | L1 | VTSDSQLFNK | 361 | 10 | | 33974 |
| HPV18 | L1 | WACAGVEIGR | 161 | 10 | | 33975 |
| HPV18 | L1 | WAKGTACK | 230 | 8 | | 33976 |
| HPV18 | L1 | WAKGTACKSR | 230 | 10 | | 33977 |
| HPV18 | L1 | WLHKAQGH | 373 | 8 | | 33978 |
| HPV18 | L1 | YDATKFKQY | 417 | 9 | | 33979 |
| HPV18 | L1 | YDATKFKQYSR | 417 | 11 | | 33980 |
| HPV18 | L1 | YFRVPAGGGNK | 110 | 11 | | 33981 |
| HPV18 | L1 | YGDSMFFCLR | 303 | 10 | | 33982 |
| HPV18 | L1 | YGDSMFFCLRR | 303 | 11 | | 33983 |
| HPV18 | L1 | YGPLYHPR | 18 | 8 | | 33984 |
| HPV18 | L1 | YIKGTGMPA | 337 | 9 | | 33985 |
| HPV18 | L1 | YLPPPSVA | 73 | 8 | | 33986 |
| HPV18 | L1 | YLPPPSVAR | 73 | 9 | | 33987 |
| HPV18 | L1 | YLQMSADPY | 295 | 9 | | 33988 |
| HPV18 | L1 | YMVHIIICGH | 35 | 10 | | 33989 |
| HPV18 | L1 | YMVHIIICGHY | 35 | 11 | | 33990 |
| HPV18 | L1 | YSRHVEEY | 425 | 8 | | 33991 |
| HPV18 | L1 | YTRVLILH | 4 | 8 | | 33992 |
| HPV18 | L1 | YTRVLILHY | 4 | 9 | | 33993 |
| HPV18 | L1 | YTRVLILHYH | 4 | 10 | | 33994 |
| HPV18 | L1 | YVTPTSIF | 88 | 8 | | 33995 |
| HPV18 | L1 | YVTPTSIFY | 88 | 9 | | 33996 |
| HPV18 | L1 | YVTPTSIFYH | 88 | 10 | | 33997 |
| HPV18 | L1 | YVTPTSIFYHA | 88 | 11 | | 33998 |
| HPV18 | L2 | AFEPVDTTLTF | 255 | 11 | | 33999 |
| HPV18 | L2 | AGPRLYSR | 222 | 8 | | 34000 |
| HPV18 | L2 | AGPRLYSRA | 222 | 9 | | 34001 |
| HPV18 | L2 | AGPRLYSRAY | 222 | 10 | | 34002 |
| HPV18 | L2 | ALTSRRGTVR | 286 | 10 | | 34003 |
| HPV18 | L2 | ALTSRRGTVRF | 286 | 11 | | 34004 |
| HPV18 | L2 | ASTQYIGIH | 423 | 9 | | 34005 |
| HPV18 | L2 | ASVTDLYK | 12 | 8 | | 34006 |
| HPV18 | L2 | ASVTDLYKTCK | 12 | 11 | | 34007 |
| HPV18 | L2 | ATEDNDLF | 341 | 8 | | 34008 |
| HPV18 | L2 | ATEDNDLFDIY | 341 | 11 | | 34009 |
| HPV18 | L2 | DFMDIIRLH | 275 | 9 | | 34010 |
| HPV18 | L2 | DFMDIIRLHR | 275 | 10 | | 34011 |
| HPV18 | L2 | DIIRLHRPA | 278 | 9 | | 34012 |
| HPV18 | L2 | DISPIAPSPEY | 322 | 11 | | 34013 |
| HPV18 | L2 | DITSAGTTTPA | 129 | 11 | | 34014 |
| HPV18 | L2 | DIYADDMDPA | 349 | 10 | | 34015 |
| HPV18 | L2 | DMDPAVPVPSR | 354 | 11 | | 34016 |
| HPV18 | L2 | DSDFMDIIR | 273 | 9 | | 34017 |
| HPV18 | L2 | DSDFMDIIRLH | 273 | 11 | | 34018 |
| HPV18 | L2 | DSSVVTSGA | 109 | 9 | | 34019 |
| HPV18 | L2 | DSSVVTSGAPR | 109 | 11 | | 34020 |
| HPV18 | L2 | DTTLTFDPR | 260 | 9 | | 34021 |
| HPV18 | L2 | EDNDLFDIY | 343 | 9 | | 34022 |
| HPV18 | L2 | EDNDLFDIYA | 343 | 10 | | 34023 |
| HPV18 | L2 | EDSSVVTSGA | 108 | 10 | | 34024 |
| HPV18 | L2 | EGTTLADK | 36 | 8 | | 34025 |
| HPV18 | L2 | EIPLQTFA | 194 | 8 | | 34026 |
| HPV18 | L2 | ELQPLVSA | 334 | 8 | | 34027 |
| HPV18 | L2 | EVPQTGEVA | 169 | 9 | | 34028 |
| HPV18 | L2 | FADGFVAA | 455 | 8 | | 34029 |
| HPV18 | L2 | FDIYADDMDPA | 348 | 11 | | 34030 |
| HPV18 | L2 | FFADGFVA | 454 | 8 | | 34031 |
| HPV18 | L2 | FFADGFVAA | 454 | 9 | | 34032 |
| HPV18 | L2 | FFKYSPTISSA | 371 | 11 | | 34033 |
| HPV18 | L2 | FIPKKRKR | 443 | 8 | | 34034 |
| HPV18 | L2 | FIPKKRKRVPY | 443 | 11 | | 34035 |
| HPV18 | L2 | FLTRPSSLITY | 241 | 11 | | 34036 |
| HPV18 | L2 | FMDIIRLH | 276 | 8 | | 34037 |
| HPV18 | L2 | FMDIIRLHR | 276 | 9 | | 34038 |
| HPV18 | L2 | FMDIIRLHRPA | 276 | 11 | | 34039 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | L2 | FSRLGQRA | 296 | 8 | | 34040 |
| HPV18 | L2 | FSRLGQRATMF | 296 | 11 | | 34041 |
| HPV18 | L2 | FTRSGTQIGA | 306 | 10 | | 34042 |
| HPV18 | L2 | FTRSGTQIGAR | 306 | 11 | | 34043 |
| HPV18 | L2 | FVGTPTSGTH | 181 | 10 | | 34044 |
| HPV18 | L2 | GARVHFYH | 314 | 8 | | 34045 |
| HPV18 | L2 | GIGTGSGTGGR | 58 | 11 | | 34046 |
| HPV18 | L2 | GIHGTHYY | 429 | 8 | | 34047 |
| HPV18 | L2 | GSGTGGRTGY | 62 | 10 | | 34048 |
| HPV18 | L2 | GTCPPDVVPK | 25 | 10 | | 34049 |
| HPV18 | L2 | GTGGRTGY | 64 | 8 | | 34050 |
| HPV18 | L2 | GTGSGTGGR | 60 | 9 | | 34051 |
| HPV18 | L2 | GTHYYLWPLY | 432 | 10 | | 34052 |
| HPV18 | L2 | GTHYYLWPLYY | 432 | 11 | | 34053 |
| HPV18 | L2 | GTPTSGTH | 183 | 8 | | 34054 |
| HPV18 | L2 | GTPTSGTHGY | 183 | 10 | | 34055 |
| HPV18 | L2 | GTQIGARVH | 310 | 9 | | 34056 |
| HPV18 | L2 | GTQIGARVHF | 310 | 10 | | 34057 |
| HPV18 | L2 | GTQIGARVHFY | 310 | 11 | | 34058 |
| HPV18 | L2 | GTSGFDITSA | 124 | 10 | | 34059 |
| HPV18 | L2 | GTVRFSRLGQR | 292 | 11 | | 34060 |
| HPV18 | L2 | HFYHDISPIA | 318 | 10 | | 34061 |
| HPV18 | L2 | HGTHYYLWPLY | 431 | 11 | | 34062 |
| HPV18 | L2 | HGYEEIPLQTF | 190 | 11 | | 34063 |
| HPV18 | L2 | IGARVHFY | 313 | 8 | | 34064 |
| HPV18 | L2 | IGARVHFYH | 313 | 9 | | 34065 |
| HPV18 | L2 | IGIHGTHY | 428 | 8 | | 34066 |
| HPV18 | L2 | IGIHGTHYY | 428 | 9 | | 34067 |
| HPV18 | L2 | IGTGSGTGGR | 59 | 10 | | 34068 |
| HPV18 | L2 | IIEVPQTGEVA | 167 | 11 | | 34069 |
| HPV18 | L2 | IIRLHRPA | 279 | 8 | | 34070 |
| HPV18 | L2 | ILQWSSLGIF | 44 | 10 | | 34071 |
| HPV18 | L2 | ISPIAPSPEY | 323 | 10 | | 34072 |
| HPV18 | L2 | ISSTPLPTVR | 210 | 10 | | 34073 |
| HPV18 | L2 | ISSTPLPTVRR | 210 | 11 | | 34074 |
| HPV18 | L2 | ISTTNFTNPA | 152 | 10 | | 34075 |
| HPV18 | L2 | ISTTNFTNPAF | 152 | 11 | | 34076 |
| HPV18 | L2 | ITSAGTTTPA | 130 | 10 | | 34077 |
| HPV18 | L2 | ITYDNPAF | 249 | 8 | | 34078 |
| HPV18 | L2 | IVSPTAPA | 416 | 8 | | 34079 |
| HPV18 | L2 | KILQWSSLGIF | 43 | 11 | | 34080 |
| HPV18 | L2 | KVEGTTLA | 34 | 8 | | 34081 |
| HPV18 | L2 | KVEGTTLADK | 34 | 10 | | 34082 |
| HPV18 | L2 | LGQRATMF | 299 | 8 | | 34083 |
| HPV18 | L2 | LGQRATMFTR | 299 | 10 | | 34084 |
| HPV18 | L2 | LITYDNPA | 248 | 8 | | 34085 |
| HPV18 | L2 | LITYDNPAF | 248 | 9 | | 34086 |
| HPV18 | L2 | LTRPSSLITY | 242 | 10 | | 34087 |
| HPV18 | L2 | LTSRRGTVR | 287 | 9 | | 34088 |
| HPV18 | L2 | LTSRRGTVRF | 287 | 10 | | 34089 |
| HPV18 | L2 | LTSSWDVPVY | 391 | 10 | | 34090 |
| HPV18 | L2 | LVSATEDNDLF | 338 | 11 | | 34091 |
| HPV18 | L2 | MDIIRLHR | 277 | 8 | | 34092 |
| HPV18 | L2 | MDIIRLHRPA | 277 | 10 | | 34093 |
| HPV18 | L2 | MDPAVPVPSR | 355 | 10 | | 34094 |
| HPV18 | L2 | MFTRSGTQIGA | 305 | 11 | | 34095 |
| HPV18 | L2 | MVSHRAAR | 1 | 8 | | 34096 |
| HPV18 | L2 | MVSHRAARR | 1 | 9 | | 34097 |
| HPV18 | L2 | MVSHRAARRK | 1 | 10 | | 34098 |
| HPV18 | L2 | MVSHRAARRKR | 1 | 11 | | 34099 |
| HPV18 | L2 | NDLFDIYA | 345 | 8 | | 34100 |
| HPV18 | L2 | NTVVDVGPTR | 79 | 10 | | 34101 |
| HPV18 | L2 | PALTSRRGTVR | 285 | 11 | | 34102 |
| HPV18 | L2 | PASTQYIGIH | 422 | 10 | | 34103 |
| HPV18 | L2 | PAVPVPSR | 357 | 8 | | 34104 |
| HPV18 | L2 | PDSDFMDIIR | 272 | 10 | | 34105 |
| HPV18 | L2 | PIAPSPEY | 325 | 8 | | 34106 |
| HPV18 | L2 | PISSTPLPTVR | 209 | 11 | | 34107 |
| HPV18 | L2 | PIVSPTAPA | 415 | 9 | | 34108 |
| HPV18 | L2 | PLPTVRRVA | 214 | 9 | | 34109 |
| HPV18 | L2 | PLTSSWDVPVY | 390 | 11 | | 34110 |
| HPV18 | L2 | PLYYFIPK | 439 | 8 | | 34111 |
| HPV18 | L2 | PLYYFIPKK | 439 | 9 | | 34112 |
| HPV18 | L2 | PLYYFIPKKR | 439 | 10 | | 34113 |
| HPV18 | L2 | PLYYFIPKKRK | 439 | 11 | | 34114 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | L2 | PSRSTTSF | 362 | 8 | | 34115 |
| HPV18 | L2 | PSRSTTSFA | 362 | 9 | | 34116 |
| HPV18 | L2 | PSRSTTSFAF | 362 | 10 | | 34117 |
| HPV18 | L2 | PSRSTTSFAFF | 362 | 11 | | 34118 |
| HPV18 | L2 | PSSLITYDNPA | 245 | 11 | | 34119 |
| HPV18 | L2 | PTAPASTQY | 419 | 9 | | 34120 |
| HPV18 | L2 | PTFTGTSGF | 120 | 9 | | 34121 |
| HPV18 | L2 | PTISSASSY | 376 | 9 | | 34122 |
| HPV18 | L2 | PTSGTHGY | 185 | 8 | | 34123 |
| HPV18 | L2 | PTVRRVAGPR | 216 | 10 | | 34124 |
| HPV18 | L2 | PVDTTLTF | 258 | 8 | | 34125 |
| HPV18 | L2 | PVDTTLTFDPR | 258 | 11 | | 34126 |
| HPV18 | L2 | PVPSRSTTSF | 360 | 10 | | 34127 |
| HPV18 | L2 | PVPSRSTTSFA | 360 | 11 | | 34128 |
| HPV18 | L2 | QIGARVHF | 312 | 8 | | 34129 |
| HPV18 | L2 | QIGARVHFY | 312 | 9 | | 34130 |
| HPV18 | L2 | QIGARVHFYH | 312 | 10 | | 34131 |
| HPV18 | L2 | QTGEVAGNVF | 172 | 10 | | 34132 |
| HPV18 | L2 | QVSVANPEF | 233 | 9 | | 34133 |
| HPV18 | L2 | RAARRKRA | 5 | 8 | | 34134 |
| HPV18 | L2 | RASVTDLY | 11 | 8 | | 34135 |
| HPV18 | L2 | RASVTDLYK | 11 | 9 | | 34136 |
| HPV18 | L2 | RAYQQVSVA | 229 | 9 | | 34137 |
| HPV18 | L2 | RFSRLGQR | 295 | 8 | | 34138 |
| HPV18 | L2 | RFSRLGQRA | 295 | 9 | | 34139 |
| HPV18 | L2 | RGTVRFSR | 291 | 8 | | 34140 |
| HPV18 | L2 | RLGQRATMF | 298 | 9 | | 34141 |
| HPV18 | L2 | RLGQRATMFTR | 298 | 11 | | 34142 |
| HPV18 | L2 | RLHRPALTSR | 281 | 10 | | 34143 |
| HPV18 | L2 | RLHRPALTSRR | 281 | 11 | | 34144 |
| HPV18 | L2 | RSDVPDSDF | 268 | 9 | | 34145 |
| HPV18 | L2 | RSGTQIGA | 308 | 8 | | 34146 |
| HPV18 | L2 | RSGTQIGAR | 308 | 9 | | 34147 |
| HPV18 | L2 | RSGTQIGARVH | 308 | 11 | | 34148 |
| HPV18 | L2 | RSTTSFAF | 364 | 8 | | 34149 |
| HPV18 | L2 | RSTTSFAFF | 364 | 9 | | 34150 |
| HPV18 | L2 | RSTTSFAFFK | 364 | 10 | | 34151 |
| HPV18 | L2 | RSTTSFAFFKY | 364 | 11 | | 34152 |
| HPV18 | L2 | RTGYIPLGGR | 68 | 10 | | 34153 |
| HPV18 | L2 | RVAGPRLY | 220 | 8 | | 34154 |
| HPV18 | L2 | RVAGPRLYSR | 220 | 10 | | 34155 |
| HPV18 | L2 | RVAGPRLYSRA | 220 | 11 | | 34156 |
| HPV18 | L2 | RVPYFFADGF | 450 | 10 | | 34157 |
| HPV18 | L2 | SAGTTTPA | 132 | 8 | | 34158 |
| HPV18 | L2 | SATEDNDLF | 340 | 9 | | 34159 |
| HPV18 | L2 | SDFMDIIR | 274 | 8 | | 34160 |
| HPV18 | L2 | SDFMDIIRLH | 274 | 10 | | 34161 |
| HPV18 | L2 | SDFMDIIRLHR | 274 | 11 | | 34162 |
| HPV18 | L2 | SDVPDSDF | 269 | 8 | | 34163 |
| HPV18 | L2 | SGAPRPTF | 115 | 8 | | 34164 |
| HPV18 | L2 | SGFDITSA | 126 | 8 | | 34165 |
| HPV18 | L2 | SGTCPPDVVPK | 24 | 11 | | 34166 |
| HPV18 | L2 | SGTGGRTGY | 63 | 9 | | 34167 |
| HPV18 | L2 | SGTQIGAR | 309 | 8 | | 34168 |
| HPV18 | L2 | SGTQIGARVH | 309 | 10 | | 34169 |
| HPV18 | L2 | SGTQIGARVHF | 309 | 11 | | 34170 |
| HPV18 | L2 | SISTTNFTNPA | 151 | 11 | | 34171 |
| HPV18 | L2 | SLITYDNPA | 247 | 9 | | 34172 |
| HPV18 | L2 | SLITYDNPAF | 247 | 10 | | 34173 |
| HPV18 | L2 | SSLITYDNPA | 246 | 10 | | 34174 |
| HPV18 | L2 | SSLITYDNPAF | 246 | 11 | | 34175 |
| HPV18 | L2 | SSTPLPTVR | 211 | 9 | | 34176 |
| HPV18 | L2 | SSTPLPTVRR | 211 | 10 | | 34177 |
| HPV18 | L2 | SSVVTSGA | 110 | 8 | | 34178 |
| HPV18 | L2 | SSVVTSGAPR | 110 | 10 | | 34179 |
| HPV18 | L2 | SSWDVPVY | 393 | 8 | | 34180 |
| HPV18 | L2 | STPLPTVR | 212 | 8 | | 34181 |
| HPV18 | L2 | STPLPTVRR | 212 | 9 | | 34182 |
| HPV18 | L2 | STPLPTVRRVA | 212 | 11 | | 34183 |
| HPV18 | L2 | STQYIGIH | 424 | 8 | | 34184 |
| HPV18 | L2 | STQYIGIHGTH | 424 | 11 | | 34185 |
| HPV18 | L2 | STSVSISTTNF | 147 | 11 | | 34186 |
| HPV18 | L2 | STTNFTNPA | 153 | 9 | | 34187 |
| HPV18 | L2 | STTNFTNPAF | 153 | 10 | | 34188 |
| HPV18 | L2 | STTSFAFF | 365 | 8 | | 34189 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV18 | L2 | STTSFAFFK | 365 | 9 | | 34190 |
| HPV18 | L2 | STTSFAFFKY | 365 | 10 | | 34191 |
| HPV18 | L2 | SVANPEFLTR | 235 | 10 | | 34192 |
| HPV18 | L2 | SVSISTTNF | 149 | 9 | | 34193 |
| HPV18 | L2 | SVTDLYKTCK | 13 | 10 | | 34194 |
| HPV18 | L2 | SVVTSGAPR | 111 | 9 | | 34195 |
| HPV18 | L2 | SVWPIVSPTA | 412 | 10 | | 34196 |
| HPV18 | L2 | TAPASTQY | 420 | 8 | | 34197 |
| HPV18 | L2 | TCPPDVVPK | 26 | 9 | | 34198 |
| HPV18 | L2 | TDLYKTCK | 15 | 8 | | 34199 |
| HPV18 | L2 | TFTGTSGF | 121 | 8 | | 34200 |
| HPV18 | L2 | TGEVAGNVF | 173 | 9 | | 34201 |
| HPV18 | L2 | TGSGTGGR | 61 | 8 | | 34202 |
| HPV18 | L2 | TGSGTGGRTGY | 61 | 11 | | 34203 |
| HPV18 | L2 | TGTSGFDITSA | 123 | 11 | | 34204 |
| HPV18 | L2 | TGYIPLGGR | 69 | 9 | | 34205 |
| HPV18 | L2 | TISSASSY | 377 | 8 | | 34206 |
| HPV18 | L2 | TSAGTTTPA | 131 | 9 | | 34207 |
| HPV18 | L2 | TSFAFFKY | 367 | 8 | | 34208 |
| HPV18 | L2 | TSGAPRPTF | 114 | 9 | | 34209 |
| HPV18 | L2 | TSGFDITSA | 125 | 9 | | 34210 |
| HPV18 | L2 | TSRRGTVR | 288 | 8 | | 34211 |
| HPV18 | L2 | TSRRGTVRF | 288 | 9 | | 34212 |
| HPV18 | L2 | TSRRGTVRFSR | 288 | 11 | | 34213 |
| HPV18 | L2 | TSSWDVPVY | 392 | 9 | | 34214 |
| HPV18 | L2 | TSVSISTTNF | 148 | 10 | | 34215 |
| HPV18 | L2 | TSVWPIVSPTA | 411 | 11 | | 34216 |
| HPV18 | L2 | TTLTFDPR | 261 | 8 | | 34217 |
| HPV18 | L2 | TTNFTNPA | 154 | 8 | | 34218 |
| HPV18 | L2 | TTNFTNPAF | 154 | 9 | | 34219 |
| HPV18 | L2 | TTSFAFFK | 366 | 8 | | 34220 |
| HPV18 | L2 | TTSFAFFKY | 366 | 9 | | 34221 |
| HPV18 | L2 | TVRFSRLGQR | 293 | 10 | | 34222 |
| HPV18 | L2 | TVRFSRLGQRA | 293 | 11 | | 34223 |
| HPV18 | L2 | TVRRVAGPR | 217 | 9 | | 34224 |
| HPV18 | L2 | TVRRVAGPRLY | 217 | 11 | | 34225 |
| HPV18 | L2 | TVVDVGPTR | 80 | 9 | | 34226 |
| HPV18 | L2 | VAGPRLYSR | 221 | 9 | | 34227 |
| HPV18 | L2 | VAGPRLYSRA | 221 | 10 | | 34228 |
| HPV18 | L2 | VAGPRLYSRAY | 221 | 11 | | 34229 |
| HPV18 | L2 | VANPEFLTR | 236 | 9 | | 34230 |
| HPV18 | L2 | VDTTLTFDPR | 259 | 10 | | 34231 |
| HPV18 | L2 | VFVGTPTSGTH | 180 | 11 | | 34232 |
| HPV18 | L2 | VGTPTSGTH | 182 | 9 | | 34233 |
| HPV18 | L2 | VGTPTSGTHGY | 182 | 11 | | 34234 |
| HPV18 | L2 | VSATEDNDLF | 339 | 10 | | 34235 |
| HPV18 | L2 | VSHRAARR | 2 | 8 | | 34236 |
| HPV18 | L2 | VSHRAARRK | 2 | 9 | | 34237 |
| HPV18 | L2 | VSHRAARRKR | 2 | 10 | | 34238 |
| HPV18 | L2 | VSHRAARRKRA | 2 | 11 | | 34239 |
| HPV18 | L2 | VSISTTNF | 150 | 8 | | 34240 |
| HPV18 | L2 | VSPTAPASTQY | 417 | 11 | | 34241 |
| HPV18 | L2 | VSVANPEF | 234 | 8 | | 34242 |
| HPV18 | L2 | VSVANPEFLTR | 234 | 11 | | 34243 |
| HPV18 | L2 | VTDLYKTCK | 14 | 9 | | 34244 |
| HPV18 | L2 | VTSGAPRPTF | 113 | 10 | | 34245 |
| HPV18 | L2 | VVDVGPTR | 81 | 8 | | 34246 |
| HPV18 | L2 | VVPKVEGTTLA | 31 | 11 | | 34247 |
| HPV18 | L2 | VVTSGAPR | 112 | 8 | | 34248 |
| HPV18 | L2 | VVTSGAPRPTF | 112 | 11 | | 34249 |
| HPV18 | L2 | YADDMDPA | 351 | 8 | | 34250 |
| HPV18 | L2 | YFFADGFVA | 453 | 9 | | 34251 |
| HPV18 | L2 | YFFADGFVAA | 453 | 10 | | 34252 |
| HPV18 | L2 | YFIPKKRK | 442 | 8 | | 34253 |
| HPV18 | L2 | YFIPKKRKR | 442 | 9 | | 34254 |
| HPV18 | L2 | YIELQPLVSA | 332 | 10 | | 34255 |
| HPV18 | L2 | YIGIHGTH | 427 | 8 | | 34256 |
| HPV18 | L2 | YIGIHGTHY | 427 | 9 | | 34257 |
| HPV18 | L2 | YIGIHGTHYY | 427 | 10 | | 34258 |
| HPV18 | L2 | YLWPLYYF | 436 | 8 | | 34259 |
| HPV18 | L2 | YLWPLYYFIPK | 436 | 11 | | 34260 |
| HPV18 | L2 | YSPTISSA | 374 | 8 | | 34261 |
| HPV18 | L2 | YSPTISSASSY | 374 | 11 | | 34262 |
| HPV18 | L2 | YSRAYQQVSVA | 227 | 11 | | 34263 |
| HPV31 | E1 | AAALYWYR | 296 | 8 | | 34264 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E1 | AAFGVTGTVA | 219 | 10 | | 34265 |
| HPV31 | E1 | AAMLGKFK | 185 | 8 | | 34266 |
| HPV31 | E1 | AAMLGKFKELY | 185 | 11 | | 34267 |
| HPV31 | E1 | ACAFLKSNSQA | 369 | 11 | | 34268 |
| HPV31 | E1 | ADAKIGMLDDA | 494 | 11 | | 34269 |
| HPV31 | E1 | ADSDSNACA | 363 | 9 | | 34270 |
| HPV31 | E1 | ADSDSNACAF | 363 | 10 | | 34271 |
| HPV31 | E1 | AFGVTGTVA | 220 | 9 | | 34272 |
| HPV31 | E1 | AFLKSNSQA | 371 | 9 | | 34273 |
| HPV31 | E1 | AFLKSNSQAK | 371 | 10 | | 34274 |
| HPV31 | E1 | AGKDDRWPY | 550 | 9 | | 34275 |
| HPV31 | E1 | AGKDDRWPYLH | 550 | 11 | | 34276 |
| HPV31 | E1 | AICIENNSK | 111 | 9 | | 34277 |
| HPV31 | E1 | AICIENNSKTA | 111 | 11 | | 34278 |
| HPV31 | E1 | ALFHAQEA | 68 | 8 | | 34279 |
| HPV31 | E1 | ALFHAQEAEEH | 68 | 11 | | 34280 |
| HPV31 | E1 | ALKLFLKGVPK | 439 | 11 | | 34281 |
| HPV31 | E1 | AMLGKFKELY | 186 | 10 | | 34282 |
| HPV31 | E1 | ATTPCWHY | 504 | 8 | | 34283 |
| HPV31 | E1 | AVQVLKRK | 81 | 8 | | 34284 |
| HPV31 | E1 | AVQVLKRKY | 81 | 9 | | 34285 |
| HPV31 | E1 | CAFLKSNSQA | 370 | 10 | | 34286 |
| HPV31 | E1 | CAFLKSNSQAK | 370 | 11 | | 34287 |
| HPV31 | E1 | CAKNRITIEK | 263 | 10 | | 34288 |
| HPV31 | E1 | CDKVSDEGDWR | 410 | 11 | | 34289 |
| HPV31 | E1 | CGTMCRHY | 385 | 8 | | 34290 |
| HPV31 | E1 | CGTMCRHYK | 385 | 9 | | 34291 |
| HPV31 | E1 | CGTMCRHYKR | 385 | 10 | | 34292 |
| HPV31 | E1 | CGTMCRHYKRA | 385 | 11 | | 34293 |
| HPV31 | E1 | CIENNSKTA | 113 | 9 | | 34294 |
| HPV31 | E1 | CIENNSKTAK | 113 | 10 | | 34295 |
| HPV31 | E1 | CIENNSKTAKR | 113 | 11 | | 34296 |
| HPV31 | E1 | CIISYANSK | 477 | 9 | | 34297 |
| HPV31 | E1 | CIISYANSKSH | 477 | 11 | | 34298 |
| HPV31 | E1 | CLYCHLQSLA | 239 | 10 | | 34299 |
| HPV31 | E1 | CMLIQPPK | 284 | 8 | | 34300 |
| HPV31 | E1 | CMLIQPPKLR | 284 | 10 | | 34301 |
| HPV31 | E1 | CTDWCVAA | 213 | 8 | | 34302 |
| HPV31 | E1 | CTDWCVAAF | 213 | 9 | | 34303 |
| HPV31 | E1 | CVDYNISPR | 100 | 9 | | 34304 |
| HPV31 | E1 | CVDYNISPRLK | 100 | 11 | | 34305 |
| HPV31 | E1 | CVSGQNIR | 620 | 8 | | 34306 |
| HPV31 | E1 | DAKIGMLDDA | 495 | 10 | | 34307 |
| HPV31 | E1 | DATTPCWH | 503 | 8 | | 34308 |
| HPV31 | E1 | DATTPCWHY | 503 | 9 | | 34309 |
| HPV31 | E1 | DCGTMCRH | 384 | 8 | | 34310 |
| HPV31 | E1 | DCGTMCRHY | 384 | 9 | | 34311 |
| HPV31 | E1 | DCGTMCRHYK | 384 | 10 | | 34312 |
| HPV31 | E1 | DCGTMCRHYKR | 384 | 11 | | 34313 |
| HPV31 | E1 | DDATTPCWH | 502 | 9 | | 34314 |
| HPV31 | E1 | DDATTPCWHY | 502 | 10 | | 34315 |
| HPV31 | E1 | DDRWPYLH | 553 | 8 | | 34316 |
| HPV31 | E1 | DDRWPYLHSR | 553 | 10 | | 34317 |
| HPV31 | E1 | DDSEIAYK | 351 | 8 | | 34318 |
| HPV31 | E1 | DDSEIAYKY | 351 | 9 | | 34319 |
| HPV31 | E1 | DDSEIAYKYA | 351 | 10 | | 34320 |
| HPV31 | E1 | DFIDNCNVY | 49 | 9 | | 34321 |
| HPV31 | E1 | DGDSFSTF | 611 | 8 | | 34322 |
| HPV31 | E1 | DGDSFSTFK | 611 | 9 | | 34323 |
| HPV31 | E1 | DGEGTGCNGWF | 8 | 11 | | 34324 |
| HPV31 | E1 | DGNPVSIDVK | 521 | 10 | | 34325 |
| HPV31 | E1 | DGNPVSIDVKH | 521 | 11 | | 34326 |
| HPV31 | E1 | DISSCVDY | 96 | 8 | | 34327 |
| HPV31 | E1 | DIVKFLRY | 421 | 8 | | 34328 |
| HPV31 | E1 | DLSQMVQWA | 336 | 9 | | 34329 |
| HPV31 | E1 | DLSQMVQWAY | 336 | 10 | | 34330 |
| HPV31 | E1 | DSDSNACA | 364 | 8 | | 34331 |
| HPV31 | E1 | DSDSNACAF | 364 | 9 | | 34332 |
| HPV31 | E1 | DSDSNACAFLK | 364 | 11 | | 34333 |
| HPV31 | E1 | DSEIAYKY | 352 | 8 | | 34334 |
| HPV31 | E1 | DSEIAYKYA | 352 | 9 | | 34335 |
| HPV31 | E1 | DSNACAFLK | 366 | 9 | | 34336 |
| HPV31 | E1 | DTGEDMVDF | 42 | 9 | | 34337 |
| HPV31 | E1 | DVKHKALMQLK | 528 | 11 | | 34338 |
| HPV31 | E1 | DVMDDSEIA | 348 | 9 | | 34339 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E1 | DVMDDSEIAY | 348 | 10 | | 34340 |
| HPV31 | E1 | DVMDDSEIAYK | 348 | 11 | | 34341 |
| HPV31 | E1 | EAEEHAEA | 74 | 8 | | 34342 |
| HPV31 | E1 | EAETAQALF | 62 | 9 | | 34343 |
| HPV31 | E1 | EAETAQALFH | 62 | 10 | | 34344 |
| HPV31 | E1 | EAETAQALFHA | 62 | 11 | | 34345 |
| HPV31 | E1 | EAVQVLKR | 80 | 8 | | 34346 |
| HPV31 | E1 | EAVQVLKRK | 80 | 9 | | 34347 |
| HPV31 | E1 | EAVQVLKRKY | 80 | 10 | | 34348 |
| HPV31 | E1 | EDKENDGDSF | 606 | 10 | | 34349 |
| HPV31 | E1 | EFVSFLSA | 432 | 8 | | 34350 |
| HPV31 | E1 | EFVSFLSALK | 432 | 10 | | 34351 |
| HPV31 | E1 | EGDWRDIVK | 416 | 9 | | 34352 |
| HPV31 | E1 | EGDWRDIVKF | 416 | 10 | | 34353 |
| HPV31 | E1 | EGFKTLLQPY | 229 | 10 | | 34354 |
| HPV31 | E1 | EGTGCNGWF | 10 | 9 | 0.0008 | 34355 |
| HPV31 | E1 | EGTGCNGWFY | 10 | 10 | 0.0005 | 34356 |
| HPV31 | E1 | EIAYKYAQLA | 354 | 10 | | 34357 |
| HPV31 | E1 | ELIRPFQSNK | 201 | 10 | | 34358 |
| HPV31 | E1 | ELSDKNWK | 583 | 8 | | 34359 |
| HPV31 | E1 | ELSDKNWKSF | 583 | 10 | | 34360 |
| HPV31 | E1 | ELSDKNWKSFF | 583 | 11 | | 34361 |
| HPV31 | E1 | ETAQALFH | 64 | 8 | | 34362 |
| HPV31 | E1 | ETAQALFHA | 64 | 9 | | 34363 |
| HPV31 | E1 | ETPEWIER | 315 | 8 | | 34364 |
| HPV31 | E1 | FDKNGNPVY | 574 | 9 | | 34365 |
| HPV31 | E1 | FDLSQMVQWA | 335 | 10 | | 34366 |
| HPV31 | E1 | FDLSQMVQWAY | 335 | 11 | | 34367 |
| HPV31 | E1 | FFSRTWCR | 592 | 8 | | 34368 |
| HPV31 | E1 | FGMSLISF | 466 | 8 | | 34369 |
| HPV31 | E1 | FGVTGTVA | 221 | 8 | | 34370 |
| HPV31 | E1 | FGVTGTVAEGF | 221 | 11 | | 34371 |
| HPV31 | E1 | FIDNCNVY | 50 | 8 | | 34372 |
| HPV31 | E1 | FLKGVPKK | 443 | 8 | | 34373 |
| HPV31 | E1 | FLKSNSQA | 372 | 8 | | 34374 |
| HPV31 | E1 | FLKSNSQAK | 372 | 9 | 0.0013 | 34375 |
| HPV31 | E1 | FLQGCIISY | 473 | 9 | | 34376 |
| HPV31 | E1 | FLQGCIISYA | 473 | 10 | | 34377 |
| HPV31 | E1 | FLRYQQIEF | 425 | 9 | | 34378 |
| HPV31 | E1 | FLSALKLF | 436 | 8 | | 34379 |
| HPV31 | E1 | FLSALKLFLK | 436 | 10 | | 34380 |
| HPV31 | E1 | FMELIRPF | 199 | 8 | | 34381 |
| HPV31 | E1 | FSRTWCRLNLH | 593 | 11 | | 34382 |
| HPV31 | E1 | FTFPNPFPF | 566 | 9 | 0.0008 | 34383 |
| HPV31 | E1 | FTFPNPFPFDK | 566 | 11 | | 34384 |
| HPV31 | E1 | FVSFLSALK | 433 | 9 | | 34385 |
| HPV31 | E1 | FVSFLSALKLF | 433 | 11 | | 34386 |
| HPV31 | E1 | GAPNTGKSY | 457 | 9 | | 34387 |
| HPV31 | E1 | GAPNTGKSYF | 457 | 10 | | 34388 |
| HPV31 | E1 | CCIISYANSK | 476 | 10 | | 34389 |
| HPV31 | E1 | GCNGWFYVEA | 13 | 10 | | 34390 |
| HPV31 | E1 | GDSFSTFK | 612 | 8 | | 34391 |
| HPV31 | E1 | GDWRDIVK | 417 | 8 | | 34392 |
| HPV31 | E1 | GDWRDIVKF | 417 | 9 | | 34393 |
| HPV31 | E1 | GDWRDIVKFLR | 417 | 11 | | 34394 |
| HPV31 | E1 | GFKTLLQPY | 230 | 9 | | 34395 |
| HPV31 | E1 | GMSNISDVY | 305 | 9 | | 34396 |
| HPV31 | E1 | GMVMLMLVR | 252 | 9 | | 34397 |
| HPV31 | E1 | GMVMLMLVRF | 252 | 10 | | 34398 |
| HPV31 | E1 | GMVMLMLVRFK | 252 | 11 | | 34399 |
| HPV31 | E1 | GSDGTHSER | 157 | 9 | | 34400 |
| HPV31 | E1 | GTGCNGWF | 11 | 8 | | 34401 |
| HPV31 | E1 | GTGCNGWFY | 11 | 9 | 0.0004 | 34402 |
| HPV31 | E1 | GTMCRHYK | 386 | 8 | | 34403 |
| HPV31 | E1 | GTMCRHYKR | 386 | 9 | | 34404 |
| HPV31 | E1 | GTMCRHYKRA | 386 | 10 | | 34405 |
| HPV31 | E1 | GTVAEGFK | 225 | 8 | | 34406 |
| HPV31 | E1 | GVPKKNCILIH | 446 | 11 | | 34407 |
| HPV31 | E1 | GVSFMELIR | 196 | 9 | | 34408 |
| HPV31 | E1 | GVSFMELIRPF | 196 | 11 | | 34409 |
| HPV31 | E1 | GVTGTVAEGF | 222 | 10 | | 34410 |
| HPV31 | E1 | GVTGTVAEGFK | 222 | 11 | | 34411 |
| HPV31 | E1 | HAEAVQVLK | 78 | 9 | | 34412 |
| HPV31 | E1 | HAEAVQVLKR | 78 | 10 | | 34413 |
| HPV31 | E1 | HAEAVQVLKRK | 78 | 11 | | 34414 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E1 | HAQEAEEH | 71 | 8 | | 34415 |
| HPV31 | E1 | HAQEAEEHA | 71 | 9 | | 34416 |
| HPV31 | E1 | HAQEAEEHAEA | 71 | 11 | | 34417 |
| HPV31 | E1 | HFWLQPLA | 487 | 8 | | 34418 |
| HPV31 | E1 | HFWLQPLADA | 487 | 10 | | 34419 |
| HPV31 | E1 | HFWLQPLADAK | 487 | 11 | | 34420 |
| HPV31 | E1 | HGAPNTGK | 456 | 8 | | 34421 |
| HPV31 | E1 | HGAPNTGKSY | 456 | 10 | | 34422 |
| HPV31 | E1 | HGAPNTGKSYF | 456 | 11 | | 34423 |
| HPV31 | E1 | HSERENETPTR | 162 | 11 | | 34424 |
| HPV31 | E1 | HSFNDTTF | 328 | 8 | | 34425 |
| HPV31 | E1 | HSRLVVFTF | 560 | 9 | | 34426 |
| HPV31 | E1 | IAYKYAQLA | 355 | 9 | | 34427 |
| HPV31 | E1 | ICIENNSK | 112 | 8 | | 34428 |
| HPV31 | E1 | ICIENNSKTA | 112 | 10 | | 34429 |
| HPV31 | E1 | ICIENNSKTAK | 112 | 11 | | 34430 |
| HPV31 | E1 | IDNCNVYNNQA | 51 | 11 | | 34431 |
| HPV31 | E1 | IDNYLRNA | 512 | 8 | | 34432 |
| HPV31 | E1 | IISYANSK | 478 | 8 | | 34433 |
| HPV31 | E1 | IISYANSKSH | 478 | 10 | | 34434 |
| HPV31 | E1 | IISYANSKSHF | 478 | 11 | | 34435 |
| HPV31 | E1 | ILIHGAPNTGK | 453 | 11 | | 34436 |
| HPV31 | E1 | ILQVLKTSNGK | 174 | 11 | | 34437 |
| HPV31 | E1 | ISFLQGCIISY | 471 | 11 | | 34438 |
| HPV31 | E1 | ISYANSKSH | 479 | 9 | | 34439 |
| HPV31 | E1 | ISYANSKSHF | 479 | 10 | | 34440 |
| HPV31 | E1 | ITIEKLLEK | 268 | 9 | | 34441 |
| HPV31 | E1 | ITSNINAGK | 544 | 9 | | 34442 |
| HPV31 | E1 | IVKDCGTMCR | 381 | 10 | | 34443 |
| HPV31 | E1 | IVKDCGTMCRH | 381 | 11 | | 34444 |
| HPV31 | E1 | KAAMLGKF | 184 | 8 | | 34445 |
| HPV31 | E1 | KAAMLGKFK | 184 | 9 | | 34446 |
| HPV31 | E1 | KAICIENNSK | 110 | 10 | | 34447 |
| HPV31 | E1 | KCAKNRITIEK | 262 | 11 | | 34448 |
| HPV31 | E1 | KCVSGQNIR | 619 | 9 | | 34449 |
| HPV31 | E1 | KDCGTMCR | 383 | 8 | | 34450 |
| HPV31 | E1 | KDCGTMCRH | 383 | 9 | | 34451 |
| HPV31 | E1 | KDCGTMCRHY | 383 | 10 | | 34452 |
| HPV31 | E1 | KDCGTMCRHYK | 383 | 11 | | 34453 |
| HPV31 | E1 | KDDRWPYLH | 552 | 9 | | 34454 |
| HPV31 | E1 | KDDRWPYLHSR | 552 | 11 | | 34455 |
| HPV31 | E1 | KFKELYGVSF | 190 | 10 | | 34456 |
| HPV31 | E1 | KFLRYQQIEF | 424 | 10 | | 34457 |
| HPV31 | E1 | KIGMLDDA | 497 | 8 | | 34458 |
| HPV31 | E1 | KIVKDCGTMCR | 380 | 11 | | 34459 |
| HPV31 | E1 | KLFLKGVPK | 441 | 9 | | 34460 |
| HPV31 | E1 | KLFLKGVPKK | 441 | 10 | | 34461 |
| HPV31 | E1 | KLRSTAAA | 291 | 8 | | 34462 |
| HPV31 | E1 | KLRSTAAALY | 291 | 10 | | 34463 |
| HPV31 | E1 | KSFFSRTWCR | 590 | 10 | | 34464 |
| HPV31 | E1 | KSHFWLQPLA | 485 | 10 | | 34465 |
| HPV31 | E1 | KSNSQAKIVK | 374 | 10 | | 34466 |
| HPV31 | E1 | KSTCTDWCVA | 210 | 10 | | 34467 |
| HPV31 | E1 | KSTCTDWCVAA | 210 | 11 | | 34468 |
| HPV31 | E1 | KSYFGMSLISF | 463 | 11 | | 34469 |
| HPV31 | E1 | KTAKRRLF | 119 | 8 | | 34470 |
| HPV31 | E1 | KTLLQPYCLY | 232 | 10 | | 34471 |
| HPV31 | E1 | KTSNGKAA | 179 | 8 | | 34472 |
| HPV31 | E1 | KVSDEGDWR | 412 | 9 | | 34473 |
| HPV31 | E1 | LADSDSNA | 362 | 8 | | 34474 |
| HPV31 | E1 | LADSDSNACA | 362 | 10 | | 34475 |
| HPV31 | E1 | LADSDSNACAF | 362 | 11 | | 34476 |
| HPV31 | E1 | LDDATTPCWH | 501 | 10 | | 34477 |
| HPV31 | E1 | LDDATTPCWHY | 501 | 11 | | 34478 |
| HPV31 | E1 | LDGNPVSIDVK | 520 | 11 | | 34479 |
| HPV31 | E1 | LFELPDSGY | 125 | 9 | | 34480 |
| HPV31 | E1 | LFHAQEAEEH | 69 | 10 | | 34481 |
| HPV31 | E1 | LFHAQEAEEHA | 69 | 11 | | 34482 |
| HPV31 | E1 | LFLKGVPK | 442 | 8 | | 34483 |
| HPV31 | E1 | LFLKGVPKK | 442 | 9 | | 34484 |
| HPV31 | E1 | LGKFKELY | 188 | 8 | | 34485 |
| HPV31 | E1 | LIHGAPNTGK | 454 | 10 | | 34486 |
| HPV31 | E1 | LIQPPKLR | 286 | 8 | | 34487 |
| HPV31 | E1 | LIQPPKLRSTA | 286 | 11 | | 34488 |
| HPV31 | E1 | LIRPFQSNK | 202 | 9 | | 34489 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E1 | LITSNINA | 543 | 8 | | 34490 |
| HPV31 | E1 | LITSNINAGK | 543 | 10 | | 34491 |
| HPV31 | E1 | LLITSNINA | 542 | 9 | | 34492 |
| HPV31 | E1 | LLITSNINAGK | 542 | 11 | | 34493 |
| HPV31 | E1 | LLQPYCLY | 234 | 8 | | 34494 |
| HPV31 | E1 | LLQPYCLYCH | 234 | 10 | | 34495 |
| HPV31 | E1 | LMLVRFKCA | 256 | 9 | | 34496 |
| HPV31 | E1 | LMLVRFKCAK | 256 | 10 | | 34497 |
| HPV31 | E1 | LSALKLFLK | 437 | 9 | | 34498 |
| HPV31 | E1 | LSCNGSDGTH | 153 | 10 | | 34499 |
| HPV31 | E1 | LSDISSCVDY | 94 | 10 | | 34500 |
| HPV31 | E1 | LSDKNWKSF | 584 | 9 | | 34501 |
| HPV31 | E1 | LSDKNWKSFF | 584 | 10 | | 34502 |
| HPV31 | E1 | LSQMVQWA | 337 | 8 | | 34503 |
| HPV31 | E1 | LSQMVQWAY | 337 | 9 | | 34504 |
| HPV31 | E1 | LVRFKCAK | 258 | 8 | | 34505 |
| HPV31 | E1 | LVRFKCAKNR | 258 | 10 | | 34506 |
| HPV31 | E1 | LVVFTFPNPF | 563 | 10 | | 34507 |
| HPV31 | E1 | MCRHYKRA | 388 | 8 | | 34508 |
| HPV31 | E1 | MCRHYKRAEK | 388 | 10 | | 34509 |
| HPV31 | E1 | MCRHYKRAEKR | 388 | 11 | | 34510 |
| HPV31 | E1 | MDDSEIAY | 350 | 8 | | 34511 |
| HPV31 | E1 | MDDSEIAYK | 350 | 9 | | 34512 |
| HPV31 | E1 | MDDSEIAYKY | 350 | 10 | | 34513 |
| HPV31 | E1 | MDDSEIAYKYA | 350 | 11 | | 34514 |
| HPV31 | E1 | MGQWIKSR | 402 | 8 | | 34515 |
| HPV31 | E1 | MGQWIKSRCDK | 402 | 11 | | 34516 |
| HPV31 | E1 | MLDDATTPCWH | 500 | 11 | | 34517 |
| HPV31 | E1 | MLGKFKELY | 187 | 9 | | 34518 |
| HPV31 | E1 | MLIQPPKLR | 285 | 9 | 0.0005 | 34519 |
| HPV31 | E1 | MLMLVRFK | 255 | 8 | | 34520 |
| HPV31 | E1 | MLMLVRFKCA | 255 | 10 | | 34521 |
| HPV31 | E1 | MLMLVRFKCAK | 255 | 11 | | 34522 |
| HPV31 | E1 | MLVRFKCA | 257 | 8 | | 34523 |
| HPV31 | E1 | MLVRFKCAK | 257 | 9 | | 34524 |
| HPV31 | E1 | MLVRFKCAKNR | 257 | 11 | | 34525 |
| HPV31 | E1 | MSMGQWIK | 400 | 8 | | 34526 |
| HPV31 | E1 | MSMGQWIKSR | 400 | 10 | | 34527 |
| HPV31 | E1 | MSNISDVY | 306 | 8 | | 34528 |
| HPV31 | E1 | MVDFIDNCNVY | 47 | 11 | | 34529 |
| HPV31 | E1 | MVMLMLVR | 253 | 8 | | 34530 |
| HPV31 | E1 | MVMLMLVRF | 253 | 9 | | 34531 |
| HPV31 | E1 | MVMLMLVRFK | 253 | 10 | | 34532 |
| HPV31 | E1 | NAGKDDRWPY | 549 | 10 | | 34533 |
| HPV31 | E1 | NCILIHGA | 451 | 8 | | 34534 |
| HPV31 | E1 | NCMLIQPPK | 283 | 9 | | 34535 |
| HPV31 | E1 | NCMLIQPPKLR | 283 | 11 | | 34536 |
| HPV31 | E1 | NCNVYNNQA | 53 | 9 | | 34537 |
| HPV31 | E1 | NCNVYNNQAEA | 53 | 11 | | 34538 |
| HPV31 | E1 | NDGDSFSTF | 610 | 9 | | 34539 |
| HPV31 | E1 | NDGDSFSTFK | 610 | 10 | | 34540 |
| HPV31 | E1 | NDVMDDSEIA | 347 | 10 | | 34541 |
| HPV31 | E1 | NDVMDDSEIAY | 347 | 11 | | 34542 |
| HPV31 | E1 | NGKAAMLGK | 182 | 9 | | 34543 |
| HPV31 | E1 | NGKAAMLGKF | 182 | 10 | | 34544 |
| HPV31 | E1 | NGKAAMLGKFK | 182 | 11 | | 34545 |
| HPV31 | E1 | NGNPVYELSDK | 577 | 11 | | 34546 |
| HPV31 | E1 | NGSDGTHSER | 156 | 10 | | 34547 |
| HPV31 | E1 | NGWFYVEA | 15 | 8 | | 34548 |
| HPV31 | E1 | NINAGKDDR | 547 | 9 | | 34549 |
| HPV31 | E1 | NISPRLKA | 104 | 8 | | 34550 |
| HPV31 | E1 | NLHEEEDK | 601 | 8 | | 34551 |
| HPV31 | E1 | NSKTAKRR | 117 | 8 | | 34552 |
| HPV31 | E1 | NSKTAKRRLF | 117 | 10 | | 34553 |
| HPV31 | E1 | NSQAKIVK | 376 | 8 | | 34554 |
| HPV31 | E1 | NVYNNQAEA | 55 | 9 | | 34555 |
| HPV31 | E1 | PCWHYIDNY | 507 | 9 | | 34556 |
| HPV31 | E1 | PCWHYIDNYLR | 507 | 11 | | 34557 |
| HPV31 | E1 | PFDKNGNPVY | 573 | 10 | | 34558 |
| HPV31 | E1 | PLLITSNINA | 541 | 10 | | 34559 |
| HPV31 | E1 | PLSDISSCVDY | 93 | 11 | | 34560 |
| HPV31 | E1 | PTRNILQVLK | 170 | 10 | | 34561 |
| HPV31 | E1 | PVSIDVKH | 524 | 8 | | 34562 |
| HPV31 | E1 | PVSIDVKHK | 524 | 9 | | 34563 |
| HPV31 | E1 | PVSIDVKHKA | 524 | 10 | | 34564 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E1 | PVYELSDK | 580 | 8 | | 34565 |
| HPV31 | E1 | PVYELSDKNWK | 580 | 11 | | 34566 |
| HPV31 | E1 | QAEAETAQA | 60 | 9 | | 34567 |
| HPV31 | E1 | QAEAETAQALF | 60 | 11 | | 34568 |
| HPV31 | E1 | QALFHAQEA | 67 | 9 | | 34569 |
| HPV31 | E1 | QGCIISYA | 475 | 8 | | 34570 |
| HPV31 | E1 | QGCIISYANSK | 475 | 11 | | 34571 |
| HPV31 | E1 | QIEFVSFLSA | 430 | 10 | | 34572 |
| HPV31 | E1 | QLADSDSNA | 361 | 9 | | 34573 |
| HPV31 | E1 | QLADSDSNACA | 361 | 11 | | 34574 |
| HPV31 | E1 | QMSMGQWIK | 399 | 9 | | 34575 |
| HPV31 | E1 | QMSMGQWIKSR | 399 | 11 | | 34576 |
| HPV31 | E1 | QTVLQHSF | 323 | 8 | | 34577 |
| HPV31 | E1 | QVLKTSNGK | 176 | 9 | | 34578 |
| HPV31 | E1 | QVLKTSNGKA | 176 | 10 | | 34579 |
| HPV31 | E1 | QVLKTSNGKAA | 176 | 11 | | 34580 |
| HPV31 | E1 | RDIVKFLR | 420 | 8 | | 34581 |
| HPV31 | E1 | RDIVKFLRY | 420 | 9 | | 34582 |
| HPV31 | E1 | RFKCAKNR | 260 | 8 | | 34583 |
| HPV31 | E1 | RITIEKLLEK | 267 | 10 | | 34584 |
| HPV31 | E1 | RLFELPDSGY | 124 | 10 | | 34585 |
| HPV31 | E1 | RLNLHEEEDK | 599 | 10 | | 34586 |
| HPV31 | E1 | RLVVFTFPNPF | 562 | 11 | | 34587 |
| HPV31 | E1 | RSTAAALY | 293 | 8 | | 34588 |
| HPV31 | E1 | RSTAAALYWY | 293 | 10 | | 34589 |
| HPV31 | E1 | RSTAAALYWYR | 293 | 11 | | 34590 |
| HPV31 | E1 | RTGMSNISDVY | 303 | 11 | | 34591 |
| HPV31 | E1 | RTWCRLNLH | 595 | 9 | | 34592 |
| HPV31 | E1 | SALKLFLK | 438 | 8 | | 34593 |
| HPV31 | E1 | SCNGSDGTH | 154 | 9 | | 34594 |
| HPV31 | E1 | SCVDYNISPR | 99 | 10 | | 34595 |
| HPV31 | E1 | SDEGDWRDIVK | 414 | 11 | | 34596 |
| HPV31 | E1 | SDGTHSER | 158 | 8 | | 34597 |
| HPV31 | E1 | SDISSCVDY | 95 | 9 | | 34598 |
| HPV31 | E1 | SDKNWKSF | 585 | 8 | | 34599 |
| HPV31 | E1 | SDKNWKSFF | 585 | 9 | | 34600 |
| HPV31 | E1 | SDKNWKSFFSR | 585 | 11 | | 34601 |
| HPV31 | E1 | SDSNACAF | 365 | 8 | | 34602 |
| HPV31 | E1 | SDSNACAFLK | 365 | 10 | | 34603 |
| HPV31 | E1 | SDTGEDMVDF | 41 | 10 | | 34604 |
| HPV31 | E1 | SFFSRTWCR | 591 | 9 | | 34605 |
| HPV31 | E1 | SFLQGCIISY | 472 | 10 | | 34606 |
| HPV31 | E1 | SFLQGCIISYA | 472 | 11 | | 34607 |
| HPV31 | E1 | SFLSALKLF | 435 | 9 | | 34608 |
| HPV31 | E1 | SFLSALKLFLK | 435 | 11 | | 34609 |
| HPV31 | E1 | SFMELIRPF | 198 | 9 | | 34610 |
| HPV31 | E1 | SIDVKHKA | 526 | 8 | | 34611 |
| HPV31 | E1 | SMGQWIKSR | 401 | 9 | | 34612 |
| HPV31 | E1 | SSCVDYNISPR | 98 | 11 | | 34613 |
| HPV31 | E1 | SSDTGEDMVDF | 40 | 11 | | 34614 |
| HPV31 | E1 | STAAALYWY | 294 | 9 | | 34615 |
| HPV31 | E1 | STAAALYWYR | 294 | 10 | | 34616 |
| HPV31 | E1 | STCTDWCVA | 211 | 9 | | 34617 |
| HPV31 | E1 | STCTDWCVAA | 211 | 10 | | 34618 |
| HPV31 | E1 | STCTDWCVAAF | 211 | 11 | | 34619 |
| HPV31 | E1 | STNCMLIQPPK | 281 | 11 | | 34620 |
| HPV31 | E1 | TAAALYWY | 295 | 8 | | 34621 |
| HPV31 | E1 | TAAALYWYR | 295 | 9 | | 34622 |
| HPV31 | E1 | TAQALFHA | 65 | 8 | | 34623 |
| HPV31 | E1 | TAQALFHAQEA | 65 | 11 | | 34624 |
| HPV31 | E1 | TCTDWCVA | 212 | 8 | | 34625 |
| HPV31 | E1 | TCTDWCVAA | 212 | 9 | | 34626 |
| HPV31 | E1 | TCTDWCVAAF | 212 | 10 | | 34627 |
| HPV31 | E1 | TDWCVAAF | 214 | 8 | | 34628 |
| HPV31 | E1 | TFDLSQMVQWA | 334 | 11 | | 34629 |
| HPV31 | E1 | TFKCVSGQNIR | 617 | 11 | | 34630 |
| HPV31 | E1 | TFPNPFPF | 567 | 8 | | 34631 |
| HPV31 | E1 | TFPNPFPFDK | 567 | 10 | | 34632 |
| HPV31 | E1 | TGCNGWFY | 12 | 8 | | 34633 |
| HPV31 | E1 | TGCNGWFYVEA | 12 | 11 | | 34634 |
| HPV31 | E1 | TGEDMVDF | 43 | 8 | | 34635 |
| HPV31 | E1 | TGMSNISDVY | 304 | 10 | | 34636 |
| HPV31 | E1 | TGTVAEGF | 224 | 8 | | 34637 |
| HPV31 | E1 | TGTVAEGFK | 224 | 9 | | 34638 |
| HPV31 | E1 | TIEKLLEK | 269 | 8 | | 34639 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E1 | TLLQPYCLY | 233 | 9 | | 34640 |
| HPV31 | E1 | TLLQPYCLYCH | 233 | 11 | | 34641 |
| HPV31 | E1 | TLSCNGSDGTH | 152 | 11 | | 34642 |
| HPV31 | E1 | TMCRHYKR | 387 | 8 | | 34643 |
| HPV31 | E1 | TMCRHYKRA | 387 | 9 | | 34644 |
| HPV31 | E1 | TMCRHYKRAEK | 387 | 11 | | 34645 |
| HPV31 | E1 | TSNGKAAMLGK | 180 | 11 | | 34646 |
| HPV31 | E1 | TSNINAGK | 545 | 8 | | 34647 |
| HPV31 | E1 | TSNINAGKDDR | 545 | 11 | | 34648 |
| HPV31 | E1 | TTPCWHYIDNY | 505 | 11 | | 34649 |
| HPV31 | E1 | VAAFGVTGTVA | 218 | 11 | | 34650 |
| HPV31 | E1 | VDFIDNCNVY | 48 | 10 | | 34651 |
| HPV31 | E1 | VDYNISPR | 101 | 8 | | 34652 |
| HPV31 | E1 | VDYNISPRLK | 101 | 10 | | 34653 |
| HPV31 | E1 | VDYNISPRLKA | 101 | 11 | | 34654 |
| HPV31 | E1 | VFTFPNPF | 565 | 8 | | 34655 |
| HPV31 | E1 | VFTFPNPFPF | 565 | 10 | | 34656 |
| HPV31 | E1 | VLKTSNGK | 177 | 8 | | 34657 |
| HPV31 | E1 | VLKTSNGKA | 177 | 9 | | 34658 |
| HPV31 | E1 | VLKTSNGKAA | 177 | 10 | | 34659 |
| HPV31 | E1 | VLQHSFNDTTF | 325 | 11 | | 34660 |
| HPV31 | E1 | VMDDSEIA | 349 | 8 | | 34661 |
| HPV31 | E1 | VMDDSEIAY | 349 | 9 | | 34662 |
| HPV31 | E1 | VMDDSEIAYK | 349 | 10 | | 34663 |
| HPV31 | E1 | VMDDSEIAYKY | 349 | 11 | | 34664 |
| HPV31 | E1 | VMLMLVRF | 254 | 8 | | 34665 |
| HPV31 | E1 | VMLMLVRFK | 254 | 9 | | 34666 |
| HPV31 | E1 | VMLMLVRFKCA | 254 | 11 | | 34667 |
| HPV31 | E1 | VSDEGDWR | 413 | 8 | | 34668 |
| HPV31 | E1 | VSFLSALK | 434 | 8 | | 34669 |
| HPV31 | E1 | VSFLSALKLF | 434 | 10 | | 34670 |
| HPV31 | E1 | VSFMELIR | 197 | 8 | | 34671 |
| HPV31 | E1 | VSFMELIRPF | 197 | 10 | | 34672 |
| HPV31 | E1 | VSIDVKHK | 525 | 8 | | 34673 |
| HPV31 | E1 | VSIDVKHKA | 525 | 9 | | 34674 |
| HPV31 | E1 | VTGTVAEGF | 223 | 9 | | 34675 |
| HPV31 | E1 | VTGTVAEGFK | 223 | 10 | | 34676 |
| HPV31 | E1 | VVFTFPNPF | 564 | 9 | | 34677 |
| HPV31 | E1 | VVFTFPNPFPF | 564 | 11 | | 34678 |
| HPV31 | E1 | WFYVEAVIDR | 17 | 10 | | 34679 |
| HPV31 | E1 | WGMVMLMLVR | 251 | 10 | | 34680 |
| HPV31 | E1 | WGMVMLMLVRF | 251 | 11 | | 34681 |
| HPV31 | E1 | WIERQTVLQH | 319 | 10 | | 34682 |
| HPV31 | E1 | WIKSRCDK | 405 | 8 | | 34683 |
| HPV31 | E1 | WLQPLADA | 489 | 8 | | 34684 |
| HPV31 | E1 | WLQPLADAK | 489 | 9 | 0.0005 | 34685 |
| HPV31 | E1 | YANSKSHF | 481 | 8 | | 34686 |
| HPV31 | E1 | YAQLADSDSNA | 359 | 11 | | 34687 |
| HPV31 | E1 | YCHLQSLA | 241 | 8 | | 34688 |
| HPV31 | E1 | YCLYCHLQSLA | 238 | 11 | | 34689 |
| HPV31 | E1 | YFGMSLISF | 465 | 9 | | 34690 |
| HPV31 | E1 | YGETPEWIER | 313 | 10 | | 34691 |
| HPV31 | E1 | YGVSFMELIR | 195 | 10 | | 34692 |
| HPV31 | E1 | YIDNYLRNA | 511 | 9 | | 34693 |
| HPV31 | E1 | YLHSRLVVF | 558 | 9 | | 34694 |
| HPV31 | E1 | YLHSRLVVFTF | 558 | 11 | | 34695 |
| HPV31 | E1 | YVEAVIDR | 19 | 8 | | 34696 |
| HPV31 | E2 | AAACTNQTR | 277 | 9 | | 34697 |
| HPV31 | E2 | AAACTNQTRA | 277 | 10 | | 34698 |
| HPV31 | E2 | AACTNQTR | 278 | 8 | | 34699 |
| HPV31 | E2 | AACTNQTRA | 278 | 9 | | 34700 |
| HPV31 | E2 | ACTNQTRA | 279 | 8 | | 34701 |
| HPV31 | E2 | AGGQVIVF | 188 | 8 | | 34702 |
| HPV31 | E2 | AGIVTKLPTA | 208 | 10 | | 34703 |
| HPV31 | E2 | ALGTSEGVR | 229 | 9 | | 34704 |
| HPV31 | E2 | ALGTSEGVRR | 229 | 10 | | 34705 |
| HPV31 | E2 | ALGTSEGVRRA | 229 | 11 | | 34706 |
| HPV31 | E2 | ALSVSKAK | 61 | 8 | | 34707 |
| HPV31 | E2 | ALSVSKAKA | 61 | 9 | | 34708 |
| HPV31 | E2 | ATTPIIHLK | 291 | 9 | | 34709 |
| HPV31 | E2 | ATTSTKRPR | 239 | 9 | | 34710 |
| HPV31 | E2 | CALGTSEGVR | 228 | 10 | | 34711 |
| HPV31 | E2 | CALGTSEGVRR | 228 | 11 | | 34712 |
| HPV31 | E2 | CDHIDYWK | 27 | 8 | | 34713 |
| HPV31 | E2 | CDHIDYWKH | 27 | 9 | | 34714 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E2 | CDHIDYWKHIR | 27 | 11 | | 34715 |
| HPV31 | E2 | CGVISAAA | 272 | 8 | | 34716 |
| HPV31 | E2 | CLRYRLSK | 307 | 8 | | 34717 |
| HPV31 | E2 | CLRYRLSKY | 307 | 9 | | 34718 |
| HPV31 | E2 | CLRYRLSKYK | 307 | 10 | | 34719 |
| HPV31 | E2 | CTDGKHKNA | 330 | 9 | | 34720 |
| HPV31 | E2 | CTVVEGQVNCK | 145 | 11 | | 34721 |
| HPV31 | E2 | CVLMYKAR | 40 | 8 | | 34722 |
| HPV31 | E2 | DANILKCLR | 301 | 9 | | 34723 |
| HPV31 | E2 | DANILKCLRY | 301 | 10 | | 34724 |
| HPV31 | E2 | DANILKCLRYR | 301 | 11 | | 34725 |
| HPV31 | E2 | DDFLNTVK | 351 | 8 | | 34726 |
| HPV31 | E2 | DGDVHNTMH | 122 | 9 | | 34727 |
| HPV31 | E2 | DGDVHNTMHY | 122 | 10 | | 34728 |
| HPV31 | E2 | DSKRLCDH | 22 | 8 | | 34729 |
| HPV31 | E2 | DSKRLCDHIDY | 22 | 11 | | 34730 |
| HPV31 | E2 | DSVNCGVISA | 268 | 10 | | 34731 |
| HPV31 | E2 | DSVNCGVISAA | 268 | 11 | | 34732 |
| HPV31 | E2 | DVHNTMHY | 124 | 8 | | 34733 |
| HPV31 | E2 | EAKKYGTGK | 174 | 9 | | 34734 |
| HPV31 | E2 | EAKKYGTGKK | 174 | 10 | | 34735 |
| HPV31 | E2 | ECVLMYKA | 39 | 8 | | 34736 |
| HPV31 | E2 | ECVLMYKAR | 39 | 9 | | 34737 |
| HPV31 | E2 | EGHITYFVNF | 162 | 10 | | 34738 |
| HPV31 | E2 | EGQVNCKGIY | 149 | 10 | | 34739 |
| HPV31 | E2 | EGQVNCKGIYY | 149 | 11 | | 34740 |
| HPV31 | E2 | EGVRRATTSTK | 234 | 11 | | 34741 |
| HPV31 | E2 | EISFAGIVTK | 204 | 10 | | 34742 |
| HPV31 | E2 | EMGIHSINH | 48 | 9 | | 34743 |
| HPV31 | E2 | ESVFSSDEISF | 197 | 11 | | 34744 |
| HPV31 | E2 | ETLNNTEY | 80 | 8 | | 34745 |
| HPV31 | E2 | ETLNNTEYK | 80 | 9 | | 34746 |
| HPV31 | E2 | EVHAGGQVIVF | 185 | 11 | | 34747 |
| HPV31 | E2 | EVQFDGDVH | 118 | 9 | | 34748 |
| HPV31 | E2 | FAGIVTKLPTA | 207 | 11 | | 34749 |
| HPV31 | E2 | FDGDVHNTMH | 121 | 10 | | 34750 |
| HPV31 | E2 | FDGDVHNTMHY | 121 | 11 | | 34751 |
| HPV31 | E2 | FSSDEISF | 200 | 8 | | 34752 |
| HPV31 | E2 | FSSDEISFA | 200 | 9 | | 34753 |
| HPV31 | E2 | FTEEAKKY | 171 | 8 | | 34754 |
| HPV31 | E2 | FVNFTEEA | 168 | 8 | | 34755 |
| HPV31 | E2 | FVNFTEEAK | 168 | 9 | | 34756 |
| HPV31 | E2 | FVNFTEEAKK | 168 | 10 | | 34757 |
| HPV31 | E2 | FVNFTEEAKKY | 168 | 11 | | 34758 |
| HPV31 | E2 | GCLKKHGY | 108 | 8 | | 34759 |
| HPV31 | E2 | GDANILKCLR | 300 | 10 | | 34760 |
| HPV31 | E2 | GDANILKCLRY | 300 | 11 | | 34761 |
| HPV31 | E2 | GDVHNTMH | 123 | 8 | | 34762 |
| HPV31 | E2 | GDVHNTMHY | 123 | 9 | | 34763 |
| HPV31 | E2 | GIVTKLPTA | 209 | 9 | | 34764 |
| HPV31 | E2 | GIYYVHEGH | 156 | 9 | | 34765 |
| HPV31 | E2 | GTGKKWEVH | 179 | 9 | | 34766 |
| HPV31 | E2 | GTGKKWEVHA | 179 | 10 | | 34767 |
| HPV31 | E2 | GTSEGVRR | 231 | 8 | | 34768 |
| HPV31 | E2 | GTSEGVRRA | 231 | 9 | | 34769 |
| HPV31 | E2 | GVRRATTSTK | 235 | 10 | | 34770 |
| HPV31 | E2 | GVRRATTSTKR | 235 | 11 | | 34771 |
| HPV31 | E2 | HAGGQVIVF | 187 | 9 | | 34772 |
| HPV31 | E2 | HGYTVEVQF | 113 | 9 | | 34773 |
| HPV31 | E2 | HIDYWKHIR | 29 | 9 | | 34774 |
| HPV31 | E2 | HIRLECVLMY | 35 | 10 | | 34775 |
| HPV31 | E2 | HIRLECVLMYK | 35 | 11 | | 34776 |
| HPV31 | E2 | HITYFVNF | 164 | 8 | | 34777 |
| HPV31 | E2 | HLKGDANILK | 297 | 10 | | 34778 |
| HPV31 | E2 | HSINHQVVPA | 52 | 10 | | 34779 |
| HPV31 | E2 | IDYWKHIR | 30 | 8 | | 34780 |
| HPV31 | E2 | IIHLKGDA | 295 | 8 | | 34781 |
| HPV31 | E2 | ILEHYENDSK | 15 | 10 | | 34782 |
| HPV31 | E2 | ILEHYENDSKR | 15 | 11 | | 34783 |
| HPV31 | E2 | ILKCLRYR | 304 | 8 | | 34784 |
| HPV31 | E2 | ILKCLRYRLSK | 304 | 11 | | 34785 |
| HPV31 | E2 | ISAAACTNQTR | 275 | 11 | | 34786 |
| HPV31 | E2 | ISFAGIVTK | 205 | 9 | | 34787 |
| HPV31 | E2 | ISTSQRDDF | 345 | 9 | | 34788 |
| HPV31 | E2 | ITYFVNFTEEA | 165 | 11 | | 34789 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E2 | IVFPESVF | 193 | 8 | | 34790 |
| HPV31 | E2 | IVTKLPTA | 210 | 8 | | 34791 |
| HPV31 | E2 | KAREMGIH | 45 | 8 | | 34792 |
| HPV31 | E2 | KCLRYRLSK | 306 | 9 | | 34793 |
| HPV31 | E2 | KCLRYRLSKY | 306 | 10 | | 34794 |
| HPV31 | E2 | KCLRYRLSKYK | 306 | 11 | | 34795 |
| HPV31 | E2 | KGDANILK | 299 | 8 | | 34796 |
| HPV31 | E2 | KGDANILKCLR | 299 | 11 | | 34797 |
| HPV31 | E2 | KGIYYVHEGH | 155 | 10 | | 34798 |
| HPV31 | E2 | KILEHYENDSK | 14 | 11 | | 34799 |
| HPV31 | E2 | LCDHIDYWK | 26 | 9 | | 34800 |
| HPV31 | E2 | LCDHIDYWKH | 26 | 10 | | 34801 |
| HPV31 | E2 | LGTSEGVR | 230 | 8 | | 34802 |
| HPV31 | E2 | LGTSEGVRR | 230 | 9 | | 34803 |
| HPV31 | E2 | LGTSEGVRRA | 230 | 10 | | 34804 |
| HPV31 | E2 | LMYKAREMGIH | 42 | 11 | | 34805 |
| HPV31 | E2 | LSKYKQLY | 312 | 8 | | 34806 |
| HPV31 | E2 | LSQRLNVCQDK | 4 | 11 | | 34807 |
| HPV31 | E2 | LSVSKAKA | 62 | 8 | | 34808 |
| HPV31 | E2 | LSVSKAKALQA | 62 | 11 | | 34809 |
| HPV31 | E2 | LTAPTGCLK | 103 | 9 | | 34810 |
| HPV31 | E2 | LTAPTGCLKK | 103 | 10 | | 34811 |
| HPV31 | E2 | LTAPTGCLKKH | 103 | 11 | | 34812 |
| HPV31 | E2 | LTYISTSQR | 342 | 9 | | 34813 |
| HPV31 | E2 | MGIHSINH | 49 | 8 | | 34814 |
| HPV31 | E2 | MLETLNNTEY | 78 | 10 | | 34815 |
| HPV31 | E2 | MLETLNNTEYK | 78 | 11 | | 34816 |
| HPV31 | E2 | MMLETLNNTEY | 77 | 11 | | 34817 |
| HPV31 | E2 | NAIVTLTY | 337 | 8 | | 34818 |
| HPV31 | E2 | NCGVISAA | 271 | 8 | | 34819 |
| HPV31 | E2 | NCGVISAAA | 271 | 9 | | 34820 |
| HPV31 | E2 | NCKGIYYVH | 153 | 9 | | 34821 |
| HPV31 | E2 | NDSKRLCDH | 21 | 9 | | 34822 |
| HPV31 | E2 | NFTEEAKK | 170 | 8 | | 34823 |
| HPV31 | E2 | NFTEEAKKY | 170 | 9 | | 34824 |
| HPV31 | E2 | NILKCLRY | 303 | 8 | | 34825 |
| HPV31 | E2 | NILKCLRYR | 303 | 9 | | 34826 |
| HPV31 | E2 | NTHHPNKLLR | 254 | 10 | | 34827 |
| HPV31 | E2 | NTMHYTNWK | 127 | 9 | | 34828 |
| HPV31 | E2 | NTMHYTNWKF | 127 | 10 | | 34829 |
| HPV31 | E2 | NTTTSNSK | 219 | 8 | | 34830 |
| HPV31 | E2 | NTTTSNSKTCA | 219 | 11 | | 34831 |
| HPV31 | E2 | NTVSVSTGY | 361 | 9 | | 34832 |
| HPV31 | E2 | NVCQDKILEH | 9 | 10 | | 34833 |
| HPV31 | E2 | NVCQDKILEHY | 9 | 11 | | 34834 |
| HPV31 | E2 | PALSVSKA | 60 | 8 | | 34835 |
| HPV31 | E2 | PALSVSKAK | 60 | 9 | | 34836 |
| HPV31 | E2 | PALSVSKAKA | 60 | 10 | | 34837 |
| HPV31 | E2 | PATTPIIH | 290 | 8 | | 34838 |
| HPV31 | E2 | PATTPIIHLK | 290 | 10 | | 34839 |
| HPV31 | E2 | PIIHLKGDA | 294 | 9 | | 34840 |
| HPV31 | E2 | PTGCLKKH | 106 | 8 | | 34841 |
| HPV31 | E2 | PTGCLKKHGY | 106 | 10 | | 34842 |
| HPV31 | E2 | QDKILEHY | 12 | 8 | | 34843 |
| HPV31 | E2 | QFDGDVHNTMH | 120 | 11 | | 34844 |
| HPV31 | E2 | QLYEQVSSTWH | 317 | 11 | | 34845 |
| HPV31 | E2 | QTRAVSCPA | 283 | 9 | | 34846 |
| HPV31 | E2 | QTSLELYLTA | 96 | 10 | | 34847 |
| HPV31 | E2 | QVIVFPESVF | 191 | 10 | | 34848 |
| HPV31 | E2 | QVNCKGIY | 151 | 8 | | 34849 |
| HPV31 | E2 | QVNCKGIYY | 151 | 9 | | 34850 |
| HPV31 | E2 | QVNCKGIYYVH | 151 | 11 | | 34851 |
| HPV31 | E2 | QVVPALSVSK | 57 | 10 | | 34852 |
| HPV31 | E2 | QVVPALSVSKA | 57 | 11 | | 34853 |
| HPV31 | E2 | RATTSTKR | 238 | 8 | | 34854 |
| HPV31 | E2 | RATTSTKRPR | 238 | 10 | | 34855 |
| HPV31 | E2 | RDDFLNTVK | 350 | 9 | | 34856 |
| HPV31 | E2 | RLCDHIDY | 25 | 8 | | 34857 |
| HPV31 | E2 | RLCDHIDYWK | 25 | 10 | | 34858 |
| HPV31 | E2 | RLCDHIDYWKH | 25 | 11 | | 34859 |
| HPV31 | E2 | RLECVLMY | 37 | 8 | | 34860 |
| HPV31 | E2 | RLECVLMYK | 37 | 9 | | 34861 |
| HPV31 | E2 | RLECVLMYKA | 37 | 10 | | 34862 |
| HPV31 | E2 | RLECVLMYKAR | 37 | 11 | | 34863 |
| HPV31 | E2 | RLNVCQDK | 7 | 8 | | 34864 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E2 | RLSKYKQLY | 311 | 9 | | 34865 |
| HPV31 | E2 | RTEPEHRNTH | 247 | 10 | | 34866 |
| HPV31 | E2 | RTEPEHRNTHH | 247 | 11 | | 34867 |
| HPV31 | E2 | SAAACTNQTR | 276 | 10 | | 34868 |
| HPV31 | E2 | SAAACTNQTRA | 276 | 11 | | 34869 |
| HPV31 | E2 | SCPATTPIIH | 288 | 10 | | 34870 |
| HPV31 | E2 | SFAGIVTK | 206 | 8 | | 34871 |
| HPV31 | E2 | SINHQVVPA | 53 | 9 | | 34872 |
| HPV31 | E2 | SLELYLTA | 98 | 8 | | 34873 |
| HPV31 | E2 | SSDEISFA | 201 | 8 | | 34874 |
| HPV31 | E2 | STKRPRTEPEH | 242 | 11 | | 34875 |
| HPV31 | E2 | STSQRDDF | 346 | 8 | | 34876 |
| HPV31 | E2 | STWHWTCTDGK | 324 | 11 | | 34877 |
| HPV31 | E2 | SVFSSDEISF | 198 | 10 | | 34878 |
| HPV31 | E2 | SVFSSDEISFA | 198 | 11 | | 34879 |
| HPV31 | E2 | SVNCGVISA | 269 | 9 | | 34880 |
| HPV31 | E2 | SVNCGVISAA | 269 | 10 | | 34881 |
| HPV31 | E2 | SVNCGVISAAA | 269 | 11 | | 34882 |
| HPV31 | E2 | SVSKAKALQA | 63 | 10 | | 34883 |
| HPV31 | E2 | TANNTTTSNSK | 216 | 11 | | 34884 |
| HPV31 | E2 | TAPTGCLK | 104 | 8 | | 34885 |
| HPV31 | E2 | TAPTGCLKK | 104 | 9 | | 34886 |
| HPV31 | E2 | TAPTGCLKKH | 104 | 10 | | 34887 |
| HPV31 | E2 | TCALGTSEGVR | 227 | 11 | | 34888 |
| HPV31 | E2 | TCTDGKHK | 329 | 8 | | 34889 |
| HPV31 | E2 | TCTDGKHKNA | 329 | 10 | | 34890 |
| HPV31 | E2 | TDGKHKNA | 331 | 8 | | 34891 |
| HPV31 | E2 | TGCLKKHGY | 107 | 9 | | 34892 |
| HPV31 | E2 | TGKKWEVH | 180 | 8 | | 34893 |
| HPV31 | E2 | TGKKWEVHA | 180 | 9 | | 34894 |
| HPV31 | E2 | TLNNTEYK | 81 | 8 | | 34895 |
| HPV31 | E2 | TLTYISTSQR | 341 | 10 | | 34896 |
| HPV31 | E2 | TMHYTNWK | 128 | 8 | | 34897 |
| HPV31 | E2 | TMHYTNWKF | 128 | 9 | | 34898 |
| HPV31 | E2 | TMHYTNWKFIY | 128 | 11 | | 34899 |
| HPV31 | E2 | TMQQTSLELY | 93 | 10 | | 34900 |
| HPV31 | E2 | TSEGVRRA | 232 | 8 | | 34901 |
| HPV31 | E2 | TSLELYLTA | 97 | 9 | | 34902 |
| HPV31 | E2 | TSNSKTCA | 222 | 8 | | 34903 |
| HPV31 | E2 | TTPIIHLK | 292 | 8 | | 34904 |
| HPV31 | E2 | TTPIIHLKGDA | 292 | 11 | | 34905 |
| HPV31 | E2 | TTSNSKTCA | 221 | 9 | | 34906 |
| HPV31 | E2 | TTSTKRPR | 240 | 8 | | 34907 |
| HPV31 | E2 | TTTSNSKTCA | 220 | 10 | | 34908 |
| HPV31 | E2 | TVEVQFDGDVH | 116 | 11 | | 34909 |
| HPV31 | E2 | TVSVSTGY | 362 | 8 | | 34910 |
| HPV31 | E2 | TVVEGQVNCK | 146 | 10 | | 34911 |
| HPV31 | E2 | VCQDKILEH | 10 | 9 | | 34912 |
| HPV31 | E2 | VCQDKILEHY | 10 | 10 | | 34913 |
| HPV31 | E2 | VDSVNCGVISA | 267 | 11 | | 34914 |
| HPV31 | E2 | VFSSDEISF | 199 | 9 | | 34915 |
| HPV31 | E2 | VFSSDEISFA | 199 | 10 | | 34916 |
| HPV31 | E2 | VIVFPESVF | 192 | 9 | | 34917 |
| HPV31 | E2 | VSCPATTPIIH | 287 | 11 | | 34918 |
| HPV31 | E2 | VSKAKALQA | 64 | 9 | | 34919 |
| HPV31 | E2 | VTLTYISTSQR | 340 | 11 | | 34920 |
| HPV31 | E2 | VVEGQVNCK | 147 | 9 | | 34921 |
| HPV31 | E2 | VVPALSVSK | 58 | 9 | | 34922 |
| HPV31 | E2 | VVPALSVSKA | 58 | 10 | | 34923 |
| HPV31 | E2 | VVPALSVSKAK | 58 | 11 | | 34924 |
| HPV31 | E2 | WTCTDGKH | 328 | 8 | | 34925 |
| HPV31 | E2 | WTCTDGKHK | 328 | 9 | | 34926 |
| HPV31 | E2 | WTCTDGKHKNA | 328 | 11 | | 34927 |
| HPV31 | E2 | WTMQQTSLELY | 92 | 11 | | 34928 |
| HPV31 | E2 | YFVNFTEEA | 167 | 9 | | 34929 |
| HPV31 | E2 | YFVNFTEEAK | 167 | 10 | | 34930 |
| HPV31 | E2 | YFVNFTEEAKK | 167 | 11 | | 34931 |
| HPV31 | E2 | YGTGKKWEVH | 178 | 10 | | 34932 |
| HPV31 | E2 | YGTGKKWEVHA | 178 | 11 | | 34933 |
| HPV31 | E2 | YISTSQRDDF | 344 | 10 | | 34934 |
| HPV31 | E2 | YLTAPTGCLK | 102 | 10 | | 34935 |
| HPV31 | E2 | YLTAPTGCLKK | 102 | 11 | | 34936 |
| HPV31 | E2 | YTNWKFIY | 131 | 8 | | 34937 |
| HPV31 | E2 | YVHEGHITY | 159 | 9 | | 34938 |
| HPV31 | E2 | YVHEGHITYF | 159 | 10 | | 34939 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E5 | ATSPLRCF | 53 | 8 | | 34940 |
| HPV31 | E5 | ATSPLRCFCIY | 53 | 11 | | 34941 |
| HPV31 | E5 | CFCIYVVF | 59 | 8 | | 34942 |
| HPV31 | E5 | CFCIYVVFIY | 59 | 10 | | 34943 |
| HPV31 | E5 | CFLLCFCVLLF | 14 | 11 | | 34944 |
| HPV31 | E5 | CIYVVFIY | 61 | 8 | | 34945 |
| HPV31 | E5 | CVLLFVCLVIR | 20 | 11 | | 34946 |
| HPV31 | E5 | FCIYVVFIY | 60 | 9 | | 34947 |
| HPV31 | E5 | FIYIPLFVIH | 66 | 10 | | 34948 |
| HPV31 | E5 | FLLCFCVLLF | 15 | 10 | | 34949 |
| HPV31 | E5 | FVIHTHASF | 72 | 9 | | 34950 |
| HPV31 | E5 | IATSPLRCF | 52 | 9 | | 34951 |
| HPV31 | E5 | ILWVIATSPLR | 48 | 11 | | 34952 |
| HPV31 | E5 | ISTVSIVLCF | 6 | 10 | | 34953 |
| HPV31 | E5 | IVILWVIA | 46 | 8 | | 34954 |
| HPV31 | E5 | IVLCFLLCF | 11 | 9 | | 34955 |
| HPV31 | E5 | LCFCVLLF | 17 | 8 | | 34956 |
| HPV31 | E5 | LFVCLVIR | 23 | 8 | | 34957 |
| HPV31 | E5 | LFVIHTHA | 71 | 8 | | 34958 |
| HPV31 | E5 | LFVIHTHASF | 71 | 10 | | 34959 |
| HPV31 | E5 | LIVILWVIA | 45 | 9 | | 34960 |
| HPV31 | E5 | LLCFCVLLF | 16 | 9 | | 34961 |
| HPV31 | E5 | LLFVCLVIR | 22 | 9 | | 34962 |
| HPV31 | E5 | LLIVILWVIA | 44 | 10 | | 34963 |
| HPV31 | E5 | LLLIVILWVIA | 43 | 11 | | 34964 |
| HPV31 | E5 | LVLSVSVY | 32 | 8 | | 34965 |
| HPV31 | E5 | LVLSVSVYA | 32 | 9 | | 34966 |
| HPV31 | E5 | NISTVSIVLCF | 5 | 11 | | 34967 |
| HPV31 | E5 | PLFVIHTH | 70 | 8 | | 34968 |
| HPV31 | E5 | PLFVIHTHA | 70 | 9 | | 34969 |
| HPV31 | E5 | PLFVIHTHASF | 70 | 11 | | 34970 |
| HPV31 | E5 | PLRCFCIY | 56 | 8 | | 34971 |
| HPV31 | E5 | PLRCFCIYVVF | 56 | 11 | | 34972 |
| HPV31 | E5 | PLVLSVSVY | 31 | 9 | | 34973 |
| HPV31 | E5 | PLVLSVSVYA | 31 | 10 | | 34974 |
| HPV31 | E5 | RCFCIYVVF | 58 | 9 | | 34975 |
| HPV31 | E5 | RCFCIYVVFIY | 58 | 11 | | 34976 |
| HPV31 | E5 | SIVLCFLLCF | 10 | 10 | | 34977 |
| HPV31 | E5 | STVSIVLCF | 7 | 9 | | 34978 |
| HPV31 | E5 | TSPLRCFCIY | 54 | 10 | | 34979 |
| HPV31 | E5 | TVSIVLCF | 8 | 8 | | 34980 |
| HPV31 | E5 | VFIYIPLF | 65 | 8 | | 34981 |
| HPV31 | E5 | VFIYIPLFVIH | 65 | 11 | | 34982 |
| HPV31 | E5 | VIATSPLR | 51 | 8 | | 34983 |
| HPV31 | E5 | VIATSPLRCF | 51 | 10 | | 34984 |
| HPV31 | E5 | VIHTHASF | 73 | 8 | | 34985 |
| HPV31 | E5 | VLCFLLCF | 12 | 8 | | 34986 |
| HPV31 | E5 | VLLFVCLVIR | 21 | 10 | | 34987 |
| HPV31 | E5 | VLSVSVYA | 33 | 8 | | 34988 |
| HPV31 | E5 | VSIVLCFLLCF | 9 | 11 | | 34989 |
| HPV31 | E5 | VVFIYIPLF | 64 | 9 | | 34990 |
| HPV31 | E5 | WVIATSPLR | 50 | 9 | | 34991 |
| HPV31 | E5 | WVIATSPLRCF | 50 | 11 | | 34992 |
| HPV31 | E5 | YIPLFVIH | 68 | 8 | | 34993 |
| HPV31 | E5 | YIPLFVIHTH | 68 | 10 | | 34994 |
| HPV31 | E5 | YIPLFVIHTHA | 68 | 11 | | 34995 |
| HPV31 | E5 | YVVFIYIPLF | 63 | 10 | | 34996 |
| HPV31 | E6 | AFTDLTIVY | 46 | 9 | | 34997 |
| HPV31 | E6 | AFTDLTIVYR | 46 | 10 | | 34998 |
| HPV31 | E6 | ALEIPYDELR | 18 | 10 | | 34999 |
| HPV31 | E6 | CIACWRRPR | 136 | 9 | | 35000 |
| HPV31 | E6 | CLRFYSKVSEF | 66 | 11 | | 35001 |
| HPV31 | E6 | CTKCLRFY | 63 | 8 | | 35002 |
| HPV31 | E6 | CTKCLRFYSK | 63 | 10 | | 35003 |
| HPV31 | E6 | DDTPHGVCTK | 56 | 10 | | 35004 |
| HPV31 | E6 | DFAFTDLTIVY | 44 | 11 | | 35005 |
| HPV31 | E6 | DLLIRCITCQR | 98 | 11 | | 35006 |
| HPV31 | E6 | DTPHGVCTK | 57 | 9 | | 35007 |
| HPV31 | E6 | EFRWYRYSVY | 75 | 10 | | 35008 |
| HPV31 | E6 | EIPYDELR | 20 | 8 | | 35009 |
| HPV31 | E6 | ELRLNCVY | 25 | 8 | | 35010 |
| HPV31 | E6 | ELRLNCVYCK | 25 | 10 | | 35011 |
| HPV31 | E6 | ELSSALEIPY | 14 | 10 | | 35012 |
| HPV31 | E6 | ETEVLDFA | 39 | 8 | | 35013 |
| HPV31 | E6 | ETEVLDFAF | 39 | 9 | | 35014 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E6 | FAFTDLTIVY | 45 | 10 | | 35015 |
| HPV31 | E6 | FAFTDLTIVYR | 45 | 11 | | 35016 |
| HPV31 | E6 | FTDLTIVY | 47 | 8 | | 35017 |
| HPV31 | E6 | FTDLTIVYR | 47 | 9 | | 35018 |
| HPV31 | E6 | GGRWTGRCIA | 129 | 10 | | 35019 |
| HPV31 | E6 | GICDLLIR | 95 | 8 | | 35020 |
| HPV31 | E6 | GTTLEKLTNK | 85 | 10 | | 35021 |
| HPV31 | E6 | GVCTKCLR | 61 | 8 | | 35022 |
| HPV31 | E6 | GVCTKCLRF | 61 | 9 | | 35023 |
| HPV31 | E6 | GVCTKCLRFY | 61 | 10 | | 35024 |
| HPV31 | E6 | HGVCTKCLR | 60 | 9 | | 35025 |
| HPV31 | E6 | HGVCTKCLRF | 60 | 10 | | 35026 |
| HPV31 | E6 | HGVCTKCLRFY | 60 | 11 | | 35027 |
| HPV31 | E6 | HLDKKKRF | 118 | 8 | | 35028 |
| HPV31 | E6 | HLDKKKRFH | 118 | 9 | | 35029 |
| HPV31 | E6 | IACWRRPR | 137 | 8 | | 35030 |
| HPV31 | E6 | IGGRWTGR | 128 | 8 | | 35031 |
| HPV31 | E6 | IGGRWTGRCIA | 128 | 11 | | 35032 |
| HPV31 | E6 | IVYRDDTPH | 52 | 9 | | 35033 |
| HPV31 | E6 | KCLRFYSK | 65 | 8 | | 35034 |
| HPV31 | E6 | KGICDLLIR | 94 | 9 | | 35035 |
| HPV31 | E6 | KLHELSSA | 11 | 8 | | 35036 |
| HPV31 | E6 | KVSEFRWY | 72 | 8 | | 35037 |
| HPV31 | E6 | KVSEFRWYR | 72 | 9 | | 35038 |
| HPV31 | E6 | KVSEFRWYRY | 72 | 10 | | 35039 |
| HPV31 | E6 | LCPEEKQR | 110 | 8 | | 35040 |
| HPV31 | E6 | LCPEEKQRH | 110 | 9 | 0.0003 | 35041 |
| HPV31 | E6 | LDKKKRFH | 119 | 8 | | 35042 |
| HPV31 | E6 | LIRCITCQR | 100 | 9 | | 35043 |
| HPV31 | E6 | LLIRCITCQR | 99 | 10 | | 35044 |
| HPV31 | E6 | LSSALEIPY | 15 | 9 | | 35045 |
| HPV31 | E6 | LTETEVLDF | 37 | 9 | | 35046 |
| HPV31 | E6 | LTETEVLDFA | 37 | 10 | | 35047 |
| HPV31 | E6 | LTETEVLDFAF | 37 | 11 | | 35048 |
| HPV31 | E6 | LTIVYRDDTPH | 50 | 11 | | 35049 |
| HPV31 | E6 | MFKNPAER | 1 | 8 | | 35050 |
| HPV31 | E6 | MFKNPAERPR | 1 | 10 | | 35051 |
| HPV31 | E6 | MFKNPAERPRK | 1 | 11 | | 35052 |
| HPV31 | E6 | NIGGRWTGR | 127 | 9 | | 35053 |
| HPV31 | E6 | PAERPRKLH | 5 | 9 | | 35054 |
| HPV31 | E6 | PLCPEEKQR | 109 | 9 | 0.0002 | 35055 |
| HPV31 | E6 | PLCPEEKQRH | 109 | 10 | | 35056 |
| HPV31 | E6 | QLTETEVLDF | 36 | 10 | | 35057 |
| HPV31 | E6 | QLTETEVLDFA | 36 | 11 | | 35058 |
| HPV31 | E6 | RCIACWRR | 135 | 8 | | 35059 |
| HPV31 | E6 | RCIACWRRPR | 135 | 10 | | 35060 |
| HPV31 | E6 | RDDTPHGVCTK | 55 | 11 | | 35061 |
| HPV31 | E6 | RFHNIGGR | 124 | 8 | | 35062 |
| HPV31 | E6 | RFYSKVSEF | 68 | 9 | | 35063 |
| HPV31 | E6 | RFYSKVSEFR | 68 | 10 | | 35064 |
| HPV31 | E6 | RLNCVYCK | 27 | 8 | | 35065 |
| HPV31 | E6 | SALEIPYDELR | 17 | 11 | | 35066 |
| HPV31 | E6 | SSALEIPY | 16 | 8 | | 35067 |
| HPV31 | E6 | SVYGTTLEK | 82 | 9 | | 35068 |
| HPV31 | E6 | TCQRPLCPEEK | 105 | 11 | | 35069 |
| HPV31 | E6 | TDLTIVYR | 48 | 8 | | 35070 |
| HPV31 | E6 | TGRCIACWR | 133 | 9 | | 35071 |
| HPV31 | E6 | TGRCIACWRR | 133 | 10 | | 35072 |
| HPV31 | E6 | TIVYRDDTPH | 51 | 10 | | 35073 |
| HPV31 | E6 | TLEKLTNK | 87 | 8 | | 35074 |
| HPV31 | E6 | TTLEKLTNK | 86 | 9 | | 35075 |
| HPV31 | E6 | VCTKCLRF | 62 | 8 | | 35076 |
| HPV31 | E6 | VCTKCLRFY | 62 | 9 | | 35077 |
| HPV31 | E6 | VCTKCLRFYSK | 62 | 11 | | 35078 |
| HPV31 | E6 | VSEFRWYR | 73 | 8 | | 35079 |
| HPV31 | E6 | VSEFRWYRY | 73 | 9 | | 35080 |
| HPV31 | E6 | WTGRCIACWR | 132 | 10 | | 35081 |
| HPV31 | E6 | WTGRCIACWRR | 132 | 11 | | 35082 |
| HPV31 | E6 | YDELRLNCVY | 23 | 10 | | 35083 |
| HPV31 | E6 | YGTTLEKLTNK | 84 | 11 | | 35084 |
| HPV31 | E6 | YSKVSEFR | 70 | 8 | | 35085 |
| HPV31 | E6 | YSKVSEFRWY | 70 | 10 | | 35086 |
| HPV31 | E6 | YSKVSEFRWYR | 70 | 11 | | 35087 |
| HPV31 | E6 | YSVYGTTLEK | 81 | 10 | | 35088 |
| HPV31 | E7 | AGQAEPDTSNY | 42 | 11 | | 35089 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | E7 | CCQCKSTLR | 58 | 9 | | 35090 |
| HPV31 | E7 | CVQSTQVDIR | 68 | 10 | | 35091 |
| HPV31 | E7 | DLQPEATDLH | 14 | 10 | | 35092 |
| HPV31 | E7 | DTSNYNIVTF | 48 | 10 | | 35093 |
| HPV31 | E7 | DVIDSPAGQA | 36 | 10 | | 35094 |
| HPV31 | E7 | EATDLHCY | 18 | 8 | | 35095 |
| HPV31 | E7 | EDVIDSPA | 35 | 8 | | 35096 |
| HPV31 | E7 | EDVIDSPAGQA | 35 | 11 | | 35097 |
| HPV31 | E7 | ETPTLQDY | 4 | 8 | | 35098 |
| HPV31 | E7 | FCCQCKSTLR | 57 | 10 | | 35099 |
| HPV31 | E7 | FGIVCPNSCSR | 87 | 11 | | 35100 |
| HPV31 | E7 | GIVCPNCSTR | 88 | 10 | | 35101 |
| HPV31 | E7 | IDSPAGQA | 38 | 8 | | 35102 |
| HPV31 | E7 | ILQELLMGSF | 78 | 10 | | 35103 |
| HPV31 | E7 | IVCPNCSTR | 89 | 9 | | 35104 |
| HPV31 | E7 | IVTFCCQCK | 54 | 9 | | 35105 |
| HPV31 | E7 | LCVQSTQVDIR | 67 | 11 | | 35106 |
| HPV31 | E7 | LDLQPEATDLH | 13 | 11 | | 35107 |
| HPV31 | E7 | NIVTFCCQCK | 53 | 10 | | 35108 |
| HPV31 | E7 | PDTSNYNIVTF | 47 | 11 | | 35109 |
| HPV31 | E7 | QAEPDTSNY | 44 | 9 | | 35110 |
| HPV31 | E7 | QDYVLDLQPEA | 9 | 11 | | 35111 |
| HPV31 | E7 | QSTQVDIR | 70 | 8 | | 35112 |
| HPV31 | E7 | RGETPTLQDY | 2 | 10 | | 35113 |
| HPV31 | E7 | RILQELLMGSF | 77 | 11 | | 35114 |
| HPV31 | E7 | SDEEDVIDSPA | 32 | 11 | | 35115 |
| HPV31 | E7 | TFCCQCKSTLR | 56 | 11 | | 35116 |
| HPV31 | E7 | TSNYNIVTF | 49 | 9 | | 35117 |
| HPV31 | E7 | VCPNCSTR | 90 | 8 | | 35118 |
| HPV31 | E7 | VIDSPAGQA | 37 | 9 | | 35119 |
| HPV31 | E7 | VLDLQPEA | 12 | 8 | | 35120 |
| HPV31 | E7 | VTFCCQCK | 55 | 8 | | 35121 |
| HPV31 | E7 | YVLDLQPEA | 11 | 9 | | 35122 |
| HPV31 | L1 | AAIANSDTTF | 347 | 10 | | 35123 |
| HPV31 | L1 | AAIANSDTTFK | 347 | 11 | | 35124 |
| HPV31 | L1 | ACVGLEVGR | 102 | 9 | | 35125 |
| HPV31 | L1 | ADIMTYIH | 386 | 8 | | 35126 |
| HPV31 | L1 | ADLDQFPLGR | 458 | 10 | | 35127 |
| HPV31 | L1 | ADLDQFPLGRK | 458 | 11 | | 35128 |
| HPV31 | L1 | AGGPGTDNR | 137 | 9 | | 35129 |
| HPV31 | L1 | AGKRSAPSA | 483 | 9 | | 35130 |
| HPV31 | L1 | AGSARLLTVGH | 37 | 11 | | 35131 |
| HPV31 | L1 | AGYRARPK | 473 | 8 | | 35132 |
| HPV31 | L1 | AGYRARPKF | 473 | 9 | | 35133 |
| HPV31 | L1 | AGYRARPKFK | 473 | 10 | | 35134 |
| HPV31 | L1 | AGYRARPKFKA | 473 | 11 | | 35135 |
| HPV31 | L1 | AIANSDTTF | 348 | 9 | | 35136 |
| HPV31 | L1 | AIANSDTTFK | 348 | 10 | | 35137 |
| HPV31 | L1 | AILEDWNF | 398 | 8 | | 35138 |
| HPV31 | L1 | AITCQKTA | 426 | 8 | | 35139 |
| HPV31 | L1 | AITCQKTAPQK | 426 | 11 | | 35140 |
| HPV31 | L1 | AMDFTALQDTK | 208 | 11 | | 35141 |
| HPV31 | L1 | ASTTTPAK | 491 | 8 | | 35142 |
| HPV31 | L1 | ASTTTPAKR | 491 | 9 | | 35143 |
| HPV31 | L1 | ASTTTPAKRK | 491 | 10 | | 35144 |
| HPV31 | L1 | ASTTTPAKRKK | 491 | 11 | | 35145 |
| HPV31 | L1 | ATLANSTY | 285 | 8 | | 35146 |
| HPV31 | L1 | ATLANSTYF | 285 | 9 | | 35147 |
| HPV31 | L1 | CAAIANSDTTF | 346 | 11 | | 35148 |
| HPV31 | L1 | CVGLEVGR | 103 | 8 | | 35149 |
| HPV31 | L1 | DAQIFNKPY | 304 | 9 | | 35150 |
| HPV31 | L1 | DCPPLELK | 185 | 8 | | 35151 |
| HPV31 | L1 | DDTENSNR | 128 | 8 | | 35152 |
| HPV31 | L1 | DDTENSNRY | 128 | 9 | | 35153 |
| HPV31 | L1 | DDTENSNRYA | 128 | 10 | | 35154 |
| HPV31 | L1 | DFTALQDTK | 210 | 9 | | 35155 |
| HPV31 | L1 | DGDMVDTGF | 198 | 9 | | 35156 |
| HPV31 | L1 | DGDMVDTGFGA | 198 | 11 | | 35157 |
| HPV31 | L1 | DICNSICK | 224 | 8 | | 35158 |
| HPV31 | L1 | DICNSICKY | 224 | 9 | | 35159 |
| HPV31 | L1 | DLDQFPLGR | 459 | 9 | | 35160 |
| HPV31 | L1 | DLDQFPLGRK | 459 | 10 | | 35161 |
| HPV31 | L1 | DLDQFPLGRKF | 459 | 11 | | 35162 |
| HPV31 | L1 | DLQFIFQLCK | 372 | 10 | | 35163 |
| HPV31 | L1 | DLYIKGSGSTA | 275 | 11 | | 35164 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | L1 | DMVDTGFGA | 200 | 9 | | 35165 |
| HPV31 | L1 | DTENSNRY | 129 | 8 | | 35166 |
| HPV31 | L1 | DTENSNRYA | 129 | 9 | | 35167 |
| HPV31 | L1 | DTGFGAMDG | 203 | 9 | | 35168 |
| HPV31 | L1 | DTGFGAMDFTA | 203 | 11 | | 35169 |
| HPV31 | L1 | DTLFFYLR | 245 | 8 | | 35170 |
| HPV31 | L1 | DTLFFYLRR | 245 | 9 | | 35171 |
| HPV31 | L1 | DTSFYNPETQR | 88 | 11 | | 35172 |
| HPV31 | L1 | DTTFKSSNF | 353 | 9 | | 35173 |
| HPV31 | L1 | DTTFKSSNFK | 353 | 10 | | 35174 |
| HPV31 | L1 | DTYRFVTSQA | 417 | 10 | | 35175 |
| HPV31 | L1 | ECISMDYK | 146 | 8 | | 35176 |
| HPV31 | L1 | EDPFKDYVF | 439 | 9 | | 35177 |
| HPV31 | L1 | EDTYRFVTSQA | 416 | 11 | | 35178 |
| HPV31 | L1 | EFDLQFIF | 370 | 8 | | 35179 |
| HPV31 | L1 | ESVPTDLY | 270 | 8 | | 35180 |
| HPV31 | L1 | ESVPTDLYIK | 270 | 10 | | 35181 |
| HPV31 | L1 | ETQRLVWA | 95 | 8 | | 35182 |
| HPV31 | L1 | EVNLKEKF | 449 | 8 | | 35183 |
| HPV31 | L1 | EVNLKEKFSA | 449 | 10 | | 35184 |
| HPV31 | L1 | FDDTENSNR | 127 | 9 | | 35185 |
| HPV31 | L1 | FDDTENSNRY | 127 | 10 | | 35186 |
| HPV31 | L1 | FDDTENSNRYA | 127 | 11 | | 35187 |
| HPV31 | L1 | FDLQFIFQLCK | 371 | 11 | | 35188 |
| HPV31 | L1 | FFYLRREQMF | 248 | 10 | | 35189 |
| HPV31 | L1 | FGAMDFTA | 206 | 8 | | 35190 |
| HPV31 | L1 | FGFPDTSF | 84 | 8 | | 35191 |
| HPV31 | L1 | FGFPDTSFY | 84 | 9 | | 35192 |
| HPV31 | L1 | FLLQAGYR | 469 | 8 | | 35193 |
| HPV31 | L1 | FLLQAGYRA | 469 | 9 | | 35194 |
| HPV31 | L1 | FLLQAGYRAR | 469 | 10 | | 35195 |
| HPV31 | L1 | FSADLDQF | 456 | 8 | | 35196 |
| HPV31 | L1 | FTALQDTK | 211 | 8 | | 35197 |
| HPV31 | L1 | FVRHFFNR | 257 | 8 | | 35198 |
| HPV31 | L1 | FVTSQAITCQK | 421 | 11 | | 35199 |
| HPV31 | L1 | FVTVVDTTR | 331 | 9 | | 35200 |
| HPV31 | L1 | GCKPPIGEH | 161 | 9 | | 35201 |
| HPV31 | L1 | GDCPPLELK | 184 | 9 | | 35202 |
| HPV31 | L1 | GDMVDTGF | 199 | 8 | | 35203 |
| HPV31 | L1 | GDMVDTGFGA | 199 | 10 | | 35204 |
| HPV31 | L1 | GDTLFFYLR | 244 | 9 | | 35205 |
| HPV31 | L1 | GDTLFFYLRR | 244 | 10 | | 35206 |
| HPV31 | L1 | GFGAMDFTA | 205 | 9 | | 35207 |
| HPV31 | L1 | GFPDTSFY | 85 | 8 | | 35208 |
| HPV31 | L1 | GGPGTDNR | 138 | 8 | | 35209 |
| HPV31 | L1 | GICWGNQLF | 323 | 9 | | 35210 |
| HPV31 | L1 | GISGHPLLNK | 117 | 10 | | 35211 |
| HPV31 | L1 | GISGHPLLNKF | 117 | 11 | | 35212 |
| HPV31 | L1 | GLQYRVFR | 68 | 8 | | 35213 |
| HPV31 | L1 | GLQYRVFRVR | 68 | 10 | | 35214 |
| HPV31 | L1 | GSARLLTVGH | 38 | 10 | | 35215 |
| HPV31 | L1 | GSGSTATLA | 280 | 9 | | 35216 |
| HPV31 | L1 | GSLEDTYR | 413 | 8 | | 35217 |
| HPV31 | L1 | GSLEDTYRF | 413 | 9 | | 35218 |
| HPV31 | L1 | GSMVTSDA | 298 | 8 | | 35219 |
| HPV31 | L1 | GSMVTSDAQIF | 298 | 11 | | 35220 |
| HPV31 | L1 | GSPCSNNA | 173 | 8 | | 35221 |
| HPV31 | L1 | GSTATLANSTY | 282 | 11 | | 35222 |
| HPV31 | L1 | HGEEFDLQF | 367 | 9 | | 35223 |
| HPV31 | L1 | HGEEFDLQFIF | 367 | 11 | | 35224 |
| HPV31 | L1 | IANSDTTF | 349 | 8 | | 35225 |
| HPV31 | L1 | IANSDTTFK | 349 | 9 | | 35226 |
| HPV31 | L1 | ICKYPDYLK | 229 | 9 | | 35227 |
| HPV31 | L1 | ICNSICKY | 225 | 8 | | 35228 |
| HPV31 | L1 | ICMSICKYPDY | 225 | 11 | | 35229 |
| HPV31 | L1 | ICWGNQLF | 324 | 8 | | 35230 |
| HPV31 | L1 | IFNKPYWMQR | 307 | 10 | | 35231 |
| HPV31 | L1 | IFNKPYWMQRA | 307 | 11 | | 35232 |
| HPV31 | L1 | IFQLCKITLSA | 376 | 11 | | 35233 |
| HPV31 | L1 | IMTYIHSMNPA | 388 | 11 | | 35234 |
| HPV31 | L1 | ISGHPLLNK | 118 | 9 | | 35235 |
| HPV31 | L1 | ISGHPLLNKF | 118 | 10 | | 35236 |
| HPV31 | L1 | ITCQKTAPQK | 427 | 10 | | 35237 |
| HPV31 | L1 | ITLSADIMTY | 382 | 10 | | 35238 |
| HPV31 | L1 | IVVPKVSGLQY | 61 | 11 | | 35239 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | L1 | KAGKRSAPSA | 482 | 10 | | 35240 |
| HPV31 | L1 | KDYVFWEVNLK | 443 | 11 | | 35241 |
| HPV31 | L1 | KFDDTENSNR | 126 | 10 | | 35242 |
| HPV31 | L1 | KFDDTENSNRY | 126 | 11 | | 35243 |
| HPV31 | L1 | KFGFPDTSF | 83 | 9 | | 35244 |
| HPV31 | L1 | KFGFPDTSFY | 83 | 10 | | 35245 |
| HPV31 | L1 | KFKAGKRSA | 480 | 9 | | 35246 |
| HPV31 | L1 | KFLLQAGY | 468 | 8 | | 35247 |
| HPV31 | L1 | KFLLQAGYR | 468 | 9 | | 35248 |
| HPV31 | L1 | KFLLQAGYRA | 468 | 10 | | 35249 |
| HPV31 | L1 | KFLLQAGYRAR | 468 | 11 | | 35250 |
| HPV31 | L1 | KFSADLDQF | 455 | 9 | | 35251 |
| HPV31 | L1 | KGSGSTATLA | 279 | 10 | | 35252 |
| HPV31 | L1 | KGSPCSNNA | 172 | 9 | | 35253 |
| HPV31 | L1 | KITLSADIMTY | 381 | 11 | | 35254 |
| HPV31 | L1 | KSSNFKEY | 357 | 8 | | 35255 |
| HPV31 | L1 | KSSNFKEYLR | 357 | 10 | | 35256 |
| HPV31 | L1 | KSSNFKEYLRH | 357 | 11 | | 35257 |
| HPV31 | L1 | KTAPQKPK | 431 | 8 | | 35258 |
| HPV31 | L1 | KVSGLQYR | 65 | 8 | | 35259 |
| HPV31 | L1 | KVSGLQYRVF | 65 | 10 | | 35260 |
| HPV31 | L1 | KVSGLQYRVFR | 65 | 11 | | 35261 |
| HPV31 | L1 | KVVSTDEY | 20 | 8 | | 35262 |
| HPV31 | L1 | KVVSTDEYVTR | 20 | 11 | | 35263 |
| HPV31 | L1 | LCKITLSA | 379 | 8 | | 35264 |
| HPV31 | L1 | LDICNSICK | 223 | 9 | | 35265 |
| HPV31 | L1 | LDICNSICKY | 223 | 10 | | 35266 |
| HPV31 | L1 | LDQFPLGR | 460 | 8 | | 35267 |
| HPV31 | L1 | LDQFPLGRK | 460 | 9 | | 35268 |
| HPV31 | L1 | LDQFPLGRKF | 460 | 10 | | 35269 |
| HPV31 | L1 | LFFYLRREQMF | 247 | 11 | | 35270 |
| HPV31 | L1 | LFVTVVDTTR | 330 | 10 | | 35271 |
| HPV31 | L1 | LGCKPPIGEH | 160 | 10 | | 35272 |
| HPV31 | L1 | LGRKFLLQA | 465 | 9 | | 35273 |
| HPV31 | L1 | LGRKFLLQAGY | 465 | 11 | | 35274 |
| HPV31 | L1 | LGVGISGH | 114 | 8 | | 35275 |
| HPV31 | L1 | LLGCKPPIGEH | 159 | 11 | | 35276 |
| HPV31 | L1 | LLQAGYRA | 470 | 8 | | 35277 |
| HPV31 | L1 | LLQAGYRAR | 470 | 9 | | 35278 |
| HPV31 | L1 | LLQAGYRARPK | 470 | 11 | | 35279 |
| HPV31 | L1 | LLTVGHPY | 42 | 8 | | 35280 |
| HPV31 | L1 | LLTVGHPYY | 42 | 9 | | 35281 |
| HPV31 | L1 | LSADIMTY | 384 | 8 | | 35282 |
| HPV31 | L1 | LSADIMTYIH | 384 | 10 | | 35283 |
| HPV31 | L1 | LTVGHPYY | 43 | 8 | | 35284 |
| HPV31 | L1 | MDFTALQDTK | 209 | 10 | | 35285 |
| HPV31 | L1 | MFVRHFFNR | 256 | 9 | | 35286 |
| HPV31 | L1 | MSLWRPSEA | 1 | 9 | | 35287 |
| HPV31 | L1 | MSVCAAIA | 343 | 8 | | 35288 |
| HPV31 | L1 | MTYIHSMNPA | 389 | 10 | | 35289 |
| HPV31 | L1 | MVAEPYGDTLF | 238 | 11 | | 35290 |
| HPV31 | L1 | MVDTGFGA | 201 | 8 | | 35291 |
| HPV31 | L1 | MVDTGFGAMDF | 201 | 11 | | 35292 |
| HPV31 | L1 | MVTSDAQIF | 300 | 9 | | 35293 |
| HPV31 | L1 | MVTSDAQIFNK | 300 | 11 | | 35294 |
| HPV31 | L1 | NFKEYLRH | 360 | 8 | | 35295 |
| HPV31 | L1 | NGICWGNQLF | 322 | 10 | | 35296 |
| HPV31 | L1 | NIYYHAGSA | 32 | 9 | | 35297 |
| HPV31 | L1 | NIYYHAGSAR | 32 | 10 | | 35298 |
| HPV31 | L1 | NLKEKFSA | 451 | 8 | | 35299 |
| HPV31 | L1 | NMSVCAAIA | 342 | 9 | | 35300 |
| HPV31 | L1 | NSDTTFKSSNF | 351 | 11 | | 35301 |
| HPV31 | L1 | NSICKYPDY | 227 | 9 | | 35302 |
| HPV31 | L1 | NSICKYPDYLK | 227 | 11 | | 35303 |
| HPV31 | L1 | PAILEDWNF | 397 | 9 | | 35304 |
| HPV31 | L1 | PAKRKKTK | 496 | 8 | | 35305 |
| HPV31 | L1 | PAKRKKTKK | 496 | 9 | | 35306 |
| HPV31 | L1 | PDPNKFGF | 79 | 8 | | 35307 |
| HPV31 | L1 | PDYLKMVA | 233 | 8 | | 35308 |
| HPV31 | L1 | PDYLKMVAEPY | 233 | 11 | | 35309 |
| HPV31 | L1 | PGDCPPLELK | 183 | 10 | | 35310 |
| HPV31 | L1 | PIGEHWGK | 165 | 8 | | 35311 |
| HPV31 | L1 | PLDICNSICK | 222 | 10 | | 35312 |
| HPV31 | L1 | PLDICNSICKY | 222 | 11 | | 35313 |
| HPV31 | L1 | PLGRKFLLQA | 464 | 10 | | 35314 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | L1 | PLGVGISGH | 113 | 9 | | 35315 |
| HPV31 | L1 | PSASTTTPA | 489 | 9 | | 35316 |
| HPV31 | L1 | PSASTTTPAK | 489 | 10 | | 35317 |
| HPV31 | L1 | PSASTTTPAKR | 489 | 11 | | 35318 |
| HPV31 | L1 | PSGSLEDTY | 411 | 9 | | 35319 |
| HPV31 | L1 | PSGSLEDTYR | 411 | 10 | | 35320 |
| HPV31 | L1 | PSGSLEDTYRF | 411 | 11 | | 35321 |
| HPV31 | L1 | PSGSMVTSDA | 296 | 10 | | 35322 |
| HPV31 | L1 | PVSKVVSTDEY | 17 | 11 | | 35323 |
| HPV31 | L1 | QAGYRARPK | 472 | 9 | | 35324 |
| HPV31 | L1 | QAGYRARPKF | 472 | 10 | | 35325 |
| HPV31 | L1 | QAGYRARPKFK | 472 | 11 | | 35326 |
| HPV31 | L1 | QAITCQKTA | 425 | 9 | | 35327 |
| HPV31 | L1 | QDGDMVDTGF | 197 | 10 | | 35328 |
| HPV31 | L1 | QFIFQLCK | 374 | 8 | | 35329 |
| HPV31 | L1 | QFPLGRKF | 462 | 8 | | 35330 |
| HPV31 | L1 | QIFNKPYWMQR | 306 | 11 | | 35331 |
| HPV31 | L1 | QLCKITLSA | 378 | 9 | | 35332 |
| HPV31 | L1 | QLCLLGCK | 156 | 8 | | 35333 |
| HPV31 | L1 | QLFVTVVDTTR | 329 | 11 | | 35334 |
| HPV31 | L1 | QMFVRHFF | 255 | 8 | | 35335 |
| HPV31 | L1 | QMFVRHFFNR | 255 | 10 | | 35336 |
| HPV31 | L1 | QTQLCLLGCK | 154 | 10 | | 35337 |
| HPV31 | L1 | RARPKFKA | 476 | 8 | | 35338 |
| HPV31 | L1 | RARPKFKAGK | 476 | 10 | | 35339 |
| HPV31 | L1 | RARPKFKAGKR | 476 | 11 | | 35340 |
| HPV31 | L1 | RLLTVGHPY | 41 | 9 | | 35341 |
| HPV31 | L1 | RLLTVGHPYY | 41 | 10 | | 35342 |
| HPV31 | L1 | RLPDPNKF | 77 | 8 | | 35343 |
| HPV31 | L1 | RLPDPNKFGF | 77 | 10 | | 35344 |
| HPV31 | L1 | RSTNMSVCA | 339 | 9 | | 35345 |
| HPV31 | L1 | RSTNMSVCAA | 339 | 10 | | 35346 |
| HPV31 | L1 | RTNIYYHA | 30 | 8 | | 35347 |
| HPV31 | L1 | RTNIYYHAGSA | 30 | 11 | | 35348 |
| HPV31 | L1 | RVRLPDPNK | 75 | 9 | | 35349 |
| HPV31 | L1 | RVRLPDPNKF | 75 | 10 | | 35350 |
| HPV31 | L1 | SADIMTYIH | 385 | 9 | | 35351 |
| HPV31 | L1 | SADLDQFPLGR | 457 | 11 | | 35352 |
| HPV31 | L1 | SAPSASTTTPA | 487 | 11 | | 35353 |
| HPV31 | L1 | SARLLTVGH | 39 | 9 | | 35354 |
| HPV31 | L1 | SARLLTVGHPY | 39 | 11 | | 35355 |
| HPV31 | L1 | SASTTTPA | 490 | 8 | | 35356 |
| HPV31 | L1 | SASTTTPAK | 490 | 9 | | 35357 |
| HPV31 | L1 | SASTTTPAKR | 490 | 10 | | 35358 |
| HPV31 | L1 | SASTTTPAKRK | 490 | 11 | | 35359 |
| HPV31 | L1 | SDAQIFNK | 303 | 8 | | 35360 |
| HPV31 | L1 | SDAQIFNKPY | 303 | 10 | | 35361 |
| HPV31 | L1 | SDNPKKIVVPK | 55 | 11 | | 35362 |
| HPV31 | L1 | SDTTFKSSNF | 352 | 10 | | 35363 |
| HPV31 | L1 | SDTTFKSSNFK | 352 | 11 | | 35364 |
| HPV31 | L1 | SFYNPETQR | 90 | 9 | | 35365 |
| HPV31 | L1 | SGHPLLNK | 119 | 8 | | 35366 |
| HPV31 | L1 | SGHPLLNKF | 119 | 9 | | 35367 |
| HPV31 | L1 | SGLQYRVF | 67 | 8 | | 35368 |
| HPV31 | L1 | SGLQYRVFR | 67 | 9 | | 35369 |
| HPV31 | L1 | SGLQYRVFRVR | 67 | 11 | | 35370 |
| HPV31 | L1 | SGSLEDTY | 412 | 8 | | 35371 |
| HPV31 | L1 | SGSLEDTYR | 412 | 9 | | 35372 |
| HPV31 | L1 | SGSLEDTYRF | 412 | 10 | | 35373 |
| HPV31 | L1 | SGSMVTSDA | 297 | 9 | | 35374 |
| HPV31 | L1 | SGSTATLA | 281 | 8 | | 35375 |
| HPV31 | L1 | SICKYPDY | 228 | 8 | | 35376 |
| HPV31 | L1 | SICKYPDYLK | 228 | 10 | | 35377 |
| HPV31 | L1 | SIPKSDNPK | 51 | 9 | | 35378 |
| HPV31 | L1 | SIPKSDNPKK | 51 | 10 | | 35379 |
| HPV31 | L1 | SLEDTYRF | 414 | 8 | | 35380 |
| HPV31 | L1 | SLWRPSEA | 2 | 8 | | 35381 |
| HPV31 | L1 | SLWRPSEATVY | 2 | 11 | | 35382 |
| HPV31 | L1 | SMVTSDAQIF | 299 | 10 | | 35383 |
| HPV31 | L1 | SSNFKEYLR | 358 | 9 | | 35384 |
| HPV31 | L1 | SSNFKEYLRH | 358 | 10 | | 35385 |
| HPV31 | L1 | STATLANSTY | 283 | 10 | | 35386 |
| HPV31 | L1 | STATLANSTYF | 283 | 11 | | 35387 |
| HPV31 | L1 | STDEYVTR | 23 | 8 | | 35388 |
| HPV31 | L1 | STNMSVCA | 340 | 8 | | 35389 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | L1 | STNMSVCAA | 340 | 9 | | 35390 |
| HPV31 | L1 | STNMSVCAAIA | 340 | 11 | | 35391 |
| HPV31 | L1 | STTTPAKR | 492 | 8 | | 35392 |
| HPV31 | L1 | STTTPAKRK | 492 | 9 | | 35393 |
| HPV31 | L1 | STTTPAKRKK | 492 | 10 | | 35394 |
| HPV31 | L1 | SVPTDLYIK | 271 | 9 | | 35395 |
| HPV31 | L1 | TAPQKPKEDPF | 432 | 11 | | 35396 |
| HPV31 | L1 | TATLANSTY | 284 | 9 | | 35397 |
| HPV31 | L1 | TATLANSTYF | 284 | 10 | | 35398 |
| HPV31 | L1 | TCQKTAPQK | 428 | 9 | | 35399 |
| HPV31 | L1 | TCQKTAPQKPK | 428 | 11 | | 35400 |
| HPV31 | L1 | TDEYVTRTNIY | 24 | 11 | | 35401 |
| HPV31 | L1 | TDNRECISMDY | 142 | 11 | | 35402 |
| HPV31 | L1 | TFKSSNFK | 355 | 8 | | 35403 |
| HPV31 | L1 | TFKSSNFKEY | 355 | 10 | | 35404 |
| HPV31 | L1 | TGFGAMDF | 204 | 8 | | 35405 |
| HPV31 | L1 | TGFGAMDFTA | 204 | 10 | | 35406 |
| HPV31 | L1 | TLANSTYF | 286 | 8 | | 35407 |
| HPV31 | L1 | TLFFYLRR | 246 | 8 | | 35408 |
| HPV31 | L1 | TLSADIMTY | 383 | 9 | | 35409 |
| HPV31 | L1 | TLSADIMTYIH | 383 | 11 | | 35410 |
| HPV31 | L1 | TSDAQIFNK | 302 | 9 | | 35411 |
| HPV31 | L1 | TSDAQIFNKPY | 302 | 11 | | 35412 |
| HPV31 | L1 | TSFYNPETQR | 89 | 10 | | 35413 |
| HPV31 | L1 | TSQAITCQK | 423 | 9 | | 35414 |
| HPV31 | L1 | TSQAITCQKTA | 423 | 11 | | 35415 |
| HPV31 | L1 | TTFKSSNF | 354 | 8 | | 35416 |
| HPV31 | L1 | TTFKSSNFK | 354 | 9 | | 35417 |
| HPV31 | L1 | TTFKSSNFKEY | 354 | 11 | | 35418 |
| HPV31 | L1 | TTPAKRKK | 494 | 8 | | 35419 |
| HPV31 | L1 | TTPAKRKKTK | 494 | 10 | | 35420 |
| HPV31 | L1 | TTPAKRKKTKK | 494 | 11 | | 35421 |
| HPV31 | L1 | TTRSTNMSVCA | 337 | 11 | | 35422 |
| HPV31 | L1 | TTTPAKRK | 493 | 8 | | 35423 |
| HPV31 | L1 | TTTPAKRKK | 493 | 9 | | 35424 |
| HPV31 | L1 | TTPAKRKKTK | 493 | 11 | | 35425 |
| HPV31 | L1 | TVGESVPTDLY | 267 | 11 | | 35426 |
| HPV31 | L1 | TVGHPYYSIPK | 44 | 11 | | 35427 |
| HPV31 | L1 | TVYLPPVPVSK | 10 | 11 | | 35428 |
| HPV31 | L1 | VAEPYGDTLF | 239 | 10 | | 35429 |
| HPV31 | L1 | VAEPYGDTLFF | 239 | 11 | | 35430 |
| HPV31 | L1 | VDTGFGAMDF | 202 | 10 | | 35431 |
| HPV31 | L1 | VFRVRLPDPNK | 73 | 11 | | 35432 |
| HPV31 | L1 | VFWEVNLK | 446 | 8 | | 35433 |
| HPV31 | L1 | VFWEVNLKEK | 446 | 10 | | 35434 |
| HPV31 | L1 | VFWEVNLKEKF | 446 | 11 | | 35435 |
| HPV31 | L1 | VGESVPTDLY | 268 | 10 | | 35436 |
| HPV31 | L1 | VGHPYYSIPK | 45 | 10 | | 35437 |
| HPV31 | L1 | VGISGHPLLNK | 116 | 11 | | 35438 |
| HPV31 | L1 | VSGLQYRVF | 66 | 9 | | 35439 |
| HPV31 | L1 | VSGLQYRVFR | 66 | 10 | | 35440 |
| HPV31 | L1 | VSKVVSTDEY | 18 | 10 | | 35441 |
| HPV31 | L1 | VSTDEYVTR | 22 | 9 | | 35442 |
| HPV31 | L1 | VTRTNIYY | 28 | 8 | | 35443 |
| HPV31 | L1 | VTRTNIYYH | 28 | 9 | | 35444 |
| HPV31 | L1 | VTRTNIYYHA | 28 | 10 | | 35445 |
| HPV31 | L1 | VTSDAQIF | 301 | 8 | | 35446 |
| HPV31 | L1 | VTSDAQIFNK | 301 | 10 | | 35447 |
| HPV31 | L1 | VTSQAITCQK | 422 | 10 | | 35448 |
| HPV31 | L1 | VTVVDTTR | 332 | 8 | | 35449 |
| HPV31 | L1 | VVPKVSGLQY | 62 | 10 | | 35450 |
| HPV31 | L1 | VVPKVSGLQYR | 62 | 11 | | 35451 |
| HPV31 | L1 | VVSTDEYVTR | 21 | 10 | | 35452 |
| HPV31 | L1 | WACVGLEVGR | 101 | 10 | | 35453 |
| HPV31 | L1 | WGKGSPCSNNA | 170 | 11 | | 35454 |
| HPV31 | L1 | WMQRAQGH | 313 | 8 | | 35455 |
| HPV31 | L1 | YAGGPGTDNR | 136 | 10 | | 35456 |
| HPV31 | L1 | YGDTLFFY | 243 | 8 | | 35457 |
| HPV31 | L1 | TGDTLFFYLR | 243 | 10 | | 35458 |
| HPV31 | L1 | YGDTLFFYLRR | 243 | 11 | | 35459 |
| HPV31 | L1 | YIHSMNPA | 391 | 8 | | 35460 |
| HPV31 | L1 | YIKGSGSTA | 277 | 9 | | 35461 |
| HPV31 | L1 | YLKMVAEPY | 235 | 9 | | 35462 |
| HPV31 | L1 | YLPPVPVSK | 12 | 9 | | 35463 |
| HPV31 | L1 | YLRHGEEF | 364 | 8 | | 35464 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | L1 | YLRREQMF | 250 | 8 | | 35465 |
| HPV31 | L1 | YLRREQMFVR | 250 | 10 | | 35466 |
| HPV31 | L1 | YLRREQMFVRH | 250 | 11 | | 35467 |
| HPV31 | L1 | YSIPKSDNPK | 50 | 10 | | 35468 |
| HPV31 | L1 | YSIPKSDNPKK | 50 | 11 | | 35469 |
| HPV31 | L1 | YVFWEVNLK | 445 | 9 | | 35470 |
| HPV31 | L1 | YVFWEVNLKEK | 445 | 11 | | 35471 |
| HPV31 | L1 | YVTRTNIY | 27 | 8 | | 35472 |
| HPV31 | L1 | YVTRTNIYY | 27 | 9 | | 35473 |
| HPV31 | L1 | YVTRTNIYYH | 27 | 10 | | 35474 |
| HPV31 | L1 | YVTRTNIYYHA | 27 | 11 | | 35475 |
| HPV31 | L2 | ADTDFTVDTPA | 357 | 11 | | 35476 |
| HPV31 | L2 | AGTCPSDVIPK | 25 | 11 | | 35477 |
| HPV31 | L2 | AILDVTSVSTH | 143 | 11 | | 35478 |
| HPV31 | L2 | ALHRPALTSR | 281 | 10 | | 35479 |
| HPV31 | L2 | ALHRPALTSRR | 281 | 11 | | 35480 |
| HPV31 | L2 | ALTSRRNTVR | 286 | 10 | | 35481 |
| HPV31 | L2 | ALTSRRNTVRY | 286 | 11 | | 35482 |
| HPV31 | L2 | ASATQLYQTCK | 13 | 11 | | 35483 |
| HPV31 | L2 | ATHNVSPSTA | 367 | 10 | | 35484 |
| HPV31 | L2 | ATIGARVH | 311 | 8 | | 35485 |
| HPV31 | L2 | ATIGARVHY | 311 | 9 | | 35486 |
| HPV31 | L2 | ATIGARVHYY | 311 | 10 | | 35487 |
| HPV31 | L2 | ATIGARVHYYY | 311 | 11 | | 35488 |
| HPV31 | L2 | ATQLYQTCK | 15 | 9 | | 35489 |
| HPV31 | L2 | ATQLYQTCKA | 15 | 10 | | 35490 |
| HPV31 | L2 | ATQLYQTCKAA | 15 | 11 | | 35491 |
| HPV31 | L2 | ATTADTTPA | 135 | 9 | | 35492 |
| HPV31 | L2 | AVQSTSAVSA | 376 | 10 | | 35493 |
| HPV31 | L2 | AVQSTSAVSAY | 376 | 11 | | 35494 |
| HPV31 | L2 | DFLDIIALH | 275 | 9 | | 35495 |
| HPV31 | L2 | DFLDIIALHR | 275 | 10 | | 35496 |
| HPV31 | L2 | DFTVDTPA | 360 | 8 | | 35497 |
| HPV31 | L2 | DFTVDTPATH | 360 | 10 | | 35498 |
| HPV31 | L2 | DFYLHPSY | 438 | 8 | | 35499 |
| HPV31 | L2 | DFYLHPSYY | 438 | 9 | | 35500 |
| HPV31 | L2 | DGGDFYLH | 435 | 8 | | 35501 |
| HPV31 | L2 | DGGDFYLHPSY | 435 | 11 | | 35502 |
| HPV31 | L2 | DGLYDIYA | 350 | 8 | | 35503 |
| HPV31 | L2 | DIATTADTTPA | 133 | 11 | | 35504 |
| HPV31 | L2 | DIIALHRPA | 278 | 9 | | 35505 |
| HPV31 | L2 | DISSINPA | 322 | 8 | | 35506 |
| HPV31 | L2 | DIYADTDF | 354 | 8 | | 35507 |
| HPV31 | L2 | DTDFTVDTPA | 358 | 10 | | 35508 |
| HPV31 | L2 | DVGAPAPIPH | 116 | 10 | | 35509 |
| HPV31 | L2 | DVIPKIEH | 31 | 8 | | 35510 |
| HPV31 | L2 | DVTSVSTH | 146 | 8 | | 35511 |
| HPV31 | L2 | EMQPLGASA | 334 | 9 | | 35512 |
| HPV31 | L2 | ESGIVDVGA | 111 | 9 | | 35513 |
| HPV31 | L2 | ESGIVDVGAPA | 111 | 11 | | 35514 |
| HPV31 | L2 | ESIEMQPLGA | 331 | 10 | | 35515 |
| HPV31 | L2 | ESLYFSNTSH | 259 | 10 | | 35516 |
| HPV31 | L2 | ETVNAEESLY | 253 | 10 | | 35517 |
| HPV31 | L2 | ETVNAEESLYF | 253 | 11 | | 35518 |
| HPV31 | L2 | FFTDVSVA | 458 | 8 | | 35519 |
| HPV31 | L2 | FFTDVSVAA | 458 | 9 | | 35520 |
| HPV31 | L2 | FLDIIALH | 276 | 8 | | 35521 |
| HPV31 | L2 | FLDIIALHR | 276 | 9 | | 35522 |
| HPV31 | L2 | FLDIIALHRPA | 276 | 11 | | 35523 |
| HPV31 | L2 | FLSAPKQLITY | 237 | 11 | | 35524 |
| HPV31 | L2 | FSGPDVPIEH | 404 | 10 | | 35525 |
| HPV31 | L2 | FSGPDVPIEHA | 404 | 11 | | 35526 |
| HPV31 | L2 | FSNTSHNIA | 263 | 9 | | 35527 |
| HPV31 | L2 | FTDVSVAA | 459 | 8 | | 35528 |
| HPV31 | L2 | FTVDTPATH | 361 | 9 | | 35529 |
| HPV31 | L2 | FVDGGDFY | 433 | 8 | | 35530 |
| HPV31 | L2 | FVDGGDFYLH | 433 | 10 | | 35531 |
| HPV31 | L2 | GAPAPIPH | 118 | 8 | | 35532 |
| HPV31 | L2 | GARVHYYY | 314 | 8 | | 35533 |
| HPV31 | L2 | GATIGARVH | 310 | 9 | | 35534 |
| HPV31 | L2 | GATIGARVHY | 310 | 10 | | 35535 |
| HPV31 | L2 | GATIGARVHYY | 310 | 11 | | 35536 |
| HPV31 | L2 | GDFYLHPSY | 437 | 9 | | 35537 |
| HPV31 | L2 | GDFYLHPSYY | 437 | 10 | | 35538 |
| HPV31 | L2 | GFDIATTA | 131 | 8 | | 35539 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | L2 | GGDFYLHPSY | 436 | 10 | | 35540 |
| HPV31 | L2 | GGDFYLHPSYY | 436 | 11 | | 35541 |
| HPV31 | L2 | GIGSGSGTGGR | 59 | 11 | | 35542 |
| HPV31 | L2 | GIVDVGAPA | 113 | 9 | | 35543 |
| HPV31 | L2 | GLYDIYADTDF | 351 | 11 | | 35544 |
| HPV31 | L2 | GLYSKATQQVK | 221 | 11 | | 35545 |
| HPV31 | L2 | GSGSGTGGR | 61 | 9 | | 35546 |
| HPV31 | L2 | GSGTGGRTGY | 63 | 10 | | 35547 |
| HPV31 | L2 | GTCPSDVIPK | 26 | 10 | | 35548 |
| HPV31 | L2 | GTGGRTGY | 65 | 8 | | 35549 |
| HPV31 | L2 | GVRRPARLGLY | 213 | 11 | | 35550 |
| HPV31 | L2 | HAPTQVFPF | 413 | 9 | | 35551 |
| HPV31 | L2 | HTTIADQILR | 38 | 10 | | 35552 |
| HPV31 | L2 | HTTIADQILRY | 38 | 11 | | 35553 |
| HPV31 | L2 | IADQILRY | 41 | 8 | | 35554 |
| HPV31 | L2 | IALHRPALTSR | 280 | 11 | | 35555 |
| HPV31 | L2 | IATTADTTPA | 134 | 10 | | 35556 |
| HPV31 | L2 | IDPTFLSA | 233 | 8 | | 35557 |
| HPV31 | L2 | IDPTFLSAPK | 233 | 10 | | 35558 |
| HPV31 | L2 | IFSGPDVPIEH | 403 | 11 | | 35559 |
| HPV31 | L2 | IFVDGGDF | 432 | 8 | | 35560 |
| HPV31 | L2 | IFVDGGDFY | 432 | 9 | | 35561 |
| HPV31 | L2 | IFVDGGDFYLH | 432 | 11 | | 35562 |
| HPV31 | L2 | IGARVHYY | 313 | 8 | | 35563 |
| HPV31 | L2 | IGARVHYYY | 313 | 9 | | 35564 |
| HPV31 | L2 | IGSGSGTGGR | 60 | 10 | | 35565 |
| HPV31 | L2 | IIALHRPA | 279 | 8 | | 35566 |
| HPV31 | L2 | ILDVTSVSTH | 144 | 10 | | 35567 |
| HPV31 | L2 | ILRYGSMGVF | 45 | 10 | | 35568 |
| HPV31 | L2 | ILRYGSMGVFF | 45 | 11 | | 35569 |
| HPV31 | L2 | ITSSTPIPGVR | 205 | 11 | | 35570 |
| HPV31 | L2 | ITYENPAY | 245 | 8 | | 35571 |
| HPV31 | L2 | IVDVGAPA | 114 | 8 | | 35572 |
| HPV31 | L2 | KIEHTTIA | 35 | 8 | | 35573 |
| HPV31 | L2 | KVIDPTFLSA | 231 | 10 | | 35574 |
| HPV31 | L2 | LAPTTPQVSIF | 423 | 11 | | 35575 |
| HPV31 | L2 | LDIIALHR | 277 | 8 | | 35576 |
| HPV31 | L2 | LDIIALHRPA | 277 | 10 | | 35577 |
| HPV31 | L2 | LDVTSVSTH | 145 | 9 | | 35578 |
| HPV31 | L2 | LGNKQTLR | 299 | 8 | | 35579 |
| HPV31 | L2 | LGNKQTLRTR | 299 | 10 | | 35580 |
| HPV31 | L2 | LITYENPA | 244 | 8 | | 35581 |
| HPV31 | L2 | LITYENPAY | 244 | 9 | | 35582 |
| HPV31 | L2 | LLLSSSSISTH | 176 | 11 | | 35583 |
| HPV31 | L2 | LLSSSSISTH | 177 | 10 | | 35584 |
| HPV31 | L2 | LSAPKQLITY | 238 | 10 | | 35585 |
| HPV31 | L2 | LSSSSISTH | 178 | 9 | | 35586 |
| HPV31 | L2 | LSSSSISTHNY | 178 | 11 | | 35587 |
| HPV31 | L2 | LSTGFDIPIF | 395 | 10 | | 35588 |
| HPV31 | L2 | LSTRPSTVSEA | 75 | 11 | | 35589 |
| HPV31 | L2 | LTSRRNTVR | 287 | 9 | | 35590 |
| HPV31 | L2 | LTSRRNTVRY | 287 | 10 | | 35591 |
| HPV31 | L2 | MLKRRRKR | 447 | 8 | | 35592 |
| HPV31 | L2 | MLKRRRKRVSY | 447 | 11 | | 35593 |
| HPV31 | L2 | NAEESLYF | 256 | 8 | | 35594 |
| HPV31 | L2 | NDGLYDIY | 349 | 8 | | 35595 |
| HPV31 | L2 | NDGLYDIYA | 349 | 9 | | 35596 |
| HPV31 | L2 | NIAPDPDF | 269 | 8 | | 35597 |
| HPV31 | L2 | NTTVPLSTGF | 390 | 10 | | 35598 |
| HPV31 | L2 | NTVRYSRLGNK | 292 | 11 | | 35599 |
| HPV31 | L2 | PALTSRRNTVR | 285 | 11 | | 35600 |
| HPV31 | L2 | PARLGLYSK | 217 | 9 | | 35601 |
| HPV31 | L2 | PARLGLYSKA | 217 | 10 | | 35602 |
| HPV31 | L2 | PATHNVSPSTA | 366 | 11 | | 35603 |
| HPV31 | L2 | PAYETVNA | 250 | 8 | | 35604 |
| HPV31 | L2 | PDFLDIIA | 274 | 8 | | 35605 |
| HPV31 | L2 | PDFLDIIALH | 274 | 10 | | 35606 |
| HPV31 | L2 | PDFLDIIALHR | 274 | 11 | | 35607 |
| HPV31 | L2 | PDPDFLDIIA | 272 | 10 | | 35608 |
| HPV31 | L2 | PDVPIEHA | 407 | 8 | | 35609 |
| HPV31 | L2 | PGVRRPAR | 212 | 8 | | 35610 |
| HPV31 | L2 | PIEHAPTQVF | 410 | 10 | | 35611 |
| HPV31 | L2 | PIPGVRRPA | 210 | 9 | | 35612 |
| HPV31 | L2 | PIPGVRRPAR | 210 | 10 | | 35613 |
| HPV31 | L2 | PIPHPPTTSGF | 122 | 11 | | 35614 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | L2 | PLSTGFDIPIF | 394 | 11 | | 35615 |
| HPV31 | L2 | PSDVIPKIEH | 29 | 10 | | 35616 |
| HPV31 | L2 | PSTAVQSTSA | 373 | 10 | | 35617 |
| HPV31 | L2 | PSVLQPPTPA | 161 | 10 | | 35618 |
| HPV31 | L2 | PSYYMLKR | 443 | 8 | | 35619 |
| HPV31 | L2 | PSYYMLKRR | 443 | 9 | | 35620 |
| HPV31 | L2 | PSYYMLKRRR | 443 | 10 | | 35621 |
| HPV31 | L2 | PSYYMLKRRRK | 443 | 11 | | 35622 |
| HPV31 | L2 | PTFLSAPK | 235 | 8 | | 35623 |
| HPV31 | L2 | PTPAETSGH | 167 | 9 | | 35624 |
| HPV31 | L2 | PTQVFPFPLA | 415 | 10 | | 35625 |
| HPV31 | L2 | PTTPQVSIF | 425 | 9 | | 35626 |
| HPV31 | L2 | PTTSGFDIA | 127 | 9 | | 35627 |
| HPV31 | L2 | QILRYGSMGVF | 44 | 11 | | 35628 |
| HPV31 | L2 | QLITYENPA | 243 | 9 | | 35629 |
| HPV31 | L2 | QLITYENPAY | 243 | 10 | | 35630 |
| HPV31 | L2 | QLYQTCKA | 17 | 8 | | 35631 |
| HPV31 | L2 | QLYQTCKAA | 17 | 9 | | 35632 |
| HPV31 | L2 | QSTSAVSA | 378 | 8 | | 35633 |
| HPV31 | L2 | QSTSAVSAY | 378 | 9 | | 35634 |
| HPV31 | L2 | QTLRTRSGA | 303 | 9 | | 35635 |
| HPV31 | L2 | QVFPFPLA | 417 | 8 | | 35636 |
| HPV31 | L2 | QVKVIDPTF | 229 | 9 | | 35637 |
| HPV31 | L2 | QVSIFVDGGDF | 429 | 11 | | 35638 |
| HPV31 | L2 | RASATQLY | 12 | 8 | | 35639 |
| HPV31 | L2 | RLGLYSKA | 219 | 8 | | 35640 |
| HPV31 | L2 | RLGNKQTLR | 298 | 9 | | 35641 |
| HPV31 | L2 | RLGNKQTLRTR | 298 | 11 | | 35642 |
| HPV31 | L2 | RSGATIGA | 308 | 8 | | 35643 |
| HPV31 | L2 | RSGATIGAR | 308 | 9 | | 35644 |
| HPV31 | L2 | RSGATIGARVH | 308 | 11 | | 35645 |
| HPV31 | L2 | RSKRSTKR | 2 | 8 | | 35646 |
| HPV31 | L2 | RSKRSTKRTK | 2 | 10 | | 35647 |
| HPV31 | L2 | RSKRSTKRTKR | 2 | 11 | | 35648 |
| HPV31 | L2 | RSTKRTKR | 5 | 8 | | 35649 |
| HPV31 | L2 | RSTKRTKRA | 5 | 9 | | 35650 |
| HPV31 | L2 | RSTKRTKRASA | 5 | 11 | | 35651 |
| HPV31 | L2 | RTGYVPLSTR | 69 | 10 | | 35652 |
| HPV31 | L2 | RTKRASATQLY | 9 | 11 | | 35653 |
| HPV31 | L2 | RTRSGATIGA | 306 | 10 | | 35654 |
| HPV31 | L2 | RTRSGATIGAR | 306 | 11 | | 35655 |
| HPV31 | L2 | SAPKQLITY | 239 | 9 | | 35656 |
| HPV31 | L2 | SATQLYQTCK | 14 | 10 | | 35657 |
| HPV31 | L2 | SATQLYQTCKA | 14 | 11 | | 35658 |
| HPV31 | L2 | SDVIPKIEH | 30 | 9 | | 35659 |
| HPV31 | L2 | SGATIGAR | 309 | 8 | | 35660 |
| HPV31 | L2 | SGATIGARVH | 309 | 10 | | 35661 |
| HPV31 | L2 | SGATIGARVHY | 309 | 11 | | 35662 |
| HPV31 | L2 | SGFDIATTA | 130 | 9 | | 35663 |
| HPV31 | L2 | SGIVDVGA | 112 | 8 | | 35664 |
| HPV31 | L2 | SGIVDVGAPA | 112 | 10 | | 35665 |
| HPV31 | L2 | SGPDVPIEH | 405 | 9 | | 35666 |
| HPV31 | L2 | SGPDVPIEHA | 405 | 10 | | 35667 |
| HPV31 | L2 | SGSGTGGR | 62 | 8 | | 35668 |
| HPV31 | L2 | SGSGTGGRTGY | 62 | 11 | | 35669 |
| HPV31 | L2 | SGTGGRTGY | 64 | 9 | | 35670 |
| HPV31 | L2 | SIEMQPLGA | 332 | 9 | | 35671 |
| HPV31 | L2 | SIEMQPLGASA | 332 | 11 | | 35672 |
| HPV31 | L2 | SIFVDGGDF | 431 | 9 | | 35673 |
| HPV31 | L2 | SIFVDGGDFY | 431 | 10 | | 35674 |
| HPV31 | L2 | SLYFSNTSH | 260 | 9 | | 35675 |
| HPV31 | L2 | SSISTHNY | 181 | 8 | | 35676 |
| HPV31 | L2 | SSSISTHNY | 180 | 9 | | 35677 |
| HPV31 | L2 | SSSSISTH | 179 | 8 | | 35678 |
| HPV31 | L2 | SSSSISTHNY | 179 | 10 | | 35679 |
| HPV31 | L2 | SSTPIPGVR | 207 | 9 | | 35680 |
| HPV31 | L2 | SSTPIPGVRR | 207 | 10 | | 35681 |
| HPV31 | L2 | STAVQSTSA | 374 | 9 | | 35682 |
| HPV31 | L2 | STGFDIPIF | 396 | 9 | | 35683 |
| HPV31 | L2 | STHENPTF | 151 | 8 | | 35684 |
| HPV31 | L2 | STKRTKRA | 6 | 8 | | 35685 |
| HPV31 | L2 | STKRTKRASA | 6 | 10 | | 35686 |
| HPV31 | L2 | STLNDGLY | 346 | 8 | | 35687 |
| HPV31 | L2 | STLNDGLYDIY | 346 | 11 | | 35688 |
| HPV31 | L2 | STPIPGVR | 208 | 8 | | 35689 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV31 | L2 | STPIPGVRR | 208 | 9 | | 35690 |
| HPV31 | L2 | STPIPGVRRPA | 208 | 11 | | 35691 |
| HPV31 | L2 | STRPSTVSEA | 76 | 10 | | 35692 |
| HPV31 | L2 | STSAVSAY | 379 | 8 | | 35693 |
| HPV31 | L2 | STVSEASIPIR | 80 | 11 | | 35694 |
| HPV31 | L2 | SVLQPPTPA | 162 | 9 | | 35695 |
| HPV31 | L2 | SVSTHENPTF | 149 | 10 | | 35696 |
| HPV31 | L2 | TAVQSTSA | 375 | 8 | | 35697 |
| HPV31 | L2 | TAVQSTSAVSA | 375 | 11 | | 35698 |
| HPV31 | L2 | TCPSDVIPK | 27 | 9 | | 35699 |
| HPV31 | L2 | TDFTVDTPA | 359 | 9 | | 35700 |
| HPV31 | L2 | TDFTVDTPATH | 359 | 11 | | 35701 |
| HPV31 | L2 | TGFDIPIF | 397 | 8 | | 35702 |
| HPV31 | L2 | TGYVPLSTR | 70 | 9 | | 35703 |
| HPV31 | L2 | TIADQILR | 40 | 8 | | 35704 |
| HPV31 | L2 | TIADQILRY | 40 | 9 | | 35705 |
| HPV31 | L2 | TIGARVHY | 312 | 8 | | 35706 |
| HPV31 | L2 | TIGARVHYY | 312 | 9 | | 35707 |
| HPV31 | L2 | TIGARVHYYY | 312 | 10 | | 35708 |
| HPV31 | L2 | TLNDGLYDIY | 347 | 10 | | 35709 |
| HPV31 | L2 | TLNDGLYDIYA | 347 | 11 | | 35710 |
| HPV31 | L2 | TLRTRSGA | 304 | 8 | | 35711 |
| HPV31 | L2 | TSGFDIATTA | 129 | 10 | | 35712 |
| HPV31 | L2 | TSHNIAPDPDF | 266 | 11 | | 35713 |
| HPV31 | L2 | TSRRNTVR | 288 | 8 | | 35714 |
| HPV31 | L2 | TSRRNTVRY | 288 | 9 | | 35715 |
| HPV31 | L2 | TSRRNTVRYSR | 288 | 11 | | 35716 |
| HPV31 | L2 | TSSTPIPGVR | 206 | 10 | | 35717 |
| HPV31 | L2 | TSSTPIPGVRR | 206 | 11 | | 35718 |
| HPV31 | L2 | TSTLNDGLY | 345 | 9 | | 35719 |
| HPV31 | L2 | TSVSTHENPTF | 148 | 11 | | 35720 |
| HPV31 | L2 | TTADTTPA | 136 | 8 | | 35721 |
| HPV31 | L2 | TTIADQILR | 39 | 9 | | 35722 |
| HPV31 | L2 | TTIADQILRY | 39 | 10 | | 35723 |
| HPV31 | L2 | TTPQVSIF | 426 | 8 | | 35724 |
| HPV31 | L2 | TTSGFDIA | 128 | 8 | | 35725 |
| HPV31 | L2 | TTSGFDIATTA | 128 | 11 | | 35726 |
| HPV31 | L2 | TTSTLNDGLY | 344 | 10 | | 35727 |
| HPV31 | L2 | TTTSTLNDGLY | 343 | 11 | | 35728 |
| HPV31 | L2 | TTVPLSTGF | 391 | 9 | | 35729 |
| HPV31 | L2 | TVDTPATH | 362 | 8 | | 35730 |
| HPV31 | L2 | TVNAEESLY | 254 | 9 | | 35731 |
| HPV31 | L2 | TVNAEESLYF | 254 | 10 | | 35732 |
| HPV31 | L2 | TVPLSTGF | 392 | 8 | | 35733 |
| HPV31 | L2 | TVRYSRLGNK | 293 | 10 | | 35734 |
| HPV31 | L2 | TVSEASIPIR | 81 | 10 | | 35735 |
| HPV31 | L2 | VDGGDFYLH | 434 | 9 | | 35736 |
| HPV31 | L2 | VDVGAPAPIPH | 115 | 11 | | 35737 |
| HPV31 | L2 | VGAPAPIPH | 117 | 9 | | 35738 |
| HPV31 | L2 | VIDPTFLSA | 232 | 9 | | 35739 |
| HPV31 | L2 | VIDPTFLSAPK | 232 | 11 | | 35740 |
| HPV31 | L2 | VIPKIEHTTIA | 32 | 11 | | 35741 |
| HPV31 | L2 | VLQPPTPA | 163 | 8 | | 35742 |
| HPV31 | L2 | VSEASIPIR | 82 | 9 | | 35743 |
| HPV31 | L2 | VSIFVDGGDF | 430 | 10 | | 35744 |
| HPV31 | L2 | VSIFVDGGDFY | 430 | 11 | | 35745 |
| HPV31 | L2 | VSTHENPTF | 150 | 9 | | 35746 |
| HPV31 | L2 | VSYFFTDVSVA | 455 | 11 | | 35747 |
| HPV31 | L2 | YDISSINPA | 321 | 9 | | 35748 |
| HPV31 | L2 | YDIYADTDF | 353 | 9 | | 35749 |
| HPV31 | L2 | YFFTDVSVA | 457 | 9 | | 35750 |
| HPV31 | L2 | YFFTDVSVAA | 457 | 10 | | 35751 |
| HPV31 | L2 | YFSNTSHNIA | 262 | 10 | | 35752 |
| HPV31 | L2 | YGSMGVFF | 48 | 8 | | 35753 |
| HPV31 | L2 | YLHPSYYMLK | 440 | 10 | | 35754 |
| HPV31 | L2 | YLHPSYYMLKR | 440 | 11 | | 35755 |
| HPV31 | L2 | YMLKRRRK | 446 | 8 | | 35756 |
| HPV31 | L2 | YMLKRRRKR | 446 | 9 | | 35757 |
| HPV31 | L2 | YSKATQQVK | 223 | 9 | | 35758 |
| HPV31 | L2 | YSRLGNKQTLR | 296 | 11 | | 35759 |
| HPV33 | E1 | AAAFLKSNSQA | 382 | 11 | | 35760 |
| HPV33 | E1 | AACSQSAA | 90 | 8 | | 35761 |
| HPV33 | E1 | AAEDVVDR | 96 | 8 | | 35762 |
| HPV33 | E1 | AAEDVVDRA | 96 | 9 | | 35763 |
| HPV33 | E1 | AAEDVVDRAA | 96 | 10 | | 35764 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E1 | AAFLKSNSQA | 383 | 10 | | 35765 |
| HPV33 | E1 | AAFLKSNSQAK | 383 | 11 | | 35766 |
| HPV33 | E1 | AANPCRTSINK | 104 | 11 | | 35767 |
| HPV33 | E1 | ADDSGTDLLEF | 40 | 11 | | 35768 |
| HPV33 | E1 | ADPEGTNGA | 2 | 9 | | 35769 |
| HPV33 | E1 | ADSNSNAA | 376 | 8 | | 35770 |
| HPV33 | E1 | ADSNSNAAA | 376 | 9 | | 35771 |
| HPV33 | E1 | ADSNSNAAAF | 376 | 10 | | 35772 |
| HPV33 | E1 | ADTEAARA | 61 | 8 | | 35773 |
| HPV33 | E1 | ADTEAARALF | 61 | 10 | | 35774 |
| HPV33 | E1 | AFKKFLKGIPK | 452 | 11 | | 35775 |
| HPV33 | E1 | AFLGAFKK | 448 | 8 | | 35776 |
| HPV33 | E1 | AFLGAFKKF | 448 | 9 | | 35777 |
| HPV33 | E1 | AFLGAFKKFLK | 448 | 11 | | 35778 |
| HPV33 | E1 | AFLKSNSQA | 384 | 9 | | 35779 |
| HPV33 | E1 | AFLKSNSQAK | 384 | 10 | | 35780 |
| HPV33 | E1 | AGENTRSLR | 635 | 9 | | 35781 |
| HPV33 | E1 | AGMGCTGWF | 10 | 9 | | 35782 |
| HPV33 | E1 | AGTDSRWPY | 563 | 9 | | 35783 |
| HPV33 | E1 | AGTDSRWPYLH | 563 | 11 | | 35784 |
| HPV33 | E1 | AINDENWK | 596 | 8 | | 35785 |
| HPV33 | E1 | AINDENWKSF | 596 | 10 | | 35786 |
| HPV33 | E1 | AINDENWKSFF | 596 | 11 | | 35787 |
| HPV33 | E1 | ALKRKFAA | 84 | 8 | | 35788 |
| HPV33 | E1 | ALYWFRTA | 311 | 8 | | 35789 |
| HPV33 | E1 | AVCALKRK | 81 | 8 | | 35790 |
| HPV33 | E1 | AVCALKRKF | 81 | 9 | | 35791 |
| HPV33 | E1 | AVCALKRKFA | 81 | 10 | | 35792 |
| HPV33 | E1 | AVCALKRKFAA | 81 | 11 | | 35793 |
| HPV33 | E1 | CALKRKFA | 83 | 8 | | 35794 |
| HPV33 | E1 | CALKRKFAA | 83 | 9 | | 35795 |
| HPV33 | E1 | CALYWFRTA | 310 | 9 | | 35796 |
| HPV33 | E1 | CGIMCRHY | 398 | 8 | | 35797 |
| HPV33 | E1 | CGIMCRHYK | 398 | 9 | | 35798 |
| HPV33 | E1 | CGIMCRHYKK | 398 | 10 | | 35799 |
| HPV33 | E1 | CGIMCRHYKKA | 398 | 11 | | 35800 |
| HPV33 | E1 | CGPANTGK | 469 | 8 | | 35801 |
| HPV33 | E1 | CGPANTGKSY | 469 | 10 | | 35802 |
| HPV33 | E1 | CGPANTGKSYF | 469 | 11 | | 35803 |
| HPV33 | E1 | CMLICGPA | 465 | 8 | | 35804 |
| HPV33 | E1 | CMVIEPPK | 297 | 8 | | 35805 |
| HPV33 | E1 | CMVIEPPKLR | 297 | 10 | | 35806 |
| HPV33 | E1 | CSAGENTR | 633 | 8 | | 35807 |
| HPV33 | E1 | CSAGENTRSLR | 633 | 11 | | 35808 |
| HPV33 | E1 | CSKNRLTVA | 276 | 9 | | 35809 |
| HPV33 | E1 | CSKNRLTVAK | 276 | 10 | | 35810 |
| HPV33 | E1 | CTDWCITGY | 226 | 9 | | 35811 |
| HPV33 | E1 | CTGWFEVEA | 14 | 9 | | 35812 |
| HPV33 | E1 | CVISCVNSK | 490 | 9 | | 35813 |
| HPV33 | E1 | CVISCVNSKSH | 490 | 11 | | 35814 |
| HPV33 | E1 | CVNSKSHF | 494 | 8 | | 35815 |
| HPV33 | E1 | DCGIMCRH | 397 | 8 | | 35816 |
| HPV33 | E1 | DCGIMCRHY | 397 | 9 | | 35817 |
| HPV33 | E1 | DCGIMCRHYK | 397 | 10 | | 35818 |
| HPV33 | E1 | DCGIMCRHYKK | 397 | 11 | | 35819 |
| HPV33 | E1 | DDLNAVCA | 77 | 8 | | 35820 |
| HPV33 | E1 | DDLNAVCALK | 77 | 10 | | 35821 |
| HPV33 | E1 | DDLNAVCALKR | 77 | 11 | | 35822 |
| HPV33 | E1 | DDSDIAYY | 364 | 8 | | 35823 |
| HPV33 | E1 | DDSDIAYYY | 364 | 9 | | 35824 |
| HPV33 | E1 | DDSDIAYYYA | 364 | 10 | | 35825 |
| HPV33 | E1 | DDSGTDLLEF | 41 | 10 | | 35826 |
| HPV33 | E1 | DDSMENSIQA | 52 | 10 | | 35827 |
| HPV33 | E1 | DDVTPISWTY | 515 | 10 | | 35828 |
| HPV33 | E1 | DGNEISIDVK | 534 | 10 | | 35829 |
| HPV33 | E1 | DGNEISIDVKH | 534 | 11 | | 35830 |
| HPV33 | E1 | DIAYYYAQLA | 367 | 10 | | 35831 |
| HPV33 | E1 | DLIEEEDK | 614 | 8 | | 35832 |
| HPV33 | E1 | DLIEEEDKENH | 614 | 11 | | 35833 |
| HPV33 | E1 | DLNAVCALK | 78 | 9 | | 35834 |
| HPV33 | E1 | DLNAVCALKR | 78 | 10 | | 35835 |
| HPV33 | E1 | DLNAVCALKRK | 78 | 11 | | 35836 |
| HPV33 | E1 | DLSEMVQWA | 349 | 9 | | 35837 |
| HPV33 | E1 | DLSEMVQWAY | 349 | 10 | | 35838 |
| HPV33 | E1 | DSDIAYYY | 365 | 8 | | 35839 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E1 | DSDIAYYYA | 365 | 9 | | 35840 |
| HPV33 | E1 | DSGTDLLEF | 42 | 9 | | 35841 |
| HPV33 | E1 | DSMENSIQA | 53 | 9 | | 35842 |
| HPV33 | E1 | DSNSNAAA | 377 | 8 | | 35843 |
| HPV33 | E1 | DSNSNAAAF | 377 | 9 | | 35844 |
| HPV33 | E1 | DSNSNAAAFLK | 377 | 11 | | 35845 |
| HPV33 | E1 | DSRWPYLH | 566 | 8 | | 35846 |
| HPV33 | E1 | DSRWPYLHSR | 566 | 10 | | 35847 |
| HPV33 | E1 | DTEAARALF | 62 | 9 | | 35848 |
| HPV33 | E1 | DVKHRALVQLK | 541 | 11 | | 35849 |
| HPV33 | E1 | DVTPISWTY | 516 | 9 | | 35850 |
| HPV33 | E1 | DVVDRAANPCR | 99 | 11 | | 35851 |
| HPV33 | E1 | ECTYRKRK | 117 | 8 | | 35852 |
| HPV33 | E1 | EDDLNAVCA | 76 | 9 | | 35853 |
| HPV33 | E1 | EDDLNAVCALK | 76 | 11 | | 35854 |
| HPV33 | E1 | EDVVDRAA | 98 | 8 | | 35855 |
| HPV33 | E1 | EFKNPFPF | 580 | 8 | | 35856 |
| HPV33 | E1 | EFTAFLGA | 445 | 8 | | 35857 |
| HPV33 | E1 | EFTAFLGAF | 445 | 9 | | 35858 |
| HPV33 | E1 | EFTAFLGAFK | 445 | 10 | | 35859 |
| HPV33 | E1 | EFTAFLGAFKK | 445 | 11 | | 35860 |
| HPV33 | E1 | EGEDDLNA | 74 | 8 | | 35861 |
| HPV33 | E1 | EGEDDLNAVCA | 74 | 11 | | 35862 |
| HPV33 | E1 | EISIDVKH | 537 | 8 | | 35863 |
| HPV33 | E1 | EISIDVKHR | 537 | 9 | | 35864 |
| HPV33 | E1 | EISIDVKHRA | 537 | 10 | | 35865 |
| HPV33 | E1 | ELTDDSDIA | 361 | 9 | | 35866 |
| HPV33 | E1 | ELTDDSDIAY | 361 | 10 | | 35867 |
| HPV33 | E1 | ELTDDSDIAYY | 361 | 11 | | 35868 |
| HPV33 | E1 | ELVRPFKSDK | 214 | 10 | | 35869 |
| HPV33 | E1 | ESLKVLIK | 242 | 8 | | 35870 |
| HPV33 | E1 | ESLKVLIKQH | 242 | 10 | | 35871 |
| HPV33 | E1 | ETCMVIEPPK | 295 | 10 | | 35872 |
| HPV33 | E1 | EVEAVIER | 19 | 8 | | 35873 |
| HPV33 | E1 | EVEAVIERR | 19 | 9 | | 35874 |
| HPV33 | E1 | FAACSQSA | 89 | 8 | | 35875 |
| HPV33 | E1 | FAACSQSAA | 89 | 9 | | 35876 |
| HPV33 | E1 | FDENGNPVY | 587 | 9 | | 35877 |
| HPV33 | E1 | FDENGNPVYA | 587 | 10 | | 35878 |
| HPV33 | E1 | FDLSEMVQWA | 348 | 10 | | 35879 |
| HPV33 | E1 | FDLSEMVQWAY | 348 | 11 | | 35880 |
| HPV33 | E1 | FFSRTWCK | 605 | 8 | | 35881 |
| HPV33 | E1 | FGMSLIQF | 479 | 8 | | 35882 |
| HPV33 | E1 | FGMSLIQFLK | 479 | 10 | | 35883 |
| HPV33 | E1 | FLGAFKKF | 449 | 8 | | 35884 |
| HPV33 | E1 | FLGAFKKFLK | 449 | 10 | | 35885 |
| HPV33 | E1 | FLKGIPKK | 456 | 8 | | 35886 |
| HPV33 | E1 | FLKSNSQA | 385 | 8 | | 35887 |
| HPV33 | E1 | FLKSNSQAK | 385 | 9 | 0.0013 | 35888 |
| HPV33 | E1 | FMELVRPF | 212 | 8 | | 35889 |
| HPV33 | E1 | FMELVRPFK | 212 | 9 | | 35890 |
| HPV33 | E1 | FTAFLGAF | 446 | 8 | | 35891 |
| HPV33 | E1 | FTAFLGAFK | 446 | 9 | | 35892 |
| HPV33 | E1 | FTAFLGAFKK | 446 | 10 | | 35893 |
| HPV33 | E1 | FTAFLGAFKKF | 446 | 11 | | 35894 |
| HPV33 | E1 | GAFKKFLK | 451 | 8 | | 35895 |
| HPV33 | E1 | GAGMGCTGWF | 9 | 10 | | 35896 |
| HPV33 | E1 | GCTGWFEVEA | 13 | 10 | | 35897 |
| HPV33 | E1 | GCVISCVNSK | 489 | 10 | | 35898 |
| HPV33 | E1 | GGNISTFK | 625 | 8 | | 35899 |
| HPV33 | E1 | GGNISTFKCSA | 625 | 11 | | 35900 |
| HPV33 | E1 | GIIILLIR | 265 | 9 | | 35901 |
| HPV33 | E1 | GIIILLIRF | 265 | 10 | | 35902 |
| HPV33 | E1 | GIIILLIRFR | 265 | 11 | | 35903 |
| HPV33 | E1 | GIMCRHYK | 399 | 8 | | 35904 |
| HPV33 | E1 | GIMCRHYKK | 399 | 9 | | 35905 |
| HPV33 | E1 | GIMCRHYKKA | 399 | 10 | | 35906 |
| HPV33 | E1 | GISFMELVR | 209 | 9 | | 35907 |
| HPV33 | E1 | GISFMELVRPF | 209 | 11 | | 35908 |
| HPV33 | E1 | GISPSVAESLK | 235 | 11 | | 35909 |
| HPV33 | E1 | GMGCTGWF | 11 | 8 | | 35910 |
| HPV33 | E1 | GMSLIQFLK | 480 | 9 | | 35911 |
| HPV33 | E1 | GTDSRWPY | 564 | 8 | | 35912 |
| HPV33 | E1 | GTDSRWPYLH | 564 | 10 | | 35913 |
| HPV33 | E1 | GTTPEWIDR | 327 | 9 | | 35914 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E1 | HFWLQPLSDA | 500 | 10 | | 35915 |
| HPV33 | E1 | HFWLQPLSDAK | 500 | 11 | | 35916 |
| HPV33 | E1 | HGGNISTF | 624 | 8 | | 35917 |
| HPV33 | E1 | HGGNISTFK | 624 | 9 | | 35918 |
| HPV33 | E1 | HLQCLTCDR | 256 | 9 | | 35919 |
| HPV33 | E1 | HSFNDNIF | 341 | 8 | | 35920 |
| HPV33 | E1 | HSRLTVFEF | 573 | 9 | | 35921 |
| HPV33 | E1 | HSRLTVFEFK | 573 | 10 | | 35922 |
| HPV33 | E1 | HSSNTKANILY | 192 | 11 | | 35923 |
| HPV33 | E1 | IAYYYAQLA | 368 | 9 | | 35924 |
| HPV33 | E1 | ICGPANTGK | 468 | 9 | | 35925 |
| HPV33 | E1 | ICGPANTGKSY | 468 | 11 | | 35926 |
| HPV33 | E1 | IDDSMENSIQA | 51 | 11 | | 35927 |
| HPV33 | E1 | IDDVTPISWTY | 514 | 11 | | 35928 |
| HPV33 | E1 | IDDYMRNA | 525 | 8 | | 35929 |
| HPV33 | E1 | IDELEDSGY | 125 | 9 | | 35930 |
| HPV33 | E1 | IDRLTVLQH | 333 | 9 | | 35931 |
| HPV33 | E1 | IDRLTVLQHSF | 333 | 11 | | 35932 |
| HPV33 | E1 | IFDLSEMVQWA | 347 | 11 | | 35933 |
| HPV33 | E1 | IGQWIQSR | 415 | 8 | | 35934 |
| HPV33 | E1 | IGQWIQSRCEK | 415 | 11 | | 35935 |
| HPV33 | E1 | IIILLLIR | 266 | 8 | | 35936 |
| HPV33 | E1 | IIILLLIRF | 266 | 9 | | 35937 |
| HPV33 | E1 | IIILLLIRFR | 266 | 10 | | 35938 |
| HPV33 | E1 | IILLLIRF | 267 | 8 | | 35939 |
| HPV33 | E1 | IILLLIRFR | 267 | 9 | | 35940 |
| HPV33 | E1 | ILLLIRFR | 268 | 8 | | 35941 |
| HPV33 | E1 | ILLLIRFRCSK | 268 | 11 | | 35942 |
| HPV33 | E1 | ILYKFKEA | 200 | 8 | | 35943 |
| HPV33 | E1 | ILYKFKEAY | 200 | 9 | | 35944 |
| HPV33 | E1 | IMCRHYKK | 400 | 8 | | 35945 |
| HPV33 | E1 | IMCRHYKKA | 400 | 9 | | 35946 |
| HPV33 | E1 | IMCRHYKKAEK | 400 | 11 | | 35947 |
| HPV33 | E1 | ISCVNSKSH | 492 | 9 | | 35948 |
| HPV33 | E1 | ISCVNSKSHF | 492 | 10 | | 35949 |
| HPV33 | E1 | ISEDEDETA | 32 | 9 | | 35950 |
| HPV33 | E1 | ISFMELVR | 210 | 8 | | 35951 |
| HPV33 | E1 | ISFMELVRPF | 210 | 10 | | 35952 |
| HPV33 | E1 | ISFMELVRPFK | 210 | 11 | | 35953 |
| HPV33 | E1 | ISIDVKHR | 538 | 8 | | 35954 |
| HPV33 | E1 | ISIDVKHRA | 538 | 9 | | 35955 |
| HPV33 | E1 | ISNVLHSSNTK | 187 | 11 | | 35956 |
| HPV33 | E1 | ISPSVAESLK | 236 | 10 | | 35957 |
| HPV33 | E1 | ISTFKCSA | 628 | 8 | | 35958 |
| HPV33 | E1 | ISWTYIDDY | 520 | 9 | | 35959 |
| HPV33 | E1 | ISWTYIDDYMR | 520 | 11 | | 35960 |
| HPV33 | E1 | ITGYGISPSVA | 231 | 11 | | 35961 |
| HPV33 | E1 | IVKDCGIMCR | 394 | 10 | | 35962 |
| HPV33 | E1 | IVKDCGIMCRH | 394 | 11 | | 35963 |
| HPV33 | E1 | KANILYKF | 197 | 8 | | 35964 |
| HPV33 | E1 | KANILYKFK | 197 | 9 | | 35965 |
| HPV33 | E1 | KANILYKFKEA | 197 | 11 | | 35966 |
| HPV33 | E1 | KCSAGENTR | 632 | 9 | | 35967 |
| HPV33 | E1 | KDCGIMCR | 396 | 8 | | 35968 |
| HPV33 | E1 | KDCGIMCRH | 396 | 9 | | 35969 |
| HPV33 | E1 | KDCGIMCRHY | 396 | 10 | | 35970 |
| HPV33 | E1 | KDCGIMCRHYK | 396 | 11 | | 35971 |
| HPV33 | E1 | KFAACSQSA | 88 | 9 | | 35972 |
| HPV33 | E1 | KFAACSQSAA | 88 | 10 | | 35973 |
| HPV33 | E1 | KFKEAYGISF | 203 | 10 | | 35974 |
| HPV33 | E1 | KFLKGIPK | 455 | 8 | | 35975 |
| HPV33 | E1 | KFLKGIPKK | 455 | 9 | | 35976 |
| HPV33 | E1 | KGCVISCVNSK | 488 | 11 | | 35977 |
| HPV33 | E1 | KIDELEDSGY | 124 | 10 | | 35978 |
| HPV33 | E1 | KIVKDCGIMCR | 393 | 11 | | 35979 |
| HPV33 | E1 | KLDLIEEEDK | 612 | 10 | | 35980 |
| HPV33 | E1 | KLRSQTCA | 304 | 8 | | 35981 |
| HPV33 | E1 | KLRSQTCALY | 304 | 10 | | 35982 |
| HPV33 | E1 | KMSIGQWIQSR | 412 | 11 | | 35983 |
| HPV33 | E1 | KSCMLICGPA | 463 | 10 | | 35984 |
| HPV33 | E1 | KDFFSRTWCK | 603 | 10 | | 35985 |
| HPV33 | E1 | KSNSQAKIVK | 387 | 10 | | 35986 |
| HPV33 | E1 | KSYFGMSLIQF | 476 | 11 | | 35987 |
| HPV33 | E1 | KTNDGGNWR | 425 | 9 | | 35988 |
| HPV33 | E1 | KVLIKQHSLY | 245 | 10 | | 35989 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E1 | LADSNSNA | 375 | 8 | | 35990 |
| HPV33 | E1 | LADSNSNAA | 375 | 9 | | 35991 |
| HPV33 | E1 | LADSNSNAAA | 375 | 10 | | 35992 |
| HPV33 | E1 | LADSNSNAAAF | 375 | 11 | | 35993 |
| HPV33 | E1 | LDGNEISIDVK | 533 | 11 | | 35994 |
| HPV33 | E1 | LDLIEEEDK | 613 | 9 | | 35995 |
| HPV33 | E1 | LGAFKKFLK | 450 | 9 | | 35996 |
| HPV33 | E1 | LICGPANTGK | 467 | 10 | | 35997 |
| HPV33 | E1 | LIEEEDKENH | 615 | 10 | | 35998 |
| HPV33 | E1 | LIKQHSLY | 247 | 8 | | 35999 |
| HPV33 | E1 | LIKQHSLYTH | 247 | 10 | | 36000 |
| HPV33 | E1 | LIRFRCSK | 271 | 8 | | 36001 |
| HPV33 | E1 | LIRFRCSKNR | 271 | 10 | | 36002 |
| HPV33 | E1 | LLIRFRCSK | 270 | 9 | | 36003 |
| HPV33 | E1 | LLIRFRCSKNR | 270 | 11 | | 36004 |
| HPV33 | E1 | LLLIRFRCSK | 269 | 10 | | 36005 |
| HPV33 | E1 | LLLTSNTNA | 555 | 9 | | 36006 |
| HPV33 | E1 | LLRYQNIEF | 438 | 9 | | 36007 |
| HPV33 | E1 | LLRYQNIEFTA | 438 | 11 | | 36008 |
| HPV33 | E1 | LLTSNTNA | 556 | 8 | | 36009 |
| HPV33 | E1 | LSEMVQWA | 350 | 8 | | 36010 |
| HPV33 | E1 | LSEMVQWAY | 350 | 9 | | 36011 |
| HPV33 | E1 | LTDDSDIA | 362 | 8 | | 36012 |
| HPV33 | E1 | LTDDSDIAY | 362 | 9 | | 36013 |
| HPV33 | E1 | LTDDSDIAYY | 362 | 10 | | 36014 |
| HPV33 | E1 | LTDDSDIAYYY | 362 | 11 | | 36015 |
| HPV33 | E1 | LTVFEFKNPF | 576 | 10 | | 36016 |
| HPV33 | E1 | LTVLQHSF | 336 | 8 | | 36017 |
| HPV33 | E1 | LVRPFKSDK | 215 | 9 | | 36018 |
| HPV33 | E1 | MADPEGTNGA | 1 | 10 | | 36019 |
| HPV33 | E1 | MCRHYKKA | 401 | 8 | | 36020 |
| HPV33 | E1 | MCRHYKKAEK | 401 | 10 | | 36021 |
| HPV33 | E1 | MCRHYKKAEKR | 401 | 11 | | 36022 |
| HPV33 | E1 | MGCTGWFEVEA | 12 | 11 | | 36023 |
| HPV33 | E1 | MLICGPANTGK | 466 | 11 | | 36024 |
| HPV33 | E1 | MSIGQWIQSR | 413 | 10 | | 36025 |
| HPV33 | E1 | MSLIQFLK | 481 | 8 | | 36026 |
| HPV33 | E1 | MVIEPPKLR | 298 | 9 | | 36027 |
| HPV33 | E1 | NAGTDSRWPY | 562 | 10 | | 36028 |
| HPV33 | E1 | NAVCALKR | 80 | 8 | | 36029 |
| HPV33 | E1 | NAVCALKRK | 80 | 9 | | 36030 |
| HPV33 | E1 | NAVCALKRKF | 80 | 10 | | 36031 |
| HPV33 | E1 | NAVCALKRKFA | 80 | 11 | | 36032 |
| HPV33 | E1 | NDENWKSF | 598 | 8 | | 36033 |
| HPV33 | E1 | NDENWKSFF | 598 | 9 | | 36034 |
| HPV33 | E1 | NDENWKSFFSR | 598 | 11 | | 36035 |
| HPV33 | E1 | NGAGMGCTGWF | 8 | 11 | | 36036 |
| HPV33 | E1 | NIEFTAFLGA | 443 | 10 | | 36037 |
| HPV33 | E1 | NIEFTAFLGAF | 443 | 11 | | 36038 |
| HPV33 | E1 | NILYKFKEA | 199 | 9 | | 36039 |
| HPV33 | E1 | NILYKFKEAY | 199 | 10 | | 36040 |
| HPV33 | E1 | NIQEGEDDLNA | 71 | 11 | | 36041 |
| HPV33 | E1 | NISEDEDETA | 31 | 10 | | 36042 |
| HPV33 | E1 | NISTFKCSA | 627 | 9 | | 36043 |
| HPV33 | E1 | NSIQADTEA | 57 | 9 | | 36044 |
| HPV33 | E1 | NSIQADTEAA | 57 | 10 | | 36045 |
| HPV33 | E1 | NSIQADTEAAR | 57 | 11 | | 36046 |
| HPV33 | E1 | NSNAAAFLK | 379 | 9 | 0.0057 | 36047 |
| HPV33 | E1 | NSQAKIVK | 389 | 8 | | 36048 |
| HPV33 | E1 | NTKANILY | 195 | 8 | | 36049 |
| HPV33 | E1 | NTKANILYK | 195 | 9 | | 36050 |
| HPV33 | E1 | NTKANILYKF | 195 | 10 | | 36051 |
| HPV33 | E1 | NTKANILYKFK | 195 | 11 | | 36052 |
| HPV33 | E1 | NTNAGTDSR | 560 | 9 | | 36053 |
| HPV33 | E1 | NVLHSSNTK | 189 | 9 | | 36054 |
| HPV33 | E1 | NVLHSSNTKA | 189 | 10 | | 36055 |
| HPV33 | E1 | PANTGKSY | 471 | 8 | | 36056 |
| HPV33 | E1 | PANTGKSYF | 471 | 9 | | 36057 |
| HPV33 | E1 | PCRTSINK | 107 | 8 | | 36058 |
| HPV33 | E1 | PCRTSINKNK | 107 | 10 | | 36059 |
| HPV33 | E1 | PFDENGNPVY | 586 | 10 | | 36060 |
| HPV33 | E1 | PFDENGNPVYA | 586 | 11 | | 36061 |
| HPV33 | E1 | PISWTYIDDY | 519 | 10 | | 36062 |
| HPV33 | E1 | PIVQLLRY | 434 | 8 | | 36063 |
| HPV33 | E1 | PLLLTSNTNA | 554 | 10 | | 36064 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E1 | PSVAESLK | 238 | 8 | | 36065 |
| HPV33 | E1 | PVYAINDENWK | 593 | 11 | | 36066 |
| HPV33 | E1 | QADTEAAR | 60 | 8 | | 36067 |
| HPV33 | E1 | QADTEAARA | 60 | 9 | | 36068 |
| HPV33 | E1 | QADTEAARALF | 60 | 11 | | 36069 |
| HPV33 | E1 | QGTTPEWIDR | 326 | 10 | | 36070 |
| HPV33 | E1 | QLADSNSNA | 374 | 9 | | 36071 |
| HPV33 | E1 | QLADSNSNAA | 374 | 10 | | 36072 |
| HPV33 | E1 | QLADSNSNAAA | 374 | 11 | | 36073 |
| HPV33 | E1 | QLLRYQNIEF | 437 | 10 | | 36074 |
| HPV33 | E1 | QSAAEDVVDR | 94 | 10 | | 36075 |
| HPV33 | E1 | QSAAEDVVDRA | 94 | 11 | | 36076 |
| HPV33 | E1 | QTCALYWF | 308 | 8 | | 36077 |
| HPV33 | E1 | QTCALYWFR | 308 | 9 | | 36078 |
| HPV33 | E1 | QTCALYWFRTA | 308 | 11 | | 36079 |
| HPV33 | E1 | RCSKNRLTVA | 275 | 10 | | 36080 |
| HPV33 | E1 | RCSKNRLTVAK | 275 | 11 | | 36081 |
| HPV33 | E1 | RFRCSKNR | 273 | 8 | | 36082 |
| HPV33 | E1 | RGIIILLLIR | 264 | 10 | | 36083 |
| HPV33 | E1 | RGIIILLLIRF | 264 | 11 | | 36084 |
| HPV33 | E1 | RLTVFEFK | 575 | 8 | | 36085 |
| HPV33 | E1 | RLTVFEFKNPF | 575 | 11 | | 36086 |
| HPV33 | E1 | RLTVLQHSF | 335 | 9 | | 36087 |
| HPV33 | E1 | RSQTCALY | 306 | 8 | | 36088 |
| HPV33 | E1 | RSQTCALYWF | 306 | 10 | | 36089 |
| HPV33 | E1 | RSQTCALYWFR | 306 | 11 | | 36090 |
| HPV33 | E1 | RTSINKNK | 109 | 8 | | 36091 |
| HPV33 | E1 | SAAEDVVDR | 95 | 9 | | 36092 |
| HPV33 | E1 | SAAEDVVDRA | 95 | 10 | | 36093 |
| HPV33 | E1 | SAAEDVVDRAA | 95 | 11 | | 36094 |
| HPV33 | E1 | SAGENTRSLR | 634 | 10 | | 36095 |
| HPV33 | E1 | SCMLICGPA | 464 | 9 | | 36096 |
| HPV33 | E1 | SCTDWCITGY | 225 | 10 | | 36097 |
| HPV33 | E1 | SCVNSKSH | 493 | 8 | | 36098 |
| HPV33 | E1 | SCVNSKSHF | 493 | 9 | | 36099 |
| HPV33 | E1 | SDIAYYYA | 366 | 8 | | 36100 |
| HPV33 | E1 | SDIAYYYAQLA | 366 | 11 | | 36101 |
| HPV33 | E1 | SFFSRTWCK | 604 | 9 | | 36102 |
| HPV33 | E1 | SFMELVRPF | 211 | 9 | | 36103 |
| HPV33 | E1 | SFMELVRPFK | 211 | 10 | | 36104 |
| HPV33 | E1 | SGTDLLEF | 43 | 8 | | 36105 |
| HPV33 | E1 | SIDVKHRA | 539 | 8 | | 36106 |
| HPV33 | E1 | SIGQWIQSR | 414 | 9 | | 36107 |
| HPV33 | E1 | SINKNKECTY | 111 | 10 | | 36108 |
| HPV33 | E1 | SINKNKECTYR | 111 | 11 | | 36109 |
| HPV33 | E1 | SIQADTEA | 58 | 8 | | 36110 |
| HPV33 | E1 | SIQADTEAA | 58 | 9 | | 36111 |
| HPV33 | E1 | SIQADTEAAR | 58 | 10 | | 36112 |
| HPV33 | E1 | SIQADTEAARA | 58 | 11 | | 36113 |
| HPV33 | E1 | SLKVLIKQH | 243 | 9 | | 36114 |
| HPV33 | E1 | SMENSIQA | 54 | 8 | | 36115 |
| HPV33 | E1 | SSNTKANILY | 193 | 10 | | 36116 |
| HPV33 | E1 | SSNTKANILYK | 193 | 11 | | 36117 |
| HPV33 | E1 | SVAESLKVLIK | 239 | 11 | | 36118 |
| HPV33 | E1 | TAFLGAFK | 447 | 8 | | 36119 |
| HPV33 | E1 | TAFLGAFKK | 447 | 9 | | 36120 |
| HPV33 | E1 | TAFLGAFKKF | 447 | 10 | | 36121 |
| HPV33 | E1 | TCALYWFR | 309 | 8 | | 36122 |
| HPV33 | E1 | TCALYWFRTA | 309 | 10 | | 36123 |
| HPV33 | E1 | TCMVIEPPK | 296 | 9 | | 36124 |
| HPV33 | E1 | TCMVIEPPKLR | 296 | 11 | | 36125 |
| HPV33 | E1 | TDDSDIAY | 363 | 8 | | 36126 |
| HPV33 | E1 | TDDSDIAYY | 363 | 9 | | 36127 |
| HPV33 | E1 | TDDSDIAYYY | 363 | 10 | | 36128 |
| HPV33 | E1 | TDDSDIAYYYA | 363 | 11 | | 36129 |
| HPV33 | E1 | TDSRWPYLH | 565 | 9 | | 36130 |
| HPV33 | E1 | TDSRWPYLHSR | 565 | 11 | | 36131 |
| HPV33 | E1 | TDWCITGY | 227 | 8 | | 36132 |
| HPV33 | E1 | TFKCSAGENTR | 630 | 11 | | 36133 |
| HPV33 | E1 | TGWFEVEA | 15 | 8 | | 36134 |
| HPV33 | E1 | TGYGISPSVA | 232 | 10 | | 36135 |
| HPV33 | E1 | TLQEISNVLH | 183 | 10 | | 36136 |
| HPV33 | E1 | TSCTDWCITGY | 224 | 11 | | 36137 |
| HPV33 | E1 | TSINKNKECTY | 110 | 11 | | 36138 |
| HPV33 | E1 | TSNTNAGTDSR | 558 | 11 | | 36139 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E1 | TTPEWIDR | 328 | 8 | | 36140 |
| HPV33 | E1 | TVFEFKNPF | 577 | 9 | | 36141 |
| HPV33 | E1 | TVFEFKNPFPF | 577 | 11 | | 36142 |
| HPV33 | E1 | VAESLKVLIK | 240 | 10 | | 36143 |
| HPV33 | E1 | VCALKRKF | 82 | 8 | | 36144 |
| HPV33 | E1 | VCALKRKFA | 82 | 9 | | 36145 |
| HPV33 | E1 | VCALKRKFAA | 82 | 10 | | 36146 |
| HPV33 | E1 | VDRAANPCR | 101 | 9 | | 36147 |
| HPV33 | E1 | VFEFKNPF | 578 | 8 | | 36148 |
| HPV33 | E1 | VFEFKNPFPF | 578 | 10 | | 36149 |
| HPV33 | E1 | VIEPPKLR | 299 | 8 | | 36150 |
| HPV33 | E1 | VISCVNSK | 491 | 8 | | 36151 |
| HPV33 | E1 | VISCVNSKSH | 491 | 10 | | 36152 |
| HPV33 | E1 | VISCVNSKSHF | 491 | 11 | | 36153 |
| HPV33 | E1 | VLHSSNTK | 190 | 8 | | 36154 |
| HPV33 | E1 | VLHSSNTKA | 190 | 9 | | 36155 |
| HPV33 | E1 | VLIKQHSLY | 246 | 9 | | 36156 |
| HPV33 | E1 | VLIKQHSLYTH | 246 | 11 | | 36157 |
| HPV33 | E1 | VLQHSFNDNIF | 338 | 11 | | 36158 |
| HPV33 | E1 | VTLQEISNVLH | 182 | 11 | | 36159 |
| HPV33 | E1 | VTPISWTY | 517 | 8 | | 36160 |
| HPV33 | E1 | VVDRAANPCR | 100 | 10 | | 36161 |
| HPV33 | E1 | WFEVEAVIER | 17 | 10 | | 36162 |
| HPV33 | E1 | WFEVEAVIERR | 17 | 11 | | 36163 |
| HPV33 | E1 | WIDRLTVLQH | 332 | 10 | | 36164 |
| HPV33 | E1 | WIQSRCEK | 418 | 8 | | 36165 |
| HPV33 | E1 | WLQPLSDA | 502 | 8 | | 36166 |
| HPV33 | E1 | WLQPLSDAK | 502 | 9 | | 36167 |
| HPV33 | E1 | WTYIDDYMR | 522 | 9 | | 36168 |
| HPV33 | E1 | WTYIDDYMRNA | 522 | 11 | | 36169 |
| HPV33 | E1 | YAINDENWK | 595 | 9 | | 36170 |
| HPV33 | E1 | YAINDENWKSF | 595 | 11 | | 36171 |
| HPV33 | E1 | YAQLADSNSNA | 372 | 11 | | 36172 |
| HPV33 | E1 | YFGMSLIQF | 478 | 9 | | 36173 |
| HPV33 | E1 | YFGMSLIQFLK | 478 | 11 | | 36174 |
| HPV33 | E1 | YGISFMELVR | 208 | 10 | | 36175 |
| HPV33 | E1 | YGISPSVA | 234 | 8 | | 36176 |
| HPV33 | E1 | YIDDYMRNA | 524 | 9 | | 36177 |
| HPV33 | E1 | YLHSRLTVF | 571 | 9 | | 36178 |
| HPV33 | E1 | YLHSRLTVFEF | 571 | 11 | | 36179 |
| HPV33 | E1 | YTHLQCLTCDR | 254 | 11 | | 36180 |
| HPV33 | E2 | AAAKRRRPA | 223 | 9 | | 36181 |
| HPV33 | E2 | AAKRRRPA | 224 | 8 | | 36182 |
| HPV33 | E2 | ADIQTDNDNR | 210 | 10 | | 36183 |
| HPV33 | E2 | ADPALDNR | 246 | 8 | | 36184 |
| HPV33 | E2 | ADPALDNRTA | 246 | 10 | | 36185 |
| HPV33 | E2 | ADPALDNRTAR | 246 | 11 | | 36186 |
| HPV33 | E2 | AFQVIELQMA | 69 | 10 | | 36187 |
| HPV33 | E2 | ALDNRTAR | 249 | 8 | | 36188 |
| HPV33 | E2 | ALDNRTARTA | 249 | 10 | | 36189 |
| HPV33 | E2 | ALETLSKSQY | 78 | 10 | | 36190 |
| HPV33 | E2 | ALLYTAKQMGF | 41 | 11 | | 36191 |
| HPV33 | E2 | ATNCTNKQR | 258 | 9 | | 36192 |
| HPV33 | E2 | AVQEKILDLY | 10 | 10 | | 36193 |
| HPV33 | E2 | CADPALDNR | 245 | 9 | | 36194 |
| HPV33 | E2 | CADPALDNRTA | 245 | 11 | | 36195 |
| HPV33 | E2 | CALLYTAK | 40 | 8 | | 36196 |
| HPV33 | E2 | CLRYRLKPY | 288 | 9 | | 36197 |
| HPV33 | E2 | CLRYRLKPYK | 288 | 10 | | 36198 |
| HPV33 | E2 | CSSNVAPIVH | 269 | 10 | | 36199 |
| HPV33 | E2 | CTMVTGKVDY | 145 | 10 | | 36200 |
| HPV33 | E2 | DIQTDNDNR | 211 | 9 | | 36201 |
| HPV33 | E2 | DLPSQIEH | 25 | 8 | | 36202 |
| HPV33 | E2 | DLPSQIEHWK | 25 | 10 | | 36203 |
| HPV33 | E2 | DTAQPLTK | 235 | 8 | | 36204 |
| HPV33 | E2 | DTAQPLTKLF | 235 | 10 | | 36205 |
| HPV33 | E2 | DTCTMVTGK | 143 | 9 | | 36206 |
| HPV33 | E2 | DTTDTAQPLTK | 232 | 11 | | 36207 |
| HPV33 | E2 | ECALLYTA | 39 | 8 | | 36208 |
| HPV33 | E2 | ECALLYTAK | 39 | 9 | | 36209 |
| HPV33 | E2 | EDAAKYSK | 173 | 8 | | 36210 |
| HPV33 | E2 | EDTCTMVTGK | 142 | 10 | | 36211 |
| HPV33 | E2 | EISARLNA | 3 | 8 | | 36212 |
| HPV33 | E2 | ELQMALETLSK | 74 | 11 | | 36213 |
| HPV33 | E2 | ELYSSMSSTWH | 298 | 11 | | 36214 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E2 | ESNSLKCLR | 282 | 9 | | 36215 |
| HPV33 | E2 | ESNSLKCLRY | 282 | 10 | | 36216 |
| HPV33 | E2 | ESNSLKCLRYR | 282 | 11 | | 36217 |
| HPV33 | E2 | ETLSKSQY | 80 | 8 | | 36218 |
| HPV33 | E2 | ETVTVQYDNDK | 115 | 11 | | 36219 |
| HPV33 | E2 | EVWLCEPPK | 100 | 9 | | 36220 |
| HPV33 | E2 | EVWLCEPPKCF | 100 | 11 | | 36221 |
| HPV33 | E2 | FCADPALDNR | 244 | 10 | | 36222 |
| HPV33 | E2 | FVTEQQQQMF | 325 | 10 | | 36223 |
| HPV33 | E2 | GMYYIHNCEK | 156 | 10 | | 36224 |
| HPV33 | E2 | HLKGESNSLK | 278 | 10 | | 36225 |
| HPV33 | E2 | IGMYYIHNCEK | 155 | 11 | | 36226 |
| HPV33 | E2 | ILDLYEADK | 15 | 9 | | 36227 |
| HPV33 | E2 | ISARLNAVQEK | 4 | 11 | | 36228 |
| HPV33 | E2 | KAFQVIELQMA | 68 | 11 | | 36229 |
| HPV33 | E2 | KCLRYRLK | 287 | 8 | | 36230 |
| HPV33 | E2 | KCLRYRLKPY | 287 | 10 | | 36231 |
| HPV33 | E2 | KCLRYRLKPYK | 287 | 11 | | 36232 |
| HPV33 | E2 | KGESNSLK | 280 | 8 | | 36233 |
| HPV33 | E2 | KGESNSLKCLR | 280 | 11 | | 36234 |
| HPV33 | E2 | KILDLYEA | 14 | 8 | | 36235 |
| HPV33 | E2 | KILDLYEADK | 14 | 10 | | 36236 |
| HPV33 | E2 | KLFCADPA | 242 | 8 | | 36237 |
| HPV33 | E2 | KLIRMECA | 34 | 8 | | 36238 |
| HPV33 | E2 | KLIRMECALLY | 34 | 11 | | 36239 |
| HPV33 | E2 | KTDLPSQIEH | 23 | 10 | | 36240 |
| HPV33 | E2 | KTQMWEVH | 180 | 8 | | 36241 |
| HPV33 | E2 | KVDYIGMY | 151 | 8 | | 36242 |
| HPV33 | E2 | KVDYIGMYY | 151 | 9 | | 36243 |
| HPV33 | E2 | KVDYIGMYYIH | 151 | 11 | | 36244 |
| HPV33 | E2 | KVYFKYFK | 165 | 8 | | 36245 |
| HPV33 | E2 | KVYFKYFKEDA | 165 | 11 | | 36246 |
| HPV33 | E2 | LASKTKAF | 63 | 8 | | 36247 |
| HPV33 | E2 | LCEPPKCF | 103 | 8 | | 36248 |
| HPV33 | E2 | LCEPPKCFK | 103 | 9 | | 36249 |
| HPV33 | E2 | LCEPPKCFKK | 103 | 10 | | 36250 |
| HPV33 | E2 | LCHQVVPSLLA | 54 | 11 | | 36251 |
| HPV33 | E2 | LDLYEADK | 16 | 8 | | 36252 |
| HPV33 | E2 | LDNRTARTA | 250 | 9 | | 36253 |
| HPV33 | E2 | LFCADPALDNR | 243 | 11 | | 36254 |
| HPV33 | E2 | LIRMECALLY | 35 | 10 | | 36255 |
| HPV33 | E2 | LLASKTKA | 62 | 8 | | 36256 |
| HPV33 | E2 | LLASKTKAF | 62 | 9 | | 36257 |
| HPV33 | E2 | LLYTAKQMGF | 42 | 10 | | 36258 |
| HPV33 | E2 | LTKLFCADPA | 240 | 10 | | 36259 |
| HPV33 | E2 | MALETLSK | 77 | 8 | | 36260 |
| HPV33 | E2 | MALETLSKSQY | 77 | 11 | | 36261 |
| HPV33 | E2 | MDYTNWGEIY | 129 | 10 | | 36262 |
| HPV33 | E2 | MGFSHLCH | 49 | 8 | | 36263 |
| HPV33 | E2 | MVTGKVDY | 147 | 8 | | 36264 |
| HPV33 | E2 | NAVQEKILDLY | 9 | 11 | | 36265 |
| HPV33 | E2 | NCEKVYFK | 162 | 8 | | 36266 |
| HPV33 | E2 | NCEKVYFKY | 162 | 9 | | 36267 |
| HPV33 | E2 | NCEKVYFKYF | 162 | 10 | | 36268 |
| HPV33 | E2 | NCEKVYFKYFK | 162 | 11 | | 36269 |
| HPV33 | E2 | NDKKNTMDY | 123 | 9 | | 36270 |
| HPV33 | E2 | NDNRPPQA | 216 | 8 | | 36271 |
| HPV33 | E2 | NDNRPPQAA | 216 | 9 | | 36272 |
| HPV33 | E2 | NDNRPPQAAA | 216 | 10 | | 36273 |
| HPV33 | E2 | NDNRPPQAAAK | 216 | 11 | | 36274 |
| HPV33 | E2 | NGIVTVTF | 318 | 8 | | 36275 |
| HPV33 | E2 | NSKNGIVTVTF | 315 | 11 | | 36276 |
| HPV33 | E2 | NSLKCLRY | 284 | 8 | | 36277 |
| HPV33 | E2 | NSLKCLRYR | 284 | 9 | | 36278 |
| HPV33 | E2 | NSLKCLRYRLK | 284 | 11 | | 36279 |
| HPV33 | E2 | NVAPIVHLK | 272 | 9 | | 36280 |
| HPV33 | E2 | PADTTDTA | 230 | 8 | | 36281 |
| HPV33 | E2 | PALDNRTA | 248 | 8 | | 36282 |
| HPV33 | E2 | PALDNRTAR | 248 | 9 | | 36283 |
| HPV33 | E2 | PALDNRTARTA | 248 | 11 | | 36284 |
| HPV33 | E2 | PLTKLFCA | 239 | 8 | | 36285 |
| HPV33 | E2 | PLTKLFCADPA | 239 | 11 | | 36286 |
| HPV33 | E2 | PSLLASKTK | 60 | 9 | | 36287 |
| HPV33 | E2 | PSLLASKTKA | 60 | 10 | | 36288 |
| HPV33 | E2 | PSLLASKTKAF | 60 | 11 | | 36289 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E2 | PSQIEHWK | 27 | 8 | | 36290 |
| HPV33 | E2 | PSQIEHWKLIR | 27 | 11 | | 36291 |
| HPV33 | E2 | PTVQISTGF | 342 | 9 | | 36292 |
| HPV33 | E2 | QAAAKRRR | 222 | 8 | | 36293 |
| HPV33 | E2 | QAAAKRRRPA | 222 | 10 | | 36294 |
| HPV33 | E2 | QGETVTVQY | 113 | 9 | | 36295 |
| HPV33 | E2 | QIEHWKLIR | 29 | 9 | | 36296 |
| HPV33 | E2 | QISTTETA | 203 | 8 | | 36297 |
| HPV33 | E2 | QMALETLSK | 76 | 9 | | 36298 |
| HPV33 | E2 | QMFLGTVK | 332 | 8 | | 36299 |
| HPV33 | E2 | QMGFSHLCH | 48 | 9 | | 36300 |
| HPV33 | E2 | QTDNDNRPPQA | 213 | 11 | | 36301 |
| HPV33 | E2 | QVIELQMA | 71 | 8 | | 36302 |
| HPV33 | E2 | QVVPSLLA | 57 | 8 | | 36303 |
| HPV33 | E2 | QVVPSLLASK | 57 | 10 | | 36304 |
| HPV33 | E2 | RLKPYKELY | 292 | 9 | | 36305 |
| HPV33 | E2 | RLNAVQEK | 7 | 8 | | 36306 |
| HPV33 | E2 | RMECALLY | 37 | 8 | | 36307 |
| HPV33 | E2 | RMECALLYTA | 37 | 10 | | 36308 |
| HPV33 | E2 | RMECALLYTAK | 37 | 11 | | 36309 |
| HPV33 | E2 | RTATNCTNK | 256 | 9 | | 36310 |
| HPV33 | E2 | RTATNCTNKQR | 256 | 11 | | 36311 |
| HPV33 | E2 | RTVCSSNVA | 266 | 9 | | 36312 |
| HPV33 | E2 | SARLNAVQEK | 5 | 10 | | 36313 |
| HPV33 | E2 | SLEVWLCEPPK | 98 | 11 | | 36314 |
| HPV33 | E2 | SLKCLRYR | 285 | 8 | | 36315 |
| HPV33 | E2 | SLKCLRYRLK | 285 | 10 | | 36316 |
| HPV33 | E2 | SLLASKTK | 61 | 8 | | 36317 |
| HPV33 | E2 | SLLASKTKA | 61 | 9 | | 36318 |
| HPV33 | E2 | SLLASKTKAF | 61 | 10 | | 36319 |
| HPV33 | E2 | SSMSSTWH | 301 | 8 | | 36320 |
| HPV33 | E2 | SSNQISTTETA | 200 | 11 | | 36321 |
| HPV33 | E2 | SSNVAPIVH | 270 | 9 | | 36322 |
| HPV33 | E2 | SSNVAPIVHLK | 270 | 11 | | 36323 |
| HPV33 | E2 | SSTWHWTSDNK | 304 | 11 | | 36324 |
| HPV33 | E2 | STWHWTSDNK | 305 | 10 | | 36325 |
| HPV33 | E2 | TADIQTDNDNR | 209 | 11 | | 36326 |
| HPV33 | E2 | TAKQMGFSH | 45 | 9 | | 36327 |
| HPV33 | E2 | TAQPLTKLF | 236 | 9 | | 36328 |
| HPV33 | E2 | TAQPLTKLFCA | 236 | 11 | | 36329 |
| HPV33 | E2 | TARTATNCTNK | 254 | 11 | | 36330 |
| HPV33 | E2 | TATNCTNK | 257 | 8 | | 36331 |
| HPV33 | E2 | TATNCTNKQR | 257 | 10 | | 36332 |
| HPV33 | E2 | TCTMVTGK | 144 | 8 | | 36333 |
| HPV33 | E2 | TCTMVTGKVDY | 144 | 11 | | 36334 |
| HPV33 | E2 | TDLPSQIEH | 24 | 9 | | 36335 |
| HPV33 | E2 | TDLPSQIEHWK | 24 | 11 | | 36336 |
| HPV33 | E2 | TDNDNRPPQA | 214 | 10 | | 36337 |
| HPV33 | E2 | TDNDNRPPQAA | 214 | 11 | | 36338 |
| HPV33 | E2 | TDTAQPLTK | 234 | 9 | | 36339 |
| HPV33 | E2 | TDTAQPLTKLF | 234 | 11 | | 36340 |
| HPV33 | E2 | TFVTEQQQQMF | 324 | 11 | | 36341 |
| HPV33 | E2 | TGKVDYIGMY | 149 | 10 | | 36342 |
| HPV33 | E2 | TGKVDYIGMYY | 149 | 11 | | 36343 |
| HPV33 | E2 | TMDYTNWGEIY | 128 | 11 | | 36344 |
| HPV33 | E2 | TMVTGKVDY | 146 | 9 | | 36345 |
| HPV33 | E2 | TSDNKNSK | 310 | 8 | | 36346 |
| HPV33 | E2 | TTDTAQPLTK | 233 | 10 | | 36347 |
| HPV33 | E2 | TVCSSNVA | 267 | 8 | | 36348 |
| HPV33 | E2 | TVQISTGF | 343 | 8 | | 36349 |
| HPV33 | E2 | TVQYDNDK | 118 | 8 | | 36350 |
| HPV33 | E2 | TVQYDNDKK | 118 | 9 | | 36351 |
| HPV33 | E2 | TVTVQYDNDK | 116 | 10 | | 36352 |
| HPV33 | E2 | TVTVQYDNDKK | 116 | 11 | | 36353 |
| HPV33 | E2 | VAPIVHLK | 273 | 8 | | 36354 |
| HPV33 | E2 | VCSSNVAPIVH | 268 | 11 | | 36355 |
| HPV33 | E2 | VDYIGMYY | 152 | 8 | | 36356 |
| HPV33 | E2 | VDYIGMYYIH | 152 | 10 | | 36357 |
| HPV33 | E2 | VTEQQQQMF | 326 | 9 | | 36358 |
| HPV33 | E2 | VTGKVDYIGMY | 148 | 11 | | 36359 |
| HPV33 | E2 | VTVQYDNDK | 117 | 9 | | 36360 |
| HPV33 | E2 | VTVQYDNDKK | 117 | 10 | | 36361 |
| HPV33 | E2 | VVPSLLASK | 58 | 9 | | 36362 |
| HPV33 | E2 | VVPSLLASKTK | 58 | 11 | | 36363 |
| HPV33 | E2 | WLCEPPKCF | 102 | 9 | | 36364 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E2 | WLCEPPKCFK | 102 | 10 | | 36365 |
| HPV33 | E2 | WLCEPPKCFKK | 102 | 11 | | 36366 |
| HPV33 | E2 | WTSDNKNSK | 309 | 9 | | 36367 |
| HPV33 | E2 | YDNDKKNTMDY | 121 | 11 | | 36368 |
| HPV33 | E2 | YFKEDAAK | 170 | 8 | | 36369 |
| HPV33 | E2 | YFKEDAAKY | 170 | 9 | | 36370 |
| HPV33 | E2 | YFKEDAAKYSK | 170 | 11 | | 36371 |
| HPV33 | E2 | YFKYFKEDA | 167 | 9 | | 36372 |
| HPV33 | E2 | YFKYFKEDAA | 167 | 10 | | 36373 |
| HPV33 | E2 | YFKYFKEDAAK | 167 | 11 | | 36374 |
| HPV33 | E2 | YIGMYYIH | 154 | 8 | | 36375 |
| HPV33 | E2 | YIHNCEKVY | 159 | 9 | | 36376 |
| HPV33 | E2 | YIHNCEKVYF | 159 | 10 | | 36377 |
| HPV33 | E2 | YIHNCEKVYFK | 159 | 11 | | 36378 |
| HPV33 | E2 | YSKTQMWEVH | 178 | 10 | | 36379 |
| HPV33 | E2 | YSSMSSTWH | 300 | 9 | | 36380 |
| HPV33 | E2 | YTAKQMGF | 44 | 8 | | 36381 |
| HPV33 | E2 | YTAKQMGFSH | 44 | 10 | | 36382 |
| HPV33 | E2 | YTNWGEIY | 131 | 8 | | 36383 |
| HPV33 | E5 | CINFHAQH | 63 | 8 | | 36384 |
| HPV33 | E5 | FCYLLFLY | 51 | 8 | | 36385 |
| HPV33 | E5 | FFCYLLFLY | 50 | 9 | | 36386 |
| HPV33 | E5 | FLCLSLLLR | 12 | 9 | | 36387 |
| HPV33 | E5 | FLYLPMMCINF | 56 | 11 | | 36388 |
| HPV33 | E5 | FVFVLCFILF | 3 | 10 | | 36389 |
| HPV33 | E5 | FVGSPLKIF | 42 | 9 | | 36390 |
| HPV33 | E5 | FVGSPLKIFF | 42 | 10 | | 36391 |
| HPV33 | E5 | FVLCFILF | 5 | 8 | | 36392 |
| HPV33 | E5 | GSPLKIFF | 44 | 8 | | 36393 |
| HPV33 | E5 | GSPLKIFFCY | 44 | 10 | | 36394 |
| HPV33 | E5 | IFFCYLLF | 49 | 8 | | 36395 |
| HPV33 | E5 | IFFCYLLFLY | 49 | 10 | | 36396 |
| HPV33 | E5 | IFVFVLCF | 2 | 8 | | 36397 |
| HPV33 | E5 | IFVFVLCFILF | 2 | 11 | | 36398 |
| HPV33 | E5 | ILFLCLSLLLR | 10 | 11 | | 36399 |
| HPV33 | E5 | ILSISTYA | 23 | 8 | | 36400 |
| HPV33 | E5 | KIFFCYLLF | 48 | 9 | | 36401 |
| HPV33 | E5 | KIFFCYLLFLY | 48 | 11 | | 36402 |
| HPV33 | E5 | LCLSLLLR | 13 | 8 | | 36403 |
| HPV33 | E5 | LFLCLSLLLR | 11 | 10 | | 36404 |
| HPV33 | E5 | LILSISTY | 22 | 8 | | 36405 |
| HPV33 | E5 | LILSISTYA | 22 | 9 | | 36406 |
| HPV33 | E5 | LLVLVLLLWVF | 32 | 11 | | 36407 |
| HPV33 | E5 | LLWVFVGSPLK | 38 | 11 | | 36408 |
| HPV33 | E5 | LVLLLWVF | 35 | 8 | | 36409 |
| HPV33 | E5 | LVLVLLLWVF | 33 | 10 | | 36410 |
| HPV33 | E5 | MCINFHAQH | 62 | 9 | | 36411 |
| HPV33 | E5 | MIFVFVLCF | 1 | 9 | | 36412 |
| HPV33 | E5 | MMCINFHA | 61 | 8 | | 36413 |
| HPV33 | E5 | MMCINFHAQH | 61 | 10 | | 36414 |
| HPV33 | E5 | PLILSISTY | 21 | 9 | | 36415 |
| HPV33 | E5 | PLILSISTYA | 21 | 10 | | 36416 |
| HPV33 | E5 | PLKIFFCY | 46 | 8 | | 36417 |
| HPV33 | E5 | PLKIFFCYLLF | 46 | 11 | | 36418 |
| HPV33 | E5 | PMMCINFH | 60 | 8 | | 36419 |
| HPV33 | E5 | PMMCINFHA | 60 | 9 | | 36420 |
| HPV33 | E5 | PMMCINFHAQH | 60 | 11 | | 36421 |
| HPV33 | E5 | VFVGSPLK | 41 | 8 | | 36422 |
| HPV33 | E5 | VFVGSPLKIF | 41 | 10 | | 36423 |
| HPV33 | E5 | VFVGSPLKIFF | 41 | 11 | | 36424 |
| HPV33 | E5 | VFVLCFILF | 4 | 9 | | 36425 |
| HPV33 | E5 | VGSPLKIF | 43 | 8 | | 36426 |
| HPV33 | E5 | VGSPLKIFF | 43 | 9 | | 36427 |
| HPV33 | E5 | VGSPLKIFFCY | 43 | 11 | | 36428 |
| HPV33 | E5 | VLVLLLWVF | 34 | 9 | | 36429 |
| HPV33 | E5 | WVFVGSPLK | 40 | 9 | | 36430 |
| HPV33 | E5 | WVFVGSPLKIF | 40 | 11 | | 36431 |
| HPV33 | E5 | YLPMMCINF | 58 | 9 | | 36432 |
| HPV33 | E5 | YLPMMCINFH | 58 | 10 | | 36433 |
| HPV33 | E5 | YLPMMCINFHA | 58 | 11 | | 36434 |
| HPV33 | E6 | AACWRSRR | 137 | 8 | | 36435 |
| HPV33 | E6 | AACWRSRRR | 137 | 9 | | 36436 |
| HPV33 | E6 | ACWRSRRR | 138 | 8 | | 36437 |
| HPV33 | E6 | ACWRSRRRETA | 138 | 11 | | 36438 |
| HPV33 | E6 | ADLTVVYR | 48 | 8 | | 36439 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E6 | AFADLTVVY | 46 | 9 | | 36440 |
| HPV33 | E6 | AFADLTVVYR | 46 | 10 | | 36441 |
| HPV33 | E6 | AGRCAACWR | 133 | 9 | | 36442 |
| HPV33 | E6 | AGRCAACWRSR | 133 | 11 | | 36443 |
| HPV33 | E6 | CAACWRSR | 136 | 8 | | 36444 |
| HPV33 | E6 | CAACWRSRR | 136 | 9 | | 36445 |
| HPV33 | E6 | CAACWRSRRR | 136 | 10 | | 36446 |
| HPV33 | E6 | CLRFLSKISEY | 66 | 11 | | 36447 |
| HPV33 | E6 | CVECKKPLQR | 30 | 10 | | 36448 |
| HPV33 | E6 | DFAFADLTVVY | 44 | 11 | | 36449 |
| HPV33 | E6 | DLCQALETTIH | 14 | 11 | | 36450 |
| HPV33 | E6 | DTEEKPRTLH | 4 | 10 | | 36451 |
| HPV33 | E6 | ECKKPLQR | 32 | 8 | | 36452 |
| HPV33 | E6 | EGNPFGICK | 56 | 9 | | 36453 |
| HPV33 | E6 | EILIRCIICQR | 98 | 11 | | 36454 |
| HPV33 | E6 | ELQCVECK | 27 | 8 | | 36455 |
| HPV33 | E6 | ELQCVECKK | 27 | 9 | | 36456 |
| HPV33 | E6 | EVYDFAFA | 41 | 8 | | 36457 |
| HPV33 | E6 | FADLTVVY | 47 | 8 | | 36458 |
| HPV33 | E6 | FADLTVVYR | 47 | 9 | | 36459 |
| HPV33 | E6 | FAFADLTVVY | 45 | 10 | | 36460 |
| HPV33 | E6 | FAFADLTVVYR | 45 | 11 | | 36461 |
| HPV33 | E6 | FGICKLCLR | 60 | 9 | | 36462 |
| HPV33 | E6 | FGICKLCLRF | 60 | 10 | | 36463 |
| HPV33 | E6 | FLSKISEY | 69 | 8 | | 36464 |
| HPV33 | E6 | FLSKISEYR | 69 | 9 | | 36465 |
| HPV33 | E6 | FLSKISEYRH | 69 | 10 | | 36466 |
| HPV33 | E6 | FLSKISEYRHY | 69 | 11 | | 36467 |
| HPV33 | E6 | GICKLCLR | 61 | 8 | | 36468 |
| HPV33 | E6 | GICKLCLRF | 61 | 9 | | 36469 |
| HPV33 | E6 | HVDLNKRF | 118 | 8 | | 36470 |
| HPV33 | E6 | HVDLNKRFH | 118 | 9 | | 36471 |
| HPV33 | E6 | ICKLCLRF | 62 | 8 | | 36472 |
| HPV33 | E6 | ICKLCLRFLSK | 62 | 11 | | 36473 |
| HPV33 | E6 | ICQRPLCPQEK | 105 | 11 | | 36474 |
| HPV33 | E6 | ILIRCIICQR | 99 | 10 | | 36475 |
| HPV33 | E6 | ISEYRHYNY | 73 | 9 | | 36476 |
| HPV33 | E6 | ISGRWAGR | 128 | 8 | | 36477 |
| HPV33 | E6 | ISGRWAGRCA | 128 | 10 | | 36478 |
| HPV33 | E6 | ISGRWAGRCAA | 128 | 11 | | 36479 |
| HPV33 | E6 | KISEYRHY | 72 | 8 | | 36480 |
| HPV33 | E6 | KISEYRHYNY | 72 | 10 | | 36481 |
| HPV33 | E6 | KLCLRFLSK | 64 | 9 | | 36482 |
| HPV33 | E6 | LCLRFLSK | 65 | 8 | | 36483 |
| HPV33 | E6 | LCPQEKKR | 110 | 8 | | 36484 |
| HPV33 | E6 | LCPQEKKRH | 110 | 9 | | 36485 |
| HPV33 | E6 | LCQALETTIH | 15 | 10 | | 36486 |
| HPV33 | E6 | LIRCIICQR | 100 | 9 | | 36487 |
| HPV33 | E6 | LSKISEYR | 70 | 8 | | 36488 |
| HPV33 | E6 | LSKISEYRH | 70 | 9 | | 36489 |
| HPV33 | E6 | LSKISEYRHY | 70 | 10 | | 36490 |
| HPV33 | E6 | LTVVYREGNPF | 50 | 11 | | 36491 |
| HPV33 | E6 | MFQDTEEK | 1 | 8 | | 36492 |
| HPV33 | E6 | MFQDTEEKPR | 1 | 10 | | 36493 |
| HPV33 | E6 | NIELQCVECK | 25 | 10 | | 36494 |
| HPV33 | E6 | NIELQCVECKK | 25 | 11 | | 36495 |
| HPV33 | E6 | NISGRWAGR | 127 | 9 | | 36496 |
| HPV33 | E6 | NISGRWAGRCA | 127 | 11 | | 36497 |
| HPV33 | E6 | NTLEQTVK | 86 | 8 | | 36498 |
| HPV33 | E6 | NTLEQTVKK | 86 | 9 | | 36499 |
| HPV33 | E6 | PFGICKLCLR | 59 | 10 | | 36500 |
| HPV33 | E6 | PFGICKLCLRF | 59 | 11 | | 36501 |
| HPV33 | E6 | PLCPQEKK | 109 | 8 | | 36502 |
| HPV33 | E6 | PLCPQEKKR | 109 | 9 | | 36503 |
| HPV33 | E6 | PLCPQEKKRH | 109 | 10 | | 36504 |
| HPV33 | E6 | PLNEILIR | 95 | 8 | | 36505 |
| HPV33 | E6 | PLQRSEVY | 36 | 8 | | 36506 |
| HPV33 | E6 | PLQRSEVYDF | 36 | 10 | | 36507 |
| HPV33 | E6 | PLQRSEVYDFA | 36 | 11 | | 36508 |
| HPV33 | E6 | QALETTIH | 17 | 8 | | 36509 |
| HPV33 | E6 | QCVECKKPLQR | 29 | 11 | | 36510 |
| HPV33 | E6 | QDTEEKPR | 3 | 8 | | 36511 |
| HPV33 | E6 | QDTEEKPRTLH | 3 | 11 | | 36512 |
| HPV33 | E6 | RCAACWRSR | 135 | 9 | | 36513 |
| HPV33 | E6 | RCAACWRSRR | 135 | 10 | | 36514 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | E6 | RCAACWRSRRR | 135 | 11 | | 36515 |
| HPV33 | E6 | RFHNISGR | 124 | 8 | | 36516 |
| HPV33 | E6 | RFHNISGRWA | 124 | 10 | | 36517 |
| HPV33 | E6 | RFLSKISEY | 68 | 9 | | 36518 |
| HPV33 | E6 | RFLSKISEYR | 68 | 10 | | 36519 |
| HPV33 | E6 | RFLSKISEYRH | 68 | 11 | | 36520 |
| HPV33 | E6 | RSEVYDFA | 39 | 8 | | 36521 |
| HPV33 | E6 | RSEVYDFAF | 39 | 9 | | 36522 |
| HPV33 | E6 | RSEVYDFAFA | 39 | 10 | | 36523 |
| HPV33 | E6 | RSRRRETA | 141 | 8 | | 36524 |
| HPV33 | E6 | RTLHDLCQA | 10 | 9 | | 36525 |
| HPV33 | E6 | SGRWAGRCA | 129 | 9 | | 36526 |
| HPV33 | E6 | SGRWAGRCAA | 129 | 10 | | 36527 |
| HPV33 | E6 | TLEQTVKK | 87 | 8 | | 36528 |
| HPV33 | E6 | TLHDLCQA | 11 | 8 | | 36529 |
| HPV33 | E6 | TVVYREGNPF | 51 | 10 | | 36530 |
| HPV33 | E6 | VDLNKRFH | 119 | 8 | | 36531 |
| HPV33 | E6 | VVYREGNPF | 52 | 9 | | 36532 |
| HPV33 | E6 | WAGRCAACWR | 132 | 10 | | 36533 |
| HPV33 | E6 | YGNTLEQTVK | 84 | 10 | | 36534 |
| HPV33 | E6 | YGNTLEQTVKK | 84 | 11 | | 36535 |
| HPV33 | E7 | ADYYIVTCCH | 50 | 10 | | 36536 |
| HPV33 | E7 | CCHTCNTTVR | 57 | 10 | | 36537 |
| HPV33 | E7 | CVNSTASDLR | 68 | 10 | | 36538 |
| HPV33 | E7 | DGQAQPATA | 42 | 9 | | 36539 |
| HPV33 | E7 | DGQAQPATADY | 42 | 11 | | 36540 |
| HPV33 | E7 | DLYPEPTDLY | 14 | 10 | | 36541 |
| HPV33 | E7 | DSSDEDEGLDR | 30 | 11 | | 36542 |
| HPV33 | E7 | EGLDRPDGQA | 36 | 10 | | 36543 |
| HPV33 | E7 | GLDRPDGQA | 37 | 9 | | 36544 |
| HPV33 | E7 | GTVNIVCPTCA | 85 | 11 | | 36545 |
| HPV33 | E7 | HTCNTTVR | 59 | 8 | | 36546 |
| HPV33 | E7 | LCVNSTASDLR | 67 | 11 | | 36547 |
| HPV33 | E7 | LDLYPEPTDLY | 13 | 11 | | 36548 |
| HPV33 | E7 | LDRPDGQA | 38 | 8 | | 36549 |
| HPV33 | E7 | LDRPDGQAQPA | 38 | 11 | | 36550 |
| HPV33 | E7 | NIVCPTCA | 88 | 8 | | 36551 |
| HPV33 | E7 | NSTASDLR | 70 | 8 | | 36552 |
| HPV33 | E7 | PDGQAQPA | 41 | 8 | | 36553 |
| HPV33 | E7 | PDGQAQPATA | 41 | 10 | | 36554 |
| HPV33 | E7 | PTLKEYVLDLY | 6 | 11 | | 36555 |
| HPV33 | E7 | QAQPATADY | 44 | 9 | | 36556 |
| HPV33 | E7 | QAQPATADYY | 44 | 10 | | 36557 |
| HPV33 | E7 | RGHKPTLK | 2 | 8 | | 36558 |
| HPV33 | E7 | RGHKPTLKEY | 2 | 10 | | 36559 |
| HPV33 | E7 | RLCVNSTA | 66 | 8 | | 36560 |
| HPV33 | E7 | SDEDEGLDR | 32 | 9 | | 36561 |
| HPV33 | E7 | SSDEDEGLDR | 31 | 10 | | 36562 |
| HPV33 | E7 | TADYYIVTCCH | 49 | 11 | | 36563 |
| HPV33 | E7 | TCCHTCNTTVR | 56 | 11 | | 36564 |
| HPV33 | E7 | TLKEYVLDLY | 7 | 10 | | 36565 |
| HPV33 | E7 | TTVRLCVNSTA | 63 | 11 | | 36566 |
| HPV33 | E7 | TVNIVCPTCA | 86 | 10 | | 36567 |
| HPV33 | E7 | TVRLCVNSTA | 64 | 10 | | 36568 |
| HPV33 | L1 | AAPTSTRTSSA | 482 | 11 | | 36569 |
| HPV33 | L1 | ACTNAAPA | 175 | 8 | | 36570 |
| HPV33 | L1 | ACVGLEIGR | 102 | 9 | | 36571 |
| HPV33 | L1 | ADLDQFPLGR | 456 | 10 | | 36572 |
| HPV33 | L1 | ADLDQFPLGRK | 456 | 11 | | 36573 |
| HPV33 | L1 | ADNRECLSMDY | 142 | 11 | | 36574 |
| HPV33 | L1 | AGLKAKPK | 471 | 8 | | 36575 |
| HPV33 | L1 | AGLKAKPKLK | 471 | 10 | | 36576 |
| HPV33 | L1 | AGLKAKPKLKR | 471 | 11 | | 36577 |
| HPV33 | L1 | AGSSRLLA | 37 | 8 | | 36578 |
| HPV33 | L1 | AGSSRLLAVGH | 37 | 11 | | 36579 |
| HPV33 | L1 | AITCQKTVPPK | 424 | 11 | | 36580 |
| HPV33 | L1 | ASIQSSAF | 284 | 8 | | 36581 |
| HPV33 | L1 | ASIQSSAFF | 284 | 9 | | 36582 |
| HPV33 | L1 | ASLQDTYR | 411 | 8 | | 36583 |
| HPV33 | L1 | ASLQDTYRF | 411 | 9 | | 36584 |
| HPV33 | L1 | AVGHPYFSIK | 44 | 10 | | 36585 |
| HPV33 | L1 | AVPDDLYIK | 270 | 9 | | 36586 |
| HPV33 | L1 | CGSTCKYPDY | 225 | 10 | | 36587 |
| HPV33 | L1 | CMDFKTLQA | 207 | 9 | | 36588 |
| HPV33 | L1 | CMDFKTLQANK | 207 | 11 | | 36589 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | L1 | CTQVTSDSTY | 345 | 10 | | 36590 |
| HPV33 | L1 | CTQVTSDSTYK | 345 | 11 | | 36591 |
| HPV33 | L1 | CVGLEIGR | 103 | 8 | | 36592 |
| HPV33 | L1 | DDTETGNK | 128 | 8 | | 36593 |
| HPV33 | L1 | DDTETGNKY | 128 | 9 | | 36594 |
| HPV33 | L1 | DFKTLQANK | 209 | 9 | | 36595 |
| HPV33 | L1 | DGDMVDTGF | 197 | 9 | | 36596 |
| HPV33 | L1 | DICGSTCK | 223 | 8 | | 36597 |
| HPV33 | L1 | DICGSTCKY | 223 | 9 | | 36598 |
| HPV33 | L1 | DILEDWQF | 396 | 8 | | 36599 |
| HPV33 | L1 | DLDQFPLGR | 457 | 9 | | 36600 |
| HPV33 | L1 | DLDQFPLGRK | 457 | 10 | | 36601 |
| HPV33 | L1 | DLDQFPLGRKF | 457 | 11 | | 36602 |
| HPV33 | L1 | DLKEKFSA | 449 | 8 | | 36603 |
| HPV33 | L1 | DLQFVFQLCK | 370 | 10 | | 36604 |
| HPV33 | L1 | DLYIKGSGTTA | 274 | 11 | | 36605 |
| HPV33 | L1 | DSLFFFLR | 244 | 8 | | 36606 |
| HPV33 | L1 | DSLFFFLRR | 244 | 9 | | 36607 |
| HPV33 | L1 | DSTYKNENF | 351 | 9 | | 36608 |
| HPV33 | L1 | DSTYKNENFK | 351 | 10 | | 36609 |
| HPV33 | L1 | DTETGNKY | 129 | 8 | | 36610 |
| HPV33 | L1 | DTGFGCMDF | 202 | 9 | | 36611 |
| HPV33 | L1 | DTGFGCMDFK | 202 | 10 | | 36612 |
| HPV33 | L1 | DTQRLVWA | 95 | 8 | | 36613 |
| HPV33 | L1 | DTSFYNPDTQR | 88 | 11 | | 36614 |
| HPV33 | L1 | DTYRFVTSQA | 415 | 10 | | 36615 |
| HPV33 | L1 | EAVPDDLY | 269 | 8 | | 36616 |
| HPV33 | L1 | EAVPDDLYIK | 269 | 10 | | 36617 |
| HPV33 | L1 | ECLSMDYK | 146 | 8 | | 36618 |
| HPV33 | L1 | EDGDMVDTGF | 196 | 10 | | 36619 |
| HPV33 | L1 | EDPLGKYTF | 437 | 9 | | 36620 |
| HPV33 | L1 | ESQLFNKPY | 303 | 9 | | 36621 |
| HPV33 | L1 | EVDLKEKF | 447 | 8 | | 36622 |
| HPV33 | L1 | EVDLKEKFSA | 447 | 10 | | 36623 |
| HPV33 | L1 | EVMTYIHA | 385 | 8 | | 36624 |
| HPV33 | L1 | FDDTETGNK | 127 | 9 | | 36625 |
| HPV33 | L1 | FDDTETGNKY | 127 | 10 | | 36626 |
| HPV33 | L1 | FFFLRREQMF | 247 | 10 | | 36627 |
| HPV33 | L1 | FFLRREQMF | 248 | 9 | | 36628 |
| HPV33 | L1 | FFLRREQMFVR | 248 | 11 | | 36629 |
| HPV33 | L1 | FFNRAGTLGEA | 260 | 11 | | 36630 |
| HPV33 | L1 | FGCMDFKTLQA | 205 | 11 | | 36631 |
| HPV33 | L1 | FGFPDTSF | 84 | 8 | | 36632 |
| HPV33 | L1 | FGFPDTSFY | 84 | 9 | | 36633 |
| HPV33 | L1 | FGLTPPPSA | 403 | 9 | | 36634 |
| HPV33 | L1 | FLLQAGLK | 467 | 8 | | 36635 |
| HPV33 | L1 | FLLQAGLKA | 467 | 9 | | 36636 |
| HPV33 | L1 | FLLQAGLKAK | 467 | 10 | | 36637 |
| HPV33 | L1 | FLRREQMF | 249 | 8 | | 36638 |
| HPV33 | L1 | FLRREQMFVR | 249 | 10 | | 36639 |
| HPV33 | L1 | FLRREQMFVRH | 249 | 11 | | 36640 |
| HPV33 | L1 | FSADLDQF | 454 | 8 | | 36641 |
| HPV33 | L1 | FSIKNPTNA | 50 | 9 | | 36642 |
| HPV33 | L1 | FSIKNPTNAK | 50 | 10 | | 36643 |
| HPV33 | L1 | FSIKNPTNAKK | 50 | 11 | | 36644 |
| HPV33 | L1 | FVRHFFNR | 256 | 8 | | 36645 |
| HPV33 | L1 | FVRHFFNRA | 256 | 9 | | 36646 |
| HPV33 | L1 | FVTSQAITCQK | 419 | 11 | | 36647 |
| HPV33 | L1 | FVTVVDTTR | 330 | 9 | | 36648 |
| HPV33 | L1 | GCKPPTGEH | 161 | 9 | | 36649 |
| HPV33 | L1 | GCMDFKTLQA | 206 | 10 | | 36650 |
| HPV33 | L1 | GDMVDTGF | 198 | 8 | | 36651 |
| HPV33 | L1 | GDSLFFFLR | 243 | 9 | | 36652 |
| HPV33 | L1 | GDSLFFFLRR | 243 | 10 | | 36653 |
| HPV33 | L1 | GFGCMDFK | 204 | 8 | | 36654 |
| HPV33 | L1 | GFPDTSFY | 85 | 8 | | 36655 |
| HPV33 | L1 | GICWGNQVF | 322 | 9 | | 36656 |
| HPV33 | L1 | GISGHPLLNK | 117 | 10 | | 36657 |
| HPV33 | L1 | GISGHPLLNKF | 117 | 11 | | 36658 |
| HPV33 | L1 | GLKAKPKLK | 472 | 9 | | 36659 |
| HPV33 | L1 | GLKAKPKLKR | 472 | 10 | | 36660 |
| HPV33 | L1 | GLKAKPKLKRA | 472 | 11 | | 36661 |
| HPV33 | L1 | GLQYRVFR | 68 | 8 | | 36662 |
| HPV33 | L1 | GLQYRVFRVR | 68 | 10 | | 36663 |
| HPV33 | L1 | GLTPPPSA | 404 | 8 | | 36664 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | L1 | GSMVTSESQLF | 297 | 11 | | 36665 |
| HPV33 | L1 | GSSRLLAVGH | 38 | 10 | | 36666 |
| HPV33 | L1 | GSTCKYPDY | 226 | 9 | | 36667 |
| HPV33 | L1 | GSTCKYPDYLK | 226 | 11 | | 36668 |
| HPV33 | L1 | GTTASIQSSA | 281 | 10 | | 36669 |
| HPV33 | L1 | GTTASIQSSAF | 281 | 11 | | 36670 |
| HPV33 | L1 | GVACTNAA | 173 | 8 | | 36671 |
| HPV33 | L1 | GVACTNAAPA | 173 | 10 | | 36672 |
| HPV33 | L1 | HVEEYDLQF | 365 | 9 | | 36673 |
| HPV33 | L1 | HVEEYDLQFVF | 365 | 11 | | 36674 |
| HPV33 | L1 | ICGSTCKY | 224 | 8 | | 36675 |
| HPV33 | L1 | ICGSTCKYPDY | 224 | 11 | | 36676 |
| HPV33 | L1 | ICWGNQVF | 323 | 8 | | 36677 |
| HPV33 | L1 | IDICGSTCK | 222 | 9 | | 36678 |
| HPV33 | L1 | IDICGSTCKY | 222 | 10 | | 36679 |
| HPV33 | L1 | ISGHPLLNK | 118 | 9 | | 36680 |
| HPV33 | L1 | ISGHPLLNKF | 118 | 10 | | 36681 |
| HPV33 | L1 | ITCQKTVPPK | 425 | 10 | | 36682 |
| HPV33 | L1 | KAKPKLKR | 474 | 8 | | 36683 |
| HPV33 | L1 | KAKPKLKRA | 474 | 9 | | 36684 |
| HPV33 | L1 | KAKPKLKRAA | 474 | 10 | | 36685 |
| HPV33 | L1 | KFDDTETGNK | 126 | 10 | | 36686 |
| HPV33 | L1 | KFDDTETGNKY | 126 | 11 | | 36687 |
| HPV33 | L1 | KFGFPDTSF | 83 | 9 | | 36688 |
| HPV33 | L1 | KFGFPDTSFY | 83 | 10 | | 36689 |
| HPV33 | L1 | KFLLQAGLK | 466 | 9 | | 36690 |
| HPV33 | L1 | KFLLQAGLKA | 466 | 10 | | 36691 |
| HPV33 | L1 | KFLLQAGLKAK | 466 | 11 | | 36692 |
| HPV33 | L1 | KFSADLDQF | 453 | 9 | | 36693 |
| HPV33 | L1 | KGVACTNA | 172 | 8 | | 36694 |
| HPV33 | L1 | KGVACTNAA | 172 | 9 | | 36695 |
| HPV33 | L1 | KGVACTNAAPA | 172 | 11 | | 36696 |
| HPV33 | L1 | KLKRAAPTSTR | 478 | 11 | | 36697 |
| HPV33 | L1 | KTVPPKEK | 429 | 8 | | 36698 |
| HPV33 | L1 | KVSGLQYR | 65 | 8 | | 36699 |
| HPV33 | L1 | KVSGLQYRVF | 65 | 10 | | 36700 |
| HPV33 | L1 | KVSGLQYRVFR | 65 | 11 | | 36701 |
| HPV33 | L1 | KVTLTAEVMTY | 379 | 11 | | 36702 |
| HPV33 | L1 | KVVSTDEY | 20 | 8 | | 36703 |
| HPV33 | L1 | KVVSTDEYVSR | 20 | 11 | | 36704 |
| HPV33 | L1 | LAVGHPYF | 43 | 8 | | 36705 |
| HPV33 | L1 | LAVGHPYFSIK | 43 | 11 | | 36706 |
| HPV33 | L1 | LCKVTLTA | 377 | 8 | | 36707 |
| HPV33 | L1 | LCTQVTSDSTY | 344 | 11 | | 36708 |
| HPV33 | L1 | LDQFPLGR | 458 | 8 | | 36709 |
| HPV33 | L1 | LDQFPLGRK | 458 | 9 | | 36710 |
| HPV33 | L1 | LDQFPLGRKF | 458 | 10 | | 36711 |
| HPV33 | L1 | LFFFLRREQMF | 246 | 11 | | 36712 |
| HPV33 | L1 | LFNKPYWLQR | 306 | 10 | | 36713 |
| HPV33 | L1 | LFNKPYWLQRA | 306 | 11 | | 36714 |
| HPV33 | L1 | LGCKPPTGEH | 160 | 10 | | 36715 |
| HPV33 | L1 | LGEAVPDDLY | 267 | 10 | | 36716 |
| HPV33 | L1 | LGRKFLLQA | 463 | 9 | | 36717 |
| HPV33 | L1 | LGVGISGH | 114 | 8 | | 36718 |
| HPV33 | L1 | LLAVGHPY | 42 | 8 | | 36719 |
| HPV33 | L1 | LLAVGHPYF | 42 | 9 | | 36720 |
| HPV33 | L1 | LLGCKPPTGEH | 159 | 11 | | 36721 |
| HPV33 | L1 | LLQAGLKA | 468 | 8 | | 36722 |
| HPV33 | L1 | LLQAGLKAK | 468 | 9 | | 36723 |
| HPV33 | L1 | LLQAGLKAKPK | 468 | 11 | | 36724 |
| HPV33 | L1 | LLVPKVSGLQY | 61 | 11 | | 36725 |
| HPV33 | L1 | LTAEVMTY | 382 | 8 | | 36726 |
| HPV33 | L1 | LTAEVMTYIH | 382 | 10 | | 36727 |
| HPV33 | L1 | LTAEVMTYIHA | 382 | 11 | | 36728 |
| HPV33 | L1 | LVPKVSGLQY | 62 | 10 | | 36729 |
| HPV33 | L1 | LVPKVSGLQYR | 62 | 11 | | 36730 |
| HPV33 | L1 | MDFKTLQA | 208 | 8 | | 36731 |
| HPV33 | L1 | MDFKTLQANK | 208 | 10 | | 36732 |
| HPV33 | L1 | MFVRHFFNR | 255 | 9 | | 36733 |
| HPV33 | L1 | MFVRHFFNRA | 255 | 10 | | 36734 |
| HPV33 | L1 | MSVWRPSEA | 1 | 9 | | 36735 |
| HPV33 | L1 | MTSEPYGDSLF | 237 | 11 | | 36736 |
| HPV33 | L1 | MVDTGFGCMDF | 200 | 11 | | 36737 |
| HPV33 | L1 | MVTSESQLF | 299 | 9 | | 36738 |
| HPV33 | L1 | MVTSESQLFNK | 299 | 11 | | 36739 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | L1 | NAKKLLVPK | 57 | 9 | | 36740 |
| HPV33 | L1 | NFKEYIRH | 358 | 8 | | 36741 |
| HPV33 | L1 | NGICWGNQVF | 321 | 10 | | 36742 |
| HPV33 | L1 | PDILEDWQF | 395 | 9 | | 36743 |
| HPV33 | L1 | PDPNKFGF | 79 | 8 | | 36744 |
| HPV33 | L1 | PDTQRLVWA | 94 | 9 | | 36745 |
| HPV33 | L1 | PDYLKMTSEPY | 232 | 11 | | 36746 |
| HPV33 | L1 | PGQPGADNR | 137 | 9 | | 36747 |
| HPV33 | L1 | PIDICGSTCK | 221 | 10 | | 36748 |
| HPV33 | L1 | PIDICGSTCKY | 221 | 11 | | 36749 |
| HPV33 | L1 | PLGRKFLLQA | 462 | 10 | | 36750 |
| HPV33 | L1 | PLGVGISGH | 113 | 9 | | 36751 |
| HPV33 | L1 | PSASLQDTY | 409 | 9 | | 36752 |
| HPV33 | L1 | PSASLQDTYR | 409 | 10 | | 36753 |
| HPV33 | L1 | PSASLQDTYRF | 409 | 11 | | 36754 |
| HPV33 | L1 | PTGEHWGK | 165 | 8 | | 36755 |
| HPV33 | L1 | PTGEHWGKGVA | 165 | 11 | | 36756 |
| HPV33 | L1 | PTNAKKLLVPK | 55 | 11 | | 36757 |
| HPV33 | L1 | PTSTRTSSA | 484 | 9 | | 36758 |
| HPV33 | L1 | PTSTRTSSAK | 484 | 10 | | 36759 |
| HPV33 | L1 | PTSTRTSSAKR | 484 | 11 | | 36760 |
| HPV33 | L1 | PVSKVVSTDEY | 17 | 11 | | 36761 |
| HPV33 | L1 | QAGLKAKPK | 470 | 9 | | 36762 |
| HPV33 | L1 | QAGLKAKPKLK | 470 | 11 | | 36763 |
| HPV33 | L1 | QDTYRFVTSQA | 414 | 11 | | 36764 |
| HPV33 | L1 | QFGLTPPPSA | 402 | 10 | | 36765 |
| HPV33 | L1 | QFPLGRKF | 460 | 8 | | 36766 |
| HPV33 | L1 | QFVFQLCK | 372 | 8 | | 36767 |
| HPV33 | L1 | QLCKVTLTA | 376 | 9 | | 36768 |
| HPV33 | L1 | QLCLLGCK | 156 | 8 | | 36769 |
| HPV33 | L1 | QLFNKPYWLQR | 305 | 11 | | 36770 |
| HPV33 | L1 | QMFVRHFF | 254 | 8 | | 36771 |
| HPV33 | L1 | QMFVRHFFNR | 254 | 10 | | 36772 |
| HPV33 | L1 | QMFVRHFFNRA | 254 | 11 | | 36773 |
| HPV33 | L1 | QTQLCLLGCK | 154 | 10 | | 36774 |
| HPV33 | L1 | QVFVTVVDTTR | 328 | 11 | | 36775 |
| HPV33 | L1 | QVTSDSTY | 347 | 8 | | 36776 |
| HPV33 | L1 | QVTSDSTYK | 347 | 9 | | 36777 |
| HPV33 | L1 | RAAPTSTR | 481 | 8 | | 36778 |
| HPV33 | L1 | RAGTLGEA | 263 | 8 | | 36779 |
| HPV33 | L1 | RLLAVGHPY | 41 | 9 | | 36780 |
| HPV33 | L1 | RLLAVGHPYF | 41 | 10 | | 36781 |
| HPV33 | L1 | RLPDPNKF | 77 | 8 | | 36782 |
| HPV33 | L1 | RLPDPNKFGF | 77 | 10 | | 36783 |
| HPV33 | L1 | RTSIYYYA | 30 | 8 | | 36784 |
| HPV33 | L1 | RTSSAKRK | 488 | 8 | | 36785 |
| HPV33 | L1 | RTSSAKRKK | 488 | 9 | | 36786 |
| HPV33 | L1 | RTSSAKRKKVK | 488 | 11 | | 36787 |
| HPV33 | L1 | RVRLPDPNK | 75 | 9 | | 36788 |
| HPV33 | L1 | RVRLPDPNKF | 75 | 10 | | 36789 |
| HPV33 | L1 | SADLDQFPLGR | 455 | 11 | | 36790 |
| HPV33 | L1 | SAKRKKVK | 491 | 8 | | 36791 |
| HPV33 | L1 | SAKRKKVKK | 491 | 9 | | 36792 |
| HPV33 | L1 | SASLQDTY | 410 | 8 | | 36793 |
| HPV33 | L1 | SASLQDTYR | 410 | 9 | | 36794 |
| HPV33 | L1 | SASLQDTYRF | 410 | 10 | | 36795 |
| HPV33 | L1 | SDSTYKNENF | 350 | 10 | | 36796 |
| HPV33 | L1 | SDSTYKNENFK | 350 | 11 | | 36797 |
| HPV33 | L1 | SFYNPDTQR | 90 | 9 | | 36798 |
| HPV33 | L1 | SGHPLLNK | 119 | 8 | | 36799 |
| HPV33 | L1 | SGHPLLNKF | 119 | 9 | | 36800 |
| HPV33 | L1 | SGLQYRVF | 67 | 8 | | 36801 |
| HPV33 | L1 | SGLQYRVFR | 67 | 9 | | 36802 |
| HPV33 | L1 | SGLQYRVFRVR | 67 | 11 | | 36803 |
| HPV33 | L1 | SGTTASIQSSA | 280 | 11 | | 36804 |
| HPV33 | L1 | SIKNPTNA | 51 | 8 | | 36805 |
| HPV33 | L1 | SIKNPTNAK | 51 | 9 | | 36806 |
| HPV33 | L1 | SIKNPTNAKK | 51 | 10 | | 36807 |
| HPV33 | L1 | SIQSSAFF | 285 | 8 | | 36808 |
| HPV33 | L1 | SIYYYAGSSR | 32 | 10 | | 36809 |
| HPV33 | L1 | SLFFFLRR | 245 | 8 | | 36810 |
| HPV33 | L1 | SLQDTYRF | 412 | 8 | | 36811 |
| HPV33 | L1 | SMVTSESQLF | 298 | 10 | | 36812 |
| HPV33 | L1 | SSAKRKKVK | 490 | 9 | | 36813 |
| HPV33 | L1 | SSAKRKKVKK | 490 | 10 | | 36814 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | L1 | SSRLLAVGH | 39 | 9 | | 36815 |
| HPV33 | L1 | SSRLLAVGHPY | 39 | 11 | | 36816 |
| HPV33 | L1 | STCKYPDY | 227 | 8 | | 36817 |
| HPV33 | L1 | STCKYPDYLK | 227 | 10 | | 36818 |
| HPV33 | L1 | STDEYVSR | 23 | 8 | | 36819 |
| HPV33 | L1 | STRTSSAK | 486 | 8 | | 36820 |
| HPV33 | L1 | STRTSSAKR | 486 | 9 | | 36821 |
| HPV33 | L1 | STRTSSAKRK | 486 | 10 | | 36822 |
| HPV33 | L1 | STRTSSAKRKK | 486 | 11 | | 36823 |
| HPV33 | L1 | STYKNENF | 352 | 8 | | 36824 |
| HPV33 | L1 | STYKNENFK | 352 | 9 | | 36825 |
| HPV33 | L1 | STYKNENFKEY | 352 | 11 | | 36826 |
| HPV33 | L1 | SVWRPSEA | 2 | 8 | | 36827 |
| HPV33 | L1 | SVWRPSEATVY | 2 | 11 | | 36828 |
| HPV33 | L1 | TAEVMTYIH | 383 | 9 | | 36829 |
| HPV33 | L1 | TAEVMTYIHA | 383 | 10 | | 36830 |
| HPV33 | L1 | TASIQSSA | 283 | 8 | | 36831 |
| HPV33 | L1 | TASIQSSAF | 283 | 9 | | 36832 |
| HPV33 | L1 | TASIQSSAFF | 283 | 10 | | 36833 |
| HPV33 | L1 | TCKYPDYLK | 228 | 9 | | 36834 |
| HPV33 | L1 | TCQKTVPPK | 426 | 9 | | 36835 |
| HPV33 | L1 | TCQKTVPPKEK | 426 | 11 | | 36836 |
| HPV33 | L1 | TDEYVSRTSIY | 24 | 11 | | 36837 |
| HPV33 | L1 | TFWEVDLK | 444 | 8 | | 36838 |
| HPV33 | L1 | TFWEVDLKEK | 444 | 10 | | 36839 |
| HPV33 | L1 | TFWEVDLKEKF | 444 | 11 | | 36840 |
| HPV33 | L1 | TGEHWGKGVA | 166 | 10 | | 36841 |
| HPV33 | L1 | TGFGCMDF | 203 | 8 | | 36842 |
| HPV33 | L1 | TGFGCMDFK | 203 | 9 | | 36843 |
| HPV33 | L1 | TGNKYPGQPGA | 132 | 11 | | 36844 |
| HPV33 | L1 | TLGEAVPDDLY | 266 | 11 | | 36845 |
| HPV33 | L1 | TLTAEVMTY | 381 | 9 | | 36846 |
| HPV33 | L1 | TLTAEVMTYIH | 381 | 11 | | 36847 |
| HPV33 | L1 | TSDSTYKNENF | 349 | 11 | | 36848 |
| HPV33 | L1 | TSEPYGDSLF | 238 | 10 | | 36849 |
| HPV33 | L1 | TSEPYGDSLFF | 238 | 11 | | 36850 |
| HPV33 | L1 | TSESQLFNK | 301 | 9 | | 36851 |
| HPV33 | L1 | TSESQLFNKPY | 301 | 11 | | 36852 |
| HPV33 | L1 | TSFYNPDTQR | 89 | 10 | | 36853 |
| HPV33 | L1 | TSIYYYAGSSR | 31 | 11 | | 36854 |
| HPV33 | L1 | TSQAITCQK | 421 | 9 | | 36855 |
| HPV33 | L1 | TSSAKRKK | 489 | 8 | | 36856 |
| HPV33 | L1 | TSSAKRKKVK | 489 | 10 | | 36857 |
| HPV33 | L1 | TSSAKRKKVKK | 489 | 11 | | 36858 |
| HPV33 | L1 | TSTRTSSA | 485 | 8 | | 36859 |
| HPV33 | L1 | TSTRTSSAK | 485 | 9 | | 36860 |
| HPV33 | L1 | TSTRTSSAKR | 485 | 10 | | 36861 |
| HPV33 | L1 | TSTRTSSAKRK | 485 | 11 | | 36862 |
| HPV33 | L1 | TTASIQSSA | 282 | 9 | | 36863 |
| HPV33 | L1 | TTASIQSSAF | 282 | 10 | | 36864 |
| HPV33 | L1 | TTASIQSSAFF | 282 | 11 | | 36865 |
| HPV33 | L1 | TVYLPPVPVSK | 10 | 11 | | 36866 |
| HPV33 | L1 | VACTNAAPA | 174 | 9 | | 36867 |
| HPV33 | L1 | VDLKEKFSA | 448 | 9 | | 36868 |
| HPV33 | L1 | VDTGFGCMDF | 201 | 10 | | 36869 |
| HPV33 | L1 | VDTGFGCMDFK | 201 | 11 | | 36870 |
| HPV33 | L1 | VFQLCKVTLTA | 374 | 11 | | 36871 |
| HPV33 | L1 | VFRVRLPDPNK | 73 | 11 | | 36872 |
| HPV33 | L1 | VFVTVVDTTR | 329 | 10 | | 36873 |
| HPV33 | L1 | VGHPYFSIK | 45 | 9 | | 36874 |
| HPV33 | L1 | VGISGHPLLNK | 116 | 11 | | 36875 |
| HPV33 | L1 | VSGLQYRVF | 66 | 9 | | 36876 |
| HPV33 | L1 | VSGLQYRVFR | 66 | 10 | | 36877 |
| HPV33 | L1 | VSKVVSTDEY | 18 | 10 | | 36878 |
| HPV33 | L1 | VSRTSIYY | 28 | 8 | | 36879 |
| HPV33 | L1 | VSRTSIYYY | 28 | 9 | | 36880 |
| HPV33 | L1 | VSRTSIYYYA | 28 | 10 | | 36881 |
| HPV33 | L1 | VSTDEYVSR | 22 | 9 | | 36882 |
| HPV33 | L1 | VTLTAEVMTY | 380 | 10 | | 36883 |
| HPV33 | L1 | VTSDSTYK | 348 | 8 | | 36884 |
| HPV33 | L1 | VTSESQLF | 300 | 8 | | 36885 |
| HPV33 | L1 | VTSESQLFNK | 300 | 10 | | 36886 |
| HPV33 | L1 | VTSQAITCQK | 420 | 10 | | 36887 |
| HPV33 | L1 | VTVVDTTR | 331 | 8 | | 36888 |
| HPV33 | L1 | VVSTDEYVSR | 21 | 10 | | 36889 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | L1 | WACVGLEIGR | 101 | 10 | | 36890 |
| HPV33 | L1 | WGKGVACTNA | 170 | 10 | | 36891 |
| HPV33 | L1 | WGKGVACTNAA | 170 | 11 | | 36892 |
| HPV33 | L1 | WLQRAQGH | 312 | 8 | | 36893 |
| HPV33 | L1 | YAGSSRLLA | 36 | 9 | | 36894 |
| HPV33 | L1 | YDLQFVFQLCK | 369 | 11 | | 36895 |
| HPV33 | L1 | YFSIKNPTNA | 49 | 10 | | 36896 |
| HPV33 | L1 | YFSIKNPTNAK | 49 | 11 | | 36897 |
| HPV33 | L1 | YGDSLFFF | 242 | 8 | | 36898 |
| HPV33 | L1 | YGDSLFFFLR | 242 | 10 | | 36899 |
| HPV33 | L1 | YGDSLFFFLRR | 242 | 11 | | 36900 |
| HPV33 | L1 | YIKGSGTTA | 276 | 9 | | 36901 |
| HPV33 | L1 | YIRHVEEY | 362 | 8 | | 36902 |
| HPV33 | L1 | YLKMTSEPY | 234 | 9 | | 36903 |
| HPV33 | L1 | YLPPVPVSK | 12 | 9 | | 36904 |
| HPV33 | L1 | YTFWEVDLK | 443 | 9 | | 36905 |
| HPV33 | L1 | YTFWEVDLKEK | 443 | 11 | | 36906 |
| HPV33 | L1 | YVSRTSIY | 27 | 8 | | 36907 |
| HPV33 | L1 | YVSRTSIYY | 27 | 9 | | 36908 |
| HPV33 | L1 | YVSRTSIYYY | 27 | 10 | | 36909 |
| HPV33 | L1 | YVSRTSIYYYA | 27 | 11 | | 36910 |
| HPV33 | L2 | AAIPLQPIR | 81 | 9 | | 36911 |
| HPV33 | L2 | ADDVDNVH | 367 | 8 | | 36912 |
| HPV33 | L2 | ADFVLHPSY | 438 | 9 | | 36913 |
| HPV33 | L2 | ADFVLHPSYF | 438 | 10 | | 36914 |
| HPV33 | L2 | AFLTSPHK | 241 | 8 | | 36915 |
| HPV33 | L2 | AIPLQPIR | 82 | 8 | | 36916 |
| HPV33 | L2 | AITSRRHTVR | 291 | 10 | | 36917 |
| HPV33 | L2 | AITSRRHTVRF | 291 | 11 | | 36918 |
| HPV33 | L2 | ALHRPAITSR | 286 | 10 | | 36919 |
| HPV33 | L2 | ALHRPAITSRR | 286 | 11 | | 36920 |
| HPV33 | L2 | ASATQLYQTCK | 12 | 11 | | 36921 |
| HPV33 | L2 | ATLKTRSGK | 308 | 9 | | 36922 |
| HPV33 | L2 | ATQLYQTCK | 14 | 9 | | 36923 |
| HPV33 | L2 | ATQLYQTCKA | 14 | 10 | | 36924 |
| HPV33 | L2 | DFLDIIALH | 280 | 9 | | 36925 |
| HPV33 | L2 | DFLDIIALHR | 280 | 10 | | 36926 |
| HPV33 | L2 | DFVLHPSY | 439 | 8 | | 36927 |
| HPV33 | L2 | DFVLHPSYF | 439 | 9 | | 36928 |
| HPV33 | L2 | DGADFVLH | 436 | 8 | | 36929 |
| HPV33 | L2 | DGADFVLHPSY | 436 | 11 | | 36930 |
| HPV33 | L2 | DGLYDVYA | 360 | 8 | | 36931 |
| HPV33 | L2 | DIIALHRPA | 283 | 9 | | 36932 |
| HPV33 | L2 | DISPAPDPDF | 272 | 10 | | 36933 |
| HPV33 | L2 | DLSPIVPLDH | 327 | 10 | | 36934 |
| HPV33 | L2 | DTIVVDGA | 431 | 8 | | 36935 |
| HPV33 | L2 | DTIVVDGADF | 431 | 10 | | 36936 |
| HPV33 | L2 | DVDNVHTPMQH | 369 | 11 | | 36937 |
| HPV33 | L2 | DVTTSADTTPA | 130 | 11 | | 36938 |
| HPV33 | L2 | DVYADDVDNVH | 364 | 11 | | 36939 |
| HPV33 | L2 | EASGHFIF | 176 | 8 | | 36940 |
| HPV33 | L2 | EDTLQFQH | 263 | 8 | | 36941 |
| HPV33 | L2 | EGSTIADQILK | 36 | 11 | | 36942 |
| HPV33 | L2 | ESFDPEDTLQF | 258 | 11 | | 36943 |
| HPV33 | L2 | ESSIQTISTH | 149 | 10 | | 36944 |
| HPV33 | L2 | ETSFIEAGA | 110 | 9 | | 36945 |
| HPV33 | L2 | ETSFIEAGAPA | 110 | 11 | | 36946 |
| HPV33 | L2 | FDPEDTLQF | 260 | 9 | | 36947 |
| HPV33 | L2 | FDPEDTLQFQH | 260 | 11 | | 36948 |
| HPV33 | L2 | FDTIVVDGA | 430 | 9 | | 36949 |
| HPV33 | L2 | FDTIVVDGADF | 430 | 11 | | 36950 |
| HPV33 | L2 | FFTDVRVA | 459 | 8 | | 36951 |
| HPV33 | L2 | FFTDVRVAA | 459 | 9 | | 36952 |
| HPV33 | L2 | FIEAGAPA | 113 | 8 | | 36953 |
| HPV33 | L2 | FILRRRRK | 447 | 8 | | 36954 |
| HPV33 | L2 | FILRRRRKR | 447 | 9 | | 36955 |
| HPV33 | L2 | FILRRRRKRF | 447 | 10 | | 36956 |
| HPV33 | L2 | FLDIIALH | 281 | 8 | | 36957 |
| HPV33 | L2 | FLDIIALHR | 281 | 9 | | 36958 |
| HPV33 | L2 | FLDIIALHRPA | 281 | 11 | | 36959 |
| HPV33 | L2 | FLTSPHKLITY | 242 | 11 | | 36960 |
| HPV33 | L2 | FSRVGQKA | 301 | 8 | | 36961 |
| HPV33 | L2 | FSRVGQKATLK | 301 | 11 | | 36962 |
| HPV33 | L2 | FSSPTVSTQSY | 183 | 11 | | 36963 |
| HPV33 | L2 | FTDVRVAA | 460 | 8 | | 36964 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | L2 | FTEPSVLH | 163 | 8 | | 36965 |
| HPV33 | L2 | FTEPSVLHPPA | 163 | 11 | | 36966 |
| HPV33 | L2 | FVLHPSYF | 440 | 8 | | 36967 |
| HPV33 | L2 | FVLHPSYFILR | 440 | 11 | | 36968 |
| HPV33 | L2 | FVPISPFF | 421 | 8 | | 36969 |
| HPV33 | L2 | FVPISPFFPF | 421 | 10 | | 36970 |
| HPV33 | L2 | GADFVLHPSY | 437 | 10 | | 36971 |
| HPV33 | L2 | GADFVLHPSYF | 437 | 11 | | 36972 |
| HPV33 | L2 | GFDVTTSA | 128 | 8 | | 36973 |
| HPV33 | L2 | GIGTGSGSGGR | 58 | 11 | | 36974 |
| HPV33 | L2 | GLYSRNTQQVK | 226 | 11 | | 36975 |
| HPV33 | L2 | GSGGRTGY | 64 | 8 | | 36976 |
| HPV33 | L2 | GSGSGGRTGY | 62 | 10 | | 36977 |
| HPV33 | L2 | GSRPVARLGLY | 218 | 11 | | 36978 |
| HPV33 | L2 | GSTIADQILK | 37 | 10 | | 36979 |
| HPV33 | L2 | GSTIADQILKY | 37 | 11 | | 36980 |
| HPV33 | L2 | GTCPPDVIPK | 25 | 10 | | 36981 |
| HPV33 | L2 | GTDPPTAA | 75 | 8 | | 36982 |
| HPV33 | L2 | GTGSGSGGR | 60 | 9 | | 36983 |
| HPV33 | L2 | HDTSTSSY | 349 | 8 | | 36984 |
| HPV33 | L2 | HSYSTFATTR | 379 | 10 | | 36985 |
| HPV33 | L2 | HTPMQHSY | 374 | 8 | | 36986 |
| HPV33 | L2 | HTPMQHSYSTF | 374 | 11 | | 36987 |
| HPV33 | L2 | HTVPNEQY | 336 | 8 | | 36988 |
| HPV33 | L2 | HTVRFSRVGQK | 297 | 11 | | 36989 |
| HPV33 | L2 | IADQILKY | 40 | 8 | | 36990 |
| HPV33 | L2 | IALHRPAITSR | 285 | 11 | | 36991 |
| HPV33 | L2 | IGARIHYY | 318 | 8 | | 36992 |
| HPV33 | L2 | IGTDPPTA | 74 | 8 | | 36993 |
| HPV33 | L2 | IGTDPPTAA | 74 | 9 | | 36994 |
| HPV33 | L2 | IGTGSGSGGR | 59 | 10 | | 36995 |
| HPV33 | L2 | IIALHRPA | 284 | 8 | | 36996 |
| HPV33 | L2 | ILKYGSLGVF | 44 | 10 | | 36997 |
| HPV33 | L2 | ILKYGSLGVFF | 44 | 11 | | 36998 |
| HPV33 | L2 | ILRRRRKR | 448 | 8 | | 36999 |
| HPV33 | L2 | ILRRRRKRF | 448 | 9 | | 37000 |
| HPV33 | L2 | ILRRRRKRFPY | 448 | 11 | | 37001 |
| HPV33 | L2 | ISPAPDPDF | 273 | 9 | | 37002 |
| HPV33 | L2 | ISTHLNPTF | 155 | 9 | | 37003 |
| HPV33 | L2 | ITSRRHTVR | 292 | 9 | | 37004 |
| HPV33 | L2 | ITSRRHTVRF | 292 | 10 | | 37005 |
| HPV33 | L2 | ITYDNPAF | 250 | 8 | | 37006 |
| HPV33 | L2 | ITYDNPAFESF | 250 | 11 | | 37007 |
| HPV33 | L2 | IVSLIEETSF | 104 | 10 | | 37008 |
| HPV33 | L2 | IVVDGADF | 433 | 8 | | 37009 |
| HPV33 | L2 | IVVDGADFVLH | 433 | 11 | | 37010 |
| HPV33 | L2 | KATLKTRSGK | 307 | 10 | | 37011 |
| HPV33 | L2 | KLITYDNPA | 248 | 9 | | 37012 |
| HPV33 | L2 | KLITYDNPAF | 248 | 10 | | 37013 |
| HPV33 | L2 | KTRSGKQIGA | 311 | 10 | | 37014 |
| HPV33 | L2 | KTRSGKQIGAR | 311 | 11 | | 37015 |
| HPV33 | L2 | KVEGSTIA | 34 | 8 | | 37016 |
| HPV33 | L2 | LDHTVPNEQY | 334 | 10 | | 37017 |
| HPV33 | L2 | LDIIALHR | 282 | 8 | | 37018 |
| HPV33 | L2 | LDIIALHRPA | 282 | 10 | | 37019 |
| HPV33 | L2 | LFPTSSPF | 414 | 8 | | 37020 |
| HPV33 | L2 | LIEETSFIEA | 107 | 10 | | 37021 |
| HPV33 | L2 | LITYDNPA | 249 | 8 | | 37022 |
| HPV33 | L2 | LITYDNPAF | 249 | 9 | | 37023 |
| HPV33 | L2 | LSPIVPLDH | 328 | 9 | | 37024 |
| HPV33 | L2 | LTSPHKLITY | 243 | 10 | | 37025 |
| HPV33 | L2 | MSGPDIPSPLF | 405 | 11 | | 37026 |
| HPV33 | L2 | NDGLYDVY | 359 | 8 | | 37027 |
| HPV33 | L2 | NDGLYDVYA | 359 | 9 | | 37028 |
| HPV33 | L2 | NTQQVKVVDPA | 231 | 11 | | 37029 |
| HPV33 | L2 | NVHTPMQH | 372 | 8 | | 37030 |
| HPV33 | L2 | NVHTPMQHSY | 372 | 10 | | 37031 |
| HPV33 | L2 | NVSIPLNTGF | 391 | 10 | | 37032 |
| HPV33 | L2 | PAEASGHF | 174 | 8 | | 37033 |
| HPV33 | L2 | PAEASGHFIF | 174 | 10 | | 37034 |
| HPV33 | L2 | PAFLTSPH | 240 | 8 | | 37035 |
| HPV33 | L2 | PAFLTSPHK | 240 | 9 | | 37036 |
| HPV33 | L2 | PAITSRRH | 290 | 8 | | 37037 |
| HPV33 | L2 | PAITSRRHTVR | 290 | 11 | | 37038 |
| HPV33 | L2 | PAPAEASGH | 172 | 9 | | 37039 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | L2 | PAPAEASGHF | 172 | 10 | | 37040 |
| HPV33 | L2 | PAPSIPTPSGF | 119 | 11 | | 37041 |
| HPV33 | L2 | PDFLDIIA | 279 | 8 | | 37042 |
| HPV33 | L2 | PDFLDIIALH | 279 | 10 | | 37043 |
| HPV33 | L2 | PDFLDIIALHR | 279 | 11 | | 37044 |
| HPV33 | L2 | PDIPSPLF | 408 | 8 | | 37045 |
| HPV33 | L2 | PDPDFLDIIA | 277 | 10 | | 37046 |
| HPV33 | L2 | PFDTIVVDGA | 429 | 10 | | 37047 |
| HPV33 | L2 | PFVPISPF | 420 | 8 | | 37048 |
| HPV33 | L2 | PFVPISPFF | 420 | 9 | | 37049 |
| HPV33 | L2 | PFVPISPFFPF | 420 | 11 | | 37050 |
| HPV33 | L2 | PGSRPVAR | 217 | 8 | | 37051 |
| HPV33 | L2 | PIGTDPPTA | 73 | 9 | | 37052 |
| HPV33 | L2 | PIGTDPPTAA | 73 | 10 | | 37053 |
| HPV33 | L2 | PIPGSRPVA | 215 | 9 | | 37054 |
| HPV33 | L2 | PIPGSRPVAR | 215 | 10 | | 37055 |
| HPV33 | L2 | PISPFFPF | 423 | 8 | | 37056 |
| HPV33 | L2 | PLDHTVPNEQY | 333 | 11 | | 37057 |
| HPV33 | L2 | PLFPTSSPF | 413 | 9 | | 37058 |
| HPV33 | L2 | PLHDTSTSSY | 347 | 10 | | 37059 |
| HPV33 | L2 | PMQHSYSTF | 376 | 9 | | 37060 |
| HPV33 | L2 | PMQHSYSTFA | 376 | 10 | | 37061 |
| HPV33 | L2 | PSGFDVTTSA | 126 | 10 | | 37062 |
| HPV33 | L2 | PSIPTPSGF | 121 | 9 | | 37063 |
| HPV33 | L2 | PSPLFPTSSPF | 411 | 11 | | 37064 |
| HPV33 | L2 | PSVLHPPA | 166 | 8 | | 37065 |
| HPV33 | L2 | PSVLHPPAPA | 166 | 10 | | 37066 |
| HPV33 | L2 | PSYFILRR | 444 | 8 | | 37067 |
| HPV33 | L2 | PSYFILRRR | 444 | 9 | | 37068 |
| HPV33 | L2 | PSYFILRRRR | 444 | 10 | | 37069 |
| HPV33 | L2 | PSYFILRRRRK | 444 | 11 | | 37070 |
| HPV33 | L2 | PTAAIPLQPIR | 79 | 11 | | 37071 |
| HPV33 | L2 | PTFTEPSVLH | 161 | 10 | | 37072 |
| HPV33 | L2 | PTVSTQSY | 186 | 8 | | 37073 |
| HPV33 | L2 | PVARLGLY | 221 | 8 | | 37074 |
| HPV33 | L2 | PVARLGLYSR | 221 | 10 | | 37075 |
| HPV33 | L2 | QDLSPIVPLDH | 326 | 11 | | 37076 |
| HPV33 | L2 | QFQHSDISPA | 267 | 10 | | 37077 |
| HPV33 | L2 | QIGARIHY | 317 | 8 | | 37078 |
| HPV33 | L2 | QIGARIHYY | 317 | 9 | | 37079 |
| HPV33 | L2 | QILKYGSLGVF | 43 | 11 | | 37080 |
| HPV33 | L2 | QLYQTCKA | 16 | 8 | | 37081 |
| HPV33 | L2 | QSYENIPMDTF | 191 | 11 | | 37082 |
| HPV33 | L2 | QTISTHLNPTF | 153 | 11 | | 37083 |
| HPV33 | L2 | QVKVVDPA | 234 | 8 | | 37084 |
| HPV33 | L2 | QVKVVDPAF | 234 | 9 | | 37085 |
| HPV33 | L2 | RASATQLY | 11 | 8 | | 37086 |
| HPV33 | L2 | RFPYFFTDVR | 455 | 10 | | 37087 |
| HPV33 | L2 | RFSRVGQK | 300 | 8 | | 37088 |
| HPV33 | L2 | RFSRVGQKA | 300 | 9 | | 37089 |
| HPV33 | L2 | RSGKQIGA | 313 | 8 | | 37090 |
| HPV33 | L2 | RSGKQIGAR | 313 | 9 | | 37091 |
| HPV33 | L2 | RSGKQIGARIH | 313 | 11 | | 37092 |
| HPV33 | L2 | RSTRRKRA | 5 | 8 | | 37093 |
| HPV33 | L2 | RSTRRKRASA | 5 | 10 | | 37094 |
| HPV33 | L2 | RVGQKATLK | 303 | 9 | | 37095 |
| HPV33 | L2 | RVGQKATLKTR | 303 | 11 | | 37096 |
| HPV33 | L2 | SATQLYQTCK | 13 | 10 | | 37097 |
| HPV33 | L2 | SATQLYQTCKA | 13 | 11 | | 37098 |
| HPV33 | L2 | SDISPAPDPDF | 271 | 11 | | 37099 |
| HPV33 | L2 | SFDPEDTLQF | 259 | 10 | | 37100 |
| HPV33 | L2 | SFIEAGAPA | 112 | 9 | | 37101 |
| HPV33 | L2 | SGFDVTTSA | 127 | 9 | | 37102 |
| HPV33 | L2 | SGKQIGAR | 314 | 8 | | 37103 |
| HPV33 | L2 | SGKQIGARIH | 314 | 10 | | 37104 |
| HPV33 | L2 | SGKQIGARIHY | 314 | 11 | | 37105 |
| HPV33 | L2 | SGPDIPSPLF | 406 | 10 | | 37106 |
| HPV33 | L2 | SGSGGRTGY | 63 | 9 | | 37107 |
| HPV33 | L2 | SINDGLYDVY | 357 | 10 | | 37108 |
| HPV33 | L2 | SINDGLYDVYA | 357 | 11 | | 37109 |
| HPV33 | L2 | SIPLNTGF | 393 | 8 | | 37110 |
| HPV33 | L2 | SIPTPSGF | 122 | 8 | | 37111 |
| HPV33 | L2 | SIQTISTH | 151 | 8 | | 37112 |
| HPV33 | L2 | SIVSLIEETSF | 103 | 11 | | 37113 |
| HPV33 | L2 | SLIEETSF | 106 | 8 | | 37114 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV33 | L2 | SLIEETSFIEA | 106 | 11 | | 37115 |
| HPV33 | L2 | SSIQTISTH | 150 | 9 | | 37116 |
| HPV33 | L2 | SSPFVPISPF | 418 | 10 | | 37117 |
| HPV33 | L2 | SSPFVPISPFF | 418 | 11 | | 37118 |
| HPV33 | L2 | SSPTVSTQSY | 184 | 10 | | 37119 |
| HPV33 | L2 | SSTPIPGSR | 212 | 9 | | 37120 |
| HPV33 | L2 | SSYSINDGLY | 354 | 10 | | 37121 |
| HPV33 | L2 | STHLNPTF | 156 | 8 | | 37122 |
| HPV33 | L2 | STIADQILK | 38 | 9 | | 37123 |
| HPV33 | L2 | STIADQILKY | 38 | 10 | | 37124 |
| HPV33 | L2 | STPIPGSR | 213 | 8 | | 37125 |
| HPV33 | L2 | STPIPGSRPVA | 213 | 11 | | 37126 |
| HPV33 | L2 | STRRKRASA | 6 | 9 | | 37127 |
| HPV33 | L2 | SVLHPPAPA | 167 | 9 | | 37128 |
| HPV33 | L2 | SVLHPPAPAEA | 167 | 11 | | 37129 |
| HPV33 | L2 | TAAIPLQPIR | 80 | 10 | | 37130 |
| HPV33 | L2 | TCPPDVIPK | 26 | 9 | | 37131 |
| HPV33 | L2 | TFTEPSVLH | 162 | 9 | | 37132 |
| HPV33 | L2 | TGSGSGGR | 61 | 8 | | 37133 |
| HPV33 | L2 | TGSGSGGRTGY | 61 | 11 | | 37134 |
| HPV33 | L2 | TGTCPPDVIPK | 24 | 11 | | 37135 |
| HPV33 | L2 | TIADQILK | 39 | 8 | | 37136 |
| HPV33 | L2 | TIADQILKY | 39 | 9 | | 37137 |
| HPV33 | L2 | TISTHLNPTF | 154 | 10 | | 37138 |
| HPV33 | L2 | TIVVDGADF | 432 | 9 | | 37139 |
| HPV33 | L2 | TLKTRSGK | 309 | 8 | | 37140 |
| HPV33 | L2 | TSADTTPA | 133 | 8 | | 37141 |
| HPV33 | L2 | TSFIEAGA | 111 | 8 | | 37142 |
| HPV33 | L2 | TSFIEAGAPA | 111 | 10 | | 37143 |
| HPV33 | L2 | TSPHKLITY | 244 | 9 | | 37144 |
| HPV33 | L2 | TSRRHTVR | 293 | 8 | | 37145 |
| HPV33 | L2 | TSRRHTVRF | 293 | 9 | | 37146 |
| HPV33 | L2 | TSRRHTVRFSR | 293 | 11 | | 37147 |
| HPV33 | L2 | TSSPFVPISPF | 417 | 11 | | 37148 |
| HPV33 | L2 | TSSTPIPGSR | 211 | 10 | | 37149 |
| HPV33 | L2 | TSSYSINDGLY | 353 | 11 | | 37150 |
| HPV33 | L2 | TTSADTTPA | 132 | 9 | | 37151 |
| HPV33 | L2 | TVRFSRVGQK | 298 | 10 | | 37152 |
| HPV33 | L2 | TVRFSRVGQKA | 298 | 11 | | 37153 |
| HPV33 | L2 | VARLGLYSR | 222 | 9 | | 37154 |
| HPV33 | L2 | VDGADFVLH | 435 | 9 | | 37155 |
| HPV33 | L2 | VDNVHTPMQH | 370 | 10 | | 37156 |
| HPV33 | L2 | VDPAFLTSPH | 238 | 10 | | 37157 |
| HPV33 | L2 | VDPAFLTSPHK | 238 | 11 | | 37158 |
| HPV33 | L2 | VGQKATLK | 304 | 8 | | 37159 |
| HPV33 | L2 | VGQKATLKTR | 304 | 10 | | 37160 |
| HPV33 | L2 | VIPKVEGSTIA | 31 | 11 | | 37161 |
| HPV33 | L2 | VLHPPAPA | 168 | 8 | | 37162 |
| HPV33 | L2 | VLHPPAPAEA | 168 | 10 | | 37163 |
| HPV33 | L2 | VLHPSYFILR | 441 | 10 | | 37164 |
| HPV33 | L2 | VLHPSYFILRR | 441 | 11 | | 37165 |
| HPV33 | L2 | VSIPLNTGF | 392 | 9 | | 37166 |
| HPV33 | L2 | VSLIEETSF | 105 | 9 | | 37167 |
| HPV33 | L2 | VTSSTPIPGSR | 210 | 11 | | 37168 |
| HPV33 | L2 | VTTSADTTPA | 131 | 10 | | 37169 |
| HPV33 | L2 | VVDGADFVLH | 434 | 10 | | 37170 |
| HPV33 | L2 | VVDPAFLTSPH | 237 | 11 | | 37171 |
| HPV33 | L2 | YADDVDNVH | 366 | 9 | | 37172 |
| HPV33 | L2 | YDNPAFESF | 252 | 9 | | 37173 |
| HPV33 | L2 | YFFTDVRVA | 458 | 9 | | 37174 |
| HPV33 | L2 | YFFTDVRVAA | 458 | 10 | | 37175 |
| HPV33 | L2 | YFILRRRR | 446 | 8 | | 37176 |
| HPV33 | L2 | YFILRRRRK | 446 | 9 | | 37177 |
| HPV33 | L2 | YFILRRRRKR | 446 | 10 | | 37178 |
| HPV33 | L2 | YFILRRRRKRF | 446 | 11 | | 37179 |
| HPV33 | L2 | YGSLGVFF | 47 | 8 | | 37180 |
| HPV33 | L2 | YSINDGLY | 356 | 8 | | 37181 |
| HPV33 | L2 | YSINDGLYDVY | 356 | 11 | | 37182 |
| HPV33 | L2 | YSRNTQQVK | 228 | 9 | | 37183 |
| HPV33 | L2 | YSTFATTR | 381 | 8 | | 37184 |
| HPV33 | L2 | YVPIGTDPPTA | 71 | 11 | | 37185 |
| HPV45 | E1 | AAAFLKSNCQA | 382 | 11 | | 37186 |
| HPV45 | E1 | AAFLKSNCQA | 383 | 10 | | 37187 |
| HPV45 | E1 | AAFLKSNCQAK | 383 | 11 | | 37188 |
| HPV45 | E1 | AAMLAVFK | 198 | 8 | | 37189 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E1 | AAMLAVFKDIY | 198 | 11 | | 37190 |
| HPV45 | E1 | ADCNSNAA | 376 | 8 | | 37191 |
| HPV45 | E1 | ADCNSNAAA | 376 | 9 | | 37192 |
| HPV45 | E1 | ADCNSNAAAF | 376 | 10 | | 37193 |
| HPV45 | E1 | ADTEGIPF | 622 | 8 | | 37194 |
| HPV45 | E1 | ADTEGIPFGTF | 622 | 11 | | 37195 |
| HPV45 | E1 | ADTKVAMLDDA | 507 | 11 | | 37196 |
| HPV45 | E1 | AFLKSNCQA | 384 | 9 | | 37197 |
| HPV45 | E1 | AFLKSNCQAK | 384 | 10 | | 37198 |
| HPV45 | E1 | AFLKSNCQAKY | 384 | 11 | | 37199 |
| HPV45 | E1 | AFQYAQLA | 369 | 8 | | 37200 |
| HPV45 | E1 | AIFGVNPTVA | 232 | 10 | | 37201 |
| HPV45 | E1 | AIISFVNSNSH | 490 | 11 | | 37202 |
| HPV45 | E1 | ALDGNPISIDR | 532 | 11 | | 37203 |
| HPV45 | E1 | ALKEFLKGTPK | 452 | 11 | | 37204 |
| HPV45 | E1 | ALLRYKCGK | 270 | 9 | 0.0900 | 37205 |
| HPV45 | E1 | ALLRYKCGKNR | 270 | 11 | | 37206 |
| HPV45 | E1 | AMLAVFKDIY | 199 | 10 | | 37207 |
| HPV45 | E1 | AMLDDATH | 512 | 8 | | 37208 |
| HPV45 | E1 | ASNKKAAMLA | 193 | 10 | | 37209 |
| HPV45 | E1 | ATDTGSDMVDF | 40 | 11 | | 37210 |
| HPV45 | E1 | ATHTCWTY | 517 | 8 | | 37211 |
| HPV45 | E1 | ATHTCWTYF | 517 | 9 | | 37212 |
| HPV45 | E1 | AVFKDIYGLSF | 202 | 11 | | 37213 |
| HPV45 | E1 | AVMCRHYK | 399 | 8 | | 37214 |
| HPV45 | E1 | AVMCRHYKR | 399 | 9 | | 37215 |
| HPV45 | E1 | AVMCRHYKRA | 399 | 10 | | 37216 |
| HPV45 | E1 | CAVMCRHY | 398 | 8 | | 37217 |
| HPV45 | E1 | CAVMCRHYK | 398 | 9 | | 37218 |
| HPV45 | E1 | CAVMCRHYKR | 398 | 10 | | 37219 |
| HPV45 | E1 | CAVMCRHYKRA | 398 | 11 | | 37220 |
| HPV45 | E1 | CFFERTWSR | 604 | 9 | | 37221 |
| HPV45 | E1 | CGKNRLTVA | 276 | 9 | | 37222 |
| HPV45 | E1 | CGKNRLTVAK | 276 | 10 | | 37223 |
| HPV45 | E1 | CILLYGPA | 465 | 8 | | 37224 |
| HPV45 | E1 | CMLIEPPK | 297 | 8 | | 37225 |
| HPV45 | E1 | CMLIEPPKLR | 297 | 10 | | 37226 |
| HPV45 | E1 | CSKIDEGGDWR | 423 | 11 | | 37227 |
| HPV45 | E1 | CTDWVMAIF | 226 | 9 | | 37228 |
| HPV45 | E1 | CVTGQNTR | 634 | 8 | | 37229 |
| HPV45 | E1 | DADTEGIPF | 621 | 9 | | 37230 |
| HPV45 | E1 | DAQVLHLLK | 78 | 9 | | 37231 |
| HPV45 | E1 | DAQVLHLLKR | 78 | 10 | | 37232 |
| HPV45 | E1 | DAQVLHLLKRK | 78 | 11 | | 37233 |
| HPV45 | E1 | DATHTCWTY | 516 | 9 | | 37234 |
| HPV45 | E1 | DATHTCWTYF | 516 | 10 | | 37235 |
| HPV45 | E1 | DCAVMCRH | 397 | 8 | | 37236 |
| HPV45 | E1 | DCAVMCRHY | 397 | 9 | | 37237 |
| HPV45 | E1 | DCAVMCRHYK | 397 | 10 | | 37238 |
| HPV45 | E1 | DCAVMCRHYKR | 397 | 11 | | 37239 |
| HPV45 | E1 | DCKWGVLILA | 261 | 10 | | 37240 |
| HPV45 | E1 | DCNSNAAA | 377 | 8 | | 37241 |
| HPV45 | E1 | DCNSNAAAF | 377 | 9 | | 37242 |
| HPV45 | E1 | DCNSNAAAFLK | 377 | 11 | | 37243 |
| HPV45 | E1 | DDATHTCWTY | 515 | 10 | | 37244 |
| HPV45 | E1 | DDATHTCWTYF | 515 | 11 | | 37245 |
| HPV45 | E1 | DGEGTGCNGWF | 8 | 11 | | 37246 |
| HPV45 | E1 | DGNPISIDR | 534 | 9 | | 37247 |
| HPV45 | E1 | DGNPISIDRK | 534 | 10 | | 37248 |
| HPV45 | E1 | DGNPISIDRKH | 534 | 11 | | 37249 |
| HPV45 | E1 | DLHEDDEDA | 614 | 9 | | 37250 |
| HPV45 | E1 | DLSDMVQWA | 349 | 9 | | 37251 |
| HPV45 | E1 | DLSDMVQWAF | 349 | 10 | | 37252 |
| HPV45 | E1 | DLTDESDMA | 361 | 9 | | 37253 |
| HPV45 | E1 | DLTDESDMAF | 361 | 10 | | 37254 |
| HPV45 | E1 | DLVRNFKSDK | 214 | 10 | | 37255 |
| HPV45 | E1 | DMAFQYAQLA | 367 | 10 | | 37256 |
| HPV45 | E1 | DSGYGCSEVEA | 134 | 11 | | 37257 |
| HPV45 | E1 | DTEGIPFGTF | 623 | 10 | | 37258 |
| HPV45 | E1 | DTEGIPFGTFK | 623 | 11 | | 37259 |
| HPV45 | E1 | DTGSDMVDF | 42 | 9 | | 37260 |
| HPV45 | E1 | DTKVAMLDDA | 508 | 10 | | 37261 |
| HPV45 | E1 | DTPEWIQR | 328 | 8 | | 37262 |
| HPV45 | E1 | DTQLSICEQA | 52 | 10 | | 37263 |
| HPV45 | E1 | DVISDDEDETA | 30 | 11 | | 37264 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E1 | EDADTEGIPF | 620 | 10 | | 37265 |
| HPV45 | E1 | EFISFLRA | 445 | 8 | | 37266 |
| HPV45 | E1 | EFISFLRALK | 445 | 10 | | 37267 |
| HPV45 | E1 | EFLKGTPK | 455 | 8 | | 37268 |
| HPV45 | E1 | EFLKGTPKK | 455 | 9 | | 37269 |
| HPV45 | E1 | EGFKTLIK | 242 | 8 | | 37270 |
| HPV45 | E1 | EGFKTLIKPA | 242 | 10 | | 37271 |
| HPV45 | E1 | EGGDWRPIVQF | 428 | 11 | | 37272 |
| HPV45 | E1 | EGIPFGTF | 625 | 8 | | 37273 |
| HPV45 | E1 | EGIPFGTFK | 625 | 9 | | 37274 |
| HPV45 | E1 | EGTGCNGWF | 10 | 9 | 0.0008 | 37275 |
| HPV45 | E1 | EGTGCNGWFF | 10 | 10 | | 37276 |
| HPV45 | E1 | EINDKNWK | 596 | 8 | | 37277 |
| HPV45 | E1 | EINDKNWKCF | 596 | 10 | | 37278 |
| HPV45 | E1 | EINDKNWKCFF | 596 | 11 | | 37279 |
| HPV45 | E1 | EISLNSGH | 115 | 8 | | 37280 |
| HPV45 | E1 | EISLNSGHK | 115 | 9 | | 37281 |
| HPV45 | E1 | EISLNSGHKK | 115 | 10 | | 37282 |
| HPV45 | E1 | EISLNSGHKKA | 115 | 11 | | 37283 |
| HPV45 | E1 | ELKELLQA | 186 | 8 | | 37284 |
| HPV45 | E1 | ELKELLQASNK | 186 | 11 | | 37285 |
| HPV45 | E1 | ELLQASNK | 189 | 8 | | 37286 |
| HPV45 | E1 | ELLQASNKK | 189 | 9 | | 37287 |
| HPV45 | E1 | ELLQASNKKA | 189 | 10 | | 37288 |
| HPV45 | E1 | ELLQASNKKAA | 189 | 11 | | 37289 |
| HPV45 | E1 | ESDMAFQY | 365 | 8 | | 37290 |
| HPV45 | E1 | ESDMAFQYA | 365 | 9 | | 37291 |
| HPV45 | E1 | ESRVTVFTF | 573 | 9 | | 37292 |
| HPV45 | E1 | ESRVTVFTFPH | 573 | 11 | | 37293 |
| HPV45 | E1 | ETAQALFH | 64 | 8 | | 37294 |
| HPV45 | E1 | ETAQALFHA | 64 | 9 | | 37295 |
| HPV45 | E1 | ETCMLIEPPK | 295 | 10 | | 37296 |
| HPV45 | E1 | ETQVTVNTNA | 146 | 10 | | 37297 |
| HPV45 | E1 | EVQNDAQVLH | 74 | 10 | | 37298 |
| HPV45 | E1 | FDKNGNPVY | 587 | 9 | | 37299 |
| HPV45 | E1 | FDLSDMVQWA | 348 | 10 | | 37300 |
| HPV45 | E1 | FDLSDMVQWAF | 348 | 11 | | 37301 |
| HPV45 | E1 | FDNYMRNA | 525 | 8 | | 37302 |
| HPV45 | E1 | FFERTWSR | 605 | 8 | | 37303 |
| HPV45 | E1 | FFVETIVEK | 18 | 9 | | 37304 |
| HPV45 | E1 | FFVETIVEKK | 18 | 10 | | 37305 |
| HPV45 | E1 | FGMSFIHF | 479 | 8 | | 37306 |
| HPV45 | E1 | FGVNPTVA | 234 | 8 | | 37307 |
| HPV45 | E1 | FGVNPTVAEGF | 234 | 11 | | 37308 |
| HPV45 | E1 | FIHFLQGA | 483 | 8 | | 37309 |
| HPV45 | E1 | FISFLRALK | 446 | 9 | | 37310 |
| HPV45 | E1 | FISFLRALKEF | 446 | 11 | | 37311 |
| HPV45 | E1 | FLKGTPKK | 456 | 8 | | 37312 |
| HPV45 | E1 | FLKSNCQA | 385 | 8 | | 37313 |
| HPV45 | E1 | FLKSNCQAK | 385 | 9 | 0.0035 | 37314 |
| HPV45 | E1 | FLKSNCQAKY | 385 | 10 | | 37315 |
| HPV45 | E1 | FLQGAIISF | 486 | 9 | | 37316 |
| HPV45 | E1 | FLRALKEF | 449 | 8 | | 37317 |
| HPV45 | E1 | FLRALKEFLK | 449 | 10 | | 37318 |
| HPV45 | E1 | FLRYQGVEF | 438 | 9 | | 37319 |
| HPV45 | E1 | FTDLVRNF | 212 | 8 | | 37320 |
| HPV45 | E1 | FTDLVRNFK | 212 | 9 | | 37321 |
| HPV45 | E1 | FTFPHAFPF | 579 | 9 | | 37322 |
| HPV45 | E1 | FTFPHAFPFDK | 579 | 11 | | 37323 |
| HPV45 | E1 | FTISDSGY | 130 | 8 | | 37324 |
| HPV45 | E1 | FVETIVEK | 19 | 8 | | 37325 |
| HPV45 | E1 | FVETIVEKK | 19 | 9 | | 37326 |
| HPV45 | E1 | FVNSNSHF | 494 | 8 | | 37327 |
| HPV45 | E1 | GCSEVEAA | 138 | 8 | | 37328 |
| HPV45 | E1 | GDTPEWIQR | 327 | 9 | 0.0008 | 37329 |
| HPV45 | E1 | GDWRPIVQF | 430 | 9 | | 37330 |
| HPV45 | E1 | GDWRPIVQFLR | 430 | 11 | | 37331 |
| HPV45 | E1 | GFKTLIKPA | 243 | 9 | | 37332 |
| HPV45 | E1 | GGDSSDNA | 168 | 8 | | 37333 |
| HPV45 | E1 | GGDWRPIVQF | 429 | 10 | | 37334 |
| HPV45 | E1 | GIPFGTFK | 626 | 8 | | 37335 |
| HPV45 | E1 | GLSFTDLVR | 209 | 9 | 0.0009 | 37336 |
| HPV45 | E1 | GLSFTDLVRNF | 209 | 11 | | 37337 |
| HPV45 | E1 | GMSFIHFLQGA | 480 | 11 | | 37338 |
| HPV45 | E1 | GTGCNGWF | 11 | 8 | | 37339 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E1 | GTGCNGWFF | 11 | 9 | | 37340 |
| HPV45 | E1 | GTPKKNCILLY | 459 | 11 | | 37341 |
| HPV45 | E1 | GVEFISFLR | 443 | 9 | | 37342 |
| HPV45 | E1 | GVEFISFLRA | 443 | 10 | | 37343 |
| HPV45 | E1 | GVLILALLR | 265 | 9 | 0.0058 | 37344 |
| HPV45 | E1 | GVLILALLRY | 265 | 10 | | 37345 |
| HPV45 | E1 | GVLILALLRYK | 265 | 11 | | 37346 |
| HPV45 | E1 | GVNPTVAEGF | 235 | 10 | | 37347 |
| HPV45 | E1 | GVNPTVAEGFK | 235 | 11 | | 37348 |
| HPV45 | E1 | HAQEVQNDA | 71 | 9 | | 37349 |
| HPV45 | E1 | HCSITELK | 181 | 8 | | 37350 |
| HPV45 | E1 | HFLQGAIISF | 485 | 10 | | 37351 |
| HPV45 | E1 | HFWLEPLA | 500 | 8 | | 37352 |
| HPV45 | E1 | HFWLEPLADTK | 500 | 11 | | 37353 |
| HPV45 | E1 | HGIDDSNF | 341 | 8 | | 37354 |
| HPV45 | E1 | HIQCLDCK | 256 | 8 | | 37355 |
| HPV45 | E1 | HLLKRKFA | 83 | 8 | | 37356 |
| HPV45 | E1 | HTCWTYFDNY | 519 | 10 | | 37357 |
| HPV45 | E1 | ICEQAEQETA | 57 | 10 | | 37358 |
| HPV45 | E1 | IDEGGDWR | 426 | 8 | | 37359 |
| HPV45 | E1 | IDPAKDNK | 561 | 8 | | 37360 |
| HPV45 | E1 | IDPAKDNKWPY | 561 | 11 | | 37361 |
| HPV45 | E1 | IDTQLSICEQA | 51 | 11 | | 37362 |
| HPV45 | E1 | IFGVNPTVA | 233 | 9 | | 37363 |
| HPV45 | E1 | IIQHGIDDSNF | 338 | 11 | | 37364 |
| HPV45 | E1 | IISFVNSNSH | 491 | 10 | | 37365 |
| HPV45 | E1 | IISFVNSNSHF | 491 | 11 | | 37366 |
| HPV45 | E1 | ILALLRYK | 268 | 8 | | 37367 |
| HPV45 | E1 | ILALLRYKCGK | 268 | 11 | | 37368 |
| HPV45 | E1 | ILLTSNIDPA | 555 | 10 | | 37369 |
| HPV45 | E1 | ILLTSNIDPAK | 555 | 11 | | 37370 |
| HPV45 | E1 | ILLYGPANTGK | 466 | 11 | | 37371 |
| HPV45 | E1 | ISDDEDETA | 32 | 9 | | 37372 |
| HPV45 | E1 | ISFLRALK | 447 | 8 | | 37373 |
| HPV45 | E1 | ISFLRALKEF | 447 | 10 | | 37374 |
| HPV45 | E1 | ISFVNSNSH | 492 | 9 | | 37375 |
| HPV45 | E1 | ISFVNSNSHF | 492 | 10 | | 37376 |
| HPV45 | E1 | ISIDRKHK | 538 | 8 | | 37377 |
| HPV45 | E1 | ISLNSGHK | 116 | 8 | | 37378 |
| HPV45 | E1 | ISLNSGHKK | 116 | 9 | | 37379 |
| HPV45 | E1 | ISLNSGHKKA | 116 | 10 | | 37380 |
| HPV45 | E1 | ISLNSGHKKAK | 116 | 11 | | 37381 |
| HPV45 | E1 | ITELKELLQA | 184 | 10 | | 37382 |
| HPV45 | E1 | KAAMLAVF | 197 | 8 | | 37383 |
| HPV45 | E1 | KAAMLAVFK | 197 | 9 | | 37384 |
| HPV45 | E1 | KCFFERTWSR | 603 | 10 | | 37385 |
| HPV45 | E1 | KCGKNRLTVA | 275 | 10 | | 37386 |
| HPV45 | E1 | KCGKNRLTVAK | 275 | 11 | | 37387 |
| HPV45 | E1 | KCVTGQNTR | 633 | 9 | | 37388 |
| HPV45 | E1 | KDCAVMCR | 396 | 8 | | 37389 |
| HPV45 | E1 | KDCAVMCRH | 396 | 9 | | 37390 |
| HPV45 | E1 | KDCAVMCRHY | 396 | 10 | | 37391 |
| HPV45 | E1 | KDCAVMCRHYK | 396 | 11 | | 37392 |
| HPV45 | E1 | KDIYGLSF | 205 | 8 | | 37393 |
| HPV45 | E1 | KDNKWPYLESR | 565 | 11 | | 37394 |
| HPV45 | E1 | KGLSTLLH | 285 | 8 | | 37395 |
| HPV45 | E1 | KIDEGGDWR | 425 | 9 | | 37396 |
| HPV45 | E1 | KLRSSVAA | 304 | 8 | | 37397 |
| HPV45 | E1 | KLRSSVAALY | 304 | 10 | | 37398 |
| HPV45 | E1 | KSNCQAKY | 387 | 8 | | 37399 |
| HPV45 | E1 | KSNCQAKYLK | 387 | 10 | | 37400 |
| HPV45 | E1 | KSYFGMSF | 476 | 8 | | 37401 |
| HPV45 | E1 | KSYFGMSFIH | 476 | 10 | | 37402 |
| HPV45 | E1 | KSYFGMSFIHF | 476 | 11 | | 37403 |
| HPV45 | E1 | KTLIKPATLY | 245 | 10 | | 37404 |
| HPV45 | E1 | KTLIKPATLYA | 245 | 11 | | 37405 |
| HPV45 | E1 | KTTCTDWVMA | 223 | 10 | | 37406 |
| HPV45 | E1 | KVAMLDDA | 510 | 8 | | 37407 |
| HPV45 | E1 | KVAMLDDATH | 510 | 10 | | 37408 |
| HPV45 | E1 | LADCNSNA | 375 | 8 | | 37409 |
| HPV45 | E1 | LADCNSNAA | 375 | 9 | | 37410 |
| HPV45 | E1 | LADCNSNAAA | 375 | 10 | | 37411 |
| HPV45 | E1 | LADCNSNAAAF | 375 | 11 | | 37412 |
| HPV45 | E1 | LALLRYKCGK | 269 | 10 | | 37413 |
| HPV45 | E1 | LAVFKDIY | 201 | 8 | | 37414 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E1 | LDCKWGVLILA | 260 | 11 | | 37415 |
| HPV45 | E1 | LDDATHTCWTY | 514 | 11 | | 37416 |
| HPV45 | E1 | LDGNPISIDR | 533 | 10 | | 37417 |
| HPV45 | E1 | LDGNPISIDRK | 533 | 11 | | 37418 |
| HPV45 | E1 | LDLHEDDEDA | 613 | 10 | | 37419 |
| HPV45 | E1 | LFHAQEVQNDA | 69 | 11 | | 37420 |
| HPV45 | E1 | LFTISDSGY | 129 | 9 | | 37421 |
| HPV45 | E1 | LIEPPKLR | 299 | 8 | | 37422 |
| HPV45 | E1 | LIKPATLY | 247 | 8 | | 37423 |
| HPV45 | E1 | LIKPATLYA | 247 | 9 | | 37424 |
| HPV45 | E1 | LIKPATLYAH | 247 | 10 | | 37425 |
| HPV45 | E1 | LILALLRY | 267 | 8 | | 37426 |
| HPV45 | E1 | LILALLRYK | 267 | 9 | 0.2700 | 37427 |
| HPV45 | E1 | LLKRKFAGGSK | 84 | 11 | | 37428 |
| HPV45 | E1 | LLQASNKK | 190 | 8 | | 37429 |
| HPV45 | E1 | LLQASNKKA | 190 | 9 | | 37430 |
| HPV45 | E1 | LLQASNKKAA | 190 | 10 | | 37431 |
| HPV45 | E1 | LLRYKCGK | 271 | 8 | | 37432 |
| HPV45 | E1 | LLRYKCGKNR | 271 | 10 | | 37433 |
| HPV45 | E1 | LLTSNIDPA | 556 | 9 | | 37434 |
| HPV45 | E1 | LLTSNIDPAK | 556 | 10 | | 37435 |
| HPV45 | E1 | LLYGPANTGK | 467 | 10 | | 37436 |
| HPV45 | E1 | LSDMVQWA | 350 | 8 | | 37437 |
| HPV45 | E1 | LSDMVQWAF | 350 | 9 | | 37438 |
| HPV45 | E1 | LSFTDLVR | 210 | 8 | | 37439 |
| HPV45 | E1 | LSFTDLVRNF | 210 | 10 | | 37440 |
| HPV45 | E1 | LSFTDLVRNFK | 210 | 11 | | 37441 |
| HPV45 | E1 | LSVDTDLSPR | 103 | 10 | | 37442 |
| HPV45 | E1 | LTDESDMA | 362 | 8 | | 37443 |
| HPV45 | E1 | LTDESDMAF | 362 | 9 | | 37444 |
| HPV45 | E1 | LTDESDMAFQY | 362 | 11 | | 37445 |
| HPV45 | E1 | LTSNIDPA | 557 | 8 | | 37446 |
| HPV45 | E1 | LTSNIDPAK | 557 | 9 | | 37447 |
| HPV45 | E1 | LVRNFKSDK | 215 | 9 | 0.0005 | 37448 |
| HPV45 | E1 | MAFQYAQLA | 368 | 9 | | 37449 |
| HPV45 | E1 | MAIFGVNPTVA | 231 | 11 | | 37450 |
| HPV45 | E1 | MCRHYKRA | 401 | 8 | | 37451 |
| HPV45 | E1 | MCRHYKRAQK | 401 | 10 | | 37452 |
| HPV45 | E1 | MCRHYKRAQKR | 401 | 11 | | 37453 |
| HPV45 | E1 | MLAVFKDIY | 200 | 9 | | 37454 |
| HPV45 | E1 | MLIEPPKLR | 298 | 9 | | 37455 |
| HPV45 | E1 | MSFIHFLQGA | 481 | 10 | | 37456 |
| HPV45 | E1 | MSQWIKYR | 415 | 8 | | 37457 |
| HPV45 | E1 | MSQWIKYRCSK | 415 | 11 | | 37458 |
| HPV45 | E1 | NAENGGSVH | 154 | 9 | | 37459 |
| HPV45 | E1 | NAENVDPH | 174 | 8 | | 37460 |
| HPV45 | E1 | NCILLYGPA | 464 | 9 | | 37461 |
| HPV45 | E1 | NCQAKYLK | 389 | 8 | | 37462 |
| HPV45 | E1 | NCQAKYLKDCA | 389 | 11 | | 37463 |
| HPV45 | E1 | NDAQVLHLLK | 77 | 10 | | 37464 |
| HPV45 | E1 | NDAQVLHLLKR | 77 | 11 | | 37465 |
| HPV45 | E1 | NDKNWKCF | 598 | 8 | | 37466 |
| HPV45 | E1 | NDKNWKCFF | 598 | 9 | | 37467 |
| HPV45 | E1 | NDKNWKCFFER | 598 | 11 | | 37468 |
| HPV45 | E1 | NDLTDESDMA | 360 | 10 | | 37469 |
| HPV45 | E1 | NDLTDESDMAF | 360 | 11 | | 37470 |
| HPV45 | E1 | NFDLSDMVQWA | 347 | 11 | | 37471 |
| HPV45 | E1 | NGNPVYEINDK | 590 | 11 | | 37472 |
| HPV45 | E1 | NIDPAKDNK | 560 | 9 | | 37473 |
| HPV45 | E1 | NMSQWIKY | 414 | 8 | | 37474 |
| HPV45 | E1 | NMSQWIKYR | 414 | 9 | | 37475 |
| HPV45 | E1 | NSGHKKAK | 119 | 8 | | 37476 |
| HPV45 | E1 | NSGHKKAKR | 119 | 9 | | 37477 |
| HPV45 | E1 | NSGHKKAKRR | 119 | 10 | | 37478 |
| HPV45 | E1 | NSHFWLEPLA | 498 | 10 | | 37479 |
| HPV45 | E1 | NSNAAAFLK | 379 | 9 | 0.0057 | 37480 |
| HPV45 | E1 | NTGKSYFGMSF | 473 | 11 | | 37481 |
| HPV45 | E1 | NTNAENGGSVH | 152 | 11 | | 37482 |
| HPV45 | E1 | PAKDNKWPY | 563 | 9 | | 37483 |
| HPV45 | E1 | PANTGKSY | 471 | 8 | | 37484 |
| HPV45 | E1 | PANTGKSYF | 471 | 9 | | 37485 |
| HPV45 | E1 | PFDKNGNPVY | 586 | 10 | | 37486 |
| HPV45 | E1 | PILLTSNIDPA | 554 | 11 | | 37487 |
| HPV45 | E1 | PISIDRKH | 537 | 8 | | 37488 |
| HPV45 | E1 | PISIDRKHK | 537 | 9 | | 37489 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E1 | PIVQFLRY | 434 | 8 | | 37490 |
| HPV45 | E1 | PLADTKVA | 505 | 8 | | 37491 |
| HPV45 | E1 | PTVAEGFK | 238 | 8 | | 37492 |
| HPV45 | E1 | PVYEINDK | 593 | 8 | | 37493 |
| HPV45 | E1 | PVYEINDKNWK | 593 | 11 | | 37494 |
| HPV45 | E1 | QAEQETAQA | 60 | 9 | | 37495 |
| HPV45 | E1 | QAEQETAQALF | 60 | 11 | | 37496 |
| HPV45 | E1 | QAKYLKDCA | 391 | 9 | | 37497 |
| HPV45 | E1 | QASNKKAA | 192 | 8 | | 37498 |
| HPV45 | E1 | QASNKKAAMLA | 192 | 11 | | 37499 |
| HPV45 | E1 | QFLRYQGVEF | 437 | 10 | | 37500 |
| HPV45 | E1 | QGVEFISF | 442 | 8 | | 37501 |
| HPV45 | E1 | QGVEFISFLR | 442 | 10 | | 37502 |
| HPV45 | E1 | QGVEFISFLRA | 442 | 11 | | 37503 |
| HPV45 | E1 | QLADCNSNA | 374 | 9 | | 37504 |
| HPV45 | E1 | QLADCNSNAA | 374 | 10 | | 37505 |
| HPV45 | E1 | QLADCNSNAAA | 374 | 11 | | 37506 |
| HPV45 | E1 | QLSICEQA | 54 | 8 | | 37507 |
| HPV45 | E1 | QLSVDTDLSPR | 102 | 11 | | 37508 |
| HPV45 | E1 | QMNMSQWIK | 412 | 9 | | 37509 |
| HPV45 | E1 | QMNMSQWIKY | 412 | 10 | | 37510 |
| HPV45 | E1 | QMNMSQWIKYR | 412 | 11 | | 37511 |
| HPV45 | E1 | QSSGGDSSDNA | 165 | 11 | | 37512 |
| HPV45 | E1 | QVLHLLKR | 80 | 8 | | 37513 |
| HPV45 | E1 | QVLHLLKRK | 80 | 9 | | 37514 |
| HPV45 | E1 | QVLHLLKRKF | 80 | 10 | | 37515 |
| HPV45 | E1 | QVLHLLKRKFA | 80 | 11 | | 37516 |
| HPV45 | E1 | QVTVNTNA | 148 | 8 | | 37517 |
| HPV45 | E1 | RALKEFLK | 451 | 8 | | 37518 |
| HPV45 | E1 | RLDLHEDDEDA | 612 | 11 | | 37519 |
| HPV45 | E1 | RLFTISDSGY | 128 | 10 | | 37520 |
| HPV45 | E1 | RLQEISLNSGH | 112 | 11 | | 37521 |
| HPV45 | E1 | RSSVAALY | 306 | 8 | | 37522 |
| HPV45 | E1 | RSSVAALYWY | 306 | 10 | | 37523 |
| HPV45 | E1 | RSSVAALYWYR | 306 | 11 | | 37524 |
| HPV45 | E1 | RTWSRLDLH | 608 | 9 | | 37525 |
| HPV45 | E1 | RVTVFTFPH | 575 | 9 | | 37526 |
| HPV45 | E1 | RVTVFTFPHA | 575 | 10 | | 37527 |
| HPV45 | E1 | RVTVFTFPHAF | 575 | 11 | | 37528 |
| HPV45 | E1 | SDDEDETA | 33 | 8 | | 37529 |
| HPV45 | E1 | SDMAFQYA | 366 | 8 | | 37530 |
| HPV45 | E1 | SDMAFQYAQLA | 366 | 11 | | 37531 |
| HPV45 | E1 | SDMVQWAF | 351 | 8 | | 37532 |
| HPV45 | E1 | SDNAENVDPH | 172 | 10 | | 37533 |
| HPV45 | E1 | SFIHFLQGA | 482 | 9 | | 37534 |
| HPV45 | E1 | SFLRALKEF | 448 | 9 | | 37535 |
| HPV45 | E1 | SFLRALKEFLK | 448 | 11 | | 37536 |
| HPV45 | E1 | SFTDLVRNF | 211 | 9 | | 37537 |
| HPV45 | E1 | SFTDLVRNFK | 211 | 10 | | 37538 |
| HPV45 | E1 | SFVNSNSH | 493 | 8 | | 37539 |
| HPV45 | E1 | SFVNSNSHF | 493 | 9 | | 37540 |
| HPV45 | E1 | SGDTPEWIQR | 326 | 10 | | 37541 |
| HPV45 | E1 | SGGDSSDNA | 167 | 9 | | 37542 |
| HPV45 | E1 | SGHKKAKR | 120 | 8 | | 37543 |
| HPV45 | E1 | SGHKKAKRR | 120 | 9 | | 37544 |
| HPV45 | E1 | SGHKKAKRRLF | 120 | 11 | | 37545 |
| HPV45 | E1 | SGYGCSEVEA | 135 | 10 | | 37546 |
| HPV45 | E1 | SGYGCSEVEAA | 135 | 11 | | 37547 |
| HPV45 | E1 | SICEQAEQETA | 56 | 11 | | 37548 |
| HPV45 | E1 | SITELKELLQA | 183 | 11 | | 37549 |
| HPV45 | E1 | SLNSGHKK | 117 | 8 | | 37550 |
| HPV45 | E1 | SLNSGHKKA | 117 | 9 | | 37551 |
| HPV45 | E1 | SLNSGHKKAK | 117 | 10 | | 37552 |
| HPV45 | E1 | SLNSGHKKAKR | 117 | 11 | | 37553 |
| HPV45 | E1 | SSDNAENVDPH | 171 | 11 | | 37554 |
| HPV45 | E1 | SSGGDSSDNA | 166 | 10 | | 37555 |
| HPV45 | E1 | SSVAALYWY | 307 | 9 | | 37556 |
| HPV45 | E1 | SSVAALYWYR | 307 | 10 | | 37557 |
| HPV45 | E1 | SVAALYWY | 308 | 8 | | 37558 |
| HPV45 | E1 | SVAALYWYR | 308 | 9 | 2.9000 | 37559 |
| HPV45 | E1 | SVDTDLSPR | 104 | 9 | | 37560 |
| HPV45 | E1 | TAQALFHA | 65 | 8 | | 37561 |
| HPV45 | E1 | TCMLIEPPK | 296 | 9 | | 37562 |
| HPV45 | E1 | TCMLIEPPKLR | 296 | 11 | | 37563 |
| HPV45 | E1 | TCTDWVMA | 225 | 8 | | 37564 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E1 | TCTDWVMAIF | 225 | 10 | | 37565 |
| HPV45 | E1 | TCWTYFDNY | 520 | 9 | | 37566 |
| HPV45 | E1 | TCWTYFDNYMR | 520 | 11 | | 37567 |
| HPV45 | E1 | TDESDMAF | 363 | 8 | | 37568 |
| HPV45 | E1 | TDESDMAFQY | 363 | 10 | | 37569 |
| HPV45 | E1 | TDESDMAFQYA | 363 | 11 | | 37570 |
| HPV45 | E1 | TDLVRNFK | 213 | 8 | | 37571 |
| HPV45 | E1 | TDLVRNFKSDK | 213 | 11 | | 37572 |
| HPV45 | E1 | TDTGSDMVDF | 41 | 10 | | 37573 |
| HPV45 | E1 | TDWVMAIF | 227 | 8 | | 37574 |
| HPV45 | E1 | TFKCVTGQNTR | 631 | 11 | | 37575 |
| HPV45 | E1 | TFPHAFPF | 580 | 8 | | 37576 |
| HPV45 | E1 | TFPHAFPFDK | 580 | 10 | | 37577 |
| HPV45 | E1 | TGCNGWFF | 12 | 8 | | 37578 |
| HPV45 | E1 | TGKSYFGMSF | 474 | 10 | | 37579 |
| HPV45 | E1 | TGSDMVDF | 43 | 8 | | 37580 |
| HPV45 | E1 | TLIKPATLY | 246 | 9 | | 37581 |
| HPV45 | E1 | TLIKPATLYA | 246 | 10 | | 37582 |
| HPV45 | E1 | TLIKPATLYAH | 246 | 11 | | 37583 |
| HPV45 | E1 | TSNIDPAK | 558 | 8 | | 37584 |
| HPV45 | E1 | TSNIDPAKDNK | 558 | 11 | | 37585 |
| HPV45 | E1 | TTCTDWVMA | 224 | 9 | | 37586 |
| HPV45 | E1 | TTCTDWVMAIF | 224 | 11 | | 37587 |
| HPV45 | E1 | TVAEGFKTLIK | 239 | 11 | | 37588 |
| HPV45 | E1 | TVAKGLSTLLH | 282 | 11 | | 37589 |
| HPV45 | E1 | TVFTFPHA | 577 | 8 | | 37590 |
| HPV45 | E1 | TVFTFPHAF | 577 | 9 | | 37591 |
| HPV45 | E1 | TVFTFPHAFPF | 577 | 11 | | 37592 |
| HPV45 | E1 | VAALYWYR | 309 | 8 | | 37593 |
| HPV45 | E1 | VAEGFKTLIK | 240 | 10 | | 37594 |
| HPV45 | E1 | VAKGLSTLLH | 283 | 10 | | 37595 |
| HPV45 | E1 | VAMLDDATH | 511 | 9 | | 37596 |
| HPV45 | E1 | VDPHCSITELK | 178 | 11 | | 37597 |
| HPV45 | E1 | VDTDLSPR | 105 | 8 | | 37598 |
| HPV45 | E1 | VFKDIYGLSF | 203 | 10 | | 37599 |
| HPV45 | E1 | VFTFPHAF | 578 | 8 | | 37600 |
| HPV45 | E1 | VFTFPHAFPF | 578 | 10 | | 37601 |
| HPV45 | E1 | VISDDEDETA | 31 | 10 | | 37602 |
| HPV45 | E1 | VLHLLKRK | 81 | 8 | | 37603 |
| HPV45 | E1 | VLHLLKRKF | 81 | 9 | | 37604 |
| HPV45 | E1 | VLHLLKRKFA | 81 | 10 | | 37605 |
| HPV45 | E1 | VLILALLR | 266 | 8 | | 37606 |
| HPV45 | E1 | VLILALLRY | 266 | 9 | | 37607 |
| HPV45 | E1 | VLILALLRYK | 266 | 10 | | 37608 |
| HPV45 | E1 | VMCRHYKR | 400 | 8 | | 37609 |
| HPV45 | E1 | VMCRHYKRA | 400 | 9 | | 37610 |
| HPV45 | E1 | VMCRHYKRAQK | 400 | 11 | | 37611 |
| HPV45 | E1 | VSGDTPEWIQR | 325 | 11 | | 37612 |
| HPV45 | E1 | VTVFTFPH | 576 | 8 | | 37613 |
| HPV45 | E1 | VTVFTFPHA | 576 | 9 | | 37614 |
| HPV45 | E1 | VTVFTFPHAF | 576 | 10 | | 37615 |
| HPV45 | E1 | WFFVETIVEK | 17 | 10 | | 37616 |
| HPV45 | E1 | WFFVETIVEKK | 17 | 11 | | 37617 |
| HPV45 | E1 | WGVLILALLR | 264 | 10 | | 37618 |
| HPV45 | E1 | WGVLILALLRY | 264 | 11 | | 37619 |
| HPV45 | E1 | WIKYRCSK | 418 | 8 | | 37620 |
| HPV45 | E1 | WIQRLTIIQH | 332 | 10 | | 37621 |
| HPV45 | E1 | WLEPLADTK | 502 | 9 | | 37622 |
| HPV45 | E1 | WLEPLADTKVA | 502 | 11 | | 37623 |
| HPV45 | E1 | WTYFDNYMR | 522 | 9 | | 37624 |
| HPV45 | E1 | WTYFDNYMRNA | 522 | 11 | | 37625 |
| HPV45 | E1 | YAHIQCLDCK | 254 | 10 | | 37626 |
| HPV45 | E1 | YAQLADCNSNA | 372 | 11 | | 37627 |
| HPV45 | E1 | YFDNYMRNA | 524 | 9 | | 37628 |
| HPV45 | E1 | YFGMSFIH | 478 | 8 | | 37629 |
| HPV45 | E1 | YFGMSFIHF | 478 | 9 | | 37630 |
| HPV45 | E1 | YGCSEVEA | 137 | 8 | | 37631 |
| HPV45 | E1 | YGCSEVEAA | 137 | 9 | | 37632 |
| HPV45 | E1 | YGLSFTDLVR | 208 | 10 | | 37633 |
| HPV45 | E1 | YGPANTGK | 469 | 8 | | 37634 |
| HPV45 | E1 | YGPANTGKSY | 469 | 10 | | 37635 |
| HPV45 | E1 | YGPANTGKSYF | 469 | 11 | | 37636 |
| HPV45 | E1 | YLESRVTVF | 571 | 9 | | 37637 |
| HPV45 | E1 | YLESRVTVFTF | 571 | 11 | | 37638 |
| HPV45 | E1 | YLKDCAVMCR | 394 | 10 | | 37639 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E1 | YLKDCAVMCRH | 394 | 11 | | 37640 |
| HPV45 | E2 | AACVSYWGVY | 156 | 10 | | 37641 |
| HPV45 | E2 | AACVSYWGVYY | 156 | 11 | | 37642 |
| HPV45 | E2 | ACVSYWGVY | 157 | 9 | | 37643 |
| HPV45 | E2 | ACVSYWGVYY | 157 | 10 | | 37644 |
| HPV45 | E2 | AIELQMALK | 78 | 9 | | 37645 |
| HPV45 | E2 | AILFTAREH | 47 | 9 | | 37646 |
| HPV45 | E2 | ALKGLAQSK | 84 | 9 | | 37647 |
| HPV45 | E2 | ALKGLAQSKY | 84 | 10 | | 37648 |
| HPV45 | E2 | ALQDKILDH | 16 | 9 | | 37649 |
| HPV45 | E2 | ALQDKILDHY | 16 | 10 | | 37650 |
| HPV45 | E2 | ASTSTPKTA | 226 | 9 | | 37651 |
| HPV45 | E2 | ASVGTPKPH | 234 | 9 | | 37652 |
| HPV45 | E2 | ATQIVRQLQH | 216 | 10 | | 37653 |
| HPV45 | E2 | ATQIVRQLQHA | 216 | 11 | | 37654 |
| HPV45 | E2 | CFKKGGKTVH | 115 | 10 | | 37655 |
| HPV45 | E2 | CGLTEQHH | 254 | 8 | | 37656 |
| HPV45 | E2 | CGLTEQHHGR | 254 | 10 | | 37657 |
| HPV45 | E2 | CLRYRLRK | 305 | 8 | | 37658 |
| HPV45 | E2 | CLRYRLRKY | 305 | 9 | | 37659 |
| HPV45 | E2 | CLRYRLRKYA | 305 | 10 | | 37660 |
| HPV45 | E2 | CMNYVVWDSIY | 134 | 11 | | 37661 |
| HPV45 | E2 | CSGNTTPIIH | 286 | 10 | | 37662 |
| HPV45 | E2 | CSSTSNNK | 274 | 8 | | 37663 |
| HPV45 | E2 | CSSTSNNKR | 274 | 9 | | 37664 |
| HPV45 | E2 | CSSTSNNKRR | 274 | 10 | | 37665 |
| HPV45 | E2 | CSSTSNNKRRK | 274 | 11 | | 37666 |
| HPV45 | E2 | CSTSDDTVSA | 207 | 10 | | 37667 |
| HPV45 | E2 | CVSYWGVY | 158 | 8 | | 37668 |
| HPV45 | E2 | CVSYWGVYY | 158 | 9 | | 37669 |
| HPV45 | E2 | CVSYWGVYYIK | 158 | 11 | | 37670 |
| HPV45 | E2 | DDTVSATQIVR | 211 | 11 | | 37671 |
| HPV45 | E2 | DGDTTYYVQF | 169 | 10 | | 37672 |
| HPV45 | E2 | DGDTTYYVQFK | 169 | 11 | | 37673 |
| HPV45 | E2 | DGNKDNCMNY | 128 | 10 | | 37674 |
| HPV45 | E2 | DINSQISY | 31 | 8 | | 37675 |
| HPV45 | E2 | DSKDINSQISY | 28 | 11 | | 37676 |
| HPV45 | E2 | DTTYYVQF | 171 | 8 | | 37677 |
| HPV45 | E2 | DTTYYVQFK | 171 | 9 | | 37678 |
| HPV45 | E2 | DTVSATQIVR | 212 | 10 | | 37679 |
| HPV45 | E2 | ELQMALKGLA | 80 | 10 | | 37680 |
| HPV45 | E2 | ELWNTEPSQCF | 106 | 11 | | 37681 |
| HPV45 | E2 | ESLSERLSA | 8 | 9 | | 37682 |
| HPV45 | E2 | ETGIWDKTA | 148 | 9 | | 37683 |
| HPV45 | E2 | ETGIWDKTAA | 148 | 10 | | 37684 |
| HPV45 | E2 | FDGNKDNCMNY | 127 | 11 | | 37685 |
| HPV45 | E2 | FTAREHGITK | 50 | 10 | | 37686 |
| HPV45 | E2 | GDKNSLKCLR | 298 | 10 | | 37687 |
| HPV45 | E2 | GDKNSLKCLRY | 298 | 11 | | 37688 |
| HPV45 | E2 | GDTTYYVQF | 170 | 9 | | 37689 |
| HPV45 | E2 | GDTTYYVQFK | 170 | 10 | | 37690 |
| HPV45 | E2 | GGKTVHVY | 119 | 8 | | 37691 |
| HPV45 | E2 | GGKTVHVYF | 119 | 9 | | 37692 |
| HPV45 | E2 | GIWDKTAA | 150 | 8 | | 37693 |
| HPV45 | E2 | GLTEQHHGR | 255 | 9 | | 37694 |
| HPV45 | E2 | GTPKPHIQTPA | 237 | 11 | | 37695 |
| HPV45 | E2 | HASTSTPK | 225 | 8 | | 37696 |
| HPV45 | E2 | HASTSTPKTA | 225 | 10 | | 37697 |
| HPV45 | E2 | HGITKLNH | 55 | 8 | | 37698 |
| HPV45 | E2 | HGRVNTHVH | 261 | 9 | | 37699 |
| HPV45 | E2 | HIQTPATK | 242 | 8 | | 37700 |
| HPV45 | E2 | HIQTPATKR | 242 | 9 | | 37701 |
| HPV45 | E2 | HIQTPATKRPR | 242 | 11 | | 37702 |
| HPV45 | E2 | HLKGDKNSLK | 295 | 10 | | 37703 |
| HPV45 | E2 | HVYFDGNK | 124 | 8 | | 37704 |
| HPV45 | E2 | IIHLKGDK | 293 | 8 | | 37705 |
| HPV45 | E2 | ILDHYENDSK | 21 | 10 | | 37706 |
| HPV45 | E2 | ILFTAREH | 48 | 8 | | 37707 |
| HPV45 | E2 | ISKSKAHK | 70 | 8 | | 37708 |
| HPV45 | E2 | ISKSKAHKA | 70 | 9 | | 37709 |
| HPV45 | E2 | ISYWQLIR | 36 | 8 | | 37710 |
| HPV45 | E2 | ITETGIWDK | 146 | 9 | | 37711 |
| HPV45 | E2 | ITETGIWDKTA | 146 | 11 | | 37712 |
| HPV45 | E2 | IVRQLQHA | 219 | 8 | | 37713 |
| HPV45 | E2 | KAHKAIELQMA | 74 | 11 | | 37714 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E2 | KAIELQMA | 77 | 8 | | 37715 |
| HPV45 | E2 | KAIELQMALK | 77 | 10 | | 37716 |
| HPV45 | E2 | KCLRYRLR | 304 | 8 | | 37717 |
| HPV45 | E2 | KCLRYRLRK | 304 | 9 | | 37718 |
| HPV45 | E2 | KCLRYRLRKY | 304 | 10 | | 37719 |
| HPV45 | E2 | KCLRYRLRKYA | 304 | 11 | | 37720 |
| HPV45 | E2 | KDGDTTYY | 168 | 8 | | 37721 |
| HPV45 | E2 | KDGDTTYYVQF | 168 | 11 | | 37722 |
| HPV45 | E2 | KDINSQISY | 30 | 9 | | 37723 |
| HPV45 | E2 | KGDKNSLK | 297 | 8 | | 37724 |
| HPV45 | E2 | KGDKNSLKCLR | 297 | 11 | | 37725 |
| HPV45 | E2 | KGGKTVHVY | 118 | 9 | | 37726 |
| HPV45 | E2 | KGGKTVHVYF | 118 | 10 | | 37727 |
| HPV45 | E2 | KGLAQSKY | 86 | 8 | | 37728 |
| HPV45 | E2 | KILDHYENDSK | 20 | 11 | | 37729 |
| HPV45 | E2 | KTAACVSY | 154 | 8 | | 37730 |
| HPV45 | E2 | KTASVGTPK | 232 | 9 | | 37731 |
| HPV45 | E2 | KTASVGTPKPH | 232 | 11 | | 37732 |
| HPV45 | E2 | KTVHVYFDGNK | 121 | 11 | | 37733 |
| HPV45 | E2 | LCSSTSNNK | 273 | 9 | | 37734 |
| HPV45 | E2 | LCSSTSNNKR | 273 | 10 | | 37735 |
| HPV45 | E2 | LCSSTSNNKRR | 273 | 11 | | 37736 |
| HPV45 | E2 | LDHYENDSK | 22 | 9 | | 37737 |
| HPV45 | E2 | LFTAREHGITK | 49 | 11 | | 37738 |
| HPV45 | E2 | LIRLENAILF | 41 | 10 | | 37739 |
| HPV45 | E2 | LLCSSTSNNK | 272 | 10 | | 37740 |
| HPV45 | E2 | LLCSSTSNNKR | 272 | 11 | | 37741 |
| HPV45 | E2 | LSALQDKILDH | 14 | 11 | | 37742 |
| HPV45 | E2 | LSERLSALQDK | 10 | 11 | | 37743 |
| HPV45 | E2 | LTEQHHGR | 256 | 8 | | 37744 |
| HPV45 | E2 | LTVTYNSEVQR | 336 | 11 | | 37745 |
| HPV45 | E2 | MALKGLAQSK | 83 | 10 | | 37746 |
| HPV45 | E2 | MALKGLAQSKY | 83 | 11 | | 37747 |
| HPV45 | E2 | MCSTSDDTVSA | 206 | 11 | | 37748 |
| HPV45 | E2 | NAILFTAR | 46 | 8 | | 37749 |
| HPV45 | E2 | NAILFTAREH | 46 | 10 | | 37750 |
| HPV45 | E2 | NISKSKAH | 69 | 8 | | 37751 |
| HPV45 | E2 | NISKSKAHK | 69 | 9 | | 37752 |
| HPV45 | E2 | NISKSKAHKA | 69 | 10 | | 37753 |
| HPV45 | E2 | NSEVQRNTF | 341 | 9 | | 37754 |
| HPV45 | E2 | NSLKCLRY | 301 | 8 | | 37755 |
| HPV45 | E2 | NSLKCLRYR | 301 | 9 | | 37756 |
| HPV45 | E2 | NSLKCLRYRLR | 301 | 11 | | 37757 |
| HPV45 | E2 | NSNTWEVQY | 187 | 9 | | 37758 |
| HPV45 | E2 | NSQISYWQLIR | 33 | 11 | | 37759 |
| HPV45 | E2 | NSVQISVGY | 357 | 9 | | 37760 |
| HPV45 | E2 | NTEPSQCF | 109 | 8 | | 37761 |
| HPV45 | E2 | NTEPSQCFK | 109 | 9 | | 37762 |
| HPV45 | E2 | NTEPSQCFKK | 109 | 10 | | 37763 |
| HPV45 | E2 | NTGILTVTY | 332 | 9 | | 37764 |
| HPV45 | E2 | NTTPIIHLK | 289 | 9 | | 37765 |
| HPV45 | E2 | PIIHLKGDK | 292 | 9 | | 37766 |
| HPV45 | E2 | PINISKSK | 67 | 8 | | 37767 |
| HPV45 | E2 | PINISKSKA | 67 | 9 | | 37768 |
| HPV45 | E2 | PINISKSKAH | 67 | 10 | | 37769 |
| HPV45 | E2 | PINISKSKAHK | 67 | 11 | | 37770 |
| HPV45 | E2 | PLLCSSTSNNK | 271 | 11 | | 37771 |
| HPV45 | E2 | PSQCFKKGGK | 112 | 10 | | 37772 |
| HPV45 | E2 | QCFKKGGK | 114 | 8 | | 37773 |
| HPV45 | E2 | QCFKKGGKTVH | 114 | 11 | | 37774 |
| HPV45 | E2 | QCGLTEQH | 253 | 8 | | 37775 |
| HPV45 | E2 | QCGLTEQHH | 253 | 9 | | 37776 |
| HPV45 | E2 | QCGLTEQHHGR | 253 | 11 | | 37777 |
| HPV45 | E2 | QDKILDHY | 18 | 8 | | 37778 |
| HPV45 | E2 | QFKSECEK | 177 | 8 | | 37779 |
| HPV45 | E2 | QFKSECEKY | 177 | 9 | | 37780 |
| HPV45 | E2 | QISYWQLIR | 35 | 9 | | 37781 |
| HPV45 | E2 | QIVRQLQH | 218 | 8 | | 37782 |
| HPV45 | E2 | QIVRQLQHA | 218 | 9 | | 37783 |
| HPV45 | E2 | QLIRLENA | 40 | 8 | | 37784 |
| HPV45 | E2 | QLIRLENAILF | 40 | 11 | | 37785 |
| HPV45 | E2 | QLQHASTSTPK | 222 | 11 | | 37786 |
| HPV45 | E2 | QMALKGLA | 82 | 8 | | 37787 |
| HPV45 | E2 | QMALKGLAQSK | 82 | 11 | | 37788 |
| HPV45 | E2 | QTPATKRPR | 244 | 9 | | 37789 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E2 | QTPKESLSER | 4 | 10 | | 37790 |
| HPV45 | E2 | QVVPPINISK | 63 | 10 | | 37791 |
| HPV45 | E2 | RLENAILF | 43 | 8 | | 37792 |
| HPV45 | E2 | RLENAILFTA | 43 | 10 | | 37793 |
| HPV45 | E2 | RLENAILFTAR | 43 | 11 | | 37794 |
| HPV45 | E2 | RLRKYADH | 309 | 8 | | 37795 |
| HPV45 | E2 | RLRKYADHY | 309 | 9 | | 37796 |
| HPV45 | E2 | RLSALQDK | 13 | 8 | | 37797 |
| HPV45 | E2 | SALQDKILDH | 15 | 10 | | 37798 |
| HPV45 | E2 | SALQDKILDHY | 15 | 11 | | 37799 |
| HPV45 | E2 | SATQIVRQLQH | 215 | 11 | | 37800 |
| HPV45 | E2 | SGNTTPIIH | 287 | 9 | | 37801 |
| HPV45 | E2 | SGNTTPIIHLK | 287 | 11 | | 37802 |
| HPV45 | E2 | SLKCLRYR | 302 | 8 | | 37803 |
| HPV45 | E2 | SLKCLRYRLR | 302 | 10 | | 37804 |
| HPV45 | E2 | SLKCLRYRLRK | 302 | 11 | | 37805 |
| HPV45 | E2 | SLSERLSA | 9 | 8 | | 37806 |
| HPV45 | E2 | SSTSNNKR | 275 | 8 | | 37807 |
| HPV45 | E2 | SSTSNNKRR | 275 | 9 | | 37808 |
| HPV45 | E2 | SSTSNNKRRK | 275 | 10 | | 37809 |
| HPV45 | E2 | SSTWHWTGCNK | 321 | 11 | | 37810 |
| HPV45 | E2 | STSDDTVSA | 208 | 9 | | 37811 |
| HPV45 | E2 | STSNNKRR | 276 | 8 | | 37812 |
| HPV45 | E2 | STSNNKRRK | 276 | 9 | | 37813 |
| HPV45 | E2 | STSTPKTA | 227 | 8 | | 37814 |
| HPV45 | E2 | STWHWTGCNK | 322 | 10 | | 37815 |
| HPV45 | E2 | SVGTPKPH | 235 | 8 | | 37816 |
| HPV45 | E2 | SVQISVGY | 358 | 8 | | 37817 |
| HPV45 | E2 | TAACVSYWGVY | 155 | 11 | | 37818 |
| HPV45 | E2 | TAREHGITK | 51 | 9 | | 37819 |
| HPV45 | E2 | TASVGTPK | 233 | 8 | | 37820 |
| HPV45 | E2 | TASVGTPKPH | 233 | 10 | | 37821 |
| HPV45 | E2 | TGILTVTY | 333 | 8 | | 37822 |
| HPV45 | E2 | TGIWDKTA | 149 | 8 | | 37823 |
| HPV45 | E2 | TGIWDKTAA | 149 | 9 | | 37824 |
| HPV45 | E2 | TSDDTVSA | 209 | 8 | | 37825 |
| HPV45 | E2 | TSNNKRRK | 277 | 8 | | 37826 |
| HPV45 | E2 | TTPIIHLK | 290 | 8 | | 37827 |
| HPV45 | E2 | TTPIIHLKGDK | 290 | 11 | | 37828 |
| HPV45 | E2 | TTYYVQFK | 172 | 8 | | 37829 |
| HPV45 | E2 | TVHVYFDGNK | 122 | 10 | | 37830 |
| HPV45 | E2 | TVSATQIVR | 213 | 9 | | 37831 |
| HPV45 | E2 | TVTYNSEVQR | 337 | 10 | | 37832 |
| HPV45 | E2 | VCSGNTTPIIH | 285 | 11 | | 37833 |
| HPV45 | E2 | VSATQIVR | 214 | 8 | | 37834 |
| HPV45 | E2 | VSYWGVYY | 159 | 8 | | 37835 |
| HPV45 | E2 | VSYWGVYYIK | 159 | 10 | | 37836 |
| HPV45 | E2 | VTYNSEVQR | 338 | 9 | | 37837 |
| HPV45 | E2 | VVPPINISK | 64 | 9 | | 37838 |
| HPV45 | E2 | VVPPINISKS | 64 | 11 | | 37839 |
| HPV45 | E2 | VVWDSIYY | 138 | 8 | | 37840 |
| HPV45 | E2 | WDKTAACVSY | 152 | 10 | | 37841 |
| HPV45 | E2 | YGNSNTWEVQY | 185 | 11 | | 37842 |
| HPV45 | E2 | YIKDGDTTY | 166 | 9 | | 37843 |
| HPV45 | E2 | YIKDGDTTYY | 166 | 10 | | 37844 |
| HPV45 | E2 | YITETGIWDK | 145 | 10 | | 37845 |
| HPV45 | E2 | YSEISSTWH | 317 | 9 | | 37846 |
| HPV45 | E2 | YVQFKSECEK | 175 | 10 | | 37847 |
| HPV45 | E2 | YVQFKSECEKY | 175 | 11 | | 37848 |
| HPV45 | E2 | YVVWDSIY | 137 | 8 | | 37849 |
| HPV45 | E2 | YVVWDSIYY | 137 | 9 | | 37850 |
| HPV45 | E6 | AACHKCIDF | 63 | 9 | | 37851 |
| HPV45 | E6 | AACHKCIDFY | 63 | 10 | | 37852 |
| HPV45 | E6 | ACHKCIDF | 64 | 8 | | 37853 |
| HPV45 | E6 | ACHKCIDFY | 64 | 9 | | 37854 |
| HPV45 | E6 | ACHKCIDFYSR | 64 | 11 | | 37855 |
| HPV45 | E6 | ACVYCKATLER | 31 | 11 | | 37856 |
| HPV45 | E6 | AFKDLFIVY | 48 | 9 | | 37857 |
| HPV45 | E6 | AFKDLFIVYR | 48 | 10 | | 37858 |
| HPV45 | E6 | ATLERTEVY | 37 | 9 | | 37859 |
| HPV45 | E6 | ATLERTEVYQF | 37 | 11 | | 37860 |
| HPV45 | E6 | CCDQARQER | 141 | 9 | | 37861 |
| HPV45 | E6 | CCDQARQERLR | 141 | 11 | | 37862 |
| HPV45 | E6 | CDQARQER | 142 | 8 | | 37863 |
| HPV45 | E6 | CDQARQERLR | 142 | 10 | | 37864 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E6 | CDQARQERLRR | 142 | 11 | | 37865 |
| HPV45 | E6 | CIAYAACH | 59 | 8 | | 37866 |
| HPV45 | E6 | CIAYAACHK | 59 | 9 | | 37867 |
| HPV45 | E6 | CIDFYSRIR | 68 | 9 | 0.001 | 37868 |
| HPV45 | E6 | CLRCQKPLNPA | 105 | 11 | | 37869 |
| HPV45 | E6 | CVYCKATLER | 32 | 10 | | 37870 |
| HPV45 | E6 | DCIAYAACH | 58 | 9 | | 37871 |
| HPV45 | E6 | DCIAYAACHK | 58 | 10 | | 37872 |
| HPV45 | E6 | DDPTQRPY | 5 | 8 | | 37873 |
| HPV45 | E6 | DDPTQRPYK | 5 | 9 | | 37874 |
| HPV45 | E6 | DFYSRIRELR | 70 | 10 | 0.0002 | 37875 |
| HPV45 | E6 | DFYSRIRELRY | 70 | 11 | | 37876 |
| HPV45 | E6 | DLFIVYRDCIA | 51 | 11 | | 37877 |
| HPV45 | E6 | DVSIACVY | 27 | 8 | | 37878 |
| HPV45 | E6 | DVSIACVYCK | 27 | 10 | | 37879 |
| HPV45 | E6 | DVSIACVYCKA | 27 | 11 | | 37880 |
| HPV45 | E6 | ELRYYSNSVY | 77 | 10 | | 37881 |
| HPV45 | E6 | ELYNLLIR | 97 | 8 | | 37882 |
| HPV45 | E6 | ELYNLLIRCLR | 97 | 11 | | 37883 |
| HPV45 | E6 | EVYQFAFK | 43 | 8 | | 37884 |
| HPV45 | E6 | EVYQFAFKDLF | 43 | 11 | | 37885 |
| HPV45 | E6 | FAFKDLFIVY | 47 | 10 | | 37886 |
| HPV45 | E6 | FAFKDLFIVYR | 47 | 11 | | 37887 |
| HPV45 | E6 | FDDPTQRPY | 4 | 9 | | 37888 |
| HPV45 | E6 | FDDPTQRPYK | 4 | 10 | | 37889 |
| HPV45 | E6 | FIVYRDCIA | 53 | 9 | | 37890 |
| HPV45 | E6 | FIVYRDCIAY | 53 | 10 | | 37891 |
| HPV45 | E6 | FIVYRDCIAYA | 53 | 11 | | 37892 |
| HPV45 | E6 | HLKDKRRF | 120 | 8 | | 37893 |
| HPV45 | E6 | HLKDKRRFH | 120 | 9 | | 37894 |
| HPV45 | E6 | HSIAGQYR | 128 | 8 | | 37895 |
| HPV45 | E6 | IACVYCKA | 30 | 8 | | 37896 |
| HPV45 | E6 | IAYAACHK | 60 | 8 | | 37897 |
| HPV45 | E6 | IDFYSRIR | 69 | 8 | | 37898 |
| HPV45 | E6 | IDFYSRIRELR | 69 | 11 | | 37899 |
| HPV45 | E6 | IVYRDCIA | 54 | 8 | | 37900 |
| HPV45 | E6 | IVYRDCIAY | 54 | 9 | | 37901 |
| HPV45 | E6 | IVYRDCIAYA | 54 | 10 | | 37902 |
| HPV45 | E6 | IVYRDCIAYAA | 54 | 11 | | 37903 |
| HPV45 | E6 | KATLERTEVY | 36 | 10 | | 37904 |
| HPV45 | E6 | KCIDFYSR | 67 | 8 | | 37905 |
| HPV45 | E6 | KCIDFYSRIR | 67 | 10 | | 37906 |
| HPV45 | E6 | KDKRRFHSIA | 122 | 10 | | 37907 |
| HPV45 | E6 | KDLFIVYR | 50 | 8 | | 37908 |
| HPV45 | E6 | KITNTELY | 92 | 8 | | 37909 |
| HPV45 | E6 | LFIVYRDCIA | 52 | 10 | | 37910 |
| HPV45 | E6 | LFIVYRDCIAY | 52 | 11 | | 37911 |
| HPV45 | E6 | LIRCLRCQK | 102 | 9 | 0.0190 | 37912 |
| HPV45 | E6 | LLIRCLRCQK | 101 | 10 | 0.0470 | 37913 |
| HPV45 | E6 | MARFDDPTQR | 1 | 10 | | 37914 |
| HPV45 | E6 | NLLIRCLR | 100 | 8 | | 37915 |
| HPV45 | E6 | NLLIRCLRCQK | 100 | 11 | | 37916 |
| HPV45 | E6 | NSVYGETLEK | 83 | 10 | | 37917 |
| HPV45 | E6 | NTCCDQAR | 139 | 8 | | 37918 |
| HPV45 | E6 | NTCCDQARQER | 139 | 11 | | 37919 |
| HPV45 | E6 | NTELYNLLIR | 95 | 10 | | 37920 |
| HPV45 | E6 | NTSLQDVSIA | 22 | 10 | | 37921 |
| HPV45 | E6 | PAEKRRHLK | 114 | 9 | | 37922 |
| HPV45 | E6 | PEAKRRHLKDK | 114 | 11 | | 37923 |
| HPV45 | E6 | PLNPAEKR | 111 | 8 | | 37924 |
| HPV45 | E6 | PLNPAEKRR | 111 | 9 | | 37925 |
| HPV45 | E6 | PLNPAEKRRH | 111 | 10 | | 37926 |
| HPV45 | E6 | QARQERLR | 144 | 8 | | 37927 |
| HPV45 | E6 | QARQERLRR | 144 | 9 | | 37928 |
| HPV45 | E6 | QARQERLRRR | 144 | 10 | | 37929 |
| HPV45 | E6 | QARQERLRRRR | 144 | 11 | | 37930 |
| HPV45 | E6 | QCNTCCDQA | 137 | 9 | | 37931 |
| HPV45 | E6 | QCNTCCDQAR | 137 | 10 | | 37932 |
| HPV45 | E6 | QDVSIACVY | 26 | 9 | | 37933 |
| HPV45 | E6 | QDVSIACVYCK | 26 | 11 | | 37934 |
| HPV45 | E6 | QFAFKDLF | 46 | 8 | | 37935 |
| HPV45 | E6 | QFAFKDLFIVY | 46 | 11 | | 37936 |
| HPV45 | E6 | RCQKPLNPA | 107 | 9 | | 37937 |
| HPV45 | E6 | RCQKPLNPAEK | 107 | 11 | | 37938 |
| HPV45 | E6 | RDCIAYAA | 57 | 8 | | 37939 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E6 | RDCIAYAACH | 57 | 10 | | 37940 |
| HPV45 | E6 | RDCIAYAACHK | 57 | 11 | | 37941 |
| HPV45 | E6 | RFDDPTQR | 3 | 8 | | 37942 |
| HPV45 | E6 | RFDDPTQRPY | 3 | 10 | | 37943 |
| HPV45 | E6 | RFDDPTQRPYK | 3 | 11 | | 37944 |
| HPV45 | E6 | RFHSIAGQY | 126 | 9 | | 37945 |
| HPV45 | E6 | RFHSIAGQYR | 126 | 10 | | 37946 |
| HPV45 | E6 | RGQCNTCCDQA | 135 | 11 | | 37947 |
| HPV45 | E6 | RIRELRYY | 74 | 8 | | 37948 |
| HPV45 | E6 | RTEVYQFA | 41 | 8 | | 37949 |
| HPV45 | E6 | RTEVYQFAF | 41 | 9 | | 37950 |
| HPV45 | E6 | RTEVYQFAFK | 41 | 10 | | 37951 |
| HPV45 | E6 | SIACVYCK | 29 | 8 | | 37952 |
| HPV45 | E6 | SIACVYCKA | 29 | 9 | | 37953 |
| HPV45 | E6 | SLQDVSIA | 24 | 8 | | 37954 |
| HPV45 | E6 | SLQDVSIACVY | 24 | 11 | | 37955 |
| HPV45 | E6 | SVYGETLEK | 84 | 9 | | 37956 |
| HPV45 | E6 | TCCDQARQER | 140 | 10 | | 37957 |
| HPV45 | E6 | TLEKITNTELY | 89 | 11 | | 37958 |
| HPV45 | E6 | TLERTEVY | 38 | 8 | | 37959 |
| HPV45 | E6 | TLERTEVYQF | 38 | 10 | | 37960 |
| HPV45 | E6 | TLERTEVYQFA | 38 | 11 | | 37961 |
| HPV45 | E6 | TSLQDVSIA | 23 | 9 | | 37962 |
| HPV45 | E6 | VSIACVYCK | 28 | 9 | | 37963 |
| HPV45 | E6 | VSIACVYCKA | 28 | 10 | | 37964 |
| HPV45 | E6 | YAACHKCIDF | 62 | 10 | | 37965 |
| HPV45 | E6 | YAACHKCIDFY | 62 | 11 | | 37966 |
| HPV45 | E6 | YCKATLER | 34 | 8 | | 37967 |
| HPV45 | E6 | YSRIRELR | 72 | 8 | | 37968 |
| HPV45 | E6 | YSRIRELRY | 72 | 9 | | 37969 |
| HPV45 | E6 | YSRIRELRYY | 72 | 10 | | 37970 |
| HPV45 | E7 | ADDLRTLQQLF | 81 | 11 | | 37971 |
| HPV45 | E7 | ADGVSHAQLPA | 42 | 11 | | 37972 |
| HPV45 | E7 | ATLQEIVLH | 6 | 9 | | 37973 |
| HPV45 | E7 | CVCCKCDGR | 64 | 9 | | 37974 |
| HPV45 | E7 | DDLRTLQQLF | 82 | 10 | | 37975 |
| HPV45 | E7 | DGVSHAQLPA | 43 | 10 | | 37976 |
| HPV45 | E7 | DGVSHAQLPAR | 43 | 11 | | 37977 |
| HPV45 | E7 | DLRTLQQLF | 83 | 9 | | 37978 |
| HPV45 | E7 | EADGVSHA | 41 | 8 | | 37979 |
| HPV45 | E7 | ELDPVDLLCY | 20 | 10 | | 37980 |
| HPV45 | E7 | ELTVESSA | 74 | 8 | | 37981 |
| HPV45 | E7 | ESEEENDEA | 34 | 9 | | 37982 |
| HPV45 | E7 | ESSADDLR | 78 | 8 | | 37983 |
| HPV45 | E7 | GVSHAQLPA | 44 | 9 | | 37984 |
| HPV45 | E7 | GVSHAQLPAR | 44 | 10 | | 37985 |
| HPV45 | E7 | GVSHAQLPARR | 44 | 11 | | 37986 |
| HPV45 | E7 | HAQLPARR | 47 | 8 | | 37987 |
| HPV45 | E7 | HAQLPARRA | 47 | 9 | | 37988 |
| HPV45 | E7 | ILCVCCKCDGR | 62 | 11 | | 37989 |
| HPV45 | E7 | KILCVCCK | 61 | 8 | | 37990 |
| HPV45 | E7 | LCVCCKCDGR | 63 | 10 | | 37991 |
| HPV45 | E7 | LDPVDLLCY | 21 | 9 | | 37992 |
| HPV45 | E7 | LFLSTLSF | 90 | 8 | | 37993 |
| HPV45 | E7 | LSESEEENDEA | 32 | 11 | | 37994 |
| HPV45 | E7 | LSFVCPWCA | 95 | 9 | 0.0005 | 37995 |
| HPV45 | E7 | LTVESSADDLR | 75 | 11 | | 37996 |
| HPV45 | E7 | NDEADGVSH | 39 | 9 | | 37997 |
| HPV45 | E7 | NDEADGVSHA | 39 | 10 | | 37998 |
| HPV45 | E7 | PARRAEPQR | 51 | 9 | | 37999 |
| HPV45 | E7 | PARRAEPQRH | 51 | 10 | | 38000 |
| HPV45 | E7 | PARRAEPQRHK | 51 | 11 | | 38001 |
| HPV45 | E7 | QLFLSTLSF | 89 | 9 | | 38002 |
| HPV45 | E7 | QLPARRAEPQR | 49 | 11 | | 38003 |
| HPV45 | E7 | RAEPQRHK | 54 | 8 | | 38004 |
| HPV45 | E7 | RATLQEIVLH | 5 | 10 | | 38005 |
| HPV45 | E7 | RIELTVESSA | 72 | 10 | | 38006 |
| HPV45 | E7 | SFVCPWCA | 96 | 8 | | 38007 |
| HPV45 | E7 | STLSFVCPWCA | 93 | 11 | | 38008 |
| HPV45 | E7 | TLQEIVLH | 7 | 8 | | 38009 |
| HPV45 | E7 | TLSFVCPWCA | 94 | 10 | | 38010 |
| HPV45 | E7 | TVESSADDLR | 76 | 10 | | 38011 |
| HPV45 | E7 | VCCKCDGR | 65 | 8 | | 38012 |
| HPV45 | E7 | VSHAQLPA | 45 | 8 | | 38013 |
| HPV45 | E7 | VSHAQLPAR | 45 | 9 | | 38014 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | E7 | VSHAQLPARR | 45 | 10 | | 38015 |
| HPV45 | E7 | VSHAQLPARRA | 45 | 11 | | 38016 |
| HPV45 | L1 | AASTSTASR | 517 | 9 | | 38017 |
| HPV45 | L1 | AASTSTASRPA | 517 | 11 | | 38018 |
| HPV45 | L1 | AATAVITQDVR | 161 | 11 | | 38019 |
| HPV45 | L1 | ACVGMEIGR | 128 | 9 | | 38020 |
| HPV45 | L1 | ADPYGDSMF | 266 | 9 | | 38021 |
| HPV45 | L1 | ADPYGDSMFF | 266 | 10 | | 38022 |
| HPV45 | L1 | AGNKQAVPK | 83 | 9 | | 38023 |
| HPV45 | L1 | AIGEHWAK | 191 | 8 | | 38024 |
| HPV45 | L1 | ALPDPNKF | 103 | 8 | | 38025 |
| HPV45 | L1 | ALWRPSDSTVY | 28 | 11 | | 38026 |
| HPV45 | L1 | AMDFSTLQDTK | 234 | 11 | | 38027 |
| HPV45 | L1 | ASRPAKRVR | 523 | 9 | | 38028 |
| HPV45 | L1 | ASRPAKRVRIR | 523 | 11 | | 38029 |
| HPV45 | L1 | ASTQNPVPNTY | 375 | 11 | | 38030 |
| HPV45 | L1 | ASTSTASR | 518 | 8 | | 38031 |
| HPV45 | L1 | ASTSTASRPA | 518 | 10 | | 38032 |
| HPV45 | L1 | ASTSTASRPAK | 518 | 11 | | 38033 |
| HPV45 | L1 | ATAVITQDVR | 162 | 10 | | 38034 |
| HPV45 | L1 | AVITQDVR | 164 | 8 | | 38035 |
| HPV45 | L1 | AVPKVSAY | 88 | 8 | | 38036 |
| HPV45 | L1 | AVPKVSAYQY | 88 | 10 | | 38037 |
| HPV45 | L1 | AVPKVSAYQYR | 88 | 11 | | 38038 |
| HPV45 | L1 | CILGCVPA | 184 | 8 | | 38039 |
| HPV45 | L1 | CLRREQLF | 276 | 8 | | 38040 |
| HPV45 | L1 | CLRREQLFA | 276 | 9 | | 38041 |
| HPV45 | L1 | CLRREQLFAR | 276 | 10 | | 38042 |
| HPV45 | L1 | CLRREQLFARH | 276 | 11 | | 38043 |
| HPV45 | L1 | CVGMEIGR | 129 | 8 | | 38044 |
| HPV45 | L1 | CVPAIGEH | 188 | 8 | | 38045 |
| HPV45 | L1 | CVPAIGEHWA | 188 | 10 | | 38046 |
| HPV45 | L1 | CVPAIGEHWAK | 188 | 11 | | 38047 |
| HPV45 | L1 | DCPPLELK | 211 | 8 | | 38048 |
| HPV45 | L1 | DDTESAHA | 154 | 8 | | 38049 |
| HPV45 | L1 | DDTESAHAA | 154 | 9 | | 38050 |
| HPV45 | L1 | DDTESAHAATA | 154 | 11 | | 38051 |
| HPV45 | L1 | DDYVSRTSIF | 51 | 10 | | 38052 |
| HPV45 | L1 | DDYVSRTSIFY | 51 | 11 | | 38053 |
| HPV45 | L1 | DFSTLQDTK | 236 | 9 | | 38054 |
| HPV45 | L1 | DGDMVDTGY | 224 | 9 | | 38055 |
| HPV45 | L1 | DGDMVDTGYGA | 224 | 11 | | 38056 |
| HPV45 | L1 | DICQSICK | 250 | 8 | | 38057 |
| HPV45 | L1 | DICQSICKY | 250 | 9 | | 38058 |
| HPV45 | L1 | DLDQYPLGR | 488 | 9 | | 38059 |
| HPV45 | L1 | DLDQYPLGRK | 488 | 10 | | 38060 |
| HPV45 | L1 | DLDQYPLGRKF | 488 | 11 | | 38061 |
| HPV45 | L1 | DLYIKGTSA | 301 | 9 | | 38062 |
| HPV45 | L1 | DMVDTGYGA | 226 | 9 | | 38063 |
| HPV45 | L1 | DSMFFCLR | 271 | 8 | | 38064 |
| HPV45 | L1 | DSMFFCLRR | 271 | 9 | | 38065 |
| HPV45 | L1 | DSQLFNKPY | 332 | 9 | | 38066 |
| HPV45 | L1 | DSTIYNPETQR | 114 | 11 | | 38067 |
| HPV45 | L1 | DTESAHAA | 155 | 8 | | 38068 |
| HPV45 | L1 | DTESAHAATA | 155 | 10 | | 38069 |
| HPV45 | L1 | DTGYGAMDF | 229 | 9 | | 38070 |
| HPV45 | L1 | DTTPPEKQDPY | 461 | 11 | | 38071 |
| HPV45 | L1 | DTVPTDLY | 296 | 8 | | 38072 |
| HPV45 | L1 | DTVPTDLYIK | 296 | 10 | | 38073 |
| HPV45 | L1 | DTYRFVQSVA | 446 | 10 | | 38074 |
| HPV45 | L1 | DVRDNVSVDY | 169 | 10 | | 38075 |
| HPV45 | L1 | DVRDNVSVDYK | 169 | 11 | | 38076 |
| HPV45 | L1 | EDGDMVDTGY | 223 | 10 | | 38077 |
| HPV45 | L1 | ESAHAATA | 157 | 8 | | 38078 |
| HPV45 | L1 | ETPGSCVY | 313 | 8 | | 38079 |
| HPV45 | L1 | ETQRLVWA | 121 | 8 | | 38080 |
| HPV45 | L1 | FARHFWNR | 283 | 8 | | 38081 |
| HPV45 | L1 | FARHFWNRA | 283 | 9 | | 38082 |
| HPV45 | L1 | FCLRREQLF | 275 | 9 | | 38083 |
| HPV45 | L1 | FCLRREQLFA | 275 | 10 | | 38084 |
| HPV45 | L1 | FCLRREQLFAR | 275 | 11 | | 38085 |
| HPV45 | L1 | FFCLRREQLF | 274 | 10 | | 38086 |
| HPV45 | L1 | FFCLRREQLFA | 274 | 11 | | 38087 |
| HPV45 | L1 | FGLPDSTIY | 110 | 9 | | 38088 |
| HPV45 | L1 | FLKNVNVF | 14 | 8 | | 38089 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | L1 | FLKNVNVFPIF | 14 | 11 | | 38090 |
| HPV45 | L1 | FLQMALWR | 24 | 8 | | 38091 |
| HPV45 | L1 | FLVQAGLR | 498 | 8 | | 38092 |
| HPV45 | L1 | FLVQAGLRR | 498 | 9 | | 38093 |
| HPV45 | L1 | FLVQAGLRRR | 498 | 10 | | 38094 |
| HPV45 | L1 | FSSDLDQY | 485 | 8 | | 38095 |
| HPV45 | L1 | FSTLQDTK | 237 | 8 | | 38096 |
| HPV45 | L1 | FVQSVAVTCQK | 450 | 11 | | 38097 |
| HPV45 | L1 | FVTVVDTTR | 359 | 9 | | 38098 |
| HPV45 | L1 | GAGNKQAVPK | 82 | 10 | | 38099 |
| HPV45 | L1 | GCVPAIGEH | 187 | 9 | | 38100 |
| HPV45 | L1 | GCVPAIGEHWA | 187 | 11 | | 38101 |
| HPV45 | L1 | GDCPPLELK | 210 | 9 | | 38102 |
| HPV45 | L1 | GDMVDTGY | 225 | 8 | | 38103 |
| HPV45 | L1 | GDMVDTGYGA | 225 | 10 | | 38104 |
| HPV45 | L1 | GDSMFFCLR | 270 | 9 | | 38105 |
| HPV45 | L1 | GDSMFFCLRR | 270 | 10 | | 38106 |
| HPV45 | L1 | GDTVPTDLY | 295 | 9 | | 38107 |
| HPV45 | L1 | GDTVPTDLYIK | 295 | 11 | | 38108 |
| HPV45 | L1 | GICWHNQLF | 351 | 9 | | 38109 |
| HPV45 | L1 | GIGLSGHPF | 141 | 9 | | 38110 |
| HPV45 | L1 | GIGLSGHPFY | 141 | 10 | | 38111 |
| HPV45 | L1 | GLPDSTIY | 111 | 8 | | 38112 |
| HPV45 | L1 | GLRRRPTIGPR | 503 | 11 | | 38113 |
| HPV45 | L1 | GLSGHPFY | 143 | 8 | | 38114 |
| HPV45 | L1 | GLSGHPFYNK | 143 | 10 | | 38115 |
| HPV45 | L1 | GSITTSDSQLF | 326 | 11 | | 38116 |
| HPV45 | L1 | HGIIIFLK | 9 | 8 | | 38117 |
| HPV45 | L1 | HVEEYDLQF | 396 | 9 | | 38118 |
| HPV45 | L1 | HVEEYDLQFIF | 396 | 11 | | 38119 |
| HPV45 | L1 | ICQSICKY | 251 | 8 | | 38120 |
| HPV45 | L1 | ICQSICKYPDY | 251 | 11 | | 38121 |
| HPV45 | L1 | ICWHNQLF | 352 | 8 | | 38122 |
| HPV45 | L1 | IFLKNVNVF | 13 | 9 | | 38123 |
| HPV45 | L1 | IFLQMALWR | 23 | 9 | | 38124 |
| HPV45 | L1 | IFQLCTITLTA | 405 | 11 | | 38125 |
| HPV45 | L1 | IFYHAGSSR | 59 | 9 | | 38126 |
| HPV45 | L1 | IGLSGHPF | 142 | 8 | | 38127 |
| HPV45 | L1 | IGLSGHPFY | 142 | 9 | | 38128 |
| HPV45 | L1 | IGLSGHPFYNK | 142 | 11 | | 38129 |
| HPV45 | L1 | IGPRKRPA | 510 | 8 | | 38130 |
| HPV45 | L1 | IGPRKRPAA | 510 | 9 | | 38131 |
| HPV45 | L1 | IIFLFNVNVF | 12 | 10 | | 38132 |
| HPV45 | L1 | IIIFLKNVNVF | 11 | 11 | | 38133 |
| HPV45 | L1 | IIYGHGIIIF | 5 | 10 | | 38134 |
| HPV45 | L1 | ILGCVPAIGEH | 185 | 11 | | 38135 |
| HPV45 | L1 | ITLTAEVMSY | 411 | 10 | | 38136 |
| HPV45 | L1 | ITTSDSQLF | 328 | 9 | | 38137 |
| HPV45 | L1 | ITTSDSQLFNK | 328 | 11 | | 38138 |
| HPV45 | L1 | KDTTPPEK | 460 | 8 | | 38139 |
| HPV45 | L1 | KFGLPDSTIY | 109 | 10 | | 38140 |
| HPV45 | L1 | KFKHYSRH | 389 | 8 | | 38141 |
| HPV45 | L1 | KFLVQAGLR | 497 | 9 | | 38142 |
| HPV45 | L1 | KFLVQAGLRR | 497 | 10 | | 38143 |
| HPV45 | L1 | KFLVQAGLRRR | 497 | 11 | | 38144 |
| HPV45 | L1 | KFSSDLDQY | 484 | 9 | | 38145 |
| HPV45 | L1 | KFWTVDLK | 475 | 8 | | 38146 |
| HPV45 | L1 | KFWTVDLKEK | 475 | 10 | | 38147 |
| HPV45 | L1 | KFWTVDLKEKF | 475 | 11 | | 38148 |
| HPV45 | L1 | KGTLCKPA | 198 | 8 | | 38149 |
| HPV45 | L1 | KGTSANMR | 305 | 8 | | 38150 |
| HPV45 | L1 | KLDDTESA | 152 | 8 | | 38151 |
| HPV45 | L1 | KLDDTESAH | 152 | 9 | | 38152 |
| HPV45 | L1 | KLDDTESAHA | 152 | 10 | | 38153 |
| HPV45 | L1 | KLDDTESAHAA | 152 | 11 | | 38154 |
| HPV45 | L1 | KLKFWTVDLK | 473 | 10 | | 38155 |
| HPV45 | L1 | KVSAYQYR | 91 | 8 | | 38156 |
| HPV45 | L1 | KVSAYQYRVF | 91 | 10 | | 38157 |
| HPV45 | L1 | KVSAYQYRVFR | 91 | 11 | | 38158 |
| HPV45 | L1 | LCILGCVPA | 183 | 9 | | 38159 |
| HPV45 | L1 | LCTITLTA | 408 | 8 | | 38160 |
| HPV45 | L1 | LDDTESAH | 153 | 8 | | 38161 |
| HPV45 | L1 | LDDTESAHA | 153 | 9 | | 38162 |
| HPV45 | L1 | LDDTESAHAA | 153 | 10 | | 38163 |
| HPV45 | L1 | LDICQSICK | 249 | 9 | | 38164 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | L1 | LDICQSICKY | 249 | 10 | | 38165 |
| HPV45 | L1 | LDQYPLGR | 489 | 8 | | 38166 |
| HPV45 | L1 | LDQYPLGRK | 489 | 9 | | 38167 |
| HPV45 | L1 | LDQYPLGRKF | 489 | 10 | | 38168 |
| HPV45 | L1 | LFARHFWNR | 282 | 9 | | 38169 |
| HPV45 | L1 | LFARHFWNRA | 282 | 10 | | 38170 |
| HPV45 | L1 | LFNKPYWLH | 335 | 9 | | 38171 |
| HPV45 | L1 | LFNKPYWLHK | 335 | 10 | | 38172 |
| HPV45 | L1 | LFNKPYWLHKA | 335 | 11 | | 38173 |
| HPV45 | L1 | LFVTVVDTTR | 358 | 10 | | 38174 |
| HPV45 | L1 | LGCVPAIGEH | 186 | 10 | | 38175 |
| HPV45 | L1 | LGIGLSGH | 140 | 8 | | 38176 |
| HPV45 | L1 | LGIGLSGHPF | 140 | 10 | | 38177 |
| HPV45 | L1 | LGIGLSGHPFY | 140 | 11 | | 38178 |
| HPV45 | L1 | LGRKFLVQA | 494 | 9 | | 38179 |
| HPV45 | L1 | LLTVGNPY | 68 | 8 | | 38180 |
| HPV45 | L1 | LLTVGNPYF | 68 | 9 | | 38181 |
| HPV45 | L1 | LLTVGNPYFR | 68 | 10 | | 38182 |
| HPV45 | L1 | LSGHPFYNK | 144 | 9 | | 38183 |
| HPV45 | L1 | LTAEVMSY | 413 | 8 | | 38184 |
| HPV45 | L1 | LTAEVMSYIH | 413 | 10 | | 38185 |
| HPV45 | L1 | LTVGNPYF | 69 | 8 | | 38186 |
| HPV45 | L1 | LTVGNPYFR | 69 | 9 | | 38187 |
| HPV45 | L1 | LVQAGLRR | 499 | 8 | | 38188 |
| HPV45 | L1 | LVQAGLRRR | 499 | 9 | | 38189 |
| HPV45 | L1 | MAHNIIYGH | 1 | 9 | | 38190 |
| HPV45 | L1 | MDFSTLQDTK | 235 | 10 | | 38191 |
| HPV45 | L1 | MFFCLRREQLF | 273 | 11 | | 38192 |
| HPV45 | L1 | MGDTVPTDLY | 294 | 10 | | 38193 |
| HPV45 | L1 | MSADPYGDSMF | 264 | 11 | | 38194 |
| HPV45 | L1 | MVDTGYGA | 227 | 8 | | 38195 |
| HPV45 | L1 | MVDTGYGAMDF | 227 | 11 | | 38196 |
| HPV45 | L1 | NGICWHNQLF | 350 | 10 | | 38197 |
| HPV45 | L1 | NIIYGHGIIF | 4 | 11 | | 38198 |
| HPV45 | L1 | NMRETPGSCVY | 310 | 11 | | 38199 |
| HPV45 | L1 | NSSILENWNF | 425 | 10 | | 38200 |
| HPV45 | L1 | NTDDYVSR | 49 | 8 | | 38201 |
| HPV45 | L1 | NTYDPTKF | 383 | 8 | | 38202 |
| HPV45 | L1 | NTYDPTKFK | 383 | 9 | | 38203 |
| HPV45 | L1 | NTYDPTKFKH | 383 | 10 | | 38204 |
| HPV45 | L1 | NTYDPTKFKHY | 383 | 11 | | 38205 |
| HPV45 | L1 | NVFPIFLQMA | 19 | 10 | | 38206 |
| HPV45 | L1 | NVNVFPIF | 17 | 8 | | 38207 |
| HPV45 | L1 | PAASTSTA | 516 | 8 | | 38208 |
| HPV45 | L1 | PAASTSTASR | 516 | 10 | | 38209 |
| HPV45 | L1 | PAIGEHWA | 190 | 8 | | 38210 |
| HPV45 | L1 | PAIGEHWAK | 190 | 9 | | 38211 |
| HPV45 | L1 | PAKRVRIR | 526 | 8 | | 38212 |
| HPV45 | L1 | PAKRVRIRSK | 526 | 10 | | 38213 |
| HPV45 | L1 | PAKRVRIRSKK | 526 | 11 | | 38214 |
| HPV45 | L1 | PDYLQMSA | 259 | 8 | | 38215 |
| HPV45 | L1 | PDYLQMSADPY | 259 | 11 | | 38216 |
| HPV45 | L1 | PGDCPPLELK | 209 | 10 | | 38217 |
| HPV45 | L1 | PIFLQMALWR | 22 | 10 | | 38218 |
| HPV45 | L1 | PLDICQSICK | 248 | 10 | | 38219 |
| HPV45 | L1 | PLDICQSICKY | 248 | 11 | | 38220 |
| HPV45 | L1 | PLGIGLSGH | 139 | 9 | | 38221 |
| HPV45 | L1 | PLGIGLSGHPF | 139 | 11 | | 38222 |
| HPV45 | L1 | PLGRKFLVQA | 493 | 10 | | 38223 |
| HPV45 | L1 | PSGAGNKQA | 80 | 9 | | 38224 |
| HPV45 | L1 | PTDLYIKGTSA | 299 | 11 | | 38225 |
| HPV45 | L1 | PTIGPRKR | 508 | 8 | | 38226 |
| HPV45 | L1 | PTIGPRKRPA | 508 | 10 | | 38227 |
| HPV45 | L1 | PTIGPRKRPAA | 508 | 11 | | 38228 |
| HPV45 | L1 | PTKFKHYSR | 387 | 9 | | 38229 |
| HPV45 | L1 | PTKFKHYSRH | 387 | 10 | | 38230 |
| HPV45 | L1 | PTTSLVDTY | 440 | 9 | | 38231 |
| HPV45 | L1 | PTTSLVDTYR | 440 | 10 | | 38232 |
| HPV45 | L1 | PTTSLVDTYRF | 440 | 11 | | 38233 |
| HPV45 | L1 | PVPNTYDPTK | 380 | 10 | | 38234 |
| HPV45 | L1 | PVPNTYDPTKF | 380 | 11 | | 38235 |
| HPV45 | L1 | QAVPKVSA | 87 | 8 | | 38236 |
| HPV45 | L1 | QAVPKVSAY | 87 | 9 | | 38237 |
| HPV45 | L1 | QAVPKVSAYQY | 87 | 11 | | 38238 |
| HPV45 | L1 | QDPYDKLK | 468 | 8 | | 38239 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | L1 | QDPYDKLKF | 468 | 9 | | 38240 |
| HPV45 | L1 | QDVRDNVSVDY | 168 | 11 | | 38241 |
| HPV45 | L1 | QGHNNGICWH | 346 | 10 | | 38242 |
| HPV45 | L1 | QLCILGCVPA | 182 | 10 | | 38243 |
| HPV45 | L1 | QLCTITLTA | 407 | 9 | | 38244 |
| HPV45 | L1 | QLFARHFWNR | 281 | 10 | | 38245 |
| HPV45 | L1 | QLFARHFWNRA | 281 | 11 | | 38246 |
| HPV45 | L1 | QLFNKPYWLH | 334 | 10 | | 38247 |
| HPV45 | L1 | QLFNKPYWLHK | 334 | 11 | | 38248 |
| HPV45 | L1 | QLFVTVVDTTR | 357 | 11 | | 38249 |
| HPV45 | L1 | QSICKYPDY | 253 | 9 | | 38250 |
| HPV45 | L1 | QSVAVTCQK | 452 | 9 | | 38251 |
| HPV45 | L1 | RDNVSVDY | 171 | 8 | | 38252 |
| HPV45 | L1 | RDNVSVDYK | 171 | 9 | | 38253 |
| HPV45 | L1 | RLLTVGNPY | 67 | 9 | | 38254 |
| HPV45 | L1 | RLLTVGNPYF | 67 | 10 | | 38255 |
| HPV45 | L1 | RLLTVGNPYFR | 67 | 11 | | 38256 |
| HPV45 | L1 | RSTNLTLCA | 367 | 9 | | 38257 |
| HPV45 | L1 | RTSIFYHA | 56 | 8 | | 38258 |
| HPV45 | L1 | RVALPDPNK | 101 | 9 | | 38259 |
| HPV45 | L1 | RVALPDPNKF | 101 | 10 | | 38260 |
| HPV45 | L1 | RVRIRSKK | 529 | 8 | | 38261 |
| HPV45 | L1 | RVVNTDDY | 46 | 8 | | 38262 |
| HPV45 | L1 | RVVNTDDYVSR | 46 | 11 | | 38263 |
| HPV45 | L1 | RVVPSGAGNK | 77 | 10 | | 38264 |
| HPV45 | L1 | SADPYGDSMF | 265 | 10 | | 38265 |
| HPV45 | L1 | SADPYGDSMFF | 265 | 11 | | 38266 |
| HPV45 | L1 | SAYQYRVF | 93 | 8 | | 38267 |
| HPV45 | L1 | SAYQYRVFR | 93 | 9 | | 38268 |
| HPV45 | L1 | SAYQYRVFRVA | 93 | 11 | | 38269 |
| HPV45 | L1 | SDLDQYPLGR | 487 | 10 | | 38270 |
| HPV45 | L1 | SDLDQYPLGRK | 487 | 11 | | 38271 |
| HPV45 | L1 | SDSQLFNK | 331 | 8 | | 38272 |
| HPV45 | L1 | SDSQLFNKPY | 331 | 10 | | 38273 |
| HPV45 | L1 | SGAGNKQA | 81 | 8 | | 38274 |
| HPV45 | L1 | SGAGNKQAVPK | 81 | 11 | | 38275 |
| HPV45 | L1 | SGHPFYNK | 145 | 8 | | 38276 |
| HPV45 | L1 | SICKYPDY | 254 | 8 | | 38277 |
| HPV45 | L1 | SIFYHAGSSR | 58 | 10 | | 38278 |
| HPV45 | L1 | SILENWNF | 427 | 8 | | 38279 |
| HPV45 | L1 | SITTSDSQLF | 327 | 10 | | 38280 |
| HPV45 | L1 | SLVDTYRF | 443 | 8 | | 38281 |
| HPV45 | L1 | SMFFCLRR | 272 | 8 | | 38282 |
| HPV45 | L1 | SSDLDQYPLGR | 486 | 11 | | 38283 |
| HPV45 | L1 | SSILENWNF | 426 | 9 | | 38284 |
| HPV45 | L1 | SSRLLTVGNPY | 65 | 11 | | 38285 |
| HPV45 | L1 | STASRPAK | 521 | 8 | | 38286 |
| HPV45 | L1 | STASRPAKR | 521 | 9 | | 38287 |
| HPV45 | L1 | STASRPAKRVR | 521 | 11 | | 38288 |
| HPV45 | L1 | STIYNPETQR | 115 | 10 | | 38289 |
| HPV45 | L1 | STNLTLCA | 368 | 8 | | 38290 |
| HPV45 | L1 | STQNPVPNTY | 376 | 10 | | 38291 |
| HPV45 | L1 | STSTASRPA | 519 | 9 | | 38292 |
| HPV45 | L1 | STSTASRPAK | 519 | 10 | | 38293 |
| HPV45 | L1 | STSTASRPAKR | 519 | 11 | | 38294 |
| HPV45 | L1 | STVYLPPPSVA | 35 | 11 | | 38295 |
| HPV45 | L1 | SVARVVNTDDY | 43 | 11 | | 38296 |
| HPV45 | L1 | SVAVTCQK | 453 | 8 | | 38297 |
| HPV45 | L1 | TAEVMSYIH | 414 | 9 | | 38298 |
| HPV45 | L1 | TASRPAKR | 522 | 8 | | 38299 |
| HPV45 | L1 | TASRPAKRVR | 522 | 10 | | 38300 |
| HPV45 | L1 | TAVITQDVR | 163 | 9 | | 38301 |
| HPV45 | L1 | TCQKDTTPPEK | 457 | 11 | | 38302 |
| HPV45 | L1 | TDDYVSRTSIF | 50 | 11 | | 38303 |
| HPV45 | L1 | TDLYIKGTSA | 300 | 10 | | 38304 |
| HPV45 | L1 | TGYGAMDF | 230 | 8 | | 38305 |
| HPV45 | L1 | TIGPRKRPA | 509 | 9 | | 38306 |
| HPV45 | L1 | TIGPRKRPAA | 509 | 10 | | 38307 |
| HPV45 | L1 | TITLTAEVMSY | 410 | 11 | | 38308 |
| HPV45 | L1 | TIYNPETQR | 116 | 9 | | 38309 |
| HPV45 | L1 | TLTAEVMSY | 412 | 9 | | 38310 |
| HPV45 | L1 | TLTAEVMSYIH | 412 | 11 | | 38311 |
| HPV45 | L1 | TSDSQLFNK | 330 | 9 | | 38312 |
| HPV45 | L1 | TSDSQLFNKPY | 330 | 11 | | 38313 |
| HPV45 | L1 | TSIFYHAGSSR | 57 | 11 | | 38314 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | L1 | TSLVDTYR | 442 | 8 | | 38315 |
| HPV45 | L1 | TSLVDTYRF | 442 | 9 | | 38316 |
| HPV45 | L1 | TSTASRPA | 520 | 8 | | 38317 |
| HPV45 | L1 | TSTASRPAK | 520 | 9 | | 38318 |
| HPV45 | L1 | TSTASRPAKR | 520 | 10 | | 38319 |
| HPV45 | L1 | TTPPEKQDPY | 462 | 10 | | 38320 |
| HPV45 | L1 | TTRSTNLTLCA | 365 | 11 | | 38321 |
| HPV45 | L1 | TTSDSQLF | 329 | 8 | | 38322 |
| HPV45 | L1 | TTSDSQLFNK | 329 | 10 | | 38323 |
| HPV45 | L1 | TTSLVDTY | 441 | 8 | | 38324 |
| HPV45 | L1 | TTSLVDTYR | 441 | 9 | | 38325 |
| HPV45 | L1 | TTSLVDTYRF | 441 | 10 | | 38326 |
| HPV45 | L1 | TVDLKEKF | 478 | 8 | | 38327 |
| HPV45 | L1 | TVGNPYFR | 70 | 8 | | 38328 |
| HPV45 | L1 | TVPTDLYIK | 297 | 9 | | 38329 |
| HPV45 | L1 | TVYLPPPSVA | 36 | 10 | | 38330 |
| HPV45 | L1 | TVYLPPPSVAR | 36 | 11 | | 38331 |
| HPV45 | L1 | VALPDPNK | 102 | 8 | | 38332 |
| HPV45 | L1 | VALPDPNKF | 102 | 9 | | 38333 |
| HPV45 | L1 | VARVVNTDDY | 44 | 10 | | 38334 |
| HPV45 | L1 | VDTGYGAMDF | 228 | 10 | | 38335 |
| HPV45 | L1 | VDTYRFVQSVA | 445 | 11 | | 38336 |
| HPV45 | L1 | VFPIFLQMA | 20 | 9 | | 38337 |
| HPV45 | L1 | VFRVALPDPNK | 99 | 11 | | 38338 |
| HPV45 | L1 | VMGDTVPTDLY | 293 | 11 | | 38339 |
| HPV45 | L1 | VSAYQYRVF | 92 | 9 | | 38340 |
| HPV45 | L1 | VSAYQYRVFR | 92 | 10 | | 38341 |
| HPV45 | L1 | VSRTSIFY | 54 | 8 | | 38342 |
| HPV45 | L1 | VSRTSIFYH | 54 | 9 | | 38343 |
| HPV45 | L1 | VSRTSIFYHA | 54 | 10 | | 38344 |
| HPV45 | L1 | VTVVDTTR | 360 | 8 | | 38345 |
| HPV45 | L1 | VVNTDDYVSR | 47 | 10 | | 38346 |
| HPV45 | L1 | VVPSGAGNK | 78 | 9 | | 38347 |
| HPV45 | L1 | VVPSGAGNKQA | 78 | 11 | | 38348 |
| HPV45 | L1 | WACVGMEIGR | 127 | 10 | | 38349 |
| HPV45 | L1 | WAKGTLCK | 196 | 8 | | 38350 |
| HPV45 | L1 | WAKGTLCKPA | 196 | 10 | | 38351 |
| HPV45 | L1 | WLHKAQGH | 341 | 8 | | 38352 |
| HPV45 | L1 | WTVDLKEK | 477 | 8 | | 38353 |
| HPV45 | L1 | WTVDLKEKF | 477 | 9 | | 38354 |
| HPV45 | L1 | YDPTKFKH | 385 | 8 | | 38355 |
| HPV45 | L1 | YDPTKFKHY | 385 | 9 | | 38356 |
| HPV45 | L1 | YDPTKFKHYSR | 385 | 11 | | 38357 |
| HPV45 | L1 | YFRVVPSGA | 75 | 9 | | 38358 |
| HPV45 | L1 | YGDSMFFCLR | 269 | 10 | | 38359 |
| HPV45 | L1 | YGDSMFFCLRR | 269 | 11 | | 38360 |
| HPV45 | L1 | YGHGIIIF | 7 | 8 | | 38361 |
| HPV45 | L1 | YGHGIIIFLK | 7 | 10 | | 38362 |
| HPV45 | L1 | YIKGTSANMR | 303 | 10 | | 38363 |
| HPV45 | L1 | YLPPPSVA | 38 | 8 | | 38364 |
| HPV45 | L1 | YLPPPSVAR | 38 | 9 | | 38365 |
| HPV45 | L1 | YLQMSADPY | 261 | 9 | | 38366 |
| HPV45 | L1 | YSRHVEEY | 393 | 8 | | 38367 |
| HPV45 | L1 | YVSRTSIF | 53 | 8 | | 38368 |
| HPV45 | L1 | YVSRTSIFY | 53 | 9 | | 38369 |
| HPV45 | L1 | YVSRTSIFYH | 53 | 10 | | 38370 |
| HPV45 | L1 | YVSRTSIFYHA | 53 | 11 | | 38371 |
| HPV45 | L2 | AARRKRASA | 6 | 9 | | 38372 |
| HPV45 | L2 | ALSSRRGTVR | 286 | 10 | | 38373 |
| HPV45 | L2 | ALSSRRGTVRF | 286 | 11 | | 38374 |
| HPV45 | L2 | ASATDLYR | 12 | 8 | | 38375 |
| HPV45 | L2 | ASATDLYRTCK | 12 | 11 | | 38376 |
| HPV45 | L2 | ASGAPVPTF | 114 | 9 | | 38377 |
| HPV45 | L2 | ASTTPSTIH | 357 | 9 | | 38378 |
| HPV45 | L2 | ASTTPSTIHK | 357 | 10 | | 38379 |
| HPV45 | L2 | ASTTTYIGIH | 423 | 10 | | 38380 |
| HPV45 | L2 | ATDLYRTCK | 14 | 9 | | 38381 |
| HPV45 | L2 | ATMFTRSGK | 303 | 9 | | 38382 |
| HPV45 | L2 | ATNDSDLF | 340 | 8 | | 38383 |
| HPV45 | L2 | ATNDSDLFDVY | 340 | 11 | | 38384 |
| HPV45 | L2 | DFMDIIRLH | 275 | 9 | | 38385 |
| HPV45 | L2 | DFMDIIRLHR | 275 | 10 | | 38386 |
| HPV45 | L2 | DIIRLHRPA | 278 | 9 | | 38387 |
| HPV45 | L2 | DLFDVYADF | 345 | 9 | | 38388 |
| HPV45 | L2 | DSDFMDIIR | 273 | 9 | | 38389 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | L2 | DSDFMDIIRLH | 273 | 11 | | 38390 |
| HPV45 | L2 | DSDLFDVY | 343 | 8 | | 38391 |
| HPV45 | L2 | DSDLFDVYA | 343 | 9 | | 38392 |
| HPV45 | L2 | DSDLFDVYADF | 343 | 11 | | 38393 |
| HPV45 | L2 | DSSVVASGA | 109 | 9 | | 38394 |
| HPV45 | L2 | DSVSISSTSF | 148 | 10 | | 38395 |
| HPV45 | L2 | DVYADFPPPA | 348 | 10 | | 38396 |
| HPV45 | L2 | EDSSVVASGA | 108 | 10 | | 38397 |
| HPV45 | L2 | EGTTLADK | 36 | 8 | | 38398 |
| HPV45 | L2 | EIELQPLISA | 331 | 10 | | 38399 |
| HPV45 | L2 | EIPLQTFA | 194 | 8 | | 38400 |
| HPV45 | L2 | EITSSGTTTPA | 129 | 11 | | 38401 |
| HPV45 | L2 | ELQPLISA | 333 | 8 | | 38402 |
| HPV45 | L2 | FADGFVAA | 456 | 8 | | 38403 |
| HPV45 | L2 | FDVYADFPPPA | 347 | 11 | | 38404 |
| HPV45 | L2 | FFADGFVA | 455 | 8 | | 38405 |
| HPV45 | L2 | FFADGFVAA | 455 | 9 | | 38406 |
| HPV45 | L2 | FLTHPSSLVTF | 241 | 11 | | 38407 |
| HPV45 | L2 | FMDIIRLH | 276 | 8 | | 38408 |
| HPV45 | L2 | FMDIIRLHR | 276 | 9 | | 38409 |
| HPV45 | L2 | FMDIIRLHRPA | 276 | 11 | | 38410 |
| HPV45 | L2 | FSRLGQRA | 296 | 8 | | 38411 |
| HPV45 | L2 | FSRLGQRATMF | 296 | 11 | | 38412 |
| HPV45 | L2 | FTRSGKQIGGR | 306 | 11 | | 38413 |
| HPV45 | L2 | FVGTPTSGSH | 181 | 10 | | 38414 |
| HPV45 | L2 | GGRVHFYH | 314 | 8 | | 38415 |
| HPV45 | L2 | GIGTGSGSGGR | 58 | 11 | | 38416 |
| HPV45 | L2 | GIHGTQYY | 430 | 8 | | 38417 |
| HPV45 | L2 | GSGGRTGY | 64 | 8 | | 38418 |
| HPV45 | L2 | GSGSGGRTGY | 62 | 10 | | 38419 |
| HPV45 | L2 | GTCPPDVINK | 25 | 10 | | 38420 |
| HPV45 | L2 | GTGSGSGGR | 60 | 9 | | 38421 |
| HPV45 | L2 | GTPTSGSH | 183 | 8 | | 38422 |
| HPV45 | L2 | GTPTSGSHGY | 183 | 10 | | 38423 |
| HPV45 | L2 | GTQYYLWPWY | 433 | 10 | | 38424 |
| HPV45 | L2 | GTQYYLWPWYY | 433 | 11 | | 38425 |
| HPV45 | L2 | GTVRFSRLGQR | 292 | 11 | | 38426 |
| HPV45 | L2 | HDISPIAA | 321 | 8 | | 38427 |
| HPV45 | L2 | HFYHDISPIA | 318 | 10 | | 38428 |
| HPV45 | L2 | HFYHDISPIAA | 318 | 11 | | 38429 |
| HPV45 | L2 | HGTQYYLWPWY | 432 | 11 | | 38430 |
| HPV45 | L2 | HGYEEIPLQTF | 190 | 11 | | 38431 |
| HPV45 | L2 | IFVGTPTSGSH | 180 | 11 | | 38432 |
| HPV45 | L2 | IGGRVHFY | 313 | 8 | | 38433 |
| HPV45 | L2 | IGGRVHFYH | 313 | 9 | | 38434 |
| HPV45 | L2 | IGIHGTQY | 429 | 8 | | 38435 |
| HPV45 | L2 | IGIHGTQYY | 429 | 9 | | 38436 |
| HPV45 | L2 | IGTGSGSGGR | 59 | 10 | | 38437 |
| HPV45 | L2 | IIRLHRPA | 279 | 8 | | 38438 |
| HPV45 | L2 | ILQWSSLGIF | 44 | 10 | | 38439 |
| HPV45 | L2 | ISATNDSDLF | 338 | 10 | | 38440 |
| HPV45 | L2 | ISSTPLPTVR | 210 | 10 | | 38441 |
| HPV45 | L2 | ISSTPLPTVRR | 210 | 11 | | 38442 |
| HPV45 | L2 | ISSTSFTNPA | 152 | 10 | | 38443 |
| HPV45 | L2 | ISSTSFTNPAF | 152 | 11 | | 38444 |
| HPV45 | L2 | ITSSGTTTPA | 130 | 10 | | 38445 |
| HPV45 | L2 | KILQWSSLGIF | 43 | 11 | | 38446 |
| HPV45 | L2 | KSFTYPKY | 366 | 8 | | 38447 |
| HPV45 | L2 | KVEGTTLA | 34 | 8 | | 38448 |
| HPV45 | L2 | KVEGTTLADK | 34 | 10 | | 38449 |
| HPV45 | L2 | LFDVYADF | 346 | 8 | | 38450 |
| HPV45 | L2 | LGQRATMF | 299 | 8 | | 38451 |
| HPV45 | L2 | LGQRATMFTR | 299 | 10 | | 38452 |
| HPV45 | L2 | LISATNDSDLF | 337 | 11 | | 38453 |
| HPV45 | L2 | LSSRRGTVR | 287 | 9 | | 38454 |
| HPV45 | L2 | LSSRRGTVRF | 287 | 10 | | 38455 |
| HPV45 | L2 | LTHPSSLVTF | 242 | 10 | | 38456 |
| HPV45 | L2 | LTMPSTAA | 375 | 8 | | 38457 |
| HPV45 | L2 | LTMPSTAASSY | 375 | 11 | | 38458 |
| HPV45 | L2 | LTSAWDVPIY | 392 | 10 | | 38459 |
| HPV45 | L2 | LVEDSSVVA | 106 | 9 | | 38460 |
| HPV45 | L2 | LVTFDNPA | 248 | 8 | | 38461 |
| HPV45 | L2 | LVTFDNPAY | 248 | 9 | | 38462 |
| HPV45 | L2 | MDIIRLHR | 277 | 8 | | 38463 |
| HPV45 | L2 | MDIIRLHRPA | 277 | 10 | | 38464 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | L2 | MVSHRAAR | 1 | 8 | | 38465 |
| HPV45 | L2 | MVSHRAARR | 1 | 9 | | 38466 |
| HPV45 | L2 | MVSHRAARRK | 1 | 10 | | 38467 |
| HPV45 | L2 | MVSHRAARRKR | 1 | 11 | | 38468 |
| HPV45 | L2 | NASTTTYIGIH | 422 | 11 | | 38469 |
| HPV45 | L2 | NDSDLFDVY | 342 | 9 | | 38470 |
| HPV45 | L2 | NDSDLFDVYA | 342 | 10 | | 38471 |
| HPV45 | L2 | NTVVDVGPTR | 79 | 10 | | 38472 |
| HPV45 | L2 | NVTVPLTSA | 387 | 9 | | 38473 |
| HPV45 | L2 | PALSSRRGTVR | 285 | 11 | | 38474 |
| HPV45 | L2 | PASTTPSTIH | 356 | 10 | | 38475 |
| HPV45 | L2 | PASTTPSTIHK | 356 | 11 | | 38476 |
| HPV45 | L2 | PDIILPSH | 404 | 8 | | 38477 |
| HPV45 | L2 | PDSDFMDIIR | 272 | 10 | | 38478 |
| HPV45 | L2 | PISSTPLPTVR | 209 | 11 | | 38479 |
| HPV45 | L2 | PLDTTLSF | 258 | 8 | | 38480 |
| HPV45 | L2 | PLPTVRRVR | 214 | 9 | | 38481 |
| HPV45 | L2 | PLTSAWDVPIY | 391 | 11 | | 38482 |
| HPV45 | L2 | PMWPSTSPTNA | 413 | 11 | | 38483 |
| HPV45 | L2 | PSSLVTFDNPA | 245 | 11 | | 38484 |
| HPV45 | L2 | PSTAASSY | 378 | 8 | | 38485 |
| HPV45 | L2 | PSTIHKSF | 361 | 8 | | 38486 |
| HPV45 | L2 | PSTIHKSFTY | 361 | 10 | | 38487 |
| HPV45 | L2 | PSTSPTNA | 416 | 8 | | 38488 |
| HPV45 | L2 | PTFTGTSGF | 120 | 9 | | 38489 |
| HPV45 | L2 | PTNASTTTY | 420 | 9 | | 38490 |
| HPV45 | L2 | PTSGSHGY | 185 | 8 | | 38491 |
| HPV45 | L2 | PTSNVPDSDF | 267 | 10 | | 38492 |
| HPV45 | L2 | PTVRRVRGPR | 216 | 10 | | 38493 |
| HPV45 | L2 | PVPTFTGTSGF | 118 | 11 | | 38494 |
| HPV45 | L2 | QIGGRVHF | 312 | 8 | | 38495 |
| HPV45 | L2 | QIGGRVHFY | 312 | 9 | | 38496 |
| HPV45 | L2 | QIGGRVHFYH | 312 | 10 | | 38497 |
| HPV45 | L2 | QTGEVSGNIF | 172 | 10 | | 38498 |
| HPV45 | L2 | QVRVSTSQF | 233 | 9 | | 38499 |
| HPV45 | L2 | RAARRKRA | 5 | 8 | | 38500 |
| HPV45 | L2 | RAARRKRASA | 5 | 10 | | 38501 |
| HPV45 | L2 | RASATDLY | 11 | 8 | | 38502 |
| HPV45 | L2 | RASATDLYR | 11 | 9 | | 38503 |
| HPV45 | L2 | RATMFTRSGK | 302 | 10 | | 38504 |
| HPV45 | L2 | RFSRLGQR | 295 | 8 | | 38505 |
| HPV45 | L2 | RFSRLGQRA | 295 | 9 | | 38506 |
| HPV45 | L2 | RGPRLYSR | 222 | 8 | | 38507 |
| HPV45 | L2 | RGPRLYSRA | 222 | 9 | | 38508 |
| HPV45 | L2 | RGTVRFSR | 291 | 8 | | 38509 |
| HPV45 | L2 | RIPYFFADGF | 451 | 10 | | 38510 |
| HPV45 | L2 | RLGQRATMF | 298 | 9 | | 38511 |
| HPV45 | L2 | RLGQRATMFTR | 298 | 11 | | 38512 |
| HPV45 | L2 | RLHRPALSSR | 281 | 10 | | 38513 |
| HPV45 | L2 | RLHRPALSSRR | 281 | 11 | | 38514 |
| HPV45 | L2 | RLYSRANQQVR | 225 | 11 | | 38515 |
| HPV45 | L2 | RSGKQIGGR | 308 | 9 | | 38516 |
| HPV45 | L2 | RSGKQIGGRVH | 308 | 11 | | 38517 |
| HPV45 | L2 | RTGYVPLGGR | 68 | 10 | | 38518 |
| HPV45 | L2 | RVRGPRLY | 220 | 8 | | 38519 |
| HPV45 | L2 | RVRGPRLYSR | 220 | 10 | | 38520 |
| HPV45 | L2 | RVRGPRLYSRA | 220 | 11 | | 38521 |
| HPV45 | L2 | RVSTSQFLTH | 235 | 10 | | 38522 |
| HPV45 | L2 | SATDLYRTCK | 13 | 10 | | 38523 |
| HPV45 | L2 | SATNDSDLF | 339 | 9 | | 38524 |
| HPV45 | L2 | SAWDVPIY | 394 | 8 | | 38525 |
| HPV45 | L2 | SDFMDIIR | 274 | 8 | | 38526 |
| HPV45 | L2 | SDFMDIIRLH | 274 | 10 | | 38527 |
| HPV45 | L2 | SDFMDIIRLHR | 274 | 11 | | 38528 |
| HPV45 | L2 | SDLFDVYA | 344 | 8 | | 38529 |
| HPV45 | L2 | SDLFDVYADF | 344 | 10 | | 38530 |
| HPV45 | L2 | SGAPVPTF | 115 | 8 | | 38531 |
| HPV45 | L2 | SGKQIGGR | 309 | 8 | | 38532 |
| HPV45 | L2 | SGKQIGGRVH | 309 | 10 | | 38533 |
| HPV45 | L2 | SGKQIGGRVHF | 309 | 11 | | 38534 |
| HPV45 | L2 | SGSGGRTGY | 63 | 9 | | 38535 |
| HPV45 | L2 | SGTCPPDVINK | 24 | 11 | | 38536 |
| HPV45 | L2 | SISSTSFTNPA | 151 | 11 | | 38537 |
| HPV45 | L2 | SLTMPSTA | 374 | 8 | | 38538 |
| HPV45 | L2 | SLTMPSTAA | 374 | 9 | | 38539 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | L2 | SLVTFDNPA | 247 | 9 | | 38540 |
| HPV45 | L2 | SLVTFDNPAY | 247 | 10 | | 38541 |
| HPV45 | L2 | SSGTTTPA | 132 | 8 | | 38542 |
| HPV45 | L2 | SSLVTFDNPA | 246 | 10 | | 38543 |
| HPV45 | L2 | SSLVTFDNPAY | 246 | 11 | | 38544 |
| HPV45 | L2 | SSRRGTVR | 288 | 8 | | 38545 |
| HPV45 | L2 | SSRRGTVRF | 288 | 9 | | 38546 |
| HPV45 | L2 | SSRRGTVRFSR | 288 | 11 | | 38547 |
| HPV45 | L2 | SSTPLPTVR | 211 | 9 | | 38548 |
| HPV45 | L2 | SSTPLPTVRR | 211 | 10 | | 38549 |
| HPV45 | L2 | SSTSFTNPA | 153 | 9 | | 38550 |
| HPV45 | L2 | SSTSFTNPAF | 153 | 10 | | 38551 |
| HPV45 | L2 | SSVVASGA | 110 | 8 | | 38552 |
| HPV45 | L2 | STIHKSFTY | 362 | 9 | | 38553 |
| HPV45 | L2 | STIHKSFTYPK | 362 | 11 | | 38554 |
| HPV45 | L2 | STPLPTVR | 212 | 8 | | 38555 |
| HPV45 | L2 | STPLPTVRR | 212 | 9 | | 38556 |
| HPV45 | L2 | STPLPTVRRVR | 212 | 11 | | 38557 |
| HPV45 | L2 | STSFTNPA | 154 | 8 | | 38558 |
| HPV45 | L2 | STSFTNPAF | 154 | 9 | | 38559 |
| HPV45 | L2 | STSQFLTH | 237 | 8 | | 38560 |
| HPV45 | L2 | STTPSTIH | 358 | 8 | | 38561 |
| HPV45 | L2 | STTPSTIHK | 358 | 9 | | 38562 |
| HPV45 | L2 | STTPSTIHKSF | 358 | 11 | | 38563 |
| HPV45 | L2 | STTTYIGIH | 424 | 9 | | 38564 |
| HPV45 | L2 | SVSISSTSF | 149 | 9 | | 38565 |
| HPV45 | L2 | TCPPDVINK | 26 | 9 | | 38566 |
| HPV45 | L2 | TDLYRTCK | 15 | 8 | | 38567 |
| HPV45 | L2 | TFTGTSGF | 121 | 8 | | 38568 |
| HPV45 | L2 | TGEVSGNIF | 173 | 9 | | 38569 |
| HPV45 | L2 | TGPDIILPSH | 402 | 10 | | 38570 |
| HPV45 | L2 | TGSGSGGR | 61 | 8 | | 38571 |
| HPV45 | L2 | TGSGSGGRTGY | 61 | 11 | | 38572 |
| HPV45 | L2 | TGYVPLGGR | 69 | 9 | | 38573 |
| HPV45 | L2 | TIHKSFTY | 363 | 8 | | 38574 |
| HPV45 | L2 | TIHKSFTYPK | 363 | 10 | | 38575 |
| HPV45 | L2 | TIHKSFTYPKY | 363 | 11 | | 38576 |
| HPV45 | L2 | TLVEDSSVVA | 105 | 10 | | 38577 |
| HPV45 | L2 | TMFTRSGK | 304 | 8 | | 38578 |
| HPV45 | L2 | TMPSTAASSY | 376 | 10 | | 38579 |
| HPV45 | L2 | TSAWDVPIY | 393 | 9 | | 38580 |
| HPV45 | L2 | TSFTNPAF | 155 | 8 | | 38581 |
| HPV45 | L2 | TSNVPDSDF | 268 | 9 | | 38582 |
| HPV45 | L2 | TSPTNASTTTY | 418 | 11 | | 38583 |
| HPV45 | L2 | TSSGTTTPA | 131 | 9 | | 38584 |
| HPV45 | L2 | TTPSTIHK | 359 | 8 | | 38585 |
| HPV45 | L2 | TTPSTIHKSF | 359 | 10 | | 38586 |
| HPV45 | L2 | TTTYIGIH | 425 | 8 | | 38587 |
| HPV45 | L2 | TTYIGIHGTQY | 426 | 11 | | 38588 |
| HPV45 | L2 | TVRFSRLGQR | 293 | 10 | | 38589 |
| HPV45 | L2 | TVRFSRLGQRA | 293 | 11 | | 38590 |
| HPV45 | L2 | TVRRVRGPR | 217 | 9 | | 38591 |
| HPV45 | L2 | TVRRVRGPRLY | 217 | 11 | | 38592 |
| HPV45 | L2 | TVVDVGPTR | 80 | 9 | | 38593 |
| HPV45 | L2 | VASGAPVPTF | 113 | 10 | | 38594 |
| HPV45 | L2 | VDSVSISSTSF | 147 | 11 | | 38595 |
| HPV45 | L2 | VGTPTSGSH | 182 | 9 | | 38596 |
| HPV45 | L2 | VGTPTSGSHGY | 182 | 11 | | 38597 |
| HPV45 | L2 | VINKVEGTTLA | 31 | 11 | | 38598 |
| HPV45 | L2 | VSHRAARR | 2 | 8 | | 38599 |
| HPV45 | L2 | VSHRAARRK | 2 | 9 | | 38600 |
| HPV45 | L2 | VSHRAARRKR | 2 | 10 | | 38601 |
| HPV45 | L2 | VSHRAARRKRA | 2 | 11 | | 38602 |
| HPV45 | L2 | VSISSTSF | 150 | 8 | | 38603 |
| HPV45 | L2 | VSTSQFLTH | 236 | 9 | | 38604 |
| HPV45 | L2 | VTFDNPAY | 249 | 8 | | 38605 |
| HPV45 | L2 | VTLVEDSSVVA | 104 | 11 | | 38606 |
| HPV45 | L2 | VTVPLTSA | 388 | 8 | | 38607 |
| HPV45 | L2 | VVASGAPVPTF | 112 | 11 | | 38608 |
| HPV45 | L2 | VVDVGPTR | 81 | 8 | | 38609 |
| HPV45 | L2 | YADFPPPA | 350 | 8 | | 38610 |
| HPV45 | L2 | YFFADGFVA | 454 | 9 | | 38611 |
| HPV45 | L2 | YFFADGFVAA | 454 | 10 | | 38612 |
| HPV45 | L2 | YFPKKRKR | 444 | 8 | | 38613 |
| HPV45 | L2 | YFPKKRKRIPY | 444 | 11 | | 38614 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV45 | L2 | YIGIHGTQY | 428 | 9 | | 38615 |
| HPV45 | L2 | YIGIHGTQYY | 428 | 10 | | 38616 |
| HPV45 | L2 | YLWPWYYY | 437 | 8 | | 38617 |
| HPV45 | L2 | YLWPWYYYF | 437 | 9 | | 38618 |
| HPV45 | L2 | YLWPWYYYFPK | 437 | 11 | | 38619 |
| HPV45 | L2 | YSLTMPSTA | 373 | 9 | | 38620 |
| HPV45 | L2 | YSLTMPSTAA | 373 | 10 | | 38621 |
| HPV45 | L2 | YSNVTVPLTSA | 385 | 11 | | 38622 |
| HPV45 | L2 | YSRANQQVR | 227 | 9 | | 38623 |
| HPV45 | L2 | YTGPDIILPSH | 401 | 11 | | 38624 |
| HPV56 | E2 | AAVSHRPGK | 177 | 9 | | 38625 |
| HPV56 | E2 | AAVSHRPGKR | 177 | 10 | | 38626 |
| HPV56 | E2 | ACSAIEVQIA | 12 | 10 | | 38627 |
| HPV56 | E2 | ALESLSTTIY | 21 | 10 | | 38628 |
| HPV56 | E2 | AVSHRPGK | 178 | 8 | | 38629 |
| HPV56 | E2 | AVSHRPGKR | 178 | 9 | | 38630 |
| HPV56 | E2 | AVSHRPGKRPR | 178 | 11 | | 38631 |
| HPV56 | E2 | CCRYRFQK | 249 | 8 | | 38632 |
| HPV56 | E2 | CCRYRFQKY | 249 | 9 | | 38633 |
| HPV56 | E2 | CCRYRFQKYK | 249 | 10 | | 38634 |
| HPV56 | E2 | CFKKEGQH | 52 | 8 | | 38635 |
| HPV56 | E2 | CLQVCKAK | 4 | 8 | | 38636 |
| HPV56 | E2 | CLQVCKAKA | 4 | 9 | | 38637 |
| HPV56 | E2 | CMQYVAWK | 71 | 8 | | 38638 |
| HPV56 | E2 | CMQYVAWKY | 71 | 9 | | 38639 |
| HPV56 | E2 | CMQYVAWKYIY | 71 | 11 | | 38640 |
| HPV56 | E2 | CSAIEVQIA | 13 | 9 | | 38641 |
| HPV56 | E2 | CSGVDYRGIY | 92 | 10 | | 38642 |
| HPV56 | E2 | CSGVDYRGIYY | 92 | 11 | | 38643 |
| HPV56 | E2 | DAAVSHRPGK | 176 | 10 | | 38644 |
| HPV56 | E2 | DAAVSHRPGKR | 176 | 11 | | 38645 |
| HPV56 | E2 | DFEQEAKK | 113 | 8 | | 38646 |
| HPV56 | E2 | DFEQEAKKF | 113 | 9 | | 38647 |
| HPV56 | E2 | DGHKTYYTDF | 105 | 10 | | 38648 |
| HPV56 | E2 | DGSKNNCMQY | 65 | 10 | | 38649 |
| HPV56 | E2 | DSSRESHA | 195 | 8 | | 38650 |
| HPV56 | E2 | DSSRESHAK | 195 | 9 | | 38651 |
| HPV56 | E2 | DSVSSTCR | 140 | 8 | | 38652 |
| HPV56 | E2 | DSVSSTCRY | 140 | 9 | | 38653 |
| HPV56 | E2 | DTDNTDSR | 213 | 8 | | 38654 |
| HPV56 | E2 | DTDNTDSRSR | 213 | 10 | | 38655 |
| HPV56 | E2 | EAKKFGCK | 117 | 8 | | 38656 |
| HPV56 | E2 | EFDSSRESH | 193 | 9 | | 38657 |
| HPV56 | E2 | EFDSSRESHA | 193 | 10 | | 38658 |
| HPV56 | E2 | EFDSSRESHAK | 193 | 11 | | 38659 |
| HPV56 | E2 | EGQHIEVWF | 56 | 9 | | 38660 |
| HPV56 | E2 | ELWLTEPK | 43 | 8 | | 38661 |
| HPV56 | E2 | ELWLTEPKK | 43 | 9 | | 38662 |
| HPV56 | E2 | ELWLTEPKKCF | 43 | 11 | | 38663 |
| HPV56 | E2 | ESEFDSSR | 191 | 8 | | 38664 |
| HPV56 | E2 | ESEFDSSRESH | 191 | 11 | | 38665 |
| HPV56 | E2 | ESHAKCVTTH | 199 | 10 | | 38666 |
| HPV56 | E2 | ESLSTTIY | 23 | 8 | | 38667 |
| HPV56 | E2 | ETQRNSFLSH | 288 | 10 | | 38668 |
| HPV56 | E2 | ETVNEYNTH | 154 | 9 | | 38669 |
| HPV56 | E2 | ETVNEYNTHK | 154 | 10 | | 38670 |
| HPV56 | E2 | EVHMENESIY | 128 | 10 | | 38671 |
| HPV56 | E2 | EVWFDGSK | 61 | 8 | | 38672 |
| HPV56 | E2 | FDGSKNNCMQY | 64 | 11 | | 38673 |
| HPV56 | E2 | FDSSRESH | 194 | 8 | | 38674 |
| HPV56 | E2 | FDSSRESHA | 194 | 9 | | 38675 |
| HPV56 | E2 | FDSSRESHAK | 194 | 10 | | 38676 |
| HPV56 | E2 | FGCKNIWEVH | 121 | 10 | | 38677 |
| HPV56 | E2 | FLSHVKIPVVY | 294 | 11 | | 38678 |
| HPV56 | E2 | FVDVTSTY | 261 | 8 | | 38679 |
| HPV56 | E2 | FVDVTSTYH | 261 | 9 | | 38680 |
| HPV56 | E2 | GCKNIWEVH | 122 | 9 | | 38681 |
| HPV56 | E2 | GDKTTPVVH | 231 | 9 | | 38682 |
| HPV56 | E2 | GDKTTPVVHLK | 231 | 11 | | 38683 |
| HPV56 | E2 | GIYYVHDGH | 99 | 9 | | 38684 |
| HPV56 | E2 | GIYYVHDGHK | 99 | 10 | | 38685 |
| HPV56 | E2 | GSKNNCMQY | 66 | 9 | | 38686 |
| HPV56 | E2 | GSKNNCMQYVA | 66 | 11 | | 38687 |
| HPV56 | 12 | GVDYRGIY | 94 | 8 | | 38688 |
| HPV56 | E2 | GVDYRGIYY | 94 | 9 | | 38689 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | E2 | GVDYRGIYYVH | 94 | 11 | | 38690 |
| HPV56 | E2 | HAKCVTTH | 201 | 8 | | 38691 |
| HPV56 | E2 | HAKCVTTHTH | 201 | 10 | | 38692 |
| HPV56 | E2 | HDGHKTYY | 104 | 8 | | 38693 |
| HPV56 | E2 | HDGHKTYYTDF | 104 | 11 | | 38694 |
| HPV56 | E2 | HIEVWFDGSK | 59 | 10 | | 38695 |
| HPV56 | E2 | HISDTDNTDSR | 210 | 11 | | 38696 |
| HPV56 | E2 | HLKGEPNR | 239 | 8 | | 38697 |
| HPV56 | E2 | HLKGEPNRLK | 239 | 10 | | 38698 |
| HPV56 | E2 | HMENESIY | 130 | 8 | | 38699 |
| HPV56 | E2 | HVKIPVVY | 297 | 8 | | 38700 |
| HPV56 | E2 | HVKIPVVYR | 297 | 9 | | 38701 |
| HPV56 | E2 | IALESLSTTIY | 20 | 11 | | 38702 |
| HPV56 | E2 | IIYKDETQR | 283 | 9 | | 38703 |
| HPV56 | E2 | ISDTDNTDSR | 211 | 10 | | 38704 |
| HPV56 | E2 | ITIIYKDETQR | 281 | 11 | | 38705 |
| HPV56 | E2 | KACSAIEVQIA | 11 | 11 | | 38706 |
| HPV56 | E2 | KCCRYRFQK | 248 | 9 | | 38707 |
| HPV56 | E2 | KCCRYRFQKY | 248 | 10 | | 38708 |
| HPV56 | E2 | KCCRYRFQKYK | 248 | 11 | | 38709 |
| HPV56 | E2 | KCFKKEGQH | 51 | 9 | | 38710 |
| HPV56 | E2 | KCVTTHTH | 203 | 8 | | 38711 |
| HPV56 | E2 | KDETQRNSF | 286 | 9 | | 38712 |
| HPV56 | E2 | KFGCKNIWEVH | 120 | 11 | | 38713 |
| HPV56 | E2 | KGEPNRLK | 241 | 8 | | 38714 |
| HPV56 | E2 | KGEPNRLKCCR | 241 | 11 | | 38715 |
| HPV56 | E2 | KTLFVDVTSTY | 258 | 11 | | 38716 |
| HPV56 | E2 | KTTPVVHLK | 233 | 9 | | 38717 |
| HPV56 | E2 | KTYYTDFEQEA | 108 | 11 | | 38718 |
| HPV56 | E2 | KVCSGVDY | 90 | 8 | | 38719 |
| HPV56 | E2 | KVCSGVDYR | 90 | 9 | | 38720 |
| HPV56 | E2 | LFVDVTSTY | 260 | 9 | | 38721 |
| HPV56 | E2 | LFVDVTSTYH | 260 | 10 | | 38722 |
| HPV56 | E2 | LSHVKIPVVY | 295 | 10 | | 38723 |
| HPV56 | E2 | LSHVKIPVVYR | 295 | 11 | | 38724 |
| HPV56 | E2 | LTEPKKCF | 46 | 8 | | 38725 |
| HPV56 | E2 | LTEPKKCFK | 46 | 9 | | 38726 |
| HPV56 | E2 | LTEPKKCFKK | 46 | 10 | | 38727 |
| HPV56 | E2 | MVPCLQVCK | 1 | 9 | | 38728 |
| HPV56 | E2 | MVPCLQVCKA | 1 | 10 | | 38729 |
| HPV56 | E2 | MVPCLQVCKAK | 1 | 11 | | 38730 |
| HPV56 | E2 | NCMQYVAWK | 70 | 9 | | 38731 |
| HPV56 | E2 | NCMQYVAWKY | 70 | 10 | | 38732 |
| HPV56 | E2 | NGDCGWQK | 83 | 8 | | 38733 |
| HPV56 | E2 | NSFLSHVK | 292 | 8 | | 38734 |
| HPV56 | E2 | NVSPVETVNEY | 149 | 11 | | 38735 |
| HPV56 | E2 | PCLQVCKA | 3 | 8 | | 38736 |
| HPV56 | E2 | PCLQVCKAK | 3 | 9 | | 38737 |
| HPV56 | E2 | PCLQVCKAKA | 3 | 10 | | 38738 |
| HPV56 | E2 | PDSVSSTCR | 139 | 9 | | 38739 |
| HPV56 | E2 | PDSVSSTCRY | 139 | 10 | | 38740 |
| HPV56 | E2 | PGDKTTPVVH | 230 | 10 | | 38741 |
| HPV56 | E2 | PGKRPRLR | 183 | 8 | | 38742 |
| HPV56 | E2 | PVETVNEY | 152 | 8 | | 38743 |
| HPV56 | E2 | PVETVNEYNTH | 152 | 11 | | 38744 |
| HPV56 | E2 | PVVHLKGEPNR | 236 | 11 | | 38745 |
| HPV56 | E2 | PVVYRLVWDK | 301 | 10 | | 38746 |
| HPV56 | E2 | QDAAVSHR | 175 | 8 | | 38747 |
| HPV56 | E2 | QDAAVSHRPGK | 175 | 11 | | 38748 |
| HPV56 | E2 | QVCKAKACSA | 6 | 10 | | 38749 |
| HPV56 | E2 | RFQKYKTLF | 253 | 9 | | 38750 |
| HPV56 | E2 | RGIYYVHDGH | 98 | 10 | | 38751 |
| HPV56 | E2 | RGIYYVHDGHK | 98 | 11 | | 38752 |
| HPV56 | E2 | RLKCCRYR | 246 | 8 | | 38753 |
| HPV56 | E2 | RLKCCRYRF | 246 | 9 | | 38754 |
| HPV56 | E2 | RLKCCRYRFQK | 246 | 11 | | 38755 |
| HPV56 | E2 | RLRESEFDSSR | 188 | 11 | | 38756 |
| HPV56 | E2 | RSINNNNH | 222 | 8 | | 38757 |
| HPV56 | E2 | RSRSINNNNH | 220 | 10 | | 38758 |
| HPV56 | E2 | SAIEVQIA | 14 | 8 | | 38759 |
| HPV56 | E2 | SDTDNTDSR | 212 | 9 | | 38760 |
| HPV56 | E2 | SDTDNTDSRSR | 212 | 11 | | 38761 |
| HPV56 | E2 | SGVDYRGIY | 93 | 9 | | 38762 |
| HPV56 | E2 | SGVDYRGIYY | 93 | 10 | | 38763 |
| HPV56 | E2 | SIITIIYK | 279 | 8 | | 38764 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | E2 | SINNNNHPGDK | 223 | 11 | | 38765 |
| HPV56 | E2 | SSRESHAK | 196 | 8 | | 38766 |
| HPV56 | E2 | STSVGNQDA | 169 | 9 | | 38767 |
| HPV56 | E2 | STSVGNQDAA | 169 | 10 | | 38768 |
| HPV56 | E2 | STYHWTSTDNK | 266 | 11 | | 38769 |
| HPV56 | E2 | SVGNQDAA | 171 | 8 | | 38770 |
| HPV56 | E2 | SVGNQDAAVSH | 171 | 11 | | 38771 |
| HPV56 | E2 | SVSSTCRY | 141 | 8 | | 38772 |
| HPV56 | E2 | TCEELWLTEPK | 40 | 11 | | 38773 |
| HPV56 | E2 | TDFEQEAK | 112 | 8 | | 38774 |
| HPV56 | E2 | TDFEQEAKK | 112 | 9 | | 38775 |
| HPV56 | E2 | TDFEQEAKKF | 112 | 10 | | 38776 |
| HPV56 | E2 | TDNTDSRSR | 214 | 9 | | 38777 |
| HPV56 | E2 | TIIYKDETQR | 282 | 10 | | 38778 |
| HPV56 | E2 | TIYNNEEWTLR | 28 | 11 | | 38779 |
| HPV56 | E2 | TLFVDVTSTY | 259 | 10 | | 38780 |
| HPV56 | E2 | TLFVDVTSTYH | 259 | 11 | | 38781 |
| HPV56 | E2 | TSTDNKNY | 271 | 8 | | 38782 |
| HPV56 | E2 | TSTSVGNQDA | 168 | 10 | | 38783 |
| HPV56 | E2 | TSTSVGNQDAA | 168 | 11 | | 38784 |
| HPV56 | E2 | TSVGNQDA | 170 | 8 | | 38785 |
| HPV56 | E2 | TSVGNQDAA | 170 | 9 | | 38786 |
| HPV56 | E2 | TTPVVHLK | 234 | 8 | | 38787 |
| HPV56 | E2 | TTSTSVGNQDA | 167 | 11 | | 38788 |
| HPV56 | E2 | TVNEYNTH | 155 | 8 | | 38789 |
| HPV56 | E2 | TVNEYNTHK | 155 | 9 | | 38790 |
| HPV56 | E2 | VAWKYIYY | 75 | 8 | | 38791 |
| HPV56 | E2 | VCKAKACSA | 7 | 9 | | 38792 |
| HPV56 | E2 | VCSGVDYR | 91 | 8 | | 38793 |
| HPV56 | E2 | VCSGVDYRGIY | 91 | 11 | | 38794 |
| HPV56 | E2 | VDVTSTYH | 262 | 8 | | 38795 |
| HPV56 | E2 | VDYRGIYY | 95 | 8 | | 38796 |
| HPV56 | E2 | VDYRGIYYVH | 95 | 10 | | 38797 |
| HPV56 | E2 | VGNQDAAVSH | 172 | 10 | | 38798 |
| HPV56 | E2 | VGNQDAAVSHR | 172 | 11 | | 38799 |
| HPV56 | E2 | VSHRPGKR | 179 | 8 | | 38800 |
| HPV56 | E2 | VSHRPGKRPR | 179 | 10 | | 38801 |
| HPV56 | E2 | VSPVETVNEY | 150 | 10 | | 38802 |
| HPV56 | E2 | VVHLKGEPNR | 237 | 10 | | 38803 |
| HPV56 | E2 | VVYRLVWDK | 302 | 9 | | 38804 |
| HPV56 | E2 | WLTEPKKCF | 45 | 9 | | 38805 |
| HPV56 | E2 | WLTEPKKCFK | 45 | 10 | | 38806 |
| HPV56 | E2 | WLTEPKKCFKK | 45 | 11 | | 38807 |
| HPV56 | E2 | WTSTDNKNY | 270 | 9 | | 38808 |
| HPV56 | E2 | YCPDSVSSTCR | 137 | 11 | | 38809 |
| HPV56 | E2 | YSIITIIY | 278 | 8 | | 38810 |
| HPV56 | E2 | YSIITIIYK | 278 | 9 | | 38811 |
| HPV56 | E2 | YTDFEQEA | 111 | 8 | | 38812 |
| HPV56 | E2 | YTDFEQEAK | 111 | 9 | | 38813 |
| HPV56 | E2 | YTDFEQEAKK | 111 | 10 | | 38814 |
| HPV56 | E2 | YTDFEQEAKKF | 111 | 11 | | 38815 |
| HPV56 | E2 | YVAWKYIY | 74 | 8 | | 38816 |
| HPV56 | E2 | YVAWKYIYY | 74 | 9 | | 38817 |
| HPV56 | E2 | YVHDGHKTY | 102 | 9 | | 38818 |
| HPV56 | E2 | YVHDGHKTYY | 102 | 10 | | 38819 |
| HPV56 | E6 | ACTELKLVY | 49 | 9 | | 38820 |
| HPV56 | E6 | ACTELKLVYR | 49 | 10 | | 38821 |
| HPV56 | E6 | ATLESITK | 89 | 8 | | 38822 |
| HPV56 | E6 | ATLESITKK | 89 | 9 | | 38823 |
| HPV56 | E6 | AVCRVCLLF | 64 | 9 | | 38824 |
| HPV56 | E6 | AVCRVCLLFY | 64 | 10 | | 38825 |
| HPV56 | E6 | CDLLIRCY | 100 | 8 | | 38826 |
| HPV56 | E6 | CDLLIRCYR | 100 | 9 | | 38827 |
| HPV56 | E6 | CDRKRRFH | 122 | 8 | | 38828 |
| HPV56 | E6 | CDRKRRFHLIA | 122 | 11 | | 38829 |
| HPV56 | E6 | CLGCWRQTSR | 139 | 10 | | 38830 |
| HPV56 | E6 | CLLFYSKVR | 69 | 9 | | 38831 |
| HPV56 | E6 | CLLFYSKVRK | 69 | 10 | | 38832 |
| HPV56 | E6 | CLLFYSKVRKY | 69 | 11 | | 38833 |
| HPV56 | E6 | CTELKLVY | 50 | 8 | | 38834 |
| HPV56 | E6 | CTELKLVYR | 50 | 9 | | 38835 |
| HPV56 | E6 | CVYCKKELTR | 33 | 10 | | 38836 |
| HPV56 | E6 | CVYCKKELTRA | 33 | 11 | | 38837 |
| HPV56 | E6 | DDFPYAVCR | 59 | 9 | | 38838 |
| HPV56 | E6 | DFPYAVCR | 60 | 8 | | 38839 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | E6 | DLLIRCYR | 101 | 8 | | 38840 |
| HPV56 | E6 | DLRLSCVY | 28 | 8 | | 38841 |
| HPV56 | E6 | DLRLSCVYCK | 28 | 10 | | 38842 |
| HPV56 | E6 | DLRLSCVYCKK | 28 | 11 | | 38843 |
| HPV56 | E6 | EIPLIDLR | 23 | 8 | | 38844 |
| HPV56 | E6 | ELKLVYRDDF | 52 | 10 | | 38845 |
| HPV56 | E6 | ELTRAEVY | 39 | 8 | | 38846 |
| HPV56 | E6 | ELTRAEVYNF | 39 | 10 | | 38847 |
| HPV56 | E6 | ELTRAEVYNFA | 39 | 11 | | 38848 |
| HPV56 | E6 | EVLEIPLIDLR | 20 | 11 | | 38849 |
| HPV56 | E6 | EVYNFACTELK | 44 | 11 | | 38850 |
| HPV56 | E6 | FACTELKLVY | 48 | 10 | | 38851 |
| HPV56 | E6 | FACTELKLVYR | 48 | 11 | | 38852 |
| HPV56 | E6 | GATLESITK | 88 | 9 | | 38853 |
| HPV56 | E6 | GATLESITKK | 88 | 10 | | 38854 |
| HPV56 | E6 | GCWRQTSR | 141 | 8 | | 38855 |
| HPV56 | E6 | GCWRQTSREPR | 141 | 11 | | 38856 |
| HPV56 | E6 | GSCLGCWR | 137 | 8 | | 38857 |
| HPV56 | E6 | HCDRKRRF | 121 | 8 | | 38858 |
| HPV56 | E6 | HCDRKRRFH | 121 | 9 | | 38859 |
| HPV56 | E6 | IDLRLSCVY | 27 | 9 | | 38860 |
| HPV56 | E6 | IDLRLSCVYCK | 27 | 11 | | 38861 |
| HPV56 | E6 | KLVYRDDF | 54 | 8 | | 38862 |
| HPV56 | E6 | KLVYRDDFPY | 54 | 10 | | 38863 |
| HPV56 | E6 | KLVYRDDFPYA | 54 | 11 | | 38864 |
| HPV56 | E6 | KVRKYRYY | 75 | 8 | | 38865 |
| HPV56 | E6 | KVRKYRYYDY | 75 | 10 | | 38866 |
| HPV56 | E6 | LCDLLIRCY | 99 | 9 | | 38867 |
| HPV56 | E6 | LCDLLIRCYR | 99 | 10 | | 38868 |
| HPV56 | E6 | LFYSKVRK | 71 | 8 | | 38869 |
| HPV56 | E6 | LFYSKVRKY | 71 | 9 | | 38870 |
| HPV56 | E6 | LFYSKVRKYR | 71 | 10 | | 38871 |
| HPV56 | E6 | LFYSKVRKYRY | 71 | 11 | | 38872 |
| HPV56 | E6 | LGCWRQTSR | 140 | 9 | | 38873 |
| HPV56 | E6 | LIDLRLSCVY | 26 | 10 | | 38874 |
| HPV56 | E6 | LLFYSKVR | 70 | 8 | | 38875 |
| HPV56 | E6 | LLFYSKVRK | 70 | 9 | | 38876 |
| HPV56 | E6 | LLFYSKVRKY | 70 | 10 | | 38877 |
| HPV56 | E6 | LLFYSKVRKYR | 70 | 11 | | 38878 |
| HPV56 | E6 | LSCVYCKK | 31 | 8 | | 38879 |
| HPV56 | E6 | LTPEEKQLH | 113 | 9 | | 38880 |
| HPV56 | E6 | LTRAEVYNF | 40 | 9 | | 38881 |
| HPV56 | E6 | LTRAEVYNFA | 40 | 10 | | 38882 |
| HPV56 | E6 | LVYRDDFPY | 55 | 9 | | 38883 |
| HPV56 | E6 | LVYRDDFPYA | 55 | 10 | | 38884 |
| HPV56 | E6 | NFACTELK | 47 | 8 | | 38885 |
| HPV56 | E6 | NFACTELKLVY | 47 | 11 | | 38886 |
| HPV56 | E6 | PLIDLRLSCVY | 25 | 11 | | 38887 |
| HPV56 | E6 | PLTPEEKQLH | 112 | 10 | | 38888 |
| HPV56 | E6 | QFNNPQER | 4 | 8 | | 38889 |
| HPV56 | E6 | QFNNPQERPR | 4 | 10 | | 38890 |
| HPV56 | E6 | QLCDLLIR | 98 | 8 | | 38891 |
| HPV56 | E6 | QLCDLLIRCY | 98 | 10 | | 38892 |
| HPV56 | E6 | QLCDLLIRCYR | 98 | 11 | | 38893 |
| HPV56 | E6 | QLHCDRKR | 119 | 8 | | 38894 |
| HPV56 | E6 | QLHCDRKRR | 119 | 9 | | 38895 |
| HPV56 | E6 | QLHCDRKRRF | 119 | 10 | | 38896 |
| HPV56 | E6 | QLHCDRKRRFH | 119 | 11 | | 38897 |
| HPV56 | E6 | QSPLTPEEK | 110 | 9 | | 38898 |
| HPV56 | E6 | RAEVYNFA | 42 | 8 | | 38899 |
| HPV56 | E6 | RCQSPLTPEEK | 108 | 11 | | 38900 |
| HPV56 | E6 | RDDFPYAVCR | 58 | 10 | | 38901 |
| HPV56 | E6 | RLSCVYCK | 30 | 8 | | 38902 |
| HPV56 | E6 | RLSCVYCKK | 30 | 9 | | 38903 |
| HPV56 | E6 | RVCLLFYSK | 67 | 9 | | 38904 |
| HPV56 | E6 | RVCLLFYSKVR | 67 | 11 | | 38905 |
| HPV56 | E6 | SCLGCWRQTSR | 138 | 11 | | 38906 |
| HPV56 | E6 | SCVYCKKELTR | 32 | 11 | | 38907 |
| HPV56 | E6 | TGSCLGCWR | 136 | 9 | | 38908 |
| HPV56 | E6 | TLESITKK | 90 | 8 | | 38909 |
| HPV56 | E6 | VCLLFYSK | 68 | 8 | | 38910 |
| HPV56 | E6 | VCLLFYSKVR | 68 | 10 | | 38911 |
| HPV56 | E6 | VCLLFYSKVRK | 68 | 11 | | 38912 |
| HPV56 | E6 | VCRVCLLF | 65 | 8 | | 38913 |
| HPV56 | E6 | VCRVCLLFY | 65 | 9 | | 38914 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | E6 | VCRVCLLFYSK | 65 | 11 | | 38915 |
| HPV56 | E6 | VLEIPLIDLR | 21 | 10 | | 38916 |
| HPV56 | E6 | WTGSCLGCWR | 135 | 10 | | 38917 |
| HPV56 | E6 | YAVCRVCLLF | 63 | 10 | | 38918 |
| HPV56 | E6 | YAVCRVCLLFY | 63 | 11 | | 38919 |
| HPV56 | E6 | YCKKELTR | 35 | 8 | | 38920 |
| HPV56 | E6 | YCKKELTRA | 35 | 9 | | 38921 |
| HPV56 | E6 | YDYSVYGA | 82 | 8 | | 38922 |
| HPV56 | E6 | YGATLESITK | 87 | 10 | | 38923 |
| HPV56 | E6 | YGATLESITKK | 87 | 11 | | 38924 |
| HPV56 | E6 | YSKVRKYR | 73 | 8 | | 38925 |
| HPV56 | E6 | YSKVRKYRY | 73 | 9 | | 38926 |
| HPV56 | E6 | YSKVRKYRYY | 73 | 10 | | 38927 |
| HPV56 | E7 | ALTVTCPLCA | 93 | 10 | | 38928 |
| HPV56 | E7 | DIQSTKEDLR | 75 | 10 | | 38929 |
| HPV56 | E7 | EDEDEDEVDH | 33 | 10 | | 38930 |
| HPV56 | E7 | EDEDEVDH | 35 | 8 | | 38931 |
| HPV56 | E7 | EDEVDHLQER | 37 | 10 | | 38932 |
| HPV56 | E7 | EVDHLQER | 39 | 8 | | 38933 |
| HPV56 | E7 | FVVQLDIQSTK | 70 | 11 | | 38934 |
| HPV56 | E7 | GALTVTCPLCA | 92 | 11 | | 38935 |
| HPV56 | E7 | HLQERPQQA | 42 | 9 | | 38936 |
| HPV56 | E7 | HLQERPQQAR | 42 | 10 | | 38937 |
| HPV56 | E7 | HVPCCECK | 62 | 8 | | 38938 |
| HPV56 | E7 | HVPCCECKF | 62 | 9 | | 38939 |
| HPV56 | E7 | LDIQSTKEDLR | 74 | 11 | | 38940 |
| HPV56 | E7 | LIHVPCCECK | 60 | 10 | | 38941 |
| HPV56 | E7 | LIHVPCCECKF | 60 | 11 | | 38942 |
| HPV56 | E7 | LTVTCPLCA | 94 | 9 | | 38943 |
| HPV56 | E7 | QAKQHTCY | 52 | 8 | | 38944 |
| HPV56 | E7 | QAKQHTCYLIH | 52 | 11 | | 38945 |
| HPV56 | E7 | QARQAKQH | 49 | 8 | | 38946 |
| HPV56 | E7 | QARQAKQHTCY | 49 | 11 | | 38947 |
| HPV56 | E7 | QLDIQSTK | 73 | 8 | | 38948 |
| HPV56 | E7 | QSTKEDLR | 77 | 8 | | 38949 |
| HPV56 | E7 | RVVQQLLMGA | 84 | 10 | | 38950 |
| HPV56 | E7 | TVTCPLCA | 95 | 8 | | 38951 |
| HPV56 | E7 | VDHLQERPQQA | 40 | 11 | | 38952 |
| HPV56 | E7 | VVQLDIQSTK | 71 | 10 | | 38953 |
| HPV56 | E7 | VVQQLLMGA | 85 | 9 | | 38954 |
| HPV56 | E7 | YLIHVPCCECK | 59 | 11 | | 38955 |
| HPV56 | L1 | ACVGLEVGR | 135 | 9 | | 38956 |
| HPV56 | L1 | ADAYGDSMWF | 273 | 10 | | 38957 |
| HPV56 | L1 | ADAYGDSMWFY | 273 | 11 | | 38958 |
| HPV56 | L1 | AGKVGETIPA | 298 | 10 | | 38959 |
| HPV56 | L1 | AGLSGHPLF | 149 | 9 | | 38960 |
| HPV56 | L1 | AGLSGHPLFNR | 149 | 11 | | 38961 |
| HPV56 | L1 | AGSSRLLA | 72 | 8 | | 38962 |
| HPV56 | L1 | AGSSRLLAVGH | 72 | 11 | | 38963 |
| HPV56 | L1 | AMDFKVLQESK | 241 | 11 | | 38964 |
| HPV56 | L1 | AMGEHWTK | 198 | 8 | | 38965 |
| HPV56 | L1 | AMGEHWTKGA | 198 | 10 | | 38966 |
| HPV56 | L1 | ATDSYVKR | 58 | 8 | | 38967 |
| HPV56 | L1 | ATEQLSKY | 381 | 8 | | 38968 |
| HPV56 | L1 | ATEQLSKYDA | 381 | 10 | | 38969 |
| HPV56 | L1 | ATEQLSKYDAR | 381 | 11 | | 38970 |
| HPV56 | L1 | ATSKKRSA | 514 | 8 | | 38971 |
| HPV56 | L1 | ATSLEDKY | 444 | 8 | | 38972 |
| HPV56 | L1 | ATSLEDKYR | 444 | 9 | | 38973 |
| HPV56 | L1 | ATSLEDKYRY | 444 | 10 | | 38974 |
| HPV56 | L1 | ATWRPSENK | 37 | 9 | | 38975 |
| HPV56 | L1 | ATWRPSENKVY | 37 | 11 | | 38976 |
| HPV56 | L1 | AVATSKKR | 512 | 8 | | 38977 |
| HPV56 | L1 | AVATSKKRSA | 512 | 10 | | 38978 |
| HPV56 | L1 | AVGHPYYSVTK | 79 | 11 | | 38979 |
| HPV56 | L1 | AVNVFPIF | 26 | 8 | | 38980 |
| HPV56 | L1 | CIFLDVGA | 19 | 8 | | 38981 |
| HPV56 | L1 | CIVGCTPA | 191 | 8 | | 38982 |
| HPV56 | L1 | CTPAMGEH | 195 | 8 | | 38983 |
| HPV56 | L1 | CTPAMGEHWTK | 195 | 11 | | 38984 |
| HPV56 | L1 | CVGLEVGR | 136 | 8 | | 38985 |
| HPV56 | L1 | DARKINQY | 389 | 8 | | 38986 |
| HPV56 | L1 | DARKINQYLR | 389 | 10 | | 38987 |
| HPV56 | L1 | DARKINQYLRH | 389 | 11 | | 38988 |
| HPV56 | L1 | DAYGDSMWF | 274 | 9 | | 38989 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L1 | DAYGDSMWFY | 274 | 10 | | 38990 |
| HPV56 | L1 | DDTESSNLA | 161 | 9 | | 38991 |
| HPV56 | L1 | DFKVLQESK | 243 | 9 | | 38992 |
| HPV56 | L1 | DFKVLQESKA | 243 | 10 | | 38993 |
| HPV56 | L1 | DGDMIDTGF | 231 | 9 | | 38994 |
| HPV56 | L1 | DGDMIDTGFGA | 231 | 11 | | 38995 |
| HPV56 | L1 | DIVQSTCK | 257 | 8 | | 38996 |
| HPV56 | L1 | DIVQSTCKY | 257 | 9 | | 38997 |
| HPV56 | L1 | DLDQFPLGR | 491 | 9 | | 38998 |
| HPV56 | L1 | DLDQFPLGRK | 491 | 10 | | 38999 |
| HPV56 | L1 | DLDQFPLGRKF | 491 | 11 | | 39000 |
| HPV56 | L1 | DMIDTGFGA | 233 | 9 | | 39001 |
| HPV56 | L1 | DSFSTDLDQF | 486 | 10 | | 39002 |
| HPV56 | L1 | DSMWFYLR | 278 | 8 | | 39003 |
| HPV56 | L1 | DSMWFYLRR | 278 | 9 | | 39004 |
| HPV56 | L1 | DSRDNISVDGK | 176 | 11 | | 39005 |
| HPV56 | L1 | DSYVKRTSIF | 60 | 10 | | 39006 |
| HPV56 | L1 | DSYVKRTSIFY | 60 | 11 | | 39007 |
| HPV56 | L1 | DTESSNLA | 162 | 8 | | 39008 |
| HPV56 | L1 | DTGFGAMDF | 236 | 9 | | 39009 |
| HPV56 | L1 | DTGFGAMDFK | 236 | 10 | | 39010 |
| HPV56 | L1 | DTNIYNPDQER | 121 | 11 | | 39011 |
| HPV56 | L1 | DVGAVNVF | 23 | 8 | | 39012 |
| HPV56 | L1 | DVGAVNVFPIF | 23 | 11 | | 39013 |
| HPV56 | L1 | DVNLQDSF | 481 | 8 | | 39014 |
| HPV56 | L1 | EAQLFNKPY | 337 | 9 | | 39015 |
| HPV56 | L1 | EDGDMIDTGF | 230 | 10 | | 39016 |
| HPV56 | L1 | EDKYRYVR | 448 | 8 | | 39017 |
| HPV56 | L1 | EDKYRYVRSTA | 448 | 11 | | 39018 |
| HPV56 | L1 | ELQFVFQLCK | 404 | 10 | | 39019 |
| HPV56 | L1 | ELYLKGSNGR | 308 | 10 | | 39020 |
| HPV56 | L1 | ETIPAELY | 303 | 8 | | 39021 |
| HPV56 | L1 | ETIPAELYLK | 303 | 10 | | 39022 |
| HPV56 | L1 | EVGRGQPLGA | 140 | 10 | | 39023 |
| HPV56 | L1 | EVMAYLHNMNA | 419 | 11 | | 39024 |
| HPV56 | L1 | FARHYFNR | 290 | 8 | | 39025 |
| HPV56 | L1 | FARHYFNRA | 290 | 9 | | 39026 |
| HPV56 | L1 | FARHYFNRAGK | 290 | 11 | | 39027 |
| HPV56 | L1 | FGLPDTNIY | 117 | 9 | | 39028 |
| HPV56 | L1 | FLDVGAVNVF | 21 | 10 | | 39029 |
| HPV56 | L1 | FLMQLGTR | 501 | 8 | | 39030 |
| HPV56 | L1 | FLMQLGTRSK | 501 | 10 | | 39031 |
| HPV56 | L1 | FLQMATWR | 33 | 8 | | 39032 |
| HPV56 | L1 | FSTDLDQF | 488 | 8 | | 39033 |
| HPV56 | L1 | FVTVVDTTR | 364 | 9 | | 39034 |
| HPV56 | L1 | GAGLSGHPLF | 148 | 10 | | 39035 |
| HPV56 | L1 | GAVNVFPIF | 25 | 9 | | 39036 |
| HPV56 | L1 | GCTPAMGEH | 194 | 9 | | 39037 |
| HPV56 | L1 | GDMIDTGF | 232 | 8 | | 39038 |
| HPV56 | L1 | GDMIDTGFGA | 232 | 10 | | 39039 |
| HPV56 | L1 | GDSMWFYLR | 277 | 9 | | 39040 |
| HPV56 | L1 | GDSMWFYLRR | 277 | 10 | | 39041 |
| HPV56 | L1 | GFGAMDFK | 238 | 8 | | 39042 |
| HPV56 | L1 | GICWGNQLF | 356 | 9 | | 39043 |
| HPV56 | L1 | GLCIFLDVGA | 17 | 10 | | 39044 |
| HPV56 | L1 | GLPDTNIY | 118 | 8 | | 39045 |
| HPV56 | L1 | GLSGHPLF | 150 | 8 | | 39046 |
| HPV56 | L1 | GLSGHPLFNR | 150 | 10 | | 39047 |
| HPV56 | L1 | GSMITSEA | 331 | 8 | | 39048 |
| HPV56 | L1 | GSMITSEAQLF | 331 | 11 | | 39049 |
| HPV56 | L1 | GSSRLLAVGH | 73 | 10 | | 39050 |
| HPV56 | L1 | GTRSKPAVA | 506 | 9 | | 39051 |
| HPV56 | L1 | HAGSSRLLA | 71 | 9 | | 39052 |
| HPV56 | L1 | HVEEYELQF | 399 | 9 | | 39053 |
| HPV56 | L1 | HVEEYELQFVF | 399 | 11 | | 39054 |
| HPV56 | L1 | ICWGNQLF | 357 | 8 | | 39055 |
| HPV56 | L1 | IDTGFGAMDF | 235 | 10 | | 39056 |
| HPV56 | L1 | IDTGFGAMDFK | 235 | 11 | | 39057 |
| HPV56 | L1 | IFLDVGAVNVF | 20 | 11 | | 39058 |
| HPV56 | L1 | IFLQMATWR | 32 | 9 | | 39059 |
| HPV56 | L1 | IFYHAGSSR | 68 | 9 | | 39060 |
| HPV56 | L1 | IGLSPPVA | 437 | 8 | | 39061 |
| HPV56 | L1 | ISTATEQLSK | 378 | 10 | | 39062 |
| HPV56 | L1 | ISTATEQLSKY | 378 | 11 | | 39063 |
| HPV56 | L1 | ITLSAEVMA | 414 | 9 | | 39064 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L1 | ITLSAEVMAY | 414 | 10 | | 39065 |
| HPV56 | L1 | ITSEAQLF | 334 | 8 | | 39066 |
| HPV56 | L1 | ITSEAQLFNK | 334 | 10 | | 39067 |
| HPV56 | L1 | IVGCTPAMGEH | 192 | 11 | | 39068 |
| HPV56 | L1 | IVQSTCKY | 258 | 8 | | 39069 |
| HPV56 | L1 | IVQSTCKYPDY | 258 | 11 | | 39070 |
| HPV56 | L1 | KDNTKTNIPK | 89 | 10 | | 39071 |
| HPV56 | L1 | KFGLPDTNIY | 116 | 10 | | 39072 |
| HPV56 | L1 | KFLMQLGTR | 500 | 9 | | 39073 |
| HPV56 | L1 | KFLMQLGTRSK | 500 | 11 | | 39074 |
| HPV56 | L1 | KFWDVNLQDSF | 478 | 11 | | 39075 |
| HPV56 | L1 | KINQYLRH | 392 | 8 | | 39076 |
| HPV56 | L1 | KITLSAEVMA | 413 | 10 | | 39077 |
| HPV56 | L1 | KITLSAEVMAY | 413 | 11 | | 39078 |
| HPV56 | L1 | KTNIPKVSA | 93 | 9 | | 39079 |
| HPV56 | L1 | KTNIPKVSAY | 93 | 10 | | 39080 |
| HPV56 | L1 | KVGETIPA | 300 | 8 | | 39081 |
| HPV56 | L1 | KVGETIPAELY | 300 | 11 | | 39082 |
| HPV56 | L1 | KVLQESKA | 245 | 8 | | 39083 |
| HPV56 | L1 | KVSAYQYR | 98 | 8 | | 39084 |
| HPV56 | L1 | KVSAYQYRVF | 98 | 10 | | 39085 |
| HPV56 | L1 | KVSAYQYRVFR | 98 | 11 | | 39086 |
| HPV56 | L1 | KVVATDSY | 55 | 8 | | 39087 |
| HPV56 | L1 | KVVATDSYVK | 55 | 10 | | 39088 |
| HPV56 | L1 | KVVATDSYVKR | 55 | 11 | | 39089 |
| HPV56 | L1 | KVYLPPTPVSK | 45 | 11 | | 39090 |
| HPV56 | L1 | LANNNVIEDSR | 168 | 11 | | 39091 |
| HPV56 | L1 | LAVGHPYY | 78 | 8 | | 39092 |
| HPV56 | L1 | LCIFLDVGA | 18 | 9 | | 39093 |
| HPV56 | L1 | LCIVGCTPA | 190 | 9 | | 39094 |
| HPV56 | L1 | LCKITLSA | 411 | 8 | | 39095 |
| HPV56 | L1 | LDDTESSNLA | 160 | 10 | | 39096 |
| HPV56 | L1 | LDIVQSTCK | 256 | 9 | | 39097 |
| HPV56 | L1 | LDIVQSTCKY | 256 | 10 | | 39098 |
| HPV56 | L1 | LDQFPLGR | 492 | 8 | | 39099 |
| HPV56 | L1 | LDQFPLGRK | 492 | 9 | | 39100 |
| HPV56 | L1 | LDQFPLGRKF | 492 | 10 | | 39101 |
| HPV56 | L1 | LDVGAVNVF | 22 | 9 | | 39102 |
| HPV56 | L1 | LFARHYFNR | 289 | 9 | | 39103 |
| HPV56 | L1 | LFARHYFNRA | 289 | 10 | | 39104 |
| HPV56 | L1 | LFNKPYWLQR | 340 | 10 | | 39105 |
| HPV56 | L1 | LFNKPYWLQRA | 340 | 11 | | 39106 |
| HPV56 | L1 | LFVTVVDTTR | 363 | 10 | | 39107 |
| HPV56 | L1 | LGAGLSGH | 147 | 8 | | 39108 |
| HPV56 | L1 | LGAGLSGHPLF | 147 | 11 | | 39109 |
| HPV56 | L1 | LGTRSKPA | 505 | 8 | | 39110 |
| HPV56 | L1 | LGTRSKPAVA | 505 | 10 | | 39111 |
| HPV56 | L1 | LLAVGHPY | 77 | 8 | | 39112 |
| HPV56 | L1 | LLAVGHPYY | 77 | 9 | | 39113 |
| HPV56 | L1 | LMQLGTRSK | 502 | 9 | | 39114 |
| HPV56 | L1 | LMQLGTRSKPA | 502 | 11 | | 39115 |
| HPV56 | L1 | LSAEVMAY | 416 | 8 | | 39116 |
| HPV56 | L1 | LSAEVMAYLH | 416 | 10 | | 39117 |
| HPV56 | L1 | LSGHPLFNR | 151 | 9 | | 39118 |
| HPV56 | L1 | LSKYDARK | 385 | 8 | | 39119 |
| HPV56 | L1 | MATWRPSENK | 36 | 10 | | 39120 |
| HPV56 | L1 | MAYLHNMNA | 421 | 9 | | 39121 |
| HPV56 | L1 | MDFKVLQESK | 242 | 10 | | 39122 |
| HPV56 | L1 | MDFKVLQESKA | 242 | 11 | | 39123 |
| HPV56 | L1 | MGEHWTKGA | 199 | 9 | | 39124 |
| HPV56 | L1 | MIDTGFGA | 234 | 8 | | 39125 |
| HPV56 | L1 | MIDTGFGAMDF | 234 | 11 | | 39126 |
| HPV56 | L1 | MITSEAQLF | 333 | 9 | | 39127 |
| HPV56 | L1 | MITSEAQLFNK | 333 | 11 | | 39128 |
| HPV56 | L1 | MLPMMYIY | 2 | 8 | | 39129 |
| HPV56 | L1 | MLPMMYIYR | 2 | 9 | | 39130 |
| HPV56 | L1 | MMLPMMYIY | 1 | 9 | | 39131 |
| HPV56 | L1 | MMLPMMYIYR | 1 | 10 | | 39132 |
| HPV56 | L1 | MMYIYRDPPLH | 5 | 11 | | 39133 |
| HPV56 | L1 | NGICWGNQLF | 355 | 10 | | 39134 |
| HPV56 | L1 | NGREPPSSVY | 315 | 11 | | 39135 |
| HPV56 | L1 | NIGLSPPVA | 436 | 9 | | 39136 |
| HPV56 | L1 | NIPKVSAY | 95 | 8 | | 39137 |
| HPV56 | L1 | NIPKVSAYQY | 95 | 10 | | 39138 |
| HPV56 | L1 | NIPKVSAYQYR | 95 | 11 | | 39139 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L1 | NIYNPDQER | 123 | 9 | | 39140 |
| HPV56 | L1 | NTKTNIPK | 91 | 8 | | 39141 |
| HPV56 | L1 | NTKTNIPKVSA | 91 | 11 | | 39142 |
| HPV56 | L1 | NVFPIFLQMA | 28 | 10 | | 39143 |
| HPV56 | L1 | PAMGEHWTK | 197 | 9 | | 39144 |
| HPV56 | L1 | PAMGEHWTKGA | 197 | 11 | | 39145 |
| HPV56 | L1 | PAVATSKK | 511 | 8 | | 39146 |
| HPV56 | L1 | PAVATSKKR | 511 | 9 | | 39147 |
| HPV56 | L1 | PAVATSKKRSA | 511 | 11 | | 39148 |
| HPV56 | L1 | PDQERLVWA | 127 | 9 | | 39149 |
| HPV56 | L1 | PDYLKMSA | 266 | 8 | | 39150 |
| HPV56 | L1 | PDYLKMSADA | 266 | 10 | | 39151 |
| HPV56 | L1 | PDYLKMSADAY | 266 | 11 | | 39152 |
| HPV56 | L1 | PIFLQMATWR | 31 | 10 | | 39153 |
| HPV56 | L1 | PLDIVQSTCK | 255 | 10 | | 39154 |
| HPV56 | L1 | PLDIVQSTCKY | 255 | 11 | | 39155 |
| HPV56 | L1 | PLGAGLSGH | 146 | 9 | | 39156 |
| HPV56 | L1 | PLHYGLCIF | 13 | 9 | | 39157 |
| HPV56 | L1 | PSGSMITSEA | 329 | 10 | | 39158 |
| HPV56 | L1 | PTEKQDPLA | 467 | 9 | | 39159 |
| HPV56 | L1 | PTEKQDPLAK | 467 | 10 | | 39160 |
| HPV56 | L1 | PTEKQDPLAKY | 467 | 11 | | 39161 |
| HPV56 | L1 | PTPVSKVVA | 50 | 9 | | 39162 |
| HPV56 | L1 | PTSTSTPA | 522 | 8 | | 39163 |
| HPV56 | L1 | PTSTSTPAK | 522 | 9 | | 39164 |
| HPV56 | L1 | PTSTSTPAKR | 522 | 10 | | 39165 |
| HPV56 | L1 | PTSTSTPAKRK | 522 | 11 | | 39166 |
| HPV56 | L1 | PVATSLEDK | 442 | 9 | | 39167 |
| HPV56 | L1 | PVATSLEDKY | 442 | 10 | | 39168 |
| HPV56 | L1 | PVATSLEDKYR | 442 | 11 | | 39169 |
| HPV56 | L1 | PVSKVVATDSY | 52 | 11 | | 39170 |
| HPV56 | L1 | QDPLAKYK | 471 | 8 | | 39171 |
| HPV56 | L1 | QDPLAKYKF | 471 | 9 | | 39172 |
| HPV56 | L1 | QDSFSTDLDQF | 485 | 11 | | 39173 |
| HPV56 | L1 | QFPLGRKF | 494 | 8 | | 39174 |
| HPV56 | L1 | QFVFQLCK | 406 | 8 | | 39175 |
| HPV56 | L1 | QLCIVGCTPA | 189 | 10 | | 39176 |
| HPV56 | L1 | QLCKITLSA | 410 | 9 | | 39177 |
| HPV56 | L1 | QLFARHYF | 288 | 8 | | 39178 |
| HPV56 | L1 | QLFARHYFNR | 288 | 10 | | 39179 |
| HPV56 | L1 | QLFARHYFNRA | 288 | 11 | | 39180 |
| HPV56 | L1 | QLFNKPYWLQR | 339 | 11 | | 39181 |
| HPV56 | L1 | QLFVTVVDTTR | 362 | 11 | | 39182 |
| HPV56 | L1 | QLGTRSKPA | 504 | 9 | | 39183 |
| HPV56 | L1 | QLGTRSKPAVA | 504 | 11 | | 39184 |
| HPV56 | L1 | QLSKYDAR | 384 | 8 | | 39185 |
| HPV56 | L1 | QLSKYDARK | 384 | 9 | | 39186 |
| HPV56 | L1 | QMATWRPSENK | 35 | 11 | | 39187 |
| HPV56 | L1 | QSTCKYPDY | 260 | 9 | | 39188 |
| HPV56 | L1 | QSTCKYPDYLK | 260 | 11 | | 39189 |
| HPV56 | L1 | QVTTGDCPPLA | 213 | 11 | | 39190 |
| HPV56 | L1 | RAGKVGETIPA | 297 | 11 | | 39191 |
| HPV56 | L1 | RDNISVDGK | 178 | 9 | | 39192 |
| HPV56 | L1 | RLDDTESSNLA | 159 | 11 | | 39193 |
| HPV56 | L1 | RLLAVGHPY | 76 | 9 | | 39194 |
| HPV56 | L1 | RLLAVGHPYY | 76 | 10 | | 39195 |
| HPV56 | L1 | RLPDPNKF | 110 | 8 | | 39196 |
| HPV56 | L1 | RSAPTSTSTPA | 519 | 11 | | 39197 |
| HPV56 | L1 | RSKPAVATSK | 508 | 10 | | 39198 |
| HPV56 | L1 | RSKPAVATSKK | 508 | 11 | | 39199 |
| HPV56 | L1 | RSTAITCQR | 455 | 9 | | 39200 |
| HPV56 | L1 | RSTNMTISTA | 372 | 10 | | 39201 |
| HPV56 | L1 | RTSIFYHA | 65 | 8 | | 39202 |
| HPV56 | L1 | RVRLPDPNK | 108 | 9 | | 39203 |
| HPV56 | L1 | RVRLPDPNKF | 108 | 10 | | 39204 |
| HPV56 | L1 | SADAYGDSMWF | 272 | 11 | | 39205 |
| HPV56 | L1 | SAEVMAYLH | 417 | 9 | | 39206 |
| HPV56 | L1 | SAPTSTSTPA | 520 | 10 | | 39207 |
| HPV56 | L1 | SAPTSTSTPAK | 520 | 11 | | 39208 |
| HPV56 | L1 | SAYQYRVF | 100 | 8 | | 39209 |
| HPV56 | L1 | SAYQYRVFR | 100 | 9 | | 39210 |
| HPV56 | L1 | SAYQYRVFRVR | 100 | 11 | | 39211 |
| HPV56 | L1 | SFSTDLDQF | 487 | 9 | | 39212 |
| HPV56 | L1 | SGHPLFNR | 152 | 8 | | 39213 |
| HPV56 | L1 | SGSMITSEA | 330 | 9 | | 39214 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L1 | SIFYHAGSSR | 67 | 10 | | 39215 |
| HPV56 | L1 | SLEDKYRY | 446 | 8 | | 39216 |
| HPV56 | L1 | SLEDKYRYVR | 446 | 10 | | 39217 |
| HPV56 | L1 | SMITSEAQLF | 332 | 10 | | 39218 |
| HPV56 | L1 | SMWFYLRR | 279 | 8 | | 39219 |
| HPV56 | L1 | SSRLLAVGH | 74 | 9 | | 39220 |
| HPV56 | L1 | SSRLLAVGHPY | 74 | 11 | | 39221 |
| HPV56 | L1 | STAITCQR | 456 | 8 | | 39222 |
| HPV56 | L1 | STATEQLSK | 379 | 9 | | 39223 |
| HPV56 | L1 | STATEQLSKY | 379 | 10 | | 39224 |
| HPV56 | L1 | STCKYPDY | 261 | 8 | | 39225 |
| HPV56 | L1 | STCKYPDYLK | 261 | 10 | | 39226 |
| HPV56 | L1 | STDLDQFPLGR | 489 | 11 | | 39227 |
| HPV56 | L1 | STNMTISTA | 373 | 9 | | 39228 |
| HPV56 | L1 | STPAKRKR | 526 | 8 | | 39229 |
| HPV56 | L1 | STPAKRKRR | 526 | 9 | | 39230 |
| HPV56 | L1 | STSTPAKR | 524 | 8 | | 39231 |
| HPV56 | L1 | STSTPAKRK | 524 | 9 | | 39232 |
| HPV56 | L1 | STSTPAKRKR | 524 | 10 | | 39233 |
| HPV56 | L1 | STSTPAKRKRR | 524 | 11 | | 39234 |
| HPV56 | L1 | SVTKDNTK | 86 | 8 | | 39235 |
| HPV56 | L1 | TATEQLSK | 380 | 8 | | 39236 |
| HPV56 | L1 | TATEQLSKY | 380 | 9 | | 39237 |
| HPV56 | L1 | TATEQLSKYDA | 380 | 11 | | 39238 |
| HPV56 | L1 | TCKYPDYLK | 262 | 9 | | 39239 |
| HPV56 | L1 | TCQREQPPTEK | 460 | 11 | | 39240 |
| HPV56 | L1 | TDLDQFPLGR | 490 | 10 | | 39241 |
| HPV56 | L1 | TDLDQFPLGRK | 490 | 11 | | 39242 |
| HPV56 | L1 | TDSYVKRTSIF | 59 | 11 | | 39243 |
| HPV56 | L1 | TGDCPPLA | 216 | 8 | | 39244 |
| HPV56 | L1 | TGFGAMDF | 237 | 8 | | 39245 |
| HPV56 | L1 | TGFGAMDFK | 237 | 9 | | 39246 |
| HPV56 | L1 | TIPAELYLK | 304 | 9 | | 39247 |
| HPV56 | L1 | TISTATEQLSK | 377 | 11 | | 39248 |
| HPV56 | L1 | TLSAEVMA | 415 | 8 | | 39249 |
| HPV56 | L1 | TLSAEVMAY | 415 | 9 | | 39250 |
| HPV56 | L1 | TLSAEVMAYLH | 415 | 11 | | 39251 |
| HPV56 | L1 | TSEAQLFNK | 335 | 9 | | 39252 |
| HPV56 | L1 | TSEAQLFNKPY | 335 | 11 | | 39253 |
| HPV56 | L1 | TSIFYHAGSSR | 66 | 11 | | 39254 |
| HPV56 | L1 | TSLEDKYR | 445 | 8 | | 39255 |
| HPV56 | L1 | TSLEDKYRY | 445 | 9 | | 39256 |
| HPV56 | L1 | TSLEDKYRYVR | 445 | 11 | | 39257 |
| HPV56 | L1 | TSTPAKRK | 525 | 8 | | 39258 |
| HPV56 | L1 | TSTPAKRKR | 525 | 9 | | 39259 |
| HPV56 | L1 | TSTPAKRKRR | 525 | 10 | | 39260 |
| HPV56 | L1 | TSTSTPAK | 523 | 8 | | 39261 |
| HPV56 | L1 | TSTSTPAKR | 523 | 9 | | 39262 |
| HPV56 | L1 | TSTSTPAKRK | 523 | 10 | | 39263 |
| HPV56 | L1 | TSTSTPAKRKR | 523 | 11 | | 39264 |
| HPV56 | L1 | TTGDCPPLA | 215 | 9 | | 39265 |
| HPV56 | L1 | VATDSYVK | 57 | 8 | | 39266 |
| HPV56 | L1 | VATDSYVKR | 57 | 9 | | 39267 |
| HPV56 | L1 | VATSKKRSA | 513 | 9 | | 39268 |
| HPV56 | L1 | VATSLEDK | 443 | 8 | | 39269 |
| HPV56 | L1 | VATSLEDKY | 443 | 9 | | 39270 |
| HPV56 | L1 | VATSLEDKYR | 443 | 10 | | 39271 |
| HPV56 | L1 | VATSLEDKYRY | 443 | 11 | | 39272 |
| HPV56 | L1 | VFPIFLQMA | 29 | 9 | | 39273 |
| HPV56 | L1 | VFQLCKITLSA | 408 | 11 | | 39274 |
| HPV56 | L1 | VFRVRLPDPNK | 106 | 11 | | 39275 |
| HPV56 | L1 | VGAVNVFPIF | 24 | 10 | | 39276 |
| HPV56 | L1 | VGCTPAMGEH | 193 | 10 | | 39277 |
| HPV56 | L1 | VGETIPAELY | 301 | 10 | | 39278 |
| HPV56 | L1 | VGHPYYSVTK | 80 | 10 | | 39279 |
| HPV56 | L1 | VGRGQPLGA | 141 | 9 | | 39280 |
| HPV56 | L1 | VMAYLHNMNA | 420 | 10 | | 39281 |
| HPV56 | L1 | VSAYQYRVF | 99 | 9 | | 39282 |
| HPV56 | L1 | VSAYQYRVFR | 99 | 10 | | 39283 |
| HPV56 | L1 | VSKVVATDSY | 53 | 10 | | 39284 |
| HPV56 | L1 | VTTGDCPPLA | 214 | 10 | | 39285 |
| HPV56 | L1 | VTVVDTTR | 365 | 8 | | 39286 |
| HPV56 | L1 | VVATDSYVK | 56 | 9 | | 39287 |
| HPV56 | L1 | VVATDSYVKR | 56 | 10 | | 39288 |
| HPV56 | L1 | WACVGLEVGR | 134 | 10 | | 39289 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L1 | WDVNLQDSF | 480 | 9 | | 39290 |
| HPV56 | L1 | WFYLRREQLF | 281 | 10 | | 39291 |
| HPV56 | L1 | WFYLRREQLFA | 281 | 11 | | 39292 |
| HPV56 | L1 | WLQRAQGH | 346 | 8 | | 39293 |
| HPV56 | L1 | WTKGAVCK | 203 | 8 | | 39294 |
| HPV56 | L1 | YDARKINQY | 388 | 9 | | 39295 |
| HPV56 | L1 | YDARKINQYLR | 388 | 11 | | 39296 |
| HPV56 | L1 | YGDSMWFY | 276 | 8 | | 39297 |
| HPV56 | L1 | YGDSMWFYLR | 276 | 10 | | 39298 |
| HPV56 | L1 | YGDSMWFYLRR | 276 | 11 | | 39299 |
| HPV56 | L1 | YGLCIFLDVGA | 16 | 11 | | 39300 |
| HPV56 | L1 | YIYRDPPLH | 7 | 9 | | 39301 |
| HPV56 | L1 | YIYRDPPLHY | 7 | 10 | | 39302 |
| HPV56 | L1 | YLKGSNGR | 310 | 8 | | 39303 |
| HPV56 | L1 | YLKMSADA | 268 | 8 | | 39304 |
| HPV56 | L1 | YLKMSADAY | 268 | 9 | | 39305 |
| HPV56 | L1 | YLPPTPVSK | 47 | 9 | | 39306 |
| HPV56 | L1 | YLRHVEEY | 396 | 8 | | 39307 |
| HPV56 | L1 | YLRREQLF | 283 | 8 | | 39308 |
| HPV56 | L1 | YLRREQLFA | 283 | 9 | | 39309 |
| HPV56 | L1 | YLRREQLFAR | 283 | 10 | | 39310 |
| HPV56 | L1 | YLRREQLFARH | 283 | 11 | | 39311 |
| HPV56 | L1 | YSVTKDNTK | 85 | 9 | | 39312 |
| HPV56 | L1 | YVKRTSIF | 62 | 8 | | 39313 |
| HPV56 | L1 | YVKRTSIFY | 62 | 9 | | 39314 |
| HPV56 | L1 | YVKRTSIFYH | 62 | 10 | | 39315 |
| HPV56 | L1 | YVKRTSIFYHA | 62 | 11 | | 39316 |
| HPV56 | L1 | YVRSTAITCQR | 453 | 11 | | 39317 |
| HPV56 | L2 | AAPRLYRK | 222 | 8 | | 39318 |
| HPV56 | L2 | AAPRLYRKA | 222 | 9 | | 39319 |
| HPV56 | L2 | AAPRLYRKAF | 222 | 10 | | 39320 |
| HPV56 | L2 | ADKILQWGSLF | 41 | 11 | | 39321 |
| HPV56 | L2 | AFQQVKVTDPA | 230 | 11 | | 39322 |
| HPV56 | L2 | AFSPSGVA | 264 | 8 | | 39323 |
| HPV56 | L2 | AFTTRRGGVR | 286 | 10 | | 39324 |
| HPV56 | L2 | AFTTRRGGVRF | 286 | 11 | | 39325 |
| HPV56 | L2 | AGYVPLGSR | 69 | 9 | | 39326 |
| HPV56 | L2 | ALHRPAFTTR | 281 | 10 | | 39327 |
| HPV56 | L2 | ALHRPAFTTRR | 281 | 11 | | 39328 |
| HPV56 | L2 | ALWPVYFF | 438 | 8 | | 39329 |
| HPV56 | L2 | ALWPVYFFR | 438 | 9 | | 39330 |
| HPV56 | L2 | ALWPVYFFRR | 438 | 10 | | 39331 |
| HPV56 | L2 | ALWPVYFFRRR | 438 | 11 | | 39332 |
| HPV56 | L2 | ASATQLYK | 12 | 8 | | 39333 |
| HPV56 | L2 | ASATQLYKTCK | 12 | 11 | | 39334 |
| HPV56 | L2 | ASNTTNVTA | 383 | 9 | | 39335 |
| HPV56 | L2 | ATLVSADNPLF | 246 | 11 | | 39336 |
| HPV56 | L2 | ATPSAHLPIK | 367 | 10 | | 39337 |
| HPV56 | L2 | ATQLYKTCK | 14 | 9 | | 39338 |
| HPV56 | L2 | ATRRKRASA | 6 | 9 | | 39339 |
| HPV56 | L2 | DFMNIVALH | 275 | 9 | | 39340 |
| HPV56 | L2 | DFMNIVALHR | 275 | 10 | | 39341 |
| HPV56 | L2 | DGLYDIYA | 345 | 8 | | 39342 |
| HPV56 | L2 | DISPIAQA | 322 | 8 | | 39343 |
| HPV56 | L2 | DITPTSSTVH | 142 | 10 | | 39344 |
| HPV56 | L2 | DIYANIDDEA | 349 | 10 | | 39345 |
| HPV56 | L2 | DVVNKIEQK | 30 | 9 | | 39346 |
| HPV56 | L2 | DVYIQGSSF | 429 | 9 | | 39347 |
| HPV56 | L2 | DVYIQGSSFA | 429 | 10 | | 39348 |
| HPV56 | L2 | EAPGLSSQSVA | 357 | 11 | | 39349 |
| HPV56 | L2 | EDVVNKIEQK | 29 | 10 | | 39350 |
| HPV56 | L2 | EGTDTSLA | 257 | 8 | | 39351 |
| HPV56 | L2 | EGTDTSLAF | 257 | 9 | | 39352 |
| HPV56 | L2 | EIEMQPLLSA | 331 | 10 | | 39353 |
| HPV56 | L2 | EIPMQTFA | 194 | 8 | | 39354 |
| HPV56 | L2 | EIPMQTFAVH | 194 | 10 | | 39355 |
| HPV56 | L2 | EITSSSTTTPA | 129 | 11 | | 39356 |
| HPV56 | L2 | EMQPLLSA | 333 | 8 | | 39357 |
| HPV56 | L2 | ESGAGIPNF | 114 | 9 | | 39358 |
| HPV56 | L2 | ESSVIESGA | 109 | 9 | | 39359 |
| HPV56 | L2 | FADGDVAA | 457 | 8 | | 39360 |
| HPV56 | L2 | FALWPVYF | 437 | 8 | | 39361 |
| HPV56 | L2 | FALWPVYFF | 437 | 9 | | 39362 |
| HPV56 | L2 | FALWPVYFFR | 437 | 10 | | 39363 |
| HPV56 | L2 | FALWPVYFFRR | 437 | 11 | | 39364 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L2 | FASNTTNVTA | 382 | 10 | | 39365 |
| HPV56 | L2 | FDGLYDIY | 344 | 8 | | 39366 |
| HPV56 | L2 | FDGLYDIYA | 344 | 9 | | 39367 |
| HPV56 | L2 | FFADGDVA | 456 | 8 | | 39368 |
| HPV56 | L2 | FFADGDVAA | 456 | 9 | | 39369 |
| HPV56 | L2 | FFRRRRRK | 444 | 8 | | 39370 |
| HPV56 | L2 | FFRRRRRKR | 444 | 9 | | 39371 |
| HPV56 | L2 | FIDPPVIEA | 162 | 9 | | 39372 |
| HPV56 | L2 | FLDRPATLVSA | 241 | 11 | | 39373 |
| HPV56 | L2 | FMNIVALH | 276 | 8 | | 39374 |
| HPV56 | L2 | FMNIVALHR | 276 | 9 | | 39375 |
| HPV56 | L2 | FMNIVALHRPA | 276 | 11 | | 39376 |
| HPV56 | L2 | FSRLGRKA | 296 | 8 | | 39377 |
| HPV56 | L2 | FTTRRGGVR | 287 | 9 | | 39378 |
| HPV56 | L2 | FTTRRGGVRF | 287 | 10 | | 39379 |
| HPV56 | L2 | FVPQSPYDVTH | 418 | 11 | | 39380 |
| HPV56 | L2 | GARVHYYY | 314 | 8 | | 39381 |
| HPV56 | L2 | GFRRIAAPR | 217 | 9 | | 39382 |
| HPV56 | L2 | GFRRIAAPRLY | 217 | 11 | | 39383 |
| HPV56 | L2 | GGVRFSRLGR | 292 | 10 | | 39384 |
| HPV56 | L2 | GGVRFSRLGRK | 292 | 11 | | 39385 |
| HPV56 | L2 | GIGTGTGSGGR | 58 | 11 | | 39386 |
| HPV56 | L2 | GIPNFTGSGGF | 118 | 11 | | 39387 |
| HPV56 | L2 | GLSSQSVA | 360 | 8 | | 39388 |
| HPV56 | L2 | GSGGRAGY | 64 | 8 | | 39389 |
| HPV56 | L2 | GSSFALWPVY | 434 | 10 | | 39390 |
| HPV56 | L2 | GSSFALWPVYF | 434 | 11 | | 39391 |
| HPV56 | L2 | GTCPEDVVNK | 25 | 10 | | 39392 |
| HPV56 | L2 | GTDTSLAF | 258 | 8 | | 39393 |
| HPV56 | L2 | GTGSGGRA | 62 | 8 | | 39394 |
| HPV56 | L2 | GTGSGGRAGY | 62 | 10 | | 39395 |
| HPV56 | L2 | GTGTGSGGR | 60 | 9 | | 39396 |
| HPV56 | L2 | GTGTGSGGRA | 60 | 10 | | 39397 |
| HPV56 | L2 | GTQIGARVH | 310 | 9 | | 39398 |
| HPV56 | L2 | GTQIGARVHY | 310 | 10 | | 39399 |
| HPV56 | L2 | GTQIGARVHYY | 310 | 11 | | 39400 |
| HPV56 | L2 | GVAPDPDF | 269 | 8 | | 39401 |
| HPV56 | L2 | GVRFSRLGR | 293 | 9 | | 39402 |
| HPV56 | L2 | GVRFSRLGRK | 293 | 10 | | 39403 |
| HPV56 | L2 | GVRFSRLGRKA | 293 | 11 | | 39404 |
| HPV56 | L2 | HDVYIQGSSF | 428 | 10 | | 39405 |
| HPV56 | L2 | HDVYIQGSSFA | 428 | 11 | | 39406 |
| HPV56 | L2 | HLPIKPSTLSF | 372 | 11 | | 39407 |
| HPV56 | L2 | HSYEEIPMQTF | 190 | 11 | | 39408 |
| HPV56 | L2 | IAAPRLYR | 221 | 8 | | 39409 |
| HPV56 | L2 | IAAPRLYRK | 221 | 9 | | 39410 |
| HPV56 | L2 | IAAPRLYRKA | 221 | 10 | | 39411 |
| HPV56 | L2 | IAAPRLYRKAF | 221 | 11 | | 39412 |
| HPV56 | L2 | IDPPVIEA | 163 | 8 | | 39413 |
| HPV56 | L2 | IGARVHYY | 313 | 8 | | 39414 |
| HPV56 | L2 | IGARVHYYY | 313 | 9 | | 39415 |
| HPV56 | L2 | IGTGTGSGGR | 59 | 10 | | 39416 |
| HPV56 | L2 | IGTGTGSGGRA | 59 | 11 | | 39417 |
| HPV56 | L2 | ILISTPTSGIH | 180 | 11 | | 39418 |
| HPV56 | L2 | ILQWGSLF | 44 | 8 | | 39419 |
| HPV56 | L2 | ILQWGSLFTY | 44 | 10 | | 39420 |
| HPV56 | L2 | ILQWGSLFTYF | 44 | 11 | | 39421 |
| HPV56 | L2 | ISSTPIPGF | 210 | 9 | | 39422 |
| HPV56 | L2 | ISSTPIPGFR | 210 | 10 | | 39423 |
| HPV56 | L2 | ISSTPIPGFRR | 210 | 11 | | 39424 |
| HPV56 | L2 | ISTPTSGIH | 182 | 9 | | 39425 |
| HPV56 | L2 | ISTPTSGIHSY | 182 | 11 | | 39426 |
| HPV56 | L2 | ITPTSSTVH | 143 | 9 | | 39427 |
| HPV56 | L2 | ITSSSTTTPA | 130 | 10 | | 39428 |
| HPV56 | L2 | IVALHRPA | 279 | 8 | | 39429 |
| HPV56 | L2 | IVALHRPAF | 279 | 9 | | 39430 |
| HPV56 | L2 | IVDVTPAR | 81 | 8 | | 39431 |
| HPV56 | L2 | KATIQTRR | 302 | 8 | | 39432 |
| HPV56 | L2 | KIEQKTWA | 34 | 8 | | 39433 |
| HPV56 | L2 | KIEQKTWADK | 34 | 10 | | 39434 |
| HPV56 | L2 | KILQWGSLF | 43 | 9 | | 39435 |
| HPV56 | L2 | KILQWGSLFTY | 43 | 11 | | 39436 |
| HPV56 | L2 | KVTDPAFLDR | 235 | 10 | | 39437 |
| HPV56 | L2 | LAFSPSGVA | 263 | 9 | | 39438 |
| HPV56 | L2 | LDITPTSSTVH | 141 | 11 | | 39439 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L2 | LDRPATLVSA | 242 | 10 | | 39440 |
| HPV56 | L2 | LFEGTDTSLA | 255 | 10 | | 39441 |
| HPV56 | L2 | LFEGTDTSLAF | 255 | 11 | | 39442 |
| HPV56 | L2 | LFIDPPVIEA | 161 | 10 | | 39443 |
| HPV56 | L2 | LGNVWETPF | 393 | 9 | | 39444 |
| HPV56 | L2 | LGNVWETPFY | 393 | 10 | | 39445 |
| HPV56 | L2 | LGRKATIQTR | 299 | 10 | | 39446 |
| HPV56 | L2 | LGRKATIQTRR | 299 | 11 | | 39447 |
| HPV56 | L2 | LISTPTSGIH | 181 | 10 | | 39448 |
| HPV56 | L2 | LLSANNSF | 337 | 8 | | 39449 |
| HPV56 | L2 | LSANNSFDGLY | 338 | 11 | | 39450 |
| HPV56 | L2 | LSSQSVATPSA | 361 | 11 | | 39451 |
| HPV56 | L2 | LVSADNPLF | 248 | 9 | | 39452 |
| HPV56 | L2 | MVAHRATR | 1 | 8 | | 39453 |
| HPV56 | L2 | MVAHRATRR | 1 | 9 | | 39454 |
| HPV56 | L2 | MVAHRATRRK | 1 | 10 | | 39455 |
| HPV56 | L2 | MVAHRATRRKR | 1 | 11 | | 39456 |
| HPV56 | L2 | NFTGSGGF | 121 | 8 | | 39457 |
| HPV56 | L2 | NIVALHRPA | 278 | 9 | | 39458 |
| HPV56 | L2 | NIVALHRPAF | 278 | 10 | | 39459 |
| HPV56 | L2 | NSFDGLYDIY | 342 | 10 | | 39460 |
| HPV56 | L2 | NSFDGLYDIYA | 342 | 11 | | 39461 |
| HPV56 | L2 | NVWETPFY | 395 | 8 | | 39462 |
| HPV56 | L2 | PAFLDRPA | 239 | 8 | | 39463 |
| HPV56 | L2 | PAFTTRRGGVR | 285 | 11 | | 39464 |
| HPV56 | L2 | PDFMNIVA | 274 | 8 | | 39465 |
| HPV56 | L2 | PDFMNIVALH | 274 | 10 | | 39466 |
| HPV56 | L2 | PDFMNIVALHR | 274 | 11 | | 39467 |
| HPV56 | L2 | PDPDFMNIVA | 272 | 10 | | 39468 |
| HPV56 | L2 | PFVPQSPY | 417 | 8 | | 39469 |
| HPV56 | L2 | PGFRRIAA | 216 | 8 | | 39470 |
| HPV56 | L2 | PGFRRIAAPR | 216 | 10 | | 39471 |
| HPV56 | L2 | PGLSSQSVA | 359 | 9 | | 39472 |
| HPV56 | L2 | PIKPSTLSF | 374 | 9 | | 39473 |
| HPV56 | L2 | PIKPSTLSFA | 374 | 10 | | 39474 |
| HPV56 | L2 | PIPGFRRIA | 214 | 9 | | 39475 |
| HPV56 | L2 | PIPGFRRIAA | 214 | 10 | | 39476 |
| HPV56 | L2 | PISSTPIPGF | 209 | 10 | | 39477 |
| HPV56 | L2 | PISSTPIPGFR | 209 | 11 | | 39478 |
| HPV56 | L2 | PLFEGTDTSLA | 254 | 11 | | 39479 |
| HPV56 | L2 | PLFIDPPVIEA | 160 | 11 | | 39480 |
| HPV56 | L2 | PLGNVWETPF | 392 | 10 | | 39481 |
| HPV56 | L2 | PLGNVWETPFY | 392 | 11 | | 39482 |
| HPV56 | L2 | PLLSANNSF | 336 | 9 | | 39483 |
| HPV56 | L2 | PMQTFAVH | 196 | 8 | | 39484 |
| HPV56 | L2 | PSAHLPIK | 369 | 8 | | 39485 |
| HPV56 | L2 | PSGVAPDPDF | 267 | 10 | | 39486 |
| HPV56 | L2 | PSTIVDVTPA | 78 | 10 | | 39487 |
| HPV56 | L2 | PSTIVDVTPAR | 78 | 11 | | 39488 |
| HPV56 | L2 | PTGPSTWPF | 410 | 9 | | 39489 |
| HPV56 | L2 | PTSGIHSY | 185 | 8 | | 39490 |
| HPV56 | L2 | PVYFFRRR | 441 | 8 | | 39491 |
| HPV56 | L2 | PVYFFRRRR | 441 | 9 | | 39492 |
| HPV56 | L2 | PVYFFRRRRR | 441 | 10 | | 39493 |
| HPV56 | L2 | PVYFFRRRRRK | 441 | 11 | | 39494 |
| HPV56 | L2 | QGSSFALWPVY | 433 | 11 | | 39495 |
| HPV56 | L2 | QIGARVHY | 312 | 8 | | 39496 |
| HPV56 | L2 | QIGARVHYY | 312 | 9 | | 39497 |
| HPV56 | L2 | QIGARVHYYY | 312 | 10 | | 39498 |
| HPV56 | L2 | QSPYDVTH | 421 | 8 | | 39499 |
| HPV56 | L2 | QSPYDVTHDVY | 421 | 11 | | 39500 |
| HPV56 | L2 | QSVATPSA | 364 | 8 | | 39501 |
| HPV56 | L2 | QSVATPSAH | 364 | 9 | | 39502 |
| HPV56 | L2 | QTRRGTQIGA | 306 | 10 | | 39503 |
| HPV56 | L2 | QTRRGTQIGAR | 306 | 11 | | 39504 |
| HPV56 | L2 | QVKVTDPA | 233 | 8 | | 39505 |
| HPV56 | L2 | QVKVTDPAF | 233 | 9 | | 39506 |
| HPV56 | L2 | RAGYVPLGSR | 68 | 10 | | 39507 |
| HPV56 | L2 | RASATQLY | 11 | 8 | | 39508 |
| HPV56 | L2 | RASATQLYK | 11 | 9 | | 39509 |
| HPV56 | L2 | RATRRKRA | 5 | 8 | | 39510 |
| HPV56 | L2 | RATRRKRASA | 5 | 10 | | 39511 |
| HPV56 | L2 | RFSRLGRK | 295 | 8 | | 39512 |
| HPV56 | L2 | RFSRLGRKA | 295 | 9 | | 39513 |
| HPV56 | L2 | RGGVRFSR | 291 | 8 | | 39514 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L2 | RGGVRFSRLGR | 291 | 11 | | 39515 |
| HPV56 | L2 | RGTQIGAR | 309 | 8 | | 39516 |
| HPV56 | L2 | RGTQIGARVH | 309 | 10 | | 39517 |
| HPV56 | L2 | RGTQIGARVHY | 309 | 11 | | 39518 |
| HPV56 | L2 | RIAAPRLY | 220 | 8 | | 39519 |
| HPV56 | L2 | RIAAPRLYR | 220 | 9 | | 39520 |
| HPV56 | L2 | RIAAPRLYRK | 220 | 10 | | 39521 |
| HPV56 | L2 | RIAAPRLYRKA | 220 | 11 | | 39522 |
| HPV56 | L2 | RLGRKATIQTR | 298 | 11 | | 39523 |
| HPV56 | L2 | RLYRKAFQQVK | 225 | 11 | | 39524 |
| HPV56 | L2 | SANNSFDGLY | 339 | 10 | | 39525 |
| HPV56 | L2 | SATQLYKTCK | 13 | 10 | | 39526 |
| HPV56 | L2 | SFALWPVY | 436 | 8 | | 39527 |
| HPV56 | L2 | SFALWPVYF | 436 | 9 | | 39528 |
| HPV56 | L2 | SFALWPVYFF | 436 | 10 | | 39529 |
| HPV56 | L2 | SFALWPVYFFR | 436 | 11 | | 39530 |
| HPV56 | L2 | SFASNTTNVTA | 381 | 11 | | 39531 |
| HPV56 | L2 | SFDGLYDIY | 343 | 9 | | 39532 |
| HPV56 | L2 | SFDGLYDIYA | 343 | 10 | | 39533 |
| HPV56 | L2 | SGAGIPNF | 115 | 8 | | 39534 |
| HPV56 | L2 | SGTCPEDVVNK | 24 | 11 | | 39535 |
| HPV56 | L2 | SGVAPDPDF | 268 | 9 | | 39536 |
| HPV56 | L2 | SLAFSPSGVA | 262 | 10 | | 39537 |
| HPV56 | L2 | SSFALWPVY | 435 | 9 | | 39538 |
| HPV56 | L2 | SSFALWPVYF | 435 | 10 | | 39539 |
| HPV56 | L2 | SSFALWPVYFF | 435 | 11 | | 39540 |
| HPV56 | L2 | SSQSVATPSA | 362 | 10 | | 39541 |
| HPV56 | L2 | SSQSVATPSAH | 362 | 11 | | 39542 |
| HPV56 | L2 | SSSTTTPA | 132 | 8 | | 39543 |
| HPV56 | L2 | SSTHITNPLF | 153 | 10 | | 39544 |
| HPV56 | L2 | SSTPIPGF | 211 | 8 | | 39545 |
| HPV56 | L2 | SSTPIPGFR | 211 | 9 | | 39546 |
| HPV56 | L2 | SSTPIPGFRR | 211 | 10 | | 39547 |
| HPV56 | L2 | SSTVHVSSTH | 147 | 10 | | 39548 |
| HPV56 | L2 | SSVIESGA | 110 | 8 | | 39549 |
| HPV56 | L2 | STHITNPLF | 154 | 9 | | 39550 |
| HPV56 | L2 | STIVDVTPA | 79 | 9 | | 39551 |
| HPV56 | L2 | STIVDVTPAR | 79 | 10 | | 39552 |
| HPV56 | L2 | STPIPGFR | 212 | 8 | | 39553 |
| HPV56 | L2 | STPIPGFRR | 212 | 9 | | 39554 |
| HPV56 | L2 | STPIPGFRRIA | 212 | 11 | | 39555 |
| HPV56 | L2 | STPTSGIH | 183 | 8 | | 39556 |
| HPV56 | L2 | STPTSGIHSY | 183 | 10 | | 39557 |
| HPV56 | L2 | STVHVSSTH | 148 | 9 | | 39558 |
| HPV56 | L2 | STWPFVPQSPY | 414 | 11 | | 39559 |
| HPV56 | L2 | SVATPSAH | 365 | 8 | | 39560 |
| HPV56 | L2 | TCPEDVVNK | 26 | 9 | | 39561 |
| HPV56 | L2 | TDPAFLDR | 237 | 8 | | 39562 |
| HPV56 | L2 | TDPAFLDRPA | 237 | 10 | | 39563 |
| HPV56 | L2 | TGPSTWPF | 411 | 8 | | 39564 |
| HPV56 | L2 | TGSGGRAGY | 63 | 9 | | 38565 |
| HPV56 | L2 | TGTGSGGR | 61 | 8 | | 39566 |
| HPV56 | L2 | TGTGSGGRA | 61 | 9 | | 39567 |
| HPV56 | L2 | TGTGSGGRAGY | 61 | 11 | | 39568 |
| HPV56 | L2 | TIVDVTPA | 80 | 8 | | 39569 |
| HPV56 | L2 | TIVDVTPAR | 80 | 9 | | 39570 |
| HPV56 | L2 | TLVSADNPLF | 247 | 10 | | 39571 |
| HPV56 | L2 | TSLAFSPSGVA | 261 | 11 | | 39572 |
| HPV56 | L2 | TSSSTTTPA | 131 | 9 | | 39573 |
| HPV56 | L2 | TTSTVHVSSTH | 146 | 11 | | 39574 |
| HPV56 | L2 | TTRRGGVR | 288 | 8 | | 39575 |
| HPV56 | L2 | TTRRGGVRF | 288 | 9 | | 39576 |
| HPV56 | L2 | TTRRGGVRFSR | 288 | 11 | | 39577 |
| HPV56 | L2 | TVHVSSTH | 149 | 8 | | 39578 |
| HPV56 | L2 | VAHRATRR | 2 | 8 | | 39579 |
| HPV56 | L2 | VAHRATRRK | 2 | 9 | | 39580 |
| HPV56 | L2 | VAHRATRRKR | 2 | 10 | | 39581 |
| HPV56 | L2 | VAHRATRRKRA | 2 | 11 | | 39582 |
| HPV56 | L2 | VALHRPAF | 280 | 8 | | 39583 |
| HPV56 | L2 | VALHRPAFTTR | 280 | 11 | | 39584 |
| HPV56 | L2 | VATPSAHLPIK | 366 | 11 | | 39585 |
| HPV56 | L2 | VIESGAGIPNF | 112 | 11 | | 39586 |
| HPV56 | L2 | VLPTGPSTWPF | 408 | 11 | | 39587 |
| HPV56 | L2 | VSADNPLF | 249 | 8 | | 39588 |
| HPV56 | L2 | VSSTHITNPLF | 152 | 11 | | 39589 |

TABLE XVI-continued

A03 Motif Peptides with Binding Data

| Type | Protein | Sequence | Position | No. of Amino Acids | A*0301 | Seq. Id. No. |
|---|---|---|---|---|---|---|
| HPV56 | L2 | VTDPAFLDR | 236 | 9 | | 39590 |
| HPV56 | L2 | VTDPAFLDRPA | 236 | 11 | | 39591 |
| HPV56 | L2 | VVNKIEQK | 31 | 8 | | 39592 |
| HPV56 | L2 | VVNKIEQKTWA | 31 | 11 | | 39593 |
| HPV56 | L2 | WGSLFTYF | 47 | 8 | | 39594 |
| HPV56 | L2 | YANIDDEA | 351 | 8 | | 39595 |
| HPV56 | L2 | YDISPIAQA | 321 | 9 | | 39596 |
| HPV56 | L2 | YDIYANIDDEA | 348 | 11 | | 39597 |
| HPV56 | L2 | YDVTHDVY | 424 | 8 | | 39598 |
| HPV56 | L2 | YFFADGDVA | 455 | 9 | | 39599 |
| HPV56 | L2 | YFFADGDVAA | 455 | 10 | | 39600 |
| HPV56 | L2 | YFFRRRRR | 443 | 8 | | 39601 |
| HPV56 | L2 | YFFRRRRRK | 443 | 9 | | 39602 |
| HPV56 | L2 | YFFRRRRRKR | 443 | 10 | | 39603 |
| HPV56 | L2 | YIQGSSFA | 431 | 8 | | 39604 |

TABLE XVII

A11 Motif Peptides

| Type | Protein | Position | No. of Amino Acids | Sequeuce | A*1101 | Seq. Id. No. |
|---|---|---|---|---|---|---|
| HPV16 | E1 | 316 | 8 | AAALYWYK | | 39605 |
| HPV16 | E1 | 205 | 8 | AAMLAKFK | | 39606 |
| HPV16 | E1 | 205 | 11 | AAMLAKFKELY | | 39607 |
| HPV16 | E1 | 248 | 11 | ADSIKTLLQQY | | 39608 |
| HPV16 | E1 | 391 | 10 | AFLKSNSQAK | | 39609 |
| HPV16 | E1 | 570 | 9 | AGTDSRWPY | | 39610 |
| HPV16 | E1 | 570 | 11 | AGTDSRWPYLH | | 39611 |
| HPV16 | E1 | 112 | 9 | AICIEKQSR | 0.0057 | 39612 |
| HPV16 | E1 | 69 | 9 | ALFTAQEAK | 0.4000 | 39613 |
| HPV16 | E1 | 69 | 11 | ALFTAQEAKQH | | 39614 |
| HPV16 | E1 | 459 | 11 | ALKRFLQGIPK | | 39615 |
| HPV16 | E1 | 206 | 10 | AMLAKFKELY | | 39616 |
| HPV16 | E1 | 406 | 8 | ATMCRHYK | | 39617 |
| HPV16 | E1 | 406 | 9 | ATMCRHYKR | 1.5000 | 39618 |
| HPV16 | E1 | 524 | 8 | ATVPCWNY | | 39619 |
| HPV16 | E1 | 82 | 8 | AVQVLKRK | | 39620 |
| HPV16 | E1 | 82 | 9 | AVQVLKRKY | | 39621 |
| HPV16 | E1 | 405 | 8 | CATMCRHY | | 39622 |
| HPV16 | E1 | 405 | 9 | CATMCRHYK | 0.0098 | 39623 |
| HPV16 | E1 | 405 | 10 | CATMCRHYKR | | 39624 |
| HPV16 | E1 | 430 | 11 | CDRVDDGGDWK | | 39625 |
| HPV16 | E1 | 500 | 8 | CFVNSKSH | | 39626 |
| HPV16 | E1 | 283 | 10 | CGKNRETIEK | | 39627 |
| HPV16 | E1 | 114 | 10 | CIEKQSRAAK | | 39628 |
| HPV16 | E1 | 114 | 11 | CIEKQSRAAKR | | 39629 |
| HPV16 | E1 | 304 | 8 | CMMIEPPK | | 39630 |
| HPV16 | E1 | 304 | 10 | CMMIEPPKLR | | 39631 |
| HPV16 | E1 | 101 | 9 | CVDNNISPR | | 39632 |
| HPV16 | E1 | 101 | 11 | CVDNNISPRLK | | 39633 |
| HPV16 | E1 | 523 | 9 | DATVPCWNY | | 39634 |
| HPV16 | E1 | 81 | 8 | DAVQVLKR | | 39635 |
| HPV16 | E1 | 81 | 9 | DAVQVLKRK | | 39636 |
| HPV16 | E1 | 81 | 10 | DAVQVLKRKY | | 39637 |
| HPV16 | E1 | 404 | 8 | DCATMCRH | | 39638 |
| HPV16 | E1 | 404 | 9 | DCATMCRHY | 0.0001 | 39639 |
| HPV16 | E1 | 404 | 10 | DCATMCRHYK | 0.0130 | 39640 |
| HPV16 | E1 | 404 | 11 | DCATMCRHYKR | | 39641 |
| HPV16 | E1 | 522 | 10 | DDATVPCWNY | | 39642 |
| HPV16 | E1 | 371 | 8 | DDSEIAYK | | 39643 |
| HPV16 | E1 | 371 | 9 | DDSEIAYKY | | 39644 |
| HPV16 | E1 | 50 | 9 | DFIVNDNDY | | 39645 |
| HPV16 | E1 | 631 | 9 | DGDSLPTFK | | 39646 |
| HPV16 | E1 | 541 | 10 | DGNLVSMDVK | | 39647 |
| HPV16 | E1 | 541 | 11 | DGNLVSMDVKH | | 39648 |
| HPV16 | E1 | 368 | 10 | DIVDDSEIAY | | 39649 |
| HPV16 | E1 | 368 | 11 | DIVDDSEIAYK | | 39650 |
| HPV16 | E1 | 103 | 9 | DNNISPRLK | | 39651 |
| HPV16 | E1 | 372 | 8 | DSEIAYKY | | 39652 |
| HPV16 | E1 | 249 | 10 | DSIKTLLQQY | | 39653 |
| HPV16 | E1 | 573 | 8 | DSRWPYLH | | 39654 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV16 | E1 | 573 | 10 | DSRWPYLHNR | | 39655 |
| HPV16 | E1 | 384 | 11 | DTNSNASAFLK | | 39656 |
| HPV16 | E1 | 335 | 8 | DTPEWIQR | | 39657 |
| HPV16 | E1 | 548 | 11 | DVKHRPLVQLK | | 39658 |
| HPV16 | E1 | 452 | 10 | EFMSFLTALK | | 39659 |
| HPV16 | E1 | 452 | 11 | EFMSFLTALKR | | 39660 |
| HPV16 | E1 | 11 | 10 | EGTGCNGWFY | 0.0002 | 39661 |
| HPV16 | E1 | 603 | 8 | ELNDKNWK | | 39662 |
| HPV16 | E1 | 356 | 10 | ELSQMVQWAY | | 39663 |
| HPV16 | E1 | 221 | 10 | ELVRPFKSNK | | 39664 |
| HPV16 | E1 | 629 | 11 | ENDGDSLPTFK | | 39665 |
| HPV16 | E1 | 152 | 9 | ETETPCSQY | | 39666 |
| HPV16 | E1 | 288 | 9 | ETIEKLLSK | | 39667 |
| HPV16 | E1 | 140 | 11 | ETQQMLQVEGR | | 39668 |
| HPV16 | E1 | 594 | 9 | FDENGNPVY | | 39669 |
| HPV16 | E1 | 612 | 8 | FFSRTWSR | | 39670 |
| HPV16 | E1 | 51 | 8 | FIVNDNDY | | 39671 |
| HPV16 | E1 | 392 | 9 | FLKSNSQAK | 0.0002 | 39672 |
| HPV16 | E1 | 463 | 8 | FLQGIPKK | | 39673 |
| HPV16 | E1 | 453 | 9 | FMSFLTALK | 0.2100 | 39674 |
| HPV16 | E1 | 453 | 10 | FMSFLTALKR | | 39675 |
| HPV16 | E1 | 219 | 9 | FSELVRPFK | | 39676 |
| HPV16 | E1 | 613 | 11 | FSRTWSRLSLH | | 39677 |
| HPV16 | E1 | 71 | 9 | FTAQEAKQH | | 39678 |
| HPV16 | E1 | 71 | 10 | FTAQEAKQHR | | 39679 |
| HPV16 | E1 | 100 | 10 | GCVDNNISPR | | 39680 |
| HPV16 | E1 | 632 | 8 | GDSLPTFK | | 39681 |
| HPV16 | E1 | 334 | 9 | GDTPEWIQR | 0.0002 | 39682 |
| HPV16 | E1 | 437 | 11 | GDWKQIVMFLR | | 39683 |
| HPV16 | E1 | 176 | 8 | GGEGVSER | | 39684 |
| HPV16 | E1 | 176 | 9 | GGEGVSERH | | 39685 |
| HPV16 | E1 | 162 | 10 | GGSGGGCSQY | | 39686 |
| HPV16 | E1 | 466 | 11 | GIPKKNCILLY | | 39687 |
| HPV16 | E1 | 325 | 9 | GISNISEVY | | 39688 |
| HPV16 | E1 | 242 | 11 | GLTPSIADSIK | | 39689 |
| HPV16 | E1 | 272 | 9 | GMVVLLLVR | 0.0082 | 39690 |
| HPV16 | E1 | 272 | 10 | GMVVLLLVRY | | 39691 |
| HPV16 | E1 | 272 | 11 | GMVVLLLVRYK | | 39692 |
| HPV16 | E1 | 542 | 9 | GNLVSMDVK | | 39693 |
| HPV16 | E1 | 542 | 10 | GNLVSMDVKH | | 39694 |
| HPV16 | E1 | 542 | 11 | GNLVSMDVKHR | | 39695 |
| HPV16 | E1 | 598 | 10 | GNPVYELNDK | | 39696 |
| HPV16 | E1 | 174 | 10 | GSGGEGVSER | | 39697 |
| HPV16 | E1 | 174 | 11 | GSGGEGVSERH | | 39698 |
| HPV16 | E1 | 163 | 9 | GSGGGCSQY | | 39699 |
| HPV16 | E1 | 496 | 10 | GSVICFVNSK | | 39700 |
| HPV16 | E1 | 571 | 8 | GTDSRWPY | | 39701 |
| HPV16 | E1 | 571 | 10 | GTDSRWPYLH | | 39702 |
| HPV16 | E1 | 12 | 9 | GTGCNGWFY | 0.0720 | 39703 |
| HPV16 | E1 | 216 | 9 | GVSFSELVR | 0.0180 | 39704 |
| HPV16 | E1 | 68 | 10 | HALFTAQEAK | | 39705 |
| HPV16 | E1 | 507 | 11 | HFWLQPLADAK | | 39706 |
| HPV16 | E1 | 499 | 9 | ICFVNSKSH | | 39707 |
| HPV16 | E1 | 113 | 8 | ICIEKQSR | | 39708 |
| HPV16 | E1 | 113 | 11 | ICIEKQSRAAK | | 39709 |
| HPV16 | E1 | 473 | 11 | ILLYGAANTGK | | 39710 |
| HPV16 | E1 | 194 | 11 | ILNVLKTSNAK | | 39711 |
| HPV16 | E1 | 568 | 8 | INAGTDSR | | 39712 |
| HPV16 | E1 | 568 | 11 | INAGTDSRWPY | | 39713 |
| HPV16 | E1 | 326 | 8 | ISNISEVY | | 39714 |
| HPV16 | E1 | 369 | 9 | IVDDSEIAY | | 39715 |
| HPV16 | E1 | 369 | 10 | IVDDSEIAYK | | 39716 |
| HPV16 | E1 | 369 | 11 | IVDDSEIAYKY | | 39717 |
| HPV16 | E1 | 401 | 10 | IVKDCATMCR | | 39718 |
| HPV16 | E1 | 401 | 11 | IVKDCATMCRH | | 39719 |
| HPV16 | E1 | 204 | 9 | KAAMLAKFK | 0.1800 | 39720 |
| HPV16 | E1 | 111 | 10 | KAICIEKQSR | | 39721 |
| HPV16 | E1 | 282 | 11 | KCGKNRETIEK | | 39722 |
| HPV16 | E1 | 403 | 8 | KDCATMCR | | 39723 |
| HPV16 | E1 | 403 | 9 | KDCATMCRH | 0.0002 | 39724 |
| HPV16 | E1 | 403 | 10 | KDCATMCRHY | 0.0002 | 39725 |
| HPV16 | E1 | 403 | 11 | KDCATMCRHYK | | 39726 |
| HPV16 | E1 | 400 | 11 | KIVKDCATMCR | | 39727 |
| HPV16 | E1 | 311 | 10 | KLRSTAAALY | | 39728 |
| HPV16 | E1 | 285 | 8 | KNRETIEK | | 39729 |

TABLE XVII-continued

A11 Motif Peptides

| Type | Protein | Position | No. of Amino Acids | Sequence | A*1101 | Seq. Id. No. |
|---|---|---|---|---|---|---|
| HPV16 | E1 | 607 | 9 | KNWKSFFSR | | 39730 |
| HPV16 | E1 | 610 | 10 | KSFFSRTWSR | | 39731 |
| HPV16 | E1 | 483 | 10 | KSLFGMSLMK | | 39732 |
| HPV16 | E1 | 394 | 10 | KSNSQAKIVK | | 39733 |
| HPV16 | E1 | 323 | 11 | KTGISNISEVY | | 39734 |
| HPV16 | E1 | 252 | 10 | KTLLQQYCLY | | 39735 |
| HPV16 | E1 | 208 | 8 | LAKFKELY | | 39736 |
| HPV16 | E1 | 521 | 11 | LDDATVPCWNY | | 39737 |
| HPVi6 | E1 | 540 | 11 | LDGNLVSMDVK | | 39738 |
| HPV16 | E1 | 126 | 9 | LFESEDSGY | | 39739 |
| HPV16 | E1 | 485 | 8 | LFGMSLMK | | 39740 |
| HPV16 | E1 | 70 | 8 | LFTAQEAK | | 39741 |
| HPV16 | E1 | 70 | 10 | LFTAQEAKQH | | 39742 |
| HPV16 | E1 | 70 | 11 | LFTAQEAKQHR | | 39743 |
| HPV16 | E1 | 276 | 10 | LLLVRYKCGK | | 39744 |
| HPV16 | E1 | 254 | 8 | LLQQYCLY | | 39745 |
| HPV16 | E1 | 254 | 10 | LLQQYCLYLH | | 39746 |
| HPV16 | E1 | 277 | 9 | LLVRYKCGK | 0.0033 | 39747 |
| HPV16 | E1 | 277 | 11 | LLVRYKCGKNR | | 39748 |
| HPV16 | E1 | 474 | 10 | LLYGAANTGK | | 39749 |
| HPV16 | E1 | 195 | 10 | LNVLKTSNAK | | 39750 |
| HPV16 | E1 | 620 | 9 | LSLHEDEDK | 0.0002 | 39751 |
| HPV16 | E1 | 357 | 9 | LSQMVQWAY | | 39752 |
| HPV16 | E1 | 191 | 9 | LTNILNVLK | 0.4200 | 39753 |
| HPV16 | E1 | 243 | 10 | LTPSIADSIK | | 39754 |
| HPV16 | E1 | 59 | 10 | LTQAETETAH | | 39755 |
| HPV16 | E1 | 48 | 11 | LVDFIVNDNDY | | 39756 |
| HPV16 | E1 | 222 | 9 | LVRPFKSNK | 1.8000 | 39757 |
| HPV16 | E1 | 278 | 8 | LVRYKCGK | | 39758 |
| HPV16 | E1 | 278 | 10 | LVRYKCGKNR | | 39759 |
| HPV16 | E1 | 544 | 8 | LVSMDVKH | | 39760 |
| HPV16 | E1 | 544 | 9 | LVSMDVKHR | 0.0089 | 39761 |
| HPV16 | E1 | 303 | 9 | MCMMIEPPK | | 39762 |
| HPV16 | E1 | 303 | 11 | MCMMIEPPKLR | | 39763 |
| HPV16 | E1 | 408 | 10 | MCRHYKRAEK | | 39764 |
| HPV16 | E1 | 408 | 11 | MCRHYKRAEKK | | 39765 |
| HPV16 | E1 | 306 | 8 | MIEPPKLR | | 39766 |
| HPV16 | E1 | 207 | 9 | MLAKFKELY | | 39767 |
| HPV16 | E1 | 144 | 8 | MLQVEGRH | | 39768 |
| HPV16 | E1 | 305 | 9 | MMIEPPKLR | 0.0086 | 39769 |
| HPV16 | E1 | 454 | 8 | MSFLTALK | | 39770 |
| HPV16 | E1 | 454 | 9 | MSFLTALKR | 0.0980 | 39771 |
| HPV16 | E1 | 420 | 8 | MSMSQWIK | | 39772 |
| HPV16 | E1 | 420 | 9 | MSMSQWIKY | | 39773 |
| HPV16 | E1 | 420 | 10 | MSMSQWIKYR | | 39774 |
| HPV16 | E1 | 422 | 8 | MSQWIKYR | | 39775 |
| HPV16 | E1 | 422 | 11 | MSQWIKYRCDR | | 39776 |
| HPV16 | E1 | 273 | 8 | MVVLLLVR | | 39777 |
| HPV16 | E1 | 273 | 9 | MVVLLLVRY | | 39778 |
| HPV16 | E1 | 273 | 10 | MVVLLLVRYK | | 39779 |
| HPV16 | E1 | 569 | 10 | NAGTDSRWPY | | 39780 |
| HPV16 | E1 | 202 | 9 | NAKAAMLAK | 0.0031 | 39781 |
| HPV16 | E1 | 202 | 11 | NAKAAMLAKFK | | 39782 |
| HPV16 | E1 | 630 | 10 | NDGDSLPTFK | | 39783 |
| HPV16 | E1 | 367 | 11 | NDIVDDSEIAY | | 39784 |
| HPV16 | E1 | 605 | 11 | NDKNWKSFFSR | | 39785 |
| HPV16 | E1 | 597 | 11 | NGNPVYELNDK | | 39786 |
| HPV16 | E1 | 567 | 9 | NINAGTDSR | 0.0002 | 39787 |
| HPV16 | E1 | 543 | 8 | NLVSMDVK | | 39788 |
| HPV16 | E1 | 543 | 9 | NLVSMDVKH | | 39789 |
| HPV16 | E1 | 543 | 10 | NLVSMDVKHR | | 39790 |
| HPV16 | E1 | 104 | 8 | NNISPRLK | | 39791 |
| HPV16 | E1 | 386 | 9 | NSNASAFLK | 0.0110 | 39792 |
| HPV16 | E1 | 396 | 8 | NSQAKIVK | | 39793 |
| HPV16 | E1 | 196 | 9 | NVLKTSNAK | 0.0015 | 39794 |
| HPV16 | E1 | 527 | 11 | PCWNYIDDNLR | | 39795 |
| HPV16 | E1 | 593 | 10 | PFDENGNPVY | | 39796 |
| HPV16 | E1 | 190 | 10 | PLTNILNVLK | | 39797 |
| HPV16 | E1 | 302 | 10 | PMCMMIEPPK | | 39798 |
| HPV16 | E1 | 245 | 8 | PSIADSIK | | 39799 |
| HPV16 | E1 | 600 | 8 | PVYELNDK | | 39800 |
| HPV16 | E1 | 600 | 11 | PVYELNDKNWK | | 39801 |
| HPV16 | E1 | 61 | 8 | QAETETAH | | 39802 |
| HPV16 | E1 | 495 | 11 | QGSVICFVNSK | | 39803 |
| HPV16 | E1 | 441 | 8 | QIVMFLRY | | 39804 |

TABLE XVII-continued

A11 Motif Peptides

| Type | Protein | Position | No. of Amino Acids | Sequence | A*1101 | Seq. Id. No. |
|---|---|---|---|---|---|---|
| HPV16 | E1 | 143 | 8 | QMLQVEGR | | 39805 |
| HPV16 | E1 | 143 | 9 | QMLQVEGRH | | 39806 |
| HPV16 | E1 | 419 | 9 | QMSMSQWIK | 0.0260 | 39807 |
| HPV16 | E1 | 419 | 10 | QMSMSQWIKY | | 39808 |
| HPV16 | E1 | 419 | 11 | QMSMSQWIKYR | | 39809 |
| HPV16 | E1 | 118 | 8 | QSRAAKRR | | 39810 |
| HPV16 | E1 | 80 | 8 | RDAVQVLK | | 39811 |
| HPV16 | E1 | 80 | 9 | RDAVQVLKR | | 39812 |
| HPV16 | E1 | 80 | 10 | RDAVQVLKRK | | 39813 |
| HPV16 | E1 | 80 | 11 | RDAVQVLKRKY | | 39814 |
| HPV16 | E1 | 462 | 8 | RFLQGIPK | | 39815 |
| HPV16 | E1 | 462 | 9 | RFLQGIPKK | | 39816 |
| HPV16 | E1 | 125 | 10 | RLFESEDSGY | | 39817 |
| HPV16 | E1 | 109 | 9 | RLKAICIEK | 0.0510 | 39818 |
| HPV16 | E1 | 619 | 10 | RLSLHEDEDK | | 39819 |
| HPV16 | E1 | 313 | 8 | RSTAAALY | | 39820 |
| HPV16 | E1 | 313 | 10 | RSTAAALYWY | | 39821 |
| HPV16 | E1 | 313 | 11 | RSTAAALYWYK | | 39822 |
| HPV16 | E1 | 615 | 9 | RTWSRLSLH | | 39823 |
| HPV16 | E1 | 432 | 9 | RVDDGGDWK | | 39824 |
| HPV16 | E1 | 390 | 11 | SAFLKSNSQAK | | 39825 |
| HPV16 | E1 | 611 | 9 | SFFSRTWSR | | 39826 |
| HPV16 | E1 | 455 | 8 | SFLTALKR | | 39827 |
| HPV16 | E1 | 218 | 10 | SFSELVRPFK | | 39828 |
| HPV16 | E1 | 99 | 11 | SGCVDNNISPR | | 39829 |
| HPV16 | E1 | 175 | 9 | SGGEGVSER | | 39830 |
| HPV16 | E1 | 175 | 10 | SGGEGVSERH | | 39831 |
| HPV16 | E1 | 164 | 8 | SGGGCSQY | | 39832 |
| HPV16 | E1 | 161 | 11 | SGGSGGGCSQY | | 39833 |
| HPV16 | E1 | 173 | 11 | SGSGGEGVSER | | 39834 |
| HPV16 | E1 | 250 | 9 | SIKTLLQQY | | 39835 |
| HPV16 | E1 | 484 | 9 | SLFGMSLMK | 7.1000 | 39836 |
| HPV16 | E1 | 621 | 8 | SLHEDEDK | | 39837 |
| HPV16 | E1 | 421 | 8 | SMSQWIKY | | 39838 |
| HPV16 | E1 | 421 | 9 | SMSQWIKYR | 0.0280 | 39839 |
| HPV16 | E1 | 201 | 10 | SNAKAAMLAK | | 39840 |
| HPV16 | E1 | 387 | 8 | SNASAFLK | | 39841 |
| HPV16 | E1 | 566 | 10 | SNINAGTDSR | | 39842 |
| HPV16 | E1 | 395 | 9 | SNSQAKIVK | | 39843 |
| HPV16 | E1 | 314 | 9 | STAAALYWY | | 39844 |
| HPV16 | E1 | 314 | 10 | STAAALYWYK | | 39845 |
| HPV16 | E1 | 497 | 9 | SVICFVNSK | 0.0002 | 39846 |
| HPV16 | E1 | 497 | 11 | SVICFVNSKSH | | 39847 |
| HPV16 | E1 | 315 | 8 | TAAALYWY | | 39848 |
| HPV16 | E1 | 315 | 9 | TAAALYWYK | 20.0000 | 39849 |
| HPV16 | E1 | 72 | 8 | TAQEAKQH | | 39850 |
| HPV16 | E1 | 72 | 9 | TAQEAKQHR | 0.0025 | 39851 |
| HPV16 | E1 | 572 | 9 | TDSRWPYLH | | 39852 |
| HPV16 | E1 | 572 | 11 | TDSRWPYLHNR | | 39853 |
| HPV16 | E1 | 13 | 8 | TGCNGWFY | | 39854 |
| HPV16 | E1 | 324 | 10 | TGISNISEVY | | 39855 |
| HPV16 | E1 | 289 | 8 | TIEKLLSK | | 39856 |
| HPV16 | E1 | 253 | 9 | TLLQQYCLY | | 39857 |
| HPV16 | E1 | 253 | 11 | TLLQQYCLYLH | | 39858 |
| HPV16 | E1 | 407 | 8 | TMCRHYKR | | 39859 |
| HPV16 | E1 | 407 | 11 | TMCRHYKRAEK | | 39860 |
| HPV16 | E1 | 192 | 8 | TNILNVLK | | 39861 |
| HPV16 | E1 | 385 | 10 | TNSNASAFLK | | 39862 |
| HPV16 | E1 | 200 | 11 | TSNAKAAMLAK | | 39863 |
| HPV16 | E1 | 565 | 11 | TSNINAGTDSR | | 39864 |
| HPV16 | E1 | 433 | 8 | VDDGGDWK | | 39865 |
| HPV16 | E1 | 370 | 8 | VDDSEIAY | | 39866 |
| HPV16 | E1 | 370 | 9 | VDDSEIAYK | | 39867 |
| HPV16 | E1 | 370 | 10 | VDDSEIAYKY | | 39868 |
| HPV16 | E1 | 49 | 10 | VDFIVNDNDY | | 39869 |
| HPV16 | E1 | 102 | 8 | VDNNISPR | | 39870 |
| HPV16 | E1 | 102 | 10 | VDNNISPRLK | | 39871 |
| HPV16 | E1 | 498 | 8 | VICFVNSK | | 39872 |
| HPV16 | E1 | 498 | 10 | VICFVNSKSH | | 39873 |
| HPV16 | E1 | 197 | 8 | VLKTSNAK | | 39874 |
| HPV16 | E1 | 275 | 8 | VLLLVRYK | | 39875 |
| HPV16 | E1 | 275 | 11 | VLLLVRYKCGK | | 39876 |
| HPV16 | E1 | 217 | 8 | VSFSELVR | | 39877 |
| HPV16 | E1 | 217 | 11 | VSFSELVRPFK | | 39878 |
| HPV16 | E1 | 545 | 8 | VSMDVKHR | | 39879 |

TABLE XVII-continued

A11 Motif Peptides

| Type | Protein | Position | No. of Amino Acids | Sequence | A*1101 | Seq. Id. No. |
|---|---|---|---|---|---|---|
| HPV16 | E1 | 274 | 8 | VVLLLVRY | | 39880 |
| HPV16 | E1 | 274 | 9 | VVLLLVRYK | 0.3600 | 39881 |
| HPV16 | E1 | 18 | 10 | WFYVEAVVEK | | 39882 |
| HPV16 | E1 | 18 | 11 | WFYVEAVVEKK | | 39883 |
| HPV16 | E1 | 271 | 10 | WGMVVLLLVR | | 39884 |
| HPV16 | E1 | 271 | 11 | WGMVVLLLVRY | | 39885 |
| HPV16 | E1 | 425 | 8 | WIKYRCDR | | 39886 |
| HPV16 | E1 | 339 | 10 | WIQRQTVLQH | | 39887 |
| HPV16 | E1 | 509 | 9 | WLQPLADAK | 0.0002 | 39888 |
| HPV16 | E1 | 529 | 9 | WNYIDDNLR | | 39889 |
| HPV16 | E1 | 476 | 8 | YGAANTGK | | 39890 |
| HPV16 | E1 | 333 | 10 | YGDTPEWIQR | | 39891 |
| HPV16 | E1 | 215 | 10 | YGVSFSELVR | | 39892 |
| HPV16 | E1 | 58 | 11 | YLTQAETETAH | | 39893 |
| HPV16 | E1 | 20 | 8 | YVEAVVEK | | 39894 |
| HPV16 | E1 | 20 | 9 | YVEAVVEKK | | 39895 |
| HPV16 | E2 | 270 | 9 | AFNSSHKGR | | 39896 |
| HPV16 | E2 | 216 | 8 | ANHPAATH | | 39897 |
| HPV16 | E2 | 216 | 10 | ANRPAATHTK | | 39898 |
| HPV16 | E2 | 295 | 8 | ANTLKCLR | | 39899 |
| HPV16 | E2 | 295 | 9 | ANTLKCLRY | | 39900 |
| HPV16 | E2 | 295 | 10 | ANTLKCLRYR | | 39901 |
| HPV16 | E2 | 314 | 11 | AVSSTWHWTGH | | 39902 |
| HPV16 | E2 | 40 | 8 | CAIYYKAR | | 39903 |
| HPV16 | E2 | 300 | 8 | CLRYRFKK | | 39904 |
| HPV16 | E2 | 300 | 9 | CLRYRFKKH | | 39905 |
| HPV16 | E2 | 281 | 10 | CNSNTTPIVH | | 39906 |
| HPV16 | E2 | 126 | 11 | CNTMHYTNWTH | | 39907 |
| HPV16 | E2 | 174 | 9 | DAEKYSKNK | | 39908 |
| HPV16 | E2 | 294 | 9 | DANTLKCLR | | 39909 |
| HPV16 | E2 | 294 | 10 | DANTLKCLRY | | 39910 |
| HPV16 | E2 | 294 | 11 | DANTLKCLRYR | | 39911 |
| HPV16 | E2 | 173 | 8 | DDAEKYSK | | 39912 |
| HPV16 | E2 | 173 | 10 | DDAEKYSKNK | | 39913 |
| HPV16 | E2 | 122 | 9 | DGDICNTMH | | 39914 |
| HPV16 | E2 | 122 | 10 | DGDICNTMHY | | 39915 |
| HPV16 | E2 | 124 | 8 | DICNTMHY | | 39916 |
| HPV16 | E2 | 25 | 8 | DLRDHIDY | | 39917 |
| HPV16 | E2 | 25 | 10 | DLRDHIDYWK | | 39918 |
| HPV16 | E2 | 25 | 11 | DLRDHIDYWKH | | 39919 |
| HPV16 | E2 | 22 | 8 | DSTDLRDH | | 39920 |
| HPV16 | E2 | 22 | 11 | DSTDLRDHIDY | | 39921 |
| HPV16 | E2 | 246 | 10 | DTGNPCHTTK | | 39922 |
| HPV16 | E2 | 39 | 9 | ECAIYYKAR | | 39923 |
| HPV16 | E2 | 162 | 11 | EGIRTYFVQFK | | 39924 |
| HPV16 | E2 | 149 | 10 | EGQVDYYGLY | | 39925 |
| HPV16 | E2 | 149 | 11 | EGQVDYYGLYY | | 39926 |
| HPV16 | E2 | 209 | 10 | EIIRQHLANH | | 39927 |
| HPV16 | E2 | 74 | 10 | ELQLTLETIY | | 39928 |
| HPV16 | E2 | 48 | 9 | EMGFKHINH | | 39929 |
| HPV16 | E2 | 20 | 8 | ENDSTDLR | | 39930 |
| HPV16 | E2 | 20 | 10 | ENDSTDLRDH | | 39931 |
| HPV16 | E2 | 80 | 8 | ETIYNSQY | | 39932 |
| HPV16 | E2 | 233 | 8 | ETQTTIQR | | 39933 |
| HPV16 | E2 | 233 | 10 | ETQTTIQRPR | | 39934 |
| HPV16 | E2 | 204 | 9 | EVSSPEIIR | | 39935 |
| HPV16 | E2 | 204 | 11 | EVSSPEIIRQH | | 39936 |
| HPV16 | E2 | 121 | 10 | FDGDICNTMH | | 39937 |
| HPV16 | E2 | 121 | 11 | FDGDICNTMHY | | 39938 |
| HPV16 | E2 | 346 | 9 | FLSQVKIPK | | 39939 |
| HPV16 | E2 | 271 | 8 | FNSSHKGR | | 39940 |
| HPV16 | E2 | 168 | 10 | FVQFKDDAEK | | 39941 |
| HPV16 | E2 | 168 | 11 | FVQFKDDAEKY | | 39942 |
| HPV16 | E2 | 108 | 8 | GCIKKHGY | | 39943 |
| HPV16 | E2 | 293 | 10 | GDANTLKCLR | | 39944 |
| HPV16 | E2 | 293 | 11 | GDANTLKCLRY | | 39945 |
| HPV16 | E2 | 123 | 8 | GDICNTMH | | 39946 |
| HPV16 | E2 | 123 | 9 | GDICNTMHY | | 39947 |
| HPV16 | E2 | 163 | 10 | GIRTYFVQFK | | 39948 |
| HPV16 | E2 | 156 | 10 | GLYYVHEGIR | | 39949 |
| HPV16 | E2 | 248 | 8 | GNPCHTTK | | 39950 |
| HPV16 | E2 | 248 | 11 | GNPCHTTKLLH | | 39951 |
| HPV16 | E2 | 230 | 11 | GTEETQTTIQR | | 39952 |
| HPV16 | E2 | 29 | 9 | HIDYWKHMR | | 39953 |
| HPV16 | E2 | 214 | 10 | HLANHPAATH | | 39954 |

TABLE XVII-continued

A11 Motif Peptides

| Type | Protein | Position | No. of Amino Acids | Sequence | A*1101 | Seq. Id. No. |
|---|---|---|---|---|---|---|
| HPV16 | E2 | 290 | 10 | HLKGDANTLK | | 39955 |
| HPV16 | E2 | 35 | 9 | HMRLECAIY | | 39956 |
| HPV16 | E2 | 35 | 10 | HMRLECAIYY | | 39957 |
| HPV16 | E2 | 35 | 11 | HMRLECAIYYK | | 39958 |
| HPV16 | E2 | 252 | 8 | HTTKLLHR | | 39959 |
| HPV16 | E2 | 30 | 8 | IDYWKHMR | | 39960 |
| HPV16 | E2 | 210 | 9 | IIRQHLANH | | 39961 |
| HPV16 | E2 | 267 | 9 | ILTAFNSSH | | 39962 |
| HPV16 | E2 | 267 | 10 | ILTAFNSSHK | | 39963 |
| HPV16 | E2 | 45 | 8 | KAREMGFK | | 39964 |
| HPV16 | E2 | 45 | 9 | KAREMGFKH | | 39965 |
| HPV16 | E2 | 299 | 8 | KCLRYRFK | | 39966 |
| HPV16 | E2 | 299 | 9 | KCLRYRFKK | | 39967 |
| HPV16 | E2 | 299 | 10 | KCLRYRFKKH | | 39968 |
| HPV16 | E2 | 172 | 9 | KDDAEKYSK | | 39969 |
| HPV16 | E2 | 172 | 11 | KDDAEKYSKNK | | 39970 |
| HPV16 | E2 | 292 | 8 | KGDANTLK | | 39971 |
| HPV16 | E2 | 292 | 11 | KGDANTLKCLR | | 39972 |
| HPV16 | E2 | 180 | 8 | KNKVWEVH | | 39973 |
| HPV16 | E2 | 329 | 9 | KSAIVTLTY | | 39974 |
| HPV16 | E2 | 215 | 9 | LANHPAATH | | 39975 |
| HPV16 | E2 | 215 | 11 | LANHPAATHTK | | 39976 |
| HPV16 | E2 | 4 | 11 | LCQRLNVCQDK | | 39977 |
| HPV16 | E2 | 8 | 11 | LNVCQDKILTH | | 39978 |
| HPV16 | E2 | 347 | 8 | LSQVKIPK | | 39979 |
| HPV16 | E2 | 268 | 8 | LTAFNSSH | | 39980 |
| HPV16 | E2 | 268 | 9 | LTAFNSSHK | | 39981 |
| HPV16 | E2 | 268 | 11 | LTAFNSSHKGR | | 39982 |
| HPV16 | E2 | 103 | 9 | LTAPTGCIK | | 39983 |
| HPV16 | E2 | 103 | 10 | LTAPTGCIKK | | 39984 |
| HPV16 | E2 | 103 | 11 | LTAPTGCIKKH | | 39985 |
| HPV16 | E2 | 77 | 11 | LTLETIYNSQY | | 39986 |
| HPV16 | E2 | 335 | 9 | LTYDSEWQR | | 39987 |
| HPV16 | E2 | 49 | 8 | MGFKHINH | | 39988 |
| HPV16 | E2 | 280 | 11 | NCNSNTTPIVH | | 39989 |
| HPV16 | E2 | 21 | 9 | NDSTDLRDH | | 39990 |
| HPV16 | E2 | 282 | 9 | NSNTTPIVH | | 39991 |
| HPV16 | E2 | 282 | 11 | NSNTTPIVHLK | | 39992 |
| HPV16 | E2 | 84 | 8 | NSQYSNEK | | 39993 |
| HPV16 | E2 | 296 | 8 | NTLKCLRY | | 39994 |
| HPV16 | E2 | 296 | 9 | NTLKCLRYR | | 39995 |
| HPV16 | E2 | 296 | 11 | NTLKCLRYRFK | | 39996 |
| HPV16 | E2 | 127 | 10 | NTMHYTNWTH | | 39997 |
| HPV16 | E2 | 284 | 9 | NTTPIVHLK | | 39998 |
| HPV16 | E2 | 9 | 10 | NVCQDKILTH | | 39999 |
| HPV16 | E2 | 9 | 11 | NVCQDKILTHY | | 40000 |
| HPV16 | E2 | 250 | 9 | PCHTTKLLH | | 40001 |
| HPV16 | E2 | 250 | 10 | PCHTTKLLHR | | 40002 |
| HPV16 | E2 | 245 | 8 | PDTGNPCH | | 40003 |
| HPV16 | E2 | 245 | 11 | PDTGNPCHTTK | | 40004 |
| HPV16 | E2 | 266 | 10 | PILTAFNSSH | | 40005 |
| HPV16 | E2 | 266 | 11 | PILTAFNSSHK | | 40006 |
| HPV16 | E2 | 106 | 8 | PTGCIKKH | | 40007 |
| HPV16 | E2 | 106 | 10 | PTGCIKKHGY | | 40008 |
| HPV16 | E2 | 60 | 9 | PTLAVSKNK | | 40009 |
| HPV16 | E2 | 12 | 8 | QDKILTHY | | 40010 |
| HPV16 | E2 | 95 | 8 | QDVSLEVY | | 40011 |
| HPV16 | E2 | 120 | 11 | QFDGDICNTMH | | 40012 |
| HPV16 | E2 | 170 | 8 | QFKDDAEK | | 40013 |
| HPV16 | E2 | 170 | 9 | QFKDDAEKY | | 40014 |
| HPV16 | E2 | 170 | 11 | QFKDDAEKYSK | | 40015 |
| HPV16 | E2 | 345 | 10 | QFLSQVKIPK | | 40016 |
| HPV16 | E2 | 76 | 8 | QLTLETIY | | 40017 |
| HPV16 | E2 | 235 | 8 | QTTIQRPR | | 40018 |
| HPV16 | E2 | 151 | 8 | QVDYYGLY | | 40019 |
| HPV16 | E2 | 151 | 9 | QVDYYGLYY | | 40020 |
| HPV16 | E2 | 151 | 11 | QVDYYGLYYVH | | 40021 |
| HPV16 | E2 | 57 | 10 | QVVPTLAVSK | | 40022 |
| HPV16 | E2 | 27 | 8 | RDHIDYWK | | 40023 |
| HPV16 | E2 | 27 | 9 | RDHIDYWKH | | 40024 |
| HPV16 | E2 | 27 | 11 | RDHIDYWKHMR | | 40025 |
| HPV16 | E2 | 343 | 9 | RDQFLSQVK | | 40026 |
| HPV16 | E2 | 304 | 9 | RFKKHCTLY | | 40027 |
| HPV16 | E2 | 37 | 8 | RLECAIYY | | 40028 |
| HPV16 | E2 | 37 | 9 | RLECAIYYK | | 40029 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV16 | E2 | 37 | 11 | RLECAIYYKAR | | 40030 |
| HPY16 | E2 | 7 | 8 | RLNVCQDK | | 40031 |
| HPV16 | E2 | 242 | 11 | RSEPDTGNPCH | | 40032 |
| HPV16 | E2 | 165 | 8 | RTYFVQFK | | 40033 |
| HPV16 | E2 | 330 | 8 | SAIVTLTY | | 40034 |
| HPV16 | E2 | 202 | 11 | SNEVSSPEIIR | | 40035 |
| HPV16 | E2 | 283 | 8 | SNTTPIVH | | 40036 |
| HPV16 | E2 | 283 | 10 | SNTTPIVHLK | | 40037 |
| HPV16 | E2 | 206 | 9 | SSPEIIRQH | | 40038 |
| HPV16 | E2 | 316 | 9 | SSTWHWTGH | | 40039 |
| HPV16 | E2 | 23 | 10 | STDLRDHIDY | | 40040 |
| HPV16 | E2 | 317 | 8 | STWHWTGH | | 40041 |
| HPV16 | E2 | 317 | 11 | STWHWTGHNVK | | 40042 |
| HPV16 | E2 | 144 | 11 | SVTVVEGQVDY | | 40043 |
| HPV16 | E2 | 269 | 8 | TAFNSSHK | | 40044 |
| HPV16 | E2 | 269 | 10 | TAFNSSHKGR | | 40045 |
| HPV16 | E2 | 104 | 8 | TAPTGCIK | | 40046 |
| HPV16 | E2 | 104 | 9 | TAPTGCIKK | | 40047 |
| HPV16 | E2 | 104 | 10 | TAPTGCIKKH | | 40048 |
| HPV16 | E2 | 313 | 8 | TAVSSTWH | | 40049 |
| HPV16 | E2 | 24 | 9 | TDLRDHIDY | | 40050 |
| HPV16 | E2 | 24 | 11 | TDLRDHIDYWK | | 40051 |
| HPV16 | E2 | 107 | 9 | TGCIKKHGY | | 40052 |
| HPV16 | E2 | 322 | 8 | TGHNVKHK | | 40053 |
| HPV16 | E2 | 247 | 9 | TGNPCHTTK | | 40054 |
| HPV16 | E2 | 81 | 11 | TIYNSQYSNEK | | 40055 |
| HPV16 | E2 | 61 | 8 | TLAVSKNK | | 40056 |
| HPV16 | E2 | 78 | 10 | TLETIYNSQY | | 40057 |
| HPV16 | E2 | 297 | 8 | TLKCLRYR | | 40058 |
| HPV16 | E2 | 297 | 10 | TLKCLRYRFK | | 40059 |
| HPV16 | E2 | 297 | 11 | TLKCLRYRFKK | | 40060 |
| HPV16 | E2 | 93 | 10 | TLQDVSLEVY | | 40061 |
| HPV16 | E2 | 334 | 10 | TLTYDSEWQR | | 40062 |
| HPV16 | E2 | 310 | 11 | TLYTAVSSTWH | | 40063 |
| HPV16 | E2 | 128 | 9 | TMHYTNWTH | | 40064 |
| HPV16 | E2 | 128 | 11 | TMHYTNWTHIY | | 40065 |
| HPV16 | E2 | 285 | 8 | TTPIVHLK | | 40066 |
| HPV16 | E2 | 146 | 9 | TVVEGQVDY | | 40067 |
| HPV16 | E2 | 146 | 10 | TVVEGQVDYY | | 40068 |
| HPV16 | E2 | 10 | 9 | VCQDKILTH | | 40069 |
| HPV16 | E2 | 10 | 10 | VCQDKILTHY | | 40070 |
| HPV16 | E2 | 152 | 8 | VDYYGLYY | | 40071 |
| HPV16 | E2 | 152 | 10 | VDYYGLYYVH | | 40072 |
| HPV16 | E2 | 205 | 8 | VSSPEIR | | 40073 |
| HPV16 | E2 | 205 | 10 | VSSPEIIRQH | | 40074 |
| HPV16 | E2 | 315 | 10 | VSSTWIIWTGH | | 40075 |
| HPV16 | E2 | 333 | 11 | VTLTYDSEWQR | | 40076 |
| HPV16 | E2 | 145 | 10 | VTVVEGQVDY | | 40077 |
| HPV16 | E2 | 145 | 11 | VTVVEGQVDYY | | 40078 |
| HPV16 | E2 | 147 | 8 | VVEGQVDY | | 40079 |
| HPV16 | E2 | 147 | 9 | VVEGQVDYY | | 40080 |
| HPV16 | E2 | 58 | 9 | VVPTLAVSK | | 40081 |
| HPV16 | E2 | 58 | 11 | VVPTLAVSKNK | | 40082 |
| HPV16 | E2 | 321 | 8 | WTGHNVKH | | 40083 |
| HPV16 | E2 | 321 | 9 | WTGHNVKHK | | 40084 |
| HPV16 | E2 | 92 | 11 | WTLQDVSLEVY | | 40085 |
| HPV16 | E2 | 167 | 11 | YFVQFKDDAEK | | 40086 |
| HPV16 | E2 | 155 | 11 | YGLYYVHEGIR | | 40087 |
| HPV16 | E2 | 102 | 10 | YLTAPTGCIK | | 40088 |
| HPV16 | E2 | 102 | 11 | YLTAPTGCIKK | | 40089 |
| HPV16 | E2 | 83 | 9 | YNSQYSNEK | | 40090 |
| HPV16 | E2 | 178 | 10 | YSKNKVWEVH | | 40091 |
| HPV16 | E2 | 312 | 9 | YTAVSSTWH | | 40092 |
| HPV16 | E2 | 131 | 8 | YTNWTHIY | | 40093 |
| HPV16 | E2 | 159 | 9 | YVHEGIRTY | | 40094 |
| HPV16 | E5 | 53 | 11 | AASAFRCFIVY | | 40095 |
| HPV16 | E5 | 56 | 8 | AFRCFIVY | | 40096 |
| HPV16 | E5 | 54 | 10 | ASAFRCFIVY | | 40097 |
| HPV16 | E5 | 59 | 10 | CFIVYIIFVY | | 40098 |
| HPV16 | E5 | 20 | 11 | CVLLCVCLLIR | | 40099 |
| HPV16 | E5 | 60 | 9 | FIVYIIFVY | | 40100 |
| HPV16 | E5 | 72 | 8 | FLIHTHAR | | 40101 |
| HPV16 | E5 | 66 | 10 | FVYIPLFLIH | | 40102 |
| HPV16 | E5 | 65 | 11 | IFVYIPLFLIH | | 40103 |
| HPV16 | E5 | 51 | 8 | ITAASAFR | | 40104 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV16 | E5 | 61 | 8 | IVYIIFVY | | 40105 |
| HPV16 | E5 | 23 | 8 | LCVCLLIR | | 40106 |
| HPV16 | E5 | 71 | 9 | LFLIHTHAR | | 40107 |
| HPV16 | E5 | 22 | 9 | LLCVCLLIR | | 40108 |
| HPV16 | E5 | 32 | 8 | LLLSVSTY | | 40109 |
| HPV16 | E5 | 48 | 11 | LLWITAASAFR | | 40110 |
| HPV16 | E5 | 70 | 8 | PLFLIHTH | | 40111 |
| HPV16 | E5 | 70 | 10 | PLFLIHTHAR | | 40112 |
| HPV16 | E5 | 31 | 9 | PLLLSVSTY | | 40113 |
| HPV16 | E5 | 58 | 11 | RCFIVYIIFVY | | 40114 |
| HPV16 | E5 | 55 | 9 | SAFRCFIVY | | 40115 |
| HPV16 | E5 | 21 | 10 | VLLCVCLLIR | | 40116 |
| HPV16 | E5 | 50 | 9 | WITAASAFR | | 40117 |
| HPV16 | E5 | 68 | 8 | YIPLFLIH | | 40118 |
| HPV16 | E5 | 68 | 10 | YIPLFLIHTH | | 40119 |
| HPV16 | E6 | 53 | 9 | AFRDLCIVY | 0.0001 | 40120 |
| HPV16 | E6 | 53 | 10 | AFRDLCIVYR | | 40121 |
| HPV16 | E6 | 7 | 9 | AMFQDPQER | 0.0320 | 40122 |
| HPV16 | E6 | 7 | 11 | AMFQDPQERPR | | 40123 |
| HPV16 | E6 | 68 | 8 | AVCDKCLK | 0.0110 | 40124 |
| HPV16 | E6 | 68 | 10 | AVCDKCLKFY | 0.0190 | 40125 |
| HPV16 | E6 | 146 | 8 | CCRSSRTR | | 40126 |
| HPV16 | E6 | 146 | 9 | CCRSSRTRR | 0.0001 | 40127 |
| HPV16 | E6 | 70 | 8 | CDKCLKFY | | 40128 |
| HPV16 | E6 | 70 | 10 | CDKCLKFYSK | | 40129 |
| HPV16 | E6 | 58 | 10 | CIVYRDGNPY | 0.0004 | 40130 |
| HPV16 | E6 | 73 | 11 | CLKFYSKISEY | | 40131 |
| HPV16 | E6 | 143 | 9 | CMSCCRSSR | 0.0001 | 40132 |
| HPV16 | E6 | 143 | 11 | CMSCCRSSRTR | | 40133 |
| HPV16 | E6 | 23 | 9 | CTELQTTIH | 0.0001 | 40134 |
| HPV16 | E6 | 37 | 10 | CVYCKQQLLR | 0.0005 | 40135 |
| HPV16 | E6 | 37 | 11 | CVYCKQQLLRR | | 40136 |
| HPV16 | E6 | 51 | 11 | DFAFRDLCIVY | | 40137 |
| HPV16 | E6 | 63 | 10 | DGNPYAVCDK | | 40138 |
| HPV16 | E6 | 32 | 8 | DIILECVY | | 40139 |
| HPV16 | E6 | 32 | 10 | DIILECVYCK | 0.0210 | 40140 |
| HPV16 | E6 | 105 | 11 | DLLIRCINCQK | | 40141 |
| HPV16 | E6 | 36 | 11 | ECVYCKQQLLR | | 40142 |
| HPV16 | E6 | 48 | 8 | EVYDFAFR | 0.0025 | 40143 |
| HPV16 | E6 | 52 | 10 | FAFRDLCIVY | | 40144 |
| HPV16 | E6 | 52 | 11 | FAFRDLCIVYR | | 40145 |
| HPV16 | E6 | 64 | 9 | GNPYAVCDK | 0.0001 | 40146 |
| HPV16 | E6 | 92 | 8 | GTTLEQQY | | 40147 |
| HPV16 | E6 | 92 | 10 | GTTLEQQYNK | 0.0700 | 40148 |
| HPV16 | E6 | 31 | 9 | HDIILECVY | 0.0001 | 40149 |
| HPV16 | E6 | 31 | 11 | HDIILECVYCK | | 40150 |
| HPV16 | E6 | 125 | 9 | HLDKKQRFH | 0.0001 | 40151 |
| HPV16 | E6 | 133 | 10 | HNIRGRWTGR | | 40152 |
| HPV16 | E6 | 33 | 9 | IILECVYCK | 0.0190 | 40153 |
| HPV16 | E6 | 34 | 8 | ILECVYCK | | 40154 |
| HPV16 | E6 | 80 | 9 | ISEYRHYCY | 0.0150 | 40155 |
| HPV16 | E6 | 59 | 9 | IVYRDGNPY | 0.1500 | 40156 |
| HPV16 | E6 | 72 | 8 | KCLKFYSK | | 40157 |
| HPV16 | E6 | 75 | 9 | KFYSKISEY | 0.0002 | 40158 |
| HPV16 | E6 | 75 | 10 | KFYSKISEYR | 0.0002 | 40159 |
| HPV16 | E6 | 75 | 11 | KFYSKISEYRH | | 40160 |
| HPV16 | E6 | 79 | 8 | KISEYRHY | | 40161 |
| HPV16 | E6 | 79 | 10 | KISEYRHYCY | 0.0038 | 40162 |
| HPV16 | E6 | 57 | 11 | LCIVYRDGNPY | | 40163 |
| HPV16 | E6 | 117 | 8 | LCPEEKQR | | 40164 |
| HPV16 | E6 | 117 | 9 | LCPEEKQRH | 0.0001 | 40165 |
| HPV16 | E6 | 22 | 10 | LCTELQTTIH | | 40166 |
| HPV16 | E6 | 126 | 8 | LDKKQRFH | | 40167 |
| HPV16 | E6 | 126 | 11 | LDKKQRFHNIR | | 40168 |
| HPV16 | E6 | 107 | 9 | LIRCINCQK | 0.0009 | 40169 |
| HPV16 | E6 | 106 | 10 | LLIRCINCQK | 0.1800 | 40170 |
| HPV16 | E6 | 8 | 8 | MFQDPQER | | 40171 |
| HPV16 | E6 | 8 | 10 | MFQDPQERPR | | 40172 |
| HPV16 | E6 | 8 | 11 | MFQDPQERPRK | | 40173 |
| HPV16 | E6 | 144 | 8 | MSCCRSSR | | 40174 |
| HPV16 | E6 | 144 | 10 | MSCCRSSRTR | | 40175 |
| HPV16 | E6 | 144 | 11 | MSCCRSSRTRR | | 40176 |
| HPV16 | E6 | 112 | 11 | NCQKPLCPEEK | | 40177 |
| HPV16 | E6 | 134 | 9 | NIRGRWTGR | 0.0005 | 40178 |
| HPV16 | E6 | 102 | 8 | PLCDLLIR | | 40179 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV16 | E6 | 116 | 9 | PLCPEEKQR | 0.0005 | 40180 |
| HPV16 | E6 | 116 | 10 | PLCPEEKQRH | | 40181 |
| HPV16 | E6 | 10 | 8 | QDPQERPR | | 40182 |
| HPV16 | E6 | 10 | 9 | QDPQERPRK | | 40183 |
| HPV16 | E6 | 21 | 11 | QLCTELQTTIH | | 40184 |
| HPV16 | E6 | 43 | 8 | QLLRREVY | | 40185 |
| HPV16 | E6 | 142 | 10 | RCMSCCRSSR | | 40186 |
| HPV16 | E6 | 62 | 11 | RDGNPYAVCDK | | 40187 |
| HPV16 | E6 | 55 | 8 | RDLCIVYR | | 40188 |
| HPV16 | E6 | 131 | 8 | RFHNIRGR | | 41089 |
| HPV16 | E6 | 5 | 11 | RTAMFQDPQER | | 40190 |
| HPV16 | E6 | 145 | 9 | SCCRSSRTR | 0.0001 | 40191 |
| HPV16 | E6 | 145 | 10 | SCCRSSRTRR | | 40192 |
| HPV16 | E6 | 89 | 11 | SLYGTTLEQQY | | 40193 |
| HPV16 | E6 | 6 | 10 | TAMFQDPQER | | 40194 |
| HPV16 | E6 | 140 | 9 | TGRCMSCCR | 0.0001 | 40195 |
| HPV16 | E6 | 29 | 11 | TIHDIILECVY | | 40196 |
| HPV16 | E6 | 94 | 8 | TLEQQYNK | | 40197 |
| HPV16 | E6 | 93 | 9 | TTLEQQYNK | 0.2900 | 40198 |
| HPV16 | E6 | 69 | 9 | VCDKCLKFY | 0.0002 | 40199 |
| HPV16 | E6 | 69 | 11 | VCDKCLKFYSK | | 40200 |
| HPV16 | E6 | 139 | 10 | WTGRCMSCCR | 0.0008 | 40201 |
| HPV16 | E6 | 67 | 9 | YAVCDKCLK | 0.0010 | 40202 |
| HPV16 | E6 | 67 | 11 | YAVCDKCLKFY | | 40203 |
| HPV16 | E6 | 39 | 8 | YCKQQLLR | | 40204 |
| HPV16 | E6 | 39 | 9 | YCKQQLLRR | 0.0001 | 40205 |
| HPV16 | E6 | 91 | 9 | YGTTLEQQY | | 40206 |
| HPV16 | E6 | 91 | 11 | YGTTLEQQYNK | | 40207 |
| HPV16 | E6 | 99 | 11 | YNKPLCDLLIR | | 40208 |
| HPV16 | E6 | 77 | 8 | YSKISEYR | | 40209 |
| HPV16 | E6 | 77 | 9 | YSKISEYRH | | 40210 |
| HPV16 | E6 | 77 | 10 | YSKIESYRHY | 0.0001 | 40211 |
| HPV16 | E7 | 42 | 8 | AGQAEPDR | | 40212 |
| HPV16 | E7 | 42 | 10 | AGQAEPDRAH | | 40213 |
| HPV16 | E7 | 42 | 11 | AGQAEPDRAHY | | 40214 |
| HPV16 | E7 | 58 | 9 | CCKCDSTLR | 0.0001 | 40215 |
| HPV16 | E7 | 68 | 10 | CVQSTHVDIR | 0.0001 | 40216 |
| HPV16 | E7 | 39 | 11 | DGPAGQAEPDR | | 40217 |
| HPV16 | E7 | 14 | 10 | DLQPETTDLY | 0.0002 | 40218 |
| HPV16 | E7 | 4 | 8 | DTPTLHEY | | 40219 |
| HPV16 | E7 | 18 | 8 | ETTDLYCY | 0.0001 | 40220 |
| HPV16 | E7 | 57 | 10 | FCCKCDSTLR | | 40221 |
| HPV16 | E7 | 3 | 9 | GDTPTLHEY | | 40222 |
| HPV16 | E7 | 88 | 10 | GIVCPICSQK | 0.0670 | 40223 |
| HPV16 | E7 | 2 | 8 | HGDTPTLH | | 40224 |
| HPV16 | E7 | 2 | 10 | HGDTPTLHEY | 0.0001 | 40225 |
| HPV16 | E7 | 89 | 9 | IVCPICSQK | 0.0065 | 40226 |
| HPV16 | E7 | 67 | 11 | LCVQSTHVDIR | | 40227 |
| HPV16 | E7 | 13 | 11 | LDLQPETTDLY | | 40228 |
| HPV16 | E7 | 87 | 11 | LGIVCPICSQK | | 40229 |
| HPV16 | E7 | 53 | 8 | NIVTFCCK | | 40230 |
| HPV16 | E7 | 41 | 9 | PAGQAEPDR | | 40231 |
| HPV16 | E7 | 41 | 11 | PAGQAEPDRAH | | 40232 |
| HPV16 | E7 | 44 | 8 | QAEPDRAH | | 40233 |
| HPV16 | E7 | 44 | 9 | QAEPDRAHY | 0.0002 | 40234 |
| HPV16 | E7 | 70 | 8 | QSTHVDIR | | 40235 |
| HPV16 | E7 | 66 | 8 | RLCVQSTH | | 40236 |
| HPV16 | E7 | 63 | 11 | STLRLCVQSTH | | 40237 |
| HPV16 | E7 | 56 | 11 | TFCCKCDSTLR | | 40238 |
| HPV16 | E7 | 64 | 10 | TLRLCVQSTH | | 40239 |
| HPV16 | E7 | 90 | 8 | VCPICSQK | | 40240 |
| HPV16 | E7 | 52 | 9 | YNIVTFCCK | 0.0022 | 40241 |
| HPV16 | L1 | 372 | 10 | AAISTSETTY | | 40242 |
| HPV16 | L1 | 372 | 11 | AAISTSETTYK | | 40243 |
| HPV16 | L1 | 162 | 9 | AANAGVDNR | | 40244 |
| HPV16 | L1 | 453 | 11 | ACQKHTPPAPK | | 40245 |
| HPV16 | L1 | 127 | 9 | ACVGVEVGR | | 40246 |
| HPV16 | L1 | 483 | 10 | ADLDQFPLGR | | 40247 |
| HPV16 | L1 | 483 | 11 | ADLDQFPLGRK | | 40248 |
| HPV16 | L1 | 411 | 8 | ADVMTYIH | | 40249 |
| HPV16 | L1 | 498 | 8 | AGLKAKPK | | 40250 |
| HPV16 | L1 | 63 | 11 | AGTSRLLAVGH | | 40251 |
| HPV16 | L1 | 373 | 9 | AISTSETTY | | 40252 |
| HPV16 | L1 | 373 | 10 | AISTSETTYK | | 40253 |
| HPV16 | L1 | 233 | 11 | AMDFTTLQANK | | 40254 |

TABLE XVII-continued

A11 Motif Peptides

| Type | Protein | Position | No. of Amino Acids | Sequence | A*1101 | Seq. Id. No. |
|---|---|---|---|---|---|---|
| HPV16 | L1 | 163 | 8 | ANAGVDNR | | 40255 |
| HPV16 | L1 | 310 | 8 | ANLASSNY | | 40256 |
| HPV16 | L1 | 292 | 11 | AVGENVPDDLY | | 40257 |
| HPV16 | L1 | 70 | 10 | AVGHPYFPIK | | 40258 |
| HPV16 | L1 | 70 | 11 | AVGHPYFPIKK | | 40259 |
| HPV16 | L1 | 371 | 11 | CAAISTSETTY | | 40260 |
| HPV16 | L1 | 251 | 10 | CTSICKYPDY | | 40261 |
| HPV16 | L1 | 128 | 8 | CVGVEVGR | | 40262 |
| HPV16 | L1 | 329 | 9 | DAQIFNKPY | | 40263 |
| HPV16 | L1 | 153 | 9 | DDTENASAY | | 40264 |
| HPV16 | L1 | 235 | 9 | DFTTLQANK | | 40265 |
| HPV16 | L1 | 249 | 8 | DICTSICK | | 40266 |
| HPV16 | L1 | 249 | 9 | DICTSICKY | | 40267 |
| HPV16 | L1 | 484 | 9 | DLDQFPLGR | | 40268 |
| HPV16 | L1 | 484 | 10 | DLDQFPLGRK | | 40269 |
| HPV16 | L1 | 397 | 10 | DLQFIFQLCK | | 40270 |
| HPV16 | L1 | 168 | 10 | DNRECISMDY | | 40271 |
| HPV16 | L1 | 168 | 11 | DNRECISMDYK | | 40272 |
| HPV16 | L1 | 270 | 8 | DSLFFYLR | | 40273 |
| HPV16 | L1 | 270 | 9 | DSLFFYLRR | | 40274 |
| HPV16 | L1 | 154 | 8 | DTENASAY | | 40275 |
| HPV16 | L1 | 113 | 11 | DTSFYNPDTQR | | 40276 |
| HPV16 | L1 | 171 | 8 | ECISMDYK | | 40277 |
| HPV16 | L1 | 15 | 8 | ENDVNVYH | | 40278 |
| HPV16 | L1 | 295 | 8 | ENVPDDLY | | 40279 |
| HPV16 | L1 | 295 | 10 | ENVPDDLYIK | | 40280 |
| HPV16 | L1 | 378 | 10 | ETTYKNTNFK | | 40281 |
| HPV16 | L1 | 109 | 9 | FGFPDTSFY | | 40282 |
| HPV16 | L1 | 5 | 10 | FIYILVITCY | | 40283 |
| HPV16 | L1 | 494 | 8 | FLLQAGLK | | 40284 |
| HPV16 | L1 | 494 | 10 | FLLQAGLKAK | | 40285 |
| HPV16 | L1 | 333 | 9 | FNKPYWLQR | | 40286 |
| HPV16 | L1 | 236 | 8 | FTTLQANK | | 40287 |
| HPV16 | L1 | 282 | 8 | FVRHLFNR | | 40288 |
| HPV16 | L1 | 446 | 11 | FVTSQAIACQK | | 40289 |
| HPV16 | L1 | 356 | 9 | FVTVVDTTR | | 40290 |
| HPV16 | L1 | 186 | 9 | GCKPPIGEH | | 40291 |
| HPV16 | L1 | 269 | 9 | GDSLFFYLR | | 40292 |
| HPV16 | L1 | 269 | 10 | GDSLFFYLRR | | 40293 |
| HPV16 | L1 | 110 | 8 | GFPDTSFY | | 40294 |
| HPV16 | L1 | 437 | 8 | GGTLEDTY | | 40295 |
| HPV16 | L1 | 437 | 9 | GGTLEDTYR | | 40296 |
| HPV16 | L1 | 142 | 10 | GISGHPLLNK | | 40297 |
| HPV16 | L1 | 93 | 8 | GLQYRVFR | | 40298 |
| HPV16 | L1 | 93 | 10 | GLQYRVFRIH | | 40299 |
| HPV16 | L1 | 307 | 11 | GSTANLASSNY | | 40300 |
| HPV16 | L1 | 438 | 8 | GTLEDTYR | | 40301 |
| HPV16 | L1 | 64 | 10 | GTSRLLAVGH | | 40302 |
| HPV16 | L1 | 254 | 9 | ICKYPDYIK | | 40303 |
| HPV16 | L1 | 250 | 8 | ICTSICKY | | 40304 |
| HPV16 | L1 | 250 | 11 | ICTSICKYPDY | | 40305 |
| HPV16 | L1 | 332 | 10 | IFNKPYWLQR | | 40306 |
| HPV16 | L1 | 185 | 10 | IGCKPPIGEH | | 40307 |
| HPV16 | L1 | 86 | 11 | ILVPKVSGLQY | | 40308 |
| HPV16 | L1 | 143 | 9 | ISGHPLLNK | | 40309 |
| HPV16 | L1 | 374 | 8 | ISTSETTY | | 40310 |
| HPV16 | L1 | 374 | 9 | ISTSETTYK | | 40311 |
| HPV16 | L1 | 11 | 11 | ITCYENDVNVY | | 40312 |
| HPV16 | L1 | 407 | 10 | ITLTADVMTY | | 40313 |
| HPV16 | L1 | 501 | 10 | KAKPKFTLGK | | 40314 |
| HPV16 | L1 | 501 | 11 | KAKPKFTLGKR | | 40315 |
| HPV16 | L1 | 108 | 10 | KFGFPDTSFY | | 40316 |
| HPV16 | L1 | 493 | 9 | KFLLQAGLK | | 40317 |
| HPV16 | L1 | 493 | 11 | KFLLQAGLKAK | | 40318 |
| HPV16 | L1 | 505 | 8 | KFTLGKRK | | 40319 |
| HPV16 | L1 | 406 | 11 | KITLTADVMTY | | 40320 |
| HPV16 | L1 | 151 | 11 | KLDDTENASAY | | 40321 |
| HPV16 | L1 | 382 | 8 | KNTNFKEY | | 40322 |
| HPV16 | L1 | 382 | 10 | KNTNFKEYLR | | 40323 |
| HPV16 | L1 | 382 | 11 | KNTNFKEYLRH | | 40324 |
| HPV16 | L1 | 90 | 8 | KVSGLQYR | | 40325 |
| HPV16 | L1 | 90 | 11 | KVSGLQYRVFR | | 40326 |
| HPV16 | L1 | 46 | 8 | KVVSTDEY | | 40327 |
| HPV16 | L1 | 46 | 11 | KVVSTDEYVAR | | 40328 |
| HPV16 | L1 | 69 | 11 | LAVGHPYFPIK | | 40329 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV16 | L1 | 152 | 10 | LDDTENASAY | | 40330 |
| HPV16 | L1 | 248 | 9 | LDICTSICK | | 40331 |
| HPV16 | L1 | 248 | 10 | LDICTSICKY | | 40332 |
| HPV16 | L1 | 485 | 8 | LDQFPLGR | | 40333 |
| HPV16 | L1 | 485 | 9 | LDQFPLGRK | | 40334 |
| HPV16 | L1 | 355 | 10 | LFVTVVDTTR | | 40335 |
| HPV16 | L1 | 139 | 8 | LGVGISGH | | 40336 |
| HPV16 | L1 | 184 | 11 | LIGCKPPIGEH | | 40337 |
| HPV16 | L1 | 68 | 8 | LLAVGHPY | | 40338 |
| HPV16 | L1 | 495 | 9 | LLQAGLKAK | | 40339 |
| HPV16 | L1 | 495 | 11 | LLQAGLKAKPK | | 40340 |
| HPV16 | L1 | 409 | 8 | LTADVMTY | | 40341 |
| HPV16 | L1 | 409 | 10 | LTADVMTYIH | | 40342 |
| HPV16 | L1 | 87 | 10 | LVPKVSGLQY | | 40343 |
| HPV16 | L1 | 87 | 11 | LVPKVSGLQYR | | 40344 |
| HPV16 | L1 | 234 | 10 | MDFTTLQANK | | 40345 |
| HPV16 | L1 | 281 | 9 | MFVRHLFNR | | 40346 |
| HPV16 | L1 | 325 | 11 | MVTSDAQIFNK | | 40347 |
| HPV16 | L1 | 385 | 8 | NFKEYLRH | | 40348 |
| HPV16 | L1 | 58 | 10 | NIYYHAGTSR | | 40349 |
| HPV16 | L1 | 83 | 8 | NNKILVPK | | 40350 |
| HPV16 | L1 | 82 | 9 | NNNKILVPK | | 40351 |
| HPV16 | L1 | 383 | 9 | NTNFKEYLR | | 40352 |
| HPV16 | L1 | 383 | 10 | NTNFKEYLRH | | 40353 |
| HPV16 | L1 | 296 | 9 | NVPDDLYIK | | 40354 |
| HPV16 | L1 | 460 | 9 | PAPKEDPLK | | 40355 |
| HPV16 | L1 | 460 | 10 | PAPKEDPLKK | | 40356 |
| HPV16 | L1 | 460 | 11 | PAPKEDPLKKY | | 40357 |
| HPV16 | L1 | 258 | 11 | PDYIKMVSEPY | | 40358 |
| HPV16 | L1 | 436 | 9 | PGGTLEDTY | | 40359 |
| HPV16 | L1 | 436 | 10 | PGGTLEDTYR | | 40360 |
| HPV16 | L1 | 190 | 8 | PIGEHWGK | | 40361 |
| HPV16 | L1 | 77 | 9 | PIKKPNNNK | | 40362 |
| HPV16 | L1 | 247 | 10 | PLDICTSICK | | 40363 |
| HPV16 | L1 | 247 | 11 | PLDICTSICKY | | 40364 |
| HPV16 | L1 | 138 | 9 | PLGVGISGH | | 40365 |
| HPV16 | L1 | 81 | 10 | PNNNKILVPK | | 40366 |
| HPV16 | L1 | 515 | 11 | PTTSSTSTTAK | | 40367 |
| HPV16 | L1 | 43 | 11 | PVSKVVSTDEY | | 40368 |
| HPV16 | L1 | 497 | 9 | QAGLKAKPK | | 40369 |
| HPV16 | L1 | 450 | 8 | QAIACQKH | | 40370 |
| HPV16 | L1 | 399 | 8 | QFIFQLCK | | 40371 |
| HPV16 | L1 | 331 | 11 | QIFNKPYWLQR | | 40372 |
| HPV16 | L1 | 181 | 8 | QLCLIGCK | | 40373 |
| HPV16 | L1 | 354 | 11 | QLFVTVVDTTR | | 40374 |
| HPV16 | L1 | 280 | 10 | QMFVRHLFNR | | 40375 |
| HPV16 | L1 | 179 | 10 | QTQLCLIGCK | | 40376 |
| HPV16 | L1 | 100 | 9 | RIHLPDPNK | | 40377 |
| HPV16 | L1 | 67 | 9 | RLLAVGHPY | | 40378 |
| HPV16 | L1 | 482 | 11 | SADLDQFPLGR | | 40379 |
| HPV16 | L1 | 328 | 8 | SDAQIFNK | | 40380 |
| HPV16 | L1 | 328 | 10 | SDAQIFNKPY | | 40381 |
| HPV16 | L1 | 115 | 9 | SFYNPDTQR | | 40382 |
| HPV16 | L1 | 144 | 8 | SGHPLLNK | | 40383 |
| HPV16 | L1 | 92 | 9 | SGLQYRVFR | | 40384 |
| HPV16 | L1 | 92 | 11 | SGLQYRVFRIH | | 40385 |
| HPV16 | L1 | 253 | 8 | SICKYPDY | | 40386 |
| HPV16 | L1 | 253 | 10 | SICKYPDYIK | | 40387 |
| HPV16 | L1 | 271 | 8 | SLFFYLRR | | 40388 |
| HPV16 | L1 | 28 | 11 | SLWLPSEATVY | | 40389 |
| HPV16 | L1 | 518 | 8 | SSTSTTAK | | 40390 |
| HPV16 | L1 | 518 | 9 | SSTSTTAKR | | 40391 |
| HPV16 | L1 | 518 | 10 | SSTSTTAKRK | | 40392 |
| HPV16 | L1 | 518 | 11 | SSTSTTAKRKK | | 40393 |
| HPV16 | L1 | 308 | 10 | STANLASSNY | | 40394 |
| HPV16 | L1 | 49 | 8 | STDEYVAR | | 40395 |
| HPV16 | L1 | 375 | 8 | STSETTYK | | 40396 |
| HPV16 | L1 | 519 | 8 | STSTTAKR | | 40397 |
| HPV16 | L1 | 519 | 9 | STSTTAKRK | | 40398 |
| HPV16 | L1 | 519 | 10 | STSTTAKRKK | | 40399 |
| HPV16 | L1 | 519 | 11 | STSTTAKRKKR | | 40400 |
| HPV16 | L1 | 521 | 8 | STTAKRKK | | 40401 |
| HPV16 | L1 | 521 | 9 | STTAKRKKR | | 40402 |
| HPV16 | L1 | 521 | 10 | STTAKRKKRK | | 40403 |
| HPV16 | L1 | 410 | 9 | TADVMTYIH | | 40404 |

TABLE XVII-continued

A11 Motif Peptides

| Type | Protein | Position | No. of Amino Acids | Sequence | A*1101 | Seq. Id. No. |
|---|---|---|---|---|---|---|
| HPV16 | L1 | 523 | 8 | TAKRKKRK | | 40405 |
| HPV16 | L1 | 309 | 9 | TANLASSNY | | 40406 |
| HPV16 | L1 | 12 | 10 | TCYENDVNVY | | 40407 |
| HPV16 | L1 | 12 | 11 | TCYENDVNVYH | | 40408 |
| HPV16 | L1 | 50 | 11 | TDEYVARTNIY | | 40409 |
| HPV16 | L1 | 4 | 11 | TFIYILVITCY | | 40410 |
| HPV16 | L1 | 471 | 8 | TFWEVNLK | | 40411 |
| HPV16 | L1 | 471 | 10 | TFWEVNLKEK | | 40412 |
| HPV16 | L1 | 408 | 9 | TLTADVMTY | | 40413 |
| HPV16 | L1 | 408 | 11 | TLTADVMTYIH | | 40414 |
| HPV16 | L1 | 384 | 8 | TNFKEYLR | | 40415 |
| HPV16 | L1 | 384 | 9 | TNFKEYLRH | | 40416 |
| HPV16 | L1 | 57 | 11 | TNIYYHAGTSR | | 40417 |
| HPV16 | L1 | 327 | 9 | TSDAQIFNK | | 40418 |
| HPV16 | L1 | 327 | 11 | TSDAQIFNKPY | | 40419 |
| HPV16 | L1 | 114 | 10 | TSFYNPDTQR | | 40420 |
| HPV16 | L1 | 252 | 9 | TSICKYPDY | | 40421 |
| HPV16 | L1 | 252 | 11 | TSICKYPDYIK | | 40422 |
| HPV16 | L1 | 448 | 9 | TSQAIACQK | | 40423 |
| HPV16 | L1 | 448 | 10 | TSQAIACQKH | | 40424 |
| HPV16 | L1 | 65 | 9 | TSRLLAVGH | | 40425 |
| HPV16 | L1 | 65 | 11 | TSRLLAVGHPY | | 40426 |
| HPV16 | L1 | 517 | 9 | TSSTSTTAK | | 40427 |
| HPV16 | L1 | 517 | 10 | TSSTSTTAKR | | 40428 |
| HPV16 | L1 | 517 | 11 | TSSTSTTAKRK | | 40429 |
| HPV16 | L1 | 520 | 8 | TSTTAKRK | | 40430 |
| HPV16 | L1 | 520 | 9 | TSTTAKRKK | | 40431 |
| HPV16 | L1 | 520 | 10 | TSTTAKRKKR | | 40432 |
| HPV16 | L1 | 520 | 11 | TSTTAKRKKRK | | 40433 |
| HPV16 | L1 | 522 | 8 | TTAKRKKR | | 40434 |
| HPV16 | L1 | 522 | 9 | TTAKRKKRK | | 40435 |
| HPV16 | L1 | 516 | 10 | TTSSTSTTAK | | 40436 |
| HPV16 | L1 | 516 | 11 | TTSSTSTTAKR | | 40437 |
| HPV16 | L1 | 379 | 9 | TTYKNTNFK | | 40438 |
| HPV16 | L1 | 379 | 11 | TTYKNTNFKEY | | 40439 |
| HPV16 | L1 | 36 | 11 | TVYLPPVPVSK | | 40440 |
| HPV16 | L1 | 54 | 8 | VARTNIYY | | 40441 |
| HPV16 | L1 | 54 | 9 | VARTNIYYH | | 40442 |
| HPV16 | L1 | 167 | 11 | VDNRECISMDY | | 40443 |
| HPV16 | L1 | 98 | 11 | VFRIHLPDPNK | | 40444 |
| HPV16 | L1 | 293 | 10 | VGENVPDDLY | | 40445 |
| HPV16 | L1 | 71 | 9 | VGHPYFPIK | | 40446 |
| HPV16 | L1 | 71 | 10 | VGHPYFPIKK | | 40447 |
| HPV16 | L1 | 141 | 11 | VGISGHPLLNK | | 40448 |
| HPV16 | L1 | 91 | 10 | VSGLQYRVFR | | 40449 |
| HPV16 | L1 | 44 | 10 | VSKVVSTDEY | | 40450 |
| HPV16 | L1 | 48 | 9 | VSTDEYVAR | | 40451 |
| HPV16 | L1 | 326 | 10 | VTSDAQIFNK | | 40452 |
| HPV16 | L1 | 447 | 10 | VTSQAIACQK | | 40453 |
| HPV16 | L1 | 447 | 11 | VTSQAIACQKH | | 40454 |
| HPV16 | L1 | 357 | 8 | VTVVDTTR | | 40455 |
| HPV16 | L1 | 47 | 10 | VVSTDEYVAR | | 40456 |
| HPV16 | L1 | 126 | 10 | WACVGVEVGR | | 40457 |
| HPV16 | L1 | 30 | 9 | WLPSEATVY | | 40458 |
| HPV16 | L1 | 338 | 8 | WLQRAQGH | | 40459 |
| HPV16 | L1 | 161 | 10 | YAANAGVDNR | | 40460 |
| HPV16 | L1 | 396 | 11 | YDLQFIFQLCK | | 40461 |
| HPV16 | L1 | 75 | 11 | YFPIKKPNNNK | | 40462 |
| HPV16 | L1 | 268 | 8 | YGDSLFFY | | 40463 |
| HPV16 | L1 | 268 | 10 | YGDSLFFYLR | | 40464 |
| HPV16 | L1 | 268 | 11 | YGDSLFFYLRR | | 40465 |
| HPV16 | L1 | 260 | 9 | YIKMVSEPY | | 40466 |
| HPV16 | L1 | 7 | 8 | YILVITCY | | 40467 |
| HPV16 | L1 | 38 | 9 | YLPPVPVSK | | 40468 |
| HPV16 | L1 | 389 | 8 | YLRHGEEY | | 40469 |
| HPV16 | L1 | 275 | 10 | YLRREQMFVR | | 40470 |
| HPV16 | L1 | 275 | 11 | YLRREQMFVRH | | 40471 |
| HPV16 | L1 | 470 | 9 | YTFWEVNLK | | 40472 |
| HPV16 | L1 | 470 | 11 | YTFWEVNLKEK | | 40473 |
| HPV16 | L1 | 53 | 8 | YVARTNIY | | 40474 |
| HPV16 | L1 | 53 | 9 | YVARTNIYY | | 40475 |
| HPV16 | L1 | 53 | 10 | YVARTNIYYH | | 40476 |
| HPV16 | L2 | 441 | 9 | ADAGDFYLH | | 40477 |
| HPV16 | L2 | 241 | 8 | AFITTPTK | | 40478 |
| HPV16 | L2 | 443 | 10 | AGDFYLHPSY | | 40479 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV16 | L2 | 443 | 11 | AGDFYLHPSYY | | 40480 |
| HPV16 | L2 | 25 | 11 | AGTCPPDIIPK | | 40481 |
| HPV16 | L2 | 288 | 10 | ALHRPALTSR | | 40482 |
| HPV16 | L2 | 288 | 11 | ALHRPALTSRR | | 40483 |
| HPV16 | L2 | 356 | 11 | ALPTSINNGLY | | 40484 |
| HPV16 | L2 | 293 | 10 | ALTSRRTGIR | | 40485 |
| HPV16 | L2 | 293 | 11 | ALTSRRTGIRY | | 40486 |
| HPV16 | L2 | 396 | 11 | ANTTIPFGGAY | | 40487 |
| HPV16 | L2 | 13 | 8 | ASATQLYK | | 40488 |
| HPV16 | L2 | 13 | 11 | ASATQLYKTCK | | 40489 |
| HPV16 | L2 | 82 | 9 | ATDTLAPVR | | 40490 |
| HPV16 | L2 | 15 | 9 | ATQLYKTCK | | 40491 |
| HPV16 | L2 | 442 | 8 | DAGDFYLH | | 40492 |
| HPV16 | L2 | 442 | 11 | DAGDFYLHPSY | | 40493 |
| HPV16 | L2 | 282 | 9 | DFLDIVALH | | 40494 |
| HPV16 | L2 | 282 | 10 | DFLDIVALHR | | 40495 |
| HPV16 | L2 | 445 | 8 | DFYLHPSY | | 40496 |
| HPV16 | L2 | 445 | 9 | DFYLHPSYY | | 40497 |
| HPV16 | L2 | 31 | 9 | DIIPKVEGK | | 40498 |
| HPV16 | L2 | 258 | 10 | EGIDVDNTLY | | 40499 |
| HPV16 | L2 | 340 | 10 | ELQTITPSTY | | 40500 |
| HPV16 | L2 | 242 | 11 | FITTPTKLITY | | 40501 |
| HPV16 | L2 | 283 | 8 | FLDIVALH | | 40502 |
| HPV16 | L2 | 283 | 9 | FLDIVALHR | | 40503 |
| HPV16 | L2 | 181 | 11 | FTLSSSTISTH | | 40504 |
| HPV16 | L2 | 321 | 8 | GAKVHYYY | | 40505 |
| HPV16 | L2 | 444 | 9 | GDFYLHPSY | | 40506 |
| HPV16 | L2 | 444 | 10 | GDFYLHPSYY | | 40507 |
| HPV16 | L2 | 259 | 9 | GIDVDNTLY | | 40508 |
| HPV16 | L2 | 59 | 11 | GIGTGSGTGGR | | 40509 |
| HPV16 | L2 | 300 | 10 | GIRYSRIGNK | | 40510 |
| HPV16 | L2 | 226 | 11 | GLYSRTTQQVK | | 40511 |
| HPV16 | L2 | 307 | 9 | GNKQTLRTR | | 40512 |
| HPV16 | L2 | 63 | 10 | GSGTGGRTGY | | 40513 |
| HPV16 | L2 | 218 | 11 | GSRPVARLGLY | | 40514 |
| HPV16 | L2 | 26 | 10 | GTCPPDIIPK | | 40515 |
| HPV16 | L2 | 65 | 8 | GTGGRTGY | | 40516 |
| HPV16 | L2 | 61 | 9 | GTGSGTGGR | | 40517 |
| HPV16 | L2 | 440 | 8 | IADAGDFY | | 40518 |
| HPV16 | L2 | 440 | 10 | IADAGDFYLH | | 40519 |
| HPV16 | L2 | 41 | 8 | IADQILQY | | 40520 |
| HPV16 | L2 | 260 | 8 | IDVDNTLY | | 40521 |
| HPV16 | L2 | 320 | 8 | IGAKVHYY | | 40522 |
| HPV16 | L2 | 320 | 9 | IGAKVHYYY | | 40523 |
| HPV16 | L2 | 306 | 8 | IGNKQTLR | | 40524 |
| HPV16 | L2 | 306 | 10 | IGNKQTLRTR | | 40525 |
| HPV16 | L2 | 60 | 10 | IGTGSGTGGR | | 40526 |
| HPV16 | L2 | 439 | 9 | IIADAGDFY | | 40527 |
| HPV16 | L2 | 439 | 11 | IIADAGDFYLH | | 40528 |
| HPV16 | L2 | 32 | 8 | IIPKVEGK | | 40529 |
| HPV16 | L2 | 361 | 9 | INNGLYDIY | | 40530 |
| HPV16 | L2 | 148 | 11 | INNTVTTVTTH | | 40531 |
| HPV16 | L2 | 344 | 11 | ITPSTYTTTSH | | 40532 |
| HPV16 | L2 | 243 | 10 | ITTPTKLITY | | 40533 |
| HPV16 | L2 | 250 | 8 | ITYDNPAY | | 40534 |
| HPV16 | L2 | 430 | 8 | IVPGSPQY | | 40535 |
| HPV16 | L2 | 248 | 10 | KLITYDNPAY | | 40536 |
| HPV16 | L2 | 318 | 8 | KSIGAKVH | | 40537 |
| HPV16 | L2 | 318 | 9 | KSIGAKVHY | | 40538 |
| HPV16 | L2 | 318 | 10 | KSIGAKVHYY | | 40539 |
| HPV16 | L2 | 318 | 11 | KSIGAKVHYYY | | 40540 |
| HPV16 | L2 | 39 | 10 | KTIADQILQY | | 40541 |
| HPV16 | L2 | 284 | 8 | LDIVALHR | | 40542 |
| HPV16 | L2 | 427 | 11 | LIPIVPGSPQY | | 40543 |
| HPV16 | L2 | 249 | 9 | LITYDNPAY | | 40544 |
| HPV16 | L2 | 183 | 9 | LSSSTISTH | | 40545 |
| HPV16 | L2 | 183 | 11 | LSSSTISTHNY | | 40546 |
| HPV16 | L2 | 294 | 9 | LTSRRTGIR | | 40547 |
| HPV16 | L2 | 294 | 10 | LTSRRTGIRY | | 40548 |
| HPV16 | L2 | 454 | 8 | MLRKRRKR | | 40549 |
| HPV16 | L2 | 454 | 11 | MLRKRRKRLPY | | 40550 |
| HPV16 | L2 | 362 | 8 | NNGLYDIY | | 40551 |
| HPV16 | L2 | 149 | 10 | NNTVTTVTTH | | 40552 |
| HPV16 | L2 | 397 | 10 | NTTIPFGGAY | | 40553 |
| HPV16 | L2 | 150 | 9 | NTVTTVTTH | | 40554 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV16 | L2 | 240 | 9 | PAFITTPTK | | 40555 |
| HPV16 | L2 | 292 | 11 | PALTSRRTGIR | | 40556 |
| HPV16 | L2 | 281 | 10 | PDFLDIVALH | | 40557 |
| HPV16 | L2 | 281 | 11 | PDFLDIVALHR | | 40558 |
| HPV16 | L2 | 30 | 10 | PDIIPKVEGK | | 40559 |
| HPV16 | L2 | 217 | 8 | PGSRPVAR | | 40560 |
| HPV16 | L2 | 215 | 10 | PIPGSRPVAR | | 40561 |
| HPV16 | L2 | 429 | 9 | PIVPGSPQY | | 40562 |
| HPV16 | L2 | 386 | 8 | PSTSLSGY | | 40563 |
| HPV16 | L2 | 346 | 9 | PSTYTITSH | | 40564 |
| HPV16 | L2 | 383 | 11 | PSVPSTSLSGY | | 40565 |
| HPV16 | L2 | 450 | 8 | PSYYMLRK | | 40566 |
| HPV16 | L2 | 450 | 9 | PSYYMLRKR | | 40567 |
| HPV16 | L2 | 450 | 10 | PSYYMLRKRR | | 40568 |
| HPV16 | L2 | 450 | 11 | PSYYMLRKRRK | | 40569 |
| HPV16 | L2 | 80 | 11 | PTATDTLAPVR | | 40570 |
| HPV16 | L2 | 172 | 9 | PTPAETGGH | | 40571 |
| HPV16 | L2 | 358 | 9 | PTSINNGLY | | 40572 |
| HPV16 | L2 | 221 | 8 | PVARLGLY | | 40573 |
| HPV16 | L2 | 221 | 10 | PVARLGLYSR | | 40574 |
| HPV16 | L2 | 342 | 8 | QTITPSTY | | 40575 |
| HPV16 | L2 | 310 | 9 | QTLRTRSGK | | 40576 |
| HPV16 | L2 | 12 | 8 | RASATQLY | | 40577 |
| HPV16 | L2 | 12 | 9 | RASATQLYK | | 40578 |
| HPV16 | L2 | 305 | 9 | RIGNKQTLR | | 40579 |
| HPV16 | L2 | 305 | 11 | RIGNKQTLRTR | | 40580 |
| HPV16 | L2 | 5 | 8 | RSAKRTKR | | 40581 |
| HPV16 | L2 | 315 | 9 | RSGKSIGAK | | 40582 |
| HPV16 | L2 | 315 | 11 | RSGKSIGAKVH | | 40583 |
| HPV16 | L2 | 298 | 8 | RTGIRYSR | | 40584 |
| HPV16 | L2 | 69 | 10 | RTGYIPLGTR | | 40585 |
| HPV16 | L2 | 9 | 11 | RTKRASATQLY | | 40586 |
| HPV16 | L2 | 313 | 11 | RTRSGKSIGAK | | 40587 |
| HPV16 | L2 | 14 | 10 | SATQLYKTCK | | 40588 |
| HPV16 | L2 | 316 | 8 | SGKSIGAK | | 40589 |
| HPV16 | L2 | 316 | 10 | SGKSIGAKVH | | 40590 |
| HPV16 | L2 | 316 | 11 | SGKSIGAKVHY | | 40591 |
| HPV16 | L2 | 64 | 9 | SGTGGRTGY | | 40592 |
| HPV16 | L2 | 319 | 8 | SIGAKVHY | | 40593 |
| HPV16 | L2 | 319 | 9 | SIGAKVHYY | | 40594 |
| HPV16 | L2 | 319 | 10 | SIGAKVHYYY | | 40595 |
| HPV16 | L2 | 360 | 10 | SINNGLYDIY | | 40596 |
| HPV16 | L2 | 184 | 8 | SSSTISTH | | 40597 |
| HPV16 | L2 | 184 | 10 | SSSTISTHNY | | 40598 |
| HPV16 | L2 | 185 | 9 | SSTISTHNY | | 40599 |
| HPV16 | L2 | 212 | 9 | SSTPIPGSR | | 40600 |
| HPV16 | L2 | 186 | 8 | STISTHNY | | 40601 |
| HPV16 | L2 | 213 | 8 | STPIPGSR | | 40602 |
| HPV16 | L2 | 347 | 8 | STYTTTSH | | 40603 |
| HPV16 | L2 | 384 | 10 | SVPSTSLSGY | | 40604 |
| HPV16 | L2 | 81 | 10 | TATDTLAPVR | | 40605 |
| HPV16 | L2 | 27 | 9 | TCPPDIIPK | | 40606 |
| HPV16 | L2 | 83 | 8 | TDTLAPVR | | 40607 |
| HPV16 | L2 | 299 | 11 | TGIRYSRIGNK | | 40608 |
| HPV16 | L2 | 62 | 8 | TGSGTGGR | | 40609 |
| HPV16 | L2 | 62 | 11 | TGSGTGGRTGY | | 40610 |
| HPV16 | L2 | 70 | 9 | TGYIPLGTR | | 40611 |
| HPV16 | L2 | 40 | 9 | TIADQILQY | | 40612 |
| HPV16 | L2 | 438 | 10 | TIIADAGDFY | | 40613 |
| HPV16 | L2 | 399 | 8 | TIPFGGAY | | 40614 |
| HPV16 | L2 | 311 | 8 | TLRTRSGK | | 40615 |
| HPV16 | L2 | 182 | 10 | TLSSSTISTH | | 40616 |
| HPV16 | L2 | 359 | 8 | TSINNGLY | | 40617 |
| HPV16 | L2 | 359 | 11 | TSINNGLYDIY | | 40618 |
| HPV16 | L2 | 295 | 8 | TSRRTGIR | | 40619 |
| HPV16 | L2 | 295 | 9 | TSRRTGIRY | | 40620 |
| HPV16 | L2 | 295 | 11 | TSRRTGIRYSR | | 40621 |
| HPV16 | L2 | 211 | 10 | TSSTPIPGSR | | 40622 |
| HPV16 | L2 | 398 | 9 | TTIPFGGAY | | 40623 |
| HPV16 | L2 | 244 | 9 | TTPTKLITY | | 40624 |
| HPV16 | L2 | 151 | 8 | TVTTVTTH | | 40625 |
| HPV16 | L2 | 287 | 11 | VALHRPALTSR | | 40626 |
| HPV16 | L2 | 222 | 9 | VARLGLYSR | | 40627 |
| HPV16 | L2 | 238 | 11 | VDPAFITTPTK | | 40628 |
| HPV16 | L2 | 210 | 11 | VTSSTPIPGSR | | 40629 |

TABLE XVII-continued

A11 Motif Peptides

| Type | Protein | Position | No. of Amino Acids | Sequence | A*1101 | Seq. Id. No. |
|---|---|---|---|---|---|---|
| HPV16 | L2 | 447 | 10 | YLHPSYYMLR | | 40630 |
| HPV16 | L2 | 447 | 11 | YLHPSYYMLRK | | 40631 |
| HPV16 | L2 | 453 | 8 | YMLRKRRK | | 40632 |
| HPV16 | L2 | 453 | 9 | YMLRKRRKR | | 40633 |
| HPV16 | L2 | 303 | 11 | YSRIGNKQTLR | | 40634 |
| HPV16 | L2 | 228 | 9 | YSRTTQQVK | | 40635 |
| HPV16 | L2 | 437 | 11 | YTIIADAGDFY | | 40636 |
| HPV18 | E1 | 397 | 11 | AAFLKSNCQAK | | 40637 |
| HPV18 | E1 | 398 | 10 | AFLKSNCQAK | | 40638 |
| HPV18 | E1 | 398 | 11 | AFLKSNCQAKY | | 40639 |
| HPV18 | E1 | 546 | 11 | ALDGNPISIDR | | 40640 |
| HPV18 | E1 | 68 | 9 | ALFHAQEVH | | 40641 |
| HPV18 | E1 | 466 | 11 | ALKSFLKGTPK | | 40642 |
| HPV18 | E1 | 284 | 9 | ALLRYKCGK | 0.1400 | 40643 |
| HPV18 | E1 | 284 | 11 | ALLRYKCGKSR | | 40644 |
| HPV18 | E1 | 213 | 10 | AMLAVFKDTY | | 40645 |
| HPV18 | E1 | 413 | 8 | ATMCKHYR | | 40646 |
| HPV18 | E1 | 413 | 9 | ATMCKHYRR | 0.2800 | 40647 |
| HPV18 | E1 | 531 | 8 | ATTTCWTY | | 40648 |
| HPV18 | E1 | 504 | 11 | AVISFVNSTSH | | 40649 |
| HPV18 | E1 | 412 | 8 | CATMCKHY | | 40650 |
| HPV18 | E1 | 412 | 9 | CATMCKHYR | 0.0110 | 40651 |
| HPV18 | E1 | 412 | 10 | CATMCKHYRR | | 40652 |
| HPV18 | E1 | 618 | 9 | CFFERTWSR | | 40653 |
| HPV18 | E1 | 290 | 10 | CGKSRLTVAK | | 40654 |
| HPV18 | E1 | 483 | 8 | CGPANTGK | | 40655 |
| HPV18 | E1 | 483 | 10 | CGPANTGKSY | | 40656 |
| HPV18 | E1 | 311 | 8 | CMLIQPPK | | 40657 |
| HPV18 | E1 | 311 | 10 | CMLIQPPKLR | | 40658 |
| HPV18 | E1 | 437 | 11 | CSKIDEGGDWR | | 40659 |
| HPV18 | E1 | 196 | 11 | CTIAQLKDLLK | | 40660 |
| HPV18 | E1 | 78 | 9 | DAQVLHVLK | | 40661 |
| HPV18 | E1 | 78 | 10 | DAQVLHVLKR | | 40662 |
| HPV18 | E1 | 78 | 11 | DAQVLHVLKRK | | 40663 |
| HPV18 | E1 | 530 | 9 | DATTTCWTY | | 40664 |
| HPV18 | E1 | 411 | 8 | DCATMCKH | | 40665 |
| HPV18 | E1 | 411 | 9 | DCATMCKHY | | 40666 |
| HPV18 | E1 | 411 | 10 | DCATMCKHYR | | 40667 |
| HPV18 | E1 | 411 | 11 | DCATMCKHYRR | | 40668 |
| HPV18 | E1 | 529 | 10 | DDATTTCWTY | | 40669 |
| HPV18 | E1 | 548 | 9 | DGNPISIDR | | 40670 |
| HPV18 | E1 | 548 | 10 | DGNPISIDRK | | 40671 |
| HPV18 | E1 | 548 | 11 | DGNPISIDRKH | | 40672 |
| HPV18 | E1 | 203 | 8 | DLLKVNNK | | 40673 |
| HPV18 | E1 | 228 | 10 | DLVRNFKSDK | | 40674 |
| HPV18 | E1 | 580 | 10 | DNRWPYLESR | | 40675 |
| HPV18 | E1 | 391 | 11 | DSNSNAAAFLK | | 40676 |
| HPV18 | E1 | 637 | 11 | DTEGNPFGTFK | | 40677 |
| HPV18 | E1 | 342 | 8 | DTPEWIQR | | 40678 |
| HPV18 | E1 | 459 | 10 | EFITFLGALK | | 40679 |
| HPV18 | E1 | 594 | 10 | EFPNAFPFDK | | 40680 |
| HPV18 | E1 | 639 | 9 | EGNPFGTFK | | 40681 |
| HPV18 | E1 | 639 | 11 | EGNPFGTFKLR | | 40682 |
| HPV18 | E1 | 10 | 10 | EGTGCNGWFY | 0.0002 | 40683 |
| HPV18 | E1 | 610 | 8 | EINDKNWK | | 40684 |
| HPV18 | E1 | 115 | 9 | EISLNSGQK | | 40685 |
| HPV18 | E1 | 115 | 10 | EISLNSGQKK | | 40686 |
| HPV18 | E1 | 62 | 10 | ELETAQALFH | | 40687 |
| HPV18 | E1 | 95 | 8 | ENSPLGER | | 40688 |
| HPV18 | E1 | 379 | 8 | ESDMAFEY | | 40689 |
| HPV18 | E1 | 64 | 8 | ETAQALFH | | 40690 |
| HPV18 | E1 | 309 | 10 | ETCMLIQPPK | | 40691 |
| HPV18 | E1 | 104 | 9 | EVDTELSPR | | 40692 |
| HPV18 | E1 | 74 | 10 | EVHNDAQVLH | | 40693 |
| HPV18 | E1 | 482 | 9 | FCGPANTGK | | 40694 |
| HPV18 | E1 | 482 | 11 | FCGPANTGKSY | | 40695 |
| HPV18 | E1 | 601 | 9 | FDKNGNPVY | | 40696 |
| HPV18 | E1 | 619 | 8 | FFERTWSR | | 40697 |
| HPV18 | E1 | 460 | 9 | FITFLGALK | 0.0370 | 40698 |
| HPV18 | E1 | 463 | 10 | FLGALKSFLK | | 40699 |
| HPV18 | E1 | 470 | 8 | FLKGTPKK | | 40700 |
| HPV18 | E1 | 399 | 9 | FLKSNCQAK | 0.0007 | 40701 |
| HPV18 | E1 | 399 | 10 | FLKSNCQAKY | | 40702 |
| HPV18 | E1 | 226 | 9 | FTDLVRNFK | | 40703 |
| HPV18 | E1 | 130 | 8 | FTISDSGY | | 40704 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | E1 | 465 | 8 | GALKSFLK | | 40705 |
| HPV18 | E1 | 212 | 8 | GAMLAVFK | | 40706 |
| HPV18 | E1 | 212 | 11 | GAMLAVFKDTY | | 40707 |
| HPV18 | E1 | 341 | 9 | GDTPEWIQR | 0.0002 | 40708 |
| HPV18 | E1 | 444 | 11 | GDWRPIVQFLR | | 40709 |
| HPV18 | E1 | 223 | 9 | GLSFTDLVR | 0.0025 | 40710 |
| HPV18 | E1 | 640 | 8 | GNPFGTFK | | 40711 |
| HPV18 | E1 | 640 | 10 | GNPFGTFKLR | | 40712 |
| HPV18 | E1 | 549 | 8 | GNPISIDR | | 40713 |
| HPV18 | E1 | 549 | 9 | GNPISIDRK | | 40714 |
| HPV18 | E1 | 549 | 10 | GNPISIDRKH | | 40715 |
| HPV18 | E1 | 549 | 11 | GNPISIDRKHK | | 40716 |
| HPV18 | E1 | 605 | 10 | GNPVYEINDK | | 40717 |
| HPV18 | E1 | 92 | 11 | GSTENSPLGER | | 40718 |
| HPV18 | E1 | 644 | 11 | GTFKLRAGQNH | | 40719 |
| HPV18 | E1 | 11 | 9 | GTGCNGWFY | 0.0720 | 40720 |
| HPV18 | E1 | 279 | 9 | GVLILALLR | 0.1400 | 40721 |
| HPV18 | E1 | 279 | 10 | GVLILALLRY | | 40722 |
| HPV18 | E1 | 279 | 11 | GVLILALLRYK | | 40723 |
| HPV18 | E1 | 249 | 11 | GVNPTIAEGFK | | 40724 |
| HPV18 | E1 | 514 | 11 | HFWLEPLTDTK | | 40725 |
| HPV18 | E1 | 270 | 8 | HIQCLDCK | | 40726 |
| HPV18 | E1 | 76 | 8 | HNDAQVLH | | 40727 |
| HPV18 | E1 | 76 | 11 | HNDAQVLHVLK | | 40728 |
| HPV18 | E1 | 198 | 9 | IAQLKDLLK | 0.0027 | 40729 |
| HPV18 | E1 | 440 | 8 | IDEGGDWR | | 40730 |
| HPV18 | E1 | 282 | 8 | ILALLRYK | | 40731 |
| HPV18 | E1 | 282 | 11 | ILALLRYKCGK | | 40732 |
| HPV18 | E1 | 569 | 8 | ILLTTNIH | | 40733 |
| HPV18 | E1 | 569 | 11 | ILLTTNIHPAK | | 40734 |
| HPV18 | E1 | 506 | 9 | ISFVNSTSH | | 40735 |
| HPV18 | E1 | 552 | 8 | ISIDRKHK | | 40736 |
| HPV18 | E1 | 116 | 8 | ISLNSGQK | | 40737 |
| HPV18 | E1 | 116 | 9 | ISLNSGQKK | 0.0026 | 40738 |
| HPV18 | E1 | 116 | 11 | ISLNSGQKKAK | | 40739 |
| HPV18 | E1 | 461 | 8 | ITFLGALK | | 40740 |
| HPV18 | E1 | 617 | 10 | KCFFERTWSR | | 40741 |
| HPV18 | E1 | 289 | 11 | KCGKSRLTVAK | | 40742 |
| HPV18 | E1 | 410 | 8 | KDCATMCK | | 40743 |
| HPV18 | E1 | 410 | 9 | KDCATMCKH | | 40744 |
| HPV18 | E1 | 410 | 10 | KDCATMCKHY | | 40745 |
| HPV18 | E1 | 410 | 11 | KDCATMCKHYR | | 40746 |
| HPV18 | E1 | 202 | 9 | KDLLKVNNK | | 40747 |
| HPV18 | E1 | 579 | 11 | KDNRWPYLESR | | 40748 |
| HPV18 | E1 | 299 | 8 | KGLSTLLH | | 40749 |
| HPV18 | E1 | 439 | 9 | KIDEGGDWR | | 40750 |
| HPV18 | E1 | 647 | 8 | KLRAGQNH | | 40751 |
| HPV18 | E1 | 647 | 9 | KLRAGQNHR | 0.0013 | 40752 |
| HPV18 | E1 | 318 | 10 | KLRSSVAALY | | 40753 |
| HPV18 | E1 | 614 | 9 | KNWKCFFER | | 40754 |
| HPV18 | E1 | 468 | 9 | KSFLKGTPK | 0.0015 | 40755 |
| HPV18 | E1 | 468 | 10 | KSFLKGTPKK | | 40756 |
| HPV18 | E1 | 401 | 8 | KSNCQAKY | | 40757 |
| HPV18 | E1 | 401 | 10 | KSNCQAKYLK | | 40758 |
| HPV18 | E1 | 292 | 8 | KSRLTVAK | | 40759 |
| HPV18 | E1 | 490 | 10 | KSYFGMSFIH | | 40760 |
| HPV18 | E1 | 259 | 10 | KTLIQPFILY | | 40761 |
| HPV18 | E1 | 283 | 10 | LALLRYKCGK | | 40762 |
| HPV18 | E1 | 215 | 8 | LAVFKDTY | | 40763 |
| HPV18 | E1 | 528 | 11 | LDDATTTCWTY | | 40764 |
| HPV18 | E1 | 547 | 10 | LDGNPISIDR | | 40765 |
| HPV18 | E1 | 547 | 11 | LDGNPISIDRK | | 40766 |
| HPV18 | E1 | 69 | 8 | LFHAQEVH | | 40767 |
| HPV18 | E1 | 129 | 9 | LFTISDSGY | | 40768 |
| HPV18 | E1 | 464 | 9 | LGALKSFLK | | 40769 |
| HPV18 | E1 | 281 | 8 | LILALLRY | | 40770 |
| HPV18 | E1 | 281 | 9 | LILALLRYK | 0.1800 | 40771 |
| HPV18 | E1 | 261 | 8 | LIQPFILY | | 40772 |
| HPV18 | E1 | 261 | 10 | LIQPFILYAH | | 40773 |
| HPV18 | E1 | 313 | 8 | LIQPPKLR | | 40774 |
| HPV18 | E1 | 285 | 8 | LLRYKCGK | | 40775 |
| HPV18 | E1 | 285 | 10 | LLRYKCGKSR | | 40776 |
| HPV18 | E1 | 570 | 10 | LLTTNIHPAK | | 40777 |
| HPV18 | E1 | 118 | 9 | LNSGQKKAK | | 40778 |
| HPV18 | E1 | 118 | 10 | LNSGQKKAKR | | 40779 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | E1 | 118 | 11 | LSNGQKKAKRR | | 40780 |
| HPV18 | E1 | 224 | 8 | LSFTDLVR | | 40781 |
| HPV18 | E1 | 224 | 11 | LSFTDLVRNFK | | 40782 |
| HPV18 | E1 | 376 | 11 | LTDESDMAFEY | | 40783 |
| HPV18 | E1 | 571 | 9 | LTTNIHPAK | 0.1200 | 40784 |
| HPV18 | E1 | 480 | 11 | LVFCGPANTGK | | 40785 |
| HPV18 | E1 | 229 | 9 | LVRNFKSDK | 0.0002 | 40786 |
| HPV18 | E1 | 415 | 10 | MCKHYRRAQK | | 40787 |
| HPV18 | E1 | 415 | 11 | MCKHYRRAQKR | | 40788 |
| HPV18 | E1 | 340 | 10 | MGDTPEWIQR | | 40789 |
| HPV18 | E1 | 214 | 9 | MLAVFKDTY | | 40790 |
| HPV18 | E1 | 312 | 9 | MLIQPPKLR | 0.0014 | 40791 |
| HPV18 | E1 | 427 | 8 | MNMSQWIR | | 40792 |
| HPV18 | E1 | 427 | 10 | MNMSQWIRFR | | 40793 |
| HPV18 | E1 | 429 | 8 | MSQWIRFR | | 40794 |
| HPV18 | E1 | 429 | 11 | MSQWIRFRCSK | | 40795 |
| HPV18 | E1 | 403 | 8 | NCQAKYLK | | 40796 |
| HPV18 | E1 | 77 | 10 | NDAQVLHVLK | | 40797 |
| HPV18 | E1 | 77 | 11 | NDAQVLHVLKR | | 40798 |
| HPV18 | E1 | 612 | 11 | NDKNWKCFFER | | 40799 |
| HPV18 | E1 | 604 | 11 | NGNPVYEINDK | | 40800 |
| HPV18 | E1 | 574 | 9 | NIHPAKDNR | 0.0002 | 40801 |
| HPV18 | E1 | 428 | 9 | NMSQWIRFR | 0.0012 | 40802 |
| HPV18 | E1 | 119 | 8 | NSGQKKAK | | 40803 |
| HPV18 | E1 | 119 | 9 | NSGQKKAKR | 0.0002 | 40804 |
| HPV18 | E1 | 119 | 10 | NSGQKKAKRR | | 40805 |
| HPV18 | E1 | 393 | 9 | NSNAAAFLK | 0.3700 | 40806 |
| HPV18 | E1 | 577 | 9 | PAKDNRWPY | | 40807 |
| HPV18 | E1 | 485 | 8 | PANTGKSY | | 40808 |
| HPV18 | E1 | 600 | 10 | PFDKNGNPVY | | 40809 |
| HPV18 | E1 | 642 | 8 | PFGTFKLR | | 40810 |
| HPV18 | E1 | 568 | 9 | PILLTTNIH | | 40811 |
| HPV18 | E1 | 551 | 8 | PISIDRKH | | 40812 |
| HPV18 | E1 | 551 | 9 | PISIDRKHK | | 40813 |
| HPV18 | E1 | 448 | 8 | PIVQFLRY | | 40814 |
| HPV18 | E1 | 596 | 8 | PNAFPFDK | | 40815 |
| HPV18 | E1 | 252 | 8 | PTIAEGFK | | 40816 |
| HPV18 | E1 | 607 | 8 | PVYEINDK | | 40817 |
| HPV18 | E1 | 607 | 11 | PVYEINDKNWK | | 40818 |
| HPV18 | E1 | 67 | 10 | QALFHAQEVH | | 40819 |
| HPV18 | E1 | 195 | 8 | QCTIAQLK | | 40820 |
| HPV18 | E1 | 211 | 9 | QGAMLAVFK | | 40821 |
| HPV18 | E1 | 146 | 10 | QIQVTTNGEH | | 40822 |
| HPV18 | E1 | 200 | 11 | QLKDLLKVNNK | | 40823 |
| HPV18 | E1 | 426 | 9 | QMNMSQWIR | 0.0023 | 40824 |
| HPV18 | E1 | 426 | 11 | QMNMSQWIRFR | | 40825 |
| HPV18 | E1 | 80 | 8 | QVLHVLKR | | 40826 |
| HPV18 | E1 | 80 | 9 | QVLHVLKRK | 0.0020 | 40827 |
| HPV18 | E1 | 148 | 8 | QVTTNGEH | | 40828 |
| HPV18 | E1 | 102 | 11 | RLEVDTELSPR | | 40829 |
| HPV18 | E1 | 128 | 10 | RLFTISDSGY | | 40830 |
| HPV18 | E1 | 320 | 8 | RSSVAALY | | 40831 |
| HPV18 | E1 | 320 | 10 | RSSVAALYWY | | 40832 |
| HPV18 | E1 | 320 | 11 | RSSVAALYWYR | | 40833 |
| HPV18 | E1 | 622 | 9 | RTWSRLDLH | | 40834 |
| HPV18 | E1 | 469 | 8 | SFLKGTPK | | 40835 |
| HPV18 | E1 | 469 | 9 | SFLKGTPKK | | 40836 |
| HPV18 | E1 | 225 | 10 | SFTDLVRNFK | | 40837 |
| HPV18 | E1 | 507 | 8 | SFVNSTSH | | 40838 |
| HPV18 | E1 | 120 | 8 | SGQKKAKR | | 40839 |
| HPV18 | E1 | 120 | 9 | SGQKKAKRR | | 40840 |
| HPV18 | E1 | 117 | 8 | SLNSGQKK | | 40841 |
| HPV18 | E1 | 117 | 10 | SLNSGQKKAK | | 40842 |
| HPV18 | E1 | 117 | 11 | SLNSGQKKAKR | | 40843 |
| HPV18 | E1 | 394 | 8 | SNAAAFLK | | 40844 |
| HPV18 | E1 | 402 | 9 | SNCQAKYLK | | 40845 |
| HPV18 | E1 | 392 | 10 | SNSNAAAFLK | | 40846 |
| HPV18 | E1 | 321 | 9 | SSVAALYWY | | 40847 |
| HPV18 | E1 | 321 | 10 | SSVAALYWYR | | 40848 |
| HPV18 | E1 | 93 | 10 | STENSPLGER | | 40849 |
| HPV18 | E1 | 322 | 8 | SVAALYWY | | 40850 |
| HPV18 | E1 | 322 | 9 | SVAALYWYR | 8.8000 | 40851 |
| HPV18 | E1 | 310 | 9 | TCMLIQPPK | | 40852 |
| HPV18 | E1 | 310 | 11 | TCMLIQPPKLR | | 40853 |
| HPV18 | E1 | 534 | 9 | TCWTYFDTY | | 40854 |

TABLE XVII-continued

A11 Motif Peptides

| Type | Protein | Position | No. of Amino Acids | Sequence | A*1101 | Seq. Id. No. |
|---|---|---|---|---|---|---|
| HPV18 | E1 | 534 | 11 | TCWTYFDTYMR | | 40855 |
| HPV18 | E1 | 377 | 10 | TDESDMAFEY | | 40856 |
| HPV18 | E1 | 227 | 8 | TDLVRNFK | | 40857 |
| HPV18 | E1 | 227 | 11 | TDLVRNFKSDK | | 40858 |
| HPV18 | E1 | 645 | 10 | TFKLRAGQNH | | 40859 |
| HPV18 | E1 | 645 | 11 | TFKLRAGQNHR | | 40860 |
| HPV18 | E1 | 462 | 11 | TFLGALKSFLK | | 40861 |
| HPV18 | E1 | 12 | 8 | TGCNGWFY | | 40862 |
| HPV18 | E1 | 197 | 10 | TIAQLKDLLK | | 40863 |
| HPV18 | E1 | 260 | 9 | TLIQPFILY | | 40864 |
| HPV18 | E1 | 260 | 11 | TLIQPFILYAH | | 40865 |
| HPV18 | E1 | 414 | 8 | TMCKHYRR | | 40866 |
| HPV18 | E1 | 414 | 11 | TMCKHYRRAQK | | 40867 |
| HPV18 | E1 | 573 | 10 | TNIHPAKDNR | | 40868 |
| HPV18 | E1 | 533 | 10 | TTCWTYFDTY | | 40869 |
| HPV18 | E1 | 572 | 8 | TTNIHPAK | | 40870 |
| HPV18 | E1 | 572 | 11 | TTNIHPAKDNR | | 40871 |
| HPV18 | E1 | 532 | 11 | TTTCWTYFDTY | | 40872 |
| HPV18 | E1 | 296 | 11 | TVAKGLSTLLH | | 40873 |
| HPV18 | E1 | 323 | 8 | VAALYWYR | | 40874 |
| HPV18 | E1 | 297 | 10 | VAKGLSTLLH | | 40875 |
| HPV18 | E1 | 105 | 8 | VDTELSPR | | 40876 |
| HPV18 | E1 | 481 | 10 | VFCGPANTGK | | 40877 |
| HPV18 | E1 | 505 | 10 | VISFVNSTSH | | 40878 |
| HPV18 | E1 | 81 | 8 | VLHVLKRK | | 40879 |
| HPV18 | E1 | 280 | 8 | VLILALLR | | 40880 |
| HPV18 | E1 | 280 | 9 | VLILALLRY | | 40881 |
| HPV18 | E1 | 280 | 10 | VLILALLRYK | | 40882 |
| HPV18 | E1 | 339 | 11 | VMGDTPEWIQR | | 40883 |
| HPV18 | E1 | 192 | 11 | VNPQCTIAQLK | | 40884 |
| HPV18 | E1 | 250 | 10 | VNPTIAEGFK | | 40885 |
| HPV18 | E1 | 17 | 10 | WFYVQAIVDK | | 40886 |
| HPV18 | E1 | 17 | 11 | WFYVQAIVDKK | | 40887 |
| HPV18 | E1 | 278 | 10 | WGVLILALLR | | 40888 |
| HPV18 | E1 | 278 | 11 | WGVLILALLRY | | 40889 |
| HPV18 | E1 | 346 | 10 | WIQRLTIIQH | | 40890 |
| HPV18 | E1 | 432 | 8 | WIRFRCSK | | 40891 |
| HPV18 | E1 | 516 | 9 | WLEPLTDTK | | 40892 |
| HPV18 | E1 | 536 | 9 | WTYFDTYMR | 0.0120 | 40893 |
| HPV18 | E1 | 268 | 10 | YAHIQCLDCK | | 40894 |
| HPV18 | E1 | 492 | 8 | YFGMSFIH | | 40895 |
| HPV18 | E1 | 222 | 10 | YGLSFTDLVR | | 40896 |
| HPV18 | E1 | 408 | 10 | YLKDCATMCK | | 40897 |
| HPV18 | E1 | 408 | 11 | YLKDCATMCKH | | 40898 |
| HPV18 | E1 | 19 | 8 | YVQAIVDK | | 40899 |
| HPV18 | E1 | 19 | 9 | YVQAIVDKK | 0.0290 | 40900 |
| HPV18 | E2 | 269 | 9 | AATPTGNNK | | 40901 |
| HPV18 | E2 | 269 | 10 | AATPTGNNKR | | 40902 |
| HPV18 | E2 | 269 | 11 | AATPTGNNKRR | | 40903 |
| HPV18 | E2 | 45 | 9 | AIFFAAREH | | 40904 |
| HPV18 | E2 | 82 | 9 | ALQGLAQSR | | 40905 |
| HPV18 | E2 | 82 | 10 | ALQGLAQSRY | | 40906 |
| HPV18 | E2 | 82 | 11 | ALQGLAQSRYK | | 40907 |
| HPV18 | E2 | 154 | 10 | ATCVSHRGLY | | 40908 |
| HPV18 | E2 | 154 | 11 | ATCVSHRGLYY | | 40909 |
| HPV18 | E2 | 270 | 8 | ATPTGNNK | | 40910 |
| HPV18 | E2 | 270 | 9 | ATPTGNNKR | | 40911 |
| HPV18 | E2 | 270 | 10 | ATPTGNNKRR | | 40912 |
| HPV18 | E2 | 270 | 11 | ATPTGNNKRRK | | 40913 |
| HPV18 | E2 | 214 | 10 | ATQLVKQLQH | | 40914 |
| HPV18 | E2 | 252 | 8 | CGLAEKQH | | 40915 |
| HPV18 | E2 | 301 | 8 | CLRYRLRK | | 40916 |
| HPV18 | E2 | 301 | 9 | CLRYRLRKH | | 40917 |
| HPV18 | E2 | 132 | 11 | CMTYVAWDSVY | | 40918 |
| HPV18 | E2 | 282 | 10 | CSGNTTPIIH | | 40919 |
| HPV18 | E2 | 14 | 9 | CVQDKIIDH | | 40920 |
| HPV18 | E2 | 14 | 10 | CVQDKIIDHY | | 40921 |
| HPV18 | E2 | 156 | 8 | CVSHRGLY | | 40922 |
| HPV18 | E2 | 156 | 9 | CVSHRGLYY | | 40923 |
| HPV18 | E2 | 156 | 11 | CVSHRGLYYVK | | 40924 |
| HPV18 | E2 | 209 | 11 | DDTVSATQLVK | | 40925 |
| HPV18 | E2 | 126 | 10 | DGNKDNCMTY | | 40926 |
| HPV18 | E2 | 29 | 8 | DIDSQIQY | | 40927 |
| HPV18 | E2 | 26 | 11 | DSKDIDSQIQY | | 40928 |
| HPV18 | E2 | 31 | 11 | DSQIQYWQLIR | | 40929 |

TABLE XVII-continued

A11 Motif Peptides

| Type | Protein | Position | No. of Amino Acids | Sequence | A*1101 | Seq. Id. No. |
|---|---|---|---|---|---|---|
| HPV18 | E2 | 354 | 9 | DSVQILVGY | | 40930 |
| HPV18 | E2 | 210 | 10 | DTVSATQLVK | | 40931 |
| HPV18 | E2 | 175 | 8 | EFKSECEK | | 40932 |
| HPV18 | E2 | 175 | 9 | EFKSECEKY | | 40933 |
| HPV18 | E2 | 167 | 11 | EGYNTFYIEFK | | 40934 |
| HPV18 | E2 | 104 | 9 | ELWNTEPTH | | 40935 |
| HPV18 | E2 | 43 | 9 | ENAIFFAAR | | 40936 |
| HPV18 | E2 | 43 | 11 | ENAIFFAAREH | | 40937 |
| HPV18 | E2 | 125 | 11 | FDGNKDNCMTY | | 40938 |
| HPV18 | E2 | 268 | 10 | GAATPTGNNK | | 40939 |
| HPV18 | E2 | 268 | 11 | GAATPTGNNKR | | 40940 |
| HPV18 | E2 | 294 | 10 | GDRNSLKCLR | | 40941 |
| HPV18 | E2 | 294 | 11 | GDRNSLKCLRY | | 40942 |
| HPV18 | E2 | 117 | 8 | GGQTVQVY | | 40943 |
| HPV18 | E2 | 331 | 8 | GILTVTYH | | 40944 |
| HPV18 | E2 | 85 | 8 | GLAQSRYK | | 40945 |
| HPV18 | E2 | 161 | 9 | GLYYVKEGY | | 40946 |
| HPV18 | E2 | 127 | 9 | GNKDNCMTY | | 40947 |
| HPV18 | E2 | 184 | 9 | GNTGTWEVH | | 40948 |
| HPV18 | E2 | 284 | 8 | GNTTPIIH | | 40949 |
| HPV18 | E2 | 284 | 10 | GNTTPIIHLK | | 40950 |
| HPV18 | E2 | 251 | 9 | HCGLAEKQH | | 40951 |
| HPV18 | E2 | 53 | 8 | HGIQTLNH | | 40952 |
| HPV18 | E2 | 291 | 10 | HLKGDRNSLK | | 40953 |
| HPV18 | E2 | 338 | 8 | HSETQRTK | | 40954 |
| HPV18 | E2 | 20 | 9 | IDHYENDSK | | 40955 |
| HPV18 | E2 | 46 | 8 | IFFAAREH | | 40956 |
| HPV18 | E2 | 19 | 10 | IIDHYENDSK | | 40957 |
| HPV18 | E2 | 289 | 8 | IIHLKGDR | | 40958 |
| HPV18 | E2 | 68 | 8 | ISKSKAHK | | 40959 |
| HPV18 | E2 | 300 | 8 | KCLRYRLR | | 40960 |
| HPV18 | E2 | 300 | 9 | KCLRYRLRK | | 40961 |
| HPV18 | E2 | 300 | 10 | KCLRYRLRKH | | 40962 |
| HPV18 | E2 | 28 | 9 | KDIDSQIQY | | 40963 |
| HPV18 | E2 | 293 | 8 | KGDRNSLK | | 40964 |
| HPV18 | E2 | 293 | 11 | KGDRNSLKCLR | | 40965 |
| HPV18 | E2 | 116 | 9 | KGGQTVQVY | | 40966 |
| HPV18 | E2 | 18 | 11 | KIIDHYENDSK | | 40967 |
| HPV18 | E2 | 152 | 8 | KTATCVSH | | 40968 |
| HPV18 | E2 | 152 | 9 | KTATCVSHR | | 40969 |
| HPV18 | E2 | 329 | 9 | KTGILTVTY | | 40970 |
| HPV18 | E2 | 329 | 10 | KTGILTVTYH | | 40971 |
| HPV18 | E2 | 238 | 11 | KTYGQTSAATR | | 40972 |
| HPV18 | E2 | 281 | 11 | LCSGNTTPIIH | | 40973 |
| HPV18 | E2 | 267 | 11 | LGAATPTGNNK | | 40974 |
| HPV18 | E2 | 58 | 9 | LNHQVVPAY | | 40975 |
| HPV18 | E2 | 12 | 11 | LSCVQDKIIDH | | 40976 |
| HPV18 | E2 | 8 | 11 | LSERLSCVQDK | | 40977 |
| HPV18 | E2 | 333 | 11 | LTVTYHSETQR | | 40978 |
| HPV18 | E2 | 81 | 10 | MALQGLAQSR | | 40979 |
| HPV18 | E2 | 81 | 11 | MALQGLAQSRY | | 40980 |
| HPV18 | E2 | 144 | 9 | MTDAGTWDK | | 40981 |
| HPV18 | E2 | 133 | 10 | MTYVAWDSVY | | 40982 |
| HPV18 | E2 | 133 | 11 | MTYVAWDSVYY | | 40983 |
| HPV18 | E2 | 44 | 8 | NAIFFAAR | | 40984 |
| HPV18 | E2 | 44 | 10 | NAIFFAAREH | | 40985 |
| HPV18 | E2 | 67 | 8 | NISKSKAH | | 40986 |
| HPV18 | E2 | 67 | 9 | NISKSKAHK | | 40987 |
| HPV18 | E2 | 297 | 8 | NSLKCLRY | | 40988 |
| HPV18 | E2 | 297 | 9 | NSLKCLRYR | | 40989 |
| HPV18 | E2 | 297 | 11 | NSLKCLRYRLR | | 40990 |
| HPV18 | E2 | 107 | 9 | NTEPTHCFK | | 40991 |
| HPV18 | E2 | 107 | 10 | NTEPTHCFKK | | 40992 |
| HPV18 | E2 | 170 | 8 | NTFYIEFK | | 40993 |
| HPV18 | E2 | 185 | 8 | NTGTWEVH | | 40994 |
| HPV18 | E2 | 285 | 9 | NTTPIIHLK | | 40995 |
| HPV18 | E2 | 64 | 9 | PAYNISKSK | | 40996 |
| HPV18 | E2 | 64 | 11 | PAYNISKSKAH | | 40997 |
| HPV18 | E2 | 353 | 10 | PDSVQILVGY | | 40998 |
| HPV18 | E2 | 249 | 9 | PGHCGLAEK | | 40999 |
| HPV18 | E2 | 249 | 11 | PGHCGLAEKQH | | 41000 |
| HPV18 | E2 | 288 | 9 | PIIHLKGDR | | 41001 |
| HPV18 | E2 | 272 | 8 | PTGNNKRR | | 41002 |
| HPV18 | E2 | 272 | 9 | PTGNNKRRK | | 41003 |
| HPV18 | E2 | 16 | 8 | QDKIIDHY | | 41004 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | E2 | 84 | 8 | QGLAQSRY | | 41005 |
| HPV18 | E2 | 84 | 9 | QGLAQSRYK | | 41006 |
| HPV18 | E2 | 33 | 9 | QIQYWQLIR | | 41007 |
| HPV18 | E2 | 220 | 9 | QLQHTPSPY | | 41008 |
| HPV18 | E2 | 216 | 8 | QLVKQLQH | | 41009 |
| HPV18 | E2 | 80 | 11 | QMALQGLAQSR | | 41010 |
| HPV18 | E2 | 56 | 11 | QTLNHQVVPAY | | 41011 |
| HPV18 | E2 | 2 | 10 | QTPKETLSER | | 41012 |
| HPV18 | E2 | 242 | 10 | QTSAATRPGH | | 41013 |
| HPV18 | E2 | 119 | 11 | QTVQVYFDGNK | | 41014 |
| HPV18 | E2 | 61 | 10 | QVVPAYNISK | | 41015 |
| HPV18 | E2 | 122 | 8 | QVYFDGNK | | 41016 |
| HPV18 | E2 | 314 | 8 | RDISSTWH | | 41017 |
| HPV18 | E2 | 160 | 10 | RGLYYVKEGY | | 41018 |
| HPV18 | E2 | 305 | 8 | RLRKHSDH | | 41019 |
| HPV18 | E2 | 305 | 9 | RLRKHSDHY | | 41020 |
| HPV18 | E2 | 305 | 10 | RLRKHSDHYR | | 41021 |
| HPV18 | E2 | 11 | 8 | RLSCVQDK | | 41022 |
| HPV18 | E2 | 296 | 8 | RNSLKCLR | | 41023 |
| HPV18 | E2 | 296 | 9 | RNSLKCLRY | | 41024 |
| HPV18 | E2 | 296 | 10 | RNSLKCLRYR | | 41025 |
| HPV18 | E2 | 244 | 8 | SAATRPGH | | 41026 |
| HPV18 | E2 | 213 | 11 | SATQLVKQLQH | | 41027 |
| HPV18 | E2 | 13 | 10 | SCVQDKIIDH | | 41028 |
| HPV18 | E2 | 13 | 11 | SCVQDKIIDHY | | 41029 |
| HPV18 | E2 | 283 | 9 | SGNTTPIIH | | 41030 |
| HPV18 | E2 | 283 | 11 | SGNTTPIIHLK | | 41031 |
| HPV18 | E2 | 298 | 8 | SLKCLRYR | | 41032 |
| HPV18 | E2 | 298 | 10 | SLKCLRYRLR | | 41033 |
| HPV18 | E2 | 298 | 11 | SLKCLRYRLRK | | 41034 |
| HPV18 | E2 | 229 | 10 | SSTVSVGTAK | | 41035 |
| HPV18 | E2 | 230 | 9 | STVSVGTAK | | 41036 |
| HPV18 | E2 | 230 | 11 | STVSVGTAKTY | | 41037 |
| HPV18 | E2 | 233 | 8 | SVGTAKTY | | 41038 |
| HPV18 | E2 | 355 | 8 | SVQILVGY | | 41039 |
| HPV18 | E2 | 153 | 8 | TATCVSHR | | 41040 |
| HPV18 | E2 | 153 | 11 | TATCVSHRGLY | | 41041 |
| HPV18 | E2 | 155 | 9 | TCVSHRGLY | | 41042 |
| HPV18 | E2 | 155 | 10 | TCVSHRGLYY | | 41043 |
| HPV18 | E2 | 145 | 8 | TDAGTWDK | | 41044 |
| HPV18 | E2 | 330 | 8 | TGILTVTY | | 41045 |
| HPV18 | E2 | 330 | 9 | TGILTVTYH | | 41046 |
| HPV18 | E2 | 273 | 8 | TGNNKRRK | | 41047 |
| HPV18 | E2 | 57 | 10 | TLNHQVVPAY | | 41048 |
| HPV18 | E2 | 243 | 9 | TSAATRPGH | | 41049 |
| HPV18 | E2 | 286 | 8 | TTPIIHLK | | 41050 |
| HPV18 | E2 | 286 | 11 | TTPIIHLKGDR | | 41051 |
| HPV18 | E2 | 120 | 10 | TVQVYFDGNK | | 41052 |
| HPV18 | E2 | 211 | 9 | TVSATQLVK | | 41053 |
| HPV18 | E2 | 231 | 8 | TVSVGTAK | | 41054 |
| HPV18 | E2 | 231 | 10 | TVSVGTAKTY | | 41055 |
| HPV18 | E2 | 334 | 10 | TVTYHSETQR | | 41056 |
| HPV18 | E2 | 136 | 8 | VAWDSVYY | | 41057 |
| HPV18 | E2 | 212 | 8 | VSATQLVK | | 41058 |
| HPV18 | E2 | 157 | 8 | VSHRGLYY | | 41059 |
| HPV18 | E2 | 157 | 10 | VSHRGLYYVK | | 41060 |
| HPV18 | E2 | 232 | 9 | VSVGTAKTY | | 41061 |
| HPV18 | E2 | 335 | 9 | VTYHSETQR | | 41062 |
| HPV18 | E2 | 335 | 11 | VTYHSETQRTK | | 41063 |
| HPV18 | E2 | 62 | 9 | VVPAYNISK | | 41064 |
| HPV18 | E2 | 62 | 11 | VVPAYNISKSK | | 41065 |
| HPV18 | E2 | 150 | 10 | WDKTATCVSH | | 41066 |
| HPV18 | E2 | 150 | 11 | WDKTATCVSHR | | 41067 |
| HPV18 | E2 | 106 | 10 | WNTEPTHCFK | | 41068 |
| HPV18 | E2 | 106 | 11 | WNTEPTHCFKK | | 41069 |
| HPV18 | E2 | 322 | 8 | WTGAGNEK | | 41070 |
| HPV18 | E2 | 183 | 10 | YGNTGTWEVH | | 41071 |
| HPV18 | E2 | 240 | 9 | YGQTSAATR | | 41072 |
| HPV18 | E2 | 173 | 10 | YIEFKSECEK | | 41073 |
| HPV18 | E2 | 173 | 11 | YIEFKSECEKY | | 41074 |
| HPV18 | E2 | 143 | 10 | YMTDAGTWDK | | 41075 |
| HPV18 | E2 | 66 | 9 | YNISKSKAH | | 41076 |
| HPV18 | E2 | 66 | 10 | YNISKSKAHK | | 41077 |
| HPV18 | E2 | 169 | 9 | YNTFYIEFK | | 41078 |
| HPV18 | E2 | 228 | 11 | YSSTVSVGTAK | | 41079 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | E2 | 135 | 8 | YVAWDSVY | | 41080 |
| HPV18 | E2 | 135 | 9 | YVAWDSVYY | | 41081 |
| HPV18 | E2 | 164 | 10 | YVKEGYNTFY | | 41082 |
| HPV18 | E5 | 29 | 11 | CAYAWVLVFVY | | 41083 |
| HPV18 | E5 | 9 | 11 | CFCVCMYVCCH | | 41084 |
| HPV18 | E5 | 56 | 10 | CFLLPMLLLH | | 41085 |
| HPV18 | E5 | 11 | 9 | CVCMYVCCH | | 41086 |
| HPV18 | E5 | 8 | 8 | FCFCVCMY | | 41087 |
| HPV18 | E5 | 55 | 11 | FCFLLPMLLLH | | 41088 |
| HPV18 | E5 | 10 | 10 | FCVCMYVCCH | | 41089 |
| HPV18 | E5 | 6 | 10 | FLFCFCVCMY | | 41090 |
| HPV18 | E5 | 57 | 9 | FLLPMLLLH | | 41091 |
| HPV18 | E5 | 57 | 11 | FLLPMLLLHIH | | 41092 |
| HPV18 | E5 | 5 | 11 | IFLFCFCVCMY | | 41093 |
| HPV18 | E5 | 43 | 11 | ITSPATAFTVY | | 41094 |
| HPV18 | E5 | 7 | 9 | LFCFCVCMY | | 41095 |
| HPV18 | E5 | 58 | 8 | LLPMLLH | | 41096 |
| HPV18 | E5 | 58 | 10 | LLPMLLLHIH | | 41097 |
| HPV18 | E5 | 22 | 10 | LLPSVCMCAY | | 41098 |
| HPV18 | E5 | 46 | 8 | PATAFTVY | | 41099 |
| HPV18 | E5 | 21 | 11 | PLLPSVCMCAY | | 41100 |
| HPV18 | E5 | 60 | 8 | PMLLLHIH | | 41101 |
| HPV18 | E5 | 24 | 8 | PSVCMCAY | | 41102 |
| HPV18 | E5 | 44 | 10 | TSPATAFTVY | | 41103 |
| HPV18 | E5 | 12 | 8 | VCMYVCCH | | 41104 |
| HPV18 | E5 | 31 | 9 | YAWVLVFVY | | 41105 |
| HPV18 | E6 | 63 | 10 | AACHKCIDFY | | 41106 |
| HPV18 | E6 | 64 | 9 | ACHKCIDFY | | 41107 |
| HPV18 | E6 | 64 | 11 | ACHKCIDFYSR | | 41108 |
| HPV18 | E6 | 48 | 9 | AFKDLFVVY | | 41109 |
| HPV18 | E6 | 48 | 10 | AFKDLFVVYR | | 41110 |
| HPV18 | E6 | 131 | 9 | AGHYRGQCH | 0.0002 | 41111 |
| HPV18 | E6 | 141 | 9 | CCNRARQER | | 41112 |
| HPV18 | E6 | 68 | 9 | CIDFYSRIR | 0.0001 | 41113 |
| HPV18 | E6 | 142 | 8 | CNRARQER | | 41114 |
| HPV18 | E6 | 142 | 11 | CNRARQERLQR | | 41115 |
| HPV18 | E6 | 70 | 10 | DFYSRIRELR | 0.0001 | 41116 |
| HPV18 | E6 | 70 | 11 | DFYSRIRELRH | | 41117 |
| HPV18 | E6 | 27 | 8 | DIEITCVY | | 41118 |
| HPV18 | E6 | 27 | 10 | DIEITCVYCK | 0.0021 | 41119 |
| HPV18 | E6 | 58 | 9 | DSIPHAACH | 0.0002 | 41120 |
| HPV18 | E6 | 58 | 10 | DSIPHAACHK | | 41121 |
| HPV18 | E6 | 83 | 10 | DSVYGDTLEK | 0.0051 | 41122 |
| HPV18 | E6 | 5 | 8 | EDPTRRPY | | 41123 |
| HPV18 | E6 | 5 | 9 | EDPTRRPYK | | 41124 |
| HPV18 | E6 | 46 | 11 | EFAFKDLFVVY | | 41125 |
| HPV18 | E6 | 29 | 8 | EITCVYCK | | 41126 |
| HPV18 | E6 | 77 | 10 | ELRHYSDSVY | 0.0002 | 41127 |
| HPV18 | E6 | 40 | 11 | ELTEVFEFAFK | | 41128 |
| HPV18 | E6 | 43 | 8 | EVFEFAFK | 0.0180 | 41129 |
| HPV18 | E6 | 47 | 10 | FAFKDLFVVY | | 41130 |
| HPV18 | E6 | 47 | 11 | FAFKDLFVVYR | | 41131 |
| HPV18 | E6 | 53 | 10 | FVVYRDSIPH | | 41132 |
| HPV18 | E6 | 97 | 8 | GLYNLLIR | | 41133 |
| HPV18 | E6 | 97 | 11 | GLYNLLIRCLR | | 41134 |
| HPV18 | E6 | 62 | 11 | HAACHKCIDFY | | 41135 |
| HPV18 | E6 | 120 | 9 | HLNEKRRFH | | 41136 |
| HPV18 | E6 | 128 | 8 | HNIAGHYR | | 41137 |
| HPV18 | E6 | 139 | 8 | HSCCNRAR | | 41138 |
| HPV18 | E6 | 139 | 11 | HSCCNRARQER | | 41139 |
| HPV18 | E6 | 130 | 10 | IAGHYRGQCH | | 41140 |
| HPV18 | E6 | 69 | 8 | IDFYSRIR | | 41141 |
| HPV18 | E6 | 69 | 11 | IDFYSRIRELR | | 41142 |
| HPV18 | E6 | 67 | 8 | KCIDFYSR | | 41143 |
| HPV18 | E6 | 67 | 10 | KCIDFYSRIR | | 41144 |
| HPV18 | E6 | 50 | 8 | KDLFVVYR | | 41145 |
| HPV18 | E6 | 117 | 8 | KLRHLNEK | | 41146 |
| HPV18 | E6 | 117 | 9 | KLRHLNEKR | 0.0005 | 41147 |
| HPV18 | E6 | 117 | 10 | KLRHLNEKRR | 0.0001 | 41148 |
| HPV18 | E6 | 92 | 8 | KLTNTGLY | | 41149 |
| HPV18 | E6 | 52 | 11 | LFVVYRDSIPH | | 41150 |
| HPV18 | E6 | 102 | 9 | LIRCLRCQK | 0.0012 | 41151 |
| HPV18 | E6 | 101 | 10 | LLIRCLRCQK | 0.1200 | 41152 |
| HPV18 | E6 | 121 | 8 | LNEKRRFH | | 41153 |
| HPV18 | E6 | 112 | 8 | LNPAEKLR | | 41154 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | E6 | 112 | 9 | LNPAEKLRH | | 41155 |
| HPV18 | E6 | 41 | 10 | LTEVFEFAFK | 0.0360 | 41156 |
| HPV18 | E6 | 1 | 9 | MARFEDPTR | | 41157 |
| HPV18 | E6 | 1 | 10 | MARFEDPTRR | | 41158 |
| HPV18 | E6 | 129 | 11 | NIAGHYRGQCH | | 41159 |
| HPV18 | E6 | 100 | 8 | NLLIRCLR | | 41160 |
| HPV18 | E6 | 100 | 11 | NLLIRCLRCQK | | 41161 |
| HPV18 | E6 | 95 | 10 | NTGLYNLLIR | 0.0013 | 41162 |
| HPV18 | E6 | 114 | 11 | PAEKLRHLNEK | | 41163 |
| HPV18 | E6 | 111 | 9 | PLNPAEKLR | 0.0005 | 41164 |
| HPV18 | E6 | 111 | 10 | PLNPAEKLRH | | 41165 |
| HPV18 | E6 | 137 | 8 | QCHSCCNR | | 41166 |
| HPV18 | E6 | 137 | 10 | QCHSCCNRAR | | 41167 |
| HPV18 | E6 | 26 | 9 | QDIEITCVY | | 41168 |
| HPV18 | E6 | 26 | 11 | QDIEITCVYCK | | 41169 |
| HPV18 | E6 | 144 | 9 | RARQERLQR | 0.0002 | 41170 |
| HPV18 | E6 | 144 | 10 | RARQERLQRR | | 41171 |
| HPV18 | E6 | 144 | 11 | RARQERLQRRR | | 41172 |
| HPV18 | E6 | 107 | 11 | RCQKPLNPAEK | | 41173 |
| HPV18 | E6 | 57 | 10 | RDSIPHAACH | | 41174 |
| HPV18 | E6 | 57 | 11 | RDSIPHAACHK | | 41175 |
| HPV18 | E6 | 3 | 8 | RFEDPTRR | | 41176 |
| HPV18 | E6 | 3 | 10 | RFEDPTRRPY | 0.0002 | 41177 |
| HPV18 | E6 | 3 | 11 | RFEDPTRRPYK | | 41178 |
| HPV18 | E6 | 126 | 8 | RFHNIAGH | | 41179 |
| HPV18 | E6 | 126 | 9 | RFHNIAGHY | 0.0002 | 41180 |
| HPV18 | E6 | 126 | 10 | RFHNIAGHYR | 0.0057 | 41181 |
| HPV18 | E6 | 135 | 10 | RGQCHSCCNR | | 41182 |
| HPV18 | E6 | 74 | 8 | RIRELRHY | | 41183 |
| HPV18 | E6 | 140 | 10 | SCCNRARQER | | 41184 |
| HPV18 | E6 | 82 | 11 | SDSVYGDTLEK | | 41185 |
| HPV18 | E6 | 59 | 8 | SIPHAACH | | 41186 |
| HPV18 | E6 | 59 | 9 | SIPHAACHK | 0.1200 | 41187 |
| HPV18 | E6 | 24 | 11 | SLQDIEITCVY | | 41188 |
| HPV18 | E6 | 84 | 9 | SVYGDTLEK | 0.2300 | 41189 |
| HPV18 | E6 | 96 | 9 | TGLYNLLIR | 0.0002 | 41190 |
| HPV18 | E6 | 89 | 11 | TLEKLTNTGLY | 0.0002 | 41191 |
| HPV18 | E6 | 94 | 11 | TNTGLYNLLIR | | 41192 |
| HPV18 | E6 | 54 | 9 | VVYRDSIPH | 0.3800 | 41193 |
| HPV18 | E6 | 99 | 9 | YNLLIRCLR | | 41194 |
| HPV18 | E6 | 72 | 8 | YSRIRELR | | 41195 |
| HPV18 | E6 | 72 | 9 | YSRIRELRH | | 41196 |
| HPV18 | E6 | 72 | 10 | YSRIRELRHY | 0.0001 | 41197 |
| HPV18 | E7 | 6 | 9 | ATLQDIVLH | | 41198 |
| HPV18 | E7 | 65 | 9 | CCKCEARIK | | 41199 |
| HPV18 | E7 | 63 | 9 | CMCCKCEAR | | 41200 |
| HPV18 | E7 | 63 | 11 | CMCCKCEARIK | 0.0002 | 41201 |
| HPV18 | E7 | 42 | 11 | DGVNHQHLPAR | | 41202 |
| HPV18 | E7 | 40 | 9 | EIDGVNHQH | | 41203 |
| HPV18 | E7 | 20 | 9 | EIPVDLLCH | | 41204 |
| HPV18 | E7 | 37 | 10 | ENDEIDGVNH | | 41205 |
| HPV18 | E7 | 77 | 8 | ESSADDLR | | 41206 |
| HPV18 | E7 | 43 | 10 | GVNHQHLPAR | | 41207 |
| HPV18 | E7 | 43 | 11 | GVNHQHLPARR | | 41208 |
| HPV18 | E7 | 48 | 11 | HLPARRAEPQR | | 41209 |
| HPV18 | E7 | 59 | 9 | HTMLCMCCK | 0.0940 | 41210 |
| HPV18 | E7 | 41 | 8 | IDGVNHQH | | 41211 |
| HPV18 | E7 | 5 | 10 | KATLQDIVLH | | 41212 |
| HPV18 | E7 | 62 | 10 | LCMCCKCEAR | | 41213 |
| HPV18 | E7 | 74 | 11 | LVVESSADDLR | | 41214 |
| HPV18 | E7 | 64 | 8 | MCCKCEAR | | 41215 |
| HPV18 | E7 | 64 | 10 | MCCKCEARIK | | 41216 |
| HPV18 | E7 | 61 | 11 | MLCMCCKCEAR | | 41217 |
| HPV18 | E7 | 38 | 9 | NDEIDGVNH | | 41218 |
| HPV18 | E7 | 38 | 11 | NDEIDGVNHQH | | 41219 |
| HPV18 | E7 | 50 | 9 | PARRAEPQR | | 41220 |
| HPV18 | E7 | 50 | 10 | PARRAEPQRH | | 41221 |
| HPV18 | E7 | 18 | 11 | QNEIPVDLLCH | | 41222 |
| HPV18 | E7 | 7 | 8 | TLQDIVLH | | 41223 |
| HPV18 | E7 | 60 | 8 | TMLCMCCK | 0.0240 | 41224 |
| HPV18 | E7 | 44 | 9 | VNHQHLPAR | 0.0007 | 41225 |
| HPV18 | E7 | 44 | 10 | VNHQHLPARR | | 41226 |
| HPV18 | E7 | 75 | 10 | VVESSADDLR | | 41227 |
| HPV18 | L1 | 494 | 10 | AAPAENKDPY | | 41228 |
| HPV18 | L1 | 195 | 11 | AATSNVSEDVR | | 41229 |

TABLE XVII-continued

A11 Motif Peptides

| Type | Protein | Position | No. of Amino Acids | Sequence | A*1101 | Seq. Id. No. |
|---|---|---|---|---|---|---|
| HPV18 | L1 | 162 | 9 | ACAGVEIGR | | 41230 |
| HPV18 | L1 | 447 | 8 | ADVMSYIH | | 41231 |
| HPV18 | L1 | 115 | 11 | AGGGNKQDIPK | | 41232 |
| HPV18 | L1 | 225 | 8 | AIGEHWAK | | 41233 |
| HPV18 | L1 | 63 | 11 | ALWRPSDNTVY | | 41234 |
| HPV18 | L1 | 268 | 11 | AMDFSTLQDTK | | 41235 |
| HPV18 | L1 | 345 | 8 | ASPGSCVY | | 41236 |
| HPV18 | L1 | 407 | 11 | ASTQSPVPGQY | | 41237 |
| HPV18 | L1 | 419 | 9 | ATKFKQYSR | | 41238 |
| HPV18 | L1 | 419 | 10 | ATKFKQYSRH | | 41239 |
| HPV18 | L1 | 196 | 10 | ATSNVSEDVR | | 41240 |
| HPV18 | L1 | 552 | 9 | ATTSSKPAK | | 41241 |
| HPV18 | L1 | 552 | 10 | ATTSSKPAKR | | 41242 |
| HPV18 | L1 | 163 | 8 | CAGVEIGR | | 41243 |
| HPV18 | L1 | 222 | 8 | CAPAIGEH | | 41244 |
| HPV18 | L1 | 222 | 11 | CAPAIGEHWAK | | 41245 |
| HPV18 | L1 | 42 | 10 | CGHYIILFLR | | 41246 |
| HPV18 | L1 | 310 | 10 | CLRREQLFAR | | 41247 |
| HPV18 | L1 | 310 | 11 | CLRREQLFARH | | 41248 |
| HPV18 | L1 | 2 | 10 | CLYTRVLILH | | 41249 |
| HPV18 | L1 | 2 | 11 | CLYTRVLILHY | | 41250 |
| HPV18 | L1 | 493 | 8 | DAAPAENK | | 41251 |
| HPV18 | L1 | 493 | 11 | DAAPAENKDPY | | 41252 |
| HPV18 | L1 | 418 | 8 | DATKFKQY | | 41253 |
| HPV18 | L1 | 418 | 10 | DATKFKQYSR | | 41254 |
| HPV18 | L1 | 418 | 11 | DATKFKQYSRH | | 41255 |
| HPV18 | L1 | 245 | 8 | DCPPLELK | | 41256 |
| HPV18 | L1 | 86 | 11 | DDYVTPTSIFY | | 41257 |
| HPV18 | L1 | 270 | 9 | DFSTLQDTK | | 41258 |
| HPV18 | L1 | 258 | 9 | DGDMVDTGY | | 41259 |
| HPV18 | L1 | 284 | 8 | DICQSICK | | 41260 |
| HPV18 | L1 | 284 | 9 | DICQSICKY | | 41261 |
| HPV18 | L1 | 122 | 8 | DIPKVSAY | | 41262 |
| HPV18 | L1 | 122 | 10 | DIPKVSAYQY | | 41263 |
| HPV18 | L1 | 122 | 11 | DIPKVSAYQYR | | 41264 |
| HPV18 | L1 | 520 | 9 | DLDQYPLGR | | 41265 |
| HPV18 | L1 | 520 | 10 | DLDQYPLGRK | | 41266 |
| HPV18 | L1 | 206 | 8 | DNVSVDYK | | 41267 |
| HPV18 | L1 | 305 | 8 | DSMFFCLR | | 41268 |
| HPV18 | L1 | 305 | 9 | DSMFFCLRR | | 41269 |
| HPV18 | L1 | 364 | 9 | DSQLFNKPY | | 41270 |
| HPV18 | L1 | 148 | 11 | DTSIYNPETQR | | 41271 |
| HPV18 | L1 | 330 | 8 | DTVPQSLY | | 41272 |
| HPV18 | L1 | 330 | 10 | DTVPQSLYIK | | 41273 |
| HPV18 | L1 | 203 | 10 | DVRDNVSVDY | | 41274 |
| HPV18 | L1 | 203 | 11 | DVRDNVSVDYK | | 41275 |
| HPV18 | L1 | 257 | 10 | EDGDMVDTGY | | 41276 |
| HPV18 | L1 | 202 | 11 | EDVRDNVSVDY | | 41277 |
| HPV18 | L1 | 498 | 8 | ENKDPYDK | | 41278 |
| HPV18 | L1 | 498 | 10 | ENKDPYDKLK | | 41279 |
| HPV18 | L1 | 317 | 8 | FARHFWNR | | 41280 |
| HPV18 | L1 | 309 | 11 | FCLRREQLFAR | | 41281 |
| HPV18 | L1 | 144 | 9 | FGLPDTSIY | | 41282 |
| HPV18 | L1 | 59 | 8 | FLQMALWR | | 41283 |
| HPV18 | L1 | 530 | 8 | FLVQAGLR | | 41284 |
| HPV18 | L1 | 530 | 9 | FLVQAGLRR | | 41285 |
| HPV18 | L1 | 530 | 10 | FLVQAGLRRK | | 41286 |
| HPV18 | L1 | 368 | 8 | FNKPYWLH | | 41287 |
| HPV18 | L1 | 368 | 9 | FNKPYWLHK | | 41288 |
| HPV18 | L1 | 517 | 8 | FSLDLDQY | | 41289 |
| HPV18 | L1 | 271 | 8 | FSTLQDTK | | 41290 |
| HPV18 | L1 | 482 | 11 | FVQSVAITCQK | | 41291 |
| HPV18 | L1 | 221 | 9 | GCAPAIGEH | | 41292 |
| HPV18 | L1 | 244 | 9 | GDCPPLELK | | 41293 |
| HPV18 | L1 | 259 | 8 | GDMVDTGY | | 41294 |
| HPV18 | L1 | 304 | 9 | GDSMFFCLR | | 41295 |
| HPV18 | L1 | 304 | 10 | GDSMFFCLRR | | 41296 |
| HPV18 | L1 | 329 | 9 | GDTVPQSLY | | 41297 |
| HPV18 | L1 | 329 | 11 | GDTVPQSLYIK | | 41298 |
| HPV18 | L1 | 116 | 10 | GGGNKQDIPK | | 41299 |
| HPV18 | L1 | 117 | 9 | GGNKQDIPK | | 41300 |
| HPV18 | L1 | 145 | 8 | GLPDTSIY | | 41301 |
| HPV18 | L1 | 535 | 11 | GLRRKPTIGPR | | 41302 |
| HPV18 | L1 | 177 | 8 | GLSGHPFY | | 41303 |
| HPV18 | L1 | 177 | 10 | GLSGHPFYNK | | 41304 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | L1 | 342 | 11 | GMPASPGSCVY | | 41305 |
| HPV18 | L1 | 118 | 8 | GNKQDIPK | | 41306 |
| HPV18 | L1 | 175 | 10 | GVGLSGHPFY | | 41307 |
| HPV18 | L1 | 38 | 8 | HIIICGHY | | 41308 |
| HPV18 | L1 | 13 | 10 | HLLPLYGPLY | | 41309 |
| HPV18 | L1 | 13 | 11 | HLLPLYGPLYH | | 41310 |
| HPV18 | L1 | 380 | 8 | HNNGVCWH | | 41311 |
| HPV18 | L1 | 30 | 9 | HSILVYMVH | | 41312 |
| HPV18 | L1 | 41 | 11 | ICGHYIILFLR | | 41313 |
| HPV18 | L1 | 285 | 8 | ICQSICKY | | 41314 |
| HPV18 | L1 | 285 | 11 | ICQSICKYPDY | | 41315 |
| HPV18 | L1 | 58 | 9 | IFLQMALWR | | 41316 |
| HPV18 | L1 | 94 | 9 | IFYHAGSSR | | 41317 |
| HPV18 | L1 | 219 | 11 | ILGCAPAIGEH | | 41318 |
| HPV18 | L1 | 9 | 10 | ILHYHLLPLY | | 41319 |
| HPV18 | L1 | 443 | 10 | ITLTADVMSY | | 41320 |
| HPV18 | L1 | 360 | 11 | IVTSDSQLFNK | | 41321 |
| HPV18 | L1 | 492 | 9 | KDAAPAENK | | 41322 |
| HPV18 | L1 | 500 | 8 | KDPYDKLK | | 41323 |
| HPV18 | L1 | 143 | 10 | KFGLPDTSIY | | 41324 |
| HPV18 | L1 | 421 | 8 | KFKQYSRH | | 41325 |
| HPV18 | L1 | 529 | 9 | KFLVQAGLR | | 41326 |
| HPV18 | L1 | 529 | 10 | KFLVQAGLRR | | 41327 |
| HPV18 | L1 | 529 | 11 | KFLVQAGLRRK | | 41328 |
| HPV18 | L1 | 516 | 9 | KFSLDLDQY | | 41329 |
| HPV18 | L1 | 507 | 8 | KFWNVDLK | | 41330 |
| HPV18 | L1 | 507 | 10 | KFWNVDLKEK | | 41331 |
| HPV18 | L1 | 232 | 8 | KGTACKSR | | 41332 |
| HPV18 | L1 | 186 | 9 | KLDDTESSH | | 41333 |
| HPV18 | L1 | 505 | 10 | KLKFWNVDLK | | 41334 |
| HPV18 | L1 | 125 | 8 | KVSAYQYR | | 41335 |
| HPV18 | L1 | 125 | 11 | KVSAYQYRVFR | | 41336 |
| HPV18 | L1 | 187 | 8 | LDDTESSH | | 41337 |
| HPV18 | L1 | 283 | 9 | LDICQSICK | | 41338 |
| HPV18 | L1 | 283 | 10 | LDICQSICKY | | 41339 |
| HPV18 | L1 | 519 | 10 | LDLDQYPLGR | | 41340 |
| HPV18 | L1 | 519 | 11 | LDLDQYPLGRK | | 41341 |
| HPV18 | L1 | 521 | 8 | LDQYPLGR | | 41342 |
| HPV18 | L1 | 521 | 9 | LDQYPLGRK | | 41343 |
| HPV18 | L1 | 316 | 9 | LFARHFWNR | | 41344 |
| HPV18 | L1 | 367 | 9 | LFNKPYWLH | | 41345 |
| HPV18 | L1 | 367 | 10 | LFNKPYWLHK | | 41346 |
| HPV18 | L1 | 220 | 10 | LGCAPAIGEH | | 41347 |
| HPV18 | L1 | 174 | 8 | LGVGLSGH | | 41348 |
| HPV18 | L1 | 174 | 11 | LGVGLSGHPFY | | 41349 |
| HPV18 | L1 | 8 | 11 | LILHYHLLPLY | | 41350 |
| HPV18 | L1 | 14 | 9 | LLPLYGPLY | | 41351 |
| HPV18 | L1 | 14 | 10 | LLPLYGPLYH | | 41352 |
| HPV18 | L1 | 103 | 8 | LLTVGNPY | | 41353 |
| HPV18 | L1 | 103 | 10 | LLTVGNPYFR | | 41354 |
| HPV18 | L1 | 178 | 9 | LSGHPFYNK | | 41355 |
| HPV18 | L1 | 445 | 8 | LTADVMSY | | 41356 |
| HPV18 | L1 | 445 | 10 | LTADVMSYIH | | 41357 |
| HPV18 | L1 | 104 | 9 | LTVGNPYFR | | 41358 |
| HPV18 | L1 | 531 | 8 | LVQAGLRR | | 41359 |
| HPV18 | L1 | 531 | 9 | LVQAGLRRK | | 41360 |
| HPV18 | L1 | 1 | 11 | MCLYTRVLILH | | 41361 |
| HPV18 | L1 | 269 | 10 | MDFSTLQDTK | | 41362 |
| HPV18 | L1 | 328 | 10 | MGDTVPQSLY | | 41363 |
| HPV18 | L1 | 36 | 9 | MVHIIICGH | | 41364 |
| HPV18 | L1 | 36 | 10 | MVHIIICGHY | | 41365 |
| HPV18 | L1 | 496 | 8 | PAENKDPY | | 41366 |
| HPV18 | L1 | 496 | 10 | PAENKDPYDK | | 41367 |
| HPV18 | L1 | 224 | 9 | PAIGEHWAK | | 41368 |
| HPV18 | L1 | 558 | 8 | PAKRVRVR | | 41369 |
| HPV18 | L1 | 558 | 10 | PAKRVRVRAR | | 41370 |
| HPV18 | L1 | 558 | 11 | PAKRVRVRARK | | 41371 |
| HPV18 | L1 | 344 | 9 | PASPGSCVY | | 41372 |
| HPV18 | L1 | 293 | 11 | PDYLQMSADPY | | 41373 |
| HPV18 | L1 | 414 | 8 | PGQYDATK | | 41374 |
| HPV18 | L1 | 414 | 10 | PGQYDATKFK | | 41375 |
| HPV18 | L1 | 57 | 10 | PIFLQMALWR | | 41376 |
| HPV18 | L1 | 282 | 10 | PLDICQSICK | | 41377 |
| HPV18 | L1 | 282 | 11 | PLDICQSICKY | | 41378 |
| HPV18 | L1 | 173 | 9 | PLGVGLSGH | | 41379 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | L1 | 28 | 8 | PLHSILVY | | 41380 |
| HPV18 | L1 | 28 | 11 | PLHSILVYMVH | | 41381 |
| HPV18 | L1 | 26 | 10 | PLPLHSILVY | | 41382 |
| HPV18 | L1 | 16 | 8 | PLYGPLYH | | 41383 |
| HPV18 | L1 | 16 | 10 | PLYGPLYHPR | | 41384 |
| HPV18 | L1 | 20 | 11 | PLYHPRPLPLH | | 41385 |
| HPV18 | L1 | 550 | 8 | PSATTSSK | | 41386 |
| HPV18 | L1 | 550 | 11 | PSATTSSKPAK | | 41387 |
| HPV18 | L1 | 540 | 8 | PTIGPRKR | | 41388 |
| HPV18 | L1 | 472 | 9 | PTTSLVDTY | | 41389 |
| HPV18 | L1 | 472 | 10 | PTTSLVDTYR | | 41390 |
| HPV18 | L1 | 412 | 10 | PVPGQYDATK | | 41391 |
| HPV18 | L1 | 121 | 9 | QDIPKVSAY | | 41392 |
| HPV18 | L1 | 121 | 11 | QDIPKVSAYQY | | 41393 |
| HPV18 | L1 | 243 | 10 | QGDCPPLELK | | 41394 |
| HPV18 | L1 | 378 | 10 | QGHNNGVCWH | | 41395 |
| HPV18 | L1 | 315 | 10 | QLFARHFWNR | | 41396 |
| HPV18 | L1 | 366 | 10 | QLFNKPYWLH | | 41397 |
| HPV18 | L1 | 366 | 11 | QLFNKPYWLHK | | 41398 |
| HPV18 | L1 | 287 | 9 | QSICKYPDY | | 41399 |
| HPV18 | L1 | 410 | 8 | QSPVPGQY | | 41400 |
| HPV18 | L1 | 484 | 9 | QSVAITCQK | | 41401 |
| HPV18 | L1 | 205 | 8 | RDNVSVDY | | 41402 |
| HPV18 | L1 | 205 | 9 | RDNVSVDYK | | 41403 |
| HPV18 | L1 | 102 | 9 | RLLTVGNPY | | 41404 |
| HPV18 | L1 | 102 | 11 | RLLTVGNPYFR | | 41405 |
| HPV18 | L1 | 547 | 11 | RSAPSATTSSK | | 41406 |
| HPV18 | L1 | 6 | 8 | RVLILHYH | | 41407 |
| HPV18 | L1 | 112 | 9 | RVPAGGGNK | | 41408 |
| HPV18 | L1 | 135 | 9 | RVQLPDPNK | | 41409 |
| HPV18 | L1 | 561 | 8 | RVRVRARK | | 41410 |
| HPV18 | L1 | 81 | 8 | RVVNTDDY | | 41411 |
| HPV18 | L1 | 548 | 10 | SAPSATTSSK | | 41412 |
| HPV18 | L1 | 551 | 10 | SATTSSKPAK | | 41413 |
| HPV18 | L1 | 551 | 11 | SATTSSKPAKR | | 41414 |
| HPV18 | L1 | 127 | 9 | SAYQYRVFR | | 41415 |
| HPV18 | L1 | 363 | 8 | SDSQLFNK | | 41416 |
| HPV18 | L1 | 363 | 10 | SDSQLFNKPY | | 41417 |
| HPV18 | L1 | 179 | 8 | SGHPFYNK | | 41418 |
| HPV18 | L1 | 288 | 8 | SICKYPDY | | 41419 |
| HPV18 | L1 | 93 | 10 | SIFYHAGSSR | | 41420 |
| HPV18 | L1 | 31 | 8 | SILVYMVH | | 41421 |
| HPV18 | L1 | 150 | 9 | SIYNPETQR | | 41422 |
| HPV18 | L1 | 518 | 11 | SLDLDQYPLGR | | 41423 |
| HPV18 | L1 | 306 | 8 | SMFFCLRR | | 41424 |
| HPV18 | L1 | 198 | 8 | SNVSEDVR | | 41425 |
| HPV18 | L1 | 555 | 9 | SSKPAKRVR | | 41426 |
| HPV18 | L1 | 555 | 11 | SSKPAKRVRVR | | 41427 |
| HPV18 | L1 | 100 | 11 | SSRLLTVGNPY | | 41428 |
| HPV18 | L1 | 408 | 10 | STQSPVPGQY | | 41429 |
| HPV18 | L1 | 485 | 8 | SVAITCQK | | 41430 |
| HPV18 | L1 | 78 | 11 | SVARVVNTDDY | | 41431 |
| HPV18 | L1 | 446 | 9 | TADVMSYIH | | 41432 |
| HPV18 | L1 | 442 | 11 | TITLTADVMSY | | 41433 |
| HPV18 | L1 | 444 | 9 | TLTADVMSY | | 41434 |
| HPV18 | L1 | 444 | 11 | TLTADVMSYIH | | 41435 |
| HPV18 | L1 | 327 | 11 | TMGDTVPQSLY | | 41436 |
| HPV18 | L1 | 362 | 9 | TSDSQLFNK | | 41437 |
| HPV18 | L1 | 362 | 11 | TSDSQLFNKPY | | 41438 |
| HPV18 | L1 | 92 | 11 | TSIFYHAGSSR | | 41439 |
| HPV18 | L1 | 149 | 10 | TSIYNPETQR | | 41440 |
| HPV18 | L1 | 474 | 8 | TSLVDTYR | | 41441 |
| HPV18 | L1 | 197 | 9 | TSNVSEDVR | | 41442 |
| HPV18 | L1 | 554 | 8 | TSSKPAKR | | 41443 |
| HPV18 | L1 | 554 | 10 | TSSKPAKRVR | | 41444 |
| HPV18 | L1 | 473 | 8 | TTSLVDTY | | 41445 |
| HPV18 | L1 | 473 | 9 | TTSLVDTYR | | 41446 |
| HPV18 | L1 | 553 | 8 | TTSSKPAK | | 41447 |
| HPV18 | L1 | 553 | 9 | TTSSKPAKR | | 41448 |
| HPV18 | L1 | 553 | 11 | TTSSKPAKRVR | | 41449 |
| HPV18 | L1 | 105 | 8 | TVGNPYFR | | 41450 |
| HPV18 | L1 | 331 | 9 | TVPQSLYIK | | 41451 |
| HPV18 | L1 | 71 | 11 | TVYLPPPSVAR | | 41452 |
| HPV18 | L1 | 79 | 10 | VARVVNTDDY | | 41453 |
| HPV18 | L1 | 133 | 11 | VFRVQLPDPNK | | 41454 |

TABLE XVII-continued

A11 Motif Peptides

| Type | Protein | Position | No. of Amino Acids | Sequence | A*1101 | Seq. Id. No. |
|---|---|---|---|---|---|---|
| HPV18 | L1 | 176 | 9 | VGLSGHPFY | | 41455 |
| HPV18 | L1 | 176 | 11 | VGLSGHPFYNK | | 41456 |
| HPV18 | L1 | 126 | 10 | VSAYQYRVFR | | 41457 |
| HPV18 | L1 | 89 | 8 | VTPTSIFY | | 41458 |
| HPV18 | L1 | 89 | 9 | VTPTSIFYH | | 41459 |
| HPV18 | L1 | 361 | 10 | VTSDSQLFNK | | 41460 |
| HPV18 | L1 | 161 | 10 | WACAGVEIGR | | 41461 |
| HPV18 | L1 | 230 | 8 | WAKGTACK | | 41462 |
| HPV18 | L1 | 230 | 10 | WAKGTACKSR | | 41463 |
| HPV18 | L1 | 373 | 8 | WLHKAQGH | | 41464 |
| HPV18 | L1 | 509 | 8 | WNVDLKEK | | 41465 |
| HPV18 | L1 | 417 | 9 | YDATKFKQY | | 41466 |
| HPV18 | L1 | 417 | 11 | YDATKFKQYSR | | 41467 |
| HPV18 | L1 | 110 | 11 | YFRVPAGGGNK | | 41468 |
| HPV18 | L1 | 303 | 10 | YGDSMFFCLR | | 41469 |
| HPV18 | L1 | 303 | 11 | YGDSMFFCLRR | | 41470 |
| HPV18 | L1 | 18 | 8 | YGPLYHPR | | 41471 |
| HPV18 | L1 | 73 | 9 | YLPPPSVAR | | 41472 |
| HPV18 | L1 | 295 | 9 | YLQMSADPY | | 41473 |
| HPV18 | L1 | 35 | 10 | YMVHIIICGH | | 41474 |
| HPV18 | L1 | 35 | 11 | YMVHIIICGHY | | 41475 |
| HPV18 | L1 | 184 | 11 | YNKLDDTESSH | | 41476 |
| HPV18 | L1 | 425 | 8 | YSRHVEEY | | 41477 |
| HPV18 | L1 | 4 | 8 | YTRVLILH | | 41478 |
| HPV18 | L1 | 4 | 9 | YTRVLILHY | | 41479 |
| HPV18 | L1 | 4 | 10 | YTRVLILHYH | | 41480 |
| HPV18 | L1 | 88 | 9 | YVTPTSIFY | | 41481 |
| HPV18 | L1 | 88 | 10 | YVTPTSIFYH | | 41482 |
| HPV18 | L2 | 222 | 8 | AGPRLYSR | | 41483 |
| HPV18 | L2 | 222 | 10 | AGPRLYSRAY | | 41484 |
| HPV18 | L2 | 286 | 10 | ALTSRRGTVR | | 41485 |
| HPV18 | L2 | 237 | 8 | ANPEFLTR | | 41486 |
| HPV18 | L2 | 423 | 9 | ASTQYIGIH | | 41487 |
| HPV18 | L2 | 12 | 8 | ASVTDLYK | | 41488 |
| HPV18 | L2 | 12 | 11 | ASVTDLYKTCK | | 41489 |
| HPV18 | L2 | 341 | 11 | ATEDNDLFDIY | | 41490 |
| HPV18 | L2 | 275 | 9 | DFMDIIRLH | | 41491 |
| HPV18 | L2 | 275 | 10 | DFMDIIRLHR | | 41492 |
| HPV18 | L2 | 322 | 11 | DISPIAPSPEY | | 41493 |
| HPV18 | L2 | 354 | 11 | DMDPAVPVPSR | | 41494 |
| HPV18 | L2 | 344 | 8 | DNDLFDIY | | 41495 |
| HPV18 | L2 | 273 | 9 | DSDFMDIIR | | 41496 |
| HPV18 | L2 | 273 | 11 | DSDFMDIIRLH | | 41497 |
| HPV18 | L2 | 109 | 11 | DSSVVTSGAPR | | 41498 |
| HPV18 | L2 | 260 | 9 | DTTLTFDPR | | 41499 |
| HPV18 | L2 | 343 | 9 | EDNDLFDIY | | 41500 |
| HPV18 | L2 | 36 | 8 | EGTTLADK | | 41501 |
| HPV18 | L2 | 443 | 8 | FIPKKRKR | | 41502 |
| HPV18 | L2 | 443 | 11 | FIPKKRKRVPY | | 41503 |
| HPV18 | L2 | 241 | 11 | FLTRPSSLITY | | 41504 |
| HPV18 | L2 | 276 | 8 | FMDIIRLH | | 41505 |
| HPV18 | L2 | 276 | 9 | FMDIIRLHR | | 41506 |
| HPV18 | L2 | 306 | 11 | FTRSGTQIGAR | | 41507 |
| HPV18 | L2 | 181 | 10 | FVGTPTSGTH | | 41508 |
| HPV18 | L2 | 314 | 8 | GARVHFYH | | 41509 |
| HPV18 | L2 | 58 | 11 | GIGTGSGTGGR | | 41510 |
| HPV18 | L2 | 429 | 8 | GIHGTHYY | | 41511 |
| HPV18 | L2 | 62 | 10 | GSGTGGRTGY | | 41512 |
| HPV18 | L2 | 25 | 10 | GTCPPDVVPK | | 41513 |
| HPV18 | L2 | 64 | 8 | GTGGRTGY | | 41514 |
| HPV18 | L2 | 60 | 9 | GTGSGTGGR | | 41515 |
| HPV18 | L2 | 432 | 10 | GTHYYLWPLY | | 41516 |
| HPV18 | L2 | 432 | 11 | GTHYYLWPLYY | | 41517 |
| HPV18 | L2 | 183 | 8 | GTPTSGTH | | 41518 |
| HPV18 | L2 | 183 | 10 | GTPTSGTHGY | | 41519 |
| HPV18 | L2 | 310 | 9 | GTQIGARVH | | 41520 |
| HPV18 | L2 | 310 | 11 | GTQIGARVHFY | | 41521 |
| HPV18 | L2 | 292 | 11 | GTVRFSRLGQR | | 41522 |
| HPV18 | L2 | 431 | 11 | HGTHYYLWPLY | | 41523 |
| HPV18 | L2 | 313 | 8 | IGARVHFY | | 41524 |
| HPV18 | L2 | 313 | 9 | IGARVHFYH | | 41525 |
| HPV18 | L2 | 428 | 8 | IGIHGTHY | | 41526 |
| HPV18 | L2 | 428 | 9 | IGIHGTHYY | | 41527 |
| HPV18 | L2 | 59 | 10 | IGTGSGTGGR | | 41528 |
| HPV18 | L2 | 323 | 10 | ISPIAPSPEY | | 41529 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | L2 | 210 | 10 | ISSTPLPTVR | | 41530 |
| HPV18 | L2 | 210 | 11 | ISSTPLPTVRR | | 41531 |
| HPV18 | L2 | 34 | 10 | KVEGTTLADK | | 41532 |
| HPV18 | L2 | 299 | 10 | LGQRATMFTR | | 41533 |
| HPV18 | L2 | 242 | 10 | LTRPSSLITY | | 41534 |
| HPV18 | L2 | 287 | 9 | LTSRRGTVR | | 41535 |
| HPV18 | L2 | 391 | 10 | LTSSWDVPVY | | 41536 |
| HPV18 | L2 | 277 | 8 | MDIIRLHR | | 41537 |
| HPV18 | L2 | 355 | 10 | MDPAVPVPSR | | 41538 |
| HPV18 | L2 | 1 | 8 | MVSHRAAR | | 41539 |
| HPV18 | L2 | 1 | 9 | MVSHRAARR | | 41540 |
| HPV18 | L2 | 1 | 10 | MVSHRAARRK | | 41541 |
| HPV18 | L2 | 1 | 11 | MVSHRAARRKR | | 41542 |
| HPV18 | L2 | 79 | 10 | NTVVDVGPTR | | 41543 |
| HPV18 | L2 | 285 | 11 | PALTSRRGTVR | | 41544 |
| HPV18 | L2 | 422 | 10 | PASTQYIGIH | | 41545 |
| HPV18 | L2 | 357 | 8 | PAVPVPSR | | 41546 |
| HPV18 | L2 | 272 | 10 | PDSDFMDIIR | | 41547 |
| HPV18 | L2 | 325 | 8 | PIAPSPEY | | 41548 |
| HPV18 | L2 | 209 | 11 | PISSTPLPTVR | | 41549 |
| HPV18 | L2 | 390 | 11 | PLTSSWDVPVY | | 41550 |
| HPV18 | L2 | 439 | 8 | PLYYFIPK | | 41551 |
| HPV18 | L2 | 439 | 9 | PLYYFIPKK | | 41552 |
| HPV18 | L2 | 439 | 10 | PLYYFIPKKR | | 41553 |
| HPV18 | L2 | 439 | 11 | PLYYFIPKKRK | | 41554 |
| HPV18 | L2 | 419 | 9 | PTAPASTQY | | 41555 |
| HPV18 | L2 | 376 | 9 | PTISSASSY | | 41556 |
| HPV18 | L2 | 185 | 8 | PTSGTHGY | | 41557 |
| HPV18 | L2 | 216 | 10 | PTVRRVAGPR | | 41558 |
| HPV18 | L2 | 258 | 11 | PVDTTLTFDPR | | 41559 |
| HPV18 | L2 | 312 | 9 | QIGARVHFY | | 41560 |
| HPV18 | L2 | 312 | 10 | QIGARVHFYH | | 41561 |
| HPV18 | L2 | 11 | 8 | RASVTDLY | | 41562 |
| HPV18 | L2 | 11 | 9 | RASVTDLYK | | 41563 |
| HPV18 | L2 | 295 | 8 | RFSRLGQR | | 41564 |
| HPV18 | L2 | 291 | 8 | RGTVRFSR | | 41565 |
| HPV18 | L2 | 298 | 11 | RLGQRATMFTR | | 41566 |
| HPV18 | L2 | 281 | 10 | RLHRPALTSR | | 41567 |
| HPV18 | L2 | 281 | 11 | RLHRPALTSRR | | 41568 |
| HPV18 | L2 | 308 | 9 | RSGTQIGAR | | 41569 |
| HPV18 | L2 | 308 | 11 | RSGTQIGARVH | | 41570 |
| HPV18 | L2 | 364 | 10 | RSTTSFAFFK | | 41571 |
| HPV18 | L2 | 364 | 11 | RSTTSFAFFKY | | 41572 |
| HPV18 | L2 | 68 | 10 | RTGYIPLGGR | | 41573 |
| HPV18 | L2 | 220 | 8 | RVAGPRLY | | 41574 |
| HPV18 | L2 | 220 | 10 | RVAGPRLYSR | | 41575 |
| HPV18 | L2 | 274 | 8 | SDFMDIIR | | 41576 |
| HPV18 | L2 | 274 | 10 | SDFMDIIRLH | | 41577 |
| HPV18 | L2 | 274 | 11 | SDFMDIIRLHR | | 41578 |
| HPV18 | L2 | 24 | 11 | SGTCPPDVVPK | | 41579 |
| HPV18 | L2 | 63 | 9 | SGTGGRTGY | | 41580 |
| HPV18 | L2 | 309 | 8 | SGTQIGAR | | 41581 |
| HPV18 | L2 | 309 | 10 | SGTQIGARVH | | 41582 |
| HPV18 | L2 | 78 | 11 | SNTVVDVGPTR | | 41583 |
| HPV18 | L2 | 211 | 9 | SSTPLPTVR | | 41584 |
| HPV18 | L2 | 211 | 10 | SSTPLPTVRR | | 41585 |
| HPV18 | L2 | 110 | 10 | SSVVTSGAPR | | 41586 |
| HPV18 | L2 | 393 | 8 | SSWDVPVY | | 41587 |
| HPV18 | L2 | 212 | 8 | STPLPTVR | | 41588 |
| HPV18 | L2 | 212 | 9 | STPLPTVRR | | 41589 |
| HPV18 | L2 | 424 | 8 | STQYIGIH | | 41590 |
| HPV18 | L2 | 424 | 11 | STQYIGIHGTH | | 41591 |
| HPV18 | L2 | 365 | 9 | STTSFAFFK | | 41592 |
| HPV18 | L2 | 365 | 10 | STTSFAFFKY | | 41593 |
| HPV18 | L2 | 235 | 10 | SVANPEFLTR | | 41594 |
| HPV18 | L2 | 13 | 10 | SVTDLYKTCK | | 41595 |
| HPV18 | L2 | 111 | 9 | SVVTSGAPR | | 41596 |
| HPV18 | L2 | 420 | 8 | TAPASTQY | | 41597 |
| HPV18 | L2 | 26 | 9 | TCPPDVVPK | | 41598 |
| HPV18 | L2 | 15 | 8 | TDLYKTCK | | 41599 |
| HPV18 | L2 | 61 | 8 | TGSGTGGR | | 41600 |
| HPV18 | L2 | 61 | 11 | TGSGTGGRTGY | | 41601 |
| HPV18 | L2 | 69 | 9 | TGYIPLGGR | | 41602 |
| HPV18 | L2 | 377 | 8 | TISSASSY | | 41603 |
| HPV18 | L2 | 367 | 8 | TSFAFFKY | | 41604 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV18 | L2 | 288 | 8 | TSRRGTVR | | 41605 |
| HPV18 | L2 | 288 | 11 | TSRRGTVRFSR | | 41606 |
| HPV18 | L2 | 392 | 9 | TSSWDVPVY | | 41607 |
| HPV18 | L2 | 261 | 8 | TTLTFDPR | | 41608 |
| HPV18 | L2 | 366 | 8 | TTSFAFFK | | 41609 |
| HPV18 | L2 | 366 | 9 | TTSFAFFKY | | 41610 |
| HPV18 | L2 | 293 | 10 | TVRFSRLGQR | | 41611 |
| HPV18 | L2 | 217 | 9 | TVRRVAGPR | | 41612 |
| HPV18 | L2 | 217 | 11 | TVRRVAGPRLY | | 41613 |
| HPV18 | L2 | 80 | 9 | TVVDVGPTR | | 41614 |
| HPV18 | L2 | 221 | 9 | VAGPRLYSR | | 41615 |
| HPV18 | L2 | 221 | 11 | VAGPRLYSRAY | | 41616 |
| HPV18 | L2 | 236 | 9 | VANPEFLTR | | 41617 |
| HPV18 | L2 | 259 | 10 | VDTTLTFDPR | | 41618 |
| HPV18 | L2 | 180 | 11 | VFVGTPTSGTH | | 41619 |
| HPV18 | L2 | 182 | 9 | VGTPTSGTH | | 41620 |
| HPV18 | L2 | 182 | 11 | VGTPTSGTHGY | | 41621 |
| HPV18 | L2 | 2 | 8 | VSHRAARR | | 41622 |
| HPV18 | L2 | 2 | 9 | VSHRAARRK | | 41623 |
| HPV18 | L2 | 2 | 10 | VSHRAARRKR | | 41624 |
| HPV18 | L2 | 417 | 11 | VSPTAPASTQY | | 41625 |
| HPV18 | L2 | 234 | 11 | VSVANPEFLTR | | 41626 |
| HPV18 | L2 | 14 | 9 | VTDLYKTCK | | 41627 |
| HPV18 | L2 | 81 | 8 | VVDVGPTR | | 41628 |
| HPV18 | L2 | 112 | 8 | VVTSGAPR | | 41629 |
| HPV18 | L2 | 442 | 8 | YFIPKKRK | | 41630 |
| HPV18 | L2 | 442 | 9 | YFIPKKRKR | | 41631 |
| HPV18 | L2 | 427 | 8 | YIGIHGTH | | 41632 |
| HPV18 | L2 | 427 | 9 | YIGIHGTHY | | 41633 |
| HPV18 | L2 | 427 | 10 | YIGIHGTHYY | | 41634 |
| HPV18 | L2 | 436 | 11 | YLWPLYYFIPK | | 41635 |
| HPV18 | L2 | 374 | 11 | YSPTISSASSY | | 41636 |
| HPV31 | E1 | 296 | 8 | AAALYWYR | | 41637 |
| HPV31 | E1 | 185 | 8 | AAMLGKFK | | 41638 |
| HPV31 | E1 | 185 | 11 | AAMLGKFKELY | | 41639 |
| HPV31 | E1 | 371 | 10 | AFLKSNSQAK | | 41640 |
| HPV31 | E1 | 550 | 9 | AGKDDRWPY | | 41641 |
| HPV31 | E1 | 550 | 11 | AGKDDRWPYLH | | 41642 |
| HPV31 | E1 | 111 | 9 | AICIENNSK | | 41643 |
| HPV31 | E1 | 68 | 11 | ALFHAQEAEEH | | 41644 |
| HPV31 | E1 | 439 | 11 | ALKLFLKGVPK | | 41645 |
| HPV31 | E1 | 186 | 10 | AMLGKFKELY | | 41646 |
| HPV31 | E1 | 504 | 8 | ATTPCWHY | | 41647 |
| HPV31 | E1 | 81 | 8 | AVQVLKRK | | 41648 |
| HPV31 | E1 | 81 | 9 | AVQVLKRKY | | 41649 |
| HPV31 | E1 | 370 | 11 | CAFLKSNSQAK | | 41650 |
| HPV31 | E1 | 263 | 10 | CAKNRITIEK | | 41651 |
| HPV31 | E1 | 410 | 11 | CDKVSDEGDWR | | 41652 |
| HPV31 | E1 | 385 | 8 | CGTMCRHY | | 41653 |
| HPV31 | E1 | 385 | 9 | CGTMCRHYK | | 41654 |
| HPV31 | E1 | 385 | 10 | CGTMCRHYKR | | 41655 |
| HPV31 | E1 | 113 | 10 | CIENNSKTAK | | 41656 |
| HPV31 | E1 | 113 | 11 | CIENNSKTAKR | | 41657 |
| HPV31 | E1 | 477 | 9 | CIISYANSK | | 41658 |
| HPV31 | E1 | 477 | 11 | CIISYANSKSH | | 41659 |
| HPV31 | E1 | 284 | 8 | CMLIQPPK | | 41660 |
| HPV31 | E1 | 284 | 10 | CMLIQPPKLR | | 41661 |
| HPV31 | E1 | 155 | 8 | CNGSDGTH | | 41662 |
| HPV31 | E1 | 155 | 11 | CNGSDGTHSER | | 41663 |
| HPV31 | E1 | 100 | 9 | CVDYNISPR | | 41664 |
| HPV31 | E1 | 100 | 11 | CVDYNISPRLK | | 41665 |
| HPV31 | E1 | 620 | 8 | CVSGQNIR | | 41666 |
| HPV31 | E1 | 503 | 8 | DATTPCWH | | 41667 |
| HPV31 | E1 | 503 | 9 | DATTPCWHY | | 41668 |
| HPV31 | E1 | 384 | 8 | DCGTMCRH | | 41669 |
| HPV31 | E1 | 384 | 9 | DCGTMCRHY | | 41670 |
| HPV31 | E1 | 384 | 10 | DCGTMCRHYK | | 41671 |
| HPV31 | E1 | 384 | 11 | DCGTMCRHYKR | | 41672 |
| HPV31 | E1 | 502 | 9 | DDATTPCWH | | 41673 |
| HPV31 | E1 | 502 | 10 | DDATTPCWHY | | 41674 |
| HPV31 | E1 | 553 | 8 | DDRWPYLH | | 41675 |
| HPV31 | E1 | 553 | 10 | DDRWPYLHSR | | 41676 |
| HPV31 | E1 | 351 | 8 | DDSEIAYK | | 41677 |
| HPV31 | E1 | 351 | 9 | DDSEIAYKY | | 41678 |
| HPV31 | E1 | 49 | 9 | DFIDNCNVY | | 41679 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV31 | E1 | 611 | 9 | DGDSFSTFK | | 41680 |
| HPV31 | E1 | 521 | 10 | DGNPVSIDVK | | 41681 |
| HPV31 | E1 | 521 | 11 | DGNPVSIDVKH | | 41682 |
| HPV31 | E1 | 96 | 8 | DISSCVDY | | 41683 |
| HPV31 | E1 | 421 | 8 | DIVKFLRY | | 41684 |
| HPV31 | E1 | 336 | 10 | DLSQMVQWAY | | 41685 |
| HPV31 | E1 | 364 | 11 | DSDSNACAFLK | | 41686 |
| HPV31 | E1 | 352 | 8 | DSEIAYKY | | 41687 |
| HPV31 | E1 | 366 | 9 | DSNACAFLK | | 41688 |
| HPV31 | E1 | 528 | 11 | DVKHKALMQLK | | 41689 |
| HPV31 | E1 | 348 | 10 | DVMDDSEIAY | | 41690 |
| HPV31 | E1 | 348 | 11 | DVMDDSEIAYK | | 41691 |
| HPV31 | E1 | 62 | 10 | EAETAQALFH | | 41692 |
| HPV31 | E1 | 80 | 8 | EAVQVLKR | | 41693 |
| HPV31 | E1 | 80 | 9 | EAVQVLKRK | | 41694 |
| HPV31 | E1 | 80 | 10 | EAVQVLKRKY | | 41695 |
| HPV31 | E1 | 432 | 10 | EFVSFLSALK | | 41696 |
| HPV31 | E1 | 416 | 9 | EGDWRDIVK | | 41697 |
| HPV31 | E1 | 229 | 10 | EGFKTLLQPY | | 41698 |
| HPV31 | E1 | 10 | 10 | EGTGCNGWFY | 0.0002 | 41699 |
| HPV31 | E1 | 201 | 10 | ELIRPFQSNK | | 41700 |
| HPV31 | E1 | 583 | 8 | ELSDKNWK | | 41701 |
| HPV31 | E1 | 609 | 11 | ENDGDSFSTFK | | 41702 |
| HPV31 | E1 | 115 | 8 | ENNSKTAK | | 41703 |
| HPV31 | E1 | 115 | 9 | ENNSKTAKR | | 41704 |
| HPV31 | E1 | 115 | 10 | ENNSKTAKRR | | 41705 |
| HPV31 | E1 | 64 | 8 | ETAQALFH | | 41706 |
| HPV31 | E1 | 315 | 8 | ETPEWIER | | 41707 |
| HPV31 | E1 | 574 | 9 | FDKNGNPVY | | 41708 |
| HPV31 | E1 | 335 | 11 | FDLSQMVQWAY | | 41709 |
| HPV31 | E1 | 592 | 8 | FFSRTWCR | | 41710 |
| HPV31 | E1 | 50 | 8 | FIDNCNVY | | 41711 |
| HPV31 | E1 | 443 | 8 | FLKGVPKK | | 41712 |
| HPV31 | E1 | 372 | 9 | FLKSNSQAK | 0.0002 | 41713 |
| HPV31 | E1 | 473 | 9 | FLQGCIISY | | 41714 |
| HPV31 | E1 | 436 | 10 | FLSALKLFLK | | 41715 |
| HPV31 | E1 | 593 | 11 | FSRTWCRLNLH | | 41716 |
| HPV31 | E1 | 566 | 11 | FTFPNPFPFDK | | 41717 |
| HPV31 | E1 | 433 | 9 | FVSFLSALK | | 41718 |
| HPV31 | E1 | 457 | 9 | GAPNTGKSY | | 41719 |
| HPV31 | E1 | 476 | 10 | GCIISYANSK | | 41720 |
| HPV31 | E1 | 612 | 8 | GDSFSTFK | | 41721 |
| HPV31 | E1 | 417 | 8 | GDWRDIVK | | 41722 |
| HPV31 | E1 | 417 | 11 | GDWRDIVKFLR | | 41723 |
| HPV31 | E1 | 230 | 9 | GFKTLLQPY | | 41724 |
| HPV31 | E1 | 305 | 9 | GMSNISDVY | | 41725 |
| HPV31 | E1 | 252 | 9 | GMVMLMLVR | | 41726 |
| HPV31 | E1 | 252 | 11 | GMVMLMLVRFK | | 41727 |
| HPV31 | E1 | 522 | 9 | GNPVSIDVK | | 41728 |
| HPV31 | E1 | 522 | 10 | GNPVSIDVKH | | 41729 |
| HPV31 | E1 | 522 | 11 | GNPVSIDVKHK | | 41730 |
| HPV31 | E1 | 578 | 10 | GNPVYELSDK | | 41731 |
| HPV31 | E1 | 157 | 9 | GSDGTHSER | | 41732 |
| HPV31 | E1 | 11 | 9 | GTGCNGWFY | 0.0720 | 41733 |
| HPV31 | E1 | 386 | 8 | GTMCRHYK | | 41734 |
| HPV31 | E1 | 386 | 9 | GTMCRHYKR | | 41735 |
| HPV31 | E1 | 225 | 8 | GTVAEGFK | | 41736 |
| HPV31 | E1 | 446 | 11 | GVPKKNCILIH | | 41737 |
| HPV31 | E1 | 196 | 9 | GVSFMELIR | | 41738 |
| HPV31 | E1 | 222 | 11 | GVTGTVAEGFK | | 41739 |
| HPV31 | E1 | 78 | 9 | HAEAVQVLK | | 41740 |
| HPV31 | E1 | 78 | 10 | HAEAVQVLKR | | 41741 |
| HPV31 | E1 | 78 | 11 | HAEAVQVLKRK | | 41742 |
| HPV31 | E1 | 71 | 8 | HAQEAEEH | | 41743 |
| HPV31 | E1 | 487 | 11 | HFWLQPLADAK | | 41744 |
| HPV31 | E1 | 456 | 8 | HGAPNTGK | | 41745 |
| HPV31 | E1 | 456 | 10 | HGAPNTGKSY | | 41746 |
| HPV31 | E1 | 162 | 11 | HSERENETPTR | | 41747 |
| HPV31 | E1 | 112 | 8 | ICIENNSK | | 41748 |
| HPV31 | E1 | 112 | 11 | ICIENNSKTAK | | 41749 |
| HPV31 | E1 | 478 | 8 | IISYANSK | | 41750 |
| HPV31 | E1 | 478 | 10 | IISYANSKSH | | 41751 |
| HPV31 | E1 | 453 | 11 | ILIHGAPNTGK | | 41752 |
| HPV31 | E1 | 174 | 11 | ILQVLKTSNGK | | 41753 |
| HPV31 | E1 | 548 | 8 | INAGKDDR | | 41754 |

TABLE XVII-continued

A11 Motif Peptides

| Type | Protein | Position | No. of Amino Acids | Sequence | A*1101 | Seq. Id. No. |
|---|---|---|---|---|---|---|
| HPV31 | E1 | 548 | 11 | INAGKDDRWPY | | 41755 |
| HPV31 | E1 | 471 | 11 | ISFLQGCIISY | | 41756 |
| HPV31 | E1 | 479 | 9 | ISYANSKSH | | 41757 |
| HPV31 | E1 | 268 | 9 | ITIEKLLEK | | 41758 |
| HPV31 | E1 | 544 | 9 | ITSNINAGK | | 41759 |
| HPV31 | E1 | 381 | 10 | IVKDCGTMCR | | 41760 |
| HPV31 | E1 | 381 | 11 | IVKDCGTMCRH | | 41761 |
| HPV31 | E1 | 184 | 9 | KAAMLGKFK | | 41762 |
| HPV31 | E1 | 110 | 10 | KAICIENNSK | | 41763 |
| HPV31 | E1 | 262 | 11 | KCAKNRITIEK | | 41764 |
| HPV31 | E1 | 619 | 9 | KCVSGQNIR | | 41765 |
| HPV31 | E1 | 383 | 8 | KDCGTMCR | | 41766 |
| HPV31 | E1 | 383 | 9 | KDCGTMCRH | | 41767 |
| HPV31 | E1 | 383 | 10 | KDCGTMCRHY | | 41768 |
| HPV31 | E1 | 383 | 11 | KDCGTMCRHYK | | 41769 |
| HPV31 | E1 | 552 | 9 | KDDRWPYLH | | 41770 |
| HPV31 | E1 | 552 | 11 | KDDRWPYLHSR | | 41771 |
| HPV31 | E1 | 380 | 11 | KIVKDCGTMCR | | 41772 |
| HPV31 | E1 | 441 | 9 | KLFLKGVPK | | 41773 |
| HPV31 | E1 | 441 | 10 | KLFLKGVPKK | | 41774 |
| HPV31 | E1 | 291 | 10 | KLRSTAAALY | | 41775 |
| HPV31 | E1 | 265 | 8 | KNRITIEK | | 41776 |
| HPV31 | E1 | 587 | 9 | KNWKSFFSR | | 41777 |
| HPV31 | E1 | 590 | 10 | KSFFSRTWCR | | 41778 |
| HPV31 | E1 | 374 | 10 | KSNSQAKIVK | | 41779 |
| HPV31 | E1 | 232 | 10 | KTLLQPYCLY | | 41780 |
| HPV31 | E1 | 412 | 9 | KVSDEGDWR | | 41781 |
| HPV31 | E1 | 501 | 10 | LDDATTPCWH | | 41782 |
| HPV31 | E1 | 501 | 11 | LDDATTPCWHY | | 41783 |
| HPV31 | E1 | 520 | 11 | LDGNPVSIDVK | | 41784 |
| HPV31 | E1 | 125 | 9 | LFELPDSGY | | 41785 |
| HPV31 | E1 | 69 | 10 | LFHAQEAEEH | | 41786 |
| HPV31 | E1 | 442 | 8 | LFLKGVPK | | 41787 |
| HPV31 | E1 | 442 | 9 | LFLKGVPKK | | 41788 |
| HPV31 | E1 | 188 | 8 | LGKFKELY | | 41789 |
| HPV31 | E1 | 454 | 10 | LIHGAPNTGK | | 41790 |
| HPV31 | E1 | 286 | 8 | LIQPPKLR | | 41791 |
| HPV31 | E1 | 202 | 9 | LIRPFQSNK | | 41792 |
| HPV31 | E1 | 543 | 10 | LITSNINAGK | | 41793 |
| HPV31 | E1 | 542 | 11 | LLITSNINAGK | | 41794 |
| HPV31 | E1 | 234 | 8 | LLQPYCLY | | 41795 |
| HPV31 | E1 | 234 | 10 | LLQPYCLYCH | | 41796 |
| HPV31 | E1 | 256 | 10 | LMLVRFKCAK | | 41797 |
| HPV31 | E1 | 600 | 9 | LNLHEEEDK | | 41798 |
| HPV31 | E1 | 437 | 9 | LSALKLFLK | | 41799 |
| HPV31 | E1 | 153 | 10 | LSCNGSDGTH | | 41800 |
| HPV31 | E1 | 94 | 10 | LSDISSCVDY | | 41801 |
| HPV31 | E1 | 337 | 9 | LSQMVQWAY | | 41802 |
| HPV31 | E1 | 258 | 8 | LVRFKCAK | | 41803 |
| HPV31 | E1 | 258 | 10 | LVRFKCAKNR | | 41804 |
| HPV31 | E1 | 388 | 10 | MCRHYKRAEK | | 41805 |
| HPV31 | E1 | 388 | 11 | MCRHYKRAEKR | | 41806 |
| HPV31 | E1 | 350 | 8 | MDDSEIAY | | 41807 |
| HPV31 | E1 | 350 | 9 | MDDSEIAYK | | 41808 |
| HPV31 | E1 | 350 | 10 | MDDSEIAYKY | | 41809 |
| HPV31 | E1 | 402 | 8 | MGQWIKSR | | 41810 |
| HPV31 | E1 | 402 | 11 | MGQWIKSRCDK | | 41811 |
| HPV31 | E1 | 500 | 11 | MLDDATTPCWH | | 41812 |
| HPV31 | E1 | 187 | 9 | MLGKFKELY | | 41813 |
| HPV31 | E1 | 285 | 9 | MLIQPPKLR | 0.0014 | 41814 |
| HPV31 | E1 | 255 | 8 | MLMLVRFK | | 41815 |
| HPV31 | E1 | 255 | 11 | MLMLVRFKCAK | | 41816 |
| HPV31 | E1 | 257 | 9 | MLVRFKCAK | | 41817 |
| HPV31 | E1 | 257 | 11 | MLVRFKCAKNR | | 41818 |
| HPV31 | E1 | 400 | 8 | MSMGQWIK | | 41819 |
| HPV31 | E1 | 400 | 10 | MSMGQWIKSR | | 41820 |
| HPV31 | E1 | 306 | 8 | MSNISDVY | | 41821 |
| HPV31 | E1 | 47 | 11 | MVDFIDNCNVY | | 41822 |
| HPV31 | E1 | 253 | 8 | MVMLMLVR | | 41823 |
| HPV31 | E1 | 253 | 10 | MVMLMLVRFK | | 41824 |
| HPV31 | E1 | 549 | 10 | NAGKDDRWPY | | 41825 |
| HPV31 | E1 | 283 | 9 | NCMLIQPPK | | 41826 |
| HPV31 | E1 | 283 | 11 | NCMLIQPPKLR | | 41827 |
| HPV31 | E1 | 610 | 10 | NDGDSFSTFK | | 41828 |
| HPV31 | E1 | 347 | 11 | NDVMDDSEIAY | | 41829 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV31 | E1 | 182 | 9 | NGKAAMLGK | | 41830 |
| HPV31 | E1 | 182 | 11 | NGKAAMLGKFK | | 41831 |
| HPV31 | E1 | 577 | 11 | NGNPVYELSDK | | 41832 |
| HPV31 | E1 | 156 | 10 | NGSDGTHSER | | 41833 |
| HPV31 | E1 | 547 | 9 | NINAGKDDR | | 41834 |
| HPV31 | E1 | 601 | 8 | NLHEEEDK | | 41835 |
| HPV31 | E1 | 116 | 8 | NNSKTAKR | | 41836 |
| HPV31 | E1 | 116 | 9 | NNSKTAKRR | | 41837 |
| HPV31 | E1 | 117 | 8 | NSKTAKRR | | 41838 |
| HPV31 | E1 | 376 | 8 | NSQAKIVK | | 41839 |
| HPV31 | E1 | 507 | 9 | PCWHYIDNY | | 41840 |
| HPV31 | E1 | 507 | 11 | PCWHYIDNYLR | | 41841 |
| HPV31 | E1 | 573 | 10 | PFDKNGNPVY | | 41842 |
| HPV31 | E1 | 93 | 11 | PLSDISSCVDY | | 41843 |
| HPV31 | E1 | 569 | 8 | PNPFPFDK | | 41844 |
| HPV31 | E1 | 170 | 10 | PTRNILQVLK | | 41845 |
| HPV31 | E1 | 524 | 8 | PVSIDVKH | | 41846 |
| HPV31 | E1 | 524 | 9 | PVSIDVKHK | | 41847 |
| HPV31 | E1 | 580 | 8 | PVYELSDK | | 41848 |
| HPV31 | E1 | 580 | 11 | PVYELSDKNWK | | 41849 |
| HPV31 | E1 | 475 | 11 | QGCIISYANSK | | 41850 |
| HPV31 | E1 | 399 | 9 | QMSMGQWIK | | 41851 |
| HPV31 | E1 | 399 | 11 | QMSMGQWIKSR | | 41852 |
| HPV31 | E1 | 176 | 9 | QVLKTSNGK | | 41853 |
| HPV31 | E1 | 420 | 8 | RDIVKFLR | | 41854 |
| HPV31 | E1 | 420 | 9 | RDIVKFLRY | | 41855 |
| HPV31 | E1 | 260 | 8 | RFKCAKNR | | 41856 |
| HPV31 | E1 | 267 | 10 | RITIEKLLEK | | 41857 |
| HPV31 | E1 | 124 | 10 | RLFELPDSGY | | 41858 |
| HPV31 | E1 | 599 | 10 | RLNHEEEDK | | 41859 |
| HPV31 | E1 | 172 | 8 | RNILQVLK | | 41860 |
| HPV31 | E1 | 293 | 8 | RSTAAALY | | 41861 |
| HPV31 | E1 | 293 | 10 | RSTAAALYWY | | 41862 |
| HPV31 | E1 | 293 | 11 | RSTAAALYWYR | | 41863 |
| HPV31 | E1 | 303 | 11 | RTGMSNISDVY | | 41864 |
| HPV31 | E1 | 595 | 9 | RTWCRLNLH | | 41865 |
| HPV31 | E1 | 438 | 8 | SALKLFLK | | 41866 |
| HPV31 | E1 | 154 | 9 | SCNGSDGTH | | 41867 |
| HPV31 | E1 | 99 | 10 | SCVDYNISPR | | 41868 |
| HPV31 | E1 | 414 | 11 | SDEGDWRDIVK | | 41869 |
| HPV31 | E1 | 158 | 8 | SDGTHSER | | 41870 |
| HPV31 | E1 | 95 | 9 | SDISSCVDY | | 41871 |
| HPV31 | E1 | 585 | 11 | SDKNWKSFFSR | | 41872 |
| HPV31 | E1 | 365 | 10 | SDSNACAFLK | | 41873 |
| HPV31 | E1 | 591 | 9 | SFFSRTWCR | | 41874 |
| HPV31 | E1 | 472 | 10 | SFLQGCIISY | | 41875 |
| HPV31 | E1 | 435 | 11 | SFLSALKLFLK | | 41876 |
| HPV31 | E1 | 401 | 9 | SMGQWIKSR | | 41877 |
| HPV31 | E1 | 367 | 8 | SNACAFLK | | 41878 |
| HPV31 | E1 | 181 | 10 | SNGKAAMLGK | | 41879 |
| HPV31 | E1 | 546 | 10 | SNINAGKDDR | | 41880 |
| HPV31 | E1 | 375 | 9 | SNSQAKIVK | | 41881 |
| HPV31 | E1 | 98 | 11 | SSCVDYNISPR | | 41882 |
| HPV31 | E1 | 294 | 9 | STAAALYWY | | 41883 |
| HPV31 | E1 | 294 | 10 | STAAALYWYR | | 41884 |
| HPV31 | E1 | 281 | 11 | STNCMLIQPPK | | 41885 |
| HPV31 | E1 | 295 | 8 | TAAALYWY | | 41886 |
| HPV31 | E1 | 295 | 9 | TAAALYWYR | | 41887 |
| HPV31 | E1 | 617 | 11 | TFKCVSGQNIR | | 41888 |
| HPV31 | E1 | 567 | 10 | TFPNPFPFDK | | 41889 |
| HPV31 | E1 | 12 | 8 | TGCNGWFY | | 41890 |
| HPV31 | E1 | 304 | 10 | TGMSNISDVY | | 41891 |
| HPV31 | E1 | 224 | 9 | TGTVAEGFK | | 41892 |
| HPV31 | E1 | 269 | 8 | TIEKLLEK | | 41893 |
| HPV31 | E1 | 233 | 9 | TLLQPYCLY | | 41894 |
| HPV31 | E1 | 233 | 11 | TLLQPYCLYCH | | 41895 |
| HPV31 | E1 | 152 | 11 | TLSCNGSDGTH | | 41896 |
| HPV31 | E1 | 387 | 8 | TMCRHYKR | | 41897 |
| HPV31 | E1 | 387 | 11 | TMCRHYKRAEK | | 41898 |
| HPV31 | E1 | 282 | 10 | TNCMLIQPPK | | 41899 |
| HPV31 | E1 | 180 | 11 | TSNGKAAMLGK | | 41900 |
| HPV31 | E1 | 545 | 8 | TSNINAGK | | 41901 |
| HPV31 | E1 | 545 | 11 | TSNINAGKDDR | | 41902 |
| HPV31 | E1 | 505 | 11 | TTPCWHYIDNY | | 41903 |
| HPV31 | E1 | 48 | 10 | VDFIDNCNVY | | 41904 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV31 | E1 | 101 | 8 | VDYNISPR | | 41905 |
| HPV31 | E1 | 101 | 10 | VDYNISPRLK | | 41906 |
| HPV31 | E1 | 177 | 8 | VLKTSNGK | | 41907 |
| HPV31 | E1 | 349 | 9 | VMDDSEIAY | | 41908 |
| HPV31 | E1 | 349 | 10 | VMDDSEIAYK | | 41909 |
| HPV31 | E1 | 349 | 11 | VMDDSEIAYKY | | 41910 |
| HPV31 | E1 | 254 | 9 | VMLMLVRFK | | 41911 |
| HPV31 | E1 | 413 | 8 | VSDEGDWR | | 41912 |
| HPV31 | E1 | 434 | 8 | VSFLSALK | | 41913 |
| HPV31 | E1 | 197 | 8 | VSFMELIR | | 41914 |
| HPV31 | E1 | 525 | 8 | VSIDVKHK | | 41915 |
| HPV31 | E1 | 223 | 10 | VTGTVAEGFK | | 41916 |
| HPV31 | E1 | 17 | 10 | WFYVEAVIDR | | 41917 |
| HPV31 | E1 | 251 | 10 | WGMVMLMLVR | | 41918 |
| HPV31 | E1 | 319 | 10 | WIERQTVLQH | | 41919 |
| HPV31 | E1 | 405 | 8 | WIKSRCDK | | 41920 |
| HPV31 | E1 | 489 | 9 | WLQPLADAK | 0.0002 | 41921 |
| HPV31 | E1 | 313 | 10 | YGETPEWIER | | 41922 |
| HPV31 | E1 | 195 | 10 | YGVSFMELIR | | 41923 |
| HPV31 | E1 | 103 | 8 | YNISPRLK | | 41924 |
| HPV31 | E1 | 19 | 8 | YVEAVIDR | | 41925 |
| HPV31 | E2 | 277 | 9 | AAAQACTNQTR | | 41926 |
| HPV31 | E2 | 278 | 8 | AACTNQTR | | 41927 |
| HPV31 | E2 | 229 | 9 | ALGTSEGVR | | 41928 |
| HPV31 | E2 | 229 | 10 | ALGTSEGVRR | | 41929 |
| HPV31 | E2 | 61 | 8 | ALSVSKAK | | 41930 |
| HPV31 | E2 | 302 | 8 | ANILKCLR | | 41931 |
| HPV31 | E2 | 302 | 9 | ANILKCLRY | | 41932 |
| HPV31 | E2 | 302 | 10 | ANILKCLRYR | | 41933 |
| HPV31 | E2 | 217 | 10 | ANNTTTSNSK | | 41934 |
| HPV31 | E2 | 291 | 9 | ATTPIIHLK | | 41935 |
| HPV31 | E2 | 239 | 9 | ATTSTKRPR | | 41936 |
| HPV31 | E2 | 228 | 10 | CALGTSEGVR | | 41937 |
| HPV31 | E2 | 228 | 11 | CALGTSEGVRR | | 41938 |
| HPV31 | E2 | 27 | 8 | CDHIDYWK | | 41939 |
| HPV31 | E2 | 27 | 9 | CDHIDYWKH | | 41940 |
| HPV31 | E2 | 27 | 11 | CDHIDYWKHIR | | 41941 |
| HPV31 | E2 | 307 | 8 | CLRYRLSK | | 41942 |
| HPV31 | E2 | 307 | 9 | CLRYRLSKY | | 41943 |
| HPV31 | E2 | 307 | 10 | CLRYRLSKYK | | 41944 |
| HPV31 | E2 | 145 | 11 | CTVVEGQVNCK | | 41945 |
| HPV31 | E2 | 40 | 8 | CVLMYKAR | | 41946 |
| HPV31 | E2 | 301 | 9 | DANILKCLR | | 41947 |
| HPV31 | E2 | 301 | 10 | DANILKCLRY | | 41948 |
| HPV31 | E2 | 301 | 11 | DANILKCLRYR | | 41949 |
| HPV31 | E2 | 351 | 8 | DDFLNTVK | | 41950 |
| HPV31 | E2 | 122 | 9 | DGDVHNTMH | | 41951 |
| HPV31 | E2 | 122 | 10 | DGDVHNTMHY | | 41952 |
| HPV31 | E2 | 22 | 8 | DSKRLCDH | | 41953 |
| HPV31 | E2 | 22 | 11 | DSKRLCDHIDY | | 41954 |
| HPV31 | E2 | 124 | 8 | DVHNTMHY | | 41955 |
| HPV31 | E2 | 174 | 9 | EAKKYGTGK | | 41956 |
| HPV31 | E2 | 174 | 10 | EAKKYGTGKK | | 41957 |
| HPV31 | E2 | 39 | 9 | ECVLMYKAR | | 41958 |
| HPV31 | E2 | 149 | 10 | EGQVNCKGIY | | 41959 |
| HPV31 | E2 | 149 | 11 | EGQVNCKGIYY | | 41960 |
| HPV31 | E2 | 234 | 11 | EGVRRATTSTK | | 41961 |
| HPV31 | E2 | 204 | 10 | EISFAGIVTK | | 41962 |
| HPV31 | E2 | 48 | 9 | EMGIHSINH | | 41963 |
| HPV31 | E2 | 20 | 10 | ENDSKRLCDH | | 41964 |
| HPV31 | E2 | 80 | 8 | ETLNNTEY | | 41965 |
| HPV31 | E2 | 80 | 9 | ETLNNTEYK | | 41966 |
| HPV31 | E2 | 118 | 9 | EVQFDGDVH | | 41967 |
| HPV31 | E2 | 121 | 10 | FDGDVHNTMH | | 41968 |
| HPV31 | E2 | 121 | 11 | FDGDVHNTMHY | | 41969 |
| HPV31 | E2 | 171 | 8 | FTEEAKKY | | 41970 |
| HPV31 | E2 | 168 | 9 | FVNFTEEAK | | 41971 |
| HPV31 | E2 | 168 | 10 | FVNFTEEAKK | | 41972 |
| HPV31 | E2 | 168 | 11 | FVNFTEEAKKY | | 41973 |
| HPV31 | E2 | 108 | 8 | GCLKKHGY | | 41974 |
| HPV31 | E2 | 300 | 10 | GDANILKCLR | | 41975 |
| HPV31 | E2 | 300 | 11 | GDANILKCLRY | | 41976 |
| HPV31 | E2 | 123 | 8 | GDVHNTMH | | 41977 |
| HPV31 | E2 | 123 | 9 | GDVHNTMHY | | 41978 |
| HPV31 | E2 | 156 | 9 | GIYYVHEGH | | 41979 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV31 | E2 | 179 | 9 | GTGKKWEVH | | 41980 |
| HPV31 | E2 | 231 | 8 | GTSEGVRR | | 41981 |
| HPV31 | E2 | 235 | 10 | GVRRATTSTK | | 41982 |
| HPV31 | E2 | 235 | 11 | GVRRATTSTKR | | 41983 |
| HPV31 | E2 | 29 | 9 | HIDYWKHIR | | 41984 |
| HPV31 | E2 | 35 | 10 | HIRLECVLMY | | 41985 |
| HPV31 | E2 | 35 | 11 | HIRLECVLMYK | | 41986 |
| HPV31 | E2 | 297 | 10 | HLKGDANILK | | 41987 |
| HPV31 | E2 | 126 | 10 | HNTMHYTNWK | | 41988 |
| HPV31 | E2 | 30 | 8 | IDYWKHIR | | 41989 |
| HPV31 | E2 | 15 | 10 | ILEHYENDSK | | 41990 |
| HPV31 | E2 | 15 | 11 | ILEHYENDSKR | | 41991 |
| HPV31 | E2 | 304 | 8 | ILKCLRYR | | 41992 |
| HPV31 | E2 | 304 | 11 | ILKCLRYRLSK | | 41993 |
| HPV31 | E2 | 275 | 11 | ISAAACTNQTR | | 41994 |
| HPV31 | E2 | 205 | 9 | ISFAGIVTK | | 41995 |
| HPV31 | E2 | 45 | 8 | KAREMGIH | | 41996 |
| HPV31 | E2 | 306 | 9 | KCLRYRLSK | | 41997 |
| HPV31 | E2 | 306 | 10 | KCLRYRLSKY | | 41998 |
| HPV31 | E2 | 306 | 11 | KCLRYRLSKYK | | 41999 |
| HPV31 | E2 | 299 | 8 | KGDANILK | | 42000 |
| HPV31 | E2 | 299 | 11 | KGDANILKCLR | | 42001 |
| HPV31 | E2 | 155 | 10 | KGIYYVHEGH | | 42002 |
| HPV31 | E2 | 14 | 11 | KILEHYENDSK | | 42003 |
| HPV31 | E2 | 336 | 9 | KNAIVTLTY | | 42004 |
| HPV31 | E2 | 26 | 9 | LCDHIDYWK | | 42005 |
| HPV31 | E2 | 26 | 10 | LCDHIDYWKH | | 42006 |
| HPV31 | E2 | 230 | 8 | LGTSEGVR | | 42007 |
| HPV31 | E2 | 230 | 9 | LGTSEGVRR | | 42008 |
| HPV31 | E2 | 42 | 11 | LMYKAREMGIH | | 42009 |
| HPV31 | E2 | 8 | 11 | LNVCQDKILEH | | 42010 |
| HPV31 | E2 | 312 | 8 | LSKYKQLY | | 42011 |
| HPV31 | E2 | 4 | 11 | LSQRLNVCQDK | | 42012 |
| HPV31 | E2 | 103 | 9 | LTAPTGCLK | | 42013 |
| HPV31 | E2 | 103 | 10 | LTAPTGCLKK | | 42014 |
| HPV31 | E2 | 103 | 11 | LTAPTGCLKKH | | 42015 |
| HPV31 | E2 | 342 | 9 | LTYISTSQR | | 42016 |
| HPV31 | E2 | 49 | 8 | MGIHSINH | | 42017 |
| HPV31 | E2 | 78 | 10 | MLETLNNTEY | | 42018 |
| HPV31 | E2 | 78 | 11 | MLETLNNTEYK | | 42019 |
| HPV31 | E2 | 77 | 11 | MMLETLNNTEY | | 42020 |
| HPV31 | E2 | 337 | 8 | NAIVTLTY | | 42021 |
| HPV31 | E2 | 153 | 9 | NCKGIYYVH | | 42022 |
| HPV31 | E2 | 21 | 9 | NDSKRLCDH | | 42023 |
| HPV31 | E2 | 170 | 8 | NFTEEAKK | | 42024 |
| HPV31 | E2 | 170 | 9 | NFTEEAKKY | | 42025 |
| HPV31 | E2 | 303 | 8 | NILKCLRY | | 42026 |
| HPV31 | E2 | 303 | 9 | NILKCLRYR | | 42027 |
| HPV31 | E2 | 218 | 9 | NNTTTSNSK | | 42028 |
| HPV31 | E2 | 254 | 10 | NTHHPNKLLR | | 42029 |
| HPV31 | E2 | 127 | 9 | NTMHYTNWK | | 42030 |
| HPV31 | E2 | 219 | 8 | NTTTSNSK | | 42031 |
| HPV31 | E2 | 361 | 9 | NTVSVSTGY | | 42032 |
| HPV31 | E2 | 9 | 10 | NVCQDKILEH | | 42033 |
| HPV31 | E2 | 9 | 11 | NVCQDKILEHY | | 42034 |
| HPV31 | E2 | 60 | 9 | PALSVSKAK | | 42035 |
| HPV31 | E2 | 290 | 8 | PATTPIIH | | 42036 |
| HPV31 | E2 | 290 | 10 | PATTPIIHLK | | 42037 |
| HPV31 | E2 | 360 | 10 | PNTVSVSTGY | | 42038 |
| HPV31 | E2 | 106 | 8 | PTGCLKKH | | 42039 |
| HPV31 | E2 | 106 | 10 | PTGCLKKHGY | | 42040 |
| HPV31 | E2 | 12 | 8 | QDKILEHY | | 42041 |
| HPV31 | E2 | 120 | 11 | QFDGDVHNTMH | | 42042 |
| HPV31 | E2 | 317 | 11 | QLYEQVSSTWH | | 42043 |
| HPV31 | E2 | 151 | 8 | QVNCKGIY | | 42044 |
| HPV31 | E2 | 151 | 9 | QVNCKGIYY | | 42045 |
| HPV31 | E2 | 151 | 11 | QVNCKGIYYVH | | 42046 |
| HPV31 | E2 | 57 | 10 | QVVPALSVSK | | 42047 |
| HPV31 | E2 | 238 | 8 | RATTSTKR | | 42048 |
| HPV31 | E2 | 238 | 10 | RATTSTKRPR | | 42049 |
| HPV31 | E2 | 350 | 9 | RDDFLNTVK | | 42050 |
| HPV31 | E2 | 25 | 8 | RLCDHIDY | | 42051 |
| HPV31 | E2 | 25 | 10 | RLCDHIDYWK | | 42052 |
| HPV31 | E2 | 25 | 11 | RLCDHIDYWKH | | 42053 |
| HPV31 | E2 | 37 | 8 | RLECVLMY | | 42054 |

TABLE XVII-continued

A11 Motif Peptides

| Type | Protein | Position | No. of Amino Acids | Sequence | A*1101 | Seq. Id. No. |
|---|---|---|---|---|---|---|
| HPV31 | E2 | 37 | 9 | RLECVLMYK | | 42055 |
| HPV31 | E2 | 37 | 11 | RLECVLMYKAR | | 42056 |
| HPV31 | E2 | 7 | 8 | RLNVCQDK | | 42057 |
| HPV31 | E2 | 311 | 9 | RLSKYKQLY | | 42058 |
| HPV31 | E2 | 253 | 8 | RNTHHPNK | | 42059 |
| HPV31 | E2 | 253 | 11 | RNTHHPNKLLR | | 42060 |
| HPV31 | E2 | 247 | 10 | RTEPEHRNTH | | 42061 |
| HPV31 | E2 | 247 | 11 | RTEPEHRNTHH | | 42062 |
| HPV31 | E2 | 276 | 10 | SAAACTNQTR | | 42063 |
| HPV31 | E2 | 288 | 10 | SCPATTPIIH | | 42064 |
| HPV31 | E2 | 206 | 8 | SFAGIVTK | | 42065 |
| HPV31 | E2 | 242 | 11 | STKRPRTEPEH | | 42066 |
| HPV31 | E2 | 324 | 11 | STWHWTCTDGK | | 42067 |
| HPV31 | E2 | 216 | 11 | TANNTTTSNSK | | 42068 |
| HPV31 | E2 | 104 | 8 | TAPTGCLK | | 42069 |
| HPV31 | E2 | 104 | 9 | TAPTGCLKK | | 42070 |
| HPV31 | E2 | 104 | 10 | TAPTGCLKKH | | 42071 |
| HPV31 | E2 | 227 | 11 | TCALGTSEGVR | | 42072 |
| HPV31 | E2 | 329 | 8 | TCTDGKHK | | 42073 |
| HPV31 | E2 | 107 | 9 | TGCLKKHGY | | 42074 |
| HPV31 | E2 | 180 | 8 | TGKKWEVH | | 42075 |
| HPV31 | E2 | 81 | 8 | TLNNTEYK | | 42076 |
| HPV31 | E2 | 341 | 10 | TLTYISTSQR | | 42077 |
| HPV31 | E2 | 128 | 8 | TMHYTNWK | | 42078 |
| HPV31 | E2 | 128 | 11 | TMHYTNWKFIY | | 42079 |
| HPV31 | E2 | 93 | 10 | TMQQTSLELY | | 42080 |
| HPV31 | E2 | 292 | 8 | TTPIIHLK | | 42081 |
| HPV31 | E2 | 240 | 8 | TTSTKRPR | | 42082 |
| HPV31 | E2 | 116 | 11 | TVEVQFDGDVH | | 42083 |
| HPV31 | E2 | 362 | 8 | TVSVSTGY | | 42084 |
| HPV31 | E2 | 146 | 10 | TVVEGQVNCK | | 42085 |
| HPV31 | E2 | 10 | 9 | VCQDKILEH | | 42086 |
| HPV31 | E2 | 10 | 10 | VCQDKILEHY | | 42087 |
| HPV31 | E2 | 152 | 8 | VNCKGIYY | | 42088 |
| HPV31 | E2 | 152 | 10 | VNCKGIYYVH | | 42089 |
| HPV31 | E2 | 169 | 8 | VNFTEEAK | | 42090 |
| HPV31 | E2 | 169 | 9 | VNFTEEAKK | | 42091 |
| HPV31 | E2 | 169 | 10 | VNFTEEAKKY | | 42092 |
| HPV31 | E2 | 287 | 11 | VSCPATTPIIH | | 42093 |
| HPV31 | E2 | 340 | 11 | VTLTYISTSQR | | 42094 |
| HPV31 | E2 | 147 | 9 | VVEGQVNCK | | 42095 |
| HPV31 | E2 | 58 | 9 | VVPALSVSK | | 42096 |
| HPV31 | E2 | 58 | 11 | VVPALSVSKAK | | 42097 |
| HPV31 | E2 | 328 | 8 | WTCTDGKH | | 42098 |
| HPV31 | E2 | 328 | 9 | WTCTDGKHK | | 42099 |
| HPV31 | E2 | 92 | 11 | WTMQQTSLELY | | 42100 |
| HPV31 | E2 | 167 | 10 | YFVNFTEEAK | | 42101 |
| HPV31 | E2 | 167 | 11 | YFVNFTEEAKK | | 42102 |
| HPV31 | E2 | 178 | 10 | YGTGKKWEVH | | 42103 |
| HPV31 | E2 | 102 | 10 | YLTAPTGCLK | | 42104 |
| HPV31 | E2 | 102 | 11 | YLTAPTGCLKK | | 42105 |
| HPV31 | E2 | 131 | 8 | YTNWKFIY | | 42106 |
| HPV31 | E2 | 159 | 9 | YVHEGHITY | | 42107 |
| HPV31 | E5 | 53 | 11 | ATSPLRCFCIY | | 42108 |
| HPV31 | E5 | 59 | 10 | CFCIYVVFIY | | 42109 |
| HPV31 | E5 | 61 | 8 | CIYVVFIY | | 42110 |
| HPV31 | E5 | 20 | 11 | CVLLFVCLVIR | | 42111 |
| HPV31 | E5 | 60 | 9 | FCIYVVFIY | | 42112 |
| HPV31 | E5 | 66 | 10 | FIYIPLFVIH | | 42113 |
| HPV31 | E5 | 48 | 11 | ILWVIATSPLR | | 42114 |
| HPV31 | E5 | 23 | 8 | LFVCLVIR | | 42115 |
| HPV31 | E5 | 22 | 9 | LLFVCLVIR | | 42116 |
| HPV31 | E5 | 32 | 8 | LVLSVSVY | | 42117 |
| HPV31 | E5 | 70 | 8 | PLFVIHTH | | 42118 |
| HPV31 | E5 | 56 | 8 | PLRCFCIY | | 42119 |
| HPV31 | E5 | 31 | 9 | PLVLSVSVY | | 42120 |
| HPV31 | E5 | 58 | 11 | RCFCIYVVFIY | | 42121 |
| HPV31 | E5 | 54 | 10 | TSPLRCFCIY | | 42122 |
| HPV31 | E5 | 65 | 11 | VFIYIPLFVIH | | 42123 |
| HPV31 | E5 | 51 | 8 | VIATSPLR | | 42124 |
| HPV31 | E5 | 21 | 10 | VLLFVCLVIR | | 42125 |
| HPV31 | E5 | 50 | 9 | WVIATSPLR | | 42126 |
| HPV31 | E5 | 68 | 8 | YIPLFVIH | | 42127 |
| HPV31 | E5 | 68 | 10 | YIPLFVIHTH | | 42128 |
| HPV31 | E6 | 46 | 9 | AFTDLTIVY | | 42129 |

TABLE XVII-continued

A11 Motif Peptides

| Type | Protein | Position | No. of Amino Acids | Sequence | A*1101 | Seq. Id. No. |
|---|---|---|---|---|---|---|
| HPV31 | E6 | 46 | 10 | AFTDLTIVYR | | 42130 |
| HPV31 | E6 | 18 | 10 | ALEIPYDELR | | 42131 |
| HPV31 | E6 | 136 | 9 | CIACWRRPR | | 42132 |
| HPV31 | E6 | 63 | 8 | CTKCLRFY | | 42133 |
| HPV31 | E6 | 63 | 10 | CTKCLRFYSK | | 42134 |
| HPV31 | E6 | 56 | 10 | DDTPHGVCTK | | 42135 |
| HPV31 | E6 | 44 | 11 | DFAFTDLTIVY | | 42136 |
| HPV31 | E6 | 98 | 11 | DLLIRCITCQR | | 42137 |
| HPV31 | E6 | 57 | 9 | DTPHGVCTK | | 42138 |
| HPV31 | E6 | 75 | 10 | EFRWYRYSVY | | 42139 |
| HPV31 | E6 | 20 | 8 | EIPYDELR | | 42140 |
| HPV31 | E6 | 25 | 8 | ELRLNCVY | | 42141 |
| HPV31 | E6 | 25 | 10 | ELRLNCVYCK | | 42142 |
| HPV31 | E6 | 14 | 10 | ELSSALEIPY | | 42143 |
| HPV31 | E6 | 45 | 10 | FAFTDLTIVY | | 42144 |
| HPV31 | E6 | 45 | 11 | FAFTDLTIVYR | | 42145 |
| HPV31 | E6 | 47 | 8 | FTDLTIVY | | 42146 |
| HPV31 | E6 | 47 | 9 | FTDLTIVYR | | 42147 |
| HPV31 | E6 | 95 | 8 | GICDLLIR | | 42148 |
| HPV31 | E6 | 85 | 10 | GTTLEKLTNK | | 42149 |
| HPV31 | E6 | 61 | 8 | GVCTKCLR | | 42150 |
| HPV31 | E6 | 61 | 10 | GVCTKCLRFY | | 42151 |
| HPV31 | E6 | 60 | 9 | HGVCTKCLR | | 42152 |
| HPV31 | E6 | 60 | 11 | HGVCTKCLRFY | | 42153 |
| HPV31 | E6 | 118 | 9 | HLDKKKRFH | | 42154 |
| HPV31 | E6 | 126 | 10 | HNIGGRWTGR | | 42155 |
| HPV31 | E6 | 137 | 8 | IACWRRPR | | 42156 |
| HPV31 | E6 | 128 | 8 | IGGRWTGR | | 42157 |
| HPV31 | E6 | 52 | 9 | IVYRDDTPH | | 42158 |
| HPV31 | E6 | 65 | 8 | KCLRFYSK | | 42159 |
| HPV31 | E6 | 94 | 9 | KGICDLLIR | | 42160 |
| HPV31 | E6 | 3 | 8 | KNPAERPR | | 42161 |
| HPV31 | E6 | 3 | 9 | KNPAERPRK | | 42162 |
| HPV31 | E6 | 3 | 11 | KNPAERPRKLH | | 42163 |
| HPV31 | E6 | 72 | 8 | KVSEFRWY | | 42164 |
| HPV31 | E6 | 72 | 9 | KVSEFRWYR | | 42165 |
| HPV31 | E6 | 72 | 10 | KVSEFRWYRY | | 42166 |
| HPV31 | E6 | 110 | 8 | LCPEEKQR | | 42167 |
| HPV31 | E6 | 110 | 9 | LCPEEKQRH | 0.0001 | 42168 |
| HPV31 | E6 | 119 | 8 | LDKKKRFH | | 42169 |
| HPV31 | E6 | 100 | 9 | LIRCITCQR | | 42170 |
| HPV31 | E6 | 99 | 10 | LLIRCITCQR | | 42171 |
| HPV31 | E6 | 15 | 9 | LSSALEIPY | | 42172 |
| HPV31 | E6 | 50 | 11 | LTIVYRDDTPH | | 42173 |
| HPV31 | E6 | 1 | 8 | MFKNPAER | | 42174 |
| HPV31 | E6 | 1 | 10 | MFKNPAERPR | | 42175 |
| HPV31 | E6 | 1 | 11 | MFKNPAERPRK | | 42176 |
| HPV31 | E6 | 127 | 9 | NIGGRWTGR | | 42177 |
| HPV31 | E6 | 5 | 9 | PAERPRKLH | | 42178 |
| HPV31 | E6 | 109 | 9 | PLCPEEKQR | 0.0005 | 42179 |
| HPV31 | E6 | 109 | 10 | PLCPEEKQRH | | 42180 |
| HPV31 | E6 | 135 | 8 | RCIACWRR | | 42181 |
| HPV31 | E6 | 135 | 10 | RCIACWRRPR | | 42182 |
| HPV31 | E6 | 55 | 11 | RDDTPHGVCTK | | 42183 |
| HPV31 | E6 | 124 | 8 | RFHNIGGR | | 42184 |
| HPV31 | E6 | 68 | 10 | RFYSKVSEFR | | 42185 |
| HPV31 | E6 | 27 | 8 | RLNCVYCK | | 42186 |
| HPV31 | E6 | 17 | 11 | SALEIPYDELR | | 42187 |
| HPV31 | E6 | 16 | 8 | SSALEIPY | | 42188 |
| HPV31 | E6 | 82 | 9 | SVYGTTLEK | | 42189 |
| HPV31 | E6 | 105 | 11 | TCQRPLCPEEK | | 42190 |
| HPV31 | E6 | 48 | 8 | TDLTIVYR | | 42191 |
| HPV31 | E6 | 133 | 9 | TGRCIACWR | | 42192 |
| HPV31 | E6 | 133 | 10 | TGRCIACWRR | | 42193 |
| HPV31 | E6 | 51 | 10 | TIVYRDDTPH | | 42194 |
| HPV31 | E6 | 87 | 8 | TLEKLTNK | | 42195 |
| HPV31 | E6 | 92 | 11 | TNKGICDLLIR | | 42196 |
| HPV31 | E6 | 86 | 9 | TTLEKLTNK | | 42197 |
| HPV31 | E6 | 62 | 9 | VCTKCLRFY | | 42198 |
| HPV31 | E6 | 62 | 11 | VCTKCLRFYSK | | 42199 |
| HPV31 | E6 | 73 | 8 | VSEFRWYR | | 42200 |
| HPV31 | E6 | 73 | 9 | VSEFRWYRY | | 42201 |
| HPV31 | E6 | 132 | 10 | WTGRCIACWR | | 42202 |
| HPV31 | E6 | 132 | 11 | WTGRCIACWRR | | 42203 |
| HPV31 | E6 | 23 | 10 | YDELRLNCVY | | 42204 |

TABLE XVII-continued

A11 Motif Peptides

| Type | Protein | Position | No. of Amino Acids | Sequence | A*1101 | Seq. Id. No. |
|---|---|---|---|---|---|---|
| HPV31 | E6 | 84 | 11 | YGTTLEKLTNK | | 42205 |
| HPV31 | E6 | 70 | 8 | YSKVSEFR | | 42206 |
| HPV31 | E6 | 70 | 10 | YSKVSEFRWY | | 42207 |
| HPV31 | E6 | 70 | 11 | YSKVSEFRWYR | | 42208 |
| HPV31 | E6 | 81 | 10 | YSVYGTTLEK | | 42209 |
| HPV31 | E7 | 42 | 11 | AGQAEPDTSNY | | 42210 |
| HPV31 | E7 | 58 | 9 | CCQCKSTLR | | 42211 |
| HPV31 | E7 | 68 | 10 | CVQSTQVDIR | | 42212 |
| HPV31 | E7 | 14 | 10 | DLQPEATDLH | | 42213 |
| HPV31 | E7 | 18 | 8 | EATDLHCY | | 42214 |
| HPV31 | E7 | 4 | 8 | ETPTLQDY | | 42215 |
| HPV31 | E7 | 57 | 10 | FCCQCKSTLR | | 42216 |
| HPV31 | E7 | 87 | 11 | FGIVCPNCSTR | | 42217 |
| HPV31 | E7 | 88 | 10 | GIVCPNCSTR | | 42218 |
| HPV31 | E7 | 89 | 9 | IVCPNCSTR | | 42219 |
| HPV31 | E7 | 54 | 9 | IVTFCCQCK | | 42220 |
| HPV31 | E7 | 67 | 11 | LCVQSTQVDIR | | 42221 |
| HPV31 | E7 | 13 | 11 | LDLQPEATDLH | | 42222 |
| HPV31 | E7 | 53 | 10 | NIVTFCCQCK | | 42223 |
| HPV31 | E7 | 44 | 9 | QAEPDTSNY | | 42224 |
| HPV31 | E7 | 70 | 8 | QSTQVDIR | | 42225 |
| HPV31 | E7 | 2 | 10 | RGETPTLQDY | | 42226 |
| HPV31 | E7 | 56 | 11 | TFCCQCKSTLR | | 42227 |
| HPV31 | E7 | 90 | 8 | VCPNCSTR | | 42228 |
| HPV31 | E7 | 55 | 8 | VTFCCQCK | | 42229 |
| HPV31 | E7 | 52 | 11 | YNIVTFCCQCK | | 42230 |
| HPV31 | L1 | 347 | 11 | AAIANSDTTFK | | 42231 |
| HPV31 | L1 | 102 | 9 | ACVGLEVGR | | 42232 |
| HPV31 | L1 | 386 | 8 | ADIMTYIH | | 42233 |
| HPV31 | L1 | 458 | 10 | ADLDQFPLGR | | 42234 |
| HPV31 | L1 | 458 | 11 | ADLDQFPLGRK | | 42235 |
| HPV31 | L1 | 137 | 9 | AGGPGTDNR | | 42236 |
| HPV31 | L1 | 37 | 11 | AGSARLLTVGH | | 42237 |
| HPV31 | L1 | 473 | 8 | AGYRARPK | | 42238 |
| HPV31 | L1 | 473 | 10 | AGYRARPKFK | | 42239 |
| HPV31 | L1 | 348 | 10 | AIANSDTTFK | | 42240 |
| HPV31 | L1 | 426 | 11 | AITCQKTAPQK | | 42241 |
| HPV31 | L1 | 208 | 11 | AMDFTALQDTK | | 42242 |
| HPV31 | L1 | 350 | 8 | ANSDTTFK | | 42243 |
| HPV31 | L1 | 491 | 8 | ASTTTPAK | | 42244 |
| HPV31 | L1 | 491 | 9 | ASTTTPAKR | | 42245 |
| HPV31 | L1 | 491 | 10 | ASTTTPAKRK | | 42246 |
| HPV31 | L1 | 491 | 11 | ASTTTPAKRKK | | 42247 |
| HPV31 | L1 | 285 | 8 | ATLANSTY | | 42248 |
| HPV31 | L1 | 226 | 10 | CNSICKYPDY | | 42249 |
| HPV31 | L1 | 103 | 8 | CVGLEVGR | | 42250 |
| HPV31 | L1 | 304 | 9 | DAQIFNKPY | | 42251 |
| HPV31 | L1 | 185 | 8 | DCPPLELK | | 42252 |
| HPV31 | L1 | 128 | 8 | DDTENSNR | | 42253 |
| HPV31 | L1 | 128 | 9 | DDTENSNRY | | 42254 |
| HPV31 | L1 | 210 | 9 | DFTALQDTK | | 42255 |
| HPV31 | L1 | 224 | 8 | DICNSICK | | 42256 |
| HPV31 | L1 | 224 | 9 | DICNSICKY | | 42257 |
| HPV31 | L1 | 459 | 9 | DLDQFPLGR | | 42258 |
| HPV31 | L1 | 459 | 10 | DLDQFPLGRK | | 42259 |
| HPV31 | L1 | 372 | 10 | DLQFIFQLCK | | 42260 |
| HPV31 | L1 | 56 | 10 | DNPKKIVVPK | | 42261 |
| HPV31 | L1 | 143 | 10 | DNRECISMDY | | 42262 |
| HPV31 | L1 | 143 | 11 | DNRECISMDYK | | 42263 |
| HPV31 | L1 | 129 | 8 | DTENSNRY | | 42264 |
| HPV31 | L1 | 245 | 8 | DTLFFYLR | | 42265 |
| HPV31 | L1 | 245 | 9 | DTLFFYLRR | | 42266 |
| HPV31 | L1 | 88 | 11 | DTSFYNPETQR | | 42267 |
| HPV31 | L1 | 353 | 10 | DTTFKSSNFK | | 42268 |
| HPV31 | L1 | 146 | 8 | ECISMDYK | | 42269 |
| HPV31 | L1 | 270 | 8 | ESVPTDLY | | 42270 |
| HPV31 | L1 | 270 | 10 | ESVPTDLYIK | | 42271 |
| HPV31 | L1 | 127 | 9 | FDDTENSNR | | 42272 |
| HPV31 | L1 | 127 | 10 | FDDTENSNRY | | 42273 |
| HPV31 | L1 | 371 | 11 | FDLQFIFQLCK | | 42274 |
| HPV31 | L1 | 84 | 9 | FGFPDTSFY | | 42275 |
| HPV31 | L1 | 469 | 8 | FLLQAGYR | | 42276 |
| HPV31 | L1 | 469 | 10 | FLLQAGYRAR | | 42277 |
| HPV31 | L1 | 308 | 9 | FNKPYWMQR | | 42278 |
| HPV31 | L1 | 211 | 8 | FTALQDTK | | 42279 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV31 | L1 | 257 | 8 | FVRHFFNR | | 42280 |
| HPV31 | L1 | 421 | 11 | FVTSQAITCQK | | 42281 |
| HPV31 | L1 | 331 | 9 | FVTVVDTTR | | 42282 |
| HPV31 | L1 | 161 | 9 | GCKPPIGEH | | 42283 |
| HPV31 | L1 | 184 | 9 | GDCPPLELK | | 42284 |
| HPV31 | L1 | 244 | 9 | GDTLFFYLR | | 42285 |
| HPV31 | L1 | 244 | 10 | GDTLFFYLRR | | 42286 |
| HPV31 | L1 | 85 | 8 | GFPDTSFY | | 42287 |
| HPV31 | L1 | 138 | 8 | GGPGTDNR | | 42288 |
| HPV31 | L1 | 117 | 10 | GISGHPLLNK | | 42289 |
| HPV31 | L1 | 68 | 8 | GLQYRVFR | | 42290 |
| HPV31 | L1 | 68 | 10 | GLQYRVFRVR | | 42291 |
| HPV31 | L1 | 38 | 10 | GSARLLTVGH | | 42292 |
| HPV31 | L1 | 413 | 8 | GSLEDTYR | | 42293 |
| HPV31 | L1 | 282 | 11 | GSTATLANSTY | | 42294 |
| HPV31 | L1 | 349 | 9 | IANSDTTFK | | 42295 |
| HPV31 | L1 | 229 | 9 | ICKYPDYLK | | 42296 |
| HPV31 | L1 | 225 | 8 | ICNSICKY | | 42297 |
| HPV31 | L1 | 225 | 11 | ICNSICKYPDY | | 42298 |
| HPV31 | L1 | 307 | 10 | IFNKPYWMQR | | 42299 |
| HPV31 | L1 | 118 | 9 | ISGHPLLNK | | 42300 |
| HPV31 | L1 | 427 | 10 | ITCQKTAPQK | | 42301 |
| HPV31 | L1 | 382 | 10 | ITLSADIMTY | | 42302 |
| HPV31 | L1 | 61 | 11 | IVVPKVSGLQY | | 42303 |
| HPV31 | L1 | 443 | 11 | KDYVFWEVNLK | | 42304 |
| HPV31 | L1 | 126 | 10 | KFDDTENSNR | | 42305 |
| HPV31 | L1 | 126 | 11 | KFDDTENSNRY | | 42306 |
| HPV31 | L1 | 83 | 10 | KFGFPDTSFY | | 42307 |
| HPV31 | L1 | 468 | 8 | KFLLQAGY | | 42308 |
| HPV31 | L1 | 468 | 9 | KFLLQAGYR | | 42309 |
| HPV31 | L1 | 468 | 11 | KFLLQAGYRAR | | 42310 |
| HPV31 | L1 | 381 | 11 | KITLSADIMTY | | 42311 |
| HPV31 | L1 | 357 | 8 | KSSNFKEY | | 42312 |
| HPV31 | L1 | 357 | 10 | KSSNFKEYLR | | 42313 |
| HPV31 | L1 | 357 | 11 | KSSNFKEYLRH | | 42314 |
| HPV31 | L1 | 431 | 8 | KTAPQKPK | | 42315 |
| HPV31 | L1 | 65 | 8 | KVSGLQYR | | 42316 |
| HPV31 | L1 | 65 | 11 | KVSGLQYRVFR | | 42317 |
| HPV31 | L1 | 20 | 8 | KVVSTDEY | | 42318 |
| HPV31 | L1 | 20 | 11 | KVVSTDEYVTR | | 42319 |
| HPV31 | L1 | 223 | 9 | LDICNSICK | | 42320 |
| HPV31 | L1 | 223 | 10 | LDICNSICKY | | 42321 |
| HPV31 | L1 | 460 | 8 | LDQFPLGR | | 42322 |
| HPV31 | L1 | 460 | 9 | LDQFPLGRK | | 42323 |
| HPV31 | L1 | 330 | 10 | LFVTVVDTTR | | 42324 |
| HPV31 | L1 | 160 | 10 | LGCKPPIGEH | | 42325 |
| HPV31 | L1 | 465 | 11 | LGRKFLLQAGY | | 42326 |
| HPV31 | L1 | 114 | 8 | LGVGISGH | | 42327 |
| HPV31 | L1 | 159 | 11 | LLGCKPPIGEH | | 42328 |
| HPV31 | L1 | 470 | 9 | LLQAGYRAR | | 42329 |
| HPV31 | L1 | 470 | 11 | LLQAGYRARPK | | 42330 |
| HPV31 | L1 | 42 | 8 | LLTVGHPY | | 42331 |
| HPV31 | L1 | 42 | 9 | LLTVGHPYY | | 42332 |
| HPV31 | L1 | 384 | 8 | LSADIMTY | | 42333 |
| HPV31 | L1 | 384 | 10 | LSADIMTYIH | | 42334 |
| HPV31 | L1 | 43 | 8 | LTVGHPYY | | 42335 |
| HPV31 | L1 | 209 | 10 | MDFTALQDTK | | 42336 |
| HPV31 | L1 | 256 | 9 | MFVRHFFNR | | 42337 |
| HPV31 | L1 | 300 | 11 | MVTSDAQIFNK | | 42338 |
| HPV31 | L1 | 360 | 8 | NFKEYLRH | | 42339 |
| HPV31 | L1 | 32 | 10 | NIYYHAGSAR | | 42340 |
| HPV31 | L1 | 227 | 9 | NSICKYPDY | | 42341 |
| HPV31 | L1 | 227 | 11 | NSICKYPDYLK | | 42342 |
| HPV31 | L1 | 496 | 8 | PAKRKKTK | | 42343 |
| HPV31 | L1 | 496 | 9 | PAKRKKTKK | | 42344 |
| HPV31 | L1 | 233 | 11 | PDYLKMVAEPY | | 42345 |
| HPV31 | L1 | 183 | 10 | PGDCPPLELK | | 42346 |
| HPV31 | L1 | 165 | 8 | PIGEHWGK | | 42347 |
| HPV31 | L1 | 222 | 10 | PLDICNSICK | | 42348 |
| HPV31 | L1 | 222 | 11 | PLDICNSICKY | | 42349 |
| HPV31 | L1 | 113 | 9 | PLGVGISGH | | 42350 |
| HPV31 | L1 | 489 | 10 | PSASTTTPAK | | 42351 |
| HPV31 | L1 | 489 | 11 | PSASTTTPAKR | | 42352 |
| HPV31 | L1 | 411 | 9 | PSGSLEDTY | | 42353 |
| HPV31 | L1 | 411 | 10 | PSGSLEDTYR | | 42354 |

TABLE XVII-continued

A11 Motif Peptides

| Type | Protein | Position | No. of Amino Acids | Sequence | A*1101 | Seq. Id. No. |
|---|---|---|---|---|---|---|
| HPV31 | L1 | 17 | 11 | PVSKVVSTDEY | | 42355 |
| HPV31 | L1 | 472 | 9 | QAGYRARPK | | 42356 |
| HPV31 | L1 | 472 | 11 | QAGYRARPKFK | | 42357 |
| HPV31 | L1 | 374 | 8 | QFIFQLCK | | 42358 |
| HPV31 | L1 | 306 | 11 | QIFNKPYWMQR | | 42359 |
| HPV31 | L1 | 156 | 8 | QLCLLGCK | | 42360 |
| HPV31 | L1 | 329 | 11 | QLFVTVVDTTR | | 42361 |
| HPV31 | L1 | 255 | 10 | QMFVRHFFNR | | 42362 |
| HPV31 | L1 | 154 | 10 | QTQLCLLGCK | | 42363 |
| HPV31 | L1 | 476 | 10 | RARPKFKAGK | | 42364 |
| HPV31 | L1 | 476 | 11 | RARPKFKAGKR | | 42365 |
| HPV31 | L1 | 41 | 9 | RLLTVGHPY | | 42366 |
| HPV31 | L1 | 41 | 10 | RLLTVGHPYY | | 42367 |
| HPV31 | L1 | 75 | 9 | RVRLPDPNK | | 42368 |
| HPV31 | L1 | 385 | 9 | SADIMTYIH | | 42369 |
| HPV31 | L1 | 457 | 11 | SADLDQFPLGR | | 42370 |
| HPV31 | L1 | 39 | 9 | SARLLTVGH | | 42371 |
| HPV31 | L1 | 39 | 11 | SARLLTVGHPY | | 42372 |
| HPV31 | L1 | 490 | 9 | SASTTTPAK | | 42373 |
| HPV31 | L1 | 490 | 10 | SASTTTPAKR | | 42374 |
| HPV31 | L1 | 490 | 11 | SASTTTPAKRK | | 42375 |
| HPV31 | L1 | 303 | 8 | SDAQIFNK | | 42376 |
| HPV31 | L1 | 303 | 10 | SDAQIFNKPY | | 42377 |
| HPV31 | L1 | 55 | 11 | SDNPKKIVVPK | | 42378 |
| HPV31 | L1 | 352 | 11 | SDTTFKSSNFK | | 42379 |
| HPV31 | L1 | 90 | 9 | SFYNPETQR | | 42380 |
| HPV31 | L1 | 119 | 8 | SGHPLLNK | | 42381 |
| HPV31 | L1 | 67 | 9 | SGLQYRVFR | | 42382 |
| HPV31 | L1 | 67 | 11 | SGLQYRVFRVR | | 42383 |
| HPV31 | L1 | 412 | 8 | SGSLEDTY | | 42384 |
| HPV31 | L1 | 412 | 9 | SGSLEDTYR | | 42385 |
| HPV31 | L1 | 228 | 8 | SICKYPDY | | 42386 |
| HPV31 | L1 | 228 | 10 | SICKYPDYLK | | 42387 |
| HPV31 | L1 | 51 | 9 | SIPKSDNPK | | 42388 |
| HPV31 | L1 | 51 | 10 | SIPKSDNPKK | | 42389 |
| HPV31 | L1 | 2 | 11 | SLWRPSEATVY | | 42390 |
| HPV31 | L1 | 359 | 8 | SNFKEYLR | | 42391 |
| HPV31 | L1 | 359 | 9 | SNFKEYLRH | | 42392 |
| HPV31 | L1 | 358 | 9 | SSNFKEYLR | | 42393 |
| HPV31 | L1 | 358 | 10 | SSNFKEYLRH | | 42394 |
| HPV31 | L1 | 283 | 10 | STATLANSTY | | 42395 |
| HPV31 | L1 | 23 | 8 | STDEYVTR | | 42396 |
| HPV31 | L1 | 492 | 8 | STTTPAKR | | 42397 |
| HPV31 | L1 | 492 | 9 | STTTPAKRK | | 42398 |
| HPV31 | L1 | 492 | 10 | STTTPAKRKK | | 42399 |
| HPV31 | L1 | 271 | 9 | SVPTDLYIK | | 42400 |
| HPV31 | L1 | 284 | 9 | TATLANSTY | | 42401 |
| HPV31 | L1 | 428 | 9 | TCQKTAPQK | | 42402 |
| HPV31 | L1 | 428 | 11 | TCQKTAPQKPK | | 42403 |
| HPV31 | L1 | 24 | 11 | TDEYVTRTNIY | | 42404 |
| HPV31 | L1 | 142 | 11 | TDNRECISMDY | | 42405 |
| HPV31 | L1 | 355 | 8 | TFKSSNFK | | 42406 |
| HPV31 | L1 | 355 | 10 | TFKSSNFKEY | | 42407 |
| HPV31 | L1 | 246 | 8 | TLFFYLRR | | 42408 |
| HPV31 | L1 | 383 | 9 | TLSADIMTY | | 42409 |
| HPV31 | L1 | 383 | 11 | TLSADIMTYIH | | 42410 |
| HPV31 | L1 | 31 | 11 | TNIYYHAGSAR | | 42411 |
| HPV31 | L1 | 302 | 9 | TSDAQIFNK | | 42412 |
| HPV31 | L1 | 302 | 11 | TSDAQIFNKPY | | 42413 |
| HPV31 | L1 | 89 | 10 | TSFYNPETQR | | 42414 |
| HPV31 | L1 | 423 | 9 | TSQAITCQK | | 42415 |
| HPV31 | L1 | 354 | 9 | TTFKSSNFK | | 42416 |
| HPV31 | L1 | 354 | 11 | TTFKSSNFKEY | | 42417 |
| HPV31 | L1 | 494 | 8 | TTAPKRKK | | 42418 |
| HPV31 | L1 | 494 | 10 | TTAPKRKKTK | | 42419 |
| HPV31 | L1 | 494 | 11 | TTAPKRKKTKK | | 42420 |
| HPV31 | L1 | 493 | 8 | TTTPAKRK | | 42421 |
| HPV31 | L1 | 493 | 9 | TTTPAKRKK | | 42422 |
| HPV31 | L1 | 493 | 11 | TTTPAKRKKTK | | 42423 |
| HPV31 | L1 | 267 | 11 | TVGESVPTDLY | | 42424 |
| HPV31 | L1 | 44 | 11 | TVGHPYYSIPK | | 42425 |
| HPV31 | L1 | 10 | 11 | TVYLPPVPVSK | | 42426 |
| HPV31 | L1 | 73 | 11 | VFRVRLPDPNK | | 42427 |
| HPV31 | L1 | 446 | 8 | VFWEVNLK | | 42428 |
| HPV31 | L1 | 446 | 10 | VFWEVNLKEK | | 42429 |

TABLE XVII-continued

A11 Motif Peptides

| Type | Protein | Position | No. of Amino Acids | Sequence | A*1101 | Seq. Id. No. |
|---|---|---|---|---|---|---|
| HPV31 | L1 | 268 | 10 | VGESVPTDLY | | 42430 |
| HPV31 | L1 | 45 | 10 | VGHPYYSIPK | | 42431 |
| HPV31 | L1 | 116 | 11 | VGISGHPLLNK | | 42432 |
| HPV31 | L1 | 66 | 10 | VSGLQYRVFR | | 42433 |
| HPV31 | L1 | 18 | 10 | VSKVVSTDEY | | 42434 |
| HPV31 | L1 | 22 | 9 | VSTDEYVTR | | 42435 |
| HPV31 | L1 | 28 | 8 | VTRTNIYY | | 42436 |
| HPV31 | L1 | 28 | 9 | VTRTNIYYH | | 42437 |
| HPV31 | L1 | 301 | 10 | VTSDAQIFNK | | 42438 |
| HPV31 | L1 | 422 | 10 | VTSQAITCQK | | 42439 |
| HPV31 | L1 | 332 | 8 | VTVVDTTR | | 42440 |
| HPV31 | L1 | 62 | 10 | VVPKVSGLQY | | 42441 |
| HPV31 | L1 | 62 | 11 | VVPKVSGLQYR | | 42442 |
| HPV31 | L1 | 21 | 10 | VVSTDEYVTR | | 42443 |
| HPV31 | L1 | 101 | 10 | WACVGLEVGR | | 42444 |
| HPV31 | L1 | 313 | 8 | WMQRAQGH | | 42445 |
| HPV31 | L1 | 136 | 10 | YAGGPGTDNR | | 42446 |
| HPV31 | L1 | 243 | 8 | YGDTLFFY | | 42447 |
| HPV31 | L1 | 243 | 10 | YGDTLFFYLR | | 42448 |
| HPV31 | L1 | 243 | 11 | YGDTLFFYLRR | | 42449 |
| HPV31 | L1 | 235 | 9 | YLKMVAEPY | | 42450 |
| HPV31 | L1 | 12 | 9 | YLPPVPVSK | | 42451 |
| HPV31 | L1 | 250 | 10 | YLRREQMFVR | | 42452 |
| HPV31 | L1 | 250 | 11 | YLRREQMFVRH | | 42453 |
| HPV31 | L1 | 50 | 10 | YSIPKSDNPK | | 42454 |
| HPV31 | L1 | 50 | 11 | YSIPKSDNPKK | | 42455 |
| HPV31 | L1 | 445 | 9 | YVFWEVNLK | | 42456 |
| HPV31 | L1 | 445 | 11 | YVFWEVNLKEK | | 42457 |
| HPV31 | L1 | 27 | 8 | YVTRTNIY | | 42458 |
| HPV31 | L1 | 27 | 9 | YVTRTNIYY | | 42459 |
| HPV31 | L1 | 27 | 10 | YVTRTNIYYH | | 42460 |
| HPV31 | L2 | 25 | 11 | AGTCPSDVIPK | | 42461 |
| HPV31 | L2 | 143 | 11 | AILDVTSVSTH | | 42462 |
| HPV31 | L2 | 281 | 10 | ALHRPALTSR | | 42463 |
| HPV31 | L2 | 281 | 11 | ALHRPALTSRR | | 42464 |
| HPV31 | L2 | 286 | 10 | ALTSRRNTVR | | 42465 |
| HPV31 | L2 | 286 | 11 | ALTSRRNTVRY | | 42466 |
| HPV31 | L2 | 13 | 11 | ASATQLYQTCK | | 42467 |
| HPV31 | L2 | 311 | 8 | ATIGARVH | | 42468 |
| HPV31 | L2 | 311 | 9 | ATIGARVHY | | 42469 |
| HPV31 | L2 | 311 | 10 | ATIGARVHYY | | 42470 |
| HPV31 | L2 | 311 | 11 | ATIGARVHYYY | | 42471 |
| HPV31 | L2 | 15 | 9 | ATQLYQTCK | | 42472 |
| HPV31 | L2 | 376 | 11 | AVQSTSAVSAY | | 42473 |
| HPV31 | L2 | 275 | 9 | DFLDIIALH | | 42474 |
| HPV31 | L2 | 275 | 10 | DFLDIIALHR | | 42475 |
| HPV31 | L2 | 360 | 10 | DFTVDTPATH | | 42476 |
| HPV31 | L2 | 438 | 8 | DFYLHPSY | | 42477 |
| HPV31 | L2 | 438 | 9 | DFYLHPSYY | | 42478 |
| HPV31 | L2 | 435 | 8 | DGGDFYLH | | 42479 |
| HPV31 | L2 | 435 | 11 | DGGDFYLHPSY | | 42480 |
| HPV31 | L2 | 116 | 10 | DVGAPAPIPH | | 42481 |
| HPV31 | L2 | 31 | 8 | DVIPKIEH | | 42482 |
| HPV31 | L2 | 146 | 8 | DVTSVSTH | | 42483 |
| HPV31 | L2 | 259 | 10 | ESLYFSNTSH | | 42484 |
| HPV31 | L2 | 253 | 10 | ETVNAEESLY | | 42485 |
| HPV31 | L2 | 276 | 8 | FLDIIALH | | 42486 |
| HPV31 | L2 | 276 | 9 | FLDIIALHR | | 42487 |
| HPV31 | L2 | 237 | 11 | FLSAPKQLITY | | 42488 |
| HPV31 | L2 | 404 | 10 | FSGPDVPIEH | | 42489 |
| HPV31 | L2 | 361 | 9 | FTVDTPATH | | 42490 |
| HPV31 | L2 | 433 | 8 | FVDGGDFY | | 42491 |
| HPV31 | L2 | 433 | 10 | FVDGGDFYLH | | 42492 |
| HPV31 | L2 | 118 | 8 | GAPAPIPH | | 42493 |
| HPV31 | L2 | 314 | 8 | GARVHYYY | | 42494 |
| HPV31 | L2 | 310 | 9 | GATIGARVH | | 42495 |
| HPV31 | L2 | 310 | 10 | GATIGARVHY | | 42496 |
| HPV31 | L2 | 310 | 11 | GATIGARVHYY | | 42497 |
| HPV31 | L2 | 437 | 9 | GDFYLHPSY | | 42498 |
| HPV31 | L2 | 437 | 10 | GDFYLHPSYY | | 42499 |
| HPV31 | L2 | 436 | 10 | GGDFYLHPSY | | 42500 |
| HPV31 | L2 | 436 | 11 | GGDFYLHPSYY | | 42501 |
| HPV31 | L2 | 59 | 11 | GIGSGSGTGGR | | 42502 |
| HPV31 | L2 | 221 | 11 | GLYSKATQQVK | | 42503 |
| HPV31 | L2 | 300 | 9 | GNKQTLRTR | | 42504 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV31 | L2 | 61 | 9 | GSGSGTGGR | | 42505 |
| HPV31 | L2 | 63 | 10 | GSGTGGRTGY | | 42506 |
| HPV31 | L2 | 26 | 10 | GTCPSDVIPK | | 42507 |
| HPV31 | L2 | 65 | 8 | GTGGRTGY | | 42508 |
| HPV31 | L2 | 213 | 11 | GVRRPARLGLY | | 42509 |
| HPV31 | L2 | 38 | 10 | HTTIADQILR | | 42510 |
| HPV31 | L2 | 38 | 11 | HTTIADQILRY | | 42511 |
| HPV31 | L2 | 41 | 8 | IADQILRY | | 42512 |
| HPV31 | L2 | 280 | 11 | IALHRPALTSR | | 42513 |
| HPV31 | L2 | 233 | 10 | IDPTFLSAPK | | 42514 |
| HPV31 | L2 | 403 | 11 | IFSGPDVPIEH | | 42515 |
| HPV31 | L2 | 432 | 9 | IFVDGGDFY | | 42516 |
| HPV31 | L2 | 432 | 11 | IFVDGGDFYLH | | 42517 |
| HPV31 | L2 | 313 | 8 | IGARVHYY | | 42518 |
| HPV31 | L2 | 313 | 9 | IGARVHYYY | | 42519 |
| HPV31 | L2 | 60 | 10 | IGSGSGTGGR | | 42520 |
| HPV31 | L2 | 144 | 10 | ILDVTSVSTH | | 42521 |
| HPV31 | L2 | 205 | 11 | ITSSTPIPGVR | | 42522 |
| HPV31 | L2 | 245 | 8 | ITYENPAY | | 42523 |
| HPV31 | L2 | 277 | 8 | LDIIALHR | | 42524 |
| HPV31 | L2 | 145 | 9 | LDVTSVSTH | | 42525 |
| HPV31 | L2 | 299 | 8 | LGNKQTLR | | 42526 |
| HPV31 | L2 | 299 | 10 | LGNKQTLRTR | | 42527 |
| HPV31 | L2 | 244 | 9 | LITYENPAY | | 42528 |
| HPV31 | L2 | 176 | 11 | LLLSSSSISTH | | 42529 |
| HPV31 | L2 | 177 | 10 | LLSSSSISTH | | 42530 |
| HPV31 | L2 | 348 | 9 | LNDGLYDIY | | 42531 |
| HPV31 | L2 | 238 | 10 | LSAPKQLITY | | 42532 |
| HPV31 | L2 | 178 | 9 | LSSSSISTH | | 42533 |
| HPV31 | L2 | 178 | 11 | LSSSSISTHNY | | 42534 |
| HPV31 | L2 | 287 | 9 | LTSRRNTVR | | 42535 |
| HPV31 | L2 | 287 | 10 | LTSRRNTVRY | | 42536 |
| HPV31 | L2 | 447 | 8 | MLKRRRKR | | 42537 |
| HPV31 | L2 | 447 | 11 | MLKRRRKRVSY | | 42538 |
| HPV31 | L2 | 349 | 8 | NDGLYDIY | | 42539 |
| HPV31 | L2 | 292 | 11 | NTVRYSRLGNK | | 42540 |
| HPV31 | L2 | 285 | 11 | PALTSRRNTVR | | 42541 |
| HPV31 | L2 | 217 | 9 | PARLGLYSK | | 42542 |
| HPV31 | L2 | 274 | 10 | PDFLDIIALH | | 42543 |
| HPV31 | L2 | 274 | 11 | PDFLDIIALHR | | 42544 |
| HPV31 | L2 | 212 | 8 | PGVRRPAR | | 42545 |
| HPV31 | L2 | 210 | 10 | PIPGVRRPAR | | 42546 |
| HPV31 | L2 | 29 | 10 | PSDVIPKIEH | | 42547 |
| HPV31 | L2 | 443 | 8 | PSYYMLKR | | 42548 |
| HPV31 | L2 | 443 | 9 | PSYYMLKRR | | 42549 |
| HPV31 | L2 | 443 | 10 | PSYYMLKRRR | | 42550 |
| HPV31 | L2 | 443 | 11 | PSYYMLKRRRK | | 42551 |
| HPV31 | L2 | 235 | 8 | PTFLSAPK | | 42552 |
| HPV31 | L2 | 167 | 9 | PTPAETSGH | | 42553 |
| HPV31 | L2 | 243 | 10 | QLITYENPAY | | 42554 |
| HPV31 | L2 | 378 | 9 | QSTSAVSAY | | 42555 |
| HPV31 | L2 | 12 | 8 | RASATQLY | | 42556 |
| HPV31 | L2 | 298 | 9 | RLGNKQTLR | | 42557 |
| HPV31 | L2 | 298 | 11 | RLGNKQTLRTR | | 42558 |
| HPV31 | L2 | 291 | 8 | RNTVRYSR | | 42559 |
| HPV31 | L2 | 308 | 9 | RSGATIGAR | | 42560 |
| HPV31 | L2 | 308 | 11 | RSGATIGARVH | | 42561 |
| HPV31 | L2 | 2 | 8 | RSKRSTKR | | 42562 |
| HPV31 | L2 | 2 | 10 | RSKRSTKRTK | | 42563 |
| HPV31 | L2 | 2 | 11 | RSKRSTKRTKR | | 42564 |
| HPV31 | L2 | 5 | 8 | RSTKRTKR | | 42565 |
| HPV31 | L2 | 69 | 10 | RTGYVPLSTR | | 42566 |
| HPV31 | L2 | 9 | 11 | RTKRASATQLY | | 42567 |
| HPV31 | L2 | 306 | 11 | RTRSGATIGAR | | 42568 |
| HPV31 | L2 | 239 | 9 | SAPKQLITY | | 42569 |
| HPV31 | L2 | 14 | 10 | SATQLYQTCK | | 42570 |
| HPV31 | L2 | 30 | 9 | SDVIPKIEH | | 42571 |
| HPV31 | L2 | 309 | 8 | SGATIGAR | | 42572 |
| HPV31 | L2 | 309 | 10 | SGATIGARVH | | 42573 |
| HPV31 | L2 | 309 | 11 | SGATIGARVHY | | 42574 |
| HPV31 | L2 | 405 | 9 | SGPDVPIEH | | 42575 |
| HPV31 | L2 | 62 | 8 | SGSGTGGR | | 42576 |
| HPV31 | L2 | 62 | 11 | SGSGTGGRTGY | | 42577 |
| HPV31 | L2 | 64 | 9 | SGTGGRTGY | | 42578 |
| HPV31 | L2 | 431 | 10 | SIFVDGGDFY | | 42579 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV31 | L2 | 260 | 9 | SLYFSNTSH | | 42580 |
| HPV31 | L2 | 181 | 8 | SSISTHNY | | 42581 |
| HPV31 | L2 | 180 | 9 | SSSISTHNY | | 42582 |
| HPV31 | L2 | 179 | 8 | SSSSISTH | | 42583 |
| HPV31 | L2 | 179 | 10 | SSSSISTHNY | | 42584 |
| HPV31 | L2 | 207 | 9 | SSTPIPGVR | | 42585 |
| HPV31 | L2 | 207 | 10 | SSTPIPGVRR | | 42586 |
| HPV31 | L2 | 346 | 8 | STLNDGLY | | 42587 |
| HPV31 | L2 | 346 | 11 | STLNDGLYDIY | | 42588 |
| HPV31 | L2 | 208 | 8 | STPIPGVR | | 42589 |
| HPV31 | L2 | 208 | 9 | STPIPGVRR | | 42590 |
| HPV31 | L2 | 379 | 8 | STSAVSAY | | 42591 |
| HPV31 | L2 | 80 | 11 | STVSEASIPIR | | 42592 |
| HPV31 | L2 | 27 | 9 | TCPSDVIPK | | 42593 |
| HPV31 | L2 | 359 | 11 | TDFTVDTPATH | | 42594 |
| HPV31 | L2 | 70 | 9 | TGYVPLSTR | | 42595 |
| HPV31 | L2 | 40 | 8 | TIADQILR | | 42596 |
| HPV31 | L2 | 40 | 9 | TIADQILRY | | 42597 |
| HPV31 | L2 | 312 | 8 | TIGARVHY | | 42598 |
| HPV31 | L2 | 312 | 9 | TIGARVHYY | | 42599 |
| HPV31 | L2 | 312 | 10 | TIGARVHYYY | | 42600 |
| HPV31 | L2 | 347 | 10 | TLNDGLYDIY | | 42601 |
| HPV31 | L2 | 288 | 8 | TSRRNTVR | | 42602 |
| HPV31 | L2 | 288 | 9 | TSRRNTVRY | | 42603 |
| HPV31 | L2 | 288 | 11 | TSRRNTVRYSR | | 42604 |
| HPV31 | L2 | 206 | 10 | TSSTPIPGVR | | 42605 |
| HPV31 | L2 | 206 | 11 | TSSTPIPGVRR | | 42606 |
| HPV31 | L2 | 345 | 9 | TSTLNDGLY | | 42607 |
| HPV31 | L2 | 39 | 9 | TTIADQILR | | 42608 |
| HPV31 | L2 | 39 | 10 | TTIADQILRY | | 42609 |
| HPV31 | L2 | 344 | 10 | TTSTLNDGLY | | 42610 |
| HPV31 | L2 | 343 | 11 | TTTSTLNDGLY | | 42611 |
| HPV31 | L2 | 362 | 8 | TVDTPATH | | 42612 |
| HPV31 | L2 | 254 | 9 | TVNAEESLY | | 42613 |
| HPV31 | L2 | 293 | 10 | TVRYSRLGNK | | 42614 |
| HPV31 | L2 | 81 | 10 | TVSEASIPIR | | 42615 |
| HPV31 | L2 | 434 | 9 | VDGGDFYLH | | 42616 |
| HPV31 | L2 | 115 | 11 | VDVGAPAPIPH | | 42617 |
| HPV31 | L2 | 117 | 9 | VGAPAPIPH | | 42618 |
| HPV31 | L2 | 232 | 11 | VIDPTFLSAPK | | 42619 |
| HPV31 | L2 | 255 | 8 | VNAEESLY | | 42620 |
| HPV31 | L2 | 82 | 9 | VSEASIPIR | | 42621 |
| HPV31 | L2 | 430 | 11 | VSIFVDGGDFY | | 42622 |
| HPV31 | L2 | 440 | 10 | YLHPSYYMLK | | 42623 |
| HPV31 | L2 | 440 | 11 | YLHPSYYMLKR | | 42624 |
| HPV31 | L2 | 446 | 8 | YMLKRRRK | | 42625 |
| HPV31 | L2 | 446 | 9 | YMLKRRRKR | | 42626 |
| HPV31 | L2 | 223 | 9 | YSKATQQVK | | 42627 |
| HPV31 | L2 | 296 | 11 | YSRLGNKQTLR | | 42628 |
| HPV33 | E1 | 96 | 8 | AAEDVVDR | | 42629 |
| HPV33 | E1 | 383 | 11 | AAFLKSNSQAK | | 42630 |
| HPV33 | E1 | 104 | 11 | AANPCRTSINK | | 42631 |
| HPV33 | E1 | 452 | 11 | AFKKFLKGIPK | | 42632 |
| HPV33 | E1 | 448 | 8 | AFLGAFKK | | 42633 |
| HPV33 | E1 | 448 | 11 | AFLGAFKKFLK | | 42634 |
| HPV33 | E1 | 384 | 10 | AFLKSNSQAK | | 42635 |
| HPV33 | E1 | 635 | 9 | AGENTRSLR | | 42636 |
| HPV33 | E1 | 563 | 9 | AGTDSRWPY | | 42637 |
| HPV33 | E1 | 563 | 11 | AGTDSRWPYLH | | 42638 |
| HPV33 | E1 | 596 | 8 | AINDENWK | | 42639 |
| HPV33 | E1 | 198 | 8 | ANILYKFK | | 42640 |
| HPV33 | E1 | 198 | 11 | ANILYKFKEAY | | 42641 |
| HPV33 | E1 | 105 | 10 | ANPCRTSINK | | 42642 |
| HPV33 | E1 | 81 | 8 | AVCALKRK | | 42643 |
| HPV33 | E1 | 398 | 8 | CGIMCRHY | | 42644 |
| HPV33 | E1 | 398 | 9 | CGIMCRHYK | | 42645 |
| HPV33 | E1 | 398 | 10 | CGIMCRHYKK | | 42646 |
| HPV33 | E1 | 469 | 8 | CGPANTGK | | 42647 |
| HPV33 | E1 | 469 | 10 | CGPANTGKSY | | 42648 |
| HPV33 | E1 | 297 | 8 | CMVIEPPK | | 42649 |
| HPV33 | E1 | 297 | 10 | CMVIEPPKLR | | 42650 |
| HPV33 | E1 | 633 | 8 | CSAGENTR | | 42651 |
| HPV33 | E1 | 633 | 11 | CSAGENTRSLR | | 42652 |
| HPV33 | E1 | 276 | 10 | CSKNRLTVAK | | 42653 |
| HPV33 | E1 | 226 | 9 | CTDWCITGY | | 42654 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | E1 | 490 | 9 | CVISCVNSK | | 42655 |
| HPV33 | E1 | 490 | 11 | CVISCVNSKSH | | 42656 |
| HPV33 | E1 | 397 | 8 | DCGIMCRH | | 42657 |
| HPV33 | E1 | 397 | 9 | DCGIMCRHY | | 42658 |
| HPV33 | E1 | 397 | 10 | DCGIMCRHYK | | 42659 |
| HPV33 | E1 | 397 | 11 | DCGIMCRHYKK | | 42660 |
| HPV33 | E1 | 77 | 10 | DDLNAVCALK | | 42661 |
| HPV33 | E1 | 77 | 11 | DDLNAVCALKR | | 42662 |
| HPV33 | E1 | 364 | 8 | DDSDIAYY | | 42663 |
| HPV33 | E1 | 364 | 9 | DDSDIAYYY | | 42664 |
| HPV33 | E1 | 515 | 10 | DDVTPISWTY | | 42665 |
| HPV33 | E1 | 534 | 10 | DGNEISIDVK | | 42666 |
| HPV33 | E1 | 534 | 11 | DGNEISIDVKH | | 42667 |
| HPV33 | E1 | 614 | 8 | DLIEEEDK | | 42668 |
| HPV33 | E1 | 614 | 11 | DLIEEEDKENH | | 42669 |
| HPV33 | E1 | 78 | 9 | DLNAVCALK | | 42670 |
| HPV33 | E1 | 78 | 10 | DLNAVCALKR | | 42671 |
| HPV33 | E1 | 78 | 11 | DLNAVCALKRK | | 42672 |
| HPV33 | E1 | 349 | 10 | DLSEMVQWAY | | 42673 |
| HPV33 | E1 | 365 | 8 | DSDIAYYY | | 42674 |
| HPV33 | E1 | 377 | 11 | DSNSNAAAFLK | | 42675 |
| HPV33 | E1 | 566 | 8 | DSRWPYLH | | 42676 |
| HPV33 | E1 | 566 | 10 | DSRWPYLHSR | | 42677 |
| HPV33 | E1 | 541 | 11 | DVKHRALVQLK | | 42678 |
| HPV33 | E1 | 516 | 9 | DVTPISWTY | | 42679 |
| HPV33 | E1 | 99 | 11 | DVVDRAANPCR | | 42680 |
| HPV33 | E1 | 117 | 8 | ECTYRKRK | | 42681 |
| HPV33 | E1 | 76 | 11 | EDDLNAVCALK | | 42682 |
| HPV33 | E1 | 445 | 10 | EFTAFLGAFK | | 42683 |
| HPV33 | E1 | 445 | 11 | EFTAFLGAFKK | | 42684 |
| HPV33 | E1 | 537 | 8 | EISIDVKH | | 42685 |
| HPV33 | E1 | 537 | 9 | EISIDVKHR | | 42686 |
| HPV33 | E1 | 361 | 10 | ELTDDSDIAY | | 42687 |
| HPV33 | E1 | 361 | 11 | ELTDDSDIAYY | | 42688 |
| HPV33 | E1 | 214 | 10 | ELVRPFKSDK | | 42689 |
| HPV33 | E1 | 622 | 11 | ENHGGNISTFK | | 42690 |
| HPV33 | E1 | 600 | 9 | ENWKSFFSR | | 42691 |
| HPV33 | E1 | 242 | 8 | ESLKVLIK | | 42692 |
| HPV33 | E1 | 242 | 10 | ESLKVLIKQH | | 42693 |
| HPV33 | E1 | 295 | 10 | ETCMVIEPPK | | 42694 |
| HPV33 | E1 | 19 | 8 | EVEAVIER | | 42695 |
| HPV33 | E1 | 19 | 9 | EVEAVIERR | | 42696 |
| HPV33 | E1 | 587 | 9 | FDENGNPVY | | 42697 |
| HPV33 | E1 | 348 | 11 | FDLSEMVQWAY | | 42698 |
| HPV33 | E1 | 605 | 8 | FFSRTWCK | | 42699 |
| HPV33 | E1 | 479 | 10 | FGMSLIQFLK | | 42700 |
| HPV33 | E1 | 449 | 10 | FLGAFKKFLK | | 42701 |
| HPV33 | E1 | 456 | 8 | FLKGIPKK | | 42702 |
| HPV33 | E1 | 385 | 9 | FLKSNSQAK | 0.0002 | 42703 |
| HPV33 | E1 | 212 | 9 | FMELVRPFK | | 42704 |
| HPV33 | E1 | 446 | 9 | FTAFLGAFK | | 42705 |
| HPV33 | E1 | 446 | 10 | FTAFLGAFKK | | 42706 |
| HPV33 | E1 | 451 | 8 | GAFKKFLK | | 42707 |
| HPV33 | E1 | 489 | 10 | GCVISCVNSK | | 42708 |
| HPV33 | E1 | 625 | 8 | GGNISTFK | | 42709 |
| HPV33 | E1 | 265 | 9 | GIIILLIR | | 42710 |
| HPV33 | E1 | 265 | 11 | GIIILLIRFR | | 42711 |
| HPV33 | E1 | 399 | 8 | GIMCRHYK | | 42712 |
| HPV33 | E1 | 399 | 9 | GIMCRHYKK | | 42713 |
| HPV33 | E1 | 209 | 9 | GISFMELVR | | 42714 |
| HPV33 | E1 | 235 | 11 | GISPSVAESLK | | 42715 |
| HPV33 | E1 | 480 | 9 | GMSLIQFLK | | 42716 |
| HPV33 | E1 | 535 | 9 | GNEISIDVK | | 42717 |
| HPV33 | E1 | 535 | 10 | GNEISIDVKH | | 42718 |
| HPV33 | E1 | 535 | 11 | GNEISIDVKHR | | 42719 |
| HPV33 | E1 | 430 | 11 | GNWRPIVQLLR | | 42720 |
| HPV33 | E1 | 564 | 8 | GTDSRWPY | | 42721 |
| HPV33 | E1 | 564 | 10 | GTDSRWPYLH | | 42722 |
| HPV33 | E1 | 327 | 9 | GTTPEWIDR | | 42723 |
| HPV33 | E1 | 500 | 11 | HFWLQPLSDAK | | 42724 |
| HPV33 | E1 | 624 | 9 | HGGNISTFK | | 42725 |
| HPV33 | E1 | 256 | 9 | HLQCLTCDR | | 42726 |
| HPV33 | E1 | 573 | 10 | HSRLTVFEFK | | 42727 |
| HPV33 | E1 | 192 | 11 | HSSNTKANILY | | 42728 |
| HPV33 | E1 | 468 | 9 | ICGPANTGK | | 42729 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV33 | E1 | 468 | 11 | ICGPANTGKSY | | 42730 |
| HPV33 | E1 | 514 | 11 | IDDVTPISWTY | | 42731 |
| HPV33 | E1 | 125 | 9 | IDELEDSGY | | 42732 |
| HPV33 | E1 | 333 | 9 | IDRLTVLQH | | 42733 |
| HPV33 | E1 | 415 | 8 | IGQWIQSR | | 42734 |
| HPV33 | E1 | 415 | 11 | IGQWIQSRCEK | | 42735 |
| HPV33 | E1 | 266 | 8 | IIILLLIR | | 42736 |
| HPV33 | E1 | 266 | 10 | IIILLLIRFR | | 42737 |
| HPV33 | E1 | 267 | 9 | IILLLIRFR | | 42738 |
| HPV33 | E1 | 268 | 8 | ILLLIRFR | | 42739 |
| HPV33 | E1 | 268 | 11 | ILLLIRFRCSK | | 42740 |
| HPV33 | E1 | 200 | 9 | ILYKFKEAY | | 42741 |
| HPV33 | E1 | 400 | 8 | IMCRHYKK | | 42742 |
| HPV33 | E1 | 400 | 11 | IMCRHYKKAEK | | 42743 |
| HPV33 | E1 | 112 | 9 | INKNKECTY | | 42744 |
| HPV33 | E1 | 112 | 10 | INKNKECTYR | | 42745 |
| HPV33 | E1 | 112 | 11 | INKNKECTYRK | | 42746 |
| HPV33 | E1 | 492 | 9 | ISCVNSKSH | | 42747 |
| HPV33 | E1 | 210 | 8 | ISFMELVR | | 42748 |
| HPV33 | E1 | 210 | 11 | ISFMELVRPFK | | 42749 |
| HPV33 | E1 | 538 | 8 | ISIDVKHR | | 42750 |
| HPV33 | E1 | 187 | 11 | ISNVLHSSNTK | | 42751 |
| HPV33 | E1 | 236 | 10 | ISPSVAESLK | | 42752 |
| HPV33 | E1 | 520 | 9 | ISWTYIDDY | | 42753 |
| HPV33 | E1 | 520 | 11 | ISWTYIDDYMR | | 42754 |
| HPV33 | E1 | 394 | 10 | IVKDCGIMCR | | 42755 |
| HPV33 | E1 | 394 | 11 | IVKDCGIMCRH | | 42756 |
| HPV33 | E1 | 197 | 9 | KANILYKFK | | 42757 |
| HPV33 | E1 | 632 | 9 | KCSAGENTR | | 42758 |
| HPV33 | E1 | 396 | 8 | KDCGIMCR | | 42759 |
| HPV33 | E1 | 396 | 9 | KDCGIMCRH | | 42760 |
| HPV33 | E1 | 396 | 10 | KDCGIMCRHY | | 42761 |
| HPV33 | E1 | 396 | 11 | KDCGIMCRHYK | | 42762 |
| HPV33 | E1 | 455 | 8 | KFLKGIPK | | 42763 |
| HPV33 | E1 | 455 | 9 | KFLKGIPKK | | 42764 |
| HPV33 | E1 | 488 | 11 | KGCVISCVNSK | | 42765 |
| HPV33 | E1 | 124 | 10 | KIDELEDSGY | | 42766 |
| HPV33 | E1 | 393 | 11 | KIVKDCGIMCR | | 42767 |
| HPV33 | E1 | 612 | 10 | KLDLIEEEDK | | 42768 |
| HPV33 | E1 | 304 | 10 | KLRSQTCALY | | 42769 |
| HPV33 | E1 | 412 | 11 | KMSIGQWIQSR | | 42770 |
| HPV33 | E1 | 114 | 8 | KNKECTYR | | 42771 |
| HPV33 | E1 | 114 | 9 | KNKECTYRK | | 42772 |
| HPV33 | E1 | 114 | 10 | KNKECTYRKR | | 42773 |
| HPV33 | E1 | 114 | 11 | KNKECTYRKRK | | 42774 |
| HPV33 | E1 | 278 | 8 | KNRLTVAK | | 42775 |
| HPV33 | E1 | 603 | 10 | KSFFSRTWCK | | 42776 |
| HPV33 | E1 | 387 | 10 | KSNSQAKIVK | | 42777 |
| HPV33 | E1 | 425 | 9 | KTNDGGNWR | | 42778 |
| HPV33 | E1 | 245 | 10 | KVLIKQHSLY | | 42779 |
| HPV33 | E1 | 533 | 11 | LDGNEISIDVK | | 42780 |
| HPV33 | E1 | 613 | 9 | LDLIEEEDK | | 42781 |
| HPV33 | E1 | 450 | 9 | LGAFKKFLK | | 42782 |
| HPV33 | E1 | 467 | 10 | LICGPANTGK | | 42783 |
| HPV33 | E1 | 615 | 10 | LIEEEDKENH | | 42784 |
| HPV33 | E1 | 247 | 8 | LIKQHSLY | | 42785 |
| HPV33 | E1 | 247 | 10 | LIKQHSLYTH | | 42786 |
| HPV33 | E1 | 271 | 8 | LIRFRCSK | | 42787 |
| HPV33 | E1 | 271 | 10 | LIRFRCSKNR | | 42788 |
| HPV33 | E1 | 270 | 9 | LLIRFRCSK | | 42789 |
| HPV33 | E1 | 270 | 11 | LLIRFRCSKNR | | 42790 |
| HPV33 | E1 | 269 | 10 | LLLIRFRCSK | | 42791 |
| HPV33 | E1 | 79 | 8 | LNAVCALK | | 42792 |
| HPV33 | E1 | 79 | 9 | LNAVCALKR | | 42793 |
| HPV33 | E1 | 79 | 10 | LNAVCALKRK | | 42794 |
| HPV33 | E1 | 350 | 9 | LSEMVQWAY | | 42795 |
| HPV33 | E1 | 362 | 9 | LTDDSDIAY | | 42796 |
| HPV33 | E1 | 362 | 10 | LTDDSDIAYY | | 42797 |
| HPV33 | E1 | 362 | 11 | LTDDSDIAYYY | | 42798 |
| HPV33 | E1 | 215 | 9 | LVRPFKSDK | | 42799 |
| HPV33 | E1 | 401 | 10 | MCRHYKKAEK | | 42800 |
| HPV33 | E1 | 401 | 11 | MCRHYKKAEKR | | 42801 |
| HPV33 | E1 | 466 | 11 | MLICGPANTGK | | 42802 |
| HPV33 | E1 | 413 | 10 | MSIGQWIQSR | | 42803 |
| HPV33 | E1 | 481 | 8 | MSLIQFLK | | 42804 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | E1 | 298 | 9 | MVIEPPKLR | | 42805 |
| HPV33 | E1 | 562 | 10 | NAGTDSRWPY | | 42806 |
| HPV33 | E1 | 80 | 8 | NAVCALKR | | 42807 |
| HPV33 | E1 | 80 | 9 | NAVCALKRK | | 42808 |
| HPV33 | E1 | 598 | 11 | NDENWKSFFSR | | 42809 |
| HPV33 | E1 | 199 | 10 | NILYKFKEAY | | 42810 |
| HPV33 | E1 | 57 | 11 | NSIQADTEAAR | | 42811 |
| HPV33 | E1 | 379 | 9 | NSNAAAFLK | 0.3700 | 42812 |
| HPV33 | E1 | 389 | 8 | NSQAKIVK | | 42813 |
| HPV33 | E1 | 195 | 8 | NTKANILY | | 42814 |
| HPV33 | E1 | 195 | 9 | NTKANILYK | | 42815 |
| HPV33 | E1 | 195 | 11 | NTKANILYKFK | | 42816 |
| HPV33 | E1 | 560 | 9 | NTNAGTDSR | | 42817 |
| HPV33 | E1 | 189 | 9 | NVLHSSNTK | | 42818 |
| HPV33 | E1 | 471 | 8 | PANTGKSY | | 42819 |
| HPV33 | E1 | 107 | 8 | PCRTSINK | | 42820 |
| HPV33 | E1 | 107 | 10 | PCRTSINKNK | | 42821 |
| HPV33 | E1 | 586 | 10 | PFDENGNPVY | | 42822 |
| HPV33 | E1 | 519 | 10 | PISWTYIDDY | | 42823 |
| HPV33 | E1 | 434 | 8 | PIVQLLRY | | 42824 |
| HPV33 | E1 | 238 | 8 | PSVAESLK | | 42825 |
| HPV33 | E1 | 593 | 11 | PVYAINDENWK | | 42826 |
| HPV33 | E1 | 60 | 8 | QADTEAAR | | 42827 |
| HPV33 | E1 | 326 | 10 | QGTTPEWIDR | | 42828 |
| HPV33 | E1 | 94 | 10 | QSAAEDVVDR | | 42829 |
| HPV33 | E1 | 308 | 9 | QTCALYWFR | | 42830 |
| HPV33 | E1 | 275 | 11 | RCSKNRLTVAK | | 42831 |
| HPV33 | E1 | 273 | 8 | RFRCSKNR | | 42832 |
| HPV33 | E1 | 264 | 10 | RGIIILLLIR | | 42833 |
| HPV33 | E1 | 575 | 8 | RLTVFEFK | | 42834 |
| HPV33 | E1 | 306 | 8 | RSQTCALY | | 42835 |
| HPV33 | E1 | 306 | 11 | RSQTCALYWFR | | 42836 |
| HPV33 | E1 | 109 | 8 | RTSINKNK | | 42837 |
| HPV33 | E1 | 95 | 9 | SAAEDVVDR | | 42838 |
| HPV33 | E1 | 634 | 10 | SAGENTRSLR | | 42839 |
| HPV33 | E1 | 225 | 10 | SCTDWCITGY | | 42840 |
| HPV33 | E1 | 493 | 8 | SCVNSKSH | | 42841 |
| HPV33 | E1 | 604 | 9 | SFFSRTWCK | | 42842 |
| HPV33 | E1 | 211 | 10 | SFMELVRPFK | | 42843 |
| HPV33 | E1 | 414 | 9 | SIGQWIQSR | | 42844 |
| HPV33 | E1 | 111 | 10 | SINKNKECTY | | 42845 |
| HPV33 | E1 | 111 | 11 | SINKNKECTYR | | 42846 |
| HPV33 | E1 | 58 | 10 | SIQADTEAAR | | 42847 |
| HPV33 | E1 | 243 | 9 | SLKVLIKQH | | 42848 |
| HPV33 | E1 | 380 | 8 | SNAAAFLK | | 42849 |
| HPV33 | E1 | 378 | 10 | SNSNAAAFLK | | 42850 |
| HPV33 | E1 | 388 | 9 | SNSQAKIVK | | 42851 |
| HPV33 | E1 | 194 | 9 | SNTKANILY | | 42852 |
| HPV33 | E1 | 194 | 10 | SNTKANILYK | | 42853 |
| HPV33 | E1 | 559 | 10 | SNTNAGTDSR | | 42854 |
| HPV33 | E1 | 188 | 10 | SNVLHSSNTK | | 42855 |
| HPV33 | E1 | 193 | 10 | SSNTKANILY | | 42856 |
| HPV33 | E1 | 193 | 11 | SSNTKANILYK | | 42857 |
| HPV33 | E1 | 239 | 11 | SVAESLKVLIK | | 42858 |
| HPV33 | E1 | 447 | 8 | TAFLGAFK | | 42859 |
| HPV33 | E1 | 447 | 9 | TAFLGAFKK | | 42860 |
| HPV33 | E1 | 309 | 8 | TCALYWFR | | 42861 |
| HPV33 | E1 | 296 | 9 | TCMVIEPPK | | 42862 |
| HPV33 | E1 | 296 | 11 | TCMVIEPPKLR | | 42863 |
| HPV33 | E1 | 363 | 8 | TDDSDIAY | | 42864 |
| HPV33 | E1 | 363 | 9 | TDDSDIAYY | | 42865 |
| HPV33 | E1 | 363 | 10 | TDDSDIAYYY | | 42866 |
| HPV33 | E1 | 565 | 9 | TDSRWPYLH | | 42867 |
| HPV33 | E1 | 565 | 11 | TDSRWPYLHSR | | 42868 |
| HPV33 | E1 | 227 | 8 | TDWCITGY | | 42869 |
| HPV33 | E1 | 630 | 11 | TFKCSAGENTR | | 42870 |
| HPV33 | E1 | 183 | 10 | TLQEISNVLH | | 42871 |
| HPV33 | E1 | 561 | 8 | TNAGTDSR | | 42872 |
| HPV33 | E1 | 561 | 11 | TNAGTDSRWPY | | 42873 |
| HPV33 | E1 | 426 | 8 | TNDGGNWR | | 42874 |
| HPV33 | E1 | 224 | 11 | TSCTDWCITGY | | 42875 |
| HPV33 | E1 | 110 | 11 | TSINKNKECTY | | 42876 |
| HPV33 | E1 | 558 | 11 | TSNTNAGTDSR | | 42877 |
| HPV33 | E1 | 328 | 8 | TTPEWIDR | | 42878 |
| HPV33 | E1 | 240 | 10 | VAESLKVLIK | | 42879 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | E1 | 101 | 9 | VDRAANPCR | | 42880 |
| HPV33 | E1 | 299 | 8 | VIEPPKLR | | 42881 |
| HPV33 | E1 | 491 | 8 | VISCVNSK | | 42882 |
| HPV33 | E1 | 491 | 10 | VISCVNSKSH | | 42883 |
| HPV33 | E1 | 190 | 8 | VLHSSNTK | | 42884 |
| HPV33 | E1 | 246 | 9 | VLIKQHSLY | | 42885 |
| HPV33 | E1 | 246 | 11 | VLIKQHSLYTH | | 42886 |
| HPV33 | E1 | 182 | 11 | VTLQEISNVLH | | 42887 |
| HPV33 | E1 | 517 | 8 | VTPISWTY | | 42888 |
| HPV33 | E1 | 100 | 10 | VVDRAANPCR | | 42889 |
| HPV33 | E1 | 17 | 10 | WFEVEAVIER | | 42890 |
| HPV33 | E1 | 17 | 11 | WFEVEAVIERR | | 42891 |
| HPV33 | E1 | 332 | 10 | WIDRLTVLQH | | 42892 |
| HPV33 | E1 | 418 | 8 | WIQSRCEK | | 42893 |
| HPV33 | E1 | 502 | 9 | WLQPLSDAK | | 42894 |
| HPV33 | E1 | 522 | 9 | WTYIDDYMR | | 42895 |
| HPV33 | E1 | 595 | 9 | YAINDENWK | | 42896 |
| HPV33 | E1 | 478 | 11 | YFGMSLIQFLK | | 42897 |
| HPV33 | E1 | 208 | 10 | YGISFMELVR | | 42898 |
| HPV33 | E1 | 254 | 11 | YTHLQCLTCDR | | 42899 |
| HPV33 | E2 | 210 | 10 | ADIQTDNDNR | | 42900 |
| HPV33 | E2 | 246 | 8 | ADPALDNR | | 42901 |
| HPV33 | E2 | 246 | 11 | ADPALDNRTAR | | 42902 |
| HPV33 | E2 | 249 | 8 | ALDNRTAR | | 42903 |
| HPV33 | E2 | 78 | 10 | ALETLSKSQY | | 42904 |
| HPV33 | E2 | 258 | 9 | ATNCTNKQR | | 42905 |
| HPV33 | E2 | 10 | 10 | AVQEKILDLY | | 42906 |
| HPV33 | E2 | 245 | 9 | CADPALDNR | | 42907 |
| HPV33 | E2 | 40 | 8 | CALLYTAK | | 42908 |
| HPV33 | E2 | 288 | 9 | CLRYRLKPY | | 42909 |
| HPV33 | E2 | 288 | 10 | CLRYRLKPYK | | 42910 |
| HPV33 | E2 | 269 | 10 | CSSNVAPIVH | | 42911 |
| HPV33 | E2 | 145 | 10 | CTMVTGKVDY | | 42912 |
| HPV33 | E2 | 211 | 9 | DIQTDNDNR | | 42913 |
| HPV33 | E2 | 25 | 8 | DLPSQIEH | | 42914 |
| HPV33 | E2 | 25 | 10 | DLPSQIEHWK | | 42915 |
| HPV33 | E2 | 122 | 10 | DNDKKNTMDY | | 42916 |
| HPV33 | E2 | 217 | 10 | DNRPPQAAAK | | 42917 |
| HPV33 | E2 | 217 | 11 | DNRPPQAAAKR | | 42918 |
| HPV33 | E2 | 235 | 8 | DTAQPLTK | | 42919 |
| HPV33 | E2 | 143 | 9 | DTCTMVTGK | | 42920 |
| HPV33 | E2 | 232 | 11 | DTTDTAQPLTK | | 42921 |
| HPV33 | E2 | 39 | 9 | ECALLYTAK | | 42922 |
| HPV33 | E2 | 173 | 8 | EDAAKYSK | | 42923 |
| HPV33 | E2 | 142 | 10 | EDTCTMVTGK | | 42924 |
| HPV33 | E2 | 74 | 11 | ELQMALETLSK | | 42925 |
| HPV33 | E2 | 298 | 11 | ELYSSMSSTWH | | 42926 |
| HPV33 | E2 | 282 | 9 | ESNSLKCLR | | 42927 |
| HPV33 | E2 | 282 | 10 | ESNSLKCLRY | | 42928 |
| HPV33 | E2 | 282 | 11 | ESNSLKCLRYR | | 42929 |
| HPV33 | E2 | 80 | 8 | ETLSKSQY | | 42930 |
| HPV33 | E2 | 115 | 11 | ETVTVQYDNDK | | 42931 |
| HPV33 | E2 | 100 | 9 | EVWLCEPPK | | 42932 |
| HPV33 | E2 | 244 | 10 | FCADPALDNR | | 42933 |
| HPV33 | E2 | 156 | 10 | GMYYIHNCEK | | 42934 |
| HPV33 | E2 | 278 | 10 | HLKGESNSLK | | 42935 |
| HPV33 | E2 | 161 | 9 | HNCEKVYFK | | 42936 |
| HPV33 | E2 | 161 | 10 | HNCEKVYFKY | | 42937 |
| HPV33 | E2 | 155 | 11 | IGMYYIHNCEK | | 42938 |
| HPV33 | E2 | 15 | 9 | ILDLYEADK | | 42939 |
| HPV33 | E2 | 4 | 11 | ISARLNAVQEK | | 42940 |
| HPV33 | E2 | 287 | 8 | KCLRYRLK | | 42941 |
| HPV33 | E2 | 287 | 10 | KCLRYRLKPY | | 42942 |
| HPV33 | E2 | 287 | 11 | KCLRYRLKPYK | | 42943 |
| HPV33 | E2 | 280 | 8 | KGESNSLK | | 42944 |
| HPV33 | E2 | 280 | 11 | KGESNSLKCLR | | 42945 |
| HPV33 | E2 | 14 | 10 | KILDLYEADK | | 42946 |
| HPV33 | E2 | 34 | 11 | KLIRMECALLY | | 42947 |
| HPV33 | E2 | 23 | 10 | KTDLPSQIEH | | 42948 |
| HPV33 | E2 | 180 | 8 | KTQMWEVH | | 42949 |
| HPV33 | E2 | 151 | 8 | KVDYIGMY | | 42950 |
| HPV33 | E2 | 151 | 9 | KVDYIGMYY | | 42951 |
| HPV33 | E2 | 151 | 11 | KVDYIGMYYIH | | 42952 |
| HPV33 | E2 | 165 | 8 | KVYFKYFK | | 42953 |
| HPV33 | E2 | 103 | 9 | LCEPPKCFK | | 42954 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | E2 | 103 | 10 | LCEPPKCFKK | | 42955 |
| HPV33 | E2 | 16 | 8 | LDLYEADK | | 42956 |
| HPV33 | E2 | 243 | 11 | LFCADPALDNR | | 42957 |
| HPV33 | E2 | 35 | 10 | LIRMECALLY | | 42958 |
| HPV33 | E2 | 77 | 8 | MALETLSK | | 42959 |
| HPV33 | E2 | 77 | 11 | MALETLSKSQY | | 42960 |
| HPV33 | E2 | 129 | 10 | MDYTNWGEIY | | 42961 |
| HPV33 | E2 | 49 | 8 | MGFSHLCH | | 42962 |
| HPV33 | E2 | 147 | 8 | MVTGKVDY | | 42963 |
| HPV33 | E2 | 9 | 11 | NAVQEKILDLY | | 42964 |
| HPV33 | E2 | 162 | 8 | NCEKVYFK | | 42965 |
| HPV33 | E2 | 162 | 9 | NCEKVYFKY | | 42966 |
| HPV33 | E2 | 162 | 11 | NCEKVYFKYFK | | 42967 |
| HPV33 | E2 | 123 | 9 | NDKKNTMDY | | 42968 |
| HPV33 | E2 | 216 | 11 | NDNRPPQAAAK | | 42969 |
| HPV33 | E2 | 284 | 8 | NSLKCLRY | | 42970 |
| HPV33 | E2 | 284 | 9 | NSLKCLRYR | | 42971 |
| HPV33 | E2 | 284 | 11 | NSLKCLRYRLK | | 42972 |
| HPV33 | E2 | 272 | 9 | NVAPIVHLK | | 42973 |
| HPV33 | E2 | 248 | 9 | PALDNRTAR | | 42974 |
| HPV33 | E2 | 60 | 9 | PSLLASKTK | | 42975 |
| HPV33 | E2 | 27 | 8 | PSQIEHWK | | 42976 |
| HPV33 | E2 | 27 | 11 | PSQIEHWKLIR | | 42977 |
| HPV33 | E2 | 222 | 8 | QAAAKRRR | | 42978 |
| HPV33 | E2 | 113 | 9 | QGETVTVQY | | 42979 |
| HPV33 | E2 | 29 | 9 | QIEHWKLIR | | 42980 |
| HPV33 | E2 | 76 | 9 | QMALETLSK | | 42981 |
| HPV33 | E2 | 332 | 8 | QMFLGTVK | | 42982 |
| HPV33 | E2 | 48 | 9 | QMGFSHLCH | | 42983 |
| HPV33 | E2 | 57 | 10 | QVVPSLLASK | | 42984 |
| HPV33 | E2 | 292 | 9 | RLKPYKELY | | 42985 |
| HPV33 | E2 | 7 | 8 | RLNAVQEK | | 42986 |
| HPV33 | E2 | 37 | 8 | RMECALLY | | 42987 |
| HPV33 | E2 | 37 | 11 | RMECALLYTAK | | 42988 |
| HPV33 | E2 | 256 | 9 | RTATNCTNK | | 42989 |
| HPV33 | E2 | 256 | 11 | RTATNCTNKQR | | 42990 |
| HPV33 | E2 | 5 | 10 | SARLNAVQEK | | 42991 |
| HPV33 | E2 | 98 | 11 | SLEVWLCEPPK | | 42992 |
| HPV33 | E2 | 285 | 8 | SLKCLRYR | | 42993 |
| HPV33 | E2 | 285 | 10 | SLKCLRYRLK | | 42994 |
| HPV33 | E2 | 61 | 8 | SLLASKTK | | 42995 |
| HPV33 | E2 | 283 | 8 | SNSLKCLR | | 42996 |
| HPV33 | E2 | 283 | 9 | SNSLKCLRY | | 42997 |
| HPV33 | E2 | 283 | 10 | SNSLKCLRYR | | 42998 |
| HPV33 | E2 | 271 | 8 | SNVAPIVH | | 42999 |
| HPV33 | E2 | 271 | 10 | SNVAPIVHLK | | 43000 |
| HPV33 | E2 | 301 | 8 | SSMSSTWH | | 43001 |
| HPV33 | E2 | 270 | 9 | SSNVAPIVH | | 43002 |
| HPV33 | E2 | 270 | 11 | SSNVAPIVHLK | | 43003 |
| HPV33 | E2 | 304 | 11 | SSTWHWTSDNK | | 43004 |
| HPV33 | E2 | 305 | 10 | STWHWTSDNK | | 43005 |
| HPV33 | E2 | 209 | 11 | TADIQTDNDNR | | 43006 |
| HPV33 | E2 | 45 | 9 | TAKQMGFSH | | 43007 |
| HPV33 | E2 | 254 | 11 | TARTATNCTNK | | 43008 |
| HPV33 | E2 | 257 | 8 | TATNCTNK | | 43009 |
| HPV33 | E2 | 257 | 10 | TATNCTNKQR | | 43010 |
| HPV33 | E2 | 144 | 8 | TCTMVTGK | | 43011 |
| HPV33 | E2 | 144 | 11 | TCTMVTGKVDY | | 43012 |
| HPV33 | E2 | 24 | 9 | TDLPSQIEH | | 43013 |
| HPV33 | E2 | 24 | 11 | TDLPSQIEHWK | | 43014 |
| HPV33 | E2 | 234 | 9 | TDTAQPLTK | | 43015 |
| HPV33 | E2 | 149 | 10 | TGKVDYIGMY | | 43016 |
| HPV33 | E2 | 149 | 11 | TGKVDYIGMYY | | 43017 |
| HPV33 | E2 | 128 | 11 | TMDYTNWGEIY | | 43018 |
| HPV33 | E2 | 146 | 9 | TMVTGKVDY | | 43019 |
| HPV33 | E2 | 259 | 8 | TNCTNKQR | | 43020 |
| HPV33 | E2 | 310 | 8 | TSDNKNSK | | 43021 |
| HPV33 | E2 | 233 | 10 | TTDTAQPLTK | | 43022 |
| HPV33 | E2 | 118 | 8 | TVQYDNDK | | 43023 |
| HPV33 | E2 | 118 | 9 | TVQYDNDKK | | 43024 |
| HPV33 | E2 | 116 | 10 | TVTVQYDNDK | | 43025 |
| HPV33 | E2 | 116 | 11 | TVTVQYDNDKK | | 43026 |
| HPV33 | E2 | 273 | 8 | VAPIVHLK | | 43027 |
| HPV33 | E2 | 268 | 11 | VCSSNVAPIVH | | 43028 |
| HPV33 | E2 | 152 | 8 | VDYIGMYY | | 43029 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | E2 | 152 | 10 | VDYIGMYYIH | | 43030 |
| HPV33 | E2 | 148 | 11 | VTGKVDYIGMY | | 43031 |
| HPV33 | E2 | 117 | 9 | VTVQYDNDK | | 43032 |
| HPV33 | E2 | 117 | 10 | VTVQYDNDKK | | 43033 |
| HPV33 | E2 | 58 | 9 | VVPSLLASK | | 43034 |
| HPV33 | E2 | 58 | 11 | VVPSLLASKTK | | 43035 |
| HPV33 | E2 | 102 | 10 | WLCEPPKCFK | | 43036 |
| HPV33 | E2 | 102 | 11 | WLCEPPKCFKK | | 43037 |
| HPV33 | E2 | 309 | 9 | WTSDNKNSK | | 43038 |
| HPV33 | E2 | 121 | 11 | YDNDKKNTMDY | | 43039 |
| HPV33 | E2 | 170 | 8 | YFKEDAAK | | 43040 |
| HPV33 | E2 | 170 | 9 | YFKEDAAKY | | 43041 |
| HPV33 | E2 | 170 | 11 | YFKEDAAKYSK | | 43042 |
| HPV33 | E2 | 167 | 11 | YFKYFKEDAAK | | 43043 |
| HPV33 | E2 | 154 | 8 | YIGMYYIH | | 43044 |
| HPV33 | E2 | 159 | 9 | YIHNCEKVY | | 43045 |
| HPV33 | E2 | 159 | 11 | YIHNCEKVYFK | | 43046 |
| HPV33 | E2 | 178 | 10 | YSKTQMWEVH | | 43047 |
| HPV33 | E2 | 300 | 9 | YSSMSSTWH | | 43048 |
| HPV33 | E2 | 44 | 10 | YTAKQMGFSH | | 43049 |
| HPV33 | E2 | 131 | 8 | YTNWGEIY | | 43050 |
| HPV33 | E5 | 63 | 8 | CINFHAQH | | 43051 |
| HPV33 | E5 | 51 | 8 | FCYLLFLY | | 43052 |
| HPV33 | E5 | 50 | 9 | FFCYLLFLY | | 43053 |
| HPV33 | E5 | 12 | 9 | FLCLSLLLR | | 43054 |
| HPV33 | E5 | 44 | 10 | GSPLKIFFCY | | 43055 |
| HPV33 | E5 | 49 | 10 | IFFCYLLFLY | | 43056 |
| HPV33 | E5 | 10 | 11 | ILFLCLSLLLR | | 43057 |
| HPV33 | E5 | 48 | 11 | KIFFCYLLFLY | | 43058 |
| HPV33 | E5 | 13 | 8 | LCLSLLLR | | 43059 |
| HPV33 | E5 | 11 | 10 | LFLCLSLLLR | | 43060 |
| HPV33 | E5 | 22 | 8 | LILSISTY | | 43061 |
| HPV33 | E5 | 38 | 11 | LLWVFVGSPLK | | 43062 |
| HPV33 | E5 | 62 | 9 | MCINFHAQH | | 43063 |
| HPV33 | E5 | 61 | 10 | MMCINFHAQH | | 43064 |
| HPV33 | E5 | 21 | 9 | PLILSISTY | | 43065 |
| HPV33 | E5 | 46 | 8 | PLKIFFCY | | 43066 |
| HPV33 | E5 | 60 | 8 | PMMCINFH | | 43067 |
| HPV33 | E5 | 60 | 11 | PMMCINFHAQH | | 43068 |
| HPV33 | E5 | 41 | 8 | VFVGSPLK | | 43069 |
| HPV33 | E5 | 43 | 11 | VGSPLKIFFCY | | 43070 |
| HPV33 | E5 | 40 | 9 | WVFVGSPLK | | 43071 |
| HPV33 | E5 | 58 | 10 | YLPMMCINFH | | 43072 |
| HPV33 | E6 | 137 | 8 | AACWRSRR | | 43073 |
| HPV33 | E6 | 137 | 9 | AACWRSRRR | | 43074 |
| HPV33 | E6 | 138 | 8 | ACWRSRRR | | 43075 |
| HPV33 | E6 | 48 | 8 | ADLTVVYR | | 43076 |
| HPV33 | E6 | 46 | 9 | AFADLTVVY | | 43077 |
| HPV33 | E6 | 46 | 10 | AFADLTVVYR | | 43078 |
| HPV33 | E6 | 133 | 9 | AGRCAACWR | | 43079 |
| HPV33 | E6 | 133 | 11 | AGRCAACWRSR | | 43080 |
| HPV33 | E6 | 136 | 8 | CAACWRSR | | 43081 |
| HPV33 | E6 | 136 | 9 | CAACWRSRR | | 43082 |
| HPV33 | E6 | 136 | 10 | CAACWRSRRR | | 43083 |
| HPV33 | E6 | 66 | 11 | CLRFLSKISEY | | 43084 |
| HPV33 | E6 | 30 | 10 | CVECKKPLQR | | 43085 |
| HPV33 | E6 | 44 | 11 | DFAFADLTVVY | | 43086 |
| HPV33 | E6 | 14 | 11 | DLCQALETTIH | | 43087 |
| HPV33 | E6 | 4 | 10 | DTEEKPRTLH | | 43088 |
| HPV33 | E6 | 32 | 8 | ECKKPLQR | | 43089 |
| HPV33 | E6 | 56 | 9 | EGNPFGICK | | 43090 |
| HPV33 | E6 | 98 | 11 | EILIRCIICQR | | 43091 |
| HPV33 | E6 | 27 | 8 | ELQCVECK | | 43092 |
| HPV33 | E6 | 27 | 9 | ELQCVECKK | | 43093 |
| HPV33 | E6 | 47 | 8 | FADLTVVY | | 43094 |
| HPV33 | E6 | 47 | 9 | FADLTVVYR | | 43095 |
| HPV33 | E6 | 45 | 10 | FAFADLTVVY | | 43096 |
| HPV33 | E6 | 45 | 11 | FAFADLTVVYR | | 43097 |
| HPV33 | E6 | 60 | 9 | FGICKLCLR | | 43098 |
| HPV33 | E6 | 69 | 8 | FLSKISEY | | 43099 |
| HPV33 | E6 | 69 | 9 | FLSKISEYR | | 43100 |
| HPV33 | E6 | 69 | 10 | FLSKISEYRH | | 43101 |
| HPV33 | E6 | 69 | 11 | FLSKISEYRHY | | 43102 |
| HPV33 | E6 | 61 | 8 | GICKLCLR | | 43103 |
| HPV33 | E6 | 57 | 8 | GNPFGICK | | 43104 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV33 | E6 | 85 | 9 | GNTLEQTVK | | 43105 |
| HPV33 | E6 | 85 | 10 | GNTLEQTVKK | | 43106 |
| HPV33 | E6 | 24 | 11 | HNIELQCVECK | | 43107 |
| HPV33 | E6 | 126 | 10 | HNISGRWAGR | | 43108 |
| HPV33 | E6 | 118 | 9 | HVDLNKRFH | | 43109 |
| HPV33 | E6 | 62 | 11 | ICKLCLRFLSK | | 43110 |
| HPV33 | E6 | 105 | 11 | ICQRPLCPQEK | | 43111 |
| HPV33 | E6 | 99 | 10 | ILIRCIICQR | | 43112 |
| HPV33 | E6 | 73 | 9 | ISEYRHYNY | | 43113 |
| HPV33 | E6 | 128 | 8 | ISGRWAGR | | 43114 |
| HPV33 | E6 | 72 | 8 | KISEYRHY | | 43115 |
| HPV33 | E6 | 72 | 10 | KISEYRHYNY | | 43116 |
| HPV33 | E6 | 64 | 9 | KLCLRFLSK | | 43117 |
| HPV33 | E6 | 65 | 8 | LCLRFLSK | | 43118 |
| HPV33 | E6 | 110 | 8 | LCPQEKKR | | 43119 |
| HPV33 | E6 | 110 | 9 | LCPQEKKRH | | 43120 |
| HPV33 | E6 | 15 | 10 | LCQALETTIH | | 43121 |
| HPV33 | E6 | 100 | 9 | LIRCIICQR | | 43122 |
| HPV33 | E6 | 121 | 11 | LNKRFHNISGR | | 43123 |
| HPV33 | E6 | 70 | 8 | LSKISEYR | | 43124 |
| HPV33 | E6 | 70 | 9 | LSKISEYRH | | 43125 |
| HPV33 | E6 | 70 | 10 | LSKISEYRHY | | 43126 |
| HPV33 | E6 | 1 | 8 | MFQDTEEK | | 43127 |
| HPV33 | E6 | 1 | 10 | MFQDTEEKPR | | 43128 |
| HPV33 | E6 | 25 | 10 | NIELQCVECK | | 43129 |
| HPV33 | E6 | 25 | 11 | NIELQCVECKK | | 43130 |
| HPV33 | E6 | 127 | 9 | NISGRWAGR | | 43131 |
| HPV33 | E6 | 86 | 8 | NTLEQTVK | | 43132 |
| HPV33 | E6 | 86 | 9 | NTLEQTVKK | | 43133 |
| HPV33 | E6 | 59 | 10 | PFGICKLCLR | | 43134 |
| HPV33 | E6 | 109 | 8 | PLCPQEKK | | 43135 |
| HPV33 | E6 | 109 | 9 | PLCPQEKKR | | 43136 |
| HPV33 | E6 | 109 | 10 | PLCPQEKKRH | | 43137 |
| HPV33 | E6 | 95 | 8 | PLNEILIR | | 43138 |
| HPV33 | E6 | 36 | 8 | PLQRSEVY | | 43139 |
| HPV33 | E6 | 17 | 8 | QALETTIH | | 43140 |
| HPV33 | E6 | 29 | 11 | QCVECKKPLQR | | 43141 |
| HPV33 | E6 | 3 | 8 | QDTEEKPR | | 43142 |
| HPV33 | E6 | 3 | 11 | QDTEEKPRTLH | | 43143 |
| HPV33 | E6 | 135 | 9 | RCAACWRSR | | 43144 |
| HPV33 | E6 | 135 | 10 | RCAACWRSRR | | 43145 |
| HPV33 | E6 | 135 | 11 | RCAACWRSRRR | | 43146 |
| HPV33 | E6 | 124 | 8 | RFHNISGR | | 43147 |
| HPV33 | E6 | 68 | 9 | RFLSKISEY | | 43148 |
| HPV33 | E6 | 68 | 10 | RFLSKISEYR | | 43149 |
| HPV33 | E6 | 68 | 11 | RFLSKISEYRH | | 43150 |
| HPV33 | E6 | 87 | 8 | TLEQTVKK | | 43151 |
| HPV33 | E6 | 119 | 8 | VDLNKRFH | | 43152 |
| HPV33 | E6 | 132 | 10 | WAGRCAACWR | | 43153 |
| HPV33 | E6 | 84 | 10 | YGNTLEQTVK | | 43154 |
| HPV33 | E6 | 84 | 11 | YGNTLEQTVKK | | 43155 |
| HPV33 | E7 | 50 | 10 | ADYYIVTCCH | | 43156 |
| HPV33 | E7 | 57 | 10 | CCHTCNTTVR | | 43157 |
| HPV33 | E7 | 68 | 10 | CVNSTASDLR | | 43158 |
| HPV33 | E7 | 42 | 11 | DGQAQPATADY | | 43159 |
| HPV33 | E7 | 14 | 10 | DLYPEPTDLY | | 43160 |
| HPV33 | E7 | 30 | 11 | DSSDEDEGLDR | | 43161 |
| HPV33 | E7 | 59 | 8 | HTCNTTVR | | 43162 |
| HPV33 | E7 | 67 | 11 | LCVNSTASDLR | | 43163 |
| HPV33 | E7 | 13 | 11 | LDLYPEPTDLY | | 43164 |
| HPV33 | E7 | 70 | 8 | NSTASDLR | | 43165 |
| HPV33 | E7 | 6 | 11 | PTLKEYVLDLY | | 43166 |
| HPV33 | E7 | 44 | 9 | QAQPATADY | | 43167 |
| HPV33 | E7 | 44 | 10 | QAQPATADYY | | 43168 |
| HPV33 | E7 | 2 | 8 | RGHKPTLK | | 43169 |
| HPV33 | E7 | 2 | 10 | RGHKPTLKEY | | 43170 |
| HPV33 | E7 | 32 | 9 | SDEDEGLDR | | 43171 |
| HPV33 | E7 | 31 | 10 | SSDEDEGLDR | | 43172 |
| HPV33 | E7 | 49 | 11 | TADYYIVTCCH | | 43173 |
| HPV33 | E7 | 56 | 11 | TCCHTCNTTVR | | 43174 |
| HPV33 | E7 | 7 | 10 | TLKEYVLDLY | | 43175 |
| HPV33 | E7 | 69 | 9 | VNSTASDLR | | 43176 |
| HPV33 | L1 | 102 | 9 | ACVGLEIGR | | 43177 |
| HPV33 | L1 | 456 | 10 | ADLDQFPLGR | | 43178 |
| HPV33 | L1 | 456 | 11 | ADLDQFPLGRK | | 43179 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV33 | L1 | 142 | 11 | ADNRECLSMDY | | 43180 |
| HPV33 | L1 | 471 | 8 | AGLKAKPK | | 43181 |
| HPV33 | L1 | 471 | 10 | AGLKAKPKLK | | 43182 |
| HPV33 | L1 | 471 | 11 | AGLKAKPKLKR | | 43183 |
| HPV33 | L1 | 37 | 11 | AGSSRLLAVGH | | 43184 |
| HPV33 | L1 | 424 | 11 | AITCQKTVPPK | | 43185 |
| HPV33 | L1 | 411 | 8 | ASLQDTYR | | 43186 |
| HPV33 | L1 | 44 | 10 | AVGHPYFSIK | | 43187 |
| HPV33 | L1 | 270 | 9 | AVPDDLYIK | | 43188 |
| HPV33 | L1 | 225 | 10 | CGSTCKYPDY | | 43189 |
| HPV33 | L1 | 207 | 11 | CMDFKTLQANK | | 43190 |
| HPV33 | L1 | 345 | 10 | CTQVTSDSTY | | 43191 |
| HPV33 | L1 | 345 | 11 | CTQVTSDSTYK | | 43192 |
| HPV33 | L1 | 103 | 8 | CVGLEIGR | | 43193 |
| HPV33 | L1 | 128 | 8 | DDTETGNK | | 43194 |
| HPV33 | L1 | 128 | 9 | DDTETGNKY | | 43195 |
| HPV33 | L1 | 209 | 9 | DFKTLQANK | | 43196 |
| HPV33 | L1 | 223 | 8 | DICGSTCK | | 43197 |
| HPV33 | L1 | 223 | 9 | DICGSTCKY | | 43198 |
| HPV33 | L1 | 457 | 9 | DLDQFPLGR | | 43199 |
| HPV33 | L1 | 457 | 10 | DLDQFPLGRK | | 43200 |
| HPV33 | L1 | 370 | 10 | DLQFVFQLCK | | 43201 |
| HPV33 | L1 | 143 | 10 | DNRECLSMDY | | 43202 |
| HPV33 | L1 | 143 | 11 | DNRECLSMDYK | | 43203 |
| HPV33 | L1 | 244 | 8 | DSLFFFLR | | 43204 |
| HPV33 | L1 | 244 | 9 | DSLFFFLRR | | 43205 |
| HPV33 | L1 | 351 | 10 | DSTYKNENFK | | 43206 |
| HPV33 | L1 | 129 | 8 | DTETGNKY | | 43207 |
| HPV33 | L1 | 202 | 10 | DTGFGCMDFK | | 43208 |
| HPV33 | L1 | 88 | 11 | DTSFYNPDTQR | | 43209 |
| HPV33 | L1 | 269 | 8 | EAVPDDLY | | 43210 |
| HPV33 | L1 | 269 | 10 | EAVPDDLYIK | | 43211 |
| HPV33 | L1 | 146 | 8 | ECLSMDYK | | 43212 |
| HPV33 | L1 | 357 | 8 | ENFKEYIR | | 43213 |
| HPV33 | L1 | 357 | 9 | ENFKEYIRH | | 43214 |
| HPV33 | L1 | 303 | 9 | ESQLFNKPY | | 43215 |
| HPV33 | L1 | 127 | 9 | FDDTETGNK | | 43216 |
| HPV33 | L1 | 127 | 10 | FDDTETGNKY | | 43217 |
| HPV33 | L1 | 248 | 11 | FFLRREQMFVR | | 43218 |
| HPV33 | L1 | 84 | 9 | FGFPDTSFY | | 43219 |
| HPV33 | L1 | 467 | 8 | FLLQAGLK | | 43220 |
| HPV33 | L1 | 467 | 10 | FLLQAGLKAK | | 43221 |
| HPV33 | L1 | 249 | 10 | FLRREQMFVR | | 43222 |
| HPV33 | L1 | 249 | 11 | FLRREQMFVRH | | 43223 |
| HPV33 | L1 | 307 | 9 | FNKPYWLQR | | 43224 |
| HPV33 | L1 | 50 | 10 | FSIKNPTNAK | | 43225 |
| HPV33 | L1 | 50 | 11 | FSIKNPTNAKK | | 43226 |
| HPV33 | L1 | 256 | 8 | FVRHFFNR | | 43227 |
| HPV33 | L1 | 419 | 11 | FVTSQAITCQK | | 43228 |
| HPV33 | L1 | 330 | 9 | FVTVVDTTR | | 43229 |
| HPV33 | L1 | 161 | 9 | GCKPPTGEH | | 43230 |
| HPV33 | L1 | 243 | 9 | GDSLFFFLR | | 43231 |
| HPV33 | L1 | 243 | 10 | GDSLFFFLRR | | 43232 |
| HPV33 | L1 | 204 | 8 | GFGCMDFK | | 43233 |
| HPV33 | L1 | 85 | 8 | GFPDTSFY | | 43234 |
| HPV33 | L1 | 117 | 10 | GISGHPLLNK | | 43235 |
| HPV33 | L1 | 472 | 9 | GLKAKPKLK | | 43236 |
| HPV33 | L1 | 472 | 10 | GLKAKPKLKR | | 43237 |
| HPV33 | L1 | 68 | 8 | GLQYRVFR | | 43238 |
| HPV33 | L1 | 68 | 10 | GLQYRVFRVR | | 43239 |
| HPV33 | L1 | 38 | 10 | GSSRLLAVGH | | 43240 |
| HPV33 | L1 | 226 | 9 | GSTCKYPDY | | 43241 |
| HPV33 | L1 | 226 | 11 | GSTCKYPDYLK | | 43242 |
| HPV33 | L1 | 224 | 8 | ICGSTCKY | | 43243 |
| HPV33 | L1 | 224 | 11 | ICGSTCKYPDY | | 43244 |
| HPV33 | L1 | 222 | 9 | IDICGSTCK | | 43245 |
| HPV33 | L1 | 222 | 10 | IDICGSTCKY | | 43246 |
| HPV33 | L1 | 118 | 9 | ISGHPLLNK | | 43247 |
| HPV33 | L1 | 425 | 10 | ITCQKTVPPK | | 43248 |
| HPV33 | L1 | 474 | 8 | KAKPKLKR | | 43249 |
| HPV33 | L1 | 126 | 10 | KFDDTETGNK | | 43250 |
| HPV33 | L1 | 126 | 11 | KFDDTETGNKY | | 43251 |
| HPV33 | L1 | 83 | 10 | KFGFPDTSFY | | 43252 |
| HPV33 | L1 | 466 | 9 | KFLLQAGLK | | 43253 |
| HPV33 | L1 | 466 | 11 | KFLLQAGLKAK | | 43254 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | L1 | 478 | 11 | KLKRAAPTSTR | | 43255 |
| HPV33 | L1 | 355 | 8 | KNENFKEY | | 43256 |
| HPV33 | L1 | 355 | 10 | KNENFKEYIR | | 43257 |
| HPV33 | L1 | 355 | 11 | KNENFKEYIRH | | 43258 |
| HPV33 | L1 | 53 | 8 | KNPTNAKK | | 43259 |
| HPV33 | L1 | 429 | 8 | KTVPPKEK | | 43260 |
| HPV33 | L1 | 65 | 8 | KVSGLQYR | | 43261 |
| HPV33 | L1 | 65 | 11 | KVSGLQYRVFR | | 43262 |
| HPV33 | L1 | 379 | 11 | KVTLTAEVMTY | | 43263 |
| HPV33 | L1 | 20 | 8 | KVVSTDEY | | 43264 |
| HPV33 | L1 | 20 | 11 | KVVSTDEYVSR | | 43265 |
| HPV33 | L1 | 43 | 11 | LAVGHPYFSIK | | 43266 |
| HPV33 | L1 | 344 | 11 | LCTQVTSDSTY | | 43267 |
| HPV33 | L1 | 458 | 8 | LDQFPLGR | | 43268 |
| HPV33 | L1 | 458 | 9 | LDQFPLGRK | | 43269 |
| HPV33 | L1 | 306 | 10 | LFNKPYWLQR | | 43270 |
| HPV33 | L1 | 160 | 10 | LGCKPPTGEH | | 43271 |
| HPV33 | L1 | 267 | 10 | LGEAVPDDLY | | 43272 |
| HPV33 | L1 | 114 | 8 | LGVGISGH | | 43273 |
| HPV33 | L1 | 42 | 8 | LLAVGHPY | | 43274 |
| HPV33 | L1 | 159 | 11 | LLGCKPPTGEH | | 43275 |
| HPV33 | L1 | 468 | 9 | LLQAGLKAK | | 43276 |
| HPV33 | L1 | 468 | 11 | LLQAGLKAKPK | | 43277 |
| HPV33 | L1 | 61 | 11 | LLVPKVSGLQY | | 43278 |
| HPV33 | L1 | 382 | 8 | LTAEVMTY | | 43279 |
| HPV33 | L1 | 382 | 10 | LTAEVMTYIH | | 43280 |
| HPV33 | L1 | 62 | 10 | LVPKVSGLQY | | 43281 |
| HPV33 | L1 | 62 | 11 | LVPKVSGLQYR | | 43282 |
| HPV33 | L1 | 208 | 10 | MDFKTLQANK | | 43283 |
| HPV33 | L1 | 255 | 9 | MFVRHFFNR | | 43284 |
| HPV33 | L1 | 299 | 11 | MVTSESQLFNK | | 43285 |
| HPV33 | L1 | 57 | 9 | NAKKLLVPK | | 43286 |
| HPV33 | L1 | 358 | 8 | NFKEYIRH | | 43287 |
| HPV33 | L1 | 232 | 11 | PDYLKMTSEPY | | 43288 |
| HPV33 | L1 | 137 | 9 | PGQPGADNR | | 43289 |
| HPV33 | L1 | 221 | 10 | PIDICGSTCK | | 43290 |
| HPV33 | L1 | 221 | 11 | PIDICGSTCKY | | 43291 |
| HPV33 | L1 | 113 | 9 | PLGVGISGH | | 43292 |
| HPV33 | L1 | 409 | 9 | PSASLQDTY | | 43293 |
| HPV33 | L1 | 409 | 10 | PSASLQDTYR | | 43294 |
| HPV33 | L1 | 165 | 8 | PTGEHWGK | | 43295 |
| HPV33 | L1 | 55 | 11 | PTNAKKLLVPK | | 43296 |
| HPV33 | L1 | 484 | 10 | PTSTRTSSAK | | 43297 |
| HPV33 | L1 | 484 | 11 | PTSTRTSSAKR | | 43298 |
| HPV33 | L1 | 17 | 11 | PVSKVVSTDEY | | 43299 |
| HPV33 | L1 | 470 | 9 | QAGLKAKPK | | 43300 |
| HPV33 | L1 | 470 | 11 | QAGLKAKPKLK | | 43301 |
| HPV33 | L1 | 372 | 8 | QFVFQLCK | | 43302 |
| HPV33 | L1 | 156 | 8 | QLCLLGCK | | 43303 |
| HPV33 | L1 | 305 | 11 | QLFNKPYWLQR | | 43304 |
| HPV33 | L1 | 254 | 10 | QMFVRHFFNR | | 43305 |
| HPV33 | L1 | 154 | 10 | QTQLCLLGCK | | 43306 |
| HPV33 | L1 | 328 | 11 | QVFVTVVDTTR | | 43307 |
| HPV33 | L1 | 347 | 8 | QVTSDSTY | | 43308 |
| HPV33 | L1 | 347 | 9 | QVTSDSTYK | | 43309 |
| HPV33 | L1 | 481 | 8 | RAAPTSTR | | 43310 |
| HPV33 | L1 | 41 | 9 | RLLAVGHPY | | 43311 |
| HPV33 | L1 | 488 | 8 | RTSSAKRK | | 43312 |
| HPV33 | L1 | 488 | 9 | RTSSAKRKK | | 43313 |
| HPV33 | L1 | 488 | 11 | RTSSAKRKKVK | | 43314 |
| HPV33 | L1 | 75 | 9 | RVRLPDPNK | | 43315 |
| HPV33 | L1 | 455 | 11 | SADLDQFFLGR | | 43316 |
| HPV33 | L1 | 491 | 8 | SAKRKKVK | | 43317 |
| HPV33 | L1 | 491 | 9 | SAKRKKVKK | | 43318 |
| HPV33 | L1 | 410 | 8 | SASLQDTY | | 43319 |
| HPV33 | L1 | 410 | 9 | SASLQDTYR | | 43320 |
| HPV33 | L1 | 350 | 11 | SDSTYKNENFK | | 43321 |
| HPV33 | L1 | 90 | 9 | SFYNPDTQR | | 43322 |
| HPV33 | L1 | 119 | 8 | SGHPLLNK | | 43323 |
| HPV33 | L1 | 67 | 9 | SGLQYRVFR | | 43324 |
| HPV33 | L1 | 67 | 11 | SGLQYRVFRVR | | 43325 |
| HPV33 | L1 | 51 | 9 | SIKNPTNAK | | 43326 |
| HPV33 | L1 | 51 | 10 | SIKNPTNAKK | | 43327 |
| HPV33 | L1 | 32 | 10 | SIYYYAGSSR | | 43328 |
| HPV33 | L1 | 245 | 8 | SLFFFLRR | | 43329 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | L1 | 490 | 9 | SSAKRKKVK | | 43330 |
| HPV33 | L1 | 490 | 10 | SSAKRKKVKK | | 43331 |
| HPV33 | L1 | 39 | 9 | SSRLLAVGH | | 43332 |
| HPV33 | L1 | 39 | 11 | SSRLLAVGHPY | | 43333 |
| HPV33 | L1 | 227 | 8 | STCKYPDY | | 43334 |
| HPV33 | L1 | 227 | 10 | STCKYPDYLK | | 43335 |
| HPV33 | L1 | 23 | 8 | STDEYVSR | | 43336 |
| HPV33 | L1 | 486 | 8 | STRTSSAK | | 43337 |
| HPV33 | L1 | 486 | 9 | STRTSSAKR | | 43338 |
| HPV33 | L1 | 486 | 10 | STRTSSAKRK | | 43339 |
| HPV33 | L1 | 486 | 11 | STRTSSAKRKK | | 43340 |
| HPV33 | L1 | 352 | 9 | STYKNENFK | | 43341 |
| HPV33 | L1 | 352 | 11 | STYKNENFKEY | | 43342 |
| HPV33 | L1 | 2 | 11 | SVWRPSEATVY | | 43343 |
| HPV33 | L1 | 383 | 9 | TAEVMTYIH | | 43344 |
| HPV33 | L1 | 228 | 9 | TCKYPDYLK | | 43345 |
| HPV33 | L1 | 426 | 9 | TCQKTVPPK | | 43346 |
| HPV33 | L1 | 426 | 11 | TCQKTVPPKEK | | 43347 |
| HPV33 | L1 | 24 | 11 | TDEYVSRTSIY | | 43348 |
| HPV33 | L1 | 444 | 8 | TFWEVDLK | | 43349 |
| HPV33 | L1 | 444 | 10 | TFWEVDLKEK | | 43350 |
| HPV33 | L1 | 203 | 9 | TGFGCMDFK | | 43351 |
| HPV33 | L1 | 266 | 11 | TLGEAVPDDLY | | 43352 |
| HPV33 | L1 | 381 | 9 | TLTAEVMTY | | 43353 |
| HPV33 | L1 | 381 | 11 | TLTAEVMTYIH | | 43354 |
| HPV33 | L1 | 56 | 10 | TNAKKLLVPK | | 43355 |
| HPV33 | L1 | 301 | 9 | TSESQLFNK | | 43356 |
| HPV33 | L1 | 301 | 11 | TSESQLFNKPY | | 43357 |
| HPV33 | L1 | 89 | 10 | TSFYNPDTQR | | 43358 |
| HPV33 | L1 | 31 | 11 | TSIYYYAGSSR | | 43359 |
| HPV33 | L1 | 421 | 9 | TSQAITCQK | | 43360 |
| HPV33 | L1 | 489 | 8 | TSSAKRKK | | 43361 |
| HPV33 | L1 | 489 | 10 | TSSAKRKKVK | | 43362 |
| HPV33 | L1 | 489 | 11 | TSSAKRKKVKK | | 43363 |
| HPV33 | L1 | 485 | 9 | TSTRTSSAK | | 43364 |
| HPV33 | L1 | 485 | 10 | TSTRTSSAKR | | 43365 |
| HPV33 | L1 | 485 | 11 | TSTRTSSAKRK | | 43366 |
| HPV33 | L1 | 10 | 11 | TVYLPPVPVSK | | 43367 |
| HPV33 | L1 | 201 | 11 | VDTGFGCMDFK | | 43368 |
| HPV33 | L1 | 73 | 11 | VFRVRLPDPNK | | 43369 |
| HPV33 | L1 | 329 | 10 | VFVTVVDTTR | | 43370 |
| HPV33 | L1 | 45 | 9 | VGHPYFSIK | | 43371 |
| HPV33 | L1 | 116 | 11 | VGISGHPLLNK | | 43372 |
| HPV33 | L1 | 66 | 10 | VSGLQYRVFR | | 43373 |
| HPV33 | L1 | 18 | 10 | VSKVVSTDEY | | 43374 |
| HPV33 | L1 | 28 | 8 | VSRTSIYY | | 43375 |
| HPV33 | L1 | 28 | 9 | VSRTSIYYY | | 43376 |
| HPV33 | L1 | 22 | 9 | VSTDEYVSR | | 43377 |
| HPV33 | L1 | 380 | 10 | VTLTAEVMTY | | 43378 |
| HPV33 | L1 | 348 | 8 | VTSDSTYK | | 43379 |
| HPV33 | L1 | 300 | 10 | VTSESQLFNK | | 43380 |
| HPV33 | L1 | 420 | 10 | VTSQAITCQK | | 43381 |
| HPV33 | L1 | 331 | 8 | VTVVDTTR | | 43382 |
| HPV33 | L1 | 21 | 10 | VVSTDEYVSR | | 43383 |
| HPV33 | L1 | 101 | 10 | WACVGLEIGR | | 43384 |
| HPV33 | L1 | 312 | 8 | WLQRAQGH | | 43385 |
| HPV33 | L1 | 369 | 11 | YDLQFVFQLCK | | 43386 |
| HPV33 | L1 | 49 | 11 | YFSIKNPTNAK | | 43387 |
| HPV33 | L1 | 242 | 10 | YGDSLFFFLR | | 43388 |
| HPV33 | L1 | 242 | 11 | YGDSLFFFLRR | | 43389 |
| HPV33 | L1 | 362 | 8 | YIRHVEEY | | 43390 |
| HPV33 | L1 | 234 | 9 | YLKMTSEPY | | 43391 |
| HPV33 | L1 | 12 | 9 | YLPPVPVSK | | 43392 |
| HPV33 | L1 | 443 | 9 | YTFWEVDLK | | 43393 |
| HPV33 | L1 | 443 | 11 | YTFWEVDLKEK | | 43394 |
| HPV33 | L1 | 27 | 8 | YVSRTSIY | | 43395 |
| HPV33 | L1 | 27 | 9 | YVSRTSIYY | | 43396 |
| HPV33 | L1 | 27 | 10 | YVSRTSIYYY | | 43397 |
| HPV33 | L2 | 81 | 9 | AAIPLQPIR | | 43398 |
| HPV33 | L2 | 367 | 8 | ADDVDNVH | | 43399 |
| HPV33 | L2 | 438 | 9 | ADFVLHPSY | | 43400 |
| HPV33 | L2 | 241 | 8 | AFLTSPHK | | 43401 |
| HPV33 | L2 | 82 | 8 | AIPLQPIR | | 43402 |
| HPV33 | L2 | 291 | 10 | AITSRRHTVR | | 43403 |
| HPV33 | L2 | 286 | 10 | ALHRPAITSR | | 43404 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | L2 | 286 | 11 | ALHRPAITSRR | | 43405 |
| HPV33 | L2 | 12 | 11 | ASATQLYQTCK | | 43406 |
| HPV33 | L2 | 308 | 9 | ATLKTRSGK | | 43407 |
| HPV33 | L2 | 14 | 9 | ATQLYQTCK | | 43408 |
| HPV33 | L2 | 280 | 9 | DFLDIIALH | | 43409 |
| HPV33 | L2 | 280 | 10 | DFLDIIALHR | | 43410 |
| HPV33 | L2 | 439 | 8 | DFVLHPSY | | 43411 |
| HPV33 | L2 | 436 | 8 | DGADFVLH | | 43412 |
| HPV33 | L2 | 436 | 11 | DGADFVLHPSY | | 43413 |
| HPV33 | L2 | 327 | 10 | DLSPIVPLDH | | 43414 |
| HPV33 | L2 | 371 | 9 | DNVHTPMQH | | 43415 |
| HPV33 | L2 | 371 | 11 | DNVHTPMQHSY | | 43416 |
| HPV33 | L2 | 369 | 11 | DVDNVHTPMQH | | 43417 |
| HPV33 | L2 | 364 | 11 | DVYADDVDNVH | | 43418 |
| HPV33 | L2 | 263 | 8 | EDTLQFQH | | 43419 |
| HPV33 | L2 | 36 | 11 | EGSTIADQILK | | 43420 |
| HPV33 | L2 | 149 | 10 | ESSIQTISTH | | 43421 |
| HPV33 | L2 | 260 | 11 | FDPEDTLQFQH | | 43422 |
| HPV33 | L2 | 447 | 8 | FILRRRRK | | 43423 |
| HPV33 | L2 | 447 | 9 | FILRRRRKR | | 43424 |
| HPV33 | L2 | 281 | 8 | FLDIIALH | | 43425 |
| HPV33 | L2 | 281 | 9 | FLDIIALHR | | 43426 |
| HPV33 | L2 | 242 | 11 | FLTSPHKLITY | | 43427 |
| HPV33 | L2 | 301 | 11 | FSRVGQKATLK | | 43428 |
| HPV33 | L2 | 183 | 11 | FSSPTVSTQSY | | 43429 |
| HPV33 | L2 | 163 | 8 | FTEPSVLH | | 43430 |
| HPV33 | L2 | 440 | 11 | FVLHPSYFILR | | 43431 |
| HPV33 | L2 | 437 | 10 | GADFVLHPSY | | 43432 |
| HPV33 | L2 | 58 | 11 | GIGTGSGSGGR | | 43433 |
| HPV33 | L2 | 226 | 11 | GLYSRNTQQVK | | 43434 |
| HPV33 | L2 | 64 | 8 | GSGGRTGY | | 43435 |
| HPV33 | L2 | 62 | 10 | GSGSGGRTGY | | 43436 |
| HPV33 | L2 | 218 | 11 | GSRPVARLGLY | | 43437 |
| HPV33 | L2 | 37 | 10 | GSTIADQILK | | 43438 |
| HPV33 | L2 | 37 | 11 | GSTIADQILKY | | 43439 |
| HPV33 | L2 | 25 | 10 | GTCPPDVIPK | | 43440 |
| HPV33 | L2 | 60 | 9 | GTGSGSGGR | | 43441 |
| HPV33 | L2 | 349 | 8 | HDTSTSSY | | 43442 |
| HPV33 | L2 | 379 | 10 | HSYSTFATTR | | 43443 |
| HPV33 | L2 | 374 | 8 | HTPMQHSY | | 43444 |
| HPV33 | L2 | 336 | 8 | HTVPNEQY | | 43445 |
| HPV33 | L2 | 297 | 11 | HTVRFSRVGQK | | 43446 |
| HPV33 | L2 | 40 | 8 | IADQILKY | | 43447 |
| HPV33 | L2 | 285 | 11 | IALHRPAITSR | | 43448 |
| HPV33 | L2 | 318 | 8 | IGARIHYY | | 43449 |
| HPV33 | L2 | 59 | 10 | IGTGSGSGGR | | 43450 |
| HPV33 | L2 | 448 | 8 | ILRRRRKR | | 43451 |
| HPV33 | L2 | 448 | 11 | ILRRRRKRFPY | | 43452 |
| HPV33 | L2 | 358 | 9 | INDGLYDVY | | 43453 |
| HPV33 | L2 | 292 | 9 | ITSRRHTVR | | 43454 |
| HPV33 | L2 | 433 | 11 | IVVDGADFVLH | | 43455 |
| HPV33 | L2 | 307 | 10 | KATLKTRSGK | | 43456 |
| HPV33 | L2 | 311 | 11 | KTRSGKQIGAR | | 43457 |
| HPV33 | L2 | 334 | 10 | LDHTVPNEQY | | 43458 |
| HPV33 | L2 | 282 | 8 | LDIIALHR | | 43459 |
| HPV33 | L2 | 328 | 9 | LSPIVPLDH | | 43460 |
| HPV33 | L2 | 243 | 10 | LTSPHKLITY | | 43461 |
| HPV33 | L2 | 359 | 8 | NDGLYDVY | | 43462 |
| HPV33 | L2 | 372 | 8 | NVHTPMQH | | 43463 |
| HPV33 | L2 | 372 | 10 | NVHTPMQHSY | | 43464 |
| HPV33 | L2 | 240 | 8 | PAFLTSPH | | 43465 |
| HPV33 | L2 | 240 | 9 | PAFLTSPHK | | 43466 |
| HPV33 | L2 | 290 | 8 | PAITSRRH | | 43467 |
| HPV33 | L2 | 290 | 11 | PAITSRRHTVR | | 43468 |
| HPV33 | L2 | 172 | 9 | PAPAEASGH | | 43469 |
| HPV33 | L2 | 279 | 10 | PDFLDIIALH | | 43470 |
| HPV33 | L2 | 279 | 11 | PDFLDIIALHR | | 43471 |
| HPV33 | L2 | 217 | 8 | PGSRPVAR | | 43472 |
| HPV33 | L2 | 215 | 10 | PIPGSRPVAR | | 43473 |
| HPV33 | L2 | 333 | 11 | PLDHTVPNEQY | | 43474 |
| HPV33 | L2 | 347 | 10 | PLHDTSTSSY | | 43475 |
| HPV33 | L2 | 339 | 11 | PNEQYELQPLH | | 43476 |
| HPV33 | L2 | 444 | 8 | PSYFILRR | | 43477 |
| HPV33 | L2 | 444 | 9 | PSYFILRRR | | 43478 |
| HPV33 | L2 | 444 | 10 | PSYFILRRRR | | 43479 |

TABLE XVII-continued

A11 Motif Peptides

| Type | Protein | Position | No. of Amino Acids | Sequence | A*1101 | Seq. Id. No. |
|---|---|---|---|---|---|---|
| HPV33 | L2 | 444 | 11 | PSYFILRRRRK | | 43480 |
| HPV33 | L2 | 79 | 11 | PTAAIPLQPIR | | 43481 |
| HPV33 | L2 | 161 | 10 | PTFTEPSVLH | | 43482 |
| HPV33 | L2 | 186 | 8 | PTVSTQSY | | 43483 |
| HPV33 | L2 | 221 | 8 | PVARLGLY | | 43484 |
| HPV33 | L2 | 221 | 10 | PVARLGLYSR | | 43485 |
| HPV33 | L2 | 326 | 11 | QDLSPIVPLDH | | 43486 |
| HPV33 | L2 | 317 | 8 | QIGARIHY | | 43487 |
| HPV33 | L2 | 317 | 9 | QIGARIHYY | | 43488 |
| HPV33 | L2 | 11 | 8 | RASATQLY | | 43489 |
| HPV33 | L2 | 455 | 10 | RFPYFFTDVR | | 43490 |
| HPV33 | L2 | 300 | 8 | RFSRVGQK | | 43491 |
| HPV33 | L2 | 313 | 9 | RSGKQIGAR | | 43492 |
| HPV33 | L2 | 313 | 11 | RSGKQIGARIH | | 43493 |
| HPV33 | L2 | 303 | 9 | RVGQKATLK | | 43494 |
| HPV33 | L2 | 303 | 11 | RVGQKATLKTR | | 43495 |
| HPV33 | L2 | 13 | 10 | SATQLYQTCK | | 43496 |
| HPV33 | L2 | 314 | 8 | SGKQIGAR | | 43497 |
| HPV33 | L2 | 314 | 10 | SGKQIGARIH | | 43498 |
| HPV33 | L2 | 314 | 11 | SGKQIGARIHY | | 43499 |
| HPV33 | L2 | 63 | 9 | SGSGGRTGY | | 43500 |
| HPV33 | L2 | 357 | 10 | SINDGLYDVY | | 43501 |
| HPV33 | L2 | 151 | 8 | SIQTISTH | | 43502 |
| HPV33 | L2 | 150 | 9 | SSIQTISTH | | 43503 |
| HPV33 | L2 | 184 | 10 | SSPTVSTQSY | | 43504 |
| HPV33 | L2 | 212 | 9 | SSTPIPGSR | | 43505 |
| HPV33 | L2 | 354 | 10 | SSYSINDGLY | | 43506 |
| HPV33 | L2 | 38 | 9 | STIADQILK | | 43507 |
| HPV33 | L2 | 38 | 10 | STIADQILKY | | 43508 |
| HPV33 | L2 | 213 | 8 | STPIPGSR | | 43509 |
| HPV33 | L2 | 80 | 10 | TAAIPLQPIR | | 43510 |
| HPV33 | L2 | 26 | 9 | TCPPDVIPK | | 43511 |
| HPV33 | L2 | 162 | 9 | TFTEPSVLH | | 43512 |
| HPV33 | L2 | 61 | 8 | TGSGSGGR | | 43513 |
| HPV33 | L2 | 61 | 11 | TGSGSGGRTGY | | 43514 |
| HPV33 | L2 | 24 | 11 | TGTCPPDVIPK | | 43515 |
| HPV33 | L2 | 39 | 8 | TIADQILK | | 43516 |
| HPV33 | L2 | 39 | 9 | TIADQILKY | | 43517 |
| HPV33 | L2 | 309 | 8 | TLKTRSGK | | 43518 |
| HPV33 | L2 | 244 | 9 | TSPHKLITY | | 43519 |
| HPV33 | L2 | 293 | 8 | TSRRHTVR | | 43520 |
| HPV33 | L2 | 293 | 11 | TSRRHTVRFSR | | 43521 |
| HPV33 | L2 | 211 | 10 | TSSTPIPGSR | | 43522 |
| HPV33 | L2 | 353 | 11 | TSSYSINDGLY | | 43523 |
| HPV33 | L2 | 298 | 10 | TVRFSRVGQK | | 43524 |
| HPV33 | L2 | 222 | 9 | VARLGLYSR | | 43525 |
| HPV33 | L2 | 435 | 9 | VDGADFVLH | | 43526 |
| HPV33 | L2 | 370 | 10 | VDNVHTPMQH | | 43527 |
| HPV33 | L2 | 238 | 10 | VDPAFLTSPH | | 43528 |
| HPV33 | L2 | 238 | 11 | VDPAFLTSPHK | | 43529 |
| HPV33 | L2 | 304 | 8 | VGQKATLK | | 43530 |
| HPV33 | L2 | 304 | 10 | VGQKATLKTR | | 43531 |
| HPV33 | L2 | 441 | 10 | VLHPSYFILR | | 43532 |
| HPV33 | L2 | 441 | 11 | VLHPSYFILRR | | 43533 |
| HPV33 | L2 | 210 | 11 | VTSSTPIPGSR | | 43534 |
| HPV33 | L2 | 434 | 10 | VVDGADFVLH | | 43535 |
| HPV33 | L2 | 237 | 11 | VVDPAFLTSPH | | 43536 |
| HPV33 | L2 | 366 | 9 | YADDVDNVH | | 43537 |
| HPV33 | L2 | 446 | 8 | YFILRRRR | | 43538 |
| HPV33 | L2 | 446 | 9 | YFILRRRRK | | 43539 |
| HPV33 | L2 | 446 | 10 | YFILRRRRKR | | 43540 |
| HPV33 | L2 | 356 | 8 | YSINDGLY | | 43541 |
| HPV33 | L2 | 356 | 11 | YSINDGLYDVY | | 43542 |
| HPV33 | L2 | 228 | 9 | YSRNTQQVK | | 43543 |
| HPV33 | L2 | 381 | 8 | YSTFATTR | | 43544 |
| HPV45 | E1 | 383 | 11 | AAFLKSNCQAK | | 43545 |
| HPV45 | E1 | 198 | 8 | AAMLAVFK | | 43546 |
| HPV45 | E1 | 198 | 11 | AAMLAVFKDIY | | 43547 |
| HPV45 | E1 | 384 | 10 | AFLKSNCQAK | | 43548 |
| HPV45 | E1 | 384 | 11 | AFLKSNCQAKY | | 43549 |
| HPV45 | E1 | 490 | 11 | AIISFVNSNSH | | 43550 |
| HPV45 | E1 | 532 | 11 | ALDGNPISIDR | | 43551 |
| HPV45 | E1 | 452 | 11 | ALKEFLKGTPK | | 43552 |
| HPV45 | E1 | 270 | 9 | ALLRYKCGK | 0.1400 | 43553 |
| HPV45 | E1 | 270 | 11 | ALLRYKCGKNR | | 43554 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV45 | E1 | 199 | 10 | AMLAVFKDIY | | 43555 |
| HPV45 | E1 | 512 | 8 | AMLDDATH | | 43556 |
| HPV45 | E1 | 517 | 8 | ATHTCWTY | | 43557 |
| HPV45 | E1 | 399 | 8 | AVMCRHYK | | 43558 |
| HPV45 | E1 | 399 | 9 | AVMCRHYKR | | 43559 |
| HPV45 | E1 | 398 | 8 | CAVMCRHY | | 43560 |
| HPV45 | E1 | 398 | 9 | CAVMCRHYK | | 43561 |
| HPV45 | E1 | 398 | 10 | CAVMCRHYKR | | 43562 |
| HPV45 | E1 | 604 | 9 | CFFERTWSR | | 43563 |
| HPV45 | E1 | 276 | 10 | CGKNRLTVAK | | 43564 |
| HPV45 | E1 | 297 | 8 | CMLIEPPK | | 43565 |
| HPV45 | E1 | 297 | 10 | CMLIEPPKLR | | 43566 |
| HPV45 | E1 | 378 | 10 | CNSNAAAFLK | | 43567 |
| HPV45 | E1 | 423 | 11 | CSKIDEGGDWR | | 43568 |
| HPV45 | E1 | 634 | 8 | CVTGQNTR | | 43569 |
| HPV45 | E1 | 78 | 9 | DAQVLHLLK | | 43570 |
| HPV45 | E1 | 78 | 10 | DAQVLHLLKR | | 43571 |
| HPV45 | E1 | 78 | 11 | DAQVLHLLKRK | | 43572 |
| HPV45 | E1 | 516 | 9 | DATHTCWTY | | 43573 |
| HPV45 | E1 | 397 | 8 | DCAVMCRH | | 43574 |
| HPV45 | E1 | 397 | 9 | DCAVMCRHY | | 43575 |
| HPV45 | E1 | 397 | 10 | DCAVMCRHYK | | 43576 |
| HPV45 | E1 | 397 | 11 | DCAVMCRHYKR | | 43577 |
| HPV45 | E1 | 377 | 11 | DCNSNAAAFLK | | 43578 |
| HPV45 | E1 | 515 | 10 | DDATHTCWTY | | 43579 |
| HPV45 | E1 | 534 | 9 | DGNPISIDR | | 43580 |
| HPV45 | E1 | 534 | 10 | DGNPISIDRK | | 43581 |
| HPV45 | E1 | 534 | 11 | DGNPISIDRKH | | 43582 |
| HPV45 | E1 | 214 | 10 | DLVRNFKSDK | | 43583 |
| HPV45 | E1 | 173 | 9 | DNAENVDPH | | 43584 |
| HPV45 | E1 | 566 | 10 | DNKQPYLESR | | 43585 |
| HPV45 | E1 | 623 | 11 | DTEGIPFGTFK | | 43586 |
| HPV45 | E1 | 328 | 8 | DTPEWIQR | | 43587 |
| HPV45 | E1 | 445 | 10 | EFISFLRALK | | 43588 |
| HPV45 | E1 | 455 | 8 | EFLKGTPK | | 43589 |
| HPV45 | E1 | 455 | 9 | EFLKGTPKK | | 43590 |
| HPV45 | E1 | 242 | 8 | EGFKTLIK | | 43591 |
| HPV45 | E1 | 625 | 9 | EGIPFGTFK | | 43592 |
| HPV45 | E1 | 596 | 8 | EINDKNWK | | 43593 |
| HPV45 | E1 | 115 | 8 | EISLNSGH | | 43594 |
| HPV45 | E1 | 115 | 9 | EISLNSGHK | | 43595 |
| HPV45 | E1 | 115 | 10 | EISLNSGHKK | | 43596 |
| HPV45 | E1 | 186 | 11 | ELKELLQASNK | | 43597 |
| HPV45 | E1 | 189 | 8 | ELLQASNK | | 43598 |
| HPV45 | E1 | 189 | 9 | ELLQASNKK | | 43599 |
| HPV45 | E1 | 365 | 8 | ESDMAFQY | | 43600 |
| HPV45 | E1 | 573 | 11 | ESRVTVFTFPH | | 43601 |
| HPV45 | E1 | 64 | 8 | ETAQALFH | | 43602 |
| HPV45 | E1 | 295 | 10 | ETCMLIEPPK | | 43603 |
| HPV45 | E1 | 74 | 10 | EVQNDAQVLH | | 43604 |
| HPV45 | E1 | 587 | 9 | FDKNGNPVY | | 43605 |
| HPV45 | E1 | 605 | 8 | FFERTWSR | | 43606 |
| HPV45 | E1 | 18 | 9 | FFVETIVEK | | 43607 |
| HPV45 | E1 | 18 | 10 | FFVETIVEKK | | 43608 |
| HPV45 | E1 | 446 | 9 | FISFLRALK | | 43609 |
| HPV45 | E1 | 456 | 8 | FLKGTPKK | | 43610 |
| HPV45 | E1 | 385 | 9 | FLKSNCQAK | 0.0007 | 43611 |
| HPV45 | E1 | 385 | 10 | FLKSNCQAKY | | 43612 |
| HPV45 | E1 | 449 | 10 | FLRALKEFLK | | 43613 |
| HPV45 | E1 | 212 | 9 | FTDLVRNFK | | 43614 |
| HPV45 | E1 | 579 | 11 | FTFPHAFPFDK | | 43615 |
| HPV45 | E1 | 130 | 8 | FTISDSGY | | 43616 |
| HPV45 | E1 | 19 | 8 | FVETIVEK | | 43617 |
| HPV45 | E1 | 19 | 9 | FVETIVEKK | | 43618 |
| HPV45 | E1 | 327 | 9 | GDTPEWIQR | 0.0002 | 43619 |
| HPV45 | E1 | 430 | 11 | GDWRPIVQFLR | | 43620 |
| HPV45 | E1 | 626 | 8 | GIPFGTFK | | 43621 |
| HPV45 | E1 | 209 | 9 | GLSFTDLVR | 0.0025 | 43622 |
| HPV45 | E1 | 535 | 8 | GNPISIDR | | 43623 |
| HPV45 | E1 | 535 | 9 | GNPISIDRK | | 43624 |
| HPV45 | E1 | 535 | 10 | GNPISIDRKH | | 43625 |
| HPV45 | E1 | 535 | 11 | GNPISIDRKHK | | 43626 |
| HPV45 | E1 | 591 | 10 | GNPVYEINDK | | 43627 |
| HPV45 | E1 | 459 | 11 | GTPKKNCILLY | | 43628 |
| HPV45 | E1 | 443 | 9 | GVEFISFLR | | 43629 |

TABLE XVII-continued

All Motif Peptides

| Type | Protein | Position | No. of Amino Acids | Sequeuce | A*1101 | Seq. Id. No. |
|---|---|---|---|---|---|---|
| HPV45 | E1 | 265 | 9 | GVLILALLR | 0.1400 | 43630 |
| HPV45 | E1 | 265 | 10 | GVLILALLRY | | 43631 |
| HPV45 | E1 | 265 | 11 | GVLILALLRYK | | 43632 |
| HPV45 | E1 | 235 | 11 | GVNPTVAEGFK | | 43633 |
| HPV45 | E1 | 181 | 8 | HCSITELK | | 43634 |
| HPV45 | E1 | 500 | 11 | HFWLEPLADTK | | 43635 |
| HPV45 | E1 | 256 | 8 | HIQCLDCK | | 43636 |
| HPV45 | E1 | 519 | 10 | HTCWTYFDNY | | 43637 |
| HPV45 | E1 | 426 | 8 | IDEGGDWR | | 43638 |
| HPV45 | E1 | 561 | 8 | IDPAKDNK | | 43639 |
| HPV45 | E1 | 561 | 11 | IDPAKDNKWPY | | 43640 |
| HPV45 | E1 | 491 | 10 | IISFVNSNSH | | 43641 |
| HPV45 | E1 | 268 | 8 | ILALLRYK | | 43642 |
| HPV45 | E1 | 268 | 11 | ILALLRYKCGK | | 43643 |
| HPV45 | E1 | 555 | 11 | ILLTSNIDPAK | | 43644 |
| HPV45 | E1 | 466 | 11 | ILLYGPANTGK | | 43645 |
| HPV45 | E1 | 447 | 8 | ISFLRALK | | 43646 |
| HPV45 | E1 | 492 | 9 | ISFVNSNSH | | 43647 |
| HPV45 | E1 | 538 | 8 | ISIDRKHK | | 43648 |
| HPV45 | E1 | 116 | 8 | ISLNSGHK | | 43649 |
| HPV45 | E1 | 116 | 9 | ISLNSGHKK | | 43650 |
| HPV45 | E1 | 116 | 11 | ISLNSGHKKAK | | 43651 |
| HPV45 | E1 | 197 | 9 | KAAMLAVFK | | 43652 |
| HPV45 | E1 | 603 | 10 | KCFFERTWSR | | 43653 |
| HPV45 | E1 | 275 | 11 | KCGKNRUTVAK | | 43654 |
| HPV45 | E1 | 633 | 9 | KCVTGQNTR | | 43655 |
| HPV45 | E1 | 396 | 8 | KDCAVMCR | | 43656 |
| HPV45 | E1 | 396 | 9 | KDCAVMCRH | | 43657 |
| HPV45 | E1 | 396 | 10 | KDCAVMCRHY | | 43658 |
| HPV45 | E1 | 396 | 11 | KDCAVMCRHYK | | 43659 |
| HPV45 | E1 | 565 | 11 | KDNKWPYLESR | | 43660 |
| HPV45 | E1 | 285 | 8 | KGLSTLLH | | 43661 |
| HPV45 | E1 | 425 | 9 | KIDEGGDWR | | 43662 |
| HPV45 | E1 | 304 | 10 | KLRSSVAALY | | 43663 |
| HPV45 | E1 | 278 | 8 | KNRLTVAK | | 43664 |
| HPV45 | E1 | 600 | 9 | KNWKCFFER | | 43665 |
| HPV45 | E1 | 387 | 8 | KSNCQAKY | | 43666 |
| HPV45 | E1 | 387 | 10 | KSNCQAKYLK | | 43667 |
| HPV45 | E1 | 476 | 10 | KSYFGMSFIH | | 43668 |
| HPV45 | E1 | 245 | 10 | KTLIKPATLY | | 43669 |
| HPV45 | E1 | 510 | 10 | KVAMLDDATH | | 43670 |
| HPV45 | E1 | 269 | 10 | LALLRYKCGK | | 43671 |
| HPV45 | E1 | 201 | 8 | LAVFKDIY | | 43672 |
| HPV45 | E1 | 514 | 11 | LDDATHTCWTY | | 43673 |
| HPV45 | E1 | 533 | 10 | LDGNPISIDR | | 43674 |
| HPV45 | E1 | 533 | 11 | LDGNPISIDRK | | 43675 |
| HPV45 | E1 | 129 | 9 | LFTISDSGY | | 43676 |
| HPV45 | E1 | 299 | 8 | LIEPPKLR | | 43677 |
| HPV45 | E1 | 247 | 8 | LIKPATLY | | 43678 |
| HPV45 | E1 | 247 | 10 | LIKPATLYAH | | 43679 |
| HPV45 | E1 | 267 | 8 | LILALLRY | | 43680 |
| HPV45 | E1 | 267 | 9 | LILALLRYK | 0.1800 | 43681 |
| HPV45 | E1 | 84 | 11 | LLKRKFAGGSK | | 43682 |
| HPV45 | E1 | 190 | 8 | LLQASNKK | | 43683 |
| HPV45 | E1 | 271 | 8 | LLRYKCGK | | 43684 |
| HPV45 | E1 | 271 | 10 | LLRYKCGKNR | | 43685 |
| HPV45 | E1 | 556 | 10 | LLTSNIDPAK | | 43686 |
| HPV45 | E1 | 467 | 10 | LLYGPANTGK | | 43687 |
| HPV45 | E1 | 118 | 9 | LNSGHKKAK | | 43688 |
| HPV45 | E1 | 118 | 10 | LNSGHKKAKR | | 43689 |
| HPV45 | E1 | 118 | 11 | LNSGHKKAKRR | | 43690 |
| HPV45 | E1 | 210 | 8 | LSFTDLVR | | 43691 |
| HPV45 | E1 | 210 | 11 | LSFTDLVRNFK | | 43692 |
| HPV45 | E1 | 103 | 10 | LSVDTDLSPR | | 43693 |
| HPV45 | E1 | 362 | 11 | LTDESDMAFQY | | 43694 |
| HPV45 | E1 | 557 | 9 | LTSNIDPAK | | 43695 |
| HPV45 | E1 | 215 | 9 | LVRNFKSDK | 0.0002 | 43696 |
| HPV45 | E1 | 401 | 10 | MCRHYKRAQK | | 43697 |
| HPV45 | E1 | 401 | 11 | MCRHYKRAQKR | | 43698 |
| HPV45 | E1 | 200 | 9 | MLAVFKDIY | | 43699 |
| HPV45 | E1 | 298 | 9 | MLIEPPKLR | | 43700 |
| HPV45 | E1 | 413 | 8 | MNMSQWIK | | 43701 |
| HPV45 | E1 | 413 | 9 | MNMSQWIKY | | 43702 |
| HPV45 | E1 | 413 | 10 | MNMSQWIKYR | | 43703 |
| HPV45 | E1 | 415 | 8 | MSQWIKYR | | 43704 |

TABLE XVII-continued

A11 Motif Peptides

| Type | Protein | Position | No. of Amino Acids | Sequence | A*1101 | Seq. Id. No. |
|---|---|---|---|---|---|---|
| HPV45 | E1 | 415 | 11 | MSQWIKYRCSK | | 43705 |
| HPV45 | E1 | 154 | 9 | NAENGGSVH | | 43706 |
| HPV45 | E1 | 174 | 8 | NAENVDPH | | 43707 |
| HPV45 | E1 | 389 | 8 | NCQAKYLK | | 43708 |
| HPV45 | E1 | 77 | 10 | NDAQVLHLLK | | 43709 |
| HPV45 | E1 | 77 | 11 | NDAQVLHLLKR | | 43710 |
| HPV45 | E1 | 598 | 11 | NDKNWKCFFER | | 43711 |
| HPV45 | E1 | 590 | 11 | NGNPVYEINDK | | 43712 |
| HPV45 | E1 | 560 | 9 | NIDPAKDNK | | 43713 |
| HPV45 | E1 | 414 | 8 | NMSQWIKY | | 43714 |
| HPV45 | E1 | 414 | 9 | NMSQWIKYR | | 43715 |
| HPV45 | E1 | 119 | 8 | NSGHKKAK | | 43716 |
| HPV45 | E1 | 119 | 9 | NSGHKKAKR | | 43717 |
| HPV45 | E1 | 119 | 10 | NSGHKKAKRR | | 43718 |
| HPV45 | E1 | 379 | 9 | NSNAAAFLK | 0.3700 | 43719 |
| HPV45 | E1 | 152 | 11 | NTNAENGGSVH | | 43720 |
| HPV45 | E1 | 563 | 9 | PAKDNKWPY | | 43721 |
| HPV45 | E1 | 471 | 8 | PANTGKSY | | 43722 |
| HPV45 | E1 | 586 | 10 | PFDKNGNPVY | | 43723 |
| HPV45 | E1 | 537 | 8 | PISIDRKH | | 43724 |
| HPV45 | E1 | 537 | 9 | PISIDRKHK | | 43725 |
| HPV45 | E1 | 434 | 8 | PIVQFLRY | | 43726 |
| HPV45 | E1 | 238 | 8 | PTVAEGFK | | 43727 |
| HPV45 | E1 | 593 | 8 | PVYEINDK | | 43728 |
| HPV45 | E1 | 593 | 11 | PVYEINDKNWK | | 43729 |
| HPV45 | E1 | 442 | 10 | QGVEFISFLR | | 43730 |
| HPV45 | E1 | 102 | 11 | QLSVDTDLSPR | | 43731 |
| HPV45 | E1 | 412 | 9 | QMNMSQWIK | | 43732 |
| HPV45 | E1 | 412 | 10 | QMNMSQWIKY | | 43733 |
| HPV45 | E1 | 412 | 11 | QMNMSQWIKYR | | 43734 |
| HPV45 | E1 | 76 | 8 | QNDAQVLH | | 43735 |
| HPV45 | E1 | 76 | 11 | QNDAQVLHLLK | | 43736 |
| HPV45 | E1 | 80 | 8 | QVLHLLKR | | 43737 |
| HPV45 | E1 | 80 | 9 | QVLHLLKRK | | 43738 |
| HPV45 | E1 | 451 | 8 | RALKEFLK | | 43739 |
| HPV45 | E1 | 128 | 10 | RLFTISDSGY | | 43740 |
| HPV45 | E1 | 112 | 11 | RLQEISLNSGH | | 43741 |
| HPV45 | E1 | 306 | 8 | RSSVAALY | | 43742 |
| HPV45 | E1 | 306 | 10 | RSSVAALYWY | | 43743 |
| HPV45 | E1 | 306 | 11 | RSSVAALYWYR | | 43744 |
| HPV45 | E1 | 608 | 9 | RTWSRLDLH | | 43745 |
| HPV45 | E1 | 575 | 9 | RVTVFTFPH | | 43746 |
| HPV45 | E1 | 172 | 10 | SDNAENVDPH | | 43747 |
| HPV45 | E1 | 448 | 11 | SFLRALKEFLK | | 43748 |
| HPV45 | E1 | 211 | 10 | SFTDLVRNFK | | 43749 |
| HPV45 | E1 | 493 | 8 | SFVNSNSH | | 43750 |
| HPV45 | E1 | 326 | 10 | SGDTPEWIQR | | 43751 |
| HPV45 | E1 | 120 | 8 | SGHKKAKR | | 43752 |
| HPV45 | E1 | 120 | 9 | SGHKKAKRR | | 43753 |
| HPV45 | E1 | 117 | 8 | SLNSGHKK | | 43754 |
| HPV45 | E1 | 117 | 10 | SLNSGHKKAK | | 43755 |
| HPV45 | E1 | 117 | 11 | SLNSGHKKAKR | | 43756 |
| HPV45 | E1 | 380 | 8 | SNAAAFLK | | 43757 |
| HPV45 | E1 | 388 | 9 | SNCQAKYLK | | 43758 |
| HPV45 | E1 | 559 | 10 | SNIDPAKDNK | | 43759 |
| HPV45 | E1 | 171 | 11 | SSDNAENVDPH | | 43760 |
| HPV45 | E1 | 307 | 9 | SSVAALYWY | | 43761 |
| HPV45 | E1 | 307 | 10 | SSVAALYWYR | | 43762 |
| HPV45 | E1 | 308 | 8 | SVAALYWY | | 43763 |
| HPV45 | E1 | 308 | 9 | SVAALYWYR | 8.8000 | 43764 |
| HPV45 | E1 | 104 | 9 | SVDTDLSPR | | 43765 |
| HPV45 | E1 | 296 | 9 | TCMLIEPPK | | 43766 |
| HPV45 | E1 | 296 | 11 | TCMLIEPPKLR | | 43767 |
| HPV45 | E1 | 520 | 9 | TCWTYFDNY | | 43768 |
| HPV45 | E1 | 520 | 11 | TCWTYFDNYMR | | 43769 |
| HPV45 | E1 | 363 | 10 | TDESDMAFQY | | 43770 |
| HPV45 | E1 | 213 | 8 | TDLVRNFK | | 43771 |
| HPV45 | E1 | 213 | 11 | TDLVRNFKSDK | | 43772 |
| HPV45 | E1 | 631 | 11 | TFKCVTGQNTR | | 43773 |
| HPV45 | E1 | 580 | 10 | TFPHAFPFDK | | 43774 |
| HPV45 | E1 | 246 | 9 | TLIKPATLY | | 43775 |
| HPV45 | E1 | 246 | 11 | TLIKPATLYAH | | 43776 |
| HPV45 | E1 | 153 | 10 | TNAENGGSVH | | 43777 |
| HPV45 | E1 | 558 | 8 | TSNIDPAK | | 43778 |
| HPV45 | E1 | 558 | 11 | TSNIDPAKDNK | | 43779 |

TABLE XVII-continued

A11 Motif Peptides

| Type | Protein | Position | No. of Amino Acids | Sequence | A*1101 | Seq. Id. No. |
|---|---|---|---|---|---|---|
| HPV45 | E1 | 239 | 11 | TVAEGFKTLIK | | 43780 |
| HPV45 | E1 | 282 | 11 | TVAKGLSTLLH | | 43781 |
| HPV45 | E1 | 309 | 8 | VAALYWYR | | 43782 |
| HPV45 | E1 | 240 | 10 | VAEGFKTLIK | | 43783 |
| HPV45 | E1 | 283 | 10 | VAKGLSTLLH | | 43784 |
| HPV45 | E1 | 511 | 9 | VAMLDDATH | | 43785 |
| HPV45 | E1 | 178 | 11 | VDPHCSITELK | | 43786 |
| HPV45 | E1 | 105 | 8 | VDTDLSPR | | 43787 |
| HPV45 | E1 | 81 | 8 | VLHLLKRK | | 43788 |
| HPV45 | E1 | 266 | 8 | VLILALLR | | 43789 |
| HPV45 | E1 | 266 | 9 | VLILALLRY | | 43790 |
| HPV45 | E1 | 266 | 10 | VLILALLRYK | | 43791 |
| HPV45 | E1 | 400 | 8 | VMCRHYKR | | 43792 |
| HPV45 | E1 | 400 | 11 | VMCRHYKRAQK | | 43793 |
| HPV45 | E1 | 236 | 10 | VNPTVAEGFK | | 43794 |
| HPV45 | E1 | 325 | 11 | VSGDTPEWIQR | | 43795 |
| HPV45 | E1 | 576 | 8 | VTVFTFPH | | 43796 |
| HPV45 | E1 | 17 | 10 | WFFVETIVEK | | 43797 |
| HPV45 | E1 | 17 | 11 | WFFVETIVEKK | | 43798 |
| HPV45 | E1 | 264 | 10 | WGVLILALLR | | 43799 |
| HPV45 | E1 | 264 | 11 | WGVLILALLRY | | 43800 |
| HPV45 | E1 | 418 | 8 | WIKYRCSK | | 43801 |
| HPV45 | E1 | 332 | 10 | WIQRLTIIQH | | 43802 |
| HPV45 | E1 | 502 | 9 | WLEPLADTK | | 43803 |
| HPV45 | E1 | 522 | 9 | WTYFDNYMR | | 43804 |
| HPV45 | E1 | 254 | 10 | YAHIQCLDCK | | 43805 |
| HPV45 | E1 | 478 | 8 | YFGMSFIH | | 43806 |
| HPV45 | E1 | 208 | 10 | YGLSFTDLVR | | 43807 |
| HPV45 | E1 | 469 | 8 | YGPANTGK | | 43808 |
| HPV45 | E1 | 469 | 10 | YGPANTGKY | | 43809 |
| HPV45 | E1 | 394 | 10 | YLKDCAVMCR | | 43810 |
| HPV45 | E1 | 394 | 11 | YLKDCAVMCRH | | 43811 |
| HPV45 | E2 | 156 | 10 | AACVSYWGVY | | 43812 |
| HPV45 | E2 | 156 | 11 | AACVSYWGVYY | | 43813 |
| HPV45 | E2 | 157 | 9 | ACVSYWGVY | | 43814 |
| HPV45 | E2 | 157 | 10 | ACVSYWGVYY | | 43815 |
| HPV45 | E2 | 78 | 9 | AIELQMALK | | 43816 |
| HPV45 | E2 | 47 | 9 | AILFTAREH | | 43817 |
| HPV45 | E2 | 84 | 9 | ALKGLAQSK | | 43818 |
| HPV45 | E2 | 84 | 10 | ALKGLAQSKY | | 43819 |
| HPV45 | E2 | 16 | 9 | ALQDKILDH | | 43820 |
| HPV45 | E2 | 16 | 10 | ALQDKILDHY | | 43821 |
| HPV45 | E2 | 234 | 9 | ASVGTPKPH | | 43822 |
| HPV45 | E2 | 216 | 10 | ATQIVRQLQH | | 43823 |
| HPV45 | E2 | 115 | 10 | CFKKGGKTVH | | 43824 |
| HPV45 | E2 | 254 | 8 | CGLTEQHH | | 43825 |
| HPV45 | E2 | 254 | 10 | CGLTEQHHGR | | 43826 |
| HPV45 | E2 | 305 | 8 | CLRYRLRK | | 43827 |
| HPV45 | E2 | 305 | 9 | CLRYRLRKY | | 43828 |
| HPV45 | E2 | 134 | 11 | CMNYVVWDSIY | | 43829 |
| HPV45 | E2 | 286 | 10 | CSGNTTPIIH | | 43830 |
| HPV45 | E2 | 274 | 8 | CSSTSNNK | | 43831 |
| HPV45 | E2 | 274 | 9 | CSSTSNNKR | | 43832 |
| HPV45 | E2 | 274 | 10 | CSSTSNNKRR | | 43833 |
| HPV45 | E2 | 274 | 11 | CSSTSNNKRRK | | 43834 |
| HPV45 | E2 | 158 | 8 | CVSYWGVY | | 43835 |
| HPV45 | E2 | 158 | 9 | CVSYWGVYY | | 43836 |
| HPV45 | E2 | 158 | 11 | CVSYWGVYYIK | | 43837 |
| HPV45 | E2 | 211 | 11 | DDTVSATQIVR | | 43838 |
| HPV45 | E2 | 169 | 11 | DGDTTYYVQFK | | 43839 |
| HPV45 | E2 | 128 | 10 | DGNKDNCMNY | | 43840 |
| HPV45 | E2 | 31 | 8 | DINSQISY | | 43841 |
| HPV45 | E2 | 28 | 11 | DSKDINSQISY | | 43842 |
| HPV45 | E2 | 171 | 9 | DTTYYVQFK | | 43843 |
| HPV45 | E2 | 212 | 10 | DTVSATQIVR | | 43844 |
| HPV45 | E2 | 45 | 9 | ENAILFTAR | | 43845 |
| HPV45 | E2 | 45 | 11 | ENAILFTAREH | | 43846 |
| HPV45 | E2 | 127 | 11 | FDGNKDNCMNY | | 43847 |
| HPV45 | E2 | 50 | 10 | FTAREHGITK | | 43848 |
| HPV45 | E2 | 298 | 10 | GDKNSLKCLR | | 43849 |
| HPV45 | E2 | 298 | 11 | GDKNSLKCLRY | | 43850 |
| HPV45 | E2 | 170 | 10 | GDTTYYVQFK | | 43851 |
| HPV45 | E2 | 119 | 8 | GGKTVHVY | | 43852 |
| HPV45 | E2 | 255 | 9 | GLTEQHHGR | | 43853 |
| HPV45 | E2 | 129 | 9 | GNKDNCMNY | | 43854 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV45 | E2 | 186 | 10 | GNSNTWEVQY | | 43855 |
| HPV45 | E2 | 288 | 8 | GNTTPIIH | | 43856 |
| HPV45 | E2 | 288 | 10 | GNTTPIIHLK | | 43857 |
| HPV45 | E2 | 225 | 8 | HASTSTPK | | 43858 |
| HPV45 | E2 | 55 | 8 | HGITKLNH | | 43859 |
| HPV45 | E2 | 261 | 9 | HGTVNTHVH | | 43860 |
| HPV45 | E2 | 242 | 8 | HIQTPATK | | 43861 |
| HPV45 | E2 | 242 | 9 | HIQTPATKR | | 43862 |
| HPV45 | E2 | 242 | 11 | HIQTPATKRPR | | 43863 |
| HPV45 | E2 | 295 | 10 | HLKGDKNSLK | | 43864 |
| HPV45 | E2 | 124 | 8 | HVYFDGNK | | 43865 |
| HPV45 | E2 | 293 | 8 | IIHLKGDK | | 43866 |
| HPV45 | E2 | 21 | 10 | ILDHYENDSK | | 43867 |
| HPV45 | E2 | 48 | 8 | ILFTAREH | | 43868 |
| HPV45 | E2 | 68 | 9 | INISKSKAH | | 43869 |
| HPV45 | E2 | 68 | 10 | INISKSKAHK | | 43870 |
| HPV45 | E2 | 70 | 8 | ISKSKAHK | | 43871 |
| HPV45 | E2 | 36 | 8 | ISYWQLIR | | 43872 |
| HPV45 | E2 | 146 | 9 | ITETGIWDK | | 43873 |
| HPV45 | E2 | 77 | 10 | KAIELQMALK | | 43874 |
| HPV45 | E2 | 304 | 8 | KCLRYRLR | | 43875 |
| HPV45 | E2 | 304 | 9 | KCLRYRLRK | | 43876 |
| HPV45 | E2 | 304 | 10 | KCLRYRLRKY | | 43877 |
| HPV45 | E2 | 168 | 8 | KDGDTTYY | | 43878 |
| HPV45 | E2 | 30 | 9 | KDINSQISY | | 43879 |
| HPV45 | E2 | 297 | 8 | KGDKNSLK | | 43880 |
| HPV45 | E2 | 297 | 11 | KGDKNSLKCLR | | 43881 |
| HPV45 | E2 | 118 | 9 | KGGKTVHVY | | 43882 |
| HPV45 | E2 | 86 | 8 | KGLAQSKY | | 43883 |
| HPV45 | E2 | 20 | 11 | KILDHYENDSK | | 43884 |
| HPV45 | E2 | 300 | 8 | KNSLKCLR | | 43885 |
| HPV45 | E2 | 300 | 9 | KNSLKCLRY | | 43886 |
| HPV45 | E2 | 300 | 10 | KNSLKCLRYR | | 43887 |
| HPV45 | E2 | 331 | 10 | KNTGILTVTY | | 43888 |
| HPV45 | E2 | 154 | 8 | KTAACVSY | | 43889 |
| HPV45 | E2 | 232 | 9 | KTASVGTPK | | 43890 |
| HPV45 | E2 | 232 | 11 | KTASVGTPKPH | | 43891 |
| HPV45 | E2 | 121 | 11 | KTVHVYFDGNK | | 43892 |
| HPV45 | E2 | 273 | 9 | LCSSTSNNK | | 43893 |
| HPV45 | E2 | 273 | 10 | LCSSTSNNKR | | 43894 |
| HPV45 | E2 | 273 | 11 | LCSSTSNNKRR | | 43895 |
| HPV45 | E2 | 22 | 9 | LDHYENDSK | | 43896 |
| HPV45 | E2 | 49 | 11 | LFTAREHGITK | | 43897 |
| HPV45 | E2 | 272 | 10 | LLCSSTSNNK | | 43898 |
| HPV45 | E2 | 272 | 11 | LLCSSTSNNKR | | 43899 |
| HPV45 | E2 | 14 | 11 | LSALQDKILDH | | 43900 |
| HPV45 | E2 | 10 | 11 | LSERLSALQDK | | 43901 |
| HPV45 | E2 | 256 | 8 | LTEQHHGR | | 43902 |
| HPV45 | E2 | 336 | 11 | LTVTYNSEVQR | | 43903 |
| HPV45 | E2 | 83 | 10 | MALKGLAQSK | | 43904 |
| HPV45 | E2 | 83 | 11 | MALKGLAQSKY | | 43905 |
| HPV45 | E2 | 135 | 10 | MNYVVWDSIY | | 43906 |
| HPV45 | E2 | 135 | 11 | MNYVVWDSIYY | | 43907 |
| HPV45 | E2 | 46 | 8 | NAILFTAR | | 43908 |
| HPV45 | E2 | 46 | 10 | NAILFTAREH | | 43909 |
| HPV45 | E2 | 69 | 8 | NISKSKAH | | 43910 |
| HPV45 | E2 | 69 | 9 | NISKSKAHK | | 43911 |
| HPV45 | E2 | 301 | 8 | NSLKCLRY | | 43912 |
| HPV45 | E2 | 301 | 9 | NSLKCLRYR | | 43913 |
| HPV45 | E2 | 301 | 11 | NSLKCLRYRLR | | 43914 |
| HPV45 | E2 | 187 | 9 | NSNTWEVQY | | 43915 |
| HPV45 | E2 | 33 | 11 | NSQISYWQLIR | | 43916 |
| HPV45 | E2 | 357 | 9 | NSVQISVGY | | 43917 |
| HPV45 | E2 | 109 | 9 | NTEPSQCFK | | 43918 |
| HPV45 | E2 | 109 | 10 | NTEPSQCFKK | | 43919 |
| HPV45 | E2 | 332 | 9 | NTGILTVTY | | 43920 |
| HPV45 | E2 | 289 | 9 | NTTPIIHLK | | 43921 |
| HPV45 | E2 | 292 | 9 | PIIHLKGDK | | 43922 |
| HPV45 | E2 | 67 | 8 | PINISKSK | | 43923 |
| HPV45 | E2 | 67 | 10 | PINISKSKAH | | 43924 |
| HPV45 | E2 | 67 | 11 | PINISKSKAHK | | 43925 |
| HPV45 | E2 | 271 | 11 | PLLCSSTSNNK | | 43926 |
| HPV45 | E2 | 356 | 10 | PNSVQISVGY | | 43927 |
| HPV45 | E2 | 112 | 10 | PSQCFKKGGK | | 43928 |
| HPV45 | E2 | 114 | 8 | QCFKKGGK | | 43929 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV45 | E2 | 114 | 11 | QCFKKGGKTVH | | 43930 |
| HPV45 | E2 | 253 | 8 | QCGLTEQH | | 43931 |
| HPV45 | E2 | 253 | 9 | QCGLTEQHH | | 43932 |
| HPV45 | E2 | 253 | 11 | QCGLTEQHHGR | | 43933 |
| HPV45 | E2 | 18 | 8 | QDKILDHY | | 43934 |
| HPV45 | E2 | 177 | 8 | QFKSECEK | | 43935 |
| HPV45 | E2 | 177 | 9 | QFKSECEKY | | 43936 |
| HPV45 | E2 | 35 | 9 | QISYWQLIR | | 43937 |
| HPV45 | E2 | 218 | 8 | QIVRQLQH | | 43938 |
| HPV45 | E2 | 222 | 11 | QLQHASTSTPK | | 43939 |
| HPV45 | E2 | 82 | 11 | QMALKGLAQSK | | 43940 |
| HPV45 | E2 | 244 | 9 | QTPATKRPR | | 43941 |
| HPV45 | E2 | 4 | 10 | QTPKESLSER | | 43942 |
| HPV45 | E2 | 63 | 10 | QVVPPINISK | | 43943 |
| HPV45 | E2 | 43 | 11 | RLENAILFTAR | | 43944 |
| HPV45 | E2 | 309 | 8 | RLRKYADH | | 43945 |
| HPV45 | E2 | 309 | 9 | RLRKYADHY | | 43946 |
| HPV45 | E2 | 13 | 8 | RLSALQDK | | 43947 |
| HPV45 | E2 | 15 | 10 | SALQDKILDH | | 43948 |
| HPV45 | E2 | 15 | 11 | SALQDKILDHY | | 43949 |
| HPV45 | E2 | 215 | 11 | SATQIVRQLQH | | 43950 |
| HPV45 | E2 | 287 | 9 | SGNTTPIIH | | 43951 |
| HPV45 | E2 | 287 | 11 | SGNTTPIIHLK | | 43952 |
| HPV45 | E2 | 302 | 8 | SLKCLRYR | | 43953 |
| HPV45 | E2 | 302 | 10 | SLKCLRYRLR | | 43954 |
| HPV45 | E2 | 302 | 11 | SLKCLRYRLRK | | 43955 |
| HPV45 | E2 | 188 | 8 | SNTWEVQY | | 43956 |
| HPV45 | E2 | 275 | 8 | SSTSNNKR | | 43957 |
| HPV45 | E2 | 275 | 9 | SSTSNNKRR | | 43958 |
| HPV45 | E2 | 275 | 10 | SSTSNNKRRK | | 43959 |
| HPV45 | E2 | 321 | 11 | SSTWHWTGCNK | | 43960 |
| HPV45 | E2 | 276 | 8 | STSNNKRR | | 43961 |
| HPV45 | E2 | 276 | 9 | STSNNKRRK | | 43962 |
| HPV45 | E2 | 322 | 10 | STWHWTGCNK | | 43963 |
| HPV45 | E2 | 235 | 8 | SVGTPKPH | | 43964 |
| HPV45 | E2 | 358 | 8 | SVQISVGY | | 43965 |
| HPV45 | E2 | 155 | 11 | TAACVSYWGVY | | 43966 |
| HPV45 | E2 | 51 | 9 | TAREHGITK | | 43967 |
| HPV45 | E2 | 233 | 8 | TASVGTPK | | 43968 |
| HPV45 | E2 | 233 | 10 | TASVGTPKPH | | 43969 |
| HPV45 | E2 | 333 | 8 | TGILTVTY | | 43970 |
| HPV45 | E2 | 277 | 8 | TSNNKRRK | | 43971 |
| HPV45 | E2 | 290 | 8 | TTPIIHLK | | 43972 |
| HPV45 | E2 | 290 | 11 | TTPIIHLKGDK | | 43973 |
| HPV45 | E2 | 172 | 8 | TTYYVQFK | | 43974 |
| HPV45 | E2 | 122 | 10 | TVHVYFDGNK | | 43975 |
| HPV45 | E2 | 213 | 9 | TVSATQIVR | | 43976 |
| HPV45 | E2 | 337 | 10 | TVTYNSEVQR | | 43977 |
| HPV45 | E2 | 285 | 11 | VCSGNTTPIIH | | 43978 |
| HPV45 | E2 | 214 | 8 | VSATQIVR | | 43979 |
| HPV45 | E2 | 159 | 8 | VSYWGVYY | | 43980 |
| HPV45 | E2 | 159 | 10 | VSYWGVYYIK | | 43981 |
| HPV45 | E2 | 338 | 9 | VTYNSEVQR | | 43982 |
| HPV45 | E2 | 64 | 9 | VVPPINISK | | 43983 |
| HPV45 | E2 | 64 | 11 | VVPPINISKSK | | 43984 |
| HPV45 | E2 | 138 | 8 | VVWDSIYY | | 43985 |
| HPV45 | E2 | 152 | 10 | WDKTAACVSY | | 43986 |
| HPV45 | E2 | 108 | 10 | WNTEPSQCFK | | 43987 |
| HPV45 | E2 | 108 | 11 | WNTEPSQCFKK | | 43988 |
| HPV45 | E2 | 185 | 11 | YGNSNTWEVQY | | 43989 |
| HPV45 | E2 | 166 | 9 | YIKDGDTTY | | 43990 |
| HPV45 | E2 | 166 | 10 | YIKDGDTTYY | | 43991 |
| HPV45 | E2 | 145 | 10 | YITETGIWDK | | 43992 |
| HPV45 | E2 | 317 | 9 | YSEISSTWH | | 43993 |
| HPV45 | E2 | 175 | 10 | YVQFKSECEK | | 43994 |
| HPV45 | E2 | 175 | 11 | YVQFKSECEKY | | 43995 |
| HPV45 | E2 | 137 | 8 | YVVWDSIY | | 43996 |
| HPV45 | E2 | 137 | 9 | YVVWDSIYY | | 43997 |
| HPV45 | E6 | 63 | 10 | AACHKCIDFY | | 43998 |
| HPV45 | E6 | 64 | 9 | ACHKCIDFY | | 43999 |
| HPV45 | E6 | 64 | 11 | ACHKCIDFYSR | | 44000 |
| HPV45 | E6 | 31 | 11 | ACVYCKATLER | | 44001 |
| HPV45 | E6 | 48 | 9 | AFKDLFIVY | | 44002 |
| HPV45 | E6 | 48 | 10 | AFKDLFIVYR | | 44003 |
| HPV45 | E6 | 37 | 9 | ATLERTEVY | | 44004 |

TABLE XVII-continued

All Motif Peptides

| Type | Protein | Position | No. of Amino Acids | Sequence | A*1101 | Seq. Id. No. |
|---|---|---|---|---|---|---|
| HPV45 | E6 | 141 | 9 | CCDQARQER | | 44005 |
| HPV45 | E6 | 141 | 11 | CCDQARQERLR | | 44006 |
| HPV45 | E6 | 142 | 8 | CDQARQER | | 44007 |
| HPV45 | E6 | 142 | 10 | CDQARQERLR | | 44008 |
| HPV45 | E6 | 142 | 11 | CDQARQERLRR | | 44009 |
| HPV45 | E6 | 59 | 8 | CIAYAACH | | 44010 |
| HPV45 | E6 | 59 | 9 | CIAYAACHK | | 44011 |
| HPV45 | E6 | 68 | 9 | CIDFYSRIR | 0.0001 | 44012 |
| HPV45 | E6 | 138 | 9 | CNTCCDQAR | | 44013 |
| HPV45 | E6 | 32 | 10 | CVYCKATLER | | 44014 |
| HPV45 | E6 | 58 | 9 | DCIAYAACH | | 44015 |
| HPV45 | E6 | 58 | 10 | DCIAYAACHK | | 44016 |
| HPV45 | E6 | 5 | 8 | DDPTQRPY | | 44017 |
| HPV45 | E6 | 5 | 9 | DDPTQRPYK | | 44018 |
| HPV45 | E6 | 70 | 10 | DFYSRIRELR | 0.0001 | 44019 |
| HPV45 | E6 | 70 | 11 | DFYSRIRELRY | | 44020 |
| HPV45 | E6 | 27 | 8 | DVSIACVY | | 44021 |
| HPV45 | E6 | 27 | 10 | DVSIACVYCK | | 44022 |
| HPV45 | E6 | 77 | 10 | ELRYYSNSVY | | 44023 |
| HPV45 | E6 | 97 | 8 | ELYNLLIR | | 44024 |
| HPV45 | E6 | 97 | 11 | ELYNLLIRCLR | | 44025 |
| HPV45 | E6 | 43 | 8 | EVYQFAFK | | 44026 |
| HPV45 | E6 | 47 | 10 | FAFKDLFIVY | | 44027 |
| HPV45 | E6 | 47 | 11 | FAFKDLFIVYR | | 44028 |
| HPV45 | E6 | 4 | 9 | FDDPTQRPY | | 44029 |
| HPV45 | E6 | 4 | 10 | FDDPTQRPYK | | 44030 |
| HPV45 | E6 | 53 | 10 | FIVYRDCIAY | | 44031 |
| HPV45 | E6 | 120 | 9 | HLKDKRRFH | | 44032 |
| HPV45 | E6 | 128 | 8 | HSIAGQYR | | 44033 |
| HPV45 | E6 | 60 | 8 | IAYAACHK | | 44034 |
| HPV45 | E6 | 69 | 8 | IDFYSRIR | | 44035 |
| HPV45 | E6 | 69 | 11 | IDFYSRIRELR | | 44036 |
| HPV45 | E6 | 54 | 9 | IVYRDCIAY | | 44037 |
| HPV45 | E6 | 36 | 10 | KATLERTEVY | | 44038 |
| HPV45 | E6 | 67 | 8 | KCIDFYSR | | 44039 |
| HPV45 | E6 | 67 | 10 | KCIDFYSRIR | | 44040 |
| HPV45 | E6 | 50 | 8 | KDLFIVYR | | 44041 |
| HPV45 | E6 | 92 | 8 | KITNETELY | | 44042 |
| HPV45 | E6 | 52 | 11 | LFIVYRDCIAY | | 44043 |
| HPV45 | E6 | 102 | 9 | LIRCLRCQK | 0.0012 | 44044 |
| HPV45 | E6 | 101 | 10 | LLIRCLRCQK | 0.1200 | 44045 |
| HPV45 | E6 | 112 | 8 | LNPAEKRR | | 44046 |
| HPV45 | E6 | 112 | 9 | LNPAEKRRH | | 44047 |
| HPV45 | E6 | 112 | 11 | LNPAEKRRHLK | | 44048 |
| HPV45 | E6 | 1 | 10 | MARFDDPTQR | | 44049 |
| HPV45 | E6 | 100 | 8 | NLLIRCLR | | 44050 |
| HPV45 | E6 | 100 | 11 | NLLIRCLRCQK | | 44051 |
| HPV45 | E6 | 83 | 10 | NSVYGETLEK | | 44052 |
| HPV45 | E6 | 139 | 8 | NTCCDQAR | | 44053 |
| HPV45 | E6 | 139 | 11 | NTCCDQARQER | | 44054 |
| HPV45 | E6 | 95 | 10 | NTELYNLLIR | | 44055 |
| HPV45 | E6 | 114 | 9 | PAEKRRHLK | | 44056 |
| HPV45 | E6 | 114 | 11 | PAEKRRHLKDK | | 44057 |
| HPV45 | E6 | 111 | 8 | PLNPAEKR | | 44058 |
| HPV45 | E6 | 111 | 9 | PLNPAEKRR | | 44059 |
| HPV45 | E6 | 111 | 10 | PLNPAEKRRH | | 44060 |
| HPV45 | E6 | 144 | 8 | QARQERLR | | 44061 |
| HPV45 | E6 | 144 | 9 | QARQERLRR | | 44062 |
| HPV45 | E6 | 144 | 10 | QARQERLRRR | | 44063 |
| HPV45 | E6 | 144 | 11 | QARQERLRRRR | | 44064 |
| HPV45 | E6 | 137 | 10 | QCNTCCDQAR | | 44065 |
| HPV45 | E6 | 26 | 9 | QDVSIACVY | | 44066 |
| HPV45 | E6 | 26 | 11 | QDVSIACVYCK | | 44067 |
| HPV45 | E6 | 46 | 11 | QFAFKDLFIVY | | 44068 |
| HPV45 | E6 | 107 | 11 | RCQKPLNPAEK | | 44069 |
| HPV45 | E6 | 57 | 10 | RDCIAYAACH | | 44070 |
| HPV45 | E6 | 57 | 11 | RDCIAYAACHK | | 44071 |
| HPV45 | E6 | 3 | 8 | RFDDPTQR | | 44072 |
| HPV45 | E6 | 3 | 10 | RFDDPTQRPY | | 44073 |
| HPV45 | E6 | 3 | 11 | RFDDPTQRPYK | | 44074 |
| HPV45 | E6 | 126 | 9 | RFHSIAGQY | | 44075 |
| HPV45 | E6 | 126 | 10 | RFHSIAGQYR | | 44076 |
| HPV45 | E6 | 74 | 8 | RIRELRYY | | 44077 |
| HPV45 | E6 | 41 | 10 | RTEVYQFAFK | | 44078 |
| HPV45 | E6 | 29 | 8 | SIACVYCK | | 44079 |

TABLE XVII-continued

A11 Motif Peptides

| Type | Protein | Position | No. of Amino Acids | Sequence | A*1101 | Seq. Id. No. |
|---|---|---|---|---|---|---|
| HPV45 | E6 | 24 | 11 | SLQDVSIACVY | | 44080 |
| HPV45 | E6 | 82 | 11 | SNSVYGETLEK | | 44081 |
| HPV45 | E6 | 84 | 9 | SVYGETLEK | | 44082 |
| HPV45 | E6 | 140 | 10 | TCCDQARQER | | 44083 |
| HPV45 | E6 | 89 | 11 | TLEKITNTELY | | 44084 |
| HPV45 | E6 | 38 | 8 | TLERTEVY | | 44085 |
| HPV45 | E6 | 94 | 11 | TNTELYNLLIR | | 44086 |
| HPV45 | E6 | 28 | 9 | VSIACVYCK | | 44087 |
| HPV45 | E6 | 62 | 11 | YAACHKCIDFY | | 44088 |
| HPV45 | E6 | 34 | 8 | YCKATLER | | 44089 |
| HPV45 | E6 | 99 | 9 | YNLLIRCLR | | 44090 |
| HPV45 | E6 | 72 | 8 | YSRIRELR | | 44091 |
| HPV45 | E6 | 72 | 9 | YSRIRELRY | | 44092 |
| HPV45 | E6 | 72 | 10 | YSRIRELRYY | | 44093 |
| HPV45 | E7 | 6 | 9 | ATLQEIVLH | | 44094 |
| HPV45 | E7 | 64 | 9 | CVCCKCDGR | | 44095 |
| HPV45 | E7 | 43 | 11 | DGVSHAQLPAR | | 44096 |
| HPV45 | E7 | 20 | 10 | ELDPVDLLCY | | 44097 |
| HPV45 | E7 | 38 | 10 | ENDEADGVSH | | 44098 |
| HPV45 | E7 | 78 | 8 | ESSADDLR | | 44099 |
| HPV45 | E7 | 44 | 10 | GVSHAQLPAR | | 44100 |
| HPV45 | E7 | 44 | 11 | GVSHAQLPARR | | 44101 |
| HPV45 | E7 | 47 | 8 | HAQLPARR | | 44102 |
| HPV45 | E7 | 62 | 11 | ILCVCCKCDGR | | 44103 |
| HPV45 | E7 | 61 | 8 | KILCVCCK | | 44104 |
| HPV45 | E7 | 63 | 10 | LCVCCKCDGR | | 44105 |
| HPV45 | E7 | 21 | 9 | LDPVDLLCY | | 44106 |
| HPV45 | E7 | 75 | 11 | LTVESSADDLR | | 44107 |
| HPV45 | E7 | 39 | 9 | NDEADGVSH | | 44108 |
| HPV45 | E7 | 51 | 9 | PARRAEPQR | | 44109 |
| HPV45 | E7 | 51 | 10 | PARRAEPQRH | | 44110 |
| HPV45 | E7 | 51 | 11 | PARRAEPQRHK | | 44111 |
| HPV45 | E7 | 49 | 11 | QLPARRAEPQR | | 44112 |
| HPV45 | E7 | 54 | 8 | RAEPQRHK | | 44113 |
| HPV45 | E7 | 5 | 10 | RATLQEIVLH | | 44114 |
| HPV45 | E7 | 7 | 8 | TLQEIVLH | | 44115 |
| HPV45 | E7 | 76 | 10 | TVESSADDLR | | 44116 |
| HPV45 | E7 | 65 | 8 | VCCKCDGR | | 44117 |
| HPV45 | E7 | 45 | 9 | VSHAQLPAR | | 44118 |
| HPV45 | E7 | 45 | 10 | VSHAQLPARR | | 44119 |
| HPV45 | L1 | 517 | 9 | AASTSTASR | | 44120 |
| HPV45 | L1 | 161 | 11 | AATAVITQDVR | | 44121 |
| HPV45 | L1 | 128 | 9 | ACVGMEIGR | | 44122 |
| HPV45 | L1 | 83 | 9 | AGNKQAVPK | | 44123 |
| HPV45 | L1 | 191 | 8 | AIGEHWAK | | 44124 |
| HPV45 | L1 | 28 | 11 | ALWRPSDSTVY | | 44125 |
| HPV45 | L1 | 234 | 11 | AMDFSTLQDTK | | 44126 |
| HPV45 | L1 | 523 | 9 | ASRPAKRVR | | 44127 |
| HPV45 | L1 | 523 | 11 | ASRPAKRVRIR | | 44128 |
| HPV45 | L1 | 375 | 11 | ASTQNPVPNTY | | 44129 |
| HPV45 | L1 | 518 | 8 | ASTSTASR | | 44130 |
| HPV45 | L1 | 518 | 11 | ASTSTASRPAK | | 44131 |
| HPV45 | L1 | 162 | 10 | ATAVITQDVR | | 44132 |
| HPV45 | L1 | 164 | 8 | AVITQDVR | | 44133 |
| HPV45 | L1 | 88 | 8 | AVPKVSAY | | 44134 |
| HPV45 | L1 | 88 | 10 | AVPKVSAYQY | | 44135 |
| HPV45 | L1 | 88 | 11 | AVPKVSAYQYR | | 44136 |
| HPV45 | L1 | 276 | 10 | CLRREQLFAR | | 44137 |
| HPV45 | L1 | 276 | 11 | CLRREQLFARH | | 44138 |
| HPV45 | L1 | 129 | 8 | CVGMEIGR | | 44139 |
| HPV45 | L1 | 188 | 8 | CVPAIGEH | | 44140 |
| HPV45 | L1 | 188 | 11 | CVPAIGEHWAK | | 44141 |
| HPV45 | L1 | 211 | 8 | DCPPLELK | | 44142 |
| HPV45 | L1 | 51 | 11 | DDYVSRTSIFY | | 44143 |
| HPV45 | L1 | 236 | 9 | DFSTLQDTK | | 44144 |
| HPV45 | L1 | 224 | 9 | DGDMVDTGY | | 44145 |
| HPV45 | L1 | 250 | 8 | DICQSICK | | 44146 |
| HPV45 | L1 | 250 | 9 | DICQSICKY | | 44147 |
| HPV45 | L1 | 488 | 9 | DLDQYPLGR | | 44148 |
| HPV45 | L1 | 488 | 10 | DLDQYPLGRK | | 44149 |
| HPV45 | L1 | 172 | 8 | DNVSVDYK | | 44150 |
| HPV45 | L1 | 271 | 8 | DSMFFCLR | | 44151 |
| HPV45 | L1 | 271 | 9 | DSMFFCLRR | | 44152 |
| HPV45 | L1 | 332 | 9 | DSQLFNKPY | | 44153 |
| HPV45 | L1 | 114 | 11 | DSTIYNPETQR | | 44154 |

TABLE XVII-continued

A11 Motif Peptides

| Type | Protein | Position | No. of Amino Acids | Sequence | A*1101 | Seq. Id. No. |
|---|---|---|---|---|---|---|
| HPV45 | L1 | 461 | 11 | DTTPPEKQDPY | | 44155 |
| HPV45 | L1 | 296 | 8 | DTVPTDLY | | 44156 |
| HPV45 | L1 | 296 | 10 | DTVPTDLYIK | | 44157 |
| HPV45 | L1 | 169 | 10 | DVRDNVSVDY | | 44158 |
| HPV45 | L1 | 169 | 11 | DVRDNVSVDYK | | 44159 |
| HPV45 | L1 | 223 | 10 | EDGDMVDTGY | | 44160 |
| HPV45 | L1 | 313 | 8 | ETPGSCVY | | 44161 |
| HPV45 | L1 | 283 | 8 | FARHFWNR | | 44162 |
| HPV45 | L1 | 275 | 11 | FCLRREQLFAR | | 44163 |
| HPV45 | L1 | 110 | 9 | FGLPDSTIY | | 44164 |
| HPV45 | L1 | 24 | 8 | FLQMALWR | | 44165 |
| HPV45 | L1 | 498 | 8 | FLVQAGLR | | 44166 |
| HPV45 | L1 | 498 | 9 | FLVQAGLRR | | 44167 |
| HPV45 | L1 | 498 | 10 | FLVQAGLRRR | | 44168 |
| HPV45 | L1 | 336 | 8 | FNKPYWLH | | 44169 |
| HPV45 | L1 | 336 | 9 | FNKPYWLHK | | 44170 |
| HPV45 | L1 | 485 | 8 | FSSDLDQY | | 44171 |
| HPV45 | L1 | 237 | 8 | FSTLQDTK | | 44172 |
| HPV45 | L1 | 450 | 11 | FVQSVAVTCQK | | 44173 |
| HPV45 | L1 | 359 | 9 | FVTVVDTTR | | 44174 |
| HPV45 | L1 | 82 | 10 | GAGNKQAVPK | | 44175 |
| HPV45 | L1 | 187 | 9 | GCVPAIGEH | | 44176 |
| HPV45 | L1 | 210 | 9 | GDCPPLELK | | 44177 |
| HPV45 | L1 | 225 | 8 | GDMVDTGY | | 44178 |
| HPV45 | L1 | 270 | 9 | GDSMFFCLR | | 44179 |
| HPV45 | L1 | 270 | 10 | GDSMFFCLRR | | 44180 |
| HPV45 | L1 | 295 | 9 | GDTVPTDLY | | 44181 |
| HPV45 | L1 | 295 | 11 | GDTVPTDLYIK | | 44182 |
| HPV45 | L1 | 141 | 10 | GIGLSGHPFY | | 44183 |
| HPV45 | L1 | 111 | 8 | GLPDSTIY | | 44184 |
| HPV45 | L1 | 503 | 11 | GLRRRPTIGPR | | 44185 |
| HPV45 | L1 | 143 | 8 | GLSGHPFY | | 44186 |
| HPV45 | L1 | 143 | 10 | GLSGHPFYNK | | 44187 |
| HPV45 | L1 | 84 | 8 | GNKQAVPK | | 44188 |
| HPV45 | L1 | 9 | 8 | HGIIIFLK | | 44189 |
| HPV45 | L1 | 348 | 8 | HNNGICWH | | 44190 |
| HPV45 | L1 | 251 | 8 | ICQSICKY | | 44191 |
| HPV45 | L1 | 251 | 11 | ICQSICKYPDY | | 44192 |
| HPV45 | L1 | 23 | 9 | IFLQMALWR | | 44193 |
| HPV45 | L1 | 59 | 9 | IFYHAGSSR | | 44194 |
| HPV45 | L1 | 142 | 9 | IGLSGHPFY | | 44195 |
| HPV45 | L1 | 142 | 11 | IGLSGHPFYNK | | 44196 |
| HPV45 | L1 | 185 | 11 | ILGCVPAIGEH | | 44197 |
| HPV45 | L1 | 411 | 10 | ITLTAEVMSY | | 44198 |
| HPV45 | L1 | 328 | 11 | ITTSDSQLFNK | | 44199 |
| HPV45 | L1 | 460 | 8 | KDTTPPEK | | 44200 |
| HPV45 | L1 | 109 | 10 | KFGLPDSTIY | | 44201 |
| HPV45 | L1 | 389 | 8 | KFKHYSRH | | 44202 |
| HPV45 | L1 | 497 | 9 | KFLVQAGLR | | 44203 |
| HPV45 | L1 | 497 | 10 | KFLVQAGLRR | | 44204 |
| HPV45 | L1 | 497 | 11 | KFLVQAGLRRR | | 44205 |
| HPV45 | L1 | 484 | 9 | KFSSDLDQY | | 44206 |
| HPV45 | L1 | 475 | 8 | KFWTVDLK | | 44207 |
| HPV45 | L1 | 475 | 10 | KFWTVDLKEK | | 44208 |
| HPV45 | L1 | 305 | 8 | KGTSANMR | | 44209 |
| HPV45 | L1 | 152 | 9 | KLDDTESAH | | 44210 |
| HPV45 | L1 | 473 | 10 | KLKFWTVDLK | | 44211 |
| HPV45 | L1 | 91 | 8 | KVSAYQYR | | 44212 |
| HPV45 | L1 | 91 | 11 | KVSAYQYRVFR | | 44213 |
| HPV45 | L1 | 153 | 8 | LDDTESAH | | 44214 |
| HPV45 | L1 | 249 | 9 | LDICQSICK | | 44215 |
| HPV45 | L1 | 249 | 10 | LDICQSICKY | | 44216 |
| HPV45 | L1 | 489 | 8 | LDQYPLGR | | 44217 |
| HPV45 | L1 | 489 | 9 | LDQYPLGRK | | 44218 |
| HPV45 | L1 | 282 | 9 | LFARHFWNR | | 44219 |
| HPV45 | L1 | 335 | 9 | LFNKPYWLH | | 44220 |
| HPV45 | L1 | 335 | 10 | LFNKPYWLHK | | 44221 |
| HPV45 | L1 | 358 | 10 | LFVTVVDTTR | | 44222 |
| HPV45 | L1 | 186 | 10 | LGCVPAIGEH | | 44223 |
| HPV45 | L1 | 140 | 8 | LGIGLSGH | | 44224 |
| HPV45 | L1 | 140 | 11 | LGIGLSGHPFY | | 44225 |
| HPV45 | L1 | 68 | 8 | LLTVGNPY | | 44226 |
| HPV45 | L1 | 68 | 10 | LLTVGNPYFR | | 44227 |
| HPV45 | L1 | 144 | 9 | LSGHPFYNK | | 44228 |
| HPV45 | L1 | 413 | 8 | LTAEVMSY | | 44229 |

TABLE XVII-continued

A11 Motif Peptides

| Type | Protein | Position | No. of Amino Acids | Sequence | A*1101 | Seq. Id. No. |
|---|---|---|---|---|---|---|
| HPV45 | L1 | 413 | 10 | LTAEVMSYIH | | 44230 |
| HPV45 | L1 | 69 | 9 | LTVGNPYFR | | 44231 |
| HPV45 | L1 | 499 | 8 | LVQAGLRR | | 44232 |
| HPV45 | L1 | 499 | 9 | LVQAGLRRR | | 44233 |
| HPV45 | L1 | 1 | 9 | MAHNIIYGH | | 44234 |
| HPV45 | L1 | 235 | 10 | MDFSTLQDTK | | 44235 |
| HPV45 | L1 | 294 | 10 | MGDTVPTDLY | | 44236 |
| HPV45 | L1 | 310 | 11 | NMRETPGSCVY | | 44237 |
| HPV45 | L1 | 49 | 8 | NTDDYVSR | | 44238 |
| HPV45 | L1 | 383 | 9 | NTYDPTKFK | | 44239 |
| HPV45 | L1 | 383 | 10 | NTYDPTKFKH | | 44240 |
| HPV45 | L1 | 383 | 11 | NTYDPTKFKHY | | 44241 |
| HPV45 | L1 | 516 | 10 | PAASTSTASR | | 44242 |
| HPV45 | L1 | 190 | 9 | PAIGEHWAK | | 44243 |
| HPV45 | L1 | 526 | 8 | PAKRVRIR | | 44244 |
| HPV45 | L1 | 526 | 10 | PAKRVRIRSK | | 44245 |
| HPV45 | L1 | 526 | 11 | PAKRVRIRSKK | | 44246 |
| HPV45 | L1 | 259 | 11 | PDYLQMSADPY | | 44247 |
| HPV45 | L1 | 209 | 10 | PGDCPPLELK | | 44248 |
| HPV45 | L1 | 22 | 10 | PIFLQMALWR | | 44249 |
| HPV45 | L1 | 248 | 10 | PLDICQSICK | | 44250 |
| HPV45 | L1 | 248 | 11 | PLDICQSICKY | | 44251 |
| HPV45 | L1 | 139 | 9 | PLGIGLSGH | | 44252 |
| HPV45 | L1 | 382 | 8 | PNTYDPTK | | 44253 |
| HPV45 | L1 | 382 | 10 | PNTYDPTKFK | | 44254 |
| HPV45 | L1 | 382 | 11 | PNTYDPTKFKH | | 44255 |
| HPV45 | L1 | 508 | 8 | PTIGPRKR | | 44256 |
| HPV45 | L1 | 387 | 9 | PTKFKHYSR | | 44257 |
| HPV45 | L1 | 387 | 10 | PTKFKHYSRH | | 44258 |
| HPV45 | L1 | 440 | 9 | PTTSLVDTY | | 44259 |
| HPV45 | L1 | 440 | 10 | PTTSLVDTYR | | 44260 |
| HPV45 | L1 | 380 | 10 | PVPNTYDPTK | | 44261 |
| HPV45 | L1 | 87 | 9 | QAVPKVSAY | | 44262 |
| HPV45 | L1 | 87 | 11 | QAVPKVSAYQY | | 44263 |
| HPV45 | L1 | 468 | 8 | QDPYDKLK | | 44264 |
| HPV45 | L1 | 168 | 11 | QDVRDNVSVDY | | 44265 |
| HPV45 | L1 | 346 | 10 | QGHNNGICWH | | 44266 |
| HPV45 | L1 | 281 | 10 | QLFARHFWNR | | 44267 |
| HPV45 | L1 | 334 | 10 | QLFNKPYWLH | | 44268 |
| HPV45 | L1 | 334 | 11 | QLFNKPYWLHK | | 44269 |
| HPV45 | L1 | 357 | 11 | QLFVTVVDTTR | | 44270 |
| HPV45 | L1 | 378 | 8 | QNPVPNTY | | 44271 |
| HPV45 | L1 | 253 | 9 | QSICKYPDY | | 44272 |
| HPV45 | L1 | 452 | 9 | QSVAVTCQK | | 44273 |
| HPV45 | L1 | 171 | 8 | RDNVSVDY | | 44274 |
| HPV45 | L1 | 171 | 9 | RDNVSVDYK | | 44275 |
| HPV45 | L1 | 67 | 9 | RLLTVGNPY | | 44276 |
| HPV45 | L1 | 67 | 11 | RLLTVGNPYFR | | 44277 |
| HPV45 | L1 | 101 | 9 | RVALPDPNK | | 44278 |
| HPV45 | L1 | 529 | 8 | RVRIRSKK | | 44279 |
| HPV45 | L1 | 46 | 8 | RVVNTDDY | | 44280 |
| HPV45 | L1 | 46 | 11 | RVVNTDDYVSR | | 44281 |
| HPV45 | L1 | 77 | 10 | RVVPSGAGNK | | 44282 |
| HPV45 | L1 | 93 | 9 | SAYQYRVFR | | 44283 |
| HPV45 | L1 | 487 | 10 | SDLDQYPLGR | | 44284 |
| HPV45 | L1 | 487 | 11 | SDLDQYPLGRK | | 44285 |
| HPV45 | L1 | 331 | 8 | SDSQLFNK | | 44286 |
| HPV45 | L1 | 331 | 10 | SDSQLFNKPY | | 44287 |
| HPV45 | L1 | 81 | 11 | SGAGNKQAVPK | | 44288 |
| HPV45 | L1 | 145 | 8 | SGHPFYNK | | 44289 |
| HPV45 | L1 | 254 | 8 | SICKYPDY | | 44290 |
| HPV45 | L1 | 58 | 10 | SIFYHAGSSR | | 44291 |
| HPV45 | L1 | 272 | 8 | SMFFCLRR | | 44292 |
| HPV45 | L1 | 486 | 11 | SSDLDQYPLGR | | 44293 |
| HPV45 | L1 | 65 | 11 | SSRLLTVGNPY | | 44294 |
| HPV45 | L1 | 521 | 8 | STASRPAK | | 44295 |
| HPV45 | L1 | 521 | 9 | STASRPAKR | | 44296 |
| HPV45 | L1 | 521 | 11 | STASRPAKRVR | | 44297 |
| HPV45 | L1 | 115 | 10 | STIYNPETQR | | 44298 |
| HPV45 | L1 | 376 | 10 | STQNPVPNTY | | 44299 |
| HPV45 | L1 | 519 | 10 | STSTASRPAK | | 44300 |
| HPV45 | L1 | 519 | 11 | STSTASRPAKR | | 44301 |
| HPV45 | L1 | 43 | 11 | SVARVVNTDDY | | 44302 |
| HPV45 | L1 | 453 | 8 | SVAVTCQK | | 44303 |
| HPV45 | L1 | 414 | 9 | TAEVMSYIH | | 44304 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV45 | L1 | 522 | 8 | TASRPAKR | | 44305 |
| HPV45 | L1 | 522 | 10 | TASRPAKRVR | | 44306 |
| HPV45 | L1 | 163 | 9 | TAVITQDVR | | 44307 |
| HPV45 | L1 | 457 | 11 | TCQKDTTPPEK | | 44308 |
| HPV45 | L1 | 410 | 11 | TITLTAEVMSY | | 44309 |
| HPV45 | L1 | 116 | 9 | TIYNPETQR | | 44310 |
| HPV45 | L1 | 412 | 9 | TLTAEVMSY | | 44311 |
| HPV45 | L1 | 412 | 11 | TLTAEVMSYIH | | 44312 |
| HPV45 | L1 | 330 | 9 | TSDSQLFNK | | 44313 |
| HPV45 | L1 | 330 | 11 | TSDSQLFNKPY | | 44314 |
| HPV45 | L1 | 57 | 11 | TSIFYHAGSSR | | 44315 |
| HPV45 | L1 | 442 | 8 | TSLVDTYR | | 44316 |
| HPV45 | L1 | 520 | 9 | TSTASRPAK | | 44317 |
| HPV45 | L1 | 520 | 10 | TSTASRPAKR | | 44318 |
| HPV45 | L1 | 462 | 10 | TTPPEKQDPY | | 44319 |
| HPV45 | L1 | 329 | 10 | TTSDSQLFNK | | 44320 |
| HPV45 | L1 | 441 | 8 | TTSLVDTY | | 44321 |
| HPV45 | L1 | 441 | 9 | TTSLVDTYR | | 44322 |
| HPV45 | L1 | 70 | 8 | TVGNPYFR | | 44323 |
| HPV45 | L1 | 297 | 9 | TVPTDLYIK | | 44324 |
| HPV45 | L1 | 36 | 11 | TVYLPPPSVAR | | 44325 |
| HPV45 | L1 | 102 | 8 | VALPDPNK | | 44326 |
| HPV45 | L1 | 44 | 10 | VARVVNTDDY | | 44327 |
| HPV45 | L1 | 99 | 11 | VFRVALPDPNK | | 44328 |
| HPV45 | L1 | 293 | 11 | VMGDTVPTDLY | | 44329 |
| HPV45 | L1 | 48 | 9 | VNTDDYVSR | | 44330 |
| HPV45 | L1 | 92 | 10 | VSAYQYRVFR | | 44331 |
| HPV45 | L1 | 54 | 8 | VSRTSIFY | | 44332 |
| HPV45 | L1 | 54 | 9 | VSRTSIFYH | | 44333 |
| HPV45 | L1 | 360 | 8 | VTVVDTTR | | 44334 |
| HPV45 | L1 | 47 | 10 | VVNTDDYVSR | | 44335 |
| HPV45 | L1 | 78 | 9 | VVPSGAGNK | | 44336 |
| HPV45 | L1 | 127 | 10 | WACVGMEIGR | | 44337 |
| HPV45 | L1 | 196 | 8 | WAKGTLCK | | 44338 |
| HPV45 | L1 | 341 | 8 | WLHKAQGH | | 44339 |
| HPV45 | L1 | 477 | 8 | WTVDLKEK | | 44340 |
| HPV45 | L1 | 385 | 8 | YDPTKFKH | | 44341 |
| HPV45 | L1 | 385 | 9 | YDPTKFKHY | | 44342 |
| HPV45 | L1 | 385 | 11 | YDPTKFKHYSR | | 44343 |
| HPV45 | L1 | 269 | 10 | YGDSMFFCLR | | 44344 |
| HPV45 | L1 | 269 | 11 | YGDSMFFCLRR | | 44345 |
| HPV45 | L1 | 7 | 10 | YGHGIIIFLK | | 44346 |
| HPV45 | L1 | 303 | 10 | YIKGTSANMR | | 44347 |
| HPV45 | L1 | 38 | 9 | YLPPPSVAR | | 44348 |
| HPV45 | L1 | 261 | 9 | YLQMSADPY | | 44349 |
| HPV45 | L1 | 150 | 11 | YNKLDDTESAH | | 44350 |
| HPV45 | L1 | 393 | 8 | YSRHVEEY | | 44351 |
| HPV45 | L1 | 53 | 9 | YVSRTSIFY | | 44352 |
| HPV45 | L1 | 53 | 10 | YVSRTSIFYH | | 44353 |
| HPV45 | L2 | 286 | 10 | ALSSRRGTVR | | 44354 |
| HPV45 | L2 | 12 | 8 | ASATDLYR | | 44355 |
| HPV45 | L2 | 12 | 11 | ASATDLYRTCK | | 44356 |
| HPV45 | L2 | 357 | 9 | ASTTPSTIH | | 44357 |
| HPV45 | L2 | 357 | 10 | ASTTPSTIHK | | 44358 |
| HPV45 | L2 | 423 | 10 | ASTTTYIGIH | | 44359 |
| HPV45 | L2 | 14 | 9 | ATDLYRTCK | | 44360 |
| HPV45 | L2 | 303 | 9 | ATMFTRSGK | | 44361 |
| HPV45 | L2 | 340 | 11 | ATNDSDLFDVY | | 44362 |
| HPV45 | L2 | 275 | 9 | DFMDIIRLH | | 44363 |
| HPV45 | L2 | 275 | 10 | DFMDIIRLHR | | 44364 |
| HPV45 | L2 | 273 | 9 | DSDFMDIIR | | 44365 |
| HPV45 | L2 | 273 | 11 | DSDFMDIIRLH | | 44366 |
| HPV45 | L2 | 343 | 8 | DSDLFDVY | | 44367 |
| HPV45 | L2 | 36 | 8 | EGTTLADK | | 44368 |
| HPV45 | L2 | 276 | 8 | FMDIIRLH | | 44369 |
| HPV45 | L2 | 276 | 9 | FMDIIRLHR | | 44370 |
| HPV45 | L2 | 306 | 11 | FTRSGKQIGGR | | 44371 |
| HPV45 | L2 | 181 | 10 | FVGTPTSGSH | | 44372 |
| HPV45 | L2 | 314 | 8 | GGRVHFYH | | 44373 |
| HPV45 | L2 | 58 | 11 | GIGTGSGSGGR | | 44374 |
| HPV45 | L2 | 430 | 8 | GIHGTQYY | | 44375 |
| HPV45 | L2 | 64 | 8 | GSGGRTGY | | 44376 |
| HPV45 | L2 | 62 | 10 | GSGSGGRTGY | | 44377 |
| HPV45 | L2 | 25 | 10 | GTCPPDVINK | | 44378 |
| HPV45 | L2 | 60 | 9 | GTGSGSGGR | | 44379 |

TABLE XVII-continued

A11 Motif Peptides

| Type | Protein | Position | No. of Amino Acids | Sequence | A*1101 | Seq. Id. No. |
|---|---|---|---|---|---|---|
| HPV45 | L2 | 183 | 8 | GTPTSGSH | | 44380 |
| HPV45 | L2 | 183 | 10 | GTPTSGSHGY | | 44381 |
| HPV45 | L2 | 433 | 10 | GTQYYLWPWY | | 44382 |
| HPV45 | L2 | 433 | 11 | GTQYYLWPWYY | | 44383 |
| HPV45 | L2 | 292 | 11 | GTVRFSRLGQR | | 44384 |
| HPV45 | L2 | 432 | 11 | HGTQYYLWPWY | | 44385 |
| HPV45 | L2 | 180 | 11 | IFVGTPTSGSH | | 44386 |
| HPV45 | L2 | 313 | 8 | IGGRVHFY | | 44387 |
| HPV45 | L2 | 313 | 9 | IGGRVHFYH | | 44388 |
| HPV45 | L2 | 429 | 8 | IGIHGTQY | | 44389 |
| HPV45 | L2 | 429 | 9 | IGIHGTQYY | | 44390 |
| HPV45 | L2 | 59 | 10 | IGTGSGSGGR | | 44391 |
| HPV45 | L2 | 210 | 10 | ISSTPLPTVR | | 44392 |
| HPV45 | L2 | 210 | 11 | ISSTPLPTVRR | | 44393 |
| HPV45 | L2 | 366 | 8 | KSFTYPKY | | 44394 |
| HPV45 | L2 | 34 | 10 | KVEGTTLADK | | 44395 |
| HPV45 | L2 | 299 | 10 | LGQRATMFTR | | 44396 |
| HPV45 | L2 | 287 | 9 | LSSRRGTVR | | 44397 |
| HPV45 | L2 | 375 | 11 | LTMPSTAASSY | | 44398 |
| HPV45 | L2 | 392 | 10 | LTSAWDVPIY | | 44399 |
| HPV45 | L2 | 248 | 9 | LVTFDNPAY | | 44400 |
| HPV45 | L2 | 277 | 8 | MDIIRLHR | | 44401 |
| HPV45 | L2 | 1 | 8 | MVSHRAAR | | 44402 |
| HPV45 | L2 | 1 | 9 | MVSHRAARR | | 44403 |
| HPV45 | L2 | 1 | 10 | MVSHRAARRK | | 44404 |
| HPV45 | L2 | 1 | 11 | MVSHRAARRKR | | 44405 |
| HPV45 | L2 | 422 | 11 | NASTTTYIGIH | | 44406 |
| HPV45 | L2 | 342 | 9 | NDSDLFDVY | | 44407 |
| HPV45 | L2 | 79 | 10 | NTVVDVGPTR | | 44408 |
| HPV45 | L2 | 285 | 11 | PALSSRRGTVR | | 44409 |
| HPV45 | L2 | 356 | 10 | PASTTPSTIH | | 44410 |
| HPV45 | L2 | 356 | 11 | PASTTPSTIHK | | 44411 |
| HPV45 | L2 | 404 | 8 | PDIILPSH | | 44412 |
| HPV45 | L2 | 272 | 10 | PDSDFMDIIR | | 44413 |
| HPV45 | L2 | 209 | 11 | PISSTPLPTVR | | 44414 |
| HPV45 | L2 | 214 | 9 | PLPTVRRVR | | 44415 |
| HPV45 | L2 | 391 | 11 | PLTSAWDVPIY | | 44416 |
| HPV45 | L2 | 378 | 8 | PSTAASSY | | 44417 |
| HPV45 | L2 | 361 | 10 | PSTIHKSFTY | | 44418 |
| HPV45 | L2 | 420 | 9 | PTNASTTTY | | 44419 |
| HPV45 | L2 | 185 | 8 | PTSGSHGY | | 44420 |
| HPV45 | L2 | 216 | 10 | PTVRRVRGPR | | 44421 |
| HPV45 | L2 | 312 | 9 | QIGGRVHFY | | 44422 |
| HPV45 | L2 | 312 | 10 | QIGGRVHFYH | | 44423 |
| HPV45 | L2 | 11 | 8 | RASATDLY | | 44424 |
| HPV45 | L2 | 11 | 9 | RASATDLYR | | 44425 |
| HPV45 | L2 | 302 | 10 | RATMFTRSGK | | 44426 |
| HPV45 | L2 | 295 | 8 | RFSRLGQR | | 44427 |
| HPV45 | L2 | 222 | 8 | RGPRLYSR | | 44428 |
| HPV45 | L2 | 291 | 8 | RGTVRFSR | | 44429 |
| HPV45 | L2 | 298 | 11 | RLGQRATMFTR | | 44430 |
| HPV45 | L2 | 281 | 10 | RLHRPALSSR | | 44431 |
| HPV45 | L2 | 281 | 11 | RLHRPALSSRR | | 44432 |
| HPV45 | L2 | 225 | 11 | RLYSRANQQVR | | 44433 |
| HPV45 | L2 | 308 | 9 | RSGKQIGGR | | 44434 |
| HPV45 | L2 | 308 | 11 | RSGKQIGGRVH | | 44435 |
| HPV45 | L2 | 68 | 10 | RTGYVPLGGR | | 44436 |
| HPV45 | L2 | 220 | 8 | RVRGPRLY | | 44437 |
| HPV45 | L2 | 220 | 10 | RVRGPRLYSR | | 44438 |
| HPV45 | L2 | 235 | 10 | RVSTSQFLTH | | 44439 |
| HPV45 | L2 | 13 | 10 | SATDLYRTCK | | 44440 |
| HPV45 | L2 | 394 | 8 | SAWDVPIY | | 44441 |
| HPV45 | L2 | 274 | 8 | SDFMDIIR | | 44442 |
| HPV45 | L2 | 274 | 10 | SDFMDIIRLH | | 44443 |
| HPV45 | L2 | 274 | 11 | SDFMDIIRLHR | | 44444 |
| HPV45 | L2 | 309 | 8 | SGKQIGGR | | 44445 |
| HPV45 | L2 | 309 | 10 | SGKQIGGRVH | | 44446 |
| HPV45 | L2 | 63 | 9 | SGSGGRTGY | | 44447 |
| HPV45 | L2 | 24 | 11 | SGTCPPDVINK | | 44448 |
| HPV45 | L2 | 247 | 10 | SLVTFDNPAY | | 44449 |
| HPV45 | L2 | 78 | 11 | SNTVVDVGPTR | | 44450 |
| HPV45 | L2 | 246 | 11 | SSLVTFDNPAY | | 44451 |
| HPV45 | L2 | 288 | 8 | SSRRGTVR | | 44452 |
| HPV45 | L2 | 288 | 11 | SSRRGTVRFSR | | 44453 |
| HPV45 | L2 | 211 | 9 | SSTPLPTVR | | 44454 |

TABLE XVII-continued

A11 Motif Peptides

| Type | Protein | Position | No. of Amino Acids | Sequence | A*1101 | Seq. Id. No. |
|---|---|---|---|---|---|---|
| HPV45 | L2 | 211 | 10 | SSTPLPTVRR | | 44455 |
| HPV45 | L2 | 362 | 9 | STIHKSFTY | | 44456 |
| HPV45 | L2 | 362 | 11 | STIHKSFTYPK | | 44457 |
| HPV45 | L2 | 212 | 8 | STPLPTVR | | 44458 |
| HPV45 | L2 | 212 | 9 | STPLPTVRR | | 44459 |
| HPV45 | L2 | 212 | 11 | STPLPTVRRVR | | 44460 |
| HPV45 | L2 | 237 | 8 | STSQFLTH | | 44461 |
| HPV45 | L2 | 358 | 8 | STTPSTIH | | 44462 |
| HPV45 | L2 | 358 | 9 | STTPSTIHK | | 44463 |
| HPV45 | L2 | 424 | 9 | STTTYIGIH | | 44464 |
| HPV45 | L2 | 26 | 9 | TCPPDVINK | | 44465 |
| HPV45 | L2 | 15 | 8 | TDLYRTCK | | 44466 |
| HPV45 | L2 | 402 | 10 | TGPDIILPSH | | 44467 |
| HPV45 | L2 | 61 | 8 | TGSGSGGR | | 44468 |
| HPV45 | L2 | 61 | 11 | TGSGSGGRTGY | | 44469 |
| HPV45 | L2 | 69 | 9 | TGYVPLGGR | | 44470 |
| HPV45 | L2 | 363 | 8 | TIHKSFTY | | 44471 |
| HPV45 | L2 | 363 | 10 | TIHKSFTYPK | | 44472 |
| HPV45 | L2 | 363 | 11 | TIHKSFTYPKY | | 44473 |
| HPV45 | L2 | 304 | 8 | TMFTRSGK | | 44474 |
| HPV45 | L2 | 376 | 10 | TMPSTAASSY | | 44475 |
| HPV45 | L2 | 421 | 8 | TNASTTTY | | 44476 |
| HPV45 | L2 | 341 | 10 | TNDSDLFDVY | | 44477 |
| HPV45 | L2 | 393 | 9 | TSAWDVPIY | | 44478 |
| HPV45 | L2 | 418 | 11 | TSPTNASTTTY | | 44479 |
| HPV45 | L2 | 359 | 8 | TTPSTIHK | | 44480 |
| HPV45 | L2 | 425 | 8 | TTTYIGIH | | 44481 |
| HPV45 | L2 | 426 | 11 | TTYIGIHGTQY | | 44482 |
| HPV45 | L2 | 293 | 10 | TVRFSRLGQR | | 44483 |
| HPV45 | L2 | 217 | 9 | TVRRVRGPR | | 44484 |
| HPV45 | L2 | 217 | 11 | TVRRVRGPRLY | | 44485 |
| HPV45 | L2 | 80 | 9 | TVVDVGPTR | | 44486 |
| HPV45 | L2 | 182 | 9 | VGTPTSGSH | | 44487 |
| HPV45 | L2 | 182 | 11 | VGTPTSGSHGY | | 44488 |
| HPV45 | L2 | 2 | 8 | VSHRAARR | | 44489 |
| HPV45 | L2 | 2 | 9 | VSHRAARRK | | 44490 |
| HPV45 | L2 | 2 | 10 | VSHRAARRKR | | 44491 |
| HPV45 | L2 | 236 | 9 | VSTSQFLTH | | 44492 |
| HPV45 | L2 | 249 | 8 | VTFDNPAY | | 44493 |
| HPV45 | L2 | 81 | 8 | VVDVGPTR | | 44494 |
| HPV45 | L2 | 444 | 8 | YFPKKRKR | | 44495 |
| HPV45 | L2 | 444 | 11 | YFPKKRKRIPY | | 44496 |
| HPV45 | L2 | 428 | 9 | YIGIHGTQY | | 44497 |
| HPV45 | L2 | 428 | 10 | YIGIHGTQYY | | 44498 |
| HPV45 | L2 | 437 | 8 | YLWPWYYY | | 44499 |
| HPV45 | L2 | 437 | 11 | YLWPWYYYFPK | | 44500 |
| HPV45 | L2 | 227 | 9 | YSRANQQVR | | 44501 |
| HPV45 | L2 | 401 | 11 | YTGPDIILPSH | | 44502 |
| HPV56 | E2 | 177 | 9 | AAVSHRPGK | | 44503 |
| HPV56 | E2 | 177 | 10 | AAVSHRPGKR | | 44504 |
| HPV56 | E2 | 21 | 10 | ALESLSTTIY | | 44505 |
| HPV56 | E2 | 178 | 8 | AVSHRPGK | | 44506 |
| HPV56 | E2 | 178 | 9 | AVSHRPGKR | | 44507 |
| HPV56 | E2 | 178 | 11 | AVSHRPGKRPR | | 44508 |
| HPV56 | E2 | 249 | 8 | CCRYRFQK | | 44509 |
| HPV56 | E2 | 249 | 9 | CCRYRFQKY | | 44510 |
| HPV56 | E2 | 249 | 10 | CCRYRFQKYK | | 44511 |
| HPV56 | E2 | 52 | 8 | CFKKEGQH | | 44512 |
| HPV56 | E2 | 4 | 8 | CLQVCKAK | | 44513 |
| HPV56 | E2 | 71 | 8 | CMQYVAWK | | 44514 |
| HPV56 | E2 | 71 | 9 | CMQYVAWKY | | 44515 |
| HPV56 | E2 | 71 | 11 | CMQYVAWKYIY | | 44516 |
| HPV56 | E2 | 92 | 10 | CSGVDYRGIY | | 44517 |
| HPV56 | E2 | 92 | 11 | CSGVDYRGIYY | | 44518 |
| HPV56 | E2 | 176 | 10 | DAAVSHRPGK | | 44519 |
| HPV56 | E2 | 176 | 11 | DAAVSHRPGKR | | 44520 |
| RPV56 | E2 | 113 | 8 | DFEQEAKK | | 44521 |
| HPV56 | E2 | 65 | 10 | DGSKNNCMQY | | 44522 |
| HPV56 | E2 | 215 | 8 | DNTDSRSR | | 44523 |
| HPV56 | E2 | 195 | 9 | DSSRESHAK | | 44524 |
| HPV56 | E2 | 140 | 8 | DSVSSTCR | | 44525 |
| HPV56 | E2 | 140 | 9 | DSVSSTCRY | | 44526 |
| HPV56 | E2 | 213 | 8 | DTDNTDSR | | 44527 |
| HPV56 | E2 | 213 | 10 | DTDNTDSRSR | | 44528 |
| HPV56 | E2 | 117 | 8 | EAKKFGCK | | 44529 |

TABLE XVII-continued

A11 Motif Peptides

| Type | Protein | Position | No. of Amino Acids | Sequence | A*1101 | Seq. Id. No. |
|---|---|---|---|---|---|---|
| HPV56 | E2 | 193 | 9 | EFDSSRESH | | 44530 |
| HPV56 | E2 | 193 | 11 | EFDSSRESHAK | | 44531 |
| HPV56 | E2 | 43 | 8 | ELWLTEPK | | 44532 |
| HPV56 | E2 | 43 | 9 | ELWLTEPKK | | 44533 |
| HPV56 | E2 | 191 | 8 | ESEFDSSR | | 44534 |
| HPV56 | E2 | 191 | 11 | ESEFDSSRESH | | 44535 |
| HPV56 | E2 | 199 | 10 | ESHAKCVTTH | | 44536 |
| HPV56 | E2 | 23 | 8 | ESLSTTIY | | 44537 |
| HPV56 | E2 | 288 | 10 | ETQRNSFLSH | | 44538 |
| HPV56 | E2 | 154 | 9 | ETVNEYNTH | | 44539 |
| HPV56 | E2 | 154 | 10 | ETVNEYNTHK | | 44540 |
| HPV56 | E2 | 128 | 10 | EVHMENESIY | | 44541 |
| HPV56 | E2 | 61 | 8 | EVWFDGSK | | 44542 |
| HPV56 | E2 | 64 | 11 | FDGSKNNCMQY | | 44543 |
| HPV56 | E2 | 194 | 8 | FDSSRESH | | 44544 |
| HPV56 | E2 | 194 | 10 | FDSSRESHAK | | 44545 |
| HPV56 | E2 | 121 | 10 | FGCKNIWEVH | | 44546 |
| HPV56 | E2 | 294 | 11 | FLSHVKIPVVY | | 44547 |
| HPV56 | E2 | 261 | 8 | FVDVTSTY | | 44548 |
| HPV56 | E2 | 261 | 9 | FVDVTSTYH | | 44549 |
| HPV56 | E2 | 122 | 9 | GCKNIWEVH | | 44550 |
| HPV56 | E2 | 231 | 9 | GDKTTPVVH | | 44551 |
| HPV56 | E2 | 231 | 11 | GDKTTPVVHLK | | 44552 |
| HPV56 | E2 | 99 | 9 | GIYYVHDGH | | 44553 |
| HPV56 | E2 | 99 | 10 | GIYYVHDGHK | | 44554 |
| HPV56 | E2 | 173 | 9 | GNQDAAVSH | | 44555 |
| HPV56 | E2 | 173 | 10 | GNQDAAVSHR | | 44556 |
| HPV56 | E2 | 66 | 9 | GSKNNCMQY | | 44557 |
| HPV56 | E2 | 94 | 8 | GVDYRGIY | | 44558 |
| HPV56 | E2 | 94 | 9 | GVDYRGIYY | | 44559 |
| HPV56 | E2 | 94 | 11 | GVDYRGIYYVH | | 44560 |
| HPV56 | E2 | 201 | 8 | HAKCVTTH | | 44561 |
| HPV56 | E2 | 201 | 10 | HAKCVTTHTH | | 44562 |
| HPV56 | E2 | 104 | 8 | HDGHKTYY | | 44563 |
| RPV56 | E2 | 59 | 10 | HIEVWFDGSK | | 44564 |
| HPV56 | E2 | 210 | 11 | HISDTDNTDSR | | 44565 |
| HPV56 | E2 | 239 | 8 | HLKGEPNR | | 44566 |
| HPV56 | E2 | 239 | 10 | HLKGEPNRLK | | 44567 |
| HPV56 | E2 | 130 | 8 | HMENESIY | | 44568 |
| HPV56 | E2 | 297 | 8 | HVKIPVVY | | 44569 |
| HPV56 | E2 | 297 | 9 | HVKIPVVYR | | 44570 |
| HPV56 | E2 | 20 | 11 | IALESLSTTIY | | 44571 |
| HPV56 | E2 | 283 | 9 | IIYKDETQR | | 44572 |
| HPV56 | E2 | 224 | 10 | INNNNHPGDK | | 44573 |
| HPV56 | E2 | 211 | 10 | ISDTDNTDSR | | 44574 |
| HPV56 | E2 | 281 | 11 | ITIIYKDETQR | | 44575 |
| HPV56 | E2 | 248 | 9 | KCCRYRFQK | | 44576 |
| HPV56 | E2 | 248 | 10 | KCCRYRFQKY | | 44577 |
| HPV56 | E2 | 248 | 11 | KCCRYRFQKYK | | 44578 |
| HPV56 | E2 | 51 | 9 | KCFKKEGQH | | 44579 |
| HPV56 | E2 | 203 | 8 | KCVTTHTH | | 44580 |
| HPV56 | E2 | 120 | 11 | KFGCKNIWEVH | | 44581 |
| HPV56 | E2 | 241 | 8 | KGEPNRLK | | 44582 |
| HPV56 | E2 | 241 | 11 | KGEPNRLKCCR | | 44583 |
| HPV56 | E2 | 68 | 11 | KNNCMQYVAWK | | 44584 |
| HPV56 | E2 | 276 | 10 | KNYSIITIIY | | 44585 |
| HPV56 | E2 | 276 | 11 | KNYSIITIIYK | | 44586 |
| HPV56 | E2 | 258 | 11 | KTLFVDVTSTY | | 44587 |
| HPV56 | E2 | 233 | 9 | KTTPVVHLK | | 44588 |
| HPV56 | E2 | 90 | 8 | KVCSGVDY | | 44589 |
| HPV56 | E2 | 90 | 9 | KVCSGVDYR | | 44590 |
| HPV56 | E2 | 260 | 9 | LFVDVTSTY | | 44591 |
| HPV56 | E2 | 260 | 10 | LFVDVTSTYH | | 44592 |
| HPV56 | E2 | 295 | 10 | LSHVKIPVVY | | 44593 |
| HPV56 | E2 | 295 | 11 | LSHVKIPVVYR | | 44594 |
| HPV56 | E2 | 46 | 9 | LTEPKKCFK | | 44595 |
| HPV56 | E2 | 46 | 10 | LTEPKKCFKK | | 44596 |
| HPV56 | E2 | 1 | 9 | MVPCLQVCK | | 44597 |
| HPV56 | E2 | 1 | 11 | MVPCLQVCKAK | | 44598 |
| HPV56 | E2 | 70 | 9 | NCMQYVAWK | | 44599 |
| HPV56 | E2 | 70 | 10 | NCMQYVAWKY | | 44600 |
| HPV56 | E2 | 83 | 8 | NGDCGWQK | | 44601 |
| HPV56 | E2 | 69 | 10 | NNCMQYVAWK | | 44602 |
| HPV56 | E2 | 69 | 11 | NNCMQYVAWKY | | 44603 |
| HPV56 | E2 | 31 | 8 | NNEEWTLR | | 44604 |

TABLE XVII-continued

A11 Motif Peptides

| Type | Protein | Position | No. of Amino Acids | Sequence | A*1101 | Seq. Id. No. |
|---|---|---|---|---|---|---|
| HPV56 | E2 | 226 | 8 | NNNHPGDK | | 44605 |
| HPV56 | E2 | 225 | 9 | NNNNHPGDK | | 44606 |
| HPV56 | E2 | 292 | 8 | NSFLSHVK | | 44607 |
| HPV56 | E2 | 149 | 11 | NVSPVETVNEY | | 44608 |
| HPV56 | E2 | 3 | 9 | PCLQVCKAK | | 44609 |
| HPV56 | E2 | 139 | 9 | PDSVSSTCR | | 44610 |
| HPV56 | E2 | 139 | 10 | PDSVSSTCRY | | 44611 |
| HPV56 | E2 | 230 | 10 | PGDKTTPVVH | | 44612 |
| HPV56 | E2 | 183 | 8 | PGKRPRLR | | 44613 |
| HPV56 | E2 | 244 | 8 | PNRLKCCR | | 44614 |
| HPV56 | E2 | 244 | 9 | PNRLKCCRY | | 44615 |
| HPV56 | E2 | 244 | 10 | PNRLKCCRYR | | 44616 |
| HPV56 | E2 | 152 | 8 | PVETVNEY | | 44617 |
| HPV56 | E2 | 152 | 11 | PVETVNEYNTH | | 44618 |
| HPV56 | E2 | 236 | 11 | PVVHLKGEPNR | | 44619 |
| HPV56 | E2 | 301 | 10 | PVVYRLVWDK | | 44620 |
| HPV56 | E2 | 175 | 8 | QDAAVSHR | | 44621 |
| HPV56 | E2 | 175 | 11 | QDAAVSHRPGK | | 44622 |
| HPV56 | E2 | 98 | 10 | RGIYYVHDGH | | 44623 |
| HPV56 | E2 | 98 | 11 | RGIYYVHDGHK | | 44624 |
| HPV56 | E2 | 246 | 8 | RLKCCRYR | | 44625 |
| HPV56 | E2 | 246 | 11 | RLKCCRYRFQK | | 44626 |
| HPV56 | E2 | 188 | 11 | RLRESEFDSSR | | 44627 |
| HPV56 | E2 | 291 | 9 | RNSFLSHVK | | 44628 |
| HPV56 | E2 | 222 | 8 | RSINNNNH | | 44629 |
| HPV56 | E2 | 220 | 10 | RSRSINNNNH | | 44630 |
| HPV56 | E2 | 212 | 9 | SDTDNTDSR | | 44631 |
| HPV56 | E2 | 212 | 11 | SDTDNTDSRSR | | 44632 |
| HPV56 | E2 | 93 | 9 | SGVDYRGIY | | 44633 |
| HPV56 | E2 | 93 | 10 | SGVDYRGIYY | | 44634 |
| HPV56 | E2 | 279 | 8 | SIITIIYK | | 44635 |
| HPV56 | E2 | 223 | 11 | SINNNNHPGDK | | 44636 |
| HPV56 | E2 | 196 | 8 | SSRESHAK | | 44637 |
| HPV56 | E2 | 266 | 11 | STYHWTSTDNK | | 44638 |
| HPV56 | E2 | 171 | 11 | SVGNQDAAVSH | | 44639 |
| HPV56 | E2 | 141 | 8 | SVSSTCRY | | 44640 |
| HPV56 | E2 | 40 | 11 | TCEELWLTEPK | | 44641 |
| HPV56 | E2 | 112 | 8 | TDFEQEAK | | 44642 |
| HPV56 | E2 | 112 | 9 | TDFEQEAKK | | 44643 |
| HPV56 | E2 | 214 | 9 | TDNTDSRSR | | 44644 |
| HPV56 | E2 | 282 | 10 | TIIYKDETQR | | 44645 |
| HPV56 | E2 | 28 | 11 | TIYNNEEWTLR | | 44646 |
| HPV56 | E2 | 259 | 10 | TLFVDVTSTY | | 44647 |
| HPV56 | E2 | 259 | 11 | TLFVDVTSTYH | | 44648 |
| HPV56 | E2 | 271 | 8 | TSTDNKNY | | 44649 |
| HPV56 | E2 | 234 | 8 | TTPVVHLK | | 44650 |
| HPV56 | E2 | 155 | 8 | TVNEYNTH | | 44651 |
| HPV56 | E2 | 155 | 9 | TVNEYNTHK | | 44652 |
| HPV56 | E2 | 75 | 8 | VAWKYIYY | | 44653 |
| HPV56 | E2 | 91 | 8 | VCSGVDYR | | 44654 |
| HPV56 | E2 | 91 | 11 | VCSGVDYRGIY | | 44655 |
| HPV56 | E2 | 262 | 8 | VDVTSTYH | | 44656 |
| HPV56 | E2 | 95 | 8 | VDYRGIYY | | 44657 |
| HPV56 | E2 | 95 | 10 | VDYRGIYYVH | | 44658 |
| HPV56 | E2 | 172 | 10 | VGNQDAAVSH | | 44659 |
| HPV56 | E2 | 172 | 11 | VGNQDAAVSHR | | 44660 |
| HPV56 | E2 | 156 | 8 | VNEYNTHK | | 44661 |
| HPV56 | E2 | 179 | 8 | VSHRPGKR | | 44662 |
| HPV56 | E2 | 179 | 10 | VSHRPGKRPR | | 44663 |
| HPV56 | E2 | 150 | 10 | VSPVETVNEY | | 44664 |
| HPV56 | E2 | 237 | 10 | VVHLKGEPNR | | 44665 |
| HPV56 | E2 | 302 | 9 | VVYRLVWDK | | 44666 |
| HPV56 | E2 | 45 | 10 | WLTEPKKCFK | | 44667 |
| HPV56 | E2 | 45 | 11 | WLTEPKKCFKK | | 44668 |
| HPV56 | E2 | 270 | 9 | WTSTDNKNY | | 44669 |
| HPV56 | E2 | 137 | 11 | YCPDSVSSTCR | | 44670 |
| HPV56 | E2 | 82 | 9 | YNGDCGWQK | | 44671 |
| HPV56 | E2 | 30 | 9 | YNNEEWTLR | | 44672 |
| HPV56 | E2 | 278 | 8 | YSIITIIY | | 44673 |
| HPV56 | E2 | 278 | 9 | YSIITIIYK | | 44674 |
| HPV56 | E2 | 111 | 9 | YTDFEQEAK | | 44675 |
| HPV56 | E2 | 111 | 10 | YTDFEQEAKK | | 44676 |
| HPV56 | E2 | 74 | 8 | YVAWKYIY | | 44677 |
| HPV56 | E2 | 74 | 9 | YVAWKYIYY | | 44678 |
| HPV56 | E2 | 102 | 9 | YVHDGHKTY | | 44679 |

TABLE XVII-continued

A11 Motif Peptides

| Type | Protein | Position | No. of Amino Acids | Sequence | A*1101 | Seq. Id. No. |
|---|---|---|---|---|---|---|
| HPV56 | E2 | 102 | 10 | YVHDGHKTYY | | 44680 |
| HPV56 | E6 | 49 | 9 | ACTELKLVY | | 44681 |
| HPV56 | E6 | 49 | 10 | ACTELKLVYR | | 44682 |
| HPV56 | E6 | 89 | 8 | ATLESITK | | 44683 |
| HPV56 | E6 | 89 | 9 | ATLESITKK | | 44684 |
| HPV56 | E6 | 64 | 10 | AVCRVCLLFY | | 44685 |
| HPV56 | E6 | 100 | 8 | CDLLIRCY | | 44686 |
| HPV56 | E6 | 100 | 9 | CDLLIRCYR | | 44687 |
| HPV56 | E6 | 122 | 8 | CDRKRRFH | | 44688 |
| HPV56 | E6 | 139 | 10 | CLGCWRQTSR | | 44689 |
| HPV56 | E6 | 69 | 9 | CLLFYSKVR | | 44690 |
| HPV56 | E6 | 69 | 10 | CLLFYSKVRK | | 44691 |
| HPV56 | E6 | 69 | 11 | CLLFYSKVRKY | | 44692 |
| HPV56 | E6 | 50 | 8 | CTELKLVY | | 44693 |
| HPV56 | E6 | 50 | 9 | CTELKLVYR | | 44694 |
| HPV56 | E6 | 33 | 10 | CVYCKKELTR | | 44695 |
| HPV56 | E6 | 59 | 9 | DDFPYAVCR | | 44696 |
| HPV56 | E6 | 60 | 8 | DFPYAVCR | | 44697 |
| HPV56 | E6 | 101 | 8 | DLLIRCYR | | 44698 |
| HPV56 | E6 | 28 | 8 | DLRLSCVY | | 44699 |
| HPV56 | E6 | 28 | 10 | DLRLSCVYCK | | 44700 |
| HPV56 | E6 | 28 | 11 | DLRLSCVYCKK | | 44701 |
| HPV56 | E6 | 23 | 8 | EIPLIDLR | | 44702 |
| HPV56 | E6 | 39 | 8 | ELTRAEVY | | 44703 |
| HPV56 | E6 | 20 | 11 | EVLEIPLIDLR | | 44704 |
| HPV56 | E6 | 44 | 11 | EVYNFACTELK | | 44705 |
| HPV56 | E6 | 48 | 10 | FACTELKLVY | | 44706 |
| HPV56 | E6 | 48 | 11 | FACTELKLVYR | | 44707 |
| HPV56 | E6 | 5 | 9 | FNNPQERPR | | 44708 |
| HPV56 | E6 | 88 | 9 | GATLESITK | | 44709 |
| HPV56 | E6 | 88 | 10 | GATLESITKK | | 44710 |
| HPV56 | E6 | 141 | 8 | GCWRQTSR | | 44711 |
| HPV56 | E6 | 141 | 11 | GCWRQTSREPR | | 44712 |
| HPV56 | E6 | 137 | 8 | GSCLGCWR | | 44713 |
| HPV56 | E6 | 121 | 9 | HCDRKRRFH | | 44714 |
| HPV56 | E6 | 27 | 9 | IDLRLSCVY | | 44715 |
| HPV56 | E6 | 27 | 11 | IDLRLSCVYCK | | 44716 |
| HPV56 | E6 | 54 | 10 | KLVYRDDFPY | | 44717 |
| HPV56 | E6 | 75 | 8 | KVRKYRYY | | 44718 |
| HPV56 | E6 | 75 | 10 | KVRKYRYYDY | | 44719 |
| HPV56 | E6 | 99 | 9 | LCDLLIRCY | | 44720 |
| HPV56 | E6 | 99 | 10 | LCDLLIRCYR | | 44721 |
| HPV56 | E6 | 71 | 8 | LFYSKVRK | | 44722 |
| HPV56 | E6 | 71 | 9 | LFYSKVRKY | | 44723 |
| HPV56 | E6 | 71 | 10 | LFYSKVRKYR | | 44724 |
| HPV56 | E6 | 71 | 11 | LFYSKVRKYRY | | 44725 |
| HPV56 | E6 | 140 | 9 | LGCWRQTSR | | 44726 |
| HPV56 | E6 | 26 | 10 | LIDLRLSCVY | | 44727 |
| HPV56 | E6 | 70 | 8 | LLFYSKVR | | 44728 |
| HPV56 | E6 | 70 | 9 | LLFYSKVRK | | 44729 |
| HPV56 | E6 | 70 | 10 | LLFYSKVRKY | | 44730 |
| HPV56 | E6 | 70 | 11 | LLFYSKVRKYR | | 44731 |
| HPV56 | E6 | 31 | 8 | LSCVYCKK | | 44732 |
| HPV56 | E6 | 113 | 9 | LTPEEKQLH | | 44733 |
| HPV56 | E6 | 55 | 9 | LVYRDDFPY | | 44734 |
| HPV56 | E6 | 47 | 8 | NFACTELK | | 44735 |
| HPV56 | E6 | 47 | 11 | NFACTELKLVY | | 44736 |
| HPV56 | E6 | 6 | 8 | NNPQERPR | | 44737 |
| HPV56 | E6 | 6 | 11 | NNPQERPRSLH | | 44738 |
| HPV56 | E6 | 25 | 11 | PLIDLRLSCVY | | 44739 |
| HPV56 | E6 | 112 | 10 | PLTPEEKQLH | | 44740 |
| HPV56 | E6 | 4 | 8 | QFNNPQER | | 44741 |
| HPV56 | E6 | 4 | 10 | QFNNPQERPR | | 44742 |
| HPV56 | E6 | 98 | 8 | QLCDLLIR | | 44743 |
| HPV56 | E6 | 98 | 10 | QLCDLLIRCY | | 44744 |
| HPV56 | E6 | 98 | 11 | QLCDLLIRCYR | | 44745 |
| HPV56 | E6 | 119 | 8 | QLHCDRKR | | 44746 |
| HPV56 | E6 | 119 | 9 | QLHCDRKRR | | 44747 |
| HPV56 | E6 | 119 | 11 | QLHCDRKRRFH | | 44748 |
| HPV56 | E6 | 110 | 9 | QSPLTPEEK | | 44749 |
| HPV56 | E6 | 108 | 11 | RCQSPLTPEEK | | 44750 |
| HPV56 | E6 | 58 | 10 | RDDFPYAVCR | | 44751 |
| HPV56 | E6 | 30 | 8 | RLSCVYCK | | 44752 |
| HPV56 | E6 | 30 | 9 | RLSCVYCKK | | 44753 |
| HPV56 | E6 | 67 | 9 | RVCLLFYSK | | 44754 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV56 | E6 | 67 | 11 | RVCLLFYSKVR | | 44755 |
| HPV56 | E6 | 138 | 11 | SCLGCWRQTSR | | 44756 |
| HPV56 | E6 | 32 | 11 | SCVYCKKELTR | | 44757 |
| HPV56 | E6 | 136 | 9 | TGSCLGCWR | | 44758 |
| HPV56 | E6 | 90 | 8 | TLESITKK | | 44759 |
| HPV56 | E6 | 68 | 8 | VCLLFYSK | | 44760 |
| HPV56 | E6 | 68 | 10 | VCLLFYSKVR | | 44761 |
| HPV56 | E6 | 68 | 11 | VCLLFYSKVRK | | 44762 |
| HPV56 | E6 | 65 | 9 | VCRVCLLFY | | 44763 |
| HPV56 | E6 | 65 | 11 | VCRVCLLFYSK | | 44764 |
| HPV56 | E6 | 21 | 10 | VLEIPLIDLR | | 44765 |
| HPV56 | E6 | 135 | 10 | WTGSCLGCWR | | 44766 |
| HPV56 | E6 | 63 | 11 | YAVCRVCLLFY | | 44767 |
| HPV56 | E6 | 35 | 8 | YCKKELTR | | 44768 |
| HPV56 | E6 | 87 | 10 | YGATLESITK | | 44769 |
| HPV56 | E6 | 87 | 11 | YGATLESITKK | | 44770 |
| HPV56 | E6 | 46 | 9 | YNFACTELK | | 44771 |
| HPV56 | E6 | 73 | 8 | YSKVRKYR | | 44772 |
| HPV56 | E6 | 73 | 9 | YSKVRKYRY | | 44773 |
| HPV56 | E6 | 73 | 10 | YSKVRKYRYY | | 44774 |
| HPV56 | E7 | 75 | 10 | DIQSTKEDLR | | 44775 |
| HPV56 | E7 | 33 | 10 | EDEDEDEVDH | | 44776 |
| HPV56 | E7 | 35 | 8 | EDEDEVDH | | 44777 |
| HPV56 | E7 | 37 | 10 | EDEVDHLQER | | 44778 |
| HPV56 | E7 | 39 | 8 | EVDHLQER | | 44779 |
| HPV56 | E7 | 70 | 11 | FVVQLDIQSTK | | 44780 |
| HPV56 | E7 | 42 | 10 | HLQERPQQAR | | 44781 |
| HPV56 | E7 | 62 | 8 | HVPCCECK | | 44782 |
| HPV56 | E7 | 74 | 11 | LDIQSTKEDLR | | 44783 |
| HPV56 | E7 | 60 | 10 | LIHVPCCECK | | 44784 |
| HPV56 | E7 | 52 | 8 | QAKQHTCY | | 44785 |
| HPV56 | E7 | 52 | 11 | QAKQHTCYLIH | | 44786 |
| HPV56 | E7 | 49 | 8 | QARQAKQH | | 44787 |
| HPV56 | E7 | 49 | 11 | QARQAKQHTCY | | 44788 |
| HPV56 | E7 | 73 | 8 | QLDIQSTK | | 44789 |
| HPV56 | E7 | 77 | 8 | QSTKEDLR | | 44790 |
| HPV56 | E7 | 71 | 10 | VVQLDIQSTK | | 44791 |
| HPV56 | E7 | 59 | 11 | YLIHVPCCECK | | 44792 |
| HPV56 | L1 | 135 | 9 | ACVGLEVGR | | 44793 |
| HPV56 | L1 | 273 | 11 | ADAYGDSMWFY | | 44794 |
| HPV56 | L1 | 149 | 11 | AGLSGHPLFNR | | 44795 |
| HPV56 | L1 | 72 | 11 | AGSSRLLAVGH | | 44796 |
| HPV56 | L1 | 241 | 11 | AMDFKVLQESK | | 44797 |
| HPV56 | L1 | 198 | 8 | AMGEHWTK | | 44798 |
| HPV56 | L1 | 169 | 10 | ANNNVIEDSR | | 44799 |
| HPV56 | L1 | 58 | 8 | ATDSYVKR | | 44800 |
| HPV56 | L1 | 381 | 8 | ATEQLSKY | | 44801 |
| HPV56 | L1 | 381 | 11 | ATEQLSKYDAR | | 44802 |
| HPV56 | L1 | 444 | 8 | ATSLEDKY | | 44803 |
| HPV56 | L1 | 444 | 9 | ATSLEDKYR | | 44804 |
| HPV56 | L1 | 444 | 10 | ATSLEDKYRY | | 44805 |
| HPV56 | L1 | 37 | 9 | ATWRPSENK | | 44806 |
| HPV56 | L1 | 37 | 11 | ATWRPSENKVY | | 44807 |
| HPV56 | L1 | 512 | 8 | AVATSKKR | | 44808 |
| HPV56 | L1 | 79 | 11 | AVGHPYYSVTK | | 44809 |
| HPV56 | L1 | 195 | 8 | CTPAMGEH | | 44810 |
| HPV56 | L1 | 195 | 11 | CTPAMGEHWTK | | 44811 |
| HPV56 | L1 | 136 | 8 | CVGLEVGR | | 44812 |
| HPV56 | L1 | 389 | 8 | DARKINQY | | 44813 |
| HPV56 | L1 | 389 | 10 | DARKINQYLR | | 44814 |
| HPV56 | L1 | 389 | 11 | DARKINQYLRH | | 44815 |
| HPV56 | L1 | 274 | 10 | DAYGDSMWFY | | 44816 |
| HPV56 | L1 | 243 | 9 | DFKVLQESK | | 44817 |
| HPV56 | L1 | 257 | 8 | DIVQSTCK | | 44818 |
| HPV56 | L1 | 257 | 9 | DIVQSTCKY | | 44819 |
| HPV56 | L1 | 491 | 9 | DLDQFPLGR | | 44820 |
| HPV56 | L1 | 491 | 10 | DLDQFPLGRK | | 44821 |
| HPV56 | L1 | 179 | 8 | DNISVDGK | | 44822 |
| HPV56 | L1 | 90 | 9 | DNTKTNIPK | | 44823 |
| HPV56 | L1 | 278 | 8 | DSMWFYLR | | 44824 |
| HPV56 | L1 | 278 | 9 | DSMWFYLRR | | 44825 |
| HPV56 | L1 | 176 | 11 | DSRDNISVDGK | | 44826 |
| HPV56 | L1 | 60 | 11 | DSYVKRTSIFY | | 44827 |
| HPV56 | L1 | 236 | 10 | DTGFGAMDFK | | 44828 |
| HPV56 | L1 | 121 | 11 | DTNIYNPDQER | | 44829 |

TABLE XVII-continued

A11 Motif Peptides

| Type | Protein | Position | No. of Amino Acids | Sequence | A*1101 | Seq. Id. No. |
|---|---|---|---|---|---|---|
| HPV56 | L1 | 337 | 9 | EAQLFNKPY | | 44830 |
| HPV56 | L1 | 448 | 8 | EDKYRYVR | | 44831 |
| HPV56 | L1 | 404 | 10 | ELQFVFQLCK | | 44832 |
| HPV56 | L1 | 308 | 10 | ELYLKGSNGR | | 44833 |
| HPV56 | L1 | 303 | 8 | ETIPAELY | | 44834 |
| HPV56 | L1 | 303 | 10 | ETIPAELYLK | | 44835 |
| HPV56 | L1 | 290 | 8 | FARHYFNR | | 44836 |
| HPV56 | L1 | 290 | 11 | FARHYFNRAGK | | 44837 |
| HPV56 | L1 | 117 | 9 | FGLPDTNIY | | 44838 |
| HPV56 | L1 | 501 | 8 | FLMQLGTR | | 44839 |
| HPV56 | L1 | 501 | 10 | FLMQLGTRSK | | 44840 |
| HPV56 | L1 | 33 | 8 | FLQMATWR | | 44841 |
| HPV56 | L1 | 341 | 9 | FNKPYWLQR | | 44842 |
| HPV56 | L1 | 364 | 9 | FVTVVDTTR | | 44843 |
| HPV56 | L1 | 194 | 9 | GCTPAMGEH | | 44844 |
| HPV56 | L1 | 277 | 9 | GDSMWFYLR | | 44845 |
| HPV56 | L1 | 277 | 10 | GDSMWFYLRR | | 44846 |
| HPV56 | L1 | 238 | 8 | GFGAMDFK | | 44847 |
| HPV56 | L1 | 118 | 8 | GLPDTNIY | | 44848 |
| HPV56 | L1 | 150 | 10 | GLSGHPLFNR | | 44849 |
| HPV56 | L1 | 73 | 10 | GSSRLLAVGH | | 44850 |
| HPV56 | L1 | 235 | 11 | IDTGFGAMDFK | | 44851 |
| HPV56 | L1 | 32 | 9 | IFLQMATWR | | 44852 |
| HPV56 | L1 | 68 | 9 | IFYHAGSSR | | 44853 |
| HPV56 | L1 | 393 | 11 | INQYLRHVEEY | | 44854 |
| HPV56 | L1 | 378 | 10 | ISTATEQLSK | | 44855 |
| HPV56 | L1 | 378 | 11 | ISTATEQLSKY | | 44856 |
| HPV56 | L1 | 414 | 10 | ITLSAEVMAY | | 44857 |
| HPV56 | L1 | 334 | 10 | ITSEAQLFNK | | 44858 |
| HPV56 | L1 | 192 | 11 | IVGCTPAMGEH | | 44859 |
| HPV56 | L1 | 258 | 8 | IVQSTCKY | | 44860 |
| HPV56 | L1 | 258 | 11 | IVQSTCKYPDY | | 44861 |
| HPV56 | L1 | 89 | 10 | KDNTKTNIPK | | 44862 |
| HPV56 | L1 | 116 | 10 | KFGLPDTNIY | | 44863 |
| HPV56 | L1 | 500 | 9 | KFLMQLGTR | | 44864 |
| HPV56 | L1 | 500 | 11 | KFLMQLGTRSK | | 44865 |
| HPV56 | L1 | 392 | 8 | KINQYLRH | | 44866 |
| HPV56 | L1 | 413 | 11 | KITLSAEVMAY | | 44867 |
| HPV56 | L1 | 93 | 10 | KTNIPKVSAY | | 44868 |
| HPV56 | L1 | 300 | 11 | KVGETIPAELY | | 44869 |
| HPV56 | L1 | 98 | 8 | KVSAYQYR | | 44870 |
| HPV56 | L1 | 98 | 11 | KVSAYQYRVFR | | 44871 |
| HPV56 | L1 | 55 | 8 | KVVATDSY | | 44872 |
| HPV56 | L1 | 55 | 10 | KVVATDSYVK | | 44873 |
| HPV56 | L1 | 55 | 11 | KVVATDSYVKR | | 44874 |
| HPV56 | L1 | 45 | 11 | KVYLPPTPVSK | | 44875 |
| HPV56 | L1 | 168 | 11 | LANNNVIEDSR | | 44876 |
| HPV56 | L1 | 78 | 8 | LAVGHPYY | | 44877 |
| HPV56 | L1 | 256 | 9 | LDIVQSTCK | | 44878 |
| HPV56 | L1 | 256 | 10 | LDIVQSTCKY | | 44879 |
| HPV56 | L1 | 492 | 8 | LDQFPLGR | | 44880 |
| HPV56 | L1 | 492 | 9 | LDQFPLGRK | | 44881 |
| HPV56 | L1 | 289 | 9 | LFARHYFNR | | 44882 |
| HPV56 | L1 | 340 | 10 | LFNKPYWLQR | | 44883 |
| HPV56 | L1 | 363 | 10 | LFVTVVDTTR | | 44884 |
| HPV56 | L1 | 147 | 8 | LGAGLSGH | | 44885 |
| HPV56 | L1 | 77 | 8 | LLAVGHPY | | 44886 |
| HPV56 | L1 | 77 | 9 | LLAVGHPYY | | 44887 |
| HPV56 | L1 | 502 | 9 | LMQLGTRSK | | 44888 |
| HPV56 | L1 | 416 | 8 | LSAEVMAY | | 44889 |
| HPV56 | L1 | 416 | 10 | LSAEVMAYLH | | 44890 |
| HPV56 | L1 | 151 | 9 | LSGHPLFNR | | 44891 |
| HPV56 | L1 | 385 | 8 | LSKYDARK | | 44892 |
| HPV56 | L1 | 36 | 10 | MATWRPSENK | | 44893 |
| HPV56 | L1 | 242 | 10 | MDFKVLQESK | | 44894 |
| HPV56 | L1 | 333 | 11 | MITSEAQLFNK | | 44895 |
| HPV56 | L1 | 2 | 8 | MLPMMYIY | | 44896 |
| HPV56 | L1 | 2 | 9 | MLPMMYIYR | | 44897 |
| HPV56 | L1 | 1 | 9 | MMLPMMYIY | | 44898 |
| HPV56 | L1 | 1 | 10 | MMLPMMYIYR | | 44899 |
| HPV56 | L1 | 5 | 11 | MMYIYRDPPLH | | 44900 |
| HPV56 | L1 | 315 | 11 | NGREPPPSSVY | | 44901 |
| HPV56 | L1 | 95 | 8 | NIPKVSAY | | 44902 |
| HPV56 | L1 | 95 | 10 | NIPKVSAYQY | | 44903 |
| HPV56 | L1 | 95 | 11 | NIPKVSAYQYR | | 44904 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV56 | L1 | 123 | 9 | NIYNPDQER | | 44905 |
| HPV56 | L1 | 170 | 9 | NNNVIEDSR | | 44906 |
| HPV56 | L1 | 171 | 8 | NNVIEDSR | | 44907 |
| HPV56 | L1 | 91 | 8 | NTKTNIPK | | 44908 |
| HPV56 | L1 | 197 | 9 | PAMGEHWTK | | 44909 |
| HPV56 | L1 | 511 | 8 | PAVATSKK | | 44910 |
| HPV56 | L1 | 511 | 9 | PAVATSKKR | | 44911 |
| HPV56 | L1 | 266 | 11 | PDYLKMSADAY | | 44912 |
| HPV56 | L1 | 31 | 10 | PIFLQMATWR | | 44913 |
| HPV56 | L1 | 255 | 10 | PLDIVQSTCK | | 44914 |
| HPV56 | L1 | 255 | 11 | PLDIVQSTCKY | | 44915 |
| HPV56 | L1 | 146 | 9 | PLGAGLSGH | | 44916 |
| HPV56 | L1 | 467 | 10 | PTEKQDPLAK | | 44917 |
| HPV56 | L1 | 467 | 11 | PTEKQDPLAKY | | 44918 |
| HPV56 | L1 | 522 | 9 | PTSTSTPAK | | 44919 |
| HPV56 | L1 | 522 | 10 | PTSTSTPAKR | | 44920 |
| HPV56 | L1 | 522 | 11 | PTSTSTPAKRK | | 44921 |
| HPV56 | L1 | 442 | 9 | PVATSLEDK | | 44922 |
| HPV56 | L1 | 442 | 10 | PVATSLEDKY | | 44923 |
| HPV56 | L1 | 442 | 11 | PVATSLEDKYR | | 44924 |
| HPV56 | L1 | 52 | 11 | PVSKVVATDSY | | 44925 |
| HPV56 | L1 | 471 | 8 | QDPLAKYK | | 44926 |
| HPV56 | L1 | 406 | 8 | QFVFQLCK | | 44927 |
| HPV56 | L1 | 288 | 10 | QLFARHYFNR | | 44928 |
| HPV56 | L1 | 339 | 11 | QLFNKPYWLQR | | 44929 |
| HPV56 | L1 | 362 | 11 | QLFVTVVDTTR | | 44930 |
| HPV56 | L1 | 384 | 8 | QLSKYDAR | | 44931 |
| HPV56 | L1 | 384 | 9 | QLSKYDARK | | 44932 |
| HPV56 | L1 | 35 | 11 | QMATWRPSENK | | 44933 |
| HPV56 | L1 | 260 | 9 | QSTCKYPDY | | 44934 |
| HPV56 | L1 | 260 | 11 | QSTCKYPDYLK | | 44935 |
| HPV56 | L1 | 178 | 9 | RDNISVDGK | | 44936 |
| HPV56 | L1 | 76 | 9 | RLLAVGHPY | | 44937 |
| HPV56 | L1 | 76 | 10 | RLLAVGHPYY | | 44938 |
| HPV56 | L1 | 508 | 10 | RSKPAVATSK | | 44939 |
| HPV56 | L1 | 508 | 11 | RSKPAVATSKK | | 44940 |
| HPV56 | L1 | 455 | 9 | RSTAITCQR | | 44941 |
| HPV56 | L1 | 108 | 9 | RVRLPDPNK | | 44942 |
| HPV56 | L1 | 417 | 9 | SAEVMAYLH | | 44943 |
| HPV56 | L1 | 520 | 11 | SAPTSTSTPAK | | 44944 |
| HPV56 | L1 | 100 | 9 | SAYQYRVFR | | 44945 |
| HPV56 | L1 | 100 | 11 | SAYQYRVFRVR | | 44946 |
| HPV56 | L1 | 152 | 8 | SGHPLFNR | | 44947 |
| HPV56 | L1 | 67 | 10 | SIFYHAGSSR | | 44948 |
| HPV56 | L1 | 446 | 8 | SLEDKYRY | | 44949 |
| HPV56 | L1 | 446 | 10 | SLEDKYRYVR | | 44950 |
| HPV56 | L1 | 279 | 8 | SMWFYLRR | | 44951 |
| HPV56 | L1 | 74 | 9 | SSRLLAVGH | | 44952 |
| HPV56 | L1 | 74 | 11 | SSRLLAVGHPY | | 44953 |
| HPV56 | L1 | 456 | 8 | STAITCQR | | 44954 |
| HPV56 | L1 | 379 | 9 | STATEQLSK | | 44955 |
| HPV56 | L1 | 379 | 10 | STATEQLSKY | | 44956 |
| HPV56 | L1 | 261 | 8 | STCKYPDY | | 44957 |
| HPV56 | L1 | 261 | 10 | STCKYPDYLK | | 44958 |
| HPV56 | L1 | 489 | 11 | STDLDQFPLGR | | 44959 |
| HPV56 | L1 | 526 | 8 | STPAKRKR | | 44960 |
| HPV56 | L1 | 526 | 9 | STPAKRKRR | | 44961 |
| HPV56 | L1 | 524 | 8 | STSTPAKR | | 44962 |
| HPV56 | L1 | 524 | 9 | STSTPAKRK | | 44963 |
| HPV56 | L1 | 524 | 10 | STSTPAKRKR | | 44964 |
| HPV56 | L1 | 524 | 11 | STSTPAKRKRR | | 44965 |
| HPV56 | L1 | 86 | 8 | SVTKDNTK | | 44966 |
| HPV56 | L1 | 380 | 8 | TATEQLSK | | 44967 |
| HPV56 | L1 | 380 | 9 | TATEQLSKY | | 44968 |
| HPV56 | L1 | 262 | 9 | TCKYPDYLK | | 44969 |
| HPV56 | L1 | 460 | 11 | TCQREQPPTEK | | 44970 |
| HPV56 | L1 | 490 | 10 | TDLDQFPLGR | | 44971 |
| HPV56 | L1 | 490 | 11 | TDLDQFPLGRK | | 44972 |
| HPV56 | L1 | 237 | 9 | TGFGAMDFK | | 44973 |
| HPV56 | L1 | 304 | 9 | TIPAELYLK | | 44974 |
| HPV56 | L1 | 377 | 11 | TISTATEQLSK | | 44975 |
| HPV56 | L1 | 415 | 9 | TLSAEVMAY | | 44976 |
| HPV56 | L1 | 415 | 11 | TLSAEVMAYLH | | 44977 |
| HPV56 | L1 | 94 | 9 | TNIPKVSAY | | 44978 |
| HPV56 | L1 | 94 | 11 | TNIPKVSAYQY | | 44979 |

TABLE XVII-continued

A11 Motif Peptides

| Type | Protein | Position | No. of Amino Acids | Sequence | A*1101 | Seq. Id. No. |
|---|---|---|---|---|---|---|
| HPV56 | L1 | 122 | 10 | TNIYNPDQER | | 44980 |
| HPV56 | L1 | 335 | 9 | TSEAQLFNK | | 44981 |
| HPV56 | L1 | 335 | 11 | TSEAQLFNKPY | | 44982 |
| HPV56 | L1 | 66 | 11 | TSIFYHAGSSR | | 44983 |
| HPV56 | L1 | 445 | 8 | TSLEDKYR | | 44984 |
| HPV56 | L1 | 445 | 9 | TSLEDKYRY | | 44985 |
| HPV56 | L1 | 445 | 11 | TSLEDKYRYVR | | 44986 |
| HPV56 | L1 | 525 | 8 | TSTPAKRK | | 44987 |
| HPV56 | L1 | 525 | 9 | TSTPAKRKR | | 44988 |
| HPV56 | L1 | 525 | 10 | TSTPAKRKRR | | 44989 |
| HPV56 | L1 | 523 | 8 | TSTSTPAK | | 44990 |
| HPV56 | L1 | 523 | 9 | TSTSTPAKR | | 44991 |
| HPV56 | L1 | 523 | 10 | TSTSTPAKRK | | 44992 |
| HPV56 | L1 | 523 | 11 | TSTSTPAKRKR | | 44993 |
| HPV56 | L1 | 57 | 8 | VATDSYVK | | 44994 |
| HPV56 | L1 | 57 | 9 | VATDSYVKR | | 44995 |
| HPV56 | L1 | 443 | 8 | VATSLEDK | | 44996 |
| HPV56 | L1 | 443 | 9 | VATSLEDKY | | 44997 |
| HPV56 | L1 | 443 | 10 | VATSLEDKYR | | 44998 |
| HPV56 | L1 | 443 | 11 | VATSLEDKYRY | | 44999 |
| HPV56 | L1 | 106 | 11 | VFRVRLPDPNK | | 45000 |
| HPV56 | L1 | 193 | 10 | VGCTPAMGEH | | 45001 |
| HPV56 | L1 | 301 | 10 | VGETIPAELY | | 45002 |
| HPV56 | L1 | 80 | 10 | VGHPYYSVTK | | 45003 |
| HPV56 | L1 | 99 | 10 | VSAYQYRVFR | | 45004 |
| HPV56 | L1 | 53 | 10 | VSKVVATDSY | | 45005 |
| HPV56 | L1 | 365 | 8 | VTVVDTTR | | 45006 |
| HPV56 | L1 | 56 | 9 | VVATDSYVK | | 45007 |
| HPV56 | L1 | 56 | 10 | VVATDSYVKR | | 45008 |
| HPV56 | L1 | 134 | 10 | WACVGLEVGR | | 45009 |
| HPV56 | L1 | 346 | 8 | WLQRAQGH | | 45010 |
| HPV56 | L1 | 203 | 8 | WTKGAVCK | | 45011 |
| HPV56 | L1 | 388 | 9 | YDARKINQY | | 45012 |
| HPV56 | L1 | 388 | 11 | YDARKINQYLR | | 45013 |
| HPV56 | L1 | 276 | 8 | YGDSMWFY | | 45014 |
| HPV56 | L1 | 276 | 10 | YGDSMWFYLR | | 45015 |
| HPV56 | L1 | 276 | 11 | YGDSMWFYLRR | | 45016 |
| HPV56 | L1 | 7 | 9 | YIYRDPPLH | | 45017 |
| HPV56 | L1 | 7 | 10 | YIYRDPPLHY | | 45018 |
| HPV56 | L1 | 310 | 8 | YLKGSNGR | | 45019 |
| HPV56 | L1 | 268 | 9 | YLKMSADAY | | 45020 |
| HPV56 | L1 | 47 | 9 | YLPPTPVSK | | 45021 |
| HPV56 | L1 | 396 | 8 | YLRHVEEY | | 45022 |
| HPV56 | L1 | 283 | 10 | YLRREQLFAR | | 45023 |
| HPV56 | L1 | 283 | 11 | YLRREQLFARH | | 45024 |
| HPV56 | L1 | 85 | 9 | YSVTKDNTK | | 45025 |
| HPV56 | L1 | 62 | 9 | YVKRTSIFY | | 45026 |
| HPV56 | L1 | 62 | 10 | YVKRTSIFYH | | 45027 |
| HPV56 | L1 | 453 | 11 | YVRSTAITCQR | | 45028 |
| HPV56 | L2 | 222 | 8 | AAPRLYRK | | 45029 |
| HPV56 | L2 | 286 | 10 | AFTTRRGGVR | | 45030 |
| HPV56 | L2 | 69 | 9 | AGYVPLGSR | | 45031 |
| HPV56 | L2 | 281 | 10 | ALHRPAFTTR | | 45032 |
| HPV56 | L2 | 281 | 11 | ALHRPAFTTRR | | 45033 |
| HPV56 | L2 | 438 | 9 | ALWPVYFFR | | 45034 |
| HPV56 | L2 | 438 | 10 | ALWPVYFFRR | | 45035 |
| HPV56 | L2 | 438 | 11 | ALWPVYFFRRR | | 45036 |
| HPV56 | L2 | 340 | 9 | ANNSFDGLY | | 45037 |
| HPV56 | L2 | 12 | 8 | ASATQLYK | | 45038 |
| HPV56 | L2 | 12 | 11 | ASATQLYKTCK | | 45039 |
| HPV56 | L2 | 367 | 10 | ATPSAHLPIK | | 45040 |
| HPV56 | L2 | 14 | 9 | ATQLYKTCK | | 45041 |
| HPV56 | L2 | 275 | 9 | DFMNIVALH | | 45042 |
| HPV56 | L2 | 275 | 10 | DFMNIVALHR | | 45043 |
| HPV56 | L2 | 142 | 10 | DITPTSSTVH | | 45044 |
| HPV56 | L2 | 30 | 9 | DVVNKIEQK | | 45045 |
| HPV56 | L2 | 29 | 10 | EDVVNKIEQK | | 45046 |
| HPV56 | L2 | 194 | 10 | EIPMQTFAVH | | 45047 |
| HPV56 | L2 | 437 | 10 | FALWPVYFFR | | 45048 |
| HPV56 | L2 | 437 | 11 | FALWPVYFFRR | | 45049 |
| HPV56 | L2 | 344 | 8 | FDGLYDIY | | 45050 |
| HPV56 | L2 | 444 | 8 | FFRRRRRK | | 45051 |
| HPV56 | L2 | 444 | 9 | FFRRRRRKR | | 45052 |
| HPV56 | L2 | 276 | 8 | FMNIVALH | | 45053 |
| HPV56 | L2 | 276 | 9 | FMNIVALHR | | 45054 |

TABLE XVII-continued

A11 Motif Peptides

| Type | Protein | Position | No. of Amino Acids | Sequeuce | A*1101 | Seq. Id. No. |
|---|---|---|---|---|---|---|
| HPV56 | L2 | 287 | 9 | FTTRRGGVR | | 45055 |
| HPV56 | L2 | 418 | 11 | FVPQSPYDVTH | | 45056 |
| HPV56 | L2 | 314 | 8 | GARVHYYY | | 45057 |
| HPV56 | L2 | 217 | 9 | GFRRIAAPR | | 45058 |
| HPV56 | L2 | 217 | 11 | GFRRIAAPRLY | | 45059 |
| HPV56 | L2 | 292 | 10 | GGVRFSRLGR | | 45060 |
| HPV56 | L2 | 292 | 11 | GGVRFSRLGRK | | 45061 |
| HPV56 | L2 | 58 | 11 | GIGTGTGSGGR | | 45062 |
| HPV56 | L2 | 394 | 9 | GNVWETPFY | | 45063 |
| HPV56 | L2 | 64 | 8 | GSGGRAGY | | 45064 |
| HPV56 | L2 | 434 | 10 | GSSFALWPVY | | 45065 |
| HPV56 | L2 | 25 | 10 | GTCPEDVVNK | | 45066 |
| HPV56 | L2 | 62 | 10 | GTGSGGRAGY | | 45067 |
| HPV56 | L2 | 60 | 9 | GTGTGSGGR | | 45068 |
| HPV56 | L2 | 310 | 9 | GTQIGARVH | | 45069 |
| HPV56 | L2 | 310 | 10 | GTQIGARVHY | | 45070 |
| HPV56 | L2 | 310 | 11 | GTQIGARVHYY | | 45071 |
| HPV56 | L2 | 293 | 9 | GVRFSRLGR | | 45072 |
| HPV56 | L2 | 293 | 10 | GVRFSRLGRK | | 45073 |
| HPV56 | L2 | 221 | 8 | IAAPRLYR | | 45074 |
| HPV56 | L2 | 221 | 9 | IAAPRLYRK | | 45075 |
| HPV56 | L2 | 313 | 8 | IGARVHYY | | 45076 |
| HPV56 | L2 | 313 | 9 | IGARVHYYY | | 45077 |
| HPV56 | L2 | 59 | 10 | IGTGTGSGGR | | 45078 |
| HPV56 | L2 | 180 | 11 | ILISTPTSGIH | | 45079 |
| HPV56 | L2 | 44 | 10 | ILQWGSLFTY | | 45080 |
| HPV56 | L2 | 210 | 10 | ISSTPIPGFR | | 45081 |
| HPV56 | L2 | 210 | 11 | ISSTPIPGFRR | | 45082 |
| HPV56 | L2 | 182 | 9 | ISTPTSGIH | | 45083 |
| HPV56 | L2 | 182 | 11 | ISTPTSGIHSY | | 45084 |
| HPV56 | L2 | 143 | 9 | ITPTSSTVH | | 45085 |
| HPV56 | L2 | 81 | 8 | IVDVTPAR | | 45086 |
| HPV56 | L2 | 302 | 8 | KATIQTRR | | 45087 |
| HPV56 | L2 | 34 | 10 | KIEQKTWADK | | 45088 |
| HPV56 | L2 | 43 | 11 | KILQWGSLFTY | | 45089 |
| HPV56 | L2 | 235 | 10 | KVTDPAFLDR | | 45090 |
| HPV56 | L2 | 141 | 11 | LDITPTSSTVH | | 45091 |
| HPV56 | L2 | 393 | 10 | LGNVWETPFY | | 45092 |
| HPV56 | L2 | 299 | 10 | LGRKATIQTR | | 45093 |
| HPV56 | L2 | 299 | 11 | LGRKATIQTRR | | 45094 |
| HPV56 | L2 | 181 | 10 | LISTPTSGIH | | 45095 |
| HPV56 | L2 | 338 | 11 | LSANNSFDGLY | | 45096 |
| HPV56 | L2 | 277 | 8 | MNIVALHR | | 45097 |
| HPV56 | L2 | 1 | 8 | MVAHRATR | | 45098 |
| HPV56 | L2 | 1 | 9 | MVAHRATRR | | 45099 |
| HPV56 | L2 | 1 | 10 | MVAHRATRRK | | 45100 |
| HPV56 | L2 | 1 | 11 | MVAHRATRRKR | | 45101 |
| HPV56 | L2 | 341 | 8 | NNSFDGLY | | 45102 |
| HPV56 | L2 | 341 | 11 | NNSFDGLYDIY | | 45103 |
| HPV56 | L2 | 342 | 10 | NSFDGLYDIY | | 45104 |
| HPV56 | L2 | 395 | 8 | NVWETPFY | | 45105 |
| HPV56 | L2 | 285 | 11 | PAFTTRRGGVR | | 45106 |
| HPV56 | L2 | 274 | 10 | PDFMNIVALH | | 45107 |
| HPV56 | L2 | 274 | 11 | PDFMNIVALHR | | 45108 |
| HPV56 | L2 | 417 | 8 | PFVPQSPY | | 45109 |
| HPV56 | L2 | 216 | 10 | PGFRRIAAPR | | 45110 |
| HPV56 | L2 | 209 | 11 | PISSTPIPGFR | | 45111 |
| HPV56 | L2 | 392 | 11 | PLGNVWETPFY | | 45112 |
| HPV56 | L2 | 196 | 8 | PMQTFAVH | | 45113 |
| HPV56 | L2 | 369 | 8 | PSAHLPIK | | 45114 |
| HPV56 | L2 | 78 | 11 | PSTIVDVTPAR | | 45115 |
| HPV56 | L2 | 185 | 8 | PTSGIHSY | | 45116 |
| HPV56 | L2 | 441 | 8 | PVYFFRRR | | 45117 |
| HPV56 | L2 | 441 | 9 | PVYFFRRRR | | 45118 |
| HPV56 | L2 | 441 | 10 | PVYFFRRRRR | | 45119 |
| HPV56 | L2 | 441 | 11 | PVYFFRRRRRK | | 45120 |
| HPV56 | L2 | 433 | 11 | QGSSFALWPVY | | 45121 |
| HPV56 | L2 | 312 | 8 | QIGARVHY | | 45122 |
| HPV56 | L2 | 312 | 9 | QIGARVHYY | | 45123 |
| HPV56 | L2 | 312 | 10 | QIGARVHYYY | | 45124 |
| HPV56 | L2 | 421 | 8 | QSPYDVTH | | 45125 |
| HPV56 | L2 | 421 | 11 | QSPYDVTHDVY | | 45126 |
| HPV56 | L2 | 364 | 9 | QSVATPSAH | | 45127 |
| HPV56 | L2 | 306 | 11 | QTRRGTQIGAR | | 45128 |
| HPV56 | L2 | 68 | 10 | RAGYVPLGSR | | 45129 |

TABLE XVII-continued

A11 Motif Peptides

| Type | Protein | Position | No. of Amino Acids | Sequence | A*1101 | Seq. Id. No. |
|---|---|---|---|---|---|---|
| HPV56 | L2 | 11 | 8 | RASATQLY | | 45130 |
| HPV56 | L2 | 11 | 9 | RASATQLYK | | 45131 |
| HPV56 | L2 | 295 | 8 | RFSRLGRK | | 45132 |
| HPV56 | L2 | 291 | 8 | RGGVRFSR | | 45133 |
| HPV56 | L2 | 291 | 11 | RGGVRFSRLGR | | 45134 |
| HPV56 | L2 | 309 | 8 | RGTQIGAR | | 45135 |
| HPV56 | L2 | 309 | 10 | RGTQIGARVH | | 45136 |
| HPV56 | L2 | 309 | 11 | RGTQIGARVHY | | 45137 |
| HPV56 | L2 | 220 | 8 | RIAAPRLY | | 45138 |
| HPV56 | L2 | 220 | 9 | RIAAPRLYR | | 45139 |
| HPV56 | L2 | 220 | 10 | RIAAPRLYRK | | 45140 |
| HPV56 | L2 | 298 | 11 | RLGRKATIQTR | | 45141 |
| HPV56 | L2 | 225 | 11 | RLYRKAFQQVK | | 45142 |
| HPV56 | L2 | 339 | 10 | SANNSFDGLY | | 45143 |
| HPV56 | L2 | 13 | 10 | SATQLYKTCK | | 45144 |
| HPV56 | L2 | 436 | 8 | SFALWPVY | | 45145 |
| HPV56 | L2 | 436 | 11 | SFALWPVYFFR | | 45146 |
| HPV56 | L2 | 343 | 9 | SFDGLYDIY | | 45147 |
| HPV56 | L2 | 24 | 11 | SGTCPEDVVNK | | 45148 |
| HPV56 | L2 | 435 | 9 | SSFALWPVY | | 45149 |
| HPV56 | L2 | 362 | 11 | SSQSVATPSAH | | 45150 |
| HPV56 | L2 | 211 | 9 | SSTPIPGFR | | 45151 |
| HPV56 | L2 | 211 | 10 | SSTPIPGFRR | | 45152 |
| HPV56 | L2 | 147 | 10 | SSTVHVSSTH | | 45153 |
| HPV56 | L2 | 79 | 10 | STIVDVTPAR | | 45154 |
| HPV56 | L2 | 212 | 8 | STPIPGFR | | 45155 |
| HPV56 | L2 | 212 | 9 | STPIPGFRR | | 45156 |
| HPV56 | L2 | 183 | 8 | STPTSGIH | | 45157 |
| HPV56 | L2 | 183 | 10 | STPTSGIHSY | | 45158 |
| HPV56 | L2 | 148 | 9 | STVHVSSTH | | 45159 |
| HPV56 | L2 | 414 | 11 | STWPFVPQSPY | | 45160 |
| HPV56 | L2 | 365 | 8 | SVATPSAH | | 45161 |
| HPV56 | L2 | 26 | 9 | TCPEDVVNK | | 45162 |
| HPV56 | L2 | 237 | 8 | TDPAFLDR | | 45163 |
| HPV56 | L2 | 63 | 9 | TGSGGRAGY | | 45164 |
| HPV56 | L2 | 61 | 8 | TGTGSGGR | | 45165 |
| HPV56 | L2 | 61 | 11 | TGTGSGGRAGY | | 45166 |
| HPV56 | L2 | 80 | 9 | TIVDVTPAR | | 45167 |
| HPV56 | L2 | 146 | 11 | TSSTVHVSSTH | | 45168 |
| HPV56 | L2 | 288 | 8 | TTRRGGVR | | 45169 |
| HPV56 | L2 | 288 | 11 | TTRRGGVRFSR | | 45170 |
| HPV56 | L2 | 149 | 8 | TVHVSSTH | | 45171 |
| HPV56 | L2 | 2 | 8 | VAHRATRR | | 45172 |
| HPV56 | L2 | 2 | 9 | VAHRATRRK | | 45173 |
| HPV56 | L2 | 2 | 10 | VAHRATRRKR | | 45174 |
| HPV56 | L2 | 280 | 11 | VALHRPAFTTR | | 45175 |
| HPV56 | L2 | 366 | 11 | VATPSAHLPIK | | 45176 |
| HPV56 | L2 | 236 | 9 | VTDPAFLDR | | 45177 |
| HPV56 | L2 | 31 | 7 | VVNKIEQK | | 45178 |
| HPV56 | L2 | 424 | 8 | YDVTHDVY | | 45179 |
| HPV56 | L2 | 443 | 8 | YFFRRRRR | | 45180 |
| HPV56 | L2 | 443 | 9 | YFFRRRRRK | | 45181 |
| HPV56 | L2 | 443 | 10 | YFFRRRRRKR | | 45182 |

TABLE XVIII

A24 Motif Peptides

| Type | Protein | Position | No. of Amino Acids | Sequence | A*2402 | Seq. Id. No. |
|---|---|---|---|---|---|---|
| HPV16 | E1 | 240 | 8 | AFGLTPSI | | 45183 |
| HPV16 | E1 | 391 | 11 | AFLKSNSQAKI | | 45184 |
| HPV16 | E1 | 206 | 9 | AMLAKFKEL | | 45185 |
| HPV16 | E1 | 500 | 9 | CFVNSKSHF | | 45186 |
| HPV16 | E1 | 500 | 10 | CFVNSKSHFW | | 45187 |
| HPV16 | E1 | 500 | 11 | CFVNSKSHFWL | | 45188 |
| HPV16 | E1 | 304 | 9 | CMMIEPPKL | | 45189 |
| HPV16 | E1 | 528 | 9 | CWNYIDDNL | | 45190 |
| HPV16 | E1 | 50 | 10 | DFIVNDNDYL | | 45191 |
| HPV16 | E1 | 235 | 9 | DWCIAAFGL | | 45192 |
| HPV16 | E1 | 438 | 8 | DWKQIVMF | | 45193 |

TABLE XVIII-continued

A24 Motif Peptides

| Type | Protein | Position | No. of Amino Acids | Sequence | A*2402 | Seq. Id. No. |
|---|---|---|---|---|---|---|
| HPV16 | E1 | 438 | 9 | DWKQIVMFL | | 45194 |
| HPV16 | E1 | 452 | 9 | EFMSFLTAL | | 45195 |
| HPV16 | E1 | 338 | 9 | EWIQRQTVL | | 45196 |
| HPV16 | E1 | 612 | 9 | FFSRTWSRL | | 45197 |
| HPV16 | E1 | 612 | 11 | FFSRTWSRLSL | | 45198 |
| HPV16 | E1 | 453 | 8 | FMSFLTAL | | 45199 |
| HPV16 | E1 | 453 | 11 | FMSFLTALKRF | | 45200 |
| HPV16 | E1 | 508 | 11 | FWLQPLADAKI | | 45201 |
| HPV16 | E1 | 519 | 11 | GMLDDATVPCW | | 45202 |
| HPV16 | E1 | 487 | 8 | GMSLMKFL | | 45203 |
| HPV16 | E1 | 210 | 10 | KFKELYGVSF | | 45204 |
| HPV16 | E1 | 492 | 8 | KFLQGSVI | | 45205 |
| HPV16 | E1 | 492 | 10 | KFLQGSVICF | | 45206 |
| HPV16 | E1 | 89 | 10 | KYLVSPLSDI | | 45207 |
| HPV16 | E1 | 485 | 9 | LFGMSLMKF | | 45208 |
| HPV16 | E1 | 485 | 10 | LFGMSLMKFL | | 45209 |
| HPV16 | E1 | 490 | 10 | LMKFLQGSVI | | 45210 |
| HPV16 | E1 | 475 | 11 | LYGAANTGKSL | | 45211 |
| HPV16 | E1 | 214 | 9 | LYGVSFSEL | | 45212 |
| HPV16 | E1 | 260 | 8 | LYLHIQSL | | 45213 |
| HPV16 | E1 | 319 | 8 | LYWYKTGI | | 45214 |
| HPV16 | E1 | 319 | 11 | LYWYKTGISNI | | 45215 |
| HPV16 | E1 | 444 | 10 | MFLRYQGVEF | | 45216 |
| HPV16 | E1 | 305 | 8 | MMIEPPKL | | 45217 |
| HPV16 | E1 | 608 | 10 | NWKSFFSRTW | | 45218 |
| HPV16 | E1 | 530 | 11 | NYIDDNLRNAL | | 45219 |
| HPV16 | E1 | 302 | 11 | PMCMMIEPPKL | | 45220 |
| HPV16 | E1 | 577 | 10 | PYLHNRLVVF | | 45221 |
| HPV16 | E1 | 419 | 8 | QMSMSQWI | | 45222 |
| HPV16 | E1 | 359 | 11 | QMVQWAYDNDI | | 45223 |
| HPV16 | E1 | 362 | 8 | QWAYDNDI | | 45224 |
| HPV16 | E1 | 257 | 8 | QYCLYLHI | | 45225 |
| HPV16 | E1 | 257 | 11 | QYCLYLHIQSL | | 45226 |
| HPV16 | E1 | 575 | 9 | RWPYLHNRL | | 45227 |
| HPV16 | E1 | 280 | 11 | RYKCGKNRETI | | 45228 |
| HPV16 | E1 | 447 | 10 | RYQGVEFMSF | | 45229 |
| HPV16 | E1 | 447 | 11 | RYQGVEFMSFL | | 45230 |
| HPV16 | E1 | 611 | 10 | SFFSRTWSRL | | 45231 |
| HPV16 | E1 | 455 | 9 | SFLTALKRF | | 45232 |
| HPV16 | E1 | 455 | 10 | SFLTALKRFL | | 45233 |
| HPV16 | E1 | 349 | 9 | SFNDCTFEL | | 45234 |
| HPV16 | E1 | 218 | 9 | SFSELVRPF | | 45235 |
| HPV16 | E1 | 546 | 9 | SMDVKHRPL | | 45236 |
| HPV16 | E1 | 270 | 8 | SWGMVVLL | | 45237 |
| HPV16 | E1 | 270 | 9 | SWGMVVLLL | | 45238 |
| HPV16 | E1 | 354 | 10 | TFELSQMVQW | | 45239 |
| HPV16 | E1 | 587 | 8 | TFPNEFPF | | 45240 |
| HPV16 | E1 | 585 | 8 | VFTFPNEF | | 45241 |
| HPV16 | E1 | 585 | 10 | VFTFPNEFPF | | 45242 |
| HPV16 | E1 | 443 | 11 | VMFLRYQGVEF | | 45243 |
| HPV16 | E1 | 601 | 9 | VYELNDKNW | | 45244 |
| HPV16 | E1 | 332 | 8 | VYGDTPEW | | 45245 |
| HPV16 | E1 | 332 | 9 | VYGDTPEWI | | 45246 |
| HPV16 | E1 | 321 | 9 | WYKTGISNI | | 45247 |
| HPV16 | E1 | 320 | 10 | YWYKTGISNI | | 45248 |
| HPV16 | E2 | 270 | 10 | AFNSSHKGRI | | 45249 |
| HPV16 | E2 | 31 | 8 | DYWKHMRL | | 45250 |
| HPV16 | E2 | 340 | 8 | EWQRDQFL | | 45251 |
| HPV16 | E2 | 114 | 8 | GYTVEVQF | | 45252 |
| HPV16 | E2 | 35 | 8 | HMRLECAI | | 45253 |
| HPV16 | E2 | 18 | 9 | HYENDSTDL | | 45254 |
| HPV16 | E2 | 130 | 8 | HYTNWTHI | | 45255 |
| HPV16 | E2 | 130 | 10 | HYTNWTHIYI | | 45256 |
| HPV16 | E2 | 82 | 11 | IYNSQYSNEKW | | 45257 |
| HPV16 | E2 | 42 | 10 | IYYKAREMGF | | 45258 |
| HPV16 | E2 | 91 | 9 | KWTLQDVSL | | 45259 |
| HPV16 | E2 | 177 | 8 | KYSKNKVW | | 45260 |
| HPV16 | E2 | 311 | 9 | LYTAVSSTW | | 45261 |
| HPV16 | E2 | 311 | 11 | LYTAVSSTWHW | | 45262 |
| HPV16 | E2 | 157 | 8 | LYYVHEGI | | 45263 |
| HPV16 | E2 | 345 | 8 | QFLSQVKI | | 45264 |
| HPV16 | E2 | 86 | 9 | QYSNEKWTL | | 45265 |
| HPV16 | E2 | 304 | 8 | RFKKHCTL | | 45266 |
| HPV16 | E2 | 302 | 10 | RYRFKKHCTL | | 45267 |

TABLE XVIII-continued

A24 Motif Peptides

| Type | Protein | Position | No. of Amino Acids | Sequence | A*2402 | Seq. Id. No. |
|---|---|---|---|---|---|---|
| HPV16 | E2 | 128 | 10 | TMHYTNWTHI | | 45268 |
| HPV16 | E2 | 336 | 11 | TYDSEWQRDQF | | 45269 |
| HPV16 | E2 | 183 | 11 | VWEVHAGGQVI | | 45270 |
| HPV16 | E2 | 101 | 10 | VYLTAPTGCI | | 45271 |
| HPV16 | E2 | 32 | 11 | YWKHMRLECAI | | 45272 |
| HPV16 | E2 | 154 | 11 | YYGLYYVHEGI | | 45273 |
| HPV16 | E2 | 43 | 9 | YYKAREMGF | | 45274 |
| HPV16 | E2 | 158 | 11 | YYVHEGIRTYF | | 45275 |
| HPV16 | E5 | 56 | 9 | AFRCFIVYI | | 45276 |
| HPV16 | E5 | 56 | 10 | AFRCFIVYII | | 45277 |
| HPV16 | E5 | 56 | 11 | AFRCFIVYIIF | | 45278 |
| HPV16 | E5 | 18 | 10 | CFCVLLCVCL | | 45279 |
| HPV16 | E5 | 18 | 11 | CFCVLLCVCLL | | 45280 |
| HPV16 | E5 | 59 | 8 | CFIVYIIF | | 45281 |
| HPV16 | E5 | 59 | 11 | CFIVYIIFVYI | | 45282 |
| HPV16 | E5 | 14 | 9 | CFLLCFCVL | | 45283 |
| HPV16 | E5 | 14 | 10 | CFLLCFCVLL | | 45284 |
| HPV16 | E5 | 65 | 8 | IFVYIPLF | | 45285 |
| HPV16 | E5 | 65 | 9 | IFVYIPLFL | | 45286 |
| HPV16 | E5 | 65 | 10 | IFVYIPLFLI | | 45287 |
| HPV16 | E5 | 71 | 10 | LFLIHTHARF | | 45288 |
| HPV16 | E5 | 71 | 11 | LFLIHTHARFL | | 45289 |
| HPV16 | E5 | 49 | 9 | LWITAASAF | | 45290 |
| HPV16 | E5 | 38 | 8 | TYTSLIIL | | 45291 |
| HPV16 | E5 | 38 | 10 | TYTSLIILVL | | 45292 |
| HPV16 | E5 | 38 | 11 | TYTSLIILVLL | | 45293 |
| HPV16 | E5 | 62 | 8 | VYIIFVYI | | 45294 |
| HPV16 | E5 | 62 | 10 | VYIIFVYIPL | | 45295 |
| HPV16 | E5 | 62 | 11 | VYIIFVYIPLF | | 45296 |
| HPV16 | E5 | 67 | 8 | VYIPLFLI | | 45297 |
| HPV16 | E6 | 87 | 9 | CYSLYGTTL | 0.0460 | 45298 |
| HPV16 | E6 | 51 | 9 | DFAFRDLCI | 0.0003 | 45299 |
| HPV16 | E6 | 82 | 9 | EYRHYCYSL | 0.0051 | 45300 |
| HPV16 | E6 | 85 | 11 | HYCYSLYGTTL | 0.0650 | 45301 |
| HPV16 | E6 | 66 | 9 | PYAVCDKCL | 0.0078 | 45302 |
| HPV16 | E6 | 66 | 11 | PYAVCDKCLKF | 0.1100 | 45303 |
| HPV16 | E6 | 98 | 9 | QYNKPLCDL | 0.0001 | 45304 |
| HPV16 | E6 | 98 | 10 | QYNKPLCDLL | 0.0015 | 45305 |
| HPV16 | E6 | 98 | 11 | QYNKPLCDLLI | | 45306 |
| HPV16 | E6 | 131 | 9 | RFHNIRGRW | 0.0220 | 45307 |
| HPV16 | E6 | 38 | 8 | VYCKQQLL | 0.0069 | 45308 |
| HPV16 | E6 | 49 | 9 | VYDFAFRDL | 0.0150 | 45309 |
| HPV16 | E6 | 49 | 11 | VYDFAFRDLCI | | 45310 |
| HPV16 | E7 | 83 | 11 | LMGTLGIVCPI | | 45311 |
| HPV16 | E7 | 56 | 10 | TFCCKCDSTL | | 45312 |
| HPV16 | L1 | 13 | 11 | CYENDVNVYHI | | 45313 |
| HPV16 | L1 | 176 | 9 | DYKQTQLCL | | 45314 |
| HPV16 | L1 | 176 | 10 | DYKQTQLCLI | | 45315 |
| HPV16 | L1 | 395 | 8 | EYDLQFIF | | 45316 |
| HPV16 | L1 | 395 | 10 | EYDLQFIFQL | | 45317 |
| HPV16 | L1 | 388 | 11 | EYLRHGEEYDL | | 45318 |
| HPV16 | L1 | 52 | 8 | EYVARTNI | | 45319 |
| HPV16 | L1 | 24 | 8 | FFQMSLWL | | 45320 |
| HPV16 | L1 | 273 | 10 | FFYLRREQMF | | 45321 |
| HPV16 | L1 | 472 | 10 | FWEVNLKEKF | | 45322 |
| HPV16 | L1 | 274 | 9 | FYLRREQMF | | 45323 |
| HPV16 | L1 | 116 | 9 | FYNPDTQRL | | 45324 |
| HPV16 | L1 | 116 | 11 | FYNPDTQRLVW | | 45325 |
| HPV16 | L1 | 230 | 10 | GFGAMDFTTL | | 45326 |
| HPV16 | L1 | 23 | 8 | IFFQMSLW | | 45327 |
| HPV16 | L1 | 23 | 9 | IFFQMSLWL | | 45328 |
| HPV16 | L1 | 332 | 8 | IFNKPYWL | | 45329 |
| HPV16 | L1 | 401 | 9 | IFQLCKITL | | 45330 |
| HPV16 | L1 | 59 | 10 | IYYHAGTSRL | | 45331 |
| HPV16 | L1 | 59 | 11 | IYYHAGTSRLL | | 45332 |
| HPV16 | L1 | 108 | 9 | KFGFPDTSF | | 45333 |
| HPV16 | L1 | 493 | 8 | KFLLQAGL | | 45334 |
| HPV16 | L1 | 480 | 9 | KFSADLDQF | | 45335 |
| HPV16 | L1 | 480 | 11 | KFSADLDQFPL | | 45336 |
| HPV16 | L1 | 262 | 11 | KMVSEPYGDSL | | 45337 |
| HPV16 | L1 | 469 | 9 | KYTFWEVNL | | 45338 |
| HPV16 | L1 | 272 | 11 | LFFYLRREQMF | | 45339 |
| HPV16 | L1 | 29 | 11 | LWLPSEATVYL | | 45340 |
| HPV16 | L1 | 367 | 8 | NMSLCAAI | | 45341 |

TABLE XVIII-continued

A24 Motif Peptides

| Type | Protein | Position | No. of Amino Acids | Sequence | A*2402 | Seq. Id. No. |
|---|---|---|---|---|---|---|
| HPV16 | L1 | 267 | 8 | PYGDSLFF | | 45342 |
| HPV16 | L1 | 267 | 10 | PYGDSLFFYL | | 45343 |
| HPV16 | L1 | 399 | 9 | QFIFQLCKI | | 45344 |
| HPV16 | L1 | 399 | 11 | QFIFQLCKITL | | 45345 |
| HPV16 | L1 | 487 | 8 | QFPLGRKF | | 45346 |
| HPV16 | L1 | 487 | 9 | QFPLGRKFL | | 45347 |
| HPV16 | L1 | 487 | 10 | QFPLGRKFLL | | 45348 |
| HPV16 | L1 | 280 | 8 | QMFVRHLF | | 45349 |
| HPV16 | L1 | 95 | 9 | QYRVFRIHL | | 45350 |
| HPV16 | L1 | 445 | 8 | RFVTSQAI | | 45351 |
| HPV16 | L1 | 115 | 10 | SFYNPDTQRL | | 45352 |
| HPV16 | L1 | 174 | 9 | SMDYKQTQL | | 45353 |
| HPV16 | L1 | 174 | 11 | SMDYKQTQLCL | | 45354 |
| HPV16 | L1 | 419 | 10 | SMNSTILEDW | | 45355 |
| HPV16 | L1 | 324 | 9 | SMVTSDAQI | | 45356 |
| HPV16 | L1 | 324 | 10 | SMVTSDAQIF | | 45357 |
| HPV16 | L1 | 4 | 8 | TFIYILVI | | 45358 |
| HPV16 | L1 | 471 | 11 | TFWEVNLKEKF | | 45359 |
| HPV16 | L1 | 415 | 10 | TYIHSMNSTI | | 45360 |
| HPV16 | L1 | 415 | 11 | TYIHSMNSTIL | | 45361 |
| HPV16 | L1 | 380 | 11 | TYKNTNFKEYL | | 45362 |
| HPV16 | L1 | 443 | 10 | TYRFVTSQAI | | 45363 |
| HPV16 | L1 | 20 | 10 | VYHIFFQMSL | | 45364 |
| HPV16 | L1 | 20 | 11 | VYHIFFQMSLW | | 45365 |
| HPV16 | L1 | 60 | 9 | YYHAGTSRL | | 45366 |
| HPV16 | L1 | 60 | 10 | YYHAGTSRLL | | 45367 |
| HPV16 | L2 | 241 | 9 | AFITTPTKL | | 45368 |
| HPV16 | L2 | 241 | 10 | AFITTPTKLI | | 45369 |
| HPV16 | L2 | 256 | 11 | AYEGIDVDNTL | | 45370 |
| HPV16 | L2 | 282 | 8 | DFLDIVAL | | 45371 |
| HPV16 | L2 | 329 | 11 | DFSTIDSAEEI | | 45372 |
| HPV16 | L2 | 445 | 11 | DFYLHPSYYML | | 45373 |
| HPV16 | L2 | 446 | 10 | FYLHPSYYML | | 45374 |
| HPV16 | L2 | 392 | 9 | GYIPANTTI | | 45375 |
| HPV16 | L2 | 392 | 11 | GYIPANTTIPF | | 45376 |
| HPV16 | L2 | 180 | 9 | HFTLSSSTI | | 45377 |
| HPV16 | L2 | 325 | 9 | HYYYDFSTI | | 45378 |
| HPV16 | L2 | 365 | 9 | LYDIYADDF | | 45379 |
| HPV16 | L2 | 365 | 10 | LYDIYADDFI | | 45380 |
| HPV16 | L2 | 266 | 10 | LYFSSNDNSI | | 45381 |
| HPV16 | L2 | 192 | 10 | NYEEIPMDTF | | 45382 |
| HPV16 | L2 | 192 | 11 | NYEEIPMDTFI | | 45383 |
| HPV16 | L2 | 401 | 8 | PFGGAYNI | | 45384 |
| HPV16 | L2 | 401 | 10 | PFGGAYNIPL | | 45385 |
| HPV16 | L2 | 463 | 9 | PYFFSDVSL | | 45386 |
| HPV16 | L2 | 47 | 8 | QYGSMGVF | | 45387 |
| HPV16 | L2 | 47 | 9 | QYGSMGVFF | | 45388 |
| HPV16 | L2 | 436 | 11 | QYTIIADAGDF | | 45389 |
| HPV16 | L2 | 302 | 11 | RYSRIGNKQTL | | 45390 |
| HPV16 | L2 | 50 | 9 | SMGVFFGGL | | 45391 |
| HPV16 | L2 | 50 | 11 | SMGVFFGGLGI | | 45392 |
| HPV16 | L2 | 162 | 8 | TFTDPSVL | | 45393 |
| HPV16 | L2 | 251 | 10 | TYDNPAYEGI | | 45394 |
| HPV16 | L2 | 348 | 10 | TYTTSHAAL | | 45395 |
| HPV16 | L2 | 53 | 8 | VFFGGLGI | | 45396 |
| HPV16 | L2 | 464 | 8 | YFFSDVSL | | 45397 |
| HPV16 | L2 | 267 | 9 | YFSSNDNSI | | 45398 |
| HPV16 | L2 | 267 | 11 | YFSSNDNSINI | | 45399 |
| HPV16 | L2 | 453 | 10 | YMLRKRRKRL | | 45400 |
| HPV16 | L2 | 452 | 11 | YYMLRKRRKRL | | 45401 |
| HPV16 | L2 | 326 | 8 | YYYDFSTI | | 45402 |
| HPV18 | E1 | 526 | 11 | AMLDDATTTCW | | 45403 |
| HPV18 | E1 | 618 | 10 | CFFERTWSRL | | 45404 |
| HPV18 | E1 | 311 | 9 | CMLIQPPKL | | 45405 |
| HPV18 | E1 | 49 | 9 | DFIDTQGTF | | 45406 |
| HPV18 | E1 | 381 | 8 | DMAFEYAL | | 45407 |
| HPV18 | E1 | 381 | 9 | DMAFEYALL | | 45408 |
| HPV18 | E1 | 445 | 8 | DWRPIVQF | | 45409 |
| HPV18 | E1 | 445 | 9 | DWRPIVQFL | | 45410 |
| HPV18 | E1 | 459 | 9 | EFITFLGAL | | 45411 |
| HPV18 | E1 | 594 | 8 | EFPNAFPF | | 45412 |
| HPV18 | E1 | 366 | 11 | EMVQWAFDNEL | | 45413 |
| HPV18 | E1 | 345 | 8 | EWIQRLTI | | 45414 |
| HPV18 | E1 | 345 | 9 | EWIQRLTII | | 45415 |

TABLE XVIII-continued

A24 Motif Peptides

| Type | Protein | Position | No. of Amino Acids | Sequence | A*2402 | Seq. Id. No. |
|---|---|---|---|---|---|---|
| HPV18 | E1 | 619 | 9 | FFERTWSRL | | 45416 |
| HPV18 | E1 | 619 | 11 | FFERTWSRLDL | | 45417 |
| HPV18 | E1 | 257 | 9 | GFKTLIQPF | | 45418 |
| HPV18 | E1 | 257 | 10 | GFKTLIQPFI | | 45419 |
| HPV18 | E1 | 257 | 11 | GFKTLIQPFIL | | 45420 |
| HPV18 | E1 | 494 | 8 | GMSFIHFI | | 45421 |
| HPV18 | E1 | 16 | 8 | GWFYVQAI | | 45422 |
| HPV18 | E1 | 499 | 8 | HFIQGAVI | | 45423 |
| HPV18 | E1 | 499 | 10 | HFIQGAVISF | | 45424 |
| HPV18 | E1 | 247 | 8 | IFGVNPTI | | 45425 |
| HPV18 | E1 | 277 | 9 | KWGVLILAL | | 45426 |
| HPV18 | E1 | 277 | 10 | KWGVLILALL | | 45427 |
| HPV18 | E1 | 267 | 8 | LYAHIQCL | | 45428 |
| HPV18 | E1 | 326 | 8 | LYWYRTGI | | 45429 |
| HPV18 | E1 | 326 | 11 | LYWYRTGISNI | | 45430 |
| HPV18 | E1 | 361 | 10 | NFDLSEMVQW | | 45431 |
| HPV18 | E1 | 428 | 8 | NMSQWIRF | | 45432 |
| HPV18 | E1 | 615 | 10 | NWKCFFERTW | | 45433 |
| HPV18 | E1 | 264 | 8 | PFILYAHI | | 45434 |
| HPV18 | E1 | 264 | 11 | PFILYAHIQCL | | 45435 |
| HPV18 | E1 | 584 | 10 | PYLESRITVF | | 45436 |
| HPV18 | E1 | 451 | 8 | QFLRYQQI | | 45437 |
| HPV18 | E1 | 451 | 10 | QFLRYQQIEF | | 45438 |
| HPV18 | E1 | 451 | 11 | QFLRYQQIEFI | | 45439 |
| HPV18 | E1 | 426 | 8 | QMNSQWI | | 45440 |
| HPV18 | E1 | 426 | 10 | QMNSQWIRF | | 45441 |
| HPV18 | E1 | 369 | 8 | QWAFDNEL | | 45442 |
| HPV18 | E1 | 431 | 10 | QWIRFCSKI | | 45443 |
| HPV18 | E1 | 582 | 9 | RWPYLESRI | | 45444 |
| HPV18 | E1 | 287 | 9 | RYKCGKSRL | | 45445 |
| HPV18 | E1 | 454 | 8 | RYQQIEFI | | 45446 |
| HPV18 | E1 | 454 | 10 | RYQQIEFITF | | 45447 |
| HPV18 | E1 | 454 | 11 | RYQQIEFITFL | | 45448 |
| HPV18 | E1 | 496 | 11 | SFIHFIQGAVI | | 45449 |
| HPV18 | E1 | 225 | 9 | SFTDLVRNF | | 45450 |
| HPV18 | E1 | 507 | 9 | SFVNSTSHF | | 45451 |
| HPV18 | E1 | 507 | 10 | SFVNSTSHFW | | 45452 |
| HPV18 | E1 | 507 | 11 | SFVNSTSHFWL | | 45453 |
| HPV18 | E1 | 491 | 8 | SYFGMSFI | | 45454 |
| HPV18 | E1 | 491 | 10 | SYFGMSFIHF | | 45455 |
| HPV18 | E1 | 491 | 11 | SYFGMSFIHFI | | 45456 |
| HPV18 | E1 | 56 | 8 | TFCEQAEL | | 45457 |
| HPV18 | E1 | 462 | 9 | TFLGALKSF | | 45458 |
| HPV18 | E1 | 462 | 10 | TFLGALKSFL | | 45459 |
| HPV18 | E1 | 537 | 11 | TYFDTYMRNAL | | 45460 |
| HPV18 | E1 | 221 | 9 | TYGLSFTDL | | 45461 |
| HPV18 | E1 | 592 | 8 | VFEFPNAF | | 45462 |
| HPV18 | E1 | 592 | 10 | VFEFPNAFPF | | 45463 |
| HPV18 | E1 | 217 | 8 | VFKDTYGL | | 45464 |
| HPV18 | E1 | 217 | 10 | VFKDTYGLSF | | 45465 |
| HPV18 | E1 | 339 | 8 | VMGDTPEW | | 45466 |
| HPV18 | E1 | 339 | 9 | VMGDTPEWI | | 45467 |
| HPV18 | E1 | 608 | 9 | VYEINDKNW | | 45468 |
| HPV18 | E1 | 328 | 9 | WYRTGISNI | | 45469 |
| HPV18 | E1 | 538 | 10 | YFDTYMRNAL | | 45470 |
| HPV18 | E1 | 492 | 9 | YFGMSFIHF | | 45471 |
| HPV18 | E1 | 492 | 10 | YFGMSFIHFI | | 45472 |
| HPV18 | E1 | 542 | 11 | YMRNALDGNPI | | 45473 |
| HPV18 | E1 | 327 | 10 | YWYRTGISNI | | 45474 |
| HPV18 | E2 | 95 | 11 | DWTLQDTCEEL | | 45475 |
| HPV18 | E2 | 47 | 9 | FFAAREHGI | | 45476 |
| HPV18 | E2 | 168 | 9 | GYNTFYIEF | | 45477 |
| HPV18 | E2 | 22 | 9 | HYENDSKDI | | 45478 |
| HPV18 | E2 | 312 | 9 | HYRDISSTW | | 45479 |
| HPV18 | E2 | 312 | 11 | HYRDISSTWHW | | 45480 |
| HPV18 | E2 | 46 | 10 | IFFAAREHGI | | 45481 |
| HPV18 | E2 | 345 | 8 | KFLNTVAI | | 45482 |
| HPV18 | E2 | 182 | 8 | KYGNTGTW | | 45483 |
| HPV18 | E2 | 105 | 10 | LWNTEPTHCF | | 45484 |
| HPV18 | E2 | 162 | 11 | LYYVKEGYNTF | | 45485 |
| HPV18 | E2 | 35 | 8 | QYWQLIRW | | 45486 |
| HPV18 | E2 | 41 | 8 | RWENAIFF | | 45487 |
| HPV18 | E2 | 90 | 9 | RYKTEDWTL | | 45488 |
| HPV18 | E2 | 188 | 11 | TWEVHFGNNVI | | 45489 |

TABLE XVIII-continued

A24 Motif Peptides

| Type | Protein | Position | No. of Amino Acids | Sequence | A*2402 | Seq. Id. No. |
|---|---|---|---|---|---|---|
| HPV18 | E2 | 336 | 11 | TYHSETQRTKF | | 45490 |
| HPV18 | E2 | 141 | 10 | VYYMTDAGTW | | 45491 |
| HPV18 | E2 | 143 | 8 | YMTDAGTW | | 45492 |
| HPV18 | E2 | 36 | 11 | YWQLIRWENAI | | 45493 |
| HPV18 | E2 | 142 | 9 | YYMTDAGTW | | 45494 |
| HPV18 | E2 | 163 | 10 | YYVKEGYNTF | | 45495 |
| HPV18 | E5 | 49 | 9 | AFTVYVFCF | | 45496 |
| HPV18 | E5 | 49 | 10 | AFTVYVFCFL | | 45497 |
| HPV18 | E5 | 49 | 11 | AFTVYVFCFLL | | 45498 |
| HPV18 | E5 | 32 | 9 | AWVLVFVYI | | 45499 |
| HPV18 | E5 | 30 | 8 | AYAWVLVF | | 45500 |
| HPV18 | E5 | 30 | 11 | AYAWVLVFVYI | | 45501 |
| HPV18 | E5 | 56 | 8 | CFLLPMLL | | 45502 |
| HPV18 | E5 | 56 | 9 | CFLLPMLLL | | 45503 |
| HPV18 | E5 | 56 | 11 | CFLLPMLLLHI | | 45504 |
| HPV18 | E5 | 27 | 9 | CMCAYAWVL | | 45505 |
| HPV18 | E5 | 27 | 11 | CMCAYAWVLVF | | 45506 |
| HPV18 | E5 | 13 | 10 | CMYVCCHVPL | | 45507 |
| HPV18 | E5 | 13 | 11 | CMYVCCHVPLL | | 45508 |
| HPV18 | E5 | 14 | 9 | MYVCCHVPL | | 45509 |
| HPV18 | E5 | 14 | 10 | MYVCCHVPLL | | 45510 |
| HPV18 | E5 | 60 | 10 | PMLLLHIHAI | | 45511 |
| HPV18 | E5 | 60 | 11 | PMLLLHIHAIL | | 45512 |
| HPV18 | E5 | 54 | 9 | VFCFLLPML | | 45513 |
| HPV18 | E5 | 54 | 10 | VFCFLLPMLL | | 45514 |
| HPV18 | E5 | 54 | 11 | VFCFLLPMLLL | | 45515 |
| HPV18 | E5 | 36 | 8 | VFVYIVVI | | 45516 |
| HPV18 | E5 | 52 | 8 | VYVFCLL | | 45517 |
| HPV18 | E5 | 52 | 11 | VYVFCFLLPML | | 45518 |
| HPV18 | E6 | 70 | 9 | DFYSRIREL | | 45519 |
| HPV18 | E6 | 46 | 8 | EFAFKDLF | | 45520 |
| HPV18 | E6 | 71 | 8 | FYSRIREL | 0.0260 | 45521 |
| HPV18 | E6 | 80 | 11 | HYSDSVYGDTL | 0.0069 | 45522 |
| HPV18 | E6 | 52 | 9 | LFVVYRDSI | | 45523 |
| HPV18 | E6 | 98 | 9 | LYNLLIRCL | 0.0001 | 45524 |
| HPV18 | E6 | 11 | 11 | PYKLPDLCTEL | 0.0064 | 45525 |
| HPV18 | E6 | 44 | 9 | VFEFAFKDL | | 45526 |
| HPV18 | E6 | 44 | 10 | VFEFAFKDLF | 0.0360 | 45527 |
| HPV18 | E6 | 33 | 9 | VYCKTVLEL | 0.0220 | 45528 |
| HPV18 | E6 | 85 | 9 | VYGDTLEKL | 0.0150 | 45529 |
| HPV18 | E7 | 85 | 10 | AFQQLFLNTL | | 45530 |
| HPV18 | E7 | 63 | 10 | CMCCKCEARI | 0.0001 | 45531 |
| HPV18 | E7 | 89 | 8 | LFLNTLSF | | 45532 |
| HPV18 | L1 | 128 | 11 | AYQYRVFRVQL | | 45533 |
| HPV18 | L1 | 211 | 9 | DYKQTQLCI | | 45534 |
| HPV18 | L1 | 211 | 10 | DYKQTQLCIL | | 45535 |
| HPV18 | L1 | 87 | 8 | DYVTPTSI | | 45536 |
| HPV18 | L1 | 87 | 9 | DYVTPTSIF | | 45537 |
| HPV18 | L1 | 431 | 8 | EYDLQFIF | | 45538 |
| HPV18 | L1 | 431 | 10 | EYDLQFIFQL | | 45539 |
| HPV18 | L1 | 308 | 9 | FFCLRREQL | | 45540 |
| HPV18 | L1 | 308 | 10 | FFCLRREQLF | | 45541 |
| HPV18 | L1 | 508 | 10 | FWNVDLKEKF | | 45542 |
| HPV18 | L1 | 95 | 9 | FYHAGSSRL | | 45543 |
| HPV18 | L1 | 95 | 10 | FYHAGSSRLL | | 45544 |
| HPV18 | L1 | 265 | 10 | GYGAMDFSTL | | 45545 |
| HPV18 | L1 | 11 | 11 | HYHLLPLYGPL | | 45546 |
| HPV18 | L1 | 58 | 8 | IFLQMALW | | 45547 |
| HPV18 | L1 | 437 | 9 | IFQLCTITL | | 45548 |
| HPV18 | L1 | 94 | 10 | IFYHAGSSRL | | 45549 |
| HPV18 | L1 | 94 | 11 | IFYHAGSSRLL | | 45550 |
| HPV18 | L1 | 151 | 9 | IYNPETQRL | | 45551 |
| HPV18 | L1 | 151 | 11 | IYNPETQRLVW | | 45552 |
| HPV18 | L1 | 143 | 9 | KFGLPDTSI | | 45553 |
| HPV18 | L1 | 529 | 8 | KFLVQAGL | | 45554 |
| HPV18 | L1 | 516 | 11 | KFSLDLDQYPL | | 45555 |
| HPV18 | L1 | 507 | 11 | KFWNVDLKEKF | | 45556 |
| HPV18 | L1 | 48 | 9 | LFLRNVNVF | | 45557 |
| HPV18 | L1 | 48 | 11 | LFLRNVNVFPI | | 45558 |
| HPV18 | L1 | 367 | 8 | LFNKPYWL | | 45559 |
| HPV18 | L1 | 64 | 11 | LWRPSDNTVYL | | 45560 |
| HPV18 | L1 | 17 | 11 | LYGPLYHPRPL | | 45561 |
| HPV18 | L1 | 21 | 9 | LYHPRPLPL | | 45562 |
| HPV18 | L1 | 3 | 8 | LYTRVLIL | | 45563 |

TABLE XVIII-continued

A24 Motif Peptides

| Type | Protein | Position | No. of Amino Acids | Sequence | A*2402 | Seq. Id. No. |
|---|---|---|---|---|---|---|
| HPV18 | L1 | 307 | 10 | MFFCLRREQL | | 45564 |
| HPV18 | L1 | 307 | 11 | MFFCLRREQLF | | 45565 |
| HPV18 | L1 | 502 | 8 | PYDKLKFW | | 45566 |
| HPV18 | L1 | 302 | 8 | PYGDSMFF | | 45567 |
| HPV18 | L1 | 302 | 10 | PYGDSMFFCL | | 45568 |
| HPV18 | L1 | 435 | 9 | QFIFQLCTI | | 45569 |
| HPV18 | L1 | 435 | 11 | QFIFQLCTITL | | 45570 |
| HPV18 | L1 | 523 | 8 | QYPLGRKF | | 45571 |
| HPV18 | L1 | 523 | 9 | QYPLGRKFL | | 45572 |
| HPV18 | L1 | 130 | 9 | QYRVFRVQL | | 45573 |
| HPV18 | L1 | 424 | 11 | QYSRHVEEYDL | | 45574 |
| HPV18 | L1 | 481 | 8 | RFVQSVAI | | 45575 |
| HPV18 | L1 | 306 | 11 | SMFFCLRREQL | | 45576 |
| HPV18 | L1 | 455 | 10 | SMNSSILEDW | | 45577 |
| HPVIS | L1 | 451 | 10 | SYIHSMNSSI | | 45578 |
| HPV18 | L1 | 451 | 11 | SYIHSMNSSIL | | 45579 |
| HPV18 | L1 | 327 | 10 | TMGDTVPQSL | | 45580 |
| HPV18 | L1 | 479 | 10 | TYRFVQSVAI | | 45581 |
| HPV18 | L1 | 55 | 10 | VFPIFLQMAL | | 45582 |
| HPV18 | L1 | 55 | 11 | VFPIFLQMALW | | 45583 |
| HPV18 | L1 | 160 | 9 | VWACAGVEI | | 45584 |
| HPV18 | L1 | 34 | 8 | VYMVHIII | | 45585 |
| HPV18 | L1 | 351 | 10 | VYSPSPSGSI | | 45586 |
| HPV18 | L2 | 255 | 9 | AFEPVDTTL | | 45587 |
| HPV18 | L2 | 255 | 11 | AFEPVDTTLTF | | 45588 |
| HPV18 | L2 | 370 | 9 | AFFKYSPTI | | 45589 |
| HPV18 | L2 | 161 | 8 | AFSDPSII | | 45590 |
| HPV18 | L2 | 275 | 8 | DFMDIIRL | | 45591 |
| HPV18 | L2 | 240 | 9 | EFLTRPSSL | | 45592 |
| HPV18 | L2 | 240 | 10 | EFLTRPSSLI | | 45593 |
| HPV18 | L2 | 331 | 8 | EYIELQPL | | 45594 |
| HPV18 | L2 | 371 | 8 | FFKYSPTI | | 45595 |
| HPV18 | L2 | 319 | 8 | FYHDISPI | | 45596 |
| HPV18 | L2 | 191 | 10 | GYEEIPLQTF | | 45597 |
| HPV18 | L2 | 318 | 9 | HFYHDISPI | | 45598 |
| HPV18 | L2 | 434 | 10 | HYYLWPLYYF | | 45599 |
| HPV18 | L2 | 434 | 11 | HYYLWPLYYFI | | 45600 |
| HPV18 | L2 | 52 | 8 | IFLGGLGI | | 45601 |
| HPV18 | L2 | 437 | 8 | LWPLYYFI | | 45602 |
| HPV18 | L2 | 305 | 9 | MFTRSGTQI | | 45603 |
| HPV18 | L2 | 452 | 8 | PYFFADGF | | 45604 |
| HPV18 | L2 | 46 | 8 | QWSSLGIF | | 45605 |
| HPV18 | L2 | 46 | 9 | QWSSLGIFL | | 45606 |
| HPV18 | L2 | 368 | 11 | SFAFFKYSPTI | | 45607 |
| HPV18 | L2 | 383 | 9 | SYSNVTVPL | | 45608 |
| HPV18 | L2 | 121 | 8 | TFTGTSGF | | 45609 |
| HPV18 | L2 | 121 | 10 | TFTGTSGFDI | | 45610 |
| HPV18 | L2 | 304 | 10 | TMFTRSGTQI | | 45611 |
| HPV18 | L2 | 399 | 9 | VYTGPDITL | | 45612 |
| HPV18 | L2 | 435 | 9 | YYLWPLYYF | | 45613 |
| HPV18 | L2 | 435 | 10 | YYLWPLYYFI | | 45614 |
| HPV31 | E1 | 371 | 11 | AFLKSNSQAKI | | 45615 |
| HPV31 | E1 | 186 | 9 | AMLGKFKEL | | 45616 |
| HPV31 | E1 | 284 | 9 | CMLIQPPKL | | 45617 |
| HPV31 | E1 | 508 | 9 | CWHYIDNYL | | 45618 |
| HPV31 | E1 | 418 | 8 | DWRDIVKF | | 45619 |
| HPV31 | E1 | 418 | 9 | DWRDIVKFL | | 45620 |
| HPV31 | E1 | 102 | 8 | DYNISPRL | | 45621 |
| HPV31 | E1 | 102 | 11 | DYNISPRLKAI | | 45622 |
| HPV31 | E1 | 432 | 9 | EFVSFLSAL | | 45623 |
| HPV31 | E1 | 432 | 11 | EFVSFLSALKL | | 45624 |
| HPV31 | E1 | 318 | 9 | EWIERQTVL | | 45625 |
| HPV31 | E1 | 592 | 9 | FFSRTWCRL | | 45626 |
| HPV31 | E1 | 592 | 11 | FFSRTWCRLNL | | 45627 |
| HPV31 | E1 | 199 | 8 | FMELIRPF | | 45628 |
| HPV31 | E1 | 488 | 11 | FWLQPLADAKI | | 45629 |
| HPV31 | E1 | 230 | 11 | GFKTLLQPYCL | | 45630 |
| HPV31 | E1 | 499 | 11 | GMLDDATTPCW | | 45631 |
| HPV31 | E1 | 467 | 8 | GMSLISFL | | 45632 |
| HPV31 | E1 | 252 | 10 | GMVMLMLVRF | | 45633 |
| HPV31 | E1 | 16 | 9 | GWFYVEAVI | | 45634 |
| HPV31 | E1 | 510 | 11 | HYIDNYLRNAL | | 45635 |
| HPV31 | E1 | 190 | 10 | KFKELYGVSF | | 45636 |
| HPV31 | E1 | 424 | 8 | KFLRYQQI | | 45637 |

TABLE XVIII-continued

A24 Motif Peptides

| Type | Protein | Position | No. of Amino Acids | Sequence | A*2402 | Seq. Id. No. |
|---|---|---|---|---|---|---|
| HPV31 | E1 | 424 | 10 | KFLRYQQIEF | | 45638 |
| HPV31 | E1 | 88 | 10 | KYVGSPLSDI | | 45639 |
| HPV31 | E1 | 534 | 9 | LMQLKCPPL | | 45640 |
| HPV31 | E1 | 534 | 10 | LMQLKCPPLL | | 45641 |
| HPV31 | E1 | 534 | 11 | LMQLKCPPLLI | | 45642 |
| HPV31 | E1 | 240 | 8 | LYCHLQSL | | 45643 |
| HPV31 | E1 | 194 | 9 | LYGVSFMEL | | 45644 |
| HPV31 | E1 | 194 | 10 | LYGVSFMELI | | 45645 |
| HPV31 | E1 | 299 | 11 | LYWYRTGMSNI | | 45646 |
| HPV31 | E1 | 588 | 10 | NWKSFFSRTW | | 45647 |
| HPV31 | E1 | 237 | 8 | PYCLYCHL | | 45648 |
| HPV31 | E1 | 237 | 11 | PYCLYCHLQSL | | 45649 |
| HPV31 | E1 | 557 | 10 | PYLHSRLVVF | | 45650 |
| HPV31 | E1 | 399 | 8 | QMSMGQWI | | 45651 |
| HPV31 | E1 | 260 | 9 | RFKCAKNRI | | 45652 |
| HPV31 | E1 | 260 | 11 | RFKCAKNRITI | | 45653 |
| HPV31 | E1 | 555 | 9 | RWPYLHSRL | | 45654 |
| HPV31 | E1 | 427 | 10 | RYQQIEFVSF | | 45655 |
| HPV31 | E1 | 427 | 11 | RYQQIEFVSFL | | 45656 |
| HPV31 | E1 | 591 | 10 | SFFSRTWCRL | | 45657 |
| HPV31 | E1 | 472 | 8 | SFLQGCII | | 45658 |
| HPV31 | E1 | 435 | 8 | SPLSALKL | | 45659 |
| HPV31 | E1 | 435 | 9 | SFLSALKLF | | 45660 |
| HPV31 | E1 | 435 | 10 | SFLSALKLFL | | 45661 |
| HPV31 | E1 | 198 | 9 | SFMELIRPF | | 45662 |
| HPV31 | E1 | 329 | 9 | SFNDTTFDL | | 45663 |
| HPV31 | E1 | 250 | 9 | SWGMVMLML | | 45664 |
| HPV31 | E1 | 480 | 9 | SYANSKSHF | | 45665 |
| HPV31 | E1 | 480 | 10 | SYANSKSHFW | | 45666 |
| HPV31 | E1 | 480 | 11 | SYANSKSHFWL | | 45667 |
| HPV31 | E1 | 464 | 8 | SYFGMSLI | | 45668 |
| HPV31 | E1 | 464 | 10 | SYFGMSLISF | | 45669 |
| HPV31 | E1 | 464 | 11 | SYFGMSLISFL | | 45670 |
| HPV31 | E1 | 334 | 10 | TFDLSQMVQW | | 45671 |
| HPV31 | E1 | 617 | 10 | TFKCVSGQNI | | 45672 |
| HPV31 | E1 | 567 | 8 | TFPNPFPF | | 45673 |
| HPV31 | E1 | 565 | 8 | VFTFPNPF | | 45674 |
| HPV31 | E1 | 565 | 10 | VFTFPNPFPF | | 45675 |
| HPV31 | E1 | 254 | 8 | VMLMLVRF | | 45676 |
| HPV31 | E1 | 581 | 9 | VYELSDKNW | | 45677 |
| HPV31 | E1 | 312 | 8 | VYGETPEW | | 45678 |
| HPV31 | E1 | 312 | 9 | VYGETPEWI | | 45679 |
| HPV31 | E1 | 17 | 8 | WFYVEAVI | | 45680 |
| HPV31 | E1 | 301 | 9 | WYRTGMSNI | | 45681 |
| HPV31 | E1 | 465 | 9 | YFGMSLISF | | 45682 |
| HPV31 | E1 | 465 | 10 | YFGMSLISFL | | 45683 |
| HPV31 | E1 | 300 | 10 | YWYRTGMSNI | | 45684 |
| HPV31 | E2 | 352 | 8 | DFLNTVKI | | 45685 |
| HPV31 | E2 | 91 | 9 | DWTMQQTSL | | 45686 |
| HPV31 | E2 | 91 | 11 | DWTMQQTSLEL | | 45687 |
| HPV31 | E2 | 31 | 8 | DYWKHIRL | | 45688 |
| HPV31 | E2 | 114 | 8 | GYTVEVQF | | 45689 |
| HPV31 | E2 | 18 | 9 | HYENDSKRL | | 45690 |
| HPV31 | E2 | 130 | 8 | HYTNWKFI | | 45691 |
| HPV31 | E2 | 130 | 10 | HYTNWKFIYL | | 45692 |
| HPV31 | E2 | 157 | 9 | IYYVHEGHI | | 45693 |
| HPV31 | E2 | 183 | 11 | KWEVHAGGQVI | | 45694 |
| HPV31 | E2 | 177 | 8 | KYGTGKKW | | 45695 |
| HPV31 | E2 | 42 | 10 | LMYKAREMGI | | 45696 |
| HPV31 | E2 | 318 | 9 | LYEQVSSTW | | 45697 |
| HPV31 | E2 | 318 | 11 | LYEQVSSTWHW | | 45698 |
| HPV31 | E2 | 101 | 10 | LYLTAPTGCL | | 45699 |
| HPV31 | E2 | 43 | 9 | MYKAREMGI | | 45700 |
| HPV31 | E2 | 133 | 9 | NWKFIYLCI | | 45701 |
| HPV31 | E2 | 309 | 10 | RYRLSKYKQL | | 45702 |
| HPV31 | E2 | 206 | 9 | SFAGIVTKL | | 45703 |
| HPV31 | E2 | 128 | 9 | TMHYTNWKF | | 45704 |
| HPV31 | E2 | 128 | 10 | TMHYTNWKFI | | 45705 |
| HPV31 | E2 | 93 | 9 | TMQQTSLEL | | 45706 |
| HPV31 | E2 | 93 | 11 | TMQQTSLELYL | | 45707 |
| HPV31 | E2 | 343 | 11 | TYISTSQRDDF | | 45708 |
| HPV31 | E2 | 199 | 9 | VFSSDEISF | | 45709 |
| HPV31 | E2 | 32 | 11 | YWKHIRLECVL | | 45710 |
| HPV31 | E2 | 158 | 8 | YYVHEGHI | | 45711 |

TABLE XVIII-continued

A24 Motif Peptides

| Type | Protein | Position | No. of Amino Acids | Sequence | A*2402 | Seq. Id. No. |
|---|---|---|---|---|---|---|
| HPV31 | E2 | 158 | 11 | YYVHEGHITYF | | 45712 |
| HPV31 | E5 | 59 | 8 | CFCIYVVF | | 45713 |
| HPV31 | E5 | 59 | 9 | CFCIYVVFI | | 45714 |
| HPV31 | E5 | 59 | 11 | CFCIYVVFIYI | | 45715 |
| HPV31 | E5 | 18 | 10 | CFCVLLFVCL | | 45716 |
| HPV31 | E5 | 14 | 9 | CFLLCFCVL | | 45717 |
| HPV31 | E5 | 14 | 10 | CFLLCFCVLL | | 45718 |
| HPV31 | E5 | 14 | 11 | CFLLCFCVLLF | | 45719 |
| HPV31 | E5 | 67 | 8 | IYIPLFVI | | 45720 |
| HPV31 | E5 | 62 | 8 | IYVVFIYI | | 45721 |
| HPV31 | E5 | 62 | 10 | IYVVFIYIPL | | 45722 |
| HPV31 | E5 | 62 | 11 | IYVVFIYIPLF | | 45723 |
| HPV31 | E5 | 23 | 10 | LFVCLVIRPL | | 45724 |
| HPV31 | E5 | 71 | 10 | LFVIHTHASF | | 45725 |
| HPV31 | E5 | 71 | 11 | LFVIHTHASFL | | 45726 |
| HPV31 | E5 | 49 | 9 | LWVIATSPL | | 45727 |
| HPV31 | E5 | 65 | 8 | VFIYIPLF | | 45728 |
| HPV31 | E5 | 65 | 10 | VFIYIPLFVI | | 45729 |
| HPV31 | E5 | 38 | 8 | VYATLLLL | | 45730 |
| HPV31 | E5 | 38 | 9 | VYATLLLLI | | 45731 |
| HPV31 | E5 | 38 | 11 | VYATLLLLIVI | | 45732 |
| HPV31 | E6 | 44 | 9 | DFAFTDLTI | | 45733 |
| HPV31 | E6 | 69 | 8 | FYSKVSEF | | 45734 |
| HPV31 | E6 | 69 | 10 | FYSKVSEFRW | | 45735 |
| HPV31 | E6 | 124 | 9 | RFHNIGGRW | | 45736 |
| HPV31 | E6 | 68 | 9 | RFYSKVSEF | | 45737 |
| HPV31 | E6 | 68 | 11 | RFYSKVSEFRW | | 45738 |
| HPV31 | E6 | 131 | 10 | RWTGRCIACW | | 45739 |
| HPV31 | E6 | 80 | 9 | RYSVYGTTL | | 45740 |
| HPV31 | E6 | 83 | 9 | VYGTTLEKL | | 45741 |
| HPV31 | E6 | 78 | 11 | WYRYSVYGTTL | | 45742 |
| HPV31 | E7 | 56 | 10 | TFCCQCKSTL | | 45743 |
| HPV31 | L1 | 151 | 9 | DYKQTQLCL | | 45744 |
| HPV31 | L1 | 151 | 10 | DYKQTQLCLL | | 45745 |
| HPV31 | L1 | 444 | 9 | DYVFWEVNL | | 45746 |
| HPV31 | L1 | 370 | 8 | EFDLQFIF | | 45747 |
| HPV31 | L1 | 370 | 10 | EFDLQFIFQL | | 45748 |
| HPV31 | L1 | 363 | 9 | EYLRHGEEF | | 45749 |
| HPV31 | L1 | 363 | 11 | EYLRHGEEFDL | | 45750 |
| HPV31 | L1 | 26 | 8 | EYVTRTNI | | 45751 |
| HPV31 | L1 | 248 | 10 | FFYLRREQMF | | 45752 |
| HPV31 | L1 | 447 | 10 | FWEVNLKEKF | | 45753 |
| HPV31 | L1 | 249 | 9 | FYLRREQMF | | 45754 |
| HPV31 | L1 | 91 | 9 | FYNPETQRL | | 45755 |
| HPV31 | L1 | 91 | 11 | FYNPETQRLVW | | 45756 |
| HPV31 | L1 | 205 | 10 | GFGAMDFTAL | | 45757 |
| HPV31 | L1 | 474 | 8 | GYRARPKF | | 45758 |
| HPV31 | L1 | 376 | 9 | IFQLCKITL | | 45759 |
| HPV31 | L1 | 33 | 10 | IYYHAGSARL | | 45760 |
| HPV31 | L1 | 33 | 11 | IYYHAGSARLL | | 45761 |
| HPV31 | L1 | 83 | 9 | KFGFPDTSF | | 45762 |
| HPV31 | L1 | 455 | 9 | KFSADLDQF | | 45763 |
| HPV31 | L1 | 455 | 11 | KFSADLDQFPL | | 45764 |
| HPV31 | L1 | 237 | 11 | KMVAEPYGDTL | | 45765 |
| HPV31 | L1 | 247 | 11 | LFFYLRREQMF | | 45766 |
| HPV31 | L1 | 3 | 11 | LWRPSEATVYL | | 45767 |
| HPV31 | L1 | 342 | 8 | NMSVCAAI | | 45768 |
| HPV31 | L1 | 441 | 8 | PFKDYVFW | | 45769 |
| HPV31 | L1 | 242 | 8 | PYGDTLFF | | 45770 |
| HPV31 | L1 | 242 | 10 | PYGDTLFFYL | | 45771 |
| HPV31 | L1 | 374 | 9 | QFIFQLCKI | | 45772 |
| HPV31 | L1 | 374 | 11 | QFIFQLCKITL | | 45773 |
| HPV31 | L1 | 462 | 8 | QFPLGRKF | | 45774 |
| HPV31 | L1 | 462 | 9 | QFPLGRKFL | | 45775 |
| HPV31 | L1 | 462 | 10 | QFPLGRKFLL | | 45776 |
| HPV31 | L1 | 255 | 8 | QMFVRHFF | | 45777 |
| HPV31 | L1 | 70 | 9 | QYRVFRVRL | | 45778 |
| HPV31 | L1 | 420 | 8 | RFVTSQAI | | 45779 |
| HPV31 | L1 | 90 | 10 | SFYNPETQRL | | 45780 |
| HPV31 | L1 | 149 | 9 | SMDYKQTQL | | 45781 |
| HPV31 | L1 | 149 | 11 | SMDYKQTQLCL | | 45782 |
| HPV31 | L1 | 394 | 10 | SMNPAILEDW | | 45783 |
| HPV31 | L1 | 299 | 9 | SMVTSDAQI | | 45784 |
| HPV31 | L1 | 299 | 10 | SMVTSDAQIF | | 45785 |

TABLE XVIII-continued

A24 Motif Peptides

| Type | Protein | Position | No. of Amino Acids | Sequence | A*2402 | Seq. Id. No. |
|---|---|---|---|---|---|---|
| HPV31 | L1 | 355 | 11 | TFKSSNFKEYL | | 45786 |
| HPV31 | L1 | 390 | 10 | TYIHSMNPAI | | 45787 |
| HPV31 | L1 | 390 | 11 | TYIHSMNPAIL | | 45788 |
| HPV31 | L1 | 418 | 10 | TYRFVTSQAI | | 45789 |
| HPV31 | L1 | 446 | 11 | VFWEVNLKEKF | | 45790 |
| HPV31 | L1 | 34 | 9 | YYHAGSARL | | 45791 |
| HPV31 | L1 | 34 | 10 | YYHAGSARLL | | 45792 |
| HPV31 | L2 | 251 | 11 | AYETVNAEESL | | 45793 |
| HPV31 | L2 | 385 | 11 | AYVPTNTTVPL | | 45794 |
| HPV31 | L2 | 275 | 8 | DFLDIIAL | | 45795 |
| HPV31 | L2 | 438 | 11 | DFYLHPSYYML | | 45796 |
| HPV31 | L2 | 439 | 10 | FYLHPSYYML | | 45797 |
| HPV31 | L2 | 318 | 9 | HYYYDISSI | | 45798 |
| HPV31 | L2 | 403 | 9 | IFSGPDVPI | | 45799 |
| HPV31 | L2 | 432 | 8 | IFVDGGDF | | 45800 |
| HPV31 | L2 | 432 | 10 | IFVDGGDFYL | | 45801 |
| HPV31 | L2 | 352 | 10 | LYDIYADTDF | | 45802 |
| HPV31 | L2 | 261 | 10 | LYFSNTSHNI | | 45803 |
| HPV31 | L2 | 187 | 10 | NYEEIPMDTF | | 45804 |
| HPV31 | L2 | 187 | 11 | NYEEIPMDTFI | | 45805 |
| HPV31 | L2 | 47 | 8 | RYGSMGVF | | 45806 |
| HPV31 | L2 | 47 | 9 | RYGSMGVFF | | 45807 |
| HPV31 | L2 | 295 | 11 | RYSRLGNKQTL | | 45808 |
| HPV31 | L2 | 50 | 9 | SMGVFFGGL | | 45809 |
| HPV31 | L2 | 50 | 11 | SMGVFFGGLGI | | 45810 |
| HPV31 | L2 | 195 | 11 | TFIVSTNNENI | | 45811 |
| HPV31 | L2 | 236 | 9 | TFLSAPKQL | | 45812 |
| HPV31 | L2 | 236 | 10 | TFLSAPKQLI | | 45813 |
| HPV31 | L2 | 157 | 8 | TFTDPSVL | | 45814 |
| HPV31 | L2 | 53 | 8 | VFFGGLGI | | 45815 |
| HPV31 | L2 | 262 | 9 | YFSNTSHNI | | 45816 |
| HPV31 | L2 | 319 | 8 | YYYDISSI | | 45817 |
| HPV33 | E1 | 452 | 9 | AFKKFLKGI | | 45818 |
| HPV33 | E1 | 448 | 9 | AFLGAFKKF | | 45819 |
| HPV33 | E1 | 448 | 10 | AFLGAFKKFL | | 45820 |
| HPV33 | E1 | 384 | 11 | AFLKSNSQAKI | | 45821 |
| HPV33 | E1 | 207 | 9 | AYGISFMEL | | 45822 |
| HPV33 | E1 | 297 | 9 | CMVIEPPKL | | 45823 |
| HPV33 | E1 | 228 | 9 | DWCITGYGI | | 45824 |
| HPV33 | E1 | 49 | 11 | EFIDDSMENSI | | 45825 |
| HPV33 | E1 | 580 | 8 | EFKNPFPF | | 45826 |
| HPV33 | E1 | 445 | 9 | EFTAFLGAF | | 45827 |
| HPV33 | E1 | 352 | 11 | EMVQWAYDNEL | | 45828 |
| HPV33 | E1 | 331 | 9 | EWIDRLTVL | | 45829 |
| HPV33 | E1 | 605 | 9 | FFSRTWCKL | | 45830 |
| HPV33 | E1 | 605 | 11 | FFSRTWCKLDL | | 45831 |
| HPV33 | E1 | 212 | 8 | FMELVRPF | | 45832 |
| HPV33 | E1 | 501 | 11 | FWLQPLSDAKI | | 45833 |
| HPV33 | E1 | 11 | 8 | GMGCTGWF | | 45834 |
| HPV33 | E1 | 512 | 9 | GMIDDVTPI | | 45835 |
| HPV33 | E1 | 512 | 11 | GMIDDVTPISW | | 45836 |
| HPV33 | E1 | 480 | 8 | GMSLIQFL | | 45837 |
| HPV33 | E1 | 16 | 9 | GWFEVEAVI | | 45838 |
| HPV33 | E1 | 347 | 10 | IFDLSEMVQW | | 45839 |
| HPV33 | E1 | 203 | 8 | KFKEAYGI | | 45840 |
| HPV33 | E1 | 203 | 10 | KFKEAYGISF | | 45841 |
| HPV33 | E1 | 412 | 8 | KMSIGQWI | | 45842 |
| HPV33 | E1 | 69 | 11 | LFNIQEGEDDL | | 45843 |
| HPV33 | E1 | 286 | 8 | LMSNLLSI | | 45844 |
| HPV33 | E1 | 201 | 10 | LYKFKEAYGI | | 45845 |
| HPV33 | E1 | 253 | 8 | LYTHLQCL | | 45846 |
| HPV33 | E1 | 312 | 11 | LYWFRTAMSNI | | 45847 |
| HPV33 | E1 | 601 | 10 | NWKSFFSRTW | | 45848 |
| HPV33 | E1 | 431 | 8 | NWRPIVQL | | 45849 |
| HPV33 | E1 | 431 | 9 | NWRPIVQLL | | 45850 |
| HPV33 | E1 | 570 | 10 | PYLHSRLTVF | | 45851 |
| HPV33 | E1 | 485 | 8 | QFLKGCVI | | 45852 |
| HPV33 | E1 | 355 | 8 | QWAYDNEL | | 45853 |
| HPV33 | E1 | 273 | 9 | RFRCSKNRL | | 45854 |
| HPV33 | E1 | 568 | 9 | RWPYLHSRL | | 45855 |
| HPV33 | E1 | 440 | 10 | RYQNIEFTAF | | 45856 |
| HPV33 | E1 | 440 | 11 | RYQNIEFTAFL | | 45857 |
| HPV33 | E1 | 604 | 10 | SFFSRTWCKL | | 45858 |
| HPV33 | E1 | 211 | 9 | SFMELVRPF | | 45859 |

TABLE XVIII-continued

A24 Motif Peptides

| Type | Protein | Position | No. of Amino Acids | Sequence | A*2402 | Seq. Id. No. |
|---|---|---|---|---|---|---|
| HPV33 | E1 | 342 | 9 | SFNDNIFDL | | 45860 |
| HPV33 | E1 | 477 | 8 | SYFGMSLI | | 45861 |
| HPV33 | E1 | 477 | 10 | SYFGMSLIQF | | 45862 |
| HPV33 | E1 | 477 | 11 | SYFGMSLIQFL | | 45863 |
| HPV33 | E1 | 609 | 8 | TWCKLDLI | | 45864 |
| HPV33 | E1 | 523 | 11 | TYIDDYMRNAL | | 45865 |
| HPV33 | E1 | 119 | 10 | TYRKRKIDEL | | 45866 |
| HPV33 | E1 | 578 | 8 | VFEFKNPF | | 45867 |
| HPV33 | E1 | 578 | 10 | VFEFKNPFPF | | 45868 |
| HPV33 | E1 | 594 | 9 | VYAINDENW | | 45869 |
| HPV33 | E1 | 17 | 8 | WFEVEAVI | | 45870 |
| HPV33 | E1 | 314 | 9 | WFRTAMSNI | | 45871 |
| HPV33 | E1 | 478 | 9 | YFGMSLIQF | | 45872 |
| HPV33 | E1 | 478 | 10 | YFGMSLIQFL | | 45873 |
| HPV33 | E1 | 528 | 11 | YMRNALDGNEI | | 45874 |
| HPV33 | E1 | 313 | 10 | YWFRTAMSNI | | 45875 |
| HPV33 | E2 | 69 | 11 | AFQVIELQMAL | | 45876 |
| HPV33 | E2 | 153 | 8 | DYIGMYYI | | 45877 |
| HPV33 | E2 | 130 | 8 | DYTNWGEI | | 45878 |
| HPV33 | E2 | 130 | 10 | DYTNWGEIYI | | 45879 |
| HPV33 | E2 | 130 | 11 | DYTNWGEIYII | | 45880 |
| HPV33 | E2 | 32 | 11 | HWKLIRMECAL | | 45881 |
| HPV33 | E2 | 177 | 8 | KYSKTQMW | | 45882 |
| HPV33 | E2 | 243 | 8 | LFCADPAL | | 45883 |
| HPV33 | E2 | 18 | 9 | LYEADKTDL | | 45884 |
| HPV33 | E2 | 299 | 9 | LYSSMSSTW | | 45885 |
| HPV33 | E2 | 299 | 11 | LYSSMSSTWHW | | 45886 |
| HPV33 | E2 | 43 | 9 | LYTAKQMGF | | 45887 |
| HPV33 | E2 | 333 | 8 | MFLGTVKI | | 45888 |
| HPV33 | E2 | 183 | 11 | MWEVHVGGQVI | | 45889 |
| HPV33 | E2 | 133 | 8 | NWGEIYII | | 45890 |
| HPV33 | E2 | 332 | 9 | QMFLGTVKI | | 45891 |
| HPV33 | E2 | 91 | 9 | QWTLQQTSL | | 45892 |
| HPV33 | E2 | 86 | 9 | QYSTSQWTL | | 45893 |
| HPV33 | E2 | 290 | 10 | RYRLKPYKEL | | 45894 |
| HPV33 | E2 | 302 | 8 | SMSSTWHW | | 45895 |
| HPV33 | E2 | 324 | 11 | TFVTEQQQQMF | | 45896 |
| HPV33 | E2 | 128 | 10 | TMDYTNWGEI | | 45897 |
| HPV33 | E2 | 146 | 10 | TMVTGKVDYI | | 45898 |
| HPV33 | E2 | 101 | 10 | VWLCEPPKCF | | 45899 |
| HPV33 | E2 | 158 | 11 | YYIHNCEKVYF | | 45900 |
| HPV33 | E5 | 30 | 8 | AWLLVLVL | | 45901 |
| HPV33 | E5 | 30 | 9 | AWLLVLVLL | | 45902 |
| HPV33 | E5 | 30 | 10 | AWLLVLVLLL | | 45903 |
| HPV33 | E5 | 30 | 11 | AWLLVLVLLLW | | 45904 |
| HPV33 | E5 | 8 | 8 | CFILFLCL | | 45905 |
| HPV33 | E5 | 8 | 10 | CFILFLCLSL | | 45906 |
| HPV33 | E5 | 8 | 11 | CFILFLCLSLL | | 45907 |
| HPV33 | E5 | 52 | 8 | CYLLFLYL | | 45908 |
| HPV33 | E5 | 50 | 8 | FFCYLLFL | | 45909 |
| HPV33 | E5 | 50 | 10 | FFCYLLFLYL | | 45910 |
| HPV33 | E5 | 49 | 8 | IFFCYLLF | | 45911 |
| HPV33 | E5 | 49 | 9 | IFFCYLLFL | | 45912 |
| HPV33 | E5 | 49 | 11 | IFFCYLLFLYL | | 45913 |
| HPV33 | E5 | 2 | 8 | IFVFVLCF | | 45914 |
| HPV33 | E5 | 2 | 9 | IFVFVLCFI | | 45915 |
| HPV33 | E5 | 2 | 10 | IFVFVLCFIL | | 45916 |
| HPV33 | E5 | 2 | 11 | IFVFVLCFILF | | 45917 |
| HPV33 | E5 | 11 | 8 | LFLCLSLL | | 45918 |
| HPV33 | E5 | 11 | 9 | LFLCLSLLL | | 45919 |
| HPV33 | E5 | 55 | 10 | LFLYLPMMCI | | 45920 |
| HPV33 | E5 | 39 | 9 | LWVFVGSPL | | 45921 |
| HPV33 | E5 | 39 | 11 | LWVFVGSPLKI | | 45922 |
| HPV33 | E5 | 57 | 8 | LYLPMMCI | | 45923 |
| HPV33 | E5 | 57 | 10 | LYLPMMCINF | | 45924 |
| HPV33 | E5 | 28 | 8 | TYAWLLVL | | 45925 |
| HPV33 | E5 | 28 | 10 | TYAWLLVLVL | | 45926 |
| HPV33 | E5 | 28 | 11 | TYAWLLVLVLL | | 45927 |
| HPV33 | E5 | 41 | 9 | VFVGSPLKI | | 45928 |
| HPV33 | E5 | 41 | 10 | VFVGSPLKIF | | 45929 |
| HPV33 | E5 | 41 | 11 | VFVGSPLKIFF | | 45930 |
| HPV33 | E5 | 4 | 8 | VFVLCFIL | | 45931 |
| HPV33 | E5 | 4 | 9 | VFVLCFILF | | 45932 |
| HPV33 | E5 | 4 | 10 | VFVLCFILFL | | 45933 |

TABLE XVIII-continued

A24 Motif Peptides

| Type | Protein | Position | No. of Amino Acids | Sequence | A*2402 | Seq. Id. No. |
|---|---|---|---|---|---|---|
| HPV33 | E6 | 139 | 11 | CWRSRRRETAL | | 45934 |
| HPV33 | E6 | 78 | 11 | HYNYSVYGNTL | | 45935 |
| HPV33 | E6 | 80 | 9 | NYSVYGNTL | | 45936 |
| HPV33 | E6 | 59 | 9 | PFGICKLCL | | 45937 |
| HPV33 | E6 | 59 | 11 | PFGICKLCLRF | | 45938 |
| HPV33 | E6 | 124 | 9 | RFHNISGRW | | 45939 |
| HPV33 | E6 | 131 | 10 | RWAGRCAACW | | 45940 |
| HPV33 | E6 | 42 | 9 | VYDFAFADL | | 45941 |
| HPV33 | E6 | 53 | 8 | VYREGNPF | | 45942 |
| HPV33 | E6 | 53 | 10 | VYREGNPFGI | | 45943 |
| HPV33 | E7 | 15 | 8 | LYPEPTDL | | 45944 |
| HPV33 | L1 | 392 | 10 | AMNPDILEDW | | 45945 |
| HPV33 | L1 | 151 | 9 | DYKQTQLCL | | 45946 |
| HPV33 | L1 | 151 | 10 | DYKQTQLCLL | | 45947 |
| HPV33 | L1 | 368 | 8 | EYDLQFVF | | 45948 |
| HPV33 | L1 | 368 | 10 | EYDLQFVFQL | | 45949 |
| HPV33 | L1 | 361 | 11 | EYIRHVEEYDL | | 45950 |
| HPV33 | L1 | 26 | 8 | EYVSRTSI | | 45951 |
| HPV33 | L1 | 247 | 10 | FFFLRREQMF | | 45952 |
| HPV33 | L1 | 248 | 9 | FFLRREQMF | | 45953 |
| HPV33 | L1 | 260 | 8 | FFNRAGTL | | 45954 |
| HPV33 | L1 | 445 | 10 | FWEVDLKEKF | | 45955 |
| HPV33 | L1 | 91 | 9 | FYNPDTQRL | | 45956 |
| HPV33 | L1 | 91 | 11 | FYNPDTQRLVW | | 45957 |
| HPV33 | L1 | 204 | 10 | GFGCMDFKTL | | 45958 |
| HPV33 | L1 | 259 | 9 | HFFNRAGTL | | 45959 |
| HPV33 | L1 | 33 | 10 | IYYYAGSSRL | | 45960 |
| HPV33 | L1 | 33 | 11 | IYYYAGSSRLL | | 45961 |
| HPV33 | L1 | 83 | 9 | KFGFPDTSF | | 45962 |
| HPV33 | L1 | 466 | 8 | KFLLQAGL | | 45963 |
| HPV33 | L1 | 453 | 9 | KFSADLDQF | | 45964 |
| HPV33 | L1 | 453 | 11 | KFSADLDQFPL | | 45965 |
| HPV33 | L1 | 236 | 11 | KMTSEPYGDSL | | 45966 |
| HPV33 | L1 | 442 | 9 | KYTFWEVDL | | 45967 |
| HPV33 | L1 | 246 | 11 | LFFFLRREQMF | | 45968 |
| HPV33 | L1 | 306 | 8 | LFNKPYWL | | 45969 |
| HPV33 | L1 | 241 | 8 | PYGDSLFF | | 45970 |
| HPV33 | L1 | 241 | 9 | PYGDSLFFF | | 45971 |
| HPV33 | L1 | 241 | 10 | PYGDSLFFFL | | 45972 |
| HPV33 | L1 | 460 | 8 | QFPLGRKF | | 45973 |
| HPV33 | L1 | 460 | 9 | QFPLGRKFL | | 45974 |
| HPV33 | L1 | 460 | 10 | QFPLGRKFLL | | 45975 |
| HPV33 | L1 | 372 | 11 | QFVFQLCKVTL | | 45976 |
| HPV33 | L1 | 254 | 8 | QMFVRHFF | | 45977 |
| HPV33 | L1 | 70 | 9 | QYRVFRVRL | | 45978 |
| HPV33 | L1 | 418 | 8 | RFVTSQAI | | 45979 |
| HPV33 | L1 | 90 | 10 | SFYNPDTQRL | | 45980 |
| HPV33 | L1 | 149 | 9 | SMDYKQTQL | | 45981 |
| HPV33 | L1 | 149 | 11 | SMDYKQTQLCL | | 45982 |
| HPV33 | L1 | 298 | 9 | SMVTSESQL | | 45983 |
| HPV33 | L1 | 298 | 10 | SMVTSESQLF | | 45984 |
| HPV33 | L1 | 444 | 11 | TFWEVDLKEKF | | 45985 |
| HPV33 | L1 | 388 | 10 | TYIHAMNPDI | | 45986 |
| HPV33 | L1 | 388 | 11 | TYIHAMNPDIL | | 45987 |
| HPV33 | L1 | 353 | 11 | TYKNENFKEYI | | 45988 |
| HPV33 | L1 | 416 | 10 | TYRFVTSQAI | | 45989 |
| HPV33 | L1 | 374 | 9 | VFQLCKVTL | | 45990 |
| HPV33 | L1 | 100 | 9 | VWACVGLEI | | 45991 |
| HPV33 | L1 | 3 | 11 | VWRPSEATVYL | | 45992 |
| HPV33 | L1 | 35 | 8 | YYAGSSRL | | 45993 |
| HPV33 | L1 | 35 | 9 | YYAGSSRLL | | 45994 |
| HPV33 | L1 | 34 | 9 | YYYAGSSRL | | 45995 |
| HPV33 | L1 | 34 | 10 | YYYAGSSRLL | | 45996 |
| HPV33 | L2 | 256 | 11 | AFESFDPEDTL | | 45997 |
| HPV33 | L2 | 241 | 9 | AFLTSPHKL | | 45998 |
| HPV33 | L2 | 241 | 10 | AFLTSPHKLI | | 45999 |
| HPV33 | L2 | 280 | 8 | DFLDIIAL | | 46000 |
| HPV33 | L2 | 439 | 9 | DFVLHPSYF | | 46001 |
| HPV33 | L2 | 439 | 10 | DFVLHPSYFI | | 46002 |
| HPV33 | L2 | 439 | 11 | DFVLHPSYFIL | | 46003 |
| HPV33 | L2 | 323 | 9 | HYYQDLSPI | | 46004 |
| HPV33 | L2 | 46 | 8 | KYGSLGVF | | 46005 |
| HPV33 | L2 | 46 | 9 | KYGSLGVFF | | 46006 |
| HPV33 | L2 | 414 | 8 | LFPTSSPF | | 46007 |

TABLE XVIII-continued

A24 Motif Peptides

| Type | Protein | Position | No. of Amino Acids | Sequence | A*2402 | Seq. Id. No. |
|---|---|---|---|---|---|---|
| HPV33 | L2 | 414 | 11 | LFPTSSPFVPI | | 46008 |
| HPV33 | L2 | 426 | 8 | PFFPFDTI | | 46009 |
| HPV33 | L2 | 420 | 8 | PFVPISPF | | 46010 |
| HPV33 | L2 | 420 | 9 | PFVPISPFF | | 46011 |
| HPV33 | L2 | 420 | 11 | PFVPISPFFPF | | 46012 |
| HPV33 | L2 | 376 | 9 | PMQHSYSTF | | 46013 |
| HPV33 | L2 | 300 | 11 | RFSRVGQKATL | | 46014 |
| HPV33 | L2 | 259 | 8 | SFDPEDTL | | 46015 |
| HPV33 | L2 | 259 | 10 | SFDPEDTLQF | | 46016 |
| HPV33 | L2 | 192 | 10 | SYENIPMDTF | | 46017 |
| HPV33 | L2 | 355 | 8 | SYSINDGL | | 46018 |
| HPV33 | L2 | 162 | 8 | TFTEPSVL | | 46019 |
| HPV33 | L2 | 251 | 10 | TYDNPAFESF | | 46020 |
| HPV33 | L2 | 52 | 8 | VFFGGLGI | | 46021 |
| HPV33 | L2 | 404 | 11 | VMSGPDIPSPL | | 46022 |
| HPV33 | L2 | 446 | 11 | YFILRRRKRF | | 46023 |
| HPV33 | L2 | 324 | 8 | YYQDLSPI | | 46024 |
| HPV33 | L2 | 324 | 11 | YYQDLSPIVPL | | 46025 |
| HPV45 | E1 | 199 | 9 | AMLAVFKDI | | 46026 |
| HPV45 | E1 | 512 | 11 | AMLDDATHTCW | | 46027 |
| HPV45 | E1 | 604 | 10 | CFFERTWSRL | | 46028 |
| HPV45 | E1 | 297 | 9 | CMLIEPPKL | | 46029 |
| HPV45 | E1 | 49 | 9 | DFIDTQLSI | | 46030 |
| HPV45 | E1 | 367 | 9 | DMAFQYAQL | | 46031 |
| HPV45 | E1 | 46 | 10 | DMVDFIDTQL | | 46032 |
| HPV45 | E1 | 352 | 11 | DMVQWAFDNDL | | 46033 |
| HPV45 | E1 | 431 | 8 | DWRPIVQF | | 46034 |
| HPV45 | E1 | 431 | 9 | DWRPIVQFL | | 46035 |
| HPV45 | E1 | 445 | 9 | EFISFLRAL | | 46036 |
| HPV45 | E1 | 331 | 8 | EWIQRLTI | | 46037 |
| HPV45 | E1 | 331 | 9 | EWIQRLTII | | 46038 |
| HPV45 | E1 | 605 | 9 | FFERTWSRL | | 46039 |
| HPV45 | E1 | 605 | 11 | FFERTWSRLDL | | 46040 |
| HPV45 | E1 | 243 | 11 | GFKTLIKPATL | | 46041 |
| HPV45 | E1 | 480 | 8 | GMSFIHFL | | 46042 |
| HPV45 | E1 | 16 | 8 | GWFFVETI | | 46043 |
| HPV45 | E1 | 485 | 8 | HFLQGAII | | 46044 |
| HPV45 | E1 | 485 | 10 | HFLQGAIISF | | 46045 |
| HPV45 | E1 | 207 | 9 | IYGLSFTDL | | 46046 |
| HPV45 | E1 | 263 | 9 | KWGVLILAL | | 46047 |
| HPV45 | E1 | 263 | 10 | KWGVLILALL | | 46048 |
| HPV45 | E1 | 253 | 8 | LYAHIQCL | | 46049 |
| HPV45 | E1 | 312 | 8 | LYWYRTGI | | 46050 |
| HPV45 | E1 | 312 | 11 | LYWYRTGISNI | | 46051 |
| HPV45 | E1 | 347 | 10 | NFDLSDMVQW | | 46052 |
| HPV45 | E1 | 601 | 10 | NWKCFFERTW | | 46053 |
| HPV45 | E1 | 570 | 10 | PYLESRVTVF | | 46054 |
| HPV45 | E1 | 437 | 10 | QFLRYQGVEF | | 46055 |
| HPV45 | E1 | 437 | 11 | QFLRYQGVEFI | | 46056 |
| HPV45 | E1 | 412 | 8 | QMNMSQWI | | 46057 |
| HPV45 | E1 | 355 | 8 | QWAFDNDL | | 46058 |
| HPV45 | E1 | 417 | 10 | QWIKYRCSKI | | 46059 |
| HPV45 | E1 | 273 | 9 | RYKCGKNRL | | 46060 |
| HPV45 | E1 | 440 | 8 | RYQGVEFI | | 46061 |
| HPV45 | E1 | 440 | 10 | RYQGVEFISF | | 46062 |
| HPV45 | E1 | 440 | 11 | RYQGVEFISFL | | 46063 |
| HPV45 | E1 | 482 | 10 | SFIHFLQGAI | | 46064 |
| HPV45 | E1 | 482 | 11 | SFIHFLQGAII | | 46065 |
| HPV45 | E1 | 448 | 9 | SFLRALKEF | | 46066 |
| HPV45 | E1 | 448 | 10 | SFLRALKEFL | | 46067 |
| HPV45 | E1 | 211 | 9 | SFTDLVRNF | | 46068 |
| HPV45 | E1 | 493 | 9 | SFVNSNSHF | | 46069 |
| HPV45 | E1 | 493 | 10 | SFVNSNSHFW | | 46070 |
| HPV45 | E1 | 493 | 11 | SFVNSNSHFWL | | 46071 |
| HPV45 | E1 | 477 | 8 | SYFGMSFI | | 46072 |
| HPV45 | E1 | 477 | 10 | SYFGMSFIHF | | 46073 |
| HPV45 | E1 | 477 | 11 | SYFGMSFIHFL | | 46074 |
| HPV45 | E1 | 580 | 8 | TFPHAFPF | | 46075 |
| HPV45 | E1 | 523 | 11 | TYFDNYMRNAL | | 46076 |
| HPV45 | E1 | 203 | 8 | VFKDIYGL | | 46077 |
| HPV45 | E1 | 203 | 10 | VFKDIYGLSF | | 46078 |
| HPV45 | E1 | 578 | 8 | VFTFPHAF | | 46079 |
| HPV45 | E1 | 578 | 10 | VFTFPHAFPF | | 46080 |
| HPV45 | E1 | 594 | 9 | VYEINDKNW | | 46081 |

TABLE XVIII-continued

A24 Motif Peptides

| Type | Protein | Position | No. of Amino Acids | Sequence | A*2402 | Seq. Id. No. |
|---|---|---|---|---|---|---|
| HPV45 | E1 | 314 | 9 | WYRTGISNI | | 46082 |
| HPV45 | E1 | 524 | 10 | YFDNYMRNAL | | 46083 |
| HPV45 | E1 | 478 | 9 | YFGMSFIHF | | 46084 |
| HPV45 | E1 | 478 | 10 | YFGMSFIHFL | | 46085 |
| HPV45 | E1 | 528 | 11 | YMRNALDGNPI | | 46086 |
| HPV45 | E1 | 313 | 10 | YWYRTGISNI | | 46087 |
| HPV45 | E2 | 134 | 10 | CMNYVVWDSI | | 46088 |
| HPV45 | E2 | 97 | 11 | EWTLQDTCEEL | | 46089 |
| HPV45 | E2 | 325 | 11 | HWTGCNKNTGI | | 46090 |
| HPV45 | E2 | 24 | 9 | HYENDSKDI | | 46091 |
| HPV45 | E2 | 316 | 9 | HYSEISSTW | | 46092 |
| HPV45 | E2 | 316 | 11 | HYSEISSTWHW | | 46093 |
| HPV45 | E2 | 143 | 9 | IYYITETGI | | 46094 |
| HPV45 | E2 | 143 | 10 | IYYITETGIW | | 46095 |
| HPV45 | E2 | 2 | 9 | KMQTPKESL | | 46096 |
| HPV45 | E2 | 312 | 9 | KYADHYSEI | | 46097 |
| HPV45 | E2 | 184 | 8 | KYGNSNTW | | 46098 |
| HPV45 | E2 | 92 | 9 | KYNNEEWTL | | 46099 |
| HPV45 | E2 | 49 | 9 | LFTAREHGI | | 46100 |
| HPV45 | E2 | 107 | 10 | LWNTEPSQCF | | 46101 |
| HPV45 | E2 | 136 | 8 | NYVVWDSI | | 46102 |
| HPV45 | E2 | 136 | 11 | NYVVWDSIYYI | | 46103 |
| HPV45 | E2 | 160 | 8 | SYWGVYYI | | 46104 |
| HPV45 | E2 | 37 | 8 | SYWQLIRL | | 46105 |
| HPV45 | E2 | 348 | 8 | TFLDVVTI | | 46106 |
| HPV45 | E2 | 190 | 11 | TWEVQYGGNVI | | 46107 |
| HPV45 | E2 | 339 | 11 | TYNSEVQRNTF | | 46108 |
| HPV45 | E2 | 139 | 8 | VWDSIYYI | | 46109 |
| HPV45 | E2 | 38 | 11 | YWQLIRLENAI | | 46110 |
| HPV45 | E2 | 144 | 8 | YYITETGI | | 46111 |
| HPV45 | E2 | 144 | 9 | YYITETGIW | | 46112 |
| HPV45 | E6 | 61 | 9 | AYAACHKCI | | 46113 |
| HPV45 | E6 | 61 | 11 | AYAACHKCIDF | | 46114 |
| HPV45 | E6 | 70 | 9 | DFYSRIREL | | 46115 |
| HPV45 | E6 | 71 | 8 | FYSRIREL | 0.0260 | 46116 |
| HPV45 | E6 | 52 | 9 | LFIVYRDCI | | 46117 |
| HPV45 | E6 | 98 | 9 | LYNLLIRCL | 0.0001 | 46118 |
| HPV45 | E6 | 11 | 11 | PYKLPDLCTEL | 0.0064 | 46119 |
| HPV45 | E6 | 46 | 8 | QFAFKDLF | | 46120 |
| HPV45 | E6 | 46 | 9 | QFAFKDLFI | | 46121 |
| HPV45 | E6 | 85 | 9 | VYGETLEKI | | 46122 |
| HPV45 | E6 | 44 | 9 | VYQFAFKDL | | 46123 |
| HPV45 | E6 | 44 | 10 | VYQFAFKDLF | | 46124 |
| HPV45 | E6 | 44 | 11 | VYQFAFKDLFI | | 46125 |
| HPV45 | E6 | 80 | 11 | YYSNSVYGETL | | 46126 |
| HPV45 | E7 | 90 | 8 | LFLSTLSF | | 46127 |
| HPV45 | L1 | 94 | 11 | AYQYRVFRVAL | | 46128 |
| HPV45 | L1 | 177 | 9 | DYKQTQLCI | | 46129 |
| HPV45 | L1 | 177 | 10 | DYKQTQLCIL | | 46130 |
| HPV45 | L1 | 52 | 8 | DYVSRTSI | | 46131 |
| HPV45 | L1 | 52 | 9 | DYVSRTSIF | | 46132 |
| HPV45 | L1 | 399 | 8 | EYDLQFIF | | 46133 |
| HPV45 | L1 | 399 | 10 | EYDLQFIFQL | | 46134 |
| HPV45 | L1 | 274 | 9 | FFCLRREQL | | 46135 |
| HPV45 | L1 | 274 | 10 | FFCLRREQLF | | 46136 |
| HPV45 | L1 | 476 | 10 | FWTVDLKEKF | | 46137 |
| HPV45 | L1 | 60 | 9 | FYHAGSSRL | | 46138 |
| HPV45 | L1 | 60 | 10 | FYHAGSSRLL | | 46139 |
| HPV45 | L1 | 131 | 10 | GMEIGRGQPL | | 46140 |
| HPV45 | L1 | 231 | 10 | GYGAMDFSTL | | 46141 |
| HPV45 | L1 | 392 | 11 | HYSRHVEEYDL | | 46142 |
| HPV45 | L1 | 13 | 9 | IFLKNVNVF | | 46143 |
| HPV45 | L1 | 13 | 11 | IFLKNVNVFPI | | 46144 |
| HPV45 | L1 | 23 | 8 | IFLQMALW | | 46145 |
| HPV45 | L1 | 405 | 9 | IFQLCTITL | | 46146 |
| HPV45 | L1 | 59 | 10 | IFYHAGSSRL | | 46147 |
| HPV45 | L1 | 59 | 11 | IFYHAGSSRLL | | 46148 |
| HPV45 | L1 | 6 | 8 | IYGHGIII | | 46149 |
| HPV45 | L1 | 6 | 9 | IYGHGIIIF | | 46150 |
| HPV45 | L1 | 6 | 10 | IYGHGIIIFL | | 46151 |
| HPV45 | L1 | 117 | 9 | IYNPETQRL | | 46152 |
| HPV45 | L1 | 117 | 11 | IYNPETQRLVW | | 46153 |
| HPV45 | L1 | 109 | 9 | KFGLPDSTI | | 46154 |
| HPV45 | L1 | 497 | 8 | KFLVQAGL | | 46155 |

TABLE XVIII-continued

A24 Motif Peptides

| Type | Protein | Position | No. of Amino Acids | Sequence | A*2402 | Seq. Id. No. |
|---|---|---|---|---|---|---|
| HPV45 | L1 | 484 | 11 | KFSSDLDQYPL | | 46156 |
| HPV45 | L1 | 475 | 11 | KFWTVDLKEKF | | 46157 |
| HPV45 | L1 | 335 | 8 | LFNKPYWL | | 46158 |
| HPV45 | L1 | 29 | 11 | LWRPSDSTVYL | | 46159 |
| HPV45 | L1 | 273 | 10 | MFFCLRREQL | | 46160 |
| HPV45 | L1 | 273 | 11 | MFFCLRREQLF | | 46161 |
| HPV45 | L1 | 470 | 8 | PYDKLKFW | | 46162 |
| HPV45 | L1 | 268 | 8 | PYGDSMFF | | 46163 |
| HPV45 | L1 | 268 | 10 | PYGDSMFFCL | | 46164 |
| HPV45 | L1 | 403 | 9 | QFIFQLCTI | | 46165 |
| HPV45 | L1 | 403 | 11 | QFIFQLCTITL | | 46166 |
| HPV45 | L1 | 491 | 8 | QYPLGRKF | | 46167 |
| HPV45 | L1 | 491 | 9 | QYPLGRKFL | | 46168 |
| HPV45 | L1 | 96 | 9 | QYRVFRVAL | | 46169 |
| HPV45 | L1 | 272 | 11 | SMFFCLRREQL | | 46170 |
| HPV45 | L1 | 423 | 10 | SMNSSILENW | | 46171 |
| HPV45 | L1 | 419 | 10 | SYIHSMNSSI | | 46172 |
| HPV45 | L1 | 419 | 11 | SYIHSMNSSIL | | 46173 |
| HPV45 | L1 | 20 | 10 | VFPIFLQMAL | | 46174 |
| HPV45 | L1 | 20 | 11 | VFPIFLQMALW | | 46175 |
| HPV45 | L1 | 293 | 10 | VMGDTVPTDL | | 46176 |
| HPV45 | L1 | 126 | 9 | VWACVGMEI | | 46177 |
| HPV45 | L1 | 319 | 10 | VYSPSPSGSI | | 46178 |
| HPV45 | L2 | 161 | 8 | AFSDPSII | | 46179 |
| HPV45 | L2 | 255 | 9 | AYEPLDTTL | | 46180 |
| HPV45 | L2 | 255 | 11 | AYEPLDTTLSF | | 46181 |
| HPV45 | L2 | 275 | 8 | DFMDIIRL | | 46182 |
| HPV45 | L2 | 319 | 8 | FYHDISPI | | 46183 |
| HPV45 | L2 | 191 | 10 | GYEEIPLQTF | | 46184 |
| HPV45 | L2 | 318 | 9 | HFYHDISPI | | 46185 |
| HPV45 | L2 | 52 | 8 | IFLGGLGI | | 46186 |
| HPV45 | L2 | 400 | 8 | IYTGPDII | | 46187 |
| HPV45 | L2 | 400 | 9 | IYTGPDIIL | | 46188 |
| HPV45 | L2 | 346 | 8 | LFDVYADF | | 46189 |
| HPV45 | L2 | 438 | 8 | LWPWYYYF | | 46190 |
| HPV45 | L2 | 305 | 9 | MFTRSGKQI | | 46191 |
| HPV45 | L2 | 453 | 8 | PYFFADGF | | 46192 |
| HPV45 | L2 | 240 | 9 | QFLTHPSSL | | 46193 |
| HPV45 | L2 | 46 | 8 | QWSSLGIF | | 46194 |
| HPV45 | L2 | 46 | 9 | QWSSLGIFL | | 46195 |
| HPV45 | L2 | 435 | 11 | QYYLWPWYYYF | | 46196 |
| HPV45 | L2 | 367 | 9 | SFTYPKYSL | | 46197 |
| HPV45 | L2 | 384 | 9 | SYSNVTVPL | | 46198 |
| HPV45 | L2 | 250 | 10 | TFDNPAYEPL | | 46199 |
| HPV45 | L2 | 121 | 8 | TFTGTSGF | | 46200 |
| HPV45 | L2 | 121 | 10 | TFTGTSGFEI | | 46201 |
| HPV45 | L2 | 304 | 10 | TMFTRSGKQI | | 46202 |
| HPV45 | L2 | 444 | 9 | YFPKKRKRI | | 46203 |
| HPV45 | L2 | 443 | 10 | YYFPKKRKRI | | 46204 |
| HPV45 | L2 | 436 | 10 | YYLWPWYYYF | | 46205 |
| HPV45 | L2 | 442 | 11 | YYYFPKKRKRI | | 46206 |
| HPV56 | E2 | 52 | 9 | CFKKEGQHI | | 46207 |
| HPV56 | E2 | 71 | 10 | CMQYVAWKYI | | 46208 |
| HPV56 | E2 | 113 | 9 | DFEQEAKKF | | 46209 |
| HPV56 | E2 | 34 | 11 | EWTLRDTCEEL | | 46210 |
| HPV56 | E2 | 126 | 11 | IWEVHMENESI | | 46211 |
| HPV56 | E2 | 284 | 11 | IYKDETQRNSF | | 46212 |
| HPV56 | E2 | 29 | 9 | IYNNEEWTL | | 46213 |
| HPV56 | E2 | 80 | 9 | IYYNGDCGW | | 46214 |
| HPV56 | E2 | 120 | 8 | KFGCKNIW | | 46215 |
| HPV56 | E2 | 78 | 11 | KYIYYNGDCGW | | 46216 |
| HPV56 | E2 | 260 | 11 | LFVDVTSTYHW | | 46217 |
| HPV56 | E2 | 44 | 10 | LWLTEPKKCF | | 46218 |
| HPV56 | E2 | 277 | 8 | NYSIITII | | 46219 |
| HPV56 | E2 | 73 | 8 | QYVAWKYI | | 46220 |
| HPV56 | E2 | 253 | 8 | RFQKYKTL | | 46221 |
| HPV56 | E2 | 253 | 9 | RFQKYKTLF | | 46222 |
| HPV56 | E2 | 251 | 10 | RYRFQKYKTL | | 46223 |
| HPV56 | E2 | 251 | 11 | RYRFQKYKTLF | | 46224 |
| HPV56 | E2 | 293 | 8 | SFLSHVKI | | 46225 |
| HPV56 | E2 | 81 | 8 | YYNGDCGW | | 46226 |
| HPV56 | E6 | 106 | 8 | CYRCQSPL | | 46227 |
| HPV56 | E6 | 60 | 11 | DFPYAVCRVCL | | 46228 |
| HPV56 | E6 | 83 | 9 | DYSVYGATL | | 46229 |

TABLE XVIII-continued

A24 Motif Peptides

| Type | Protein | Position | No. of Amino Acids | Sequence | A*2402 | Seq. Id. No. |
|---|---|---|---|---|---|---|
| HPV56 | E6 | 134 | 10 | GWTGSCLGCW | | 46230 |
| HPV56 | E6 | 47 | 9 | NFACTELKL | | 46231 |
| HPV56 | E6 | 62 | 9 | PYAVCRVCL | | 46232 |
| HPV56 | E6 | 62 | 10 | PYAVCRVCLL | | 46233 |
| HPV56 | E6 | 62 | 11 | PYAVCRVCLLF | | 46234 |
| HPV56 | E6 | 127 | 9 | RFHLIAHGW | | 46235 |
| HPV56 | E6 | 86 | 9 | VYGATLESI | | 46236 |
| HPV56 | E6 | 45 | 9 | VYNFACTEL | | 46237 |
| HPV56 | E6 | 45 | 11 | VYNFACTELKL | | 46238 |
| HPV56 | E6 | 81 | 11 | YYDYSVYGATL | | 46239 |
| HPV56 | E7 | 69 | 8 | KFVVQLDI | | 46240 |
| HPV56 | E7 | 90 | 11 | LMGALTVTCPL | | 46241 |
| HPV56 | L1 | 275 | 8 | AYGDSMWF | | 46242 |
| HPV56 | L1 | 275 | 10 | AYGDSMWFYL | | 46243 |
| HPV56 | L1 | 422 | 10 | AYLHNMNANL | | 46244 |
| HPV56 | L1 | 422 | 11 | AYLHNMNANLL | | 46245 |
| HPV56 | L1 | 101 | 11 | AYQYRVFRVRL | | 46246 |
| HPV56 | L1 | 402 | 8 | EYELQFVF | | 46247 |
| HPV56 | L1 | 402 | 10 | EYELQFVFQL | | 46248 |
| HPV56 | L1 | 479 | 10 | FWDVNLQDSF | | 46249 |
| HPV56 | L1 | 69 | 9 | FYHAGSSRL | | 46250 |
| HPV56 | L1 | 69 | 10 | FYHAGSSRLL | | 46251 |
| HPV56 | L1 | 282 | 8 | FYLRREQL | | 46252 |
| HPV56 | L1 | 282 | 9 | FYLRREQLF | | 46253 |
| HPV56 | L1 | 238 | 10 | GFGAMDFKVL | | 46254 |
| HPV56 | L1 | 15 | 8 | HYGLCIFL | | 46255 |
| HPV56 | L1 | 20 | 11 | IFLDVGAVNVF | | 46256 |
| HPV56 | L1 | 32 | 8 | IFLQMATW | | 46257 |
| HPV56 | L1 | 68 | 10 | IFYHAGSSRL | | 46258 |
| HPV56 | L1 | 68 | 11 | IFYHAGSSRLL | | 46259 |
| HPV56 | L1 | 124 | 9 | IYNPDQERL | | 46260 |
| HPV56 | L1 | 124 | 11 | IYNPDQERLVW | | 46261 |
| HPV56 | L1 | 8 | 11 | IYRDPPLHYGL | | 46262 |
| HPV56 | L1 | 116 | 9 | KFGLPDTNI | | 46263 |
| HPV56 | L1 | 478 | 11 | KFWDVNLQDSF | | 46264 |
| HPV56 | L1 | 387 | 11 | KYDARKINQYL | | 46265 |
| HPV56 | L1 | 476 | 9 | KYKFWDVNL | | 46266 |
| HPV56 | L1 | 450 | 10 | KYRYVRSTAI | | 46267 |
| HPV56 | L1 | 340 | 8 | LFNKPYWL | | 46268 |
| HPV56 | L1 | 1 | 8 | MMLPMMYI | | 46269 |
| HPV56 | L1 | 5 | 10 | MMYIYRDPPL | | 46270 |
| HPV56 | L1 | 280 | 10 | MWFYLRREQL | | 46271 |
| HPV56 | L1 | 280 | 11 | MWFYLRREQLF | | 46272 |
| HPV56 | L1 | 6 | 9 | MYIYRDPPL | | 46273 |
| HPV56 | L1 | 426 | 10 | NMNANLLEDW | | 46274 |
| HPV56 | L1 | 375 | 11 | NMTISTATEQL | | 46275 |
| HPV56 | L1 | 4 | 11 | PMMYIYRDPPL | | 46276 |
| HPV56 | L1 | 494 | 8 | QFPLGRKF | | 46277 |
| HPV56 | L1 | 494 | 9 | QFPLGRKFL | | 46278 |
| HPV56 | L1 | 406 | 9 | QFVFQLCKI | | 46279 |
| HPV56 | L1 | 406 | 11 | QFVFQLCKITL | | 46280 |
| HPV56 | L1 | 395 | 11 | QYLRHVEEYEL | | 46281 |
| HPV56 | L1 | 103 | 9 | QYRVFRVRL | | 46282 |
| HPV56 | L1 | 452 | 8 | RYVRSTAI | | 46283 |
| HPV56 | L1 | 487 | 9 | SFSTDLDQF | | 46284 |
| HPV56 | L1 | 487 | 11 | SFSTDLDQFPL | | 46285 |
| HPV56 | L1 | 332 | 9 | SMITSEAQL | | 46286 |
| HPV56 | L1 | 332 | 10 | SMITSEAQLF | | 46287 |
| HPV56 | L1 | 279 | 11 | SMWFYLRREQL | | 46288 |
| HPV56 | L1 | 61 | 8 | SYVKRTSI | | 46289 |
| HPV56 | L1 | 61 | 9 | SYVKRTSIF | | 46290 |
| HPV56 | L1 | 38 | 11 | TWRPSENKVYL | | 46291 |
| HPV56 | L1 | 29 | 11 | VFPIFLQMATW | | 46292 |
| HPV56 | L1 | 408 | 9 | VFQLCKITL | | 46293 |
| HPV56 | L1 | 324 | 11 | VYVATPSGSMI | | 46294 |
| HPV56 | L1 | 281 | 9 | WFYLRREQL | | 46295 |
| HPV56 | L1 | 281 | 10 | WFYLRREQLF | | 46296 |
| HPV56 | L2 | 240 | 9 | AFLDRPATL | | 46297 |
| HPV56 | L2 | 286 | 11 | AFTTRRGGVRF | | 46298 |
| HPV56 | L2 | 275 | 8 | DFMNIVAL | | 46299 |
| HPV56 | L2 | 444 | 10 | FFRRRRRKRI | | 46300 |
| HPV56 | L2 | 401 | 9 | FYSGPDIVL | | 46301 |
| HPV56 | L2 | 217 | 10 | GFRRIAAPRL | | 46302 |
| HPV56 | L2 | 318 | 9 | HYYYDISPI | | 46303 |

TABLE XVIII-continued

A24 Motif Peptides

| Type | Protein | Position | No. of Amino Acids | Sequence | A*2402 | Seq. Id. No. |
|---|---|---|---|---|---|---|
| HPV56 | L2 | 255 | 9 | LFEGTDTSL | | 46304 |
| HPV56 | L2 | 255 | 11 | LFEGTDTSLAF | | 46305 |
| HPV56 | L2 | 161 | 8 | LFIDPPVI | | 46306 |
| HPV56 | L2 | 50 | 8 | LFTYFGGL | | 46307 |
| HPV56 | L2 | 50 | 10 | LFTYFGGLGI | | 46308 |
| HPV56 | L2 | 347 | 8 | LYDIYANI | | 46309 |
| HPV56 | L2 | 121 | 8 | NFTGSGGF | | 46310 |
| HPV56 | L2 | 121 | 10 | NFTGSGGFEI | | 46311 |
| HPV56 | L2 | 400 | 8 | PFYSGPDI | | 46312 |
| HPV56 | L2 | 400 | 10 | PFYSGPDIVL | | 46313 |
| HPV56 | L2 | 423 | 10 | PYDVTHDVYI | | 46314 |
| HPV56 | L2 | 46 | 9 | QWGSLFTYF | | 46315 |
| HPV56 | L2 | 295 | 11 | RFSRLGRKATI | | 46316 |
| HPV56 | L2 | 436 | 9 | SFALWPVYF | | 46317 |
| HPV56 | L2 | 436 | 10 | SFALWPVYFF | | 46318 |
| HPV56 | L2 | 343 | 8 | SFDGLYDI | | 46319 |
| HPV56 | L2 | 191 | 10 | SYEEIPMQTF | | 46320 |
| HPV56 | L2 | 39 | 9 | TWADKILQW | | 46321 |
| HPV56 | L2 | 52 | 8 | TYFGGLGI | | 46322 |
| HPV56 | L2 | 430 | 8 | VYIQGSSF | | 46323 |
| HPV56 | L2 | 430 | 10 | VYIQGSSFAL | | 46324 |
| HPV56 | L2 | 430 | 11 | VYIQGSSFALW | | 46325 |
| HPV56 | L2 | 443 | 11 | YFFRRRRRKRI | | 46326 |
| HPV56 | L2 | 319 | 8 | YYYDISPI | | 46327 |

TABLE XIX

DR Supermotif Peptides

| Type | Protein | Position | Sequence | Sequence Id. No. | Core Sequence | Core Seq. Id. No. |
|---|---|---|---|---|---|---|
| HPV16 | E1 | 319 | AAALYWYKTGISNIS | 46328 | LYWYKTGIS | 48425 |
| HPV16 | E1 | 271 | ACSWGMVVLLLVRYK | 46329 | WGMVVLLLV | 48426 |
| HPV16 | E1 | 243 | AFGLTPSIADSIKTL | 46330 | LTPSIADSI | 48427 |
| HPV16 | E1 | 402 | AKIVKDCATMCRHYK | 46331 | VKDCATMCR | 48428 |
| HPV16 | E1 | 321 | ALYWYKTGISNISEV | 46332 | WYKTGISNI | 48429 |
| HPV16 | E1 | 392 | ASAFLKSNSQAKIVK | 46333 | FLKSNSQAK | 48430 |
| HPV16 | E1 | 262 | CLYLHIQSLACSWGM | 46334 | LHIQSLACS | 48431 |
| HPV16 | E1 | 307 | CMMIEPPKLRSTAAA | 46335 | IEPPKLRST | 48432 |
| HPV16 | E1 | 18 | CNGWFYVEAVVEKKT | 46336 | WFYVEAVVE | 48433 |
| HPV16 | E1 | 531 | CWNYIDDNLRNALDG | 46337 | YIDDNLRNA | 48434 |
| HPV16 | E1 | 355 | DCTFELSQMVQWAYD | 46338 | FELSQMVQW | 48435 |
| HPV16 | E1 | 544 | DGNLVSMDVKHRPLV | 46339 | LVSMDVKHR | 48436 |
| HPV16 | E1 | 609 | DKNWKSFFSRTWSRL | 46340 | WKSFFSRTW | 48437 |
| HPV16 | E1 | 375 | DSEIAYKYAQLADTN | 46341 | IAYKYAQLA | 48438 |
| HPV16 | E1 | 134 | DSGYGNTEVETQQML | 46342 | YGNTEVETQ | 48439 |
| HPV16 | E1 | 238 | DWCIAAFGLTPSIAD | 46343 | IAAFGLTPS | 48440 |
| HPV16 | E1 | 377 | EIAYKYAQLADTNSN | 46344 | YKYAQLADT | 48441 |
| HPV16 | E1 | 294 | EKLLSKLLCVSPMCM | 46345 | LSKLLCVSP | 48442 |
| HPV16 | E1 | 641 | FKCVSGQNTNTL--- | 46346 | VSGQNTNTL | 48443 |
| HPV16 | E1 | 635 | GDSLPTFKCVSGQNT | 46347 | LPTFKCVSG | 48444 |
| HPV16 | E1 | 48 | GEDLVDFIVNDNDYL | 46348 | LVDFIVNDN | 48445 |
| HPV16 | E1 | 180 | GEGVSERHTICQTPL | 46349 | VSERHTICQ | 48446 |
| HPV16 | E1 | 439 | GGDWKQIVMFLRYQG | 46350 | WKQIVMFLR | 48447 |
| HPV16 | E1 | 485 | GKSLFGMSLMKFLQG | 46351 | LFGMSLMKF | 48448 |
| HPV16 | E1 | 499 | GSVICFVNSKSHFWL | 46352 | ICFVNSKSH | 48449 |
| HPV16 | E1 | 453 | GVEFMSFLTALKRFL | 46353 | FMSFLTALK | 48450 |
| HPV16 | E1 | 20 | GWFYVEAVVEKKTGD | 46354 | YVEAVVEKK | 48451 |
| HPV16 | E1 | 71 | HALFTAQEAKQHRDA | 46355 | FTAQEAKQH | 48452 |
| HPV16 | E1 | 554 | HRPLVQLKCPPLLIT | 46356 | LVQLKCPPL | 48453 |
| HPV16 | E1 | 241 | IAAFGLTPSIADSIK | 46357 | FGLTPSIAD | 48454 |
| HPV16 | E1 | 293 | IEKLLSKLLCVSPMC | 46358 | LLSKLLCVS | 48455 |
| HPV16 | E1 | 521 | IGMLDDATVPCWNYI | 46359 | LDDATVPCW | 48456 |
| HPV16 | E1 | 254 | IKTLLQQYCLYLHIQ | 46360 | LLQQYCLYL | 48457 |
| HPV16 | E1 | 476 | ILLYGAANTGKSLFG | 46361 | YGAANTGKS | 48458 |
| HPV16 | E1 | 332 | ISEVYGDTPEWIQRQ | 46362 | VYGDTPEWI | 48459 |
| HPV16 | E1 | 215 | KELYGVSFSELVRPF | 46363 | YGVSFSELV | 48460 |
| HPV16 | E1 | 520 | KIGMLDDATVPCWNY | 46364 | MLDDATVPC | 48461 |
| HPV16 | E1 | 473 | KNCILLYGAANTGKS | 46365 | ILLYGAANT | 48462 |
| HPV16 | E1 | 90 | KRKYLVSPLSDISGC | 46366 | YLVSPLSDI | 48463 |
| HPV16 | E1 | 613 | KSFFSRTWSRLSLHE | 46367 | FSRTWSRLS | 48464 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV16 | E1 | 508 | KSHFWLQPLADAKIG | 46368 | FWLQPLADA | 48465 |
| HPV16 | E1 | 486 | KSLFGMSLMKFLQGS | 46369 | FGMSLMKFL | 48466 |
| HPV16 | E1 | 255 | KTLLQQYCLYLHIQS | 46370 | LQQYCLYLH | 48467 |
| HPV16 | E1 | 463 | LKRFLQGIPKKNCIL | 46371 | FLQGIPKKN | 48468 |
| HPV16 | E1 | 300 | LLCVSPMCMMIEPPK | 46372 | VSPMCMMIE | 48469 |
| HPV16 | E1 | 493 | LMKFLQGSVICFVNS | 46373 | FLQGSVICF | 48470 |
| HPV16 | E1 | 198 | LNVLKTSNAKAAMLA | 46374 | LKTSNAKAA | 48471 |
| HPV16 | E1 | 467 | LQGIPKKNCILLYGA | 46375 | IPKKNCILL | 48472 |
| HPV16 | E1 | 513 | LQPLADAKIGMLDDA | 46376 | LADAKIGML | 48473 |
| HPV16 | E1 | 297 | LSKLLCVSPMCMMIE | 46377 | LLCVSPMCM | 48474 |
| HPV16 | E1 | 557 | LVQLKCPPLLITSNI | 46378 | LKCPPLLIT | 48475 |
| HPV16 | E1 | 217 | LYGVSFSELVRPFKS | 46379 | VSFSELVRP | 48476 |
| HPV16 | E1 | 322 | LYWYKTGISNISEVY | 46380 | YKTGISNIS | 48477 |
| HPV16 | E1 | 494 | MKFLQGSVICFVNSK | 46381 | LQGSVICFV | 48478 |
| HPV16 | E1 | 425 | MSQWIKYRCDRVDDG | 46382 | WIKYRCDRV | 48479 |
| HPV16 | E1 | 474 | NCILLYGAANTGKSL | 46383 | LLYGAANTG | 48480 |
| HPV16 | E1 | 370 | NDIVDDSEIAYKYAQ | 46384 | VDDSEIAYK | 48481 |
| HPV16 | E1 | 59 | NDYLTQAETETAHAL | 46385 | LTQAETETA | 48482 |
| HPV16 | E1 | 19 | NGWFYVEAVVEKKTG | 46386 | FYVEAVVEK | 48483 |
| HPV16 | E1 | 584 | NRLVVFTFPNEFPFD | 46387 | VVFTFPNEF | 48484 |
| HPV16 | E1 | 139 | NTEVETQQMLQVEGR | 46388 | VETQQMLQV | 48485 |
| HPV16 | E1 | 340 | PEWIQRQTVLQHSFN | 46389 | IQRQTVLQH | 48486 |
| HPV16 | E1 | 305 | PMCMMIEPPKLRSTA | 46390 | MMIEPPKLR | 48487 |
| HPV16 | E1 | 312 | PPKLRSTAAALYWYK | 46391 | LRSTAAALY | 48488 |
| HPV16 | E1 | 563 | PPLLITSNINAGTDS | 46392 | LITSNINAG | 48489 |
| HPV16 | E1 | 401 | QAKIVKDCATMCRHY | 46393 | IVKDCATMC | 48490 |
| HPV16 | E1 | 365 | QWAYDNDIVDDSEIA | 46394 | YDNDIVDDS | 48491 |
| HPV16 | E1 | 290 | RETIEKLLSKLLCVS | 46395 | IEKLLSKLL | 48492 |
| HPV16 | E1 | 186 | RHTICQTPLTNILNV | 46396 | ICQTPLTNI | 48493 |
| HPV16 | E1 | 91 | RKYLVSPLSDISGCV | 46397 | LVSPLSDIS | 48494 |
| HPV16 | E1 | 540 | RNALDGNLVSMDVKH | 46398 | LDGNLVSMD | 48495 |
| HPV16 | E1 | 555 | RPLVQLKCPPLLITS | 46399 | VQLKCPPLL | 48496 |
| HPV16 | E1 | 127 | RRLFESEDSGYGNTE | 46400 | FESEDSGYG | 48497 |
| HPV16 | E1 | 578 | RWPYLHNRLVVFTFP | 46401 | YLHNRLVVF | 48498 |
| HPV16 | E1 | 223 | SELVRPFKSNKSTCC | 46402 | VRPFKSNKS | 48499 |
| HPV16 | E1 | 102 | SGCVDNNISPRLKAI | 46403 | VDNNISPRL | 48500 |
| HPV16 | E1 | 509 | SHFWLQPLADAKIGM | 46404 | WLQPLADAK | 48501 |
| HPV16 | E1 | 298 | SKLLCVSPMCMMIEP | 46405 | LCVSPMCMM | 48502 |
| HPV16 | E1 | 549 | SMDVKHRPLVQLKCP | 46406 | VKHRPLVQL | 48503 |
| HPV16 | E1 | 110 | SPRLKAICIEKQSRA | 46407 | LKAICIEKQ | 48504 |
| HPV16 | E1 | 617 | SRTWSRLSLHEDEDK | 46408 | WSRLSLHED | 48505 |
| HPV16 | E1 | 273 | SWGMVVLLLVRYKCG | 46409 | MVVLLLVRY | 48506 |
| HPV16 | E1 | 195 | TNILNVLKTSNAKAA | 46410 | LNVLKTSNA | 48507 |
| HPV16 | E1 | 339 | TPEWIQRQTVLQHSF | 46411 | WIQRQTVLQ | 48508 |
| HPV16 | E1 | 24 | VEAVVEKKTGDAISD | 46412 | VVEKKTGDA | 48509 |
| HPV16 | E1 | 454 | VEFMSFLTALKRFLQ | 46413 | MSFLTALKR | 48510 |
| HPV16 | E1 | 588 | VFTFPNEFPFDENGN | 46414 | FPNEFPFDE | 48511 |
| HPV16 | E1 | 501 | VICFVNSKSHFWLQP | 46415 | FVNSKSHFW | 48512 |
| HPV16 | E1 | 278 | VLLLVRYKCGKNRET | 46416 | LVRYKCGKN | 48513 |
| HPV16 | E1 | 446 | VMFLRYQGVEFMSFL | 46417 | LRYQGVEFM | 48514 |
| HPV16 | E1 | 86 | VQVLKRKYLVSPLSD | 46418 | LKRKYLVSP | 48515 |
| HPV16 | E1 | 226 | VRPFKSNKSTCCDWC | 46419 | FKSNKSTCC | 48516 |
| HPV16 | E1 | 274 | WGMVVLLLVRYKCGK | 46420 | VVLLLVRYK | 48517 |
| HPV16 | E1 | 428 | WIKYRCDRVDDGGDW | 46421 | YRCDRVDDG | 48518 |
| HPV16 | E1 | 579 | WPYLHNRLVVFTFPN | 46422 | LHNRLVVFT | 48519 |
| HPV16 | E1 | 382 | YAQLADTNSNASAFL | 46423 | LADTNSNAS | 48520 |
| HPV16 | E1 | 261 | YCLYLHIQSLACSWG | 46424 | YLHIQSLAC | 48521 |
| HPV16 | E1 | 264 | YLHIQSLACSWGMVV | 46425 | IQSLACSWG | 48522 |
| HPV16 | E2 | 178 | AEKYSKNKVWEVHAG | 46426 | YSKNKVWEV | 48523 |
| HPV16 | E2 | 44 | AIYYKAREMGFKHIN | 46427 | YKAREMGFK | 48524 |
| HPV16 | E2 | 268 | APILTAFNSSHKGRI | 46428 | LTAFNSSHK | 48525 |
| HPV16 | E2 | 49 | AREMGFKHINHQVVP | 46429 | MGFKHINHQ | 48526 |
| HPV16 | E2 | 229 | AVALGTEETQTTIQR | 46430 | LGTEETQTT | 48527 |
| HPV16 | E2 | 312 | CTLYTAVSSTWHWTG | 46431 | YTAVSSTWH | 48528 |
| HPV16 | E2 | 347 | DQFLSQVKIPKTITV | 46432 | LSQVKIPKT | 48529 |
| HPV16 | E2 | 99 | DVSLEVYLTAPTGCI | 46433 | LEVYLTAPT | 48530 |
| HPV16 | E2 | 152 | EGQVDYYGLYYVHEG | 46434 | VDYYGLYYV | 48531 |
| HPV16 | E2 | 77 | ELQLTLETIYNSQYS | 46435 | LTLETIYNS | 48532 |
| HPV16 | E2 | 83 | ETIYNSQYSNEKWTL | 46436 | YNSQYSNEK | 48533 |
| HPV16 | E2 | 121 | EVQFDGDICNTMHYT | 46437 | FDGDICNTM | 48534 |
| HPV16 | E2 | 54 | FKHINHQVVPTLAVS | 46438 | INHQVVPTL | 48535 |
| HPV16 | E2 | 192 | GGQVILCPTSVFSSN | 46439 | VILCPTSVF | 48536 |
| HPV16 | E2 | 326 | GHNVKHKSAIVTLTY | 46440 | VKHKSAIVT | 48537 |
| HPV16 | E2 | 159 | GLYYVHEGIRTYFVQ | 46441 | YVHEGIRTY | 48538 |
| HPV16 | E2 | 193 | GQVILCPTSVFSSNE | 46442 | ILCPTSVFS | 48539 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV16 | E2 | 311 | HCTLYTAVSSTWHWT | 46443 | LYTAVSSTW | 48540 |
| HPV16 | E2 | 164 | HEGIRTYFVQFKDDA | 46444 | IRTYFVQFK | 48541 |
| HPV16 | E2 | 139 | HIYICEEASVTVVEG | 46445 | ICEEASVTV | 48542 |
| HPV16 | E2 | 59 | HQVVPTLAVSKNKAL | 46446 | VPTLAVSKN | 48543 |
| HPV16 | E2 | 33 | IDYWKHMRLECAIYY | 46447 | WKHMRLECA | 48544 |
| HPV16 | E2 | 183 | KNKVWEVHAGGQVIL | 46448 | VWEVHAGGQ | 48545 |
| HPV16 | E2 | 94 | KWTLQDVSLEVYLTA | 46449 | LQDVSLEVY | 48546 |
| HPV16 | E2 | 102 | LEVYLTAPTGCIKKH | 46450 | YLTAPTGCI | 48547 |
| HPV16 | E2 | 73 | LQAIELQLTLETIYN | 46451 | IELQLTLET | 48548 |
| HPV16 | E2 | 350 | LSQVKIPKTITVSTG | 46452 | VKIPKTITV | 48549 |
| HPV16 | E2 | 19 | LTHYENDSTDLRDHI | 46453 | YENDSTDLR | 48550 |
| HPV16 | E2 | 92 | NEKWTLQDVSLEVYL | 46454 | WTLQDVSLE | 48551 |
| HPV16 | E2 | 58 | NHQVVPTLAVSKNKA | 46455 | VVPTLAVSK | 48552 |
| HPV16 | E2 | 70 | NKALQAIELQLTLET | 46456 | LQAIELQLT | 48553 |
| HPV16 | E2 | 211 | PEIIRQHLANHPAAT | 46457 | IRQHLANHP | 48554 |
| HPV16 | E2 | 238 | QTTIQRPRSEPDTGN | 46458 | IQRPRSEPD | 48555 |
| HPV16 | E2 | 194 | QVILCPTSVFSSNEV | 46459 | LCPTSVFSS | 48556 |
| HPV16 | E2 | 352 | QVKIPKTITVSTGFM | 46460 | IPKTITVST | 48557 |
| HPV16 | E2 | 262 | RDSVDSAPILTAFNS | 46461 | VDSAPILTA | 48558 |
| HPV16 | E2 | 10 | RLNVCQDKILTHYEN | 46462 | VCQDKILTH | 48559 |
| HPV16 | E2 | 215 | RQHLANHPAATHTKA | 46463 | LANHPAATH | 48560 |
| HPV16 | E2 | 305 | RYRFKKHCTLYTAVS | 46464 | FKKHCTLYT | 48561 |
| HPV16 | E2 | 101 | SLEVYLTAPTGCIKK | 46465 | VYLTAPTGC | 48562 |
| HPV16 | E2 | 205 | SNEVSSPEIIRQHLA | 46466 | VSSPEIIRQ | 48563 |
| HPV16 | E2 | 210 | SPEIIRQHLANHPAA | 46467 | IIRQHLANH | 48564 |
| HPV16 | E2 | 147 | SVTVVEGQVDYYGLY | 46468 | VVEGQVDYY | 48565 |
| HPV16 | E2 | 138 | THIYICEEASVTVVE | 46469 | YICEEASVT | 48566 |
| HPV16 | E2 | 257 | TKLLHRDSVDSAPIL | 46470 | LHRDSVDSA | 48567 |
| HPV16 | E2 | 64 | TLAVSKNKALQAIEL | 46471 | VSKNKALQA | 48568 |
| HPV16 | E2 | 200 | TSVFSSNEVSSPEII | 46472 | FSSNEVSSP | 48569 |
| HPV16 | E2 | 256 | TTKLLHRDSVDSAPI | 46473 | LLHRDSVDS | 48570 |
| HPV16 | E2 | 321 | TWHWTGHNVKHKSAI | 46474 | WTGHNVKHK | 48571 |
| HPV16 | E2 | 155 | VDYYGLYYVHEGIRT | 46475 | YGLYYVHEG | 48572 |
| HPV16 | E2 | 36 | WKHMRLECAIYYKAR | 46476 | MRLECAIYY | 48573 |
| HPV16 | E2 | 134 | YTNWTHIYICEEASV | 46477 | WTHIYICEE | 48574 |
| HPV16 | E5 | 1 | ---MTNLDTASTTLL | 46478 | MTNLDTAST | 48575 |
| HPV16 | E5 | 16 | ACFLLCFCVLLCVCL | 46479 | LLCFCVLLC | 48576 |
| HPV16 | E5 | 57 | ASAFRCFIVYIIFVY | 46480 | FRCFIVYII | 48577 |
| HPV16 | E5 | 21 | CFCVLLCVCLLIRPL | 46481 | VLLCVCLLI | 48578 |
| HPV16 | E5 | 62 | CFIVYIIFVYIPLFL | 46482 | VYIIFVYIP | 48579 |
| HPV16 | E5 | 17 | CFLLCFCVLLCVCLL | 46483 | LCFCVLLCV | 48580 |
| HPV16 | E5 | 29 | CLLIRPLLLSVSTYT | 46484 | IRPLLLSVS | 48581 |
| HPV16 | E5 | 27 | CVCLLIRPLLLSVST | 46485 | LLIRPLLLS | 48582 |
| HPV16 | E5 | 23 | CVLLCVCLLIRPLLL | 46486 | LCVCLLIRP | 48583 |
| HPV16 | E5 | 22 | FCVLLCVCLLIRPLL | 46487 | LLCVCLLIR | 48584 |
| HPV16 | E5 | 60 | FRCFIVYIIFVYIPL | 46488 | FIVYIIFVY | 48585 |
| HPV16 | E5 | 69 | FVYIPLFLIHTHARF | 46489 | IPLFLIHTH | 48586 |
| HPV16 | E5 | 68 | IFVYIPLFLIHTHAR | 46490 | YIPLFLIHT | 48587 |
| HPV16 | E5 | 46 | IILVLLLWITAASAF | 46491 | VLLLWITAA | 48588 |
| HPV16 | E5 | 47 | ILVLLLWITAASAFR | 46492 | LLLWITAAS | 48589 |
| HPV16 | E5 | 32 | IRPLLLSVSTYTSLI | 46493 | LLLSVSTYT | 48590 |
| HPV16 | E5 | 64 | IVYIIFVYIPLFLIH | 46494 | IIFVYIPLF | 48591 |
| HPV16 | E5 | 15 | LACFLLCFCVLLCVC | 46495 | FLLCFCVLL | 48592 |
| HPV16 | E5 | 19 | LLCFCVLLCVCLLIR | 46496 | FCVLLCVCL | 48593 |
| HPV16 | E5 | 50 | LLLWITAASAFRCFI | 46497 | WITAASAFR | 48594 |
| HPV16 | E5 | 36 | LLSVSTYTSLIILVL | 46498 | VSTYTSLII | 48595 |
| HPV16 | E5 | 51 | LLWITAASAFRCFIV | 46499 | ITAASAFRC | 48596 |
| HPV16 | E5 | 48 | LVLLLWITAASAFRC | 46500 | LLWITAASA | 48597 |
| HPV16 | E5 | 4 | MTNLDTASTTLLACF | 46501 | LDTASTTLL | 48598 |
| HPV16 | E5 | 73 | PLFLIHTHARFLIT- | 46502 | LIHTHARFL | 48599 |
| HPV16 | E5 | 33 | RPLLLSVSTYTSLII | 46503 | LLSVSTYTS | 48600 |
| HPV16 | E5 | 44 | SLIILVLLLWITAAS | 46504 | ILVLLLWIT | 48601 |
| HPV16 | E5 | 11 | STTLLACFLLCFCVL | 46505 | LLACFLLCF | 48602 |
| HPV16 | E5 | 43 | TSLIILVLLLWITAA | 46506 | IILVLLLWI | 48603 |
| HPV16 | E5 | 12 | TTLLACFLLCFCVLL | 46507 | LACFLLCFC | 48604 |
| HPV16 | E5 | 28 | VCLLIRPLLLSVSTY | 46508 | LIRPLLLSV | 48605 |
| HPV16 | E5 | 49 | VLLLWITAASAFRCF | 46509 | LWITAASAF | 48606 |
| HPV16 | E5 | 39 | VSTYTSLIILVLLLW | 46510 | YTSLIILVL | 48607 |
| HPV16 | E5 | 65 | VYIIFVYIPLFLIHT | 46511 | IFVYIPLFL | 48608 |
| HPV16 | E5 | 66 | YIIFVYIPLFLIHTH | 46512 | FVYIPLFLI | 48609 |
| HPV16 | E5 | 71 | YIPLFLIHTHARFLI | 46513 | LFLIHTHAR | 48610 |
| HPV16 | E5 | 42 | YTSLIILVLLLWITA | 46514 | LIILVLLLW | 48611 |
| HPV16 | E6 | 1 | ---MHQKRTAMFQDP | 46515 | MHQKRTAMF | 48612 |
| HPV16 | E6 | 61 | CIVYRDGNPYAVCDK | 46516 | YRDGNPYAV | 48613 |
| HPV16 | E6 | 76 | CLKFYSKISEYRHYC | 46517 | FYSKISEYR | 48614 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV16 | E6 | 90 | CYSLYGTTLEQQYNK | 46518 | LYGTTLEQQ | 48615 |
| HPV16 | E6 | 54 | DFAFRDLCIVYRDGN | 46519 | FRDLCIVYR | 48616 |
| HPV16 | E6 | 35 | DIILECVYCKQQLLR | 46520 | LECVYCKQQ | 48617 |
| HPV16 | E6 | 108 | DLLIRCINCQKPLCP | 46521 | IRCINCQKP | 48618 |
| HPV16 | E6 | 39 | ECVYCKQQLLRREVY | 46522 | YCKQQLLRR | 48619 |
| HPV16 | E6 | 99 | EQQYNKPLCDLLIRC | 46523 | YNKPLCDLL | 48620 |
| HPV16 | E6 | 135 | FHNIRGRWTGRCMSC | 46524 | IRGRWTGRC | 48621 |
| HPV16 | E6 | 144 | GRCMSCCRSSRTRRE | 46525 | MSCCRSSRT | 48622 |
| HPV16 | E6 | 88 | HYCSLYGTTLEQQY | 46526 | YSLYGTTLE | 48623 |
| HPV16 | E6 | 33 | IHDIILECVYCKQQL | 46527 | IILECVYCK | 48624 |
| HPV16 | E6 | 111 | IRCINCQKPLCPEEK | 46528 | INCQKPLCP | 48625 |
| HPV16 | E6 | 44 | KQQLLRREVYDFAFR | 46529 | LLRREVYDF | 48626 |
| HPV16 | E6 | 106 | LCDLLIRCINCQKPL | 46530 | LLIRCINCQ | 48627 |
| HPV16 | E6 | 103 | NKPLCDLLIRCINCQ | 46531 | LCDLLIRCI | 48628 |
| HPV16 | E6 | 19 | PRKLPQLCTELQTTI | 46532 | LPQLCTELQ | 48629 |
| HPV16 | E6 | 69 | PYAVCDKCLKFYSKI | 46533 | VCDKCLKFY | 48630 |
| HPV16 | E6 | 30 | QTTIHDIILECVYCK | 46534 | IHDIILECV | 48631 |
| HPV16 | E6 | 139 | RGRWTGRCMSCCRSS | 46535 | WTGRCMSCC | 48632 |
| HPV16 | E6 | 52 | VYDFAFRDLCIVYRD | 46536 | FAFRDLCIV | 48633 |
| HPV16 | E7 | 1 | ---MHGDTPTLHEYM | 46537 | MHGDTPTLH | 48634 |
| HPV16 | E7 | 84 | DLLMGTLGIVCPICS | 46538 | MGTLGIVCP | 48635 |
| HPV16 | E7 | 12 | HEYMLDLQPETTDLY | 46539 | MLDLQPETT | 48636 |
| HPV16 | E7 | 54 | HYNIVTFCCKCDSTL | 46540 | IVTFCCKCD | 48637 |
| HPV16 | E7 | 79 | IRTLEDLLMGTLGIV | 46541 | LEDLLMGTL | 48638 |
| HPV16 | E7 | 82 | LEDLLMGTLGIVCPI | 46542 | LLMGTLGIV | 48639 |
| HPV16 | E7 | 90 | LGIVCPICSQKP--- | 46543 | VCPICSQKP | 48640 |
| HPV16 | E7 | 87 | MGTLGIVCPICSQKP | 46544 | LGIVCPICS | 48641 |
| HPV16 | E7 | 15 | MLDLQPETTDLYCYE | 46545 | LQPETTDLY | 48642 |
| HPV16 | E7 | 69 | RLCVQSTHVDIRTLE | 46546 | VQSTHVDIR | 48643 |
| HPV16 | E7 | 74 | STHVDIRTLEDLLMG | 46547 | VDIRTLEDL | 48644 |
| HPV16 | E7 | 23 | TDLYCYEQLNDSSEE | 46548 | YCYEQLNDS | 48645 |
| HPV16 | E7 | 89 | TLGIVCPICSQKP-- | 46549 | IVCPICSQK | 48646 |
| HPV16 | E7 | 67 | TLRLCVQSTHVDIRT | 46550 | LCVQSTHVD | 48647 |
| HPV16 | E7 | 8 | TPTLHEYMLDLQPET | 46551 | LHEYMLDLQ | 48648 |
| HPV16 | L1 | 1 | ---MQVTFIYILVIT | 46552 | MQVTFIYIL | 48649 |
| HPV16 | L1 | 3 | -MQVTFIYILVITCY | 46553 | VTFIYILVI | 48650 |
| HPV16 | L1 | 414 | ADVMTYIHSMNSTIL | 46554 | MTYIHSMNS | 48651 |
| HPV16 | L1 | 293 | AGAVGENVPDDLYIK | 46555 | VGENVPDDL | 48652 |
| HPV16 | L1 | 236 | AMDFTTLQANKSEVP | 46556 | FTTLQANKS | 48653 |
| HPV16 | L1 | 38 | ATVYLPPVPVSKVVS | 46557 | YLPPVPVSK | 48654 |
| HPV16 | L1 | 374 | CAAISTSETTYKNTN | 46558 | ISTSETTYK | 48655 |
| HPV16 | L1 | 175 | CISMDYKQTQLCLIG | 46559 | MDYKQTQLC | 48656 |
| HPV16 | L1 | 214 | CPPLELINTVIQDGD | 46560 | LELINTVIQ | 48657 |
| HPV16 | L1 | 54 | DEYVARTNIYYHAGT | 46561 | VARTNIYYH | 48658 |
| HPV16 | L1 | 400 | DLQFIFQLCKITLTA | 46562 | FIFQLCKIT | 48659 |
| HPV16 | L1 | 303 | DLYIKGSGSTANLAS | 46563 | IKGSGSTAN | 48660 |
| HPV16 | L1 | 116 | DTSFYNPDTQRLVWA | 46564 | FYNPDTQRL | 48661 |
| HPV16 | L1 | 430 | DWNFGLQPPPGGTLE | 46565 | FGLQPPPGG | 48662 |
| HPV16 | L1 | 37 | EATVYLPPVPVSKVV | 46566 | VYLPPVPVS | 48663 |
| HPV16 | L1 | 444 | EDTYRFVTSQAIACQ | 46567 | YRFVTSQAI | 48664 |
| HPV16 | L1 | 18 | ENDVNVYHIFFQMSL | 46568 | VNVYHIFFQ | 48665 |
| HPV16 | L1 | 477 | EVNLKEKFSADLDQF | 46569 | LKEKFSADL | 48666 |
| HPV16 | L1 | 248 | EVPLDICTSICKYPD | 46570 | LDICTSICK | 48667 |
| HPV16 | L1 | 27 | FFQMSLWLPSEATVY | 46571 | MSLWLPSEA | 48668 |
| HPV16 | L1 | 276 | FFYLRREQMFVRHLF | 46572 | LRREQMFVR | 48669 |
| HPV16 | L1 | 234 | FGAMDFTTLQANKSE | 46573 | MDFTTLQAN | 48670 |
| HPV16 | L1 | 8 | FIYILVITCYENDVN | 46574 | ILVITCYEN | 48671 |
| HPV16 | L1 | 239 | FTTLQANKSEVPLDI | 46575 | LQANKSEVP | 48672 |
| HPV16 | L1 | 396 | GEEYDLQFIFQLCKI | 46576 | YDLQFIFQL | 48673 |
| HPV16 | L1 | 195 | GEHWGKGSPCTNVAV | 46577 | WGKGSPCTN | 48674 |
| HPV16 | L1 | 96 | GLQYRVFRIHLPDPN | 46578 | YRVFRIHLP | 48675 |
| HPV16 | L1 | 355 | GNQLFVTVVDTTRST | 46579 | LFVTVVDTT | 48676 |
| HPV16 | L1 | 139 | GQPLGVGISGHPLLN | 46580 | LGVGISGHP | 48677 |
| HPV16 | L1 | 133 | GVEVGRGQPLGVGIS | 46581 | VGRGQPLGV | 48678 |
| HPV16 | L1 | 143 | GVGISGHPLLNKLDD | 46582 | ISGHPLLNK | 48679 |
| HPV16 | L1 | 76 | HPYFPIKKPNNNKIL | 46583 | FPIKKPNNN | 48680 |
| HPV16 | L1 | 404 | IFQLCKITLTADVMT | 46584 | LCKITLTAD | 48681 |
| HPV16 | L1 | 420 | IHSMNSTILEDWNFG | 46585 | MNSTILEDW | 48682 |
| HPV16 | L1 | 508 | KFTLGKRKATPTTSS | 46586 | LGKRKATPT | 48683 |
| HPV16 | L1 | 409 | KITLTADVMTYIHSM | 46587 | LTADVMTYI | 48684 |
| HPV16 | L1 | 246 | KSEVPLDICTSICKY | 46588 | VPLDICTSI | 48685 |
| HPV16 | L1 | 472 | KYTFWEVNLKEKFSA | 46589 | FWEVNLKEK | 48686 |
| HPV16 | L1 | 185 | LCLIGCKPPIGEHWG | 46590 | IGCKPPIGE | 48687 |
| HPV16 | L1 | 470 | LKKYTFWEVNLKEKF | 46591 | YTFWEVNLK | 48688 |
| HPV16 | L1 | 42 | LPPVPVSKVVSTDEY | 46592 | VPVSKVVST | 48689 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV16 | L1 | 30 | MSLWLPSEATVYLPP | 46593 | WLPSEATVY | 48690 |
| HPV16 | L1 | 417 | MTYIHSMNSTILEDW | 46594 | IHSMNSTIL | 48691 |
| HPV16 | L1 | 167 | NAGVDNRECISMDYK | 46595 | VDNRECISM | 48692 |
| HPV16 | L1 | 61 | NIYYHAGTSRLLAVG | 46596 | YHAGTSRLL | 48693 |
| HPV16 | L1 | 87 | NKILVPKVSGLQYRV | 46597 | LVPKVSGLQ | 48694 |
| HPV16 | L1 | 337 | NKPYWLQRAQGHNNG | 46598 | YWLQRAQGH | 48695 |
| HPV16 | L1 | 370 | NMSLCAAISTSETTY | 46599 | LCAAISTSE | 48696 |
| HPV16 | L1 | 86 | NNKILVPKVSGLQYR | 46600 | ILVPKVSGL | 48697 |
| HPV16 | L1 | 221 | NTVIQDGDMVDTGFG | 46601 | IQDGDMVDT | 48698 |
| HPV16 | L1 | 206 | NVAVNPGDCPPLELI | 46602 | VNPGDCPPL | 48699 |
| HPV16 | L1 | 301 | PDDLYIKGSGSTANL | 46603 | LYIKGSGST | 48700 |
| HPV16 | L1 | 250 | PLDICTSICKYPDYI | 46604 | ICTSICKYP | 48701 |
| HPV16 | L1 | 216 | PLELINTVIQDGDMV | 46605 | LINTVIQDG | 48702 |
| HPV16 | L1 | 109 | PNKFGFPDTSFYNPD | 46606 | FGFPDTSFY | 48703 |
| HPV16 | L1 | 44 | PVPVSKVVSTDEYVA | 46607 | VSKVVSTDE | 48704 |
| HPV16 | L1 | 402 | QFIFQLCKITLTADV | 46608 | FQLCKITLT | 48705 |
| HPV16 | L1 | 490 | QFPLGRKFLLQAGLK | 46609 | LGRKFLLQA | 48706 |
| HPV16 | L1 | 184 | QLCLIGCKPPIGEHW | 46610 | LIGCKPPIG | 48707 |
| HPV16 | L1 | 357 | QLFVTVVDTTRSTNM | 46611 | VTVVDTTRS | 48708 |
| HPV16 | L1 | 182 | QTQLCLIGCKPPIGE | 46612 | LCLIGCKPP | 48709 |
| HPV16 | L1 | 5 | QVTFIYILVITCYEN | 46613 | FIYILVITC | 48710 |
| HPV16 | L1 | 98 | QYRVFRIHLPDPNKF | 46614 | VFRIHLPDP | 48711 |
| HPV16 | L1 | 281 | REQMFVRHLFNRAGA | 46615 | MFVRHLFNR | 48712 |
| HPV16 | L1 | 287 | RHLFNRAGAVGENVP | 46616 | FNRAGAVGE | 48713 |
| HPV16 | L1 | 495 | RKFLLQAGLKAKPKF | 46617 | LLQAGLKAK | 48714 |
| HPV16 | L1 | 126 | RLVWACVGVEVGRGQ | 46618 | WACVGVEVG | 48715 |
| HPV16 | L1 | 485 | SADLDQFPLGRKFLL | 46619 | LDQFPLGRK | 48716 |
| HPV16 | L1 | 325 | SGSMVTSDAQIFNKP | 46620 | MVTSDAQIF | 48717 |
| HPV16 | L1 | 31 | SLWLPSEATVYLPPV | 46621 | LPSEATVYL | 48718 |
| HPV16 | L1 | 177 | SMDYKQTQLCLIGCK | 46622 | YKQTQLCLI | 48719 |
| HPV16 | L1 | 69 | SRLLAVGHPYFPIKK | 46623 | LAVGHPYFP | 48720 |
| HPV16 | L1 | 317 | SSNYFPTPSGSMVTS | 46624 | YFPTPSGSM | 48721 |
| HPV16 | L1 | 368 | STNMSLCAAISTSET | 46625 | MSLCAAIST | 48722 |
| HPV16 | L1 | 7 | TFIYILVITCYENDV | 46626 | YILVITCYE | 48723 |
| HPV16 | L1 | 60 | TNIYYHAGTSRLLAV | 46627 | YYHAGTSRL | 48724 |
| HPV16 | L1 | 124 | TQRLVWACVGVEVGR | 46628 | LVWACVGVE | 48725 |
| HPV16 | L1 | 39 | TVYLPPVPVSKVVST | 46629 | LPPVPVSKV | 48726 |
| HPV16 | L1 | 446 | TYRFVTSQAIACQKH | 46630 | FVTSQAIAC | 48727 |
| HPV16 | L1 | 101 | VFRIHLPDPNKFGFP | 46631 | IHLPDPNKF | 48728 |
| HPV16 | L1 | 6 | VTFIYILVITCYEND | 46632 | IYILVITCY | 48729 |
| HPV16 | L1 | 360 | VTVVDTTRSTNMSLC | 46633 | VDTTRSTNM | 48730 |
| HPV16 | L1 | 23 | VYHIFFQMSLWLPSE | 46634 | IFFQMSLWL | 48731 |
| HPV16 | L1 | 24 | YHIFFQMSLWLPSEA | 46635 | FFQMSLWLP | 48732 |
| HPV16 | L1 | 260 | YPDYIKMVSEPYGDS | 46636 | YIKMVSEPY | 48733 |
| HPV16 | L1 | 447 | YRFVTSQAIACQKHT | 46637 | VTSQAIACQ | 48734 |
| HPV16 | L1 | 99 | YRVFRIHLPDPNKFG | 46638 | FRIHLPDPN | 48735 |
| HPV16 | L2 | 1 | ---MRHKRSAKRTKR | 46639 | MRHKRSAKR | 48736 |
| HPV16 | L2 | 373 | ADDFITDTSTTPVPS | 46640 | FITDTSTTP | 48737 |
| HPV16 | L2 | 45 | ADQILQYGSMGVFFG | 46641 | ILQYGSMGV | 48738 |
| HPV16 | L2 | 339 | AEEIELQTITPSTYT | 46642 | IELQTITPS | 48739 |
| HPV16 | L2 | 446 | AGDFYLHPSYYMLRK | 46643 | FYLHPSYYM | 48740 |
| HPV16 | L2 | 427 | APSLIPIVPGSPQYT | 46644 | LIPIVPGSP | 48741 |
| HPV16 | L2 | 374 | DDFITDTSTTPVPSV | 46645 | ITDTSTTPV | 48742 |
| HPV16 | L2 | 242 | DPAFITTPTKLITYD | 46646 | FITTPTKLI | 48743 |
| HPV16 | L2 | 283 | DPDFLDIVALHRPAL | 46647 | FLDIVALHR | 48744 |
| HPV16 | L2 | 168 | DPSVLQPPTPAETGG | 46648 | VLQPPTPAE | 48745 |
| HPV16 | L2 | 46 | DQILQYGSMGVFFGG | 46649 | LQYGSMGVF | 48746 |
| HPV16 | L2 | 202 | DTFIVSTNPNTVTSS | 46650 | IVSTNPNTV | 48747 |
| HPV16 | L2 | 341 | EIELQTITPSTYTTT | 46651 | LQTITPSTY | 48748 |
| HPV16 | L2 | 198 | EIPMDTFIVSTNPNT | 46652 | MDTFIVSTN | 48749 |
| HPV16 | L2 | 114 | ETSFIDAGAPTSVPS | 46653 | FIDAGAPTS | 48750 |
| HPV16 | L2 | 406 | GGAYNIPLVSGPDIP | 46654 | YNIPLVSGP | 48751 |
| HPV16 | L2 | 181 | GGHFTLSSSTISTHN | 46655 | FTLSSSTIS | 48752 |
| HPV16 | L2 | 41 | GKTIADQILQYGSMG | 46656 | IADQILQYG | 48753 |
| HPV16 | L2 | 416 | GPDIPINITDQAPSL | 46657 | IPINITDQA | 48754 |
| HPV16 | L2 | 55 | GVFFGGLGIGTGSGT | 46658 | FGGLGIGTG | 48755 |
| HPV16 | L2 | 183 | HFTLSSSTISTHNYE | 46659 | LSSSTISTH | 48756 |
| HPV16 | L2 | 328 | HYYYDFSTIDSAEEI | 46660 | YDFSTIDSA | 48757 |
| HPV16 | L2 | 148 | ILDINNTVTTVTTHN | 46661 | INNTVTTVT | 48758 |
| HPV16 | L2 | 48 | ILQYGSMGVFFGGLG | 46662 | YGSMGVFFG | 48759 |
| HPV16 | L2 | 36 | IPKVEGKTIADQILQ | 46663 | VEGKTIADQ | 48760 |
| HPV16 | L2 | 411 | IPLVSGPDIPINITD | 46664 | VSGPDIPIN | 48761 |
| HPV16 | L2 | 289 | IVALHRPALTSRRTG | 46665 | LHRPALTSR | 48762 |
| HPV16 | L2 | 108 | IVSLVEETSFIDAGA | 46666 | LVEETSFID | 48763 |
| HPV16 | L2 | 326 | KVHYYYDFSTIDSAE | 46667 | YYYDFSTID | 48764 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV16 | L2 | 89 | LAPVRPPLTVDPVGP | 46668 | VRPPLTVDP | 48765 |
| HPV16 | L2 | 287 | LDIVALHRPALTSRR | 46669 | VALHRPALT | 48766 |
| HPV16 | L2 | 430 | LIPIVPGSPQYTIIA | 46670 | IVPGSPQYT | 48767 |
| HPV16 | L2 | 465 | LPYFFSDVSLAA--- | 46671 | FFSDVSLAA | 48768 |
| HPV16 | L2 | 393 | LSGYIPANTTIPFGG | 46672 | YIPANTTIP | 48769 |
| HPV16 | L2 | 365 | NNGLYDIYADDFITD | 46673 | LYDIYADDF | 48770 |
| HPV16 | L2 | 152 | NNTVTTVTTHNNPTF | 46674 | VTTVTTHNN | 48771 |
| HPV16 | L2 | 257 | NPAYEGIDVDNTLYF | 46675 | YEGIDVDNT | 48772 |
| HPV16 | L2 | 163 | NPTFTDPSVLQPPTP | 46676 | FTDPSVLQP | 48773 |
| HPV16 | L2 | 400 | NTTIPFGGAYNIPLV | 46677 | IPFGGAYNI | 48774 |
| HPV16 | L2 | 146 | PAILDINNTVTTVTT | 46678 | LDINNTVTT | 48775 |
| HPV16 | L2 | 284 | PDFLDIVALHRPALT | 46679 | LDIVALHRP | 48776 |
| HPV16 | L2 | 420 | PINITDQAPSLIPIV | 46680 | ITDQAPSLI | 48777 |
| HPV16 | L2 | 95 | PLTVDPVGPSDPSIV | 46681 | VDPVGPSDP | 48778 |
| HPV16 | L2 | 210 | PNTVTSSTPIPGSRP | 46682 | VTSSTPIPG | 48779 |
| HPV16 | L2 | 130 | PPDVSGFSITTSTDT | 46683 | VSGFSITTS | 48780 |
| HPV16 | L2 | 169 | PSVLQPPTPAETGGH | 46684 | LQPPTPAET | 48781 |
| HPV16 | L2 | 123 | PTSVPSIPPDVSGFS | 46685 | VPSIPPDVS | 48782 |
| HPV16 | L2 | 462 | RKRLPYFFSDVSLAA | 46686 | LPYFFSDVS | 48783 |
| HPV16 | L2 | 227 | RLGLYSRTTQQVKVV | 46687 | LYSRTTQQV | 48784 |
| HPV16 | L2 | 464 | RLPYFFSDVSLAA-- | 46688 | YFFSDVSLA | 48785 |
| HPV16 | L2 | 294 | RPALTSRRTGIRYSR | 46689 | LTSRRTGIR | 48786 |
| HPV16 | L2 | 93 | RPPLTVDPVGPSDPS | 46690 | LTVDPVGPS | 48787 |
| HPV16 | L2 | 301 | RTGIRYSRIGNKQTL | 46691 | IRYSRIGNK | 48788 |
| HPV16 | L2 | 72 | RTGYIPLGTRPPTAT | 46692 | YIPLGTRPP | 48789 |
| HPV16 | L2 | 394 | SGYIPANTTIPFGGA | 46693 | IPANTTIPF | 48790 |
| HPV16 | L2 | 53 | SMGVFFGGLGIGTGS | 46694 | VFFGGLGIG | 48791 |
| HPV16 | L2 | 222 | SRPVARLGLYSRTTQ | 46695 | VARLGLYSR | 48792 |
| HPV16 | L2 | 216 | STPIPGSRPVARLGL | 46696 | IPGSRPVAR | 48793 |
| HPV16 | L2 | 390 | STSLSGYIPANTTIP | 46697 | LSGYIPANT | 48794 |
| HPV16 | L2 | 86 | TDTLAPVRPPLTVDP | 46698 | LAPVRPPLT | 48795 |
| HPV16 | L2 | 193 | THNYEEIPMDTFIVS | 46699 | YEEIPMDTF | 48796 |
| HPV16 | L2 | 250 | TKLITYDNPAYEGID | 46700 | ITYDNPAYE | 48797 |
| HPV16 | L2 | 235 | TQQVKVVDPAFITTP | 46701 | VKVVDPAFI | 48798 |
| HPV16 | L2 | 115 | TSFIDAGAPTSVPSI | 46702 | IDAGAPTSV | 48799 |
| HPV16 | L2 | 382 | TTPVPSVPSTSLSGY | 46703 | VPSVPSTSL | 48800 |
| HPV16 | L2 | 98 | VDPVGPSDPSIVSLV | 46704 | VGPSDPSIV | 48801 |
| HPV16 | L2 | 327 | VHYYYDFSTIDSAEE | 46705 | YYDFSTIDS | 48802 |
| HPV16 | L2 | 238 | VKVVDPAFITTPTKL | 46706 | VDPAFITTP | 48803 |
| HPV16 | L2 | 126 | VPSIPPDVSGFSITT | 46707 | IPPDVSGFS | 48804 |
| HPV16 | L2 | 385 | VPSVPSTSLSGYIPA | 46708 | VPSTSLSGY | 48805 |
| HPV16 | L2 | 133 | VSGFSITTSTDTTPA | 46709 | FSITTSTDT | 48806 |
| HPV16 | L2 | 369 | YDIYADDFITDTSTT | 46710 | YADDFITDT | 48807 |
| HPV16 | L2 | 260 | YEGIDVDNTLYFSSN | 46711 | IDVDNTLYF | 48808 |
| HPV16 | L2 | 75 | YIPLGTRPPTATDTL | 46712 | LGTRPPTAT | 48809 |
| HPV16 | L2 | 306 | YSRIGNKQTLRTRSG | 46713 | IGNKQTLRT | 48810 |
| HPV16 | L2 | 330 | YYDFSTIDSAEEIEL | 46714 | FSTIDSAEE | 48811 |
| HPV18 | E1 | 399 | AAAFLKSNCQAKYLK | 46715 | FLKSNCQAK | 48812 |
| HPV18 | E1 | 409 | AKYLKDCATMCKHYR | 46716 | LKDCATMCK | 48813 |
| HPV18 | E1 | 328 | ALYWYRTGISNISEV | 46717 | WYRTGISNI | 48814 |
| HPV18 | E1 | 314 | CMLIQPPKLRSSVAA | 46718 | IQPPKLRSS | 48815 |
| HPV18 | E1 | 17 | CNGWFYVQAIVDKKT | 46719 | WFYVQAIVD | 48816 |
| HPV18 | E1 | 142 | CSEVEATQIQVTTNG | 46720 | VEATQIQVT | 48817 |
| HPV18 | E1 | 538 | CWTYFDTYMRNALDG | 46721 | YFDTYMRNA | 48818 |
| HPV18 | E1 | 278 | DCKWGVLILALLRYK | 46722 | WGVLILALL | 48819 |
| HPV18 | E1 | 384 | DMAFEYALLADSNSN | 46723 | FEYALLADS | 48820 |
| HPV18 | E1 | 583 | DNRWPYLESRITVFE | 46724 | WPYLESRIT | 48821 |
| HPV18 | E1 | 137 | DSGYGCSEVEATQIQ | 46725 | YGCSEVEAT | 48822 |
| HPV18 | E1 | 362 | DSNFDLSEMVQWAFD | 46726 | FDLSEMVQW | 48823 |
| HPV18 | E1 | 624 | ERTWSRLDLHEEEED | 46727 | WSRLDLHEE | 48824 |
| HPV18 | E1 | 382 | ESDMAFEYALLADSN | 46728 | MAFEYALLA | 48825 |
| HPV18 | E1 | 312 | ETCMLIQPPKLRSSV | 46729 | MLIQPPKLR | 48826 |
| HPV18 | E1 | 542 | FDTYMRNALDGNPIS | 46730 | YMRNALDGN | 48827 |
| HPV18 | E1 | 500 | FIHFIQGAVISFVNS | 46731 | FIQGAVISF | 48828 |
| HPV18 | E1 | 268 | FILYAHIQCLDCKWG | 46732 | YAHIQCLDC | 48829 |
| HPV18 | E1 | 261 | FKTLIQPFILYAHIQ | 46733 | LIQPFILYA | 48830 |
| HPV18 | E1 | 506 | GAVISFVNSTSHFWL | 46734 | ISFVNSTSH | 48831 |
| HPV18 | E1 | 159 | GGNVCSGGSTEAIDN | 46735 | VCSGGSTEA | 48832 |
| HPV18 | E1 | 643 | GNPFGTFKLRAGQNH | 46736 | FGTFKLRAG | 48833 |
| HPV18 | E1 | 19 | GWFYVQAIVDKKTGD | 46737 | YVQAIVDKK | 48834 |
| HPV18 | E1 | 561 | HKPLIQLKCPPILLT | 46738 | LIQLKCPPI | 48835 |
| HPV18 | E1 | 461 | IEFITFLGALKSFLK | 46739 | ITFLGALKS | 48836 |
| HPV18 | E1 | 192 | IENVNPQCTIAQLKD | 46740 | VNPQCTIAQ | 48837 |
| HPV18 | E1 | 250 | IFGVNPTIAEGFKTL | 46741 | VNPTIAEGF | 48838 |
| HPV18 | E1 | 501 | IHFIQGAVISFVNST | 46742 | IQGAVISFV | 48839 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV18 | E1 | 285 | ILALLRYKCGKSRLT | 46743 | LLRYKCGKS | 48840 |
| HPV18 | E1 | 339 | ISEVMGDTPEWIQRL | 46744 | VMGDTPEWI | 48841 |
| HPV18 | E1 | 464 | ITFLGALKSFLKGTP | 46745 | LGALKSFLK | 48842 |
| HPV18 | E1 | 593 | ITVFEFPNAFPFDKN | 46746 | FEFPNAFPF | 48843 |
| HPV18 | E1 | 620 | KCFFERTWSRLDLHE | 46747 | FERTWSRLD | 48844 |
| HPV18 | E1 | 222 | KDTYGLSFTDLVRNF | 46748 | YGLSFTDLV | 48845 |
| HPV18 | E1 | 480 | KNCLVFCGPANTGKS | 46749 | LVFCGPANT | 48846 |
| HPV18 | E1 | 562 | KPLIQLKCPPILLTT | 46750 | IQLKCPPIL | 48847 |
| HPV18 | E1 | 89 | KRKFAGGSTENSPLG | 46751 | FAGGSTENS | 48848 |
| HPV18 | E1 | 493 | KSYFGMSFIHFIQGA | 46752 | FGMSFIHFI | 48849 |
| HPV18 | E1 | 262 | KTLIQPFILYAHIQC | 46753 | IQPFILYAH | 48850 |
| HPV18 | E1 | 527 | KVAMLDDATTTCWTY | 46754 | MLDDATTTC | 48851 |
| HPV18 | E1 | 280 | KWGVLILALLRYKCG | 46755 | VLILALLRY | 48852 |
| HPV18 | E1 | 520 | LEPLTDTKVAMLDDA | 46756 | LTDTKVAML | 48853 |
| HPV18 | E1 | 85 | LHVLKRKFAGGSTEN | 46757 | LKRKFAGGS | 48854 |
| HPV18 | E1 | 564 | LIQLKCPPILLTTNI | 46758 | LKCPPILLT | 48855 |
| HPV18 | E1 | 470 | LKSFLKGTPKKNCLV | 46759 | FLKGTPKKN | 48856 |
| HPV18 | E1 | 307 | LLHVPETCMLIQPPK | 46760 | VPETCMLIQ | 48857 |
| HPV18 | E1 | 288 | LLRYKCGKSRLTVAK | 46761 | YKCGKSRLT | 48858 |
| HPV18 | E1 | 329 | LYWYRTGISNISEVM | 46762 | YRTGISNIS | 48859 |
| HPV18 | E1 | 432 | MSQWIRFRCSKIDEG | 46763 | WIRFRCSKI | 48860 |
| HPV18 | E1 | 481 | NCLVFCGPANTGKSY | 46764 | VFCGPANTG | 48861 |
| HPV18 | E1 | 18 | NGWFYVQAIVDKKTG | 46765 | FYVQAIVDK | 48862 |
| HPV18 | E1 | 189 | NSNIENVNPQCTIAQ | 46766 | IENVNPQCT | 48863 |
| HPV18 | E1 | 347 | PEWIQRLTIIQHGID | 46767 | IQRLTIIQH | 48864 |
| HPV18 | E1 | 570 | PPILLTTNIHPAKDN | 46768 | LLTTNIHPA | 48865 |
| HPV18 | E1 | 319 | PPKLRSSVAALYWYR | 46769 | LRSSVAALY | 48866 |
| HPV18 | E1 | 63 | QAELETAQALFHAQE | 46770 | LETAQALFH | 48867 |
| HPV18 | E1 | 408 | QAKYLKDCATMCKHY | 46771 | YLKDCATMC | 48868 |
| HPV18 | E1 | 70 | QALFHAQEVHNDAQV | 46772 | FHAQEVHND | 48869 |
| HPV18 | E1 | 266 | QPFILYAHIQCLDCK | 46773 | ILYAHIQCL | 48870 |
| HPV18 | E1 | 372 | QWAFDNELTDESDMA | 46774 | FDNELTDES | 48871 |
| HPV18 | E1 | 105 | RLEVDTELSPRLQEI | 46775 | VDTELSPRL | 48872 |
| HPV18 | E1 | 352 | RLTIIQHGIDDSNFD | 46776 | IIQHGIDDS | 48873 |
| HPV18 | E1 | 297 | RLTVAKGLSTLLHVP | 46777 | VAKGLSTLL | 48874 |
| HPV18 | E1 | 547 | RNALDGNPISIDRKH | 46778 | LDGNPISID | 48875 |
| HPV18 | E1 | 130 | RRLFTISDSGYGCSE | 46779 | FTISDSGYG | 48876 |
| HPV18 | E1 | 585 | RWPYLESRITVFEFP | 46780 | YLESRITVF | 48877 |
| HPV18 | E1 | 48 | SDMVDFIDTQGTFCE | 46781 | VDFIDTQGT | 48878 |
| HPV18 | E1 | 516 | SHFWLEPLTDTKVAM | 46782 | WLEPLTDTK | 48879 |
| HPV18 | E1 | 113 | SPRLQEISLNSGQKK | 46783 | LQEISLNSG | 48880 |
| HPV18 | E1 | 433 | SQWIRFRCSKIDEGG | 46784 | IRFRCSKID | 48881 |
| HPV18 | E1 | 305 | STLLHVPETCMLIQP | 46785 | LHVPETCML | 48882 |
| HPV18 | E1 | 248 | TAIFGVNPTIAEGFK | 46786 | FGVNPTIAE | 48883 |
| HPV18 | E1 | 230 | TDLVRNFKSDKTTCT | 46787 | VRNFKSDKT | 48884 |
| HPV18 | E1 | 168 | TEAIDNGGTEGNNSS | 46788 | IDNGGTEGN | 48885 |
| HPV18 | E1 | 346 | TPEWIQRLTIIQHGI | 46789 | WIQRLTIIQ | 48886 |
| HPV18 | E1 | 515 | TSHFWLEPLTDTKVA | 46790 | FWLEPLTDT | 48887 |
| HPV18 | E1 | 536 | TTCWTYFDTYMRNAL | 46791 | WTYFDTYMR | 48888 |
| HPV18 | E1 | 224 | TYGLSFTDLVRNFKS | 46792 | LSFTDLVRN | 48889 |
| HPV18 | E1 | 326 | VAALYWYRTGISNIS | 46793 | LYWYRTGIS | 48890 |
| HPV18 | E1 | 528 | VAMLDDATTTCWTYF | 46794 | LDDATTTCW | 48891 |
| HPV18 | E1 | 51 | VDFIDTQGTFCEQAE | 46795 | IDTQGTFCE | 48892 |
| HPV18 | E1 | 595 | VFEFPNAFPFDKNGN | 46796 | FPNAFPFDK | 48893 |
| HPV18 | E1 | 508 | VISFVNSTSHFWLEP | 46797 | FVNSTSHFW | 48894 |
| HPV18 | E1 | 23 | VQAIVDKKTGDVISD | 46798 | IVDKKTGDV | 48895 |
| HPV18 | E1 | 453 | VQFLRYQQIEFITFL | 46799 | LRYQQIEFI | 48896 |
| HPV18 | E1 | 233 | VRNFKSDKTTCTDWV | 46800 | FKSDKTTCT | 48897 |
| HPV18 | E1 | 247 | VTAIFGVNPTIAEGF | 46801 | IFGVNPTIA | 48898 |
| HPV18 | E1 | 281 | WGVLILALLRYKCGK | 46802 | LILALLRYK | 48899 |
| HPV18 | E1 | 435 | WIRFRCSKIDEGGDW | 46803 | FRCSKIDEG | 48900 |
| HPV18 | E1 | 586 | WPYLESRITVFEFPN | 46804 | LESRITVFE | 48901 |
| HPV18 | E1 | 271 | YAHIQCLDCKWGVLI | 46805 | IQCLDCKWG | 48902 |
| HPV18 | E1 | 389 | YALLADSNSNAAAFL | 46806 | LADSNSNAA | 48903 |
| HPV18 | E2 | 150 | AGTWDKTATCVSHRG | 46807 | WDKTATCVS | 48904 |
| HPV18 | E2 | 240 | AKTYGQTSAATRPGH | 46808 | YGQTSAATR | 48905 |
| HPV18 | E2 | 157 | ATCVSHRGLYYVKEG | 46809 | VSHRGLYYV | 48906 |
| HPV18 | E2 | 68 | AYNISKSKAHKAIEL | 46810 | ISKSKAHKA | 48907 |
| HPV18 | E2 | 105 | CEELWNTEPTHCFKK | 46811 | LWNTEPTHC | 48908 |
| HPV18 | E2 | 183 | CEKYGNTGTWEVHFG | 46812 | YGNTGTWEV | 48909 |
| HPV18 | E2 | 135 | CMTYVAWDSVYYMTD | 46813 | YVAWDSVYY | 48910 |
| HPV18 | E2 | 212 | DDTVSATQLVKQLQH | 46814 | VSATQLVKQ | 48911 |
| HPV18 | E2 | 34 | DSQIQYWQLIRWENA | 46815 | IQYWQLIRW | 48912 |
| HPV18 | E2 | 142 | DSVYYMTDAGTWDKT | 46816 | YYMTDAGTW | 48913 |
| HPV18 | E2 | 106 | EELWNTEPTHCFKKG | 46817 | WNTEPTHCF | 48914 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV18 | E2 | 81 | ELQMALQGLAQSRYK | 46818 | MALQGLAQS | 48915 |
| HPV18 | E2 | 193 | EVHFGNNVIDCNDSM | 46819 | FGNNVIDCN | 48916 |
| HPV18 | E2 | 77 | HKAIELQMALQGLAQ | 46820 | IELQMALQG | 48917 |
| HPV18 | E2 | 63 | HQVVPAYNISKSKAH | 46821 | VPAYNISKS | 48918 |
| HPV18 | E2 | 58 | IQTLNHQVVPAYNIS | 46822 | LNHQVVPAY | 48919 |
| HPV18 | E2 | 169 | KEGYNTFYIEFKSEC | 46823 | YNTFYIEFK | 48920 |
| HPV18 | E2 | 8 | KETLSERLSCVQDKI | 46824 | LSERLSCVQ | 48921 |
| HPV18 | E2 | 350 | LNTVAIPDSVQILVG | 46825 | VAIPDSVQI | 48922 |
| HPV18 | E2 | 15 | LSCVQDKIIDHYEND | 46826 | VQDKIIDHY | 48923 |
| HPV18 | E2 | 136 | MTYVAWDSVYYMTDA | 46827 | VAWDSVYYM | 48924 |
| HPV18 | E2 | 198 | NNVIDCNDSMCSTSD | 46828 | IDCNDSMCS | 48925 |
| HPV18 | E2 | 267 | NPLLGAATPTGNNKR | 46829 | LGAATPTGN | 48926 |
| HPV18 | E2 | 173 | NTFYIEFKSECEKYG | 46830 | YIEFKSECE | 48927 |
| HPV18 | E2 | 228 | PSPYSSTVSVGTAKT | 46831 | YSSTVSVGT | 48928 |
| HPV18 | E2 | 281 | RRKLCSGNTTPIIHL | 46832 | LCSGNTTPI | 48929 |
| HPV18 | E2 | 346 | RTKFLNTVAIPDSVQ | 46833 | FLNTVAIPD | 48930 |
| HPV18 | E2 | 313 | SDHYRDISSTWHWTG | 46834 | YRDISSTWH | 48931 |
| HPV18 | E2 | 232 | SSTVSVGTAKTYGQT | 46835 | VSVGTAKTY | 48932 |
| HPV18 | E2 | 320 | SSTWHWTGAGNEKTG | 46836 | WHWTGAGNE | 48933 |
| HPV18 | E2 | 96 | TEDWTLQDTCEELWN | 46837 | WTLQDTCEE | 48934 |
| HPV18 | E2 | 347 | TKFLNTVAIPDSVQI | 46838 | LNTVAIPDS | 48935 |
| HPV18 | E2 | 234 | TVSVGTAKTYGQTSA | 46839 | VGTAKTYGQ | 48936 |
| HPV18 | E2 | 221 | VKQLQHTPSPYSSTV | 46840 | LQHTPSPYS | 48937 |
| HPV18 | E2 | 266 | VNPLLGAATPTGNNK | 46841 | LLGAATPTG | 48938 |
| HPV18 | E2 | 66 | VPAYNISKSKAHKAI | 46842 | YNISKSKAH | 48939 |
| HPV18 | E2 | 144 | VYYMTDAGTWDKTAT | 46843 | MTDAGTWDK | 48940 |
| HPV18 | E2 | 40 | WQLIRWENAIFFAAR | 46844 | IRWENAIFF | 48941 |
| HPV18 | E5 | 2 | --MLSLIFLFCFCVC | 46845 | LSLIFLFCF | 48942 |
| HPV18 | E5 | 35 | AWVLVFVYIVVITSP | 46846 | LVFVYIVVI | 48943 |
| HPV18 | E5 | 33 | AYAWVLVFVYIVVIT | 46847 | WVLVFVYIV | 48944 |
| HPV18 | E5 | 20 | CCHVPLLPSVCMCAY | 46848 | VPLLPSVCM | 48945 |
| HPV18 | E5 | 12 | CFCVCMYVCCHVPLL | 46849 | VCMYVCCHV | 48946 |
| HPV18 | E5 | 59 | CFLLPMLLLHIHAIL | 46850 | LPMLLLHIH | 48947 |
| HPV18 | E5 | 16 | CMYVCCHVPLLPSVC | 46851 | VCCHVPLLP | 48948 |
| HPV18 | E5 | 58 | FCFLLPMLLLHIHAI | 46852 | LLPMLLLHI | 48949 |
| HPV18 | E5 | 53 | FTVYVFCFLLPMLLL | 46853 | YVFCFLLPM | 48950 |
| HPV18 | E5 | 40 | FVYIVVITSPATAFT | 46854 | IVVITSPAT | 48951 |
| HPV18 | E5 | 22 | HVPLLPSVCMCAYAW | 46855 | LLPSVCMCA | 48952 |
| HPV18 | E5 | 8 | IFLFCFCVCMYVCCH | 46856 | FCFCVCMYV | 48953 |
| HPV18 | E5 | 43 | IVVITSPATAFTVYV | 46857 | ITSPATAFT | 48954 |
| HPV18 | E5 | 7 | LIFLFCFCVCMYVCC | 46858 | LFCFCVCMY | 48955 |
| HPV18 | E5 | 61 | LLPMLLLHIHAILSL | 46859 | MLLLHIHAI | 48956 |
| HPV18 | E5 | 38 | LVFVYIVVITSPATA | 46860 | VYIVVITSP | 48957 |
| HPV18 | E5 | 31 | MCAYAWVLVFVYIVV | 46861 | YAWVLVFVY | 48958 |
| HPV18 | E5 | 64 | MLLLHIHAILSLQ-- | 46862 | LHIHAILSL | 48959 |
| HPV18 | E5 | 4 | MLSLIFLFCFCVCMY | 46863 | LIFLFCFCV | 48960 |
| HPV18 | E5 | 63 | PMLLLHIHAILSLQ- | 46864 | LLHIHAILS | 48961 |
| HPV18 | E5 | 6 | SLIFLFCFCVCMYVC | 46865 | FLFCFCVCM | 48962 |
| HPV18 | E5 | 54 | TVYVFCFLLPMLLLH | 46866 | VFCFLLPML | 48963 |
| HPV18 | E5 | 15 | VCMYVCCHVPLLPSV | 46867 | YVCCHVPLL | 48964 |
| HPV18 | E5 | 57 | VFCFLLPMLLLHIHA | 46868 | FLLPMLLLH | 48965 |
| HPV18 | E5 | 39 | VFVYIVVITSPATAF | 46869 | YIVVITSPA | 48966 |
| HPV18 | E5 | 37 | VLVFVYIVVITSPAT | 46870 | FVYIVVITS | 48967 |
| HPV18 | E5 | 23 | VPLLPSVCMCAYAWV | 46871 | LPSVCMCAY | 48968 |
| HPV18 | E5 | 41 | VYIVVITSPATAFTV | 46872 | VVITSPATA | 48969 |
| HPV18 | E5 | 55 | VYVFCFLLPMLLLHI | 46873 | FCFLLPMLL | 48970 |
| HPV18 | E5 | 36 | WVLVFVYIVVITSPA | 46874 | VFVYIVVIT | 48971 |
| HPV18 | E5 | 42 | YIVVITSPATAFTVY | 46875 | VITSPATAF | 48972 |
| HPV18 | E6 | 30 | DIEITCVYCKTVLEL | 46876 | ITCVYCKTV | 48973 |
| HPV18 | E6 | 54 | DLFVVYRDSIPHAAC | 46877 | VVYRDSIPH | 48974 |
| HPV18 | E6 | 49 | EFAFKDLFVVYRDSI | 46878 | FKDLFVVYR | 48975 |
| HPV18 | E6 | 56 | FVVYRDSIPHAACHK | 46879 | YRDSIPHAA | 48976 |
| HPV18 | E6 | 106 | IRCLRCQKPLNPAEK | 46880 | LRCQKPLNP | 48977 |
| HPV18 | E6 | 33 | ITCVYCKTVLELTEV | 46881 | VYCKTVLEL | 48978 |
| HPV18 | E6 | 39 | KTVLELTEVFEFAFK | 46882 | LELTEVFEF | 48979 |
| HPV18 | E6 | 93 | LEKLTNTGLYNLLIR | 46883 | LTNTGLYNL | 48980 |
| HPV18 | E6 | 55 | LFVVYRDSIPHAACH | 46884 | VYRDSIPHA | 48981 |
| HPV18 | E6 | 28 | LQDIEITCVYCKTVL | 46885 | IEITCVYCK | 48982 |
| HPV18 | E6 | 101 | LYNLLIRCLRCQKPL | 46886 | LLIRCLRCQ | 48983 |
| HPV18 | E6 | 103 | NLLIRCLRCQKPLNP | 46887 | IRCLRCQKP | 48984 |
| HPV18 | E6 | 98 | NTGLYNLLIRCLRCQ | 46888 | LYNLLIRCL | 48985 |
| HPV18 | E6 | 25 | NTSLQDIEITCVYCK | 46889 | LQDIEITCV | 48986 |
| HPV18 | E6 | 14 | PYKLPDLCTELNTSL | 46890 | LPDLCTELN | 48987 |
| HPV18 | E6 | 60 | RDSIPHAACHKCIDF | 46891 | IPHAACHKC | 48988 |
| HPV18 | E6 | 12 | RRPYKLPDLCTELNT | 46892 | YKLPDLCTE | 48989 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV18 | E6 | 85 | SDSVYGDTLEKLTNT | 46893 | VYGDTLEKL | 48990 |
| HPV18 | E6 | 34 | TCVYCKTVLELTEVF | 46894 | YCKTVLELT | 48991 |
| HPV18 | E6 | 47 | VFEFAFKDLFVVYRD | 46895 | FAFKDLFVV | 48992 |
| HPV18 | E7 | 1 | ---MHGPKATLQDIV | 46896 | MHGPKATLQ | 48993 |
| HPV18 | E7 | 89 | FQQLFLNTLSFVCPW | 46897 | LFLNTLSFV | 48994 |
| HPV18 | E7 | 49 | HQHLPARRAEPQRHT | 46898 | LPARRAEPQ | 48995 |
| HPV18 | E7 | 44 | IDGVNHQHLPARRAE | 46899 | VNHQHLPAR | 48996 |
| HPV18 | E7 | 75 | IKLVVESSADDLRAF | 46900 | VVESSADDL | 48997 |
| HPV18 | E7 | 8 | KATLQDIVLHLEPQN | 46901 | LQDIVLHLE | 48998 |
| HPV18 | E7 | 94 | LNTLSFVCPWCASQQ | 46902 | LSFVCPWCA | 48999 |
| HPV18 | E7 | 86 | LRAFQQLFLNTLSFV | 46903 | FQQLFLNTL | 49000 |
| HPV18 | E7 | 97 | LSFVCPWCASQQ--- | 46904 | VCPWCASQQ | 49001 |
| HPV18 | E7 | 12 | QDIVLHLEPQNEIPV | 46905 | VLHLEPQNE | 49002 |
| HPV18 | E7 | 21 | QNEIPVDLLCHEQLS | 46906 | IPVDLLCHE | 49003 |
| HPV18 | E7 | 90 | QQLFLNTLSFVCPWC | 46907 | FLNTLSFVC | 49004 |
| HPV18 | E7 | 61 | RHTMLCMCCKCEARI | 46908 | MLCMCCKCE | 49005 |
| HPV18 | E7 | 74 | RIKLVVESSADDLRA | 46909 | LVVESSADD | 49006 |
| HPV18 | E7 | 96 | TLSFVCPWCASQQ-- | 46910 | FVCPWCASQ | 49007 |
| HPV18 | E7 | 26 | VDLLCHEQLSDSEEE | 46911 | LCHEQLSDS | 49008 |
| HPV18 | L1 | 3 | -MCLYTRVLILHYHL | 46912 | LYTRVLILH | 49009 |
| HPV18 | L1 | 450 | ADVMSYIHSMNSSIL | 46913 | MSYIHSMNS | 49010 |
| HPV18 | L1 | 328 | AGTMGDTVPQSLYIK | 46914 | MGDTVPQSL | 49011 |
| HPV18 | L1 | 226 | APAIGEHWAKGTACK | 46915 | IGEHWAKGT | 49012 |
| HPV18 | L1 | 131 | AYQYRVFRVQLPDPN | 46916 | YRVFRVQLP | 49013 |
| HPV18 | L1 | 45 | CGHYIILFLRNVNVF | 46917 | YIILFLRNV | 49014 |
| HPV18 | L1 | 249 | CPPLELKNTVLEDGD | 46918 | LELKNTVLE | 49015 |
| HPV18 | L1 | 89 | DDYVTPTSIFYHAGS | 46919 | VTPTSIFYH | 49016 |
| HPV18 | L1 | 436 | DLQFIFQLCTITLTA | 46920 | FIFQLCTIT | 49017 |
| HPV18 | L1 | 72 | DNTVYLPPPSVARVV | 46921 | VYLPPPSVA | 49018 |
| HPV18 | L1 | 151 | DTSIYNPETQRLVWA | 46922 | IYNPETQRL | 49019 |
| HPV18 | L1 | 466 | DWNFGVPPPPTTSLV | 46923 | FGVPPPPTT | 49020 |
| HPV18 | L1 | 283 | EVPLDICQSICKYPD | 46924 | LDICQSICK | 49021 |
| HPV18 | L1 | 311 | FFCLRREQLFARHFW | 46925 | LRREQLFAR | 49022 |
| HPV18 | L1 | 62 | FLQMALWRPSDNTVY | 46926 | MALWRPSDN | 49023 |
| HPV18 | L1 | 59 | FPIFLQMALWRPSDN | 46927 | FLQMALWRP | 49024 |
| HPV18 | L1 | 274 | FSTLQDTKCEVPLDI | 46928 | LQDTKCEVP | 49025 |
| HPV18 | L1 | 394 | FVTVVDTTPSTNLTI | 46929 | VVDTTPSTN | 49026 |
| HPV18 | L1 | 230 | GEHWAKGTACKSRPL | 46930 | WAKGTACKS | 49027 |
| HPV18 | L1 | 110 | GNPYFRVPAGGGNKQ | 46931 | YFRVPAGGG | 49028 |
| HPV18 | L1 | 22 | GPLYHPRPLPLHSIL | 46932 | YHPRPLPLH | 49029 |
| HPV18 | L1 | 174 | GQPLGVGLSGHPFYN | 46933 | LGVGLSGHP | 49030 |
| HPV18 | L1 | 351 | GSCVYSPSPSGSIVT | 46934 | VYSPSPSGS | 49031 |
| HPV18 | L1 | 168 | GVEIGRGQPLGVGLS | 46935 | IGRGQPLGV | 49032 |
| HPV18 | L1 | 41 | HIIICGHYIILFLRN | 46936 | ICGHYIILF | 49033 |
| HPV18 | L1 | 390 | HNQLFVTVVDTTPST | 46937 | LFVTVVDTT | 49034 |
| HPV18 | L1 | 440 | IFQLCTITLTADVMS | 46938 | LCTITLTAD | 49035 |
| HPV18 | L1 | 456 | IHSMNSSILEDWNFG | 46939 | MNSSILEDW | 49036 |
| HPV18 | L1 | 50 | ILFLRNVNVFPIFLQ | 46940 | LRNVNVFPI | 49037 |
| HPV18 | L1 | 12 | ILHYHLLPLYGPLYH | 46941 | YHLLPLYGP | 49038 |
| HPV18 | L1 | 35 | ILVYMVHIIICGHYI | 46942 | YMVHIIICG | 49039 |
| HPV18 | L1 | 281 | KCEVPLDICQSICKY | 46943 | VPLDICQSI | 49040 |
| HPV18 | L1 | 146 | KFGLPDTSIYNPETQ | 46944 | LPDTSIYNP | 49041 |
| HPV18 | L1 | 508 | KLKFWNVDLKEKFSL | 46945 | FWNVDLKEK | 49042 |
| HPV18 | L1 | 123 | KQDIPKVSAYQYRVF | 46946 | IPKVSAYQY | 49043 |
| HPV18 | L1 | 220 | LCILGCAPAIGEHWA | 46947 | LGCAPAIGE | 49044 |
| HPV18 | L1 | 464 | LEDWNFGVPPPPTTS | 46948 | WNFGVPPPP | 49045 |
| HPV18 | L1 | 32 | LHSILVYMVHIIICG | 46949 | ILVYMVHII | 49046 |
| HPV18 | L1 | 437 | LQFIFQLCTITLTAD | 46950 | IFQLCTITL | 49047 |
| HPV18 | L1 | 53 | LRNVNVFPIFLQMAL | 46951 | VNVFPIFLQ | 49048 |
| HPV18 | L1 | 36 | LVYMVHIIICGHYII | 46952 | MVHIIICGH | 49049 |
| HPV18 | L1 | 4 | MCLYTRVLILHYHLL | 46953 | YTRVLILHY | 49050 |
| HPV18 | L1 | 453 | MSYIHSMNSSILEDW | 46954 | IHSMNSSIL | 49051 |
| HPV18 | L1 | 468 | NFGVPPPPTTSLVDT | 46955 | VPPPPTTSL | 49052 |
| HPV18 | L1 | 372 | NKPYWLHKAQGHNNG | 46956 | YWLHKAQGH | 49053 |
| HPV18 | L1 | 256 | NTVLEDGDMVDTGYG | 46957 | LEDGDMVDT | 49054 |
| HPV18 | L1 | 73 | NTVYLPPPSVARVVN | 46958 | YLPPPSVAR | 49055 |
| HPV18 | L1 | 513 | NVDLKEKFSLDLDQY | 46959 | LKEKFSLDL | 49056 |
| HPV18 | L1 | 55 | NVNVFPIFLQMALWR | 46960 | VFPIFLQMA | 49057 |
| HPV18 | L1 | 210 | NVSVDYKQTQLCILG | 46961 | VDYKQTQLC | 49058 |
| HPV18 | L1 | 285 | PLDICQSICKYPDYL | 46962 | ICQSICKYP | 49059 |
| HPV18 | L1 | 251 | PLELKNTVLEDGDMV | 46963 | LKNTVLEDG | 49060 |
| HPV18 | L1 | 29 | PLPLHSILVYMVHII | 46964 | LHSILVYMV | 49061 |
| HPV18 | L1 | 144 | PNKFGLPDTSIYNPE | 46965 | FGLPDTSIY | 49062 |
| HPV18 | L1 | 336 | PQSLYIKGTGMPASP | 46966 | LYIKGTGMP | 49063 |
| HPV18 | L1 | 27 | PRPLPLHSILVYMVH | 46967 | LPLHSILVY | 49064 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV18 | L1 | 536 | QAGLRRKPTIGPRKR | 46968 | LRRKPTIGP | 49065 |
| HPV18 | L1 | 438 | QFIFQLCTITLTADV | 46969 | FQLCTITLT | 49066 |
| HPV18 | L1 | 219 | QLCILGCAPAIGEHW | 46970 | ILGCAPAIG | 49067 |
| HPV18 | L1 | 392 | QLFVTVVDTTPSTNL | 46971 | VTVVDTTPS | 49068 |
| HPV18 | L1 | 217 | QTQLCILGCAPAIGE | 46972 | LCILGCAPA | 49069 |
| HPV18 | L1 | 526 | QYPLGRKFLVQAGLR | 46973 | LGRKFLVQA | 49070 |
| HPV18 | L1 | 133 | QYRVFRVQLPDPNKF | 46974 | VFRVQLPDP | 49071 |
| HPV18 | L1 | 322 | RHFWNRAGTMGDTVP | 46975 | WNRAGTMGD | 49072 |
| HPV18 | L1 | 531 | RKFLVQAGLRRKPTI | 46976 | LVQAGLRRK | 49073 |
| HPV18 | L1 | 161 | RLVWACAGVEIGRGQ | 46977 | WACAGVEIG | 49074 |
| HPV18 | L1 | 9 | RVLILHYHLLPLYGP | 46978 | ILHYHLLPL | 49075 |
| HPV18 | L1 | 352 | SCVYSPSPSGSIVTS | 46979 | YSPSPSGSI | 49076 |
| HPV18 | L1 | 204 | SEDVRDNVSVDYKQT | 46980 | VRDNVSVDY | 49077 |
| HPV18 | L1 | 360 | SGSIVTSDSQLFNKP | 46981 | IVTSDSQLF | 49078 |
| HPV18 | L1 | 96 | SIFYHAGSSRLLTVG | 46982 | YHAGSSRLL | 49079 |
| HPV18 | L1 | 34 | SILVYMVHIIICGHY | 46983 | VYMVHIIIC | 49080 |
| HPV18 | L1 | 521 | SLDLDQYPLGRKFLV | 46984 | LDQYPLGRK | 49081 |
| HPV18 | L1 | 338 | SLYIKGTGMPASPGS | 46985 | IKGTGMPAS | 49082 |
| HPV18 | L1 | 429 | SRHVEEYDLQFIFQL | 46986 | VEEYDLQFI | 49083 |
| HPV18 | L1 | 104 | SRLLTVGNPYFRVPA | 46987 | LTVGNPYFR | 49084 |
| HPV18 | L1 | 241 | SRPLSQGDCPPLELK | 46988 | LSQGDCPPL | 49085 |
| HPV18 | L1 | 403 | STNLTICASTQSPVP | 46989 | LTICASTQS | 49086 |
| HPV18 | L1 | 212 | SVDYKQTQLCILGCA | 46990 | YKQTQLCIL | 49087 |
| HPV18 | L1 | 88 | TDDYVTPTSIFYHAG | 46991 | YVTPTSIFY | 49088 |
| HPV18 | L1 | 445 | TITLTADVMSYIHSM | 46992 | LTADVMSYI | 49089 |
| HPV18 | L1 | 159 | TQRLVWACAGVEIGR | 46993 | LVWACAGVE | 49090 |
| HPV18 | L1 | 95 | TSIFYHAGSSRLLTV | 46994 | FYHAGSSRL | 49091 |
| HPV18 | L1 | 74 | TVYLPPPSVARVVNT | 46995 | LPPPSVARV | 49092 |
| HPV18 | L1 | 482 | TYRFVQSVAITCQKD | 46996 | FVQSVAITC | 49093 |
| HPV18 | L1 | 480 | VDTYRFVQSVAITCQ | 46997 | YRFVQSVAI | 49094 |
| HPV18 | L1 | 432 | VEEYDLQFIFQLCTI | 46998 | YDLQFIFQL | 49095 |
| HPV18 | L1 | 58 | VFPIFLQMALWRPSD | 46999 | IFLQMALWR | 49096 |
| HPV18 | L1 | 136 | VFRVQLPDPNKFGLP | 47000 | VQLPDPNKF | 49097 |
| HPV18 | L1 | 10 | VLILHYHLLPLYGPL | 47001 | LHYHLLPLY | 49098 |
| HPV18 | L1 | 395 | VTVVDTTPSTNLTIC | 47002 | VDTTPSTNL | 49099 |
| HPV18 | L1 | 37 | VYMVHIIICGHYIIL | 47003 | VHIIICGHY | 49100 |
| HPV18 | L1 | 506 | YDKLKFWNVDLKEKF | 47004 | LKFWNVDLK | 49101 |
| HPV18 | L1 | 269 | YGAMDFSTLQDTKCE | 47005 | MDFSTLQDT | 49102 |
| HPV18 | L1 | 21 | YGPLYHPRPLPLHSI | 47006 | LYHPRPLPL | 49103 |
| HPV18 | L1 | 15 | YHLLPLYGPLYHPRP | 47007 | LPLYGPLYH | 49104 |
| HPV18 | L1 | 48 | YIILFLRNVNVFPIF | 47008 | LFLRNVNVF | 49105 |
| HPV18 | L1 | 187 | YNKLDDTESSHAATS | 47009 | LDDTESSHA | 49106 |
| HPV18 | L1 | 295 | YPDYLQMSADPYGDS | 47010 | YLQMSADPY | 49107 |
| HPV18 | L1 | 483 | YRFVQSVAITCQKDA | 47011 | VQSVAITCQ | 49108 |
| HPV18 | L1 | 134 | YRVFRVQLPDPNKFG | 47012 | FRVQLPDPN | 49109 |
| HPV18 | L2 | 1 | ---MVSHRAARRKRA | 47013 | MVSHRAARR | 49110 |
| HPV18 | L2 | 2 | --MVSHRAARRKRAS | 47014 | VSHRAARRK | 49111 |
| HPV18 | L2 | 355 | ADDMDPAVPVPSRST | 47015 | MDPAVPVPS | 49112 |
| HPV18 | L2 | 44 | ADKILQWSSLGIFLG | 47016 | ILQWSSLGI | 49113 |
| HPV18 | L2 | 180 | AGNVFVGTPTSGTHG | 47017 | VFVGTPTSG | 49114 |
| HPV18 | L2 | 384 | ASSYSNVTVPLTSSW | 47018 | YSNVTVPLT | 49115 |
| HPV18 | L2 | 306 | ATMFTRSGTQIGARV | 47019 | FTRSGTQIG | 49116 |
| HPV18 | L2 | 361 | AVPVPSRSTTSFAFF | 47020 | VPSRSTTSF | 49117 |
| HPV18 | L2 | 407 | DITLPSTTSVWPIVS | 47021 | LPSTTSVWP | 49118 |
| HPV18 | L2 | 45 | DKILQWSSLGIFLGG | 47022 | LQWSSLGIF | 49119 |
| HPV18 | L2 | 347 | DNDLFDIYADDMDPA | 47023 | LFDIYADDM | 49120 |
| HPV18 | L2 | 112 | DSSVVTSGAPRPTFT | 47024 | VVTSGAPRP | 49121 |
| HPV18 | L2 | 210 | EEPISSTPLPTVRRV | 47025 | ISSTPLPTV | 49122 |
| HPV18 | L2 | 197 | EIPLQTFASSGTEEE | 47026 | LQTFASSGT | 49123 |
| HPV18 | L2 | 372 | FAFFKYSPTISSASS | 47027 | FKYSPTISS | 49124 |
| HPV18 | L2 | 259 | FEPVDTTLTFDPRSD | 47028 | VDTTLTFDP | 49125 |
| HPV18 | L2 | 374 | FFKYSPTISSASSYS | 47029 | YSPTISSAS | 49126 |
| HPV18 | L2 | 299 | FSRLGQRATMFTRSG | 47030 | LGQRATMFT | 49127 |
| HPV18 | L2 | 130 | GFDITSAGTTTPAVL | 47031 | ITSAGTTTP | 49128 |
| HPV18 | L2 | 54 | GIFLGGLGIGTGSGT | 47032 | LGGLGIGTG | 49129 |
| HPV18 | L2 | 181 | GNVFVGTPTSGTHGY | 47033 | FVGTPTSGT | 49130 |
| HPV18 | L2 | 405 | GPDITLPSTTSVWPI | 47034 | ITLPSTTSV | 49131 |
| HPV18 | L2 | 435 | GTHYYLWPLYYFIPK | 47035 | YYLWPLYYF | 49132 |
| HPV18 | L2 | 40 | GTTLADKILQWSSLG | 47036 | LADKILQWS | 49133 |
| HPV18 | L2 | 96 | IEPVGPTDPSIVTLI | 47037 | VGPTDPSIV | 49134 |
| HPV18 | L2 | 282 | IIRLHRPALTSRRGT | 47038 | LHRPALTSR | 49135 |
| HPV18 | L2 | 47 | ILQWSSLGIFLGGLG | 47039 | WSSLGIFLG | 49136 |
| HPV18 | L2 | 106 | IVTLIEDSSVVTSGA | 47040 | LIEDSSVVT | 49137 |
| HPV18 | L2 | 350 | LFDIYADDMDPAVPV | 47041 | IYADDMDPA | 49138 |
| HPV18 | L2 | 200 | LQTFASSGTEEPIS | 47042 | FASSGTEE | 49139 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV18 | L2 | 440 | LWPLYYFIPKKRKRV | 47043 | LYYFIPKKR | 49140 |
| HPV18 | L2 | 280 | MDIIRLHRPALTSRR | 47044 | IRLHRPALT | 49141 |
| HPV18 | L2 | 256 | NPAFEPVDTTLTFDP | 47045 | FEPVDTTLT | 49142 |
| HPV18 | L2 | 162 | NPAFSDPSIIEVPQT | 47046 | FSDPSIIEV | 49143 |
| HPV18 | L2 | 241 | NPEFLTRPSSLITYD | 47047 | FLTRPSSLI | 49144 |
| HPV18 | L2 | 82 | NTVVDVGPTRPPVVI | 47048 | VDVGPTRPP | 49145 |
| HPV18 | L2 | 182 | NVFVGTPTSGTHGYE | 47049 | VGTPTSGTH | 49146 |
| HPV18 | L2 | 389 | NVTVPLTSSWDVPVY | 47050 | VPLTSSWDV | 49147 |
| HPV18 | L2 | 141 | PAVLDITPSSTSVSI | 47051 | LDITPSSTS | 49148 |
| HPV18 | L2 | 242 | PEFLTRPSSLITYDN | 47052 | LTRPSSLIT | 49149 |
| HPV18 | L2 | 333 | PEYIELQPLVSATED | 47053 | IELQPLVSA | 49150 |
| HPV18 | L2 | 168 | PSIIEVPQTGEVAGN | 47054 | IEVPQTGEV | 49151 |
| HPV18 | L2 | 93 | PVVIEPVGPTDPSIV | 47055 | IEPVGPTDP | 49152 |
| HPV18 | L2 | 294 | RGTVRFSRLGQRATM | 47056 | VRFSRLGQR | 49153 |
| HPV18 | L2 | 451 | RKRVPYFFADGFVAA | 47057 | VPYFFADGF | 49154 |
| HPV18 | L2 | 91 | RPPVVIEPVGPTDPS | 47058 | VVIEPVGPT | 49155 |
| HPV18 | L2 | 319 | RVHFYHDISPIAPSP | 47059 | FYHDISPIA | 49156 |
| HPV18 | L2 | 277 | SDFMDIIRLHRPALT | 47060 | MDIIRLHRP | 49157 |
| HPV18 | L2 | 371 | SFAFFKYSPTISSAS | 47061 | FFKYSPTIS | 49158 |
| HPV18 | L2 | 52 | SLGIFLGGLGIGTGS | 47062 | IFLGGLGIG | 49159 |
| HPV18 | L2 | 81 | SNTVVDVGPTRPPVV | 47063 | VVDVGPTRP | 49160 |
| HPV18 | L2 | 332 | SPEYIELQPLVSATE | 47064 | YIELQPLVS | 49161 |
| HPV18 | L2 | 378 | SPTISSASSYSNVTV | 47065 | ISSASSYSN | 49162 |
| HPV18 | L2 | 231 | SRAYQQVSVANPEFL | 47066 | YQQVSVANP | 49163 |
| HPV18 | L2 | 249 | SSLITYDNPAFEPVD | 47067 | ITYDNPAFE | 49164 |
| HPV18 | L2 | 113 | SSVVTSGAPRPTFTG | 47068 | VTSGAPRPT | 49165 |
| HPV18 | L2 | 150 | STSVSISTTNFTNPA | 47069 | VSISTTNFT | 49166 |
| HPV18 | L2 | 192 | THGYEEIPLQTFASS | 47070 | YEEIPLQTF | 49167 |
| HPV18 | L2 | 140 | TPAVLDITPSSTSVS | 47071 | VLDITPSST | 49168 |
| HPV18 | L2 | 428 | TQYIGIHGTHYYLWP | 47072 | IGIHGTHYY | 49169 |
| HPV18 | L2 | 128 | TSGFDITSAGTTTPA | 47073 | FDITSAGTT | 49170 |
| HPV18 | L2 | 414 | TSVWPIVSPTAPAST | 47074 | WPIVSPTAP | 49171 |
| HPV18 | L2 | 413 | TTSVWPIVSPTAPAS | 47075 | VWPIVSPTA | 49172 |
| HPV18 | L2 | 320 | VHFYHDISPIAPSPE | 47076 | YHDISPIAP | 49173 |
| HPV18 | L2 | 143 | VLDITPSSTSVSIST | 47077 | ITPSSTSVS | 49174 |
| HPV18 | L2 | 35 | VPKVEGTTLADKILQ | 47078 | VEGTTLADK | 49175 |
| HPV18 | L2 | 400 | VPVYTGPDITLPSTT | 47079 | YTGPDITLP | 49176 |
| HPV18 | L2 | 221 | VRRVAGPRLYSRAYQ | 47080 | VAGPRLYSR | 49177 |
| HPV18 | L2 | 107 | VTLIEDSSVVTSGAP | 47081 | IEDSSVVTS | 49178 |
| HPV18 | L2 | 84 | VVDVGPTRPPVVIEP | 47082 | VGPTRPPVV | 49179 |
| HPV18 | L2 | 416 | VWPIVSPTAPASTQY | 47083 | IVSPTAPAS | 49180 |
| HPV18 | L2 | 417 | WPIVSPTAPASTQYI | 47084 | VSPTAPAST | 49181 |
| HPV18 | L2 | 323 | YHDISPIAPSPEYIE | 47085 | ISPIAPSPE | 49182 |
| HPV18 | L2 | 335 | YIELQPLVSATEDND | 47086 | LQPLVSATE | 49183 |
| HPV18 | L2 | 234 | YQQVSVANPEFLTRP | 47087 | VSVANPEFL | 49184 |
| HPV18 | L2 | 387 | YSNVTVPLTSSWDVP | 47088 | VTVPLTSSW | 49185 |
| HPV31 | E1 | 299 | AAALYWYRTGMSNIS | 47089 | LYWYRTGMS | 49186 |
| HPV31 | E1 | 372 | ACAFLKSNSQAKIVK | 47090 | FLKSNSQAK | 49187 |
| HPV31 | E1 | 251 | ACSWGMVMLMLVRFK | 47091 | WGMVMLMLV | 49188 |
| HPV31 | E1 | 223 | AFGVTGTVAEGFKTL | 47092 | VTGTVAEGF | 49189 |
| HPV31 | E1 | 382 | AKIVKDCGTMCRHYK | 47093 | VKDCGTMCR | 49190 |
| HPV31 | E1 | 442 | ALKLFLKGVPKKNCI | 47094 | LFLKGVPKK | 49191 |
| HPV31 | E1 | 301 | ALYWYRTGMSNISDV | 47095 | WYRTGMSNI | 49192 |
| HPV31 | E1 | 287 | CMLIQPPKLRSTAAA | 47096 | IQPPKLRST | 49193 |
| HPV31 | E1 | 17 | CNGWFYVEAVIDRQT | 47097 | WFYVEAVID | 49194 |
| HPV31 | E1 | 511 | CWHYIDNYLRNALDG | 47098 | YIDNYLRNA | 49195 |
| HPV31 | E1 | 556 | DDRWPYLHSRLVVFT | 47099 | WPYLHSRLV | 49196 |
| HPV31 | E1 | 589 | DKNWKSFFSRTWCRL | 47100 | WKSFFSRTW | 49197 |
| HPV31 | E1 | 355 | DSEIAYKYAQLADSD | 47101 | IAYKYAQLA | 49198 |
| HPV31 | E1 | 133 | DSGYGNTEVETQQMV | 47102 | YGNTEVETQ | 49199 |
| HPV31 | E1 | 335 | DTTFDLSQMVQWAYD | 47103 | FDLSQMVQW | 49200 |
| HPV31 | E1 | 218 | DWCVAAFGVTGTVAE | 47104 | VAAFGVTGT | 49201 |
| HPV31 | E1 | 357 | EIAYKYAQLADSDSN | 47105 | YKYAQLADS | 49202 |
| HPV31 | E1 | 274 | EKLLEKLLCISTNCM | 47106 | LEKLLCIST | 49203 |
| HPV31 | E1 | 621 | FKCVSGQNIRTL--- | 47107 | VSGQNIRTL | 49204 |
| HPV31 | E1 | 234 | FKTLLQPYCLYCHLQ | 47108 | LLQPYCLYC | 49205 |
| HPV31 | E1 | 479 | GCIISYANSKSHFWL | 47109 | ISYANSKSH | 49206 |
| HPV31 | E1 | 615 | GDSFSTFKCVSGQNI | 47110 | FSTFKCVSG | 49207 |
| HPV31 | E1 | 465 | GKSYFGMSLISFLQG | 47111 | YFGMSLISF | 49208 |
| HPV31 | E1 | 94 | GSPLSDISSCVDYNI | 47112 | LSDISSCVD | 49209 |
| HPV31 | E1 | 19 | GWFYVEAVIDRQTGD | 47113 | YVEAVIDRQ | 49210 |
| HPV31 | E1 | 534 | HKALMQLKCPPLLIT | 47114 | LMQLKCPPL | 49211 |
| HPV31 | E1 | 515 | IDNYLRNALDGNPVS | 47115 | YLRNALDGN | 49212 |
| HPV31 | E1 | 434 | IEFVSFLSALKLFLK | 47116 | VSFLSALKL | 49213 |
| HPV31 | E1 | 273 | IEKLLEKLLCISTNC | 47117 | LLEKLLCIS | 49214 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV31 | E1 | 501 | IGMLDDATTPCWHYI | 47118 | LDDATTPCW | 49215 |
| HPV31 | E1 | 481 | IISYANSKSHFWLQP | 47119 | YANSKSHFW | 49216 |
| HPV31 | E1 | 206 | IRPFQSNKSTCTDWC | 47120 | FQSNKSTCT | 49217 |
| HPV31 | E1 | 312 | ISDVYGETPEWIERQ | 47121 | VYGETPEWI | 49218 |
| HPV31 | E1 | 474 | ISFLQGCIISYANSK | 47122 | LQGCIISYA | 49219 |
| HPV31 | E1 | 535 | KALMQLKCPPLLITS | 47123 | MQLKCPPLL | 49220 |
| HPV31 | E1 | 195 | KELYGVSFMELIRPF | 47124 | YGVSFMELI | 49221 |
| HPV31 | E1 | 500 | KIGMLDDATTPCWHY | 47125 | MLDDATTPC | 49222 |
| HPV31 | E1 | 453 | KNCILIHGAPNTGKS | 47126 | ILIHGAPNT | 49223 |
| HPV31 | E1 | 268 | KNRITIEKLLEKLLC | 47127 | ITIEKLLEK | 49224 |
| HPV31 | E1 | 89 | KRKYVGSPLSDISSC | 47128 | YVGSPLSDI | 49225 |
| HPV31 | E1 | 593 | KSFFSRTWCRLNLHE | 47129 | FSRTWCRLN | 49226 |
| HPV31 | E1 | 488 | KSHFWLQPLADAKIG | 47130 | FWLQPLADA | 49227 |
| HPV31 | E1 | 466 | KSYFGMSLISFLQGC | 47131 | FGMSLISFL | 49228 |
| HPV31 | E1 | 235 | KTLLQPYCLYCHLQS | 47132 | LQPYCLYCH | 49229 |
| HPV31 | E1 | 277 | LEKLLCISTNCMLIQ | 47133 | LLCISTNCM | 49230 |
| HPV31 | E1 | 473 | LISFLQGCIISYANS | 47134 | FLQGCIISY | 49231 |
| HPV31 | E1 | 447 | LKGVPKKNCILIHGA | 47135 | VPKKNCILI | 49232 |
| HPV31 | E1 | 443 | LKLFLKGVPKKNCIL | 47136 | FLKGVPKKN | 49233 |
| HPV31 | E1 | 280 | LLCISTNCMLIQPPK | 47137 | ISTNCMLIQ | 49234 |
| HPV31 | E1 | 259 | LMLVRFKCAKNRITI | 47138 | VRFKCAKNR | 49235 |
| HPV31 | E1 | 537 | LMQLKCPPLLITSNI | 47139 | LKCPPLLIT | 49236 |
| HPV31 | E1 | 493 | LQPLADAKIGMLDDA | 47140 | LADAKIGML | 49237 |
| HPV31 | E1 | 566 | LVVFTFPNPFPFDKN | 47141 | FTFPNPFPF | 49238 |
| HPV31 | E1 | 197 | LYGVSFMELIRPFQS | 47142 | VSFMELIRP | 49239 |
| HPV31 | E1 | 302 | LYWYRTGMSNISDVY | 47143 | YRTGMSNIS | 49240 |
| HPV31 | E1 | 203 | MELIRPFQSNKSTCT | 47144 | IRPFQSNKS | 49241 |
| HPV31 | E1 | 405 | MGQWIKSRCDKVSDE | 47145 | WIKSRCDKV | 49242 |
| HPV31 | E1 | 258 | MLMLVRFKCAKNRIT | 47146 | LVRFKCAKN | 49243 |
| HPV31 | E1 | 146 | MVQVEEQQTTLSCNG | 47147 | VEEQQTTLS | 49244 |
| HPV31 | E1 | 454 | NCILIHGAPNTGKSY | 47148 | LIHGAPNTG | 49245 |
| HPV31 | E1 | 56 | NCNVYNNQAEAETAQ | 47149 | VYNNQAEAE | 49246 |
| HPV31 | E1 | 350 | NDVMDDSEIAYKYAQ | 47150 | MDDSEIAYK | 49247 |
| HPV31 | E1 | 18 | NGWFYVEAVIDRQTG | 47151 | FYVEAVIDR | 49248 |
| HPV31 | E1 | 138 | NTEVETQQMVQVEEQ | 47152 | VETQQMVQV | 49249 |
| HPV31 | E1 | 320 | PEWIERQTVLQHSFN | 47153 | IERQTVLQH | 49250 |
| HPV31 | E1 | 292 | PPKLRSTAAALYWYR | 47154 | LRSTAAALY | 49251 |
| HPV31 | E1 | 543 | PPLLITSNINAGKDD | 47155 | LITSNINAG | 49252 |
| HPV31 | E1 | 70 | QALFHAQEAEEHAEA | 47156 | FHAQEAEEH | 49253 |
| HPV31 | E1 | 433 | QIEFVSFLSALKLFL | 47157 | FVSFLSALK | 49254 |
| HPV31 | E1 | 153 | QTTLSCNGSDGTHSE | 47158 | LSCNGSDGT | 49255 |
| HPV31 | E1 | 345 | QWAYDNDVMDDSEIA | 47159 | YDNDVMDDS | 49256 |
| HPV31 | E1 | 90 | RKYVGSPLSDISSCV | 47160 | VGSPLSDIS | 49257 |
| HPV31 | E1 | 520 | RNALDGNPVSIDVKH | 47161 | LDGNPVSID | 49258 |
| HPV31 | E1 | 175 | RNILQVLKTSNGKAA | 47162 | LQVLKTSNG | 49259 |
| HPV31 | E1 | 126 | RRLFELPDSGYGNTE | 47163 | FELPDSGYG | 49260 |
| HPV31 | E1 | 558 | RWPYLHSRLVVFTFP | 47164 | YLHSRLVVF | 49261 |
| HPV31 | E1 | 489 | SHFWLQPLADAKIGM | 47165 | WLQPLADAK | 49262 |
| HPV31 | E1 | 529 | SIDVKHKALMQLKCP | 47166 | VKHKALMQL | 49263 |
| HPV31 | E1 | 109 | SPRLKAICIENNSKT | 47167 | LKAICIENN | 49264 |
| HPV31 | E1 | 564 | SRLVVFTFPNPFPFD | 47168 | VVFTFPNPF | 49265 |
| HPV31 | E1 | 597 | SRTWCRLNLHEEEDK | 47169 | WCRLNLHEE | 49266 |
| HPV31 | E1 | 101 | SSCVDYNISPRLKAI | 47170 | VDYNISPRL | 49267 |
| HPV31 | E1 | 253 | SWGMVMLMLVRFKCA | 47171 | MVMLMLVRF | 49268 |
| HPV31 | E1 | 285 | TNCMLIQPPKLRSTA | 47172 | MLIQPPKLR | 49269 |
| HPV31 | E1 | 319 | TPEWIERQTVLQHSF | 47173 | WIERQTVLQ | 49270 |
| HPV31 | E1 | 221 | VAAFGVTGTVAEGFK | 47174 | FGVTGTVAE | 49271 |
| HPV31 | E1 | 51 | VDFIDNCNVYNNQAE | 47175 | IDNCNVYNN | 49272 |
| HPV31 | E1 | 23 | VEAVIDRQTGDNISE | 47176 | VIDRQTGDN | 49273 |
| HPV31 | E1 | 568 | VFTFPNPFPFDKNGN | 47177 | FPNPFPFDK | 49274 |
| HPV31 | E1 | 426 | VKFLRYQQIEFVSFL | 47178 | LRYQQIEFV | 49275 |
| HPV31 | E1 | 85 | VQVLKRKYVGSPLSD | 47179 | LKRKYVGSP | 49276 |
| HPV31 | E1 | 437 | VSFLSALKLFLKGVP | 47180 | LSALKLFLK | 49277 |
| HPV31 | E1 | 200 | VSFMELIRPFQSNKS | 47181 | MELIRPFQS | 49278 |
| HPV31 | E1 | 254 | WGMVMLMLVRFKCAK | 47182 | VMLMLVRFK | 49279 |
| HPV31 | E1 | 559 | WPYLHSRLVVFTFPN | 47183 | LHSRLVVFT | 49280 |
| HPV31 | E1 | 362 | YAQLADSDSNACAFL | 47184 | LADSDSNAC | 49281 |
| HPV31 | E1 | 244 | YCHLQSLACSWGMVM | 47185 | LQSLACSWG | 49282 |
| HPV31 | E1 | 241 | YCLYCHLQSLACSWG | 47186 | YCHLQSLAC | 49283 |
| HPV31 | E2 | 211 | AGIVTKLPTANNTTT | 47187 | VTKLPTANN | 49284 |
| HPV31 | E2 | 70 | AKALQAIELQMMLET | 47188 | LQAIELQMM | 49285 |
| HPV31 | E2 | 64 | ALSVSKAKALQAIEL | 47189 | VSKAKALQA | 49286 |
| HPV31 | E2 | 49 | AREMGIHSINHQVVP | 47190 | MGIHSINHQ | 49287 |
| HPV31 | E2 | 275 | CGVISAAACTNQTRA | 47191 | ISAAACTNQ | 49288 |
| HPV31 | E2 | 354 | DDFLNTVKIPNTVSV | 47192 | LNTVKIPNT | 49289 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV31 | E2 | 94 | DWTMQQTSLELYLTA | 47193 | MQQTSLELY | 49290 |
| HPV31 | E2 | 152 | EGQVNCKGIYYVHEG | 47194 | VNCKGIYYV | 49291 |
| HPV31 | E2 | 207 | EISFAGIVTKLPTAN | 47195 | FAGIVTKLP | 49292 |
| HPV31 | E2 | 77 | ELQMMLETLNNTEYK | 47196 | MMLETLNNT | 49293 |
| HPV31 | E2 | 200 | ESVFSSDEISFAGIV | 47197 | FSSDEISFA | 49294 |
| HPV31 | E2 | 210 | FAGIVTKLPTANNTT | 47198 | IVTKLPTAN | 49295 |
| HPV31 | E2 | 267 | GDSVDSVNCGVISAA | 47199 | VDSVNCGVI | 49296 |
| HPV31 | E2 | 193 | GQVIVFPESVFSSDE | 47200 | IVFPESVFS | 49297 |
| HPV31 | E2 | 38 | HIRLECVLMYKAREM | 47201 | LECVLMYKA | 49298 |
| HPV31 | E2 | 167 | HITYFVNFTEEAKKY | 47202 | YFVNFTEEA | 49299 |
| HPV31 | E2 | 59 | HQVVPALSVSKAKAL | 47203 | VPALSVSKA | 49300 |
| HPV31 | E2 | 33 | IDYWKHIRLECVLMY | 47204 | WKHIRLECV | 49301 |
| HPV31 | E2 | 54 | IHSINHQVVPALSVS | 47205 | INHQVVPAL | 49302 |
| HPV31 | E2 | 342 | IVTLTYISTSQRDDF | 47206 | LTYISTSQR | 49303 |
| HPV31 | E2 | 160 | IYYVHEGHITYFVNF | 47207 | VHEGHITYF | 49304 |
| HPV31 | E2 | 319 | KQLYEQVSSTWHWTC | 47208 | YEQVSSTWH | 49305 |
| HPV31 | E2 | 41 | LECVLMYKAREMGIH | 47209 | VLMYKAREM | 49306 |
| HPV31 | E2 | 102 | LELYLTAPTGCLKKH | 47210 | YLTAPTGCL | 49307 |
| HPV31 | E2 | 308 | LKCLRYRLSKYKQLY | 47211 | LRYRLSKYK | 49308 |
| HPV31 | E2 | 357 | LNTVKIPNTVSVSTG | 47212 | VKIPNTVSV | 49309 |
| HPV31 | E2 | 73 | LQAIELQMMLETLNN | 47213 | IELQMMLET | 49310 |
| HPV31 | E2 | 340 | NAIVTLTYISTSQRD | 47214 | VTLTYISTS | 49311 |
| HPV31 | E2 | 274 | NCGVISAAACTNQTR | 47215 | VISAAACTN | 49312 |
| HPV31 | E2 | 92 | NEDWTMQQTSLELYL | 47216 | WTMQQTSLE | 49313 |
| HPV31 | E2 | 58 | NHQVVPALSVSKAKA | 47217 | VVPALSVSK | 49314 |
| HPV31 | E2 | 262 | NKLLRGDSVDSVNCG | 47218 | LRGDSVDSV | 49315 |
| HPV31 | E2 | 136 | NWKFIYLCIDGQCTV | 47219 | FIYLCIDGQ | 49316 |
| HPV31 | E2 | 261 | PNKLLRGDSVDSVNC | 47220 | LLRGDSVDS | 49317 |
| HPV31 | E2 | 147 | QCTVVEGQVNCKGIY | 47221 | VVEGQVNCK | 49318 |
| HPV31 | E2 | 99 | QTSLELYLTAPTGCL | 47222 | LELYLTAPT | 49319 |
| HPV31 | E2 | 194 | QVIVFPESVFSSDEI | 47223 | VFPESVFSS | 49320 |
| HPV31 | E2 | 10 | RLNVCQDKILEHYEN | 47224 | VCQDKILEH | 49321 |
| HPV31 | E2 | 205 | SDEISFAGIVTKLPT | 47225 | ISFAGIVTK | 49322 |
| HPV31 | E2 | 236 | SEGVRRATTSTKRPR | 47226 | VRRATTSTK | 49323 |
| HPV31 | E2 | 101 | SLELYLTAPTGCLKK | 47227 | LYLTAPTGC | 49324 |
| HPV31 | E2 | 326 | SSTWHWTCTDGKHKN | 47228 | WHWTCTDGK | 49325 |
| HPV31 | E2 | 287 | TRAVSCPATTPIIHL | 47229 | VSCPATTPI | 49326 |
| HPV31 | E2 | 359 | TVKIPNTVSVSTGYM | 47230 | IPNTVSVST | 49327 |
| HPV31 | E2 | 270 | VDSVNCGVISAAACT | 47231 | VNCGVISAA | 49328 |
| HPV31 | E2 | 44 | VLMYKAREMGIHSIN | 47232 | YKAREMGIH | 49329 |
| HPV31 | E2 | 62 | VPALSVSKAKALQAI | 47233 | LSVSKAKAL | 49330 |
| HPV31 | E2 | 36 | WKHIRLECVLMYKAR | 47234 | IRLECVLMY | 49331 |
| HPV31 | E2 | 318 | YKQLYEQVSSTWHWT | 47235 | LYEQVSSTW | 49332 |
| HPV31 | E2 | 141 | YLCIDGQCTVVEGQV | 47236 | IDGQCTVVE | 49333 |
| HPV31 | E2 | 134 | YTNWKFIYLCIDGQC | 47237 | WKFIYLCID | 49334 |
| HPV31 | E5 | 1 | ---MIELNISTVSIV | 47238 | MIELNISTV | 49335 |
| HPV31 | E5 | 2 | --MIELNISTVSIVL | 47239 | IELNISTVS | 49336 |
| HPV31 | E5 | 43 | ATLLLLIVILWVIAT | 47240 | LLLIVILWV | 49337 |
| HPV31 | E5 | 62 | CFCIYVVFIYIPLFV | 47241 | IYVVFIYIP | 49338 |
| HPV31 | E5 | 21 | CFCVLLFVCLVIRPL | 47242 | VLLFVCLVI | 49339 |
| HPV31 | E5 | 17 | CFLLCFCVLLFVCLV | 47243 | LCFCVLLFV | 49340 |
| HPV31 | E5 | 64 | CIYVVFIYIPLFVIH | 47244 | VVFIYIPLF | 49341 |
| HPV31 | E5 | 29 | CLVIRPLVLSVSVYA | 47245 | IRPLVLSVS | 49342 |
| HPV31 | E5 | 23 | CVLLFVCLVIRPLVL | 47246 | LFVCLVIRP | 49343 |
| HPV31 | E5 | 6 | ELNISTVSIVLCFLL | 47247 | ISTVSIVLC | 49344 |
| HPV31 | E5 | 22 | FCVLLFVCLVIRPLV | 47248 | LLFVCLVIR | 49345 |
| HPV31 | E5 | 69 | FIYIPLFVIHTHASF | 47249 | IPLFVIHTH | 49346 |
| HPV31 | E5 | 27 | FVCLVIRPLVLSVSV | 47250 | LVIRPLVLS | 49347 |
| HPV31 | E5 | 51 | ILWVIATSPLRCFCI | 47251 | VIATSPLRC | 49348 |
| HPV31 | E5 | 32 | IRPLVLSVSVYATLL | 47252 | LVLSVSVYA | 49349 |
| HPV31 | E5 | 9 | ISTVSIVLCFLLCFC | 47253 | VSIVLCFLL | 49350 |
| HPV31 | E5 | 49 | IVILWVIATSPLRCF | 47254 | LWVIATSPL | 49351 |
| HPV31 | E5 | 65 | IYVVFIYIPLFVIHT | 47255 | VFIYIPLFV | 49352 |
| HPV31 | E5 | 16 | LCFLLCFCVLLFVCL | 47256 | LLCFCVLLF | 49353 |
| HPV31 | E5 | 74 | LFVIHTHASFLSQQ- | 47257 | IHTHASFLS | 49354 |
| HPV31 | E5 | 48 | LIVILWVIATSPLRC | 47258 | ILWVIATSP | 49355 |
| HPV31 | E5 | 47 | LLIVILWVIATSPLR | 47259 | VILWVIATS | 49356 |
| HPV31 | E5 | 46 | LLLIVILWVIATSPL | 47260 | IVILWVIAT | 49357 |
| HPV31 | E5 | 60 | LRCFCIYVVFIYIPL | 47261 | FCIYVVFIY | 49358 |
| HPV31 | E5 | 52 | LWVIATSPLRCFCIY | 47262 | IATSPLRCF | 49359 |
| HPV31 | E5 | 4 | MIELNISTVSIVLCF | 47263 | LNISTVSIV | 49360 |
| HPV31 | E5 | 73 | PLFVIHTHASFLSQQ | 47264 | VIHTHASFL | 49361 |
| HPV31 | E5 | 33 | RPLVLSVSVYATLLL | 47265 | VLSVSVYAT | 49362 |
| HPV31 | E5 | 13 | SIVLCFLLCFCVLLF | 47266 | LCFLLCFCV | 49363 |
| HPV31 | E5 | 38 | SVSVYATLLLLIVIL | 47267 | VYATLLLLI | 49364 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV31 | E5 | 44 | TLLLLIVILWVIATS | 47268 | LLIVILWVI | 49365 |
| HPV31 | E5 | 57 | TSPLRCFCIYVVFIY | 47269 | LRCFCIYVV | 49366 |
| HPV31 | E5 | 11 | TVSIVLCFLLCFCVL | 47270 | IVLCFLLCF | 49367 |
| HPV31 | E5 | 28 | VCLVIRPLVLSVSVY | 47271 | VIRPLVLSV | 49368 |
| HPV31 | E5 | 68 | VFIYIPLFVIHTHAS | 47272 | YIPLFVIHT | 49369 |
| HPV31 | E5 | 50 | VILWVIATSPLRCFC | 47273 | WVIATSPLR | 49370 |
| HPV31 | E5 | 15 | VLCFLLCFCVLLFVC | 47274 | FLLCFCVLL | 49371 |
| HPV31 | E5 | 24 | VLLFVCLVIRPLVLS | 47275 | FVCLVIRPL | 49372 |
| HPV31 | E5 | 36 | VLSVSVYATLLLLIV | 47276 | VSVYATLLL | 49373 |
| HPV31 | E5 | 12 | VSIVLCFLLCFCVLL | 47277 | VLCFLLCFC | 49374 |
| HPV31 | E5 | 39 | VSVYATLLLLIVILW | 47278 | YATLLLLIV | 49375 |
| HPV31 | E5 | 42 | YATLLLLIVILWVIA | 47279 | LLLLIVILW | 49376 |
| HPV31 | E5 | 71 | YIPLFVIHTHASFLS | 47280 | LFVIHTHAS | 49377 |
| HPV31 | E5 | 66 | YVVFIYIPLFVIHTH | 47281 | FIYIPLFVI | 49378 |
| HPV31 | E6 | 1 | ---MFKNPAERPRKL | 47282 | MFKNPAERP | 49379 |
| HPV31 | E6 | 21 | ALEIPYDELRLNCVY | 47283 | IPYDELRLN | 49380 |
| HPV31 | E6 | 100 | CDLLIRCITCQRPLC | 47284 | LIRCITCQR | 49381 |
| HPV31 | E6 | 69 | CLRFYSKVSEFRWYR | 47285 | FYSKVSEFR | 49382 |
| HPV31 | E6 | 47 | DFAFTDLTIVYRDDT | 47286 | FTDLTIVYR | 49383 |
| HPV31 | E6 | 101 | DLLIRCITCQRPLCP | 47287 | IRCITCQRP | 49384 |
| HPV31 | E6 | 78 | EFRWYRYSVYGTTLE | 47288 | WYRYSVYGT | 49385 |
| HPV31 | E6 | 23 | EIPYDELRLNCVYCK | 47289 | YDELRLNCV | 49386 |
| HPV31 | E6 | 28 | ELRLNCVYCKGQLTE | 47290 | LNCVYCKGQ | 49387 |
| HPV31 | E6 | 128 | FHNIGGRWTGRCIAC | 47291 | IGGRWTGRC | 49388 |
| HPV31 | E6 | 132 | GGRWTGRCIACWRRP | 47292 | WTGRCIACW | 49389 |
| HPV31 | E6 | 140 | IACWRRPRTETQV-- | 47293 | WRRPRTETQ | 49390 |
| HPV31 | E6 | 99 | ICDLLIRCITCQRPL | 47294 | LLIRCITCQ | 49391 |
| HPV31 | E6 | 104 | IRCITCQRPLCPEEK | 47295 | ITCQRPLCP | 49392 |
| HPV31 | E6 | 37 | KGQLTETEVLDFAFT | 47296 | LTETEVLDF | 49393 |
| HPV31 | E6 | 91 | LEKLTNKGICDLLIR | 47297 | LTNKGICDL | 49394 |
| HPV31 | E6 | 53 | LTIVYRDDTPHGVCT | 47298 | VYRDDTPHG | 49395 |
| HPV31 | E6 | 32 | NCVYCKGQLTETEVL | 47299 | YCKGQLTET | 49396 |
| HPV31 | E6 | 96 | NKGICDLLIRCITCQ | 47300 | ICDLLIRCI | 49397 |
| HPV31 | E6 | 62 | PHGVCTKCLRFYSKV | 47301 | VCTKCLRFY | 49398 |
| HPV31 | E6 | 12 | PRKLHELSSALEIPY | 47302 | LHELSSALE | 49399 |
| HPV31 | E6 | 83 | RYSVYGTTLEKLTNK | 47303 | VYGTTLEKL | 49400 |
| HPV31 | E6 | 43 | TEVLDFAFTDLTIVY | 47304 | LDFAFTDLT | 49401 |
| HPV31 | E6 | 54 | TIVYRDDTPHGVCTK | 47305 | YRDDTPHGV | 49402 |
| HPV31 | E6 | 45 | VLDFAFTDLTIVYRD | 47306 | FAFTDLTIV | 49403 |
| HPV31 | E6 | 81 | WYRYSVYGTTLEKLT | 47307 | YSVYGTTLE | 49404 |
| HPV31 | E6 | 26 | YDELRLNCVYCKGQL | 47308 | LRLNCVYCK | 49405 |
| HPV31 | E7 | 1 | ---MRGETPTLQDYV | 47309 | MRGETPTLQ | 49406 |
| HPV31 | E7 | 78 | DIRILQELLMGSFGI | 47310 | ILQELLMGS | 49407 |
| HPV31 | E7 | 37 | EEDVIDSPAGQAEPD | 47311 | VIDSPAGQA | 49408 |
| HPV31 | E7 | 84 | ELLMGSFGIVCPNCS | 47312 | MGSFGIVCP | 49409 |
| HPV31 | E7 | 90 | FGIVCPNCSTRL--- | 47313 | VCPNCSTRL | 49410 |
| HPV31 | E7 | 79 | IRILQELLMGSFGIV | 47314 | LQELLMGSF | 49411 |
| HPV31 | E7 | 87 | MGSFGIVCPNCSTRL | 47315 | FGIVCPNCS | 49412 |
| HPV31 | E7 | 54 | NYNIVTFCCQCKSTL | 47316 | IVTFCCQCK | 49413 |
| HPV31 | E7 | 12 | QDYVLDLQPEATDLH | 47317 | VLDLQPEAT | 49414 |
| HPV31 | E7 | 69 | RLCVQSTQVDIRILQ | 47318 | VQSTQVDIR | 49415 |
| HPV31 | E7 | 89 | SFGIVCPNCSTRL-- | 47319 | IVCPNCSTR | 49416 |
| HPV31 | E7 | 74 | STQVDIRILQELLMG | 47320 | VDIRILQEL | 49417 |
| HPV31 | E7 | 67 | TLRLCVQSTQVDIRI | 47321 | LCVQSTQVD | 49418 |
| HPV31 | E7 | 8 | TPTLQDYVLDLQPEA | 47322 | LQDYVLDLQ | 49419 |
| HPV31 | E7 | 15 | VLDLQPEATDLHCYE | 47323 | LQPEATDLH | 49420 |
| HPV31 | L1 | 1 | ---MSLWRPSEATVY | 47324 | MSLWRPSEA | 49421 |
| HPV31 | L1 | 389 | ADIMTYIHSMNPAIL | 47325 | MTYIHSMNP | 49422 |
| HPV31 | L1 | 43 | ARLLTVGHPYYSIPK | 47326 | LTVGHPYYS | 49423 |
| HPV31 | L1 | 12 | ATVYLPPVPVSKVVS | 47327 | YLPPVPVSK | 49424 |
| HPV31 | L1 | 349 | CAAIANSDTTFKSSN | 47328 | IANSDTTFK | 49425 |
| HPV31 | L1 | 150 | CISMDYKQTQLCLLG | 47329 | MDYKQTQLC | 49426 |
| HPV31 | L1 | 189 | CPPLELKNSVIQDGD | 47330 | LELKNSVIQ | 49427 |
| HPV31 | L1 | 28 | DEYVTRTNIYYHAGS | 47331 | VTRTNIYYH | 49428 |
| HPV31 | L1 | 375 | DLQFIFQLCKITLSA | 47332 | FIFQLCKIT | 49429 |
| HPV31 | L1 | 278 | DLYIKGSGSTATLAN | 47333 | IKGSGSTAT | 49430 |
| HPV31 | L1 | 91 | DTSFYNPETQRLVWA | 47334 | FYNPETQRL | 49431 |
| HPV31 | L1 | 405 | DWNFGLTTPPSGSLE | 47335 | FGLTTPPSG | 49432 |
| HPV31 | L1 | 447 | DYVFWEVNLKEKFSA | 47336 | FWEVNLKEK | 49433 |
| HPV31 | L1 | 11 | EATVYLPPVPVSKVV | 47337 | VYLPPVPVS | 49434 |
| HPV31 | L1 | 419 | EDTYRFVTSQAITCQ | 47338 | YRFVTSQAI | 49435 |
| HPV31 | L1 | 452 | EVNLKEKFSADLDQF | 47339 | LKEKFSADL | 49436 |
| HPV31 | L1 | 251 | FFYLRREQMFVRHFF | 47340 | LRREQMFVR | 49437 |
| HPV31 | L1 | 209 | FGAMDFTALQDTKSN | 47341 | MDFTALQDT | 49438 |
| HPV31 | L1 | 445 | FKDYVFWEVNLKEKF | 47342 | YVFWEVNLK | 49439 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV31 | L1 | 214 | FTALQDTKSNVPLDI | 47343 | LQDTKSNVP | 49440 |
| HPV31 | L1 | 371 | GEEFDLQFIFQLCKI | 47344 | FDLQFIFQL | 49441 |
| HPV31 | L1 | 170 | GEHWGKGSPCSNNAI | 47345 | WGKGSPCSN | 49442 |
| HPV31 | L1 | 108 | GLEVGRGQPLGVGIS | 47346 | VGRGQPLGV | 49443 |
| HPV31 | L1 | 71 | GLQYRVFRVRLPDPN | 47347 | YRVFRVRLP | 49444 |
| HPV31 | L1 | 330 | GNQLFVTVVDTTRST | 47348 | LFVTVVDTT | 49445 |
| HPV31 | L1 | 114 | GQPLGVGISGHPLLN | 47349 | LGVGISGHP | 49446 |
| HPV31 | L1 | 118 | GVGISGHPLLNKFDD | 47350 | ISGHPLLNK | 49447 |
| HPV31 | L1 | 50 | HPYYSIPKSDNPKKI | 47351 | YSIPKSDNP | 49448 |
| HPV31 | L1 | 379 | IFQLCKITLSADIMT | 47352 | LCKITLSAD | 49449 |
| HPV31 | L1 | 395 | IHSMNPAILEDWNFG | 47353 | MNPAILEDW | 49450 |
| HPV31 | L1 | 384 | KITLSADIMTYIHSM | 47354 | LSADIMTYI | 49451 |
| HPV31 | L1 | 62 | KKIVVPKVSGLQYRV | 47355 | VVPKVSGLQ | 49452 |
| HPV31 | L1 | 221 | KSNVPLDICNSICKY | 47356 | VPLDICNSI | 49453 |
| HPV31 | L1 | 160 | LCLLGCKPPIGEHWG | 47357 | LGCKPPIGE | 49454 |
| HPV31 | L1 | 403 | LEDWNFGLTTPPSGS | 47358 | WNFGLTTPP | 49455 |
| HPV31 | L1 | 16 | LPPVPVSKVVSTDEY | 47359 | VPVSKVVST | 49456 |
| HPV31 | L1 | 4 | MSLWRPSEATVYLPP | 47360 | WRPSEATVY | 49457 |
| HPV31 | L1 | 392 | MTYIHSMNPAILEDW | 47361 | IHSMNPAIL | 49458 |
| HPV31 | L1 | 407 | NFGLTTPPSGSLEDT | 47362 | LTTPPSGSL | 49459 |
| HPV31 | L1 | 35 | NIYYHAGSARLLTVG | 47363 | YHAGSARLL | 49460 |
| HPV31 | L1 | 312 | NKPYWMQRAQGHNNG | 47364 | YWMQRAQGH | 49461 |
| HPV31 | L1 | 345 | NMSVCAAIANSDTTF | 47365 | VCAAIANSD | 49462 |
| HPV31 | L1 | 181 | NNAITPGDCPPLELK | 47366 | ITPGDCPPL | 49463 |
| HPV31 | L1 | 292 | NSTYFPTPSGSMVTS | 47367 | YFPTPSGSM | 49464 |
| HPV31 | L1 | 196 | NSVIQDGDMVDTGFG | 47368 | IQDGDMVDT | 49465 |
| HPV31 | L1 | 223 | NVPLDICNSICKYPD | 47369 | LDICNSICK | 49466 |
| HPV31 | L1 | 61 | PKKIVVPKVSGLQYR | 47370 | IVVPKVSGL | 49467 |
| HPV31 | L1 | 225 | PLDICNSICKYPDYL | 47371 | ICNSICKYP | 49468 |
| HPV31 | L1 | 191 | PLELKNSVIQDGDMV | 47372 | LKNSVIQDG | 49469 |
| HPV31 | L1 | 84 | PNKFGFPDTSFYNPE | 47373 | FGFPDTSFY | 49470 |
| HPV31 | L1 | 276 | PTDLYIKGSGSTATL | 47374 | LYIKGSGST | 49471 |
| HPV31 | L1 | 18 | PVPVSKVVSTDEYVT | 47375 | VSKVVSTDE | 49472 |
| HPV31 | L1 | 377 | QFIFQLCKITLSADI | 47376 | FQLCKITLS | 49473 |
| HPV31 | L1 | 465 | QFPLGRKFLLQAGYR | 47377 | LGRKFLLQA | 49474 |
| HPV31 | L1 | 159 | QLCLLGCKPPIGEHW | 47378 | LLGCKPPIG | 49475 |
| HPV31 | L1 | 332 | QLFVTVVDTTRSTNM | 47379 | VTVVDTTRS | 49476 |
| HPV31 | L1 | 157 | QTQLCLLGCKPPIGE | 47380 | LCLLGCKPP | 49477 |
| HPV31 | L1 | 73 | QYRVFRVRLPDPNKF | 47381 | VFRVRLPDP | 49478 |
| HPV31 | L1 | 262 | RHFFNRSGTVGESVP | 47382 | FNRSGTVGE | 49479 |
| HPV31 | L1 | 101 | RLVWACVGLEVGRGQ | 47383 | WACVGLEVG | 49480 |
| HPV31 | L1 | 460 | SADLDQFPLGRKFLL | 47384 | LDQFPLGRK | 49481 |
| HPV31 | L1 | 300 | SGSMVTSDAQIFNKP | 47385 | MVTSDAQIF | 49482 |
| HPV31 | L1 | 268 | SGTVGESVPTDLYIK | 47386 | VGESVPTDL | 49483 |
| HPV31 | L1 | 152 | SMDYKQTQLCLLGCK | 47387 | YKQTQLCLL | 49484 |
| HPV31 | L1 | 427 | SQAITCQKTAPQKPK | 47388 | ITCQKTAPQ | 49485 |
| HPV31 | L1 | 343 | STNMSVCAAIANSDT | 47389 | MSVCAAIAN | 49486 |
| HPV31 | L1 | 34 | TNIYYHAGSARLLTV | 47390 | YYHAGSARL | 49487 |
| HPV31 | L1 | 99 | TQRLVWACVGLEVGR | 47391 | LVWACVGLE | 49488 |
| HPV31 | L1 | 13 | TVYLPPVPVSKVVST | 47392 | LPPVPVSKV | 49489 |
| HPV31 | L1 | 421 | TYRFVTSQAITCQKT | 47393 | FVTSQAITC | 49490 |
| HPV31 | L1 | 76 | VFRVRLPDPNKFGFP | 47394 | VRLPDPNKF | 49491 |
| HPV31 | L1 | 335 | VTVVDTTRSTNMSVC | 47395 | VDTTRSTNM | 49492 |
| HPV31 | L1 | 235 | YPDYLKMVAEPYGDT | 47396 | YLKMVAEPY | 49493 |
| HPV31 | L1 | 422 | YRFVTSQAITCQKTA | 47397 | VTSQAITCQ | 49494 |
| HPV31 | L1 | 74 | YRVFRVRLPDPNKFG | 47398 | FRVRLPDPN | 49495 |
| HPV31 | L2 | 1 | ---MRSKRSTKRTKR | 47399 | MRSKRSTKR | 49496 |
| HPV31 | L2 | 45 | ADQILRYGSMGVFFG | 47400 | ILRYGSMGV | 49497 |
| HPV31 | L2 | 363 | DFTVDTPATHNVSPS | 47401 | VDTPATHNV | 49498 |
| HPV31 | L2 | 276 | DPDFLDIIALHRPAL | 47402 | FLDIIALHR | 49499 |
| HPV31 | L2 | 163 | DPSVLQPPTPAETSG | 47403 | VLQPPTPAE | 49500 |
| HPV31 | L2 | 46 | DQILRYGSMGVFFGG | 47404 | LRYGSMGVF | 49501 |
| HPV31 | L2 | 361 | DTDFTVDTPATHNVS | 47405 | FTVDTPATH | 49502 |
| HPV31 | L2 | 411 | DVPIEHAPTQVFPFP | 47406 | IEHAPTQVF | 49503 |
| HPV31 | L2 | 87 | EASIPIRPPVSIDPV | 47407 | IPIRPPVSI | 49504 |
| HPV31 | L2 | 261 | EESLYFSNTSHNIAP | 47408 | LYFSNTSHN | 49505 |
| HPV31 | L2 | 193 | EIPMDTFIVSTNNEN | 47409 | MDTFIVSTN | 49506 |
| HPV31 | L2 | 114 | ESGIVDVGAPAPIPH | 47410 | IVDVGAPAP | 49507 |
| HPV31 | L2 | 262 | ESLYFSNTSHNIAPD | 47411 | YFSNTSHNI | 49508 |
| HPV31 | L2 | 333 | GESIEMQPLGASATT | 47412 | IEMQPLGAS | 49509 |
| HPV31 | L2 | 439 | GGDFYLHPSYYMLKR | 47413 | FYLHPSYYM | 49510 |
| HPV31 | L2 | 177 | GHLLLSSSSISTHNY | 47414 | LLSSSSIST | 49511 |
| HPV31 | L2 | 409 | GPDVPIEHAPTQVFP | 47415 | VPIEHAPTQ | 49512 |
| HPV31 | L2 | 55 | GVFFGGLGIGSGSGT | 47416 | FGGLGIGSG | 49513 |
| HPV31 | L2 | 178 | HLLLSSSSISTHNYE | 47417 | LSSSSISTH | 49514 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV31 | L2 | 41 | HTTIADQILRYGSMG | 47418 | IADQILRYG | 49515 |
| HPV31 | L2 | 321 | HYYYDISSINPAGES | 47419 | YDISSINPA | 49516 |
| HPV31 | L2 | 98 | IDPVGPLDPSIVSLV | 47420 | VGPLDPSIV | 49517 |
| HPV31 | L2 | 282 | IIALHRPALTSRRNT | 47421 | LHRPALTSR | 49518 |
| HPV31 | L2 | 147 | ILDVTSVSTHENPTF | 47422 | VTSVSTHEN | 49519 |
| HPV31 | L2 | 48 | ILRYGSMGVFFGGLG | 47423 | YGSMGVFFG | 49520 |
| HPV31 | L2 | 404 | IPIFSGPDVPIEHAP | 47424 | FSGPDVPIE | 49521 |
| HPV31 | L2 | 36 | IPKIEHTTIADQILR | 47425 | IEHTTIADQ | 49522 |
| HPV31 | L2 | 117 | IVDVGAPAPIPHPPT | 47426 | VGAPAPIPH | 49523 |
| HPV31 | L2 | 245 | KQLITYENPAYETVN | 47427 | ITYENPAYE | 49524 |
| HPV31 | L2 | 280 | LDIIALHRPALTSRR | 47428 | IALHRPALT | 49525 |
| HPV31 | L2 | 338 | MQPLGASATTTSTLN | 47429 | LGASATTTS | 49526 |
| HPV31 | L2 | 352 | NDGLYDIYADTDFTV | 47430 | LYDIYADTD | 49527 |
| HPV31 | L2 | 205 | NENITSSTPIPGVRR | 47431 | ITSSTPIPG | 49528 |
| HPV31 | L2 | 252 | NPAYETVNAEESLYF | 47432 | YETVNAEES | 49529 |
| HPV31 | L2 | 158 | NPTFTDPSVLQPPTP | 47433 | FTDPSVLQP | 49530 |
| HPV31 | L2 | 145 | PAILDVTSVSTHENP | 47434 | LDVTSVSTH | 49531 |
| HPV31 | L2 | 123 | PAPIPHPPTTSGFDI | 47435 | IPHPPTTSG | 49532 |
| HPV31 | L2 | 277 | PDFLDIIALHRPALT | 47436 | LDIIALHRP | 49533 |
| HPV31 | L2 | 423 | PFPLAPTTPQVSIFV | 47437 | LAPTTPQVS | 49534 |
| HPV31 | L2 | 82 | PSTVSEASIPIRPPV | 47438 | VSEASIPIR | 49535 |
| HPV31 | L2 | 164 | PSVLQPPTPAETSGH | 47439 | LQPPTPAET | 49536 |
| HPV31 | L2 | 418 | PTQVFPFPLAPTTPQ | 47440 | VFPFPLAPT | 49537 |
| HPV31 | L2 | 95 | PVSIDPVGPLDPSIV | 47441 | IDPVGPLDP | 49538 |
| HPV31 | L2 | 455 | RKRVSYFFTDVSVAA | 47442 | VSYFFTDVS | 49539 |
| HPV31 | L2 | 222 | RLGLYSKATQQVKVI | 47443 | LYSKATQQV | 49540 |
| HPV31 | L2 | 294 | RNTVRYSRLGNKQTL | 47444 | VRYSRLGNK | 49541 |
| HPV31 | L2 | 93 | RPPVSIDPVGPLDPS | 47445 | VSIDPVGPL | 49542 |
| HPV31 | L2 | 72 | RTGYVPLSTRPSTVS | 47446 | YVPLSTRPS | 49543 |
| HPV31 | L2 | 319 | RVHYYYDISSINPAG | 47447 | YYYDISSIN | 49544 |
| HPV31 | L2 | 457 | RVSYFFTDVSVAA-- | 47448 | YFFTDVSVA | 49545 |
| HPV31 | L2 | 387 | SAYVPTNTTVPLSTG | 47449 | VPTNTTVPL | 49546 |
| HPV31 | L2 | 176 | SGHLLLSSSSISTHN | 47450 | LLLSSSSIS | 49547 |
| HPV31 | L2 | 115 | SGIVDVGAPAPIPHP | 47451 | VDVGAPAPI | 49548 |
| HPV31 | L2 | 335 | SIEMQPLGASATTTS | 47452 | MQPLGASAT | 49549 |
| HPV31 | L2 | 89 | SIPIRPPVSIDPVGP | 47453 | IRPPVSIDP | 49550 |
| HPV31 | L2 | 53 | SMGVFFGGLGIGSGS | 47454 | VFFGGLGIG | 49551 |
| HPV31 | L2 | 377 | STAVQSTSAVSAYVP | 47455 | VQSTSAVSA | 49552 |
| HPV31 | L2 | 371 | THNVSPSTAVQSTSA | 47456 | VSPSTAVQS | 49553 |
| HPV31 | L2 | 188 | THNYEEIPMDTFIVS | 47457 | YEEIPMDTF | 49554 |
| HPV31 | L2 | 144 | TPAILDVTSVSTHEN | 47458 | ILDVTSVST | 49555 |
| HPV31 | L2 | 19 | TQLYQTCKAAGTCPS | 47459 | YQTCKAAGT | 49556 |
| HPV31 | L2 | 230 | TQQVKVIDPTFLSAP | 47460 | VKVIDPTFL | 49557 |
| HPV31 | L2 | 419 | TQVFPFPLAPTTPQV | 47461 | FPFPLAPTT | 49558 |
| HPV31 | L2 | 383 | TSAVSAYVPTNTTVP | 47462 | VSAYVPTNT | 49559 |
| HPV31 | L2 | 132 | TSGFDIATTADTTPA | 47463 | FDIATTADT | 49560 |
| HPV31 | L2 | 421 | VFPFPLAPTTPQVSI | 47464 | FPLAPTTPQ | 49561 |
| HPV31 | L2 | 101 | VGPLDPSIVSLVEES | 47465 | LDPSIVSLV | 49562 |
| HPV31 | L2 | 320 | VHYYYDISSINPAGE | 47466 | YYDISSINP | 49563 |
| HPV31 | L2 | 233 | VKVIDPTFLSAPKQL | 47467 | IDPTFLSAP | 49564 |
| HPV31 | L2 | 386 | VSAYVPTNTTVPLST | 47468 | YVPTNTTVP | 49565 |
| HPV31 | L2 | 109 | VSLVEESGIVDVGAP | 47469 | VEESGIVDV | 49566 |
| HPV31 | L2 | 458 | VSYFFTDVSVAA--- | 47470 | FFTDVSVAA | 49567 |
| HPV31 | L2 | 255 | YETVNAEESLYFSNT | 47471 | VNAEESLYF | 49568 |
| HPV31 | L2 | 299 | YSRLGNKQTLRTRSG | 47472 | LGNKQTLRT | 49569 |
| HPV31 | L2 | 75 | YVPLSTRPSTVSEAS | 47473 | LSTRPSTVS | 49570 |
| HPV31 | L2 | 323 | YYDISSINPAGESIE | 47474 | ISSINPAGE | 49571 |
| HPV33 | E1 | 385 | AAAFLKSNSQAKIVK | 47475 | FLKSNSQAK | 49572 |
| HPV33 | E1 | 100 | AEDVVDRAANPCRTS | 47476 | VVDRAANPC | 49573 |
| HPV33 | E1 | 395 | AKIVKDCGIMCRHYK | 47477 | VKDCGIMCR | 49574 |
| HPV33 | E1 | 287 | AKLMSNLLSIPETCM | 47478 | MSNLLSIPE | 49575 |
| HPV33 | E1 | 314 | ALYWFRTAMSNISDV | 47479 | WFRTAMSNI | 49576 |
| HPV33 | E1 | 210 | AYGISFMELVRPFKS | 47480 | ISFMELVRP | 49577 |
| HPV33 | E1 | 313 | CALYWFRTAMSNISD | 47481 | YWFRTAMSN | 49578 |
| HPV33 | E1 | 182 | CENVTLQEISNVLHS | 47482 | VTLQEISNV | 49579 |
| HPV33 | E1 | 300 | CMVIEPPKLRSQTCA | 47483 | IEPPKLRSQ | 49580 |
| HPV33 | E1 | 17 | CTGWFEVEAVIERRT | 47484 | WFEVEAVIE | 49581 |
| HPV33 | E1 | 602 | DENWKSFFSRTWCKL | 47485 | WKSFFSRTW | 49582 |
| HPV33 | E1 | 370 | DIAYYYAQLADSNSN | 47486 | YYYAQLADS | 49583 |
| HPV33 | E1 | 348 | DNIFDLSEMVQWAYD | 47487 | FDLSEMVQW | 49584 |
| HPV33 | E1 | 266 | DRGIIILLLIRFRCS | 47488 | IIILLLIRF | 49585 |
| HPV33 | E1 | 368 | DSDIAYYYAQLADSN | 47489 | IAYYYAQLA | 49586 |
| HPV33 | E1 | 133 | DSGYGNTEVETQQMV | 47490 | YGNTEVETQ | 49587 |
| HPV33 | E1 | 569 | DSRWPYLHSRLTVFE | 47491 | WPYLHSRLT | 49588 |
| HPV33 | E1 | 156 | DTNLNDLESSGVGDD | 47492 | LNDLESSGV | 49589 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV33 | E1 | 231 | DWCITGYGISPSVAE | 47493 | ITGYGISPS | 49590 |
| HPV33 | E1 | 120 | ECTYRKRKIDELEDS | 47494 | YRKRKIDEL | 49591 |
| HPV33 | E1 | 79 | EDDLNAVCALKRKFA | 47495 | LNAVCALKR | 49592 |
| HPV33 | E1 | 298 | ETCMVIEPPKLRSQT | 47496 | MVIEPPKLR | 49593 |
| HPV33 | E1 | 456 | FKKFLKGIPKKSCML | 47497 | FLKGIPKKS | 49594 |
| HPV33 | E1 | 492 | GCVISCVNSKSHFWL | 47498 | ISCVNSKSH | 49595 |
| HPV33 | E1 | 628 | GGNISTFKCSAGENT | 47499 | ISTFKCSAG | 49596 |
| HPV33 | E1 | 478 | GKSYFGMSLIQFLKG | 47500 | YFGMSLIQF | 49597 |
| HPV33 | E1 | 236 | GYGISPSVAESLKVL | 47501 | ISPSVAESL | 49598 |
| HPV33 | E1 | 547 | HRALVQLKCPPLLLT | 47502 | LVQLKCPPL | 49599 |
| HPV33 | E1 | 254 | HSLYTHLQCLTCDRG | 47503 | YTHLQCLTC | 49600 |
| HPV33 | E1 | 371 | IAYYYAQLADSNSNA | 47504 | YYAQLADSN | 49601 |
| HPV33 | E1 | 528 | IDDYMRNALDGNEIS | 47505 | YMRNALDGN | 49602 |
| HPV33 | E1 | 514 | IGMIDDVTPISWTYI | 47506 | IDDVTPISW | 49603 |
| HPV33 | E1 | 418 | IGQWIQSRCEKTNDG | 47507 | WIQSRCEKT | 49604 |
| HPV33 | E1 | 271 | ILLLIRFRCSKNRLT | 47508 | LIRFRCSKN | 49605 |
| HPV33 | E1 | 487 | IQFLKGCVISCVNSK | 47509 | LKGCVISCV | 49606 |
| HPV33 | E1 | 325 | ISDVQGTTPEWIDRL | 47510 | VQGTTPEWI | 49607 |
| HPV33 | E1 | 213 | ISFMELVRPFKSDKT | 47511 | MELVRPFKS | 49608 |
| HPV33 | E1 | 234 | ITGYGISPSVAESLK | 47512 | YGISPSVAE | 49609 |
| HPV33 | E1 | 208 | KEAYGISFMELVRPF | 47513 | YGISFMELV | 49610 |
| HPV33 | E1 | 513 | KIGMIDDVTPISWTY | 47514 | MIDDVTPIS | 49611 |
| HPV33 | E1 | 281 | KNRLTVAKLMSNLLS | 47515 | LTVAKLMSN | 49612 |
| HPV33 | E1 | 466 | KSCMLICGPANTGKS | 47516 | MLICGPANT | 49613 |
| HPV33 | E1 | 606 | KSFFSRTWCKLDLIE | 47517 | FSRTWCKLD | 49614 |
| HPV33 | E1 | 501 | KSHFWLQPLSDAKIG | 47518 | FWLQPLSDA | 49615 |
| HPV33 | E1 | 479 | KSYFGMSLIQFLKGC | 47519 | FGMSLIQFL | 49616 |
| HPV33 | E1 | 248 | KVLIKQHSLYTHLQC | 47520 | IKQHSLYTH | 49617 |
| HPV33 | E1 | 486 | LIQFLKGCVISCVNS | 47521 | FLKGCVISC | 49618 |
| HPV33 | E1 | 460 | LKGIPKKSCMLICGP | 47522 | IPKKSCMLI | 49619 |
| HPV33 | E1 | 247 | LKVLIKQHSLYTHLQ | 47523 | LIKQHSLYT | 49620 |
| HPV33 | E1 | 50 | LLEFIDDSMENSIQA | 47524 | FIDDSMENS | 49621 |
| HPV33 | E1 | 272 | LLLIRFRCSKNRLTV | 47525 | IRFRCSKNR | 49622 |
| HPV33 | E1 | 293 | LLSIPETCMVIEPPK | 47526 | IPETCMVIE | 49623 |
| HPV33 | E1 | 159 | LNDLESSGVGDDSEV | 47527 | LESSGVGDD | 49624 |
| HPV33 | E1 | 506 | LQPLSDAKIGMIDDV | 47528 | LSDAKIGMI | 49625 |
| HPV33 | E1 | 579 | LTVFEFKNPFPFDEN | 47529 | FEFKNPFPF | 49626 |
| HPV33 | E1 | 550 | LVQLKCPPLLLTSNT | 47530 | LKCPPLLLT | 49627 |
| HPV33 | E1 | 315 | LYWFRTAMSNISDVQ | 47531 | FRTAMSNIS | 49628 |
| HPV33 | E1 | 216 | MELVRPFKSDKTSCT | 47532 | VRPFKSDKT | 49629 |
| HPV33 | E1 | 202 | NILYKFKEAYGISFM | 47533 | YKFKEAYGI | 49630 |
| HPV33 | E1 | 138 | NTEVETQQMVQQVES | 47534 | VETQQMVQQ | 49631 |
| HPV33 | E1 | 333 | PEWIDRLTVLQHSFN | 47535 | IDRLTVLQH | 49632 |
| HPV33 | E1 | 305 | PPKLRSQTCALYWFR | 47536 | LRSQTCALY | 49633 |
| HPV33 | E1 | 556 | PPLLLTSNTNAGTDS | 47537 | LLTSNTNAG | 49634 |
| HPV33 | E1 | 144 | QQMVQQVESQNGDTN | 47538 | VQQVESQNG | 49635 |
| HPV33 | E1 | 358 | QWAYDNELTDDSDIA | 47539 | YDNELTDDS | 49636 |
| HPV33 | E1 | 548 | RALVQLKCPPLLLTS | 47540 | VQLKCPPLL | 49637 |
| HPV33 | E1 | 267 | RGIIILLLIRFRCSK | 47541 | IILLLIRFR | 49638 |
| HPV33 | E1 | 283 | RLTVAKLMSNLLSIP | 47542 | VAKLMSNLL | 49639 |
| HPV33 | E1 | 533 | RNALDGNEISIDVKH | 47543 | LDGNEISID | 49640 |
| HPV33 | E1 | 571 | RWPYLHSRLTVFEFK | 47544 | YLHSRLTVF | 49641 |
| HPV33 | E1 | 467 | SCMLICGPANTGKSY | 47545 | LICGPANTG | 49642 |
| HPV33 | E1 | 502 | SHFWLQPLSDAKIGM | 47546 | WLQPLSDAK | 49643 |
| HPV33 | E1 | 542 | SIDVKHRALVQLKCP | 47547 | VKHRALVQL | 49644 |
| HPV33 | E1 | 291 | SNLLSIPETCMVIEP | 47548 | LSIPETCMV | 49645 |
| HPV33 | E1 | 191 | SNVLHSSNTKANILY | 47549 | LHSSNTKAN | 49646 |
| HPV33 | E1 | 610 | SRTWCKLDLIEEEDK | 47550 | WCKLDLIEE | 49647 |
| HPV33 | E1 | 524 | SWTYIDDYMRNALDG | 47551 | YIDDYMRNA | 49648 |
| HPV33 | E1 | 312 | TCALYWFRTAMSNIS | 47552 | LYWFRTAMS | 49649 |
| HPV33 | E1 | 18 | TGWFEVEAVIERRTG | 47553 | FEVEAVIER | 49650 |
| HPV33 | E1 | 332 | TPEWIDRLTVLQHSF | 47554 | WIDRLTVLQ | 49651 |
| HPV33 | E1 | 286 | VAKLMSNLLSIPETC | 47555 | LMSNLLSIP | 49652 |
| HPV33 | E1 | 85 | VCALKRKFAACSQSA | 47556 | LKRKFAACS | 49653 |
| HPV33 | E1 | 23 | VEAVIERRTGDNISE | 47557 | VIERRTGDN | 49654 |
| HPV33 | E1 | 581 | VFEFKNPFPFDENGN | 47558 | FKNPFPFDE | 49655 |
| HPV33 | E1 | 439 | VQLLRYQNIEFTAFL | 47559 | LRYQNIEFT | 49656 |
| HPV33 | E1 | 219 | VRPFKSDKTSCTDWC | 47560 | FKSDKTSCT | 49657 |
| HPV33 | E1 | 520 | VTPISWTYIDDYMRN | 47561 | ISWTYIDDY | 49658 |
| HPV33 | E1 | 572 | WPYLHSRLTVFEFKN | 47562 | LHSRLTVFE | 49659 |
| HPV33 | E1 | 375 | YAQLADSNSNAAAFL | 47563 | LADSNSNAA | 49660 |
| HPV33 | E1 | 257 | YTHLQCLTCDRGIII | 47564 | LQCLTCDRG | 49661 |
| HPV33 | E2 | 1 | ---MEEISARLNAVQ | 47565 | MEEISARLN | 49662 |
| HPV33 | E2 | 178 | AAKYSKTQMWEVHVG | 47566 | YSKTQMWEV | 49663 |
| HPV33 | E2 | 72 | AFQVIELQMALETLS | 47567 | VIELQMALE | 49664 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV33 | E2 | 49 | AKQMGFSHLCHQVVP | 47568 | MGFSHLCHQ | 49665 |
| HPV33 | E2 | 44 | ALLYTAKQMGFSHLC | 47569 | YTAKQMGFS | 49666 |
| HPV33 | E2 | 240 | AQPLTKLFCADPALD | 47570 | LTKLFCADP | 49667 |
| HPV33 | E2 | 58 | CHQVVPSLLASKTKA | 47571 | VVPSLLASK | 49668 |
| HPV33 | E2 | 250 | DPALDNRTARTATNC | 47572 | LDNRTARTA | 49669 |
| HPV33 | E2 | 139 | EIYIIEEDTCTMVTG | 47573 | IIEEDTCTM | 49670 |
| HPV33 | E2 | 16 | EKILDLYEADKTDLP | 47574 | LDLYEADKT | 49671 |
| HPV33 | E2 | 77 | ELQMALETLSKSQYS | 47575 | MALETLSKS | 49672 |
| HPV33 | E2 | 188 | EVHVGGQVIVCPTSI | 47576 | VGGQVIVCP | 49673 |
| HPV33 | E2 | 171 | FKYFKEDAAKYSKTQ | 47577 | FKEDAAKYS | 49674 |
| HPV33 | E2 | 73 | FQVIELQMALETLSK | 47578 | IELQMALET | 49675 |
| HPV33 | E2 | 54 | FSHLCHQVVPSLLAS | 47579 | LCHQVVPSL | 49676 |
| HPV33 | E2 | 192 | GGQVIVCPTSISSNQ | 47580 | VIVCPTSIS | 49677 |
| HPV33 | E2 | 193 | GQVIVCPTSISSNQI | 47581 | IVCPTSISS | 49678 |
| HPV33 | E2 | 59 | HQVVPSLLASKTKAF | 47582 | VPSLLASKT | 49679 |
| HPV33 | E2 | 35 | HWKLIRMECALLYTA | 47583 | LIRMECALL | 49680 |
| HPV33 | E2 | 33 | IEHWKLIRMECALLY | 47584 | WKLIRMECA | 49681 |
| HPV33 | E2 | 158 | IGMYYIHNCEKVYFK | 47585 | YYIHNCEKV | 49682 |
| HPV33 | E2 | 140 | IYIIEEDTCTMVTGK | 47586 | IEEDTCTMV | 49683 |
| HPV33 | E2 | 300 | KELYSSMSSTWHWTS | 47587 | YSSMSSTWH | 49684 |
| HPV33 | E2 | 183 | KTQMWEVHVGGQVIV | 47588 | MWEVHVGGQ | 49685 |
| HPV33 | E2 | 19 | LDLYEADKTDLPSQI | 47589 | YEADKTDLP | 49686 |
| HPV33 | E2 | 102 | LEVWLCEPPKCFKKQ | 47590 | WLCEPPKCF | 49687 |
| HPV33 | E2 | 338 | LGTVKIPPTVQISTG | 47591 | VKIPPTVQI | 49688 |
| HPV33 | E2 | 38 | LIRMECALLYTAKQM | 47592 | MECALLYTA | 49689 |
| HPV33 | E2 | 296 | LKPYKELYSSMSSTW | 47593 | YKELYSSMS | 49690 |
| HPV33 | E2 | 11 | LNAVQEKILDLYEAD | 47594 | VQEKILDLY | 49691 |
| HPV33 | E2 | 243 | LTKLFCADPALDNRT | 47595 | LFCADPALD | 49692 |
| HPV33 | E2 | 321 | NGIVTVTFVTEQQQQ | 47596 | VTVTFVTEQ | 49693 |
| HPV33 | E2 | 30 | PSQIEHWKLIRMECA | 47597 | IEHWKLIRM | 49694 |
| HPV33 | E2 | 199 | PTSISSNQISTTETA | 47598 | ISSNQISTT | 49695 |
| HPV33 | E2 | 335 | QMFLGTVKIPPTVQI | 47599 | LGTVKIPPT | 49696 |
| HPV33 | E2 | 333 | QQQMFLGTVKIPPTV | 47600 | MFLGTVKIP | 49697 |
| HPV33 | E2 | 268 | QRTVCSSNVAPIVHL | 47601 | VCSSNVAPI | 49698 |
| HPV33 | E2 | 99 | QTSLEVWLCEPPKCF | 47602 | LEVWLCEPP | 49699 |
| HPV33 | E2 | 194 | QVIVCPTSISSNQIS | 47603 | VCPTSISSN | 49700 |
| HPV33 | E2 | 94 | QWTLQQTSLEVWLCE | 47604 | LQQTSLEVW | 49701 |
| HPV33 | E2 | 101 | SLEVWLCEPPKCFKK | 47605 | VWLCEPPKC | 49702 |
| HPV33 | E2 | 204 | SNQISTTETADIQTD | 47606 | ISTTETADI | 49703 |
| HPV33 | E2 | 147 | TCTMVTGKVDYIGMY | 47607 | MVTGKVDYI | 49704 |
| HPV33 | E2 | 152 | TGKVDYIGMYYIHNC | 47608 | VDYIGMYYI | 49705 |
| HPV33 | E2 | 70 | TKAFQVIELQMALET | 47609 | FQVIELQMA | 49706 |
| HPV33 | E2 | 244 | TKLFCADPALDNRTA | 47610 | FCADPALDN | 49707 |
| HPV33 | E2 | 92 | TSQWTLQQTSLEVWL | 47611 | WTLQQTSLE | 49708 |
| HPV33 | E2 | 155 | VDYIGMYYIHNCEKV | 47612 | IGMYYIHNC | 49709 |
| HPV33 | E2 | 62 | VPSLLASKTKAFQVI | 47613 | LLASKTKAF | 49710 |
| HPV33 | E2 | 36 | WKLIRMECALLYTAK | 47614 | IRMECALLY | 49711 |
| HPV33 | E2 | 170 | YFKYFKEDAAKYSKT | 47615 | YFKEDAAKY | 49712 |
| HPV33 | E2 | 299 | YKELYSSMSSTWHWT | 47616 | LYSSMSSTW | 49713 |
| HPV33 | E2 | 134 | YTNWGEIYIIEEDTC | 47617 | WGEIYIIEE | 49714 |
| HPV33 | E5 | 1 | ---MIFVFVLCILF | 47618 | MIFVFVLCF | 49715 |
| HPV33 | E5 | 2 | --MIFVFVLCFILFL | 47619 | IFVFVLCFI | 49716 |
| HPV33 | E5 | 3 | -MIFVFVLCFILFLC | 47620 | FVFVLCFIL | 49717 |
| HPV33 | E5 | 33 | AWLLVLVLLLWVFVG | 47621 | LVLVLLLWV | 49718 |
| HPV33 | E5 | 11 | CFILFLCLSLLLRPL | 47622 | LFLCLSLLL | 49719 |
| HPV33 | E5 | 66 | CINFHAQHMTQQE-- | 47623 | FHAQHMTQQ | 49720 |
| HPV33 | E5 | 17 | CLSLLLRPLILSIST | 47624 | LLLRPLILS | 49721 |
| HPV33 | E5 | 55 | CYLLFLYLPMMCINF | 47625 | LFLYLPMMC | 49722 |
| HPV33 | E5 | 54 | FCYLLFLYLPMMCIN | 47626 | LLFLYLPMM | 49723 |
| HPV33 | E5 | 12 | FILFLCLSLLLRPLI | 47627 | FLCLSLLLR | 49724 |
| HPV33 | E5 | 59 | FLYLPMMCINFHAQH | 47628 | LPMMCINFH | 49725 |
| HPV33 | E5 | 6 | FVFVLCFILFLCLSL | 47629 | VLCFILFLC | 49726 |
| HPV33 | E5 | 47 | GSPLKIFFCYLLFLY | 47630 | LKIFFCYLL | 49727 |
| HPV33 | E5 | 5 | IFVFVLCFILFLCLS | 47631 | FVLCFILFL | 49728 |
| HPV33 | E5 | 13 | ILFLCLSLLLRPLIL | 47632 | LCLSLLLRP | 49729 |
| HPV33 | E5 | 29 | ISTYAWLLVLVLLLW | 47633 | YAWLLVLVL | 49730 |
| HPV33 | E5 | 10 | LCFILFLCLSLLLRP | 47634 | ILFLCLSLL | 49731 |
| HPV33 | E5 | 58 | LFLYLPMMCINFHAQ | 47635 | YLPMMCINF | 49732 |
| HPV33 | E5 | 50 | LKIFFCYLLFLYLPM | 47636 | FFCYLLFLY | 49733 |
| HPV33 | E5 | 57 | LLFLYLPMMCINFHA | 47637 | LYLPMMCIN | 49734 |
| HPV33 | E5 | 40 | LLLWVFVGSPLKIFF | 47638 | WVFVGSPLK | 49735 |
| HPV33 | E5 | 41 | LLWVFVGSPLKIFFC | 47639 | VFVGSPLKI | 49736 |
| HPV33 | E5 | 22 | LRPLILSISTYAWLL | 47640 | LILSISTYA | 49737 |
| HPV33 | E5 | 18 | LSLLLRPLILSISTY | 47641 | LLRPLILSI | 49738 |
| HPV33 | E5 | 38 | LVLLLWVFVGSPLKI | 47642 | LLWVFVGSP | 49739 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV33 | E5 | 36 | LVLVLLLWVFVGSPL | 47643 | VLLLWVFVG | 49740 |
| HPV33 | E5 | 42 | LWVFVGSPLKIFFCY | 47644 | FVGSPLKIF | 49741 |
| HPV33 | E5 | 49 | PLKIFFCYLLFLYLP | 47645 | IFFCYLLFL | 49742 |
| HPV33 | E5 | 23 | RPLILSISTYAWLLV | 47646 | ILSISTYAW | 49743 |
| HPV33 | E5 | 19 | SLLLRPLILSISTYA | 47647 | LRPLILSIS | 49744 |
| HPV33 | E5 | 31 | TYAWLLVLVLLLWVF | 47648 | WLLVLVLLL | 49745 |
| HPV33 | E5 | 9 | VLCFILFLCLSLLLR | 47649 | FILFLCLSL | 49746 |
| HPV33 | E5 | 34 | WLLVLVLLLWVFVGS | 47650 | VLVLLLWVF | 49747 |
| HPV33 | E5 | 32 | YAWLLVLVLLLWVFV | 47651 | LLVLVLLLW | 49748 |
| HPV33 | E5 | 56 | YLLFLYLPMMCINFH | 47652 | FLYLPMMCI | 49749 |
| HPV33 | E6 | 69 | CLRFLSKISEYRHYN | 47653 | FLSKISEYR | 49750 |
| HPV33 | E6 | 47 | DFAFADLTVVYREGN | 47654 | FADLTVVYR | 49751 |
| HPV33 | E6 | 101 | EILIRCIICQRPLCP | 47655 | IRCIICQRP | 49752 |
| HPV33 | E6 | 23 | ETTIHNIELQCVECK | 47656 | IHNIELQCV | 49753 |
| HPV33 | E6 | 128 | FHNISGRWAGRCAAC | 47657 | ISGRWAGRC | 49754 |
| HPV33 | E6 | 60 | GNPFGICKLCLRFLS | 47658 | FGICKLCLR | 49755 |
| HPV33 | E6 | 65 | ICKLCLRFLSKISEY | 47659 | LCLRFLSKI | 49756 |
| HPV33 | E6 | 26 | IHNIELQCVECKKPL | 47660 | IELQCVECK | 49757 |
| HPV33 | E6 | 104 | IRCIICQRPLCPQEK | 47661 | IICQRPLCP | 49758 |
| HPV33 | E6 | 96 | KKPLNEILIRCIICQ | 47662 | LNEILIRCI | 49759 |
| HPV33 | E6 | 37 | KKPLQRSEVYDFAFA | 47663 | LQRSEVYDF | 49760 |
| HPV33 | E6 | 99 | LNEILIRCIICQRPL | 47664 | ILIRCIICQ | 49761 |
| HPV33 | E6 | 31 | LQCVECKKPLQRSEV | 47665 | VECKKPLQR | 49762 |
| HPV33 | E6 | 100 | NEILIRCIICQRPLC | 47666 | LIRCIICQR | 49763 |
| HPV33 | E6 | 28 | NIELQCVECKKPLQR | 47667 | LQCVECKKP | 49764 |
| HPV33 | E6 | 83 | NYSVYGNTLEQTVKK | 47668 | VYGNTLEQT | 49765 |
| HPV33 | E6 | 62 | PFGICKLCLRFLSKI | 47669 | ICKLCLRFL | 49766 |
| HPV33 | E6 | 105 | RCIICQRPLCPQEKK | 47670 | ICQRPLCPQ | 49767 |
| HPV33 | E6 | 43 | SEVYDFAFADLTVVY | 47671 | YDFAFADLT | 49768 |
| HPV33 | E6 | 132 | SGRWAGRCAACWRSR | 47672 | WAGRCAACW | 49769 |
| HPV33 | E6 | 54 | TVVYREGNPFGICKL | 47673 | YREGNPFGI | 49770 |
| HPV33 | E6 | 45 | VYDFAFADLTVVYRE | 47674 | FAFADLTVV | 49771 |
| HPV33 | E7 | 1 | ---MRGHKPTLKEYV | 47675 | MRGHKPTLK | 49772 |
| HPV33 | E7 | 53 | ADYYIVTCCHTCNTT | 47676 | YIVTCCHTC | 49773 |
| HPV33 | E7 | 82 | IQQLLMGTVNIVCPT | 47677 | LLMGTVNIV | 49774 |
| HPV33 | E7 | 12 | KEYVLDLYPEPTDLY | 47678 | VLDLYPEPT | 49775 |
| HPV33 | E7 | 8 | KPTLKEYVLDLYPEP | 47679 | LKEYVLDLY | 49776 |
| HPV33 | E7 | 79 | LRTIQQLLMGTVNIV | 47680 | IQQLLMGTV | 49777 |
| HPV33 | E7 | 87 | MGTVNIVCPTCAQQ- | 47681 | VNIVCPTCA | 49778 |
| HPV33 | E7 | 84 | QLLMGTVNIVCPTCA | 47682 | MGTVNIVCP | 49779 |
| HPV33 | E7 | 69 | RLCVNSTASDLRTIQ | 47683 | VNSTASDLR | 49780 |
| HPV33 | E7 | 52 | TADYYIVTCCHTCNT | 47684 | YYIVTCCHT | 49781 |
| HPV33 | E7 | 23 | TDLYCYEQLSDSSDE | 47685 | YCYEQLSDS | 49782 |
| HPV33 | E7 | 89 | TVNIVCPTCAQQ--- | 47686 | IVCPTCAQQ | 49783 |
| HPV33 | E7 | 67 | TVRLCVNSTASDLRT | 47687 | LCVNSTASD | 49784 |
| HPV33 | E7 | 15 | VLDLYPEPTDLYCYE | 47688 | LYPEPTDLY | 49785 |
| HPV33 | E7 | 55 | YYIVTCCHTCNTTVR | 47689 | VTCCHTCNT | 49786 |
| HPV33 | L1 | 1 | ---MSVWRPSEATVY | 47690 | MSVWRPSEA | 49787 |
| HPV33 | L1 | 387 | AEVMTYIHAMNPDIL | 47691 | MTYIHAMNP | 49788 |
| HPV33 | L1 | 267 | AGTLGEAVPDDLYIK | 47692 | LGEAVPDDL | 49789 |
| HPV33 | L1 | 61 | AKKLLVPKVSGLQYR | 47693 | LLVPKVSGL | 49790 |
| HPV33 | L1 | 12 | ATVYLPPVPVSKVVS | 47694 | YLPPVPVSK | 49791 |
| HPV33 | L1 | 150 | CLSMDYKQTQLCLLG | 47695 | MDYKQTQLC | 49792 |
| HPV33 | L1 | 210 | CMDFKTLQANKSDVP | 47696 | FKTLQANKS | 49793 |
| HPV33 | L1 | 188 | CPPLELINTIIEDGD | 47697 | LELINTIIE | 49794 |
| HPV33 | L1 | 348 | CTQVTSDSTYKNENF | 47698 | VTSDSTYKN | 49795 |
| HPV33 | L1 | 28 | DEYVSRTSIYYYAGS | 47699 | VSRTSIYYY | 49796 |
| HPV33 | L1 | 373 | DLQFVFQLCKVTLTA | 47700 | FVFQLCKVT | 49797 |
| HPV33 | L1 | 277 | DLYIKGSGTTASIQS | 47701 | IKGSGTTAS | 49798 |
| HPV33 | L1 | 91 | DTSFYNPDTQRLVWA | 47702 | FYNPDTQRL | 49799 |
| HPV33 | L1 | 222 | DVPIDICGSTCKYPD | 47703 | IDICGSTCK | 49800 |
| HPV33 | L1 | 403 | DWQFGLTPPPSASLQ | 47704 | FGLTPPPSA | 49801 |
| HPV33 | L1 | 11 | EATVYLPPVPVSKVV | 47705 | VYLPPVPVS | 49802 |
| HPV33 | L1 | 450 | EVDLKEKFSADLDQF | 47706 | LKEKFSADL | 49803 |
| HPV33 | L1 | 250 | FFFLRREQMFVRHFF | 47707 | LRREQMFVR | 49804 |
| HPV33 | L1 | 208 | FGCMDFKTLQANKSD | 47708 | MDFKTLQAN | 49805 |
| HPV33 | L1 | 213 | FKTLQANKSDVPIDI | 47709 | LQANKSDVP | 49806 |
| HPV33 | L1 | 170 | GEHWGKGVACTNAAP | 47710 | WGKGVACTN | 49807 |
| HPV33 | L1 | 174 | GKGVACTNAAPANDC | 47711 | VACTNAAPA | 49808 |
| HPV33 | L1 | 108 | GLEIGRGQPLGVGIS | 47712 | IGRGQPLGV | 49809 |
| HPV33 | L1 | 71 | GLQYRVFRVRLPDPN | 47713 | YRVFRVRLP | 49810 |
| HPV33 | L1 | 329 | GNQVFVTVVDTTRST | 47714 | VFVTVVDTT | 49811 |
| HPV33 | L1 | 114 | GQPLGVGISGHPLLN | 47715 | LGVGISGHP | 49812 |
| HPV33 | L1 | 118 | GVGISGHPLLNKFDD | 47716 | ISGHPLLNK | 49813 |
| HPV33 | L1 | 50 | HPYFSIKNPTNAKKL | 47717 | FSIKNPTNA | 49814 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV33 | L1 | 393 | IHAMNPDILEDWQFG | 47718 | MNPDILEDW | 49815 |
| HPV33 | L1 | 366 | IRHVEEYDLQFVFQL | 47719 | VEEYDLQFV | 49816 |
| HPV33 | L1 | 62 | KKLLVPKVSGLQYRV | 47720 | LVPKVSGLQ | 49817 |
| HPV33 | L1 | 479 | KPKLKRAAPTSTRTS | 47721 | LKRAAPTST | 49818 |
| HPV33 | L1 | 220 | KSDVPIDICGSTCKY | 47722 | VPIDICGST | 49819 |
| HPV33 | L1 | 382 | KVTLTAEVMTYIHAM | 47723 | LTAEVMTYI | 49820 |
| HPV33 | L1 | 445 | KYTFWEVDLKEKFSA | 47724 | FWEVDLKEK | 49821 |
| HPV33 | L1 | 160 | LCLLGCKPPTGEHWG | 47725 | LGCKPPTGE | 49822 |
| HPV33 | L1 | 401 | LEDWQFGLTPPPSAS | 47726 | WQFGLTPPP | 49823 |
| HPV33 | L1 | 443 | LGKYTFWEVDLKEKF | 47727 | YTFWEVDLK | 49824 |
| HPV33 | L1 | 127 | LNKFDDTETGNKYPG | 47728 | FDDTETGNK | 49825 |
| HPV33 | L1 | 16 | LPPVPVSKVVSTDEY | 47729 | VPVSKVVST | 49826 |
| HPV33 | L1 | 4 | MSVWRPSEATVYLPP | 47730 | WRPSEATVY | 49827 |
| HPV33 | L1 | 390 | MTYIHAMNPDILEDW | 47731 | IHAMNPDIL | 49828 |
| HPV33 | L1 | 311 | NKPYWLQRAQGHNNG | 47732 | YWLQRAQGH | 49829 |
| HPV33 | L1 | 344 | NMTLCTQVTSDSTYK | 47733 | LCTQVTSDS | 49830 |
| HPV33 | L1 | 195 | NTIIEDGDMVDTGFG | 47734 | IEDGDMVDT | 49831 |
| HPV33 | L1 | 275 | PDDLYIKGSGTTASI | 47735 | LYIKGSGTT | 49832 |
| HPV33 | L1 | 224 | PIDICGSTCKYPDYL | 47736 | ICGSTCKYP | 49833 |
| HPV33 | L1 | 190 | PLELINTIIEDGDMV | 47737 | LINTIIEDG | 49834 |
| HPV33 | L1 | 84 | PNKFGFPDTSFYNPD | 47738 | FGFPDTSFY | 49835 |
| HPV33 | L1 | 18 | PVPVSKVVSTDEYVS | 47739 | VSKVVSTDE | 49836 |
| HPV33 | L1 | 417 | QDTYRFVTSQAITCQ | 47740 | YRFVTSQAI | 49837 |
| HPV33 | L1 | 405 | QFGLTPPPSASLQDT | 47741 | LTPPPSASL | 49838 |
| HPV33 | L1 | 463 | QFPLGRKFLLQAGLK | 47742 | LGRKFLLQA | 49839 |
| HPV33 | L1 | 375 | QFVFQLCKVTLTAEV | 47743 | FQLCKVTLT | 49840 |
| HPV33 | L1 | 159 | QLCLLGCKPPTGEHW | 47744 | LLGCKPPTG | 49841 |
| HPV33 | L1 | 157 | QTQLCLLGCKPPTGE | 47745 | LCLLGCKPP | 49842 |
| HPV33 | L1 | 331 | QVFVTVVDTTRSTNM | 47746 | VTVVDTTRS | 49843 |
| HPV33 | L1 | 73 | QYRVFRVRLPDPNKF | 47747 | VFRVRLPDP | 49844 |
| HPV33 | L1 | 261 | RHFFNRAGTLGEAVP | 47748 | FNRAGTLGE | 49845 |
| HPV33 | L1 | 468 | RKFLLQAGLKAKPKL | 47749 | LLQAGLKAK | 49846 |
| HPV33 | L1 | 101 | RLVWACVGLEIGRGQ | 47750 | WACVGLEIG | 49847 |
| HPV33 | L1 | 458 | SADLDQFPLGRKFLL | 47751 | LDQFPLGRK | 49848 |
| HPV33 | L1 | 299 | SGSMVTSESQLFNKP | 47752 | MVTSESQLF | 49849 |
| HPV33 | L1 | 35 | SIYYYAGSSRLLAVG | 47753 | YYAGSSRLL | 49850 |
| HPV33 | L1 | 152 | SMDYKQTQLCLLGCK | 47754 | YKQTQLCLL | 49851 |
| HPV33 | L1 | 425 | SQAITCQKTVPPKEK | 47755 | ITCQKTVPP | 49852 |
| HPV33 | L1 | 43 | SRLLAVGHPYFSIKN | 47756 | LAVGHPYFS | 49853 |
| HPV33 | L1 | 291 | SSAFFPTPSGSMVTS | 47757 | FFPTPSGSM | 49854 |
| HPV33 | L1 | 27 | TDEYVSRTSIYYYAG | 47758 | YVSRTSIYY | 49855 |
| HPV33 | L1 | 99 | TQRLVWACVGLEIGR | 47759 | LVWACVGLE | 49856 |
| HPV33 | L1 | 34 | TSIYYYAGSSRLLAV | 47760 | YYYAGSSRL | 49857 |
| HPV33 | L1 | 13 | TVYLPPVPVSKVVST | 47761 | LPPVPVSKV | 49858 |
| HPV33 | L1 | 419 | TYRFVTSQAITCQKT | 47762 | FVTSQAITC | 49859 |
| HPV33 | L1 | 369 | VEEYDLQFVFQLCKV | 47763 | YDLQFVFQL | 49860 |
| HPV33 | L1 | 377 | VFQLCKVTLTAEVMT | 47764 | LCKVTLTAE | 49861 |
| HPV33 | L1 | 76 | VFRVRLPDPNKFGFP | 47765 | VRLPDPNKF | 49862 |
| HPV33 | L1 | 334 | VTVVDTTRSTNMTLC | 47766 | VDTTRSTNM | 49863 |
| HPV33 | L1 | 234 | YPDYLKMTSEPYGDS | 47767 | YLKMTSEPY | 49864 |
| HPV33 | L1 | 420 | YRFVTSQAITCQKTV | 47768 | VTSQAITCQ | 49865 |
| HPV33 | L1 | 74 | YRVFRVRLPDPNKFG | 47769 | FRVRLPDPN | 49866 |
| HPV33 | L2 | 1 | ---MRHKRSTRRKRA | 47770 | MRHKRSTRR | 49867 |
| HPV33 | L2 | 370 | ADDVDNVHTPMQHSY | 47771 | VDNVHTPMQ | 49868 |
| HPV33 | L2 | 44 | ADQILKYGSLGVFFG | 47772 | ILKYGSLGV | 49869 |
| HPV33 | L2 | 85 | AIPLQPIRPPVTVDT | 47773 | LQPIRPPVT | 49870 |
| HPV33 | L2 | 281 | DPDFLDIIALHRPAI | 47774 | FLDIIALHR | 49871 |
| HPV33 | L2 | 45 | DQILKYGSLGVFFGG | 47775 | LKYGSLGVF | 49872 |
| HPV33 | L2 | 202 | DTFVVSTDSSNVTSS | 47776 | VVSTDSSNV | 49873 |
| HPV33 | L2 | 266 | EDTLQFQHSDISPAP | 47777 | LQFQHSDIS | 49874 |
| HPV33 | L2 | 168 | EPSVLHPPAPAEASG | 47778 | VLHPPAPAE | 49875 |
| HPV33 | L2 | 152 | ESSIQTISTHLNPTF | 47779 | IQTISTHLN | 49876 |
| HPV33 | L2 | 113 | ETSFIEAGAPAPSIP | 47780 | FIEAGAPAP | 49877 |
| HPV33 | L2 | 433 | FDTIVVDGADFVLHP | 47781 | IVVDGADFV | 49878 |
| HPV33 | L2 | 260 | FESFDPEDTLQFQHS | 47782 | FDPEDTLQF | 49879 |
| HPV33 | L2 | 430 | FFPFDTIVVDGADFV | 47783 | FDTIVVDGA | 49880 |
| HPV33 | L2 | 304 | FSRVGKATLKTRSG | 47784 | VGQKATLKT | 49881 |
| HPV33 | L2 | 424 | FVPISPFFPFDTIVV | 47785 | ISPFFPFDT | 49882 |
| HPV33 | L2 | 440 | GADFVLHPSYFILRR | 47786 | FVLHPSYFI | 49883 |
| HPV33 | L2 | 182 | GHFIFSSPTVSTQSY | 47787 | IFSSPTVST | 49884 |
| HPV33 | L2 | 40 | GSTIADQILKYGSLG | 47788 | IADQILKYG | 49885 |
| HPV33 | L2 | 54 | GVFFGGLGIGTGSGS | 47789 | FGGLGIGTG | 49886 |
| HPV33 | L2 | 183 | HFIFSSPTVSTQSYE | 47790 | FSSPTVSTQ | 49887 |
| HPV33 | L2 | 250 | HKLITYDNPAFESFD | 47791 | ITYDNPAFE | 49888 |
| HPV33 | L2 | 377 | HTPMQHSYSTFATTR | 47792 | MQHSYSTFA | 49889 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV33 | L2 | 325 | IHYYQDLSPIVPLDH | 47793 | YQDLSPIVP | 49890 |
| HPV33 | L2 | 287 | IIALHRPAITSRRHT | 47794 | LHRPAITSR | 49891 |
| HPV33 | L2 | 47 | ILKYGSLGVFFGGLG | 47795 | YGSLGVFFG | 49892 |
| HPV33 | L2 | 35 | IPKVEGSTIADQILK | 47796 | VEGSTIADQ | 49893 |
| HPV33 | L2 | 427 | ISPFFPFDTIVVDGA | 47797 | FFPFDTIVV | 49894 |
| HPV33 | L2 | 334 | IVPLDHTVPNEQYEL | 47798 | LDHTVPNEQ | 49895 |
| HPV33 | L2 | 107 | IVSLIEETSFIEAGA | 47799 | LIEETSFIE | 49896 |
| HPV33 | L2 | 285 | LDIIALHRPAITSRR | 47800 | IALHRPAIT | 49897 |
| HPV33 | L2 | 88 | LQPIRPPVTVDTVGP | 47801 | IRPPVTVDT | 49898 |
| HPV33 | L2 | 348 | LQPLHDTSTSSYSIN | 47802 | LHDTSTSSY | 49899 |
| HPV33 | L2 | 365 | LYDVYADDVDNVHTP | 47803 | VYADDVDNV | 49900 |
| HPV33 | L2 | 362 | NDGLYDVYADDVDNV | 47804 | LYDVYADDV | 49901 |
| HPV33 | L2 | 343 | NEQYELQPLHDTSTS | 47805 | YELQPLHDT | 49902 |
| HPV33 | L2 | 198 | NIPMDTFVVSTDSSN | 47806 | MDTFVVSTD | 49903 |
| HPV33 | L2 | 257 | NPAFESFDPEDTLQF | 47807 | FESFDPEDT | 49904 |
| HPV33 | L2 | 163 | NPTFTEPSVLHPPAP | 47808 | FTEPSVLHP | 49905 |
| HPV33 | L2 | 400 | NTGFDTPVMSGPDIP | 47809 | FDTPVMSGP | 49906 |
| HPV33 | L2 | 142 | PAIINVSSVGESSIQ | 47810 | INVSSVGES | 49907 |
| HPV33 | L2 | 282 | PDFLDIIALHRPAIT | 47811 | LDIIALHRP | 49908 |
| HPV33 | L2 | 129 | PSGFDVTTSADTTPA | 47812 | FDVTTSADT | 49909 |
| HPV33 | L2 | 414 | PSPLFPTSSPFVPIS | 47813 | LFPTSSPFV | 49910 |
| HPV33 | L2 | 169 | PSVLHPPAPAEASGH | 47814 | LHPPAPAEA | 49911 |
| HPV33 | L2 | 94 | PVTVDTVGPLDSSIV | 47815 | VDTVGPLDS | 49912 |
| HPV33 | L2 | 381 | QHSYSTFATTRTSNV | 47816 | YSTFATTRT | 49913 |
| HPV33 | L2 | 458 | RFPYFFTDVRVAA-- | 47817 | YFFTDVRVA | 49914 |
| HPV33 | L2 | 299 | RHTVRFSRVGQKATL | 47818 | VRFSRVGQK | 49915 |
| HPV33 | L2 | 324 | RIHYYQDLSPIVPLD | 47819 | YYQDLSPIV | 49916 |
| HPV33 | L2 | 456 | RKRFPYFFTDVRVAA | 47820 | FPYFFTDVR | 49917 |
| HPV33 | L2 | 227 | RLGLYSRNTQQVKVV | 47821 | LYSRNTQQV | 49918 |
| HPV33 | L2 | 92 | RPPVTVDTVGPLDSS | 47822 | VTVDTVGPL | 49919 |
| HPV33 | L2 | 71 | RTGYVPIGTDPPTAA | 47823 | YVPIGTDPP | 49920 |
| HPV33 | L2 | 181 | SGHFIFSSPTVSTQS | 47824 | FIFSSPTVS | 49921 |
| HPV33 | L2 | 52 | SLGVFFGGLGIGTGS | 47825 | VFFGGLGIG | 49922 |
| HPV33 | L2 | 428 | SPFFPFDTIVVDGAD | 47826 | FPFDTIVVD | 49923 |
| HPV33 | L2 | 332 | SPIVPLDHTVPNEQY | 47827 | VPLDHTVPN | 49924 |
| HPV33 | L2 | 415 | SPLFPTSSPFVPISP | 47828 | FPTSSPFVP | 49925 |
| HPV33 | L2 | 222 | SRPVARLGLYSRNTQ | 47829 | VARLGLYSR | 49926 |
| HPV33 | L2 | 210 | SSNVTSSTPIPGSRP | 47830 | VTSSTPIPG | 49927 |
| HPV33 | L2 | 421 | SSPFVPISPFFPFDT | 47831 | FVPISPFFP | 49928 |
| HPV33 | L2 | 159 | STHLNPTFTEPSVLH | 47832 | LNPTFTEPS | 49929 |
| HPV33 | L2 | 216 | STPIPGSRPVARLGL | 47833 | IPGSRPVAR | 49930 |
| HPV33 | L2 | 83 | TAAIPLQPIRPPVTV | 47834 | IPLQPIRPP | 49931 |
| HPV33 | L2 | 203 | TFVVSTDSSNVTSST | 47835 | VSTDSSNVT | 49932 |
| HPV33 | L2 | 268 | TLQFQHSDISPAPDP | 47836 | FQHSDISPA | 49933 |
| HPV33 | L2 | 141 | TPAIINVSSVGESSI | 47837 | IINVSSVGE | 49934 |
| HPV33 | L2 | 405 | TPVMSGPDIPSPLFP | 47838 | MSGPDIPSP | 49935 |
| HPV33 | L2 | 18 | TQLYQTCKATGTCPP | 47839 | YQTCKATGT | 49936 |
| HPV33 | L2 | 235 | TQQVKVVDPAFLTSP | 47840 | VKVVDPAFL | 49937 |
| HPV33 | L2 | 193 | TQSYENIPMDTFVVS | 47841 | YENIPMDTF | 49938 |
| HPV33 | L2 | 114 | TSFIEAGAPAPSIPT | 47842 | IEAGAPAPS | 49939 |
| HPV33 | L2 | 97 | VDTVGPLDSSIVSLI | 47843 | VGPLDSSIV | 49940 |
| HPV33 | L2 | 100 | VGPLDSSIVSLIEET | 47844 | LDSSIVSLI | 49941 |
| HPV33 | L2 | 238 | VKVVDPAFLTSPHKL | 47845 | VDPAFLTSP | 49942 |
| HPV33 | L2 | 147 | VSSVGESSIQTISTH | 47846 | VGESSIQTI | 49943 |
| HPV33 | L2 | 328 | YQDLSPIVPLDHTVP | 47847 | LSPIVPLDH | 49944 |
| HPV33 | L2 | 384 | YSTFATTRTSNVSIP | 47848 | FATTRTSNV | 49945 |
| HPV33 | L2 | 74 | YVPIGTDPPTAAIPL | 47849 | IGTDPPTAA | 49946 |
| HPV45 | E1 | 385 | AAAFLKSNCQAKYLK | 47850 | FLKSNCQAK | 49947 |
| HPV45 | E1 | 178 | AENVDPHCSITELKE | 47851 | VDPHCSITE | 49948 |
| HPV45 | E1 | 395 | AKYLKDCAVMCRHYK | 47852 | LKDCAVMCR | 49949 |
| HPV45 | E1 | 314 | ALYWYRTGISNISEV | 47853 | WYRTGISNI | 49950 |
| HPV45 | E1 | 254 | ATLYAHIQCLDCKWG | 47854 | YAHIQCLDC | 49951 |
| HPV45 | E1 | 300 | CMLIEPPKLRSSVAA | 47855 | IEPPKLRSS | 49952 |
| HPV45 | E1 | 17 | CNGWFFVETIVEKKT | 47856 | WFFVETIVE | 49953 |
| HPV45 | E1 | 142 | CSEVEAAETQVTVNT | 47857 | VEAAETQVT | 49954 |
| HPV45 | E1 | 524 | CWTYFDNYMRNALDG | 47858 | YFDNYMRNA | 49955 |
| HPV45 | E1 | 264 | DCKWGVLILALLRYK | 47859 | WGVLILALL | 49956 |
| HPV45 | E1 | 370 | DMAFQYAQLADCNSN | 47860 | FQYAQLADC | 49957 |
| HPV45 | E1 | 569 | DNKWPYLESRVTVFT | 47861 | WPYLESRVT | 49958 |
| HPV45 | E1 | 137 | DSGYGCSEVEAAETQ | 47862 | YGCSEVEAA | 49959 |
| HPV45 | E1 | 348 | DSNFDLSDMVQWAFD | 47863 | FDLSDMVQW | 49960 |
| HPV45 | E1 | 231 | DWVMAIFGVNPTVAE | 47864 | MAIFGVNPT | 49961 |
| HPV45 | E1 | 610 | ERTWSRLDLHEDDED | 47865 | WSRLDLHED | 49962 |
| HPV45 | E1 | 368 | ESDMAFQYAQLADCN | 47866 | MAFQYAQLA | 49963 |
| HPV45 | E1 | 298 | ETCMLIEPPKLRSSV | 47867 | MLIEPPKLR | 49964 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV45 | E1 | 528 | FDNYMRNALDGNPIS | 47868 | YMRNALDGN | 49965 |
| HPV45 | E1 | 486 | FIHFLQGAIISFVNS | 47869 | FLQGAIISF | 49966 |
| HPV45 | E1 | 635 | FKCVTGQNTRPL--- | 47870 | VTGQNTRPL | 49967 |
| HPV45 | E1 | 247 | FKTLIKPATLYAHIQ | 47871 | LIKPATLYA | 49968 |
| HPV45 | E1 | 492 | GAIISFVNSNSHFWL | 47872 | ISFVNSNSH | 49969 |
| HPV45 | E1 | 161 | GGSVHSTQSSGGDSS | 47873 | VHSTQSSGG | 49970 |
| HPV45 | E1 | 629 | GIPFGTFKCVTGQNT | 47874 | FGTFKCVTG | 49971 |
| HPV45 | E1 | 19 | GWFFVETIVEKKTGD | 47875 | FVETIVEKK | 49972 |
| HPV45 | E1 | 547 | HKPLLQLKCPPILLT | 47876 | LLQLKCPPI | 49973 |
| HPV45 | E1 | 236 | IFGVNPTVAEGFKTL | 47877 | VNPTVAEGF | 49974 |
| HPV45 | E1 | 487 | IHFLQGAIISFVNSN | 47878 | LQGAIISFV | 49975 |
| HPV45 | E1 | 494 | IISFVNSNSHFWLEP | 47879 | FVNSNSHFW | 49976 |
| HPV45 | E1 | 271 | ILALLRYKCGKNRLT | 47880 | LLRYKCGKN | 49977 |
| HPV45 | E1 | 469 | ILLYGPANTGKSYFG | 47881 | YGPANTGKS | 49978 |
| HPV45 | E1 | 325 | ISEVSGDTPEWIQRL | 47882 | VSGDTPEWI | 49979 |
| HPV45 | E1 | 210 | IYGLSFTDLVRNFKS | 47883 | LSFTDLVRN | 49980 |
| HPV45 | E1 | 606 | KCFFERTWSRLDLHE | 47884 | FERTWSRLD | 49981 |
| HPV45 | E1 | 208 | KDIYGLSFTDLVRNF | 47885 | YGLSFTDLV | 49982 |
| HPV45 | E1 | 466 | KNCILLYGPANTGKS | 47886 | ILLYGPANT | 49983 |
| HPV45 | E1 | 548 | KPLLQLKCPPILLTS | 47887 | LQLKCPPIL | 49984 |
| HPV45 | E1 | 479 | KSYFGMSFIHFLQGA | 47888 | FGMSFIHFL | 49985 |
| HPV45 | E1 | 248 | KTLIKPATLYAHIQC | 47889 | IKPATLYAH | 49986 |
| HPV45 | E1 | 513 | KVAMLDDATHTCWTY | 47890 | MLDDATHTC | 49987 |
| HPV45 | E1 | 266 | KWGVLILALLRYKCG | 47891 | VLILALLRY | 49988 |
| HPV45 | E1 | 571 | KWPYLESRVTVFTFP | 47892 | YLESRVTVF | 49989 |
| HPV45 | E1 | 506 | LEPLADTKVAMLDDA | 47893 | LADTKVAML | 49990 |
| HPV45 | E1 | 85 | LHLLKRKFAGGSKEN | 47894 | LKRKFAGGS | 49991 |
| HPV45 | E1 | 456 | LKEFLKGTPKKNCIL | 47895 | FLKGTPKKN | 49992 |
| HPV45 | E1 | 293 | LLHVPETCMLIEPPK | 47896 | VPETCMLIE | 49993 |
| HPV45 | E1 | 550 | LLQLKCPPILLTSNI | 47897 | LKCPPILLT | 49994 |
| HPV45 | E1 | 315 | LYWYRTGISNISEVS | 47898 | YRTGISNIS | 49995 |
| HPV45 | E1 | 234 | MAIFGVNPTVAEGFK | 47899 | FGVNPTVAE | 49996 |
| HPV45 | E1 | 418 | MSQWIKYRCSKIDEG | 47900 | WIKYRCSKI | 49997 |
| HPV45 | E1 | 50 | MVDFIDTQLSICEQA | 47901 | FIDTQLSIC | 49998 |
| HPV45 | E1 | 467 | NCILLYGPANTGKSY | 47902 | LLYGPANTG | 49999 |
| HPV45 | E1 | 18 | NGWFFVETIVEKKTG | 47903 | FFVETIVEK | 50000 |
| HPV45 | E1 | 501 | NSHFWLEPLADTKVA | 47904 | FWLEPLADT | 50001 |
| HPV45 | E1 | 99 | NSPLGEQLSVDTDLS | 47905 | LGEQLSVDT | 50002 |
| HPV45 | E1 | 333 | PEWIQRLTIIQHGID | 47906 | IQRLTIIQH | 50003 |
| HPV45 | E1 | 556 | PPILLTSNIDPAKDN | 47907 | LLTSNIDPA | 50004 |
| HPV45 | E1 | 305 | PPKLRSSVAALYWYR | 47908 | LRSSVAALY | 50005 |
| HPV45 | E1 | 394 | QAKYLKDCAVMCRHY | 47909 | YLKDCAVMC | 50006 |
| HPV45 | E1 | 70 | QALFHAQEVQNDAQV | 47910 | FHAQEVQND | 50007 |
| HPV45 | E1 | 105 | QLSVDTDLSPRLQEI | 47911 | VDTDLSPRL | 50008 |
| HPV45 | E1 | 358 | QWAFDNDLTDESDMA | 47912 | FDNDLTDES | 50009 |
| HPV45 | E1 | 338 | RLTIIQHGIDDSNFD | 47913 | IIQHGIDDS | 50010 |
| HPV45 | E1 | 283 | RLTVAKGLSTLLHVP | 47914 | VAKGLSTLL | 50011 |
| HPV45 | E1 | 533 | RNALDGNPISIDRKH | 47915 | LDGNPISID | 50012 |
| HPV45 | E1 | 130 | RRLFTISDSGYGCSE | 47916 | FTISDSGYG | 50013 |
| HPV45 | E1 | 48 | SDMVDFIDTQLSICE | 47917 | VDFIDTQLS | 50014 |
| HPV45 | E1 | 502 | SHFWLEPLADTKVAM | 47918 | WLEPLADTK | 50015 |
| HPV45 | E1 | 113 | SPRLQEISLNSGHKK | 47919 | LQEISLNSG | 50016 |
| HPV45 | E1 | 419 | SQWIKYRCSKIDEGG | 47920 | IKYRCSKID | 50017 |
| HPV45 | E1 | 291 | STLLHVPETCMLIEP | 47921 | LHVPETCML | 50018 |
| HPV45 | E1 | 216 | TDLVRNFKSDKTTCT | 47922 | VRNFKSDKT | 50019 |
| HPV45 | E1 | 332 | TPEWIQRLTIIQHGI | 47923 | WIQRLTIIQ | 50020 |
| HPV45 | E1 | 312 | VAALYWYRTGISNIS | 47924 | LYWYRTGIS | 50021 |
| HPV45 | E1 | 51 | VDFIDTQLSICEQAE | 47925 | IDTQLSICE | 50022 |
| HPV45 | E1 | 447 | VEFISFLRALKEFLK | 47926 | ISFLRALKE | 50023 |
| HPV45 | E1 | 23 | VETIVEKKTGDVISD | 47927 | IVEKKTGDV | 50024 |
| HPV45 | E1 | 581 | VFTFPHAFPFDKNGN | 47928 | FPHAFPFDK | 50025 |
| HPV45 | E1 | 233 | VMAIFGVNPTVAEGF | 47929 | IFGVNPTVA | 50026 |
| HPV45 | E1 | 439 | VQFLRYQGVEFISFL | 47930 | LRYQGVEFI | 50027 |
| HPV45 | E1 | 219 | VRNFKSDKTTCTDWV | 47931 | FKSDKTTCT | 50028 |
| HPV45 | E1 | 579 | VTVFTFPHAFPFDKN | 47932 | FTFPHAFPF | 50029 |
| HPV45 | E1 | 267 | WGVLILALLRYKCGK | 47933 | LILALLRYK | 50030 |
| HPV45 | E1 | 421 | WIKYRCSKIDEGGDW | 47934 | YRCSKIDEG | 50031 |
| HPV45 | E1 | 572 | WPYLESRVTVFTFPH | 47935 | LESRVTVFT | 50032 |
| HPV45 | E1 | 257 | YAHIQCLDCKWGVLI | 47936 | IQCLDCKWG | 50033 |
| HPV45 | E1 | 375 | YAQLADCNSAAAFL | 47937 | LADCNSAA | 50034 |
| HPV45 | E2 | 1 | ---MKMQTPKESLSE | 47938 | MKMQTPKES | 50035 |
| HPV45 | E2 | 159 | AACVSYWGVYYIKDG | 47939 | VSYWGVYYI | 50036 |
| HPV45 | E2 | 317 | ADHYSEISSTWHWTG | 47940 | YSEISSTWH | 50037 |
| HPV45 | E2 | 107 | CEELWNTEPSQCFKK | 47941 | LWNTEPSQC | 50038 |
| HPV45 | E2 | 185 | CEKYGNSNTWEVQYG | 47942 | YGNSNTWEV | 50039 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV45 | E2 | 137 | CMNYVVWDSIYYITE | 47943 | YVVWDSIYY | 50040 |
| HPV45 | E2 | 214 | DDTVSATQIVRQLQH | 47944 | VSATQIVRQ | 50041 |
| HPV45 | E2 | 144 | DSIYYITETGIWDKT | 47945 | YYITETGIW | 50042 |
| HPV45 | E2 | 108 | EELWNTEPSQCFKKG | 47946 | WNTEPSQCF | 50043 |
| HPV45 | E2 | 83 | ELQMALKGLAQSKYN | 47947 | MALKGLAQS | 50044 |
| HPV45 | E2 | 151 | ETGIWDKTAACVSYW | 47948 | IWDKTAACV | 50045 |
| HPV45 | E2 | 195 | EVQYGGNVIDCNDSM | 47949 | YGGNVIDCN | 50046 |
| HPV45 | E2 | 200 | GNVIDCNDSMCSTSD | 47950 | IDCNDSMCS | 50047 |
| HPV45 | E2 | 79 | HKAIELQMALKGLAQ | 47951 | IELQMALKG | 50048 |
| HPV45 | E2 | 272 | HNPLLCSSTSNNKRR | 47952 | LLCSSTSNN | 50049 |
| HPV45 | E2 | 65 | HQVVPPINISKSKAH | 47953 | VPPINISKS | 50050 |
| HPV45 | E2 | 39 | ISYWQLIRLENAILF | 47954 | WQLIRLENA | 50051 |
| HPV45 | E2 | 60 | ITKLNHQVVPPINIS | 47955 | LNHQVVPPI | 50052 |
| HPV45 | E2 | 146 | IYYITETGIWDKTAA | 47956 | ITETGIWDK | 50053 |
| HPV45 | E2 | 10 | KESLSERLSALQDKI | 47957 | LSERLSALQ | 50054 |
| HPV45 | E2 | 243 | KPHIQTPATKRPRQC | 47958 | IQTPATKRP | 50055 |
| HPV45 | E2 | 353 | LDVVTIPNSVQISVG | 47959 | VTIPNSVQI | 50056 |
| HPV45 | E2 | 44 | LIRLENAILFTAREH | 47960 | LENAILFTA | 50057 |
| HPV45 | E2 | 313 | LRKYADHYSEISSTW | 47961 | YADHYSEIS | 50058 |
| HPV45 | E2 | 17 | LSALQDKILDHYEND | 47962 | LQDKILDHY | 50059 |
| HPV45 | E2 | 138 | MNYVVWDSIYYITET | 47963 | VVWDSIYYI | 50060 |
| HPV45 | E2 | 98 | NEEWTLQDTCEELWN | 47964 | WTLQDTCEE | 50061 |
| HPV45 | E2 | 273 | NPLLCSSTSNNKRRK | 47965 | LCSSTSNNK | 50062 |
| HPV45 | E2 | 36 | NSQISYWQLIRLENA | 47966 | ISYWQLIRL | 50063 |
| HPV45 | E2 | 350 | NTFLDVVTIPNSVQI | 47967 | LDVVTIPNS | 50064 |
| HPV45 | E2 | 268 | NTHVHNPLLCSSTSN | 47968 | VHNPLLCSS | 50065 |
| HPV45 | E2 | 70 | PINISKSKAHKAIEL | 47969 | ISKSKAHKA | 50066 |
| HPV45 | E2 | 349 | RNTFLDVVTIPNSVQ | 47970 | FLDVVTIPN | 50067 |
| HPV45 | E2 | 285 | RRKVCSGNTTPIIHL | 47971 | VCSGNTTPI | 50068 |
| HPV45 | E2 | 32 | SKDINSQISYWQLIR | 47972 | INSQISYWQ | 50069 |
| HPV45 | E2 | 324 | SSTWHWTGCNKNTGI | 47973 | WHWTGCNKN | 50070 |
| HPV45 | E2 | 236 | TASVGTPKPHIQTPA | 47974 | VGTPKPHIQ | 50071 |
| HPV45 | E2 | 152 | TGIWDKTAACVSYWG | 47975 | WDKTAACVS | 50072 |
| HPV45 | E2 | 175 | TTYYVQFKSECEKYG | 47976 | YVQFKSECE | 50073 |
| HPV45 | E2 | 68 | VPPINISKSKAHKAI | 47977 | INISKSKAH | 50074 |
| HPV45 | E2 | 223 | VRQLQHASTSTPKTA | 47978 | LQHASTSTP | 50075 |
| HPV45 | E2 | 162 | VSYWGVYYIKDGDTT | 47979 | WGVYYIKDG | 50076 |
| HPV45 | E2 | 167 | VYYIKDGDTTYYVQF | 47980 | IKDGDTTYY | 50077 |
| HPV45 | E2 | 42 | WQLIRLENAILFTAR | 47981 | IRLENAILF | 50078 |
| HPV45 | E6 | 34 | ACVYCKATLERTEVY | 47982 | YCKATLERT | 50079 |
| HPV45 | E6 | 54 | DLFIVYRDCIAYAAC | 47983 | IVYRDCIAY | 50080 |
| HPV45 | E6 | 30 | DVSIACVYCKATLER | 47984 | IACVYCKAT | 50081 |
| HPV45 | E6 | 80 | ELRYYSNSVYGETLE | 47985 | YYSNSVYGE | 50082 |
| HPV45 | E6 | 56 | FIVYRDCIAYAACHK | 47986 | YRDCIAYAA | 50083 |
| HPV45 | E6 | 33 | IACVYCKATLERTEV | 47987 | VYCKATLER | 50084 |
| HPV45 | E6 | 106 | IRCLRCQKPLNPAEK | 47988 | LRCQKPLNP | 50085 |
| HPV45 | E6 | 39 | KATLERTEVYQFAFK | 47989 | LERTEVYQF | 50086 |
| HPV45 | E6 | 93 | LEKITNTELYNLLIR | 47990 | ITNTELYNL | 50087 |
| HPV45 | E6 | 55 | LFIVYRDCIAYAACH | 47991 | VYRDCIAYA | 50088 |
| HPV45 | E6 | 28 | LQDVSIACVYCKATL | 47992 | VSIACVYCK | 50089 |
| HPV45 | E6 | 101 | LYNLLIRCLRCQKPL | 47993 | LLIRCLRCQ | 50090 |
| HPV45 | E6 | 103 | NLLIRCLRCQKPLNP | 47994 | IRCLRCQKP | 50091 |
| HPV45 | E6 | 98 | NTELYNLLIRCLRCQ | 47995 | LYNLLIRCL | 50092 |
| HPV45 | E6 | 25 | NTSLQDVSIACVYCK | 47996 | LQDVSIACV | 50093 |
| HPV45 | E6 | 14 | PYKLPDLCTELNTSL | 47997 | LPDLCTELN | 50094 |
| HPV45 | E6 | 49 | QFAFKDLFIVYRDCI | 47998 | FKDLFIVYR | 50095 |
| HPV45 | E6 | 12 | QRPYKLPDLCTELNT | 47999 | YKLPDLCTE | 50096 |
| HPV45 | E6 | 60 | RDCIAYAACHKCIDF | 48000 | IAYAACHKC | 50097 |
| HPV45 | E6 | 85 | SNSVYGETLEKITNT | 48001 | VYGETLEKI | 50098 |
| HPV45 | E6 | 47 | VYQFAFKDLFIVYRD | 48002 | FAFKDLFIV | 50099 |
| HPV45 | E7 | 1 | ---MHGPRATLQEIV | 48003 | MHGPRATLQ | 50100 |
| HPV45 | E7 | 45 | ADGVSHAQLPARRAE | 48004 | VSHAQLPAR | 50101 |
| HPV45 | E7 | 50 | HAQLPARRAEPQRHK | 48005 | LPARRAEPQ | 50102 |
| HPV45 | E7 | 90 | LQQLFLSTLSFVCPW | 48006 | LFLSTLSFV | 50103 |
| HPV45 | E7 | 87 | LRTLQQLFLSTLSFV | 48007 | LQQLFLSTL | 50104 |
| HPV45 | E7 | 98 | LSFVCPWCATNQ--- | 48008 | VCPWCATNQ | 50105 |
| HPV45 | E7 | 95 | LSTLSFVCPWCATNQ | 48009 | LSFVCPWCA | 50106 |
| HPV45 | E7 | 12 | QEIVLHLEPQNELDP | 48010 | VLHLEPQNE | 50107 |
| HPV45 | E7 | 21 | QNELDPVDLLCYEQL | 48011 | LDPVDLLCY | 50108 |
| HPV45 | E7 | 91 | QQLFLSTLSFVCPWC | 48012 | FLSTLSFVC | 50109 |
| HPV45 | E7 | 8 | RATLQEIVLHLEPQN | 48013 | LQEIVLHLE | 50110 |
| HPV45 | E7 | 62 | RHKILCVCCKCDGRI | 48014 | ILCVCCKCD | 50111 |
| HPV45 | E7 | 75 | RIELTVESSADDLRT | 48015 | LTVESSADD | 50112 |
| HPV45 | E7 | 97 | TLSFVCPWCATNQ-- | 48016 | FVCPWCATN | 50113 |
| HPV45 | E7 | 27 | VDLLCYEQLSESEEE | 48017 | LCYEQLSES | 50114 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV45 | L1 | 1 | ---MAHNIIYGHGII | 48018 | MAHNIIYGH | 50115 |
| HPV45 | L1 | 418 | AEVMSYIHSMNSSIL | 48019 | MSYIHSMNS | 50116 |
| HPV45 | L1 | 294 | AGVMGDTVPTDLYIK | 48020 | MGDTVPTDL | 50117 |
| HPV45 | L1 | 165 | ATAVITQDVRDNVSV | 48021 | VITQDVRDN | 50118 |
| HPV45 | L1 | 97 | AYQYRVFRVALPDPN | 48022 | YRVFRVALP | 50119 |
| HPV45 | L1 | 215 | CPPLELKNTIIEDGD | 48023 | LELKNTIIE | 50120 |
| HPV45 | L1 | 54 | DDYVSRTSIFYHAGS | 48024 | VSRTSIFYH | 50121 |
| HPV45 | L1 | 404 | DLQFIFQLCTITLTA | 48025 | FIFQLCTIT | 50122 |
| HPV45 | L1 | 304 | DLYIKGTSANMRETP | 48026 | IKGTSANMR | 50123 |
| HPV45 | L1 | 117 | DSTIYNPETQRLVWA | 48027 | IYNPETQRL | 50124 |
| HPV45 | L1 | 37 | DSTVYLPPPSVARVV | 48028 | VYLPPPSVA | 50125 |
| HPV45 | L1 | 249 | EVPLDICQSICKYPD | 48029 | LDICQSICK | 50126 |
| HPV45 | L1 | 277 | FFCLRREQLFARHFW | 48030 | LRREQLFAR | 50127 |
| HPV45 | L1 | 27 | FLQMALWRPSDSTVY | 48031 | MALWRPSDS | 50128 |
| HPV45 | L1 | 24 | FPIFLQMALWRPSDS | 48032 | FLQMALWRP | 50129 |
| HPV45 | L1 | 240 | FSTLQDTKCEVPLDI | 48033 | LQDTKCEVP | 50130 |
| HPV45 | L1 | 196 | GEHWAKGTLCKPAQL | 48034 | WAKGTLCKP | 50131 |
| HPV45 | L1 | 13 | GIIIFLKNVNVFPIF | 48035 | IFLKNVNVF | 50132 |
| HPV45 | L1 | 134 | GMEIGRGQPLGIGLS | 48036 | IGRGQPLGI | 50133 |
| HPV45 | L1 | 75 | GNPYFRVVPSGAGNK | 48037 | YFRVVPSGA | 50134 |
| HPV45 | L1 | 140 | GQPLGIGLSGHPFYN | 48038 | LGIGLSGHP | 50135 |
| HPV45 | L1 | 319 | GSCVYSPSPSGSITT | 48039 | VYSPSPSGS | 50136 |
| HPV45 | L1 | 6 | HNIIYGHGIIIFLKN | 48040 | IYGHGIIIF | 50137 |
| HPV45 | L1 | 358 | HNQLFVTVVDTTRST | 48041 | LFVTVVDTT | 50138 |
| HPV45 | L1 | 408 | IFQLCTITLTAEVMS | 48042 | LCTITLTAE | 50139 |
| HPV45 | L1 | 424 | IHSMNSSILENWNFG | 48043 | MNSSILENW | 50140 |
| HPV45 | L1 | 15 | IIFLKNVNVFPIFLQ | 48044 | LKNVNVFPI | 50141 |
| HPV45 | L1 | 247 | KCEVPLDICQSICKY | 48045 | VPLDICQSI | 50142 |
| HPV45 | L1 | 112 | KFGLPDSTIYNPETQ | 48046 | LPDSTIYNP | 50143 |
| HPV45 | L1 | 476 | KLKFWTVDLKEKFSS | 48047 | FWTVDLKEK | 40144 |
| HPV45 | L1 | 89 | KQAVPKVSAYQYRVF | 48048 | VPKVSAYQY | 50145 |
| HPV45 | L1 | 186 | LCILGCVPAIGEHWA | 48049 | LGCVPAIGE | 50146 |
| HPV45 | L1 | 432 | LENWNFGVPPPPTTS | 48050 | WNFGVPPPP | 50147 |
| HPV45 | L1 | 18 | LKNVNVFPIFLQMAL | 48051 | VNVFPIFLQ | 50148 |
| HPV45 | L1 | 405 | LQFIFQLCTITLTAE | 48052 | IFQLCTITL | 50149 |
| HPV45 | L1 | 30 | MALWRPSDSTVYLPP | 48053 | WRPSDSTVY | 50150 |
| HPV45 | L1 | 421 | MSYIHSMNSSILENW | 48054 | IHSMNSSIL | 50151 |
| HPV45 | L1 | 436 | NFGVPPPPTTSLVDT | 48055 | VPPPPTTSL | 50152 |
| HPV45 | L1 | 7 | NIIYGHGIIIFLKNV | 48056 | YGHGIIIFL | 50153 |
| HPV45 | L1 | 340 | NKPYWLHKAQGHNNG | 48057 | YWLHKAQGH | 50154 |
| HPV45 | L1 | 76 | NPYFRVVPSGAGNKQ | 48058 | FRVVPSGAG | 50155 |
| HPV45 | L1 | 222 | NTIIEDGDMVDTGYG | 48059 | IEDGDMVDT | 50156 |
| HPV45 | L1 | 20 | NVNVFPIFLQMALWR | 48060 | VFPIFLQMA | 50157 |
| HPV45 | L1 | 176 | NVSVDYKQTQLCILG | 48061 | VDYKQTQLC | 50158 |
| HPV45 | L1 | 434 | NWNFGVPPPPTTSLV | 48062 | FGVPPPPTT | 50159 |
| HPV45 | L1 | 207 | PAQLQPGDCPPLELK | 48063 | LQPGDCPPL | 50160 |
| HPV45 | L1 | 251 | PLDICQSICKYPDYL | 48064 | ICQSICKYP | 50161 |
| HPV45 | L1 | 217 | PLELKNTIIEDGDMV | 48065 | LKNTIIEDG | 50162 |
| HPV45 | L1 | 110 | PNKFGLPDSTIYNPE | 48066 | FGLPDSTIY | 50163 |
| HPV45 | L1 | 302 | PTDLYIKGTSANMRE | 48067 | LYIKGTSAN | 50164 |
| HPV45 | L1 | 504 | QAGLRRRPTIGPRKR | 48068 | LRRRPTIGP | 50165 |
| HPV45 | L1 | 406 | QFIFQLCTITLTAEV | 48069 | FQLCTITLT | 50166 |
| HPV45 | L1 | 185 | QLCILGCVPAIGEHW | 48070 | ILGCVPAIG | 50167 |
| HPV45 | L1 | 360 | QLFVTVVDTTRSTNL | 48071 | VTVVDTTRS | 50168 |
| HPV45 | L1 | 183 | QTQLCILGCVPAIGE | 48072 | LCILGCVPA | 50169 |
| HPV45 | L1 | 494 | QYPLGRKFLVQAGLR | 48073 | LGRKFLVQA | 50170 |
| HPV45 | L1 | 99 | QYRVFRVALPDPNKF | 48074 | VFRVALPDP | 50171 |
| HPV45 | L1 | 293 | RAGVMGDTVPTDLYI | 48075 | VMGDTVPTD | 50172 |
| HPV45 | L1 | 288 | RHFWNRAGVMGDTVP | 48076 | WNRAGVMGD | 50173 |
| HPV45 | L1 | 499 | RKFLVQAGLRRRPTI | 48077 | LVQAGLRRR | 50174 |
| HPV45 | L1 | 127 | RLVWACVGMEIGRGQ | 48078 | WACVGMEIG | 50175 |
| HPV45 | L1 | 320 | SCVYSPSPSGSITTS | 48079 | YSPSPSGSI | 50176 |
| HPV45 | L1 | 328 | SGSITTSDSQLFNKP | 48080 | ITTSDSQLF | 50177 |
| HPV45 | L1 | 61 | SIFYHAGSSRLLTVG | 48081 | YHAGSSRLL | 50178 |
| HPV45 | L1 | 397 | SRHVEEYDLQFIFQL | 48082 | VEEYDLQFI | 50179 |
| HPV45 | L1 | 69 | SRLLTVGNPYFRVVP | 48083 | LTVGNPYFR | 50180 |
| HPV45 | L1 | 489 | SSDLDQYPLGRKFLV | 48084 | LDQYPLGRK | 50181 |
| HPV45 | L1 | 371 | STNLTLCASTQNPVP | 48085 | LTLCASTQN | 50182 |
| HPV45 | L1 | 38 | STVYLPPPSVARVVN | 48086 | YLPPPSVAR | 50183 |
| HPV45 | L1 | 178 | SVDYKQTQLCILGCV | 48087 | YKQTQLCIL | 50184 |
| HPV45 | L1 | 53 | TDDYVSRTSIFYHAG | 48088 | YVSRTSIFY | 50185 |
| HPV45 | L1 | 303 | TDLYIKGTSANMRET | 48089 | YIKGTSANM | 50186 |
| HPV45 | L1 | 413 | TITLTAEVMSYIHSM | 48090 | LTAEVMSYI | 50187 |
| HPV45 | L1 | 170 | TQDVRDNVSVDYKQT | 48091 | VRDNVSVDY | 50188 |
| HPV45 | L1 | 125 | TQRLVWACVGMEIGR | 48092 | LVWACVGME | 50189 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV45 | L1 | 60 | TSIFYHAGSSRLLTV | 48093 | FYHAGSSRL | 50190 |
| HPV45 | L1 | 481 | TVDLKEKFSSDLDQY | 48094 | LKEKFSSDL | 50191 |
| HPV45 | L1 | 39 | TVYLPPPSVARVVNT | 48095 | LPPPSVARV | 50192 |
| HPV45 | L1 | 450 | TYRFVQSVAVTCQKD | 48096 | FVQSVAVTC | 50193 |
| HPV45 | L1 | 448 | VDTYRFVQSVAVTCQ | 48097 | YRFVQSVAV | 50194 |
| HPV45 | L1 | 400 | VEEYDLQFIFQLCTI | 48098 | YDLQFIFQL | 50195 |
| HPV45 | L1 | 23 | VFPIFLQMALWRPSD | 48099 | IFLQMALWR | 50196 |
| HPV45 | L1 | 102 | VFRVALPDPNKFGLP | 48100 | VALPDPNKF | 50197 |
| HPV45 | L1 | 192 | VPAIGEHWAKGTLCK | 48101 | IGEHWAKGT | 50198 |
| HPV45 | L1 | 363 | VTVVDTTRSTNLTLC | 48102 | VDTTRSTNL | 50199 |
| HPV45 | L1 | 474 | YDKLKFWTVDLKEKF | 48103 | LKFWTVDLK | 50200 |
| HPV45 | L1 | 78 | YFRVVPSGAGNKQAV | 48104 | VVPSGAGNK | 50201 |
| HPV45 | L1 | 235 | YGAMDFSTLQDTKCE | 48105 | MDFSTLQDT | 50202 |
| HPV45 | L1 | 153 | YNKLDDTESAHAATA | 48106 | LDDTESAHA | 50203 |
| HPV45 | L1 | 261 | YPDYLQMSADPYGDS | 48107 | YLQMSADPY | 50204 |
| HPV45 | L1 | 451 | YRFVQSVAVTCQKDT | 48108 | VQSVAVTCQ | 50205 |
| HPV45 | L1 | 100 | YRVFRVALPDPNKFG | 48109 | FRVALPDPN | 50206 |
| HPV45 | L2 | 1 | ---MVSHRAARRKRA | 48110 | MVSHRAARR | 50207 |
| HPV45 | L2 | 2 | --MVSHRAARRKRAS | 48111 | VSHRAARRK | 50208 |
| HPV45 | L2 | 44 | ADKILQWSSLGIFLG | 48112 | ILQWSSLGI | 50209 |
| HPV45 | L2 | 385 | ASSYSNVTVPLTSAW | 48113 | YSNVTVPLT | 50210 |
| HPV45 | L2 | 408 | DIILPSHTPMWPSTS | 48114 | LPSHTPMWP | 50211 |
| HPV45 | L2 | 45 | DKILQWSSLGIFLGG | 48115 | LQWSSLGIF | 50212 |
| HPV45 | L2 | 346 | DSDLFDVYADFPPPA | 48116 | LFDVYADFP | 50213 |
| HPV45 | L2 | 112 | DSSVVASGAPVPTFT | 48117 | VVASGAPVP | 50214 |
| HPV45 | L2 | 263 | DTTLSFEPTSNVPDS | 48118 | LSFEPTSNV | 50215 |
| HPV45 | L2 | 334 | EIELQPLISATNDSD | 48119 | LQPLISATN | 50216 |
| HPV45 | L2 | 197 | EIPLQTFASSGSGTE | 48120 | LQTFASSGS | 50217 |
| HPV45 | L2 | 350 | FDVYADFPPPASTTP | 48121 | YADFPPPAS | 50218 |
| HPV45 | L2 | 299 | FSRLGQRATMFTRSG | 48122 | LGQRATMFT | 50219 |
| HPV45 | L2 | 130 | GFEITSSGTTTPAVL | 48123 | ITSSGTTTP | 50220 |
| HPV45 | L2 | 54 | GIFLGGLGIGTGSGS | 48124 | LGGLGIGTG | 50221 |
| HPV45 | L2 | 181 | GNIFVGTPTSGSHGY | 48125 | FVGTPTSGS | 50222 |
| HPV45 | L2 | 40 | GTTLADKILQWSSLG | 48126 | LADKILQWS | 50223 |
| HPV45 | L2 | 414 | HTPMWPSTSPTNAST | 48127 | MWPSTSPTN | 50224 |
| HPV45 | L2 | 96 | IEPVGPTDPSIVTLV | 48128 | VGPTDPSIV | 50225 |
| HPV45 | L2 | 282 | IIRLHRPALSSRRGT | 48129 | LHRPALSSR | 50226 |
| HPV45 | L2 | 47 | ILQWSSLGIFLGGLG | 48130 | WSSLGIFLG | 50227 |
| HPV45 | L2 | 35 | INKVEGTTLADKILQ | 48131 | VEGTTLADK | 50228 |
| HPV45 | L2 | 106 | IVTLVEDSSVVASGA | 48132 | LVEDSSVVA | 50229 |
| HPV45 | L2 | 375 | KYSLTMPSTAASSYS | 48133 | LTMPSTAAS | 50230 |
| HPV45 | L2 | 349 | LFDVYADFPPPASTT | 48134 | VYADFPPPA | 50231 |
| HPV45 | L2 | 200 | LQTFASSGSGTEPIS | 48135 | FASSGSGTE | 50232 |
| HPV45 | L2 | 441 | LWPWYYYFPKKRKRI | 48136 | WYYYFPKKR | 50233 |
| HPV45 | L2 | 280 | MDIIRLHRPALSSRR | 48137 | IRLHRPALS | 50234 |
| HPV45 | L2 | 182 | NIFVGTPTSGSHGYE | 48138 | VGTPTSGSH | 50235 |
| HPV45 | L2 | 162 | NPAFSDPSIIEVPQT | 48139 | FSDPSIIEV | 50236 |
| HPV45 | L2 | 256 | NPAYEPLDTTLSFEP | 48140 | YEPLDTTLS | 50237 |
| HPV45 | L2 | 234 | NQQVRVSTSQFLTHP | 48141 | VRVSTSQFL | 50238 |
| HPV45 | L2 | 82 | NTVVDVGPTRPPVVI | 48142 | VDVGPTRPP | 50239 |
| HPV45 | L2 | 390 | NVTVPLTSAWDVPIY | 48143 | VPLTSAWDV | 50240 |
| HPV45 | L2 | 141 | PAVLDITPTVDSVSI | 48144 | LDITPTVDS | 50241 |
| HPV45 | L2 | 407 | PDIILPSHTPMWPST | 48145 | ILPSHTPMW | 50242 |
| HPV45 | L2 | 168 | PSIIEVPQTGEVSGN | 48146 | IEVPQTGEV | 50243 |
| HPV45 | L2 | 364 | PSTIHKSFTYPKYSL | 48147 | IHKSFTYPK | 50244 |
| HPV45 | L2 | 93 | PVVIEPVGPTDPSIV | 48148 | IEPVGPTDP | 50245 |
| HPV45 | L2 | 294 | RGTVRFSRLGQRATM | 48149 | VRFSRLGQR | 50246 |
| HPV45 | L2 | 452 | RKRIPYFFADGFVAA | 48150 | IPYFFADGF | 50247 |
| HPV45 | L2 | 91 | RPPVVIEPVGPTDPS | 48151 | VVIEPVGPT | 50248 |
| HPV45 | L2 | 319 | RVHFYHDISPIAATE | 48152 | FYHDISPIA | 50249 |
| HPV45 | L2 | 277 | SDFMDIIRLHRPALS | 48153 | MDIIRLHRP | 50250 |
| HPV45 | L2 | 370 | SFTYPKYSLTMPSTA | 48154 | YPKYSLTMP | 50251 |
| HPV45 | L2 | 180 | SGNIFVGTPTSGSHG | 48155 | IFVGTPTSG | 50252 |
| HPV45 | L2 | 192 | SHGYEEIPLQTFASS | 48156 | YEEIPLQTF | 50253 |
| HPV45 | L2 | 52 | SLGIFLGGLGIGTGS | 48157 | IFLGGLGIG | 50254 |
| HPV45 | L2 | 377 | SLTMPSTAASSYSNV | 48158 | MPSTAASSY | 50255 |
| HPV45 | L2 | 81 | SNTVVDVGPTRPPVV | 48159 | VVDVGPTRP | 50256 |
| HPV45 | L2 | 242 | SQFLTHPSSLVTFDN | 48160 | LTHPSSLVT | 50257 |
| HPV45 | L2 | 249 | SSLVTFDNPAYEPLD | 48161 | VTFDNPAYE | 50258 |
| HPV45 | L2 | 113 | SSVVASGAPVPTFTG | 48162 | VASGAPVPT | 50259 |
| HPV45 | L2 | 332 | TEEIELQPLISATND | 48163 | IELQPLISA | 50260 |
| HPV45 | L2 | 210 | TEPISSTPLPTVRRV | 48164 | ISSTPLPTV | 50261 |
| HPV45 | L2 | 140 | TPAVLDITPTVDSVS | 48165 | VLDITPTVD | 50262 |
| HPV45 | L2 | 415 | TPMWPSTSPTNASTT | 48166 | WPSTSPTNA | 50263 |
| HPV45 | L2 | 147 | TPTVDSVSISSTSFT | 48167 | VDSVSISST | 50264 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV45 | L2 | 128 | TSGFEITSSGTTTPA | 48168 | FEITSSGTT | 50265 |
| HPV45 | L2 | 241 | TSQFLTHPSSLVTFD | 48169 | FLTHPSSLV | 50266 |
| HPV45 | L2 | 429 | TTYIGIHGTQYYLWP | 48170 | IGIHGTQYY | 50267 |
| HPV45 | L2 | 150 | VDSVSISSTSFTNPA | 48171 | VSISSTSFT | 50268 |
| HPV45 | L2 | 320 | VHFYHDISPIAATEE | 48172 | YHDISPIAA | 50269 |
| HPV45 | L2 | 401 | VPIYTGPDIILPSHT | 48173 | YTGPDIILP | 50270 |
| HPV45 | L2 | 221 | VRRVRGPRLYSRANQ | 48174 | VRGPRLYSR | 50271 |
| HPV45 | L2 | 107 | VTLVEDSSVVASGAP | 48175 | VEDSSVVAS | 50272 |
| HPV45 | L2 | 84 | VVDVGPTRPPVVIEP | 48176 | VGPTRPPVV | 50273 |
| HPV45 | L2 | 353 | YADFPPPASTTPSTI | 48177 | FPPPASTTP | 50274 |
| HPV45 | L2 | 259 | YEPLDTTLSFEPTSN | 48178 | LDTTLSFEP | 50275 |
| HPV45 | L2 | 323 | YHDISPIAATEEIEL | 48179 | ISPIAATEE | 50276 |
| HPV45 | L2 | 373 | YPKYSLTMPSTAASS | 48180 | YSLTMPSTA | 50277 |
| HPV45 | L2 | 388 | YSNVTVPLTSAWDVP | 48181 | VTVPLTSAW | 50278 |
| HPV56 | E2 | 2 | --MVPCLQVCKAKAC | 48182 | VPCLQVCKA | 50279 |
| HPV56 | E2 | 121 | AKKFGCKNIWEVHME | 48183 | FGCKNIWEV | 50280 |
| HPV56 | E2 | 44 | CEELWLTEPKKCFKK | 48184 | LWLTEPKKC | 50281 |
| HPV56 | E2 | 126 | CKNIWEVHMENESIY | 48185 | IWEVHMENE | 50282 |
| HPV56 | E2 | 7 | CLQVCKAKACSAIEV | 48186 | VCKAKACSA | 50283 |
| HPV56 | E2 | 16 | CSAIEVQIALESLST | 48187 | IEVQIALES | 50284 |
| HPV56 | E2 | 95 | CSGVDYRGIYYVHDG | 48188 | VDYRGIYYV | 50285 |
| HPV56 | E2 | 88 | DCGWQKVCSGVDYRG | 48189 | WQKVCSGVD | 50286 |
| HPV56 | E2 | 137 | ESIYCPDSVSSTCRY | 48190 | YCPDSVSST | 50287 |
| HPV56 | E2 | 131 | EVHMENESIYCPDSV | 48191 | MENESIYCP | 50288 |
| HPV56 | E2 | 20 | EVQIALESLSTTIYN | 48192 | IALESLSTT | 50289 |
| HPV56 | E2 | 257 | FQKYKTLFVDVTSTY | 48193 | YKTLFVDVT | 50290 |
| HPV56 | E2 | 62 | HIEVWFDGSKNNCMQ | 48194 | VWFDGSKNN | 50291 |
| HPV56 | E2 | 284 | ITIIYKDETQRNSFL | 48195 | IYKDETQRN | 50292 |
| HPV56 | E2 | 302 | KIPVVYRLVWDK--- | 48196 | VVYRLVWDK | 50293 |
| HPV56 | E2 | 261 | KTLFVDVTSTYHWTS | 48197 | FVDVTSTYH | 50294 |
| HPV56 | E2 | 81 | KYIYYNGDCGWQKVC | 48198 | YYNGDCGWQ | 50295 |
| HPV56 | E2 | 298 | LSHVKIPVVYRLVWD | 48199 | VKIPVVYRL | 50296 |
| HPV56 | E2 | 75 | MQYVAWKYIYYNGDC | 48200 | VAWKYIYYN | 50297 |
| HPV56 | E2 | 35 | NEEWTLRDTCEELWL | 48201 | WTLRDTCEE | 50298 |
| HPV56 | E2 | 136 | NESIYCPDSVSSTCR | 48202 | IYCPDSVSS | 50299 |
| HPV56 | E2 | 278 | NKNYSIITIIYKDET | 48203 | YSIITIIYK | 50300 |
| HPV56 | E2 | 295 | NSFLSHVKIPVVYRL | 48204 | LSHVKIPVV | 50301 |
| HPV56 | E2 | 22 | QIALESLSTTIYNNE | 48205 | LESLSTTIY | 50302 |
| HPV56 | E2 | 150 | RYNVSPVETVNEYNT | 48206 | VSPVETVNE | 50303 |
| HPV56 | E2 | 254 | RYRFQKYKTLFVDVT | 48207 | FQKYKTLFV | 50304 |
| HPV56 | E2 | 172 | STSVGNQDAAVSHRP | 48208 | VGNQDAAVS | 50305 |
| HPV56 | E2 | 148 | TCRYNVSPVETVNEY | 48209 | YNVSPVETV | 50306 |
| HPV56 | E2 | 262 | TLFVDVTSTYHWTST | 48210 | VDVTSTYHW | 50307 |
| HPV56 | E2 | 268 | TSTYHWTSTDNKNYS | 48211 | YHWTSTDNK | 50308 |
| HPV56 | E2 | 156 | VETVNEYNTHKTTTT | 48212 | VNEYNTHKT | 50309 |
| HPV56 | E2 | 159 | VNEYNTHKTTTTTST | 48213 | YNTHKTTTT | 50310 |
| HPV56 | E2 | 5 | VPCLQVCKAKACSAI | 48214 | LQVCKAKAC | 50311 |
| HPV56 | E2 | 260 | YKTLFVDVTSTYHWT | 48215 | LFVDVTSTY | 50312 |
| HPV56 | E6 | 46 | AEVYNFACTELKLVY | 48216 | YNFACTELK | 50313 |
| HPV56 | E6 | 135 | AHGWTGSCLGCWRQT | 48217 | WTGSCLGCW | 50314 |
| HPV56 | E6 | 63 | DFPYAVCRVCLLFYS | 48218 | YAVCRVCLL | 50315 |
| HPV56 | E6 | 104 | DLLIRCYRCQSPLTP | 48219 | IRCYRCQSP | 50316 |
| HPV56 | E6 | 31 | DLRLSCVYCKKELTR | 48220 | LSCVYCKKE | 50317 |
| HPV56 | E6 | 86 | DYSVYGATLESITKK | 48221 | VYGATLESI | 50318 |
| HPV56 | E6 | 26 | EIPLIDLRLSCVYCK | 48222 | LIDLRLSCV | 50319 |
| HPV56 | E6 | 131 | FHLIAHGWTGSCLGC | 48223 | IAHGWTGSC | 50320 |
| HPV56 | E6 | 27 | IPLIDLRLSCVYCKK | 48224 | IDLRLSCVY | 50321 |
| HPV56 | E6 | 107 | IRCYRCQSPLTPEEK | 48225 | YRCQSPLTP | 50322 |
| HPV56 | E6 | 40 | KKELTRAEVYNFACT | 48226 | LTRAEVYNF | 50323 |
| HPV56 | E6 | 99 | KKQLCDLLIRCYRCQ | 48227 | LCDLLIRCY | 50324 |
| HPV56 | E6 | 57 | KLVYRDDFPYAVCRV | 48228 | YRDDFPYAV | 50325 |
| HPV56 | E6 | 81 | KYRYYDYSVYGATLE | 48229 | YYDYSVYGA | 50326 |
| HPV56 | E6 | 94 | LESITKKQLCDLLIR | 48230 | ITKKQLCDL | 50327 |
| HPV56 | E6 | 29 | LIDLRLSCVYCKKEL | 48231 | LRLSCVYCK | 50328 |
| HPV56 | E6 | 21 | LSEVLEIPLIDLRLS | 48232 | VLEIPLIDL | 50329 |
| HPV56 | E6 | 65 | PYAVCRVCLLFYSKV | 48233 | VCRVCLLFY | 50330 |
| HPV56 | E6 | 45 | RAEVYNFACTELKLV | 48234 | VYNFACTEL | 50331 |
| HPV56 | E6 | 61 | RDDFPYAVCRVCLLF | 48235 | FPYAVCRVC | 50332 |
| HPV56 | E6 | 35 | SCVYCKKELTRAEVY | 48236 | YCKKELTRA | 50333 |
| HPV56 | E6 | 22 | SEVLEIPLIDLRLSC | 48237 | LEIPLIDLR | 50334 |
| HPV56 | E6 | 71 | VCLLFYSKVRKYRYY | 48238 | LFYSKVRKY | 50335 |
| HPV56 | E6 | 24 | VLEIPLIDLRLSCVY | 48239 | IPLIDLRLS | 50336 |
| HPV56 | E6 | 48 | VYNFACTELKLVYRD | 48240 | FACTELKLV | 50337 |
| HPV56 | E6 | 84 | YYDYSVYGATLESIT | 48241 | YSVYGATLE | 50338 |
| HPV56 | E7 | 1 | ---MHGKVPTLQDVV | 48242 | MHGKVPTLQ | 50339 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV56 | E7 | 96 | ALTVTCPLCASSN-- | 48243 | VTCPLCASS | 50340 |
| HPV56 | E7 | 71 | CKFVVQLDIQSTKED | 48244 | VVQLDIQST | 50341 |
| HPV56 | E7 | 61 | CYLIHVPCCECKFVV | 48245 | IHVPCCECK | 50342 |
| HPV56 | E7 | 85 | DLRVVQQLLMGALTV | 48246 | VVQQLLMGA | 50343 |
| HPV56 | E7 | 59 | HTCYLIHVPCCECKF | 48247 | YLIHVPCCE | 50344 |
| HPV56 | E7 | 63 | LIHVPCCECKFVVQL | 48248 | VPCCECKFV | 50345 |
| HPV56 | E7 | 11 | LQDVVLELTPQTEID | 48249 | VVLELTPQT | 50346 |
| HPV56 | E7 | 86 | LRVVQQLLMGALTVT | 48250 | VQQLLMGAL | 50347 |
| HPV56 | E7 | 94 | MGALTVTCPLCASSN | 48251 | LTVTCPLCA | 50348 |
| HPV56 | E7 | 12 | QDVVLELTPQTEIDL | 48252 | VLELTPQTE | 50349 |
| HPV56 | E7 | 91 | QLLMGALTVTCPLCA | 48253 | MGALTVTCP | 50350 |
| HPV56 | E7 | 90 | QQLLMGALTVTCPLC | 48254 | LMGALTVTC | 50351 |
| HPV56 | E7 | 60 | TCYLIHVPCCECKFV | 48255 | LIHVPCCEC | 50352 |
| HPV56 | E7 | 8 | VPTLQDVVLELTPQT | 48256 | LQDVVLELT | 50353 |
| HPV56 | E7 | 89 | VQQLLMGALTVTCPL | 48257 | LLMGALTVT | 50354 |
| HPV56 | E7 | 74 | VVQLDIQSTKEDLRV | 48258 | LDIQSTKED | 50355 |
| HPV56 | L1 | 1 | ---MMLPMMYIRDP | 48259 | MMLPMMYIY | 50356 |
| HPV56 | L1 | 3 | -MMLPMMYIRDPPL | 48260 | LPMMYIRD | 50357 |
| HPV56 | L1 | 301 | AGKVGETIPAELYLK | 48261 | VGETIPAEL | 50358 |
| HPV56 | L1 | 432 | ANLLEDWNIGLSPPV | 48262 | LEDWNIGLS | 50359 |
| HPV56 | L1 | 29 | AVNVFPIFLQMATWR | 48263 | VFPIFLQMA | 50360 |
| HPV56 | L1 | 104 | AYQYRVFRVRLPDPN | 48264 | YRVFRVRLP | 50361 |
| HPV56 | L1 | 22 | CIFLDVGAVNVFPIF | 48265 | LDVGAVNVF | 50362 |
| HPV56 | L1 | 222 | CPPLALINTPIEDGD | 48266 | LALINTPIE | 50363 |
| HPV56 | L1 | 14 | DPPLHYGLCIFLDVG | 48267 | LHYGLCIFL | 50364 |
| HPV56 | L1 | 63 | DSYVKRTSIFYHAGS | 48268 | VKRTSIFYH | 50365 |
| HPV56 | L1 | 484 | DVNLQDSFSTDLDQF | 48269 | LQDSFSTDL | 50366 |
| HPV56 | L1 | 437 | DWNIGLSPPVATSLE | 48270 | IGLSPPVAT | 50367 |
| HPV56 | L1 | 451 | EDKYRYVRSTAITCQ | 48271 | YRYVRSTAI | 50368 |
| HPV56 | L1 | 407 | ELQFVFQLCKITLSA | 48272 | FVFQLCKIT | 50369 |
| HPV56 | L1 | 46 | ENKVYLPPTPVSKVV | 48273 | VYLPPTPVS | 50370 |
| HPV56 | L1 | 256 | EVPLDIVQSTCKYPD | 48274 | LDIVQSTCK | 50371 |
| HPV56 | L1 | 242 | FGAMDFKVLQESKAE | 48275 | MDFKVLQES | 50372 |
| HPV56 | L1 | 247 | FKVLQESKAEVPLDI | 48276 | LQESKAEVP | 50373 |
| HPV56 | L1 | 24 | FLDVGAVNVFPIFLQ | 48277 | VGAVNVFPI | 50374 |
| HPV56 | L1 | 36 | FLQMATWRPSENKVY | 48278 | MATWRPSEN | 50375 |
| HPV56 | L1 | 160 | FNRLDDTESSNLANN | 48279 | LDDTESSNL | 50376 |
| HPV56 | L1 | 33 | FPIFLQMATWRPSEN | 48280 | FLQMATWRP | 50377 |
| HPV56 | L1 | 482 | FWDVNLQDSFSTDLD | 48281 | VNLQDSFST | 50378 |
| HPV56 | L1 | 151 | GAGLSGHPLFNRLDD | 48282 | LSGHPLFNR | 50379 |
| HPV56 | L1 | 203 | GEHWTKGAVCKSTQV | 48283 | WTKGAVCKS | 50380 |
| HPV56 | L1 | 141 | GLEVGRGQPLGAGLS | 48284 | VGRGQPLGA | 50381 |
| HPV56 | L1 | 363 | GNQLFVTVVDTTRST | 48285 | LFVTVVDTT | 50382 |
| HPV56 | L1 | 147 | GQPLGAGLSGHPLFN | 48286 | LGAGLSGHP | 50383 |
| HPV56 | L1 | 254 | KAEVPLDIVQSTCKY | 48287 | VPLDIVQST | 50384 |
| HPV56 | L1 | 119 | KFGLPDTNIYNPDQE | 48288 | LPDTNIYNP | 50385 |
| HPV56 | L1 | 416 | KITLSAEVMAYLHNM | 48289 | LSAEVMAYL | 50386 |
| HPV56 | L1 | 96 | KTNIPKVSAYQYRVF | 48290 | IPKVSAYQY | 50387 |
| HPV56 | L1 | 48 | KVYLPPTPVSKVVAT | 48291 | LPPTPVSKV | 50388 |
| HPV56 | L1 | 479 | KYKFWDVNLQDSFST | 48292 | FWDVNLQDS | 50389 |
| HPV56 | L1 | 453 | KYRYVRSTAITCQRE | 48293 | YVRSTAITC | 50390 |
| HPV56 | L1 | 477 | LAKYKFWDVNLQDSF | 48294 | YKFWDVNLQ | 50391 |
| HPV56 | L1 | 21 | LCIFLDVGAVNVFPI | 48295 | FLDVGAVNV | 50392 |
| HPV56 | L1 | 193 | LCIVGCTPAMGEHWT | 48296 | VGCTPAMGE | 50393 |
| HPV56 | L1 | 435 | LEDWNIGLSPPVATS | 48297 | WNIGLSPPV | 50394 |
| HPV56 | L1 | 427 | LHNMNANLLEDWNIG | 48298 | MNANLLEDW | 50395 |
| HPV56 | L1 | 400 | LRHVEEYELQFVFQL | 48299 | VEEYELQFV | 50396 |
| HPV56 | L1 | 388 | LSKYDARKINQYLRH | 48300 | YDARKINQY | 50397 |
| HPV56 | L1 | 424 | MAYLHNMNANLLEDW | 48301 | LHNMNANLL | 50398 |
| HPV56 | L1 | 8 | MMYIRDPPLHYGLC | 48302 | IYRDPPLHY | 50399 |
| HPV56 | L1 | 9 | MYIRDPPLHYGLCI | 48303 | YRDPPLHYG | 50400 |
| HPV56 | L1 | 439 | NIGLSPPVATSLEDK | 48304 | LSPPVATSL | 50401 |
| HPV56 | L1 | 183 | NISVDGKQTQLCIVG | 48305 | VDGKQTQLC | 50402 |
| HPV56 | L1 | 345 | NKPYWLQRAQGHNNG | 48306 | YWLQRAQGH | 50403 |
| HPV56 | L1 | 47 | NKVYLPPTPVSKVVA | 48307 | YLPPTPVSK | 50404 |
| HPV56 | L1 | 229 | NTPIEDGDMIDTGFG | 48308 | IEDGDMIDT | 50405 |
| HPV56 | L1 | 309 | PAELYLKGSNGREPP | 48309 | LYLKGSNGR | 50406 |
| HPV56 | L1 | 224 | PLALINTPIEDGDMI | 48310 | LINTPIEDG | 50407 |
| HPV56 | L1 | 258 | PLDIVQSTCKYPDYL | 48311 | IVQSTCKYP | 50408 |
| HPV56 | L1 | 7 | PMMYIRDPPLHYGL | 48312 | YIYRDPPLH | 50409 |
| HPV56 | L1 | 117 | PNKFGLPDTNIYNPD | 48313 | FGLPDTNIY | 50410 |
| HPV56 | L1 | 324 | PSSVYVATPSGSMIT | 48314 | VYVATPSGS | 50411 |
| HPV56 | L1 | 53 | PTPVSKVVATDSYVK | 48315 | VSKVVATDS | 50412 |
| HPV56 | L1 | 132 | QERLVWACVGLEVGR | 48316 | LVWACVGLE | 50413 |
| HPV56 | L1 | 497 | QFPLGRKFLMQLGTR | 48317 | LGRKFLMQL | 50414 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV56 | L1 | 409 | QFVFQLCKITLSAEV | 48318 | FQLCKITLS | 50415 |
| HPV56 | L1 | 192 | QLCIVGCTPAMGEHW | 48319 | IVGCTPAMG | 50416 |
| HPV56 | L1 | 365 | QLFVTVVDTTRSTNM | 48320 | VTVVDTTRS | 50417 |
| HPV56 | L1 | 190 | QTQLCIVGCTPAMGE | 48321 | LCIVGCTPA | 50418 |
| HPV56 | L1 | 106 | QYRVFRVRLPDPNKF | 48322 | VFRVRLPDP | 50419 |
| HPV56 | L1 | 502 | RKFLMQLGTRSKPAV | 48323 | LMQLGTRSK | 50420 |
| HPV56 | L1 | 134 | RLVWACVGLEVGRGQ | 48324 | WACVGLEVG | 50421 |
| HPV56 | L1 | 333 | SGSMITSEAQLFNKP | 48325 | MITSEAQLF | 50422 |
| HPV56 | L1 | 70 | SIFYHAGSSRLLAVG | 48326 | YHAGSSRLL | 50423 |
| HPV56 | L1 | 78 | SRLLAVGHPYYSVTK | 48327 | LAVGHPYYS | 50424 |
| HPV56 | L1 | 168 | SSNLANNNVIEDSRD | 48328 | LANNNVIED | 50425 |
| HPV56 | L1 | 325 | SSVYVATPSGSMITS | 48329 | YVATPSGSM | 50426 |
| HPV56 | L1 | 492 | STDLDQFPLGRKFLM | 48330 | LDQFPLGRK | 50427 |
| HPV56 | L1 | 376 | STNMTISTATEQLSK | 48331 | MTISTATEQ | 50428 |
| HPV56 | L1 | 214 | STQVTTGDCPPLALI | 48332 | VTTGDCPPL | 50429 |
| HPV56 | L1 | 62 | TDSYVKRTSIFYHAG | 48333 | YVKRTSIFY | 50430 |
| HPV56 | L1 | 385 | TEQLSKYDARKINQY | 48334 | LSKYDARKI | 50431 |
| HPV56 | L1 | 199 | TPAMGEHWTKGAVCK | 48335 | MGEHWTKGA | 50432 |
| HPV56 | L1 | 69 | TSIFYHAGSSRLLAV | 48336 | FYHAGSSRL | 50433 |
| HPV56 | L1 | 403 | VEEYELQFVFQLCKI | 48337 | YELQFVFQL | 50434 |
| HPV56 | L1 | 32 | VFPIFLQMATWRPSE | 48338 | IFLQMATWR | 50435 |
| HPV56 | L1 | 411 | VFQLCKITLSAEVMA | 48339 | LCKITLSAE | 50436 |
| HPV56 | L1 | 109 | VFRVRLPDPNKFGLP | 48340 | VRLPDPNKF | 50437 |
| HPV56 | L1 | 27 | VGAVNVFPIFLQMAT | 48341 | VNVFPIFLQ | 50438 |
| HPV56 | L1 | 56 | VSKVVATDSYVKRTS | 48342 | VVATDSYVK | 50439 |
| HPV56 | L1 | 368 | VTVVDTTRSTNMTIS | 48343 | VDTTRSTNM | 50440 |
| HPV56 | L1 | 284 | WFYLRREQLFARHYF | 48344 | LRREQLFAR | 50441 |
| HPV56 | L1 | 268 | YPDYLKMSADAYGDS | 48345 | YLKMSADAY | 50442 |
| HPV56 | L1 | 107 | YRVFRVRLPDPNKFG | 48346 | FRVRLPDPN | 50443 |
| HPV56 | L1 | 454 | YRYVRSTAITCQREQ | 48347 | VRSTAITCQ | 50444 |
| HPV56 | L1 | 87 | YYSVTKDNTKTNIPK | 48348 | VTKDNTKTN | 50445 |
| HPV56 | L2 | 1 | ---MVAHRATRRKRA | 48349 | MVAHRATRR | 50446 |
| HPV56 | L2 | 2 | --MVAHRATRRKRAS | 48350 | VAHRATRRK | 50447 |
| HPV56 | L2 | 44 | ADKILQWGSLFTYFG | 48351 | ILQWGSLFT | 50448 |
| HPV56 | L2 | 332 | AEEIEMQPLLSANNS | 48352 | IEMQPLLSA | 50449 |
| HPV56 | L2 | 361 | APGLSSQSVATPSAH | 48353 | LSSQSVATP | 50450 |
| HPV56 | L2 | 249 | ATLVSADNPLFEGTD | 48354 | VSADNPLFE | 50451 |
| HPV56 | L2 | 409 | DIVLPTGPSTWPFVP | 48355 | LPTGPSTWP | 50452 |
| HPV56 | L2 | 45 | DKILQWGSLFTYFGG | 48356 | LQWGSLFTY | 50453 |
| HPV56 | L2 | 241 | DPAFLDRPATLVSAD | 48357 | FLDRPATLV | 50454 |
| HPV56 | L2 | 276 | DPDFMNIVALHRPAF | 48358 | FMNIVALHR | 50455 |
| HPV56 | L2 | 263 | DTSLAFSPSGVAPDP | 48359 | LAFSPSGVA | 50456 |
| HPV56 | L2 | 334 | EIEMQPLLSANNSFD | 48360 | MQPLLSANN | 50457 |
| HPV56 | L2 | 197 | EIPMQTFAVHGSGTE | 48361 | MQTFAVHGS | 50458 |
| HPV56 | L2 | 112 | ESSVIESGAGIPNFT | 48362 | VIESGAGIP | 50459 |
| HPV56 | L2 | 347 | FDGLYDIYANIDDEA | 48363 | LYDIYANID | 50460 |
| HPV56 | L2 | 234 | FQQVKVTDPAFLDRP | 48364 | VKVTDPAFL | 50461 |
| HPV56 | L2 | 221 | FRRIAAPRLYRKAFQ | 48365 | IAAPRLYRK | 50462 |
| HPV56 | L2 | 299 | FSRLGRKATIQTRRG | 48366 | LGRKATIQT | 50463 |
| HPV56 | L2 | 54 | FTYFGGLGIGTGTGS | 48367 | FGGLGIGTG | 50464 |
| HPV56 | L2 | 130 | GFEITSSSTTTPAVL | 48368 | ITSSSTTTP | 50465 |
| HPV56 | L2 | 181 | GNILISTPTSGIHSY | 48369 | LISTPTSGI | 50466 |
| HPV56 | L2 | 437 | GSSFALWPVYFFRRR | 48370 | FALWPVYFF | 50467 |
| HPV56 | L2 | 431 | HDVYIQGSSFALWPV | 48371 | YIQGSSFAL | 50468 |
| HPV56 | L2 | 375 | HLPIKPSTLSFASNT | 48372 | IKPSTLSFA | 50469 |
| HPV56 | L2 | 321 | HYYYDISPIAQAEEI | 48373 | YDISPIAQA | 50470 |
| HPV56 | L2 | 192 | IHSYEEIPMQTFAVH | 48374 | YEEIPMQTF | 50471 |
| HPV56 | L2 | 47 | ILQWGSLFTYFGGLG | 48375 | WGSLFTYFG | 50472 |
| HPV56 | L2 | 218 | IPGFRRIAAPRLYRK | 48376 | FRRIAAPRL | 50473 |
| HPV56 | L2 | 84 | IVDVTPARPPIVVES | 48377 | VTPARPPIV | 50474 |
| HPV56 | L2 | 106 | IVTLVEESSVIESGA | 48378 | LVEESSVIE | 50475 |
| HPV56 | L2 | 280 | MNIVALHRPAFTTRR | 48379 | VALHRPAFT | 50476 |
| HPV56 | L2 | 200 | MQTFAVHGSGTEPIS | 48380 | FAVHGSGTE | 50477 |
| HPV56 | L2 | 182 | NILISTPTSGIHSYE | 48381 | ISTPTSGIH | 50478 |
| HPV56 | L2 | 256 | NPLFEGTDTSLAFSP | 48382 | FEGTDTSLA | 50479 |
| HPV56 | L2 | 162 | NPLFIDPPVIEAPQT | 48383 | FIDPPVIEA | 50480 |
| HPV56 | L2 | 242 | PAFLDRPATLVSADN | 48384 | LDRPATLVS | 50481 |
| HPV56 | L2 | 141 | PAVLDITPTSSTVHV | 48385 | LDITPTSST | 50482 |
| HPV56 | L2 | 277 | PDFMNIVALHRPAFT | 48386 | MNIVALHRP | 50483 |
| HPV56 | L2 | 408 | PDIVLPTGPSTWPFV | 48387 | VLPTGPSTW | 50484 |
| HPV56 | L2 | 93 | PIVVESVGPTDPSIV | 48388 | VESVGPTDP | 50485 |
| HPV56 | L2 | 163 | PLFIDPPVIEAPQTG | 48389 | IDPPVIEAP | 50486 |
| HPV56 | L2 | 168 | PPVIEAPQTGEVSGN | 48390 | IEAPQTGEV | 50487 |
| HPV56 | L2 | 81 | PSTIVDVTPARPPIV | 48391 | IVDVTPARP | 50488 |
| HPV56 | L2 | 40 | QKTWADKILQWGSLF | 48392 | WADKILQWG | 50489 |

TABLE XIX-continued

DR Supermotif Peptides

| Type | Protein | Position | Sequence | Sequence Id. No. | Core Sequence | Core Seq. Id. No. |
|---|---|---|---|---|---|---|
| HPV56 | L2 | 338 | QPLLSANNSFDGLYD | 48393 | LSANNSFDG | 50490 |
| HPV56 | L2 | 71 | RAGYVPLGSRPSTIV | 48394 | YVPLGSRPS | 50491 |
| HPV56 | L2 | 294 | RGGVRFSRLGRKATI | 48395 | VRFSRLGRK | 50492 |
| HPV56 | L2 | 231 | RKAFQQVKVTDPAFL | 48396 | FQQVKVTDP | 50493 |
| HPV56 | L2 | 453 | RKRIPYFFADGDVAA | 48397 | IPYFFADGD | 50494 |
| HPV56 | L2 | 91 | RPPIVVESVGPTDPS | 48398 | IVVESVGPT | 50495 |
| HPV56 | L2 | 319 | RVHYYYDISPIAQAE | 48399 | YYYDISPIA | 50496 |
| HPV56 | L2 | 373 | SAHLPIKPSTLSFAS | 48400 | LPIKPSTLS | 50497 |
| HPV56 | L2 | 128 | SGGFEITSSSTTTPA | 48401 | FEITSSSTT | 50498 |
| HPV56 | L2 | 180 | SGNILISTPTSGIHS | 48402 | ILISTPTSG | 50499 |
| HPV56 | L2 | 265 | SLAFSPSGVAPDPDF | 48403 | FSPSGVAPD | 50500 |
| HPV56 | L2 | 366 | SQSVATPSAHLPIKP | 48404 | VATPSAHLP | 50501 |
| HPV56 | L2 | 150 | SSTVHVSSTHITNPL | 48405 | VHVSSTHIT | 50502 |
| HPV56 | L2 | 82 | STIVDVTPARPPIVV | 48406 | VDVTPARPP | 50503 |
| HPV56 | L2 | 23 | TCKLSGTCPEDVVNK | 48407 | LSGTCPEDV | 50504 |
| HPV56 | L2 | 210 | TEPISSTPIPGFRRI | 48408 | ISSTPIPGF | 50505 |
| HPV56 | L2 | 202 | TFAVHGSGTEPISST | 48409 | VHGSGTEPI | 50506 |
| HPV56 | L2 | 176 | TGEVSGNILISTPTS | 48410 | VSGNILIST | 50507 |
| HPV56 | L2 | 430 | THDVYIQGSSFALWP | 48411 | VYIQGSSFA | 50508 |
| HPV56 | L2 | 382 | TLSFASNTTNVTAPL | 48412 | FASNTTNVT | 50509 |
| HPV56 | L2 | 161 | TNPLFIDPPVIEAPQ | 48413 | LFIDPPVIE | 50510 |
| HPV56 | L2 | 140 | TPAVLDITPTSSTVH | 48414 | VLDITPTSS | 50511 |
| HPV56 | L2 | 402 | TPFYSGPDIVLPTGP | 48415 | YSGPDIVLP | 50512 |
| HPV56 | L2 | 18 | TQLYKTCKLSGTCPE | 48416 | YKTCKLSGT | 50513 |
| HPV56 | L2 | 152 | TVHVSSTHITNPLFI | 48417 | VSSTHITNP | 50514 |
| HPV56 | L2 | 418 | TWPFVPQSPYDVTHD | 48418 | FVPQSPYDV | 50515 |
| HPV56 | L2 | 96 | VESVGPTDPSIVTLV | 48419 | VGPTDPSIV | 50516 |
| HPV56 | L2 | 320 | VHYYYDISPIAQAEE | 48420 | YYDISPIAQ | 50517 |
| HPV56 | L2 | 143 | VLDITPTSSTVHVSS | 48421 | ITPTSSTVH | 50518 |
| HPV56 | L2 | 107 | VTLVEESSVIESGAG | 48422 | VEESSVIES | 50519 |
| HPV56 | L2 | 354 | YANIDDEAPGLSSQS | 48423 | IDDEAPGLS | 50520 |
| HPV56 | L2 | 74 | YVPLGSRPSTIVDVT | 48424 | LGSRPSTIV | 50521 |

TABLE XXa

DR 3a Submotif Peptides

| Type | Protein | Position | Sequence | Sequence Id. No. | Core Sequence | Core Seq. Id. No. |
|---|---|---|---|---|---|---|
| HPV16 | E1 | 531 | CWNYIDDNLRNALDG | 50522 | YIDDNLRNA | 50853 |
| HPV16 | E1 | 369 | DNDIVDDSEIAYKYA | 50523 | IVDDSEIAY | 50854 |
| HPV16 | E1 | 33 | GDAISDDENENDSDT | 50524 | ISDDENEND | 50855 |
| HPV16 | E1 | 332 | ISEVYGDTPEWIQRQ | 50525 | VYGDTPEWI | 50856 |
| HPV16 | E1 | 520 | KIGMLDDATVPCWNY | 50526 | MLDDATVPC | 50857 |
| HPV16 | E1 | 113 | LKAICIEKQSRAAKR | 50527 | ICIEKQSRA | 50858 |
| HPV16 | E1 | 19 | NGWFYVEAVVEKKTG | 50528 | FYVEAVVEK | 50859 |
| HPV16 | E1 | 305 | PMCMMIEPPKLRSTA | 50529 | MMIEPPKLR | 50860 |
| HPV16 | E1 | 592 | PNEFPFDENGNPVYE | 50530 | FPFDENGNP | 50861 |
| HPV16 | E1 | 401 | QAKIVKDCATMCRHY | 50531 | IVKDCATMC | 50862 |
| HPV16 | E1 | 365 | QWAYDNDIVDDSEIA | 50532 | YDNDIVDDS | 50863 |
| HPV16 | E1 | 622 | RLSLHEDEDKENDGD | 50533 | LHEDEDKEN | 50864 |
| HPV16 | E1 | 127 | RRLFESEDSGYGNTE | 50534 | FESEDSGYG | 50865 |
| HPV16 | E1 | 52 | VDFIVNDNDYLTQAE | 50535 | IVNDNDYLT | 50866 |
| HPV16 | E1 | 588 | VFTFPNEFPFDENGN | 50536 | FPNEFPFDE | 50867 |
| HPV16 | E1 | 428 | WIKYRCDRVDDGGDW | 50537 | YRCDRVDDG | 50868 |
| HPV16 | E2 | 229 | AVALGTEETQTTIQR | 50538 | LGTEETQTT | 50869 |
| HPV16 | E2 | 77 | ELQLTLETIYNSQYS | 50539 | LTLETIYNS | 50870 |
| HPV16 | E2 | 121 | EVQFDGDICNTMHYT | 50540 | FDGDICNTM | 50871 |
| HPV16 | E2 | 171 | FVQFKDDAEKYSKNK | 50541 | FKDDAEKYS | 50872 |
| HPV16 | E2 | 159 | GLYYVHEGIRTYFVQ | 50542 | YVHEGIRTY | 50873 |
| HPV16 | E2 | 139 | HIYICEEASVTVVEG | 50543 | ICEEASVTV | 50874 |
| HPV16 | E2 | 291 | IVHLKGDANTLKCLR | 50544 | LKGDANTLK | 50875 |
| HPV16 | E2 | 335 | IVTLTYDSEWQRDQF | 50545 | LTYDSEWQR | 50876 |
| HPV16 | E2 | 115 | KHGYTVEVQFDGDIC | 50546 | YTVEVQFDG | 50877 |
| HPV16 | E2 | 97 | LQDVSLEVYLTAPTG | 50547 | VSLEVYLTA | 50878 |
| HPV16 | E2 | 19 | LTHYENDSTDLRDHI | 50548 | YENDSTDLR | 50879 |
| HPV16 | E2 | 87 | NSQYSNEKWTLQDVS | 50549 | YSNEKWTLQ | 50880 |
| HPV16 | E2 | 10 | RLNVCQDKILTHYEN | 50550 | VCQDKILTH | 50881 |
| HPV16 | E2 | 138 | THIYICEEASVTVVE | 50551 | YICEEASVT | 50882 |
| HPV16 | E2 | 257 | TKLLHRDSVDSAPIL | 50552 | LHRDSVDSA | 50883 |
| HPV16 | E2 | 337 | TLTYDSEWQRDQFLS | 50553 | YDSEWQRDQ | 50884 |
| HPV16 | E2 | 119 | TVEVQFDGDICNTMH | 50554 | VQFDGDICN | 50885 |

TABLE XXa-continued

DR 3a Submotif Peptides

| Type | Protein | Position | Sequence | Sequence Id. No. | Core Sequence | Core Seq. Id. No. |
|---|---|---|---|---|---|---|
| HPV16 | E2 | 36 | WKHMRLECAIYYKAR | 50555 | MRLECAIYY | 50886 |
| HPV16 | E6 | 33 | IHDIILECVYCKQQL | 50556 | IILECVYCK | 50887 |
| HPV16 | E6 | 60 | LCIVYRDGNPYAVCD | 50557 | VYRDGNPYA | 50888 |
| HPV16 | E6 | 22 | LPQLCTELQTTIHDI | 50558 | LCTELQTTI | 50889 |
| HPV16 | E6 | 45 | QQLLRREVYDFAFRD | 50559 | LRREVYDFA | 50890 |
| HPV16 | E6 | 8 | RTAMFQDPQERPRKL | 50560 | MFQDPQERP | 50891 |
| HPV16 | E7 | 1 | MHGDTPTLHEYM | 50561 | MHGDTPTLH | 50892 |
| HPV16 | E7 | 11 | LHEYMLDLQPETTDL | 50562 | YMLDLQPET | 50893 |
| HPV16 | E7 | 15 | MLDLQPETTDLYCYE | 50563 | LQPETTDLY | 50894 |
| HPV16 | E7 | 23 | TDLYCYEQLNDSSEE | 50564 | YCYEQLNDS | 50895 |
| HPV16 | L1 | 276 | FFYLRREQMFVRHLF | 50565 | LRREQMFVR | 50896 |
| HPV16 | L1 | 297 | GENVPDDLYIKGSGS | 50566 | VPDDLYIKG | 50897 |
| HPV16 | L1 | 326 | GSMVTSDAQIFNKPY | 50567 | VTSDAQIFN | 50898 |
| HPV16 | L1 | 220 | INTVIQDGDMVDTGF | 50568 | VIQDGDMVD | 50899 |
| HPV16 | L1 | 14 | ITCYENDVNVYHIFF | 50569 | YENDVNVYH | 50900 |
| HPV16 | L1 | 481 | KEKFSADLDQFPLGR | 50570 | FSADLDQFP | 50901 |
| HPV16 | L1 | 409 | KITLTADVMTYIHSM | 50571 | LTADVMTYI | 50902 |
| HPV16 | L1 | 246 | KSEVPLDICTSICKY | 50572 | VPLDICTSI | 50903 |
| HPV16 | L1 | 424 | NSTILEDWNFGLQPP | 50573 | ILEDWNFGL | 50904 |
| HPV16 | L1 | 48 | SKVVSTDEYVARTNI | 50574 | VSTDEYVAR | 50905 |
| HPV16 | L1 | 31 | SLWLPSEATVYLPPV | 50575 | LPSEATVYL | 50906 |
| HPV16 | L1 | 117 | TSFYNPDTQRLVWAC | 50576 | YNPDTQRLV | 50907 |
| HPV16 | L1 | 129 | WACVGVEVGRGQPLG | 50577 | VGVEVGRGQ | 50908 |
| HPV16 | L1 | 263 | YIKMVSEPYGDSLFF | 50578 | MVSEPYGDS | 50909 |
| HPV16 | L2 | 373 | ADDFITDTSTTPVPS | 50579 | FITDTSTTP | 50910 |
| HPV16 | L2 | 108 | IVSLVEETSFIDAGA | 50580 | LVEETSFID | 50911 |
| HPV16 | L2 | 326 | KVHYYYDFSTIDSAE | 50581 | YYYDFSTID | 50912 |
| HPV16 | L2 | 465 | LPYFFSDVSLAA | 50582 | FFSDVSLAA | 50913 |
| HPV16 | L2 | 368 | LYDIYADDFITDTST | 50583 | IYADDFITD | 50914 |
| HPV16 | L2 | 439 | QYTIIADAGDFYLHP | 50584 | IIADAGDFY | 50915 |
| HPV16 | L2 | 93 | RPPLTVDPVGPSDPS | 50585 | LTVDPVGPS | 50916 |
| HPV16 | L2 | 277 | SINIAPDPDFLDIVA | 50586 | IAPDPDFLD | 50917 |
| HPV16 | L2 | 250 | TKLITYDNPAYEGID | 50587 | ITYDNPAYE | 50918 |
| HPV16 | L2 | 126 | VPSIPPDVSGFSITT | 50588 | IPPDVSGFS | 50919 |
| HPV16 | L2 | 369 | YDIYADDFITDTSTT | 50589 | YADDFITDT | 50920 |
| HPV16 | L2 | 196 | YEEIPMDTFIVSTNP | 50590 | IPMDTFIVS | 50921 |
| HPV16 | L2 | 260 | YEGIDVDNTLYFSSN | 50591 | IDVDNTLYF | 50922 |
| HPV18 | E1 | 75 | AQEVHNDAQVLHVLK | 50592 | VHNDAQVLH | 50923 |
| HPV18 | E1 | 376 | DNELTDESDMAFEYA | 50593 | LTDESDMAF | 50924 |
| HPV18 | E1 | 382 | ESDMAFEYALLADSN | 50594 | MAFEYALLA | 50925 |
| HPV18 | E1 | 388 | EYALLADSNSNAAAF | 50595 | LLADSNSNA | 50926 |
| HPV18 | E1 | 32 | GDVISDDEDENATDT | 50596 | ISDDEDENA | 50927 |
| HPV18 | E1 | 103 | GERLEVDTELSPRLQ | 50597 | LEVDTELSP | 50928 |
| HPV18 | E1 | 339 | ISEVMGDTPEWIQRL | 50598 | VMGDTPEWI | 50929 |
| HPV18 | E1 | 527 | KVAMLDDATTTCWTY | 50599 | MLDDATTTC | 50930 |
| HPV18 | E1 | 217 | MLAVFKDTYGLSFTD | 50600 | VFKDTYGLS | 50931 |
| HPV18 | E1 | 599 | PNAFPFDKNGNPVYE | 50601 | FPFDKNGNP | 50932 |
| HPV18 | E1 | 408 | QAKYLKDCATMCKHY | 50602 | YLKDCATMC | 50933 |
| HPV18 | E1 | 372 | QWAFDNELTDESDMA | 50603 | FDNELTDES | 50934 |
| HPV18 | E1 | 629 | RLDLHEEEEDADTEG | 50604 | LHEEEEDAD | 50935 |
| HPV18 | E1 | 105 | RLEVDTELSPRLQEI | 50605 | VDTELSPRL | 50936 |
| HPV18 | E1 | 31 | TGDVISDDEDENATD | 50606 | VISDDEDEN | 50937 |
| HPV18 | E1 | 515 | TSHFWLEPLTDTKVA | 50607 | FWLEPLTDT | 50938 |
| HPV18 | E1 | 233 | VRNFKSDKTTCTDWV | 50608 | FKSDKTTCT | 50939 |
| HPV18 | E2 | 164 | GLYYVKEGYNTFYIE | 50609 | YVKEGYNTF | 50940 |
| HPV18 | E2 | 292 | IIHLKGDRNSLKCLR | 50610 | LKGDRNSLK | 50941 |
| HPV18 | E2 | 136 | MTYVAWDSVYYMTDA | 50611 | VAWDSVYYM | 50942 |
| HPV18 | E2 | 91 | QSRYKTEDWTLQDTC | 50612 | YKTEDWTLQ | 50943 |
| HPV18 | E2 | 143 | SVYYMTDAGTWDKTA | 50613 | YMTDAGTWD | 50944 |
| HPV18 | E2 | 123 | TVQVYFDGNKDNCMT | 50614 | VYFDGNKDN | 50945 |
| HPV18 | E2 | 337 | TVTYHSETQRTKFLN | 50615 | YHSETQRTK | 50946 |
| HPV18 | E2 | 40 | WQLIRWENAIFFAAR | 50616 | IRWENAIFF | 50947 |
| HPV18 | E2 | 176 | YIEFKSECEKYGNTG | 50617 | FKSECEKYG | 50948 |
| HPV18 | E6 | 55 | LFVVYRDSIPHAACH | 50618 | VYRDSIPHA | 50949 |
| HPV18 | E6 | 17 | LPDLCTELNTSLQDI | 50619 | LCTELNTSL | 50950 |
| HPV18 | E6 | 85 | SDSVYGDTLEKLTNT | 50620 | VYGDTLEKL | 50951 |
| HPV18 | E7 | 13 | DIVLHLEPQNEIPVD | 50621 | LHLEPQNEI | 50952 |
| HPV18 | E7 | 21 | QNEIPVDLLCHEQLS | 50622 | IPVDLLCHE | 50953 |
| HPV18 | E7 | 74 | RIKLVVESSADDLRA | 50623 | LVVESSADD | 50954 |
| HPV18 | E7 | 26 | VDLLCHEQLSDSEEE | 50624 | LCHEQLSDS | 50955 |
| HPV18 | L1 | 83 | ARVVNTDDYVTPTSI | 50625 | VNTDDYVTP | 50956 |
| HPV18 | L1 | 311 | FFCLRREQLFARHFW | 50626 | LRREQLFAR | 50957 |
| HPV18 | L1 | 361 | GSIVTSDSQLFNKPY | 50627 | VTSDSQLFN | 50958 |
| HPV18 | L1 | 281 | KCEVPLDICQSICKY | 50628 | VPLDICQSI | 50959 |
| HPV18 | L1 | 517 | KEKFSLDLDQYPLGR | 50629 | FSLDLDQYP | 50960 |

TABLE XXa-continued

DR 3a Submotif Peptides

| Type | Protein | Position | Sequence | Sequence Id. No. | Core Sequence | Core Seq. Id. No. |
|---|---|---|---|---|---|---|
| HPV18 | L1 | 519 | KFSLDLDQYPLGRKF | 50630 | LDLDQYPLG | 50961 |
| HPV18 | L1 | 255 | KNTVLEDGDMVDTGY | 50631 | VLEDGDMVD | 50962 |
| HPV18 | L1 | 460 | NSSILEDWNFGVPPP | 50632 | ILEDWNFGV | 50963 |
| HPV18 | L1 | 445 | TITLTADVMSYIHSM | 50633 | LTADVMSYI | 50964 |
| HPV18 | L1 | 152 | TSIYNPETQRLVWAC | 50634 | YNPETQRLV | 50965 |
| HPV18 | L1 | 298 | YLQMSADPYGDSMFF | 50635 | MSADPYGDS | 50966 |
| HPV18 | L2 | 351 | FDIYADDMDPAVPVP | 50636 | YADDMDPAV | 50967 |
| HPV18 | L2 | 106 | IVTLIEDSSVVTSGA | 50637 | LIEDSSVVT | 50968 |
| HPV18 | L2 | 350 | LFDIYADDMDPAVPV | 50638 | IYADDMDPA | 50969 |
| HPV18 | L2 | 91 | RPPVVIEPVGPTDPS | 50639 | VVIEPVGPT | 50970 |
| HPV18 | L2 | 319 | RVHFYHDISPIAPSP | 50640 | FYHDISPIA | 50971 |
| HPV18 | L2 | 249 | SSLITYDNPAFEPVD | 50641 | ITYDNPAFE | 50972 |
| HPV18 | L2 | 454 | VPYFFADGFVAA | 50642 | FFADGFVAA | 50973 |
| HPV31 | E1 | 413 | CDKVSDEGDWRDIVK | 50643 | VSDEGDWRD | 50974 |
| HPV31 | E1 | 349 | DNDVMDDSEIAYKYA | 50644 | VMDDSEIAY | 50975 |
| HPV31 | E1 | 32 | GDNISEDENEDSSDT | 50645 | ISEDENEDS | 50976 |
| HPV31 | E1 | 312 | ISDVYGETPEWIERQ | 50646 | VYGETPEWI | 50977 |
| HPV31 | E1 | 500 | KIGMLDDATTPCWHY | 50647 | MLDDATTPC | 50978 |
| HPV31 | E1 | 268 | KNRITIEKLLEKLLC | 50648 | ITIEKLLEK | 50979 |
| HPV31 | E1 | 112 | LKAICIENNSKTAKR | 50649 | ICIENNSKT | 50980 |
| HPV31 | E1 | 18 | NGWFYVEAVIDRQTG | 50650 | FYVEAVIDR | 50981 |
| HPV31 | E1 | 572 | PNPFPFDKNGNPVYE | 50651 | FPFDKNGNP | 50982 |
| HPV31 | E1 | 381 | QAKIVKDCGTMCRHY | 50652 | IVKDCGTMC | 50983 |
| HPV31 | E1 | 144 | QQMVQVEEQQTTLSC | 50653 | VQVEEQQTT | 50984 |
| HPV31 | E1 | 345 | QWAYDNDVMDDSEIA | 50654 | YDNDVMDDS | 50985 |
| HPV31 | E1 | 602 | RLNLHEEEDKENDGD | 50655 | LHEEEDKEN | 50986 |
| HPV31 | E2 | 77 | ELQMMLETLNNTEYK | 50656 | MMLETLNNT | 50987 |
| HPV31 | E2 | 200 | ESVFSSDEISFAGIV | 50657 | FSSDEISFA | 50988 |
| HPV31 | E2 | 139 | FIYLCIDGQCTVVEG | 50658 | LCIDGQCTV | 50989 |
| HPV31 | E2 | 298 | IIHLKGDANILKCLR | 50659 | LKGDANILK | 50990 |
| HPV31 | E2 | 115 | KHGYTVEVQFDGDVH | 50660 | YTVEVQFDG | 50991 |
| HPV31 | E2 | 262 | NKLLRGDSVDSVNCG | 50661 | LRGDSVDSV | 50992 |
| HPV31 | E2 | 87 | NTEYKNEDWTMQQTS | 50662 | YKNEDWTMQ | 50993 |
| HPV31 | E2 | 194 | QVIVFPESVFSSDEI | 50663 | VFPESVFSS | 50994 |
| HPV31 | E2 | 10 | RLNVCQDKILEHYEN | 50664 | VCQDKILEH | 50995 |
| HPV31 | E2 | 119 | TVEVQFDGDVHNTMH | 50665 | VQFDGDVHN | 50996 |
| HPV31 | E2 | 36 | WKHIRLECVLMYKAR | 50666 | IRLECVLMY | 50997 |
| HPV31 | E6 | 21 | ALEIPYDELRLNCVY | 50667 | IPYDELRLN | 50998 |
| HPV31 | E6 | 53 | LTIVYRDDTPHGVCT | 50668 | VYRDDTPHG | 50999 |
| HPV31 | E6 | 54 | TIVYRDDTPHGVCTK | 50669 | YRDDTPHGV | 51000 |
| HPV31 | E7 | 1 | MRGETPTLQDYV | 50670 | MRGETPTLQ | 51001 |
| HPV31 | E7 | 78 | DIRILQELLMGSFGI | 50671 | ILQELLMGS | 51002 |
| HPV31 | E7 | 11 | LQDYVLDLQPEATDL | 50672 | YVLDLQPEA | 51003 |
| HPV31 | E7 | 15 | VLDLQPEATDLHCYE | 50673 | LQPEATDLH | 51004 |
| HPV31 | L1 | 251 | FFYLRREQMFVRHFF | 50674 | LRREQMFVR | 51005 |
| HPV31 | L1 | 272 | GESVPTDLYIKGSGS | 50675 | VPTDLYIKG | 51006 |
| HPV31 | L1 | 301 | GSMVTSDAQIFNKPY | 50676 | VTSDAQIFN | 51007 |
| HPV31 | L1 | 446 | KDYVFWEVNLKEKFS | 50677 | VFWEVNLKE | 51008 |
| HPV31 | L1 | 456 | KEKFSADLDQFPLGR | 50678 | FSADLDQFP | 51009 |
| HPV31 | L1 | 384 | KITLSADIMTYIHSM | 50679 | LSADIMTYI | 51010 |
| HPV31 | L1 | 195 | KNSVIQDGDMVDTGF | 50680 | VIQDGDMVD | 51011 |
| HPV31 | L1 | 221 | KSNVPLDICNSICKY | 50681 | VPLDICNSI | 51012 |
| HPV31 | L1 | 399 | NPAILEDWNFGLTTP | 50682 | ILEDWNFGL | 51013 |
| HPV31 | L1 | 22 | SKVVSTDEYVTRTNI | 50683 | VSTDEYVTR | 51014 |
| HPV31 | L1 | 92 | TSFYNPETQRLVWAC | 50684 | YNPETQRLV | 51015 |
| HPV31 | L1 | 104 | WACVGLEVGRGQPLG | 50685 | VGLEVGRGQ | 51016 |
| HPV31 | L1 | 238 | YLKMVAEPYGDTLFF | 50686 | MVAEPYGDT | 51017 |
| HPV31 | L2 | 361 | DTDFTVDTPATHNVS | 50687 | FTVDTPATH | 51018 |
| HPV31 | L2 | 409 | GPDVPIEHAPTQVFP | 50688 | VPIEHAPTQ | 51019 |
| HPV31 | L2 | 108 | IVSLVEESGIVDVGA | 50689 | LVEESGIVD | 51020 |
| HPV31 | L2 | 245 | KQLITYENPAYETVN | 50690 | ITYENPAYE | 51021 |
| HPV31 | L2 | 355 | LYDIYADTDFTVDTP | 50691 | IYADTDFTV | 51022 |
| HPV31 | L2 | 432 | QVSIFVDGGDFYLHP | 50692 | IFVDGGDFY | 51023 |
| HPV31 | L2 | 93 | RPPVSIDPVGPLDPS | 50693 | VSIDPVGPL | 51024 |
| HPV31 | L2 | 319 | RVHYYYDISSINPAG | 50694 | YYYDISSIN | 51025 |
| HPV31 | L2 | 270 | SHNIAPDPDFLDIIA | 50695 | IAPDPDFLD | 51026 |
| HPV31 | L2 | 458 | VSYFFTDVSVAA | 50696 | FFTDVSVAA | 51027 |
| HPV31 | L2 | 191 | YEEIPMDTFIVSTNN | 50697 | IPMDTFIVS | 51028 |
| HPV31 | L2 | 255 | YETVNAEESLYFSNT | 50698 | VNAEESLYF | 51029 |
| HPV33 | E1 | 362 | DNELTDDSDIAYYYA | 50699 | LTDDSDIAY | 51030 |
| HPV33 | E1 | 170 | DSEVSCETNVDSCEN | 50700 | VSCETNVDS | 51031 |
| HPV33 | E1 | 59 | ENSIQADTEAARALF | 50701 | IQADTEAAR | 51032 |
| HPV33 | E1 | 298 | ETCMVIEPPKLRSQT | 50702 | MVIEPPKLR | 51033 |
| HPV33 | E1 | 32 | GDNISEDEDETADDS | 50703 | ISEDEDETA | 51034 |
| HPV33 | E1 | 513 | KIGMIDDVTPISWTY | 50704 | MIDDVTPIS | 51035 |

TABLE XXa-continued

DR 3a Submotif Peptides

| Type | Protein | Position | Sequence | Sequence Id. No. | Core Sequence | Core Seq. Id. No. |
|---|---|---|---|---|---|---|
| HPV33 | E1 | 615 | KLDLIEEEDKENHGG | 50705 | LIEEEDKEN | 51036 |
| HPV33 | E1 | 585 | KNPFPFDENGNPVYA | 50706 | FPFDENGNP | 51037 |
| HPV33 | E1 | 50 | LLEFIDDSMENSIQA | 50707 | FIDDSMENS | 51038 |
| HPV33 | E1 | 260 | LQCLTCDRGIIILLL | 50708 | LTCDRGIII | 51039 |
| HPV33 | E1 | 394 | QAKIVKDCGIMCRHY | 50709 | IVKDCGIMC | 51040 |
| HPV33 | E1 | 358 | QWAYDNELTDDSDIA | 50710 | YDNELTDDS | 51041 |
| HPV33 | E1 | 164 | SSGVGDDSEVSCETN | 50711 | VGDDSEVSC | 51042 |
| HPV33 | E1 | 524 | SWTYIDDYMRNALDG | 50712 | YIDDYMRNA | 51043 |
| HPV33 | E1 | 18 | TGWFEVEAVIERRTG | 50713 | FEVEAVIER | 51044 |
| HPV33 | E1 | 219 | VRPFKSDKTSCTDWC | 50714 | FKSDKTSCT | 51045 |
| HPV33 | E1 | 597 | VYAINDENWKSFFSR | 50715 | INDENWKSF | 51046 |
| HPV33 | E2 | 139 | EIYIIEEDTCTMVTG | 50716 | IIEEDTCTM | 51047 |
| HPV33 | E2 | 77 | ELQMALETLSKSQYS | 50717 | MALETLSKS | 51048 |
| HPV33 | E2 | 171 | FKYFKEDAAKYSKTQ | 50718 | FKEDAAKYS | 51049 |
| HPV33 | E2 | 138 | GEIYIIEEDTCTMVT | 50719 | YIIEEDTCT | 51050 |
| HPV33 | E2 | 279 | IVHLKGESNSLKCLR | 50720 | LKGESNSLK | 51051 |
| HPV33 | E2 | 140 | IYIIEEDTCTMVTGK | 50721 | IEEDTCTMV | 51052 |
| HPV33 | E2 | 19 | LDLYEADKTDLPSQI | 50722 | YEADKTDLP | 51053 |
| HPV33 | E2 | 212 | TADIQTDNDNRPPQA | 50723 | IQTDNDNRP | 51054 |
| HPV33 | E2 | 244 | TKLFCADPALDNRTA | 50724 | FCADPALDN | 51055 |
| HPV33 | E2 | 325 | TVTFVTEQQQQMFLG | 50725 | FVTEQQQQM | 51056 |
| HPV33 | E2 | 119 | TVTVQYDNDKKNTMD | 50726 | VQYDNDKKN | 51057 |
| HPV33 | E2 | 36 | WKLIRMECALLYTAK | 50727 | IRMECALLY | 51058 |
| HPV33 | E2 | 170 | YFKYFKEDAAKYSKT | 50728 | YFKEDAAKY | 51059 |
| HPV33 | E6 | 1 | MFQDTEEKPRTL | 50729 | MFQDTEEKP | 51060 |
| HPV33 | E6 | 53 | LTVVYREGNPFGICK | 50730 | VYREGNPFG | 51061 |
| HPV33 | E7 | 11 | LKEYVLDLYPEPTDL | 50731 | YVLDLYPEP | 51062 |
| HPV33 | E7 | 23 | TDLYCYEQLSDSSDE | 50732 | YCYEQLSDS | 51063 |
| HPV33 | E7 | 15 | VLDLYPEPTDLYCYE | 50733 | LYPEPTDLY | 51064 |
| HPV33 | L1 | 348 | CTQVTSDSTYKNENF | 50734 | VTSDSTYKN | 51065 |
| HPV33 | L1 | 354 | DSTYKNENFKEYIRH | 50735 | YKNENFKEY | 51066 |
| HPV33 | L1 | 250 | FFFLRREQMFVRHFF | 50736 | LRREQMFVR | 51067 |
| HPV33 | L1 | 271 | GEAVPDDLYIKGSGT | 50737 | VPDDLYIKG | 51068 |
| HPV33 | L1 | 300 | GSMVTSESQLFNKPY | 50738 | VTSESQLFN | 51069 |
| HPV33 | L1 | 393 | IHAMNPDILEDWQFG | 50739 | MNPDILEDW | 51070 |
| HPV33 | L1 | 194 | INTIIEDGDMVDTGF | 50740 | IIEDGDMVD | 51071 |
| HPV33 | L1 | 454 | KEKFSADLDQFPLGR | 50741 | FSADLDQFP | 51072 |
| HPV33 | L1 | 220 | KSDVPIDICGSTCKY | 50742 | VPIDICGST | 51073 |
| HPV33 | L1 | 382 | KVTLTAEVMTYIHAM | 50743 | LTAEVMTYI | 51074 |
| HPV33 | L1 | 397 | NPDILEDWQFGLTPP | 50744 | ILEDWQFGL | 51075 |
| HPV33 | L1 | 22 | SKVVSTDEYVSRTSI | 50745 | VSTDEYVSR | 51076 |
| HPV33 | L1 | 92 | TSFYNPDTQRLVWAC | 50746 | YNPDTQRLV | 51077 |
| HPV33 | L1 | 104 | WACVGLEIGRGQPLG | 50747 | VGLEIGRGQ | 51078 |
| HPV33 | L1 | 237 | YLKMTSEPYGDSLFF | 50748 | MTSEPYGDS | 51079 |
| HPV33 | L2 | 338 | DHTVPNEQYELQPLH | 50749 | VPNEQYELQ | 51080 |
| HPV33 | L2 | 433 | FDTIVVDGADFVLHP | 50750 | IVVDGADFV | 51081 |
| HPV33 | L2 | 260 | FESFDPEDTLQFQHS | 50751 | FDPEDTLQF | 51082 |
| HPV33 | L2 | 250 | HKLITYDNPAFESFD | 50752 | ITYDNPAFE | 51083 |
| HPV33 | L2 | 107 | IVSLIEETSFIEAGA | 50753 | LIEETSFIE | 51084 |
| HPV33 | L2 | 365 | LYDVYADDVDNVHTP | 50754 | VYADDVDNV | 51085 |
| HPV33 | L2 | 324 | RIHYYQDLSPIVPLD | 50755 | YYQDLSPIV | 51086 |
| HPV33 | L2 | 92 | RPPVTVDTVGPLDSS | 50756 | VTVDTVGPL | 51087 |
| HPV33 | L2 | 428 | SPFFPFDTIVVDGAD | 50757 | FPFDTIVVD | 51088 |
| HPV33 | L2 | 332 | SPIVPLDHTVPNEQY | 50758 | VPLDHTVPN | 51089 |
| HPV33 | L2 | 203 | TFVVSTDSSNVTSST | 50759 | VSTDSSNVT | 51090 |
| HPV33 | L2 | 366 | YDVYADDVDNVHTPM | 50760 | YADDVDNVH | 51091 |
| HPV33 | L2 | 196 | YENIPMDTFVVSTDS | 50761 | IPMDTFVVS | 51092 |
| HPV33 | L2 | 74 | YVPIGTDPPTAAIPL | 50762 | IGTDPPTAA | 51093 |
| HPV45 | E1 | 75 | AQEVQNDAQVLHLLK | 50763 | VQNDAQVLH | 51094 |
| HPV45 | E1 | 362 | DNDLTDESDMAFQYA | 50764 | LTDESDMAF | 51095 |
| HPV45 | E1 | 298 | ETCMLIEPPKLRSSV | 50765 | MLIEPPKLR | 51096 |
| HPV45 | E1 | 32 | GDVISDDEDETATDT | 50766 | ISDDEDETA | 51097 |
| HPV45 | E1 | 103 | GEQLSVDTDLSPRLQ | 50767 | LSVDTDLSP | 51098 |
| HPV45 | E1 | 325 | ISEVSGDTPEWIQRL | 50768 | VSGDTPEWI | 51099 |
| HPV45 | E1 | 513 | KVAMLDDATHTCWTY | 50769 | MLDDATHTC | 51100 |
| HPV45 | E1 | 203 | MLAVFKDIYGLSFTD | 50770 | VFKDIYGLS | 51101 |
| HPV45 | E1 | 18 | NGWFFVETIVEKKTG | 50771 | FFVETIVEK | 51102 |
| HPV45 | E1 | 501 | NSHFWLEPLADTKVA | 50772 | FWLEPLADT | 51103 |
| HPV45 | E1 | 585 | PHAFPFDKNGNPVYE | 50773 | FPFDKNGNP | 51104 |
| HPV45 | E1 | 394 | QAKYLKDCAVMCRHY | 50774 | YLKDCAVMC | 51105 |
| HPV45 | E1 | 105 | QLSVDTDLSPRLQEI | 50775 | VDTDLSPRL | 51106 |
| HPV45 | E1 | 358 | QWAFDNDLTDESDMA | 50776 | FDNDLTDES | 51107 |
| HPV45 | E1 | 615 | RLDLHEDDEDADTEG | 50777 | LHEDDEDAD | 51108 |
| HPV45 | E1 | 31 | TGDVISDDEDETATD | 50778 | VISDDEDET | 51109 |
| HPV45 | E1 | 219 | VRNFKSDKTTCTDWV | 50779 | FKSDKTTCT | 51110 |

TABLE XXa-continued

DR 3a Submotif Peptides

| Type | Protein | Position | Sequence | Sequence Id. No. | Core Sequence | Core Seq. Id. No. |
|---|---|---|---|---|---|---|
| HPV45 | E2 | 166 | GVYYIKDGDTTYYVQ | 50780 | YIKDGDTTY | 51111 |
| HPV45 | E2 | 296 | IIHLKGDKNSLKCLR | 50781 | LKGDKNSLK | 51112 |
| HPV45 | E2 | 138 | MNYVVWDSIYYITET | 50782 | VVWDSIYYI | 51113 |
| HPV45 | E2 | 93 | QSKYNNEEWTLQDTC | 50783 | YNNEEWTLQ | 51114 |
| HPV45 | E2 | 145 | SIYYITETGIWDKTA | 50784 | YITETGIWD | 51115 |
| HPV45 | E2 | 125 | TVHVYFDGNKDNCMN | 50785 | VYFDGNKDN | 51116 |
| HPV45 | E2 | 340 | TVTYNSEVQRNTFLD | 50786 | YNSEVQRNT | 51117 |
| HPV45 | E2 | 42 | WQLIRLENAILFTAR | 50787 | IRLENAILF | 51118 |
| HPV45 | E2 | 178 | YVQFKSECEKYGNSN | 50788 | FKSECEKYG | 51119 |
| HPV45 | E6 | 55 | LFIVYRDCIAYAACH | 50789 | VYRDCIAYA | 51120 |
| HPV45 | E6 | 17 | LPDLCTELNTSLQDV | 50790 | LCTELNTSL | 51121 |
| HPV45 | E6 | 85 | SNSVYGETLEKITNT | 50791 | VYGETLEKI | 51122 |
| HPV45 | E7 | 13 | EIVLHLEPQNELDPV | 50792 | LHLEPQNEL | 51123 |
| HPV45 | E7 | 75 | RIELTVESSADDLRT | 50793 | LTVESSADD | 51124 |
| HPV45 | E7 | 27 | VDLLCYEQLSESEEE | 50794 | LCYEQLSES | 51125 |
| HPV45 | L1 | 48 | ARVVNTDDYVSRTSI | 50795 | VNTDDYVSR | 51126 |
| HPV45 | L1 | 277 | FFCLRREQLFARHFW | 50796 | LRREQLFAR | 51127 |
| HPV45 | L1 | 298 | GDTVPTDLYIKGTSA | 50797 | VPTDLYIKG | 51128 |
| HPV45 | L1 | 247 | KCEVPLDICQSICKY | 50798 | VPLDICQSI | 51129 |
| HPV45 | L1 | 485 | KEKFSSDLDQYPLGR | 50799 | FSSDLDQYP | 51130 |
| HPV45 | L1 | 221 | KNTIIEDGDMVDTGY | 50800 | IIEDGDMVD | 51131 |
| HPV45 | L1 | 293 | RAGVMGDTVPTDLYI | 50801 | VMGDTVPTD | 51132 |
| HPV45 | L1 | 118 | STIYNPETQRLVWAC | 50802 | YNPETQRLV | 51133 |
| HPV45 | L1 | 413 | TITLTAEVMSYIHSM | 50803 | LTAEVMSYI | 51134 |
| HPV45 | L1 | 130 | WACVGMEIGRGQPLG | 50804 | VGMEIGRGQ | 51135 |
| HPV45 | L1 | 264 | YLQMSADPYGDSMFF | 50805 | MSADPYGDS | 51136 |
| HPV45 | L2 | 263 | DTTLSFEPTSNVPDS | 50806 | LSFEPTSNV | 51137 |
| HPV45 | L2 | 455 | IPYFFADGFVAA | 50807 | FFADGFVAA | 51138 |
| HPV45 | L2 | 106 | IVTLVEDSSVVASGA | 50808 | LVEDSSVVA | 51139 |
| HPV45 | L2 | 349 | LFDVYADFPPPASTT | 50809 | VYADFPPPA | 51140 |
| HPV45 | L2 | 91 | RPPVVIEPVGPTDPS | 50810 | VVIEPVGPT | 51141 |
| HPV45 | L2 | 319 | RVHFYHDISPIAATE | 50811 | FYHDISPIA | 51142 |
| HPV45 | L2 | 249 | SSLVTFDNPAYEPLD | 50812 | VTFDNPAYE | 51143 |
| HPV56 | E2 | 137 | ESIYCPDSVSSTCRY | 50813 | YCPDSVSST | 51144 |
| HPV56 | E2 | 131 | EVHMENESIYCPDSV | 50814 | MENESIYCP | 51145 |
| HPV56 | E2 | 20 | EVQIALESLSTTIYN | 50815 | IALESLSTT | 51146 |
| HPV56 | E2 | 62 | HIEVWFDGSKNNCMQ | 50816 | VWFDGSKNN | 51147 |
| HPV56 | E2 | 110 | HKTYYTDFEQEAKKF | 50817 | YYTDFEQEA | 51148 |
| HPV56 | E2 | 284 | ITIYKDETQRNSFL | 50818 | IYKDETQRN | 51149 |
| HPV56 | E2 | 129 | IWEVHMENESIYCPD | 50819 | VHMENESIY | 51150 |
| HPV56 | E2 | 53 | KKCFKKEGQHIEVWF | 50820 | FKKEGQHIE | 51151 |
| HPV56 | E2 | 285 | TIIYKDETQRNSFLS | 50821 | YKDETQRNS | 51152 |
| HPV56 | E2 | 30 | TTIYNNEEWTLRDTC | 50822 | YNNEEWTLR | 51153 |
| HPV56 | E2 | 240 | VVHLKGEPNRLKCCR | 50823 | LKGEPNRLK | 51154 |
| HPV56 | E2 | 82 | YIYYNGDCGWQKVCS | 50824 | YNGDCGWQK | 51155 |
| HPV56 | E2 | 260 | YKTLFVDVTSTYHWT | 50825 | LFVDVTSTY | 51156 |
| HPV56 | E6 | 57 | KLVYRDDFPYAVCRV | 50826 | YRDDFPYAV | 51157 |
| HPV56 | E6 | 56 | LKLVYRDDFPYAVCR | 50827 | VYRDDFPYA | 51158 |
| HPV56 | E7 | 72 | KFVVQLDIQSTKEDL | 50828 | VQLDIQSTK | 51159 |
| HPV56 | E7 | 11 | LQDVVLELTPQTEID | 50829 | VVLELTPQT | 51160 |
| HPV56 | L1 | 305 | GETIPAELYLKGSNG | 50830 | IPAELYLKG | 51161 |
| HPV56 | L1 | 20 | GLCIFLDVGAVNVFP | 50831 | IFLDVGAVN | 51162 |
| HPV56 | L1 | 334 | GSMITSEAQLFNKPY | 50832 | ITSEAQLFN | 51163 |
| HPV56 | L1 | 254 | KAEVPLDIVQSTCKY | 50833 | VPLDIVQST | 51164 |
| HPV56 | L1 | 416 | KITLSAEVMAYLHNM | 50834 | LSAEVMAYL | 51165 |
| HPV56 | L1 | 8 | MMYIYRDPPLHYGLC | 50835 | IYRDPPLHY | 51166 |
| HPV56 | L1 | 431 | NANLLEDWNIGLSPP | 50836 | LLEDWNIGL | 51167 |
| HPV56 | L1 | 488 | QDSFSTDLDQFPLGR | 50837 | FSTDLDQFP | 51168 |
| HPV56 | L1 | 57 | SKVVATDSYVKRTSI | 50838 | VATDSYVKR | 51169 |
| HPV56 | L1 | 125 | TNIYNPDQERLVWAC | 50839 | YNPDQERLV | 51170 |
| HPV56 | L1 | 137 | WACVGLEVGRGQPLG | 50840 | VGLEVGRGQ | 51171 |
| HPV56 | L1 | 284 | WFYLRREQLFARHYF | 50841 | LRREQLFAR | 51172 |
| HPV56 | L1 | 271 | YLKMSADAYGDSMWF | 50842 | MSADAYGDS | 51173 |
| HPV56 | L1 | 87 | YYSVTKDNTKTNIPK | 50843 | VTKDNTKTN | 51174 |
| HPV56 | L2 | 249 | ATLVSADNPLFEGTD | 50844 | VSADNPLFE | 51175 |
| HPV56 | L2 | 456 | IPYFFADGDVAA | 50845 | FFADGDVAA | 51176 |
| HPV56 | L2 | 106 | IVTLVEESSVIESGA | 50846 | LVEESSVIE | 51177 |
| HPV56 | L2 | 270 | PSGVAPDPDFMNIVA | 50847 | VAPDPDFMN | 51178 |
| HPV56 | L2 | 426 | PYDVTHDVYIQGSSF | 50848 | VTHDVYIQG | 51179 |
| HPV56 | L2 | 91 | RPPIVVESVGPTDPS | 50849 | IVVESVGPT | 51180 |
| HPV56 | L2 | 319 | RVHYYYDISPIAQAE | 50850 | YYYDISPIA | 51181 |
| HPV56 | L2 | 161 | TNPLFIDPPVIEAPQ | 50851 | LFIDPPVIE | 51182 |
| HPV56 | L2 | 354 | YANIDDEAPGLSSQS | 50852 | IDDEAPGLS | 51183 |

TABLE XXb

DR3b Supermotif Peptides

| Type | Protein | Position | Sequence | Sequence Id. No. | Core Sequence | Core Seq. Id. No. |
|---|---|---|---|---|---|---|
| HPV16 | E1 | 115 | AICIEKQSRAAKRRL | 51184 | IEKQSRAAK | 51334 |
| HPV16 | E1 | 545 | GNLVSMDVKHRPLVQ | 51185 | VSMDVKHRP | 51335 |
| HPV16 | E1 | 478 | LYGAANTGKSLFGMS | 51186 | AANTGKSLF | 51336 |
| HPV16 | E1 | 570 | NINAGTDSRWPYLHN | 51187 | AGTDSRWPY | 51337 |
| HPV16 | E1 | 602 | NPVYELNDKNWKSFF | 51188 | YELNDKNWK | 51338 |
| HPV16 | E1 | 145 | QQMLQVEGRHETETP | 51189 | LQVEGRHET | 51339 |
| HPV16 | E1 | 247 | TPSIADSIKTLLQQY | 51190 | IADSIKTLL | 51340 |
| HPV16 | E1 | 532 | WNYIDDNLRNALDGN | 51191 | IDDNLRNAL | 51341 |
| HPV16 | E1 | 23 | YVEAVVEKKTGDAIS | 51192 | AVVEKKTGD | 51342 |
| HPV16 | E2 | 125 | DGDICNTMHYTNWTH | 51193 | ICNTMHYTN | 51343 |
| HPV16 | E2 | 270 | ILTAFNSSHKGRINC | 51194 | AFNSSHKGR | 51344 |
| HPV16 | E2 | 167 | IRTYFVQFKDDAEKY | 51195 | YFVQFKDDA | 51345 |
| HPV16 | E2 | 271 | LTAFNSSHKGRINCN | 51196 | FNSSHKGRI | 51346 |
| HPV16 | E2 | 346 | RDQFLSQVKIPKTIT | 51197 | FLSQVKIPK | 51347 |
| HPV16 | E2 | 315 | YTAVSSTWHWTGHNV | 51198 | VSSTWHWTG | 51348 |
| HPV16 | E6 | 26 | CTELQTTIHDIILEC | 51199 | LQTTIHDII | 51349 |
| HPV16 | E6 | 117 | QKPLCPEEKQRHLDK | 51200 | LCPEEKQRH | 51350 |
| HPV16 | L1 | 165 | AANAGVDNRECISMD | 51201 | AGVDNRECI | 51351 |
| HPV16 | L1 | 359 | FVTVVDTTRSTNMSL | 51202 | VVDTTRSTN | 51352 |
| HPV16 | L1 | 440 | GGTLEDTYRFVTSQA | 51203 | LEDTYRFVT | 51353 |
| HPV16 | L1 | 141 | PLGVGISGHPLLNKL | 51204 | VGISGHPLL | 51354 |
| HPV16 | L1 | 173 | RECISMDYKQTQLCL | 51205 | ISMDYKQTQ | 51355 |
| HPV16 | L1 | 452 | SQAIACQKHTPPAPK | 51206 | IACQKHTPP | 51356 |
| HPV16 | L2 | 18 | ATQLYKTCKQAGTCP | 51207 | LYKTCKQAG | 51357 |
| HPV16 | L2 | 293 | HRPALTSRRTGIRYS | 51208 | ALTSRRTGI | 51358 |
| HPV16 | L2 | 7 | KRSAKRTKRASATQL | 51209 | AKRTKRASA | 51359 |
| HPV16 | L2 | 349 | PSTYTTTSHAALPTS | 51210 | YTTTSHAAL | 51360 |
| HPV18 | E1 | 229 | FTDLVRNFKSDKTTC | 51211 | LVRNFKSDK | 51361 |
| HPV18 | E1 | 552 | GNPISIDRKHKPLIQ | 51212 | ISIDRKHKP | 51362 |
| HPV18 | E1 | 509 | ISFVNSTHFWLEPL | 51213 | VNSTSHFWL | 51363 |
| HPV18 | E1 | 205 | KDLLKVNNKQGAMLA | 51214 | LKVNNKQGA | 51364 |
| HPV18 | E1 | 471 | KSFLKGTPKKNCLVF | 51215 | LKGTPKKNC | 51365 |
| HPV18 | E1 | 609 | NPVYEINDKNWKCFF | 51216 | YEINDKNWK | 51366 |
| HPV18 | E1 | 571 | PILLTTNIHPAKDNR | 51217 | LTTNIHPAK | 51367 |
| HPV18 | E1 | 22 | YVQAIVDKKTGDVIS | 51218 | AIVDKKTGD | 51368 |
| HPV18 | E2 | 23 | IDHYENDSKDIDSQI | 51219 | YENDSKDID | 51369 |
| HPV18 | E2 | 333 | TGILTVTYHSETQRT | 51220 | LTVTYHSET | 51370 |
| HPV18 | E2 | 172 | YNTFYIEFKSECEKY | 51221 | FYIEFKSEC | 51371 |
| HPV18 | E2 | 316 | YRDISSTWHWTGAGN | 51222 | ISSTWHWTG | 51372 |
| HPV18 | E6 | 134 | AGHYRGQCHSCCNRA | 51223 | YRGQCHSCC | 51373 |
| HPV18 | E7 | 54 | ARRAEPQRHTMLCMC | 51224 | AEPQRHTML | 51374 |
| HPV18 | L1 | 552 | APSATTSSKPAKRVR | 51225 | ATTSSKPAK | 51375 |
| HPV18 | L1 | 495 | KDAAPAENKDPYDKL | 51226 | APAENKDPY | 51376 |
| HPV18 | L1 | 176 | PLGVGLSGHPFYNKL | 51227 | VGLSGHPFY | 51377 |
| HPV18 | L1 | 208 | RDNVSVDYKQTQLCI | 51228 | VSVDYKQTQ | 51378 |
| HPV18 | L1 | 200 | TSNVSEDVRDNVSVD | 51229 | VSEDVRDNV | 51379 |
| HPV18 | L1 | 476 | TTSLVDTYRFVQSVA | 51230 | LVDTYRFVQ | 51380 |
| HPV18 | L2 | 263 | DTTLTFDPRSDVPDS | 51231 | LTFDPRSDV | 51381 |
| HPV18 | L2 | 286 | HRPALTSRRGTVRFS | 51232 | ALTSRRGTV | 51382 |
| HPV18 | L2 | 17 | VTDLYKTCKQSGTCP | 51233 | LYKTCKQSG | 51383 |
| HPV31 | E1 | 114 | AICIENNSKTAKRRL | 51234 | IENNSKTAK | 51384 |
| HPV31 | E1 | 103 | CVDYNISPRLKAICI | 51235 | YNISPRLKA | 51385 |
| HPV31 | E1 | 525 | GNPVSIDVKHKALMQ | 51236 | VSIDVKHKA | 51386 |
| HPV31 | E1 | 458 | IHGAPNTGKSYFGMS | 51237 | APNTGKSYF | 51387 |
| HPV31 | E1 | 533 | KHKALMQLKCPPLLI | 51238 | ALMQLKCPP | 51388 |
| HPV31 | E1 | 550 | NINAGKDDRWPYLHS | 51239 | AGKDDRWPY | 51389 |
| HPV31 | E1 | 582 | NPVYELSDKNWKSFF | 51240 | YELSDKNWK | 51390 |
| HPV31 | E2 | 125 | DGDVHNTMHYTNWKF | 51241 | VHNTMHYTN | 51391 |
| HPV31 | E2 | 121 | EVQFDGDVHNTMHYT | 51242 | FDGDVHNTM | 51392 |
| HPV31 | E2 | 171 | FVNFTEEAKKYGTGK | 51243 | FTEEAKKYG | 51393 |
| HPV31 | E2 | 159 | GIYYVHEGHITYFVN | 51244 | YVHEGHITY | 51394 |
| HPV31 | E2 | 19 | LEHYENDSKRLCDHI | 51245 | YENDSKRLC | 51395 |
| HPV31 | E2 | 345 | LTYISTSQRDDFLNT | 51246 | ISTSQRDDF | 51396 |
| HPV31 | E2 | 353 | RDDFLNTVKIPNTVS | 51247 | FLNTVKIPN | 51397 |
| HPV31 | E2 | 239 | VRRATTSTKRPRTEP | 51248 | ATTSTKRPR | 51398 |
| HPV31 | E2 | 322 | YEQVSSTWHWTCTDG | 51249 | VSSTWHWTC | 51399 |
| HPV31 | E6 | 110 | QRPLCPEEKQRHLDK | 51250 | LCPEEKQRH | 51400 |
| HPV31 | E7 | 57 | IVTFCCQCKSTLRLC | 51251 | FCCQCKSTL | 51401 |
| HPV31 | L1 | 213 | DFTALQDTKSNVPLD | 51252 | ALQDTKSNV | 51402 |
| HPV31 | L1 | 334 | FVTVVDTTRSTNMSV | 51253 | VVDTTRSTN | 51403 |

TABLE XXb-continued

DR3b Supermotif Peptides

| Type | Protein | Position | Sequence | Sequence Id. No. | Core Sequence | Core Seq. Id. No. |
|---|---|---|---|---|---|---|
| HPV31 | L1 | 116 | PLGVGISGHPLLNKF | 51254 | VGISGHPLL | 51404 |
| HPV31 | L1 | 148 | RECISMDYKQTQLCL | 51255 | ISMDYKQTQ | 51405 |
| HPV31 | L1 | 415 | SGSLEDTYRFVTSQA | 51256 | LEDTYRFVT | 51406 |
| HPV31 | L2 | 18 | ATQLYQTCKAAGTCP | 51257 | LYQTCKAAG | 51407 |
| HPV31 | L2 | 286 | HRPALTSRRNTVRYS | 51258 | ALTSRRNTV | 51408 |
| HPV31 | L2 | 170 | PTPAETSGHLLLSSS | 51259 | AETSGHLLL | 51409 |
| HPV31 | L2 | 263 | SLYFSNTSHNIAPDP | 51260 | FSNTSHNIA | 51410 |
| HPV31 | L2 | 73 | TGYVPLSTRPSTVSE | 51261 | VPLSTRPST | 51411 |
| HPV31 | L2 | 226 | YSKATQQVKVIDPTF | 51262 | ATQQVKVID | 51412 |
| HPV33 | E1 | 22 | EVEAVIERRTGDNIS | 51263 | AVIERRTGD | 51413 |
| HPV33 | E1 | 538 | GNEISIDVKHRALVQ | 51264 | ISIDVKHRA | 51414 |
| HPV33 | E1 | 635 | KCSAGENTRSLRS | 51265 | AGENTRSLR | 51415 |
| HPV33 | E1 | 546 | KHRALVQLKCPPLLL | 51266 | ALVQLKCPP | 51416 |
| HPV33 | E1 | 616 | LDLIEEEDKENHGGN | 51267 | IEEEDKENH | 51417 |
| HPV33 | E1 | 563 | NTNAGTDSRWPYLHS | 51268 | AGTDSRWPY | 51418 |
| HPV33 | E1 | 240 | SPSVAESLKVLIKQH | 51269 | VAESLKVLI | 51419 |
| HPV33 | E2 | 42 | ECALLYTAKQMGFSH | 51270 | LLYTAKQMG | 51420 |
| HPV33 | E2 | 334 | QQMFLGTVKIPPTVQ | 51271 | FLGTVKIPP | 51421 |
| HPV33 | E2 | 121 | TVQYDNDKKNTMDYT | 51272 | YDNDKKNTM | 51422 |
| HPV33 | E2 | 303 | YSSMSSTWHWTSDNK | 51273 | MSSTWHWTS | 51423 |
| HPV33 | E5 | 62 | LPMMCINFHAQHMTQ | 51274 | MCINFHAQH | 51424 |
| HPV33 | E6 | 19 | CQALETTIHNIELQC | 51275 | LETTIHNIE | 51425 |
| HPV33 | E6 | 88 | GNTLEQTVKKPLNEI | 51276 | LEQTVKKPL | 51426 |
| HPV33 | E6 | 119 | KRHVDLNKRFHNISG | 51277 | VDLNKRFHN | 51427 |
| HPV33 | E6 | 110 | QRPLCPQEKKRHVDL | 51278 | LCPQEKKRH | 51428 |
| HPV33 | L1 | 333 | FVTVVDTTRSTNMTL | 51279 | VVDTTRSTN | 51429 |
| HPV33 | L1 | 36 | IYYYAGSSRLLAVGH | 51280 | YAGSSRLLA | 51430 |
| HPV33 | L1 | 483 | KRAAPTSTRTSSAKR | 51281 | APTSTRTSS | 51431 |
| HPV33 | L1 | 116 | PLGVGISGHPLLNKF | 51282 | VGISGHPLL | 51432 |
| HPV33 | L1 | 148 | RECLSMDYKQTQLCL | 51283 | LSMDYKQTQ | 51433 |
| HPV33 | L1 | 413 | SASLQDTYRFVTSQA | 51284 | LQDTYRFVT | 51434 |
| HPV33 | L2 | 17 | ATQLYQTCKATGTCP | 51285 | LYQTCKATG | 51435 |
| HPV33 | L2 | 242 | DPAFLTSPHKLITYD | 51286 | FLTSPHKLI | 51436 |
| HPV33 | L2 | 459 | FPYFFTDVRVAA | 51287 | FFTDVRVAA | 51437 |
| HPV33 | L2 | 291 | HRPAITSRRHTVRFS | 51288 | AITSRRHTV | 51438 |
| HPV33 | L2 | 175 | PAPAEASGHFIFSSP | 51289 | AEASGHFIF | 51439 |
| HPV45 | E1 | 215 | FTDLVRNFKSDKTTC | 51290 | LVRNFKSDK | 51440 |
| HPV45 | E1 | 538 | GNPISIDRKHKPLLQ | 51291 | ISIDRKHKP | 51441 |
| HPV45 | E1 | 495 | ISFVNSNSHFWLEPL | 51292 | VNSNSHFWL | 51442 |
| HPV45 | E1 | 457 | KEFLKGTPKKNCILL | 51293 | LKGTPKKNC | 51443 |
| HPV45 | E1 | 191 | KELLQASNKKAAMLA | 51294 | LQASNKKAA | 51444 |
| HPV45 | E1 | 595 | NPVYEINDKNWKCFF | 51295 | YEINDKNWK | 51445 |
| HPV45 | E2 | 174 | DTTYYVQFKSECEKY | 51296 | YYVQFKSEC | 51446 |
| HPV45 | E2 | 48 | ENAILFTAREHGITK | 51297 | ILFTAREHG | 51447 |
| HPV45 | E2 | 25 | LDHYENDSKDINSQI | 51298 | YENDSKDIN | 51448 |
| HPV45 | E2 | 256 | QCGLTEQHHGRVNTH | 51299 | LTEQHHGRV | 51449 |
| HPV45 | E2 | 320 | YSEISSTWHWTGCNK | 51300 | ISSTWHWTG | 51450 |
| HPV45 | E6 | 130 | FHSIAGQYRGQCNTC | 51301 | IAGQYRGQC | 51451 |
| HPV45 | E7 | 55 | ARRAEPQRHKILCVC | 51302 | AEPQRHKIL | 51452 |
| HPV45 | L1 | 362 | FVTVVDTTRSTNLTL | 51303 | VVDTTRSTN | 51453 |
| HPV45 | L1 | 142 | PLGIGLSGHPFYNKL | 51304 | IGLSGHPFY | 51454 |
| HPV45 | L1 | 174 | RDNVSVDYKQTQLCI | 51305 | VSVDYKQTQ | 51455 |
| HPV45 | L1 | 166 | TAVITQDVRDNVSVD | 51306 | ITQDVRDNV | 51456 |
| HPV45 | L1 | 444 | TTSLVDTYRFVQSVA | 51307 | LVDTYRFVQ | 51457 |
| HPV45 | L2 | 17 | ATDLYRTCKQSGTCP | 51308 | LYRTCKQSG | 51458 |
| HPV45 | L2 | 306 | ATMFTRSGKQIGGRV | 51309 | FTRSGKQIG | 51459 |
| HPV45 | L2 | 286 | HRPALSSRRGTVRFS | 51310 | ALSSRRGTV | 51460 |
| HPV45 | L2 | 230 | YSRANQQVRVSTSQF | 51311 | ANQQVRVST | 51461 |
| HPV56 | E2 | 264 | FVDVTSTYHWTSTDN | 51312 | VTSTYHWTS | 51462 |
| HPV56 | E2 | 102 | GIYYVHDGHKTYYTD | 51313 | YVHDGHKTY | 51463 |
| HPV56 | E2 | 177 | NQDAAVSHRPGKRPR | 51314 | AAVSHRPGK | 51464 |
| HPV56 | E2 | 142 | PDSVSSTCRYNVSPV | 51315 | VSSTCRYNV | 51465 |
| HPV56 | E2 | 224 | SRSINNNNHPGDKTT | 51316 | INNNNHPGD | 51466 |
| HPV56 | E2 | 114 | YTDFEQEAKKFGCKN | 51317 | FEQEAKKFG | 51467 |
| HPV56 | E6 | 120 | EKQLHCDRKRRFHLI | 51318 | LHCDRKRRF | 51468 |
| HPV56 | E6 | 113 | QSPLTPEEKQLHCDR | 51319 | LTPEEKQLH | 51469 |
| HPV56 | E6 | 49 | YNFACTELKLVYRDD | 51320 | ACTELKLVY | 51470 |
| HPV56 | L1 | 246 | DFKVLQESKAEVPLD | 51321 | VLQESKAEV | 51471 |
| HPV56 | L1 | 367 | FVTVVDTTRSTNMTI | 51322 | VVDTTRSTN | 51472 |

TABLE XXb-continued

DR3b Supermotif Peptides

| Type | Protein | Position | Sequence | Sequence Id. No. | Core Sequence | Core Seq. Id. No. |
|---|---|---|---|---|---|---|
| HPV56 | L1 | 513 | KPAVATSKKRSAPTS | 51323 | VATSKKRSA | 51473 |
| HPV56 | L1 | 259 | LDIVQSTCKYPDYLK | 51324 | VQSTCKYPD | 51474 |
| HPV56 | L1 | 173 | NNNVIEDSRDNISVD | 51325 | VIEDSRDNI | 51475 |
| HPV56 | L1 | 149 | PLGAGLSGHPLFNRL | 51326 | AGLSGHPLF | 51476 |
| HPV56 | L1 | 181 | RDNISVDGKQTQLCI | 51327 | ISVDGKQTQ | 51477 |
| HPV56 | L1 | 512 | SKPAVATSKKRSAPT | 51328 | AVATSKKRS | 51478 |
| HPV56 | L2 | 17 | ATQLYKTCKLSGTCP | 51329 | LYKTCKLSG | 51479 |
| HPV56 | L2 | 303 | GRKATIQTRRGTQIG | 51330 | ATIQTRRGT | 51480 |
| HPV56 | L2 | 286 | HRPAFTTRRGGVRFS | 51331 | AFTTRRGGV | 51481 |
| HPV56 | L2 | 367 | QSVATPSAHLPIKPS | 51332 | ATPSAHLPI | 51482 |
| HPV56 | L2 | 230 | YRKAFQQVKVTDPAF | 51333 | AFQQVKVTD | 51483 |

TABLE XXI

Population coverage with combined HLA Supertypes

| | PHENOTYPIC FREQUENCY | | | | | |
|---|---|---|---|---|---|---|
| HLA-SUPERTYPES | Caucasian | North American Black | Japanese | Chinese | Hispanic | Average |
| a. Individual Supertypes | | | | | | |
| A2 | 45.8 | 39.0 | 42.4 | 45.9 | 43.0 | 43.2 |
| A3 | 37.5 | 42.1 | 45.8 | 52.7 | 43.1 | 44.2 |
| B7 | 43.2 | 55.1 | 57.1 | 43.0 | 49.3 | 49.5 |
| A1 | 47.1 | 16.1 | 21.8 | 14.7 | 26.3 | 25.2 |
| A24 | 23.9 | 38.9 | 58.6 | 40.1 | 38.3 | 40.0 |
| B44 | 43.0 | 21.2 | 42.9 | 39.1 | 39.0 | 37.0 |
| B27 | 28.4 | 26.1 | 13.3 | 13.9 | 35.3 | 23.4 |
| B62 | 12.6 | 4.8 | 36.5 | 25.4 | 11.1 | 18.1 |
| B58 | 10.0 | 25.1 | 1.6 | 9.0 | 5.9 | 10.3 |
| b. Combined Supertypes | | | | | | |
| A2, A3, B7 | 84.3 | 86.8 | 89.5 | 89.8 | 86.8 | 87.4 |
| A2, A3, B7, A24, B44, A1 | 99.5 | 98.1 | 100.0 | 99.5 | 99.4 | 99.3 |
| A2, A3, B7, A24, B44, A1, B27, B62, B58 | 99.9 | 99.6 | 100.0 | 99.8 | 99.9 | 99.8 |

TABLE XXII

ACCESSION NUMBERS

| | | |
|---|---|---|
| HPV16 | E1 | W1SLHS |
| HPV16 | E2 | W2WLHS |
| HPV16 | E5 | W5WLHS |
| HPV16 | E6 | W6WLHS |
| HPV16 | E7 | W7WLHS |
| HPV16 | L1 | AAD33259 |
| HPV16 | L2 | AAD33258 |
| HPV18 | E1 | W1WL18 |
| HPV18 | E2 | W2WL18 |
| HPV18 | E5 | W5WL18 |
| HPV18 | E6 | W6WL18 |
| HPV18 | E7 | PO6788 |
| HPV18 | L1 | CAA28671 |
| HPV18 | L2 | P2WL18 |
| HPV31 | E1 | W1WL31 |
| HPV31 | E2 | W2WL3 |
| HPV31 | E5 | W5WL31 |
| HPV31 | E6 | W6WL31 |
| HPV31 | E7 | W7WL31 |
| HPV31 | L1 | P1WL31 |
| HPV31 | L2 | P2WL31 |
| HPV45 | E1 | S36563 |
| HPV45 | E2 | S36564 |
| HPV45 | E6 | CAB44706 |
| HPV45 | E7 | CAB44707 |
| HPV45 | L1 | CAB44705 |
| HPV45 | L2 | S36565 |
| HPV33 | E1 | W1WL33 |
| HPV33 | E2 | W2WL33 |
| HPV33 | E5 | W5WL33 |
| HPV33 | E6 | W6WL33 |
| HPV33 | E7 | W7WL33 |
| HPV33 | L1 | P1WL33 |
| HPV33 | L2 | P2WL33 |
| HPV56 | E2 | S36581 |
| HPV56 | E6 | W6WL56 |
| HPV56 | E7 | S36580 |
| HPV56 | L1 | S38563 |
| HPV56 | L2 | S36582 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07026443B1). An electronic copy of the "Sequence Listing" will also be available from the USPTO upon request and payment of the fee set forth in 37 CFR 1.19(b)(3).

What is claimed is:

1. A composition comprising an isolated oligopeptide 13 residues or less in length, which comprises the sequence ATLERTEVY (SEQ ID NO:31040).

2. The composition of claim 1, wherein the oligopeptide is joined to an amino acid linker.

3. The composition of claim 1, further comprising a CTL epitope wherein the CTL epitope is admixed or joined to the oligopeptide.

4. The composition of claim 1, further comprising an HTL epitope, wherein the HTL epitope is admixed or joined to the oligopeptide.

5. The composition of claim 4, wherein the HTL epitope is a PD-DR binding molecule.

6. The composition of claim 1, further comprising a liposome, wherein the oligopeptide is on or within the liposome.

7. The composition of claim 1, wherein the oligopeptide is joined to a lipid.

8. The composition of claim 1, wherein the oligopeptide is a heteropolymer.

9. The composition of claim 1, wherein the oligopeptide is a homopolymer.

10. The composition of claim 1, wherein the oligopeptide is bound to an HLA heavy chain, $\beta$2-microglobulin, and strepavidin complex, whereby a tetramer is formed.

* * * * *

UNITED STATES PATENT AND TRADEMARK OFFICE
CERTIFICATE OF CORRECTION

| | | |
|---|---|---|
| PATENT NO. | : 7,026,443 B1 | Page 1 of 1 |
| APPLICATION NO. | : 09/641528 | |
| DATED | : April 11, 2006 | |
| INVENTOR(S) | : Sette et al. | |

It is certified that error appears in the above-identified patent and that said Letters Patent is hereby corrected as shown below:

Claim 5
In column 1375, line 27, the term "PD-DR" should be replaced with --Pan-DR--.

Signed and Sealed this

Twelfth Day of June, 2007

JON W. DUDAS
*Director of the United States Patent and Trademark Office*